US011986531B2

(12) United States Patent
Crew et al.

(10) Patent No.: US 11,986,531 B2
(45) Date of Patent: May 21, 2024

(54) COMPOUNDS AND METHODS FOR THE TARGETED DEGRADATION OF RAPIDLY ACCELERATED FIBROSARCOMA POLYPEPTIDES

(71) Applicants: ARVINAS OPERATIONS, INC., New Haven, CT (US); YALE UNIVERSITY, New Haven, CT (US)

(72) Inventors: Andrew P. Crew, Chester, CT (US); Keith R. Hornberger, Southbury, CT (US); Jing Wang, Milford, CT (US); Saul Jaime-Figueroa, Morris Plains, NJ (US); Hanqing Dong, Madison, CT (US); Kurt Zimmermann, Durham, CT (US); Craig M. Crews, New Haven, CT (US)

(73) Assignees: Arvinas Operations, Inc., New Haven, CT (US); Yale University, New Haven, CT (US)

( * ) Notice: Subject to any disclaimer, the term of this patent is extended or adjusted under 35 U.S.C. 154(b) by 75 days.

(21) Appl. No.: 17/387,621

(22) Filed: Jul. 28, 2021

(65) Prior Publication Data

US 2023/0000994 A1 Jan. 5, 2023

Related U.S. Application Data

(63) Continuation of application No. 16/563,842, filed on Sep. 7, 2019, now Pat. No. 11,173,211, which is a continuation-in-part of application No. 15/853,166, filed on Dec. 22, 2017, now Pat. No. 10,723,717.

(60) Provisional application No. 62/728,581, filed on Sep. 7, 2018, provisional application No. 62/582,698, filed on Nov. 7, 2017, provisional application No. 62/438,803, filed on Dec. 23, 2016.

(51) Int. Cl.

| | |
|---|---|
| ***C07D 401/14*** | (2006.01) |
| ***A61K 31/437*** | (2006.01) |
| ***A61K 47/55*** | (2017.01) |
| ***A61P 35/00*** | (2006.01) |
| ***C07D 413/14*** | (2006.01) |
| ***C07D 417/14*** | (2006.01) |
| ***C07D 471/04*** | (2006.01) |
| ***C07D 519/00*** | (2006.01) |

(52) U.S. Cl.

CPC ............ *A61K 47/55* (2017.08); *C07D 413/14* (2013.01); *C07D 417/14* (2013.01); *C07D 471/04* (2013.01); *C07D 519/00* (2013.01)

(58) Field of Classification Search

CPC .. C07D 401/14; C07D 471/04; C07D 519/00; A61K 31/437; A61P 35/00

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Dashaies et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,447,070 | B2 | 9/2016 | Muller et al. |
| 9,500,653 | B2 | 11/2016 | Crews et al. |
| 9,632,089 | B2 | 4/2017 | Crews et al. |
| 2003/0096841 | A1 | 5/2003 | Robarge et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0269140 | A1 | 10/2008 | Wang et al. |

(Continued)

FOREIGN PATENT DOCUMENTS

| | | |
|---|---|---|
| CN | 1844118 A | 10/2006 |
| CN | 103688176 A | 3/2014 |

(Continued)

OTHER PUBLICATIONS

Ahn, et al., "HIF-lalpha peptide derivatives with modifications at the hydroxyproline residue as activators of HIF-lalpha", Bioorg Med Chem Lett. 19(15), 2009, 4403-4405.

(Continued)

*Primary Examiner* — Bruck Kifle

(74) *Attorney, Agent, or Firm* — McCarter & English, LLP; Michael J. DeGrazia; James M. Alburger

(57) ABSTRACT

The present disclosure relates to bifunctional compounds, which find utility as modulators of Rapidly Accelerated Fibrosarcoma (RAF, such as c-RAF, A-RAF and/or B-RAF; the target protein). In particular, the present disclosure is directed to bifunctional compounds, which contain on one end a Von Hippel-Lindau, cereblon, Inhibitors of Apotosis Proteins or mouse double-minute homolog 2 ligand which binds to the respective E3 ubiquitin ligase and on the other end a moiety which binds the target protein RAF, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein, or the constitutive activation of the target protein, are treated or prevented with compounds and compositions of the present disclosure.

19 Claims, 385 Drawing Sheets

(56) References Cited

U.S. PATENT DOCUMENTS

| | | | |
|---|---|---|---|
| 2010/0203012 | A1 | 8/2010 | Laurent et al. |
| 2011/0195043 | A1 | 8/2011 | Sun et al. |
| 2011/0230457 | A1 | 9/2011 | Berghausen et al. |
| 2012/0270800 | A1 | 10/2012 | Verdine et al. |
| 2013/0029993 | A1 | 1/2013 | Stadtmueller |
| 2014/0088143 | A1 | 3/2014 | Jain |
| 2014/0235629 | A1 | 8/2014 | Bartberger et al. |
| 2014/0243372 | A1 | 8/2014 | Rew |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0141470 | A1 | 5/2015 | Garraway et al. |
| 2015/0259288 | A1 | 9/2015 | Nam et al. |
| 2015/0291562 | A1 | 10/2015 | Crew et al. |
| 2015/0344473 | A1 | 10/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |
| 2018/0353501 | A1 | 12/2018 | Crew et al. |
| 2019/0151295 | A1 | 5/2019 | Crew et al. |

FOREIGN PATENT DOCUMENTS

| | | | |
|---|---|---|---|
| CN | 103159736 | B | 5/2015 |
| EP | 2985285 | | 2/2016 |
| JP | A 2010-502627 | | 1/2010 |
| KR | 20180011759 | A | 2/2018 |
| RU | 2008112221 | A | 10/2009 |
| RU | 2418800 | | 5/2011 |
| RU | 2448101 | C2 | 4/2012 |
| RU | 2011121567 | A | 10/2012 |
| RU | 2012138709 | A | 3/2014 |
| WO | WO 1998/003502 | | 1/1998 |
| WO | WO 2000/066119 | | 11/2000 |
| WO | WO 2002/066512 | | 8/2002 |
| WO | WO 2002/100845 | | 12/2002 |
| WO | WO 2005/016326 | | 2/2005 |
| WO | WO 2005/097791 | | 10/2005 |
| WO | WO 2006/069063 | | 6/2006 |
| WO | WO 2006/084015 | A2 | 8/2006 |
| WO | WO 2006/113942 | | 10/2006 |
| WO | WO 2007/101347 | | 9/2007 |
| WO | WO 2007/106670 | | 9/2007 |
| WO | WO 2007/115289 | | 10/2007 |
| WO | WO 2007/130626 | | 11/2007 |
| WO | WO 2008/011392 | | 1/2008 |
| WO | WO 2008/014236 | | 1/2008 |
| WO | WO 2008/109057 | | 9/2008 |
| WO | WO 2008/128121 | | 10/2008 |
| WO | WO 2008/128171 | | 10/2008 |
| WO | WO 2008/134679 | | 11/2008 |
| WO | WO 2009/015254 | | 1/2009 |
| WO | WO 2009/060292 | | 5/2009 |
| WO | WO 2010/107485 | | 9/2010 |
| WO | WO 2010/141805 | | 12/2010 |
| WO | WO 2011/008260 | | 1/2011 |
| WO | WO 2012/003281 | | 1/2012 |
| WO | WO 2012/007409 | | 1/2012 |
| WO | WO 2012/040527 | | 3/2012 |
| WO | WO 2012/078559 | | 6/2012 |
| WO | WO 2012/090104 | | 7/2012 |
| WO | WO 2017/176958 | | 10/2012 |
| WO | WO 2013/071035 | | 5/2013 |
| WO | WO 2013/071039 | | 5/2013 |
| WO | WO 2013/097224 | | 7/2013 |
| WO | WO 2013/106643 | | 7/2013 |
| WO | WO 2013/106646 | | 7/2013 |
| WO | WO 2013/170147 | | 11/2013 |
| WO | WO 2013/175417 | | 11/2013 |
| WO | WO 2013/178570 | | 12/2013 |
| WO | WO 2014/011712 | | 1/2014 |
| WO | WO 2014/020502 | | 2/2014 |
| WO | WO 2014/025759 | | 2/2014 |
| WO | WO 2014/038606 | | 3/2014 |
| WO | WO 2014/047024 | | 3/2014 |
| WO | WO 2014/055461 | | 4/2014 |
| WO | WO 2014/074658 | | 5/2014 |
| WO | WO 2014/100065 | | 6/2014 |
| WO | WO 2014/100071 | | 6/2014 |
| WO | WO 2014/107713 | | 7/2014 |
| WO | WO 2014/108452 | | 7/2014 |
| WO | WO 2014/123418 | | 8/2014 |
| WO | WO 2014/134201 | | 9/2014 |
| WO | WO 2014/151863 | | 9/2014 |
| WO | WO 2015/000868 | | 1/2015 |
| WO | WO 2015/006524 | | 1/2015 |
| WO | WO 2015/097621 | | 7/2015 |
| WO | WO 2015/160845 | | 10/2015 |
| WO | WO 2016/105518 | | 6/2016 |
| WO | 2016/149668 | A1 | 9/2016 |
| WO | WO 2016/146985 | | 9/2016 |
| WO | WO 2016/169989 | | 10/2016 |
| WO | WO 2016/172134 | | 10/2016 |
| WO | WO 2016/197114 | | 12/2016 |
| WO | WO 2017/007612 | A1 | 1/2017 |
| WO | WO 2017/011590 | | 1/2017 |
| WO | WO 2017/024317 | | 2/2017 |
| WO | WO 2017/024318 | A1 | 2/2017 |
| WO | WO 2017/024319 | A1 | 2/2017 |
| WO | WO 2017/030814 | | 2/2017 |
| WO | WO 2017/046036 | | 3/2017 |
| WO | WO 2017/079267 | | 5/2017 |
| WO | WO 2017/117473 | | 7/2017 |
| WO | WO 2017/117474 | | 7/2017 |
| WO | WO 2017/161119 | | 9/2017 |
| WO | WO 2017/176957 | | 10/2017 |
| WO | WO 2017/185023 | | 10/2017 |
| WO | WO 2017/185031 | | 10/2017 |
| WO | WO 2017/185034 | | 10/2017 |
| WO | WO 2017/185036 | | 10/2017 |
| WO | WO 2017/197051 | | 11/2017 |
| WO | WO 2017/197055 | | 11/2017 |
| WO | WO 2017/197056 | A1 | 11/2017 |
| WO | WO 2017/223415 | | 12/2017 |
| WO | WO 2017/223452 | | 12/2017 |
| WO | WO 2018/052949 | | 3/2018 |
| WO | WO 2018/064589 | A1 | 4/2018 |
| WO | WO 2018/098275 | | 5/2018 |
| WO | WO 2018/098280 | A1 | 5/2018 |
| WO | WO 2018/098288 | | 5/2018 |
| WO | WO 2018/106870 | | 6/2018 |
| WO | WO 2018/148440 | | 8/2018 |
| WO | WO 2018/200981 | | 11/2018 |

OTHER PUBLICATIONS

Ardecky, RJ, et al., "Design, synthesis and evaluation of inhibitor of apoptosis protein (IAP) antagonists that are highly selective for the

(56) References Cited

OTHER PUBLICATIONS

BIR2 domain of XIAP", Bioorg. Med. Chem., 23(14): 4253-4257 (2013).
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).
Bargagna-Mohan, et al., "Use of PROTACS as molecular probes of angiogenesis", Bioorg Med Chem Left. 15(11) 2005, 2724-2727.
Bondeson DP, et al. (2018) "Lessons in PROTAC Design from Selective Degradation with a Promiscuous Warhead." *Cell Chem Biol* 25(1):78-87 e75.
Bondeson, et al., (2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIF1a", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.
Burslem GM, et al. (2018) "The Advantages of Targeted Protein Degradation Over Inhibition: An RTK Case Study." *Cell Chem Biol* 25(1):67-77 e63.
Burslem, et al., (2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS Registry No. 1004933-70-3, which entered STN on Feb. 21, 2008.
CAS Registry No. 1226974-40-8, indexed in the Registry file on STN CAS Online Jun. 4, 2010.
CAS Registry No. 871986-52-6 entered STN Jan. 16, 2006.
Cas RN 1542127-97-8 STN Entry, Feb. 11, 2014.
Chan, et al., (2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds." *J Med Chem* 61(2):504-513.
Chene, P., et al., "Inhibiting the p53-MDM2 interaction: an important target for cancer therapy" Nat. Rev. Cancer (2003), 3, 102-109.
Churcher I (2018) "Protac-Induced Protein Degradation in Drug Discovery: Breaking the Rules or Just Making New Ones?" *J Med Chem* 61(2):444-452.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antogonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crew AP, et al. (2018) "Identification and Characterization of Von Hippel-Lindau-Recruiting Proteolysis Targeting Chimeras (PROTACs) of TANK-Binding Kinase 1." *J Med Chem* 61(2):583-598.
Crews, C. M., "Targeting the undruggable proteome: the small molecules of my dreams", *Chem Biol 17*, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al.).
Dixon, S. J. et al., "Identifying druggable disease-modifying gene products",. *Curr Opin Chem Biol 13*, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 ( 2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Grasso, et al., "Chemically linked vemurafenib inhibitors promote an inactive BRAF V600E Conformation" ACS Chem. Biol. Aug. 29, 2016, 11, 2876-2888.
Graves, Lee M., et al, "The dynamic nature of the kinome", Biochemical Journal, Feb. 15; 450(1), 1-8 (2013).
Han, Xin, et al., Discovery of ARD-69 as a Highly Potent Proteolysis Targeting Chimera (PROTAC) Degrader of Androgen Receptor (AR) for the Treatment of Prostate Cancer, Journal of Medicinal Chemistry 2019 62 (2), 941-964, DOI: 10.1021/acs.jmedchem.8b01631.
Hansen, J.D., et al., Potent and selective pyrazole-based inhibitors of B-Raf kinase, Bioorganic & Medicinal Chemistry Letters 18 (2008) 4692-4695, Jul. 5, 2008.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in Hlf-1 alpha by pVHL", Nature 417, Jun. 27, 2002, 975-978.
Hu, Jiantao, et al., Discovery of ERD-308 as a Highly Potent Proteolysis Targeting Chimera (PROTAC) Degrader of Estrogen Receptor (ER), DOI: 10.1021/acs.jmedchem.8b01572, Journal of Medicinal Chemistry, vol. 62, pp. 1420-1442, 2019, http://dx.doi.org/10.1021/acs.jmedchem.8b01572.

(56) References Cited

OTHER PUBLICATIONS

Huang HT, et al. (2018) "A Chemoproteomic Approach to Query the Degradable Kinome Using a Multi-kinase Degrader." *Cell Chem Biol* 25(1):88-99 e86.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
International Search Report and Written Opinion for PCT/US2019/050114, dated Jan. 2, 2020.
Ishikawa, T. et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry 2011, 54 (23), 8030-8050.
Itoh, et al., "Development of target protein selective degradation inducer for protein knockdown," Bioorg. Med. Chem., 2011, 19, 3229-3241.
Itoh, et al., "Protein knockdown using methyl bestatin-ligand hybrid molecules: design and synthesis of inducers of ubiquitination-mediated degradation of cellular retinoic acid-binding proteins," J. Am. Chem. Soc., 2010, 132, 5820-5826.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Kim, Minjung, et al., Design, synthesis and biological evaluation of benzyl 2-(1H-imidazole-1-yl) pyrimidine analogues as selective and potent Raf inhibitors, Bioorganic & Medicinal Chemistry Letters, 24 (May 17, 2014) 3600-3604.
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Kronke, et al, "Lenalidomide Causes Selective Degradation of IKZF1 and IKZF3 in Multiple Myeloma Cells", Science 343, 301-305 (2014).
Lackey, K. et al., "The discovery of potent cRaf1 kinase inhibitors", Bioorganic and Medicinal Chemistry Letters, 10 (2000), 223-226.
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Mahalingam, D., et al., "Targeting HSP90 for cancer therapy", Br J Cancer 100, 1523-1529 (2009).
Maniaci C, et al. (2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (2010).
Medline Plus Trusted Health Information for You, www.nim.nih.gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Noguchi-Yachide, et al., BET Bromodomain as a Target of Epigenitic Therapy, Chemical and Pharmaceutical Bulletin, Jun. 1, 2016, vol. 64, Iss 6, pp. 540-547.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL," Discovery of potent heterodimeric antagonists of inhibitor of apoptosis proteins (IAPs) with sustained antitumor activity", J. Med. Chem. 58(3), 1556-1562 (2015).
Poulikakos, P. I., Zhang, C., Bollag, G., Shokat, K. M. & Rosen, N. RAF inhibitors transactivate RAF dimers and ERK signalling in cells with wild-type BRAF. Nature 464, 427-430 (2010).
Powell, C. E. et al. Chemically Induced Degradation of Anaplastic Lymphoma Kinase (ALK). J. Med. Chem. 61, 4249-4255 (2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina et al., "Chemical Inducers of Targeted Protein Degradation," The Journal of Biological Chemistry, 2010, vol. 285, No. 15, pp. 11057-11060.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. Pub Med PMID: 25384157.

(56) References Cited

OTHER PUBLICATIONS

Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal-An attractive strategy for cancer therapy. Science 355, 1163-1167 (2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stanton, et al., (2018) "Chemically induced proximity in biology and medicine." *Science* 359(6380).
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, B. et al. BET protein proteolysis targeting chimera (PROTAC) exerts potent lethal activity against mantle cell lymphoma cells. Leukemia 32, 343-352 (2018).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Takeuchi, et al., "Receptor Tyrosine Kinases and Targeted Cancer Therapeutics", Biol Pharm Bull 34, 1774-1780 (2011).
Takle, A. K., et al., (378) The identification of potent and selective imidazole-based inhibitors of B-Raf kinase, Bioorganic & Medicinal Chemistry Letters 16 (2006) 378-381, (Jan. 2006).
Toure, et al., (2016) "Small-Molecule PROTACS: New Approaches to Protein Degradation." *Angew Chem Int Ed Engl* 55(6):1966-1973.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Waizenegger, I.C., et al., A Novel RAF Kinase Inhibitor with DFG-Out-Binding Mode: High Efficacy in BRAF-Mutant Tumor Xenograft Models in the Absence of Normal Tissue Hyperproliferation, Mol Cancer Ther; 15(3) Mar. 2016, 354-365.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Winter, et al., "Phthalimide Conjugation as a strategy for in vivo target protein degradation", Science, 2015 vol. 348 (6241), pp. 1376-1381 [Pub online: May 21, 2015].
Yao, Z. et al. BRAF Mutants Evade ERK-Dependent Feedback by Different Mechanisms that Determine Their Sensitivity to Pharmacologic Inhibition. Cancer Cell 28, 370-383 (2015).
Yao, Z. et al. Tumors with class 3 BRAF mutants are sensitive to the inhibition of activated RAS. Nature 548, 234- 238 (2017).
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, C., et al., RAF inhibitors that evade paradoxical MAPK, pathway activation2015 (583), Oct. 22, 2015, Nature, vol. 526, 583.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).
U.S. Appl. No. 15/853,166, filed Dec. 22, 2017, U.S. Pat. No. 10,723,717.
U.S. Appl. No. 16/563,842, filed Sep. 7, 2019, US 2020-0129627 A1.
Knott, Compounds containing sulphur chromophores. Part I. The action of bases on heterocyclic sulphide quartemary salts. Journal of the Chemical Society. 1955, pp. 916-927.
Knott, Compounds containing sulphur chromophores. Part V. Complex Cyanines. Journal of the Chemical Society. 1955, Part I, pp. 949-954.
Stanton et al., Chemically induced proximity in biology and medicine. Science. Mar. 9, 2018;359(6380):eaao5902, 9 pages.
Stanton et al., Chemically induced proximity in biology and medicine. Science. Mar. 9, 2018;359:1117.
U.S. Appl. No. 16/563,842, filed Sep. 7, 2019, U.S. Pat. No. 11,173,211, Issued.

FIG. 2A

Table 1A. Exemplary protein targeting moieties and compounds of the present disclosure.

| No. | Structure | Compound Name | MH+ | Synthetic Scheme |
|---|---|---|---|---|
| 307 | 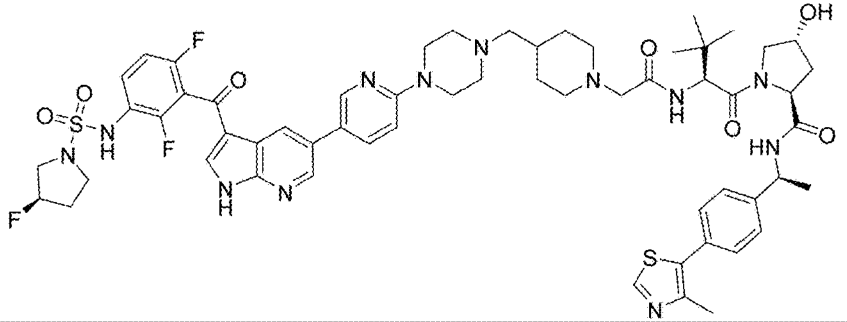 | (2S,4R)-1-((S)-2-(2-(4-((4-(5-(3-(2,6-difluoro-3-(((R)-3-fluoropyrrolidine)-1-sulfonamido)benzoyl)-1H-pyrrolo[2,3-b]pyridin-5-yl)pyridin-2-yl)piperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1167.8<br>1167.76 | 3 |
| 308 | 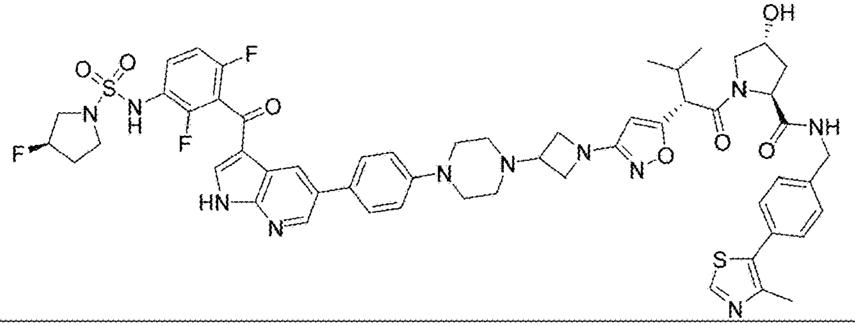 | (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N-(4-(4-methylthiazol-5-yl)benzyl)pyrrolidine-2-carboxamide | 1106.66<br>1106.77 | 13 |

FIG. 2A. Continued

| No. | Structure | Compound Name | MH+ | Synthetic Scheme |
|---|---|---|---|---|
| 309 | 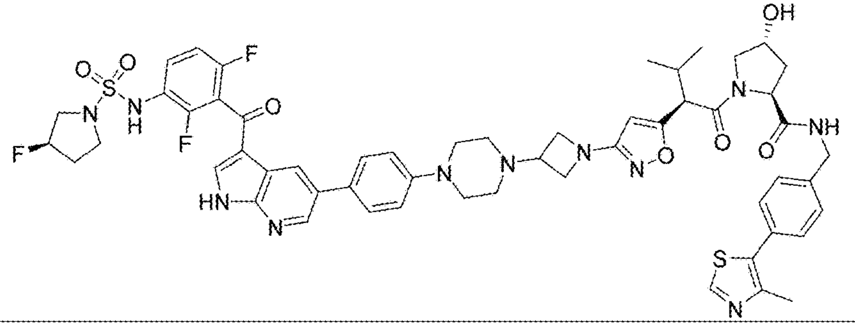 | (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N-(4-(4-methylthiazol-5-yl)benzyl)pyrrolidine-2-carboxamide | 1106.66<br>1106.78 | 13 |
| 310 | 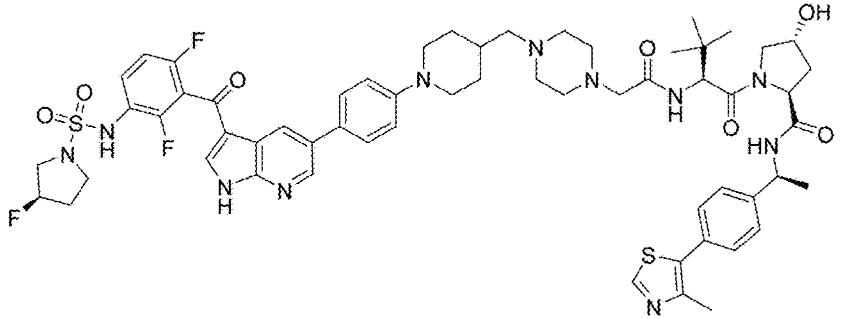 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.76<br>1166.8 | 3 |
| 311 | 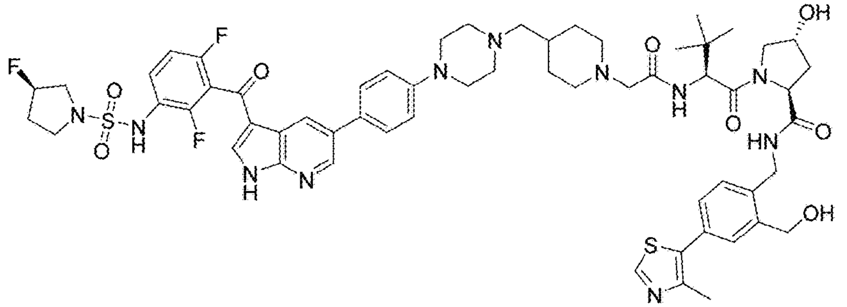 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(2-(hydroxymethyl)-4-(4-methylthiazol-5-yl)benzyl)pyrrolidine-2-carboxamide | 1182.76<br>1182.8 | 3 |

FIG. 2A. Continued

| No. | Structure | Compound Name | MH+ | Synthetic Scheme |
|---|---|---|---|---|
| 312 | 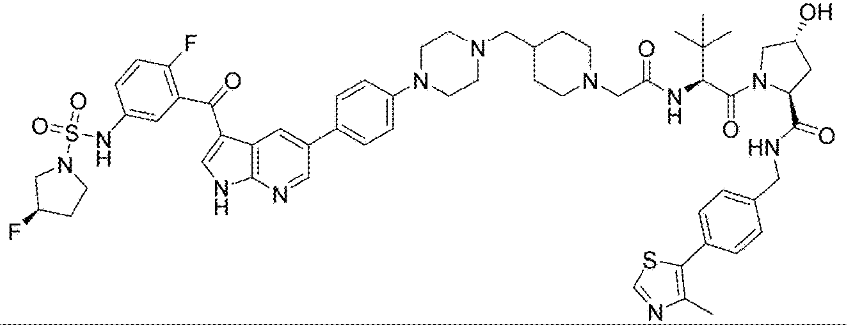 | (2S,4R)-1-((S)-2-(2-(4-((4-(4-(3-(2-fluoro-5-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1134.75 | Custom |
| 313 | 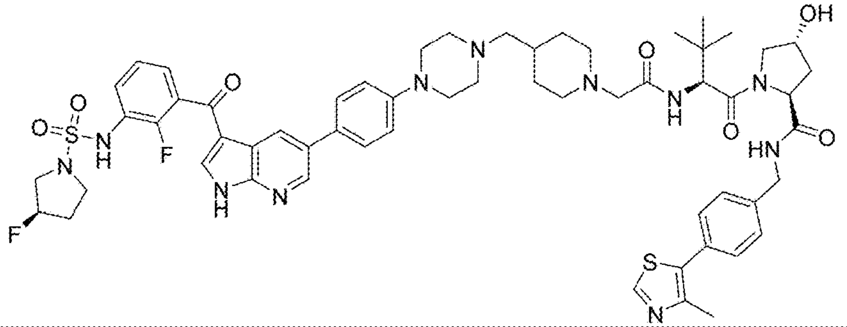 | (2S,4R)-1-((S)-2-(2-(4-((4-(4-(3-(2-fluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1134.75 | Custom |
| 314 | 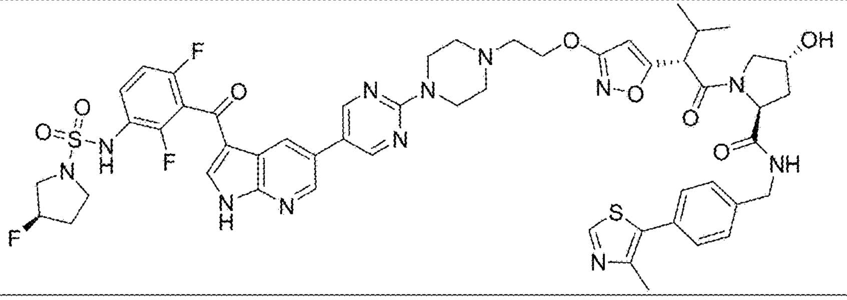 | (2S,4R)-1-((S)-2-(3-(2-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide | 1097.6 | 13 |

FIG. 2A. Continued

| No. | Structure | Compound Name | MH+ | Synthetic Scheme |
|---|---|---|---|---|
| 315 | 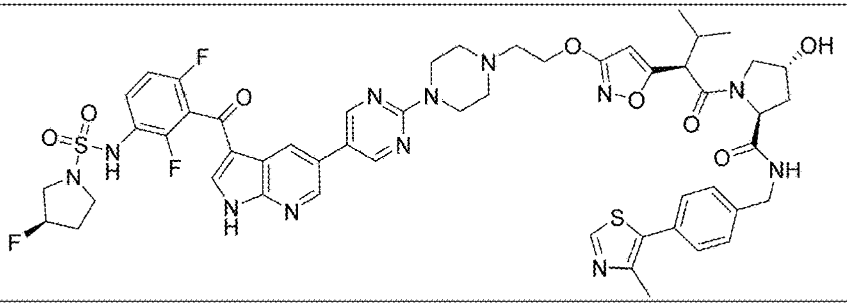 | (2S,4R)-1-((R)-2-(3-(2-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide | 1097.6 | 13 |
| 316 | 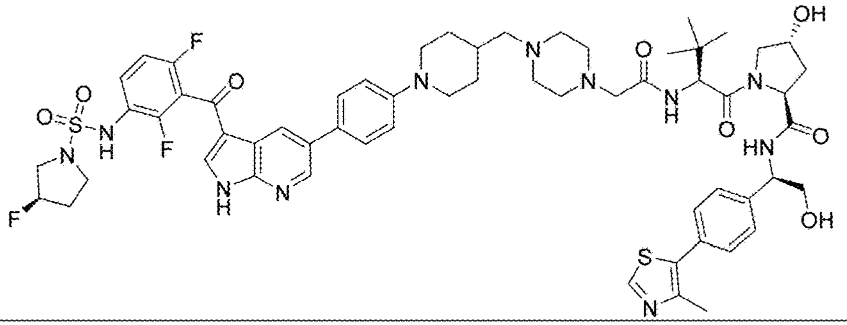 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1182.8<br>1182.76<br>1182.8<br>1182.75 | 3 |
| 317 | 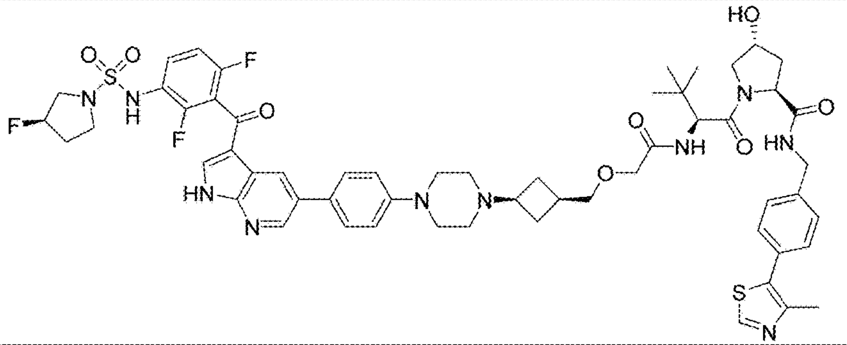 | (2S,4R)-1-((S)-2-(2-(((1s,3R)-3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)cyclobutyl)methoxy)acetamido)-3,3-dimethylbutanoyl)-4-hydroxy-N-(4-(4-methylthiazol-5-yl)benzyl)pyrrolidine-2-carboxamide | 1139.7 | 3 |

FIG. 2A. Continued

| No. | Structure | Compound Name | MH+ | Synthetic Scheme |
|---|---|---|---|---|
| 318 | 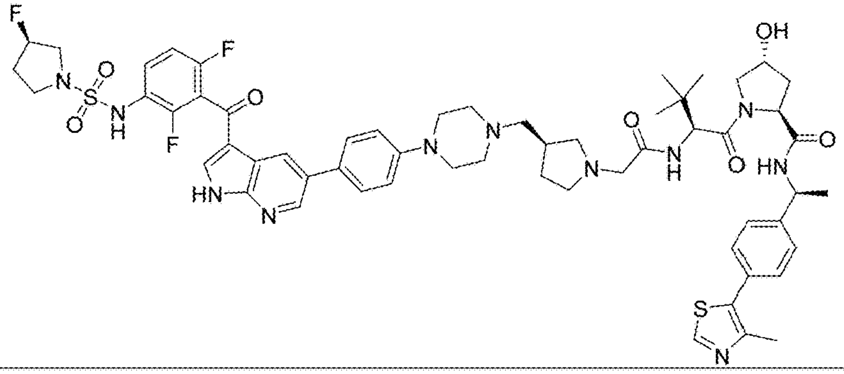 | (2S,4R)-1-((S)-2-(2-((S)-3-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)pyrrolidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.74<br>1152.74 | 3 |
| 319 | 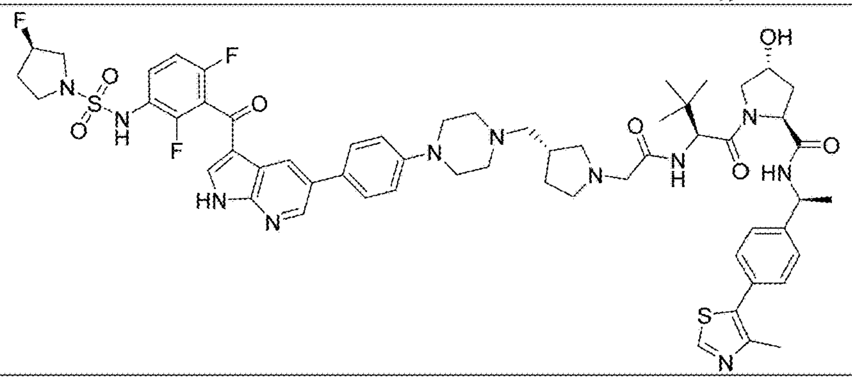 | (2S,4R)-1-((S)-2-(2-((R)-3-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)pyrrolidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.74<br>1152.74 | 3 |

FIG. 2A. Continued

| No. | Structure | Compound Name | MH+ | Synthetic Scheme |
|---|---|---|---|---|
| 320 | 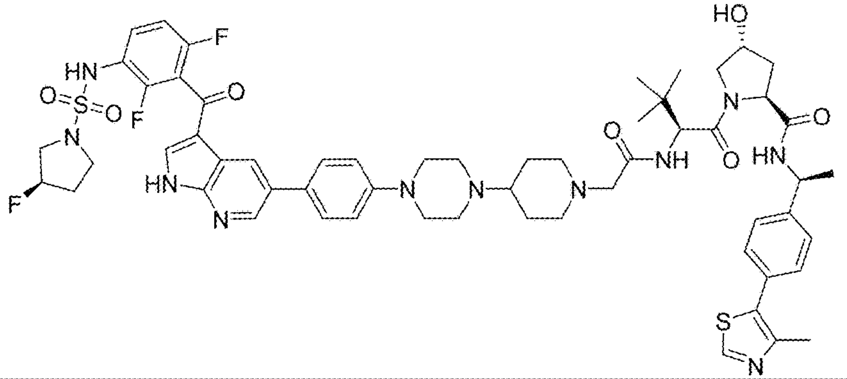 | (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.74<br>1152.74 | 3 |
| 321 | 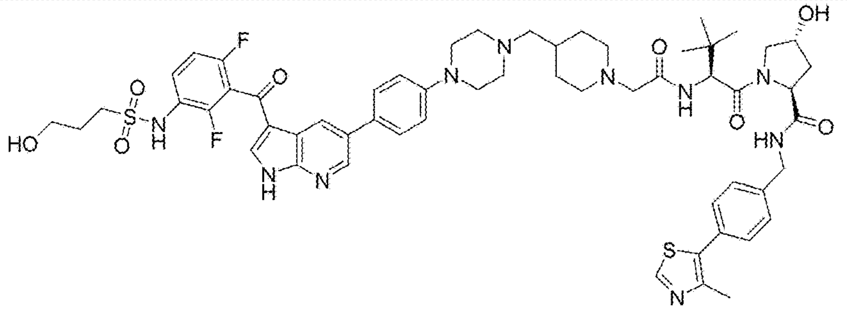 | (2S,4R)-1-((S)-2-(2-(4-((4-(4-(3-(2,6-difluoro-3-((3-hydroxypropyl)sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1123.73<br>1123.73 | Custom |
| 322 | 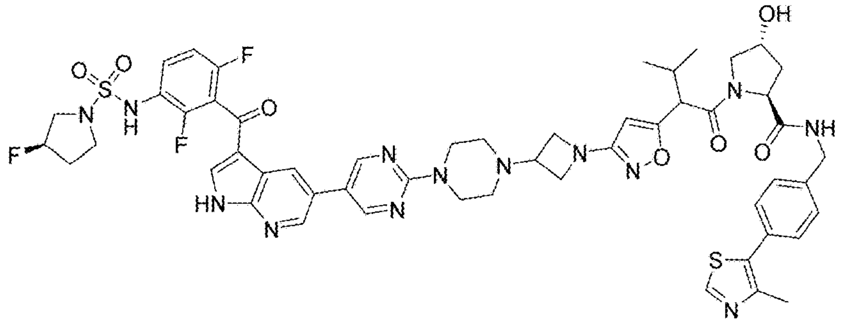 | (2S,4R)-1-(2-(3-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl)isoxazol-5-yl)-3-methylbutanoyl)-4-hydroxy-N-(4-(4-methylthiazol-5-yl)benzyl)pyrrolidine-2-carboxamide | 1108.65 | Custom |

FIG. 2A. Continued

| No. | Structure | Compound Name | MH+ | Synthetic Scheme |
|---|---|---|---|---|
| 323 | 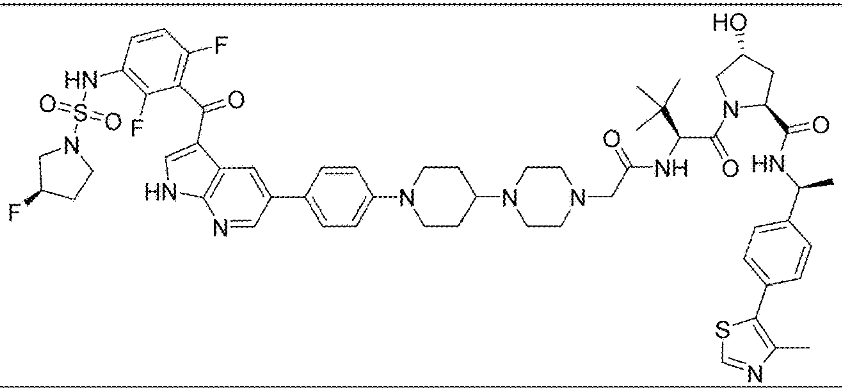 | (2S,4R)-1-((S)-2-(2-(4-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.74<br>1152.74 | 3 |
| 324 | 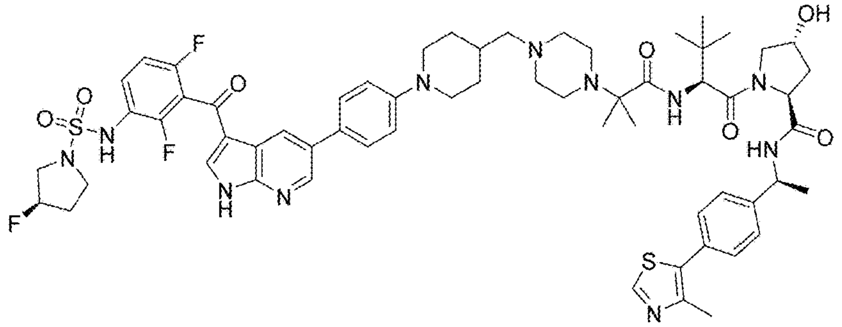 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-2-methylpropanamido)-3,3-dimethylbutanoyl)-4-hydroxy-N-((S)-1-(4-(4-methylthiazol-5-yl)phenyl)ethyl)pyrrolidine-2-carboxamide | 1194.8<br>1194.93 | 3 |

FIG. 2A. Continued

| No. | Structure | Compound Name | MH+ | Synthetic Scheme |
|---|---|---|---|---|
| 325 | 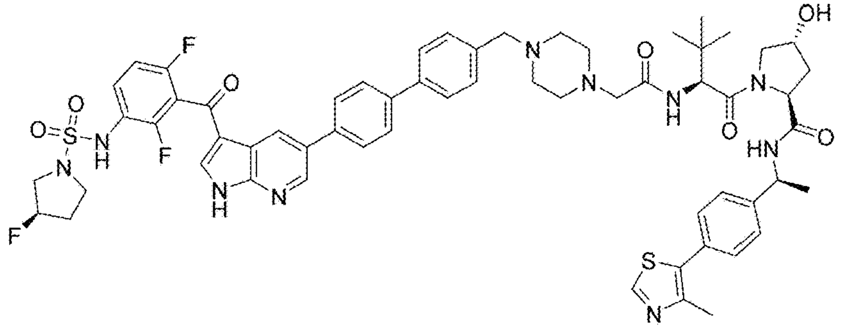 | (2S,4R)-1-((S)-2-(2-(4-((4'-(3-(2,6-difluoro-3-(((R)-3-fluoropyrrolidine)-1-sulfonamido)benzoyl)-1H-pyrrolo[2,3-b]pyridin-5-yl)-[1,1'-biphenyl]-4-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1159.71 | 3 |
| 326 | 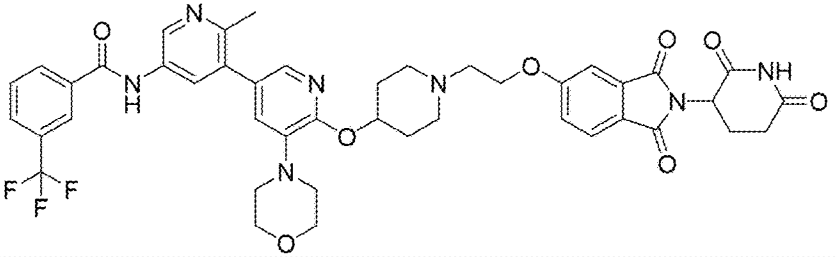 | N-(6'-((1-(2-((2-(2,6-dioxopiperidin-3-yl)-1,3-dioxoisoindolin-5-yl)oxy)ethyl)piperidin-4-yl)oxy)-2-methyl-5'-morpholino-[3,3'-bipyridin]-5-yl)-3-(trifluoromethyl)benzamide | 842.52 | 16 |
| 327 | 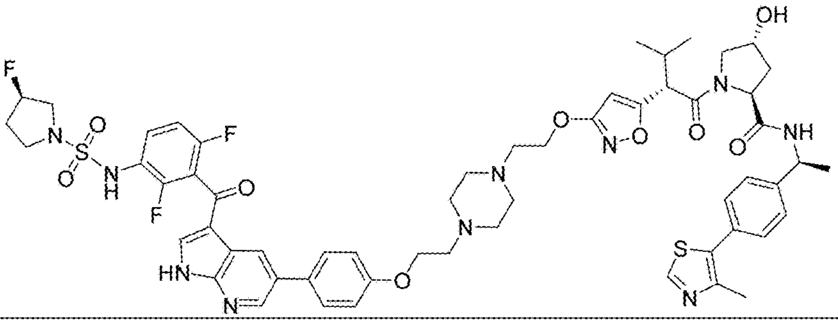 | (2S,4R)-1-((S)-2-(3-(2-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 1153.69<br>1153.7 | 13 |

FIG. 2A. Continued

| No. | Structure | Compound Name | MH+ | Synthetic Scheme |
|---|---|---|---|---|
| 328 | 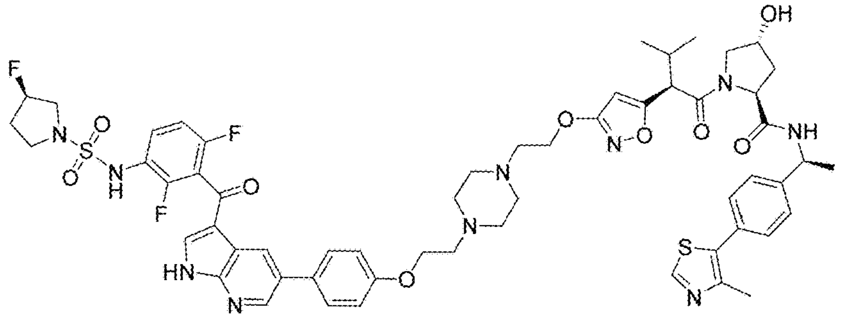 | (2S,4R)-1-((R)-2-(3-(2-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 1153.69<br>1153.7 | 13 |
| 329 | 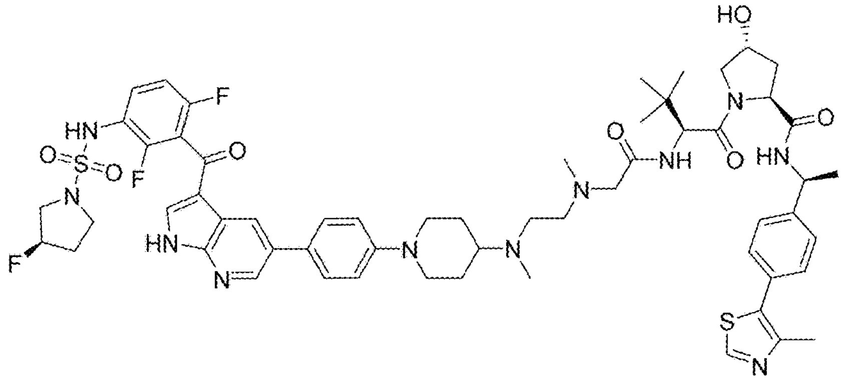 | (2S,4R)-1-((S)-2-(2-((2-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)(methyl)amino)ethyl)(methyl)amino)acetamido)-3,3-dimethylbutanoyl)-4-hydroxy-N-((S)-1-(4-(4-methylthiazol-5-yl)phenyl)ethyl)pyrrolidine-2-carboxamide | 1154.76<br>1154.75 | 3 |

FIG. 2A. Continued

| No. | Structure | Compound Name | MH+ | Synthetic Scheme |
|---|---|---|---|---|
| 330 | 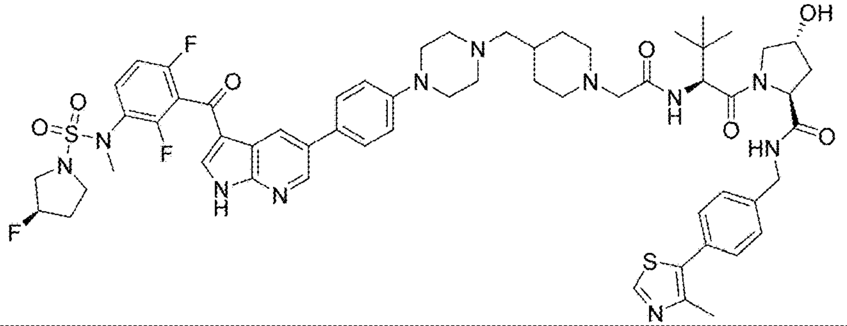 | (2S,4R)-1-((S)-2-(2-(4-((4-(4-(3-(2,6-difluoro-3-(((R)-3-fluoro-N-methylpyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1166.75 | Custom |
| 331 | 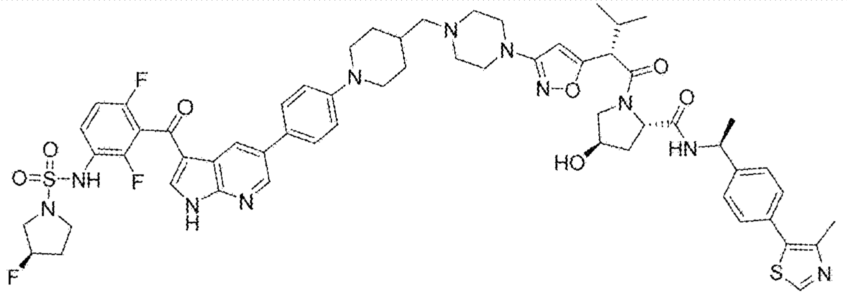 | (2S,4R)-1-((S)-2-(3-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1162.71 | 18 |
| 332 | 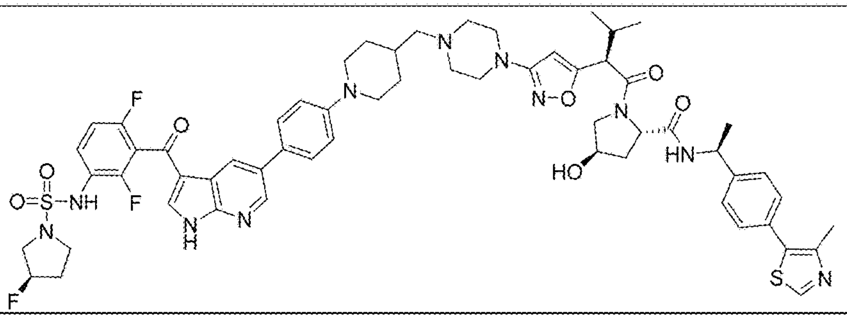 | (2S,4R)-1-((R)-2-(3-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1162.71 | 18 |

FIG. 2A. Continued

| No. | Structure | Compound Name | MH+ | Synthetic Scheme |
|---|---|---|---|---|
| 333 | 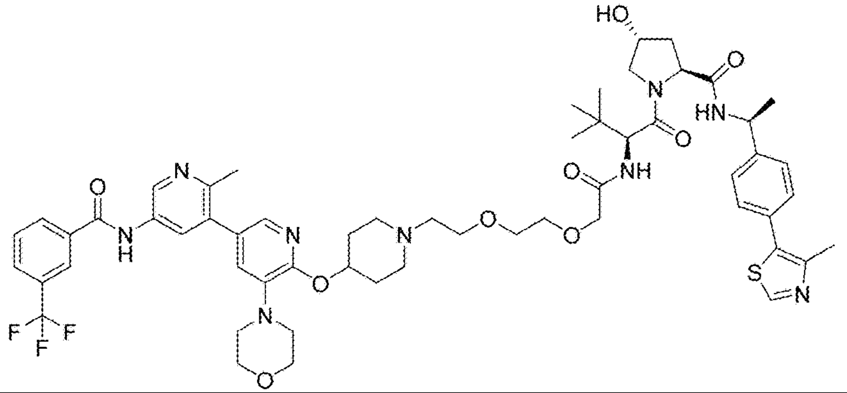 | (2S,4R)-1-((S)-3,3-dimethyl-2-(2-(2-(2-(4-((2'-methyl-5-morpholino-5'-(3-(trifluoromethyl)benzamido)-[3,3'-bipyridin]-6-yl)oxy)piperidin-1-yl)ethoxy)ethoxy)acetamido)butanoyl)-4-hydroxy-N-((S)-1-(4-(4-methylthiazol-5-yl)phenyl)ethyl)pyrrolidine-2-carboxamide | 1114.75 | 15 |
| 334 | 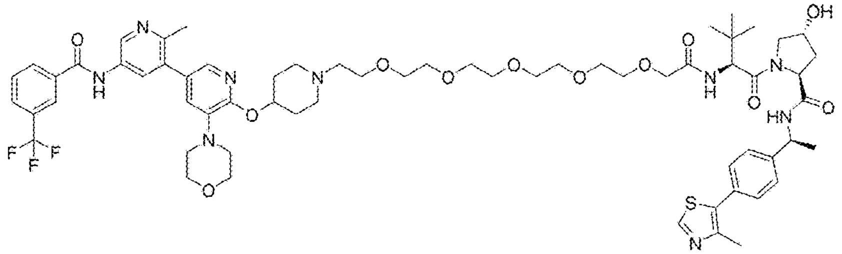 | (2S,4R)-1-((S)-2-(tert-butyl)-20-(4-((2'-methyl-5-morpholino-5'-(3-(trifluoromethyl)benzamido)-[3,3'-bipyridin]-6-yl)oxy)piperidin-1-yl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 1246.85 | 15 |
| 335 | 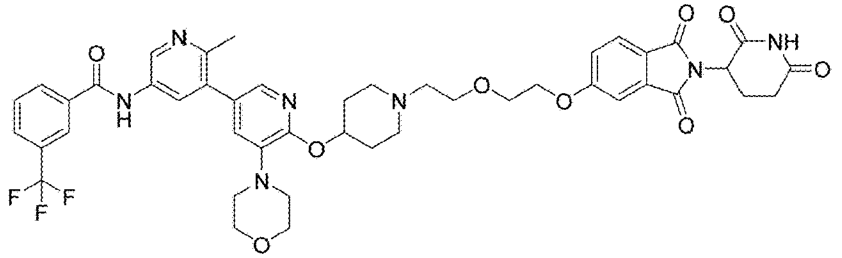 | N-(6'-((1-(2-(2-((2-(2,6-dioxopiperidin-3-yl)-1,3-dioxoisoindolin-5-yl)oxy)ethoxy)ethyl)piperidin-4-yl)oxy)-2-methyl-5'-morpholino-[3,3'-bipyridin]-5-yl)-3-(trifluoromethyl)benzamide | 886.55 | 16 |

FIG. 2A. Continued

| No. | Structure | Compound Name | MH+ | Synthetic Scheme |
|---|---|---|---|---|
| 336 | 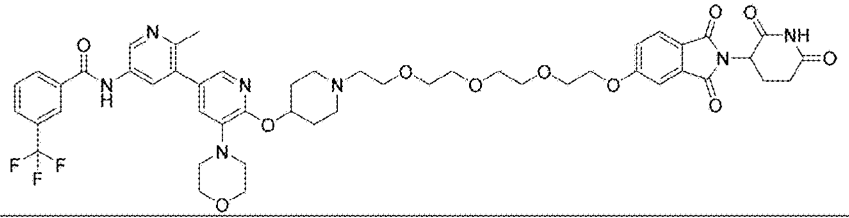 | N-(6'-((1-(2-(2-(2-(2-((2-(2,6-dioxopiperidin-3-yl)-1,3-dioxoisoindolin-5-yl)oxy)ethoxy)ethoxy)ethoxy)ethyl)piperidin-4-yl)oxy)-2-methyl-5'-morpholino-[3,3'-bipyridin]-5-yl)-3-(trifluoromethyl)benzamide | 974.61 | 16 |
| 337 | 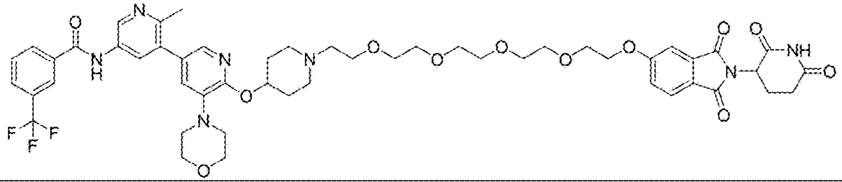 | N-(6'-((1-(14-((2-(2,6-dioxopiperidin-3-yl)-1,3-dioxoisoindolin-5-yl)oxy)-3,6,9,12-tetraoxatetradecyl)piperidin-4-yl)oxy)-2-methyl-5'-morpholino-[3,3'-bipyridin]-5-yl)-3-(trifluoromethyl)benzamide | 1018.65 | 16 |
| 338 | 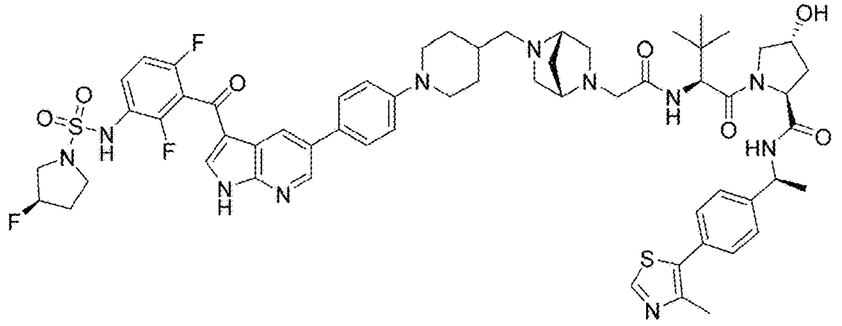 | (2S,4R)-1-((S)-2-(2-((1S,4S)-5-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,5-diazabicyclo[2.2.1]heptan-2-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.75<br>1178.75 | 3 |

FIG. 2A. Continued

| No. | Structure | Compound Name | MH+ | Synthetic Scheme |
|---|---|---|---|---|
| 339 | 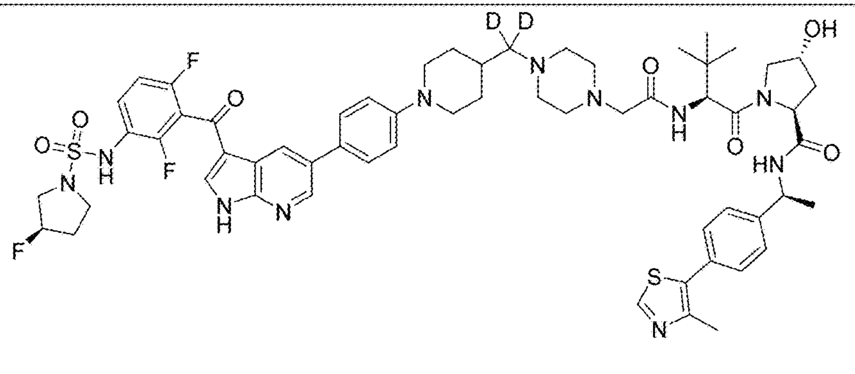 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl-d2)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1168.76<br>1168.76 | 3 |
| 340 | 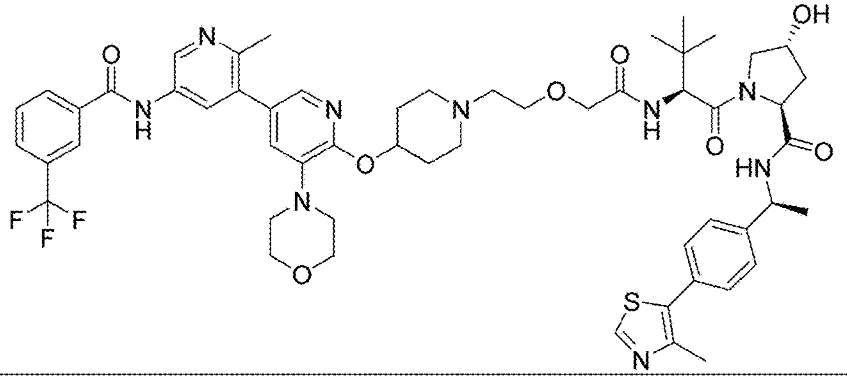 | (2S,4R)-1-((S)-3,3-dimethyl-2-(2-(2-(4-((2'-methyl-5-morpholino-5'-(3-(trifluoromethyl)benzamido)-[3,3'-bipyridin]-6-yl)oxy)piperidin-1-yl)ethoxy)acetamido)butanoyl)-4-hydroxy-N-((S)-1-(4-(4-methylthiazol-5-yl)phenyl)ethyl)pyrrolidine-2-carboxamide | 1070.72 | 15 |

FIG. 2A. Continued

| No. | Structure | Compound Name | MH+ | Synthetic Scheme |
|---|---|---|---|---|
| 341 | 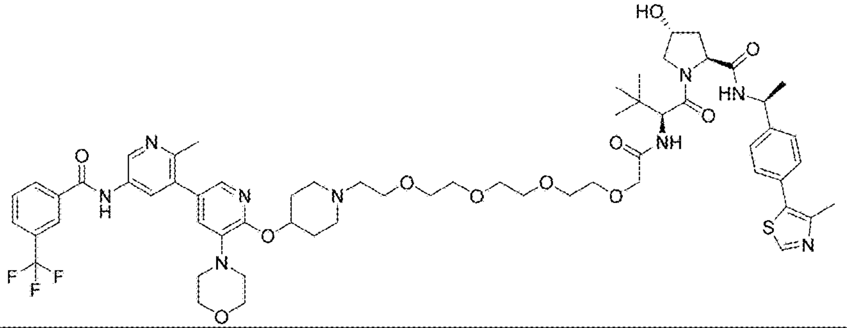 | (2S,4R)-1-((S)-2-(tert-butyl)-17-(4-((2'-methyl-5-morpholino-5'-(3-(trifluoromethyl)benzamido)-[3,3'-bipyridin]-6-yl)oxy)piperidin-1-yl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | 1202.82 | 15 |
| 342 | 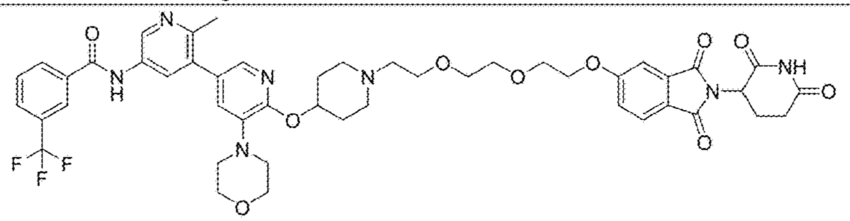 | N-(6'-((1-(2-(2-(2-((2-(2,6-dioxopiperidin-3-yl)-1,3-dioxoisoindolin-5-yl)oxy)ethoxy)ethoxy)ethyl)piperidin-4-yl)oxy)-2-methyl-5'-morpholino-[3,3'-bipyridin]-5-yl)-3-(trifluoromethyl)benzamide | 930.58 | 16 |
| 343 | 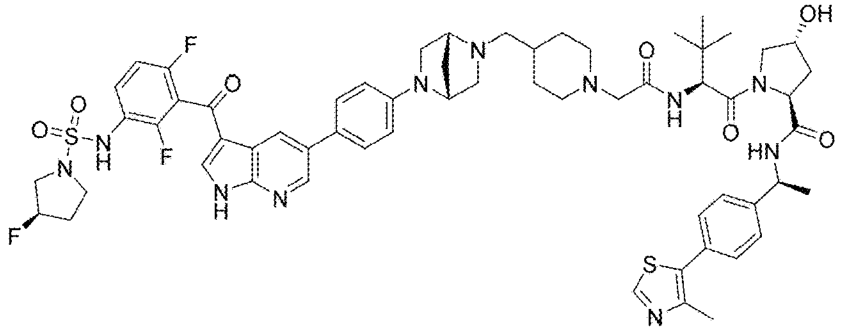 | (2S,4R)-1-((S)-2-(2-(4-(((1R,4R)-5-(4-(3-(2,6-difluoro-3-(((R)-3-fluoropyrrolidine)-1-sulfonamido)benzoyl)-1H-pyrrolo[2,3-b]pyridin-5-yl)phenyl)-2,5-diazabicyclo[2.2.1]heptan-2-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.76 | 3 |

FIG. 2A. Continued

| No. | Structure | Compound Name | MH+ | Synthetic Scheme |
|---|---|---|---|---|
| 344 | 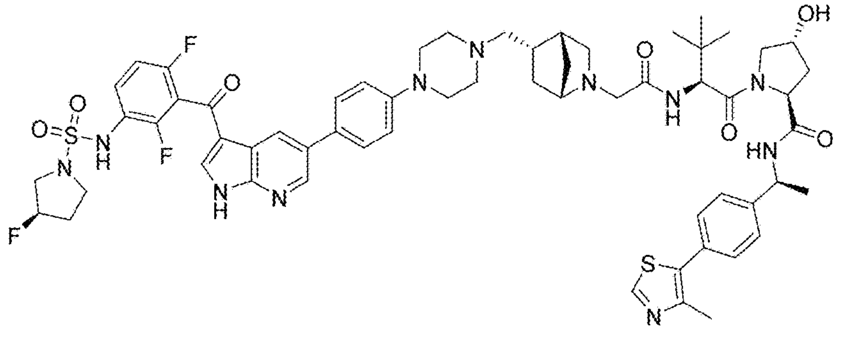 | (2S,4R)-1-((S)-2-(2-((1S,4R,5S)-5-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)-2-azabicyclo[2.2.1]heptan-2-yl)acetamido)-3,3-dimethylbutanoyl)-4-hydroxy-N-((S)-1-(4-(4-methylthiazol-5-yl)phenyl)ethyl)pyrrolidine-2-carboxamide | | 3 |
| 345 | 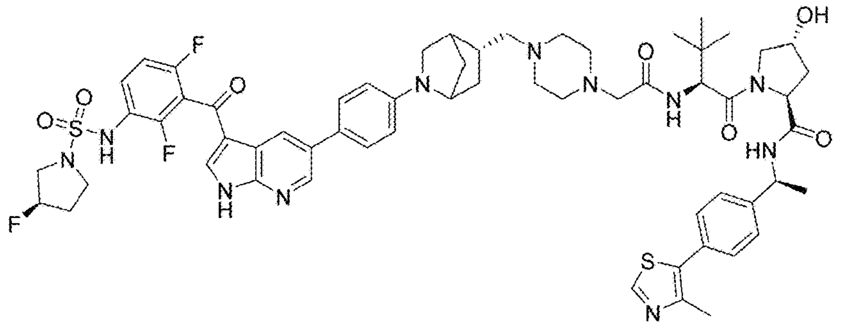 | (2S,4R)-1-((2S)-2-(2-(4-(((5R)-2-(4-(3-(2,6-difluoro-3-(((R)-3-fluoropyrrolidine)-1-sulfonamido)benzoyl)-1H-pyrrolo[2,3-b]pyridin-5-yl)phenyl)-2-azabicyclo[2.2.1]heptan-5-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.76 | 3 |

FIG. 2A. Continued

| No. | Structure | Compound Name | MH+ | Synthetic Scheme |
|---|---|---|---|---|
| 346 | 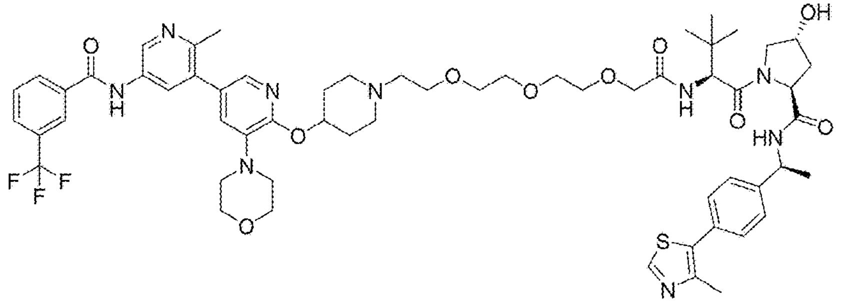 | (2S,4R)-1-((S)-2-(tert-butyl)-14-(4-((2'-methyl-5-morpholino-5'-(3-(trifluoromethyl)benzamido)-[3,3'-bipyridin]-6-yl)oxy)piperidin-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 1158.78 | 15 |
| 347 | 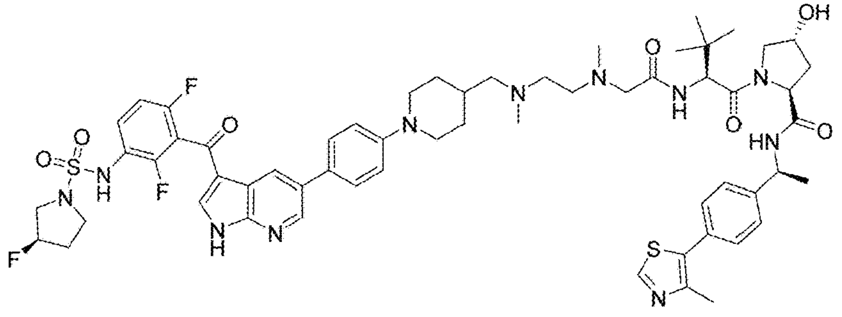 | (2S,4R)-1-((S)-2-(2-((2-(((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)(methyl)amino)ethyl)(methyl)amino)acetamido)-3,3-dimethylbutanoyl)-4-hydroxy-N-((S)-1-(4-(4-methylthiazol-5-yl)phenyl)ethyl)pyrrolidine-2-carboxamide | 1168.77<br>1168.76 | 3 |

FIG. 2A. Continued

| No. | Structure | Compound Name | MH+ | Synthetic Scheme |
|---|---|---|---|---|
| 348 | 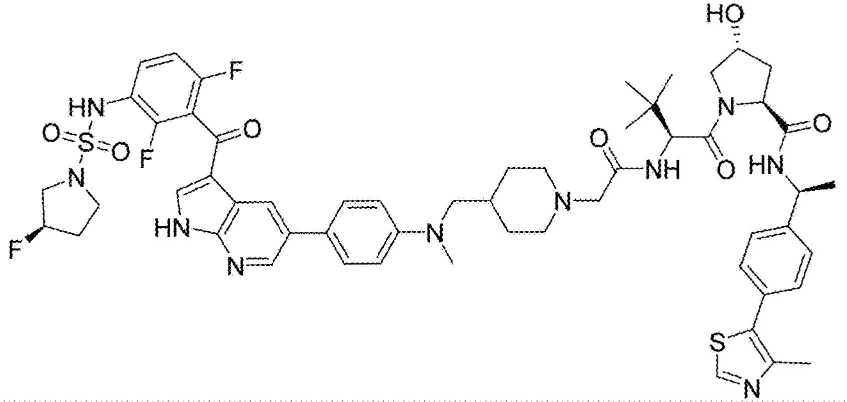 | (2S,4R)-1-((S)-2-(2-(4-(((4-(3-(2,6-difluoro-3-(((R)-3-fluoropyrrolidine)-1-sulfonamido)benzoyl)-1H-pyrrolo[2,3-b]pyridin-5-yl)phenyl)(methyl)amino)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1111.7<br>1111.7 | 3 |
| 349 | 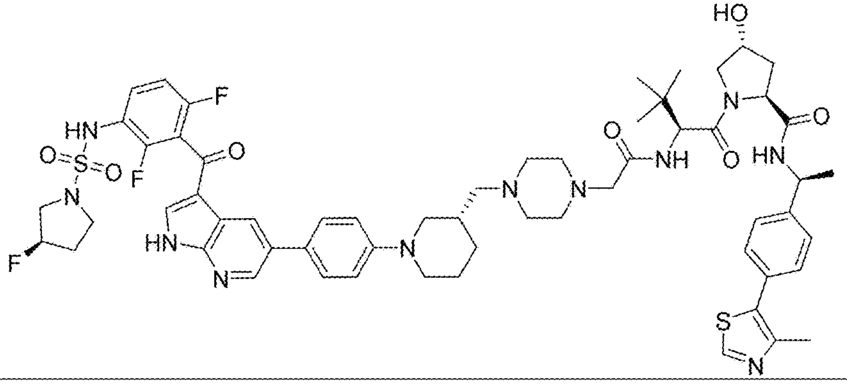 | (2S,4R)-1-((S)-2-(2-(4-(((S)-1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-3-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.8<br>1166.8 | 3 |

FIG. 2A. Continued

| No. | Structure | Compound Name | MH+ | Synthetic Scheme |
|---|---|---|---|---|
| 350 | 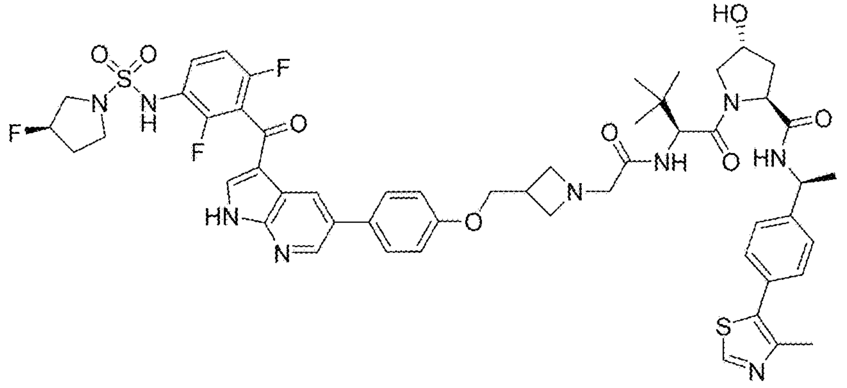 | (2S,4R)-1-((S)-2-(2-(3-((4-(3-(2,6-difluoro-3-(((R)-3-fluoropyrrolidine)-1-sulfonamido)benzoyl)-1H-pyrrolo[2,3-b]pyridin-5-yl)phenoxy)methyl)azetidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1070.6<br>1070.6 | 3 |
| 351 | 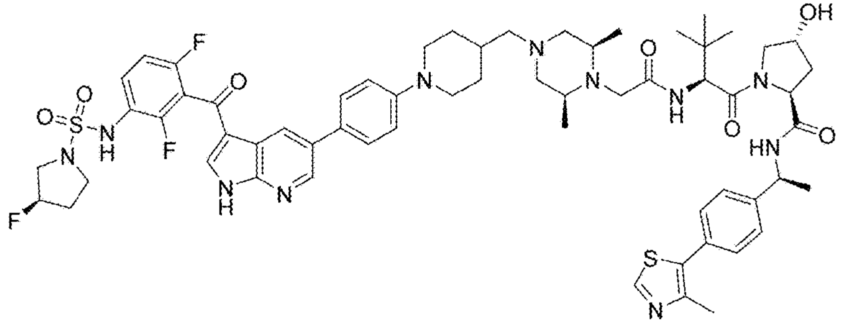 | (2S,4R)-1-((S)-2-(2-((2S,6R)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-dimethylpiperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.8 | Custom 1 |

FIG. 2A. Continued

| No. | Structure | Compound Name | MH+ | Synthetic Scheme |
|---|---|---|---|---|
| 352 | 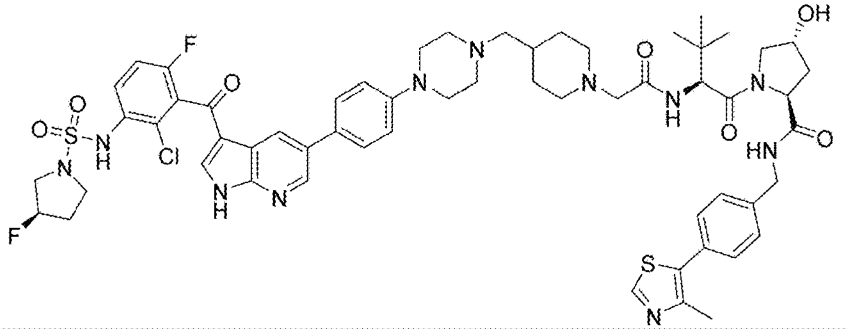 | (2S,4R)-1-((S)-2-(2-(4-((4-(4-(3-(2-chloro-6-fluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1168.7 | Custom |
| 353 | 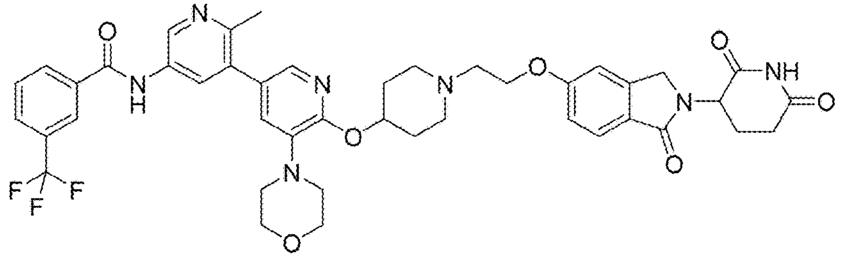 | N-(6'-((1-(2-((2-(2,6-dioxopiperidin-3-yl)-1-oxoisoindolin-5-yl)oxy)ethyl)piperidin-4-yl)oxy)-2-methyl-5'-morpholino-[3,3'-bipyridin]-5-yl)-3-(trifluoromethyl)benzamide | 828.54 | 16 |
| 354 | 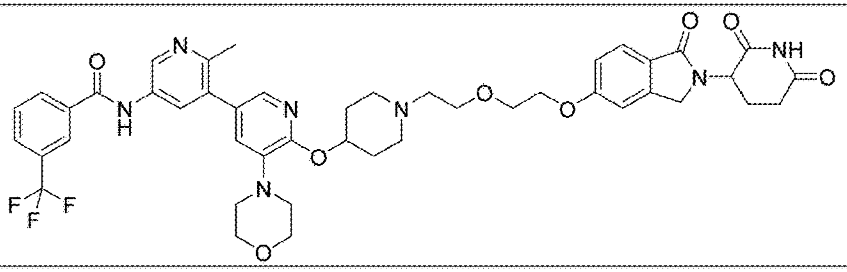 | N-(6'-((1-(2-(2-((2-(2,6-dioxopiperidin-3-yl)-1-oxoisoindolin-5-yl)oxy)ethoxy)ethyl)piperidin-4-yl)oxy)-2-methyl-5'-morpholino-[3,3'-bipyridin]-5-yl)-3-(trifluoromethyl)benzamide | 872.57 | 16 |

FIG. 2A. Continued

| No. | Structure | Compound Name | MH+ | Synthetic Scheme |
|---|---|---|---|---|
| 355 | 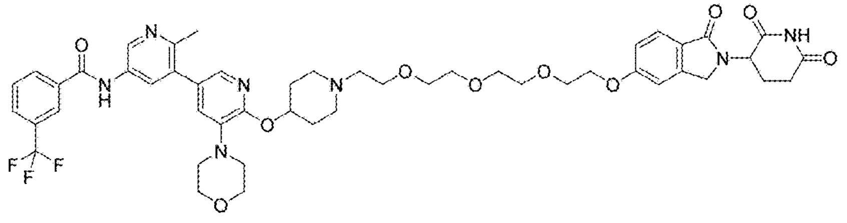 | N-(6'-((1-(2-(2-(2-(2-((2-(2,6-dioxopiperidin-3-yl)-1-oxoisoindolin-5-yl)oxy)ethoxy)ethoxy)ethoxy)ethyl)piperidin-4-yl)oxy)-2-methyl-5'-morpholino-[3,3'-bipyridin]-5-yl)-3-(trifluoromethyl)benzamide | 960.64 | 16 |
| 356 | 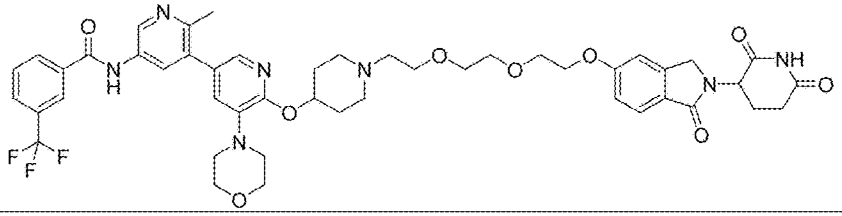 | N-(6'-((1-(2-(2-(2-((2-(2,6-dioxopiperidin-3-yl)-1-oxoisoindolin-5-yl)oxy)ethoxy)ethoxy)ethyl)piperidin-4-yl)oxy)-2-methyl-5'-morpholino-[3,3'-bipyridin]-5-yl)-3-(trifluoromethyl)benzamide | 916.55 | 16 |
| 357 | 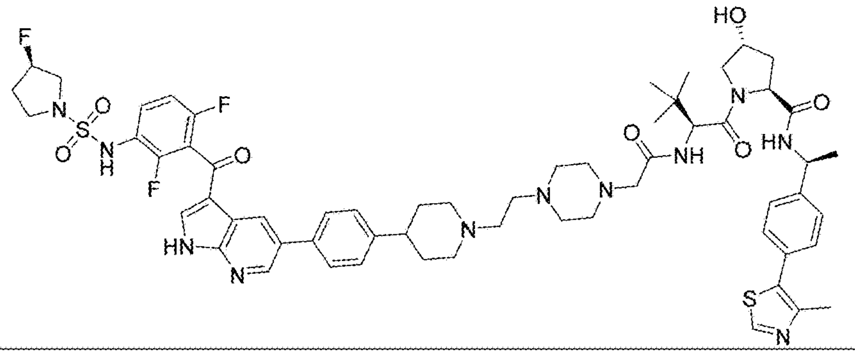 | (2S,4R)-1-((S)-2-(2-(4-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)ethyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.78 | 3 |

FIG. 2A. Continued

| No. | Structure | Compound Name | MH+ | Synthetic Scheme |
|---|---|---|---|---|
| 358 | 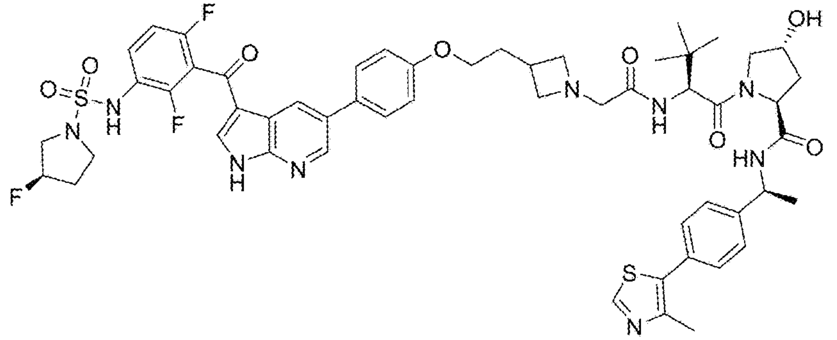 | (2S,4R)-1-((S)-2-(2-(3-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethyl)azetidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1084.65 | 3 |
| 359 | 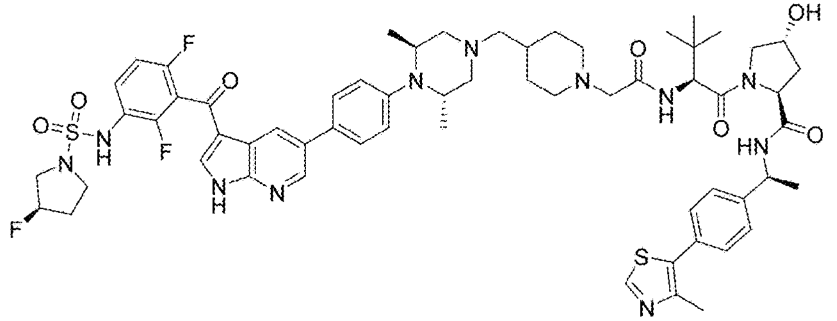 | (2S,4R)-1-((S)-2-(2-(4-(((3S,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.8 | 3 |
| 360 | 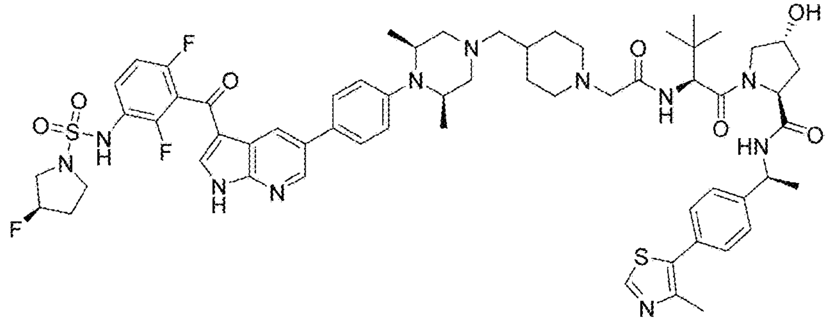 | (2S,4R)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.8 | 3 |

FIG. 2A. Continued

| No. | Structure | Compound Name | MH+ | Synthetic Scheme |
|---|---|---|---|---|
| 361 | 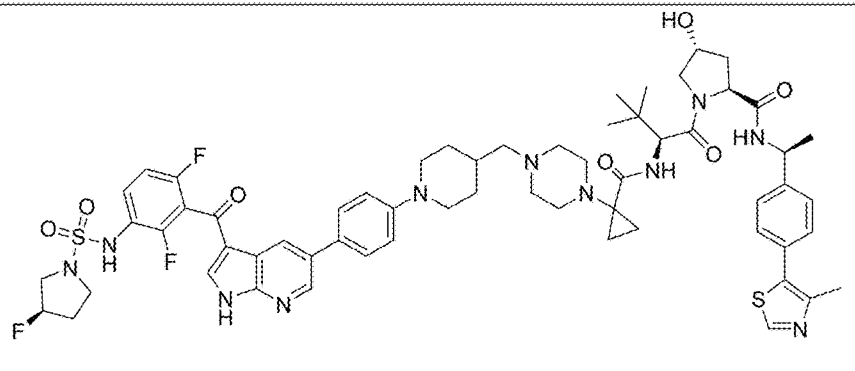 | (2S,4R)-1-((S)-2-(1-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)cyclopropane-1-carboxamido)-3,3-dimethylbutanoyl)-4-hydroxy-N-((S)-1-(4-(4-methylthiazol-5-yl)phenyl)ethyl)pyrrolidine-2-carboxamide | 1192.77 1192.77 | Custom 1 |
| 362 | 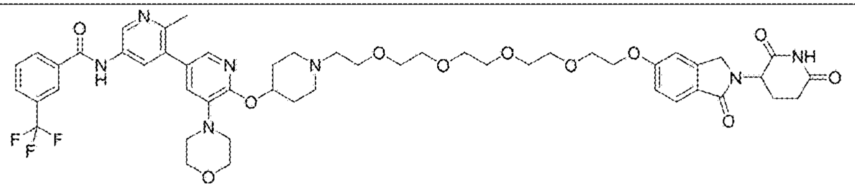 | N-(6'-((1-(14-((2-(2,6-dioxopiperidin-3-yl)-1-oxoisoindolin-5-yl)oxy)-3,6,9,12-tetraoxatetradecyl)piperidin-4-yl)oxy)-2-methyl-5'-morpholino-[3,3'-bipyridin]-5-yl)-3-(trifluoromethyl)benzamide | 1004.67 | 16 |
| 363 | 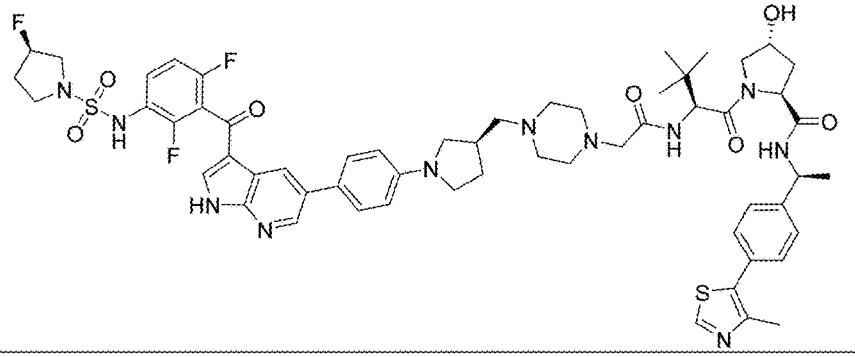 | (2S,4R)-1-((S)-2-(2-(4-(((R)-1-(4-(3-(2,6-difluoro-3-(((R)-3-fluoropyrrolidine)-1-sulfonamido)benzoyl)-1H-pyrrolo[2,3-b]pyridin-5-yl)phenyl)pyrrolidin-3-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.73 | 3 |

FIG. 2A. Continued

| No. | Structure | Compound Name | MH+ | Synthetic Scheme |
|---|---|---|---|---|
| 364 | 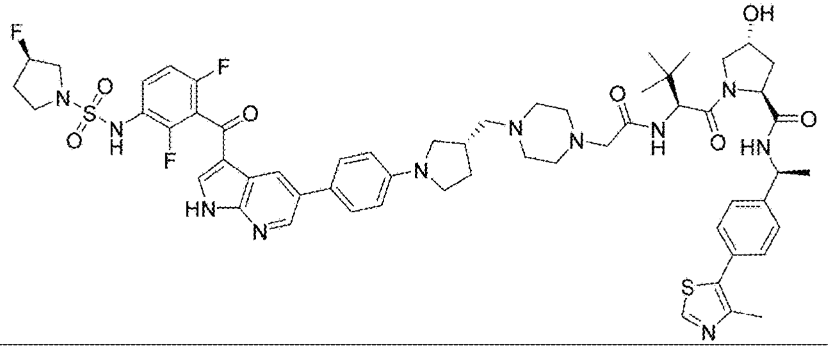 | (2S,4R)-1-((S)-2-(2-(4-(((S)-1-(4-(3-(2,6-difluoro-3-(((R)-3-fluoropyrrolidine)-1-sulfonamido)benzoyl)-1H-pyrrolo[2,3-b]pyridin-5-yl)phenyl)pyrrolidin-3-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.73 | 3 |
| 365 | 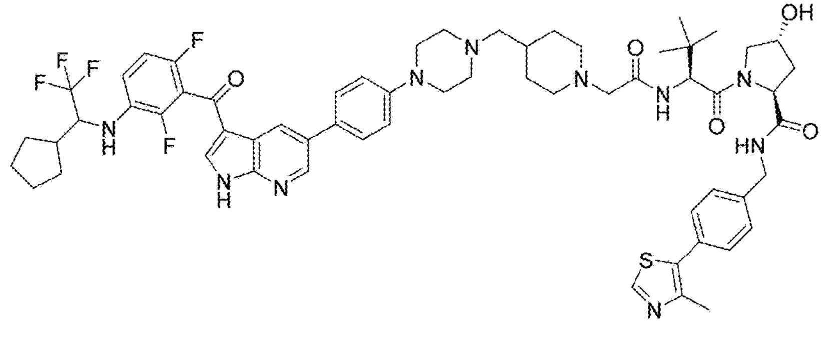 | (2S,4R)-1-((2S)-2-(2-(4-((4-(4-(3-(3-((1-cyclopentyl-2,2,2-trifluoroethyl)amino)-2,6-difluorobenzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1151.79 | Custom |
| 366 | 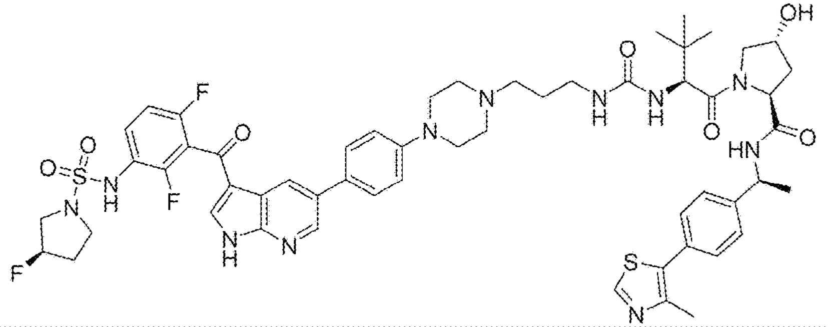 | (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propyl)ureido)-3,3-dimethylbutanoyl)-4-hydroxy-N-((S)-1-(4-(4-methylthiazol-5-yl)phenyl)ethyl)pyrrolidine-2-carboxamide | 1112.69 | Custom |

FIG. 2A. Continued

| No. | Structure | Compound Name | MH+ | Synthetic Scheme |
|---|---|---|---|---|
| 367 | 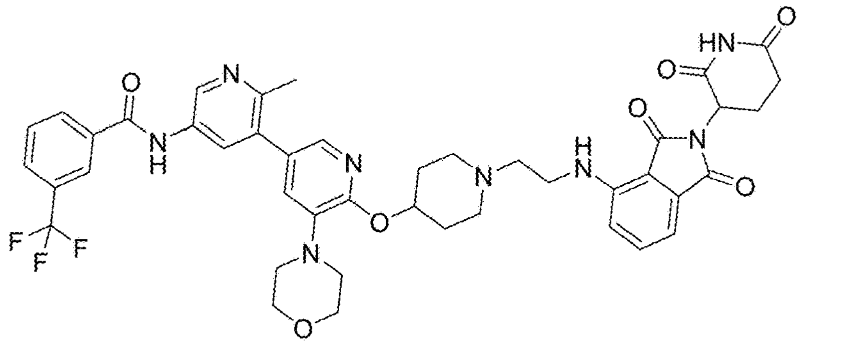 | N-(6'-((1-(2-((2-(2,6-dioxopiperidin-3-yl)-1,3-dioxoisoindolin-4-yl)amino)ethyl)piperidin-4-yl)oxy)-2-methyl-5'-morpholino-[3,3'-bipyridin]-5-yl)-3-(trifluoromethyl)benzamide | 841.53 | 16 |
| 368 | 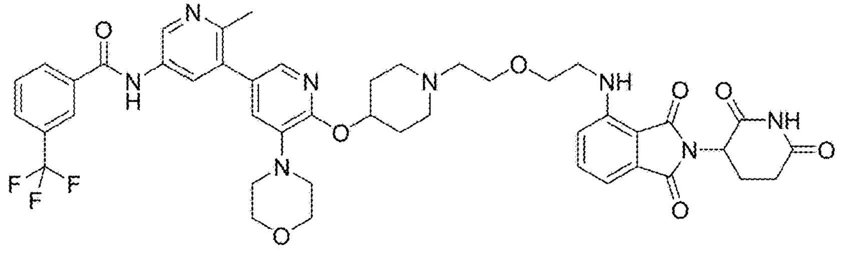 | N-(6'-((1-(2-(2-((2-(2,6-dioxopiperidin-3-yl)-1,3-dioxoisoindolin-4-yl)amino)ethoxy)ethyl)piperidin-4-yl)oxy)-2-methyl-5'-morpholino-[3,3'-bipyridin]-5-yl)-3-(trifluoromethyl)benzamide | 885.56 | 16 |
| 369 | 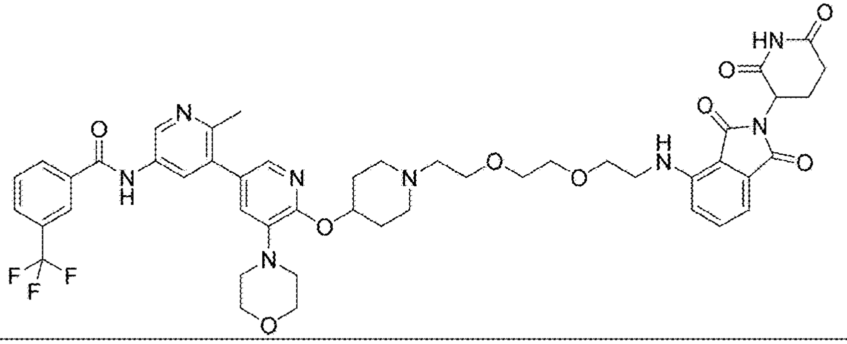 | N-(6'-((1-(2-(2-(2-((2-(2,6-dioxopiperidin-3-yl)-1,3-dioxoisoindolin-4-yl)amino)ethoxy)ethoxy)ethyl)piperidin-4-yl)oxy)-2-methyl-5'-morpholino-[3,3'-bipyridin]-5-yl)-3-(trifluoromethyl)benzamide | 929.6 | 16 |

FIG. 2A. Continued

| No. | Structure | Compound Name | MH+ | Synthetic Scheme |
| --- | --- | --- | --- | --- |
| 370 | 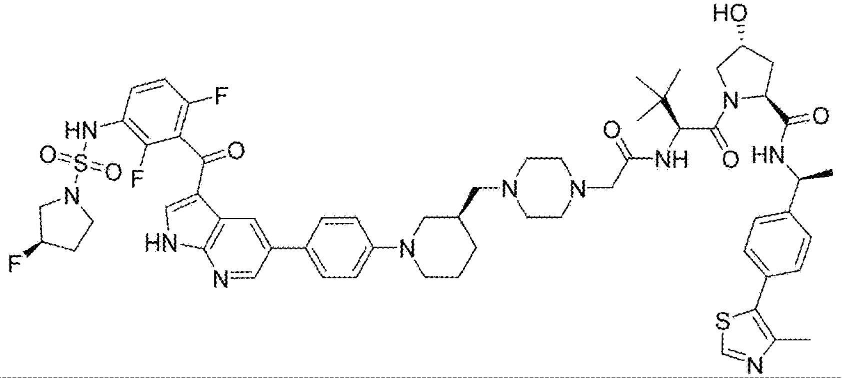 | (2S,4R)-1-((S)-2-(2-(4-(((R)-1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-3-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.75 | 3 |
| 371 | 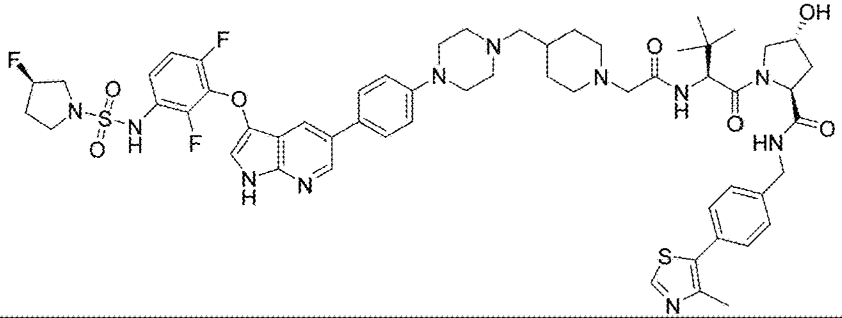 | (2S,4R)-1-((S)-2-(2-(4-((4-(4-(3-(2,6-difluoro-3-(((R)-3-fluoropyrrolidine)-1-sulfonamido)phenoxy)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1140.73 | Custom |
| 372 | 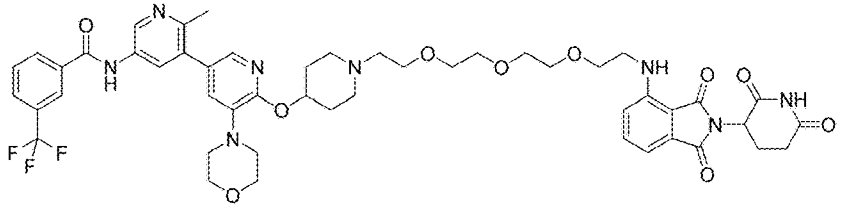 | N-(6'-((1-(2-(2-(2-(2-((2-(2,6-dioxopiperidin-3-yl)-1,3-dioxoisoindolin-4-yl)amino)ethoxy)ethoxy)ethoxy)ethyl)piperidin-4-yl)oxy)-2-methyl-5'-morpholino-[3,3'-bipyridin]-5-yl)-3-(trifluoromethyl)benzamide | 973.63 | 16 |

FIG. 2A. Continued

| No. | Structure | Compound Name | MH+ | Synthetic Scheme |
| --- | --- | --- | --- | --- |
| 373 | 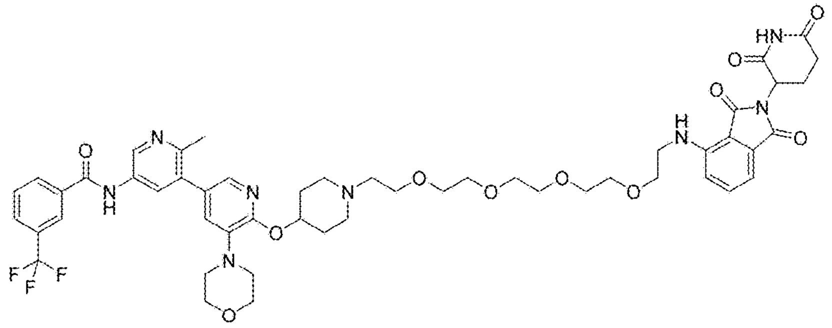 | N-(6'-((1-(14-((2-(2,6-dioxopiperidin-3-yl)-1,3-dioxoisoindolin-4-yl)amino)-3,6,9,12-tetraoxatetradecyl)piperidin-4-yl)oxy)-2-methyl-5'-morpholino-[3,3'-bipyridin]-5-yl)-3-(trifluoromethyl)benzamide | 1017.67 | 16 |
| 374 | 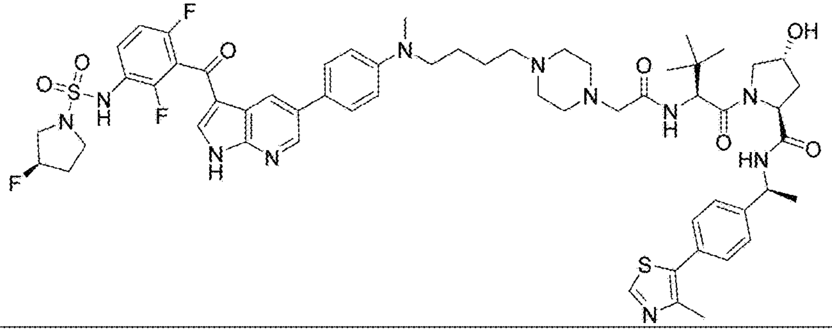 | (2S,4R)-1-((S)-2-(2-(4-(4-((4-(3-(2,6-difluoro-3-(((R)-3-fluoropyrrolidine)-1-sulfonamido)benzoyl)-1H-pyrrolo[2,3-b]pyridin-5-yl)phenyl)(methyl)amino)butyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1154.73 | 3 |
| 375 | 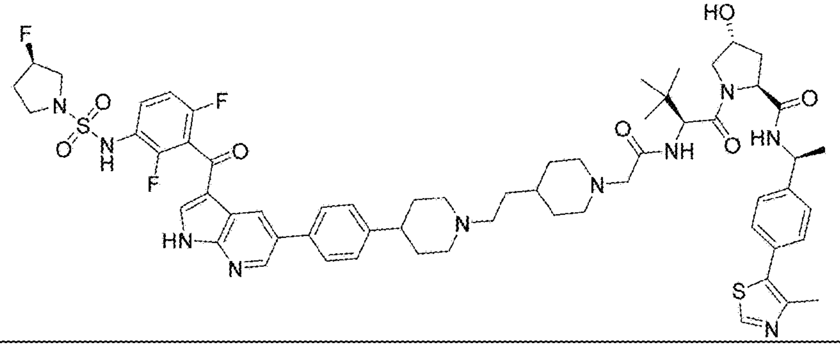 | (2S,4R)-1-((S)-2-(2-(4-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)ethyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1179.76 | 3 |

FIG. 2A. Continued

| No. | Structure | Compound Name | MH+ | Synthetic Scheme |
|---|---|---|---|---|
| 376 | 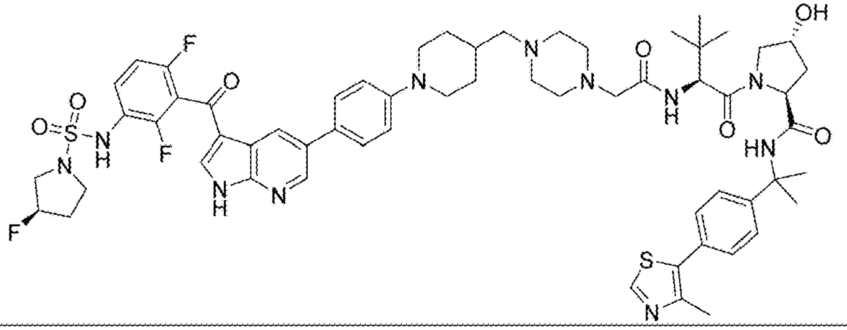 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(2-(4-(4-methylthiazol-5-yl)phenyl)propan-2-yl)pyrrolidine-2-carboxamide | 1180.75 | 17 |
| 377 | 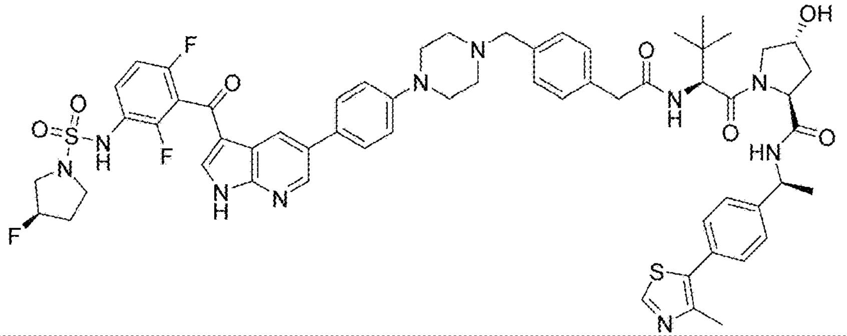 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)phenyl)acetamido)-3,3-dimethylbutanoyl)-4-hydroxy-N-((S)-1-(4-(4-methylthiazol-5-yl)phenyl)ethyl)pyrrolidine-2-carboxamide | 1159.69 | Custom 1 |
| 378 | 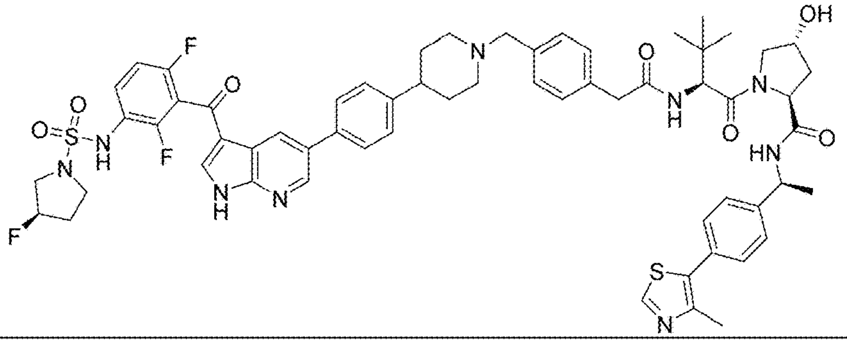 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)methyl)phenyl)acetamido)-3,3-dimethylbutanoyl)-4-hydroxy-N-((S)-1-(4-(4-methylthiazol-5-yl)phenyl)ethyl)pyrrolidine-2-carboxamide | 1158.69 | 3 |

FIG. 2A. Continued

| No. | Structure | Compound Name | MH+ | Synthetic Scheme |
|---|---|---|---|---|
| 379 | 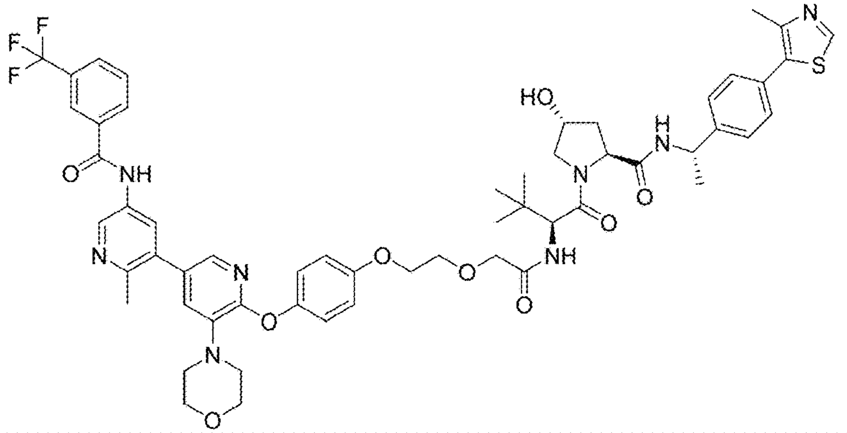 | (2S,4R)-1-((S)-3,3-dimethyl-2-(2-(2-(4-((2'-methyl-5-morpholino-5'-(3-(trifluoromethyl)benzamido)-[3,3'-bipyridin]-6-yl)oxy)phenoxy)ethoxy)acetamido)butanoyl)-4-hydroxy-N-((S)-1-(4-(4-methylthiazol-5-yl)phenyl)ethyl)pyrrolidine-2-carboxamide | 1079.66 | 15 |
| 380 | 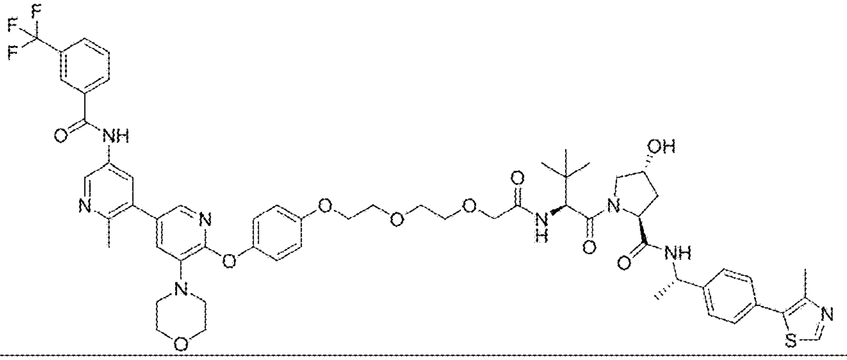 | (2S,4R)-1-((S)-3,3-dimethyl-2-(2-(2-(2-(4-((2'-methyl-5-morpholino-5'-(3-(trifluoromethyl)benzamido)-[3,3'-bipyridin]-6-yl)oxy)phenoxy)ethoxy)ethoxy)acetamido)butanoyl)-4-hydroxy-N-((S)-1-(4-(4-methylthiazol-5-yl)phenyl)ethyl)pyrrolidine-2-carboxamide | 1123.69 | 15 |

FIG. 2A. Continued

| No. | Structure | Compound Name | MH+ | Synthetic Scheme |
|---|---|---|---|---|
| 381 | 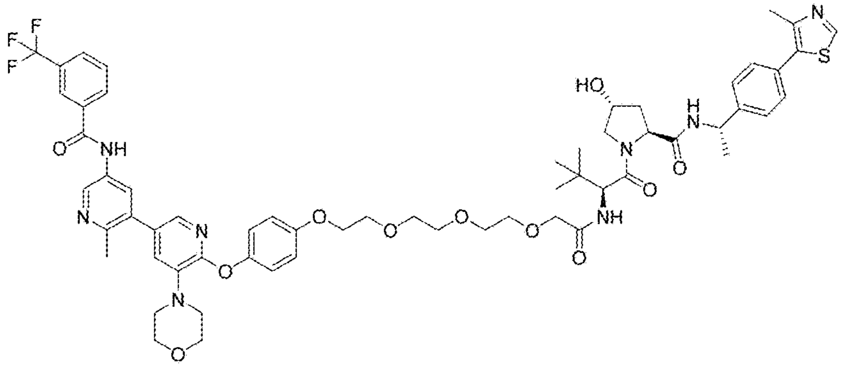 | (2S,4R)-1-((S)-2-(tert-butyl)-14-(4-((2'-methyl-5-morpholino-5'-(3-(trifluoromethyl)benzamido)-[3,3'-bipyridin]-6-yl)oxy)phenoxy)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 1167.73 | 15 |
| 382 | 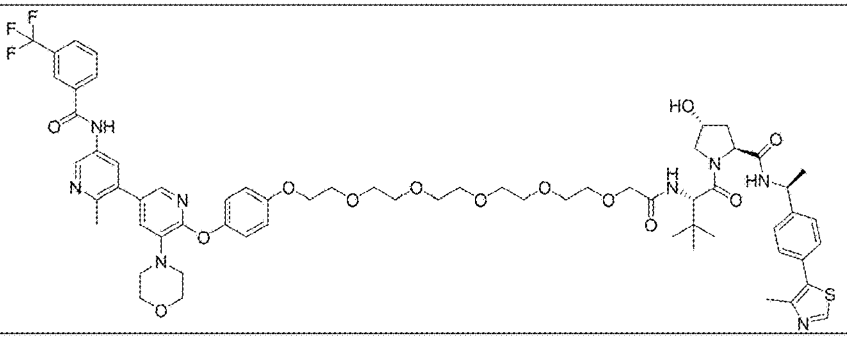 | (2S,4R)-1-((S)-2-(tert-butyl)-20-(4-((2'-methyl-5-morpholino-5'-(3-(trifluoromethyl)benzamido)-[3,3'-bipyridin]-6-yl)oxy)phenoxy)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 1255.79 | 15 |
| 383 | 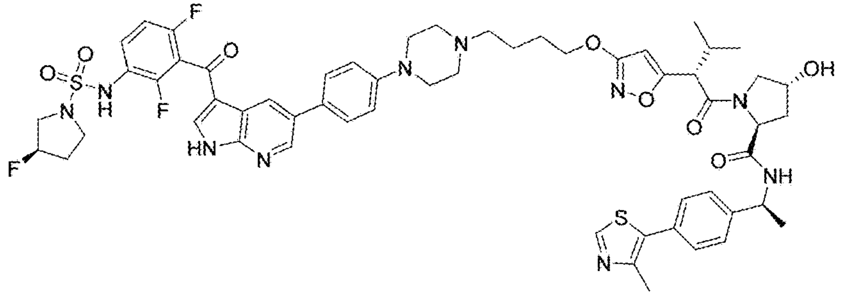 | (2S,4R)-1-((S)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoyl)-4-hydroxy-N-((S)-1-(4-(4-methylthiazol-5-yl)phenyl)ethyl)pyrrolidine-2-carboxamide | 1137.84 | Custom 2 |

FIG. 2A. Continued

| No. | Structure | Compound Name | MH+ | Synthetic Scheme |
|---|---|---|---|---|
| 384 | 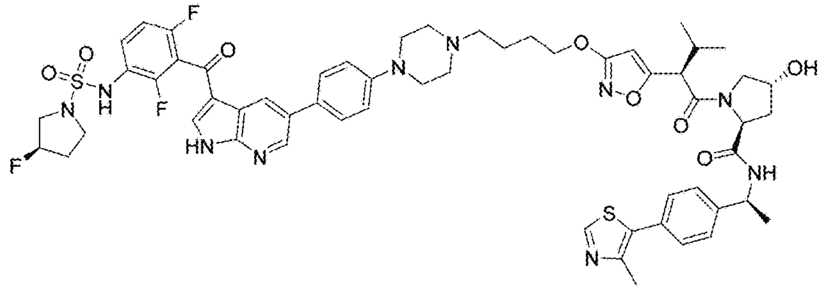 | (2S,4R)-1-((R)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoyl)-4-hydroxy-N-((S)-1-(4-(4-methylthiazol-5-yl)phenyl)ethyl)pyrrolidine-2-carboxamide | 1137.84 | Custom 2 |
| 385 | 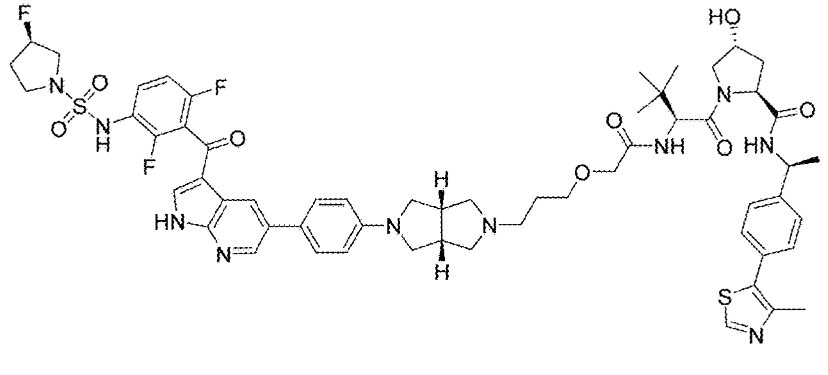 | (2S,4R)-1-((S)-2-(2-(3-((3aR,6aS)-5-(4-(3-(2,6-difluoro-3-(((R)-3-fluoropyrrolidine)-1-sulfonamido)benzoyl)-1H-pyrrolo[2,3-b]pyridin-5-yl)phenyl)hexahydropyrrolo[3,4-c]pyrrol-2(1H)-yl)propoxy)acetamido)-3,3-dimethylbutanoyl)-4-hydroxy-N-((S)-1-(4-(4-methylthiazol-5-yl)phenyl)ethyl)pyrrolidine-2-carboxamide | 1153.87 | 3 |
| 386 | 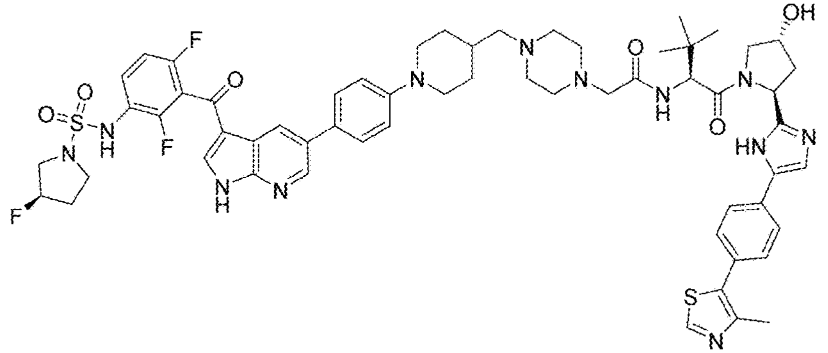 | 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N-((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)acetamide | 1161.89 | Custom |

FIG. 2A. Continued

| No. | Structure | Compound Name | MH+ | Synthetic Scheme |
| --- | --- | --- | --- | --- |
| 387 | 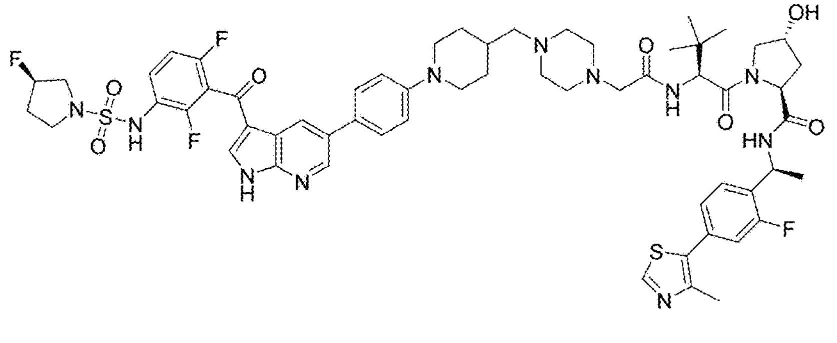 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-N-((S)-1-(2-fluoro-4-(4-methylthiazol-5-yl)phenyl)ethyl)-4-hydroxypyrrolidine-2-carboxamide | 1184.9 | 3 |
| 388 | 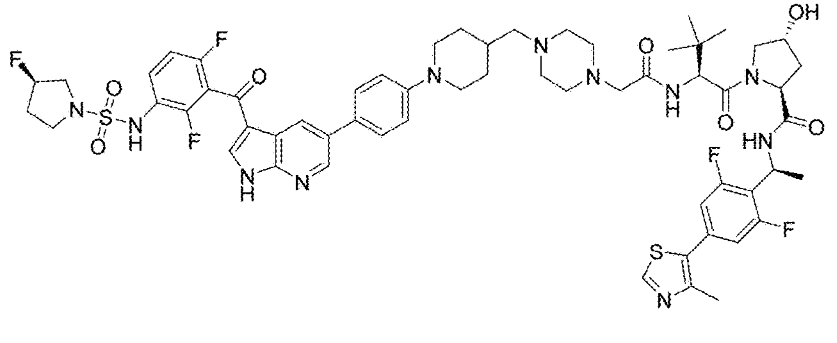 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-N-((S)-1-(2,6-difluoro-4-(4-methylthiazol-5-yl)phenyl)ethyl)-4-hydroxypyrrolidine-2-carboxamide | 1202.89 | 3 |
| 389 | 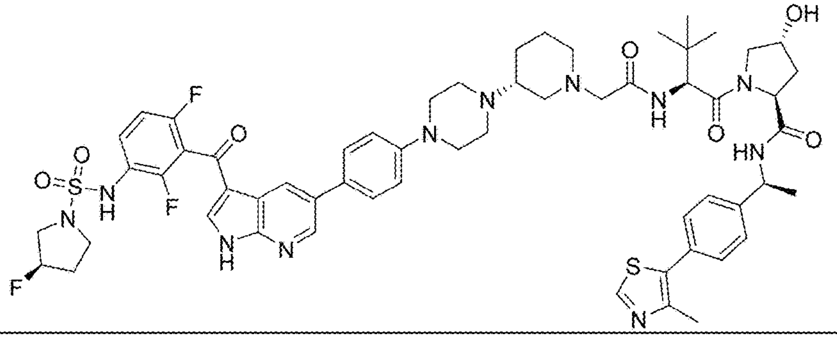 | (2S,4R)-1-((S)-2-(2-((R)-3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.88 | 3 |

FIG. 2A. Continued

| No. | Structure | Compound Name | MH+ | Synthetic Scheme |
| --- | --- | --- | --- | --- |
| 390 | 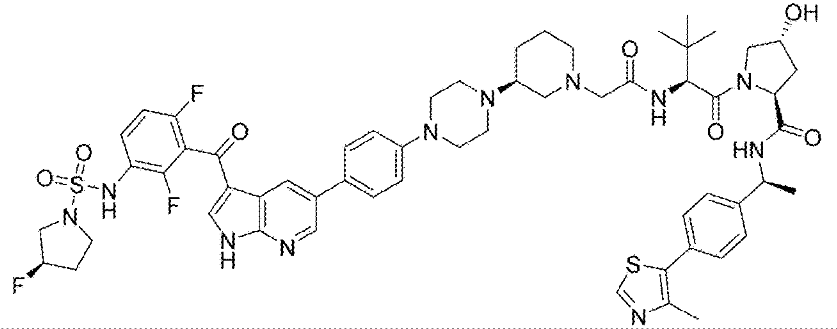 | (2S,4R)-1-((S)-2-(2-((S)-3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1152.88 | 3 |
| 391 | 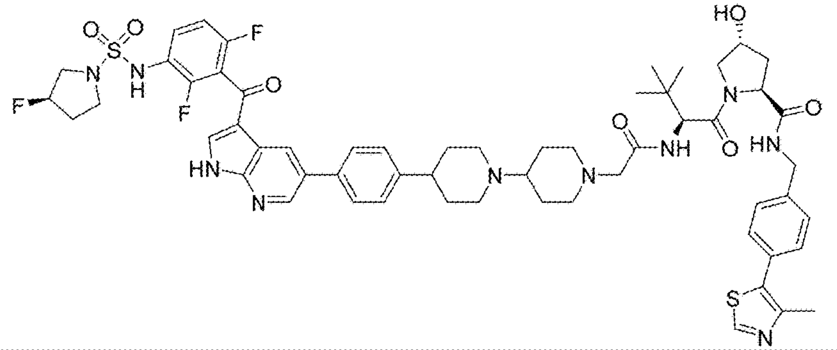 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)-[1,4'-bipiperidin]-1'-yl)acetamido)-3,3-dimethylbutanoyl)-4-hydroxy-N-(4-(4-methylthiazol-5-yl)benzyl)pyrrolidine-2-carboxamide | 1137.87 | 3 |
| 392 | 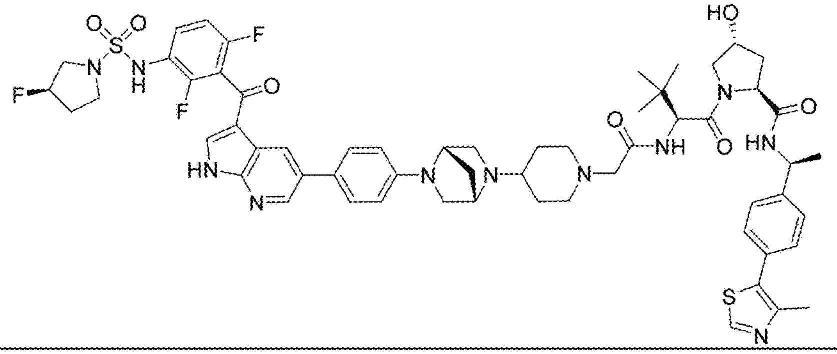 | (2S,4R)-1-((S)-2-(2-(4-((1S,4S)-5-(4-(3-(2,6-difluoro-3-(((R)-3-fluoropyrrolidine)-1-sulfonamido)benzoyl)-1H-pyrrolo[2,3-b]pyridin-5-yl)phenyl)-2,5-diazabicyclo[2.2.1]heptan-2-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1164.88 | 3 |

FIG. 2A. Continued

| No. | Structure | Compound Name | MH+ | Synthetic Scheme |
|---|---|---|---|---|
| 393 | 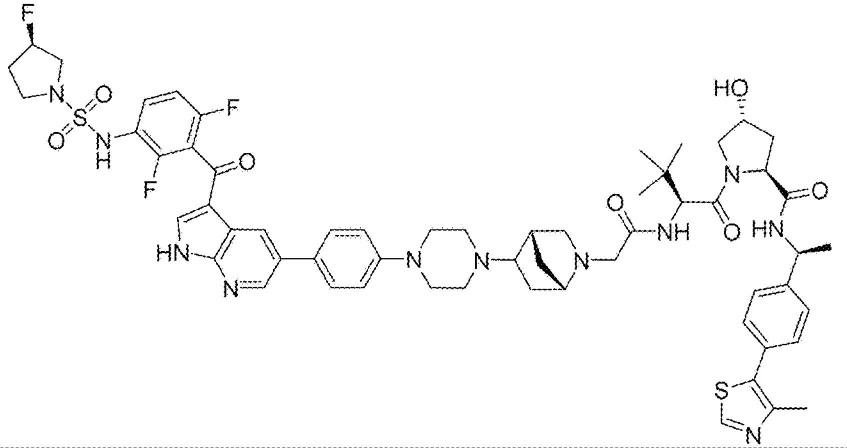 | (2S,4R)-1-((2S)-2-(2-((1S,4S)-5-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)-2-azabicyclo[2.2.1]heptan-2-yl)acetamido)-3,3-dimethylbutanoyl)-4-hydroxy-N-((S)-1-(4-(4-methylthiazol-5-yl)phenyl)ethyl)pyrrolidine-2-carboxamide | 1164.88 | 3 |
| 394 | 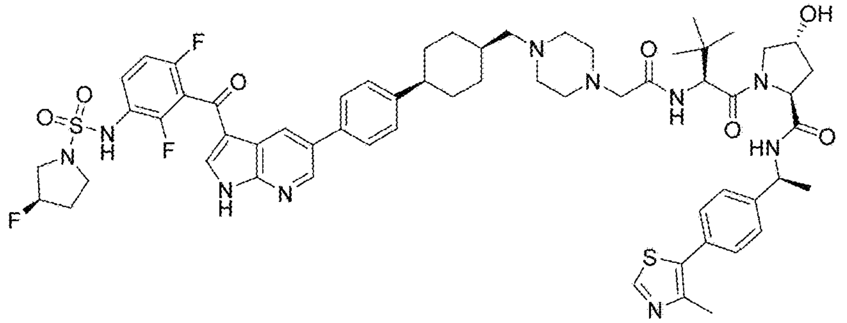 | (2S,4R)-1-((S)-2-(2-(4-(((1s,4R)-4-(4-(3-(2,6-difluoro-3-(((R)-3-fluoropyrrolidine)-1-sulfonamido)benzoyl)-1H-pyrrolo[2,3-b]pyridin-5-yl)phenyl)cyclohexyl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1165.9 | 3 |

FIG. 2A. Continued

| No. | Structure | Compound Name | MH+ | Synthetic Scheme |
|---|---|---|---|---|
| 395 | 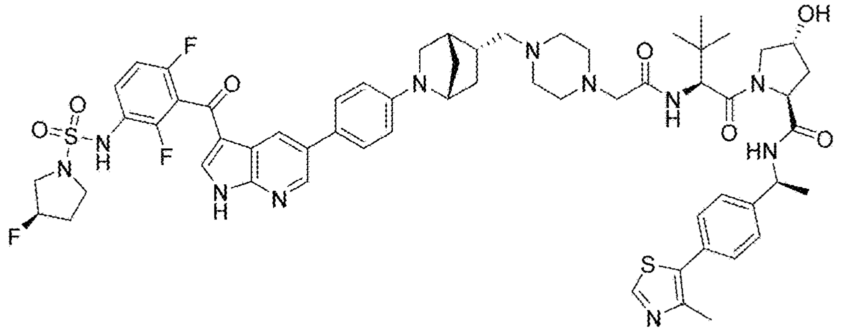 | (2S,4R)-1-((S)-2-(2-(4-(((1S,4S,5R)-2-(4-(3-(2,6-difluoro-3-(((R)-3-fluoropyrrolidine)-1-sulfonamido)benzoyl)-1H-pyrrolo[2,3-b]pyridin-5-yl)phenyl)-2-azabicyclo[2.2.1]heptan-5-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.9 | 3 |
| 396 | 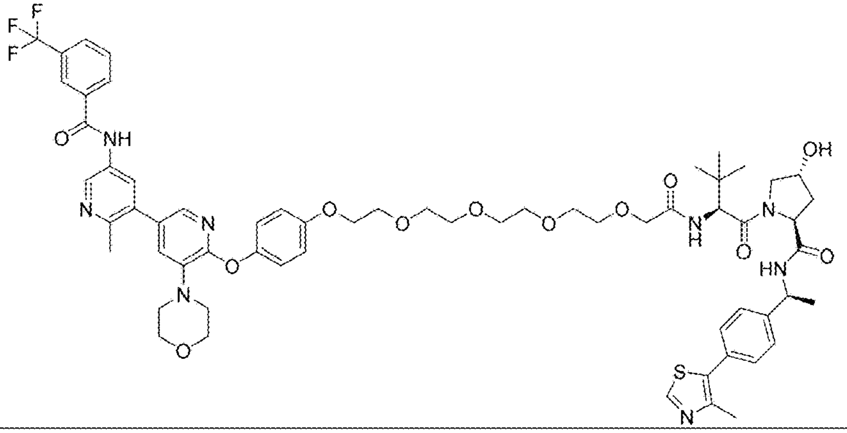 | (2S,4R)-1-((S)-2-(tert-butyl)-17-(4-((2'-methyl-5-morpholino-5'-(3-(trifluoromethyl)benzamido)-[3,3'-bipyridin]-6-yl)oxy)phenoxy)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | 1211.92 | 15 |

FIG. 2A. Continued

| No. | Structure | Compound Name | MH+ | Synthetic Scheme |
|---|---|---|---|---|
| 397 | 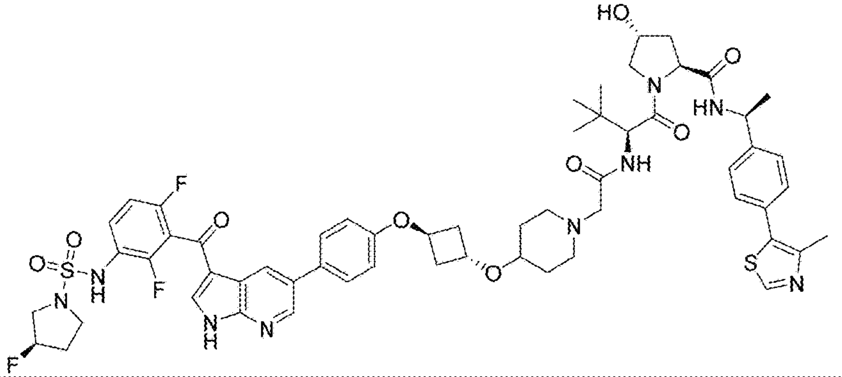 | (2S,4R)-1-((S)-2-(2-(4-((1r,3S)-3-(4-(3-(2,6-difluoro-3-(((R)-3-fluoropyrrolidine)-1-sulfonamido)benzoyl)-1H-pyrrolo[2,3-b]pyridin-5-yl)phenoxy)cyclobutoxy)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1154.85 | 3 |
| 398 | 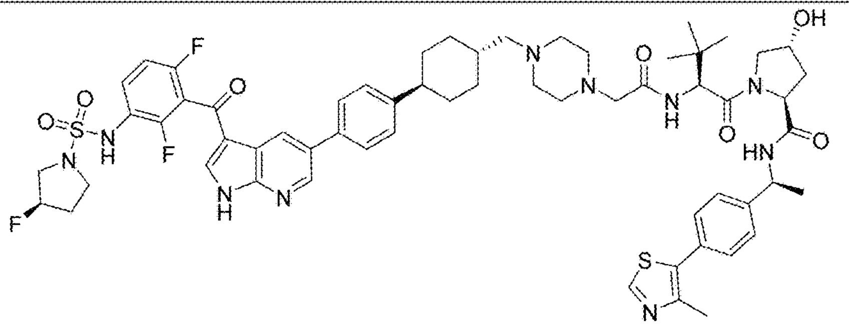 | (2S,4R)-1-((S)-2-(2-(4-(((1r,4S)-4-(4-(3-(2,6-difluoro-3-(((R)-3-fluoropyrrolidine)-1-sulfonamido)benzoyl)-1H-pyrrolo[2,3-b]pyridin-5-yl)phenyl)cyclohexyl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1165.9 | 3 |
| 399 | 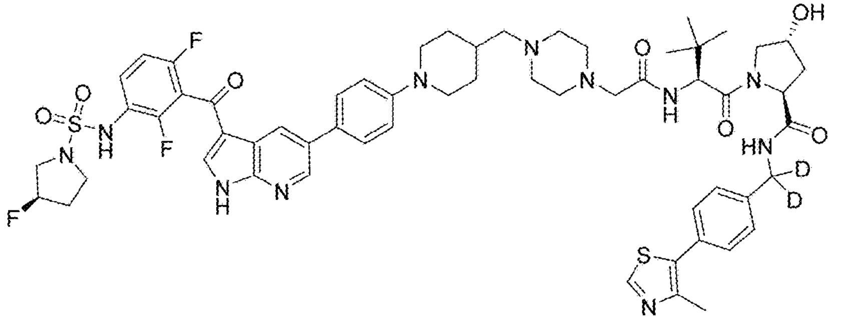 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((4-(4-methylthiazol-5-yl)phenyl)methyl-d2)pyrrolidine-2-carboxamide | 1154.89 | 3 |

FIG. 2A. Continued

| No. | Structure | Compound Name | MH+ | Synthetic Scheme |
|---|---|---|---|---|
| 400 | 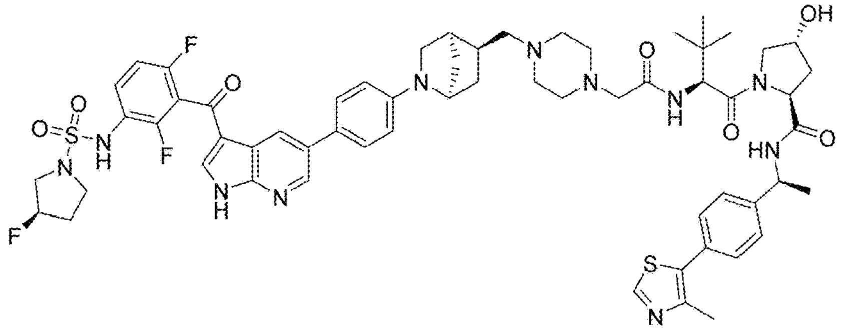 | (2S,4R)-1-((S)-2-(2-(4-(((1R,4R,5S)-2-(4-(3-(2,6-difluoro-3-(((R)-3-fluoropyrrolidine)-1-sulfonamido)benzoyl)-1H-pyrrolo[2,3-b]pyridin-5-yl)phenyl)-2-azabicyclo[2.2.1]heptan-5-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.9 | 3 |
| 401 | 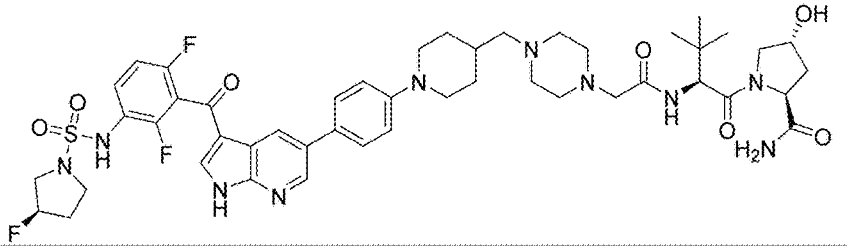 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxamide | 965.78 | |
| 402 | 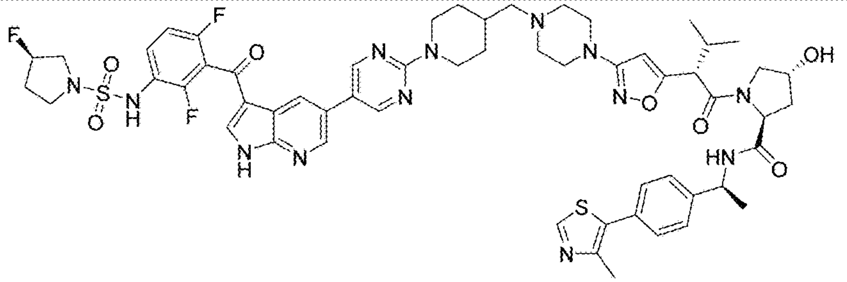 | (2S,4R)-1-((S)-2-(3-(4-((1-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1164.85 | 18 |

FIG. 2A. Continued

| No. | Structure | Compound Name | MH+ | Synthetic Scheme |
|---|---|---|---|---|
| 403 | 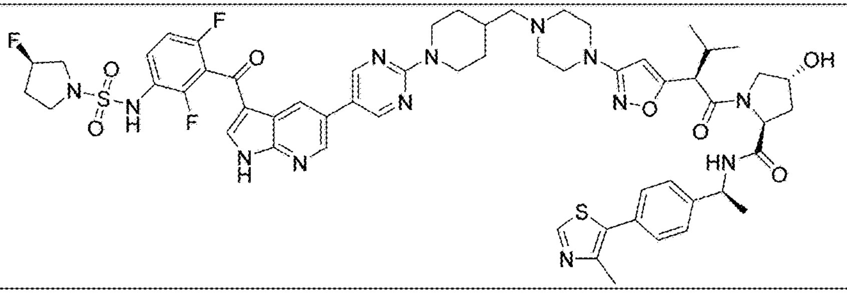 | (2S,4R)-1-((R)-2-(3-(4-((1-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1164.86 | 18 |
| 404 | 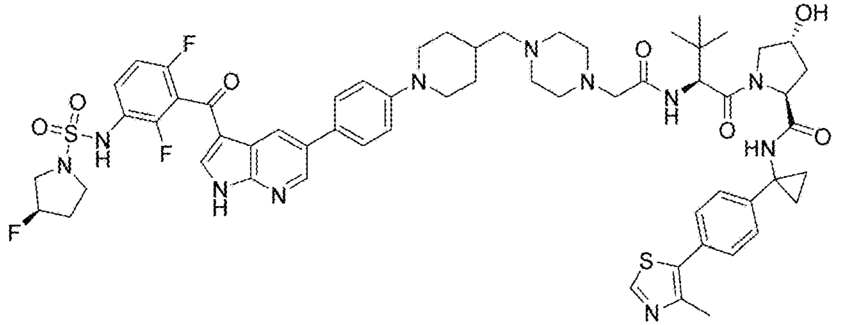 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(1-(4-(4-methylthiazol-5-yl)phenyl)cyclopropyl)pyrrolidine-2-carboxamide | 1178.9 | 17 |
| 405 | 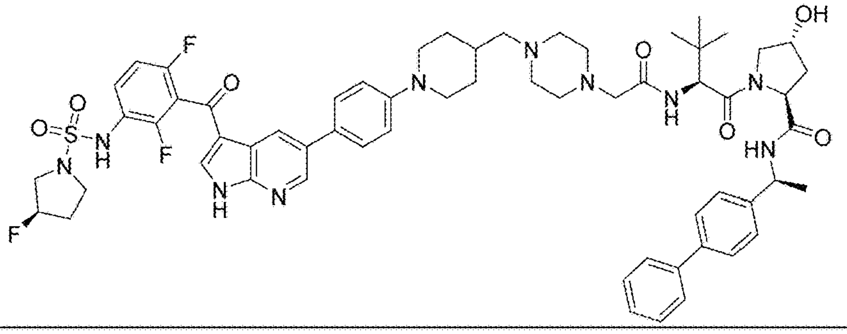 | (2S,4R)-N-((S)-1-([1,1'-biphenyl]-4-yl)ethyl)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxamide | 1145.92 | 17 |

FIG. 2A. Continued

| No. | Structure | Compound Name | MH+ | Synthetic Scheme |
|---|---|---|---|---|
| 406 | 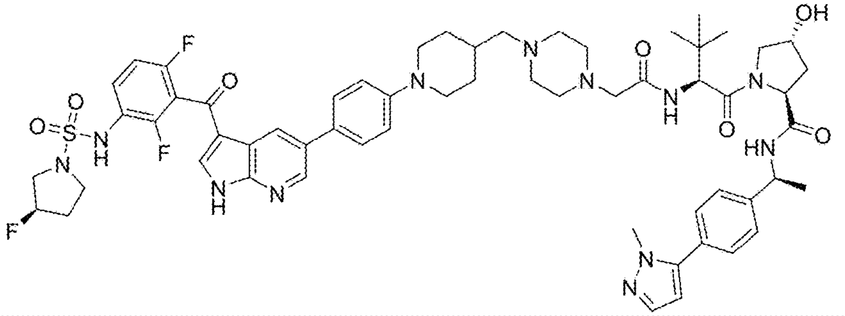 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((S)-1-(4-(1-methyl-1H-pyrazol-5-yl)phenyl)ethyl)pyrrolidine-2-carboxamide | 1149.93 | 17 |
| 407 | 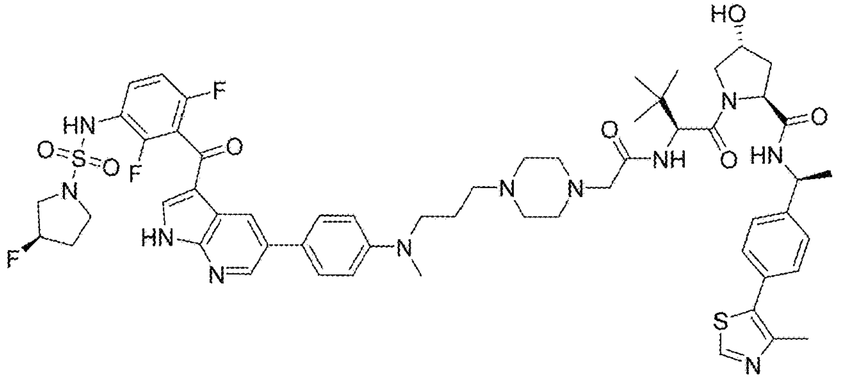 | (2S,4R)-1-((S)-2-(2-(4-(3-((4-(3-(2,6-difluoro-3-(((R)-3-fluoropyrrolidine)-1-sulfonamido)benzoyl)-1H-pyrrolo[2,3-b]pyridin-5-yl)phenyl)(methyl)amino)propyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1140.87 | 3 |

FIG. 2A. Continued

| No. | Structure | Compound Name | MH+ | Synthetic Scheme |
|---|---|---|---|---|
| 408 | 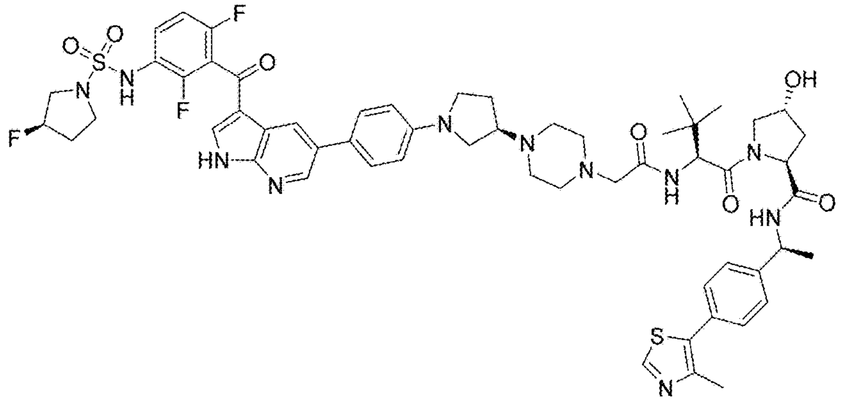 | (2S,4R)-1-((S)-2-(2-(4-((R)-1-(4-(3-(2,6-difluoro-3-(((R)-3-fluoropyrrolidine)-1-sulfonamido)benzoyl)-1H-pyrrolo[2,3-b]pyridin-5-yl)phenyl)pyrrolidin-3-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1138.87 | 4 |
| 409 | 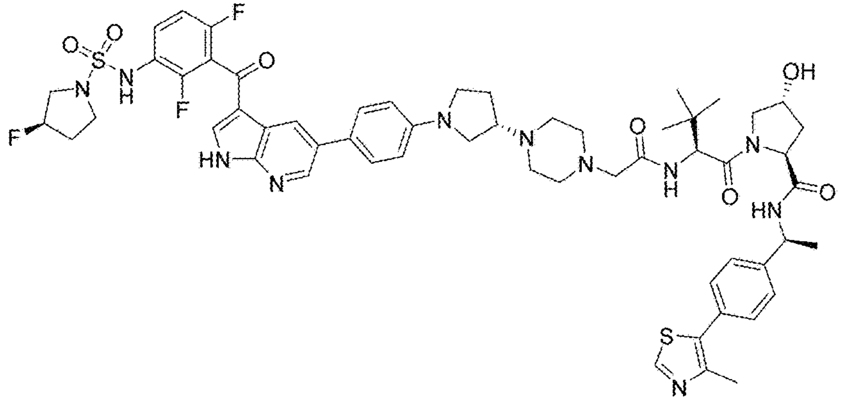 | (2S,4R)-1-((S)-2-(2-(4-((S)-1-(4-(3-(2,6-difluoro-3-(((R)-3-fluoropyrrolidine)-1-sulfonamido)benzoyl)-1H-pyrrolo[2,3-b]pyridin-5-yl)phenyl)pyrrolidin-3-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1138.86 | 4 |

FIG. 2A. Continued

| No. | Structure | Compound Name | MH+ | Synthetic Scheme |
|---|---|---|---|---|
| 410 | 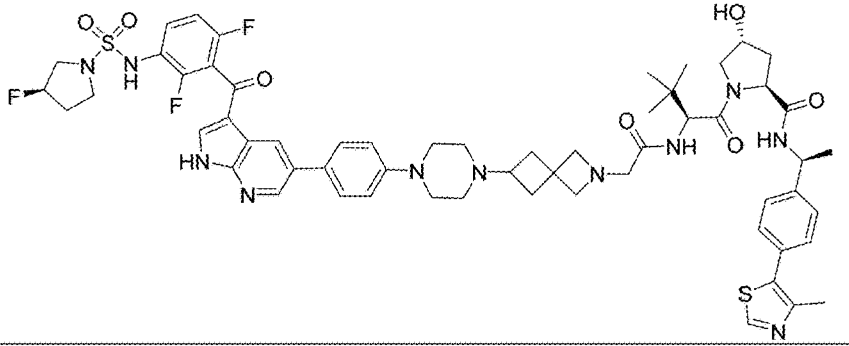 | (2S,4R)-1-((S)-2-(2-(6-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)-2-azaspiro[3.3]heptan-2-yl)acetamido)-3,3-dimethylbutanoyl)-4-hydroxy-N-((S)-1-(4-(4-methylthiazol-5-yl)phenyl)ethyl)pyrrolidine-2-carboxamide | 1164.88 | 3 |
| 411 | 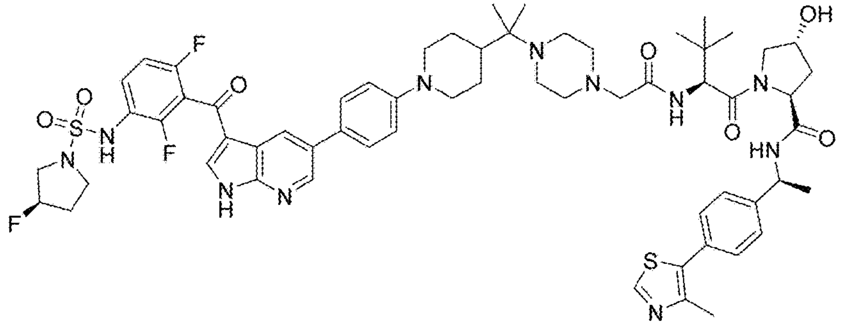 | (2S,4R)-1-((S)-2-(2-(4-(2-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)propan-2-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.93 | 3 |

FIG. 2A. Continued

| No. | Structure | Compound Name | MH+ | Synthetic Scheme |
|---|---|---|---|---|
| 412 | 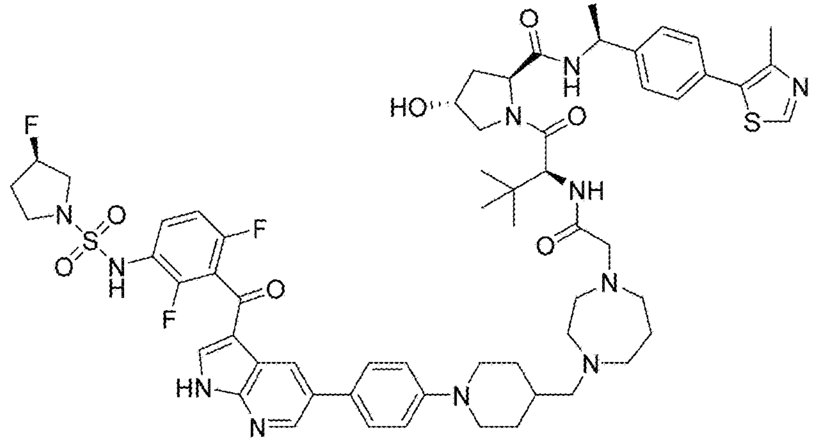 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-1,4-diazepan-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.9 | Custom 1 |
| 413 | 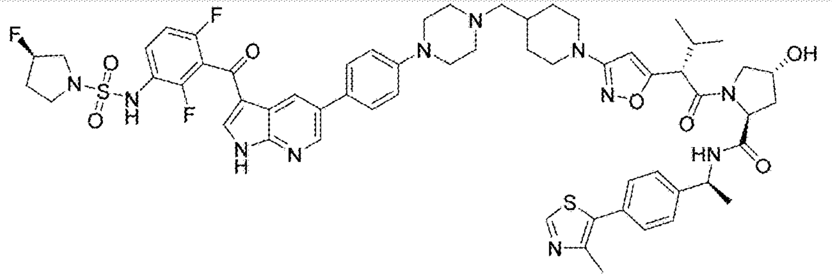 | (2S,4R)-1-((S)-2-(3-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1162.86 | 18 |
| 414 | 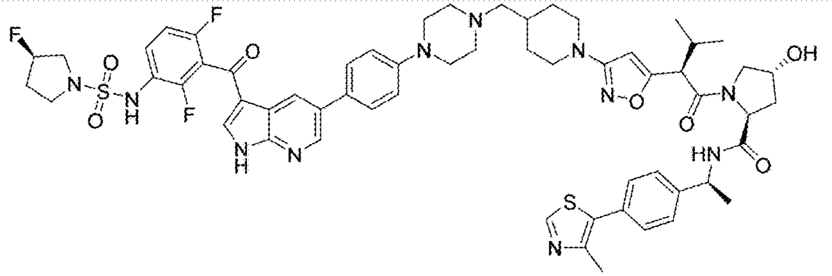 | (2S,4R)-1-((R)-2-(3-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1162.86 | 18 |

FIG. 2A. Continued

| No. | Structure | Compound Name | MH+ | Synthetic Scheme |
|---|---|---|---|---|
| 415 | 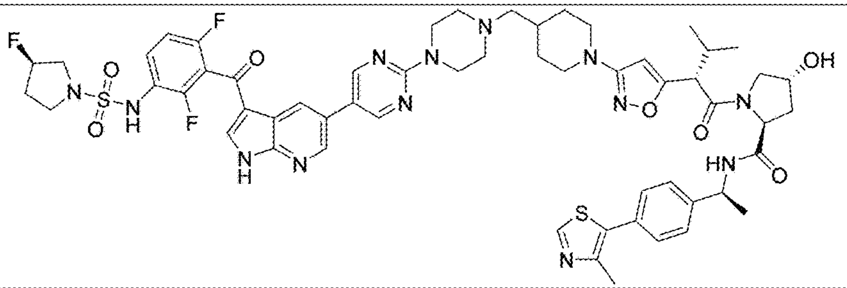 | (2S,4R)-1-((S)-2-(3-(4-((4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1164.83 | 18 |
| 416 | 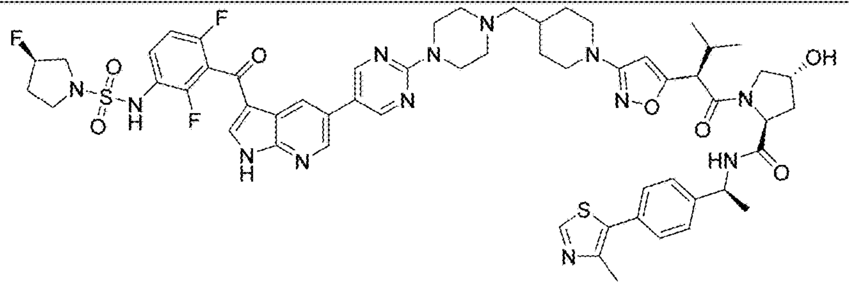 | (2S,4R)-1-((R)-2-(3-(4-((4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1164.85 | 18 |
| 417 | 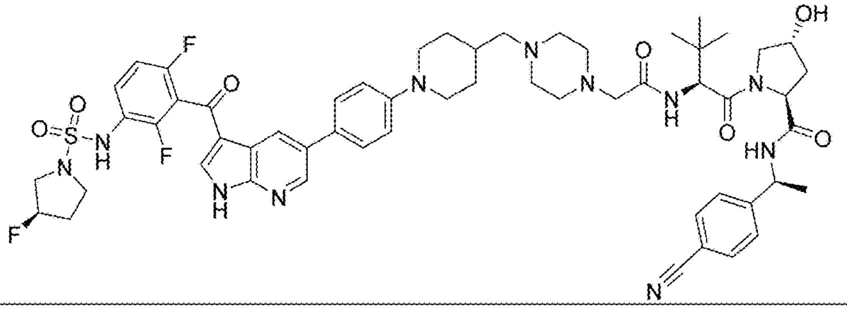 | (2S,4R)-N-((S)-1-(4-cyanophenyl)ethyl)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxamide | 1094.87 | 17 |

FIG. 2A. Continued

| No. | Structure | Compound Name | MH+ | Synthetic Scheme |
|---|---|---|---|---|
| 418 | 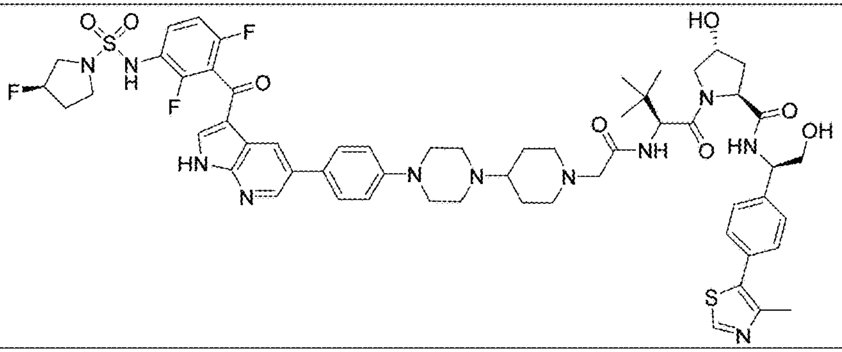 | (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1168.87 | 3 |
| 419 | 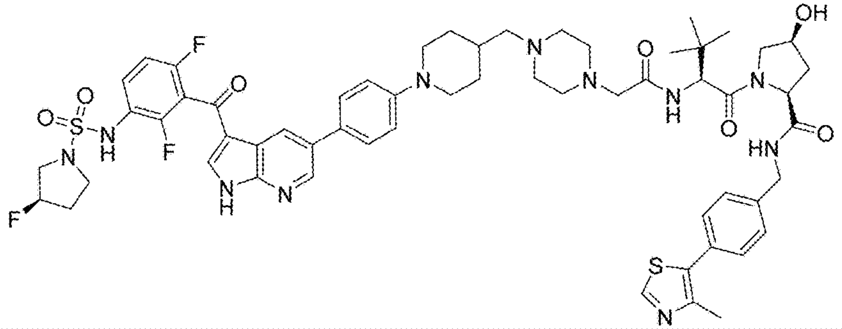 | (2S,4S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide | 1152.87 | 3 |
| 420 | 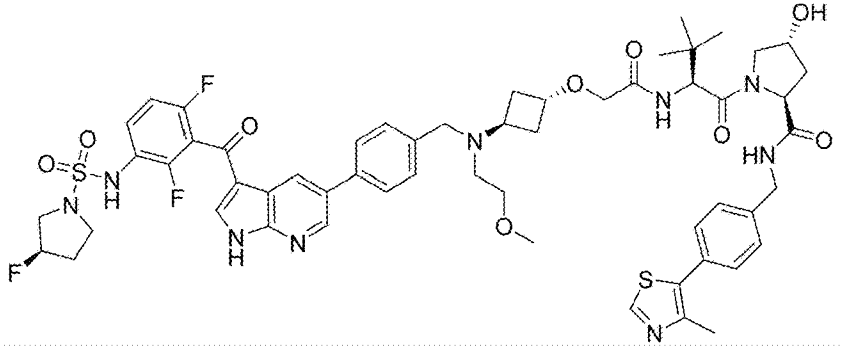 | (2S,4R)-1-((S)-2-(2-((1r,3S)-3-((4-(3-(2,6-difluoro-3-(((R)-3-fluoropyrrolidine)-1-sulfonamido)benzoyl)-1H-pyrrolo[2,3-b]pyridin-5-yl)benzyl)(2-methoxyethyl)amino)cyclobutoxy)acetamido)-3,3-dimethylbutanoyl)-4-hydroxy-N-(4-(4-methylthiazol-5-yl)benzyl)pyrrolidine-2-carboxamide | 1128.82 | 3 |

FIG. 2A. Continued

| No. | Structure | Compound Name | MH+ | Synthetic Scheme |
|---|---|---|---|---|
| 421 | 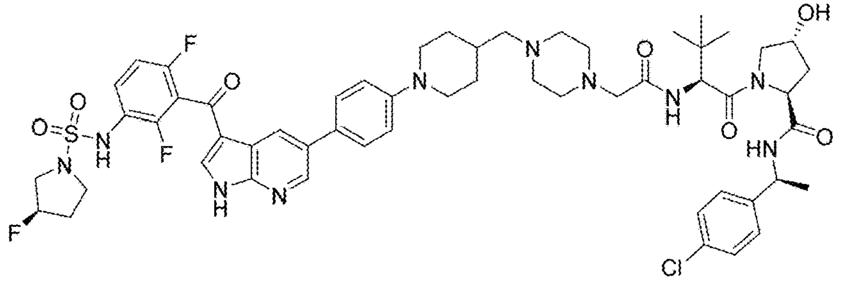 | (2S,4R)-N-((S)-1-(4-chlorophenyl)ethyl)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxamide | 1103.84 | 17 |
| 422 | 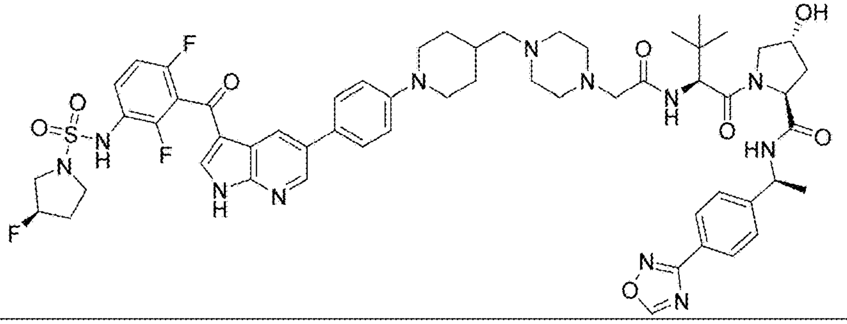 | (2S,4R)-N-((S)-1-(4-(1,2,4-oxadiazol-3-yl)phenyl)ethyl)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxamide | 1137.89 | 17 |
| 423 | 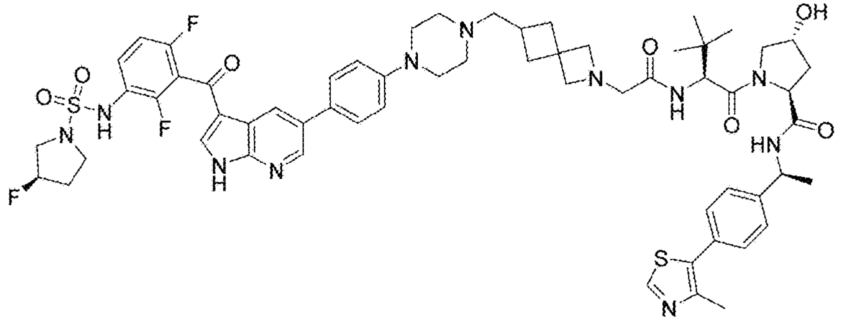 | (2S,4R)-1-((S)-2-(2-(6-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)-2-azaspiro[3.3]heptan-2-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.89 | 3 |

FIG. 2A. Continued

| No. | Structure | Compound Name | MH+ | Synthetic Scheme |
|---|---|---|---|---|
| 424 | 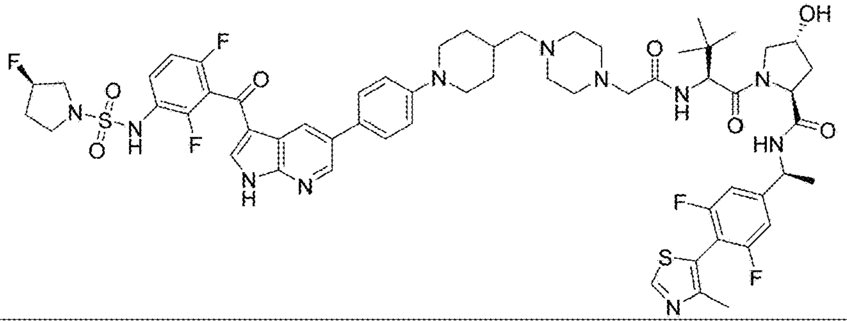 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-N-((S)-1-(3,5-difluoro-4-(4-methylthiazol-5-yl)phenyl)ethyl)-4-hydroxypyrrolidine-2-carboxamide | 1202.88 | 3 |
| 425 | 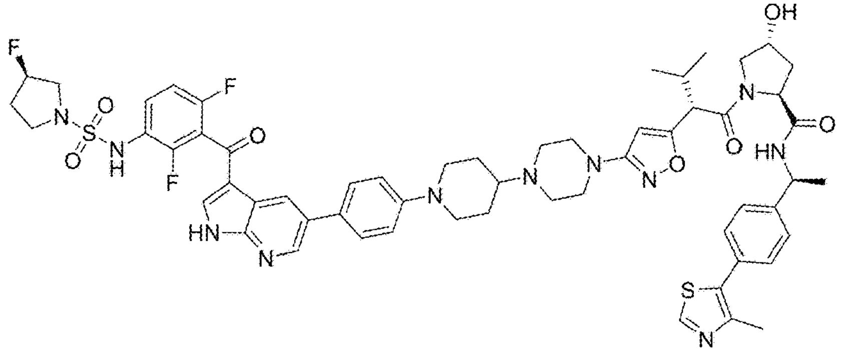 | (2S,4R)-1-((S)-2-(3-(4-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1148.84 | 18 |
| 426 | 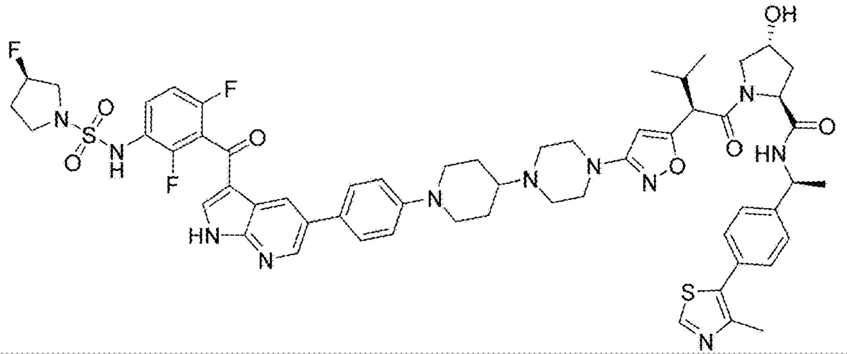 | (2S,4R)-1-((R)-2-(3-(4-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1148.84 | 18 |

FIG. 2A. Continued

| No. | Structure | Compound Name | MH+ | Synthetic Scheme |
|---|---|---|---|---|
| 427 | 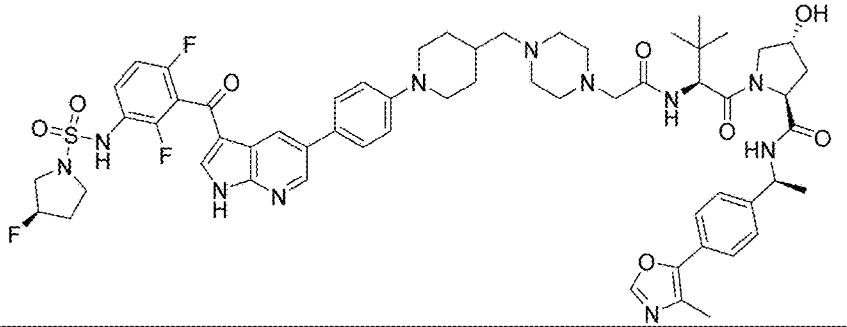 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((S)-1-(4-(4-methyloxazol-5-yl)phenyl)ethyl)pyrrolidine-2-carboxamide | 1150.91 | 17 |
| 428 | 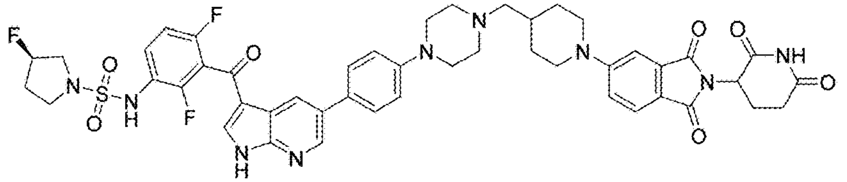 | (3R)-N-(3-(5-(4-(4-((1-(2-(2,6-dioxopiperidin-3-yl)-1,3-dioxoisoindolin-5-yl)piperidin-4-yl)methyl)piperazin-1-yl)phenyl)-1H-pyrrolo[2,3-b]pyridine-3-carbonyl)-2,4-difluorophenyl)-3-fluoropyrrolidine-1-sulfonamide | 938.67 | 1 |
| 429 | 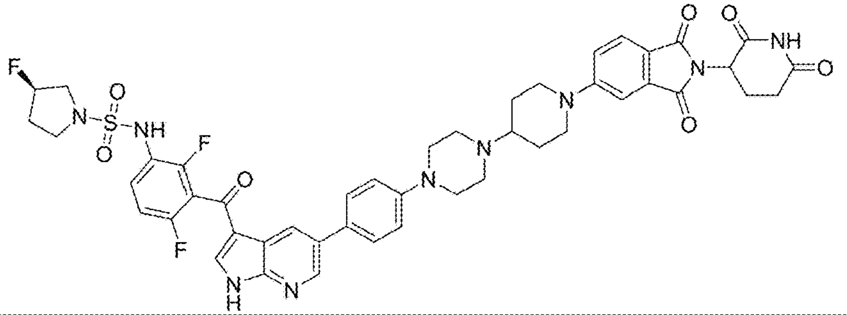 | (3R)-N-(3-(5-(4-(4-(1-(2-(2,6-dioxopiperidin-3-yl)-1,3-dioxoisoindolin-5-yl)piperidin-4-yl)piperazin-1-yl)phenyl)-1H-pyrrolo[2,3-b]pyridine-3-carbonyl)-2,4-difluorophenyl)-3-fluoropyrrolidine-1-sulfonamide | 924.65 | 1 |

FIG. 2A. Continued

| No. | Structure | Compound Name | MH+ | Synthetic Scheme |
|---|---|---|---|---|
| 430 | 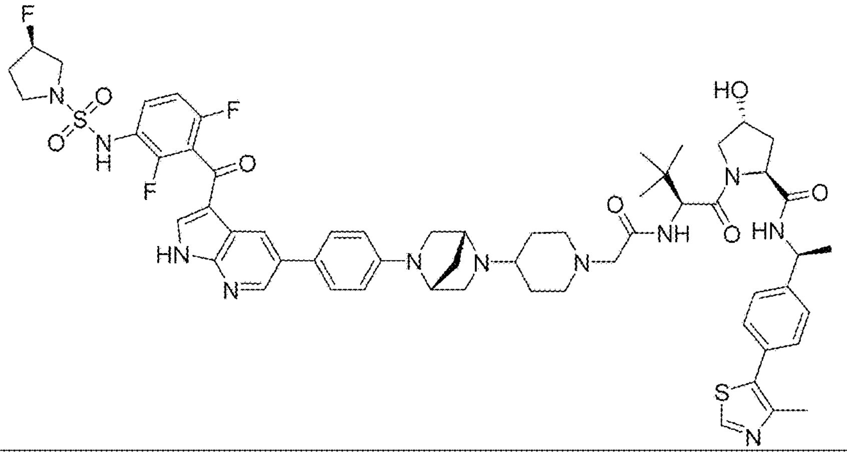 | (2S,4R)-1-((S)-2-(2-(4-((1R,4R)-5-(4-(3-(2,6-difluoro-3-(((R)-3-fluoropyrrolidine)-1-sulfonamido)benzoyl)-1H-pyrrolo[2,3-b]pyridin-5-yl)phenyl)-2,5-diazabicyclo[2.2.1]heptan-2-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1164.6 | 3 |
| 431 | 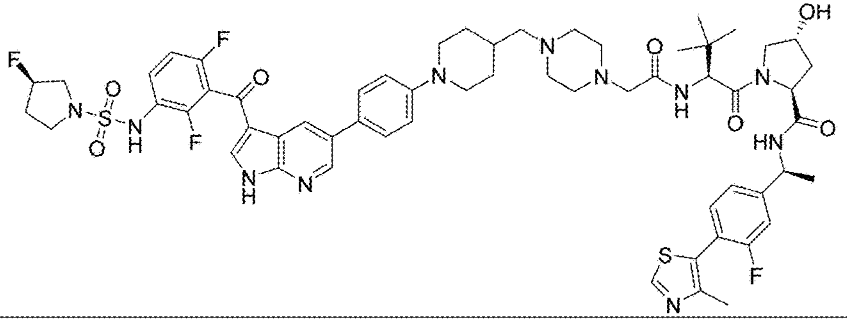 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-N-((S)-1-(3-fluoro-4-(4-methylthiazol-5-yl)phenyl)ethyl)-4-hydroxypyrrolidine-2-carboxamide | 1184.88 | 3 |

FIG. 2A. Continued

| No. | Structure | Compound Name | MH+ | Synthetic Scheme |
|---|---|---|---|---|
| 432 | 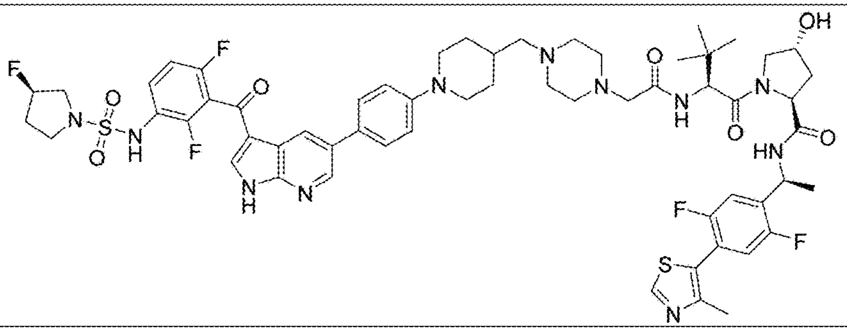 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-N-((S)-1-(2,5-difluoro-4-(4-methylthiazol-5-yl)phenyl)ethyl)-4-hydroxypyrrolidine-2-carboxamide | 1202.62 | 3 |
| 433 | 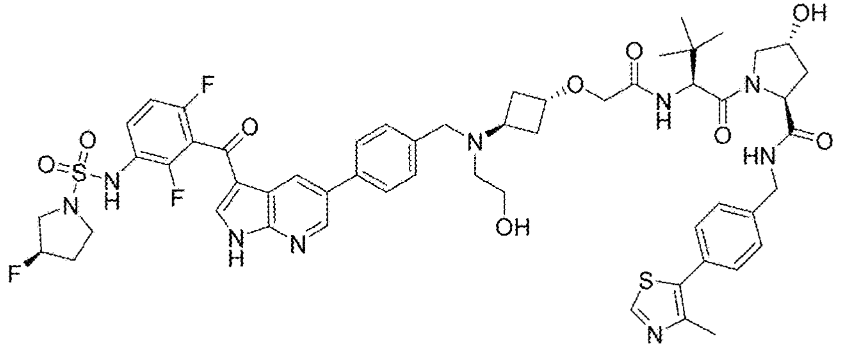 | (2S,4R)-1-((S)-2-(2-((1r,3S)-3-((4-(3-(2,6-difluoro-3-(((R)-3-fluoropyrrolidine)-1-sulfonamido)benzoyl)-1H-pyrrolo[2,3-b]pyridin-5-yl)benzyl)(2-hydroxyethyl)amino)cyclobutoxy)acetamido)-3,3-dimethylbutanoyl)-4-hydroxy-N-(4-(4-methylthiazol-5-yl)benzyl)pyrrolidine-2-carboxamide | 1114.57 | 3 |
| 434 | 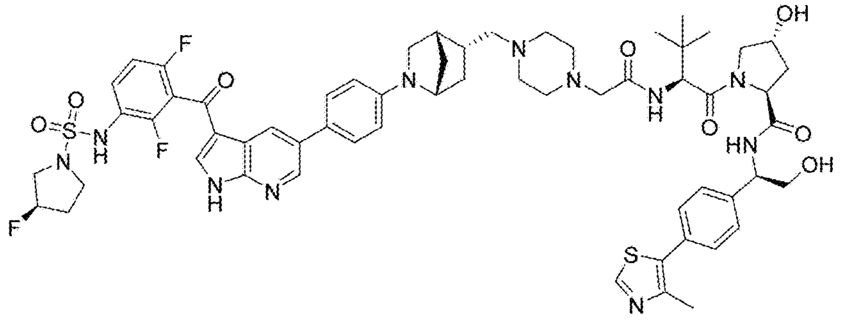 | (2S,4R)-1-((S)-2-(2-(4-(((1S,4S,5R)-2-(4-(3-(2,6-difluoro-3-(((R)-3-fluoropyrrolidine)-1-sulfonamido)benzoyl)-1H-pyrrolo[2,3-b]pyridin-5-yl)phenyl)-2-azabicyclo[2.2.1]heptan-5-yl)methyl)piperazin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1194.88 | 3 |

FIG. 2A. Continued

| No. | Structure | Compound Name | MH+ | Synthetic Scheme |
|---|---|---|---|---|
| 435 | 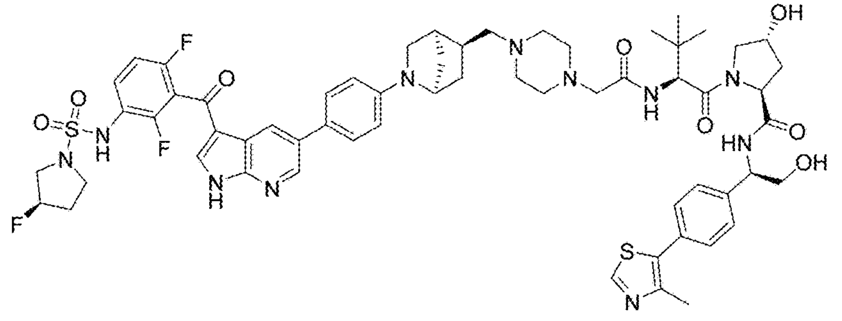 | (2S,4R)-1-((S)-2-(2-(4-(((1R,4R,5S)-2-(4-(3-(2,6-difluoro-3-(((R)-3-fluoropyrrolidine)-1-sulfonamido)benzoyl)-1H-pyrrolo[2,3-b]pyridin-5-yl)phenyl)-2-azabicyclo[2.2.1]heptan-5-yl)methyl)piperazin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1194.88 | 3 |
| 436 | 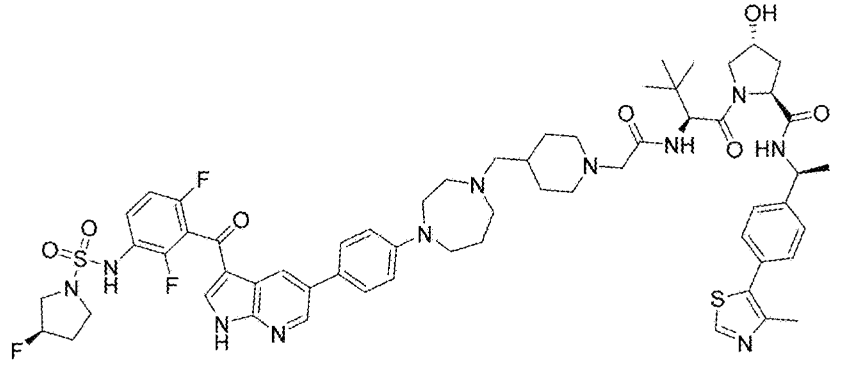 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)-1,4-diazepan-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.91 | 3 |
| 437 | 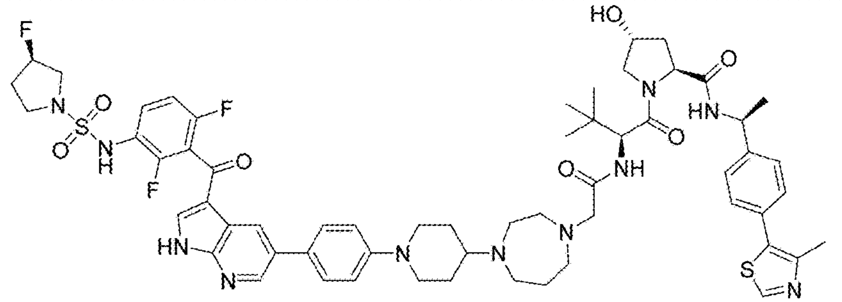 | (2S,4R)-1-((S)-2-(2-(4-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)-1,4-diazepan-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.88 | Custom 1 |

FIG. 2A. Continued

| No. | Structure | Compound Name | MH+ | Synthetic Scheme |
|---|---|---|---|---|
| 438 | 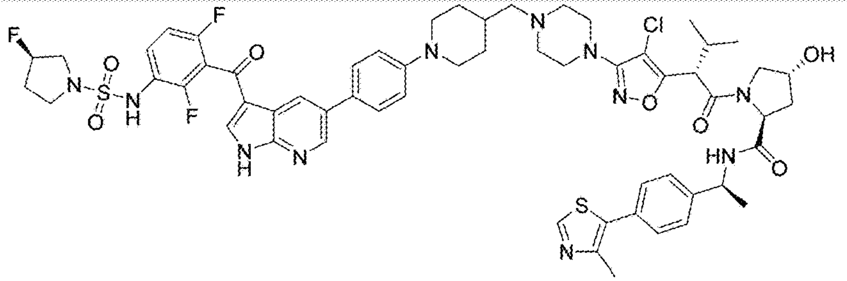 | (2S,4R)-1-((S)-2-(4-chloro-3-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1196.82 | 18 |
| 439 | 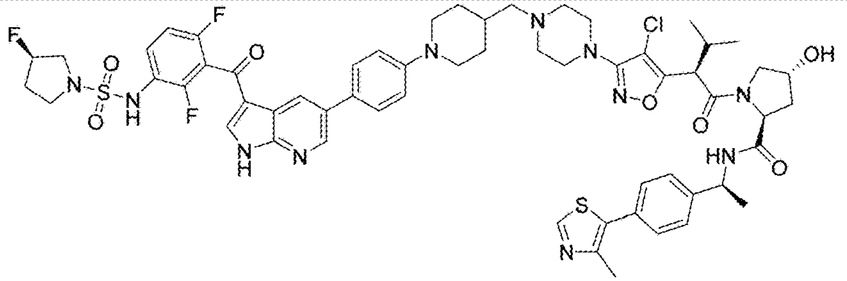 | (2S,4R)-1-((R)-2-(4-chloro-3-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1196.82 | 18 |
| 440 | 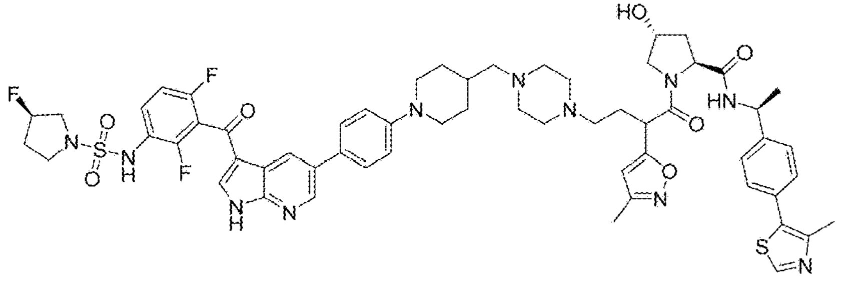 | (2S,4R)-1-(4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-2-(3-methylisoxazol-5-yl)butanoyl)-4-hydroxy-N-((S)-1-(4-(4-methylthiazol-5-yl)phenyl)ethyl)pyrrolidine-2-carboxamide | 1162.86 | Custom |

FIG. 2A. Continued

| No. | Structure | Compound Name | MH+ | Synthetic Scheme |
|---|---|---|---|---|
| 441 | 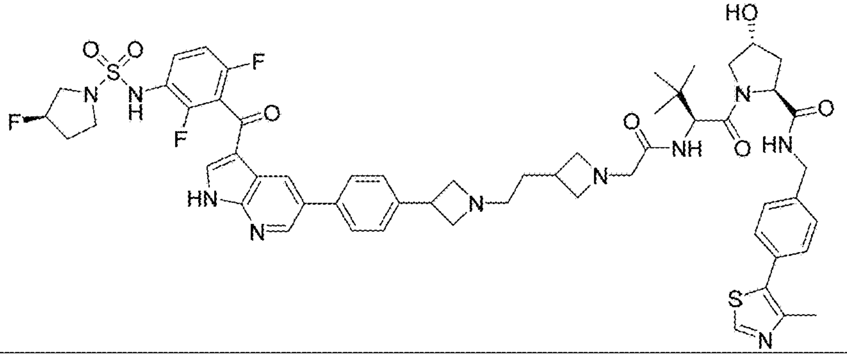 | (2S,4R)-1-((S)-2-(2-(3-(2-(3-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-1-yl)ethyl)azetidin-1-yl)acetamido)-3,3-dimethylbutanoyl)-4-hydroxy-N-(4-(4-methylthiazol-5-yl)benzyl)pyrrolidine-2-carboxamide | 1109.8 | Custom |
| 442 | 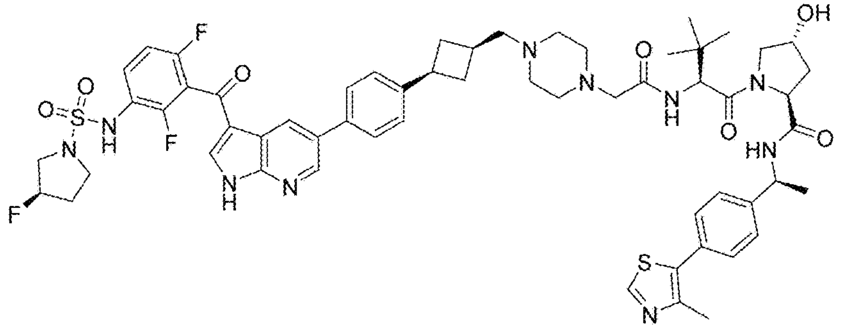 | (2S,4R)-1-((S)-2-(2-(4-(((1s,3R)-3-(4-(3-(2,6-difluoro-3-(((R)-3-fluoropyrrolidine)-1-sulfonamido)benzoyl)-1H-pyrrolo[2,3-b]pyridin-5-yl)phenyl)cyclobutyl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1137.9 | 3 |
| 443 | 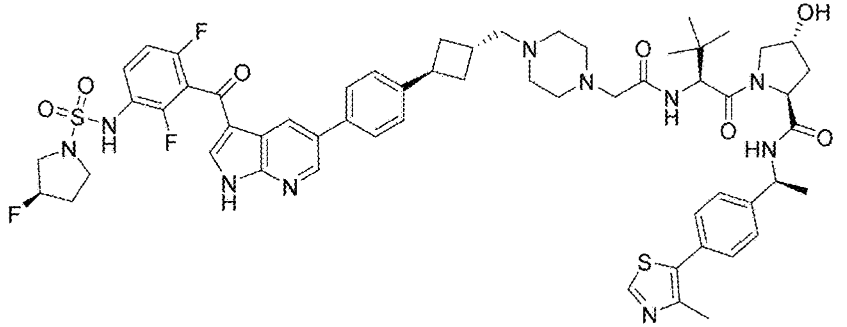 | (2S,4R)-1-((S)-2-(2-(4-(((1r,3S)-3-(4-(3-(2,6-difluoro-3-(((R)-3-fluoropyrrolidine)-1-sulfonamido)benzoyl)-1H-pyrrolo[2,3-b]pyridin-5-yl)phenyl)cyclobutyl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1137.9 | 3 |

FIG. 2A. Continued

| No. | Structure | Compound Name | MH+ | Synthetic Scheme |
| --- | --- | --- | --- | --- |
| 444 | 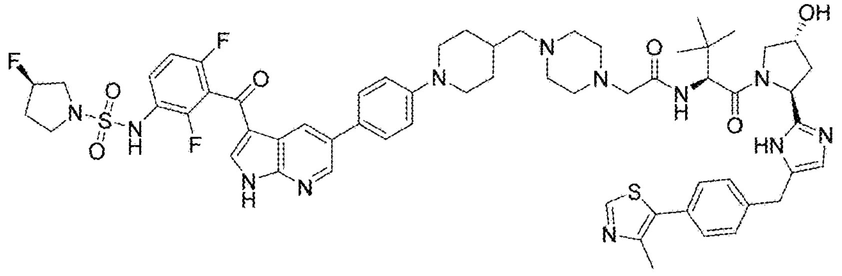 | 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N-((S)-1-((2S,4R)-4-hydroxy-2-(5-(4-(4-methylthiazol-5-yl)benzyl)-1H-imidazol-2-yl)pyrrolidin-1-yl)-3,3-dimethyl-1-oxobutan-2-yl)acetamide | 1175.9 | Custom |
| 445 | 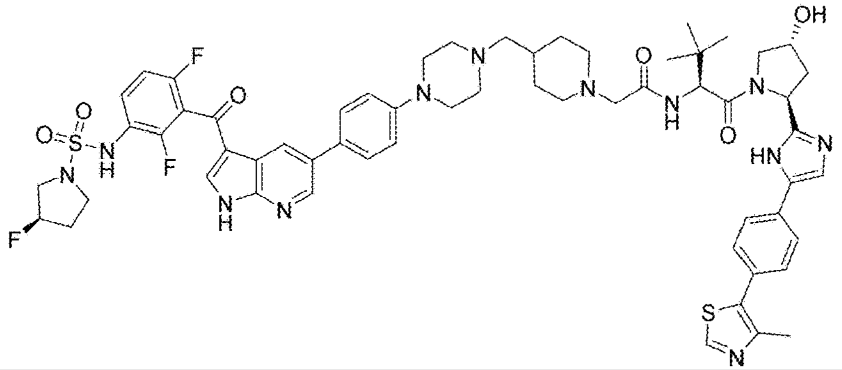 | 2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)-N-((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)acetamide | 1161.9 | Custom |
| 446 | 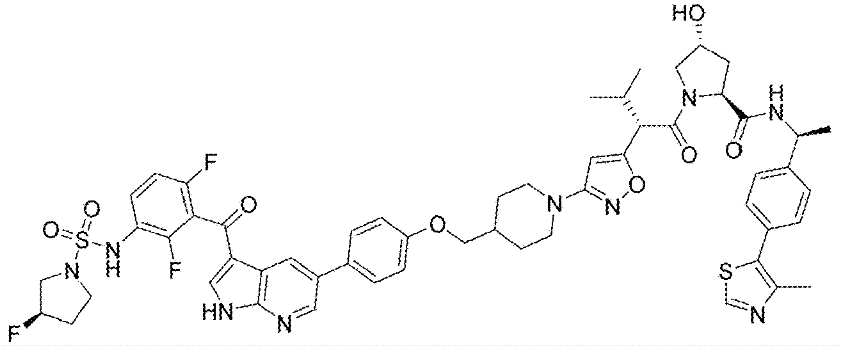 | (2S,4R)-1-((S)-2-(3-(4-((4-(3-(2,6-difluoro-3-(((R)-3-fluoropyrrolidine)-1-sulfonamido)benzoyl)-1H-pyrrolo[2,3-b]pyridin-5-yl)phenoxy)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1094.8 | 13 |

FIG. 2A. Continued

| No. | Structure | Compound Name | MH+ | Synthetic Scheme |
|---|---|---|---|---|
| 447 | 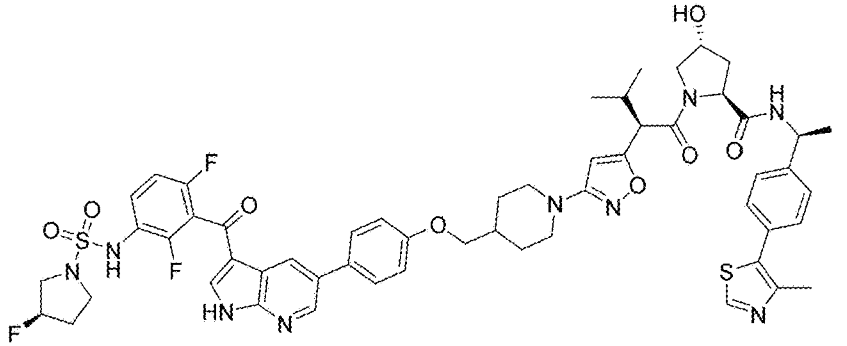 | (2S,4R)-1-((R)-2-(3-(4-((4-(3-(2,6-difluoro-3-(((R)-3-fluoropyrrolidine)-1-sulfonamido)benzoyl)-1H-pyrrolo[2,3-b]pyridin-5-yl)phenoxy)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1094.8 | 13 |
| 448 | 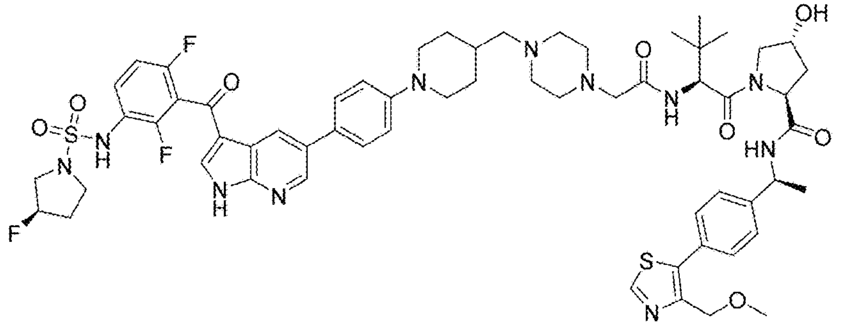 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((S)-1-(4-(4-(methoxymethyl)thiazol-5-yl)phenyl)ethyl)pyrrolidine-2-carboxamide | 1196.9 | 17 |
| 449 | 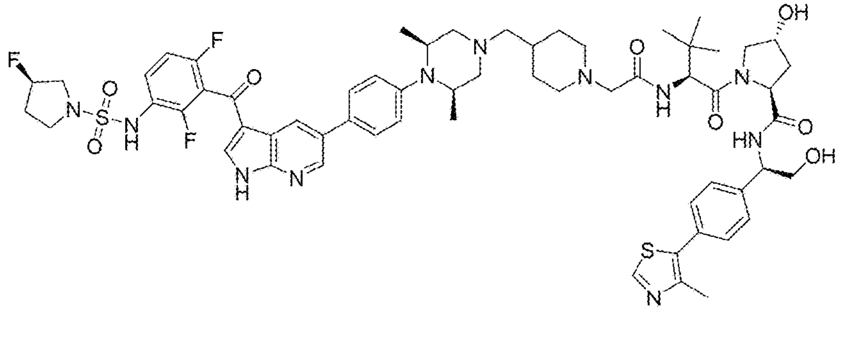 | (2S,4R)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1210.93 | 3 |

FIG. 2A. Continued

| No. | Structure | Compound Name | MH+ | Synthetic Scheme |
|---|---|---|---|---|
| 450 | 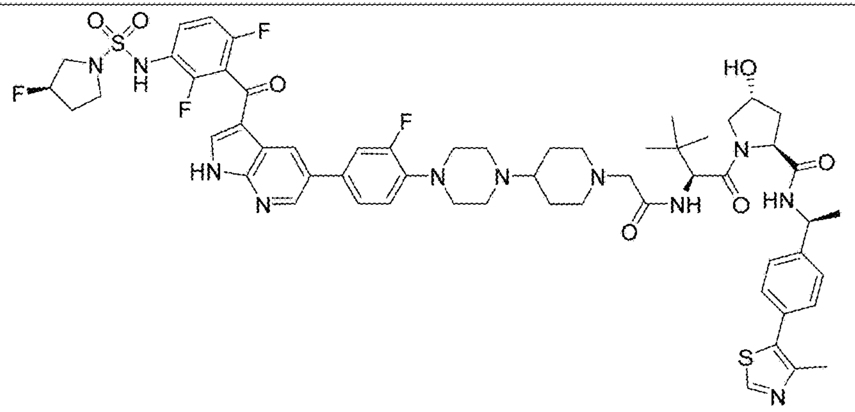 | (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)-2-fluorophenyl)piperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1170.86 | 3 |
| 451 | 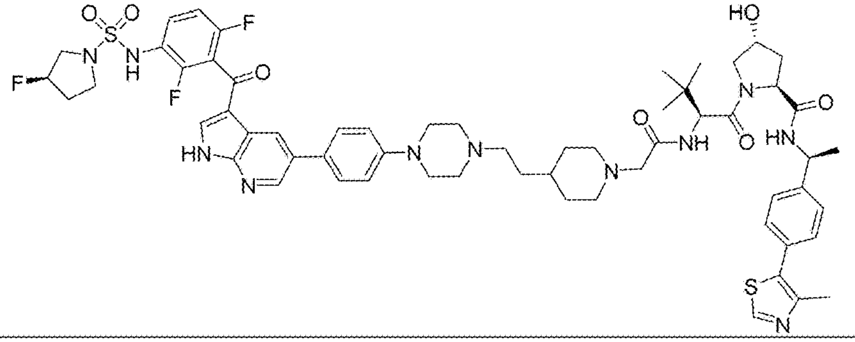 | (2S,4R)-1-((S)-2-(2-(4-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.91 | 3 |

FIG. 2A. Continued

| No. | Structure | Compound Name | MH+ | Synthetic Scheme |
|---|---|---|---|---|
| 452 | 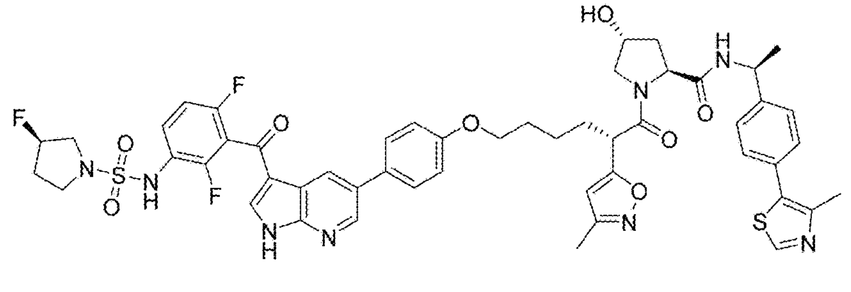 | (2S,4R)-1-((S)-6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoyl)-4-hydroxy-N-((S)-1-(4-(4-methylthiazol-5-yl)phenyl)ethyl)pyrrolidine-2-carboxamide | 1025.69 | Custom |
| 453 | 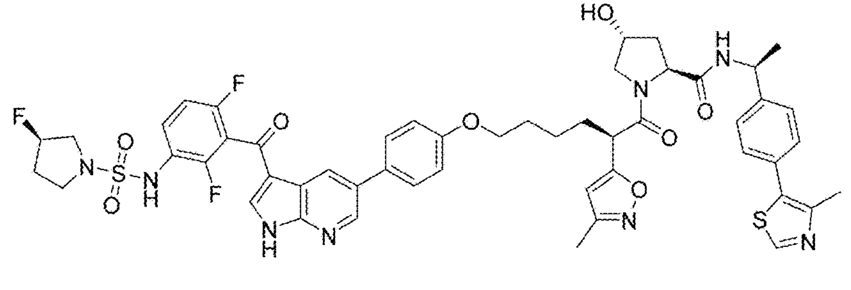 | (2S,4R)-1-((R)-6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoyl)-4-hydroxy-N-((S)-1-(4-(4-methylthiazol-5-yl)phenyl)ethyl)pyrrolidine-2-carboxamide | 1025.69 | Custom |
| 454 | 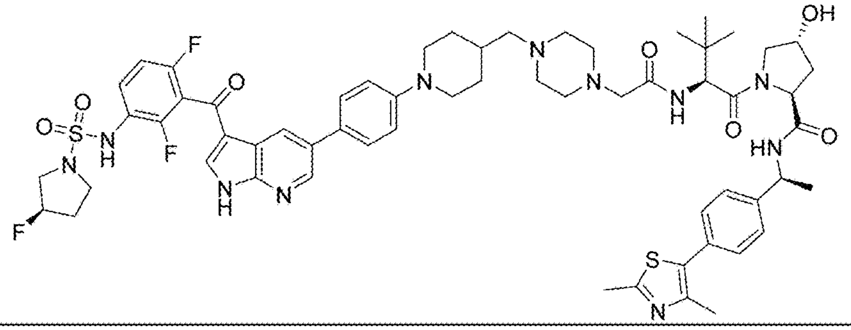 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-N-((S)-1-(4-(2,4-dimethylthiazol-5-yl)phenyl)ethyl)-4-hydroxypyrrolidine-2-carboxamide | 1180.91 | 17 |

FIG. 2A. Continued

| No. | Structure | Compound Name | MH+ | Synthetic Scheme |
|---|---|---|---|---|
| 455 | 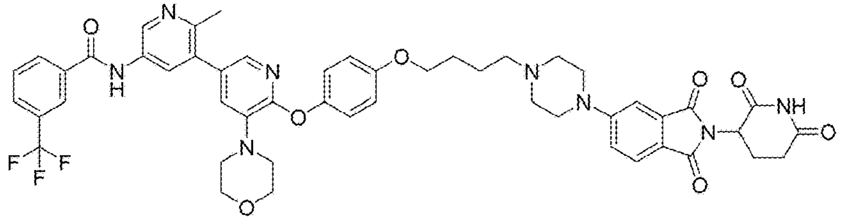 | N-(6'-(4-(4-(4-(2-(2,6-dioxopiperidin-3-yl)-1,3-dioxoisoindolin-5-yl)piperazin-1-yl)butoxy)phenoxy)-2-methyl-5'-morpholino-[3,3'-bipyridin]-5-yl)-3-(trifluoromethyl)benzamide | 947.72 | 16 |
| 456 | 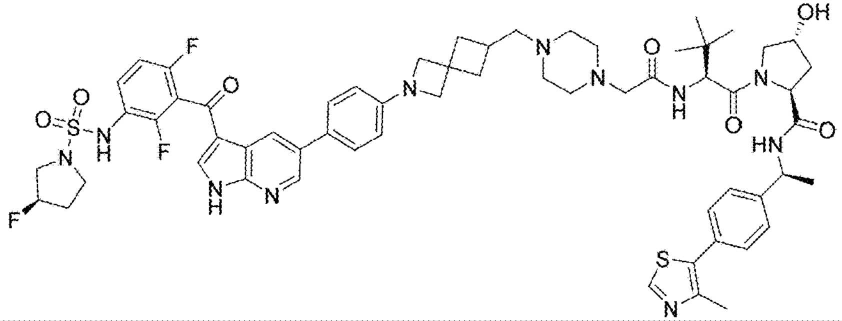 | (2S,4R)-1-((S)-2-(2-(4-((2-(4-(3-(2,6-difluoro-3-(((R)-3-fluoropyrrolidine)-1-sulfonamido)benzoyl)-1H-pyrrolo[2,3-b]pyridin-5-yl)phenyl)-2-azaspiro[3.3]heptan-6-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1178.89 | 3 |
| 457 | 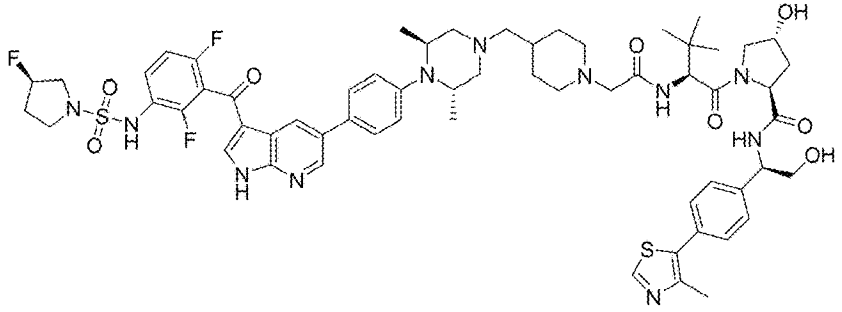 | (2S,4R)-1-((S)-2-(2-(4-(((3S,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1210.93 | 3 |

FIG. 2A. Continued

| No. | Structure | Compound Name | MH+ | Synthetic Scheme |
|---|---|---|---|---|
| 458 | 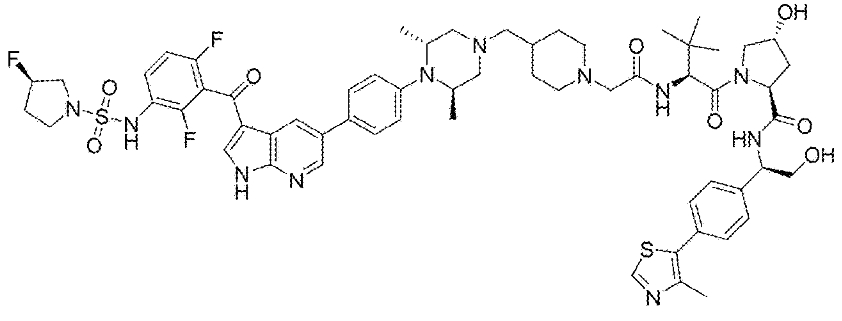 | (2S,4R)-1-((S)-2-(2-(4-(((3R,5R)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1210.93 | 3 |
| 459 | 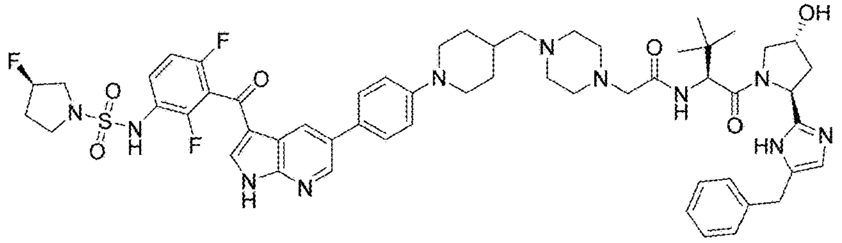 | N-((S)-1-((2S,4R)-2-(5-benzyl-1H-imidazol-2-yl)-4-hydroxypyrrolidin-1-yl)-3,3-dimethyl-1-oxobutan-2-yl)-2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamide | 1078.88 | Custom |
| 460 | 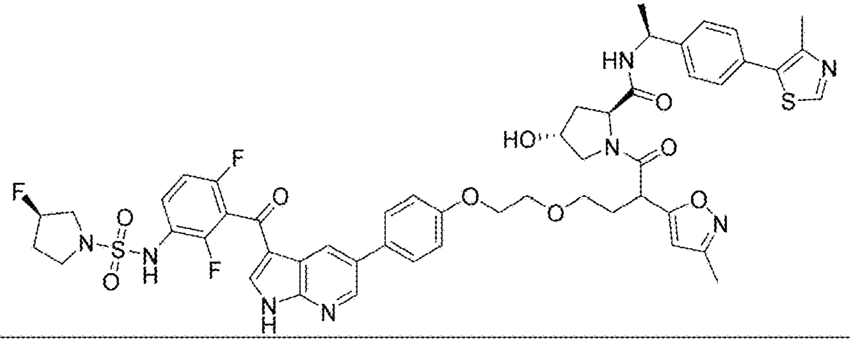 | (2S,4R)-1-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | 1041.69 | Custom |

FIG. 2A. Continued

| No. | Structure | Compound Name | MH+ | Synthetic Scheme |
|---|---|---|---|---|
| 461 | 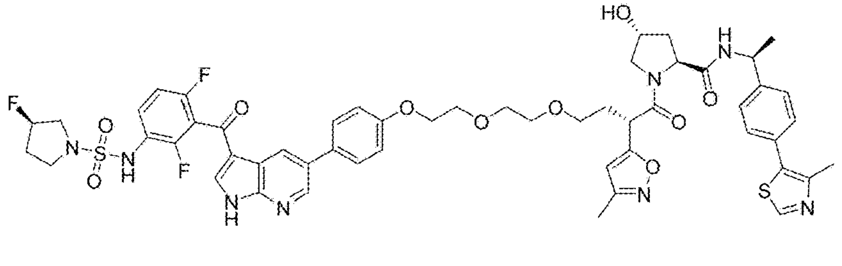 | (2S,4R)-1-((S)-4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | 1085.73 | Custom |
| 462 | 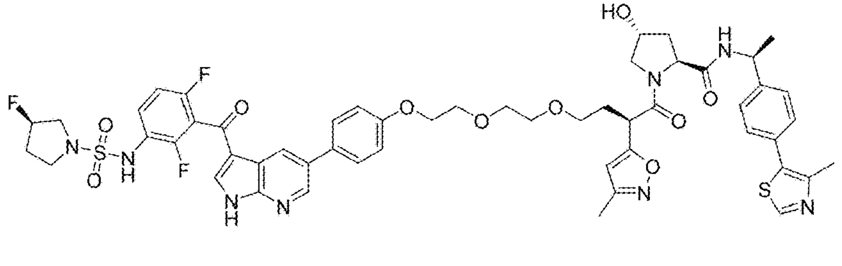 | (2S,4R)-1-((R)-4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | 1085.73 | Custom |
| 463 | 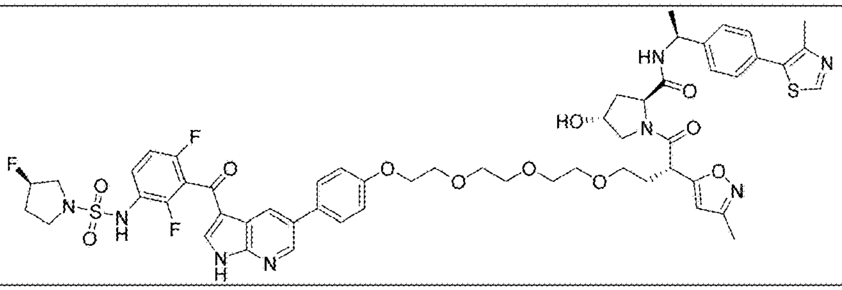 | (2S,4R)-1-((S)-4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | 1129.76 | Custom |

FIG. 2A. Continued

| No. | Structure | Compound Name | MH+ | Synthetic Scheme |
|---|---|---|---|---|
| 464 | 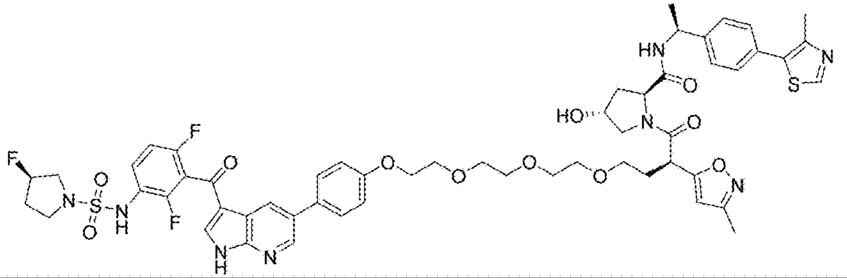 | (2S,4R)-1-((R)-4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoyl)-4-hydroxy-N-((S)-1-(4-(4-methylthiazol-5-yl)phenyl)ethyl)pyrrolidine-2-carboxamide | 1129.76 | Custom |
| 465 | 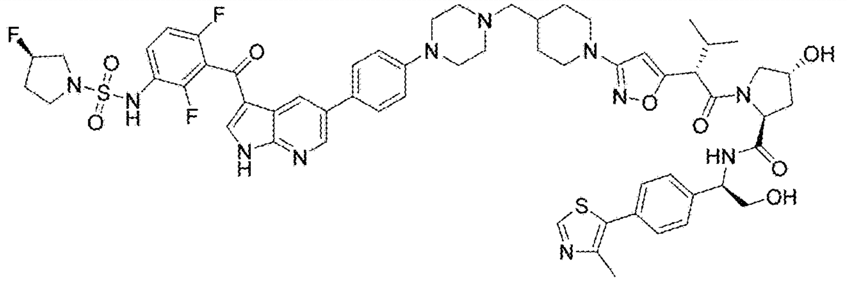 | (2S,4R)-1-((S)-2-(3-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1178.85<br>1178.85 | 13 |
| 466 | 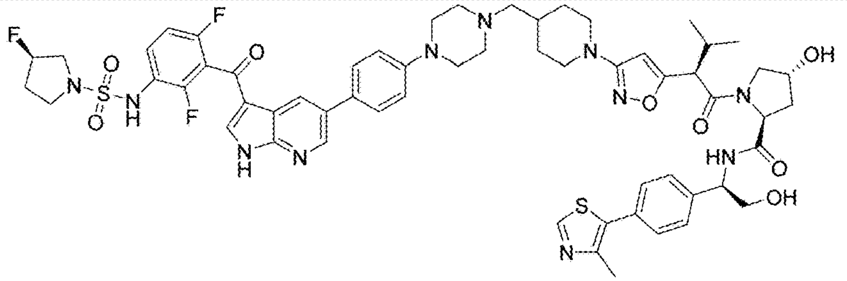 | (2S,4R)-1-((R)-2-(3-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1178.85<br>1178.85 | 13 |

FIG. 2A. Continued

| No. | Structure | Compound Name | MH+ | Synthetic Scheme |
|---|---|---|---|---|
| 467 | 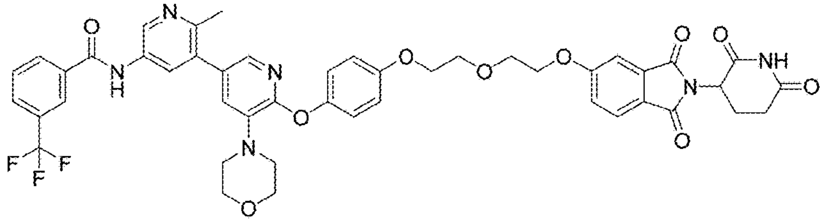 | N-(6'-(4-(2-(2-((2-(2,6-dioxopiperidin-3-yl)-1,3-dioxoisoindolin-5-yl)oxy)ethoxy)ethoxy)phenoxy)-2-methyl-5'-morpholino-[3,3'-bipyridin]-5-yl)-3-(trifluoromethyl)benzamide | 895.62 | 16 |
| 468 | 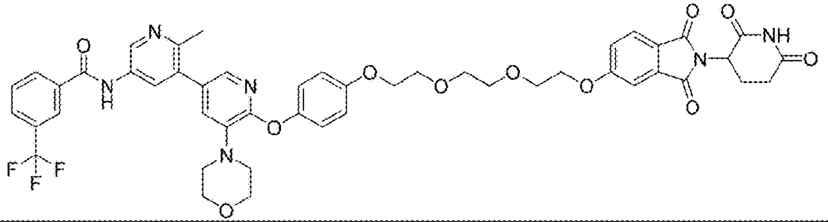 | N-(6'-(4-(2-(2-(2-((2-(2,6-dioxopiperidin-3-yl)-1,3-dioxoisoindolin-5-yl)oxy)ethoxy)ethoxy)ethoxy)phenoxy)-2-methyl-5'-morpholino-[3,3'-bipyridin]-5-yl)-3-(trifluoromethyl)benzamide | 939.66 | 16 |
| 469 | 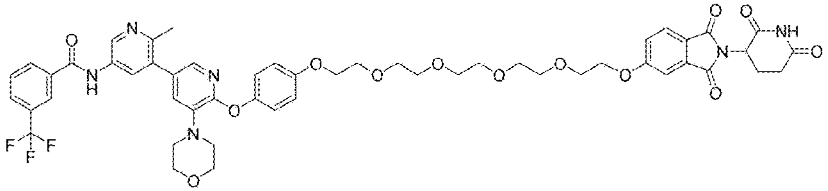 | N-(6'-(4-((14-((2-(2,6-dioxopiperidin-3-yl)-1,3-dioxoisoindolin-5-yl)oxy)-3,6,9,12-tetraoxatetradecyl)oxy)phenoxy)-2-methyl-5'-morpholino-[3,3'-bipyridin]-5-yl)-3-(trifluoromethyl)benzamide | 1027.73 | 16 |
| 470 | 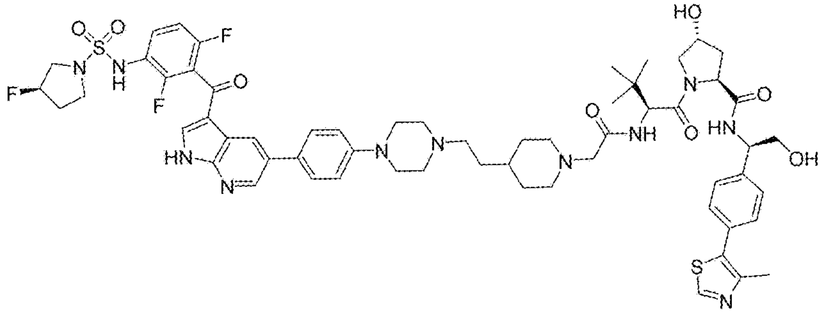 | (2S,4R)-1-((S)-2-(2-(4-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethyl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1196.9 | 3 |

FIG. 2A. Continued

| No. | Structure | Compound Name | MH+ | Synthetic Scheme |
|---|---|---|---|---|
| 471 | 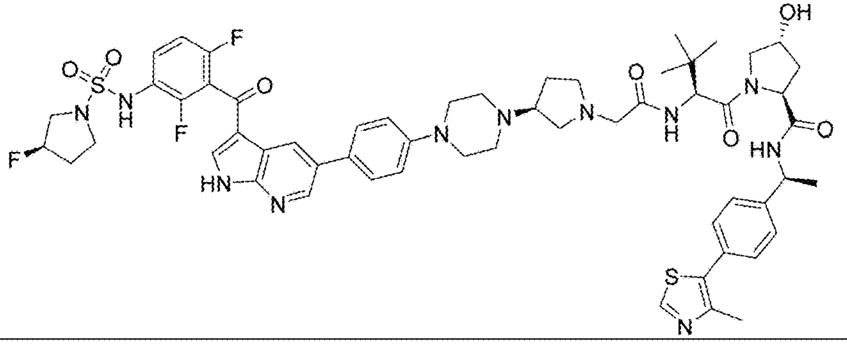 | (2S,4R)-1-((S)-2-(2-((S)-3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)pyrrolidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1138.85 | 3 |
| 472 | 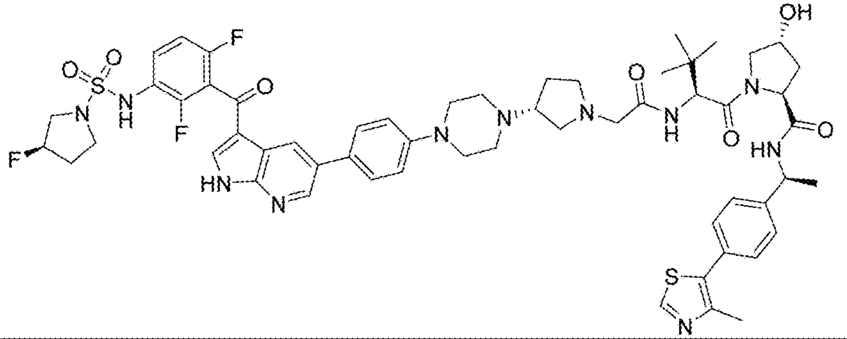 | (2S,4R)-1-((S)-2-(2-((R)-3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)pyrrolidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1138.85 | 3 |
| 473 | 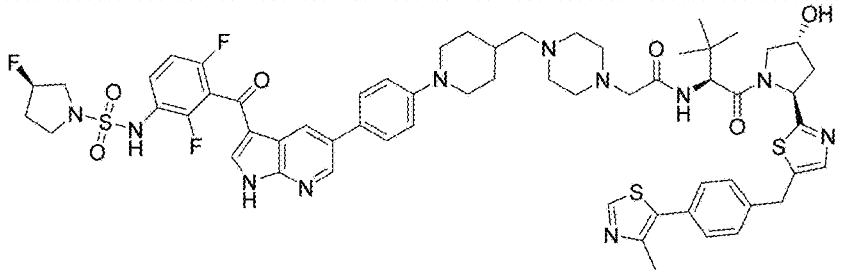 | 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N-((S)-1-((2S,4R)-4-hydroxy-2-(5-(4-(4-methylthiazol-5-yl)benzyl)thiazol-2-yl)pyrrolidin-1-yl)-3,3-dimethyl-1-oxobutan-2-yl)acetamide | 1192.85 | Custom |

FIG. 2A. Continued

| No. | Structure | Compound Name | MH+ | Synthetic Scheme |
|---|---|---|---|---|
| 474 | 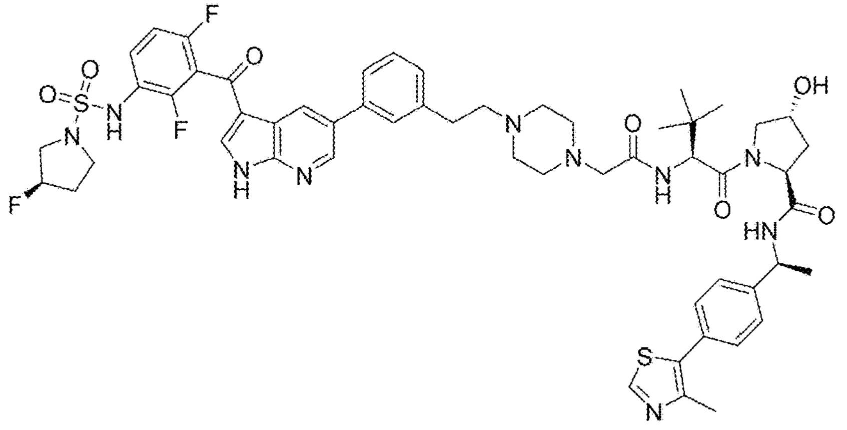 | (2S,4R)-1-((S)-2-(2-(4-(3-(3-(2,6-difluoro-3-(((R)-3-fluoropyrrolidine)-1-sulfonamido)benzoyl)-1H-pyrrolo[2,3-b]pyridin-5-yl)phenethyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1097.81 | 4 |
| 475 | 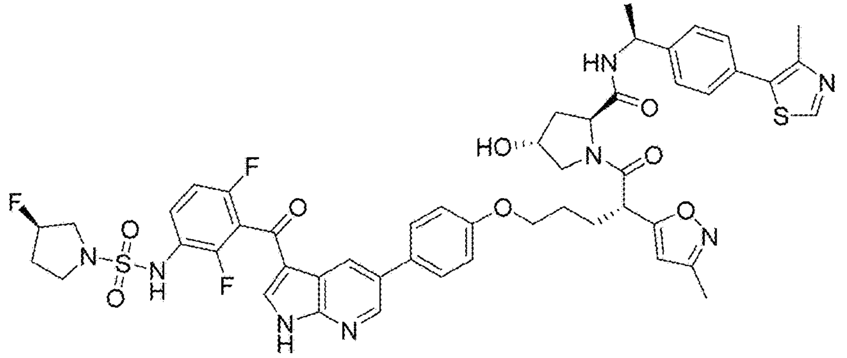 | (2S,4R)-1-((S)-5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoyl)-4-hydroxy-N-((S)-1-(4-(4-methylthiazol-5-yl)phenyl)ethyl)pyrrolidine-2-carboxamide | 1011.68 | Custom |

FIG. 2A. Continued

| No. | Structure | Compound Name | MH+ | Synthetic Scheme |
|---|---|---|---|---|
| 476 | 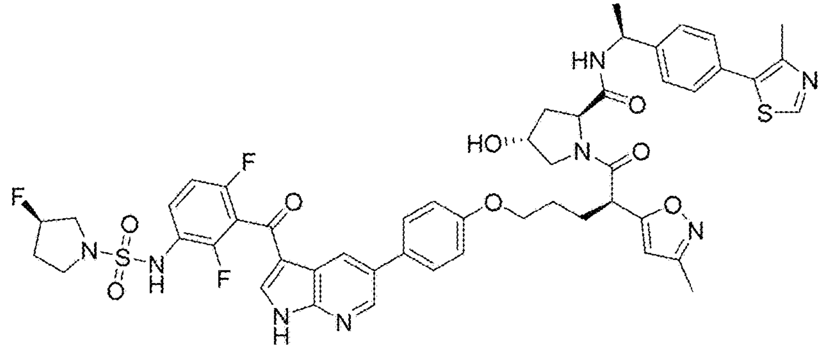 | (2S,4R)-1-((R)-5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoyl)-4-hydroxy-N-((S)-1-(4-(4-methylthiazol-5-yl)phenyl)ethyl)pyrrolidine-2-carboxamide | 1011.68 | Custom |
| 477 | 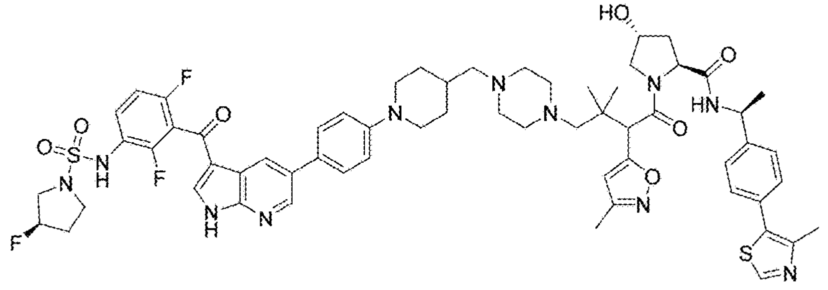 | (2S,4R)-1-(4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N-((S)-1-(4-(4-methylthiazol-5-yl)phenyl)ethyl)pyrrolidine-2-carboxamide | 1190.89 | Custom |
| 478 | 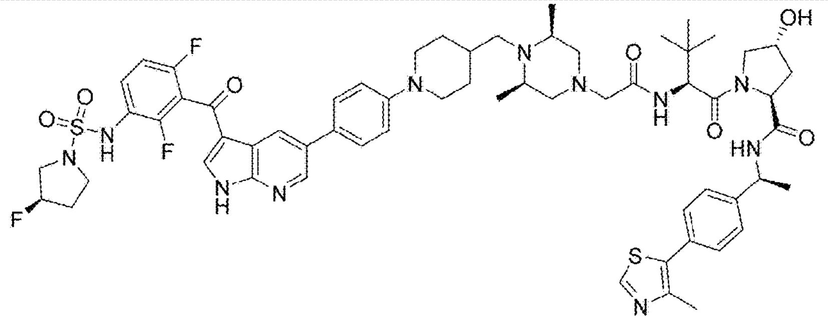 | (2S,4R)-1-((S)-2-(2-((3R,5S)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-3,5-dimethylpiperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.93 | 3 |

FIG. 2A. Continued

| No. | Structure | Compound Name | MH+ | Synthetic Scheme |
|---|---|---|---|---|
| 479 | 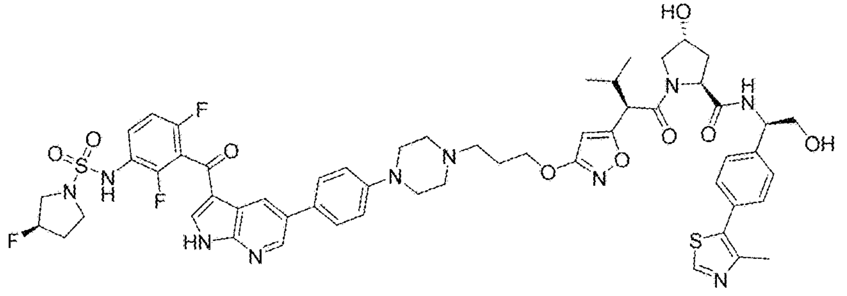 | (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1139.8 | Custom 2 |
| 480 | 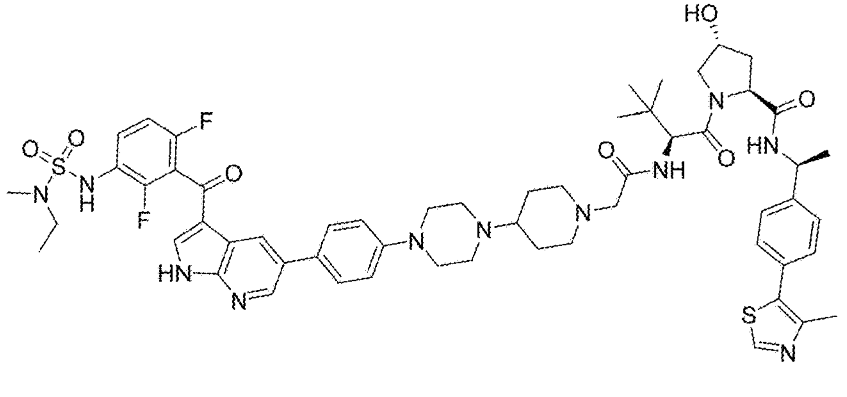 | (2S,4R)-1-((S)-2-(2-(4-(4-(4-(3-(3-((N-ethyl-N-methylsulfamoyl)amino)-2,6-difluorobenzoyl)-1H-pyrrolo[2,3-b]pyridin-5-yl)phenyl)piperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1122.87 | Custom |
| 481 | 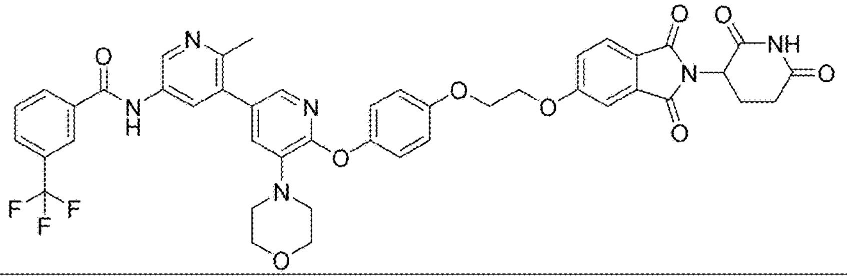 | N-(6'-(4-(2-((2-(2,6-dioxopiperidin-3-yl)-1,3-dioxoisoindolin-5-yl)oxy)ethoxy)phenoxy)-2-methyl-5'-morpholino-[3,3'-bipyridin]-5-yl)-3-(trifluoromethyl)benzamide | 851.58 | 16 |

FIG. 2A. Continued

| No. | Structure | Compound Name | MH+ | Synthetic Scheme |
| --- | --- | --- | --- | --- |
| 482 | 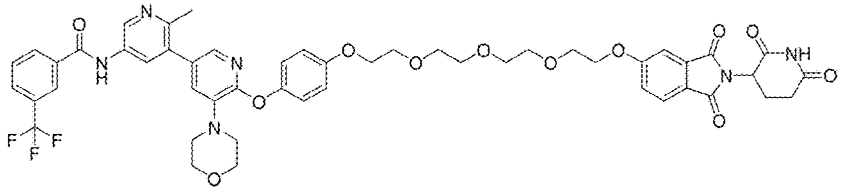 | N-(6'-(4-(2-(2-(2-(2-((2-(2,6-dioxopiperidin-3-yl)-1,3-dioxoisoindolin-5-yl)oxy)ethoxy)ethoxy)ethoxy)ethoxy)phenoxy)-2-methyl-5'-morpholino-[3,3'-bipyridin]-5-yl)-3-(trifluoromethyl)benzamide | 983.7 | 16 |
| 483 | 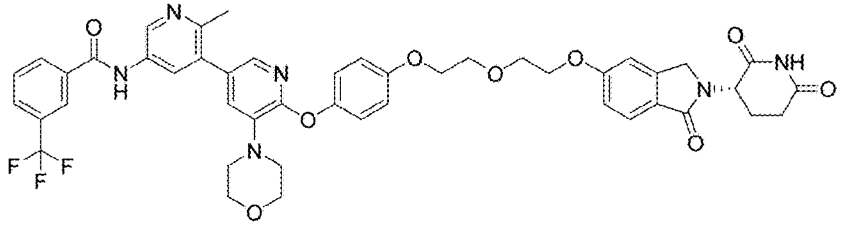 | (S)-N-(6'-(4-(2-(2-((2-(2,6-dioxopiperidin-3-yl)-1-oxoisoindolin-5-yl)oxy)ethoxy)ethoxy)phenoxy)-2-methyl-5'-morpholino-[3,3'-bipyridin]-5-yl)-3-(trifluoromethyl)benzamide | 881.64 | 16 |
| 484 | 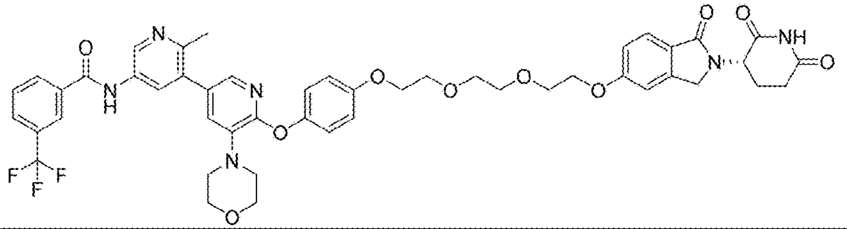 | (S)-N-(6'-(4-(2-(2-(2-((2-(2,6-dioxopiperidin-3-yl)-1-oxoisoindolin-5-yl)oxy)ethoxy)ethoxy)ethoxy)phenoxy)-2-methyl-5'-morpholino-[3,3'-bipyridin]-5-yl)-3-(trifluoromethyl)benzamide | 925.68 | 16 |
| 485 | 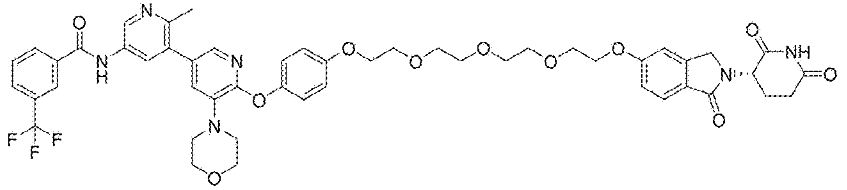 | (S)-N-(6'-(4-(2-(2-(2-(2-((2-(2,6-dioxopiperidin-3-yl)-1-oxoisoindolin-5-yl)oxy)ethoxy)ethoxy)ethoxy)ethoxy)phenoxy)-2-methyl-5'-morpholino-[3,3'-bipyridin]-5-yl)-3-(trifluoromethyl)benzamide | 969.71 | 16 |

FIG. 2A. Continued

| No. | Structure | Compound Name | MH+ | Synthetic Scheme |
|---|---|---|---|---|
| 486 | 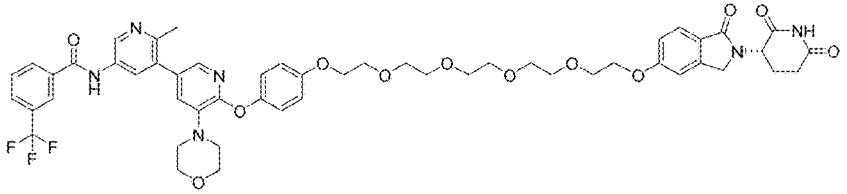 | (S)-N-(6'-(4-((14-((2-(2,6-dioxopiperidin-3-yl)-1-oxoisoindolin-5-yl)oxy)-3,6,9,12-tetraoxatetradecyl)oxy)phenoxy)-2-methyl-5'-morpholino-[3,3'-bipyridin]-5-yl)-3-(trifluoromethyl)benzamide | 1013.75 | 16 |
| 487 | 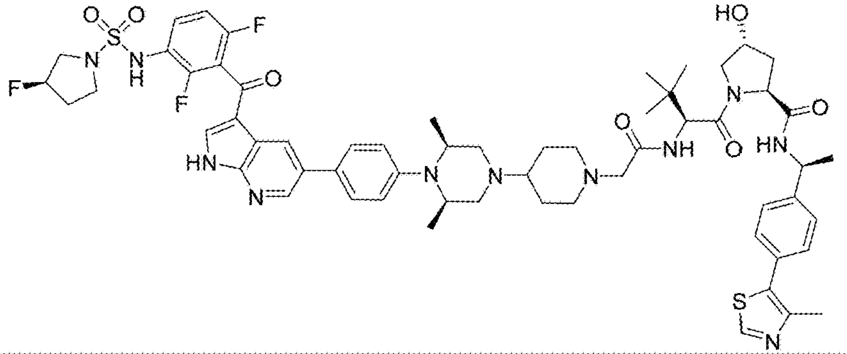 | (2S,4R)-1-((S)-2-(2-(4-((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.91 | 3 |
| 488 | 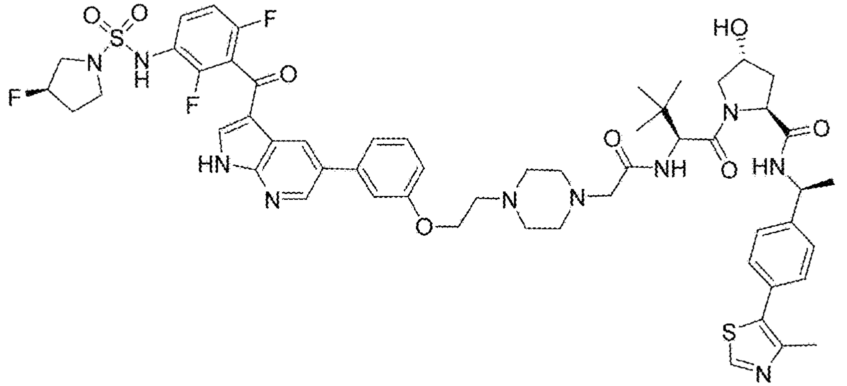 | (2S,4R)-1-((S)-2-(2-(4-(2-(3-(3-(2,6-difluoro-3-(((R)-3-fluoropyrrolidine)-1-sulfonamido)benzoyl)-1H-pyrrolo[2,3-b]pyridin-5-yl)phenoxy)ethyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1113.81 | 3 |

FIG. 2A. Continued

| No. | Structure | Compound Name | MH+ | Synthetic Scheme |
|---|---|---|---|---|
| 489 | 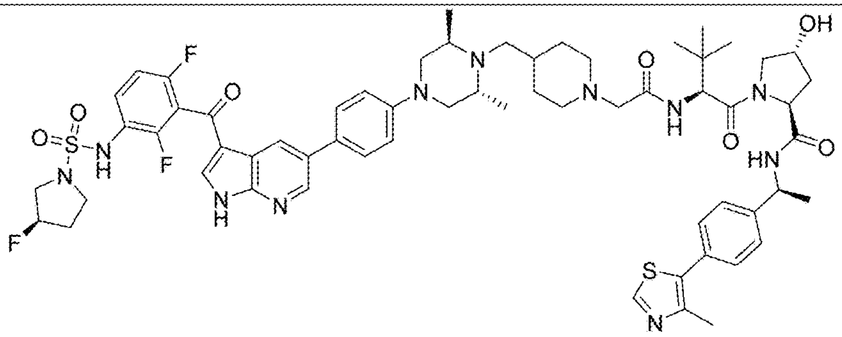 | (2S,4R)-1-((S)-2-(2-(4-(((2R,6R)-4-(4-(3-(2,6-difluoro-3-(((R)-3-fluoropyrrolidine)-1-sulfonamido)benzoyl)-1H-pyrrolo[2,3-b]pyridin-5-yl)phenyl)-2,6-dimethylpiperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.93 | 3 |
| 490 | 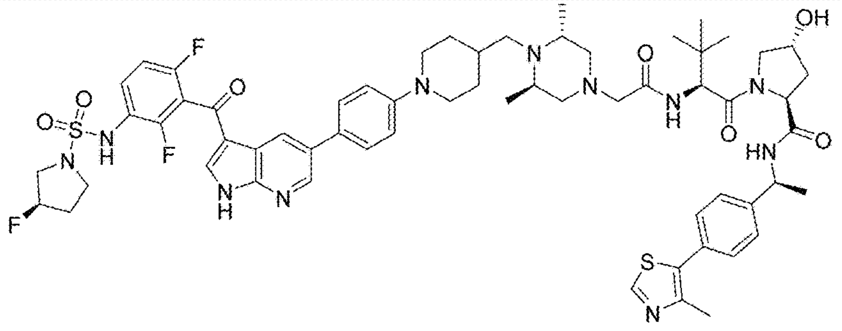 | (2S,4R)-1-((S)-2-(2-((3R,5R)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-3,5-dimethylpiperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.92 | 3 |

FIG. 2A. Continued

| No. | Structure | Compound Name | MH+ | Synthetic Scheme |
|---|---|---|---|---|
| 491 | 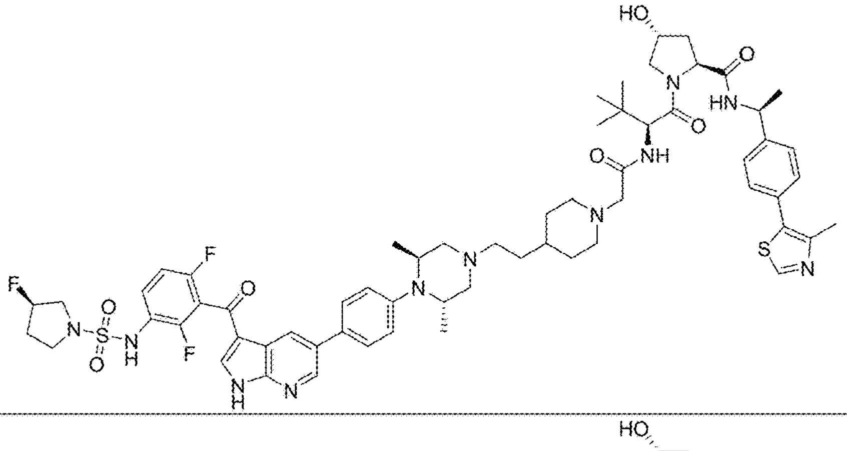 | (2S,4R)-1-((S)-2-(2-(4-(2-((3S,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)ethyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1208.94 | 3 |
| 492 | 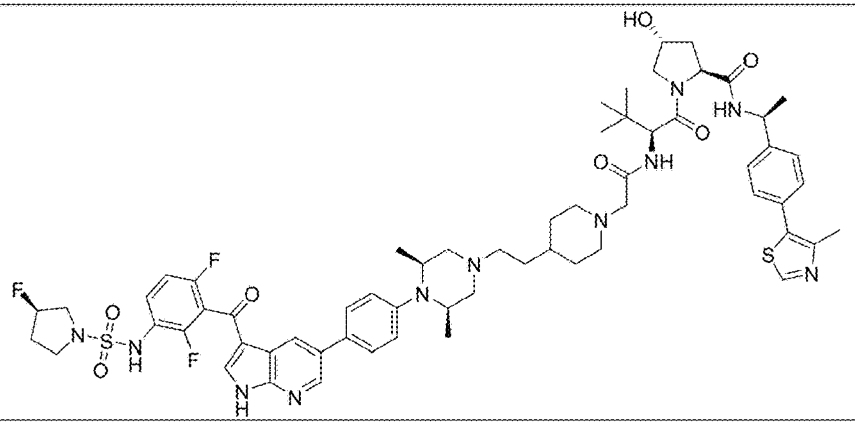 | (2S,4R)-1-((S)-2-(2-(4-(2-((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)ethyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1208.94 | 3 |

FIG. 2A. Continued

| No. | Structure | Compound Name | MH+ | Synthetic Scheme |
|---|---|---|---|---|
| 493 | 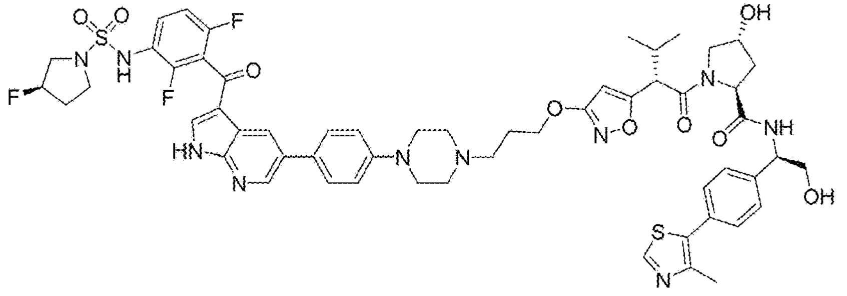 | (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1139.8 | Custom 2 |
| 494 | 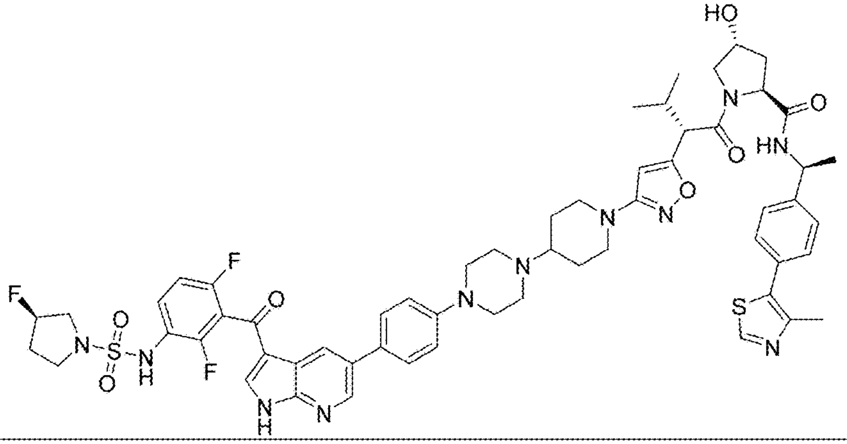 | (2S,4R)-1-((S)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1148.84 | 13 |

FIG. 2A. Continued

| No. | Structure | Compound Name | MH+ | Synthetic Scheme |
|---|---|---|---|---|
| 495 | 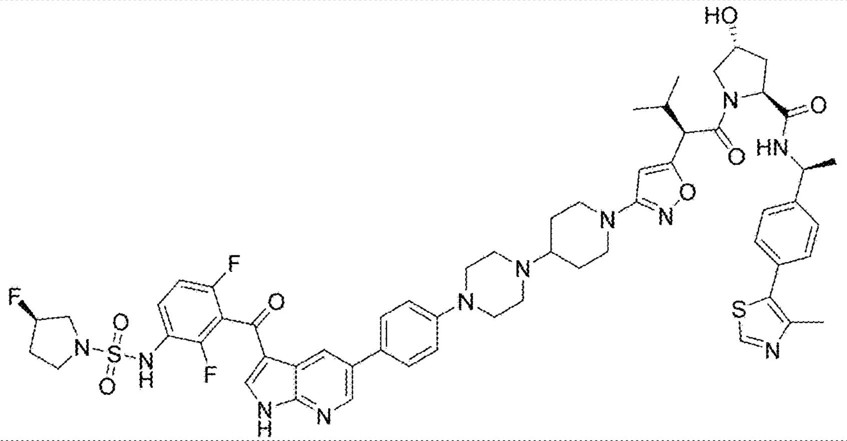 | (2S,4R)-1-((R)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 1148.83 | 13 |
| 496 | 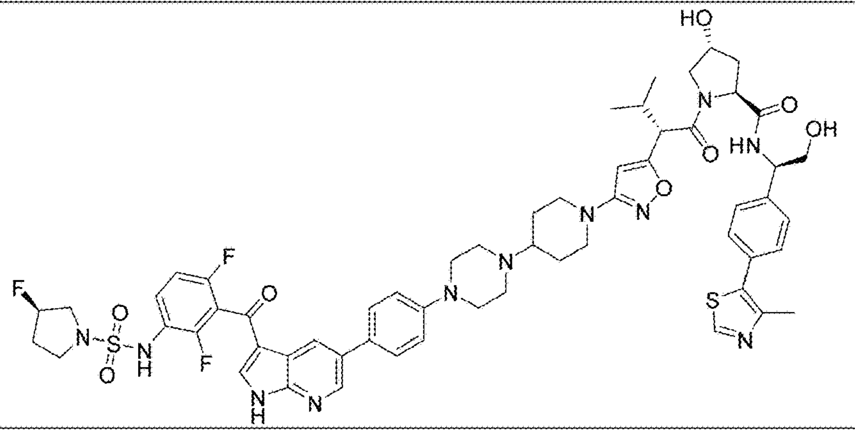 | (2S,4R)-1-((S)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1164.83 | 13 |

FIG. 2A. Continued

| No. | Structure | Compound Name | MH+ | Synthetic Scheme |
|---|---|---|---|---|
| 497 | 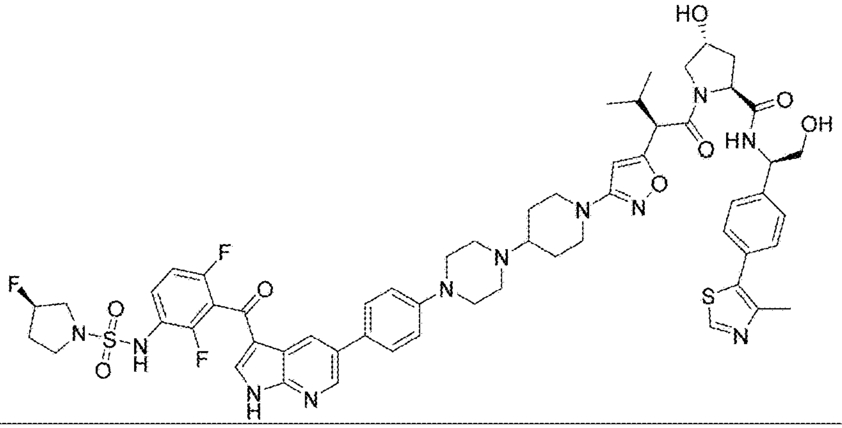 | (2S,4R)-1-((R)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1164.83 | 13 |
| 498 | 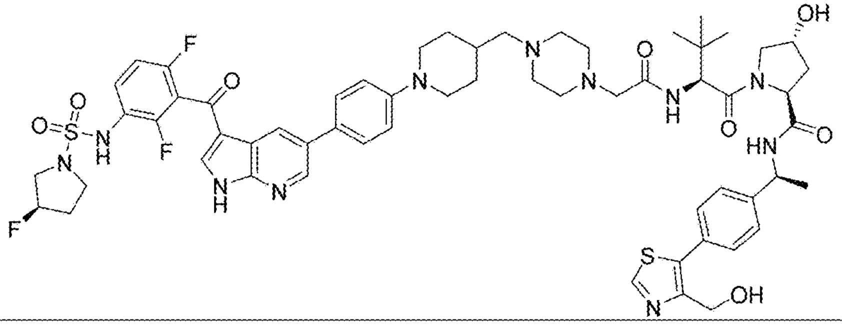 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-((S)-1-(4-(4-(hydroxymethyl)thiazol-5-yl)phenyl)ethyl)pyrrolidine-2-carboxamide | 1182.88 | 17 |

FIG. 2A. Continued

| No. | Structure | Compound Name | MH+ | Synthetic Scheme |
|---|---|---|---|---|
| 499 | 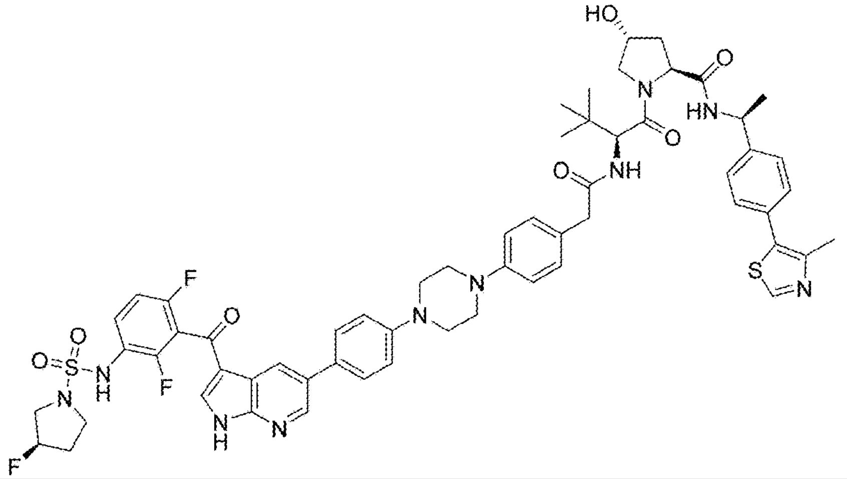 | (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)phenyl)acetamido)-3,3-dimethylbutanoyl)-4-hydroxy-N-((S)-1-(4-(4-methylthiazol-5-yl)phenyl)ethyl)pyrrolidine-2-carboxamide | 1145.82 | 3 |
| 500 | 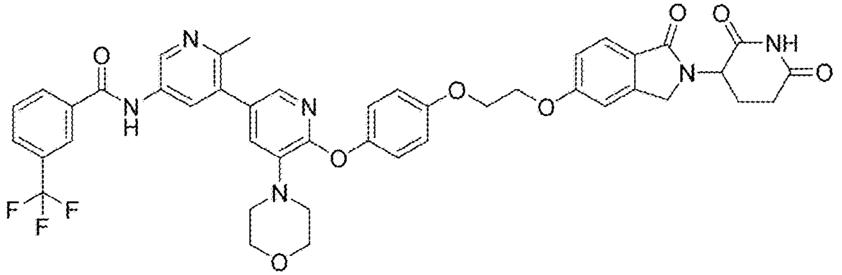 | N-(6'-(4-(2-((2-(2,6-dioxopiperidin-3-yl)-1-oxoisoindolin-5-yl)oxy)ethoxy)phenoxy)-2-methyl-5'-morpholino-[3,3'-bipyridin]-5-yl)-3-(trifluoromethyl)benzamide | 837.61 | 16 |

FIG. 2A. Continued

| No. | Structure | Compound Name | MH+ | Synthetic Scheme |
|---|---|---|---|---|
| 501 | 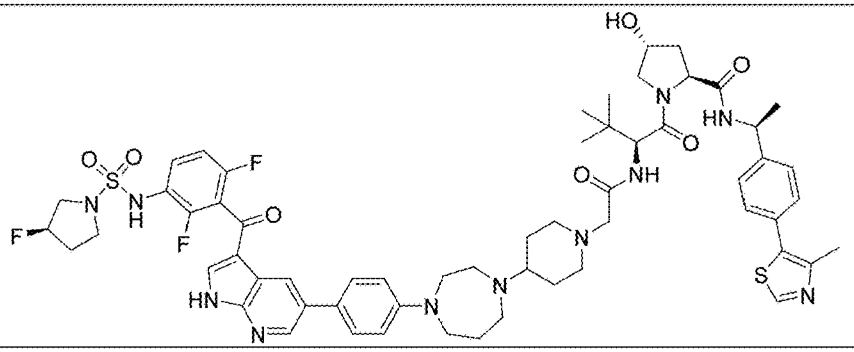 | (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)-1,4-diazepan-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.90 12 | 3 |
| 502 | 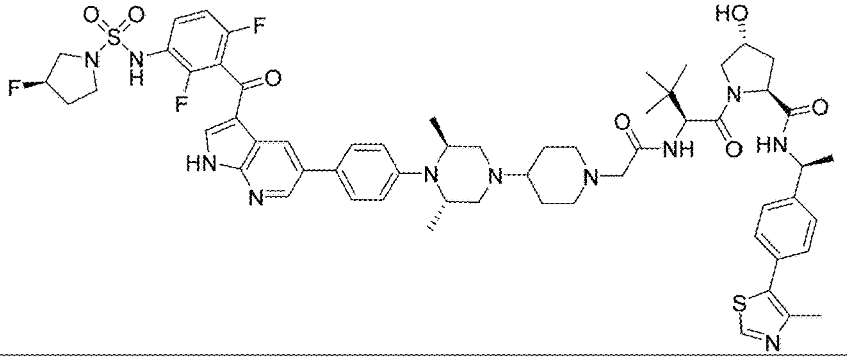 | (2S,4R)-1-((S)-2-(2-(4-((3S,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.91 | 3 |
| 503 | 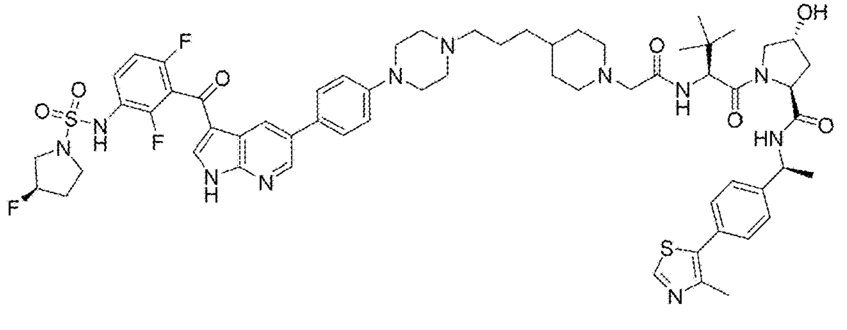 | (2S,4R)-1-((S)-2-(2-(4-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1194.92 | 3 |

FIG. 2A. Continued

| No. | Structure | Compound Name | MH+ | Synthetic Scheme |
|---|---|---|---|---|
| 504 | 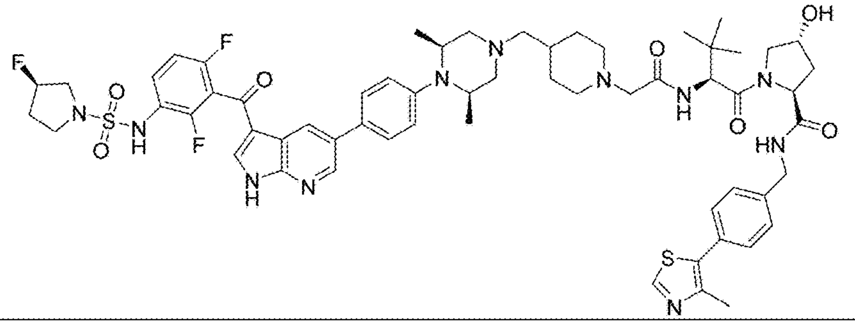 | (2S,4R)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1180.9 | 3 |
| 505 | 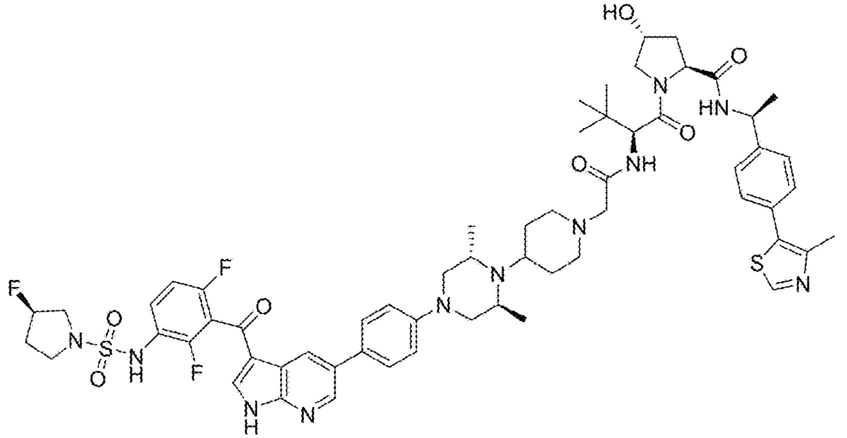 | (2S,4R)-1-((S)-2-(2-(4-((2S,6S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-2,6-dimethylpiperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.9 | 3 |

FIG. 2A. Continued

| No. | Structure | Compound Name | MH+ | Synthetic Scheme |
|---|---|---|---|---|
| 506 | 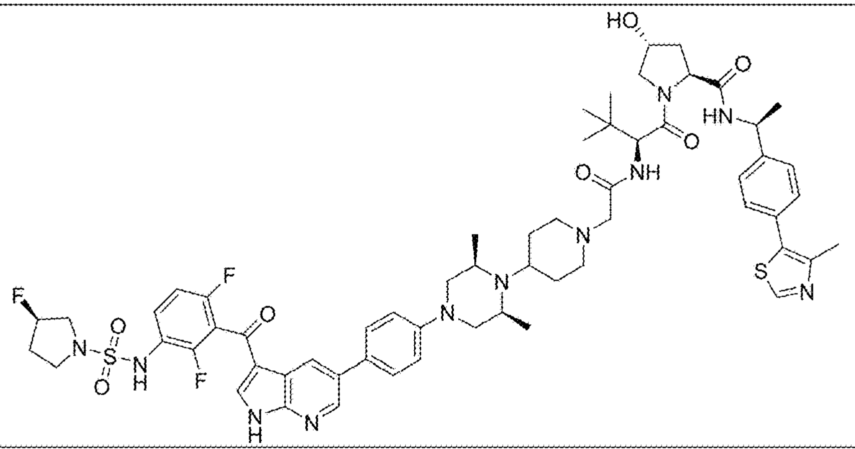 | (2S,4R)-1-((S)-2-(2-(4-((2S,6R)-4-(4-(3-(2,6-difluoro-3-(((R)-3-fluoropyrrolidine)-1-sulfonamido)benzoyl)-1H-pyrrolo[2,3-b]pyridin-5-yl)phenyl)-2,6-dimethylpiperazin-1-yl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1180.9 | 3 |
| 507 | 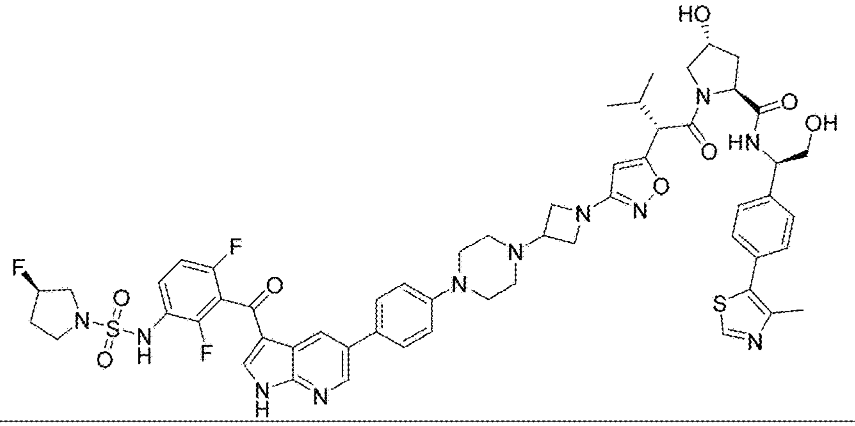 | (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1136.79 | Custom 2 |

FIG. 2A. Continued

| No. | Structure | Compound Name | MH+ | Synthetic Scheme |
|---|---|---|---|---|
| 508 | 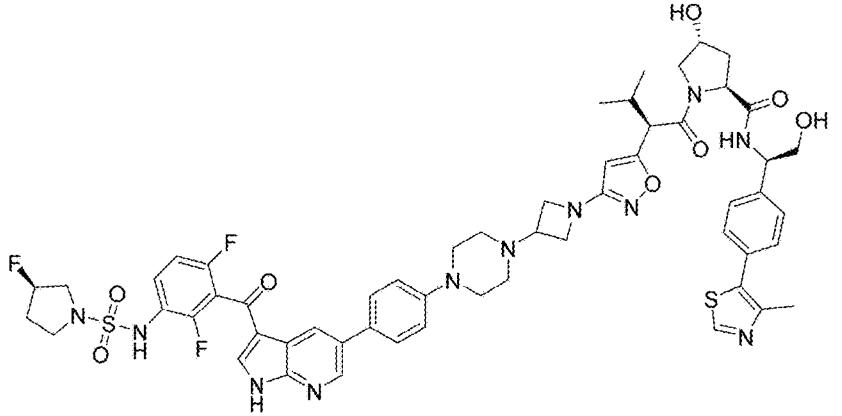 | (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide | 1136.79 | Custom 2 |
| 509 | 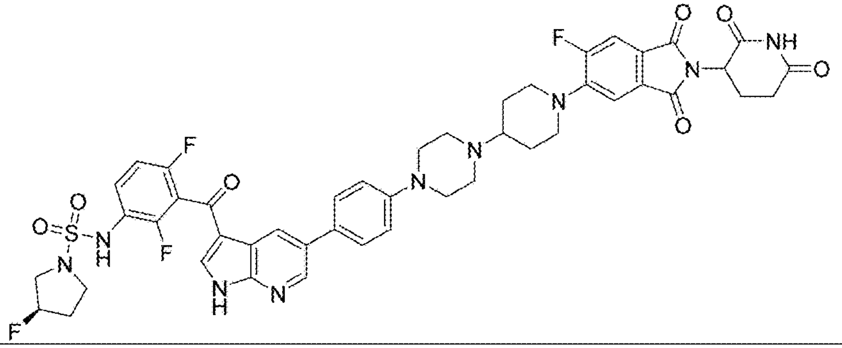 | (3R)-N-(3-(5-(4-(4-(1-(2-(2,6-dioxopiperidin-3-yl)-6-fluoro-1,3-dioxoisoindolin-5-yl)piperidin-4-yl)piperazin-1-yl)phenyl)-1H-pyrrolo[2,3-b]pyridine-3-carbonyl)-2,4-difluorophenyl)-3-fluoropyrrolidine-1-sulfonamide | 942.64 | 1 |
| 510 | 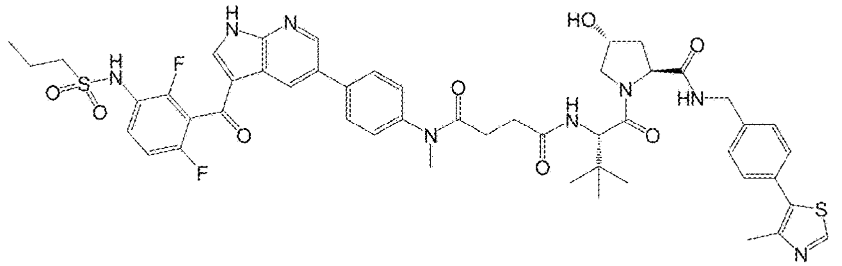 | | | B |

| No. | Structure | Compound Name | MH+ | Synthetic Scheme |
|---|---|---|---|---|
| 511 |  | | | E |
| 512 |  | | | F |
| 513 |  | | | E |

| No. | Structure | Compound Name | MH+ | Synthetic Scheme |
|---|---|---|---|---|
| 514 |  | | | A |
| 515 |  | | | G |
| 516 |  | | | F |

| No. | Structure | Compound Name | MH+ | Synthetic Scheme |
|---|---|---|---|---|
| 517 |  | | | A |

Table 1B. Exemplary protein targeting moieties and compounds of the present disclosure.

| No. | Structure | MH+ (1) [MH+ (2)] | Synthetic Scheme |
|---|---|---|---|
| 518 |  | 956.66 | 1 |
| 519 |  | 954.66 | 1 |

| | | | |
|---|---|---|---|
| 520 |  | 952.68 | 1 |
| 521 |  | 885.58 | 1 |
| 522 |  | 924.68<br>924.48 | 1 |

| | | | |
|---|---|---|---|
| 523 |  | 953.67 | 1 |
| 524 |  | 968.69 | 1 |
| 525 |  | 983.69 | 1 |

| | | | |
|---|---|---|---|
| 526 |  | 952.68 | 1 |
| 527 |  | 924.68<br>924.62<br>924.63 | 1 |

| | | | |
|---|---|---|---|
| 528 |  | 903.59 | 1 |
| 529 |  | 915.62 | 1 |

| | | | |
|---|---|---|---|
| 530 |  | 871.61 | 1 |
| 531 |  | 871.61 | 1 |

| | | | |
|---|---|---|---|
| 532 |  | | 1 |
| 533 |  | 913.59 | 1 |

| | | | |
|---|---|---|---|
| 534 |  | 964.64 | 1 |
| 535 |  | 978.66 | 1 |

| | | | |
|---|---|---|---|
| 536 |  | 911.56 | 1 |
| 537 |  | 925.45 | 1 |

| | | | |
|---|---|---|---|
| 538 |  | 896.43<br>896.44 | 1 |
| 539 |  | 923.47 | 1 |

| | | | |
|---|---|---|---|
| 540 |  | 992.54 | 1 |
| 541 |  | 1180.86 | 1 |
| 542 |  | 956.67 | 1 |

| | | | |
|---|---|---|---|
| 543 |  | 939.7 | 1 |
| 544 |  | 1184.64 | 1 |
| 545 |  | 997.5 | 1 |

| | | | |
|---|---|---|---|
| 546 |  | 1196.67 | 1 |
| 547 |  | 1196.67 | 1 |

| | | | |
|---|---|---|---|
| 548 |  | 938.5 | 1 |
| 549 |  | 817.31 | 1 |

| | | | |
|---|---|---|---|
| 550 |  | 1196.68 | 1 |
| 551 |  | 1240.7 | 1 |

| | | | |
|---|---|---|---|
| 552 |  | 936.48 | 1 |
| 553 |  | 869.43 | 1 |

| | | | |
|---|---|---|---|
| 554 |  | 1095.68 [1097.68] | 1 |
| 555 |  | 1238.72 | 1 |
| 556 |  | 954.5 | 1 |
| 557 |  | 885.53 | 1 |

| | | | |
|---|---|---|---|
| 558 |  | 1100.63 | 1 |
| 559 |  | 1232.73 | 1 |

| | | | |
|---|---|---|---|
| 560 |  | 1208.87 | 1 |
| 561 |  | 885.57 | 1 |
| 562 |  | 939.62 | 1 |

| | | | |
|---|---|---|---|
| 563 |  | 885.57 | 1 |
| 564 |  | 869.57 | 1 |
| 565 |  | 911.6 | 1 |

| | | | |
|---|---|---|---|
| 566 |  | 1298.86 | 1 |
| 567 |  | 1144.67 | 1 |
| 568 |  | 1188.7 | 1 |

| | | | |
|---|---|---|---|
| 569 |  | 1184.81 | 1 |
| 570 |  | 967.67 | 1 |

| | | | |
|---|---|---|---|
| 571 |  | 901.58 | 1 |
| 572 |  | 915.59 | 1 |
| 573 |  | 981.64 | 1 |
| 574 |  | 936.62 | 1 |

| | | | |
|---|---|---|---|
| 575 |  | 946.65 | 1 |
| 576 |  | 910.6 | 1 |
| 577 |  | 968.6 | 1 |

| | | | |
|---|---|---|---|
| 578 |  | 869.59 | 1 |
| 579 |  | 969.64 | 1 |
| 580 |  | 893.57 | 1 |

| | | | |
|---|---|---|---|
| 581 |  | 950.63<br>950.62 | 1 |
| 582 |  | 923.61<br>923.61 | 1 |
| 583 |  | 901.55 | 1 |

| | | | |
|---|---|---|---|
| 584 |  | 969.63 | 1 |
| 585 |  | 937.63 | 1 |

| | | | |
|---|---|---|---|
| 586 |  | 950.49 | 1 |
| 587 |  | 964.51 | 1 |
| 588 |  | 966.49 | 1 |

| | | | |
|---|---|---|---|
| 589 |  | 881.43<br>881.43 | 1 |
| 590 |  | 895.45 | 1 |
| 591 |  | 910.45 | 1 |

| | | | |
|---|---|---|---|
| 592 |  | 881.42 | 1 |
| 593 |  | 966.49 | 1 |
| 594 |  | 926.46 | 1 |

| | | | |
|---|---|---|---|
| 595 |  | 865.39<br>865.39 | 1 |
| 596 |  | 855.41<br>855.27 | 1 |

| | | | |
|---|---|---|---|
| 597 |  | 867.41 | 1 |
| 598 |  | 881.43 | 1 |

| | | | |
|---|---|---|---|
| 599 |  | 881.43 | 1 |
| 600 |  | 895.44 | 1 |
| 601 |  | 915.44<br>915.29<br>915.29 | 1 |

| | | | |
|---|---|---|---|
| 602 |  | 935.48 | 1 |
| 603 |  | 895.45 | 1 |
| 604 |  | 841.25<br>841.26 | 1 |

| | | | |
|---|---|---|---|
| 605 |  | 877.26 | 1 |
| 606 |  | 935.33 | 1 |
| 607 |  | 950.34 | 1 |

| | | | |
|---|---|---|---|
| 608 |  | 925.31 | 1 |
| 609 |  | 895.3 | 1 |

| | | | |
|---|---|---|---|
| 610 |  | 953.35<br>953.35 | 1 |
| 611 |  | 867.28 | 1 |

| | | | |
|---|---|---|---|
| 612 |  | 899.3 | 1 |
| 613 |  | 827.24 | 1 |

| | | | |
|---|---|---|---|
| 614 |  | 927.29 | 1 |
| 615 |  | 910.32 | 1 |
| 616 |  | 950.35 | 1 |

| | | | |
|---|---|---|---|
| 617 |  | 897.28 | 1 |
| 618 |  | 853.26 | 1 |
| 619 |  | 853.26 | 1 |

| | | | |
|---|---|---|---|
| 620 |  | 895.31 | 1 |
| 621 |  | 936.34<br>936.34 | 1 |

| | | | |
|---|---|---|---|
| 622 |  | 936.33<br>936.34 | 1 |
| 623 |  | 841.26 | 1 |

| | | | |
|---|---|---|---|
| 624 |  | 950.34 | 1 |
| 625 |  | 950.34 | 1 |
| 626 |  | 855.27 | 1 |

| | | | |
|---|---|---|---|
| 627 |  | 897.28 | 1 |
| 628 |  | 935.34 | 1 |
| 629 |  | 867.28<br>867.29<br>[869.2965] | 1 |

| | | | |
|---|---|---|---|
| 630 |  | 865.26 | 1 |
| 631 |  | 885.28 | 1 |

| | | | |
|---|---|---|---|
| 632 |  | 885.28 | 1 |
| 633 |  | 937.32 | 1 |

| | | | |
|---|---|---|---|
| 634 |  | 885.28 | 1 |
| 635 |  | 885.28 | 1 |

| | | | |
|---|---|---|---|
| 636 |  | 980.35 | 1 |
| 637 |  | 950.34 | 1 |

| | | | |
|---|---|---|---|
| 638 |  | 895.3 | 1 |
| 639 |  | 950.31 | 1 |

| | | | |
|---|---|---|---|
| 640 |  | 938.32 | 1 |
| 641 |  | | 1 |

| | | | |
|---|---|---|---|
| 642 |  | 894.97 | 1 |
| 643 |  | | 1 |

| | | | |
|---|---|---|---|
| 644 |  | | 1 |
| 645 |  | | 1 |

| | | | |
|---|---|---|---|
| 646 |  | 952.69 | 2 |
| 647 |  | 952.69 | 2 |

| | | | |
|---|---|---|---|
| 648 |  | 938.67 | 2 |
| 649 |  | 896.61 | 2 |

| | | | |
|---|---|---|---|
| 650 |  | 885.6 | 2 |
| 651 |  | 938.67 | 2 |

| | | | |
|---|---|---|---|
| 652 |  | 1041.76 | 2 |
| 653 |  | 896.62 | 2 |

| | | | |
|---|---|---|---|
| 654 |  | 950.59 | 2 |
| 655 |  | 950.63<br>950.48 | 2 |
| 656 |  | 898.44 | 2 |

| | | | |
|---|---|---|---|
| 657 |  | 899.44 | 2 |
| 658 |  | 1127.83 | 3 |

| | | | |
|---|---|---|---|
| 659 |  | 1141.85 | 3 |
| 660 |  | 1151.87 | 3 |

| | | | |
|---|---|---|---|
| 661 |  | 1151.87 | 3 |
| 662 |  | 1194.92 | 3 |

| | | | |
|---|---|---|---|
| 663 |  | 1170.87 | 3 |
| 664 |  | 1195.92 | 3 |

| | | | |
|---|---|---|---|
| 665 |  | 1166.88 | 3 |
| 666 |  | 1210.91 | 3 |

| | | | |
|---|---|---|---|
| 667 |  | 1210.91 | 3 |
| 668 |  | 1196.91 | 3 |

| | | | |
|---|---|---|---|
| 669 |  | 1196.91 | 3 |
| 670 |  | 1124.84 | 3 |

| | | | |
|---|---|---|---|
| 671 |  | 1145.91 | 3 |
| 672 |  | 1180.9 | 3 |

| | | | |
|---|---|---|---|
| 673 |  | 1161.82 | 3 |
| 674 |  | 1194.88 | 3 |

| | | | |
|---|---|---|---|
| 675 |  | 1196.9 | 3 |
| 676 |  | 1240.94 | 3 |

| | | | |
|---|---|---|---|
| 677 |  | 1194.93 | 3 |
| 678 |  | 1167.89 | 3 |

| | | | |
|---|---|---|---|
| 679 |  | 1284.98 | 3 |
| 680 |  | 1224.94 | 3 |

| | | | |
|---|---|---|---|
| 681 |  | 1154.86 | 3 |

| | | | |
|---|---|---|---|
| 682 |  | 1186.87 | 3 |

| | | | |
|---|---|---|---|
| 683 |  | 1181.89<br>1181.83 | 3 |
| 684 |  | 1197.90<br>1197.82 | 3 |

| | | | |
|---|---|---|---|
| 685 |  | 1162.82 | 3 |
| 686 |  | 1210.93 | 3 |

| | | | |
|---|---|---|---|
| 687 |  | 1180.86 | 3 |
| 688 |  | 924.61 | 3 |

| | | | |
|---|---|---|---|
| 689 |  | | 3 |
| 690 |  | 966.63 | 3 |

| | | | |
|---|---|---|---|
| 691 |  | 936.61<br>936.47 | 3 |

| | | | |
|---|---|---|---|
| 692 |  | 899.57 | 3 |

| | | | |
|---|---|---|---|
| 693 |  | 978.52 | 3 |

| | | | |
|---|---|---|---|
| 694 |  | 992.54 | 3 |

| | | | |
|---|---|---|---|
| 695 |  | 1184.65 | 3 |
| 696 |  | 1151.64 | 3 |

| | | | |
|---|---|---|---|
| 697 |  | 911.56 | 12 |
| 698 |  | 856.39 | 12 |

| | | | |
|---|---|---|---|
| 699 |  | 1184.81 | 12 |
| 700 |  | 915.6 | 12 |
| 701 |  | 910.6 | 12 |

| | | | |
|---|---|---|---|
| 702 |  | 952.65 | 12 |
| 703 |  | 858.41 | 12 |
| 704 |  | 926.46 | 12 |

| | | | |
|---|---|---|---|
| 705 |  | 895.44 | 12 |
| 706 |  | 865.25<br>865.26 | 12 |
| 707 |  | 896.3 | 12 |

| | | | |
|---|---|---|---|
| 708 |  | 882.28<br>882.28 | 12 |
| 709 |  | 940.31<br>940.31 | 12 |

| | | | |
|---|---|---|---|
| 710 |  | 896.3 | 12 |
| 711 |  | 955.33 | 12 |
| 712 |  | 940.31 | 12 |

| | | | |
|---|---|---|---|
| 713 |  | 858.23<br>858.24 | 12 |
| 714 |  | 948.33 | 12 |
| 715 |  | 935.33 | 12 |

| | | | |
|---|---|---|---|
| 716 |  | 860.25<br>860.25 | 12 |
| 717 |  | 911.3 | 12 |
| 718 |  | 884.3 | 12 |

| | | | |
|---|---|---|---|
| 719 |  | 871.27 | 12 |
| 720 |  | 857.24 | 12 |
| 721 |  | 842.25 | 12 |

| | | | |
|---|---|---|---|
| 722 |  | 828.23<br>828.22 | 12 |
| 723 |  | 952.37 | 12 |

| | | | |
|---|---|---|---|
| 724 |  | 881.29 | 12 |
| 725 |  | 840.27 | 12 |
| 726 |  | 948.33 | 12 |

| | | | |
|---|---|---|---|
| 727 |  | 950.35 | 12 |
| 728 |  | 842.24 | 12 |

| | | | |
|---|---|---|---|
| 729 |  | 842.24 | 12 |
| 730 |  | 926.29 | 12 |

| | | | |
|---|---|---|---|
| 731 |  | 828.22 | 12 |
| 732 |  | 909.31 | 12 |

| | | | |
|---|---|---|---|
| 733 |  | 950.34 | 12 |
| 734 |  | 926.29 | 12 |
| 735 |  | 842.24<br>842.26 | 12 |

| | | | |
|---|---|---|---|
| 736 |  | 910.31 | 12 |
| 737 |  | | 12 |

| | | | |
|---|---|---|---|
| 738 |  | | 12 |
| 739 |  | | 12 |

| | | | |
|---|---|---|---|
| 740 |  | | 12 |
| 741 |  | | 12 |
| 742 |  | 1156.91 | 15 |

| | | | |
|---|---|---|---|
| 743 |  | 1289.01 | 15 |
| 744 |  | 1200.93 | 15 |

| | | | |
|---|---|---|---|
| 745 |  | 1244.97 | 15 |
| 746 |  | 1112.87 | 15 |

| | | | |
|---|---|---|---|
| 747 |  | 954.75 | 16 |
| 748 |  | 1196.83 [1198.83] | 18 |

| | | | |
|---|---|---|---|
| 749 |  | 1196.83<br>[1198.83] | 18 |
| 750 |  | 1113.53 | 18 |

| | | | |
|---|---|---|---|
| 751 |  | 1113.53 | 18 |
| 752 |  | 1172.87 | Custom |

| | | | |
|---|---|---|---|
| 753 |  | 1122.81 | Custom |
| 754 |  | 1190.89 | Custom |

| | | | |
|---|---|---|---|
| 755 |  | 1190.89 | Custom |
| 756 |  | 1085.85 | Custom |

| | | | |
|---|---|---|---|
| 757 |  | 1122.4 | Custom |
| 758 |  | 782.36 | Custom |

| | | | |
|---|---|---|---|
| 759 |  | 1196.67 | Custom |
| 760 |  | 936.48<br>936.47 | Custom |
| 761 |  | 952.48 | Custom |

| | | | |
|---|---|---|---|
| 762 |  | 1283.85 | Custom |
| 763 |  | 1109.7 | Custom |

| | | | |
|---|---|---|---|
| 764 |  | 1175.8 | Custom |
| 765 |  | 1175.80<br>1175.81 | Custom |

| | | | |
|---|---|---|---|
| 766 |  | 885.42 | Custom |
| 767 |  | 896.45 | Custom |
| 768 |  | 869.32 | Custom |

| | | | |
|---|---|---|---|
| 769 |  | 1182.88 | Custom 1 |

| | | | |
|---|---|---|---|
| 770 |  | 1196.91<br>1196.89 | Custom 1 |

| | | | |
|---|---|---|---|
| 771 |  | 1182.88 | Custom 1 |

| | | | |
|---|---|---|---|
| 772 |  | 1196.91 | Custom 1 |

| | | | |
|---|---|---|---|
| 773 |  | 912.61 | Custom 1 |
| 774 |  | 1146.9 | Custom 4 |
| 775 |  | 1146.91 | Custom 4 |

| | | | |
|---|---|---|---|
| 776 |  | 1146.91 | Custom 4 |
| 777 |  | 1149.92 | Custom 4 |
| 778 |  | 1108.9983 [1110.902] | Custom 4 |

| | | | |
|---|---|---|---|
| 779 |  | 1186.83 [1188.83] | Custom 4 |
| 780 |  | 1125.9 | Custom 4 |

| | | | |
|---|---|---|---|
| 781 |  | 1165.92 | Custom 4 |
| 782 |  | 1139.93 | Custom 4 |

| | | | |
|---|---|---|---|
| 783 |  | 1196.91 | Custom 4 |
| 784 |  | 952.5 | Custom 4 |

| | | | |
|---|---|---|---|
| 785 |  | 950.48 | Custom 4 |
| 786 |  | 950.48 | Custom 4 |

| | | | |
|---|---|---|---|
| 787 |  | 954.49 | Custom 4 |
| 788 |  | 980.51 | Custom 5 |
| 789 |  | 980.52 | Custom 5 |

| | | | |
|---|---|---|---|
| 790 |  | 954.49 | Custom 6 |
| 791 |  | 954.49 | Custom 6 |
| 792 |  | 942.47 | Custom 7 |

| | | | |
|---|---|---|---|
| 793 |  | 942.47 | Custom 7 |
| 794 |  | 1046.47<br>1046.31 | |
| 795 |  | 1046.3 | |

Table 1C. Exemplary protein targeting moieties and compounds of the present disclosure.

| No. | Parent No. | Structure | Synthesis | Observed M/E+ (2+) [3+] |
|---|---|---|---|---|
| 796 | 99 |  | General Scheme Prodrug 1, synthesis described in detail | 2140.42 (1070.77) [714.21] |

| | | | | |
|---|---|---|---|---|
| 797 | 114 |  | General Scheme Prodrug 1 | 1887.26 (944.18) [629.81] |
| 798 | 114 |  | General Scheme Prodrug 1 | 2151.43 (1076.28) [717.88] |

| | | | | |
|---|---|---|---|---|
| 799 | 114 |  | General Scheme Prodrug 2, synthesis described in detail | 2179.44 (1090.29) [727.22] |
| 800 | 99 |  | General Scheme Prodrug 3, synthesis described in detail | 2154.45 (1077.79) [718.88] |

| | | | | |
|---|---|---|---|---|
| 801 | 99 |  | General Scheme Prodrug 4, synthesis described in detail | 2168.46 (1084.8) [723.56] |
| 802 | 114 |  | General Scheme Prodrug 5, synthesis described in detail | 2165.45 (1083.29) [722.55] |

| | | | | |
|---|---|---|---|---|
| 803 | 99 |  | General Scheme Prodrug 6, synthesis described in detail | 2168.45 (1084.79) [723.55] |
| 804 | 114 |  | General Scheme Prodrug 7 | 2192.47 (1096.8) [731.56] |

| | | | | |
|---|---|---|---|---|
| 805 | 114 |  | General Scheme Prodrug 11 | 2216.48 (1108.81) [739.57] |
| 806 | 226 |  | General Scheme Prodrug 1 | 2193.49 (1097.31) [731.9] |

| | | | | |
|---|---|---|---|---|
| 807 | 227 |  | General Scheme Prodrug 1 | 2193.47 (1097.3) [731.89] |
| 808 | 225 |  | General Scheme Prodrug 1 | 2153.62 (1077.41) [718.65] |

| | | | | |
|---|---|---|---|---|
| 809 | 243 |  | Esterification as described in General Scheme Prodrug 1, on mono-TBS-protected diol intermediate from General Scheme Prodrug 9 | 2223.49 (1112.31) [741.9] |
| 810 | 99 |  | General Scheme Prodrug 1 | 1523.97 (762.52) [508.69] |

| | | | | |
|---|---|---|---|---|
| 811 | 226 |  | General Scheme Prodrug 1 | 1577.04 (789.06) [526.39] |
| 812 | 227 |  | General Scheme Prodrug 7 | 2234.5 (1117.82) [745.57] |

| | | | | |
|---|---|---|---|---|
| 813 | 311 |  | Esterification as described in General Scheme Prodrug 1, on mono-TBS-protected diol intermediate from General Scheme Prodrug 9 | 2223.44 (1112.3) [741.89] |
| 814 | 227 |  | General Scheme Prodrug 7 | 2250.47 (1125.81) [750.89] |

| | | | | |
|---|---|---|---|---|
| 815 | 227 |  | General Scheme Prodrug 10, synthesis described in detail | 2251.46 (1126.29) [751.22] |
| 816 | 227 |  | General Scheme Prodrug 8, synthesis described in detail | 2248.5 (1124.81) [750.23] |

| | | | | |
|---|---|---|---|---|
| 817 | 100 |  | General Scheme Prodrug 1 | 2154.4 (1077.76) [718.86] |
| 818 | 316 |  | General Scheme Prodrug 9 | 2264.67 (1132.94) [755.67] |

| | | | | |
|---|---|---|---|---|
| 819 | 288 |  | General Scheme Prodrug 1 | 2150.37 (1075.75) [717.52] |
| 820 | 226 |  | General Scheme Prodrug 1 | 1533 (767.04) [511.7] |

| | | | | |
|---|---|---|---|---|
| 821 | 287 |  | General Scheme Prodrug 1 | 2150.38 (1075.75) [717.52] |
| 822 | 226 |  | General Scheme Prodrug 1 | 1400.9 (700.99) [467.67] |

| | | | | |
|---|---|---|---|---|
| 823 | 286 |  | General Scheme Prodrug 1 | 2136.34 (1068.72) [712.83] |
| 824 | 226 |  | General Scheme Prodrug 1 | 1445.11 (723.12) [482.44] |

| | | | | |
|---|---|---|---|---|
| 825 | 226 |  | General Scheme Prodrug 1 | 1489.14 (745.14) [497.12] |
| 826 | 320 |  | General Scheme Prodrug 1 | 2193.67 (1097.43) [731.99] |

| | | | | |
|---|---|---|---|---|
| 827 | 243 |  | General Scheme Prodrug 9, synthesis described in detail | 2264.7 (1132.95) [755.68] |
| 828 | 320 |  | General Scheme Prodrug 7, synthesis described in detail | 2234.68 (1117.94) [745.67] |

| | | | | |
|---|---|---|---|---|
| 829 | 419 |  | General Scheme Prodrug 1 | 2193.66 (1097.43) [731.99] |
| 830 | 226 |  | General Scheme Prodrug 1 | 1753.02 (877.06) [585.06] |

| | | | | |
|---|---|---|---|---|
| 831 | 226 |  | General Scheme Prodrug 1 | 1885.43 (943.3) [629.24] |
| 832 | 413 |  | General Scheme Prodrug 1 | 2203.63 (1102.42) [735.32] |

| | | | | |
|---|---|---|---|---|
| 833 | 414 |  | General Scheme Prodrug 1 | 2203.63 (1102.42) [735.32] |
| 834 | 331 |  | General Scheme Prodrug 1 | 2203.63 (1102.41) [735.32] |

| | | | | |
|---|---|---|---|---|
| 835 | 332 |  | General Scheme Prodrug 1 | 2203.63 (1102.41) [735.32] |
| 836 | 504 |  | General Scheme Prodrug 1 | 2221.68 (1111.44) [741.34] |

| | | | | |
|---|---|---|---|---|
| 837 | 451 |  | General Scheme Prodrug 1 | 2221.68 (1111.43) [741.34] |
| 838 | 239 |  | General Scheme Prodrug 7 | 2248.69 (1124.95) [750.35] |

| | | | | |
|---|---|---|---|---|
| 839 | 309 |  | General Scheme Prodrug 1 | 1839.34 (920.26) [613.87] |
| 840 | 418 |  | General Scheme Prodrug 9 | 2250.66 (1125.93) [751] |

| | | | | |
|---|---|---|---|---|
| 841 | 429 |  | General Scheme Prodrug 12 | 1981.44 (991.31) [661.24] |
| 842 | 243 |  | General Scheme Prodrug 9, synthesis described in detail | 2278.71 (1139.96) [760.35] |

| | | | | |
|---|---|---|---|---|
| 843 | 408 |  | General Scheme Prodrug 1 | not observed (1089.55) [726.55] |
| 844 | 239 |  | General Scheme Prodrug 1 | not observed (1103.8) [736.25] |

| | | | | |
|---|---|---|---|---|
| 845 | 409 |  | General Scheme Prodrug 1 | not observed (1090.25) [727.2] |
| 846 | 457 |  | General Scheme Prodrug 9 | 2292.73 (1146.97) [765.02] |

| | | | | |
|---|---|---|---|---|
| 847 | 458 |  | General Scheme Prodrug 9 | 2292.73 (1146.97) [765.02] |
| 848 | 360 |  | General Scheme Prodrug 1 | 2235.71 (1118.45) [746.01] |

| | | | | |
|---|---|---|---|---|
| 849 | 519 |  | General Scheme Prodrug 12 | 2011.16 (1006.11) [671.07] |
| 850 | 418 |  | General Scheme Prodrug 9 | 1810.07 (906.06) [604.37] |

| | | | | |
|---|---|---|---|---|
| 851 | 243 |  | General Scheme Prodrug 9 | 2280.59 (1140.88) [760.95] |
| 852 | 243 |  | General Scheme Prodrug 10 | 2281.54 (1141.35) [761.26] |

| | | | | |
|---|---|---|---|---|
| 853 | 243 |  | General Scheme Prodrug 10 | 2265.55 (1133.35) [755.93] |
| 854 | 243 |  | General Scheme Prodrug 9 | 2294.58 (1147.87) [765.61] |

| | | | | |
|---|---|---|---|---|
| 855 | 497 |  | General Scheme Prodrug 9, but acylating the unprotected diol selectively at the primary alcohol (no TBS protection) | 2246.52 (1123.84) [749.59] |
| 856 | 527 |  | General Scheme Prodrug 12 | 1981.37 (991.25) [661.19] |

| | | | | |
|---|---|---|---|---|
| 857 | 522 |  | General Scheme Prodrug 15, synthesis described in detail | 1981.36 (991.23) [661.18] |
| 858 | 96 |  | General Scheme Prodrug 12 | 1970.1 (985.58) [657.39] |

| | | | | |
|---|---|---|---|---|
| 859 | 522 |  | General Scheme Prodrug 15 | 1540.87 (770.95) [514.3] |
| 860 | 522 |  | General Scheme Prodrug 14, synthesis described in detail | 1995.17 (998.11) [665.74] |

| | | | | |
|---|---|---|---|---|
| 861 | 522 |  | General Scheme Prodrug 14 | 1554.88 (777.95) [518.97] |
| 862 | 522 |  | General Scheme Prodrug 12, synthesis described in detail | 1981.18 (991.12) [661.08] |

| | | | | |
|---|---|---|---|---|
| 863 | 536 |  | General Scheme Prodrug 12 | 1992.91 (996.96) [664.98] |
| 864 | 536 |  | General Scheme Prodrug 15 | 1993.18 (997.11) [665.07] |

| | | | | |
|---|---|---|---|---|
| 865 | 522 |  | General Scheme Prodrug 13, synthesis described in detail | 2008.93 (1004.97) [670.31] |
| 866 | 522 |  | General Scheme Prodrug 13 | 1568.7 (784.86) [523.58] |

| | | | | |
|---|---|---|---|---|
| 867 | 596 |  | General Scheme Prodrug 12 | 1911.85 (956.43) [637.96] |
| 868 | 579 |  | General Scheme Prodrug 12 | 1979.9 (990.46) [660.64] |

| | | | | |
|---|---|---|---|---|
| 869 | 537 |  | General Scheme Prodrug 12 | 1992.89 (996.95) [664.97] |
| 870 | 540 |  | General Scheme Prodrug 12 | 2010.91 (1005.96) [670.98] |

| | | | | |
|---|---|---|---|---|
| 871 | 593 |  | General Scheme Prodrug 12 | 2022.91 (1011.96) [674.98] |
| 872 | 586 |  | General Scheme Prodrug 12 | not observed (1004.3) [not observed ] |

| | | | | |
|---|---|---|---|---|
| 873 | 596 |  | General Scheme Prodrug 14 | 1925.6 (963.45) [642.4] |

FIG. 2D

Table 1D. Exemplary protein targeting moieties and compounds of the present disclosure.

| No. | Structure | Compound Name | MH+ | Synthetic Scheme |
|---|---|---|---|---|
| 96 | 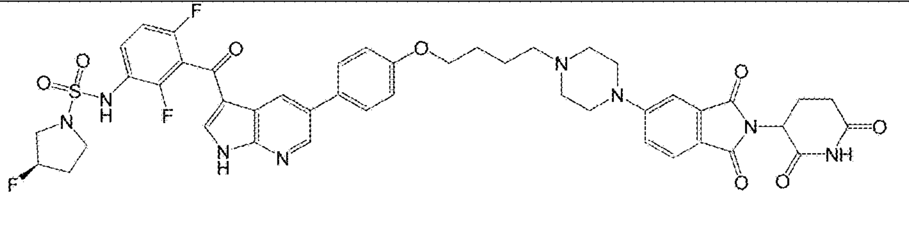 | (3R)-N-(3-(5-(4-(4-(4-(2-(2,6-dioxopiperidin-3-yl)-1,3-dioxoisoindolin-5-yl)piperazin-1-yl)butoxy)phenyl)-1H-pyrrolo[2,3-b]pyridine-3-carbonyl)-2,4-difluorophenyl)-3-fluoropyrrolidine-1-sulfonamide | 913.53 | 2 |
| 99 | 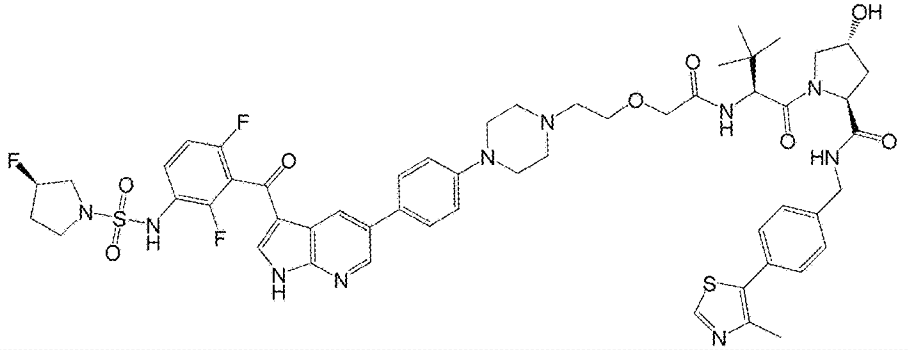 | (2S,4R)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-(4-(4-methylthiazol-5-yl)benzyl)pyrrolidine-2-carboxamide | 1099.68 | 3 |

FIG. 2D. Continued

| | | | | |
|---|---|---|---|---|
| 100 | 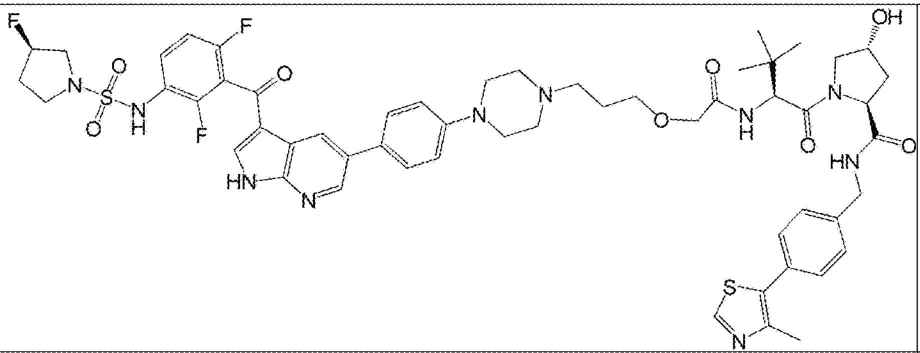 | (2S,4R)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide | 1113.38 | 3 |
| 114 | 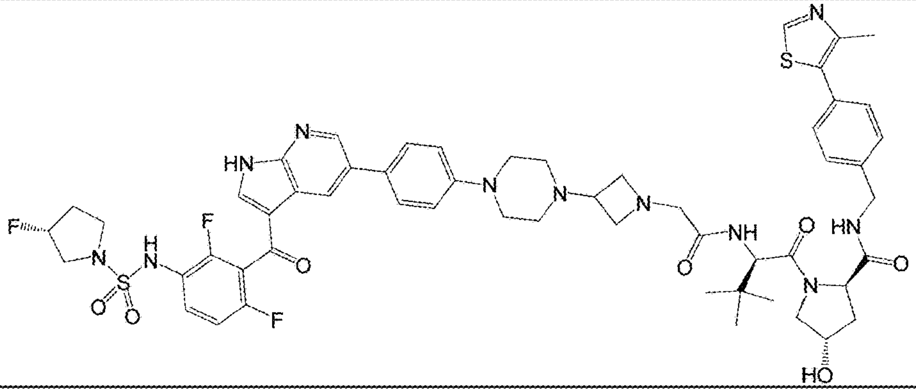 | (2S,4R)-1-((R)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide | 1110.70 | 4 |
| 225 | 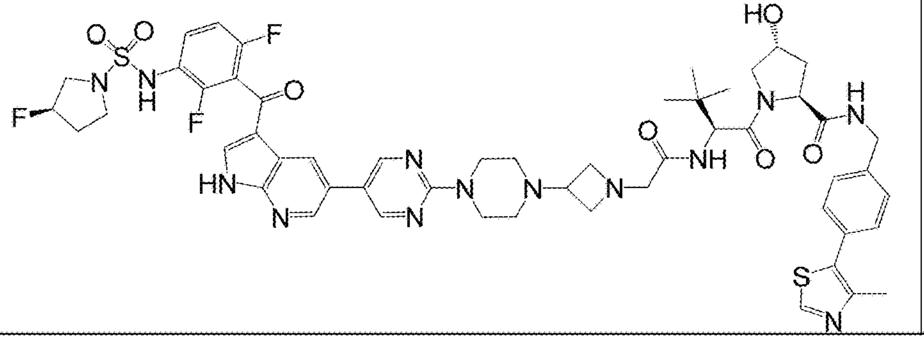 | (2S,4R)-1-((S)-2-(2-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide | 1112.69 | 3 |

FIG. 2D. Continued

| | | | | |
|---|---|---|---|---|
| 226 | 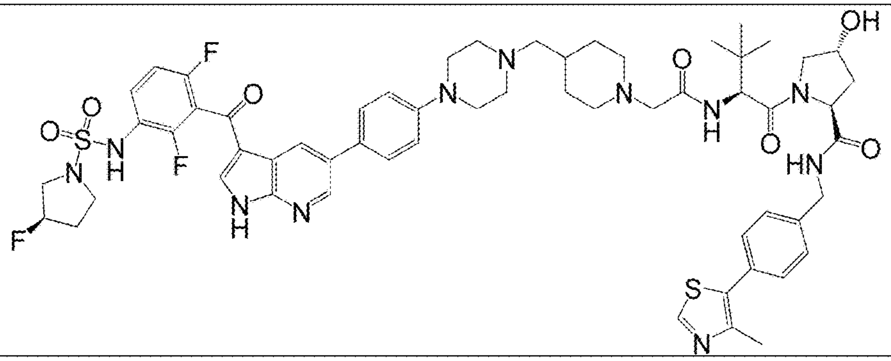 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1152.76 | 3 |
| 227 | 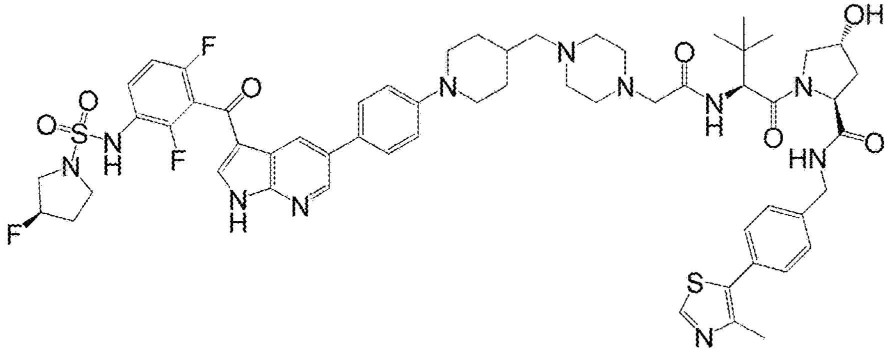 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide | 1152.80 | 3 |
| 231 | 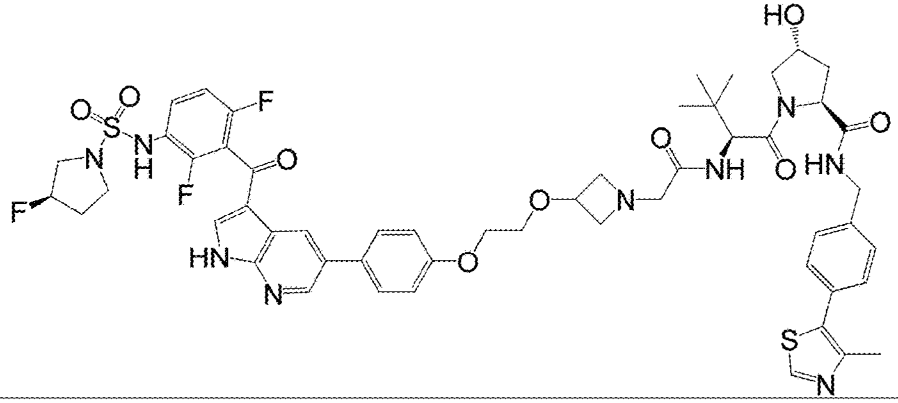 | (2S,4R)-1-((S)-2-(2-(3-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)azetidin-1-yl)acetamido)-3,3-dimethylbutanoyl)-4-hydroxy-N-(4-(4-methylthiazol-5-yl)benzyl)pyrrolidine-2-carboxamide | 1086.65 | 3 |

FIG. 2D. Continued

| | | | | |
|---|---|---|---|---|
| 239 | 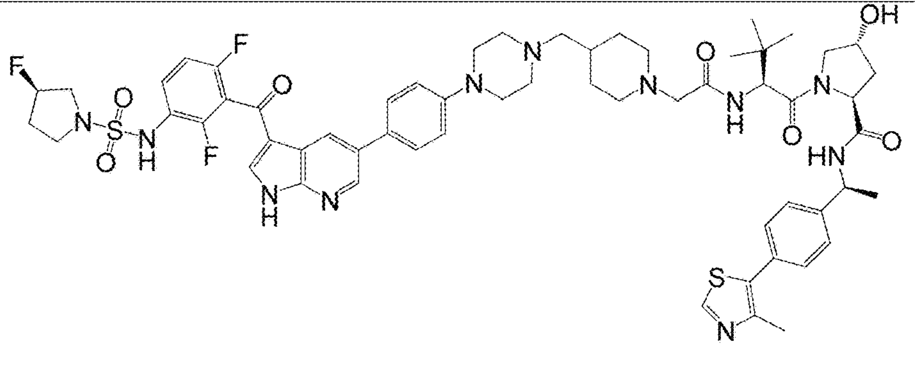 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.77 | 3 |
| 243 | 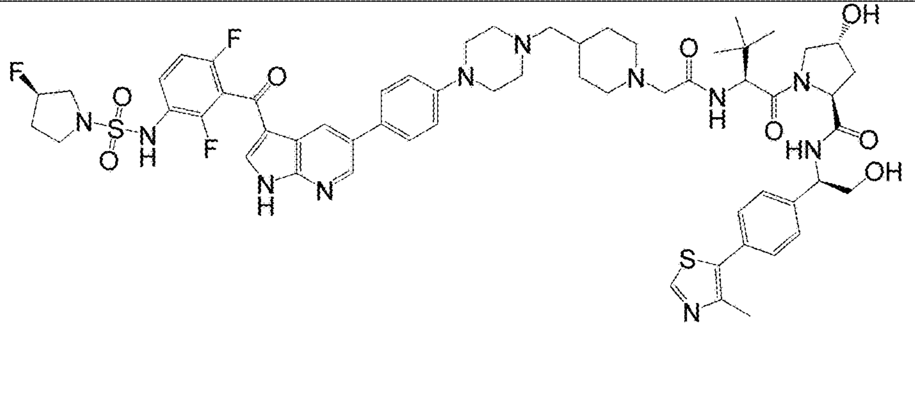 | (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1182.77 | 3 |
| 286 | 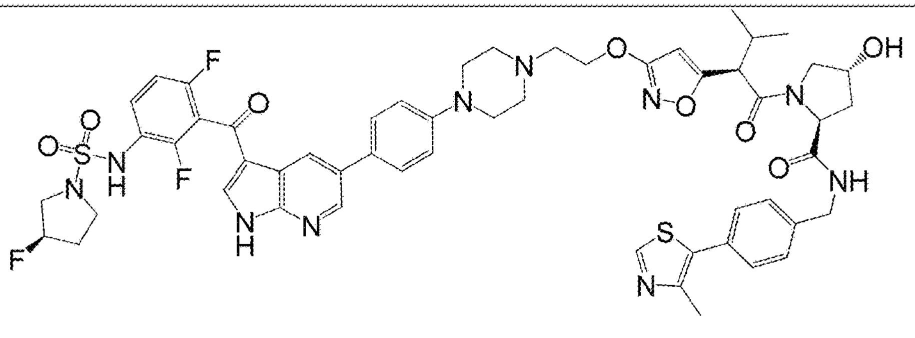 | (2S,4R)-1-((R)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide | 1095.70 | 13 |

FIG. 2D. Continued

| | | | | |
|---|---|---|---|---|
| 287 | 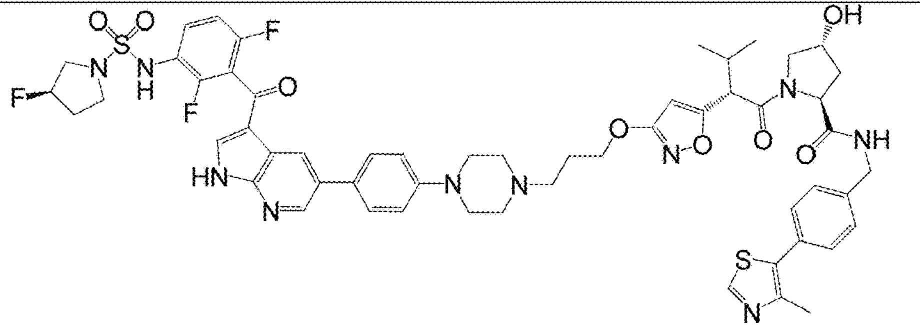 | (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N-(4-(4-methylthiazol-5-yl)benzyl)pyrrolidine-2-carboxamide | 1109.67 | 13 |
| 288 | 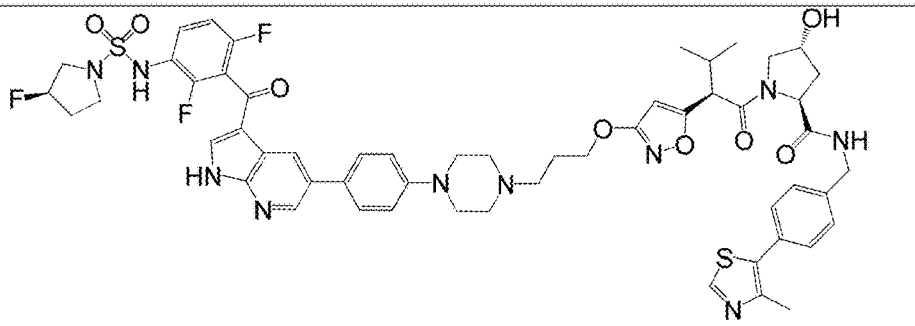 | (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N-(4-(4-methylthiazol-5-yl)benzyl)pyrrolidine-2-carboxamide | 1109.67 | 13 |

FIG. 3A

Table 2A. Data of exemplary protein targeting moieties and compounds of the present disclosure.

| No. | BRafV600E DC50 (nM) | BRafV600E Dmax (%) | NMR Transcript |
|---|---|---|---|
| 307 | C | A | $^1$H NMR (300 MHz, $CD_3OD$) δ 8.90 (s, 1H), 8.71 (s, 1H), 8.61 (d, *J* = 2.2 Hz, 1H), 8.46 (d, *J* = 2.5 Hz, 1H), 7.94 (m, 2H), 7.85-7.70 (m, 1H), 7.46 (m, 4H), 7.16 (t, *J* = 8.8 Hz, 1H), 6.98 (d, *J* = 9.0 Hz, 1H), 5.35-5.17 (m, 1H), 5.03 (t, *J* = 7.0 Hz, 1H), 4.70-4.47 (m, 3H), 3.90 (d, *J* = 11.2 Hz, 1H), 3.78 (dd, *J* = 11.1, 3.9 Hz, 1H), 3.67-3.36 (m, 9H), 3.06 (s, 2H), 2.91 (m, 2H), 2.60 (m, 4H), 2.51 (m, 3H), 2.29-2.10 (m, 6H), 2.06-1.92 (m, 2H), 1.86-1.58 (m, 3H), 1.44- 1.29 (m, 5H), 1.07 (d, *J* = 7.0 Hz, 9H). |
| 308 | D | C | $^1$H NMR: (400MHz, DMSO-$d_6$) δ: 9.28 (s, 2H), 9.05 - 8.97 (m, 1H), 8.56 (s, 1H), 8.46 - 8.40 (m, 1H), 7.89 (s, 1H), 7.58 (d, J=8.4 Hz, 2H), 7.53 - 7.39 (m, 4H), 7.37 - 7.33 (m, 1H), 7.06 (d, J=8.8 Hz, 2H), 6.83 (t, J=9.2 Hz, 1H), 5.97 - 5.77 (m, 1H), 5.36 - 5.09 (m, 1H), 4.44 (t, J=7.6 Hz, 1H), 4.40 - 4.24 (m, 3H), 4.01 - 3.81 (m, 2H), 3.79 - 3.54 (m, 5H), 3.46 (br d, J=4.4 Hz, 2H), 3.27 - 3.15 (m, 8H), 3.14 - 3.04 (m, 2H), 2.47 (s, 2H), 2.41 (s, 3H), 2.29 - 2.18 (m, 1H), 2.13 - 2.06 (m, 5H), 0.97 (d, J=6.4 Hz, 2H), 0.84 (d, J=6.8 Hz, 2H), 0.74 - 0.55 (m, 2H). |
| 309 | C | B | $^1$H NMR: (400MHz, DMSO-d6) δ: 12.91 (s, 1H), 8.99 (s, 1H), 8.65 (d, *J*=2.4 Hz, 1H), 8.53 (t, *J*=5.6 Hz, 2H), 8.15 (s, 1H), 8.07 (s, 1H), 7.68 - 7.56 (m, 3H), 7.48 - 7.41 (m, 2H), 7.40 - 7.34 (m, 2H), 7.25 (t, *J*=9.2 Hz, 1H), 7.08 (d, *J*=8.8 Hz, 2H), 5.88 (s, 1H), 5.42 - 5.18 (m, 1H), 5.13 (d, *J*=3.2 Hz, 1H), 4.45 - 4.27 (m, 4H), 4.03 - 3.86 (m, 2H), 3.80 - 3.71 (m, 2H), 3.62 (d, *J*=9.6 Hz, 1H), 3.50 - 3.39 (m, 6H), 3.25 (d, *J*=12.8 Hz, 2H), 2.54 - 2.52 (m, 2H), 2.45 (s, 4H), 2.43 (s, 1H), 2.32 (d, *J*=2.0 Hz, 1H), 2.23 (s, 2H), 2.17 - 2.00 (m, 4H), 1.98 - 1.72 (m, 2H), 0.94 (d, *J*=6.4 Hz, 3H), 0.80 (d, *J*=6.8 Hz, 3H). |

FIG. 3A. Continued

| No. | BRafV600E DC50 (nM) | BRafV600E Dmax (%) | NMR Transcript |
|---|---|---|---|
| 310 | D | B | $^1$H NMR (300 MHz, $CD_3OD$) δ8.90 (s, 1H), 8.70 (s, 1H), 8.62 (d, $J$ = 2.1 Hz, 1H), 7.91 (s, 1H), 7.81-7.73 (m, 1H), 7.62 (d, $J$ = 8.7 Hz, 2H), 7.46 (m, 4H), 7.17-7.14 (m, 3H), 5.25 (d, $J$ = 52.2 Hz, 1H), 5.08-5.03 (m, 1H), 4.66-4.47 (m, 3H), 3.91-3.75 (m, 4H), 3.60-3.42 (m, 5H), 3.10 (s, 2H), 2.84-2.76 (m, 2H), 2.65-2.60 (m, 7H), 2.51 (s, 3H), 2.35-2.32 (m, 2H), 2.28-2.16 (m, 2H), 2.03-1.92 (m, 3H), 1.78 (m, 1H), 1.62-1.54 (m, 3H), 1.46-1.32 (m, 3H), 1.09 (m, 9H) |
| 311 | C | A | $^1$H NMR: (300 MHz, DMSO-*d6*, ppm) δ 8.99 (s, 1H), 8.62 (d, $J$=2.1Hz, 1H), 8.50 (s, 1H), 7.95 (s, 1H), 7.60-7.48 (m, 5H), 7.29 (d, $J$ = 9Hz, 1H), 7.05 (d, $J$ = 9Hz, 2H), 6.94-6.88 (m, 1H), 5.32-5.24 (m, 1H), 4.57 (s, 2H), 4.49-4.46 (m, 2H), 4.35-4.31 (m, 3H), 3.66-3.62 (m, 2H), 3.34-3.32 (m, 1H), 3.29-3.28 (m, 1H), 3.28-3.13 (m, 6H), 3.10-2.99 (m, 2H), 2.92-2.80 (m, 3H), 2.46-2.43 (m, 5H), 2.19-2.17 (m, 3H), 2.11-2.03 (m, 3H), 1.94-1.90 (m, 2H), 1.81-1.72 (m, 2H), 1.58-1.54 (m, 1H), 1.23-1.14 (m, 3H), 0.95 (s, 9H) |
| 312 | D | A | $^1$H NMR: (400MHz, DMSO-$d_6$) *δ:* 12.91 (s, 1H), 9.00 (s, 1H), 8.65 - 8.55 (m, 3H), 8.19 (s, 1H), 7.97 (s, 1H), 7.81 (d, $J$=9.2 Hz, 1H), 7.59 (d, $J$=8.8 Hz, 2H), 7.45 - 7.40 (m, 4H), 7.40 - 7.31 (m, 3H), 7.06 (d, $J$=8.8 Hz, 2H), 5.34 (s, 1H), 5.21 (s, 1H), 4.50 (d, $J$=9.6 Hz, 1H), 4.47 - 4.41 (m, 1H), 4.41 - 4.32 (m, 2H), 4.30 - 4.24 (m, 1H), 3.71 - 3.54 (m, 2H), 3.47 (d, $J$=3.2 Hz, 2H), 3.18 (s, 5H), 3.05 - 2.87 (m, 3H), 2.83 (s, 2H), 2.52 (d, $J$=2.0 Hz, 3H), 2.45 (s, 3H), 2.25 - 1.85 (m, 10H), 1.81 - 1.69 (m, 2H), 1.55 (s, 1H), 1.23 - 1.09 (m, 2H), 0.99 - 0.91 (m, 9H) |
| 313 | D | A | $^1$H NMR: (400 MHz, DMSO-d6) *δ:* 9.00 (s, 1H), 8.63 (s, 2H), 8.56 (s, 1H), 8.25 (s, 2H), 7.92 (s, 1H), 7.82 (br d, $J$ = 9.6 Hz, 1H), 7.67 - 7.56 (m, 3H), 7.48 - 7.38 (m, 4H), 7.35 - 7.23 (m, 2H), 7.06 (br d, $J$ = 8.8 Hz, 2H), 5.37 - 5.20 (m, 1H), 4.54 - 4.21 (m, 7H), 3.63 (br d, $J$ = 14.2 Hz, 1H), 3.18 (br s, 3H), 3.04 - 2.76 (m, 4H), 2.45 (br s, 7H), 2.23 - 1.85 (m, 12H), 1.82 - 1.69 (m, 2H), 1.56 (br s, 1H), 1.25 - 1.07 (m, 3H), 0.94 (s, 10H). |

FIG. 3A. Continued

| No. | BRafV600E DC50 (nM) | BRafV600 E Dmax (%) | NMR Transcript |
|---|---|---|---|
| 314 | D | Not calculated | $^1$H NMR (300 MHz, DMSO-$d_6$, *ppm*): δ 13.00 (s, 1H), 9.86 (brs, 1H), 8.98 (s, 1H), 8.77 (d, J = 2.8 Hz, 2H), 8.66 (d, J = 2.2 Hz, 1H), 8.59-8.44 (m, 2H), 8.12 (s, 1H), 7.70-7.63 (m, 1H), 7.51-7.38 (m, 2H), 7.38-7.22 (m, 3H), 6.12 (d, J = 6.5 Hz, 1H), 5.40 (s, 1H), 5.22-5.15 (m, 1H), 4.45-4.12 (m, 6H), 3.85-3.71 (m, 4H), 3.66-3.48 (m, 6H), 3.24-3.11 (m, 1H), 2.89-2.73 (m, 4H), 2.51-2.43 (m, 3H), 2.31-1.97 (m, 5H), 1.25 (t, J = 7.0 Hz, 2H), 0.98-0.85 (m, 6H). |
| 315 | D | B | $^1$H NMR (300 MHz, DMSO-$d_6$, ppm): δ 13.02 (s, 1H), 9.86 (s, 1H), 9.00 (s, 1H), 8.95-8.81 (m, 2H), 8.68-8.55 (m, 3H), 8.13 (s, 1H), 7.71-7.57 (m, 1H), 7.42 -7.28 (m, 5H), 6.17 (s, 1H), 5.40-5.15 (m, 2H), 4.80-4.2.0 (m, 6H), 4.00-3.60 (m, 5H), 3.54-3.38 (m, 2H), 3.31-3.22 (m, 1H),2.72-2.60 (m, 2H), 2.48-2.41 (m, 4H), 2.35-2.25 (m, 2H), 2.20-1.89 (m, 5H),1.31-1.18 (m, 4H), 0.97 (d, *J* = 6.4 Hz, 3H), 0.83 (d, *J* = 6.6 Hz, 3H). |
| 316 | C | B | $^1$H NMR (300 MHz, $CD_3OD$) δ 8.87 (s, 1H), 8.67 (s, 1H), 8.57 (d, *J* = 2.1 Hz, 1H), 7.88 (s, 1H), 7.79-7.71 (m, 1H), 7.58 (d, *J* = 8.7 Hz, 2H), 7.46 (m, 4H), 7.17-7.10 (m, 3H), 5.22 (d, *J* = 52.8 Hz, 1H), 5.05-5.01 (m, 1H), 4.64-4.59 (m, 2H), 4.49-4.39 (m, 1H), 3.96-3.75 (m, 6H), 3.58-3.34 (m, 5H), 3.07 (s, 2H), 2.79-2.71 (m, 2H), 2.62-2.56 (m, 7H), 2.48 (s, 3H), 2.31-2.28 (m, 2H), 2.24-2.11 (m, 2H), 2.04-1.88 (m, 4H), 1.74 (m, 1H), 1.41-1.30 (m, 2H), 1.05 (m, 9H) |
| 317 | C | A | $^1$H NMR: (400MHz, DMSO-$d_6$) δ = 12.95 (s, 1H), 8.98 (s, 1H), 8.66 - 8.59 (m, 2H), 8.56 (s, 1H), 8.20 (s, 1H), 8.08 (s, 1H), 7.65 - 7.55 (m, 3H), 7.40 (br d, *J*=6.3 Hz, 5H), 7.27 - 7.18 (m, 1H), 7.04 (s, 2H), 5.39 - 5.16 (m, 1H), 4.59 - 4.52 (d, *J* = 12 Hz 1H), 4.49 - 4.41 (m, 1H), 4.41 - 4.33 (m, 1H), 4.30 - 4.19 (m, 1H), 3.94 (s, 2H), 3.71 - 3.59 (m, 2H), 3.49 - 3.43 (m, 3H), 3.40 - 3.36 (m, 2H), 3.31 - 3.23 (m, 3H), 3.15 (s, 4H), 2.69 - 2.62 (m, 1H), 2.46 - 2.42 (m, 4H), 2.41 - 2.35 (m, 4H), 2.27 - 2.20 (m, 1H), 2.19 - 2.03 (m, 5H), 1.96 - 1.85 (m, 1H), 1.72 - 1.57 (m, 2H), 1.00 - 0.90 (s, 9H). |

FIG. 3A. Continued

| No. | BRafV600E DC50 (nM) | BRafV600 E Dmax (%) | NMR Transcript |
|---|---|---|---|
| 318 | D | B | $^1$H NMR (400 MHz, Methanol-$d_4$): δ 8.83 (d, J = 35.9 Hz, 1H), 8.71 (s, 1H), 8.62-8.50 (m, 1H), 8.41 (brs, 1H), 7.91 (s, 1H), 7.80-7.70 (m, 1H), 8.65-7.59 (m, 2H), 7.50-7.36 (m, 4H), 7.23-6.96 (m, 3H), 5.30-5.15 (m, 1H), 5.04-4.96 (m, 1H), 4.68 (s, 1H), 4.63- 4.53 (m, 1H), 4.53-4.43 (m, 1H), 3.90-3.83 (m, 1H), 3.83-3.68 (m, 3H), 3.68-3.38 (m, 6H), 3.35-3.30 (m, 2H), 3.25-3.10 (m, 3H), 3.00-2.61 (m, 8H), 2.45-2.40 (m, 3H), 2.33-2.08 (m, 3H), 2.07-1.89 (m, 2H), 1.76 (brs, 1H), 1.65 (d, J = 7.1 Hz, 1H), 1.53 (d, J = 7.1 Hz, 2H), 1.07 (d, J = 11.1 Hz, 9H). |
| 319 | C | A | $^1$H NMR (400 MHz, Methanol-$d_4$): δ 8.85 (s, 1H), 8.69 (brs, 1H), 8.60 (d, J = 2.2 Hz, 1H), 7.90 (s, 1H), 7.80-7.70 (m, 1H), 7.65-7.54 (m, 2H), 7.48-7.36 (m, 4H), 7.20-7.04 (m, 3H), 5.35-5.15 (m, 1H), 5.02-4.95 (m, 1H), 4.67 (s, 1H), 4.64-4.51 (m, 1H), 4.46 (s, 1H), 3.88 (d, J = 11.1 Hz, 1H), 3.77 (dd, J = 11.1, 3.9 Hz, 1H), 3.65-3.37 (m, 5H), 3.29-3.20 (m, 4H), 2.84-2.71 (m, 7H), 2.61-2.47 (m, 4H) , 2.46 (s, 3H), 2.27-2.08 (m, 4H), 2.08-1.91(m, 1H), 1.66-1.57 (m, 2H), 1.56-1.49 (m, 3H), 1.08 (s, 9H). |
| 320 | B | B | $^1$H NMR (300 MHz, DMSO-$d_6$): δ12.87 (brs, 1H), 9.96 (brs, 1H), 8.96 (d, $J$ = 2.1 Hz, 1H), 8.63 (d, $J$ = 2.3 Hz, 1H), 8.51 (s, 1H), 8.40 (d, $J$ = 7.6 Hz, 1H), 8.04 (s, 1H), 7.74 (d, $J$ = 9.6 Hz, 1H), 7.70-7.60 (m, 3H), 7.47-7.42 (m, 2H), 7.40-7.31 (m, 2H), 7.23 (t, $J$ = 8.9 Hz, 1H), 7.05 (d, $J$ = 8.5 Hz, 2H), 5.36-5.15 (m, 1H), 5.19 (s, 1H), 4.88 (t, $J$ = 7.1 Hz, 1H), 4.54-4.38 (m, 2H), 4.27-4.21 (m, 1H), 3.60-3.52 (m, 2H), 3.47-3.41 (m, 1H), 3.37-3.31 (m, 2H), 3.30-3.24 (m, 5H),3.03 (d, $J$ = 16.1 Hz, 1H), 2.89-2.80 (m, 3H), 2.70-2.55 (m, 5H), 2.34-2.03 (m, 7H), 1.87-1.72 (m,3H), 1.47-1.37 (m, 6H), 0.93 (s, 9H). |
| 321 | D | B | $^1$H NMR (300 MHz, $CD_3OD$) δ 8.90 (s, 1H), 8.73 (s, 1H), 8.62 (d, J = 2.1 Hz, 1H), 7.98 (s, 1H), 7.72 - 7.54 (m, 3H), 7.48 - 7.34 (m, 4H), 7.25 – 7.07 (m, 3H), 4.65 (d, J = 10.9 Hz, 1H), 4.62 – 4.51 (m, 3H), 4.39 (d, J = 15.5 Hz, 1H), 3.98 – 3.79 (m, 2H), 3.66 (t, J = 6.0 Hz, 2H), 3.34 - 3.12 (m, 8H), 3.06- 2.90 (m, 2H), 2.86 - 2.69 (m, 4H), 2.54 - 2.45 (m, 3H), 2.44 - 2.18 (m, 5H), 2.17 - 1.97 (m, 3H), 1.94 - 1.62 (m, 3H), 1.49 - 1.22 (m, 2H), 1.06 (d, J = 8.1 Hz, 9H). |

FIG. 3A. Continued

| No. | BRafV600E DC50 (nM) | BRafV600E Dmax (%) | NMR Transcript |
|---|---|---|---|
| 322 | D | B | $^1$H NMR (300 MHz, DMSO-$d_6$, *ppm*): δ 13.00 (s, 1H), 11.30( brs,1H), 9.80 (s, 1H), 8.97 (s, 1H), 8.85 (s, 2H), 8.67 (d, J = 2.2 Hz, 1H), 8.58 (s, 1H), 8.50-8.46 (m, 1H), 8.14- 8.06 (m, 1H), 7.69-7.55 (m, 1H), 7.46-6.91 (m, 5H), 5.97 (d, J = 2.7 Hz, 1H), 5.38 (s, 1H), 5.20 (s, 1H), 4.85-4.60(m, 2H), 4.43-4.26 (m, 4H), 4.25-4.15 (m, 4H), 3.83-3.74 (m, 2H), 3.69-3.28 (m, 10H), 3.12-2.98 (m, 1H), 2.43-2.40 (m, 3H), 2.27-1.83(m, 5H), 1.23 (d, J = 10.7 Hz, 1H), 0.95-0.90 (m, 2H), 0.85-0.71 (m, 2H), 0.63-0.52 (m, 1H) |
| 323 | D | A | $^1$H NMR (300 MHz, DMSO-$d_6$) δ 12.93 (d, *J* = 3.4 Hz, 1H), 9.85 (s, 1H), 9.00 (s, 1H), 8.67 (d, *J* = 2.2 Hz, 1H), 8.57 (s, 1H), 8.40 (d, *J* = 7.7 Hz, 1H), 8.09 (d, *J* = 3.1 Hz, 1H), 7.80 – 8.00 (s, 1H),7.65 (dd, *J* = 8.8, 6.2 Hz, 3H), 7.51 – 7.30 (m, 4H), 7.34 – 7.21 (m, 1H), 7.18 – 7.07 (m, 2H), 5.40 (s, 1H), 5.22 (s, 1H), 4.91 (q, *J* = 7.3 Hz, 2H), 4.54 (d, *J* = 9.4 Hz, 1H), 4.43 (t, *J* = 8.2 Hz, 1H), 4.31 (s, 1H), 3.99 (d, *J* = 12.4 Hz, 3H), 3.47 – 3.23 (m, 5H), 3.15 (d, *J* = 14.1 Hz, 6H), 2.81 (dd, *J* = 16.1, 11.4 Hz, 3H), 2.54 (d, *J* = 3.2 Hz, 1H), 2.46 (s, 4H), 2.14 (s, 6H), 1.49 (d, *J* = 6.9 Hz, 3H), 1.39 (d, *J* = 7.0 Hz, 3H), 1.25 (s, 1H), 0.96 (d, *J* = 4.7 Hz, 9H). |
| 324 | D | A | $^1$H NMR, (400MHz, DMSO-$d_6$) δ: 13.17 - 12.66 (m, 1H), 8.98 (s, 1H), 8.64 (d, J=2.0 Hz, 1H), 8.51 (br s, 1H), 8.43 (d, J=8.0 Hz, 1H), 8.21 (s, 1H), 8.04 (s, 1H), 7.78 (d, J=10.0 Hz, 1H), 7.63 - 7.55 (m, 3H), 7.46 - 7.40 (m, 2H), 7.39 - 7.31 (m, 2H), 7.19 (t, J=8.4 Hz, 1H), 7.06 (d, J=8.8 Hz, 2H), 5.44 - 5.02 (m, 2H), 4.95 - 4.83 (m, 1H), 4.50 - 4.35 (m, 2H), 4.28 (s, 1H), 3.78 (d, J=12.0 Hz, 2H), 3.57 (s, 2H), 3.44 (s, 2H), 3.24 (s, 3H), 2.78 - 2.68 (m, 2H), 2.52 (s, 4H), 2.45 (s, 6H), 2.19 (d, J=6.8 Hz, 3H), 2.06 (d, J=10.4 Hz, 3H), 1.86 - 1.68 (m, 4H), 1.39 (d, J=7.2 Hz, 3H), 1.22 (d, J=12.1 Hz, 2H), 1.13 (s, 3H), 1.05 (s, 3H), 0.97 - 0.91 (m, 9H) |

FIG. 3A. Continued

| No. | BRafV600E DC50 (nM) | BRafV600 E Dmax (%) | NMR Transcript |
|---|---|---|---|
| 325 | D | A | $^1$H NMR: (400MHz, DMSO-$d_6$) *δ:* 13.00 (s, 1H), 9.86 (s, 1H), 8.98 (s, 1H), 8.77 (d, *J*=2.4 Hz, 1H), 8.69 (s, 1H), 8.44 (d, *J*=7.6 Hz, 1H), 8.13 (s, 1H), 7.88 - 7.79 (m, 4H), 7.76 - 7.69 (m, 3H), 7.63 (dt, *J*=6.0, 9.2 Hz, 1H), 7.44 (d, *J*=8.0 Hz, 4H), 7.40 - 7.33 (m, 2H), 7.28 (t, *J*=8.4 Hz, 1H), 5.40 - 5.20 (m, 1H), 5.12 (d, *J*=4.0 Hz, 1H), 4.90 (quin, *J*=7.2 Hz, 1H), 4.50 (d, *J*=9.6 Hz, 1H), 4.44 (t, *J*=8.4 Hz, 1H), 4.28 (s, 1H), 3.64 - 3.52 (m, 4H), 3.49 (s, 1H), 3.46 - 3.37 (m, 3H), 3.33 - 3.24 (m, 4H), 3.10 - 3.00 (m, 1H), 2.97 - 2.89 (m, 1H), 2.52 (s, 2H), 2.45 (s, 3H), 2.22 - 1.93 (m, 4H), 1.76 (ddd, *J*=4.4, 8.4, 12.8 Hz, 1H), 1.39 (d, *J*=7.2 Hz, 3H), 0.94 (s, 8H), 0.97 - 0.90 (m, 1H) |
| 326 | D | Not calculated | $^1$H NMR: (400MHz, DMSO-*$d_6$*) δ = 11.11 (s, 1H), 10.66 (s, 1H), 8.85 (d, *J*=2.4 Hz, 1H), 8.33 (s, 1H), 8.29 (d, *J*=7.6 Hz, 1H), 8.04 - 8.03 (m, 1H), 8.00 (d, *J*=7.2 Hz, 1H), 7.86 - 7.77 (m, 3H), 7.49 (d, *J*=2.0 Hz, 1H), 7.39 (dd, *J*=2.4, 8.4 Hz, 1H), 7.21 (d, *J*=2.0 Hz, 1H), 5.25 - 5.19 (m, 1H), 5.13 (dd, *J*=5.2, 12.9 Hz, 1H), 4.33 (t, *J*=5.6 Hz, 2H), 3.77 - 3.69 (m, 4H), 3.25 - 3.08 (m, 4H), 2.95 - 2.74 (m, 5H), 2.64 - 2.53 (m, 4H), 2.46 - 2.44 (m, 3H), 2.10 - 1.96 (m, 3H), 1.83 - 1.73 (m, 2H). |
| 327 | D | Not calculated | $^1$H NMR (400 MHz, DMSO-*$d_6$*): δ 12.93 (s, 1H), 9.84 (s, 1H), 9.04- 8.84 (m, 1H), 8.66 (d, J = 2.2 Hz, 1H), 8.56 (s, 1H), 8.28 (d, J = 7.8 Hz, 1H), 8.09 (s, 1H), 7.70-7.64 (m, 3H), 7.53-7.37 (m, 3H),7.37-7.20 (m, 3H), 7.21-7.03 (m, 2H), 6.25-6.08 (m, 1H), 5.42-5.18 (m, 1H), 5.10 (d, J = 3.7 Hz, 1H), 5.05-4.84 (m, 1H), 4.61-4.40 (m, 1H), 4.33-4.18 (m, 3H), 4.13 (t, J = 5.6 Hz, 2H), 3.75 (d, J = 8.5 Hz, 1H), 3.61- 3.45 (m, 3H), 3.45- 3.35 (m, 3H), 3.29-3.21(m, 1H), 2.82-2.68 (m, 5H), 2.47-2.39 (m, 5H), 2.35-1.91 (m, 6H), 1.82- 1.77 (m, 1H), 1.50-1.31 (m, 3H), 0.97 (d, J = 6.6 Hz, 3H), 0.89-0.70 (m, 4H). |
| 328 | C | B | $^1$H NMR (400 MHz, DMSO-*$d_6$*): δ 12.93 (s, 1H), 9.84 (s, 1H), 8.98 (s, 1H), 8.66 (d, J = 2.3 Hz, 1H), 8.56 (s, 1H), 8.40 (d, J = 7.7 Hz, 1H), 8.08 (s, 1H), 7.76-7.55 (m, 3H), 7.53-7.18 (m, 6H), 7.09 (d, J = 8.2 Hz, 2H), 6.15-5.85 (m, 1H), 5.52-4.98 (m, 2H), 4.98-4.68 (m, 1H), 4.48-4.09 (m, 6H), 3.83-3.56 (m, 2H), 3.56-3.33 (m, 5H), 3.29-3.18(m, 1H), 2.71 (d, J = 22.7 Hz, 5H), 2.49-2.43 (m, 6H), 2.36-1.90 (m, 6H), 1.85-1.70 (m, 1H), 1.50-1.42 (m, 3H), 0.96 (d, J = 6.5 Hz, 3H), 0.82 (dd, J = 14.2, 6.5 Hz, 3H). |

FIG. 3A. Continued

| No. | BRafV600E DC50 (nM) | BRafV600 E Dmax (%) | NMR Transcript |
|---|---|---|---|
| 329 | D | B | $^1$H NMR (300 MHz, DMSO-*d*$_6$, *ppm*): δ12.90 (br s, 1H), 8.98 (s, 1H), 8.65 (s, 1H), 8.54 (s, 1H), 8.39 (d, J = 7.7 Hz, 1H), 8.05 (s, 1H), 7.77 (d, J = 9.7 Hz, 1H), 7.74-7.55 (m, 3H), 7.50-7.34 (m, 4H), 7.27-7.18 (m, 1H), 7.18-6.98 (m, 2H), 5.46-5.04 (m, 2H), 4.98-4.84 (m, 1H), 4.63-4.41 (m, 2H), 4.31-4.27 (m, 1H), 3.89-3.75 (m, 2H), 3.63-3.49 (m, 2H), 3.47-3.42 (m, 4H), 3.32-3.26 (m, 1H), 3.05 (s, 2H), 2.75 (t, J = 11.9 Hz, 2H), 2.69-2.57 (m, 4H), 2.55-2.45 (m, 3H), 2.45-2.21 (m, 6H), 2.19-1.91 (m, 3H), 1.86-1.72 (m, 3H), 1.57-1.50 (m, 2H), 1.41 (s, 3H), 0.97 (s, 9H) |
| 330 | D | Not calculated | $^1$H NMR: (400MHz, DMSO-*d*$_6$) δ: 12.98 (s, 1H), 10.12 - 9.59 (m, 2H), 9.03 - 8.97 (m, 1H), 8.78 (d, J=8.4 Hz, 1H), 8.61 (d, J=6.0 Hz, 2H), 8.12 (s, 1H), 7.76 (dt, J=6.0, 8.8 Hz, 1H), 7.68 (d, J=8.8 Hz, 2H), 7.41 (q, J=8.4 Hz, 4H), 7.33 (t, J=8.8 Hz, 1H), 7.17 (d, J=8.8 Hz, 2H), 5.41 (s, 1H), 5.28 (s, 1H), 4.60 (d, J=9.2 Hz, 2H), 4.52 - 4.34 (m, 5H), 4.22 (dd, J=5.2, 15.6 Hz, 1H), 4.15 - 3.84 (m, 5H), 3.71 (d, J=7.2 Hz, 1H), 3.68 - 3.55 (m, 4H), 3.54 - 3.44 (m, 4H), 3.43 - 3.34 (m, 1H), 3.14 (s, 3H), 3.06 (s, 1H), 2.20 (d, J=6.4 Hz, 2H), 2.13 (d, J=7.6 Hz, 2H), 2.10 - 2.02 (m, 3H), 2.01 - 1.84 (m, 5H), 1.56 (s, 3H), 0.99 - 0.93 (m, 9H) |
| 331 | D | Not calculated | $^1$H NMR: (400MHz, DMSO-d$_6$) δ = 12.91 (s, 1H), 9.86 (s, 1H), 9.01 - 8.98 (m, 1H), 8.92 (d, *J*=8.0 Hz, 1H), 8.66 (d, *J*=2.0 Hz, 1H), 8.53 (s, 1H), 8.23 (d, *J*=8.0 Hz, 1H), 8.14 (s, 1H), 8.08 (s, 1H), 7.69 - 7.55 (m, 4H), 7.49 - 7.41 (m, 3H), 7.36 - 7.24 (m, 3H), 7.07 (d, *J*=8.8 Hz, 3H), 6.18 (s, 1H), 5.37 (s, 1H), 5.24 (s, 1H), 5.11 (d, *J*=3.6 Hz, 1H), 5.06 - 4.96 (m, 1H), 4.89 (t, *J*=7.2 Hz, 1H), 4.53 (t, *J*=7.6 Hz, 1H), 4.43 (t, *J*=7.6 Hz, 1H), 4.29 (d, *J*=3.6 Hz, 1H), 3.88 - 3.64 (m, 4H), 3.59 - 3.36 (m, 8H), 3.31 - 3.10 (m, 8H), 2.74 (t, *J*=11.2 Hz, 3H), 2.48 - 2.42 (m, 13H), 2.32 - 1.91 (m, 7H), 1.82 (d, *J*=7.8 Hz, 5H), 1.47 (d, *J*=7.2 Hz, 1H), 1.36 (d, *J*=7.2 Hz, 3H), 1.26 (s, 3H), 0.97 (d, *J*=6.4 Hz, 3H), 0.87 - 0.80 (m, 4H), 0.77 (d, *J*=6.4 Hz, 1H) |

FIG. 3A. Continued

| No. | BRafV600E DC50 (nM) | BRafV600E Dmax (%) | NMR Transcript |
|---|---|---|---|
| 332 | C | B | $^1$H NMR: (400MHz, DMSO-$d_6$) δ = 13.16 - 12.60 (m, 1H), 9.02 - 8.96 (m, 1H), 8.80 (d, *J*=7.6 Hz, 1H), 8.65 (d, *J*=2.0 Hz, 1H), 8.53 (s, 1H), 8.41 (d, *J*=7.6 Hz, 1H), 8.22 (s, 1H), 8.06 (s, 1H), 7.66 - 7.54 (m, 4H), 7.47 - 7.35 (m, 6H), 7.24 (t, *J*=8.6 Hz, 1H), 7.07 (d, *J*=8.8 Hz, 3H), 6.16 (s, 1H), 5.36 (s, 1H), 5.23 (s, 1H), 4.99 - 4.87 (m, 2H), 4.38 (t, *J*=7.6 Hz, 1H), 4.30 (s, 1H), 3.86 - 3.66 (m, 5H), 3.59 (d, *J*=10.0 Hz, 1H), 3.51 - 3.24 (m, 14H), 3.19 (s, 6H), 2.74 (t, *J*=11.2 Hz, 3H), 2.48 - 2.40 (m, 14H), 2.27 - 2.18 (m, 4H), 2.14 - 1.96 (m, 4H), 1.88 - 1.74 (m, 5H), 1.47 (d, *J*=7.2 Hz, 1H), 1.39 (d, *J*=7.2 Hz, 4H), 1.31 - 1.17 (m, 3H), 1.00 - 0.91 (m, 4H), 0.86 - 0.73 (m, 5H) |
| 333 | D | Not calculated | $^1$H NMR: (400 MHz, DMSO-d6) *δ:* 10.66 (s, 1H), 8.97 (s, 1H), 8.84 (s, 1H), 8.45 (s, 1H), 8.46 - 8.41 (m, 1H), 8.33 - 8.26 (m, 2H), 8.22 (s, 2H), 8.05 - 7.97 (m, 2H), 7.81 - 7.77 (m, 1H), 7.43 - 7.33 (m, 4H), 7.20 (s, 1H), 5.19 (s, 1H), 4.88 (br d, *J* = 7.2 Hz, 1H), 4.55 (d, *J* = 8.8 Hz, 1H), 4.44 (s, 1H), 4.27 (br s, 1H), 3.97 (s, 2H), 3.75 (br s, 4H), 3.65 – 3.45 (m, 9H),3.09 (br s, 4H), 2.43 (br d, *J* = 2.8 Hz, 9H), 2.13 - 1.90 (m, 4H), 1.82 - 1.65 (m, 3H), 1.44 - 1.30 (m, 3H), 0.94 (s, 9H). |
| 334 | D | C | $^1$H NMR: (400 MHz, DMSO-d6) *δ:* 10.66 (s, 1H), 8.97 (s, 1H), 8.84 (d, *J* = 2.4 Hz, 1H), 8.44 (d, *J* = 8.0 Hz, 1H), 8.32 (s, 1H), 8.28 (d, *J* = 6.8 Hz, 1H), 8.19 (s, 2H), 8.05 - 7.98 (m, 2H), 7.81 - 7.77 (m, 1H), 7.44 - 7.35 (m, 4H), 7.20 (s, 1H), 5.18 (br s, 1H), 4.90 (t, *J* = 6.8 Hz, 1H), 4.54 (d, *J* = 9.6 Hz, 1H), 4.47 - 4.41 (m, 1H), 4.27 (br s, 1H), 3.95 (s, 2H), 3.75 (br s, 5H), 3.68 – 3.12 (m, 23H),3.09 (br s, 4H), 2.44 (d, *J* = 4.8 Hz, 9H), 2.17 - 1.89 (m, 4H), 1.74 (br s, 3H), 1.48 - 1.30 (m, 3H), 0.93 (s, 9H). |
| 335 | D | Not calculated | $^1$H NMR: (400MHz, DMSO-$d_6$) δ = 11.10 (s, 1H), 10.66 (s, 1H), 8.84 (d, *J*=2.4 Hz, 1H), 8.34 - 8.27 (m, 2H), 8.17 (s, 1H), 8.06 - 7.97 (m, 2H), 7.85 - 7.76 (m, 3H), 7.47 (d, *J*=2.1 Hz, 1H), 7.37 (dd, *J*=2.3, 8.4 Hz, 1H), 7.20 (d, *J*=2.1 Hz, 1H), 5.21 - 5.05 (m, 2H), 4.40 - 4.26 (m, 2H), 3.80 - 3.72 (m, 6H), 3.66 - 3.56 (m, 3H), 3.09 (s, 4H), 2.94 - 2.84 (m, 1H), 2.74 - 2.64 (m, 3H), 2.55 - 2.52 (m, 5H), 2.46 - 2.42 (m, 5H), 2.38 - 2.19 (m, 3H), 2.16 - 1.91 (m, 3H), 1.84 - 1.67 (m, 2H) |

FIG. 3A. Continued

| No. | BRafV600E DC50 (nM) | BRafV600 E Dmax (%) | NMR Transcript |
|---|---|---|---|
| 336 | D | Not calculated | $^1$H NMR (400MHz, DMSO-$d_6$) δ = 11.14 - 11.03 (m, 1H), 10.66 (s, 1H), 8.84 (s, 1H), 8.35 - 8.26 (m, 2H), 8.07 - 7.98 (m, 2H), 7.85 - 7.74 (m, 3H), 7.48 - 7.44 (m, 1H), 7.37 (d, *J*=7.6 Hz, 1H), 7.26 - 7.15 (m, 1H), 5.28 - 5.04 (m, 2H), 4.32 (s, 2H), 3.83 - 3.73 (m, 6H), 3.64 - 3.48 (m, 10H), 3.10 (s, 4H), 2.97 - 2.81 (m, 2H), 2.74 - 2.55 (m, 8H), 2.44 (s, 3H), 2.11 - 1.89 (m, 3H), 1.79 - 1.70 (m, 1H). |
| 337 | D | Not calculated | $^1$H NMR (400MHz, DMSO-$d_6$) δ = 11.11 (s, 1H), 10.66 (s, 1H), 8.84 (d, *J*=2.3 Hz, 1H), 8.34 - 8.27 (m, 2H), 8.04 (s, 1H), 8.00 (d, *J*=8.0 Hz, 1H), 7.85 - 7.77 (m, 3H), 7.46 (d, *J*=2.0 Hz, 1H), 7.37 (m, 1H), 7.25 - 7.19 (m, 1H), 5.27 - 5.07 (m, 2H), 4.36 - 4.26 (m, 2H), 3.82 - 3.73 (m, 6H), 3.63 - 3.45 (m, 15H), 3.17 - 3.03 (m, 4H), 2.94 - 2.83 (m, 1H), 2.62 - 2.53 (m, 5H), 2.45 - 2.43 (m, 5H), 2.14 - 1.94 (m, 4H), 1.87 - 1.72 (m, 2H). |
| 338 | D | A | $^1$H NMR: (400 MHz, DMSO-d6) *δ:* 8.97 (s, 1H), 8.64 (d, *J* = 2.0 Hz, 1H), 8.52 (br s, 1H), 8.43 (br d, *J* = 7.6 Hz, 1H), 8.17 (s, 1H), 8.07 - 8.02 (m, 1H), 7.75 (br d, *J* = 9.6 Hz, 1H), 7.67 - 7.48 (m, 1H), 7.45 - 7.33 (m, 4H), 7.24 (br t, *J* = 8.0 Hz, 1H), 7.06 (br d, *J* = 8.8 Hz, 2H), 5.39 - 5.18 (m, 1H), 4.90 (br t, *J* = 7.2 Hz, 1H), 4.52 (d, *J* = 9.8 Hz, 1H), 4.45 (br t, *J* = 8.0 Hz, 1H), 4.29 (br s, 1H), 3.83 - 3.46 (m, 3H), 3.28 - 3.15 (m, 12H), 2.81 - 2.65 (m, 4H), 2.45 (s, 6H), 2.13 - 2.01 (m, 3H), 1.89 - 1.75 (m, 3H), 1.69 - 1.49 (m, 3H), 1.39 (br d, *J* = 7.2 Hz, 3H), 1.31 - 1.08 (m, 2H), 0.94 (s, 9H) |
| 339 | D | A | $^1$H NMR: (400MHz, DMSO-$d_6$) *δ*: 8.98 (s, 1H), 8.62 (d, *J*=2.0 Hz, 1H), 8.55 - 8.41 (m, 2H), 8.20 (s, 1H), 8.03 (s, 1H), 7.73 (d, *J*=9.2 Hz, 1H), 7.65 - 7.53 (m, 3H), 7.48 - 7.40 (m, 2H), 7.39 - 7.33 (m, 2H), 7.23 (t, *J*=8.6 Hz, 1H), 6.65 (d, *J*=8.8 Hz, 2H), 5.39 - 5.18 (m, 1H), 4.90 (t, *J*=7.2 Hz, 1H), 4.55 - 4.36 (m, 2H), 4.28 (s, 1H), 3.58 (d, *J*=5.6 Hz, 1H), 3.46 (s, 8H), 3.17 (s, 3H), 3.05 (d, *J*=16.4 Hz, 2H), 2.91 ( d, *J*=16.0 Hz, 1H), 2.45 (s, 6H), 2.42 - 2.35 (m, 3H), 2.31 - 2.22 (m, 2H), 2.21 - 1.92 (m, 5H), 1.81 - 1.55 (m, 4H), 1.42 - 1.31 (m, 3H), 0.94 (s, 9H) |

FIG. 3A. Continued

| No. | BRafV600E DC50 (nM) | BRafV600E Dmax (%) | NMR Transcript |
|---|---|---|---|
| 340 | D | A | $^1$H NMR: (400 MHz, DMSO-d6) δ: 10.66 (s, 1H), 8.97 (s, 1H), 8.84 (d, J = 2.4 Hz, 1H), 8.44 (d, J = 7.2 Hz, 1H), 8.32 (s, 1H), 8.28 (br d, J = 7.2 Hz, 1H), 8.19 (s, 2H), 8.05 - 7.97 (m, 2H), 7.84 - 7.76 (m, 2H), 7.44 - 7.39 (m, 2H), 7.39 - 7.32 (m, 3H), 7.20 (s, 1H), 5.20 (br s, 1H), 4.88 (br d, J = 7.2 Hz, 1H), 4.55 (d, J = 9.2 Hz, 1H), 4.44 (t, J = 8.0 Hz, 1H), 4.28 (br s, 1H), 3.96 (d, J = 2.8 Hz, 2H), 3.76 (br s, 4H), 3.66 - 3.54 (m, 5H), 3.10 (br s, 5H), 2.72 (br s, 2H), 2.60 - 2.57 (m, 1H), 2.57 (br s, 2H), 2.45 - 2.43 (m, 6H), 2.10 - 1.94 (m, 3H), 1.77 (br s, 3H), 1.34 (d, J = 7.2 Hz, 3H), 0.94 (s, 9H). |
| 341 | D | A | $^1$H NMR: (400 MHz, DMSO-d6) δ: 10.67 (s, 1H), 8.98 (s, 1H), 8.84 (d, J = 2.4 Hz, 1H), 8.44 (d, J = 7.6 Hz, 1H), 8.32 (s, 1H), 8.28 (br d, J = 7.2 Hz, 1H), 8.20 (s, 2H), 8.04 - 7.97 (m, 2H), 7.84 - 7.76 (m, 2H), 7.46 - 7.41 (m, 2H), 7.40 - 7.34 (m, 3H), 7.20 (s, 1H), 5.18 (br s, 1H), 4.95 - 4.86 (m, 1H), 4.54 (d, J = 9.8 Hz, 1H), 4.44 (br t, J = 8.4 Hz, 1H), 4.27 (br s, 1H), 3.96 (s, 2H), 3.75 (br s, 4H), 3.64 - 3.51 (m, 14H), 3.09 (br s, 4H), 2.46 - 2.34 (m, 12H), 2.07 - 1.93 (m, 3H), 1.75 (br d, J = 8.0 Hz, 3H), 1.37 (d, J = 7.2 Hz, 3H), 0.93 (s, 9H). |
| 342 | D | A | $^1$H NMR: (400MHz, DMSO-$d_6$) δ = 11.20 - 11.02 (m, 1H), 10.71 - 10.61 (m, 1H), 8.84 (d, J=2.4 Hz, 1H), 8.34 - 8.13 (m, 2H), 8.10 - 7.97 (m, 2H), 7.94 - 7.71 (m, 3H), 7.49 - 7.30 (m, 2H), 7.28 - 7.16 (m, 1H), 5.30 - 5.06 (m, 2H), 4.43 - 4.17 (m, 2H), 3.84 - 3.79 (m, 2H), 3.75 (s, 4H), 3.71 - 3.42 (m, 7H), 3.41 - 3.13 - 3.06 (m, 4H), 2.89 (d, J=5.6, 14.4, 17.2 Hz, 1H), 2.65 - 2.53 (m, 5H), 2.49 - 2.47 (m, 5H), 2.10 - 1.91 (m, 3H), 1.85 - 1.60 (m, 2H). |
| 343 | D | A | $^1$H NMR: (400MHz, DMSO-$d_6$) δ: 8.98 (s, 1H), 8.63 (d, J=2.0 Hz, 1H), 8.45 (d, J=7.6 Hz, 1H), 8.20 (s, 2H), 8.05 (s, 1H), 7.73 (d, J=9.6 Hz, 1H), 7.66 - 7.57 (m, 1H), 7.54 (d, J=8.4 Hz, 2H), 7.46 - 7.40 (m, 2H), 7.35 (d, J=8.0 Hz, 2H), 7.25 (br t, J=8.4 Hz, 1H), 6.71 (d, J=8.8 Hz, 2H), 5.39 - 5.17 (m, 1H), 4.88 (t, J=7.2 Hz, 1H), 4.48 (d, J=9.6 Hz, 1H), 4.42 (t, J=8.0 Hz, 1H), 4.37 (s, 1H), 4.27 (s, 1H), 3.56 (s, 4H), 3.39 (d, J=3.2 Hz, 4H), 3.32 - 3.18 (m, 4H), 2.93 - 2.72 (m, 4H), 2.45 (s, 3H), 2.37 (s, 2H), 2.17 - 1.94 (m, 6H), 1.90 - 1.59 (m, 6H), 1.36 (d, J=7.2 Hz, 4H), 1.20 - 0.99 (m, 2H), 0.92 (s, 9H) |

FIG. 3A. Continued

| No. | BRafV600E DC50 (nM) | BRafV600 E Dmax (%) | NMR Transcript |
|---|---|---|---|
| 344 | D | A | $^1$H NMR: (400MHz, DMSO-$d_6$) δ: 12.80 (s, 1H), 8.98 (d, J=1.2 Hz, 1H), 8.65 (s, 1H), 8.54 (s, 1H), 8.49 - 8.42 (m, 1H), 8.22 (s, 2H), 8.06 (s, 1H), 7.87 (t, J=8.8 Hz, 1H), 7.66 - 7.55 (m, 3H), 7.49 - 7.42 (m, 2H), 7.41 - 7.33 (m, 2H), 7.24 (t, J=8.8 Hz, 1H), 7.07 (d, J=8.8 Hz, 2H), 5.39 - 5.20 (m, 1H), 4.99 - 4.85 (m, 1H), 4.54 - 4.42 (m, 2H), 4.29 (s, 1H), 3.66 - 3.53 (m, 2H), 3.49 - 3.45 (m, 2H), 3.41 - 3.35 (m, 3H), 3.32 - 3.24 (m, 3H), 3.19 - 2.96 (m, 5H), 2.94 - 2.81 (m, 1H), 2.65 - 2.56 (m, 3H), 2.46 (s, 3H), 2.42 - 2.37 (m, 2H), 2.24 - 1.94 (m, 5H), 1.84 - 1.70 (m, 2H), 1.69 - 1.61 (m, 1H), 1.50 - 1.36 (m, 4H), 1.17 - 1.07 (m, 1H), 1.04 - 0.66 (m, 9H) |
| 345 | D | A | $^1$H NMR: (400MHz, DMSO-$d_6$) δ: 12.90 (s, 1H), 9.85 (s, 1H), 8.99 (s, 1H), 8.63 (d, J=2.0 Hz, 1H), 8.52 (s, 1H), 8.40 (d, J=7.2 Hz, 1H), 8.06 (s, 1H), 7.63 (dt, J=6.0, 9.0 Hz, 1H), 7.56 (d, J=8.4 Hz, 2H), 7.44 (d, J=8.4 Hz, 2H), 7.40 - 7.32 (m, 2H), 7.28 (t, J=8.8 Hz, 1H), 6.69 (d, J=8.8 Hz, 2H), 5.42 - 5.20 (m, 2H), 4.97 - 4.85 (m, 1H), 4.52 (d, J=9.6 Hz, 4H), 4.46 - 4.38 (m, 3H), 4.32 - 4.17 (m, 2H), 3.70 - 3.28 (m, 9H), 3.19 - 2.95 (m, 6H), 2.77 - 2.70 (m, 1H), 2.63 - 2.54 (m, 2H), 2.46 (s, 3H), 2.19 - 1.93 (m, 5H), 1.92 - 1.83 (m, 1H), 1.82 - 1.74 (m, 1H), 1.73 - 1.64 (m, 1H), 1.51 - 1.33 (m, 3H), 1.30 - 1.19 (m, 1H), 0.95 (s, 9H) |
| 346 | D | A | $^1$H NMR: (400 MHz, DMSO-d6) δ: 10.66 (s, 1H), 8.97 (s, 1H), 8.84 (d, J = 2.4 Hz, 1H), 8.43 (d, J = 7.6 Hz, 1H), 8.32 (s, 1H), 8.28 (d, J = 8.0 Hz, 1H), 8.16 (s, 2H), 8.03 (d, J = 2.4 Hz, 1H), 7.99 (d, J = 7.6 Hz, 1H), 7.84 - 7.74 (m, 2H), 7.46 - 7.32 (m, 5H), 7.20 (d, J = 2.0 Hz, 1H), 5.19 (br s, 1H), 4.95 - 4.85 (m, 1H), 4.55 (d, J = 9.6 Hz, 1H), 4.44 (t, J = 8.0 Hz, 1H), 4.28 (br s, 1H), 3.96 (s, 2H), 3.75 (br s, 4H), 3.67 - 3.49 (m, 12H), 3.09 (br s, 4H), 2.75 - 2.64 (m, 2H), 2.55 (br t, J = 5.6 Hz, 1H), 2.44 (d, J = 4.4 Hz, 9H), 2.09 - 1.94 (m, 3H), 1.82 - 1.70 (m, 3H), 1.37 (d, J = 7.2 Hz, 3H), 0.94 (s, 9H). |
| 347 | D | A | $^1$H NMR (300 MHz, $CD_3OD$, ppm): δ 8.90-8.80 (m, 1H), 8.61-8.52 (m, 2H), 7.88 (s, 1H), 7.80-7.69 (m, 1H), 7.62-7.48 (m, 2H), 7.46-7.31 (m, 4H), 7.30-7.00 (m, 3H), 5.30-5.102 (m, 1H), 5.08-4.92 (m, 1H), 4.70-4.30 (m, 3H), 4.00-3.70 (m, 4H), 3.60-3.31 (m, 4H), 3.18 (s, 2H), 2.90-2.70 (m, 2H), 2.70-2.57 (m, 4H), 2.50-2.41 (m, 3H), 2.40-2.28 (m, 8H), 2.14-2.09 (m, 2H), 2.00-1.80 (m, 3H), 1.80-1.62 (m, 1H), 1.61-1.43 (m, 3H), 1.42-1.22 (m, 3H),1.06 (s, 9H) |

FIG. 3A. Continued

| No. | BRafV600E DC50 (nM) | BRafV600E Dmax (%) | NMR Transcript |
|---|---|---|---|
| 348 | D | A | $^1$H NMR (400 MHz, Methanol-$d_4$): δ 8.90-8.86 (m, 1H), 8.65-8.59 (m, 2H), 7.88 (s, 1H), 7.76 (d, J = 5.9 Hz, 1H), 7.56 (d, J = 8.3 Hz, 2H), 7.48-7.33 (m, 4H), 7.14 (t, J = 8.7 Hz, 1H), 6.88 (d, J = 8.4 Hz, 2H), 5.29-5.16 (m, 1H), 5.03-4.95 (m, 1H), 4.68-4.45 (m, 3H), 3.87-3.76 (m, 2H), 3.58-3.36 (m, 5H), 3.05 (d, J = 6.0 Hz, 5H), 2.93 (m, 2H), 2.50-2.46 (m, 3H), 2.27-2.10 (m, 4H), 1.99-1.86 (m, 2H), 1.89-1.77 (m, 3H), 1.56-1.47 (m, 5H), 1.32 (d, J = 17.9 Hz, 1H), 1.06 (s, 9H). |
| 349 | D | Not calculated | $^1$H NMR (400 MHz, DMSO-$d_6$): δ 12.93 (s, 1H), 9.84 (s, 1H), 9.00 (s, 1H), 8.67 (d, *J* = 2.2 Hz, 1H), 8.57 (s, 1H), 8.08 (s, 1H), 7.68-7.60 (m, 3H), 7.48-7.41(m, 4H), 7.35-7.00 (m, 5H), 5.39 (s, 1H), 5.24 (s, 1H), 4.97-4.88 (m, 1H), 4.55 (d, *J* = 9.4 Hz, 1H), 4.44 (t, *J* = 8.1 Hz, 1H), 4.31 (s, 1H), 3.82-3.77 (m, 1H), 3.68-3.54 (m, 3H), 3.53-3.50 (m, 2H), 3.49-3.44 (m, 3H), 3.32 (m, 2H),3.21-2.92 (m, 7H), 2.83 (m, 1H), 2.63 (t, *J* = 11.0 Hz, 1H), 2.60-2.46 (m, 3H), 2.39-1.95 (m, 4H), 1.90-1.86 (m, 3H), 1.70-1.56 (m, 1H), 1.39 (d, *J* = 7.0 Hz, 3H), 1.27-1.15 (m, 3H), 0.97 (d, *J* = 7.1 Hz, 9H). |
| 350 | D | A | $^1$H NMR (400 MHz, DMSO-$d_6$, ppm): δ 12.95 (brs, 1H), 9.85 (brs, 1H), 9.02 (s, 1H), 8.38-8.8 (m, 3H), 8.19 (s, 1H), 7.55-7.92 (m, 4H), 7.22-7.55 (m, 5H), 6.88-7.22 (m, 2H), 4.85-5.50 (m, 2H), 4.40-4.65 (m, 2H), 4.08-4.39 (m, 3H), 3.40-3.73 (m, 6H),2.82-3.28 (m, 5H), 2.55-2.68 (m, 2H), 2.51 (s,3H), 1.93-2.24 (m,3H), 1.70-1.90 (m,1H), 1.32-1.57 (m, 3H),1.10-1.32 (m, 1H), 0.68-1.10 (s, 9H) |
| 351 | D | A | $^1$H NMR: (400MHz, DMSO-$d_6$) δ: 8.98 (s, 1H), 8.64 (d, *J*=2.0 Hz, 1H), 8.49 (d, *J*=7.5 Hz, 1H), 8.21 (s, 1H), 8.07 (s, 1H), 8.02 - 7.94 (m, 1H), 7.67 - 7.53 (m, 3H), 7.47 - 7.41 (m, 2H), 7.39 - 7.32 (m, 2H), 7.25 (t, *J*=8.4 Hz, 1H), 7.06 (d, *J*=8.8 Hz, 2H), 5.39 - 5.19 (m, 1H), 4.93 - 4.86 (m, 1H), 4.51 - 4.42 (m, 2H), 4.27 (s, 1H), 3.79 (s, 1H), 3.32 - 3.24 (m, 4H), 3.14 (d, *J*=18.0 Hz, 3H), 2.96 (d, *J*=18.0 Hz, 2H), 2.82 - 2.67 (m, 4H), 2.57 (s, 2H), 2.45 (s, 4H), 2.17 - 1.92 (m, 6H), 1.90 - 1.61 (m, 7H), 1.41 - 1.35 (m, 3H), 1.21 (d, *J*=11.6 Hz, 2H), 0.98 (d, *J*=6.0 Hz, 3H), 0.94 (s, 10H), 0.86 (d, *J*=6.0 Hz, 3H), 0.89 - 0.83 (m, 1H) |

FIG. 3A. Continued

| No. | BRafV600E DC50 (nM) | BRafV600 E Dmax (%) | NMR Transcript |
|---|---|---|---|
| 352 | C | B | $^1$H NMR: (400MHz, DMSO-$d_6$) δ: 13.04 - 12.70 (m, 1H), 9.00 (s, 1H), 8.66 - 8.61 (m, 2H), 8.17 (s, 1H), 8.19 - 8.15 (m, 1H), 7.98 (s, 1H), 7.83 (d, J=9.6 Hz, 1H), 7.66 (dd, J=6.0, 8.8 Hz, 1H), 7.58 (d, J=7.6 Hz, 2H), 7.48 - 7.30 (m, 6H), 7.06 (d, J=8.0 Hz, 2H), 5.37 - 5.21 (m, 1H), 4.50 (d, J=9.2 Hz, 1H), 4.48 - 4.40 (m, 2H), 4.37 (d, J=6.4 Hz, 2H), 4.32 - 4.23 (m, 2H), 3.70 - 3.57 (m, 1H), 3.46 (s, 4H), 3.19 (s, 2H), 3.02 (d, J=16.0 Hz, 3H), 2.94 - 2.79 (m, 3H), 2.21 - 2.02 (m, 13H), 1.90 (s, 2H), 1.73 (d, J=14.8 Hz, 2H), 1.55 (s, 1H), 1.22 - 1.10 (m, 2H), 0.95 (s, 9H) |
| 353 | D | Not calculated | $^1$H NMR: (400MHz, DMSO-$d_6$) δ: 10.96 (s, 1H), 10.82 (s, 1H), 9.96 - 9.58 (m, 1H), 8.90 (s, 1H), 8.40 - 8.25 (m, 2H), 8.18 (s, 1H), 8.01 (d, J=8.0 Hz, 1H), 7.89 - 7.76 (m, 2H), 7.70 (d, J=8.4 Hz, 1H), 7.28 (d, J=11.2 Hz, 2H), 7.16 (d, J=8.4 Hz, 1H), 5.57 - 5.30 (m, 2H), 5.09 (dd, J=5.2, 13.2 Hz, 2H), 4.49 (s, 2H), 4.46 - 4.22 (m, 4H), 3.82 - 3.59 (m, 8H), 3.35 (s, 1H), 3.25 - 3.02 (m, 5H), 2.99 - 2.84 (m, 1H), 2.62 (s, 1H), 2.24 (s, 2H), 2.08 - 1.84 (m, 2H) |
| 354 | D | Not calculated | $^1$H NMR: (400MHz, DMSO-$d_6$), δ = 10.96 (s, 1H), 10.66 (s, 1H), 8.85 (d, J=2.4 Hz, 1H), 8.40 - 8.22 (m, 2H), 8.09 - 7.96 (m, 2H), 7.88 - 7.75 (m, 2H), 7.63 (d, J=8.4 Hz, 1H), 7.27 - 7.16 (m, 2H), 7.07 (m, 1H), 5.26 - 4.99 (m, 2H), 4.45 - 4.26 (m, 2H), 4.22 (s, 2H), 3.83 - 3.71 (m, 6H), 3.66 - 3.56 (m, 2H), 3.10 (s, 4H), 2.90 (s, 1H), 2.67 - 2.55 (m, 7H), 2.47 - 2.40 (m, 5H), 2.09 - 1.87 (m, 3H), 1.83 - 1.67 (m, 2H) |
| 355 | D | Not calculated | $^1$H NMR: (400MHz, DMSO-$d_6$) δ: 10.96 (s, 1H), 10.68 (s, 1H), 8.84 (d, J=2.4 Hz, 1H), 8.39 - 8.20 (m, 2H), 8.07 - 7.94 (m, 2H), 7.83 - 7.72 (m, 2H), 7.64 - 7.50 (m, 1H), 7.22 (s, 1H), 7.17 (s, 1H), 7.10 - 6.99 (m, 1H), 5.20 (s, 1H), 5.06 (dd, J=5.2, 13.2 Hz, 1H), 5.10 - 4.99 (m, 1H), 4.41 - 4.32 (m, 1H), 4.31 - 4.25 (m, 1H), 4.21 - 4.13 (m, 2H), 3.76 (d, J=4.4 Hz, 7H), 3.66 - 3.48 (m, 12H), 3.09 (s, 4H), 2.98 - 2.81 (m, 2H), 2.60 (s, 1H), 2.43 (s, 9H), 1.98 (d, J=7.6 Hz, 3H), 1.75 (s, 2H) |

FIG. 3A. Continued

| No. | BRafV600E DC50 (nM) | BRafV600 E Dmax (%) | NMR Transcript |
| --- | --- | --- | --- |
| 356 | D | Not calculated | $^1$H NMR: (400MHz, DMSO-$d_6$) δ: 10.94 (s, 1H), 10.65 (s, 1H), 8.84 (s, 1H), 8.36 - 8.23 (m, 2H), 8.08 - 7.94 (m, 2H), 7.87 - 7.74 (m, 2H), 7.61 (d, *J*=8.8 Hz, 1H), 7.24 - 7.14 (m, 2H), 7.06 (d, *J*=8.4 Hz, 1H), 5.20 (s, 1H), 5.06 (dd, *J*=5.2, 13.2 Hz, 1H), 4.39 - 4.17 (m, 4H), 3.84 - 3.73 (m, 6H), 3.66 - 3.50 (m, 6H), 3.09 (s, 5H), 2.59 (s, 4H), 2.45 - 2.36 (m, 7H), 1.99 (s, 3H), 1.75 (s, 2H), 1.82 - 1.68 (m, 1H) |
| 357 | D | A | $^1$H-NMR (400 MHz, $CD_3OD$, ppm) δ8.88 (s, 1H), 8.73 (s, 1H), 8.64 (s, 1H), 7.93 (s, 1H), 7.77-7.65 (m, 1H), 7.46 (d, *J* = 3Hz, 2H), 7.44-7.42 (m, 6H), 7.19-7.11 (m, 1H), 5.31-516 (m, 1H), 5.09-5.00 (m, 1H), 4.84(s, 1H), 4.65-4.59 (m, 1H), 4.51-4.40 (s, 1H), 3.90-3.86 (m, 1H), 3.79-3.70 (m, 1H), 3.58-3.3.41 (m, 4H), 3.33-3.16 (m, 2H), 3.09 (s, 2H), 2.78-2.61 (m, 12H), 2.49 (s, 3H), 2.30-2.14 (m, 5H), 2.01-1.86 (m, 6H), 1.54-1.52 (m, 3H), 1.47 (s, 1H), 1.40-1.30 (m, 1H), 1.02 (s, 9H) |
| 358 | D | A | $^1$H NMR: (300 MHz, DMSO-d6) δ 12.80-13.00 (s, 1H), 9.70-9.90 (s, 1H), δ 8.97 (s, 1H), 8.65 (d, *J* = 2.2 Hz, 1H), 8.56 (s, 1H), 8.43 (d, *J* = 7.7 Hz, 1H), 8.08 (s, 1H), 7.68 – 7.60 (m, 4H), 7.44-7.34 (m, 4H), 7.27 (t, *J* = 8.6 Hz, 1H), 7.08 (d, *J* = 8.4 Hz, 2H), 5.38-5.11 (m, 2H), 4.90 (t, *J* = 7.2 Hz, 1H), 4.52 – 4.43 (m, 2H), 4.28 (s, 1H), 4.06 (m, 2H), 3.65-3.31 (m, 7H), 3.30 – 3.27 (m, 1H), 3.12 – 3.02 (m, 4H), 2.65 (m, 1H), 2.45 (m, 3H), 2.12-2.00 (m, 5H), 1.77 (m, 1H), 1.37 – 1.24 (m, 5H), 0.942 (m, 10H). |
| 359 | D | B | $^1$H NMR: (400MHz, DMSO-$d_6$) *δ:* 12.93 (s, 1H), 8.99 (s, 1H), 8.69 (d, *J*=2.0 Hz, 1H), 8.58 (s, 1H), 8.43 (d, *J*=7.6 Hz, 1H), 8.17 (s, 1H), 8.08 (s, 1H), 7.76 (d, *J*=8.8 Hz, 1H), 7.69 - 7.59 (m, 3H), 7.47 - 7.42 (m, 2H), 7.41 - 7.33 (m, 2H), 7.27 (t, *J*=8.8 Hz, 1H), 7.15 (d, *J*=8.4 Hz, 2H), 5.43 - 5.21 (m, 1H), 5.11 (s, 1H), 4.97 - 4.85 (m, 1H), 4.55 - 4.42 (m, 2H), 4.29 (s, 1H), 3.65 - 3.57 (m, 3H), 3.50 - 3.47 (m, 2H), 3.08 - 2.99 (m, 2H), 2.94 - 2.78 (m, 3H), 2.64 - 2.60 (m, 1H), 2.46 (s, 3H), 2.32 - 2.23 (m, 3H), 2.23 - 2.06 (m, 7H), 2.05 - 1.95 (m, 1H), 1.82 - 1.71 (m, 3H), 1.65 - 1.45 (m, 2H), 1.43 - 1.35 (m, 3H), 1.27 - 1.13 (m, 2H), 0.99 - 0.92 (m, 15H) |

FIG. 3A. Continued

| No. | BRafV600E DC50 (nM) | BRafV600 E Dmax (%) | NMR Transcript |
|---|---|---|---|
| 360 | C | A | $^1$H NMR: (400MHz, DMSO-$d_6$) δ: 112.92 (s, 1H), 8.99 (s, 1H), 8.68 (d, *J*=2.0 Hz, 1H), 8.57 (s, 1H), 8.44 (d, *J*=7.6 Hz, 1H), 8.19 (s, 1H), 8.07 (s, 1H), 7.78 (d, *J*=10.0 Hz, 1H), 7.67 - 7.59 (m, 3H), 7.49 - 7.42 (m, 2H), 7.40 - 7.35 (m, 2H), 7.26 (t, *J*=8.0 Hz, 1H), 7.08 (d, *J*=8.4 Hz, 2H), 5.39 - 5.21 (m, 1H), 4.91 (q, *J*=7.2 Hz, 1H), 4.52 (d, *J*=10.0 Hz, 1H), 4.46 (t, *J*=8.4 Hz, 1H), 4.30 (s, 1H), 3.69 - 3.56 (m, 3H), 3.33 - 3.25 (m, 6H), 3.08 - 3.00 (m, 2H), 2.94 - 2.79 (m, 3H), 2.46 (s, 3H), 2.44 - 2.37 (m, 2H), 2.21 (d, *J*=6.4 Hz, 3H), 2.17 - 1.94 (m, 6H), 1.88 - 1.72 (m, 3H), 1.68 - 1.51 (m, 1H), 1.40 (d, *J*=7.2 Hz, 3H), 1.31 - 1.16 (m, 2H), 1.03 (br d, *J*=6.0 Hz, 6H), 0.96 (s, 10H) |
| 361 | B | A | $^1$H NMR: (400MHz, DMSO-$d_6$) δ: 13.16 - 12.44 (m, 1H), 8.98 (s, 1H), 8.64 (d, *J*=2.0 Hz, 1H), 8.51 (s, 1H), 8.45 (d, *J*=7.6 Hz, 1H), 8.36 (d, *J*=10.0 Hz, 1H), 8.23 (s, 1H), 8.04 (s, 1H), 7.65 - 7.55 (m, 3H), 7.46 - 7.41 (m, 2H), 7.40 - 7.32 (m, 2H), 7.21 (t, *J*=8.8 Hz, 1H), 7.06 (d, *J*=8.8 Hz, 2H), 5.39 - 5.18 (m, 1H), 4.95 - 4.83 (m, 1H), 4.53 - 4.40 (m, 2H), 4.28 (s, 1H), 3.77 (d, *J*=12.8 Hz, 2H), 3.58 (d, *J*=7.6 Hz, 1H), 3.45 (s, 1H), 3.27 (d, *J*=6.8 Hz, 3H), 2.72 (t, *J*=11.2 Hz, 2H), 2.46 (s, 3H), 2.40 (s, 6H), 2.21 (d, *J*=6.8 Hz, 3H), 2.13 - 2.00 (m, 4H), 1.85 - 1.65 (m, 5H), 1.40 (d, *J*=7.2 Hz, 3H), 1.30 - 1.15 (m, 2H), 1.08 (d, *J*=7.0 Hz, 1H), 1.04 - 0.89 (m, 13H) |
| 362 | D | Not calculated | $^1$H NMR: (400 MHz, DMSO-d6) δ: 10.94 (s, 1H), 10.67 (s, 1H), 8.84 (d, *J* = 2.4 Hz, 1H), 8.33 (s, 1H), 8.29 (br d, *J* = 7.6 Hz, 1H), 8.17 (s, 1H), 8.03 (d, *J* = 2.4 Hz, 1H), 7.99 (br d, *J* = 7.6 Hz, 1H), 7.81 (t, *J* = 7.6 Hz, 1H), 7.77 (d, *J* = 2.0 Hz, 1H), 7.61 (d, *J* = 8.4 Hz, 1H), 7.20 (d, *J* = 2.0 Hz, 1H), 7.17 (s, 1H), 7.05 (dd, *J* = 2.0, 8.4 Hz, 1H), 5.18 (br s, 1H), 5.06 (dd, *J* = 5.2, 13.4 Hz, 1H), 4.41 - 4.23 (m, 3H), 4.21 - 4.09 (m, 3H), 3.75 (br d, *J* = 3.2 Hz, 6H), 3.61 - 3.50 (m, 12H), 3.09 (br s, 4H), 2.95 - 2.83 (m, 2H), 2.59-2.55 (m, 4H), 2.44 - 2.34 (m, 8H), 1.98- 1.9 (m, 3H), 1.79 - 1.68 (m, 3H) |

FIG. 3A. Continued

| No. | BRafV600E DC50 (nM) | BRafV600 E Dmax (%) | NMR Transcript |
|---|---|---|---|
| 363 | C | B | $^1$H NMR (300 MHz, DMSO-$d_6$, *ppm*): δ13.20 (brs, 1H), 10.10 (brs, 1H), 8.99 (s, 1H), 8.75-8.60 (m, 1H), 8.58-8.35 (m, 2H), 8.04 (s, 1H), 7.79-7.64 (m, 1H), 7.63-7.52 (m, 3H), 7.49-7.42 (m, 2H), 7.42-7.38 (m, 2H), 7.30-7.20 (m, 1H), 6.67 (d, J = 8.4 Hz, 2H), 5.48-5.02 (m, 2H), 5.02-4.87 (m, 1H), 4.57-4.41 (m, 2H), 4.40-4.20 (m, 1H), 3.80-3.55 (m, 2H), 3.55-3.40 (m, 5H), 3.30-3.20 (m, 2H),3.15-2.75 (m, 4H), 2.82-2.60 (m, 4H),2.52-2.25 (m, 7H), 2.21-1.89 (m, 5H), 1.90-1.71 (m, 2H), 1.75-1.11 (m, 4H), 0.96 (s, 9H) |
| 364 | C | A | $^1$H NMR (400 MHz, DMSO-$d_6$, ppm): δ 12.86 (brs, 1H), 9.85 (brs, 1H), 8.98 (s, 1H), 8.62 (d, J = 2.3 Hz, 1H), 8.52-8.41 (m, 2H), 8.04 (s, 1H), 7.73 (d, J = 9.7 Hz, 1H), 7.62-7.56 (m, 3H), 7.49-7.41 (m, 2H), 7.40-7.32 (m, 2H), 7.24-7.16 (m, 1H), 6.66 (d, J = 8.4 Hz, 2H), 5.38-5.21 (m, 1H), 5.23-5.12 (m, 1H), 4.90 (t, J = 7.2 Hz, 1H), 4.54-4.38 (m, 2H), 4.28 (s, 1H), 3.65-3.52 (m, 2H), 3.47-3.38(m,6H), 3.36-3.34 (m, 2H), 3.27-3.06 (m, 3H), 2.93-2.46 (m, 5H), 2.45-2.40(m,5H), 2.38 (d, J = 7.7 Hz, 2H), 2.20-1.95 (m, 4H), 1.82-1.68 (m, 2H), 1.39 (d, J = 7.0 Hz, 3H), 1.24 (s, 1H), 0.95 (s, 9H). |
| 365 | D | Not calculated | $^1$H NMR (300 MHz, $d_6$-DMSO) *δ* 0.96 (s, 9H), 1.10-1.27 (m, 2H), 1.28-1.62 (m, 6H), 1.63-1.98 (m, 6H), 1.99-2.38 (m, 6H), 2.47 (s, 6H), 2.75-3.09 (m, 4H), 3.11-3.26 (m, 4H), 3.56-3.78 (m, 3H), 4.13-4.57 (m, 6H), 5.17 (s, 1H), 5.73 (d, *J* = 7.5Hz, 1H), 6.96-7.27 (m, 4H), 7.43 (s, 4H), 7.59 (d, *J* = 7.5Hz, 2H), 7.83 (d, *J* = 9.6Hz, 1H), 8.10 (s, 1H), 8.48 (s, 1H), 8.65 (s, 2H), 9.01 (s, 1H), 12.8 (br., 1H) |
| 366 | D | Not calculated | $^1$H NMR: (400MHz, DMSO-$d_6$) *δ:* 12.90 (s, 1H), 8.97 (s, 1H), 8.65 (d, *J*=2.0 Hz, 1H), 8.53 (s, 1H), 8.36 (d, *J*=7.6 Hz, 1H), 8.19 (s, 1H), 8.05 (s, 1H), 7.66 - 7.56 (m, 3H), 7.46 - 7.41 (m, 2H), 7.40 - 7.35 (m, 2H), 7.25 (t, *J*=8.0 Hz, 1H), 7.12 - 7.01 (m, 2H), 6.15 (t, *J*=5.6 Hz, 1H), 6.08 (d, *J*=9.6 Hz, 1H), 5.38 - 5.19 (m, 1H), 4.91 (q, *J*=7.2 Hz, 1H), 4.44 (t, *J*=8.0 Hz, 1H), 4.35 - 4.26 (m, 2H), 3.66 - 3.57 (m, 2H), 3.48 (s, 1H), 3.43 - 3.36 (m, 2H), 3.33 - 3.27 (m, 1H), 3.26 - 3.12 (m, 5H), 3.11 - 2.97 (m, 2H), 2.55 - 2.53 (m, 2H), 2.45 (s, 3H), 2.35 (br t, *J*=7.2 Hz, 2H), 2.15 - 1.94 (m, 3H), 1.80 (ddd, *J*=4.8, 8.4, 12.8 Hz, 1H), 1.62 - 1.53 (m, 2H), 1.38 (d, *J*=7.2 Hz, 3H), 1.00 (s, 2H), 0.93 (s, 9H) |

FIG. 3A. Continued

| No. | BRafV600E DC50 (nM) | BRafV600 E Dmax (%) | NMR Transcript |
|---|---|---|---|
| 367 | D | Not calculated | $^1$H NMR: (400MHz, DMSO-$d_6$), δ = 11.09 (s, 1H), 10.66 (s, 1H), 8.85 (d, *J*=2.4 Hz, 1H), 8.38 - 8.24 (m, 2H), 8.07 - 7.95 (m, 2H), 7.87 - 7.75 (m, 2H), 7.61 (m, 1H), 7.22 (d, *J*=2.0 Hz, 1H), 7.12 (d, *J*=8.8 Hz, 1H), 7.05 (d, *J*=7.2 Hz, 1H), 6.81 (s, 1H), 5.30 - 5.19 (m, 1H), 5.09 (m, , 1H), 3.77 (s, 4H), 3.44 - 3.36 (m, 4H), 3.12 (s, 4H), 2.97 - 2.83 (m, 1H), 2.73 - 2.57 (m, 6H), 2.45 (s, 3H), 2.10 - 1.98 (m, 3H), 1.86 - 1.75 (m, 2H) |
| 368 | D | Not calculated | $^1$H NMR: (400 MHz, DMSO-d6) δ = 11.06 (s, 1H), 10.65 (s, 1H), 8.84 (d, *J*=2.4 Hz, 1H), 8.36 - 8.25 (m, 2H), 8.18 (s, 1H), 8.05 - 7.95 (m, 2H), 7.86 - 7.73 (m, 2H), 7.58 (m, 1H), 7.23 - 7.12 (m, 2H), 7.04 (d, *J*=7.2 Hz, 1H), 6.61 (m, 1H), 5.23 - 5.11 (m, 1H), 5.04 (m, 1H), 3.74 (d, *J*=4.4 Hz, 4H), 3.63 - 3.56 (m, 4H), 3.51 - 3.47 (m, 2H), 3.09 (s, 3H), 2.91 - 2.81 (m, 1H), 2.67 (m, 2H), 2.55 - 2.51 (m, 5H), 2.44 (s, 5H), 2.04 - 1.91 (m, 3H), 1.77 - 1.65 (m, 2H). |
| 369 | D | Not calculated | $^1$H NMR: (400MHz, DMSO-$d_6$), δ: 11.11 (s, 1H), 10.67 (s, 1H), 8.86 (s, 1H), 8.37 - 8.24 (m, 2H), 8.07 - 7.98 (m, 2H), 7.86 - 7.74 (m, 2H), 7.64 - 7.54 (m, 1H), 7.23 - 7.13 (m, 2H), 7.04 (d, *J*=7.2 Hz, 1H), 6.62 (t, *J*=5.6 Hz, 1H), 5.16 (d, *J*=3.2 Hz, 1H), 5.06 (m, 1H), 3.75 (s, 4H), 3.66 - 3.48 (m, 12H), 3.09 (s, 4H), 2.94 - 2.83 (m, 1H), 2.67 - 2.55 (m, 3H), 2.45 - 2.34 (m, 6H), 2.09 - 1.90 (m, 3H), 1.77 - 1.67 (m, 2H) |
| 370 | D | A | $^1$H NMR (400 MHz, DMSO-*d*$_6$, ppm): δ9.84 (s, 1H), 9.01 (s, 1H), 8.88-8.55 (m, 2H), 8.40 (d, *J* = 7.7 Hz, 1H), 8.07 (d, *J* = 3.2 Hz, 1H), 7.73-7.44 (d, *J* = 8.0 Hz, 3H), 7.40-7.23 (m, 4H), 7.26-7.22 (m, 1H), 7.15-7.10 (m, 2H), 5.37-5.12 (m, 2H), 4.96-4.91 (m, 1H), 4.60-4.41 (m, 2H), 4.43-4.29 (m, 1H), 3.88-3.40 (m, 9H), 3.39-2.87 (m, 6H), 2.85-2.71 (m, 2H), 2.71-2.56 (m, 3H), 2.50-2.42 (m, 3H), 2.38-1.95 (m, 4H), 1.88-1.67 (m, 3H), 1.65-1.62 (m, 1H), 1.38 (d, *J* = 7.0 Hz, 3H), 1.26-1.14 (m, 2H), 0.96 (s, 9H) |

FIG. 3A. Continued

| No. | BRafV600E DC50 (nM) | BRafV600E Dmax (%) | NMR Transcript |
|---|---|---|---|
| 371 | D | A | $^1$H NMR (300 MHz, $CD_3OD$) δ8.87 (s, 1H), 8.43 (s, 1H), 7.99 (s, 1H), 7.51-7.40 (m, 7H), 7.09-7.03 (m, 4H), 5.08 (d, *J*=53.0 Hz, 1H), 4.63-4.48 (m, 4H), 4.38-4.33 (m, 1H), 3.91-3.76 (m, 2H), 3.63-3.34 (m, 4H), 3.22-3.19 (m, 4H), 3.02 (s, 2H), 2.91-2.84 (m, 2H), 2.57-2.54 (m, 4H), 2.47 (s, 3H), 2.25-2.16 (m, 5H), 2.12-1.97 (m, 2H), 1.87-1.76 (m, 3H), 1.60 (s, 1H), 1.36-1.27 (m, 2H), 1.04 (s, 9H) |
| 372 | D | Not calculated | $^1$H NMR: (400 MHz, DMSO-d6) δ = 11.09 (s, 1H), 10.65 (s, 1H), 8.87 - 8.78 (m, 1H), 8.36 - 8.25 (m, 2H), 8.08 - 7.95 (m, 2H), 7.87 - 7.74 (m, 2H), 7.60 - 7.56 (m, 1H), 7.21 (s, 1H), 7.15 (d, *J*=8.8 Hz, 1H), 7.04 (d, *J*=7.2 Hz, 1H), 6.61 (t, *J*=6.0 Hz, 1H), 5.18 (s, 1H), 5.06 (m, 1H), 3.76 (s, 4H), 3.67 - 3.44 (m, 14H), 3.10 (s, 4H), 2.95 - 2.83 (m, 1H), 2.70 - 2.53 (m, 5H), 2.47 - 2.38 (m, 6H), 2.09 - 1.93 (m, 3H), 1.75 (s, 2H). |
| 373 | D | Not calculated | $^1$H NMR: (400 MHz, DMSO-d6) δ = 11.09 (s, 1H), 10.65 (s, 1H), 8.84 (d, *J*=2.4 Hz, 1H), 8.36 - 8.26 (m, 2H), 8.21 (s, 1H), 8.08 - 7.94 (m, 2H), 7.87 - 7.73 (m, 2H), 7.63 - 7.52 (m, 1H), 7.26 - 7.08 (m, 2H), 7.03 (d, *J*=7.2 Hz, 1H), 6.60 (m, 1H), 5.18 (s, 1H), 5.05 (m, 1H), 3.75 (s, 4H), 3.66 - 3.44 (m, 22H), 3.09 (s, 4H), 2.71 - 2.59 (m, 4H), 2.43 (s, 3H), 2.09 - 1.90 (m, 3H), 1.81 - 1.62 (m, 2H) |
| 374 | D | Not calculated | $^1$H NMR (400 MHz, DMSO-$d_6$, ppm): δ 12.85 (brs, 1H), 9.82 (brs, 1H), 8.98 (s, 1H), 8.63 (d, *J* = 2.2 Hz, 1H), 8.50 (s, 1H), 8.42 (d, *J* = 7.6 Hz, 1H), 8.04 (s, 1H), 7.71 (d, *J* = 9.7 Hz, 1H), 7.67-7.52 (m, 3H), 7.47-7.30 (m, 4H), 7.25 (t, *J* = 8.7 Hz, 1H), 6.84 (d, *J* = 8.4 Hz, 2H), 5.36-5.22 (m, 1H), 5.10 (d, *J* = 3.5 Hz, 1H), 4.89 (t, *J* = 7.2 Hz, 1H), 4.52-4.45 (m, 2H), 4.44-4.28 (m, 1H), 4.14-3.52 (m, 2H), 3.47 (s, 1H), 3.34-3.23 (m, 4H), 3.15 (s, 1H), 3.04 (d, *J* = 16.1 Hz, 1H), 2.95-2.91 (m, 4H), 2.90-2.45 (m, 8H), 2.40-2.31 (m, 3H), 2.34-1.86 (m, 4H), 1.83-1.75 (m, 1H), 1.58-1.45 (m, 4H), 1.38 (d, *J* = 7.0 Hz, 3H), 0.93 (s, 9H) |

FIG. 3A. Continued

| No. | BRafV600E DC50 (nM) | BRafV600E Dmax (%) | NMR Transcript |
|---|---|---|---|
| 375 | D | B | $^1$H NMR: (300 MHz, $CD_3OD$, ppm) δ 8.87 (s, 1H), 8.72 (s, 1H), 8.62-8.61 (d, *J* = 2.1MHz, 1H), 7.91 (s, 1H), 7.75-7.73 (m, 1H), 7.65-7.62 (m, 2H), 7.43-7.38 (m, 6H), 7.11-7.08 (m, 1H), 5.30-5.13 (m, 1H), 5.02-5.00 (m, 1H), 4.63-4.56 (m, 2H), 4.44-4.38 (m, 1H), 3.89-3.73 (m, 2H), 3.67-3.40 (m, 4H), 3.18-3.14 (m, 2H), 3.02 (s, 2H), 2.92-2.88 (m, 2H), 2.68-2.63 (m, 1H), 2.53-2.50 (m, 2H), 2.47 (s, 3H), 2.24-2.18 (m, 6H), 1.95-1.75 (m, 8H), 1.58-1.50 (m, 5H), 1.38-1.34 (m, 3H), 1.05-1.03 (m, 9H) |
| 376 | D | Not calculated | $^1$H NMR: (400MHz, DMSO-$d_6$) *δ:* 12.87 (s, 1H), 8.97 (s, 1H), 8.64 (d, *J*=2.4 Hz, 1H), 8.52 (s, 1H), 8.31 (s, 1H), 8.18 (s, 1H), 8.05 (s, 1H), 7.82 (d, *J*=9.6 Hz, 1H), 7.66 - 7.58 (m, 2H), 7.58 - 7.52 (m, 3H), 7.33 (d, *J*=8.4 Hz, 2H), 7.24 (t, *J*=8.0 Hz, 1H), 7.12 - 7.00 (m, 2H), 5.41 - 5.20 (m, 1H), 4.58 - 4.45 (m, 2H), 4.33 (s, 1H), 3.76 (d, J=12.0 Hz, 2H), 3.64 - 3.52 (m, 3H), 3.48 - 3.42 (m, 3H), 3.37 (dd, J=2.8, 12.0 Hz, 5H), 3.32 - 3.28 (m, 2H), 3.27 - 3.22 (m, 2H), 3.17 (s, 1H), 3.06 (d, J=16.0 Hz, 2H), 2.93 (d, J=16.0 Hz, 2H), 2.77 - 2.69 (m, 1H), 2.17 (d, J=7.2 Hz, 2H), 2.14 - 1.93 (m, 4H), 1.84 (ddd, J=4.4, 8.8, 12.8 Hz, 1H), 1.80 - 1.66 (m, 3H), 1.60 (s, 3H), 1.50 (s, 3H), 1.30 - 1.13 (m, 2H), 1.05 (t, *J*=7.2 Hz, 1H), 0.96 - 0.86 (m, 9H) |
| 377 | B | A | $^1$H NMR: (400MHz, DMSO-$d_6$) *δ:* 12.90 (s, 1H), 9.01 - 8.95 (m, 1H), 8.64 (d, J=2.4 Hz, 1H), 8.53 (s, 1H), 8.44 - 8.36 (m, 1H), 8.15 (s, 1H), 8.06 (s, 1H), 7.99 (d, J=9.2 Hz, 1H), 7.69 - 7.53 (m, 3H), 7.47 - 7.41 (m, 2H), 7.41 - 7.35 (m, 2H), 7.30 - 7.21 (m, 5H), 7.06 (d, J=8.8 Hz, 2H), 5.41 - 5.19 (m, 1H), 5.10 (s, 1H), 5.00 - 4.84 (m, 1H), 4.50 (d, J=9.2 Hz, 1H), 4.43 (t, J=8.0 Hz, 1H), 4.27 (s, 1H), 3.66 - 3.55 (m, 3H), 3.49 (d, J=14.4 Hz, 4H), 3.39 (s, 3H), 3.21 (s, 3H), 2.56 - 2.53 (m, 2H), 2.52 (s, 3H), 2.45 (s, 3H), 2.25 - 1.87 (m, 4H), 1.84 - 1.67 (m, 1H), 1.38 (d, J=7.2 Hz, 3H), 1.00 - 0.80 (m, 9H) |
| 378 | D | Not calculated | $^1$H NMR: (400MHz, DMSO-$d_6$) *δ:* 12.96 (s, 1H), 8.98 (s, 1H), 8.68 (d, *J*=2.0 Hz, 1H), 8.58 (s, 1H), 8.39 (d, *J*=7.6 Hz, 1H), 8.19 (s, 1H), 8.10 (s, 1H), 7.98 (d, *J*=9.2 Hz, 1H), 7.66 (d, *J*=8.0 Hz, 2H), 7.63 - 7.58 (m, 1H), 7.45 - 7.42 (m, 2H), 7.41 - 7.36 (m, 4H), 7.27 - 7.21 (m, 6H), 5.37 - 5.19 (m, 1H), 5.09 (s, 1H), 4.91 (t, *J*=7.6 Hz, 1H), 4.49 (d, *J*=9.2 Hz, 1H), 4.43 (t, *J*=8.0 Hz, 1H), 4.27 (s, 1H), 3.68 - 3.54 (m, 4H), 3.31 - 3.23 (m, 3H), 2.93 (d, *J*=10.4 Hz, 2H), 2.45 (s, 3H), 2.12 - 1.97 (m, 6H), 1.83 - 1.66 (m, 6H), 1.37 (d, *J*=7.2 Hz, 3H), 0.97 - 0.85 (m, 11H) |

FIG. 3A. Continued

| No. | BRafV600E DC50 (nM) | BRafV600E Dmax (%) | NMR Transcript |
|---|---|---|---|
| 379 | D | Not calculated | $^1$H NMR: (400 MHz, DMSO-d6) δ = 10.68 (s, 1H), 8.97 (s, 1H), 8.84 (d, *J*=2.4 Hz, 1H), 8.44 (d, *J*=8.0 Hz, 1H), 8.38 - 8.26 (m, 2H), 8.06 - 7.98 (m, 2H), 7.82 - 7.71 (m, 2H), 7.50- 7.34 (m, 6H), 7.16 - 7.02 (m, 4H), 5.14 (s, 1H), 4.99 - 4.74 (m, 1H), 4.58 (d, *J*=9.6 Hz, 1H), 4.64 - 4.53 (m, 1H), 4.28 (s, 1H), 4.16 - 4.14 (m, 2H ), 4.02 (d, *J*=8.0 Hz, 2H), 3.89 - 3.71 (m, 6H), 3.55-3.64 (m, 2H), 3.18 (s, 4H), 2.45-2.42 (m, 6H), 2.07 – 2.01 (m, 1H), 1.80 - 1.74 (m, 1H), 1.48 - 1.34 (m, 3H), 0.96 (s, 9H). |
| 380 | D | Not calculated | $^1$H NMR: (400 MHz, DMSO-d6) δ: 10.85 (s, 1H), 9.06 - 8.91 (m, 2H), 8.44 (d, *J*=7.6 Hz, 1H), 8.34 (s, 1H), 8.30 (d, *J*=8.8 Hz, 1H), 8.21 (d, *J*=2.0 Hz, 1H), 8.02 (d, *J*=7.2 Hz, 1H), 7.83 (t, *J*=8.0 Hz, 1H), 7.75 (d, *J*=2.0 Hz, 1H), 7.42 (d, *J*=8.4 Hz, 4H), 7.38 - 7.32 (m, 2H), 7.15 - 7.06 (m, 2H), 7.00 (d, *J*=9.0 Hz, 2H), 4.94 - 4.86 (m, 1H), 4.56 (d, *J*=9.6 Hz, 1H), 4.48 - 4.42 (m, 1H), 4.31 - 4.27 (m, 1H), 4.18 - 4.13 (m, 2H), 3.99 (s, 2H), 3.78 (br s, 7H), 3.67 (s, 6H), 3.20 (s, 4H), 2.53 (s, 3H), 2.44 (s, 3H), 2.10 - 2.01 (m, 1H), 1.78 (m, 1H), 1.49 - 1.32 (m, 3H), 0.95 (s, 9H) |
| 381 | D | Not calculated | $^1$H NMR: (400MHz, DMSO-$d_6$) δ: 10.68 (s, 1H), 8.98 (s, 1H), 8.85 (d, *J*=2.4 Hz, 1H), 8.44 (d, *J*=7.6 Hz, 1H), 8.38 - 8.25 (m, 2H), 8.06 (d, *J*=2.4 Hz, 1H), 8.00 (d, *J*=7.6 Hz, 1H), 7.81 (t, *J*=8.0 Hz, 1H), 7.72 (d, *J*=2.0 Hz, 1H), 7.49 - 7.30 (m, 6H), 7.15 - 7.06 (m, 2H), 7.03 - 6.93 (m, 2H), 5.13 (s, 1H), 4.90 (t, *J*=7.2 Hz, 1H), 4.55 (d, *J*=9.6 Hz, 1H), 4.45 (t, *J*=8.0 Hz, 1H), 4.32 - 4.25 (m, 1H), 4.15 - 4.06 (m, 2H), 3.97 (s, 2H), 3.81 - 3.73 (m, 6H), 3.66 - 3.55 (m, 10H), 3.19 (s, 4H), 2.44 (d, *J*=2.8 Hz, 6H), 2.12 - 1.99 (m, 1H), 1.83 - 1.73 (m, 1H), 1.51 - 1.32 (m, 3H), 0.94 (s, 9H) |
| 382 | D | Not calculated | $^1$H NMR: (400MHz, DMSO-$d_6$) δ = 10.68 (s, 1H), 8.97 (s, 1H), 8.84 (d, *J*=2.4 Hz, 1H), 8.44 (d, *J*=8.0 Hz, 1H), 8.38 - 8.26 (m, 2H), 8.06 - 7.98 (m, 2H), 7.82 - 7.71 (m, 2H), 7.50- 7.34 (m, 6H), 7.16 - 7.02 (m, 4H), 5.14 (s, 1H), 4.99 - 4.74 (m, 1H), 4.58 (d, *J*=9.6 Hz, 1H), 4.64 - 4.53 (m, 1H), 4.28 (s, 1H), 4.16 - 4.14 (m, 2H ), 4.02 (d, *J*=8.0 Hz, 2H), 3.89 - 3.71 (m, 6H), 3.55-3.64 (m, 18H), 3.18 (s, 4H), 2.45-2.42 (m, 6H), 2.07 – 2.01 (m, 1H), 1.80 - 1.74 (m, 1H), 1.48 - 1.34 (m, 3H), 0.96 (s, 9H). |

FIG. 3A. Continued

| No. | BRafV600E DC50 (nM) | BRafV600E Dmax (%) | NMR Transcript |
|---|---|---|---|
| 383 | C | B | $^1$H NMR: (400MHz, DMSO-$d_6$) *δ:* 12.86 (s, 1H), 9.01 - 8.96 (m, 1H), 8.95 - 8.82 (m, 1H), 8.63 (d, *J*=2.1 Hz, 1H), 8.52 (s, 1H), 8.30 (d, *J*=7.6 Hz, 1H), 8.03 (s, 1H), 7.63 - 7.46 (m, 4H), 7.45 - 7.38 (m, 2H), 7.35 - 7.30 (m, 2H), 7.13 (s, 1H), 7.05 (d, *J*=8.8 Hz, 2H), 6.16 - 6.07 (m, 1H), 5.37 - 5.17 (m, 1H), 5.11 (d, *J*=3.2 Hz, 1H), 5.05 - 4.96 (m, 1H), 4.90 (t, *J*=7.2 Hz, 1H), 4.42 (t, *J*=7.6 Hz, 1H), 4.26 (s, 1H), 4.22 - 4.11 (m, 2H), 3.75 (d, *J*=8.8 Hz, 1H), 3.59 - 3.36 (m, 4H), 3.29 - 3.12 (m, 6H), 2.45 (s, 3H), 2.41 - 2.31 (m, 3H), 2.30 - 2.22 (m, 1H), 2.11 - 2.02 (m, 3H), 1.82 - 1.68 (m, 3H), 1.56 (dd, *J*=7.6, 14.5 Hz, 2H), 1.48 - 1.41 (m, 1H), 1.35 (d, *J*=7.2 Hz, 3H), 0.96 (d, *J*=6.4 Hz, 3H), 0.83 (d, *J*=6.8 Hz, 3H) |
| 384 | D | A | $^1$H NMR: (400MHz, DMSO-$d_6$) *δ:* 12.95 (s, 1H), 9.90 (s, 1H), 8.99 (s, 1H), 8.92 (s, 1H), 8.67 (d, *J*=2.0 Hz, 1H), 8.56 (s, 1H), 8.44 (d, *J*=7.6 Hz, 1H), 8.17 - 8.06 (m, 1H), 7.69 - 7.58 (m, 3H), 7.50 - 7.42 (m, 2H), 7.41 - 7.34 (m, 2H), 7.28 (t, *J*=8.0 Hz, 1H), 7.12 (d, *J*=8.4 Hz, 2H), 6.14 - 5.93 (m, 1H), 5.39 - 5.22 (m, 1H), 5.39 - 5.22 (m, 1H), 5.15 - 5.01 (m, 1H), 4.99 - 4.84 (m, 1H), 4.37 (t, *J*=8.0 Hz, 1H), 4.29 (s, 1H), 4.20 (s, 2H), 3.75 - 3.62 (m, 2H), 3.53 - 3.36 (m, 6H), 2.54 - 2.52 (m, 3H), 2.46 (s, 3H), 2.35 (td, *J*=2.0, 8.4 Hz, 2H), 2.30 - 2.17 (m, 2H), 2.10 - 2.01 (m, 2H), 1.84 - 1.72 (m, 5H), 1.49 - 1.42 (m, 1H), 1.41 - 1.34 (m, 3H), 1.24 (s, 1H), 1.00 - 0.94 (m, 3H), 0.87 - 0.78 (m, 4H) |
| 385 | D | A | $^1$H NMR (300 MHz, DMSO-$d_6$) δ 12.87 (s, 1H), 9.85 (s, 1H), 8.96 (s, 1H), 8.64-8.62 (m, 1H), 8.50 (s, 1H), 8.45-8.42 (m, 1H), 8.04 (s, 1H), 7.59-7.56 (m, 3H), 7.45 -7.30 (m, 5H), 7.25-7.23 (m, 1H), 6.79-6.76 (m, 2H), 5.37 (s, 1H), 5.22-5.09 (m, 2H), 4.88-4.81 (m, 1H), 4.55-4.37 (m, 2H), 4.27 (s, 1H), 3.90 (s, 2H), 3.57-3.51 (m, 6H), 3.37- 3.20 (m, 4H), 2.95-2.86 (m, 4H), 2.73-2.66 (m, 2H), 2.43 (s, 3H), 2.24-212 (m, 4H), 1.77-1.75 (m, 3H), 1.35 (d, *J* = 7.0 Hz, 3H), 1.24-1.22 (m, 2H), 0.91 (s, 9H) |

FIG. 3A. Continued

| No. | BRafV600E DC50 (nM) | BRafV600E Dmax (%) | NMR Transcript |
|---|---|---|---|
| 386 | D | A | $^1$H NMR (400 MHz, $CD_3OD$ ppm) δ 8.88 (s, 1H), 8.69 (s, 1H), 8.61 (s, 1H), 7.90 (s, 1H), 7.82 - 7.71 (m, 3H), 7.63 -7.58 (m, 2H), 7.51 - 7.46 (m, 2H), 7.41 - 7.37 (m, 1H), 7.15 - 7.08 (m, 3H), 5.33 – 5.24 (m, 2H), 4.65 - 4.48 (m, 2H), 3.99 (s, 2H), 3.80 - 3.75 (m, 2H), 3.61 – 3.39 (m, 5H), 3.09 (s, 1H), 2.84 - 2.72 (m, 2H), 2.63 (s, 3H), 2.55 - 2.38 (m, 8H), 2.36 - 2.02 (m, 5H), 1.93 - 1.86(m, 2H), 1.81 - 1.69 (m, 1H),1.40 - 1.26(m,3H), 1.05 (s, 2H), 0.98 (s, 7H) |
| 387 | D | Not calculated | $^1$H NMR (300 MHz, DMSO-*d*$_6$, ppm): δ 12.89 (brs, 1H), 9.80 (brs, 1H), 9.04 (s, 1H), 8.69-8.60 (m, 2H), 8.54 (s, 1H), 8.07 (s, 1H), 7.82-7.70 (m, 2H), 7.68-7.50 (m, 3H), 7.35-7.16 (m, 3H), 7.07 (d, *J* = 8.5 Hz, 2H), 5.40-5.22 (m, 1H), 5.14 (d, *J* = 3.4 Hz, 1H), 4.91 (t, *J* = 7.2 Hz, 1H), 4.56-4.41(m, 2H), 4.40-4.30 (m, 1H), 4.39-3.88 (m, 2H), 3.62-3.50 (m, 2H), 3.50 (s, 1H), 3.45-3.40 (m, 2H), 3.32-3.21 (m, 2H), 3.06-2.94 (m, 2H), 2.81-2.62 (m, 3H), 2.48-2.30 (m, 8H), 2.17-1.91 (m, 6H), 1.86-1.55 (m, 3H), 1.41 (d, *J* = 7.0 Hz, 3H), 1.21 -1.01(m, 2H), 0.86 (s, 9H) |
| 388 | D | Not calculated | $^1$H NMR (300 MHz, DMSO-*d*$_6$, *ppm*): δ 12.91 (br s, 1H), 9.85 (br s, 1H), 9.07 (s, 1H), 8.70-8.61 (m, 1H), 8.54 (s, 1H), 8.50-8.40 (m, 1H), 8.08 (s, 1H), 7.70-7.50 (m, 4H), 7.35-7.25 (m, 1H)7.20-6.80 (m, 4H), 5.50-5.00 (m, 3H), 4.60-4.20 (m, 3H), 3.90-3.70 (m, 2H), 3.70-3.60 (m,4H), 3.08-2.83 (m, 4H), 2.80-2.62 (m, 3H), 2.60-2.50 (m, 2H), 2.40-2.30 (m, 3H), 2.30-2.00 (m, 5H), 2.00-1.90 (m, 3H), 1.90-1.55 (m, 4H), 1.55-1.40 (m, 3H), 1.30-1.10 (m, 3H), 0.90 (s, 1H), 0.76 (s, 9H) |
| 389 | D | B | $^1$H NMR: (400MHz, DMSO-*d*$_6$/$D_2O$) *δ*= 8.95 (s, 1H), 8.63 (d, *J*=2.0 Hz, 1H), 8.51 (s, 1H), 8.45 (d, *J*=7.2 Hz, 1H), 8.19 (s, 1H), 8.03 (s, 1H), 7.56 - 7.64 (m, 3H), 7.40 - 7.44 (m, 2H), 7.33 - 7.38 (m, 2H), 7.25 (t, *J*=8.8 Hz, 1H), 7.06 (br d, *J*=8.8 Hz, 2H), 5.19 - 5.38 (m, 1H), 4.83 - 4.93 (m, 1H), 4.37 - 4.51 (m, 2H), 4.27 (s, 1H), 3.35 - 3.48 (m, 4H), 3.25 - 3.32 (m, 1H), 3.18 (s, 4H), 2.89 - 3.11 (m, 3H), 2.53 - 2.83 (m, 6H), 2.43 (s, 3H), 2.30 - 2.39 (m, 1H), 1.99 - 2.12 (m, 4H), 1.84 - 1.99 (m, 2H), 1.68 - 1.81 (m, 2H), 1.44 - 1.53 (m, 1H), 1.37 (d, *J*=6.8 Hz, 3H), 1.21 (d, *J*=8.8 Hz, 1H), 0.95 (s, 9H). |

FIG. 3A. Continued

| No. | BRafV600E DC50 (nM) | BRafV600 E Dmax (%) | NMR Transcript |
|---|---|---|---|
| 375 | D | B | $^1$H NMR: (300 MHz, $CD_3OD$, ppm) δ 8.87 (s, 1H), 8.72 (s, 1H), 8.62-8.61 (d, *J* = 2.1MHz, 1H), 7.91 (s, 1H), 7.75-7.73 (m, 1H), 7.65-7.62 (m, 2H), 7.43-7.38 (m, 6H), 7.11-7.08 (m, 1H), 5.30-5.13 (m, 1H), 5.02-5.00 (m, 1H), 4.63-4.56 (m, 2H), 4.44-4.38 (m, 1H), 3.89-3.73 (m, 2H), 3.67-3.40 (m, 4H), 3.18-3.14 (m, 2H), 3.02 (s, 2H), 2.92-2.88 (m, 2H), 2.68-2.63 (m, 1H), 2.53-2.50 (m, 2H), 2.47 (s, 3H), 2.24-2.18 (m, 6H), 1.95-1.75 (m, 8H), 1.58-1.50 (m, 5H), 1.38-1.34 (m, 3H), 1.05-1.03 (m, 9H) |
| 376 | D | Not calculated | $^1$H NMR: (400MHz, DMSO-$d_6$) *δ:* 12.87 (s, 1H), 8.97 (s, 1H), 8.64 (d, *J*=2.4 Hz, 1H), 8.52 (s, 1H), 8.31 (s, 1H), 8.18 (s, 1H), 8.05 (s, 1H), 7.82 (d, *J*=9.6 Hz, 1H), 7.66 - 7.58 (m, 2H), 7.58 - 7.52 (m, 3H), 7.33 (d, *J*=8.4 Hz, 2H), 7.24 (t, *J*=8.0 Hz, 1H), 7.12 - 7.00 (m, 2H), 5.41 - 5.20 (m, 1H), 4.58 - 4.45 (m, 2H), 4.33 (s, 1H), 3.76 (d, J=12.0 Hz, 2H), 3.64 - 3.52 (m, 3H), 3.48 - 3.42 (m, 3H), 3.37 (dd, J=2.8, 12.0 Hz, 5H), 3.32 - 3.28 (m, 2H), 3.27 - 3.22 (m, 2H), 3.17 (s, 1H), 3.06 (d, J=16.0 Hz, 2H), 2.93 (d, J=16.0 Hz, 2H), 2.77 - 2.69 (m, 1H), 2.17 (d, J=7.2 Hz, 2H), 2.14 - 1.93 (m, 4H), 1.84 (ddd, J=4.4, 8.8, 12.8 Hz, 1H), 1.80 - 1.66 (m, 3H), 1.60 (s, 3H), 1.50 (s, 3H), 1.30 - 1.13 (m, 2H), 1.05 (t, *J*=7.2 Hz, 1H), 0.96 - 0.86 (m, 9H) |
| 377 | B | A | $^1$H NMR: (400MHz, DMSO-$d_6$) *δ:* 12.90 (s, 1H), 9.01 - 8.95 (m, 1H), 8.64 (d, J=2.4 Hz, 1H), 8.53 (s, 1H), 8.44 - 8.36 (m, 1H), 8.15 (s, 1H), 8.06 (s, 1H), 7.99 (d, J=9.2 Hz, 1H), 7.69 - 7.53 (m, 3H), 7.47 - 7.41 (m, 2H), 7.41 - 7.35 (m, 2H), 7.30 - 7.21 (m, 5H), 7.06 (d, J=8.8 Hz, 2H), 5.41 - 5.19 (m, 1H), 5.10 (s, 1H), 5.00 - 4.84 (m, 1H), 4.50 (d, J=9.2 Hz, 1H), 4.43 (t, J=8.0 Hz, 1H), 4.27 (s, 1H), 3.66 - 3.55 (m, 3H), 3.49 (d, J=14.4 Hz, 4H), 3.39 (s, 3H), 3.21 (s, 3H), 2.56 - 2.53 (m, 2H), 2.52 (s, 3H), 2.45 (s, 3H), 2.25 - 1.87 (m, 4H), 1.84 - 1.67 (m, 1H), 1.38 (d, J=7.2 Hz, 3H), 1.00 - 0.80 (m, 9H) |
| 378 | D | Not calculated | $^1$H NMR: (400MHz, DMSO-$d_6$) *δ:* 12.96 (s, 1H), 8.98 (s, 1H), 8.68 (d, *J*=2.0 Hz, 1H), 8.58 (s, 1H), 8.39 (d, *J*=7.6 Hz, 1H), 8.19 (s, 1H), 8.10 (s, 1H), 7.98 (d, *J*=9.2 Hz, 1H), 7.66 (d, *J*=8.0 Hz, 2H), 7.63 - 7.58 (m, 1H), 7.45 - 7.42 (m, 2H), 7.41 - 7.36 (m, 4H), 7.27 - 7.21 (m, 6H), 5.37 - 5.19 (m, 1H), 5.09 (s, 1H), 4.91 (t, *J*=7.6 Hz, 1H), 4.49 (d, *J*=9.2 Hz, 1H), 4.43 (t, *J*=8.0 Hz, 1H), 4.27 (s, 1H), 3.68 - 3.54 (m, 4H), 3.31 - 3.23 (m, 3H), 2.93 (d, *J*=10.4 Hz, 2H), 2.45 (s, 3H), 2.12 - 1.97 (m, 6H), 1.83 - 1.66 (m, 6H), 1.37 (d, *J*=7.2 Hz, 3H), 0.97 - 0.85 (m, 11H) |

FIG. 3A. Continued

| No. | BRafV600E DC50 (nM) | BRafV600E Dmax (%) | NMR Transcript |
|---|---|---|---|
| 379 | D | Not calculated | $^1$H NMR: (400 MHz, DMSO-d6) δ = 10.68 (s, 1H), 8.97 (s, 1H), 8.84 (d, *J*=2.4 Hz, 1H), 8.44 (d, *J*=8.0 Hz, 1H), 8.38 - 8.26 (m, 2H), 8.06 - 7.98 (m, 2H), 7.82 - 7.71 (m, 2H), 7.50- 7.34 (m, 6H), 7.16 - 7.02 (m, 4H), 5.14 (s, 1H), 4.99 - 4.74 (m, 1H), 4.58 (d, *J*=9.6 Hz, 1H), 4.64 - 4.53 (m, 1H), 4.28 (s, 1H), 4.16 - 4.14 (m, 2H ), 4.02 (d, *J*=8.0 Hz, 2H), 3.89 - 3.71 (m, 6H), 3.55-3.64 (m, 2H), 3.18 (s, 4H), 2.45-2.42 (m, 6H), 2.07 – 2.01 (m, 1H), 1.80 - 1.74 (m, 1H), 1.48 - 1.34 (m, 3H), 0.96 (s, 9H). |
| 380 | D | Not calculated | $^1$H NMR: (400 MHz, DMSO-d6) δ: 10.85 (s, 1H), 9.06 - 8.91 (m, 2H), 8.44 (d, *J*=7.6 Hz, 1H), 8.34 (s, 1H), 8.30 (d, *J*=8.8 Hz, 1H), 8.21 (d, *J*=2.0 Hz, 1H), 8.02 (d, *J*=7.2 Hz, 1H), 7.83 (t, *J*=8.0 Hz, 1H), 7.75 (d, *J*=2.0 Hz, 1H), 7.42 (d, *J*=8.4 Hz, 4H), 7.38 - 7.32 (m, 2H), 7.15 - 7.06 (m, 2H), 7.00 (d, *J*=9.0 Hz, 2H), 4.94 - 4.86 (m, 1H), 4.56 (d, *J*=9.6 Hz, 1H), 4.48 - 4.42 (m, 1H), 4.31 - 4.27 (m, 1H), 4.18 - 4.13 (m, 2H), 3.99 (s, 2H), 3.78 (br s, 7H), 3.67 (s, 6H), 3.20 (s, 4H), 2.53 (s, 3H), 2.44 (s, 3H), 2.10 - 2.01 (m, 1H), 1.78 (m, 1H), 1.49 - 1.32 (m, 3H), 0.95 (s, 9H) |
| 381 | D | Not calculated | $^1$H NMR: (400MHz, DMSO-$d_6$) δ: 10.68 (s, 1H), 8.98 (s, 1H), 8.85 (d, *J*=2.4 Hz, 1H), 8.44 (d, *J*=7.6 Hz, 1H), 8.38 - 8.25 (m, 2H), 8.06 (d, *J*=2.4 Hz, 1H), 8.00 (d, *J*=7.6 Hz, 1H), 7.81 (t, *J*=8.0 Hz, 1H), 7.72 (d, *J*=2.0 Hz, 1H), 7.49 - 7.30 (m, 6H), 7.15 - 7.06 (m, 2H), 7.03 - 6.93 (m, 2H), 5.13 (s, 1H), 4.90 (t, *J*=7.2 Hz, 1H), 4.55 (d, *J*=9.6 Hz, 1H), 4.45 (t, *J*=8.0 Hz, 1H), 4.32 - 4.25 (m, 1H), 4.15 - 4.06 (m, 2H), 3.97 (s, 2H), 3.81 - 3.73 (m, 6H), 3.66 - 3.55 (m, 10H), 3.19 (s, 4H), 2.44 (d, *J*=2.8 Hz, 6H), 2.12 - 1.99 (m, 1H), 1.83 - 1.73 (m, 1H), 1.51 - 1.32 (m, 3H), 0.94 (s, 9H) |
| 382 | D | Not calculated | $^1$H NMR: (400MHz, DMSO-$d_6$) δ = 10.68 (s, 1H), 8.97 (s, 1H), 8.84 (d, *J*=2.4 Hz, 1H), 8.44 (d, *J*=8.0 Hz, 1H), 8.38 - 8.26 (m, 2H), 8.06 - 7.98 (m, 2H), 7.82 - 7.71 (m, 2H), 7.50- 7.34 (m, 6H), 7.16 - 7.02 (m, 4H), 5.14 (s, 1H), 4.99 - 4.74 (m, 1H), 4.58 (d, *J*=9.6 Hz, 1H), 4.64 - 4.53 (m, 1H), 4.28 (s, 1H), 4.16 - 4.14 (m, 2H ), 4.02 (d, *J*=8.0 Hz, 2H), 3.89 - 3.71 (m, 6H), 3.55-3.64 (m, 18H), 3.18 (s, 4H), 2.45-2.42 (m, 6H), 2.07 – 2.01 (m, 1H), 1.80 - 1.74 (m, 1H), 1.48 - 1.34 (m, 3H), 0.96 (s, 9H). |

FIG. 3A. Continued

| No. | BRafV600E DC50 (nM) | BRafV600 E Dmax (%) | NMR Transcript |
|---|---|---|---|
| 383 | C | B | $^1$H NMR: (400MHz, DMSO-$d_6$) $\delta$: 12.86 (s, 1H), 9.01 - 8.96 (m, 1H), 8.95 - 8.82 (m, 1H), 8.63 (d, $J$=2.1 Hz, 1H), 8.52 (s, 1H), 8.30 (d, $J$=7.6 Hz, 1H), 8.03 (s, 1H), 7.63 - 7.46 (m, 4H), 7.45 - 7.38 (m, 2H), 7.35 - 7.30 (m, 2H), 7.13 (s, 1H), 7.05 (d, $J$=8.8 Hz, 2H), 6.16 - 6.07 (m, 1H), 5.37 - 5.17 (m, 1H), 5.11 (d, $J$=3.2 Hz, 1H), 5.05 - 4.96 (m, 1H), 4.90 (t, $J$=7.2 Hz, 1H), 4.42 (t, $J$=7.6 Hz, 1H), 4.26 (s, 1H), 4.22 - 4.11 (m, 2H), 3.75 (d, $J$=8.8 Hz, 1H), 3.59 - 3.36 (m, 4H), 3.29 - 3.12 (m, 6H), 2.45 (s, 3H), 2.41 - 2.31 (m, 3H), 2.30 - 2.22 (m, 1H), 2.11 - 2.02 (m, 3H), 1.82 - 1.68 (m, 3H), 1.56 (dd, $J$=7.6, 14.5 Hz, 2H), 1.48 - 1.41 (m, 1H), 1.35 (d, $J$=7.2 Hz, 3H), 0.96 (d, $J$=6.4 Hz, 3H), 0.83 (d, $J$=6.8 Hz, 3H) |
| 384 | D | A | $^1$H NMR: (400MHz, DMSO-$d_6$) $\delta$: 12.95 (s, 1H), 9.90 (s, 1H), 8.99 (s, 1H), 8.92 (s, 1H), 8.67 (d, $J$=2.0 Hz, 1H), 8.56 (s, 1H), 8.44 (d, $J$=7.6 Hz, 1H), 8.17 - 8.06 (m, 1H), 7.69 - 7.58 (m, 3H), 7.50 - 7.42 (m, 2H), 7.41 - 7.34 (m, 2H), 7.28 (t, $J$=8.0 Hz, 1H), 7.12 (d, $J$=8.4 Hz, 2H), 6.14 - 5.93 (m, 1H), 5.39 - 5.22 (m, 1H), 5.39 - 5.22 (m, 1H), 5.15 - 5.01 (m, 1H), 4.99 - 4.84 (m, 1H), 4.37 (t, $J$=8.0 Hz, 1H), 4.29 (s, 1H), 4.20 (s, 2H), 3.75 - 3.62 (m, 2H), 3.53 - 3.36 (m, 6H), 2.54 - 2.52 (m, 3H), 2.46 (s, 3H), 2.35 (td, $J$=2.0, 8.4 Hz, 2H), 2.30 - 2.17 (m, 2H), 2.10 - 2.01 (m, 2H), 1.84 - 1.72 (m, 5H), 1.49 - 1.42 (m, 1H), 1.41 - 1.34 (m, 3H), 1.24 (s, 1H), 1.00 - 0.94 (m, 3H), 0.87 - 0.78 (m, 4H) |
| 385 | D | A | $^1$H NMR (300 MHz, DMSO-$d_6$) $\delta$ 12.87 (s, 1H), 9.85 (s, 1H), 8.96 (s, 1H), 8.64-8.62 (m, 1H), 8.50 (s, 1H), 8.45-8.42 (m, 1H), 8.04 (s, 1H), 7.59-7.56 (m, 3H), 7.45 -7.30 (m, 5H), 7.25-7.23 (m, 1H), 6.79-6.76 (m, 2H), 5.37 (s, 1H), 5.22-5.09 (m, 2H), 4.88-4.81 (m, 1H), 4.55-4.37 (m, 2H), 4.27 (s, 1H), 3.90 (s, 2H), 3.57-3.51 (m, 6H), 3.37- 3.20 (m, 4H), 2.95-2.86 (m, 4H), 2.73-2.66 (m, 2H), 2.43 (s, 3H), 2.24-212 (m, 4H), 1.77-1.75 (m, 3H), 1.35 (d, $J$ = 7.0 Hz, 3H), 1.24-1.22 (m, 2H), 0.91 (s, 9H) |

FIG. 3A. Continued

| No. | BRafV600E DC50 (nM) | BRafV600E Dmax (%) | NMR Transcript |
|---|---|---|---|
| 386 | D | A | $^1$H NMR (400 MHz, $CD_3OD$ ppm) δ 8.88 (s, 1H), 8.69 (s, 1H), 8.61 (s, 1H), 7.90 (s, 1H), 7.82 - 7.71 (m, 3H), 7.63 -7.58 (m, 2H), 7.51 - 7.46 (m, 2H), 7.41 - 7.37 (m, 1H), 7.15 - 7.08 (m, 3H), 5.33 – 5.24 (m, 2H), 4.65 - 4.48 (m, 2H), 3.99 (s, 2H), 3.80 - 3.75 (m, 2H), 3.61 – 3.39 (m, 5H), 3.09 (s, 1H), 2.84 - 2.72 (m, 2H), 2.63 (s, 3H), 2.55 - 2.38 (m, 8H), 2.36 - 2.02 (m, 5H), 1.93 - 1.86(m, 2H), 1.81 - 1.69 (m, 1H),1.40 - 1.26(m,3H), 1.05 (s, 2H), 0.98 (s, 7H) |
| 387 | D | Not calculated | $^1$H NMR (300 MHz, DMSO-$d_6$, ppm): δ 12.89 (brs, 1H), 9.80 (brs, 1H), 9.04 (s, 1H), 8.69-8.60 (m, 2H), 8.54 (s, 1H), 8.07 (s, 1H), 7.82-7.70 (m, 2H), 7.68-7.50 (m, 3H), 7.35-7.16 (m, 3H), 7.07 (d, $J$ = 8.5 Hz, 2H), 5.40-5.22 (m, 1H), 5.14 (d, $J$ = 3.4 Hz, 1H), 4.91 (t, $J$ = 7.2 Hz, 1H), 4.56-4.41(m, 2H), 4.40-4.30 (m, 1H), 4.39-3.88 (m, 2H), 3.62-3.50 (m, 2H), 3.50 (s, 1H), 3.45-3.40 (m, 2H), 3.32-3.21 (m, 2H), 3.06-2.94 (m, 2H), 2.81-2.62 (m, 3H), 2.48-2.30 (m, 8H), 2.17-1.91 (m, 6H), 1.86-1.55 (m, 3H), 1.41 (d, $J$ = 7.0 Hz, 3H), 1.21 -1.01(m, 2H), 0.86 (s, 9H) |
| 388 | D | Not calculated | $^1$H NMR (300 MHz, DMSO-$d_6$, *ppm*): δ 12.91 (br s, 1H), 9.85 (br s, 1H), 9.07 (s, 1H), 8.70-8.61 (m, 1H), 8.54 (s, 1H), 8.50-8.40 (m, 1H), 8.08 (s, 1H), 7.70-7.50 (m, 4H), 7.35-7.25 (m, 1H)7.20-6.80 (m, 4H), 5.50-5.00 (m, 3H), 4.60-4.20 (m, 3H), 3.90-3.70 (m, 2H), 3.70-3.60 (m,4H), 3.08-2.83 (m, 4H), 2.80-2.62 (m, 3H), 2.60-2.50 (m, 2H), 2.40-2.30 (m, 3H), 2.30-2.00 (m, 5H), 2.00-1.90 (m, 3H), 1.90-1.55 (m, 4H), 1.55-1.40 (m, 3H), 1.30-1.10 (m, 3H), 0.90 (s, 1H), 0.76 (s, 9H) |
| 389 | D | B | $^1$H NMR: (400MHz, DMSO-$d_6$/$D_2O$) $\delta$= 8.95 (s, 1H), 8.63 (d, $J$=2.0 Hz, 1H), 8.51 (s, 1H), 8.45 (d, $J$=7.2 Hz, 1H), 8.19 (s, 1H), 8.03 (s, 1H), 7.56 - 7.64 (m, 3H), 7.40 - 7.44 (m, 2H), 7.33 - 7.38 (m, 2H), 7.25 (t, $J$=8.8 Hz, 1H), 7.06 (br d, $J$=8.8 Hz, 2H), 5.19 - 5.38 (m, 1H), 4.83 - 4.93 (m, 1H), 4.37 - 4.51 (m, 2H), 4.27 (s, 1H), 3.35 - 3.48 (m, 4H), 3.25 - 3.32 (m, 1H), 3.18 (s, 4H), 2.89 - 3.11 (m, 3H), 2.53 - 2.83 (m, 6H), 2.43 (s, 3H), 2.30 - 2.39 (m, 1H), 1.99 - 2.12 (m, 4H), 1.84 - 1.99 (m, 2H), 1.68 - 1.81 (m, 2H), 1.44 - 1.53 (m, 1H), 1.37 (d, $J$=6.8 Hz, 3H), 1.21 (d, $J$=8.8 Hz, 1H), 0.95 (s, 9H). |

FIG. 3A. Continued

| No. | BRafV600E DC50 (nM) | BRafV600 E Dmax (%) | NMR Transcript |
|---|---|---|---|
| 390 | D | A | $^1$H NMR: (400MHz, DMSO/$D_2O$-$d_6$) $\delta$= 8.91 (s, 1H), 8.62 (d, $J$=2.0 Hz, 1H), 8.45 (d, $J$=7.2 Hz, 1H), 8.21 (s, 1H), 8.01 (s, 1H), 7.54 - 7.64 (m, 3H), 7.38 - 7.43 (m, 2H), 7.32 - 7.37 (m, 2H), 7.25 (t, $J$=8.4 Hz, 1H), 6.99 - 7.09 (m, 2H), 5.18 - 5.36 (m, 1H), 4.87 (t, $J$=7.2 Hz, 1H), 4.36 - 4.49 (m, 2H), 4.26 - 4.33 (m, 1H), 3.59 (s, 1H), 3.36 - 3.46 (m, 3H), 3.15 - 3.26 (m, 4H), 2.94 - 3.05 (m, 3H), 2.66 - 2.76 (m, 5H), 2.41 (s, 3H), 2.33 (s, 1H), 1.92 - 2.12 (m, 6H), 1.75 (d, $J$=8.8 Hz, 3H), 1.45 (d, $J$=6.8 Hz, 1H), 1.36 (d, $J$=6.8 Hz, 3H), 1.11 - 1.19 (m, 2H), 0.92 (s, 9H). |
| 391 | D | A | $^1$H NMR: (400MHz, DMSO-$d_6$/$D_2O$) $\delta$: 8.90 - 8.94 (m, 1H), 8.53 - 8.70 (m, 3H), 8.29 (s, 1H), 8.04 (s, 1H), 7.68 (d, $J$=8.0 Hz, 2H), 7.62 (td, $J$=8.8, 5.6 Hz, 1H), 7.37 - 7.40 (m, 5H), 7.37 - 7.42 (m, 1H), 7.24 (t, $J$=8.8 Hz, 1H), 5.19 - 5.35 (m, 1H), 4.23 - 4.53 (m, 6H), 3.65 (s, 1H), 3.25 - 3.46 (m, 6H), 2.66 - 3.11 (m, 9H), 2.41 - 2.44 (m, 3H), 2.14 - 2.35 (m, 3H), 1.89 - 2.09 (m, 8H), 1.61 - 1.73 (m, 2H), 0.90 - 0.95 (m, 9H). |
| 392 | D | A | $^1$H NMR (400 MHz, DMSO-$d_6$, *ppm*): δ 12.86 (brs, 1H), 9.79 (brs, 1H), 8.99 (s, 1H), 8.64 (d, J = 2.2 Hz, 1H), 8.52-8.39 (m, 2H), 8.05 (s, 1H), 7.79-7.20 (m, 9H), 6.73 (d, J = 8.3 Hz, 2H), 5.39-4.85 (m, 3H), 4.50-4.25 (m, 4H), 3.80 (s, 1H), 3.56-3.38 (m, 6H), 3.31-3.25 (m, 2H), 3.11-2.72 (m, 5H), 2.60-2.55 (m, 2H), 2.46-2.41 (m, 1H), 2.22-2.03 (m, 6H), 1.82-1.62 (m, 5H), 1.48-1.35 (m, 5H), 0.93 (s, 9H) |
| 393 | D | A | $^1$H NMR (400 MHz, DMSO-$d_6$, ppm): δ 12.90 (brs, 1H), 9.84 (brs, 1H), 8.98 (s, 1H), 8.65 (d, J = 2.2 Hz, 1H), 8.54 (s, 1H), 8.44 (d, J = 7.7 Hz, 1H), 8.06 (s, 1H), 7.90-7.65 (m, 1H), 7.62-7.50 (m, 3H), 7.43-7.36 (m, 4H), 7.24 (t, J = 8.9 Hz, 1H), 7.07 (d, J = 8.2 Hz, 2H), 5.41-5.21 (m, 1H), 5.22- 5.10 (m, 1H), 4.89 (t, J = 7.2 Hz, 1H), 4.55-4.39 (m, 2H), 4.28 (s, 1H), 4.65-3.58 (m, 2H), 3.55-3.47(m,1H), 3.37-3.31 (m, 2H), 3.27-3.03 (m, 8H), 2.55-2.46 (m, 3H), 2.45-2.40 (m, 4H), 2.44-2.36 (m, 2H), 2.07 (m, 3H),1.70 (m, 3H), 1.45 (s, 2H), 1.41-1.35 (m, 3H), 1.24 (s, 2H), 0.94 (d, J = 3.3 Hz, 9H). |

FIG. 3A. Continued

| No. | BRafV600E DC50 (nM) | BRafV600E Dmax (%) | NMR Transcript |
|---|---|---|---|
| 394 | D | A | $^1$H NMR (300 MHz, $CD_3OD$) δ8.86 (s, 1H), 8.71 (s, 1H), 8.62-8.61 (m, 1H), 7.91 (s, 1H), 7.78-7.71 (m, 1H), 7.61 (d, *J*=9.0Hz, 2H), 7.45-7.37 (m, 6H), 7.15-7.09 (m, 1H), 5.21 (d, *J*=53.2Hz, 1H), 5.04-4.97 (m, 1H), 4.63-4.50 (m, 2H), 4.43-4.37 (m, 1H), 3.88-3.84 (m, 1H), 3.77-3.72 (m, 1H), 3.61-3.35 (m, 5H), 3.06 (s, 2H), 2.68-2.62 (m, 8H), 2.48-2.47 (m, 5H), 2.24-2.10 (m, 3H), 2.03-1.91 (m, 3H), 1.79-1.68 (m, 7H), 1.58-1.50 (m, 3H), 1.05-1.03 (m, 9H) |
| 395 | D | A | $^1$H NMR: (400MHz, DMSO-*d*$_6$) *δ:* 12.86 (br s, 1H), 8.98 (s, 1H), 8.62 (d, *J*=2.0 Hz, 1H), 8.48 (s, 1H), 8.42 (d, *J*=8.0 Hz, 1H), 8.15 (s, 1H), 8.04 (s, 1H), 7.69 (d, *J*=9.6 Hz, 1H), 7.62 (dt, *J*=6.0, 9.2 Hz, 1H), 7.52 (d, *J*=8.4 Hz, 2H), 7.45 - 7.40 (m, 2H), 7.38 - 7.33 (m, 2H), 7.25 (t, *J*=8.8 Hz, 1H), 6.65 (d, *J*=8.8 Hz, 2H), 5.38 - 5.19 (m, 1H), 5.11 (s, 1H), 4.88 (t, *J*=7.3 Hz, 1H), 4.48 (d, *J*=9.8 Hz, 1H), 4.42 (t, *J*=8.4 Hz, 1H), 4.27 (s, 1H), 4.16 (s, 1H), 3.64 - 3.53 (m, 2H), 3.48 - 3.45 (m, 1H), 3.41 - 3.37 (m, 4H), 3.27 - 3.25 (m, 2H), 3.09 - 3.00 (m, 2H), 2.93 - 2.86 (m, 1H), 2.61 - 2.54 (m, 1H), 2.52 - 2.51 (m, 4H), 2.45 (s, 3H), 2.24 - 1.93 (m, 7H), 1.91 - 1.70 (m, 4H), 1.66 (d, *J*=7.2 Hz, 1H), 1.36 (d, *J*=7.2 Hz, 3H), 1.11 (d, *J*=11.2 Hz, 1H), 0.92 (s, 9H) |
| 396 | D | Not calculated | $^1$H NMR: (400 MHz, DMSO-d6) *δ:* 10.67 (s, 1H), 8.97 (s, 1H), 8.85 (d, *J* = 2.4 Hz, 1H), 8.43 (d, *J* = 7.2 Hz, 1H), 8.32 (s, 1H), 8.28 (d, *J* = 8.0 Hz, 1H), 8.05 (d, *J* = 2.4 Hz, 1H), 7.99 (d, *J* = 8.0 Hz, 1H), 7.84 - 7.78 (m, 1H), 7.71 (d, *J* = 2.4 Hz, 1H), 7.45 - 7.40 (m, 2H), 7.38 - 7.34 (m, 3H), 7.09 (d, *J* = 9.2 Hz, 2H), 6.98 (d, *J* = 8.8 Hz, 2H), 5.12 (s, 1H), 4.89 (d, *J* = 6.8 Hz, 1H), 4.54 (d, *J* = 9.2 Hz, 1H), 4.44 (t, *J* = 8.0 Hz, 1H), 4.27 (s, 1H), 4.09 (d, *J* = 5.2 Hz, 2H), 3.96 (s, 2H), 3.76 (s, 6H), 3.63 - 3.54 (m, 14H), 3.18 (s, 4H), 2.44 (d, *J* = 3.6 Hz, 6H), 2.05 (s, 1H), 1.77 (s, 1H), 1.36 (d, *J* = 7.2 Hz, 2H), 1.41 - 1.32 (m, 1H), 0.93 (s, 9H). |

FIG. 3A. Continued

| No. | BRafV600E DC50 (nM) | BRafV600E Dmax (%) | NMR Transcript |
|---|---|---|---|
| 397 | D | A | $^1$H NMR: (400MHz, DMSO-$d_6$) *δ:* 12.86 (s, 1H), 8.98 (s, 1H), 8.71 - 8.62 (m, 1H), 8.55 (s, 1H), 8.42 (d, *J*=7.6 Hz, 1H), 8.41 - 8.39 (m, 1H), 8.17 (s, 1H), 8.07 (s, 1H), 7.76 (d, *J*=9.6 Hz, 1H), 7.65 (d, *J*=8.4 Hz, 2H), 7.63 - 7.58 (m, 1H), 7.48 - 7.40 (m, 2H), 7.39 - 7.33 (m, 2H), 7.28 - 7.22 (m, 1H), 7.28 - 7.22 (m, 1H), 6.96 (d, *J*=8.8 Hz, 2H), 5.36 (s, 1H), 5.39 - 5.19 (m, 1H), 5.23 (s, 1H), 4.96 - 4.84 (m, 2H), 4.54 - 4.42 (m, 2H), 4.40 - 4.32 (m, 1H), 4.28 (s, 1H), 3.64 - 3.53 (m, 3H), 3.47 (s, 2H), 3.08 - 2.97 (m, 2H), 2.94 - 2.87 (m, 1H), 2.71 (s, 2H), 2.45 (s, 3H), 2.44 - 2.35 (m, 5H), 2.30 - 2.18 (m, 2H), 2.17 - 1.94 (m, 4H), 1.85 (s, 2H), 1.81 - 1.72 (m, 1H), 1.55 - 1.44 (m, 2H), 1.39 (d, *J*=7.2 Hz, 3H), 0.94 (s, 9H) |
| 398 | D | A | $^1$H NMR (300 MHz, $CD_3OD$) δ8.87 (s, 1H), 8.72 (s, 1H), 8.62-8.61 (m, 1H), 7.91 (s, 1H), 7.79-7.71 (m, 1H), 7.61 (d, *J*=8.1Hz, 2H), 7.46-7.36 (m, 6H), 7.17-7.11 (m, 1H), 5.22 (d, *J* = 53.2Hz, 1H), 5.05-4.98 (m, 1H), 4.64-4.54 (m, 2H), 4.49-4.38 (m, 1H), 3.88-3.84 (m, 1H), 3.77-3.72 (m, 1H), 3.62-3.35 (m, 5H), 3.17-3.03 (m, 2H), 2.67-2.53 (m, 9H), 2.48 (s, 3H), 2.40-2.37 (m, 2H), 2.25-2.11 (m, 2H), 2.04-1.91 (m, 5H), 1.71-1.64 (m, 1H), 1.59-1.51 (m, 5H), 1.32-1.14 (m, 2H), 1.05-1.03 (m, 9H) |
| 399 | D | A | $^1$H NMR (400 MHz, $CD_3OD$) δ 12.80 (s, 1H), 9.82 (s, 1H), 8.92 (s, 1H), 8.57-8.45 (m, 3H), 7.99 (s, 1H), 7.75 (s, 1H), 7.52-7.49 (s, 3H), 7.34-7.21 (m, 4H), 7.18-7.16 (m, 1H), 6.99-6.97 (m, 2H), 5.13-5.08 (m, 2H), 4.44-4.29 (m, 3H), 3.71-3.61 (m, 5H), 3.41- 3.31 (m, 4H), 2.94-2.82 (m, 3H), 2.75-2.73 (m, 2H), 2.63-2.59 (m, 7H), 2.18-1.90 (m, 7H), 1.86-1.83 (m, 3H), 1.16-1.11 (m, 3H), 0.87 (s, 9H) |

FIG. 3A. Continued

| No. | BRafV600E DC50 (nM) | BRafV600E Dmax (%) | NMR Transcript |
|---|---|---|---|
| 400 | D | A | $^{1}$H NMR: (400MHz, DMSO-$d_6$) $\delta$: 12.82 (s, 1H), 8.97 (s, 1H), 8.62 (d, $J$=2.0 Hz, 1H), 8.47 (s, 1H), 8.40 (d, $J$=7.2 Hz, 1H), 8.17 (s, 1H), 8.03 (s, 1H), 7.69 (d, $J$=9.2 Hz, 1H), 7.61 (dt, $J$=6.0, 9.0 Hz, 1H), 7.52 (d, $J$=8.4 Hz, 2H), 7.44 - 7.39 (m, 2H), 7.37 - 7.33 (m, 2H), 7.24 (t, $J$=8.4 Hz, 1H), 6.65 (d, $J$=8.0 Hz, 2H), 5.39 - 5.19 (m, 1H), 4.88 (t, $J$=7.2 Hz, 1H), 4.51 - 4.37 (m, 2H), 4.27 (s, 1H), 4.16 (s, 1H), 3.62 - 3.52 (m, 2H), 3.47 (s, 1H), 3.42 - 3.24 (m, 9H), 3.13 - 2.98 (m, 3H), 2.94 - 2.86 (m 1H), 2.52 - 2.51 (m, 2H), 2.45 (s, 3H), 2.37 -2.28 (m, 3H), 2.25 - 1.93 (m, 6H), 1.92 - 1.71 (m, 3H), 1.70 - 1.61 (m, 1H), 1.36 (d, $J$=7.2 Hz, 3H), 1.11 (d, $J$=13.2 Hz, 1H), 0.92 (s, 9H) |
| 401 | | | $^{1}$H NMR: (400 MHz, DMSO-$d_6$) $\delta$: 12.94 (s, 1H), 9.86 (s, 1H), 8.60 (d, $J$=41.2 Hz, 2H) 8.08 (s, 1H), 7.70-7.57 (m, 3H), 7.45-7.21 (m, 2H), 7.14 (d, $J$=6.8 Hz, 2H), 6.85 (s, 1H), 5.29 (d, $J$=53.2 Hz, 1H), 4.74-4.20 (m, 3H), 3.82 (d, $J$=11.2 Hz, 6 H), 3.68-3.61 (m, 2H), 3.55 (d, $J$=9.6 Hz, 2 H), 3.49 (d, $J$=9.2 Hz, 2 H), 3.39 (d, $J$=10.4 Hz, 4 H), 3.35 - 3.23 (m, 3H), 2.89 - 2.74 (m, 4H), 2.15 - 1.92 (m, 5H), 1.92 - 1.71 (m, 3H), 1.39 - 1.30 (m, 2H), 0.94 (d, $J$=18.8 Hz, 9 H) |
| 402 | D | Not calculated | $^{1}$H NMR: (400 MHz, DMSO-$d_6$) $\delta$ : 12.97 (s, 1H), 9.82 (s, 1H), 9.05 - 8.88 (m, 1H), 8.74 (s, 2H), 8.65 (s, 1H), 8.54 (s, 1H), 8.18 (s, 1H), 8.10 (s, 1H), 7.62 (d, $J$=6.0 Hz, 1H), 7.52 - 7.39 (m, 2H), 7.36 - 7.20 (m, 2H), 6.18 (s, 1H), 5.44 - 5.18 (m, 1H), 5.10 (s, 1H), 5.03 - 4.86 (m, 1H), 4.73 (d, $J$=11.2 Hz, 2H), 4.58 - 4.38 (m, 1H), 4.28 (s, 1H), 3.70 (s, 1H), 3.56 (s, 2H), 3.49 (s, 2H), 3.40 (d, $J$=8.4 Hz, 4H), 3.15 (s, 5H), 2.97 (s, 1H), 2.67 (s, 3H), 2.47 - 2.42 (m, 4H), 2.36 - 2.23 (m, 2H), 2.17 - 2.02 (m, 4H), 1.99 - 1.74 (m, 3H), 1.46 (d, $J$=7.2 Hz, 1H), 1.36 (d, $J$=7.2 Hz, 2H), 1.26 - 1.02 (m, 3H), 0.97 (d, $J$=6.4 Hz, 2H), 0.87 - 0.65 (m, 3H). |

FIG. 3A. Continued

| No. | BRafV600E DC50 (nM) | BRafV600E Dmax (%) | NMR Transcript |
|---|---|---|---|
| 403 | D | A | $^1$H NMR: (400MHz, DMSO-$d_6$) δ : 12.99 (s, 1H), 9.82 (s, 1H), 8.98 (s, 1H), 8.76 (s, 2H), 8.66 (s, 1H), 8.56 (s, 1H), 8.37 (d, J=6.8 Hz, 1H), 8.11 (s, 1H), 7.69 - 7.56 (m, 1H), 7.51 - 7.41 (m, 2H), 7.40 - 7.33 (m, 2H), 7.27 (t, J=8.8 Hz, 1H), 6.34 - 6.16 (m, 1H), 5.43 - 5.21 (m, 1H), 5.11 (s, 1H), 4.99 - 4.84 (m, 1H), 4.75 (d, J=12.0 Hz, 2H), 4.52 - 4.20 (m, 2H), 3.80 (s, 2H), 3.73 (d, J=6.4 Hz, 1H), 3.63 (d, J=9.2 Hz, 3H), 3.47 (d, J=13.6 Hz, 3H), 3.41 (s, 3H), 3.24 (s, 2H), 3.13 (s, 3H), 3.07 - 2.96 (m, 2H), 2.49 - 2.44 (m, 1H), 2.46 (s, 3H), 2.30 - 2.10 (m, 4H), 2.08 - 1.97 (m, 2H), 1.92 - 1.76 (m, 2H), 1.52 - 1.34 (m, 3H), 1.24 (s, 3H), 0.98 (d, J=6.0 Hz, 2H), 0.90 - 0.77 (m, 3H). |
| 404 | D | A | $^1$H NMR: (400MHz, DMSO-$d_6$) δ: 12.94 (s, 1H), 9.88 (s, 1H), 8.98 (s, 1H), 8.84 (s, 1H), 8.66 (d, J=2.4 Hz, 1H), 8.56 (s, 1H), 8.09 (s, 1H), 7.68 - 7.56 (m, 3H), 7.35 - 7.22 (m, 5H), 7.13 (d, J=7.2 Hz, 2H), 5.43 - 5.20 (m, 1H), 4.57 (d, J=9.6 Hz, 1H), 4.45 - 4.31 (m, 2H), 4.00 - 3.79 (m, 1H), 3.48 (s, 3H), 3.43 - 3.37 (m, 4H), 3.30 (dd, J=6.8, 10.5 Hz, 3H), 3.14 (d, J=17.6 Hz, 4H), 2.98 (s, 4H), 2.80 ( s, 3H), 2.48 - 2.47 (m, 2H), 2.44 (s, 3H), 2.20 - 1.75 (m, 8H), 1.42 - 1.08 (m, 6H), 1.02 - 0.88 (m, 9H) |
| 405 | D | B | $^1$H NMR: (400MHz, DMSO-$d_6$) δ: 12.95 (s, 1H), 9.88 (s, 1H), 8.66 (d, J=2.0 Hz, 1H), 8.56 (s, 1H), 8.41 (d, J=7.6 Hz, 1H), 8.09 (s, 1H), 7.66 - 7.56 (m, 7H), 7.49 - 7.42 (m, 2H), 7.39 - 7.31 (m, 3H), 7.28 (t, J=8.8 Hz, 1H), 7.13 (d, J=7.2 Hz, 2H), 5.39 - 5.19 (m, 1H), 4.96 - 4.83 (m, 1H), 4.54 (d, J=9.2 Hz, 1H), 4.47 - 4.37 (m, 2H), 4.30 (s, 2H), 3.48 (s, 3H), 3.45 - 3.35 (m, 5H), 3.35 - 3.24 (m, 3H), 3.23 - 2.91 (m, 7H), 2.90 - 2.72 (m, 4H), 2.17 - 1.93 (m, 3H), 1.91 - 1.67 (m, 4H), 1.52 - 1.20 (m, 6H), 1.04 - 0.84 (m, 9H) |
| 406 | D | C | $^1$H NMR: (400 MHz, DMSO-$d_6$) δ: 12.94 (s, 1H), 9.86 (s, 1H), 8.66 (d, J=2.0 Hz, 1H), 8.56 (s, 1H), 8.43 (d, J=8.0 Hz, 1H), 8.08 (s, 1H), 7.69 - 7.58 (m, 3H), 7.53 - 7.43 (m, 3H), 7.42 - 7.33 (m, 2H), 7.27 (m, 1H), 7.15 (d, J=7.6 Hz, 2H), 6.37 (d, J=1.6 Hz, 1H), 5.38 - 5.20 (m, 1H), 4.97 - 4.88 (m, 1H), 4.54 (d, J=9.6 Hz, 1H), 4.43 (m, 2H), 4.30 (s, 1H), 3.85 - 3.79 (m, 4H), 3.66 - 3.25 (m, 12H), 3.21 - 2.61 (m, 10H), 2.17 - 1.71 (m, 7H), 1.52 - 1.27 (m, 5H), 1.04 - 0.90 (m, 9H) |

FIG. 3A. Continued

| No. | BRafV600E DC50 (nM) | BRafV600 E Dmax (%) | NMR Transcript |
|---|---|---|---|
| 407 | D | Not calculated | $^1$H NMR (400 MHz, DMSO-$d_6$, *ppm*): δ 12.86 (brs, 1H), 9.84 (brs, 1H), 8.98 (s, 1H), 8.71-8.63 (m, 1H), 8.55-8.50 (m, 1H), 8.42 (d, *J* = 7.6 Hz, 1H), 8.04 (s, 1H), 7.73 (d, *J* = 9.7 Hz, 1H), 7.62-7.51 (m, 1H), 7.56 (d, *J* = 8.4 Hz, 2H), 7.47-7.40 (m, 2H), 7.40-7.31 (m, 2H), 7.30-7.21 (m, 1H), 6.85 (d, *J* = 8.8 Hz, 2H), 5.40-5.21 (m, 1H), 5.11 (s, 1H), 4.89-4.81 (m, 1H), 4.50-4.44 (m, 2H), 4.28 (s, 1H), 3.64-3.52 (m, 2H), 3.48-3.45 (m, 1H), 3.44-3.40 (m, 4H), 3.33-3.23 (m, 1H), 3.06 (d, *J* = 16.2 Hz, 1H), 2.95-2.83 (m, 4H), 2.60-2.43 (m, 4H), 2.53-2.36 (m, 6H), 2.35-2.30 (m, 2H), 2.16-1.90 (m, 3H), 1.81-1.66 (m, 3H), 1.37 (d, *J* = 7.0 Hz, 3H), 0.94 (s, 9H) |
| 408 | D | A | $^1$H NMR (300 MHz, DMSO-$d_6$, ppm): δ 8.99 (s, 1H), 8.63 (s, 1H), 8.58-8.47 (m, 2H), 8.31 (s, 1H), 8.01 (s, 1H), 7.80-7.75 (m, 1H), 7.65-7.57 (m, 3H), 7.49-7.34 (m, 4H), 7.20-7.08 (m, 1H), 6.81-6.55 (m, 2H), 5.37-5.11 (m, 1H), 5.02-4.91 (m, 1H),4.55-4.45 (m, 2H), 4.30-4.20 (m, 1H), 3.55-3.42 (m, 9H), 3.28-3.15 (m, 5H), 3.09-2.97 (m, 4H), 2.47-2.45 (m, 3H), 2.28-2.36 (m, 2H),2.15-1.97(m, 3H), 1.93-1.70 (m, 2H), 1.49-1.33 (m, 3H), 1.21-1.15 (m, 3H), 0.96 (s, 9H) |
| 409 | D | A | $^1$H NMR (300 MHz, DMSO-$d_6$, ppm): δ 8.99 (s, 1H), 8.64 (s, 1H), 8.54-8.42 (m, 2H), 8.27 (s, 1H), 8.03 (s, 1H), 7.74-7.65 (m, 1H), 7.71-7.60 (m, 3H), 7.50-7.34 (m, 4H), 7.25-7.12 (m, 1H), 6.79-6.50 (m, 2H), 5.43-5.00 (m, 1H), 4.97-4.86 (m, 1H), 4.61-4.35 (m, 2H), 4.30 (s, 1H), 3.69-3.46 (m, 8H), 3.08 -2.87(m, 6H), 2.71-2.62 (m, 3H), 2.49-2.47 (m, 3H),2.27-2.25 (m, 2H), 2.11-1.78 (m, 6H), 1.55-1.36(m, 3H), 1.25 (s, 1H), 1.16 (t, *J* = 7.3 Hz, 2H), 0.96 (s, 9H). |
| 410 | D | B | $^1$H NMR (400 MHz, DMSO-$d_6$, *ppm*): δ 12.88 (brs, 1H), 9.85 (brs, 1H), 8.98 (s, 1H),8.80-8.60 (m, 1H), 8.60-8.50 (m, 1H), 8.43 (d, J = 7.6 Hz, 1H), 8.06 (s, 1H), 7.67-7.52 (m, 4H), 7.70-7.50 (m, 4H), 7.30-7.20 (m, 1H), 7.15-7.00 (m, 2H), 5.40-5.21 (m, 1H), 5.12 (d, J = 3.4 Hz, 1H), 5.00-4.85 (m, 1H), 4.53-4.40 (m, 2H), 4.28-4.22 (m, 1H), 3.64-3.51 (m, 2H), 3.55-3.35 (m, 4H), 3.25-3.15 (m, 7H), 3.20-3.00 (m, 2H), 2.70-2.60 (m, 1H), 2.60-2.50(m,3H),2.45-2.35 (m, 4H), 2.30-2.20 (m, 2H), 2.30-2.20 (m, 3H), 2.20-2.00 (m, 3H), 2.00-1.85-1.70(m,1H), 1.50-1.30 (m, 3H), 0.94 (s, 9H) |

FIG. 3A. Continued

| No. | BRafV600E DC50 (nM) | BRafV600 E Dmax (%) | NMR Transcript |
|---|---|---|---|
| 411 | D | B | $^1$H NMR: (400MHz, DMSO-$d_6$) δ = 8.98 (s, 1H), 8.64 (d, *J*=2.0 Hz, 1H), 8.58 - 8.40 (m, 2H), 8.20 (s, 2H), 8.05 (s, 1H), 7.71 (d, *J*=10.0 Hz, 1H), 7.65 - 7.51 (m, 4H), 7.48 - 7.33 (m, 5H), 7.23 (t, *J*=8.8 Hz, 1H), 7.06 (d, *J*=8.8 Hz, 2H), 5.40 - 5.19 (m, 1H), 4.89 (s, *J*=6.8 Hz, 1H), 4.55 - 4.33 (m, 3H), 4.28 (s, 1H), 3.89 - 3.81 (m, 3H), 3.58 (d, *J*=6.0 Hz, 1H), 3.46 (s, 1H), 3.28 (dd, *J*=6.4, 10.0 Hz, 4H), 3.09 - 3.05 (m, 1H), 3.02 (s, 1H), 2.92 - 2.86 (m, 1H), 2.66 - 2.56 (m, 3H), 2.45 (s, 5H), 2.14 - 1.98 (m, 4H), 1.83 - 1.65 (m, 5H), 1.45 - 1.23 (m, 6H), 0.94 (s, 9H), 0.91 (s, 5H), 0.92 - 0.89 (m, 1H), 0.89 - 0.84 (m, 1H), 0.86 - 0.84 (m, 1H) |
| 412 | D | B | $^1$H NMR: (400MHz, DMSO-$d_6$) *δ:* 8.97 (s, 1H), 8.64 (d, *J*=2.0 Hz, 1H), 8.52 (s, 1H), 8.42 (d, J=8.4 Hz, 1H), 8.20 (s, 1H), 8.03 (s, 1H), 7.81 (d, *J*=10.0 Hz, 1H), 7.64 - 7.54 (m, 3H), 7.45 - 7.41 (m, 2H), 7.39 - 7.34 (m, 2H), 7.24 - 7.17 (m, 1H), 7.06 (d, *J*=8.8 Hz, 2H), 5.41 - 5.17 (m, 1H), 5.02 - 4.83 (m, 1H), 4.61 - 4.39 (m, 2H), 4.29 (s, 1H), 3.78 (d, *J*=12.4 Hz, 3H), 3.64 - 3.52 (m, 2H), 3.13 - 3.10 (m, 2H), 2.73 - 2.65 (m, 10H), 2.45 (s, 4H), 2.40 - 2.25 (m, 5H), 2.17 - 1.96 (m, 4H), 1.91 - 1.68 (m, 6H), 1.64 (s, 1H), 1.43 - 1.34 (m, 3H), 1.29 - 1.15 (m, 2H), 0.95 (s, 9H) |
| 413 | D | Not calculated | $^1$H NMR: (400MHz, DMSO-$d_6$) : 12.95 (d, J=2.8 Hz, 1H), 9.86 (s, 1H), 9.46 - 9.31 (m, 1H), 9.00 (s, 1H), 8.68 (d, *J*=2.0 Hz, 1H), 8.58 (s, 1H), 8.31 (d, J=7.6 Hz, 1H), 8.09 (d, *J*=2.8 Hz, 1H), 7.71 - 7.59 (m, 3H), 7.50 - 7.38 (m, 3H), 7.37 - 7.24 (m, 3H), 7.17 (d, *J*=8.8 Hz, 2H), 6.19 (s, 1H), 6.20 (d, *J*=4.4 Hz, 1H), 5.44 - 5.19 (m, 1H), 5.08 - 4.80 (m, 2H), 4.58 - 4.38 (m, 1H), 4.34 - 4.20 (m, 1H), 3.93 (d, *J*=10.4 Hz, 5H), 3.72 - 3.60 (m, 6H), 3.59 - 3.51 (m, 2H), 3.49 (s, 1H), 3.45 - 3.37 (m, 3H), 3.34 - 3.25 (m, 2H), 3.15 (d, J=12.1 Hz, 5H), 2.88 - 2.72 (m, 2H), 2.47 - 2.43 (m, 5H), 2.26 (dd, *J*=6.8, 14.8 Hz, 1H), 2.13 - 1.96 (m, 6H), 1.87 - 1.72 (m, 3H), 1.46 (d, *J*=7.2 Hz, 1H), 1.36 (d, J=7.2 Hz, 2H), 1.32 - 1.21 (m, 2H), 0.96 (d, J=6.4 Hz, 2H), 0.86 - 0.80 (m, 3H), 0.76 (d, *J*=6.4 Hz, 1H) |

FIG. 3A. Continued

| No. | BRafV600E DC50 (nM) | BRafV600E Dmax (%) | NMR Transcript |
|---|---|---|---|
| 414 | C | A | $^1$H NMR: (400MHz, DMSO-d6) $\delta$ : 12.95 (d, J=2.8 Hz, 1H), 9.86 (s, 1H), 9.46 - 9.31 (m, 1H), 9.00 (s, 1H), 8.68 (d, J=2.0 Hz, 1H), 8.58 (s, 1H), 8.31 (d, J=7.6 Hz, 1H), 8.09 (d, J=2.8 Hz, 1H), 7.71 - 7.59 (m, 3H), 7.50 - 7.38 (m, 3H), 7.37 - 7.24 (m, 3H), 7.17 (d, J=8.8 Hz, 2H), 6.19 (s, 1H), 6.20 (d, J=4.4 Hz, 1H), 5.44 - 5.19 (m, 1H), 5.08 - 4.80 (m, 2H), 4.58 - 4.38 (m, 1H), 4.34 - 4.20 (m, 1H), 3.93 (d, J=10.4 Hz, 5H), 3.72 - 3.60 (m, 6H), 3.59 - 3.51 (m, 2H), 3.49 (s, 1H), 3.45 - 3.37 (m, 3H), 3.34 - 3.25 (m, 2H), 3.15 (d, J=12.1 Hz, 5H), 2.88 - 2.72 (m, 2H), 2.47 - 2.43 (m, 5H), 2.26 (dd, J=6.8, 14.8 Hz, 1H), 2.13 - 1.96 (m, 6H), 1.87 - 1.72 (m, 3H), 1.46 (d, J=7.2 Hz, 1H), 1.36 (d, J=7.2 Hz, 2H), 1.32 - 1.21 (m, 2H), 0.96 (d, J=6.4 Hz, 2H), 0.86 - 0.80 (m, 3H), 0.76 (d, J=6.4 Hz, 1H) |
| 415 | D | Not calculated | $^1$H NMR: (400MHz, DMSO-$d_6$) δ: 9.01 - 8.89 (m, 1H), 8.75 (s, 2H), 8.65 (d, *J*=2.0 Hz, 1H), 8.54 (s, 1H), 8.24 - 8.15 (m, 1H), 8.09 (s, 1H), 7.66 - 7.56 (m, 1H), 7.50 - 7.39 (m, 2H), 7.35 - 7.30 (m, 1H), 7.24 (t, *J*=8.4 Hz, 1H), 6.14 (s, 1H), 5.39 - 5.20 (m, 1H), 5.06 - 4.84 (m, 1H), 4.56 - 4.38 (m, 1H), 4.29 (s, 1H), 3.80 (s, 4H), 3.71 - 3.55 (m, 8H), 3.51 - 3.47 (m, 6H), 2.85 - 2.64 (m, 2H), 2.47 - 2.39 (m, 7H), 2.30 - 1.90 (m, 7H), 1.81 - 1.65 (m, 3H), 1.51 - 1.32 (m, 3H), 1.23 - 1.01 (m, 2H), 0.96 (d, *J*=6.4 Hz, 2H), 0.88 - 0.65 (m, 4H) |
| 416 | D | A | $^1$H NMR: (400MHz, DMSO-$d_6$) δ: 8.97 (s, 1H), 8.81 - 8.65 (m, 3H), 8.59 - 8.32 (m, 2H), 8.25 - 8.03 (m, 2H), 7.61 (d, *J*=6.4 Hz, 1H), 7.51 - 7.32 (m, 5H), 7.24 (s, 1H), 6.20 - 5.93 (m, 1H), 5.44 - 5.19 (m, 1H), 4.92 (s, 1H), 4.45 - 4.26 (m, 2H), 3.81 (s, 5H), 2.84 - 2.65 (m, 5H), 2.46 (s, 10H), 2.17 - 1.98 (m, 5H), 1.78 (d, *J*=10.4 Hz, 4H), 1.48 - 1.32 (m, 4H), 1.16 (d, *J*=9.2 Hz, 3H), 0.96 (s, 3H), 0.80 (d, *J*=5.2 Hz, 3H) |

FIG. 3A. Continued

| No. | BRafV600E DC50 (nM) | BRafV600E Dmax (%) | NMR Transcript |
|---|---|---|---|
| 417 | D | A | $^1$H NMR: (400 MHz, DMSO-$d_6$) δ: 12.88 (s, 1H), 9.83 (s, 1H), 8.64 (d, J=2.4 Hz, 1H), 8.51 (d, J=7.2 Hz, 2H), 8.06 (s, 1H), 7.78 (d, J=8.4 Hz, 2H), 7.71 ( d, J=9.2 Hz, 1H), 7.66 - 7.60 (m, 1H), 7.58 (d, J=8.8 Hz, 2H), 7.50 - 7.42 (m, 2H), 7.26 (t, J=8.4 Hz, 1H), 7.06 (d, J=8.8 Hz, 2H), 5.39 - 5.20 (m, 1H), 5.11 (d, J=3.6 Hz, 1H), 4.99 - 4.83 (m, 1H), 4.53 - 4.37 (m, 2H), 4.26 (s, 1H), 3.78 (d, J=12.4 Hz, 2H), 3.57 (s, 2H), 3.48 (s, 1H), 3.43 - 3.33 (m, 3H), 3.29 - 3.25 (m, 2H), 3.04 (d, J=16.0 Hz, 1H), 2.96 - 2.85 (m, 1H), 2.72 ( t, J=11.6 Hz, 2H), 2.44 - 2.36 (m, 3H), 2.20 (d, J=7.2 Hz, 3H), 2.14 - 1.92 (m, 4H), 1.86 - 1.76 (m, 2H), 1.70 (d, J=4.4 Hz, 2H), 1.36 (d, J=7.2 Hz, 3H), 1.22 (d, J=12.8 Hz, 3H), 0.93 (s, 9H) |
| 418 | | | $^1$H-NMR: (300 MHz, $CD_3OD$, ppm) δ 8.88-8.86 (m, 1H), 8.68 (s, 1H), 8.60 (d, J = 2.4Hz, 1H), 7.89 (s, 1H), 7.76-7.74 (m, 1H), 7.59 (d, J = 8.7Hz, 2H), 7.45-7.43 (m, 4H), 7.12-7.09 (m, 3H), 5.30-5.13 (m, 1H), 5.03-5.00 (m, 1H), 4.64-4.62 (m, 2H), 4.50-4.46 (m, 1H), 3.87-3.78 (m, 4H), 3.58-3.41 (m, 5H), 3.31-3.29 (m, 2H), 3.06 (s, 2H), 2.98-2.93 (m, 2H), 2.80 (m, 4H), 2.47 (s, 3H), 2.26-2.19 (m, 6H), 2.03-1.95 (m, 4H), 1.71-1.63 (m, 2H), 1.06-1.04 (m, 9H) |
| 419 | D | Not calculated | $^1$H NMR (400 MHz, DMSO-$d_6$, ppm): δ 12.88 (brs, 1H), 9.84 (brs, 1H), 8.99 (s, 1H), 8.71-8.62 (m, 2H), 8.52 (s, 1H), 8.06 (s, 1H), 7.76-7.72 (m, 1H), 7.67-57 (m, 3H), 7.46-7.37 (m, 4H), 7.25 (m, 1H), 7.06 (m, 2H), 5.45 (d, J = 7.3 Hz, 1H), 5.36-5.23 (m, 1H) , 4.49-4.33 (m, 3H), 4.33-4.19 (m, 2H), 3.88 (m, 1H), 3.77 (m, 2H), 3.46 (m, 2H), 3.40 (m, 2H),3.28(m,2H), 3.25(m,1H) ,3.00-2.94 (m, 2H), 2.71 (m, 2H), 2.45-2.42 (s, 9H), 2.17 (m, 2H), 2.13-2.03(m,2H), 2.01-1.93(m,1H), 1.75-1.69 (m, 4H), 1.27-1.16 (m, 2H), 0.96-0.92 (s, 9H) |
| 420 | D | A | $^1$H NMR (400 MHz, DMSO- $d_6$, *ppm*): δ 8.96 (s, 1H), 8.70 (d, J = 2.2 Hz, 1H), 8.72-8.63 (m, 2H), 8.08 (s, 1H), 7.88-7.62 (m, 4H), 7.57-7.37 (m, 7H), 7.30-7.24 (m, 1H), 5.36-5.18 (m, 2H), 4.59-4.53 (m, 1H), 4.50-4.40 (m, 2H), 4.39-4.32 (m, 2H), 4.31-4.22 (m, 2H),4.13-4.01 (m, 1H), 3.87 (s, 2H), 3.72- 3.61(m, 6H), 3.18 (s, 3H), 2.70-2.60 (m, 2H), 2.44 (s, 3H), 2.11-1.91 (m, 8H), 1.24 (s, 2H), 0.95 (s, 9H) |

FIG. 3A. Continued

| No. | BRafV600E DC50 (nM) | BRafV600E Dmax (%) | NMR Transcript |
|---|---|---|---|
| 421 | D | A | $^1$H NMR: (400 MHz, $CDCl_3$) *δ:* 11.29 (s, 1H), 8.87 (d, *J*=1.6 Hz, 1H), 8.60 (d, *J*=2.0 Hz, 1H), 7.91 (d, *J*=8.4 Hz, 1H), 7.80 - 7.66 (m, 2H), 7.56 (d, *J*=8.8 Hz, 2H), 7.46 (d, *J*=7.6 Hz, 1H), 7.32 - 7.29 (m, 1H), 7.26 - 7.20 (m, 2H), 7.07 - 6.98 (m, 3H), 5.22 (d, *J*=52.4 Hz, 1H), 5.01 (m, 1H), 4.75 (m, 1H), 4.54 - 4.43 (m, 2H), 4.20 (d, *J*=11.6 Hz, 1H), 3.75 (d, *J*=11.6 Hz, 2H), 3.69 - 3.53 (m, 4H), 3.53 - 3.42 (m, 2H), 3.00 (s, 2H), 2.72 (m, 2H), 2.62 - 2.35 (m, 9H), 2.33 - 1.92 (m, 7H), 1.90 - 1.84 (m, 2H), 1.45 - 1.24 (m, 6H), 1.07 (s, 9H) |
| 422 | D | A | $^1$H NMR: (400MHz, DMSO-$d_6$), *δ:* 13.14 - 12.63 (m, 1H), 9.69 (s, 1H), 8.65 (d, *J*=2.0 Hz, 1H), 8.58 - 8.46 (m, 2H), 8.17 (d, *J*=2.0 Hz, 1H), 8.07 (s, 1H), 7.99 (d, *J*=8.4 Hz, 2H), 7.74 (d, *J*=9.6 Hz, 1H), 7.69 - 7.53 (m, 4H), 7.51 - 7.45 (m, 1H), 7.51 - 7.45 (m, 2H), 7.26 (t, *J*=8.8 Hz, 1H), 7.07 (d, *J*=8.8 Hz, 2H), 5.37 - 5.20 (m, 1H), 5.15 - 4.88 (m, 2H), 4.55 - 4.43 (m, 2H), 4.29 - 4.20 (m, 1H), 3.82 - 3.73 (m, 3H), 3.58 (s, 3H), 3.06 - 2.86 (m, 2H), 2.76 - 2.64 (m, 3H), 2.22 - 1.94 (m, 5H), 1.87 - 1.63 (m, 6H), 1.50 - 1.35 (m, 4H), 1.30 - 1.13 (m, 3H), 1.04 - 0.80 (m, 12H) |
| 423 | D | B | $^1$H NMR (400 MHz, DMSO-*d6*, ppm): δ 12.89 (brs, 1H), 8.98 (s, 1H), 8.70-8.62 (m, 1H), 8.53 (s, 1H), 8.44 (d, J = 7.6 Hz, 1H), 8.05 (s, 1H), 7.78- 7.50 (m, 4H), 7.50-7.29 (m, 4H), 7.21 (t, J = 9.3 Hz, 1H), 7.06 (d, J = 8.4 Hz, 2H), 5.48-5.21 (m, 1H), 5.13 (s, 1H), 4.99-4.86 (m, 1H), 4.58-4.35 (m, 2H), 4.28 (s, 1H), 4.08-3.80(m, 1H), 3.72-3.40 (m, 6H), 3.25-3.00 (m, 9H), 2.46 (s, 3H), 2.36 (s, 3H), 2.27-1.90 (m, 8H), 1.90-1.69 (brs, 4H), 1.50- 1.35 (m, 3H), 0.93 (s, 9H). |
| 424 | D | Not calculated | $^1$H NMR (400 MHz, Methanol-$d_4$, ppm): *δ* 9.09 (s, 1H), 8.69 (s, 1H), 8.61 (d, *J* = 2.2 Hz, 1H), 7.90 (s, 1H), 7.80-7.74 (m, 1H), 7.59 (d, *J* = 8.8 Hz, 2H), 7.35 (d, *J* = 8.9 Hz, 2H), 7.20-7.09 (m, 3H), 5.31-5.15 (m, 1H), 4.97 (q, *J* = 7.0 Hz, 1H), 4.66-4.56 (m, 2H), 4.52 (s, 1H), 3.90-3.72 (m, 4H), 3.64-3.38 (m, 4H), 3.07 (s, 2H), 2.80-2.48 (m, 10H), 2.32 (s, 3H), 2.27-1.98 (m, 6H), 1.84-1.80 (m, 2H), 1.70 (s, 1H), 1.52 (d, *J* = 7.1 Hz, 3H), 1.40-1.23 (m, 2H), 0.98 (s, 9H) |

FIG. 3A. Continued

| No. | BRafV600E DC50 (nM) | BRafV600E Dmax (%) | NMR Transcript |
|---|---|---|---|
| 425 | D | A | $^1$H NMR: (400MHz, DMSO-$d_6$) *δ:* 13.03 - 12.82 (m, 1H), 9.00 - 8.97 (m, 1H), 8.65 (d, *J*=2.0 Hz, 1H), 8.53 (s, 1H), 8.22 (d, *J*=8.0 Hz, 1H), 8.15 (s, 1H), 8.07 (s, 1H), 7.65 - 7.56 (m, 3H), 7.50 - 7.46 (m, 1H), 7.45 - 7.38 (m, 2H), 7.34 - 7.23 (m, 3H), 7.08 (d, *J*=8.8 Hz, 2H), 6.16 (s, 1H), 6.15 - 6.15 (m, 1H), 5.38 - 5.12 (m, 1H), 4.88 (t, *J*=7.0 Hz, 1H), 4.42 (t, *J*=7.6 Hz, 1H), 4.28 (s, 1H), 3.83 (d, *J*=11.6 Hz, 2H), 3.70 (d, *J*=8.8 Hz, 1H), 3.55 (d, *J*=3.2 Hz, 3H), 3.12 (s, 5H), 2.74 (t, *J*=12.0 Hz, 2H), 2.61 (s, 1H), 2.55 (s, 3H), 2.47 - 2.43 (m, 4H), 2.25 (dd, *J*=6.8, 15.2 Hz, 1H), 2.19 - 1.97 (m, 4H), 1.94 - 1.73 (m, 4H), 1.58 - 1.43 (m, 3H), 1.35 (d, *J*=7.0 Hz, 2H), 0.96 (d, *J*=6.4 Hz, 2H), 0.82 (d, *J*=6.8 Hz, 3H), 0.75 (d, *J*=6.8 Hz, 1H) |
| 426 | C | A | $^1$H NMR: (400MHz, DMSO-$d_6$) *δ:* 12.90 (s, 1H), 9.00 - 8.97 (m, 1H), 8.65 (d, *J*=2.0 Hz, 1H), 8.53 (s, 1H), 8.41 (d, *J*=7.6 Hz, 1H), 8.15 (s, 1H), 8.07 (s, 1H), 7.67 - 7.55 (m, 4H), 7.46 - 7.41 (m, 2H), 7.39 - 7.35 (m, 2H), 7.27 (t, *J*=8.4 Hz, 1H), 7.08 (d, *J*=8.8 Hz, 2H), 6.15 (s, 1H), 5.38 - 5.20 (m, 1H), 5.12 (s, 1H), 4.91 (quin, *J*=7.2 Hz, 1H), 4.36 (t, *J*=8.0 Hz, 1H), 4.28 (s, 1H), 3.84 (d, *J*=11.6 Hz, 2H), 3.71 (dd, *J*=4.4, 10.0 Hz, 2H), 3.57 (d, *J*=10.0 Hz, 1H), 2.75 (t, *J*=11.4 Hz, 2H), 2.61 (s, 5H), 2.45 (s, 5H), 2.29 - 2.14 (m, 2H), 2.14 - 1.94 (m, 4H), 1.88 (d, *J*=10.8 Hz, 3H), 1.78 (ddd, *J*=4.8, 7.6, 12.4 Hz, 1H), 1.61 - 1.43 (m, 3H), 1.38 (d, *J*=7.2 Hz, 3H), 0.99 - 0.90 (m, 4H), 0.85 - 0.75 (m, 4H) |
| 427 | D | B | $^1$H NMR: (400MHz, DMSO-$d_6$), δ = 12.90 (s, 1H), 9.85 (d, *J*=2.4 Hz, 1H), 8.65 (d, *J*=2.0 Hz, 1H), 8.53 (s, 1H), 8.44 (d, *J*=7.6 Hz, 1H), 8.32 (s, 1H), 8.07 (s, 1H), 7.77 - 7.66 (m, 1H), 7.63 - 7.54 (m, 5H), 7.40 (d, *J*=8.4 Hz, 2H), 7.33 - 7.22 (m, 1H), 7.07 (d, *J*=8.8 Hz, 2H), 5.42 - 5.20 (m, 1H), 5.12 (d, *J*=3.2 Hz, 1H), 4.90 (t, *J*=7.2 Hz, 1H), 4.57 - 4.39 (m, 2H), 4.28 (s, 1H), 3.79 (d, *J*=12.4 Hz, 2H), 3.65 - 3.53 (m, 2H), 3.38 (d, *J*=1.6 Hz, 3H), 3.31 - 3.27 (m, 2H), 3.11 - 2.89 (m, 2H), 2.81 - 2.67 (m, 2H), 2.47 - 2.38 (m, 4H), 2.38 - 2.32 (m, 4H), 2.24 - 1.96 (m, 6H), 1.86 - 1.70 (m, 4H), 1.51 - 1.34 (m, 3H), 1.29 - 1.18 (m, 2H), 0.95 (s, 9H) |

FIG. 3A. Continued

| No. | BRafV600E DC50 (nM) | BRafV600 E Dmax (%) | NMR Transcript |
|---|---|---|---|
| 428 | B | B | $^1$H NMR: (400MHz, DMSO-$d_6$) *δ:* 12.96 (s, 1H), 11.10 (s, 1H), 9.87 (s, 1H), 9.41 (s, 1H), 8.68 (d, *J*=2.0 Hz, 1H), 8.58 (s, 1H), 8.09 (s, 1H), 7.68 (dd, *J*=4.8, 8.4 Hz, 3H), 7.64 - 7.59 (m, 1H), 7.38 (s, 1H), 7.32 - 7.23 (m, 2H), 7.17 (d, *J*=8.4 Hz, 2H), 5.39 - 5.20 (m, 1H), 5.07 (dd, *J*=5.2, 12.8 Hz, 1H), 4.12 (d, *J*=12.8 Hz, 2H), 4.00 - 3.87 (m, 2H), 3.73 - 3.59 (m, 3H), 3.41 - 3.40 (m, 2H), 3.23 - 3.09 (m, 6H), 3.02 (t, *J*=12.0 Hz, 2H), 2.94 - 2.83 (m, 1H), 2.64 - 2.55 (m, 2H), 2.24 - 1.94 (m, 4H), 1.92 - 1.80 (m, 2H), 1.36 - 1.20 (m, 2H) |
| 429 | B | B | $^1$H NMR: (400MHz, DMSO-$d_6$) *δ:* 112.96 (s, 1H), 11.10 (s, 1H), 9.87 (s, 1H), 9.63 (s, 1H), 8.67 (d, *J*=2.0 Hz, 1H), 8.57 (s, 1H), 8.09 (s, 1H), 7.74 - 7.58 (m, 4H), 7.44 (s, 1H), 7.35 (d, *J*=8.8 Hz, 1H), 7.27 (t, *J*=8.8 Hz, 1H), 7.17 (d, *J*=8.8 Hz, 2H), 5.40 - 5.17 (m, 1H), 5.09 (dd, *J*=5.2, 12.8 Hz, 1H), 4.28 (d, *J*=11.6 Hz, 2H), 3.98 (d, *J*=11.6 Hz, 2H), 3.73 - 3.61 (m, 2H), 3.39 - 3.36 (m, 2H), 3.34- 3.25 (m, 3H), 3.10 - 2.97 (m, 4H), 2.91 - 2.83 (m, 1H), 2.63 - 2.56 (m, 2H), 2.26 - 2.15 (m, 2H), 2.15 - 1.98 (m, 3H), 1.78 - 1.63 (m, 2H) |
| 430 | D | B | $^1$H NMR (400 MHz, Methanol-$d_4$, ppm): δ 8.89 (d, J = 3.0 Hz, 1H), 8.59 (s, 2H), 7.91 (s, 1H), 7.80-7.73 (m, 1H), 7.59-7.52 (m, 2H), 7.51-7.44 (m, 4H), 7.18-7.09 (m, 1H), 6.82-6.74 (m, 2H), 5.29-5.14 (m, 1H), 5.02 -4.95 (m, 1H), 4.63-4.53 (m, 1H), 4.44-4.38 (m, 2H), 3.91-3.81 (m, 2H), 3.75-3.70 (m, 1H), 3.62-3.48 (m, 8H), 3.20-3.11 (m, 1H), 3.09-2.92 (m, 2H), 2.97-2.79 (m, 2H), 2.75-2.63 (m, 1H), 2.50-2.42 (m, 3H), 2.40-2.07 (m, 5H), 1.99-1.90 (m, 4H), 1.85-1.80 (m, 1H), 1.59-1.50 (m, 5H), 1.05 (s, 9H). |
| 431 | D | Not calculated | $^1$H NMR (400 MHz, $CDCl_3$, *ppm*): δ 11.80 (br s, 1H), 8.86 (s, 1H), 8.80 (s, 1H), 8.60 (s, 1H), 7.91-7.81 (m, 1H), 7.80-7.70 (m, 2H), 7.69-7.53 (m, 3H), 7.23-7.20 (m, 1H), 7.19-7.15 (m, 2H), 7.11-6.98 (m, 3H), 5.33-5.12 (m, 1H), 5.11-5.00 (m, 1H), 4.83-4.70 (m, 1H), 4.67-4.47 (m, 1H), 4.46-4.31 (m, 1H), 4.22-4.05 (m,1H), 3.86-3.68 (m, 2H), 3.62-3.57(m, 3H), 3.52-3.41 (m, 2H), 3.10-2.91 (m, 2H), 2.81-2.62(m, 2H), 2.61-2.46 (m, 5H), 2.44-2.32 (m, 6H), 2.30-2.05 (m, 6H), 2.01-1.92 (m, 1H), 1.91-1.85 (m, 3H), 1.55-1.46 ( m, 3H), 1.40-1.23 (m, 2H), 0.76 (s, 9H) |

FIG. 3A. Continued

| No. | BRafV600E DC50 (nM) | BRafV600E Dmax (%) | NMR Transcript |
|---|---|---|---|
| 432 | D | A | $^1$H NMR (300 MHz, DMSO-$d_6$, *ppm*): δ 12.90 (br s, 1H), 9.85 (br s, 1H), 9.07 (s, 1H), 8.70-8.61 (m, 1H), 8.54 (s, 1H), 8.50-8.40 (m, 1H), 8.08 (s, 1H), 7.95-7.80 (m, 1H), 7.80-7.70 (m, 1H), 7.70-7.40 (m, 3H), 7.40-7.15 (m, 2H), 7.20-6.80 (m, 2H), 5.50-5.20 (m, 1H), 5.20-5.10 (m, 1H), 5.10-4.80 (m, 1H), 4.70-4.60 (m,1H), 4.60-4.50 (m, 2H), 4.50-4.20 (m, 2H), 3.90-3.70 (m, 2H), 3.65-3.40 (m, 4H), 3.20-3.10 (m,1H), 3.08-2.83 (m, 2H), 2.80-2.62 (m, 3H), 2.40-2.30 (m, 8H), 2.30-2.00 (m, 7H), 1.80-1.50 (m, 3H), 1.55-1.35 (m, 3H), 1.35-1.05 (m, 2H), 0.76 (s, 9H) |
| 433 | D | Not calculated | $^1$H NMR (400 MHz, DMSO-$d_6$, *ppm*): δ 8.97 (s, 1H), 8.70 (d, *J* = 2.3 Hz, 1H), 8.67-8.55 (m, 2H), 8.11 (s, 1H), 7.68-7.62 (m, 3H), 7.47-7.38 (m, 7H), 7.30-7.25 (m, 1H), 5.40-5.20 (m, 1H), 5.23-5.16 (m, 1H), 4.59-4.53 (m, 1H), 4.45-4.33 (m, 4H), 4.30-4.26 (m, 1H), 4.12-4.06 (m, 1H), 3.87 (s, 2H), 3.67-3.55 (m, 4H), 3.50-3.35 (m, 6H), 3.33-3.23 (m, 1H), 2.46-2.44 (m, 6H) 2.11-1.85 (m, 7H), 0.95 (s, 9H) |
| 434 | D | A | $^1$H NMR: (400MHz, DMSO-$d_6$) *δ:* 12.85 (s, 1H), 8.98 (s, 1H), 8.62 (d, *J*=2.4 Hz, 1H), 8.48 (s, 1H), 8.41 (d, *J*=8.0 Hz, 1H), 8.03 (s, 1H), 7.69 (d, *J*=9.2 Hz, 1H), 7.61 (dt, *J*=6.0, 9.2 Hz, 1H), 7.52 (d, *J*=8.8 Hz, 2H), 7.45 - 7.40 (m, 2H), 7.40 - 7.33 (m, 2H), 7.25 (t, *J*=8.8 Hz, 1H), 6.65 - 6.65 (m, 1H), 6.65 - 6.65 (m, 1H), 6.65 (d, *J*=8.8 Hz, 1H), 5.38 - 5.18 (m, 1H), 5.11 (d, *J*=3.6 Hz, 1H), 4.90 - 4.74 (m, 2H), 4.54 - 4.41 (m, 2H), 4.27 (s, 1H), 4.16 (s, 1H), 3.67 - 3.51 (m, 4H), 3.49 - 3.45 (m, 1H), 3.42 - 3.36 (m, 4H), 3.30 - 3.22 (m, 4H), 3.09 - 3.00 (m, 2H), 2.94 - 2.86 (m, 1H), 2.59 - 2.53 (m, 2H), 2.52 - 2.51 (m, 4H), 2.45 (s, 3H), 2.22 - 2.14 (m, 2H), 2.12 - 1.93 (m, 3H), 1.90 - 1.73 (m, 3H), 1.69 - 1.62 (m, 1H), 1.17 - 1.06 (m, 1H), 0.92 (s, 9H) |
| 435 | C | A | $^1$H NMR: (400MHz, DMSO-$d_6$) *δ:* 12.86 (s, 1H), 8.98 (s, 1H), 8.62 (s, 1H), 8.53 - 8.37 (m, 2H), 8.17 (s, 1H), 8.04 (s, 1H), 7.71 (d, *J*=9.2 Hz, 1H), 7.66 - 7.57 (m, 1H), 7.52 (d, *J*=8.4 Hz, 2H), 7.46 - 7.40 (m, 2H), 7.39 - 7.33 (m, 2H), 7.25 (t, *J*=8.4 Hz, 1H), 6.65 (d, *J*=8.4 Hz, 2H), 5.39 - 5.20 (m, 1H), 5.13 (s, 1H), 4.90 - 4.71 (m, 2H), 4.52 - 4.42 (m, 2H), 4.27 (s, 1H), 4.15 (s, 1H), 3.66 - 3.54 (m, 2H), 3.47 - 3.46 (m, 2H), 3.10 - 2.99 (m, 4H), 2.94 - 2.86 (m, 1H), 2.60 - 2.52 (m, 4H), 2.45 (s, 3H), 2.36 - 2.24 (m, 4H), 2.24 - 2.14 (m, 3H), 2.13 - 1.92 (m, 5H), 1.89 - 1.70 (m, 4H), 1.68 - 1.58 (m, 1H), 1.14 - 1.03 (m, 1H), 0.92 (s, 9H) |

FIG. 3A. Continued

| No. | BRafV600E DC50 (nM) | BRafV600 E Dmax (%) | NMR Transcript |
|---|---|---|---|
| 436 | D | B | $^1$H NMR: (400 MHz, DMSO-d6) *δ:* 12.91 (s, 1H), 9.83 (s, 1H), 9.68 (s, 1H), 9.45 (s, 1H), 8.99 (s, 1H), 8.70 (s, 1H), 8.65 (d, *J*=2.0 Hz, 1H), 8.55 (s, 1H), 8.38 (d, *J*=7.6 Hz, 1H), 8.07 (s, 1H), 7.67 - 7.58 (m, 3H), 7.48 - 7.33 (m, 4H), 7.32 - 7.23 (m, 1H), 6.92 (d, *J*=8.8 Hz, 2H), 5.37 - 5.24 (d, *J*=52.0 Hz, 1H), 4.96 - 4.87 (m, 2H), 4.68 (s, 1H), 4.57 (d, *J*=9.2 Hz, 1H), 4.43 (t, *J*=8.0 Hz, 2H), 4.31 (s, 1H), 4.00 (s, 1H), 3.90 (d, *J*=14.4 Hz, 1H), 3.74 (d, *J*=7.2 Hz, 1H), 3.65 (s, 2H), 3.57 (s, 1H), 3.53 (s, 3H), 3.49 (s, 2H), 3.44 - 3.37 (m, 2H), 3.34 - 3.25 (m, 2H), 3.18 - 2.92 (m, 3H), 2.46 (s, 5H), 2.24 (s, 2H), 2.16 - 1.87 (m, 5H), 1.85 - 1.74 (m, 1H), 1.62 - 1.51 (m, 1H), 1.52 - 1.29 (m, 3H), 1.07 - 0.86 (m, 9H). |
| 437 | D | C | $^1$H NMR: (400MHz, DMSO-$d_6$) *δ:* 12.94 (s, 1H), 8.98 (s, 1H), 8.64 (d, *J*=2.0 Hz, 1H), 8.53 (s, 1H), 8.45 (d, *J*=7.6 Hz, 1H), 8.17 (s, 2H), 8.06 (s, 1H), 7.82 (d, *J*=9.6 Hz, 1H), 7.66 - 7.54 (m, 3H), 7.46 - 7.40 (m, 2H), 7.40 - 7.33 (m, 2H), 7.25 (t, *J*=8.4 Hz, 1H), 7.07 (d, *J*=8.8 Hz, 2H), 5.39 - 5.20 (m, 1H), 4.98 - 4.84 (m, 1H), 4.50 (d, *J*=9.6 Hz, 1H), 4.44 (t, *J*=8.4 Hz, 1H), 4.28 (s, 1H), 3.84 (d, *J*=11.2 Hz, 2H), 3.63 - 3.53 (m, 2H), 3.47 (s, 3H), 3.11 (d, *J*=8.8 Hz, 2H), 2.79 (d, *J*=15.2 Hz, 4H), 2.75 - 2.68 (m, 6H), 2.45 (s, 4H), 2.14 - 2.01 (m, 3H), 1.85 - 1.69 (m, 6H), 1.63 - 1.44 (m, 3H), 1.38 (d, *J*=6.8 Hz, 3H), 0.95 (s, 9H) |
| 438 | D | A | $^1$H NMR: (400MHz, DMSO-$d_6$) δ: 12.90 (s, 1H), 9.03 - 8.93 (m, 1H), 8.65 (d, *J*=2.0 Hz, 1H), 8.52 (s, 1H), 8.26 (d, *J*=7.6 Hz, 1H), 8.18 - 8.01 (m, 2H), 7.66 - 7.53 (m, 3H), 7.42 (d, *J*=8.0 Hz, 2H), 7.31 (d, *J*=8.0 Hz, 2H), 7.28 - 7.22 (m, 1H), 7.06 (d, *J*=8.8 Hz, 2H), 5.39 - 5.19 (m, 1H), 5.15 - 4.96 (m, 1H), 4.85 (t, *J*=7.2 Hz, 1H), 4.50 - 4.35 (m, 1H), 4.33 - 4.12 (m, 1H), 3.88 - 3.70 (m, 3H), 3.62 (d, *J*=9.6 Hz, 1H), 3.54 - 3.45 (m, 2H), 3.43 - 3.38 (m, 3H), 3.29 - 3.26 (m, 4H), 3.25 - 3.11 (m, 2H), 2.73 (t, *J*=11.6 Hz, 2H), 2.53 - 2.52 (m, 2H), 2.47 - 2.45 (m, 4H), 2.27 - 2.17 (m, 2H), 2.11 - 1.91 (m, 3H), 1.86 - 1.69 (m, 4H), 1.45 (d, *J*=7.2 Hz, 1H), 1.35 (d, *J*=7.2 Hz, 3H), 1.28 -1.14 (m, 2H), 1.04 - 0.82 (m, 3H), 0.81 - 0.67 (m, 3H) |

FIG. 3A. Continued

| No. | BRafV600E DC50 (nM) | BRafV600 E Dmax (%) | NMR Transcript |
|---|---|---|---|
| 439 | D | A | $^1$H NMR: (400MHz, DMSO-$d_6$) δ: 12.91 (s, 1H), 8.98 (s, 1H), 8.65 (d, $J$=2.0 Hz, 1H), 8.53 (s, 1H), 8.43 (d, $J$=8.0 Hz, 1H), 8.13 (s, 1H), 8.07 (s, 1H), 7.67 - 7.54 (m, 3H), 7.47 - 7.40 (m, 2H), 7.40 - 7.33 (m, 2H), 7.27 (t, $J$=8.8 Hz, 1H), 7.07 (d, $J$=8.8 Hz, 2H), 5.41 - 5.20 (m, 1H), 5.16 (d, $J$=4.0 Hz, 1H), 4.91 (t, $J$=7.2 Hz, 1H), 4.36 (t, $J$=7.6 Hz, 1H), 4.29 (s, 1H), 3.83 - 3.73 (m, 3H), 3.71 (d, $J$=10.4 Hz, 1H), 3.55 - 3.43 (m, 5H), 3.30 - 3.28 (m, 4H), 3.22 - 3.00 (m, 2H), 2.73 (t, $J$=11.6 Hz, 2H), 2.55 - 2.52 (m, 2H), 2.45 (s, 4H), 2.43 - 2.38 (m, 1H), 2.29 - 2.20 (m, 1H), 2.24 (s, 1H), 2.13 - 1.93 (m, 3H), 1.88 - 1.68 (m, 4H), 1.45 - 1.33 (m, 3H), 1.30 - 1.17 (m, 2H), 1.06 - 0.94 (m, 3H), 0.83 - 0.69 (m, 3H) |
| 440 | D | A | $^1$H NMR: (400MHz, DMSO-$d_6$) δ: 12.89 (s, 1H), 9.03 - 8.94 (m, 1H), 8.64 (s, 1H), 8.53 (s, 1H), 8.44 - 8.28 (m, 1H), 8.06 (s, 1H), 7.68 - 7.53 (m, 3H), 7.50 - 7.22 (m, 6H), 7.06 (d, $J$=8.8 Hz, 2H), 6.30 - 6.18 (m, 1H), 5.43 - 5.10 (m, 2H), 4.98 - 4.87 (m, 1H), 4.52 - 4.37 (m, 1H), 4.30 (d, $J$=4.0 Hz, 1H), 4.24 - 4.12 (m, 1H), 3.95 - 3.72 (m, 3H), 3.63 - 3.51 (m, 2H), 3.44 (s, 6H), 2.72 (t, $J$=11.6 Hz, 2H), 2.46 (d, $J$=1.6 Hz, 4H), 2.45 - 2.25 (m, 10H), 2.22 - 2.19 (m, 2H), 2.18 - 1.95 (m, 9H), 1.88 - 1.62 (m, 5H), 1.39 - 1.33 (m, 5H), 1.24 - 1.19 (m, 2H) |
| 441 | D | Not calculated | $^1$H NMR (300 MHz, DMSO-$d6$): δ 8.96 (m, 1H), 8.67 (s, 1H), 8.56-8.54 (m, 2H), 8.01 (s, 1H), 7.95-7.89 (d, 1H), 7.78-7.75 (m, 2H), 7.54-7.45 (m, 4H), 7.39-7.37 (m, 4H), 6.86 (m, 1H), 5.32 (m, 1H), 5.18 (m, 2H), 4.66-4.39 (m, 10H), 4.30-4.28 (m, 1H), 3.69-3.62 (m, 6H), 3.20-3.07 (m, 6H), 2.60 (m, 2H), 2.43-2.41 (m, 2H), 2.12-1.65 (m, 7H), 0.97 (s, 9H) |
| 442 | D | Not calculated | $^1$H-NMR: (300 MHz, $CD_3OD$, ppm) δ 8.86 (s, 1H), 8.73 (s, 1H), 8.6 (d, $J$=2.1Hz, 1H), 7.91 (s, 1H), 7.76-7.74 (m, 1H), 7.66-7.63 (m, 2H), 7.44-7.39 (m, 6H), 7.13-7.10 (m, 1H), 5.30-5.13 (m, 1H), 5.01-4.99 (m, 1H), 4.63-4.43 (m, 3H), 3.84-3.75 (m, 2H), 3.58-3.38 (m, 5H), 3.07 (s, 2H), 2.68-2.62 (m, 11H), 2.47 (s, 3H), 2.35-1.95 (m, 8H), 1.56-1.50 (m, 3H), 1.05-1.03 (m, 9H) |

FIG. 3A. Continued

| No. | BRafV600E DC50 (nM) | BRafV600E Dmax (%) | NMR Transcript |
|---|---|---|---|
| 443 | D | B | $^1$H-NMR: (300 MHz, $CD_3OD$, ppm) δ 8.85 (s, 1H), 8.72 (s, 1H), 8.62-8.61 (d, *J* = 2.1 Hz, 1H), 7.91 (s, 1H), 7.76-7.74 (m, 1H), 7.62 (d, *J* = 8.4 Hz, 2H), 7.41-7.35 (m, 6H), 7.13-7.10 (m, 1H), 5.30-5.13 (m, 1H), 5.01-5.00 (m, 1H), 4.63-4.57 (m, 2H), 4.43-4.38 (m, 1H), 3.84-3.72 (m, 2H), 3.58-3.41 (m, 5H), 3.08-3.07 (m, 2H), 2.61-2.55 (m, 12H), 2.46 (s, 3H), 2.17-1.86 (m, 7H), 1.52-1.50 (m, 3H), 1.05-1.03 (m, 9H) |
| 444 | D | Not calculated | $^1$H NMR (300 MHz, DMSO-$d_6$, ppm): δ 12.89 (s, 1H), 9.90 (brs, 1H), 8.95 (s, 1H), 8.62 (s, 1H), 8.50 (s, 1H), 8.05 (s, 1H), 7.80-7.52 (m, 4H), 7.50-7.29 (m, 5H), 7.12-7.03 (m, 2H), 6.73 (s, 1H), 5.43-4.90 (m, 3H), 4.50-4.42 (m, 2H), 3.91-3.75 (m, 5H), 3.59-3.40 (m, 5H), 3.20-2.80 (m, 2H), 2.81-2.67 (m, 3H), 2.45-2.41 (m, 4H), 2.40-1.96(m, 7H), 1.94-1.71 (m, 3H), 1.42-1.10 (m, 7H), 0.97-0.90 (m, 1H), 0.73 (s, 9H) |
| 445 | D | Not calculated | $^1$H NMR (300 MHz, DMSO- $d_6$, *ppm*) δ 12.89 (br s, 1H), 11.95 (s, 1H), 9.83 (br s, 1H), 8.95 (s, 1H), 8.62 (d, J = 2.2 Hz, 1H), 8.51 (s, 1H), 8.05 (s, 1H), 7.78-7.70 (m, 3H), 7.57-7.50 (m, 4H), 7.42 (d, J = 8.0 Hz, 2H), 7.24-7.20 (m, 1H), 7.10-7.01 (m, 2H), 5.49-5.27 (m, 2H), 5.11-5.03 (m, 1H), 4.61-4.50 (m, 2H), 3.95-3.84 (m, 1H), 3.71-3.61 (m, 1H), 3.47-3.42 (m, 1H), 3.41-3.37 (m, 2H), 3.30- 3.20 (m, 1H), 3.19-3.10 (m, 4H), 2.93-2.72 (m, 4H), 2.46 (s, 3H), 2.41-1.89 (m, 9H), 1.89-1.70 (m, 2H), 1.68-1.52 (m, 1H), 1.28-1.22 (m, 1H), 1.21-1.11 (m, 3H), 0.95-0.91 (m, 1H), 0.85-0.72 (m, 9H) |
| 446 | D | B | $^1$H NMR: (400MHz, DMSO-$d_6$) δ: 12.94 (s, 1H), 9.85 (s, 1H), 9.00 - 8.90 (m, 1H), 8.66 (d, *J*=2.4 Hz, 1H), 8.56 (s, 1H), 8.22 (d, *J*=7.6 Hz, 1H), 8.09 (s, 1H), 7.70 - 7.58 (m, 3H), 7.50 - 7.24 (m, 5H), 7.12 - 7.04 (m, 2H), 6.25 - 6.12 (m, 1H), 5.39 - 5.20 (m, 1H), 5.16 - 4.99 (m, 1H), 4.99 - 4.84 (m, 1H), 4.43 (t, *J*=7.6 Hz, 1H), 4.33 - 4.22 (m, 1H), 3.99 - 3.84 (m, 2H), 3.77 - 3.61 (m, 3H), 3.56 (s, 1H), 3.53 - 3.42 (m, 2H), 3.42 - 3.38 (m, 2H), 3.33 - 3.26 (m, 2H), 2.91 - 2.70 (m, 2H), 2.53 - 2.51 (m, 1H), 2.46 (s, 1H), 2.44 (s, 2H), 2.31 - 2.10 (m, 2H), 2.05 - 1.93 (m, 2H), 1.84 - 1.77 (m, 2H), 1.46 (d, *J*=7.2 Hz, 1H), 1.42 - 1.27 (m, 4H), 0.96 (d, *J*=6.8 Hz, 2H), 0.88 - 0.80 (m, 3H), 0.76 (d, *J*=6.8 Hz, 1H) |

FIG. 3A. Continued

| No. | BRafV600E DC50 (nM) | BRafV600E Dmax (%) | NMR Transcript |
|---|---|---|---|
| 447 | D | B | $^1$H NMR: (400MHz, DMSO-$d_6$) δ: 12.93 (s, 1H), 9.85 (s, 1H), 8.98 (s, 1H), 8.66 (d, *J*=2.0 Hz, 1H), 8.56 (s, 1H), 8.41 (d, *J*=7.6 Hz, 1H), 8.08 (s, 1H), 7.73 - 7.56 (m, 3H), 7.50 - 7.41 (m, 2H), 7.40 - 7.33 (m, 2H), 7.26 (t, *J*=8.8 Hz, 1H), 7.09 (d, *J*=8.8 Hz, 2H), 6.15 (s, 1H), 5.40 - 5.20 (m, 1H), 5.12 (d, *J*=3.6 Hz, 1H), 4.91 (t, *J*=7.2 Hz, 1H), 4.37 (t, *J*=7.8 Hz, 1H), 4.32 - 4.22 (m, 1H), 3.94 (d, *J*=6.0 Hz, 2H), 3.77 - 3.65 (m, 3H), 3.57 (d, *J*=10.0 Hz, 1H), 3.49 - 3.42 (m, 2H), 3.42 - 3.38 (m, 3H), 3.31 - 3.25 (m, 2H), 2.82 (t, *J*=11.2 Hz, 2H), 2.45 (s, 3H), 2.29 - 2.10 (m, 2H), 2.03 - 1.94 (m, 2H), 1.85 (d, *J*=11.2 Hz, 2H), 1.81 - 1.73 (m, 1H), 1.40 - 1.36 (m, 3H), 1.36 - 1.31 (m, 1H), 1.04 - 0.89 (m, 3H), 0.87 - 0.75 (m, 3H) |
| 448 | D | C | $^1$H NMR: (400 MHz, DMSO-$d_6$) *δ:* 12.88 (s, 1H), 9.05 (s, 1H), 8.70 - 8.39 (m, 3H), 8.06 (s, 1H), 7.73 (d, *J*=9.6 Hz, 1H), 7.68 - 7.43 (m, 6H), 7.43 - 7.35 (m, 2H), 7.25 (t, *J*=8.4 Hz, 1H), 7.06 (d, *J*=8.8 Hz, 2H), 5.39 - 5.20 (m, 1H), 5.13 (s, 1H), 4.91 (m, 1H), 4.55 - 4.20 (m, 6H), 3.78 (d, *J*=11.6 Hz, 2H), 3.68 - 3.45 (m, 11H), 3.05 (d, *J*=16.4 Hz, 2H), 2.92 (d, *J*=16.0 Hz, 1H), 2.78 - 2.64 (m, 3H), 2.20 (d, *J*=7.2 Hz, 2H), 2.14 - 1.89 (m, 4H), 1.87 - 1.62 (m, 5H), 1.39 (d, *J*=7.2 Hz, 3H), 1.30 - 1.06 (m, 3H), 0.94 (s, 10H). |
| 449 | C | C | $^1$H NMR (300 MHz, $CD_3OD$) δ 8.86 (s, 1H), 8.75 (s, 1H), 8.64 (d, *J* = 2.4 Hz, 1H), 7.91 (s, 1H), 7.80-7.71 (m, 1H),7.68-7.65 (m, 2H), 7.45-7.43 (m, 4H), 7.29-7.27 (m, 2H),7.17-7.10 (m, 1H), 5.23 (d, *J*=52.5 Hz, 1H), 5.06-5.02 (m, 1H), 4.65-4.31 (m, 3H), 3.91-3.75 (m, 4H), 3.58-3.35 (m, 6H), 3.04 (s, 2H), 2.95-2.87 (m, 2H), 2.81-2.77 (m, 2H), 2.47 (s, 3H), 2.28-2.11 (m, 8H), 2.03-1.96 (m, 2H), 1.90-1.81 (m, 2H), 1.63 (s, 1H), 1.38-1.22 (m, 2H), 1.06-1.04 (m, 9H), 0.88 (d, *J* = 6.0 Hz, 6H) |
| 450 | B | C | $^1$H-NMR: (300 MHz, $CD_3OD$, ppm) δ 8.87 (s, 1H), 8.72 (s, 1H), 8.61 (s, 1H), 7.91 (s, 1H), 7.76-7.74 (m, 1H), 7.47-7.39 (m, 6H), 7.17-7.13 (m, 2H), 5.31-5.13 (m, 1H), 5.02-5.00 (m, 1H), 4.63-4.44 (m, 3H), 3.85-3.72 (m, 2H), 3.58-3.42 (m, 4H), 3.21-3.20 (m, 4H), 3.05-2.98 (m, 4H), 2.82 (s, 4H), 2.47 (s, 3H), 2.22-2.17 (m, 6H), 2.03-1.95 (m, 4H), 1.69-1.51 (m, 4H), 1.06-1.04 (m, 9H) |

FIG. 3A. Continued

| No. | BRafV600E DC50 (nM) | BRafV600 E Dmax (%) | NMR Transcript |
|---|---|---|---|
| 451 | C | C | $^1$H NMR (400 MHz, DMSO- $d_6$, *ppm*): δ 12.90 (brs, 1H), 9.84 (brs, 1H), 8.99 (s, 1H), 8.65 (s, 1H), 8.54 (s, 1H), 8.46 (d, J = 7.6 Hz, 1H), 8.06 (s, 1H), 7.75 (d, J = 9.7 Hz, 1H), 7.70-7.60 (m, 3H), 7.44 (d, J = 8.0 Hz, 2H), 7.38 (d, J = 8.0 Hz, 2H), 7.30-7.22 (m, 1H), 7.08-7.01 (m, 2H), 5.40-5.21 (m, 1H), 5.14 (s, 1H), 4.96-4.90 (m, 1H), 4.53-4.42 (m, 2H), 4.29-4.21 (m,2H), 3.61-3.57 (m, 2H), 3.52-3.46 (m, 2H), 3.32-3.21 (m, 4H), 3.07-3.01 (m, 1H), 2.90-2.77 (m, 3H), 2.46 (s, 3H), 2.43-2.38 (m, 2H), 2.17-2.00 (m, 6H), 1.74-1.60 (m, 3H), 1.50-1.13 (m, 12H), 0.95 (s, 9H) |
| 452 | D | Not calculated | $^1$H NMR: (DMSO-$d_6$) *δ*: 9.04 - 8.92 (m, 1H), 8.64 (d, *J*=2.0 Hz, 1H), 8.55 (s, 1H), 8.38 (d, *J*=8.0 Hz, 1H) , 8.06 (s, 1H), 7.75 - 7.54 (m, 3H), 7.52 - 7.27 (m, 4H), 7.19 (t, *J*=8.8 Hz, 1H), 7.11 - 6.99 (m, 2H), 6.34 - 6.02 (m, 1H), 5.38 - 5.04 (m, 2H), 5.01 - 4.80 (m, 1H), 4.76 - 4.58 (m, 1H), 4.51 - 4.35 (m, 1H), 4.30 (s, 1H), 4.10 (t, *J*=7.6 Hz, 1H), 4.05 - 3.86 (m, 3H), 3.76 (dd, *J*=4.4, 10.0 Hz, 1H), 3.56 - 3.49 (m, 2H), 3.51 - 3.43 (m, 1H), 2.47 - 2.35 (m, 5H), 2.26 - 2.14 (m, 3H), 2.13 - 1.89 (m, 4H), 1.88 - 1.64 (m, 4H), 1.59 - 1.09 (m, 5H) |
| 453 | D | Not calculated | $^1$H NMR: (DMSO-$d_6$) *δ*: 9.02 - 8.94 (m, 1H), 8.65 (d, *J*=1.6 Hz, 1H), 8.56 (s, 1H), 8.38 (d, *J*=7.6 Hz, 1H), 8.20 (s, 1H), 8.07 (s, 1H), 7.72 - 7.56 (m, 3H), 7.48 - 7.37 (m, 3H), 7.36 - 7.27 (m, 2H), 7.22 (t, *J*=8.8 Hz, 1H), 7.07 (d, *J*=8.8 Hz, 2H), 6.34 - 6.17 (m, 1H), 5.35 (s, 1H), 5.22 (s, 1H), 5.13 (s, 1H), 5.04 - 4.86 (m, 1H), 4.51 - 4.38 (m, 1H), 4.28 (s, 1H), 4.16 - 3.90 (m, 2H), 3.73 (d, *J*=7.6 Hz, 1H), 3.62 - 3.51 (m, 1H), 3.46 (s, 2H), 2.42 (d, *J*=8.8 Hz, 5H), 2.27 - 2.14 (m, 3H), 2.07 (d, *J*=15.2 Hz, 2H), 2.12 - 2.01 (m, 1H), 1.99 - 1.88 (m, 2H), 1.87 - 1.69 (m, 3H), 1.52 - 1.35 (m, 5H) |
| 454 | D | B | $^1$H NMR: (400 MHz, DMSO-$d_6$) *δ:* 12.88 (s, 1H), 8.67 - 8.61 (m, 1H), 8.51 (s, 1H), 8.41 (d, *J*=7.6 Hz, 1H), 8.15 (s, 1H), 8.05 (s, 1H), 7.71 (d, *J*=9.6 Hz, 1H), 7.67 - 7.50 (m, 4H), 7.42 - 7.20 (m, 6H), 7.05 (d, *J*=8.8 Hz, 2H), 5.38 - 5.19 (m, 1H), 5.10 (s, 1H), 4.93 - 4.83 (m, 1H), 4.54 - 4.38 (m, 2H), 4.27 (s, 1H), 3.77 (d, *J*=12.8 Hz, 2H), 3.65 - 3.50 (m, 2H), 3.46 (s, 1H), 3.44 - 3.34 (m, 4H), 3.09 - 2.99 (m, 1H), 2.90 (d, *J*=16 Hz, 1H), 2.78 - 2.63 (m, 3H), 2.32 (d, *J*=1.6 Hz, 1H), 2.19 (d, *J*=7.2 Hz, 3H), 2.13 - 1.62 (m, 10H), 1.48 - 1.32 (m, 4H), 1.28 - 1.09 (m, 4H), 0.93 (s, 12H). |

FIG. 3A. Continued

| No. | BRafV600E DC50 (nM) | BRafV600E Dmax (%) | NMR Transcript |
|---|---|---|---|
| 455 | | | $^1$H NMR: (400MHz, DMSO-$d_6$) $\delta$: 11.08 (s, 1H), 10.67 (s, 1H), 8.84 (d, *J*=2.4 Hz, 1H), 8.35 - 8.24 (m, 2H), 8.13 (s, 1H), 8.06 (d, *J*=2.4 Hz, 1H), 8.00 (d, *J*=8.0 Hz, 1H), 7.81 (t, *J*=7.6 Hz, 1H), 7.73 - 7.66 (m, 2H), 7.41 - 7.34 (m, 2H), 7.27 (d, *J*=7.6 Hz, 1H), 7.13 - 7.06 (m, 2H), 7.01 - 6.92 (m, 2H), 5.07 (dd, *J*=5.2, 12.8 Hz, 1H), 4.02 (t, *J*=6.0 Hz, 2H), 3.80 - 3.74 (m, 4H), 3.46 (s, 1H), 3.31 - 3.29 (m, 5H), 3.19 (d, *J*=4.0 Hz, 5H), 2.94 - 2.84 (m, 1H), 2.63 - 2.52 (m, 4H), 2.44 (s, 4H), 2.06 - 1.96 (m, 1H), 1.83 - 1.61 (m, 4H) |
| 456 | D | A | $^1$H NMR (400 MHz, Methanol-$d_4$, *ppm*): δ 8.87 (d, J = 3.6 Hz, 1H), 8.66 (s, 1H), 8.57 (d, J = 2.2 Hz, 1H), 7.89 (s, 1H), 7.76-7.70 (m, 1H), 7.54 (d, J = 8.2 Hz, 2H), 7.48-7.34 (m, 4H), 7.14 (t, J = 8.7 Hz, 1H), 6.63 (d, J = 8.2 Hz, 2H), 5.35-5.10 (m, 1H), 5.08-5.01 (m, 1H), 4.65 (s, 1H), 4.58 (t, J = 8.4 Hz, 1H), 4.54-4.36 (m, 1H), 3.96 (s, 2H), 3.87-3.82 (m, 1H), 3.83-3.72 (m, 3H), 3.65-3.37 (m, 6H), 3.15-3.01 (m, 2H), 2.81-2.61 (m, 6H), 2.60-2.51 (m, 3H), 2.49-2.43 (m, 3H), 2.45-2.31 (m, 2H), 2.28-2.09 (m, 2H), 2.08-1.90 (m, 3H), 1.56-1.50 (m, 3H), 1.38-1.28(m, 1H), 1.06 (d, J = 10.4 Hz, 9H) |
| 457 | C | B | $^1$H NMR (400 MHz, $CD_3OD$) δ 8.89 (s, 1H), 8.75 (s, 1H), 8.65 (s, 1H), 7.92 (s, 1H), 7.76 (s, 1H),7.67-7.65 (m, 2H), 7.24 -7.21 (m, 4H), 7.15 (m, 3H), 5.12-5.05 (m, 4H), 4.88 (s, 1H), 3.89-3.85 (m, 4H), 3.83-3.60 (m, 8H), 3.06 (m, 2H), 2.92 (m, 3H), 2.72-2.50 (m, 10H), 2.22- 2.20 (m, 2H), 2.12- 2.10 (m, 2H), 1.35-1.30 (m, 4H), 1.08-1.03(m, 15H) |
| 458 | D | C | $^1$H NMR (400 MHz, $CD_3OD$-$d_4$) δ 8.89 (s, 1H), 8.65 (s, 1H), 8.55 (s, 1H), 7.92 (s, 1H), 7.76 (s, 1H),7.67-7.65 (m, 2H),7.24 -7.21 (m, 4H), 7.15(m, 3H),5.10-5.05(m, 4H),4.88(s, 1H),3.78-3.75(m, 4H),3.83-3.60(m, 8H), 3.06 (m, 2H), 2.92 (m, 3H), 2.72-2.50 (m, 10H),2.22- 2.20 (m, 2H), 2.12- 2.10 (m, 2H),1.35-1.30(m, 4H), 1.08-1.03(m, 15H) |

FIG. 3A. Continued

| No. | BRafV600E DC50 (nM) | BRafV600E Dmax (%) | NMR Transcript |
|---|---|---|---|
| 459 | D | Not calculated | $^1$H NMR (300 MHz, DMSO-$d_6$, *ppm*): δ 12.92 (s, 1H), δ 11.50 (brs, 1H), 9.88 (brs, 1H), 8.65 (d, J = 2.2 Hz, 1H), 8.53 (s, 1H), 8.08 (s, 1H), 7.80-7.64 (m, 1H), 7.68-7.54 (m, 3H), 7.30-7.20 (m, 4H), 7.20-7.10 (m,3H), 7.07 (d, J = 8.5 Hz, 2H), 6.64 (s, 1H), 5.39-5.01 (m, 3H), 4.46 (d, J = 9.1 Hz, 2H), 3.98-3.78 (m, 5H), 3.65-3.55 (m, 3H), 3.53-3.40 (m, 2H), 3.06-2.96 (m, 3H), 2.73 (t, J = 11.9 Hz, 3H), 2.60 (s,1H), 2.40-2.20 (m,4H), 2.19-2.03 (m, 4H), 1.90-1.71 (m, 3H), 1.31-1.12 (m, 3H), 0.92-0.89 (m, 1H), 0.79 (s, 9H) |
| 460 | D | Not calculated | $^1$H NMR: (400 MHz, DMSO-d6) *δ*: 9.01 - 8.91 (m, 1H), 8.64 (dd, J=2.2, 13.6 Hz, 1H), 8.55 (s, 1H), 8.47 - 8.35 (m, 1H), 8.06 (s, 1H), 7.67 (d, J=8.6 Hz, 1H), 7.64 - 7.55 (m, 2H), 7.46 - 7.32 (m, 5H), 7.19 (t, J=8.4 Hz, 1H), 7.08 (dd, J=8.8, 18.2 Hz, 2H), 6.32 - 6.21 (m, 1H), 5.41 - 5.06 (m, 2H), 4.99 - 4.85 (m, 1H), 4.50 - 4.35 (m, 1H), 4.32 - 4.14 (m, 4H), 3.76 (d, J=4.6 Hz, 3H), 3.57 - 3.41 (m, 5H), 2.47 - 2.39 (m, 4H), 2.18 (d, J=6.4 Hz, 4H), 2.12 - 1.94 (m, 5H), 1.84 - 1.64 (m, 1H), 1.42 - 1.32 (m, 4H), 1.23 (s, 1H) |
| 461 | D | B | $^1$H NMR: (400MHz, DMSO-$d_6$) *δ*: 12.93 (s, 1H), 9.84 (s, 1H), 8.96 (s, 1H), 8.72 - 8.52 (m, 2H), 8.41 (d, J=7.6 Hz, 1H), 8.08 (s, 1H), 7.71 - 7.54 (m, 3H), 7.48 - 7.31 (m, 4H), 7.26 (t, J=8.8 Hz, 1H), 7.07 (d, J=8.8 Hz, 2H), 6.26 - 6.01 (m, 1H), 5.41 - 5.20 (m, 1H), 5.15 - 5.02 (m, 1H), 5.00 - 4.86 (m, 1H), 4.40 (t, J=7.6 Hz, 1H), 4.33 - 4.08 (m, 4H), 3.84 - 3.34 (m, 13H), 2.45 - 2.40 (m, 3H), 2.23 - 1.93 (m, 6H), 1.88 - 1.71 (m, 1H), 1.38 (d, J=6.8 Hz, 3H) |
| 462 | D | Not calculated | $^1$H NMR: (400MHz, DMSO-$d_6$) *δ*: 12.92 (s, 1H), 9.84 (s, 1H), 9.03 - 8.92 (m, 1H), 8.69 - 8.49 (m, 2H), 8.35 (d, J=7.6 Hz, 1H), 8.08 (s, 1H), 7.77 - 7.53 (m, 3H), 7.47 - 7.20 (m, 5H), 7.09 (d, J=8.4 Hz, 2H), 6.37 - 6.19 (m, 1H), 5.43 - 5.20 (m, 1H), 5.12 (d, J=3.2 Hz, 1H), 5.04 - 4.85 (m, 1H), 4.65 - 4.38 (m, 1H), 4.34 - 4.09 (m, 4H), 3.79 (s, 2H), 3.66 - 3.36 (m, 11H), 2.47 - 2.38 (m, 3H), 2.24 - 1.97 (m, 6H), 1.83 - 1.70 (m, 1H), 1.47 - 1.29 (m, 3H) |

FIG. 3A. Continued

| No. | BRafV600E DC50 (nM) | BRafV600E Dmax (%) | NMR Transcript |
|---|---|---|---|
| 463 | D | A | $^1H$ NMR: (400MHz, DMSO-$d_6$) δ: 8.96 (s, 1H), 8.71 - 8.52 (m, 2H), 8.43 (s, 1H), 8.08 (s, 1H), 7.64 (s, 3H), 7.49 - 7.19 (m, 6H), 7.08 (s, 2H), 6.34 - 6.04 (m, 1H), 5.41 - 4.81 (m, 3H), 4.45 - 4.07 (m, 4H), 3.77 (s, 2H), 3.62 - 3.50 (m, 12H), 2.43 (s, 3H), 2.28 - 1.91 (m, 10H), 1.81 (s, 1H), 1.37 (s, 4H) |
| 464 | D | A | $^1H$ NMR: (400MHz, DMSO-$d_6$) δ: 12.93 (s, 1H), 9.86 (s, 1H), 9.08 - 8.91 (m, 1H), 8.73 - 8.53 (m, 2H), 8.36 (d, J=8.0 Hz, 1H), 8.08 (s, 1H), 7.73 - 7.55 (m, 3H), 7.50 - 7.22 (m, 5H), 7.15 - 7.03 (m, 2H), 6.36 - 6.20 (m, 1H), 5.41 - 5.18 (m, 2H), 5.12 (d, J=3.6 Hz, 1H), 5.05 - 4.84 (m, 1H), 4.69 - 4.38 (m, 3H), 4.32 - 4.12 (m, 4H), 3.79 (d, J=4.8 Hz, 2H), 3.68 - 3.37 (m, 9H), 2.44 (s, 3H), 2.36 - 1.85 (m, 8H), 1.84 - 1.68 (m, 1H), 1.48 - 1.17 (m, 4H) |
| 465 | | | $^1H$ NMR: (400 MHz, DMSO-d6) δ: 8.99 (d, *J*=2.4 Hz, 1H), 8.63 (s, 1H), 8.50 (s, 1H), 8.09 (d, *J*=8.0 Hz, 1H), 7.97 (s, 1H), 7.59 (d, *J*=8.8 Hz, 2H), 7.54 - 7.38 (m, 4H), 7.36 - 7.29 (m, 1H), 7.07 (d, *J*=8.8 Hz, 2H), 6.98 (s, 1H), 6.20 - 6.12 (m, 1H), 5.36 - 5.15 (m, 1H), 5.11 (d, *J*=3.2 Hz, 1H), 5.06 - 4.90 (m, 1H), 4.82 (s, 2H), 4.47 (t, *J*=6.8 Hz, 1H), 4.30 (s, 2H), 3.75 - 3.53 (m, 9H), 3.50 - 3.41 (m, 4H), 3.21 (s, 5H), 2.72 (s, 2H), 2.46 (d, *J*=5.6 Hz, 5H), 2.21 (d, *J*=19.6 Hz, 3H), 2.08 - 1.90 (m, 3H), 1.71 (s, 3H), 1.27 - 1.06 (m, 2H), 0.97 (d, *J*=6.8 Hz, 2H), 0.88 - 0.71 (m, 4H). |
| 466 | | | $^1H$ NMR: (400 MHz, DMSO-d6) δ: 8.98 (s, 1H), 8.64 (d, *J*=2.0 Hz, 1H), 8.51 (s, 1H), 8.36 (d, *J*=7.6 Hz, 1H), 8.01 (s, 1H), 7.64 - 7.53 (m, 3H), 7.48 - 7.34 (m, 4H), 7.07 (d, *J*=8.8 Hz, 3H), 6.12 (s, 1H), 5.38 - 5.16 (m, 1H), 5.10 (d, *J*=3.6 Hz, 1H), 4.93 - 4.75 (m, 2H), 4.42 (t, *J*=7.2 Hz, 1H), 4.29 (s, 1H), 3.72 (d, *J*=10.4 Hz, 1H), 3.68 - 3.53 (m, 6H), 3.42 (d, *J*=14.0 Hz, 5H), 3.22 (s, 6H), 2.77 (t, *J*=10.8 Hz, 2H), 2.23 (s, 4H), 2.14 - 1.93 (m, 5H), 1.89 - 1.64 (m, 5H), 1.16 (d, *J*=11.2 Hz, 3H), 0.95 (d, J=6.4 Hz, 3H), 0.86 - 0.74 (m, 3H). |

FIG. 3A. Continued

| No. | BRafV600E DC50 (nM) | BRafV600E Dmax (%) | NMR Transcript |
|---|---|---|---|
| 467 | | | $^1$H NMR: (400MHz, DMSO-$d_6$) δ: 11.10 (s, 1H), 10.73 - 10.64 (m, 1H), 8.91 - 8.73 (m, 1H), 8.29 (d, *J*=8.4 Hz, 2H), 8.06 (d, *J*=2.4 Hz, 1H), 8.00 (d, *J*=7.6 Hz, 1H), 7.86 - 7.78 (m, 2H), 7.74 - 7.69 (m, 1H), 7.48 (d, *J*=2.0 Hz, 1H), 7.41 - 7.35 (m, 2H), 7.14 - 7.08 (m, 2H), 7.01 - 6.95 (m, 2H), 5.12 (m, 1H), 4.40 - 4.32 (m, 2H), 4.17 - 4.06 (m, 2H), 3.93 - 3.82 (m, 4H), 3.81 - 3.75 (m, 4H), 3.20 (d, *J*=4.4 Hz, 4H), 2.98 - 2.84 (m, 1H), 2.64 - 2.54 (m, 2H), 2.45 (s, 3H), 2.09 - 2.01 (m, 1H) |
| 468 | D | Not calculated | $^1$H NMR: (400MHz, DMSO-$d_6$) δ = 11.10 (d, *J*=1.0 Hz, 1H), 10.73 - 10.60 (m, 1H), 8.85 (d, *J*=2.4 Hz, 1H), 8.32 (s, 1H), 8.28 (d, *J*=7.7 Hz, 1H), 8.05 (d, *J*=2.3 Hz, 1H), 7.99 (d, *J*=8.0 Hz, 1H), 7.86 - 7.77 (m, 2H), 7.71 (d, *J*=2.1 Hz, 1H), 7.46 (d, *J*=2.2 Hz, 1H), 7.41 - 7.33 (m, 2H), 7.13 - 7.05 (m, 2H), 7.00 - 6.93 (m, 2H), 5.11 (dd, *J*=5.6, 12.9 Hz, 1H), 4.32 (dd, *J*=3.6, 5.2 Hz, 2H), 4.16 - 4.02 (m, 2H), 3.84 - 3.79 (m, 2H), 3.78 - 3.73 (m, 6H), 3.64 (s, 4H), 3.56 (d, *J*=8.8 Hz, 1H), 3.48 - 3.37 (m, 1H), 3.21 - 3.17 (m, 3H), 2.94 - 2.81 (m, 1H), 2.60 (d, *J*=2.4 Hz, 1H), 2.44 (s, 3H), 2.08 - 1.98 (m, 1H) |
| 469 | D | Not calculated | $^1$H NMR: (400MHz, DMSO-$d_6$) δ = 11.23 - 10.91 (m, 2H), 9.20 - 9.03 (m, 1H), 8.48 - 8.30 (m, 3H), 8.04 (d, *J*=8.4 Hz, 1H), 7.88 - 7.72 (m, 3H), 7.50 - 7.44 (m, 1H), 7.22 - 7.14 (m, 2H), 7.10 (d, *J*=9.0 Hz, 2H), 6.98 (d, *J*=9.0 Hz, 2H), 5.16 (m, 1H), 4.13 - 4.07 (m, 2H), 3.93 - 3.72 (m, 8H), 3.53 - 3.50 (m, 10H), 3.20 (s, 4H), 3.03 - 2.85 (m, 2H), 2.80 - 2.71 (m, 1H), 2.64 - 2.54 (m, 4H), 2.53 (s, 3H), 2.09 - 2.00 (m, 1H) |
| 470 | D | B | $^1$H NMR (300 MHz, DMSO-$d_6$, ppm): δ 12.95 (br s, 1H), 9.93 (br s, 1H), 9.00 (s, 1H), 8.67 (s, 1H), 8.61-8.56 (m, 1H), 8.49-8.41 (m, 1H), 8.09 (s, 1H), 7.80-7.72 (m, 1H), 7.71-7.63 (m, 3H), 7.50-7.43 (m, 4H), 7.29-7.21 (m, 1H), 7.09-7.01 (m, 2H), 5.43-5.08 (m, 2H), 4.93-4.77 (m, 2H), 4.55-4.51 (m, 2H), 4.30-4.21 (m, 1H), 3.72-3.40 (m, 7H), 3.40-3.24 (m, 5H), 3.07-3.01 (m, 1H), 2.96-2.84 (m, 3H), 2.70-2.59 (m, 3H), 2.48-2.30 (m, 5H), 2.29-2.11 (m, 5H), 1.74-1.61 (m, 3H), 1.59-1.36 (m, 6H), 0.96 (s, 9H) |

FIG. 3A. Continued

| No. | BRafV600E DC50 (nM) | BRafV600E Dmax (%) | NMR Transcript |
|---|---|---|---|
| 471 | D | B | $^1$H NMR (300 MHz, DMSO-$d_6$, *ppm*): δ 12.93 (s, 1H), 9.80(brs,1H), 8.99 (s, 1H), 8.90-8.40 (m, 3H), 8.20-7.90 (m, 1H), 7.75-7.45 (m, 4H), 7.45-7.30 (m, 4H), 7.30-7.20 (m, 1H), 7.09 (d, J = 8.5 Hz, 2H), 5.60-5.10 (m, 2H), 5.10-4.80 (m, 1H), 4.73-4.20 (m, 3H), 3.70-3.40 (m, 5H), 3.35-3.10 (m, 7H), 3.10-2.90(m, 1H), 2.90-2.80 (m, 1H), 2.80-2.60 (m, 6H), 2.50-2.40 (m, 4H), 2.20-1.90 (m, 4H), 1.85-1.60 (m, 2H), 1.55-1.35 (m, 3H), 0.98 (s, 9H) |
| 472 | D | B | $^1$H NMR (300 MHz, DMSO-$d_6$, *ppm*): δ 12.93 (s, 1H), 9.80 (brs,1H), 8.99 (s, 1H), 8.90-8.40 (m, 3H), 8.20-7.90 (m, 1H), 7.75-7.45 (m, 4H), 7.45-7.20 (m, 5H), 7.10-6.90 (m, 2H), 5.60-5.10 (m, 2H), 5.10-4.80 (m, 1H), 4.73-4.20 (m, 3H), 3.70-3.40 (m, 5H), 3.35-3.10 (m, 6H), 3.10-2.90(m, 2H), 2.80-2.60 (m, 7H), 2.50-2.40 (m, 3H), 2.20-1.90 (m, 4H), 1.85-1.60 (m, 2H), 1.55-1.35 (m, 3H), 0.98 (s, 9H) |
| 473 | D | Not calculated | $^1$H NMR (300 MHz, DMSO-$d_6$, *ppm*): *δ* 12.88 (s, 1H), 9.83 (s, 1H), 8.96 (s, 1H), 8.63 (s, 1H), 8.51 (s, 1H), 8.05 (s, 1H), 7.80-7.70 (m, 1H), 7.69-7.56 (m, 3H), 7.39 (d, *J* = 8.0 Hz, 2H), 7.35-7.18 (m, 4H), 7.04 (d, *J* = 8.4 Hz, 2H), 5.74 (s, 1H), 5.44-5.06 (m, 3H), 4.51 (d, *J* = 9.3 Hz, 1H), 4.49-4.38 (m, 1H), 4.03 (s, 2H), 3.85-3.72 (m, 3H), 3.70-3.62 (m, 1H), 3.48-3.39 (m, 3H), 3.16-2.82 (m, 2H), 2.69 (t, *J* = 11.8 Hz, 2H), 2.45-2.35 (m, 6H), 2.25-2.05 (m, 7H), 1.80-1.60 (m, 3H), 1.23-1.19 (m, 6H), 0.83 (s, 9H) |
| 474 | D | Not calculated | $^1$H NMR (400 MHz, DMSO-$d_6$, *ppm*): δ 12.97 (brs, 1H), 8.98 (s, 1H), 8.70 (d, *J* = 2.2 Hz, 1H), 8.62 (s, 1H), 8.44 (d, J = 7.6 Hz, 1H), 8.11 (s, 1H), 7.74 (d, J = 9.7 Hz, 1H), 7.68-7.58 (m, 3H), 7.56-7.27 (m, 8H), 5.36 (s, 1H), 5.12 (d, J = 3.5 Hz, 1H), 4.90-4.81 (m, 1H), 4.50-4.35 (m, 2H), 4.28 (s, 1H), 3.64- 3.53 (m, 2H), 3.51-3.44 (m, 2H), 3.42-3.38 (m, 3H), 3.05-2.86 (m, 5H), 2.67-2.59 (m, 3H), 2.57-2.51 (m, 4H), 2.45 (s, 3H), 2.18-1.90 (m, 4H), 1.81-1.67 (m, 1H), 1.37-1.32 (m, 3H), 0.94 (s, 9H) |

FIG. 3A. Continued

| No. | BRafV600E DC50 (nM) | BRafV600E Dmax (%) | NMR Transcript |
|---|---|---|---|
| 475 | D | Not calculated | $^{1}$H NMR: (DMSO-$d_6$) $\delta$: 9.04 - 8.91 (m, 1H), 8.65 (s, 1H), 8.56 (s, 1H), 8.41 (d, $J$=7.5 Hz, 1H), 8.07 (s, 1H), 7.72 - 7.55 (m, 3H), 7.49 - 7.31 (m, 5H), 7.21 (s, 1H), 7.13 - 7.00 (m, 2H), 6.36 - 6.03 (m, 1H), 5.40 - 5.19 (m, 1H), 5.13 (s, 1H), 5.00 - 4.84 (m, 1H), 4.48 - 4.37 (m, 1H), 4.31 (s, 1H), 4.18 (t, $J$=7.1 Hz, 1H), 4.11 - 3.95 (m, 2H), 3.78 (dd, $J$=4.5, 10.5 Hz, 1H), 3.58 (d, $J$=11.4 Hz, 1H), 3.45 (s, 1H), 2.47 - 2.39 (m, 4H), 2.27 - 2.16 (m, 4H), 2.15 - 2.00 (m, 4H), 2.00 - 1.88 (m, 2H), 1.88 - 1.65 (m, 3H), 1.25 - 0.98 (m, 1H), 1.38 (d, $J$=6.8 Hz, 3H). |
| 476 | D | Not calculated | $^{1}$H NMR: (DMSO-$d_6$) $\delta$: 9.04 - 8.94 (m, 1H), 8.65 (d, $J$=2.1 Hz, 1H), 8.56 (s, 1H), 8.40 (d, $J$=7.7 Hz, 1H), 8.05 (s, 1H), 7.67 (d, $J$=8.7 Hz, 2H), 7.62 - 7.53 (m, 1H), 7.48 - 7.41 (m, 2H), 7.40 - 7.30 (m, 3H), 7.21 - 7.01 (m, 1H), 7.11 - 7.01 (m, 2H), 6.28 - 6.22 (m, 1H), 6.33 (s, 1H), 5.43 - 5.19 (m, 1H), 5.17 (s, 1H), 5.03 (s, 1H), 4.92 (t, $J$=7.3 Hz, 1H), 4.65 - 4.56 (m, 1H), 4.54 - 4.37 (m, 1H), 4.29 (s, 1H), 4.21 (t, $J$=7.2 Hz, 1H), 4.06 (t, $J$=6.1 Hz, 2H), 4.02 - 3.90 (m, 1H), 3.73 (t, $J$=7.7 Hz, 1H), 3.60 (d, $J$=10.0 Hz, 1H), 2.47 - 2.43 (m, 4H), 2.33 (d, $J$=1.8 Hz, 1H), 2.25 - 2.16 (m, 4H), 2.13 - 1.91 (m, 5H), 1.78 (dd, $J$=7.5, 12.5 Hz, 3H), 1.26 - 1.13 (m, 1H), 1.44 - 1.10 (m, 5H). |
| 477 | B | B | $^{1}$H NMR: (400MHz, DMSO-$d_6$) $\delta$ : 12.94 (s, 1 H), 8.97 - 9.03 (m, 1 H), 8.65 (d, $J$=2.0 Hz, 1 H), 8.53 ( s, 1 H), 8.41 (d, $J$=8.0 Hz, 1 H), 8.18 (s, 1 H), 8.06 (s, 1 H), 7.56 - 7.66 (m, 3 H), 7.34 - 7.48 (m, 4 H), 7.25 (t, $J$=8.8 Hz, 1 H), 7.06 (d, $J$=8.8 Hz, 2 H), 6.11 - 6.28 (m, 1 H), 5.20 - 5.40 (m, 1 H), 4.87 - 4.99 (m, 1 H), 4.21 - 4.43 (m, 3 H), 4.10 (s, 1 H), 3.77 (d, $J$ = 10.4 Hz, 4 H), 3.47 (s, 8 H), 3.17 (s, 5 H), 2.71 - 2.75 (m, 1 H), 2.47 (s, 6 H), 2.05 - 2.27 (m, 8 H), 1.75 - 1.86 (m, 3 H), 1.70 (s, 1 H), 1.36 - 1.47 (m, 3 H), 1.21 (d, $J$ = 8.8 Hz, 2 H), 0.98 - 1.07 (m, 3 H), 0.88 (s, 3 H). |

FIG. 3A. Continued

| No. | BRafV600E DC50 (nM) | BRafV600E Dmax (%) | NMR Transcript |
|---|---|---|---|
| 478 | C | B | $^1$H NMR: (400 MHz, DMSO-d6) $\delta$: 8.97 (s, 1H), 8.64 (d, J = 2.0 Hz, 1H), 8.52 (br s, 1H), 8.43 (d, J = 8.0 Hz, 1H), 8.15 (s, 1H), 8.05 (s, 1H), 7.70 (d, J = 10.0 Hz, 1H), 7.64 - 7.54 (m, 3H), 7.46 - 7.41 (m, 2H), 7.39 - 7.34 (m, 2H), 7.28 - 7.21 (m, 1H), 7.06 (d, J = 9.2 Hz, 2H), 5.35 (s, 1H), 5.22 (br s, 1H), 5.12 (s, 1H), 4.89 (t, J = 7.2 Hz, 1H), 4.49 (d, J = 10.2 Hz, 1H), 4.44 (t, J = 8.8 Hz, 1H), 4.28 (br s, 1H), 3.81 (br d, J = 11.2 Hz, 3H), 3.63 - 3.51 (m, 6H), 3.00 (d, J = 16.0 Hz, 1H), 2.89 - 2.78 (m, 1H), 2.65 (br s, 1H), 2.45 (s, 5H), 2.37 (br s, 2H), 2.13 - 1.76 (m, 9H), 1.48 (s, 1H), 1.38 (d, J = 7.2 Hz, 3H), 1.20 (br d, J = 8.2 Hz, 3H), 1.01 (br d, J = 6.0 Hz, 6H), 1.00 (s, 6H). |
| 479 | D | Not calculated | $^1$H NMR: (400MHz, DMSO-$d_6$) $\delta$: 12.91 (s, 1H), 9.86 (s, 1H), 9.04 - 8.91 (m, 1H), 8.65 (d, *J*=2.4 Hz, 1H), 8.54 (s, 1H), 8.42 (d, *J*=8.0 Hz, 1H), 8.07 (s, 1H), 7.66 - 7.57 (m, 3H), 7.48 - 7.36 (m, 4H), 7.26 (t, *J*=8.8 Hz, 1H), 7.15 - 7.00 (m, 2H), 5.77 (s, 1H), 5.41 - 5.19 (m, 1H), 5.13 (d, *J*=3.6 Hz, 1H), 4.84 (t, *J*=5.6 Hz, 2H), 4.46 (t, *J*=8.0 Hz, 1H), 4.34 - 4.21 (m, 1H), 3.90 - 3.80 (m, 2H), 3.75 - 3.52 (m, 4H), 3.48 (s, 2H), 3.43 - 3.35 (m, 3H), 3.32 - 3.25 (m, 3H), 3.24 - 3.15 (m, 4H), 2.47 - 2.42 (m, 4H), 2.40 - 2.34 (m, 2H), 2.26 (d, *J*=16.0 Hz, 2H), 2.14 - 1.98 (m, 3H), 1.85 - 1.73 (m, 3H), 1.00 - 0.94 (m, 3H), 0.93 - 0.86 (m, 3H). |
| 480 | C | A | $^1$H NMR: (400MHz, DMSO-$d_6$) $\delta$: 13.15 - 12.64 (m, 1H), 8.98 (s, 1H), 8.65 (d, *J*=2.0 Hz, 1H), 8.57 - 8.43 (m, 2H), 8.18 (s, 1H), 8.09 (s, 1H), 7.77 (d, *J*=9.2 Hz, 1H), 7.64 - 7.55 (m, 3H), 7.47 - 7.41 (m, 2H), 7.40 - 7.33 (m, 2H), 7.27 (t, *J*=8.4 Hz, 1H), 7.07 (d, *J*=8.8 Hz, 2H), 4.94 - 4.85 (m, 1H), 4.53 - 4.41 (m, 2H), 4.28 (s, 1H), 3.14 - 3.06 (m, 4H), 3.03 (s, 1H), 2.90 (d, *J*=16.0 Hz, 3H), 2.72 (s, 3H), 2.67 (s, 4H), 2.45 (s, 4H), 2.30 - 2.18 (m, 2H), 2.17 (s, 1H), 2.14 - 2.02 (m, 2H), 2.14 - 2.02 (m, 1H), 1.86 (s, 2H), 1.79 - 1.72 (m, 1H), 1.57 - 1.42 (m, 3H), 1.38 (d, *J*=7.2 Hz, 3H), 1.01 (t, *J*=7.2 Hz, 3H), 0.95 (s, 9H). |

FIG. 3A. Continued

| No. | BRafV600E DC50 (nM) | BRafV600E Dmax (%) | NMR Transcript |
|---|---|---|---|
| 481 | | | $^1$H NMR: (400MHz, DMSO-$d_6$) δ: 11.20 - 10.93 (m, 1H), 10.70 (s, 1H), 8.86 (d, $J$=2.4 Hz, 1H), 8.47 - 8.40 (m, 1H), 8.33 (s, 1H), 8.29 (d, $J$=8.0 Hz, 1H), 8.06 (d, $J$=2.4 Hz, 1H), 8.01 (d, $J$=7.6 Hz, 1H), 7.87 (d, $J$=8.4 Hz, 1H), 7.85 - 7.79 (m, 1H), 7.73 (d, $J$=2.0 Hz, 1H), 7.54 (d, $J$=2.4 Hz, 1H), 7.44 (m, 1H), 7.40 (d, $J$=2.0 Hz, 1H), 7.17 - 7.10 (m, 2H), 7.07 - 7.02 (m, 2H), 5.14 (m, 1H), 4.61 - 4.55 (m, 2H), 4.39 (m, 2H), 3.80 - 3.76 (m, 4H), 3.20 (d, $J$=4.4Hz, 4H), 2.96 - 2.84 (m, 1H), 2.65 - 2.57 (m, 2H), 2.45 (s, 3H), 2.12 - 2.04 (m, 1H) |
| 482 | | | $^1$H NMR: (400MHz, DMSO-$d_6$) $\delta$ = 11.23 - 10.98 (m, 1H), 10.78 - 10.64 (m, 1H), 8.97 - 8.77 (m, 1H), 8.45 (s, 1H), 8.33 (s, 1H), 8.31 - 8.26 (m, 1H), 8.10 - 8.03 (m, 1H), 8.00 (d, $J$=7.6 Hz, 1H), 7.86 - 7.76 (m, 2H), 7.71 (d, $J$=2.0 Hz, 1H), 7.45 (d, $J$=2.4 Hz, 1H), 7.41 - 7.34 (m, 2H), 7.25 - 7.15 (m, 1H), 7.13 - 7.05 (m, 2H), 7.00 - 6.94 (m, 2H), 5.18 - 5.04 (m, 1H), 4.35 - 4.27 (m, 2H), 4.13 - 4.07 (m, 2H), 3.80 - 3.73 (m, 8H), 3.61 - 3.54 (m, 8H), 3.53 - 3.49 (m, 2H), 3.19 (s, 3H), 2.93 - 2.83 (m, 1H), 2.66 - 2.56 (m, 3H), 2.44 (s, 3H), 2.10 - 1.98 (m, 1H) |
| 483 | | | $^1$H NMR: (400MHz, DMSO-$d_6$) $\delta$: 10.96 (s, 1H), 10.68 (s, 1H), 8.85 (d, $J$=2.4 Hz, 1H), 8.32 (s, 1H), 8.28 (d, $J$=8.0 Hz, 1H), 8.05 (d, $J$=2.4 Hz, 1H), 8.00 (d, $J$=8.0 Hz, 1H), 7.84 - 7.78 (m, 1H), 7.71 (d, $J$=2.0 Hz, 1H), 7.62 (d, $J$=8.4 Hz, 1H), 7.38 (d, $J$=2.0 Hz, 1H), 7.19 (s, 1H), 7.12 - 7.04 (m, 3H), 6.98 (d, $J$=9.2 Hz, 2H), 5.06 (dd, $J$=5.2, 13.2 Hz, 1H), 4.42 - 4.20 (m, 4H), 4.17 - 4.10 (m, 2H), 3.89 - 3.82 (m, 4H), 3.77 (s, 4H), 3.18 (s, 3H), 2.95 - 2.82 (m, 1H), 2.60 (s, 2H), 2.44 (s, 3H), 2.37 (dd, $J$=4.8, 13.6 Hz, 1H), 2.03 - 1.90 (m, 1H). |
| 484 | | | $^1$H NMR: (400MHz, DMSO-$d_6$) $\delta$: 10.95 (s, 1H), 10.68 (s, 1H), 8.85 (d, $J$=2.0 Hz, 1H), 8.37 - 8.18 (m, 2H), 8.10 - 7.96 (m, 2H), 7.86 - 7.77 (m, 1H), 7.71 (d, $J$=1.2 Hz, 1H), 7.61 (d, $J$=8.4 Hz, 1H), 7.38 (s, 1H), 7.18 (s, 1H), 7.13 - 7.03 (m, 3H), 6.97 (d, $J$=8.8 Hz, 2H), 5.06 (dd, $J$=5.2, 13.6 Hz, 1H), 4.42 - 4.34 (m, 1H), 4.29 - 4.22 (m, 1H), 4.22 - 4.17 (m, 2H), 4.13 - 4.06 (m, 2H), 3.83 - 3.74 (m, 8H), 3.64 (s, 4H), 3.18 (s, 3H), 2.96 - 2.82 (m, 1H), 2.60 (s, 2H), 2.43 (s, 3H), 2.40 - 2.34 (m, 1H), 2.00 - 1.87 (m, 1H). |

FIG. 3A. Continued

| No. | BRafV600E DC50 (nM) | BRafV600E Dmax (%) | NMR Transcript |
|---|---|---|---|
| 485 | | | $^1$H NMR: (400MHz, DMSO-$d_6$) δ: 10.96 (s, 1H), 10.67 (s, 1H), 8.85 (d, J=2.4 Hz, 1H), 8.35 - 8.26 (m, 2H), 8.06 (d, J=2.4 Hz, 1H), 8.00 (d, J=7.6 Hz, 1H), 7.82 (t, J=8.0 Hz, 1H), 7.72 (d, J=2.0 Hz, 1H), 7.62 (d, J=8.4 Hz, 1H), 7.39 (d, J=2.0 Hz, 1H), 7.17 (s, 1H), 7.10 (d, J=8.8 Hz, 2H), 7.08 - 7.04 (m, 1H), 6.97 (d, J=9.2 Hz, 2H), 5.07 (dd, J=5.2, 13.2 Hz, 1H), 4.42 - 4.35 (m, 1H), 4.30 - 4.23 (m, 1H), 4.21 - 4.16 (m, 2H), 4.12 - 4.07 (m, 2H), 3.81 - 3.73 (m, 8H), 3.64 - 3.53 (m, 8H), 3.19 (s, 3H), 2.97 - 2.85 (m, 1H), 2.60 (s, 3H), 2.44 (s, 3H), 2.41 - 2.35 (m, 1H), 2.05 - 1.92 (m, 1H). |
| 486 | | | $^1$H NMR: (400MHz, DMSO-$d_6$) δ: 10.96 (s, 1H), 10.69 (s, 1H), 8.85 (d, J=2.4 Hz, 1H), 8.33 (s, 1H), 8.29 (d, J=8.0 Hz, 1H), 8.06 (d, J=2.4 Hz, 1H), 8.00 (d, J=8.0 Hz, 1H), 7.86 - 7.78 (m, 1H), 7.72 (d, J=2.0 Hz, 1H), 7.62 (d, J=8.4 Hz, 1H), 7.39 (d, J=2.0 Hz, 1H), 7.17 (s, 1H), 7.10 (d, J=9.2 Hz, 2H), 7.07 - 7.03 (m, 1H), 6.98 (d, J=9.2 Hz, 2H), 5.07 (dd, J=5.2, 13.2 Hz, 1H), 4.41 - 4.23 (m, 2H), 4.21 - 4.15 (m, 2H), 4.12 - 4.07 (m, 2H), 3.81 - 3.71 (m, 8H), 3.59 (d, J=4.4 Hz, 4H), 3.56 - 3.54 (m, 3H), 3.53 (s, 4H), 3.18 (s, 4H), 2.99 - 2.84 (m, 1H), 2.60 (s, 2H), 2.44 (s, 3H), 2.41 - 2.34 (m, 1H), 2.03 - 1.93 (m, 1H). |
| 487 | C | A | $^1$H NMR (400 MHz, DMSO-$d_6$) δ 12.95 (s, 1H), 9.89 (s, 1H), 8.98 (s, 1H), 8.68 (s, 1H), 8.46 (s, 1H), 8.44 (s, 1H), 8.07 (s, 1H),7.65 (s, 1H), 7.45-7.42 (m, 3H), 7.38-7.36 (m, 2H), 7.25 (d, 2H), 7.10-7.08 (m, 3H), 5.13 (s, 1H), 5.12 (s, 1H), 5.11(s, 1H), 4.90 (s, 1H), 4.50 (s, 1H), 4.40 (s, 1H), 3.57-3.47 (m, 8H), 3.03 (s, 1H), 2.92 (m, 3H), 2.67-2.64 (m, 2H), 2.51- 2.50 (m, 3H), 2.49-2.46 (m, 6H), 1.85(m, 3H), 1.48-1.46 (m, 2H), 1.39-1.38 (m, 3H), 0.98-0.95 (m, 14H) |
| 488 | D | Not calculated | $^1$H NMR (400 MHz, DMSO-$d_6$, *ppm*): δ 13.00 (brs, 1H), 9.89 (brs, 1H), 8.99 (s, 1H), 8.73 (s, 1H), 8.70-8.61 (m, 1H), 8.47 (s, 1H), 8.13 (s, 1H), 8.81-7.74 (m, 1H), 7.66-7.60 (m, 1H), 7.46 - 7.39 (m, 3H), 7.39 - 7.33 (m, 2H), 7.31 - 7.25 (m, 3H), 7.03 - 6.99 (m, 1H), 5.40-5.30 (m, 1H), 5.14 (s, 1H), 4.89-4.81 (m, 1H), 4.50-4.47 (m, 1H), 4.46 - 4.36 (m, 1H), 4.30-4.22 (m, 1H), 4.21-4.10 (m, 2H), 3.64 - 3.52 (m, 2H), 3.48 - 3.39 (m, 3H), 3.32 - 3.23 (m, 2H), 3.06-3.00 (m, 1H), 2.95-2.85 (m, 1H), 2.77-2.71 (m, 2H), 2.70-2.46 (m, 7H), 2.40 - 2.14 (m, 3H), 2.13 - 2.00 (m, 3H), 1.75 (s, 1H), 1.38 (s, 3H), 0.94 (s, 9H) |

FIG. 3A. Continued

| No. | BRafV600E DC50 (nM) | BRafV600 E Dmax (%) | NMR Transcript |
|---|---|---|---|
| 489 | C | A | $^1$H NMR: (400MHz, DMSO-$d_6$) δ: 8.98 (s, 1H), 8.64 (d, *J*=2.0 Hz, 1H), 8.52 (s, 1H), 8.43 (d, *J*=7.6 Hz, 1H), 8.17 (s, 1H), 8.06 (s, 1H), 7.75 (d, *J*=10.0 Hz, 1H), 7.66 - 7.54 (m, 3H), 7.45 - 7.42 (m, 2H), 7.37 (d, *J*=8.4 Hz, 2H), 7.25 (t, *J*=8.4 Hz, 1H), 7.04 (d, *J*=8.8 Hz, 2H), 5.41 - 5.17 (m, 1H), 4.90 (q, *J*=7.2 Hz, 1H), 4.51 (d, *J*=10.0 Hz, 1H), 4.45 (t, *J*=8.0 Hz, 1H), 4.28 (s, 1H), 3.64 - 3.54 (m, 2H), 3.48 - 3.46 (m, 2H), 3.23 - 3.21 (m, 2H), 3.08 - 2.89 (m, 9H), 2.87 - 2.78 (m, 2H), 2.46 (s, 3H), 2.27 - 1.94 (m, 7H), 1.83 - 1.72 (m, 3H), 1.49 - 1.41 (d, *J*=7.2 Hz, 1H), 1.39 (d, *J*=7.2 Hz, 3H), 1.25 - 1.09 (m, 2H), 1.05 (d, *J*=5.6 Hz, 6H), 0.94 (s, 9H). |
| 490 | D | A | $^1$H NMR: (400 MHz, DMSO-d6) δ: 12.92 (br s, 1H), 9.84 (s, 1H), 8.99 (s, 1H), 8.66 (d, *J* = 2.4 Hz, 1H), 8.55 (br s, 1H), 8.43 - 8.35 (m, 1H), 8.08 (br s, 1H), 7.65 - 7.60 (m, 3H), 7.44 (br d, *J* = 8.0 Hz, 2H), 7.40 - 7.34 (m, 2H), 7.27 (br t, *J* = 8.4 Hz, 1H), 7.12 (br d, *J* = 8.0 Hz, 2H), 5.36 (br s, 1H), 5.23 (br s, 1H), 4.97 - 4.84 (m, 2H), 4.53 (br d, *J* = 9.2 Hz, 1H), 4.48 - 4.37 (m, 2H), 4.36 - 4.23 (m, 3H), 3.60 (br d, *J* = 11.2 Hz, 6H), 3.45 - 3.36 (m, 3H), 3.35 - 3.21 (m, 2H), 2.96 (br s, 1H), 2.81 (br s, 4H), 2.46 (s, 3H), 2.17 - 1.86 (m, 4H), 1.78 (br s, 2H), 1.38 (br d, *J* = 7.2 Hz, 6H), 1.32 - 1.11 (m, 3H), 0.96 (s, 9H) |
| 491 | C | A | $^1$H NMR: (400MHz, DMSO-$d_6$) δ: 8.97 (s, 1H), 8.69 (d, *J*=2.0 Hz, 1H), 8.58 (s, 1H), 8.43 (d, *J*=7.6 Hz, 1H), 8.16 (s, 1H), 8.07 (s, 1H), 7.77 (d, *J*=9.6 Hz, 1H), 7.67 - 7.60 (m, 3H), 7.45 - 7.41 (m, 2H), 7.39 - 7.34 (m, 2H), 7.26 (t, *J*=8.6 Hz, 1H), 7.14 (d, *J*=8.4 Hz, 2H), 5.38 - 5.20 (m, 1H), 4.89 (m, 1H), 4.54 - 4.37 (m, 2H), 4.31 - 4.16 (m, 1H), 3.35 - 3.22 (m, 9H), 3.05 - 2.81 (m, 5H), 2.63 (d, *J*=8.0 Hz, 2H), 2.45 (s, 3H), 2.36 (d, *J*=12.0 Hz, 1H), 2.31 - 2.24 (m, 3H), 2.17 - 2.01 (m, 5H), 1.79 - 1.65 (m, 3H), 1.49 - 1.33 (m, 6H), 1.26 - 1.14 (m, 2H), 0.99 - 0.83 (m, 16H). |
| 492 | D | A | $^1$H NMR: (400MHz, DMSO-$d_6$) δ: 8.98 (s, 1H), 8.68 (d, *J*=2.0 Hz, 1H), 8.56 (s, 1H), 8.43 (d, *J*=7.6 Hz, 1H), 8.16 (s, 1H), 8.07 (s, 1H), 7.76 (d, *J*=9.8 Hz, 1H), 7.68 - 7.58 (m, 4H), 7.47 - 7.41 (m, 2H), 7.39 - 7.35 (m, 2H), 7.26 (t, *J*=8.0 Hz, 1H), 7.08 (d, *J*=8.6 Hz, 2H), 5.42 - 5.17 (m, 1H), 4.90 (q, *J*=7.2 Hz, 1H), 4.54 - 4.42 (m, 2H), 4.29 (s, 1H), 3.66 - 3.54 (m, 9H), 3.09 - 2.79 (m, 4H), 2.46 (s, 3H), 2.41 - 2.30 (m, 5H), 2.20 - 2.02 (m, 6H), 1.83 - 1.65 (m, 4H), 1.46 (d, *J*=3.6 Hz, 3H), 1.39 (d, *J*=7.2 Hz, 4H), 1.23 (t, *J*=12.0 Hz, 2H), 1.00 (d, *J*=6.4 Hz, 6H), 0.95 (s, 10H). |

FIG. 3A. Continued

| No. | BRafV600E DC50 (nM) | BRafV600 E Dmax (%) | NMR Transcript |
|---|---|---|---|
| 493 | D | Not calculated | $^{1}$H NMR: (400MHz, DMSO-$d_6$) $\delta$: 12.87 (s, 1H), 9.83 (s, 1H), 9.03 - 8.94 (m, 1H), 8.67 - 8.61 (m, 1H), 8.53 (s, 1H), 8.29 (d, $J$=8.0 Hz, 1H), 8.05 (s, 1H), 7.66 - 7.54 (m, 3H), 7.50 - 7.33 (m, 4H), 7.24 (t, $J$=8.8 Hz, 1H), 7.09 - 7.02 (m, 2H), 5.95 - 5.72 (m, 1H), 5.41 - 5.18 (m, 1H), 5.14 (d, $J$=3.6 Hz, 1H), 5.10 - 4.91 (m, 1H), 4.89 - 4.80 (m, 1H), 4.61 - 4.43 (m, 1H), 4.34 - 4.19 (m, 1H), 3.92 - 3.77 (m, 2H), 3.71 - 3.64 (m, 1H), 3.62 - 3.49 (m, 4H), 3.47 (s, 3H), 3.31 - 3.24 (m, 3H), 3.23 - 3.15 (m, 4H), 2.56 - 2.52 (m, 2H), 2.47 - 2.43 (m, 3H), 2.39 - 2.26 (m, 3H), 2.13 - 2.04 (m, 2H), 2.02 - 1.88 (m, 1H), 1.86 - 1.67 (m, 3H), 0.99 (d, $J$=6.4 Hz, 2H), 0.91 (d, $J$=6.8 Hz, 2H), 0.89 - 0.77 (m, 2H). |
| 494 | D | Not calculated | $^{1}$H NMR: (400MHz, DMSO-$d_6$) $\delta$: 12.89 (s, 1H), 9.01 - 8.96 (m, 1H), 8.64 (d, $J$=2.0 Hz, 1H), 8.52 (s, 1H), 8.24 - 8.15 (m, 1H), 8.05 (s, 1H), 7.63 - 7.57 (m, 3H), 7.52 - 7.38 (m, 3H), 7.34 - 7.31 (m, 1H), 7.23 (t, $J$=8.8 Hz, 1H), 7.06 (d, $J$=8.8 Hz, 2H), 6.16 (s, 1H), 6.19 - 6.14 (m, 1H), 5.42 - 5.18 (m, 1H), 5.11 (s, 1H), 4.89 (t, $J$=7.2 Hz, 1H), 4.43 (t, $J$=7.2 Hz, 1H), 4.31 - 4.23 (m, 1H), 3.72 - 3.60 (m, 4H), 3.57 - 3.50 (m, 2H), 3.47 - 3.43 (m, 1H), 3.20 (s, 3H), 2.82 - 2.71 (m, 2H), 2.65 - 2.61 (m, 2H), 2.45 (s, 3H), 2.31 - 2.23 (m, 1H), 2.15 - 1.96 (m, 4H), 1.91 - 1.77 (m, 3H), 1.46 (d, $J$=6.8 Hz, 3H), 1.40 - 1.32 (m, 3H), 1.23 (s, 1H), 1.04 (d, $J$=6.4 Hz, 1H), 0.96 (d, $J$=6.4 Hz, 3H), 0.83 (d, $J$=6.8 Hz, 4H), 0.76 (d, $J$=6.8 Hz, 1H). |
| 495 | B | A | $^{1}$H NMR (400MHz, DMSO-$d_6$) $\delta$: 12.89 (s, 1H), 9.02 - 8.94 (m, 1H), 8.65 (d, $J$=2.0 Hz, 1H), 8.53 (s, 1H), 8.39 (d, $J$=7.6 Hz, 1H), 8.05 (s, 1H), 7.63 - 7.56 (m, 3H), 7.48 - 7.42 (m, 2H), 7.39 - 7.34 (m, 2H), 7.24 (t, $J$=8.8 Hz, 1H), 7.07 (d, $J$=8.8 Hz, 2H), 6.15 (s, 1H), 5.38 - 5.20 (m, 1H), 5.10 (d, $J$=3.6 Hz, 1H), 4.92 (t, $J$=7.2 Hz, 1H), 4.43 - 4.33 (m, 1H), 4.29 (s, 1H), 3.72 - 3.64 (m, 3H), 3.60 - 3.55 (m, 1H), 3.48 - 3.46 (m, 1H), 3.21 (s, 3H), 2.79 (t, $J$=11.6 Hz, 2H), 2.69 - 2.65 (m, 4H), 2.46 (s, 3H), 2.28 - 2.21 (m, 1H), 2.16 - 1.92 (m, 4H), 1.92 - 1.74 (m, 3H), 1.58 - 1.43 (m, 3H), 1.38 (d, $J$=7.2 Hz, 3H), 1.23 (s, 1H), 1.04 (d, $J$=6.0 Hz, 2H), 0.98 - 0.92 (m, 3H), 0.86 - 0.75 (m, 3H). |

FIG. 3A. Continued

| No. | BRafV600E DC50 (nM) | BRafV600E Dmax (%) | NMR Transcript |
|---|---|---|---|
| 496 | D | Not calculated | $^1$H NMR: (400MHz, DMSO-*d6*) $\delta$: 13.17 - 12.49 (m, 1H), 9.03 - 8.94 (m, 1H), 8.64 (d, *J*=2.0 Hz, 1H), 8.52 (s, 1H), 8.09 (d, *J*=8.0 Hz, 1H), 8.03 (s, 1H), 7.66 - 7.55 (m, 3H), 7.50 - 7.38 (m, 3H), 7.37 - 7.31 (m, 1H), 7.24 - 7.13 (m, 1H), 7.06 (d, *J*=8.8 Hz, 2H), 6.21 - 6.13 (m, 1H), 5.39 - 5.17 (m, 1H), 5.14 - 5.00 (m, 1H), 4.98 - 4.78 (m, 2H), 4.64 - 4.43 (m, 1H), 4.35 - 4.20 (m, 1H), 3.75 - 3.60 (m, 4H), 3.60 - 3.54 (m, 3H), 3.43 (s, 2H), 3.31 - 3.26 (m, 4H), 3.20 (s, 4H), 2.87 - 2.70 (m, 2H), 2.67 (d, *J*=1.6 Hz, 2H), 2.63 (s, 2H), 2.47 - 2.44 (m, 4H), 2.42 - 2.35 (m, 1H), 2.31 - 2.21 (m, 1H), 2.06 - 2.02 (m, 1H), 1.90 - 1.75 (m, 3H), 1.52 - 1.35 (m, 2H), 0.97 (d, *J*=6.8 Hz, 2H), 0.87 - 0.78 (m, 3H), 0.75 (d, *J*=6.8 Hz, 1H). |
| 497 | B | A | $^1$H NMR: (400MHz, DMSO-$d_6$) $\delta$: 13.16 - 12.53 (m, 1H), 8.98 (s, 1H), 8.63 (s, 1H), 8.51 (s, 1H), 8.37 (d, *J*=8.0 Hz, 1H), 8.00 (s, 1H), 7.65 - 7.51 (m, 3H), 7.50 - 7.32 (m, 4H), 7.06 (d, *J*=8.8 Hz, 3H), 6.19 - 6.03 (m, 1H), 5.37 - 5.15 (m, 1H), 5.15 - 4.97 (m, 1H), 4.92 - 4.76 (m, 2H), 4.42 (t, *J*=7.6 Hz, 1H), 4.29 (s, 1H), 3.68 (d, *J*=10.4 Hz, 4H), 3.59 (d, *J*=10.4 Hz, 4H), 3.29 - 3.26 (m, 4H), 3.21 (s, 3H), 2.85 - 2.75 (m, 2H), 2.67 (s, 4H), 2.46 (s, 4H), 2.42 - 2.39 (m, 1H), 2.29 - 2.23 (m, 1H), 2.10 (s, 1H), 2.00 (s, 2H), 1.86 (d, *J*=10.8 Hz, 3H), 1.48 (d, *J*=9.2 Hz, 2H), 0.95 (d, *J*=6.0 Hz, 3H), 0.80 (d, *J*=6.4 Hz, 3H). |
| 498 | D | A | $^1$H NMR: (400 MHz, DMSO-$d_6$) $\delta$: 12.94 (s, 1H), 9.85 (s, 1H), 9.03 (d, *J*=2.8 Hz, 1H), 8.66 (d, *J*=2.0 Hz, 1H), 8.56 (s, 1H), 8.41 (d, *J*=8.0 Hz, 1H), 8.09 (s, 1H), 7.70 - 7.58 (m, 3H), 7.58 - 7.51 (m, 2H), 7.43 - 7.32 (m, 2H), 7.27 (m, 1H), 7.16 (d, *J*=8.0 Hz, 2H), 5.43 - 5.19 (m, 2H), 5.01 - 4.83 (m, 1H), 4.61 - 4.48 (m, 10H), 4.47 - 4.40 (m, 4H), 4.33 - 4.02 (m, 1H), 3.82 (br d, *J*=11.6 Hz, 2H), 3.69 - 3.46 (m, 5H), 3.06 - 2.79 (m, 6H), 2.24 - 1.58 (m, 8H), 1.52 - 1.29 (m, 5H), 1.04 - 0.88 (m, 9H). |
| 499 | B | B | $^1$H NMR: (400MHz, DMSO-$d_6$) $\delta$ : 12.92 (s, 1H), 8.98 (s, 1H), 8.69 - 8.64 (m, 1H), 8.55 (s, 1H), 8.43 - 8.36 (m, 1H), 8.07 (s, 1H), 7.88 (d, *J* = 9.0 Hz, 1H), 7.68 - 7.56 (m, 4H), 7.47 - 7.35 (m, 5H), 7.25 (t, *J* = 8.4 Hz, 2H), 7.19 - 7.12 (m, 4H), 6.99 - 6.92 (m, 2H), 5.38 - 5.20 (m, 1H), 5.15 - 5.07 (m, 1H), 4.92 (t, *J*=7.2 Hz, 1H), 4.53 - 4.36 (m, 2H), 4.31 - 4.24 (m, 1H), 3.67 - 3.46 (m, 3H), 3.29 (s, 7H), 2.45 (s, 5H), 2.09 (d, *J* = 13.6 Hz, 2H), 2.04 - 1.90 (m, 2H), 1.85 - 1.71 (m, 1H), 1.46 - 1.31 (m, 4H), 0.92 (s, 9H). |

FIG. 3A. Continued

| No. | BRafV600E DC50 (nM) | BRafV600 E Dmax (%) | NMR Transcript |
|---|---|---|---|
| 500 | | | $^1$H NMR: (400MHz, DMSO-$d_6$) *δ:* 10.96 (s, 1H), 10.68 (s, 1H), 8.85 (d, *J*=2.0 Hz, 1H), 8.39 - 8.25 (m, 2H), 8.08 - 7.95 (m, 2H), 7.86 - 7.76 (m, 1H), 7.72 (d, *J*=2.0 Hz, 1H), 7.68 - 7.53 (m, 1H), 7.39 (d, *J*=2.0 Hz, 1H), 7.24 (s, 1H), 7.12 (d, *J*=9.2 Hz, 3H), 7.07 - 6.99 (m, 2H), 5.08 (dd, *J*=5.2, 13.2 Hz, 1H), 4.49 - 4.34 (m, 5H), 4.34 - 4.25 (m, 1H), 3.77 (s, 4H), 3.19 (s, 4H), 2.96 - 2.84 (m, 1H), 2.59 (d, *J*=15.6 Hz, 1H), 2.44 (s, 3H), 2.39 (dd, *J*=4.0, 13.2 Hz, 1H), 2.05 - 1.94 (m, 1H). |
| 501 | D | A | $^1$H NMR (400 MHz, METHANOL-$d_4$) δ 8.87 (s, 1H), 8.67 (br. s., 1H), 8.59 (d, *J* = 1.96 Hz, 1H), 7.88 (s, 1H), 7.75 (dt, *J* = 5.77, 8.95 Hz, 1H), 7.60 (d, *J* = 8.61 Hz, 2H), 7.34 - 7.46 (m, 4H), 7.14 (t, *J* = 7.92 Hz, 1H), 6.97 (d, *J* = 8.80 Hz, 2H), 5.29 (br. s., 1H), 5.15 (br. s., 1H), 4.65 (s, 1H), 4.53 - 4.59 (m, 1H), 4.43 (br. s., 1H), 3.79 - 3.87 (m, 3H), 3.71 - 3.77 (m, 1H), 3.65 (t, *J* = 5.97 Hz, 2H), 3.57 (s, 1H), 3.52 - 3.56 (m, 1H), 3.50 (br. s., 1H), 3.44 - 3.49 (m, 1H), 3.37 - 3.44 (m, 2H), 2.99 - 3.16 (m, 5H), 2.46 (s, 3H), 2.11 - 2.37 (m, 7H), 1.81 - 2.10 (m, 7H), 1.50 (d, *J* = 7.04 Hz, 3H), 0.99 - 1.09 (m, 9H) |
| 502 | C | A | $^1$H NMR (300 MHz, $CD_3OD$) δ8.86 (s, 1H), 8.73 (s, 1H), 8.63 (d, *J* = 2.1 Hz, 1H), 7.90 (s, 1H), 7.79-7.71 (m, 1H),7.65-7.62 (m, 2H), 7.45-7.37 (m, 4H), 7.21-7.13 (m, 3H), 5.22 (d, *J*=53.6 Hz, 1H), 5.04-4.97 (m, 1H), 4.65-4.44 (m, 3H), 3.89-3.73 (m, 2H), 3.67-3.61 (m, 2H), 3.58-3.35 (m, 4H), 3.04 (s, 2H), 2.99-2.84 (m, 4H), 2.55-2.49 (m, 2H), 2.47 (s, 3H), 2.45-1.60 (m, 12H), 1.53-1.50 (m, 2H), 1.06-1.00 (m, 15H) |
| 503 | D | A | $^1$H-NMR (400 MHz, $CD_3OD$, ppm) δ 8.71 (s, 1H), 8.61 (d, *J* = 4.0 Hz, 2H), 7.91 (s, 1H), 7.78 (d, *J* = 4.0 Hz, 1H), 7.62 (d, *J* = 8.0 Hz, 2H), 7.47-7.42 (m, 4H), 7.41-7.13 (m, 3H), 5.18 (s, 1H), 5.04-5.02 (m, 1H), 4.90 (s, 2H), 4.66-4.61 (m, 3H), 4.46-4.44 (m, 1H), 3.87-3.83 (m, 2H), 3.59-3.50 (m, 5H), 3.05-3.04 (m, 2H), 2.9-2.89 (m, 2H), 2.73 (s, 4H), 2.46 (s, 5H), 2.36-2.21 (m, 4H), 2.01-1.97 (m, 2H), 1.82-1.80 (m, 2H), 1.64-1.61 (m, 5H), 1.35-1.33 (m, 5H), 1.05 (s, 9H) |

FIG. 3A. Continued

| No. | BRafV600E DC50 (nM) | BRafV600E Dmax (%) | NMR Transcript |
|---|---|---|---|
| 504 | C | A | $^{1}$H NMR (300 MHz, $CD_3OD$) δ 8.87 (s, 1H), 8.75 (s, 1H), 8.64 (d, *J* = 2.1 Hz, 1H), 7.91 (s, 1H), 7.79-7.66 (m, 3H), 7.49-7.41 (m, 4H), 7.30-7.27 (m, 2H),7.16-7.10 (m, 1H), 5.22 (d, *J* = 53.2 Hz, 1H), 4.64-4.34 (m, 5H), 3.91-3.78 (m, 2H), 3.64-3.38 (m, 5H), 3.04 (s, 2H), 2.99-2.76 (m, 4H), 2.48 (s, 3H), 2.26-2.01 (m, 10H), 1.89-1.80 (m, 2H), 1.63 (s, 1H), 1.39-1.28 (m, 3H), 1.05-1.03 (m, 9H), 0.87 (d, *J* = 6.3 Hz, 6H) |
| 505 | C | A | $^{1}$H NMR: (400MHz, DMSO-$d_6$) δ: 12.88 (s, 1H), 8.98 (s, 1H), 8.63 (d, *J*=2.0 Hz, 1H), 8.51 (s, 1H), 8.44 (d, *J*=7.6 Hz, 1H), 8.15 (s, 1H), 8.05 (s, 1H), 7.77 (d, *J*=10.0 Hz, 1H), 7.66 - 7.60 (m, 1H), 7.57 (d, *J*=8.8 Hz, 2H), 7.48 - 7.42 (m, 2H), 7.40 - 7.34 (m, 2H), 7.26 (t, *J*=8.8 Hz, 1H), 6.91 (d, *J*=8.8 Hz, 2H), 5.41 - 5.19 (m, 1H), 5.12 (s, 1H), 4.91 (t, *J*=7.2 Hz, 1H), 4.54 - 4.42 (m, 2H), 4.29 (s, 1H), 3.65 - 3.54 (m, 2H), 3.49 - 3.47 (m, 1H), 3.41 - 338 (m, 4H), 3.10 - 3.00 (m, 2H), 2.99 - 2.85 (m, 4H), 2.82 - 2.73 (m, 1H), 2.45 (s, 3H), 2.28 - 1.94 (m, 7H), 1.83 - 1.73 (m, 3H), 1.64 - 1.46 (m, 3H), 1.40 (d, *J*=7.2 Hz, 3H), 1.09 (d, *J*=4.4 Hz, 6H), 0.96 (s, 9H). |
| 506 | C | A | $^{1}$H NMR: (400MHz, DMSO-$d_6$) δ: 12.92 (s, 1H), 9.00 - 8.96 (m, 1H), 8.64 (d, *J*=2.0 Hz, 1H), 8.52 (s, 1H), 8.43 (br d, *J*=6.0 Hz, 1H), 8.18 (s, 2H), 8.06 (s, 1H), 7.78 (d, *J*=10.0 Hz, 1H), 7.66 - 7.60 (m, 1H), 7.58 (d, *J*=8.8 Hz, 2H), 7.48 - 7.41 (m, 2H), 7.40 - 7.34 (m, 2H), 7.25 (t, *J*=8.0 Hz, 1H), 7.03 (d, *J*=7.6 Hz, 2H), 5.38 - 5.21 (m, 1H), 4.97 - 4.84 (m, 1H), 4.57 - 4.42 (m, 2H), 4.29 (s, 1H), 3.73 - 3.55 (m, 2H), 3.49 - 3.45 (m, 2H), 3.41 - 3.38 (m, 2H), 3.25 - 3.21 (m, 2H), 3.11 - 3.01 (m, 2H), 2.98 - 2.79 (m, 7H), 2.45 (s, 3H), 2.30 - 1.89 (m, 6H), 1.86 - 1.74 (m, 3H), 1.67 - 1.49 (m, 2H), 1.39 (dd, *J*=2.8, 7.2 Hz, 3H), 1.18 - 1.07 (m, 6H), 0.95 (d, *J*=2.0 Hz, 9H). |

FIG. 3A. Continued

| No. | BRafV600E DC50 (nM) | BRafV600 E Dmax (%) | NMR Transcript |
|---|---|---|---|
| 507 | D | Not calculated | $^1$H NMR: (400MHz, DMSO-$d_6$) δ : 12.73 (s, 1H), 8.99 (s, 1H), 8.88 (d, *J*=8.4 Hz, 1H), 8.63 (d, *J*=2.0 Hz, 1H), 8.49 (s, 1H), 8.11 (d, *J*=8.4 Hz, 1H), 7.96 (s, 1H), 7.60 (d, *J*=8.4 Hz, 2H), 7.56 - 7.46 (m, 2H), 7.43 (d, *J*=8.0 Hz, 2H), 7.38 - 7.33 (m, 1H), 7.07 (d, *J*=8.8 Hz, 2H), 6.96 (s, 1H), 5.96 - 5.88 (m, 1H), 5.36 - 5.16 (m, 1H), 5.14 (d, *J*=3.6 Hz, 1H), 5.08 - 4.91 (m, 1H), 4.89 - 4.79 (m, 1H), 4.65 - 4.44 (m, 1H), 4.34 - 4.19 (m, 1H), 4.03 - 3.87 (m, 2H), 3.81 - 3.64 (m, 4H), 3.58 (dd, *J*=6.0, 12.0 Hz, 4H), 3.30 - 3.04 (m, 3H), 2.47 (d, *J*=2.4 Hz, 9H), 2.31 - 2.22 (m, 1H), 2.11 (s, 1H), 2.09 - 2.00 (m, 2H), 2.00 - 1.89 (m, 2H), 1.88 - 1.80 (m, 1H), 1.06 - 0.79 (m, 6H), 0.76 (d, *J*=6.8 Hz, 1H). |
| 508 | C | A | $^1$H NMR: (400MHz, DMSO-$d_6$) δ: 12.88 (s, 1H), 8.98 (s, 1H), 8.93 - 8.68 (m, 1H), 8.65 (d, *J*=2.0 Hz, 1H), 8.52 (s, 1H), 8.38 (d, *J*=8.0 Hz, 1H), 8.03 (s, 1H), 7.69 - 7.55 (m, 3H), 7.50 - 7.34 (m, 4H), 7.17 (t, *J*=8.8 Hz, 1H), 7.09 (d, *J*=8.8 Hz, 2H), 5.94 - 5.82 (m, 1H), 5.41 - 5.18 (m, 1H), 5.13 (d, *J*=3.6 Hz, 1H), 5.03 - 4.73 (m, 2H), 4.43 (t, *J*=8.0 Hz, 1H), 4.29 (s, 1H), 3.97 (br t, *J*=6.8 Hz, 2H), 3.83 - 3.67 (m, 4H), 3.67 - 3.54 (m, 4H), 3.29 - 3.20 (m, 6H), 3.17 (d, *J*=5.2 Hz, 1H), 2.57 - 2.52 (m, 3H), 2.46 (s, 4H), 2.28 - 2.17 (m, 1H), 2.11 (s, 1H), 2.09 - 1.91 (m, 3H), 1.87 - 1.76 (m, 1H), 1.04 - 0.74 (m, 6H). |
| 509 | | | $^1$H NMR: (400MHz, DMSO-$d_6$) δ = 12.90 (s, 1H), 11.15 - 11.06 (m, 1H), 8.65 (d, *J* = 2.0 Hz, 1H), 8.53 (s, 1H), 8.16 - 8.06 (m, 1H), 7.72 (d, *J* = 11.2 Hz, 1H), 7.68 - 7.56 (m, 3H), 7.56 - 7.41 (m, 1H), 7.26 (t, *J* = 8.8 Hz, 1H), 7.08 (d, *J* = 8.8 Hz, 2H), 5.41 - 5.18 (m, 1H), 5.10 (dd, *J* = 5.2, 12.8 Hz, 1H), 3.68 (d, *J* = 12.0 Hz, 2H), 3.48 (s, 8H), 3.23 (s, 2H), 3.00 - 2.83 (m, 5H), 2.79 - 2.65 (m, 5H), 2.18 - 1.99 (m, 3H), 1.95 (d, *J* = 11.2 Hz, 2H), 1.62 (d, *J* = 10.2 Hz, 2H). |
| 510 | B | | |
| 511 | | | |
| 512 | A | | |
| 513 | | | |
| 514 | D | | |
| 515 | B | | |

FIG. 3A. Continued

| No. | BRafV600E DC50 (nM) | BRafV600E Dmax (%) | NMR Transcript |
|---|---|---|---|
| 516 | D | | |
| 517 | D | | |

$DC_{50}$ Categories:
A<10
10<=B<=50
50<C<=100
D>100
Dmax Categories:
C>70
50<=B<=70
A<50

FIG. 3B

Table 2B. Data of exemplary protein targeting moieties and compounds of the present disclosure.

| No. | $DC_{50}$ (nM)* | $D_{MAX}$ (%)** | NMR Transcript |
|---|---|---|---|
| 518 | D | C | 1H NMR (400MHz, DIMETHYLSULFOXIDE-d6) δ 13.01 - 12.79 (m, 1H), 11.10 (s, 1H), 8.66 (d, J = 2.0 Hz, 1H), 8.54 (s, 1H), 8.16 (s, 1H), 8.07 (s, 1H), 7.71 (d, J = 11.6 Hz, 1H), 7.66 - 7.58 (m, 3H), 7.46 (d, J = 7.2 Hz, 1H), 7.26 (t, J = 8.4 Hz, 1H), 7.09 (d, J = 8.8 Hz, 2H), 5.40 - 5.21 (m, 1H), 5.11 (dd, J = 5.6, 13.2 Hz, 1H), 3.64 (d, J = 12.4 Hz, 2H), 3.48 (s, 1H), 3.40 (d, J = 2.8 Hz, 3H), 3.24 (s, 5H), 2.97 - 2.85 (m, 3H), 2.62 (s, 1H), 2.55 (br s, 5H), 2.27 (d, J = 6.8 Hz, 2H), 2.15 - 1.96 (m, 3H), 1.93 - 1.80 (m, 3H), 1.36 - 1.24 (m, 2H). |
| 519 | B | B | 1H NMR (400MHz, DIMETHYLSULFOXIDE-d6) δ 12.94 (s, 1H), 11.04 (s, 1H), 9.84 (s, 1H), 9.55 (s, 1H), 8.67 (d, J = 2.4 Hz, 1H), 8.57 (s, 1H), 8.09 (d, J = 2.8 Hz, 1H), 7.76 - 7.54 (m, 3H), 7.27 (t, J = 8.8 Hz, 1H), 7.17 (d, J = 8.8 Hz, 2H), 7.05 (s, 1H), 6.75 (s, 1H), 5.49 - 5.19 (m, 1H), 5.01 (dd, J =5.2, 12.8 Hz, 1H), 4.31 (br d, J = 12.0 Hz, 2H), 4.08 - 3.83 (m, 6H), 3.67 (d, J = 11.6 Hz, 3H), 3.30 (dt, J = 6.8, 9.9 Hz, 5H), 3.15 - 2.97 (m, 4H), 2.97 - 2.81 (m, 1H), 2.58 (d, J = 16.4 Hz, 1H), 2.20 (d, J = 10.0 Hz, 2H), 2.15 - 1.98 (m, 3H), 1.78 - 1.66 (m, 2H). |
| 520 | B | B | 1H NMR (400MHz, DMSO-d6) δ 13.19 - 12.61 (m, 1H), 11.14 (s, 1H), 8.66 (d, J=13.6 Hz, 1H), 8.53 (s, 1H), 8.20 (d, J=15.2 Hz, 1H), 8.07 (d, J=14.4 Hz, 1H), 7.75 - 7.52 (m, 4H), 7.44 - 7.18 (m, 3H), 7.17 - 6.99 (m, 2H), 5.47 - 5.16 (m, 1H), 5.07 (s, 1H), 4.18 - 3.90 (m, 2H), 3.28 - 3.09 (m, 12H), 3.04 - 2.86 (m, 2H), 2.41 (s, 4H), 2.22 - 1.92 (m, 4H), 1.87 - 1.75 (m, 2H), 1.69 - 1.58 (m, 1H), 1.51 - 1.39 (m, 2H), 1.32 - 1.17 (m, 2H). |
| 521 | C | B | 1H NMR (400MHz, DMSO-d6) δ 11.10 (s, 1H), 8.64 (d, J=2.4 Hz, 1H), 8.53 (d, J=1.0 Hz, 1H), 8.21 (s, 1H), 8.05 (s, 1H), 7.84 (d, J=8.4 Hz, 1H), 7.65 - 7.56 (m, 3H), 7.50 (d, J=2.4 Hz, 1H), 7.40 (dd, J=2.4, 8.4 Hz, 1H), 7.27 - 7.18 (m, 1H), 7.08 (d, J=8.8 Hz, 2H), 5.40 - 5.19 (m, 1H), 5.12 (dd, J=5.2, 12.9 Hz, 1H), 4.43 - 4.30 (m, 2H), 3.51 - 3.44 (m, 6H), 3.24 (s, 2H), 2.96 - 2.79 (m, 4H), 2.72 - 2.66 (m, 4H), 2.60 - 2.51 (m, 2H), 2.13 - 1.98 (m, 3H). |
| 522 | A | C | 1H NMR (DMSO-d6) δ 10.93 (s, 1H), 8.65 (d, J=2.0 Hz, 1H), 8.53 (s, 1H), 8.20 (s, 1H), 8.05 (s, 1H), 7.67 - 7.55 (m, 3H), 7.50 (d, J=8.8 Hz, 1H), 7.24 (t, J=8.3 Hz, 1H), 7.13 - 6.99 (m, 4H), 5.43 - 5.19 (m, 1H), 5.03 (dd, J=5.2, 13.2 Hz, 1H), 4.37 - 4.12 (m, 1H), 4.16 - 4.12 (m, 1H), 3.88 (d, J=12.4 Hz, 2H), 3.35 - 3.29 (m, 15H), 3.00 - 2.72 (m, 3H), 2.22 (d, J=6.4 Hz, 2H), 2.10 - 1.95 (m, 1H), 1.96 (dd, J=4.9, 10.0 Hz, 2H), 1.87 - 1.72 (m, 3H), 1.26 - 1.11 (m, 2H). |
| 523 | B | C | 1H NMR (400MHz, DMSO-d6) δ 12.90 (s, 1H), 11.11 (s, 1H), 9.85 (s, 1H), 8.70 - 8.46 (m, 2H), 8.07 (s, |

FIG. 3B. Continued

| | | | |
|---|---|---|---|
| | | | 1H), 7.87 - 7.76 (m, 1H), 7.69 - 7.51 (m, 3H), 7.34 - 7.21 (m, 3H), 7.07 (d, J=8.8 Hz, 2H), 5.40 - 5.21 (m, 1H), 5.12 (dd, J=5.2, 12.8 Hz, 1H), 5.01 - 4.92 (m, 1H), 3.79 (d, J=12.0 Hz, 2H), 3.51 - 3.37 (m, 4H), 3.30 - 3.24 (m, 1H), 3.10 - 2.98 (m, 1H), 2.95 - 2.83 (m, 1H), 2.75 (t, J=12.0 Hz, 2H), 2.68 - 2.55 (m, 2H), 2.44 - 2.35 (m, 2H), 2.26 - 2.16 (m, 2H), 2.14 - 2.01 (m, 6H), 1.82 (d, J=12.8 Hz, 2H), 1.67 (s, 1H), 1.31 - 1.16 (m, 2H). |
| 524 | B | B | 1H NMR (400MHz, DIMETHYLSULFOXIDE-d6) δ 12.95 (s, 1H), 11.05 (s, 1H), 9.86 (s, 1H), 9.30 (s, 1H), 8.68 (d, J = 2.0 Hz, 1H), 8.58 (s, 1H), 8.10 (s, 1H), 7.72 - 7.65 (m, 2H), 7.65 - 7.58 (m, 1H), 7.28 (t, J = 8.0 Hz, 1H), 7.17 (d, J = 8.8 Hz, 2H), 7.00 (s, 1H), 6.68 (s, 1H), 5.41 - 5.19 (m, 1H), 5.01 (dd, J = 5.3, 12.5 Hz, 1H), 4.15 (d, J = 13.8 Hz, 2H), 3.93 (s, 5H), 3.66 (d, J = 8.8 Hz, 2H), 3.24 - 3.11 (m, 8H), 3.04 (t, J = 12.4 Hz, 3H), 2.92 - 2.83 (m, 1H), 2.37 - 2.29 (m, 4H), 1.98 (d, J = 7.2 Hz, 2H), 1.87 (d, J = 10.8 Hz, 2H), 1.30 (d, J = 12.4 Hz, 2H). |
| 525 | C | C | 1H NMR (400 MHz, DMSO-d6) δ 12.93 (s, 1H), 11.10 (s, 1H), 9.87 (s, 1H), 9.60 - 9.38 (m, 1H), 8.78 - 8.40 (m, 2H), 8.08 (d, J=2.4 Hz, 1H), 7.75 - 7.52 (m, 3H), 7.37 - 7.02 (m, 3H), 6.98 - 6.74 (m, 2H), 5.40 - 5.19 (m, 1H), 5.16 - 5.00 (m, 2H), 4.14 - 4.00 (m, 1H), 3.94 (s, 3H), 3.85 (d, J=10.4 Hz, 2H), 3.43 - 3.22 (m, 6H), 3.09 - 2.76 (m, 10H), 2.63 - 2.54 (m, 2H), 2.16 - 1.92 (m, 5H), 1.75 (d, J=12.0 Hz, 1H), 1.47 - 1.27 (m, 2H). |
| 526 | C | C | 1H NMR (400MHz, DMSO-d6) δ 12.89 (s, 1H), 11.07 (s, 1H), 8.64 (d, J = 2.4 Hz, 1H), 8.52 (s, 1H), 8.17 (s, 1H), 8.04 (s, 1H), 7.68 (d, J = 8.8 Hz, 1H), 7.64 - 7.54 (m, 3H), 7.34 (s, 1H), 7.30 - 7.20 (m, 2H), 7.06 (d, J = 8.8 Hz, 2H), 5.39 - 5.17 (m, 1H), 5.06 (dd, J = 5.2, 12.9 Hz, 1H), 3.77 (d, J = 12.0 Hz, 4H), 3.55 - 3.43 (m, 1H), 3.15 - 2.87 (m, 2H), 2.72 (t, J = 12.4 Hz, 1H), 2.62 - 2.52 (m, 3H), 2.41 (d, J = 7.2 Hz, 6H), 2.14 - 1.95 (m, 4H), 1.80 (d, J = 11.2 Hz, 2H), 1.47 (s, 3H), 1.37 - 1.09 (m, 3H). |
| 527 | B | C | 1H NMR (400 MHz, DMSO-d6) δ 12.89 (s, 1H), 10.93 (s, 1H), 8.65 (d, J=2.0 Hz, 1H), 8.53 (s, 1H), 8.14 (s, 1H), 8.06 (s, 1H), 7.67 - 7.56 (m, 3H), 7.53 (d, J=8.8 Hz, 1H), 7.26 (t, J=8.4 Hz, 1H), 7.12 - 7.01 (m, 4H), 5.41 - 5.19 (m, 1H), 5.04 (dd, J=5.2, 13.2 Hz, 1H), 4.40 - 4.16 (m, 2H), 3.79 (d, J=12.4 Hz, 2H), 3.48 (s, 10H), 2.96 - 2.84 (m, 1H), 2.75 (t, J=11.2 Hz, 2H), 2.61 (s, 1H), 2.44 - 2.34 (m, 2H), 2.24 (d, J=7.2 Hz, 2H), 2.18 - 2.04 (m, 2H), 2.03 - 1.90 (m, 2H), 1.84 (d, J=13.2 Hz, 2H), 1.76 (d, J=4.4 Hz, 1H), 1.33 - 1.18 (m, 2H). |
| 528 | D | C | 1H NMR (400MHz, DMSO-d6) δ 12.97 (s, 1H), 11.12 (s, 1H), 10.01 (s, 1H), 9.85 (s, 1H), 8.68 (d, J = 2.4 Hz, 1H), 8.60 (s, 1H), 8.11 (d, J = 2.8 Hz, 1H), 7.83 (d, J = 11.2 Hz, 1H), 7.75 (d, J = 8.8 Hz, 2H), 7.67 - 7.57 (m, 2H), 7.27 (t, J = 8.4 Hz, 1H), 7.19 (d, J = 8.8 Hz, 2H), 5.43 - 5.21 (m, 1H), 5.13 (dd, J = 5.2, 12.8 Hz, 1H), 4.47 (s, 2H), 3.83 (s, 1H), 3.62 - 3.56 (m, 2H), 3.49 (s, 2H), 3.45 - 3.36 (m, 5H), 3.35 - 3.25 (m, 2H), 2.98 - 2.80 (m, 1H), 2.65 - 2.54 (m, 2H), 2.19 - 1.83 (m, 4H). |
| 529 | C | C | 1H NMR (400MHz, DIMETHYLSULFOXIDE-d6) δ 12.93 (s, 1H), 11.04 (s, 1H), 8.66 (d, J = 2.0 Hz, |

FIG. 3B. Continued

| | | | |
|---|---|---|---|
| | | | 1H), 8.56 (s, 1H), 8.16 - 8.08 (m, 1H), 7.71 - 7.59 (m, 3H), 7.26 (t, J = 8.5 Hz, 1H), 7.12 (d, J = 8.8 Hz, 2H), 6.97 (s, 1H), 6.70 (s, 1H), 5.41 - 5.18 (m, 1H), 5.00 (J = 5.2, 12.9 Hz, 1H), 4.21 (t, J = 5.6 Hz, 2H), 3.93 (s, 3H), 3.57 - 3.45 (m, 5H), 3.40 (d, J = 3.2 Hz, 2H), 3.36 (s, 2H), 2.93 - 2.79 (m, 3H), 2.67 (s, 4H), 2.61 - 2.53 (m, 1H), 2.37 - 2.29 (m, 1H), 2.17 - 1.91 (m, 4H). |
| 530 | A | C | 1H NMR (400 MHz, DMSO-d6) δ 12.95 (s, 1H), 10.99 (s, 1H), 9.91 (s, 1H), 9.85 (s, 1H), 8.67 (d, J=2.4 Hz, 1H), 8.58 (s, 1H), 8.09 (d, J=3.2 Hz, 1H), 7.76 - 7.57 (m, 4H), 7.34 - 7.23 (m, 2H), 7.17 (d, J=9.2 Hz, 3H), 5.44 - 5.19 (m, 1H), 5.10 (dd, J=5.2, 13.2 Hz, 1H), 4.51 (s, 2H), 4.46 - 4.25 (m, 2H), 3.97 (d, J=11.6 Hz, 1H), 3.71 (s, 3H), 3.48 (s, 1H), 3.43 - 3.37 (m, 3H), 3.29 (dd, J=3.2, 10.0 Hz, 1H), 3.14 (d, J=11.6 Hz, 2H), 2.99 - 2.84 (m, 1H), 2.52 (d, J=2.0 Hz, 2H), 2.47 - 2.35 (m, 2H), 2.22 - 2.06 (m, 2H), 2.03 - 1.96 (m, 1H). |
| 531 | B | C | 1H NMR (400MHz, DMSO-d6) δ 12.93 (s, 1H), 10.94 (s, 1H), 8.66 (d, J=2.4 Hz, 1H), 8.56 (s, 1H), 8.17 (s, 1H), 8.08 (s, 1H), 7.70 - 7.64 (m, 2H), 7.64 - 7.58 (m, 1H), 7.52 (d, J=9.2 Hz, 1H), 7.26 (t, J=8.8 Hz, 1H), 7.15 - 7.05 (m, 4H), 5.39 - 5.19 (m, 1H), 5.04 (dd, J=5.2, 13.2 Hz, 1H), 4.39 - 4.28 (m, 1H), 4.25 - 4.17 (m, 3H), 3.32 - 3.29 (m, 8H), 2.91 - 2.86 (m, 1H), 2.81 (t, J=5.6 Hz, 2H), 2.67 (d, J=4.0 Hz, 4H), 2.58 (d, J=18.0 Hz, 2H), 2.42 - 2.34 (m, 1H), 2.17 - 2.03 (m, 2H), 2.03 - 1.91 (m, 2H). |
| 532 | B | C | 1H NMR (400MHz, DMSO-d6) δ 12.92 (s, 1H), 10.95 (s, 1H), 8.65 (d, J = 2.4 Hz, 1H), 8.54 (s, 1H), 8.06 (s, 1H), 7.70 - 7.57 (m, 3H), 7.54 (d, J = 8.8 Hz, 1H), 7.27 (t, J = 8.4 Hz, 1H), 7.16 - 7.04 (m, 4H), 5.39 - 5.19 (m, 1H), 5.04 (dd, J = 4.8, 13.2 Hz, 1H), 4.46 - 3.97 (m, 3H), 3.33 - 3.29 (m, 6H), 3.26 (d, J = 6.4 Hz, 2H), 2.95 - 2.81 (m, 5H), 2.76 (s, 7H), 2.61 (s, 1H), 2.56 (s, 2H), 2.44 - 2.34 (m, 2H), 2.19 - 2.04 (m, 2H), 2.03 - 1.88 (m, 2H), 1.51 (s, 1H). |
| 533 | D | C | 1H NMR (400MHz, DMSO-d6) δ 13.27 - 12.51 (m, 1H), 11.12 (s, 1H), 8.65 (d, J=2.0 Hz, 1H), 8.53 (s, 1H), 8.21 (s, 1H), 8.06 (s, 1H), 7.89 (d, J=9.2 Hz, 1H), 7.68 - 7.53 (m, 3H), 7.43 (d, J=7.2 Hz, 1H), 7.24 (t, J=8.8 Hz, 1H), 7.07 (d, J=8.8 Hz, 2H), 5.42 - 5.19 (m, 1H), 5.18 - 5.02 (m, 2H), 3.80 (d, J=12.4 Hz, 2H), 3.29 (d, J=3.2 Hz, 4H), 3.14 - 3.03 (m, 1H), 2.95 - 2.86 (m, 1H), 2.76 (t, J=11.2 Hz, 2H), 2.60 (d, J=19.2 Hz, 1H), 2.42 (dd, J=6.8, 13.2 Hz, 3H), 2.27 (d, J=8.4 Hz, 2H), 2.15 - 2.01 (m, 8H), 1.83 (d, J=12.0 Hz, 2H), 1.68 (s, 1H), 1.33 - 1.19 (m, 2H). |
| 534 | B | C | 1H NMR (DMSO-d6) δ : 12.95 (d, J = 2.8 Hz, 1H), 10.96 (s, 1H), 9.86 (s, 1H), 9.74 - 9.59 (m, 1H), 8.67 (d, J = 2.4 Hz, 1H), 8.57 (s, 1H), 8.09 (d, J = 2.4 Hz, 1H), 7.71 - 7.65 (m, 2H), 7.64 - 7.59 (m, 1H), 7.56 (d, J = 8.4 Hz, 1H), 7.31 - 7.24 (m, 1H), 7.20 - 7.10 (m, 4H), 5.44 - 5.16 (m, 1H), 5.10 - 5.02 (m, 1H), 4.38 - 4.18 (m, 2H), 4.10 (d, J = 12.8 Hz, 2H), 4.02 - 3.96 (m, 2H), 3.62 - 3.54 (m, 3H), 3.48 (s, 1H), 3.43 - 3.38 (m, 2H), 3.33 - 3.22 (m, 3H), 3.11 - 3.00 (m, 2H), 2.97 - 2.83 (m, 3H), 2.63 - 2.56 (m, 1H), 2.42 - 2.35 (m, 1H), 2.20 (d, J = 10.0 Hz, 2H), 2.13 - 2.07 (m, 1H), 2.01 - 1.95 (m, 1H), 1.74 (d, J = 12.0 Hz, 2H). |

FIG. 3B. Continued

| | | | |
|---|---|---|---|
| 535 | C | B | 1H NMR (400 MHz, DMSO-d6) δ : 12.95 (d, J = 2.8 Hz, 1H), 10.96 (s, 1H), 9.86 (s, 1H), 9.74 - 9.59 (m, 1H), 8.67 (d, J = 2.4 Hz, 1H), 8.57 (s, 1H), 8.09 (d, J = 2.4 Hz, 1H), 7.71 - 7.65 (m, 2H), 7.64 - 7.59 (m, 1H), 7.56 (d, J = 8.4 Hz, 1H), 7.31 - 7.24 (m, 1H), 7.20 - 7.10 (m, 4H), 5.44 - 5.16 (m, 1H), 5.10 - 5.02 (m, 1H), 4.38 - 4.18 (m, 2H), 4.10 (d, J = 12.8 Hz, 2H), 4.02 - 3.96 (m, 2H), 3.62 - 3.54 (m, 3H), 3.48 (s, 1H), 3.43 - 3.38 (m, 2H), 3.33 - 3.22 (m, 3H), 3.11 - 3.00 (m, 2H), 2.97 - 2.83 (m, 3H), 2.63 - 2.56 (m, 1H), 2.42 - 2.35 (m, 1H), 2.20 (d, J = 10.0 Hz, 2H), 2.13 - 2.07 (m, 1H), 2.01 - 1.95 (m, 1H), 1.74 (d, J = 12.0 Hz, 2H). |
| 536 | A | C | 1H NMR (300 MHz, DMSO-d6) 12.90 (s, 1H), 10.96 (s, 1H), 8.62 (s, 1H), 8.50 (s, 1H), 8.07 (s, 1H), 7.66-7.49 (m, 4H), 7.29-7.23 (m, 1H), 7.05-7.02 (m, 2H), 6.58-6.55 (m, 2H), 5.30 (d, J=52.8 Hz, 1H), 5.08-5.02 (m, 1H), 4.35-4.16 (m, 2H), 3.94-3.84 (m, 6H), 3.51-3.49 (m, 1H), 3.39-3.38 (m, 5H), 3.30-3.23 (m, 1H), 2.91-2.76 (m, 3H), 2.61-2.55 (m, 1H), 2.39-2.35 (m, 3H), 2.18-1.93 (m, 3H), 1.77-1.73 (m, 2H), 1.52 (s, 1H), 1.23-1.18 (m, 4H). |
| 537 | A | C | 1H NMR (300 MHz, DMSO-d6) 12.91 (s, 1H), 10.95 (s, 1H), 8.65 (s, 1H), 8.53 (s, 1H), 8.16 (s, 1H), 8.07 (s, 1H), 7.66-7.57 (m, 3H), 7.51-7.48 (m, 1H), 7.30-7.24 (m, 1H), 7.08-7.05 (m, 2H), 6.53-6.48 (m, 2H), 5.30 (d, J = 53.1 Hz, 1H), 5.06-5.00 (m, 1H), 4.34-4.15 (m, 3H), 4.00 (s, 5H), 3.79-3.75 (m, 3H), 2.96-2.81 (m, 2H), 2.74-2.66 (m, 3H), 2.61-2.56 (m, 1H), 2.44-2.28 (m, 4H), 2.14-1.94 (m, 4H), 1.79-1.75 (m, 2H), 1.49 (s, 1H), 1.30-1.19 (m, 3H). |
| 538 | B | C | 1H NMR (400 MHz, DMSO-d6) δ 12.94 (s, 1H), 10.95 (s, 1H), 8.67- 8.56 (s, 2H), 8.17 (s, 1H), 8.09 (s, 1H), 7.68 -7.61 (m, 5.9 Hz, 3H), 7.52 (m, 1H), 7.26 (m, 1H), 7.12 – 7.03 (m, 4H), 5.37 (s, 1H), 5.23 – 5.02 (m, 2H), 4.33–4.08 (m, 5H), 4.07 – 3.51 (m, 9H), 3.00 – 2.90 (m, 2H), 2.80 –2.61 (m, 1H), 2.46 – 2.33 (m, 3H), 2.33 – 1.92 (m, 3H), 1.79 (m, 2H), 1.66 (m, 2H). |
| 539 | A | C | 1H NMR (400MHz, DMSO-d6) δ 13.07 - 12.94 (m, 1H), 11.03 - 10.87 (m, 1H), 9.91 - 9.82 (m, 1H), 9.76 - 9.37 (m, 1H), 8.84 - 8.68 (m, 1H), 8.67 - 8.53 (m, 1H), 8.19 - 8.05 (m, 1H), 7.80 - 7.68 (m, 2H), 7.67 - 7.56 (m, 2H), 7.48 - 7.36 (m, 2H), 7.33 - 7.24 (m, 1H), 7.23 - 7.07 (m, 2H), 5.41 - 5.20 (m, 1H), 5.14 - 4.99 (m, 1H), 4.40 - 4.32 (m, 1H), 4.28 - 4.19 (m, 1H), 4.08 - 3.99 (m, 2H), 3.67 - 3.63 (m, 2H), 3.48 (s, 2H), 3.25 - 3.07 (m, 7H), 2.82 (s, 3H), 2.79 - 2.70 (m, 4H), 2.14 - 2.04 (m, 3H), 2.02 - 1.93 (m, 1H). |
| 540 | A | C | 1H NMR (400MHz, DMSO-d6) δ 12.91 (s, 1H), 10.90 (s, 1H), 8.65 (d, J=2.0 Hz, 1H), 8.53 (s, 1H), 8.17 (s, 1H), 8.06 (s, 1H), 7.67 - 7.53 (m, 3H), 7.25 (t, J=8.8 Hz, 1H), 7.07 (d, J=8.8 Hz, 2H), 6.62 (s, 1H), 6.49 (s, 1H), 5.40 - 5.19 (m, 1H), 4.96 (dd, J=5.2, 13.2 Hz, 1H), 4.28 - 4.20 (m, 1H), 4.16 - 4.06 (m, 1H), 3.84 (s, 3H), 3.79 (d, J=12.2 Hz, 2H), 3.49 - 3.45 (m, 2H), 3.39 - 3.38(m, 5H), 3.28 - 3.25 (m, 4H), 2.94 - 2.84 (m, 1H), 2.75 (t, J=11.5 Hz, 2H), 2.61 - 2.54 (m, 1H), 2.46 - 2.35 (m, 1H), 2.28 - 2.21 (m, 2H), 2.17 - 2.04 (m, 2H), 2.02 - 1.67 (m, 5H), 1.26 (q, J=10.8 Hz, 2H). |

FIG. 3B. Continued

| | | | |
|---|---|---|---|
| 541 | A | C | 1H NMR (400MHz, DMSO-d6) δ 13.05 - 12.75 (m, 1H), 11.05 - 10.88 (m, 1H), 10.06 - 9.65 (m, 1H), 8.68 - 8.62 (m, 1H), 8.59 - 8.51 (m, 1H), 8.10 - 8.03 (m, 1H), 7.61 (d, J = 8.8 Hz, 4H), 7.30 - 7.23 (m, 1H), 7.21 - 7.16 (m, 1H), 7.15 - 7.03 (m, 3H), 5.41 - 5.19 (m, 1H), 5.13 - 5.02 (m, 1H), 4.48 - 4.35 (m, 1H), 4.32 - 4.23 (m, 1H), 4.19 - 4.08 (m, 2H), 3.52 - 3.42 (m, 2H), 3.31 - 3.27 (m, 2H), 3.27 - 3.21 (m, 4H), 3.00 - 2.83 (m, 1H), 2.64 - 2.55 (m, 5H), 2.46 - 2.35 (m, 2H), 2.17 - 2.06 (m, 2H), 2.05 - 1.92 (m, 4H). |
| 542 | B | C | 1H NMR (400 MHz, DMSO-d6) δ 12.90 (s, 1H), 10.96 (s, 1H), 9.86 (m, 1H), 8.65 (m, 1H), 8.54 (m, 1H), 8.06 (m, 1H), 7.69 - 7.51 (m, 4H), 7.35 - 7.21 (m, 1H), 7.13 - 6.90 (m, 4H), 5.43 - 5.18 (m, 1H), 5.13 - 4.99 (m, 1H), 4.90 - 4.78 (m, 1H), 4.44 - 4.21 (m, 2H), 3.88 - 3.72 (m, 2H), 3.51 - 3.38 (m, 2H), 3.26 - 3.18 (m, 2H), 3.13 - 2.69 (m, 5H), 2.65 - 2.54 (m, 1H), 2.41 - 2.36 (m, 3H), 2.25 - 2.16 (m, 2H), 2.14 - 2.08 (m, 5H), 2.03 - 1.92 (m, 2H), 1.86 - 1.79 (m, 2H), 1.70 - 1.61 (m, 1H), 1.30 - 1.19 (m, 2H). |
| 543 | B | C | 1H NMR (400 MHz, DMSO-d6) δ 12.96 (s, 1H), 10.96 (s, 1H), 8.67 (d, J=2.0 Hz, 1H), 8.57 (s, 1H), 8.16 (s, 1H), 8.10 (s, 1H), 7.68 (d, J=8.8 Hz, 2H), 7.65 - 7.59 (m, 1H), 7.53 (d, J=8.8 Hz, 1H), 7.27 (t, J=8.4 Hz, 1H), 7.13 - 7.05 (m, 4H), 5.40 - 5.20 (m, 1H), 5.05 (dd, J=5.2, 13.2 Hz, 1H), 4.40 - 4.28 (m, 1H), 4.26 - 4.17 (m, 1H), 4.11 (t, J=6.4 Hz, 2H), 3.48 (s, 7H), 2.97 - 2.82 (m, 2H), 2.57 (s, 8H), 2.43 - 2.37 (m, 1H), 2.20 - 2.03 (m, 2H), 2.01 - 1.94 (m, 3H). |
| 544 | A | C | 1H NMR (400MHz, DMSO-d6) δ 12.91 (s, 1H), 10.99 (s, 1H), 9.85 (s, 1H), 8.65 (d, J = 2.4 Hz, 1H), 8.54 (s, 1H), 8.07 (s, 1H), 7.67 - 7.65 (m, 1H), 7.64 - 7.62 (m, 1H), 7.60 (d, J = 8.8 Hz, 3H), 7.48 (s, 1H), 7.39 (d, J = 8.0 Hz, 1H), 7.26 (t, J = 8.8 Hz, 1H), 7.07 (d, J = 8.8 Hz, 2H), 5.3-5.2 (m, 1H), 5.11 (dd, J = 5.2, 13.2 Hz, 1H), 4.47 - 4.38 (m, 1H), 4.34 - 4.25 (m, 1H), 3.47 (s, 1H), 3.40 (d, J = 2.8 Hz, 2H), 3.37 (d, J = 2.0 Hz, 1H), 3.30 (s, 2H), 3.22 (s, 4H), 2.98 - 2.85 (m, 1H), 2.76 (t, J = 7.2 Hz, 3H), 2.64 - 2.61 (m, 1H), 2.42 - 2.34 (m, 3H), 2.19 - 2.05 (m, 2H), 2.02 - 1.96 (m, 1H), 1.88 - 1.78 (m, 2H). |
| 545 | A | B | 1H NMR (400 MHz, DMSO-d6) δ 12.93 (s, 1H), 10.94 (s, 1H), 8.66 – 8.55 (s, 2H), 8.18 (s, 1H), 8.08 (s, 1H), 7.67 – 7.60 (m, 3H), 7.53(m, 1H), 7.24 (m, 1H), 7.07 – 6.94 (m, 4H), 5.36 – 5.23 (s, 1H), 5.05 (m, 1H), 4.93 – 4.63 (m, 1H), 4.36 – 4.19 (m, 2H), 3.47 – 3.32 (m, 8H), 2.95 – 2.86 (m, 2H), 2.70 (s, 2H), 2.61 – 2.50 (s, 4H), 2.50 – 1.97 (m, 8H), 1.82 – 1.73 (m, 1H). |
| 546 | C | C | 1H NMR (400 MHz, DMSO-d6) δ 12.87 (s, 1H), 10.97 (s, 1H), 8.69 - 8.62 (m, 1H), 8.53 (s, 1H), 8.22 (s, 1H), 8.05 (s, 1H), 7.67 - 7.55 (m, 4H), 7.23 (t, J=8.8 Hz, 1H), 7.10 - 6.95 (m, 4H), 5.76 (s, 1H), 5.38 - 5.21 (m, 1H), 5.07 (dd, J=5.2, 13.2 Hz, 1H), 4.79 (s, 1H), 4.56 - 4.45 (m, 1H), 4.42 - 4.22 (m, 3H), 2.99 - 2.84 (m, 2H), 2.78 - 2.69 (m, 2H), 2.61 (s, 3H), 2.39 (dd, J=8.4, 13.6 Hz, 3H), 2.31 - 2.23 (m, 2H), 2.20 (d, J=7.2 Hz, 1H), 2.08 (s, 4H), 2.01 - 1.83 (m, 4H), 1.53 (s, 1H), 1.31 - 1.04 (m, 3H), 1.00 - 0.92 (m, 6H). |
| 547 | B | C | 1H NMR (400MHz, DMSO-d6) δ 13.09 - 12.80 (m, 1H), 10.96 - 10.87 (m, 1H), 8.69 - 8.64 (m, 1H), |

FIG. 3B. Continued

| | | | |
|---|---|---|---|
| | | | 8.64 - 8.41 (m, 1H), 8.16 - 8.12 (m, 1H), 8.12 - 8.06 (m, 1H), 7.82 - 7.55 (m, 3H), 7.31 - 7.23 (m, 1H), 7.16 - 7.08 (m, 2H), 6.76 - 6.58 (m, 1H), 6.54 - 6.35 (m, 1H), 5.38 - 5.22 (m, 1H), 4.99 - 4.92 (m, 1H), 4.21 (s, 2H), 4.14 - 4.10 (m, 2H), 3.84 - 3.82 (m, 3H), 3.48 (s, 4H), 3.18 - 3.15 (m, 4H), 2.85 (s, 1H), 2.69 - 2.66 (m, 4H), 2.58 (d, J = 1.6 Hz, 2H), 2.31 - 2.20 (m, 1H), 2.16 - 2.00 (m, 2H), 1.97 - 1.86 (m, 1H). |
| 548 | A | B | 1H NMR (400 MHz, DMSO-d6) δ 12.95 (d, J = 2.8 Hz, 1H), 10.97 (s, 1H), 9.86 (s, 2H), 8.67 (d, J = 2.0 Hz, 1H), 8.57 (s, 1H), 8.09 (d, J = 2.8 Hz, 1H), 7.72 - 7.56 (m, 4H), 7.32 - 7.23 (m, 1H), 7.21 (d, J = 1.6 Hz, 1H), 7.15 (d, J = 8.8 Hz, 2H), 7.12 - 7.07 (m, 1H), 5.43 - 5.18 (m, 1H), 5.13 - 5.04 (m, 1H), 4.43 - 4.35 (m, 1H), 4.31 - 4.23 (m, 3H), 3.99 - 3.81 (m, 12H), 3.63 (d, J = 10.8 Hz, 4H), 3.50 - 3.38 (m, 5H), 3.33 - 3.21 (m, 3H), 3.14 - 3.04 (m, 2H), 2.95 - 2.85 (m, 1H), 2.58 (d, J = 17.6 Hz, 1H), 2.42 - 2.34 (m, 1H), 2.15 - 1.94 (m, 3H). |
| 549 | C | C | 1H NMR (400 MHz, DMSO-d6) δ 12.98 (d, J = 2.2 Hz, 1H), 10.96 (s, 1H), 10.04 - 9.90 (m, 1H), 9.87 (s, 1H), 8.67 (d, J = 2.0 Hz, 1H), 8.59 (s, 1H), 8.09 (d, J = 2.0 Hz, 1H), 7.70 (d, J = 8.8 Hz, 2H), 7.66 - 7.60 (m, 1H), 7.58 (d, J = 8.4 Hz, 1H), 7.27 (t, J = 8.8 Hz, 1H), 7.18 - 7.05 (m, 4H), 5.40 - 5.20 (m, 1H), 5.10 - 4.99 (m, 1H), 4.38 - 4.16 (m, 4H), 4.06 - 3.94 (m, 2H), 3.88 (s, 4H), 3.47 - 3.37 (m, 7H), 3.34 - 3.11 (m, 6H), 2.95 - 2.86 (m, 1H), 2.62 - 2.53 (m, 2H), 2.40 - 2.33 (m, 1H), 2.19 - 2.09 (m, 1H), 2.07 - 1.85 (m, 2H). |
| 550 | A | B | 1H NMR (400 MHz, DMSO-d6) δ 12.93 (s, 1H), 10.94 (s, 1H), 8.66-8.55 (m, 2H), 8.14-8.07 (m, 1H), 7.66-7.61 (m, 3H), 7.50-7.48 (m, 1H),7.30-7.25 (m, 1H), 7.10-7.08 (m, 2H), 6.50-6.45 (m, 2H), 5.30 (d, J=53.6 Hz, 1H), 5.04-5.01 (m, 1H), 4.33-4.16 (m, 3H), 3.96-3.82 (m, 5H), 3.28-3.26 (m, 6H), 2.98-2.82 (m, 2H), 2.72 (s, 4H), 2.61-2.57 (m, 3H), 2.36-2.25 (m, 4H), 2.24-2.08 (m, 2H), 1.97-1.82 (m, 3H). |
| 551 | B | C | 1H NMR (400 MHz, DMSO-d6) δ 12.89 (d, J=2.0 Hz, 1 H) 10.97 (s, 1 H) 9.86 (s, 1 H) 8.64 (d, J=1.6 Hz, 1 H) 8.53 (s, 1 H) 8.06 (s, 1 H) 7.58 - 7.67 (m, 4 H) 7.27 (t, J=8.4 Hz, 1 H) 7.16 - 7.22 (m, 2 H) 6.75 - 6.75 (m, 1 H) 6.71 (d, J=8.4 Hz, 2 H) 5.21 - 5.38 (m, 1 H) 5.07 (dd, J=13.2, 5.0 Hz, 1 H) 4.20 - 4.43 (m, 2 H) 3.96 - 4.14 (m, 2 H) 3.65 - 3.79 (m, 2 H) 3.62 (t, J=8.8 Hz, 2 H) 3.30 (dd, J=10.4, 7.2 Hz, 4 H) 3.17 - 3.27 (m, 4 H) 3.10 - 3.17 (m, 1 H) 2.79 - 2.99 (m, 2 H) 2.60 (d, J=17.2 Hz, 1 H) 2.44 (s, 1 H) 2.39 (dd, J=13.6, 4.4 Hz, 1 H) 2.21 - 2.30 (m, 1 H) 2.03 - 2.19 (m, 2 H) 1.90 - 2.03 (m, 2 H) 1.74 - 1.88 (m, 1 H). |
| 552 | B | C | 1H NMR (400 MHz, DMSO-d6) δ 12.90 (s, 1H), 10.97 (s, 1H), 9.92 - 9.81 (m, 1H), 9.59 (s, 1H), 8.64 (d, J = 2.0 Hz, 1H), 8.54 (s, 1H), 8.06 (s, 1H), 7.65 - 7.57 (m, 4H), 7.27 (t, J = 9.2 Hz, 1H), 7.22 - 7.15 (m, 2H), 6.71 (d, J = 8.8 Hz, 2H), 5.39 - 5.21 (m, 1H), 5.07 (dd, J = 5.2, 13.2 Hz, 1H), 4.40 - 4.33 (m, 1H), 4.29 - 4.21 (m, 1H), 4.06 (d, J = 8.8 Hz, 2H), 3.76 - 3.68 (m, 2H), 3.65 - 3.59 (m, 2H), 3.32 - 3.10 (m, 9H), 2.99 - 2.82 (m, 2H), 2.59 (d, J = 16.8 Hz, 2H), 2.42 - 2.36 (m, 2H), 2.30 - 2.25 (m, 1H), 2.18 - 2.04 (m, 2H), 2.04 - 1.91 (m, 2H), 1.90 - 1.76 (m, 1H). |

FIG. 3B. Continued

| | | | |
|---|---|---|---|
| 553 | A | C | 1H NMR (400MHz, DMSO-d6) δ 12.91 (s, 1H), 10.91 (s, 1H), 8.65 (d, J=2.0 Hz, 1H), 8.53 (s, 1H), 8.15 (s, 1H), 8.07 (s, 1H), 7.66 - 7.56 (m, 3H), 7.25 (t, J=8.8 Hz, 1H), 7.08 (d, J=8.8 Hz, 2H), 6.61 (s, 1H), 6.49 (s, 1H), 5.39 - 5.20 (m, 1H), 4.96 (dd, J=5.2, 13.2 Hz, 1H), 4.28 - 4.20 (m, 1H), 4.15 - 4.05 (m, 1H), 3.83 (s, 3H), 3.49 - 3.36 (m, 8H), 3.27 - 3.18 (m, 7H), 2.99 - 2.80 (m, 1H), 2.63 - 2.56 (m, 8H), 2.54 (s, 2H), 2.30 - 2.24 (m, 1H), 2.16 - 2.03 (m, 2H), 2.02 - 1.84 (m, 2H). |
| 554 | D | B | 1H NMR (400MHz, DMSO-d6) δ 12.87 (s, 1H), 10.93 (s, 1H), 8.67 (s, 1H), 8.56 (s, 1H), 8.19 (s, 1H), 8.05 (s, 1H), 7.69 - 7.56 (m, 3H), 7.51 (d, J=8.8 Hz, 1H), 7.21 (s, 1H), 7.13 - 7.01 (m, 4H), 5.38 - 5.19 (m, 1H), 5.09 - 4.99 (m, 1H), 4.37 - 4.27 (m, 1H), 4.23 - 4.15 (m, 1H), 3.96 - 3.86 (m, 2H), 3.70 - 3.62 (m, 2H), 3.48 - 3.43 (m, 1H), 3.40 - 3.34 (m, 6H), 2.96 - 2.80 (m, 3H), 2.63 - 2.56 (m, 2H), 2.28 - 2.14 (m, 3H), 2.13 - 2.04 (m, 2H), 2.03 - 1.94 (m, 2H), 1.91 - 1.79 (m, 3H), 1.33 - 1.19 (m, 2H), 1.03 (d, J=6.0 Hz, 6H). |
| 555 | D | C | 1H NMR (400MHz, DMSO-d6) δ 13.19 - 12.84 (m, 1H), 11.17 - 10.76 (m, 1H), 9.91 - 9.80 (m, 1H), 9.66 - 9.45 (m, 1H), 8.77 - 8.67 (m, 1H), 8.62 - 8.50 (m, 1H), 8.18 - 8.04 (m, 1H), 7.73 - 7.57 (m, 2H), 7.45 - 7.36 (m, 1H), 7.33 - 7.25 (m, 2H), 7.21 - 7.16 (m, 2H), 7.12 - 7.05 (m, 1H), 5.37 - 5.23 (m, 1H), 5.10 - 5.04 (m, 1H), 4.41 - 4.34 (m, 1H), 4.29 - 4.22 (m, 1H), 4.16 - 3.96 (m, 2H), 3.94 - 3.81 (m, 2H), 3.77 - 3.59 (m, 2H), 3.51 - 3.47 (m, 1H), 3.44 - 3.36 (m, 2H), 3.34 - 3.27 (m, 1H), 3.27 - 3.15 (m, 5H), 2.98 - 2.83 (m, 3H), 2.65 - 2.56 (m, 2H), 2.43 - 2.37 (m, 2H), 2.18 - 2.04 (m, 3H), 2.03 (s, 2H), 1.95 - 1.89 (m, 2H), 1.49 - 1.32 (m, 2H). |
| 556 | A | C | 1H NMR (300 MHz, DMSO-d6, ppm) δ 12.85 (s, 1H), 11.00-10.87 (s, 1H),8.76-8.45 (m, 2H), 8.22-8.00 (m, 2H),7.78-7.46 (m, 4H), 7.44-7.20 (m, 1H),7.18-7.00 (m, 2H), 6.63-6.42 (m, 2H), 5.42-5.20 (m, 1H), 5.15-4.95 (m,1H), 4.40-4.12 (m, 2H), 4.00-3.71(m, 7H), 3.53-3.47 (m, 1H), 3.35-3.13 (m, 4H),3.08-2.83(m, 4H), 2.81-2.65 (m, 4H), 2.43-2.30 (m, 1H), 2.20-1.91 (m, 5H), 1.90-1.80(m, 2H), 1.79-1.67 (m,1H) , 1.37-1.18 (m,2H), 0.60-0.11 (m,1H). |
| 557 | B | B | 1H NMR (400 MHz, DMSO-d6) δ 12.95 (s, 1H), 10.94 (s, 1H), 8.69 (s, 1H), 8.59 (s, 1H), 8.16 (s, 1H), 8.10 (s, 1H), 7.67-7.55 (m, 3H), 7.54-7.47 (m, 1H), 7.40 (d, J = 8.0 Hz, 2H), 7.30-7.21 (m, 1H), 7.06-7.04 (m, 2H), 5.36-5.16 (d, J = 36 Hz, 1H), 5.04-5.02 (m, 1H), 4.32-4.30 (m, 1H), 4.20-4.16 (m, 1H), 3.89-3.87 (m, 2H), 3.43-3.34 (m, 4H), 3.32-3.23 (m, 2H), 3.01-2.98 (m, 3H), 2.87-2.84 (m, 3H), 2.63-2.54 (m, 1H), 2.36-2.33 (m, 2H), 2.23-2.22 (m, 2H), 2.14-1.92 (m, 5H), 1.73-1.71 (m, 6H), 1.23-1.21 (m, 2H). |
| 558 | D | C | 1H NMR (400MHz, DIMETHYLSULFOXIDE-d6) δ 12.92 (d, J = 2.4 Hz, 1H), 10.93 (s, 1H), 9.83 (s, 1H), 8.67 (d, J = 2.4 Hz, 1H), 8.58 (s, 1H), 8.08 (d, J = 3.2 Hz, 1H), 7.74 - 7.56 (m, 3H), 7.33 - 7.23 (m, 1H), 7.17 (d, J = 8.0 Hz, 2H), 6.82 (s, 1H), 6.65 (s, 1H), 5.37 - 5.22 (m, 1H), 5.00 (dd, J = 5.4, 13.0 Hz, 1H), 4.50 (s, 2H), 4.36 - 4.28 (m, 1H), 4.25 - 4.15 (m, 1H), 4.05 - 3.92 (m, 2H), 3.88 (s, 3H), 3.76 - 3.65 |

FIG. 3B. Continued

| | | | |
|---|---|---|---|
| | | | (m, 3H), 3.48 (s, 1H), 3.17 (s, 5H), 2.99 - 2.79 (m, 3H), 2.18 - 2.03 (m, 3H), 2.01 - 1.87 (m, 3H). |
| 559 | B | C | 1H NMR (400MHz, DIMETHYLSULFOXIDE-d6) δ 13.02 - 12.76 (m, 1H), 10.91 (s, 1H), 9.83 (s, 1H), 8.64 (s, 1H), 8.61 - 8.46 (m, 1H), 8.06 (s, 1H), 7.73 - 7.51 (m, 3H), 7.27 (t, J = 8.8 Hz, 1H), 7.07 (d, J = 8.8 Hz, 2H), 6.60 - 6.42 (m, 2H), 5.44 - 5.16 (m, 1H), 5.04 - 4.90 (m, 1H), 4.83 (s, 1H), 4.37 - 4.24 (m, 1H), 4.21 - 4.07 (m, 1H), 3.88 - 3.74 (m, 5H), 3.55 - 3.46 (m, 2H), 2.96 - 2.82 (m, 1H), 2.76 (s, 2H), 2.67 (s, 2H), 2.42 - 2.26 (m, 5H), 2.25 - 2.04 (m, 9H), 2.01 - 1.90 (m, 2H), 1.82 (d, J = 12.7 Hz, 2H), 1.30 - 1.20 (m, 2H). |
| 560 | B | C | 1H NMR (400 MHz, DMSO-d6) δ 10.93 (s, 1H), 8.68 (d, J=2.4 Hz, 1H), 8.58 (s, 1H), 8.17 (s, 1H), 8.09 (s, 1H), 7.70 - 7.64 (m, 2H), 7.64 - 7.58 (m, 1H), 7.50 (d, J=8.8 Hz, 1H), 7.40 (d, J=8.2 Hz, 2H), 7.25 (t, J=8.4 Hz, 1H), 7.08 - 7.01 (m, 2H), 5.40 - 5.18 (m, 1H), 5.04 (dd, J=5.2, 13.2 Hz, 1H), 4.36 - 4.28 (m, 1H), 4.24 - 4.15 (m, 1H), 3.88 (d, J=12.7 Hz, 2H), 3.47 (s, 1H), 3.08 (d, J=9.6 Hz, 4H), 2.91 - 2.77 (m, 4H), 2.61 (s, 2H), 2.58 - 2.54 (m, 2H), 2.38 (s, 1H), 2.21 - 2.04 (m, 4H), 2.02 - 1.89 (m, 2H), 1.87 - 1.68 (m, 6H), 1.56 (s, 1H), 1.47 (d, J=7.0 Hz, 2H), 1.31 - 1.21 (m, 2H). |
| 561 | D | B | 1H NMR (400 MHz, DMSO-d6) δ 13.00 (d, J = 2.8 Hz, 1H), 10.93 (s, 1H), 9.84 (s, 1H), 9.55 - 9.32 (m, 1H), 8.71 (d, J = 2.0 Hz, 1H), 8.60 (s, 1H), 8.12 (d, J = 2.4 Hz, 1H), 7.63 (dt, J = 6.0, 9.2 Hz, 1H), 7.53 (d, J = 8.8 Hz, 1H), 7.46 - 7.39 (m, 1H), 7.32 (s, 1H), 7.30 - 7.25 (m, 1H), 7.22 (d, J = 7.6 Hz, 1H), 7.13 - 7.03 (m, 3H), 5.44 - 5.18 (m, 1H), 5.04 (dd, J = 5.2, 13.2 Hz, 1H), 4.39 - 4.27 (m, 1H), 4.25 - 4.15 (m, 1H), 3.99 (d, J = 10.4 Hz, 2H), 3.93 (d, J = 12.8 Hz, 2H), 3.69 - 3.64 (m, 2H), 3.49 (d, J = 2.4 Hz, 2H), 3.41 - 3.37 (m, 2H), 3.29 (dt, J = 6.8, 10.0 Hz, 2H), 3.16 (s, 2H), 2.96 - 2.84 (m, 3H), 2.64 - 2.52 (m, 2H), 2.44 - 2.34 (m, 1H), 2.19 - 2.13 (m, 1H), 2.12 - 2.04 (m, 2H), 2.00 - 1.93 (m, 1H), 1.87 (d, J = 11.6 Hz, 2H), 1.41 - 1.27 (m, 2H). |
| 562 | B | C | 1H NMR (400MHz, DMSO-d6) δ 11.06 (s, 1 H) 8.64 (d, J=2.4 Hz, 1 H) 8.52 (s, 1 H) 8.18 (s, 1 H) 8.05 (s, 1 H) 7.60 - 7.66 (m, 2 H) 7.58 (d, J=8.4 Hz, 2 H) 7.24 (t, J=8.4 Hz, 1 H) 7.05 (d, J=8.8 Hz, 2 H) 6.79 (d, J=1.6Hz, 1 H) 6.65 (dd, J=8.4, 1.6 Hz, 1 H) 5.17 - 5.39 (m, 1 H) 5.05 (dd, J=12.8, 5.2 Hz, 1 H) 4.12 (s, 4 H) 3.76 (br d, J=12.4 Hz, 3 H) 3.47 (s, 2 H) 3.45 - 3.46 (m, 1 H) 3.39 (d, J=3.2 Hz, 3 H) 3.23 - 3.32 (m, 5 H) 2.82 - 2.93 (m, 1 H) 2.69 - 2.75 (m, 1 H) 2.67 (d, J=1.6 Hz, 1 H) 2.55 (d, J=8.4 Hz, 1 H) 2.31 - 2.35 (m, 2 H) 1.94 - 2.14 (m, 3 H) 1.77 (d, J=11.2 Hz, 2 H) 1.39 - 1.53 (m, 1 H) 1.16 - 1.31 (m, 2 H). |
| 563 | B | C | 1H NMR (400 MHz, DMSO-d6) δ 12.90 (s, 1H), 10.93 (s, 1H), 9.83 (s, 1H), 8.82 (s, 1H), 8.65 (d, J = 2.4 Hz, 1H), 8.55 (s, 1H), 8.07 (s, 1H), 7.68 - 7.58 (m, 3H), 7.51 (d, J = 8.8 Hz, 1H), 7.27 (t, J = 8.4 Hz, 1H), 7.11 - 7.04 (m, 2H), 6.84 (d, J = 8.8 Hz, 2H), 5.42 - 5.19 (m, 1H), 5.04 (dd, J = 4.4, 13.3 Hz, 1H), 4.76 - 4.66 (m, 1H), 4.49 (s, 1H), 4.36 - 4.28 (m, 1H), 4.23 - 4.14 (m, 1H), 3.91 (d, J = 10.4 Hz, 2H), 3.72 (d, J = 8.8 Hz, 2H), 3.54 (s, 8H), 3.34 - 3.24 (m, 2H), 3.20 - 3.02 (m, 2H), 2.98 - 2.78 (m, 3H), 2.58 (d, J = 17.2 Hz, 1H), 2.40 (d, J = 12.4 Hz, 1H), 2.25 - 2.07 (m, 3H), 1.98 (d, J = 8.8 Hz, 3H), 1.91 - 1.79 |

FIG. 3B. Continued

| | | | |
|---|---|---|---|
| | | | (m, 2H), 1.36 - 1.22 (m, 2H). |
| 564 | B | C | 1H NMR (400 MHz, DMSO-d6) δ 12.90 (d, J = 2.4 Hz, 1H), 10.93 (s, 1H), 9.83 (s, 1H), 8.82 (s, 1H), 8.65 (d, J = 2.0 Hz, 1H), 8.56 (s, 1H), 8.07 (s, 1H), 7.71 - 7.58 (m, 3H), 7.51 (d, J = 8.8 Hz, 1H), 7.27 (t, J = 8.4 Hz, 1H), 7.10 - 7.03 (m, 2H), 6.84 (d, J = 8.8 Hz, 2H), 5.41 - 5.20 (m, 1H), 5.04 (dd, J = 5.2, 13.3 Hz, 1H), 4.77 - 4.66 (m, 1H), 4.49 (s, 1H), 4.37 - 4.26 (m, 1H), 4.23 - 4.14 (m, 1H), 3.91 (d, J = 11.2 Hz, 2H), 3.72 (d, J = 9.6 Hz, 2H), 3.46 - 3.37 (m, 8H), 3.34 - 3.27 (m, 3H), 3.10 (s, 1H), 2.96 - 2.78 (m, 3H), 2.60 (s, 1H), 2.38 (s, 1H), 2.25 - 2.06 (m, 3H), 2.04 - 1.93 (m, 3H), 1.91 - 1.78 (m, 2H), 1.39 - 1.23 (m, 2H). |
| 565 | A | C | 1H NMR (300 MHz, DMSO-d6) δ (ppm): 12.90 (s, 1H), 10.94 (s, 1H), 8.66 (s, 1H), 8.54 (s, 1H), 8.07 (s, 1H), 7.61-7.49 (m, 4H), 7.26-7.24 (m, 1H), 7.09-7.06 (d, J = 7.5 Hz, 2H), 6.65 (m, 2H), 5.39-5.03 (m, 2H), 4.35-4.17 (m, 2H), 3.80-3.77 (d, J =9.6 Hz, 2H), 3.48-3.34 (m, 7H), 3.25-3.10 (m, 5H), 2.97-2.84 (m, 1H), 2.74-2.63 (m, 3H), 2.40-2.29(m, 4H), 2.19-2.08 (m, 3H), 1.98-1.73 (m, 4H),1.60-1.51 (m, 1H), 1.30-1.15(m, 3H). |
| 566 | D | C | 1H NMR (400MHz, DMSO-d6) δ 12.92 (d, J = 2.4 Hz, 1H), 10.92 (s, 1H), 9.83 (s, 1H), 9.51 - 9.38 (m, 1H), 8.66 (d, J = 2.0 Hz, 1H), 8.60 - 8.54 (m, 1H), 8.08 (d, J = 2.8 Hz, 1H), 7.67 (d, J = 8.8 Hz, 2H), 7.64 - 7.58 (m, 1H), 7.50 (d, J = 9.2 Hz, 1H), 7.27 (t, J = 8.4 Hz, 1H), 7.16 (d, J = 8.8 Hz, 2H), 6.86 - 6.81 (m, 2H), 5.38 - 5.22 (m, 1H), 5.03 (dd, J = 5.2, 13.2 Hz, 1H), 4.34 - 4.27 (m, 1H), 4.23 - 4.15 (m, 1H), 3.99 - 3.89 (m, 2H), 3.59 ( d, J = 10.4 Hz, 2H), 3.53 - 3.46 (m, 4H), 3.23 - 3.15 (m, 4H), 3.09 - 3.04 (m, 1H), 3.09 - 3.03 (m, 2H), 3.01 (s, 3H), 2.92 - 2.85 (m, 1H), 2.63 - 2.55 (m, 2H), 2.41 - 2.34 (m, 1H), 2.17 - 2.05 (m, 2H), 2.03 - 1.90 (m, 2H), 1.76 - 1.68 (m, 2H), 1.63 - 1.56 (m, 2H). |
| 567 | D | C | 1H NMR (400MHz, DMSO-d6) δ 13.03 - 12.89 (m, 1H), 10.99 - 10.87 (m, 1H), 9.91 - 9.75 (m, 1H), 9.34 - 9.12 (m, 1H), 8.70 - 8.65 (m, 1H), 8.63 - 8.55 (m, 1H), 8.13 - 8.07 (m, 1H), 7.80 - 7.70 (m, 2H), 7.69 - 7.58 (m, 1H), 7.55 - 7.48 (m, 1H), 7.32 - 7.22 (m, 1H), 7.21 - 7.12 (m, 2H), 7.10 - 7.04 (m, 2H), 5.41 - 5.20 (m, 1H), 5.09 - 4.98 (m, 1H), 4.50 - 4.39 (m, 2H), 4.34 - 4.17 (m, 2H), 3.97 - 3.90 (m, 3H), 3.44 - 3.36 (m, 3H), 3.23 (s, 2H), 3.13 - 3.04 (m, 1H), 2.98 - 2.92 (m, 3H), 2.92 - 2.83 (m, 3H), 2.62 - 2.53 (m, 1H), 2.42 - 2.35 (m, 1H), 2.19 - 2.06 (m, 3H), 1.98 - 1.81 (m, 3H), 1.42 - 1.20 (m, 2H). |
| 568 | A | C | 1H NMR (300 MHz, DMSO-d6) δ (ppm): 12.90 (s, 1H), 10.94 (s, 1H), 8.66 (s, 1H), 8.54 (s, 1H), 8.08 (s, 1H), 7.65-7.49 (m, 4H), 7.31-7.28 (m, 1H), 7.09-7.06 (d, J = 8.7 Hz, 2H), 6.64-6.62 (m, 2H), 5.39-5.02 (m, 2H), 4.29-4.12 (m, 2H), 3.82-3.78 (d, J =11.4Hz, 2H), 3.61-3.51 (m, 2H), 3.41-3.35 (m, 9H), 3.29-3.26(m, 1H), 3.12-3.09 (m, 1H), 2.91-2.62 (m, 5H), 2.35-2.08(m, 2H), 1.98-1.65 (m, 8H), 1.30-1.15(m, 4H). |
| 569 | B | B | 1H NMR (400MHz, DMSO-d6) δ 13.08 - 12.95 (m, 1H), 11.06 - 10.87 (m, 1H), 9.94 - 9.78 (m, 1H), 8.77 - 8.69 (m, 1H), 8.67 - 8.57 (m, 1H), 8.16 - 8.09 (m, 1H), 7.80 - 7.69 (m, 2H), 7.68 - 7.55 (m, 2H), |

FIG. 3B. Continued

| | | | |
|---|---|---|---|
| | | | 7.49 - 7.35 (m, 2H), 7.33 - 7.23 (m, 1H), 7.22 - 7.07 (m, 2H), 5.38 - 5.20 (m, 1H), 5.12 - 5.00 (m, 1H), 4.43 - 4.31 (m, 1H), 4.28 - 4.18 (m, 1H), 3.49 (s, 3H), 3.43 - 3.37 (m, 5H), 3.35 - 3.25 (m, 4H), 3.24 - 3.12 (m, 5H), 3.01 - 2.85 (m, 3H), 2.65 - 2.56 (m, 2H), 2.47 - 2.36 (m, 2H), 2.13 - 2.10 (m, 1H), 2.10 - 2.05 (m, 3H), 2.04 - 1.93 (m, 3H). |
| 570 | A | C | 1H NMR (300 MHz, DMSO-d6) δ 12.87 (s, 1H), 10.93 (s, 1H), 9.86 (s, 1H), 8.60 (s, 1H), 8.48 (s, 1H), 8.04 (s, 1H), 7.62-7.49 (m, 4H), 7.28-7.22 (m, 1H), 7.05-7.03 (m, 2H), 6.53-6.50 (m, 2H), 5.28 (d, J=52.2 Hz, 1H), 5.06-5.00 (m, 1H), 4.34-4.16 (m, 2H), 3.88 (s, 2H), 3.75 (s, 2H), 3.48-3.38 (m, 4H), 3.31-3.26 (m, 4H), 2.95-2.83 (m, 1H), 2.59-2.52 (m, 4H), 2.48-2.43 (m, 3H), 2.38-2.31 (m, 3H), 2.12-2.03 (m, 2H), 1.96-1.88 (m, 4H). |
| 571 | A | C | 1H NMR (300 MHz, DMSO ) δ 12.91 (s, 1H), 10.98 (s, 1H), 9.93 (s, 1H), 8.67-8.56 (m, 2H), 8.09 (s, 1H), 7.68-7.60 (m, 4H), 7.31-7.07 (m, 5H), 5.40-5.06 (m, 2H), 4.43-4.25 (m, 2H), 4.14-4.10 (m, 2H), 3.51-3.23 (m, 6H), 2.92-2.81 (m, 1H), 2.62-2.51 (m, 5H), 2.45-2.35 (m, 3H), 2.15-1.99 (m, 5H), 1.84-1.82 (m, 2H), 1.79-1.65 (m, 2H). |
| 572 | A | C | 1H NMR (300 MHz, DMSO-d6) δ 12.88 (s, 1H), 10.91 (s, 1H), 9.78 (s, 1H), 8.63 (s, 1H), 8.51 (s, 1H), 8.05 (s, 1H), 7.64-7.55 (m, 3H), 7.48-7.45 (m, 1H),7.27-7.21 (m, 1H), 7.06-7.03 (m, 2H), 6.62-6.60 (m, 2H), 5.27 (d, J=53.7 Hz, 1H), 5.04-4.98 (m, 1H), 4.32-4.13 (m, 2H), 3.79-3.75 (m, 2H), 3.47 (s, 1H), 3.30-3.22 (m, 4H), 3.17 (s, 2H), 2.87-2.68 (m, 4H), 2.59 (s, 1H), 2.36-2.33 (m, 3H), 2.22-2.21 (m, 2H), 2.11-2.05 (m, 2H), 1.95-1.77 (m, 6H), 1.70-1.58 (m, 5H), 1.29-1.15 (m, 3H). |
| 573 | A | C | 1H NMR (400 MHz, DMSO-d6) δ 13.36 - 12.31 (m, 1H), 10.96 (s, 1H), 8.70 - 8.47 (m, 2H), 8.27 - 8.00 (m, 2H), 7.61 (s, 5H), 7.22 (s, 1H), 7.13 - 6.91 (m, 4H), 5.41 - 5.15 (m, 1H), 5.13 - 4.79 (m, 3H), 4.47 - 4.14 (m, 4H), 3.27 - 3.23 (m, 8H), 2.91 (s, 1H), 2.38 - 2.18 (m, 11H), 2.12 - 1.94 (m, 2H). |
| 574 | A | C | 1H NMR (300 MHz, DMSO-d6) δ 12.91 (s, 1H), 10.95 (s, 1H), 9.85 (b, 1H), 8.66 (d, J = 2.3 Hz, 1H), 8.54 (s, 1H), 8.08 (s, 1H), 7.61-7.58 (m, 4H), 7.27 (t, J = 8.5 Hz, 1H), 7.08 (t, J = 4.7 Hz, 4H), 5.39 (s, 1H), 5.05 (dd, J = 13.2, 5.1 Hz, 1H), 4.33-4.20 (q, 2H), 3.79 (d, J = 12.2 Hz, 1H), 3.50 (s, 1H), 3.38-3.36 (m, 4H), 3.29-3.26 (m, 4H), 2.99-2.82 (m, 1H), 2.74 (t, J = 11.9 Hz, 2H), 2.62 (s, 3H), 2.42 (d, J = 12.4 Hz, 2H), 2.34 (d, J = 7.2 Hz, 2H), 2.12-2.10 (m, 2H), 1.97-1.85 (m, 5H), 1.64-1.63 (m, 7H), 1.25-1.23 (m, 2H). |
| 575 | A | C | 1HNMR (300 MHz, DMSO-d6) δ 12.88 (b, 1H), 10.95 (s, 1H), 8.66 (s, 1H), 8.54 (s, 1H), 8.08 (s, 1H), 7.71 – 7.51 (m, 4H), 7.27 (t, J = 8.7 Hz, 1H), 7.08-7.04 (m, 4H), 5.30 (d, J = 52.8 Hz, 1H), 5.05 (dd, J = 13.1, 5.1 Hz, 1H), 4.33-4.23 (q, 2H), 3.79 (d, J = 12.1 Hz, 2H), 3.47 – 3.36 (m, 6H), 2.92 (t, J = 13.0 Hz, 1H), 2.74- 2.62 (m, 4H), 2.45-2.29 (m, 8H), 2.12-1.97 (m, 6H), 1.55 (b, 8H), 1.25-1.22 (m, 3H). |
| 576 | A | C | 1H NMR (400MHz, DIMETHYLSULFOXIDE-d6) δ 12.95 (s, 1H), 10.95 (s, 1H), 8.74 - 8.46 (m, 2H), 8.16 (s, 1H), 8.09 (s, 1H), 7.95 (s, 1H), 7.75 - 7.56 (m, 3H), 7.52 (d, J = 8.4 Hz, 1H), 7.27 (t, J = 8.4 Hz, |

FIG. 3B. Continued

| | | | |
|---|---|---|---|
| | | | 1H), 7.15 - 6.96 (m, 4H), 5.44 - 5.18 (m, 1H), 5.05 (dd, J = 4.8, 13.2 Hz, 1H), 4.63 (d, J = 1.2 Hz, 1H), 4.46 - 4.12 (m, 3H), 3.48 (s, 2H), 3.40 (s, 2H), 2.89 (s, 3H), 2.74 - 2.65 (m, 6H), 2.41 - 2.28 (m, 2H), 2.20 - 1.91 (m, 6H), 1.75 - 1.55 (m, 2H), 1.54 - 1.35 (m, 3H). |
| 577 | A | C | 1H NMR (400 MHz, DMSO-d6) δ 12.92 (s, 1H), 10.94 (s, 1H), 9.87 (s, 1H), 8.67-8.66 (m, 1H), 8.55 (s, 1H), 8.14-8.08 (m, 1H), 7.65-7.61 (m, 3H), 7.51-7.49 (m, 1H),7.30-7.26 (m, 1H), 7.11-7.09 (m, 2H), 6.54-6.49 (m, 2H), 5.30 (d, J=52.4 Hz, 1H), 5.07-5.02 (m, 1H), 4.34-4.29 (m, 1H), 4.21-4.17 (m, 1H), 4.09-4.05 (m, 2H), 3.64-3.60 (m, 2H), 3.50-3.41 (m, 4H), 3.30-3.25 (m, 6H), 3.08-3.04 (m, 1H), 2.95-2.86 (m, 1H), 2.75-2.73 (m, 1H), 2.65-2.47 (m, 4H), 2.41-2.35 (m, 1H), 2.14-1.95 (m, 3H). |
| 578 | B | C | 1H NMR (300 MHz, DMSO ) δ 12.91 (s, 1H), 10.97 (s, 1H), 8.70 (s, 1H), 8.65 (s, 1H), 8.12 (s, 1H), 7.70-7.62 (m, 4H), 7.41-7.39 (d, J=8.4Hz, 2H), 7.27-7.19 (m, 1H), 7.10-7.09 (d, J=4.2Hz, 1H), 7.07-7.06 (d, J=2.1Hz, 1H), 5.11-5.06 (m, 2H), 4.44-4.26 (m, 2H), 4.15-4.11 (m, 2H), 2.50 (s, 4H), 3.13-3.10 (d, J=10.8Hz, 3H), 2.98-2.84 (m, 1H), 2.63 (s, 1H), 2.42-2.41 (d, J=4.5Hz, 1H), 2.19-1.97 (m, 6H), 1.87-1.67 (m, 9H). |
| 579 | A | C | 1H NMR (400 MHz, DMSO-d6) δ 12.89 (s, 1H), 10.98 (s, 1H), 9.82 (s, 1H), 8.65 (d, J = 2.2 Hz, 1H), 8.53 (s, 1H), 8.06 (s, 1H), 7.68 – 7.57 (m, 4H), 7.57 (s, 1H), 7.51 (s, 1H), 7.44 – 7.38 (m, 1H), 7.25 (t, J = 8.7 Hz, 1H), 7.07 (d, J = 8.6 Hz, 2H), 5.36 (s, 1H), 5.22 (s, 1H), 5.10 (dd, J = 13.3, 5.1 Hz, 1H), 4.43 (d, J = 17.3 Hz, 1H), 4.29 (d, J = 17.3 Hz, 1H), 3.80-3.78 (m, 2H), 3.00-2.96 (m, 3H), 2.97 – 2.84 (m, 1H), 2.74-271 (m, 2H), 2.67 – 2.55 (m, 2H), 2.46 – 2.35 (m, 1H), 2.24 (d, J = 7.0 Hz, 2H), 2.01-1.86 (m, 5H), 1.78 -1.73 (m, 7H), 1.24-1.21 (m, 3H). |
| 580 | A | C | 1H NMR (400MHz, DMSO-d6) δ 12.90 (d, J = 2.4 Hz, 1H), 10.93 (s, 1H), 9.83 (s, 1H), 9.67 - 9.47 (m, 1H), 8.63 (d, J = 2.4 Hz, 1H), 8.57 - 8.42 (m, 1H), 8.07 (d, J = 2.4 Hz, 1H), 7.66 - 7.57 (m, 3H), 7.53 (d, J = 8.8 Hz, 1H), 7.27 (s, 1H), 7.09 (s, 2H), 6.62 (d, J = 8.8 Hz, 2H), 5.23 (s, 1H), 5.07 - 5.02 (m, 1H), 4.30 (s, 1H), 4.23 (s, 1H), 3.98 - 3.92 (m, 4H), 3.88 - 3.83 (m, 1H), 3.75 - 3.64 (m, 1H), 3.52 - 3.48 (m, 1H), 3.44 - 3.36 (m, 3H), 3.35 - 3.26 (m, 1H), 3.23 - 3.10 (m, 3H), 2.97 - 2.79 (m, 3H), 2.63 - 2.55 (m, 1H), 2.47 - 2.42 (m, 2H), 2.40 - 2.34 (m, 1H), 2.30 - 2.24 (m, 1H), 2.16 - 1.76 (m, 7H), 1.31 (d, J = 12.4 Hz, 2H). |
| 581 | A | C | 1H NMR (400 MHz, DMSO-d6) δ 12.91 (s, 1H), 10.94 (s, 1H), 8.65 (d, J=2.0 Hz, 1H), 8.53 (s, 1H), 8.18 (s, 1H), 8.06 (s, 1H), 7.66 - 7.57 (m, 3H), 7.50 (d, J=8.8 Hz, 1H), 7.29 - 7.21 (m, 1H), 7.10 - 7.03 (m, 4H), 5.48 - 5.16 (m, 1H), 5.05 (dd, J=5.2, 13.2 Hz, 1H), 4.40 - 4.29 (m, 1H), 4.25 - 4.15 (m, 1H), 3.87 (d, J=11.6 Hz, 2H), 3.50 (d, J=18.8 Hz, 4H), 3.23 (s, 4H), 2.95 - 2.75 (m, 3H), 2.61 (s, 2H), 2.39 (s, 3H), 2.21 (d, J=6.0 Hz, 2H), 2.09 (d, J=14.4 Hz, 2H), 1.97 (d, J=5.2 Hz, 2H), 1.84 - 1.76 (m, 3H), 1.63 - 1.45 (m, 9H), 1.19 (d, J=10.4 Hz, 2H). |
| 582 | D | C | 1H NMR (400MHz, DMSO-d6) δ 13.01 - 12.93 (m, 1H), 10.96 - 10.90 (m, 1H), 9.88 - 9.83 (m, 1H), |

FIG. 3B. Continued

| | | | |
|---|---|---|---|
| | | | 8.72 - 8.66 (m, 1H), 8.63 - 8.56 (m, 1H), 8.15 - 8.08 (m, 1H), 7.73 - 7.58 (m, 3H), 7.53 - 7.46 (m, 1H), 7.42 - 7.33 (m, 2H), 7.32 - 7.24 (m, 1H), 6.61 - 6.47 (m, 2H), 5.38 - 5.22 (m, 1H), 5.09 - 5.00 (m, 1H), 4.50 - 4.43 (m, 1H), 4.34 - 4.28 (m, 1H), 4.22 - 4.13 (m, 4H), 3.74 (dd, J = 4.0, 8.0 Hz, 2H), 3.52 - 3.35 (m, 5H), 3.34 - 3.25 (m, 1H), 2.98 - 2.81 (m, 1H), 2.78 - 2.69 (m, 2H), 2.17 - 2.00 (m, 2H), 1.99 - 1.86 (m, 3H), 1.36 - 1.31 (m, 1H). |
| 583 | B | C | 1H NMR (300 MHz, DMSO-d6) 12.84 (s, 1H), 10.94 (s, 1H), 9.61 (s, 1H), 8.65 (s, 1H), 8.53 (s, 1H), 8.07 (s, 1H), 7.63-7.48 (m, 4H), 7.29-7.27 (m, 1H), 7.08-7.05 (m, 2H), 6.53-6.48 (m, 2H), 5.30 (d, J = 53.1 Hz, 1H), 5.07-5.00 (m, 1H), 4.34-4.15 (m, 2H), 3.89-3.85 (m, 2H), 3.58 (s, 1H), 3.39-3.35 (m, 5H), 3.28 (s, 2H), 2.99-2.86 (m, 3H), 2.61 (s, 1H), 2.51-2.49 (m, 4H), 2.22-2.20 (m, 2H), 2.11-2.06 (m, 2H), 1.97-1.81 (m, 7H), 1.77 (s, 4H), 1.21-1.16 (m, 2H) |
| 584 | A | C | 1H NMR (300 MHz, DMSO-d6) δ 12.88 (s, 1H), 10.95 (s, 1H), 9.85 (s, 1H), 8.67 (s, 1H), 8.55 (s, 1H), 8.08 (s, 1H), 7.71-7.56 (m, 4H), 7.35-7.21 (m, 1H), 7.27-7.02 (m, 4H), 5.30 (d, J = 53.0Hz, 1H), 5.06-5.03 (m, 1H), 4.49-4.17 (m, 2H), 3.88 (d, J = 12.9 Hz, 2H), 3.51 (s, 1H), 3.34-3.29 (m, 3H), 3.28-3.19 (m, 3H), 3.01-2.79 (m, 3H), 2.67-2.55 (m, 3H), 2.49-2.29 (m, 5H), 2.19-2.03 (m, 2H), 2.01-1.90 (m, 2H), 1.83-1.80 (m, 2H), 1.78-1.63 (m, 7H), 1.32-1.05 (m, 2H). |
| 585 | A | C | 1H NMR (400MHz, DIMETHYLSULFOXIDE-d6) δ 12.93 (d, J = 2.4 Hz, 1H), 10.90 (s, 1H), 9.84 (s, 1H), 9.44 - 9.25 (m, 1H), 8.68 (d, J = 2.0 Hz, 1H), 8.58 (s, 1H), 8.09 (d, J = 2.8 Hz, 1H), 7.74 - 7.53 (m, 3H), 7.27 (t, J = 8.4 Hz, 1H), 7.17 (d, J = 8.8 Hz, 2H), 6.64 (s, 1H), 6.50 (s, 1H), 5.46 - 5.18 (m, 1H), 4.97 (dd, J = 4.8, 13.2 Hz, 1H), 4.23 (d, J = 17.2 Hz, 1H), 4.15 - 4.06 (m, 1H), 3.96 (d, J = 10.0 Hz, 4H), 3.85 (s, 3H), 3.65 (d, J = 8.8 Hz, 3H), 3.38 (br d, J = 2.0 Hz, 1H), 3.30 (dt, J = 6.4, 9.6 Hz, 2H), 3.23 - 3.09 (m, 6H), 3.01 - 2.81 (m, 3H), 2.24 - 2.06 (m, 3H), 2.04 - 1.82 (m, 4H), 1.39 - 1.25 (m, 2H). |
| 586 | A | C | 1H NMR (400MHz, DIMETHYLSULFOXIDE-d6) δ 1.15 - 1.27 (m, 2 H) 1.54 (s, 1 H) 1.77 (d, J=11.6 Hz, 2 H) 1.91 - 2.04 (m, 2 H) 2.05 - 2.13 (m, 2 H) 2.16 (t, J=6.8 Hz, 2 H) 2.34 - 2.41 (m, 3 H) 2.60 (s, 1 H) 2.74 - 2.97 (m, 3 H) 3.20 - 3.28 (m, 6 H) 3.39 (d, J=3.2 Hz, 3 H) 3.43 (s, 2 H) 3.47 (s, 1 H) 3.85 (d, J=12.0 Hz, 2 H) 4.14 - 4.24 (m, 1 H) 4.27 - 4.37 (m, 1 H) 5.03 (dd, J=13.2, 5.2 Hz, 1 H) 5.20 - 5.39 (m, 1 H) 6.66 (d, J=8.8 Hz, 2 H) 6.99 - 7.08 (m, 2 H) 7.25 (t, J=8.4 Hz, 1 H) 7.49 (d, J=8.8 Hz, 1 H) 7.53 - 7.66 (m, 3 H) 8.03 (s, 1 H) 8.50 (s, 1 H) 8.62 (d, J=2.4 Hz, 1 H) 10.93 (s, 1 H) 12.86 (s, 1 H). |
| 587 | B | C | 1H NMR (400MHz, DMSO-d6) δ 13.08 - 12.71 (m, 1H), 10.93 (s, 1H), 9.84 (s, 1H), 9.68 - 9.48 (m, 1H), 8.64 (d, J = 2.0 Hz, 1H), 8.58 - 8.48 (m, 1H), 8.05 (s, 1H), 7.68 - 7.56 (m, 3H), 7.56 - 7.48 (m, 1H), 7.27 (s, 1H), 7.17 - 6.99 (m, 2H), 6.68 (dd, J = 4.0, 8.4 Hz, 1H), 5.37 - 5.21 (m, 1H), 5.04 (dd, J = 5.2, 13.6 Hz, 1H), 4.35 - 4.29 (m, 1H), 4.22 (s, 1H), 3.95 - 3.91 (m, 2H), 3.75 - 3.72 (m, 2H), 3.41 (s, 5H), 3.34 - 3.24 (m, 4H), 3.22 - 3.09 (m, 4H), 2.91 - 2.83 (m, 4H), 2.27 - 2.08 (m, 5H), 2.03 - 1.94 (m, 3H), 1.91 - 1.79 (m, 2H), 1.39 - 1.22 (m, 2H). |

FIG. 3B. Continued

| | | | |
|---|---|---|---|
| 588 | A | C | 1H NMR (400MHz, DIMETHYLSULFOXIDE-d6) δ 1.17 - 1.31 (m, 2 H) 1.46 (s, 1 H) 1.77 d, J=12.4 Hz, 2 H) 1.85 - 2.02 (m, 2 H) 2.03 - 2.15 (m, 2 H) 2.23 - 2.29 (m, 1 H) 2.32 (s, 1 H) 2.52 (d, J=2.0 Hz, 5 H) 2.57 (s, 1 H) 2.68 - 2.75 (m, 2 H) 2.83 - 2.96 (m, 1 H) 3.46 (s, 3 H) 3.76 (d, J=9.2 Hz, 3 H) 3.80 (s, 3 H) 3.99 (s, 4 H) 4.03 - 4.11 (m, 1 H) 4.15 - 4.24 (m, 1 H) 4.94 (dd, J=13.2, 4.8 Hz, 1 H) 5.20 - 5.37 (m, 1 H) 5.92 (s, 1 H) 6.07 (s, 1 H) 7.05 (d, J=8.8 Hz, 2 H) 7.24 (t, J=8.0 Hz, 1 H) 7.55 - 7.65 (m, 3 H) 8.06 (s, 1 H) 8.17 (s, 1 H) 8.52 (s, 1 H) 8.64 (d, J=2.0 Hz, 1 H) 10.90 (s, 1 H) 12.79 - 13.01 (m, 1 H). |
| 589 | B | B | 1HNMR (300 MHz, CD3OD) δ 8.74 (s, 1H), 8.65 (s, 1H), 7.93 (s, 1H), 7.77-7.76 (m, 1H), 7.63-7.61 (m, 3H), 7.38 (d, J = 8.1 Hz, 2H), 7.22 -7.09 (m, 1H), 6.55 (s, 2H), 5.33 (s, 1H), 5.18 - 5.03 (m, 2H), 4.38 (s, 2H), 4.06 (s, 4H), 3.67-3.51 (m, 6H), 3.52- 3.43 (m, 2H), 3.00-2.69 (m, 4H), 2.65- 2.53 (m, 2H), 2.46- 2.43 (m, 1H), 2.22-2.10 (m, 3H), 1.78-1.75 (m, 2H). |
| 590 | B | C | 1H-NMR (300 MHz, DMSO-d6, ppm) δ 12.96 (s, 1H), 10.94 (s, 1H), 9.86 (s, 1H), 8.70 (d, J = 2.2 Hz, 1H), 8.60 (s, 1H), 8.12 (s, 1H), 7.73 – 7.58 (m, 3H), 7.49 (d, J = 8.2 Hz, 1H), 7.38 (d, J = 8.1 Hz, 2H), 7.27 (td, J = 8.8, 1.6 Hz, 1H), 6.59 – 6.45 (m, 2H), 5.30 (d, J = 52.8 Hz, 1H), 5.04 (dd, J = 13.2, 5.1 Hz, 1H), 4.30 (d, J = 16.9 Hz, 1H), 4.17 (d, J = 16.9 Hz, 1H), 3.96 – 3.78 (m, 4H), 3.54 – 3.39 (m, 3H), 3.31 – 3.20 (m, 2H), 2.98 – 2.76 (m, 3H), 2.76 – 2.58 (m, 5H), 2.49 – 2.38 (m, 1H), 2.40 – 2.26 (m, 1H), 2.22 – 1.99 (m, 4H), 2.02 – 1.88 (m, 2H), 1.82 (p, J = 7.7 Hz, 2H). |
| 591 | D | | 1H NMR (400 MHz, DMSO ) δ 12.78 (s, 1H), 10.99 (s, 1H), 8.58 (s, 1H), 8.57 (s, 1H), 7.93 (s, 1H), 7.62-7.60 (d, J=6.3Hz, 1H), 7.52-7.48 (m, 3H), 7.20-7.17 (m, 2H), 6.85-6.75 (m, 3H), 6.02 (s, 1H), 5.32-5.04 (m, 1H), 4.39-4.22 (m, 2H), 4.00 (s, 1H), 3.80-3.63 (m, 11H), 3.37-3.08 (m, 8H), 3.94-3.91 (m, 2H), 2.62-2.50 (m, 3H), 2.37-2.33 (m, 2H), 2.01-1.92 (m, 4H). |
| 592 | A | C | 1H NMR (400 MHz, DMSO ) δ 12.91 (s, 1H), 10.99 (s, 1H), 9.81 (s, 1H), 8.62 (s, 1H), 8.61 (s, 1H), 8.05 (s, 1H), 7.65-7.61 (m, 4H), 7.56-7.54 (d, J=8.4Hz, 1H), 7.44-7.34 (m, 1H), 7.26-7.24 (d, J=8.8Hz, 1H), 6.57-6.55 (d, J=8.4Hz, 2H), 5.36-5.11 (m, 2H), 4.45-4.41 (m, 2H), 3.93 (s, 4H), 3.47-3.25 (m, 8H), 2.91-2.83 (m, 1H), 2.73-2.50 (m, 3H), 2.44-2.39 (m, 3H), 2.11-1.99 (m, 3H), 1.64-1.61 (m, 2H). |
| 593 | A | C | 1H NMR (400MHz, DIMETHYLSULFOXIDE-d6) δ 12.91 (s, 1H), 10.90 (s, 1H), 9.84 (s, 1H), 9.78 (d, J = 1.6 Hz, 1H), 8.62 (d, J = 1.6 Hz, 1H), 8.52 (s, 1H), 8.06 (s, 1H), 7.69 - 7.50 (m, 3H), 7.27 (t, J = 8.8 Hz, 1H), 6.72 - 6.56 (m, 3H), 6.48 (s, 1H), 5.42 - 5.19 (m, 1H), 4.99 - 4.88 (m, 1H), 4.43 (d, J = 5.2 Hz, 2H), 4.37 - 4.28 (m, 2H), 4.23 (br d, J = 17.2 Hz, 1H), 4.15 - 4.06 (m, 3H), 4.01 (s, 2H), 3.92 (d, J = 12.4 Hz, 2H), 3.84 (s, 3H), 3.42 - 3.36 (m, 3H), 3.34 - 3.24 (m, 2H), 3.16 (d, J = 6.0 Hz, 2H), 2.85 (t, J = 12.8 Hz, 3H), 2.59 (s, 1H), 2.33 (s, 1H), 2.16 - 2.04 (m, 2H), 1.96 - 1.87 (m, 1H), 1.74 (d, J = 14.7 Hz, 2H), 1.33 - 1.20 (m, 2H). |
| 594 | B | C | 1H NMR (400MHz, DIMETHYLSULFOXIDE-d6) δ 1.89 - 2.03 (m, 2 H) 2.05 - 2.16 (m, 2 H) 2.35 - 2.42 (m, 1 H) 2.61 (d, J=2.8 Hz, 1 H) 2.84 - 2.96 (m, 1 H) 3.06 - 3.19 (m, 2 H) 3.30 (td, J=10.0, 7.2 Hz, 4 |

FIG. 3B. Continued

| | | | |
|---|---|---|---|
| | | | H) 3.36 - 3.48 (m, 6 H) 3.82 (d, J=2.0 Hz, 2 H) 3.88 - 3.97 (m, 3 H) 4.15 - 4.23 (m, 3 H) 4.29 - 4.36 (m, 1 H) 4.54 - 4.64 (m, 1 H) 5.04 (dd, J=13.2, 5.2 Hz, 1 H) 5.17 - 5.41 (m, 1 H) 6.54 (dd, J=8.4, 2.0 Hz, 1 H) 6.57 (s, 1 H) 7.15 (d, J=8.8 Hz, 2 H) 7.27 (t, J=8.4 Hz, 1 H) 7.52 (d, J=8.4 Hz, 1 H) 7.57 - 7.73 (m, 3 H) 8.08 (d, J=2.4 Hz, 1 H) 8.55 - 8.62 (m, 1 H) 8.67 (d, J=2.0 Hz, 1 H) 9.69 - 9.80 (m, 1 H) 9.84 (s, 1 H) 10.93 (s, 1 H) 12.93 (d, J=2.8 Hz, 1 H). |
| 595 | B | B | 1H NMR (300 MHz, DMSO-d6) δ 12.92 (s, 1H), 11.01 (s, 1H), 9.86 (s, 1H), 8.61-8.58 (m, 2H), 8.09 (s, 1H), 7.77-7.70 (m, 2H), 7.70-7.58 (m, 4H), 7.40-7.23 (m, 1H), 7.11 (d, J = 8.7Hz, 2H), 5.40-5.23 (d, J=53.7Hz,1H), 5.19-5.03 (m, 1H), 4.53-4.29 (m, 2H), 3.69 (s, 2H), 3.52 (s, 1H), 3.36 (s, 2H), 3.31-3.28 (m, 5H), 3.01-2.87 (m, 1H), 2.76 (s, 4H), 2.63-2.60 (m, 1H), 2.47-2.28 (m, 1H), 2.18-1.97 (m, 3H). |
| 596 | A | C | 1H NMR (400MHz, DMSO-d6) δ 13.05 - 12.95 (m, 1H), 10.96 (s, 1H), 9.85 (s, 1H), 8.72 (d, J = 2.4Hz, 1H), 8.64 (d, J = 0.8 Hz, 1H), 8.13 (d, J = 2.8 Hz, 1H), 7.81 - 7.73 (m, 2H), 7.67 - 7.56 (m, 2H), 7.47 (d, J = 8.0 Hz, 2H), 7.28 (t, J = 8.4 Hz, 1H), 7.24 - 7.15 (m, 2H), 5.41 - 5.18 (m, 1H), 5.07 (dd, J = 5.2, 13.2 Hz, 1H), 4.42 - 4.33 (m, 1H), 4.29 - 4.22 (m, 1H), 4.14 - 4.02 (m, 3H), 3.72 (d, J = 11.2 Hz, 3H), 3.42 - 3.38 (m, 2H), 3.37 - 3.21 (m, 4H), 3.20 - 3.09 (m, 4H), 2.99 - 2.85 (m, 1H), 2.64 - 2.54 (m, 2H), 2.39 (dd, J = 4.8, 13.2 Hz, 1H), 2.13 - 2.07 (m, 1H), 2.01 - 1.95 (m, 1H). |
| 597 | A | C | 1H NMR (400MHz, DMSO-d6) δ 13.00 (d, J = 2.4 Hz, 1H), 10.94 (s, 1H), 9.85 (s, 1H), 9.82 - 9.69 (m, 1H), 8.72 (d, J = 2.4Hz, 1H), 8.65 (d, J = 1.6 Hz, 1H), 8.16 - 8.10 (m, 1H), 7.82 - 7.72 (m, 2H), 7.69 - 7.58 (m, 1H), 7.51 (d, J = 8.0 Hz, 1H), 7.45 (d, J = 8.0 Hz, 2H), 7.35 - 7.23 (m, 1H), 6.58 (s, 1H), 6.55 - 6.50 (m, 1H), 5.40 - 5.22 (m, 1H), 5.07 - 5.00 (m, 1H), 4.41- 4.32 (m, 4H),4.30 - 4.28 (m, 1H), 4.21 (s, 2H), 4.06 (s, 2H), 3.53 (d, J = 6.0 Hz, 1H), 3.51 - 3.47 (m, 2H), 3.42 - 3.37 (m, 2H), 3.34 - 3.26 (m, 1H), 2.95 - 2.82 (m, 3H), 2.61 (s, 1H), 2.57 - 2.54 (m, 1H), 2.42 - 2.35 (m, 1H), 2.15 - 2.07 (m, 1H), 1.98 - 1.89 (m, 1H). |
| 598 | B | C | 1H NMR (400MHz, DMSO-d6) δ 12.96 (s, 1H), 10.92 (s, 1H), 8.69 (d, J=2.0 Hz, 1H), 8.59 (s, 1H), 8.15 (s, 1H), 8.11 (s, 1H), 7.71 - 7.57 (m, 3H), 7.48 (d, J=8.4 Hz, 1H), 7.38 (d, J=8.0 Hz, 2H), 7.26 (t, J=8.4 Hz, 1H), 6.67 - 6.58 (m, 2H), 5.40 - 5.20 (m, 1H), 5.03 (dd, J=5.2, 13.6 Hz, 1H), 4.35 - 4.26 (m, 1H), 4.23 - 4.13 (m, 1H), 3.51 - 3.43 (m, 6H), 3.40 - 3.38 (m, 4H), 2.95 - 2.85 (m, 1H), 2.83 - 2.73 (m, 2H), 2.71 - 2.67 (m, 2H), 2.62 -2.55 (m, 2H), 2.45 - 2.35 (m, 1H), 2.23 - 2.14 (m, 2H), 2.13 - 2.04 (m, 2H), 2.04 - 1.89 (m, 2H). |
| 599 | A | B | 1H NMR (400MHz, DMSO-d6) δ 13.28 - 12.69 (m, 1H), 10.93 (s, 1H), 8.70 (d, J=2.0 Hz, 1H), 8.59 (s, 1H), 8.15 (s, 1H), 8.11 (s, 1H), 7.70 - 7.59 (m, 3H), 7.49 (d, J=8.4 Hz, 1H), 7.40 (d, J=8.4 Hz, 2H), 7.27 (t, J=8.4 Hz, 1H), 6.54 (s, 1H), 6.52 - 6.46 (m, 1H), 5.41 - 5.19 (m, 1H), 5.07 - 4.99 (m, 1H), 5.03 (dd, J=5.2, 13.2 Hz, 1H), 4.35 - 4.26 (m, 1H), 4.22 - 4.15 (m, 1H), 3.93 - 3.86 (m, 2H), 3.86 - 3.80 (m, 2H), 3.49 - 3.40 (m, 6H), 2.96 - 2.81 (m, 5H), 2.78 - 2.71 (m, 2H), 2.62 - 2.55 (m, 1H), 2.42 - 2.35 (m, 1H), |

FIG. 3B. Continued

| | | | |
|---|---|---|---|
| | | | 2.14 - 2.04 (m, 3H), 2.03 - 1.90 (m, 2H). |
| 600 | B | C | 1H NMR (400MHz, DMSO-d6) δ 10.92 (s, 1H), 8.69 (d, J = 2.4 Hz, 1H), 8.63 - 8.56 (m, 1H), 8.21 - 8.08 (m, 2H), 7.65 (d, J = 8.0 Hz, 2H), 7.63 (s, 1H), 7.48 (d, J = 8.8 Hz, 1H), 7.38 (d, J = 8.0 Hz, 2H), 7.31 - 7.21 (m, 1H), 6.68 - 6.59 (m, 2H), 5.39 - 5.20 (m, 1H), 5.06 - 4.98 (m, 1H), 4.36 - 4.26 (m, 1H), 4.19 (s, 1H), 3.52 - 3.45 (m, 2H), 3.42 - 3.35 (m, 8H), 3.27 - 3.24 (m, 2H), 2.93 - 2.78 (m, 3H), 2.77 - 2.69 (m, 3H), 2.65 - 2.57 (m, 2H), 2.56 (d, J = 2.0 Hz, 1H), 2.15 - 2.10 (m, 1H), 2.09 - 2.00 (m, 2H), 1.99 - 1.91 (m, 2H), 1.86 - 1.78 (m, 2H). |
| 601 | B | B | 1H NMR (400 MHz, DMSO-d6, ppm) δ 12.91 (s, 1H), 10.96 (s, 1H), 9.85 (s, 1H), 8.67 (s, 1H), 8.55 (s, 1H), 8.09 (s, 1H), 7.68-7.61(m, 4H), 7.26-7.19(m, 1H), 7.11(s, 1H), 7.08-7.06 (m, 3H), 5.25 (d, J = 32Hz, 1H), 5.05-5.01 (m, 1H), 4.37-4.20 (m, 2H), 4.17-4.14 (m, 4H), 3.48-3.41 (m, 4H), 2.92-2.90 (m, 1H), 2.75-2.73 (m, 4H), 2.62-2.54 (m, 7H), 2.45-2.33 (m, 2H), 2.20-1.95 (m, 4H). |
| 602 | A | C | 1H NMR (400MHz, DIMETHYLSULFOXIDE-d6) δ 13.45 - 12.26 (m, 1H), 10.97 (s, 1H), 8.64 (d, J = 2.0 Hz, 1H), 8.59 - 8.46 (m, 1H), 8.17 (s, 1H), 8.05 (s, 1H), 7.71 - 7.52 (m, 4H), 7.45 (s, 1H), 7.35 (d, J = 8.0 Hz, 1H), 7.25 (t, J = 8.8 Hz, 1H), 7.06 (d, J = 8.8 Hz, 2H), 5.41 - 5.19 (m, 1H), 5.09 (dd, J = 5.2, 13.2 Hz, 1H), 4.49 - 4.38 (m, 1H), 4.34 - 4.21 (m, 1H), 3.77 (d, J = 12.4 Hz, 4H), 3.56 (s, 5H), 3.03 - 2.84 (m, 3H), 2.77 - 2.65 (m, 3H), 2.57 (dd, J = 2.0, 8.0 Hz, 2H), 2.42 - 2.35 (m, 1H), 2.30 - 2.19 (m, 2H), 2.15 - 2.04 (m, 2H), 2.04 - 1.90 (m, 2H), 1.76 (dd, J = 1.6, 11.2 Hz, 2H), 1.60 - 1.46 (m, 1H), 1.38 - 1.17 (m, 3H). |
| 603 | A | B | 1H NMR (400 MHz, DMSO-d6) δ 12.90 (s, 1H), 10.98 (s, 1H), 9.95 (s, 1H), 9.84 (s, 1H), 8.62 (d, J = 1.6 Hz, 1H), 8.56 - 8.47 (m, 1H), 8.06 (d, J = 1.6 Hz, 1H), 7.69 (d, J = 7.6 Hz, 1H), 7.66 - 7.56 (m, 3H), 7.50 (s, 1H), 7.41 (d, J = 7.6 Hz, 1H), 7.31 - 7.23 (m, 1H), 6.60 (d, J = 8.4 Hz, 2H), 5.40 - 5.21 (m, 1H), 5.15 - 5.07 (m, 1H), 4.48 - 4.40 (m, 1H), 4.36 - 4.26 (m, 1H), 3.98 - 3.88 (m, 4H), 3.83 (d, J = 7.6 Hz, 1H), 3.42 - 3.37 (m, 3H), 3.34 - 3.25 (m, 2H), 3.18 (d, J = 6.4 Hz, 3H), 2.98 - 2.85 (m, 1H), 2.80 (t, J = 7.2 Hz, 2H), 2.64 - 2.57 (m, 1H), 2.44 - 2.36 (m, 2H), 2.31 - 2.21 (m, 1H), 2.18 - 2.05 (m, 2H), 2.03 - 1.96 (m, 3H). |
| 604 | A | A | 1H NMR (400 MHz, DMSO-d6, ppm) δ 10.93 (s, 1H), 8.72-8.60 (m, 2H), 8.11 (s, 1H),7.80-7.73 (m, 2H), 7.68- 7.51 (m, 4H), 7.31-7.20 (m, 1H), 7.09-7.01 (m, 2H), 5.45-5.01 (m, 2H), 5.04 (dd, J = 13.3, 5.2 Hz, 2H), 4.66 (s, 2H), 3.61-3.21 (m, 4H), 2.95-2.83 (m, 2H), 2.71-2.58 (m, 5H), 2.41-2.33 (m, 2H), 2.30-2.21 (m, 1H), 1.89-2.01 (m, 2H). |
| 605 | B | B | 1H NMR (300 MHz, DMSO-d6) δ 11.00 (s, 1H), 9.83 (s, 1H), 8.63 (s,1H), 8.62 (s,1H), 8.05 (s, 1H), 7.82 (s, 2H), 7.75-7.51 (m, 4H), 7.34-7.19 (m, 1H), 6.68-6.48 (m, 2H), 5.49-5.08 (m, 2H), 4.59-4.37 (m, 7H), 4.10 (s, 4H), 3.50 (s, 2H), 3.02-2.87 (m, 2H), 2.71-2.58 (m,1H), 2.48-2.37 (m, 2H), 2.18-1.97 (m, 4H), 1.23 (s, 1H). |

FIG. 3B. Continued

| | | | |
|---|---|---|---|
| 606 | B | C | 1H NMR (400MHz, DIMETHYLSULFOXIDE-d6) δ 12.99 (s, 1H), 10.94 (s, 1H), 9.85 (s, 1H), 9.81 - 9.71 (m, 1H), 8.69 (d, J = 2.0 Hz, 1H), 8.60 (s, 1H), 8.11 (s, 1H), 7.69 (d, J = 8.0 Hz, 2H), 7.63 (dt, J = 6.0, 9.2 Hz, 1H), 7.52 (d, J = 8.4 Hz, 1H), 7.38 (d, J = 8.4 Hz, 2H), 7.31 - 7.22 (m, 1H), 7.12 - 7.04 (m, 2H), 5.38 - 5.20 (m, 1H), 5.04 (dd, J = 5.2, 13.2 Hz, 1H), 4.47 - 4.38 (m, 1H), 4.36 - 4.28 (m, 1H), 4.25 - 4.14 (m, 3H), 4.05 (dd, J = 6.4, 10.8 Hz, 1H), 3.90 (d, J = 12.8 Hz, 2H), 3.43 - 3.36 (m, 3H), 3.29 (dt, J = 6.8, 9.9 Hz, 1H), 3.12 (t, J = 6.0 Hz, 2H), 2.96 - 2.80 (m, 3H), 2.79 - 2.71 (m, 1H), 2.64 - 2.55 (m, 2H), 2.47 - 2.34 (m, 3H), 2.16 - 2.05 (m, 2H), 1.97 (dd, J = 5.2, 10.4 Hz, 2H), 1.82 (dd, J = 3.6, 6.7 Hz, 1H), 1.79 - 1.69 (m, 2H), 1.36 - 1.21 (m, 2H). |
| 607 | A | C | 1H NMR (400MHz, DMSO-d6) δ 13.28 - 12.37 (m, 1H), 10.92 (s, 1H), 8.64 (d, J=2.0 Hz, 1H), 8.52 (br s, 1H), 8.21 (s, 1H), 8.05 (s, 1H), 7.66 - 7.54 (m, 3H), 7.49 (d, J=8.0 Hz, 1H), 7.22 (t, J=8.8 Hz, 1H), 7.05 (d, J=8.8 Hz, 2H), 6.57 - 6.46 (m, 2H), 5.38 - 5.19 (m, 1H), 5.03 (dd, J=5.2, 13.2 Hz, 1H), 4.34 - 4.27 (m, 1H), 4.22 - 4.15 (m, 1H), 4.12 (d, J=6.4 Hz, 1H), 3.86 (d, J=8.4 Hz, 2H), 3.80 (d, J=9.4 Hz, 3H), 3.58 (d, J=7.2 Hz, 1H), 3.45 (br s, 1H), 3.40 - 3.33 (m, 3H), 3.32 - 3.23 (m, 2H), 3.07 (d, J=6.0 Hz, 1H), 2.98 - 2.83 (m, 2H), 2.76 - 2.68 (m, 2H), 2.62 - 2.54 (m, 1H), 2.46 - 2.42 (m, 1H), 2.25 - 2.16 (m, 1H), 2.13 - 1.91 (m, 3H), 1.84 - 1.74 (m, 2H), 1.49 (br s, 1H), 1.32 - 1.18 (m, 2H), 1.15 (d, J=6.2 Hz, 3H). |
| 608 | B | C | 1H NMR (400 MHz, DMSO-d6) δ 12.94 (s, 1H), 10.98 (s, 1H), 8.67 (d, J=2.0 Hz, 1H), 8.56 (0s, 1H), 8.19 - 8.00 (m, 2H), 7.69 - 7.59 (m, 4H), 7.35 - 7.26 (m, 1H), 7.21 (d, J=3.2 Hz, 1H), 7.15 - 7.02 (m, 3H), 5.45 - 5.20 (m, 1H), 5.08 (dd, J=4.8, 13.2 Hz, 1H), 4.78 - 4.29 (m, 3H), 3.49 (s, 4H), 3.33 (d, J=6.8Hz, 4H), 3.12 - 2.86 (m, 6H), 2.60 (d, J=17.2 Hz, 1H), 2.56 - 2.52 (m, 1H), 2.45 - 2.36 (m, 1H), 2.19 (d, J=9.6 Hz, 1H), 2.15 - 2.06 (m, 2H), 2.05 - 1.92 (m, 3H), 1.85 - 1.65 (m, 3H), 1.58 - 1.37 (m, 2H). |
| 609 | B | C | 1H NMR (400MHz, DMSO-d6) δ 1.57 - 1.71 (m, 2 H) 1.90 - 2.04 (m, 2 H) 2.04 - 2.23 (m, 4 H) 2.36 - 2.45 (m, 3 H) 2.55 - 2.59 (m, 1 H) 2.58 (d, J=16.4 Hz, 1 H) 2.69 - 2.76 (m, 2 H) 2.84 - 2.98 (m, 1 H) 3.13 - 3.22 (m, 4 H) 3.23 - 3.29 (m, 2 H) 3.33 - 3.34 (m, 1 H) 3.34 - 3.50 (m, 1 H) 3.37 - 3.47 (m, 3 H) 4.23 - 4.34 (m, 1 H) 4.35 - 4.52 (m, 1 H) 5.05 - 5.16 (m, 1 H) 5.19 - 5.43 (m, 1 H) 6.56 - 6.72 (m, 2 H) 7.16 - 7.27 (m, 1 H) 7.32 - 7.38 (m, 1 H) 7.43 - 7.48 (m, 1 H) 7.52 (s, 4 H) 7.98 - 8.08 (m, 1 H) 8.43 - 8.56 (m, 1 H) 8.58 - 8.65 (m, 1 H) 9.72 (s, 1 H) 10.97 (s, 1 H) 12.76 - 12.98 (m, 1 H). |
| 610 | A | B | 1H NMR (400 MHz, CD3OD) δ 8.70 (s, 1H), 8.61 (d, J = 2.2 Hz, 1H), 7.90 (s, 1H), 7.77 (td, J = 8.9, 5.7 Hz, 1H), 7.65 – 7.58 (m, 2H), 7.20 – 7.11 (m, 3H), 7.06 (s, 1H), 6.96 (s, 1H), 5.30 (s, 1H), 5.19 – 5.06 (m, 2H), 4.49 – 4.31 (m, 2H), 3.96 (s, 3H), 3.85 (d, J = 12.3 Hz, 2H), 3.67 – 3.34 (m, 4H), 2.98 – 2.85 (m, 1H), 2.83 (s, 3H), 2.82 – 2.74 (m, 2H), 2.63 (s, 3H), 2.54 – 2.41 (m, 1H), 2.25 – 2.12 (m, 2H), 1.97 (d, J = 14.3 Hz, 6H), 1.47 (d, J = 12.2 Hz, 2H), 1.37 – 1.26 (m, 4H), 0.91 (t, J = 5.9 Hz, 1H). |

FIG. 3B. Continued

| | | | |
|---|---|---|---|
| 611 | A | B | 1HNMR (400 MHz, DMSO-d6) δ 12.90 (s, 1H), 10.98 (s, 1H), 9.84 (s, 1H), 8.66 (s, 1H), 8.54 (s, 1H), 8.07 (d, J = 2.8 Hz, 1H), 7.73 -7.57 (m, 6H), 7.27-7.25 (m, 1H), 7.09 (d, J = 8.4 Hz, 2H), 6.77-6.76 (m, 1H), 6.60 – 6.48 (m, 1H), 5.36-5.22 (d, J = 52.4 Hz, 1H), 5.13-5.10 (m, 1H), 4.48- 4.31 (q, 2H), 3.53-3.31 (m, 3H), 3.35 (s, 1H), 3.23 (s, 6H), 2.92-2.90 (m, 1H), 2.63-2.58 (m, 4H), 2.39-2..36 (m, 2H), 2.11-1.96 (m, 3H). |
| 612 | A | C | 1H NMR (400 MHz, DMSO-d6) δ 12.99 (d, J = 2.8 Hz, 1H), 10.92 (s, 1H), 9.86 (s, 1H), 9.64 - 9.54 (m, 1H), 8.71 (d, J = 2.0 Hz, 1H), 8.67 - 8.60 (m, 1H), 8.13 (d, J = 2.8 Hz, 1H), 7.73 (d, J = 8.4 Hz, 2H), 7.63 (dt, J = 6.4, 9.0 Hz, 1H), 7.42 (d, J = 8.0 Hz, 2H), 7.28 (t, J = 9.2 Hz, 1H), 6.70 (s, 1H), 6.59 (s, 1H), 5.40 - 5.19 (m, 1H), 4.98 (dd, J = 5.2, 13.6 Hz, 1H), 4.29 - 4.21 (m, 1H), 4.17 - 4.10 (m, 1H), 4.09 - 4.00 (m, 2H), 3.85 (s, 3H), 3.64 (d, J = 10.0 Hz, 2H), 3.41 (d, J = 2.4 Hz, 2H), 3.33 - 3.10 (m, 8H), 2.97 - 2.83 (m, 1H), 2.74 (t, J = 7.2 Hz, 2H), 2.62 - 2.53 (m, 1H), 2.36 - 2.29 (m, 1H), 2.16 - 2.01 (m, 4H), 1.97 - 1.88 (m, 1H). |
| 613 | D | | 1H NMR (300 MHz, DMSO-d6) δ 12.86 (s, 1H), 10.95 (s, 1H), 9.83 (s, 1H), 8.67 (s, 1H), 8.56 (s, 1H), 8.08 (s, 1H), 7.70-7.52 (m, 4H), 7.37-7.21 (m, 1H), 7.14-7.11 (m, 4H), 5.30 (d, J = 52.8 Hz, 1H), 5.09-5.06 (m, 1H), 4.41- 4.17 (q, 2H), 3.67-3.37 (m, 12H), 2.98-2.82 (m, 1H), 2.65 (s, 1H), 2.53- 2.27 (m, 1H), 2.11-1.99 (s, 3H). |
| 614 | D | B | 1H-NMR (300 MHz, DMSO-d6) δ 12.95 (s, 1H), 10.99 (s, 1H), 8.67 (d, J = 2.3 Hz, 1H), 8.57 (s, 1H), 8.10 (s, 1H), 7.79 – 7.44 (m, 5H), 7.26 (t, J = 8.7 Hz, 1H), 7.16 (d, J = 2.2 Hz, 1H), 7.05 (t, J = 8.7 Hz, 3H), 5.46 – 5.19 (m, 1H), 5.08 (dd, J = 13.3, 5.1 Hz, 1H), 4.39 (d, J = 17.2 Hz, 1H), 4.27 (d, J = 17.2 Hz, 1H), 4.01 (dt, J = 11.6, 5.4 Hz, 4H), 3.48 (d, J = 2.6 Hz, 3H), 3.39 (s, 9H), 2.99 – 2.85(m, 1H), 2.83 – 2.67 (m, 4H), 2.64 – 2.56(m, 1H), 2.44 – 2.20 (m, 1H), 2.18 – 1.92 (m, 3H). |
| 615 | D | C | 1H NMR (400MHz, DIMETHYLSULFOXIDE-d6) δ 12.96 (s, 1H), 10.94 (d, J = 2.4 Hz, 1H), 9.86 (s, 1H), 8.68 (t, J = 2.4 Hz, 1H), 8.58 (s, 1H), 8.08 (s, 1H), 7.73 - 7.58 (m, 3H), 7.55 - 7.41 (m, 1H), 7.27 (t, J = 8.4 Hz, 1H), 7.17 (dd, J = 4.0, 8.8 Hz, 2H), 6.78 - 6.69 (m, 1H), 6.57 - 6.46 (m, 1H), 5.41 - 5.18 (m, 1H), 5.03 (td, J = 4.8, 13.2 Hz, 1H), 4.36 - 4.25 (m, 1H), 4.21 - 4.13 (m, 1H), 4.11 - 4.01 (m, 2H), 3.97 (d, J = 9.0 Hz, 2H), 3.83 - 3.67 (m, 4H), 3.41 (s, 4H), 3.34 - 3.26 (m, 2H), 3.20 (s, 2H), 3.12 - 3.03 (m, 1H), 3.00 - 2.83 (m, 2H), 2.83 - 2.68 (m, 1H), 2.64 - 2.54 (m, 1H), 2.41 - 2.30 (m, 1H), 2.20 - 2.04 (m, 3H), 2.01 - 1.87 (m, 2H). |
| 616 | B | C | 1H NMR (400MHz, DMSO-d6) δ 12.88 (s, 1H), 10.93 (s, 1H), 8.64 (d, J=2.4 Hz, 1H), 8.52 (s, 1H), 8.16 (s, 1H), 8.06 (s, 1H), 7.67 - 7.55 (m, 3H), 7.49 (d, J=8.4 Hz, 1H), 7.25 (t, J=8.8 Hz, 1H), 7.05 (d, J=8.8 Hz, 2H), 6.54 (s, 1H), 6.50 (d, J=8.4 Hz, 1H), 5.40 - 5.19 (m, 1H), 5.03 (dd, J=5.2, 13.2 Hz, 1H), 4.36 - 4.26 (m, 1H), 4.21 - 4.15 (m, 1H), 4.12 (d, J=8.4 Hz, 1H), 3.86 (d, J=8.4 Hz, 2H), 3.77 (d, J=8.8 Hz, 3H), 3.60 (d, J=7.2 Hz, 1H), 3.47 (s, 1H), 3.39 (s, 2H), 3.12 (d, J=6.4 Hz, 1H), 2.97 (d, J=7.2 Hz, 1H), 2.95 - |

FIG. 3B. Continued

| | | | |
|---|---|---|---|
| | | | 2.89 (m, 1H), 2.95 - 2.83 (m, 2H), 2.77 - 2.68 (m, 2H), 2.63 - 2.54 (m, 1H), 2.45 - 2.35 (m, 1H), 2.27 - 2.18 (m, 1H), 2.14 - 2.04 (m, 2H), 2.01 - 1.91 (m, 2H), 1.84 - 1.74 (m, 2H), 1.50 (s, 1H), 1.32 - 1.19 (m, 2H), 1.16 (d, J=6.0 Hz, 3H). |
| 617 | B | C | 1H NMR (400MHz, DMSO-d6) δ 12.96 (s, 1H), 10.99 (s, 1H), 9.87 (s, 2H), 8.67 (d, J = 2.0 Hz, 1H), 8.58 (s, 1H), 8.10 (d, J = 2.4 Hz, 1H), 7.67 (dd, J = 3.6, 8.4 Hz, 3H), 7.64 - 7.59 (m, 1H), 7.32 - 7.24 (m, 1H), 7.22 - 7.12 (m, 3H), 7.10 - 6.99 (m, 1H), 5.39 - 5.20 (m, 1H), 5.16 - 5.04 (m, 1H), 4.72 (t, J = 6.4 Hz, 1H), 4.43 - 4.38 (m, 1H), 4.30 - 4.25 (m, 1H), 3.62 - 3.52 (m, 3H), 3.48 (s, 1H), 3.45 - 3.35(m, 3H), 3.33 - 3.25 (m, 1H), 3.17 - 3.09 (m, 2H), 3.07 - 2.97 (m, 4H), 2.93 - 2.87 (m, 1H), 2.64 - 2.56 (m, 2H), 2.47 - 2.39 (m, 2H), 2.18 - 2.05 (m, 2H), 2.03 - 1.95 (m, 1H). |
| 618 | C | B | 1H NMR (400 MHz, DMSO-d6) δ 10.95 (s, 1H), 8.69 (s, 1H), 8.59 (s, 1H), 8.29 (s, 2H), 8.08 (s, 1H), 7.69 (d, J=7.2 Hz, 2H), 7.59 (d, J=5.6 Hz, 1H), 7.48 (d, J=8.0 Hz, 1H), 7.42 (d, J=7.6 Hz, 2H), 7.17 (s, 1H), 6.63 - 6.33 (m, 2H), 5.44 - 5.14 (m, 1H), 5.02 (d, J=8.8 Hz, 1H), 4.39 - 4.11 (m, 2H), 4.01 (s, 8H), 3.62 (s, 1H), 3.00 - 2.79 (m, 1H), 2.59 (s, 2H), 2.34 (d, J=10.4 Hz, 3H), 2.18 - 1.86 (m, 5H). |
| 619 | C | C | 1H NMR (400 MHz, DMSO-d6) δ 12.95 - 12.80 (m, 1H), 10.98 (s, 1H), 10.13 - 9.51 (m, 1H), 8.61 (d, J = 2.0 Hz, 1H), 8.49 (s, 1H), 8.05 (s, 1H), 7.67 (d, J = 7.6 Hz, 1H), 7.61 (dt, J = 6.0, 9.1 Hz, 1H), 7.57 - 7.52 (m, 3H), 7.43 (d, J = 8.0 Hz, 1H), 7.25 (t, J = 8.8 Hz, 1H), 6.56 (d, J = 8.8 Hz, 2H), 5.38 - 5.20 (m, 1H), 5.11 (dd, J = 5.2, 13.3 Hz, 1H), 4.49 - 4.41 (m, 1H), 4.36 - 4.28 (m, 1H), 3.97 - 3.93 (m, 4H), 3.69 (s, 2H), 3.47 (s, 1H), 3.38 (s, 2H), 3.31 (s, 4H), 2.97 - 2.85 (m, 1H), 2.65 - 2.56 (m, 1H), 2.43 - 2.35 (m, 1H), 2.20 - 1.92 (m, 4H). |
| 620 | C | B | 1H NMR (400 MHz, DMSO-d6) δ 12.96 (s, 1H), 10.91 (s, 1H), 9.82 (s, 1H), 8.71 (d, J = 2.2 Hz, 1H), 8.61 (s, 1H), 8.11 (s, 1H), 7.71 (d, J = 7.9 Hz, 2H), 7.63 (td, J = 9.1, 5.9 Hz, 1H), 7.46 (dt, J = 8.3, 6.2 Hz, 3H), 7.27 (t, J = 8.5 Hz, 1H), 6.63 (d, J = 8.1 Hz, 2H), 5.36 (s, 1H), 5.23 (s, 0H), 5.03 (dd, J = 13.3, 5.1 Hz, 1H), 4.30 (d, J = 16.7 Hz, 1H), 4.18 (d, J = 16.7 Hz, 1H), 3.58 (s, 2H), 3.54 – 3.46 (m, 2H), 3.38 (t, J = 6.4 Hz, 4H), 3.21 (s, 2H), 2.97 – 2.83 (m, 2H), 2.58 (d, J = 17.9 Hz, 3H), 1.95 (d, J = 11.9 Hz, 2H), 1.89 (t, J = 6.9 Hz, 4H), 1.61 (s, 4H). |
| 621 | D | | 1H NMR (400 MHz, DMSO-d6) δ 12.92 (d, J=2.8 Hz, 1H), 10.95 (s, 1H), 9.85 (s, 1H), 9.69 (s, 1H), 8.63 (d, J=2.0 Hz, 1H), 8.53 (s, 1H), 8.08 (d, J=2.8 Hz, 1H), 7.68 - 7.49 (m, 4H), 7.28 (t, J=8.8 Hz, 1H), 7.14 - 7.02 (m, 2H), 6.62 (d, J=8.8 Hz, 2H), 5.46 - 5.18 (m, 1H), 5.05 (dd, J=5.2, 13.2 Hz, 1H), 4.43 (d, J=6.0 Hz, 2H), 4.38 - 4.27 (m, 3H), 4.23 (s, 1H), 4.13 (s, 2H), 4.01 (s, 2H), 3.92 (br d, J=12.4 Hz, 3H), 3.31 (dd, J=7.2, 10.4 Hz, 1H), 3.15 (s, 2H), 2.95 - 2.81 (m, 3H), 2.62 (s, 1H), 2.44 - 2.35 (m, 1H), 2.13 - 2.06 (m, 1H), 2.01 - 1.95 (m, 1H), 1.87 - 1.70 (m, 3H), 1.39 - 1.21 (m, 2H). |
| 622 | B | C | 1H NMR (400 MHz, DMSO-d6) δ 12.92 (d, J=2.8 Hz, 1H), 10.95 (s, 1H), 9.85 (s, 1H), 9.69 (s, 1H), 8.63 (d, J=2.0 Hz, 1H), 8.53 (s, 1H), 8.08 (d, J=2.8 Hz, 1H), 7.68 - 7.49 (m, 4H), 7.28 (t, J=8.8 Hz, 1H), |

FIG. 3B. Continued

| | | | |
|---|---|---|---|
| | | | 7.14 - 7.02 (m, 2H), 6.62 (d, J=8.8 Hz, 2H), 5.46 - 5.18 (m, 1H), 5.05 (dd, J=5.2, 13.2 Hz, 1H), 4.43 (d, J=6.0 Hz, 2H), 4.38 - 4.27 (m, 3H), 4.23 (s, 1H), 4.13 (s, 2H), 4.01 (s, 2H), 3.92 (br d, J=12.4 Hz, 3H), 3.31 (dd, J=7.2, 10.4 Hz, 1H), 3.15 (s, 2H), 2.95 - 2.81 (m, 3H), 2.62 (s, 1H), 2.44 - 2.35 (m, 1H), 2.13 - 2.06 (m, 1H), 2.01 - 1.95 (m, 1H), 1.87 - 1.70 (m, 3H), 1.39 - 1.21 (m, 2H). |
| 623 | | | 1H NMR (300 MHz, DMSO-d6, ppm) δ 12.90 (br,1H), 10.99 (br, 1H), 9.85 (br, 1H), 8.66 (s, 1H), 8.54 (s, 1H), 8.07 (s, 1H), 7.73-7.70 (d, J=7.8MHz, 1H), 7.67-7.59 (m, 4H), 7.52-7.50 (d, J=7.8MHz, 1H), 7.30-7.24 (m, 1H), 7.08-7.06 (d, J=8.7MHz, 2H), 5.38-5.21 (m, 1H), 5.16-5.09 (m, 1H), 4.51-4.31 (m, 2H), 3.68 (s, 2H), 3.50-3.40 (m, 4H), 3.24-3.10 (m, 4H), 2.97-2.86 (m, 1H), 2.63-2.59 (m, 5H), 2.43-2.35 (m, 1H), 2.14-1.98 (m, 3H). |
| 624 | | | 1H NMR (400MHz, DMSO-d6) δ 12.91 (s, 1H), 10.94 (s, 1H), 8.62 (d, J=2.0 Hz, 1H), 8.54 - 8.44 (m, 1H), 8.16 (s, 1H), 8.05 (s, 1H), 7.62 (dt, J=6.0, 8.8 Hz, 1H), 7.67 - 7.58 (m, 1H), 7.55 (d, J=8.8 Hz, 2H), 7.49 (d, J=8.8 Hz, 1H), 7.25 (t, J=8.0 Hz, 1H), 7.06 - 7.01 (m, 2H), 6.58 (d, J=8.8 Hz, 2H), 5.39 - 5.20 (m, 1H), 5.04 (dd, J=5.2, 13.2 Hz, 1H), 4.37 - 4.27 (m, 1H), 4.24 - 4.15 (m, 1H), 4.07 (d, J=7.6 Hz, 1H), 3.90 - 3.78 (m, 4H), 3.72 (d, J=8.0 Hz, 1H), 3.60 (d, J=7.6 Hz, 1H), 3.48 - 3.45 (m, 2H), 3.28 - 3.25 (m, 2H), 3.15 - 3.06 (m, 1H), 3.01 - 2.76 (m, 5H), 2.61 - 2.55 (m, 1H), 2.44 - 2.37 (m, 1H), 2.25 - 2.17 (m, 1H), 2.15 - 1.91 (m, 3H), 1.83 - 1.72 (m, 2H), 1.62 - 1.50 (m, 1H), 1.27 - 1.10 (m, 5H). |
| 625 | | | 1H NMR (400MHz, DMSO-d6) δ 12.88 (s, 1H), 10.94 (s, 1H), 8.62 (d, J=2.0 Hz, 1H), 8.50 (s, 1H), 8.16 (s, 1H), 8.05 (s, 1H), 7.67 - 7.58 (m, 1H), 7.55 (d, J=8.4 Hz, 2H), 7.50 (d, J=8.8 Hz, 1H), 7.25 (t, J=8.8 Hz, 1H), 7.08 - 7.00 (m, 2H), 6.58 (d, J=8.4 Hz, 2H), 5.38 - 5.21 (m, 1H), 5.04 (dd, J=5.2, 13.2 Hz, 1H), 4.36 - 4.27 (m, 1H), 4.23 - 4.16 (m, 1H), 4.07 (d, J=8.0 Hz, 1H), 3.91 - 3.78 (m, 4H), 3.75 - 3.70 (m, 1H), 3.601 - 3.57 (m, 1H), 3.47 (s, 1H), 3.42 -3.37 (m, 4H), 3.15 - 3.08 (m, 1H), 3.00 - 2.76 (m, 4H), 2.62 -2.55( m, 1H), 2.47 - 2.43 (m, 1H), 2.26 - 2.17 (m, 1H), 2.14 - 1.92 (m, 3H), 1.83 - 1.72 (m, 2H), 1.62 - 1.50 (m, 1H), 1.27 - 1.10 (m, 5H). |
| 626 | | | 1H NMR (400 MHz, DMSO-d6) δ 12.98 (s, 1H), 11.00 (s, 1H), 10.43 - 10.06 (m, 1H), 9.94 - 9.80 (m, 1H), 8.73 - 8.51 (m, 2H), 8.15 - 8.02 (m, 1H), 7.83 - 7.42 (m, 6H), 7.32 - 7.09 (m, 3H), 5.43 - 5.20 (m, 1H), 5.16 - 5.06 (m, 1H), 4.52 - 4.28 (m, 2H), 3.98 (d, J = 1.2 Hz, 3H), 3.59 - 3.38 (m, 5H), 3.34 - 3.06 (m, 7H), 2.73 - 2.57 (m, 2H), 2.45 - 2.30 (m, 2H), 2.09 - 1.94 (m, 2H). |
| 627 | | | 1H NMR (400MHz, DMSO-d6) δ 1.86 - 1.98 (m, 3 H) 2.03 - 2.27 (m, 2 H) 2.36 (dd, J=13.2, 4.40 Hz, 1 H) 2.46 (d, J=4.0 Hz, 6 H) 2.52 (d, J=1.6 Hz, 1 H) 2.53 - 2.57 (m, 1 H) 2.60 (s, 1 H) 2.73 (d, J=6.8 Hz, 2 H) 2.84 - 3.04 (m, 2 H) 3.38 - 3.42 (m, 3 H) 3.46 - 3.51 (m, 2 H) 4.17 - 4.24 (m, 1 H) 4.29 - 4.38 (m, 1 H) 4.50 - 4.62 (m, 1 H) 5.05 (dd, J=13.2, 4.8Hz, 1 H) 5.21 - 5.42 (m, 1 H) 6.95 - 7.11 (m, 4 H) 7.22 - 7.31 (m, 1 H) 7.52 (d, J=9.2 Hz, 1 H) 7.57 - 7.71 (m, 3 H) 8.06 - 8.12 (m, 1 H) 8.12 - 8.18 (m, 1 H) 8.50 - 8.59 (m, 1 H) 8.66 (d, J=2.0 Hz, 1 H) 10.87 - 10.98 (m, 1 H) 12.82 - 13.04 (m, 1 H). |

FIG. 3B. Continued

| | | | |
|---|---|---|---|
| 628 | | | 1H NMR (400 MHz, DMSO-d6) δ 13.04 - 12.96 (m, 1H), 10.94 (s, 1H), 9.85 (s, 1H), 9.35 - 9.22 (m, 1H), 8.75 - 8.67 (m, 1H), 8.66 - 8.55 (m, 1H), 8.12 (d, J = 2.4 Hz, 1H), 7.74 (d, J = 8.0 Hz, 2H), 7.68 - 7.58 (m, 1H), 7.50 (d, J = 8.0 Hz, 1H), 7.40 (d, J = 8.4 Hz, 2H), 7.28 (t, J = 8.4 Hz, 1H), 6.52 (s, 1H), 6.50 - 6.45 (m, 1H), 5.39 - 5.20 (m, 1H), 5.03 (dd, J = 4.8, 13.2 Hz, 1H), 4.36 - 4.27 (m, 1H), 4.23 - 4.13 (m, 1H), 4.00 (s, 2H), 3.85 (s, 2H), 3.54 - 3.50 (m, 2H), 3.50 - 3.46 (m, 2H), 3.42 - 3.37 (m, 2H), 3.34 - 3.25 (m, 2H), 3.24 - 3.18 (m, 2H), 3.13 - 3.03 (m, 2H), 2.96 - 2.84 (m, 2H), 2.73 - 2.67 (m, 1H), 2.63 - 2.56 (m, 1H), 2.46 - 2.38 (m, 2H), 2.16 - 2.10 (m, 2H), 2.08 - 2.02 (m, 2H), 1.99 - 1.90 (m, 3H). |
| 629 | | | 1H NMR (400 MHz, DMSO-d6) δ 12.97 - 12.84 (m, 1H), 11.09 - 10.93 (m, 1H), 9.85 (s, 1H), 8.62 (s, 1H), 8.57 - 8.42 (m, 1H), 8.15 - 7.97 (m, 1H), 7.79 - 7.70 (m, 1H), 7.69 - 7.60 (m, 1H), 7.59 - 7.51 (m, 2H), 7.49 - 7.39 (m, 1H), 7.35 - 7.20 (m, 1H), 6.64 - 6.57 (m, 1H), 5.37 - 5.22 (m, 1H), 5.17 - 5.07 (m, 1H), 4.49 - 4.41 (m, 1H), 4.40 - 4.26 (m, 4H), 4.11 - 4.00 (m, 3H), 3.63 - 3.53 (m, 6H), 3.41 - 3.35 (m, 3H), 3.34 - 3.27 (m, 1H), 3.00 - 2.91 (m, 2H), 2.69 - 2.58 (m, 3H), 2.33 (s, 1H), 2.11 (s, 1H), 2.04 - 1.95 (m, 1H). |
| 630 | | | 1H NMR (300 MHz, DMSO-d6) δ 10.98 (s, 1H), 8.65 (s, 1H), 8.54 (s, 1H), 8.06 (s, 1H), 7.76 – 7.68 (m, 2H), 7.59 (s, 5H), 7.25 (s, 1H), 7.10 (s, 2H), 5.46 – 5.01 (m, 2H), 4.30 – 4.48 (m, 2H), 3.66 (s, 2H), 3.38 (s, 5H), 3.12 (s, 1H), 2.90 (s, 1H), 2.74 (s, 4H), 2.59 (s, 2H), 2.39 (s, 1H), 2.07 (s, 4H). |
| 631 | | | 1H NMR (400 MHz, DMSO-d6, ppm):δ 12.89 (s, 1H), 10.98 (s, 1H), 9.85 (brs, 1H),8.65 (s, 1H), 8.53 (s, 1H), 8.06 (s, 1H), 7.68 (d, J = 7.9 Hz, 1H), 7.66-7.57 (m, 4H), 7.50 (d, J = 7.9 Hz, 1H), 7.26 (t, J = 8.7 Hz, 1H), 7.07 (d, J = 8.5 Hz, 2H), 5.40-5.21 (m, 1H), 5.15-5.05 (m, 1H), 4.80 (t, J = 6.3 Hz, 1H), 4.45 (d, J = 17.2 Hz, 1H), 4.32 (d, J = 17.2 Hz, 1H), 3.48-3.42 (m, 1H), 3.40-3.31 (m, 2H), 3.30-3.22 (m, 4H), 2.94-2.85 (m, 2H), 2.62-2.55 (m, 5H), 2.51-2.46 (m, 3H), 2.21-2.11 (m, 1H), 2.07-1.95 (m, 2H), 1.91-1.84 (m, 2H). |
| 632 | | | 1H NMR (400 MHz, DMSO-d6, ppm): δ 12.90 (s, 1H), 10.98 (s, 1H), 9.83 (s, 1H), 8.65 (s, 1H), 8.53 (s, 1H), 8.07 (s, 1H), 7.72-7.56 (m, 5H), 7.53-7.47 (m, 1H), 7.26-7.21 (m, 1H), 7.07 (d, J = 8.6 Hz, 2H), 5.61 (s, 1H), 5.41-5.29 (m, 1H), 5.18-5.11 (m, 1H), 4.80 (t, J = 6.2 Hz, 1H), 4.46 (d, J = 17.3 Hz, 1H), 4.32 (d, J = 17.2 Hz, 1H), 3.48 (s, 1H), 3.43-3.34 (m, 2H), 3.30-3.22 (m, 4H), 2.99-2.85 (m, 1H), 2.62-2.58 (m, 1H), 2.56-2.51(m, 4H), 2.48-2.40 (m, 3H), 2.43-2.36 (m, 2H), 2.20-1.95 (m, 2H), 1.89-1.81 (m, 2H). |
| 633 | | | 1H NMR (400 MHz, DMSO-d6) δ 12.96 (s, 1H), 10.95 (s, 1H), 8.64 (d, J=2.1 Hz, 1H), 8.52 (s, 1H), 8.45 (d, J=2.0 Hz, 1H), 8.16 (s, 1H), 8.10 (s, 1H), 7.93 (dd, J=2.4, 8.8 Hz, 1H), 7.63 (t, J=6.0, 9.2 Hz, 1H), 7.51 (d, J=8.8 Hz, 1H), 7.32 - 7.21 (m, 1H), 7.10 - 6.99 (m, 2H), 6.55 (d, J=8.8 Hz, 1H), 5.43 - 5.19 (m, 1H), 5.05 (dd, J=5.2, 13.2 Hz, 1H), 4.38 - 4.28 (m, 1H), 4.25 - 4.16 (m, 1H), 4.12 (s, 4H), 3.88 (d, J=12.4 Hz, 2H), 3.75 (s, 3H), 3.53 - 3.45 (m, 2H), 3.44 - 3.36 (m, 3H), 3.30 (t, J=6.8, 10.0 Hz, 2H), 3.06 |

FIG. 3B. Continued

| | | | |
|---|---|---|---|
| | | | - 2.78 (m, 3H), 2.67 - 2.56 (m, 3H), 2.43 - 2.31 (m, 1H), 2.19 - 1.93 (m, 3H), 1.75 (d, J=11.6 Hz, 2H), 1.63 (s, 1H), 1.30 - 1.14 (m, 2H). |
| 634 | | | 1H NMR (400 MHz, DMSO-d6, ppm) δ 12.89 (s, 1H), 10.98 (s, 1H), 8.70 (s, 1H),8.65 (brs, 1H), 8.10 (s, 1H), 7.71-7.60 (m, 5H), 7.58-7.51 (m, 1H), 7.32-7.22 (m, 1H), 7.10-7.02 (m, 2H), 5.40-5.21 (m, 1H), 5.15-5.05 (m, 1H), 4.80 (t, J = 6.3 Hz, 1H), 4.45 (d, J = 17.2 Hz, 1H), 4.32 (d, J = 17.2 Hz, 1H), 3.50-3.44 (m, 1H), 3.43-3.31 (m, 2H), 3.30-3.22 (m, 4H), 2.94-2.85 (m, 1H), 2.71-2.55 (m, 5H), 2.54-2.46 (m, 3H), 2.21-2.11 (m, 2H), 2.07-1.93 (m, 2H), 1.91-1.82 (m, 2H). |
| 635 | | | 1H NMR (400 MHz, DMSO-d6, ppm) δ 12.90 (s, 1H), 10.98 (s, 1H), 8.69 (s, 1H), 8.53 (s, 1H), 8.07 (s, 1H), 7.73-7.7.70 (m, 1H), 7.69-7.60 (m, 4H), 7.52-7.48 (m, 1H),7.29-7.22 (m, 1H), 7.06 (d, J = 8.6 Hz, 2H), 5.40-5.21 (m, 1H), 5.18-5.10 (m, 1H), 4.80 (t, J = 6.2 Hz, 1H), 4.46 (d, J = 17.3 Hz, 1H), 4.31 (d, J = 17.2 Hz, 1H), 3.51-3.48 (m, 1H), 3.47-3.34 (m, 3H), 3.30-3.22 (m, 4H), 2.99-2.85 (m, 1H), 2.70-2.61 (m, 5H), 2.58-2.41(m, 3H), 2.20-2.00 (m, 2H), 1.99-1.92 (m, 2H), 1.91-1.82 (m, 2H),1.25-1.10 (m, 1H). |
| 636 | | | 1H NMR (400 MHz, DMSO-d6) δ 12.92 (s, 1H), 10.91 (s, 1H), 9.85 (s, 1H), 9.73 (s, 1H), 8.63 (d, J = 2.0 Hz, 1H), 8.58 - 8.49 (m, 1H), 8.07 (s, 1H), 7.70 - 7.51 (m, 3H), 7.27 (t, J = 8.4 Hz, 1H), 6.70 - 6.55 (m, 3H), 6.49 (s, 1H), 5.39 - 5.20 (m, 1H), 5.00 - 4.93 (m, 1H), 4.26 - 4.20 (m, 1H), 4.13 - 4.08 (m, 1H), 4.02 - 3.90 (m, 8H), 3.84 (s, 3H), 3.48 (s, 1H), 3.44 - 3.36 (m, 3H), 3.34 - 3.28 (m, 1H), 3.26 - 3.19 (m, 1H), 3.17 - 3.10 (m, 2H), 2.87 (d, J = 12.0 Hz, 2H), 2.62 - 2.58 (m, 1H), 2.57 - 2.54 (m, 1H), 2.46 - 2.42 (m, 1H), 2.38 - 2.28 (m, 2H), 2.18 - 2.09 (m, 1H), 2.03 - 1.92 (m, 2H), 1.89 - 1.77 (m, 2H), 1.37 - 1.24 (m, 2H). |
| 637 | | | 1H NMR (400 MHz, DMSO-d6) δ 13.16 - 12.57 (m, 1H), 10.93 (s, 1H), 8.61 (d, J = 1.6 Hz, 1H), 8.49 (s, 1H), 8.16 (s, 1H), 8.04 (s, 1H), 7.66 - 7.58 (m, 1H), 7.57 - 7.47 (m, 3H), 7.26 (t, J = 8.8 Hz, 1H), 7.08 - 6.98 (m, 2H), 6.56 (d, J = 8.4 Hz, 2H), 5.38 - 5.20 (m, 1H), 5.03 (dd, J = 4.8, 13.2 Hz, 1H), 4.36 - 4.26 (m, 1H), 4.23 - 4.15 (m, 1H), 3.93 (s, 5H), 3.28 (s, 4H), 3.18 - 3.10 (m, 4H), 3.00 - 2.83 (m, 3H), 2.56 (s, 1H), 2.44 - 2.36 (m, 3H), 2.18 - 1.90 (m, 4H), 1.52 (t, J = 9.2 Hz, 2H), 1.40 - 1.29 (m, 2H), 0.98 - 0.92 (m, 3H). |
| 638 | | | 1H NMR (400MHz, DMSO-d6) δ 1.17 - 1.32 (m, 2 H) 1.85 (d, J=13.6 Hz, 2 H) 1.90 - 2.18 (m, 4 H) 2.33 - 2.44 (m, 3 H) 2.56 (s, 1 H) 2.59 - 2.64 (m, 1 H) 2.69 - 2.77 (m, 2 H) 2.79 - 3.02 (m, 6 H) 3.40 (d, J=2.8 Hz, 2 H) 3.48 (s, 1 H) 3.63 (s, 2 H) 3.85 - 3.95 (m, 2 H) 4.15 - 4.25 (m, 1 H) 4.27 - 4.39 (m, 1 H) 5.04 (dd, J=13.2, 5.2 Hz, 1 H) 5.20 - 5.41 (m, 1 H) 6.99 - 7.10 (m, 2 H) 7.17 - 7.33 (m, 2 H) 7.44 - 7.53 (m, 3 H) 7.63 (td, J=8.8, 6.0 Hz, 1 H) 8.10 (s, 1 H) 8.15 (s, 1 H) 8.53 - 8.63 (m, 1 H) 8.68 (d, J=2.0 Hz, 1 H) 10.93 (s, 1 H) 12.96 (d, J=3.2 Hz, 1 H). |
| 639 | | | 1H NMR (400 MHz, DMSO-d6) δ 12.89 (s, 1H), 11.07 (s, 1H), 9.85 (s, 1H), 8.62 (d, J=2.0 Hz, 1H), 8.50 (s, 1H), 8.06 (s, 1H), 7.69 - 7.52 (m, 4H), 7.34 - 7.18 (m, 3H), 6.57 (d, J=8.8 Hz, 2H), 5.41 - 5.20 |

FIG. 3B. Continued

| | | | |
|---|---|---|---|
| | | | (m, 1H), 5.07 (dd, J=5.6, 12.8 Hz, 1H), 4.04 (d, J=13.6 Hz, 2H), 3.94 (s, 4H), 3.48 (s, 1H), 3.42 - 3.34 (m, 6H), 3.29 - 3.25 (m, 1H), 3.04 - 2.87 (m, 3H), 2.64 - 2.55 (m, 2H), 2.33 (s, 1H), 2.19 - 1.98 (m, 4H), 1.77 (d, J=10.4 Hz, 2H), 1.59 (s, 1H), 1.21 - 1.12 (m, 2H). |
| 640 | | | 1H NMR (400 MHz, DMSO-d6) δ 13.08 - 12.92 (m, 1H), 10.94 (s, 1H), 8.75 (s, 2H), 8.64 (d, J = 2.4 Hz, 1H), 8.55 (s, 1H), 8.14 (s, 1H), 8.12 (s, 1H), 7.62 (dt, J = 5.6, 9.2 Hz, 1H), 7.50 (d, J = 8.8 Hz, 1H), 7.30 - 7.23 (m, 1H), 7.08 - 7.01 (m, 2H), 5.39 - 5.21 (m, 1H), 5.04 (dd, J = 5.2, 13.2 Hz, 1H), 4.35 - 4.28 (m, 1H), 4.26 - 4.16 (m, 5H), 3.87 (d, J = 12.8 Hz, 2H), 3.82 - 3.67 (m, 4H), 3.48 (s, 1H), 3.40 (s, 2H), 2.99 - 2.73 (m, 4H), 2.65 - 2.54 (m, 3H), 2.43 - 2.35 (m, 1H), 2.17 - 1.93 (m, 3H), 1.74 (d, J = 11.2 Hz, 2H), 1.69 - 1.55 (m, 1H), 1.22 (d, J = 10.0 Hz, 2H). |
| 641 | | | 1H NMR (400 MHz, DMSO-d6) δ 12.90 (s, 1H), 10.94 (s, 1H), 9.85 (s, 1H), 8.65 (m, 1H), 8.52 (s, 1H), 8.07 (s, 1H), 7.63 – 7.58 (m, 3H), 7.48 (m, 1H), 7.32 – 7.23 (m, 1H), 7.03 (s, 2H), 6.78 (m, 2H), 5.37 – 5.23 (m, 1H), 5.04 (m, 1H), 4.31 (m, 1H), 4.18 (m, 1H), 3.86 (m, 2H), 3.51 (m, 3H), 3.39 (m, 2H), 3.34 – 3.24 (m, 1H), 3.10 (m, 2H), 2.91 (m, 3H), 2.82 (m, 2H), 2.60 – 2.54 (s, 4H), 2.43 – 2.26 (m, 3H), 2.14 – 1.97 (m, 4H), 1.79 – 1.70 (m, 2H), 1.20 (m, 2H). |
| 642 | | | 1H NMR (400 MHz, DMSO-d6) δ 12.85 (s, 1H), 10.94 (s, 1H), 9.85 (s, 1H), 8.60 (d, J = 2.0 Hz, 1H), 8.46 (s, 1H), 8.03 (s, 1H), 7.62 (dt, J = 5.6, 8.8 Hz, 1H), 7.51 (d, J = 8.8 Hz, 1H), 7.34 (d, J = 8.4 Hz, 1H), 7.30 - 7.23 (m, 2H), 7.11 - 7.04 (m, 2H), 6.71 (d, J = 8.8 Hz, 1H), 5.39 - 5.18 (m, 1H), 5.03 (dd, J = 4.8, 13.2 Hz, 1H), 4.38 - 4.15 (m, 2H), 3.93 (d, J = 12.4 Hz, 2H), 3.33 - 3.26 (m, 3H), 3.20 (d, J = 6.8 Hz, 3H), 2.91 - 2.77 (m, 5H), 2.60 (s, 1H), 2.39 (dd, J = 3.6, 13.6 Hz, 1H), 2.17 - 1.85 (m, 7H), 1.79 (d, J = 12.8 Hz, 2H), 1.34 (d, J = 11.2 Hz, 2H). |
| 643 | | | 1H NMR (400 MHz, DMSO-d6) δ 13.14 - 12.80 (m, 1H), 10.91 (s, 1H), 8.70 (d, J = 2.0 Hz, 1H), 8.60 (s, 1H), 8.14 (s, 1H), 8.12 (s, 1H), 7.68 (d, J = 8.0 Hz, 2H), 7.63 (dd, J = 3.2, 9.2 Hz, 1H), 7.42 ( d, J = 8.0 Hz, 2H), 7.28 (t, J = 8.4 Hz, 1H), 6.63 (s, 1H), 6.51 (s, 1H), 5.40 - 5.21 (m, 1H), 4.97 (dd, J = 5.2, 13.2 Hz, 1H), 4.27 - 4.09 (m, 2H), 3.85 (s, 3H), 3.49 (s, 3H), 3.29 (s, 4H), 2.98 - 2.80 (m, 4H), 2.65 (s, 4H), 2.59 (d, J = 2.8 Hz, 1H), 2.57 - 2.53 (m, 2H), 2.34 - 2.26 (m, 1H), 2.19 - 2.06 (m, 2H), 1.97 - 1.87 (m, 1H). |
| 644 | | | 1H NMR (400MHz, DMSO-d6) δ 13.61 - 12.34 (m, 1H), 10.98 (s, 1H), 8.70 (s, 1H), 8.60 (s, 1H), 8.26 - 7.99 (m, 2H), 7.67 (t, J = 7.2 Hz, 4H), 7.50 (s, 1H), 7.41 (d, J = 6.0 Hz, 3H), 7.31 - 7.22 (m, 1H), 5.38 - 5.21 (m, 1H), 5.10 (dd, J = 4.4, 12.4 Hz, 1H), 4.45 - 4.28 (m, 2H), 3.40 (s, 2H), 3.31 (d, J = 8.8 Hz, 2H), 3.18 (d, J = 9.2 Hz, 3H), 3.01 - 2.80 (m, 4H), 2.71 (d, J = 5.6 Hz, 2H), 2.62 (s, 1H), 2.57 (s, 1H), 2.39 (d, J = 13.2Hz, 1H), 2.13 - 1.94 (m, 3H), 1.91 - 1.65 (m, 4H). |
| 645 | | | 1H NMR (400 MHz, DMSO-d6) δ 12.96 (s, 1H), 10.95 (s, 1H), 8.66 (s, 1H), 8.53 (s, 1H), 8.08 (s, 1H), 7.62 (d, J=5.6 Hz, 1H), 7.54 - 7.46 (m, 2H), 7.42 (d, J=8.8 Hz, 1H), 7.26 (t, J=8.8 Hz, 1H), 7.10 - 7.00 |

FIG. 3B. Continued

| | | | |
|---|---|---|---|
| | | | (m, 2H), 6.67 (t, J=8.8 Hz, 1H), 5.45 - 5.17 (m, 1H), 5.12 - 4.95 (m, 1H), 4.37 - 4.27 (m, 1H), 4.24 - 4.16 (m, 1H), 4.05 (s, 4H), 3.86 (d, J=12.4 Hz, 2H), 3.48 (s, 1H), 3.37 (s, 6H), 2.90 (s, 1H), 2.85 - 2.77 (m, 2H), 2.61 (s, 3H), 2.33 (s, 2H), 2.10 (d, J=14.4 Hz, 2H), 1.97 (s, 1H), 1.76 (d, J=11.2 Hz, 2H), 1.52 (s, 1H), 1.28 - 1.10 (m, 3H). |
| 646 | C | B | 1H NMR (400 MHz, DMSO-d6, ppm): δ 12.91 (br s, 1H), 11.09 (s, 1H), 9.85 (brs, 1H), 8.67 (d, J = 2.3 Hz, 1H), 8.56 (s, 1H), 8.07 (s, 1H), 7.78-7.47 (m, 4H), 7.35 (d, J = 2.2 Hz, 1H), 7.3-7.21 (m, 2H), 7.07 (d, J = 8.3 Hz, 2H), 5.42-5.18 (m, 1H), 5.11-5.00 (m, 1H), 4.08 (d, J = 12.5 Hz, 2H), 3.58 (s, 3H), 3.52-3.37 (m, 5H), 3.05 (t, J = 12.0 Hz, 2H), 2.96-2.78 (m, 1H), 2.70-2.54 (m, 5H), 2.24-1.94 (m, 3H), 1.89 (d, J = 12.5 Hz, 2H), 1.53 (d, J = 12.0 Hz, 2H), 0.98 (d, J = 6.2 Hz, 6H). |
| 647 | C | B | 1H NMR (400 MHz, DMSO-d6, ppm): δ 12.92 (brs, 1H), 11.08 (s, 1H), 9.85 (brs, 1H), 8.72 (s, 1H), 8.57 (s, 1H), 8.08 (s, 1H), 7.78-7.52 (m, 4H), 7.42-7.19 (m, 3H), 7.13 (d, J = 8.1 Hz, 2H), 5.45-5.15 (m, 1H), 5.11-5.02 (m, 1H), 4.09-4.01 (m, 2H), 3.59 (brs, 2H), 3.52-3.35 (m, 4H), 3.30-3.22 (m, 1H), 3.12-2.95 (m, 2H), 2.93-2.82 (m, 1H), 2.81-2.72 (m, 2H), 2.68-2.55 (m, 2H), 2.46-2.41 (m, 2H), 2.19-1.93 (m, 3H), 1.95-1.82 (m, 2H), 1.69-1.45 (m, 2H), 0.92 (d, J = 5.7 Hz, 6H). |
| 648 | D | | 1H NMR (400 MHz, DMSO-d6, ppm): δ 11.08 (s, 1H), 8.70 (d, J = 2.2 Hz, 1H), 8.54 (brs, 1H), 8.18-8.15 (m, 1H), 7.70-7.57 (m, 4H), 7.34-7.23 (m, 3H), 7.07-7.01 (m, 2H), 5.36-5.23 (m, 1H), 5.07-5.02 (m, 1H), 4.15-4.06 (m, 2H), 3.88 (s, 3H), 3.38-3.34 (m, 4H), 3.32-3.19 (m, 5H), 3.00 -2.82 (m, 4H), 2.70-2.62 (m, 4H), 2.63-2.57 (m, 2H), 2.16-2.05 (m, 3H), 1.99-1.86 (m, 2H), 1.72-1.50 (m, 2H). |
| 649 | B | B | 1H NMR (400 MHz, DMSO-d6) δ 12.93 (s, 1H), 11.09 (s, 1H), 9.87 (s, 1H), 8.77 - 8.40 (m, 2H), 8.08 (s, 1H), 7.77 - 7.51 (m, 4H), 7.27 (m, 1H), 7.10 (d, J=8.8 Hz, 2H), 6.82 (d, J=1.6 Hz, 1H), 6.68 (m, 1H), 5.42 - 5.17 (m, 1H), 5.06 (m, 1H), 4.15 (m, 2H), 3.94 (m, 2H), 3.48 (s, 1H), 3.40 (s, 3H), 3.31 - 3.19 (m, 5H), 2.97 - 2.77 (m, 1H), 2.62 - 2.54 (m, 6H), 2.19 - 1.88 (m, 3H). |
| 650 | D | | 1H NMR (400 MHz, DMSO- d6, ppm): δ12.94 (brs, 1H), 11.10 (s, 1H), 9.86 (brs, 1H), 8.67 (s, 1H), 8.57 (s, 1H), 8.10 (s, 1H), 7.74-7.67 (m, 3H), 7.66-7.59 (m, 2H), 7.37-7.32 (m, 2H), 7.27-7.22 (m, 1H), 7.13-7.10 (m, 2H), 5.35-5.15 (m, 1H), 5.11-5.02 (m, 1H), 4.22-4.15 (m, 2H), 3.48 (s, 1H), 3.43-3.40 (m, 2H), 3.31-3.25 (m, 4H), 2.94-2.81 (m, 3H), 2.73-2.70 (m, 5H), 2.64-2.54 (m, 1H), 2.16-2.00 (m, 3H). |
| 651 | D | | 1H NMR (400 MHz, DMSO- d6, ppm) δ 11.09 (s, 1H), 8.66 (s, 1H), 8.56 (s, 1H), 8.18 (s, 1H), 8.10 (s, 1H), 7.78-7.72 (m, 1H), 7.72-7.68 (m, 1H), 7.66-7.61 (m, 2H), 7.37-7.26 (m, 3H), 7.07-7.02 (m, 2H), 5.55-5.30 (m, 1H), 5.08-5.01 (m, 1H), 4.22-4.11 (m, 2H), 3.62-3.57 (m, 1H), 3.51-3.39 (m, 3H), 3.32-3.20 (m, 7H), 3.08-2.83 (m, 4H), 2.76-2.68 (m, 4H), 2.64-2.54 (m, 3H), 2.22-1.98 (m, 3H), 2.01-1.92 (m, 2H), 1.63-1.52 (m, 2H). |
| 652 | D | B | 1HNMR (300 MHz, DMSO-d6) δ 12.90 (s, 1H), 11.06 (s, 1H), 8.62 (s, 1H), 8.52 (s, 1H), 8.06 (s, 1H), 7.66-7.56 (m, 4H), 7.32 (s, 1H), 7.29-7.22 (m, 2H), 7.09-7.03 (m, 2H), 5.38-5.21 (d, J = 51.6Hz, 1H), |

FIG. 3B. Continued

| | | | |
|---|---|---|---|
| | | | 5.08-5.02 (m,1H), 3.72-3.58 (m, 9H), 3.54 (s, 1H), 3.49-3.33 (m, 7H), 3.21-3.04 (m, 5H), 2.91-2.82 (m, 2H), 2.59-2.53 (m, 12H), 2.27-1.99 (m, 3H). |
| 653 | C | C | 1H NMR (400MHz, DMSO-d6) δ 13.05 - 12.80 (m, 1H), 11.08 (s, 1H), 9.90 - 9.82 (m, 1H), 8.65 (d, J = 2.4 Hz, 1H), 8.59 - 8.52 (m, 1H), 8.10 - 8.05 (m, 1H), 7.77 (d, J = 8.4 Hz, 1H), 7.72 - 7.57 (m, 3H), 7.55 - 7.49 (m, 1H), 7.35 (d, J = 2.0 Hz, 1H), 7.32 - 7.24 (m, 1H), 6.64 (d, J = 3.6 Hz, 2H), 5.39 - 5.21 (m, 1H), 5.05 (d, J = 1.2 Hz, 1H), 4.28 - 4.09 (m, 6H), 3.48 (s, 4H), 3.31 - 3.20 (m, 4H), 2.60 (s, 1H), 2.52 (s, 4H), 2.20 - 1.92 (m, 4H). |
| 654 | D | C | 1H NMR (400 MHz, DMSO-d6) δ 11.17 (s, 1H), 8.68 -8.58 (m, 2H), 8.25-8.03 (m, 2H), 7.73-7.48 (m, 6H), 7.31 (s, 1H), 7.10 (s, 2H), 5.39-5.15 (m, 3H), 3.65-3.29 (m, 11H), 2.92-2.75 (m, 5H), 2.56-2.1026 (m, 6H), 1.85 -1.43 (m, 3 H), 1.27 (s, 3H). |
| 655 | D | C | 1H NMR (300 MHz, DMSO-d6) δ 12.08 (s, 1H), 11.07 (s, 1H), 8.64-8.53 (m, 2H), 8.06 (s, 1H), 7.65-7.57 (m, 4H), 7.33 (s, 1H), 7.26 (s, 2H), 7.07 (s, 2H), 5.38-5.20 (m, 1H), 5.05 (s, 1H), 3.56-3.54 (m, 8H), 3.36 -3.21 (m, 7H), 2.86-2.83(m, 2H) 2.59-2.50(m, 14H), 2.11-2.00 (m, 4H). |
| 656 | D | | 1H NMR (400 MHz, DMSO- d6, ppm): δ 11.09 (s, 1H), 8.71 (s, 1H), 8.56 (s, 1H), 8.25-8.22 (m, 1H), 7.73 (m, 1H), 7.72-7.64 (m, 3H), 7.39-7.22 (m, 3H), 7.10-7.03 (m, 2H), 7.45-5.35 (m, 1H), 5.15-5.08 (m, 1H), 4.16-4.10 (m, 2H), 3.89 (s, 3H), 3.58-3.55 (m, 1H), 3.49-3.42 (m, 3H), 3.41-3.39 (m, 1H), 3.22-3.18 (m, 7H), 3.05-2.95 (m, 2H), 2.89-2.82 (m, 1H), 2.71-2.64 (m, 4H), 2.58-2.55 (m, 3H), 2.24-1.96 (m, 3H), 1.91-1.85 (m, 2H), 1.60-1.51 (m, 2H). |
| 657 | D | C | 1H NMR (400 MHz, CD3OD, ppm) δ 12.98 (s, 1H), 11.04 (s, 1H), 9.82 (s, 1H), 8.65 (s, 1H), 8.64 (s, 1H), 8.05 (s, 1H), 7.62 -7.57 (m, 3H), 7.32 -7.30 (m, 1H), 7.07 (d, J = 8.8 Hz, 2H), 6.97 (s, 1H), 6.69 (s, 1H), 5.32 (d, J = 32.2 Hz, 1H), 5.02-5.00 (m, 1H), 3.93 (s, 3H), 3.82-3.78 (m, 2H), 3.49-3.46 (m, 5H), 3.38 - 3.33 (m, 4H), 2.92-2.76 (m, 3H), 2.55-2.51 (m, 2H), 2.24-2.21 (m, 3H), 2.20 – 1.90 (m, 4H), 1.86-1.83 (m, 3H),1.28-1.24 (m, 3H). |
| 658 | D | | 1HNMR (400 MHz, DMSO-d6, ppm): δ 13.00 (brs, 1H), 9.88 (brs, 1H), 8.99 (s, 1H), 8.71 (s, 1H), 8.59 (s, 1H), 8.46 (s, 1H), 8.13 (s, 1H), 7.76-7.73 (m, 1H), 7.70-7.63 (m, 1H), 7.47 -7.40 (m, 3H), 7.39-7.34 (m, 2H), 7.31-7.23 (m, 3H), 7.02-6.95 (m, 1H), 5.40-5.21 (m, 1H), 5.13 (s, 1H), 4.90 (t, J = 7.2 Hz, 1H), 4.54-4.36 (m, 2H), 4.28 (s, 1H), 4.16-4.05 (m, 2H), 3.65-3.59 (m, 2H), 3.48 (s, 1H), 3.44-3.39 (m, 2H), 3.37-3.20 (m, 9H), 3.31-3.25 (m, 1H), 3.09-2.86 (m, 2H), 2.46 (s, 3H), 2.08-2.01 (m, 3H), 1.94-1.84 (m, 3H), 1.76-1.71 (m, 1H), 1.38-1.35 (m, 3H), 0.94 (s, 9H). |
| 659 | D | C | 1H NMR (300 MHz, DMSO-d6, ppm) δ8.88 (s, 1H), 8.72 (s, 1H), 8.64 (s, 1H), 7.94 (s, 1H), 7.80-7.74 (m, 1H), 7.48-7.41 (m, 4H), 7.40-7.30 (m, 1H), 7.29-7.20 (m, 2H), 7.19-7.11 (m, 1H), 7.02-6.91 (m, 1H), 5.31-5.23 (m, 1H), 5.01-4.91 (m, 1H), 4.89-4.79 (m, 5H), 4.62-4.57 (m, 2H), 4.50-4.45 (m, 1H), 4.15-4.10 (m, 2H), 3.90-3.80 (m, 1H), 3.75-3.71 (m, 1H), 3.59-3.54 (m, 1H), 3.53-3.38 (m, 3H), 3.07 |

FIG. 3B. Continued

| | | | |
|---|---|---|---|
| | | | (s,2H),2.70-2.58 (m, 7H), 2.31-1.99 (m, 3H), 2.00-1.71 (m, 6H), 1.60-1.54 (m, 3H), 1.05 (s, 9H). |
| 660 | D | C | 1H NMR (400 MHz, CD3OD ) δ 8.86 (s, 1H), 8.69 (s, 1H), 8.59 (s, 1H), 7.89 (s, 1H), 7.75-7.73 (m, 1H), 7.59-7.57 (d, J=8.8 Hz, 2H), 7.44-7.39 (m, 4H), 7.12-7.07 (m, 3H), 5.29-5.14 (m, 1H), 5.01-4.91 (m, 1H), 4.80 (s, 1H), 4.65 (s, 1H), 4.60-4.58 (m, 1H), 4.44 (s, 1H), 3.92-3.83 (m, 1H), 3.77-3.76 (m, 1H), 3.56-3.39 (m, 4H), 3.25 (s, 4H), 2.73 (s, 4H), 2.47 (s, 3H), 2.37-2.26 (m, 3H), 2.19-2.12 (m, 3H), 2.05-1.89 (m, 2H), 1.72-1.56 (m, 6H), 1.53-1.50 (m, 4H), 1.06 (s, 9H). |
| 661 | D | C | 1H NMR (400 MHz, CD3OD ) δ 8.90 (s, 1H), 8.71 (s, 1H), 8.62 (s, 1H), 7.91 (s, 1H), 7.77-7.76 (m, 1H), 7.63-7.61 (d, J = 8.8 Hz, 2H), 7.49-7.43 (m, 4H), 7.16-7.11 (m, 3H), 5.29-5.14 (m, 1H), 5.01-4.91 (m, 1H), 4.65 (s, 1H), 4.60-4.58 (m, 1H), 4.44 (s, 1H), 3.92-3.83 (m, 1H), 3.77-3.76 (m, 1H), 3.59-3.37 (m, 4H), 3.32 (s, 4H), 2.83 (s, 4H), 2.58 (s, 3H), 2.41-2.29 (m, 1H), 2.29-2.12 (m, 4H), 2.08-1.89 (m, 4H), 1.96-61 (m, 3H), 1.51-1.50 (m, 3H), 1.45-1.26 (m, 4H), 1.08 (s, 9H). |
| 662 | D | B | 1H NMR (400MHz, DMSO-d6) δ 12.90 (s, 1H), 8.98 (s, 1H), 8.64 (d, J=2.0 Hz, 1H), 8.52 (s, 1H), 8.44 (d, J=7.6 Hz, 1H), 8.16 (s, 1H), 8.06 (s, 1H), 7.74 (d, J=10.0 Hz, 1H), 7.67 - 7.55 (m, 3H), 7.48 - 7.41 (m, 2H), 7.37 (d, J=8.4 Hz, 2H), 7.26 (t, J=8.4 Hz, 1H), 7.05 (d, J=8.8 Hz, 2H), 5.43 - 5.20 (m, 1H), 4.90 (t, J=7.2 Hz, 1H), 4.51 (d, J=10.0 Hz, 1H), 4.44 (t, J=8.0 Hz, 1H), 4.28 (s, 1H), 3.63 - 3.53 (m, 5H), 3.49 - 3.45 (m, 2H), 3.29 - 3.25 (m, 4H), 3.07 - 2.99 (m, 1H), 2.93 - 2.78 (m, 3H), 2.64 - 2.58 (m, 1H), 2.46 (s, 3H), 2.43 - 2.39 (m, 3H), 2.21 - 1.94 (m, 6H), 1.83 - 1.73 (m, 3H), 1.39 (d, J=7.2 Hz, 3H), 1.22 - 1.14 (m, 2H), 1.13 - 1.07 (m, 6H), 0.94 (s, 9H). |
| 663 | D | A | 1H-NMR: (400 MHz, CD3OD, ppm) δ 8.87 (s, 1H), 8.64 (s, 1H), 8.52 (s, 1H), 7.90 (s, 1H), 7.75-7.74 (m, 1H), 7.46-7.40 (m, 5H), 7.15-7.12 (m, 1H), 6.92-6.82 (m, 2H), 5.30-5.15 (m, 1H), 5.02-5.00 (m, 1H), 4.63-4.58 (m, 2H), 4.44-4.39 (m, 1H), 3.85-3.75 (m, 2H), 3.57-3.41 (m, 5H), 3.35-3.32 (m, 2H), 3.05 (s, 2H), 3.00-2.97 (m, 2H), 2.79-2.77 (m, 4H), 2.47 (s, 3H), 2.26-2.12 (m, 6H), 1.99-1.93 (m, 4H), 1.70-1.59 (m, 2H), 1.52-1.50 (d, J=7.2Hz, 3H), 1.06-1.03 (m, 9H). |
| 664 | D | A | 1H NMR (400MHz, DMSO-d6) δ 12.89 (s, 1H), 8.98 (s, 1H), 8.65 (d, J=2.4 Hz, 1H), 8.53 (s, 1H), 8.43 (d, J=7.6 Hz, 1H), 8.17 (d, J=3.2 Hz, 1H), 8.06 (s, 1H), 7.72 (d, J=9.6 Hz, 1H), 7.66 - 7.53 (m, 3H), 7.45 - 7.41 (m, 2H), 7.39 - 7.32 (m, 2H), 7.26 (t, J=8.8 Hz, 1H), 7.07 (d, J=8.8 Hz, 2H), 5.41 - 5.20 (m, 1H), 4.95 - 4.84 (m, 1H), 4.54 - 4.40 (m, 2H), 4.28 (s, 1H), 3.63 - 3.53 (m, 3H), 3.39 (d, J=2.8 Hz, 3H), 3.22 (s, 5H), 3.05 (d, J=16.0 Hz, 2H), 2.97 - 2.87 (m, 2H), 2.54 (s, 5H), 2.45 (s, 6H), 2.37 (s, 5H), 2.18 - 2.00 (m, 3H), 1.83 - 1.71 (m, 1H), 1.65 (d, J=7.2 Hz, 2H), 1.38 (d, J=7.2 Hz, 3H), 0.94 (s, 9H). |
| 665 | D | | 1H NMR (400 MHz, DMSO-d6, ppm): δ 8.98 (s, 1H), 8.80-8.60 (m, 1H), 8.60-8.40 (m, 2H), 8.01 (s, 1H), 7.80-7.76 (m, 1H), 7.65-7.51 (m, 3H), 7.50-7.20 (m, 4H),7.20-7.00 (m, 3H), 5.43-5.00 (m, 2H),5.00-4.80 (m, 1H), 4.60-4.39 (m, 2H), 4.28 (s, 1H), 3.90-3.78 (m, 2H), 3.70-3.50 (m, 2H), 3.10-2.60 (m, 11H), 2.50-1.70 (m, 11H), 1.55-1.10 (m, 9H), 0.94 (s, 9H). |

FIG. 3B. Continued

| | | | |
|---|---|---|---|
| 666 | B | C | 1H NMR (400MHz, DMSO-d6) δ 12.88 (s, 1H), 8.97 (s, 1H), 8.64 (s, 1H), 8.51 (s, 1H), 8.42 (d, J=6.8 Hz, 1H), 8.04 (s, 1H), 7.72 - 7.61 (m, 2H), 7.57 (d, J=8.4 Hz, 2H), 7.47 - 7.37 (m, 4H), 7.24 (t, J=8.8 Hz, 1H), 7.05 (d, J=8.4 Hz, 2H), 5.41 - 5.19 (m, 2H), 5.15 (s, 1H), 4.91 - 4.77 (m, 2H), 4.51 (d, J=7.6 Hz, 2H), 4.28 (s, 2H), 3.88 - 3.54 (m, 5H), 3.12 - 2.63 (m, 7H), 2.45 (s, 4H), 2.35 - 2.01 (m, 6H), 1.80 (s, 3H), 1.57 (s, 1H), 1.29 - 1.09 (m, 3H), 1.02 (d, J=5.4 Hz, 6H), 0.95 (s, 11H). |
| 667 | B | C | 1H NMR (400MHz, DMSO-d6) δ 12.90 (s, 1H), 9.84 (s, 1H), 8.98 (s, 1H), 8.64 (d, J=2.1 Hz, 1H), 8.53 (s, 1H), 8.41 (d, J=7.0 Hz, 1H), 8.06 (s, 1H), 7.72 (s, 1H), 7.67 - 7.55 (m, 3H), 7.51 - 7.33 (m, 4H), 7.27 (t, J=8.4 Hz, 1H), 7.06 (d, J=7.6 Hz, 1H), 7.11 - 7.02 (m, 1H), 5.38 - 5.21 (m, 1H), 5.12 (d, J=3.2 Hz, 1H), 4.90 - 4.73 (m, 2H), 4.55 - 4.41 (m, 2H), 4.29 (s, 1H), 3.83 (s, 2H), 3.67 - 3.53 (m, 4H), 3.48 (s, 1H), 3.43 - 3.33 (m, 5H), 3.23 - 2.84 (m, 4H), 2.67 (s, 4H), 2.46 (s, 3H), 2.36 (s, 2H), 2.15 - 1.73 (m, 8H), 1.52 (s, 1H), 1.40 - 1.13 (m, 3H), 1.01 (s, 4H), 0.95 (s, 9H). |
| 668 | D | | 1H NMR (400 MHz, DMSO- d6, ppm) δ 12.91 (brs, 1H), 9.87 (brs, 1H), 9.00 (s, 1H), 8.65 (s, 1H), 8.58-8.43 (m, 2H), 8.07 (s, 1H), 7.85 (s, 1H), 7.72-7.53 (m, 4H), 7.30-7.23 (m, 1H), 7.09-6.92 (m, 4H), 5.40-5.12 (m, 2H), 4.99-4.91 (m, 1H), 4.56-4.34 (m, 3H), 3.87 (s, 3H), 3.80-3.76 (m, 2H), 3.65-3.55 (m, 2H), 3.48 (s, 1H), 3.44-3.40 (m, 2H), 3.32-3.28 (m, 1H), 3.10-3.05 (m, 1H), 2.93-2.86 (m, 1H), 2.75-2.68 (m, 2H), 2.56-2.52 (m, 2H), 2.48-2.43 (m, 3H), 2.42-2.36 (m, 2H), 2.20-1.87 (m, 7H), 1.75-1.61 (m, 3H), 1.31 (s, 3H), 1.26-1.15 (m, 3H), 0.96 (s, 1H), 0.86 (s, 9H). |
| 669 | D | | 1H NMR (300 MHz, DMSO-d6, ppm): δ 12.92 (brs, 1H), 9.83 (brs, 1H),9.01 (s, 1H), 8.72-8.61 (m, 1H), 8.60-8.45 (m, 2H), 8.09 (s, 1H), 7.82-7.71 (m, 1H), 7.70-7.45 (m, 3H), 7.36-7.20 (m, 3H), 7.09-6.92 (m, 3H), 5.40-5.18 (m, 1H), 5.15 (s, 1H), 5.00-4.81 (m, 1H), 4.58-4.42 (m, 2H), 4.41-4.25 (m, 1H), 3.92 (s, 3H), 3.85-3.70 (m, 2H), 3.68-3.50 (m, 2H), 3.49-3.36 (m, 3H), 3.30-3.24 (m, 2H), 3.08-2.85(m, 2H), 2.84-2.62 (m, 2H), 2.48-2.32 (m, 4H), 2.31-2.22 (m, 3H), 2.20-1.85 (m, 7H), 1.80-1.53 (m, 4H), 1.46-1.35 (m, 3H), 1.28-1.05 (m, 3H), 0.98-0.79 (m, 9H). |
| 670 | D | B | 1H NMR (400MHz, DMSO-d6) δ 12.90 (s, 1H), 9.83 (s, 1H), 9.01 - 8.91 (m, 1H), 8.63 (d, J=2.4 Hz, 1H), 8.52 (s, 1H), 8.38 (d, J=7.6 Hz, 1H), 8.06 (s, 1H), 7.74 - 7.53 (m, 3H), 7.51 - 7.42 (m, 2H), 7.41 - 7.35 (m, 2H), 7.33 - 7.22 (m, 1H), 6.61 (d, J=8.4 Hz, 2H), 5.38 - 5.17 (m, 1H), 4.97 - 4.85 (m, 1H), 4.55 (d, J=9.2 Hz, 1H), 4.43 (t, J=8.0 Hz, 1H), 4.34 - 4.22 (m, 1H), 4.06 (s, 2H), 3.78 (s, 1H), 3.72 - 3.67 (m, 4H), 3.41 - 3.34 (m, 9H), 3.33 - 3.25 (m, 4H), 2.47 - 2.42 (m, 5H), 2.18 - 1.94 (m, 4H), 1.86 - 1.74 (m, 1H), 1.38 (d, J=6.8 Hz, 3H), 1.06 - 0.88 (m, 9H). |
| 671 | D | B | 1H NMR (400MHz, DMSO-d6) δ 12.78 (s, 1H), 8.65 (d, J=2.0 Hz, 1H), 8.53 (s, 1H), 8.44 (d, J=7.6 Hz, 1H), 8.15 (s, 2H), 8.06 (s, 1H), 7.77 (d, J=8.8 Hz, 1H), 7.70 - 7.56 (m, 9H), 7.45 (t, J=7.6 Hz, 2H), 7.40 - 7.32 (m, 4H), 7.26 (t, J=8.8 Hz, 1H), 7.07 (d, J=8.8 Hz, 2H), 5.38 - 5.20 (m, 1H), 4.95 - 4.85 (m, 1H), 4.50 (d, J=10.0 Hz, 1H), 4.45 (t, J=8.0 Hz, 1H), 3.23 - 3.18 (m, 8H), 3.07 - 3.00 (m, 1H), 2.92 - 2.82 (m, |

FIG. 3B. Continued

| | | | |
|---|---|---|---|
| | | | 3H), 2.27 - 2.18 (m, 3H), 2.18 - 1.96 (m, 7H), 1.82 - 1.67 (m, 4H), 1.64 - 1.45 (m, 2H), 1.39 (d, J=6.8 Hz, 3H), 1.28 - 1.07 (m, 3H), 0.94 (s, 11H). |
| 672 | D | | 1H NMR (300 MHz, CD3OD) 8.87 (d, J = 5.7 Hz, 1H), 8.68 (s, 1 H), 8.59 (s, 1H), 7.89 (s, 1H), 7.74 (s, 2H), 7.72-7.58 (m, 4H), 7.38-7.37 (m, 1H), 7.16-7.05 (m, 3H), 5.31 (s, 1H), 4.96-4.95 (m, 1H), 4.86-4.84 (m, 1H), 4.68-4.66 (m, 1H), 3.86-3.52 (m, 4H), 3.51-3.36 (m, 4H), 3.01 (s, 2H), 2.86 (s, 2H), 2.53-2.31(m, 14H), 2.26-2.02 (m, 6H), 1.90-1.71 (m, 4H), 1.70-1.68 (m, 2H), 1.35-1.21 (m, 2H), 1.09-0.84 (m, 9H). |
| 673 | D | B | 1H NMR (400 MHz, DMSO-d6, ppm): δ 8.98 (s, 1H), 8.67 (d, J=2.2 Hz, 1H), 8.55 (brs, 1H), 8.38 (d, J=8.2 Hz, 1H), 8.07 (s, 1H), 7.90 (d, J=9.2 Hz, 1H), 7.67-7.57 (m, 3H), 7.50-7.32 (m, 4H), 7.26 (t, J = 8.8 Hz, 1H), 7.21-7.16 (m, 4H), 6.95 (d, J = 8.4 Hz, 2H), 5.36 -5.23 (m, 1H), 4.91-4.82 (m, 1H), 4.53-4.43 (m, 2H), 4.31-4.20 (m, 1H), 3.67-3.59 (m, 4H), 3.59- 3.54 (m, 2H), 3.51-3.42(m, 5H), 3.40-3.36 (m, 7H), 3.36-3.21 (m, 4H), 2.50-2.43(m, 3H), 2.20-2.06 (m, 2H), 2.05-1.95 (m, 1H),1.90-1.81 (m, 1H), 0.92 (s, 9H). |
| 674 | D | A | 1H NMR (300 MHz, DMSO-d6, ppm) δ 12.90 (brs, 1H), 9.83 (brs, 1H), 8.99 (s, 1H), 8.65 (s, 1H), 8.61-8.51 (m, 2H), 8.07 (s, 1H), 7.80-7.71 (m, 1H), 7.70-7.60 (m, 3H), 7.32-7.23 (m, 2H), 7.11-6.98 (m, 3H), 6.90 (s, 1H), 5.38 (s, 1H), 5.24-5.12 (m, 1H), 5.00-4.90 (m, 1H), 4.55-4.46 (m, 1H), 4.41-4.20 (m, 4H), 3.87-3.57 (m, 4H), 3.48 (s, 1H), 3.47-3.38 (m, 7H), 3.15-3.07 (m, 1H), 2.96-2.87 (m, 1H), 2.80-2.62 (m , 2H), 2.50-2.45 (m,5H), 2.25-1.88 (m, 9H), 1.85-1.62 (m, 3H), 1.30-1.02 (m, 2H), 0.94 (s, 9H). |
| 675 | D | A | 1H NMR (400 MHz, DMSO-d6) δ 12.91 (s, 1H), 9.87 (s, 1H), 9.01 (s, 1H), 8.66 (d, J = 2.3 Hz, 1H), 8.56 – 8.49 (m, 2H), 8.08 (s, 1H), 7.85 (d, J = 9.7 Hz, 1H), 7.61-7.56 (m, 4H), 7.45 (d, J = 2.0 Hz, 1H), 7.35 (dd, J = 7.9, 2.0 Hz, 1H), 7.31 – 7.22 (m, 1H), 7.06 (d, J = 8.6 Hz, 2H), 5.36 (s, 1H), 5.23–5.16 (d, J = 3.4 Hz, 1H), 4.54-4.51 (m, 5H), 4.37 (s, 1H), 4.28-4.27 (m, 1H), 3.67-3.65 (m, 2H), 3.60 (d, J = 10.8 Hz, 1H), 3.48 (d, J = 2.3 Hz, 6H), 3.19 (s, 4H), 2.91 (d, J = 16.2 Hz, 2H), 2.84 (s, 2H), 2.47 (d, J = 4.2 Hz, 6H), 2.19 – 2.01 (m, 8H), 1.96 – 1.85 (m, 2H), 1.76 (t, J = 17.0 Hz, 1H), 1.56 (s, 1H), 1.23-1.19 (m, 2H), 0.95 (s, 9H). |
| 676 | D | B | 1H NMR (300 MHz, DMSO-d6) δ 12.91 (s, 1H), 9.86 (s, 1H), 9.01 (s, 1H), 8.65-8.0 (d, J = 2.2 Hz, 1H), 8.57 – 8.47 (m, 2H), 8.07 (s, 1H), 7.83 (d, J = 9.7 Hz, 1H), 7.63-7.54 (m, 4H), 7.47 (d, J = 2.0 Hz, 1H), 7.39 – 7.20 (m, 2H), 7.06 (d, J = 8.7 Hz, 2H), 5.38 (s, 1H), 5.23 – 5.12 (m, 1H), 4.59 (s, 2H), 4.46-4.21 (m, 5H), 3.64 – 3.61 (m, 4H), 3.60 – 3.50 (m, 3H), 3.49 – 3.33 (m, 4H), 3.30 – 3.29 (m, 5H), 3.26 – 3.18 (m, 4H), 2.92 (s, 1H), 2.83-2.81 (m, 2H), 2.46-2.44 (m, 5H), 2.18 – 2.09 (d, J = 8.9 Hz, 7H), 1.91-1.9 (m, 1H), 1.73-1.71-1.365 (m, 2H), 1.56-1.52 (m, 1H), 1.21-1.16 (m, 2H), 0.94 (s, 9H). |
| 677 | D | | 1H NMR (400 MHz, DMSO-d6) δ 8.99 (s, 1H), 8.64 (s 1H), 8.52 (s, 1H), 8.28 (s, 1H), 8.05 (s, 1H), 7.72 (s, 1H), 7.66 – 7.54 (m, 3H), 7.48 (s 2H), 7.42 (s, 2H), 7.22 (s, 1H), 7.05 (s, 2H), 5.29 (s, 1H), 5.13 (s, |

FIG. 3B. Continued

| | | | |
|---|---|---|---|
| | | | 1H), 4.71 – 4.62 (m, 1H), 4.57 (s, 1H), 4.46 (s, 1H), 4.35 (s, 1H), 3.76 (s, 2H), 3.66 – 3.52 (m, 2H), 3.45 (s, 1H), 3.40 – 3.35 (m, 3H), 3.31 – 3.21 (m, 3H), 3.03 (s, 1H), 2.89 (s, 1H), 2.71 (s, 2H), 2.37 (s, 8H), 2.19 – 1.85 (m, 7H), 1.75 (s, 2H), 1.67 (s, 1H), 1.19 (s, 2H), 0.83 (d, J = 24.8 Hz, 15H). |
| 678 | D | | 1H NMR (400 MHz, CD3OD ) δ 8.99 (s, 1H), 8.70-8.61 (m, 3H), 7.94-7.91 (m, 2H), 7.76 (d, J = 5.6 Hz, 1H), 7.61 (d, J = 8.8 Hz, 2H), 7.50 (d, J = 8.0 Hz, 1H), 7.16-7.13 (m, 3H), 5.09-5.08 (d, J = 7.2 Hz, 1H), 4.66-4.62 (m, 2H), 4.51-4.42 (m, 1H), 3.93-3.79 (m, 4H), 3.62-3.41 (m, 5H), 3.01 (s, 2H), 2.81-2.75 (m, 2H), 2.64-2.53 (m, 11H), 2.33-1.91 (m, 8H), 1.75 (s, 1H), 1.63-1.56 (m, 3H), 1.40-1.37 (m, 2H), 1.05 (s, 9H). |
| 679 | D | A | 1H NMR (400 MHz, DMSO-d6, ppm) δ 12.90 (brs, 1H), 9.86 (brs, 1H), 9.01 (s, 1H), 8.65 (s, 1H), 8.58-8.48 (m, 2H), 8.06 (s, 1H), 7.83-7.78 (m, 1H), 7.66-7.53 (m, 4H), 7.47 (s, 1H), 7.35-7.31 (m, 1H), 7.28-7.23 (m, 1H), 7.10-7.06 (m, 2H), 5.41-5.29 (m, 1H), 5.16 (s, 1H), 4.60 (s, 2H), 4.52-4.41 (m, 3H), 4.41-4.37 (m, 1H), 4.31-4.28 (m, 1H), 3.70-3.37 (m, 13H), 3.30-3.21 (m, 8H), 3.02-2.98 (m, 1H), 2.94-2.80 (m, 3H), 2.52-2.46 (m, 6H), 2.22-2.02 (m, 7H), 2.01-1.85 (m, 2H), 1.83-1.68 (m, 2H), 1.56-1.50 (m, 1H), 1.30-1.15 (m, 2H), 0.95 (s, 9H). |
| 680 | D | B | 1H NMR (400 MHz, DMSO-d6) δ 12.90 (s, 1H), 10.2-9.7(m,1H), 8.98 (s, 1H), 8.64 (s, 1H), 8.90-8.30 (m, 3H), 8.06 (s, 1H), 7.90-7.70(m, 1H), 7.70-7.55 (m, 3H), 7.55-7.30 (m, 4H), 7.35-7.20 (m, 1H), 7.20-7.00 (m, 2H), 5.30-5.10(m,1H), 5.10-4.80 (m,1H), 4.55-4.44 (m,2H), 4.40-4.20 (m, 1H),3.90-3.80(m,2H), 3.80-3.60(m, 2H)3.70-3.55(m,6H), 3.25-3.15(m, 5H),3.10-3.00(m,1H), 2.90-2.65 (m, 9H),2.50-2.40 (m, 3H), 2.30-2.00 (m, 5H), 1.92-1.45 (m, 9H), 1.45-1.40 (m, 2H), 1.10-0.80 (s, 9H). |
| 681 | D | A | 1H NMR (400 MHz, DMSO-d6) δ (ppm) 9.44 (s, 1H), 9.33 (s, 1H), 8.90 (s, 1H), 8.56 (s, 2H), 7.92 (s, 1H), 7.78-7.77 (m, 1H), 7.50-7.42 (m, 4H), 7.16-7.10 (m, 1H), 5.32-5.19 (m, 1H), 4.66-4.53 (m, 4H), 4.40-4.36 (m, 1H), 3.90-3.83 (m, 2H), 3.60-3.40 (m, 4H), 3.37-3.33 (m, 3H), 3.07(s, 2H), 2.93-2.80 (m, 2H), 2.60 (m, 4H), 2.50 (s, 3H), 2.29-2.11 (m, 8H), 1.85-1.60 (m, 3H), 1.36-1.30 (m, 3H), 1.07 (s, 9H). |
| 682 | D | B | 1H NMR (400MHz, DMSO-d6) δ 8.97 (s, 1H), 8.68 (d, J=2.4 Hz, 1H), 8.57 (br s, 1H), 8.43 (d, J=7.2 Hz, 1H), 8.22 (s, 2H), 8.08 (s, 1H), 7.76 (d, J=10.0 Hz, 1H), 7.65 - 7.52 (m, 2H), 7.50 (d, J=8.0 Hz, 1H), 7.45 - 7.41 (m, 2H), 7.41 - 7.37 (m, 2H), 7.22 (s, 1H), 7.14 (t, J=8.8 Hz, 1H), 5.38 - 5.20 (m, 1H), 4.87 - 4.81 (m, 1H), 4.55 - 4.44 (m, 2H), 4.29 (s, 1H), 3.69 - 3.55 (m, 3H), 3.09 (s, 4H), 2.90 (d, J=16.0 Hz, 3H), 2.68 (d, J=1.6 Hz, 4H), 2.45 (s, 3H), 2.29 - 2.03 (m, 9H), 1.98 (s, 1H), 1.92 - 1.72 (m, 4H), 1.56 - 1.40 (m, 3H), 0.95 (s, 9H). |
| 683 | D | B | 1H NMR (300 MHz, CD3OD ) δ 8.88-8.87 (d, J=3.3 Hz, 1H), 8.690 (s, 1H), 8.61-8.60 (d, J=2.1 Hz, 1H), 7.90 (s, 1H), 7.78-7.76 (d, J=6.0 Hz, 1H), 7.61-7.58 (d, J=8.4Hz, 2H), 7.47-7.41 (m, 4H), 7.15-7.12 (d, J=9.0 Hz, 3H), 5.31-5.01 (m, 2H), 4.72 (s, 1H), 4.67-4.52 (m, 1H), 4.45 (s, 1H), 4.15 (s, 1H), 3.95-3.76 (m, 5H), 3.60-3.42 (m, 5H), 3.25-3.11 (m, 1H), 2.83-2.71 (m, 2H), 2.49 (s, 3H), 2.33-2.11 (m, |

FIG. 3B. Continued

| | | | |
|---|---|---|---|
| | | | 11H), 2.05-1.90 (m, 4 H), 2.72 (s, 1H), 1.61-1.25 (m, 5H), 1.08-1.06 (d, J=5.4 Hz, 9H). |
| 684 | D | B | 1H NMR (300 MHz, CD3OD ) δ 8.88 (s, 1H), 8.69 (s, 1H), 8.61 (s, 1H), 7.90 (s, 1H), 7.77-7.75 (d, J=6.0 Hz, 1H), 7.60-7.58 (d, J=8.4Hz, 2H), 7.46 (s, 4H), 7.17-7.11 (m, 3H), 5.324-5.03 (m, 2H), 4.73 (s, 1H), 4.66-4.51 (m, 1H), 4.48 (s, 1H), 4.15 (s, 1H), 3.96-3.78 (m, 8H), 3.67-3.31 (m, 5H), 3.18-3.01 (m, 1H), 2.87-2.70 (m, 2H), 2.49 (s, 3H), 2.28-2.11 (m, 11H), 2.09-1.87 (m, 4 H), 2.71 (s, 1H), 1.37-1.33 (d, J=11.7 Hz, 2H), 1.08(s, 9H). |
| 685 | D | C | 1H NMR (300 MHz, DMSO-d6) δ 12.89 (s, 1H), 10.00-9.01 (m, 1H), 8.73-8.62 (m, 1H), 8.61-8.51 (m, 1H), 8.50-8.34 (m, 1H), 8.19-7.98 (m, 3H), 7.73-7.60 (m, 3H), 7.56-7.32 (m, 5H), 7.30-7.11 (m, 3H), 6.98-6.80(m, 1H), 5.45-5.32 (m, 1H), 5.26-5.14 (m, 1H), 5.13-5.08 (m, 1H), 5.00-4.69 (m, 2H), 4.60-4.41 (m, 2H), 4.40-4.30 (m, 2H), 3.72-3.53 (m, 11H), 2.50-2.48 (m, 4H), 2.33-2.20 (m, 1H), 2.18-2.09 (m, 1H),2.08-1.93 (m, 2H),1.90-1.71 (m, 2H), 1.30-1.21 (m, 1H), 1.12-1.02 (m, 1H),1.00-0.83 (m, 9H). |
| 686 | D | C | 1H NMR (400 MHz, DMSO-d6) δ 12.96 (s, 1H), 9.85 (s, 1H), 8.98 (s, 1H), 8.82 - 8.69 (m, 1H), 8.67 (d, J = 2.1 Hz, 1H), 8.58 (s, 1H), 8.40 (d, J = 7.6 Hz, 1H), 8.08 (s, 1H), 7.74 - 7.54 (m, 3H), 7.45 - 7.36 (m, 3H), 7.30 - 7.24 (m, 1H), 7.20 - 7.05 (m, 2H), 5.42 - 5.16 (m, 1H), 4.91 (t, J = 7.2 Hz, 1H), 4.56 (d, J = 9.2 Hz, 1H), 4.42 (t, J = 8.0 Hz, 1H), 4.30 (s, 1H), 4.09 - 3.86 (m, 6H), 3.65 - 3.53 (m, 7H), 3.52 - 3.23 (m, 13H), 3.18 - 2.93 (m, 4H), 2.46 - 2.41 (m, 3H), 2.18 - 1.95 (m, 3H), 1.93 - 1.73 (m, 4H), 1.48 (d, J = 7.0 Hz, 2H), 1.37 (d, J = 7.0 Hz, 2H), 1.03 - 0.87 (m, 9H). |
| 687 | D | | 1H NMR (300 MHz, CD3OD) δ 8.92 (s, 1H), 8.69 (s,1H), 8.59 (s, 1H), 7.89 (s, 1H), 7.79-7.71 (m, 1H), 7.57 (d, J = 8.7Hz, 2H), 7.41-7.39 (m, 1H), 7.12-7.09 (m, 3H), 7.10-7.00 (m, 1H), 6.91 (d, J=1.5Hz, 1H), 5.51-5.61 (m, 1H), 5.38-5.09 (m, 1H), 4.89-4.74 (m, 1H), 4.74-4.50 (s, 2H), 4.49-4.47 (m, 3H), 3.86-3.79 (m, 1H), 3.79-3.75 (m, 3H), 3.67-3.50 (m, 2H), 3.49-3.39 (m, 3H), 3.01 (s, 2H), 2.75-2.59 (m, 2H), 2.59-2.48 (m, 7H), 2.35-2.18 (m, 3H), 2.18-2.08 (m, 3H), 2.08-1.92 (m, 1H), 1.92-1.88 (m, J=12Hz, 2H), 1.86-1.65 (m, 1H), 1.37-1.28 (m, 3H), 1.06-1.00 (s, 9H). |
| 688 | D | C | 1H NMR (300 MHz, CD3OD): δ 8.89 (s, 1H), 8.68 (s, 1H), 8.59 (s, 1H), 7.89 (s, 1H), 7.76-7.74 (m, 1H), 7.59-7.51 (m, 3H), 7.19-7.09 (m, 3H), 7.09-6.99 (m, 1H), 6.99-6.90 (m, 1H), 5.69-5.50 (m, 1H), 5.39-5.06 (s, J=75Hz, 1H), 4.89-4.71 (m, 1H), 4.63 (s, 1H), 4.50-4.41 (m, 2H), 4.36-4.28 (m, 1H), 3.90-3.73 (m, 4H), 3.49-3.66 (m, 2H), 3.49-3.31 (m, 3H), 3.12-2.98 (m, 2H), 2.81-2.59 (m, 3H), 2.59-2.49 (m, 7H), 2.35-2.18 (m, 4H), 2,16-1.95 (m, 3H), 1.92-1.83 (m, 2H), 1.68-1.65 (m, 1H), 1.42-1.20 (m, 3H), 0.96 (s, 9H). |
| 689 | C | B | 1H NMR (400 MHz, DMSO-d6) δ 12.98 (s, 1H), 9.86 (s, 1H), 8.99 (s, 1H), 8.70 (s, 1H), 8.60 (s, 1H), 8.46 (s, 1H), 8.12 (s, 1H), 7.76 (s, 1H), 7.68 – 7.54 (m, 2H), 7.51 (s, 1H), 7.48 – 7.41 (m, 2H), 7.38 (s, 2H), 7.28 (s, 1H), 7.16 (s, 1H), 5.31 (s, 1H), 5.14 (s, 1H), 5.01 (s, 1H), 4.91 (s, 1H), 4.53 (s, 1H), 4.49 (s, 1H), 4.44 (s, 1H), 4.29 (s, 1H), 3.58 (s, 2H), 3.49 (s, 1H), 3.41 (s, 3H), 3.31 (s, 2H), 3.10 (s, 5H), 2.85 (s, |

FIG. 3B. Continued

| | | | |
|---|---|---|---|
| | | | 3H), 2.68 (s, 3H), 2.46 (s, 3H), 2.25 (s, 2H), 2.08 (s, 4H), 1.77 (s, 3H), 1.58 (s, 1H), 1.39 (s, 3H), 1.23 (s, 2H), 0.95 (s, 9H). |
| 690 | D | A | 1H NMR (400 MHz, DMSO-d6, ppm): δ 12.97 (brs, 1H), 9.86 (brs, 1H), 8.99 (s, 1H), 8.71 (s, 1H), 8.65-8.60 (m, 1H), 8.51-8.46 (m, 1H), 8.11 (s, 1H),7.80-7.74 (m, 1H), 7.71-7.63 (m, 1H), 7.62-7.56 (m, 1H), 7.55-7.51 (m, 1H), 7.49-7.44 (m, 2H), 7.43-7.38 (m, 2H), 7.36-7.27 (m, 1H), 7.22-7.16 (m, 1H), 5.40-5.20 (m, 1H), 5.18-5.11 (m, 1H), 4.95-4.82 (m, 1H), 4.55-4.50 (m, 1H), 4.49-4.45 (m, 1H), 4.32-4.21 (m, 1H), 3.71-3.62 (m, 2H), 3.60-3.48 (m, 1H), 3.47-3.39 (m, 4H), 3.38-3.35 (m, 1H), 3.34-3.31 (m, 1H), 3.30-3.27 (m, 1H), 3.10-3.06 (m, 1H), 2.99-2.89 (m, 1H), 2.80-2.71 (m, 3H), 2.70-2.46 (m, 5H), 2.36-2.31 (m, 1H), 2.26-2.23 (m, 2H), 2.17-2.03 (m, 3H), 1.98-1.94 (m, 1H), 1.87-1.72 (m, 3H), 1.69-1.60 (m, 1H), 1.39-1.21 (m, 3H), 1.36-1.22 (m, 2H), 0.95 (s, 10H). |
| 691 | D | A | 1H NMR (400MHz, DMSO-d6) δ: 12.98 (s, 1H), 9.85 (s, 1H), 9.01 - 8.98 (m, 1H), 8.71 (d, J=2.0 Hz, 1H), 8.62 (s, 1H), 8.38 (d, J=8.0 Hz, 1H), 8.11 (d, J=2.8 Hz, 1H), 7.72 (d, J=8.4 Hz, 2H), 7.67 - 7.58 (m, 1H), 7.51 - 7.33 (m, 4H), 7.32 - 7.19 (m, 3H), 5.37 - 5.22 (m, 1H), 4.92 - 4.83 (m, 1H), 4.58 (d, J=8.8 Hz, 1H), 4.49 (t, J=8.4 Hz, 1H), 4.32 (s, 1H), 4.20 - 4.03 (m, 3H), 3.93 - 3.75 (m, 5H), 3.63 - 3.55 (m, 8H), 3.38 - 3.31 (m, 4H), 3.18 - 3.00 (m, 1H), 2.52 - 2.51(m, 4H), 2.46 (s, 3H), 2.17 - 1.95 (m, 4H), 1.90 - 1.78 (m, 1H), 1.13 - 0.91 (m, 15H). |
| 692 | D | B | 1H NMR (400MHz, DMSO-d6) δ: 12.98 (s, 1H), 9.85 (s, 1H), 8.99 (s, 1H), 8.71 (d, J=2.4 Hz, 1H), 8.62 (s, 1H), 8.39 (d, J=7.6 Hz, 1H), 8.11 (s, 1H), 7.72 (d, J=8.8 Hz, 1H), 7.69 - 7.59 (m, 3H), 7.47 - 7.42 (m, 2H), 7.41 - 7.33 (m, 2H), 7.27 (t, J=8.8 Hz, 1H), 7.15 (d, J=8.4 Hz, 2H), 5.43 - 5.21 (m, 1H), 5.11 (s, 1H), 4.97 - 4.85 (m, 1H), 4.55 - 4.42 (m, 2H), 4.29 (s, 1H), 3.65 - 3.57 (m, 3H), 3.50 - 3.47 (m, 2H), 3.08 - 2.99 (m, 2H), 2.94 - 2.78 (m, 3H), 2.64 - 2.60 (m, 1H), 2.46 (s, 3H), 2.32 - 2.23 (m, 3H), 2.23 - 2.06 (m, 7H), 2.05 - 1.95 (m, 1H), 1.82 - 1.71 (m, 3H), 1.65 - 1.45 (m, 2H), 1.43 - 1.35 (m, 3H), 1.27 - 1.13 (m, 2H), 0.99 - 0.92 (m, 15H). |
| 693 | D | B | 1H NMR (400MHz, DMSO-d6) δ 12.92 (s, 1H), 9.82 (s, 1H), 9.02 - 8.95 (m, 1H), 8.68 (d, J=2.0 Hz, 1H), 8.56 (s, 1H), 8.43 (d, J=7.6 Hz, 1H), 8.07 (s, 1H), 7.76 (d, J=10.0 Hz, 1H), 7.68 - 7.58 (m, 3H), 7.48 - 7.36 (m, 4H), 7.27 (t, J=8.8 Hz, 1H), 7.10 (d, J=8.8 Hz, 2H), 5.39 - 5.20 (m, 1H), 5.14 (d, J=3.6 Hz, 1H), 4.89 - 4.75 (m, 2H), 4.55 - 4.46 (m, 2H), 4.33 - 4.21 (m, 1H), 3.67 - 3.52 (m, 6H), 3.49 - 3.39 (m, 4H), 3.32 - 3.21 (m, 2H), 3.11 - 3.00 (m, 1H), 2.95 - 2.83 (m, 2H), 2.52 - 2.51 (m, 4H), 2.47 - 2.45 (m, 3H), 2.30 - 2.03 (m, 5H), 1.93 - 1.72 (m, 3H), 1.59 - 1.37 (m, 2H), 1.02 - 0.90 (m, 15H). |
| 694 | D | B | 1H NMR (400MHz, DMSO-d6) δ 9.00 - 8.95 (m, 1H), 8.66 - 8.60 (m, 1H), 8.55 - 8.47 (m, 1H), 8.47 - 8.40 (m, 1H), 8.16 (s, 1H), 8.07 - 8.01 (m, 1H), 7.82 - 7.74 (m, 1H), 7.66 - 7.60 (m, 1H), 7.59 - 7.53 (m, 2H), 7.48 - 7.35 (m, 5H), 7.30 - 7.21 (m, 1H), 6.94 - 6.83 (m, 2H), 5.38 - 5.19 (m, 1H), 4.92 - 4.78 (m, 2H), 4.57 - 4.44 (m, 2H), 4.34 - 4.25 (m, 1H), 3.66 - 3.58 (m, 6H), 3.09 - 3.02 (m, 3H), 2.96 - 2.85 (m, |

FIG. 3B. Continued

| | | | |
|---|---|---|---|
| | | | 4H), 2.83 - 2.71 (m, 2H), 2.46 (s, 5H), 2.27 - 2.14 (m, 3H), 2.14 - 2.00 (m, 4H), 1.86 - 1.69 (m, 4H), 1.65 - 1.44 (m, 3H), 1.08 (d, J = 4.4 Hz, 6H), 0.98 - 0.93 (m, 9H). |
| 695 | D | C | 1H NMR (400 MHz, DMSO-d6) δ 13.11 - 12.65 (m, 1H), 9.04 - 8.93 (m, 1H), 8.66 (d, J=2.4 Hz, 1H), 8.54 (s, 1H), 8.45 (d, J=8.0 Hz, 1H), 8.17 (s, 1H), 8.08 (s, 1H), 7.74 (d, J=9.6 Hz, 1H), 7.67 - 7.60 (m, 3H), 7.47 - 7.42 (m, 2H), 7.42 - 7.37 (m, 2H), 7.26 (t, J=8.4 Hz, 1H), 7.09 (d, J=8.8 Hz, 2H), 5.41 - 5.20 (m, 1H), 5.15 (s, 1H), 4.91 - 4.80 (m, 2H), 4.55 - 4.47 (m, 2H), 4.29 (s, 1H), 3.97 (d, J=10.0 Hz, 1H), 3.75 (s, 2H), 3.68 (d, J=12.0 Hz, 3H), 3.65 - 3.57 (m, 7H), 3.48 (s, 7H), 3.09 (s, 1H), 3.05 (s, 1H), 2.95 (s, 1H), 2.91 (s, 1H), 2.78 - 2.69 (m, 1H), 2.46 (s, 6H), 2.09 (dd, J=5.2, 13.6 Hz, 3H), 1.79 (d, J=4.8, 8.8, 12.9 Hz, 1H), 0.95 (s, 9H). |
| 696 | D | | 1H NMR (400 MHz, DMSO-d6) δ 12.94 (d, J=3.0 Hz, 1H), 9.87 (s, 1H), 9.00 (s, 1H), 8.68 (d, J=2.0 Hz, 1H), 8.58 (s, 1H), 8.40 (d, J=8.0 Hz, 1H), 8.09 (d, J=2.4 Hz, 1H), 7.70 - 7.59 (m, 3H), 7.49 - 7.42 (m, 2H), 7.42 - 7.36 (m, 2H), 7.28 (t, J=8.8 Hz, 1H), 7.11 (d, J=9. Hz, 2H), 5.38 - 5.22 (m, 1H), 4.90 - 4.82 (m, 1H), 4.55 (d, J=9.6 Hz, 1H), 4.48 (t, J=8.1 Hz, 1H), 4.31 (s, 1H), 4.03 (br d, J=8.4 Hz, 3H), 3.80 - 3.56 (m, 2H), 3.30 (t, J=6.8, 9.8 Hz, 8H), 3.20 (d, J=18.8 Hz, 8H), 2.85 - 2.75 (m, 1H), 2.53 (d, J=2.0 Hz, 7H), 2.46 (s, 4H), 2.17 - 1.93 (m, 3H), 1.86 - 1.75 (m, 1H), 1.00 - 0.92 (m, 9H). |
| 697 | D | | 1H NMR (400 MHz, DMSO-ppm) δ 12.94 (s, 1H), 11.11 (s, 1H), 9.87 (s, 1H), 8.67 (d, J=2.2 Hz, 1H), 8.57 (s, 1H), 8.09 (s, 1H), 7.90-7.81 (m, 1H), 7.69-7.57 (m,4H), 7.50 (d, J=7.2 Hz, 1H), 7.26 (t, J=8.8 Hz, 1H), 7.15 (d, J=8.6 Hz, 2H), 5.36-5.23 (m, 2H) , 4.62 (d, J=5.2 Hz, 2H), 4.45 (d, J=4.3 Hz, 2H), 3.67-3.45 (m,2H), 3.25 (m, 1H),2.88(m,1H) ,2.67(m,2H),2.09 (m, 3H), 1.24 (m, 1H). |
| 698 | D | | 1H NMR (400 MHz, DMSO-ppm) δ 12.91 (s, 1H), 11.12 (s, 1H), 9.86 (s, 1H), 8.65 (d, J=2.2 Hz, 1H), 8.07 (s, 1H), 7.87 (m, 1H),7.79 (m, 1H), 7.60 (m, 4H), 7.47 (d, J=7.3 Hz, 1H), 7.26 (m, 1H), 7.08 (d, J= 8.6 Hz, 2H), 5.23-5.10 (m, 2H), 4.46(m,2H),3.47 (m,2H), 2.91-2.82 (m, 2H), 2.74 (m,4H), 2.60 (m, 10H), 2.06 (m,2H). |
| 699 | B | C | 1H NMR (400MHz, DMSO-d6) δ 12.87 (s, 1H), 11.07 (s, 1H), 8.64 (d, J=2.4 Hz, 1H), 8.52 (s, 1H), 8.23 (s, 1H), 8.04 (s, 1H), 7.65 (d, J=8.4 Hz, 1H), 7.61 - 7.53 (m, 3H), 7.33 (s, 1H), 7.26 - 7.15 (m, 2H), 7.07 (d, J=8.8 Hz, 1H), 7.10 - 7.04 (m, 1H), 5.37 - 5.20 (m, 1H), 5.07 (dd, J=5.2, 12.8 Hz, 1H), 3.82 (s, 2H), 3.56 - 3.41 (m, 2H), 3.26 - 3.25 (m, 2H), 3.04 - 2.98 (m, 3H), 2.91 - 2.85 (m, 1H), 2.80 - 2.71 (m, 3H), 2.63 - 2.59 (m, 2H), 2.28 - 2.15 (m, 1H), 2.14 - 1.94 (m, 3H), 1.91 - 1.79 (m, 2H), 1.75 (s, 2H), 1.70 - 1.53 (m, 1H), 1.33 - 1.10 (m, 3H), 1.01 (d, J=6.4 Hz, 6H). |
| 700 | A | B | 1H NMR (400 MHz, DMSO-d6) δ 12.95 (br s, 1H), 10.93 (s, 1H), 9.85 (s, 1H), 8.68 (d, J = 2.0 Hz, 1H), 8.58 (br s, 1H), 8.10 (br s, 1H), 7.78 - 7.68 (m, 2H), 7.67 - 7.59 (m, 1H), 7.51 (d, J = 8.2 Hz, 1H), 7.32 - 7.24 (m, 2H), 6.65 - 6.43 (m, 2H), 5.45 - 5.15 (m, 2H), 5.08 - 5.01 (m, 1H), 4.53 - 4.41 (m, 1H), 4.36 - 4.27 (m, 1H), 4.24 - 4.10 (m, 3H), 3.87 - 3.68 (m, 4H), 3.49 (s, 1H), 3.42 - 3.40 (m, 1H), 3.38 (br s, 3H), |

FIG. 3B. Continued

| | | | |
|---|---|---|---|
| | | | 2.96 - 2.83 (m, 1H), 2.64 - 2.53 (m, 1H), 2.40 - 2.30 (m, 2H), 2.17 - 2.04 (m, 2H), 1.99 - 1.95 (m, 1H), 1.86 (br d, J = 11.2 Hz, 3H), 1.55 - 1.39 (m, 2H), 1.29 (d, J = 12.3 Hz, 1H), 1.20 - 1.08 (m, 2H). |
| 701 | B | C | 1H NMR (400MHz, DMSO-d6) δ 12.92 (s, 1H), 10.95 (s, 1H), 9.84 (s, 1H), 8.75 (s, 1H), 8.65 (d, J=2.0 Hz, 1H), 8.55 (s, 1H), 8.08 (s, 1H), 7.66 - 7.58 (m, 4H), 7.27 (t, J=8.8 Hz, 1H), 7.20 (d, J=8.8 Hz, 2H), 7.11 (d, J=8.8 Hz, 2H), 5.43 - 5.19 (m, 1H), 5.06 (dd, J=5.2, 13.2 Hz, 1H), 4.40 - 4.33 (m, 1H), 4.28 - 4.21 (m, 1H), 4.12 (d, J=13.2 Hz, 1H), 3.87 (d, J=12.4 Hz, 3H), 3.60 - 3.47 (m, 3H), 3.45 - 3.37 (m, 2H), 3.35 - 3.27 (m, 1H), 3.26 - 3.20 (m, 1H), 3.13 - 2.98 (m, 3H), 2.97 - 2.86 (m, 1H), 2.84 - 2.74 (m, 2H), 2.64 - 2.56 (m, 1H), 2.43 - 2.36 (m, 1H), 2.14 - 2.06 (m, 1H), 2.03 - 1.93(m, 4H), 1.44 (d, J=6.4 Hz, 6H), 1.41 - 1.36 (m, 2H), 1.18 - 1.15 (m, 1H), 1.14 - 1.10 (m, 1H). |
| 702 | A | C | 1H NMR (400MHz, DMSO-d6) δ 12.94 (s, 1H), 10.94 (s, 1H), 9.85 (s, 1H), 8.76 (s, 1H), 8.68 (s, 1H), 8.57 (s, 1H), 8.08 (s, 1H), 7.71 - 7.59 (m, 3H), 7.53 (d, J=7.6 Hz, 1H), 7.27 (s, 1H), 7.19 (d, J=7.6 Hz, 2H), 7.09 (s, 2H), 5.42 - 5.20 (m, 1H), 5.04 (d, J=8.8 Hz, 1H), 4.38 - 4.27 (m, 1H), 4.25 - 4.16 (m, 1H), 4.08 - 3.94 (m, 4H), 3.86 - 3.75 (m, 3H), 3.43 - 3.38 (m, 3H), 3.34 - 3.19 (m, 2H), 3.10 - 3.02 (m, 1H), 3.10 -3.02 (m, 1H), 2.99 - 2.84 (m, 4H), 2.64 - 2.58 (m, 2H), 2.29 - 2.20 (m, 1H), 2.15 - 2.05 (m, 2H), 2.01 - 1.91 (m, 4H), 1.48 - 1.37 (m, 8H). |
| 703 | B | C | 1H NMR (400 MHz, DMSO-d6) δ 12.95 (d, J = 2.8 Hz, 1H), 10.91 (s, 1H), 9.84 (s, 1H), 8.67 (d, J = 2.4 Hz, 1H), 8.58 (s, 1H), 8.10 (d, J = 3.2 Hz, 1H), 7.62 (d, J = 8.4 Hz, 3H), 7.49 (d, J = 9.2 Hz, 1H), 7.30 - 7.24 (m, 3H), 6.87 - 6.82 (m, 2H), 5.38 - 5.20 (m, 1H), 5.03 (dd, J = 5.2, 13.3 Hz, 1H), 4.33 - 4.27 (m, 1H), 4.23 - 4.17 (m, 1H), 3.66 - 3.55 (m, 4H), 3.48 (s, 1H), 3.45 - 3.38 (m, 4H), 3.05 (s, 3H), 2.94 - 2.82 (m, 1H), 2.70 - 2.56 (m, 3H), 2.40 - 2.27 (m, 2H), 2.14 - 2.05 (m, 2H), 1.96 - 1.90 (m, 1H), 1.86 - 1.77 (m, 2H). |
| 704 | B | C | 1H NMR (400MHz, DMSO-d6) δ 12.97 - 12.83 (m, 1H), 10.94 (s, 1H), 9.83 (s, 2H), 8.63 (d, J = 2.0 Hz, 1H), 8.52 (d, J = 1.2 Hz, 1H), 8.06 (d, J = 2.8 Hz, 1H), 7.66 - 7.48 (m, 3H), 7.72 - 7.45 (m, 1H), 7.27 (t, J = 8.8 Hz, 1H), 7.21 ( d, J = 6.8 Hz, 2H), 6.87 - 6.52 (m, 1H), 6.62 (d, J = 8.4 Hz, 1H), 5.42 - 5.18 (m. 1H), 5.12 - 5.00 (m, 1H), 4.67 - 4.52 (m, 1H), 4.33 (s, 1H), 4.27 - 4.21 (m, 1H), 4.16 (t, J = 7.2 Hz, 2H), 4.09 - 3.98 (m, 4H), 3.72 - 3.60 (m, 4H), 3.53 - 3.36 (m, 6H), 3.30 (s, 1H), 3.28 (d, J = 2.8 Hz, 1H), 2.95 - 2.85 (m, 1H), 2.59 (d, J = 18.8 Hz, 2H), 2.44 (d, J = 2.4 Hz, 1H), 2.13 - 2.06 (m, 1H), 2.00 - 1.94 (m, 1H). |
| 705 | B | B | 1H NMR (400 MHz, DMSO-d6) δ 12.92 (s, 1H), 10.93 (s, 1H), 9.84 (s, 1H), 8.68 (s, 1H), 8.57 (s, 1H), 8.08 (s, 1H), 7.72 - 7.59 (m, 3H), 7.52 (d, J=8.4 Hz, 1H), 7.32 - 7.22 (m, 2H), 7.11 - 7.03 (m, 2H), 5.45 - 5.18 (m, 1H), 5.05 (dd, J=4.8, 13.3 Hz, 1H), 4.38 - 4.28 (m, 1H), 4.26 - 4.18 (m, 1H), 3.49 (s, 2H), 3.42 - 3.29 (m, 9H), 2.98 - 2.81 (m, 1H), 2.59 (d, J=18.0 Hz, 1H), 2.40 (d, J=10.8 Hz, 1H), 2.10 (d, J=15.2 Hz, 2H), 1.97 (d, J=4.4 Hz, 2H), 1.77 - 1.56 (m, 8H), 1.24 - 1.14 (m, 1H). |

FIG. 3B. Continued

| | | | |
|---|---|---|---|
| 706 | B | C | 1H NMR (300 MHz, DMSO-d6) δ 13.02 (brs, 1H), 10.93 (s, 1H), 9.85 (brs, 1H), 8.96-8.64 (m, 2H), 8.12 (s, 1H), 7.78-7.52 (m, 6H), 7.26-7.23 (m, 1H), 7.10 (s, 2H), 5.30 (d, J = 52.9 Hz, 1H), 5.04 (dd, J = 13.2, 5.0 Hz, 1H), 4.38-4.18 (m, 2H), 3.64-3.49 (m, 5H), 2.94-2.85 (m, 1H), 2.72-2.60 (m, 5H), 2.39-2.36 (m, 1H), 2.21-1.90 (m, 3H), 1.38-1.14 (m, 5H). |
| 707 | A | B | 1H NMR (400MHz, DMSO-d6) δ 1.11 - 1.27 (m, 1 H) 1.87 - 2.11 (m, 5 H) 2.24 - 2.30 (m, 1 H) 2.35 - 2.43 (m, 2 H) 2.54 - 2.63 (m, 2 H) 2.83 - 2.97 (m, 1 H) 2.99 - 3.11 (m, 1 H) 3.17 - 3.27 (m, 7 H) 3.39 - 3.54 (m, 5 H) 3.54 - 3.71 (m, 2 H) 4.15 - 4.24 (m, 1 H) 4.27 - 4.37 (m, 1 H) 4.99 - 5.12 (m, 1 H) 5.16 - 5.36 (m, 1 H) 6.64 - 6.73 (m, 2 H) 7.04 - 7.18 (m, 3 H) 7.50 (d, J=8.0 Hz, 1 H) 7.54 - 7.66 (m, 3 H) 8.02 (s, 1 H) 8.47 - 8.57 (m, 1 H) 8.64 (d, J=2.0 Hz, 1 H) 10.36 - 11.24 (m, 1 H). |
| 708 | A | B | 1H NMR (400 MHz, DMSO-d6) δ (ppm) 12.90 (s, 1H), 10.94 (s, 1H), 8.66 (s, 1H), 8.54 (s, 1H), 8.07 (s, 1H), 7.62-7.50 (m, 4H), 7.27-7.23 (m, 1H), 7.10-7.08 (d, J =8.4 Hz, 2H), 6.55-6.51 (m, 2H), 5.36-5.03 (m, 2H), 4.34-4.17 (m, 2H), 4.07-4.04 (m, 2H), 3.79-3.77 (d, J =10 Hz, 2H), 3.48-3.39 (m, 2H), 3.27-3.11 (m, 6H), 2.94-2.87 (m, 1H), 2.67-2.55 (m, 4H), 2.41-2.33(m, 2H), 2.11-1.96 (m, 4H). |
| 709 | B | B | 1H NMR (400 MHz, DMSO-d6) δ (ppm) 12.94 (brs, 1H), 10.95 (s, 1H), 9.87 (brs, 1H), 8.68 (s, 1H), 8.57 (brs, 1H), 8.11 (s, 1H), 7.72-7.60 (m, 3H), 7.51 (d, J = 8.4 Hz, 1H), 7.29 (t, J = 8.8 Hz, 1H), 7.17-7.03 (m, 4H), 5.31 (d, J = 53.4 Hz, 1H), 5.05 (d, J = 12.6 Hz, 1H), 4.41 (s, 1H), 4.33 (d, J = 16.7 Hz, 1H), 4.21 (d, J = 16.4 Hz, 1H), 3.79-3.55 (m, 4H), 3.50-3.39 (m, 3H), 3.13-3.03 (m, 2H), 2.98-2.84 (m, 1H), 2.45-2.32 (s, 2H), 2.20-1.85 (m, 8H), 1.84-1.72 (m, 1H), 1.58-1.45 (m, 2H), 1.43-1.05 (m, 5H). |
| 710 | A | C | 1H NMR (400MHz, DMSO-d6) δ 1.87 - 2.03 (m, 3 H) 2.04 - 2.14 (m, 2 H) 2.24 - 2.30 (m, 1 H) 2.34 - 2.40 (m, 1 H) 2.40 - 2.45 (m, 1 H) 2.52 (s, 1 H) 2.58 (d, J=18.0 Hz, 1 H) 2.82 - 2.95 (m, 1 H) 2.99 - 3.11 (m, 1 H) 3.17 - 3.22 (m, 1 H) 3.22 - 3.29 (m, 6 H) 3.36 - 3.40 (m, 4 H) 3.41 - 3.55 (m, 3 H) 3.59 - 3.68 (m, 1 H) 4.16 - 4.25 (m, 1 H) 4.28 - 4.36 (m, 1 H) 5.03 (dd, J=13.2, 4.8 Hz, 1 H) 5.19 - 5.39 (m, 1 H) 6.64 - 6.73 (m, 2 H) 7.09 (d, J=8.8 Hz, 2 H) 7.22 (br t, J=8.8 Hz, 1 H) 7.50 (d, J=8.4 Hz, 1 H) 7.56 - 7.65 (m, 3 H) 8.05 (s, 1 H) 8.53 (d, J=2.0 Hz, 1 H) 8.65 (d, J=2.0 Hz, 1 H) 10.85 - 10.99 (m, 1 H). |
| 711 | B | B | HNMR (400 MHz, DMSO-d6) δ 13.13 - 12.80 (m, 1H), 10.98 (s, 1H), 9.93 (s, 1H), 8.84 - 8.44 (m, 2H), 8.16 (s, 1H), 7.87 - 7.62 (m, 3H), 7.33 (t, J=8.4 Hz, 1H), 7.24 - 7.08 (m, 2H), 6.73 - 6.45 (m, 2H), 5.58 - 5.21 (m, 1H), 5.13 - 4.96 (m, 1H), 4.86 - 4.39 (m, 2H), 4.36 - 4.26 (m, 1H), 4.22 - 4.10 (m, 1H), 3.90 (s, 3H), 3.63 - 3.53 (m, 1H), 3.46 (s, 3H), 2.94 (d, J=12.4 Hz, 1H), 2.73 (s, 8H), 2.48 (s, 2H), 2.30 - 2.07 (m, 4H), 1.96 (s, 2H), 1.87 - 1.63 (m, 4H), 1.52 (d, J=10.0 Hz, 2H). |
| 712 | D | A | 1H NMR (400 MHz, DMSO-d6) δ (ppm): 10.91 (brs, 1H), 8.66 (d, J = 2.3 Hz, 1H), 8.55 (s, 1H), 8.07 (s, 1H), 7.64 (dd, J = 17.6, 7.7 Hz, 3H), 7.50 (d, J = 8.3 Hz, 1H), 7.24 (t, J = 8.7 Hz, 1H), 7.07 (d, J = 7.4 Hz, 4H), 5.29 (d, J = 53.2 Hz, 1H), 5.03 (dd, J = 13.2, 5.1 Hz, 1H), 4.71 (brs, 1H), 4.31 (d, J = 16.8 Hz, 1H), 4.19 (d, J = 16.8 Hz, 1H), 3.89 (s, 1H), 3.73-3.61 (m, 3H), 3.47 (s, 1H), 3.42-3.35 (m, 2H), 3.10 (t, J |

FIG. 3B. Continued

| | | | |
|---|---|---|---|
| | | | = 11.1 Hz, 2H), 2.98-2.82 (m, 1H), 2.70-2.55 (m, 1H), 2.41-2.30 (m, 1H), 2.15-2.04 (m, 1H), 1.03-1.75 (m, 7H), 1.74-1.59 (m, 4H), 1.57-1.45 (m, 3H), 1.28-1.09 (m, 2H). |
| 713 | C | B | 1H NMR (400 MHz, DMSO-d6, ppm): δ 12.90 (s, 1H), 10.91 (s, 1H), 9.82 (s, 1H), 8.70 (s, 1H), 8.61-8.56 (m, 1H), 8.07 (s, 1H), 7.68-7.56 (m, 3H), 7.50 (d, J = 8.1 Hz, 1H), 7.31-7.25 (m, 1H), 7.12 (d, J = 8.8 Hz, 2H), 6.58-6.46 (m, 2H), 5.36 (s, 1H), 5.23 (s, 1H), 5.10-5.03 (m, 1H), 4.65-4.59 (m, 1H), 4.38-4.25 (m, 4H), 4.22-4.15 (m, 1H), 3.85-3.81(m, 2H), 3.81-3.74 (m, 2H), 3.52-3.45(m, 1H), 3.42-3.35(m, 1H), 2.95-2.82 (m, 1H),2.70-2.65(m, 1H), 2.63-2.61 (m, 1H), 2.39-2.29(m, 1H), 2.12-2.05 (m, 2H), 2.02-1.92 (m, 2H). |
| 714 | B | C | 1H NMR (400 MHz, DMSO-d6) δ 13.12 - 12.51 (m, 1H), 10.93 (s, 1H), 8.61 (d, J = 2.0 Hz, 1H), 8.55 - 8.42 (m, 1H), 8.18 (s, 1H), 8.08 - 7.99 (m, 1H), 7.60 (dt, J = 6.0, 8.8 Hz, 1H), 7.54 (d, J = 8.4 Hz, 2H), 7.48 (d, J = 8.0 Hz, 1H), 7.22 (t, J = 8.4 Hz, 1H), 6.56 - 6.50 (m, 3H), 6.47 (d, J = 8.4 Hz, 1H), 5.39 - 5.18 (m, 1H), 5.03 (dd, J = 5.2, 13.2 Hz, 1H), 4.34 - 4.26 (m, 1H), 4.20 - 4.14 (m, 1H), 3.97 (s, 4H), 3.87 (s, 2H), 3.76 (s, 2H), 3.47 - 3.45 (m, 2H), 3.39 - 3.39 (m, 2H), 3.26 (s, 2H), 2.97 - 2.81 (m, 2H), 2.62 - 2.52 (m, 2H), 2.45 - 2.39 (m, 2H), 2.38 - 2.31 (m, 1H), 2.29 - 2.21 (m, 2H), 2.21 - 2.14 (m, 1H), 2.14 - 2.02 (m, 2H), 2.02 - 1.83 (m, 4H). |
| 715 | A | C | 1H NMR (400 MHz, DMSO-d6) δ 13.09 - 12.67 (m, 1H), 10.97 (s, 1H), 8.61 (s, 1H), 8.49 (dd, J = 3.2, 5.6 Hz, 1H), 8.18 (s, 1H), 8.04 (s, 1H), 7.64 (d, J = 7.6 Hz, 2H), 7.57 - 7.48 (m, 3H), 7.40 (d, J = 8.8 Hz, 1H), 7.23 (t, J = 8.8 Hz, 1H), 6.54 (d, J = 8.4 Hz, 2H), 5.37 - 5.21 (m, 1H), 5.10 (dd, J = 5.2, 13.1 Hz, 1H), 4.45 - 4.25 (m, 2H), 3.90 (s, 2H), 3.77 (s, 2H), 3.46 (s, 4H), 3.00 - 2.84 (m, 4H), 2.60 (dd, J = 1.6, 18.8 Hz, 2H), 2.40 - 2.28 (m, 4H), 2.13 - 1.89 (m, 8H), 1.80 - 1.67 (m, 4H). |
| 716 | D | B | 1H NMR (400 MHz, DMSO-d6, ppm) δ 12.92 (s, 1H), 10.89 (s, 1H), 9.83 (s, 1H), 8.65 (s, 1H), 8.56 (s, 1H), 8.08 (s, 1H), 7.69-7.59 (m, 3H), 7.52-7.42 (m, 1H), 7.32-7.21 (m, 1H), 7.09-7.02 (m, 2H), 6.88-6.78 (m, 2H), 5.36-5.23 (m, 1H), 5.05-4.97 (m, 1H), 4.31-4.21 (m, 1H), 4.19-4.14 (m, 1H), 4.12-4.09 (m, 2H), 3.78 (s, 2H), 3.72-3.67 (m, 2H),3.66-3.62 (m, 2H), 3.50-3.48 (m, 1H),3.06-3.03 (m, 3H), 2.91-2.82 (m, 2H), 2.32-2.29 (m, 1H), 2.12-2.06 (m, 1H), 2.01-1.89 (m, 2H), 1.23 (s, 2H), 1.18-1.12 (m, 1H). |
| 717 | C | C | 1H NMR (400 MHz, DMSO-d6, ppm) δ 12.91 (s, 1H), 10.93 (s, 1H), 9.83 (s, 1H), 8.72-8.40 (m, 2H), 8.05(s, 1H),7.80-7.41(m, 4H), 7.29-7.20 (m, 1H), 7.11-6.98 (m, 2H), 6.70-6.51 (m, 2H), 5.45-5.12 (m, 1H), 5.04-4.95 (m, 1H), 4.51-4.42 (m, 1H),4.41-4.32 (m, 1H), 4.31-4.01(m, 3H), 3.98-3.81(m, 2H), 3.71-3.52 (m, 2H),3.61-3.51 (m, 1H), 3.50-3.31 (m, 3H), 2.99-2.73 (m, 3H), 2.61-2.20 (m, 3H), 2.19-1.84 (m, 4H), 1.82-1.631 (m, 3H),1.35-1.10 (m, 2H). |
| 718 | B | C | 1H NMR (400 MHz, DMSO-d6) δ 12.92 (d, J = 2.8 Hz, 1H), 10.96 (s, 1H), 10.07 - 9.91 (m, 1H), 9.85 (s, 1H), 8.65 (d, J = 2.4 Hz, 1H), 8.56 (s, 1H), 8.07 (d, J = 2.4 Hz, 1H), 7.70 - 7.56 (m, 4H), 7.32 - 7.24 (m, 1H), 7.23 - 7.14 (m, 2H), 6.96 (d, J = 8.8 Hz, 2H), 5.37 (s, 1H), 5.27 - 5.20 (m, 1H), 5.07 (dd, J = 5.2, |

FIG. 3B. Continued

| | | | |
|---|---|---|---|
| | | | 13.2 Hz, 1H), 4.42 - 4.31 (m, 1H), 4.29 - 4.20 (m, 1H), 4.19 - 3.97 (m, 2H), 3.85 - 3.78 (m, 2H), 3.72 - 3.65 (m, 1H), 3.49 (s, 1H), 3.43 - 3.37 (m, 4H), 3.32 - 3.26 (m, 2H), 3.00 (s, 3H), 2.95 - 2.86 (m, 1H), 2.64 - 2.51 (m, 2H), 2.46 - 2.34 (m, 1H), 2.23 - 2.05 (m, 2H), 2.04 - 1.91 (m, 2H). |
| 719 | B | B | 1H NMR (400MHz, DMSO-d6) δ 1.87 - 2.06 (m, 2 H) 2.06 - 2.21 (m, 2 H) 2.34 - 2.43 (m, 1 H) 2.52 - 2.64 (m, 2 H) 2.84 - 2.98 (m, 1 H) 3.25 - 3.30 (m, 2 H) 3.49 (s, 3 H) 3.56 - 3.71 (m, 2 H) 3.72 - 3.82 (m, 1 H) 3.86 - 4.16 (m, 3 H) 4.19 - 4.30 (m, 1 H) 4.31 - 4.42 (m, 1 H) 5.02 - 5.12 (m, 1 H) 5.17 - 5.40 (m, 2 H) 6.43 (s, 1 H) 7.10 - 7.32 (m, 3 H) 7.55 - 7.76 (m, 4 H) 7.80 - 7.93 (m, 2 H) 8.04 - 8.21 (m, 1 H) 8.63 - 8.78 (m, 2 H) 9.68 - 10.06 (m, 1 H) 9.85 (s, 1 H) 10.92 - 11.01 (m, 1 H) 13.01 (d, J=3.2 Hz, 1 H). |
| 720 | C | C | H1 NMR (400 MHz, DMSO-d6) δ 12.94 (s, 1H), 10.97 (s, 1H), 9.86 (s, 1H), 8.67 (d, J=2.0 Hz, 1H), 8.56 (s, 1H), 8.09 (s, 1H), 7.65 (d, J=8.8, 14.0 Hz, 4H), 7.23 - 7.23 (m, 1H), 7.32 - 7.22 (m, 2H), 7.16 - 7.10 (m, 3H), 5.43 - 5.19 (m, 1H), 5.08 (d, J=4.8, 12.8 Hz, 1H), 4.75 - 4.57 (m, 2H), 4.44 - 4.36 (m, 1H), 4.31 - 4.24 (m, 1H), 3.49 (s, 1H), 3.30 (d, J=7.6 Hz, 2H), 2.89 (d, J=12.0 Hz, 1H), 2.62 (s, 1H), 2.39 (d, J=13.2 Hz, 2H), 2.10 (d, J=17.2 Hz, 2H), 1.99 (s, 2H), 1.89 (s, 8H). |
| 721 | D | C | 1H NMR (400 MHz, DMSO-d6) δ 12.94 (s, 1H), 10.93 (s, 1H), 9.85 (s, 1H), 8.67 (m, 1H), 8.57 (s, 1H), 8.10 (s, 1H), 7.69-7.63 (m, 3H), 7.50 (m, 1H), 7.27 (m, 1H), 7.14-7.07 (m, 2H), 6.56-6.46 (m, 2H), 5.37-5.24 (s, 1H), 5.04 (m, 1H), 4.32 (m, 1H), 4.19 (m, 1H), 4.15-4.06 (m, 4H), 3.69 (m, 2H), 3.50 (m, 1H), 3.43-3.36 (m, 2H), 2.92 (m, 2H), 2.68 -2.57 (m, 1H), 2.38 - 2.34 (m, 1H), 2.16-2.05 (m, 3H), 1.99-1.92 (m, 1H), 1.16 (m, 3H). |
| 722 | D | C | 1H NMR (300 MHz, DMSO, ppm) δ 10.98 (br, 1H), 8.64-8.51 (m, 2H), 8.06 (s, 1H), 7.66-7.56 (m, 4H), 7.30-7.23 (m, 2H), 7.12-7.08 (d, J=10.2Hz, 1H), 6.62-6.59 (d, J=8.7Hz, 2H), 5.39-5.21 (m, 1H), 5.11-5.05 (m, 1H), 4.43-4.25 (m, 4H), 4.04-4.02 (m, 2H), 3.77-3.73 (m, 2H), 3.50-3.40 (m, 4H), 3.28-3.19 (m, 2H), 2.91-2.86 (m, 1H), 2.62-2.58 (m, 1H), 2.42-2.37 (m, 2H), 2.14-1.97 (m, 3H). |
| 723 | C | C | 1H NMR (400 MHz, DMSO-d6) δ 13.16 - 12.66 (m, 1H), 10.94 (s, 1H), 10.10 - 9.60 (m, 1H), 8.65 (s, 1H), 8.58 - 8.48 (m, 1H), 8.06 (s, 1H), 7.69 - 7.46 (m, 4H), 7.32 - 7.19 (m, 1H), 7.06 (s, 4H), 5.44 - 5.17 (m, 1H), 5.09 - 4.94 (m, 1H), 4.42 - 4.14 (m, 2H), 4.05 - 3.88 (m, 2H), 3.51 - 3.46 (m, 2H), 3.21 - 3.17 (m, 4H), 2.83 - 2.73 (m, 3H), 2.72 - 2.63 (m, 6H), 2.37 - 2.29 (m, 2H), 2.02 - 1.90 (m, 2H), 1.87 - 1.76 (m, 3H), 1.40 - 1.17 (m, 3H), 0.93 (s, 6H). |
| 724 | B | C | 1H NMR (400MHz, DMSO-d6) δ 1.85 - 2.04 (m, 4 H) 2.05 - 2.22 (m, 4 H) 2.34 - 2.44 (m, 1 H) 2.56 - 2.64 (m, 1 H) 2.84 - 3.03 (m, 2 H) 3.04 - 3.19 (m, 2 H) 3.24 - 3.39 (m, 2 H) 3.49 (s, 2 H) 4.20 (d, J=8.8 Hz, 2 H) 4.24 - 4.42 (m, 5 H) 5.06 (dd, J=13.2, 4.8 Hz, 1 H) 5.20 - 5.40 (m, 1 H) 6.61 (d, J=8.8 Hz, 1 H) 6.66 (s, 1 H) 7.28 (t, J=8.8 Hz, 1 H) 7.41 (br d, J=7.6 Hz, 2 H) 7.56 - 7.67 (m, 2 H) 7.75 (d, J=7.6 Hz, 2 H) 8.12 (s, 1 H) 8.59 - 8.66 (m, 1 H) 8.70 (s, 1 H) 9.84 (s, 1 H) 10.18 - 10.34 (m, 1 H) 10.90 - 10.99 (m, 1 H) 12.96 - 13.05 (m, 1 H). |

FIG. 3B. Continued

| | | | |
|---|---|---|---|
| 725 | | | 1H NMR (400 MHz, DMSO-d6) δ 12.97 (s, 1H), 10.94 (s, 1H), 9.86 (s, 1H), 8.70- 8.60 (m, 2H), 8.12 (s, 1H), 7.71-7.58 (m, 3H), 7.48 (m, 1H), 7.38 (m, 2H), 7.28 (m, 1H), 6.52-6.43 (m, 2H), 5.37 -5.23 (s, 1H), 5.03 (m, 1H), 4.30 (m, 1H), 4.17 (m, 1H), 4.08-4.00 (m, 2H), 3.58-3.50 (m, 3H), 3.54-3.40 (m, 3H), 3.43-3.35 (m, 2H), 3.28 (m, 1H), 2.97-2.83 (m, 1H), 2.78 (m, 1H), 2.70 (m, 2H), 2.58 (m, 1H), 2.38 (m, 1H), 2.12-1.96 (m, 3H), 1.67 (s, 4H), 1.22-1.11 (m, 1H). |
| 726 | | | 1H NMR (400 MHz, DMSO-d6) δ 13.45 - 12.24 (m, 1H), 10.93 (s, 1H), 8.61 (d, J = 2.0 Hz, 1H), 8.54 - 8.44 (m, 1H), 8.19 (s, 1H), 8.05 (s, 1H), 7.61 (dt, J = 6.0, 9.2 Hz, 1H), 7.55 (d, J = 8.4 Hz, 2H), 7.47 (d, J = 8.0 Hz, 1H), 7.24 (t, J = 8.8 Hz, 1H), 6.56 (d, J = 8.8 Hz, 2H), 6.48 (s, 1H), 6.44 (d, J = 8.4 Hz, 1H), 5.39 - 5.19 (m, 1H), 5.02 (dd, J = 5.2, 13.2 Hz, 1H), 4.33 - 4.26 (m, 1H), 4.20 - 4.14 (m, 1H), 3.92 (s, 6H), 3.80 (s, 2H), 3.39 (s, 6H), 3.30 - 3.28 (m, 2H), 3.27 - 3.25 (m, 2H), 2.91 - 2.83 (m, 1H), 2.62 - 2.54 (m, 1H), 2.47 (s, 1H), 2.41 - 2.34 (m, 1H), 2.31 - 2.23 (m, 2H), 2.21 - 2.14 (m, 1H), 2.13 - 2.00 (m, 2H), 2.00 - 1.94 (m, 1H), 1.93 - 1.86 (m, 2H). |
| 727 | | | 1H NMR (400MHz, DMSO-d6) δ 12.93 (s, 1H), 10.96 (s, 1H), 8.61 (d, J=2.4 Hz, 1H), 8.50 (s, 1H), 8.16 (s, 1H), 8.06 (s, 1H), 7.61 (dt, J=6.0, 9.2 Hz, 1H), 7.55 (d, J=8.4 Hz, 2H), 7.50 (d, J=8.8 Hz, 1H), 7.25 (t, J=8.0 Hz, 1H), 7.08 - 7.00 (m, 2H), 6.62 (d, J=8.8 Hz, 2H), 5.40 - 5.17 (m, 1H), 5.04 (dd, J=5.2, 13.2 Hz, 1H), 4.40 - 4.27 (m, 1H), 4.23 - 4.14 (m, 1H), 4.06 (d, J=8.0 Hz, 1H), 4.03 - 3.97 (m, 1H), 3.89 - 3.81 (m, 2H), 3.74 - 3.68 (m, 2H), 3.19 (s, 5H), 2.96 - 2.84 (m, 2H), 2.83 - 2.76 (m, 2H), 2.62 - 2.55 (m, 1H), 2.40 - 2.35 (m, 1H), 2.15 - 2.04 (m, 2H), 2.02 - 1.94 (m, 2H), 1.80 - 1.69 (m, 2H), 1.53 (s, 1H), 1.42 (d, J=6.0 Hz, 3H), 1.25 - 1.14 (m, 2H). |
| 728 | | | 1H NMR (300 MHz, DMSO-d6) δ 12.90 (s, 1H), 10.92 (s, 1H), 9.80 (s, 1H), 8.66 (d, J = 2.2 Hz, 1H), 8.56 (s, 1H), 8.08 (s, 1H), 7.69 (s, 1H), 7.70 – 7.55 (m, 2H), 7.50 (d, J = 8.4 Hz, 1H), 7.32 – 7.19 (m, 1H), 7.12 (d, J = 8.7 Hz, 2H), 6.68 (s, 2H), 5.38 (s, 1H), 5.03 (dd, J = 13.2, 5.0 Hz, 1H), 4.32 (s,2H), 4.25 (s, 2H), 3.58-3.34 (m, 6H), 3.25 (d, J = 7.7 Hz, 1H), 2.89 (dt, J = 15.6, 8.0 Hz, 2H), 2.58 (d, J = 16.6 Hz, 1H), 2.45 – 2.29 (m, 1H), 2.26 (s, 1H), 2.12 (d, J = 7.0 Hz, 1H), 2.07 – 1.89 (m, 3H), 1.19 (t, J = 12.7 Hz, 1H). |
| 729 | | | 1H NMR (400 MHz, DMSO-d6) δ 12.86 (s, 1H), 10.95 (s, 1H), 9.84 (s, 1H), 8.63 (s, 1H), 8.51 (s, 1H), 8.04 (s, 1H), 7.66 – 7.54 (m, 4H), 7.31 – 7.21 (m, 2H), 7.15 – 7.07 (m, 1H), 6.72-6.70 (m , 2H), 5.30 (d, J =12Hz, 1H), 5.12 – 5.03 (m, 1H), 4.41 (d, J =2.8Hz, 1H), 4.27 - 4.41 (d, J = 2.8Hz, 1H), 4.22 – 4.11 (m, 2H), 3.59 – 3.50 (m, 1H), 3.48-3.40 (m, 4H), 3.26-3.25 (m, 2H), 2.89-2.86 (m, 2H), 2.51-2.50 (m, 1H), 2.33-2.25 (m, 1H), 2.27 – 2.19 (m, 1H), 2.11-2.01 (m, 1H), 1.98-1.95 (m, 4H). |
| 730 | | | 1H NMR (400 MHz, DMSO-d6) δ (ppm): 12.94 (s, 1H), 10.95 (s, 1H), 9.86 (s, 1H), 8.66 (d, J = 2.2 Hz, 1H), 8.56 (s, 1H), 8.09 (s, 1H), 7.70-7.56 (m, 3H), 7.50 (d, J = 8.4 Hz, 1H), 7.27 (t, J = 8.7 Hz, 1H), 7.10-6.99 (m, 4H), 5.30 (d, J = 53.0 Hz, 1H), 5.04 (dd, J = 13.2, 5.1 Hz, 1H), 4.96 (s, 1H), 4.39-4.12 (m, |

FIG. 3B. Continued

| | | | |
|---|---|---|---|
| | | | 3H), 3.77-3.54 (m, 3H), 3.49 (brs, 1H), 3.43-3.36 (m, 2H), 3.31-3.25 (m, 1H), 3.05 (t, J = 11.1 Hz, 2H), 2.98-2.82 (m, 1H), 2.61-2.54 (m, 1H), 2.45-2.25 (m, 1H), 2.24-2.09 (m, 2H), 2.09-2.00 (m, 3H), 1.99-1.85 (m, 4H), 1.82-1.60 (m, 2H), 1.59-1.42 (m, 2H). |
| 731 | | | 1H NMR (400 MHz, DMSO-d6) δ 12.91 (b, 1H), 10.95 (s, 1H), 9.90 (b, 1H), 8.67-8.64 (m, 2H), 8.09 (s, 1H), 7.69-7.63 (m, 3H), 7.553-7.51 (m, 1H), 7.27 (t, J = 8.8 Hz, 1H), 7.12 (d, J = 8.3 Hz, 2H), 6.58-6.49 (m, 2H), 5.30 (d, J = 39.9Hz, 1H), 5.05-5.03 (m, 1H), 4.36-4.20 (m, 4H), 4.09-4.07 (m, 2H), 3.80 (s, 2H), 3.60 (s, 2H), 3.49-3.46 (m, 3H), 2.89-2.86 (m, 1H), 2.59-2.56 (m, 1H), 2.43 -2.29 (m, 1H), 2.19-1.92 (m, 3H). |
| 732 | | | 1H NMR (400 MHz, DMSO-d6) δ 12.90 (s, 1H), 10.99 (s, 1H), 8.63 (s, 1H), 8.62 (s, 1H), 8.05 (s, 1H), 7.66-7.41 (m, 7H), 7.38-736 (m, 1H), 6.66 (d, J = 8.8Hz, 2H), 5.31 (d, J = 32Hz, 1H), 5.10-5.06 (m, 1H), 4.32-4.14 (m, 2H), 3.47-3.36 (m, 2H), 3.17 (s, 2H), 2.92-2.88 (m, 4H), 2.63-2.58 (m, 5H), 2.08-1.87 (m, 6H), 1.61 (s, 4H), 1.37 (s, 2H), 1.22-1.20 (m, 4H). |
| 733 | | | 1H NMR (400MHz, DMSO-d6) δ 13.27 - 12.60 (m, 1H), 10.95 (s, 1H), 8.61 (s, 1H), 8.50 (s, 1H), 8.18 (s, 1H), 8.06 (s, 1H), 7.69 - 7.44 (m, 4H), 7.26 (t, J=8.8 Hz, 1H), 7.11 - 6.97 (m, 2H), 6.62 (d, J=8.4 Hz, 2H), 5.39 - 5.20 (m, 1H), 5.04 (dd, J=5.2, 13.2 Hz, 1H), 4.35 - 4.27 (m, 1H), 4.24 - 4.15 (m, 1H), 4.14 - 3.95 (m, 3H), 3.92 - 3.80 (m, 3H), 3.76 - 3.67 (m, 3H), 2.95 - 2.75 (m, 3H), 2.62 - 2.55 (m, 1H), 2.43 - 2.28 (m, 5H), 2.17 - 2.04 (m, 2H), 2.00 - 1.89(m, 2H), 1.79 - 1.69 (m, 2H), 1.54 (s, 1H), 1.43 (d, J=6.0 Hz, 3H), 1.25 - 1.08 (m, 3H). |
| 734 | | | 1H NMR (400 MHz, DMSO-d6) δ 10.95 (s, 1H), 8.66 (d, J = 2.2 Hz, 1H), 8.56 (s, 1H), 8.09 (s, 1H), 7.64 (t, J = 10.4 Hz, 3H), 7.50 (d, J = 8.5 Hz, 1H), 7.26 (s, 1H), 7.09-7.01 (m, 4H), 6.88 (d, J = 8.2 Hz, 1H), 5.36 (s, 1H), 5.23 (s, 1H), 5.05 (m, 1H), 4.83 (s, 1H), 4.32-4.14 (m, 2H), 3.69-3.59 (s, 6H), 3.05 (s, 2H), 2.89 (d, J =13.1 Hz, 1H), 2.61 (s, 1H), 2.38 (s, 1H), 2.11-1.76 (s, 11H), 1.68 (d, J=15.2 Hz, 3H). |
| 735 | | | 1H NMR (400 MHz, DMSO-d6) δ 12.93 (s, 1H), 10.93 (s, 1H), 9.85 (s, 1H), 8.66 (d, J = 2.3 Hz, 1H), 8.56 (s, 1H), 8.09 (s, 1H), 7.68 (d, J = 8.3 Hz, 2H), 7.67 – 7.57 (m, 1H), 7.50 (d, J = 8.3 Hz, 1H), 7.26 (t, J = 8.7 Hz, 1H), 7.12 (d, J = 8.2 Hz, 2H), 6.67 (d, J = 9.4 Hz, 2H), 5.36 (s, 1H), 5.03 (dd, J = 13.3, 5.1 Hz, 1H), 4.31 (d, J = 16.7 Hz, 1H), 4.19 (d, J = 16.6 Hz, 1H), 4.18 – 4.04 (m, 2H), 3.58 (t, J = 8.8 Hz, 1H), 3.38 (d, J = 12.9 Hz, 2H), 3.32 – 3.25 (m, 3H),3.20(s ,1H) 2.89 (dd, J = 16.5, 10.8 Hz, 2H), 2.58 (d, J = 16.8 Hz, 1H), 2.35 (d, J = 15.4 Hz, 1H), 2.23 (s, 1H), 1.96 (s, 3H), 1.21 (d, J = 18.2 Hz, 1H), 1.13 (d, J = 13.5 Hz, 1H). |
| 736 | | | 1H NMR (400MHz, DIMETHYLSULFOXIDE-d6) δ 13.03 - 12.80 (m, 1H), 10.93 (s, 1H), 8.68 (d, J = 2.0 Hz, 1H), 8.57 (s, 1H), 8.14 (s, 1H), 8.07 (s, 1H), 7.70 - 7.58 (m, 3H), 7.52 (d, J = 8.0 Hz, 1H), 7.27 (t, J = 8.8 Hz, 1H), 7.12 (d, J = 8.8 Hz, 2H), 6.62 - 6.48 (m, 2H), 5.40 - 5.18 (m, 1H), 5.04 (dd, J = 5.4, 13.2 Hz, 1H), 4.38 - 4.30 (m, 1H), 4.24 - 4.17 (m, 1H), 4.07 (t, J = 7.2 Hz, 2H), 3.77 (t, J = 5.4 Hz, 2H), 3.68 - |

FIG. 3B. Continued

| | | | |
|---|---|---|---|
| | | | 3.52 (m, 3H), 3.48 (s, 2H), 3.40 (d, J = 4.4 Hz, 4H), 2.98 - 2.84 (m, 1H), 2.63 - 2.55 (m, 2H), 2.43 - 2.34 (m, 2H), 2.15 - 2.03 (m, 2H), 2.01 - 1.90 (m, 2H), 0.99 (d, J = 6.0 Hz, 6H). |
| 737 | | | 1H NMR (400 MHz, DMSO-d6, ppm) δ 12.87 (br, 1H), 10.99 (br, 1H), 9.85 (br, 1H), 8.62 (s, 1H), 8.50 (s, 1H), 8.05 (s, 1H), 7.70-7.68 (d, J=8Hz, 1H), 7.63-7.54 (m, 4H), 7.48-7.47 (m, 1H), 7.29-7.27 (m, 1H), 6.67-6.65 (d, J=8.8Hz, 2H), 5.36-5.23 (m, 1H), 5.14-5.09 (m, 1H), 4.48-4.30 (m, 2H), 3.64 (s, 2H), 3.48 (s, 1H), 3.39-3.35 (m, 4H), 3.30-3.28 (m, 1H), 3.17 (s, 2H), 2.91-2.88 (m, 1H), 2.62-2.58 (m, 2H), 2.44-2.38 (m, 4H), 2.11-1.99 (m, 3H), 1.89-1.86 (m, 2H), 1.61 (s, 4H). |
| 738 | | | 1H NMR (300 MHz, DMSO-d6) δ 12.86 (s, 1H), 10.96 (s, 1H), 9.85 (s, 1H), 8.62 (s, 1H), 8.49 (s, 1H), 8.04 (s, 1H), 7.68 – 7.49 (m, 4H), 7.31 – 7.09 (m, 3H), 6.72-6.70 (m, 2H), 5.40 – 4.99 (m, 2H), 4.45 – 3.99 (m, 5H), 3.61 – 3.37 (m, 4H), 3.30 – 3.10 (m, 2H), 2.97 – 2.80 (m, 2H), 2.60 (s, 1H), 2.45 – 1.82 (m, 7H). |
| 739 | | | 1H NMR (400 MHz, DMSO-d6) δ (ppm): 12.90 (s, 1H), 10.97 (s, 1H), 9.86 (s, 1H), 8.64 (s, 1H), 8.53 (s, 1H), 8.07 (s, 1H), 7.28 (m, 4H), 7.28-7.26 (m, 2H), 7.20-7.18 (m, 1H), 6.83 (d, J = 8.0 Hz, 2H), 5.30 (d, J = 12.0 Hz, 1H), 5.15-5.07 (m, 1H), 4.50-4.28 (m, 4H), 4.06-4.03 (m, 1H), 3.74-3.72 (m, 1H), 3.50 (s, 1H), 3.68 -3.34 (m, 6H), 2.95-2.93(m, 1H), 2.52- 2.51 (m, 2H), 2.44- 2.35 (m, 3H), 2.20- 2.12 (m, 1H), 2.00- 1.92 (m, 1H). |
| 740 | | | 1H NMR (400MHz, DMSO-d6) δ 12.90 (s, 1H), 10.93 (s, 1H), 8.65 (d, J=2.4 Hz, 1H), 8.53 (s, 1H), 8.14 (s, 1H), 8.07 (s, 1H), 7.67 - 7.56 (m, 3H), 7.49 (d, J=8.4 Hz, 1H), 7.27 (t, J=8.4 Hz, 1H), 7.06 (d, J=8.8 Hz, 2H), 6.59 (s, 1H), 6.54 (d, J=8.4 Hz, 1H), 5.38 - 5.21 (m, 1H), 5.03 (dd, J=5.2, 13.6 Hz, 1H), 4.34 - 4.27 (m, 1H), 4.18 (dd, J=3.6, 17.6 Hz, 1H), 4.11 (d, J=8.8 Hz, 2H), 3.83 - 2.73 (m, 3H), 3.48 (s, 2H), 3.42 - 3.38 (s, 3H), 3.30 - 3.25 (m, 4H), 2.95 - 2.84 (m, 1H), 2.78 - 2.67 (m, 2H), 2.63 - 2.53 (m, 1H), 2.43 - 2.35 (m, 3H), 2.13 - 2.05 (m, 1H), 1.98 - 1.93 (m, 1H), 1.83 - 1.73 (m, 2H), 1.55 - 1.47 (m, 1H), 1.43 (d, J=5.2 Hz, 3H), 1.31 - 1.20 (m, 2H). |
| 741 | | | 1H NMR (400MHz, DMSO-d6) δ 12.89 (s, 1H), 10.93 (s, 1H), 8.64 (d, J=2.4 Hz, 1H), 8.53 (s, 1H), 8.15 (s, 1H), 8.07 (s, 1H), 7.66 - 7.55 (m, 3H), 7.48 (d, J=8.4 Hz, 1H), 7.26 (t, J=8.4 Hz, 1H), 7.06 (d, J=8.8 Hz, 2H), 6.59 (s, 1H), 6.54 (d, J=8.4 Hz, 1H), 5.39 - 5.20 (m, 1H), 5.03 (dd, J=4.8, 13.2 Hz, 1H), 4.36 - 4.26 (m, 1H), 4.22 - 4.14 (m, 1H), 4.11 (d, J=8.8 Hz, 2H), 3.83 - 3.73 (m, 3H), 3.51 - 3.45 (m, 2H), 3.42 - 3.38 (m., 3H), 3.33 - 3.27 (m, 4H), 2.94 - 2.83 (m, 1H), 2.72 - 2.65 (m, 2H), 2.51 - .55 (m, 1H), 2.47 - 2.35 (m, 3H), 2.44 - 2.35 (m, 1H), 2.14 - 2.05 (m, 1H), 2.00 - 1.92 (m, 1H), 1.82 - 1.72 (m, 2H), 1.54 - 1.45 (m, 1H), 1.42 (br d, J=5.9 Hz, 3H), 1.25 (q, J=10.8 Hz, 2H) |
| 742 | D | C | 1H NMR(400MHz, DMSO-d6) δ 10.67 (s, 1H), 8.97 (s, 1H), 8.83 (d, J=2.4 Hz, 1H), 8.41 (d, J=7.6 Hz, 1H), 8.32 (s, 1H), 8.28 (d, J=8.0 Hz, 1H), 8.22 (s, 2H), 8.05 (d, J=2.4 Hz, 1H), 7.99 (d, J=7.6 Hz, 1H), 7.84 - 7.77 (m, 2H), 7.46 - 7.32 (m, 5H), 7.25 (d, J=2.0 Hz, 1H), 5.41 - 5.15 (m, 1H), 4.89 (t, J=7.2 Hz, |

FIG. 3B. Continued

| | | | |
|---|---|---|---|
| | | | 1H), 4.55 (d, J=9.6 Hz, 1H), 4.45 (t, J=8.4 Hz, 1H), 4.35 - 4.20 (m, 1H), 4.05 - 3.87 (m, 4H), 3.82 - 3.69 (m, 7H), 3.67 - 3.52 (m, 11H), 3.22 - 3.10 (m, 5H), 2.93 (d, J=11.6 Hz, 1H), 2.72 - 2.62 (m, 1H), 2.60 - 2.52 (m, 2H), 2.45 - 2.42 (m, 6H), 2.11 - 1.97 (m, 3H), 1.84 - 1.69 (m, 1H), 1.50 - 1.30 (m, 3H), 1.23 (s, 1H), 0.94 (d, J=4.4 Hz, 9H). |
| 743 | D | | 1H NMR (400 MHz, DMSO-d6) δ 10.68 (s, 1H), 8.97 (s, 1H), 8.83 (d, J=2.0 Hz, 1H), 8.44 (d, J=7.6 Hz, 1H), 8.37 - 8.20 (m, 2H), 8.12 - 7.93 (m, 2H), 7.89 - 7.72 (m, 2H), 7.47 - 7.22 (m, 6H), 5.41 - 5.07 (m, 2H), 4.95 - 4.84 (m, 1H), 4.59 - 4.38 (m, 2H), 4.27 (s, 1H), 4.05 - 3.88 (m, 4H), 3.77 (s, 7H), 3.65 - 3.46 (m, 22H), 3.13 (s, 5H), 2.44 (d, J=3.6 Hz, 8H), 2.13 - 1.95 (m, 3H), 1.82 - 1.69 (m, 1H), 1.49 - 1.31 (m, 3H), 0.99 - 0.89 (m, 9H). |
| 744 | D | | 1H NMR (400MHz, DMSO-d6) δ 10.69 (s, 1H), 9.02 - 8.95 (m, 1H), 8.85 (d, J=2.4 Hz, 1H), 8.44 (d, J=7.6 Hz, 1H), 8.33 (s, 1H), 8.29 (d, J=8.0 Hz, 1H), 8.24 (s, 1H), 8.05 (d, J=2.2 Hz, 1H), 8.00 (d, J=7.6 Hz, 1H), 7.85 - 7.78 (m, 2H), 7.45 - 7.35 (m, 5H), 7.26 (d, J=2.0 Hz, 1H), 5.20 (s, 1H), 4.91 (t, J=7.2 Hz, 1H), 4.55 (d, J=9.6 Hz, 1H), 4.45 (t, J=8.0 Hz, 1H), 4.28 (s, 1H), 4.03 - 3.91 (m, 4H), 3.85 - 3.69 (m, 6H), 3.56 - 3.31 (m, 8H), 3.15 (s, 6H), 3.24 - 3.08 (m, 1H), 2.92 (d, J=10.4 Hz, 1H), 2.56 (d, J=12.0 Hz, 2H), 2.45 (d, J=3.2 Hz, 6H), 2.08 - 1.98 (m, 3H), 1.78 (d, J= 13.1 Hz, 1H), 1.48 - 1.36 (m, 3H), 0.95 (s, 9H). |
| 745 | D | | 1H NMR (400 MHz, DMSO-d6) δ 10.67 (s, 1H), 8.98 (s, 1H), 8.84 (d, J=2.4 Hz, 1H), 8.42 (d, J=7.6 Hz, 1H), 8.35 - 8.26 (m, 2H), 8.21 (s, 1H), 8.08 - 7.95 (m, 2H), 7.86 - 7.76 (m, 2H), 7.47 - 7.32 (m, 5H), 7.26 (d, J=2.0 Hz, 1H), 5.39 - 5.18 (m, 1H), 4.97 - 4.86 (m, 1H), 4.55 (d, J=9.6 Hz, 1H), 4.45 (t, J=8.4 Hz, 1H), 4.28 (s, 1H), 4.02 - 3.88 (m, 4H), 3.84 - 3.69 (m, 6H), 3.64 - 3.51 (m, 18H), 3.23 - 3.10 (m, 5H), 2.93 (d, J=11.2 Hz, 1H), 2.69 (d, J=12.0 Hz, 1H), 2.58 (d, J=10.8 Hz, 1H), 2.46 - 2.43 (m, 6H), 2.10 - 1.99 (m, 3H), 1.78 (m, 1H), 1.38 (d, J=7.2 Hz, 3H), 0.94 (s, 9H). |
| 746 | D | | 1H NMR (400 MHz, DMSO-d6) δ 10.69 - 10.61 (m, 1H), 8.96 (s, 1H), 8.89 - 8.80 (m, 1H), 8.48 - 8.36 (m, 1H), 8.36 - 8.16 (m, 3H), 8.08 - 7.93 (m, 2H), 7.86 - 7.72 (m, 2H), 7.46 - 7.20 (m, 6H), 5.37 - 5.17 (m, 1H), 4.95 - 4.81 (m, 1H), 4.59 - 4.38 (m, 2H), 4.32 - 4.22 (m, 1H), 4.09 - 3.92 (m, 4H), 3.87 - 3.69 (m, 7H), 3.66 - 3.53 (m, 6H), 3.14 (s, 3H), 2.94 (d, J=10.0 Hz, 1H), 2.76 - 2.65 (m, 1H), 2.64 - 2.52 (m, 3H), 2.43 (s, 6H), 2.09 - 1.96 (m, 3H), 1.76 (s, 1H), 1.34 (m, 3H), 0.97 - 0.85 (m, 8H). |
| 747 | D | | 1H NMR(400MHz, DMSO-d6) δ 11.08 (s, 1H), 10.66 (s, 1H), 8.84 (d, J=2.0 Hz, 1H), 8.33 (s, 1H), 8.28 (d, J=7.6 Hz, 1H), 8.18 (s, 1H), 8.05 - 7.97 (m, 2H), 7.81 (t, J=7.6 Hz, 1H), 7.77 (d, J=1.6 Hz, 1H), 7.67 (d, J=8.4 Hz, 1H), 7.34 (s, 1H), 7.25 (d, J=8.4 Hz, 1H), 7.20 (s, 1H), 5.23 - 5.14 (m, 1H), 5.06 (dd, J=5.6, 13.2 Hz, 1H), 3.75 (s, 4H), 3.59 - 3.50 (m, 4H), 3.45 - 3.41 (m, 6H), 3.13 - 3.06 (m, 4H), 2.94 - 2.80 (m, 2H), 2.70 - 2.63 (m, 2H), 2.59 - 2.56 (m, 4H), 2.54 (s, 2H), 2.52 (s, 2H), 2.43 (s, 3H), 2.41 - 2.38 (m, 1H), 2.04 - 1.93 (m, 3H), 1.80 - 1.68 (m, 2H). |

FIG. 3B. Continued

| | | | |
|---|---|---|---|
| 748 | D | | 1H NMR (400MHz, DMSO-d6) δ 12.95 (s, 1H), 9.85 (s, 1H), 9.31 (s, 1H), 9.12 - 8.90 (m, 1H), 8.76 - 8.66 (m, 1H), 8.58 (s, 1H), 8.34 (d, J=7.6 Hz, 1H), 8.10 (d, J=2.4 Hz, 1H), 7.73 - 7.57 (m, 3H), 7.49 - 7.40 (m, 2H), 7.35 - 7.27 (m, 2H), 7.18 (d, J=8.8 Hz, 2H), 5.40 - 5.21 (m, 1H), 4.85 (t, J=7.2 Hz, 1H), 4.54 - 4.41 (m, 1H), 4.36 - 4.20 (m, 1H), 3.94 (d, J=12.0 Hz, 2H), 3.81 (d, J=9.9 Hz, 3H), 3.64 (d, J=6.8 Hz, 2H), 3.43 - 3.38 (m, 5H), 3.34 - 3.26 (m, 2H), 3.17 (s, 6H), 2.88 (t, J=11.6 Hz, 2H), 2.48 - 2.45 (m, 4H), 2.16 - 1.99 (m, 4H), 1.92 - 1.75 (m, 3H), 1.50 - 1.27 (m, 5H), 1.02 - 0.84 (m, 3H), 0.82 - 0.70 (m, 3H). |
| 749 | D | C | 1H NMR (400MHz, DMSO-d6) δ 13.01 (s, 1H), 9.53 - 9.30 (m, 1H), 9.05 (s, 1H), 8.74 (d, J=2.4 Hz, 1H), 8.64 (s, 1H), 8.47 (d, J=7.8 Hz, 1H), 8.16 (d, J=2.4 Hz, 1H), 7.74 (d, J=8.6 Hz, 2H), 7.71 - 7.65 (m, 1H), 7.56 - 7.48 (m, 2H), 7.47 - 7.39 (m, 2H), 7.34 (t, J=8.8 Hz, 1H), 7.24 (d, J=8.8 Hz, 2H), 5.56 - 5.21 (m, 1H), 5.07 - 4.91 (m, 1H), 4.52 - 4.31 (m, 2H), 4.09 - 4.09 (m, 1H), 4.00 (d, J=11.6 Hz, 2H), 3.93 - 3.81 (m, 4H), 3.78 (d, J=10.0 Hz, 2H), 3.75 - 3.69 (m, 5H), 3.49 - 3.42 (m, 4H), 3.41 - 3.33 (m, 2H), 3.23 (s, 6H), 2.95 (t, J=12.0 Hz, 2H), 2.52 (s, 4H), 2.27 - 2.06 (m, 4H), 1.97 - 1.84 (m, 3H), 1.56 - 1.34 (m, 5H), 1.07 (br d, J=6.4Hz, 3H), 0.91 - 0.78 (m, 3H). |
| 750 | | | 1H NMR (DIMETHYLSULFOXIDE -d6) δ 8.98 (s, 1H), 8.63 (d, J = 2.0 Hz, 1H), 8.59 - 8.54 (m, 1H), 8.53 - 8.46 (m, 1H), 8.28 (s, 1H), 8.00 (s, 1H), 7.62 - 7.53 (m, 3H), 7.46 - 7.30 (m, 3H), 7.12 - 7.01 (m, 3H), 6.42 (s, 1H), 5.41 - 5.06 (m, 2H), 4.61 - 4.49 (m, 1H), 4.43 - 4.20 (m, 5H), 3.78 - 3.55 (m, 4H), 3.21 - 3.16 (m, 4H), 2.72 - 2.69 (m, 2H), 2.61 - 2.55 (m, 5H), 2.46 - 2.41 (m, 6H), 2.10 - 1.81 (m, 4H), 1.07 - 0.69 (m, 6H). |
| 751 | D | A | 1H NMR (DIMETHYLSULFOXIDE -d6) δ 9.05 - 8.92 (m, 1H), 8.69 - 8.47 (m, 3H), 8.32 - 8.20 (m, 1H), 8.11 - 7.98 (m, 1H), 7.65 - 7.54 (m, 3H), 7.50 - 7.31 (m, 4H), 7.25 - 7.01 (m, 3H), 6.47 (s, 1H), 5.40 - 4.76 (m, 2H), 4.56 - 4.43 (m, 1H), 4.39 - 4.21 (m, 5H), 3.83 - 3.61 (m, 4H), 3.25 - 3.22 (m, 4H), 2.67 - 2.62 (m, 7H), 2.48 - 2.41 (m, 4H), 2.38 - 2.27 (m, 2H), 2.13 - 1.95 (m, 3H), 1.90 - 1.89 (m, 1H), 1.05 - 0.77 (m, 6H). |
| 752 | D | C | 1H NMR (400 MHz, CD3OD) δ 8.77 (s, 1H), 8.76 (s, 1H), 8.50 (s, 1H), 8.02 (s, 1H), 7.79-7.48 (m, 1H), 7.47 (s, 1H), 7.39 (s, 2H), 7.36-7.32 (m, 5H), 7.12-7.00 (m, 3H), 5.21-5.11 (m, 2H), 4.62-4.55 (m, 5H), 4.51-4.31 (m, 2H), 3.67-3.63 (m, 3H), 3.47-3.39 (m, 4H), 2.64-2.56 (m, 2H), 2.55-2.51 (m, 4H), 2.47 (s, 3H), 2.39-2.37 (m, 3H), 2.14-2.10 (m, 3H), 1.86-1.82 (m, 4H), 1.76-1.72 (m, 1H), 1.43-1.45 (t, J = 8 Hz, 2H), 1.35-1.18 (m, 5H), 1.18 (s, 3H), 0.65-0.61 (m, 3H). |
| 753 | D | | 1H NMR (400MHz, DIMETHYLSULFOXIDE-d6) δ 12.88 (s, 1H), 8.98 (s, 1H), 8.65 (s, 1H), 8.53 (s, 1H), 8.32 (d, J = 7.5 Hz, 1H), 8.05 (s, 1H), 7.60 (d, J = 8.8 Hz, 3H), 7.45 - 7.41 (m, 2H), 7.38 (s, 2H), 7.23 (d, J = 8.8 Hz, 1H), 7.08 (d, J = 9.2 Hz, 2H), 5.56 (s, 1H), 5.39 - 5.19 (m, 1H), 5.03 (d, J = 4.0 Hz, 1H), 4.95 - 4.87 (m, 1H), 4.34 - 4.24 (m, 2H), 4.18 (d, J = 5.2 Hz, 2H), 3.70 (s, 1H), 3.50 (s, 4H), 3.47 (s, |

FIG. 3B. Continued

| | | | |
|---|---|---|---|
| | | | 3H), 3.25 - 3.20 (m, 7H), 2.67 (s, 5H), 2.45 (s, 4H), 2.08 (d, J =10.4 Hz, 3H), 1.96 (s, 2H), 1.80 (s, 1H), 1.39 (d, J = 7.2 Hz, 3H), 0.92 (d, J = 6.4 Hz, 3H), 0.71 (d, J = 6.8 Hz, 3H). |
| 754 | B | B | 1H NMR (400MHz, DMSO) δ 12.91 (br s, 1H), 9.01 - 8.95 (m, 1H), 8.64 (d, J=2.2 Hz, 1H), 8.52 (br s, 1H), 8.41 (d, J=8.1 Hz, 1H), 8.18 (s, 1H), 8.07 (s, 1H), 7.65 - 7.52 (m, 3H), 7.48 - 7.32 (m, 4H), 7.25 (t, J=8.3 Hz, 1H), 7.05 (br d, J=8.8 Hz, 2H), 6.28 - 6.11 (m, 1H), 5.42 - 5.17 (m, 1H), 5.14 - 4.87 (m, 1H), 4.99 - 4.65 (m, 1H), 4.40 - 4.18 (m, 3H), 3.94 (s, 1H), 3.76 (br d, J=10.5 Hz, 2H), 3.47 (br s, 2H), 3.32 - 3.23 (m, 6H), 2.77 - 2.68 (m, 2H), 2.46 - 2.45 (m, 1H), 2.46 (s, 3H), 2.47 - 2.35 (m, 1H), 2.39 (br s, 2H), 2.24 - 1.95 (m, 11H), 1.85 - 1.62 (m, 4H), 1.46 - 1.35 (m, 3H), 1.20 (br d, J=10.1 Hz, 2H), 1.07 - 0.95 (m, 3H), 0.90 - 0.81 (m, 3H). |
| 755 | D | | 1H NMR (400MHz, DMSO) δ 12.91 (br s, 1H), 9.01 - 8.96 (m, 1H), 8.64 (d, J=2.2 Hz, 1H), 8.53 (br s, 1H), 8.31 (d, J=7.8 Hz, 1H), 8.18 (s, 1H), 8.07 (s, 1H), 7.66 - 7.54 (m, 3H), 7.48 - 7.31 (m, 4H), 7.25 (t, J=8.7 Hz, 1H), 7.06 (br d, J=8.8 Hz, 2H), 6.19 (s, 1H), 5.40 - 5.20 (m, 1H), 4.90 (quin, J=7.1 Hz, 1H), 4.41 (t, J=7.3 Hz, 1H), 4.27 (br s, 1H), 4.22 (s, 1H), 3.77 (br d, J=11.9 Hz, 2H), 3.59 (br d, J=9.0 Hz, 1H), 3.47 (br s, 2H), 3.33 - 3.28 (m, 4H), 2.76 - 2.68 (m, 2H), 2.46 - 2.28 (m, 10H), 2.20 - 1.94 (m, 10H), 1.83 - 1.63 (m, 4H), 1.37 (d, J=7.0 Hz, 2H), 1.48 (br d, J=7.2 Hz, 1H), 1.28 - 1.11 (m, 2H), 1.04 - 0.94 (m, 3H), 0.87 (s, 3H). |
| 756 | D | | 1H NMR (400MHz, DMSO-d6) δ 10.65 (s, 1H), 8.96 (s, 1H), 8.84 (d, J=2.4 Hz, 1H), 8.41 (d, J=7.2 Hz, 1H), 8.31 (s, 1H), 8.27 (d, J=7.3Hz, 1H), 8.03 (d, J=2.4 Hz, 1H), 7.99 (d, J=7.6 Hz, 1H), 7.83 - 7.75 (m, 2H), 7.46 - 7.39 (m, 2H), 7.38 - 7.30 (m, 3H), 7.19 (d, J=1.6 Hz, 1H), 5.46 (s, 1H), 5.13 (d, J=3.2 Hz, 1H), 4.95 - 4.82 (m, 1H), 4.53 (d, J=10.0 Hz, 1H), 4.43 (t, J=8.4 Hz, 1H), 4.28 (s, 1H), 4.01 - 3.93 (m, 2H), 3.79 - 3.65 (m, 6H), 3.61 (dd, J=3.6, 8.4 Hz, 5H), 3.08 (s, 4H), 2.44 (s, 6H), 2.11 - 1.97 (m, 2H), 1.92 - 1.63 (m, 6H), 1.60 - 1.43 (m, 2H), 1.35 (dd, J=3.6, 6.8 Hz, 3H), 0.92 (d, J=3.2 Hz, 9H). |
| 757 | D | | 1H NMR (400 MHz, DIMETHYLSULFOXIDE-d6) δ 12.88 (s, 1H), 8.99 - 8.96 (m, 1H), 8.64 (d, J = 2.2 Hz, 1H), 8.53 (s, 1H), 8.06 (s, 1H), 7.86 (d, J = 8.0 Hz, 1H), 7.65 - 7.56 (m, 3H), 7.44 (d, J = 4.4 Hz, 1H), 7.40 (d, J = 8.4 Hz, 2H), 7.35 - 7.25 (m, 2H), 7.11 - 6.99 (m, 2H), 5.62 - 5.52 (m, 1H), 5.41 - 5.17 (m, 1H), 5.05 (d, J = 3.6 Hz, 1H), 4.93 - 4.81 (m, 1H), 4.48 - 4.37 (m, 1H), 4.28 - 4.02 (m, 3H), 3.57 - 3.50 (m, 2H), 3.50 - 3.42 (m, 5H), 3.39 (s, 2H), 3.34 (s, 2H), 3.22 (s, 1H), 3.17 (s, 3H), 2.73 - 2.62 (m, 3H), 2.59 (s, 3H), 2.48 - 2.41 (m, 4H), 2.20 (s, 1H), 2.09 (d, J = 15.6 Hz, 2H), 1.99 (s, 1H), 1.85 (br d, J = 5.6 Hz, 1H), 1.45 (d, J = 6.4 Hz, 1H), 1.31 (d, J = 7.2 Hz, 2H), 0.94 (d, J = 6.4 Hz, 2H), 0.77 (d, J = 6.4 Hz, 3H), 0.68 (d, J = 6.4 Hz, 1H). |
| 758 | | | 1H NMR (300 MHz, DMSO-d6) δ 12.91(s, 1H), 9.83 (s, 1H), 8.99 (s, 1H), 8.65 (s, 1H), 8.60 -8.55 (m, 2H), 8.07 (s, 1H), 7.62 (s, 3H), 7.60 -7.37 (m, 4H), 7.30-7.24 (m, 1H), 7.09-7.07 (m, 2H), 5.21-5.13 (m, 2H), 4.54-4.44 (m, 2H), 4.29 -4.23 (m, 3H), 3.62-3.31 (m, 13H), 2.91-2.73 (m, 4H), 2.56-2.54 (m, 3H), |

FIG. 3B. Continued

| | | | |
|---|---|---|---|
| | | | 2.50-2.47 (m, 7H), 2.28-1.96 (m, 8H), 1.81-1.77 (m, 4H), 1.31-1.11(m, 2H), 0.95-0.86 (s, 9H). |
| 759 | D | A | 1H NMR (300 MHz, DMSO-d6) δ 8.99 (s, 1H), 8.64-8.61 (m, 2H), 8.53 (s, 1H), 8.06 (s, 1H), 7.89-7.86 (m, 1H), 7.61 (s, 3H), 7.58-7.46 (m, 4H), 7.28-7.22 (m, 1H), 7.08-7.05 (d, J = 8.1Hz, 2H), 5.31-5.19 (m, J = 2H), 4.53-4.43 (m, 2H), 4.38-4.16 (m, 6H), 4.06-3.95 (m, 3H), 3.49-3.38 (m, 3H), 3.29-3.13 (m, 6H), 3.23-2.87 (m, 6H), 2.68-2.56 (m, 3H), 2.50-2.46 (m, 3H), 2.26-2.18 (m, 8H), 1.87-1.71 (m, 3H), 1.70-1.53 (m, 1H), 1.31-1.12 (m, 3H), 1.01-0.87 (s, 9H). |
| 760 | B | C | 1H NMR (400 MHz, DMSO-d6) δ 12.89 (s, 1H), 11.10 (s, 1H), 8.65 (s, 1H), 8.52 (s, 1H), 8.15 (s, 1H), 8.06 (s, 1H), 7.83 (d, J = 8.4 Hz, 1H), 7.67-7.55 (m, 3H), 7.31- 7.21 (m, 3H), 7.10-7.03 (m, 2H), 5.36 (d, J = 32.6 Hz, 1H), 5.22-5.20 (m, 1H), 4.92 (t, J = 6.6 Hz, 1H), 3.86-3.74 (m, 4H), 3.69 (t, J = 8.1 Hz, 2H), 2.89-2.86 (m, 2H), 2.72-2.70 (m, 3H), 2.59-2.56 (m, 2H), 2.29-2.28 (m, 3H), 2.20-2.17 (m, 2H), 2.13-2.00 (m, 3H), 1.86 (d, J = 12.4 Hz, 2H), 1.54 (b, 1H), 1.26 – 1.13 (m, 3H), 0.94 (d, J = 6.6 Hz, 6H). |
| 761 | C | C | 1H NMR (400 MHz, DMSO-d6, ppm) δ 12.94 (s, 1H), 10.80 (s, 1H), 9.86 (s, 1H), 9.51 (s, 1H), 8.66 (d, J = 2.2 Hz, 1H), 8.55 (s, 1H), 8.07 (d, J = 3.0 Hz, 1H), 7.68-7.57 (m, 3H), 7.26-7.20 (m, 1H), 7.17 -7.08 (m, 4H), 6.99-6.90 (m, 2H), 5.40-5.20 (m, 1H), 3.85-3.72 (m, 5H), 3.68-3.61 (m, 2H), 3.51-3.40 (m, 2H), 3.29-3.16 (m, 5H), 2.92-2.71 (m, 2H), 2.72-2.59 (m, 1H), 2.22-2.09 (m, 3H), 2.12-1.95 (m, 2H), 1.93-1.84 (m, 2H), 1.50-1.37 (m, 2H), 1.25-1.21 (s, 2H). |
| 762 | D | | 1H NMR (400 MHz, DMSO-d6) δ 12.95 - 12.88 (m, 1H), 9.84 (s, 1H), 9.43 - 9.20 (m, 1H), 9.06 - 8.95 (m, 1H), 8.66 (d, J = 2.0 Hz, 1H), 8.55 (s, 1H), 8.30 (d, J = 8.0 Hz, 1H), 8.13 - 8.01 (m, 1H), 7.74 - 7.56 (m, 3H), 7.48 - 7.34 (m, 4H), 7.27 (t, J = 8.8 Hz, 1H), 7.13 (d, J = 8.8 Hz, 2H), 5.83 (s, 1H), 5.40 - 5.19 (m, 1H), 4.99 - 4.84 (m, 1H), 4.38 - 4.23 (m, 2H), 3.85 (d, J = 11.6 Hz, 2H), 3.75 - 3.69 (m, 2H), 3.61 (s, 4H), 3.41 (s, 2H), 3.32 - 3.23 (m, 6H), 3.19 - 3.14 (m, 2H), 3.06 - 2.91 (m, 2H), 2.83 (t, J = 11.7 Hz, 2H), 2.46 (s, 4H), 2.18 - 1.75 (m, 9H), 1.50 - 1.30 (m, 5H), 0.94 (d, J = 6.4 Hz, 3H), 0.69 (d, J = 6.4 Hz, 3H). |
| 763 | D | | 1H (400 MHz, DMSO-d6) δ 13.05 - 12.71 (m, 1H), 10.06 - 9.66 (m, 1H), 9.04 - 8.94 (m, 1H), 8.81 - 8.72 (m, 1H), 8.68 - 8.59 (m, 1H), 8.57 - 8.42 (m, 1H), 8.10 - 7.95 (m, 1H), 7.81 - 7.73 (m, 1H), 7.62 - 7.52 (m, 3H), 7.48 - 7.43 (m, 1H), 7.42 - 7.32 (m, 3H), 7.23 - 7.14 (m, 1H), 7.11 - 7.03 (m, 2H), 5.74 - 5.66 (m, 1H), 5.38 - 5.18 (m, 1H), 5.10 - 5.04 (m, 1H), 4.92 - 4.83 (m, 1H), 4.71 - 4.58 (m, 1H), 4.48 - 4.38 (m, 1H), 4.31 - 4.18 (m, 1H), 3.82 - 3.71 (m, 2H), 3.63 - 3.36 (m, 9H), 3.26 (s, 2H), 2.91 - 2.69 (m, 6H), 2.27 - 2.16 (m, 4H), 2.12 - 1.64 (m, 10H), 1.50 - 1.42 (m, 1H), 1.35 - 1.17 (m, 4H), 0.96 - 0.92 (m, 2H), 0.79 - 0.74 (m, 3H), 0.69 - 0.64 (m, 1H). |
| 764 | D | | 1H NMR (400MHz, DIMETHYLSULFOXIDE-d6) δ 10.95 (s, 1H), 10.43 - 10.21 (m, 1H), 8.96 - 8.60 (m, 3H), 7.92 - 7.84 (m, 2H), 7.81 (d, J = 5.6 Hz, 2H), 7.60 (d, J = 8.4 Hz, 1H), 7.40 (d, J = 8.0 Hz, 1H), 7.18 - 7.09 (m, 3H), 7.04 (dd, J = 2.0, 8.4 Hz, 1H), 6.96 (d, J = 2.0 Hz, 1H), 6.86 (dd, J = 2.0, 8.0 Hz, 1H), 5.05 (dd, J = 5.2, 13.3 Hz, 1H), 4.41 - 4.32 (m, 1H), 4.29 - 4.21 (m, 1H), 4.20 - 4.11 (m, 4H), 3.82 - |

FIG. 3B. Continued

| | | | |
|---|---|---|---|
| | | | 3.74 (m, 6H), 3.60 (d, J = 2.8 Hz, 6H), 2.96 - 2.80 (m, 1H), 2.59 (d, J = 2.2 Hz, 1H), 2.42 - 2.35 (m, 1H), 2.03 - 1.90 (m, 1H). |
| 765 | D | | 1H NMR (400 MHz, DMSO-d6) δ 11.07 - 10.85 (m, 1H), 8.66 (s, 1H), 8.61 - 8.54 (m, 2H), 8.40 (s, 1H), 7.87 - 7.82 (m, 2H), 7.61 (d, J = 8.4 Hz, 1H), 7.51 - 7.45 (m, 2H), 7.35 (d, J = 8.4 Hz, 1H), 7.15 (d, J = 2.0 Hz, 1H), 7.12 - 7.08 (m, 2H), 7.04 (dd, J = 2.0, 8.4 Hz, 1H), 6.95 (d, J = 2.0 Hz, 1H), 6.80 (dd, J = 2.0, 8.4 Hz, 1H), 5.06 (dd, J = 5.1, 13.3 Hz, 1H), 4.41 - 4.32 (m, 1H), 4.29 - 4.21 (m, 1H), 4.20 - 4.13 (m, 4H), 3.78 - 3.74 (m, 4H), 3.60 - 3.57 (m, 4H), 3.56 - 3.54 (m, 4H), 3.52 (s, 4H), 2.93 - 2.83 (m, 1H), 2.62 - 2.57 (m, 2H), 2.41 - 2.33 (m, 1H), 2.02 - 1.92 (m, 1H). |
| 766 | A | C | 1H NMR (400 MHz, DMSO ) δ 12.91 (s, 1H), 10.99 (s, 1H), 9.81 (s, 1H), 8.66 (s, 1H), 8.54 (s, 1H), 8.07 (s, 1H), 7.70-7.50 (m, 6H), 7.29-7.24 (m, 1H), 7.09-7.07 (d, J=8.8Hz, 2H), 5.62 (s, 1H), 5.37-5.10 (m, 2H), 4.83-4.79 (m, 1H), 4.49-4.31 (m, 2H), 3.48-3.32 (m, 3H), 3.29-3.23 (m, 5H), 2.92-2.86 (m, 1H), 2.63-2.38 (m, 8H), 2.12-2.00 (m, 3H), 1.88-1.83 (m, 2H). |
| 767 | A | C | 1H NMR (400MHz, DMSO-d6) δ 12.90 (s, 1H), 10.96 (s, 1H), 8.62 (d, J=2.0 Hz, 1H), 8.50 (s, 1H), 8.15 (s, 1H), 8.06 (s, 1H), 7.62 (dt, J=6.0, 8.8 Hz, 1H), 7.54 (dd, J=8.8, 12.0 Hz, 3H), 7.26 (t, J=8.8 Hz, 1H), 7.12 - 7.03 (m, 2H), 6.57 (d, J=8.8 Hz, 2H), 5.39 - 5.19 (m, 1H), 5.05 (dd, J=5.2, 13.2 Hz, 1H), 4.38 - 4.29 (m, 1H), 4.25 - 4.17 (m, 1H), 4.01 (t, J=7.4 Hz, 2H), 3.58 - 3.52 (m, 2H), 3.49 - 3.45 (M, 2H), 3.41 - 3.38 (m, 4H), 3.05 - 2.84 (m, 3H), 2.62 - 2.58 (m, 1H), 2.58 - 2.52 (m, 8H), 2.43 - 2.34 (m, 1H), 2.13 - 2.04 (m, 1H), 1.99 - 1.93 (m, 1H). |
| 768 | C | C | 1H NMR (400 MHz, DMSO-d6) δ (ppm): 12.90 (s, 1H), 10.80 (s, 1H), 9.86(s, 1H), 8.66 (s, 1H), 8.54 (s, 1H), 8.07 (s, 1H), 7.66-7.58 (m, 3H), 7.30-7.25 (m, 1H), 7.19-7.15 (m, 1H), 7.09-7.07 (d, J=8.0Hz, 2H), 6.85-6.82(m, 1H),6.64-6.62(d, J=8.0Hz,1H), 5.37-5.24 (m, 1H), 3.82-3.75 (m, 3H), 3.52-3.39 (m, 5H), 3.15 (m, 4H), 2.79-2.73 (m, 4H), 2.65-2.51 (m, 3H), 2.26-2.03 (m, 3H), 1.87-1.83 (m, 3H), 1.27-1.25 (m, 2H). |
| 769 | D | C | 1H NMR (400 MHz, DMSO-d6, ppm) δ 12.92 (brs, 1H), 9.82 (brs, 1H), 8.98 (s, 1H), 8.65 (d, J = 2.2 Hz, 1H), 8.53-8.46 (m, 2H), 8.07 (s, 1H), 7.75-7.70 (m, 1H), 7.68-7.55 (m, 3H), 7.44 (d, J = 7.8 Hz, 2H), 7.37 (d, J = 8.0 Hz, 2H), 7.26 (t, J = 8.6 Hz, 1H), 7.13-6.88 (m, 2H), 5.36-5.22 (m, 1H), 5.14 (d, J = 3.4 Hz, 1H), 4.90 (t, J = 7.2 Hz, 1H), 4.64 (s, 1H), 4.54-4.41 (m, 2H), 4.28 (s, 1H), 3.68-3.51 (m, 5H), 3.11-3.00 (m, 3H), 2.98-2.75 (m, 8H), 2.68 (s, 1H), 2.45 (s, 3H), 2.33-1.64 (m, 10H), 1.52-1.33 (m, 4H), 0.95 (s, 9H). |
| 770 | D | B | 1H NMR (300 MHz, CD3OD-d6, ppm): δ 8.91 (s, 1H), 8.72( s,1H), 8.55 (s, 1H), 7.94 (s, 1H), 7.84-7.71 (m, 1H), 7.71-7.58 (m, 2H), 7.49-7.38 (m, 4H), 7.28-7.04 (m, 3H), 5.28-5.16 (m, 1H), 5.09-4.98 (m, 1H), 4.69 (s, 1H), 4.64-4.33 (m, 3H), 3.94-3.84 (m, 3H), 3.82-3.68 (m,3H), 3.68-3.42(m, 8H), 3.29-3.08 (m, 5H), 2.53-2.45 (m, 4H), 2.28-2.13 (m, 3H), 2.05 (s, 2H), 2.02-1.83 (m, 4H), 1.65-1.43 (m, 6H), 1.35- |

FIG. 3B. Continued

| | | | |
|---|---|---|---|
| | | | 1.2(m, 1H), 1.12-1.04 (m, 9H). |
| 771 | D | | 1H NMR (400 MHz, DMSO-d6, ppm): δ 8.97 (s, 1H), 8.64 (s, 1H), 8.52 (brs, 1H), 8.45 (d, J = 7.6 Hz, 1H), 8.21 (s, 1H), 8.05 (s, 1H), 7.76 (d, J = 9.6 Hz, 1H), 7.70-7.61 (m, 3H), 7.43-7.37 (m, 4H), 7.25-7.20 (m, 1H), 7.03 (d, J = 8.4 Hz, 2H), 5.35-5.22 (m, 1H), 4.95-4.85 (m, 1H), 4.51-4.45 (m, 2H), 4.28 (s, 1H), 3.69-3.60 (m, 3H), 3.14-3.01 (m, 5H), 2.97-2.66 (m, 10H), 2.45-2.42 (m, 4H), 2.21-2.02 (m, 6H), 1.88-1.69 (m, 4H), 1.59-1.52 (m, 1H), 1.50-1.42 (m, 1H), 1.38 (d, J = 7.0 Hz, 3H), 0.95 (s, 9H). |
| 772 | D | B | 1H NMR (400 MHz, DMSO-d6, ppm) δ 8.98 (s, 1H), 8.73-8.65 (m, 1H), 8.53-8.47 (m, 2H), 8.22 (s, 1H), 8.06 (s, 1H), 7.85 (d, J = 9.8 Hz, 1H), 7.77-7.60 (m, 3H), 7.48-7.30 (m, 4H), 7.21-7.15(m, 1H), 7.10-7.01 (m, 2H), 5.35-5.22 (m, 1H), 4.90-4.82 (m, 1H), 4.54-4.40 (m, 2H), 4.28-4.20 (m, 1H), 3.91-3.65 (m, 6H), 3.20-3.11 (m, 2H), 3.01-2.82 (m, 9H), 2.73-2.62 (m, 1H), 2.47-2.56 (m, 3H), 2.43-2.30(m, 1H), 2.26-1.97 (m, 6H), 1.85-1.73 (m, 3H), 1.68-1.55 (s, 3H), 1.47-1.38 (m, 2H), 1.23-1.11 (m, 4H), 0.93 (s, 9H). |
| 773 | D | C | 1H NMR (400 MHz, DMSO-d6, ppm): δ 12.90 (s, 1H), 8.98 (s, 1H), 8.72 (s, 1H), 8.60-8.53 (m, 1H), 8.10 (s, 1H), 7.78-7.72 (m, 1H), 7.62-7.55 (m, 3H), 7.47 (d, J = 8.0 Hz, 2H), 7.35 (d, J = 9.5 Hz, 2H), 7.25-7.16 (m, 1H), 7.10-7.08 (m, 2H),5.35-5.20 (m, 1H), 5.12 (s, 1H), 4.93-4.80 (m, 1H), 4.65-4.60 (m, 1H), 4.51-4.45 (m, 1H), 4.30-4.20 (m, 1H), 3.75-3.70 (m, 1H), 3.65-3.57 (m, 2H),3.55-3.52 (m, 3H), 3.45-3.33 (m, 3H), 3.32-3.16 (m, 1H), 3.11-3.02 (m, 2H), 3.00-2.56 (m, 7H), 2.50-2.46 (m, 4H), 2.33 (s, 1H), 2.29-2.07 (m, 6H), 1.90-1.70 (m, 3H), 1.51(m, 1H), 1.38 (s, 3H), 1.25-1.06 (s, 3H), 0.94 (s, 9H). |
| 774 | D | C | 1H NMR (400 MHz, DMSO-d6) δ 8.64 (s, 2H), 8.58 - 8.39 (m, 2H), 8.18 (s, 1H), 8.09 - 7.98 (m, 3H), 7.96 - 7.82 (m, 2H), 7.73 (d, J=10.0 Hz, 1H), 7.65 - 7.54 (m, 3H), 7.41 - 7.31 (m, 3H), 7.25 (m, 1H), 7.06 (d, J=8.8 Hz, 2H), 5.39 - 5.18 (m, 1H), 4.91 (m, 1H), 4.53 - 4.39 (m, 2H), 4.27 (s, 1H), 3.92 - 3.56 (m, 3H), 3.05 (d, J=16.0 Hz, 4H), 2.91 (d, J=15.6 Hz, 4H), 2.79 - 2.63 (m, 4H), 2.44 - 2.41 (m, 3H), 2.37 - 2.31 (m, 2H), 2.25 - 1.96 (m, 5H), 1.86 - 1.65 (m, 5H), 1.50 - 1.32 (m, 3H), 1.31 - 1.09 (m, 3H), 0.94 (s, 9H). |
| 775 | D | C | 1H NMR (400 MHz, DMSO-d6) δ 8.88 (d, J=1.6 Hz, 1H), 8.65 (d, J=2.0 Hz, 1H), 8.58 - 8.48 (m, 2H), 8.45 (d, J=7.6 Hz, 1H), 8.12 - 8.00 (m, 2H), 7.74 (d, J=9.6 Hz, 1H), 7.67 (d, J=8.0 Hz, 2H), 7.64 - 7.53 (m, 3H), 7.48 (m, 1H), 7.41 (d, J=8.0 Hz, 2H), 7.25 (t, J=8.8 Hz, 1H), 7.07 (d, J=8.8 Hz, 2H), 5.39 - 5.20 (m, 1H), 5.13 (d, J=3.2 Hz, 1H), 4.92 (t, J=7.2 Hz, 1H), 4.55 - 4.40 (m, 2H), 4.29 (s, 1H), 3.78 (d, J=11.4 Hz, 2H), 3.64 - 3.44 (m, 5H), 3.32 - 3.23 (m, 6H), 3.11 - 2.88 (m, 2H), 2.73 (t, J=11.4 Hz, 2H), 2.45 (m, 3H), 2.20 (d, J=6.8 Hz, 2H), 2.15 - 1.99 (m, 3H), 1.87 - 1.65 (m, 4H), 1.52 - 1.37 (m, 3H), 1.30 - 1.13 (m, 3H), 0.95 (s, 9H). |
| 776 | D | C | 1H NMR (400 MHz, DMSO-d6) δ 13.14 - 12.31 (m, 1H), 8.68 - 8.59 (m, 3H), 8.56 - 8.43 (m, 2H), 8.22 - 8.13 (m, 2H), 8.06 (s, 1H), 7.81 - 7.67 (m, 5H), 7.64 - 7.54 (m, 3H), 7.47 - 7.37 (m, 2H), 7.25 (t, J=9.2 |

FIG. 3B. Continued

| | | | |
|---|---|---|---|
| | | | Hz, 1H), 7.07 (d, J=8.8 Hz, 2H), 5.41 - 5.19 (m, 1H), 5.18 - 4.87 (m, 2H), 4.55 - 4.37 (m, 2H), 4.31 - 4.23 (m, 1H), 3.83 - 3.75 (m, 2H), 3.63 - 3.53 (m, 6H), 3.01 - 2.94 (m, 2H), 2.78 - 2.68 (m, 3H), 2.44 (s, 3H), 2.21 (d, J=6.8 Hz, 3H), 2.14 - 1.99 (m, 4H), 1.86 - 1.66 (m, 5H), 1.48 - 1.37 (m, 3H), 1.30 - 1.13 (m, 3H), 0.95 (s, 9H). |
| 777 | D | B | 1H NMR (400MHz, DMSO-d6) δ 12.92 (s, 1H), 9.84 (s, 1H), 8.66 (d, J=2.4 Hz, 1H), 8.62 - 8.42 (m, 2H), 8.08 (s, 1H), 7.86 (d, J=2.0 Hz, 1H), 7.77 (d, J=2.0 Hz, 1H), 7.69 - 7.46 (m, 7H), 7.27 (t, J=9.2 Hz, 1H), 7.14 (d, J=8.4 Hz, 2H), 5.40 - 5.18 (m, 1H), 5.05 - 4.93 (m, 1H), 4.54 (d, J=9.2 Hz, 1H), 4.44 (t, J=8.4 Hz, 1H), 4.30 (s, 1H), 3.66 - 3.54 (m, 7H), 3.52 - 3.24 (m, 10H), 2.99 (s, 6H), 2.82 (t, J=10.8 Hz, 2H), 2.52 (s, 3H), 2.17 - 1.92 (m, 4H), 1.89 - 1.69 (m, 3H), 1.49 - 1.20 (m, 5H), 0.97 (s, 9H). |
| 778 | D | | 1H NMR (400MHz, DMSO-d6) δ 8.64 (d, J=2.0 Hz, 1H), 8.51 (s, 1H), 8.38 (d, J=7.6 Hz, 1H), 8.24 (s, 1H), 8.03 (s, 1H), 7.72 (d, J=9.2 Hz, 1H), 7.65 - 7.52 (m, 3H), 7.28 (s, 4H), 7.19 (t, J=8.8 Hz, 1H), 7.06 (d, J=9.2 Hz, 2H), 5.38 - 5.18 (m, 1H), 4.85 (t, J=7.2 Hz, 1H), 4.49 (d, J=9.6 Hz, 1H), 4.42 (t, J=8.4 Hz, 1H), 4.27 (s, 1H), 3.98 (s, 2H), 3.78 (d, J=12.0 Hz, 3H), 3.56 (s, 1H), 3.44 (s, 9H), 3.04 (d, J=15.6 Hz, 2H), 2.91 (d, J=16.0 Hz, 1H), 2.72 (t, J=12.0 Hz, 2H), 2.45 - 2.34 (m, 4H), 2.19 (d, J=7.2 Hz, 2H), 2.12 - 1.92 (m, 3H), 1.85 - 1.67 (m, 4H), 1.45 - 1.30 (m, 3H), 1.22 (d, J=12.8 Hz, 2H), 0.93 (s, 9H). |
| 779 | D | B | 1H NMR (400 MHz, DMSO-d6) δ 12.93 (s, 1H), 9.85 (s, 1H), 9.14 (s, 1H), 8.66 (s, 1H), 8.55 (s, 1H), 8.43 (d, J=6.8 Hz, 1H), 8.08 (s, 1H), 7.75 - 7.56 (m, 5H), 7.46 - 7.35 (m, 2H), 7.33 - 7.23 (m, 1H), 7.13 (s, 2H), 5.41 - 5.20 (m, 1H), 4.97 - 4.85 (m, 1H), 4.54 (d, J=8.8 Hz, 1H), 4.42 (t, J=8.0 Hz, 1H), 4.30 (s, 1H), 4.22 (s, 1H), 3.82 (d, J=10.8 Hz, 2H), 3.48 (s, 12H), 3.34 - 3.24 (m, 4H), 2.99 (s, 6H), 2.82 (s, 2H), 2.19 - 1.96 (m, 3H), 1.91 - 1.73 (m, 3H), 1.38 (d, J=7.2 Hz, 4H), 1.00 - 0.90 (m, 8H). |
| 780 | D | | 1H NMR (400MHz, DIMETHYLSULFOXIDE-d6) δ 13.07 - 12.69 (m, 1H), 8.65 (d, J = 2.0 Hz, 1H), 8.63 - 8.48 (m, 1H), 8.37 (d, J = 7.6 Hz, 1H), 8.06 (s, 1H), 7.73 (d, J = 9.6 Hz, 1H), 7.66 - 7.56 (m, 3H), 7.39 - 7.31 (m, 2H), 7.30 - 7.21 (m, 3H), 7.07 (d, J = 8.8 Hz, 2H), 5.39 - 5.21 (m, 1H), 5.11 (s, 1H), 4.93 (dd, J = 5.6, 8.4 Hz, 2H), 4.86 (t, J = 7.2 Hz, 1H), 4.60 (t, J = 6.4 Hz, 2H), 4.50 (d, J = 9.6 Hz, 1H), 4.43 (t, J = 8.4 Hz, 1H), 4.28 (s, 1H), 4.24 - 4.18 (m, 1H), 3.79 (d, J = 13.2 Hz, 2H), 3.60 - 3.52 (m, 2H), 3.47 (s, 3H), 3.42 - 3.38 (m, 6H), 3.05 (d, J = 16.4 Hz, 1H), 2.92 (d, J = 16.0 Hz, 1H), 2.73 (t, J = 11.6 Hz, 2H), 2.45 - 2.37 (m, 4H), 2.20 (d, J = 7.2 Hz, 2H), 2.14 - 1.93 (m, 4H), 1.84 - 1.68 (m, 4H), 1.35 (d, J = 7.2 Hz, 3H), 1.29 - 1.15 (m, 2H), 0.94 (s, 9H). |
| 781 | D | C | 1H NMR (400 MHz, DMSO-d6) δ 12.93 (s, 1H), 9.85 (s, 1H), 8.66 (d, J=2.0 Hz, 1H), 8.55 (s, 1H), 8.39 (d, J=8.4 Hz, 1H), 8.08 (s, 1H), 7.68 - 7.57 (m, 3H), 7.48 (s, 1H), 7.47 - 7.44 (m, 2H), 7.44 - 7.36 (m, 2H), 7.27 (t, J=8.8 Hz, 1H), 7.13 (br d, J=8.8 Hz, 2H), 6.37 (d, J=1.6 Hz, 1H), 5.39 - 5.18 (m, 1H), 4.87 (d, J=6.4 Hz, 1H), 4.55 (d, J=9.2 Hz, 1H), 4.48 (t, J=8.0 Hz, 1H), 4.30 (s, 2H), 3.65 (s, 2H), 3.64 - 3.58 (m, 4H), 3.57 (s, 2H), 3.48 (s, 3H), 3.45 - 3.37 (m, 4H), 3.36 - 3.24 (m, 3H), 3.03 (s, 6H), 2.83 (d, J=11.2 |

FIG. 3B. Continued

| | | | |
|---|---|---|---|
| | | | Hz, 3H), 2.21 - 1.89 (m, 6H), 1.89 - 1.72 (m, 3H), 1.35 (d, J=9.2 Hz, 3H), 0.97 (s, 9H). |
| 782 | D | | 1H NMR (400MHz, DIMETHYLSULFOXIDE-d6) δ 12.96 - 12.88 (m, 1H), 9.87 - 9.82 (m, 1H), 8.66 (d, J = 2.0 Hz, 1H), 8.56 (d, J = 2.0 Hz, 1H), 8.30 (d, J = 7.6 Hz, 1H), 8.08 (d, J = 1.6 Hz, 1H), 7.67 - 7.58 (m, 3H), 7.35 - 7.24 (m, 1H), 7.24 - 7.19 (m, 4H), 7.14 (d, J = 8.4 Hz, 2H), 5.43 - 5.19 (m, 1H), 4.89 - 4.79 (m, 1H), 4.58 - 4.50 (m, 1H), 4.47 - 4.37 (m, 1H), 4.35 - 4.26 (m, 1H), 4.06 - 3.89 (m, 3H), 3.80 (td, J = 7.6, 15.2 Hz, 4H), 3.67 - 3.52 (m, 10H), 3.20 - 2.90 (m, 8H), 2.88 - 2.75 (m, 3H), 2.30 - 2.24 (m, 1H), 2.00 (s, 5H), 1.91 - 1.76 (m, 4H), 1.45 - 1.28 (m, 5H), 0.96 (s, 10H). |
| 783 | D | B | 1H NMR (400MHz, DIMETHYLSULFOXIDE-d6) δ 12.95 (s, 1H), 9.87 - 9.82 (m, 1H), 9.74 - 9.56 (m, 1H), 8.99 (s, 1H), 8.80 - 8.70 (m, 1H), 8.67 (d, J = 2.0 Hz, 1H), 8.61 - 8.52 (m, 1H), 8.50 - 8.42 (m, 1H), 8.11 - 8.03 (m, 1H), 7.71 - 7.54 (m, 3H), 7.50 - 7.36 (m, 4H), 7.34 - 7.22 (m, 1H), 7.20 - 7.11 (m, 2H), 5.41 - 5.19 (m, 1H), 5.07 - 4.95 (m, 1H), 4.58 (br d, J = 9.2 Hz, 1H), 4.54 - 4.44 (m, 1H), 4.36 - 4.27 (m, 1H), 4.09 - 3.85 (m, 4H), 3.73 - 3.60 (m, 4H), 3.51 (s, 8H), 3.33 (d, J = 5.2 Hz, 4H), 3.29 - 3.24 (m, 5H), 3.16 - 3.05 (m, 4H), 2.20 - 2.00 (m, 5H), 1.99 - 1.91 (m, 2H), 1.87 - 1.78 (m, 1H), 1.63 - 1.47 (m, 2H), 1.02 - 0.91 (m, 9H). |
| 784 | D | B | 1H NMR (400 MHz, DMSO-d6) δ 12.96 (d, J = 2.8 Hz, 1H), 9.87 (s, 1H), 9.76 - 9.62 (m, 1H), 9.00 (s, 1H), 8.81 - 8.71 (m, 1H), 8.68 (d, J = 2.0 Hz, 1H), 8.59 (s, 1H), 8.44 (d, J = 8.4 Hz, 1H), 8.10 (d, J = 2.8 Hz, 1H), 7.72 - 7.58 (m, 3H), 7.48 - 7.40 (m, 3H), 7.37 - 7.24 (m, 1H), 7.18 (d, J = 8.8 Hz, 2H), 5.41 - 5.19 (m, 1H), 5.05 - 4.93 (m, 1H), 4.63 - 4.54 (m, 1H), 4.48 (t, J = 7.6 Hz, 1H), 4.31 (s, 1H), 4.12 - 3.99 (m, 3H), 3.98 - 3.84 (m, 9H), 3.60 - 3.53 (m, 6H), 3.49 (s, 2H), 3.47 - 3.36 (m, 5H), 3.34 - 3.25 (m, 2H), 3.23 - 3.21 (m, 3H), 3.19 - 3.07 (m, 5H), 2.19 - 1.94 (m, 6H), 1.86 - 1.76 (m, 1H), 1.64 - 1.46 (m, 2H), 1.05 - 0.86 (m, 9H). |
| 785 | D | C | 1H NMR (400 MHz, DMSO-d6) δ: 8.98 (s, 1H), 8.64 (d, J = 2.0 Hz, 1H), 8.51 (s, 1H), 8.28 (d, J = 7.6 Hz, 1H), 8.22 (s, 1H), 8.04 (s, 1H), 7.73 (d, J = 9.6 Hz, 1H), 7.62 - 7.55 (m, 3H), 7.35 (d, J = 8.4 Hz, 1H), 7.20 (t, J = 8.8 Hz, 1H), 7.12 - 7.04 (m, 4H), 5.37 - 5.21 (m, 1H), 5.20 - 5.14 (m, 1H), 4.56 - 4.37 (m, 2H), 4.29 (s, 1H), 3.78 (d, J = 11.6 Hz, 2H), 3.65 - 3.51 (m, 4H), 3.32 - 3.18 (m, 18H), 3.04 - 2.92 (m, 2H), 2.78 - 2.64 (m, 3H), 2.48 (s, 4H), 2.20 (d, J = 6.8 Hz, 3H), 2.11 - 1.93 (m, 4H), 1.86 - 1.70 (m, 4H), 1.46 - 1.40 (m, 10H), 1.30 (d, J = 7.2 Hz, 3H), 1.22 (d, J = 11.6 Hz, 2H), 0.94 (s, 9H). |
| 786 | D | | 1H NMR (400 MHz, DMSO-d6) δ 8.98 (s, 1H), 8.63 (d, J = 2.0 Hz, 1H), 8.52 (d, J = 1.2 Hz, 1H), 8.38 (d, J = 7.6 Hz, 1H), 8.23 (s, 1H), 8.03 (s, 1H), 7.79 (d, J = 9.6 Hz, 1H), 7.64 (d, J = 8.0 Hz, 1H), 7.57 (d, J = 8.8 Hz, 3H), 7.18 (t, J = 8.8 Hz, 1H), 7.10 - 6.99 (m, 4H), 5.36 - 5.19 (m, 1H), 5.12 (t, J = 7.2 Hz, 1H), 4.53 - 4.40 (m, 2H), 4.36 (s, 1H), 3.76 (d, J = 12.0 Hz, 3H), 3.66 - 3.53 (m, 4H), 3.33 - 3.17 (m, 18H), 3.03 - 2.91 (m, 2H), 2.70 (s, 1H), 2.47 (s, 4H), 2.15 (d, J = 6.8 Hz, 2H), 2.11 - 1.88 (m, 5H), 1.82 - 1.65 (m, 3H), 1.44 (s, 10H), 1.28 (d, J = 6.8 Hz, 3H), 1.24 - 1.16 (m, 2H), 0.94 (s, 1H), 0.84 (s, 9H). |

FIG. 3B. Continued

| | | | |
|---|---|---|---|
| 787 | D | | 1H NMR (400 MHz, DMSO-d6) δ 12.93 (d, J = 2.8 Hz, 1H), 9.85 (s, 1H), 9.00 (s, 1H), 8.66 (d, J = 2.0 Hz, 1H), 8.56 (s, 1H), 8.30 (d, J = 9.6 Hz, 1H), 8.08 (d, J = 2.0 Hz, 1H), 7.70 - 7.56 (m, 3H), 7.44 (s, 4H), 7.33 - 7.21 (m, 1H), 7.13 (d, J = 8.0 Hz, 2H), 5.43 - 5.18 (m, 2H), 4.79 (d, J = 10.0 Hz, 3H), 4.64 - 4.55 (m, 5H), 4.51 (d, J = 9.6 Hz, 4H), 3.80 (d, J = 12.0 Hz, 3H), 3.71 - 3.60 (m, 2H), 3.59 - 3.51 (m, 2H), 3.48 (s, 2H), 3.44 - 3.36 (m, 3H), 3.35 - 3.25 (m, 2H), 2.87 - 2.75 (m, 3H), 2.19 - 2.04 (m, 3H), 2.02 - 1.88 (m, 3H), 1.82 (d, J = 10.4 Hz, 2H), 1.42 - 1.25 (m, 2H), 0.90 (s, 9H), 0.85 (s, 9H). |
| 788 | B | C | 1H NMR (400 MHz, DMSO-d6) δ 11.13 (d, J = 6.4 Hz, 1H), 10.81 (s, 1H), 8.61 (d, J = 2.0 Hz, 1H), 8.49 (s, 1H), 8.18 (s, 1H), 8.04 (s, 1H), 7.98 (d, J = 5.6 Hz, 1H), 7.64 - 7.59 (m, 1H), 7.58 - 7.53 (m, 2H), 7.23 (t, J = 8.8 Hz, 1H), 6.68 (d, J = 5.6 Hz, 1H), 6.56 (d, J = 8.8 Hz, 2H), 5.40 - 5.19 (m, 1H), 4.61 - 4.49 (m, 1H), 4.19 - 4.01 (m, 1H), 3.94 (s, 4H), 3.82 - 3.76 (m, 2H), 3.46 (s, 2H), 3.39 - 3.37 (m, 3H), 3.35 (s, 4H), 3.28 - 3.26 (m, 2H), 3.23 - 3.20 (m, 2H), 2.79 - 2.70 (m, 1H), 2.66 - 2.59 (m, 3H), 2.35- 2.31 (m, 2H), 2.19 - 2.08 (m, 2H), 2.07 - 1.92 (m, 2H), 1.77 (d, J = 5.6 Hz, 4H), 1.51 - 1.39 (m, 1H), 1.34 - 1.19 (m, 2H). |
| 789 | B | C | 1H NMR (400 MHz, DMSO-d6) δ 11.20 (d, J = 6.8 Hz, 1H), 10.79 (s, 1H), 8.64 (s, 1H), 8.52 (d, J = 2.8 Hz, 1H), 8.17 (s, 1H), 8.05 (s, 1H), 7.79 (d, J = 5.2 Hz, 1H), 7.66 - 7.60 (m, 1H), 7.53 (d, J = 2.8 Hz, 2H), 7.24 (t, J = 8.4 Hz, 1H), 7.05 (d, J = 8.0 Hz, 2H), 6.13 (d, J = 5.6 Hz, 1H), 5.40 - 5.15 (m, 1H), 4.58 - 4.45 (m, 1H), 4.12 (s, 4H), 3.82 - 3.74 (m, 4H), 3.47 (s, 4H), 3.27 - 3.26 (m, 4H), 2.75 - 2.64 (m, 4H), 2.54 - 2.52 (m, 3H), 2.34 - 2.31 (m, 2H), 2.18 - 2.04 (m, 3H), 2.04 - 1.91 (m, 2H), 1.83 - 1.71 (m, 4H), 1.51 - 1.39 (m, 1H), 1.30 - 1.18 (m, 2H). |
| 790 | B | C | 1H NMR (400MHz, DIMETHYLSULFOXIDE-d6) δ 1.20 - 1.30 (m, 2 H) 1.47 (s, 1 H) 1.77 (d, J=10.8 Hz, 2 H) 2.02 - 2.17 (m, 3 H) 2.52 (s, 4 H) 2.69 - 2.83 (m, 2 H) 3.24 - 3.30 (m, 4 H) 3.34 - 3.42 (m, 6 H) 3.47 (s, 1 H) 3.76 (d, J=12.0 Hz, 2 H) 3.90 (s, 3 H) 3.99 (s, 3 H) 4.69 (dt, J=12.4, 6.0 Hz, 1 H) 5.20 - 5.41 (m, 1 H) 6.01 (d, J=1.6 Hz, 1 H) 6.07 (dd, J=8.8, 1.6 Hz, 1 H) 7.05 (d, J=8.8 Hz, 2 H) 7.25 (t, J=8.4 Hz, 1 H) 7.54 - 7.66 (m, 3 H) 7.76 (d, J=8.4 Hz, 1 H) 8.06 (s, 1 H) 8.39 (d, J=6.8 Hz, 1 H) 8.53 (s, 1 H) 8.64 (d, J=2.0 Hz, 1 H) 10.85 (s, 1 H) 12.89 (s, 1 H). |
| 791 | B | C | 1H NMR (400MHz, DIMETHYLSULFOXIDE-d6) δ 12.91 (d, J = 2.0 Hz, 1H), 10.87 (s, 1H), 9.84 (s, 1H), 9.79 - 9.58 (m, 1H), 8.62 (d, J = 2.0 Hz, 1H), 8.52 (s, 1H), 8.42 (d, J = 7.2 Hz, 1H), 8.07 (d, J = 2.4 Hz, 1H), 7.78 (d, J = 8.8 Hz, 1H), 7.67 - 7.52 (m, 3H), 7.27 (t, J = 8.8 Hz, 1H), 6.62 (d, J = 8.8 Hz, 3H), 6.54 (s, 1H), 5.41 - 5.19 (m, 1H), 4.73 - 4.66 (m, 1H), 4.49 - 4.40 (m, 3H), 4.36 - 4.29 (m, 3H), 4.13 (s, 3H), 4.01 (s, 3H), 3.95 (s, 2H), 3.48 (s, 1H), 3.44 - 3.37 (m, 2H), 3.35 - 3.24 (m, 1H), 3.15 (t, J = 6.0 Hz, 2H), 2.88 - 2.73 (m, 2H), 2.18 - 1.93 (m, 5H), 1.86 - 1.66 (m, 3H), 1.37 - 1.14 (m, 2H). |
| 792 | B | C | 1H NMR (400MHz, DIMETHYLSULFOXIDE-d6) δ 1.20 - 1.30 (m, 2 H) 1.46 (s, 1 H) 1.76 (d, J=11.2 Hz, 2 H) 2.02 - 2.17 (m, 3 H) 2.52 (s, 1 H) 2.64 - 2.82 (m, 3 H) 3.26 - 3.33 (m, 9 H) 3.39 (d, J=3.2 Hz, 2 |

FIG. 3B. Continued

| | | | |
|---|---|---|---|
| | | | H) 3.47 (s, 1 H) 3.76 (d, J=12.0 Hz, 2 H) 3.93 - 4.06 (m, 4 H) 4.72 (dt, J=12.8, 6.28 Hz, 1 H) 5.17 - 5.41 (m, 1 H) 6.20 - 6.31 (m, 2 H) 7.05 (d, J=8.8 Hz, 2 H) 7.25 (t, J=8.4 Hz, 1 H) 7.54 - 7.66 (m, 4 H) 7.97 (t, J=7.2 Hz, 1 H) 8.05 (s, 1 H) 8.53 (s, 1 H) 8.64 (d, J=2.0 Hz, 1 H) 10.82 (s, 1 H) 12.88 (s, 1 H). |
| 793 | A | C | 1H NMR (400MHz, DIMETHYLSULFOXIDE-d6) δ 12.90 (s, 1H), 10.83 (s, 1H), 9.83 (s, 1H), 9.77 - 9.51 (m, 1H), 8.62 (d, J = 1.6 Hz, 1H), 8.52 (d, J = 1.6 Hz, 1H), 8.07 (d, J = 2.0 Hz, 1H), 8.00 (t, J = 7.2 Hz, 1H), 7.70 - 7.55 (m, 4H), 7.27 (t, J = 8.8 Hz, 1H), 6.90 - 6.73 (m, 2H), 6.62 (d, J = 8.0 Hz, 2H), 5.41 - 5.19 (m, 1H), 4.72 (td, J = 6.0, 11.9 Hz, 1H), 4.48 - 4.40 (m, 2H), 4.31 (dd, J = 5.6, 10.5 Hz, 2H), 4.12 (s, 2H), 4.01 (s, 2H), 3.92 (d, J = 12.8 Hz, 3H), 3.49 (s, 1H), 3.42 - 3.36 (m, 2H), 3.35 - 3.25 (m, 1H), 3.14 (t, J = 6.4 Hz, 2H), 2.89 - 2.80 (m, 2H), 2.79 - 2.71 (m, 1H), 2.11 (dt, J = 3.6, 12.0 Hz, 2H), 2.04 - 1.92 (m, 2H), 1.91 - 1.76 (m, 1H), 1.75 - 1.66 (m, 2H), 1.31 - 1.17 (m, 2H). |
| 794 | B | C | 1H NMR (400MHz, DMSO-d6) δ 13.14 (s, 1H), 8.64 (s, 1H), 8.56 - 8.44 (m, 1H), 8.19 - 8.11 (m, 1H), 8.09 - 8.00 (m, 1H), 7.66 - 7.59 (m, 1H), 7.58 - 7.52 (m, 2H), 7.51 - 7.47 (m, 1H), 7.30 - 7.22 (m, 1H), 7.03 - 6.93 (m, 2H), 6.61 - 6.53 (m, 2H), 5.39 - 5.33 (m, 2H), 5.30 - 5.05 (m, 2H), 4.36 - 4.17 (m, 3H), 4.01 - 3.97 (m, 3H), 3.83 - 3.74 (m, 5H), 3.05 - 2.94 (m, 3H), 2.88 - 2.80 (m, 4H), 2.80 - 2.71 (m, 3H), 2.54 (s, 1H), 2.21 - 1.90 (m, 6H), 1.86 - 1.53 (m, 5H), 1.22 - 1.14 (m, 2H), 1.12 (t, J = 7.2 Hz, 5H). |
| 795 | | | 1H NMR (400MHz, DMSO-d6) δ 12.95 (s, 1H), 8.72 - 8.43 (m, 2H), 8.05 (s, 1H), 7.67 - 7.51 (m, 3H), 7.38 (s, 1H), 7.33 - 7.21 (m, 1H), 7.03 (s, 2H), 6.39 (s, 2H), 5.36 (s, 2H), 5.32 - 4.94 (m, 2H), 4.30 - 4.16 (m, 2H), 4.12 - 3.89 (m, 8H), 3.80 - 3.70 (m, 4H), 3.05 - 2.76 (m, 7H), 2.68 - 2.60 (m, 2H), 2.15 - 1.94 (m, 4H), 1.89 - 1.58 (m, 4H), 1.51 - 1.07 (m, 3H). |

*$DC_{50}$ Categories:
A<10
10<=B<50
50<=C<100
D>=100

**Dmax Categories:
A>=70
50<=B<70
C<50

FIG. 3C

Table 2C. Data of exemplary protein targeting moieties and compounds of the present disclosure.

| No. | Name | Plasma Stability T half (min)* | | Maximum % Released** | |
|---|---|---|---|---|---|
| | | Human | Cyno Monkey | Human | Cyno Monkey |
| 796 | (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | D | D |
| 797 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50-heptadecaoxadopentacontan-52-oate | C | C | D | D |
| 798 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | D | D | C | C |
| 799 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl (65-hydroxy-3,6,9,12,15,18,21,24,27,30,33,36,39,42,45,48,51,54,57,60,63- | D | D | D | D |

FIG. 3C. Continued

| | | | | | |
|---|---|---|---|---|---|
| | henicosaoxapentahexacontyl) succinate | | | | |
| 800 | (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxahenheptacontan-71-oate | D | D | B | B |
| 801 | (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxahenheptacontan-71-oate | D | D | B | B |
| 802 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxaheptacontan-70-oate | C | C | A | A |
| 803 | (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxadoheptacontan-72-oate | D | D | B | B |
| 804 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 69-oxo-2,5,8,11,14,17,20,23,26,29,32,35,38,41,44,47,50,53,56,59,62,65-docosaoxa-68-azadoheptacontan-72-oate | C | C | A | A |

FIG. 3C. Continued

| | | | | | |
|---|---|---|---|---|---|
| 805 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 3-(1-(2,5,8,11,14,17,20,23,26,29,32,35,38,41,44,47,50,53,56,59,62,65-docosaoxaheptahexacontan-67-yl)-1H-1,2,3-triazol-4-yl)propanoate | D | D | B | B |
| 806 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | B | A |
| 807 | (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 808 | (3R,5S)-1-((S)-2-(2-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 809 | (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl | C | C | A | A |

FIG. 3C. Continued

| | | | | | |
|---|---|---|---|---|---|
| | 2,5,8,11,14,17,20,23,26,29,32,35,38,41,44,47,50,53,56,59,62,65,68-tricosaoxaheptacontan-70-oate | | | | |
| 810 | (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26-nonaoxaoctacosan-28-oate | C | C | A | A |
| 811 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26-nonaoxaoctacosan-28-oate | C | C | A | A |
| 812 | (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 69-oxo-2,5,8,11,14,17,20,23,26,29,32,35,38,41,44,47,50,53,56,59,62,65-docosaoxa-68-azadoheptacontan-72-oate | C | C | A | B |
| 813 | 2-(((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)methyl)-5-(4-methylthiazol-5-yl)benzyl 2,5,8,11,14,17,20,23,26,29,32,35,38,41,44,47,50,53,56,59,62,65,68-tricosaoxaheptacontan-70-oate | C | C | A | A |
| 814 | (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 69-oxo-2,5,8,11,14,17,20,23,26,29,32,35,38,41,44,47,50,53,56,59,62,65,71- | B | B | B | B |

FIG. 3C. Continued

| | | | | | |
|---|---|---|---|---|---|
| | tricosaoxa-68-azatriheptacontan-73-oate | | | | |
| 815 | (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 2-((69-oxo-2,5,8,11,14,17,20,23,26,29,32,35,38,41,44,47,50,53,56,59,62,65,68-tricosaoxaheptacontan-70-yl)oxy)acetate | B | C | A | A |
| 816 | (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 68-methyl-69-oxo-2,5,8,11,14,17,20,23,26,29,32,35,38,41,44,47,50,53,56,59,62,65-docosaoxa-68-azadoheptacontan-72-oate | D | D | B | B |
| 817 | (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 818 | (R)-2-((2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate | C | C | B | B |
| 819 | (3R,5S)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68- | C | C | B | B |

FIG. 3C. Continued

| | | | | | |
|---|---|---|---|---|---|
| | tricosaoxaheptacontan-70-oate | | | | |
| 820 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23-octaoxapentacosan-25-oate | C | C | A | A |
| 821 | (3R,5S)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | Not Determined (N.D.) | N.D. | N.D. | N.D. |
| 822 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14-pentaoxahexadecan-16-oate | C | C | A | A |
| 823 | (3R,5S)-1-((R)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | B | C | B | B |
| 824 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17-hexaoxanonadecan-19-oate | C | C | A | B |
| 825 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5- | C | C | A | A |

FIG. 3C. Continued

| | | | | | |
|---|---|---|---|---|---|
| | yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20-heptaoxadocosan-22-oate | | | | |
| 826 | (3R,5S)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 827 | (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate | C | C | B | B |
| 828 | (3R,5S)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl 69-oxo-2,5,8,11,14,17,20,23,26,29,32,35,38,41,44,47,50,53,56,59,62,65-docosaoxa-68-azadoheptacontan-72-oate | C | C | B | B |
| 829 | (3S,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 830 | (3R,5S)-1-((S)-2-(2-(4-((4-(4-(3-(2,6-difluoro-3-(((R)-3- | C | C | A | A |

FIG. 3C. Continued

| | | | | | |
|---|---|---|---|---|---|
| | fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38-tridecaoxatetracontan-40-oate | | | | |
| 831 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47-hexadecaoxanonatetracontan-49-oate | C | C | A | A |
| 832 | (3R,5S)-1-((S)-2-(3-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)isoxazol-5-yl)-3-methylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | N.D. | N.D. | N.D. | N.D. |
| 833 | (3R,5S)-1-((R)-2-(3-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)isoxazol-5-yl)-3-methylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 834 | (3R,5S)-1-((S)-2-(3-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)isoxazol-5-yl)-3-methylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | N.D. | N.D. | N.D. | N.D. |

FIG. 3C. Continued

| | | | | | |
|---|---|---|---|---|---|
| 835 | (3R,5S)-1-((R)-2-(3-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)isoxazol-5-yl)-3-methylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | B | A |
| 836 | (3R,5S)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | B | B |
| 837 | (3R,5S)-1-((S)-2-(2-(4-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethyl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | B | A |
| 838 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl 69-oxo-2,5,8,11,14,17,20,23,26,29,32,35,38,41,44,47,50,53,56,59,62,65-docosaoxa-68-azadoheptacontan-72-oate | C | C | B | B |
| 839 | (3R,5S)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-5-((4-(4-methylthiazol-5-yl)benzyl)carbamoyl)pyrrolidin-3-yl | C | C | A | A |

FIG. 3C. Continued

| | | | | | |
|---|---|---|---|---|---|
| | 2,5,8,11,14,17,20,23,26,29,32,35,38,41,44,47-hexadecaoxanonatetracontan-49-oate | | | | |
| 840 | (R)-2-((2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate | C | C | B | A |
| 841 | (3-(5-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)-1,3-dioxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | C | B | D | C |
| 842 | (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 68-methyl-69-oxo-2,5,8,11,14,17,20,23,26,29,32,35,38,41,44,47,50,53,56,59,62,65-docosaoxa-68-azadoheptacontan-72-oate | D | D | B | B |
| 843 | (3R,5S)-1-((S)-2-(2-(4-((R)-1-(4-(3-(2,6-difluoro-3-(((R)-3-fluoropyrrolidine)-1-sulfonamido)benzoyl)-1H-pyrrolo[2,3-b]pyridin-5-yl)phenyl)pyrrolidin-3-yl)piperazin-1-yl)acetamido)-3,3-dimethylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 844 | (3R,5S)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-5-(((S)-1-(4-(4-methylthiazol-5- | C | C | A | A |

FIG. 3C. Continued

| | | | | | |
|---|---|---|---|---|---|
| | yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | | | | |
| 845 | (3R,5S)-1-((S)-2-(2-(4-((S)-1-(4-(3-(2,6-difluoro-3-(((R)-3-fluoropyrrolidine)-1-sulfonamido)benzoyl)-1H-pyrrolo[2,3-b]pyridin-5-yl)phenyl)pyrrolidin-3-yl)piperazin-1-yl)acetamido)-3,3-dimethylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | A | A |
| 846 | (R)-2-((2S,4R)-1-((S)-2-(2-(4-(((3S,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate | C | C | A | B |
| 847 | (R)-2-((2S,4R)-1-((S)-2-(2-(4-(((3R,5R)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate | C | C | B | B |
| 848 | (3R,5S)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl 2,5,8,11,14,17,20,23,26,29,32,35,38,41,44,47,50,53,56,59,62,65,68-tricosaoxaheptacontan-70-oate | C | C | B | B |
| 849 | (3-(6-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin- | C | B | D | D |

FIG. 3C. Continued

| | | | | | |
|---|---|---|---|---|---|
| | 1-yl)piperidin-1-yl)-4-methoxy-1,3-dioxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | | | | |
| 850 | (R)-2-((2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxypyrrolidine-2-carboxamido)-2-(4-(4-methylthiazol-5-yl)phenyl)ethyl 39-oxo-2,5,8,11,14,17,20,23,26,29,32,35-dodecaoxa-38-azadotetracontan-42-oate | C | C | B | A |
| 851 | (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65,71-tricosaoxa-68-azatriheptacontan-73-oate | B | B | A | A |
| 852 | (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 2-((69-oxo-2,5,8,11,14,17,20,23,26,29,32,35,38,41,44,47,50,53,56,59,62,65,68-tricosaoxaheptacontan-70-yl)oxy)acetate | C | C | B | A |
| 853 | (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl (2,5,8,11,14,17,20,23,26,29,32,35,38,41,44,47,50,53,56,59,62,65-docosaoxaheptahexacontan-67-yl) succinate | C | D | B | B |
| 854 | (R)-2-((2S,4R)-1-((S)-2-(2-(4-((4-(4-(3-(2,6-difluoro-3-(((R)-3- | C | C | A | A |

FIG. 3C. Continued

| | | | | | |
|---|---|---|---|---|---|
| | fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 68-methyl-69-oxo-2,5,8,11,14,17,20,23,26,29,32,35,38,41,44,47,50,53,56,59,62,65,71-tricosaoxa-68-azatriheptacontan-73-oate | | | | |
| 855 | (R)-2-((2S,4R)-1-((R)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)isoxazol-5-yl)-3-methylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate | C | C | A | A |
| 856 | (3-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | C | B | C | D |
| 857 | (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl (2,5,8,11,14,17,20,23,26,29,32,35,38,41,44,47,50,53,56,59,62,65-docosaoxaheptahexacontan-67-yl) carbonate | C | C | C | B |
| 858 | (3-(5-(4-(4-(4-(3-(2,6-difluoro-3-(((R)-3-fluoropyrrolidine)-1-sulfonamido)benzoyl)-1H-pyrrolo[2,3-b]pyridin-5-yl)phenoxy)butyl)piperazin-1-yl)-1,3-dioxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | B | B | C | C |
| 859 | (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl | C | C | B | B |

FIG. 3C. Continued

| | | | | | |
|---|---|---|---|---|---|
| | (2,5,8,11,14,17,20,23,26,29,32,35-dodecaoxaheptatriacontan-37-yl) carbonate | | | | |
| 860 | (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 2,5,8,11,14,17,20,23,26,29,32,35,38,41,44,47,50,53,56,59,62,65,68-tricosaoxaheptacontan-70-oate | B | B | B | B |
| 861 | (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 2,5,8,11,14,17,20,23,26,29,32,35,38-tridecaoxatetracontan-40-oate | B | B | A | B |
| 862 | (3-(5-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | B | B | C | C |
| 863 | (3-(5-(4-((6-(4-(3-(2,6-difluoro-3-(((R)-3-fluoropyrrolidine)-1-sulfonamido)benzoyl)-1H-pyrrolo[2,3-b]pyridin-5-yl)phenyl)-2,6-diazaspiro[3.3]heptan-2-yl)methyl)piperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | C | C | C | C |
| 864 | (3-(2,6-difluoro-3-(((R)-3-fluoropyrrolidine)-1-sulfonamido)benzoyl)-5-(4-(6-((1-(2-(2,6-dioxopiperidin-3-yl)-1-oxoisoindolin-5-yl)piperidin-4-yl)methyl)-2,6-diazaspiro[3.3]heptan-2-yl)phenyl)-1H-pyrrolo[2,3-b]pyridin-1-yl)methyl (2,5,8,11,14,17,20,23,26,29,32,35,38,41,44,47,50,53,56,59,62,65-docosaoxaheptahexacontan-67-yl) carbonate | C | C | B | B |
| 865 | (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 69-methyl- | C | B | B | B |

FIG. 3C. Continued

| | | | | | |
|---|---|---|---|---|---|
| | 2,5,8,11,14,17,20,23,26,29,32,35,38,41,44,47,50,53,56,59,62,65,68-tricosaoxaheptacontan-70-oate | | | | |
| 866 | (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 39-methyl-2,5,8,11,14,17,20,23,26,29,32,35,38-tridecaoxatetracontan-40-oate | C | B | B | B |
| 867 | (3-(5-(4-(4-(3-(2,6-difluoro-3-(((R)-3-fluoropyrrolidine)-1-sulfonamido)benzoyl)-1H-pyrrolo[2,3-b]pyridin-5-yl)phenethyl)piperazin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | C | B | C | D |
| 868 | (3-(5-(1-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperidin-4-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | C | B | C | C |
| 869 | (3-(5-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | B | B | C | D |
| 870 | (3-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-7-methoxy-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | B | B | D | D |
| 871 | (3-(5-(4-((6-(4-(3-(2,6-difluoro-3-(((R)-3-fluoropyrrolidine)-1-sulfonamido)benzoyl)-1H-pyrrolo[2,3-b]pyridin-5-yl)phenyl)-2,6- | B | B | C | C |

FIG. 3C. Continued

| | | | | | |
|---|---|---|---|---|---|
| | diazaspiro[3.3]heptan-2-yl)methyl)piperidin-1-yl)-7-methoxy-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | | | | |
| 872 | (3-(5-(4-((6-(4-(3-(2,6-difluoro-3-(((R)-3-fluoropyrrolidine)-1-sulfonamido)benzoyl)-1H-pyrrolo[2,3-b]pyridin-5-yl)phenyl)-2,6-diazaspiro[3.4]octan-2-yl)methyl)piperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate | B | B | D | C |
| 873 | (3-(2,6-difluoro-3-(((R)-3-fluoropyrrolidine)-1-sulfonamido)benzoyl)-5-(4-(2-(4-(2-(2,6-dioxopiperidin-3-yl)-1-oxoisoindolin-5-yl)piperazin-1-yl)ethyl)phenyl)-1H-pyrrolo[2,3-b]pyridin-1-yl)methyl 2,5,8,11,14,17,20,23,26,29,32,35,38,41,44,47,50,53,56,59,62,65,68-tricosaoxaheptacontan-70-oate | B | C | C | C |

*Plasma Stability T half (min):

A < 5
5 <= B < 60
60 <= C < 500
D >= 500

**Categories of % Parent Released (maximum):

Table 1D. Data of exemplary protein targeting moieties and compounds of the present disclosure.

| Ex. No. | BRafV600E DC50 (nM) | BRafV600E Dmax (%) | NMR Transcript |
|---|---|---|---|
| 96 | B | A | 1H NMR (400 MHz, DMSO-d6) δ 1.62-1.69 (2H, m), 1.77-1.82 (2H, m), 1.96-2.11 (3H, m), 2.40-2.44 (3H, m), 2.51-2.61 (4H, m), 2.84-2.93 (1H, m), 3.26-3.30 (2H, m), 3.36-3.48 (7H, m), 4.08 (2H, t, J = 6.4 Hz), 5.05-5.09 (1H, m), 5.23-5.36 (1H, m), 7.09 (2H, d, J = 8.8 Hz), 7.25-7.29 (2H, m), 7.35 (1H, s), 7.60-7.64 (1H, m), 7.66-7.69 (3H, m), 8.10 (1H, s), 8.54 (1H, brs), 8.66 (1H, d, J = 2.0 Hz), 9.86 (1H, s), 11.08 (1H, s), 12.94 (1H, s). |
| 99 | B | A | 1H NMR (400 MHz, CD3OD): δ 8.80 (s, 1H), 8.65 (s, 1H), 8.56 (s, 1H), 7.89 (s, 1H), 7.73 (m, 1H), 7.54 (d, J = 8.8 Hz, 2H), 7.44 (d, J = 7.6 Hz, 2H), 7.36 (d, J = 8.0 Hz, 2H), 7.07-7.14 (m, 3H), 5.13 - 5.30 (m, 1H), 4.71 (s, 1H), 4.50 - 4.65 (m, 4H), 4.34 (d, J = 15.6 Hz, 1H), 4.12 (m, 2H), 3.78-3.95 (m, 4H), 3.40-3.65 (m, 9H), 3.10 (m, 6H), 2.42 (s, 3H), 2.00-2.30 (m, 4H), 1.04 (s, 9H). |
| 100 | B | A | 1H NMR (400 MHz, CD3OD): δ 8.82 (s, 1H), 8.65 (s, 1H), 8.59 (s, 1H), 7.89 (s, 1H), 7.74 (m, 1H), 7.59 (d, J = 8.8 Hz, 2H), 7.30-7.50 (m, 4H), 7.07-7.20 (m, 3H), 5.15 - 5.30 (m, 1H), 4.62 (s, 1H), 4.50 - 4.60 (m, 3H), 4.30 (d, J = 7.8 Hz, 1H), 4.12 (m, 2H), 3.78-3.95 (m, 2H), 3.40-3.80 (m, 14H), 3.10 (m, 5H), 2.42 (s, 3H), 1.98-2.30 (m, 8H), 1.03 (s, 9H). |
| 114 | A | A | 1H NMR (300 MHz, DMSO-d6): δ 12.89 (s, 1H), 8.94 (s, 1H), 8.70-8.36 (m, 3H), 8.13 (s, 1H), 8.04 (s, 1H), 7.57 (dd, J = 9.0, 5.1 Hz, 4H), 7.38 (s, 4H), 7.22 (td, J = 8.8, 1.6 Hz, 1H), 7.03 (d, J = 8.7 Hz, 2H), 5.26 (d, J = 53.1 Hz, 2H), 4.54-4.16 (m, 5H), 3.68-3.50 (m, 3H), 3.42 (d, J = 19.4 Hz, 2H), 3.30 (dt, J = 25.7, 4.6 Hz, 2H), 3.15 (d, J = 18.7 Hz, 7H), 3.01 (s, 3H), 2.40 (d, J = 8.0 Hz, 7H), 2.16-1.78 (m, 4H), 1.37 (s, 1H), 0.91 (s, 9H). |
| 225 | A | A | 1H NMR (300 MHz, DMSO-d6) δ 12.97 (s, 1H),9.85(s,1H), 8.95 (s, 1H), 8.73 (s, 2H), 8.67 – 8.50 (m, 3H), 8.09 (s, 1H), 7.67 – 7.52 (m, 2H), 7.39 (s, 4H), 7.23 (t, J = 8.7 Hz, 1H), 5.22 – 5.10 (m, 2H), 4.55 – 4.17 (m, 5H), 3.78 (s, 4H), 3.66- 3.13 (s, 7H), 3.01 (s, 5H), 2.43 (s, 3H), 2.32 (s, 5H), 2.07 (d, J = 18.9 Hz, 4H), 0.92 (s, 9H) |
| 226 | A | A | 1H NMR (400 MHz, CD3OD): δ 8.77 (s, 1H), 8.59 (s, 1H), 8.49 (s, 1H), 7.79 (s, 1H), 7.61-7.69 (m, 1H), 7.49 (d, J = 8.8 Hz, 2H), 7.31-7.39 (m, 4H), 6.98-7.04 (m, 3H), 5.18 (s, 0.5H), 5.02 (s, 0.5H), 4.56 (s, 1H), 4.41-4.53 (m, 2H), 4.22-4.29 (m, 1H), 3.76-3.81 (m, 1H), 3.68-3.73 (m, 1H), 3.23-3.52 (m, 4H), 3.16 (s, 4H), 2.94 (s, 2H), 2.90 (s, 1H), 2.72—2.81 (m, 2H), 2.50 (br, 4H), 2.38 (s, 3H), 1.92-2.20 (m, 10H), 1.66-1.79 (m, 2H), 0.95 (s, 9H) |

FIG. 3D. Continued

| | | | |
|---|---|---|---|
| 227 | A | A | 1H NMR (400 MHz, CD3OD): δ 8.89 (s, 1H), 8.70 (s, 1H), 8.61 (s, 1H), 7.91 (s, 1H), 7.71-7.80 (m, 1H), 7.60 (d, J = 8.4 Hz, 2H), 7.43-7.50 (m, 4H), 7.12-7.16 (m, 3H), 5.23 (s, 0.5H), 5.18 (s, 0.5H), 4.56 (s, 1H), 4.53-4.66 (m, 4H), 4.35-4.41 (m, 1H), 3.79-3.90 (m, 4H), 3.44-3.60 (m, 6H), 3.08-3.19 (m, 2H), 2.72-2.81 (m, 10H), 2.50 (s, 3H), 2.03-2.25 (m, 5H), 1.87-1.92 (m, 3H), 1.04 (s, 9H) |
| 231 | B | A | 1H NMR (400 MHz, MeOD-d4): δ: 8.85 (s, 1H), 8.69 (s, 1H), 8.58 (d, J = 2.0 Hz, 1H), 7.90 (s, 1H), 7.76-7.74 (m, 1H), 7.62 (d, J = 8.4 Hz, 2H), 7.46-7.44 (m, 2H), 7.41-7.39 (m, 2H), 7.13-7.08 (m, 3H), 5.30 (s, 0.5H), 5.15 (s, 0.5H), 4.63 (s, 1H), 4.56-4.52 (m, 4H), 4.49-4.33 (m, 2H), 4.19 (t, J = 4.0 Hz, 2H), 3.98 (s, 2H), 3.85-3.80 (m, 4H), 3.58-3.40 (m, 9H), 2.45 (s, 3H), 2.21-1.99 (m, 5H), 1.03 (s, 9H) |
| 239 | A | A | 1H NMR (400 MHz, DMSO-d6): δ 12.93 (s, 1H), 9.85 (s, 1H), 8.99 (s, 1H), 8.66 (s, 1H), 8.55 (s, 1H), 8.46 (d, J = 7.5 Hz, 1H), 8.08 (s, 1H), 7.78 (s, 1H), 7.62 (s, 4H), 7.62-7.57 (m, 2H), 7.48-7.34 (m, 2H), 7.27 (t, J = 8.7 Hz, 1H), 7.07 (d, J = 8.4 Hz, 2H), 5.38-5.21 (m, 1H), 5.13 (s, 1H), 4.91 (d, J = 8.8 Hz, 1H), 4.55-4.42 (m, 2H), 4.28 (s, 1H), 3.58 (s, 3H), 3.48 (s, 2H), 3.40 (s, 2H), 3.22 (s, 5H), 2.95-2.83 (m, 5H), 2.48-2.42 (m, 4H), 2.26-2.22 (m, 3H), 2.12-2.07 (m, 4H), 1.76 (s, 3H), 1.39-1.35 (m, 3H), 1.20-1.18 (m, 3H), 0.94 (s, 9H) |
| 243 | | | 1H NMR (300 MHz, DMSO-d6) δ 12.90 (br, 1H), 9.85 (br, 1H), 8.99 (s, 1H), 8.66 (s, 1H), 8.53 (br, 1H), 8.43 (d, J = 9Hz, 1H), 8.07 (br, 1H), 7.75 (d, J = 9Hz, 1H), 7.63-7.58 (m, 3H), 7.46-7.37 (m, 4H), 7.28-7.25 (m, 1H), 7.07 (d, J = 9Hz, 2H), 5.38 (br, 1H), 5.13-5.12 (m, 1H), 4.86-4.81 (m, 2H), 4.53-4.50 (m, 2H), 4.29 (br, 1H), 3.64-3.61 (m, 4H), 3.48-3.38 (m, 3H), 3.32-3.21 (m, 5H), 3.07-3.01 (m, 1H), 2.91-2.83 (m, 3H), 2.59-2.51 (m, 4H), 2.46 (s, 3H), 2.24-2.04 (m, 7H), 1.79-1.75 (m, 3H), 1.60-1.52 (m, 1H), 1.21-1.05 (m, 2H), 0.95 (s, 9H) |
| 286 | A | A | 1H NMR (300 MHz, DMSO-d6): δ12.90 (brs, 1H), 9.84 (brs, 1H), 8.99-8.95 (m, 1H), 8.69-8.66 (m, 1H), 8.60-8.53 (m, 2H), 8.07 (s, 1H), 7.70-7.61 (m, 3H), 7.54-7.39 (m, 4H), 7.387.30 (m, 1H), 7.21-7.08 (m, 2H), 6.18-5.80 (m, 1H), 5.40-5.15 (m, 1H), 4.74-4.28 (m, 6H), 3.90-3.62 (m ,6H),3.41-3.22 (m, 7H), 3.21-2.81(m, 5H) 2.45-2.42(m, 3H), 2.32-2.20 (m, 1H), 2.17-1.80 (m, 4H), 0.95 (d, J = 6.5 Hz, 3H), 0.81 (d, J = 6.7 Hz, 3H) |
| 287 | | | 1H NMR (400 MHz, CD3OD): δ8.88 (d, J = 3.1 Hz, 1H), 8.70-8.68 (m, 1H), 8.60 (d, J = 2.2 Hz, 1H), 7.90 (s, 1H), 7.80-7.71 (m, 1H), 7.62-7.51 (m, 2H), 7.55-7.37 (m, 4H), 7.20-7.07 (m, 3H), 6.01 (s, 1H), 5.30-5.14 (m, 1H), 4.65-4.54 (m, 1H), 4.53-4.50 (m, 1H), 4.44-4.42 (m, 2H), 4.31-4.22 (m, 2H), 3.80-3.78 (m, 1H), 3.76-3.74 (m, 1H), 3.68-3.36 (m, 4H), 3.31-3.20 (m, 3H), 2.73-2.64 (m, 4H), 3.63-2.56 (m, 2H), 2.49-2.42 (m, 3H), 3.41-2.38 (m, 1H), 2.31 -1.94 (m, 6H), 1.40-1.31 (m, 2H), 1.10-0.87 (m, 6H) |

FIG. 3D. Continued

| | | | |
|---|---|---|---|
| 288 | | | 1H NMR (400 MHz, CD3OD): δ8.88 (d, J = 2.6 Hz, 1H), 8.72-8.67 (m, 1H), 8.61 (d, J = 2.2 Hz, 1H), 7.90-7.88 (m, 1H), 7.76-7.70 (m, 5.7 Hz, 1H), 7.66-7.55 (m, 2H), 7.51-7.43 (m, 4H), 7.20-7.06 (m, 3H), 6.03-6.01 (m, 1H), 5.44-5.10 (m, 1H), 4.57-4.43 (m, 3H), 4.32-4.21 (m, 2H), 3.91-3.84 (m, 1H), 3.83-3.36 (m, 6H), 3.29-3.26 (m, 2H), 2.80-2.54 (m, 6H), 2.52-2.31 (m, 3H), 2.44-2.34 (m, 1H), 2.32-1.95 (m, 6H), 1.40-1.31 (m, 3H), 1.10-1.01 (m, 3H), 0.97-0.88 (m, 3H) |

$DC_{50}$ Categories:
- A<10
- 10<=B<50
- 50<=C<100
- D>=100

Dmax Categories:
- A>70
- 50<=B<=70
- C<50

| Kinase: | Comp. 512 IC$_{50}$ (nM) | Degrades |
|---|---|---|
| ARAF | 1.52 | — |
| CRAF | 56.3 | — |
| BRAF | 5.2 | — |
| BRAF (V600E) | 5.4 | + |
| BRAF (V600K) | 4.64 | + |
| BRAF (G464V) | 14.5 | + |
| BRAF (G469A) | 2.11 | + |
| BRAF (K601E) | 63.9 | + |

COMPOUNDS AND METHODS FOR THE TARGETED DEGRADATION OF RAPIDLY ACCELERATED FIBROSARCOMA POLYPEPTIDES

CROSS-REFERENCE TO RELATED APPLICATIONS

The present disclosure is a continuation of U.S. patent application Ser. No. 16/563,842, filed 7 Sep. 2019, published as U.S. Patent Application Publication No. 2020/0129627 A1 on 30 Apr. 2020, which claims the benefit of and priority to U.S. Provisional Application No. 62/728,581, filed 7 Sep. 2018, and is a continuation-in-part of U.S. patent application Ser. No. 15/853,166, filed 22 Dec. 2017, published as U.S. Pat. No. 10,723,717 on 28 Jul. 2020, which claims priority to U.S. Provisional Application No. 62/438,803, filed 23 Dec. 2016 and U.S. Provisional Application No. 62/582,698, filed 7 Nov. 2017, all of which are incorporated herein by reference in their entirety.

STATEMENT REGARDING FEDERALLY FUNDED RESEARCH

This invention was made with government support under grant number NIH R35CA197589, as issued by the National Institutes of Health. The government has certain rights in the invention.

INCORPORATION BY REFERENCE

U.S. patent application Ser. No. 15/230,354, filed on Aug. 5, 2016; and U.S. patent application Ser. No. 15/206,497 filed 11, Jul. 2016; and U.S. patent application Ser. No. 15/209,648 filed 13 Jul. 2016; and U.S. Patent Application Ser. No. 62/406,888, filed on Oct. 11, 2016; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

FIELD OF THE INVENTION

The description provides bifunctional compounds comprising a target protein binding moiety and an E3 ubiquitin ligase binding moiety, and associated methods of use. The bifunctional compounds are useful as modulators of targeted ubiquitination, especially with respect to Rapidly Accelerated Fibrosarcoma (RAF) proteins, which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Fevine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev* (1993) 7, 1126-1132).

Several mechanisms can explain p53 down regulation by MDM2. First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitrochondria-derived activator of caspases or SMAC) and HTRA2 (also known as Omi). Binding of DIABLO and HTRA2 appears to block IAP activity.

SMAC interacts with essentially all known IAPs including XIAP, c-IAP1, C-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional compounds such as those that are described in U.S. Patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease associated with overexpression or aggregation of Rapidly Accelerated Librosarcoma (RAP), or the overactivation of RAP (such as constitutively active RAP). For example, current BRaf inhibitors (such as, vemurafenib and dabrafenib) may target V600 mutant BRaf. Thus, a need exists for diseases or disorders (such as, melanoma, lung cancer, pancreatic cancer, and/or colorectal cancers) that have different BRaf mutations that are insensitive to currently marketed agents. Furthermore, resistance mutations can emerge in response to BRaf/MEK inhibitor therapy. For example, the p61 splice variant can emerge in melanoma patients treated with BRaf/MEK inhibitor therapy, which leaves these patients with no clinical options. Currently marketed agents also bind to and cause paradoxical activation of wild-type BRaf, which results in clinical complications. In addition, the family of hypoactive Class III BRaf mutants that signal through heterodimerization with CRaf, constitute 40% of BRaf mutations in non-small cell lung cancer (NSCLC), and also appear sporadically across other cancers, cannot be targeted with any currently approved or clinical-stage BRaf inhibitors. Class I BRAF mutants (V600E, V600K, V600D) have high kinase activity, are Ras and dimerization independent, and are sensitive to vemuragenib. Class II BRAF mutants has high to intermediate kinase activity, are Ras-independent and dimerization dependent, and are insensitive to vemurafenib. Class III BRAF mutatns have lot to no kinase activity, are Ras and dimerization dependent, and are insensitive to vemurafenib.

Thus, non-specific effects and the inability to target and modulate RAF, remain an obstacle to the development of effective treatments. As such, small-molecule therapeutic agents that effectively targets RAF (e.g., effectively inhibiting and/or degrading mutant forms of BRaf, while sparing wild-type BRaf) and that leverage or potentiate VHL's, cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer (e.g., renal cell carcinoma, pancreatic cancer, colorectal cancer, lung cancer, ovarian cancer, thyroid cancer, pilocytic astrocytoma, prostate cancer, gastric cancer, hepatocellular carcinoma, and melanoma), cardiofaciocutaneous syndrome, neurofibromatosis type 1, Costello syndrome, Noonan Syndrome, LEOPARD (Lentigo, Electrocardiographic abnormalities, Ocular hypertelorism, Pulmonary stenosis, Abnormal genitalia, Retarded growth, Deafness) syndrome.

As such, in one aspect the disclosure provides bifunctional or PROTAC compounds, which comprise an E3 ubiquitin ligase binding moiety (i.e., a ligand for an E3 ubquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

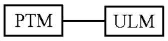

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

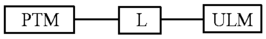

where PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

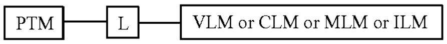

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2E3 ubiquitin ligase binding moiety; and ILM is a IAP binding moiety which binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 2D. Table 1D. Exemplary protein targeting moieties and compounds of the present disclosure.

FIG. 3A. Table 2A. Data of exemplary protein targeting moieties and compounds of the present disclosure.

FIG. 3B. Table 2B. Data of exemplary protein targeting moieties and compounds of the present disclosure.

FIG. 3C. Table 2C. Data of exemplary protein targeting moieties and compounds of the present disclosure.

FIG. 3D. Table 2D. Data of exemplary protein targeting moieties and compounds of the present disclosure.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figures 1A, 1B:
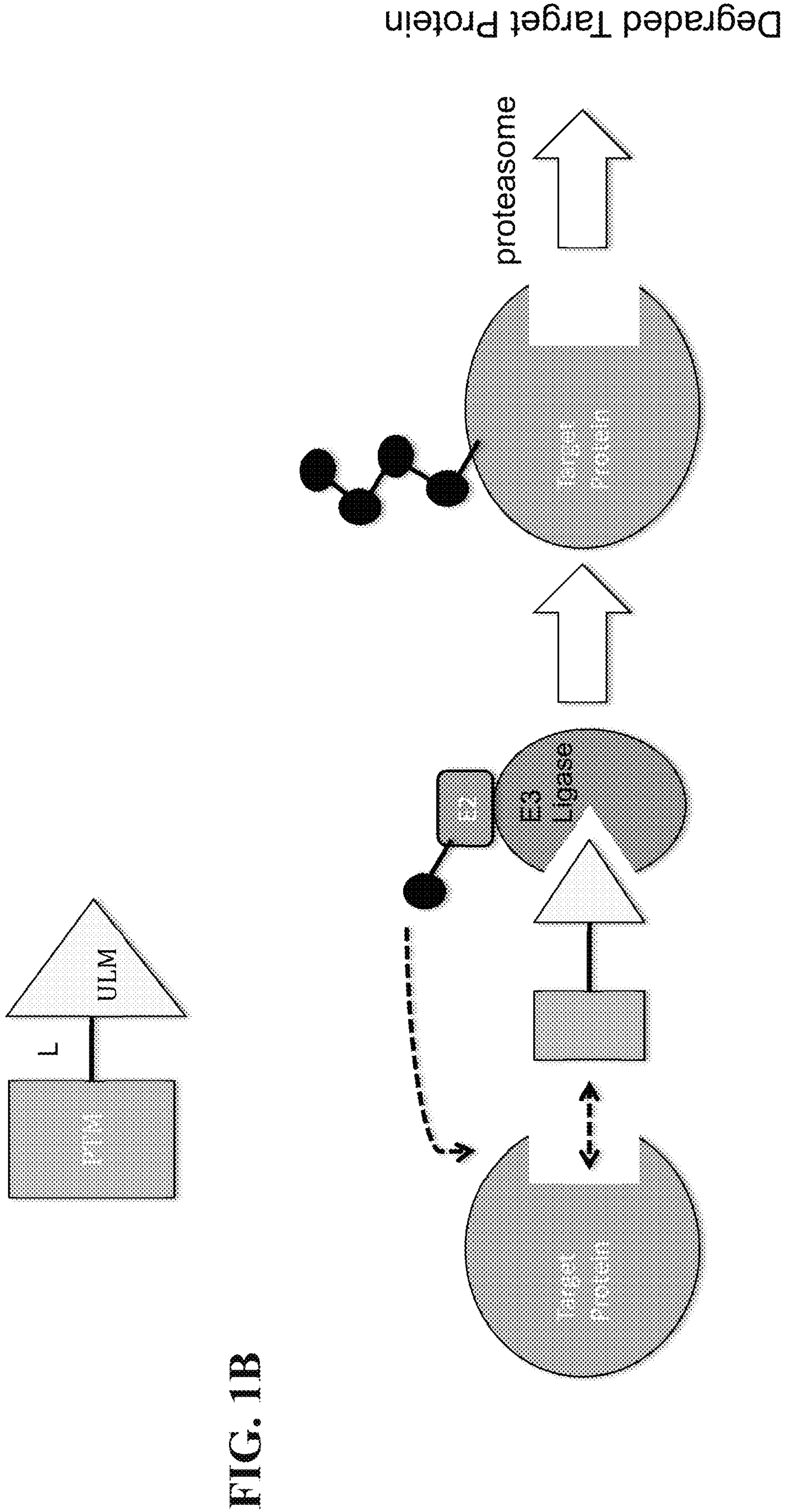
FIGS. 1A and 1B. Illustration of general principle for bifunctional compounds of the present disclosure. (A) Exemplary bifunctional compound comprises a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the bifunctional compounds as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 2A:
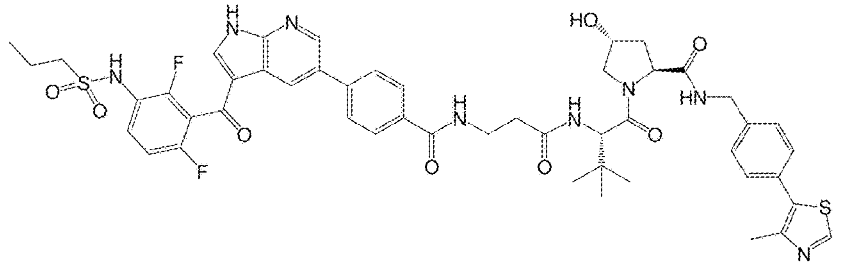
FIG. 2A. Table 1A. Exemplary protein targeting moieties and compounds of the present disclosure.
Figure 2A:
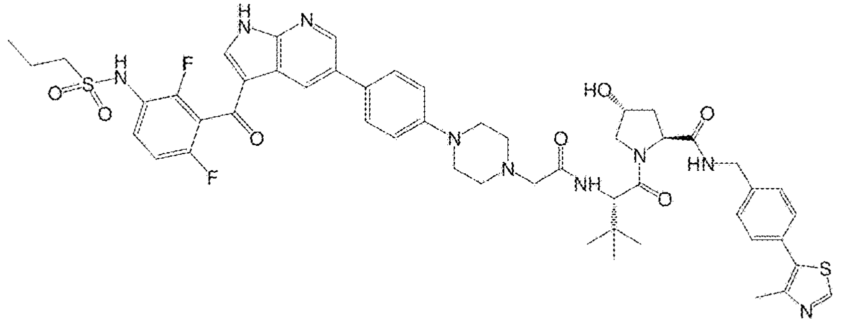
Figure 2A:
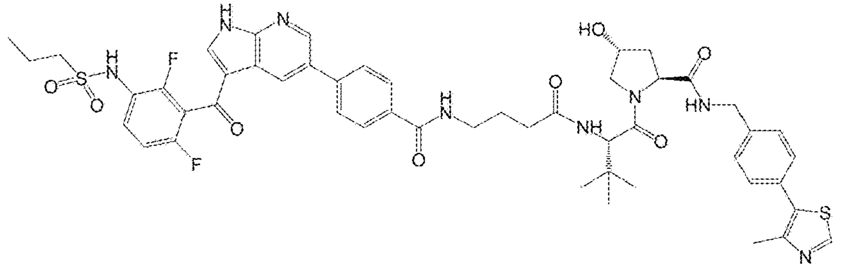
Figure 2A:
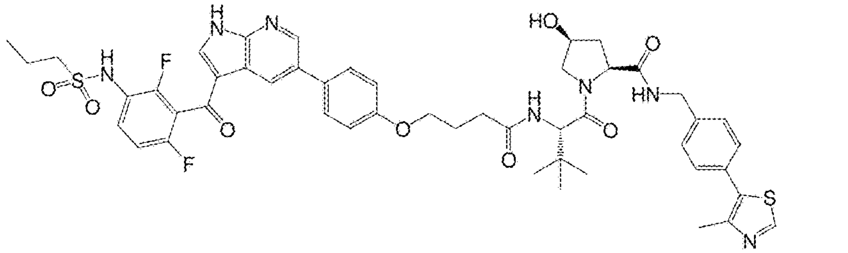
Figure 2A:
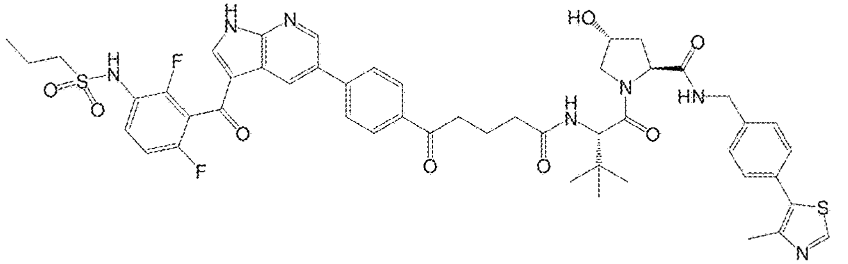
Figure 2A:
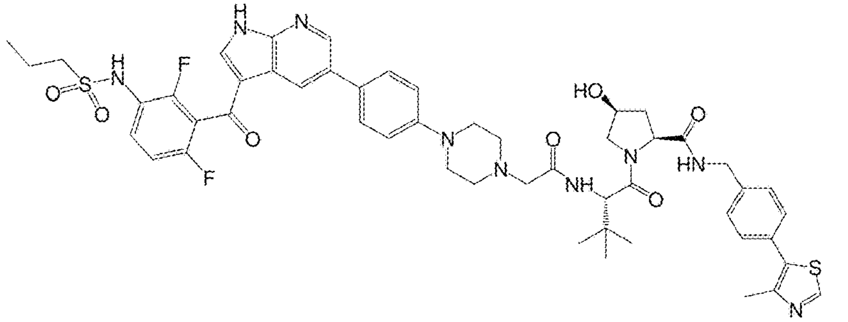
Figure 2A:
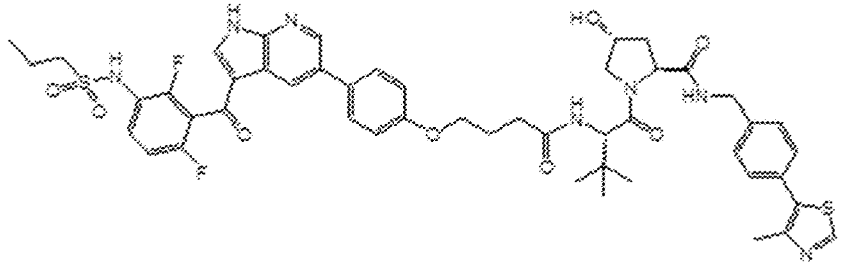
Figure 2B:
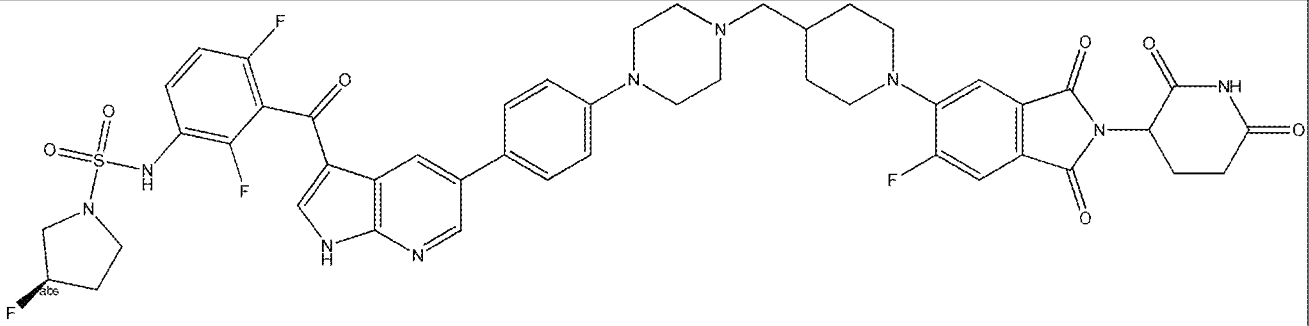
FIG. 2B. Table 1B. Exemplary protein targeting moieties and compounds of the present disclosure.
Figure 2B:
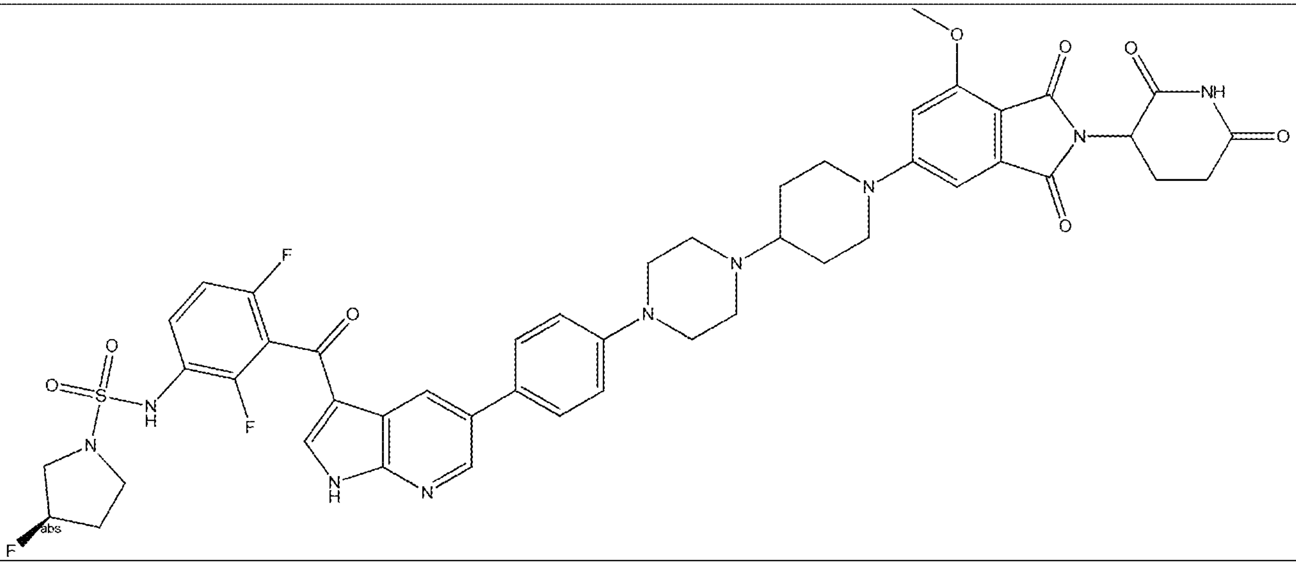
Figure 2B:
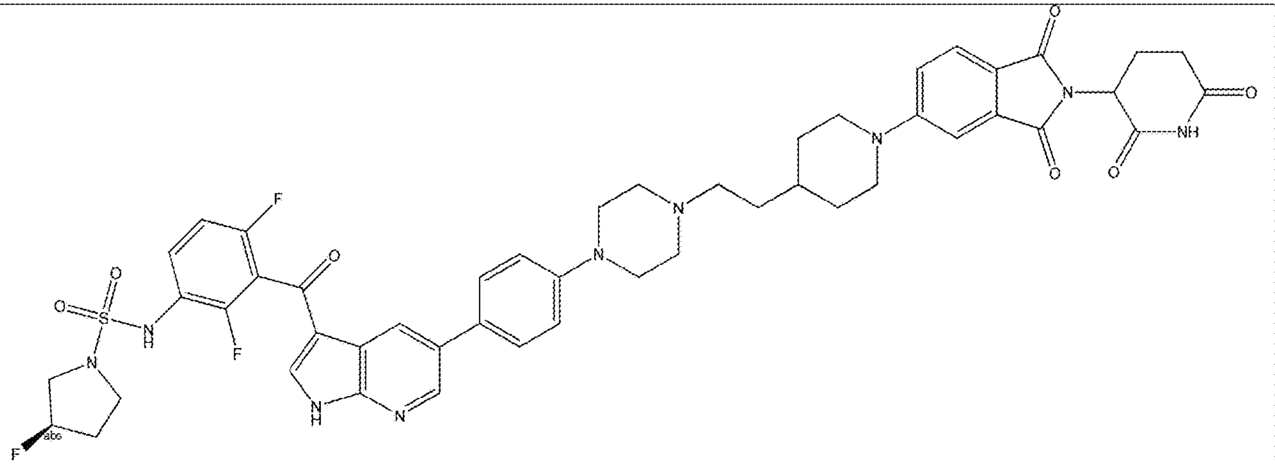
Figure 2B:
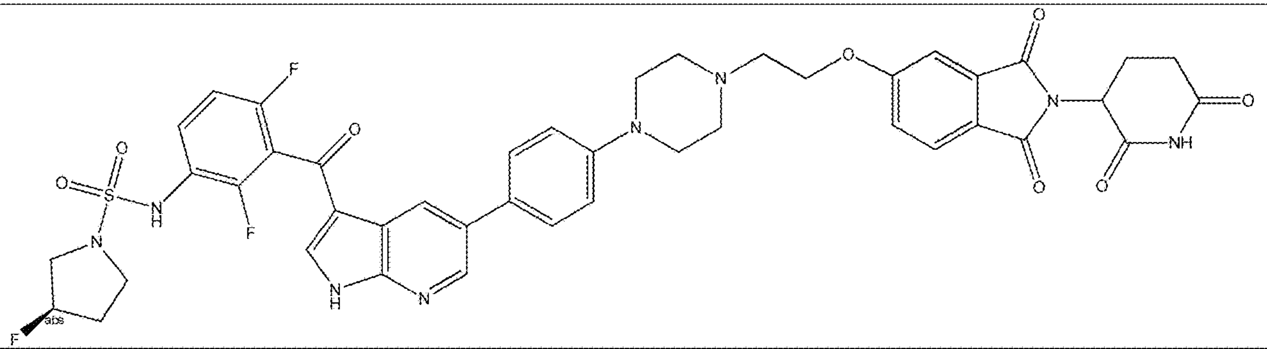
Figure 2B:
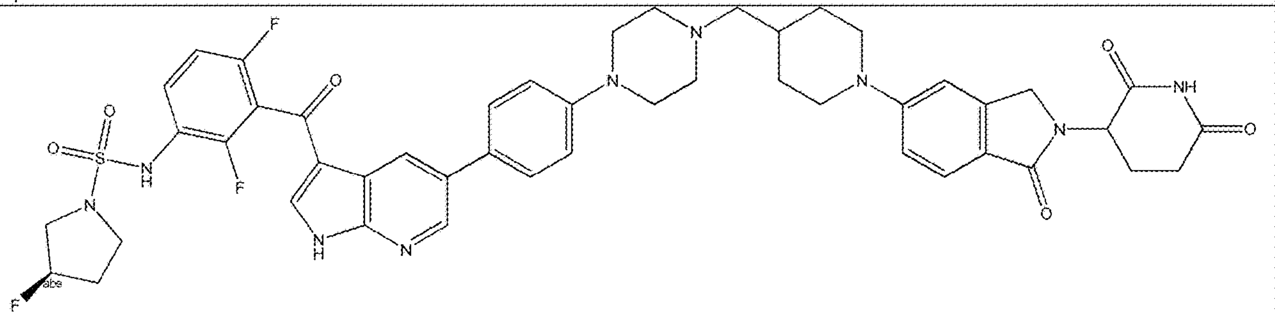
Figure 2B:
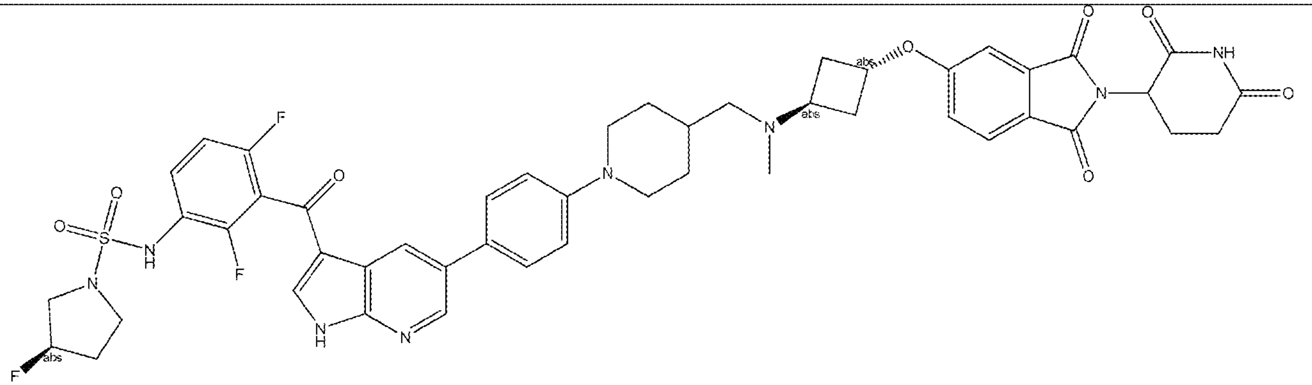
Figure 2B:
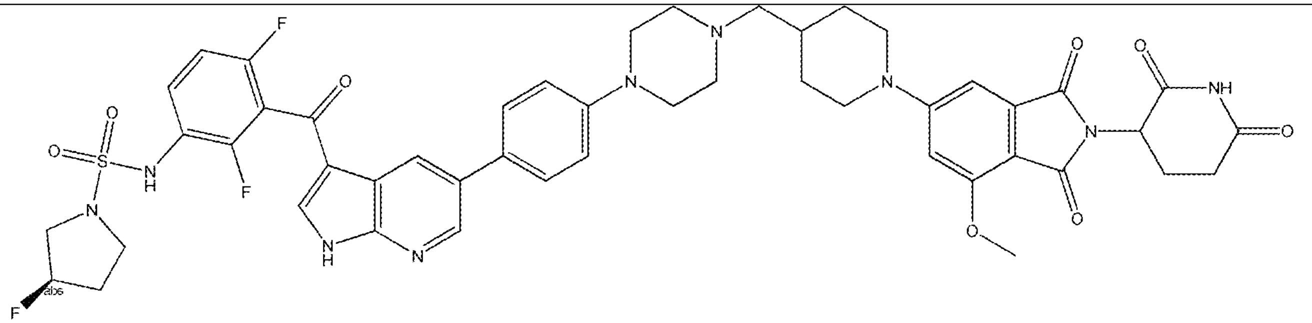
Figure 2B:
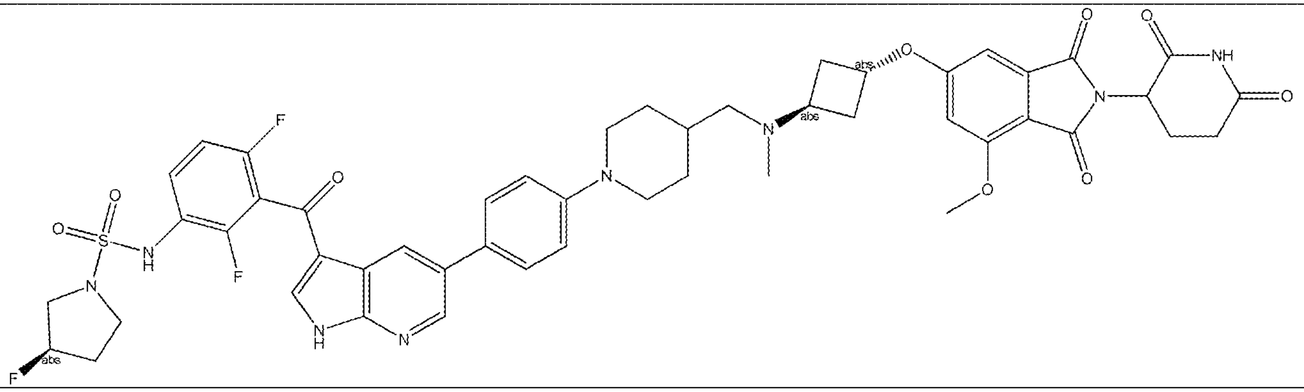
Figure 2B:
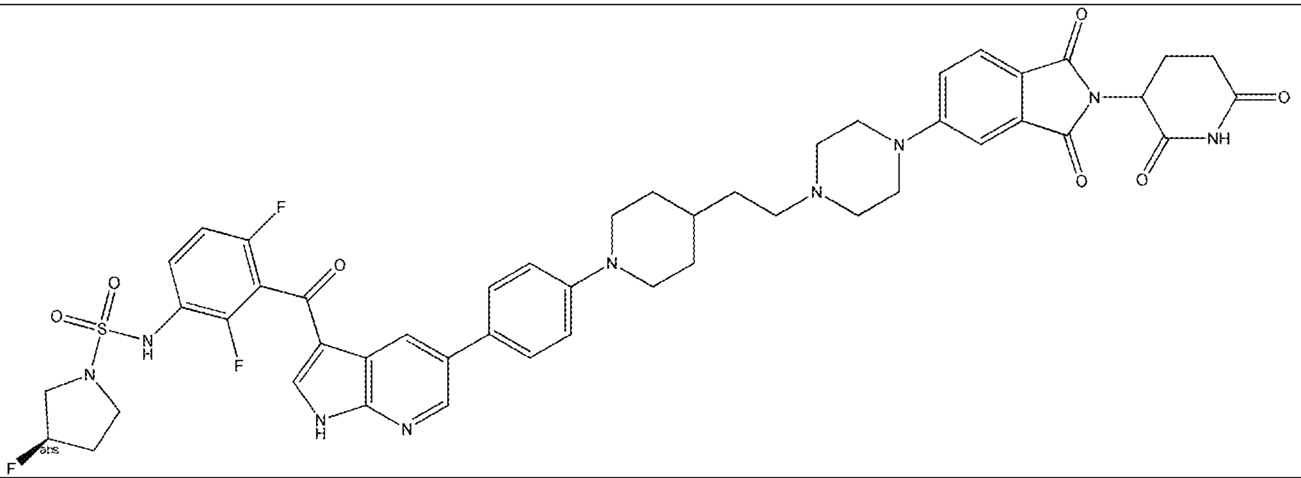
Figure 2B:
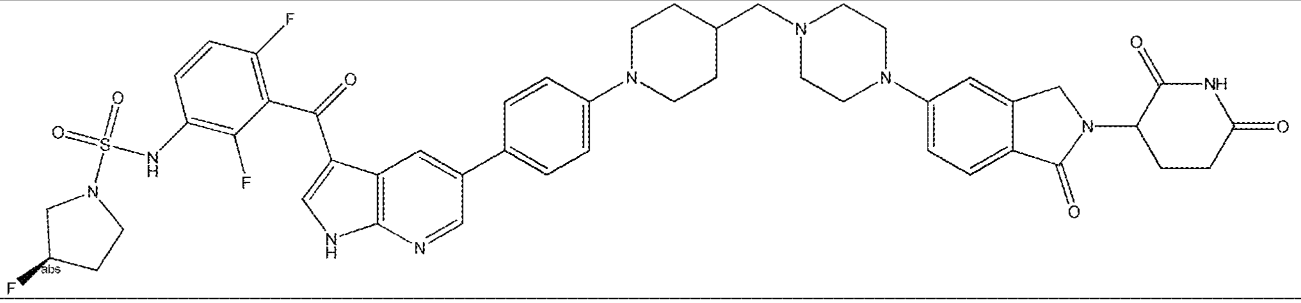
Figure 2B:
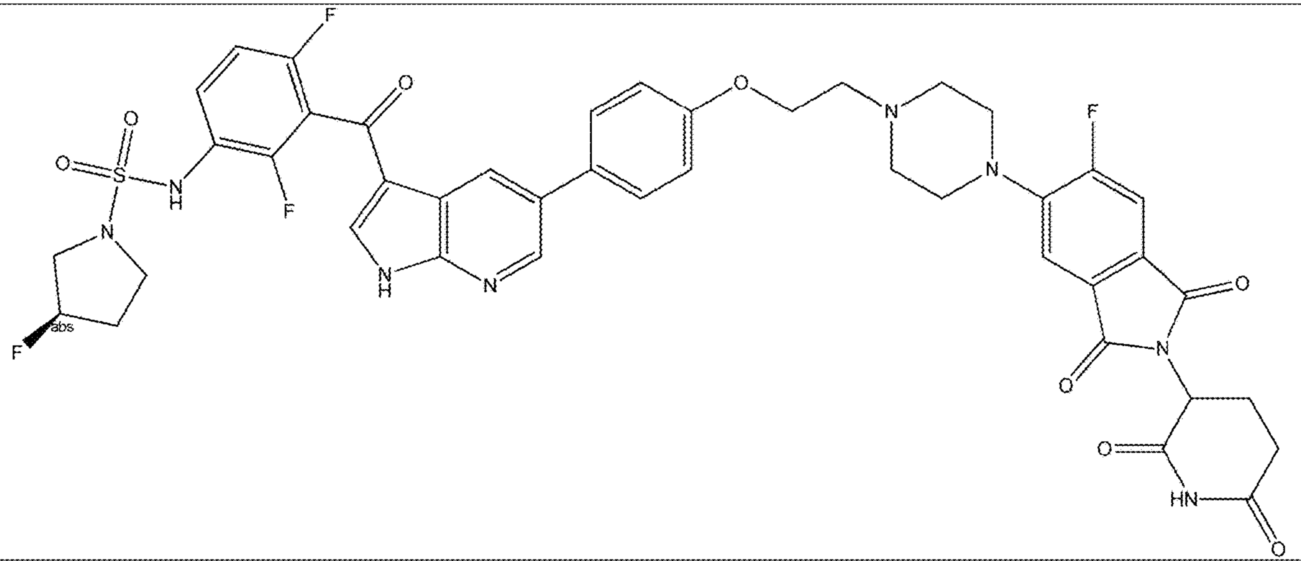
Figure 2B:
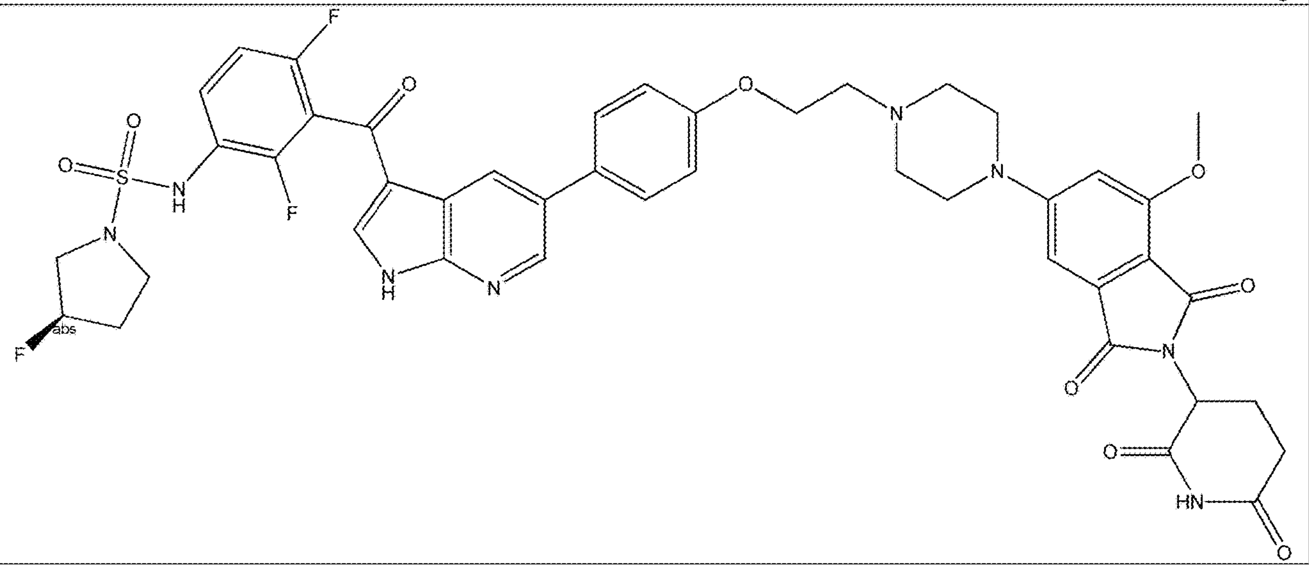
Figure 2B:
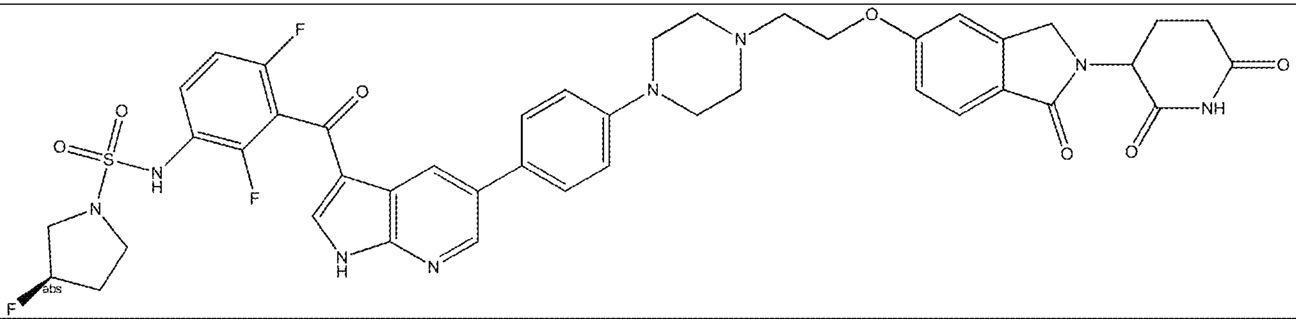
Figure 2B:
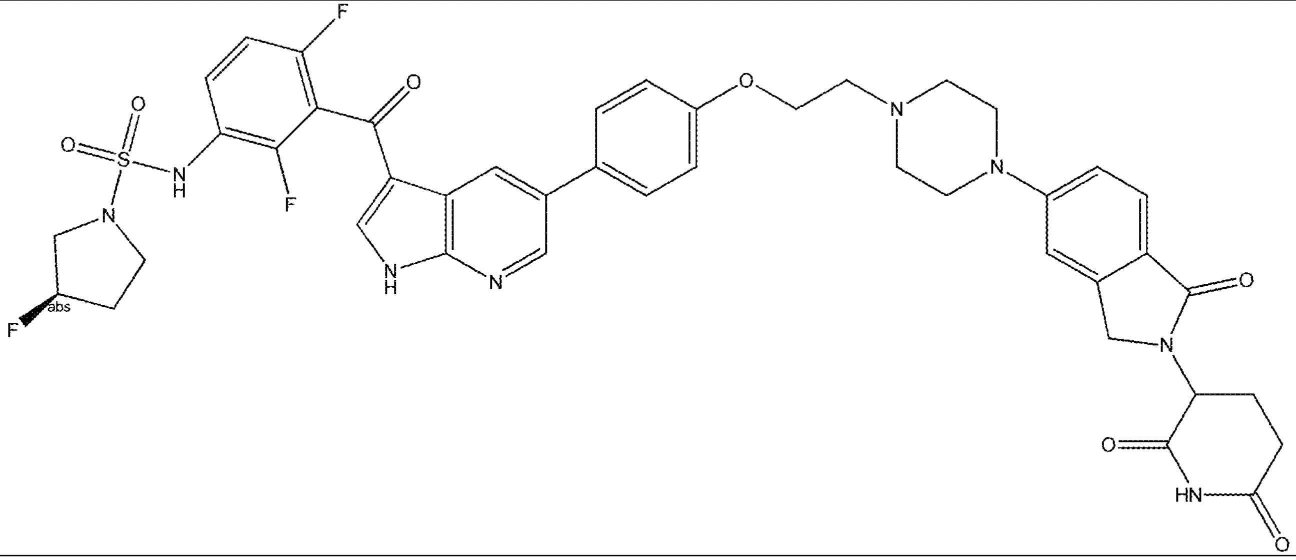
Figure 2B:
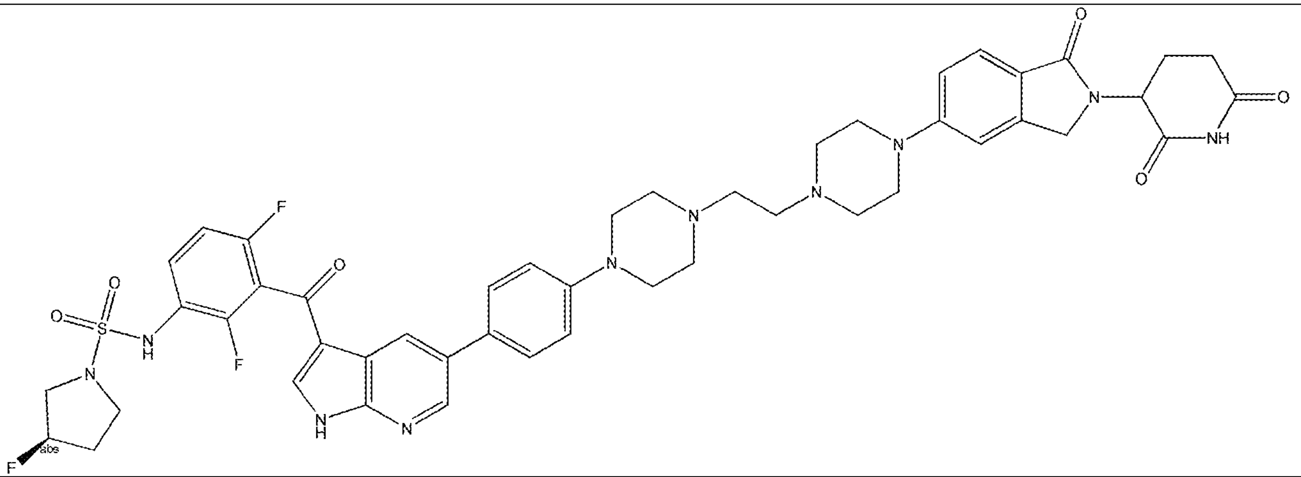
Figure 2B:
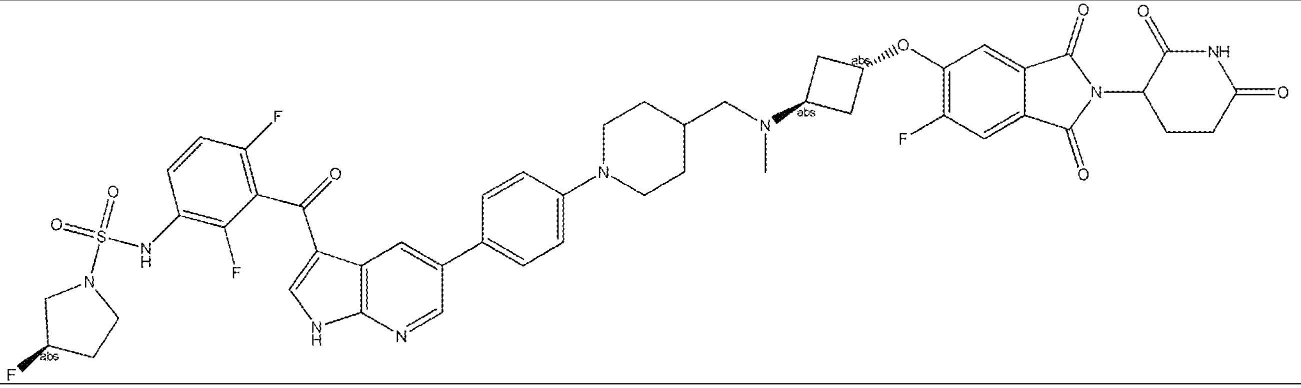
Figure 2B:
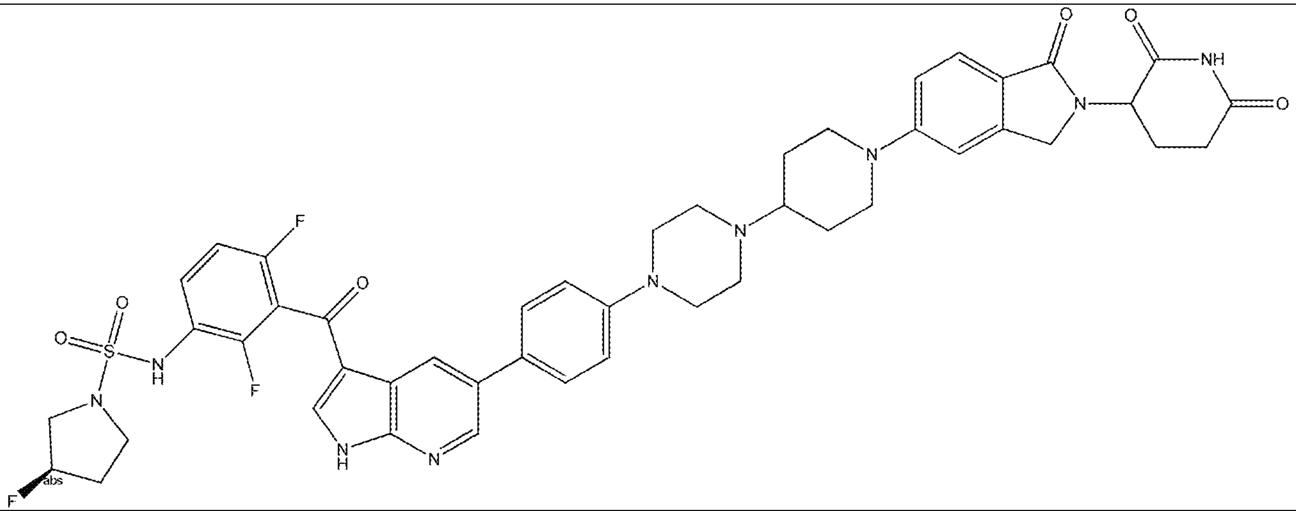
Figure 2B:
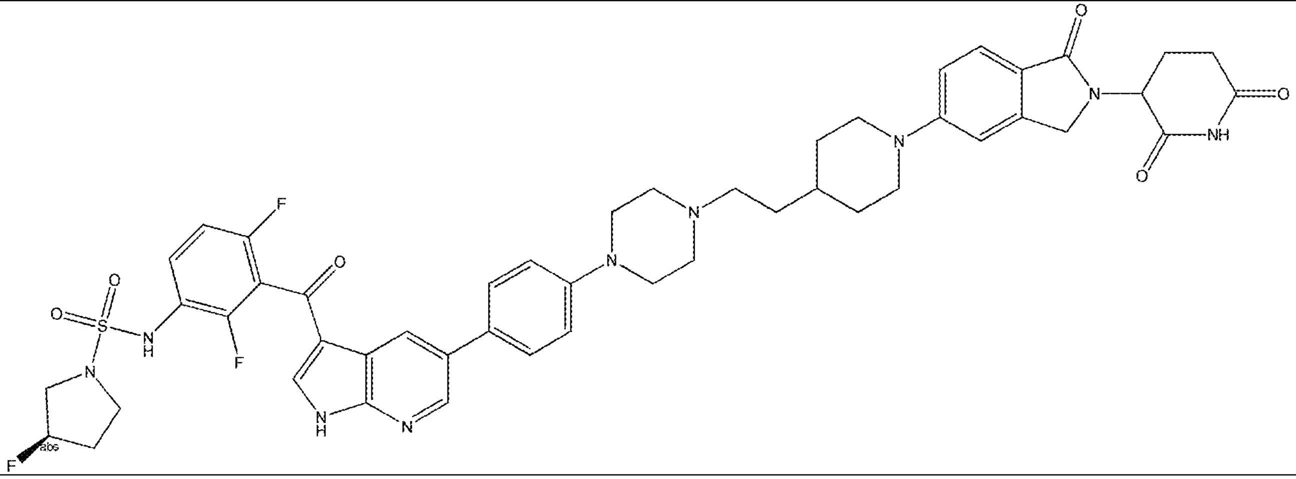
Figure 2B:
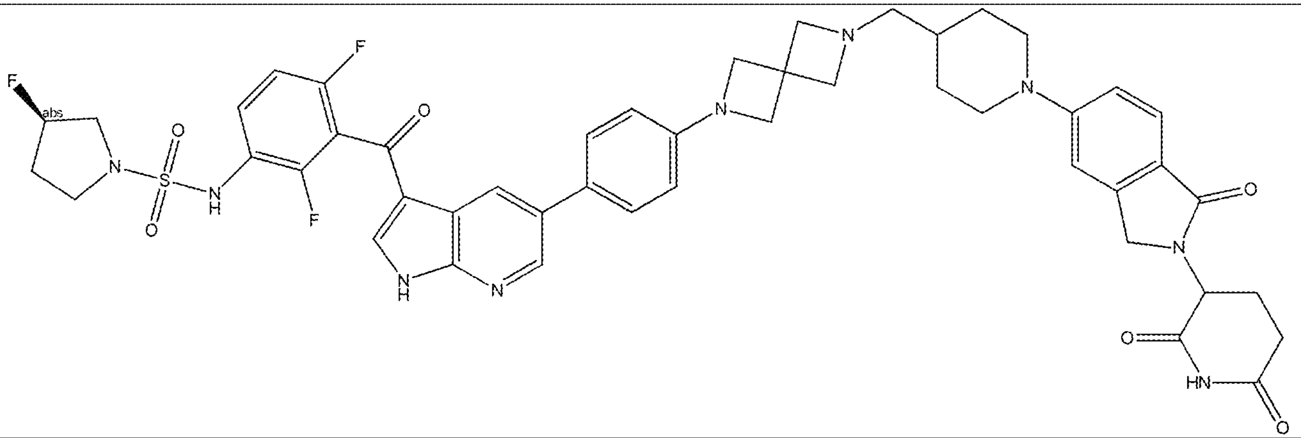
Figure 2B:
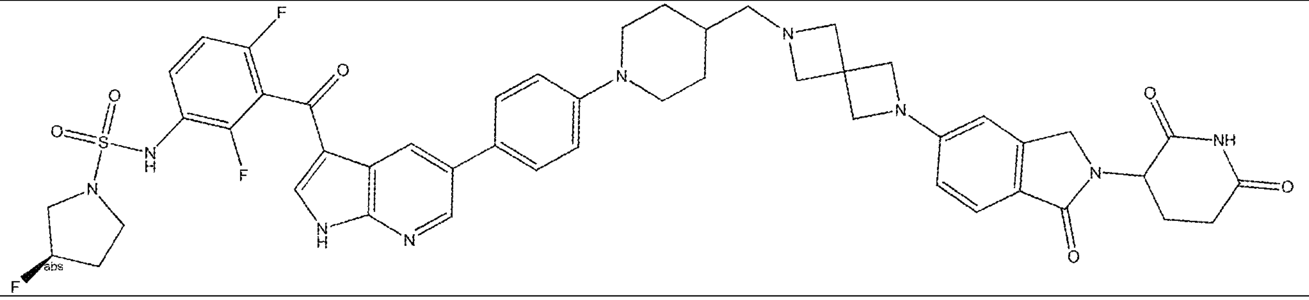
Figure 2B:
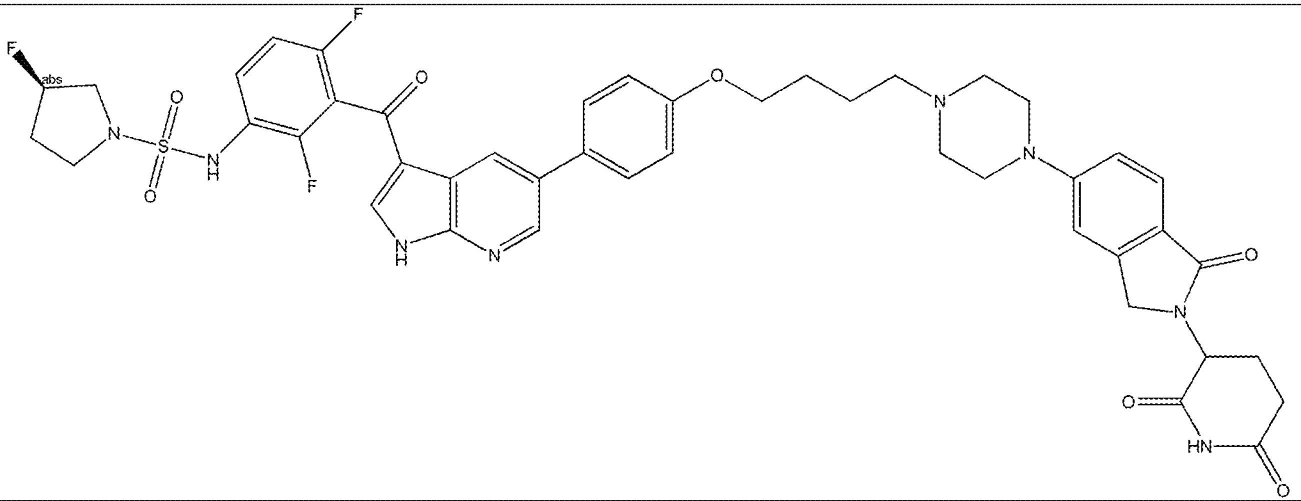
Figure 2B:
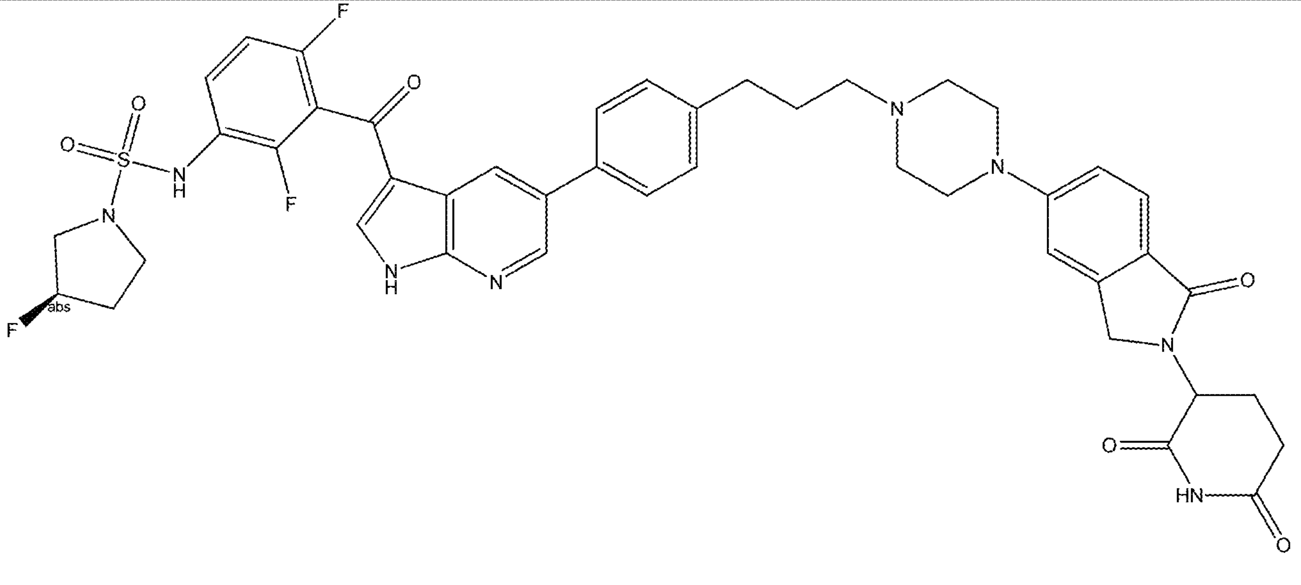
Figure 2B:
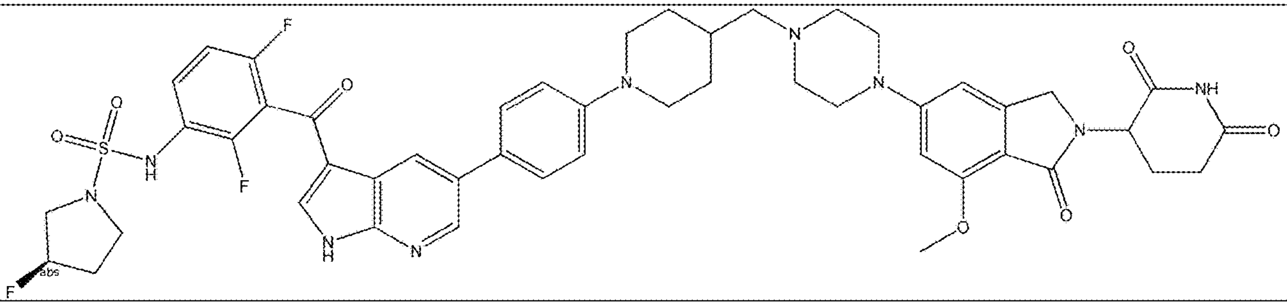
Figure 2B:
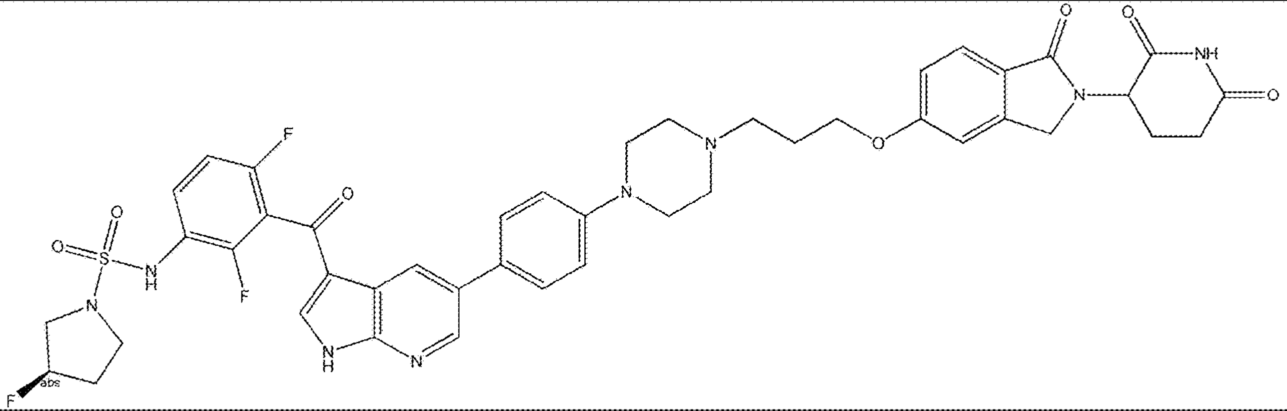
Figure 2B:
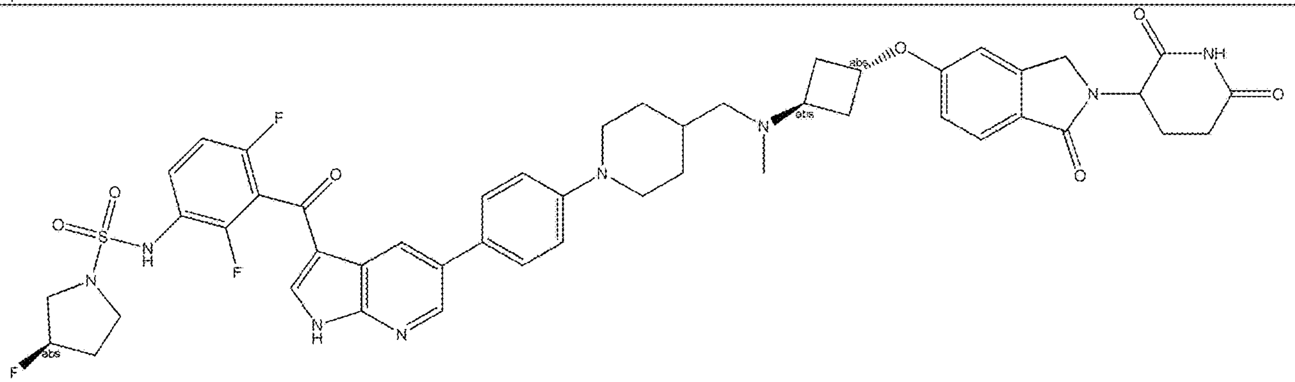
Figure 2B:
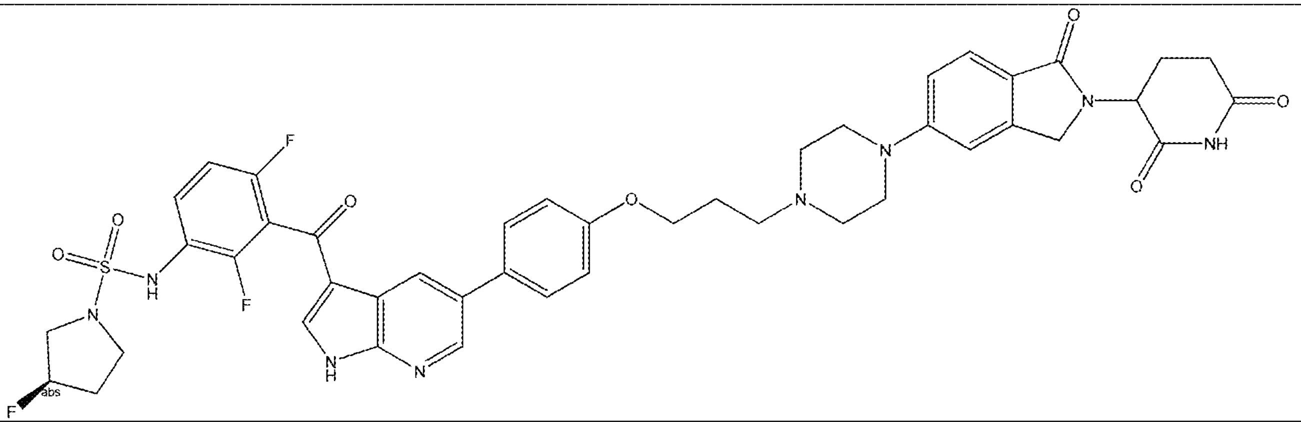
Figure 2B:
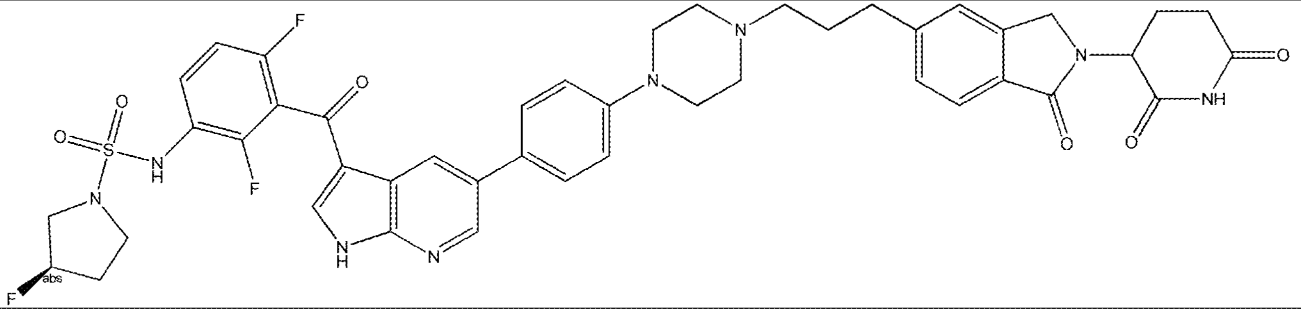
Figure 2B:
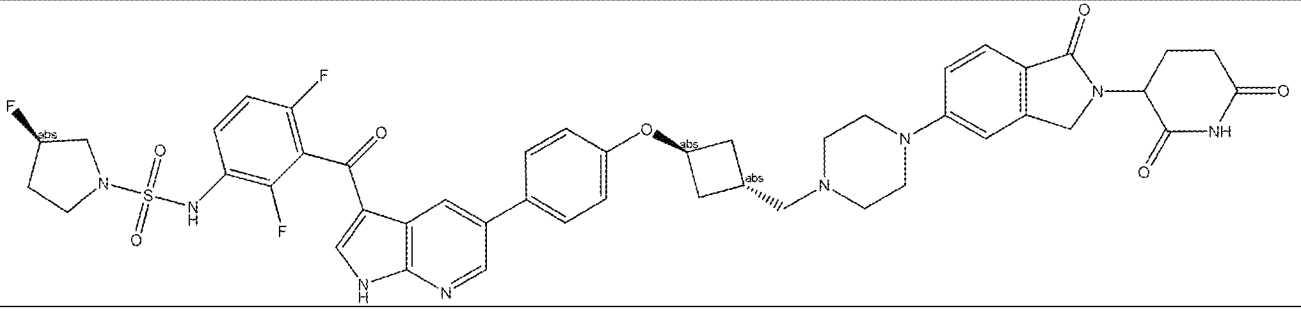
Figure 2B:
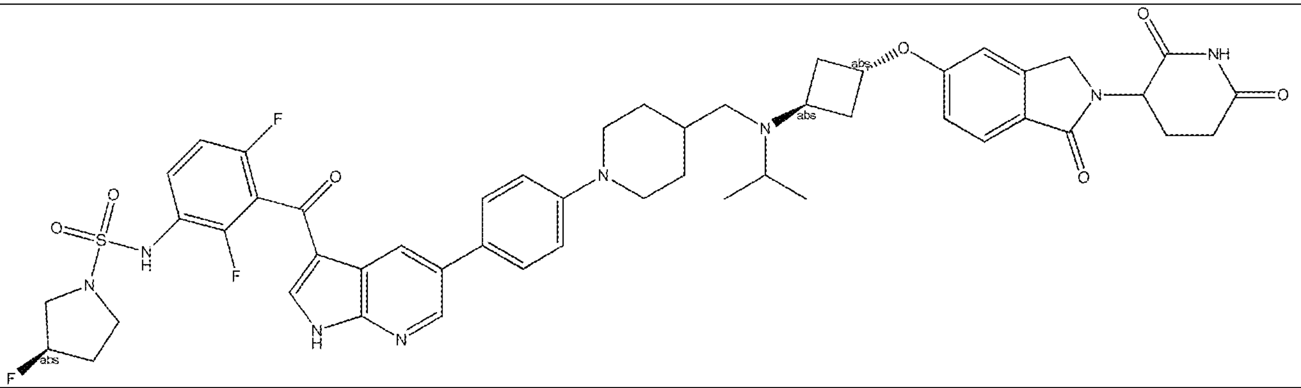
Figure 2B:
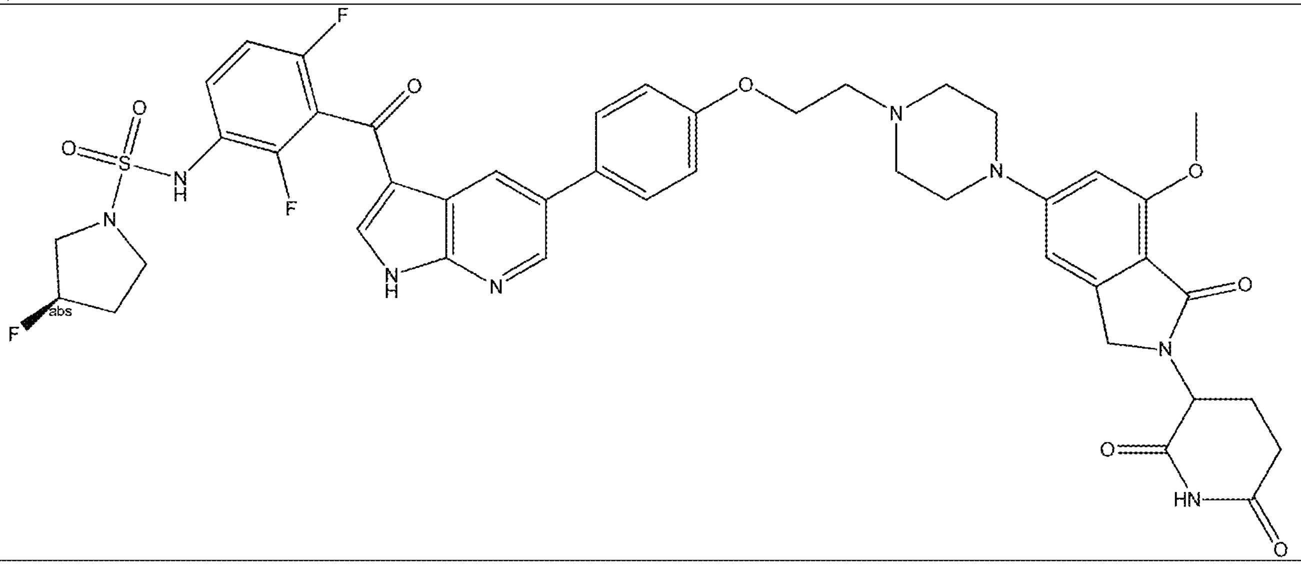
Figure 2B:
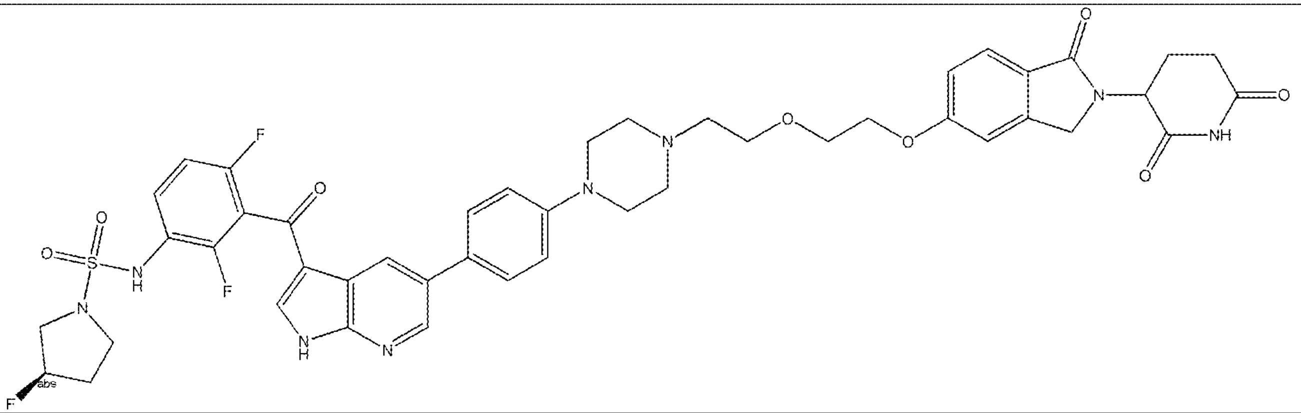
Figure 2B:
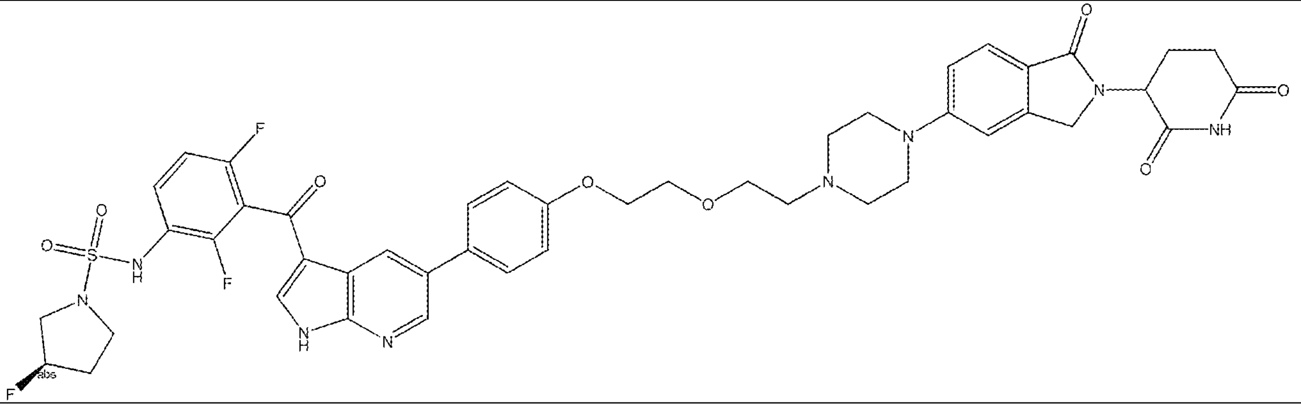
Figure 2B:
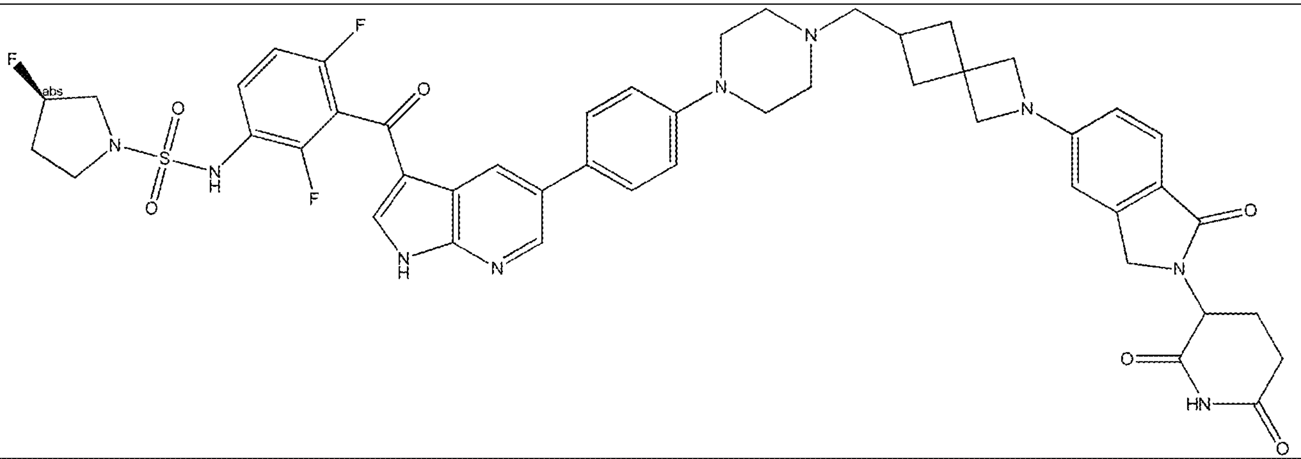
Figure 2B:
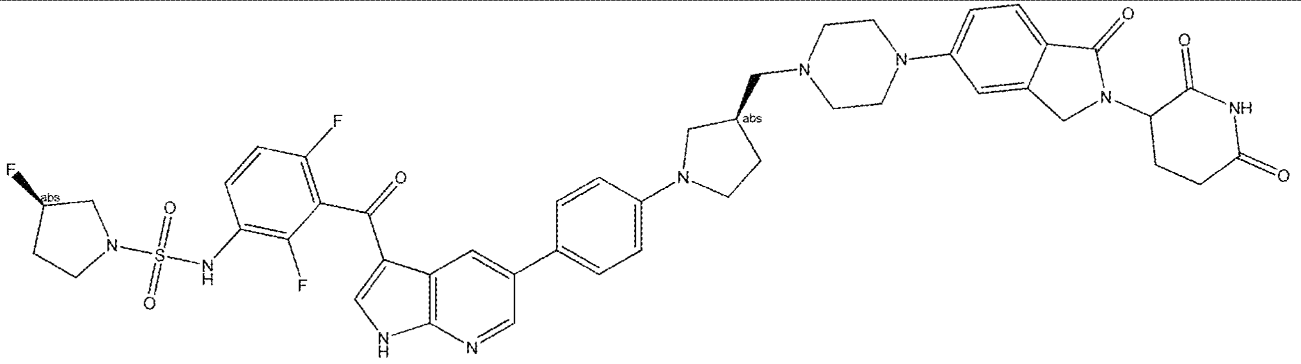
Figure 2B:
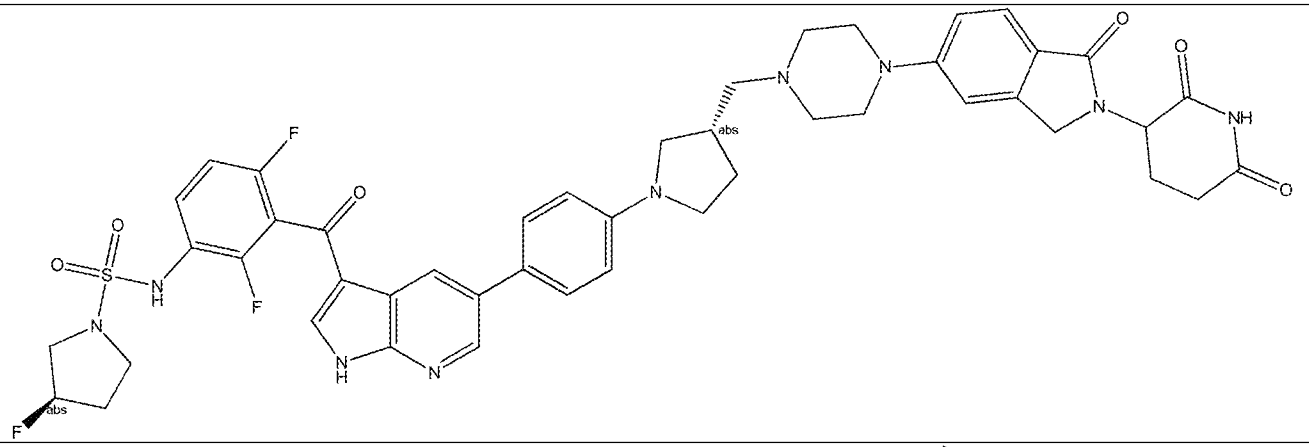
Figure 2B:
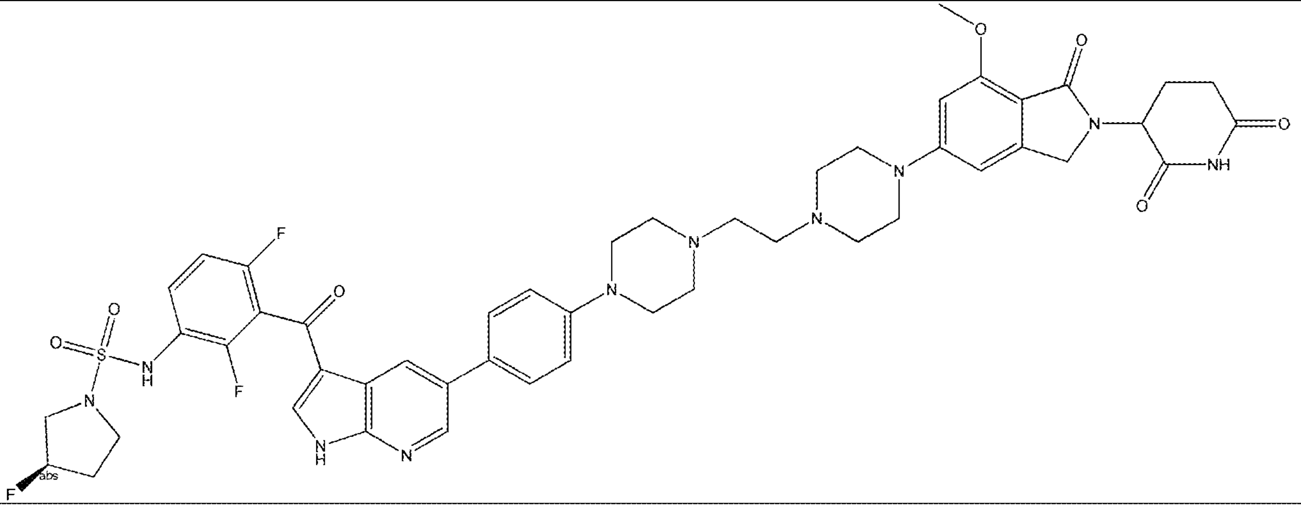
Figure 2B:
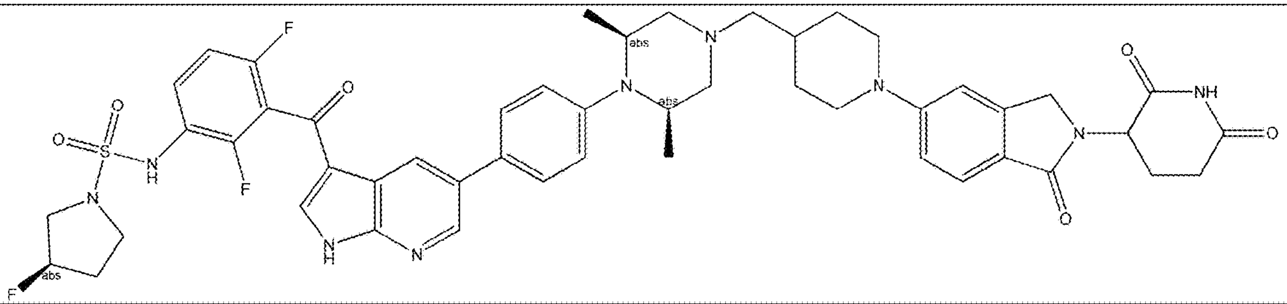
Figure 2B:
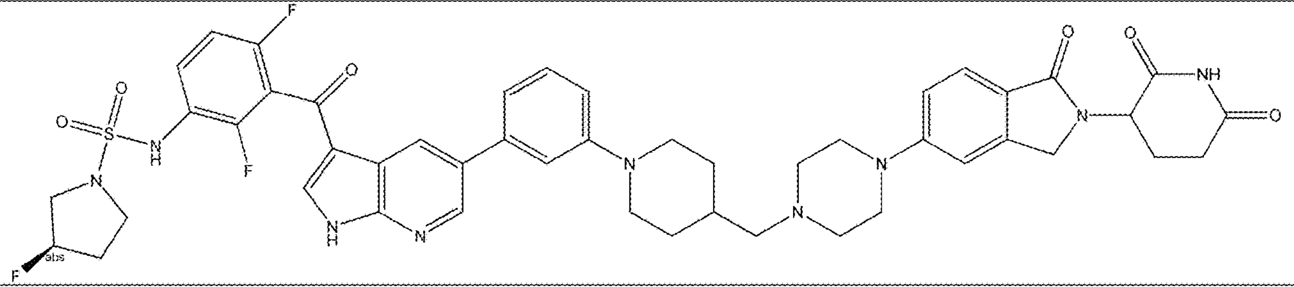
Figure 2B:
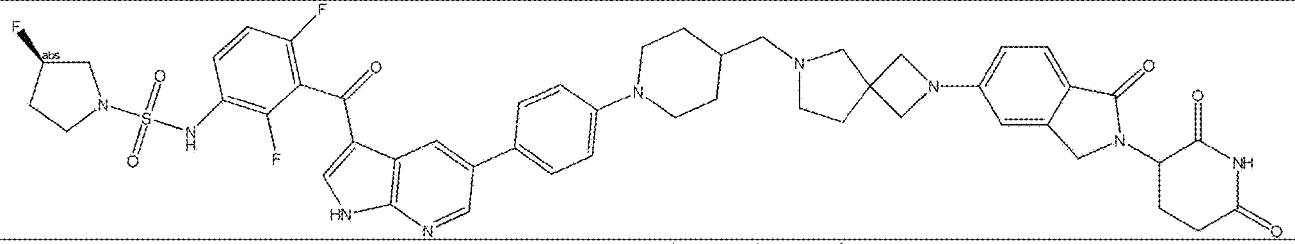
Figure 2B:
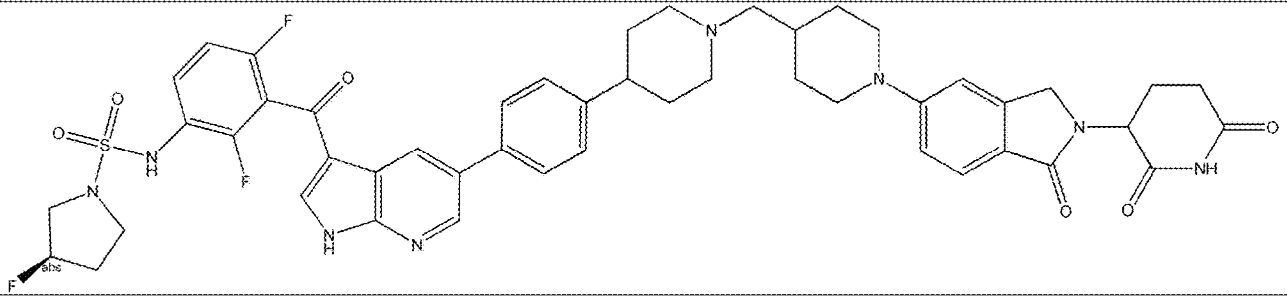
Figure 2B:
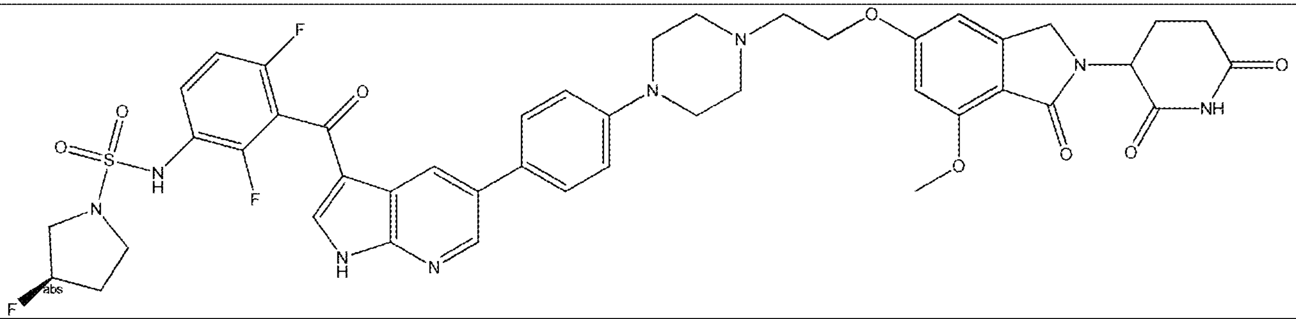
Figure 2B:
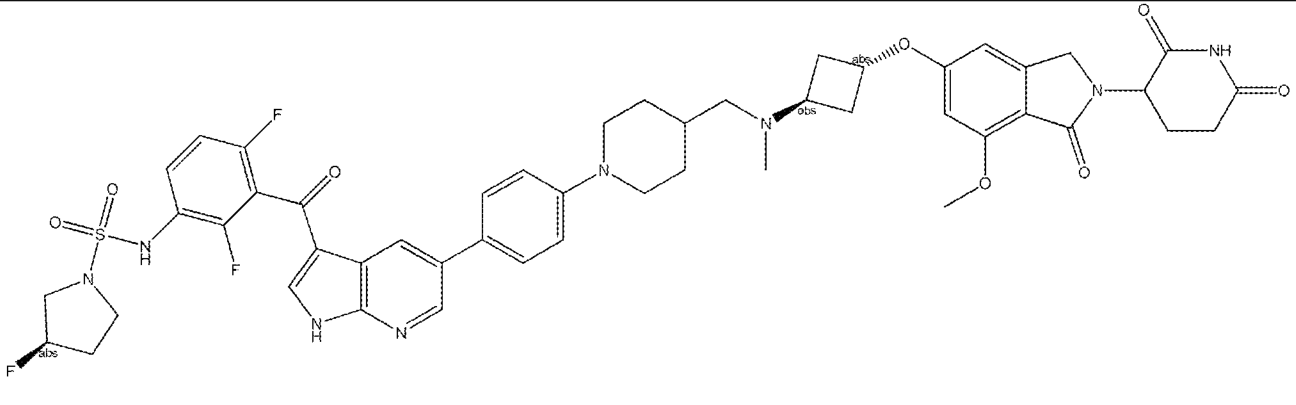
Figure 2B:
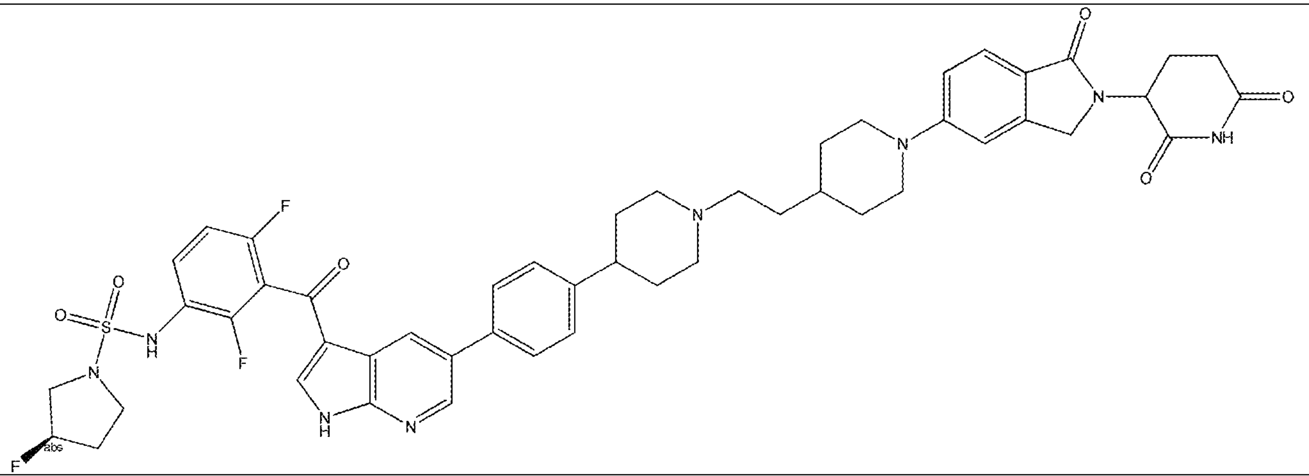
Figure 2B:
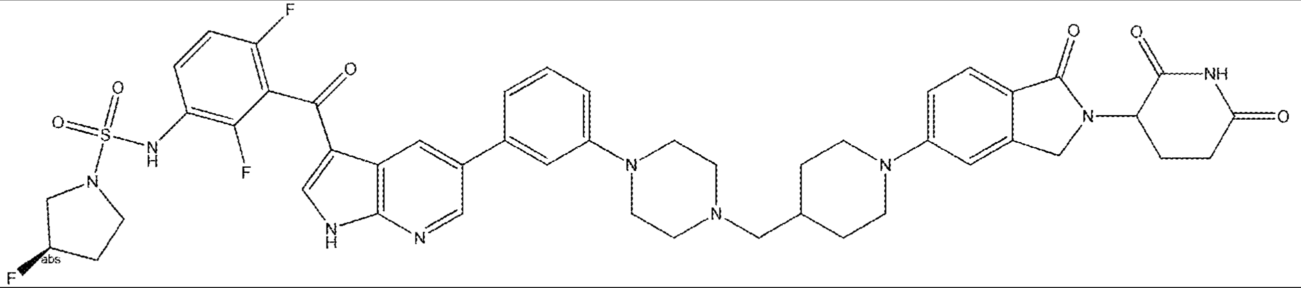
Figure 2B:
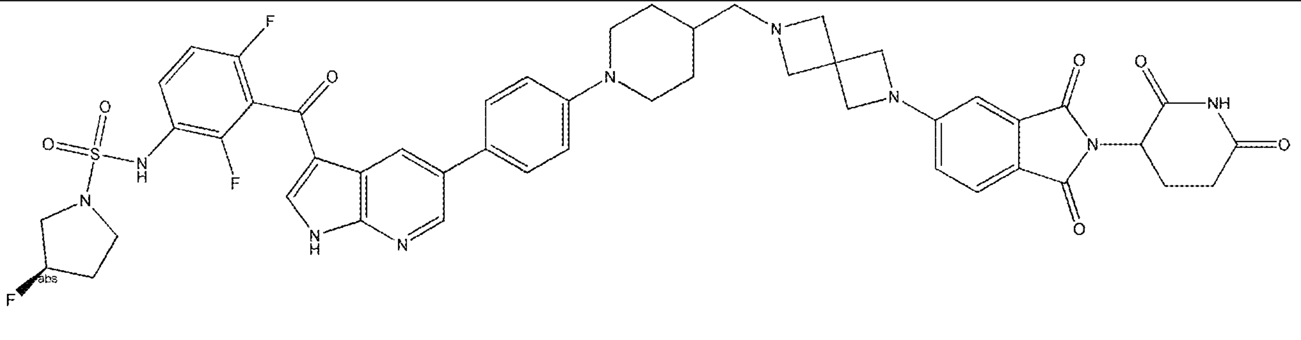
Figure 2B:
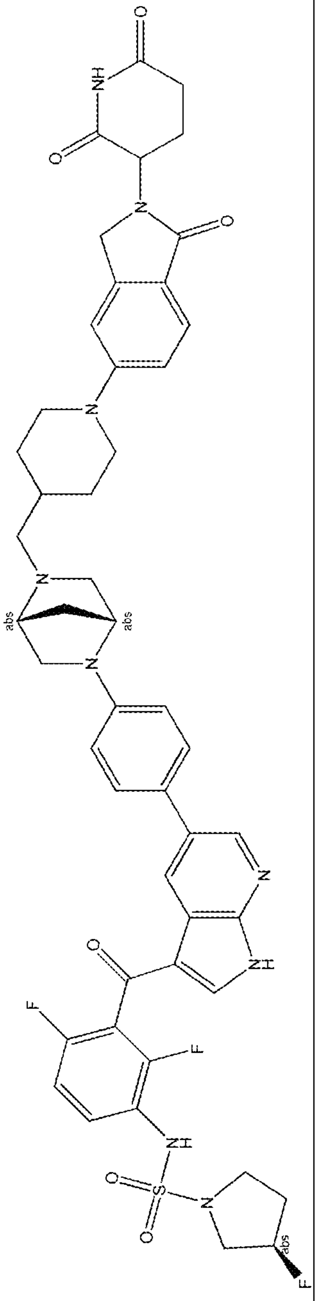
Figure 2B:
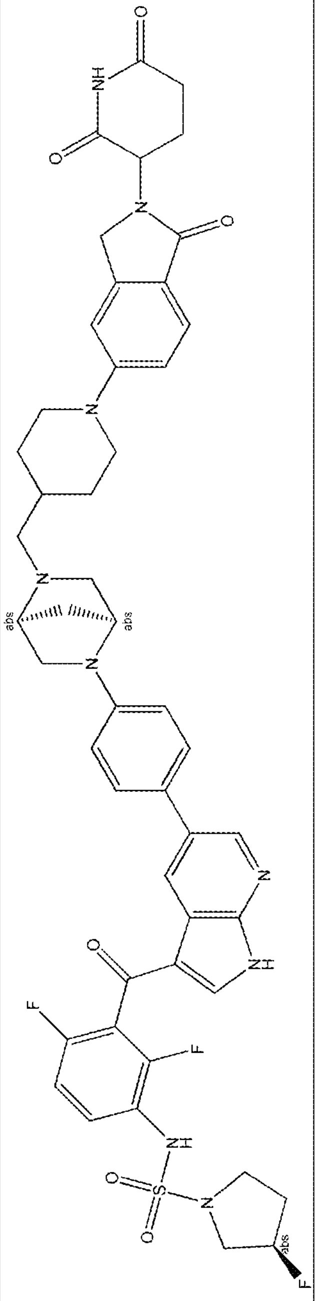
Figure 2B:
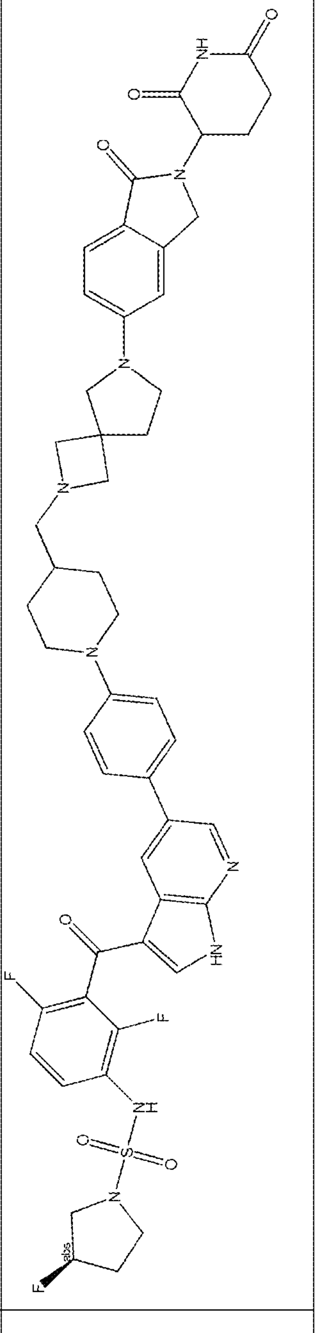
Figure 2B:
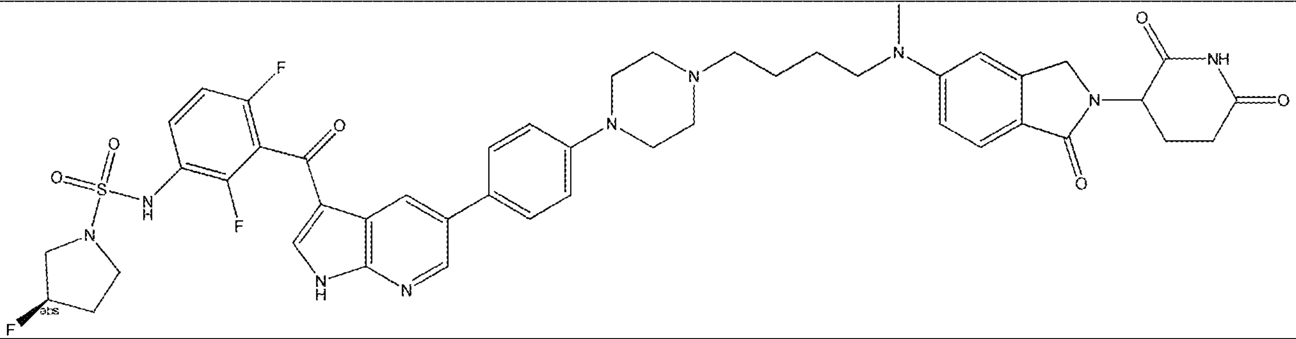
Figure 2B:
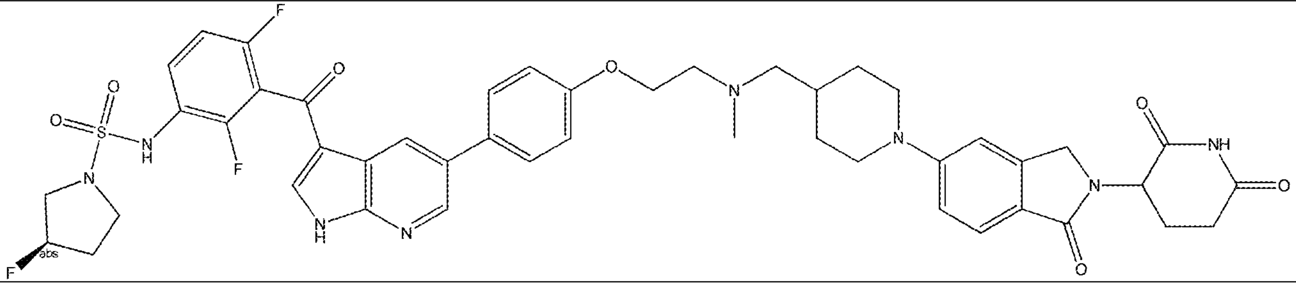
Figure 2B:
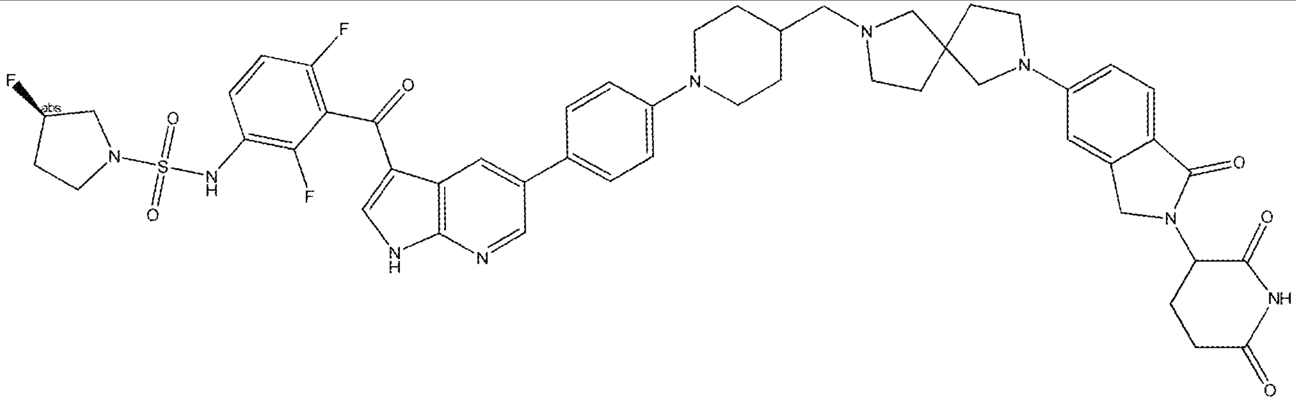
Figure 2B:
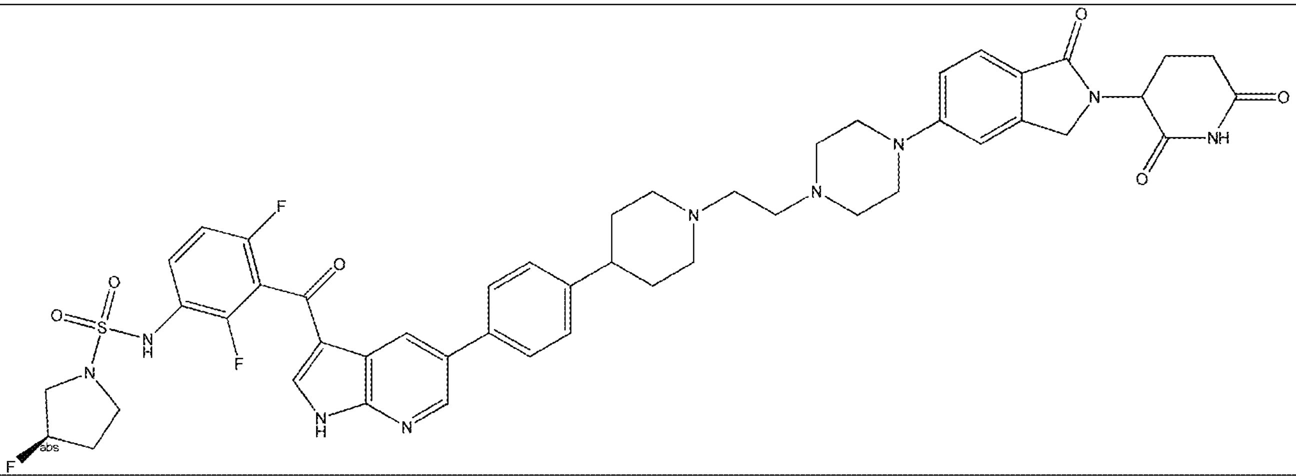
Figure 2B:
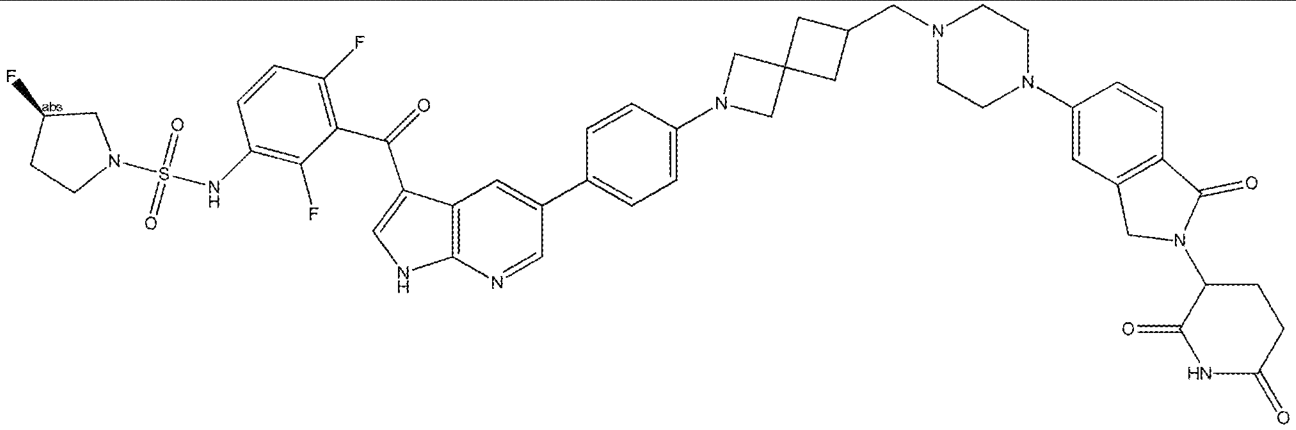
Figure 2B:
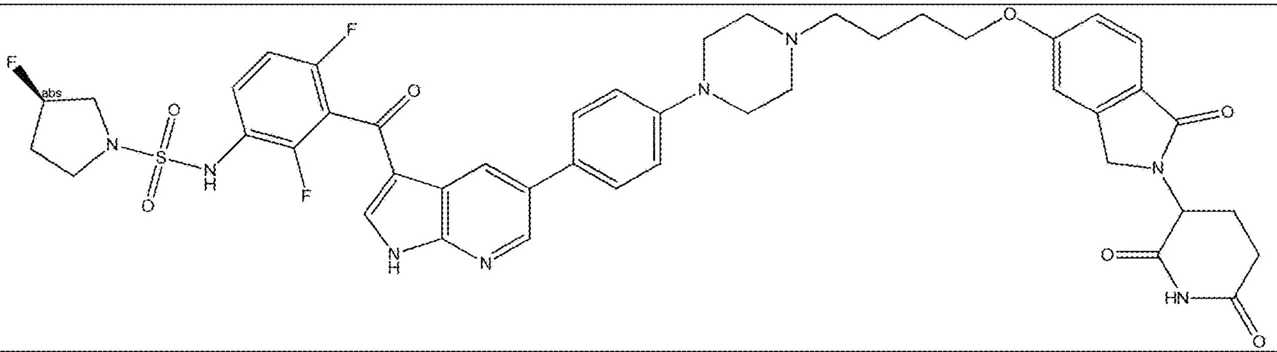
Figure 2B:
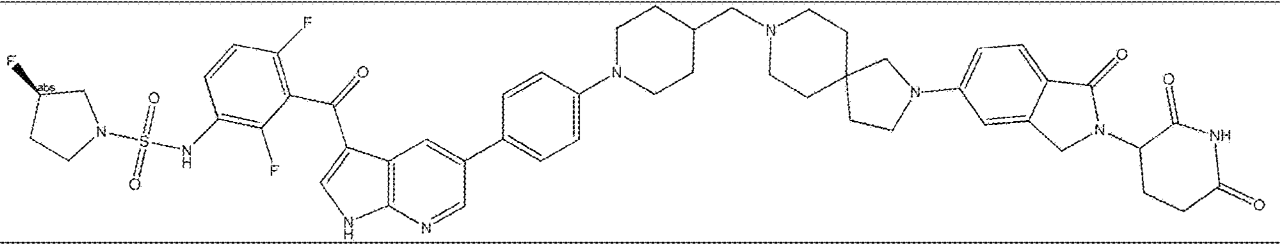
Figure 2B:
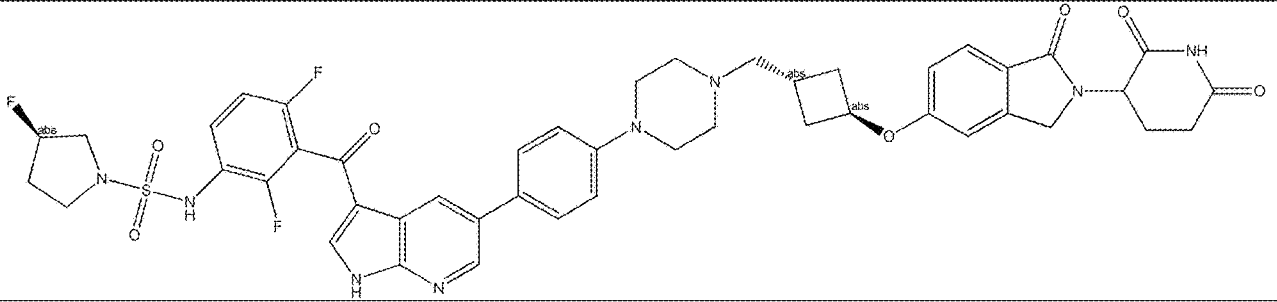
Figure 2B:
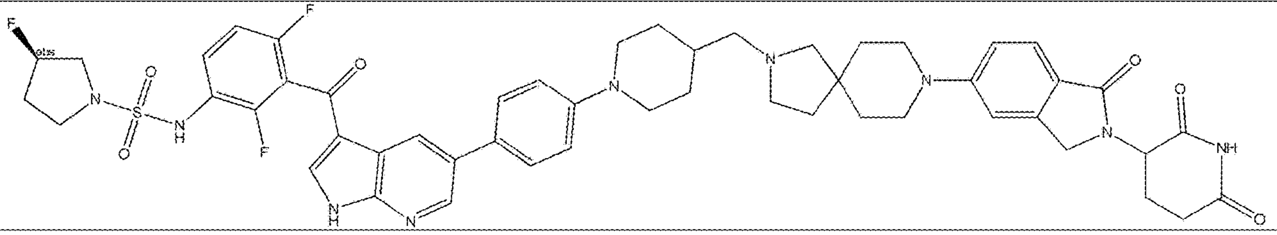
Figure 2B:
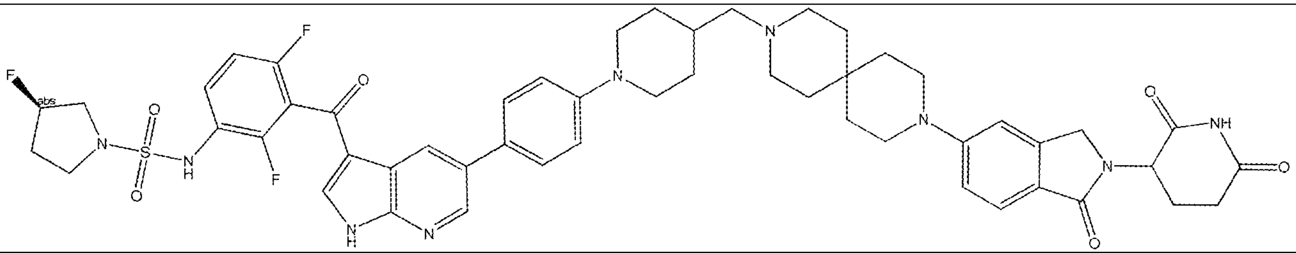
Figure 2B:
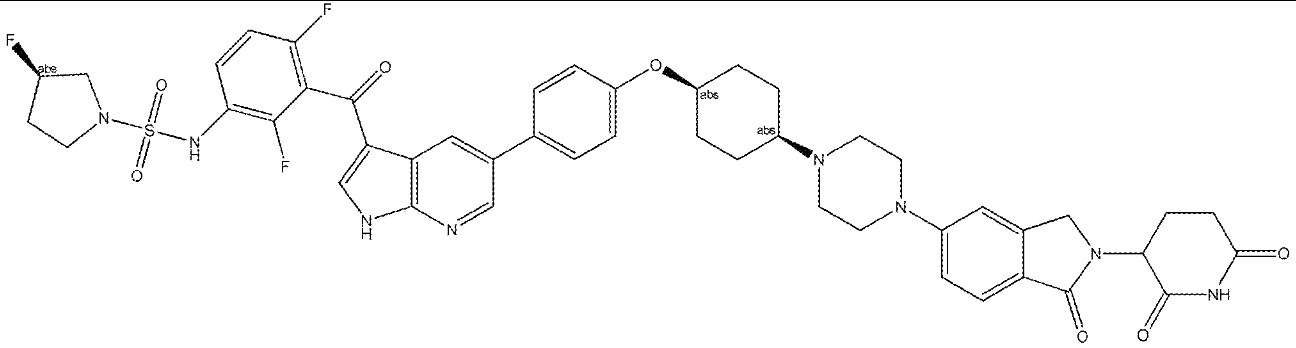
Figure 2B:
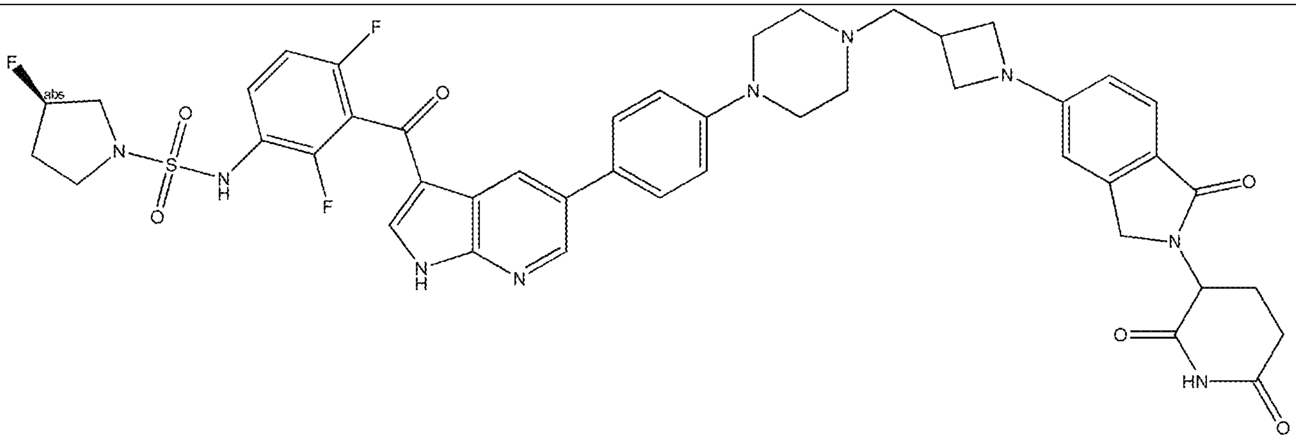
Figure 2B:
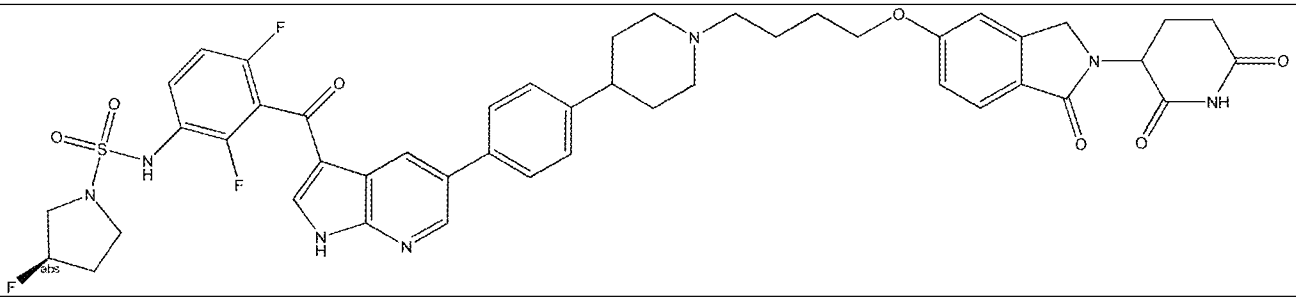
Figure 2B:
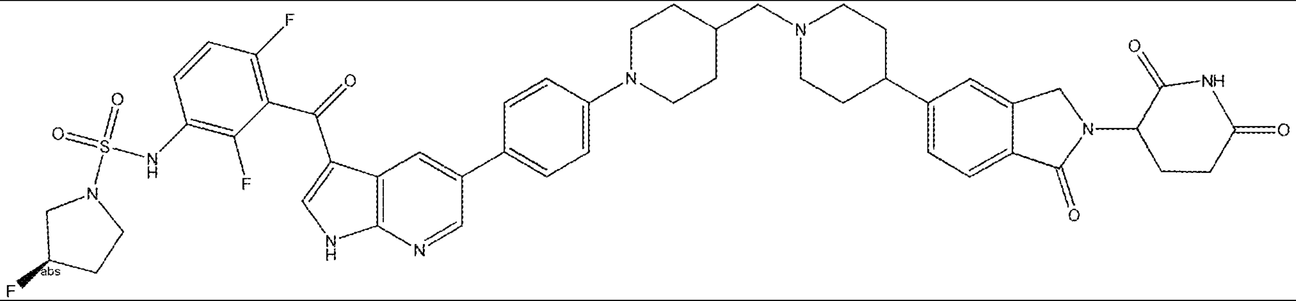
Figure 2B:
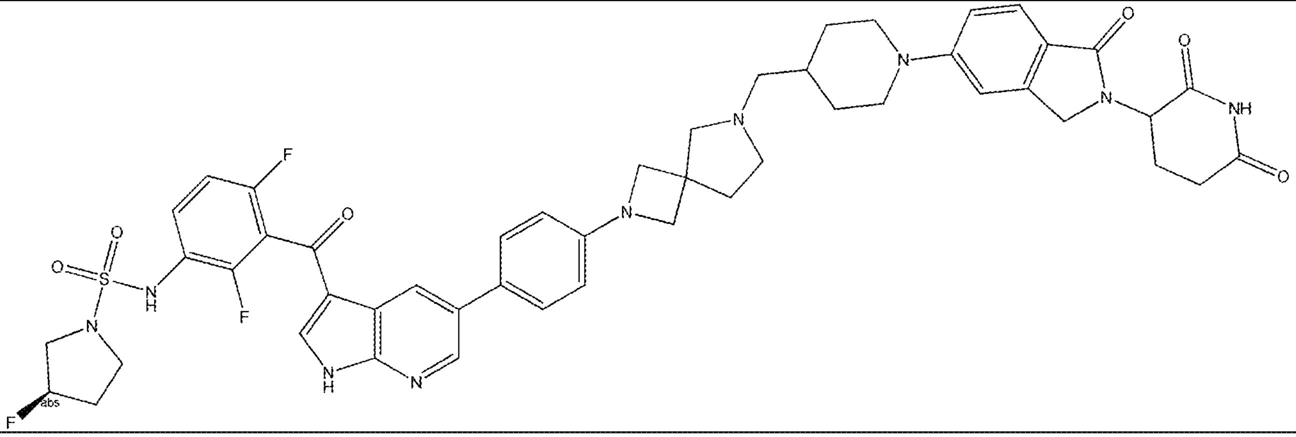
Figure 2B:
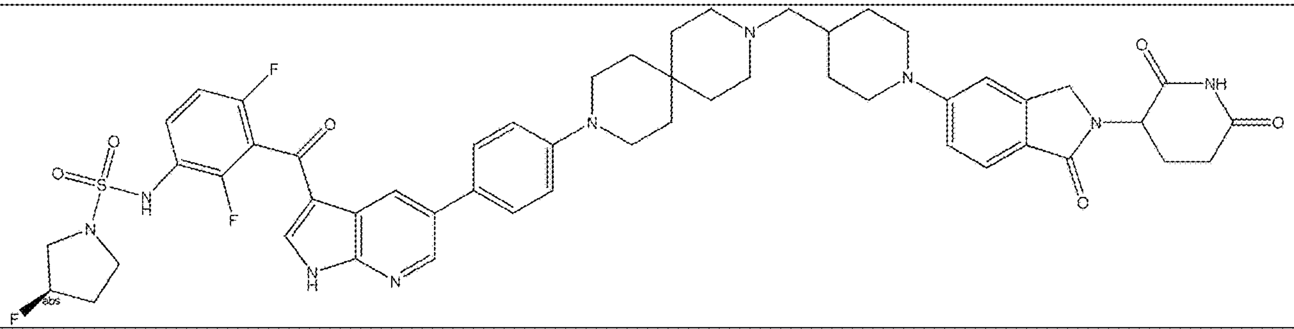
Figure 2B:
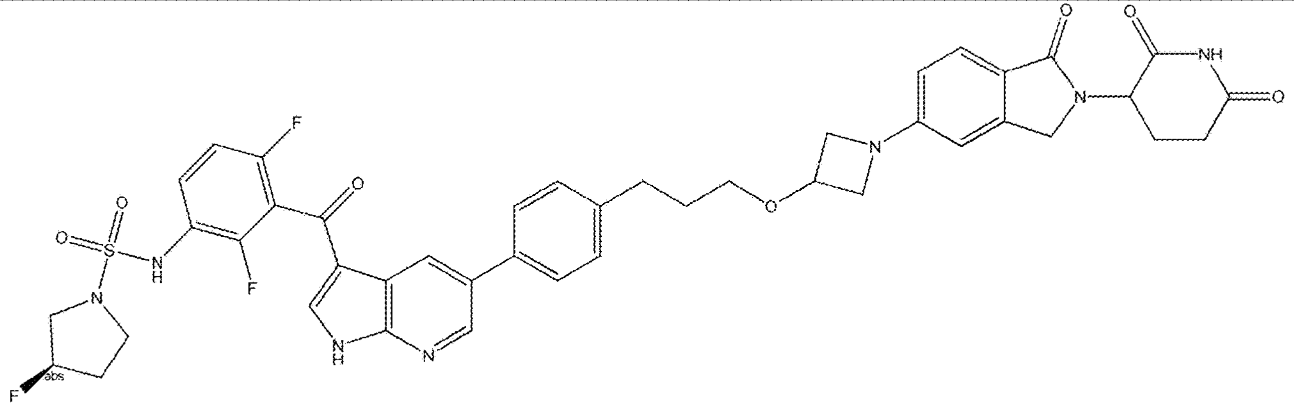
Figure 2B:
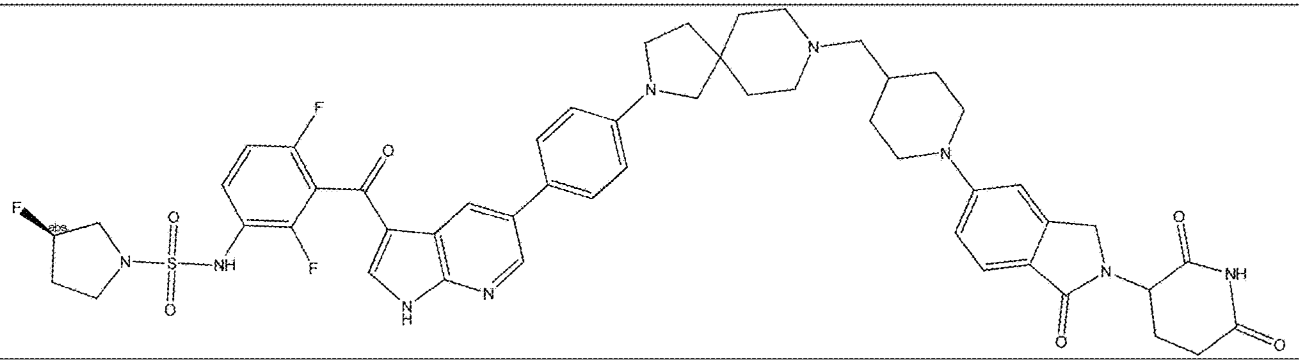
Figure 2B:
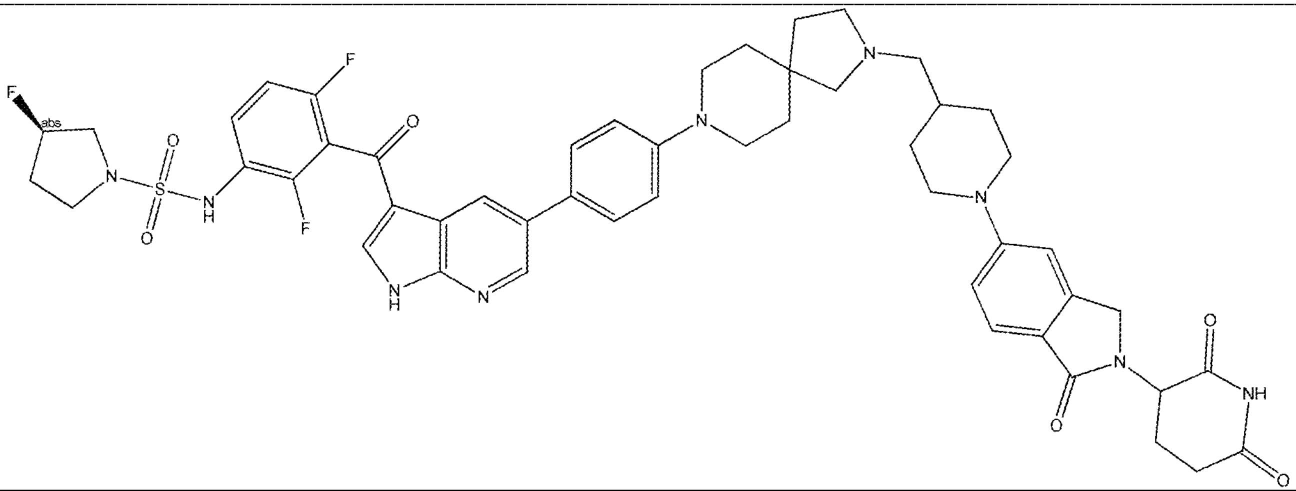
Figure 2B:
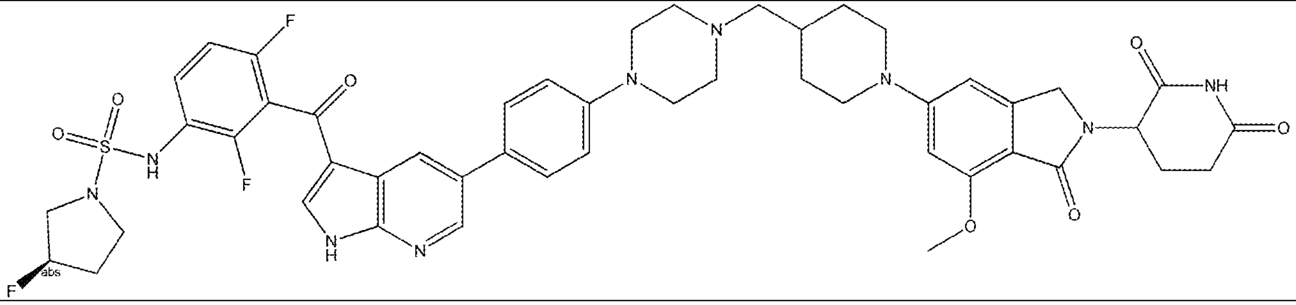
Figure 2B:
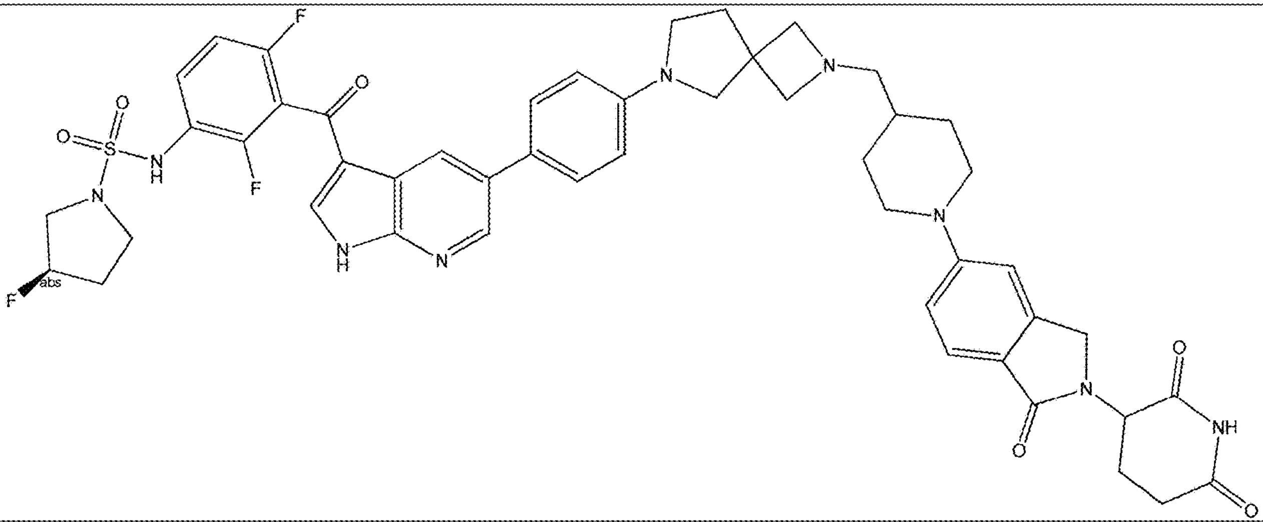
Figure 2B:
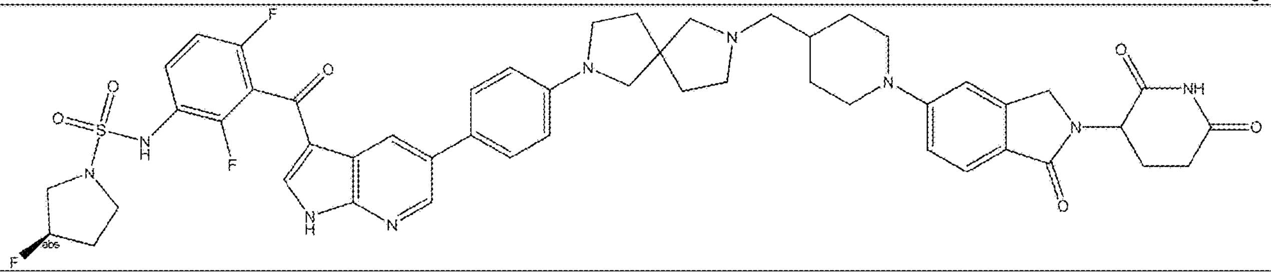
Figure 2B:
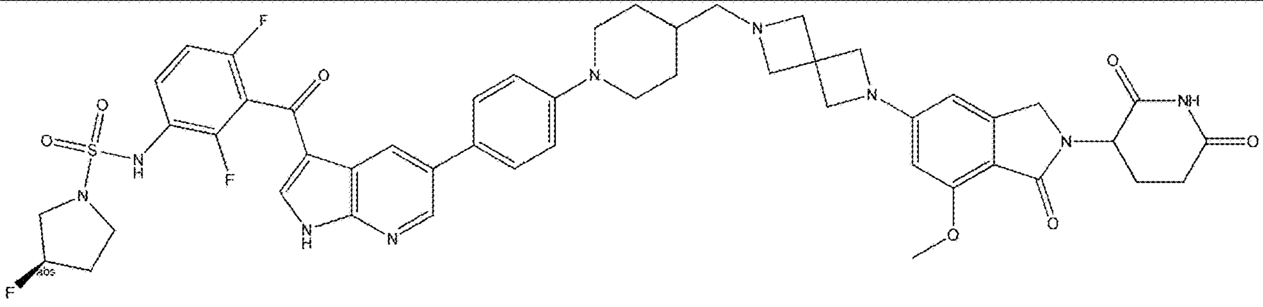
Figure 2B:
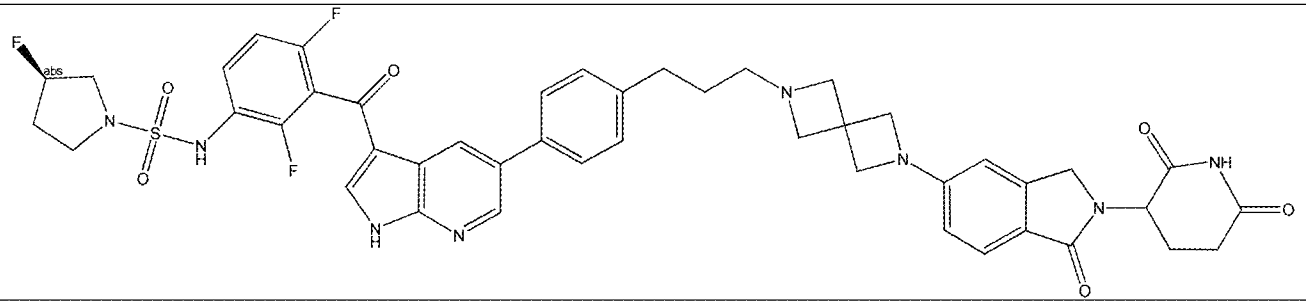
Figure 2B:
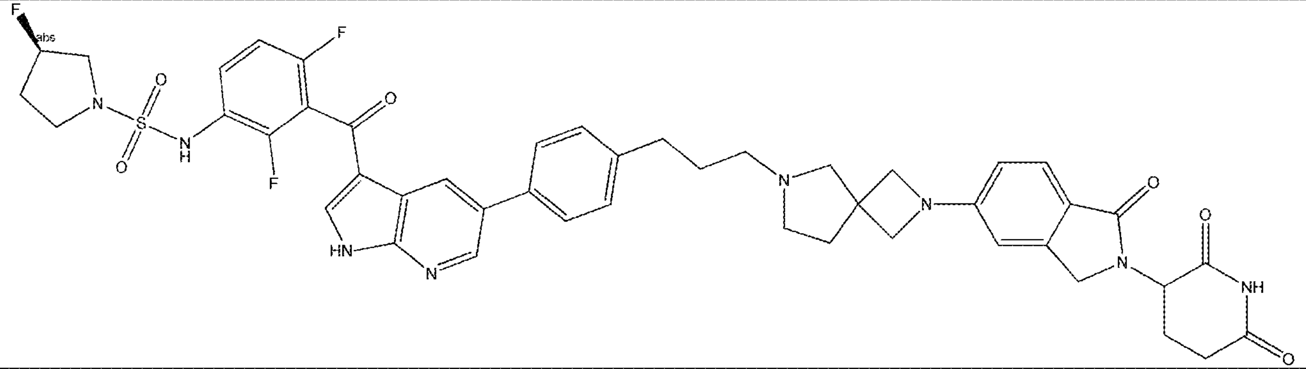
Figure 2B:
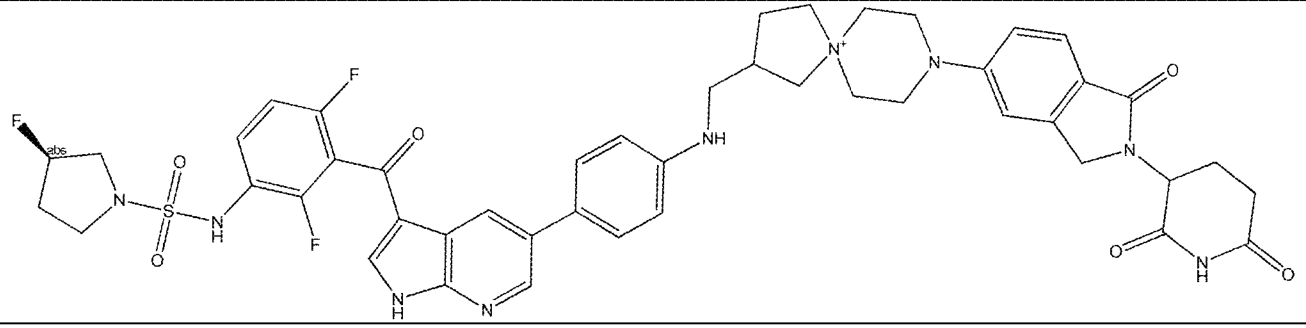
Figure 2B:
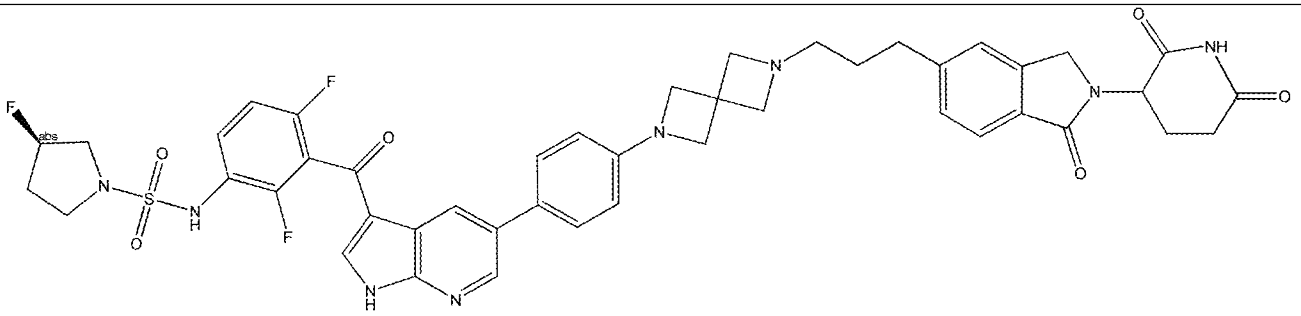
Figure 2B:
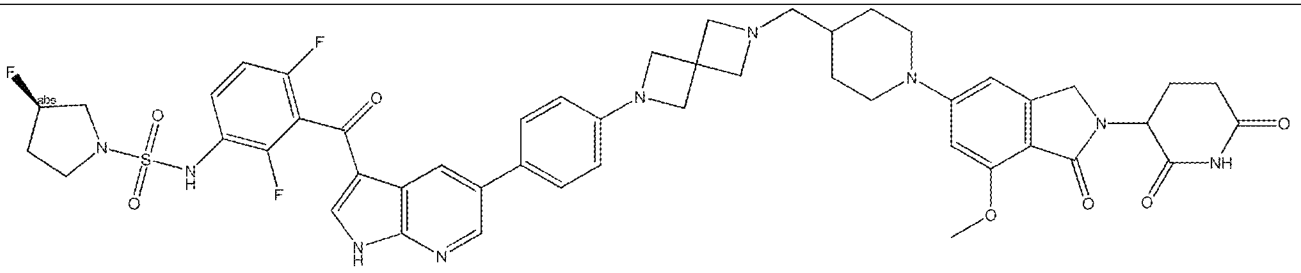
Figure 2B:
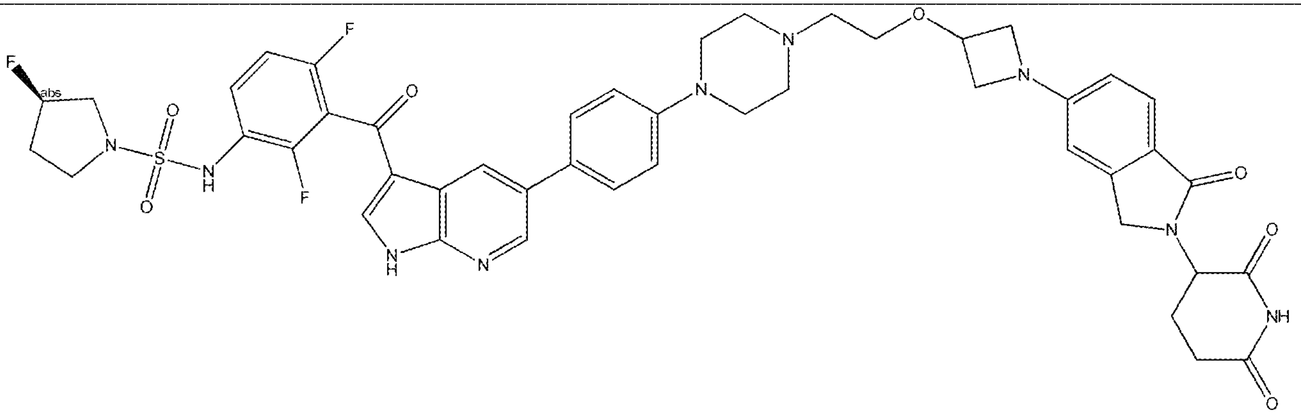
Figure 2B:
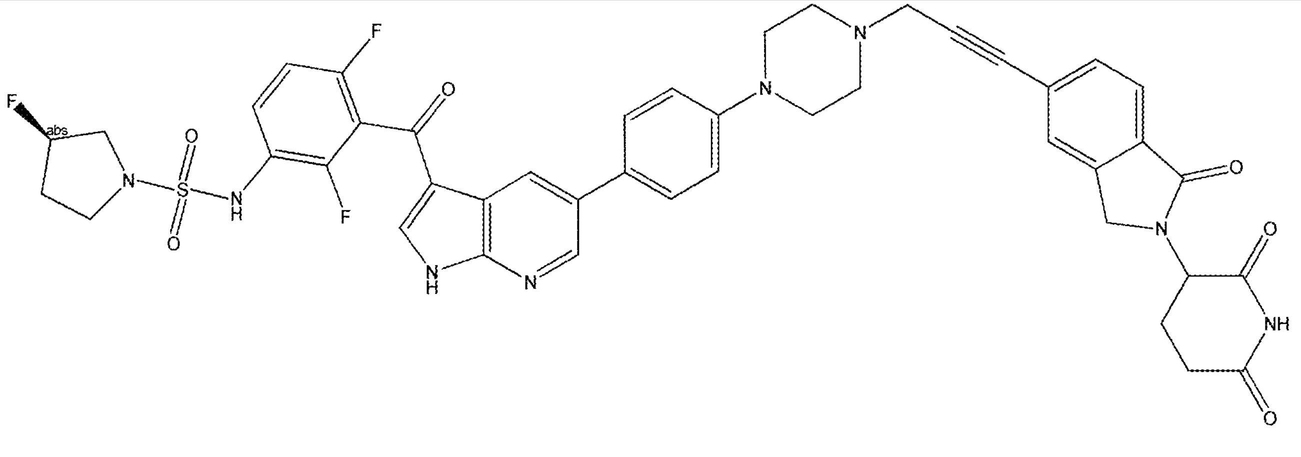
Figure 2B:
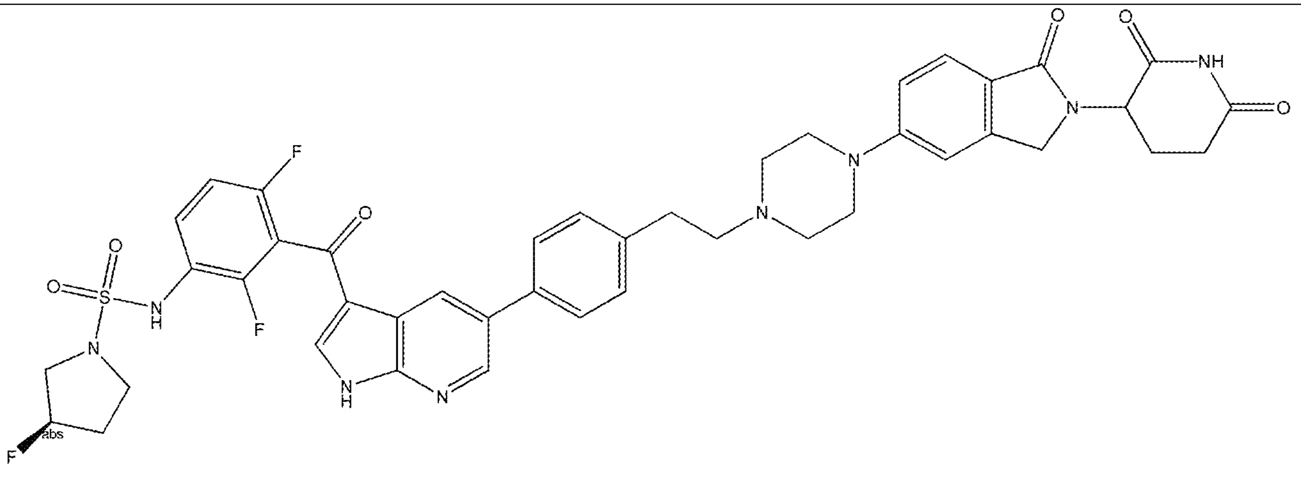
Figure 2B:
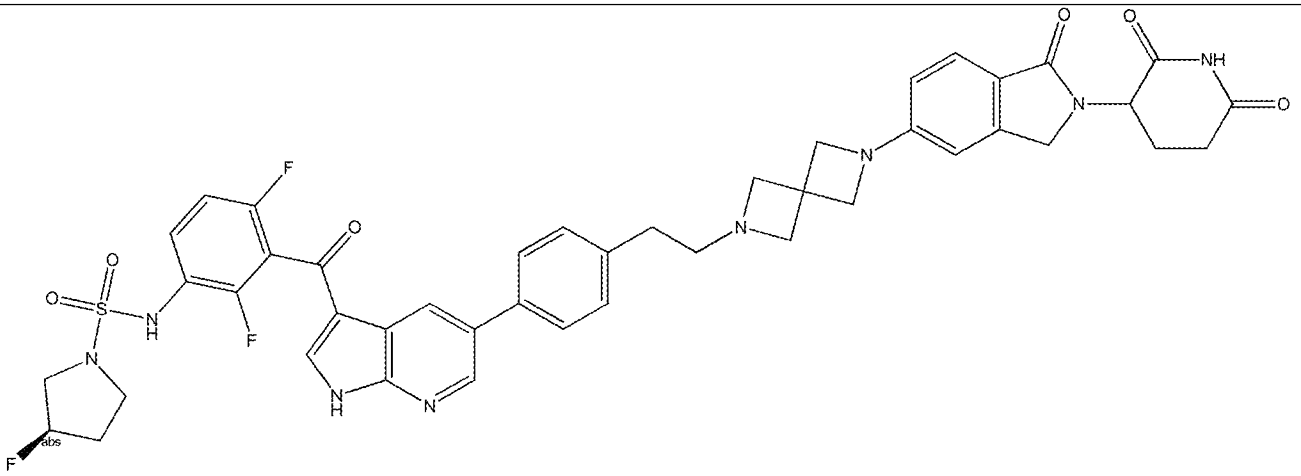
Figure 2B:
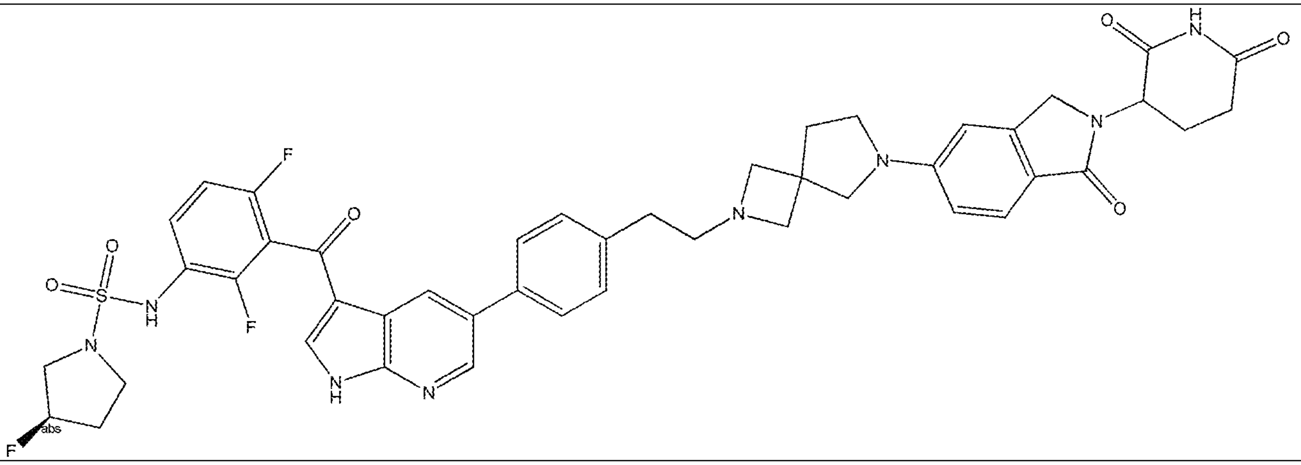
Figure 2B:
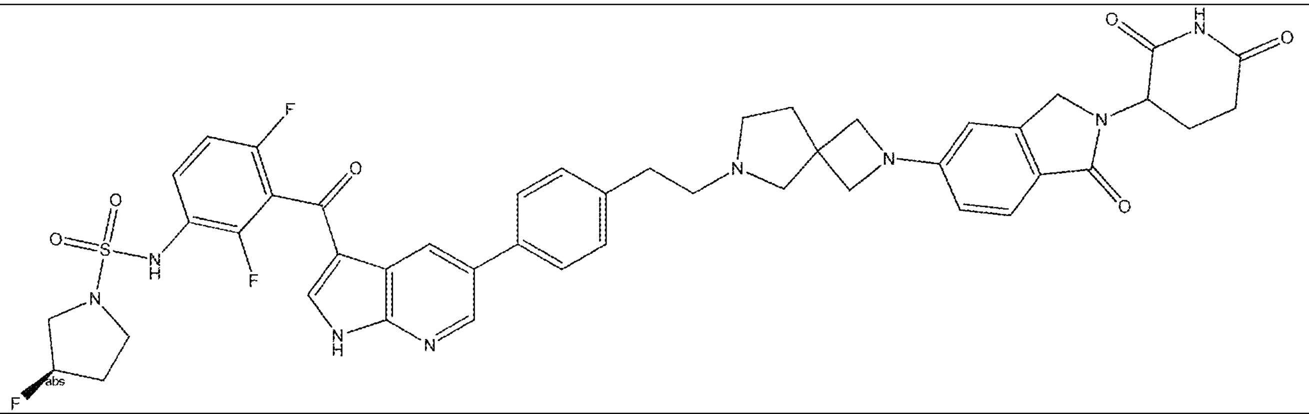
Figure 2B:
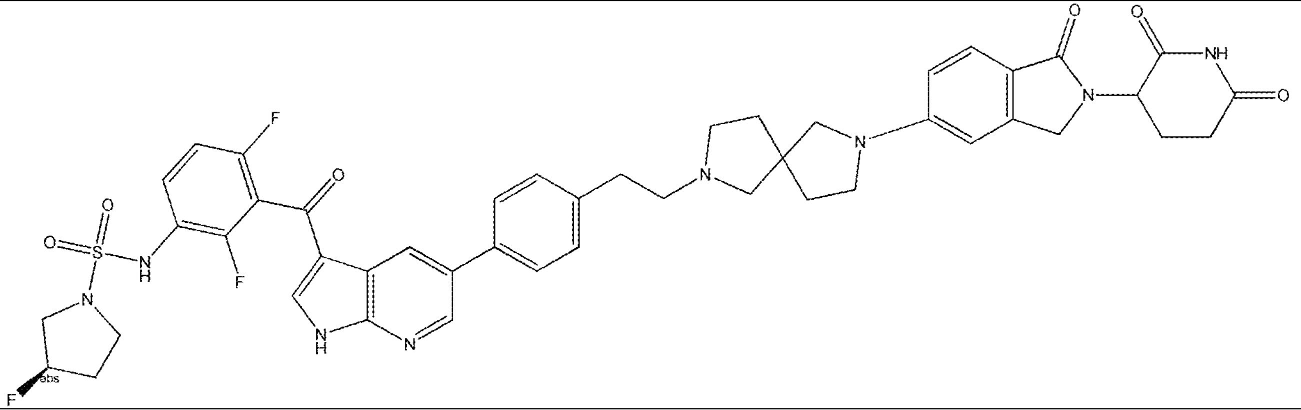
Figure 2B:
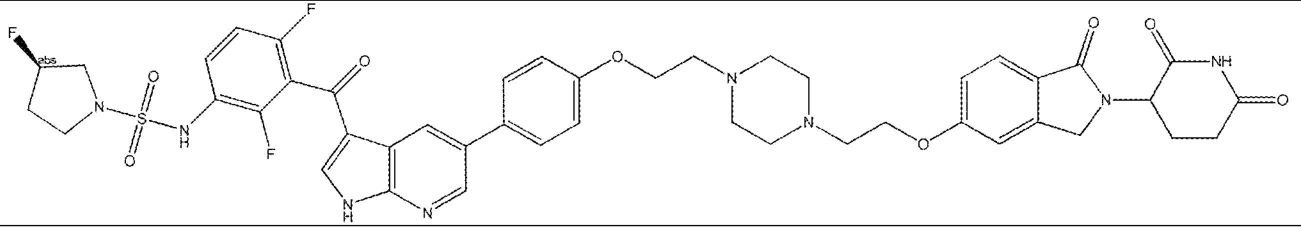
Figure 2B:
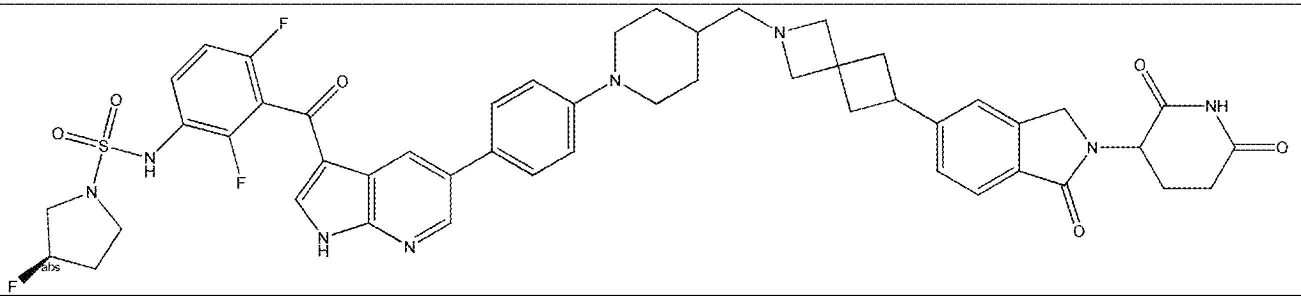
Figure 2B:
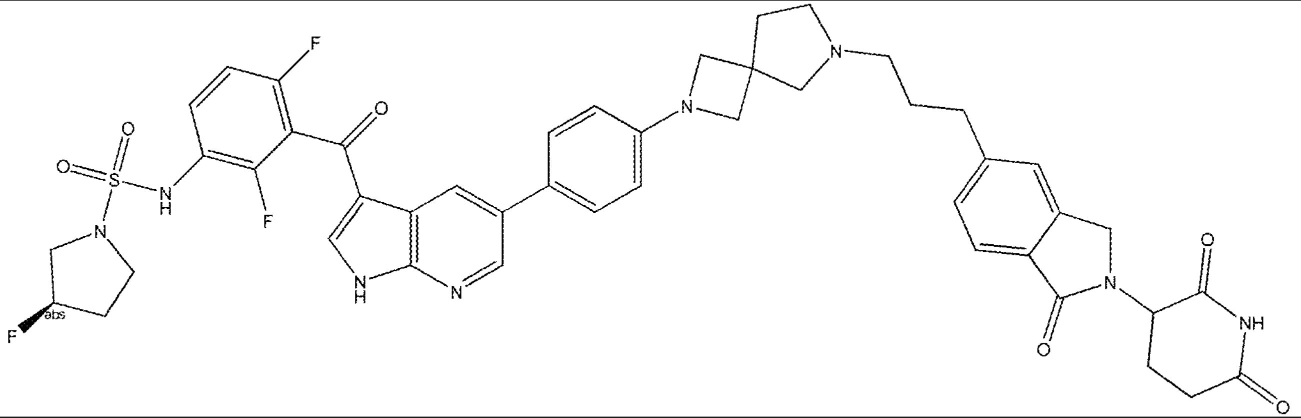
Figure 2B:
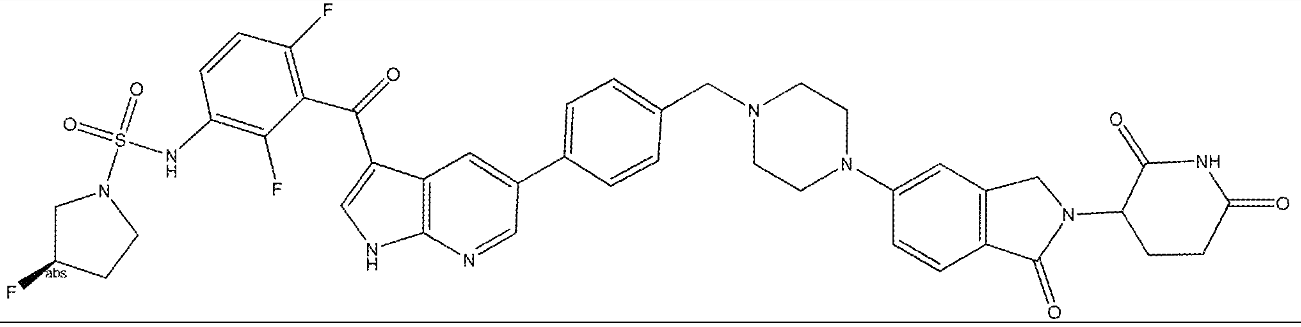
Figure 2B:
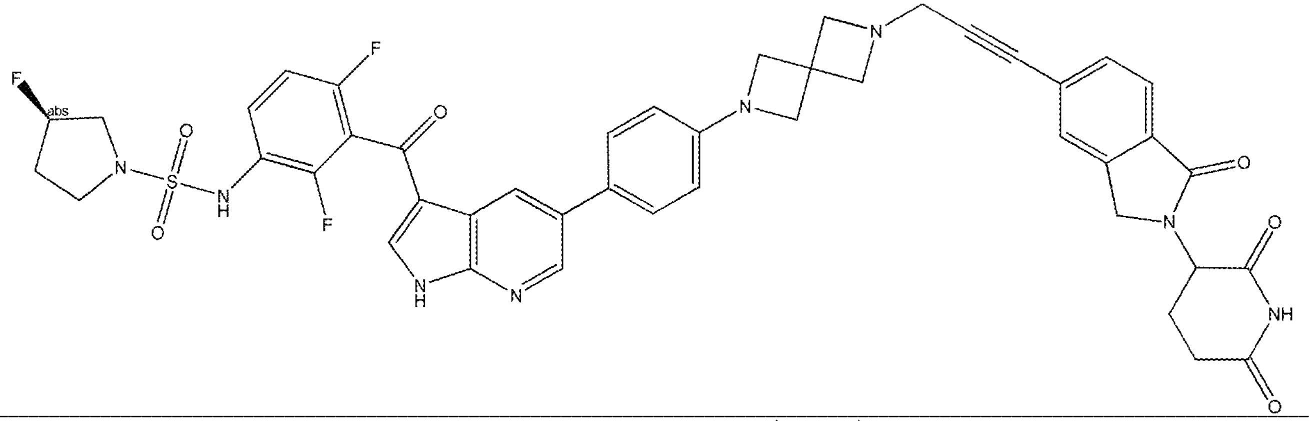
Figure 2B:
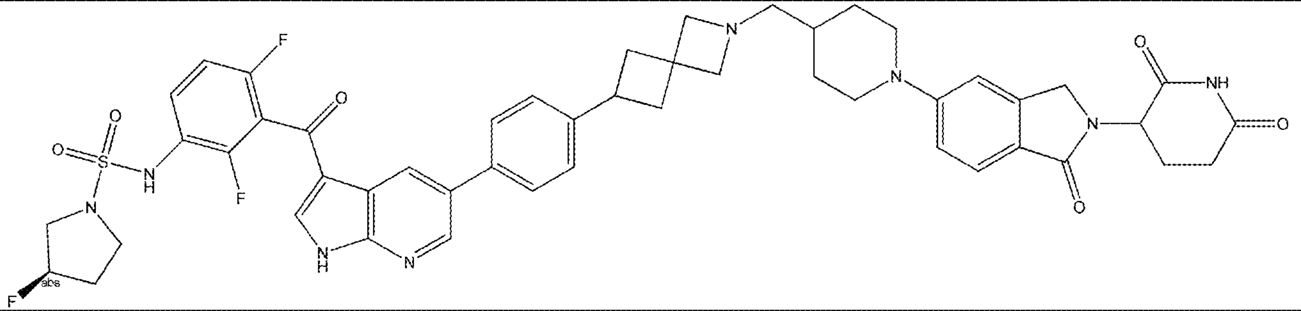
Figure 2B:
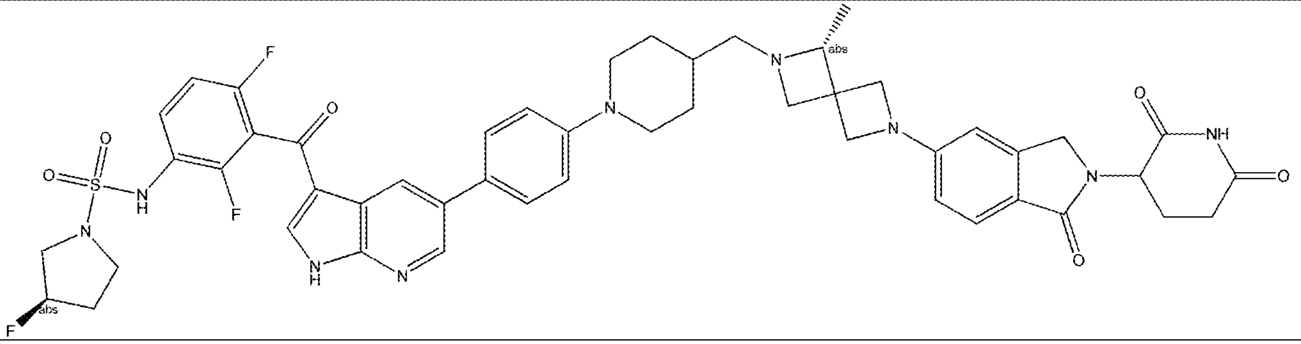
Figure 2B:
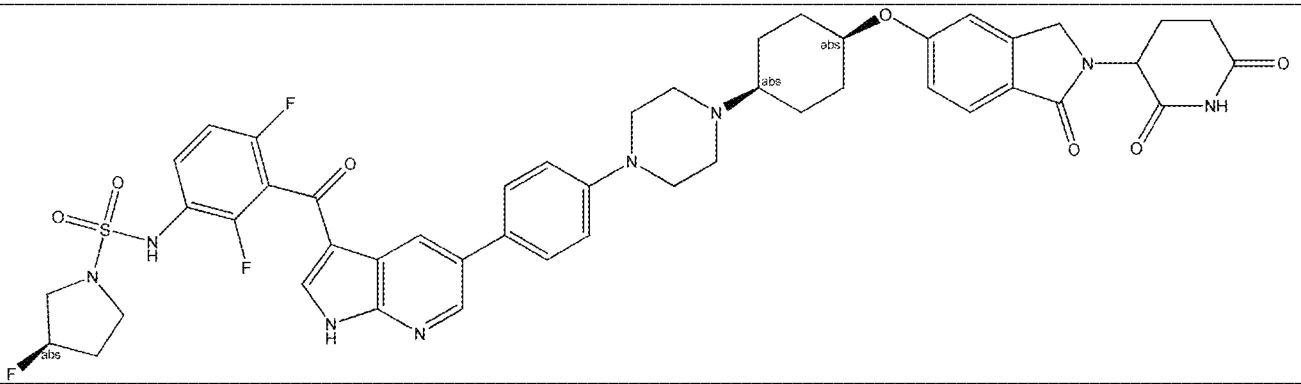
Figure 2B:
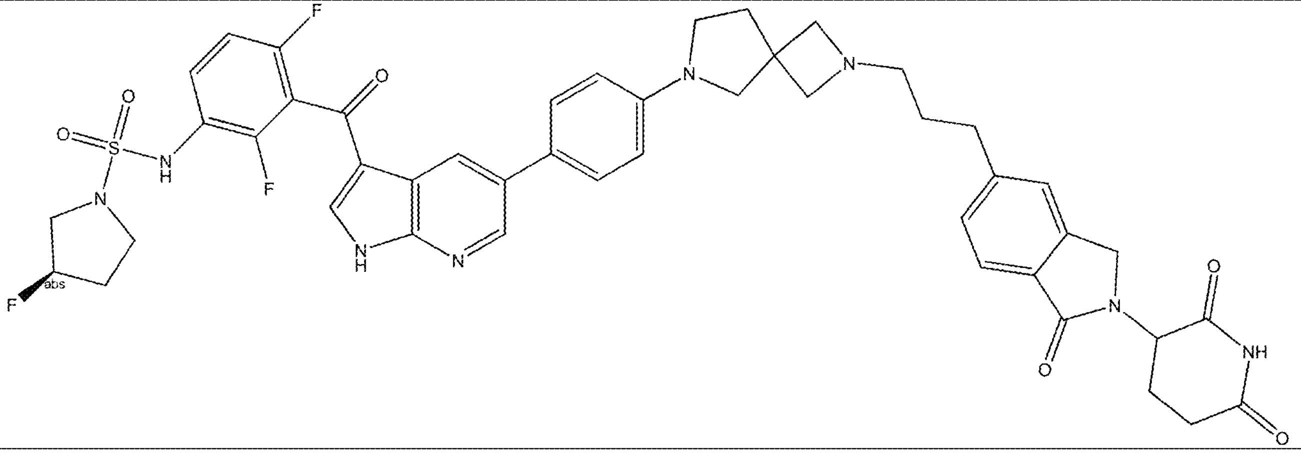
Figure 2B:
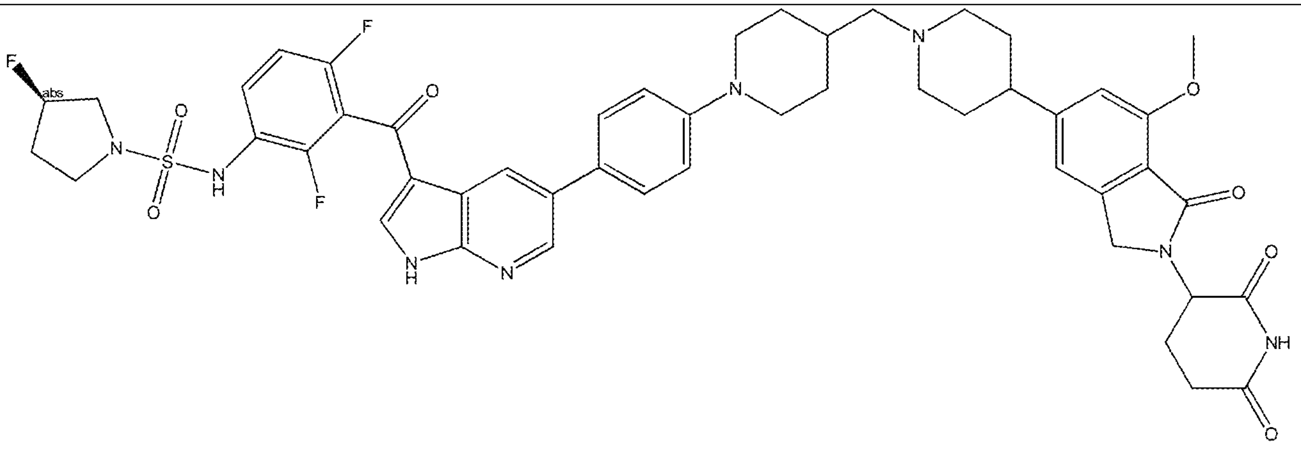
Figure 2B:
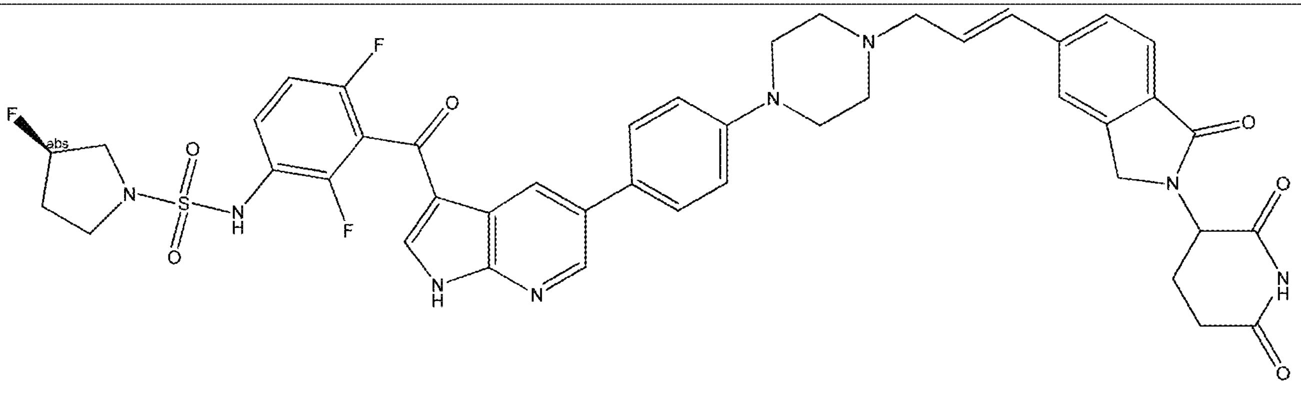
Figure 2B:
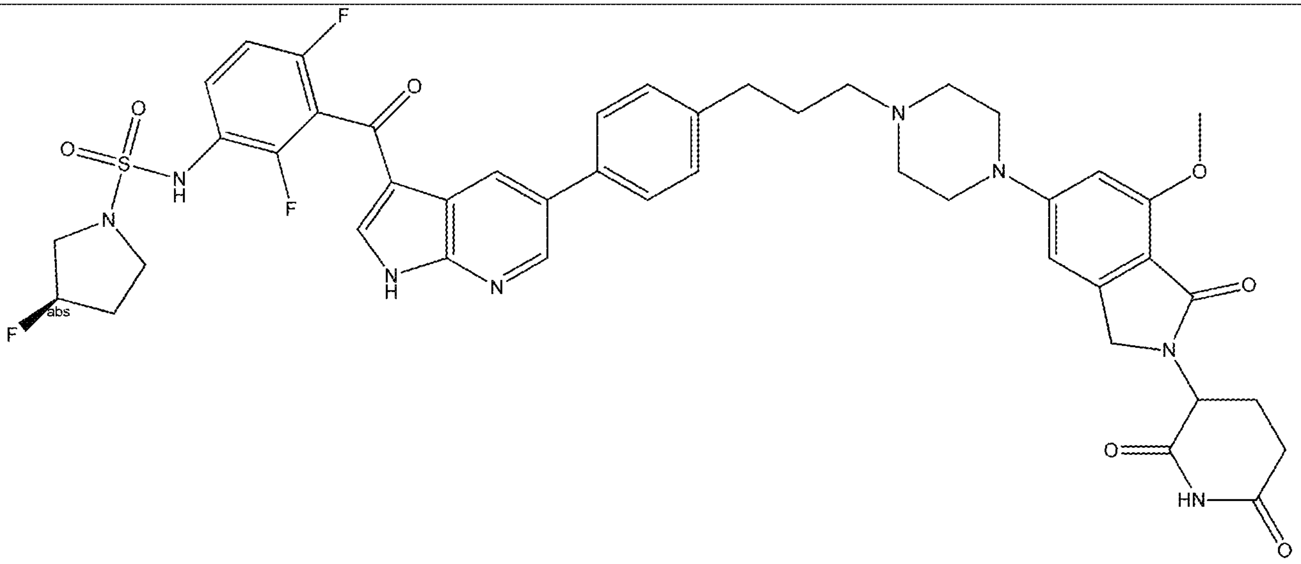
Figure 2B:
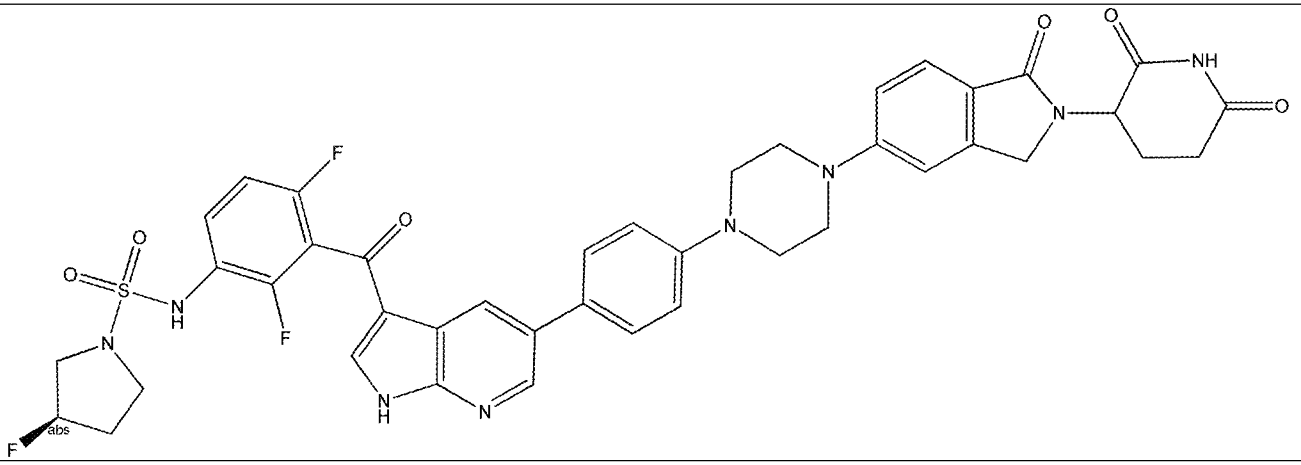
Figure 2B:
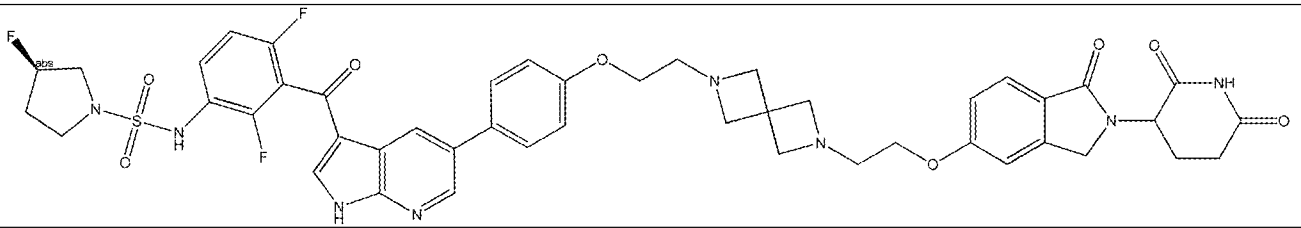
Figure 2B:
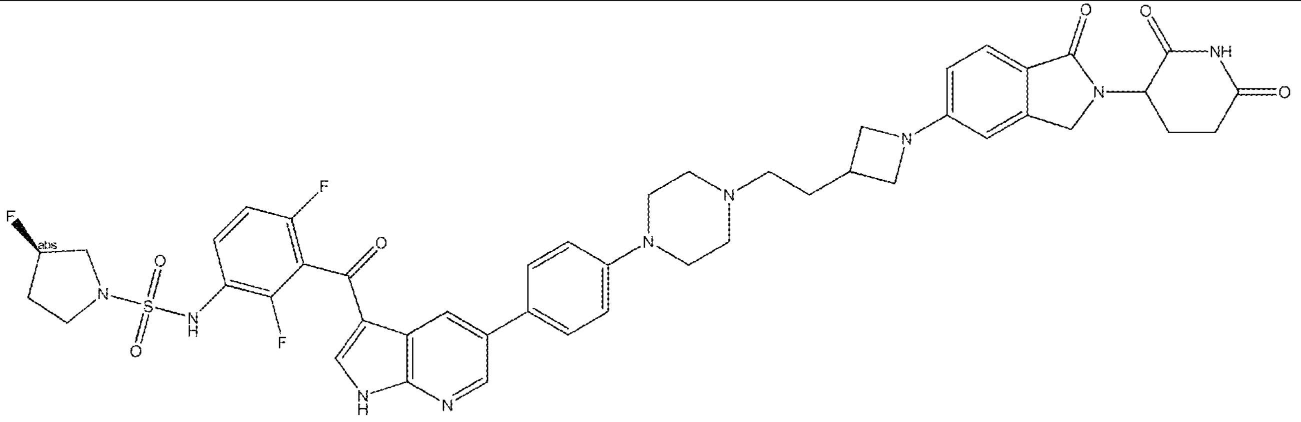
Figure 2B:
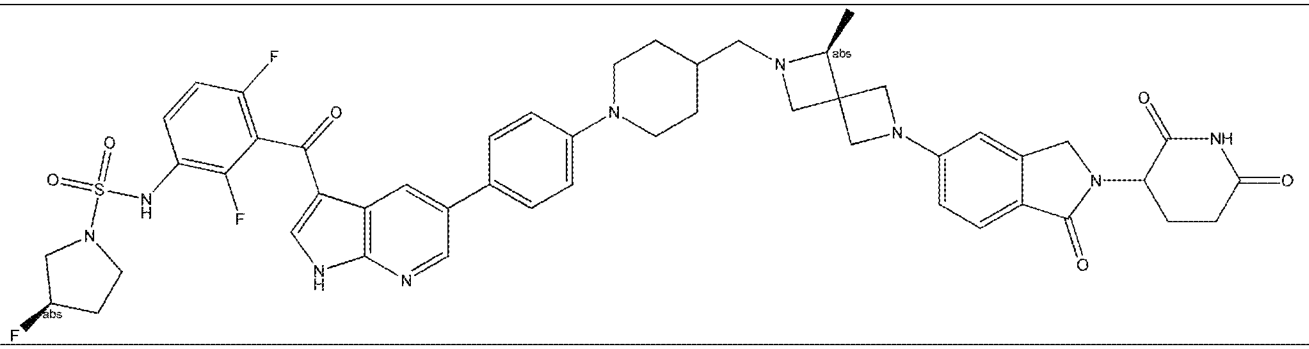
Figure 2B:
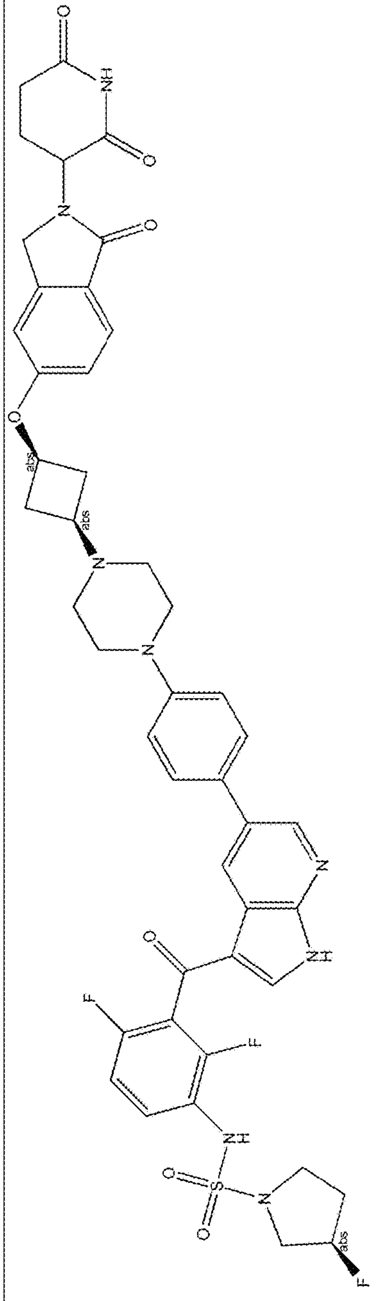
Figure 2B:
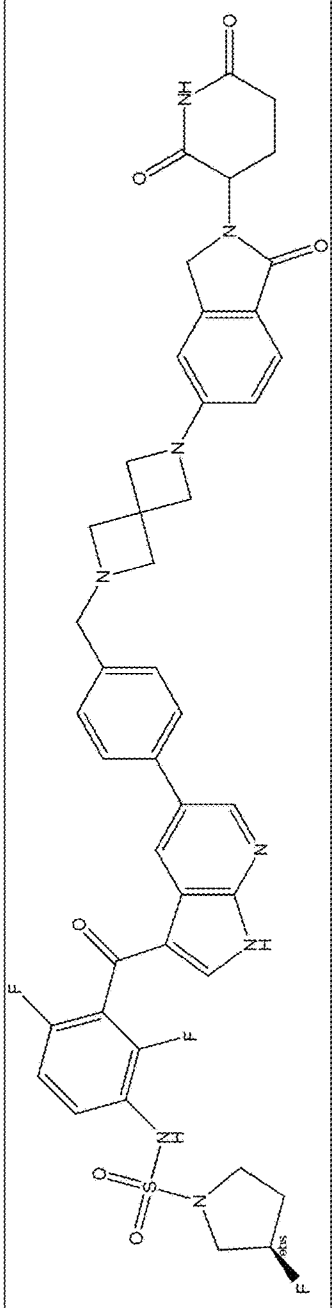
Figure 2B:
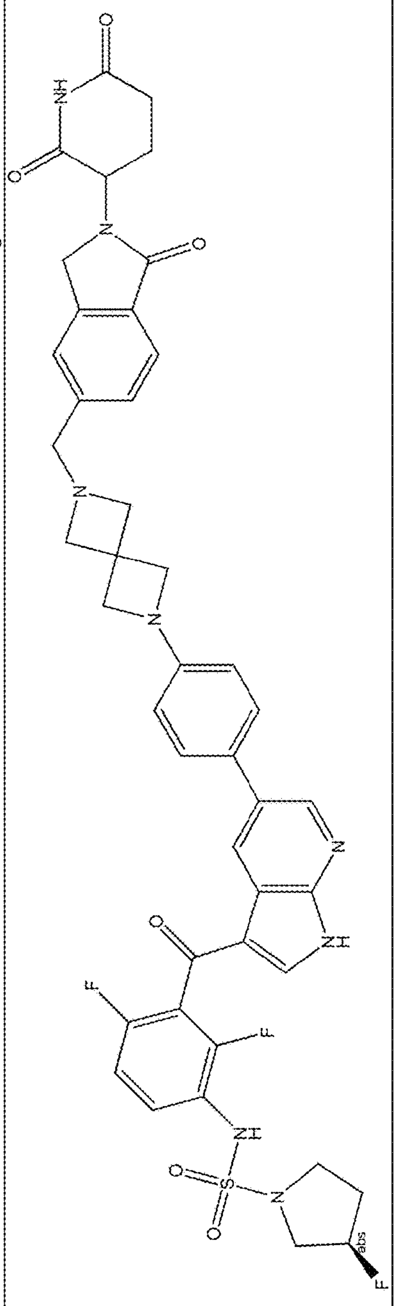
Figure 2B:
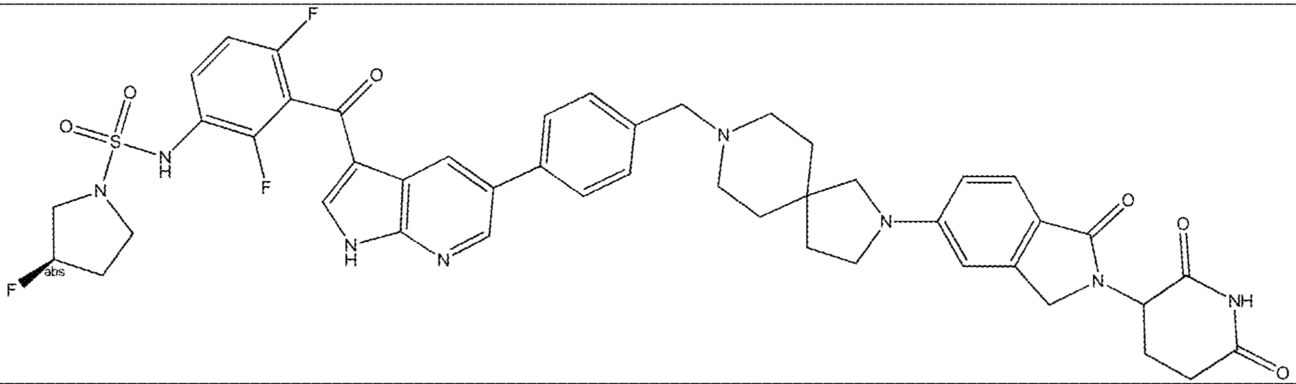
Figure 2B:
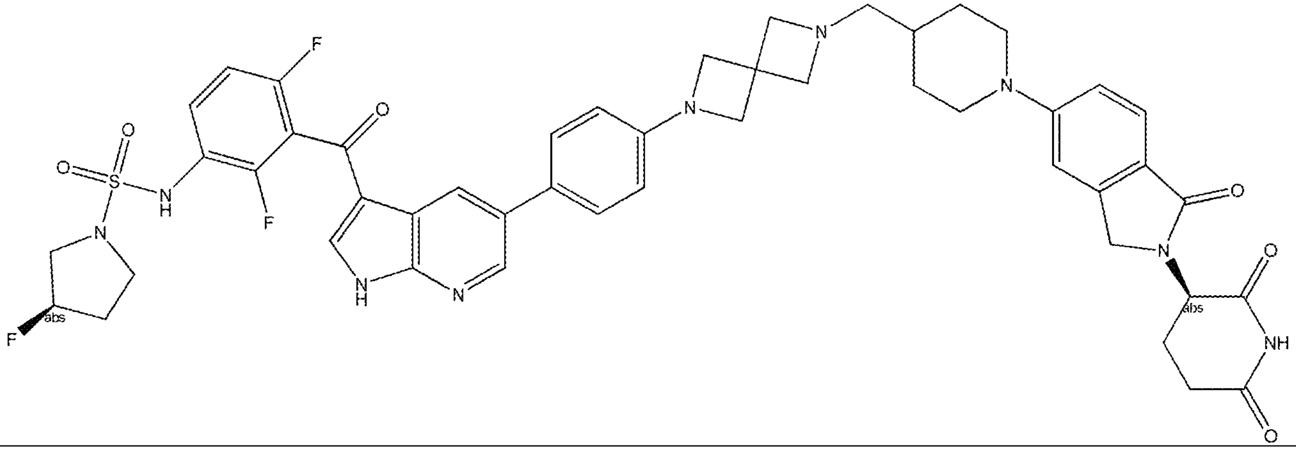
Figure 2B:
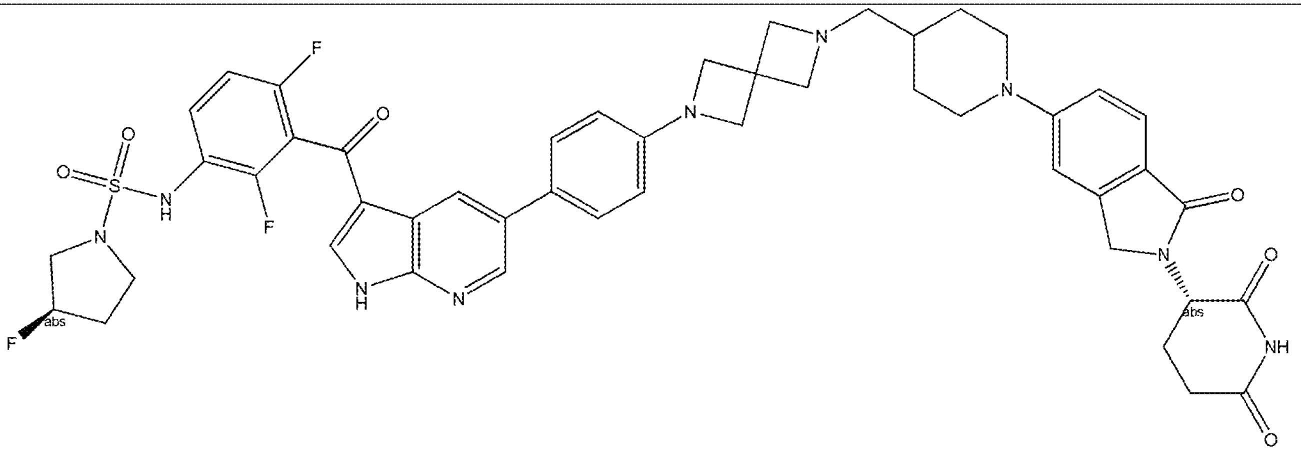
Figure 2B:
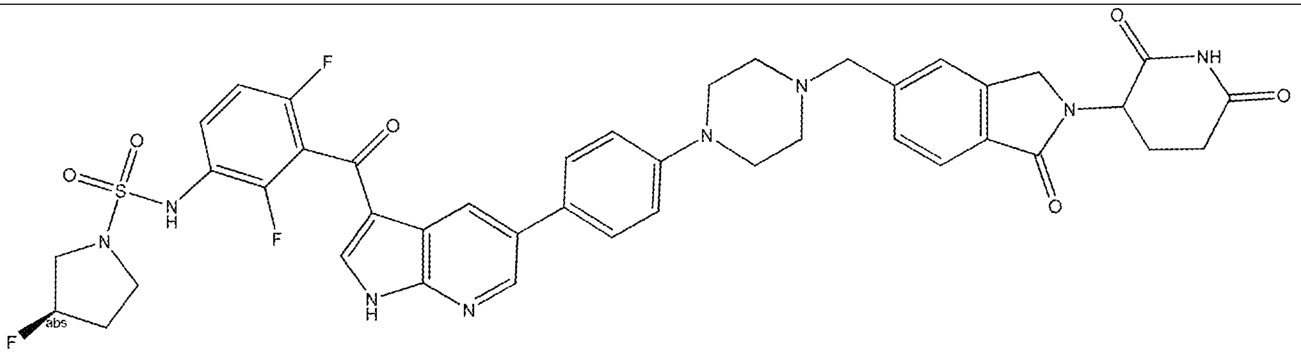
Figure 2B:
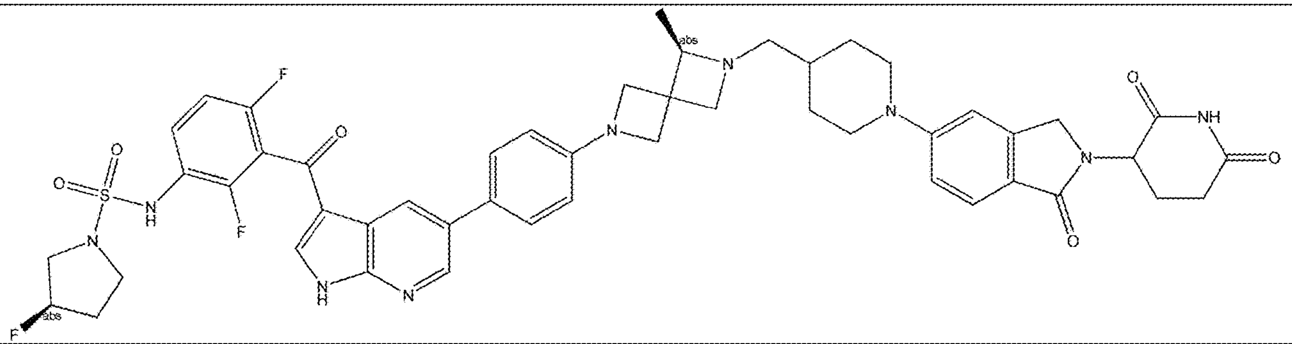
Figure 2B:
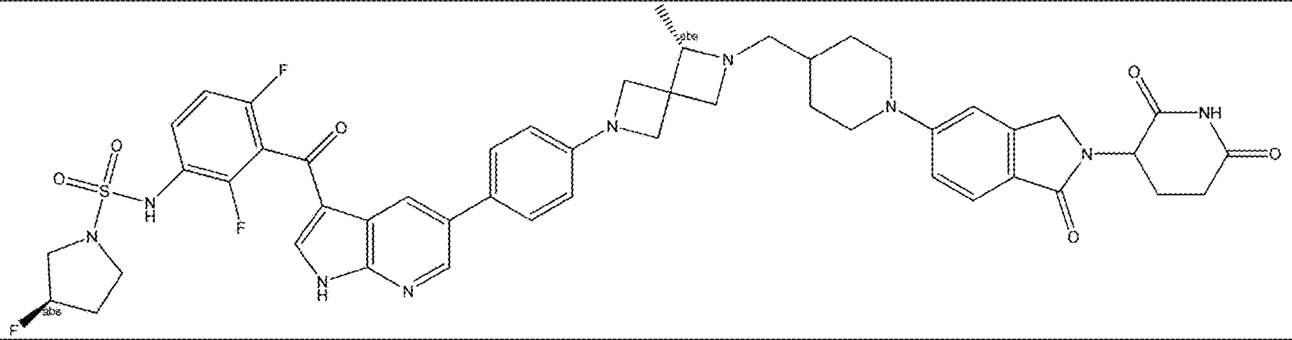
Figure 2B:
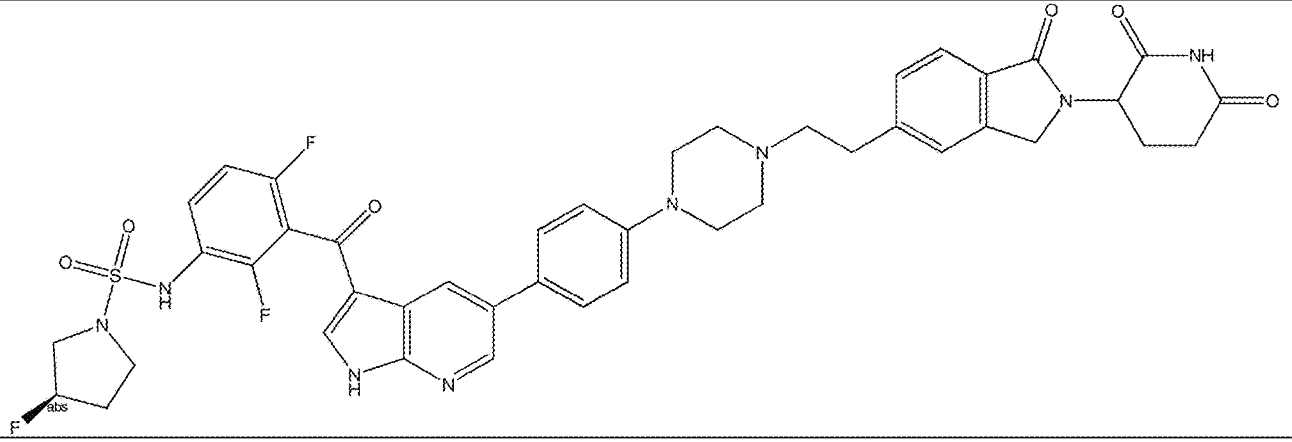
Figure 2B:
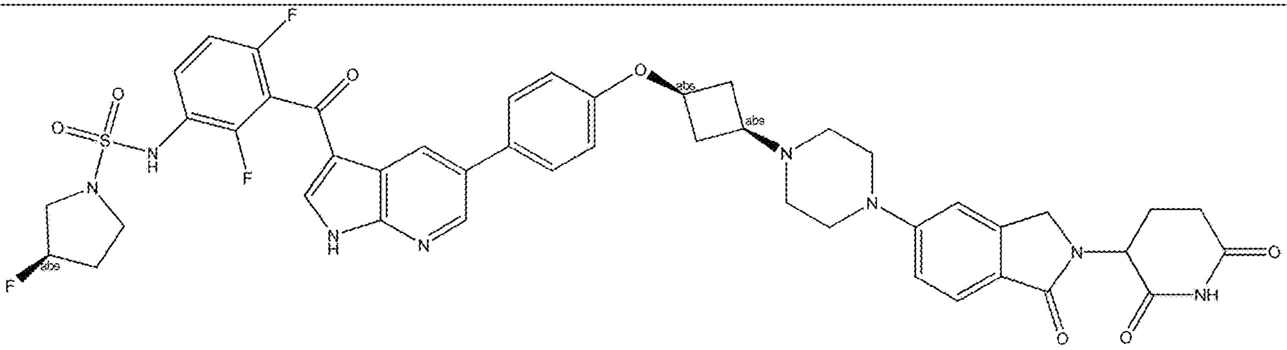
Figure 2B:
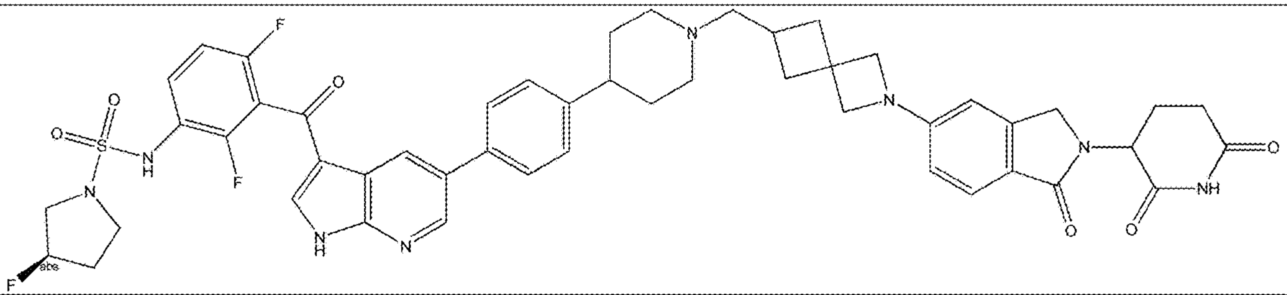
Figure 2B:
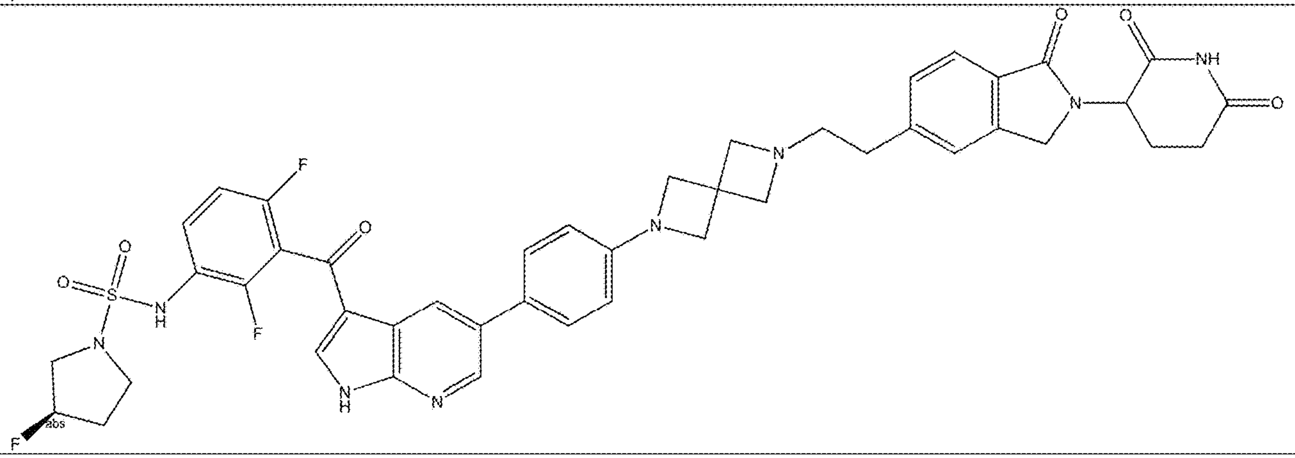
Figure 2B:
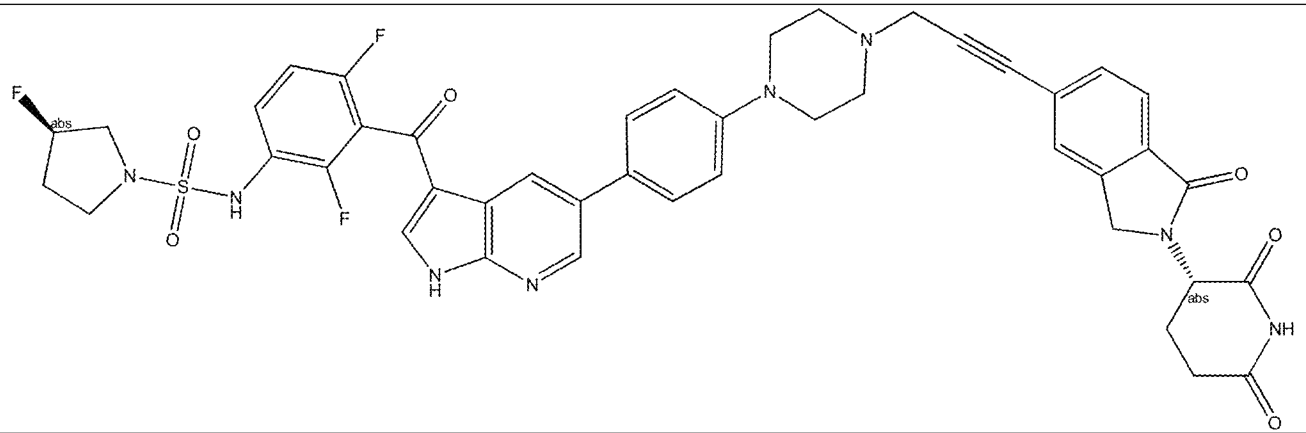
Figure 2B:
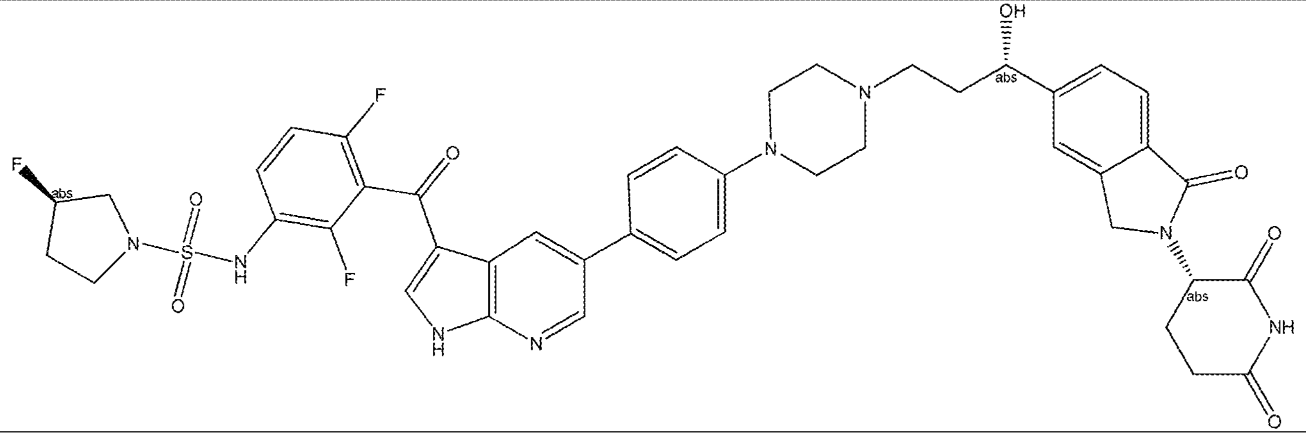
Figure 2B:
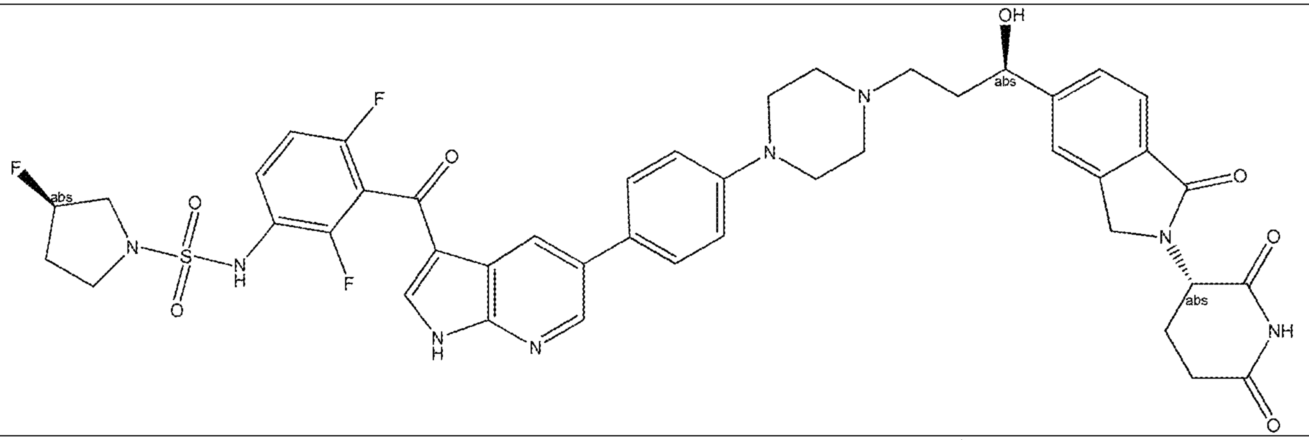
Figure 2B:
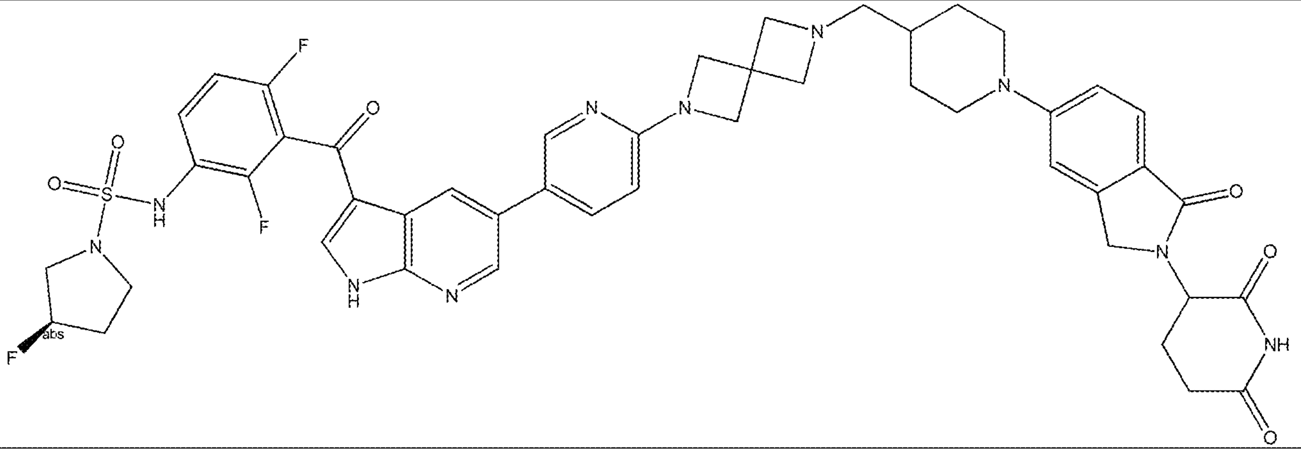
Figure 2B:
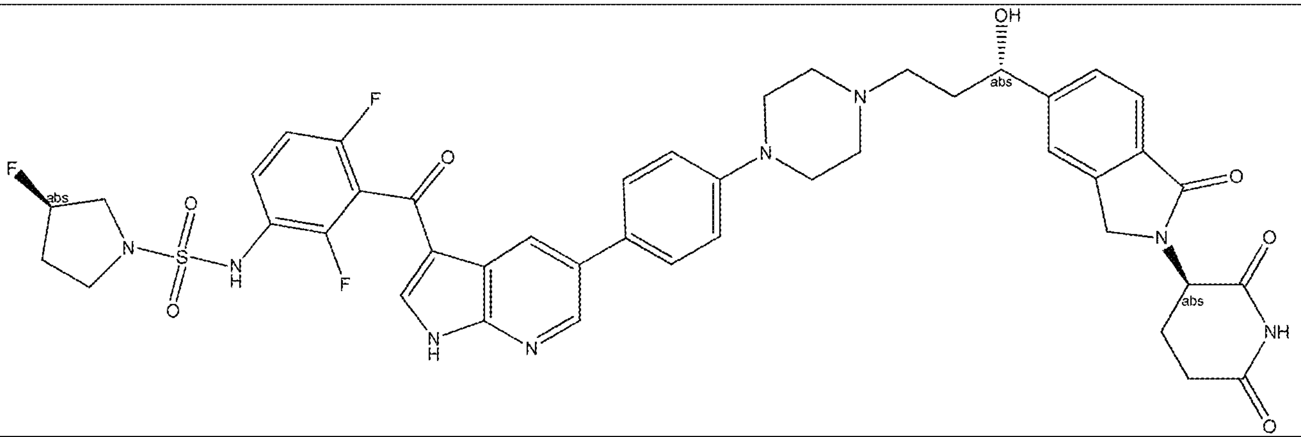
Figure 2B:
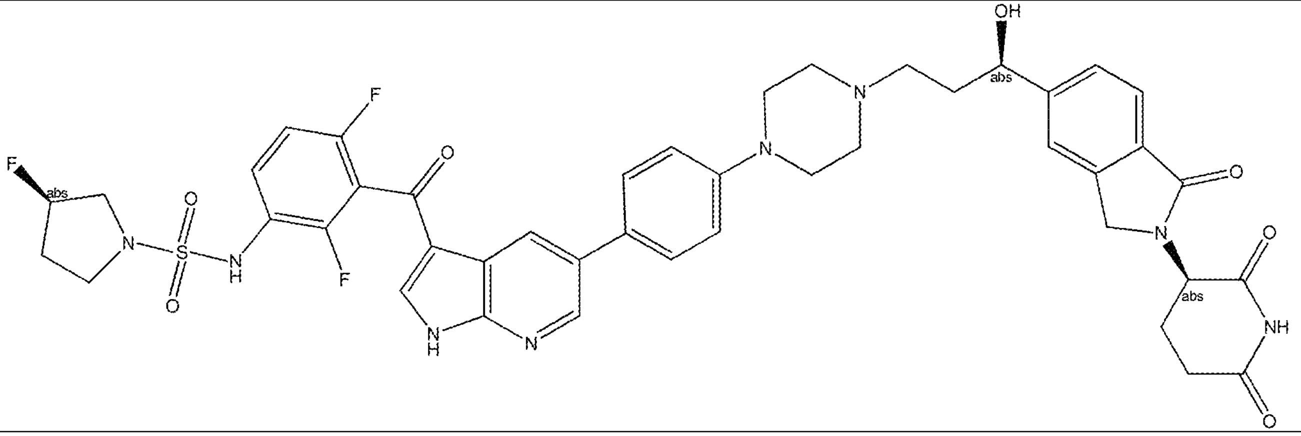
Figure 2B:
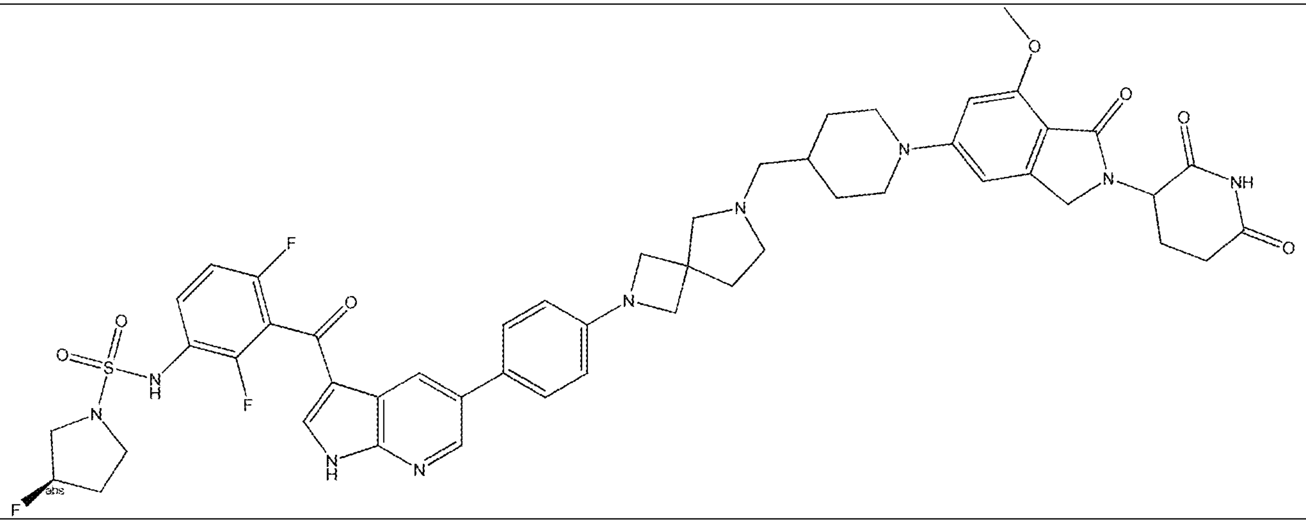
Figure 2B:
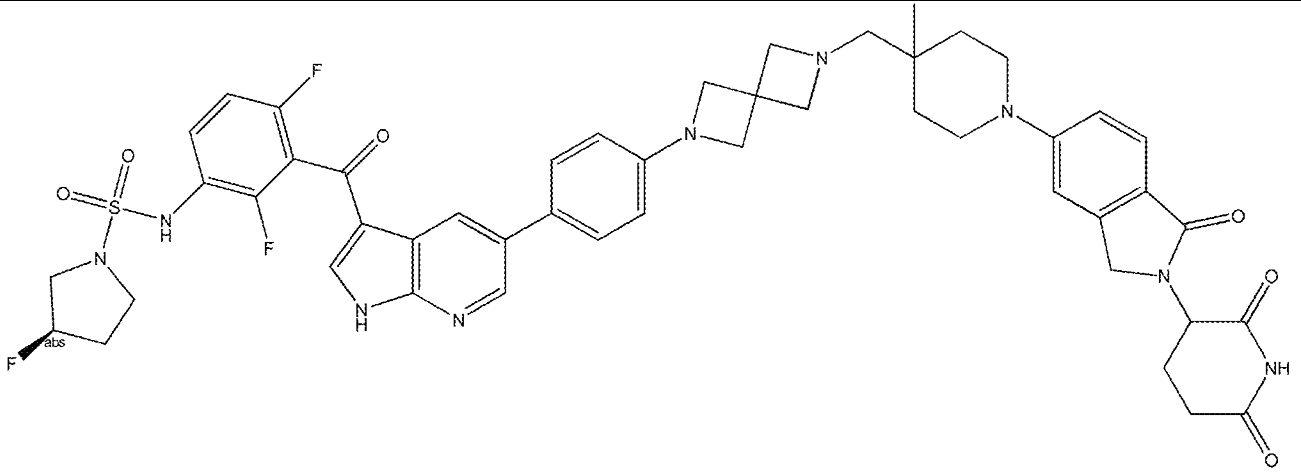
Figure 2B:
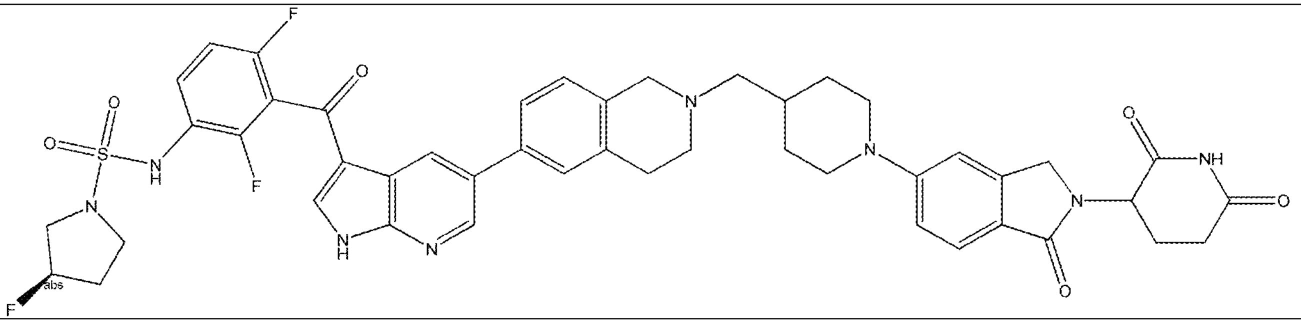
Figure 2B:
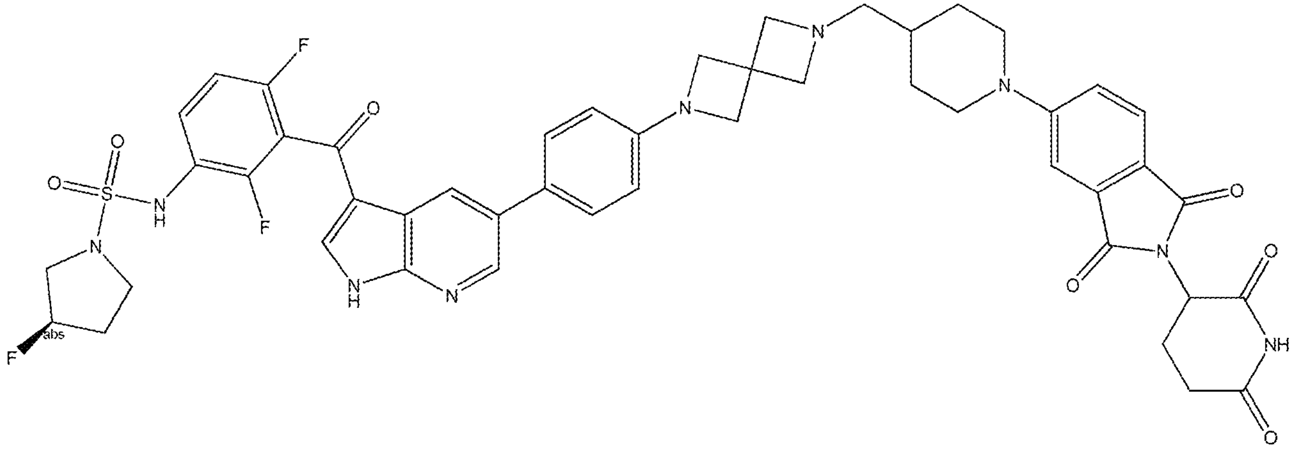
Figure 2B:
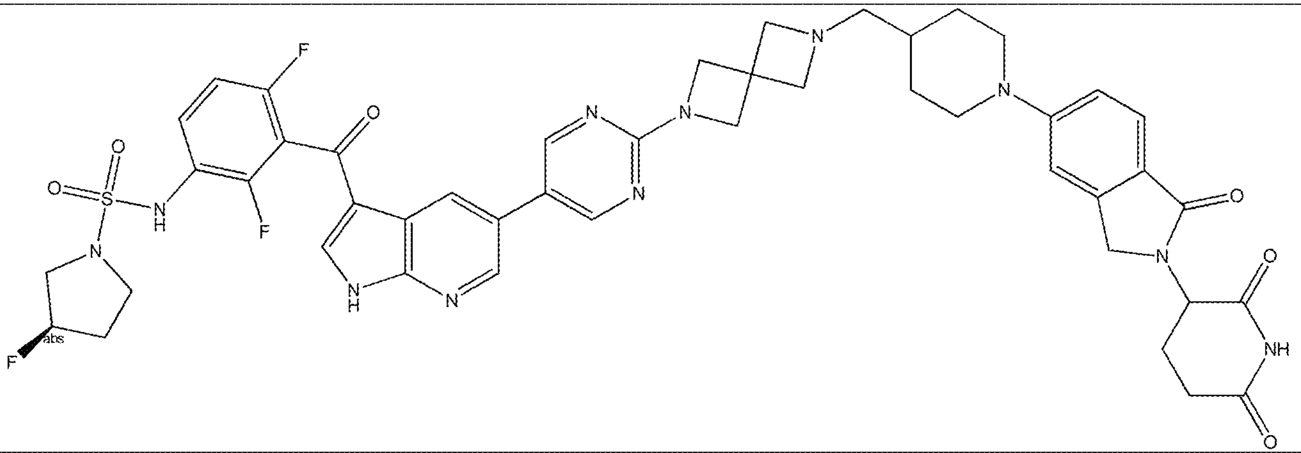
Figure 2B:
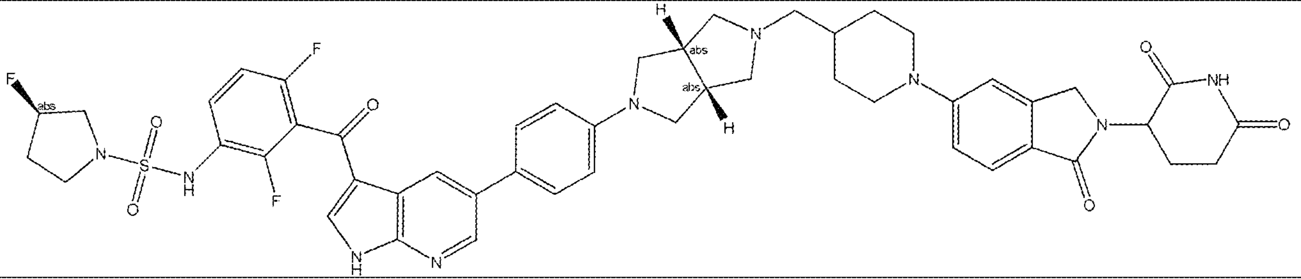
Figure 2B:
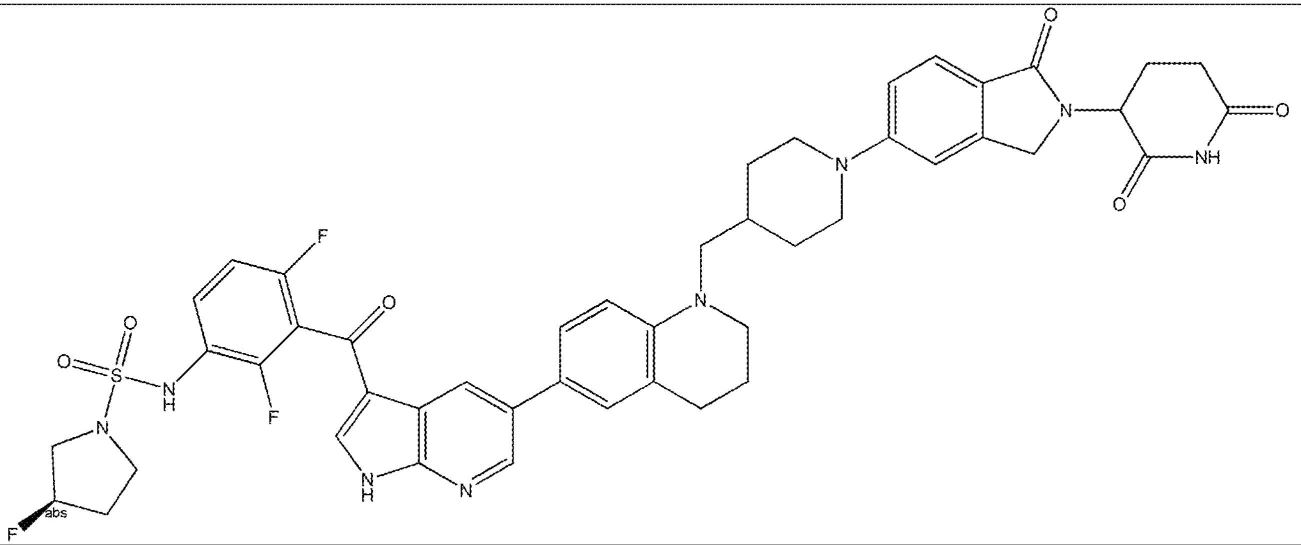
Figure 2B:
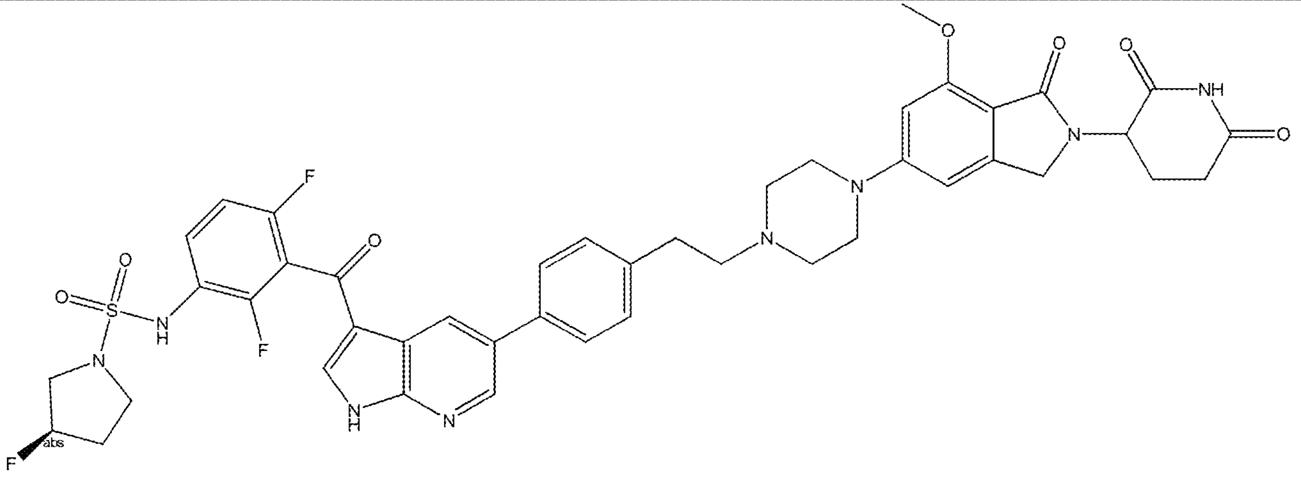
Figure 2B:
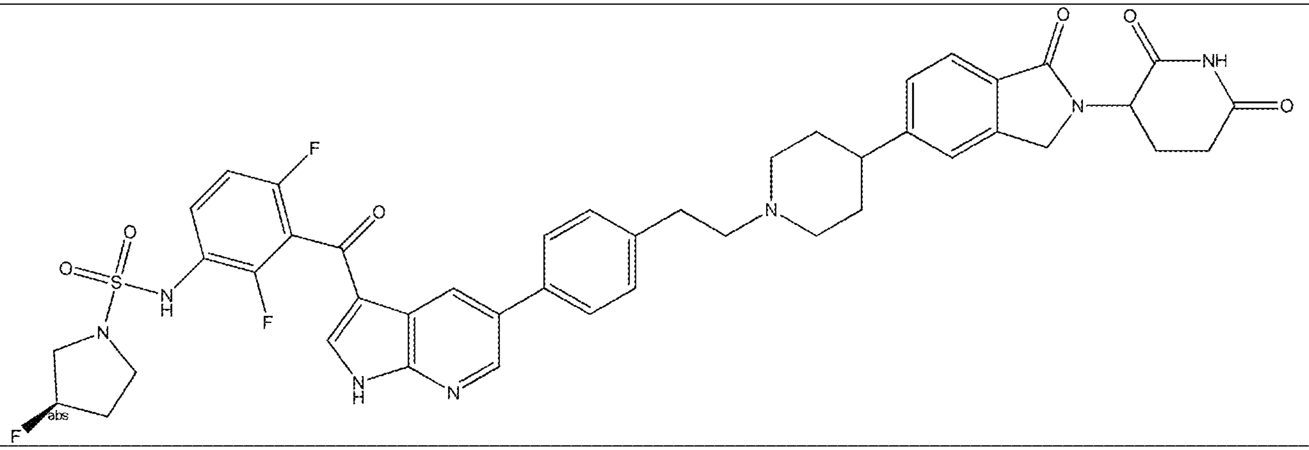
Figure 2B:
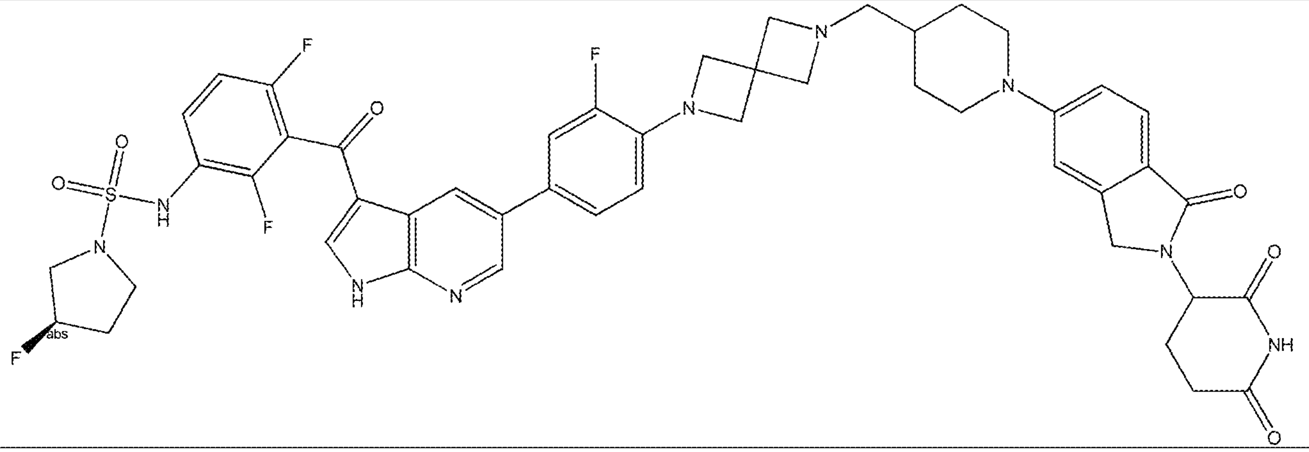
Figure 2B:
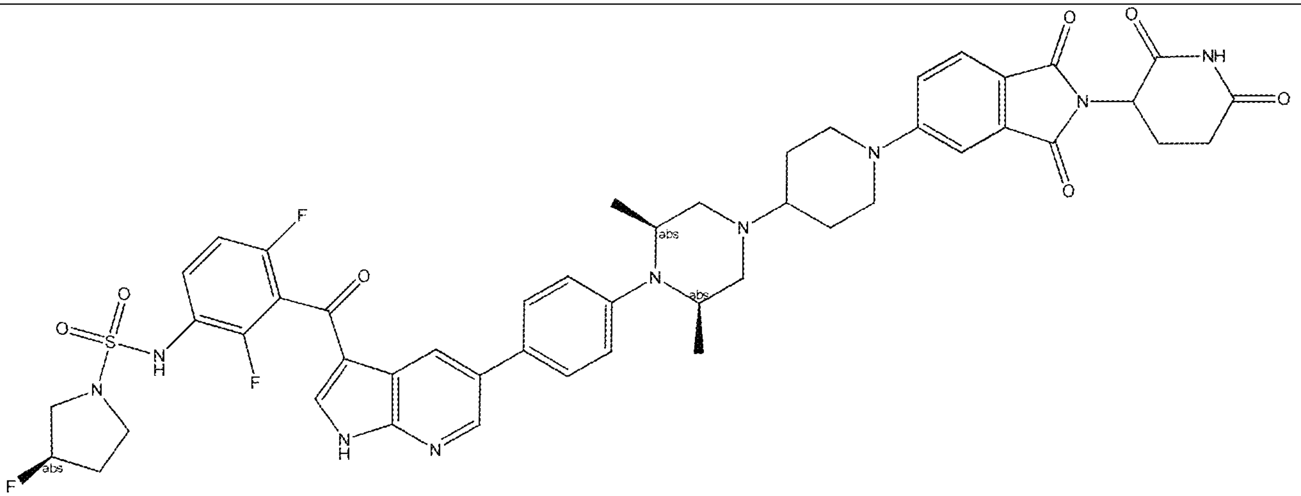
Figure 2B:
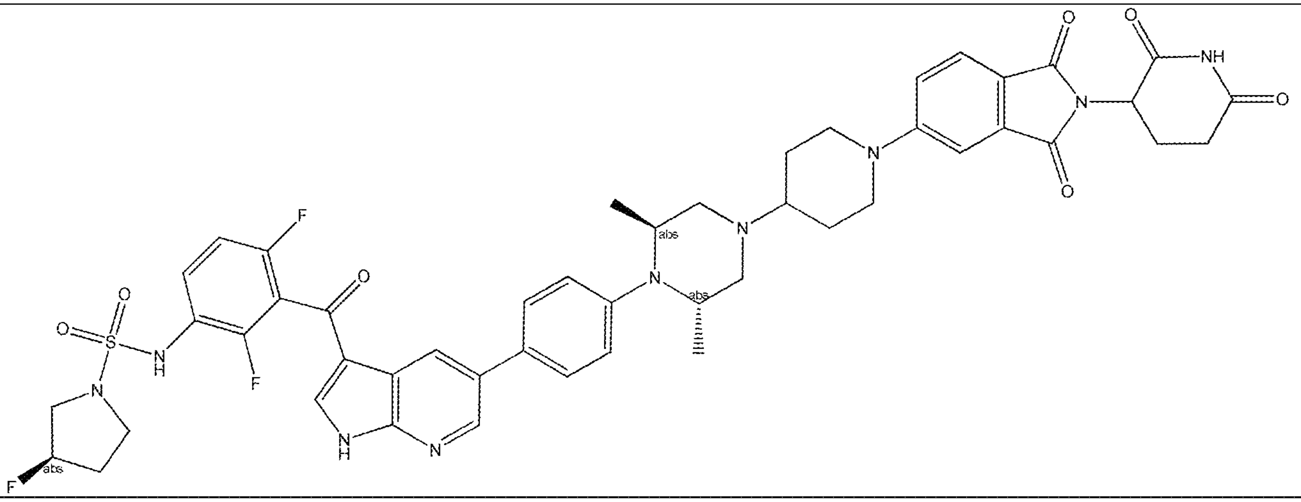
Figure 2B:
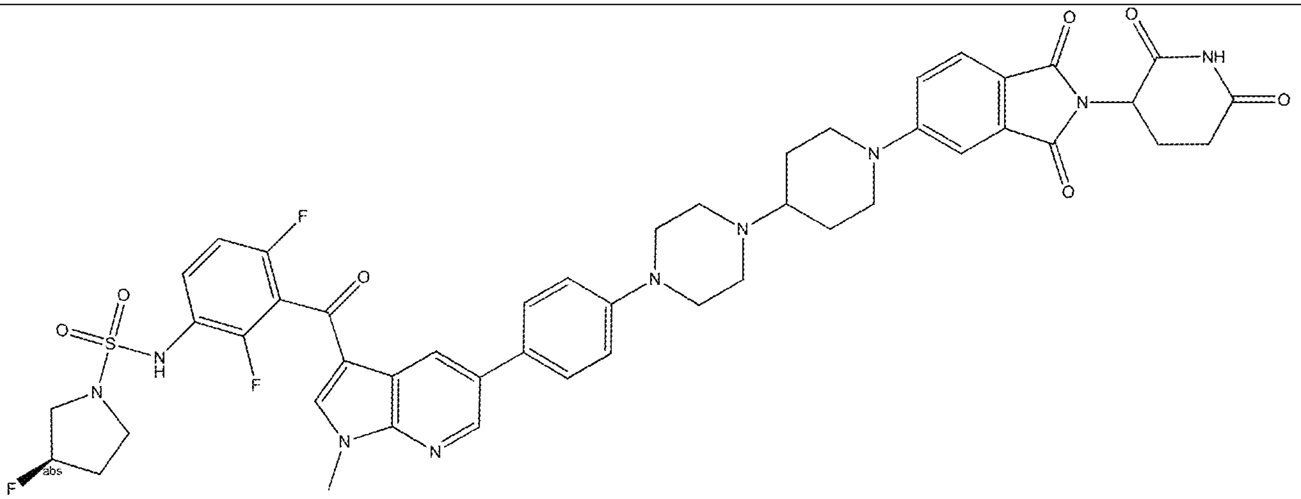
Figure 2B:
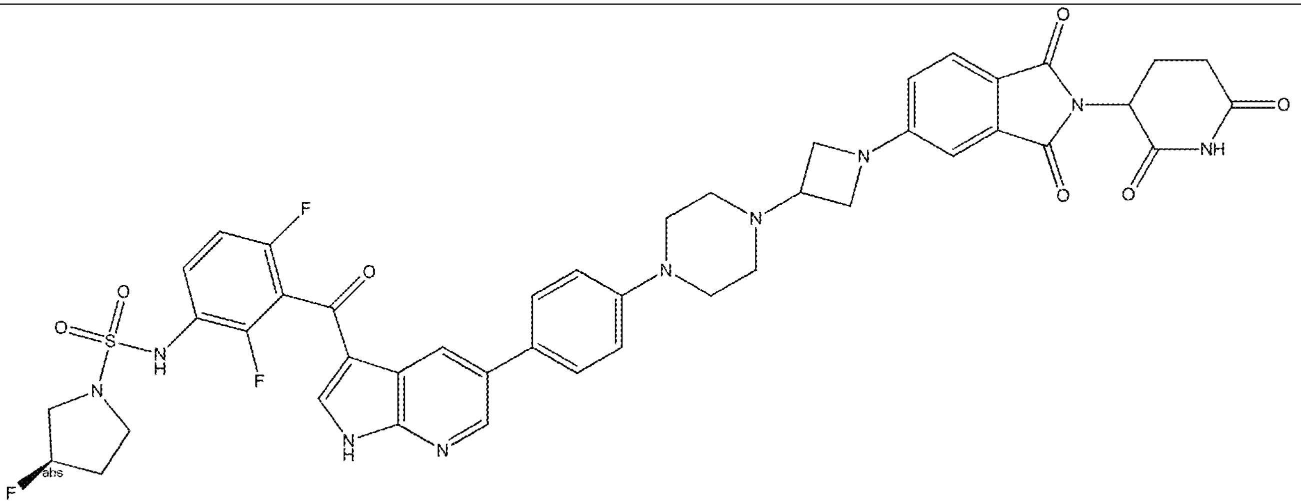
Figure 2B:
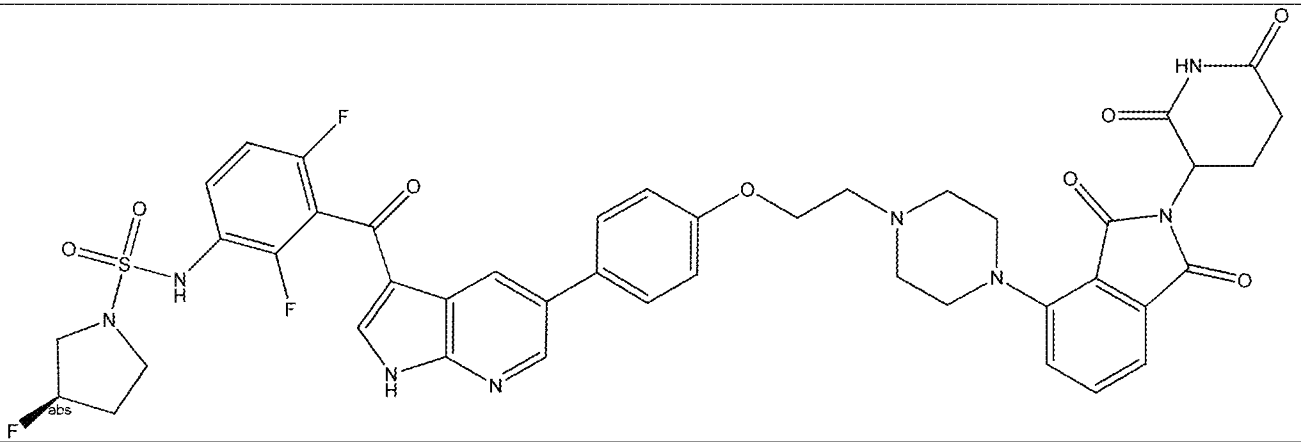
Figure 2B:
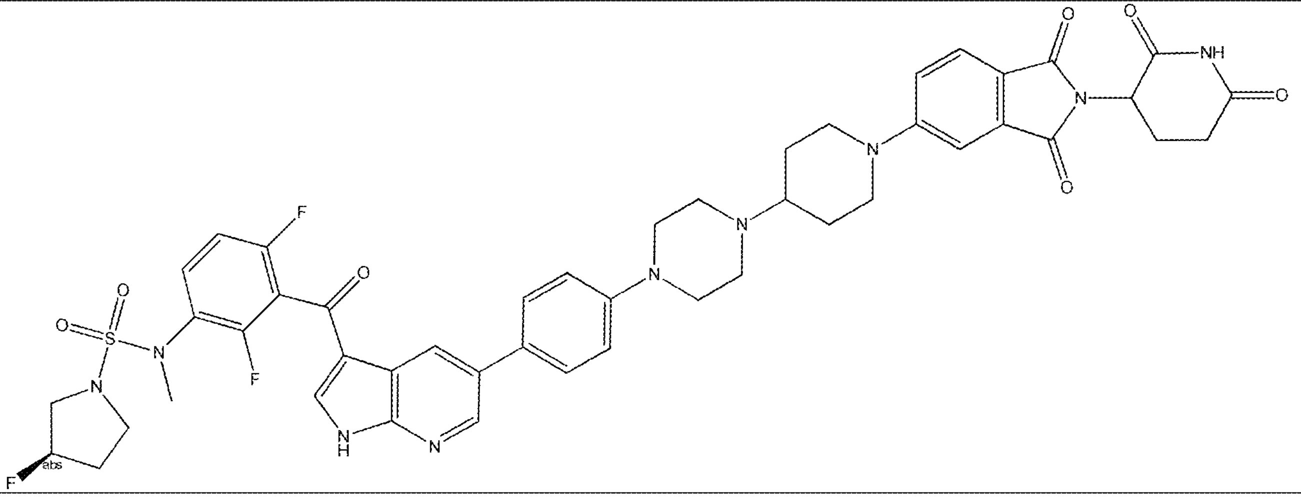
Figure 2B:
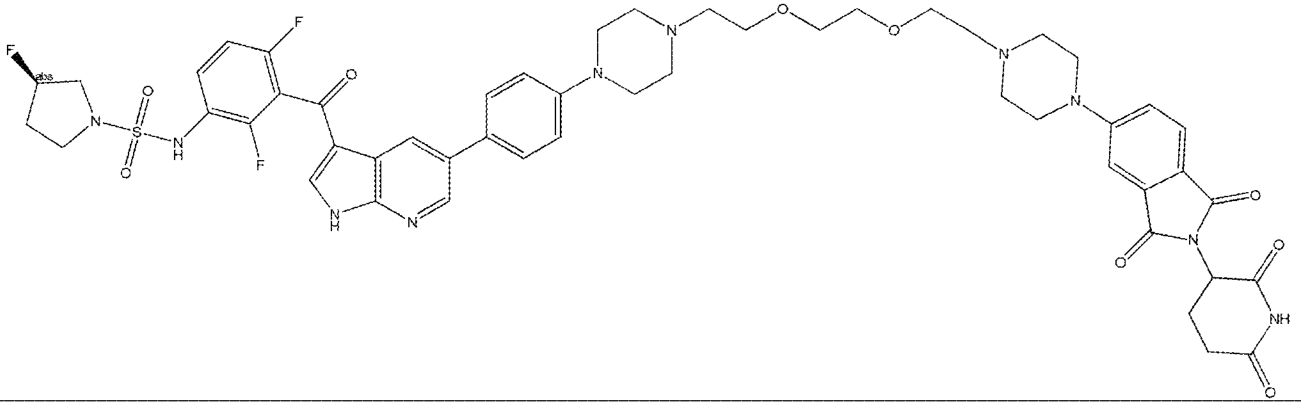
Figure 2B:
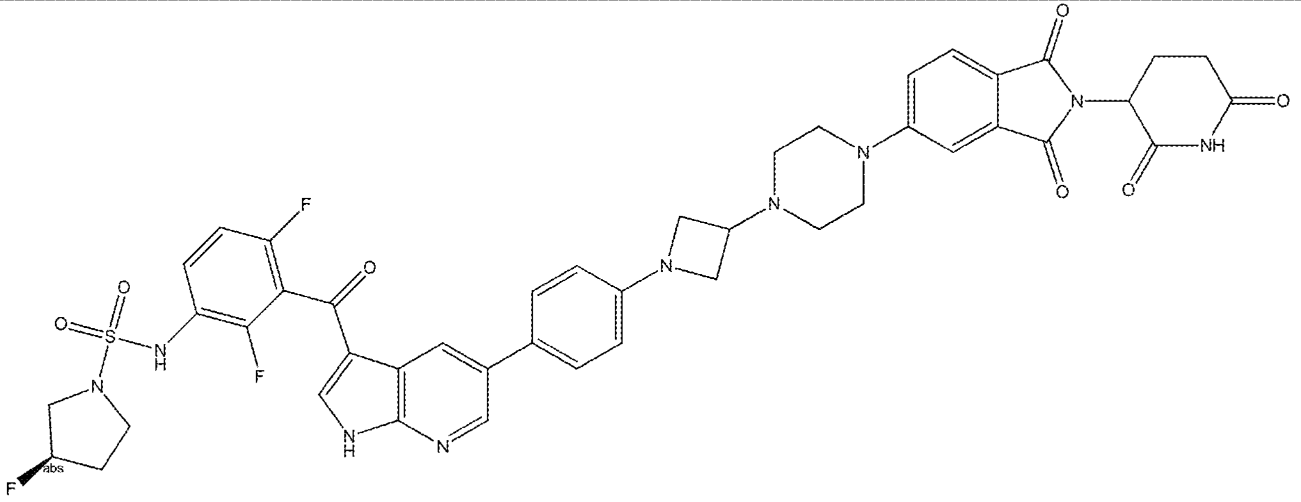
Figure 2B:
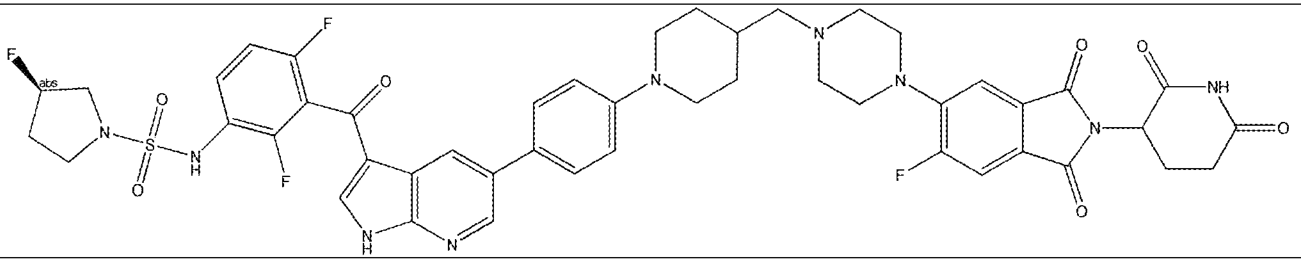
Figure 2B:
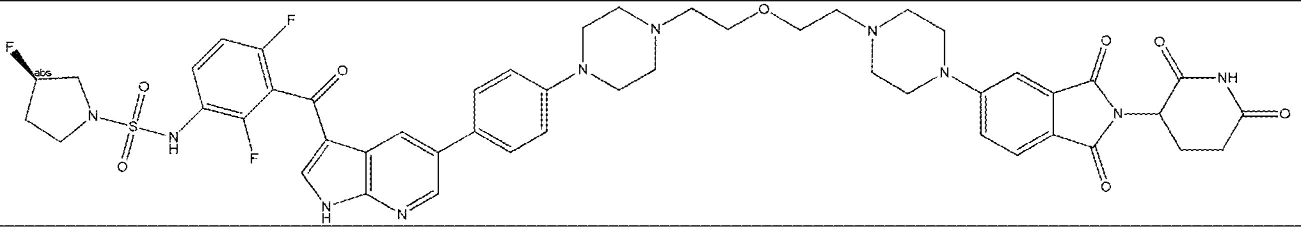
Figure 2B:
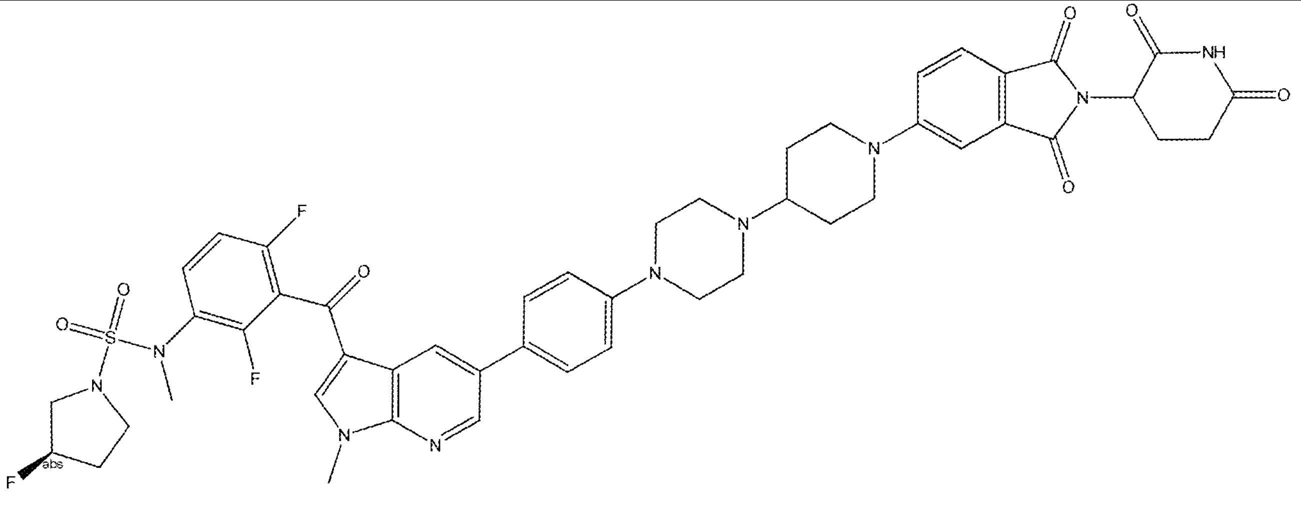
Figure 2B:
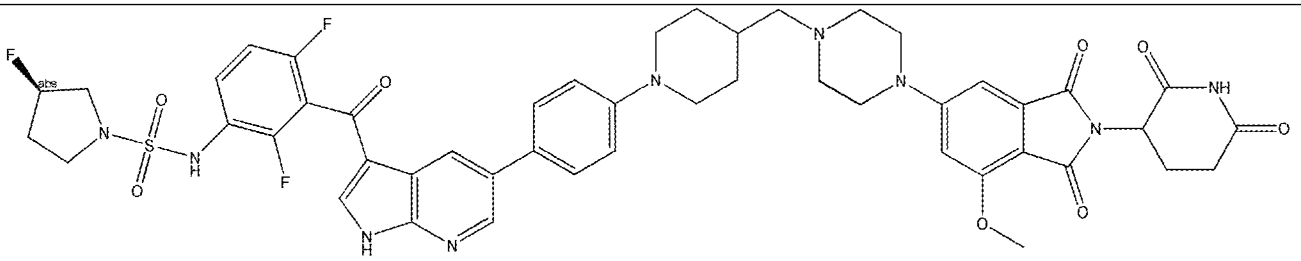
Figure 2B:
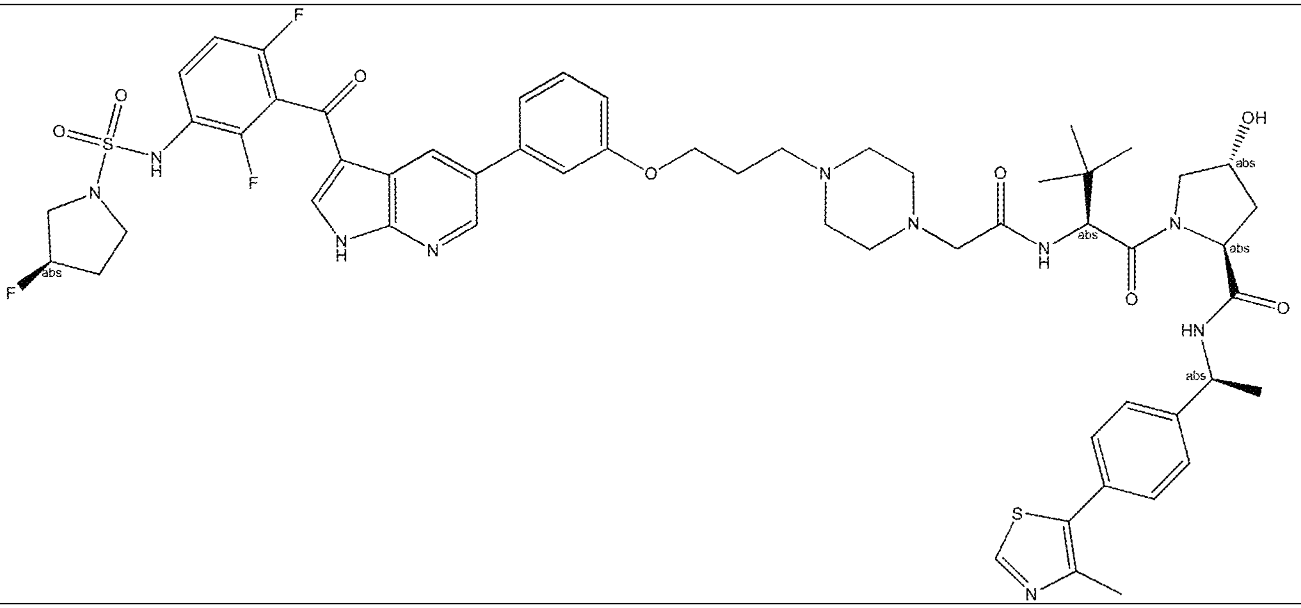
Figure 2B:
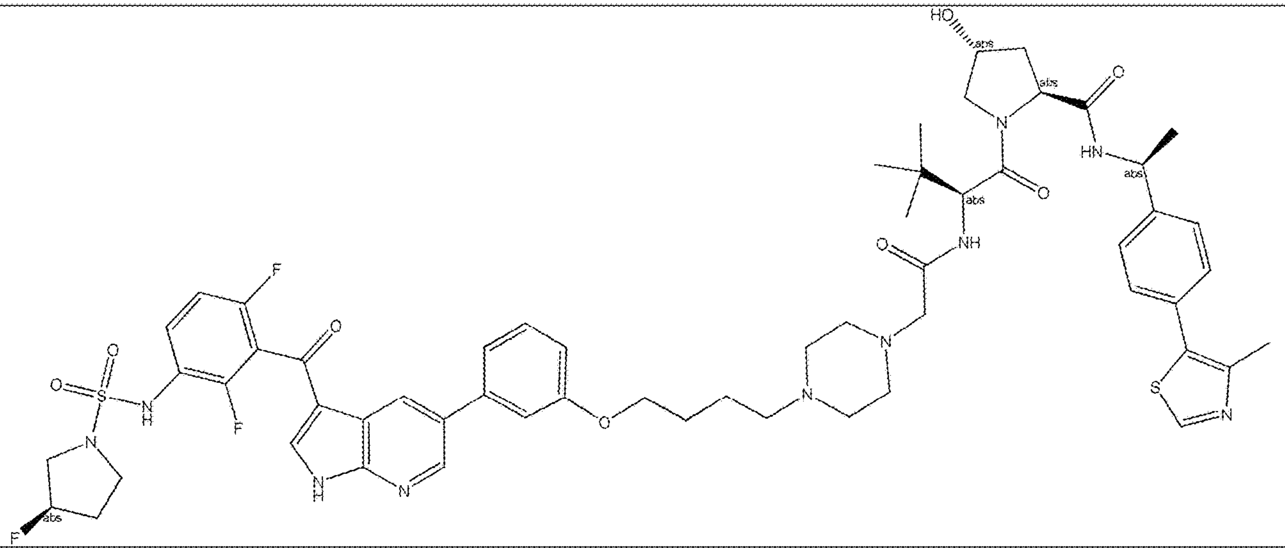
Figure 2B:
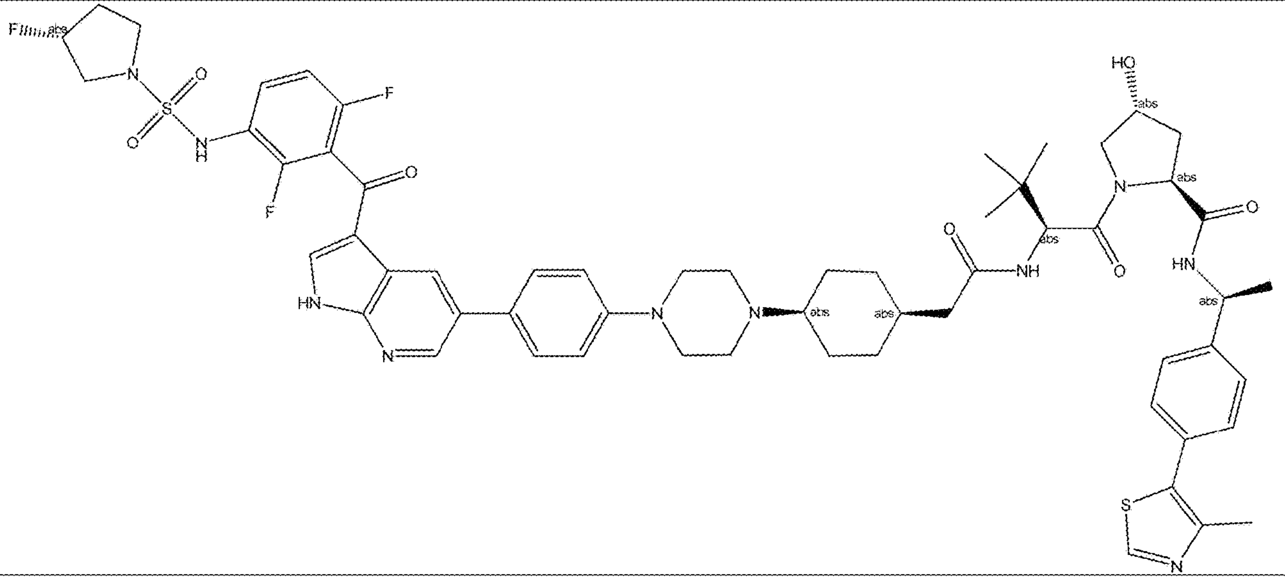
Figure 2B:
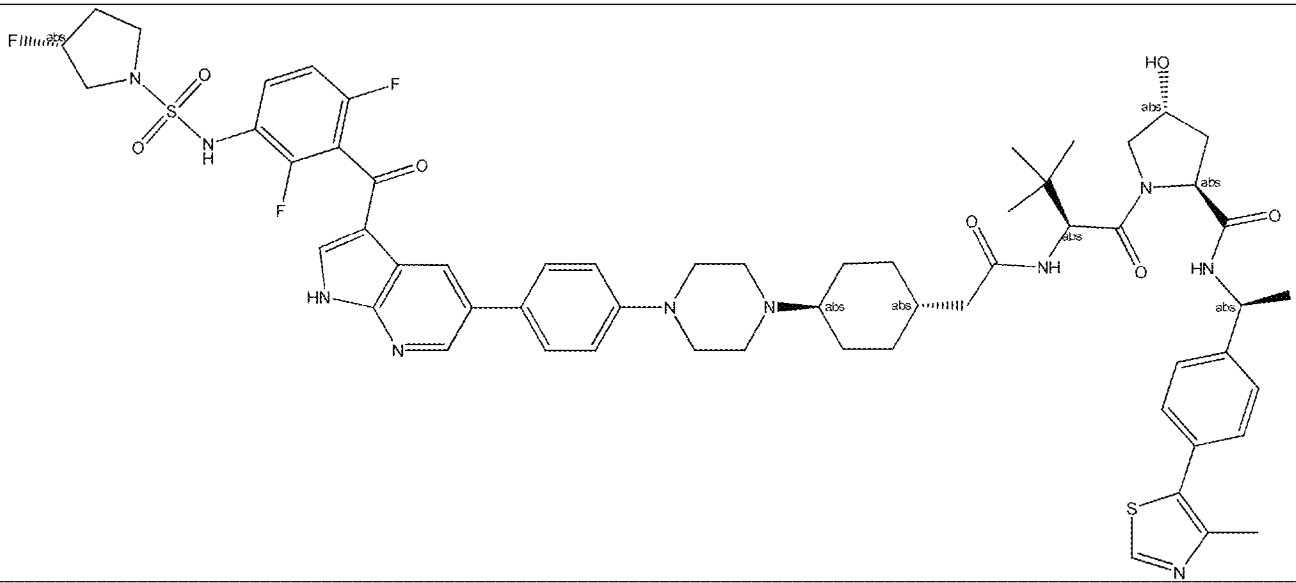
Figure 2B:
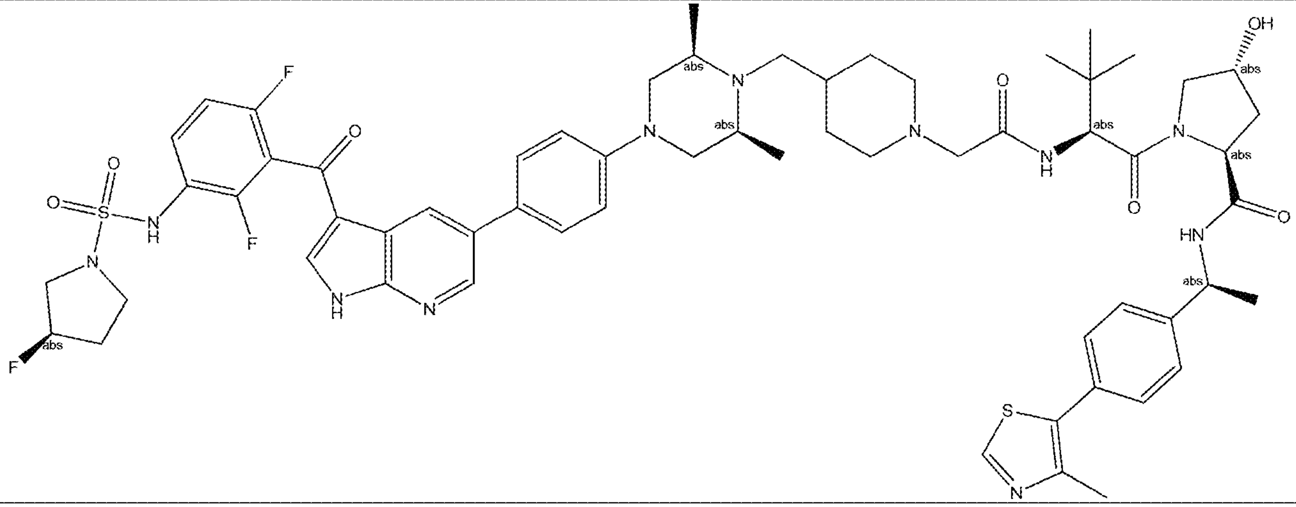
Figure 2B:
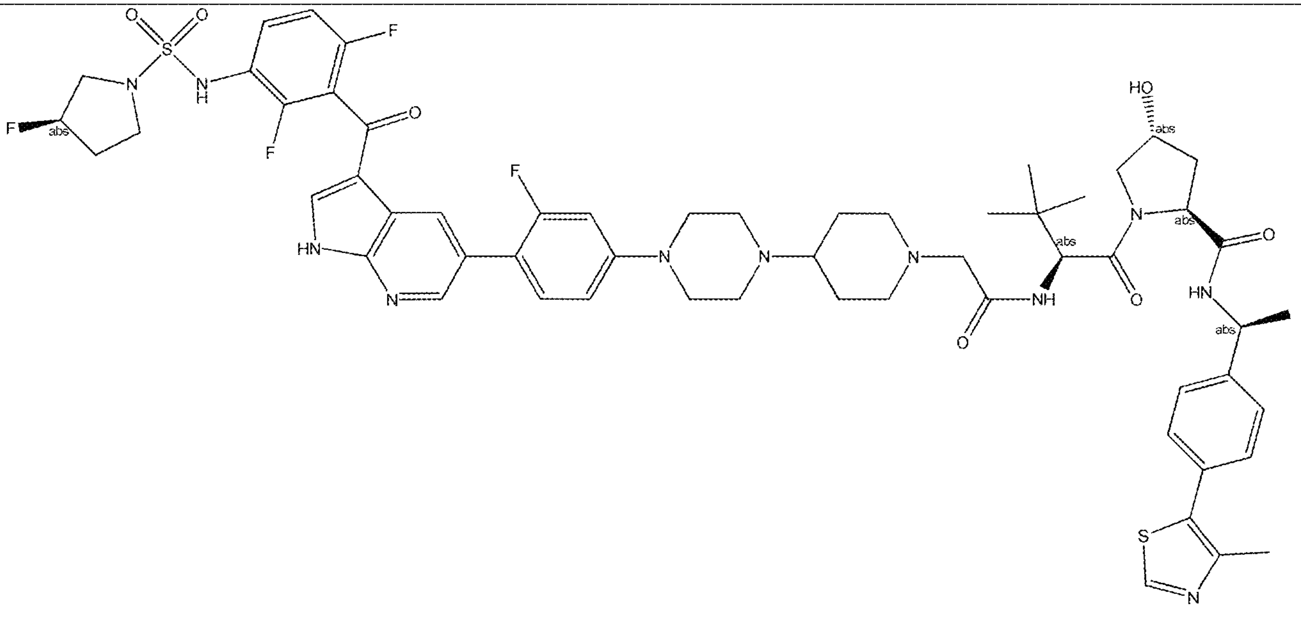
Figure 2B:
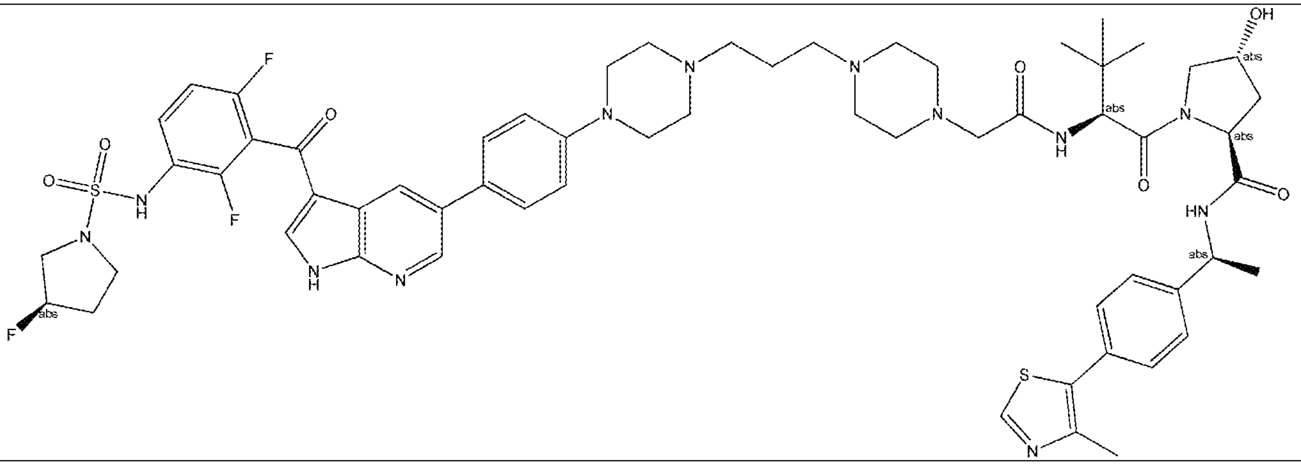
Figure 2B:
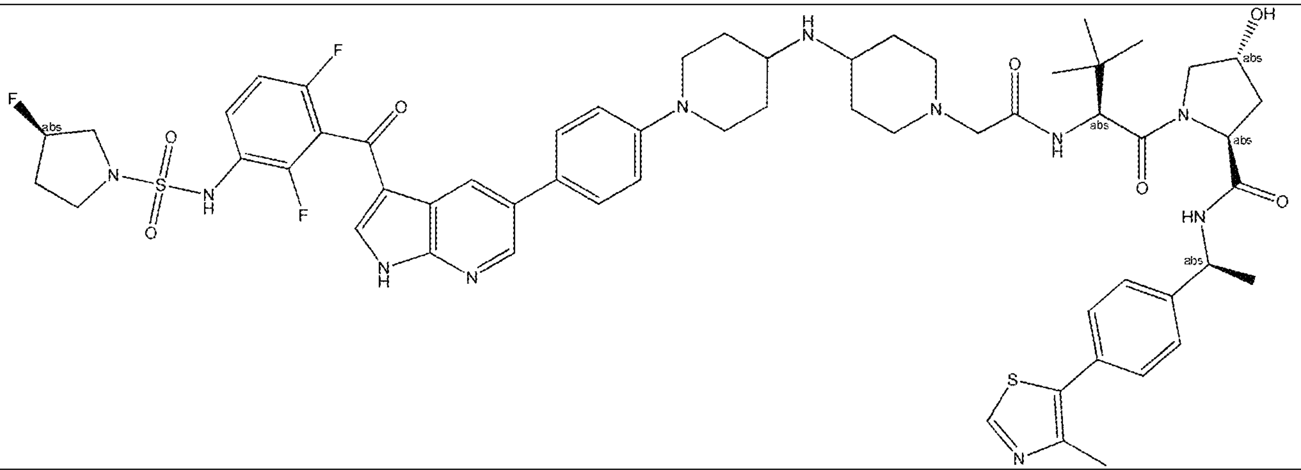
Figure 2B:
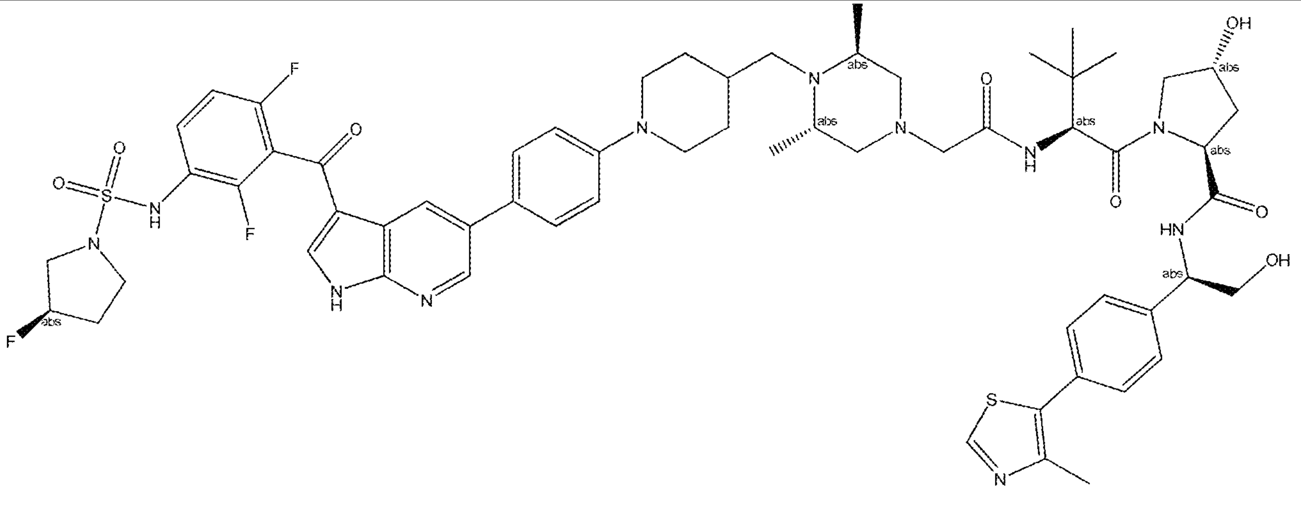
Figure 2B:
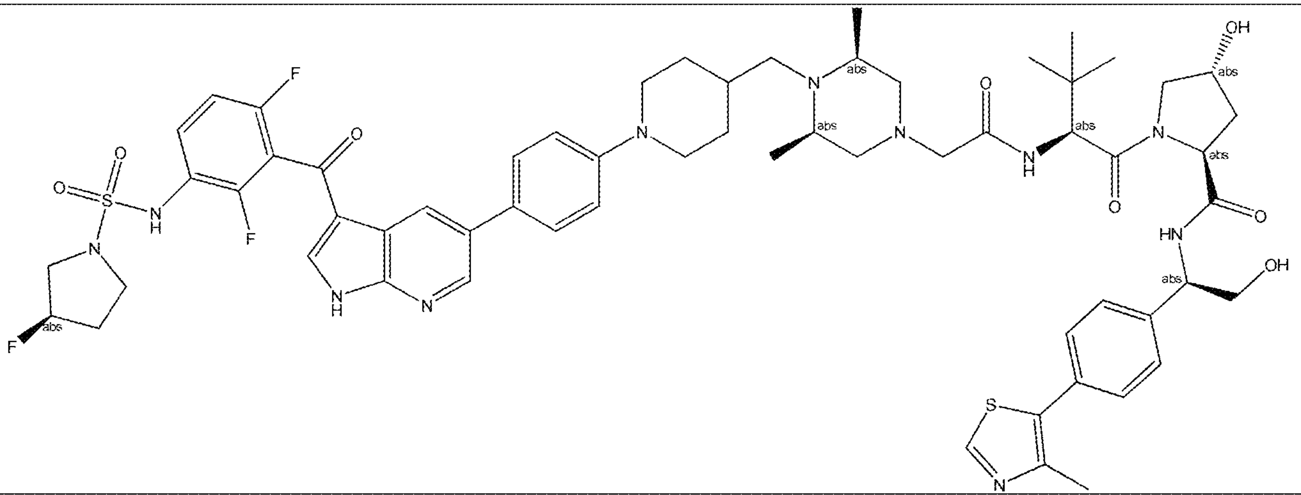
Figure 2B:
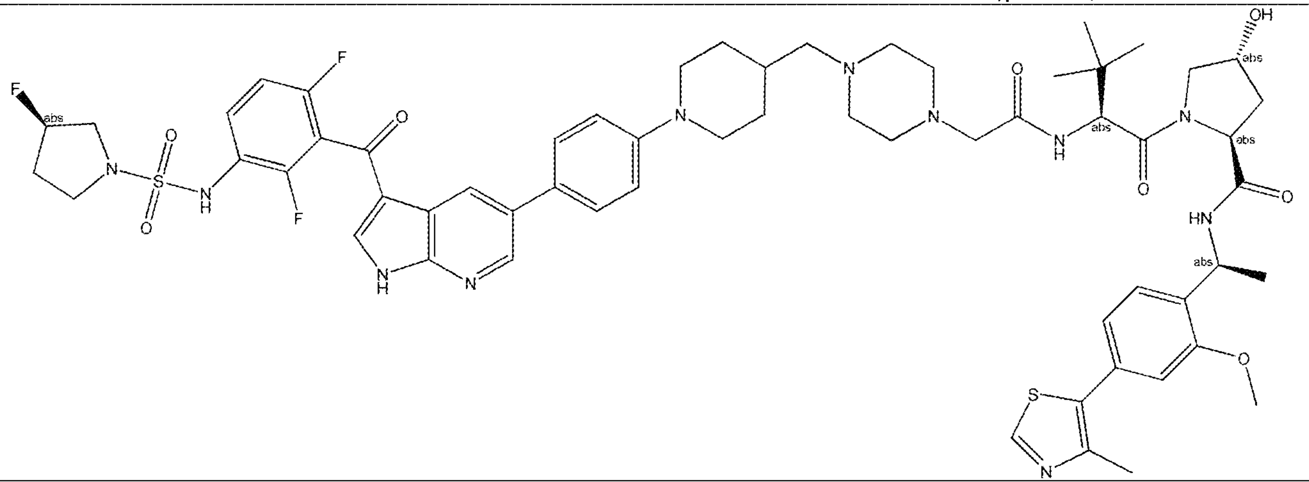
Figure 2B:
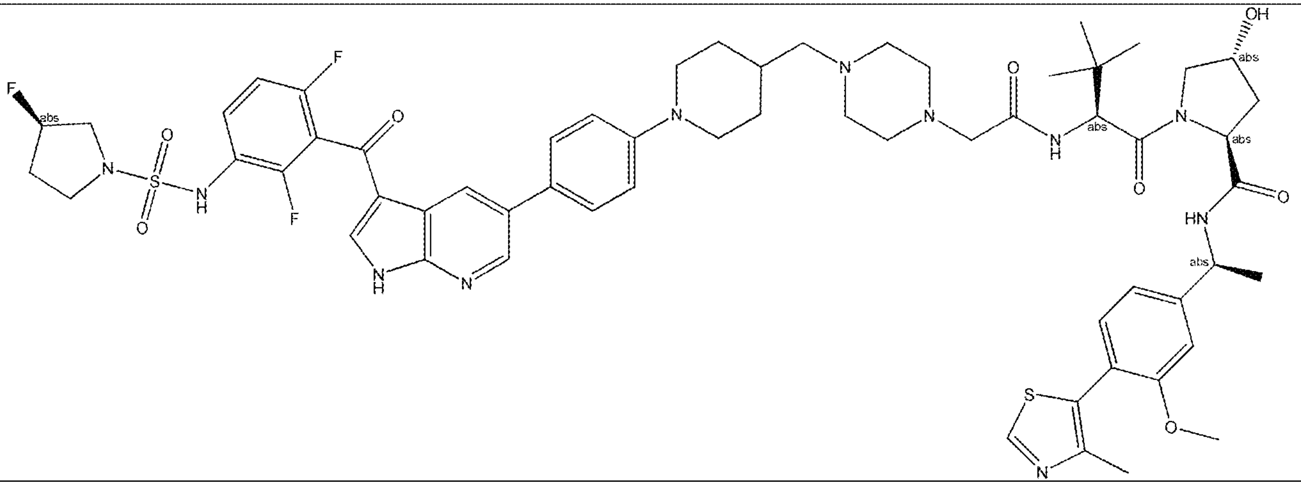
Figure 2B:
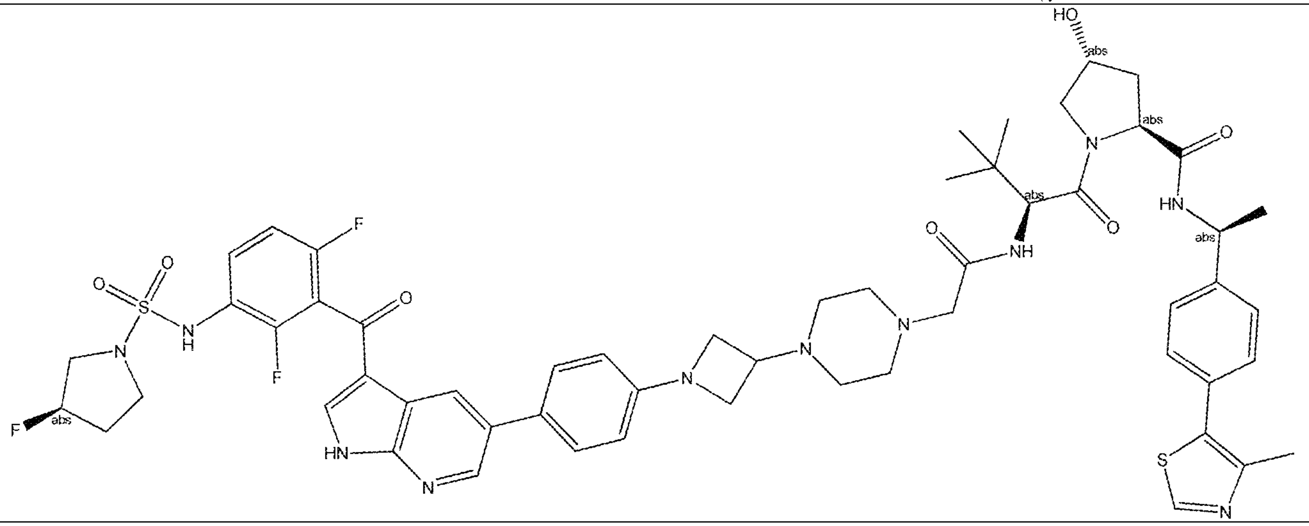
Figure 2B:
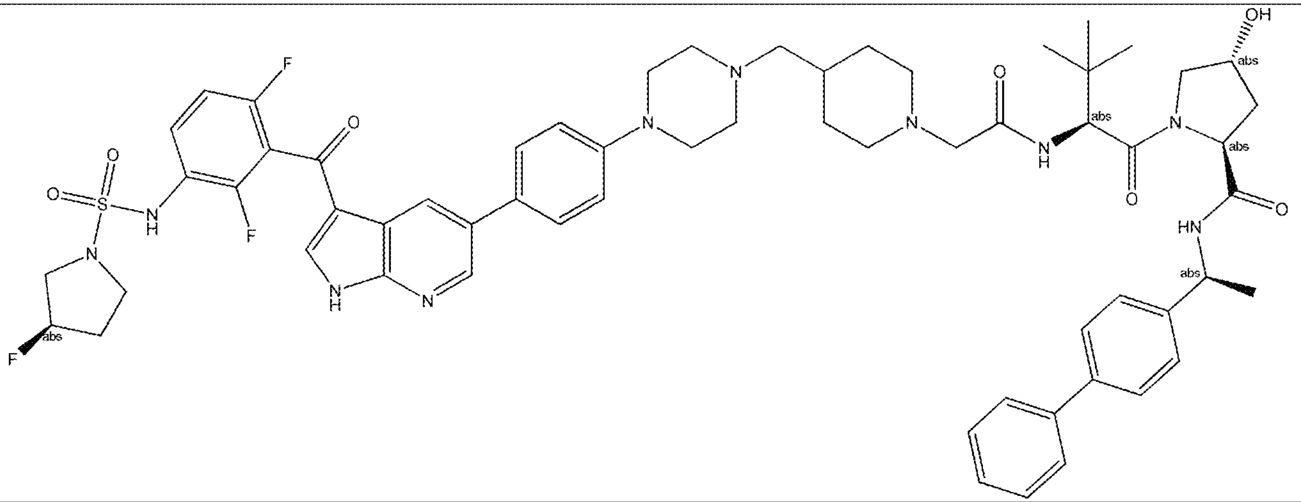
Figure 2B:
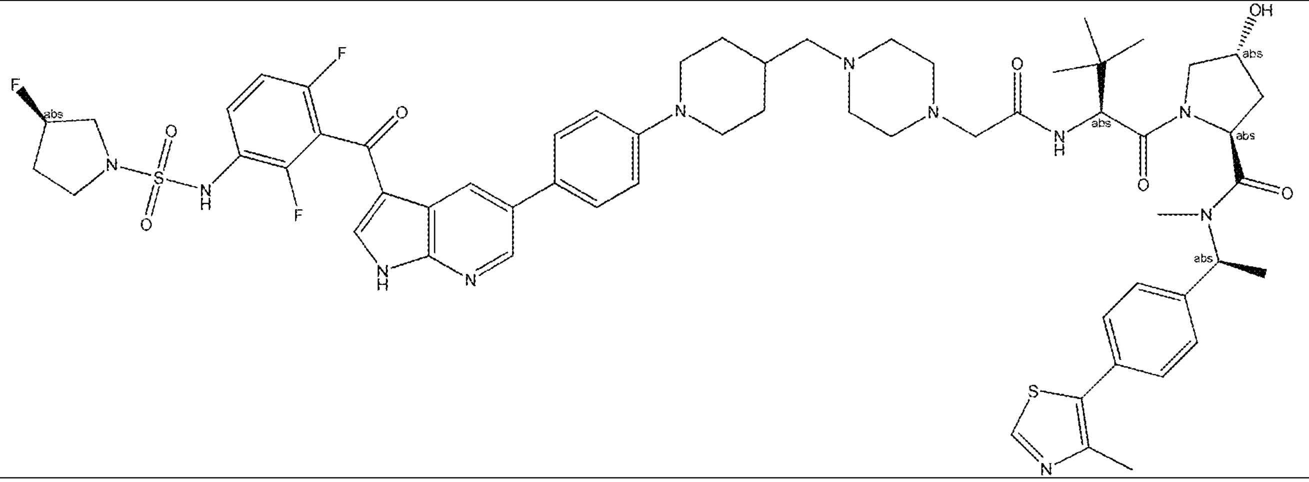
Figure 2B:
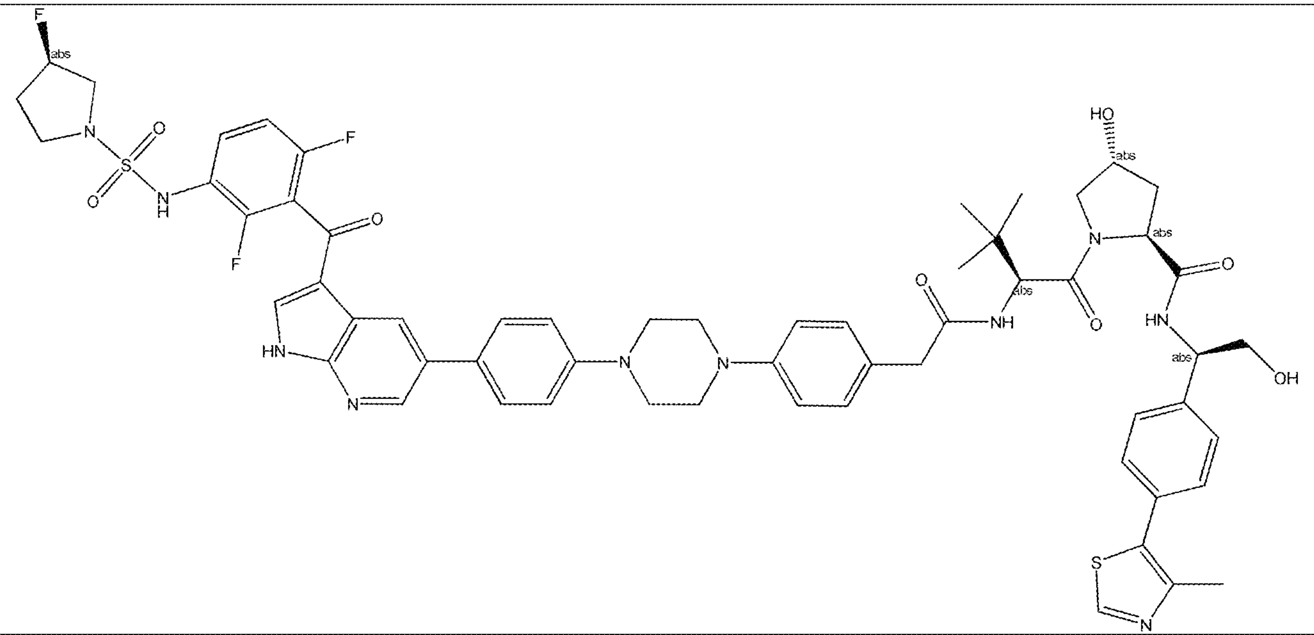
Figure 2B:
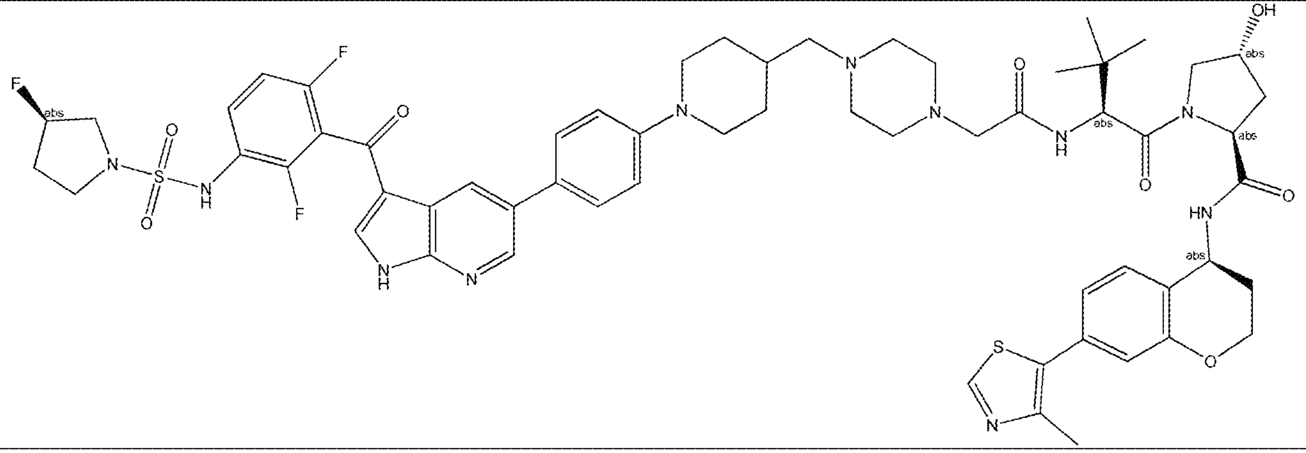
Figure 2B:
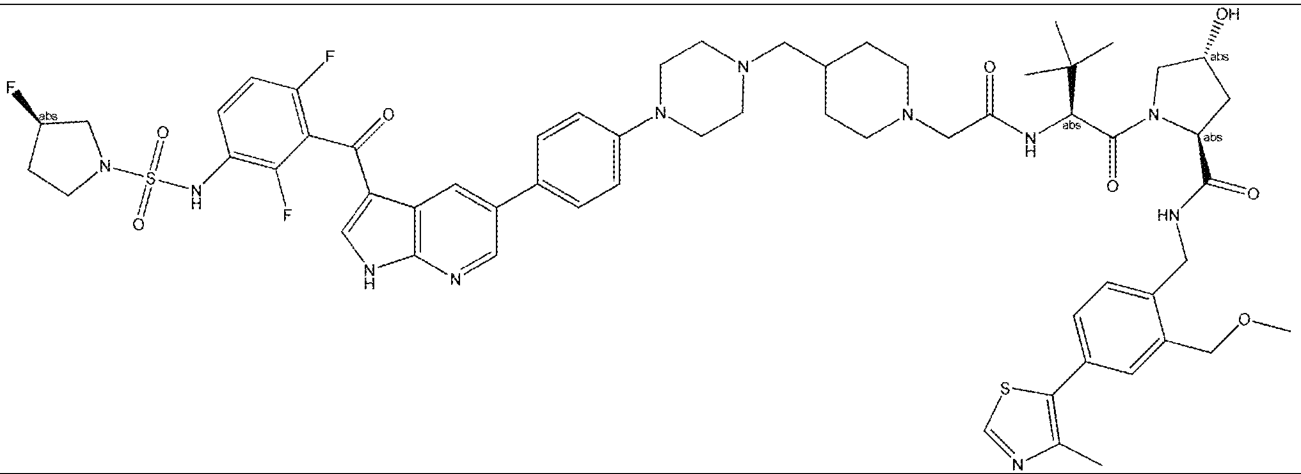
Figure 2B:
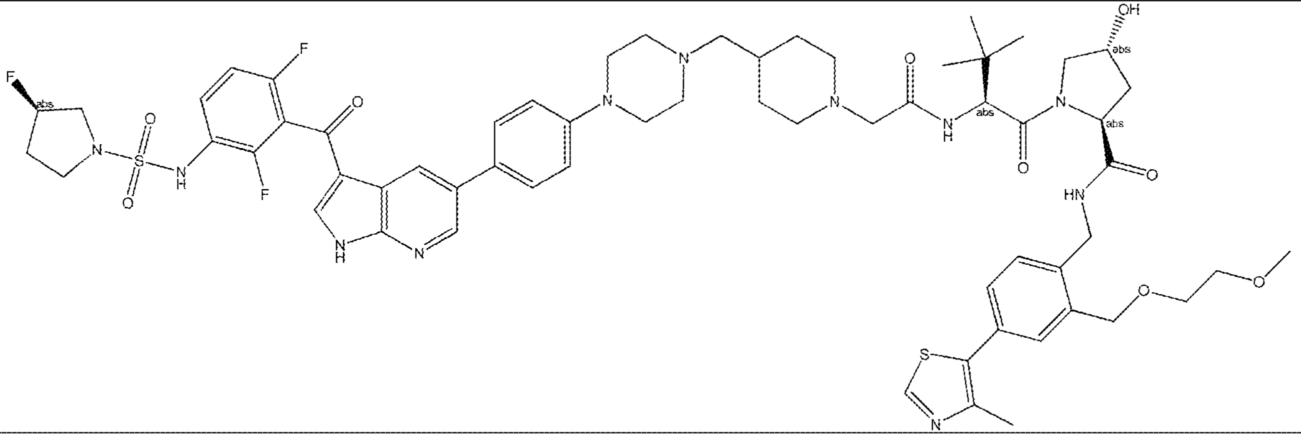
Figure 2B:
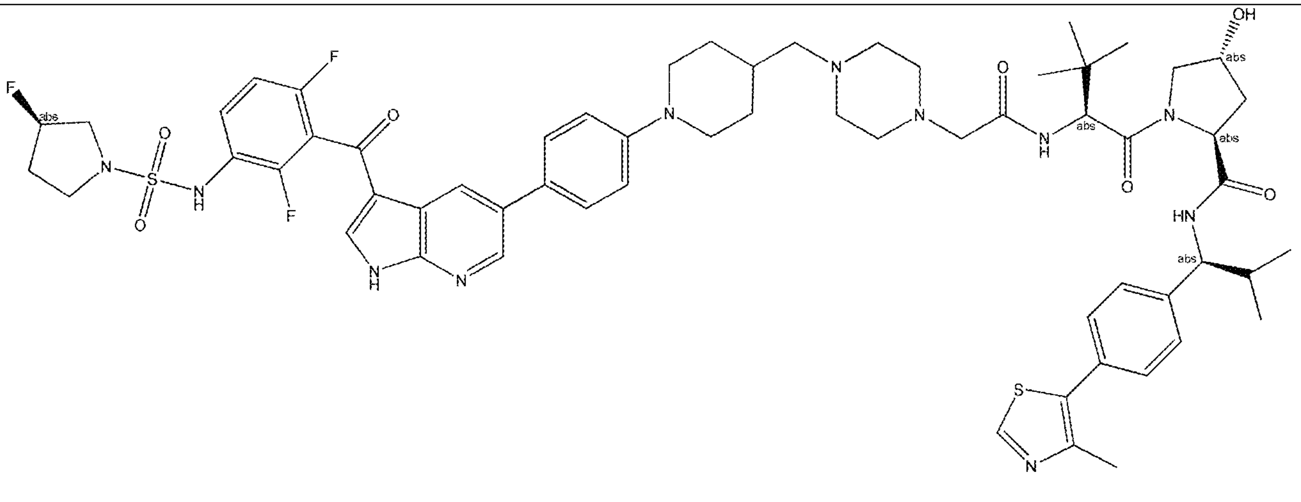
Figure 2B:
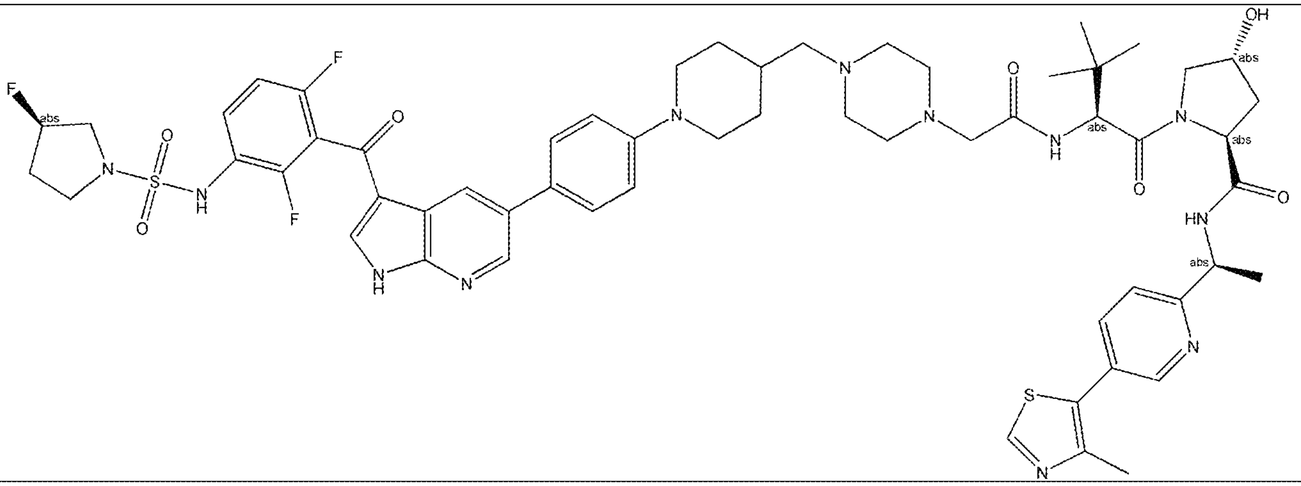
Figure 2B:
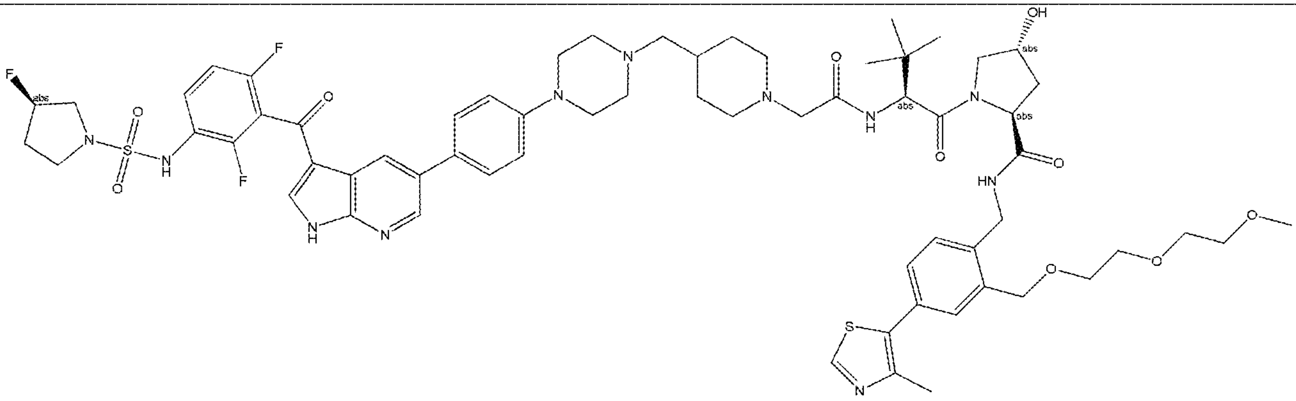
Figure 2B:
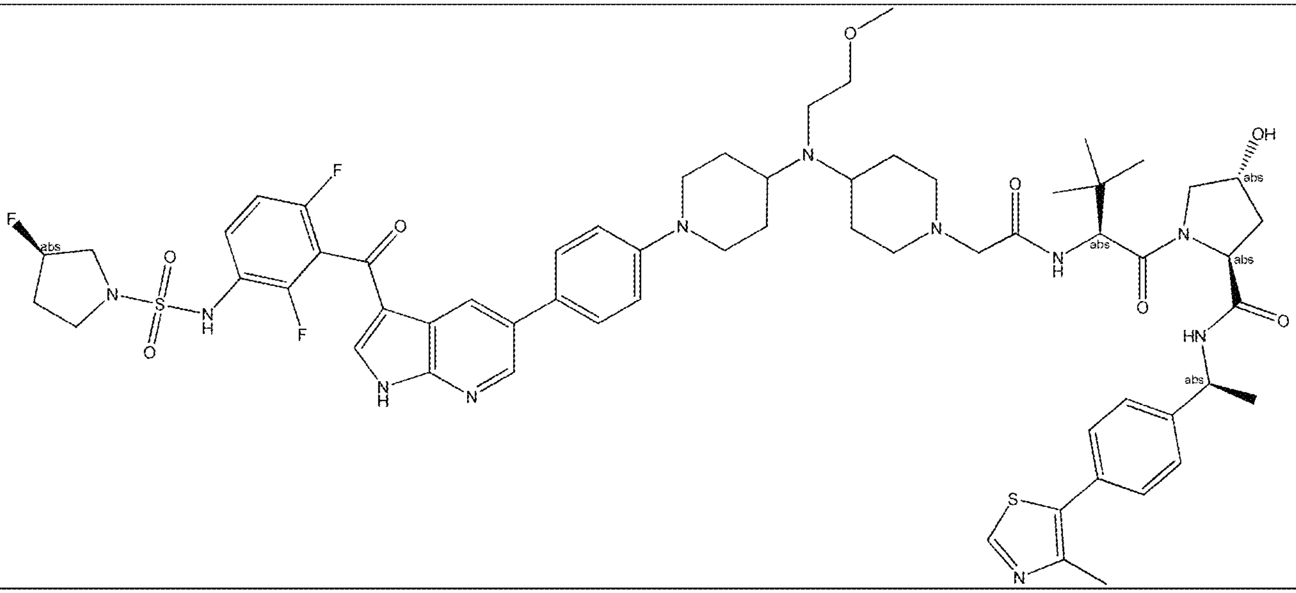
Figure 2B:
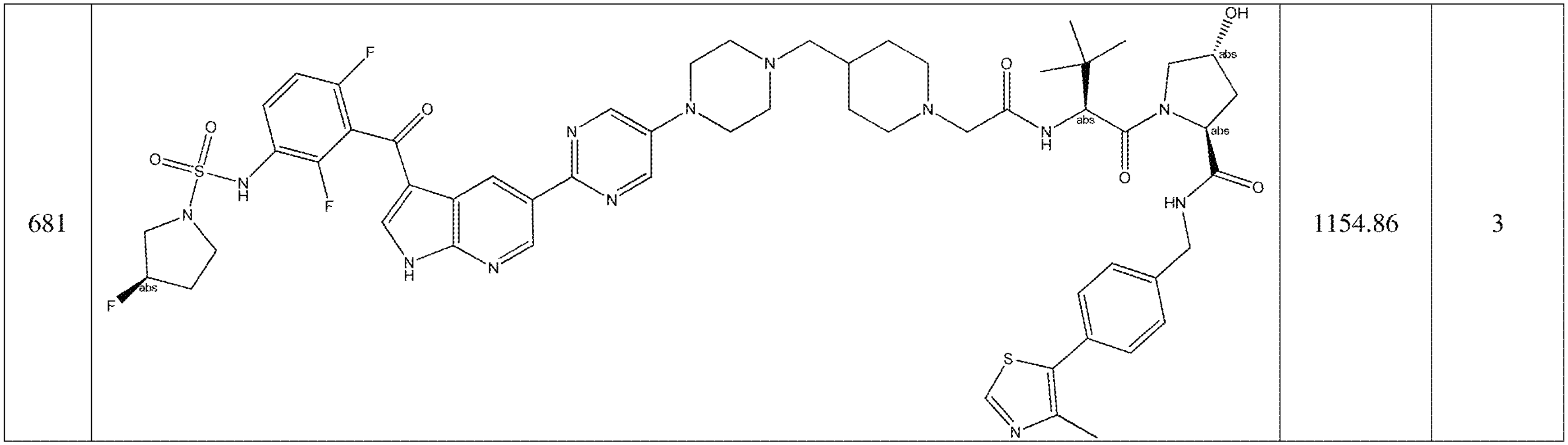
Figure 2B:
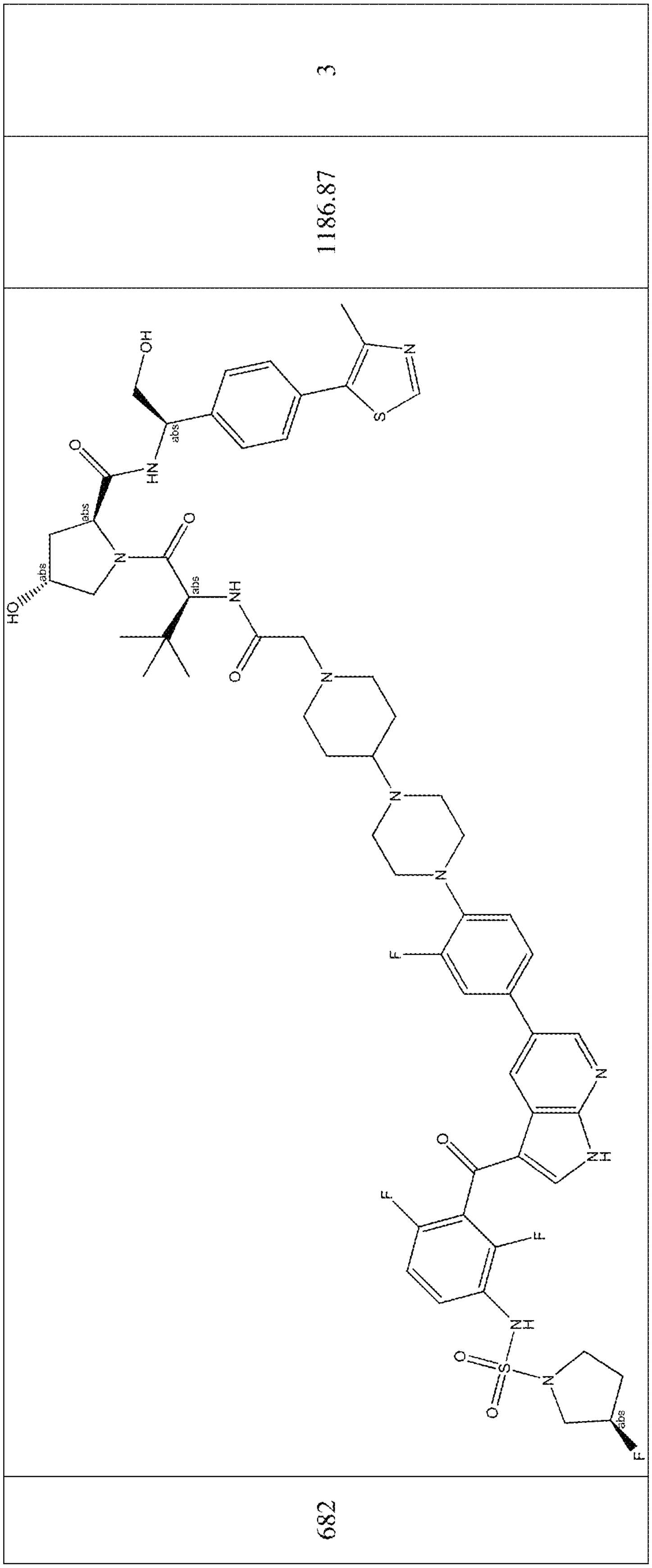
Figure 2B:
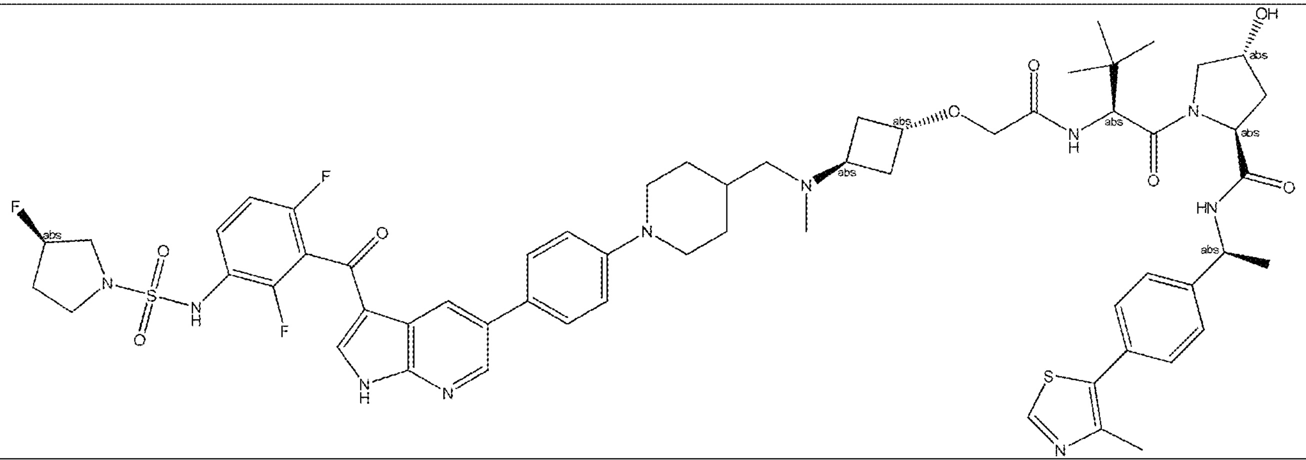
Figure 2B:
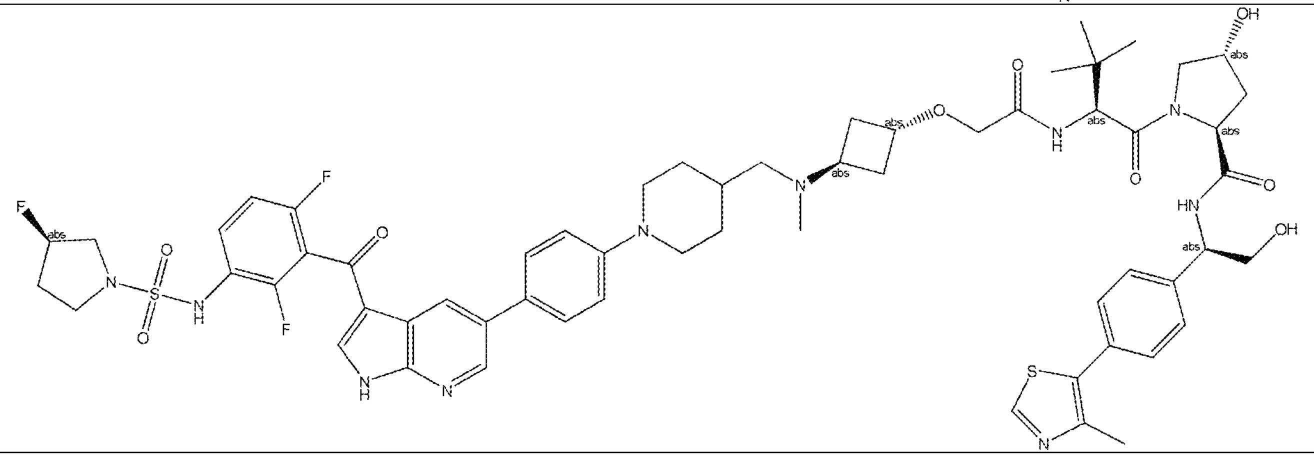
Figure 2B:
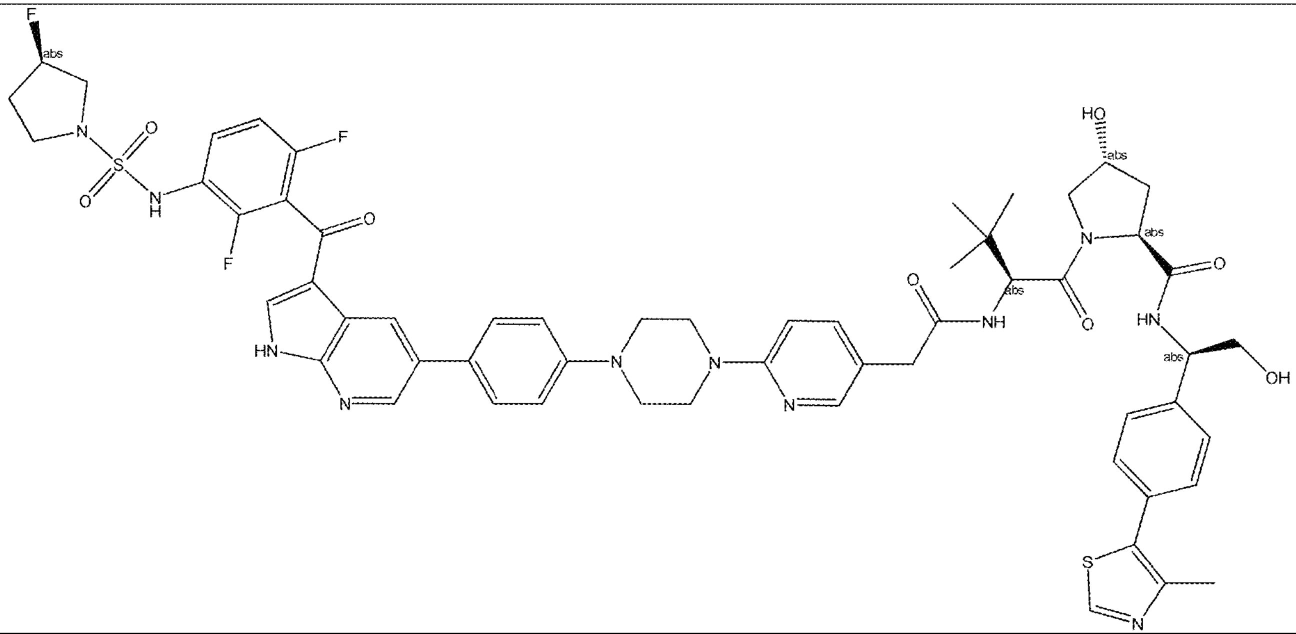
Figure 2B:
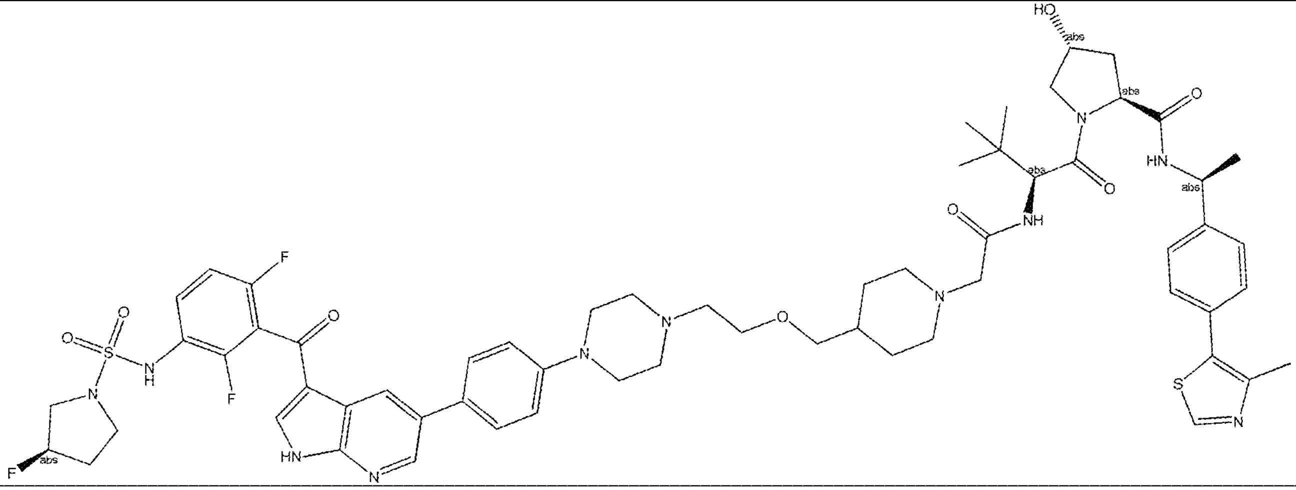
Figure 2B:
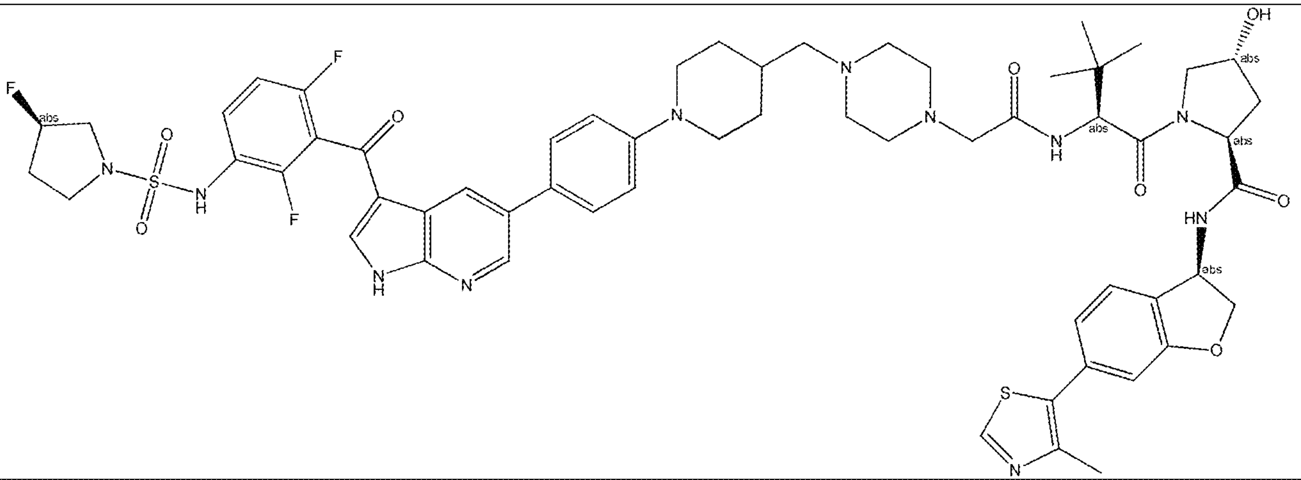
Figure 2B:
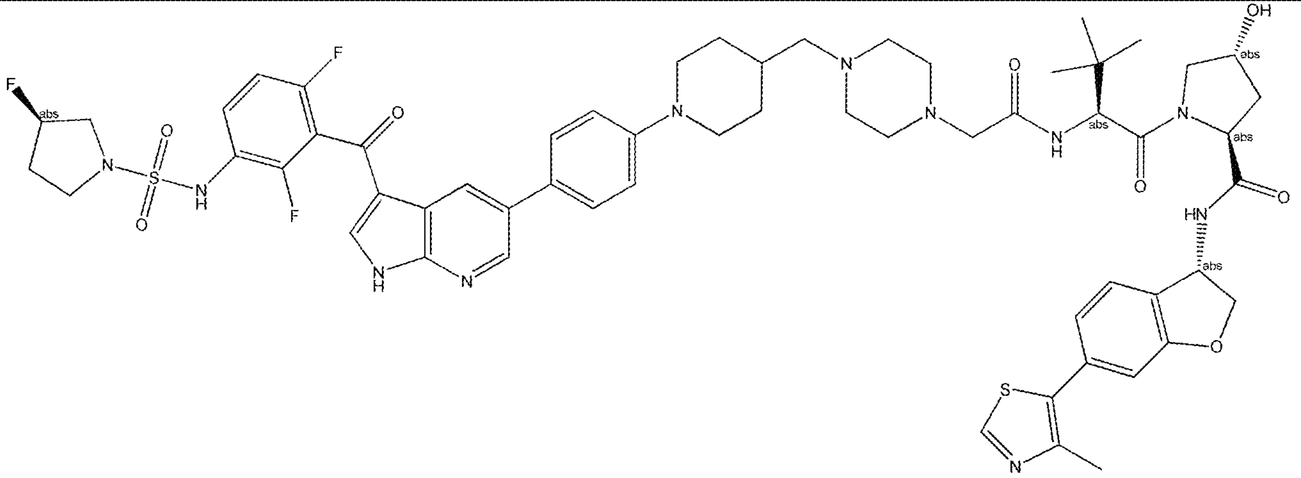
Figure 2B:
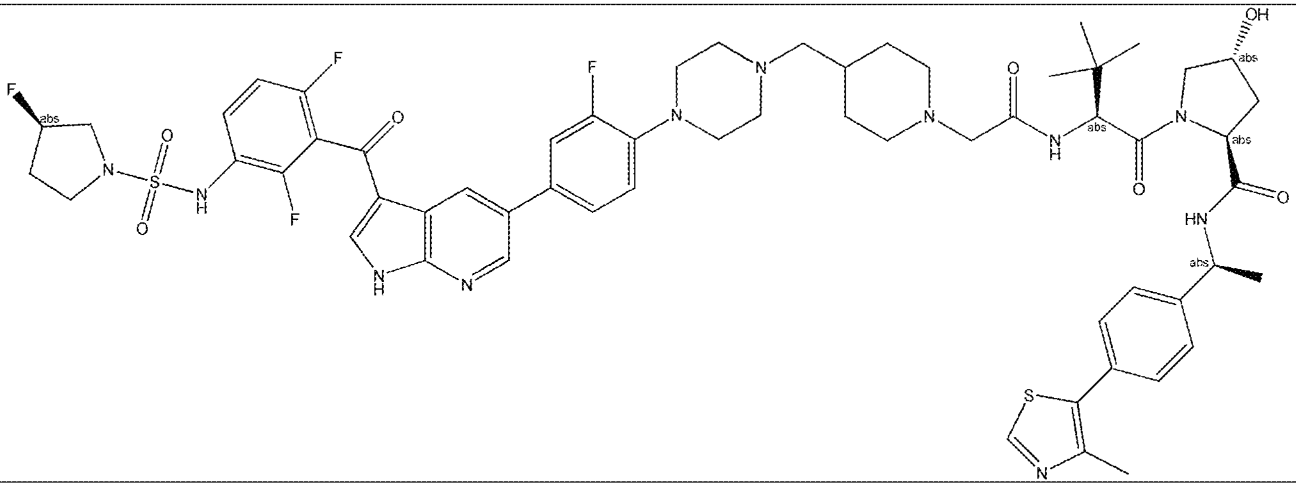
Figure 2B:
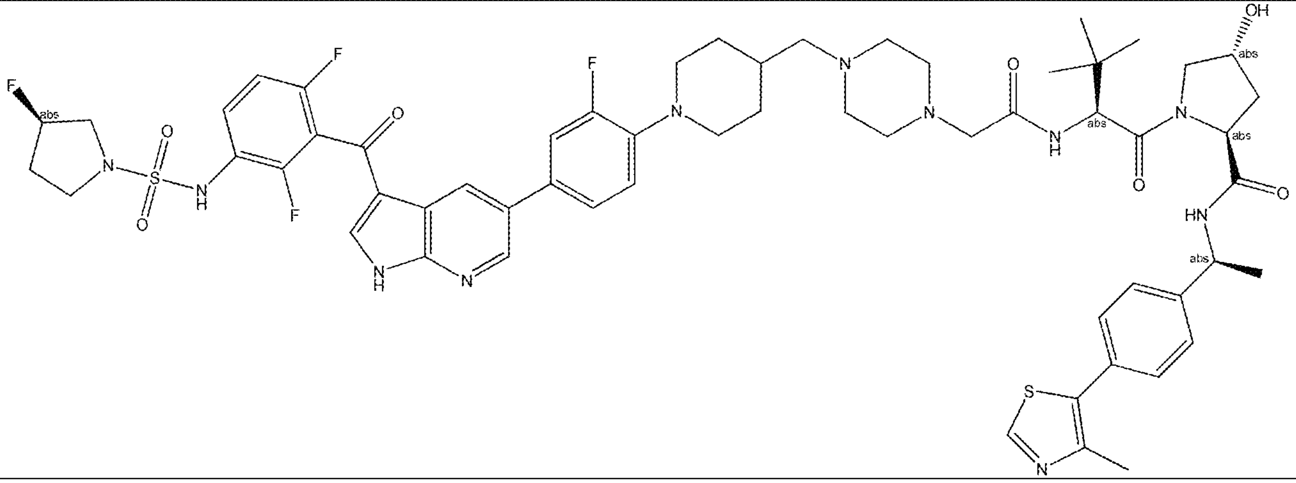
Figure 2B:
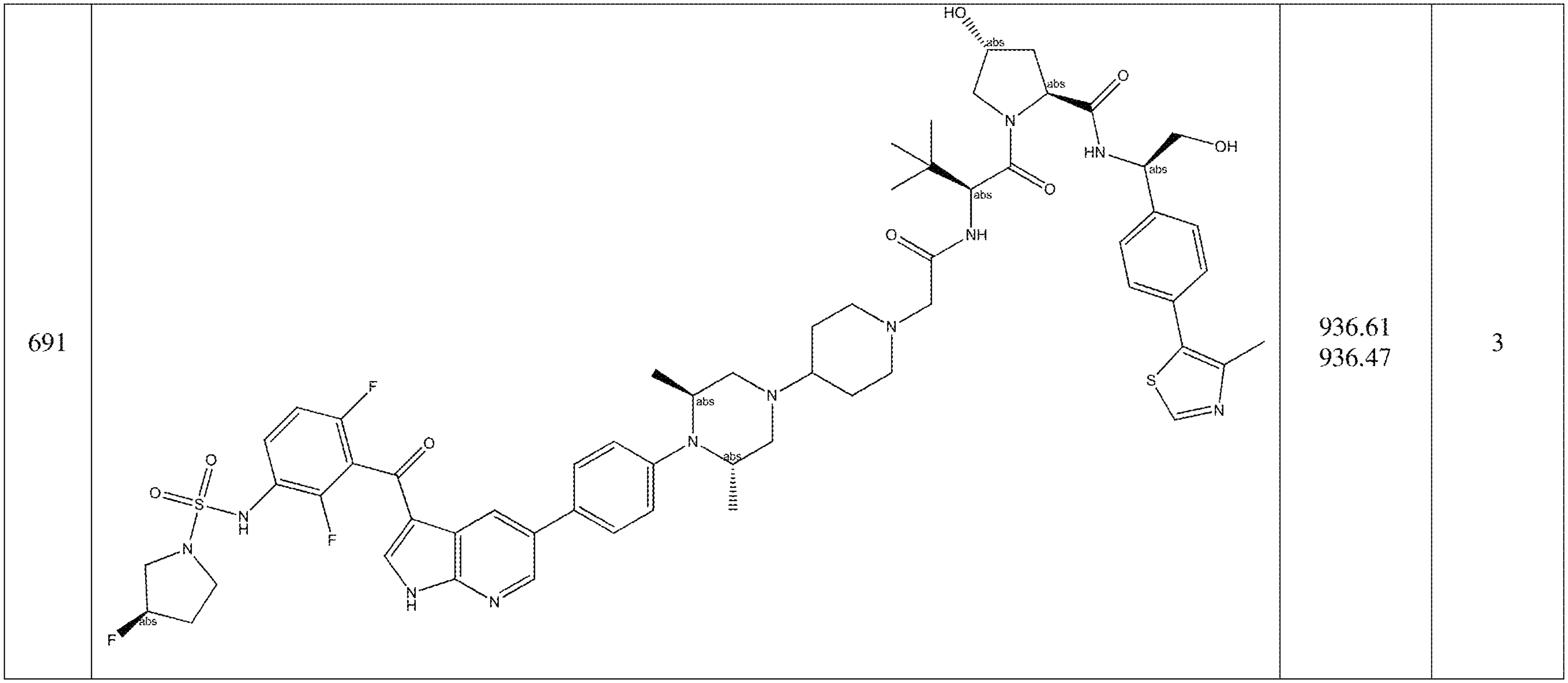
Figure 2B:
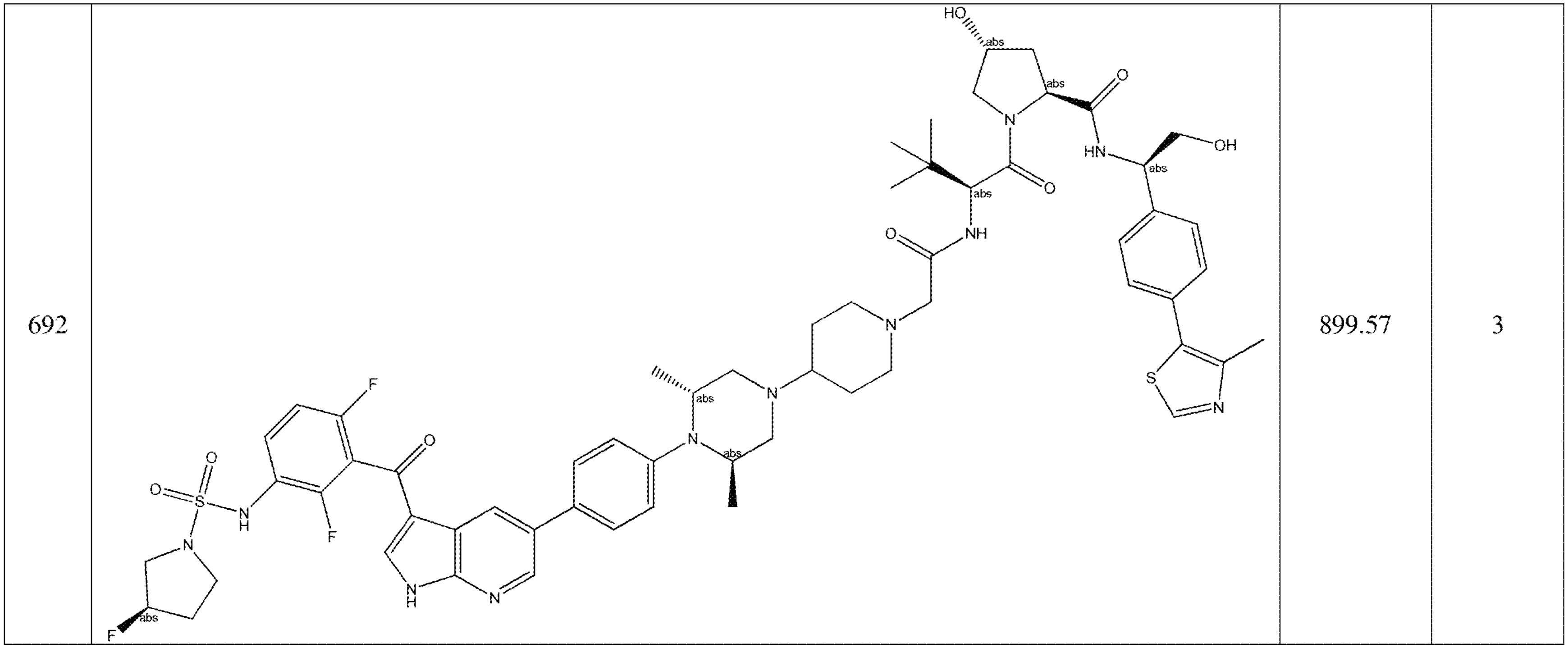
Figure 2B:
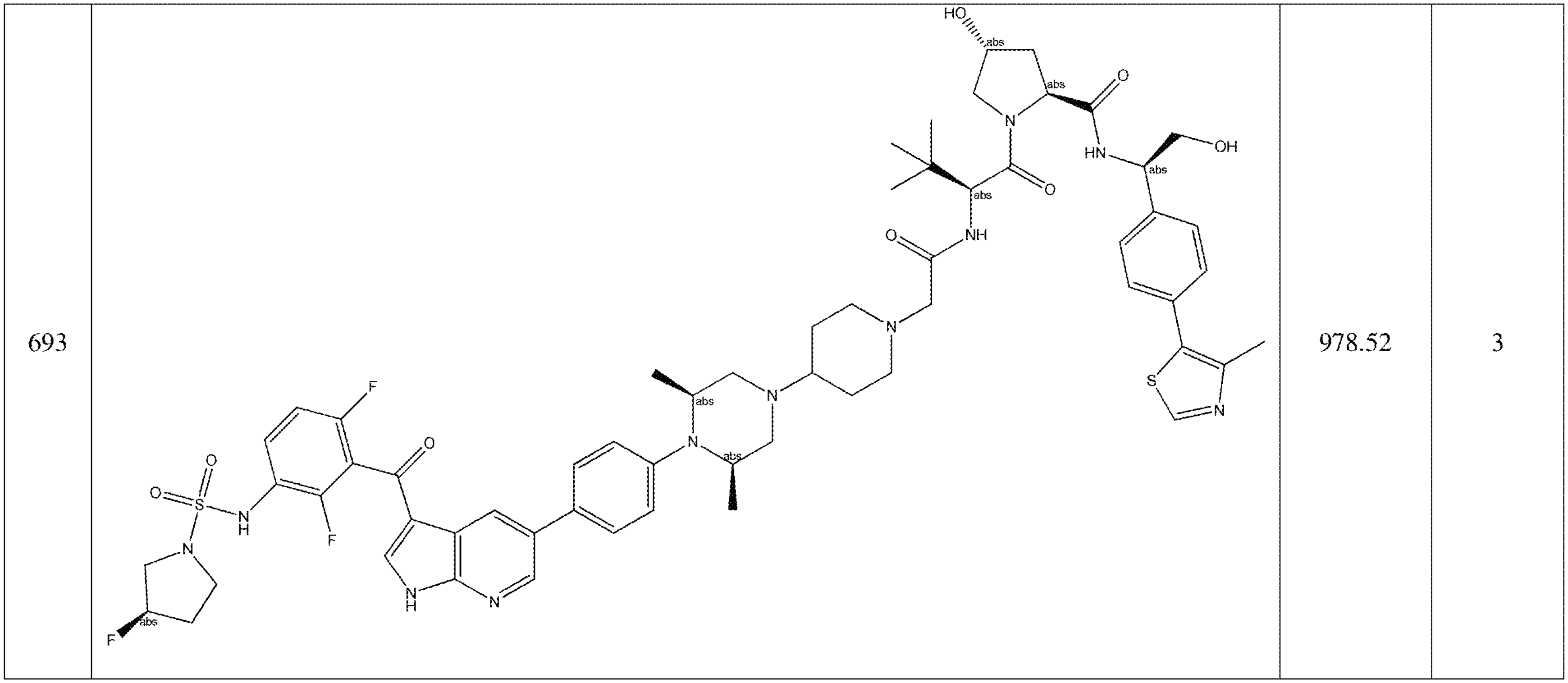
Figure 2B:
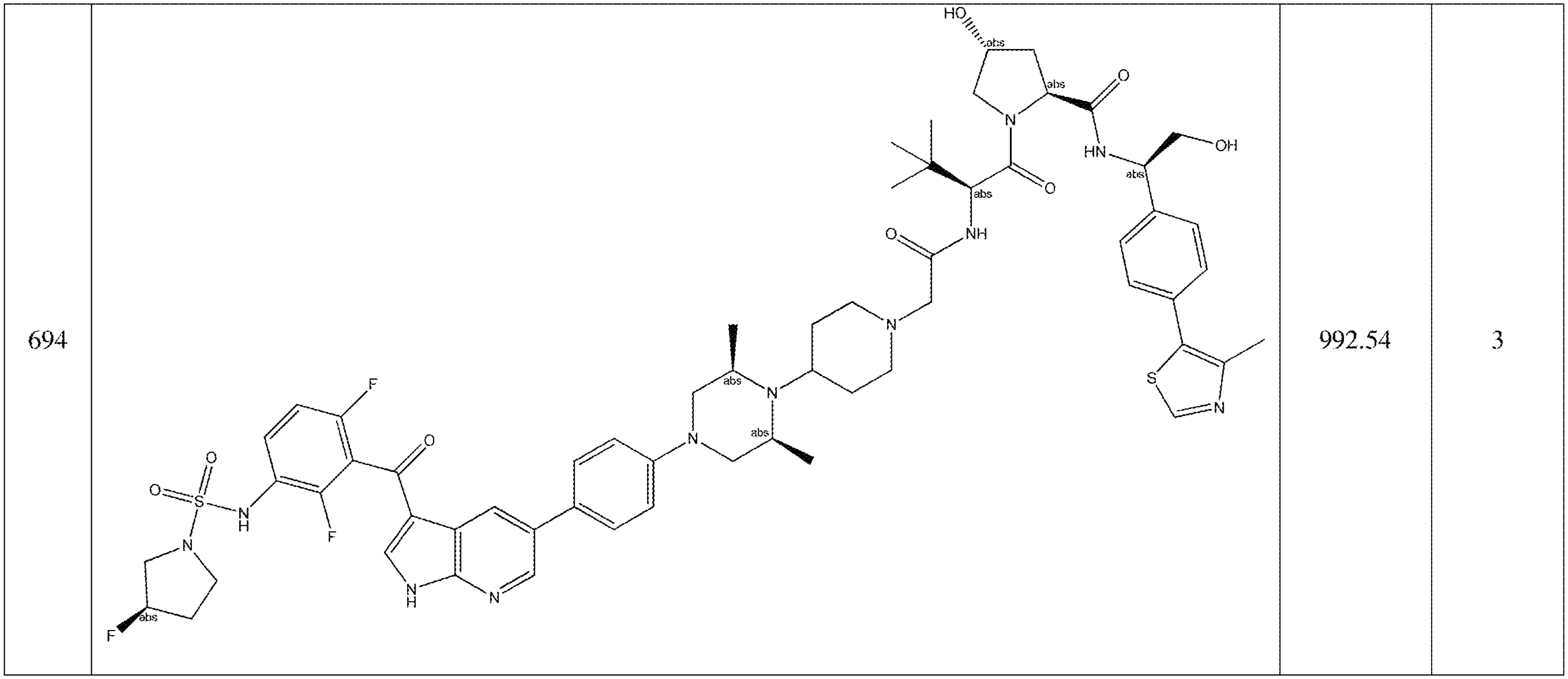
Figure 2B:
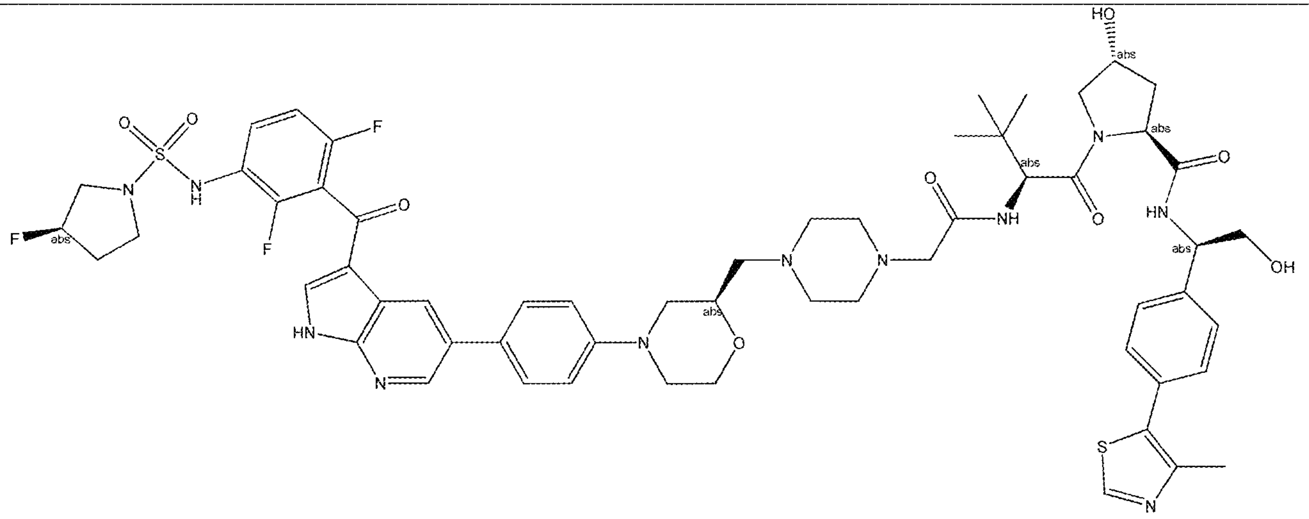
Figure 2B:
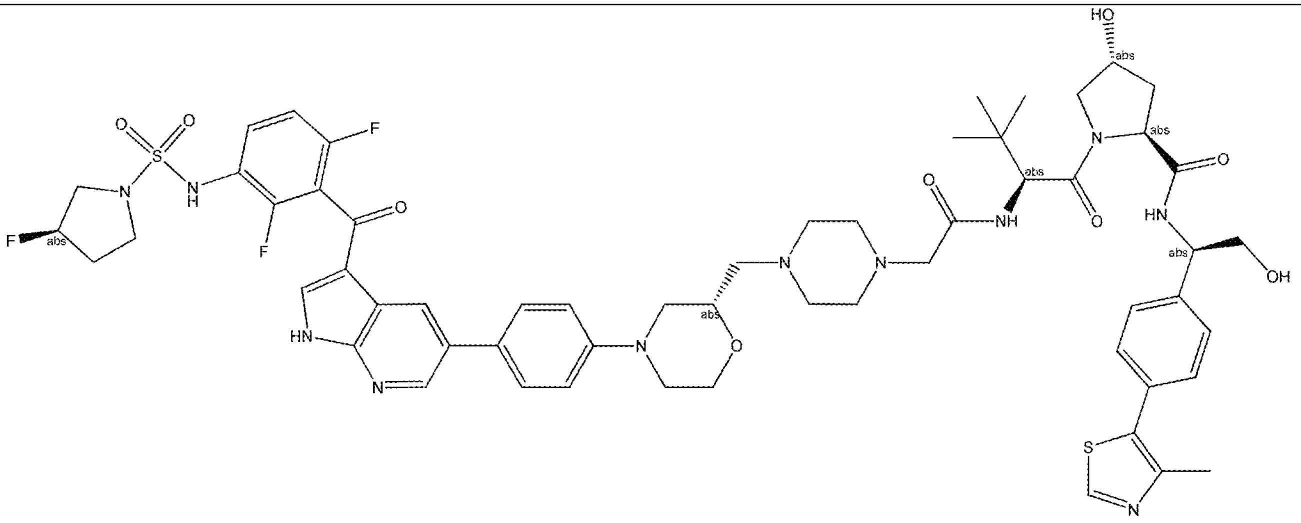
Figure 2B:
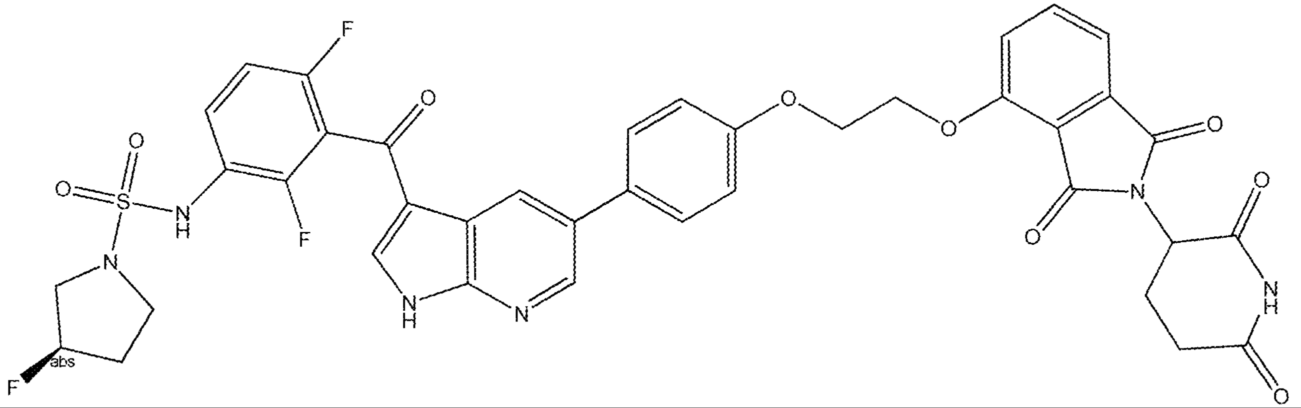
Figure 2B:
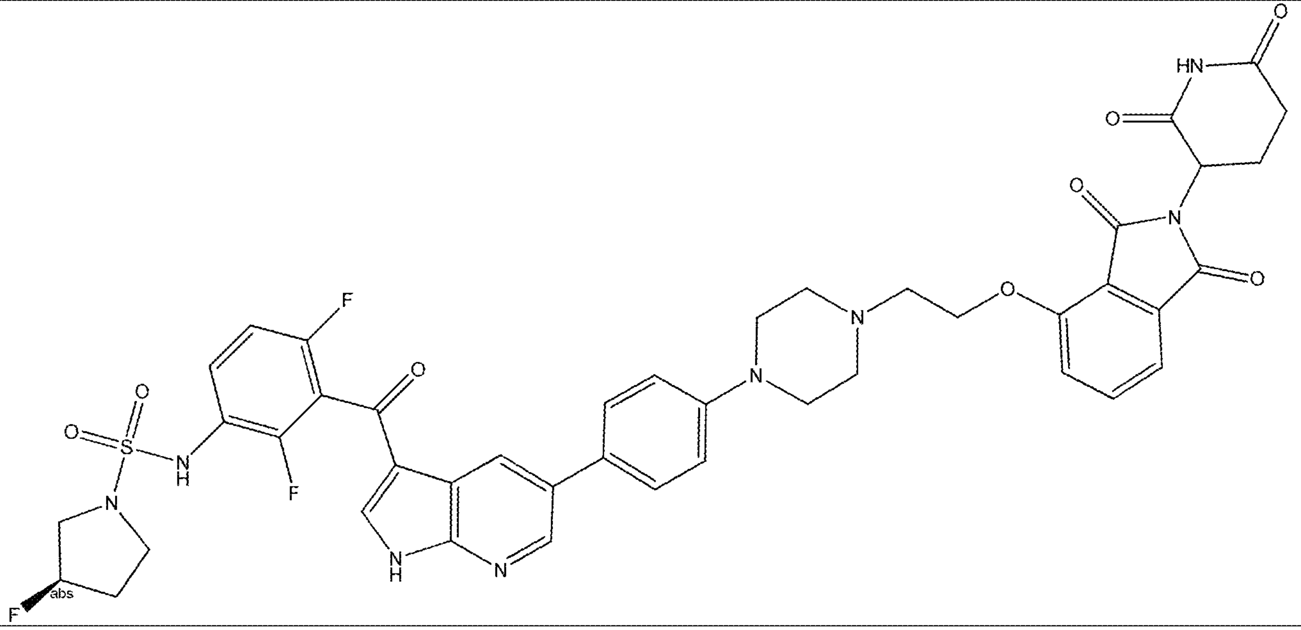
Figure 2B:
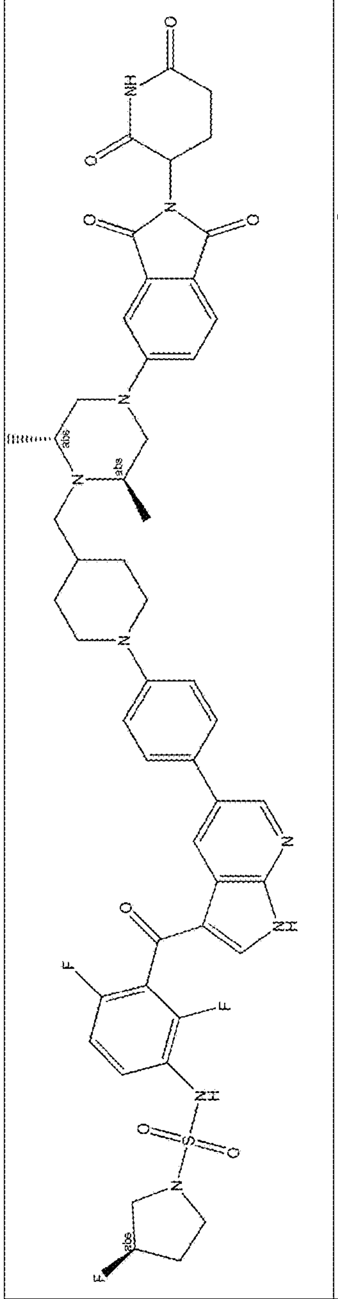
Figure 2B:
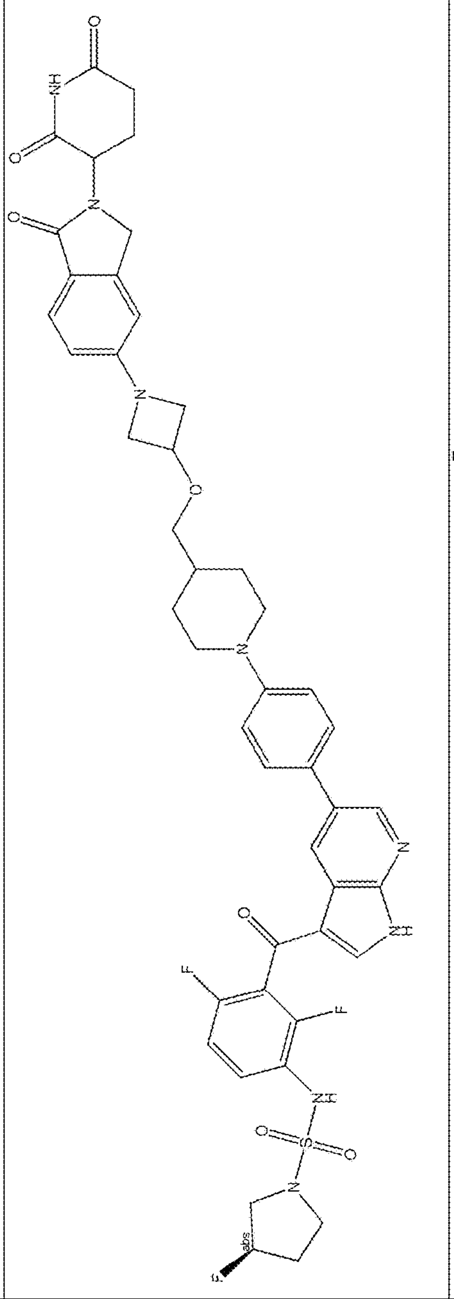
Figure 2B:
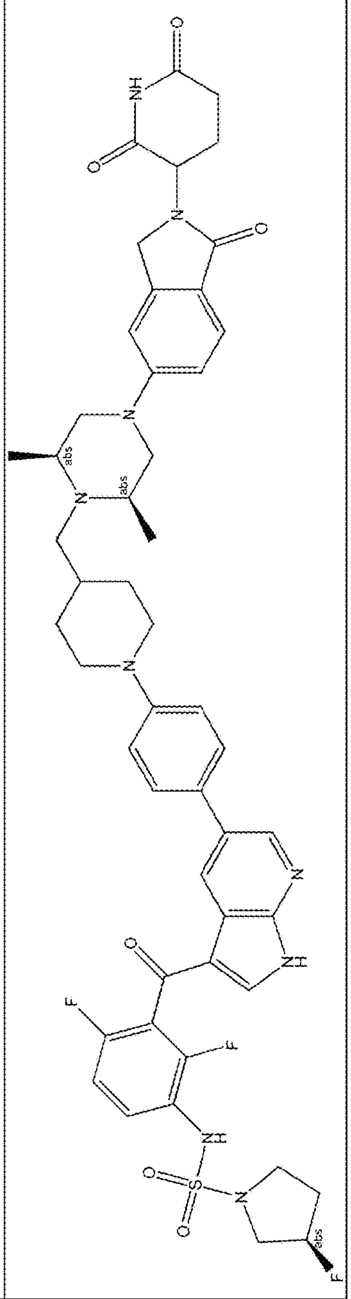
Figure 2B:
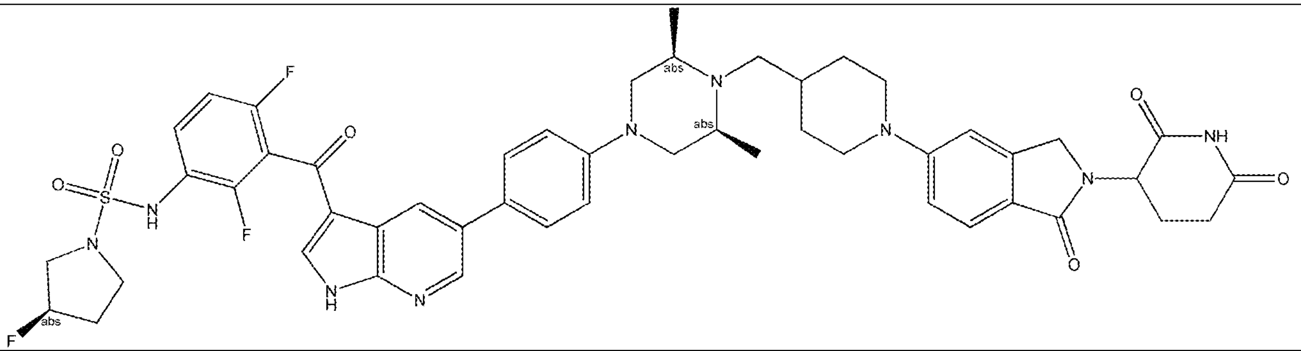
Figure 2B:
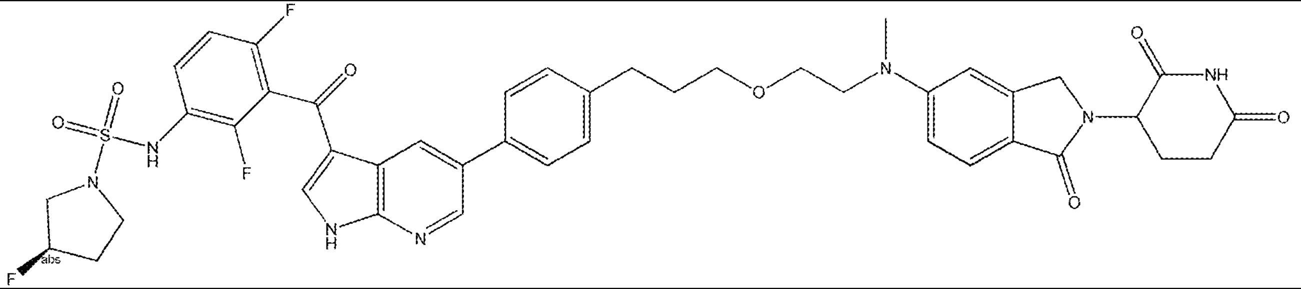
Figure 2B:
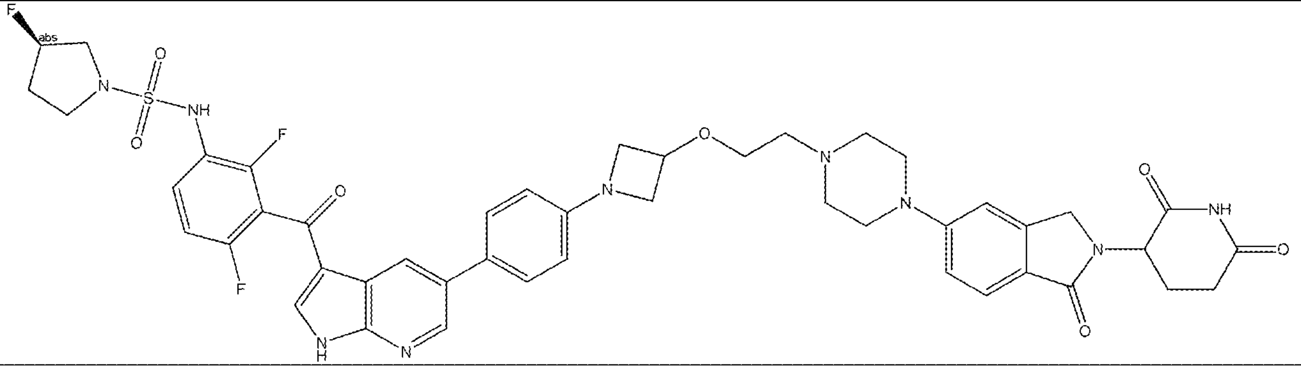
Figure 2B:
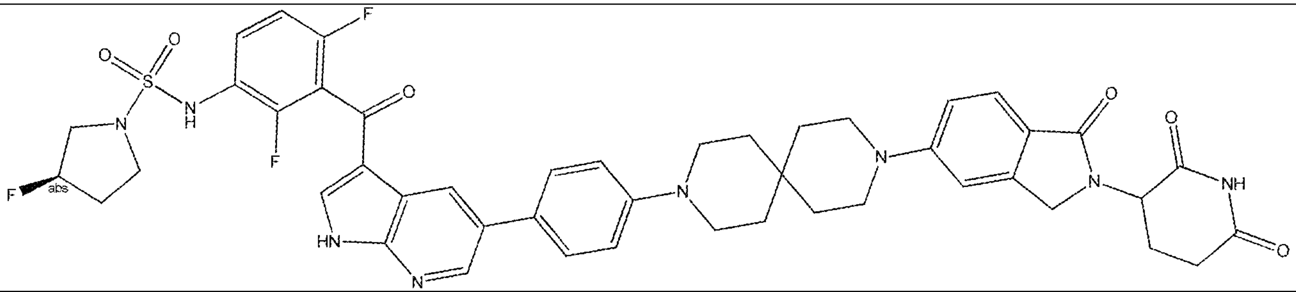
Figure 2B:
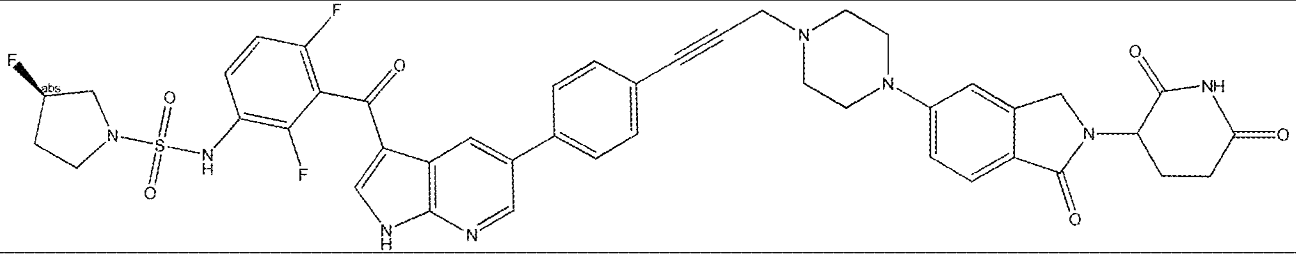
Figure 2B:
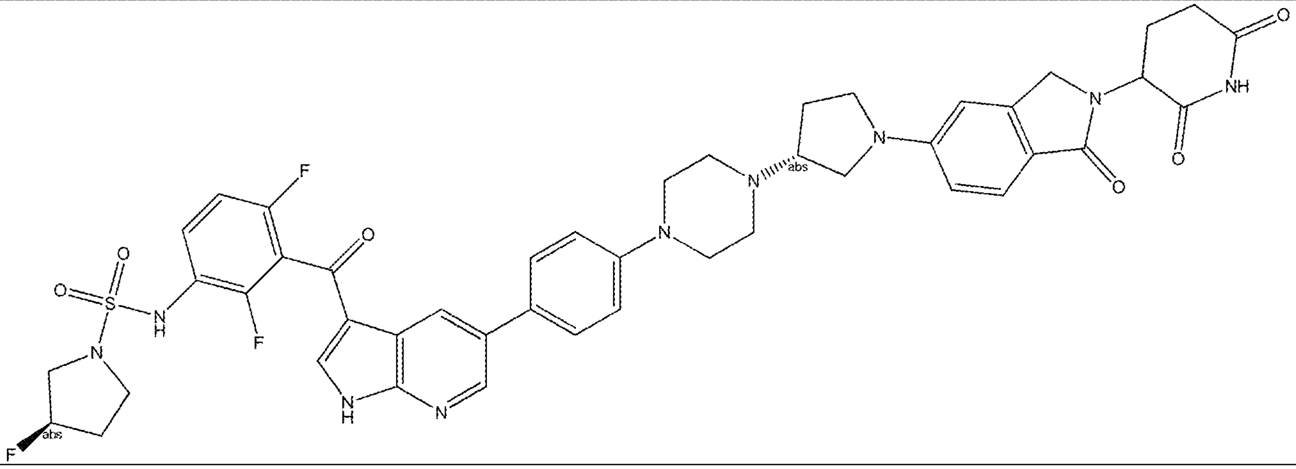
Figure 2B:
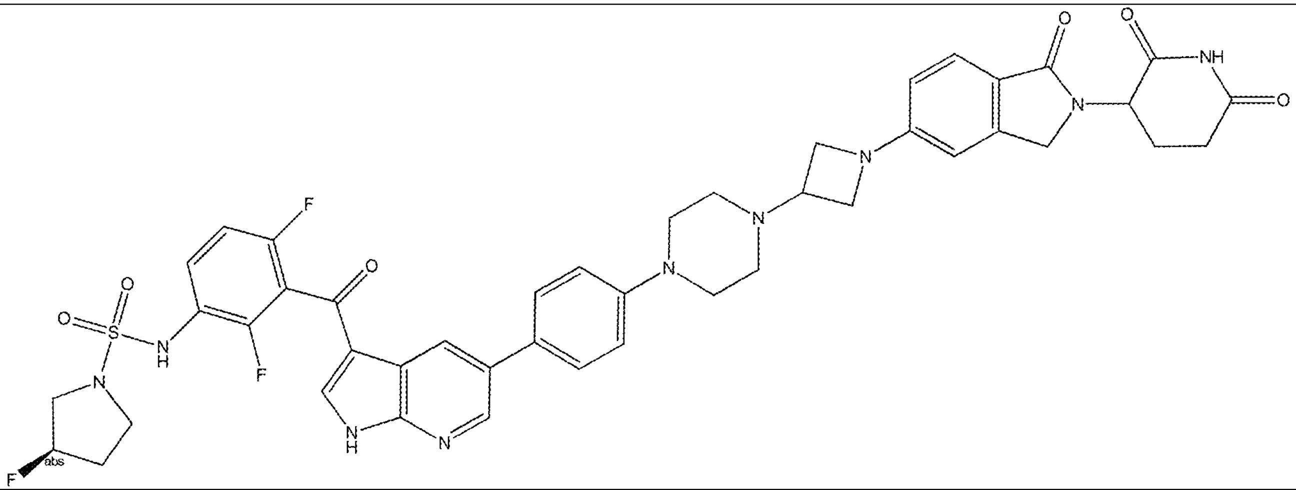
Figure 2B:
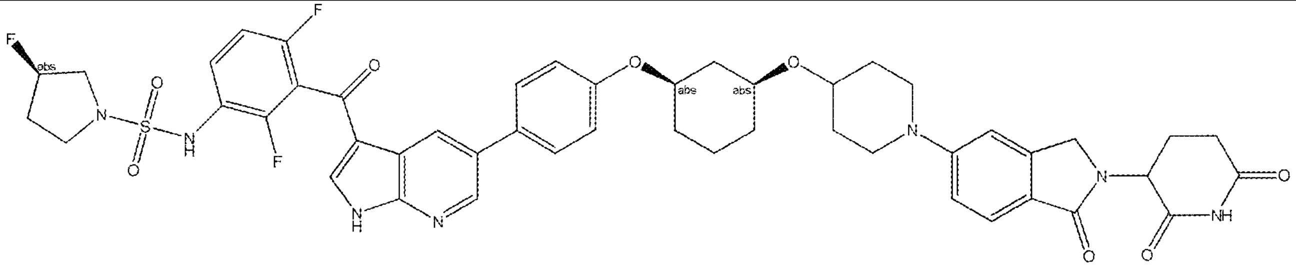
Figure 2B:
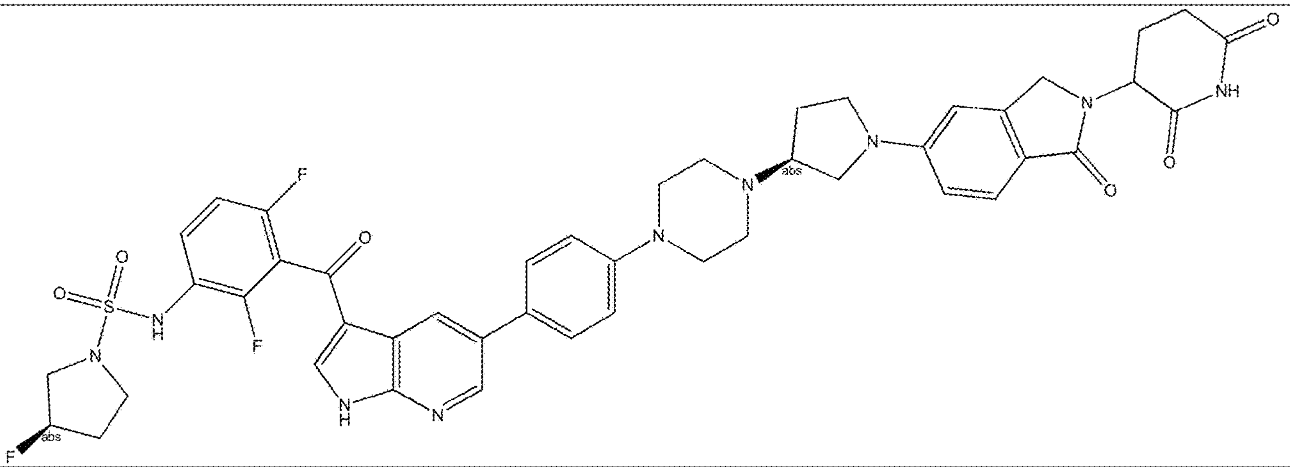
Figure 2B:
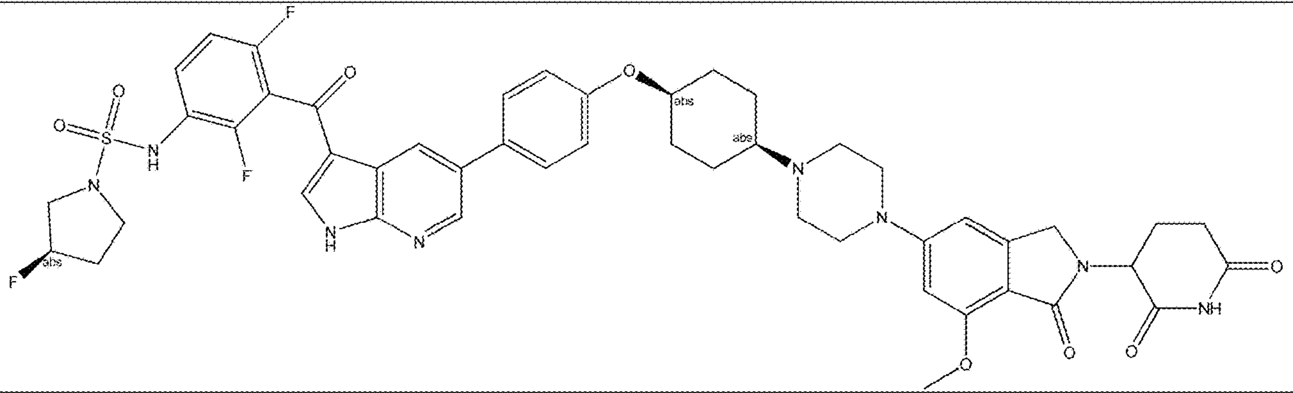
Figure 2B:
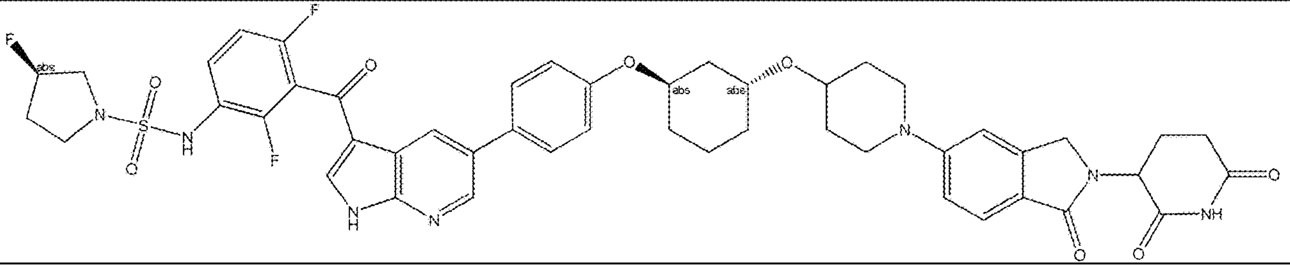
Figure 2B:
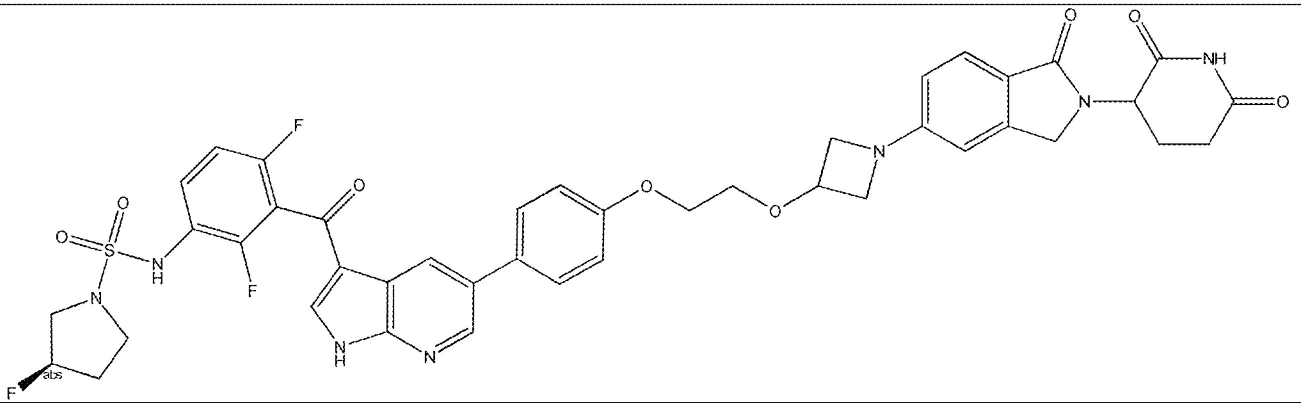
Figure 2B:
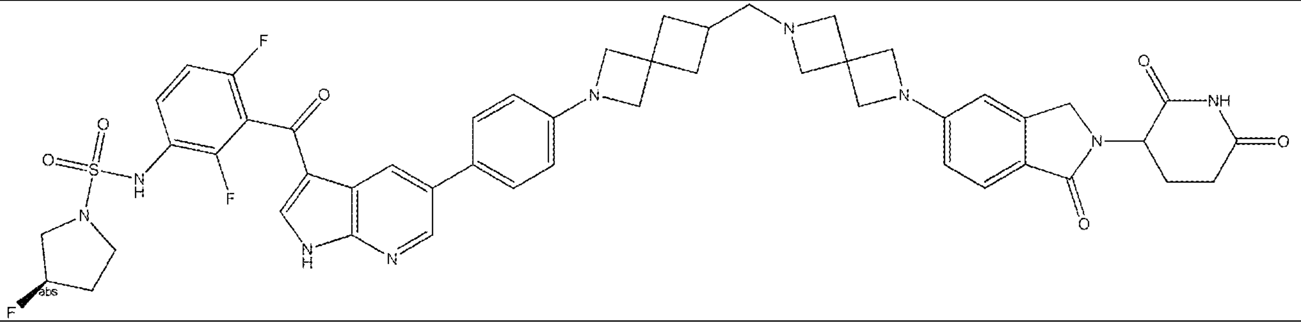
Figure 2B:
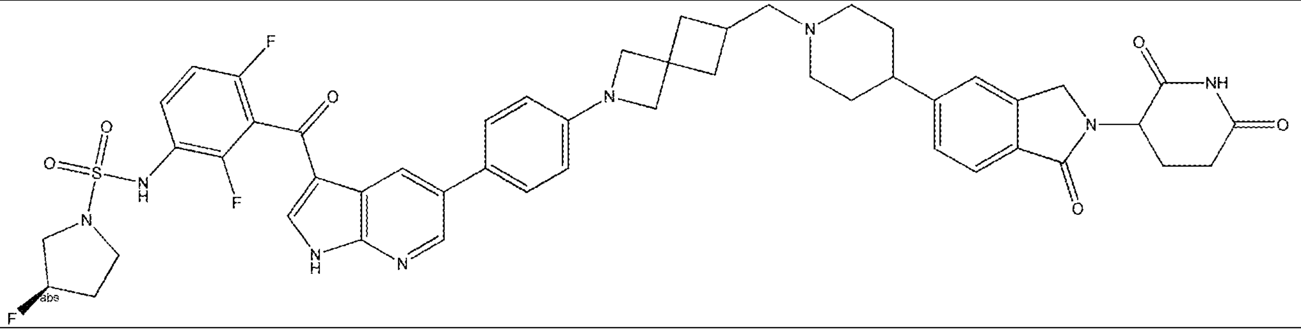
Figure 2B:
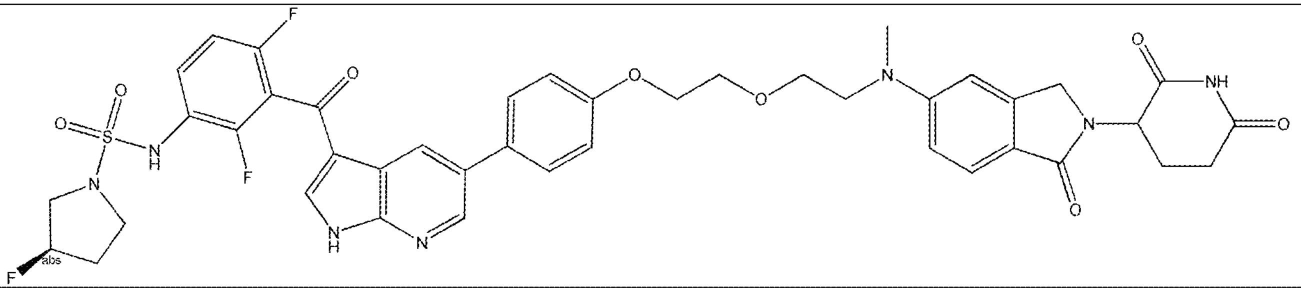
Figure 2B:
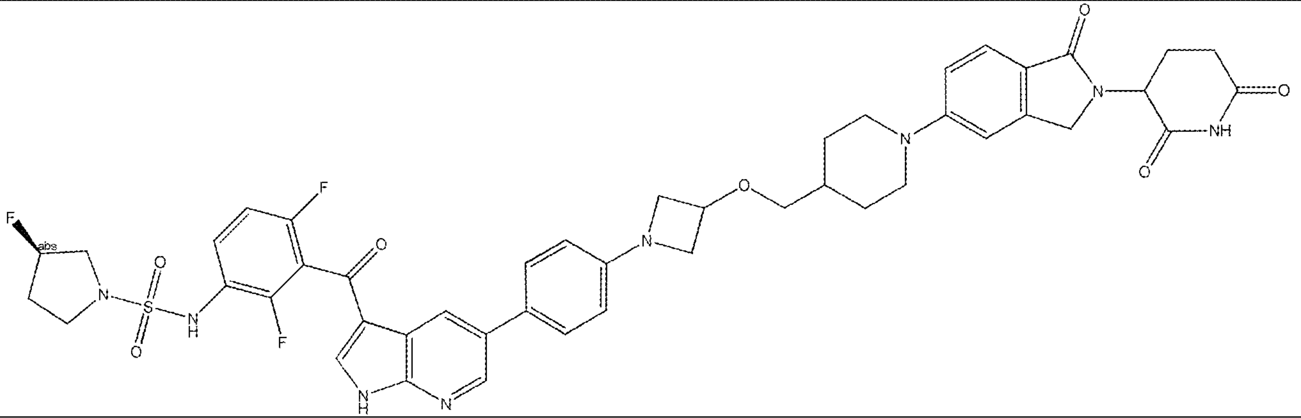
Figure 2B:
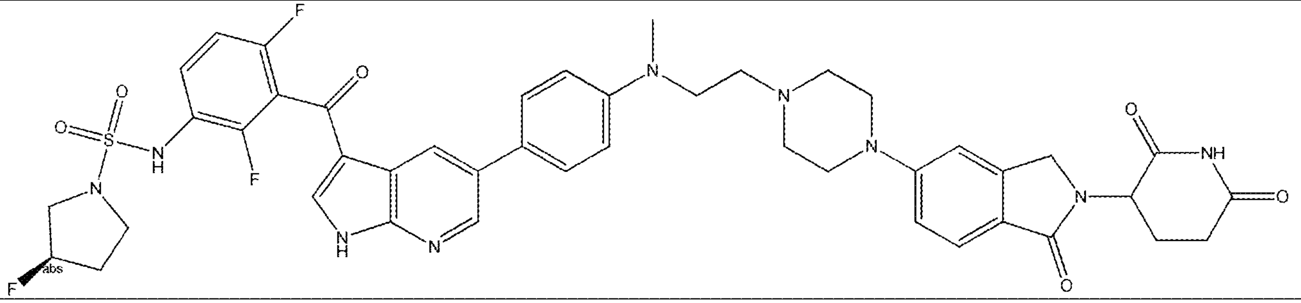
Figure 2B:
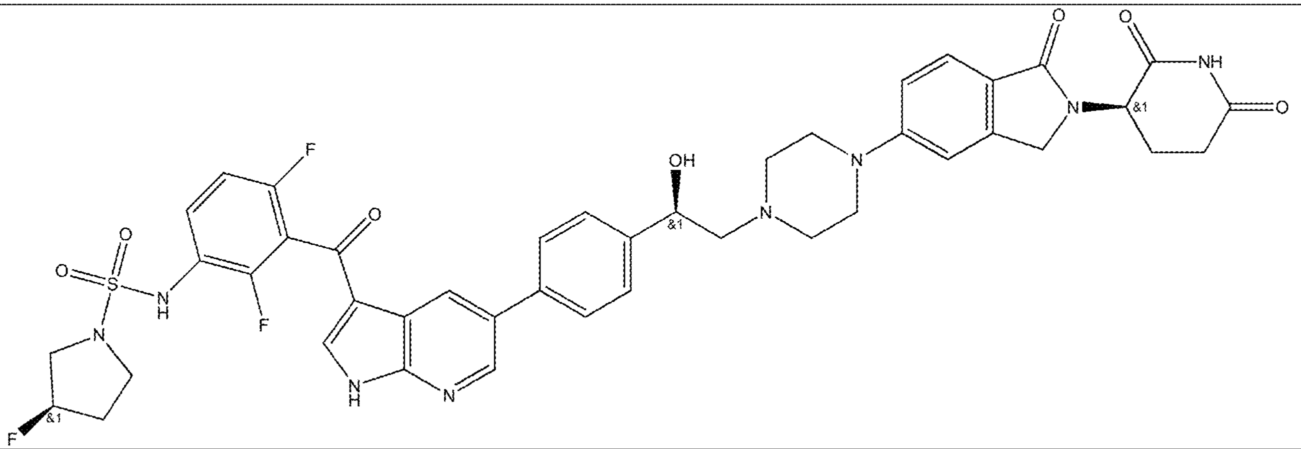
Figure 2B:
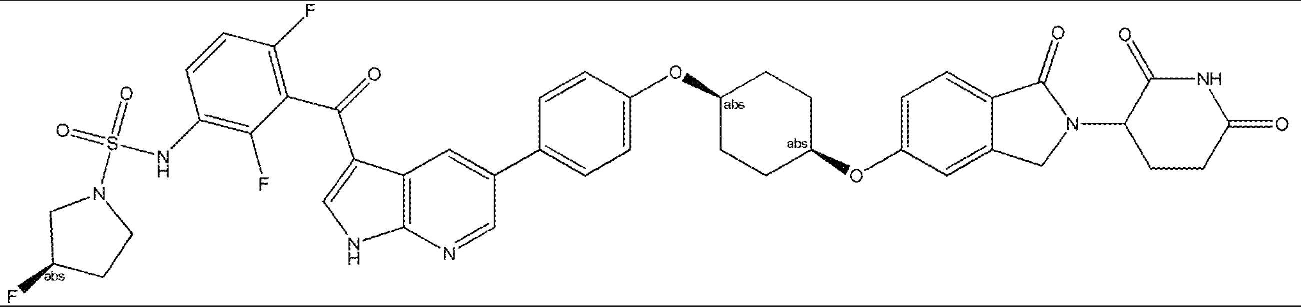
Figure 2B:
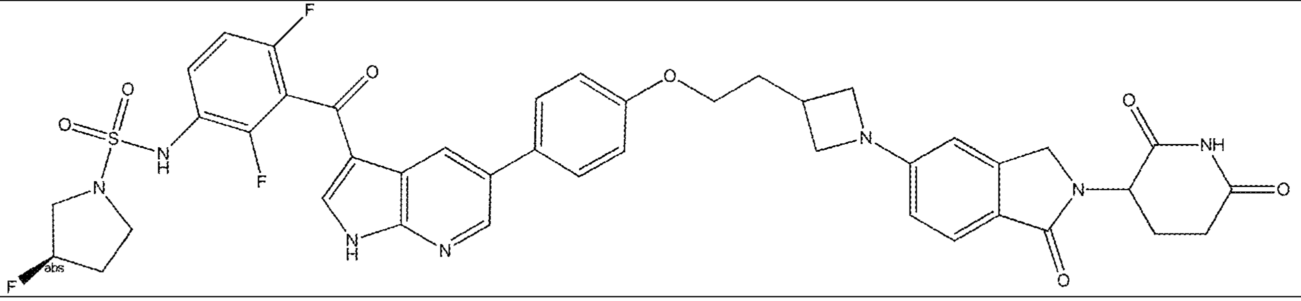
Figure 2B:
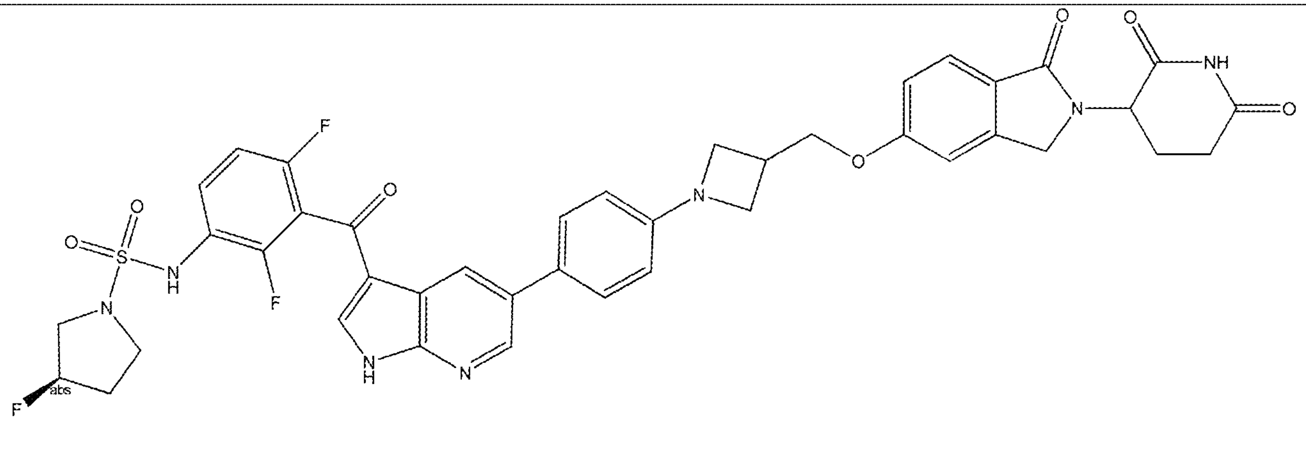
Figure 2B:
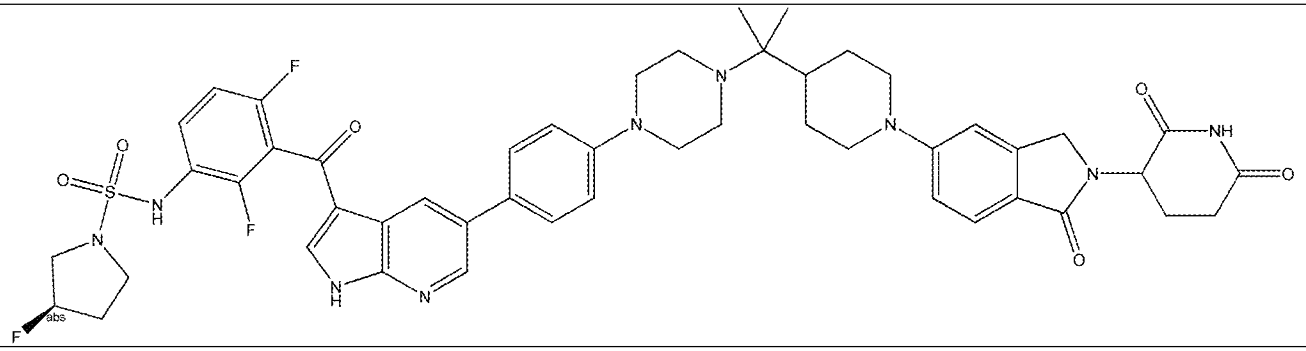
Figure 2B:
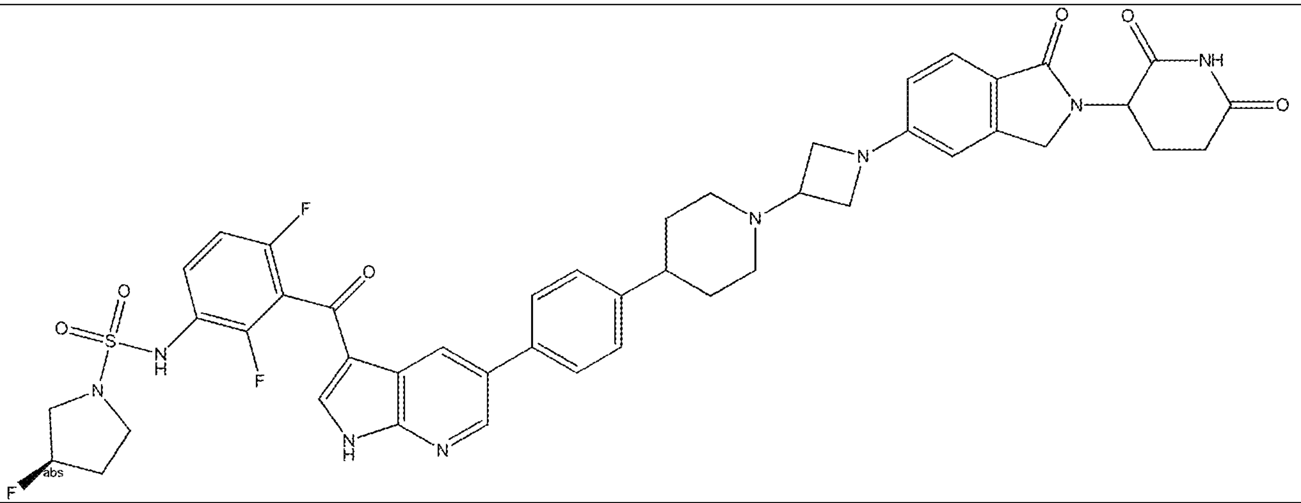
Figure 2B:
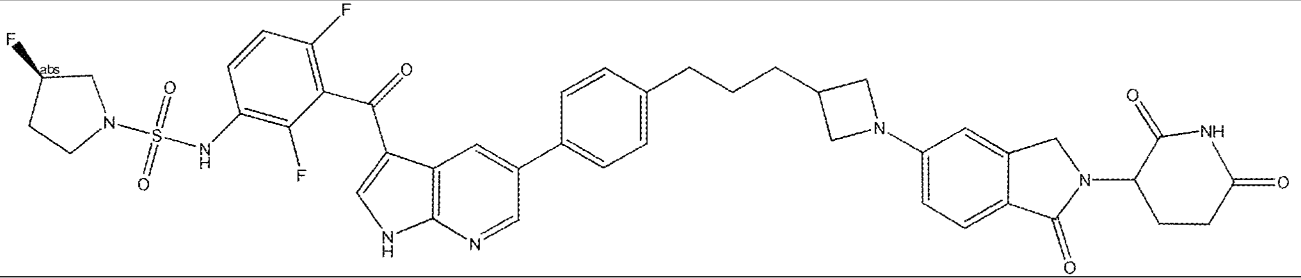
Figure 2B:
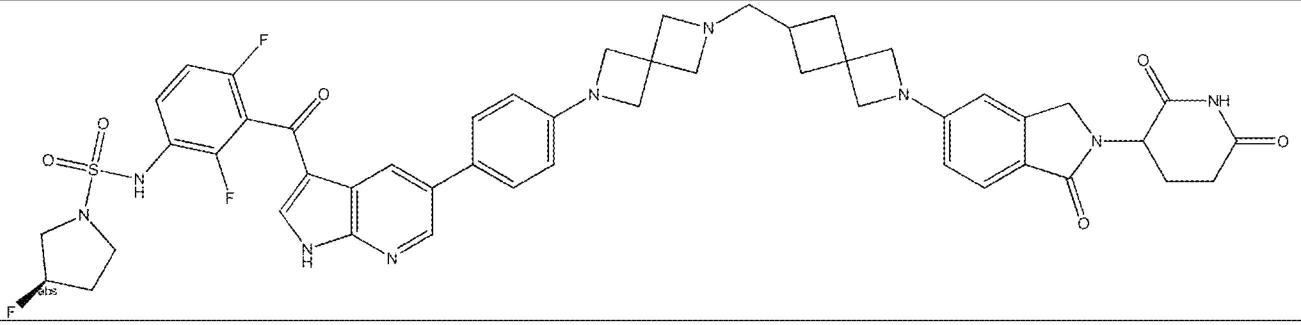
Figure 2B:
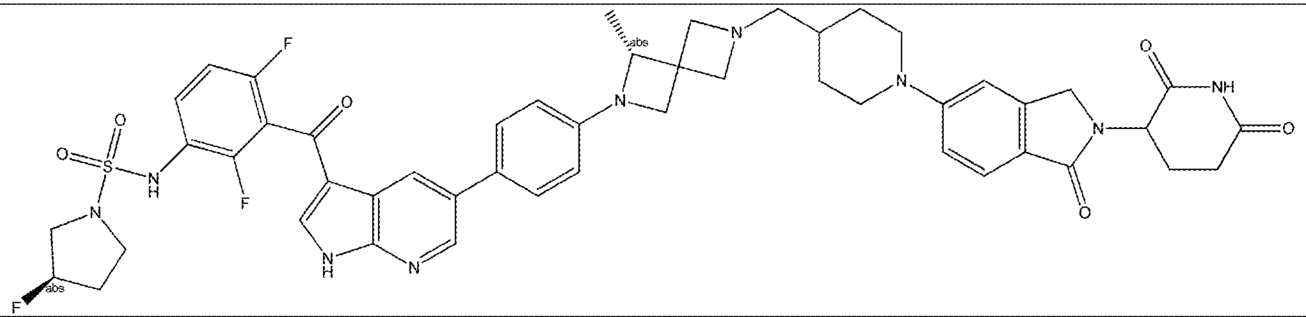
Figure 2B:
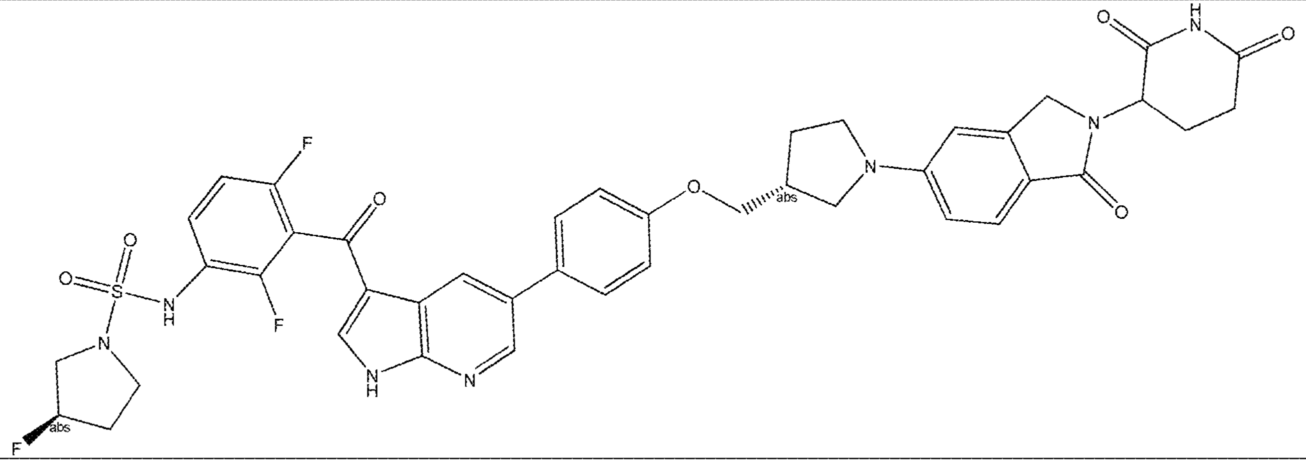
Figure 2B:
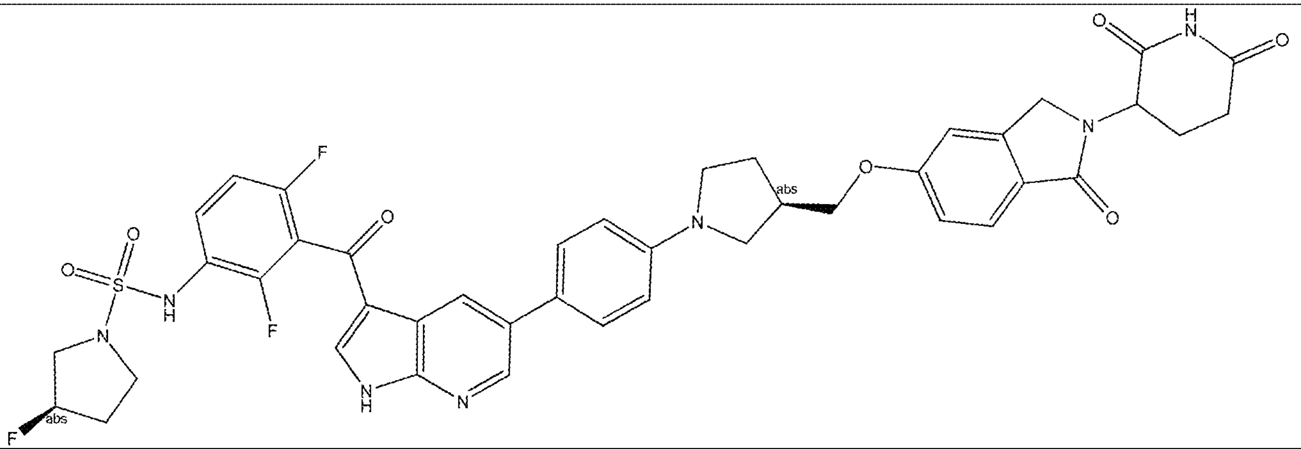
Figure 2B:
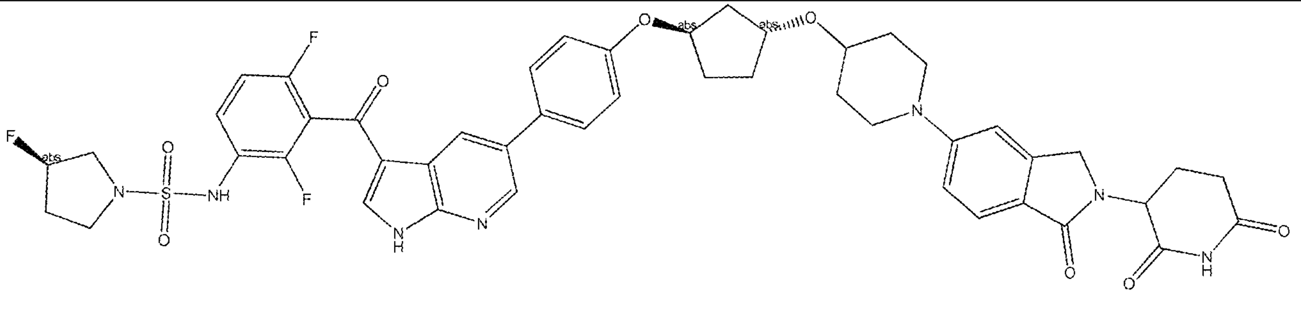
Figure 2B:
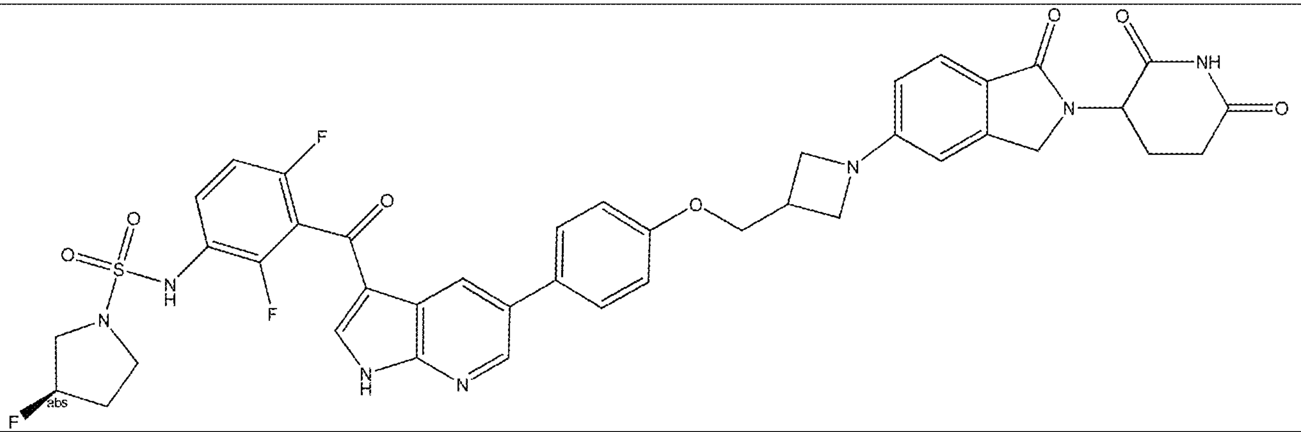
Figure 2B:
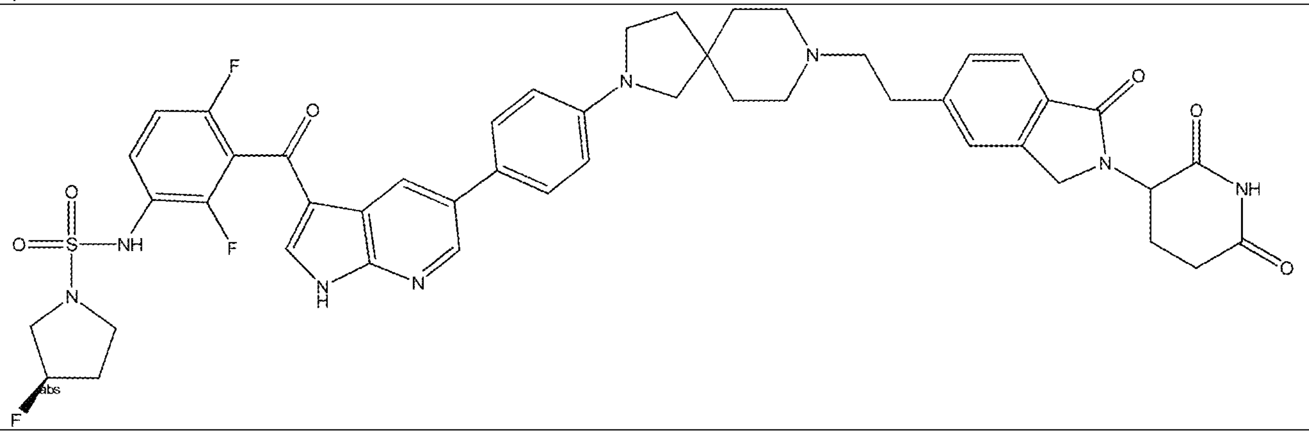
Figure 2B:
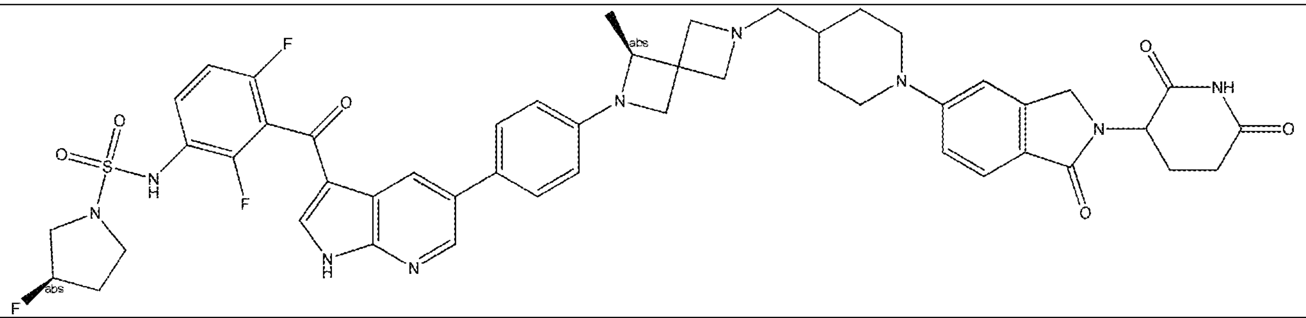
Figure 2B:
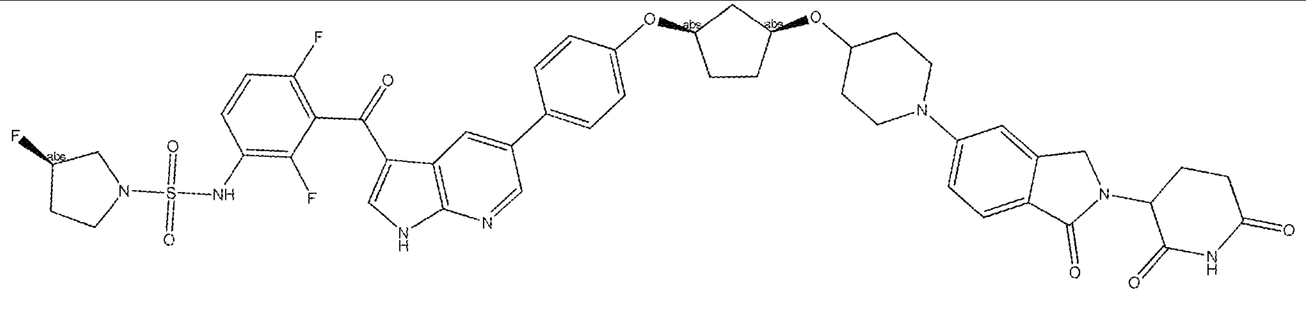
Figure 2B:
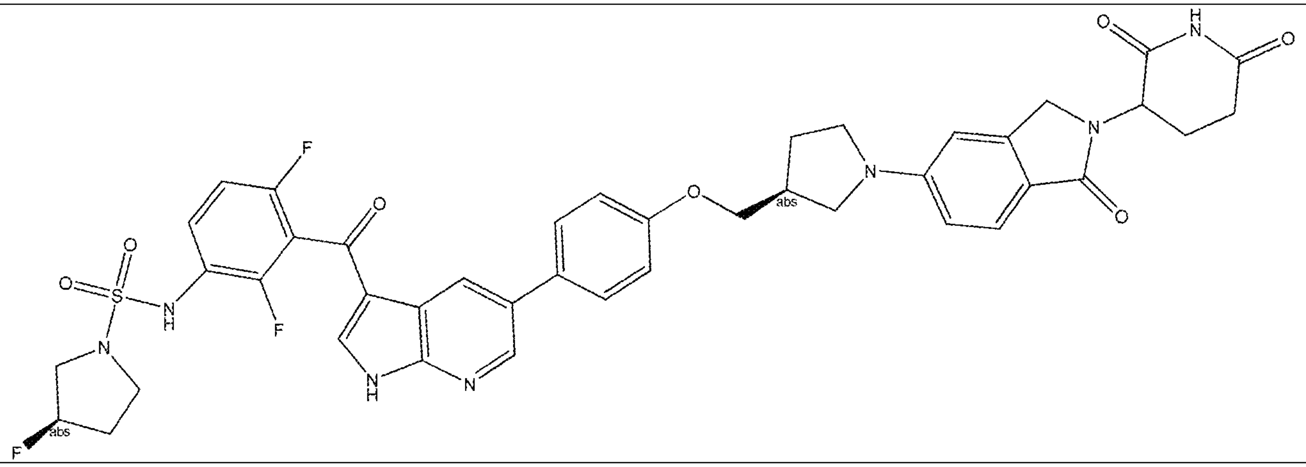
Figure 2B:
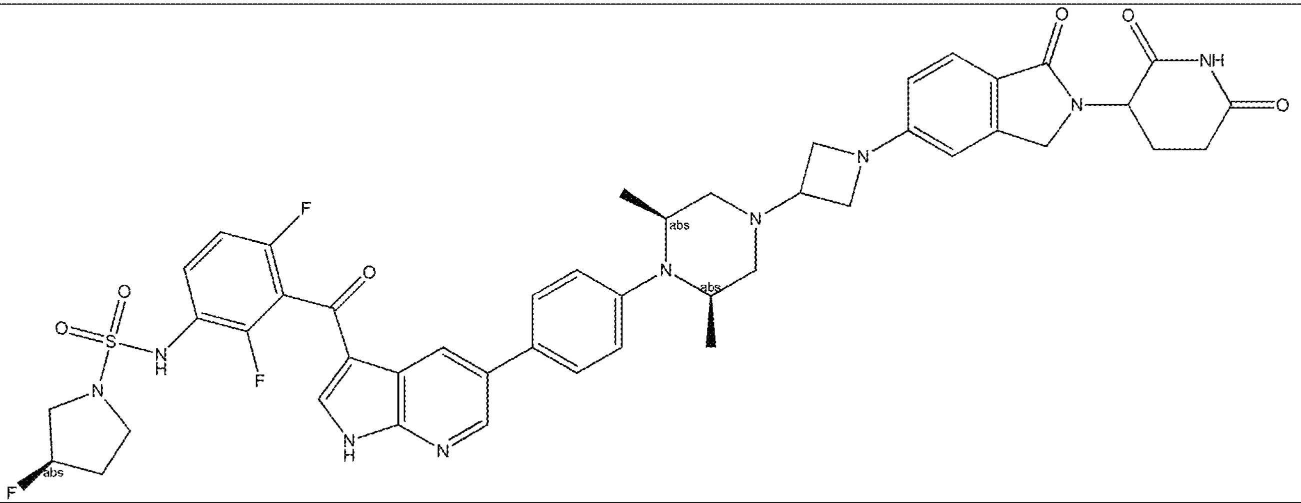
Figure 2B:
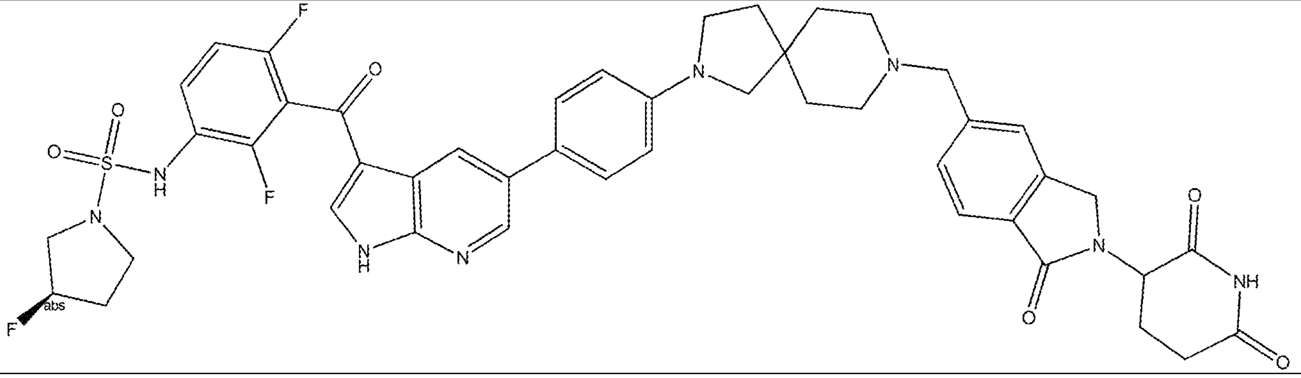
Figure 2B:
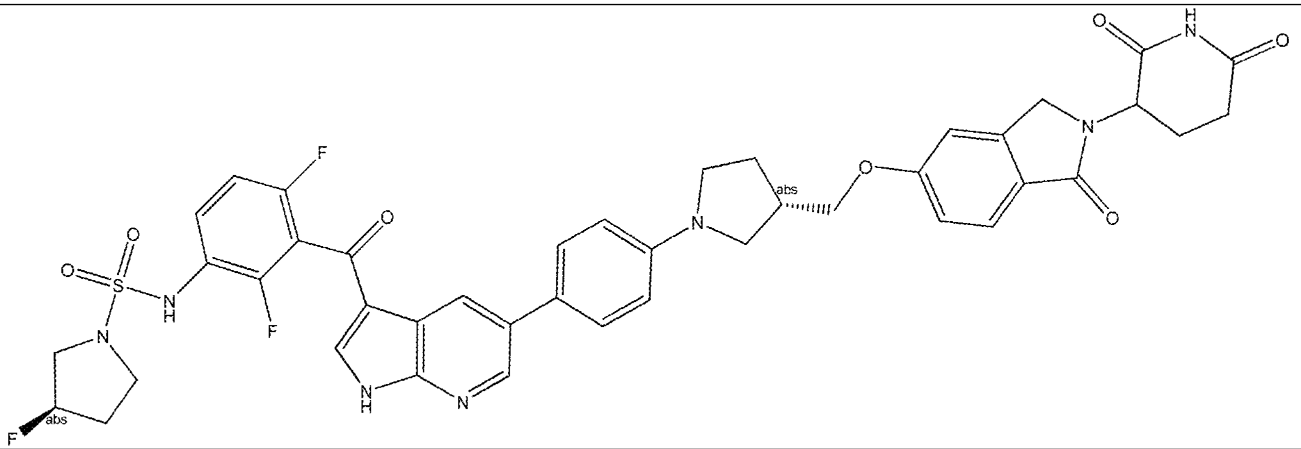
Figure 2B:
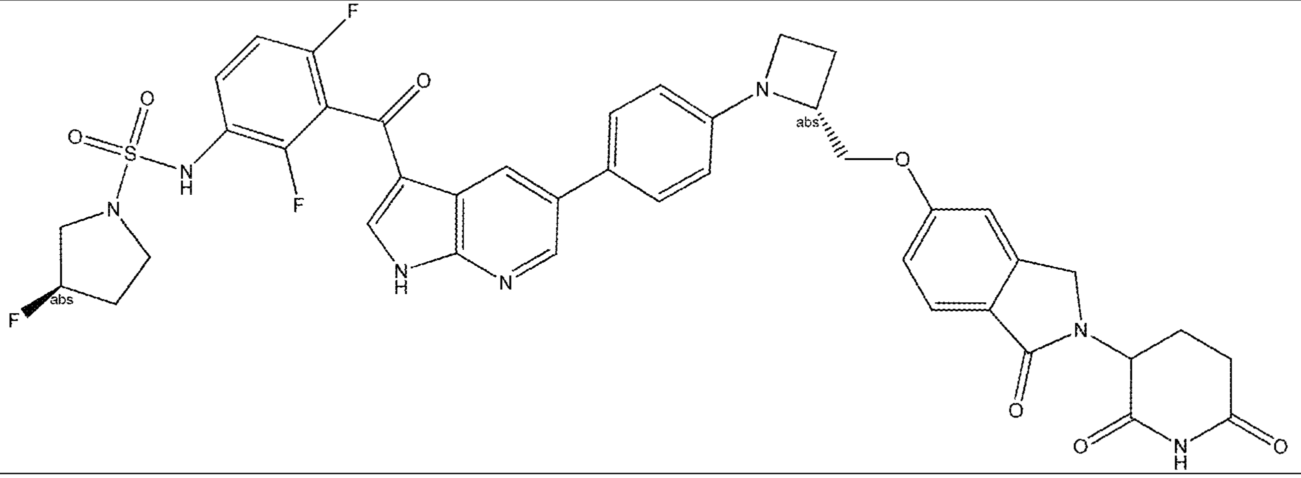
Figure 2B:
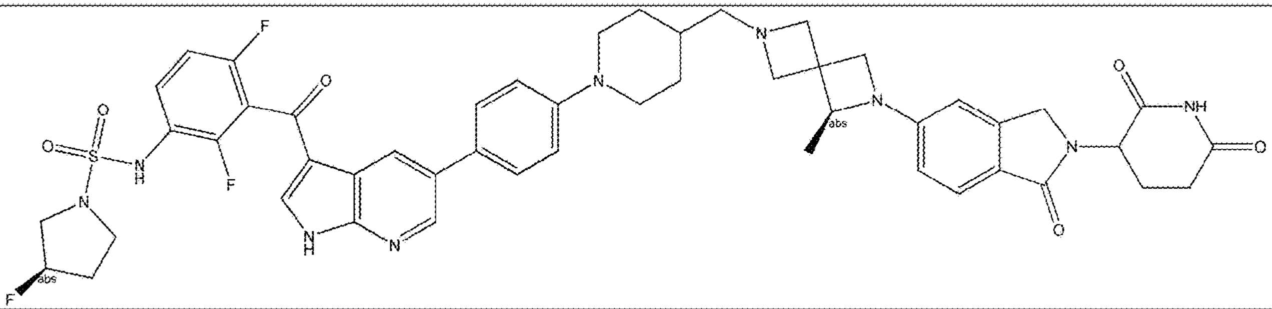
Figure 2B:
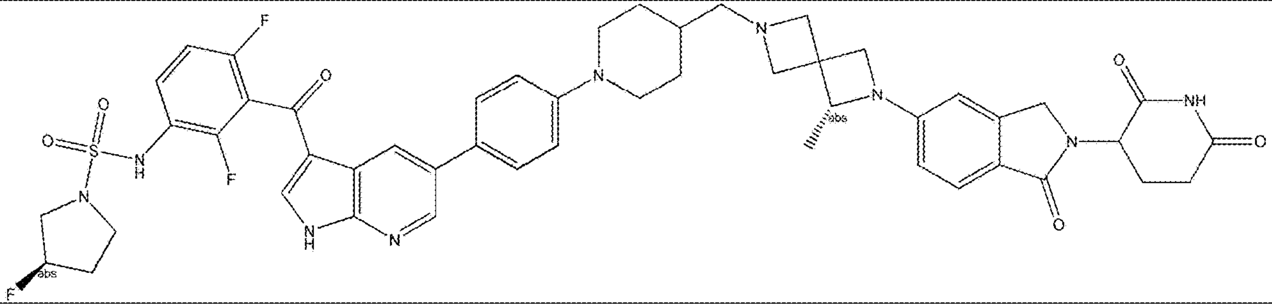
Figure 2B:
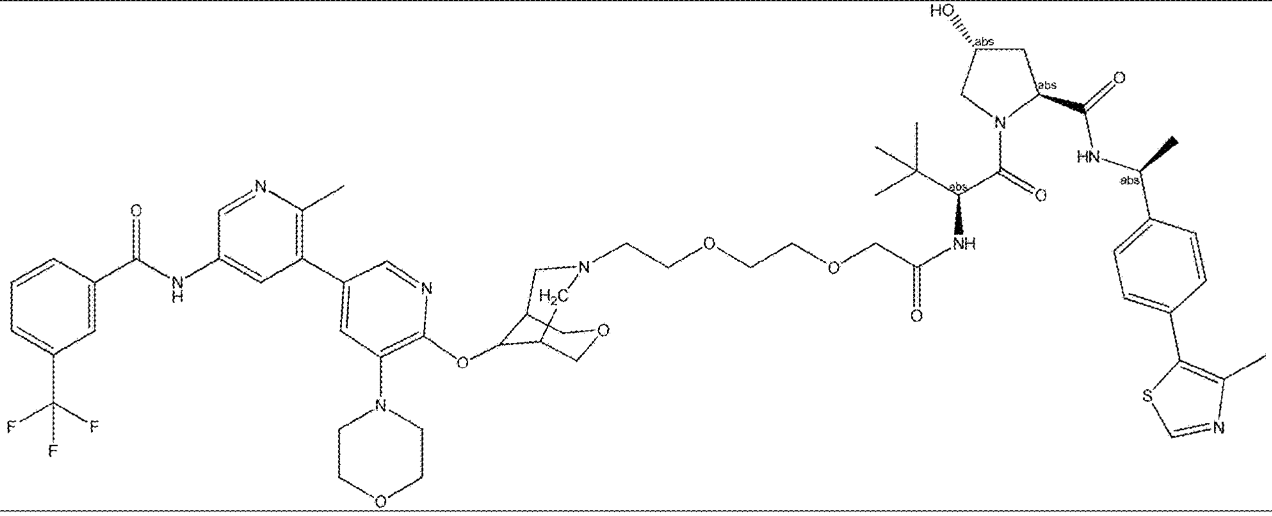
Figure 2B:
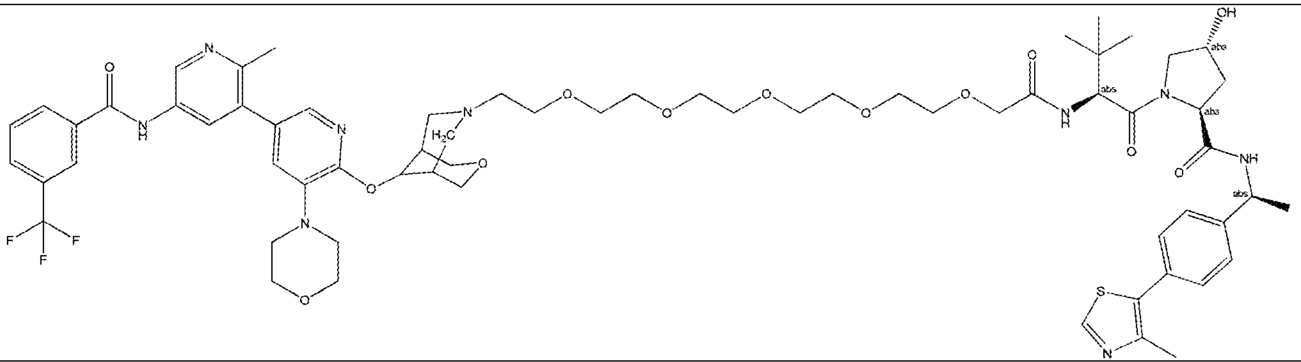
Figure 2B:
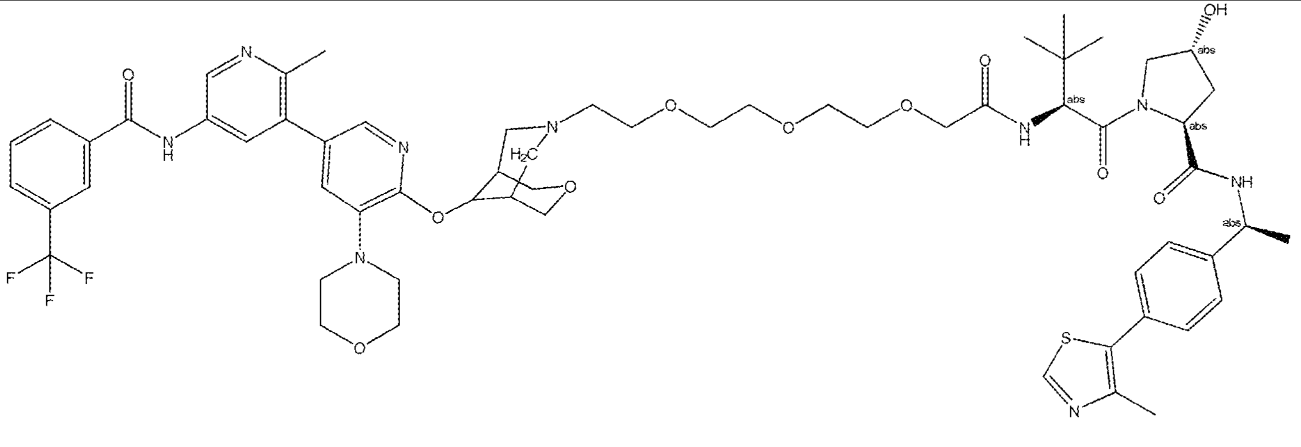
Figure 2B:
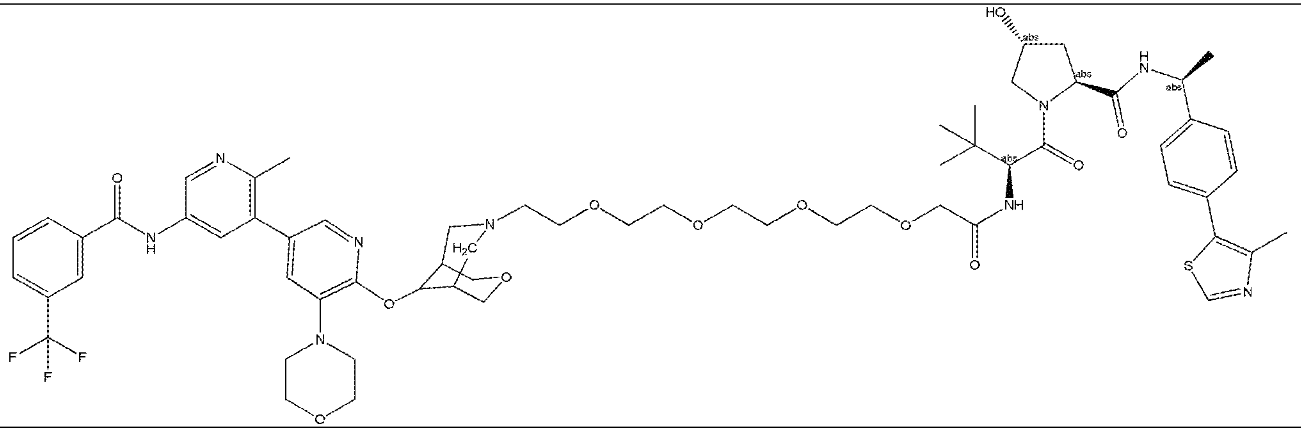
Figure 2B:
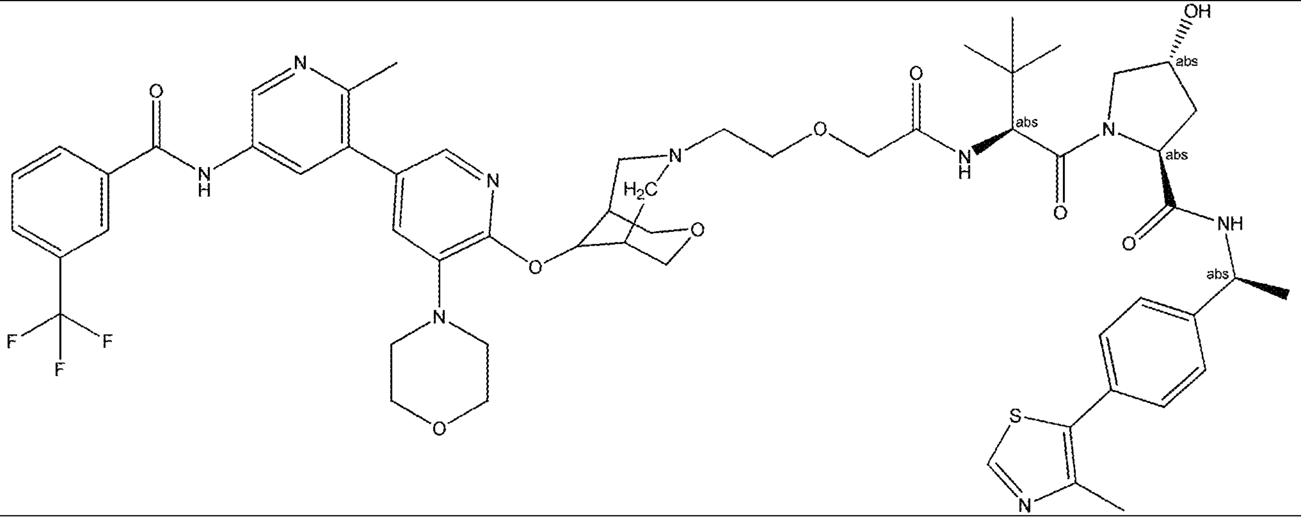
Figure 2B:
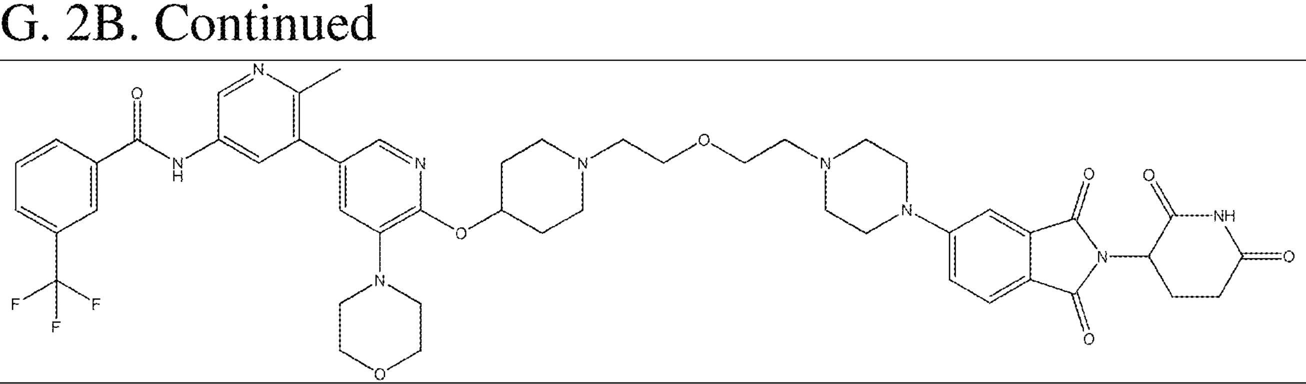
Figure 2B:
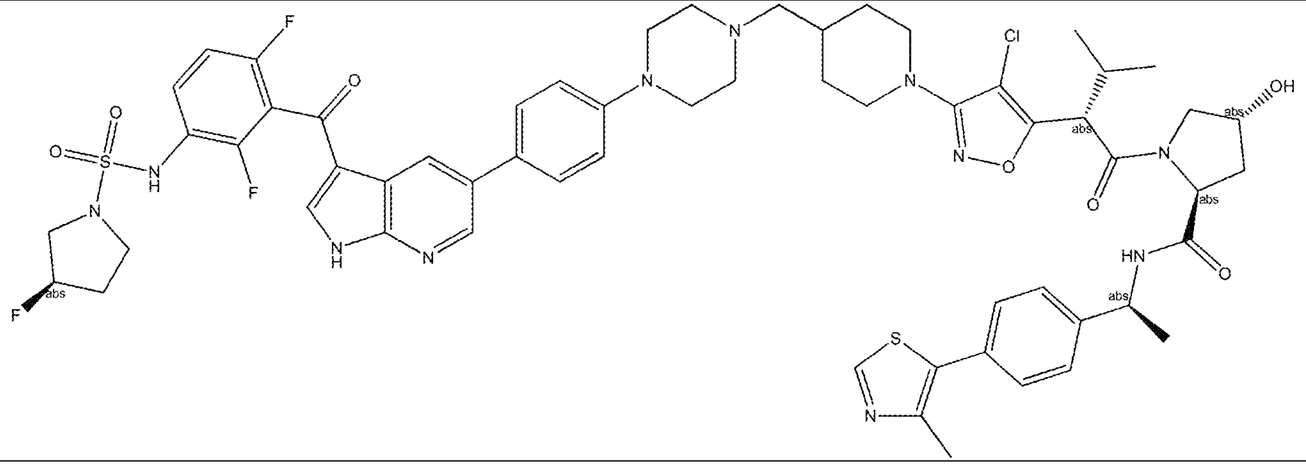
Figure 2B:
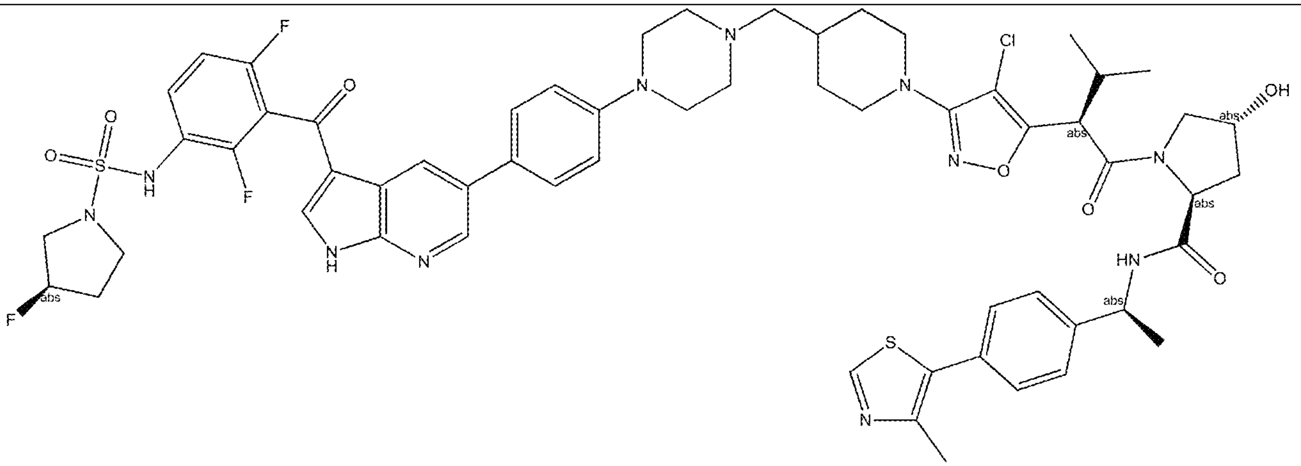
Figure 2B:
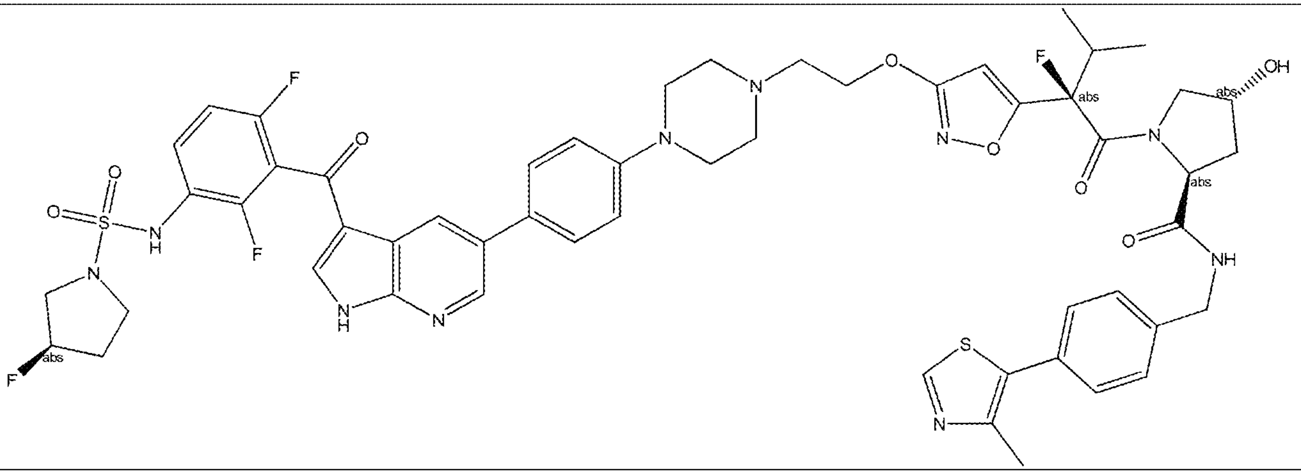
Figure 2B:
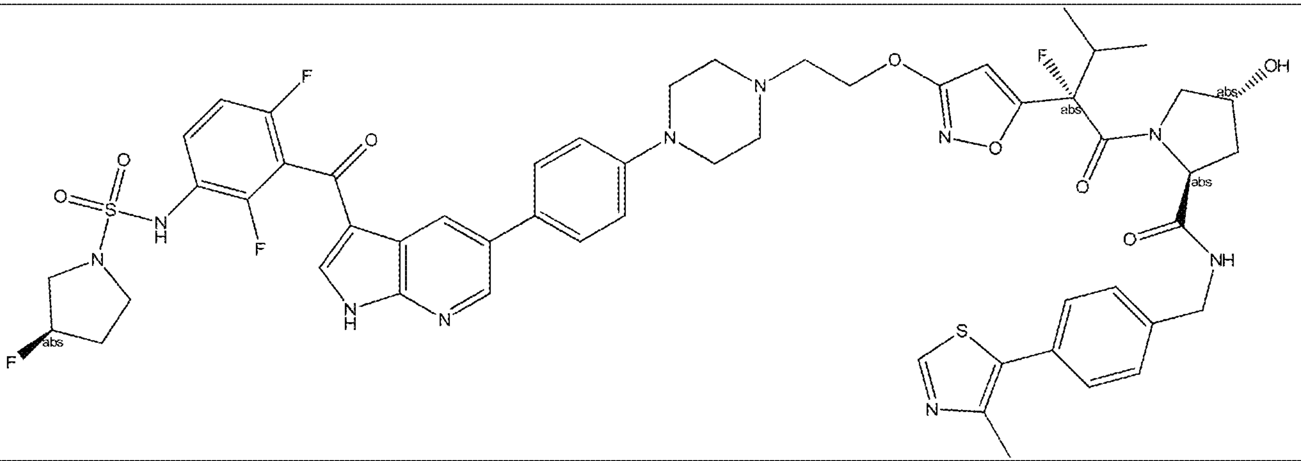
Figure 2B:
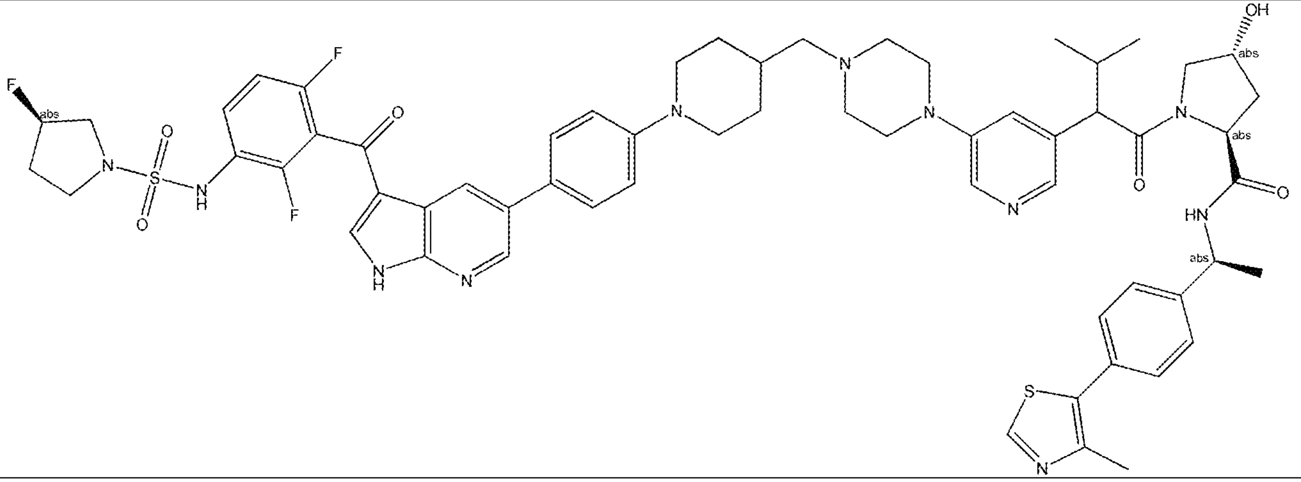
Figure 2B:
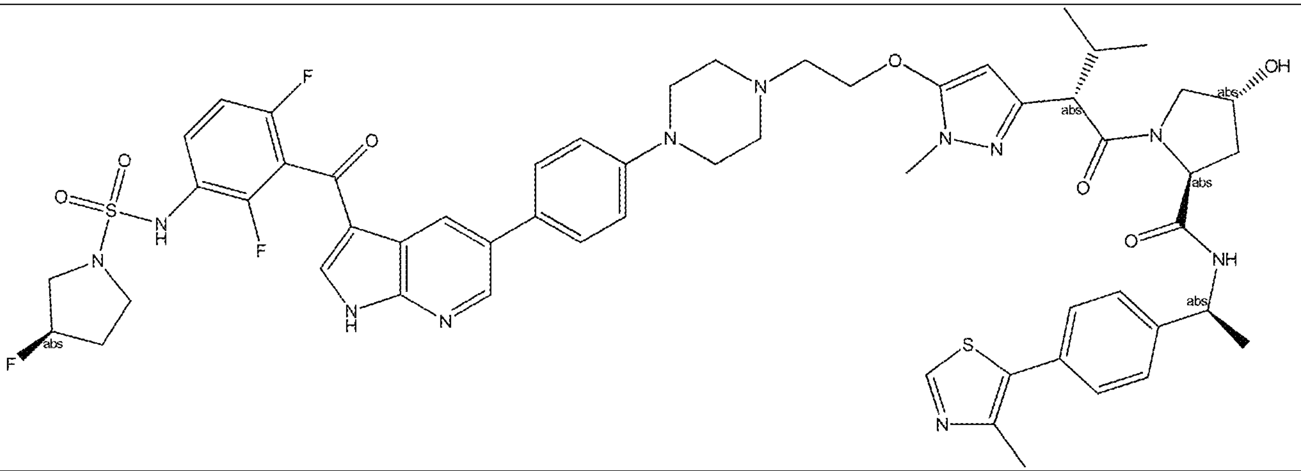
Figure 2B:
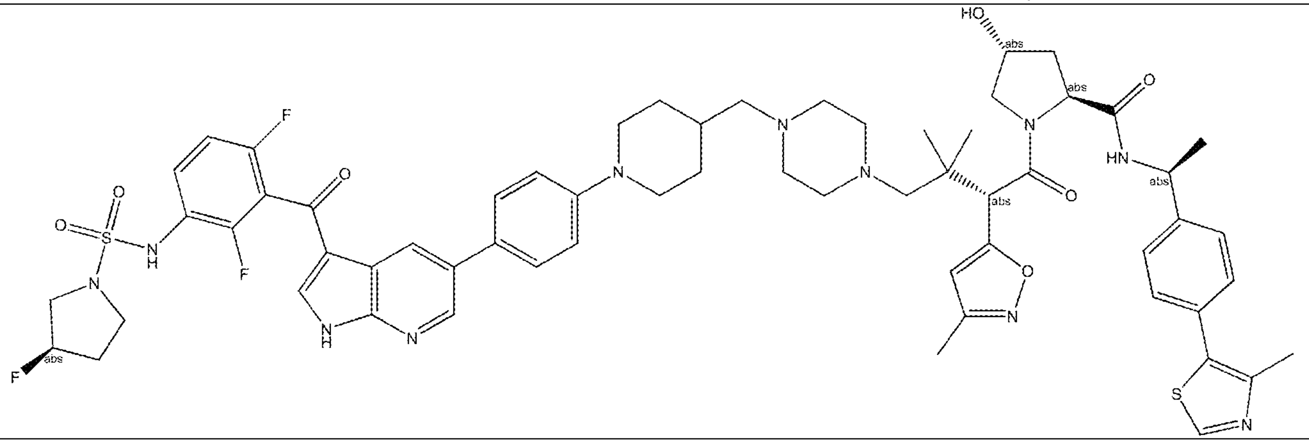
Figure 2B:
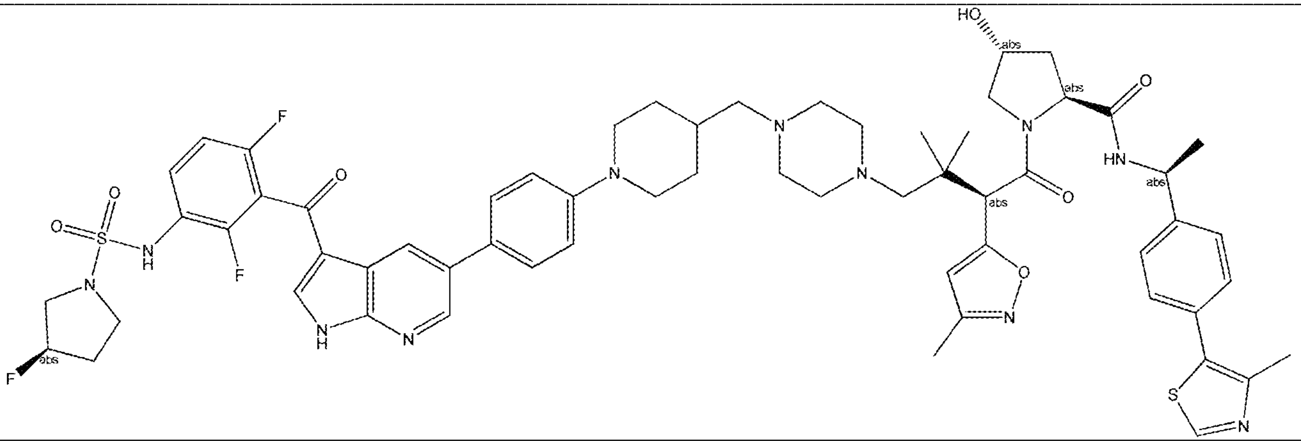
Figure 2B:
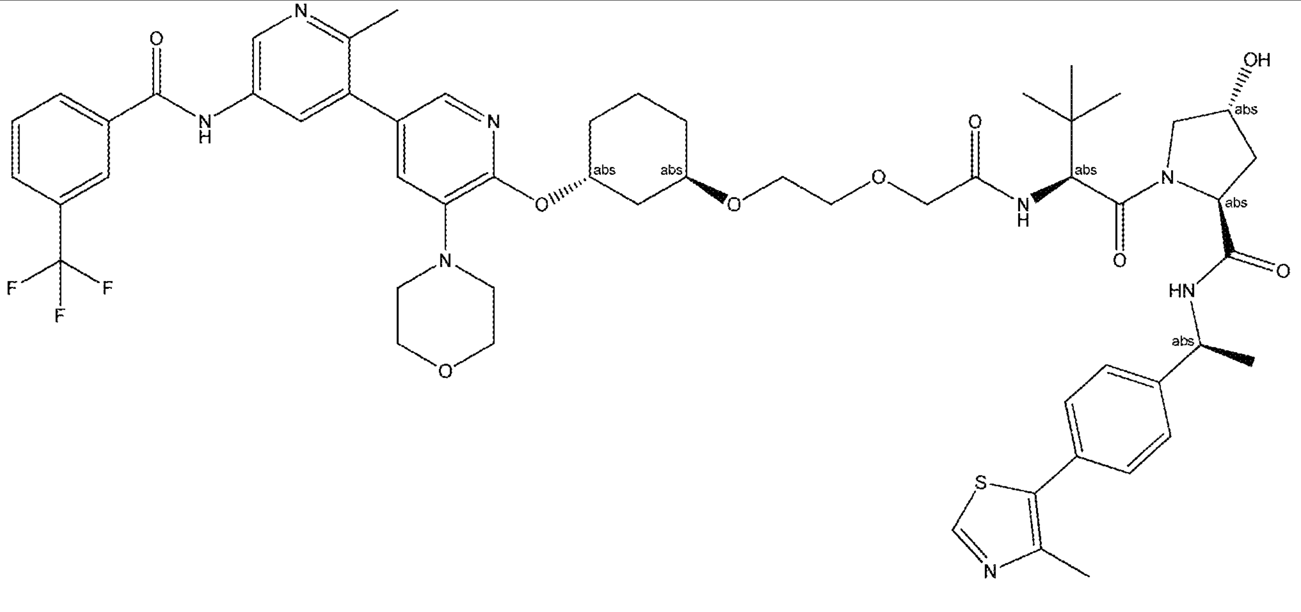
Figure 2B:
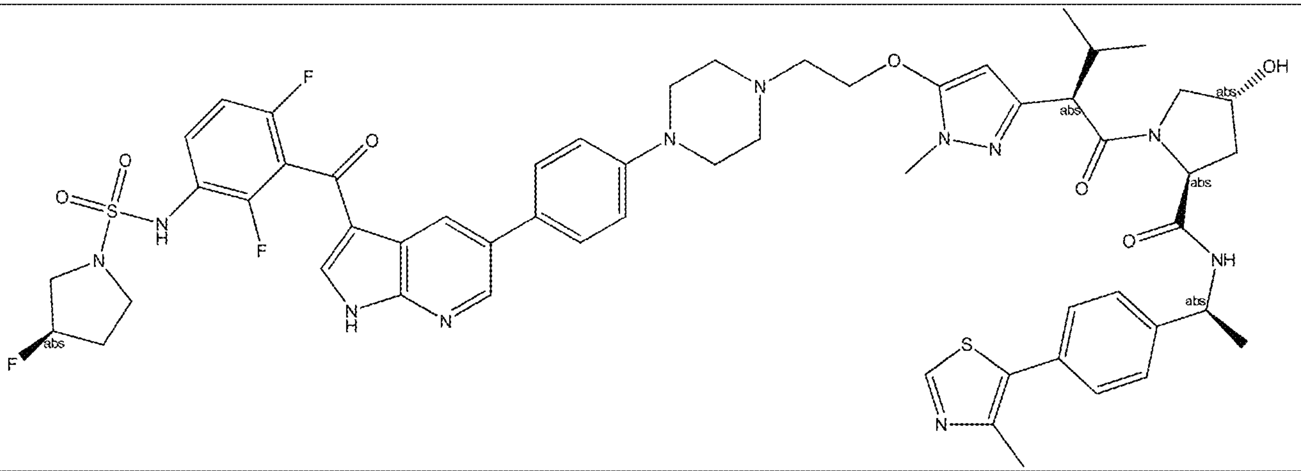
Figure 2B:
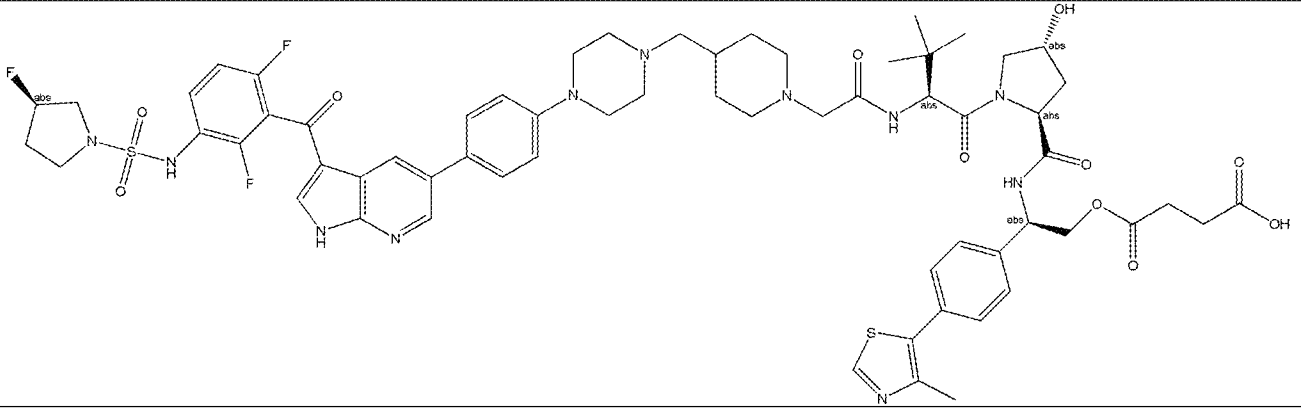
Figure 2B:
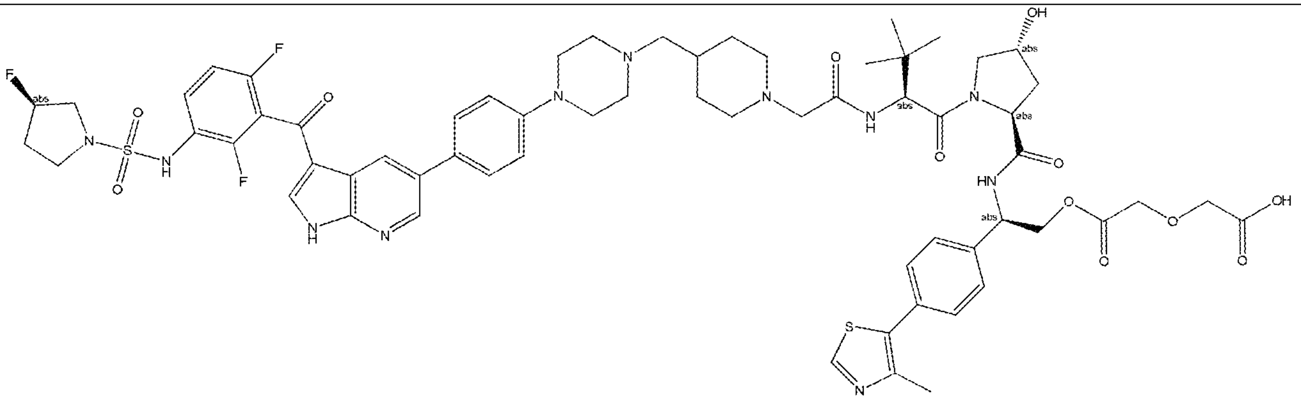
Figure 2B:
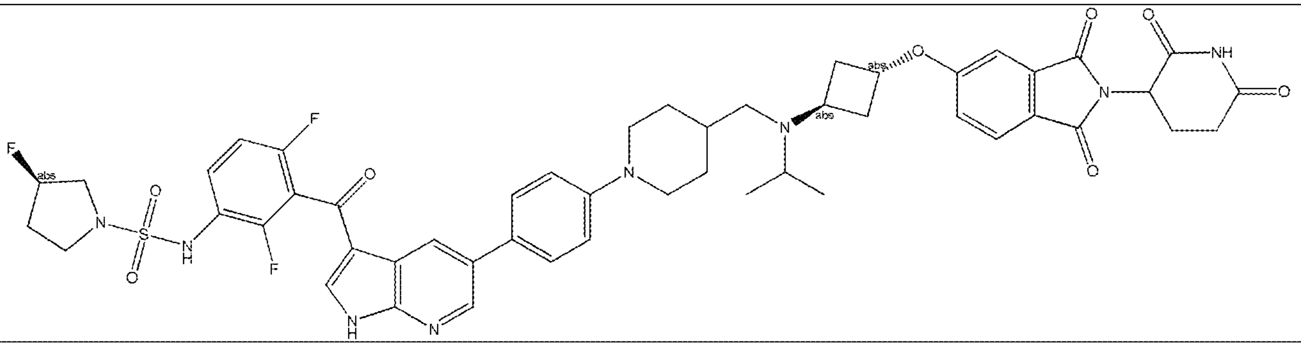
Figure 2B:
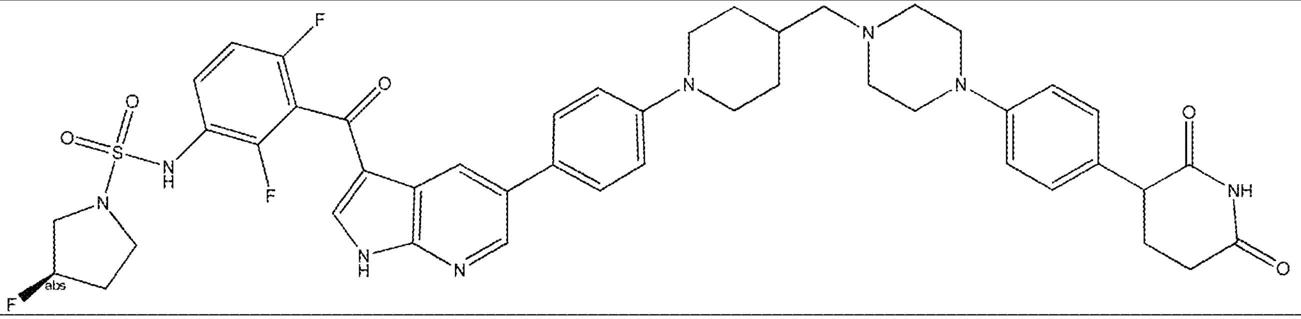
Figure 2B:
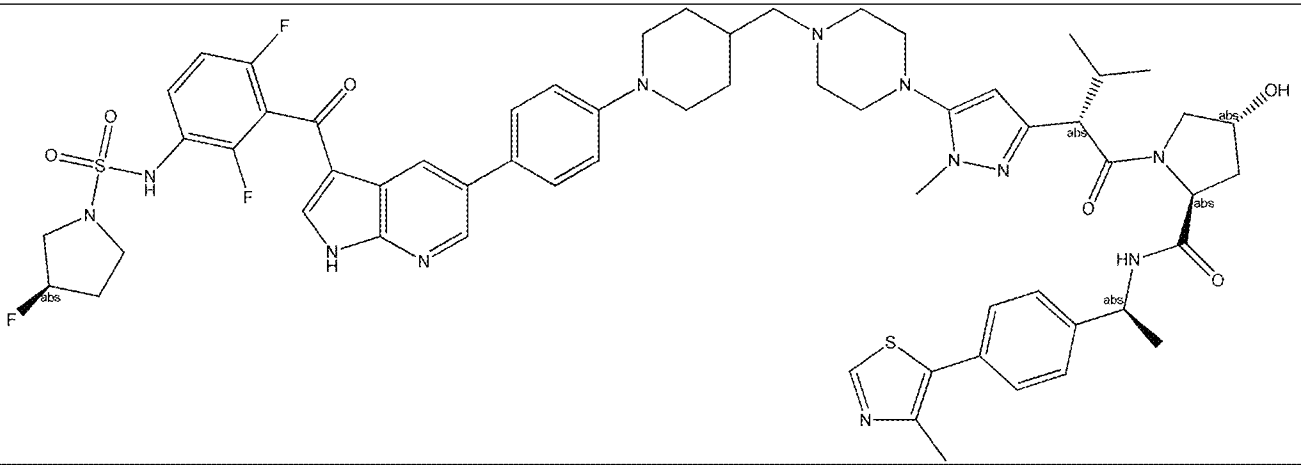
Figure 2B:
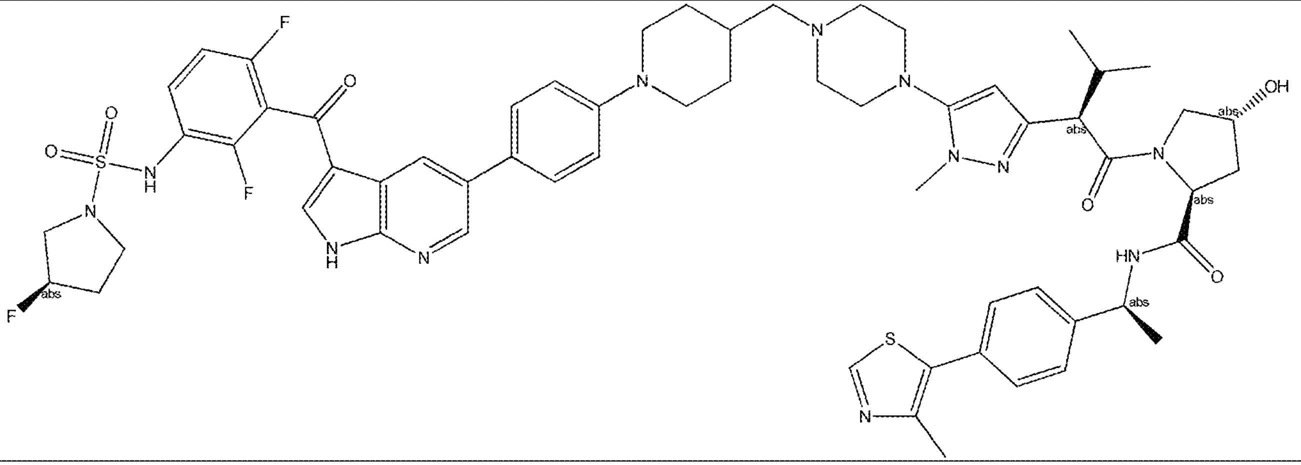
Figure 2B:
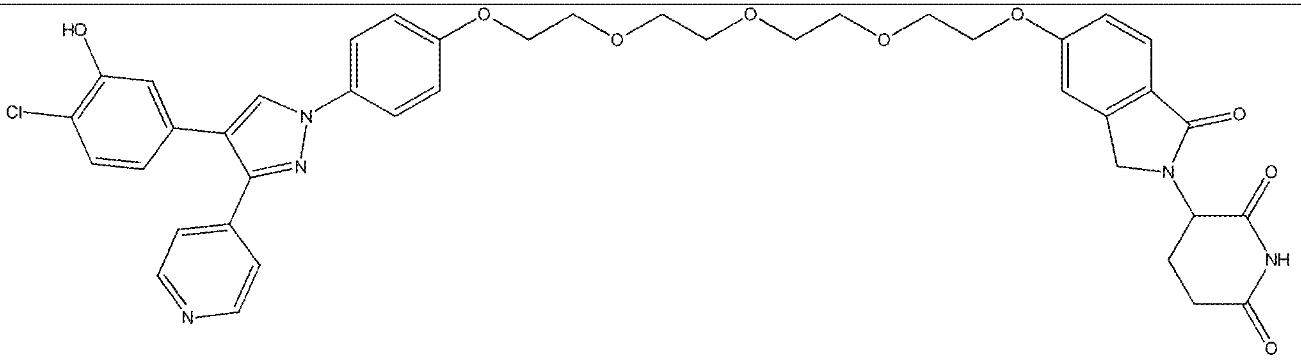
Figure 2B:
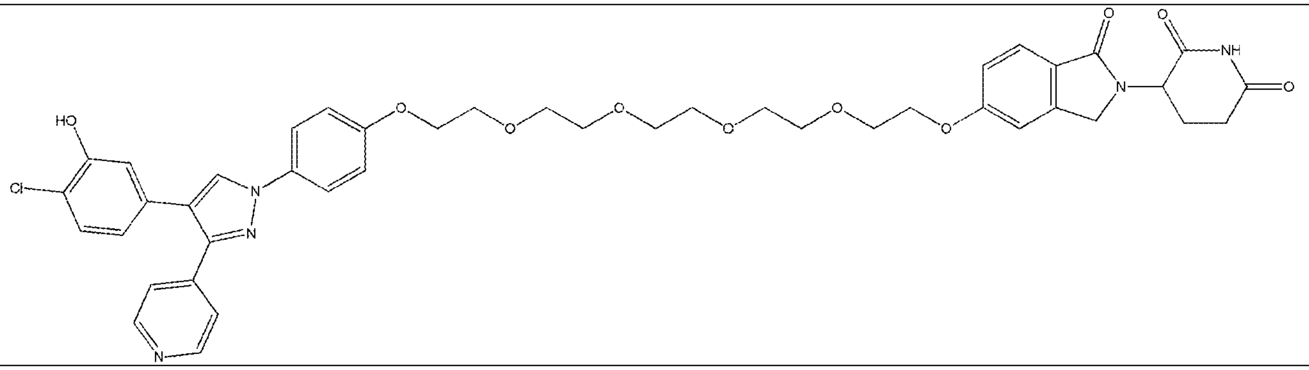
Figure 2B:
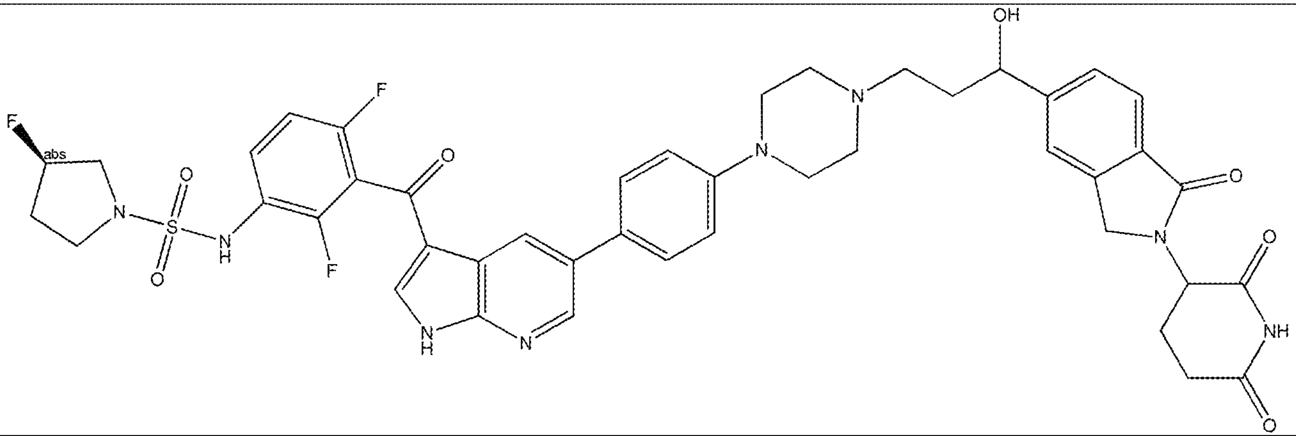
Figure 2B:
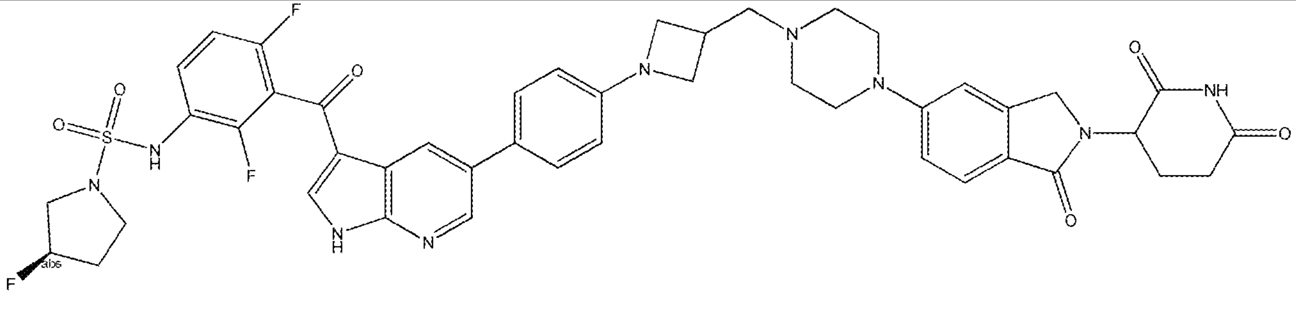
Figure 2B:
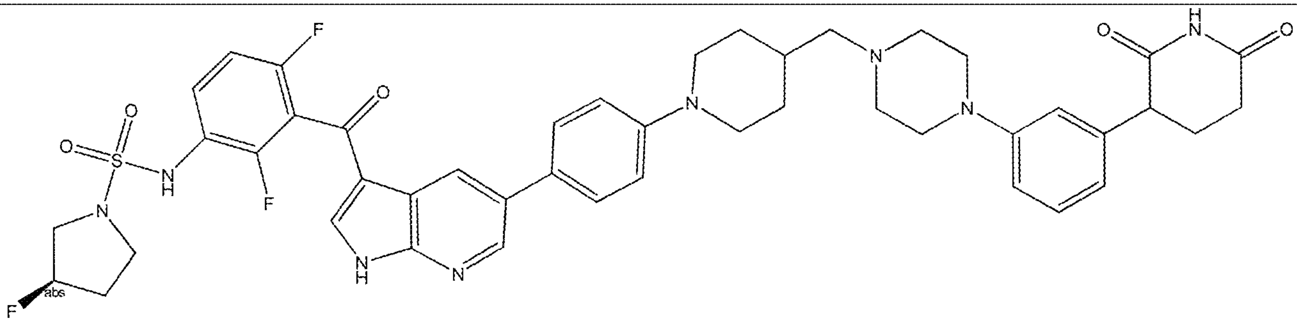
Figure 2B:
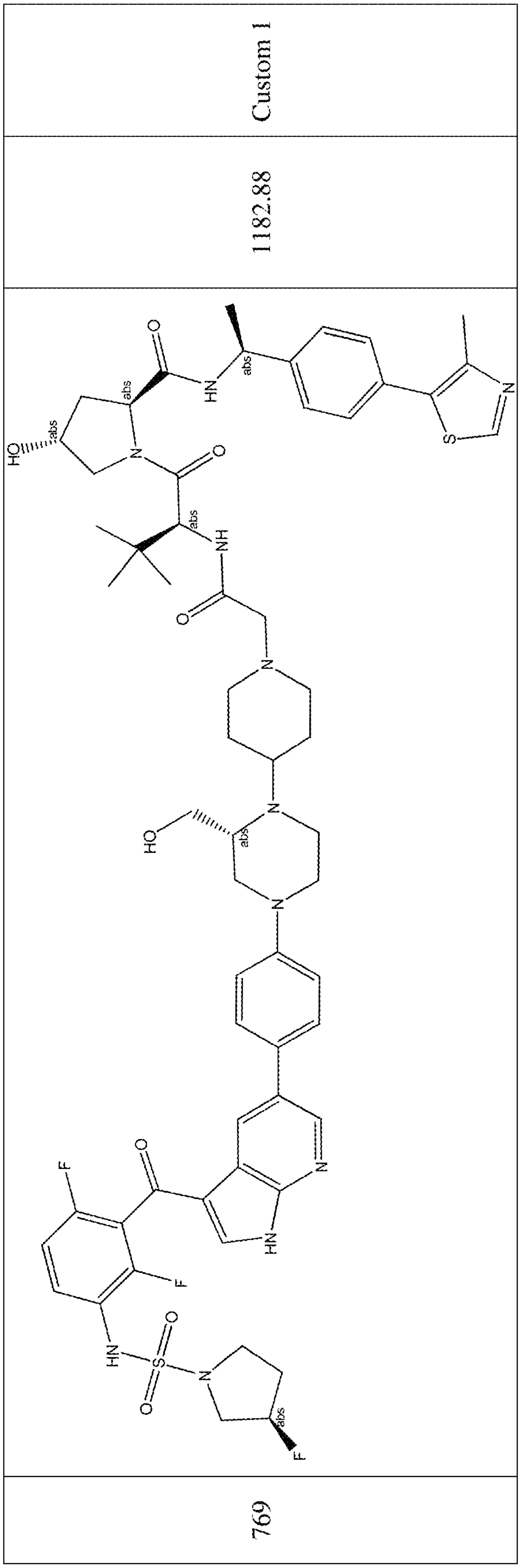
Figure 2B:
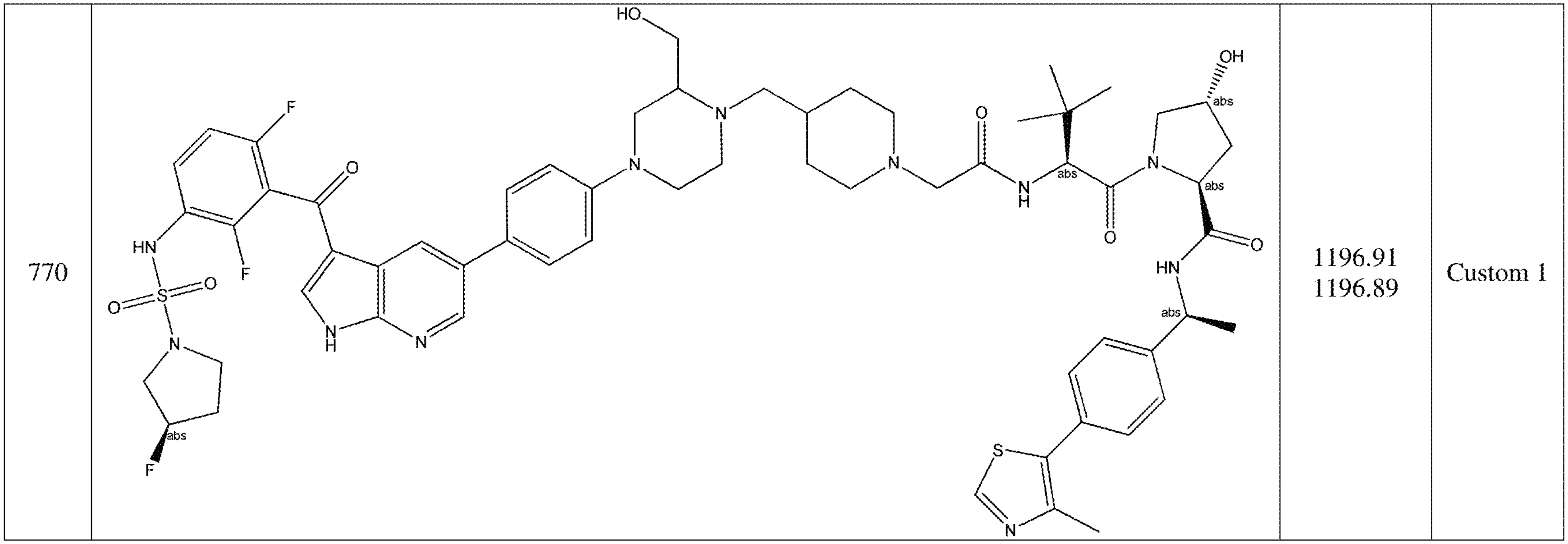
Figure 2B:
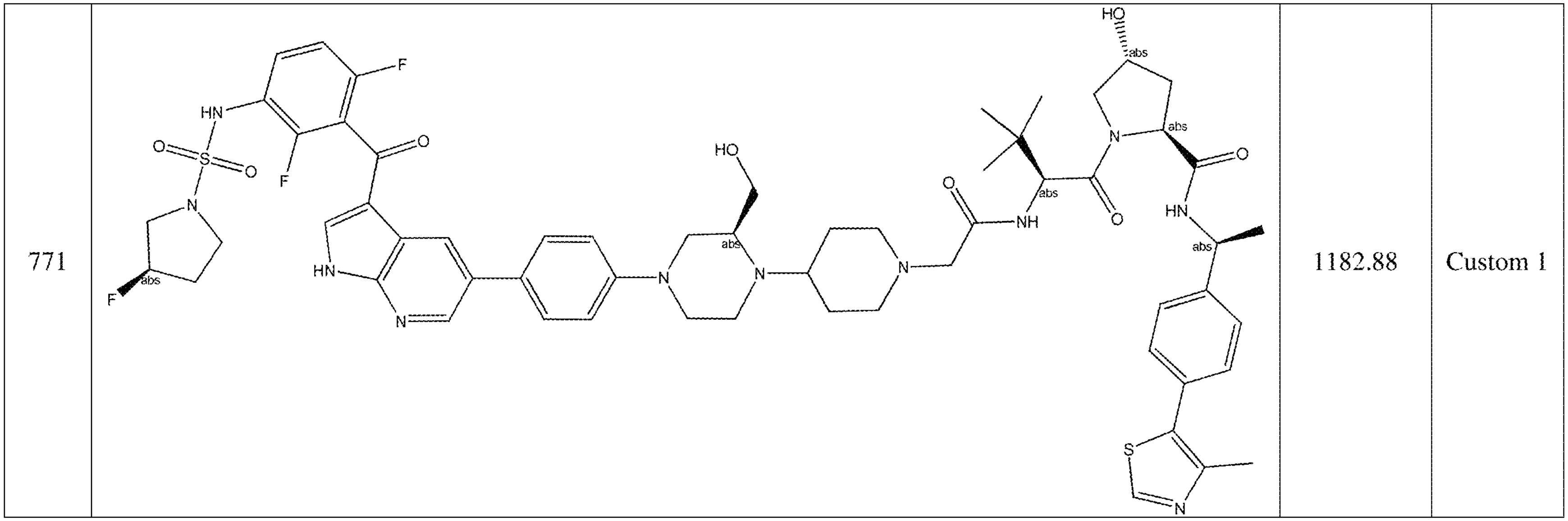
Figure 2B:
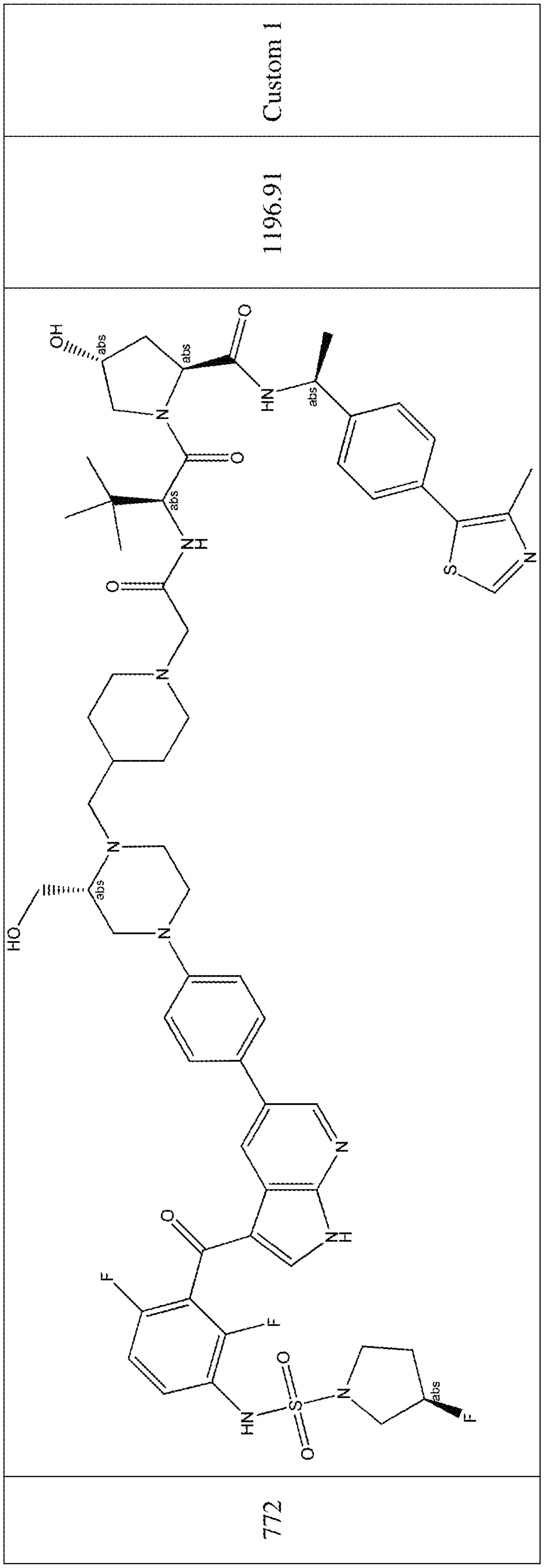
Figure 2B:
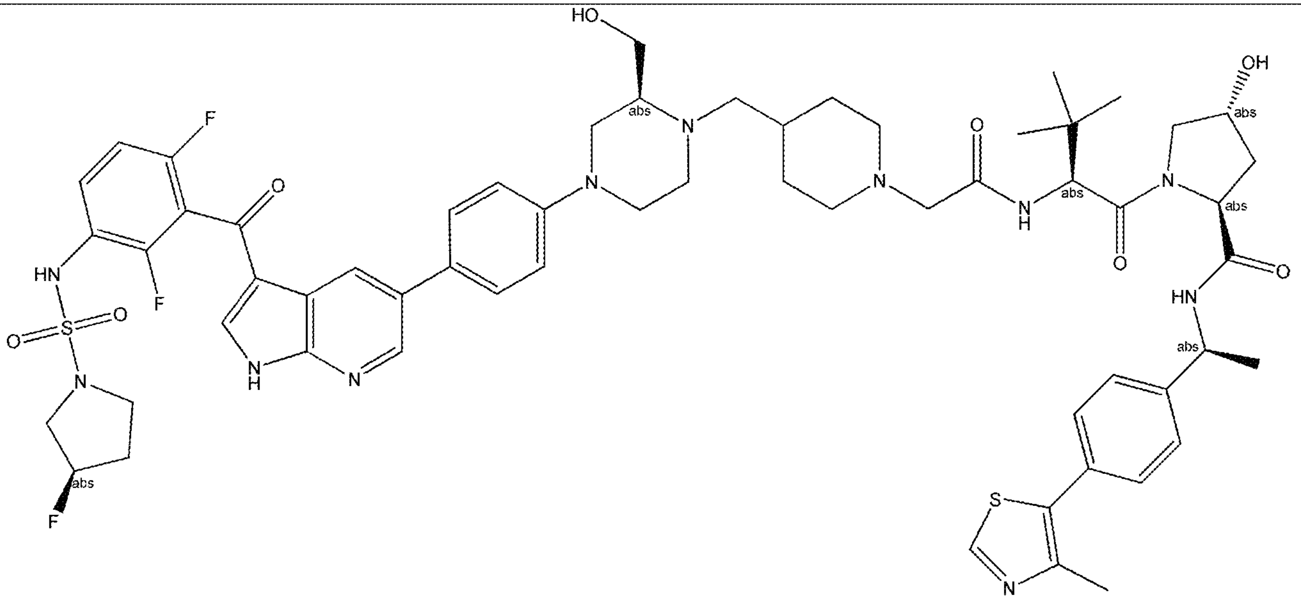
Figure 2B:
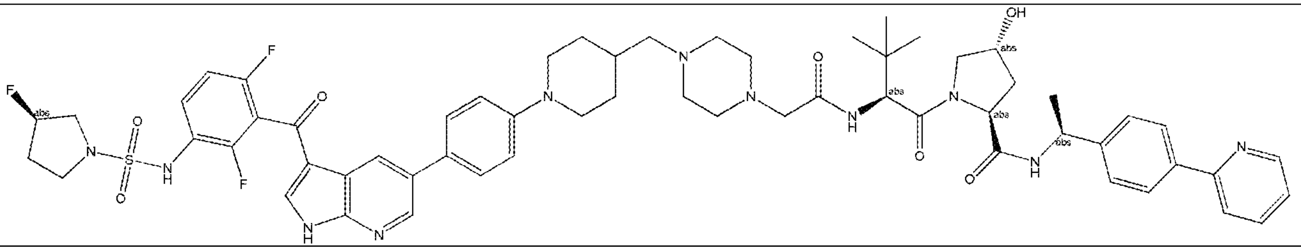
Figure 2B:
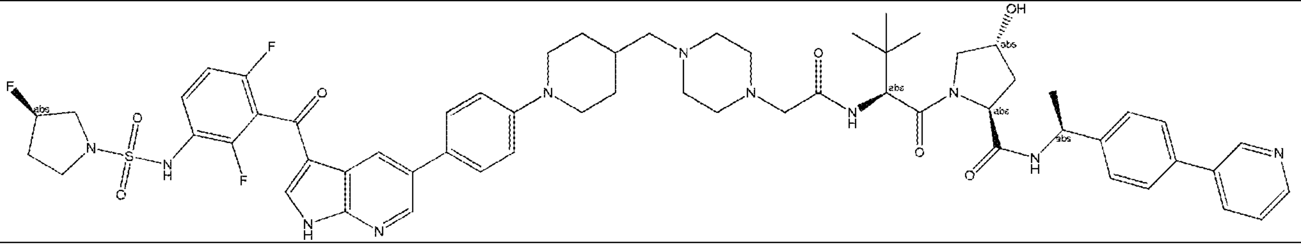
Figure 2B:
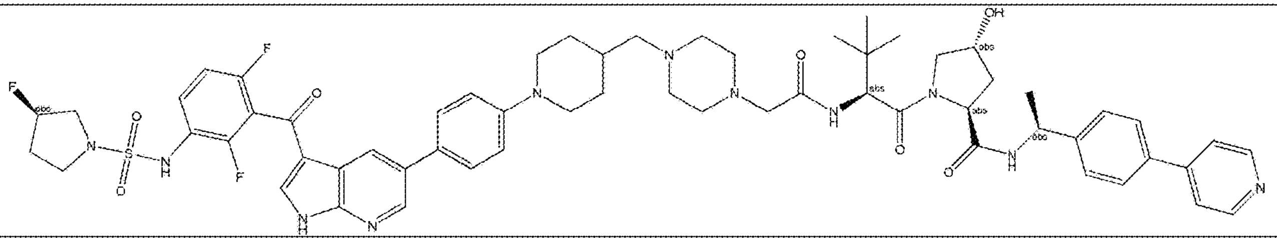
Figure 2B:
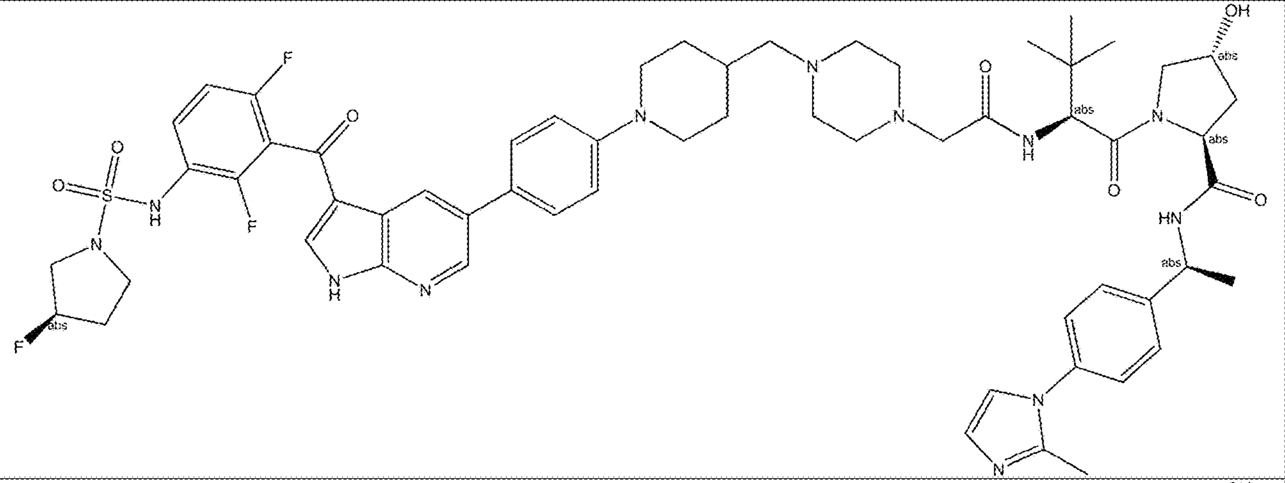
Figure 2B:
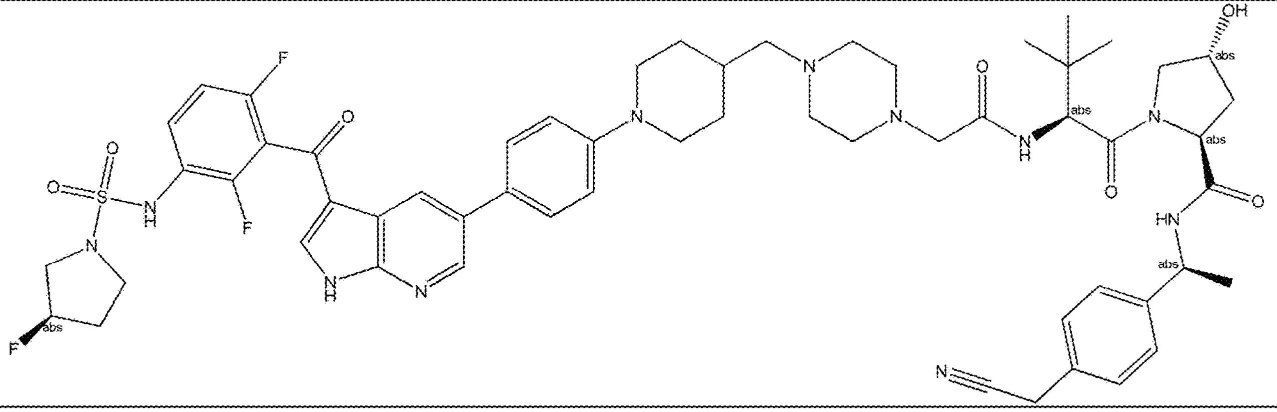
Figure 2B:
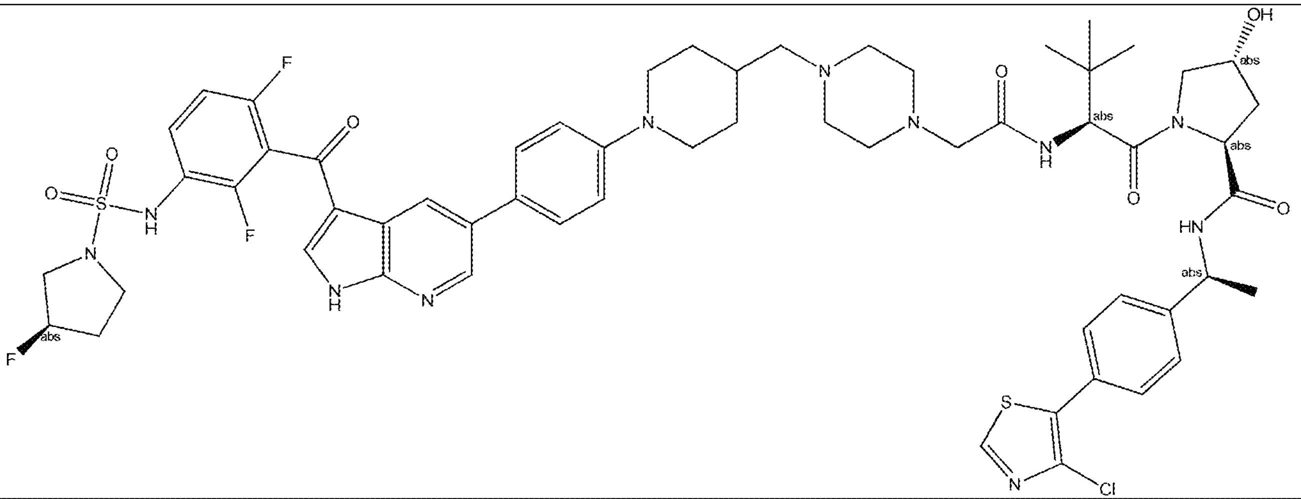
Figure 2B:
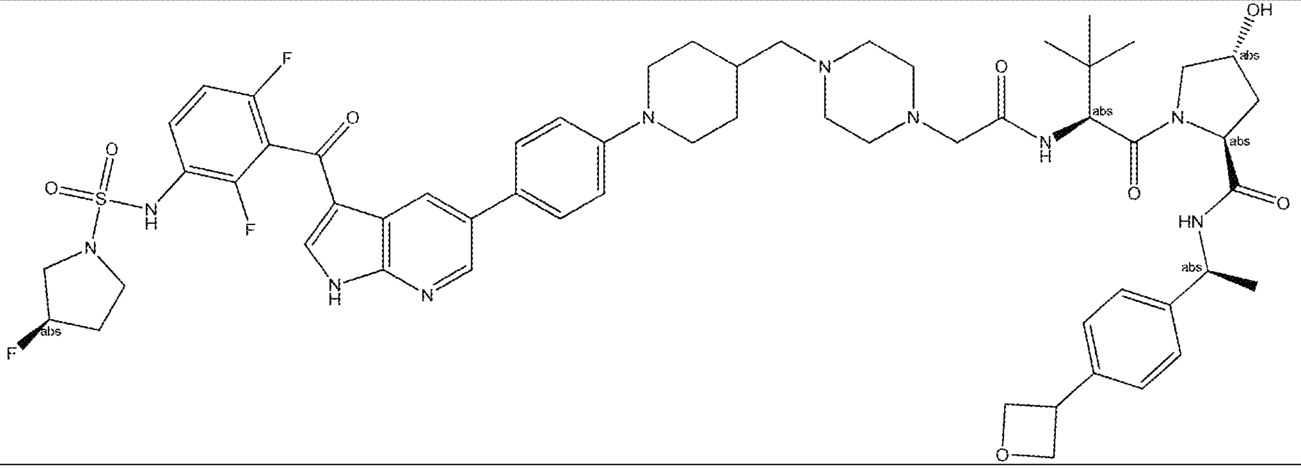
Figure 2B:
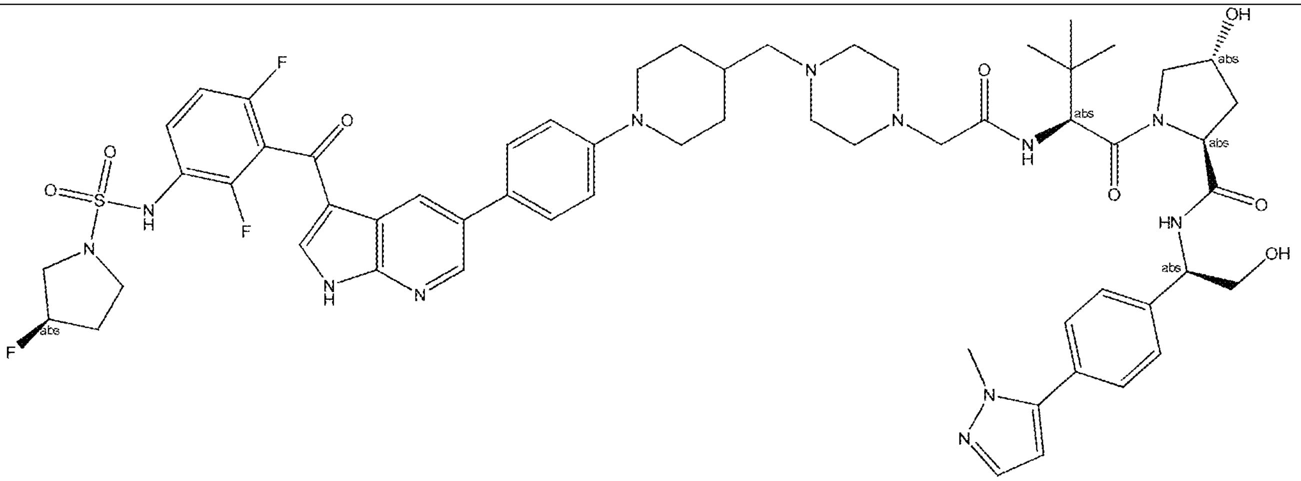
Figure 2B:
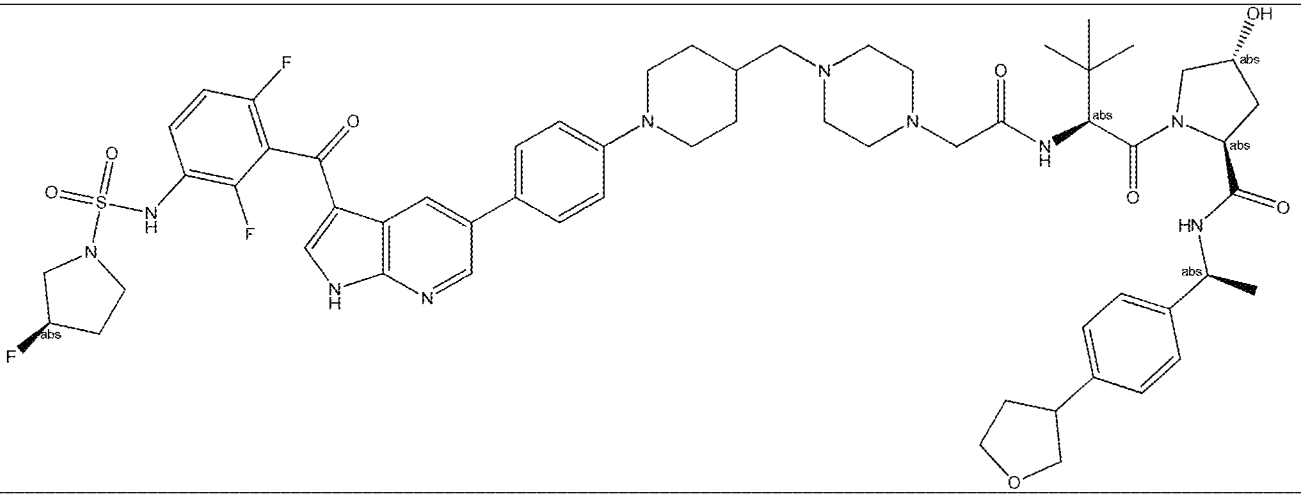
Figure 2B:
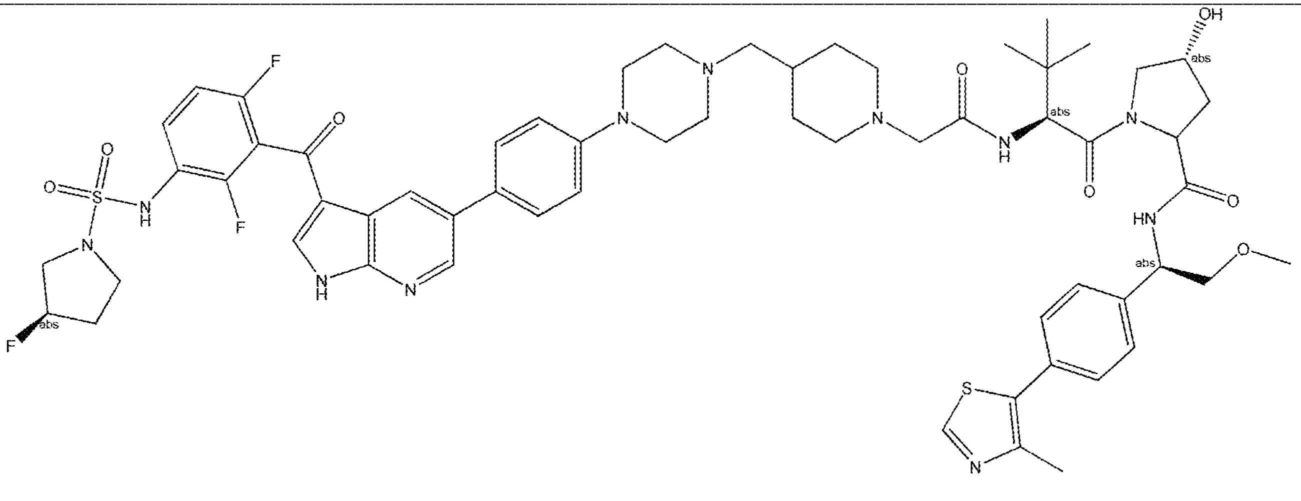
Figure 2B:
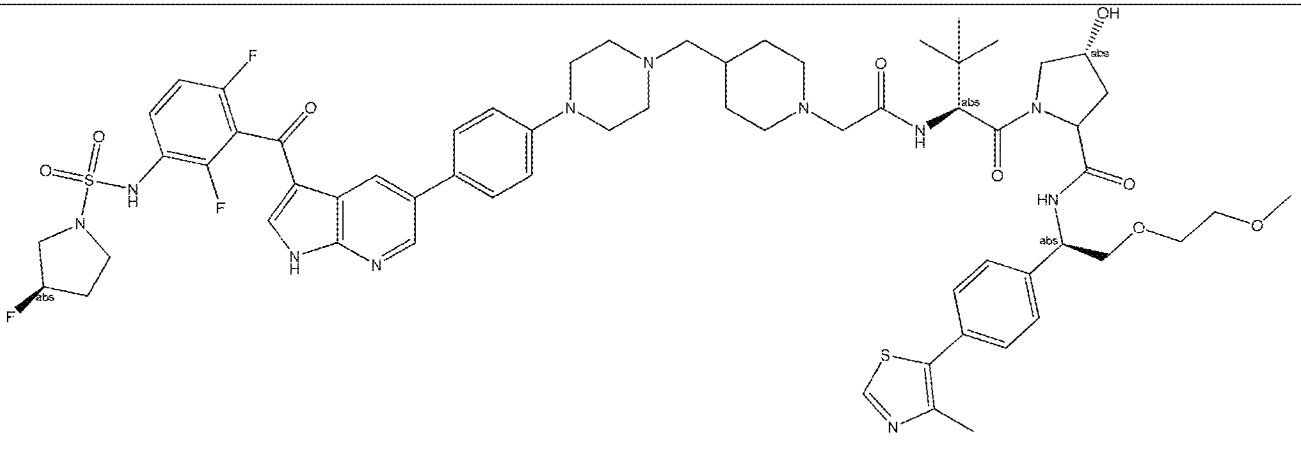
Figure 2B:
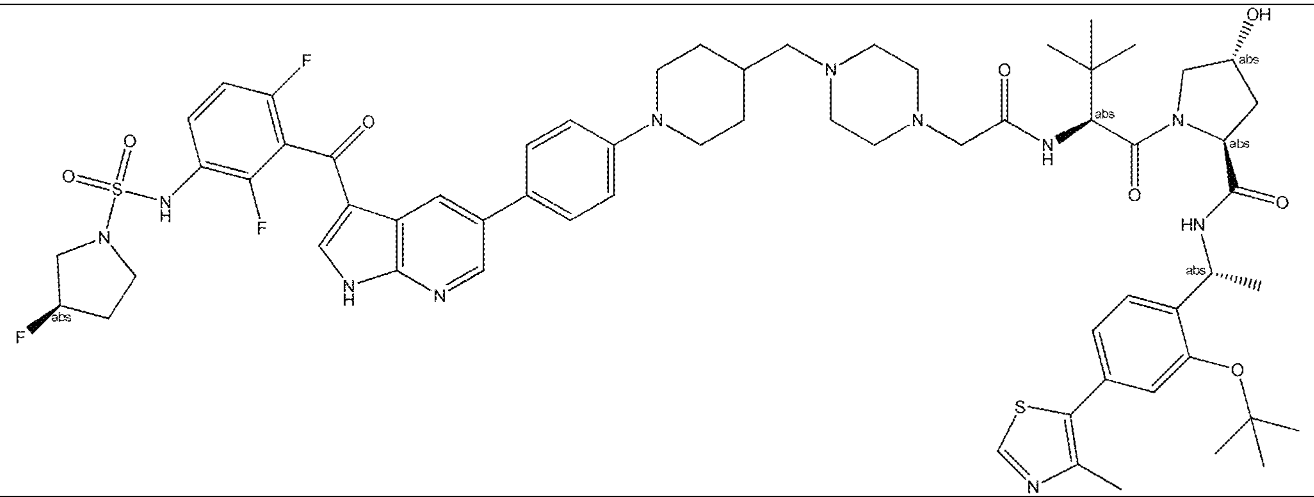
Figure 2B:
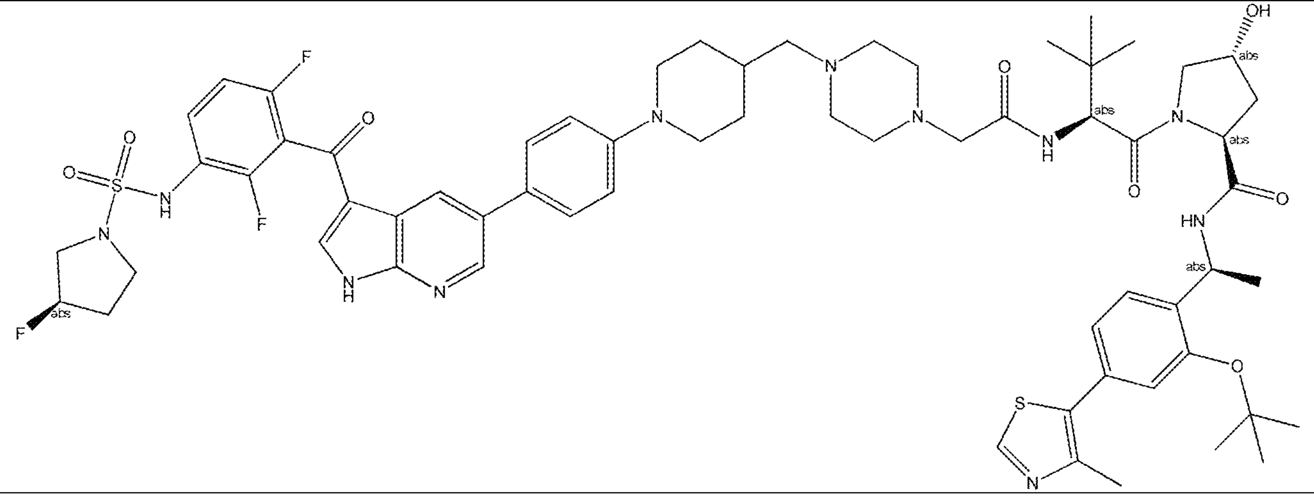
Figure 2B:
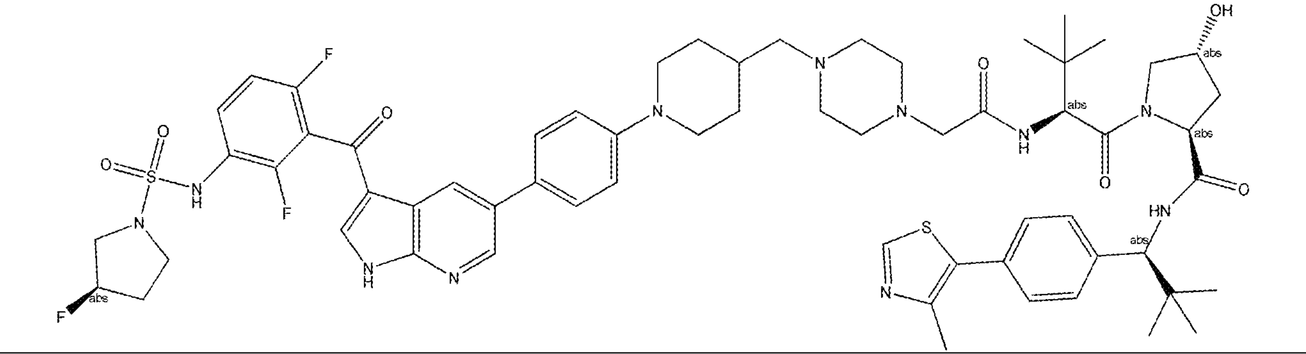
Figure 2B:
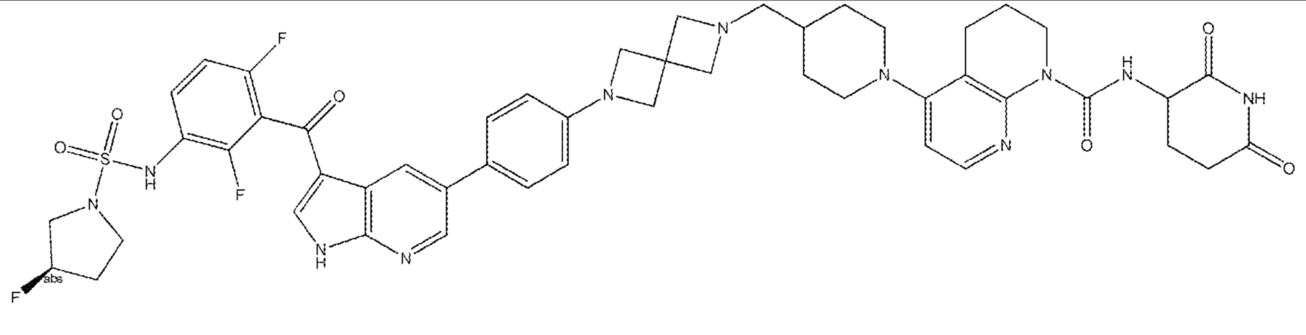
Figure 2B:
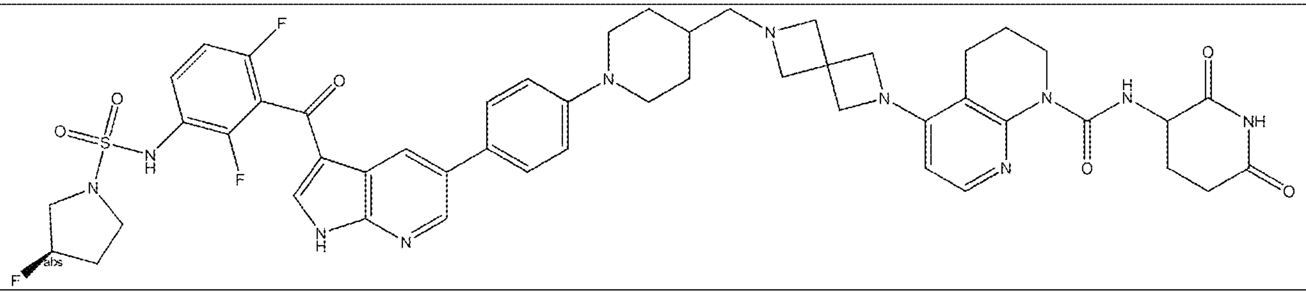
Figure 2B:
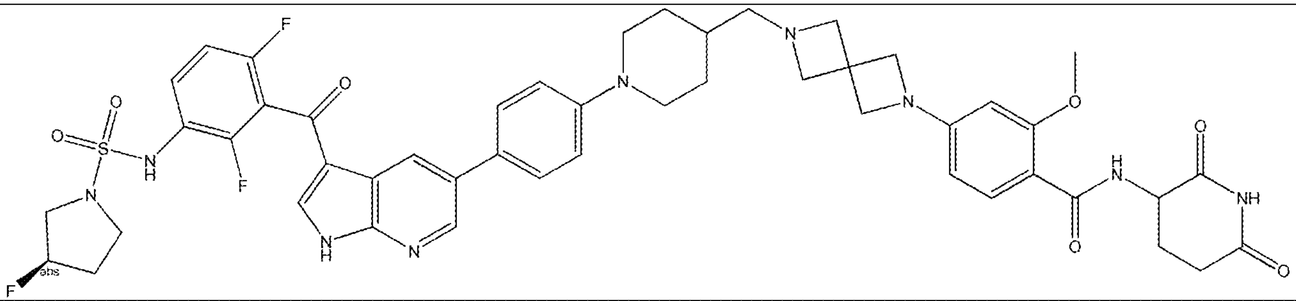
Figure 2B:
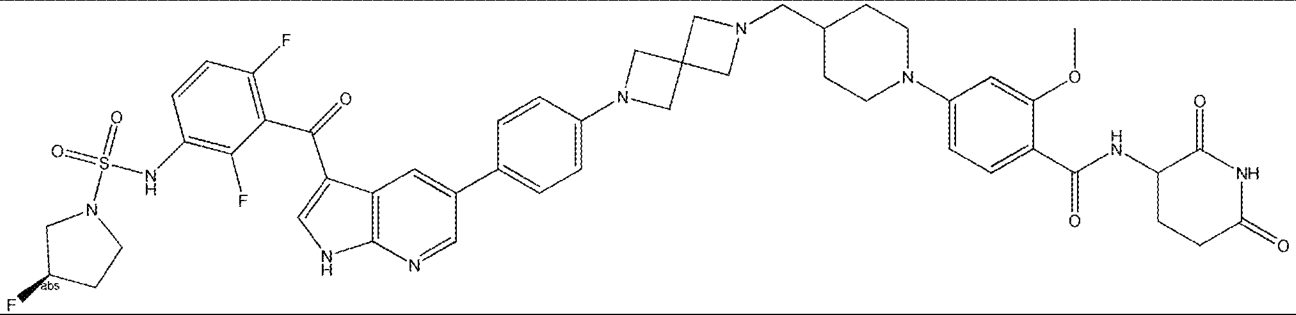
Figure 2B:
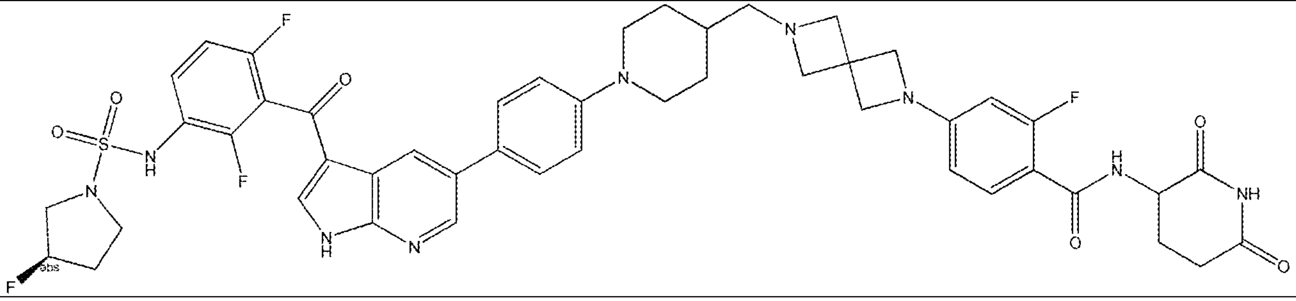
Figure 2B:
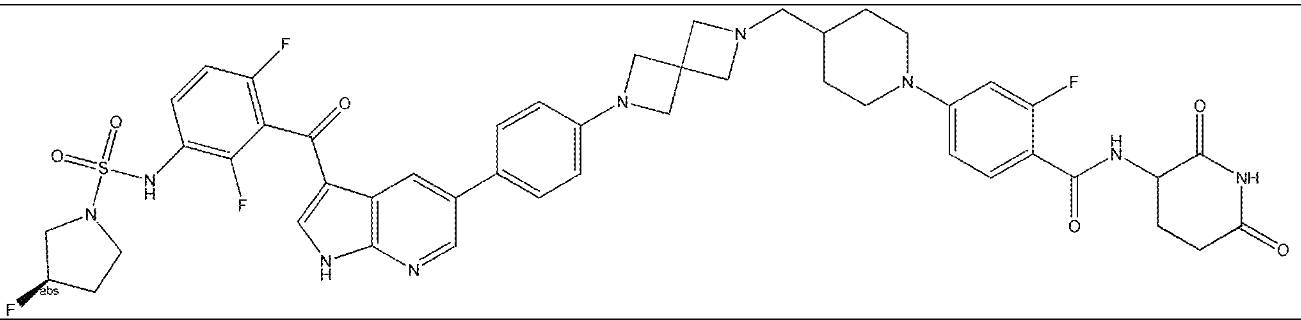
Figure 2B:
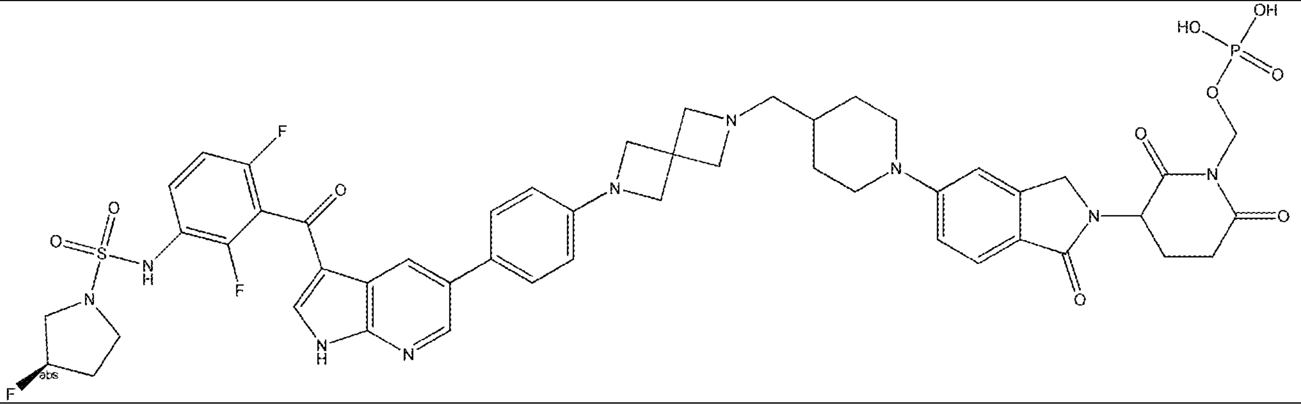
Figure 2B:
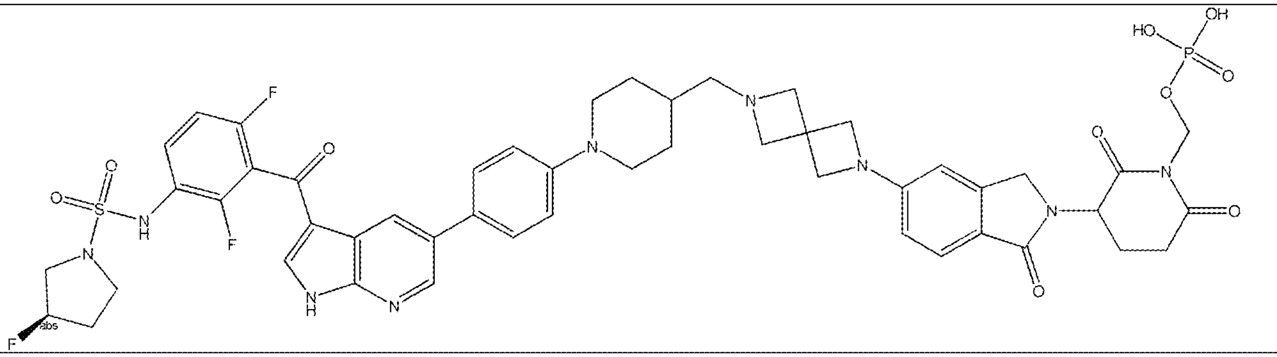
Figure 2C:
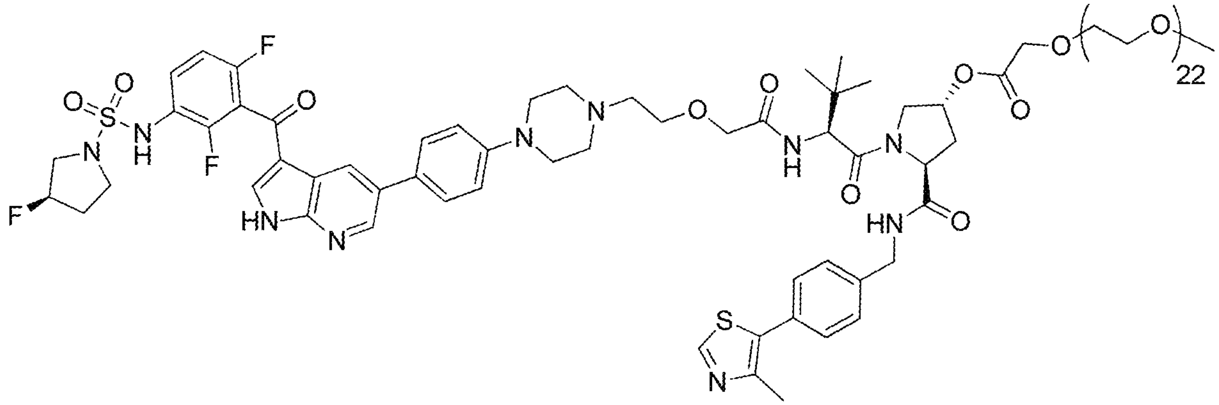
FIG. 2C. Table 1C. Exemplary protein targeting moieties and compounds of the present disclosure.
Figure 2C:
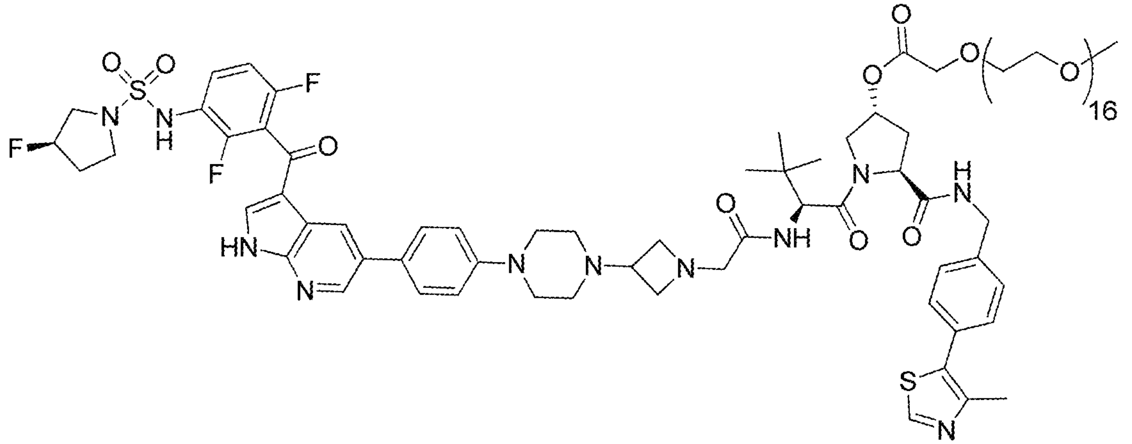
Figure 2C:
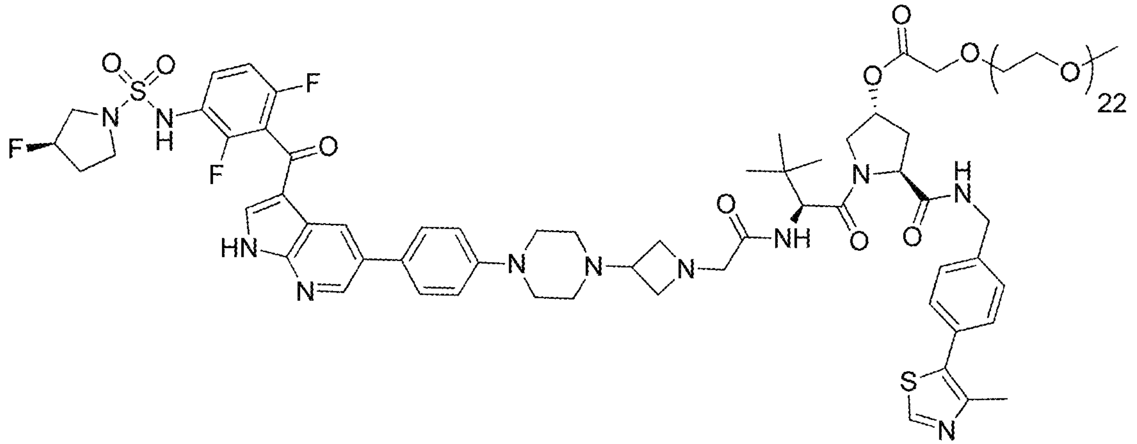
Figure 2C:
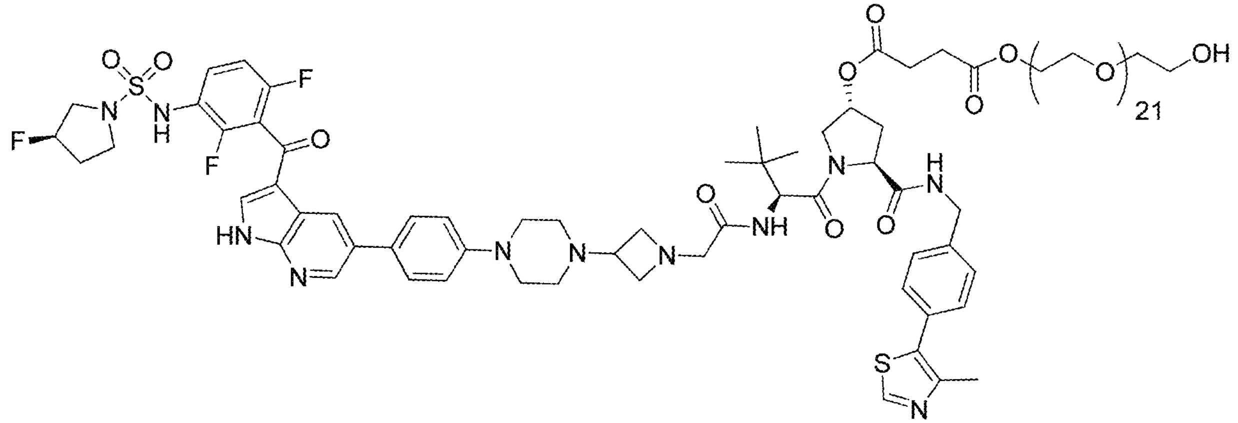
Figure 2C:
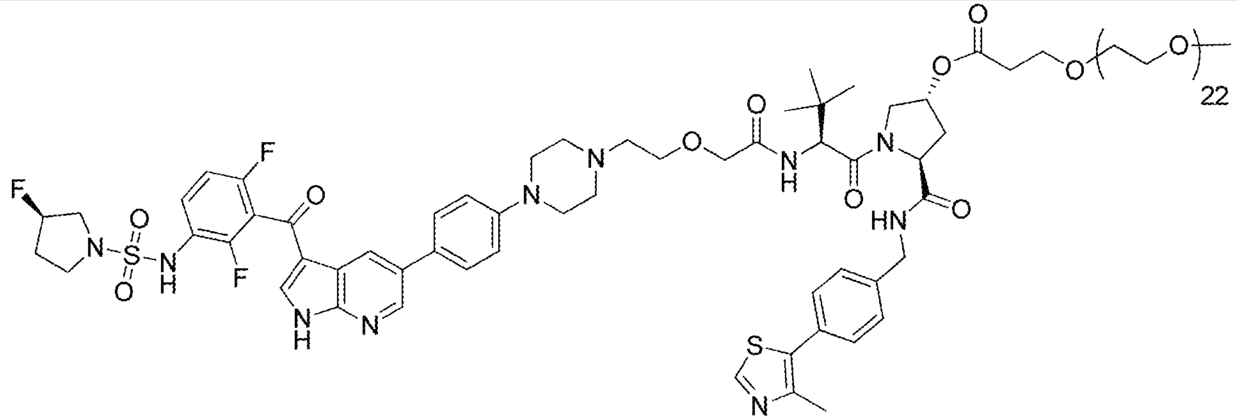
Figure 2C:
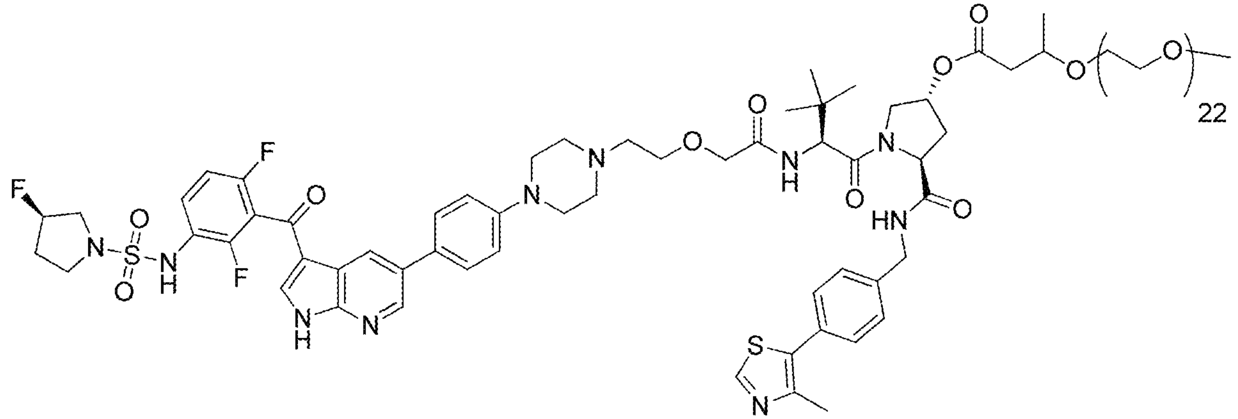
Figure 2C:
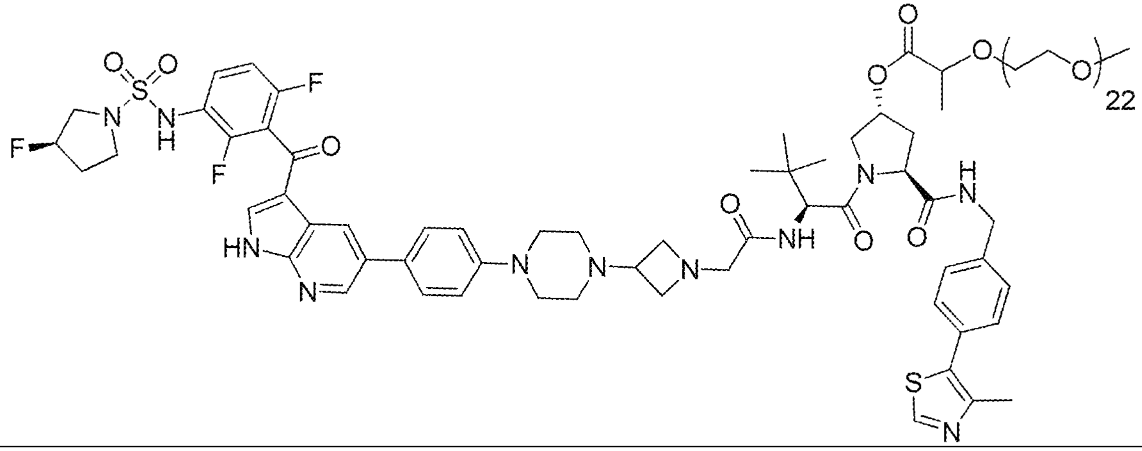
Figure 2C:
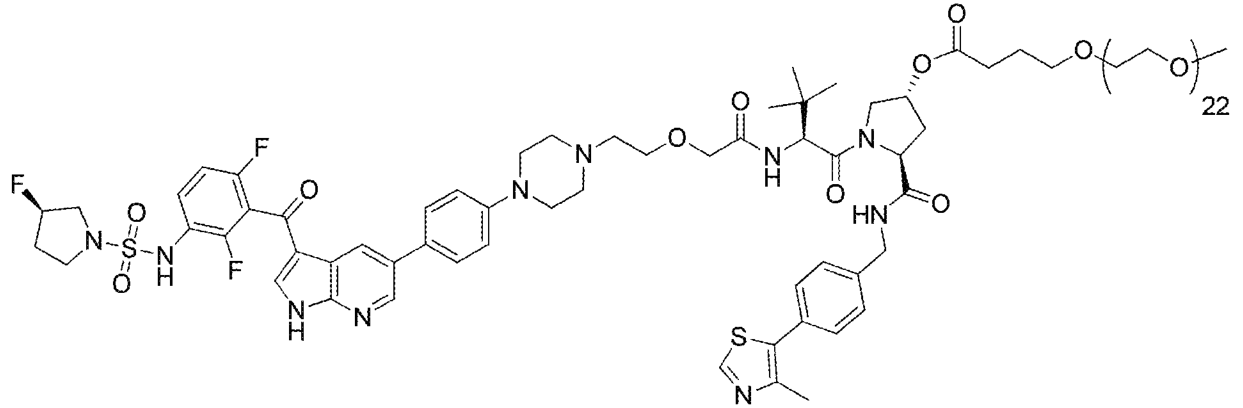
Figure 2C:
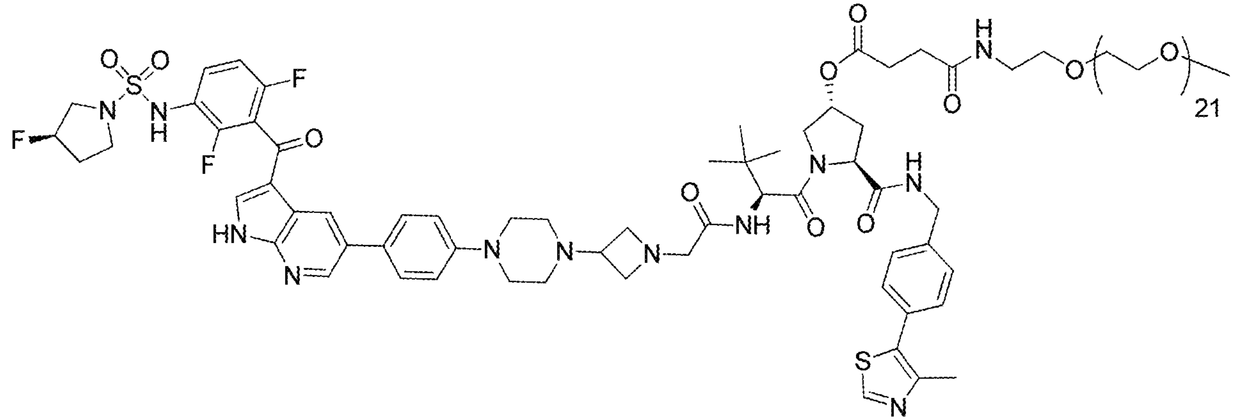
Figure 2C:
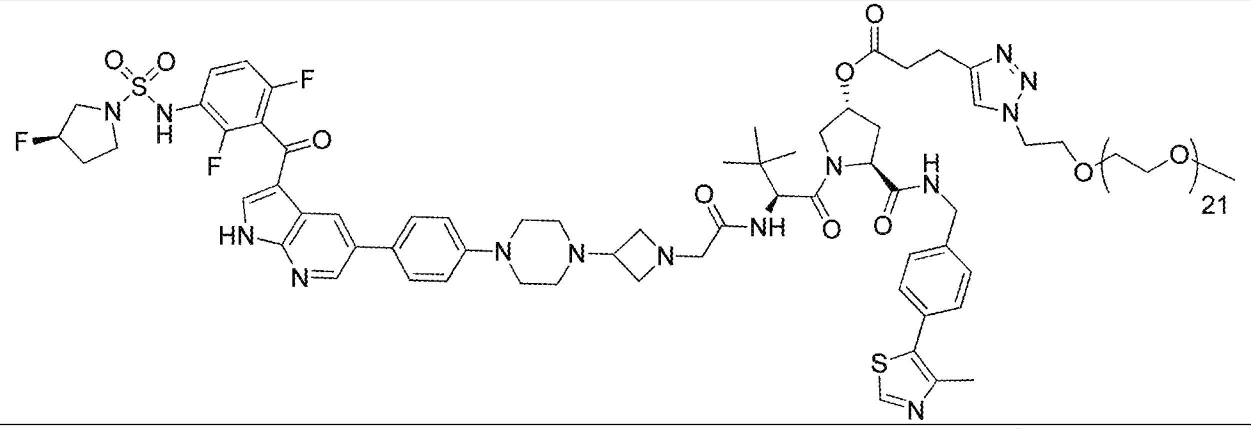
Figure 2C:
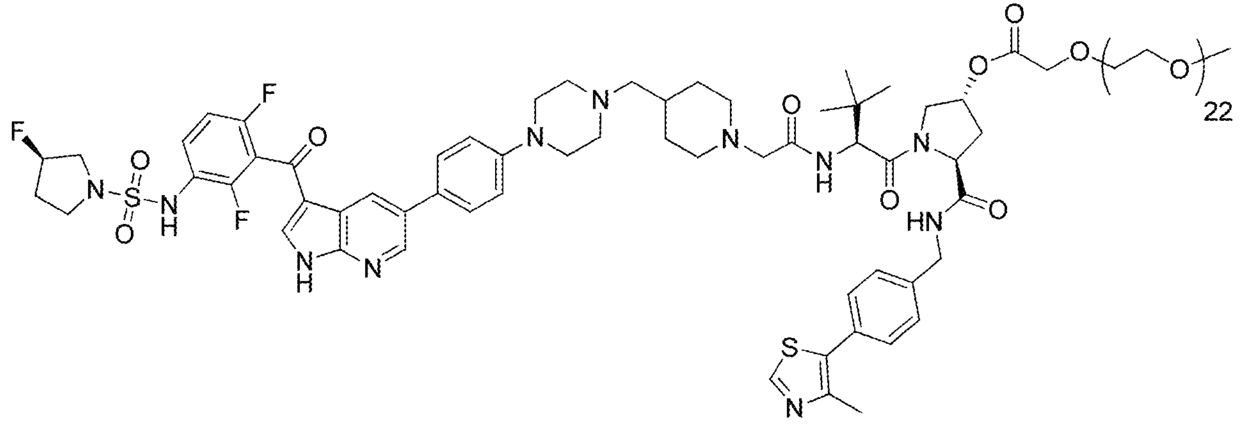
Figure 2C:
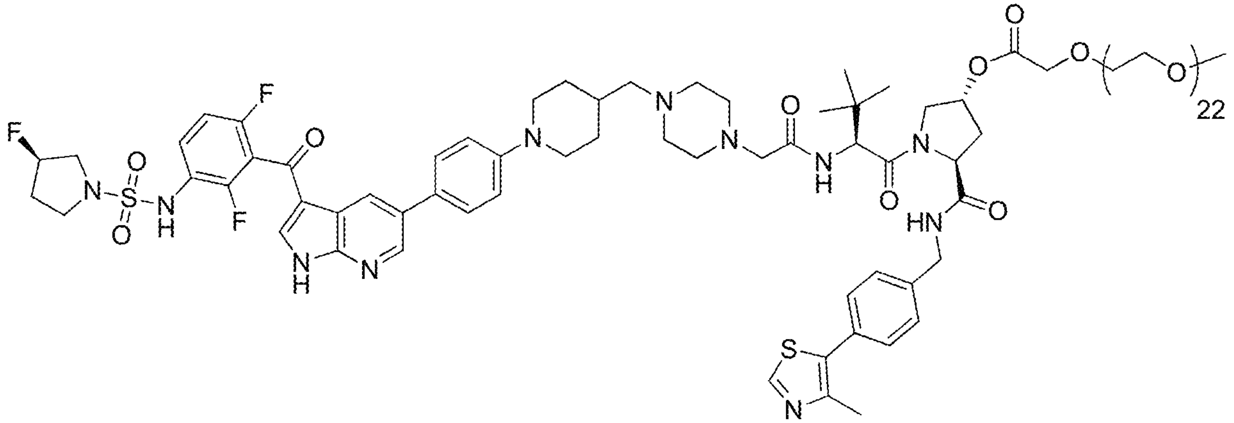
Figure 2C:
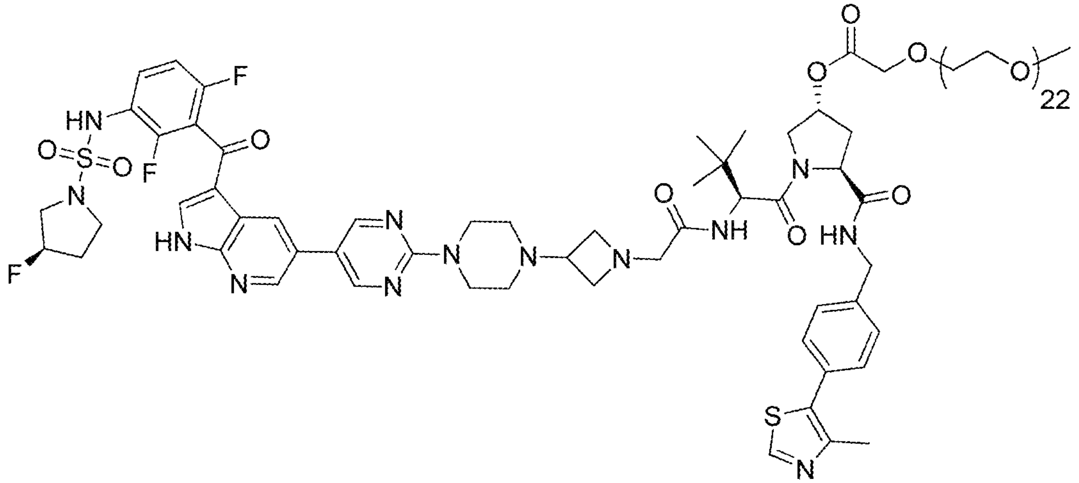
Figure 2C:
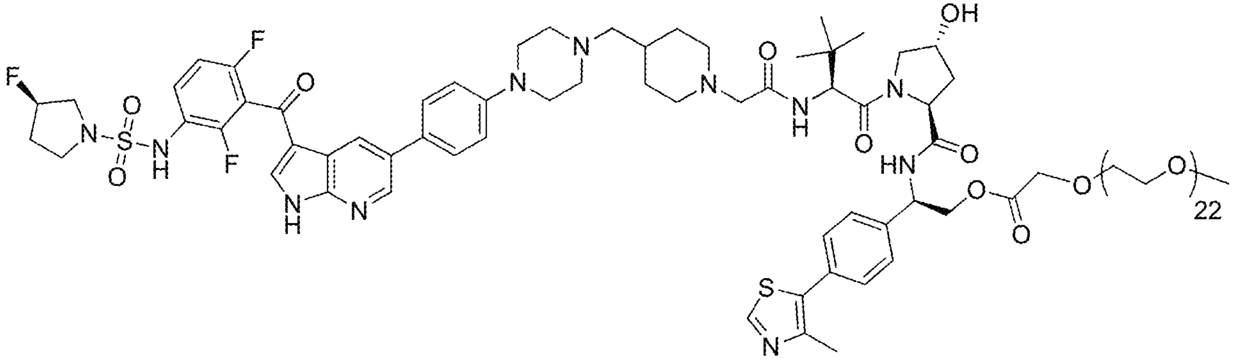
Figure 2C:
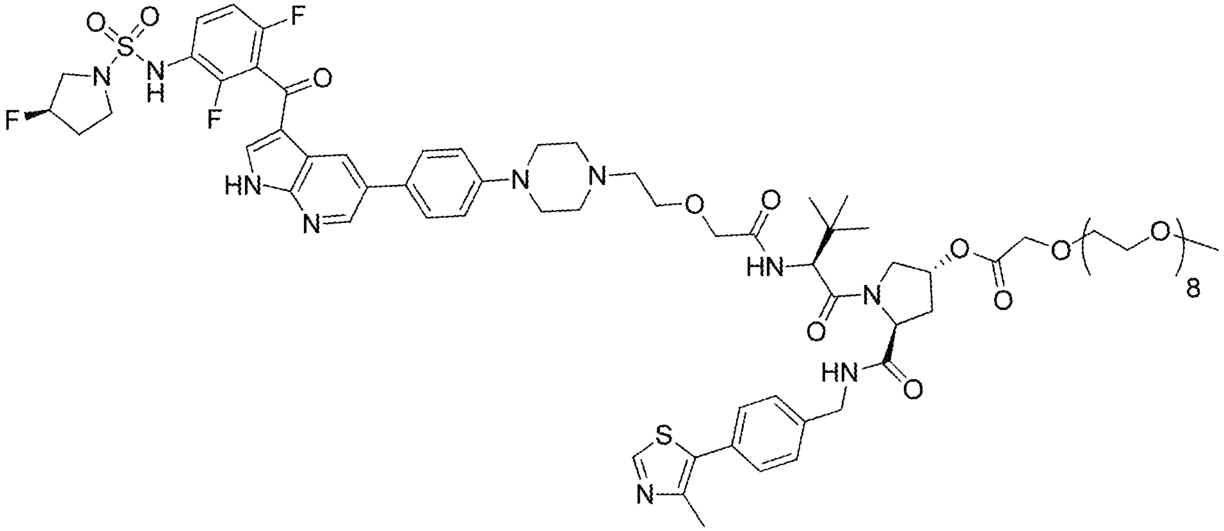
Figure 2C:
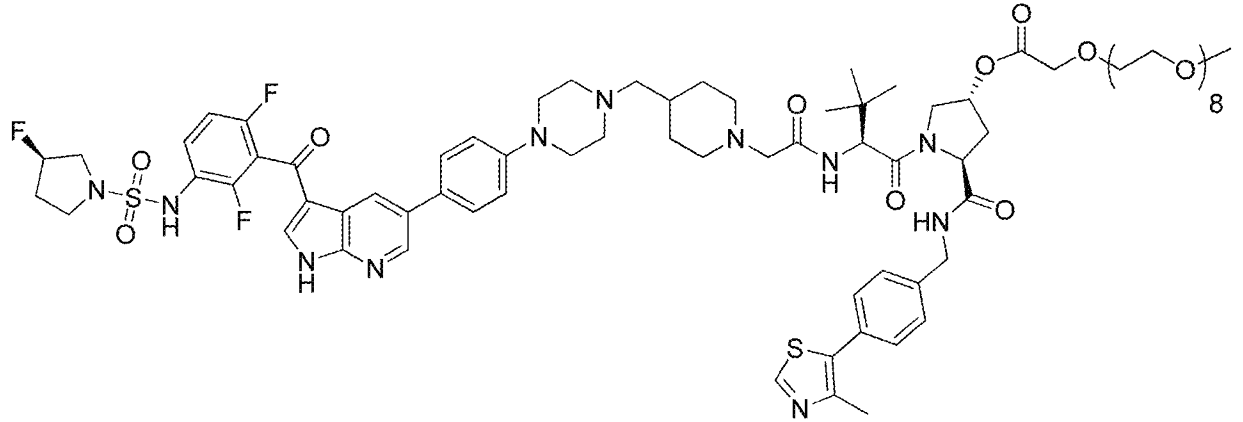
Figure 2C:
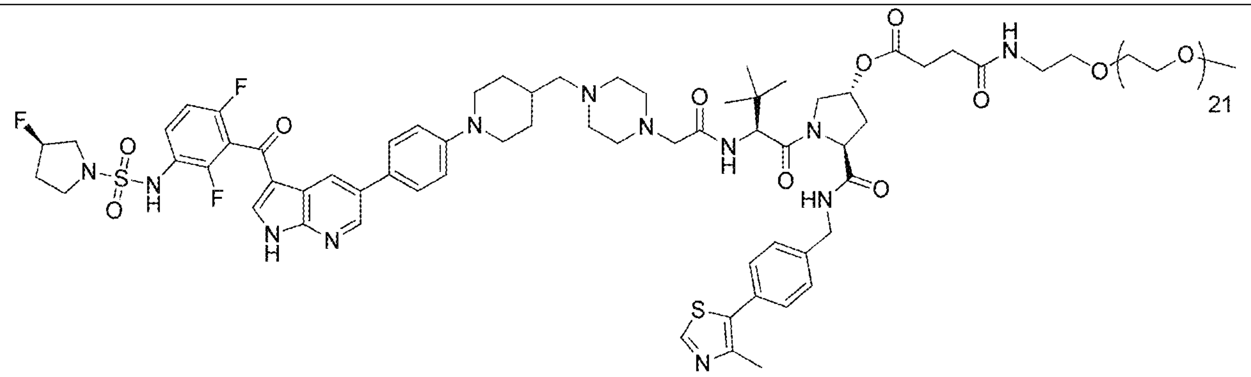
Figure 2C:
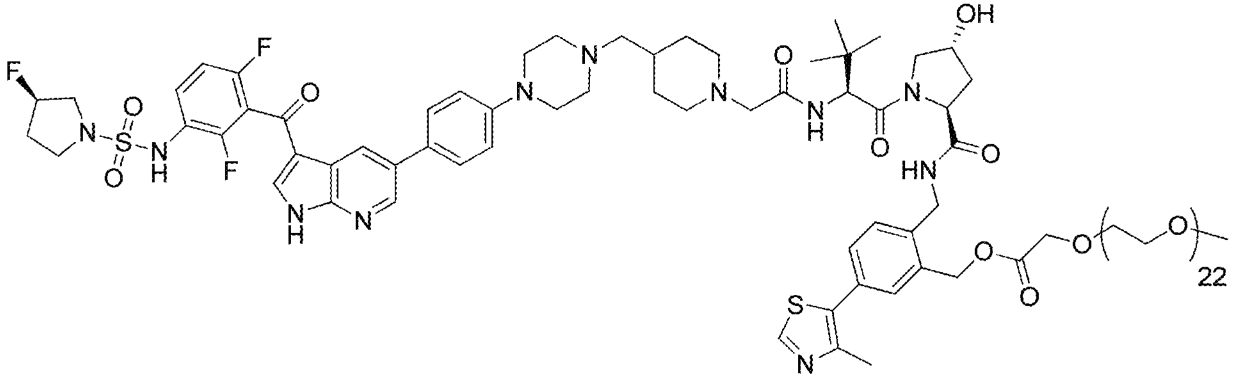
Figure 2C:
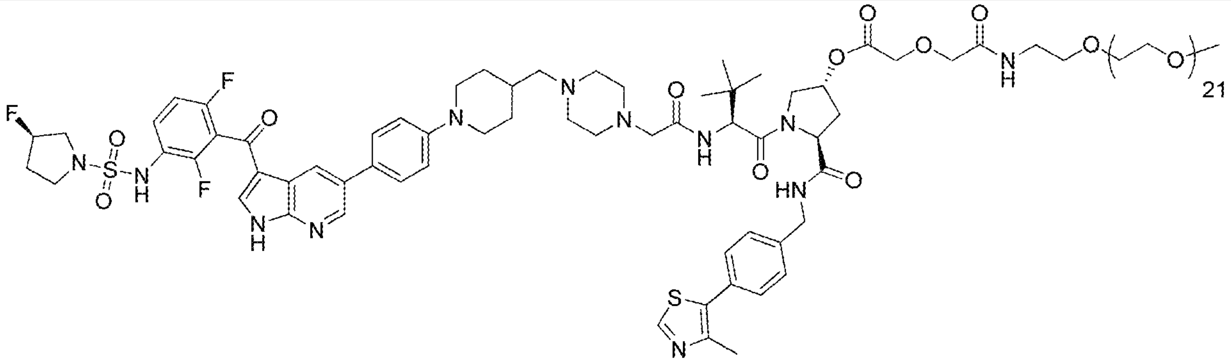
Figure 2C:
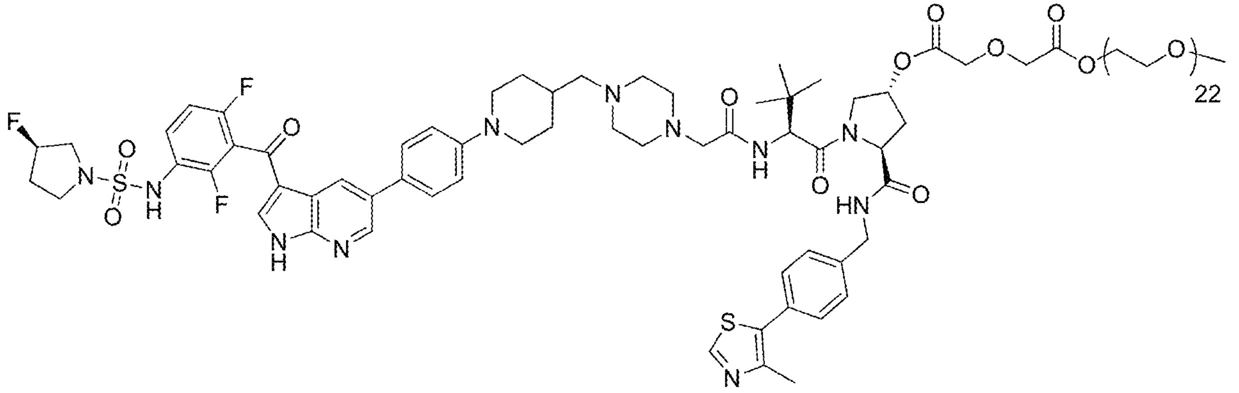
Figure 2C:
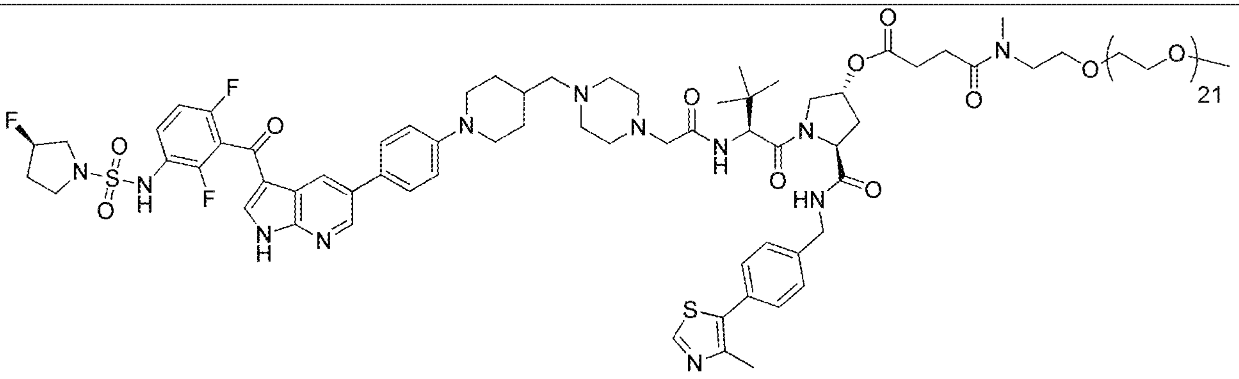
Figure 2C:
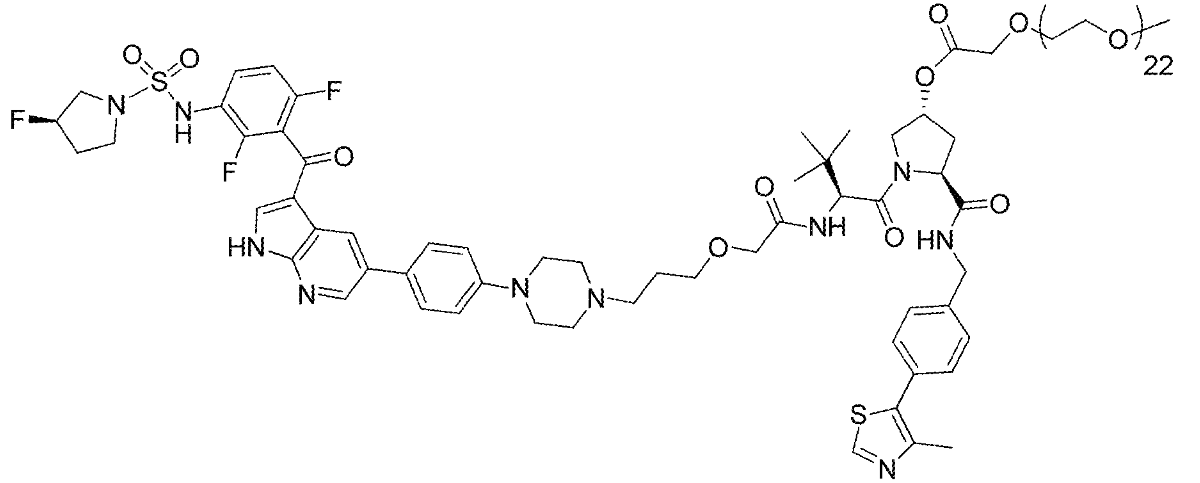
Figure 2C:
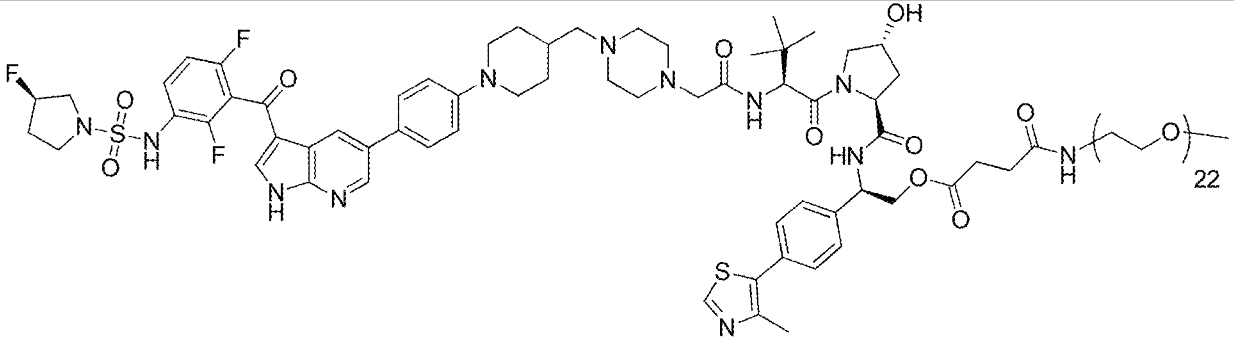
Figure 2C:
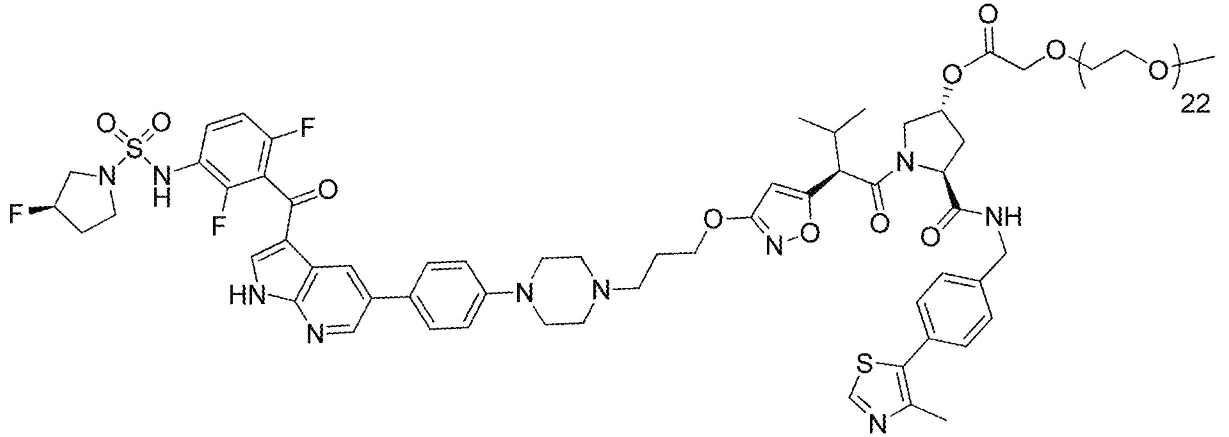
Figure 2C:
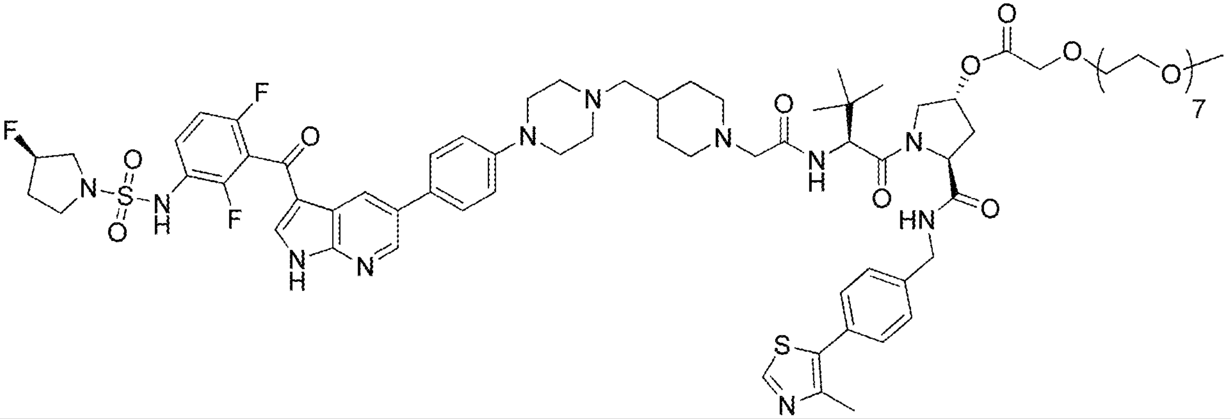
Figure 2C:
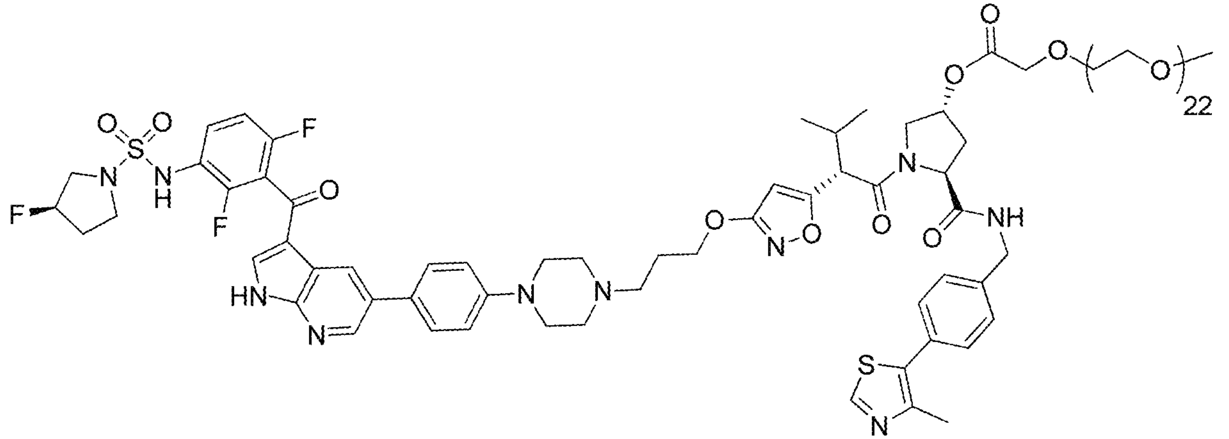
Figure 2C:
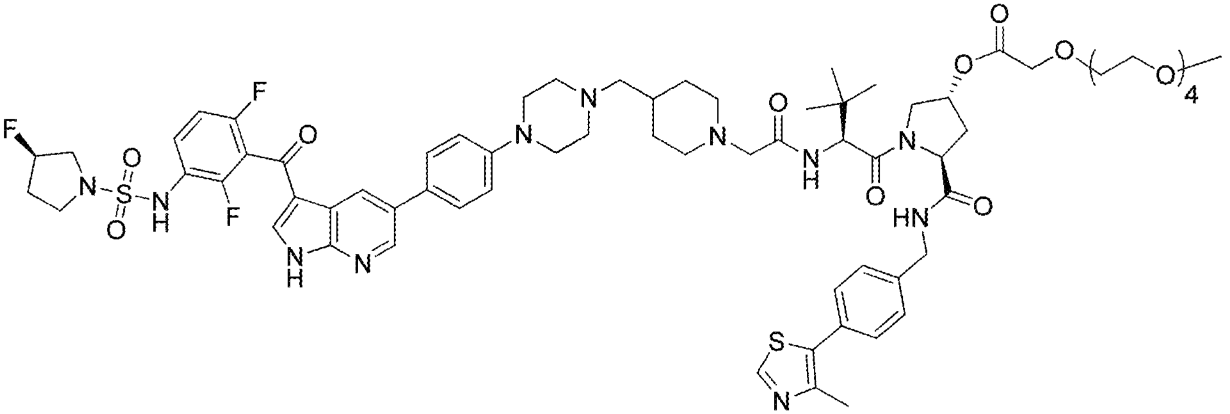
Figure 2C:
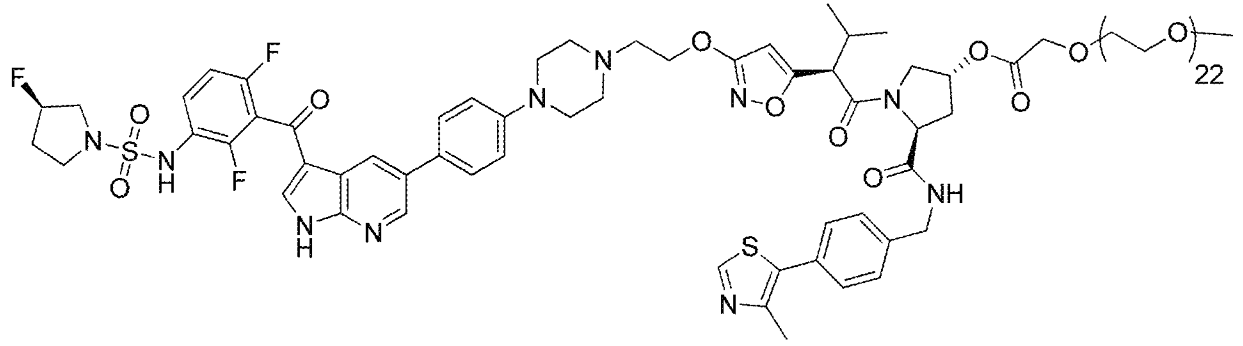
Figure 2C:
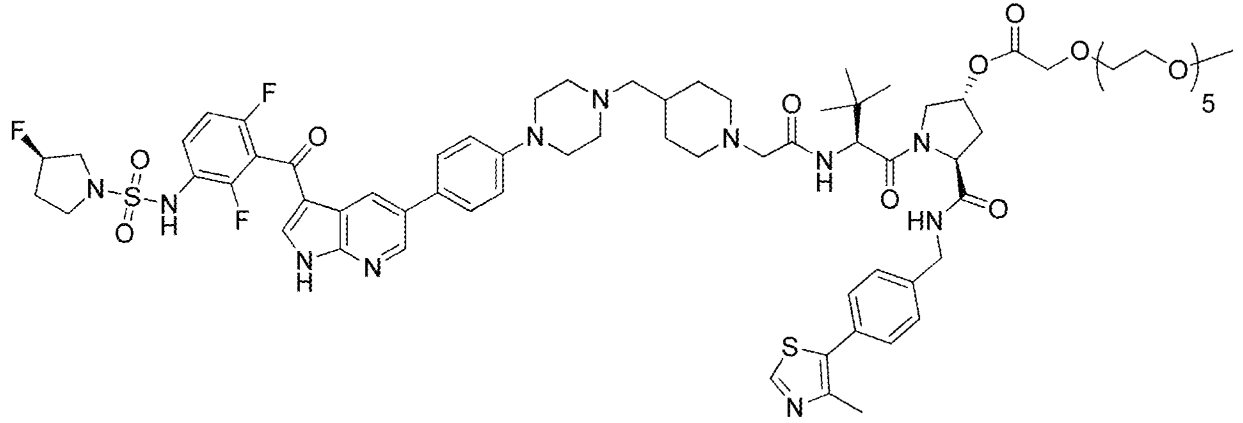
Figure 2C:
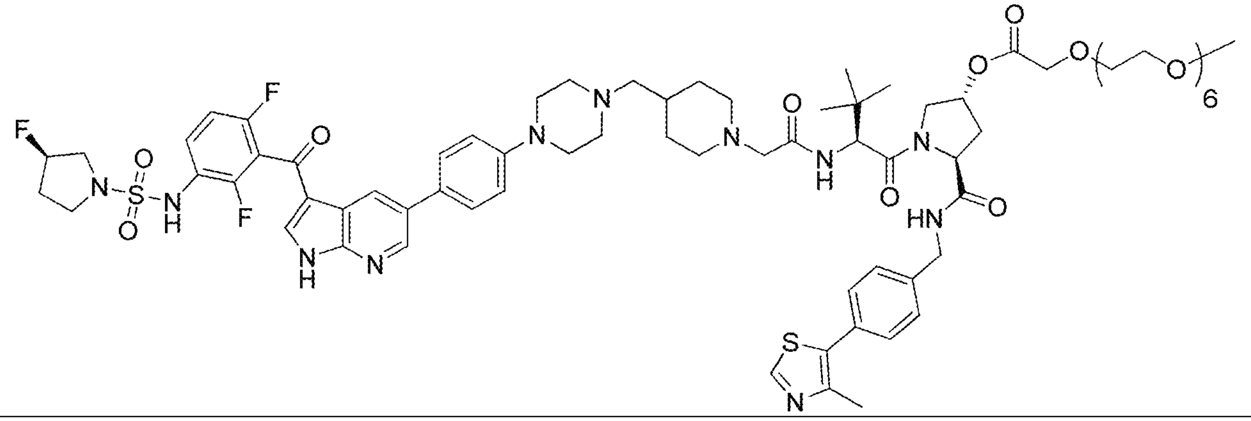
Figure 2C:
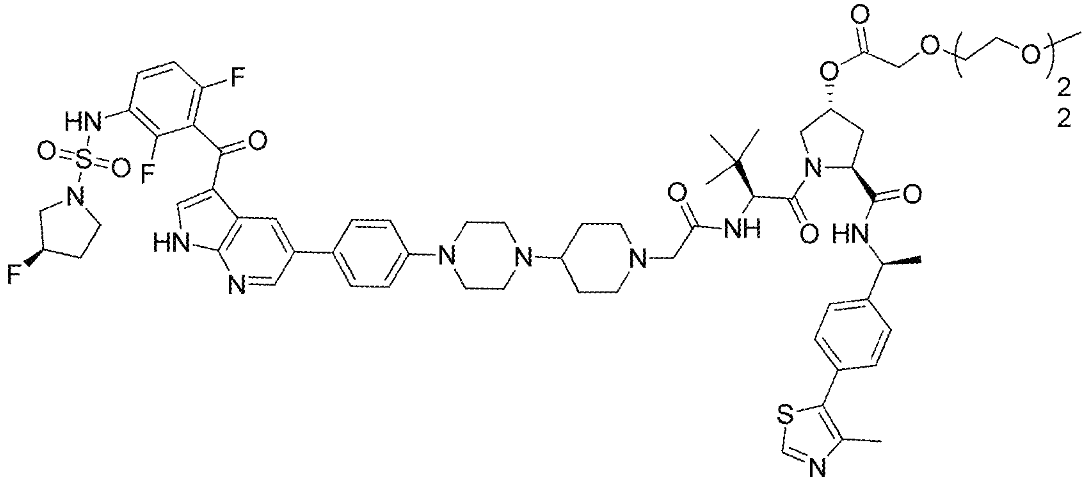
Figure 2C:
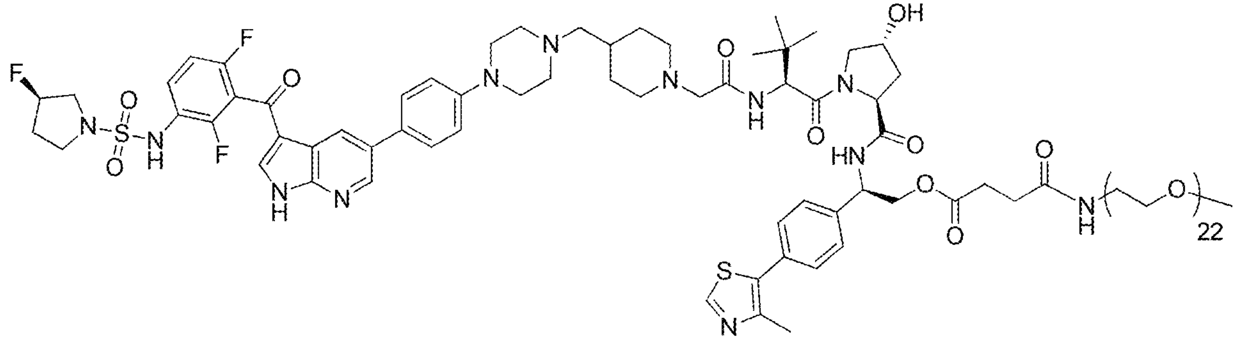
Figure 2C:
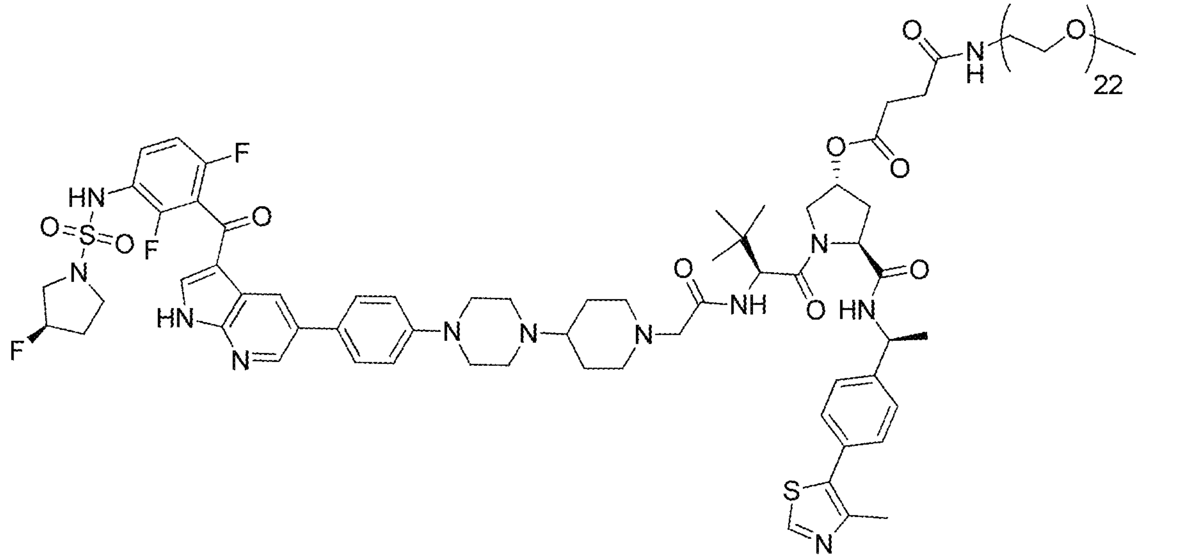
Figure 2C:
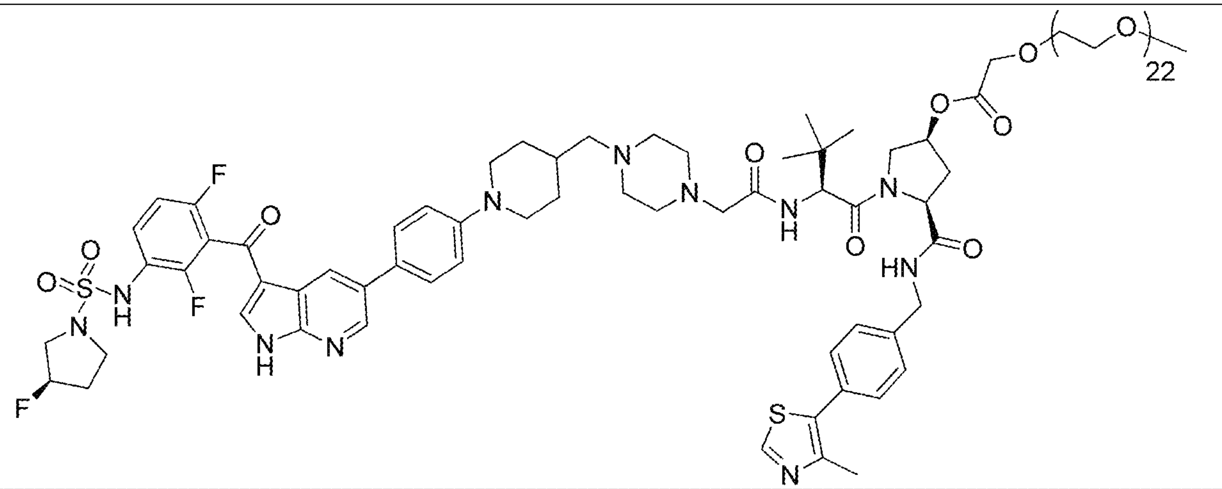
Figure 2C:
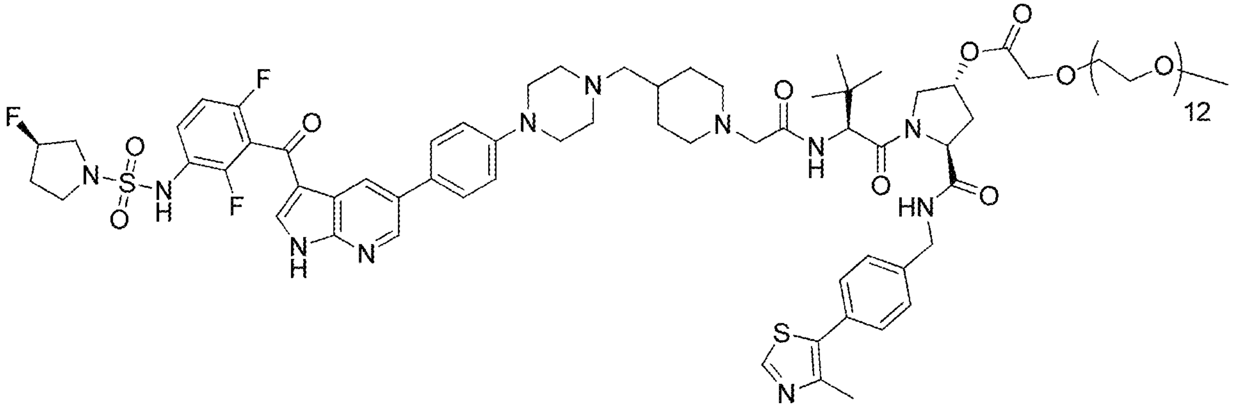
Figure 2C:
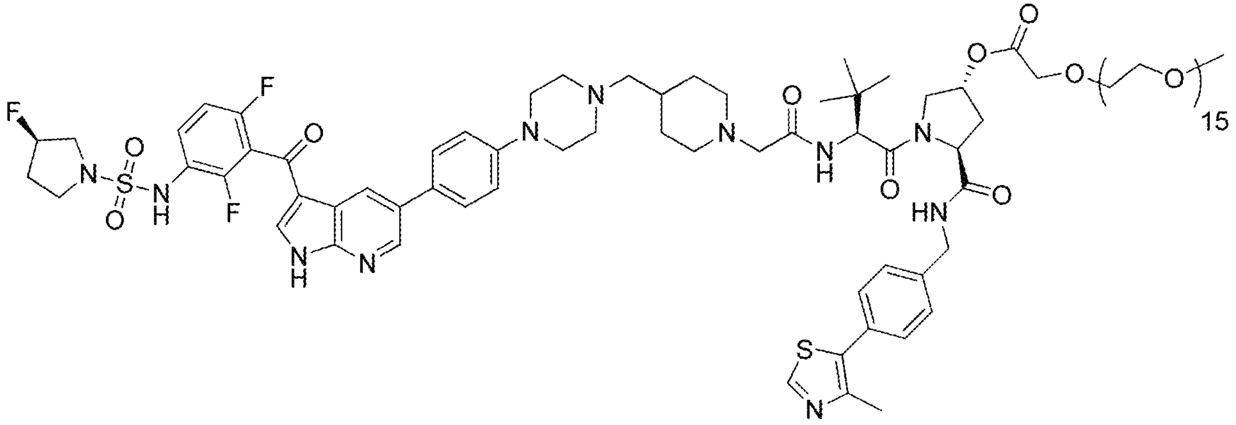
Figure 2C:
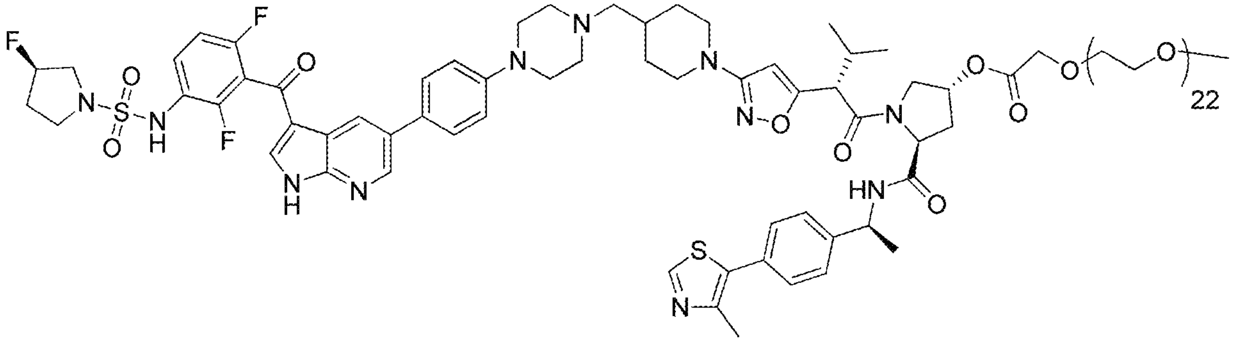
Figure 2C:
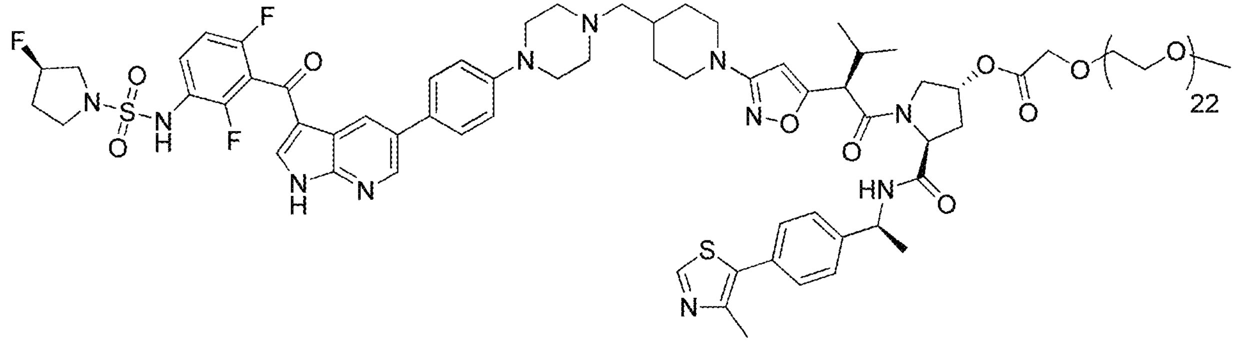
Figure 2C:
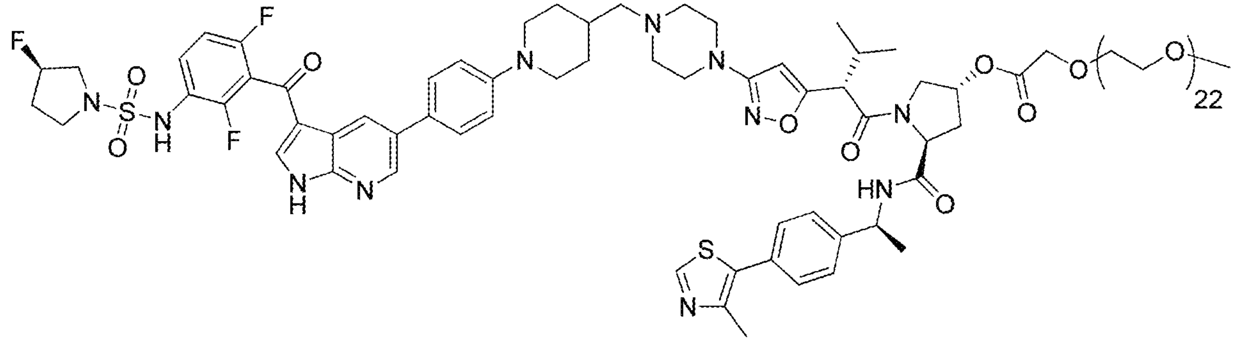
Figure 2C:
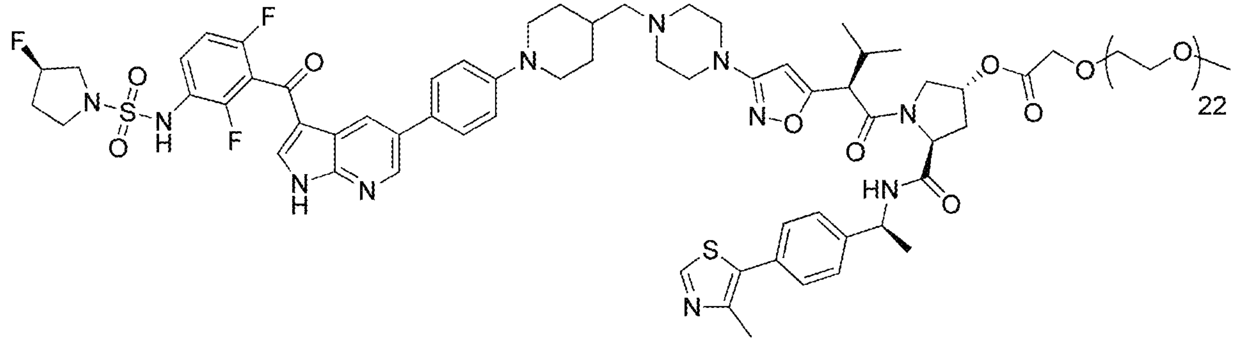
Figure 2C:
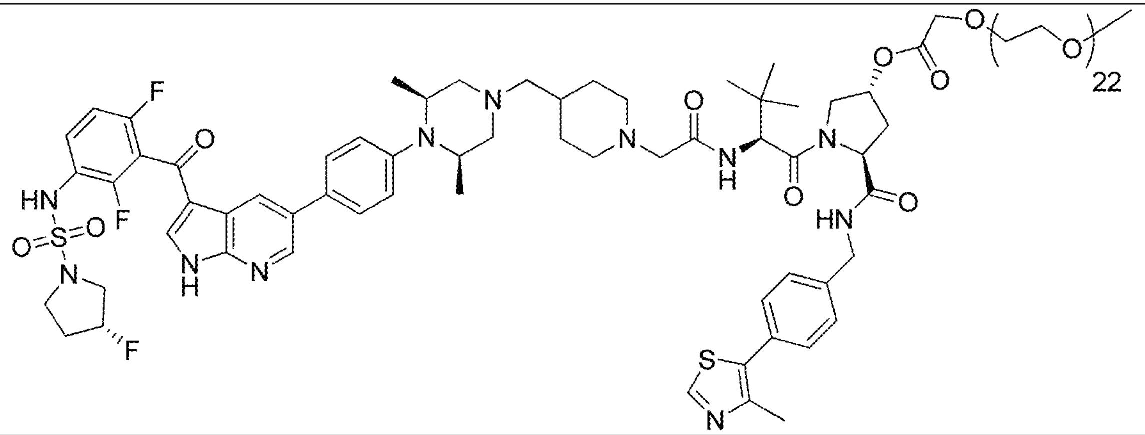
Figure 2C:
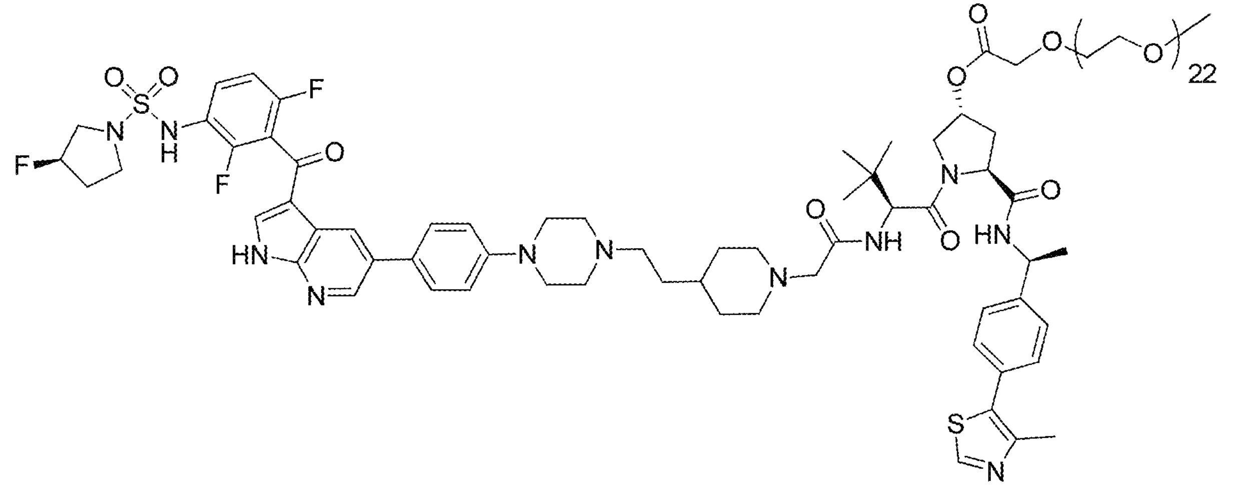
Figure 2C:
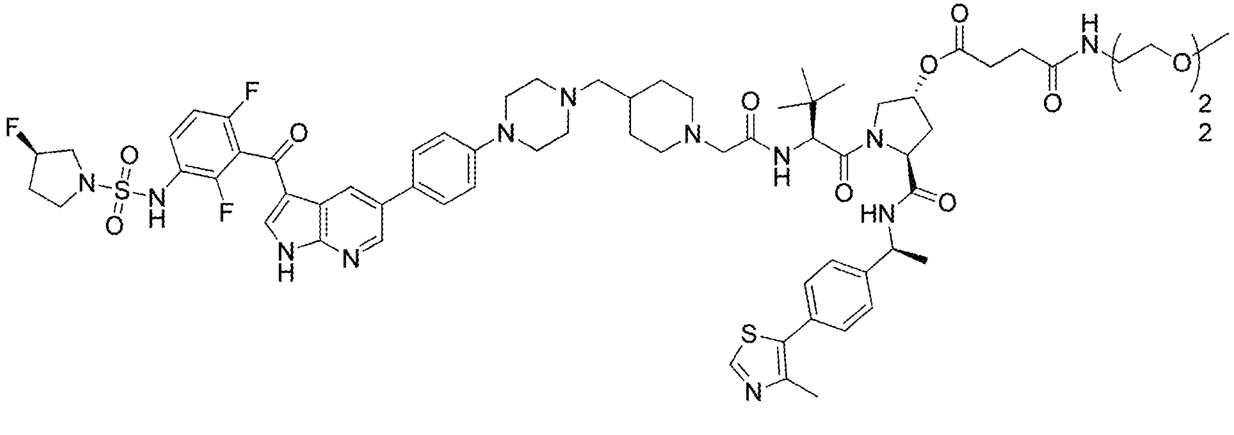
Figure 2C:
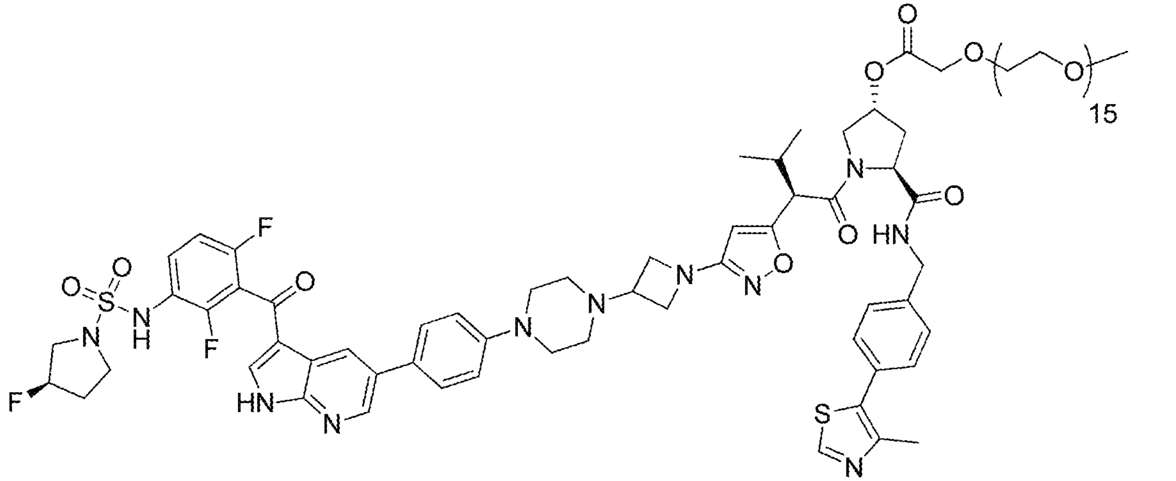
Figure 2C:
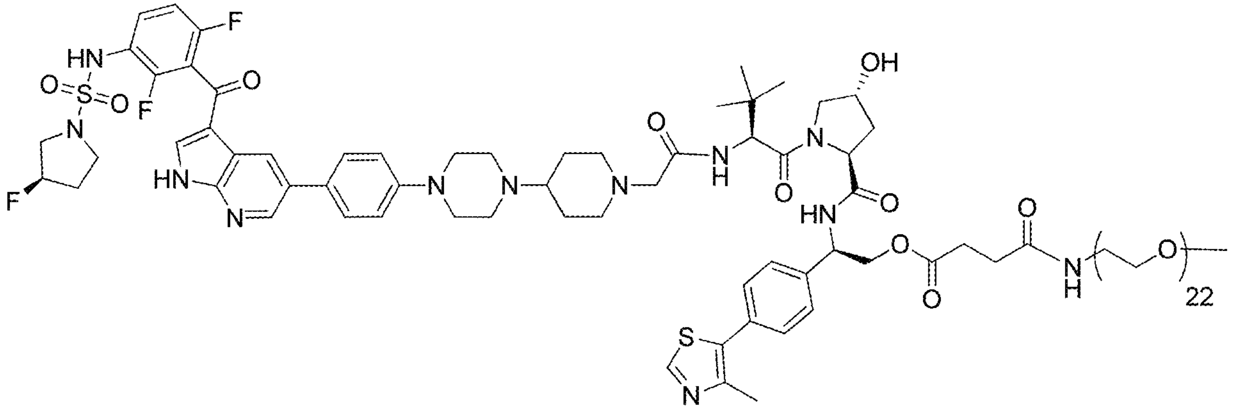
Figure 2C:
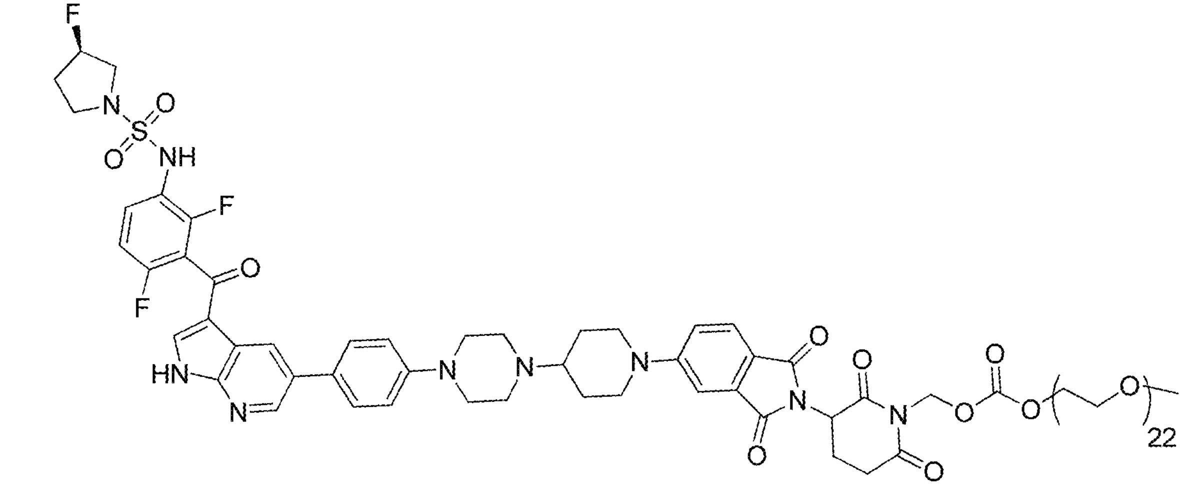
Figure 2C:
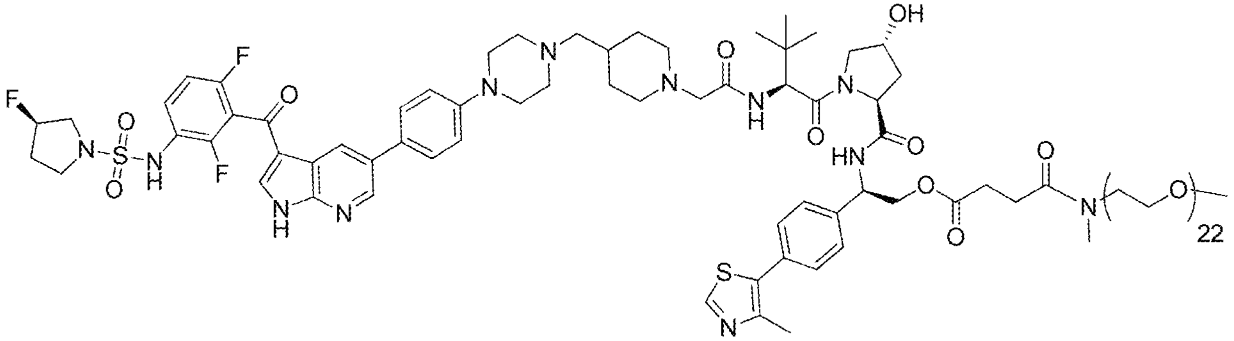
Figure 2C:
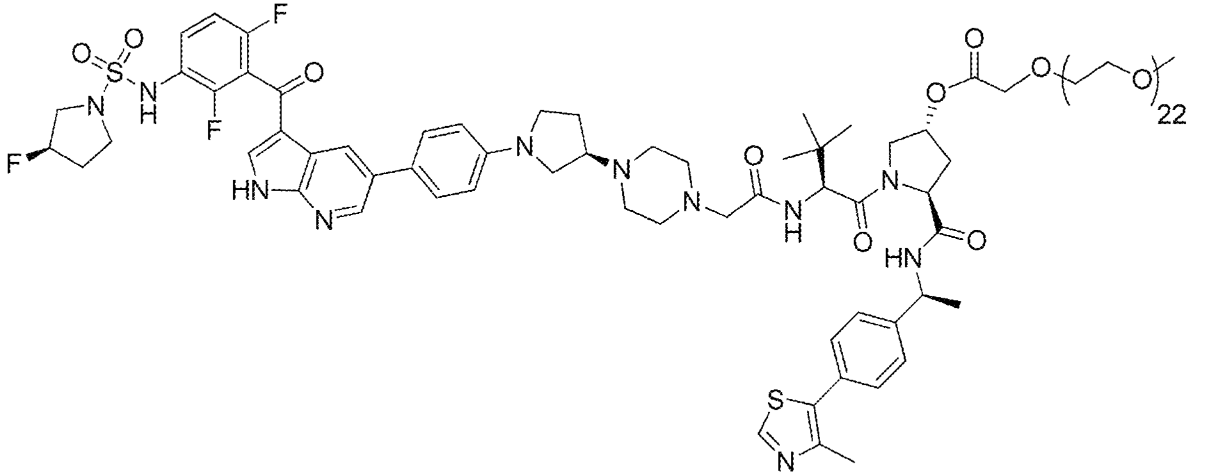
Figure 2C:
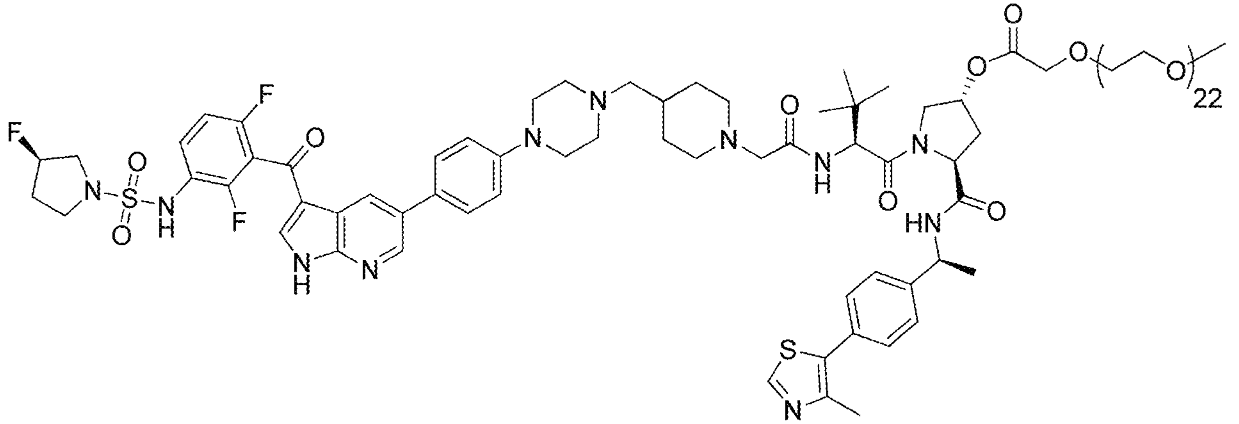
Figure 2C:
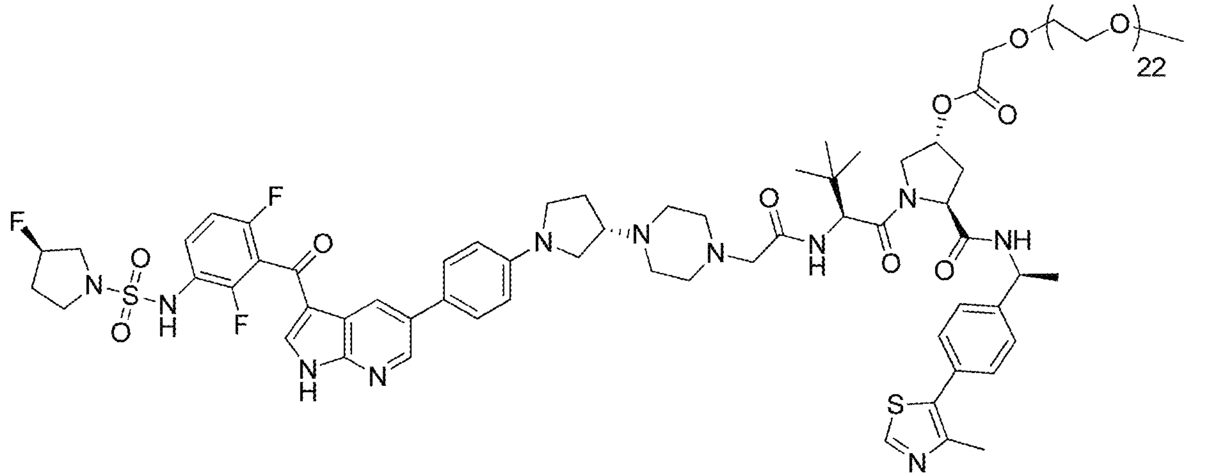
Figure 2C:
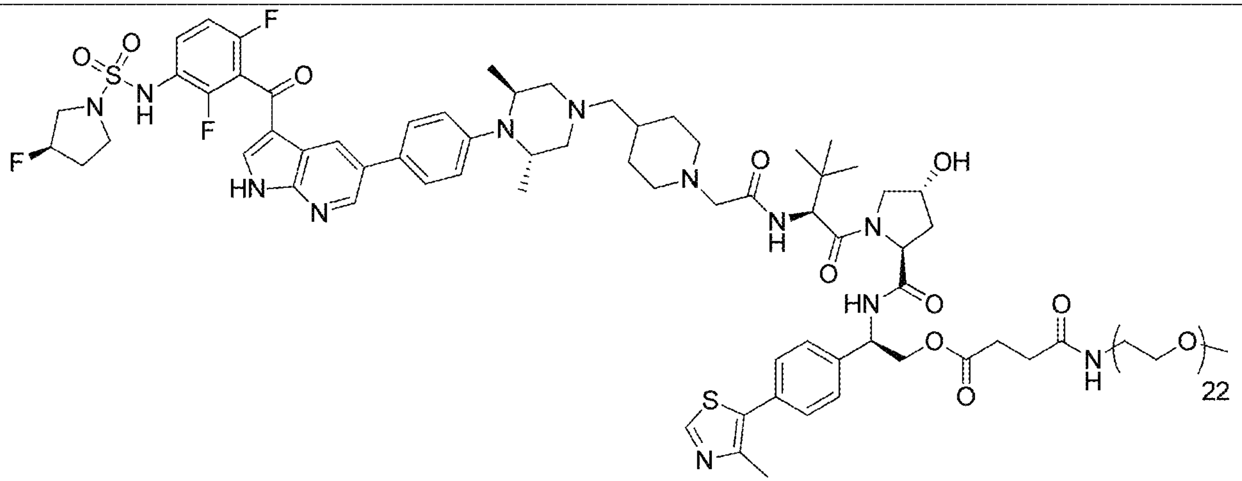
Figure 2C:
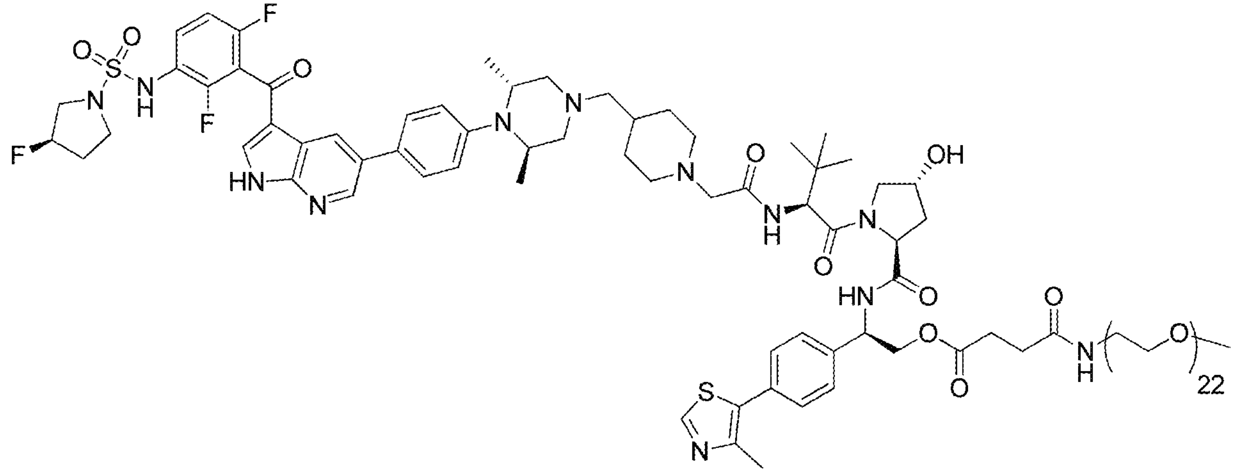
Figure 2C:
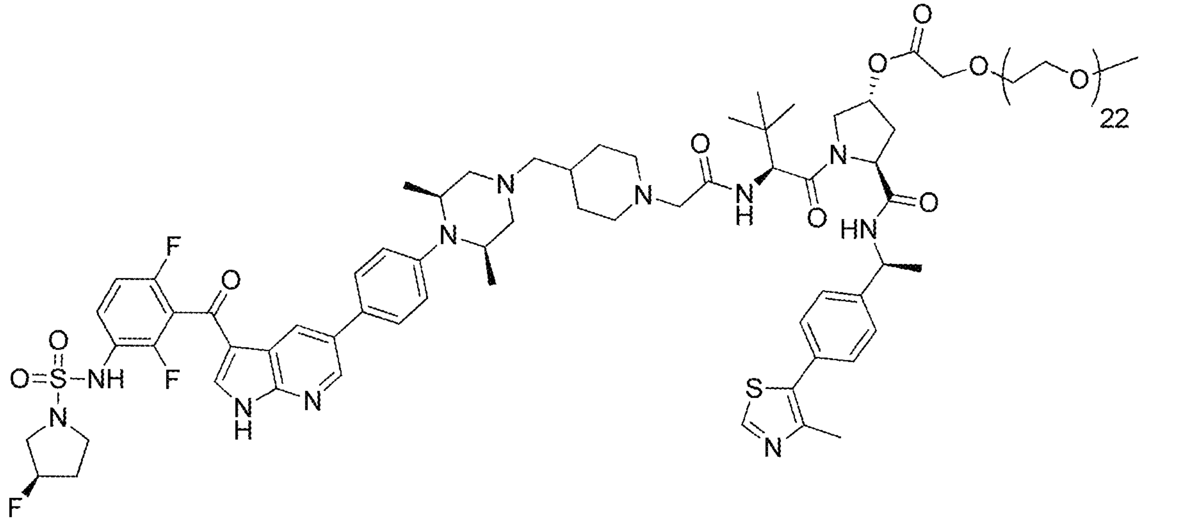
Figure 2C:
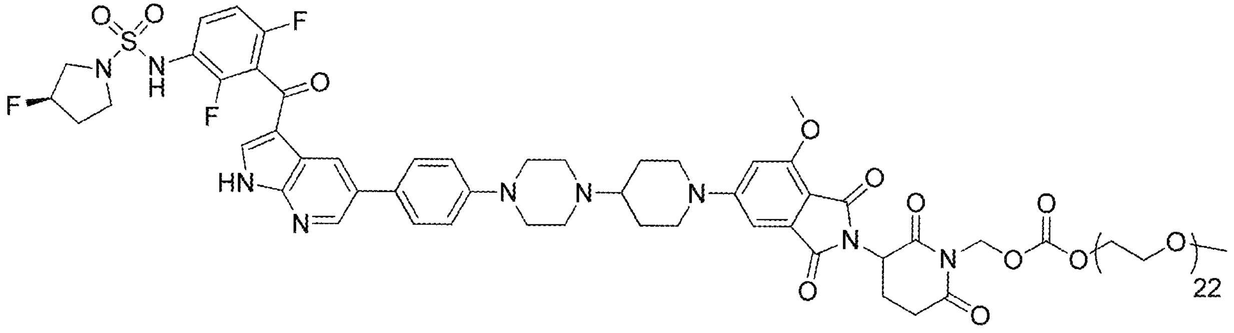
Figure 2C:
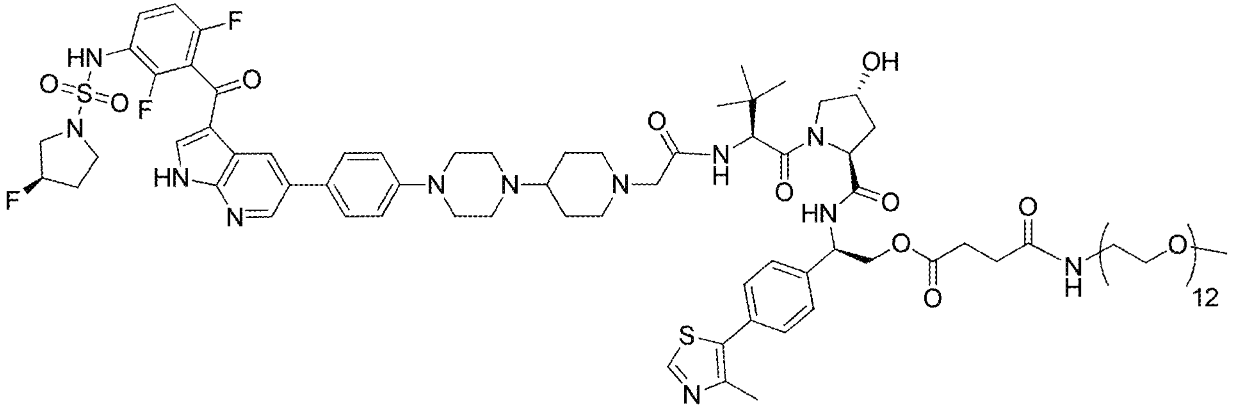
Figure 2C:
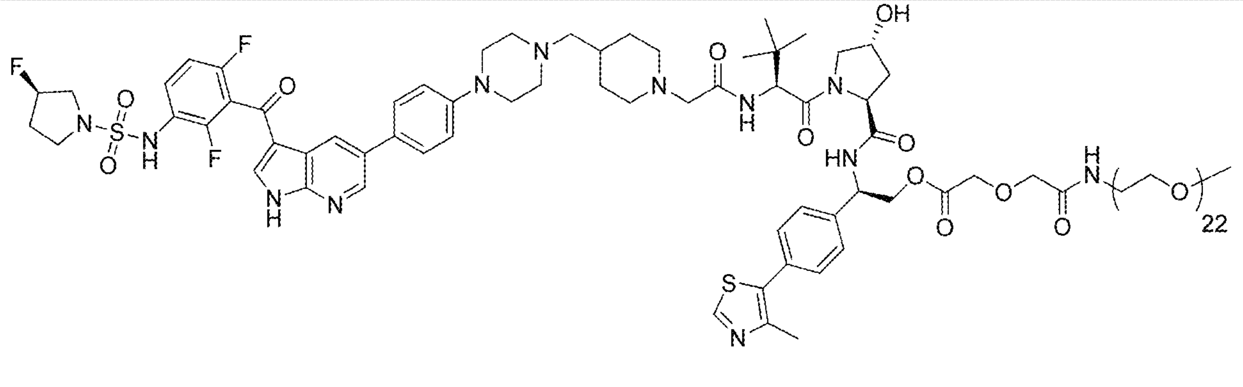
Figure 2C:
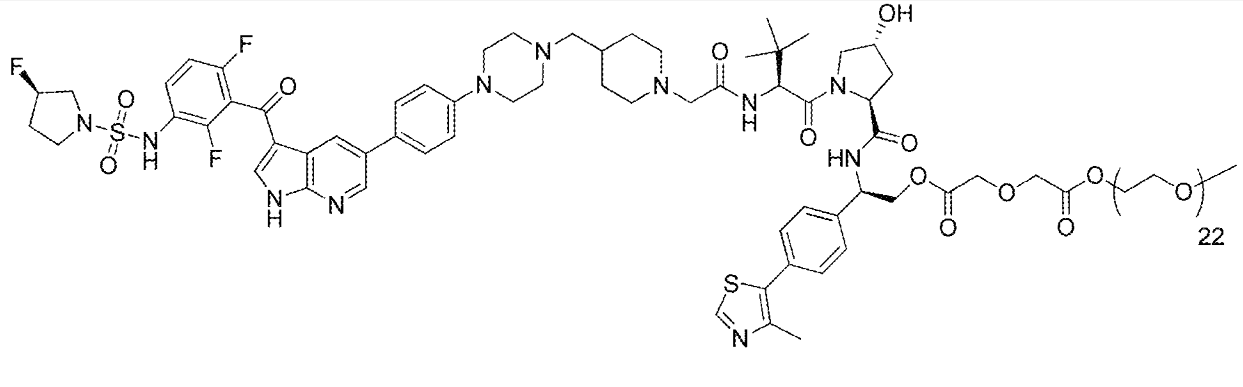
Figure 2C:
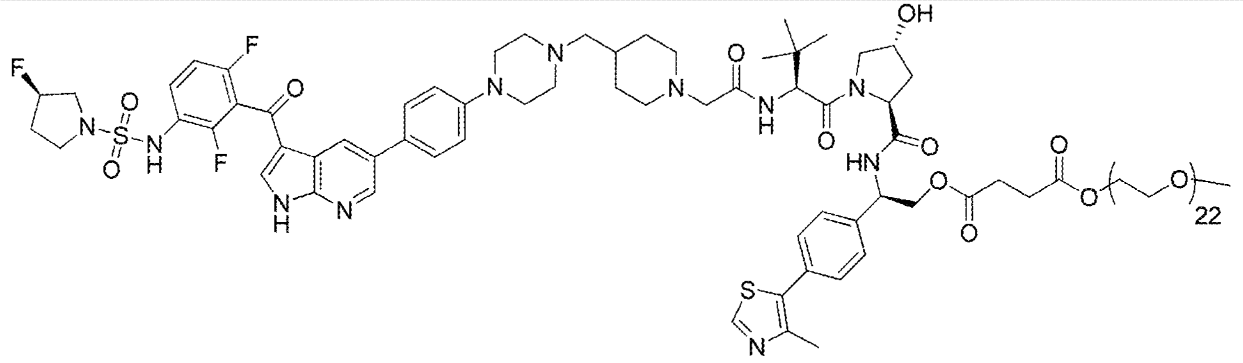
Figure 2C:
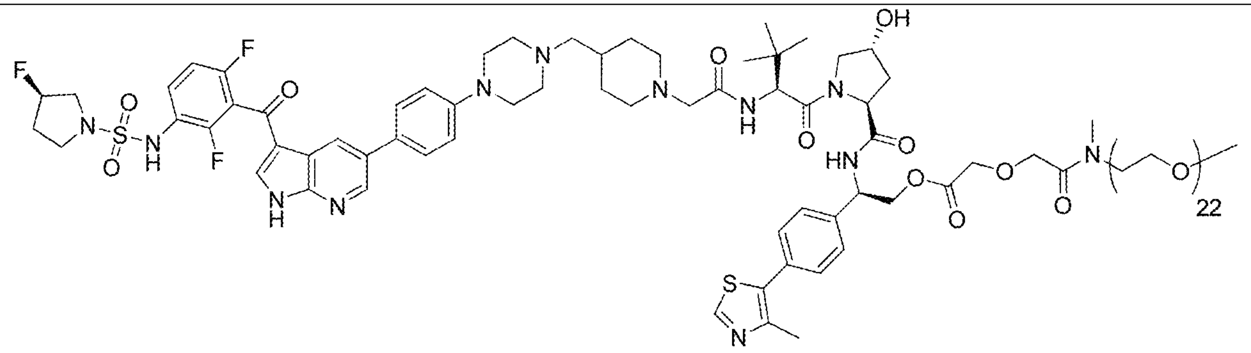
Figure 2C:
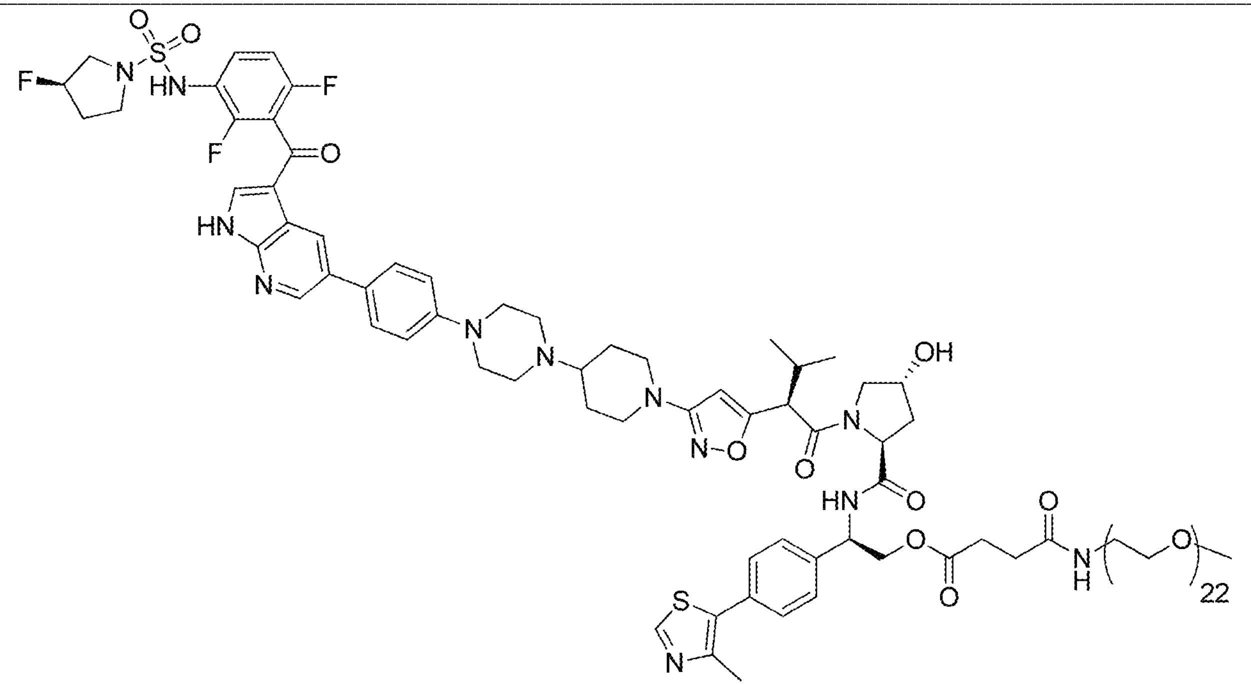
Figure 2C:
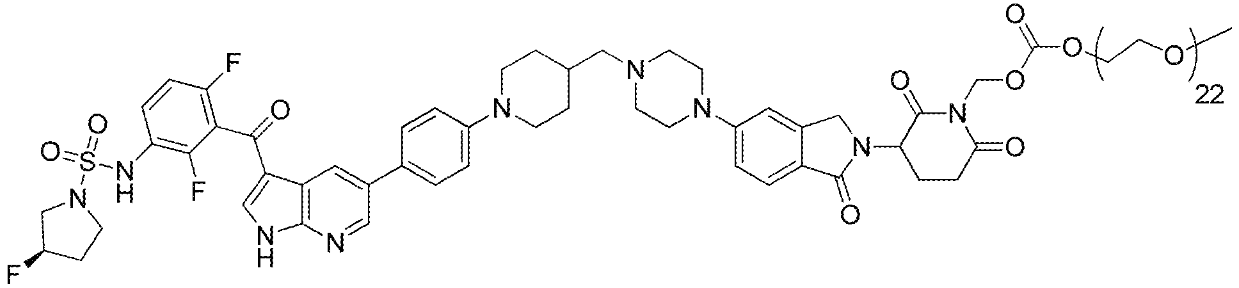
Figure 2C:
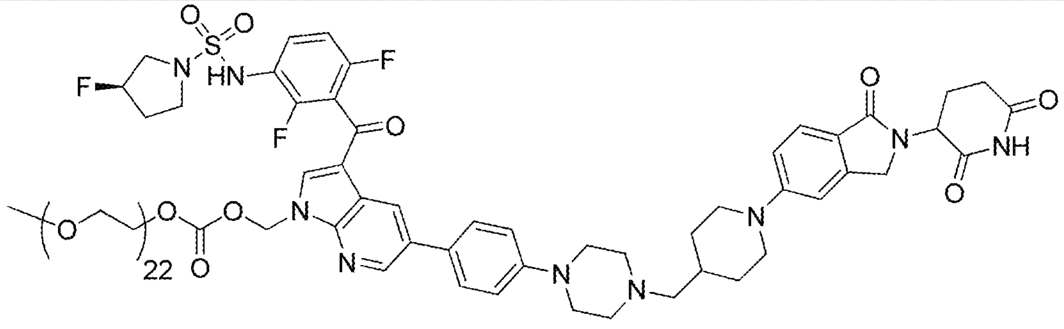
Figure 2C:
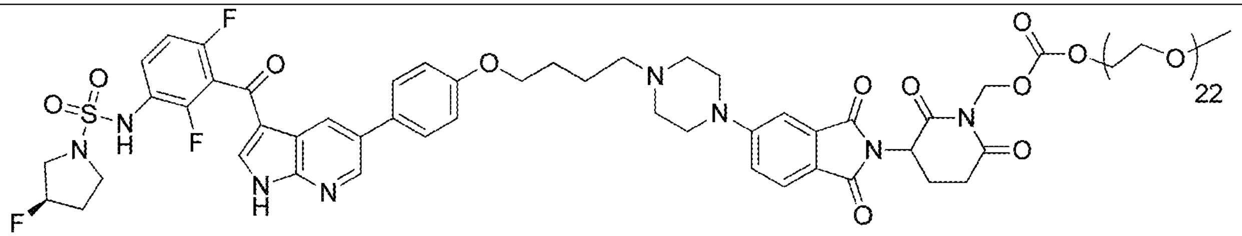
Figure 2C:
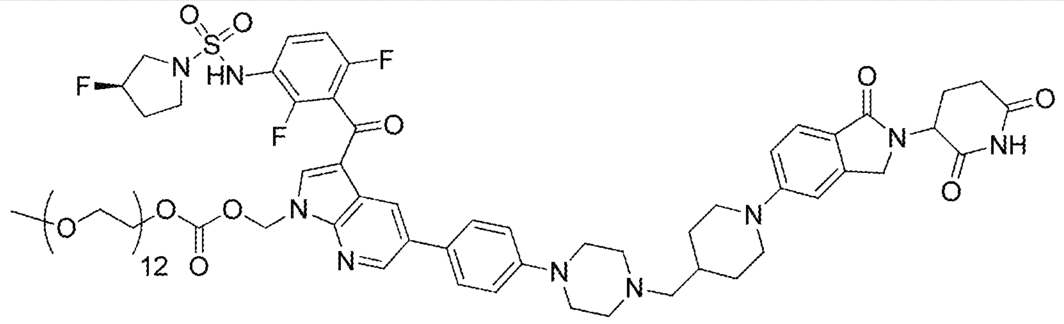
Figure 2C:
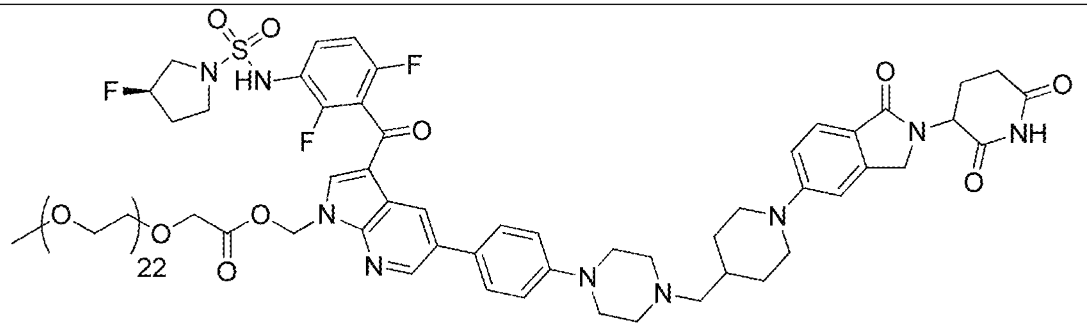
Figure 2C:
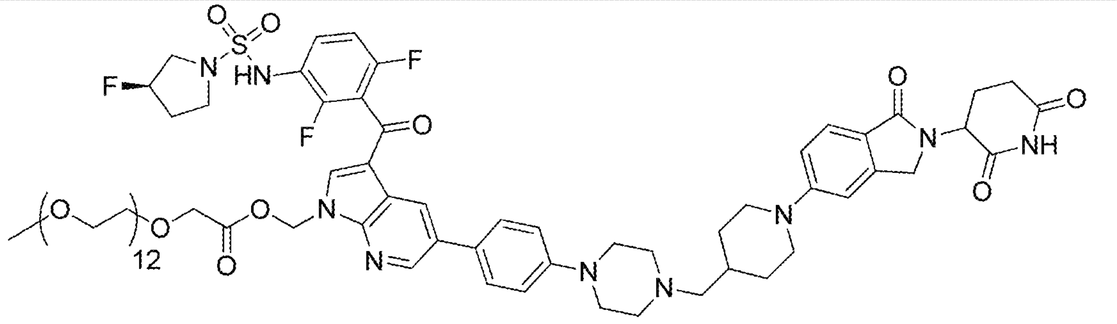
Figure 2C:
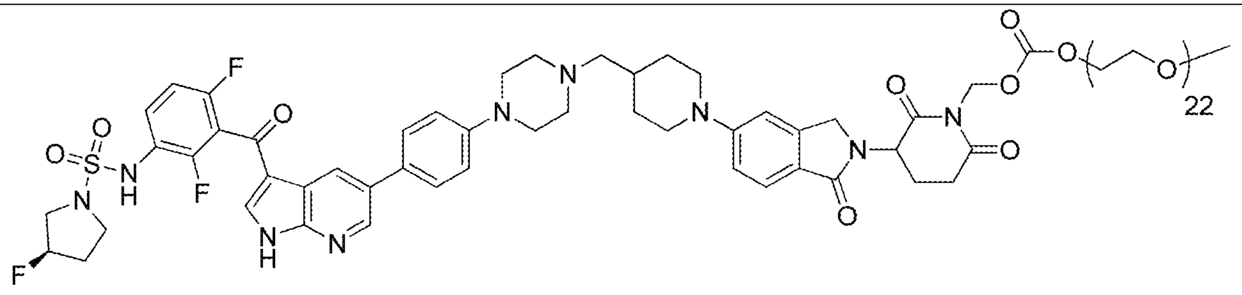
Figure 2C:
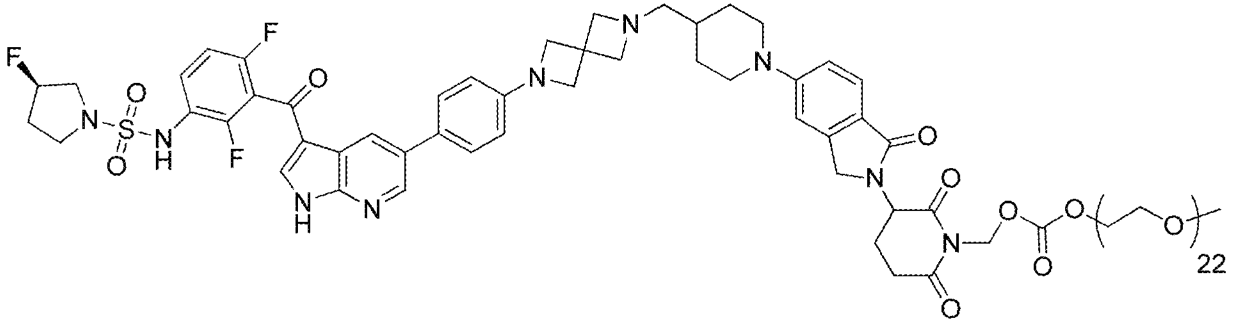
Figure 2C:
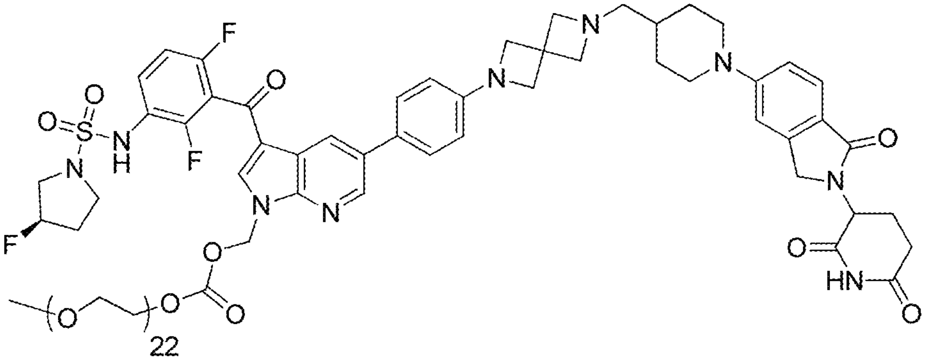
Figure 2C:
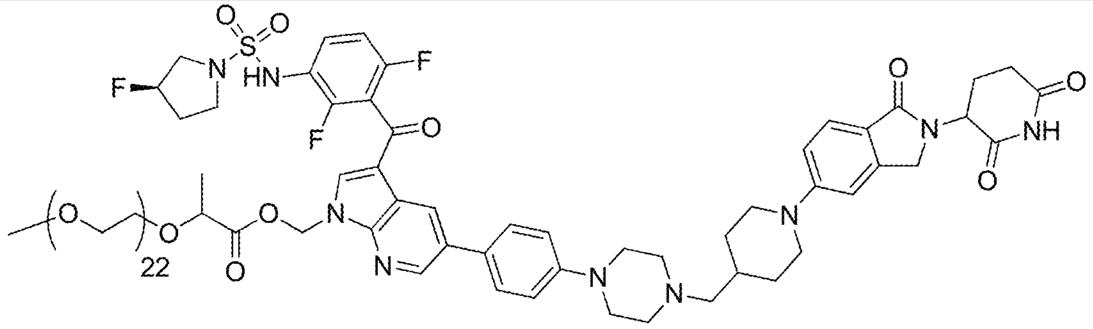
Figure 2C:
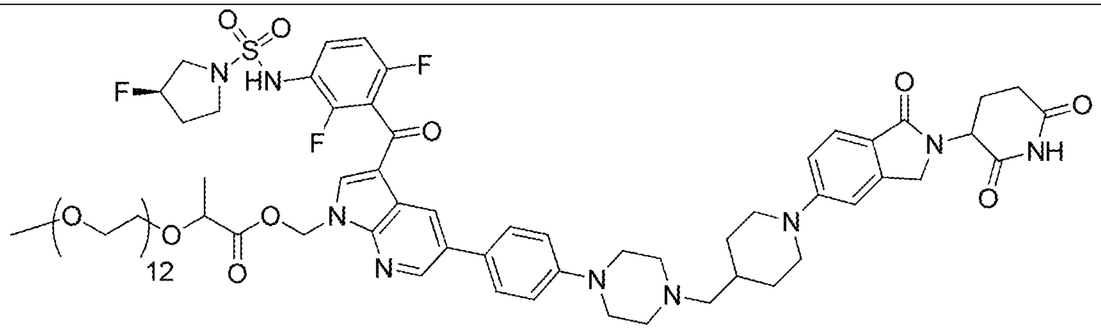
Figure 2C:
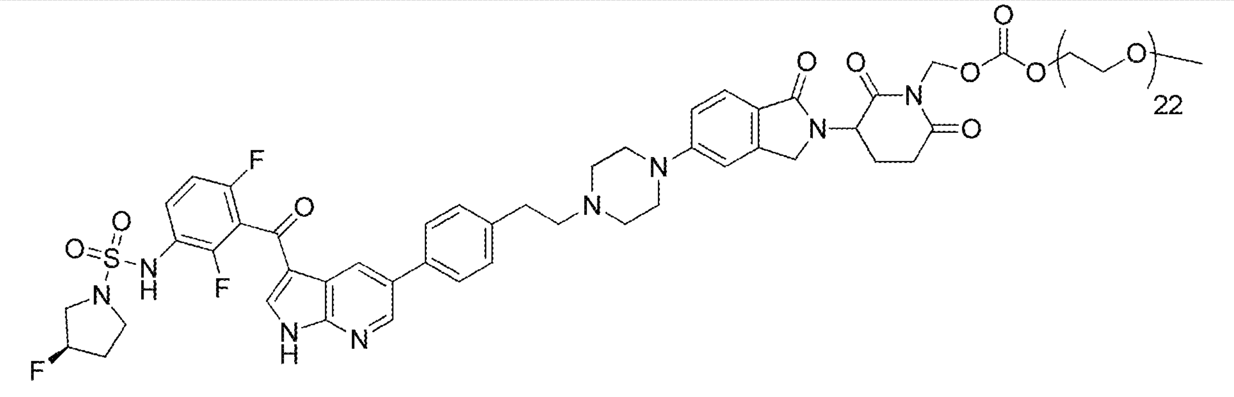
Figure 2C:
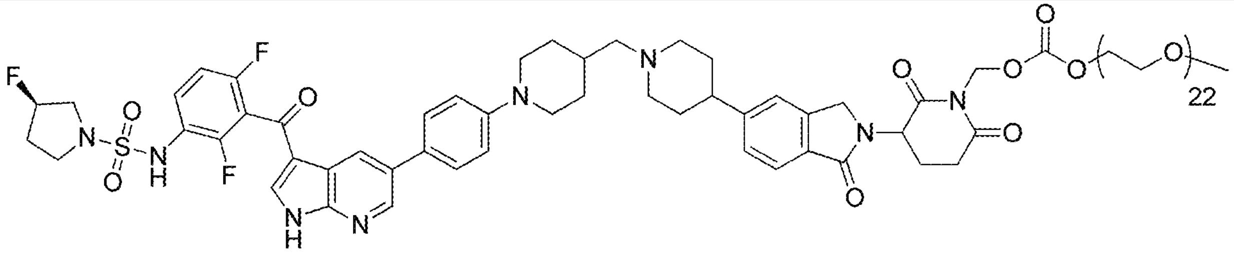
Figure 2C:
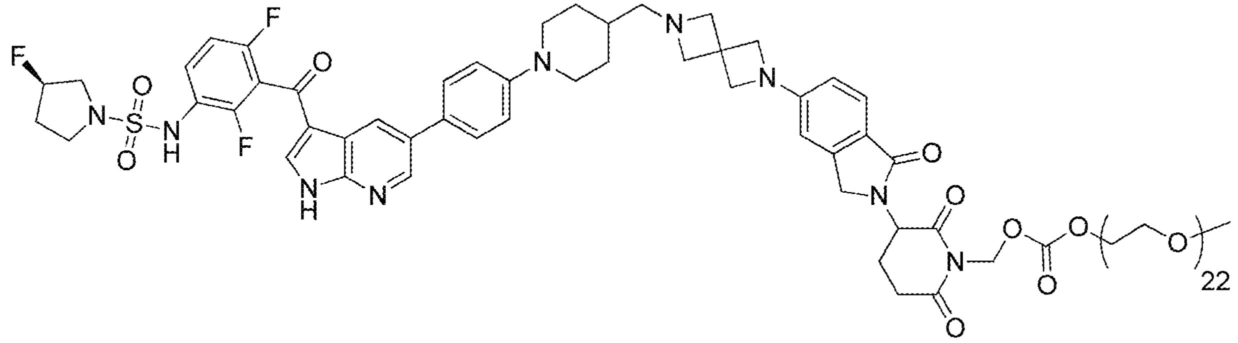
Figure 2C:
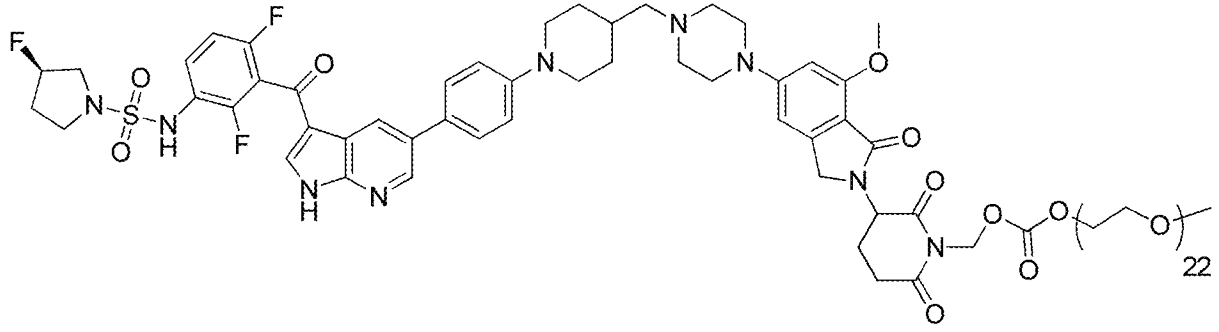
Figure 2C:
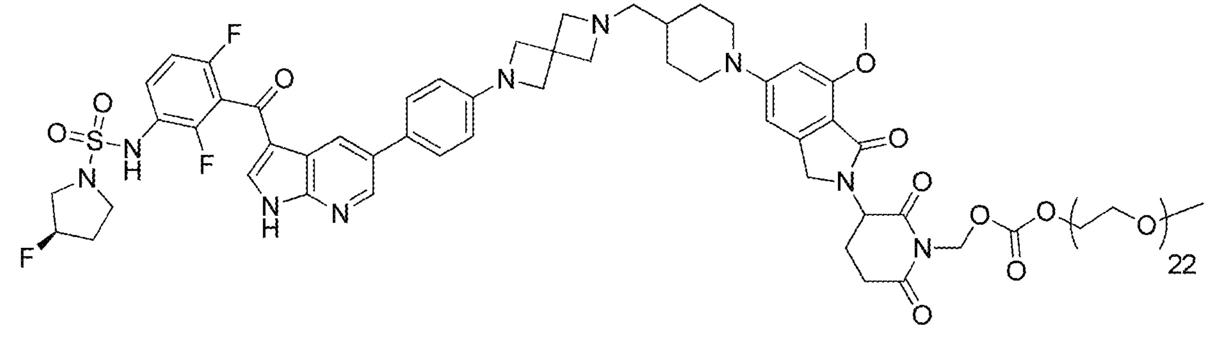
Figure 2C:
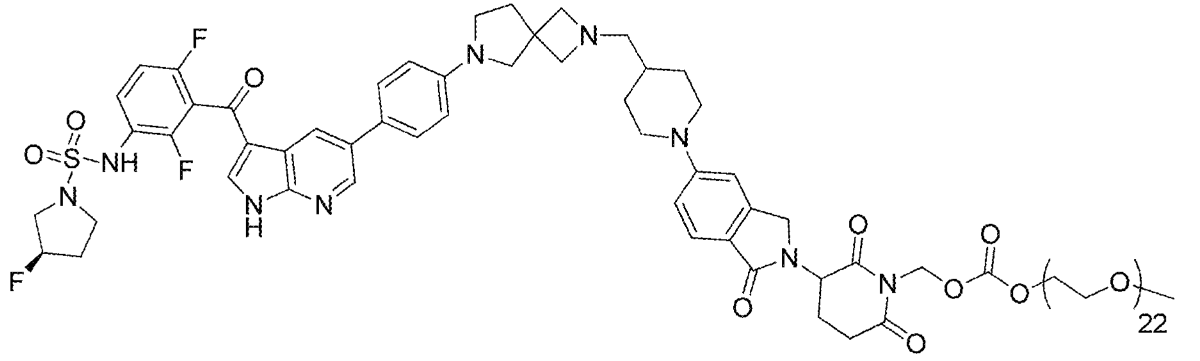
Figure 2C:
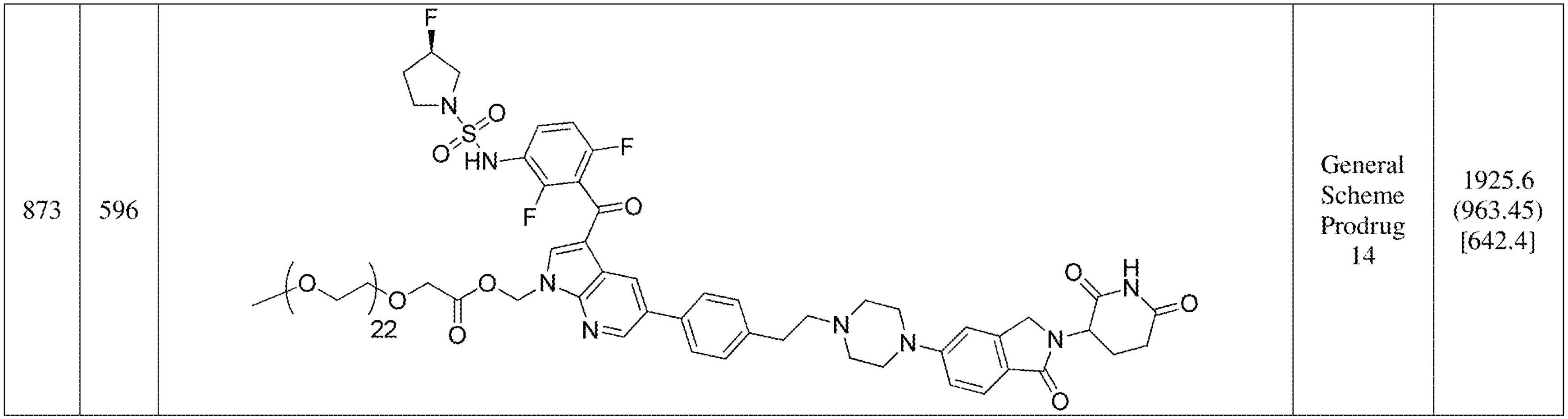
Figure 4:
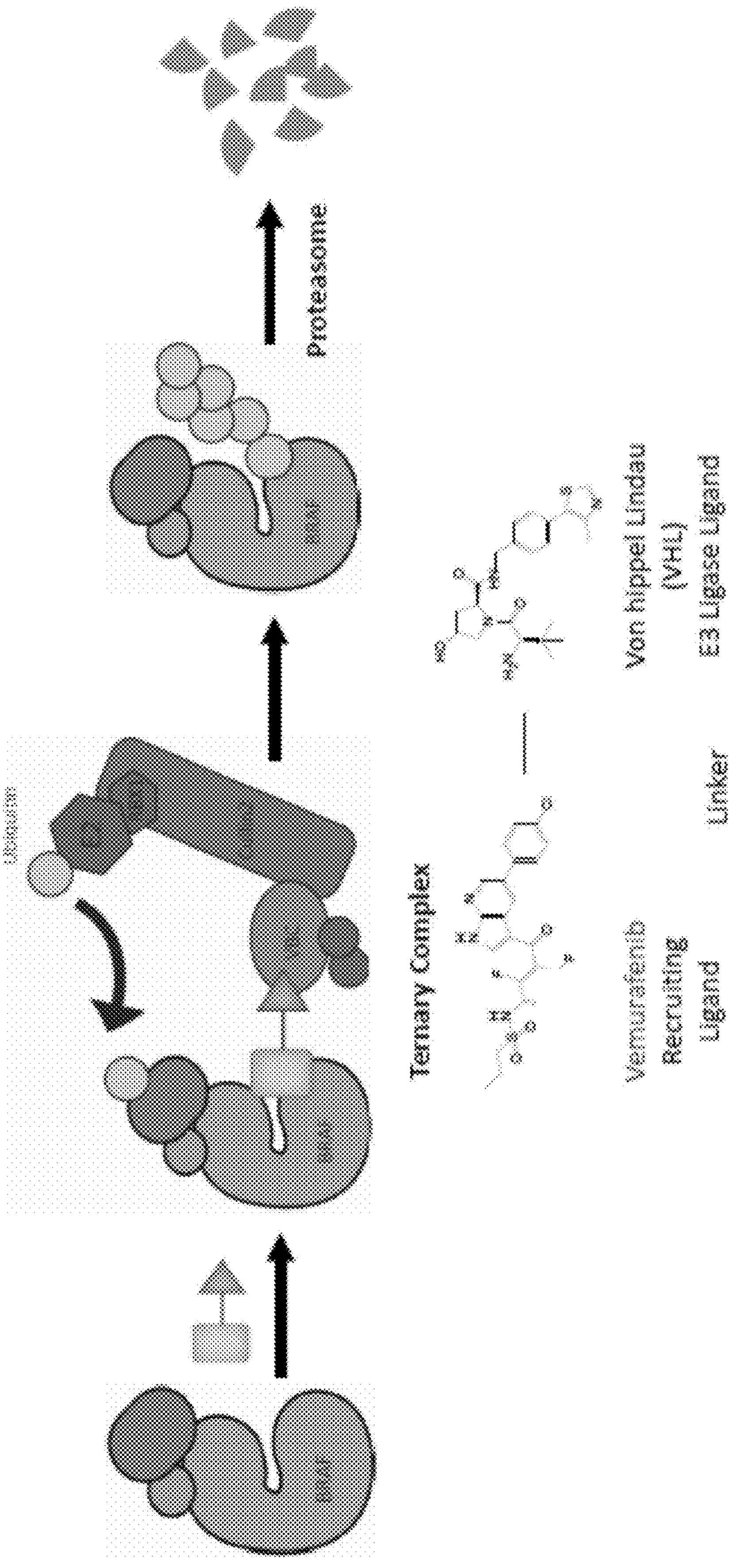
FIG. 4. Illustration of general principle of bifunctional compounds of the present disclosure.
Figure 5:
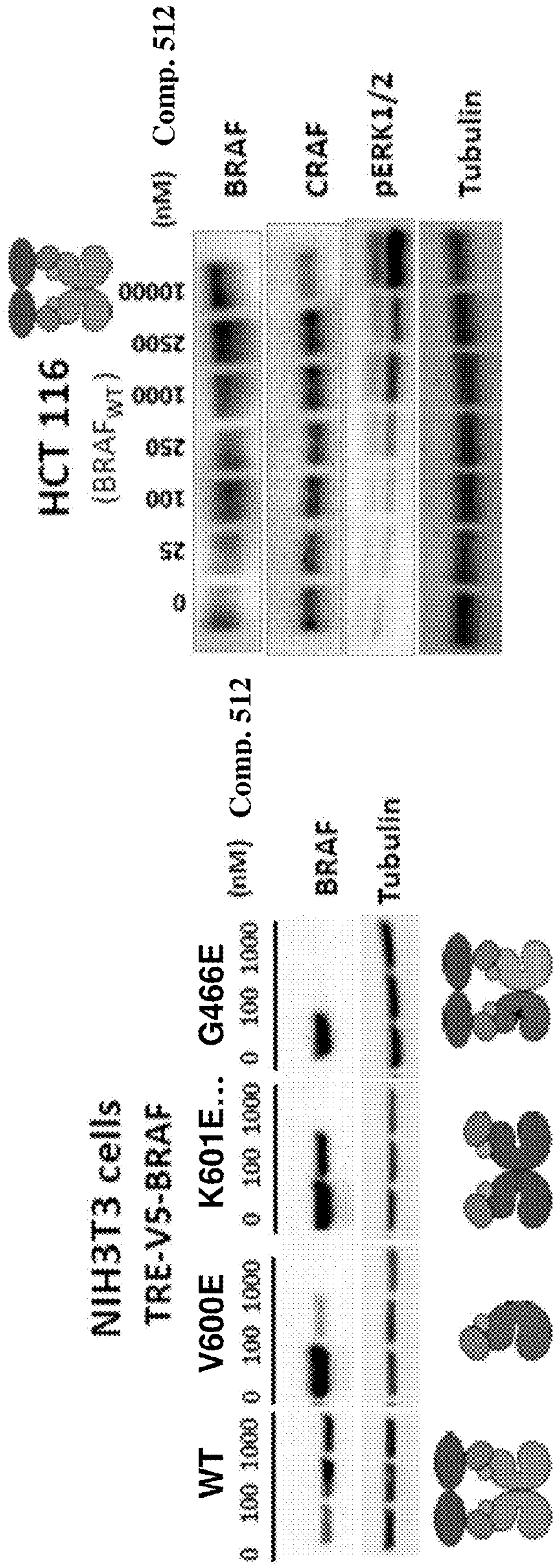
FIG. 5. Exemplary bifunctional compound of the present disclosure induces mutant selective degradation of BRAF.
Figure 6A:
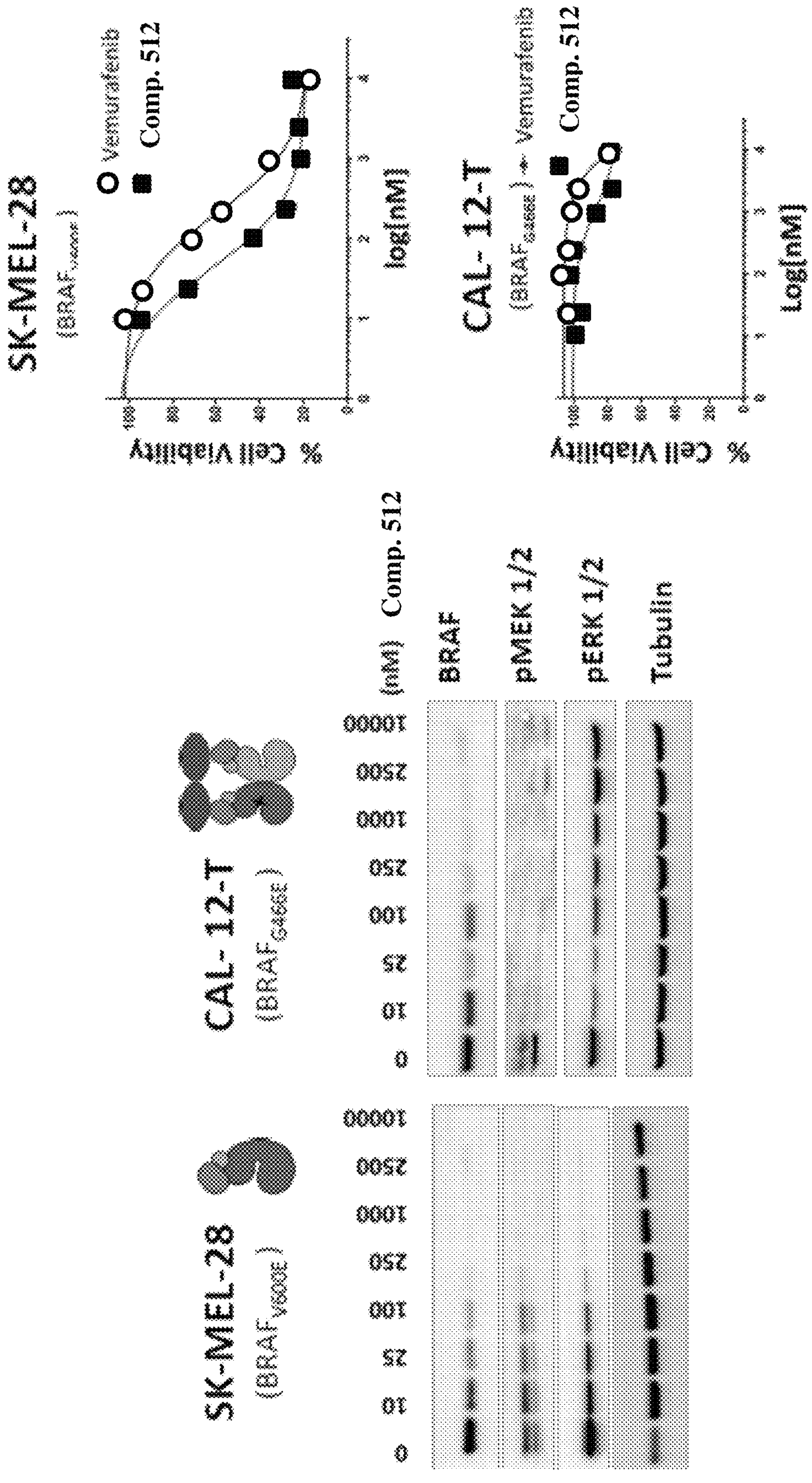
FIGS. 6A, 6B, and 6C. Exemplary bifunctional compound of the present disclosure induces mutant BRAF degradation, inhibit cell proliferation, and suppresses MAPK signaling, while sparing wild-type BRAF.
Figure 6B:
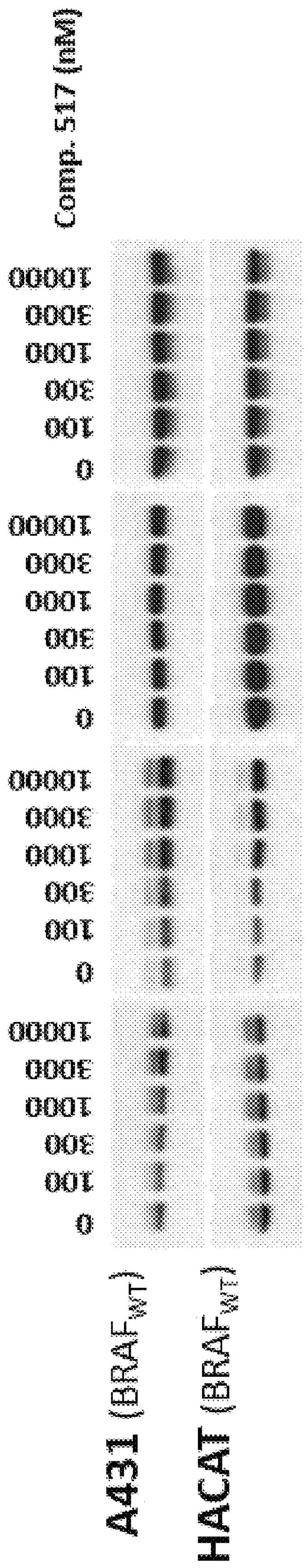
Figure 6C:
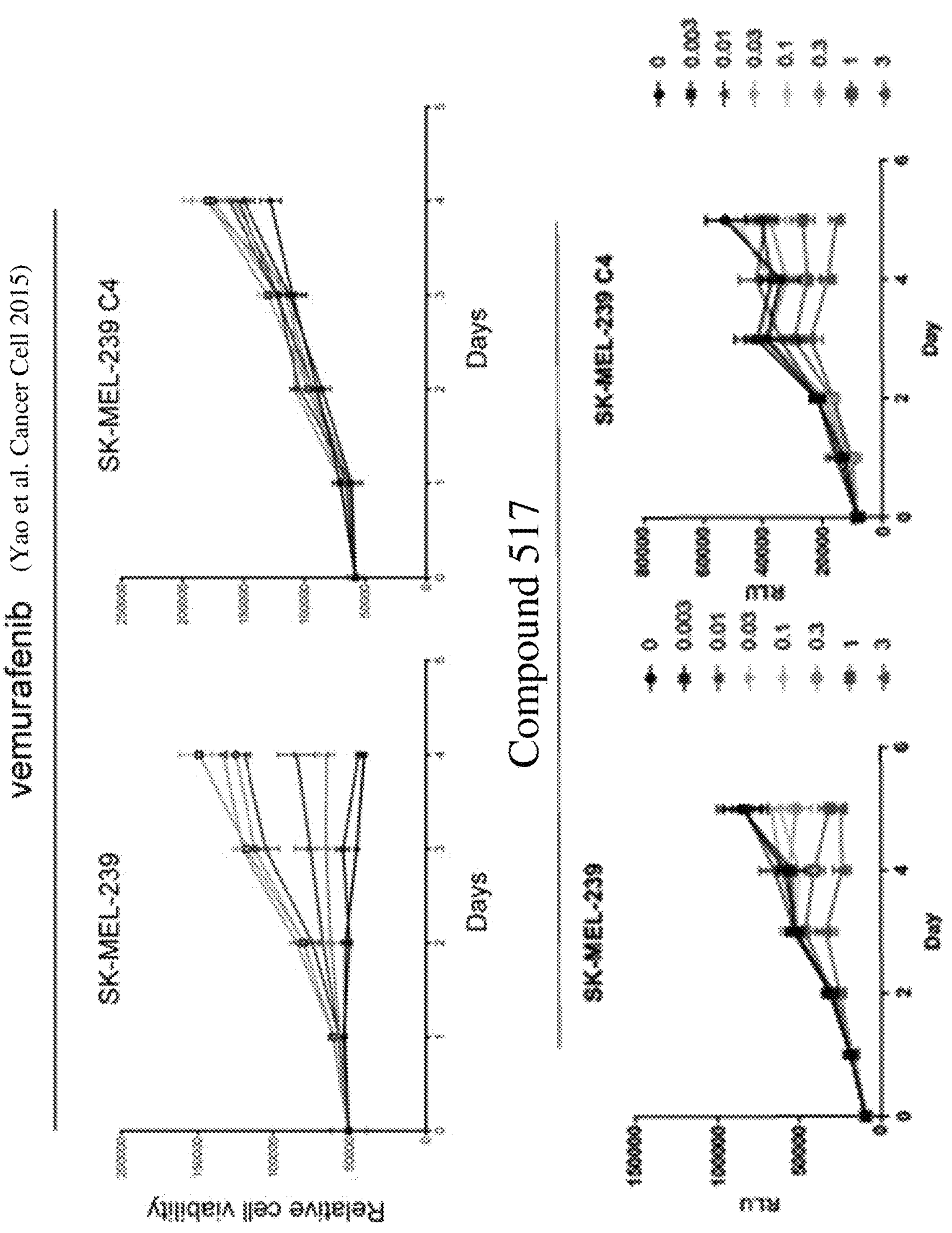
Figure 7:
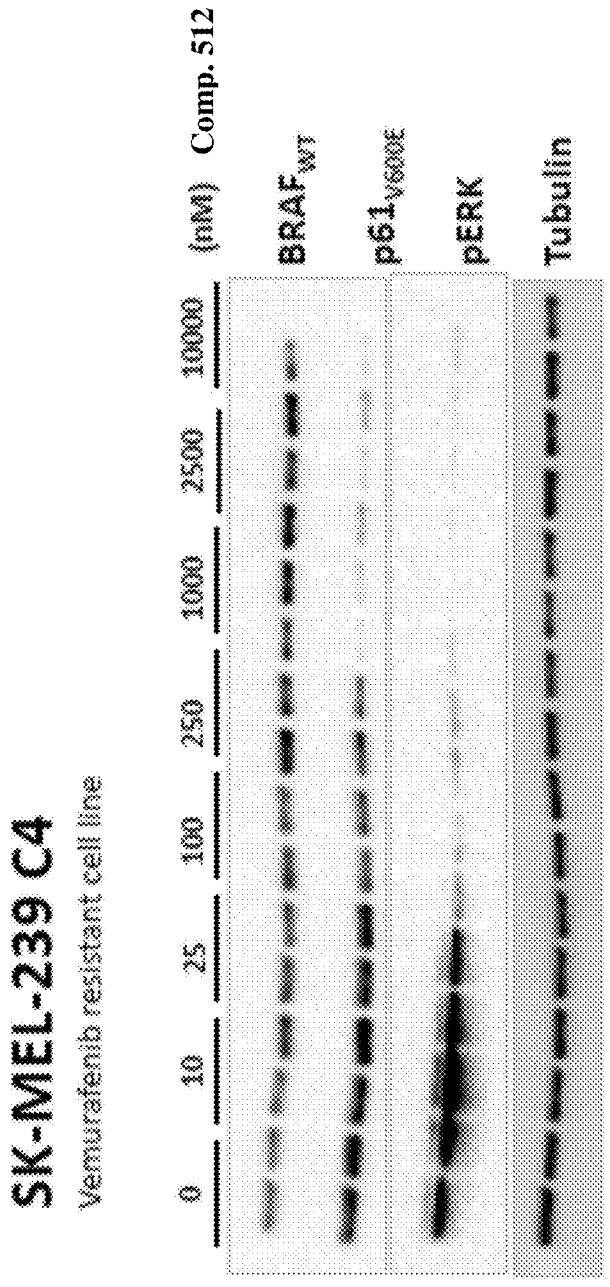
FIG. 7. Exemplary bifunctional compound of the present disclosure induces degradation of vemurafenib resistant mutant p61.
Figure 8A:
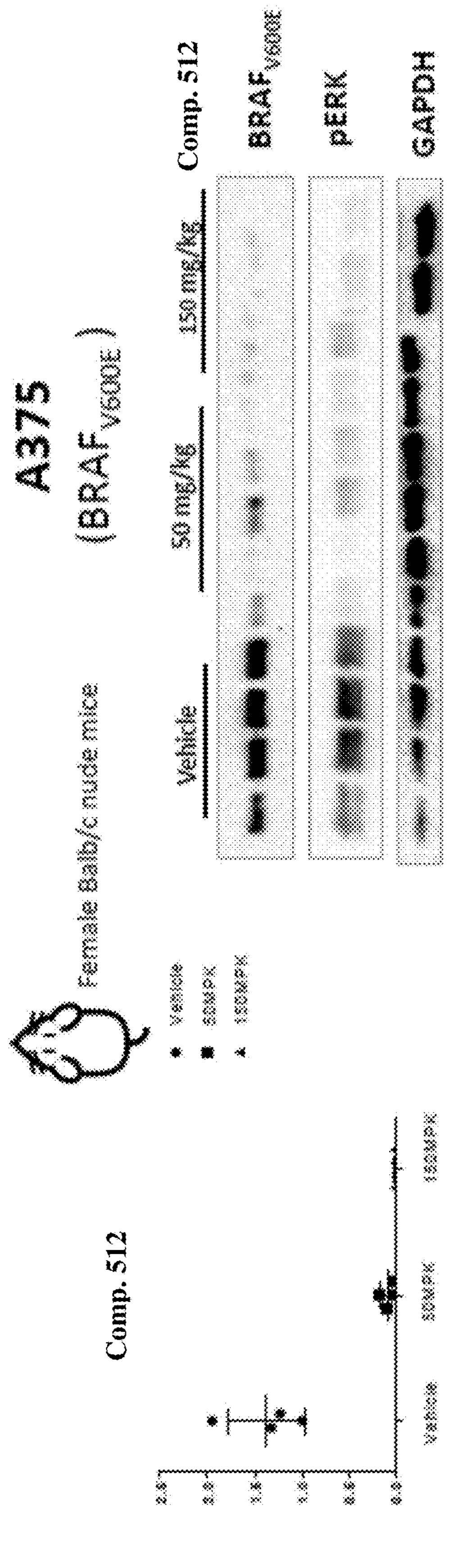
FIGS. 8A and 8B. Exemplary bifunctional compound of the present disclosure induces degradation of mutant BRAF in vivo (a) and decreases tumor volume (B).
Figure 8B:
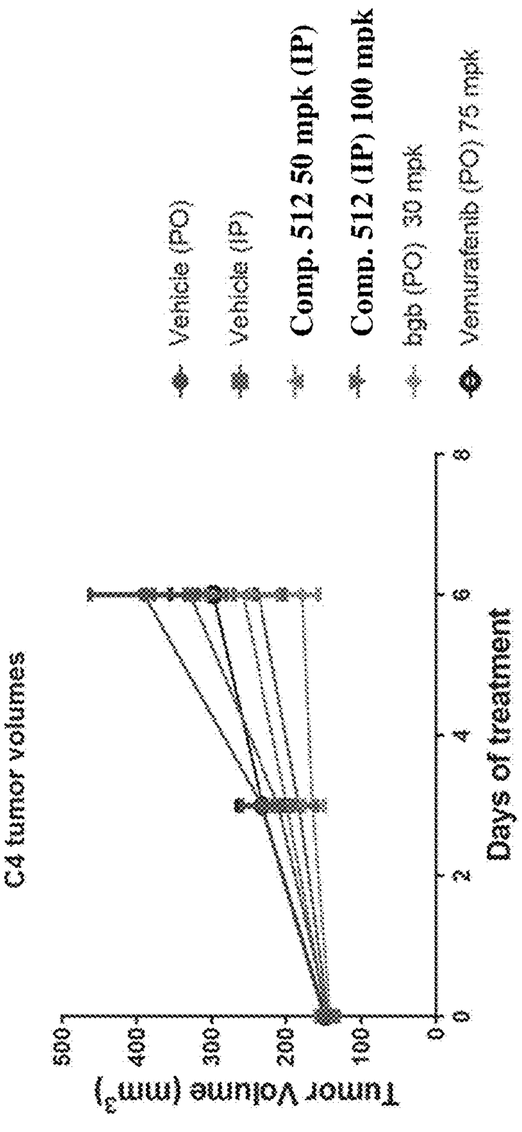
Figure 9A:
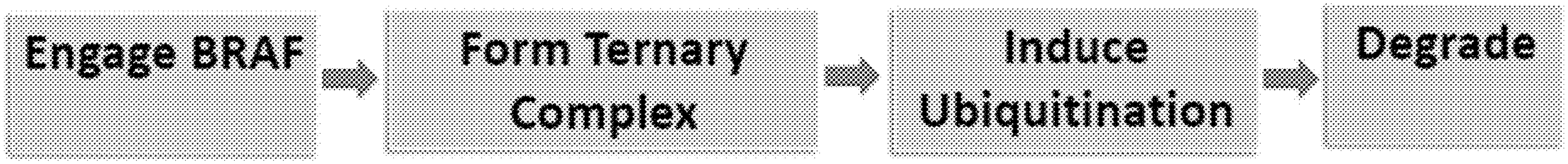
FIGS. 9A and 9B. What mechanism underlies the selectivity of the exemplary bifunctional compound.
Figure 9A:
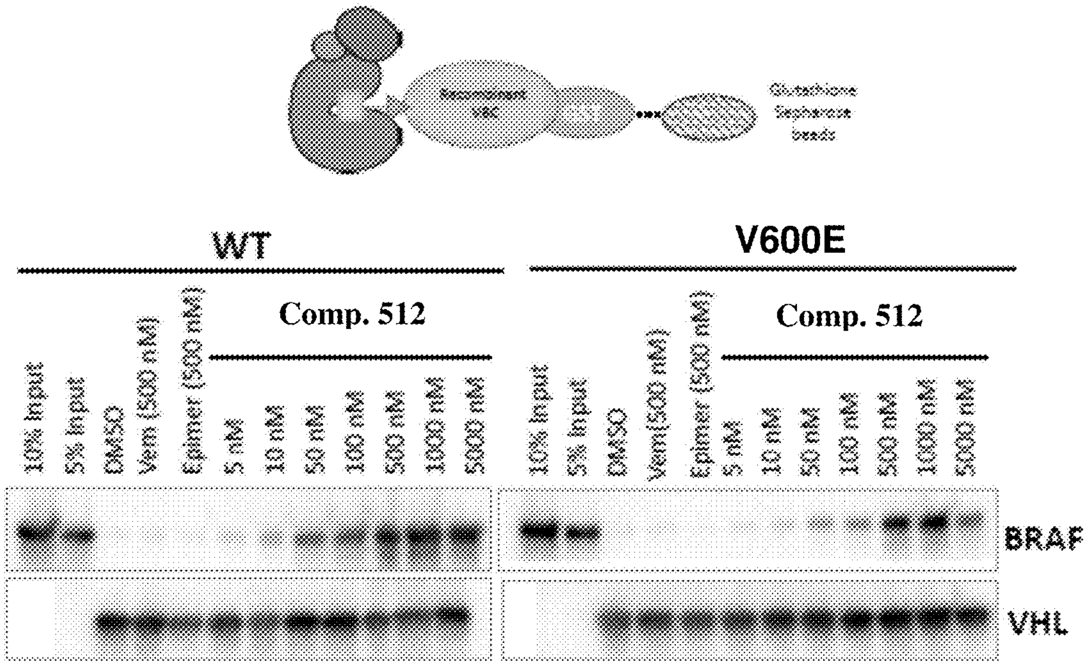
Figure 9B:
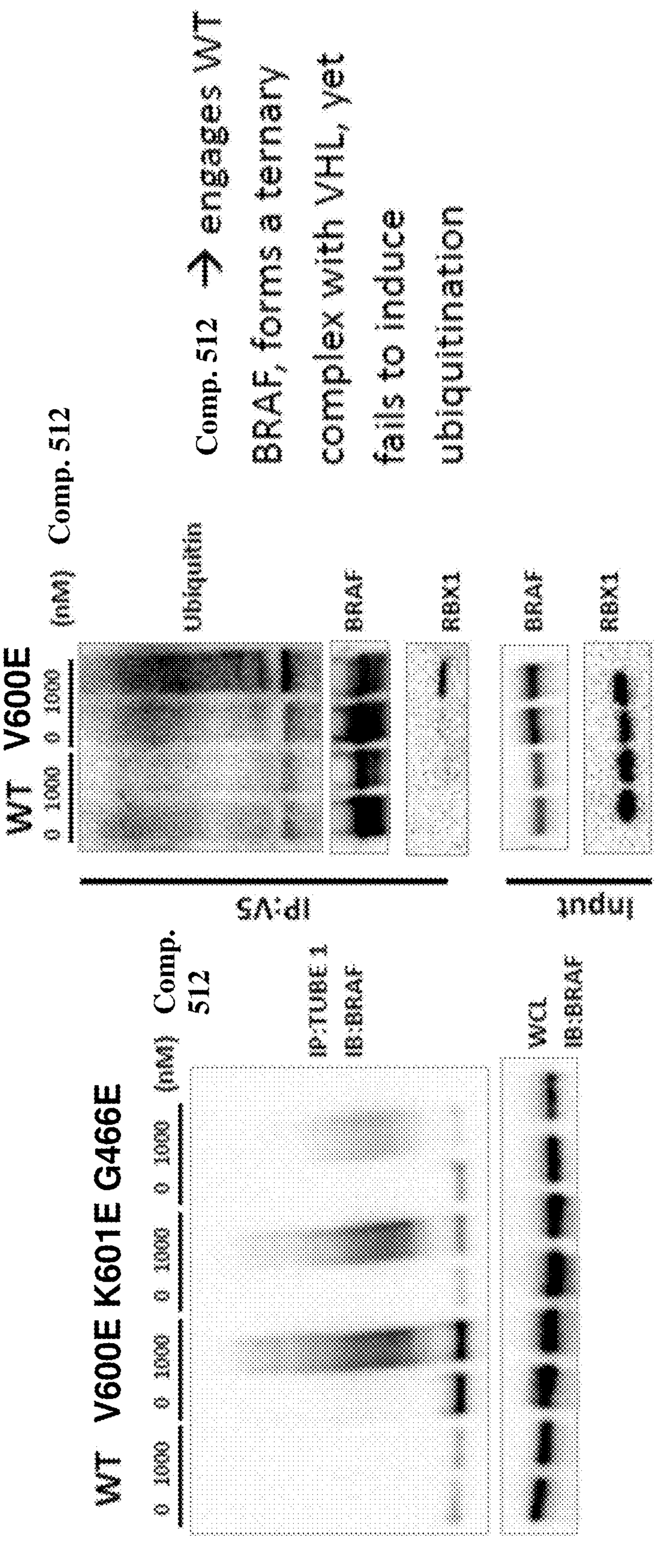
Figure 10:
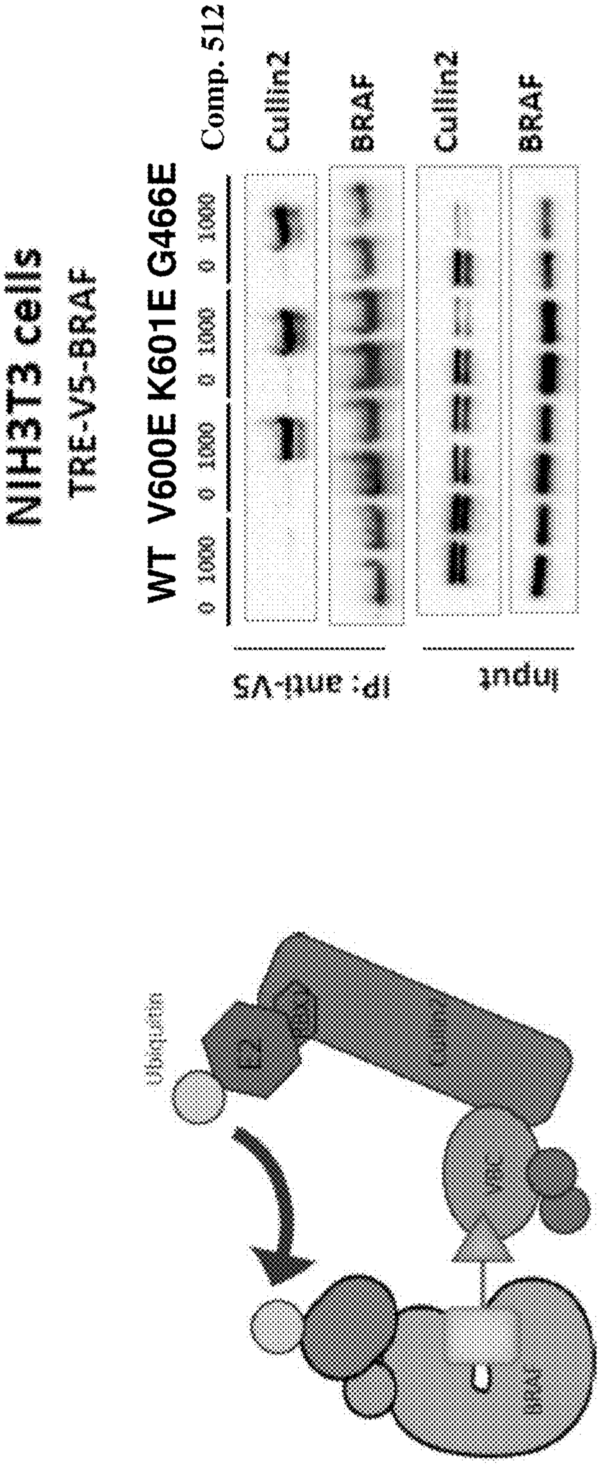
FIG. 10. Wild-type BRAF is unable to recruit Cullin 2 (active E3 ligase).

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHF, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

PTM-L-ULM (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. Lor example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-ILM (B)

PTM-CLM (C)

PTM-VLM (D)

PTM-MLM (E)

In certain embodiments, the bifunctional compound further comprises a chemical linker ("L"). For example, the bifunctional compound can be depicted as:

PTM-L-ILM (F)

PTM-L-CLM (G)

PTM-L-VLM (H)

PTM-L-MLM (I)

wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2E3 ubiquitin ligase) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 μM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ILMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C═C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a $-(CH_2)_n-$ group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted $—N(C_0-C_6$ alkyl)C(O)(O—$C_1-C_6$ alkyl) group (which may be optionally substituted with a polyethylene glycol chain to which is further bound an alkyl group containing a single halogen, preferably chlorine substituent), hydrazine, amido, which is preferably substituted with one or two $C_1-C_6$ alkyl groups (including a carboxamide which is optionally substituted with one or two $C_1-C_6$ alkyl groups), alkanol (preferably, $C_1-C_6$ alkyl or aryl), or alkanoic acid (preferably, $C_1-C_6$ alkyl or aryl). Substituents according to the present disclosure may include, for example $—SiR_1R_2R_3$ groups where each of $R_1$ and $R_2$ is as otherwise described herein and $R_3$ is H or a $C_1-C_6$ alkyl group, preferably $R_1$, $R_2$, $R_3$ in this context is a $C_1-C_3$ alkyl group (including an isopropyl or t-butyl group). Each of the above-described groups may be linked directly to the substituted moiety or alternatively, the substituent may be linked to the substituted moiety (preferably in the case of an aryl or heterarylmoiety) through an optionally substituted $—(CH_2)_m—$ or alternatively an optionally substituted $—(OCH_2)_{m'}$, $—(OCH_2CH_2)_m—$ or $—(CH_2CH_2O)_m—$ group, which may be substituted with any one or more of the above-described substituents. Alkylene groups $—(CH_2)_m—$ or $—(CH_2)_n—$ groups or other chains such as ethylene glycol chains, as identified above, may be substituted anywhere on the chain. Preferred substitutents on alkylene groups include halogen or $C_1-C_6$ (preferably $C_1-C_3$) alkyl groups, which may be optionally substituted with one or two hydroxyl groups, one or two ether groups (0-$C_1-C_6$ groups), up to three halo groups (preferably F), or a sideshain of an amino acid as otherwise described herein and optionally substituted amide (preferably carboxamide substituted as described above) or urethane groups (often with one or two $C_0-C_6$ alkyl substitutents, which group(s) may be further substituted). In certain embodiments, the alkylene group (often a single methylene group) is substituted with one or two optionally substituted $C_1-C_6$ alkyl groups, preferably $C_1-C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1-C_6$ alkyl, $C_1-C_6$ alkoxy, halogen, amido, carboxamido, sulfone, including sulfonamide, keto, carboxy, $C_1-C_6$ ester (oxyester or carbonylester), $C_1-C_6$keto, urethane $—O—C(O)—NR_1R_2$ or $—N(R_1)—C(O)—O—R_1$, nitro, cyano and amine (especially including a $C_1-C_6$ alkyl-cnc-$NR_1R_2$, a mono- or di-$C_1-C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, $—(CH_2)_m—$ (here, m and n are in context, 1, 2, 3, 4, 5 or 6), —S—, —S(O)—, $SO_2—$ or —NH—C(O)—NH—, $—(CH_2)_nOH$, $—(CH_2)_nSH$, $—(CH_2)_nCOOH$, $C_1-C_6$ alkyl, $—(CH_2)_nO—(C_1-C_6$ alkyl), $—(CH_2)_nC(O)—(C_1-C_6$ alkyl), $—(CH_2)_nOC(O)—(C_1-C_6$ alkyl), $—(CH_2)_nC(O)O—(C_1-C_6$ alkyl), $—(CH_2)_nNHC(O)—R_1$, $—(CH_2)_nC(O)—NR_1R_2$, $—(OCH_2)_nOH$, $—(CH_2O)_nCOOH$, $C_1-C_6$ alkyl, $—(OCH_2)_nO—(C_1-C_6$ alkyl), $—(CH_2O)_nC(O)—(C_1-C_6$ alkyl), $—(OCH_2)_nNHC(O)—R_1$, $—(CH_2O)_nC(O)—NR_1R_2$, $—S(O)_2—R_S$, $—S(O)—R_S$ ($R_S$ is $C_1-C_6$ alkyl or a $—(CH_2)_{m'}NR_1R_2$ group), $NO_2$, CN or halogen (F, Cl, Br, I, preferably F or Cl), depending on the context of the use of the substituent. $R_1$ and $R_2$ are each, within context, H or a $C_1-C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1-C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group $O—C(O)—NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: $-(CH_2)_nOH$, $-(CH_2)_n-O-(C_1\text{-}C_6)$alkyl, $-(CH_2)_n-O-(CH_2)_n-(C_1\text{-}C_6)$alkyl, $-(CH_2)_n-C(O)(C_0\text{-}C_6)$ alkyl, $-(CH_2)_n-C(O)O(C_0\text{-}C_6)$ alkyl, $-(CH_2)_n-OC(O)(C_0\text{-}C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

“Carboxyl” denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term “heteroaryl” or “hetaryl” can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1\text{-}C_6$ alkyl group or an optionally substituted $-(CH_2)_m-C(O)-O-C_1\text{-}C_6$ alkyl group), an optionally substituted pyridine (2-, 3, or 4-pyridine) or a group according to the chemical structure:

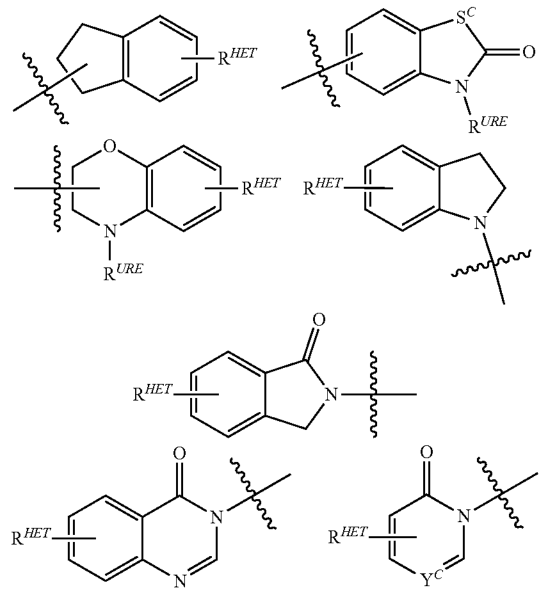

wherein:

$S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl).

The terms “aralkyl” and “heteroarylalkyl” refer to groups that comprise both aryl or, respectively, heteroaryl as well as alkyl and/or heteroalkyl and/or carbocyclic and/or heterocycloalkyl ring systems according to the above definitions.

The term “arylalkyl” as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-henzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyi, oxazolyi, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyi, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes hicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defnied herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, and A, can independently be covalently coupled to a linker and/or a linker to which is attached one or more PTM, ULM, ILM or ILM' groups.

Exemplary CLMs

Neo-Imide Compounds

In one aspect the description provides compounds useful for binding and/or inhibiting cereblon. In certain embodiments, the compound is selected from the group consisting of chemical structures:

(a1)

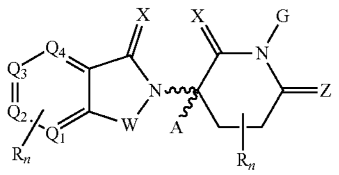

(b)

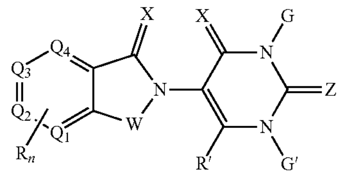

(c)

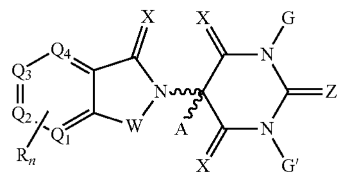

(d1)

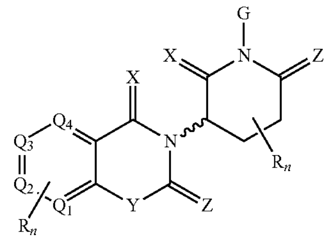

-continued (e)

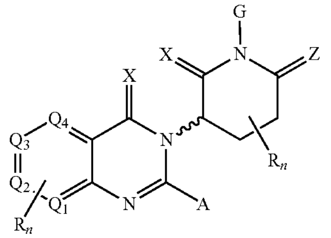

(f)

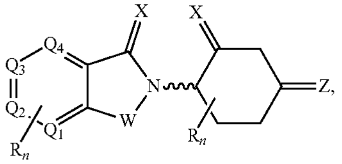

(a2)

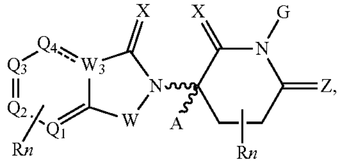

(d2)

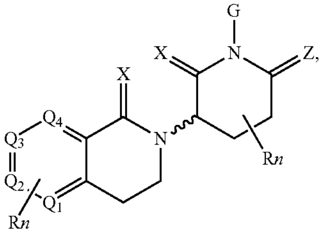

(a3)

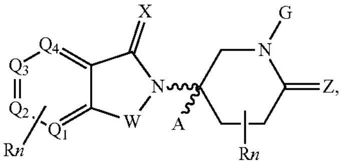

or (a4)

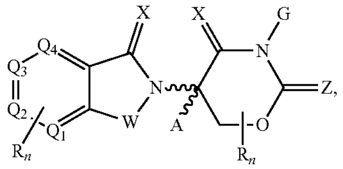

wherein:

W of Formulas (a) through (e) [e.g., (a1), (b), (c), (d1), (e), (f), (a2), (d2), (a3), and (a4)] is independently selected from the group $CH_2$, O, CHR, C═O, $SO_2$, NH, optionally substituted cycloalkyl (e.g., optionally substituted 3-6 member cycloalkyl, optionally substituted cyclopropyl group or optionally substituted cyclobutyl group), optionally substituted heterocycloalkyl, and N-alkyl;

$W_3$ is selected from C or N;

X of Formulas (a) through (e) is independently selected from the group absent, O, S and $CH_2$;

Y of Formulas (a) through (e) is independently selected from the group $CH_2$, —C═CR', NH, N-alkyl, N-aryl, N-hetaryl, N-cycloalkyl, N-heterocyclyl, O, and S;

Z of Formulas (a) through (e) is independently selected from the group absent, O, S or $CH_2$ except that both X and Z cannot be absent or $CH_2$;

G and G' of Formulas (a) through (e) are independently selected from the group H, optionally substituted linear or branched alkyl, OH, R'OCOOR, R'OCONRR", $—(CH_2)_{n''}—O—P(═O)(O—C_{1-6}alkyl)(OH)$, $—(CH_2)_{n''}—O—P(═O)(O—C_{1-6}alkyl)_2$, $—(CH_2)_{n''}—O—P(═O)(OH)_2$, $CH_2OCOO(CH_2CH_2O)_{n''}CH_3$, $CH_2$-heterocyclyl optionally substituted with R', and benzyl optionally substituted with R';

n" is an integer from 8 to 35 (e.g., 8, 9, 10, 11, 12, 13, 14, 15, 16, 17, 18, 19, 20, 21, 22, 23 24, 25, 26, 27, 28, 29, 30, 31, 32, 33, 34, or 35);

Q1-Q4 of Formulas (a) through (e) each independently represent a carbon C substituted with a group independently selected from H, R, N or N-oxide;

A of Formulas (a) through (e) is independently selected from the group H, optionally substituted linear or branched alkyl, cycloalkyl, Cl and F;

R of Formulas (a) through (e) comprises, but is not limited to: H, —CONR'R", —OR', —NR'R", —SR', $—SO_2R'$, $—SO_2NR'R"$, —CR'R"—, —CR'NR'R"—, $(—CR'O)_{n''}R"$, halogen, optionally substituted-aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted-heteroaryl (e.g., an optionally substituted C5-C7 heteroaryl), unsubstituted or substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

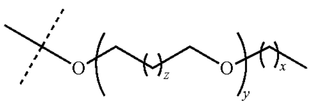

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

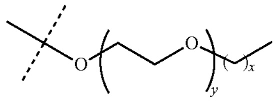

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted-cycloalkyl (e.g., optionally substituted C3-C7 cycloalkyl), optionally substituted-heterocyclyl (e.g., optionally substituted C3-C7 heterocyclyl), —P(O)(OR')R", —P(O)R'R", —OP(O)(OR')R", —OP(O)R'R", —Cl, —F, —Br, —I, $—CF_3$, —CN, $—NR'SO_2NR'R"$, —NR'CONR'R", —CONR'COR", —NR'C(═N—CN)NR'R", —C(═N—CN)NR'R", —NR'C(═N—CN)R", $—NR'C(═C—NO_2)NR'R"$, $—SO_2NR'COR"$, $—NO_2$, $—CO_2R'$, —C(C═N—OR')R", —CR'═CR'R", —CCR', —S(C═O)(C═N—R')R", $—SF_5$ and $—OCF_3$; each of x, y, and z are independently 0, 1, 2, 3, 4, 5, or 6;

R' and R" of Formulas (a) through (e) are independently selected from a H, optionally substituted linear or branched alkyl, optionally substituted cycloalkyl, optionally substituted aryl, optionally substituted heteroaryl, optionally substituted heterocyclic, —C(═O) R, optionally substituted heterocyclyl;

n and n' of Formulas (a) through (e) are each individually an integer from 1-10 (e.g., 1-4, 1, 2, 3, 4, 5, 6, 7, 8, 9, or 10);

⩦ represents a single bond or a double bond; and

〰 of Formulas (a) through (e) represents a bond that may be stereo specific ((R) or (S)) or non-stereo specific.

Exemplary CLMs

In any of the compounds described herein, the CLM comprises a chemical structure selected from the group:

(a1)

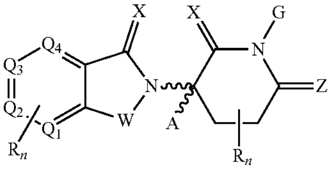

(b)

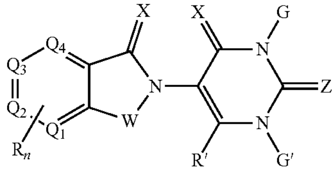

(c)

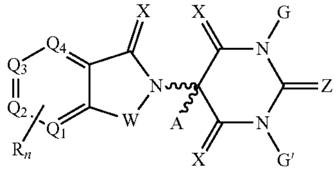

(d1)

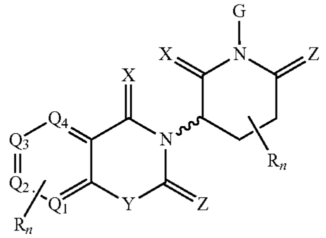

(e)

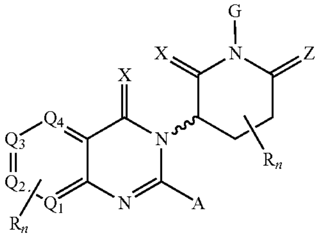

(f)

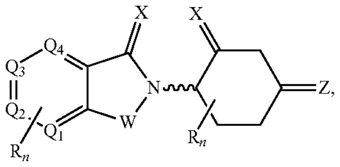

-continued (a2)

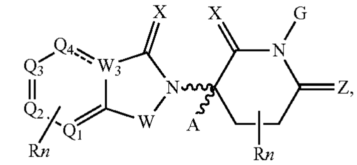

(d2)

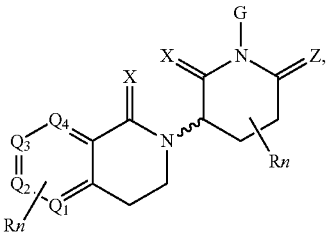

(a3)

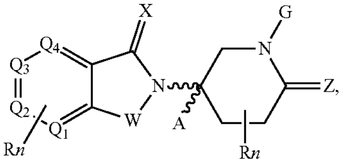

or (a4)

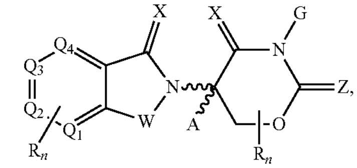

wherein:

W of Formulas (a) through (e) [e.g., (a1), (b), (c), (d1), (e), (f), (a2), (d2), (a3), and (a4)] is independently selected from the group $CH_2$, O, CHR, C═O, $SO_2$, NH, optionally substituted cycloalkyl (e.g., optionally substituted 3-6 member cycloalkyl, optionally substituted cyclopropyl group or optionally substituted cyclobutyl group), optionally substituted heterocycloalkyl (e.g., an optionally substituted 3-6 member heterocyloalkyl), and N-alkyl;

$W_3$ is selected from C or N;

X of Formulas (a) through (e) is independently selected from the group absent, O, S and $CH_2$;

Y of Formulas (a) through (e) is independently selected from the group CH2, —C═CR', NH, N-alkyl, N-aryl, N-hetaryl, N-cycloalkyl, N-heterocyclyl, O, and S;

Z of Formulas (a) through (e) is independently selected from the group absent, O, S, and $CH_2$ except that both X and Z cannot be absent or $CH_2$;

G and G' of Formulas (a) through (e) are independently selected from the group H, optionally substituted linear or branched alkyl, OH, R'OCOOR, R'OCONRR", $—(CH_2)_n—O—P(═O)(O—C_{1-6}alkyl)(OH)$, $—(CH_2)_{n'}—O—P(═O)(O—C_{1-6}alkyl)_2$, $—(CH_2)_{n'}—O—P(═O)(OH)_2$, $CH_2OCOO(CH_2CH_2O)_{n''}—CH_3$, $CH_2$-heterocyclyl optionally substituted with R', and benzyl optionally substituted with R'; — n" is an integer from 8 to 35 (e.g., 8, 9, 10, 11, 12, 13, 14, 15, 16, 17, 18, 19, 20, 21, 22, 23 24, 25, 26, 27, 28, 29, 30, 31, 32, 33, 34, or 35);

Q1-Q4 of Formulas (a) through (e) each independently represent a carbon C substituted with a group independently selected from H, R, N or N-oxide;

A of Formulas (a) through (e) is independently selected from the group H, optionally substituted linear or branched alkyl, cycloalkyl, Cl and F;

R of Formulas (a) through (e) comprises, but is not limited to: H, —CONR'R", —OR', —NR'R", —SR', —$SO_2$R', —$SO_2$NR'R", —CR'R"—, —CR'NR'R"—, (—CR'O)$_{n'}$R", halogen, optionally substituted heterocyclyl (e.g., optionally substituted C3-C7 heterocyclyl), optionally substituted-aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted-heteroaryl (e.g., an optionally substituted C5-C7 heteroaryl), optionally substituted linear or branched-alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

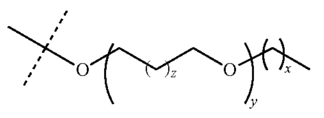

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

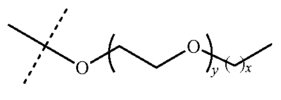

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted-cycloalkyl (e.g., optionally substituted C3-C7 cycloalkyl), optionally substituted-cycloalkyl (e.g., optionally substituted C3-C7 cycloalkyl), optionally substituted-heterocyclyl (e.g., optionally substituted C3-C7 heterocyclyl), —P(O)(OR')R", —P(O)R'R", —OP(O)(OR')R", —OP(O)R'R", —Cl, —F, —Br, —I, —$CF_3$, —CN, —NR'$SO_2$NR'R", —NR-'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$ and —$OCF_3$, wherein at least one R (e.g., at least one of O, OH, N, NH, $NH_2$, C1-C6 alkyl, C1-C6 alkoxy, optionally substituted-cycloalkyl (e.g., optionally substituted C3-C7 cycloalkyl), optionally substituted-heterocyclyl (e.g., optionally substituted C3-C7 heterocyclyl), -alkyl-aryl (e.g., an -alkyl-aryl comprising at least one of C1-C6 alkyl, C4-C7 aryl, or a combination thereof), aryl (e.g., C5-C7 aryl), heteroaryl aryl (e.g., C5-C7 heteroaryl), amine, amide, or carboxy) is modified to be covalently joined to a PTM, a chemical linker group (L), a ULM, a CLM' (e.g., CLM' is an additional CLM that has the same or different structure as a first CLM), or a combination thereof each of x, y, and z are independently 0, 1, 2, 3, 4, 5, or 6;

R' and R" of Formulas (a) through (e) are independently selected from a bond, H, optionally substituted linear or branched alkyl, optionally substituted cycloalkyl, optionally substituted aryl, optionally substituted heteroaryl, optionally substituted heterocyclic, —C(═O)R, optionally substituted heterocyclyl;

n and n' of Formulas (a) through (e) are each individually an integer from 1-10 (e.g., 1-4, 1, 2, 3, 4, 5, 6, 7, 8, 9, or 10);

⁓ of Formulas (a) through (e) represents a bond that may be stereo specific ((R) or (S)) or non-stereo specific In certain embodiments described herein, the CLM or ULM comprises a chemical structure selected from the group:

Formula (g)

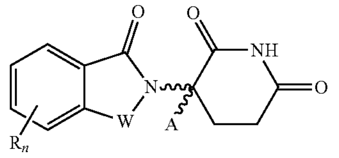

wherein:

W of Formula (g) is independently selected from the group $CH_2$, C═O, NH, and N-alkyl;

A of Formula (g) is independently selected from a H, methyl, alkyl (e.g., a or C1-C6 alkyl (linear, branched, optionally substituted));

R of Formula (g) is independently selected from a H, OH, $NH_2$, halogen, methyl, optionally substituted linear or branched alkyl (e.g., optionally substituted linear or branched C1-C6 alkyl), optionally substituted C1-C6 alkoxy, optionally substituted-cycloalkyl (e.g., optionally substituted C3-C7 cycloalkyl), optionally substituted-heterocyclyl (e.g., optionally substituted C3-C7 heterocyclyl), optionally substituted-alkyl-aryl (e.g., an -alkyl-aryl comprising at least one of C1-C6 alkyl, C4-C7 aryl, or a combination thereof), optionally substituted aryl (e.g., C5-C7 aryl), amine, amide, or carboxy);

n of Formulas (g) represent an integer from 1 to 4 (e.g., 1, 2, 3, or 4), wherein at least one R (e.g., at least one of OH, $NH_2$, halogen, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) is modified to be covalently joined to a PTM, a chemical linker group (L), a ULM, CLM (or CLM') or combination thereof; and ⁓ of Formula (g) represents a bond that may be stereospecific ((R) or (S)) or non-stereo specific.

In any of the embodiments described herein, the W, X, Y, Z, G, G, R', R', R", Q1-Q4, and A of Formulas (a) through (g) [e.g., (a1), (b), (c), (d1), (e), (f), (a2), (d2), (a3), (a4), and (g)] can independently be covalently coupled to a linker and/or a linker to which is attached one or more PTM, ULM, CLM or CLM' groups.

In any of the aspects or embodiments described herein, the CLM comprises from 1 to 4 R groups on $Q_1$, $Q_2$, $Q_3$, $Q_4$, or a combination, wherein each R is an independently selected functional groups or atoms, for example, OH, halogen, C1-C6 alkyl, C1-C6 alkoxy, optionally substituted-cycloalkyl (e.g., optionally substituted C3-C7 cycloalkyl), optionally substituted-heterocyclyl (e.g., optionally substituted C3-C7 heterocyclyl), -alkyl-aryl (e.g., an -alkyl-aryl comprising at least one of C1-C6 alkyl, C4-C7 aryl, or a combination thereof), aryl (e.g., C5-C7 aryl), amine, amide, cyano, or carboxy, and optionally, one of which is modified to be covalently joined to a PTM, a chemical linker group (L), a ULM, CLM (or CLM') or combination thereof.

In some embodiments, the CLM is represented by the following structures with the dashed lines indicating linker attachment points:

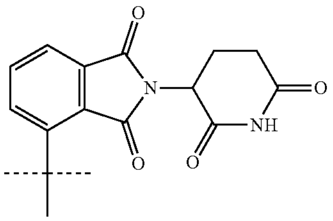

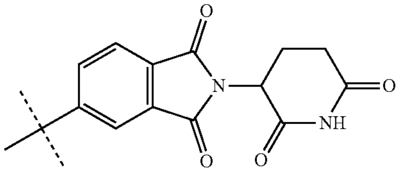

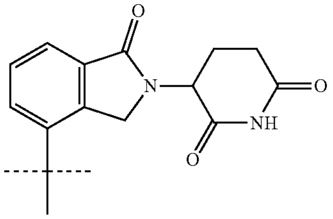

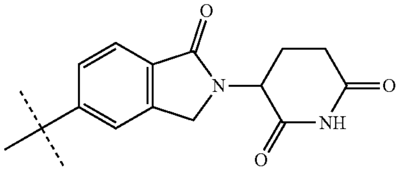

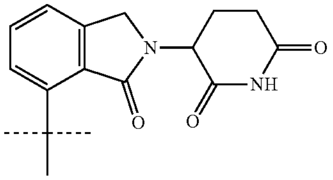

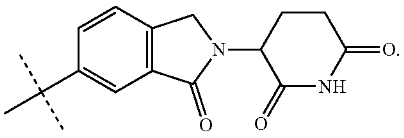

More specifically, non-limiting examples of CLMs include those shown below as well as those "hybrid" molecules that arise from the combination of 1 or more of the different features shown in the molecules below.

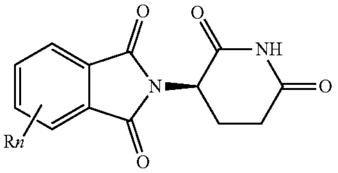

-continued

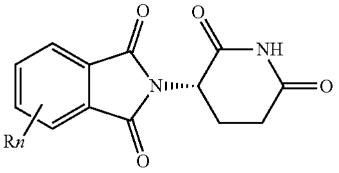

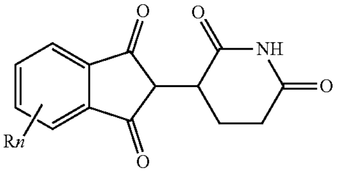

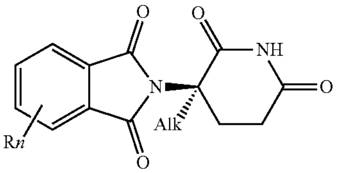

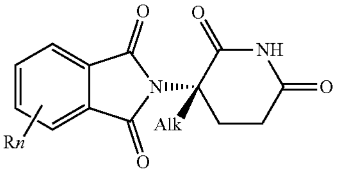

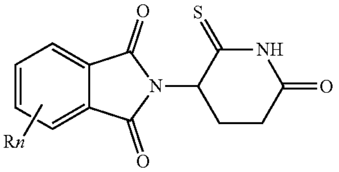

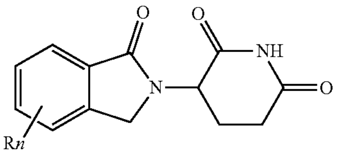

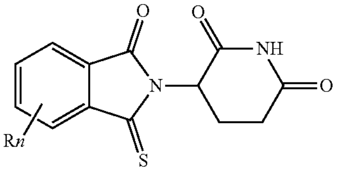

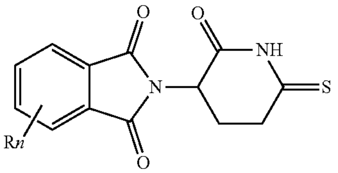

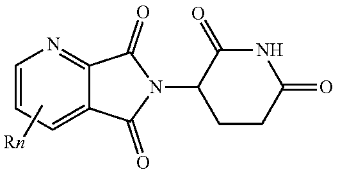

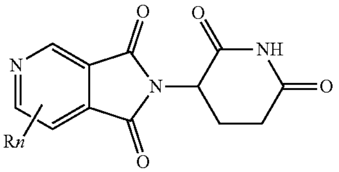

-continued
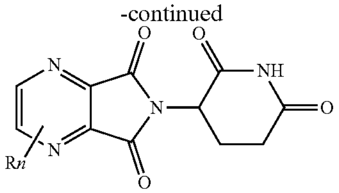
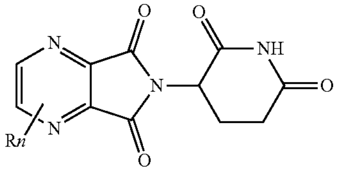
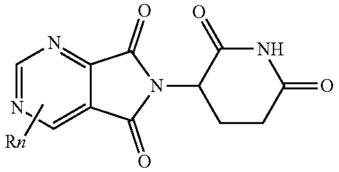
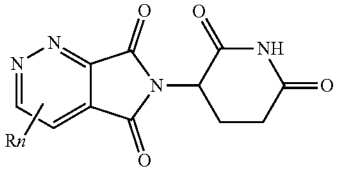
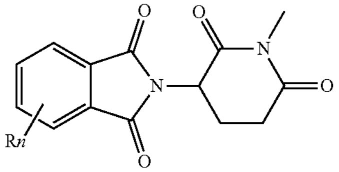
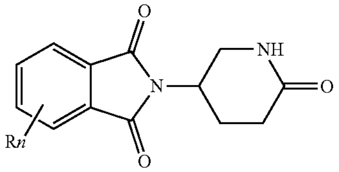
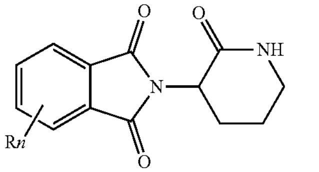
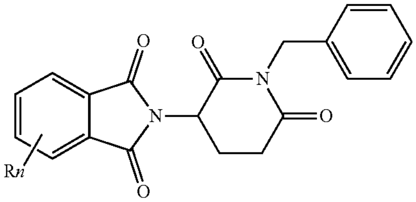
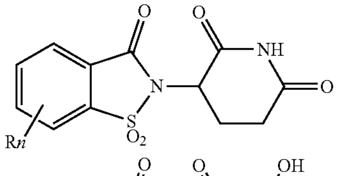
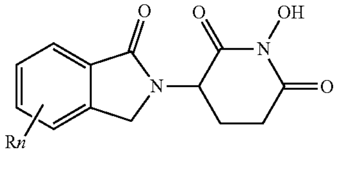
-continued
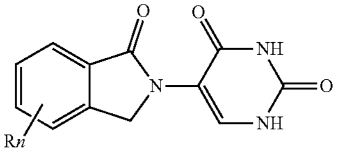
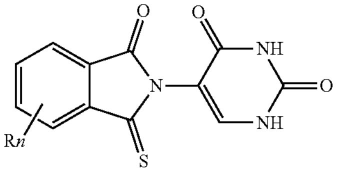
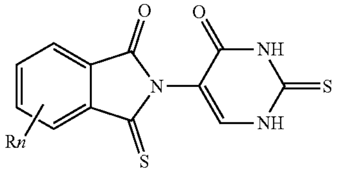
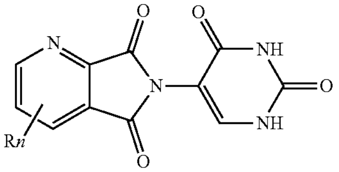
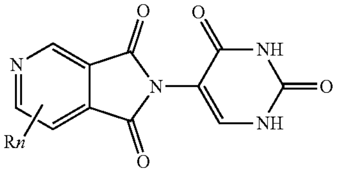
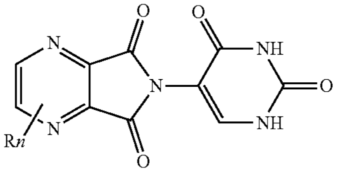
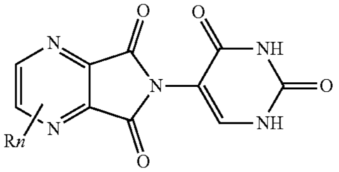
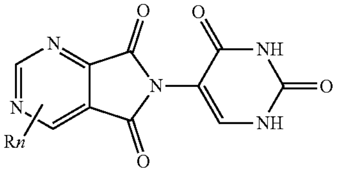
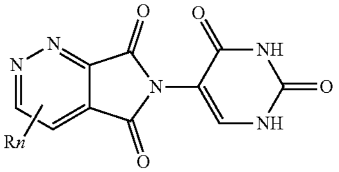
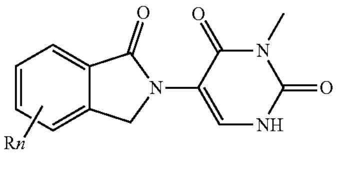

-continued
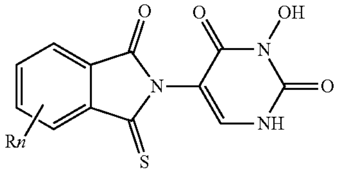
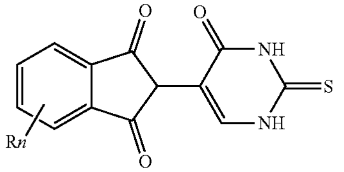
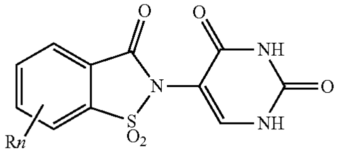
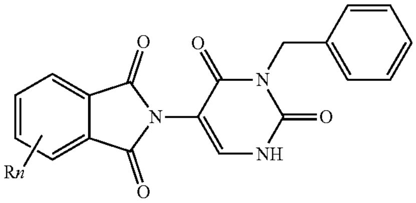
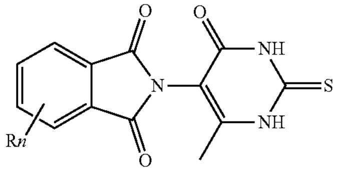
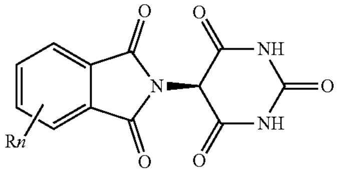
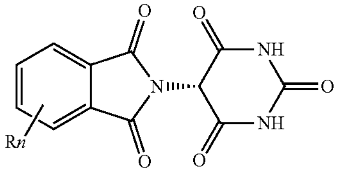
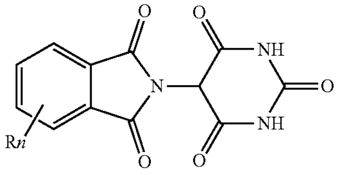
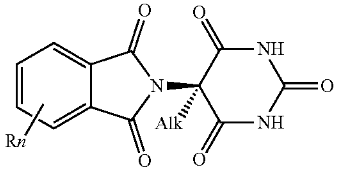
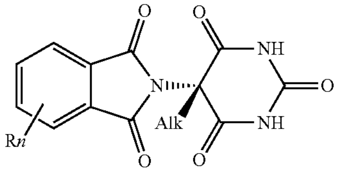
-continued
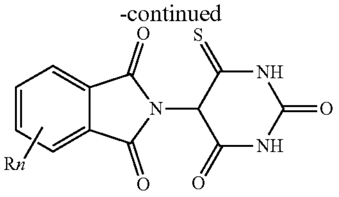
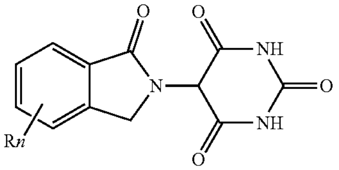
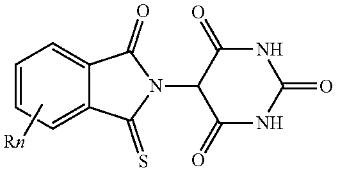
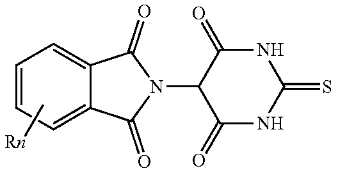
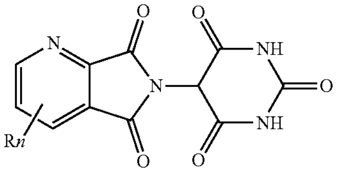
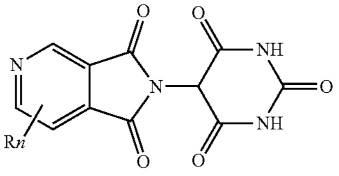
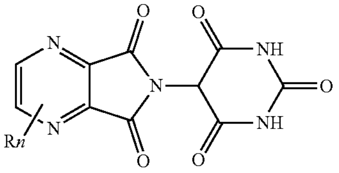
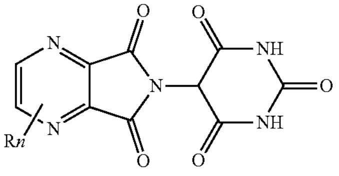
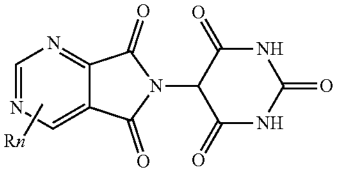
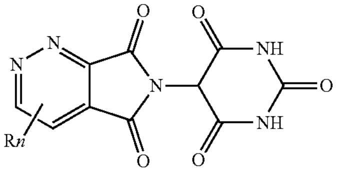

-continued
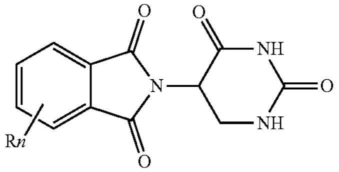
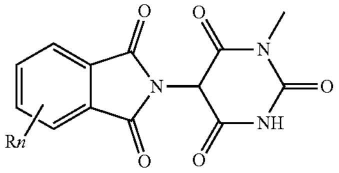
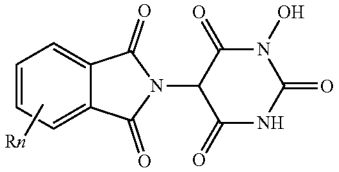
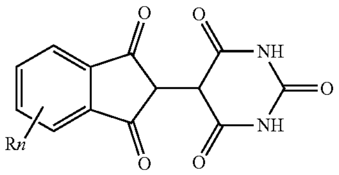
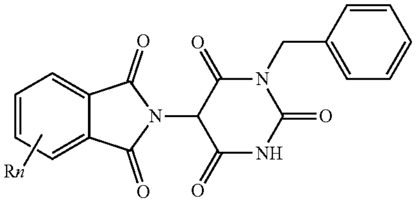
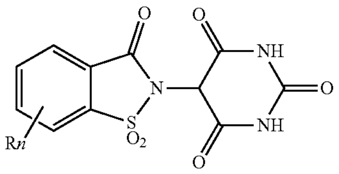
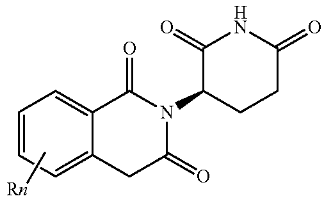
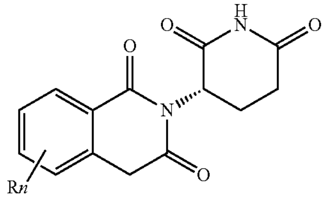
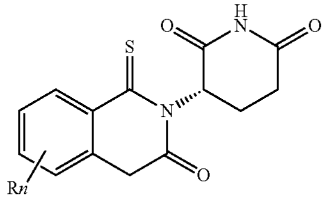
-continued
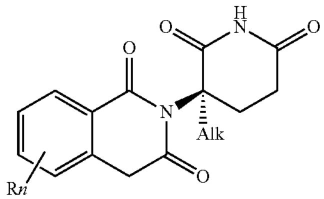
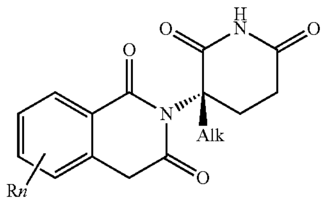
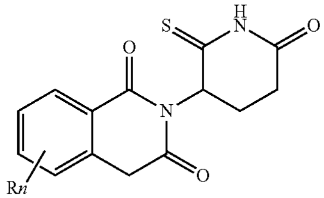
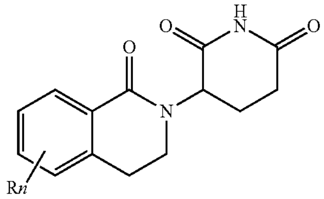
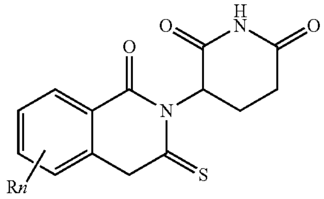
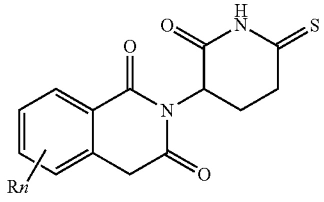
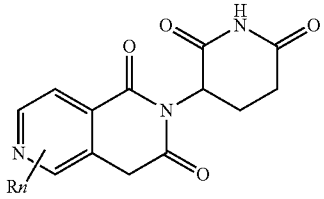
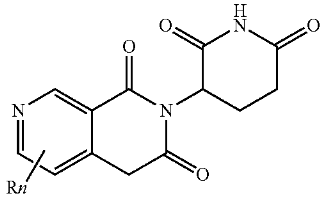

-continued
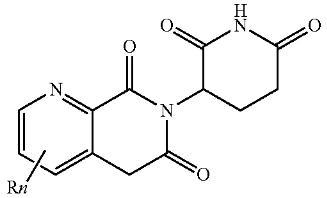
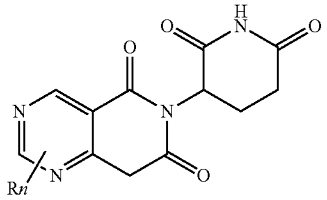
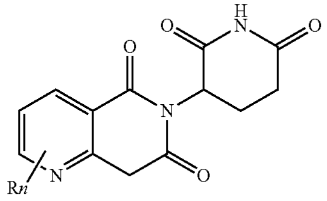
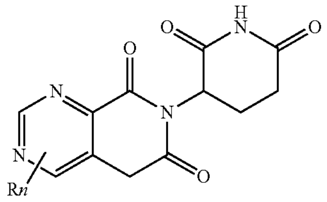
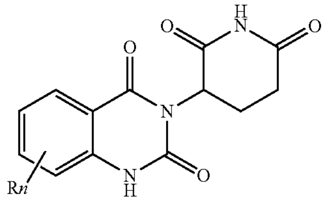
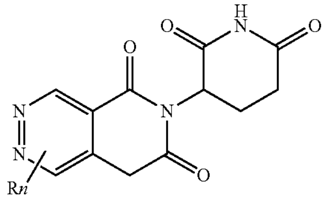
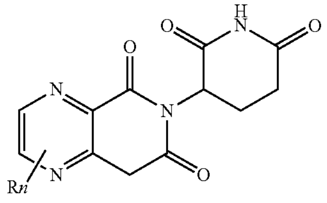
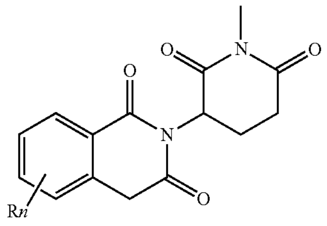
-continued
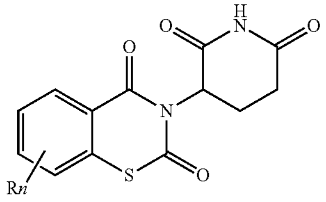
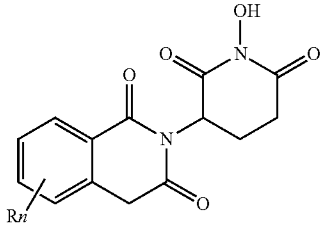
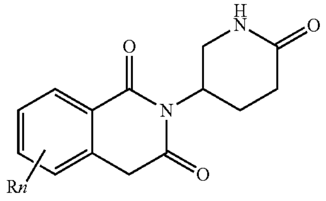
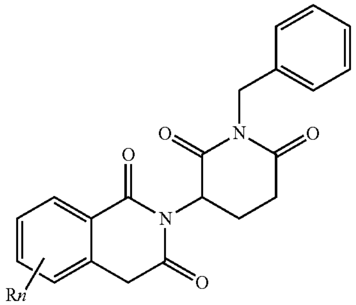
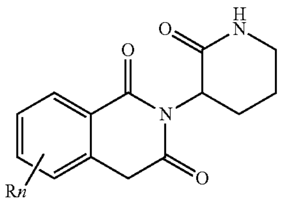
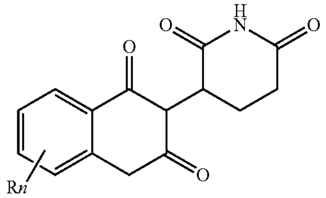
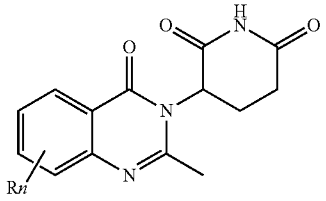
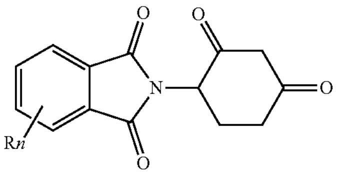

-continued
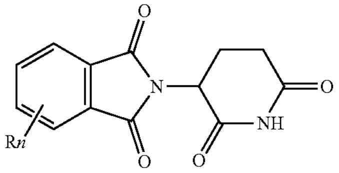
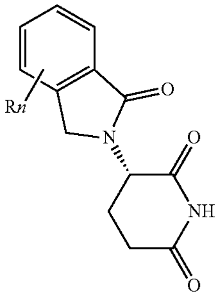
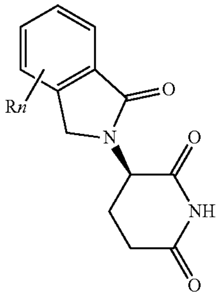
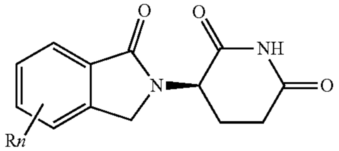
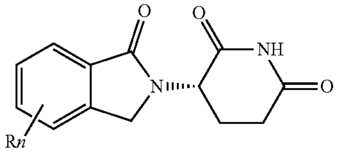
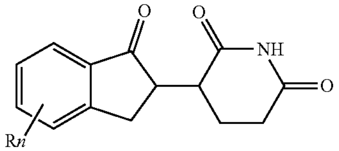
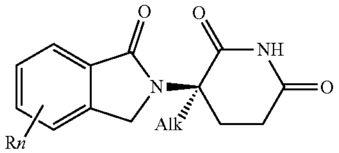
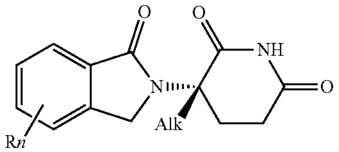
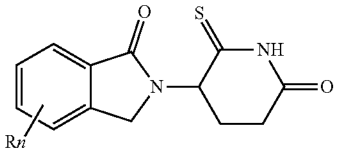
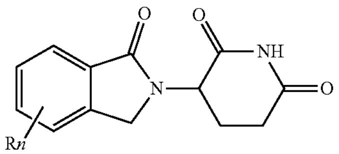
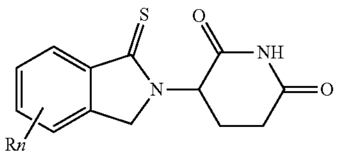
-continued
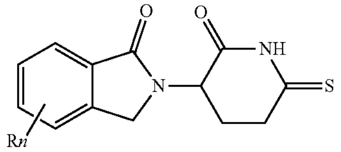
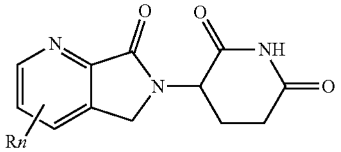
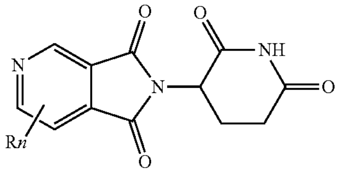
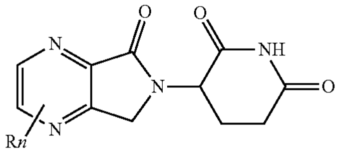
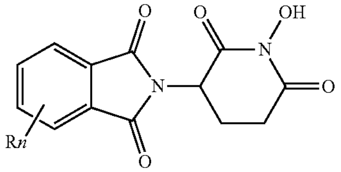
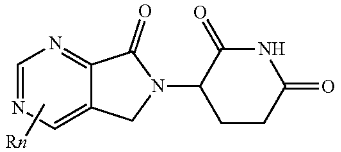
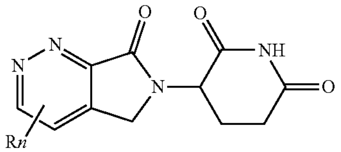
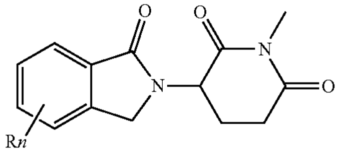
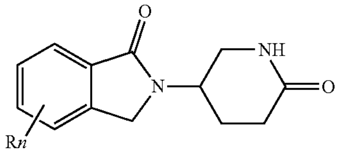
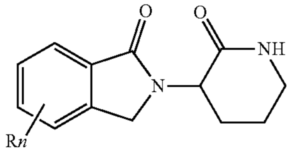

-continued
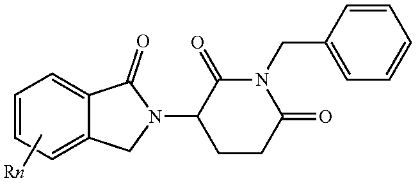
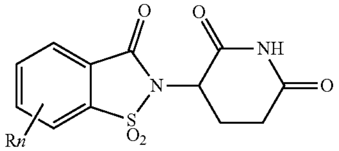
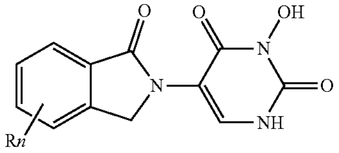
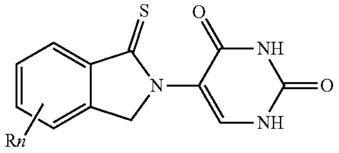
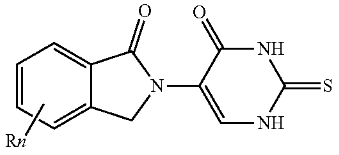
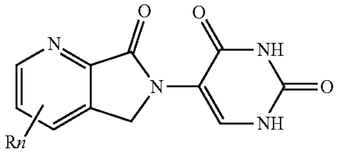
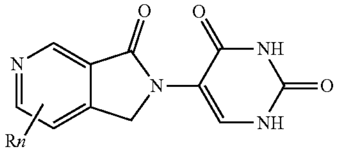
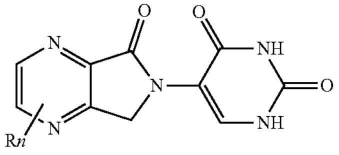
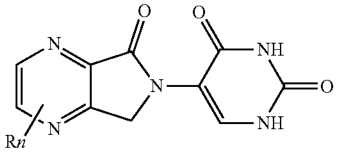
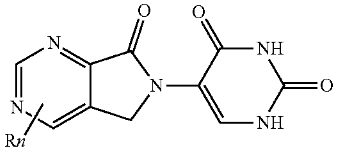
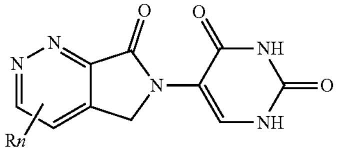
-continued
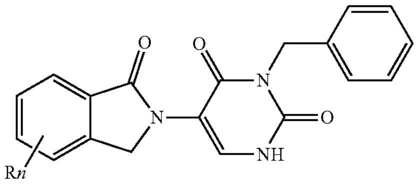
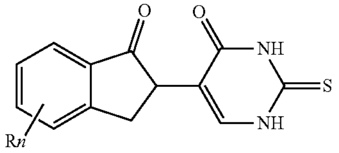
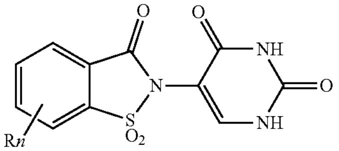
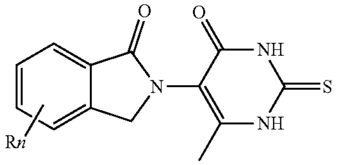
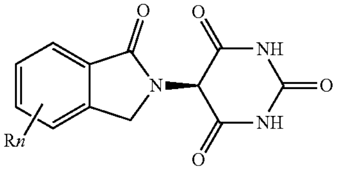
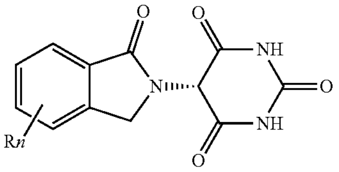
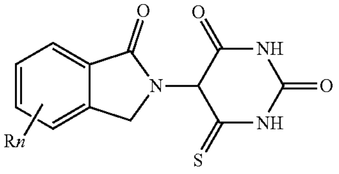
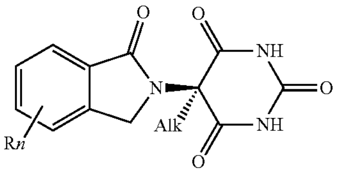
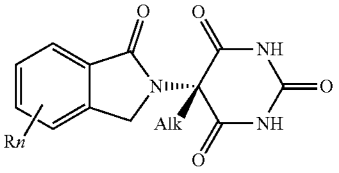
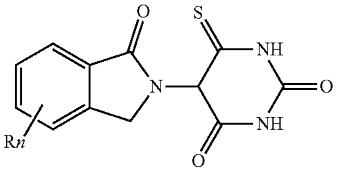

-continued
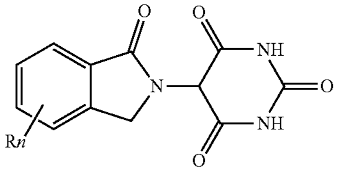
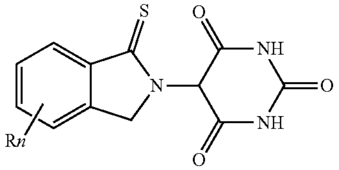
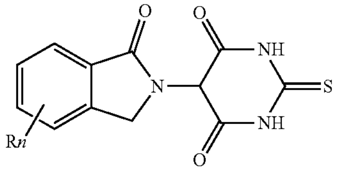
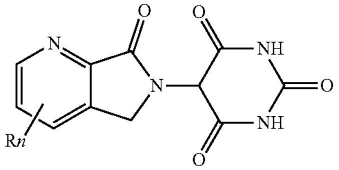
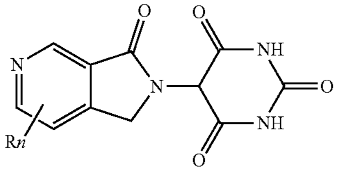
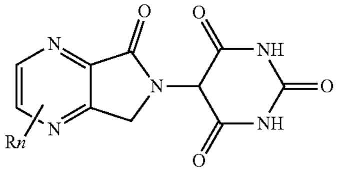
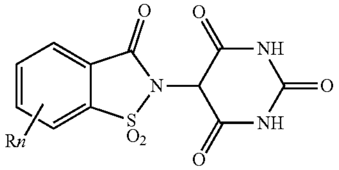
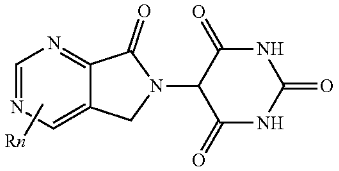
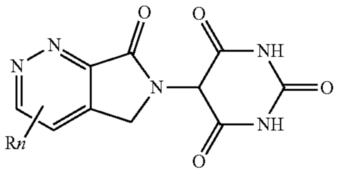
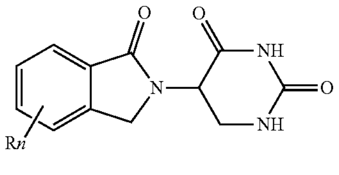
-continued
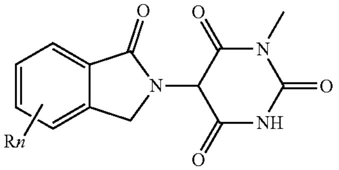
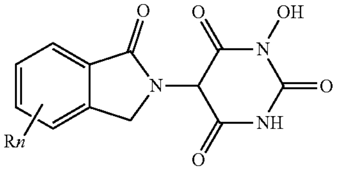
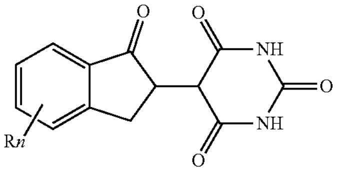
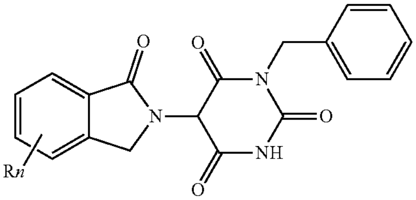
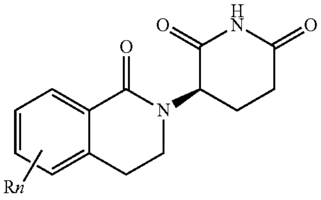
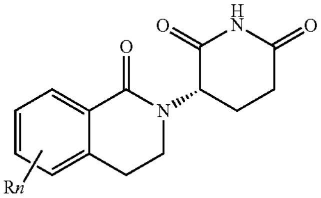
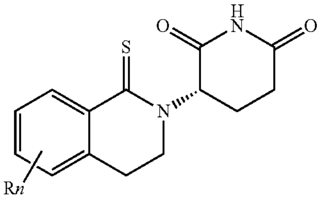
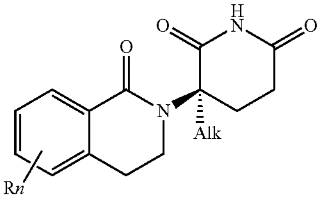
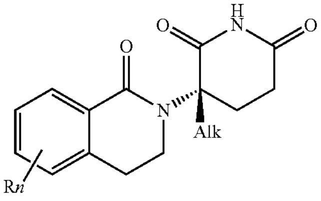

-continued
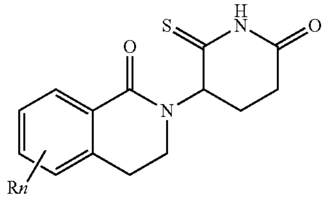
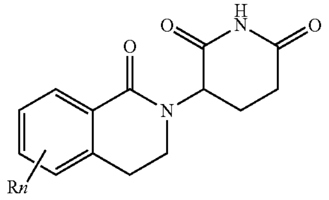
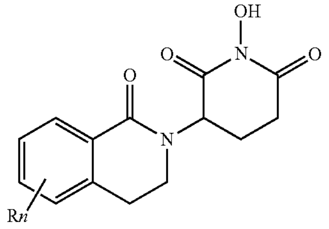
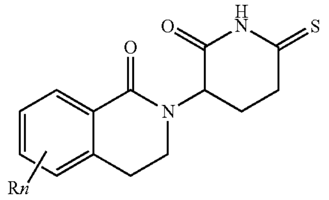
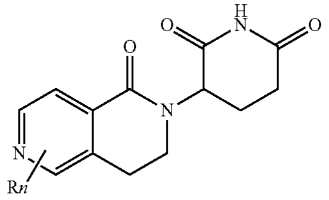
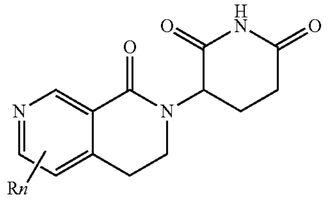
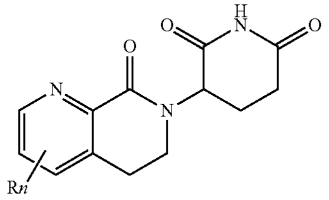
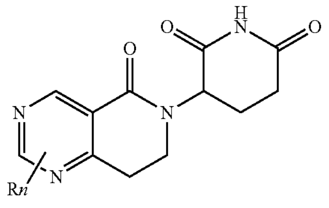
-continued
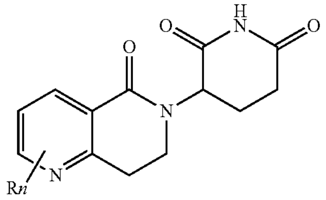
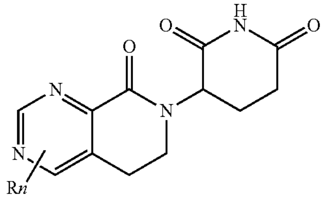
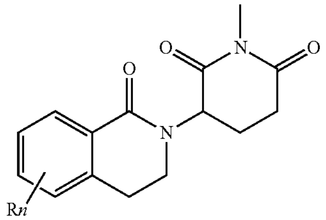
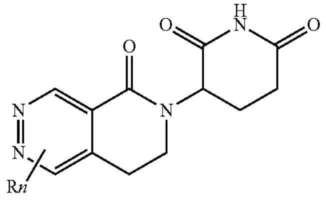
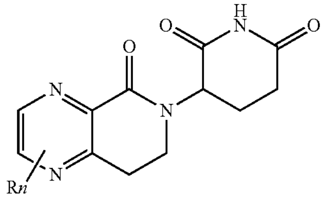
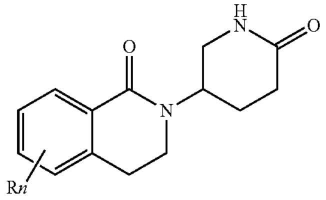
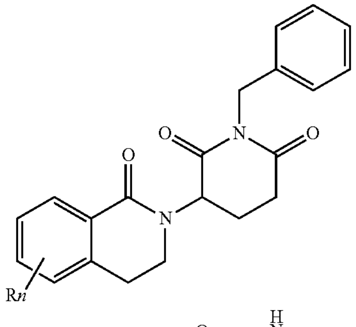
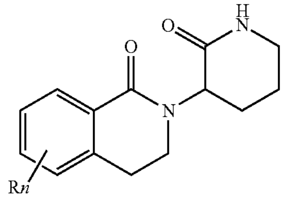

-continued
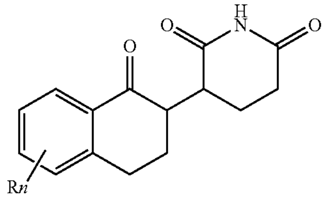
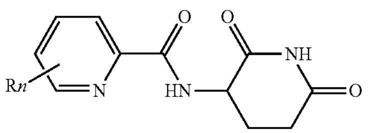
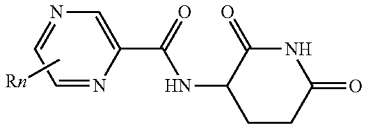
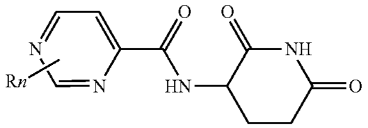
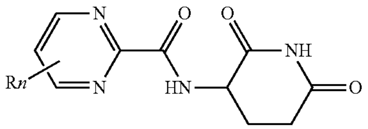
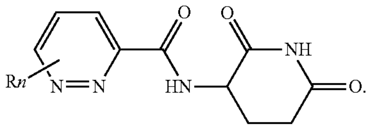
In any of the compounds described herein, the CLM comprises a chemical structure selected from the group:
(h)
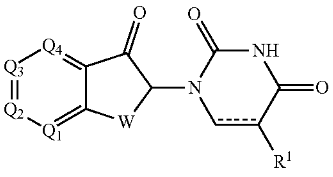
(i)
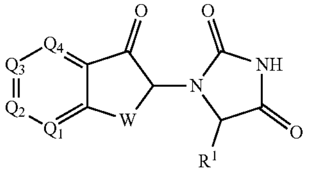
(j)
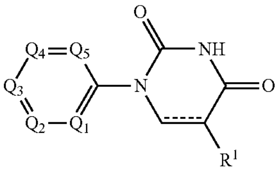
-continued
(k)
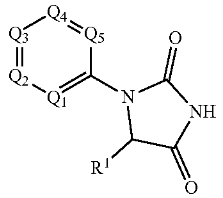
(l)
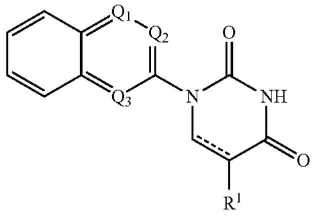
(m)
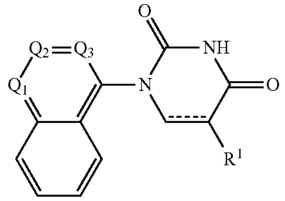
(n)
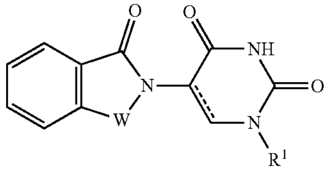
(o)
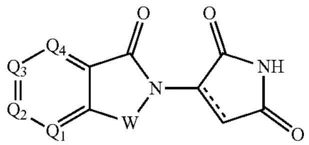
(p)
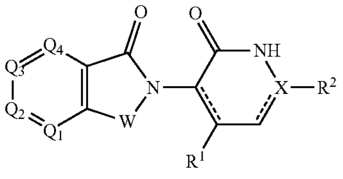
(q)
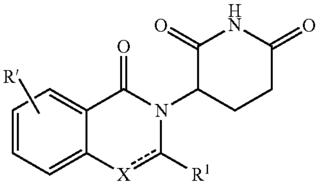
(r)
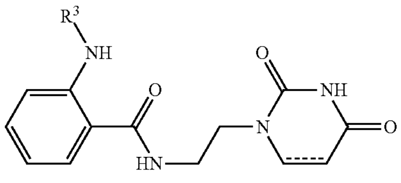

-continued
(s)
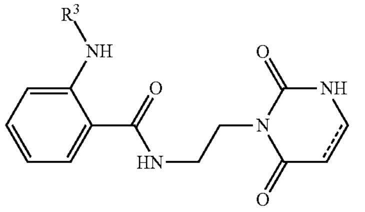
(t)
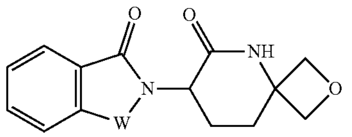
(u)
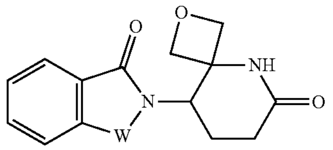
(v)
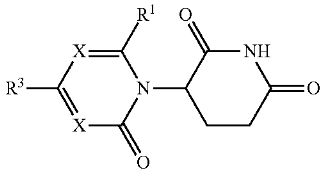
(w)
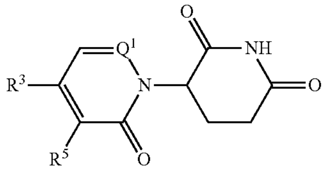
(x)
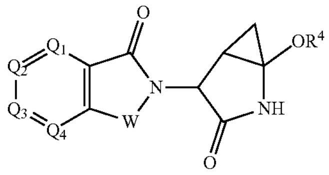
(y)
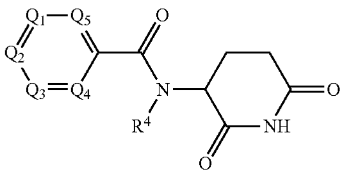
(z)
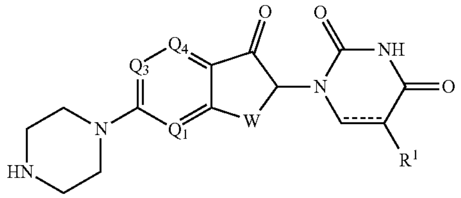
(aa)
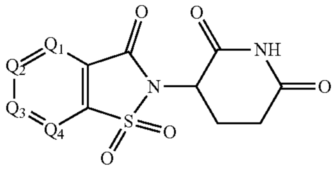
-continued
(ab)
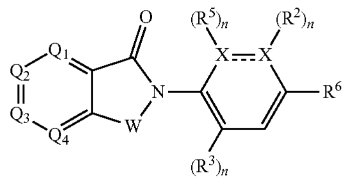
(ac)
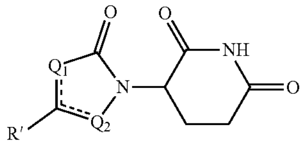
(ad)
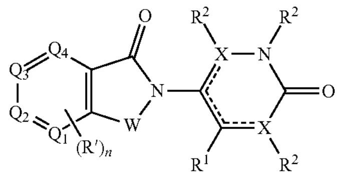
(ae)
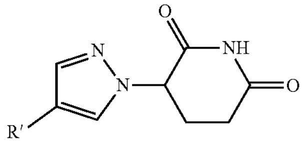
(af)
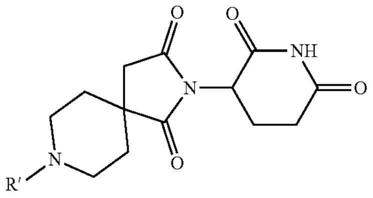
(ag)
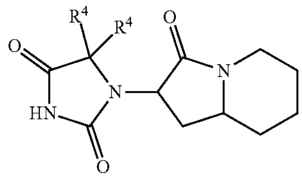
(ah)
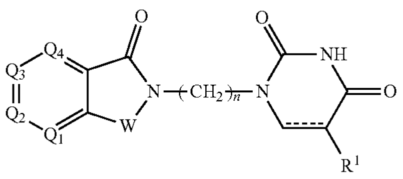
(ai)
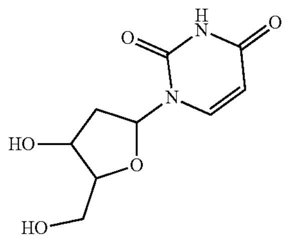

-continued (aj)

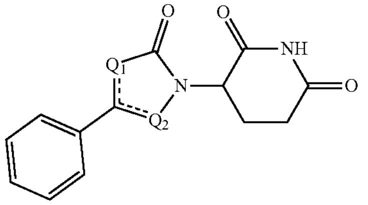

(ak)

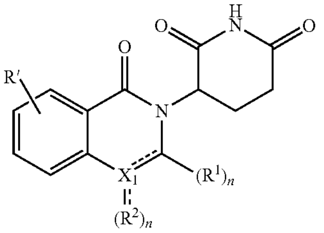

(al)

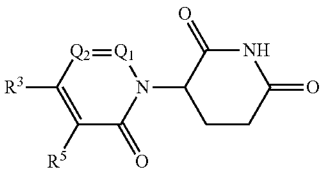

(am)

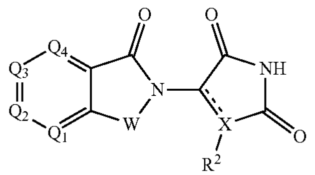

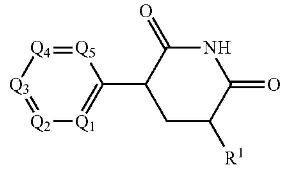

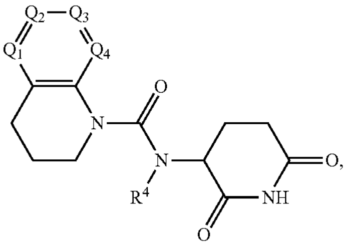

wherein:

W is independently selected from $CH_2$, O, CHR, C═O, $SO_2$, NH, optionally substituted cycloalkyl, optionally substituted heterocyclalkyl, and N-alkyl;

$Q_1$, $Q_2$, $Q_3$, $Q_4$, $Q_5$ are each independently represent a carbon C or N substituted with a group independently selected from H, R', N or N-oxide;

$R^1$ is selected from absent, H, OH, CN, C1-C3 alkyl, C═O;

$R^2$ is selected from the group absent, H, OH, CN, C1-C3 alkyl, $CHF_2$, $CF_3$, CHO, C(═O)$NH_2$;

$R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);

$R^4$ is selected from H, alkyl, substituted alkyl;

$R^5$ and $R^6$ are each independently H, halogen, C(═O)R', CN, OH, $CF_3$;

X is C, CH, C═O, or N;

$X_1$ is C═O, N, CH, or $CH_2$;

R' is selected from H, OH, halogen, amine, cyano, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(═O)$OR^2$, optionally substituted phenyl;

n is 0-4;

⫽ is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more featrues of the following compounds:

(an)

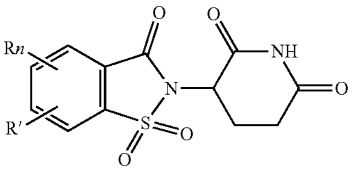

(ao)

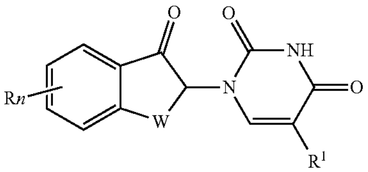

(ap)

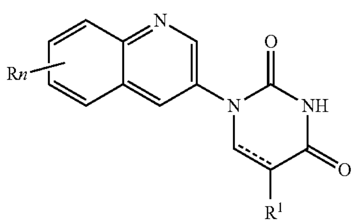

(aq)

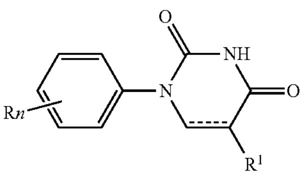

-continued
(ar)
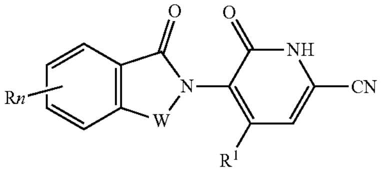
(as)
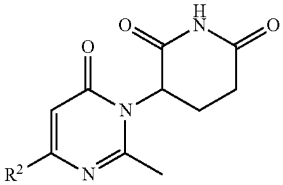
(at)
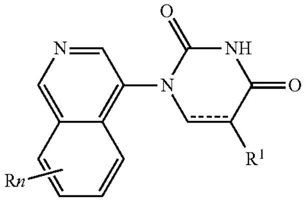
(au)
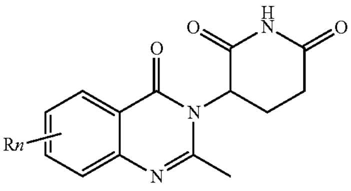
(av)
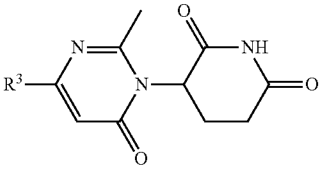
(aw)
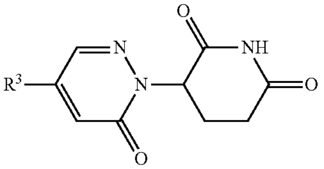
(ax)
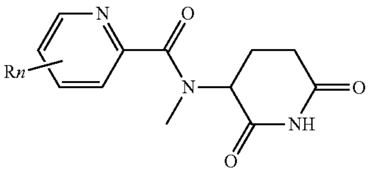
(ay)
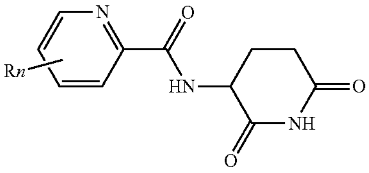
-continued
(az)
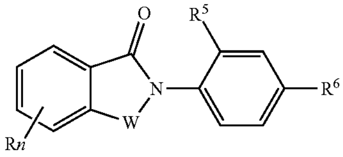
(ba)
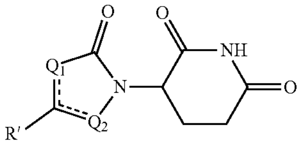
(bb)
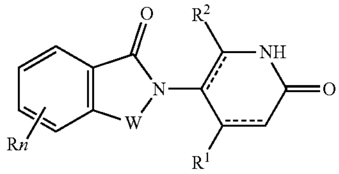
(bc)
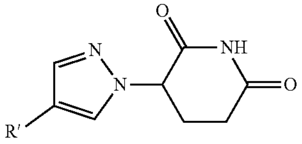
(bd)
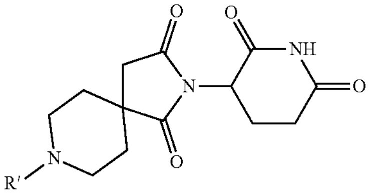
(be)
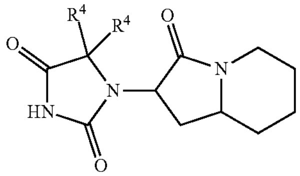
(bf)
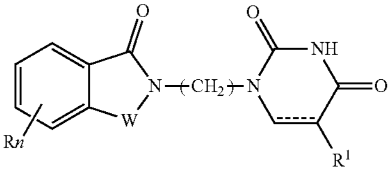
(bg)
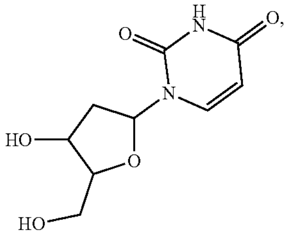
wherein:
W is independently selected from the group $CH_2$, CHR, C═O, $SO_2$, NH, and N-alkyl;
$R^1$ is selected from the group absent, H, CH, CN, C1-C3 alkyl;
$R^2$ is H or a C1-C3 alkyl;

$R^3$ is selected from H, alkyl, substituted alkyl, alkoxy, substituted alkoxy;
$R^4$ is methyl or ethyl;
$R^5$ is H or halo;
$R^6$ is H or halo;
R of the CLM is H;
R' is H or an attachment point for a PTM, a PTM', a chemical linker group (L), a ULM, a CLM, a CLM',
$Q_1$ and $Q_2$ are each independently C or N substituted with a group independently selected from H or C1-C3 alkyl;
⁄⁄ is a single or double bond;
n is an integer from 1 to 4 (e.g., 1, 2, 3, or 4); and
R comprises: H, —CONR'R", —OR', —NR'R", —SR', —$SO_2$R', —$SO_2$NR'R", —CR'R"—, —CR'NR'R"—, (—CR'O)$_n$R", halogen, optionally substituted heterocyclyl, optionally substituted -aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl (e.g., an optionally substituted C5-C7 aryl), -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

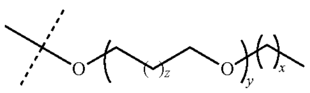

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

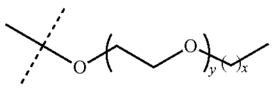

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$ and —$OCF_3$.

In any aspect or embodiment described herein, at least one R of $Q_1$, $Q_2$, $Q_3$, $Q_4$, $Q_5$, or a combination thereof (e.g., at least one of OH, $NH_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) is modified to be covalently joined to a PTM, a chemical linker group (L), a ULM, a CLM' (e.g., CLM' is an additional CLM that has the same or different structure as a first CLM), or a combination thereof.

In any of the embodiments described herein, the W, $R^1$, $R^2$, $Q_1$, $Q_2$, $Q_3$, $Q_4$, and R of Formulas (ac) through (an) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and R of Formulas (ac) through (an) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and R of Formulas (ac) through (an) can independently be covalently coupled to a linker and/or a linker to which is attached one or more PTM, ULM, ULM', CLM or CLM' groups.

In any aspect or embodiment described herein, R of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

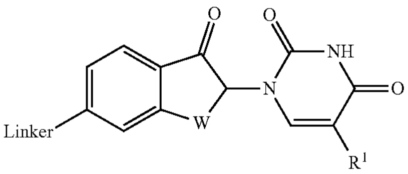

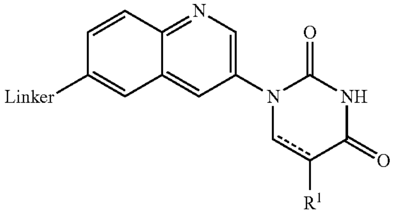

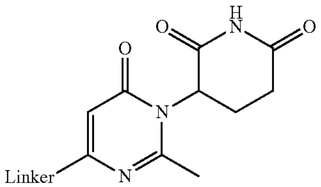

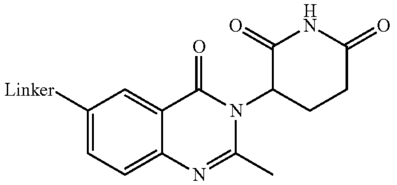

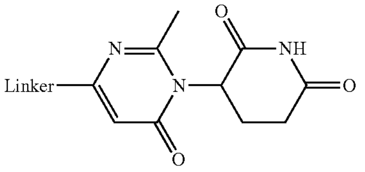

-continued
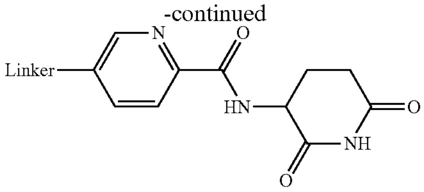
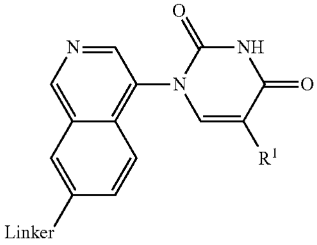
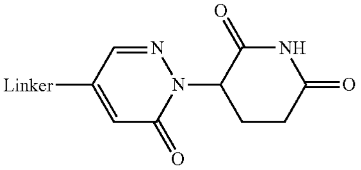
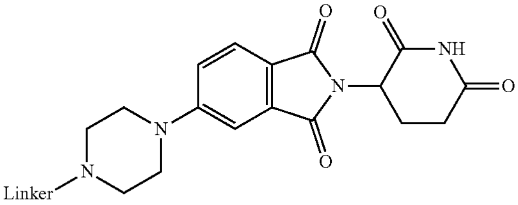
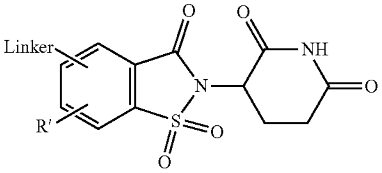
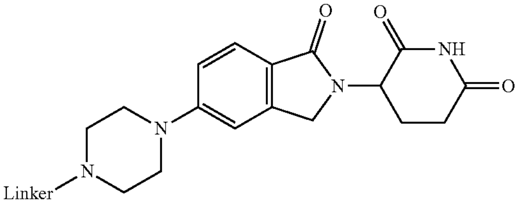
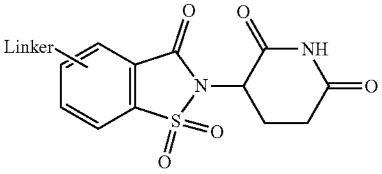
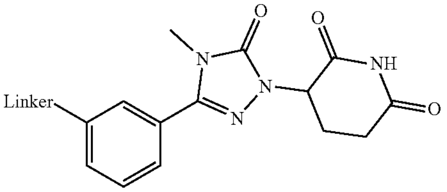
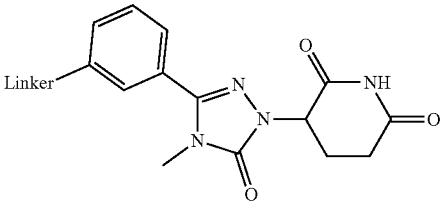
-continued
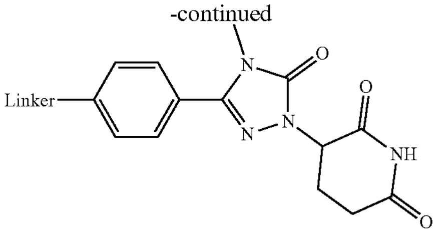
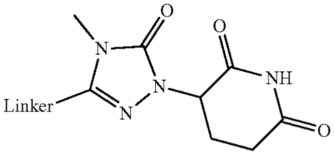
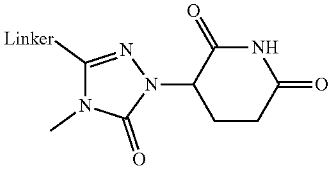
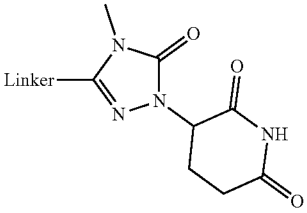
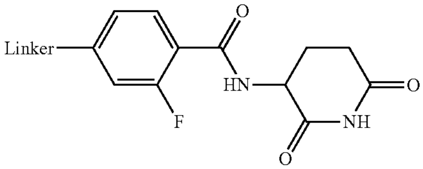
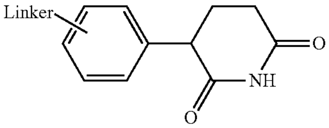
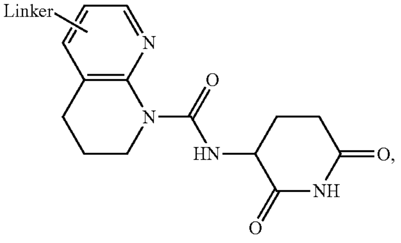
wherein R' is a halogen and $R^1$ is as described in any aspect or embodiment described herein.
In certain cases, the CLM can be imides that bind to cereblon E3 ligase. These imides and linker attachment point can be but not limited to the following structures:
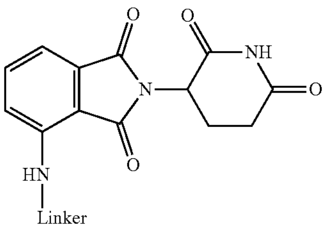

-continued

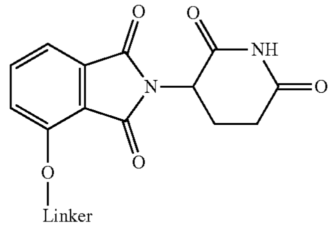

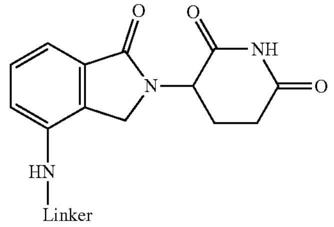

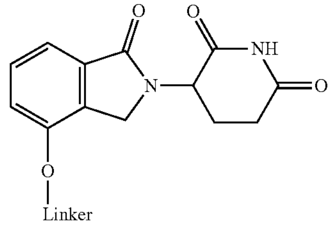

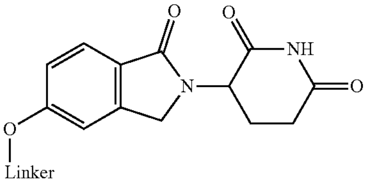

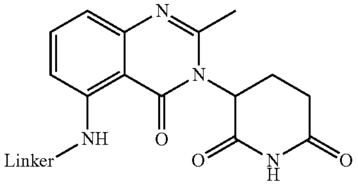

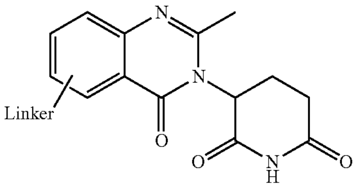

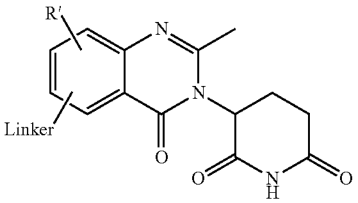

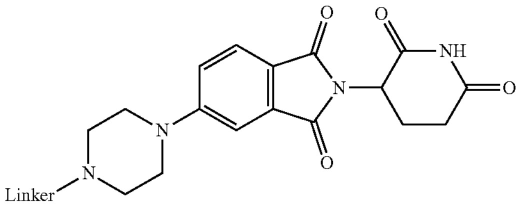

-continued

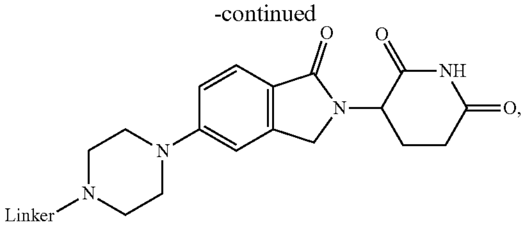

wherein R' is a halogen.

Exemplary VLMs

In certain embodiments of the compounds as described herein, the ULM is a VLM and comprises a chemical structure of ULM-a:

ULM-

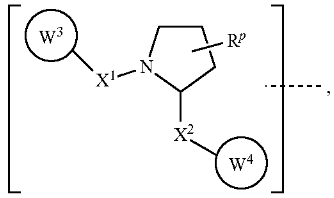

wherein:

a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;

$X^1$, $X^2$ of Formula ULM-a are each independently selected from the group of a bond, O, $NR^{Y3}$, $CR^{Y3}R^{Y4}$, C═O, C═S, SO, and $SO_2$;

$R^{Y3}$, $R^{Y4}$ of Formula ULM-a are each independently selected from the group of H, optionally substituted linear or branched $C_{1-6}$ alkyl (e.g., optionally substituted by 1 or more halo), optionally substituted $C_{1-6}$ alkoxyl (e.g., optionally substituted with 0-3 $R^P$ groups);

$R^P$ of Formula ULM-a is 0, 1, 2, or 3 groups, each independently selected from H, halo, —OH, $C_{1-3}$ alkyl, C═O;

$W^3$ of Formula ULM-a is selected from the group of an optionally substituted T, an optionally substituted -T-N$(R^{1a}R^{1b})X^3$, optionally substituted -T-N$(R^{1a}R^{1b})$, optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;

$X^3$ of Formula ULM-a is C═O, $R^1$, $R^{1a}$, $R^{1b}$;

$R^1$, $R^{1a}$, $R^{1b}$ are each independently selected from the group consisting of H, linear or branched $C_1$-$C_6$ alkyl group optionally substituted by 1 or more halo or —OH groups, $R^{Y3}C$═O, $R^{Y3}C$═S, $R^{Y3}SO$, $R^{Y3}SO_2$, $N(R^{Y3}R^{Y4})C$═O, $N(R^{Y3}R^{Y4})C$═S, $N(R^{Y3}R^{Y4})SO$, and $N(R^{Y3}R^{Y4})SO_2$;

T of Formula ULM-a is selected from the group of an optionally substituted alkyl, $—(CH_2)_n—$ group, wherein each one of the methylene groups is optionally substituted with one or two substituents selected from the group of halogen, methyl, optionally substituted alkoxy, —$(CH_2)_{m'}C(═O)(CH_2)_{m'}C(═O)(OH)$, $(CH_2)_{m'}OCOCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, a linear or branched $C_1$-$C_6$ alkyl group optionally substituted by 1 or more halogen or OH, C(O) $NR^1R^{1a}$, or $NR^1R^{1a}$ or $R^1$ and $R^{1a}$ are joined to form an optionally substituted heterocycle, or —OH groups or an amino acid side chain optionally substituted;

each m' is individually an integer from 1 to 4 (e.g., 1, 2, 3, or 4);

$W^4$ of Formula ULM-a is an optionally substituted —$NR^1$-T-Aryl, wherein the aryl group may be optionally substituted with an optionally substituted 5-6 membered heteroaryl, optionally substituted aryl, or optionally substituted alkoxy, an optionally substituted —$NR^1$-T-Heteroaryl group or an optionally substituted —$NR^1$-T-Heterocyclc, wherein —$NR^1$ is covalently bonded to $X^2$ and $R^1$ is H or $CH^3$, preferably H; and n is 0 to 6, often 0, 1, 2, or 3, preferably 0 or 1.

In any of the embodiments described herein, T is selected from the group of an optionally substituted alkyl, —$(CH_2)_n$— group, wherein each one of the methylene groups is optionally substituted with one or two substituents selected from the group of halogen, methyl, optionally substituted alkoxy, —$(CH_2)_{m'}C(═O)(CH_2)_{m'}C(═O)(OH)$, $(CH_2)_{m'}OCOCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocycle, or —OH groups or an amino acid side chain optionally substituted; each m' is individually an integer from 1 to 4 (e.g., 1, 2, 3, or 4), and n is 0 to 6, often 0, 1, 2, or 3, preferably 0 or 1.

In any aspect or embodiment described herein, $W^4$ of Formula ULM-a is

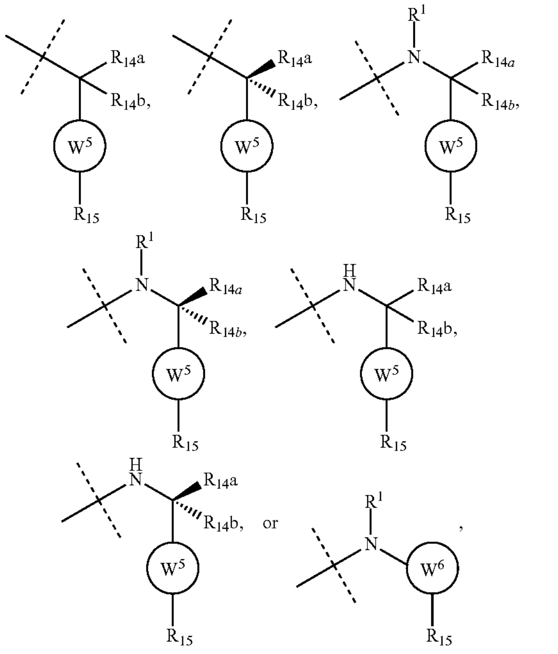

or , wherein:

$W^5$ is optionally substituted phenyl, an optionally substituted napthyl, or optionally substituted 5-10 membered heteroaryl (e.g., $W^5$ is optionally substituted with one or more [such as 1, 2, 3, 4, or 5] halo, CN, optionally substituted linear or branched C1-C12 alkyl optionally having one or more (e.g., 1, 2, 3, 4 or more) carbon atoms replaced with an oxygen atom, optionally substituted haloalkyl, optionally substituted alkoxy, hydroxy, or optionally substituted haloalkoxy);

$R_{14a}$, $R_{14b}$, are each independently selected from the group of H, haloalkyl, optionally substituted alkoxy, optionally substituted hydroxyl alkyl, —$(CH_2)_{m'}C(═O)(CH_2)_{m'}C(═O)(OH)$, $(CH_2)_{m'}OCOCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, or optionally substituted linear or branched alkyl optionally with one or more carbon atoms replaced with an oxygen;

each m' is individually an integer from 1 to 4 (e.g., 1, 2, 3, or 4);

$R^1$ is H, linear or branched $C_1$-$C_6$ alkyl group optionally substituted by 1 or more halo or —OH groups;

$W^6$ is an optionally substituted 8-14 membered bicyclic heterocycle (e.g.,

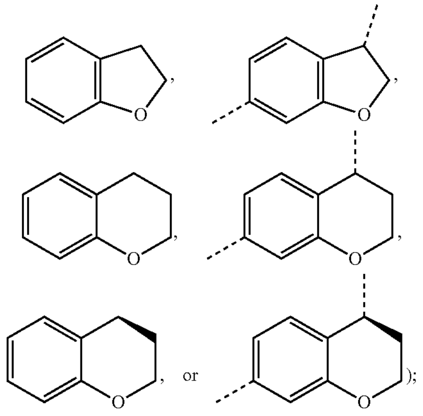

, , , , or );

and $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted alkoxy, optionally substituted haloalkoxy optionally substituted aryl, optionally substituted heteroaryl, optionally substituted cycloalkyl, or optionally substituted cycloheteroalkyl.

In any aspect or embodiment described herein, $W^5$ of Formula ULM-a is selected from the group of an optionally substituted phenyl or an optionally substituted 5-10 membered heteroaryl (e.g., $W^5$ is optionally substituted with one or more [such as 1, 2, 3, 4, or 5] halo, CN, optionally substituted linear or branched C1-C12 alkyl optionally having one or more (e.g., 1, 2, 3, 4 or more) carbon atoms replaced with an oxygen atom, optionally substituted haloalkyl, optionally substituted alkoxy, optionally substituted haloalkoxy, or hydroxy), $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted alkoxy, optionally substituted haloalkoxy, optionally substituted aryl, optionally substituted heteroaryl, optionally substituted cycloalkyl, or optionally substituted cycloheteroalkyl;

In aspect or embodiment described herein, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In aspect or embodiment described herein, ULM-a, is optionally substituted by 0-3 $R^P$ groups in the pyrrolidine moiety. Each $R^P$ is independently H, halo, —OH, C1-3alkyl, C═O.

In aspect or embodiment described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

ULM-b

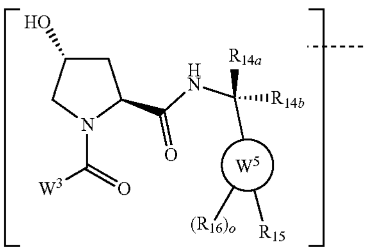

or

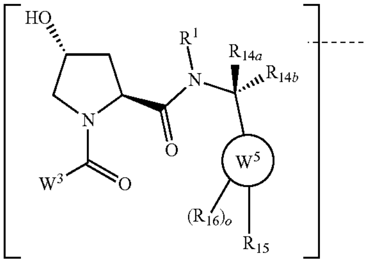

, wherein:

$W^3$ of Formula ULM-b is selected from the group of an optionally substituted aryl, optionally substituted heteroaryl, or

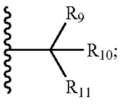

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

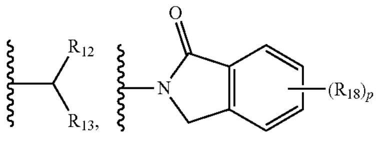

or

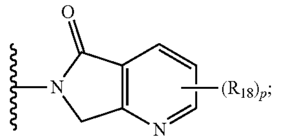

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl, optionally substituted alkoxy, optionally substituted hydroxyl alkyl, $—(CH_2)_mC(═O)(CH_2)_mC(═O)(OH)$, $(CH_2)_mOCOCH_2(CH_2)_mOCH_2(CH_2)_mCO(CH_2)_m$, OH, $(CH_2)_mOCOCH_2(CH_2)_mCO(CH_2)_mOH$, or optionally substituted linear or branched alkyl optionally with one or more carbons replaced with an oxygen;

$R^1$ is H, linear or branched $C_1$-$C_6$ alkyl group optionally substituted by 1 or more halo or —OH groups;

each m' is individually an integer from 1 to 4 (e.g., 1, 2, 3, or 4);

$W^5$ of Formula ULM-b is selected from the group of an optionally substituted phenyl or an optionally substituted 5-10 membered heteroaryl, $R_{15}$ of Formula ULM-b is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy optionally substituted aryl, optionally substituted heteroaryl, optionally substituted cycloalkyl, or optionally substituted cycloheteroalkyl;

each $R_{16}$ of Formula ULM-b is independently selected from the group of H, CN, halo, optionally substituted alkyl optionally having one or more carbon atoms replaced with an oxygen atom (e.g., optionally substituted with CN or OH), optionally substituted haloalkyl, hydroxy, or optionally substituted haloalkoxy;

o of Formula ULM-b is 0, 1, 2, 3, or 4;

$R_{18}$ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

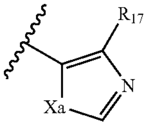

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

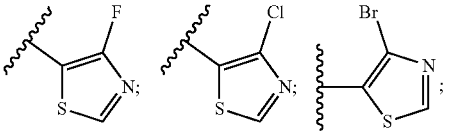
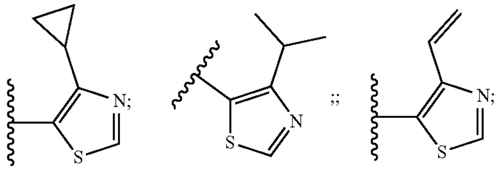
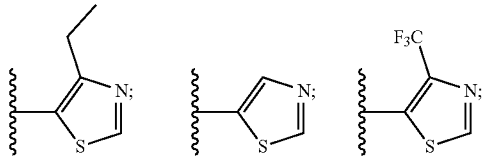
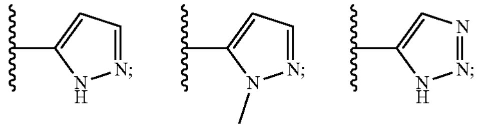
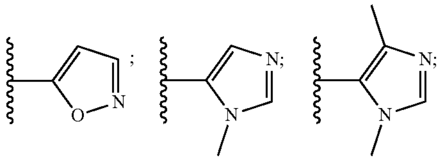
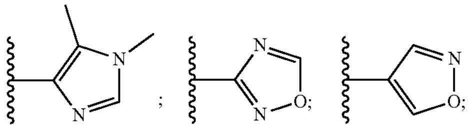
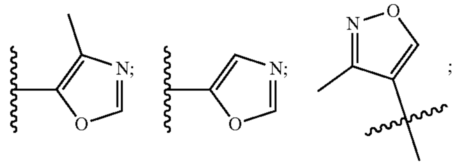
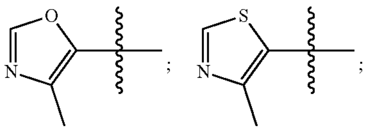

-continued

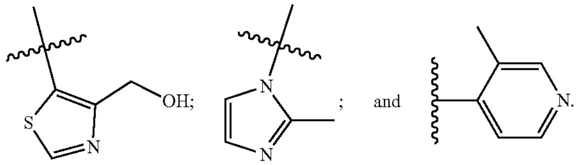

In certain embodiments, $R_{11}$ of Formula ULM-b is selected from the group consisting of:

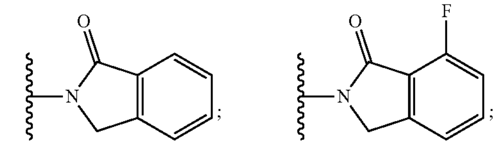
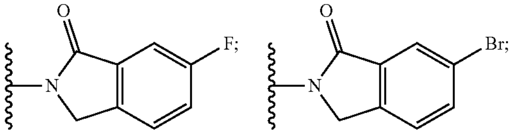
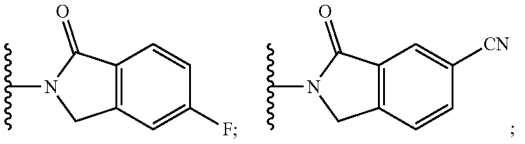
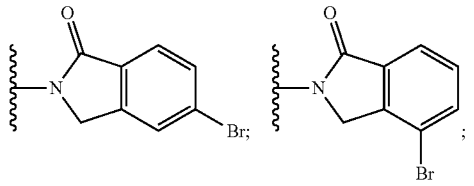
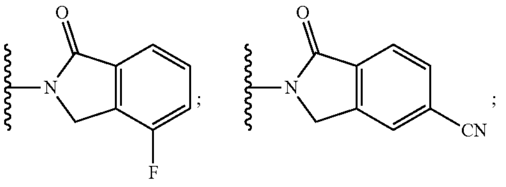
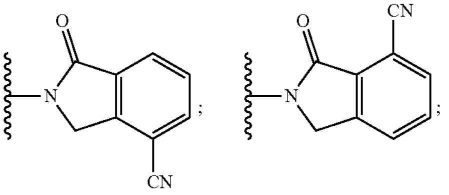
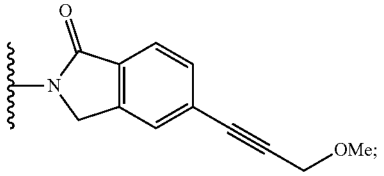
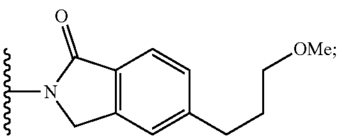

-continued

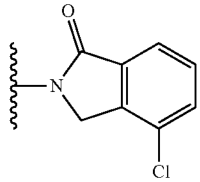
;
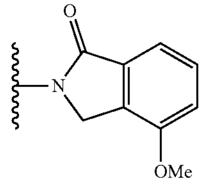
;
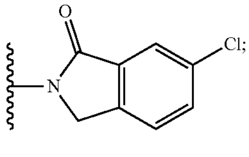
; and
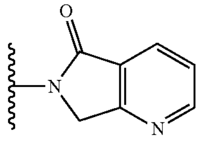
.

In certain embodiments, ULM has a chemical structure selected from the group of:

ULM-c

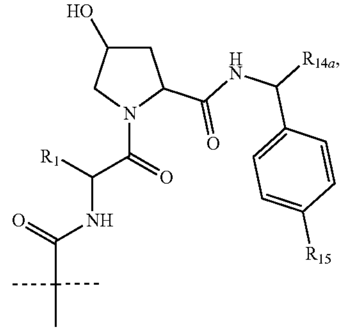

ULM-d

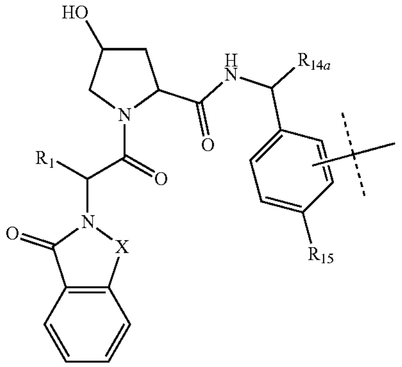

ULM-e

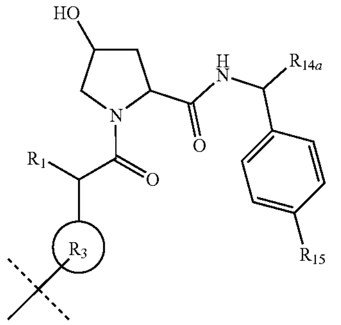

wherein:

$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, $(CH_2)_{m'}O$-$COCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, or cyclopropyl;

each m' is individually an integer from 1 to 4 (e.g., 1, 2, 3, or 4);

$R_{15}$ of Formulas ULM-c, ULM-d, and ULM-e is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, cycloalkyl, or cycloheteroalkyl;

X of Formulas ULM-c, ULM-d, and ULM-e is C, $CH_2$, or C═O $R_3$ of Formulas ULM-c, ULM-d, and ULM-e is absent or a bond or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

ULM-f

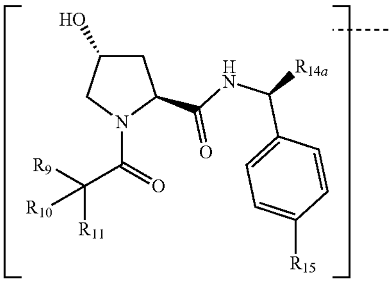
, wherein:

$R_{14a}$ of Formula ULM-f is H, haloalkyl, optionally substituted alkyl, methyl, fluoromethyl, hydroxymethyl, ethyl, isopropyl, $(CH_2)_{m'}OCOCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, or cyclopropyl;

each m' is individually an integer from 1 to 4 (e.g., 1, 2, 3, or 4);

$R_9$ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl;

$R_{11}$ of Formula ULM-f is

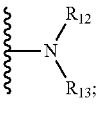
;
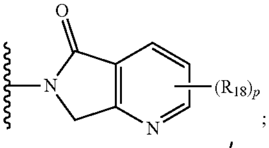
;
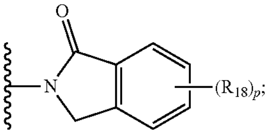
;
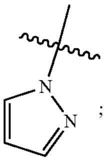
;

-continued

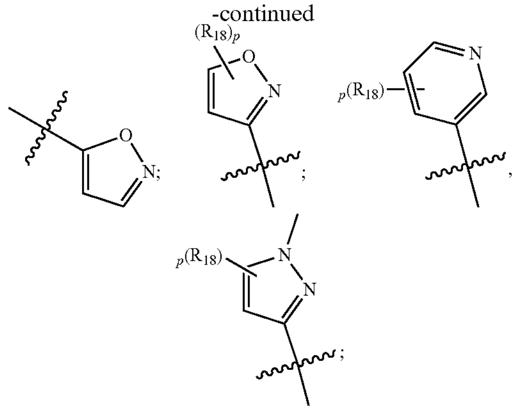

or optionally substituted heteroaryl;

p of Formula ULM-f is 0, 1, 2, 3, or 4;

each $R_{18}$ of Formula ULM-f is independently halo, optionally substituted alkoxy, cyano, optionally substituted alkyl, haloalkyl, haloalkoxy or a linker;

$R_{12}$ of Formula ULM-f is H, C═O;

$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula ULM-f is selected from the group consisting of H, halogen, Cl, CN, OH, $NO_2$, optionally substituted heteroaryl, optionally substituted aryl; optionally substituted cycloheteroalkyl;

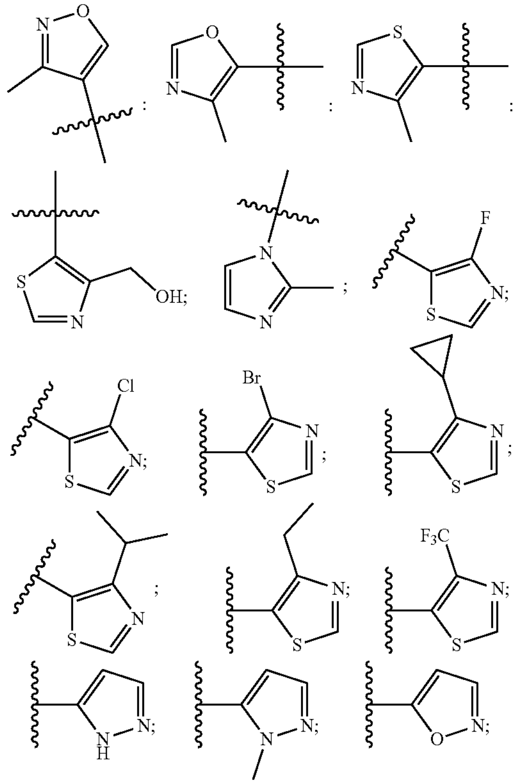

-continued

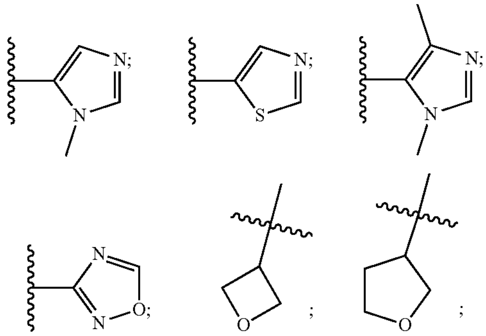

and the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

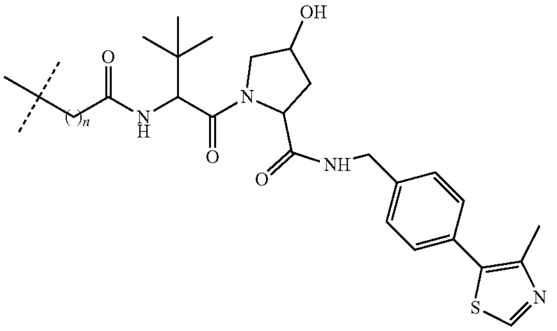

ULM-a2

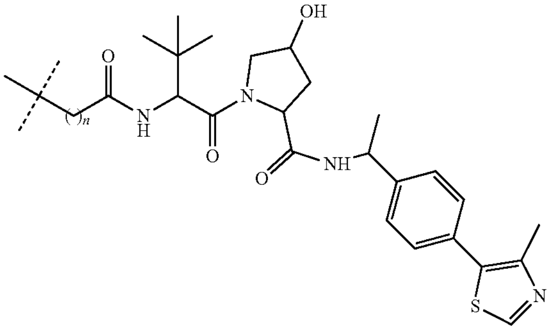

ULM-a3

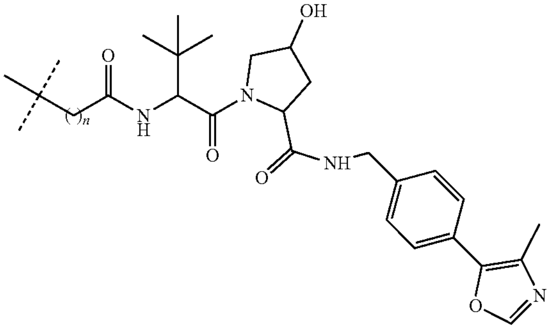

-continued
ULM-a4
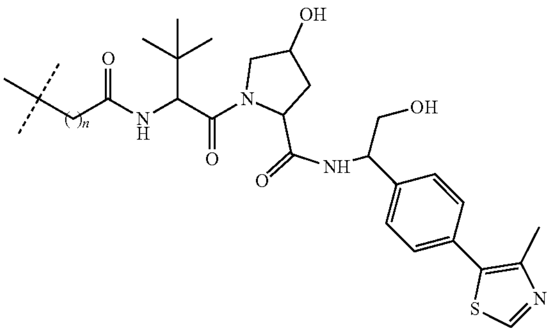
ULM-a5
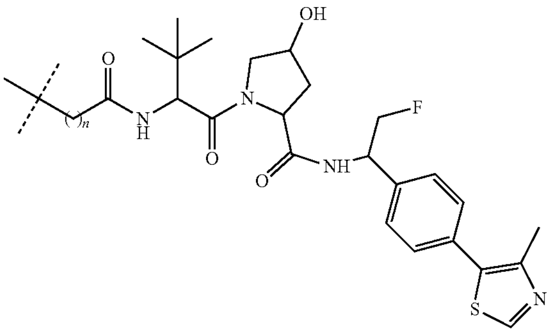
ULM-a6
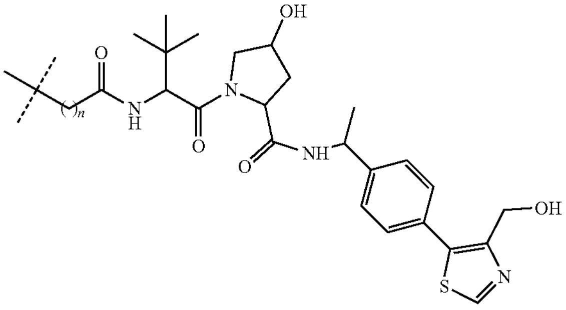
ULM-a7
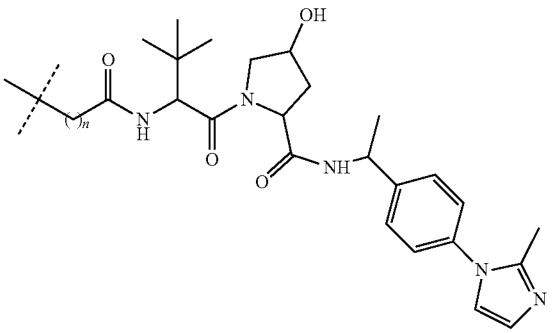
-continued
ULM-a8
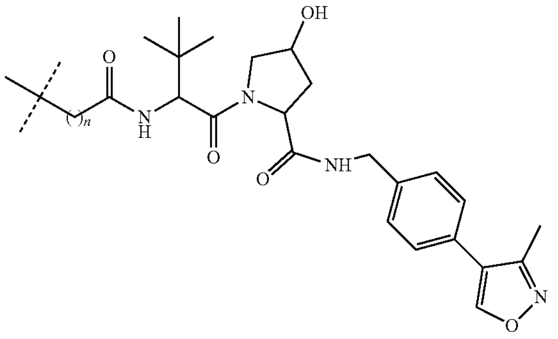
ULM-a9
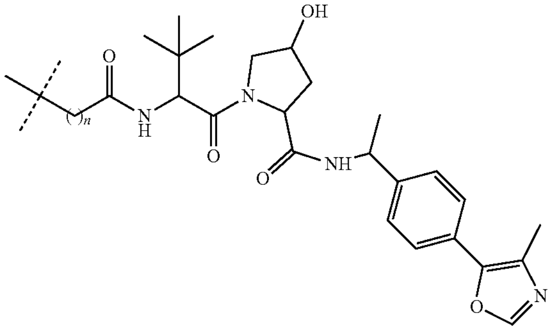
ULM-a10
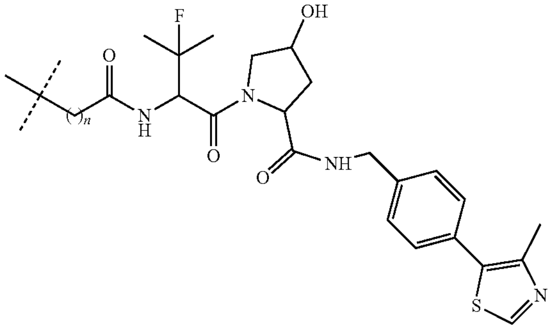
ULM-a11
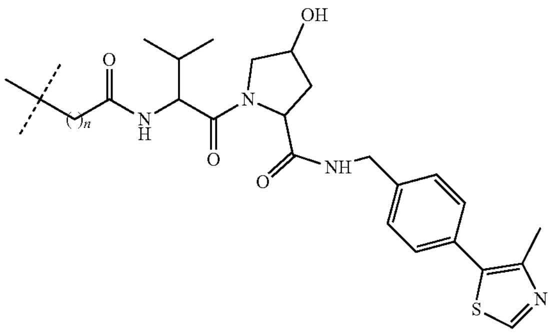

-continued
ULM-a12
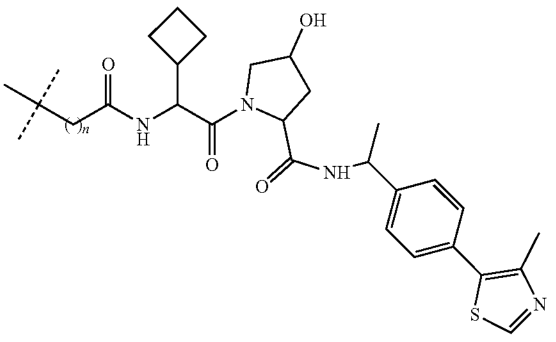
ULM-a13
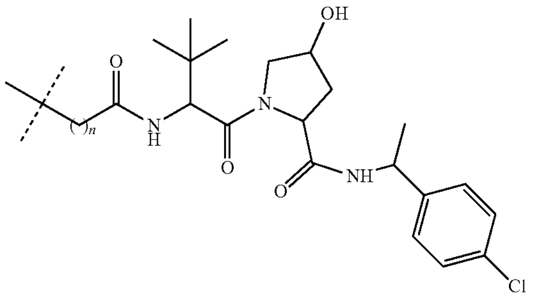
ULM-a14
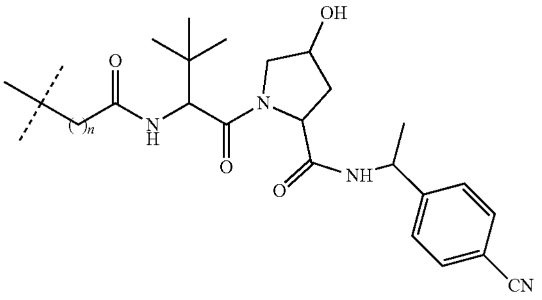
ULM-a15
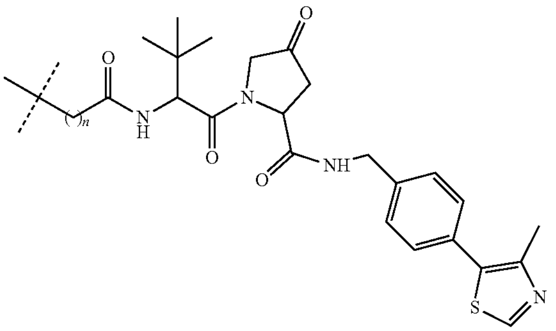
wherein n is 0 or 1.
In certain embodiments, the ULM is selected from the following structures:
ULM-b1
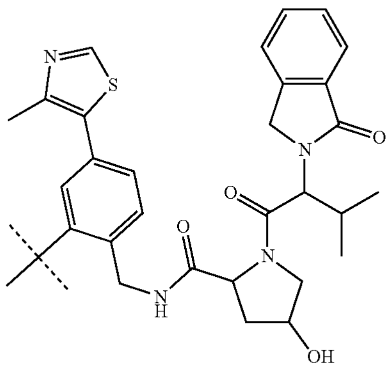
ULM-b2
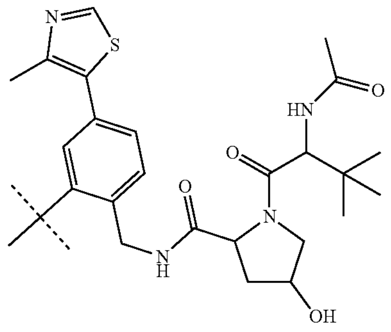
ULM-b3
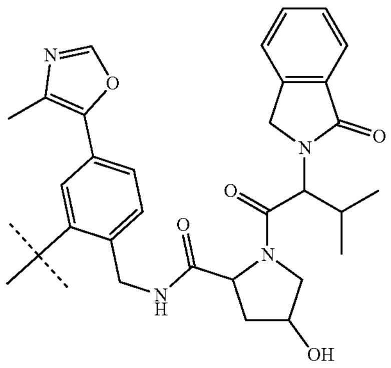
ULM-b4
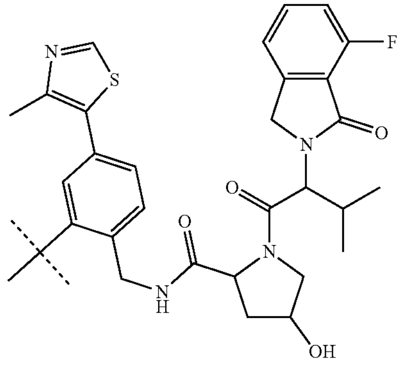

-continued
ULM-b5
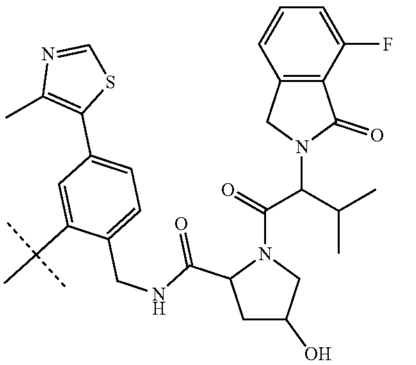
ULM-b6
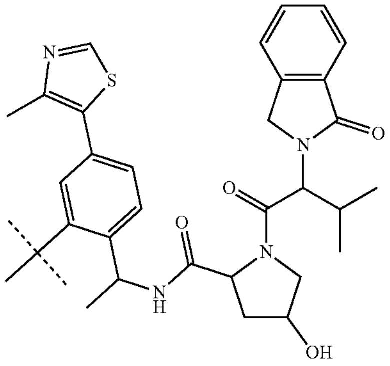
ULM-b7
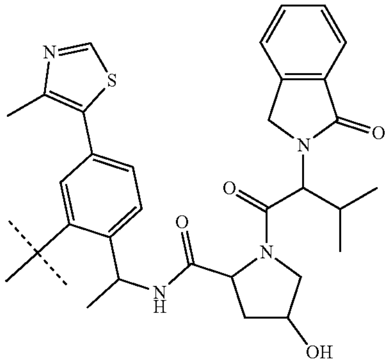
ULM-b8
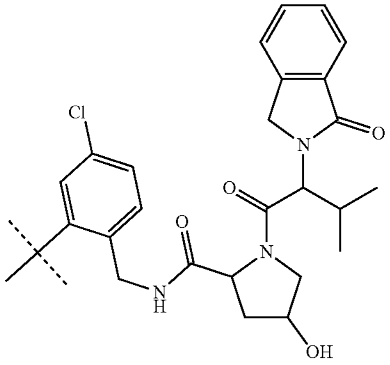
-continued
ULM-b9
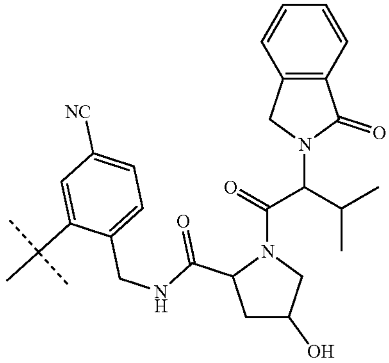
ULM-b10
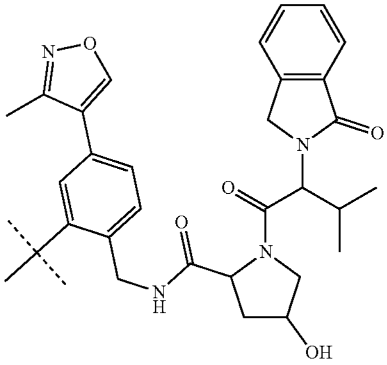
ULM-b11
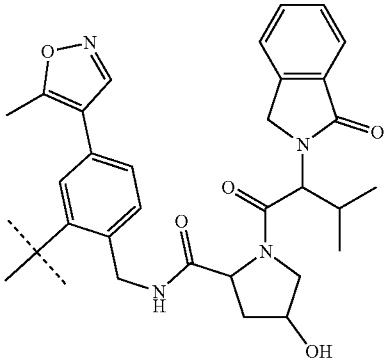
ULM-b12
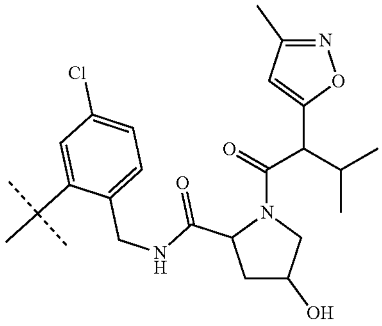

-continued
ULM-c1
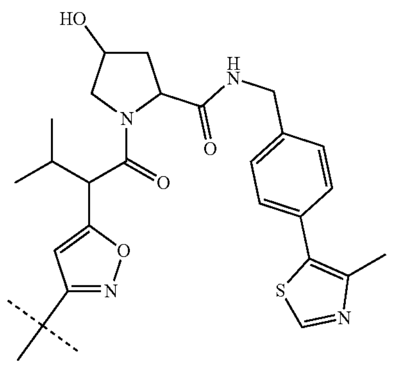
ULM-c2
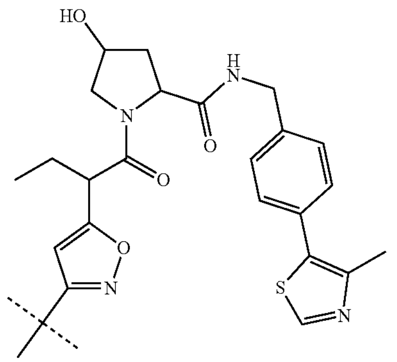
ULM-c3
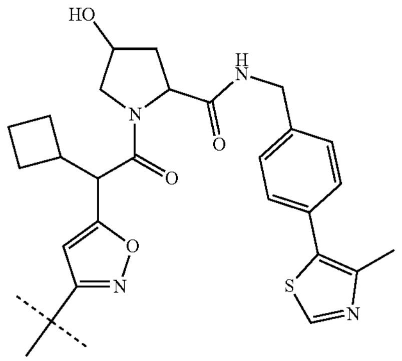
ULM-c4
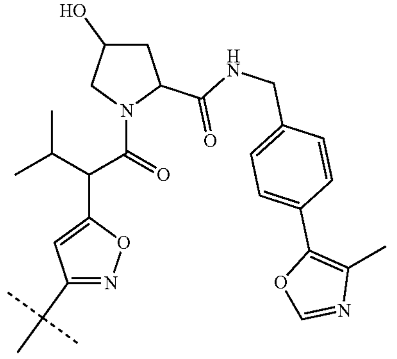
-continued
ULM-c5
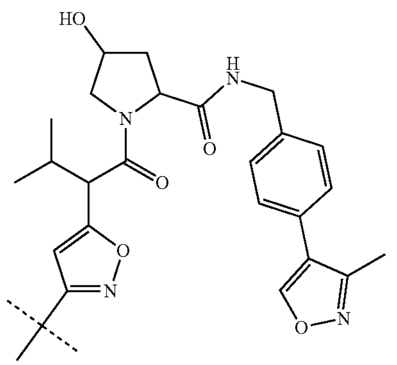
ULM-c6
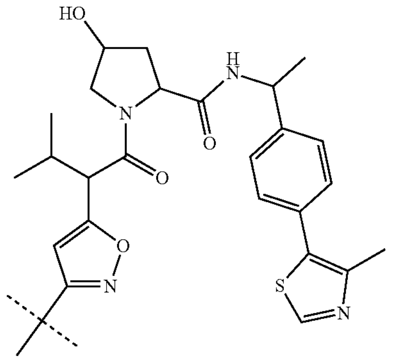
ULM-c7
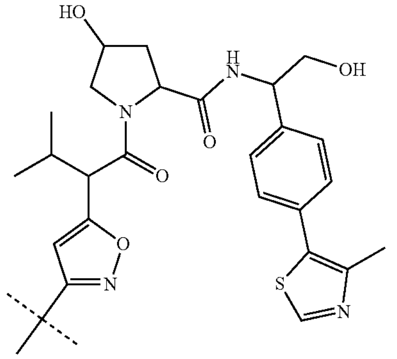
ULM-c8
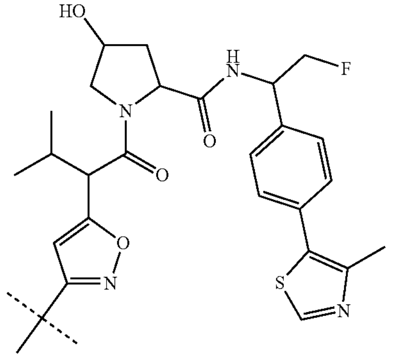

-continued
ULM-c9
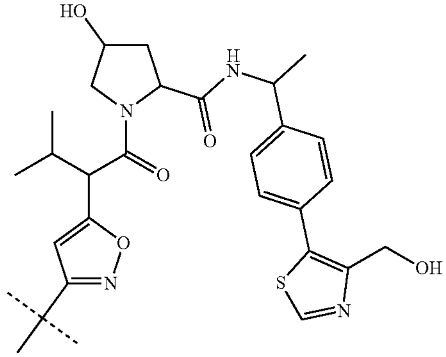
ULM-c10
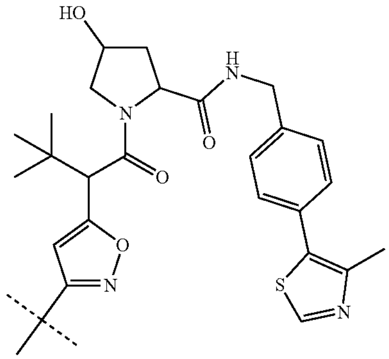
ULM-c11
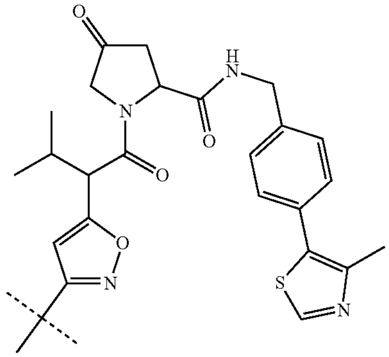
ULM-c12
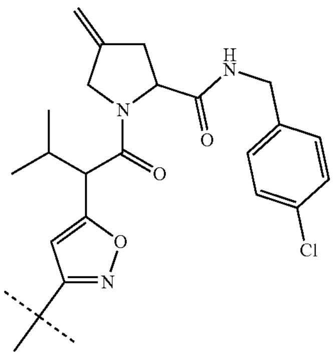
-continued
ULM-c13
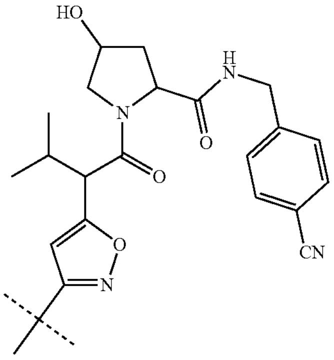
ULM-c14
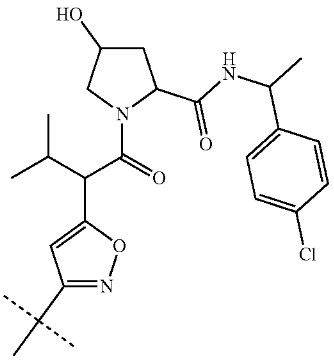
ULM-c15
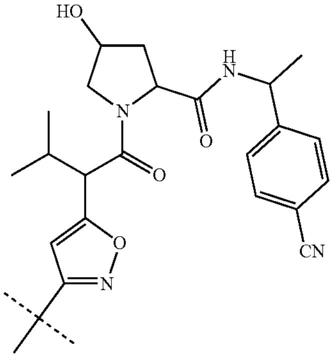
ULM-d1
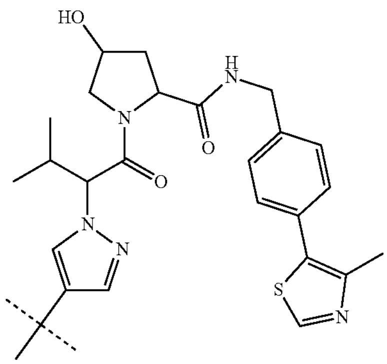

-continued
ULM-d2
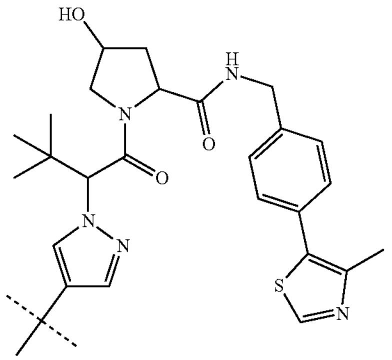
ULM-d3
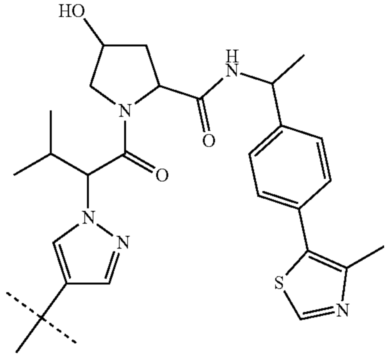
ULM-d4
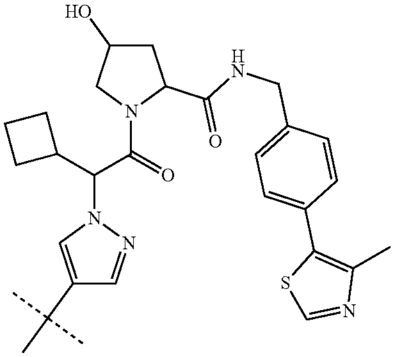
ULM-d5
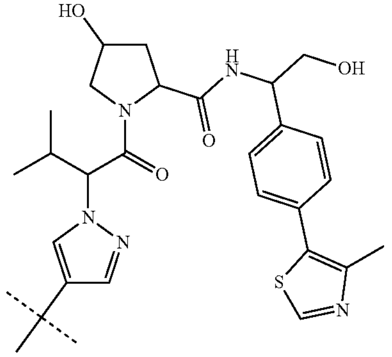
-continued
ULM-d6
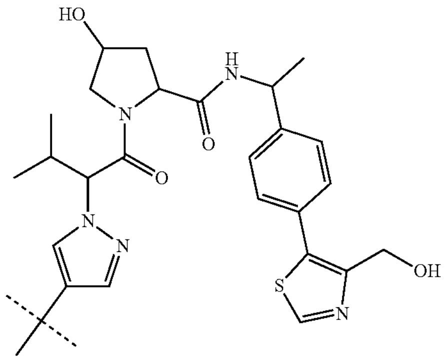
ULM-d7
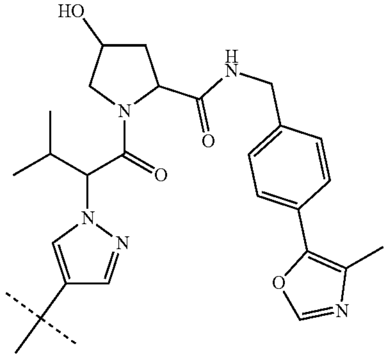
ULM-d8
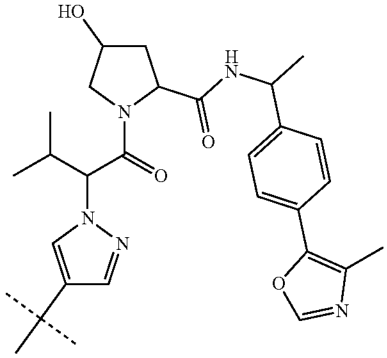
ULM-d9
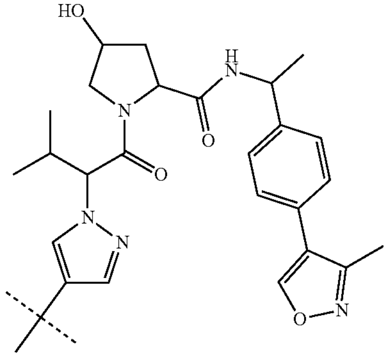

-continued

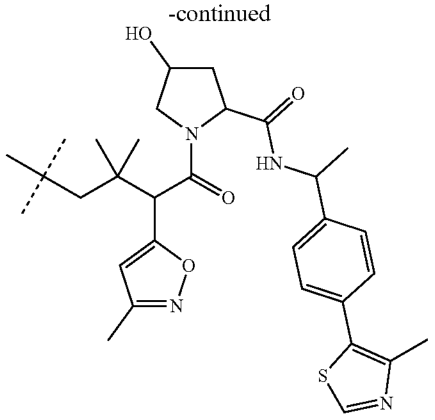

wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

ULM-g

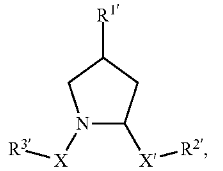

wherein:

$R^{1'}$ of ULM-g is an optionally substituted $C_1$-$C_6$ alkyl group, an optionally substituted $-(CH_2)_nOH$, an optionally substituted $-(CH_2)_nSH$, an optionally substituted $(CH_2)_n-O-(C_1$-$C_6)$alkyl group, an optionally substituted $(CH_2)_n-WCOCW-(C_0$-$C_6)$alkyl group containing an epoxide moiety WCOCW where each W is independently H or a $C_1$-$C_3$ alkyl group, an optionally substituted $-(CH_2)_nCOOH$, an optionally substituted $-(CH_2)_nC(O)-(C_1$-$C_6$ alkyl), an optionally substituted $-(CH_2)_nNHC(O)-R_1$, an optionally substituted $-(CH_2)_nC(O)-NR_1R_2$, an optionally substituted $-(CH_2)_nOC(O)-NR_1R_2$, $-(CH_2O)_nH$, an optionally substituted $-(CH_2)_nOC(O)-(C_1$-$C_6$ alkyl), an optionally substituted $-(CH_2)_nC(O)-O-(C_1$-$C_6$ alkyl), an optionally substituted $-(CH_2O)_nCOOH$, an optionally substituted $-(OCH_2)_nO-(C_1$-$C_6$ alkyl), an optionally substituted $-(CH_2O)_nC(O)-(C_1$-$C_6$ alkyl), an optionally substituted $-(OCH_2)_nNHC(O)-R_1$, an optionally substituted $-(CH_2O)_nC(O)-NR_1R_2$, $-(CH_2CH_2O)_nH$, an optionally substituted $-(CH_2CH_2O)_nCOOH$, an optionally substituted $-(OCH_2CH_2)_nO-(C_1$-$C_6$ alkyl), an optionally substituted $-(CH_2CH_2O)_nC(O)-(C_1$-$C_6$ alkyl), an optionally substituted $-(OCH_2CH_2)_nNHC(O)-R_1$, an optionally substituted $-(CH_2CH_2O)_nC(O)-NR_1R_2$, an optionally substituted $-SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a $-(CH_2)_mNR_1R_2$ group;

X and X' of ULM-g are each independently C=O, C=S, $-S(O)$, $S(O)_2$, (preferably X and X' are both C=O);

$R^{2'}$ of ULM-g is an optionally substituted $-(CH_2)_n-(C{=}O)_u(NR_1)_v(SO_2)_w$alkyl group, an optionally substituted $-(CH_2)_n-(C{=}O)_u(NR_1)_v(SO_2)_wNR_{1N}R_{2N}$ group, an optionally substituted $-(CH_2)_n-(C{=}O)_u(NR_1)_v(SO_2)_w$-Aryl, an optionally substituted $-(CH_2)_n-(C{=}O)_u(NR_1)_v(SO_2)_w$-Heteroaryl, an optionally substituted $-(CH_2)_n-(C{=}O)_vNR_1(SO_2)_w$-Heterocycle, an optionally substituted $-NR^1-(CH_2)_n-C(O)_u(NR_1)_v(SO_2)_w$-alkyl, an optionally substituted $-NR^1-(CH_2)_n-C(O)_u(NR_1)_v(SO_2)_w-NR_{1N}R_{2N}$, an optionally substituted $-NR^1-(CH_2)_n-C(O)_u(NR_1)_v(SO_2)_w-NR_1C(O)R_{1N}$, an optionally substituted $-NR^1-(CH_2)_n-(C{=}O)_u(NR_1)_v(SO_2)_w$-Aryl, an optionally substituted $-NR^1-(CH_2)_n-(C{=}O)_u(NR_1)_v(SO_2)_w$-Heteroaryl or an optionally substituted $-NR^1-(CH_2)_n-(C{=}O)_vNR_1(SO_2)_w$-Heterocycle, an optionally substituted $-X^{R2}$-alkyl group; an optionally substituted $-X^{R2}-$ Aryl group; an optionally substituted $-X^{R2}-$ Heteroaryl group; an optionally substituted $-X^{R2}-$ Heterocycle group; an optionally substituted;

$R^{3'}$ of ULM-g is an optionally substituted alkyl, an optionally substituted $-(CH_2)_n-(O)_u(NR_1)_v(SO_2)_w$-alkyl, an optionally substituted $-(CH_2)_n-C(O)_u(NR_1)_v(SO_2)_w-NR_{1N}R_{2N}$, an optionally substituted $-(CH_2)_n-C(O)_u(NR_1)_v(SO_2)_w-NR_1C(O)R_{1N}$, an optionally substituted $-(CH_2)_n-C(O)_u(NR_1)_v(SO_2)_w-C(O)NR_1R_2$, an optionally substituted $-(CH_2)_n-C(O)_u(NR_1)_v(SO_2)_w$-Aryl, an optionally substituted $-(CH_2)_n-C(O)_u(NR_1)_v(SO_2)_w$-Heteroaryl, an optionally substituted $-(CH_2)_n-C(O)_u(NR_1)_v(SO_2)_w$-Heterocycle, an optionally substituted $-NR^1-(CH_2)_n-C(O)_u(NR_1)_v(SO_2)_w$-alkyl, an optionally substituted $-NR^1-(CH_2)_n-C(O)_u(NR_1)_v(SO_2)_w-NR_{1N}R_{2N}$, an optionally substituted $-NR^1-(CH_2)_n-C(O)_u(NR_1)_v(SO_2)_w-NR_1C(O)R_{1N}$, an optionally substituted $-NR^1-(CH_2)_n-C(O)_u(NR_1)_v(SO_2)_w$-Aryl, an optionally substituted $-NR^1-(CH_2)_n-C(O)_u(NR_1)_v(SO_2)_w$-Heteroaryl, an optionally substituted $-NR^1-(CH_2)_n-C(O)_u(NR_1)_v(SO_2)_w$-Heterocycle, an optionally substituted $-O-(CH_2)_n-(C{=}O)_u(NR_1)_v(SO_2)_w$-alkyl, an optionally substituted $-O-(CH_2)_n-(C{=}O)_u(NR_1)_v(SO_2)_w-NR_{1N}R_{2N}$, an optionally substituted $-O-(CH_2)_n-(C{=}O)_u(NR_1)_v(SO_2)_w-NR_1C(O)R_{1N}$, an optionally substituted $-O-(CH_2)_n-(C{=}O)_u(NR_1)_v(SO_2)_w$-Aryl, an optionally substituted $-O-(CH_2)_n-(C{=}O)_u(NR_1)_v(SO_2)_w$-Heteroaryl or an optionally substituted $-O-(CH_2)_n-(C{=}O)_u(NR_1)_v(SO_2)_w$-

Heterocycle; $-(CH_2)_n-(V)_{n'}-(CH_2)_n-(V)_{n'}$-alkyl group, an optionally substituted $-(CH_2)_n-(V)_{n'}-(CH_2)_n-(V)_{n'}$-Aryl group, an optionally substituted $-(CH_2)_n-(V)_{n'}-(CH_2)_n-(V)_{n'}$-Heteroaryl group, an optionally substituted $-(CH_2)_n-(V)_{n'}-(CH_2)_n-(V)_{n'}$-Heterocycle group, an optionally substituted $-(CH_2)_n-N(R_{1'})(C{=}O)_{m'}-(V)_{n'}$-alkyl group, an optionally substituted $-(CH_2)_n-N(R_{1'})(C{=}O)_{m'}-(V)_{n'}$-Aryl group, an optionally substituted $-(CH_2)_n-N(R_{1'})(C{=}O)_{m'}-(V)_{n'}$-Heteroaryl group, an optionally substituted $-(CH_2)_n-N(R_{1'})(C{=}O)_{m'}-(V)_{n'}$-Heterocycle group, an optionally substituted $-X^{R3'}-$ alkyl group; an optionally substituted $-X^{R3'}-$ Aryl group; an optionally substituted $-X^{R3'}-$ Heteroaryl group; an optionally substituted $-X^{R3'}$-Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted $-(CH_2)_n$-Aryl, $-(CH_2)_n-$Heteroaryl or $-(CH_2)_n-$Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted $-CH_2)_n-$, $-CH_2)_n-CH(X_v)=CH(X_v)-$ (cis or trans), $-CH_2)_n-CH{\equiv}CH-$, $-(CH_2CH_2O)_n-$ or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

ULM-h

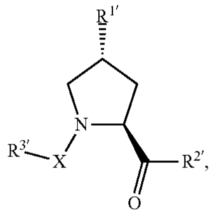

wherein:

each of $R^{1'}$, $R^{2'}$ and $R^{3'}$ of ULM-h are the same as above and X is C═O, C═S, —S(O) group or a $S(O)_2$ group, more preferably a C═O group, and any one or more of $R^1$, $R^2$ and $R^3$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

ULM-i

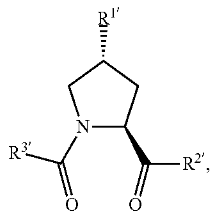

wherein:

any one or more of $R^{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In further aspects of the disclosure, $R^{1'}$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, $-(CH_2)_nOH$, $(CH_2)_n-O-(C_1$-$C_6)$alkyl group, $-(CH_2)_nCOOH$, $-(CH_2O)_nH$, an optionally substituted $-(CH_2)_nOC(O)-(C_1$-$C_6$ alkyl), or an optionally substituted $-(CH_2)_nC(O)-O-(C_1$-$C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C═O, C═S, —S(O) group or a $S(O)_2$ group, more preferably a C═O group;

$R^{2'}$ of ULM-g through ULM-i is preferably an optionally substituted $-NR_1$-T-Aryl, an optionally substituted $-NR^1$-T-Heteroaryl group or an optionally substituted $-NR^1$-T-Heterocycle, where $R^1$ is H or $CH_3$, preferably H and T is an optionally substituted $-(CH_2)_n-$ group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6 (e.g., 0, 1, 2 or 3, such as 0 or 1). Alternatively, T may also be a $-(CH_2O)_n-$ group, a $-(OCH_2)_n-$ group, a $-(CH_2CH_2O)_n-$ group, a $-(OCH_2CH_2)_n-$ group, all of which groups are optionally substituted.

Preferred Aryl groups for $R^2$ of ULM-g through ULM-i include optionally substituted phenyl or naphthyl groups, preferably phenyl groups, wherein the phenyl or naphthyl group is optionally connected to a PTM group via a linker group to which is attached a PTM group (including a ULM' group), a halogen (preferably L or Cl), an amine, monoalkyl- or dialkyl amine (preferably, dimethylamine), L, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PTM via a linker group, including a ULM' group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

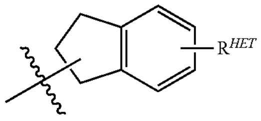

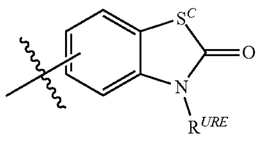

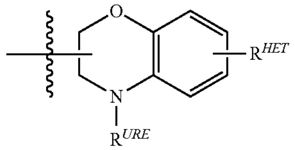

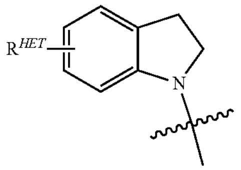

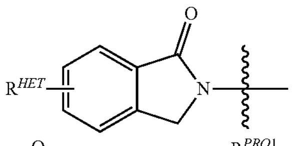

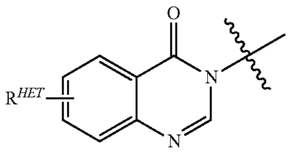

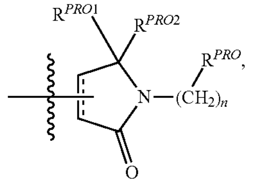

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ ofULM-g through ULM-i each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally connected to a PTM group (including a ULM' group) via a linker group.

In certain preferred aspects,

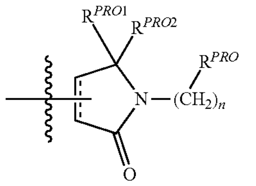

of ULM-g through ULM-i is a

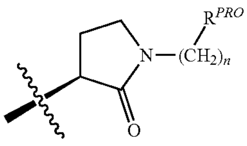

or

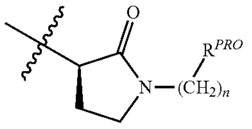

group, where $R^{PRO}$ and n of ULM-g through ULM-i are the same as above.

Preferred heteroaryl groups for $R^2$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

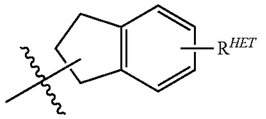

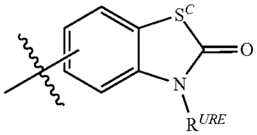

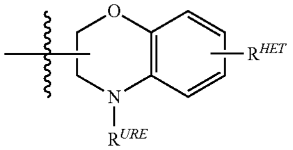

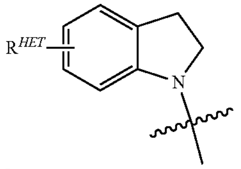

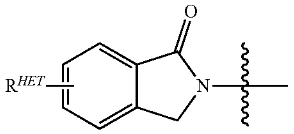

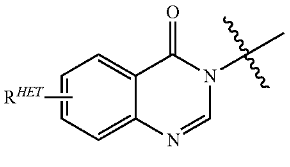

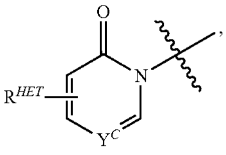

, wherein $S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^2$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

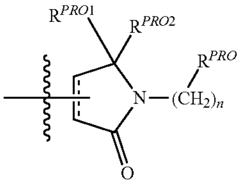

or

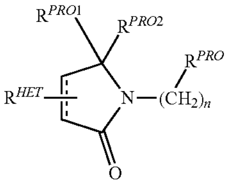

preferably, a

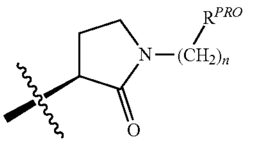

or

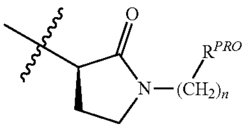

group, wherein:

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted. $C_1$-$C_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-Heterocycle, an optionally substitutcd-$NR^1$-T-Aryl, an optionally substituted —$NR^1$-T-Heteroaryl or an optionally substitutcd-$NR^1$-T-Heterocyclc. In a preferred embodiment $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_6$ alkyl group (linear, branched, optionally substituted) or the side-chain of an amino acid as otherwise described herein, preferably methyl, which may be optionally substituted; and n is 0 to 6, e.g. 0, 1, 2, or 3 (such as 0 or 1). Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or a halogen (preferably F or Cl), an amine, monoalkyl- or dialkyl amine (preferably, dimethylamine), an amido group (preferably a —$(CH_2)_m NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a a $C_1$-$C_6$ alkyl group, an optionally substituted aryl, heteroaryl or heterocycle group or a —$(CH_2)_m NR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^3$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$O—$C_1$-$C_6$ alkyl group or an optionally substituted —$(CH_2)_m$C(O)—O—$C_1$-$C_6$ alkyl group), an optionally substituted pyridine (2-, 3, or 4-pyridine) or a group according to the chemical structure:

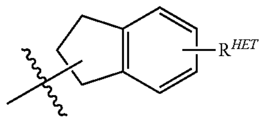
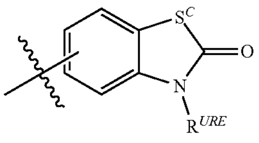
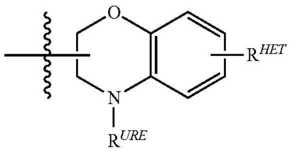
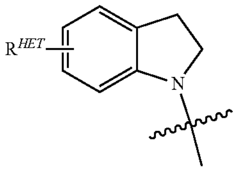
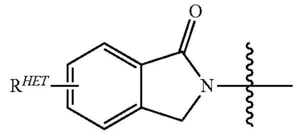
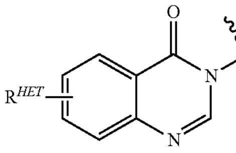
or
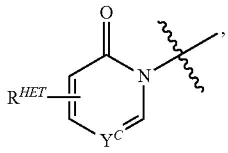, wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^3$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

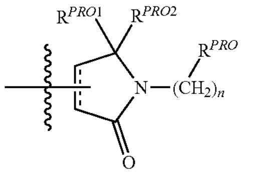

or

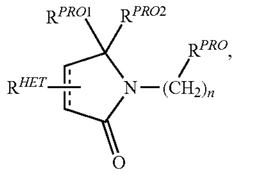

preferably, a

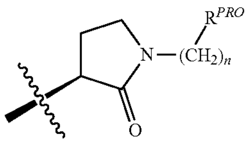

or

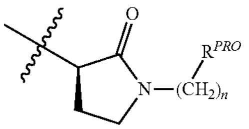

group, wherein:

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said Heterocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$— $X^{R2'}$-HET, an optionally substituted —$NR_1$—$X^{R2'}$-Aryl-HET or an optionally substituted —$NR_1$— $X^{R2'}$-HET-Aryl, wherein:

$R_1$ of ULM-g through ULM-i is H or a $C_1$-$C_3$ alkyl group (preferably H);

$X^{R2'}$ of ULM-g through ULM-i is an optionally substituted —$CH_2)_n$—, —$CH_2)_n$—CH($X_v$)=CH($X_v$)— (cis or trans), —$(CH_2)_n$—CH≡CH—, —$(CH_2CH_2O)_n$— or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted C1-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

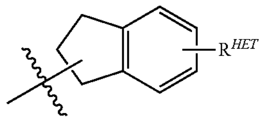

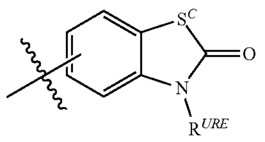

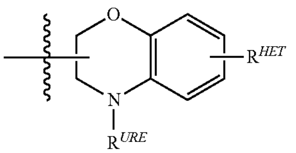

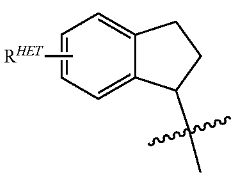

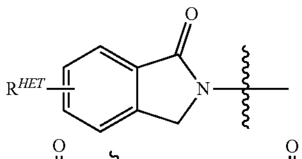

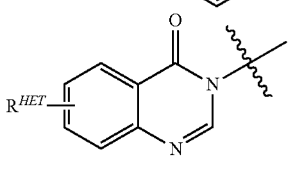

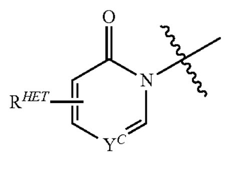

-continued

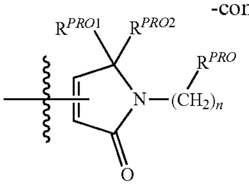

or

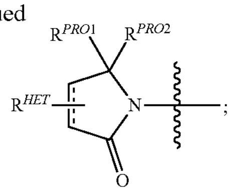

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative embodiments of the present disclosure, $R^{3'}$ of ULM-g through ULM-i is an optionally substituted $—(CH_2)_n—(V)_{n'}—(CH_2)_n—(V)_{n'}—R^{S3'}$ group, an optionally substituted-$(CH_2)_n—N(R_{1'})(C{=}O)_{m'}—(V)_{n'}—R^{S3'}$ group, an optionally substituted $—X^{R3'}$-alkyl group, an optionally substituted $—X^{R3'}$-Aryl group; an optionally substituted $—X^{R3'}$-HET group, an optionally substituted $—X^{R3'}$-Aryl-HET group or an optionally substituted $—X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is $—(CH_2)_n—$, $—(CH_2CH_2O)_n—$, $—CH_2)_n—CH(X_v){=}CH(X_v)—$ (cis or trans), $—CH_2)_n—CH{\equiv}CH—$, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

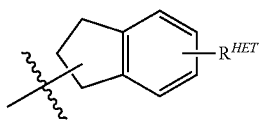

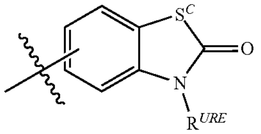

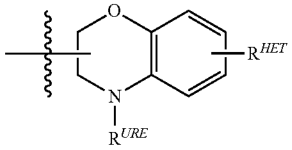

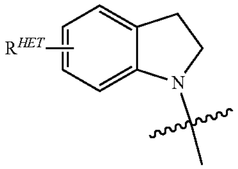

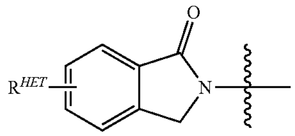

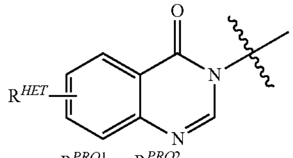

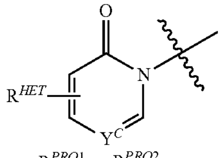

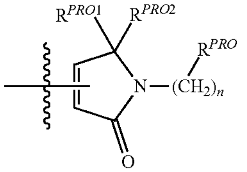

or

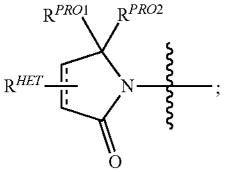

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1\text{-}C_6$ alkyl) (preferably substituted with one or two hydroxyl groups or up to three halo groups) or an optionally substituted acetylenic group —C≡C—$R_a$ where $R_a$ is H or a $C_1\text{-}C_6$ alkyl group (preferably $C_1\text{-}C_3$ alkyl);

$R^{SS}$ of ULM-g through ULM-i is H, CN, $NO_2$, halo (preferably F or Cl), optionally substituted $C_1\text{-}C_6$ alkyl (preferably substituted with one or two hydroxyl groups or up to three halo groups), optionally substituted O—($C_1\text{-}C_6$ alkyl) (preferably substituted with one or two hydroxyl groups or up to three halo groups) or an optionally substituted —C(O)($C_1\text{-}C_6$ alkyl) (preferably substituted with one or two hydroxyl groups or up to three halo groups);

$R^{URE}$ of ULM-g through ULM-i is H, a $C_1\text{-}C_6$ alkyl (preferably H or $C_1\text{-}C_3$ alkyl) or a —C(O)($C_0\text{-}C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1\text{-}C_6$ alkyl (preferably substituted with one or two hydroxyl groups or up to three halo groups (e.g. $CF_3$), optionally substituted $O(C_1\text{-}C_6$ alkyl) (preferably substituted with one or two hydroxyl groups or up to three halo groups) or an optionally substituted acetylenic group —C≡C—$R_a$ where $R_a$ is H or a $C_1\text{-}C_6$ alkyl group (preferably $C_1\text{-}C_3$ alkyl);

$R^{PRO}$ of ULM-g through ULM-i is H, optionally substituted $C_1\text{-}C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1\text{-}C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally subsituted $C_1\text{-}C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker group.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:

said Aryl of ULM-g through ULM-i is phenyl which is optionally substituted with one or two substitutents, wherein said substituent(s) is preferably selected from —$(CH_2)_n$OH, $C_1\text{-}C_6$ alkyl which itself is further optionally substituted with CN, halo (up to three halo groups), OH, —$(CH_2)_n$O($C_1\text{-}C_6$)alkyl, amine, mono- or di-($C_1\text{-}C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1\text{-}C_6$)alkyl, —$(CH_2)_n$—O—$(CH_2)_n$—($C_1\text{-}C_6$)alkyl, —$(CH_2)_n$—C(O)($C_0\text{-}C_6$) alkyl, —$(CH_2)_n$—C(O)O($C_0\text{-}C_6$)alkyl, —$(CH_2)_n$—OC(O)($C_0\text{-}C_6$)alkyl, amine, mono- or di-($C_1\text{-}C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—($C_1\text{-}C_6$)alkyl group, a —$(V)_{m'}$—$(CH_2CH_2O)_n$—$R^{PEG}$ group where V is O, S or $NR_{1'}$, $R_{1'}$ is H or a $C_1\text{-}C_3$ alkyl group (preferably H) and $R^{PEG}$ is H or a $C_1\text{-}C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1\text{-}C_3$ alkyl group, preferably methyl or a halo group, preferably F or Cl), or a group according to the chemical structure:

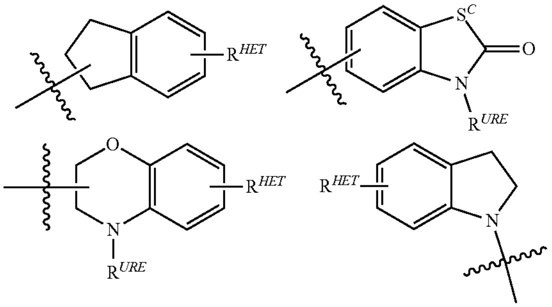

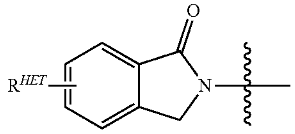

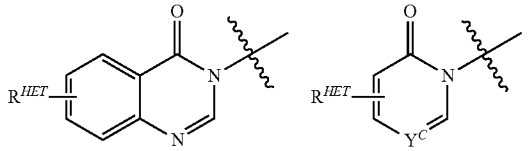

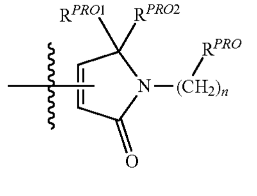

or

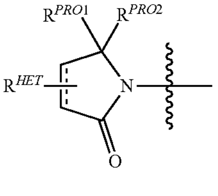

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1\text{-}C_6$ alkyl (preferably substituted with one or two hydroxyl groups or up to three halo groups (e.g. $CF_3$), optionally substituted $O(C_1\text{-}C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

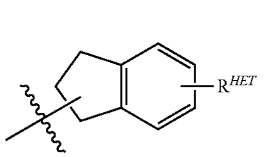
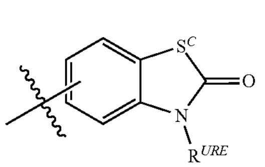
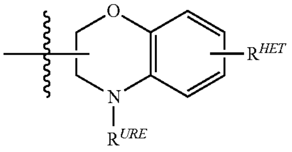
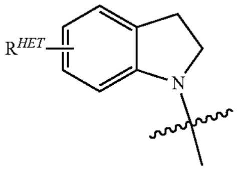

-continued

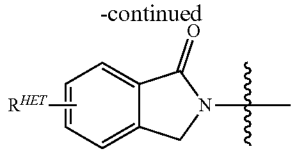
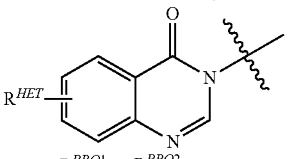
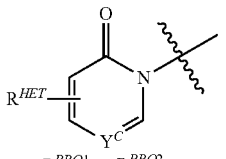
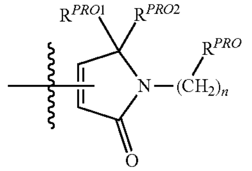
or
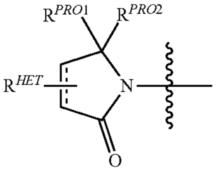

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

ULM-i

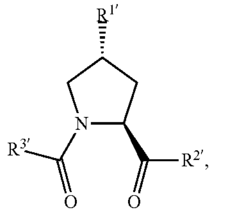

wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^{3'}$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_nOCH_3$ group where n is 1 or 2 (preferably 2), or a

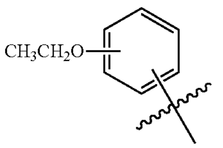

group (the ethyl ether group is preferably meta-substituted on the phenyl moiety), a morpholino group (linked to the carbonyl at the 2- or 3-position;

$R^{3P2}$ of ULM-i is a

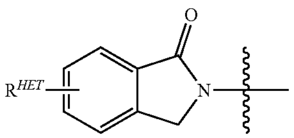

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

ULM-j1

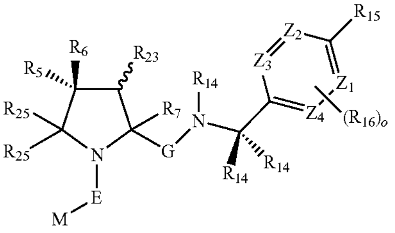

ULM-j2

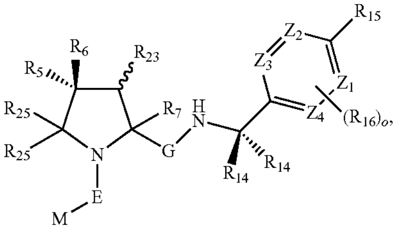

wherein:

each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C═O, or C═S;

G of ULM-j is a bond, optionally substituted alkyl, —COOH or C=J;

J of ULM-j is O or N—$R_8$;

$R_8$ of ULM-j is H, CN, optionally substituted alkyl or optionally substituted alkoxy; M of ULM-j is optionally substituted aryl, optionally substituted heteroaryl, optionally substituted heterocyclic or

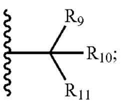

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

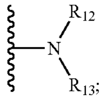

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate, each $R_{14}$ of ULM-j is independently H, haloalkyl, optionally substituted cycloalkyl, optionally substituted alkyl or optionally substituted heterocycloalkyl;

$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C═O and M is

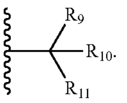

In certain embodiments, wherein E of ULM-j is C═O, $R_{11}$ is optionally substituted heterocyclic or

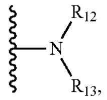

and M is

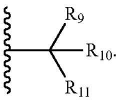

In certain embodiments, wherein E of ULM-j is C═O, M is

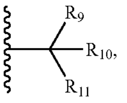

and $R_{11}$ is

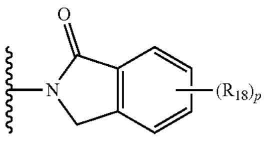

or

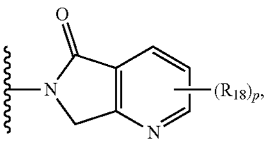

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

ULM-k

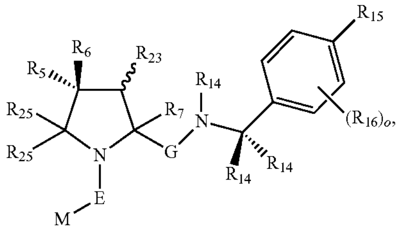

wherein:

G of ULM-k is C=J, J is O;

$R_7$ of ULM-k is H;

each $R_{14}$ of ULM-k is H;

o of ULM-k is 0;

$R_{15}$ of ULM-k is

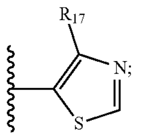

and $R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

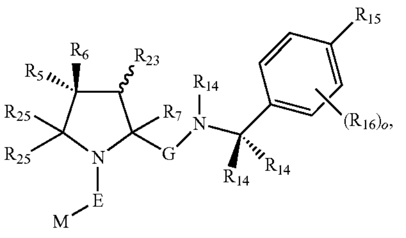

wherein:

G of ULM-k is C=J, J is O;

$R_7$ of ULM-k is H;

each $R_{14}$ of ULM-k is H;

o of ULM-k is 0; and $R_{15}$ of ULM-k is selected from the group consisting of:
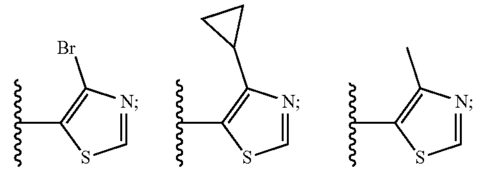
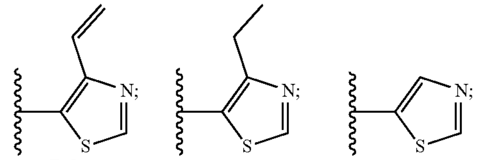
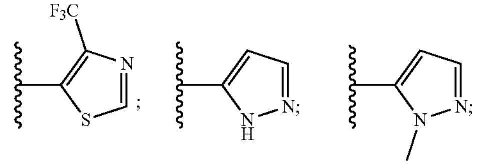
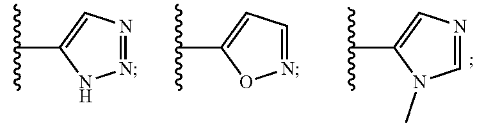
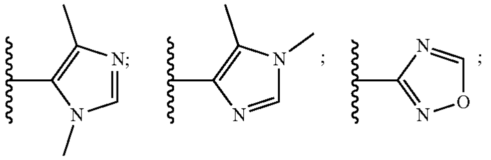
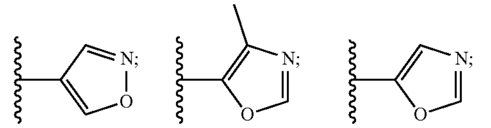
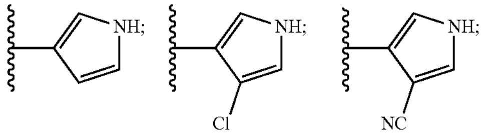
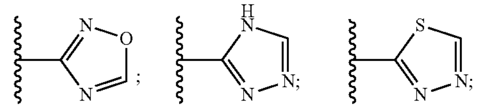
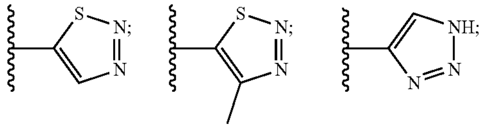
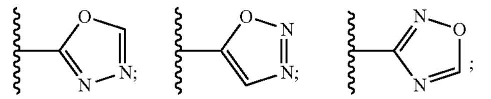
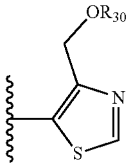
and
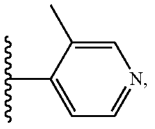
wherein $R_{30}$ of ULM-k is H or an optionally substituted alkyl.
In other embodiments, ULM and where present, ULM', are each independently a group according to the chemical structure:
ULM-k1
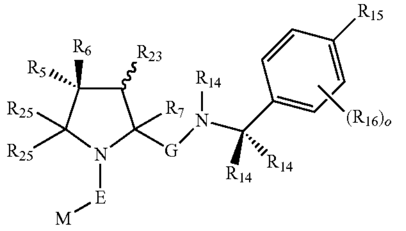
ULM-k2
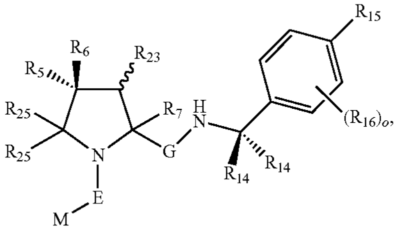
wherein:
E of ULM-k is C═O;
M of ULM-k is
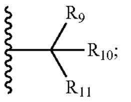
and
$R_{11}$ of ULM-k is selected from the group consisting of:
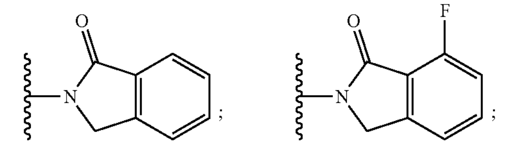
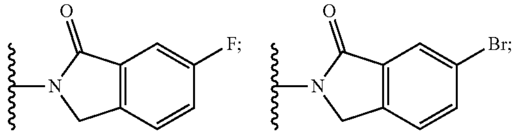
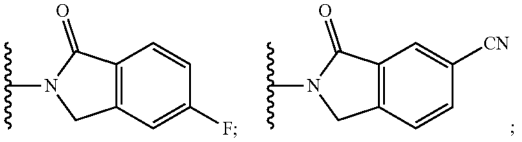
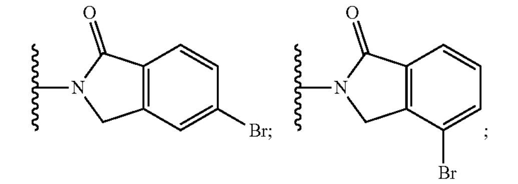
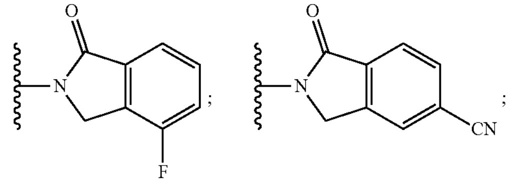

-continued

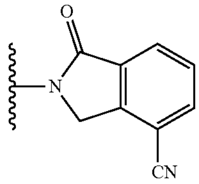 ; 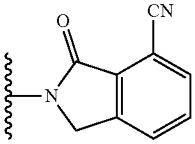 ;

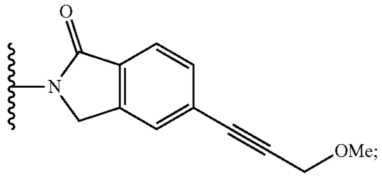

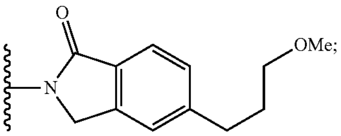

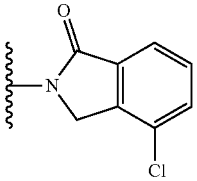 ; 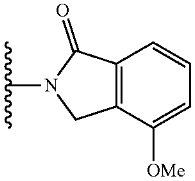 ;

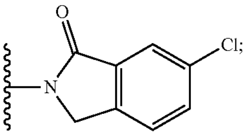 and 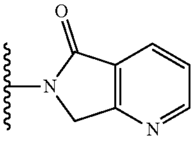 .

In still other embodiments, a compound of the chemical structure.

ULM-k1

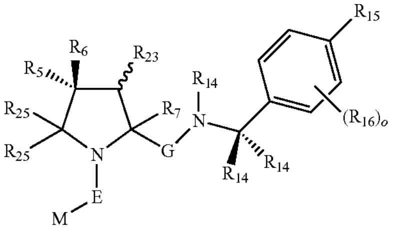

ULM-k2

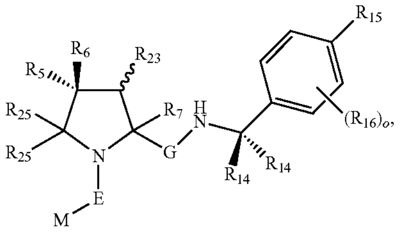

wherein E of ULM-k is C═O;

$R_{11}$ of ULM-k is

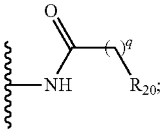

and

M of ULM-k is

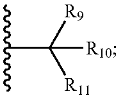

q of ULM-k is 1 or 2;

$R_{20}$ of ULM-k is H, optionally substituted alkyl, optionally substituted cycloalkyl, optionally substituted aryl, or

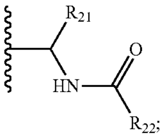

$R_{21}$ of ULM-k is H or optionally substituted alkyl; and $R_{22}$ of ULM-k is H, optionally substituted alkyl, optionally substituted alkoxy, or haloalkyl.

In any embodiment described herein, $R_{11}$ of ULM-j or ULM-k is selected from the group consisting of:

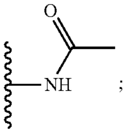 ; 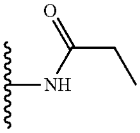 ; 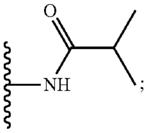 ;

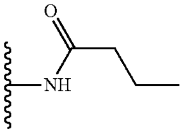 ; 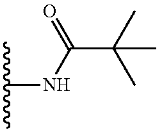 ; 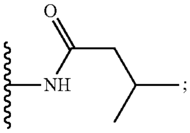 ;

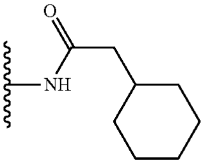 ; 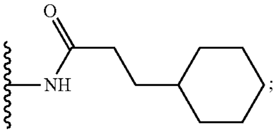 ;

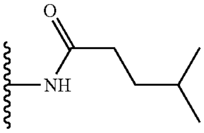 ; 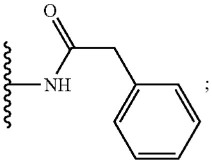 ;

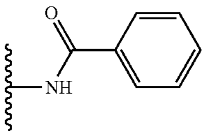 ; 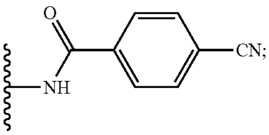

-continued
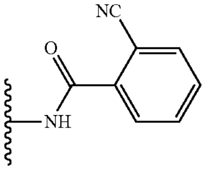
;
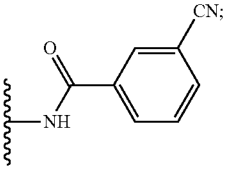
;
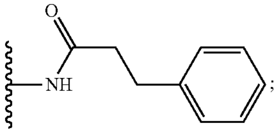
;
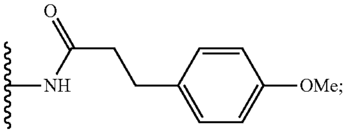
;
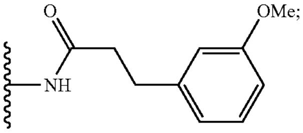
;
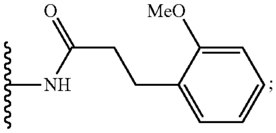
;
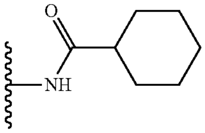
;
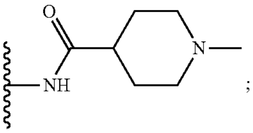
;
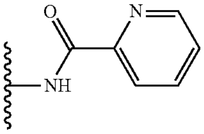
;
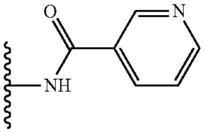
;
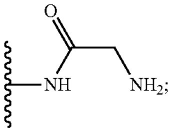
;
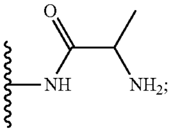
;
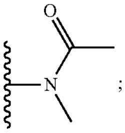
;
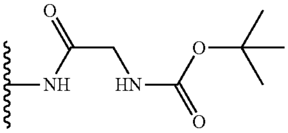
;
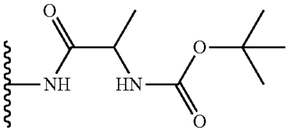
;
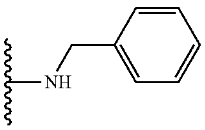
;
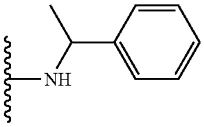
;
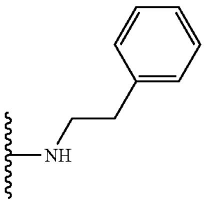
;
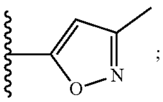
;
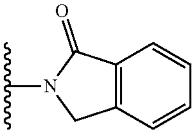
;
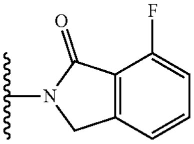
;
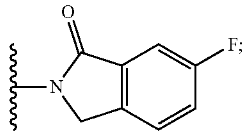
;
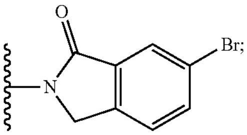
;
-continued
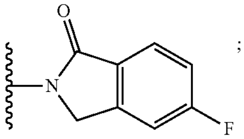
;
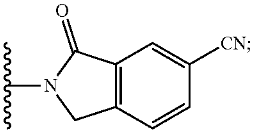
;
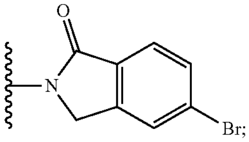
;
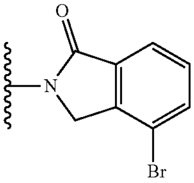
;
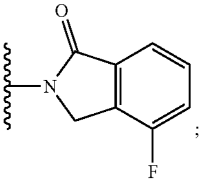
;
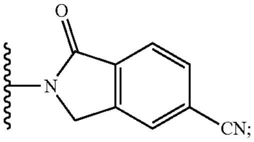
;
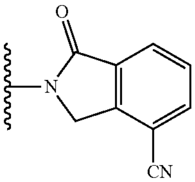
;
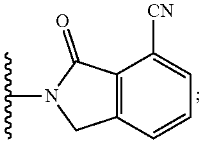
;
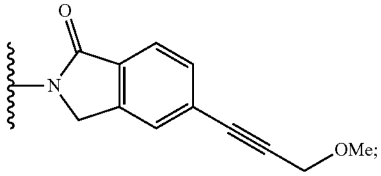
;
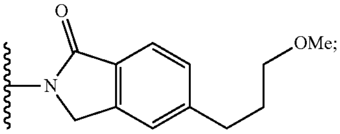
;
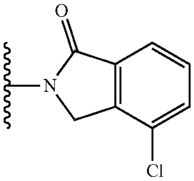
;
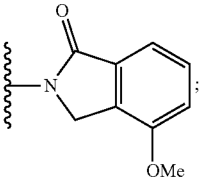
;
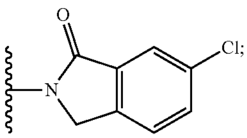
;
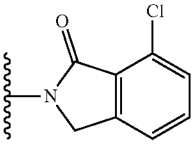
;
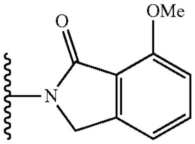
;
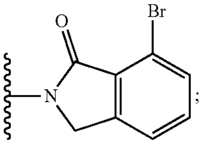
;
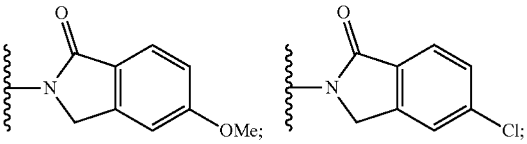
;

-continued
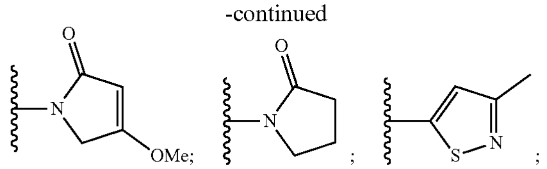
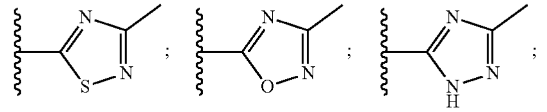
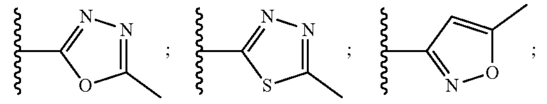
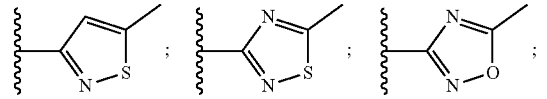
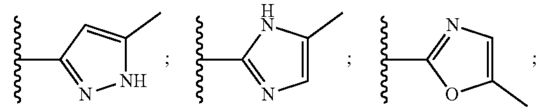
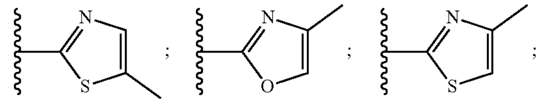
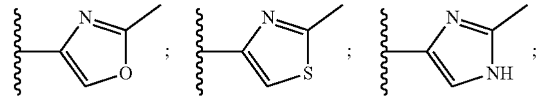
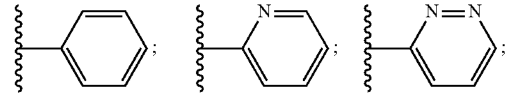
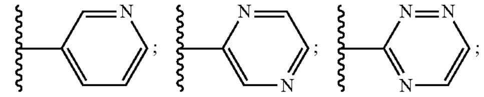
and
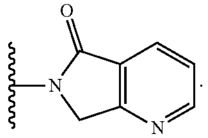
In certain embodiments, $R_{11}$ of ULM-j or ULM-k is selected from the group consisting of:
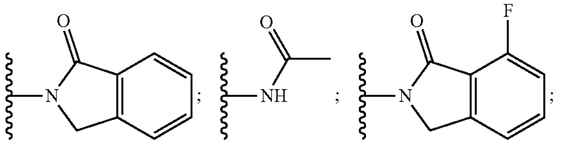
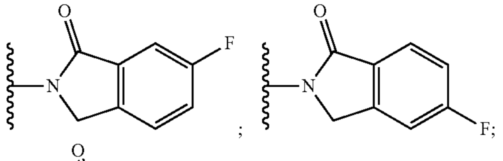
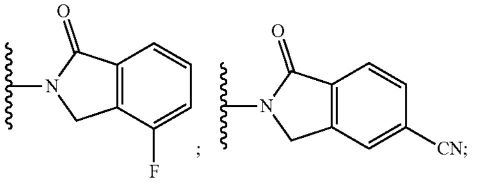
-continued
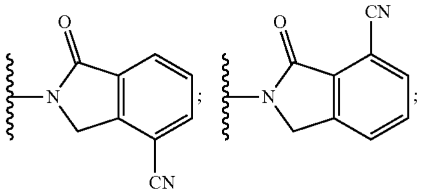
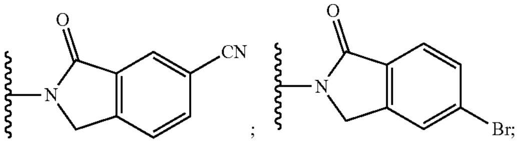
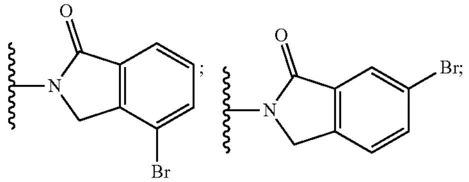
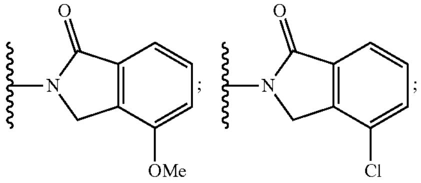
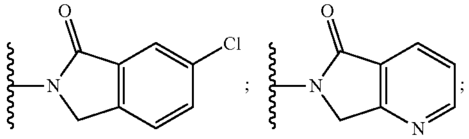
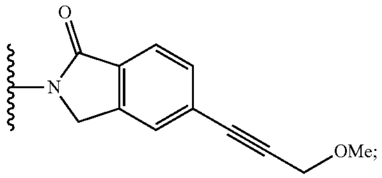
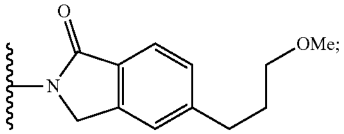
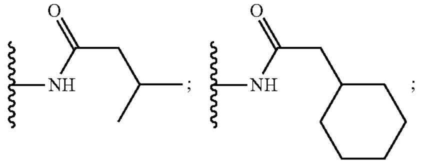
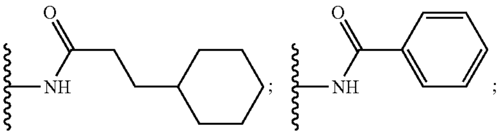
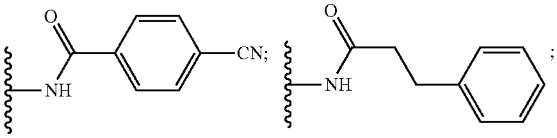
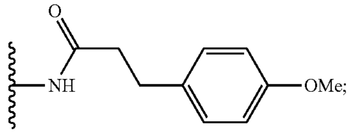

-continued

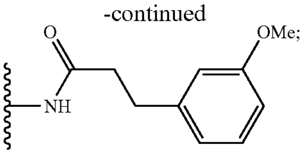

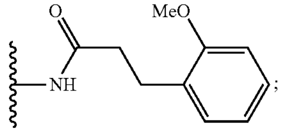
;
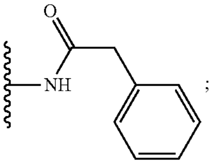
;

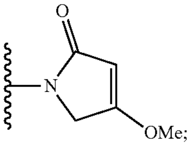
;
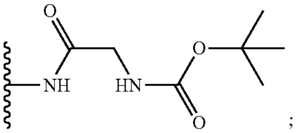
;

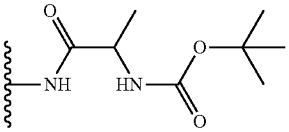
;
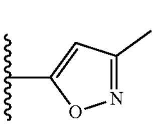

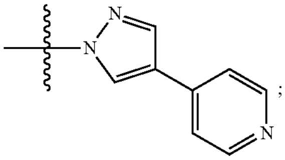
;
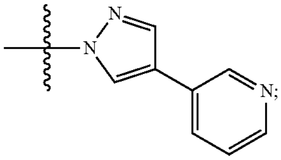
;

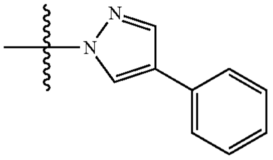

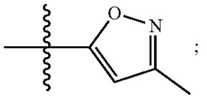
;

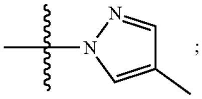
;
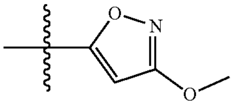
;

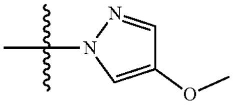

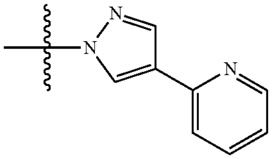
and

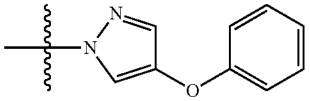 [SMILES: *n1cc(Oc2ccccc2)cn1]

In certain embodiments, ULM (or when present ULM') is a group according to the chemical structure:

ULM-1

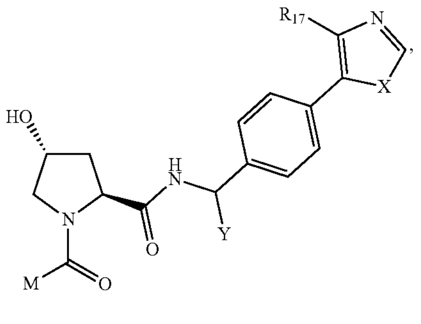

wherein:

X of ULM-1 is O or S;

Y of ULM-1 is H, methyl or ethyl;

$R_{17}$ of ULM-1 is H, methyl, ethyl, hydoxymethyl or cyclopropyl;

M of ULM-1 is optionally substituted aryl, optionally substituted heteroaryl, or

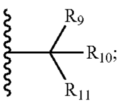

$R_{9\ of\ ULM\text{-}}1$ is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclic, optionally substituted aryl or

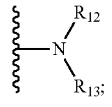

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

ULM-m

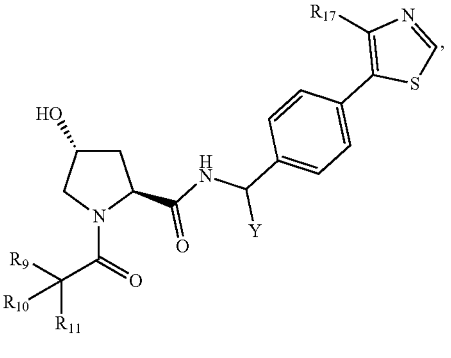

wherein:

Y of ULM-m is H, methyol or ethyl $R_9$ of ULM-m is H;

$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocycles.

In other embodiments of the disclosure, ULM and where present, ULM', are each independently a group according to the chemical structure:

ULM-n

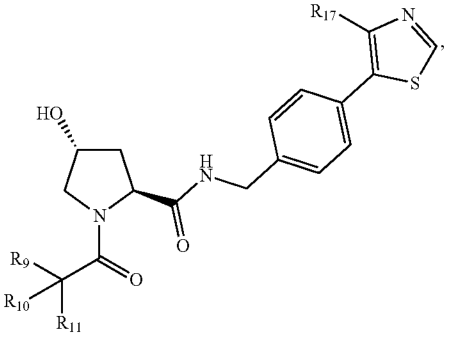

Wherein:

$R_{17}$ of ULM-n is methyl, ethyl, or cyclopropyl; and $R_9$, $R_{10}$, and $R_{11}$ of ULM-n are as defined above. In other instances, $R_9$ is H; and $R_{10}$ of ULM-n is H, alkyl, or or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

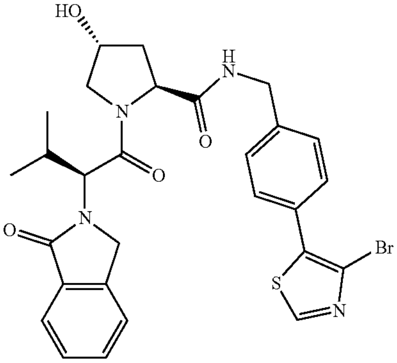

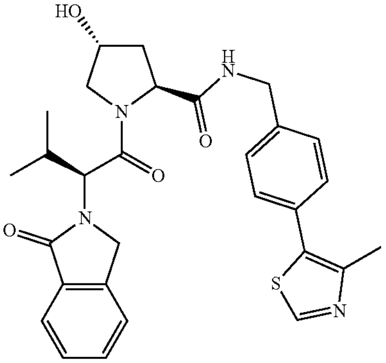

-continued

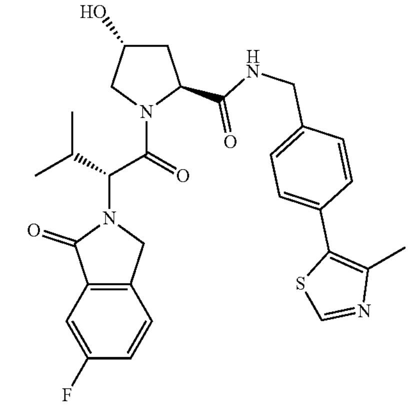

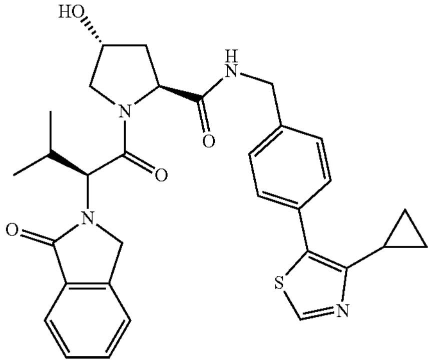

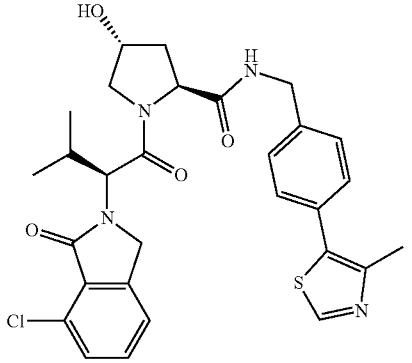

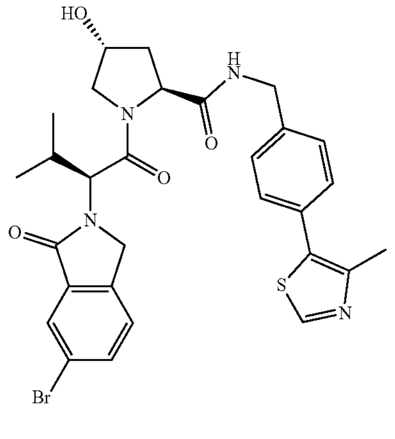

-continued
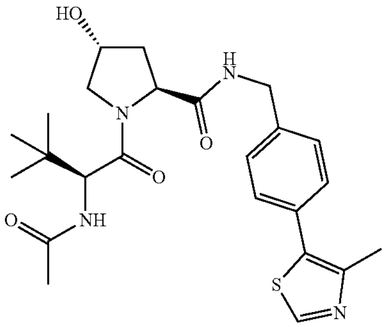
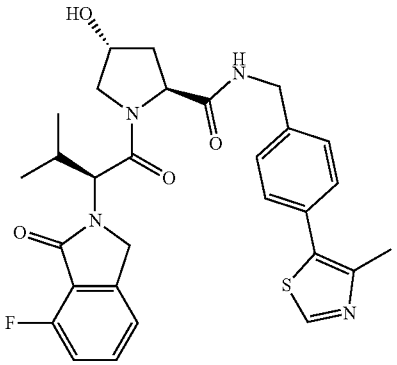
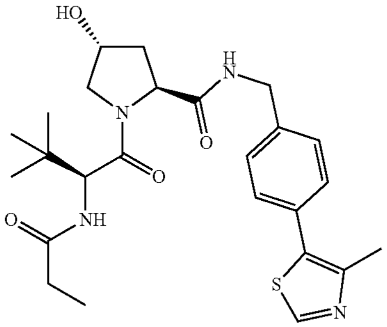
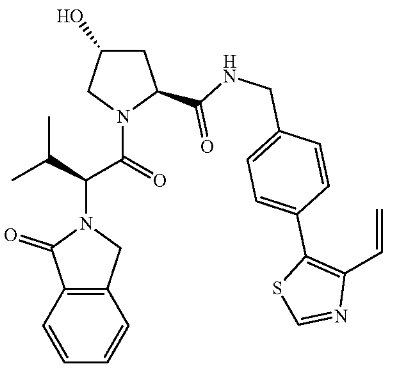
-continued
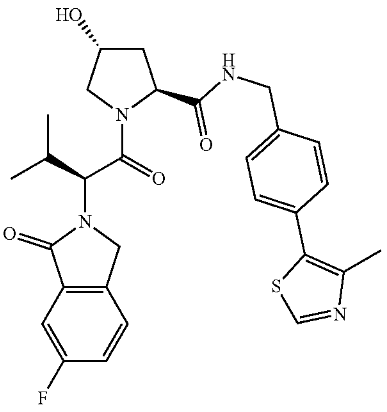
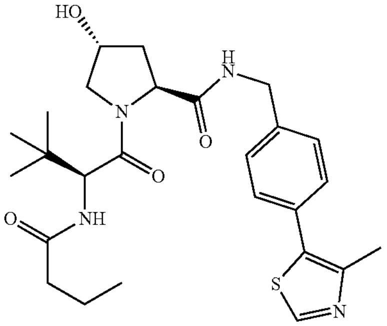
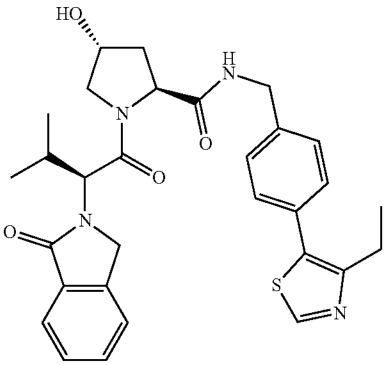
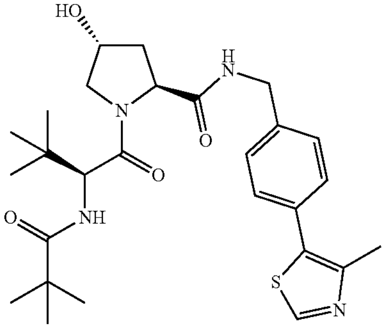

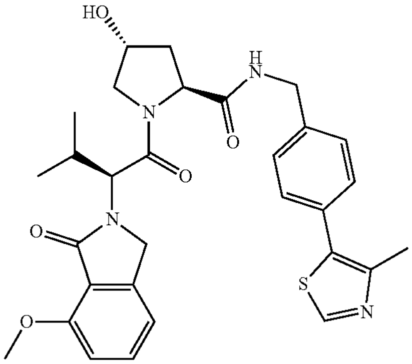
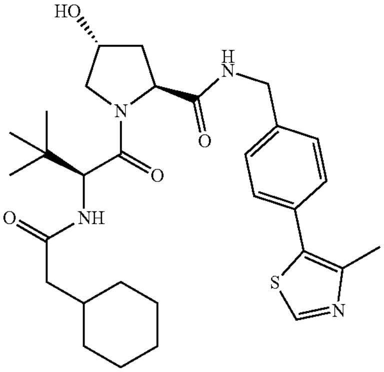
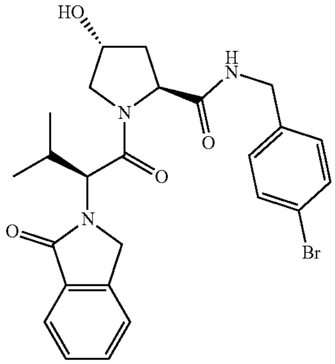
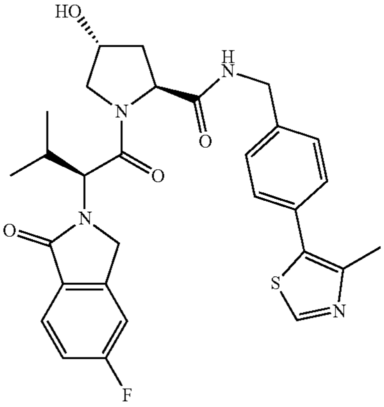
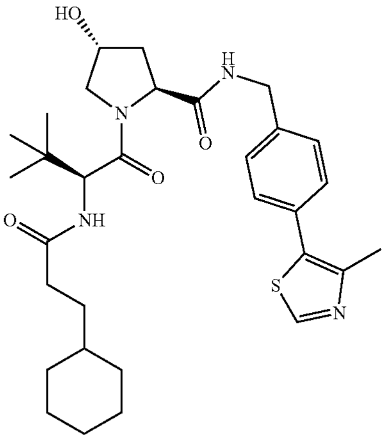
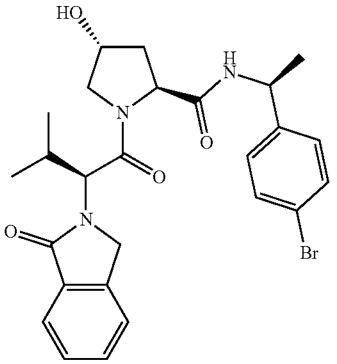
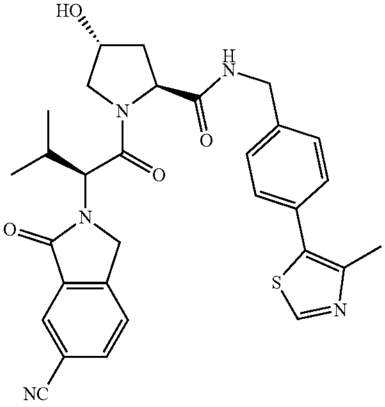
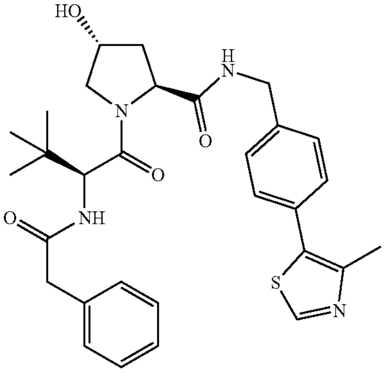

-continued
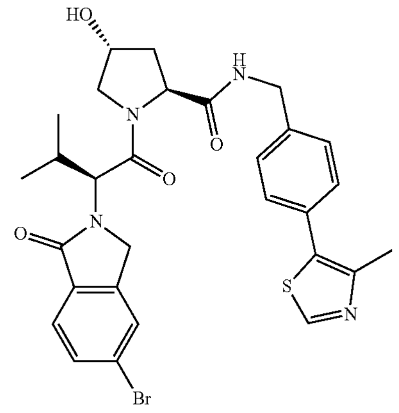
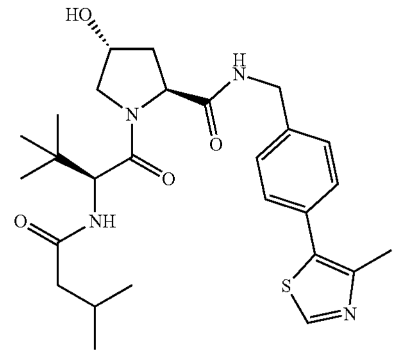
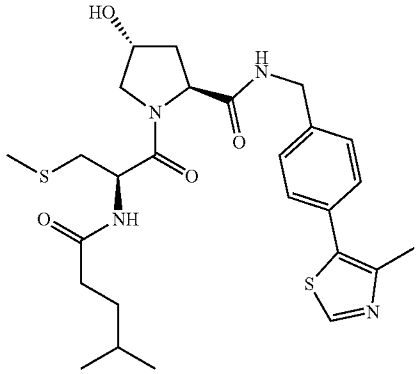
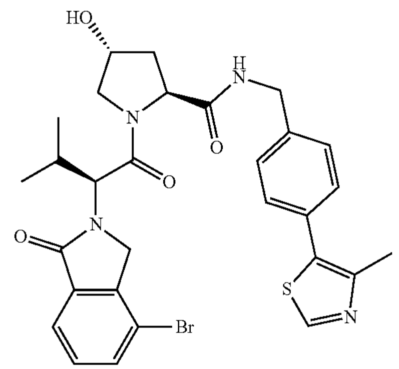
-continued
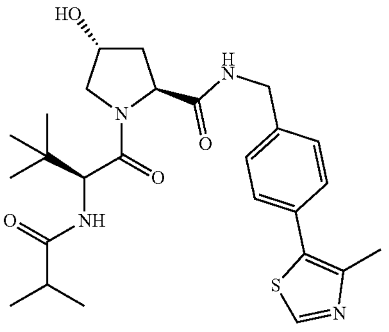
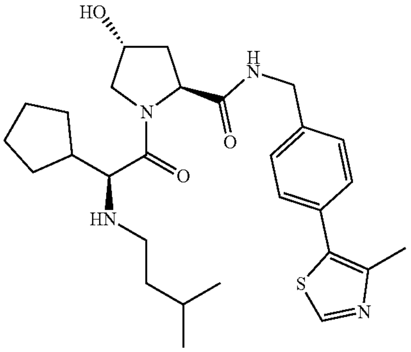
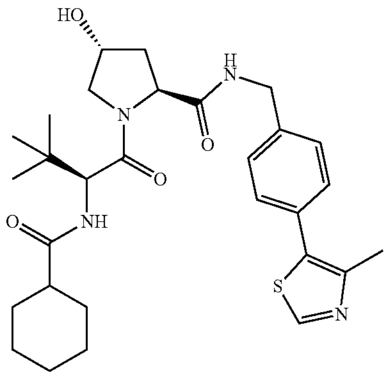
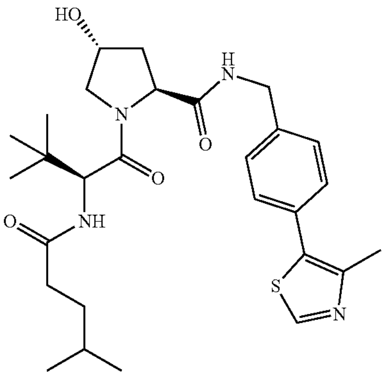

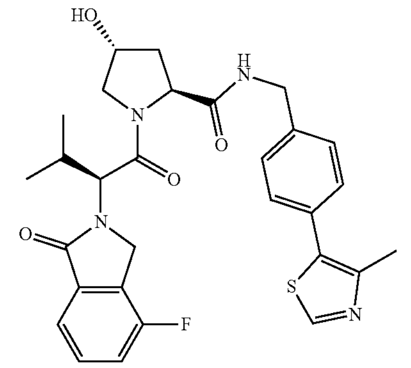
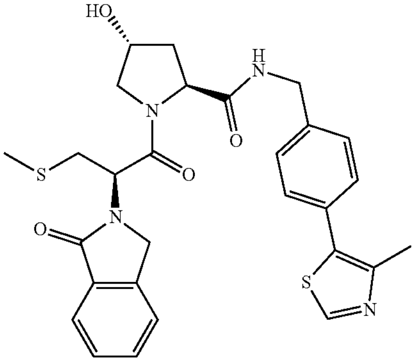
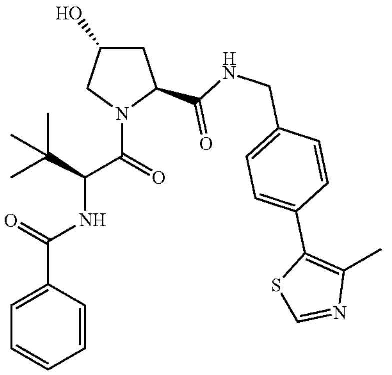
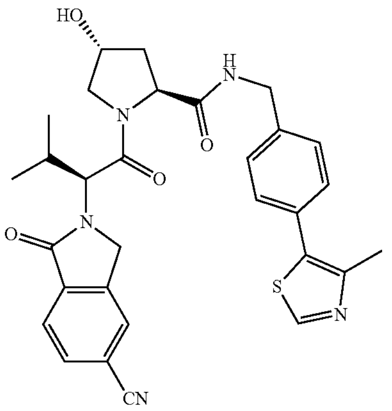
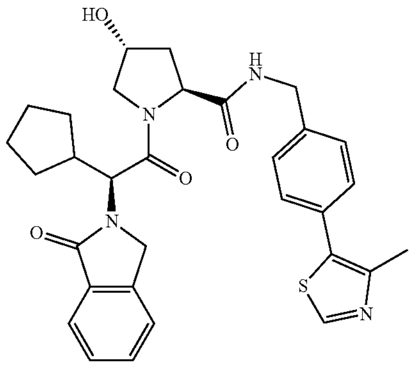
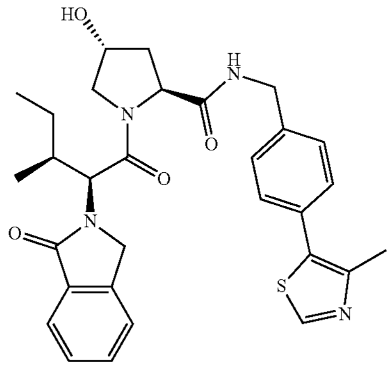
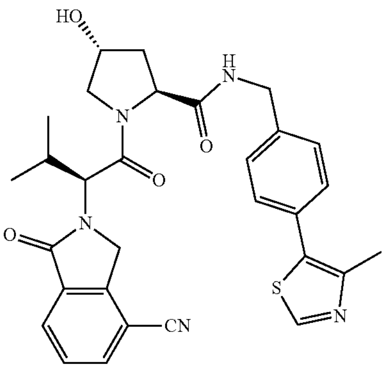
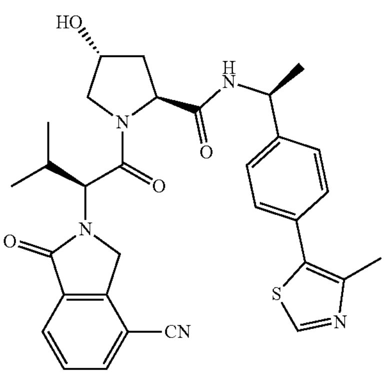

-continued
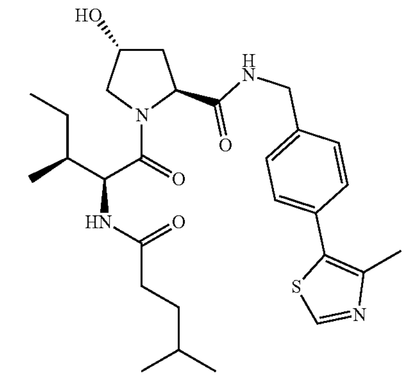
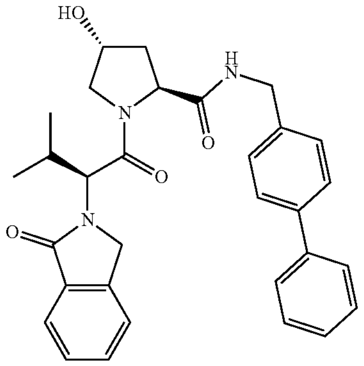
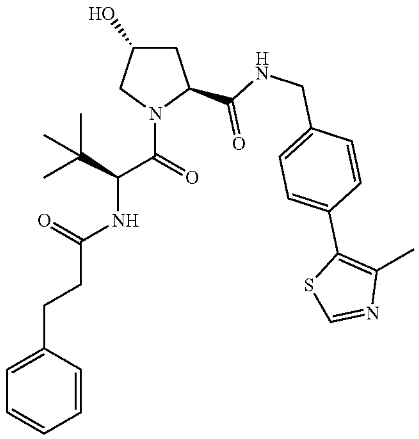
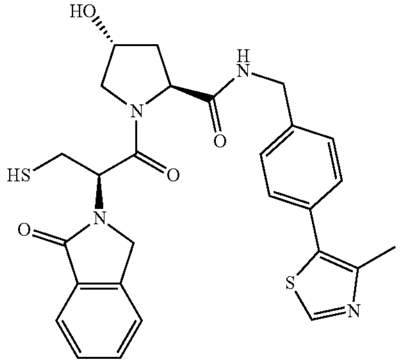
-continued
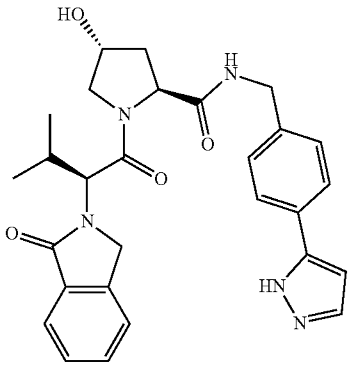
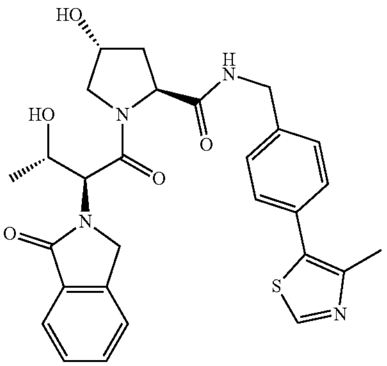
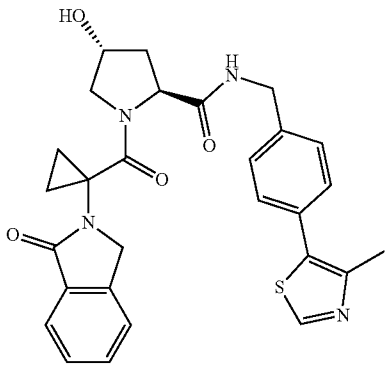
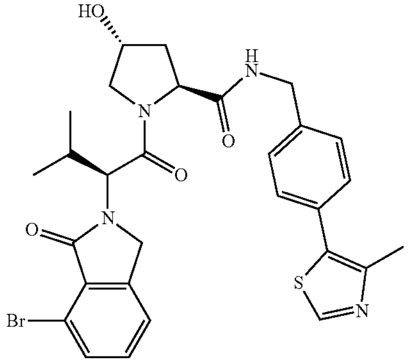

-continued
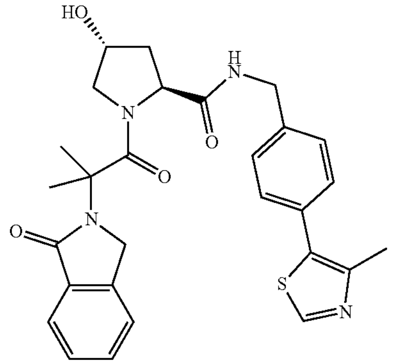
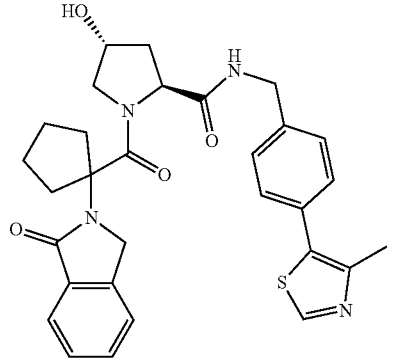
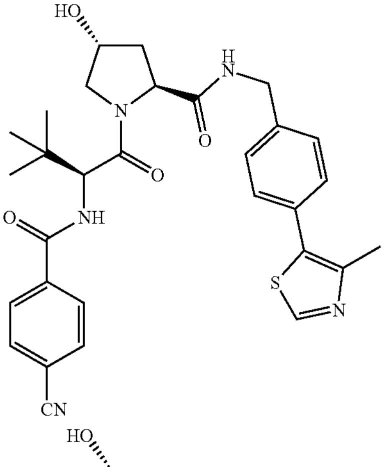
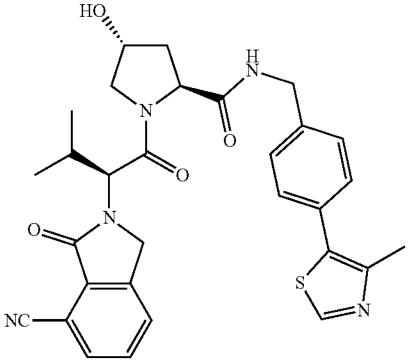
-continued
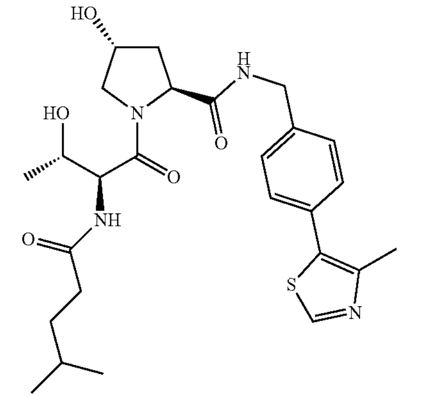
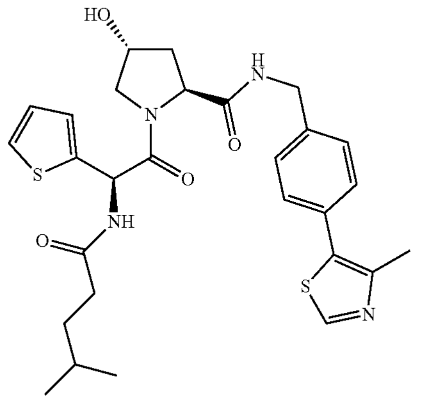
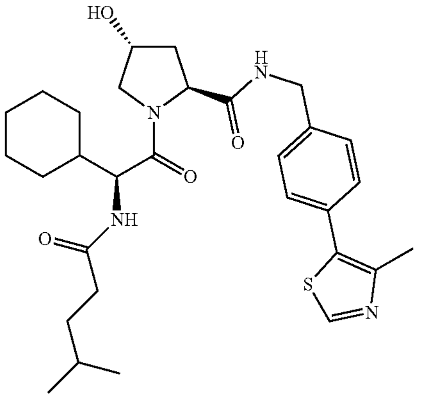
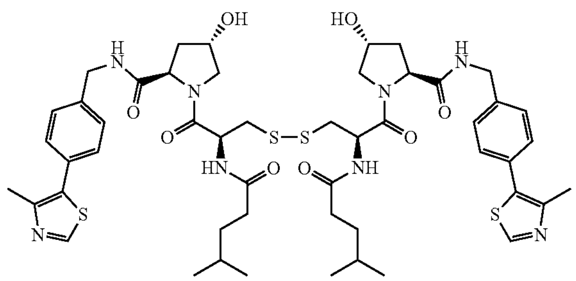

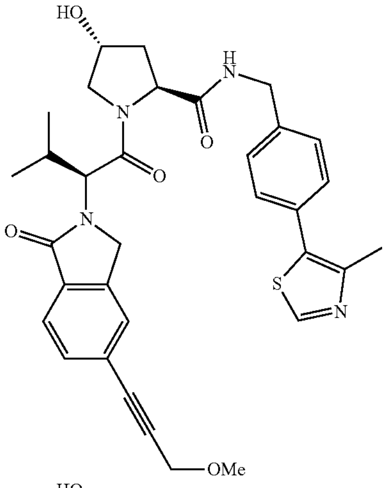
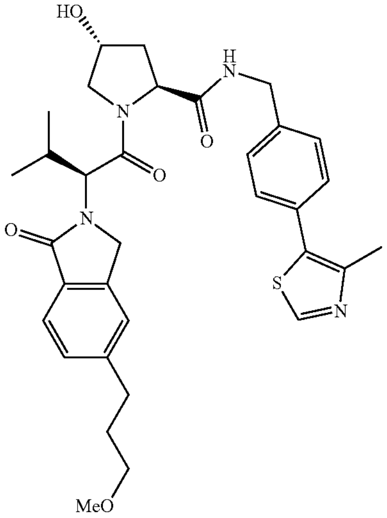
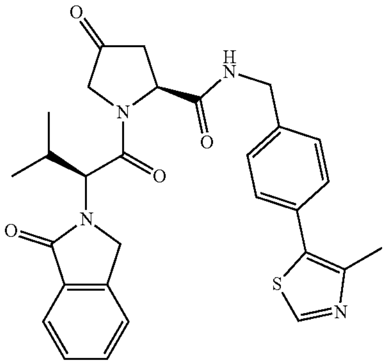
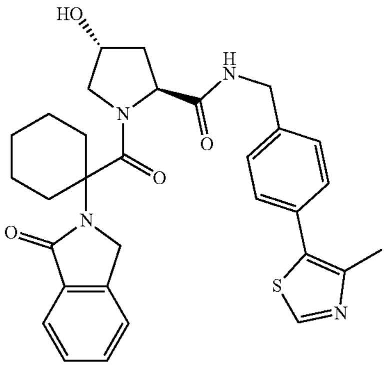
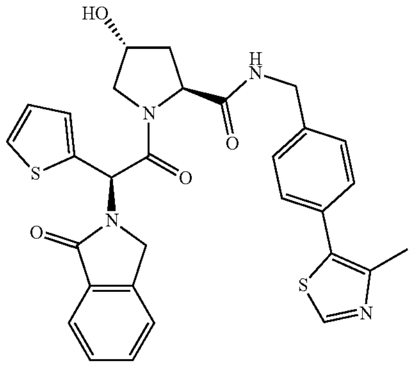
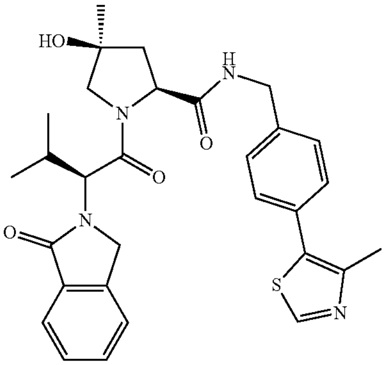
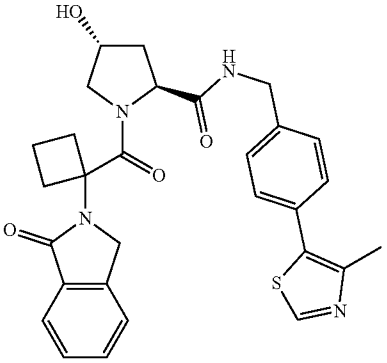
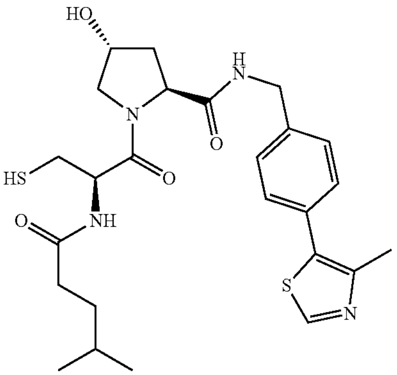

-continued
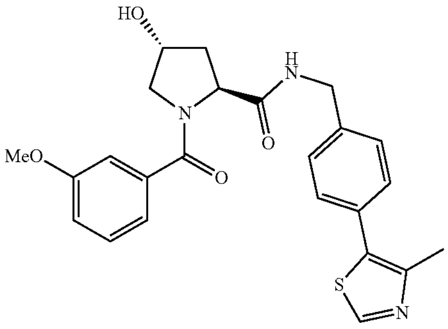
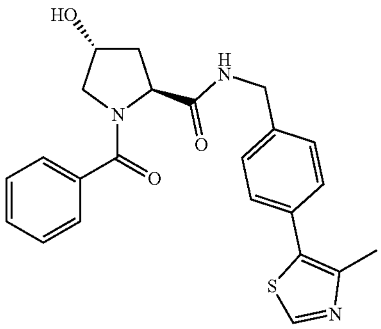
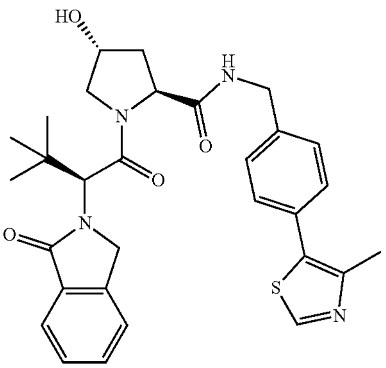
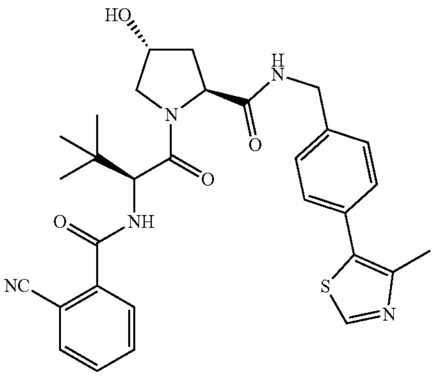
-continued
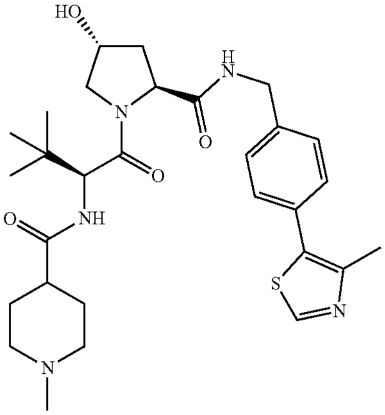
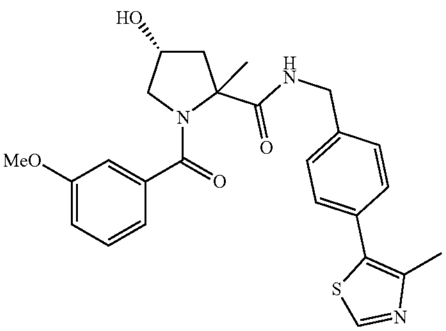
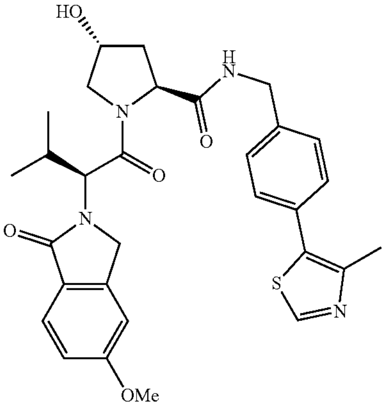
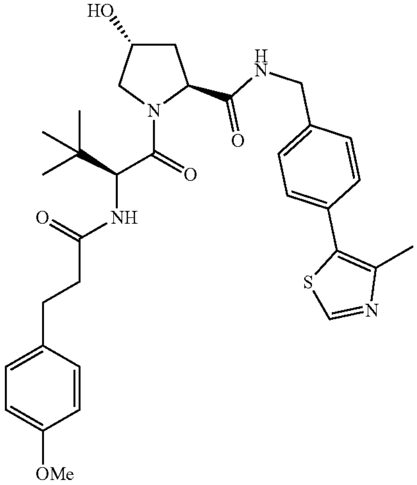

-continued
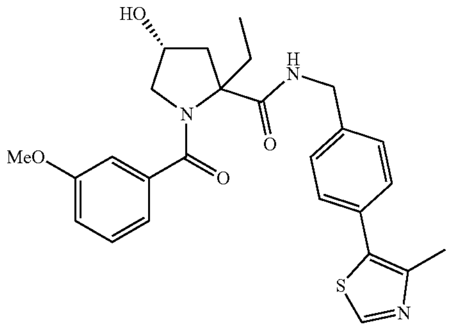
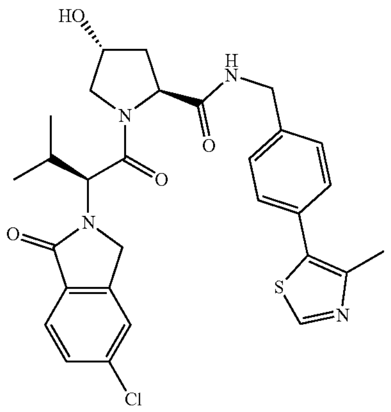
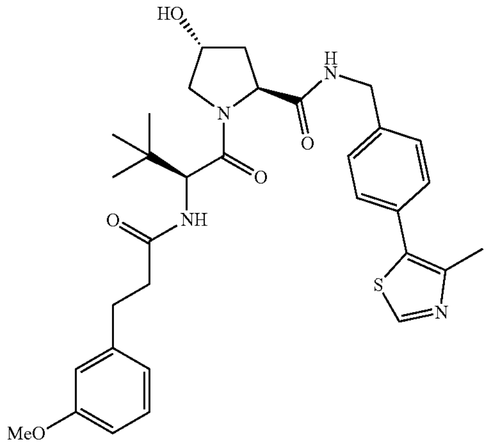
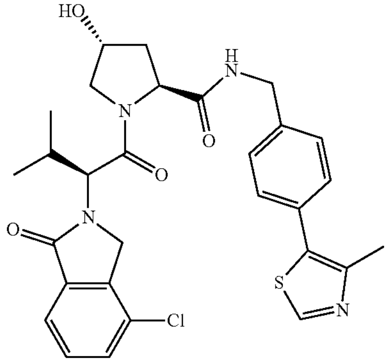
-continued
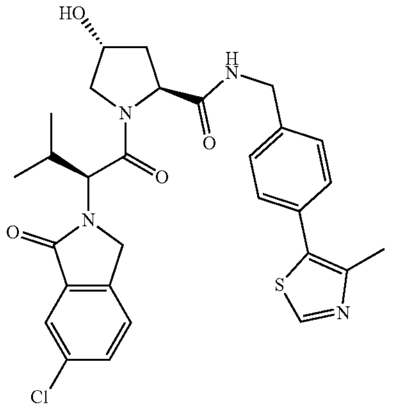
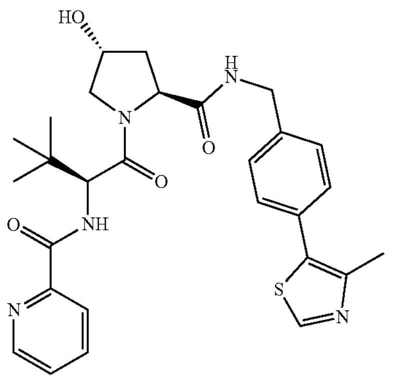
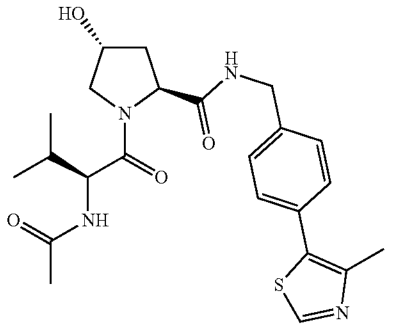
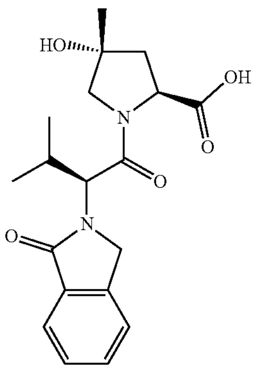

-continued
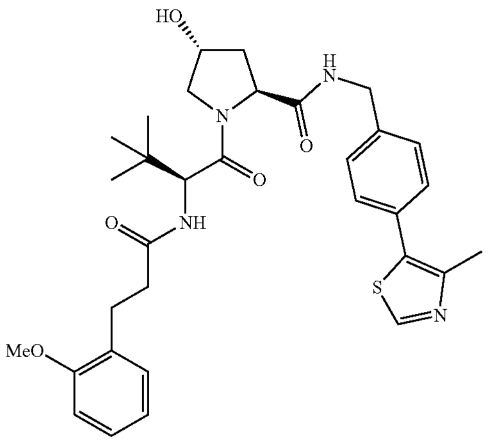
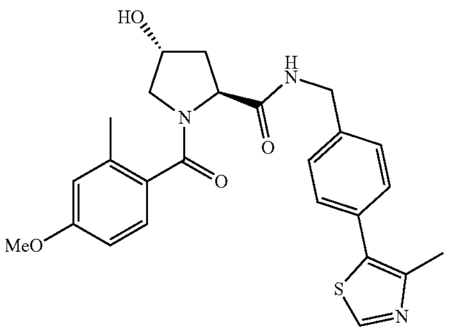
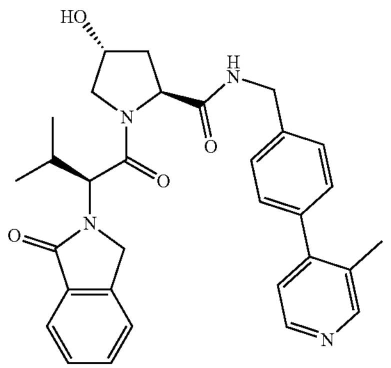
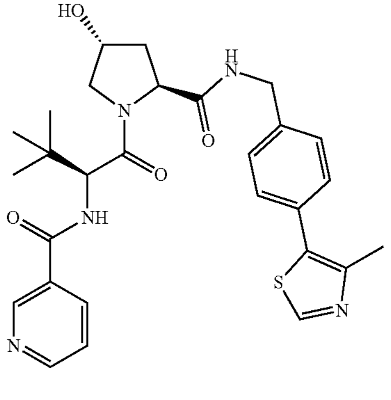
-continued
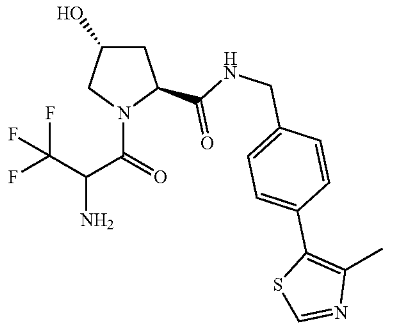
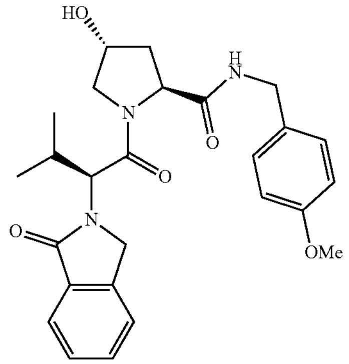
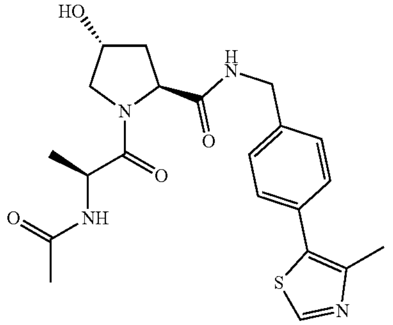
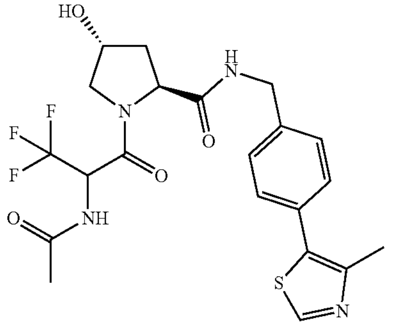
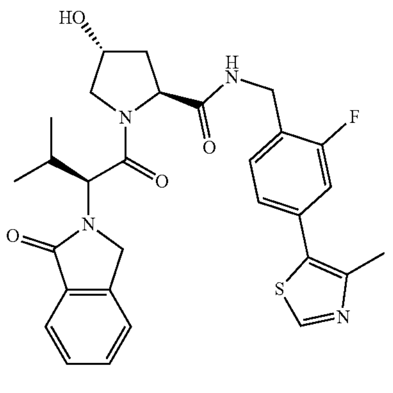

-continued
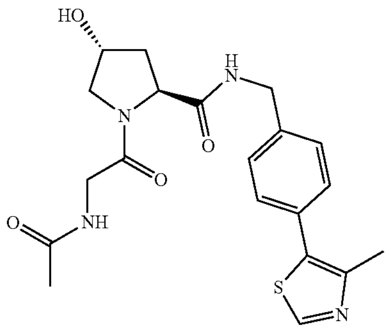
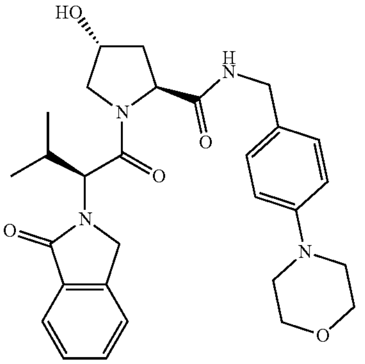
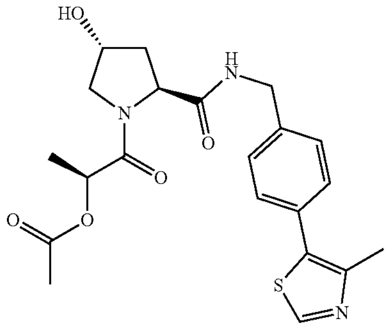
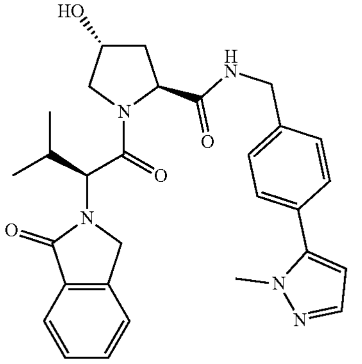
-continued
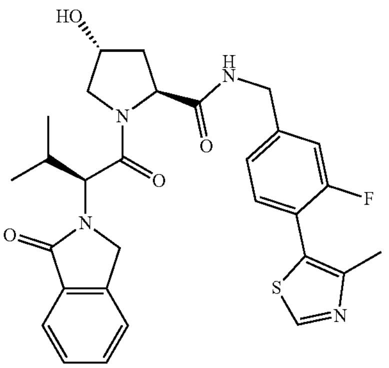
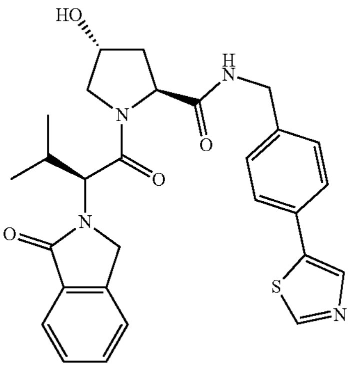
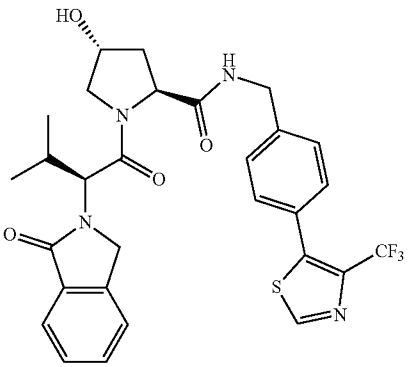
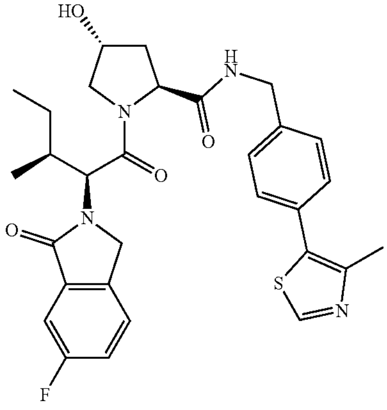

-continued
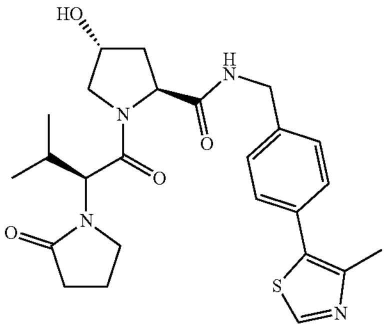
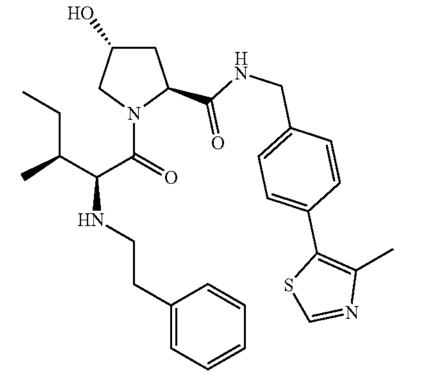
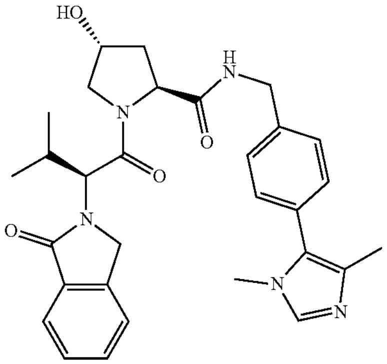
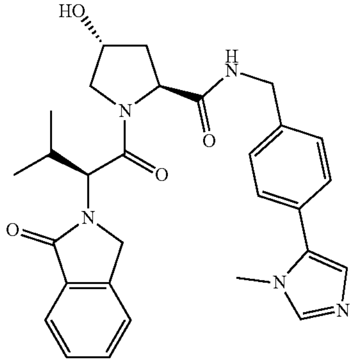
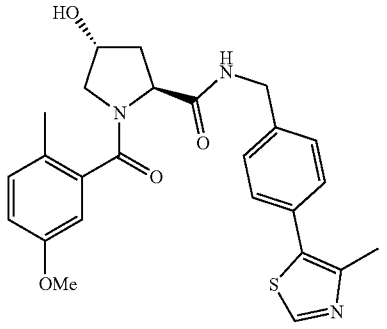
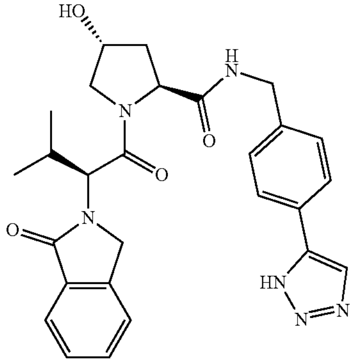
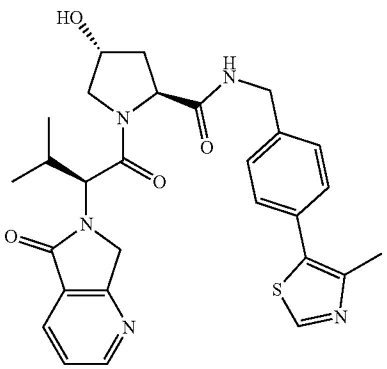
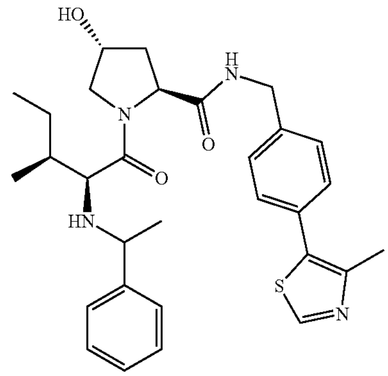
-continued -continued
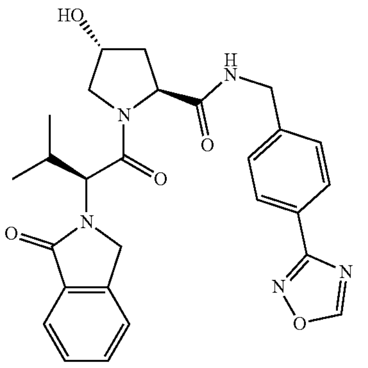
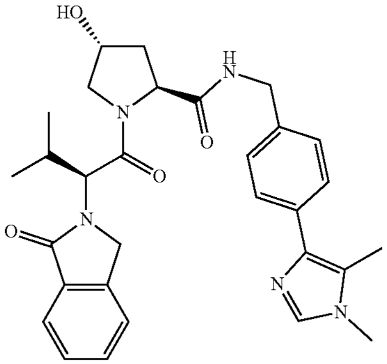
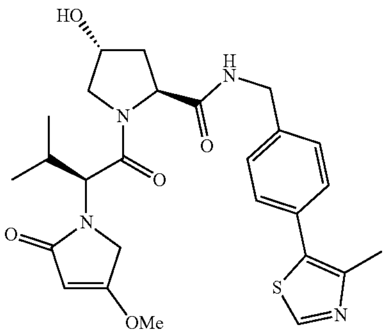
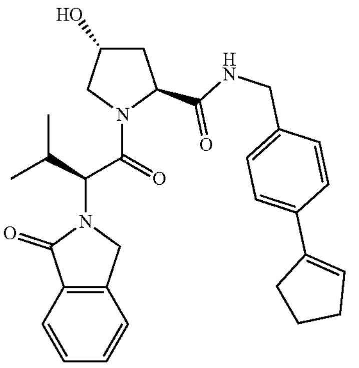
-continued
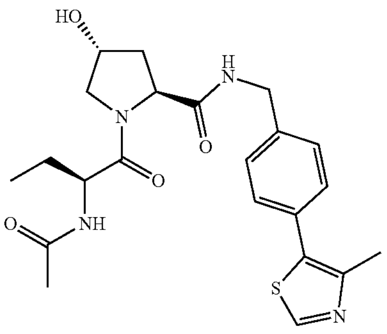
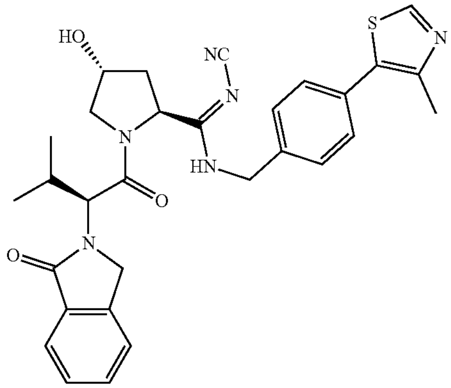
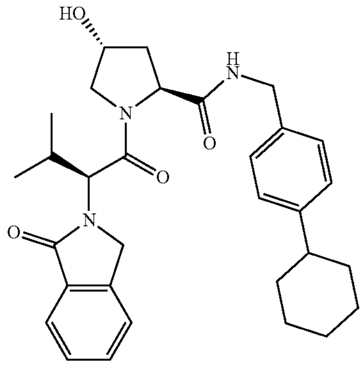
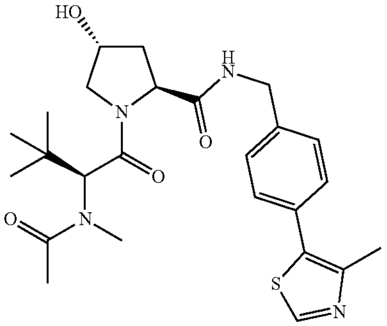

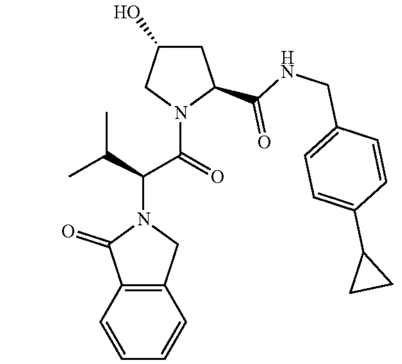
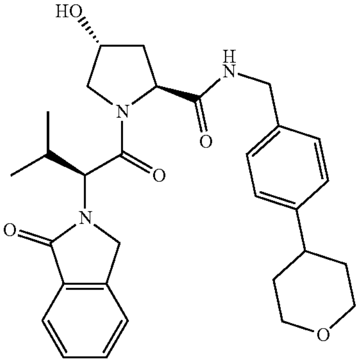
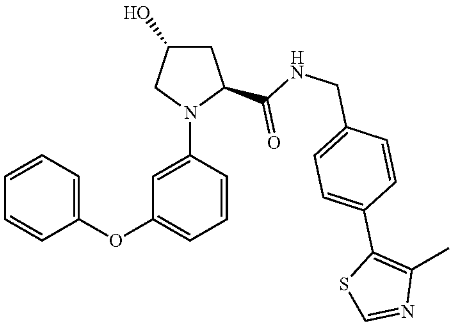
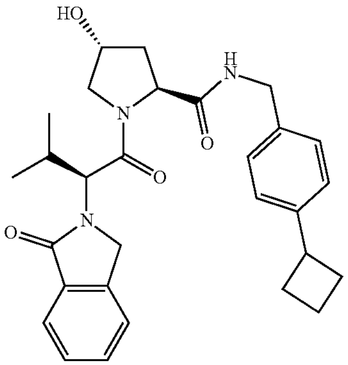
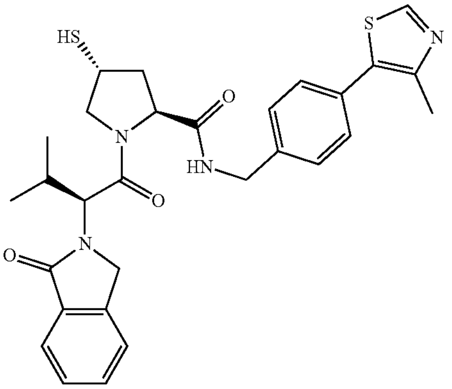
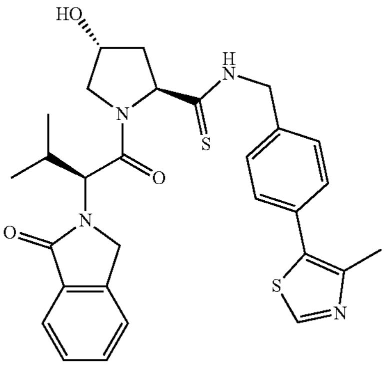
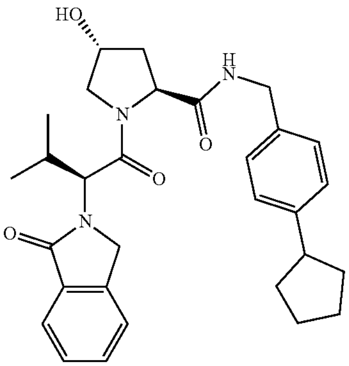
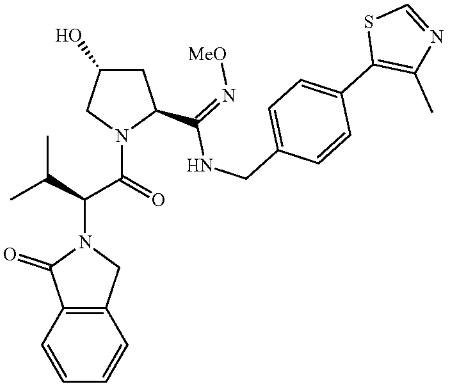

-continued
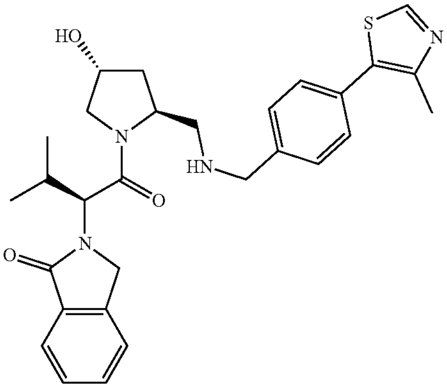
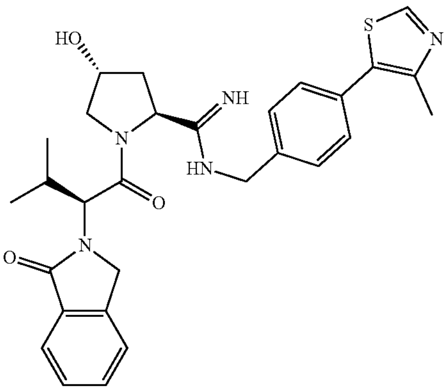
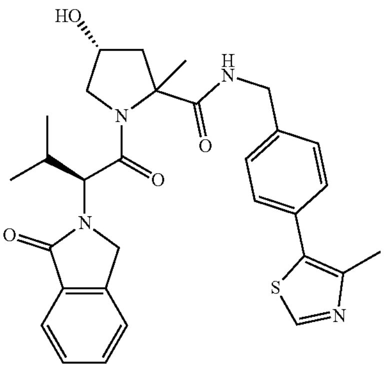
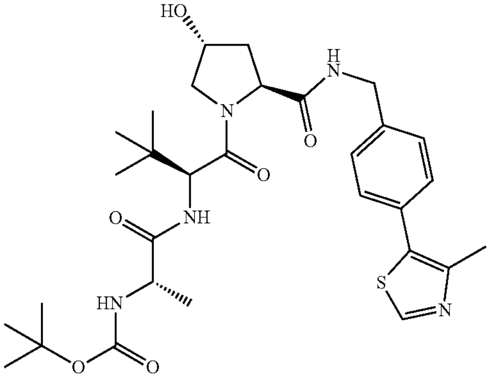
-continued
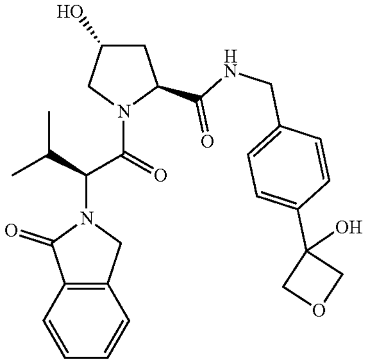
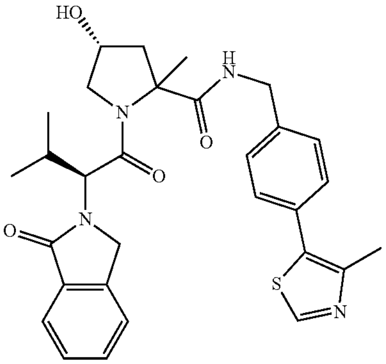
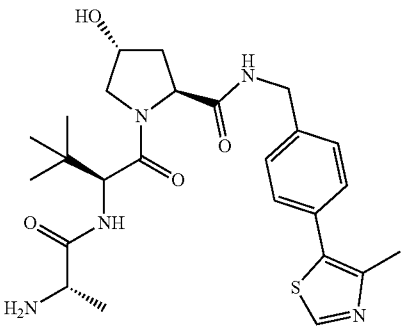
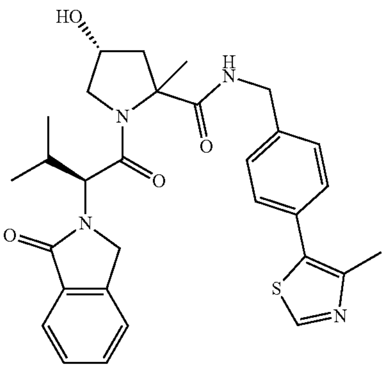

-continued
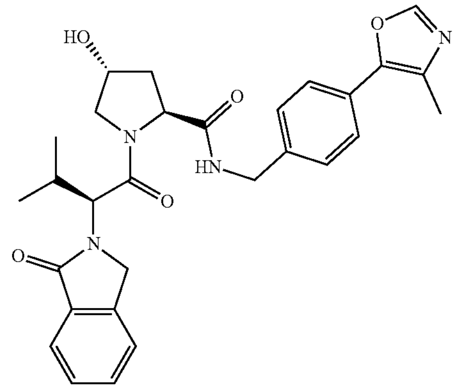
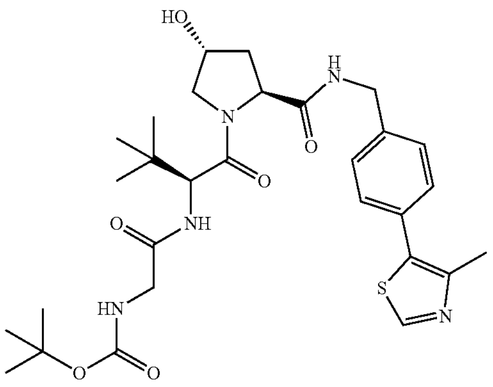
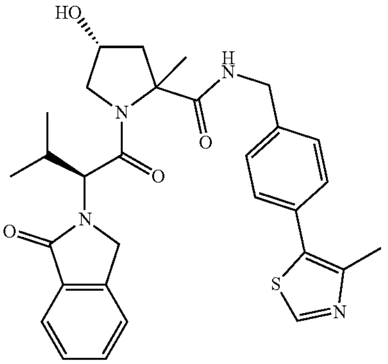
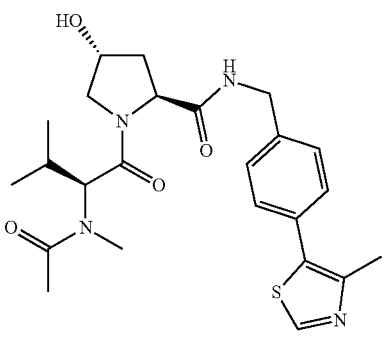
-continued
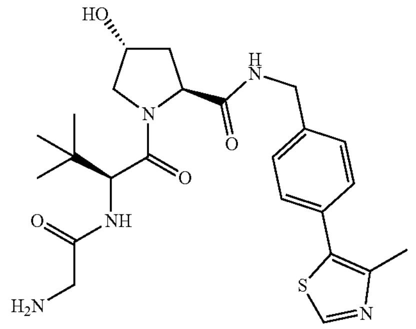
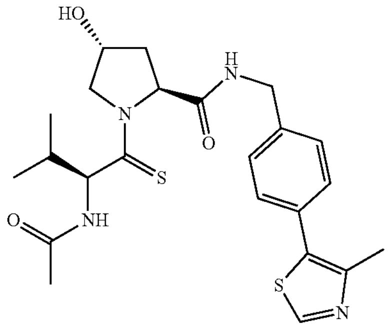
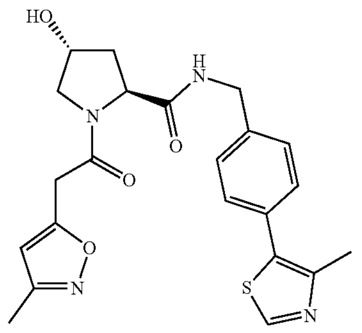
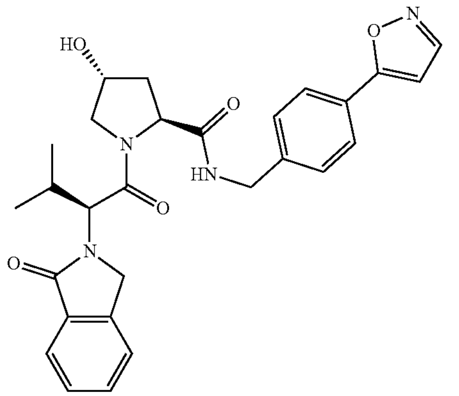
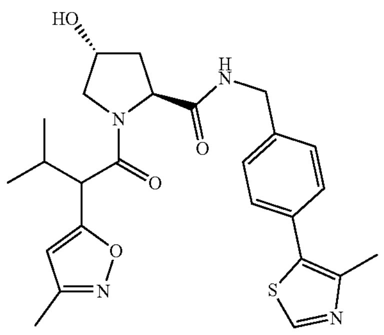

-continued
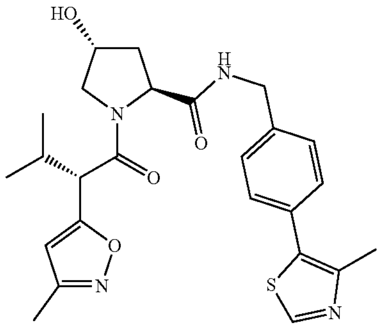
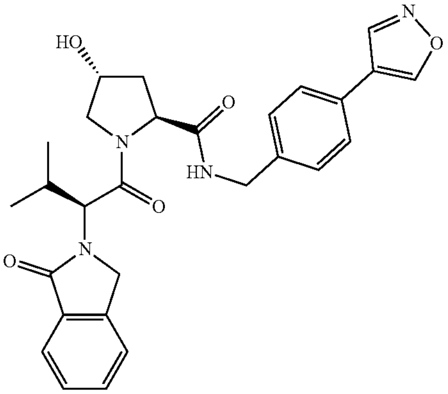
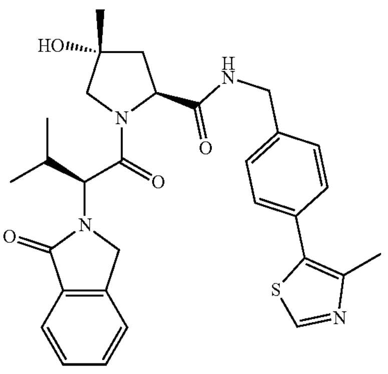
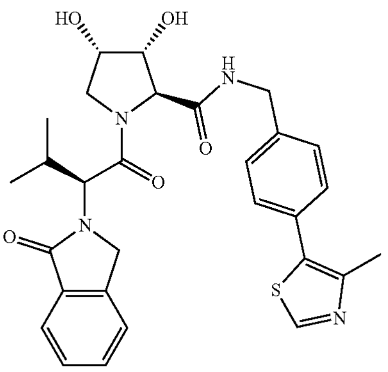
-continued
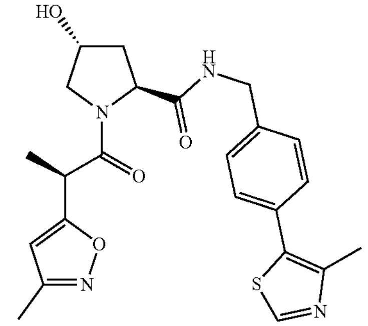
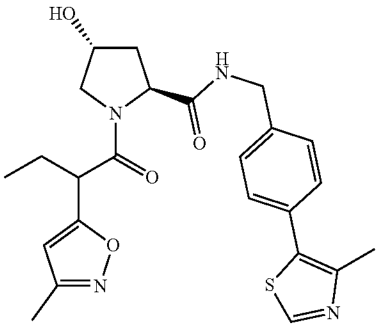
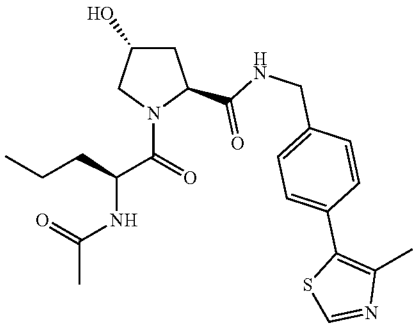
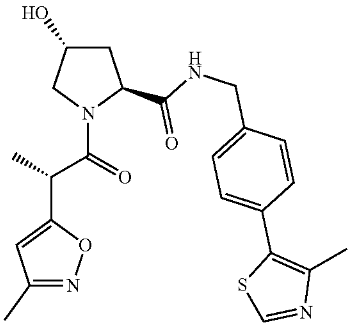
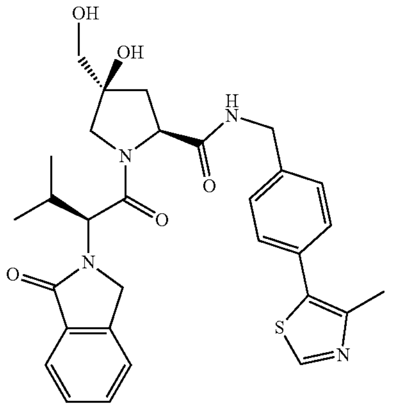

-continued
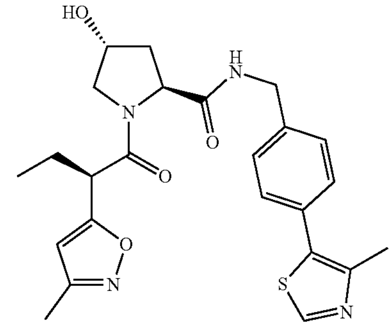
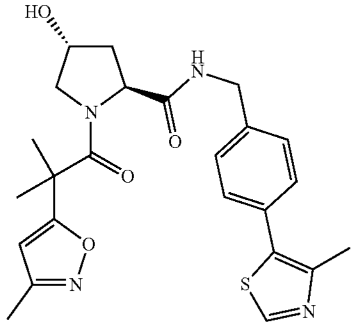
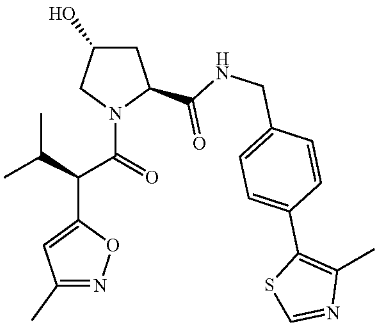
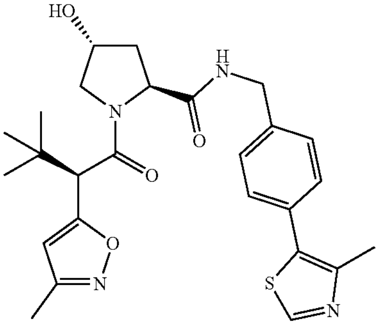
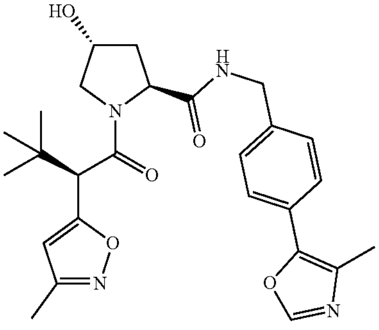
-continued
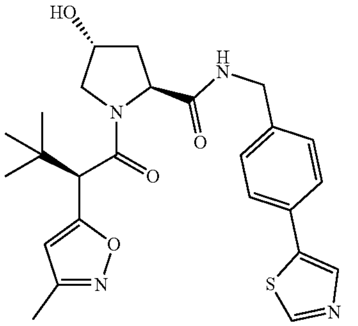
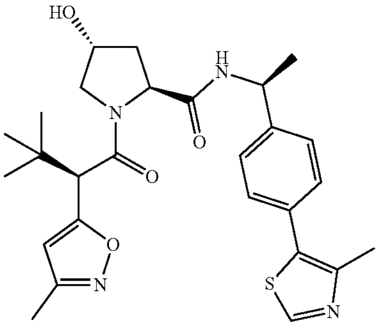
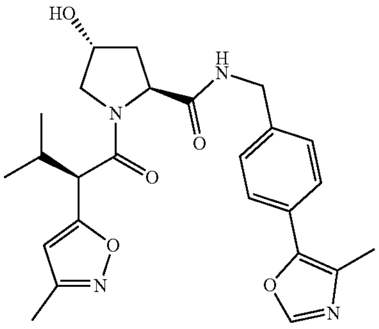
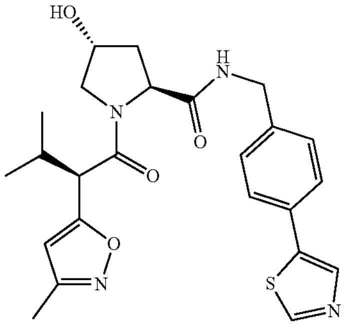
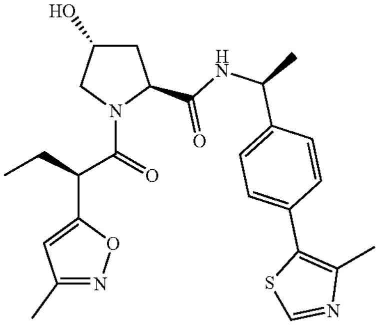

-continued
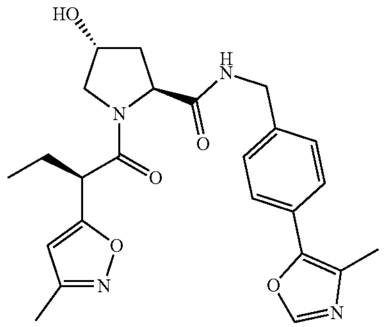
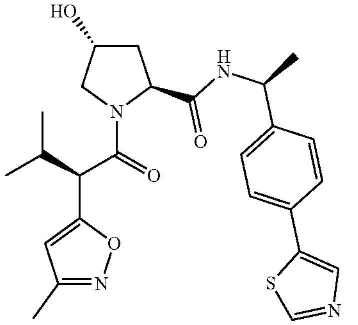
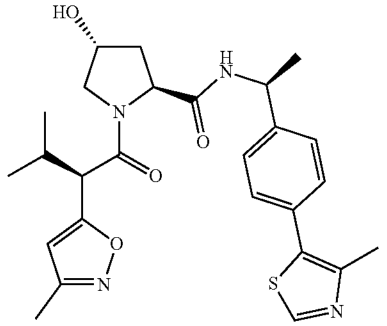
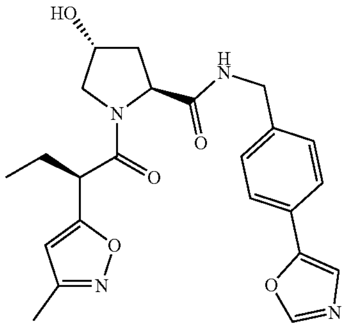
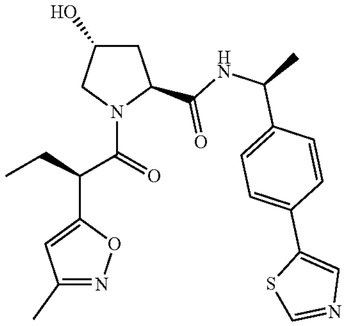
-continued
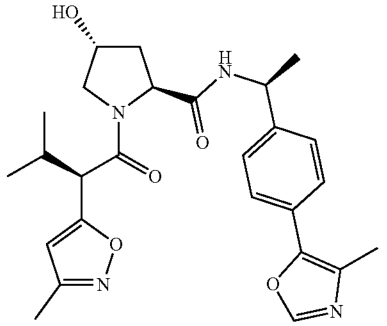
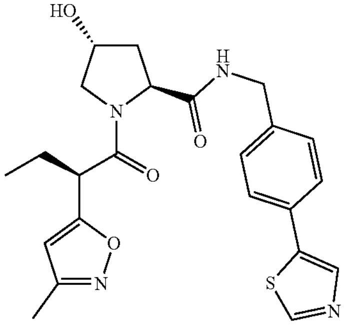
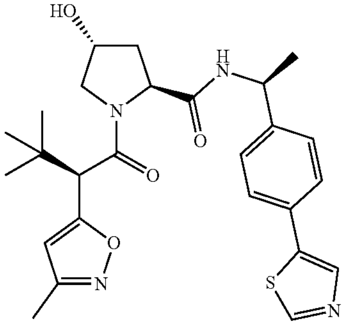
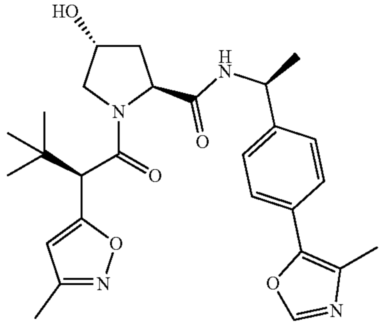
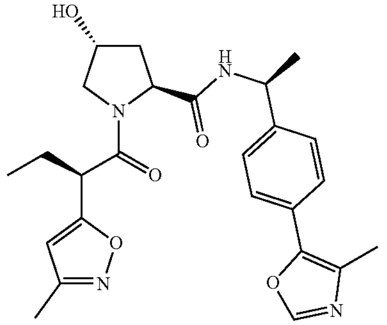

-continued
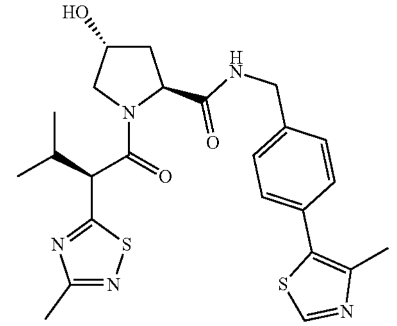
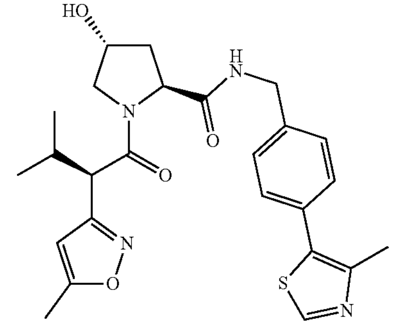
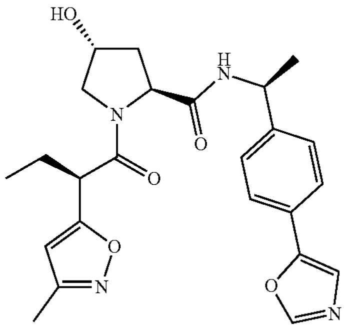
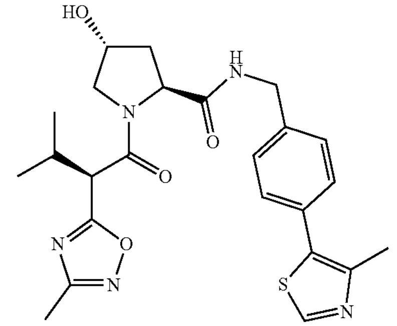
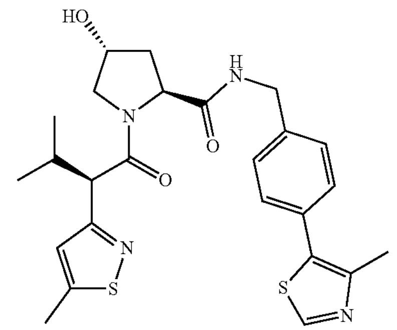
-continued
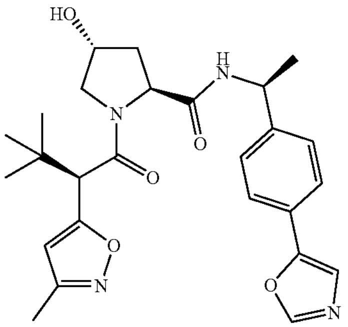
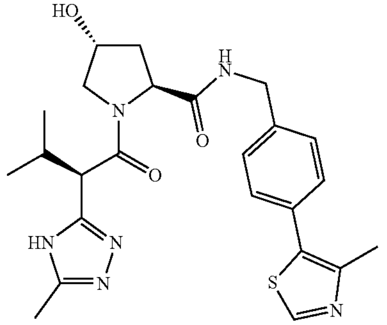
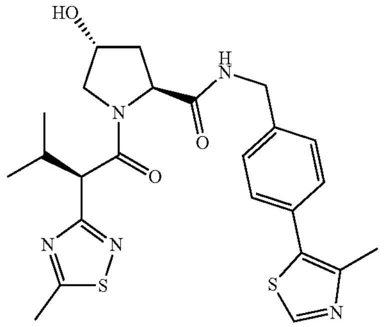
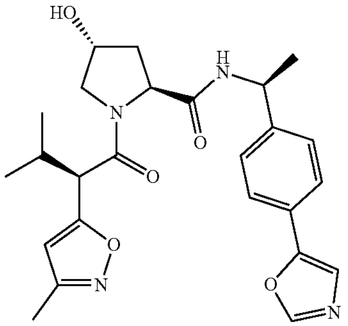
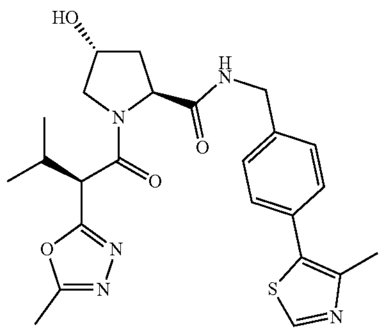

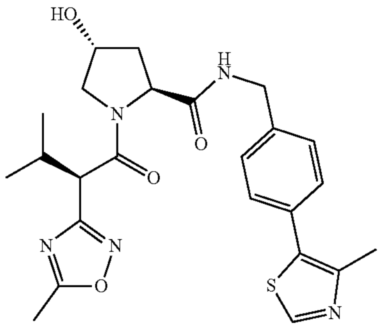
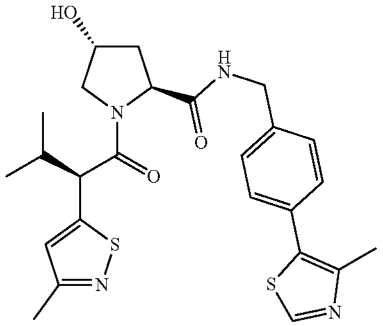
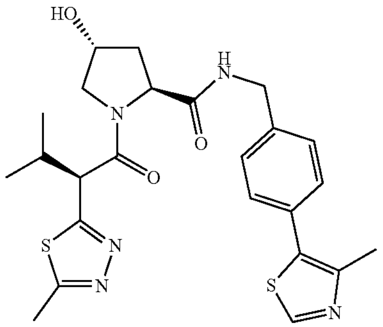
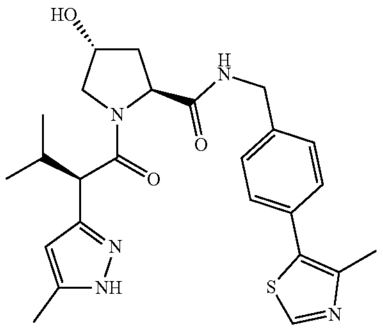
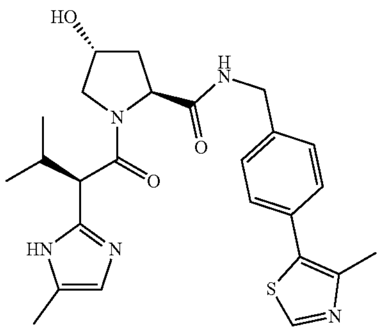
-continued
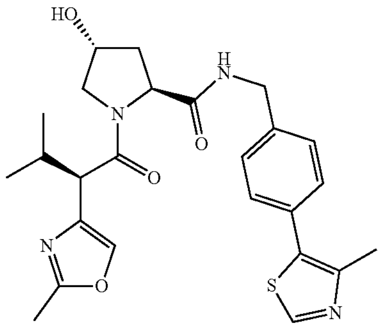
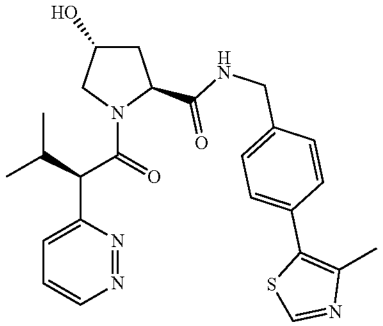
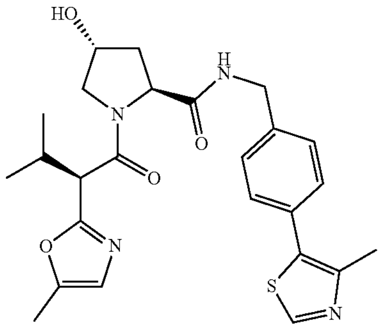
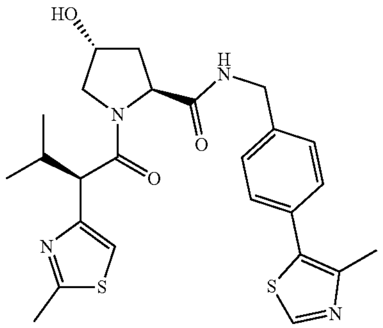
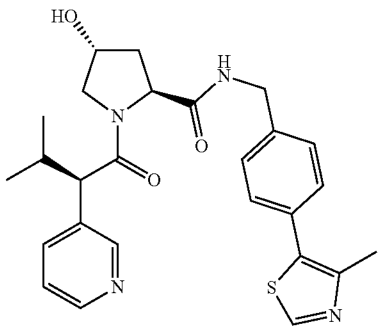

-continued
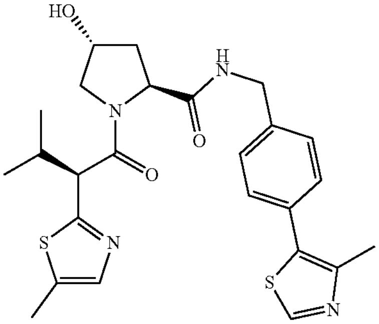
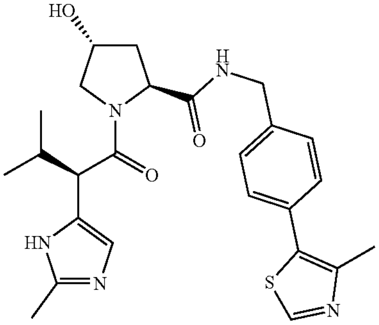
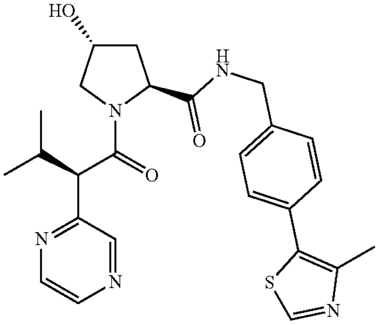
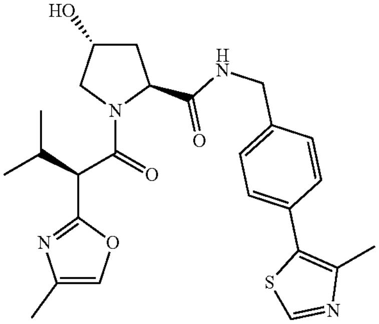
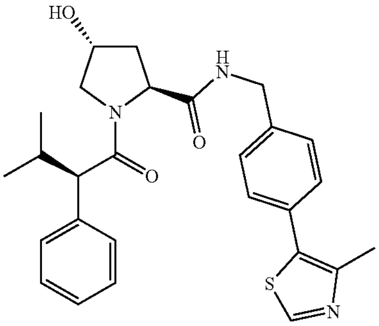
-continued
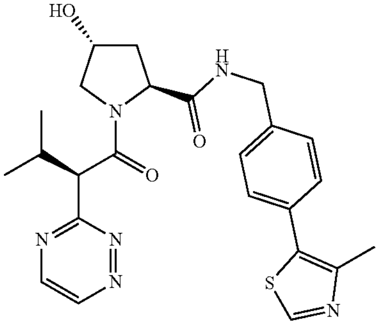
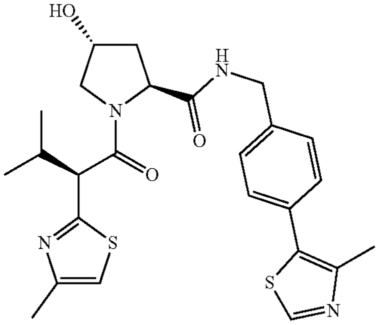
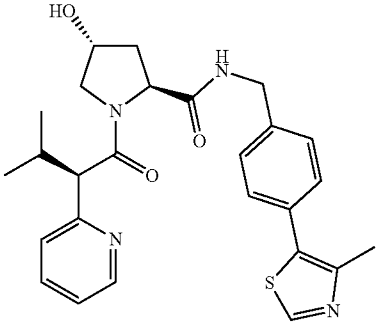
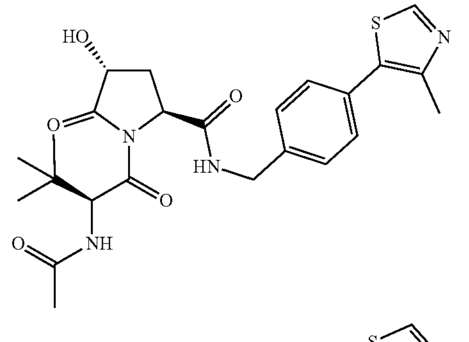
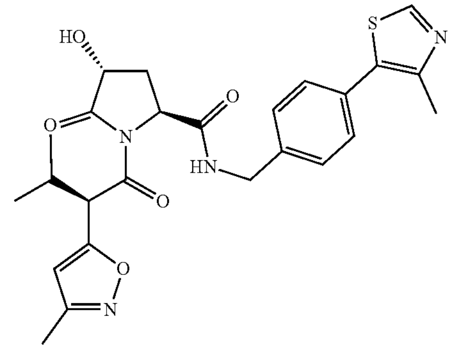

-continued
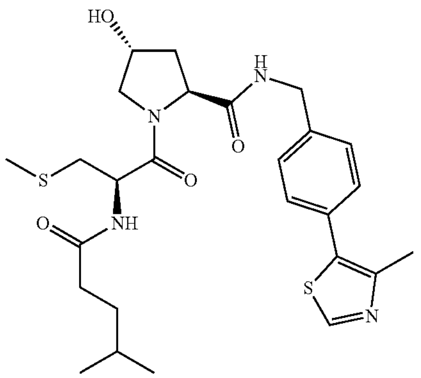
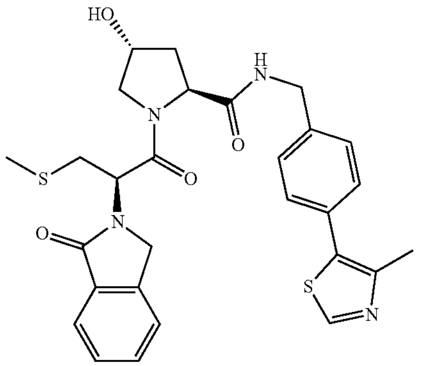
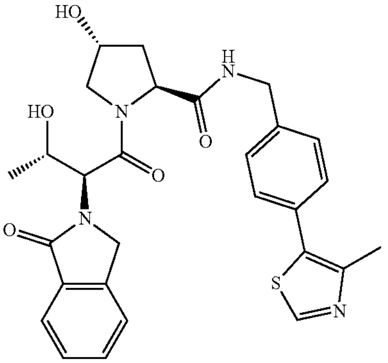
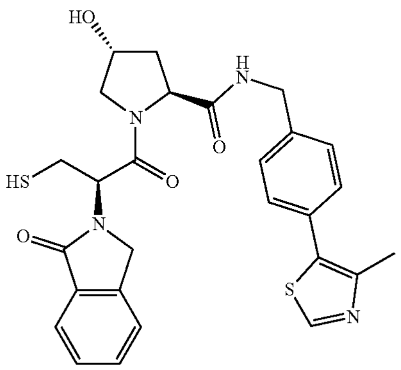
-continued
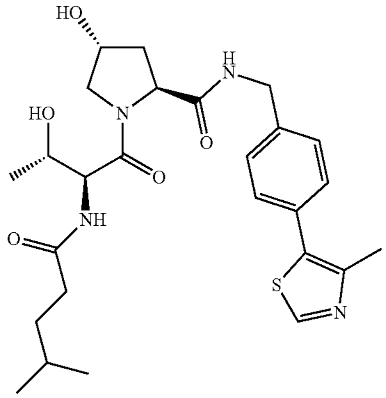
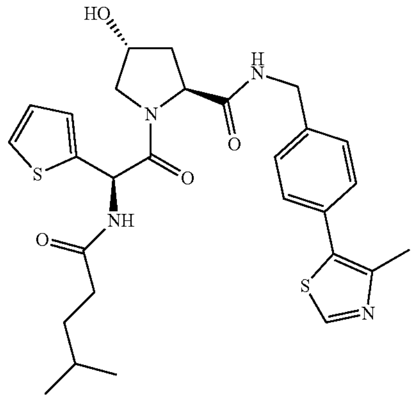
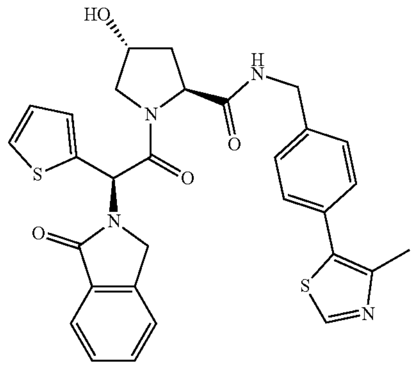
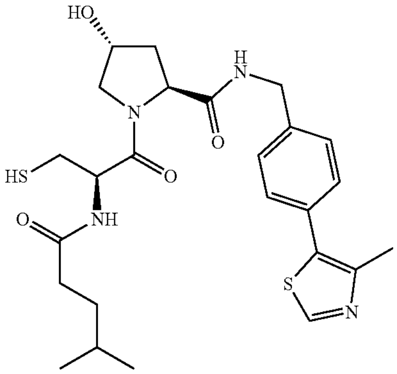

-continued
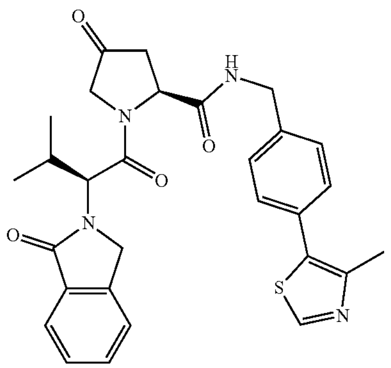
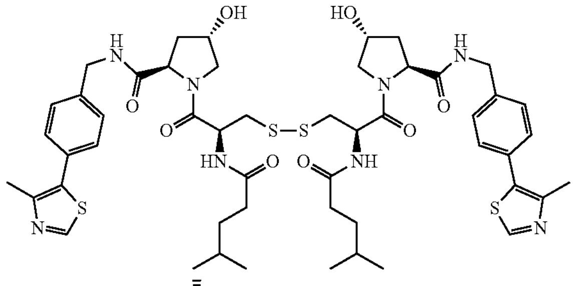
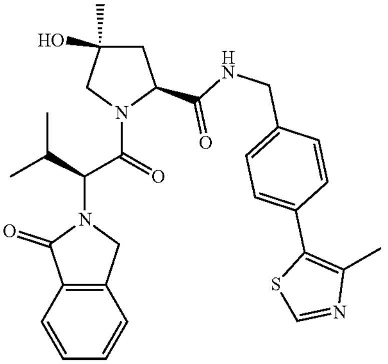
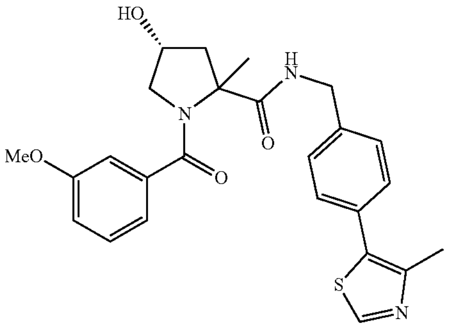
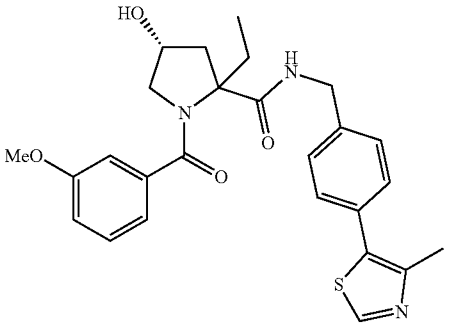
-continued
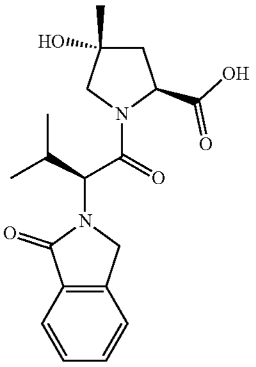
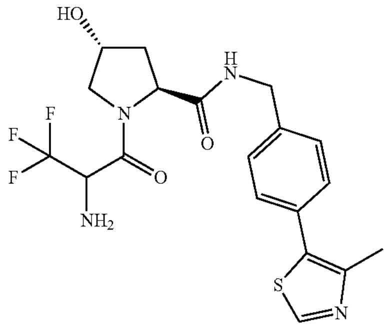
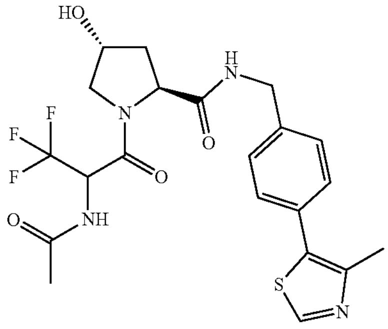
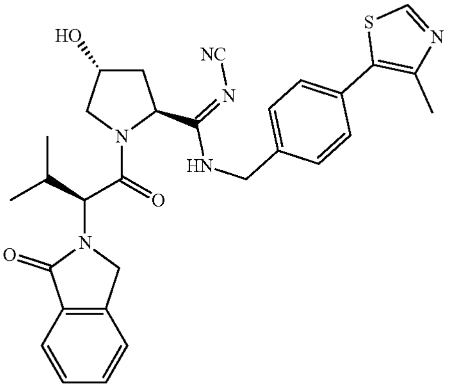

-continued
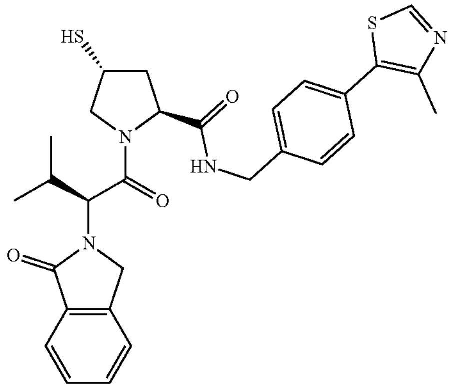
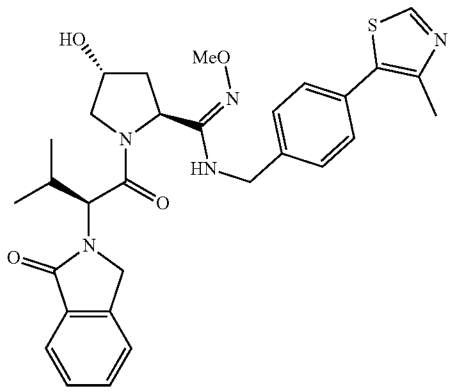
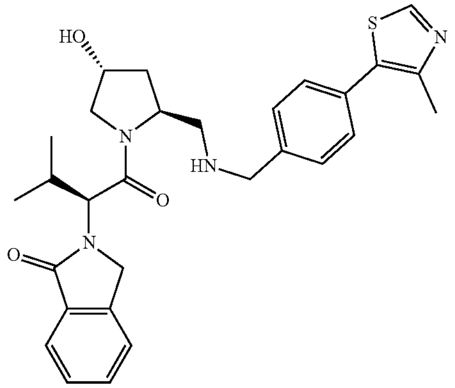
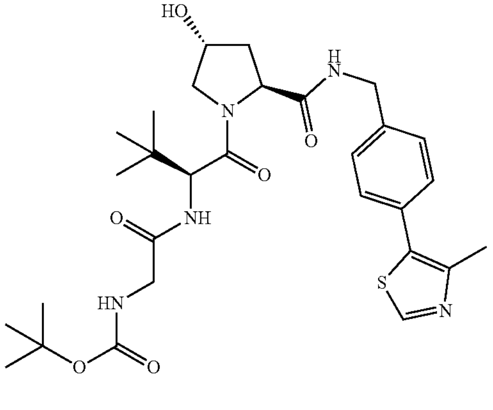
-continued
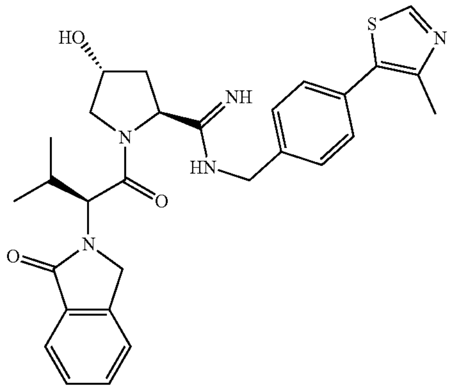
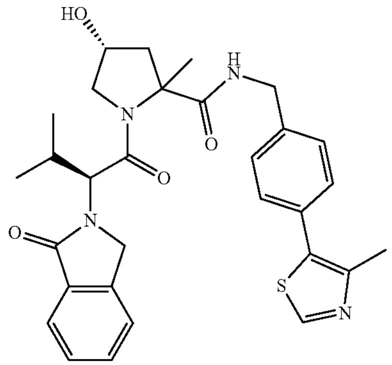
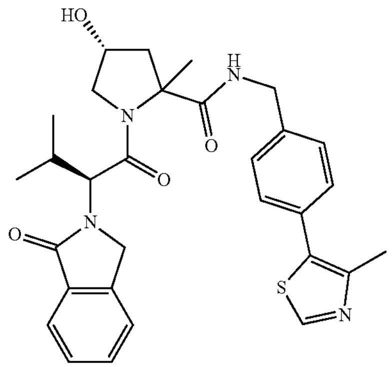
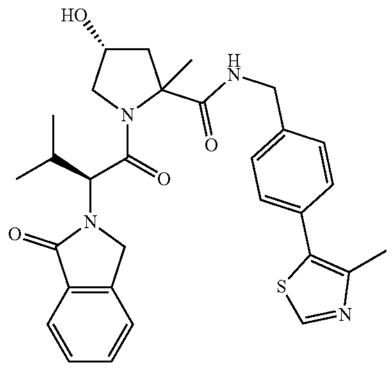

-continued
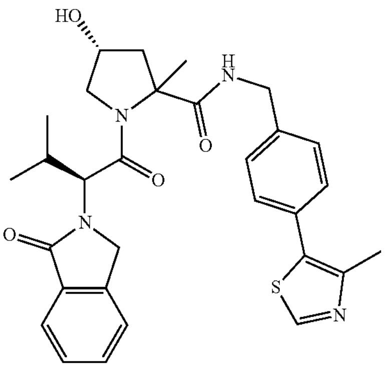
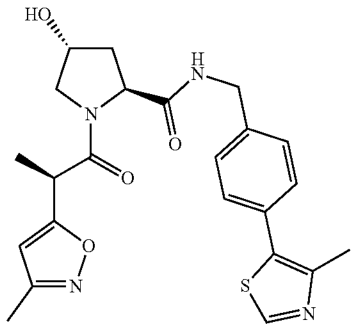
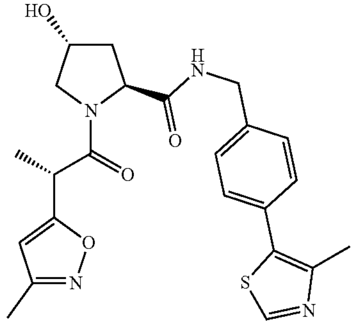
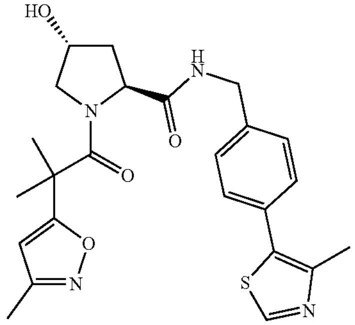
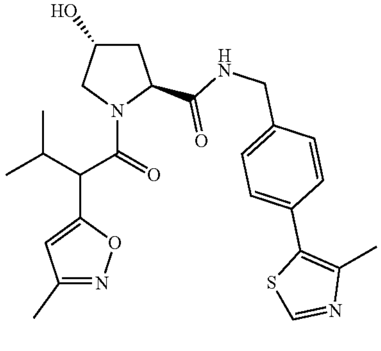
-continued
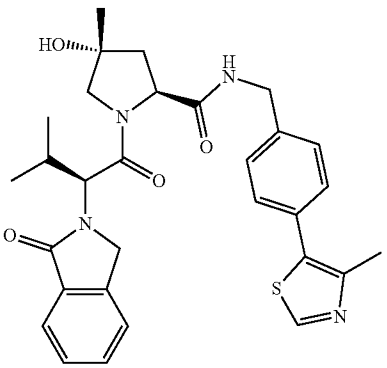
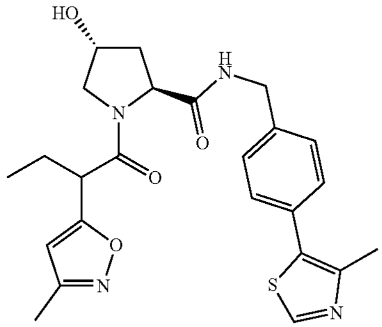
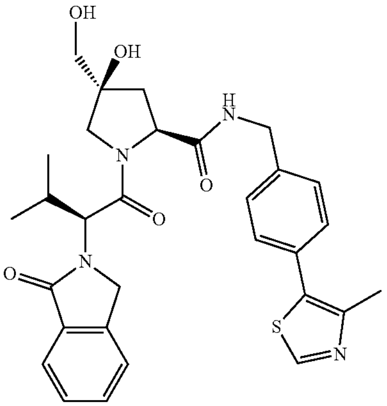
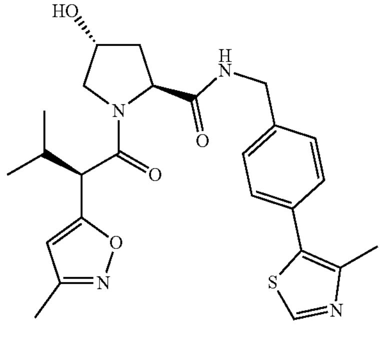

-continued
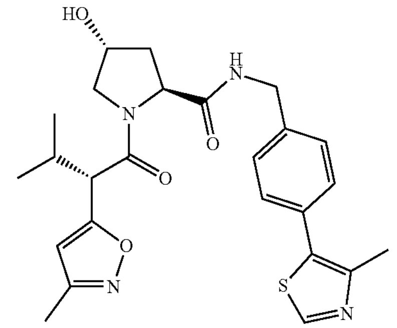
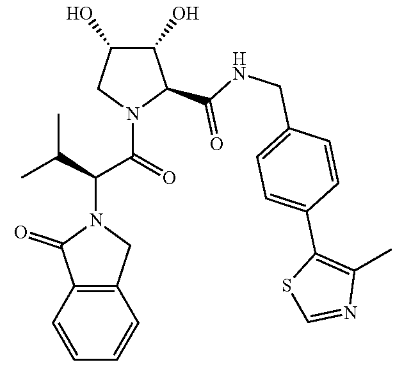
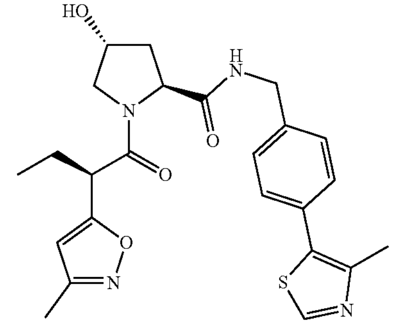
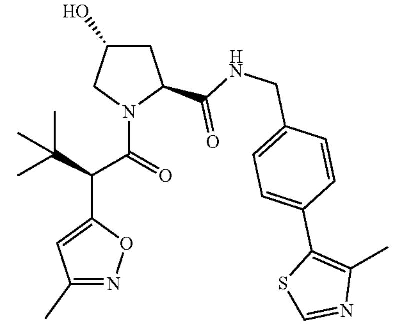
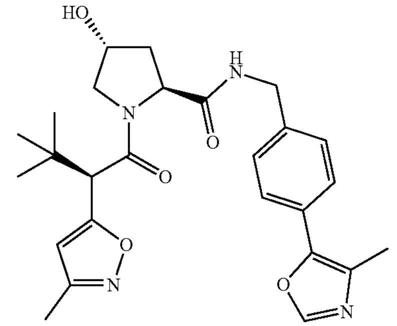
-continued
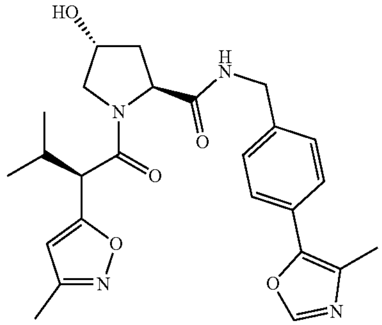
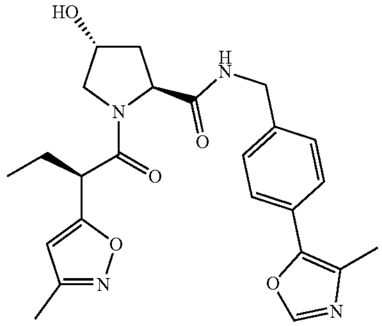
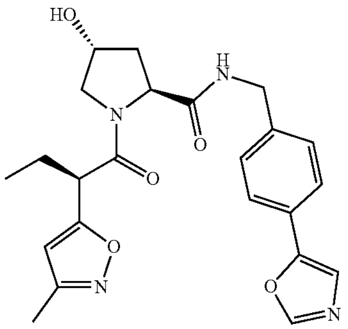
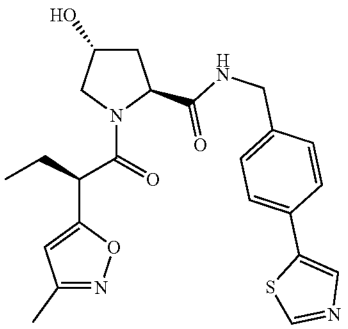
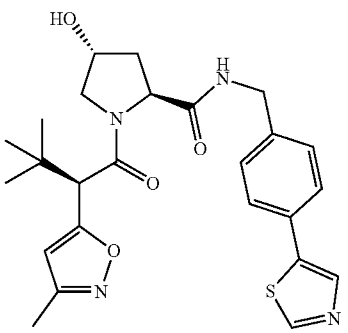

-continued
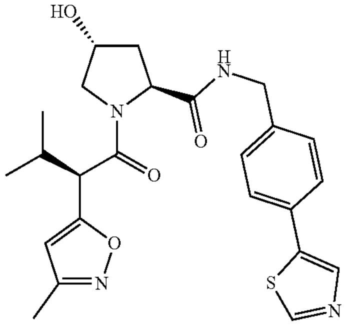
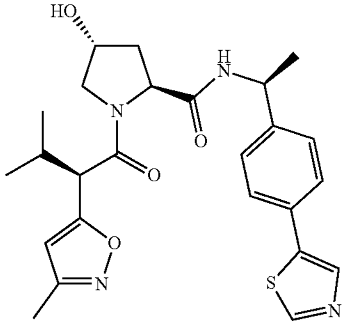
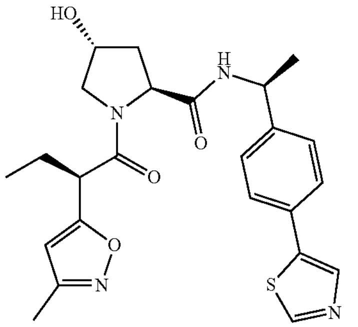
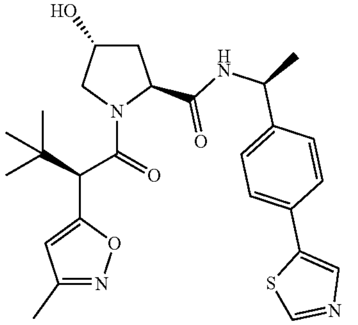
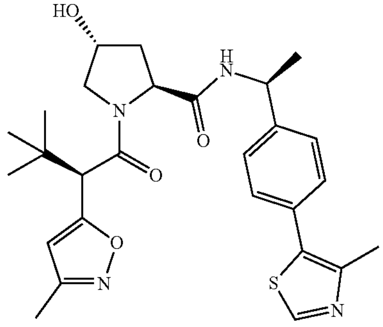
-continued
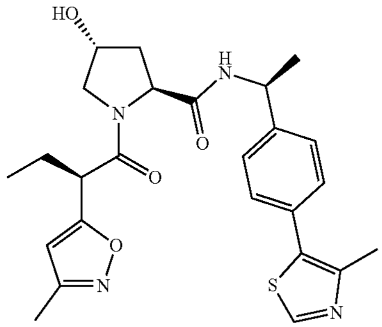
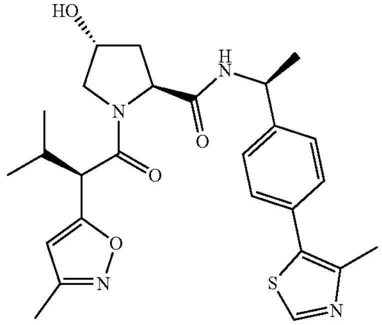
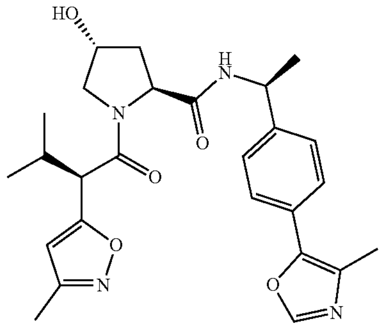
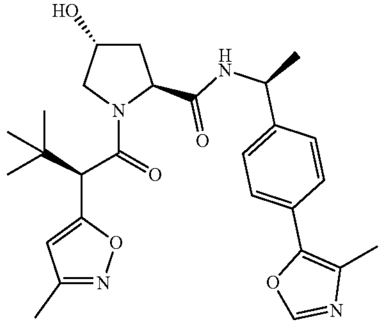
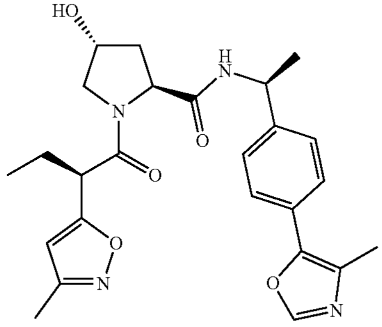

-continued
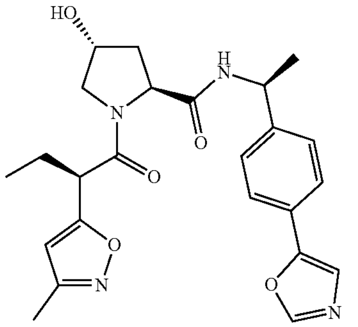
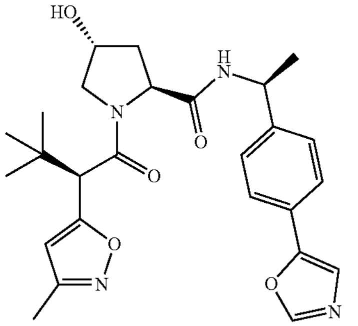
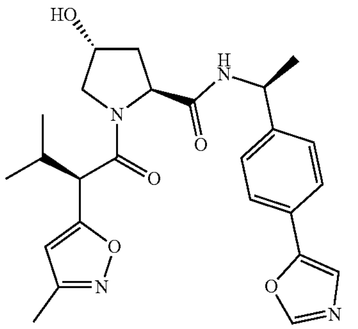
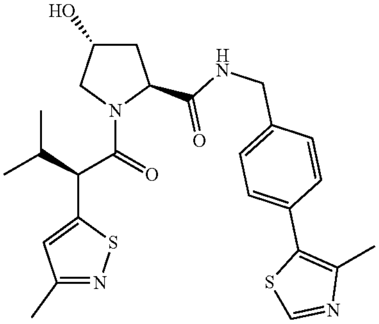
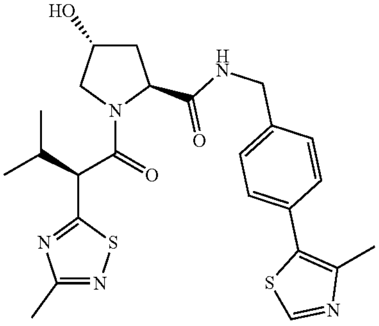
-continued
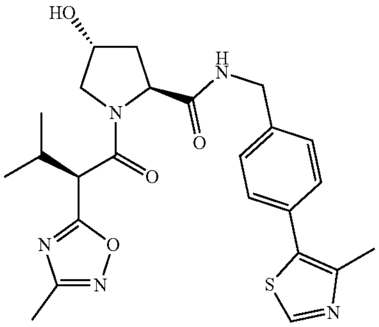
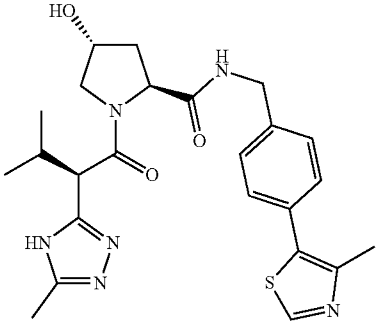
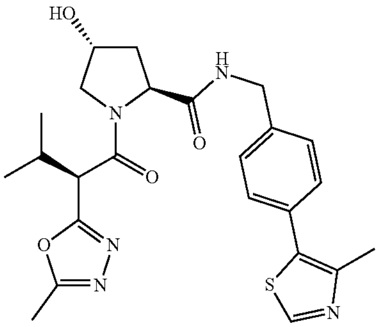
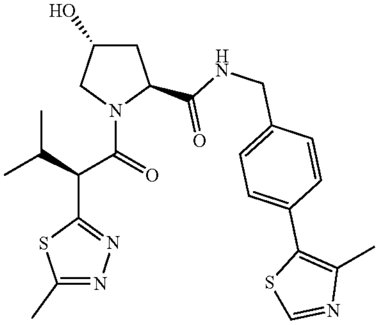
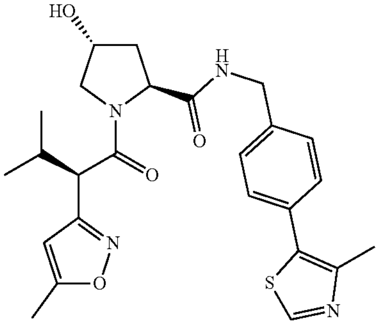

-continued
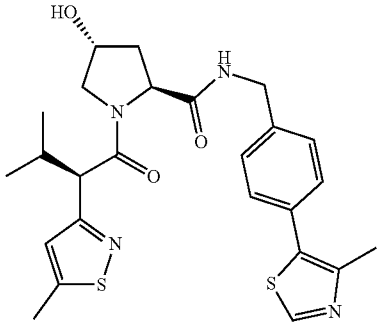
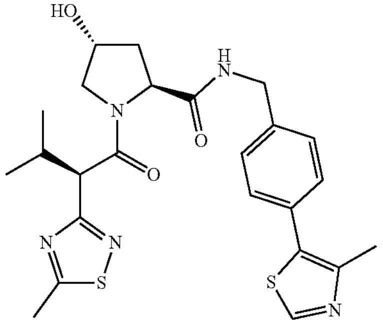
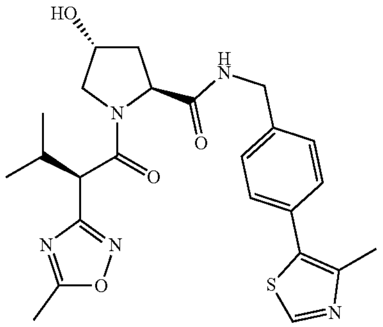
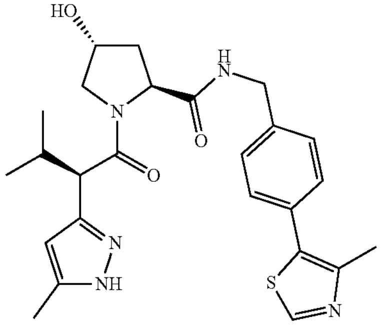
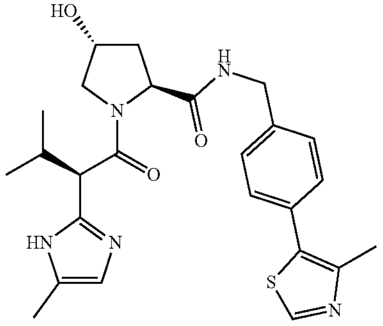
-continued
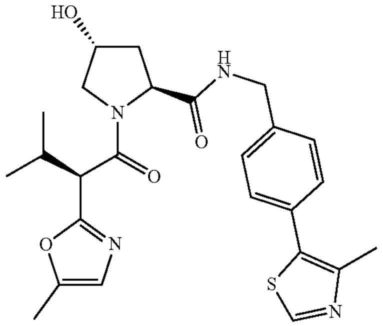
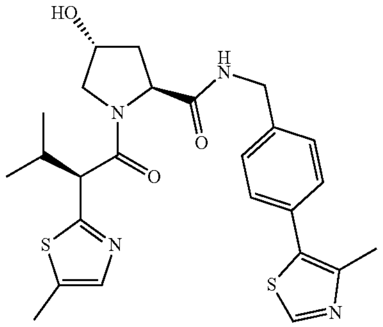
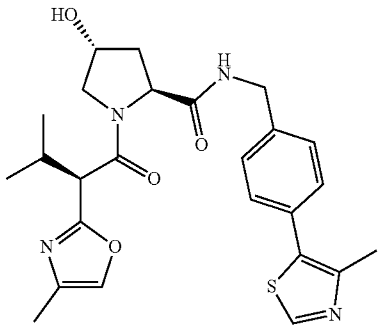
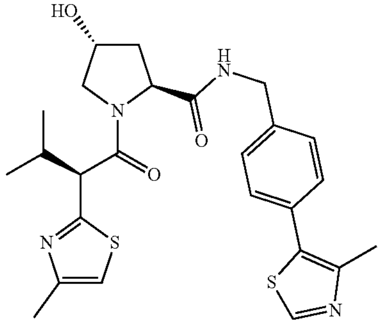
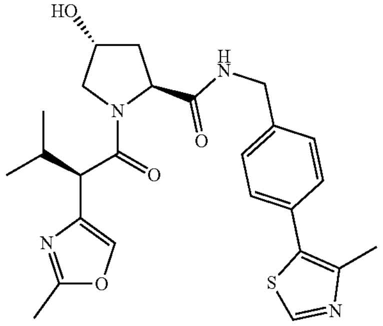

-continued
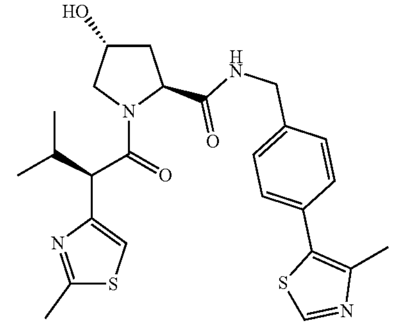
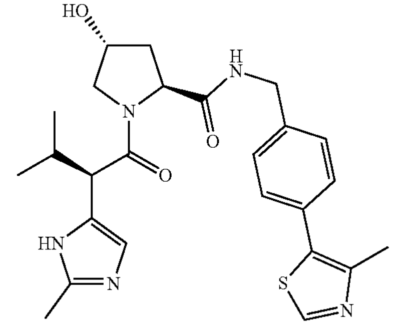
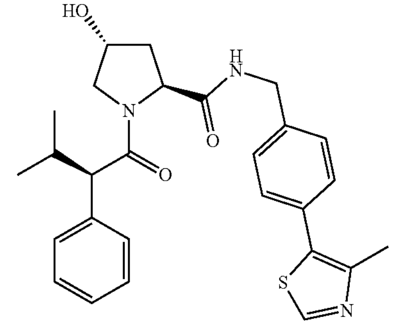
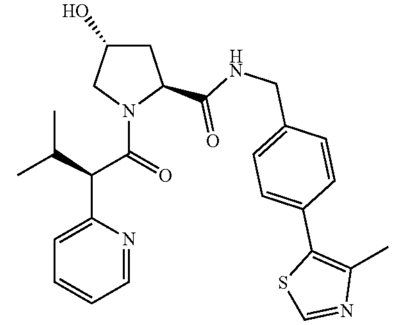
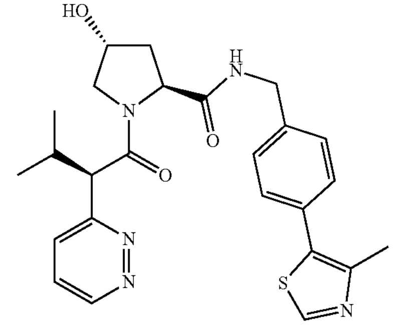
-continued
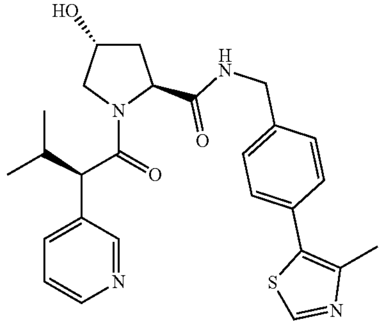
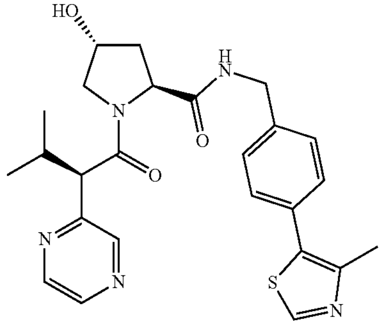
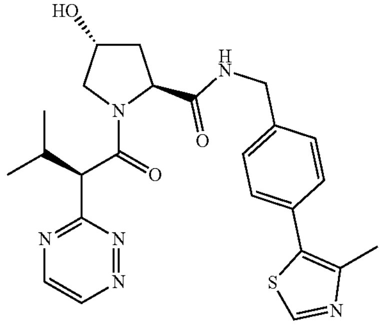
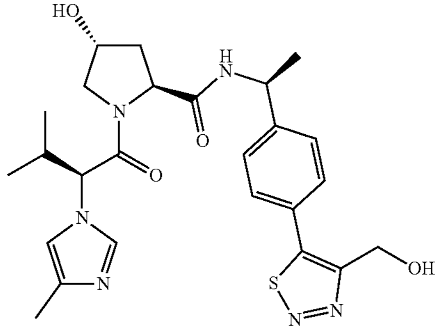
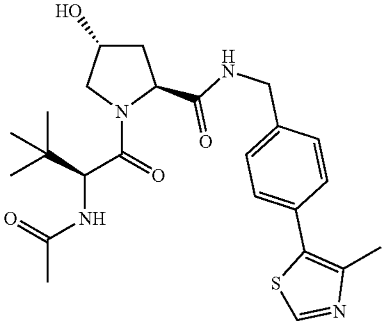

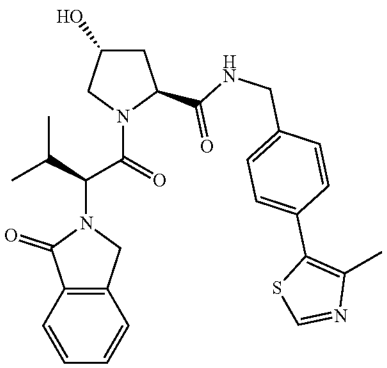
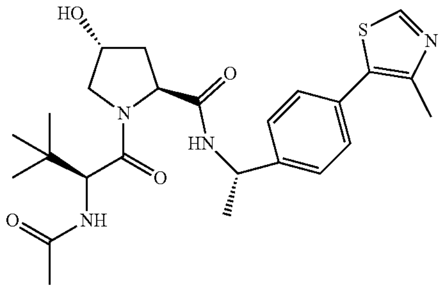
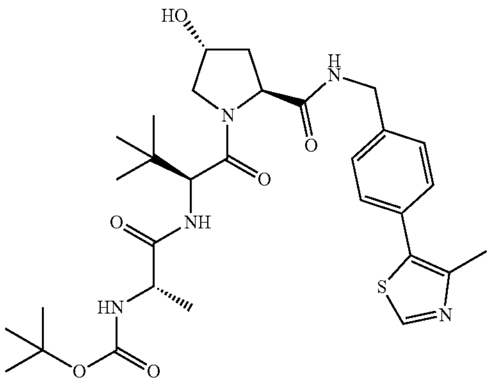
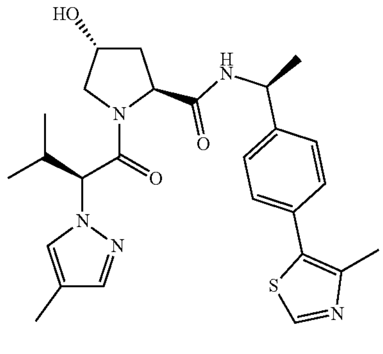
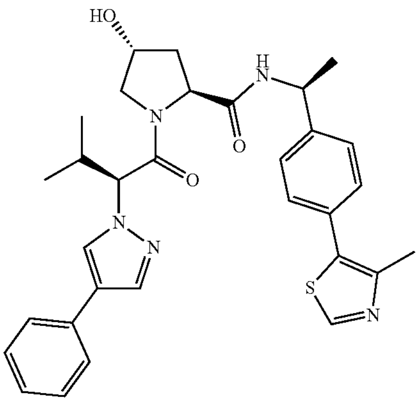
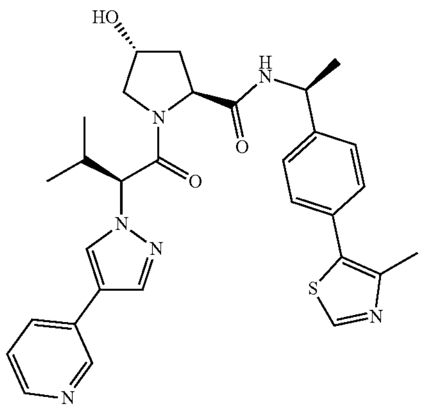
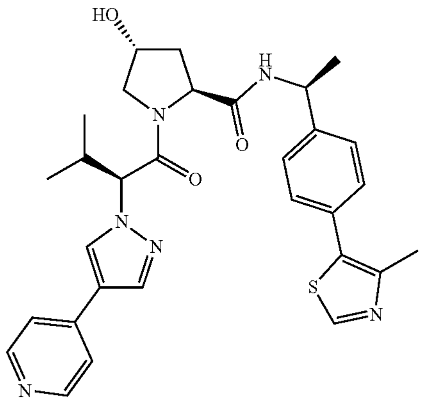
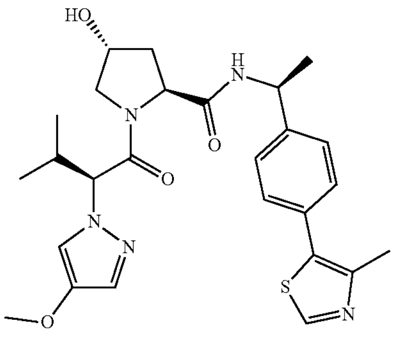

-continued

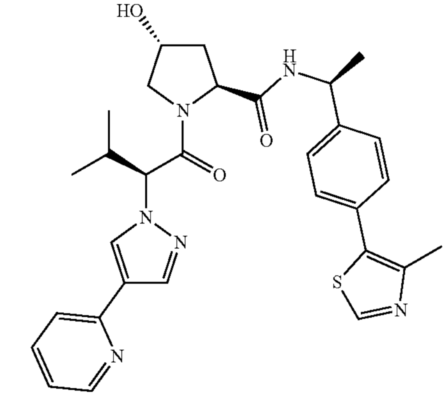

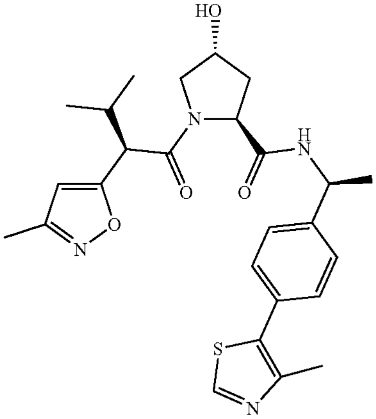

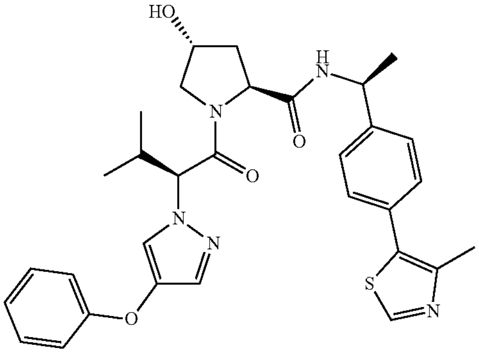

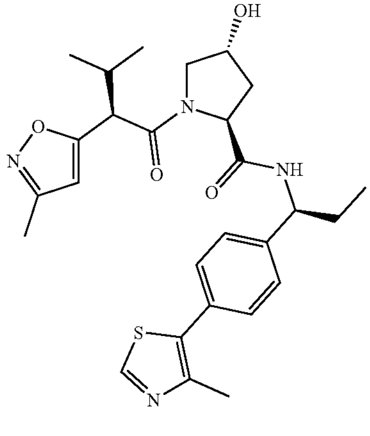

and

-continued

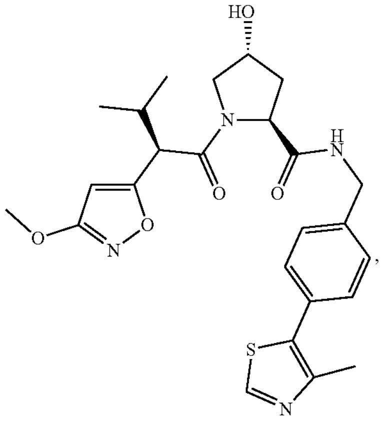

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary ILMs

AYPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

(I)

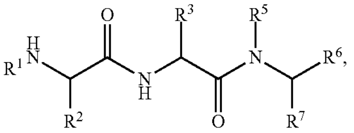

(II)

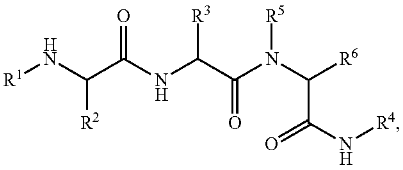

(III)

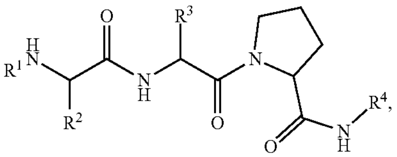

(IV)

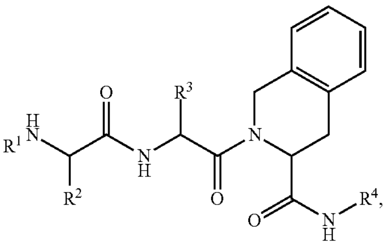

-continued (V)

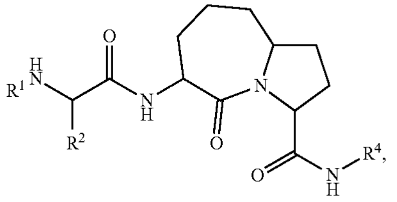

wherein:

$R^1$ for Formulas (I), (II), (III), (IV), and (V) is selected from H or alkyl;

$R^2$ for Formulas (I), (II), (III), (IV), and (V) is selected from H or alkyl;

$R^3$ for Formulas (I), (II), (III), (IV), and (V) is selected from H, alkyl, cycloalkyl and heterocycloalkyl;

$R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;

$R^3$ and $R^5$ for Formulas (I), (II), (III), (IV), and (V) taken together can form a 5-8-membered ring further optionally fused to 1-2 cycloalkyl, heterocycloalkyl, aryl or heteroaryl rings;

$R^7$ for Formulas (I), (II), (III), (IV), and (V) is selected from cycloalkyl, cycloalkylalkyl, heterocycloalkyl, heterocycloalkylalkyl, aryl, aryl-C(O)—$R^4$, arylalkyl, heteroaryl, heteroaryl-C(O)—$R^4$, heteroaryl-$R^4$, heteroaryl-naphthalene, heteroarylalkyl, or —C(O)NH—$R^4$, each one further optionally substituted with 1-3 substituents selected from halogen, alkyl, haloalkyl, hydroxyl, alkoxy, cyano, (hetero)cycloalkyl, (hetero) aryl, —C(O)NH—$R^4$, or —C(O)—$R^4$; and $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

(VI)

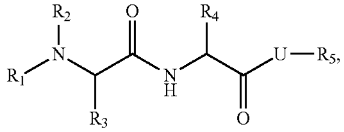

wherein:

$R_1$ of Formula (VI) is, independently selected from H, $C_1$-$C_4$-alky, $C_1$-$C_4$-alkenyl, $C_1$-$C_4$-alkynyl or $C_3$-$C_{10}$-cycloalkyl which are unsubstituted or substituted;

$R_2$ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;

$R_3$ of Formula (VI) is, independently selected from H, —$CF_3$, $C_2H_5$, $C_1$-$C_4$-alkyl, $C_1$-$C_4$-alkenyl, $C_1$-$C_4$-alkynyl, —$CH_2$—Z or any $R_2$ and $R_3$ together form a heterocyclic ring;

each Z of Formula (VI) is, independently selected from H, —OH, F, Cl, —$CH_3$, —$CF_3$, —$CH_2Cl$, —$CH_2F$ or $CH_2OH$;

$R_4$ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, —$(CH_2)_{0-6}$—$Z_1$, —$(CH_2)_{0-6}$-aryl, and —$(CH_2)_{0-6}$-het, wherein alkyl, cycloalkyl, and phenyl are unsubstituted or substituted;

$R_5$ of Formula (VI) is, independently selected from H, $C_{1-10}$-alkyl, aryl, phenyl, $C_{3-7}$-cycloalkyl, —$(CH_2)_{1-6}$—$C_{3-7}$— cycloalkyl, —$C_{1-10}$-alkyl-aryl, —$(CH_2)_{0-6}$—$C_{3-7}$-cycloalkyl-$(CH_2)_{0-6}$— phenyl, —$(CH_2)_{0-4}$—CH[$(CH_2)_{1-4}$— phenyl]$_2$, indanyl, —C(O)—$C_{1-10}$-alkyl, —C(O)—$(CH_2)_{1-6}$—$C_{3-7}$— cycloalkyl, —C(O)—$(CH_2)_{0-6}$-phenyl, $(CH_2)_{0-6}$—C(O)-phenyl, $(CH_2)_{0-6}$-het, —C(O)—$(CH_2)_{1-6}$-het, or $R_5$ is selected from a residue of an amino acid, wherein the alkyl, cycloalkyl, phenyl, and aryl substituents are unsubstituted or substituted;

$Z_1$ of Formula (VI) is, independently selected from —N($R_{10}$)—C(O)—$C_{1-10}$-alkyl, —N($R_{10}$)—C(O)—$(CH_2)_{0-6}$—$C_{3-7}$-cycloalkyl, —N($R_{10}$)—C(O)—$(CH_2)_{0-6}$-phenyl, —N($R_{10}$)—C(O)$(CH_2)_{1-6}$-het, —C(O)—N($R_{11}$)($R_{12}$), —C(O)—O—$C_{1-10}$-alkyl, —C(O)—O—$(CH_2)_{1-6}$—$C_{3-7}$-cycloalkyl, —C(O)—O—$(CH_2)_{0-6}$-phenyl, —C(O)—O— $(CH_2)_{1-6}$-het, —O—C(O)—$C_{1-10}$-alkyl, —O—C(O)—$(CH_2)_{1-6}$—$C_{3-7}$-cycloalkyl, —O—C(O)—$(CH_2)_{0-6}$-phenyl, —O—C(O)—$(CH_2)_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

$R_{10}$ of Formula (VI) is selected from H, —$CH_3$, —$CF_3$, —$CH_2OH$, or —$CH_2Cl$;

$R_{11}$ and $R_{12}$ of Formula (VI) are independently selected from H, $C_{1-4}$-alkyl, $C_{3-7}$-cycloalkyl, —$(CH_2)_{1-6}$—$C_{3-7}$— cycloakyl, $(CH_2)_{0-6}$-phenyl, wherein alkyl, cycloalkyl, and phenyl are unsubstituted or substituted; or $R_{11}$ and $R_{12}$ together with the nitrogen form het, and U of Formula (VI) is, independently, as shown in Formula (VII):

(VII)

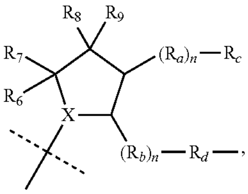

wherein:

each n of Formula (VII) is, independently selected from 0 to 5;

X of Formula (VII) is selected from the group —CH and N;

$R_a$ and $R_b$, of Formula (VII) are independently selected from the group O, S, or N atom or $C_{0-8}$-alkyl wherein one or more of the carbon atoms in the alkyl chain are optionally replaced by a heteroatom selected from O, S, or N, and where each alkyl is, independently, either unsubstituted or substituted;

$R_d$ of Formula (VII) is selected from the group Re-Q-$(R_f)_p(R_g)_q$, and $Ar_1$-D-$Ar_2$;

$R_c$ of Formula (VII) is selected from the group H or any $R_c$ and $R_d$ together form a cycloalkyl or het; where if $R_c$ and $R_d$ form a cycloalkyl or het, $R_5$ is attached to the formed ring at a C or N atom;

p and q of Formula (VII) are independently selected from 0 or 1;

$R_e$ of Formula (VII) is selected from the group Cj-s-alkyl and alkylidene, and each Re is either un substituted or substituted;

Q is selected from the group N, O, S, S(O), and $S(O)_2$;

$Ar_1$ and $Ar_2$ of Formula (VII) are independently selected from the group of substituted or unsubstituted aryl and het;

$R_f$ and $R_g$ of Formula (VII) are independently selected from Ft, —$C_{1-10}$-alkyl, $C_{1-10}$-alkylaryl, —OH, —O—$C_{1-10}$-alkyl, $(CH_2)_{0-6}$—$C_{3-7}$-cycloalky, —O—$(CH_2)_{0-6}$-aryI, phenyl, aryl, phenyl-phenyl, —$(CH_2)_{1-6}$-het, —O—$(CH_2)_{1-6}$-het, —$OR_{13}$, —C(O)—$R_{13}$, —C(O)—N($R_{13}$)($R_{14}$), —N($R_{13}$)($R_{14}$), —S—$R_{13}$, ~S(O)—$R_{13}$, —$S(O)_2$—$R_{13}$, —$Si(O)_2$ $NR_{13}R_{14}$, —$NR_{13}$—$S(O)_2$—$R_{14}$, —S—$C_{1-10}$-alkyl, aryl-$C_{1-4}$-alkyl, or het-$C_{1-4}$-alkyl, wherein alkyl, cycloalkyl, het, and aryl are unsubstituted or substituted, —$SO_2$—$C_{1-2}$-alkyl, —$SO_2$—$C_{1-2}$-alkylphenyl, —O—$C_{1-4}$-alkyl, or any $R_g$ and $R_f$ together form a ring selected from het or aryl;

D of Formula (VII) is selected from the group —CO—, —C(O)—$C_{1-7}$-alkylene or arylene, —$CF_2$—, —O—, —$S(O)_r$ where r is 0-2, 1,3-dioxalane, or $C_{1-7}$-alkyl-OH; where alkyl, alkylene, or arylene are unsubstituted or substituted with one or more halogens, OH, —O—$C_{1-6}$-alkyl, —S—$C_{1-6}$-alkyl, or —$CF_3$; or each D is, independently selected from N(Rh);

Rh is selected from the group H, unsubstituted or substituted $C_{1-7}$-alkyl, aryl, unsubstituted or substituted —O—($C_{1-7}$-cycloalkyl), —C(O)—$C_{1-10}$-alkyl, C(O)—$C_{0-10}$-alkyl-aryl, —C—O—$C_{01-10}$-alkyl, —C—O—$C_{0-10}$-alkyl-aryl, —$SO_2$—$C_{1-10}$-alkyl, or —$SO_2$—($C_{0-10}$— alkylaryl);

$R_6$, $R_7$, $R_8$, and $R_9$ of Formula (VII) are, independently, selected from the group H, —$C_{1-10}$-alkyl, —$C_{1-10}$-alkoxy, aryl-$C_{1-10}$— alkoxy, —OH, —O—$C_{1-10}$-alkyl, —$(CH_2)_{0-6}$—$C_{3-7}$-cycloalkyl, —O—$(CH_2)_{0-6}$-aryl, phenyl, —$(CH_2)_{1-6}$-het, —O—$(CH_2)_{1-6}$-het, —$OR_{13}$, —C(O)—$R_{13}$, —C(O)—N($R_{13}$)($R_{14}$), —N($R_{13}$)($R_{14}$), —S—$R_{13}$, —S(O)—$R_{13}$, —$S(O)_2$— $R_{13}$, —$S(O)_2$—$NR_{13}R_{14}$, or —$NR_{13}$—$S(O)_2$—$R_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H, $C_{1-10}$-alkyl, —$(CH_2)_{0-6}$—$C_{3-7}$-cycloalkyl, —$(CH_2)_{0-6}$— $(CH)_{0-1}$-$(aryl)_{1-2}$, —C(O)—$C_{1-10}$-alkyl, —C(O)—$(CH_2)_{1-6}$—$C_{3-7}$-cycloalkyl, —C(O)—O—$(CH_2)_{0-6}$-aryl, —C(O)—$(CH_2)_{0-6}$—O-fluorenyl, —C(O)—NH—$(CH_2)_{0-6}$-aryl, —C(O)—$(CH_2)_{0-6}$-aryl, —C(O)—$(CH_2)_{0-6}$-het, —C(S)—$C_{1-10}$-alkyl, —C(S)—$(CH_2)_{1-6}$—$C_{3-7}$-cycloalkyl, —C(S)—O—$(CH_2)_{0-6}$-aryl, —C(S)—$(CH_2)_{0-6}$—O-fluorenyl, —C(S)—NH—$(CH_2)_{0-6}$-aryl, —C(S)—$(CH_2)_{0-6}$-aryl, or —C(S)—$(CH_2)_{1-6}$-het, wherein each alkyl, cycloalkyl, and aryl is unsubstituted or substituted: or any $R_{13}$ and $R_{14}$ together with a nitrogen atom form het;

wherein alkyl substituents of $R_{13}$ and $R_{14}$ of Formula (VII) are unsubstituted or substituted and when substituted, are substituted by one or more substituents selected from $C_{1-10}$-alkyl, halogen, OH, —O—$C_{1-6}$-alkyl, —S—$C_{1-6}$-alkyl, and —$CF_3$; and substituted phenyl or and of $R_{13}$ and $R_{14}$ are substituted by one or more substituents selected from halogen, hydroxyl, $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In any of the compounds described herein, the ILM can have the structure of Formula (VIII), which is based on the IAP ligrands described in Ndubaku, C., et al. Antagonism of c-IAP and XIAP proteins is required for efficient induction of cell death by small-molecule IAP antagonists, *ACS Chem. Biol.,* 557-566, 4 (7) (2009), or an unnatural mimetic thereof:

(VIII)

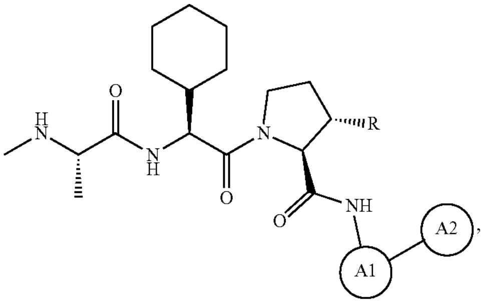

wherein each of A1 and A2 of Formula (VIII) is independently selected from optionally substituted monocyclic, fused rings, aryls and hetoroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of (A)

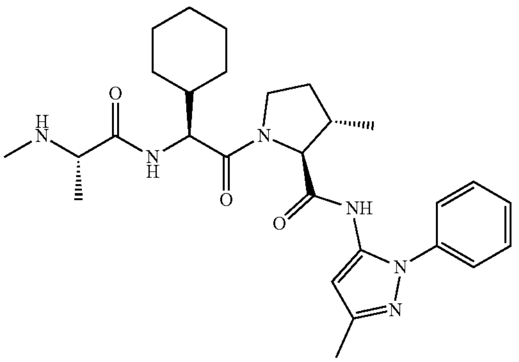

and

-continued (B)

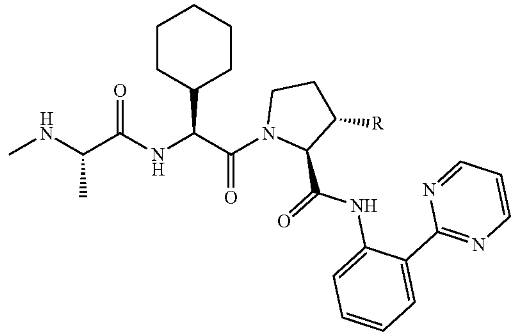

In any of the compounds described herein, the ILM can have the structure of Formula (IX), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(IX)

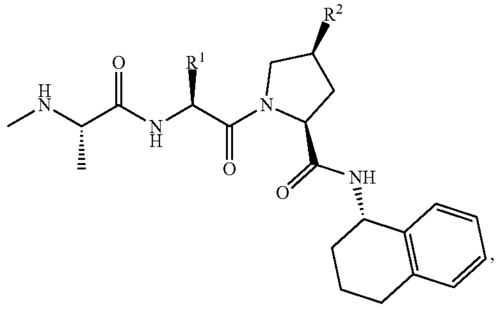

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(X)

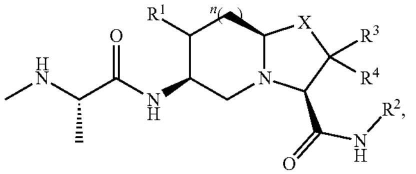

n = 1, 2, 3 wherein:

$R^1$ of Formula (X) is selected from H, $—CH_2OH$, $—CH_2CH_2OH$, $—CH_2NH_2$, $—CH_2CH_2NH_2$;

X of Formula (X) is selected from S or $CH_2$;

$R^2$ of Formula (X) is selected from:

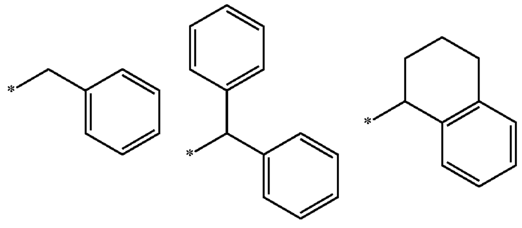

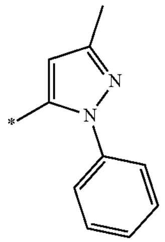

$R^3$ and $R^4$ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(XI)

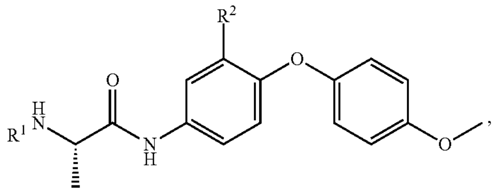

wherein $R^1$ of Formula (XI) is selected from H or Me, and $R^2$ of Formula (XI) is selected from H or

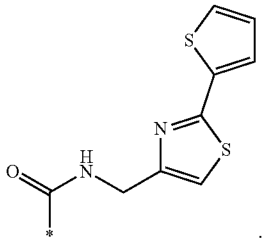

In any of the compounds described herein, the ILM can have the structure of Formula (XII), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(XII)

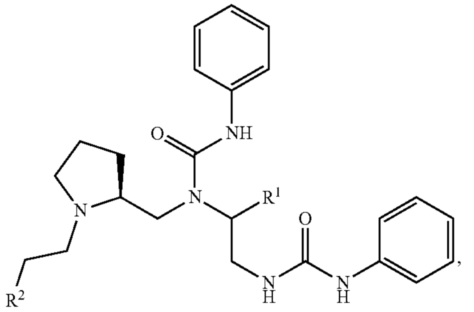

wherein:

$R^1$ of Formula (XII) is selected from:

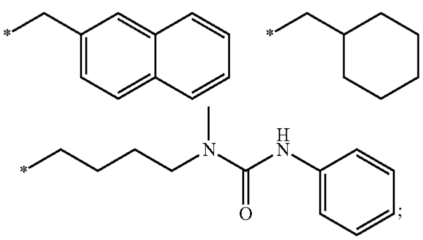

and $R^2$ of Formula (XII) is selected from:

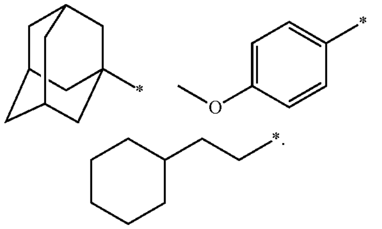

In any of the compounds described herein, the IAP E3 ubiquitin ligase binding moiety is selected from the group consisting of:

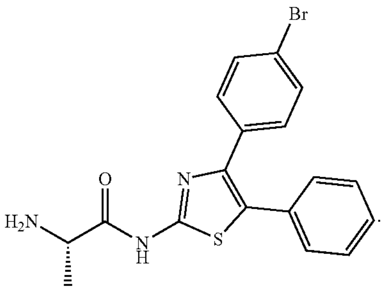 [SMILES: C[C@H](N)C(=O)Nc1nc(-c2ccc(Br)cc2)c(-c2ccccc2)s1]

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

(XIII)

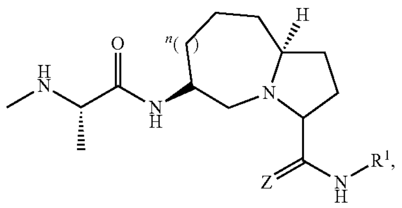

n = 0, 2 or, preferably, 1 wherein:

Z of Formula (XIII) is absent or O;

$R^1$ of Formula (XIII) is selected from:

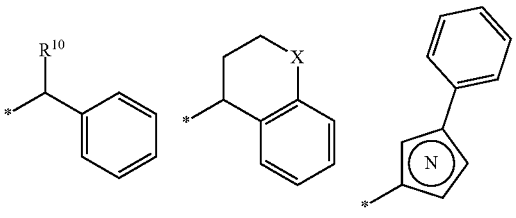

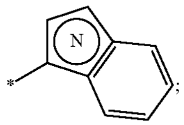

$R^{10}$ of

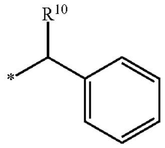

is selected from H, alkyl, or aryl;

X is selected from CH2 and O; and

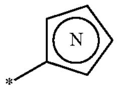

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

(XIV)

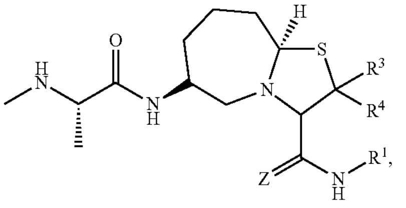

wherein:

Z of Formula (XIV) is absent or O;

$R^3$ and $R^4$ of Formula (XIV) are independently selected from H or Me;

$R^1$ of Formula (XIV) is selected from:

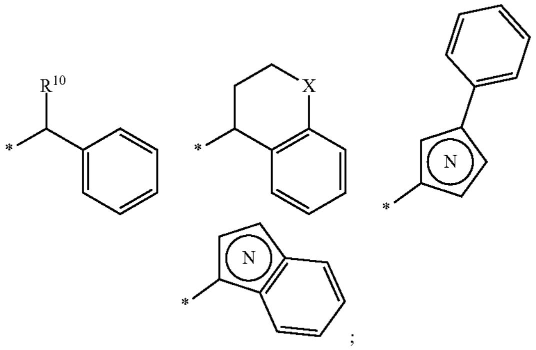

;

$R^{10}$ of

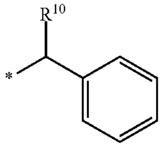

is selected from H, alkyl, or aryl;

X of

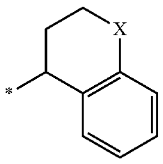

is selected from CH2 and O; and

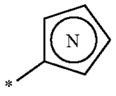

of

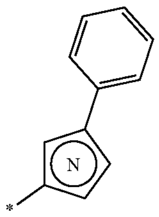

or

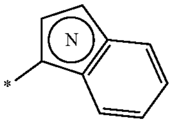

is a nitrogen-containing heterayl.

In any of the compounds described herein, the ILM is selected from the group consisting of:

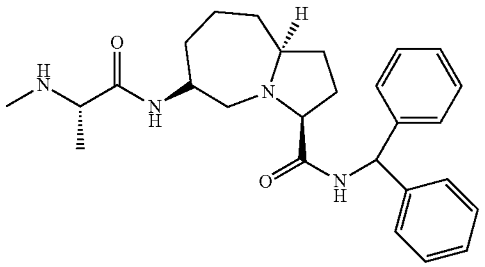

and

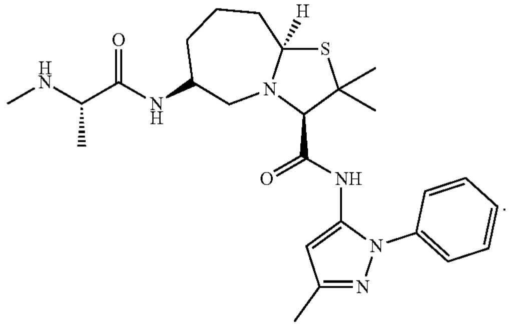

.

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

(XV)

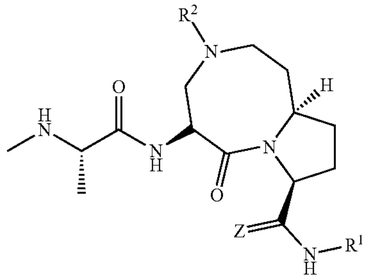

wherein:

Z of Formula (XV) is absent or O;

$R^1$ of Formula (XV) is selected from:

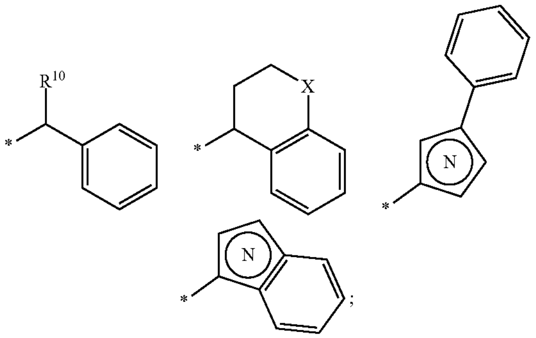

;

$R^{10}$ of

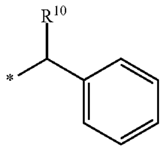

is selected from H, alkyl, or aryl;

X of

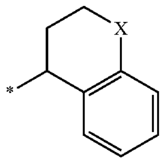

is selected from $CH_2$ and O; and

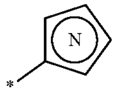
of
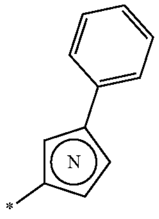
or
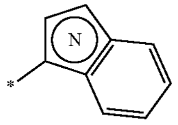

is a nitrogen-containing heterary]; and $R^2$ of Formula (XV) selected from H, alkyl, or acyl;

In a particular embodiment, the ILM has the following structure:

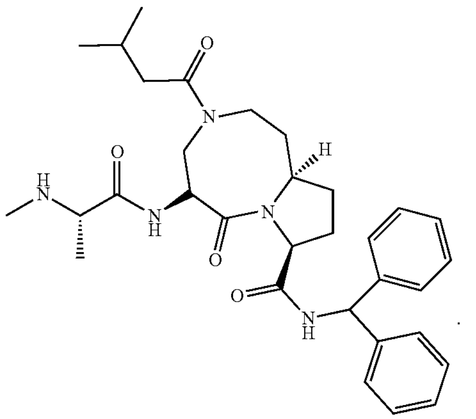

In any of the compounds described herein, the ILM can have the structure of Formula (XVI), which is based on the IAP ligand described in WO Pub. No. 2006/069063, or an unnatural mimetic thereof:

(XVI)

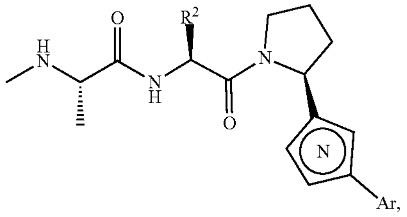

wherein:

$R^2$ of Formula (XVI) is selected from alkyl, cycloalkyl and heterocycloalkyl; more preferably, from isopropyl, tert-butyl, cyclohexyl and tetrahydropyranyl, most preferably from cyclohexyl;

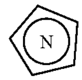

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVII)

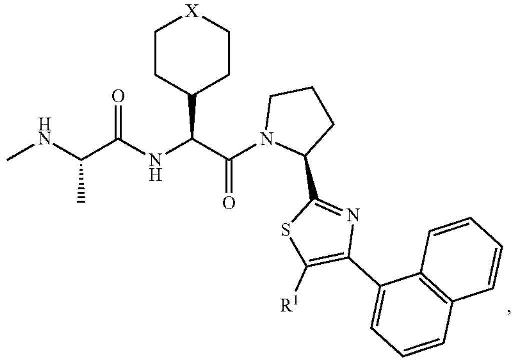

wherein:

$R^1$ of Formula (XVII) is selected from the group halogen (e.g. fluorine), cyano,

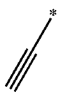
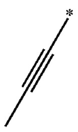
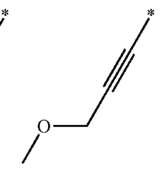
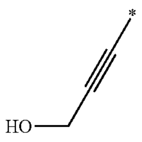
;

X of Formula (XVII) is selected from the group O or CH2.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVIII)

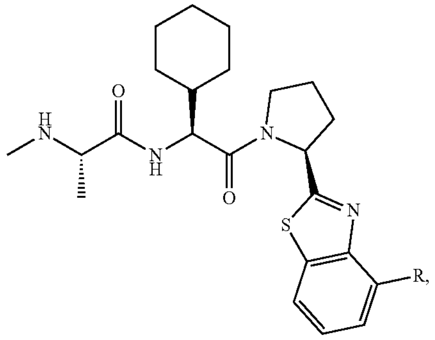

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antogonists of inhibitors of apoptosis proteins based on thiazole amide isosteres*, Bioorg. Med. Chem. Lett., 20(7), 2229-33 (2010), or an unnatural mimetic thereof:

(XIX)

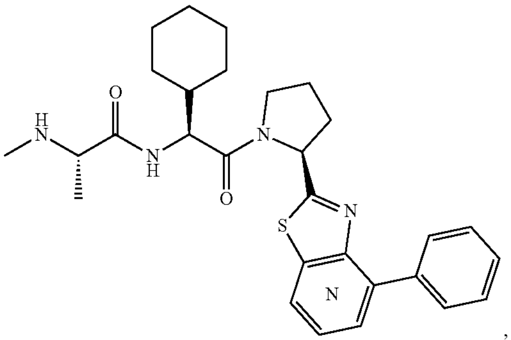

, wherein

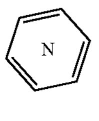

is a 6-member nitrogen heteroaryl.

In a certain embodiment, the ILM of the composition is selected from the group consisting of:

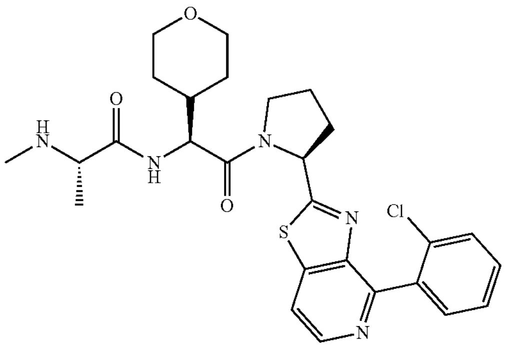

and

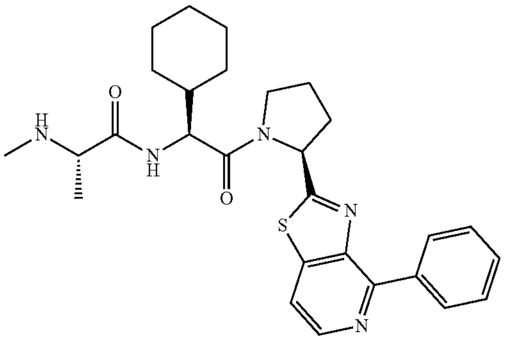

.

In certain embodiments, the ILM of the composition is selected from the group consisting of:

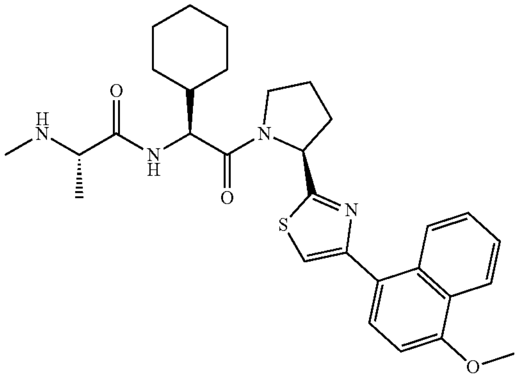

,

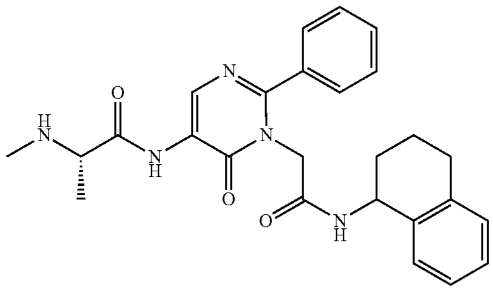

,

-continued

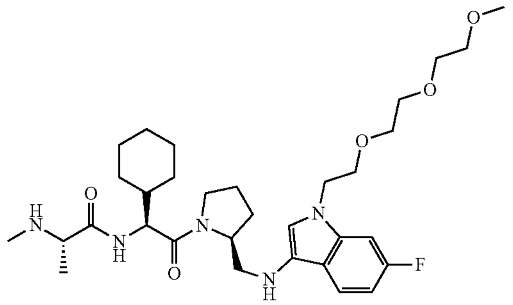

, and

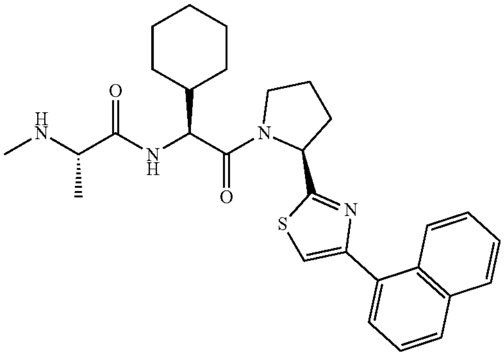

,

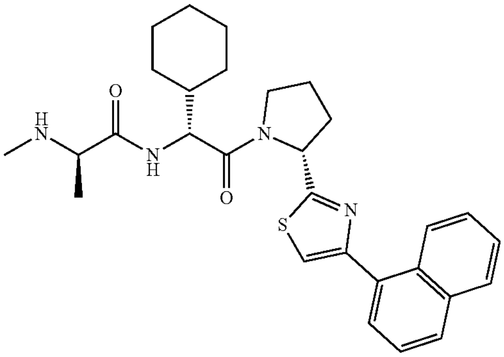

.

In any of the compounds described herein, the ILM can have the structure of Formula (XX), which is based on the IAP ligands described in WO Pub. No. 2007/101347, or an unnatural mimetic thereof:

(XX)

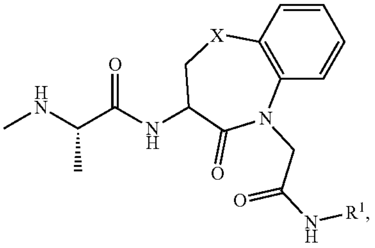

wherein X of Formula (XX) is selected from $CH_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

(XXI)

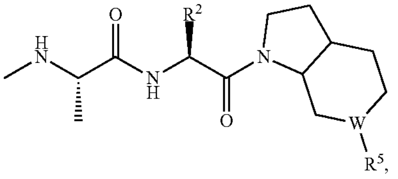

wherein:

$R^2$ of Formula (XXI) is selected from:

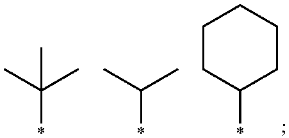

;

$R^5$ of Formula (XXI) is selected from:

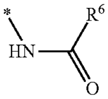

and

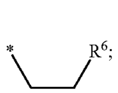

and

W of Formula (XXI) is selected from CH or N; and $R^6$ of

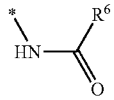

and

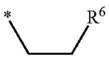

are independently a mono- or bicyclic fused aryl or heteroaryl.

In certain embodiments, the ILM of the compound is selected from the group consisting of:

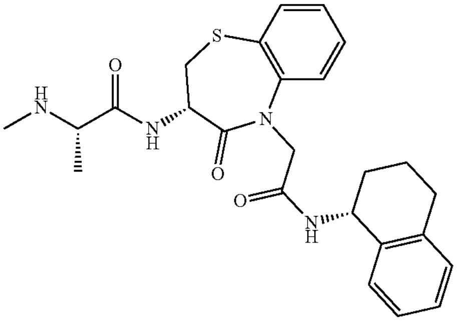

,

-continued

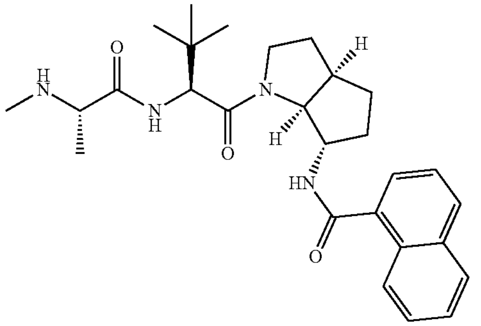

, and

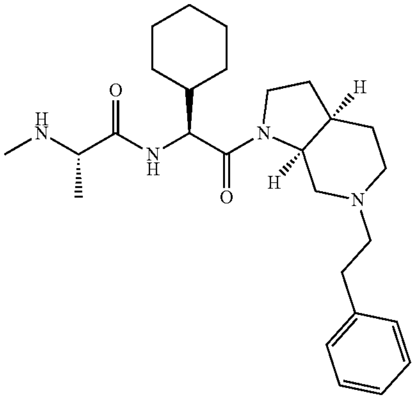

In any of the compounds described herein, the ILM can have the structure of Formula (XXII) or (XXIV), which are derived from the IAP ligands described in WO Pub. No. 2015/006524 and Perez H L, *Discovery of potent heterodimeric antagonists of inhibitor of apoptosis proteins* (*IAPs*) *with sustained antitumor activity*. J. Med. Chem. 58(3), 1556-62 (2015), or an unnatural mimetic thereof, and the chemical linker to linker group L as shown:

(XXII)

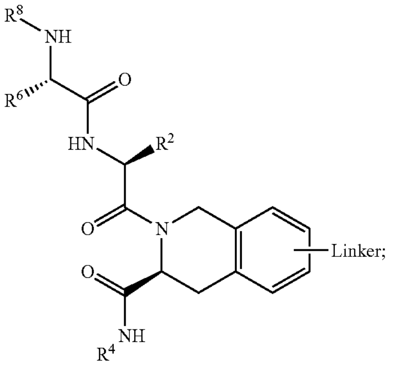

-continued (XXIII)

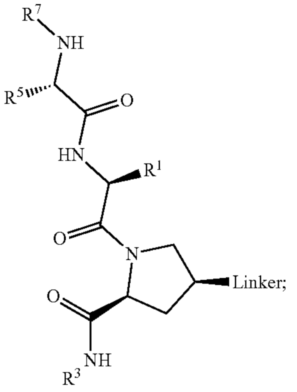

or (XXIV)

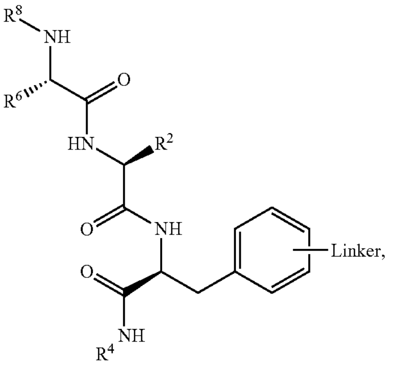

wherein:

$R^1$ of Formula (XXII), (XXIII) or (XXIV) is selected from optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXII), (XXIII) or (XXIV) is selected from optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXII), (XXIII) or (XXIV) are independently selected from optionally substituted thioalkyl wherein the substituents attached to the S atom of the thioalkyl are optionally substituted alkyl, optionally substituted branched alkyl, optionally substituted heterocyclyl, $—(CH_2)_vCOR^{20}$, $—CH_2CHR^{21}COR^{22}$ or $—CH_2R^{23}$, wherein:

v is an integer from 1-3;

$R^{20}$ and $R^{22}$ of $—(CH_2)_vCOR^{20}$ and $—CH_2R^{23}$ are independently selected from OH, $NR^{24}R^{25}$ or $OR^{26}$;

$R^{21}$ of $—CH_2CHR^{21}COR^2$ is selected from $NR^{24}R^{25}$;

$R^{23}$ of $—CH_2R^{23}$ is selected from optionally substituted aryl or optionally substituted heterocyclyl, wherein the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $—CH_2(OCH_2CH_2O)_mCH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXII), (XXIII) or (XXIV) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII), (XXIII) or (XXIV) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXIV):

$R^7$ and $R^8$ are selected from the H or Me;

$R^5$ and $R^6$ are selected from the group comprising:

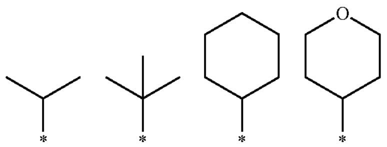

$R^3$ and $R^4$ are selected from the group comprising:

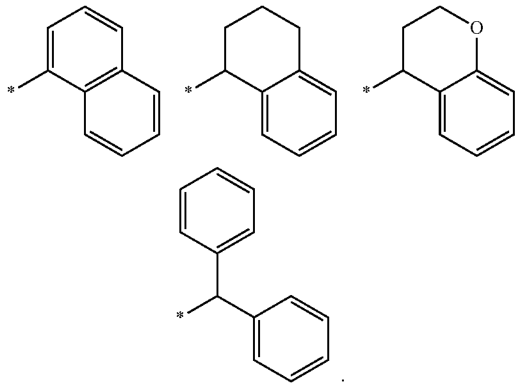

In any of the compounds described herein, the ILM can have the structure of Formula (XXV), (XXVI), (XXVII), or (XXVIII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

(XXV)

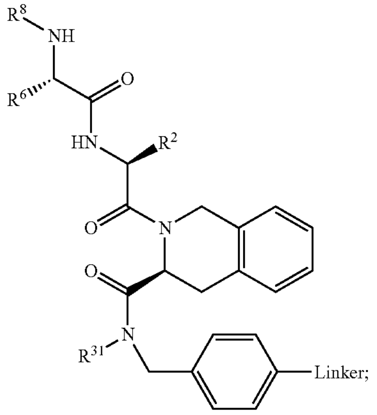

(XXVI)

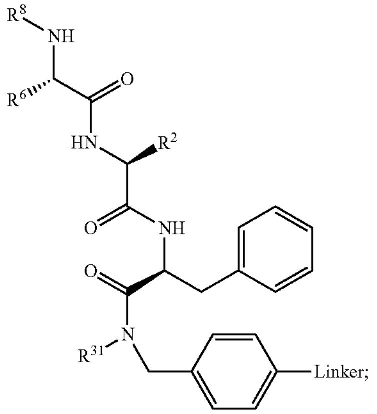

(XXVII)

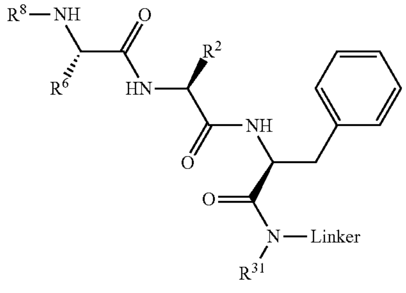

; and (XXVIII)

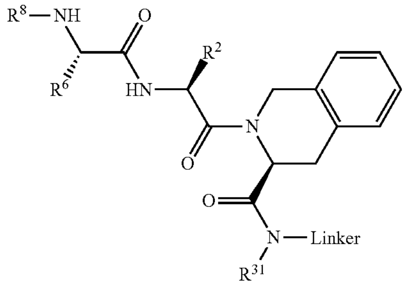

, wherein:

$R^2$ of Formula (XXV) through (XXVIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

or alternatively;

$R^1$ and $R^2$ of Formula (XXV) and (XXVIII) are independently selected from H, an optionally substituted thioalkyl —$CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{25}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)\overline{\omega}_rNH_2$, such as spermine or spermidine, wherein $\delta$=0-2, $\psi$=1-3, $\overline{\omega}$=0-2;

$R^{26}$ of $OR^{26}$ is an optionally substituted alkyl, wherein the optional substituents are OH, halogen or $NH_2$;

m is an integer from 1-8;

$R^6$ and $R^8$ of Formula (XXV) through (XXVIII) are independently selected from hydrogen, optionally substituted alkyl or optionally substituted cycloalkyl; and $R^{31}$ of Formulas (XXV) through (XXVIII) is selected from alkyl, aryl, arylalkyl, heteroaryl or heteroarylalkyl optionally further substituted, preferably selected form the group consisting of:

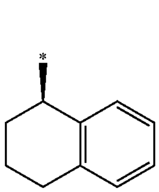
,
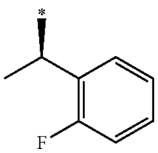
,
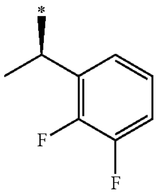
,

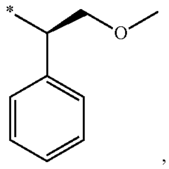
, and
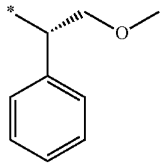
.

In any of the compounds described herein, the ILM can have the structure of Formula (XXIX) or (XXX), which are derived from the IAP ligands described in WO Pub. No. 2013/071039, or an unnatural mimetic thereof:

(XXIX)

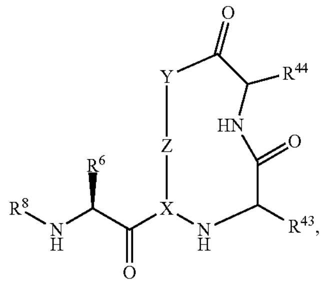

(XXX)

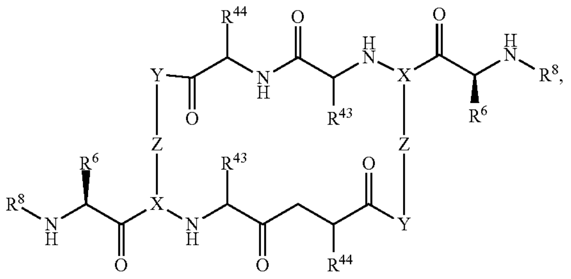

wherein:

$R^{43}$ and $R^{44}$ of Formulas (XXIX) and (XXX) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXIX) and (XXX) are independently selected from hydrogen, optionally substituted alkyl or optionally substituted cycloalkyl, each X of Formulas (XXIX) and (XXX) is independently selected from:

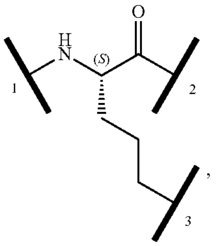
,
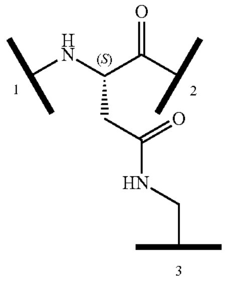
,
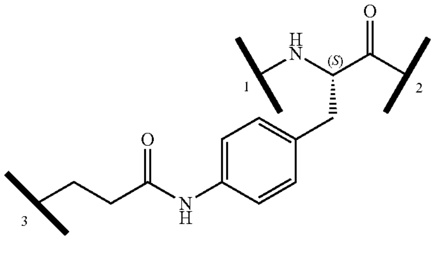
,

-continued
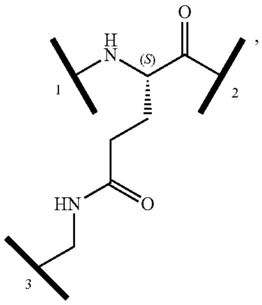,
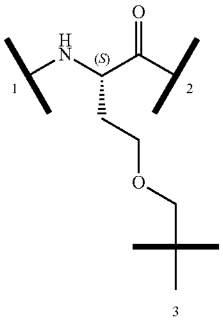,
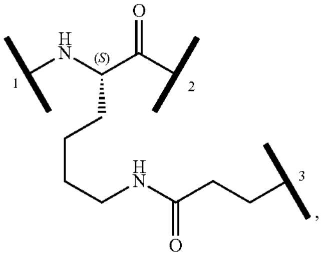,
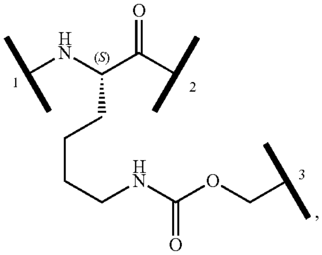,
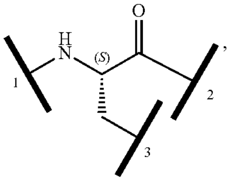,
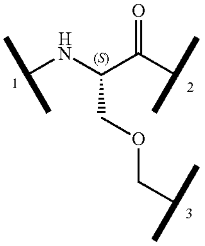,
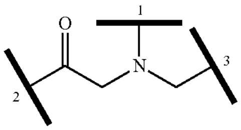,
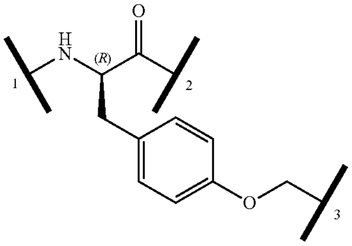,
-continued
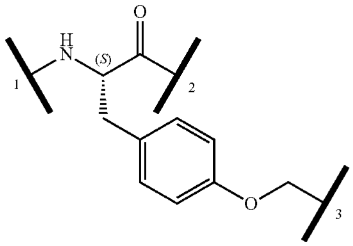,
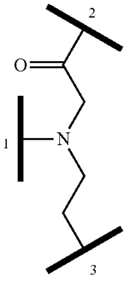,
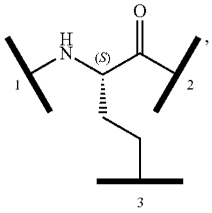, and
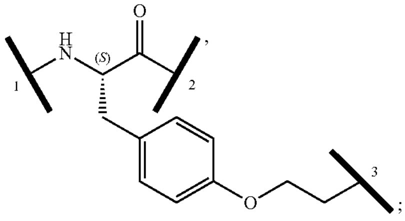;
each Z of Formulas (XXIX) and (XXX) is selected from
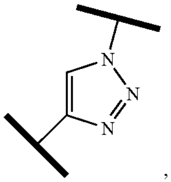,
wherein each
represents a point of attachment to the compound; and each Y is selected from:
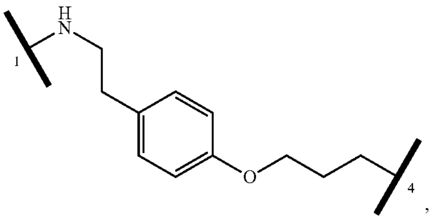, -continued
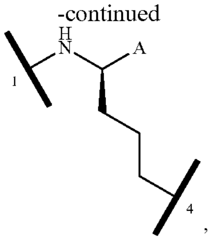
,
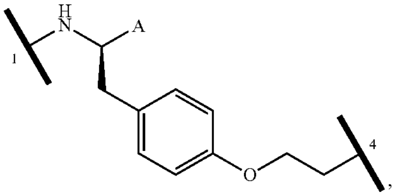
,
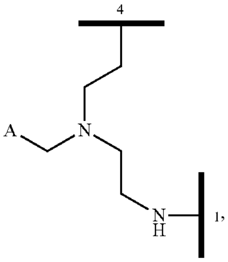
,
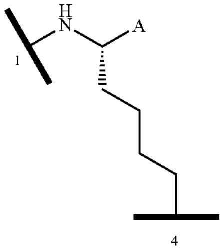
,
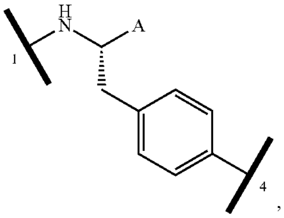
,
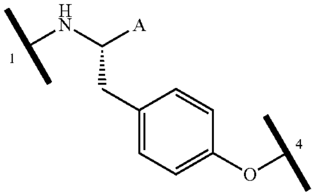
,
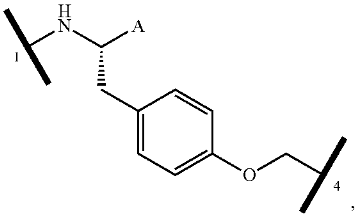
,
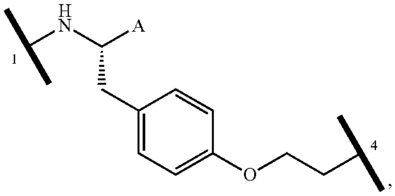
,
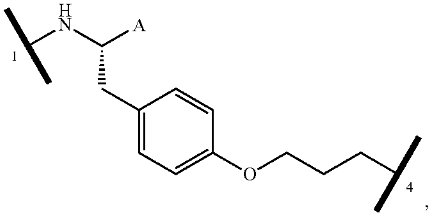
,
-continued
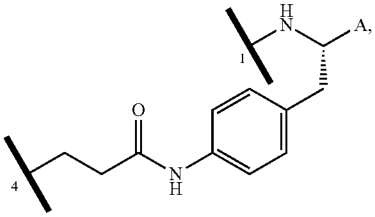
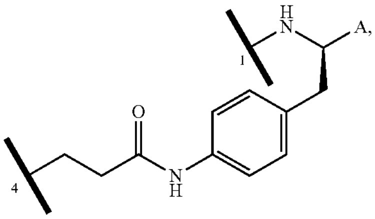
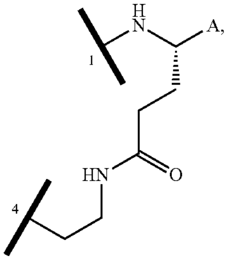
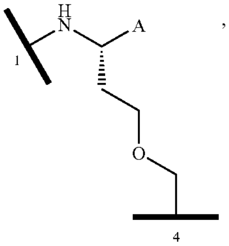
,
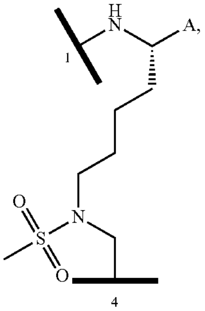
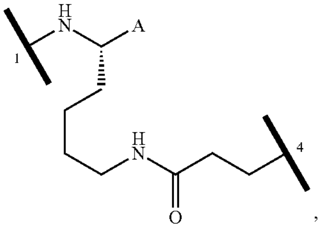
,
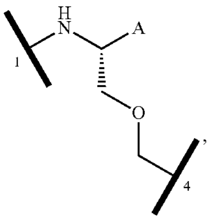
,
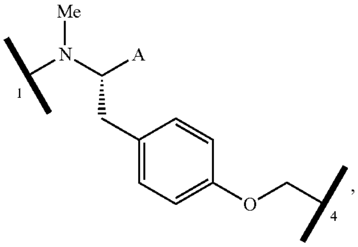
, -continued

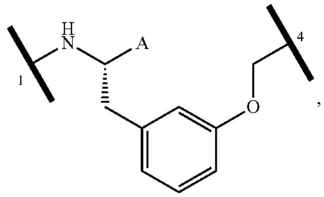

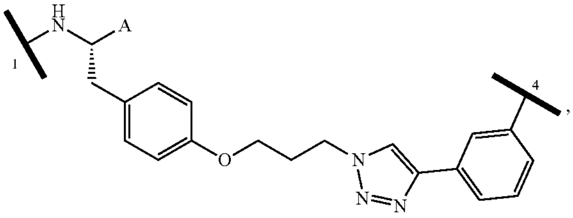

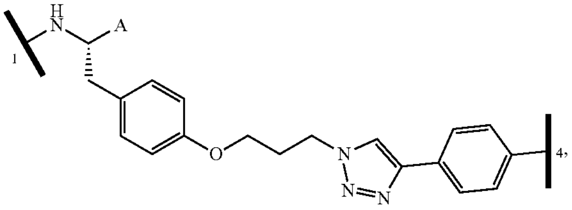

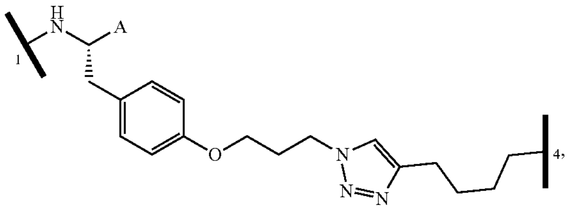

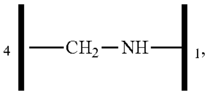

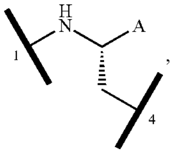

and

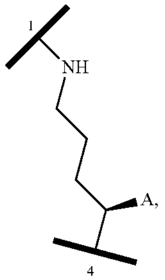

wherein:

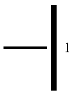

represents a point of attachment to a —C═O portion of the compound;

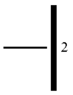

represents a point of attachment to an amino portion of the compound;

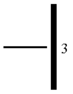

represents a first point of attachment to Z;

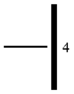

represents a second point of attachment to Z; and

A is selected from —C(O)$R^3$ or

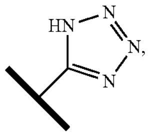

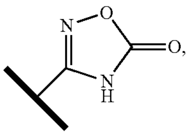

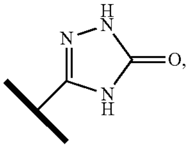

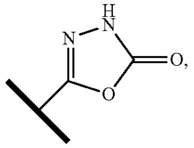

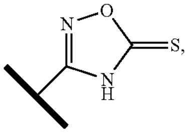

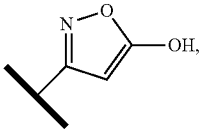

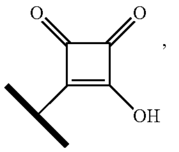

,

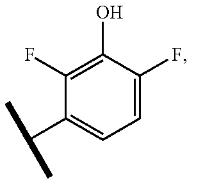

or a tautomeric form of any of the foregoing, wherein:

$R^3$ of —C(O)$R^3$ is selected from OH, NHCN, $NHSO_2R^{10}$, $NHOR^{11}$ or $N(R^{12})(R^{13})$; $R^{10}$ and $R^{11}$ of $NHSO_2R^{10}$ and $NHOR^{11}$ are independently selected from —$C_1$-$C_4$ alkyl, cycloalkyl, aryl, heteroaryl, or heterocycloalkyl, any of which are optionally substituted, and hydrogen;

each of $R^{12}$ and $R^{13}$ of $N(R^{12})(R^{13})$ are independently selected from hydrogen, —$C_1$-$C_4$ alkyl, —($C_1$-$C_4$ alkylene)-NH—($C_1$-$C_4$ alkyl), benzyl, —($C_1$-$C_4$ alkylene)-C(O)OH, —($C_1$-$C_4$ alkylene)-C(O)$CH_3$, —CH(benzyl)-COOH, —$C_1$-$C_4$ alkoxy, and —($C_1$-$C_4$ alkylene)-O—($C_1$-$C_4$ hydroxy alkyl); or $R^{12}$ and $R^{13}$ of $N(R^{12})(R^{13})$ are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXI), which are derived from the IAP ligands described in WO Pub. No. 2013/071039, or an unnatural mimetic thereof:

(XXXI)

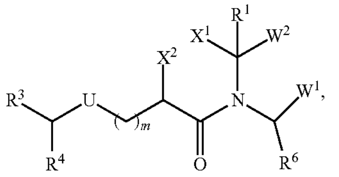

wherein:

$W^1$ of Formula (XXXI) is selected from O, S, N—$R^A$, or $C(R^{8a})(R^{8b})$;

$W^2$ of Formula (XXXI) is selected from O, S, N—$R^A$, or $C(R^{8c})(R^{8d})$; provided that $W^1$ and $W^2$ are not both O, or both S;

$R^1$ of Formula (XXXI) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ is selected from O, N—$R^A$, S, S(O), or $S(O)_2$, then $X^2$ is $C(R^{2a}R^{2b})$;

or:

$X^1$ of Formula (XXXI) is selected from $CR^{2c}R^{2d}$ and $X^2$ is $CR^{2a}R^{2b}$, and $R^{2c}$ and $R^{2a}$ together form a bond;

or:

$X^1$ and $X^2$ of Formula (XXXI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

$X^1$ of Formula (XXXI) is selected from $CH_2$ and $X^2$ is C═O, C═C$(R^C)_2$, or C═$NR^c$; where each $R^c$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$ of $CR^{2c}R^{2d}$ and $CR^{2a}R^{2b}$ are independently selected from H, substituted or unsubstituted C1-C6alkyl, substituted or unsubstituted $C_1$-$C_6$heteroalkyl substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XXXI) is selected from 0, 1 or 2;

—U— of Formula (XXXI) is selected from —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XXXI) is selected from $C_1$-$C_3$alkyl, or $C_1$-$C_3$fluoroalkyl;

$R^4$ of Formula (XXXI) is selected from —$NHR^5$, —N($R^5$)2, —N+($R^5$)3 or —$OR^5$;

each $R^5$ of —$NHR^5$, —N($R^5$)2, —N+($R^5$)3 and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXI) together with the atoms to which they are attached form a substituted or unsubstituted 5-7 membered ring;

or:

$R^3$ of Formula (XXXI) is bonded to a nitrogen atom of U to form a substituted or unsubstituted 5-7 membered ring;

$R^6$ of Formula (XXXI) is selected from —NHC(═O)$R^7$, —C(═O)$NHR^7$, —NHS(═O)2$R^7$, —S(═O)$_2$NHR$^7$; —NHC(═O)$NHR^7$, —NHS(═O)$_2$NHR$^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)2$NHR^7$; —($C_1$-$C_3$alkyl)-NHC(═O)$NHR^7$, —($C_1$-$C_3$alkyl)-NHS(═O)2$NHR^7$, substituted or unsubstituted $C_2$-$C_{10}$heterocycloalkyl, or substituted or unsubstituted heteroaryl;

each $R^7$ of —NHC(═O)$R^7$, —C(═O)$NHR^7$, —NHS(═O)2$R^7$, —S(═O)$_2$NHR$^7$; —NHC(═O)$NHR^7$, —NHS(═O)$_2$NHR$^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)2$NHR^7$; —($C_1$-$C_3$alkyl)-NHC(═O)$NHR^7$, —($C_1$-$C_3$alkyl)-NHS(═O)2$NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —($CH_2$)p-CH (substituted or unsubstituted aryl)2, —$(CH_2)_p$—CH (substituted or unsubstituted heteroaryl)2, —($CH_2$)p-CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH$(C_1$-$C_4alkyl)_2$, —C(═O)OH, —C(═O)$NH_2$, —C(═O)$C_1$-$C_3$alkyl, —S(═O)$_2$$CH_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—$(C_1$-$C_4alkyl)_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXII), which are derived from the IAP ligands described in WO Pub. No. 2013/071039, or an unnatural mimetic thereof:

(XXXII)

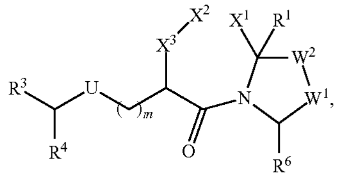

wherein:

$W^1$ of Formula (XXXII) is O, S, N—$R^A$, or $C(R^{8a})(R^{8b})$;

$W^2$ of Formula (XXXII) is O, S, N—$R^A$, or $C(R^{8c})(R^{8d})$; provided that $W^1$ and $W^2$ are not both O, or both S;

$R^1$ of Formula (XXXII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XXXII) is N—$R^A$, then $X^2$ is C═O, or $CR^{2c}R^{2d}$, and $X^3$ is $CR^{2a}R^{2b}$;

or:

when $X^1$ of Formula (XXXII) is selected from S, S(O), or $S(O)_2$, then $X^2$ is $CR^{2c}R^{2d}$, and $X^3$ is $CR^{2a}R^{2b}$;

or:

when $X^1$ of Formula (XXXII) is O, then $X^2$ is $CR^{2c}R^{2d}$ and N—$R^A$ and $X^3$ is $CR^{2a}R^{2b}$;

or:

when $X^1$ of Formula (XXXII) is $CH_3$, then $X^2$ is selected from O, N—$R^A$, S, S(O), or $S(O)_2$, and $X^3$ is $CR^{2a}R^{2b}$;

when $X^1$ of Formula (XXXII) is $CR^{2e}R^{2f}$ and $X^2$ is $CR^{2c}R^{2d}$, and $R^{2e}$ and $R^{2c}$ together form a bond, and $X^3$ of Formula (XXXII) is $CR^{2a}R^{2b}$;

or:

$X^1$ and $X^3$ of Formula (XXXII) are both $CH_2$ and $X^2$ of Formula (XXXII) is C═O, C═C($R^C$)2, or C═N$R^C$; where each $R^C$ is independently selected from H, —CN, —OH, alkoxy, substituted or unsubstituted C1-C6alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ of Formula (XXXII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula (XXXII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (XXXII) is $CR^{2e}R^{2f}$;

$R^A$ of N—$R^A$ is selected from H, $C_1$-$C_6$alkyl, —C(═O) $C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XXXII) is selected from 0, 1 or 2;

—U— of Formula (XXXII) is selected from —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XXXII) is selected from $C_1$-$C_3$alkyl, or $C_1$-$C_3$fluoroalkyl;

$R^4$ of Formula (XXXII) is selected from —$NHR^5$, —$N(R^5)_2$, —$N+(R^5)_3$ or —$OR^5$;

each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXII) together with the atoms to which they are attached form a substituted or unsubstituted 5-7 membered ring;

or:

$R^3$ of Formula (XXXII) is bonded to a nitrogen atom of U to form a substituted or unsubstituted 5-7 membered ring;

$R^6$ of Formula (XXXII) is selected from —NHC(═O)$R^7$, —C(═O)$NHR^7$, —NHS(═O)2$R^7$, —S(═O)$_2$$NHR^7$; —NHC(═O)$NHR^7$, —NHS(═O)$_2$$NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)$_2$$R^7$, —($C_1$-$C_3$alkyl)-S(═O)$_2$$NHR^7$; —($C_1$-$C_3$alkyl)-NHC(═O)$NHR^7$, —($C_1$-$C_3$alkyl)-NHS(═O)$_2$$NHR^7$, substituted or unsubstituted $C_2$-$C_{10}$heterocycloalkyl, or substituted or unsubstituted heteroaryl;

each $R^7$ of —NHC(═O)$R^7$, —C(═O)$NHR^7$, —NHS(═O)2$R^7$, —S(═O)$_2$$NHR^7$; —NHC(═O)$NHR^7$, —NHS(═O)$_2$$NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)2$NHR^7$; —($C_1$-$C_3$alkyl)-NHC(═O)$NHR^7$, —($C_1$-$C_3$alkyl)-NHS(═O)2$NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —$(CH_2)$p-CH (substituted or unsubstituted aryl)2, —$(CH_2)_p$—CH (substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2$$CH_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-

$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXIII), which is derived from the IAP ligands described in WO Pub. No. 2013/071039, or an unnatural mimetic thereof:

(XXXIII)

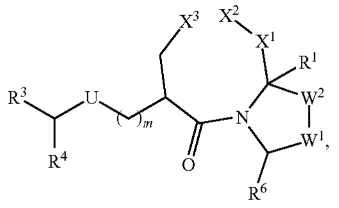

wherein:

$W^1$ of Formula (XXXIII) is selected from O, S, N—$R^A$, or C($R^{8a}$)($R^{8b}$);

$W^2$ of Formula (XXXIII) is selected from O, S, N—$R^A$, or C($R^{8c}$)($R^{8d}$); provided that $W^1$ and $W^2$ are not both O, or both S;

$R^1$ of Formula (XXXIII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XXXIII) is selected from N—$R^A$, S, S(O), or S(O)$_2$, then $X^2$ of Formula (XXXIII) is $CR^{2c}R^{2d}$, and $X^3$ of Formula (XXXIII) is $CR^{2a}R^{2b}$;

or:

when $X^1$ of Formula (XXXIII) is O, then $X^2$ of Formula (XXXIII) is selected from O, N—$R^A$, S, S(O), or S(O)$_2$, and $X^3$ of Formula (XXXIII) is $CR^{2a}R^{2b}$;

or:

when $X^1$ of Formula (XXXIII) is $CR^{2e}R^{2f}$ and $X^2$ of Formula (XXXIII) is $CR^{2c}R^{2d}$, and $R^{2e}$ and $R^{2C}$ together form a bond, and $X^3$ of Formula (XXXIII) is $CR^{2a}R^{2b}$;

or:

$X^1$ and $X^2$ of Formula (XXXIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XXXIII) is $CR^{2a}R^{2b}$;

or:

$X^2$ and $X^3$ of Formula (XXXIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered and ring, or a fused substituted or unsubstituted 5-10 membered heteroaryl ring, and $X^1$ of Formula (VLII) is $CR^{2e}R^{2f}$;

$R^A$ of N—$R^A$ is H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{21}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XXXIII) is 0, 1 or 2;

—U— of Formula (XXXIII) is —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XXXIII) is $C_1$-$C_3$alkyl, or $C_1$-$C_3$fluoroalkyl;

$R^4$ of Formula (XXXIII) is —$NHR^5$, —N($R^5$)$_2$, —N+($R^5$)$_3$ or —$OR^5$;

each $R^5$ of —$NHR^5$, —N($R^5$)$_2$, —N+($R^5$)$_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXIII) together with the atoms to which they are attached form a substituted or unsubstituted 5-7 membered ring;

or:

$R^3$ of Formula (XXXIII) is bonded to a nitrogen atom of U to form a substituted or unsubstituted 5-7 membered ring;

$R^6$ of Formula (XXXIII) is selected from —NHC(═O)$R^7$, —C(═O)$NHR^7$, —NHS(═O)2$R^7$, —S(═O)$_2NHR^7$; —NHC(═O)$NHR^7$, —NHS(═O)$_2NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)$_2$ $R^7$, —($C_1$-$C_3$alkyl)-S(═O)$_2NHR^7$; —($C_1$-$C_3$alkyl)-NHC(═O)$NHR^7$, —($C_1$-$C_3$alkyl)-NHS(═O)$_2NHR^7$, substituted or unsubstituted $C_2$-$C_{10}$heterocycloalkyl, or substituted or unsubstituted heteroaryl;

each $R^7$ of —NHC(═O)$R^7$, —C(═O)$NHR^7$, —NHS(═O)2$R^7$, —S(═O)$_2NHR^7$; —NHC(═O)$NHR^7$, —NHS(═O)$_2NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)2$NHR^7$; —($C_1$-

$C_3$alkyl)-NHC(═O)NHR$^7$, —($C_1$-$C_3$alkyl)-NHS(═O)2NHR$^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —($CH_2$)p-CH (substituted or unsubstituted aryl)2, —$(CH_2)_p$—CH (substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R$^7$ is 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R$^9$; and each R$^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2$$CH_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two R$^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXIV), which is derived from the IAP ligands described in WO Pub. No. 2013/071039, or an unnatural mimetic thereof:

(XXXIV)

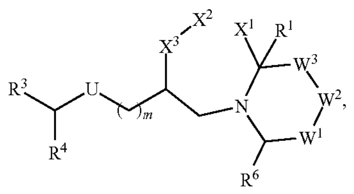

wherein:

W$^1$ of Formula (XXXIV) is selected from O, S, N—R$^A$, or C($R^{8a}$)($R^{8b}$);

W$^2$ of Formula (XXXIV) is selected from O, S, N—R$^A$, or C($R^{8c}$)($R^{8d}$); provided that W$^1$ and W$^2$ are not both O, or both S;

W$^3$ of Formula (XXXIV) is selected from O, S, N—R$^A$, or C($R^{8e}$)($R^{8f}$), providing that the ring comprising W$^1$, W$^2$, and W$^3$ does not comprise two adjacent oxygen atoms or sulfer atoms;

R$^1$ of Formula (XXXIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when X$^1$ of Formula (XXXIV) is O, then X$^2$ of Formula (XXXIV) is selected from $CR^{2c}R^{2d}$ and N—R$^a$, and X$^3$ of Formula (XXXIV) is $CR^{2a}R^{2b}$;

or:

when X$^1$ of Formula (XXXIV) is $CH_2$, then X$^2$ of Formula (XXIV) is selected from O, N—R$^A$, S, S(O), or S(O)$_2$, and X$^3$ of Formula (XXXIV) is $CR^{2a}R^{2b}$;

or:

when X$^1$ of Formula (XXXIV) is $CR^{2e}R^{2f}$ and X$^2$ of Formula (XXXIV) is $CR^{2c}R^{2d}$, and $R^{2e}$ and $R^{2C}$ together form a bond, and X$^3$ of Formula (XXXIV) is $CR^{2a}R^{2b}$;

or:

X$^1$ and X$^3$ of Formula (XXXIV) are both $CH_2$ and X$^2$ of Formula (XXXIV) is C═O, C═C($R^C$)2, or C═NR$^C$; where each R$^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

X$^1$ and X$^2$ of Formula (XXXIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XXXIV) is $CR^{2a}R^{2b}$;

or:

$X^2$ and $X^3$ of Formula (XXXIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2e}R^{2f}$;

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{21}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl));

m of Formula (XXXIV) is selected from 0, 1 or 2;

—U— of Formula (XXXIV) is selected from —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XXXIV) is selected from $C_1$-$C_3$alkyl, or $C_1$-$C_3$fluoroalkyl;

$R^4$ of Formula (XXXIV) is selected from —$NHR^5$, —N($R^5$)$_2$, —N+($R^5$)$_3$ or —$OR^5$;

each $R^5$ of —$NHR^5$, —N($R^5$)$_2$, —N+($R^5$)$_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXIV) together with the atoms to which they are attached form a substituted or unsubstituted 5-7 membered ring;

or:

$R^3$ of Formula (XXXIV) is bonded to a nitrogen atom of U to form a substituted or unsubstituted 5-7 membered ring;

$R^6$ of Formula (XXXIV) is selected from —NHC(═O)$R^7$, —C(═O)$NHR^7$, —NHS(═O)2$R^7$, —S(═O)$_2$$NHR^7$; —NHC(═O)$NHR^7$, —NHS(═O)$_2$$NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)$_2$$R^7$, —($C_1$-$C_3$alkyl)-S(═O)$_2$$NHR^7$; —($C_1$-$C_3$alkyl)-NHC(═O)$NHR^7$, —($C_1$-$C_3$alkyl)-NHS(═O)$_2$$NHR^7$, substituted or unsubstituted $C_2$-$C_{10}$heterocycloalkyl, or substituted or unsubstituted heteroaryl;

each $R^7$ of —NHC(═O)$R^7$, —C(═O)$NHR^7$, —NHS(═O)2$R^7$, —S(═O)$_2$$NHR^7$; —NHC(═O)$NHR^7$, —NHS(═O)$_2$$NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)2$NHR^7$; —($C_1$-$C_3$alkyl)-NHC(═O)$NHR^7$, —($C_1$-$C_3$alkyl)-NHS(═O)2$NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —($CH_2$)p-CH(substituted or unsubstituted aryl)2, —($CH_2$)$_p$—CH(substituted or unsubstituted heteroaryl)2, —($CH_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8C}$ together form a bond;

or:

$R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together form a bond;

or:

$R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8C}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$, and $R^{8f}$ of $C(R^{8c})(R^{8d})$ and $C(R^{8e})(R^{8f})$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of $C(R^{8a})(R^{8b})$ and $C(R^{8e})(R^{8f})$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ of $C(R^{8a})(R^{8b})$ and $C(R^{8c})(R^{8d})$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$, $R^{8d}$, $R^{8e}$, and $R^{8f}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2$$CH_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXV), (XXXVI) or (XXXVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

(XXXV)

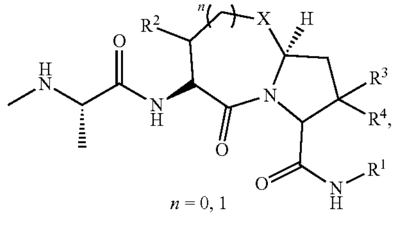

n = 0, 1

-continued (XXXVI)

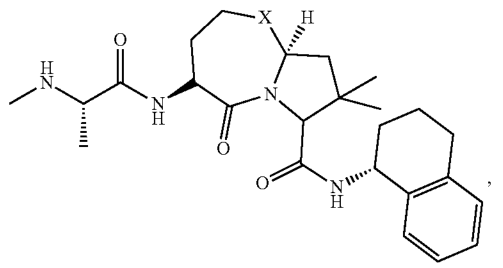

(XXXVII)

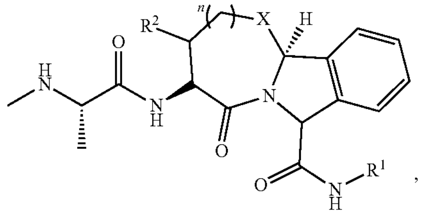

n = 0, 1 wherein:

$R^2$ of Formulas (XXXV) and (XXXVII) are independently selected from H or ME;

$R^3$ and $R^4$ of Formula (XXXV) are independently selected from H or ME;

X of Formulas (XXXV) and (XXXVII) is independently selected from O or S; and $R^1$ of Formulas (XXXV) and (XXXVII) is selected from:

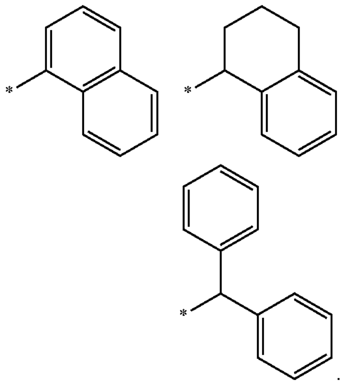

In a particular embodiment, the ILM has a structure according to Formula (XXXVIII):

(XXXVIII)

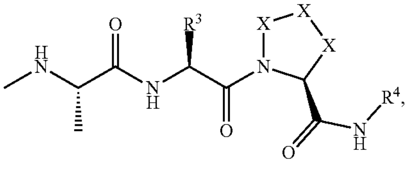

wherein $R^3$ and $R^4$ of Formula (XXXVIII) are independently selected from H or ME;

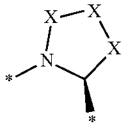

is a 5-member heterocycle selected from:

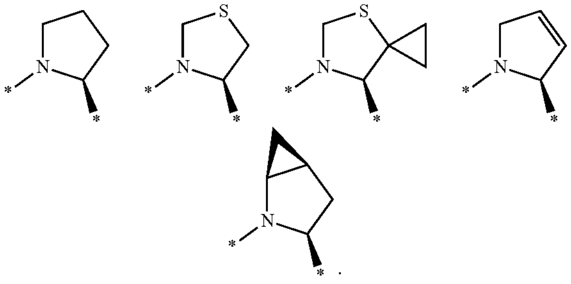

In a particular embodiment, the

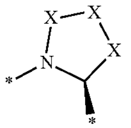

of Formula (XXXVIII) is

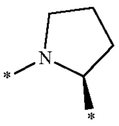 [SMILES: *[C@@H]1CCCN1*]

In a particular embodiment, the ILM has a structure and attached to a linker group L as shown below:

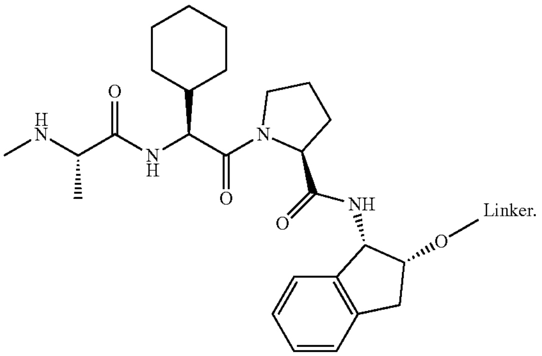

In any of the compounds described herein, the ILM can have the structure of Formula (XXXIX) or (XL), which is based on the IAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

(XXXIX)

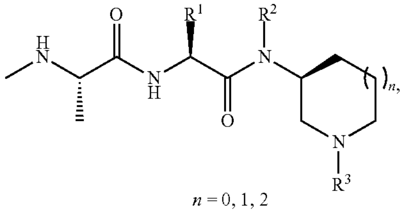

$n = 0, 1, 2$ (XL)

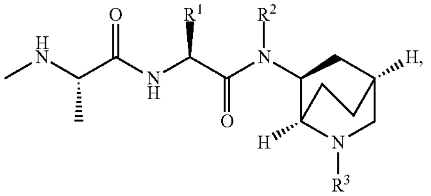

wherein:

$R^1$ of Formulas (XXXIX) and (XL) is selected from:

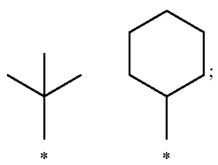

$R^2$ of Formulas (XXXIX) and (XL) is selected from H or Me;

$R^3$ of Formulas (XXXIX) and (XL) is selected from:

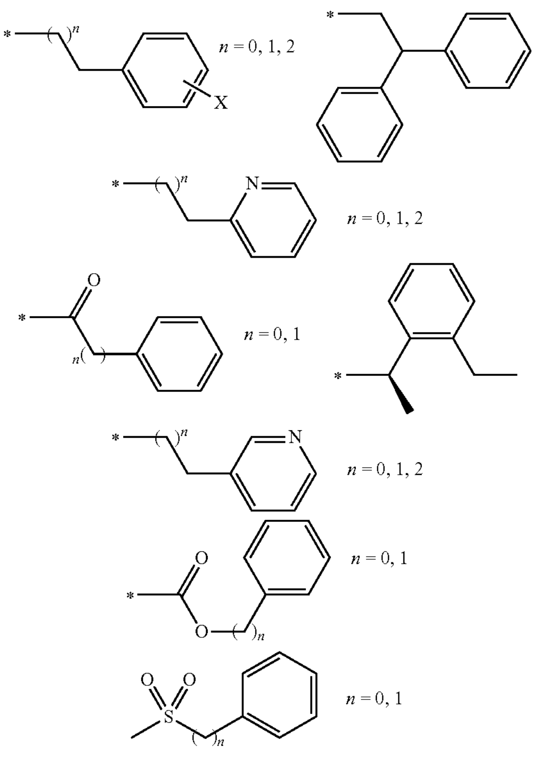

-continued

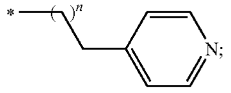

$n = 0, 1, 2$

X of is selected from H, halogen, methyl, methoxy, hydroxy, nitro or trifluoromethyl.

In any of the compounds described herein, the ILM can have the structure of and be chemically linked to the linker as shown in Formula (XLI) or (XLII), or an unnatural mimetic thereof:

(XLI)

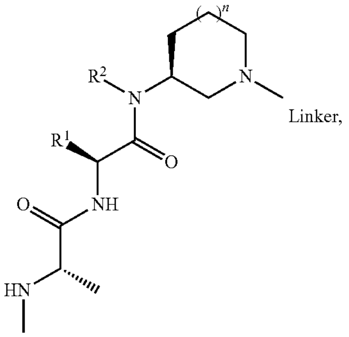

(XLII)

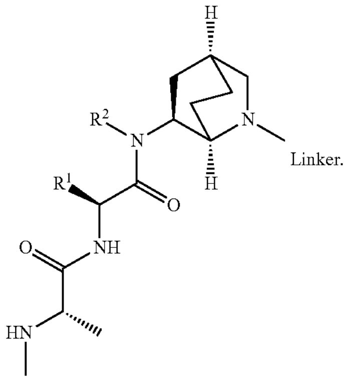

In any of the compounds described herein, the ILM can have the structure of Formula (XLIII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

(XLIII)

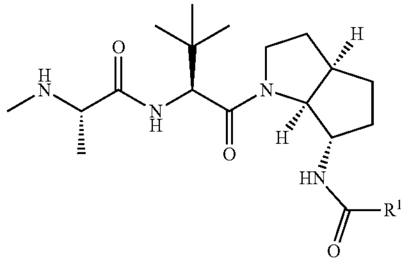

wherein:

R1 of Formulas (XLIII) is selected from:

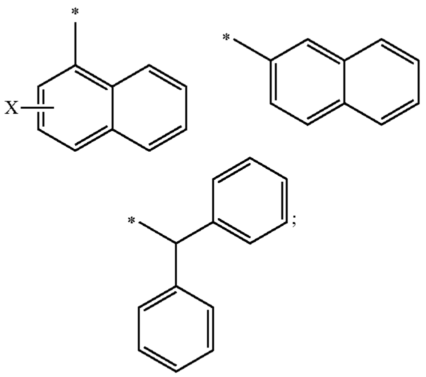

X of

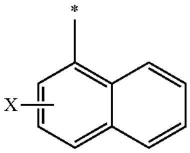

is selected from H, fluoro, methyl or methoxy.

In a particular embodiment, the ILM is represented by the following structure:

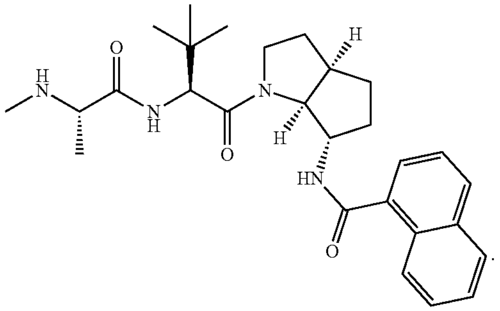 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM is selected from the group consisting of, and which the chemical link between the ILM and linker group L is shown:

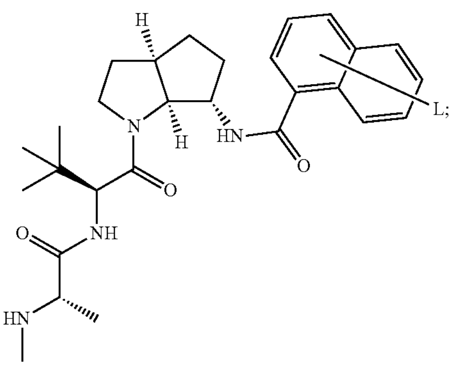

and

-continued

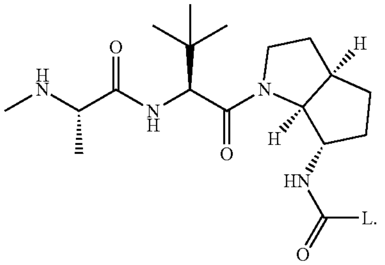

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

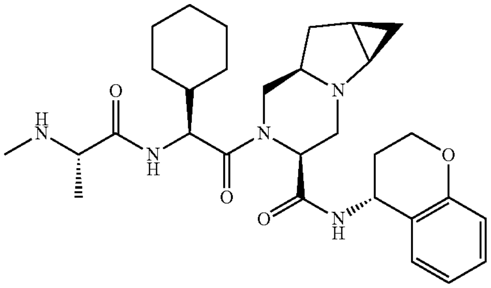

or

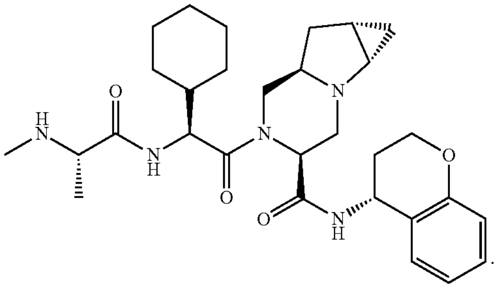

In a particular embodiment, the ILM is selected from the group consisting of, and which the chemical link between the ILM and linker group L is shown:

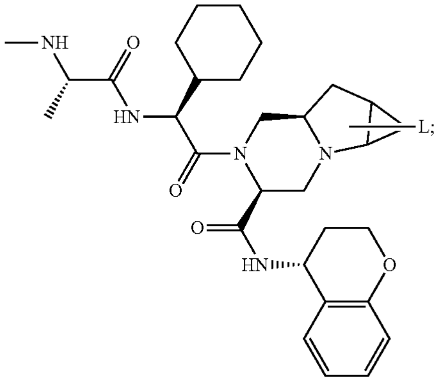

and

-continued

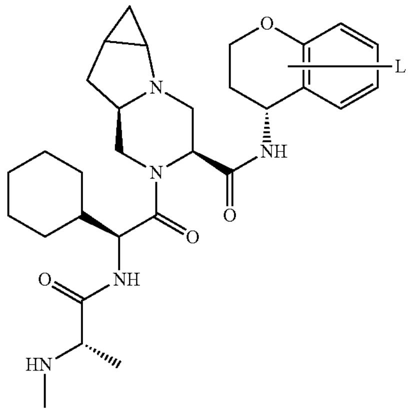

In any of the compounds described herein, the ILM can have the structure of Formula (XLIV), which is based on the IAP ligands described in Asano, M, et al., *Design, steriose-lective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

(XLIV)

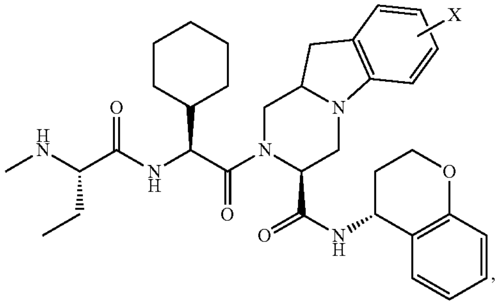

wherein X of Formula (XLIV) is one or two substituents independently selected from H, halogen or cyano.

In any of the compounds described herein, the ILM can have the structure of and be chemically linked to the linker group L as shown in Formula (XLV) or (XLVI), or an unnatural mimetic thereof:

(XLV)

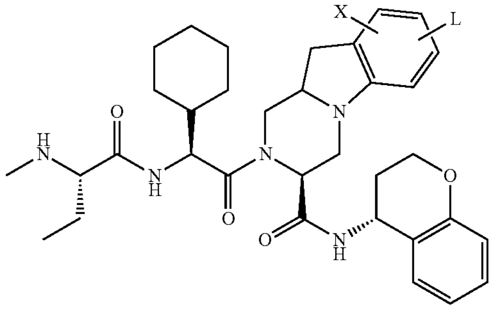

or

-continued (XLVI)

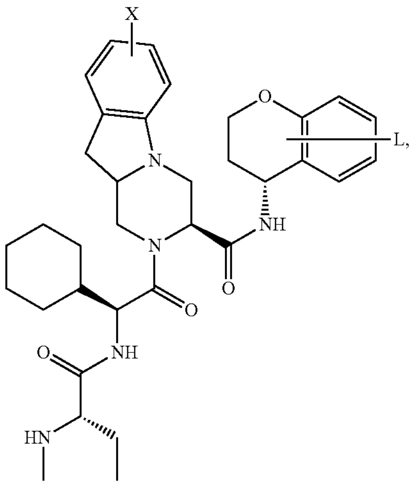

wherein X of Formula (XLV) and (XLVI) is one or two substituents independently selected from H, halogen or cyano, and; and L of Formulas (XLV) and (XLVI) is a linker group as described herein.

In any of the compounds described herein, the ILM can have the structure of Formula (XLVII), which is based on the IAP ligands described in Ardecky, R J, et al., *Design, synthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

(XLVII)

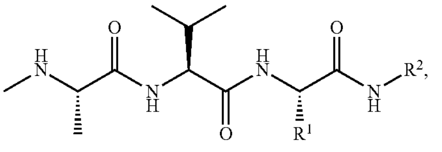

wherein:

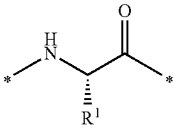

of Formula (XLVII) is a natural or unnatural amino acid; and $R^2$ of Formula (XLVII) is selected from:

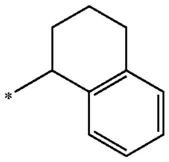

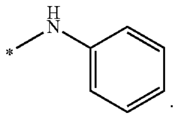

In any of the compounds described herein, the ILM can have the structure of and be chemically linked to the linker group L as shown in Formula (XLVIII) or (XLIX), or an unnatural mimetic thereof:

(XLVIII)

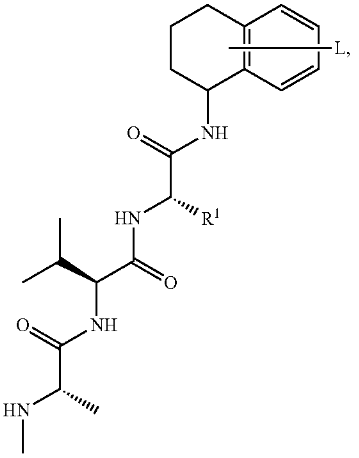

or (XLIX)

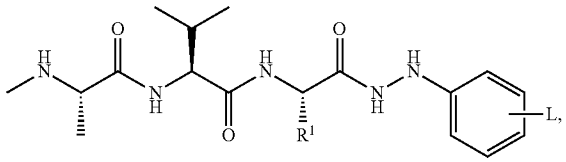

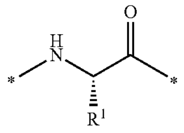

of Formulas (XLVIII) and (XLIX) is a natural or unnatural amino acid; and L of Formula (XLVIII) and (XLIX) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

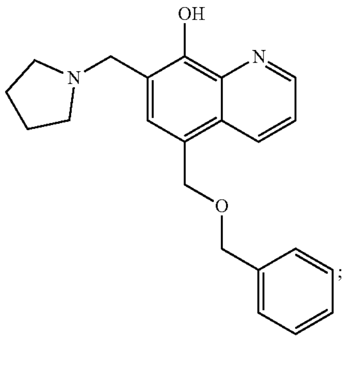

; and

-continued

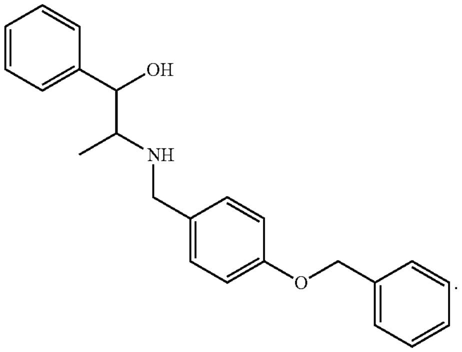

In any of the compounds described herein, the ILM has a structure according to Formula (L), which is based on the IAP ligands described in Hird, A W, et al., Structure-based design and synthesis of tricyclic IAP (Inhibitors *of Apoptosis Proteins*) *inhibitors*, Bioorg. Med. Chem. Lett., 24(7): 1820-4 (2014), or an unnatural mimetic thereof:

(L)

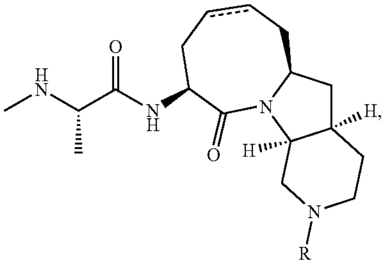

wherein R of Formula (L) is selected from the group consisting of:

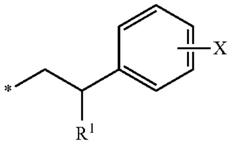

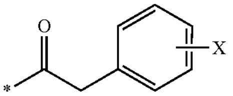

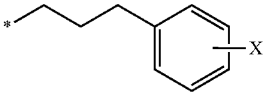

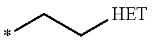

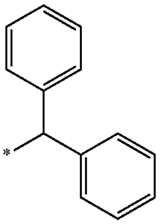

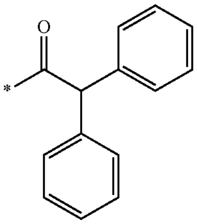

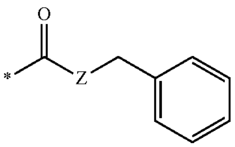

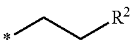

-continued

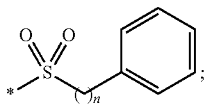

R1 of

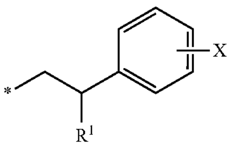

is selected from H or Me;

R2 of

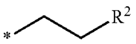

is selected from alkyl or cycloalkyl;

X of

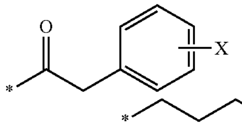

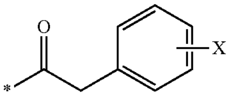

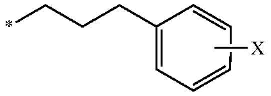

is 1-2 substitutents independently selected from halogen, hydroxy, methoxy, nitro and trifluoromethyl Z of

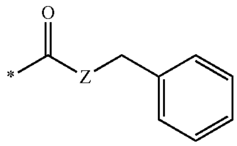

is O or NH;

HET of

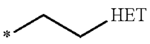

is mono- or fused bicyclic heteroaryl; and

--- of Formula (L) is an optional double bond.

In a particular embodiment, the ILM of the compound has a chemical structure selected from the group consisting of:

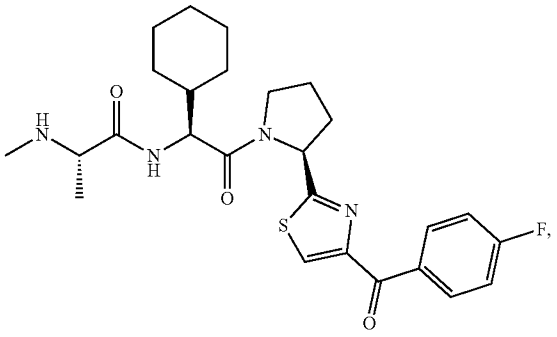
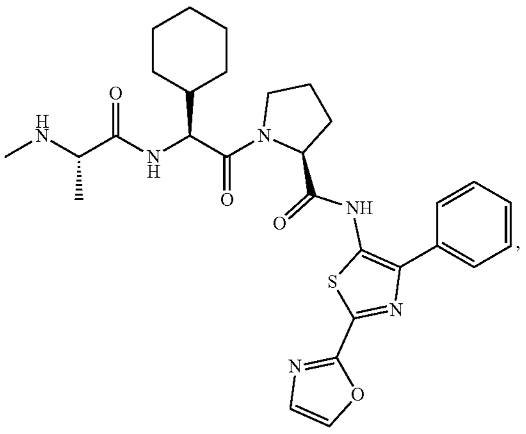
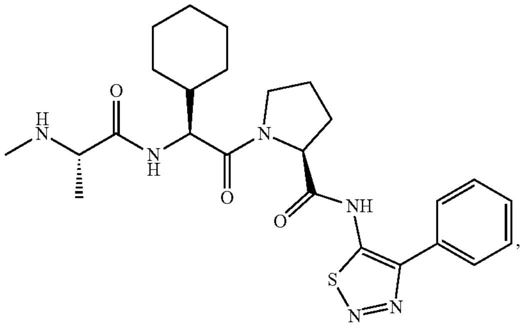
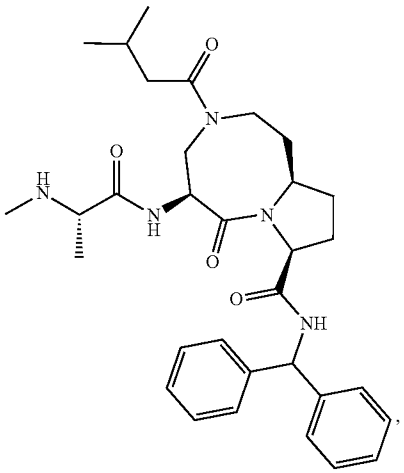
-continued
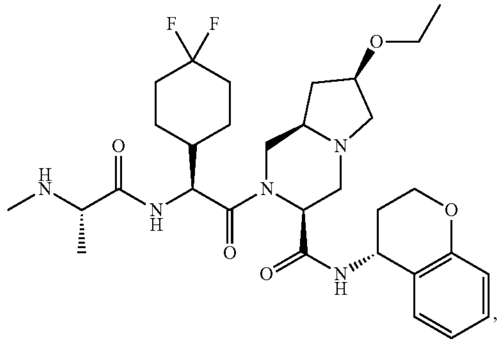
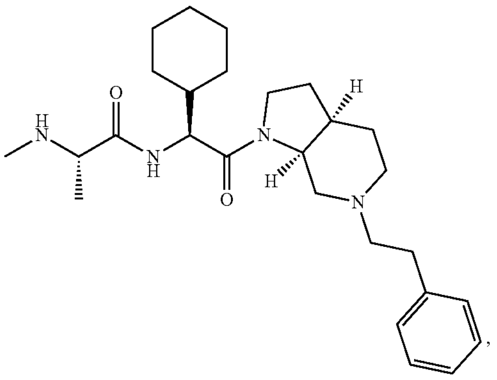
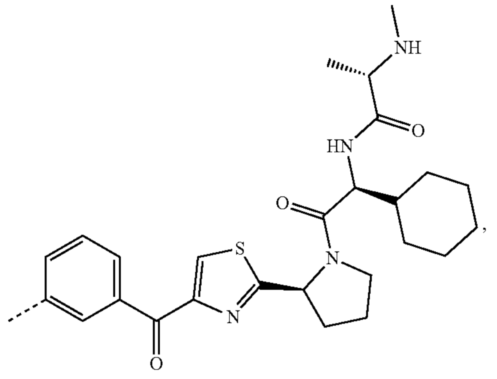
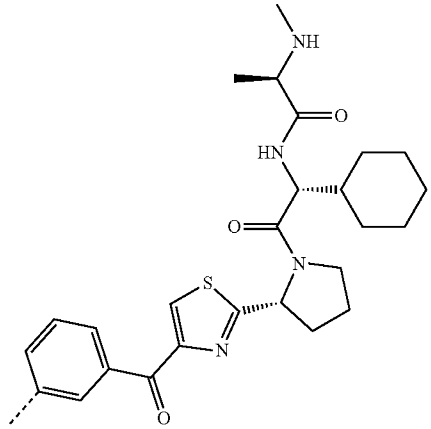

-continued

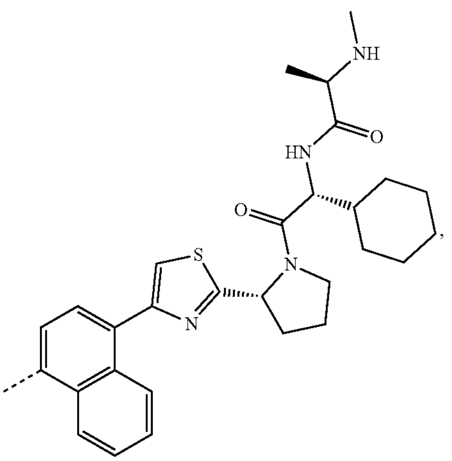

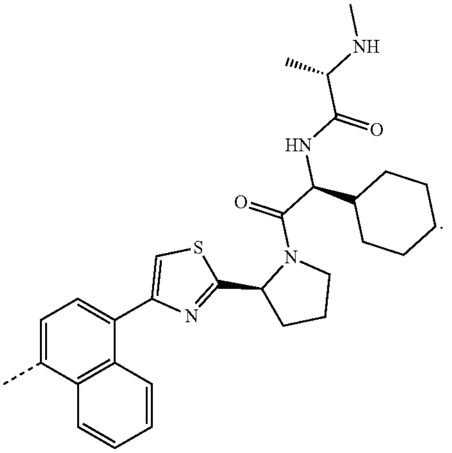

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

Formula (A-1)

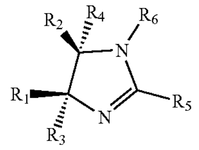

Formula (A-2)

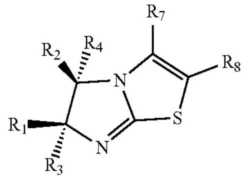

Formula (A-3)

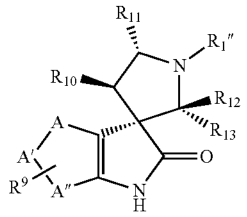

Formula (A-4)

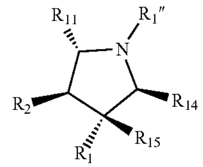

Formula (A-5)

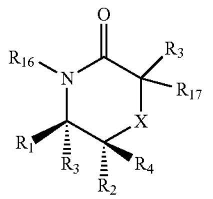

Formula (A-6)

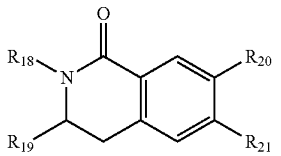

Formula (A-7)

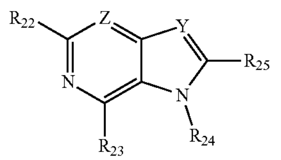

Formula (A-8)

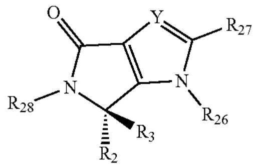

wherein above Formula (A-1) through Formula (A-8):

X of Formula (A-1) through Formula (A-8) is selected from the group consisting of carbon, oxygen, sulfur, sulfoxide, sulfone, and N—$R^a$;

$R^a$ is independently H or an alkyl group with carbon number 1 to 6;

Y and Z of Formula (A-1) through Formula (A-8) are independently carbon or nitrogen;

A, A' and A" of Formula (A-1) through Formula (A-8) are independently selected from C, N, O or S, can also be one or two atoms forming a fused bicyclic ring, or a 6,5- and 5,5-fused aromatic bicyclic group;

$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ of Formula (A-1) through Formula (A-8) are independently selected from the group consisting of H, methyl and C1 to C6 alkyl;

$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ of Formula (A-1) through Formula (A-8) is H or —C(═O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^C$-morpholinyl, 4-$R^c$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^1$), wherein $R^h$ and $R^1$ are selected from groups consisting of the following:

H; optionally substituted linear or branched C1 to C6 alkyl; alkoxy substituted alkyl; mono- and di-hydroxy substituted alkyl (e.g., a C3 to C6), sulfone substituted alkyl; optionally substituted aryl; optionally substituted heteraryl; mono-, bis- or tri-substituted aryl or heteroaryl; phenyl-4-carboxylic acid; substituted phenyl-4-carboxylic acid, alkyl carboxylic acid; optionally substituted heteroaryl carboxylic acid; alkyl carboxylic acid; fluorine substituted alkyl carboxylic acid; optionally substituted cycloalky, 3-hydroxycyclobutane, 4-hydroxycyclohehexane, aryl substituted cycloalkyl; heteroaryl substituted cycloalkyl; or Rh and Ri taken together form a ring;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of $C_{1-6}$ alkyl, $C_{1-6}$ cycloalkyl, C2-6 alkenyl, $C_{1-6}$ alkyl or C3-6 cycloalkyl with one or multiple hydrogens replaced by fluorine, alkyl or cycloalkyl with one $CH_2$ replaced by S(═O), —S, or —S(═O)$_2$, alkyl or cycloalkyl with terminal $CH_3$ replaced by S(═O)$_2$N(alkyl)(alkyl), —C(═O)N(alkyl)(alkyl), —N(alkyl)S(═O)$_2$(alkyl), —C(═O)2(alkyl), —O(alkyl), $C_{1-6}$ alkyl or alkyl-cycloalkyl with hydron replaced by hydroxyl group, a 3 to 7 membered cycloalkyl or heterocycloalkyl, optionally containing a —(C═O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, $C_{1-6}$ alkyl groups, hydroxylated $C_{1-6}$ alkyl, $C_{1-6}$ alkyl containing thioether, ether, sulfone, sulfoxide, fluorine substituted ether or cyano group;

$R_{17}$ of Formula (A-1) through Formula (A-8) is selected from the group consisting of $(CH_2)nC(O)NR^kR^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxy alkyl with one or multiple hydrogens replaced by fluorine, C1-6 alkyl with hydrogen replaced by a cyano group, 5 and 6 membered aryl or heteroaryl, aklyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or hetroaryl groups can be substituted with halogen, C1-6 alkyl, C1-6 cycloalkyl, $CF_3$, F, CN, alkyne, alkyl sulfone, the halogen substitution can be mon- bis- or tri-substituted; $R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydroxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ of Formula (A-1) through Formula (A-8) is selected from the group consisting of H, alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L'' is a connector (i.e. a linker group), and "PTM" is a ligand binding to a target protein.

In certain embodiments, the description provides a bifunctional molecule comprising a structure selected from the group consisting of:

Formula (A-9)

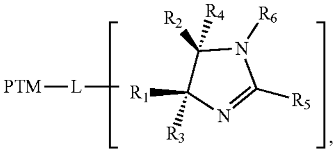

Formula (A-10)

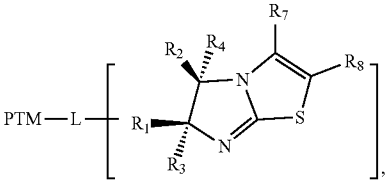

-continued

Formula (A-11)

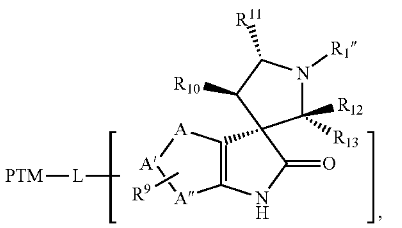

Formula (A-12)

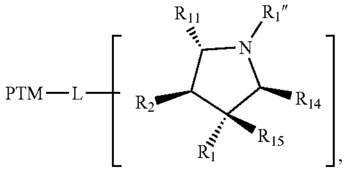

Formula (A-13)

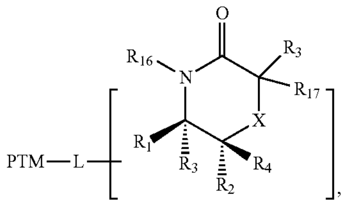

Formula (A-14)

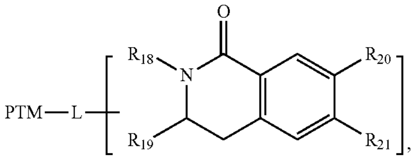

Formula (A-15)

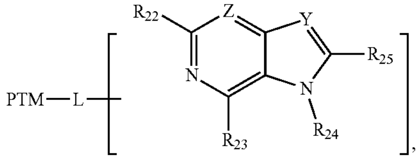

and

Formula (A-16)

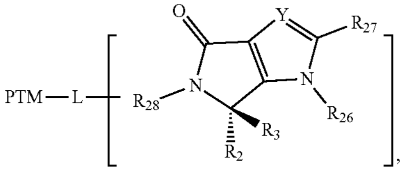

wherein X, $R^a$, Y, Z, A, A', A", $R_1R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1

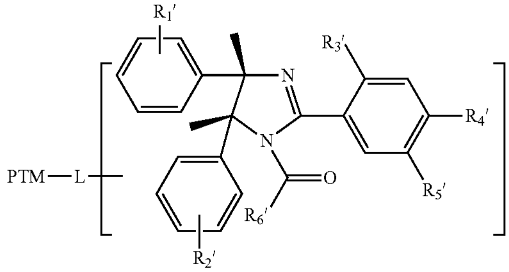

A-1-2

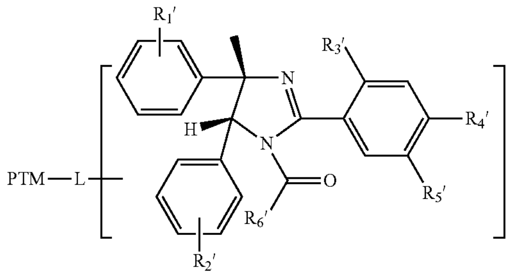

A-1-3

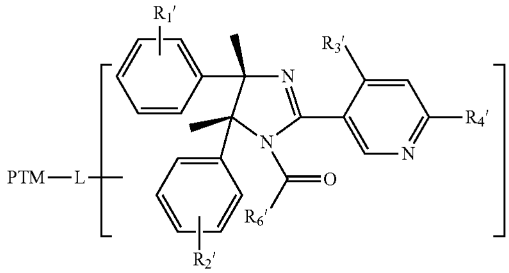

A-1-4

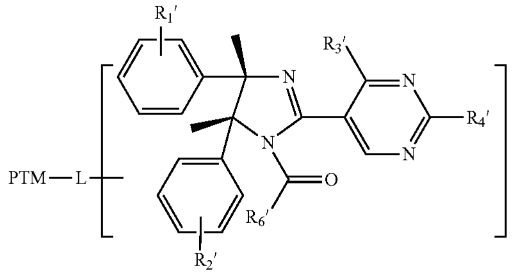

wherein:

R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$;

R3' is selected from the group consisting of $-OCH_3$, $-OCH_2CH_3$, $-OCH_2CH_2F$, $-OCH_2CH_2OCH_3$, and $-OCH(CH_3)_2$;

R4' of Formulas A-1-1 throught A-1-4 is selected from the group consisting of H, halogen, $-CH_3$, $-CF_3$, $-OCH_3$, $-C(CH_3)_3$, $-CH(CH_3)_2$, -cyclopropyl, $-CN$, $-C(CH_3)_2OH$, $-C(CH_3)_2OCH_2CH_3$, $-C(CH_3)_2CH_2OH$, $-C(CH_3)_2CH_2OCH_2CH_3$, $C(CH_3)_2CH_2OCH_2CH_2OH$, $-C(CH_3)_2$ $CH_2OCH_2CH_3$, $-C(CH_3)_2CN$, $-C(CH_3)_2C(O)CH_3$, $-C(CH_3)_2C(O)NHCH_3$, $-C(CH_3)_2C(O)N(CH_3)_2$, —$SCH_3$, —$SCH_2CH_3$, —$S(O)_2CH_3$, —$S(O_2)CH_2CH_3$, —$NHC(CH_3)_3$, —$N(CH_3)_2$, pyrrolidinyl, and 4-morpholinyl;

R5' of Formulas A-1-1 through A-1-4 is selected from the group consisting of halogen, -cyclopropyl, —$S(O)_2CH_3$, —$S(O)_2CH_2CH_3$, 1-pyrrolidinyl, —$NH_2$, —$N(CH_3)_2$, and —$NHC(CH_3)_3$; and R6' of Formulas A-1-1 through A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H,

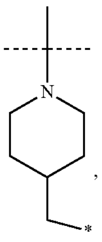, 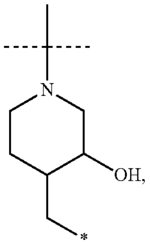, 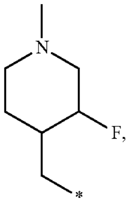,

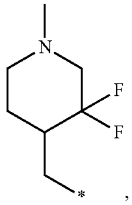, 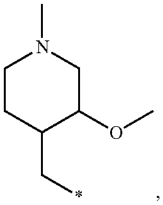, 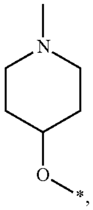,

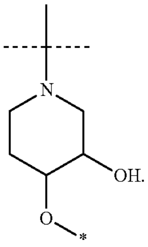. 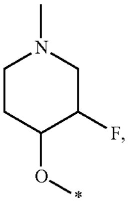, 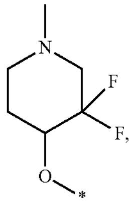,

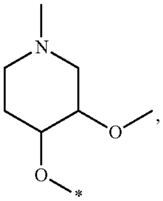, 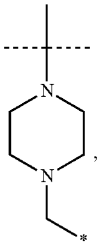, 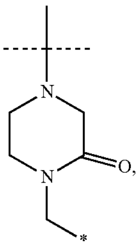,

-continued

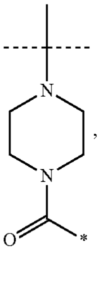, 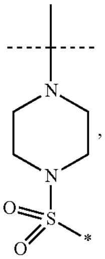, 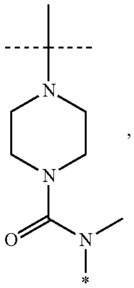,

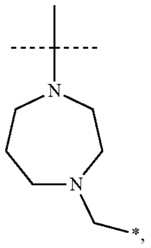, 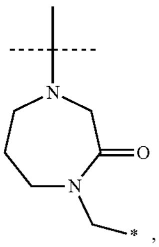, 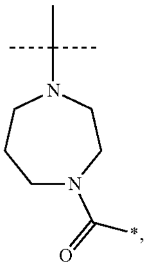,

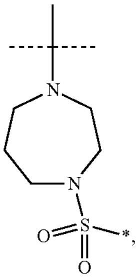, 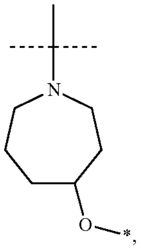, 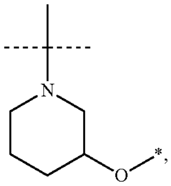,

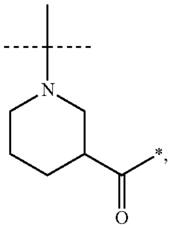, 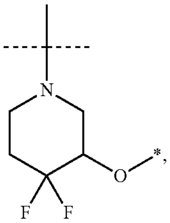, 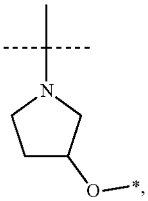,

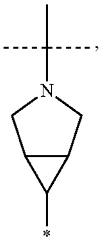, 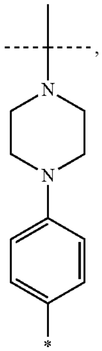, 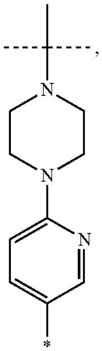

-continued

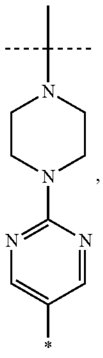
,
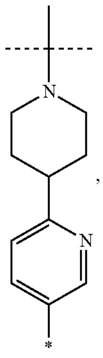
, and
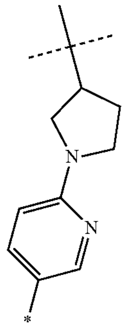

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

A-4-1

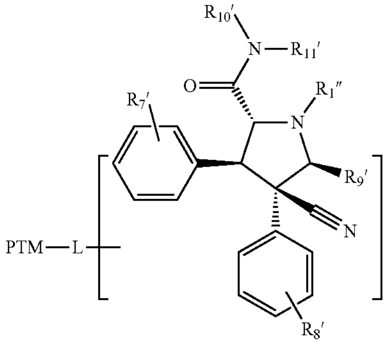

A-4-2

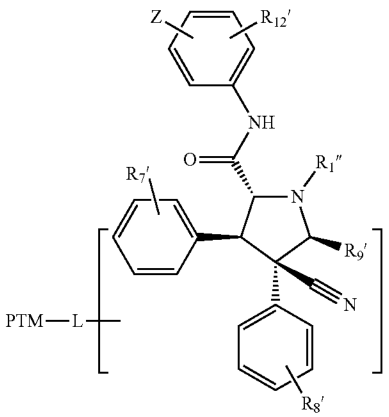

-continued

A-4-3

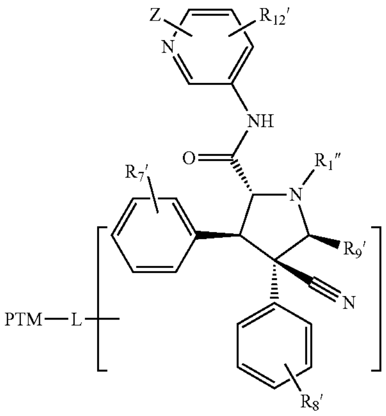

A-4-4

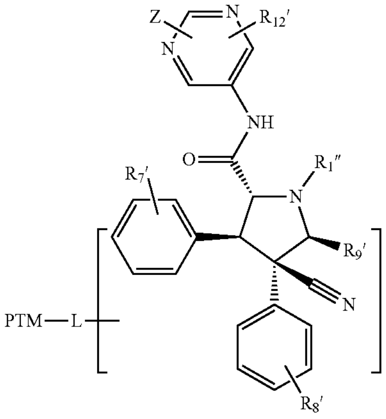

A-4-5

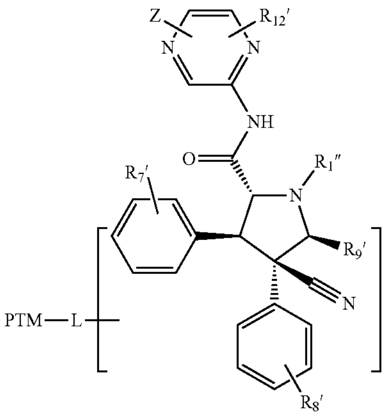

-continued

A-4-6

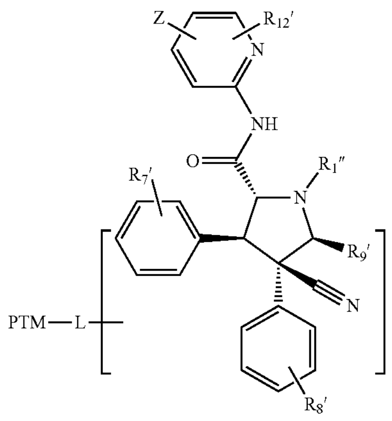

wherein:

R7' of Formula A-4-1 through A-4-6 (i.e., A-4-1, A-4-2, A-4-3, A-4-4, A-4-5, and A-4-6) is one or more (e.g., 1, 2, 3, or 4) halogens;

R8' of Formula A-4-1 through A-4-6 is one or more groups (e.g., 1, 2, 3, or 4 groups) selected from the group consisting of H, —F, —Cl, —Br, —I, —CN, —$NO_2$, ethylnyl, cyclopropyl, methyl, ethyl, isopropyl, vinyl, methoxy, ethoxy, isopropoxy, —OH, other $C_{1-6}$ alkyl, other $C_{1-6}$ alkenyl, and $C_{1-6}$ alkynyl, mono-, di- or tri-substituted;

R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z of Formula A-4-1 through A-4-6 is selected from the group consistin of H, —$OCH_3$, —$OCH_2CH_3$, and halogen;

R10' and R11' of Formula A-4-1 through A-4-6 are each independently selected from the group consisting of H, $(CH_2)$"—R', $(CH_2)$"—NR'R", $(CH_2)$"—NR'COR", $(CH_2)$"—NR'$SO_2$R", $(CH_2)$"—COOH, $(CH_2)$"—COOR', $(CH)_n$—CONR'R", $(CH_2)$"—OR', $(CH_2)$"—SR', $(CH_2)$"—SOR', $(CH_2)$"—CH(OH)—R', $(CH_2)$"—COR', $(CH_2)$"—$SO_2$R$(CH_2)$"—SONR'R", $(CH_2)$"—$SO_2$NR'R", $(CH_2CH_2O)_m$—$(CH_2)$"—R', $(CH_2CH_2O)_m$—$(CH_2)$"—OH, $(CH_2CH_2O)_m$—$(CH_2)$"—OR', $(CH_2CH_2O)_m$—$(CH_2)$"—NR'R", $(CH_2CH_2O)_m$—$(CH_2)$"—NR'COR", $(CH_2CH_2O)_m(CH_2)$"—NR'$SO_2$R", $(CH_2CH_2O)_m(CH_2)$"—COOH, $(CH_2CH_2O)_m(CH_2)$"—COOR', $(CH_2CH_2O)_m$—$(CH_2)$"—CONR'R", $(CH_2CH_2O)_m$—$(CH_2)$"—$SO_2$R', $(CH_2CH_2O)_m$—$(CH_2)$"—COR', $(CH_2CH_2O)_m$—$(CH_2)$"—SONR'R", $(CH_2CH_2O)_m$—$(CH_2)$"—$SO_2$NR'R", $(CH_2)_p$—$(CH_2CH_2O)_m$—$(CH_2)$"R', $(CH_2)_p$—$(CH_2CH_2O)_m$—$(CH_2)$"—OH, $(CH_2)_p$—$(CH_2CH_2O)_m$—$(CH_2)_n$—OR', $(CH_2)_p$—$(CH_2CH_2O)_m$—$(CH_2)$"—NR'R", $(CH_2)_p$—$(CH_2CH_2O)_m$—$(CH_2)$"—NR'COR", $(CH_2)_p$—$(CH_2CH_2O)_m$—$(CH_2)$"—NR'$SO_2$R", $(CH_2)_p$—$(CH_2CH_2O)_m$—$(CH_2)$"—COOH, $(CH_2)_p$—$(CH_2CH_2O)_m$—$(CH_2)$"—COOR', $(CH_2)_p$—$(CH_2CH_2O)_m$—$(CH_2)$"—CONR'R", $(CH_2)_p$—$(CH_2CH_2O)_m$—$(CH_2)$"—$SO_2$R', $(CH_2)_p$—$(CH_2CH_2O)_m$—$(CH_2)$"—COR', $(CH_2)_p$—$(CH_2CH_2O)_m$—$(CH_2)$"—SONR'R", $(CH_2)_p$—$(CH_2CH_2O)_m$—$(CH_2)$"—$SO_2$NR'R", Aryl-$(CH_2)$"—COOH, and heteroaryl-alkyl-CO-alkyl-NR'R"m, wherein the alkyl may be substituted with OR', and heteroaryl-$(CH_2)_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), $N(alkyl)_2$, oxo, carboxy, clcloalkyl and heteroaryl;

m, n, and p are independently 0 to 6;

R12' of Formula A-4-1 through A-4-6 is selected from the group consisting of —O-(alkyl), —O-(alkyl)-akoxy, —C(O)-(alkyl), —C(OH)-alkyl-alkoxy, —C(O)—NH-(alkyl), —C(O)—N-$(alkyl)_2$, —S(O)-(alkyl), $S(O)_2$-(alkyl), —C(O)-(cyclic amine), and —O-aryl-(alkyl), —O-aryl-(alkoxy);

R1" of Formula A-4-1 through A-4-6 is selected from the group consisting of H, alkyl, aryl substituted alkyl, alkoxy substituted alkyl, cycloalkyl, aryl-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

1. The HDM2/MDM2 inhibitors identified in Vassilev, et al., In vivo activation of the p53 pathway by small-molecule antagonists of MDM2, *SCIENCE* vol: 303, pag: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

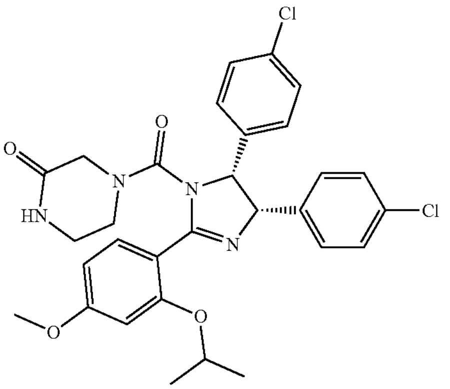 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM)group is attached, for example, at the methoxy group or as a hydroxyl group);

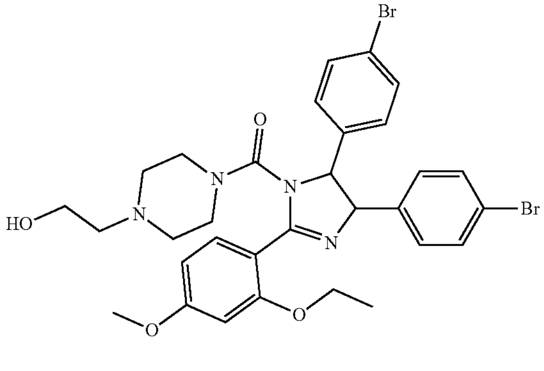 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group);

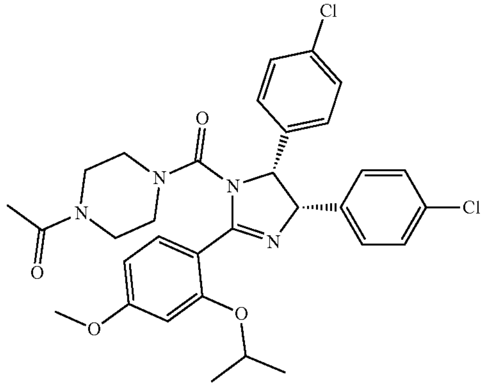 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group); and 2. Trans-4-Iodo-4'-Boranyl-Chalcone

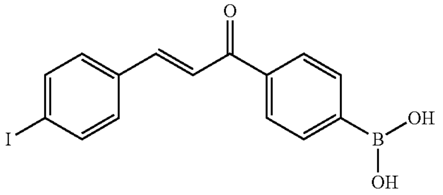 [SMILES: O=C(/C=C/c1ccc(I)cc1)c1ccc(B(O)O)cc1]

(derivatized where a linker group L or a a linker group L or a-(L-MLM) group is attached, for example, via a hydroxy group).

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A^{L}_{1} \ldots (A^{L})_q-$ or $-(A^{L})_q-$), wherein $A_1$ is a group coupled to PTM, and $(A^{L})_q$ is a group coupled to ULM.

In any aspect or embodiment described herein, the linker (L) to ULM (e.g., VLM, ILM, CLM, or MLM) connection or coupling is a stable L-ULM connection. For example, in any aspect or embodiment described herein, when a linker (L) and a ULM is connected via a heteroatom, any subsequent heteroatom, if present, is separated by at least one single carbon atom (e.g., —$CH_2$—), such as with an acetal or aminal group. By way of further example, in any aspect or embodiment described herein, when a linker (L) and a ULM is connected via a heteroatom, the heteroatom is not part of a ester.

In any aspect or embodiment described herein, the linker group L is a bond or a chemical linker group represented by the formula $-(A^{L})_q-$, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100), and wherein L is covalently bound to the PTM and the ULM, and provides for sufficient binding of the PTM to the protein target and the ULM to an E3 ubiquitin ligase to result in target protein ubiquitination.

In any aspect or embodiment described herein, the linker group L is-$(A^{L})_q$-, wherein:

$(A^{L})_q$ is a group which is connected to at least one of a ULM moiety, a PTM moiety (e.g., a CLM or a VLM), or a combination thereof;

q of the linker is an integer greater than or equal to 1 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100);

each $A^{L}$ is independently selected from the group consisting of, a bond, $CR^{L1}R^{L2}$, O, S, SO, $so_2$, $NR^{L3}$, $SO_2NR^{L3}$, $SONR^{L3}$, $CONR^{13}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{11}$, $P(O)OR^{11}$, $NR^{L3}C({=}NCN)NR^{14}$, $NR^{L3}C({=}NCN)$, $NR^{L3}C({=}CNO_2)NR^{14}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-8}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{15}$ groups; and $R^{L1}$, $R^{L2}$, $R^{L3}$, $R^{L4}$ and $R^{15}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, $NH SO_2NH(C_{1-8}alkyl)$, $NH SO_2N(C_{1-8}alkyl)_2$, $NH SO_2NH_2$.

In any aspect or embodiment described herein, q of the linker is an integer greater than or equal to 0. In certain embodiments, q is an integer greater than or equal to 1.

In any aspect or embodiment described herein, e.g., where q of the linker is greater than 2, $(A^L)_q$ is a group which is $A^L{}_1$ and $(A^L)_q$, wherein the units $A^L$ are couple a PTM to a ULM.

In any aspect or embodiment described herein, e.g., where q of the linker is 2, $(A^L)_q$ is a group which is connected to $A^L{}_1$ and to a ULM.

In any aspect or embodiment described herein, e.g., where q of the linker is 1, the structure of the linker group L is $-A^L{}_1-$, and $A^L{}_1$ is a group which is connected to a ULM moiety and a PTM moiety.

In any aspect or embodiment described herein, the linker (L) comprises a group represented by a general structure selected from the group consisting of:

$—NR(CH_2)_n$-(lower alkyl)-, $—NR(CH_2)_n$-(lower alkoxyl)-, $—NR(CH_2)_n$-(lower alkoxyl)-$OCH_2—$, $—NR(CH_2)_n$-(lower alkoxyl)-(lower alkyl)-$OCH_2—$, $—NR(CH_2)_n$-(cycloalkyl)-(lower alkyl)-$OCH_2—$, $—NR(CH_2)_n$-(hetero cycloalkyl)-, $—NR(CH_2CH_2O)_n$-(lower alkyl)-O—$CH_2—$, $—NR(CH_2CH_2O)_n$-(hetero cycloalkyl)-O—$CH_2—$, $—NR(CH_2CH_2O)_n$-Aryl-O—$CH_2—$, $NR(CH_2CH_2O)_n$-(hetero aryl)-O—$CH_2—$, $—NR(CH_2CH_2O)_n$-(cyclo alkyl)-O-(hetero aryl)-O—$CH_2—$, $—NR(CH_2CH_2O)_n$-(cyclo alkyl)-O-Aryl-O—$CH_2—$, $—NR(CH_2CH_2O)_n$-(lower alkyl)-NH-ArylO—$CH_2—$, $—NR(CH_2CH_2O)_n$-(lower alkyl)-O-Aryl-$CH_2$, $—NR(CH_2CH_2O)_n$-cycloalkyl-O-Aryl-, $—NR(CH_2CH_2O)_n$-cycloalkyl-O-(heteroaryl)l-, $—NR(CH_2CH_2)_n$-(cycloalkyl)-O-(heterocycle)-$CH_2$, $—NR(CH_2CH_2)_n$-(heterocycle)-(heterocycle)-$CH_2$, N(R1R2)-(heterocycle)-$CH_2$; wherein:

n of the linker can be 0 to 10;

R of the linker can be H, lower alkyl;

R1 and R2 of the linker can form a ring with the connecting N.

In any aspect or embodiment described herein, the linker (L) comprises a group represented by a general structure selected from the group consisting of:

$—N(R)—(CH_2)_m—O(CH_2)_n—O(CH_2)_o—O(CH_2)_p—O(CH_2)_q—O(CH_2)_r—OCH_2—$, $—O—(CH_2)_m—O(CH_2)_n—O(CH_2)_o—O(CH_2)_p—O(CH_2)_q—O(CH_2)_r—OCH_2—$, $—O—(CH_2)_m—O(CH_2)_n—O(CH_2)_o—O(CH_2)_p—O(CH_2)_q—O(CH_2)_r—O—$; $—N(R)—(CH_2)_m—O(CH_2)_n—O(CH_2)_o—O(CH_2)_p—O(CH_2)_q—O(CH_2)_r—O—$; $(CH_2)_m—O(CH_2)_n—O(CH_2)_o—O(CH_2)_p—O(CH_2)_q—O(CH_2)_r—O—$; $(CH_2)_m—O(CH_2)_n—O(CH_2)_o—O(CH_2)_p—O(CH_2)_q—O(CH_2)_r—OCH_2—$;

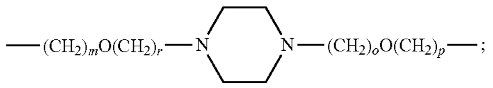

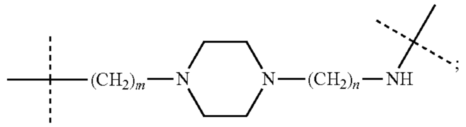

-continued

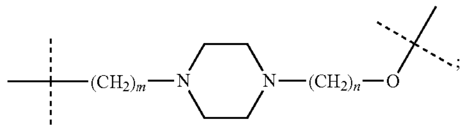

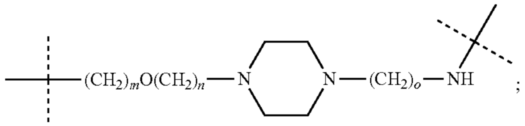

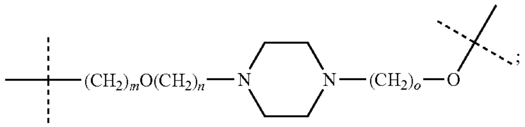

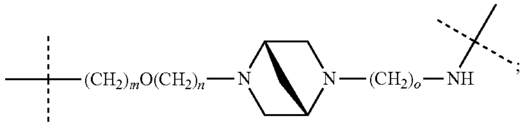

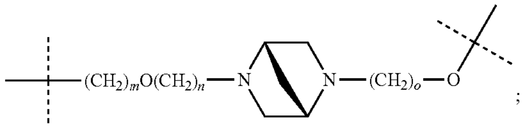

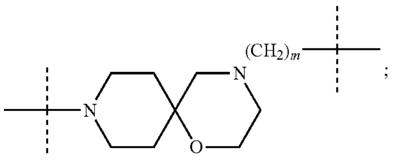

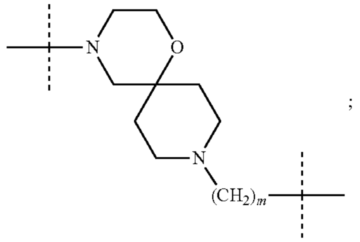

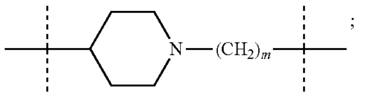

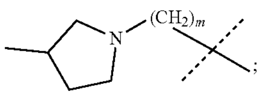

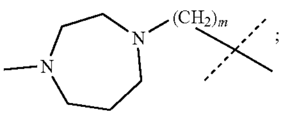

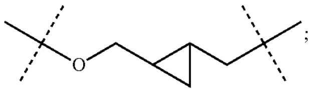

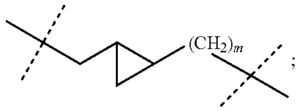

-continued
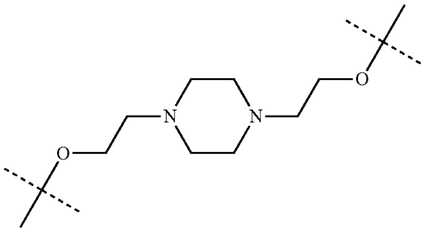
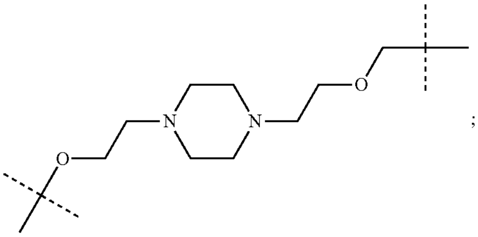
;
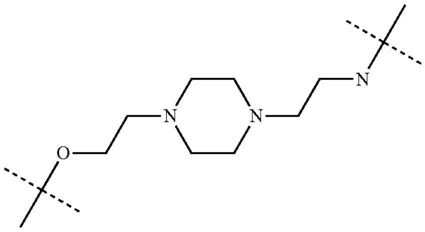
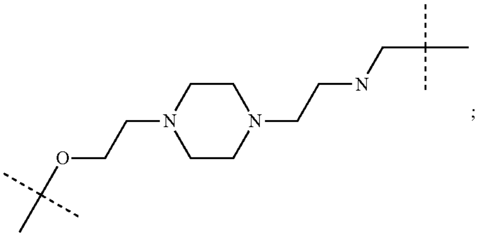
;
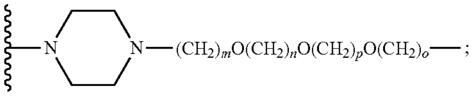
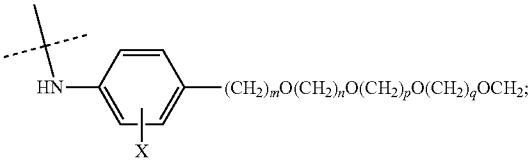
-continued
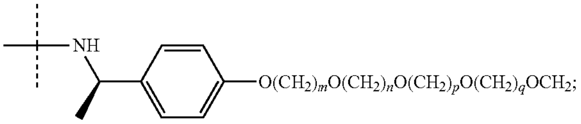
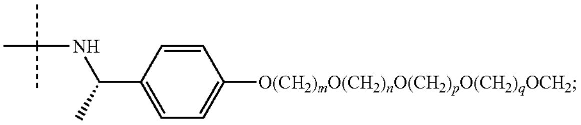
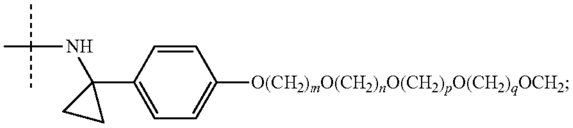
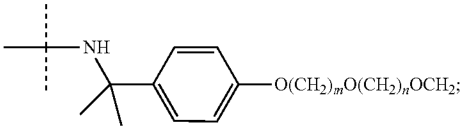
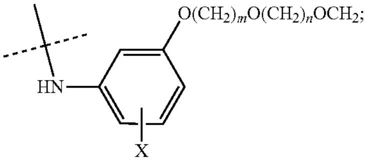
and
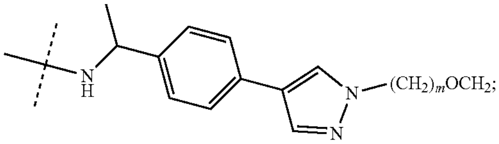
wherein
each m, n, o, p, q, and r of the linker is independently 0, 1, 2, 3, 4, 5, 6, 7, 8, 9, 10, 11, 12, 13, 14, 15, 16, 17, 18, 19, or 20;
when the number is zero, there is no N—O or O—O bond
R of the linker is H, methyl and ethyl;
X of the linker is H and F
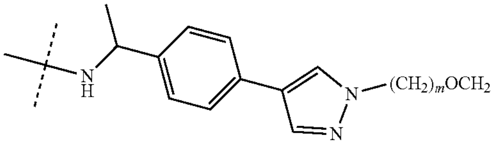
where m of the linker can be 2, 3, 4, 5
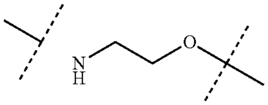
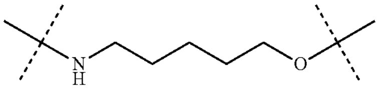
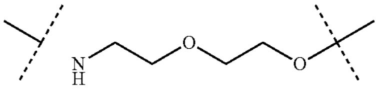
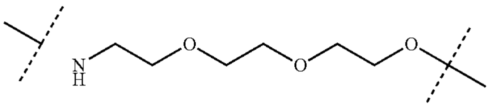
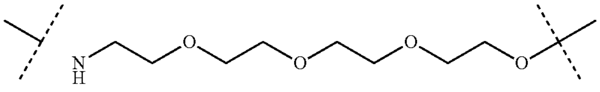
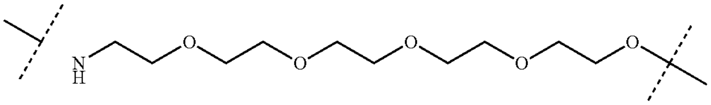
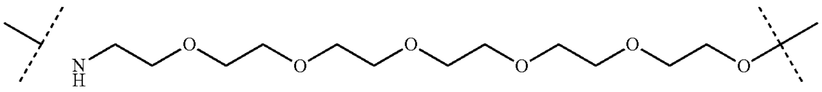

-continued
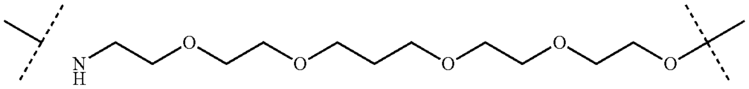
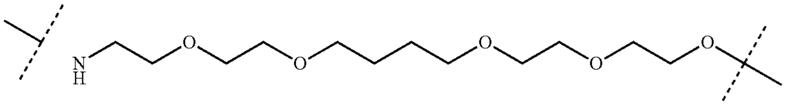
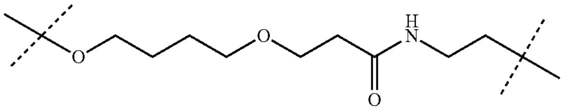
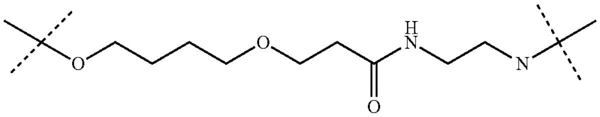
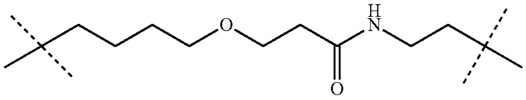
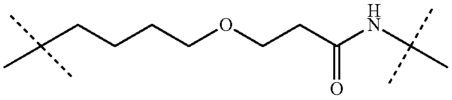
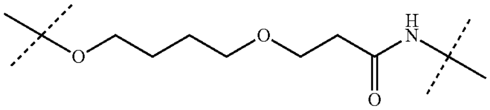
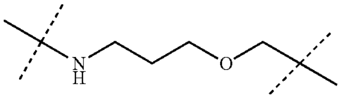
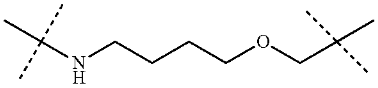
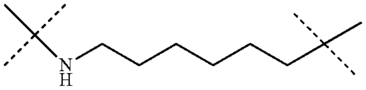
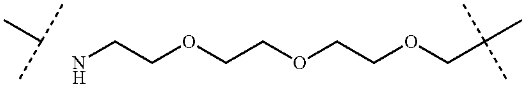
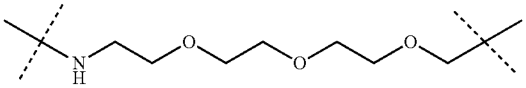
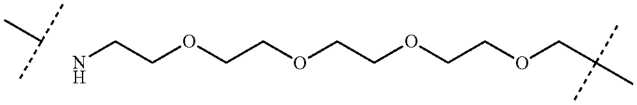
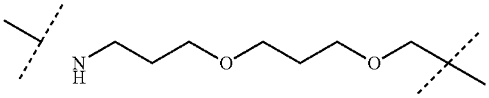
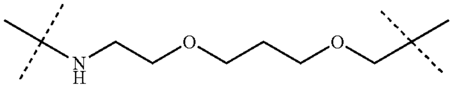
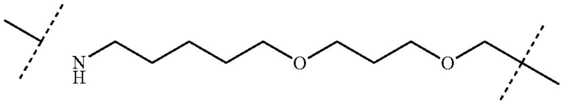
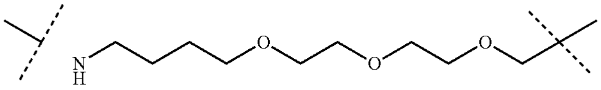
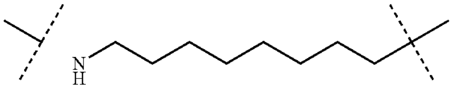
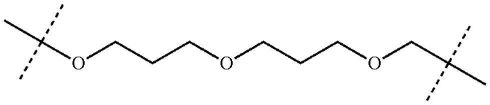
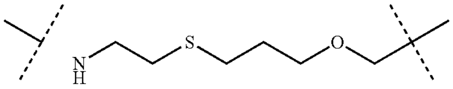
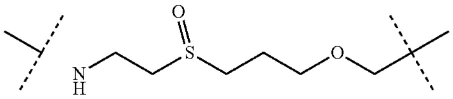
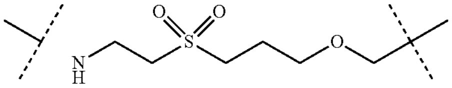
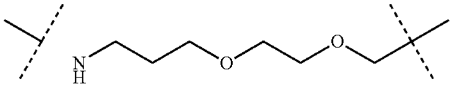
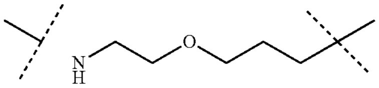
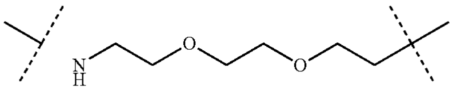
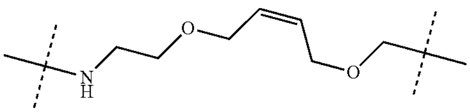
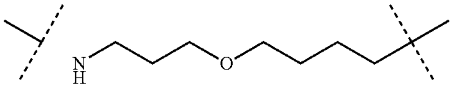
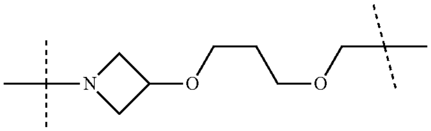
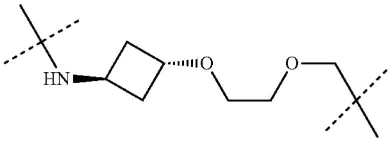
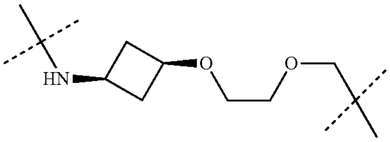

-continued
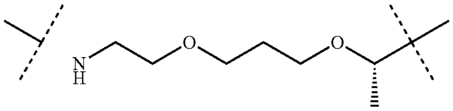
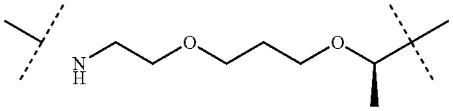
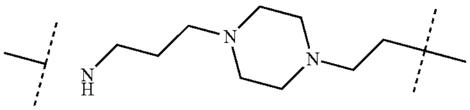
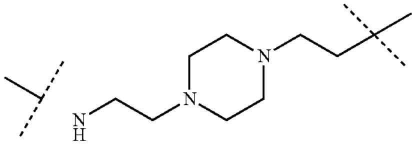
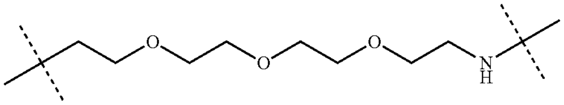
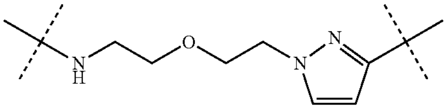
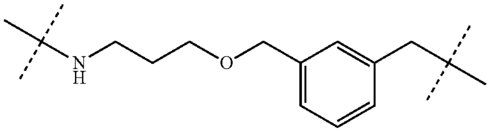
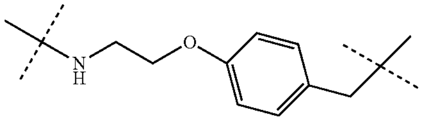
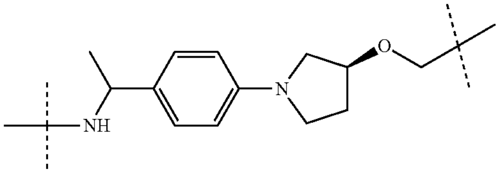
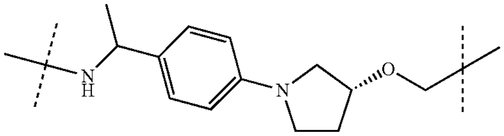
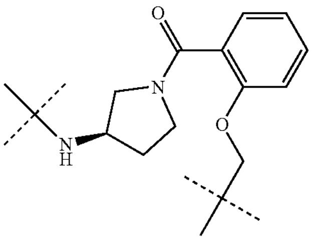
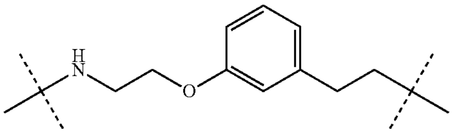
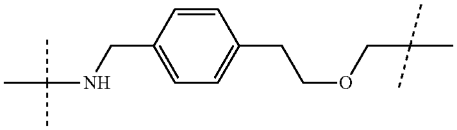
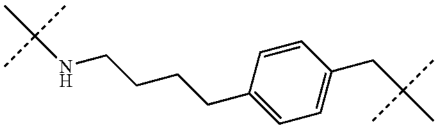
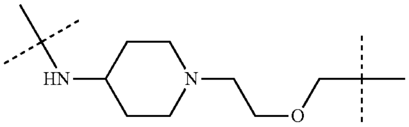
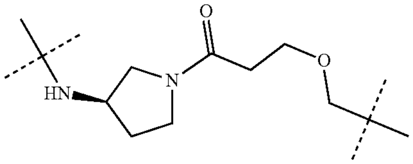
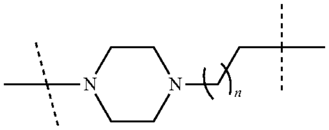
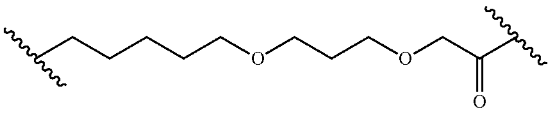;
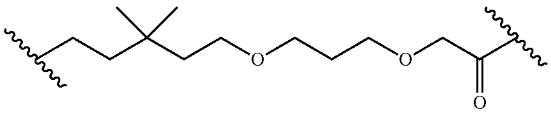;
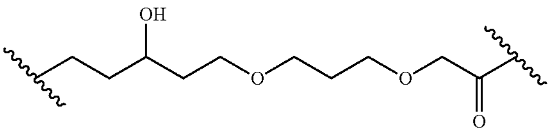;
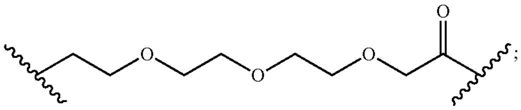;
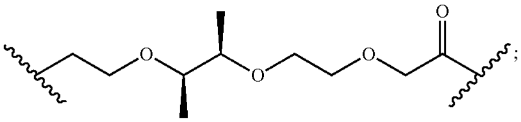;
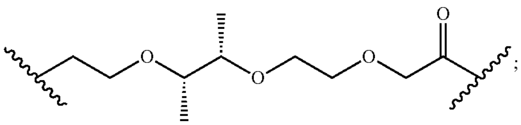;
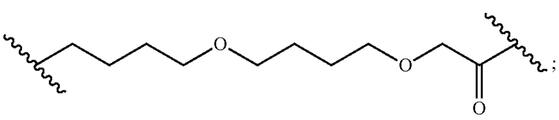;

-continued
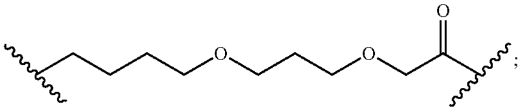 ; 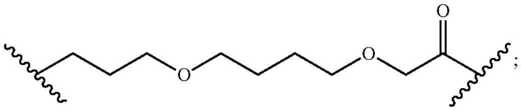 ;
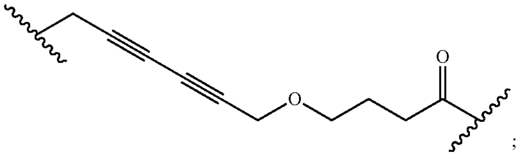 ; 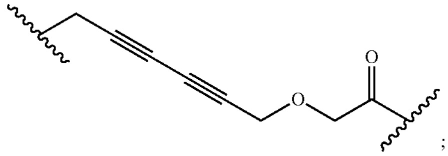 ;
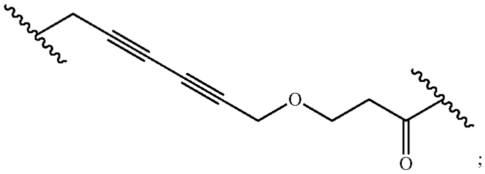 ; 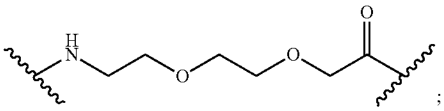 ;
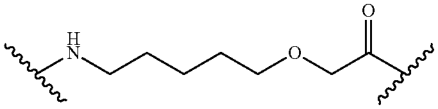 ; 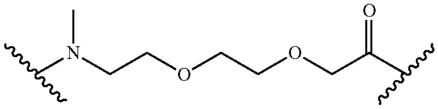 ;
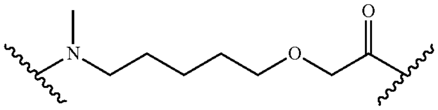 ; 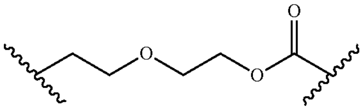 ;
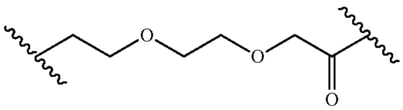 ; 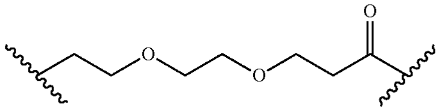 ;
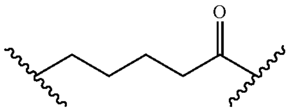 ; 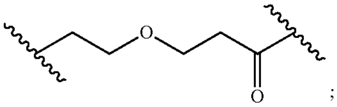 ; 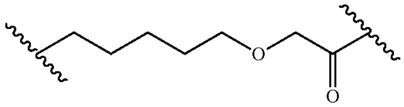 ;
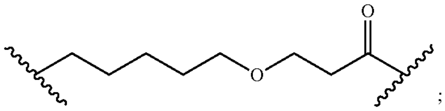 ; 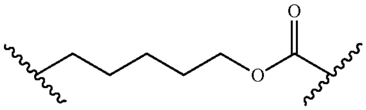 ;
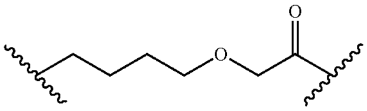 ; 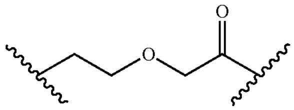 ; 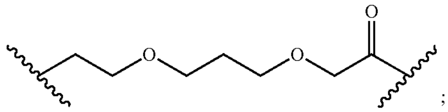 ;
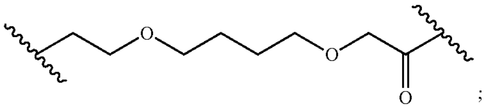 ; 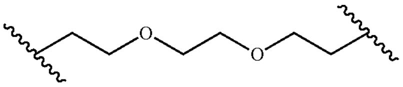 ;
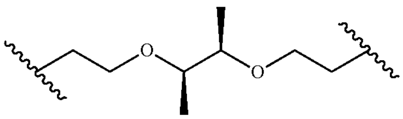 ; 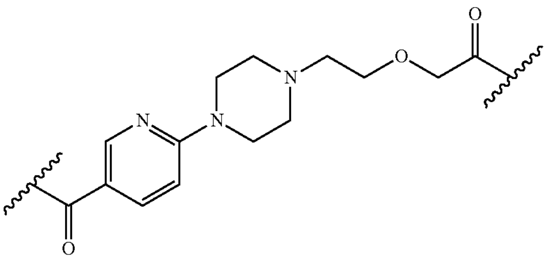 ;
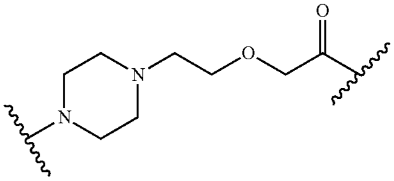 ; 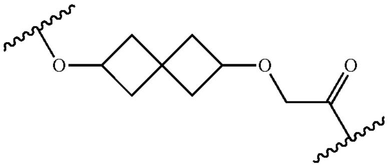 ;

-continued
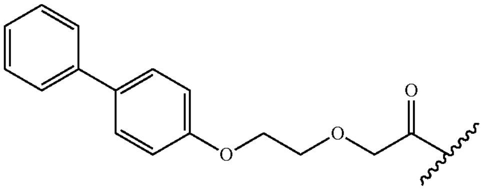
;
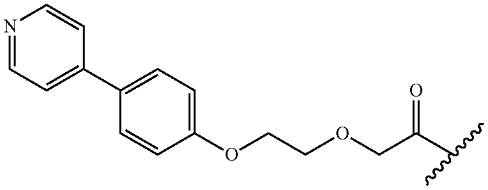
;
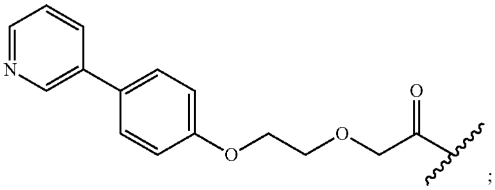
;
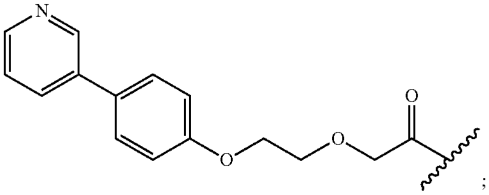
;
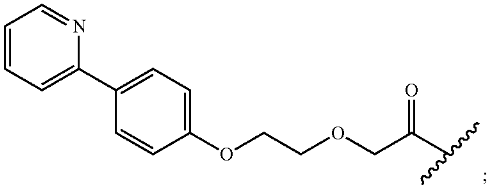
;
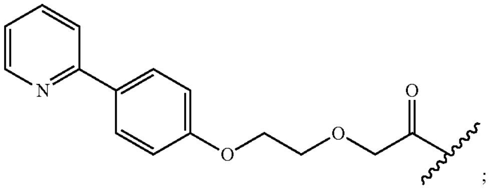
;
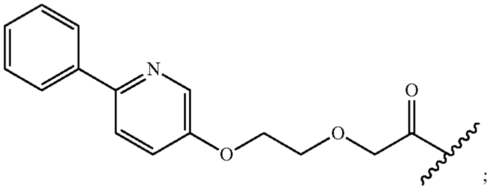
;
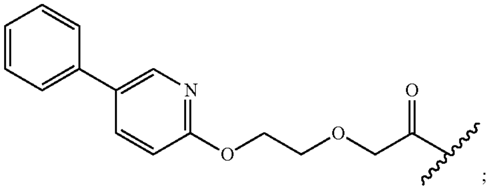
;
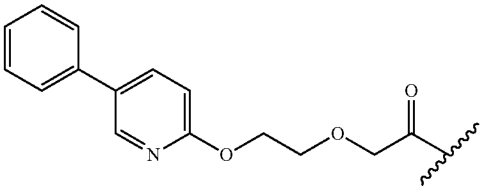
;
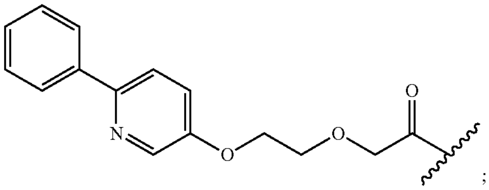
;
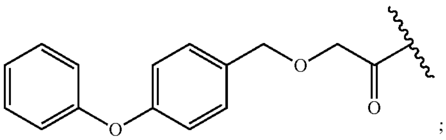
;
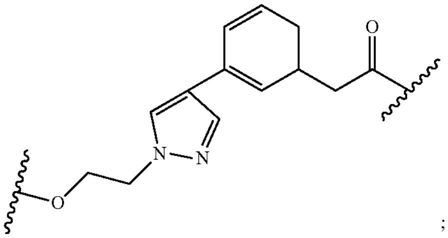
;
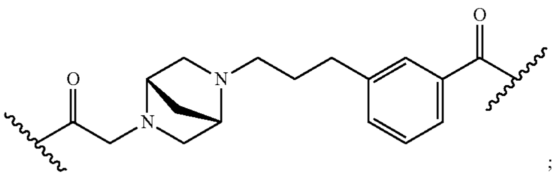
;
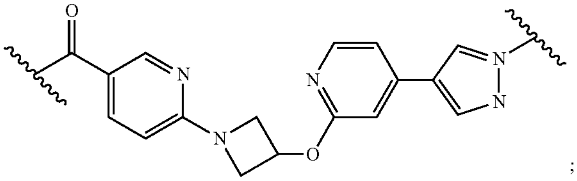
;
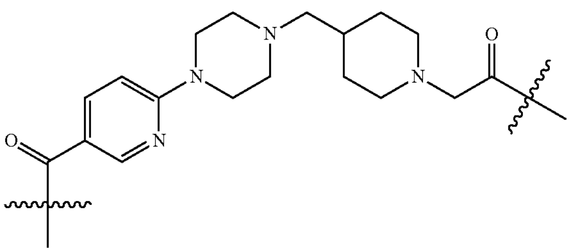
;
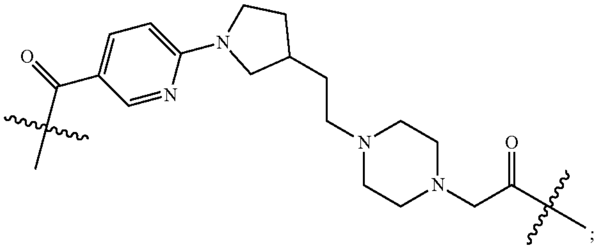
;

-continued
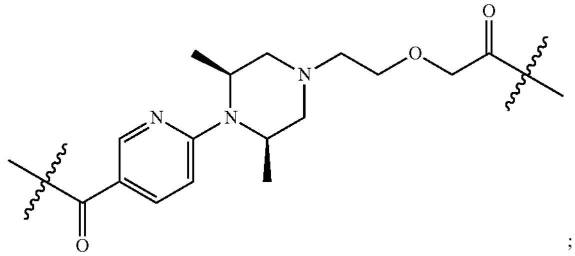
;
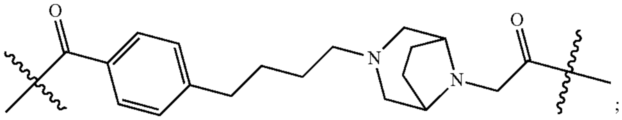
;
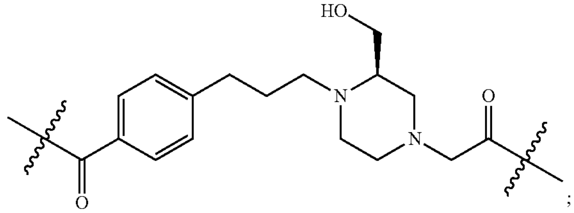
;
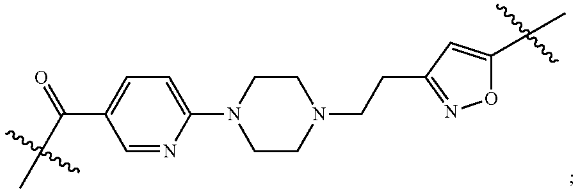
;
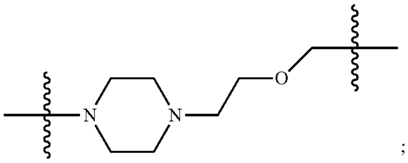
;
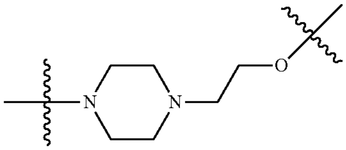
;
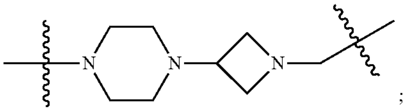
;
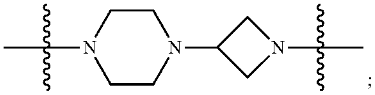
;
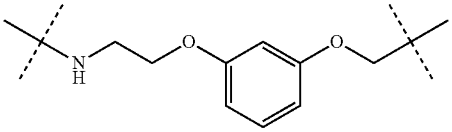
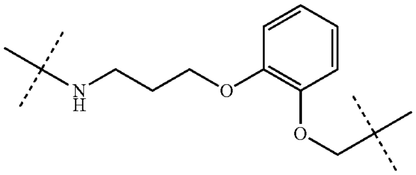
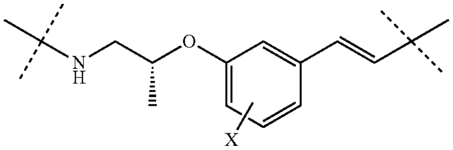
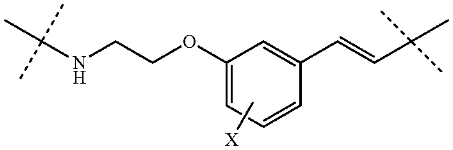
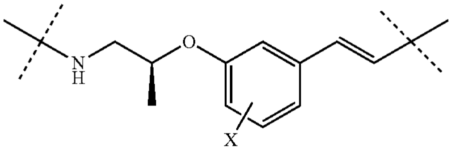
X = H, F
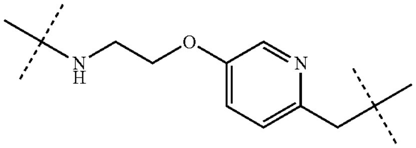
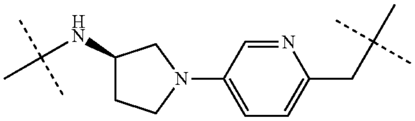
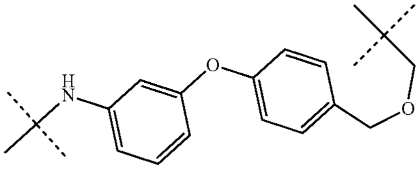
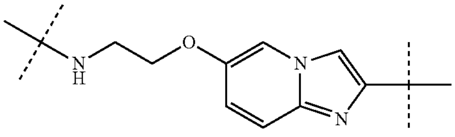

-continued
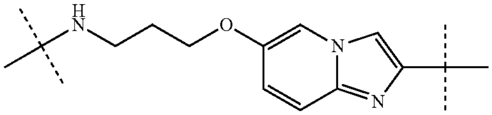
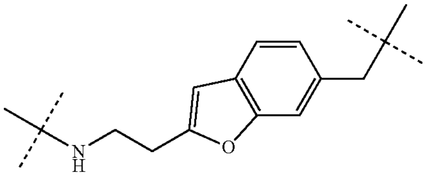
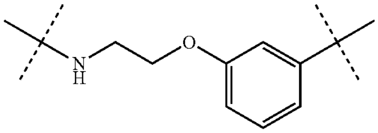
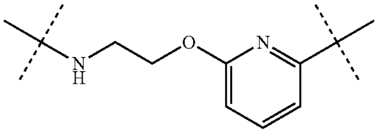
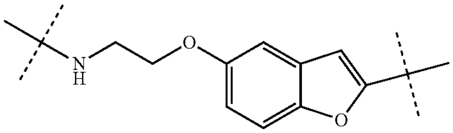
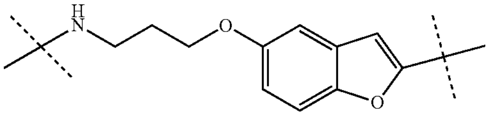
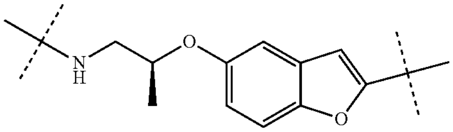
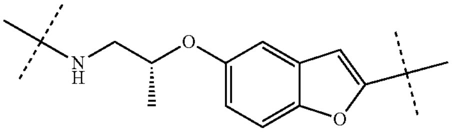
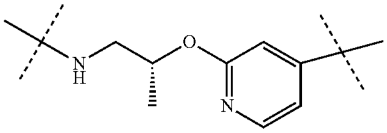
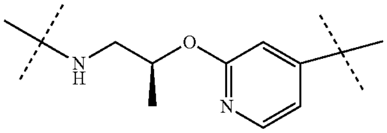
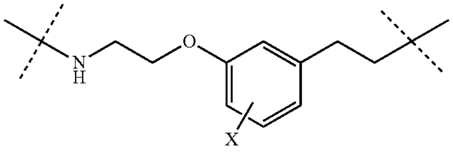
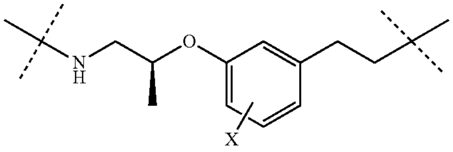
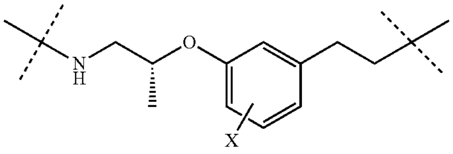
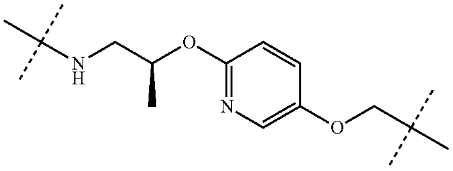
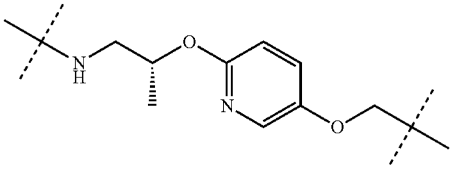
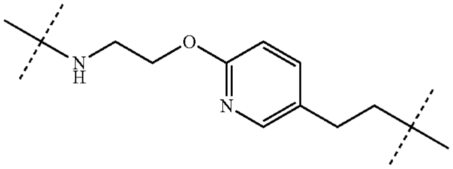
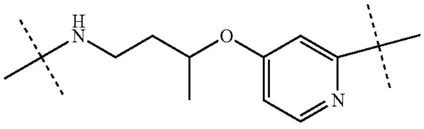
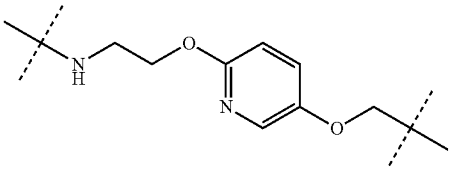
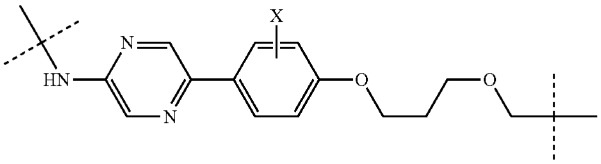
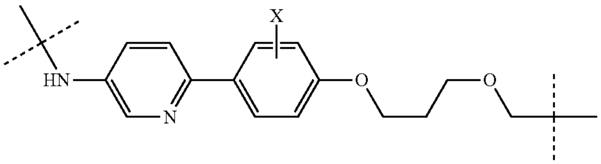
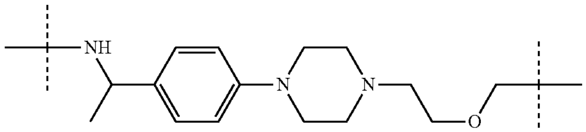

-continued
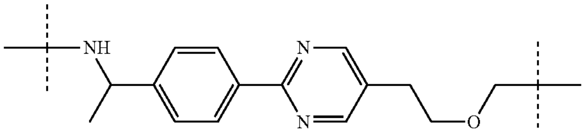
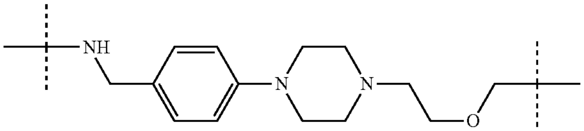
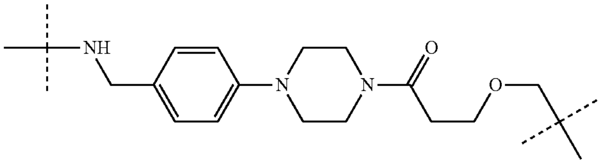
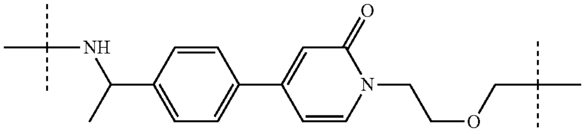
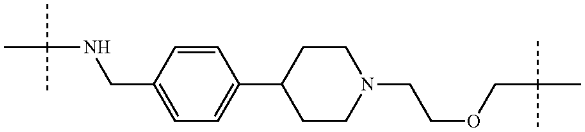
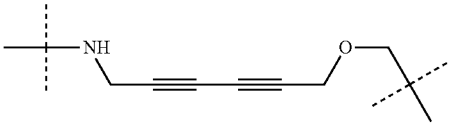
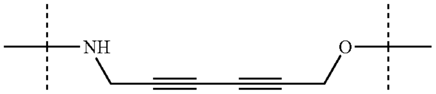
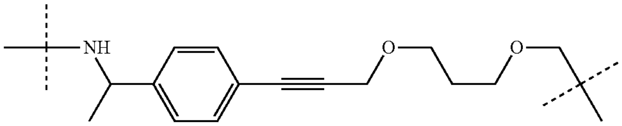
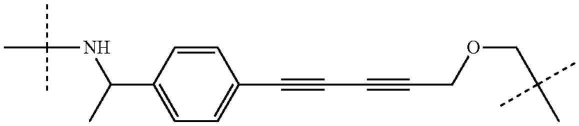
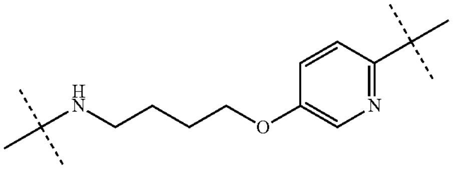
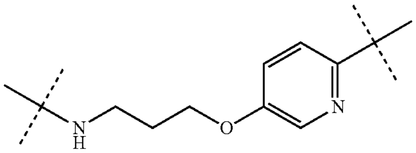
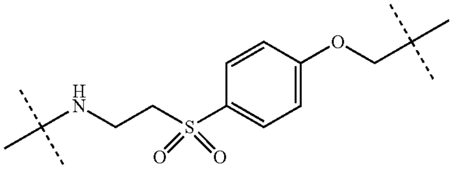
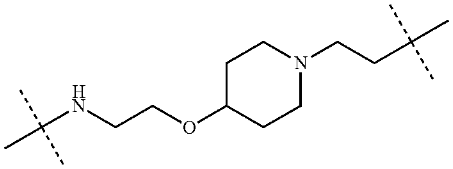
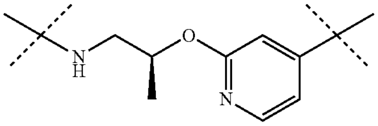
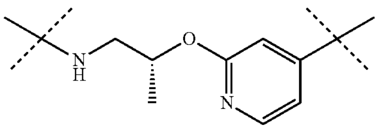
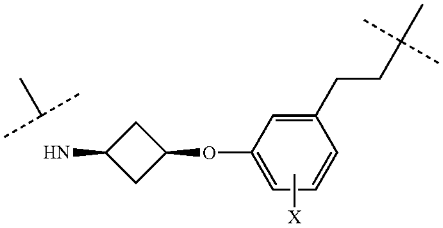
X = H, F
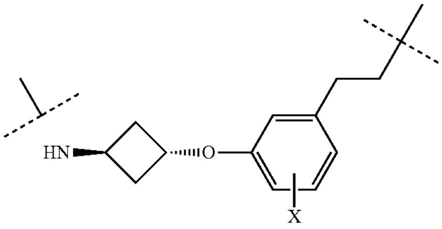
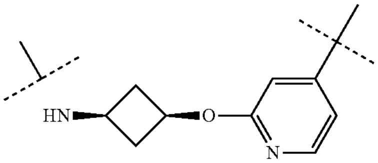
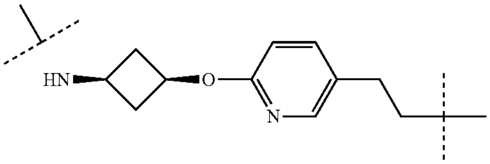
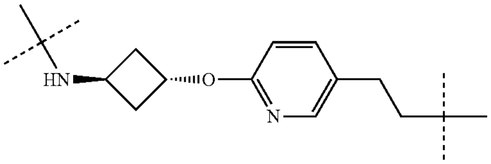

-continued
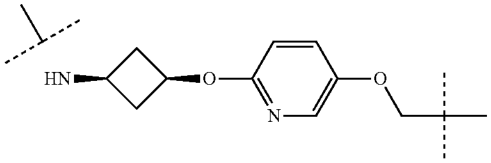
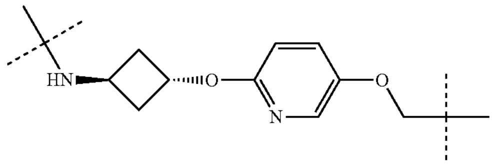
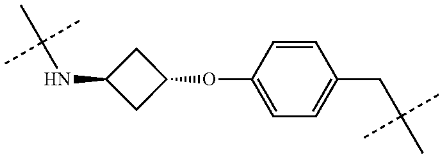
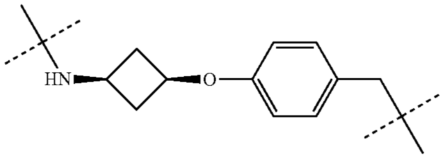
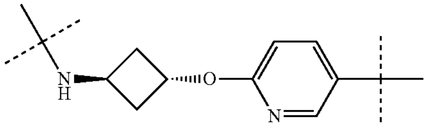
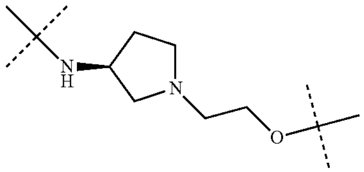
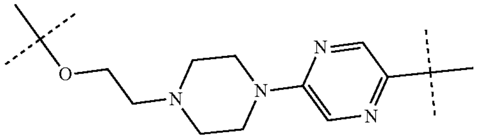
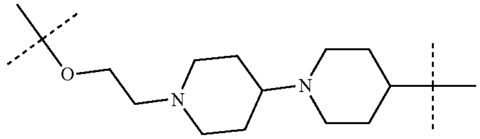
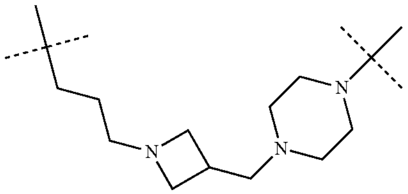
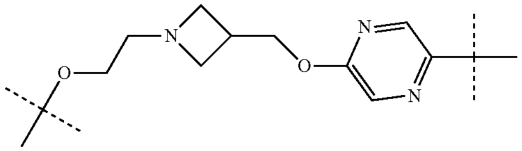
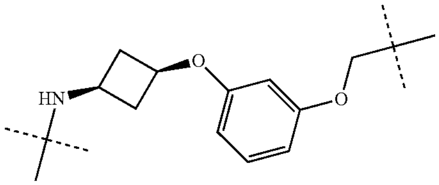
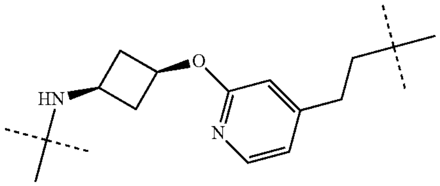
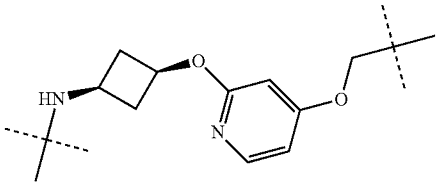
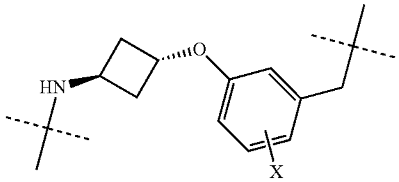
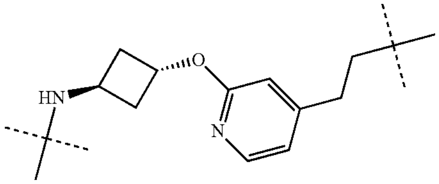
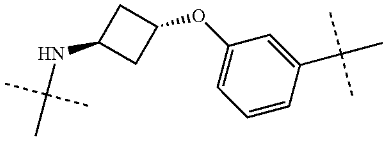
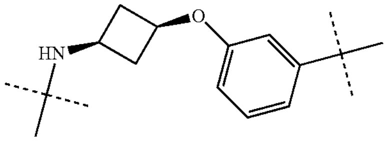
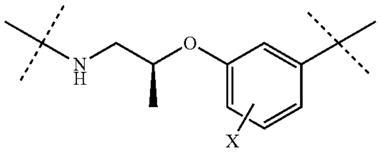

-continued
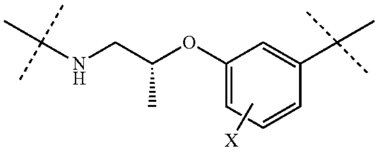
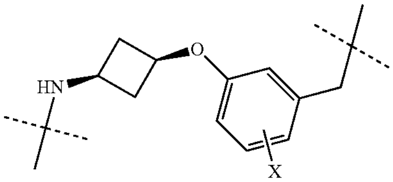
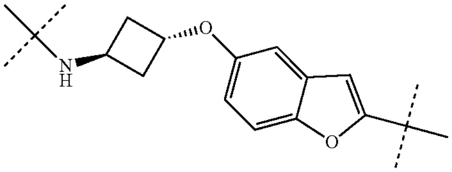
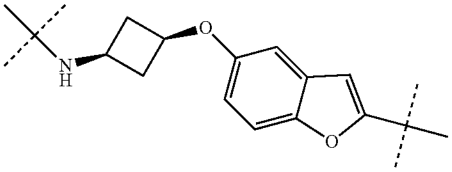
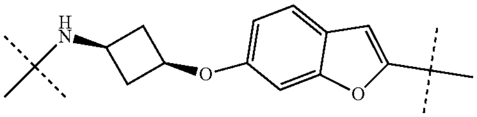
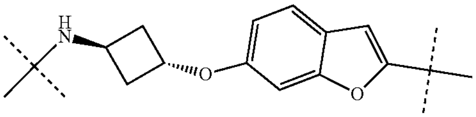
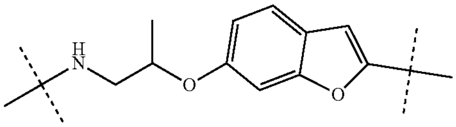
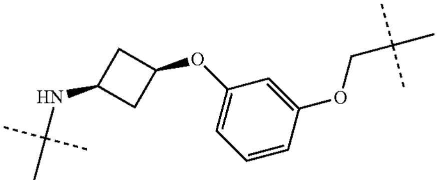
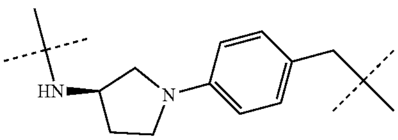
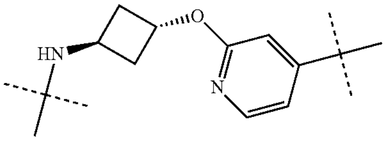
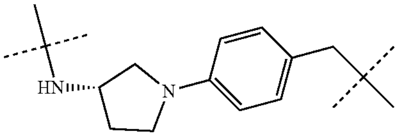
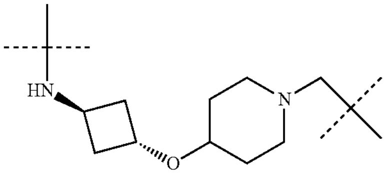
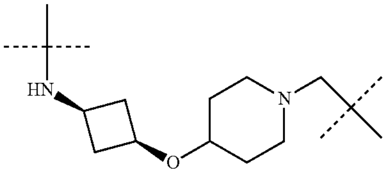
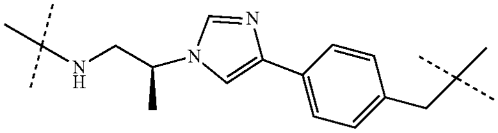
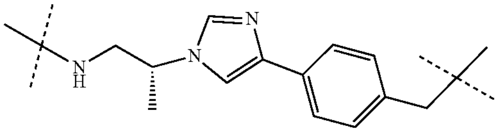
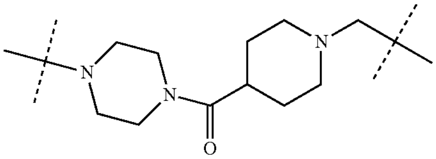
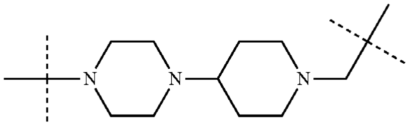
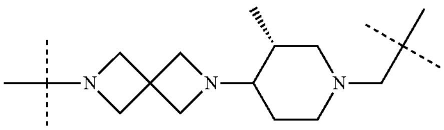
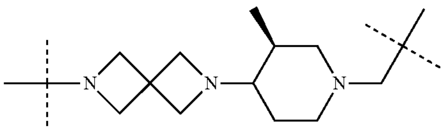
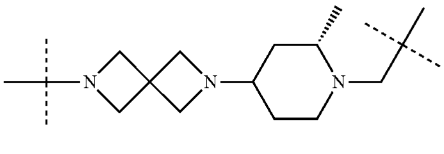

-continued
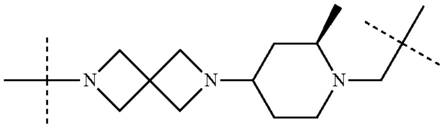
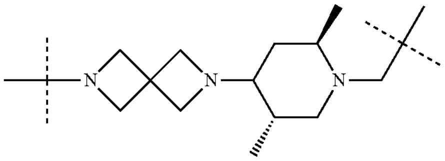
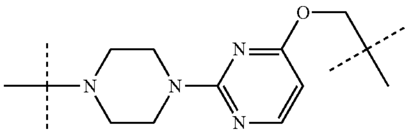
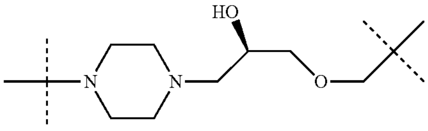
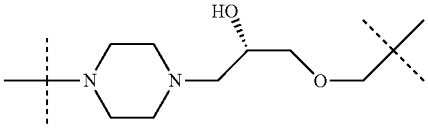
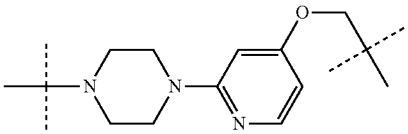
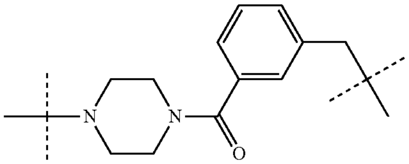
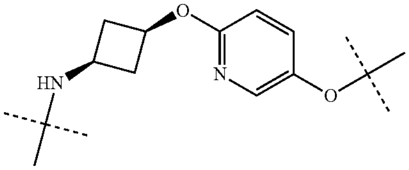
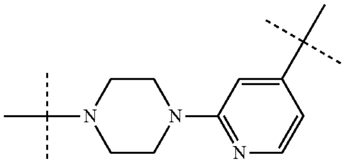
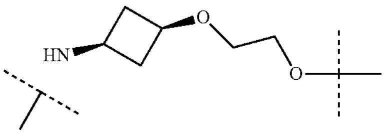
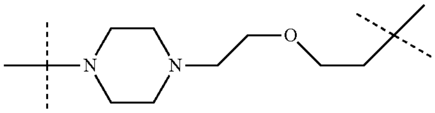
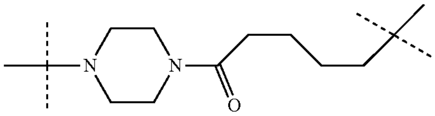
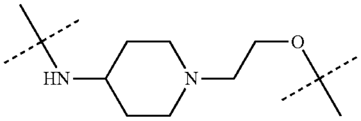
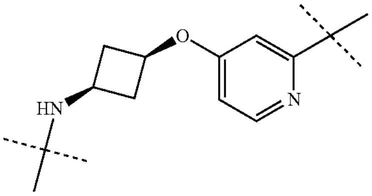
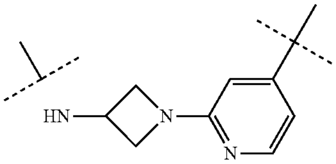
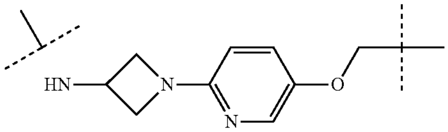
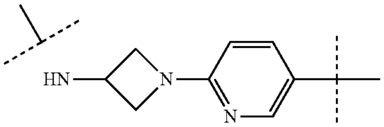
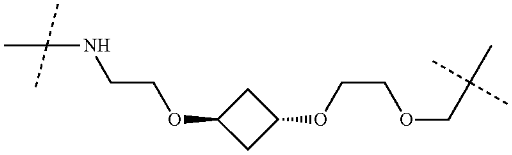
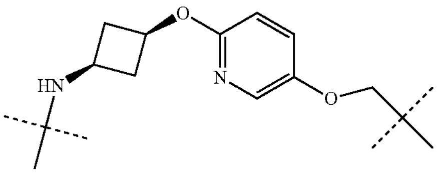
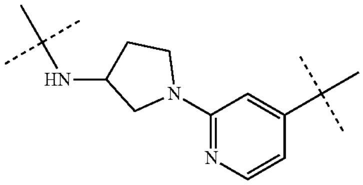

-continued
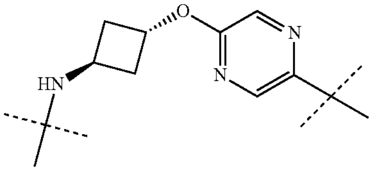
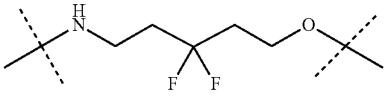
wherein each n and m of the linker can independently be 0, 1, 2, 3, 4, 5, 6.
In any aspect or embodiment described herein, the linker (L) is selected from the group consisting of:
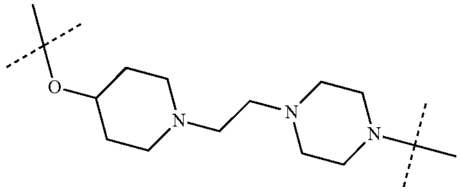
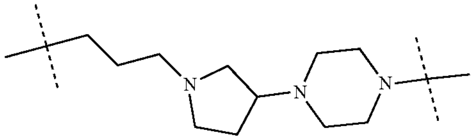
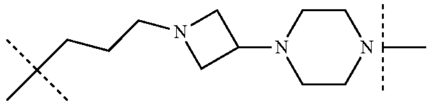
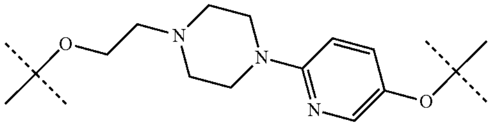
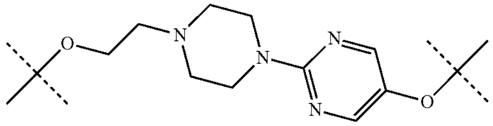
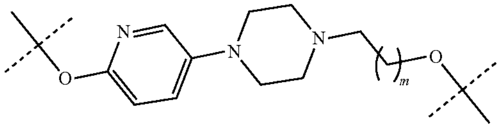
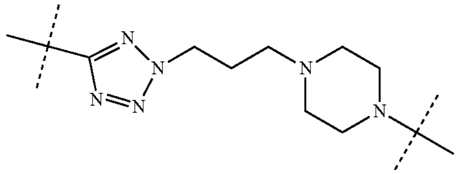
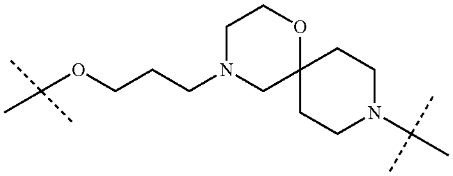
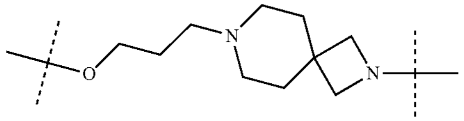
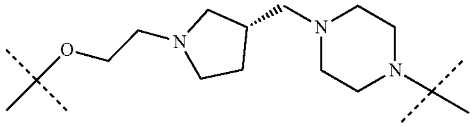
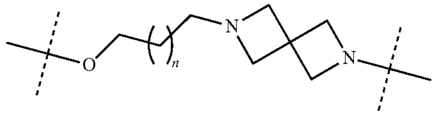
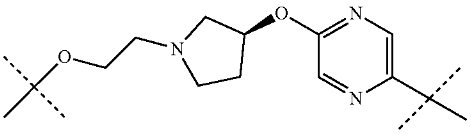
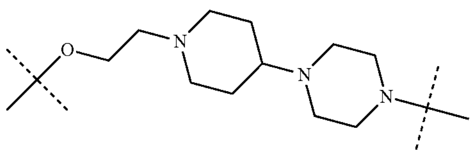
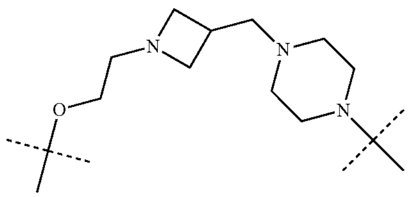
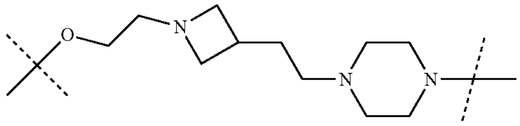
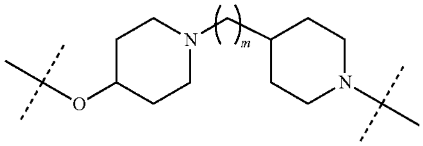
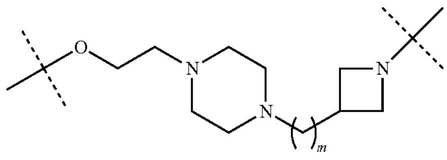
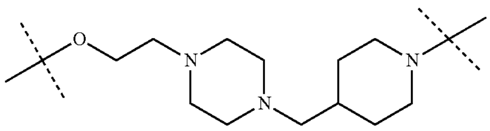

-continued
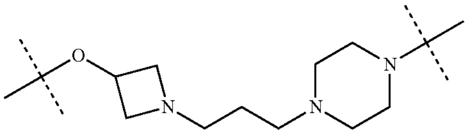
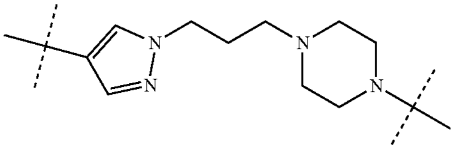
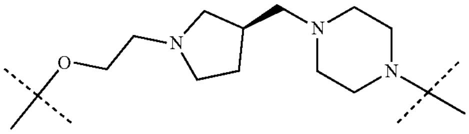
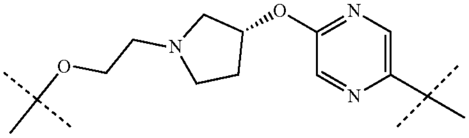
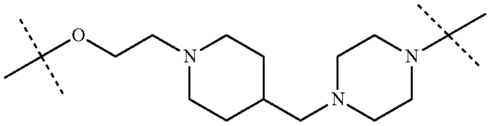
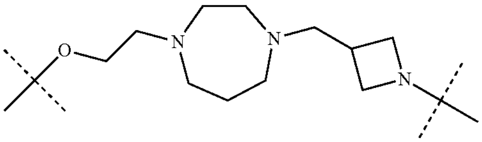
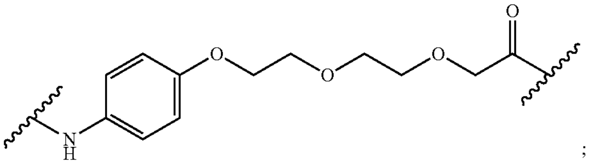
;
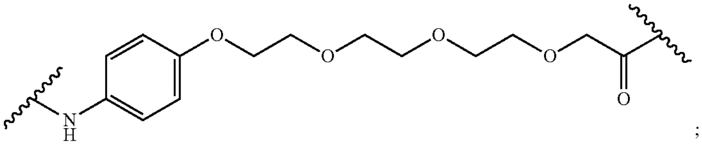
;
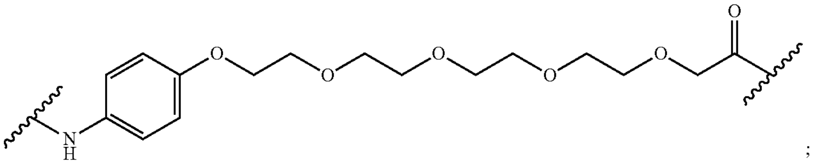
;
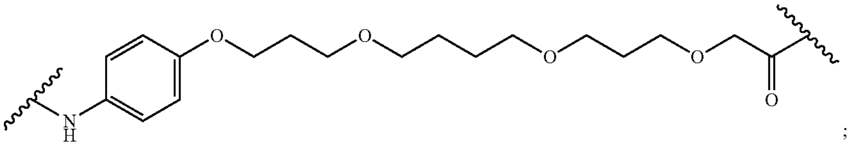
;
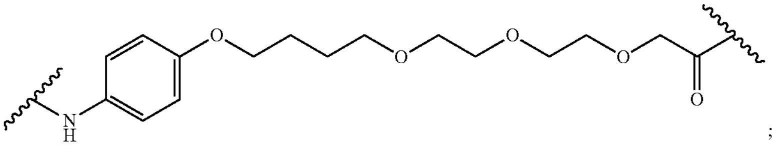
;
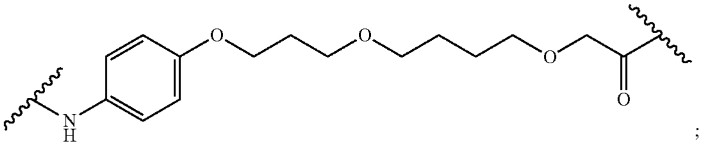
;
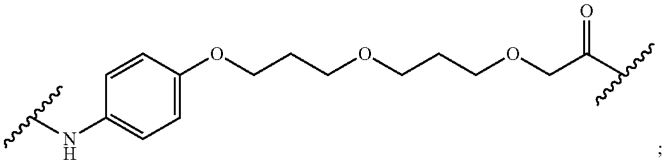
;
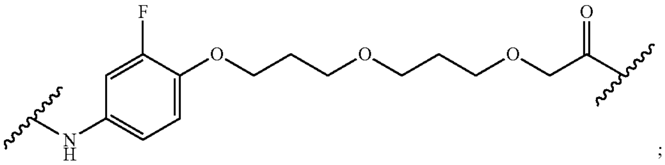
;

-continued
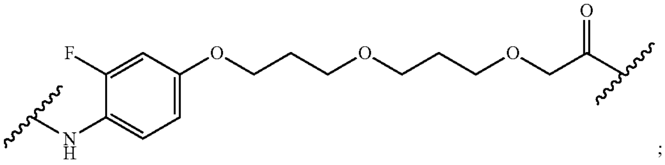
;
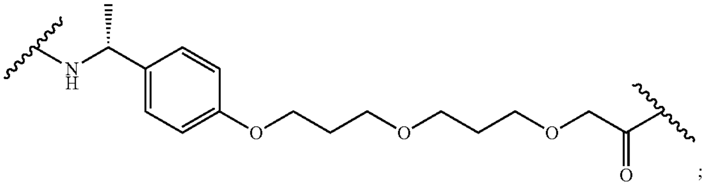
;
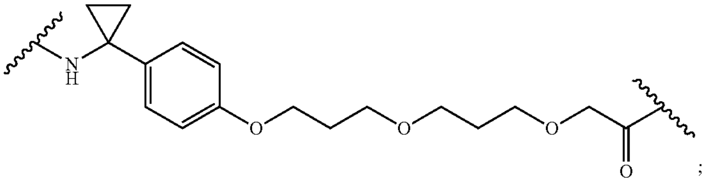
;
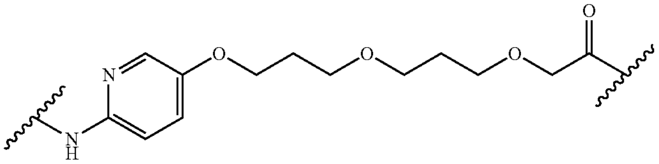
;
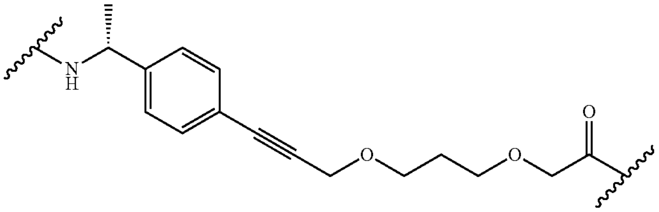
;
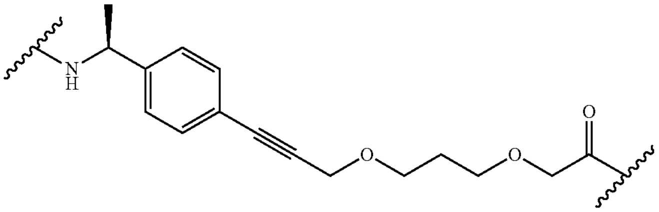
;
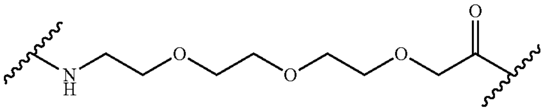
;
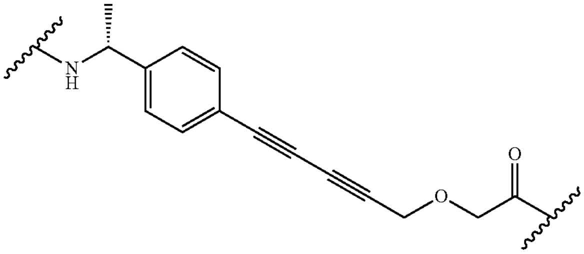
;
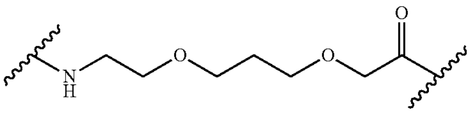
;
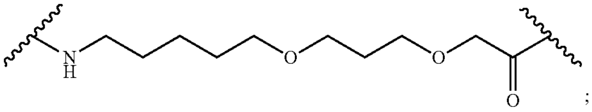
;
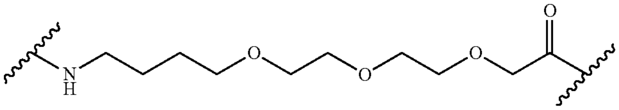
;

-continued
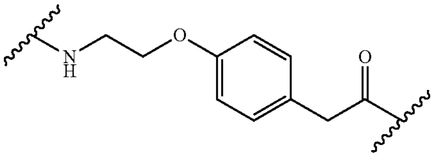
;
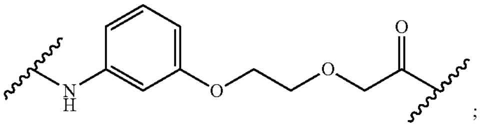
;
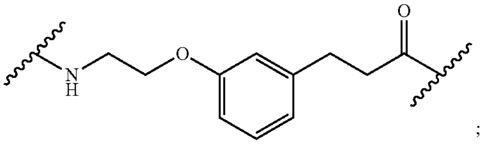
;
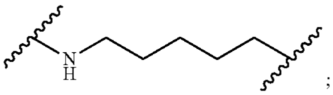
;
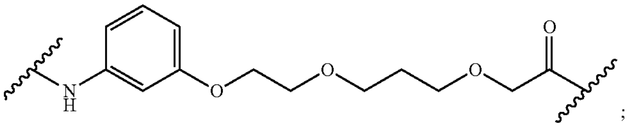
;
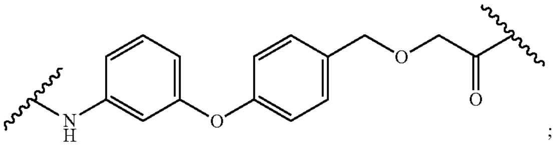
;
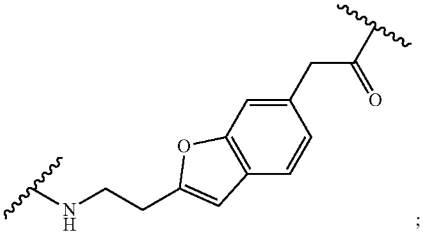
;
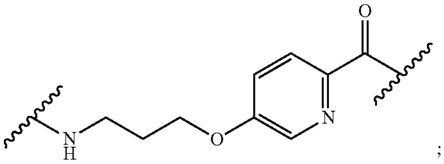
;
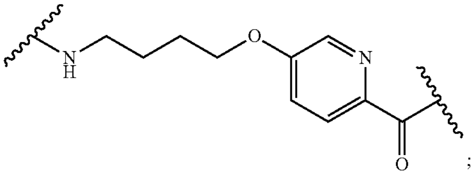
;
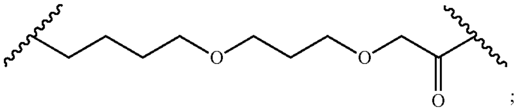
;
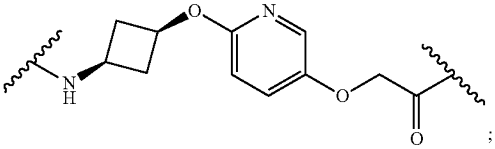
;
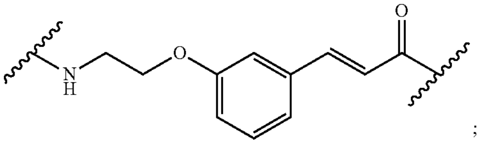
;
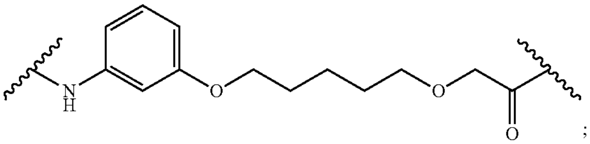
;
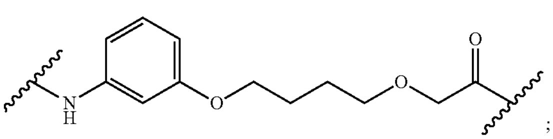
;
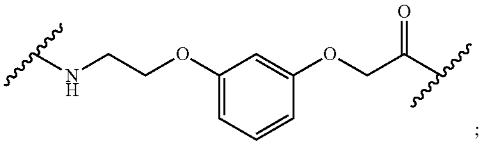
;
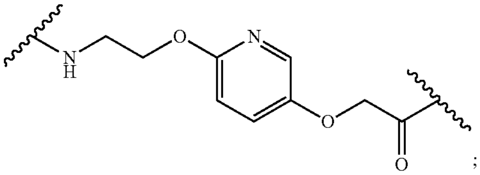
;
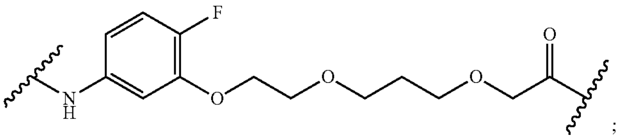
;
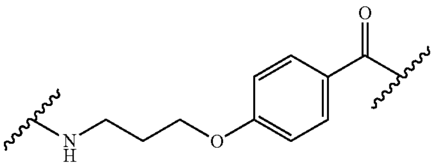
;
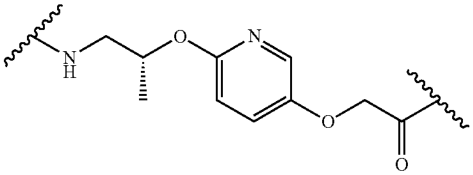
;

-continued
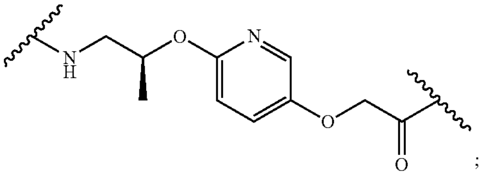
;
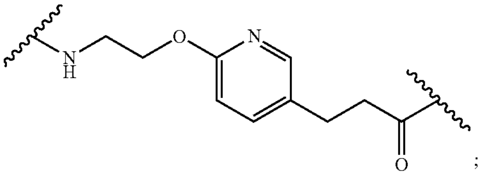
;
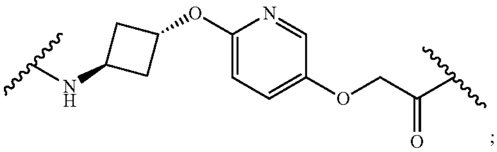
;
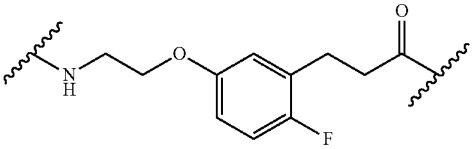
;
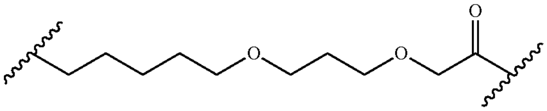
;
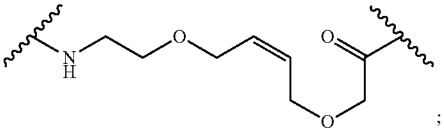
;
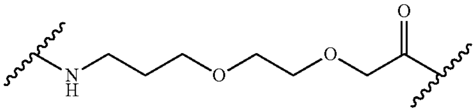
;
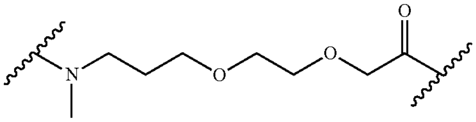
;
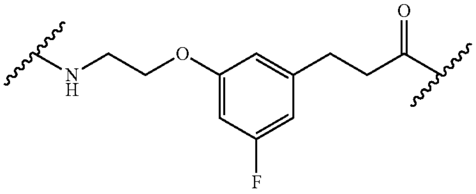
;
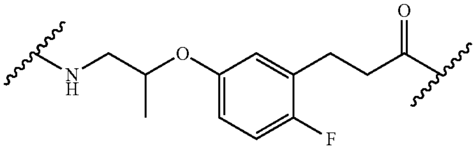
;
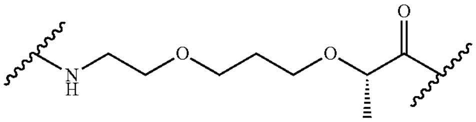
;
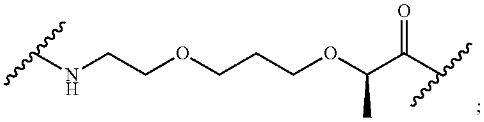
;
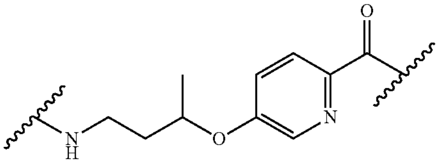
;
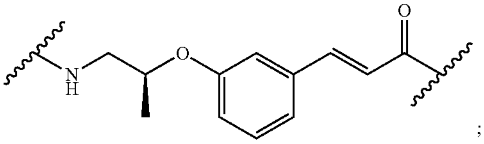
;
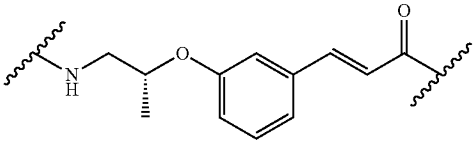
;
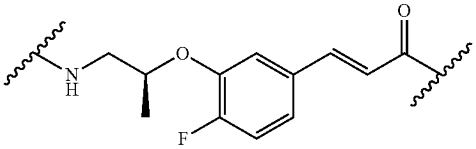
;
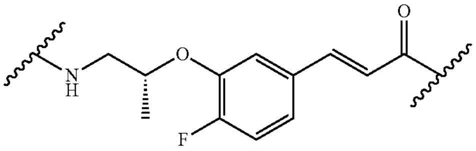
;
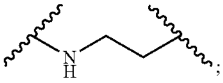
;
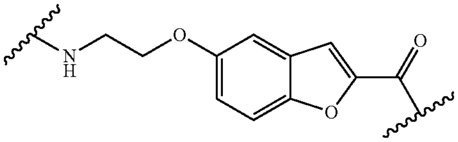
;
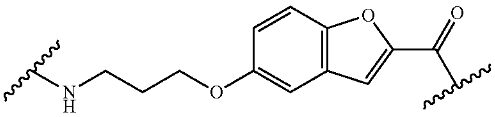
;
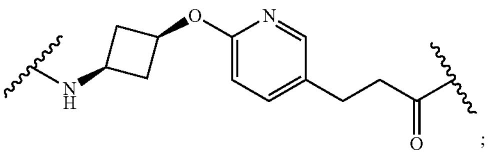
;
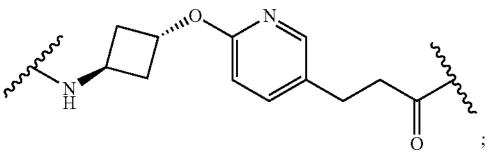
;

-continued
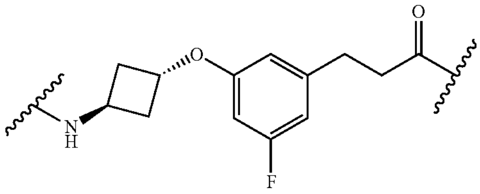
;
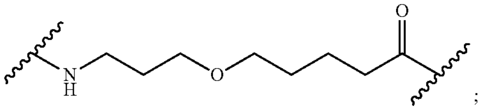
;
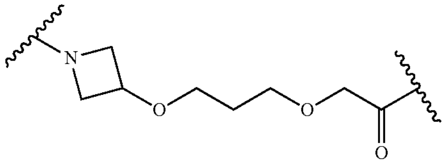
;
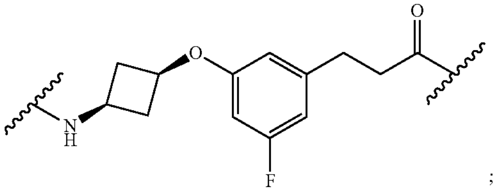
;
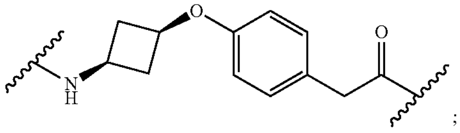
;
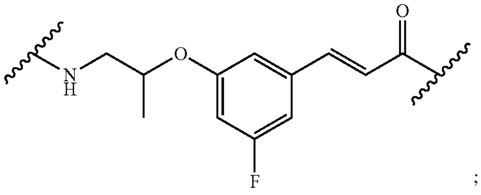
;
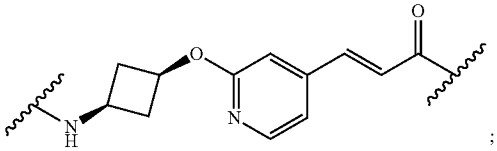
;
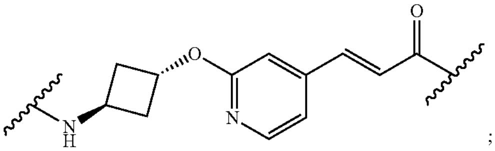
;
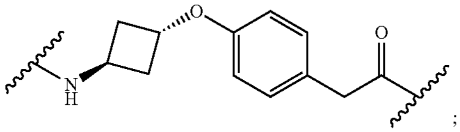
;
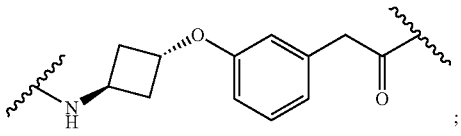
;
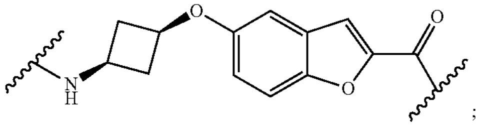
;
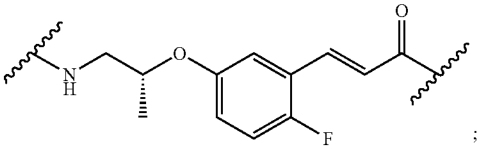
;
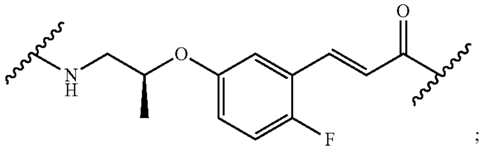
;
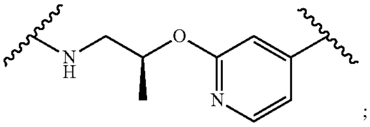
;
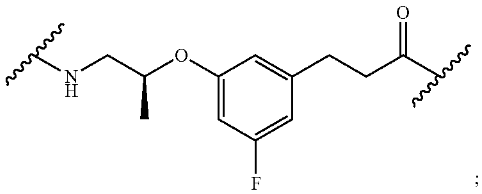
;
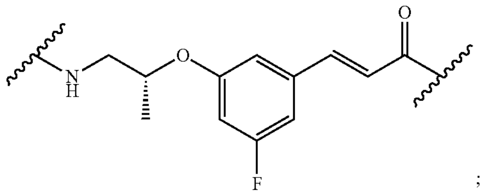
;
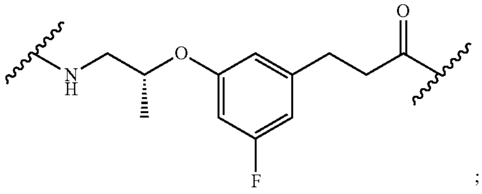
;
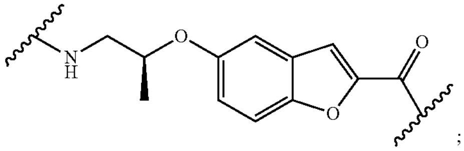
;
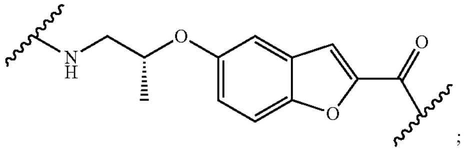
;
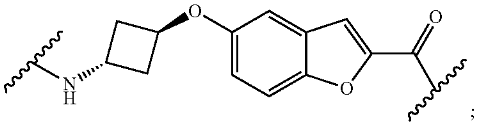
;

-continued
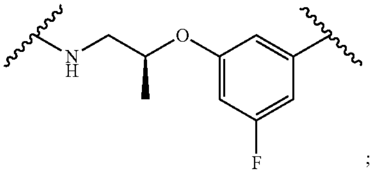
;
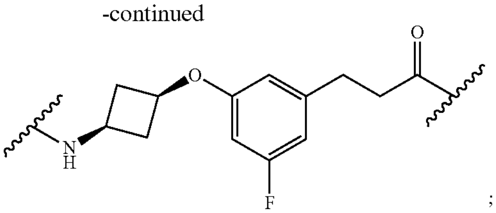
;
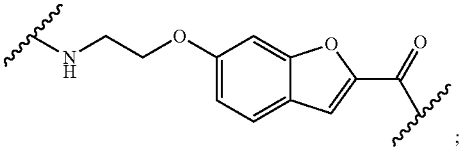
;
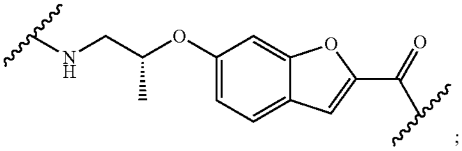
;
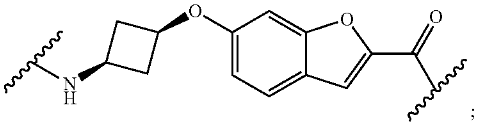
;
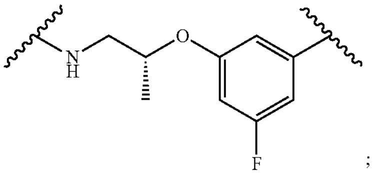
;
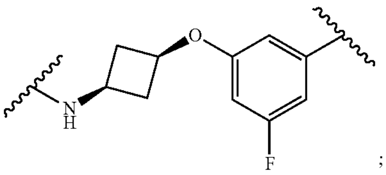
;
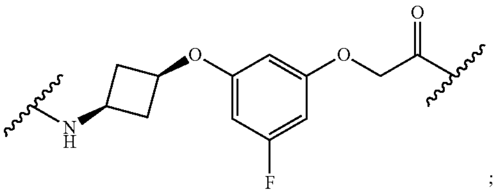
;
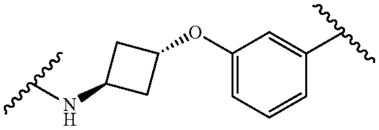
;
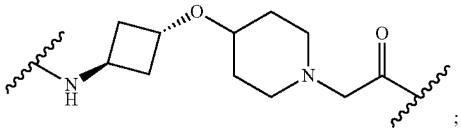
;
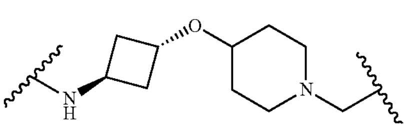
and
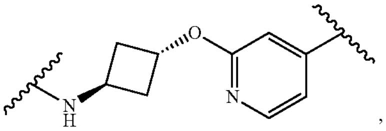
,
wherein each m and n is independently selected from 0, 1, 2, 3, 4, 5, or 6.
In any aspect or embodiment described herein, the linker (L) is selected from the group consisting of:
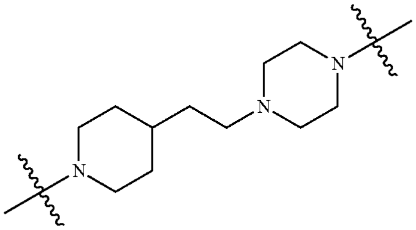
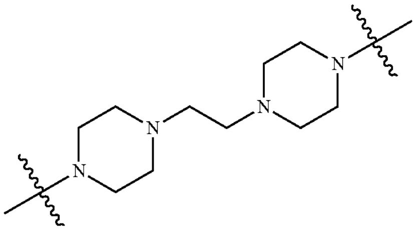
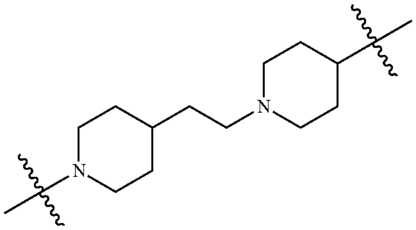
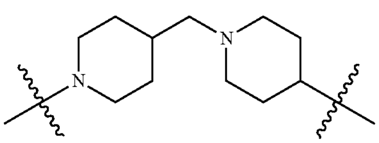
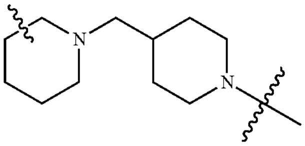

-continued
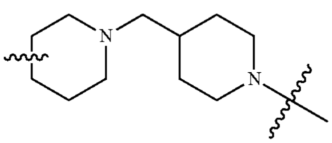
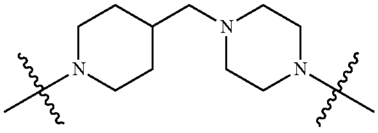
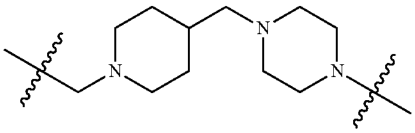
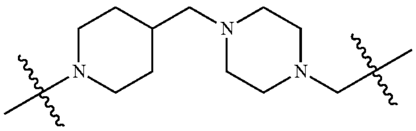
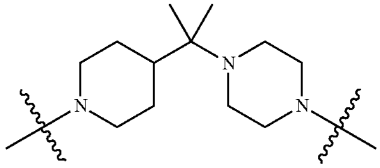
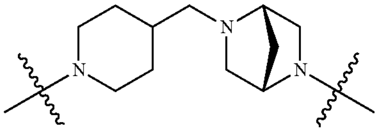
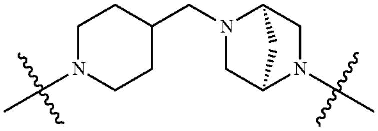
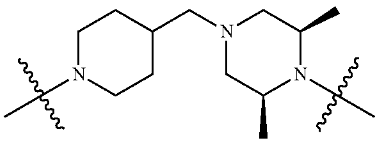
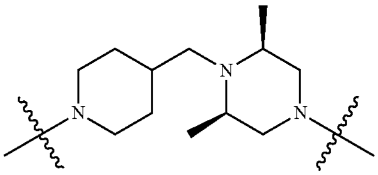
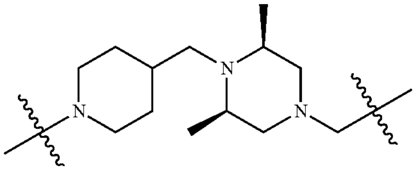
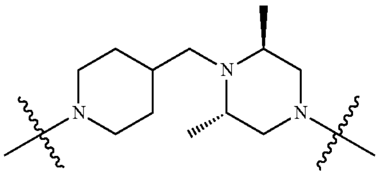
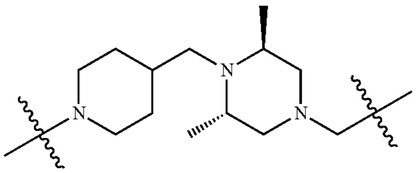
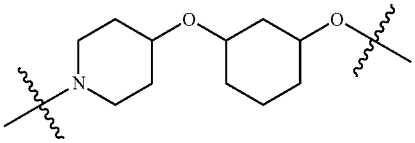
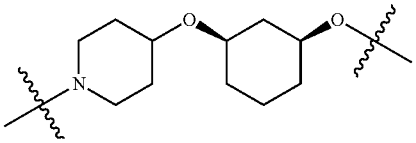
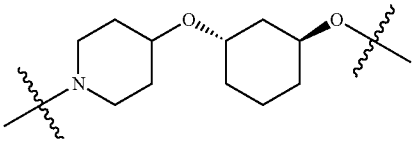
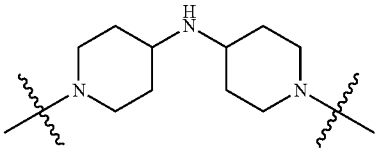
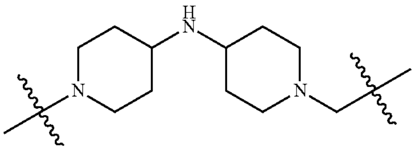
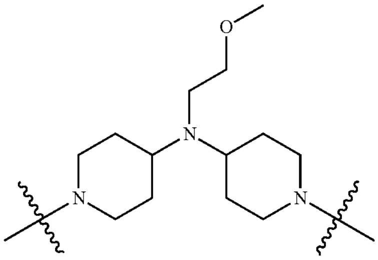
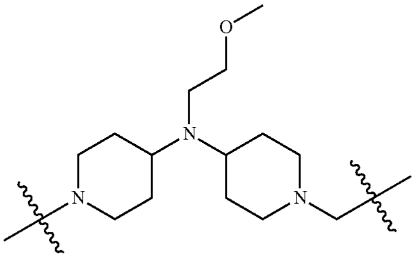
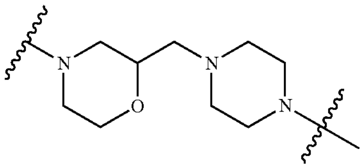
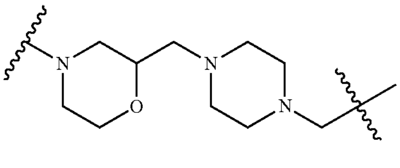
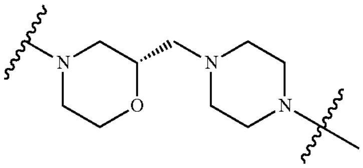

-continued
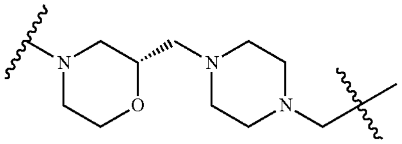
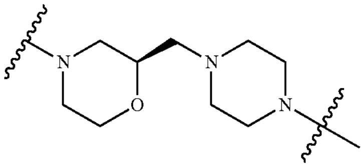
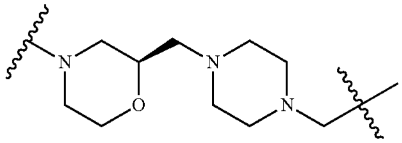
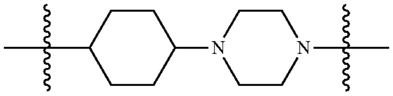
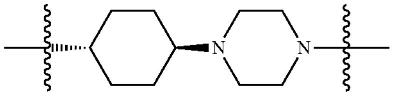
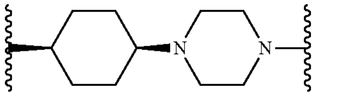
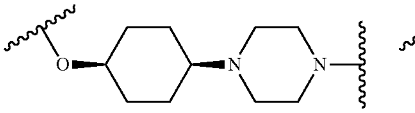
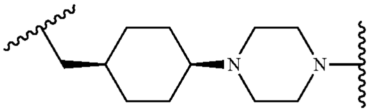
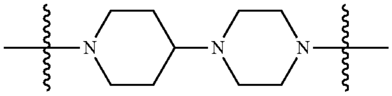
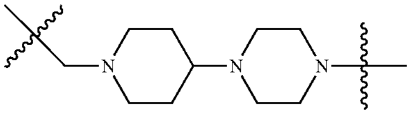
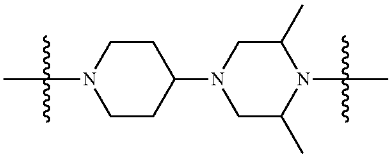
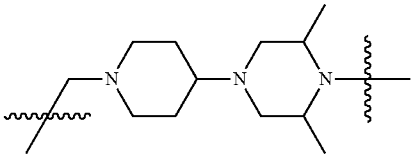
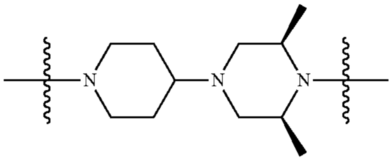
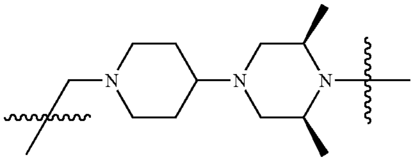
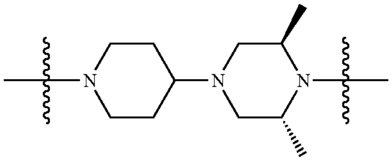
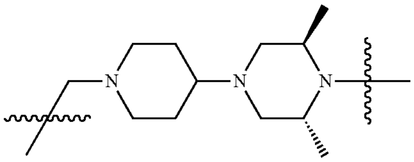
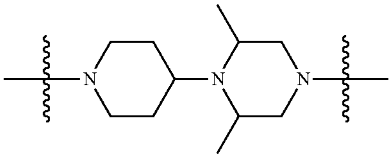
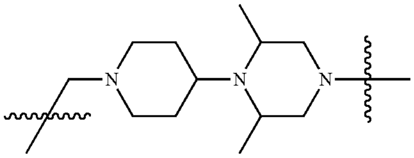
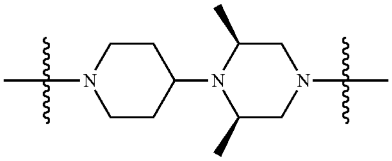
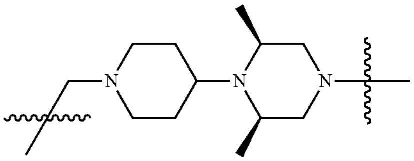
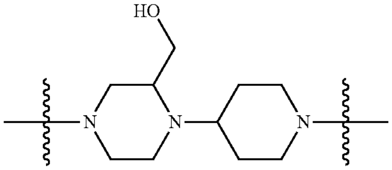
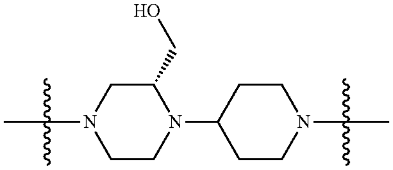
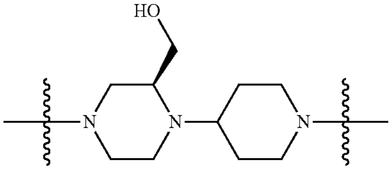
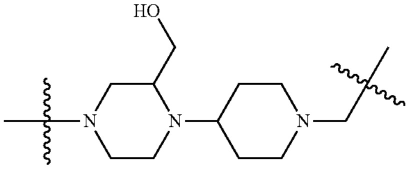
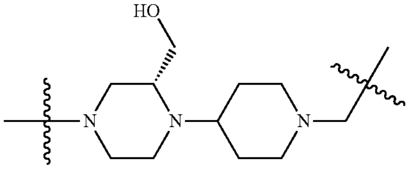

-continued
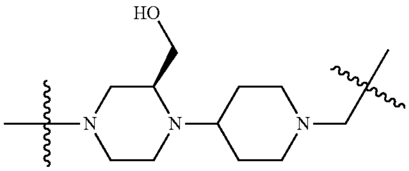
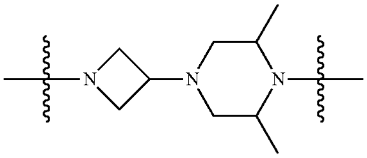
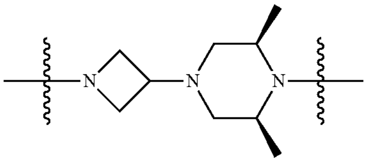
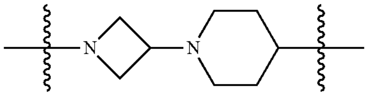
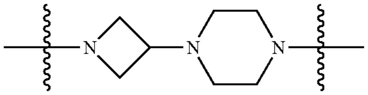
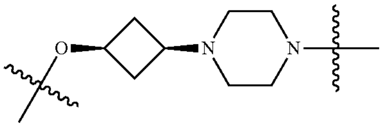
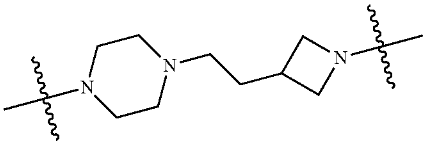
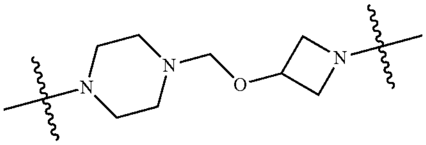
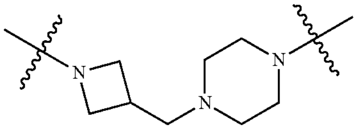
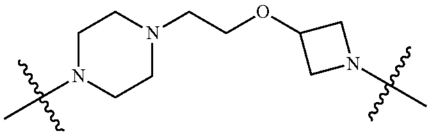
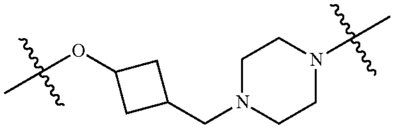
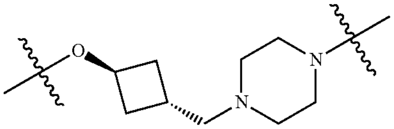
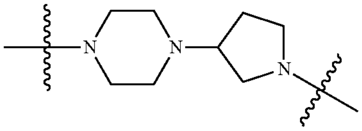
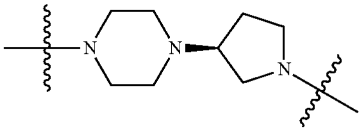
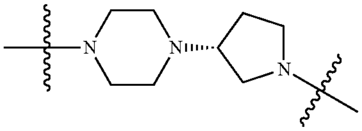
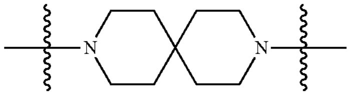
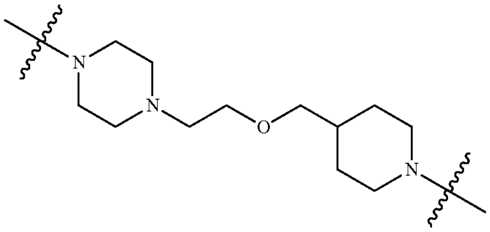
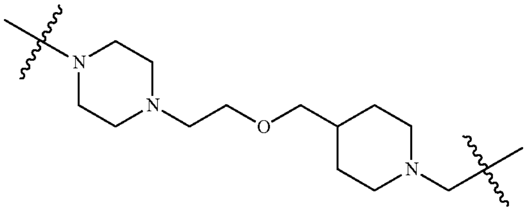
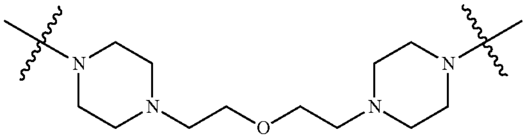
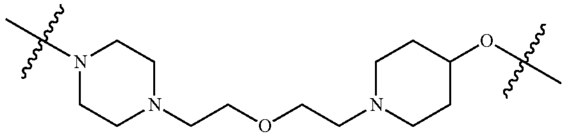
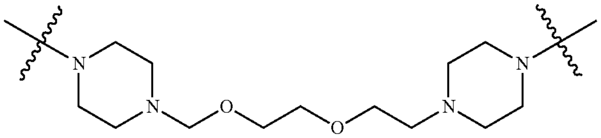
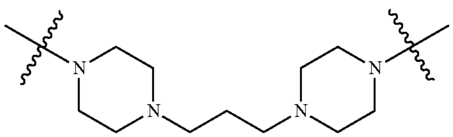
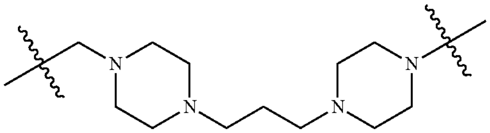
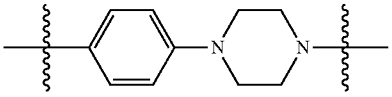
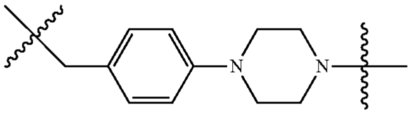
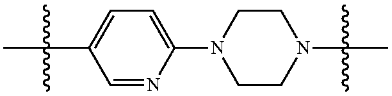

-continued
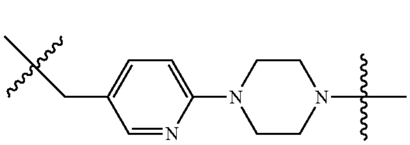
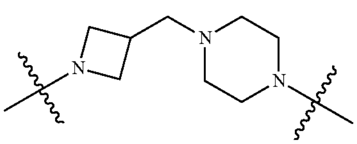
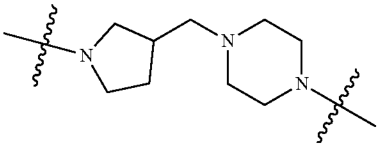
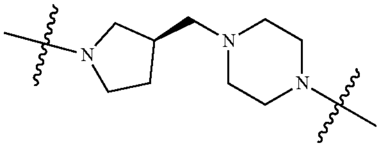
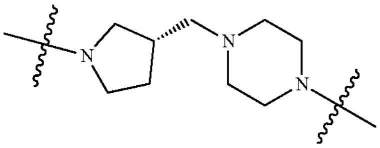
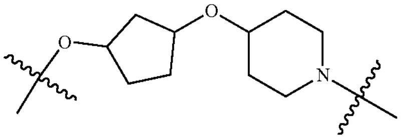
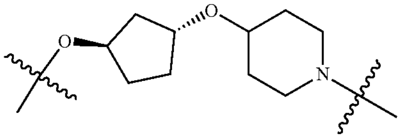
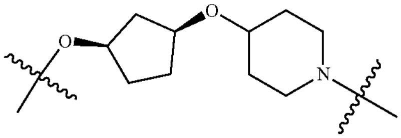
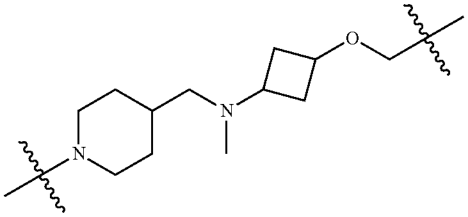
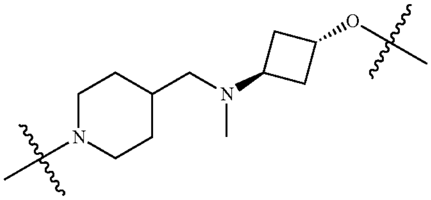
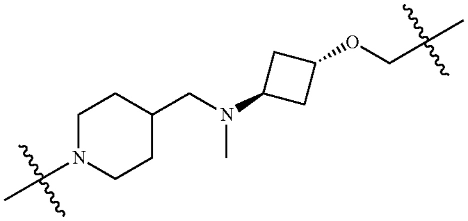
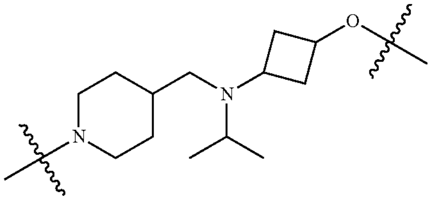
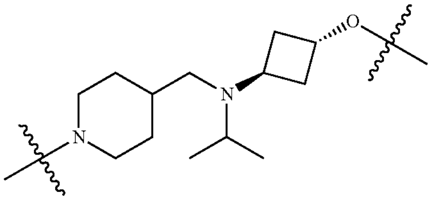
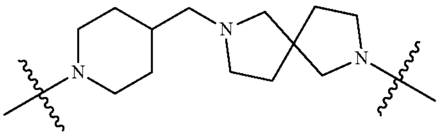
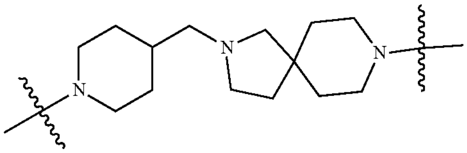
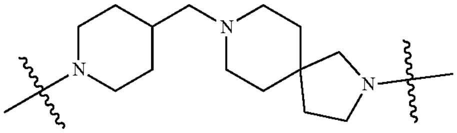
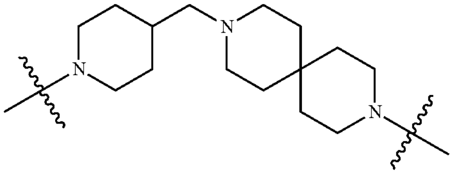
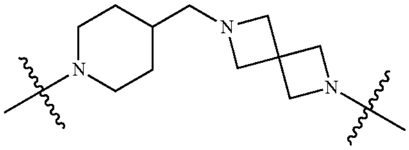
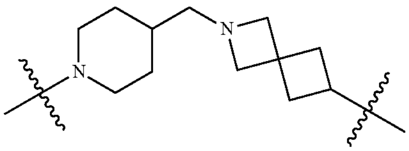
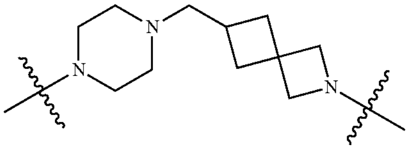
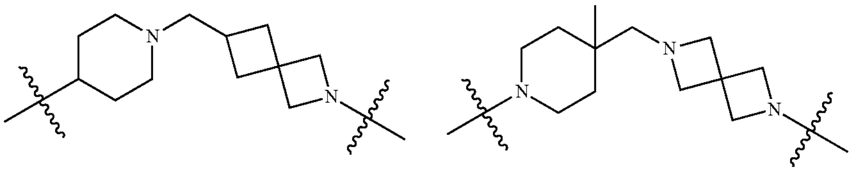

-continued
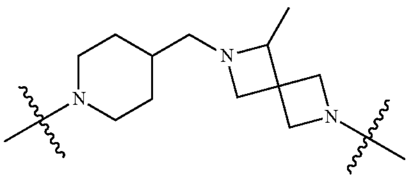
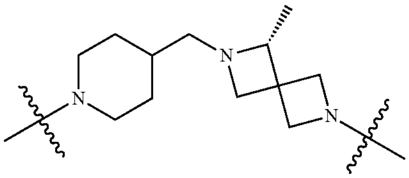
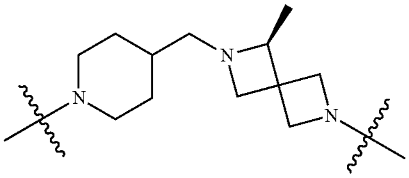
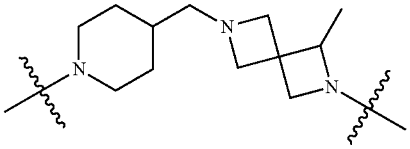
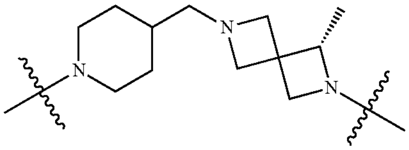
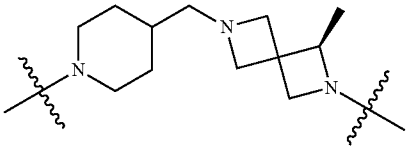
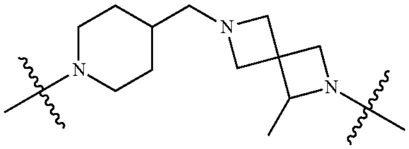
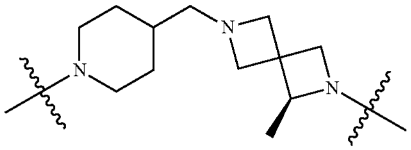
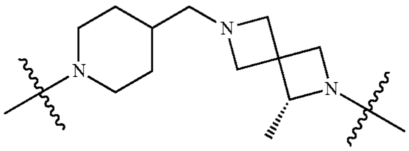
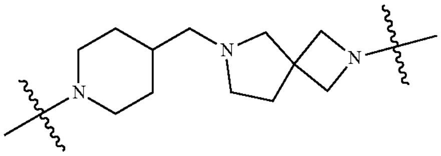
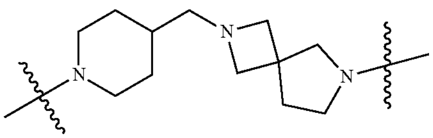
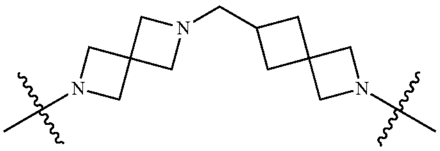
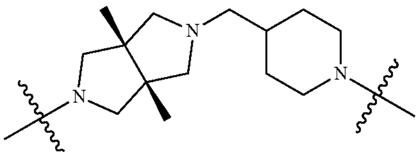
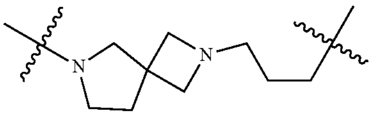
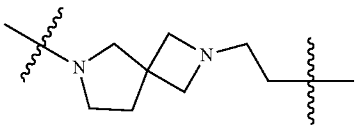
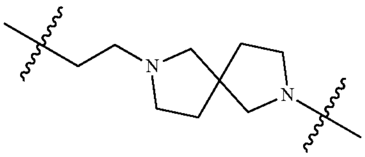
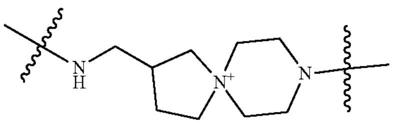
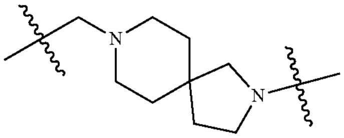
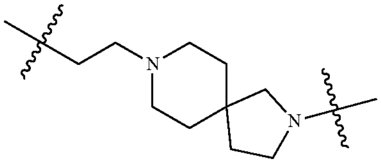
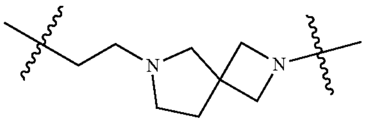
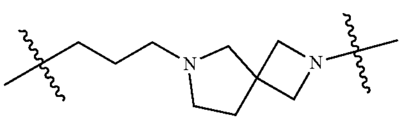
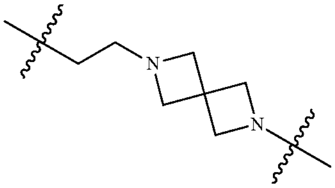
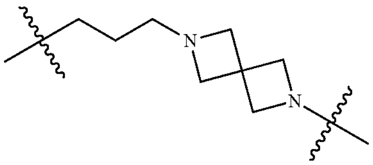

-continued
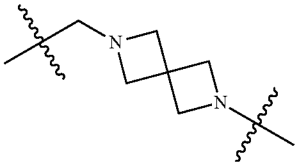 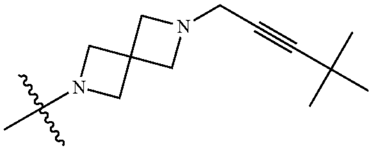 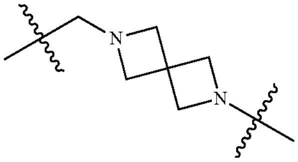
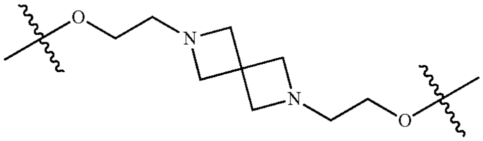 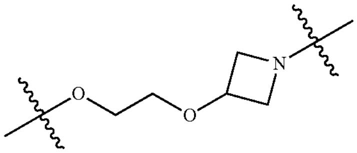
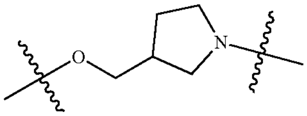 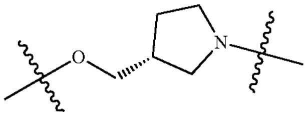 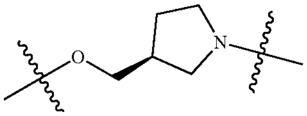
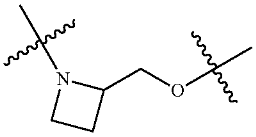 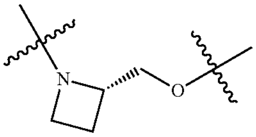 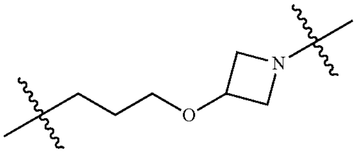
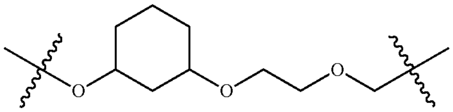 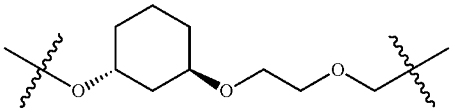
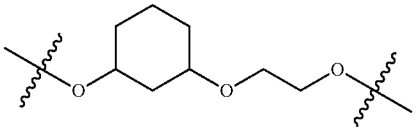 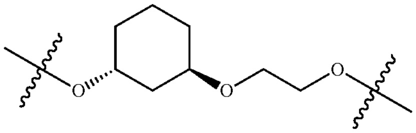 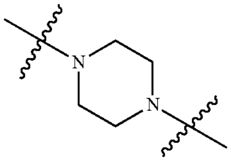
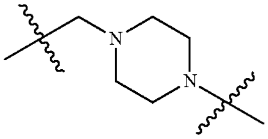 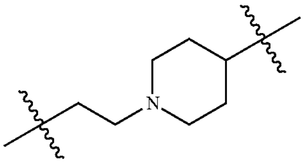 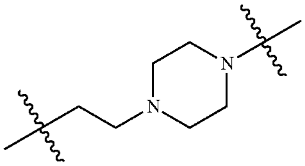
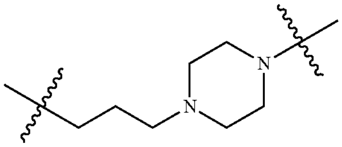 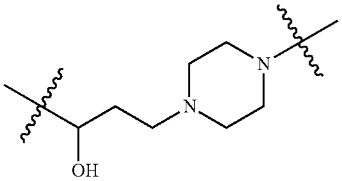 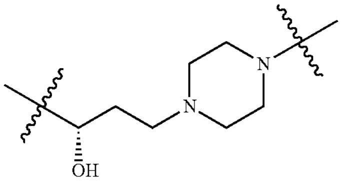
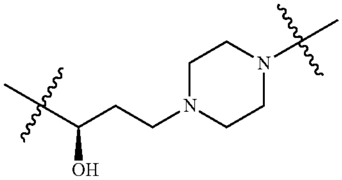 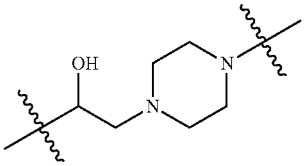 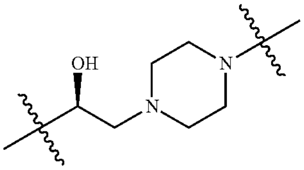
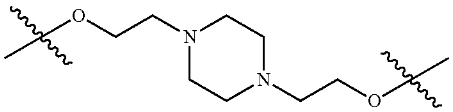 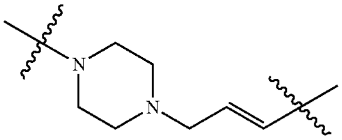
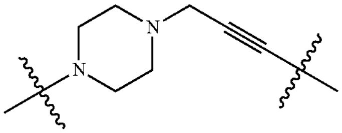 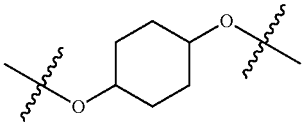 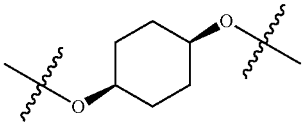

-continued
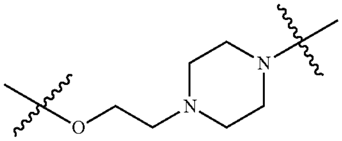
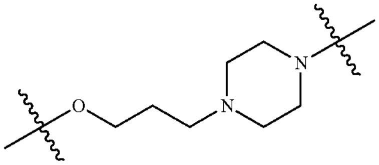
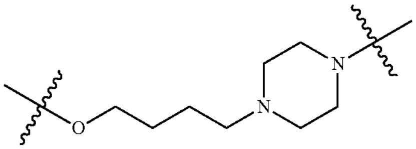
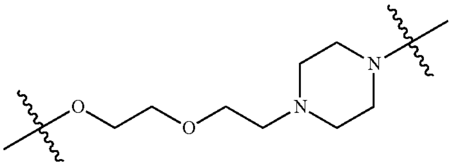
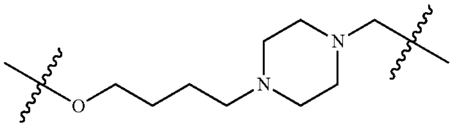
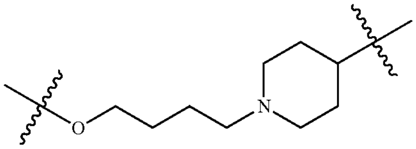
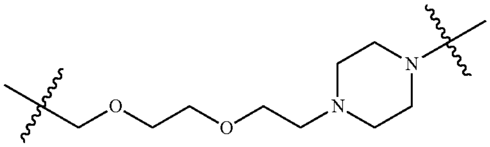
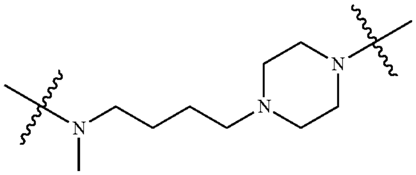
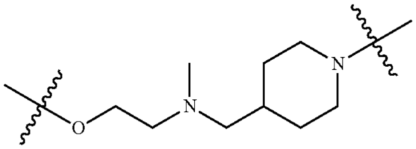
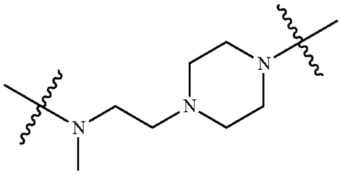
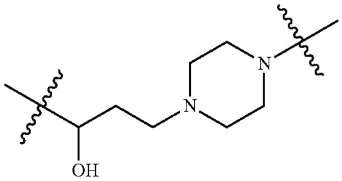
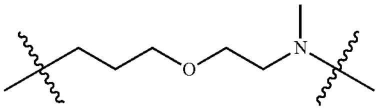
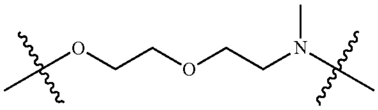
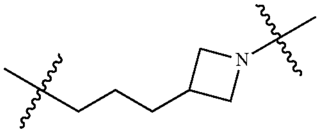
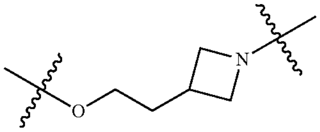
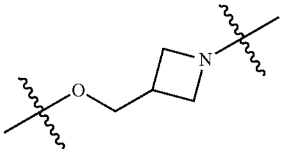
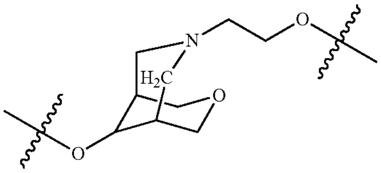
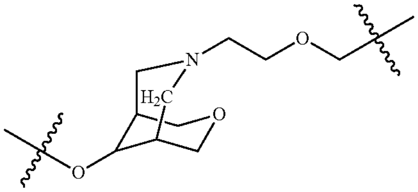
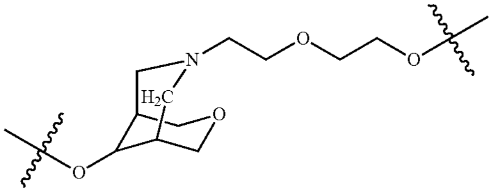
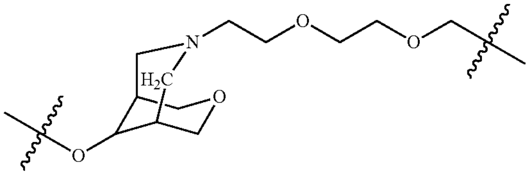
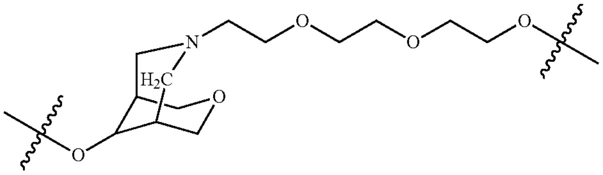
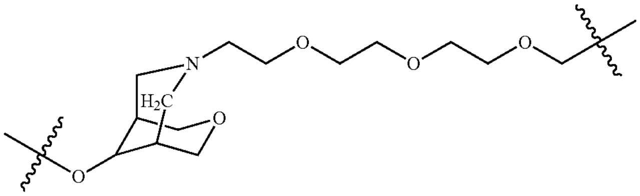

-continued
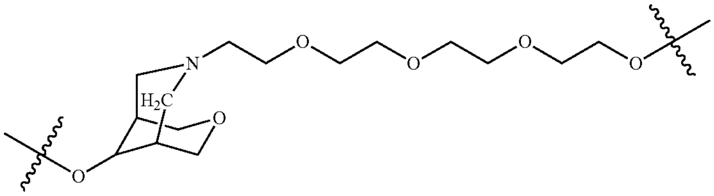
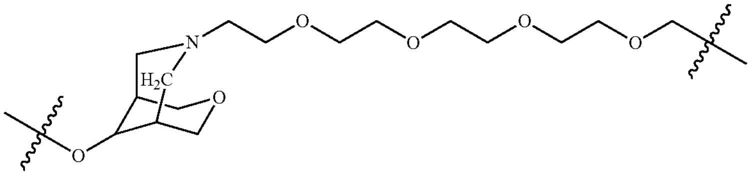
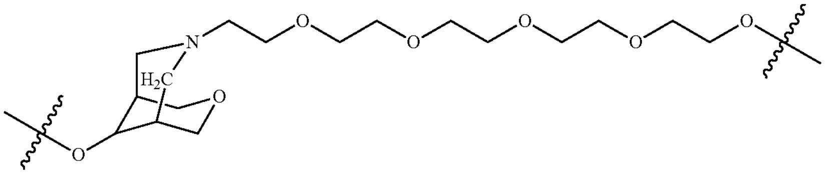
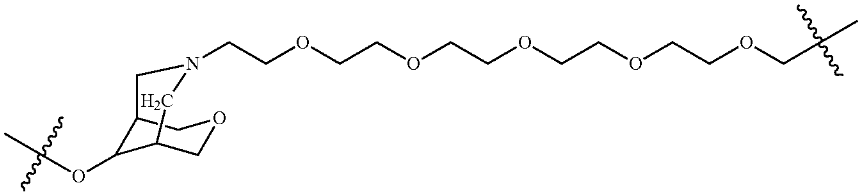
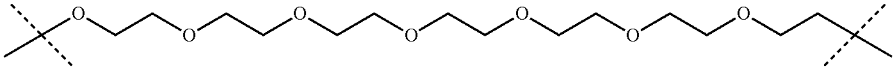
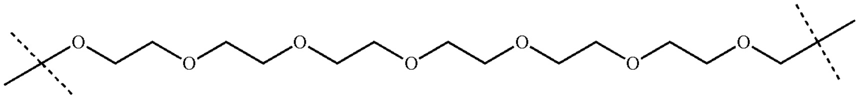
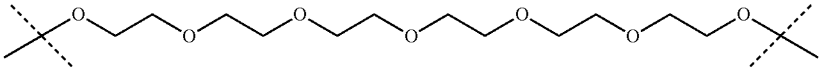
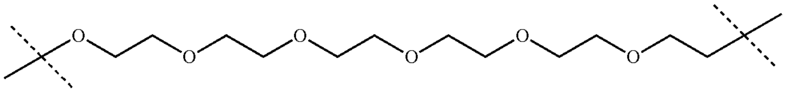
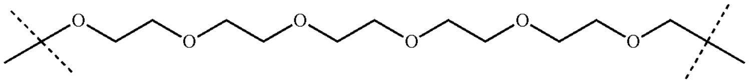
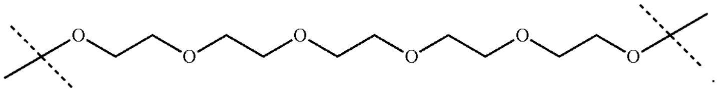
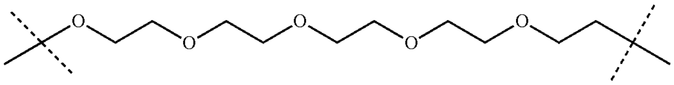
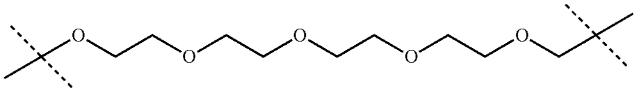
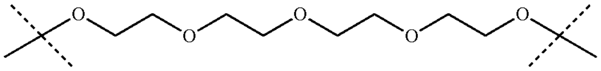
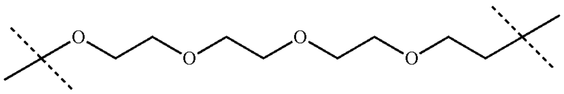
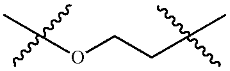
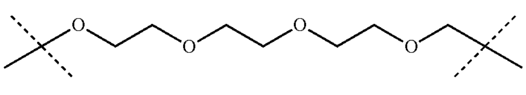
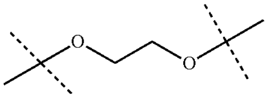

-continued
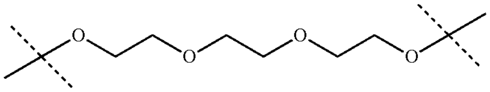
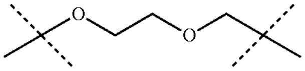
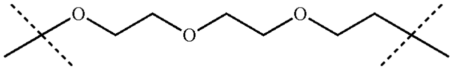
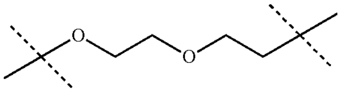
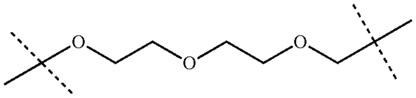
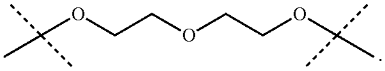
In any aspect or embodiment described herein, the linker (L) is selected from the group consisting of:
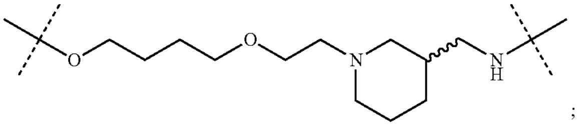
;
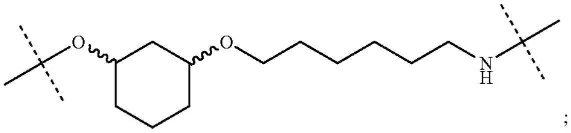
;
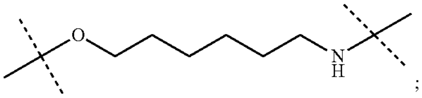
;
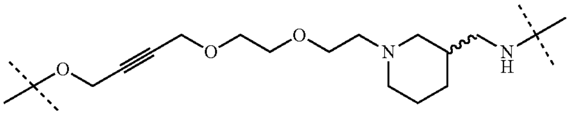
;
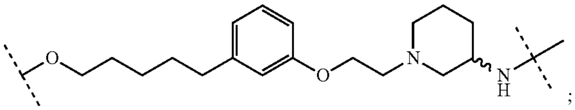
;
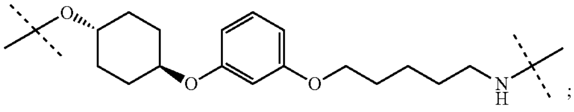
;
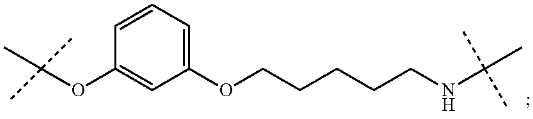
;
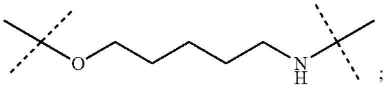
;
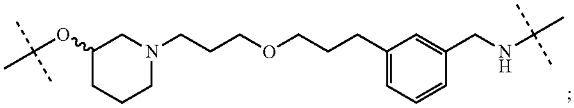
;
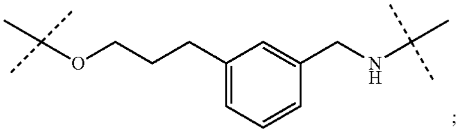
;
-continued
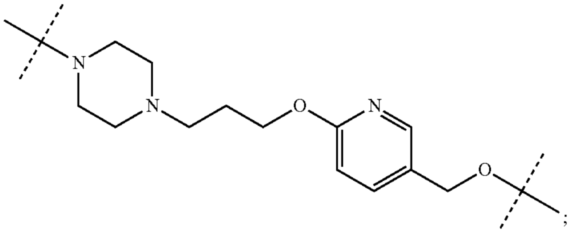
;
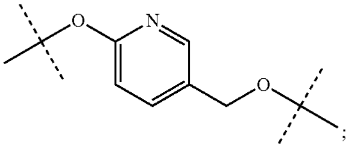
;
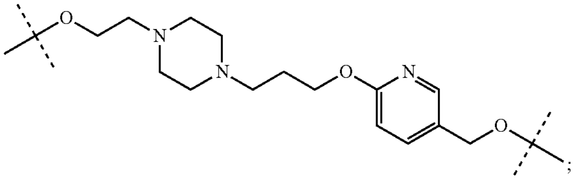
;
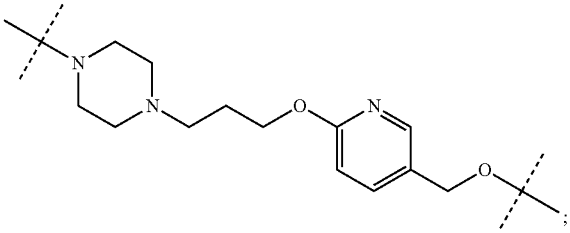
;
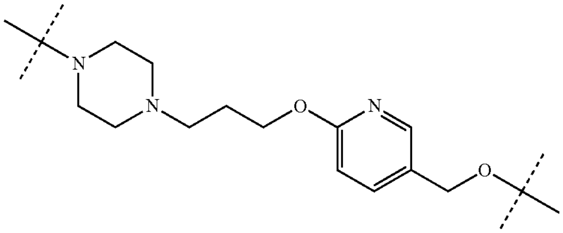
;
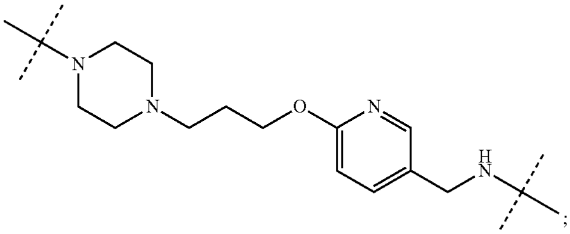
;

-continued
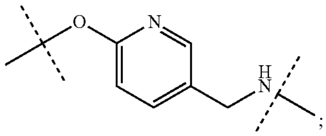
;
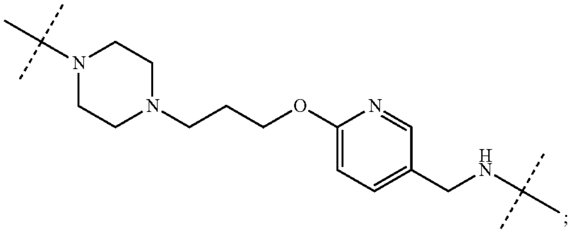
;
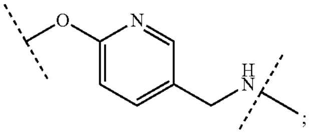
;
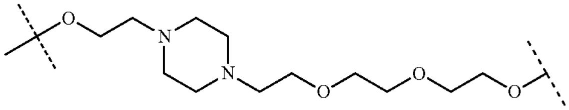
;
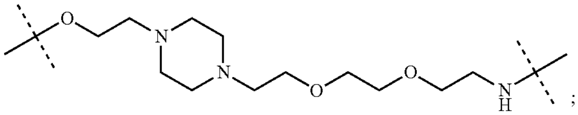
;
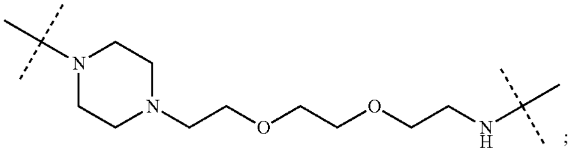
;
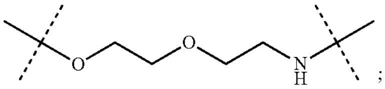
;
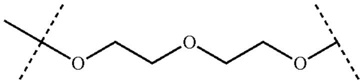
;
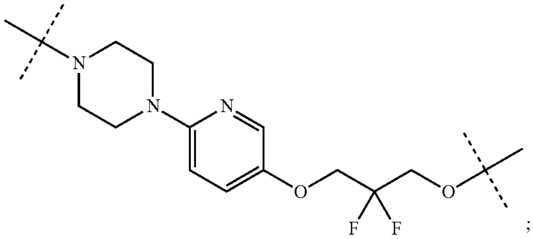
;
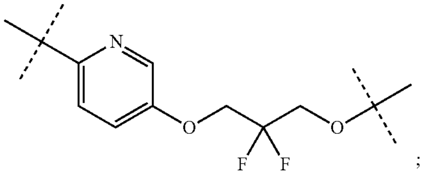
;
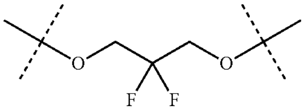
;
-continued
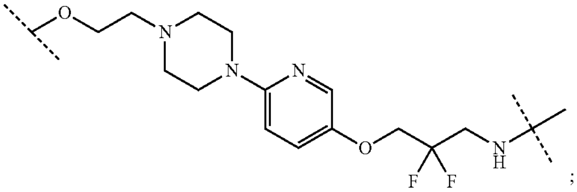
;
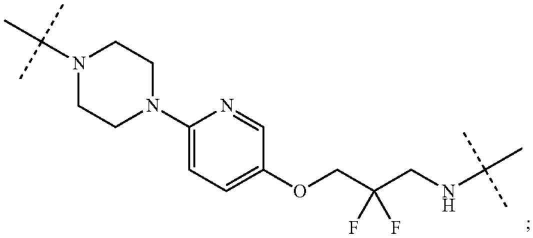
;
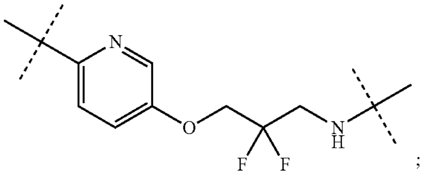
;
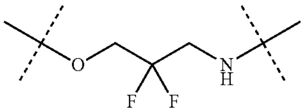
;
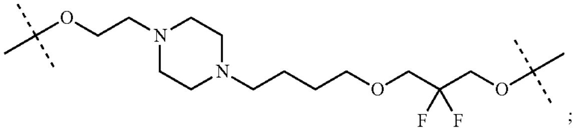
;
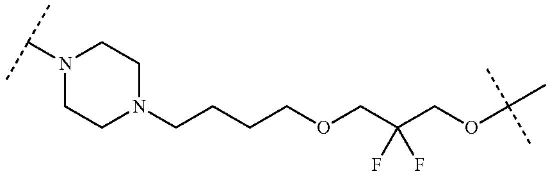
;
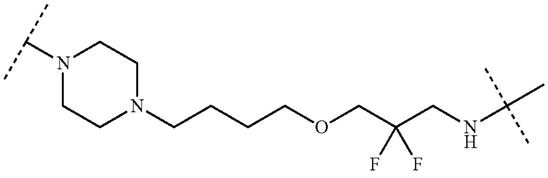
;
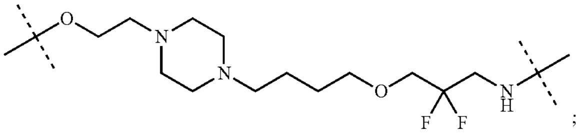
;
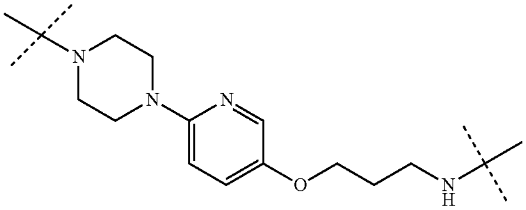
;
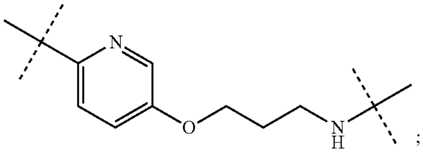
;

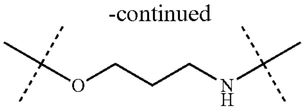
;
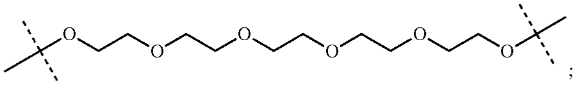
;
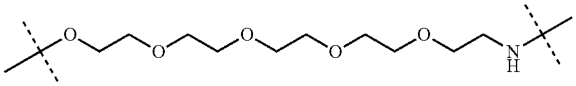
;
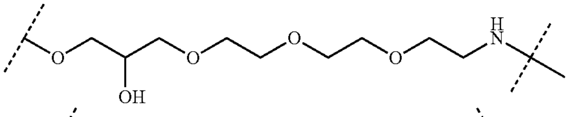
;
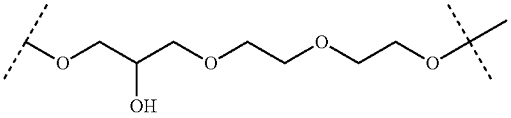
;
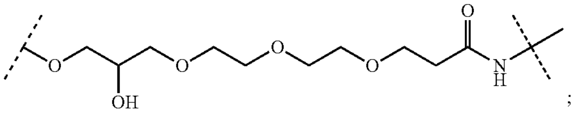
;
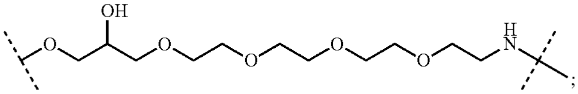
;
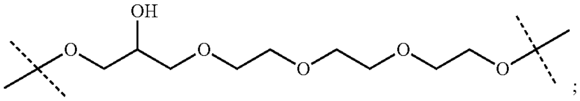
;
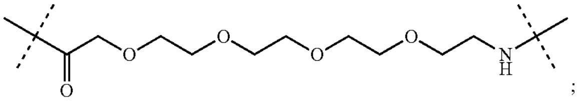
;
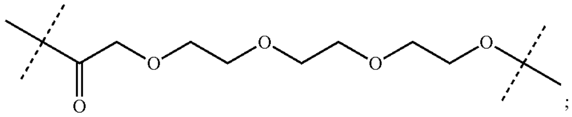
;
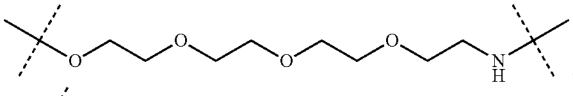
;
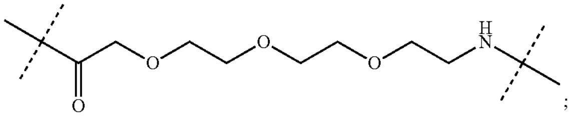
;
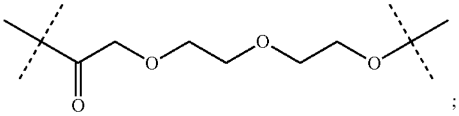
;
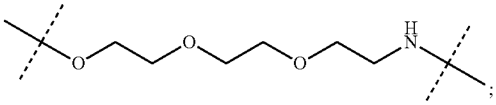
;
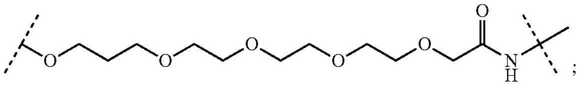
;
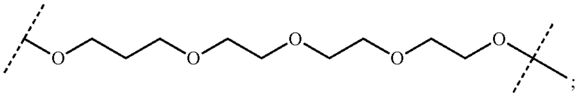
;
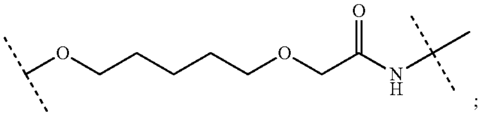
;
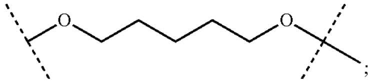
;
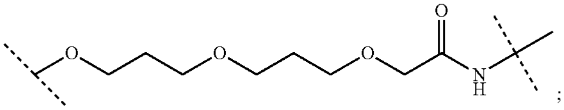
;
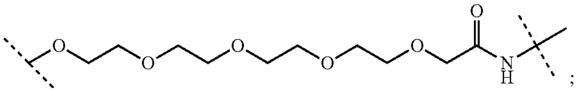
;
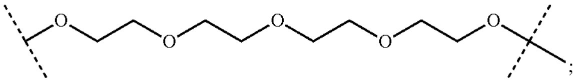
;
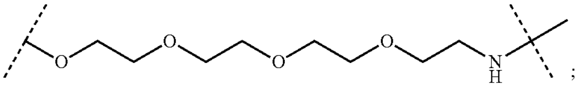
;
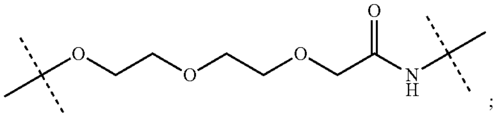
;
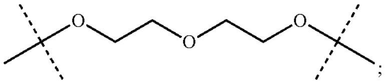
;
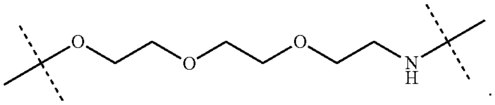
.
In any aspect or embodiment described herein, the linker (L) is selected from the group consisting of:
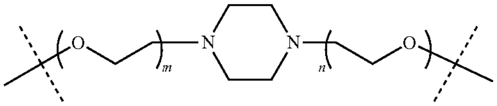
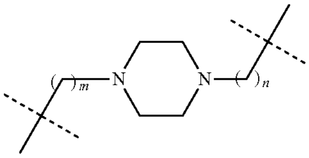
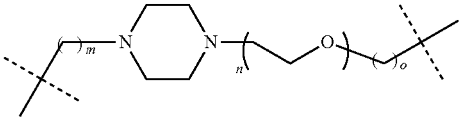
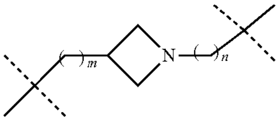

-continued
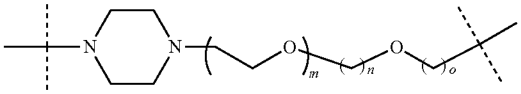
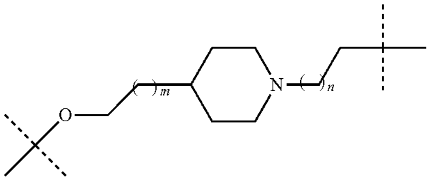
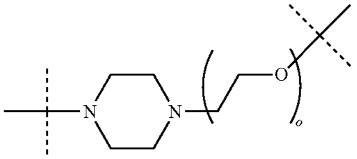
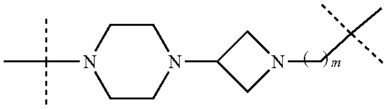
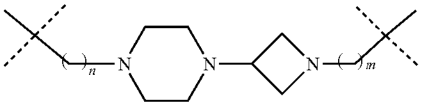
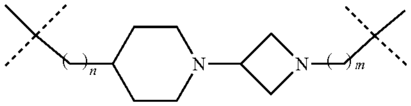
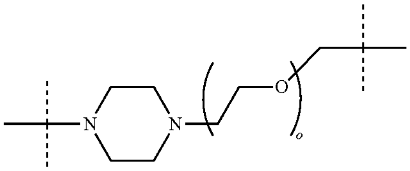
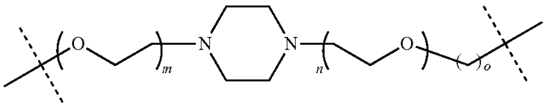
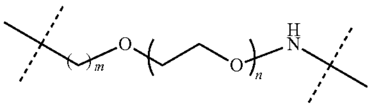
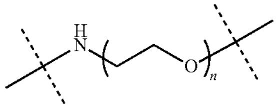
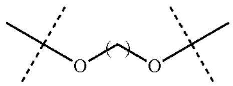
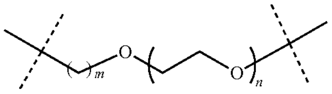
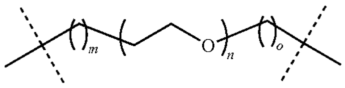
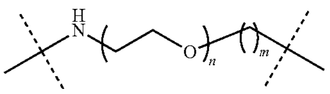
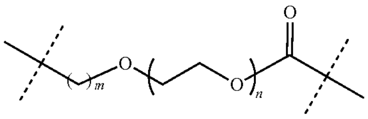
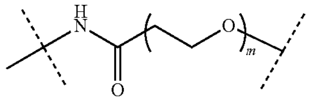
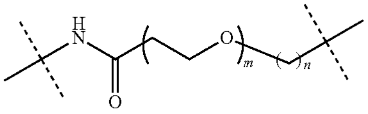
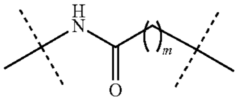
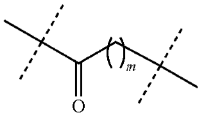
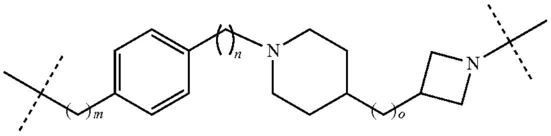
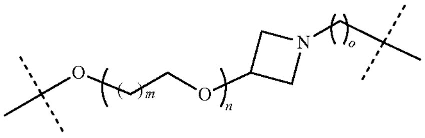
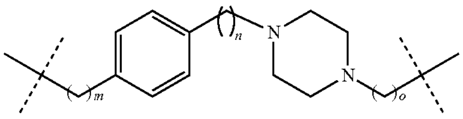
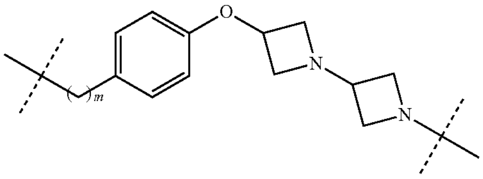
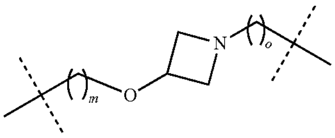
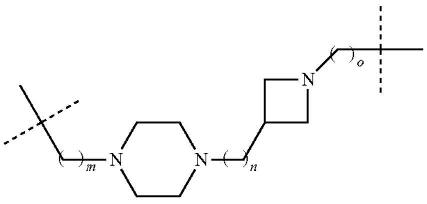
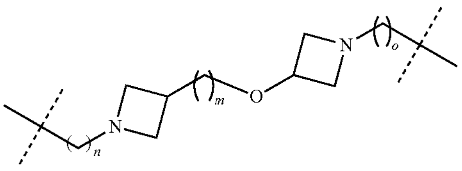

-continued
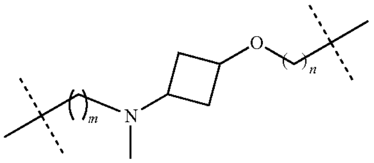
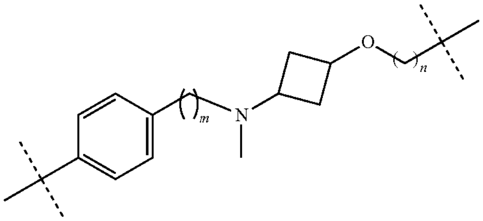
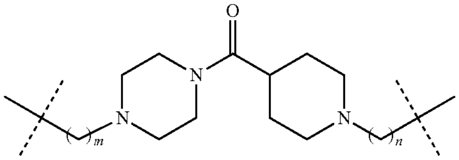
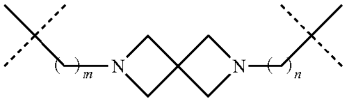
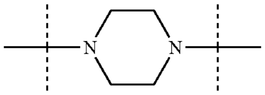
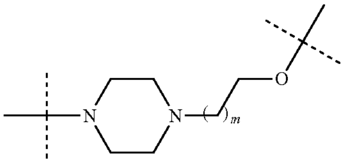
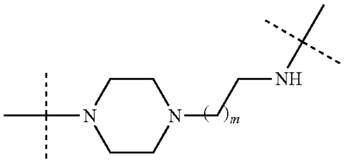
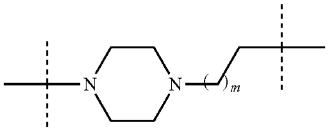
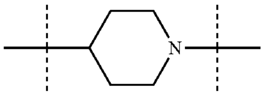
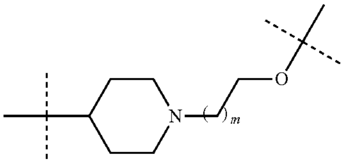
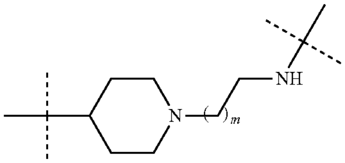
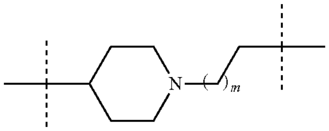
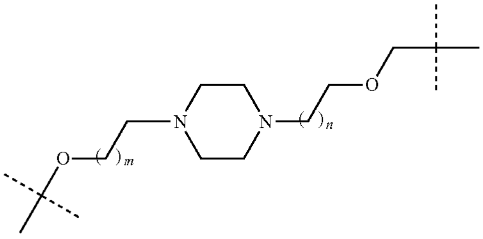
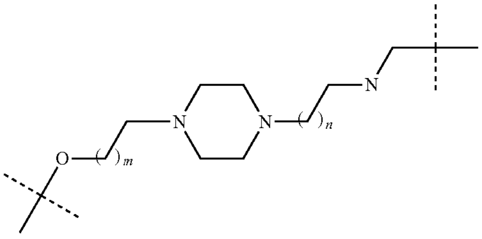
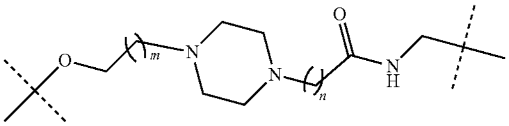
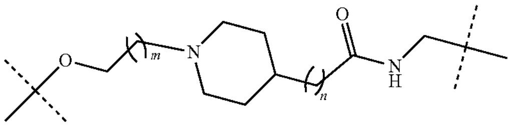
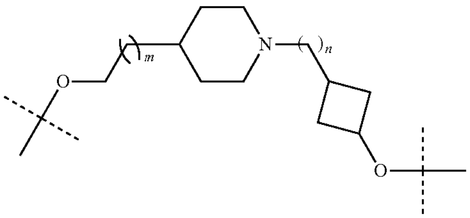
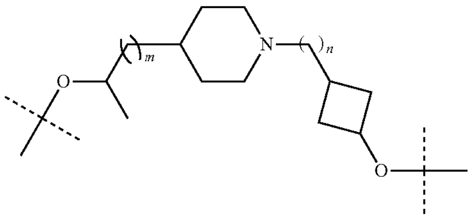
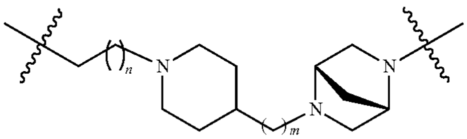
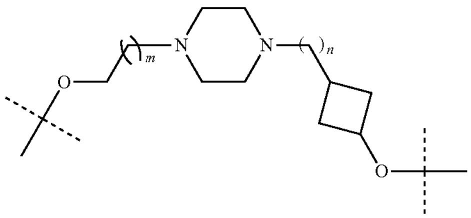

-continued
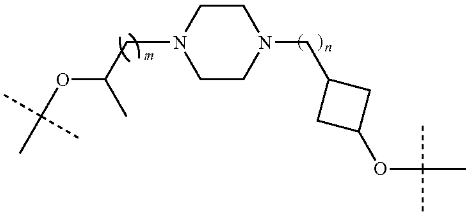
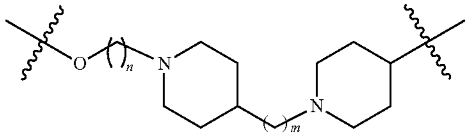
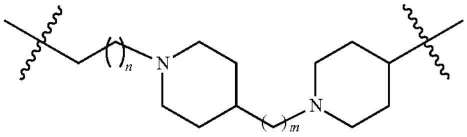
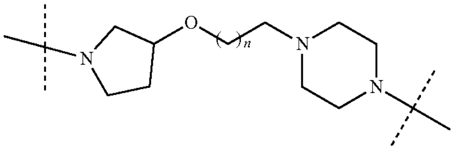
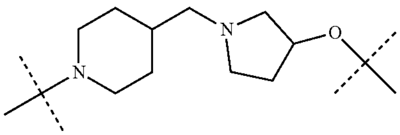
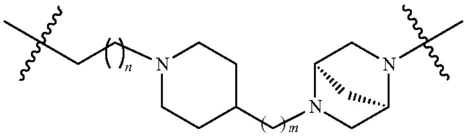
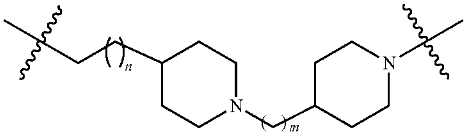
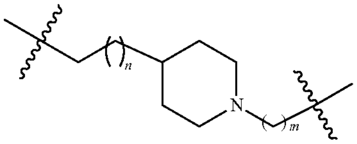
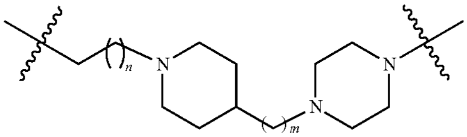
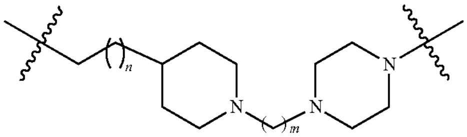
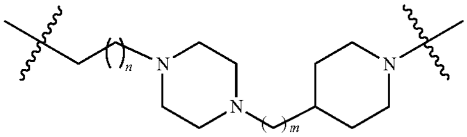
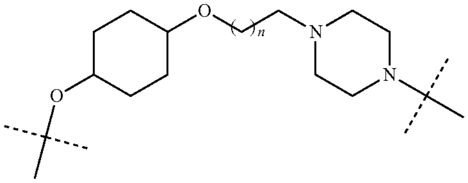
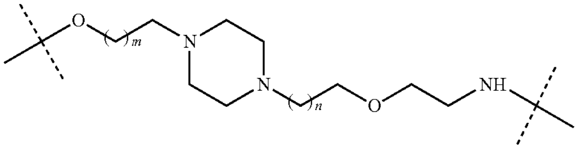
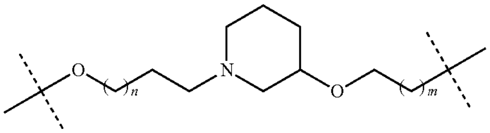
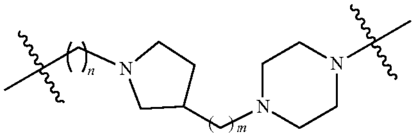
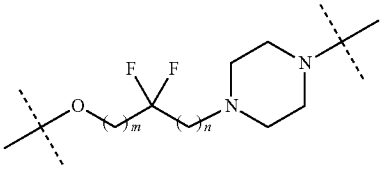
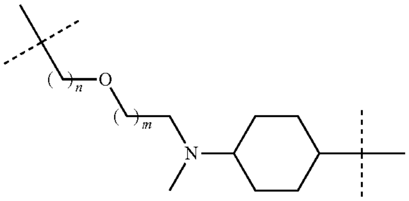
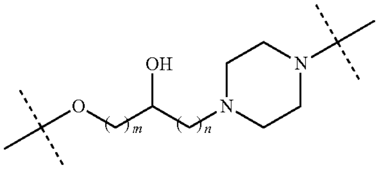
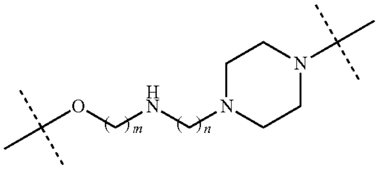
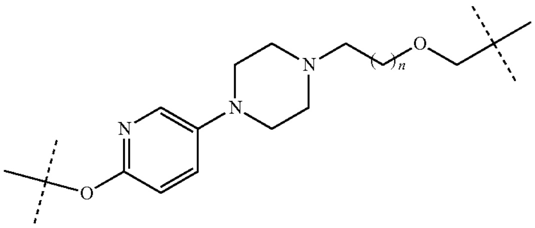
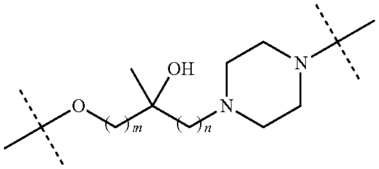

-continued
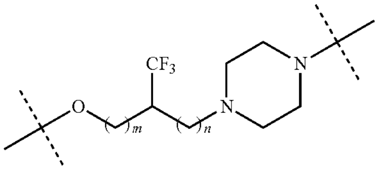
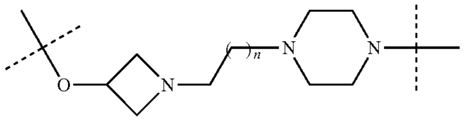
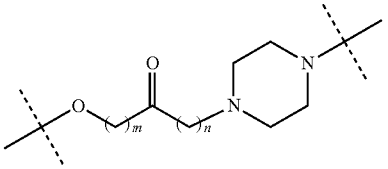
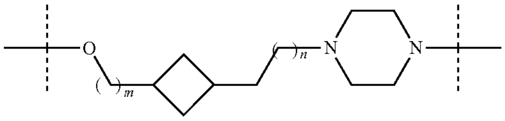
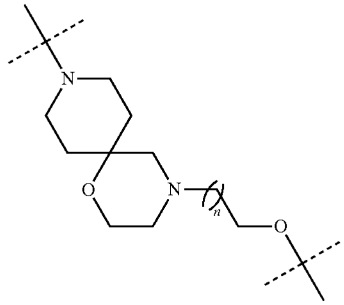
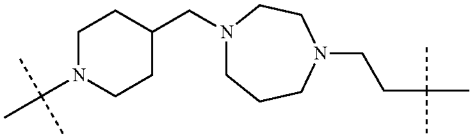
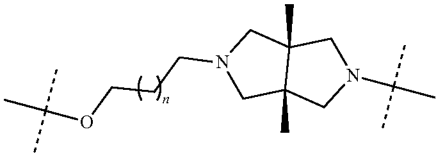
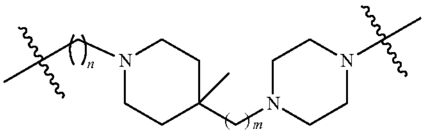
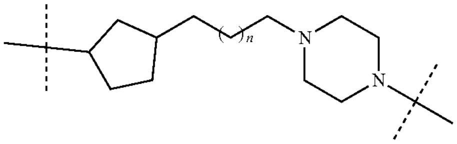
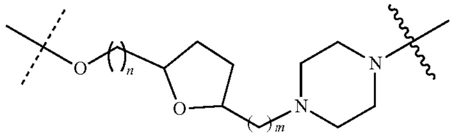
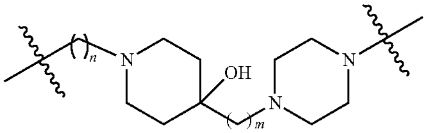
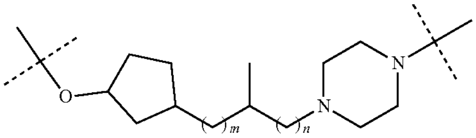
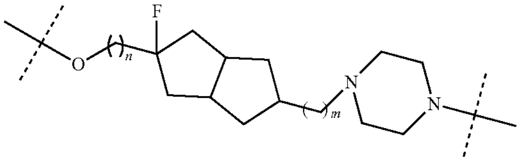
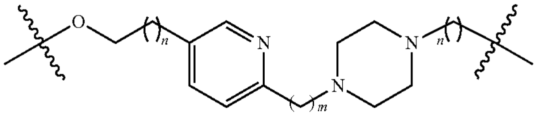
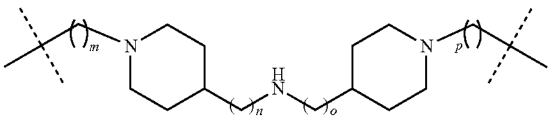
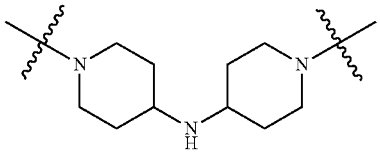
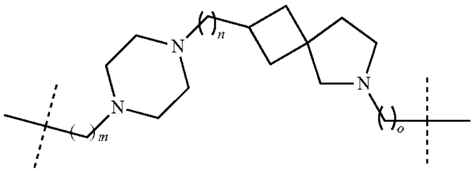
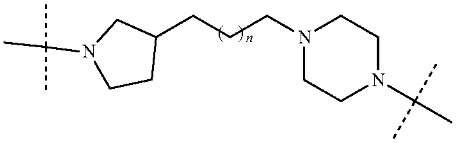
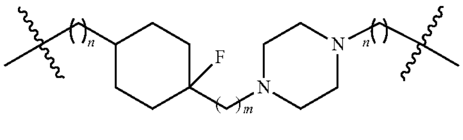
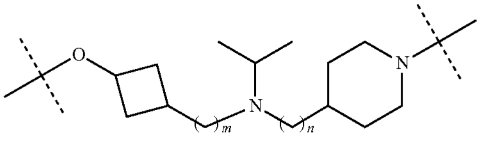

-continued
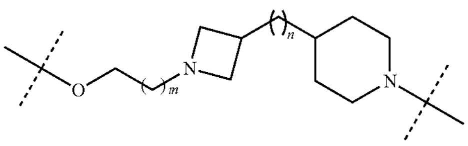
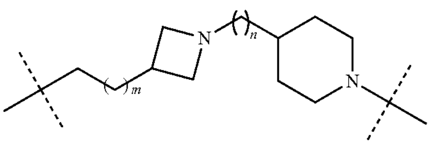
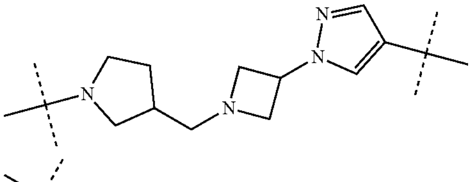
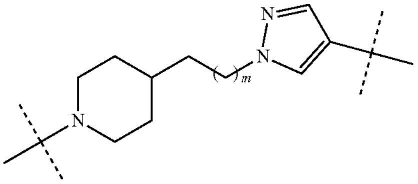
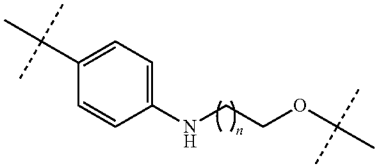
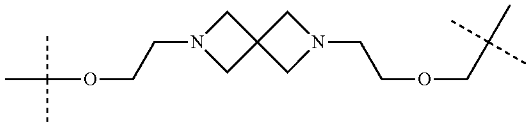
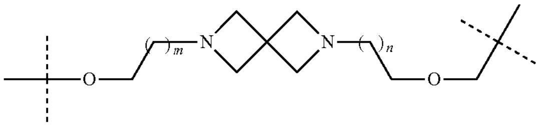
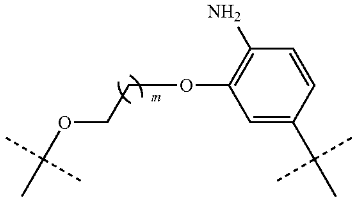
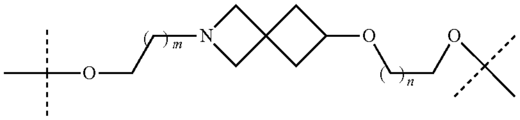
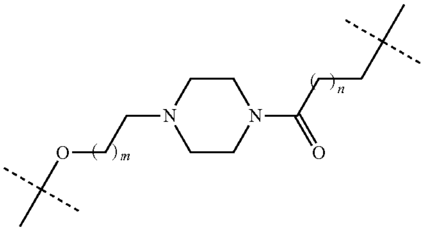
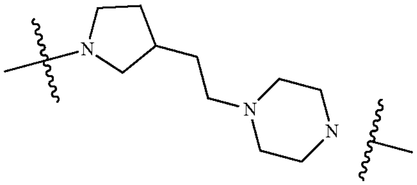
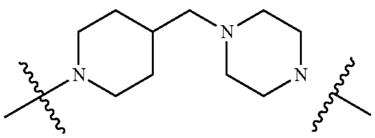
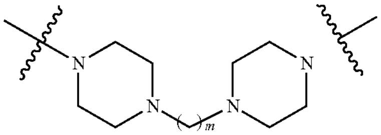
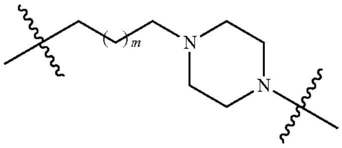
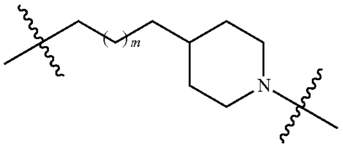
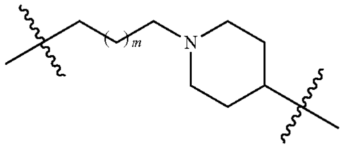
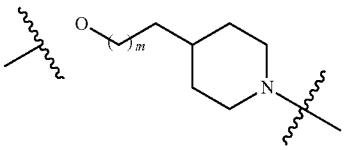
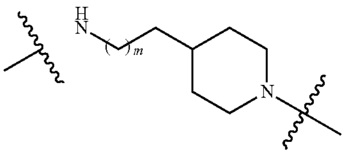
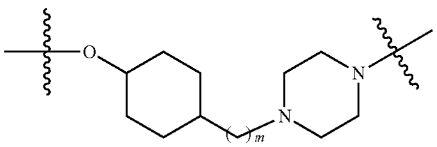
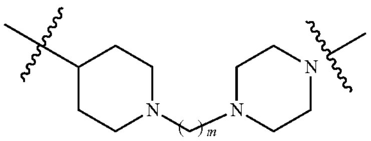
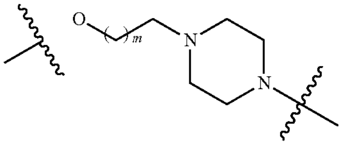
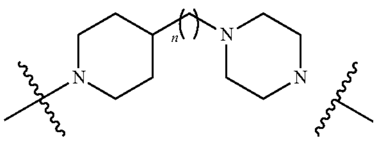

-continued
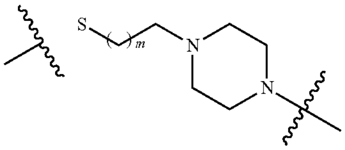
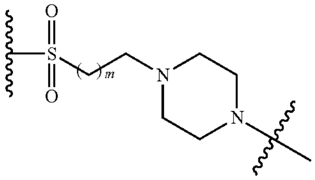
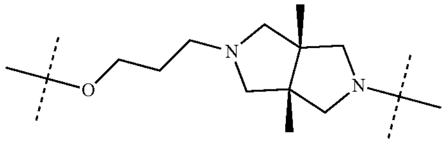
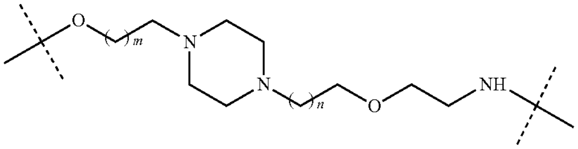
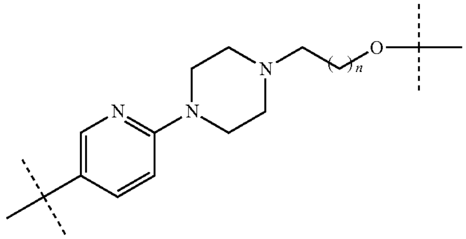
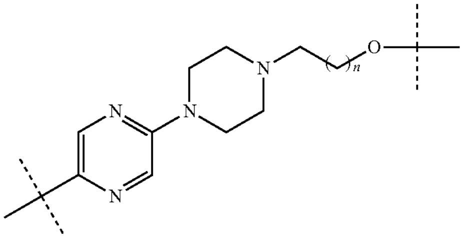
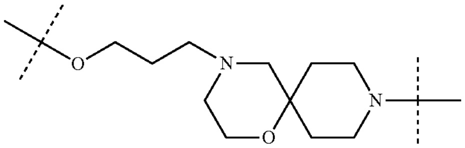
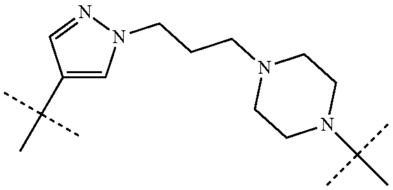
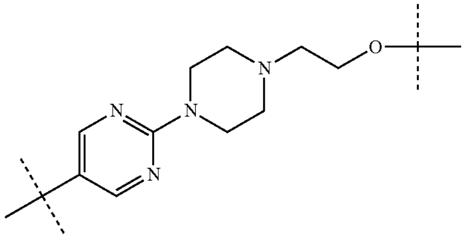
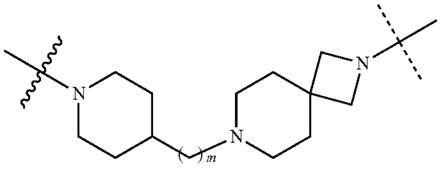
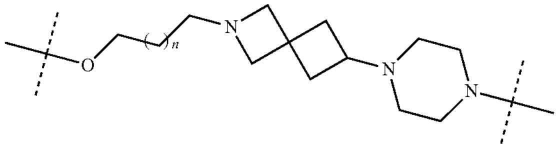
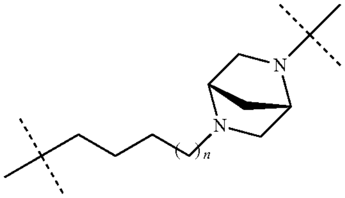
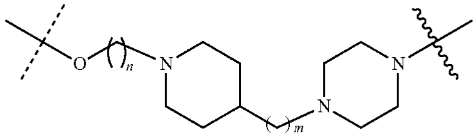
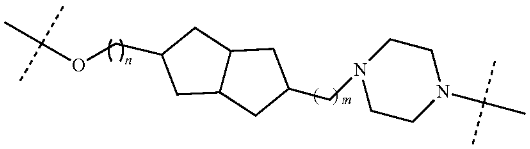
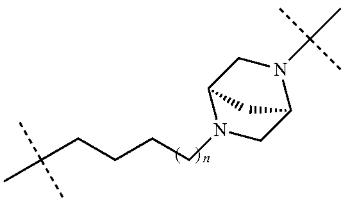
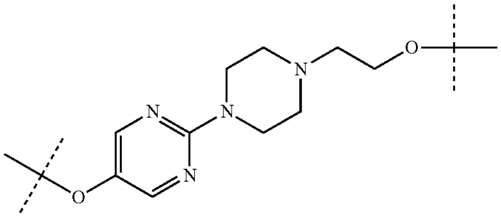
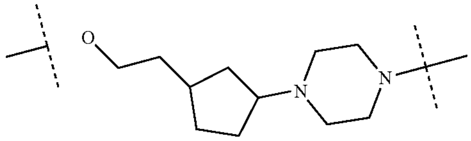

-continued
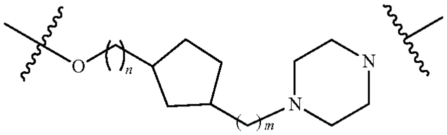
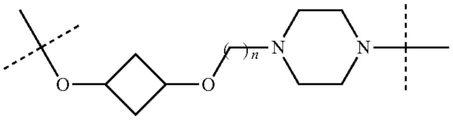
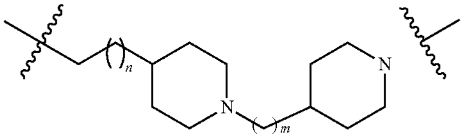
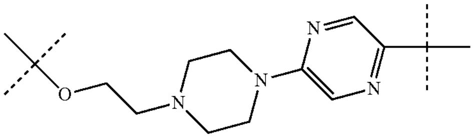
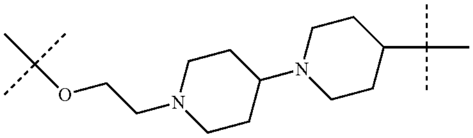
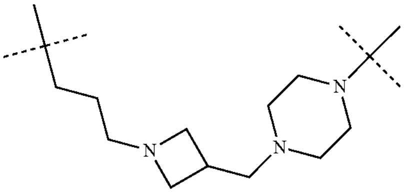
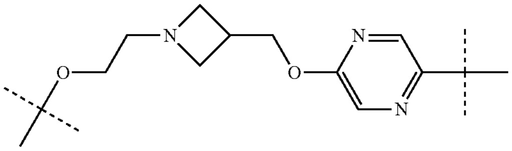
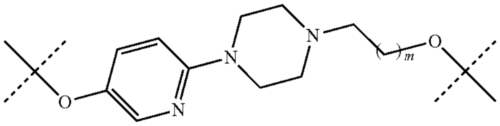
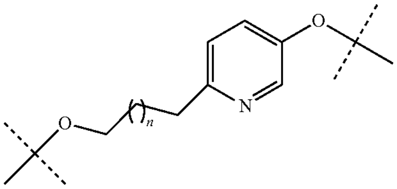
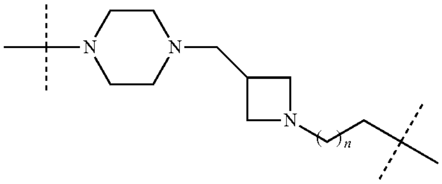
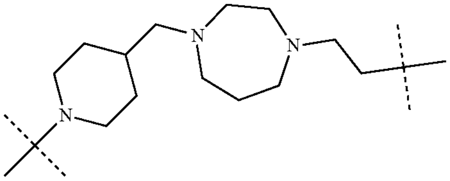
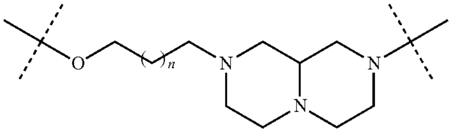
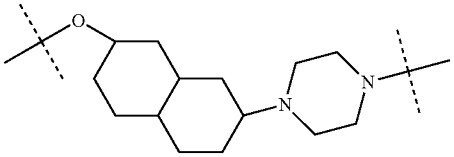
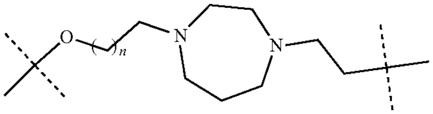
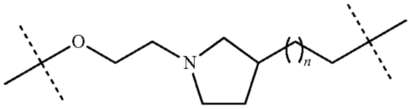
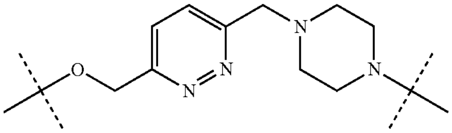
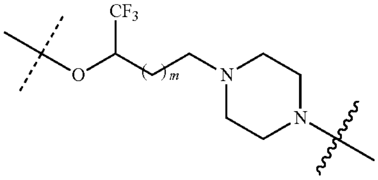
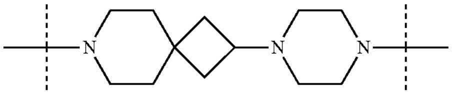
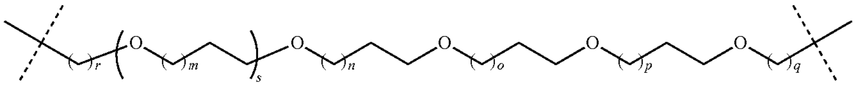
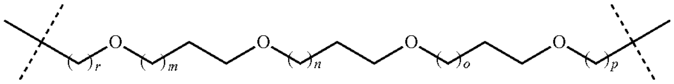
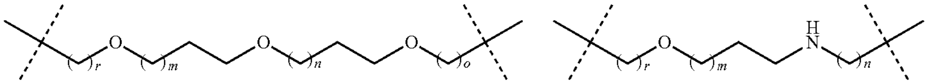

-continued
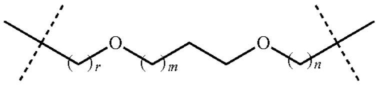
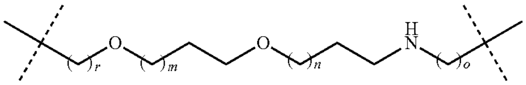
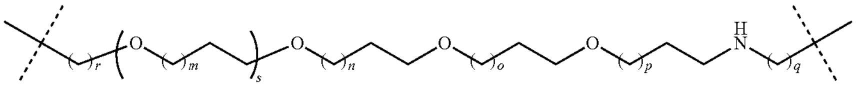
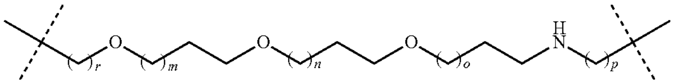
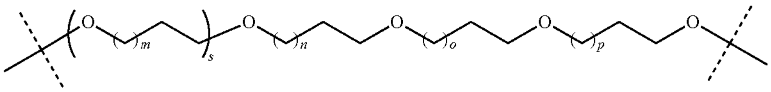
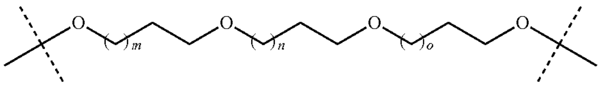
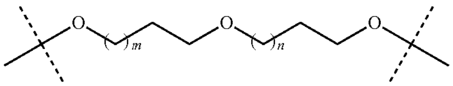
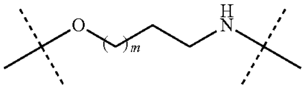
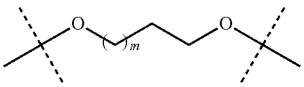
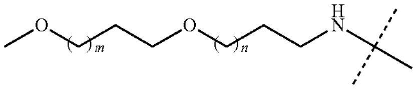
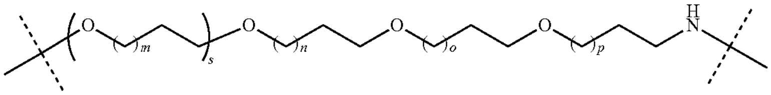
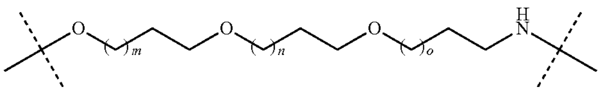
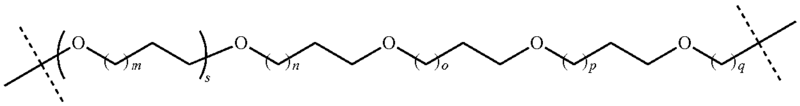
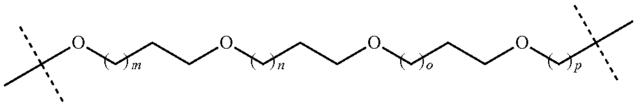
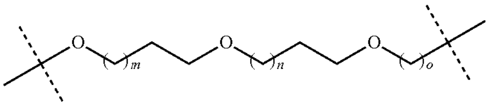
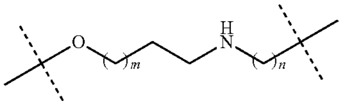
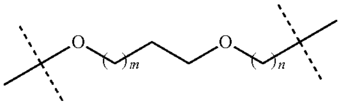
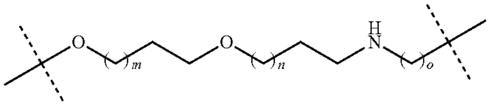
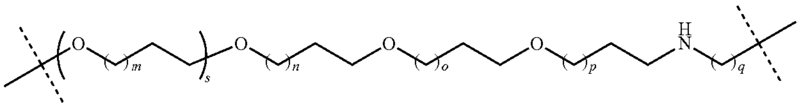
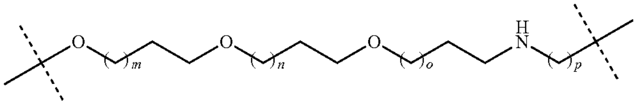
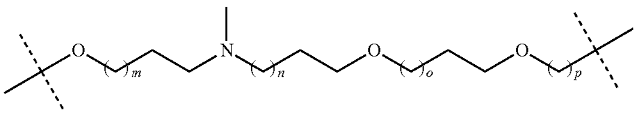
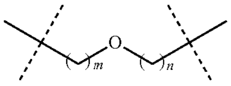
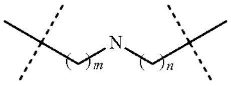
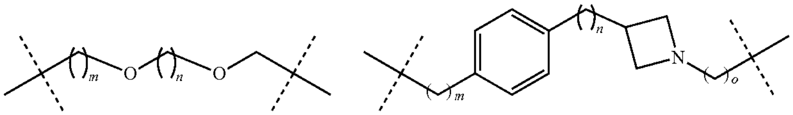

-continued
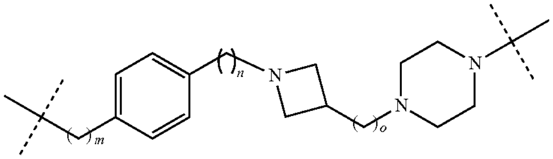
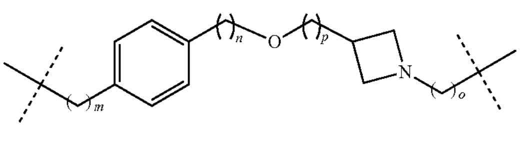
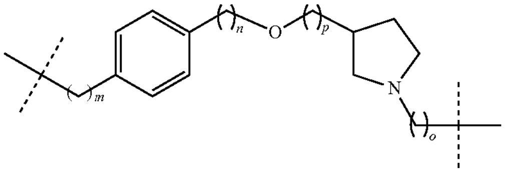
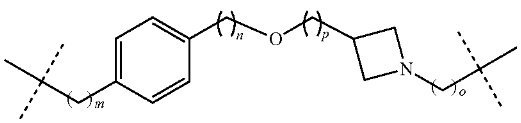
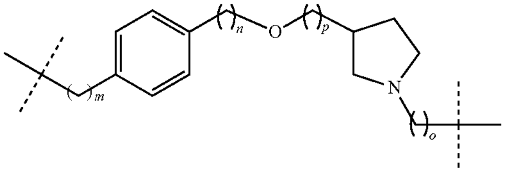
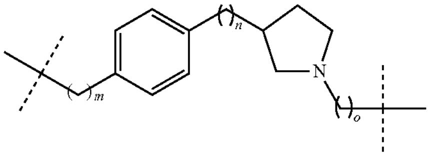
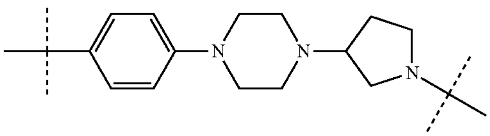
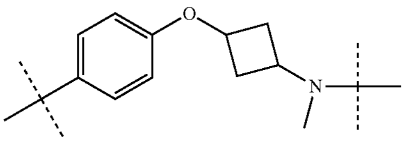
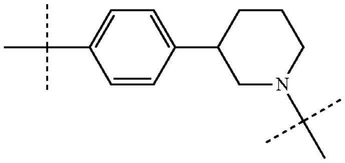
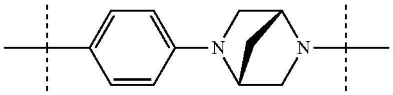
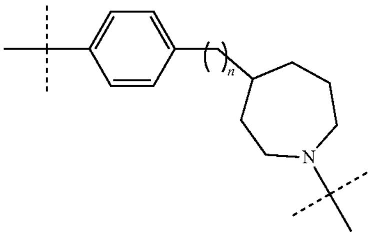
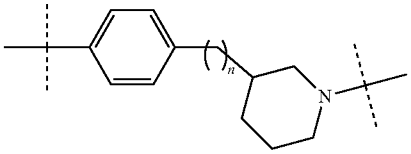
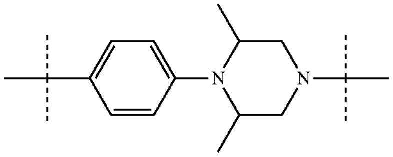
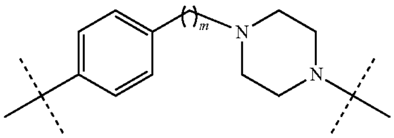
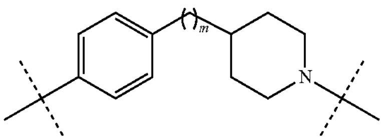
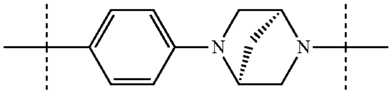
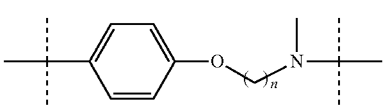
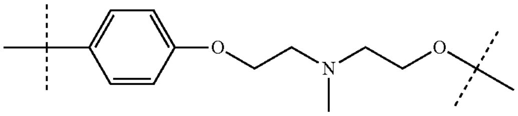
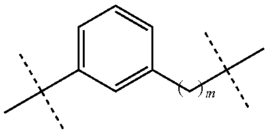
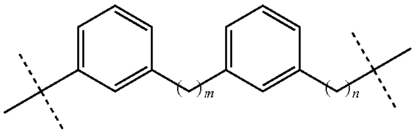
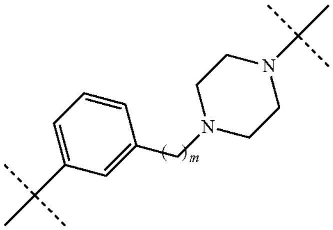

-continued
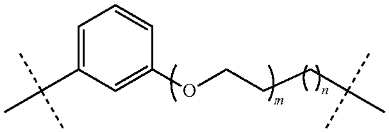
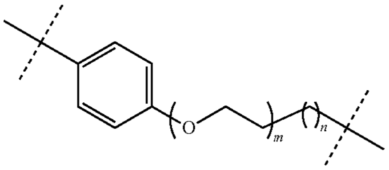
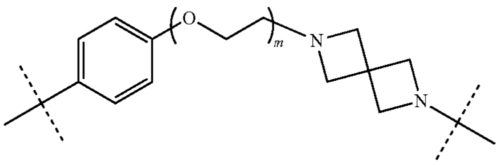
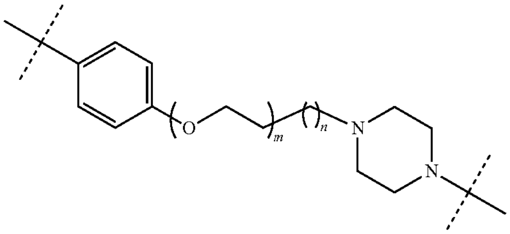
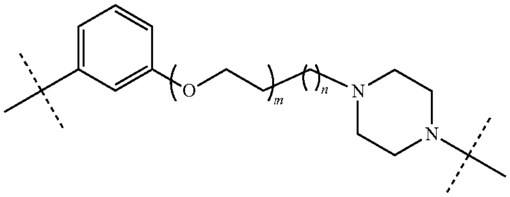
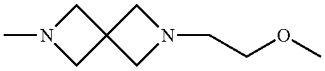
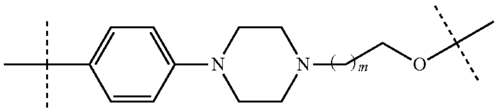
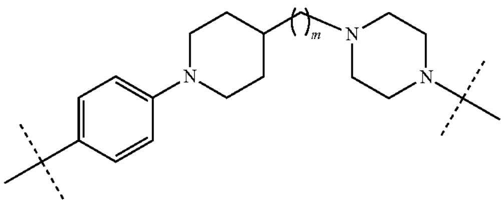
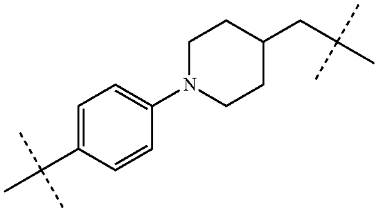
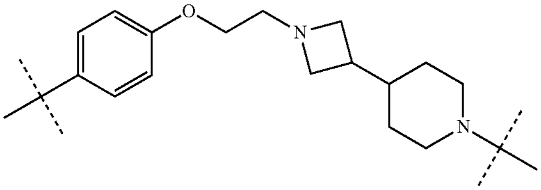
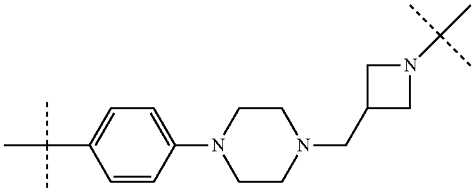
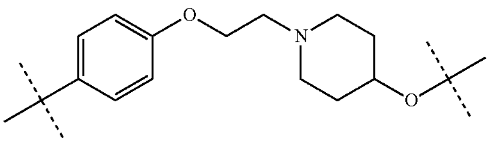
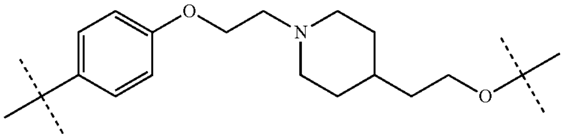
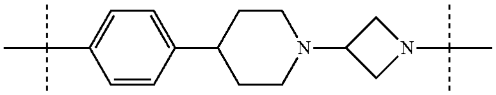
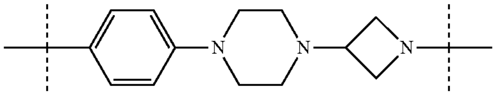
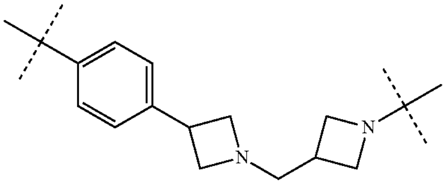

-continued
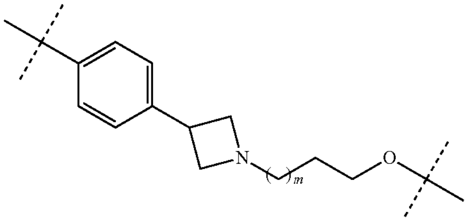
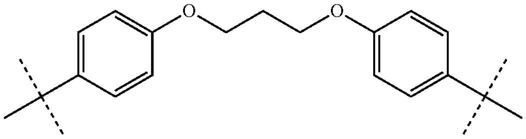
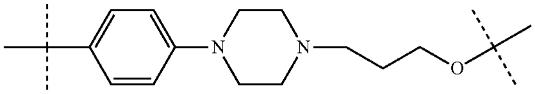
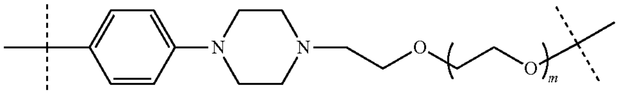
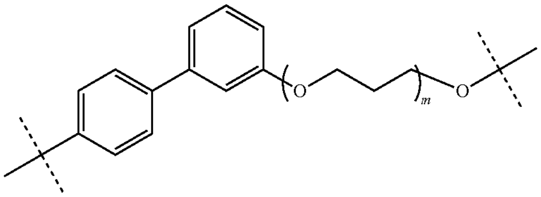
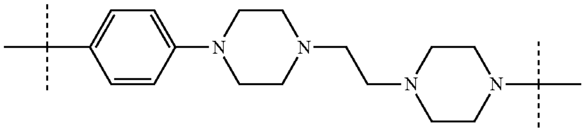
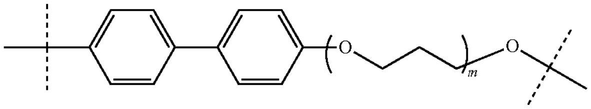
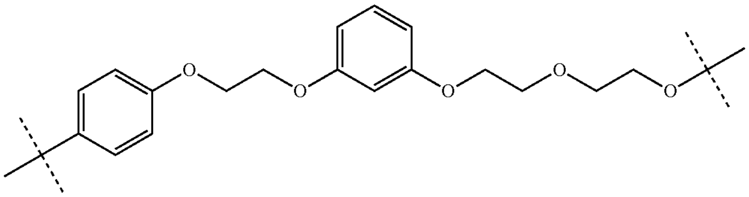
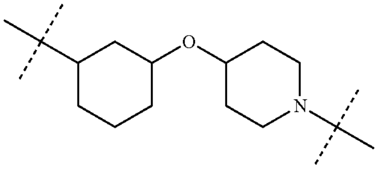
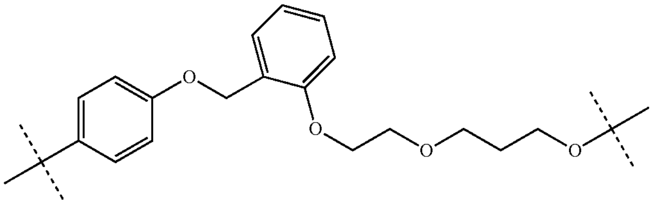
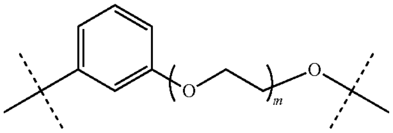
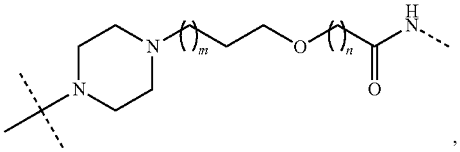
,
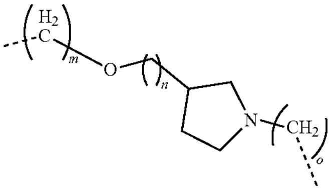
,
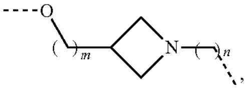
,
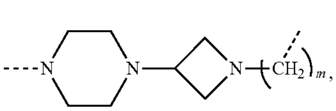
,
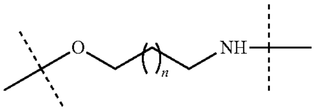
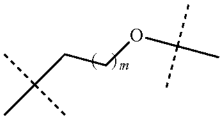
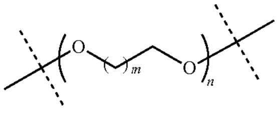
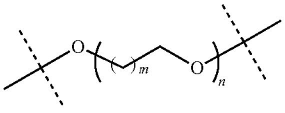
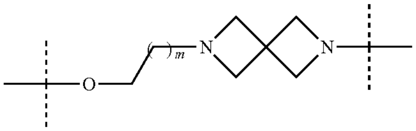
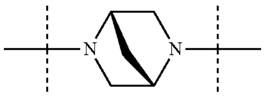
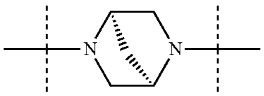
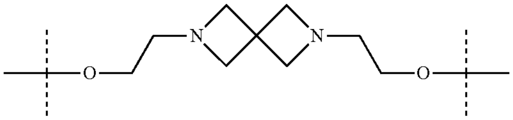

-continued
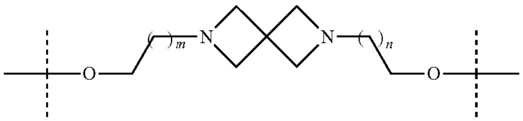
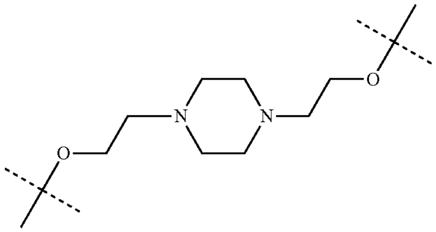
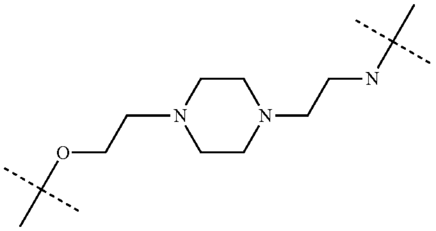
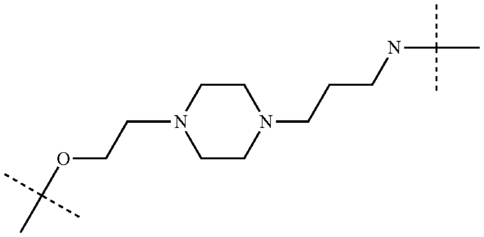
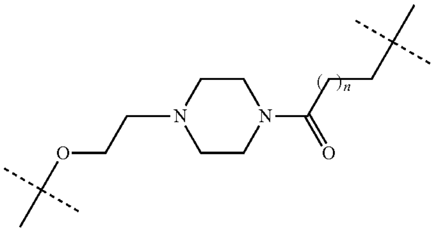
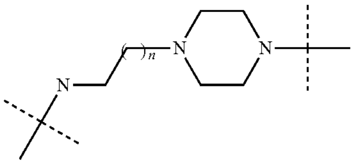
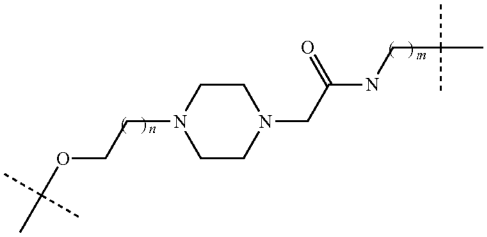
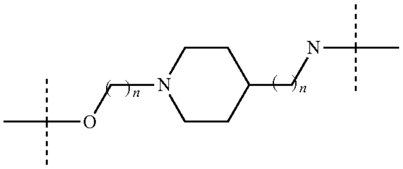
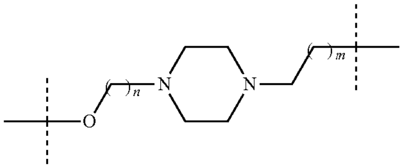
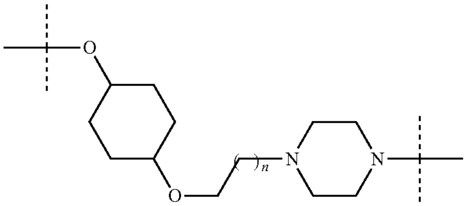
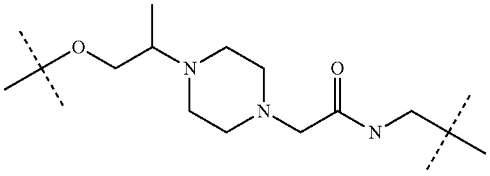
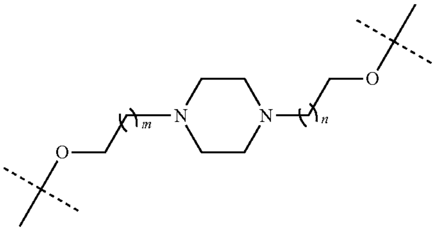
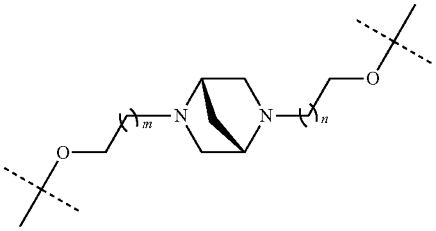
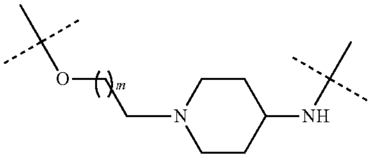

-continued
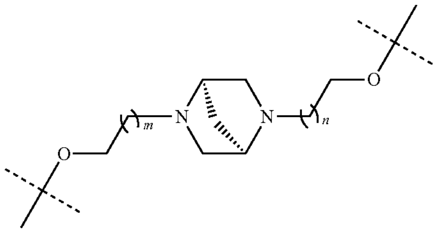
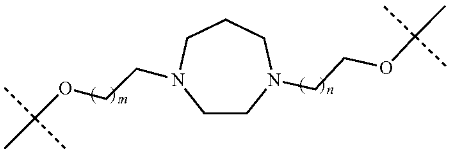
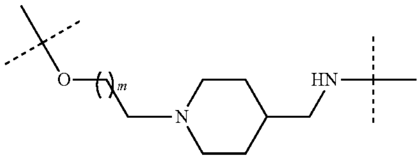
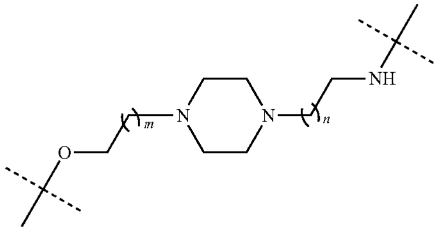
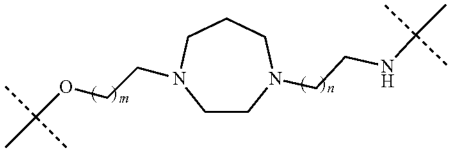
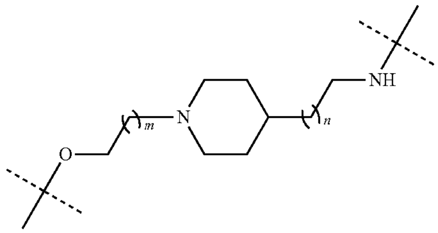
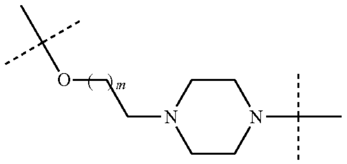
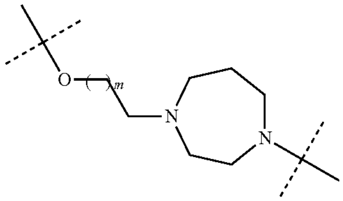
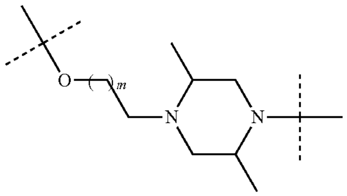
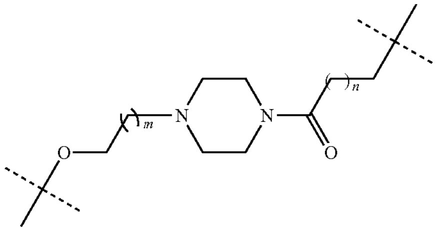
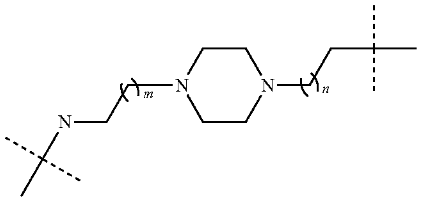
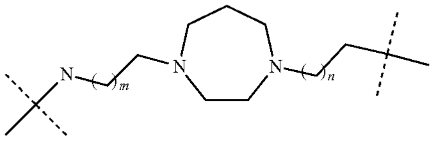
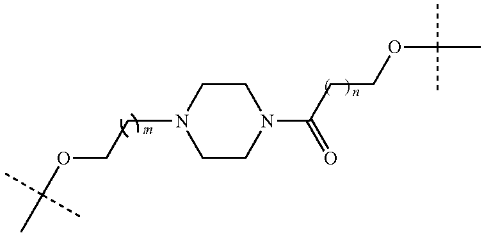
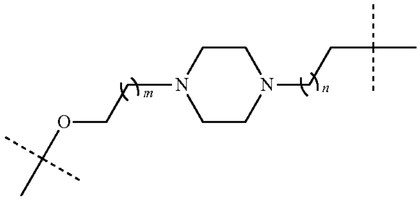
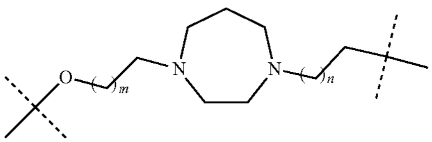

-continued
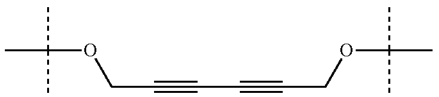
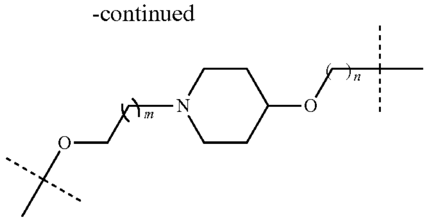
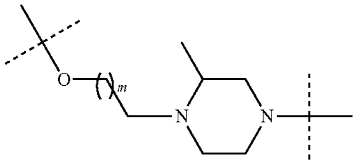
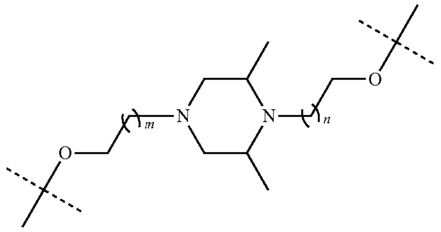
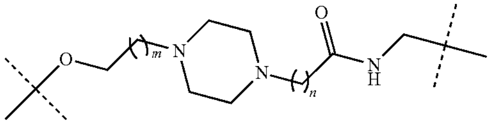
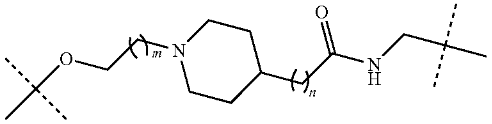
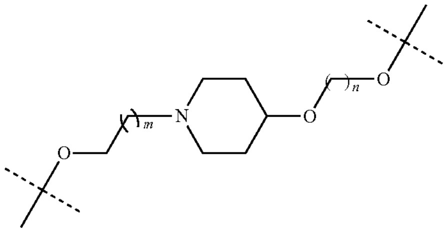
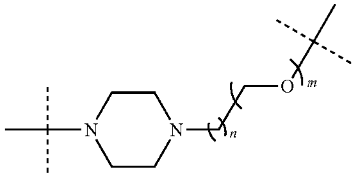
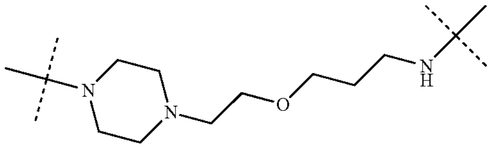
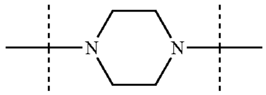
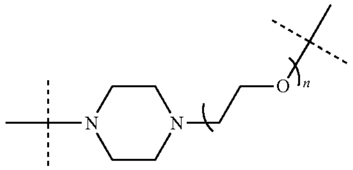
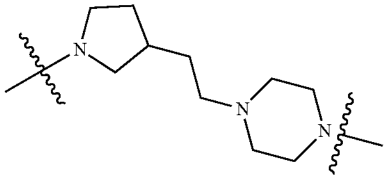
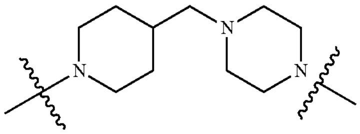
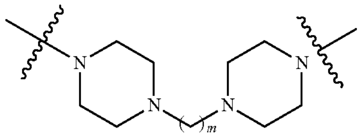
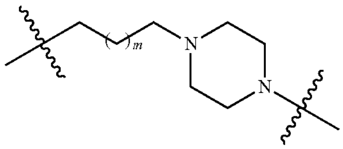
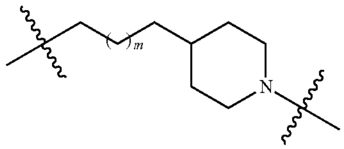
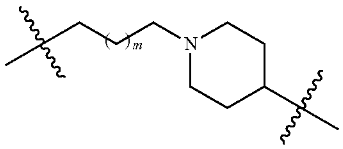
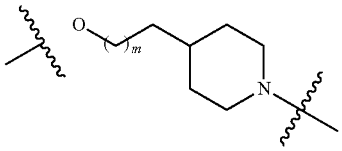
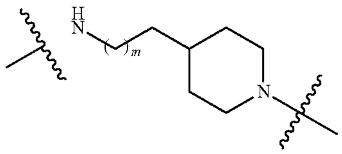
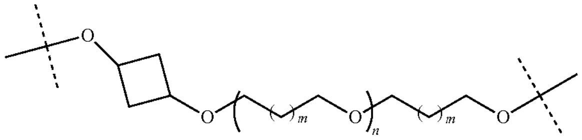
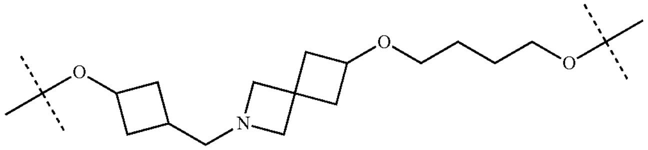

-continued
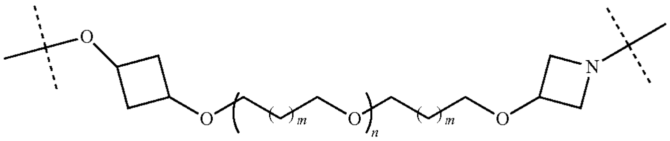
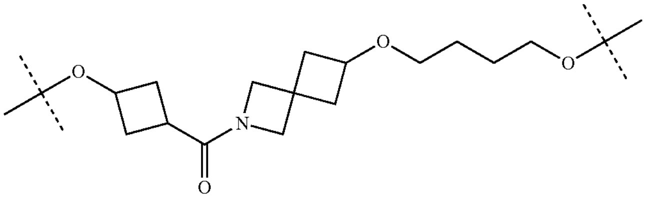
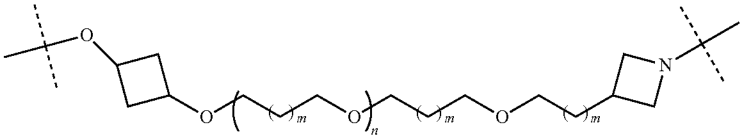
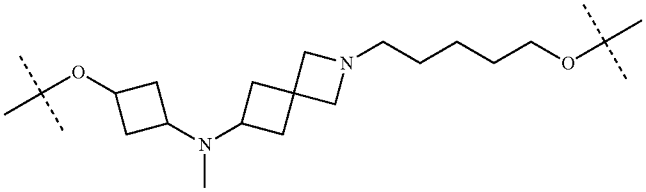
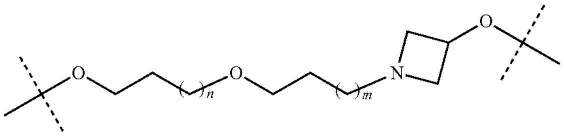
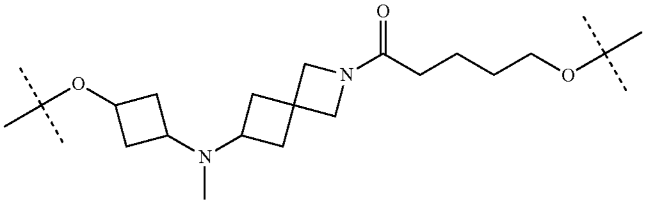
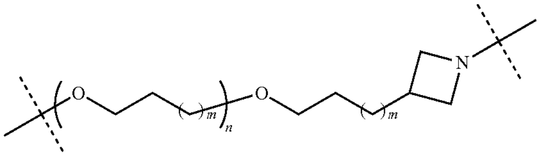
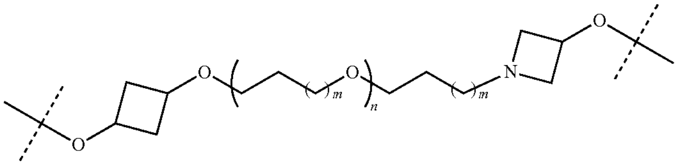
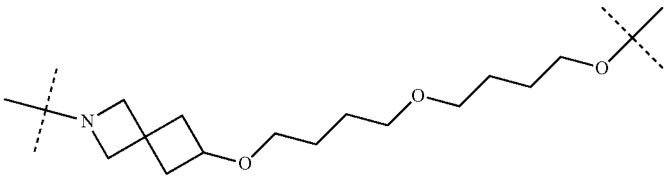
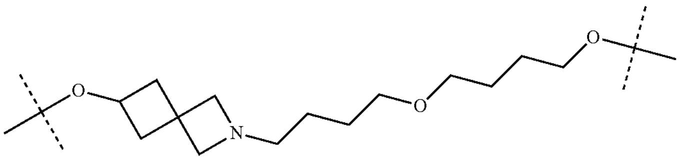

-continued
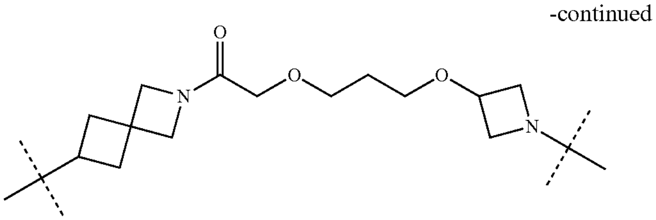
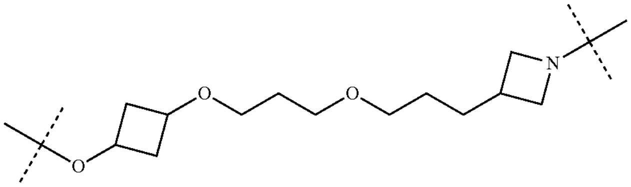
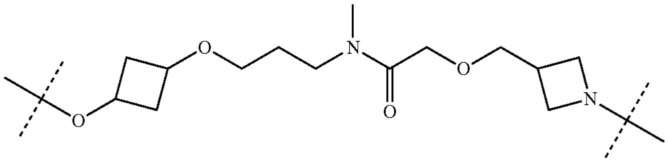
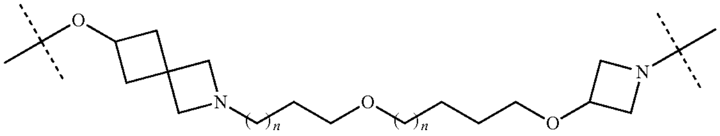
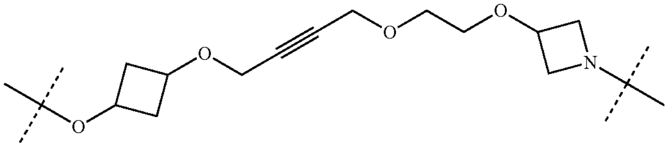
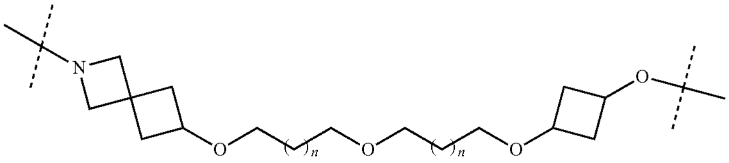
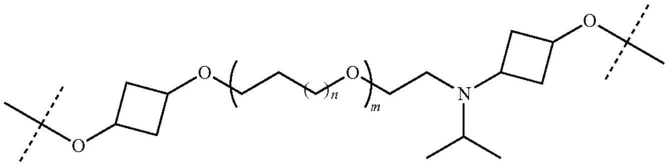
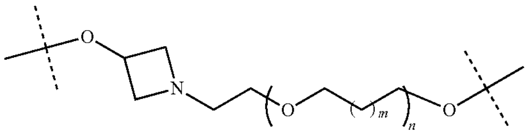
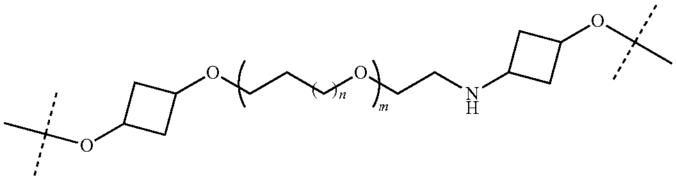
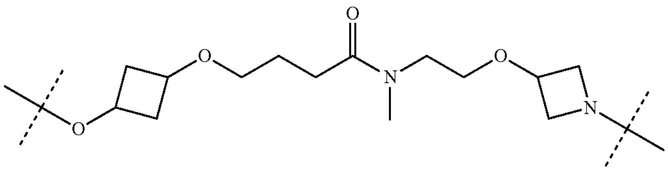
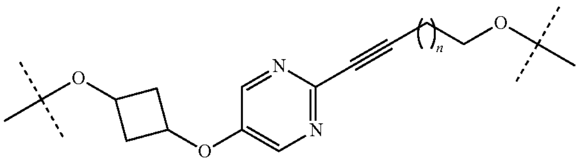
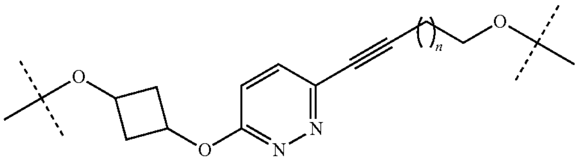

-continued
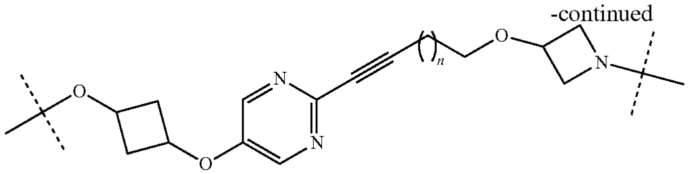
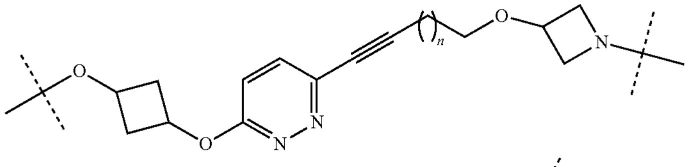
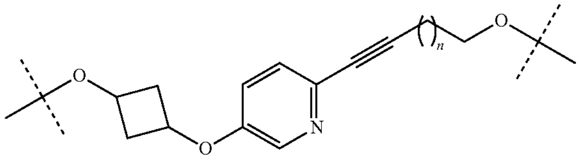
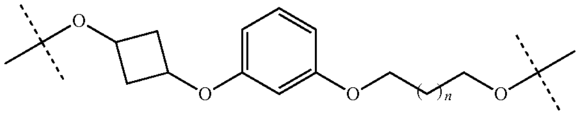
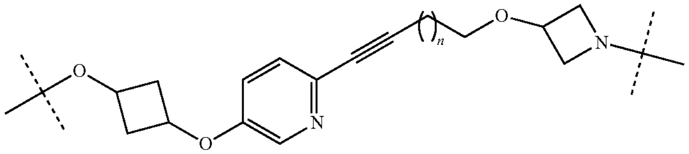
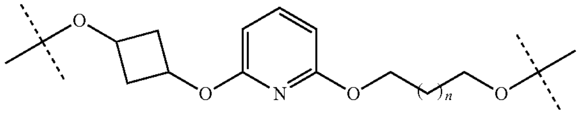
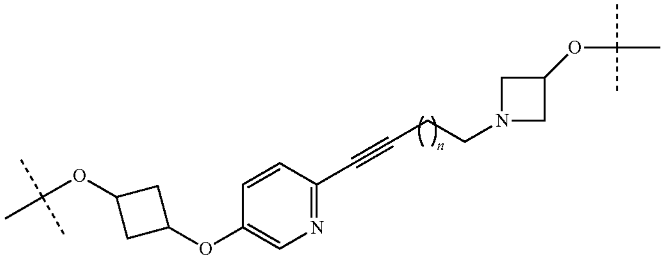
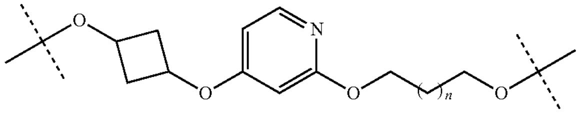
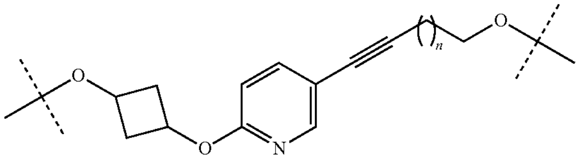
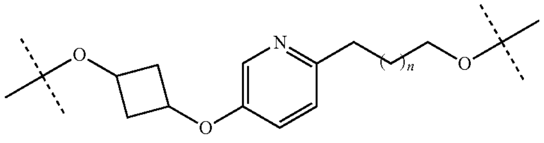
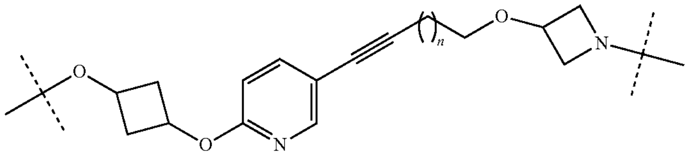
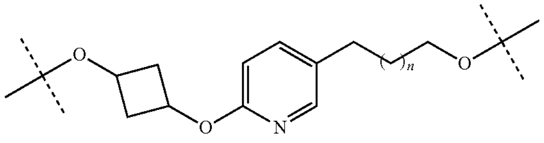
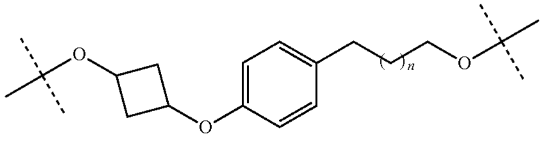
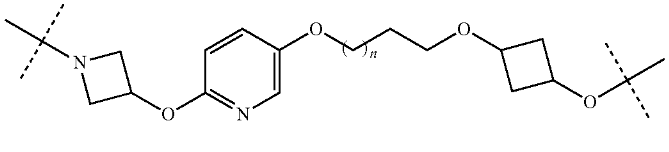

-continued
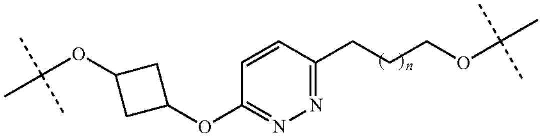
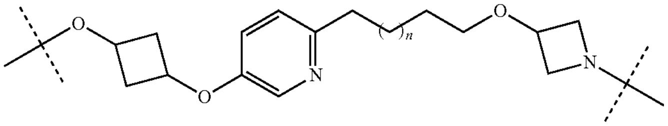
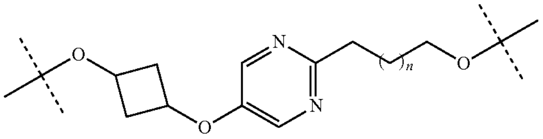
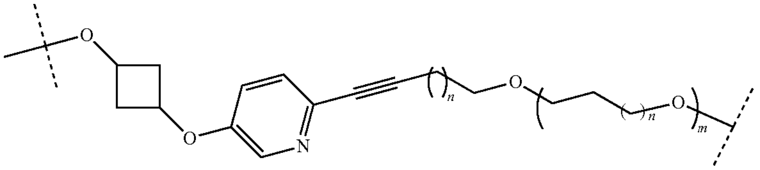
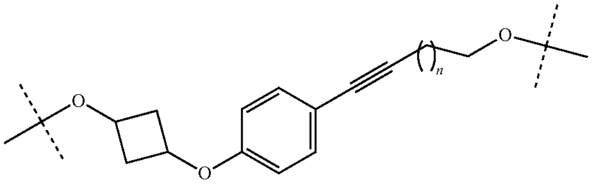
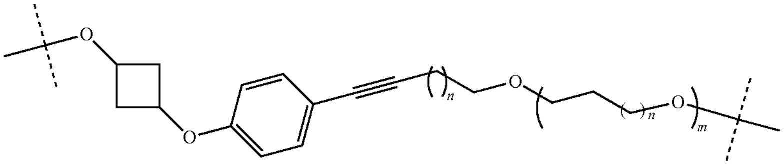
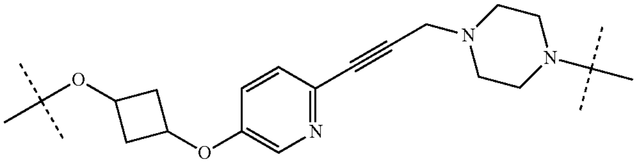
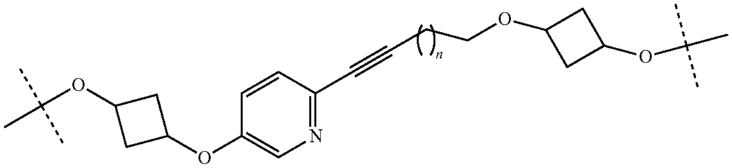
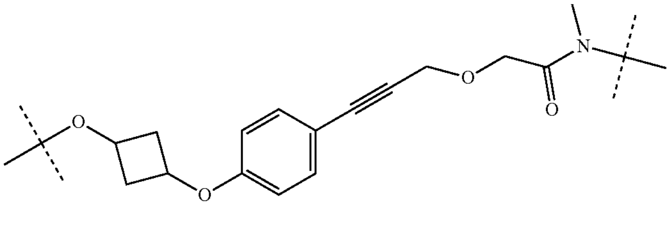
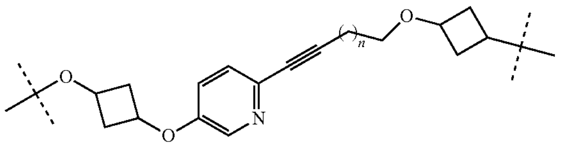
-continued
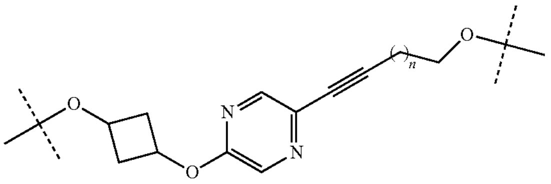

-continued
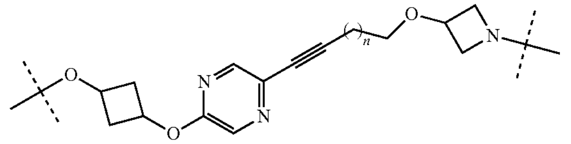
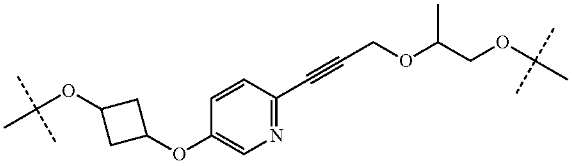
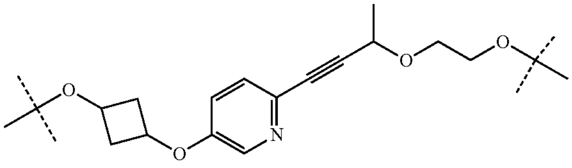
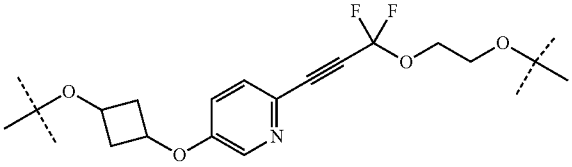
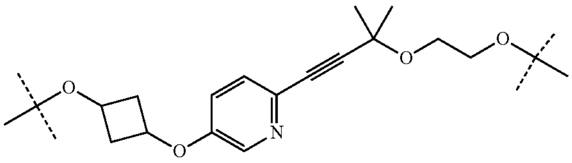
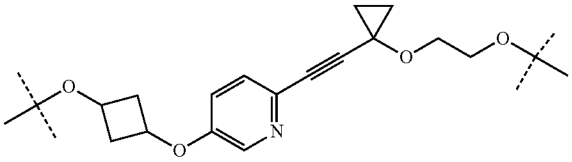
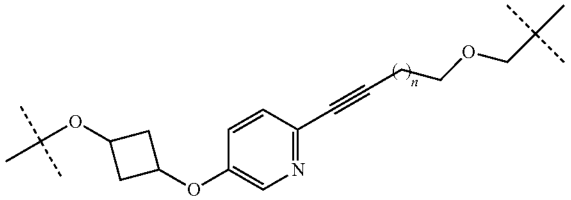
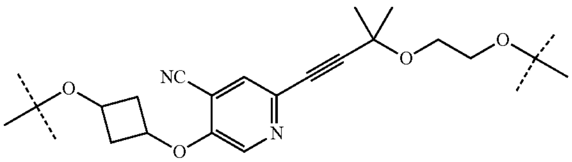
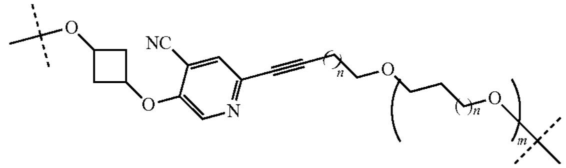
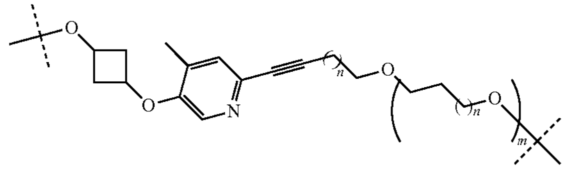
-continued
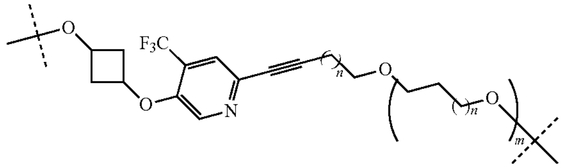
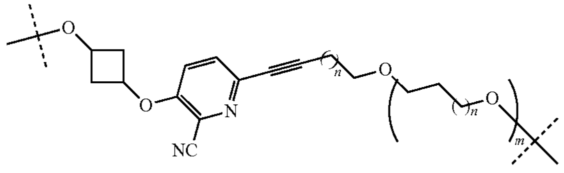
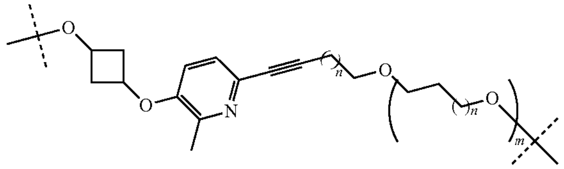
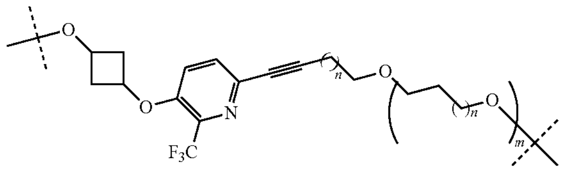
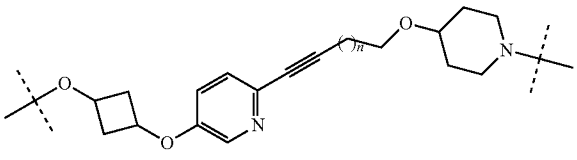
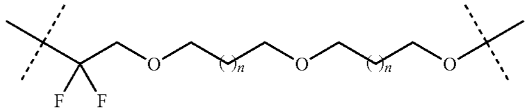
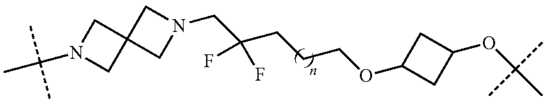
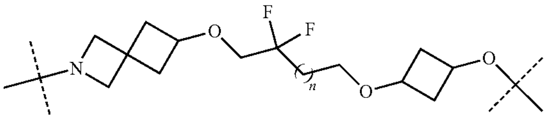
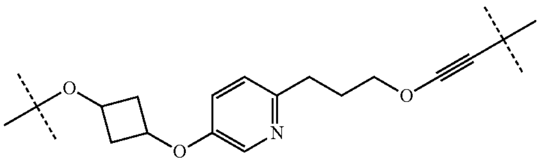
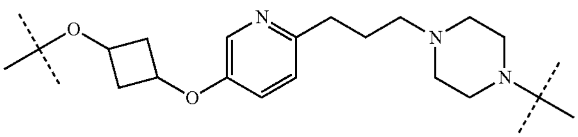
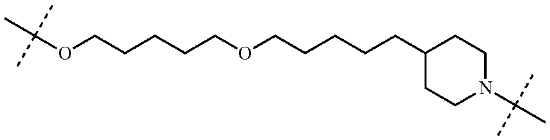

-continued
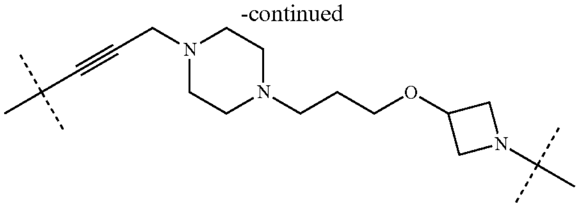
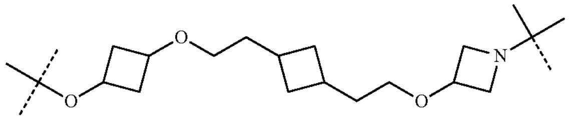
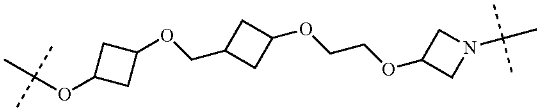
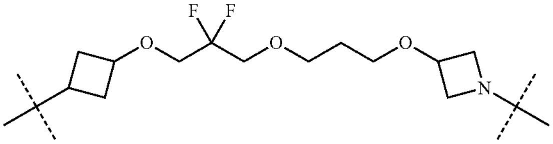
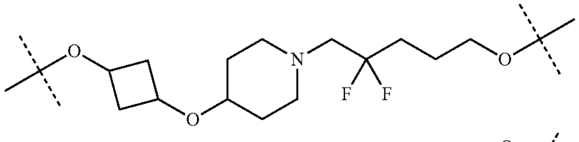
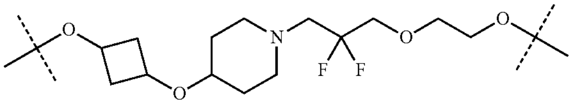
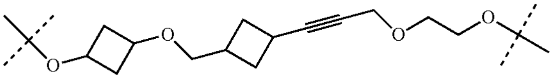
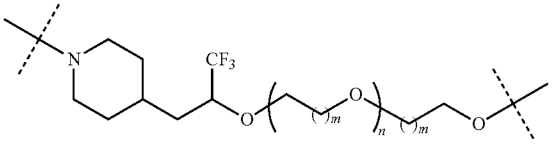
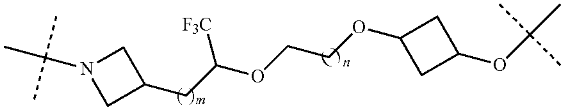
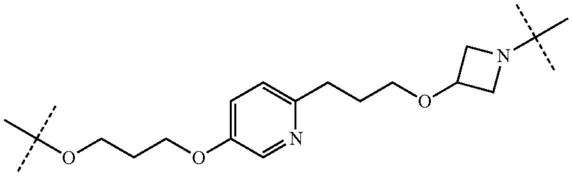
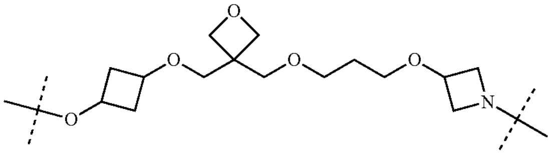
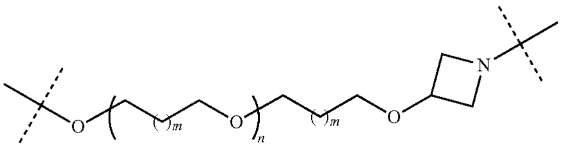
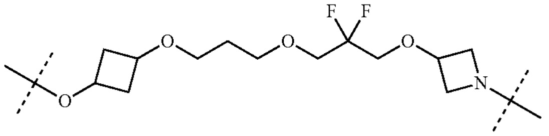
-continued
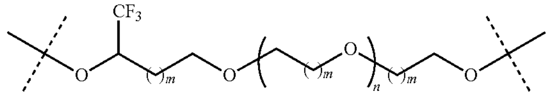
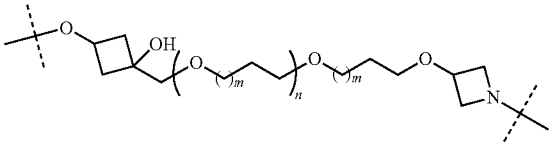
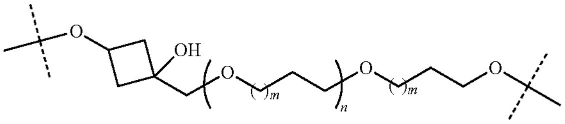
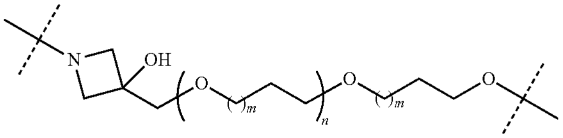
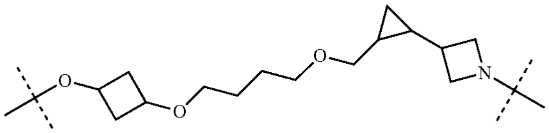
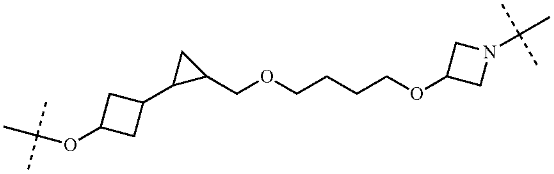
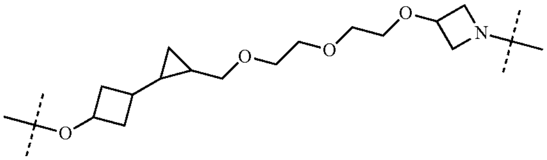
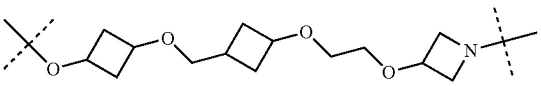
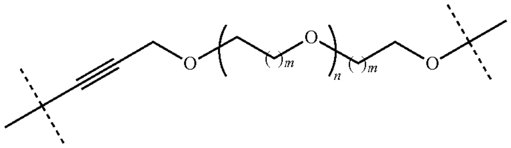
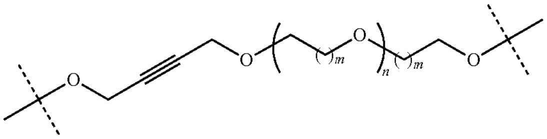
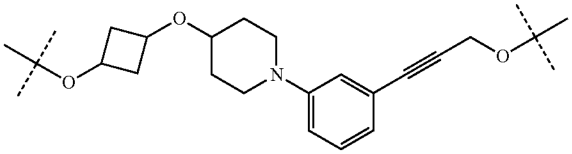
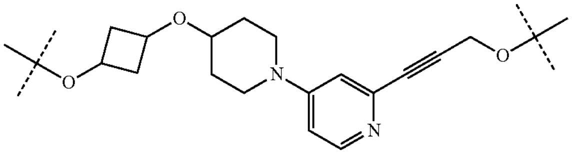

-continued
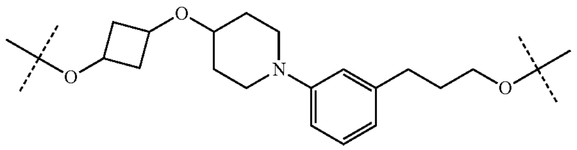
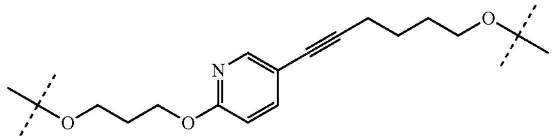
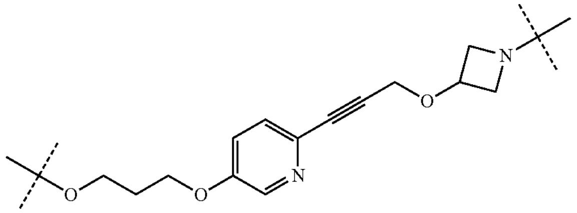
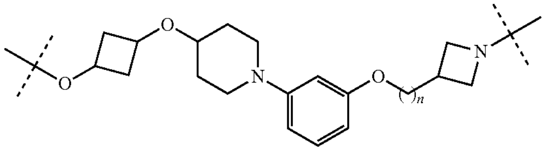
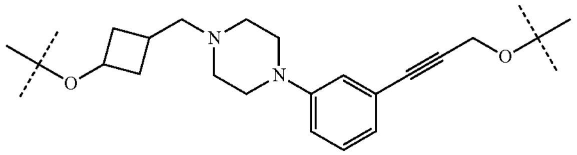
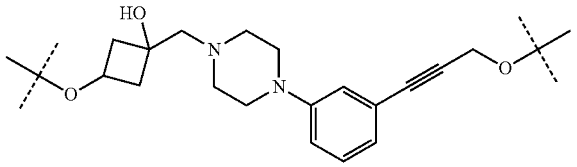
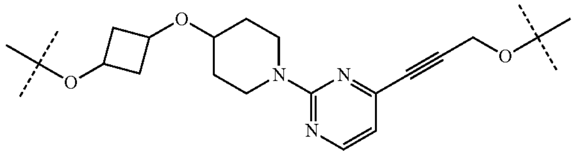
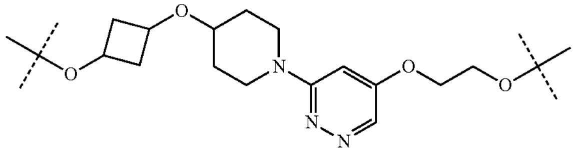
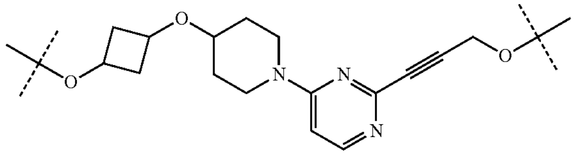
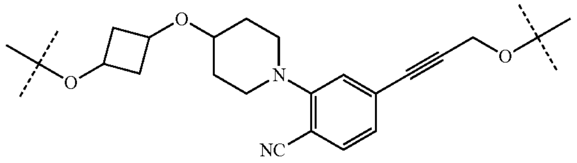
-continued
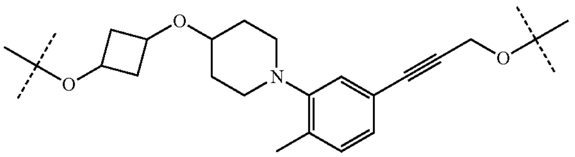
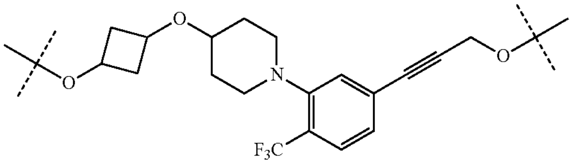
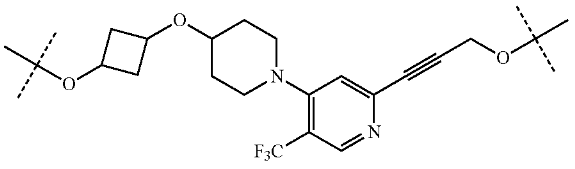
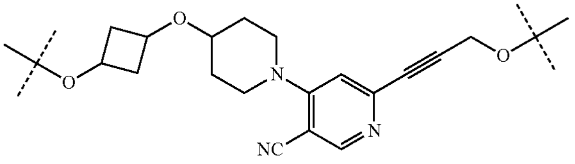
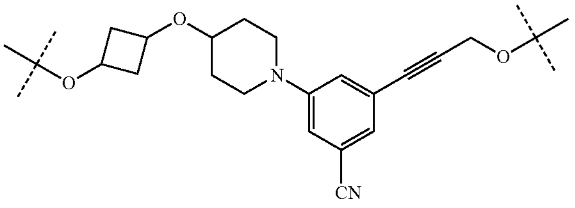
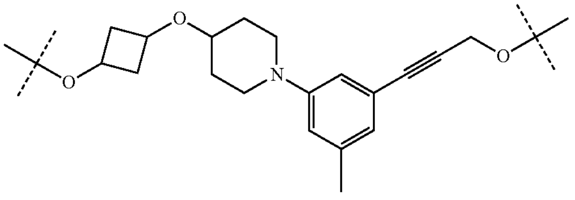
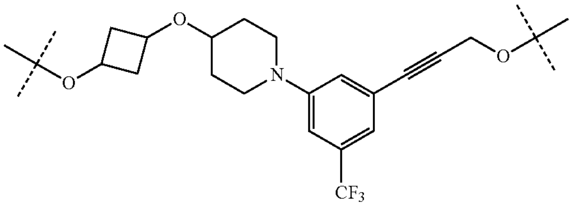
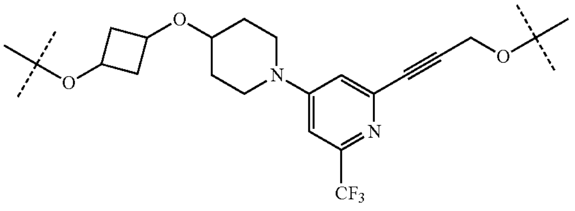
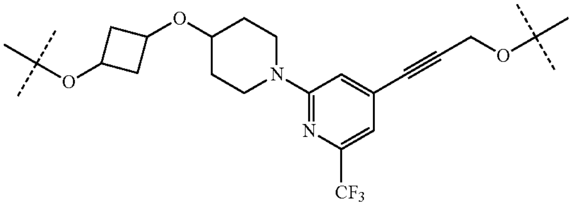

-continued
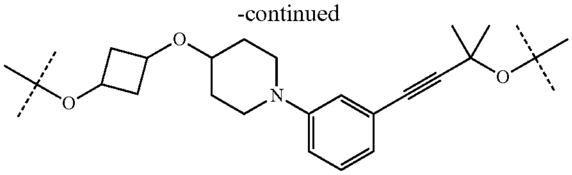
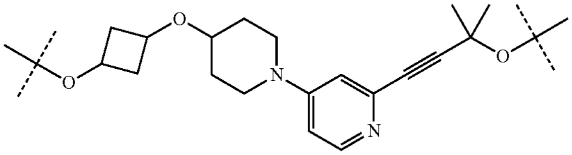
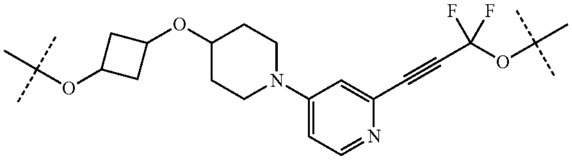
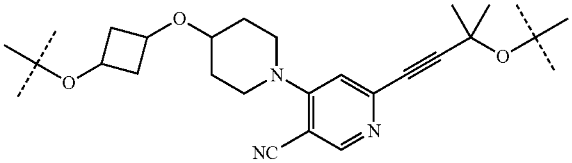
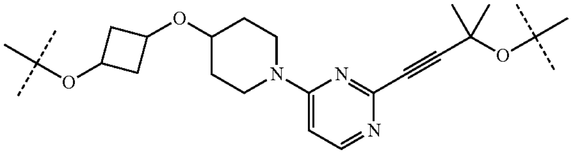
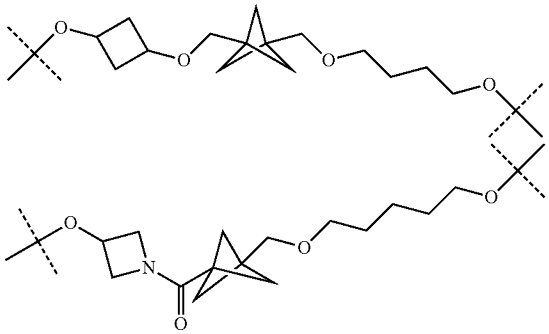
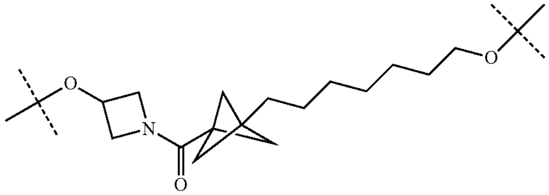
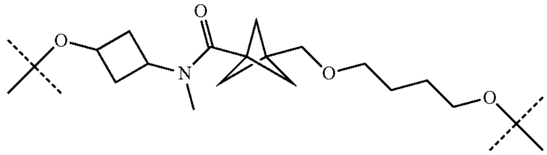
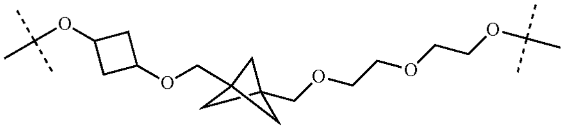
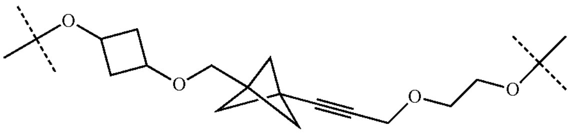
-continued
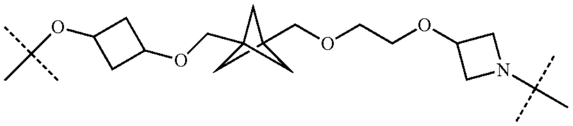
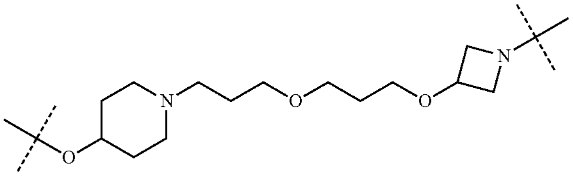
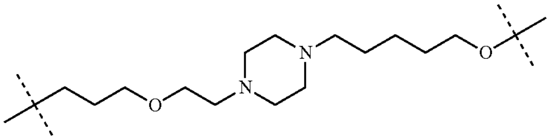
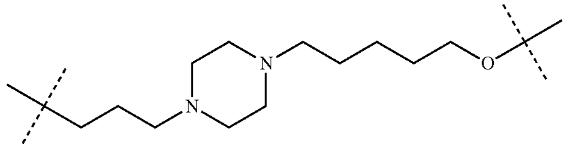
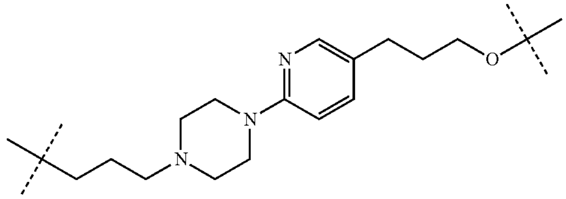
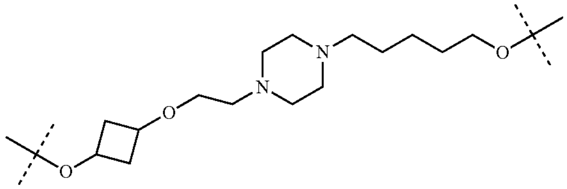
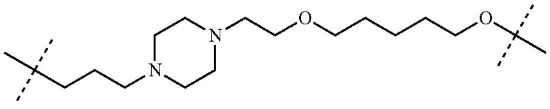
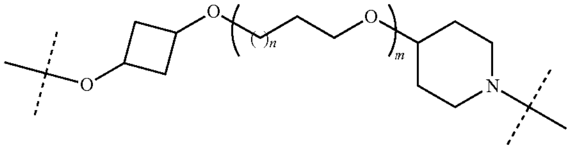
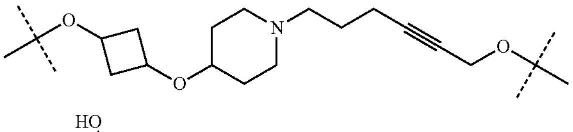
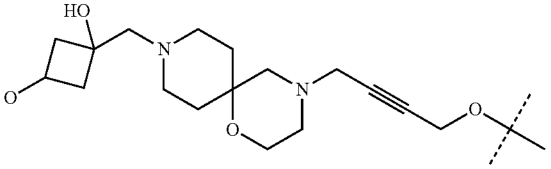
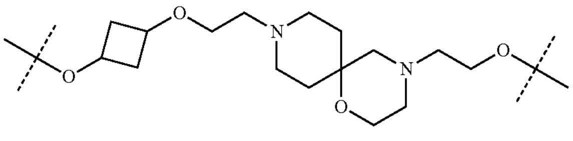

-continued
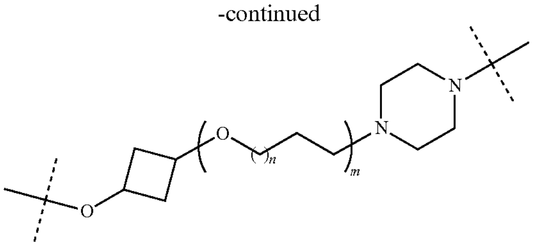
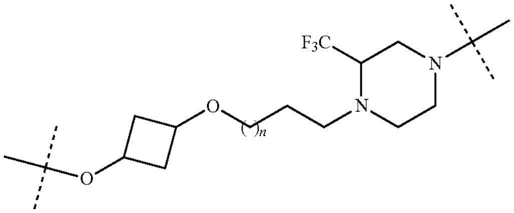
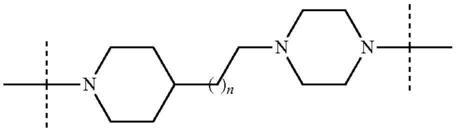
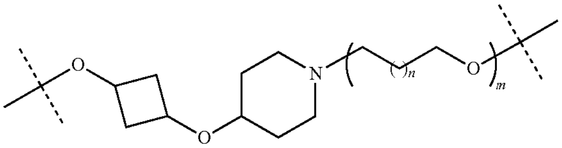
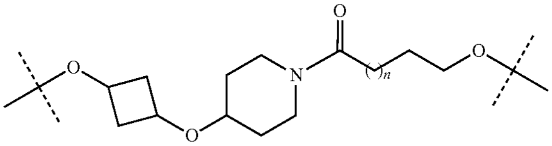
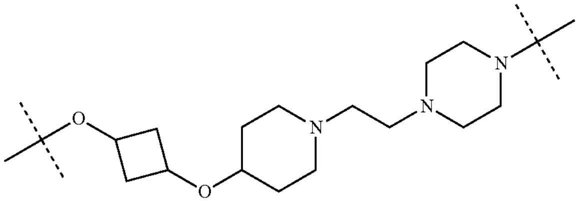
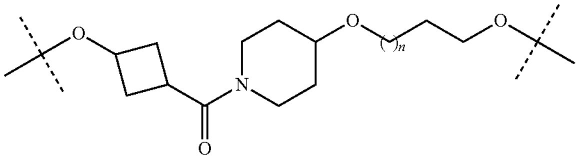
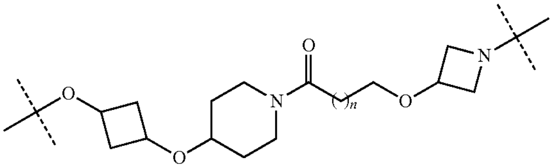
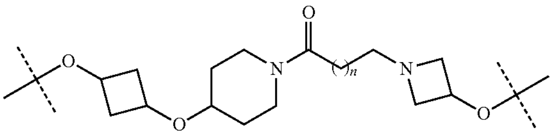
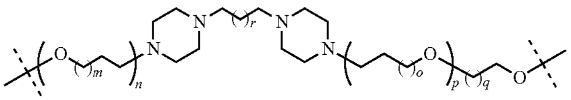
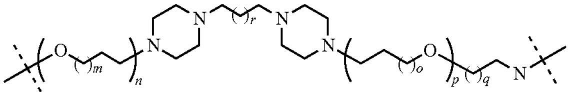
-continued
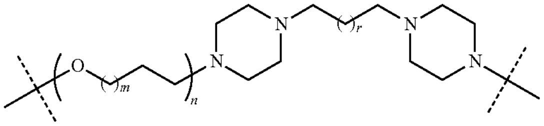
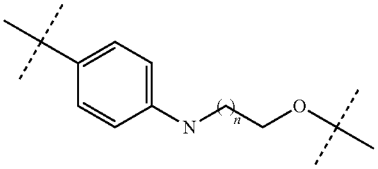
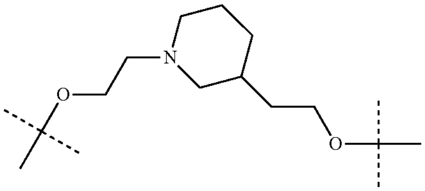
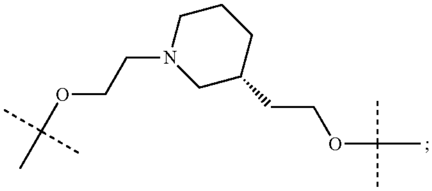
;
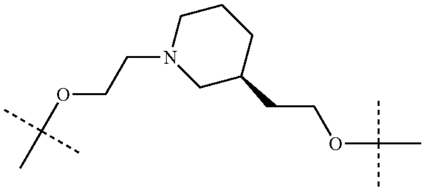
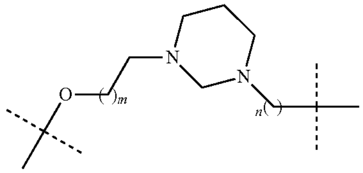
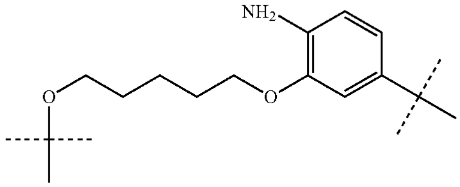
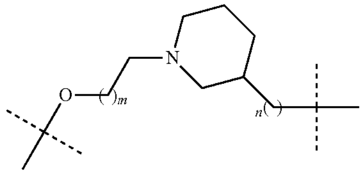
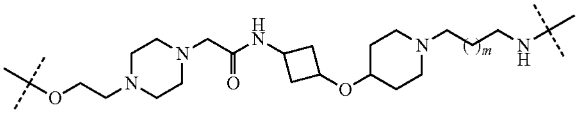
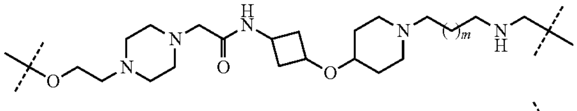
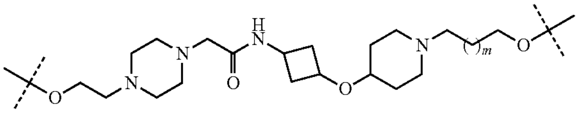

-continued
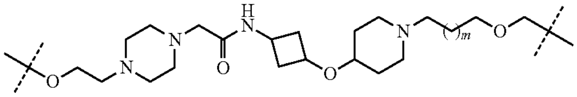
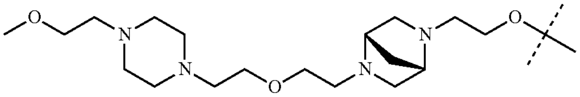
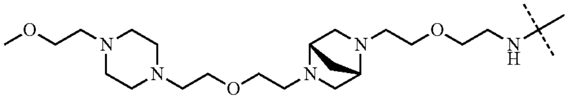
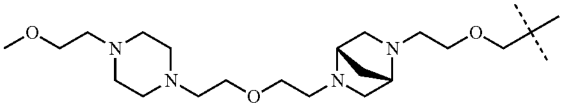
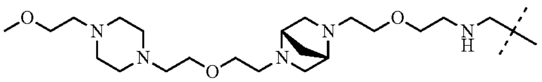
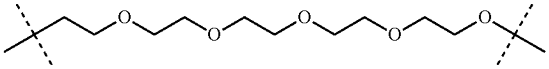
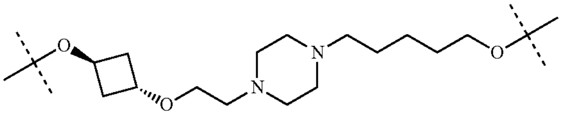
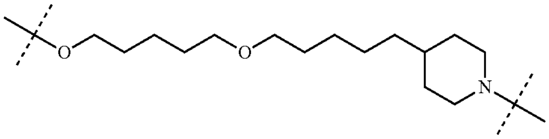
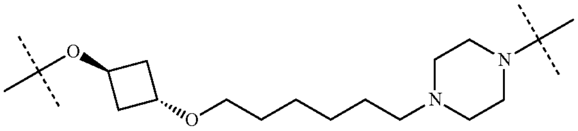
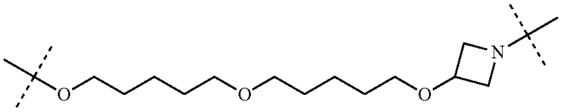
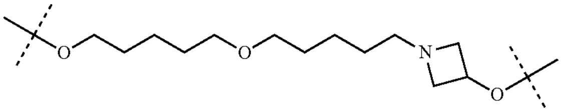
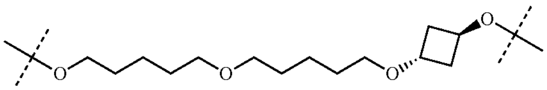
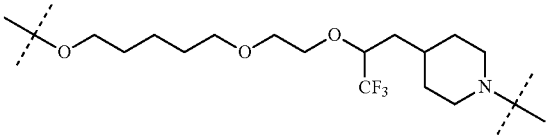
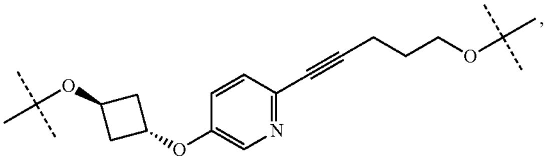,
wherein m, n, o, p, q, r, s are independently 0, 1, 2, 3, 4, 5, 6, 7, 8, 9, 10, 11, 12, 13, 14, 15, 16, 17, 18, 19, or 20.
In any aspect or embodiment described herein, the linker (L) is selected from the group consisting of:
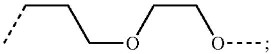;
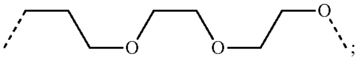;
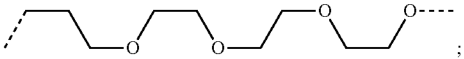;
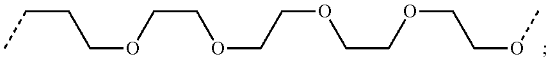;
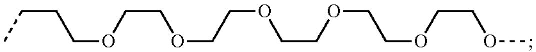;
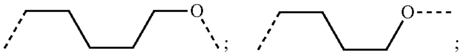; ;
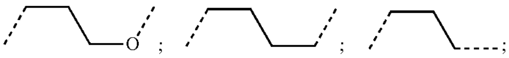; ; ;
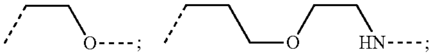; ;
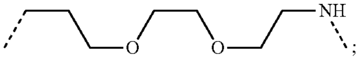;
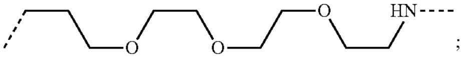;
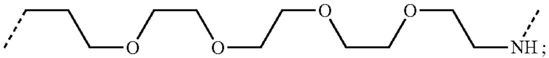;
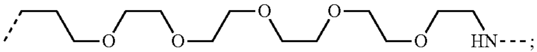;
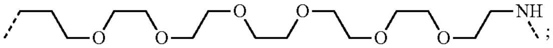;
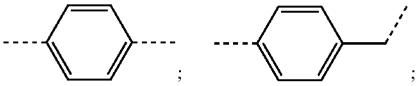; ;
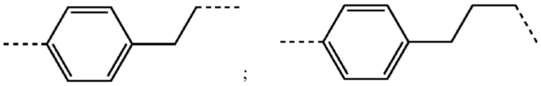; ;
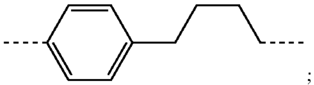;
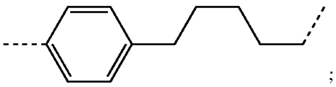;
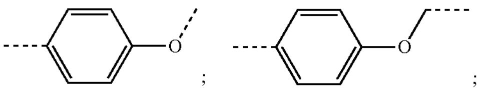; ;
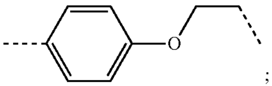;
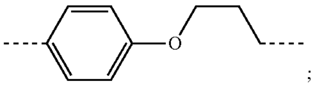;
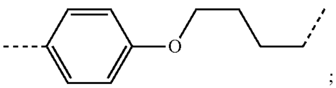;
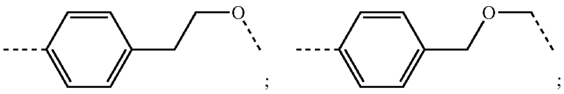; ;
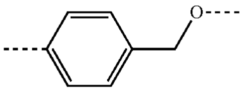;
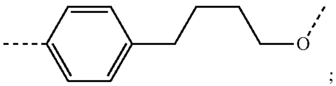;

-continued
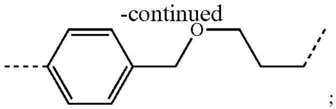
;
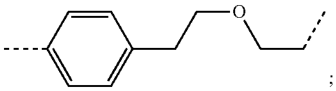
;
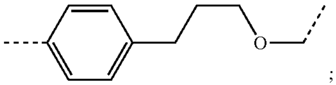
;
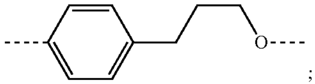
;
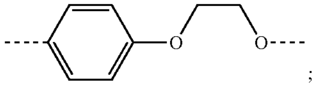
;
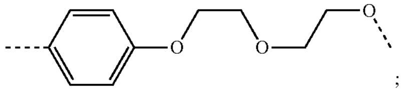
;
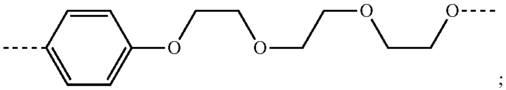
;
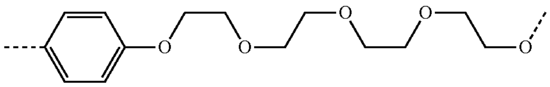
;
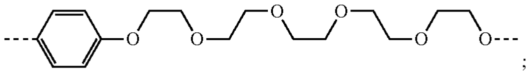
;
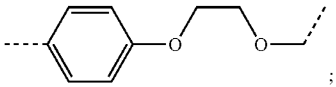
;
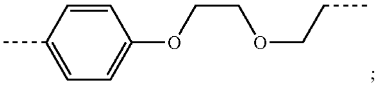
;
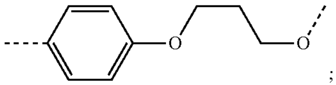
;
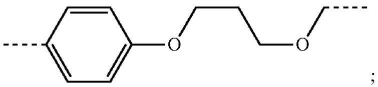
;
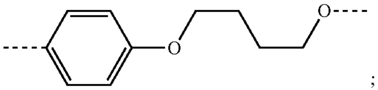
;
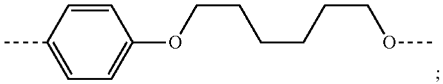
;
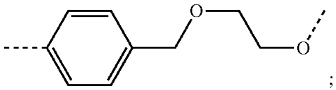
;
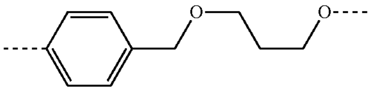
;
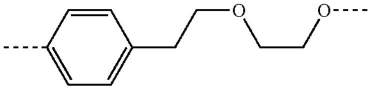
;
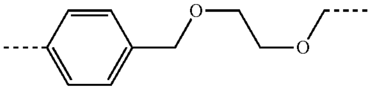
;
-continued
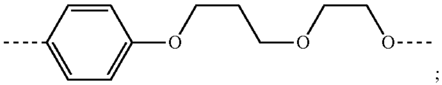
;
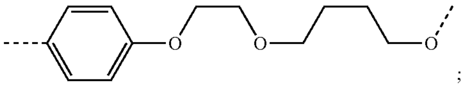
;
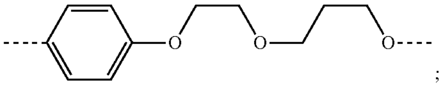
;
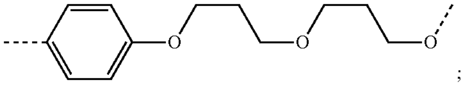
;
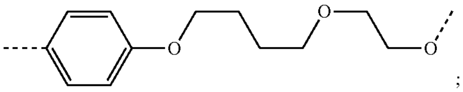
;
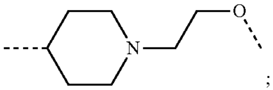
;
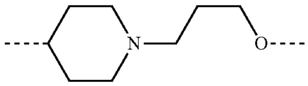
;
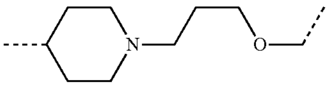
;
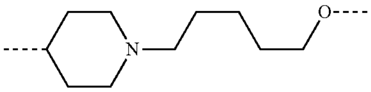
;
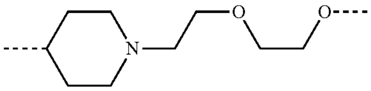
;
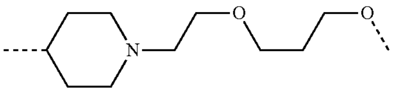
;
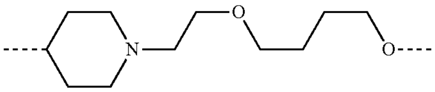
;
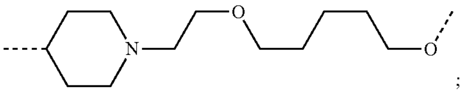
;
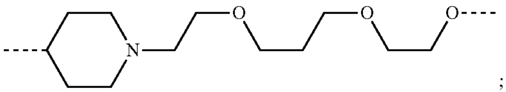
;
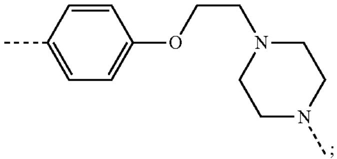
;
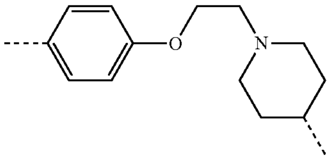
;
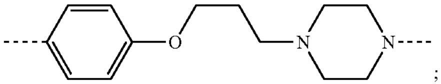
;

-continued
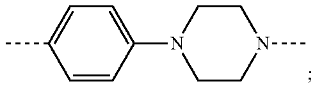
;
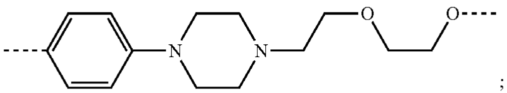
;
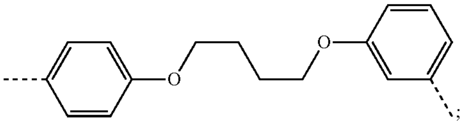
;
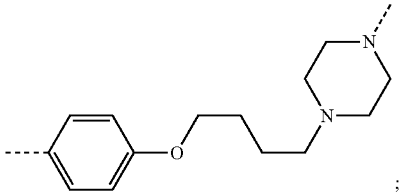
;
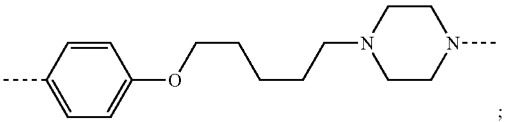
;
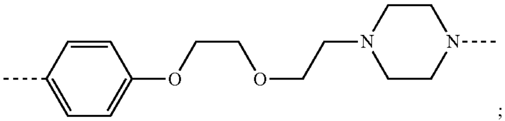
;
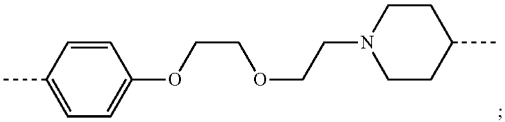
;
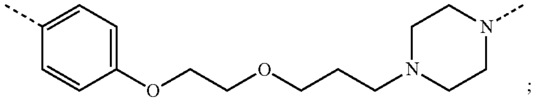
;
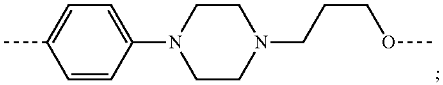
;
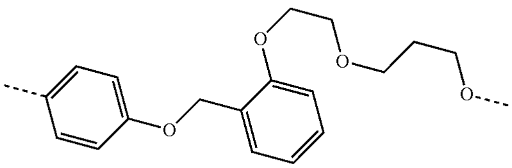
;
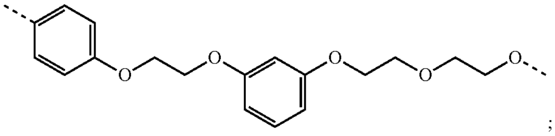
;
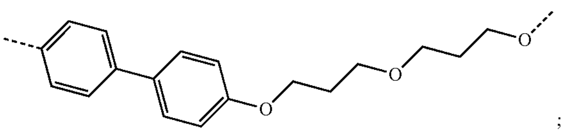
;
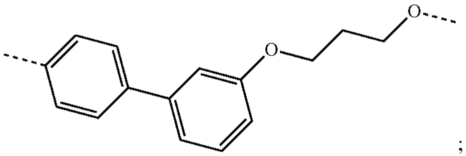
;
-continued
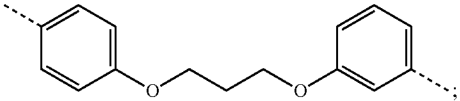
;
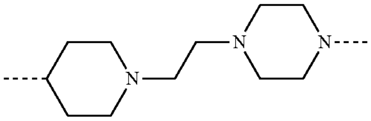
;
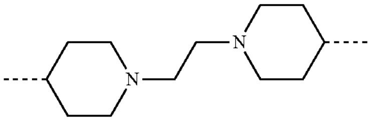
;
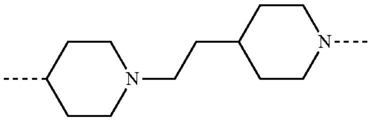
;
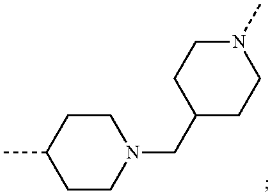
;
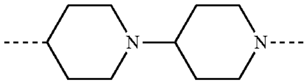
;
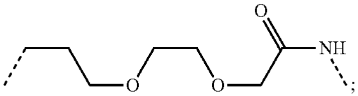
;
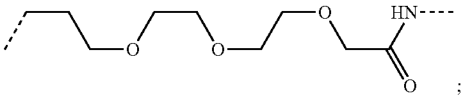
;
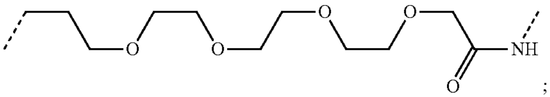
;
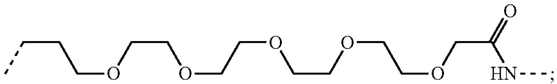
;
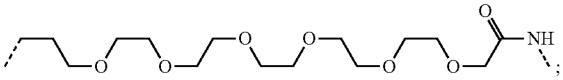
;
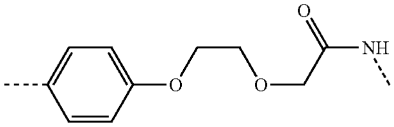
;
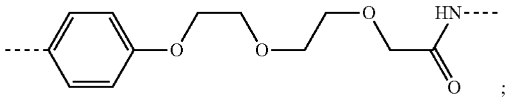
;
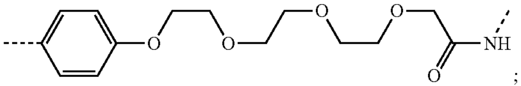
;
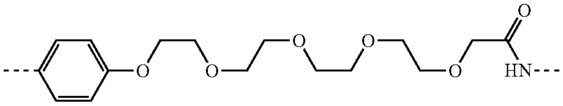
;

-continued
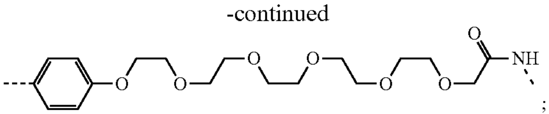
;
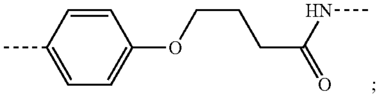
;
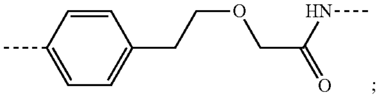
;
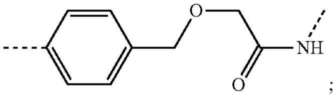
;
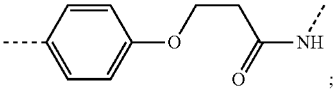
;
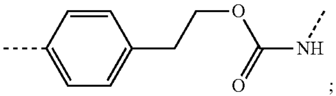
;
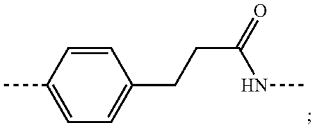
;
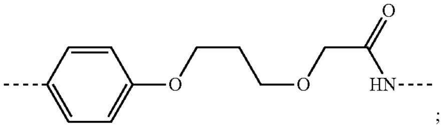
;
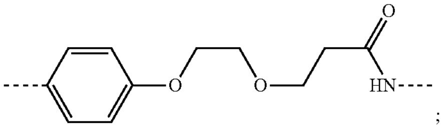
;
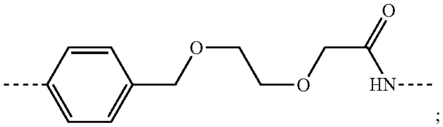
;
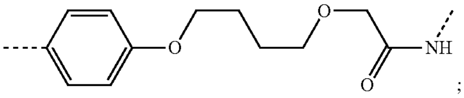
;
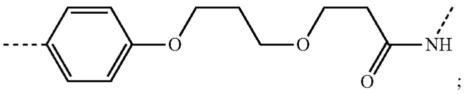
;
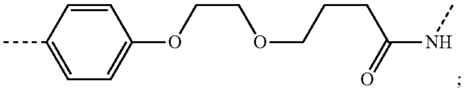
;
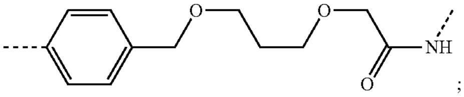
;
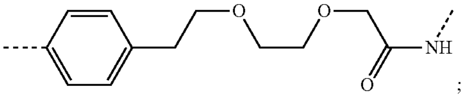
;
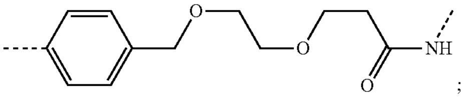
;
-continued
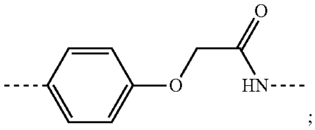
;
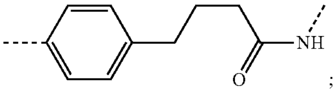
;
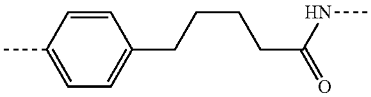
;
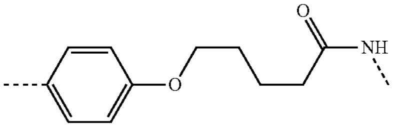
;
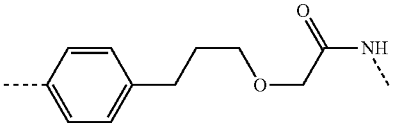
;
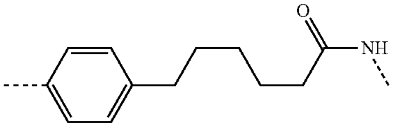
;
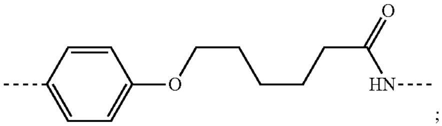
;
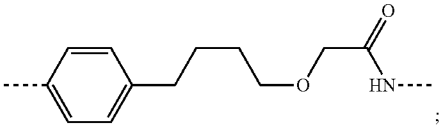
;
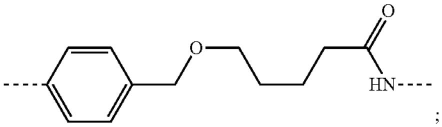
;
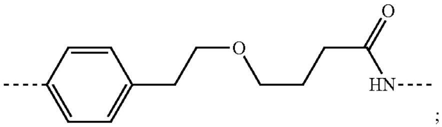
;
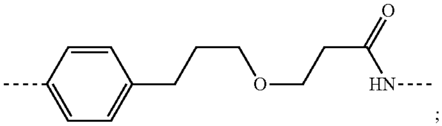
;
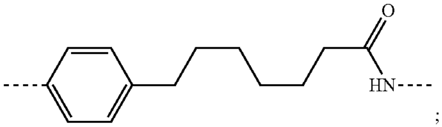
;
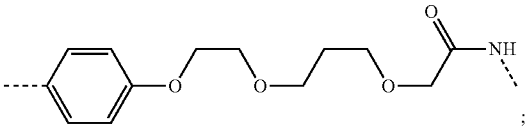
;

-continued
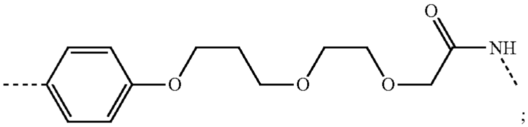
;
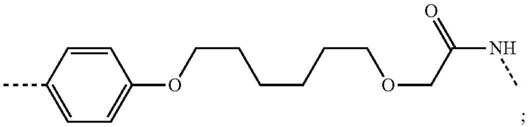
;
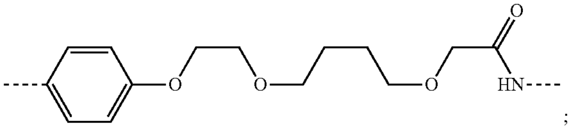
;
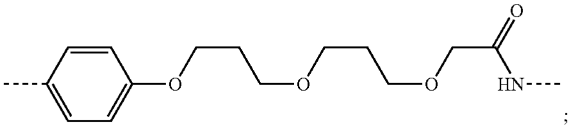
;
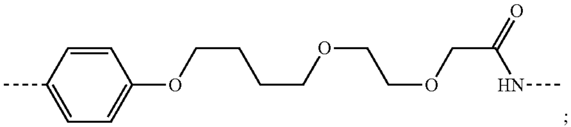
;
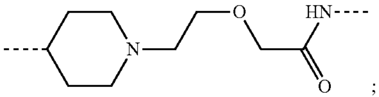
;
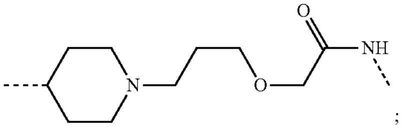
;
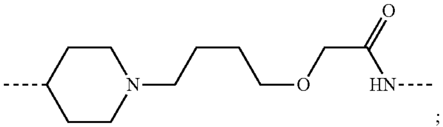
;
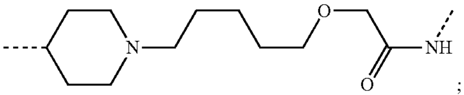
;
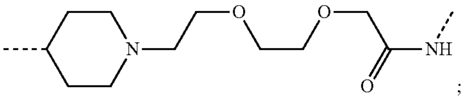
;
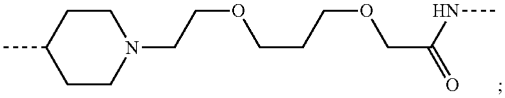
;
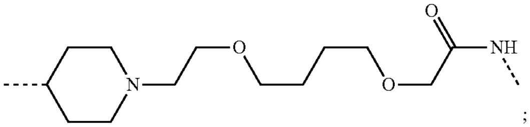
;
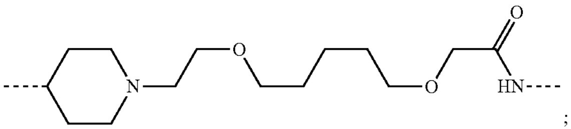
;
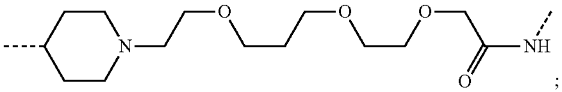
;
-continued
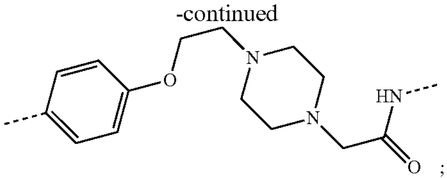
;
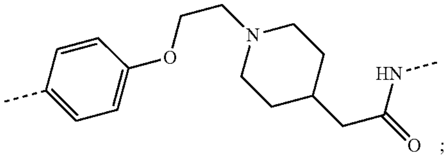
;
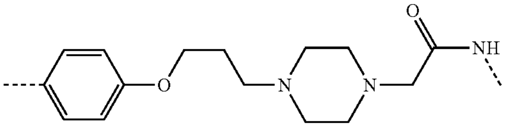
;
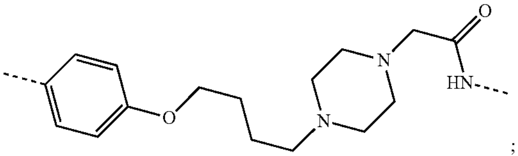
;
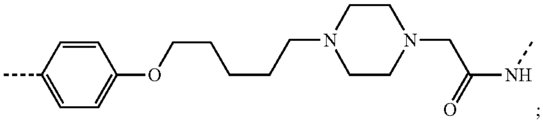
;
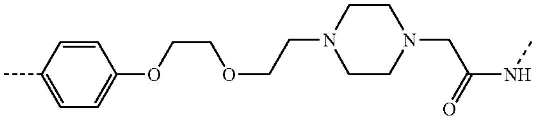
;
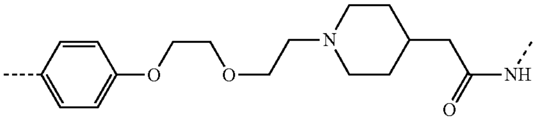
;
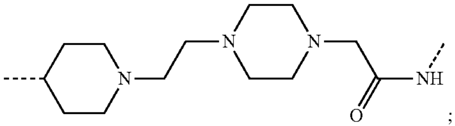
;
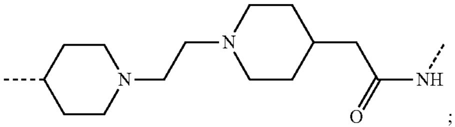
;
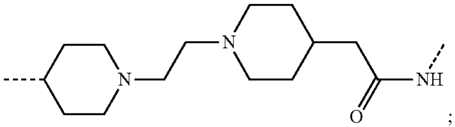
;
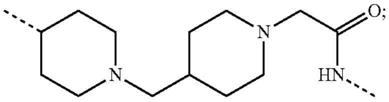
;
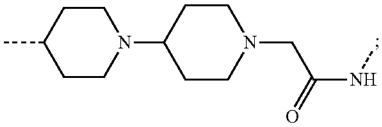
;
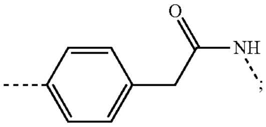
;

-continued
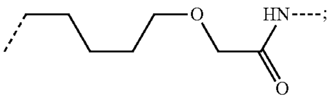
;
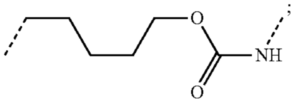
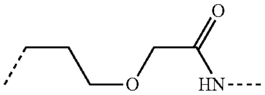
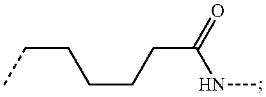
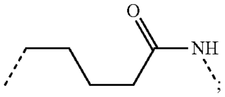
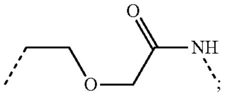
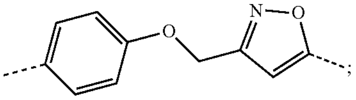
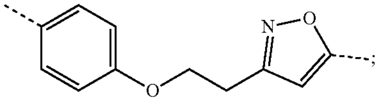
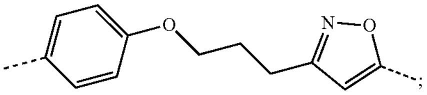
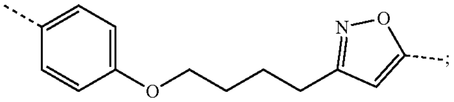
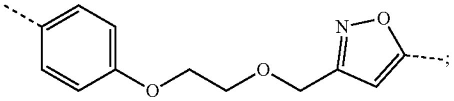
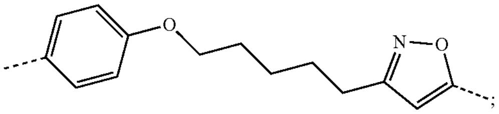
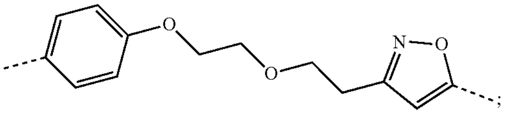
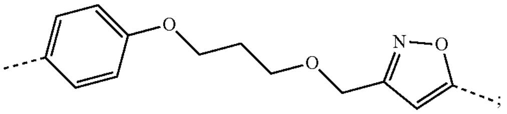
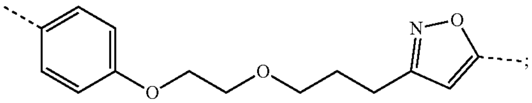
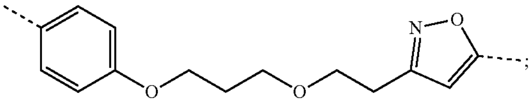
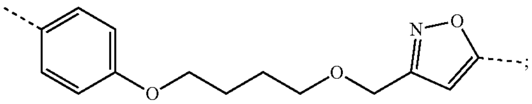
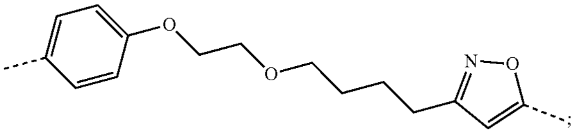
-continued
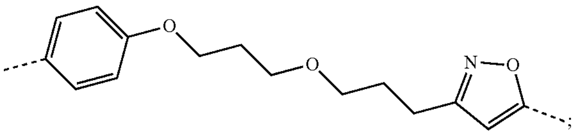
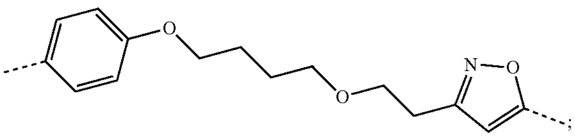
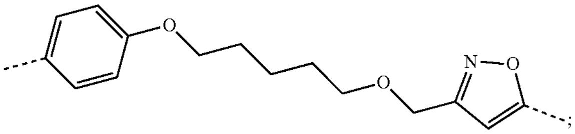
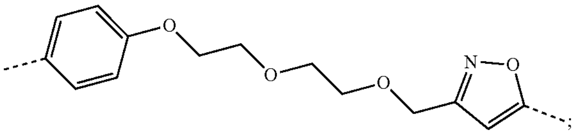
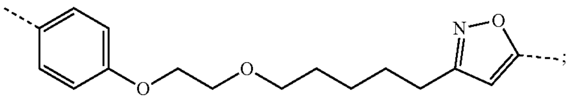
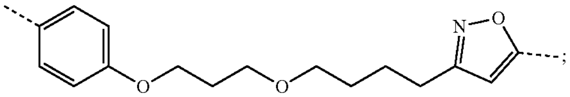
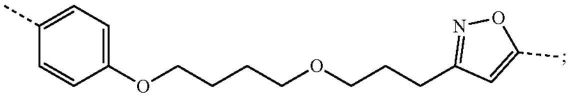
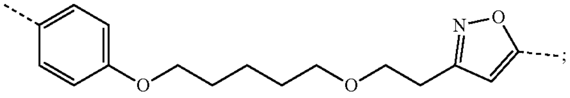
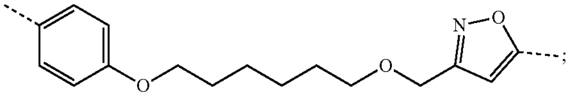
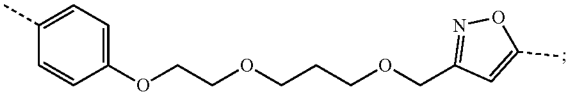
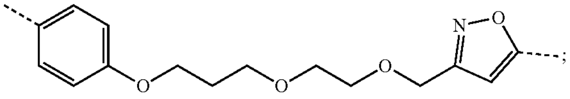
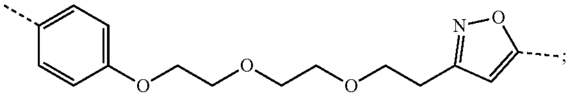
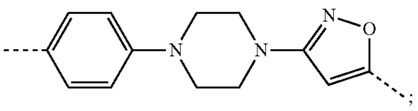
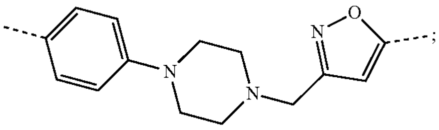

-continued
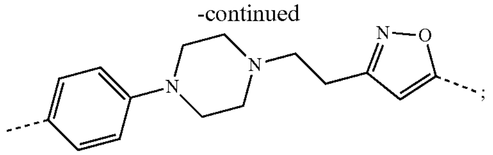
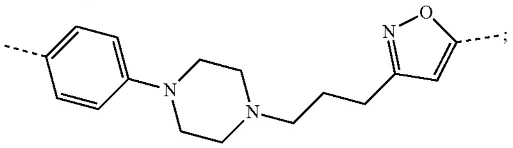
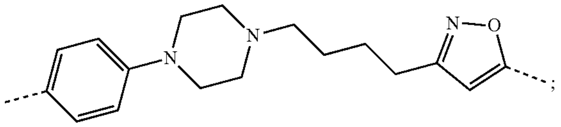
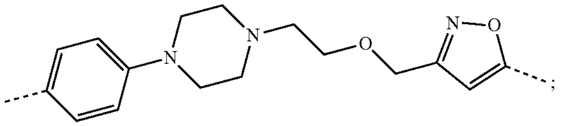
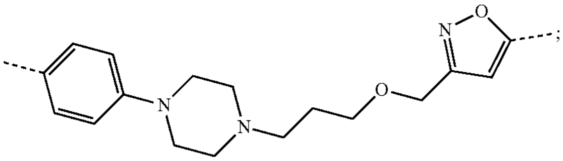
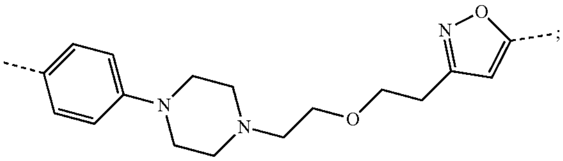
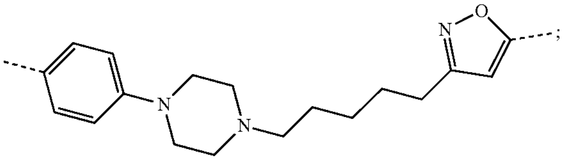
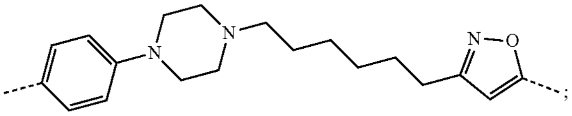
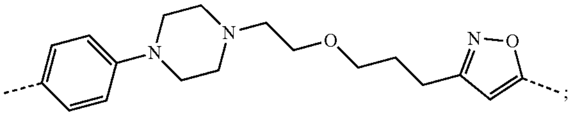
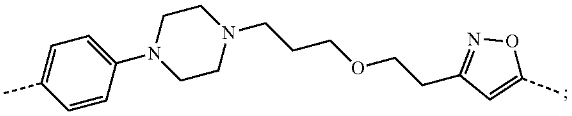
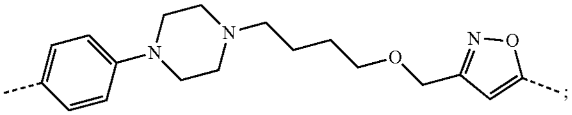
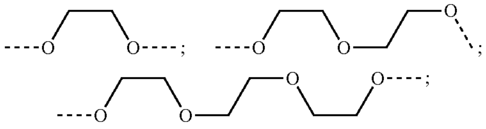
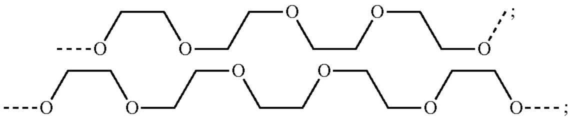
-continued
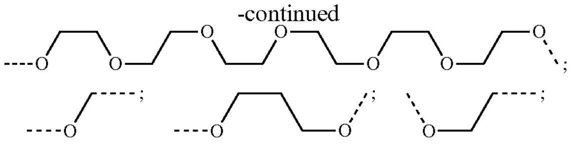
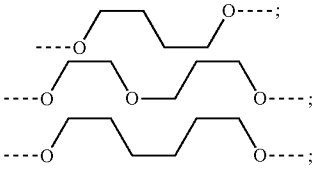
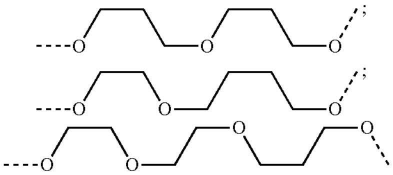
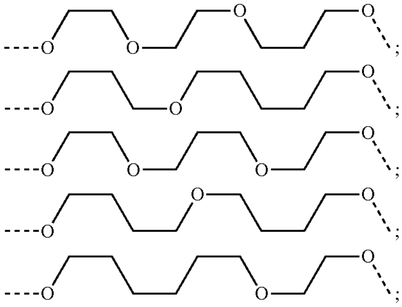
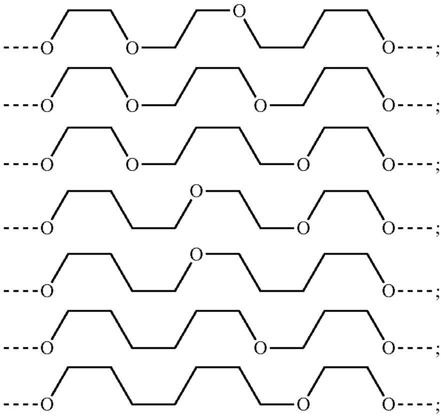
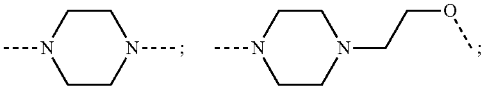
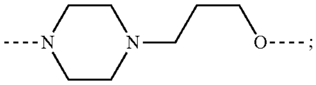
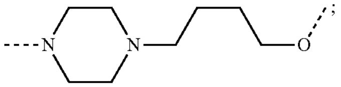
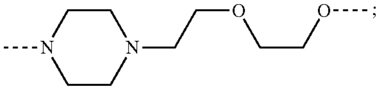
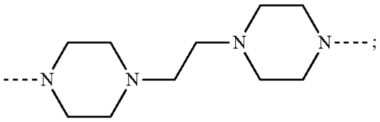
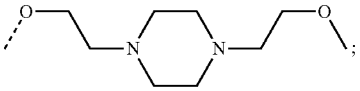

-continued
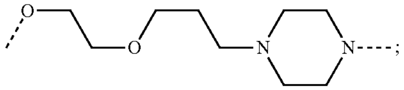
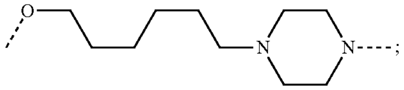
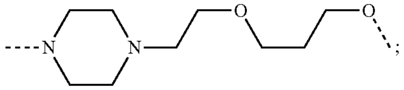
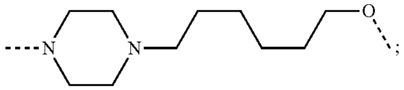
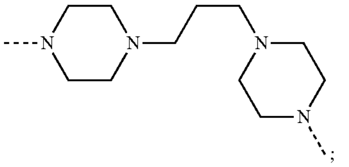
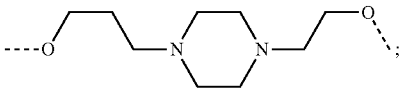
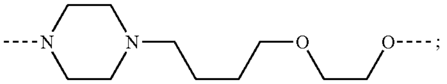
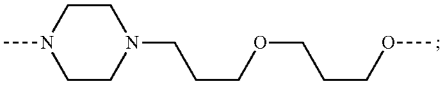
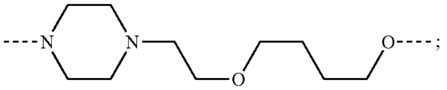
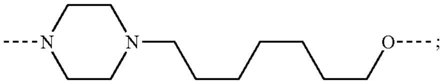
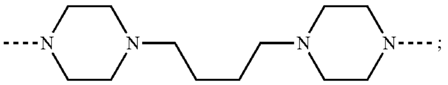
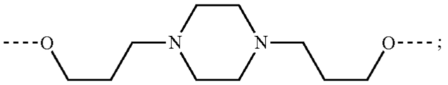
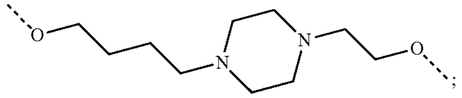
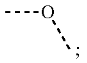
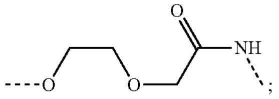
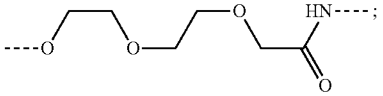
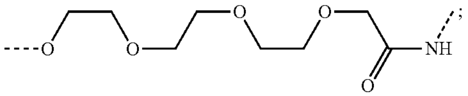
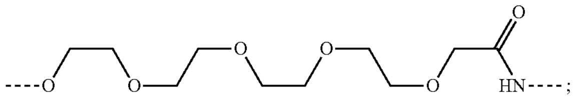
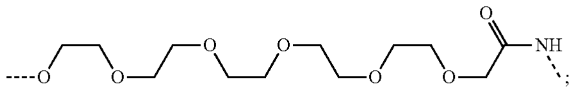
-continued
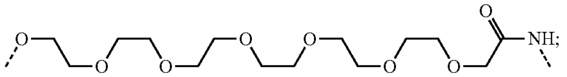
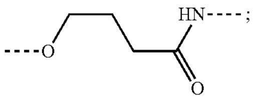
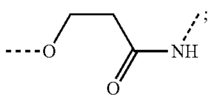
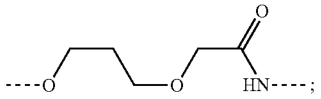
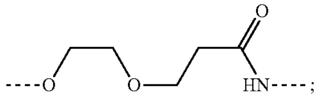
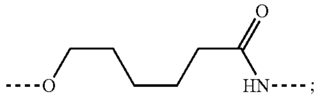
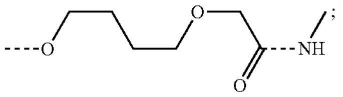
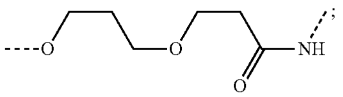
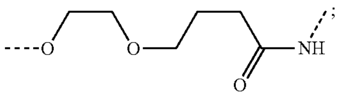
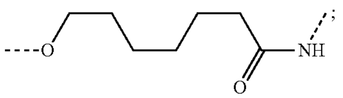
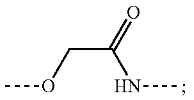
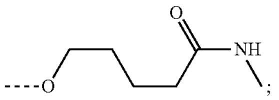
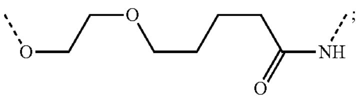
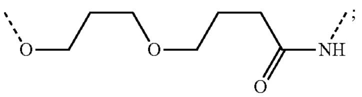
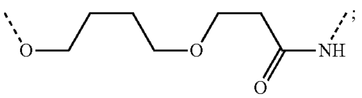
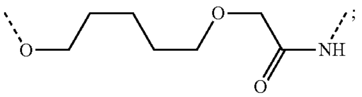
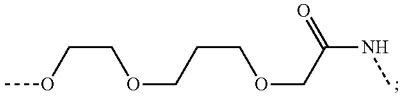
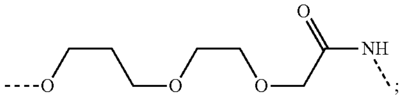
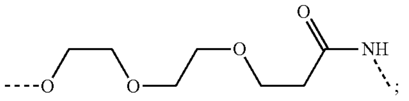

-continued
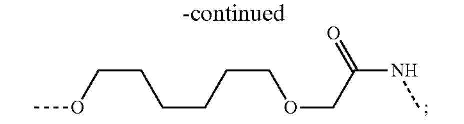
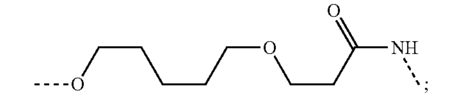
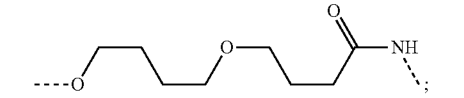
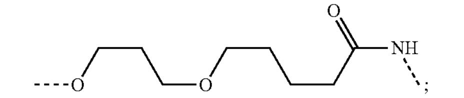
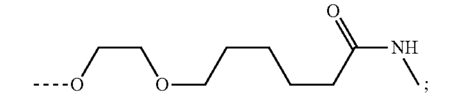
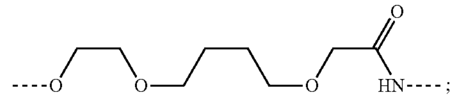
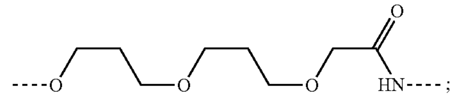
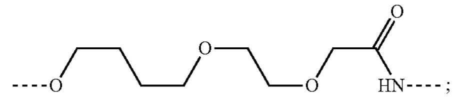
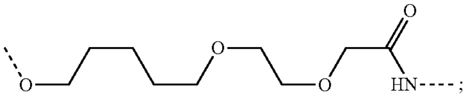
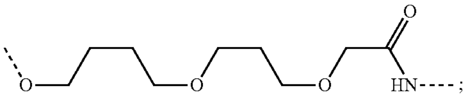
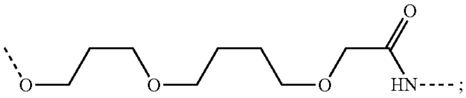
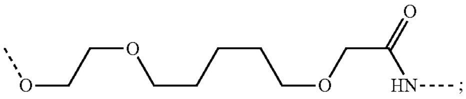
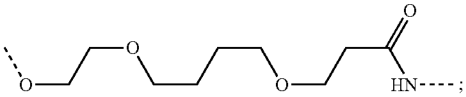
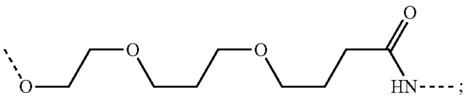
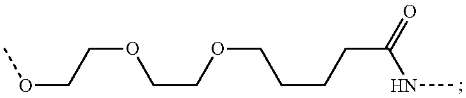
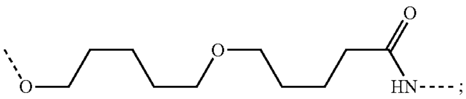
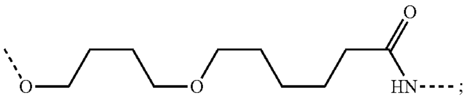
-continued
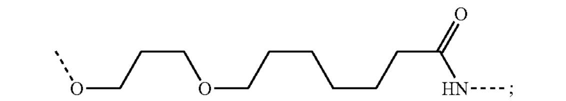
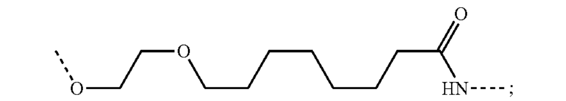
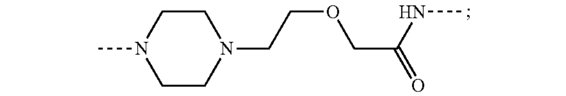
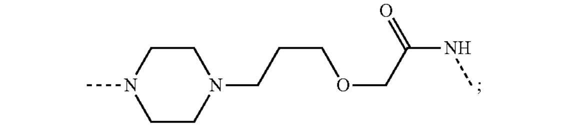
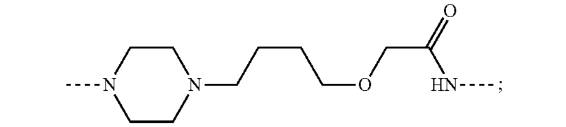
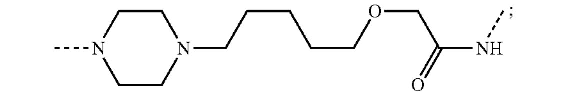
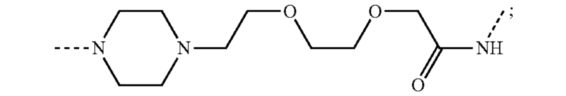
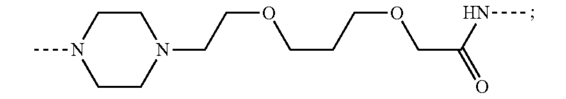
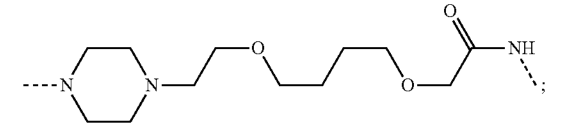
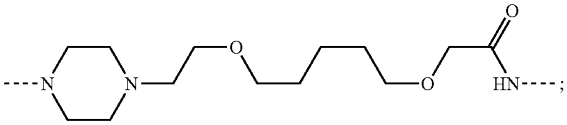
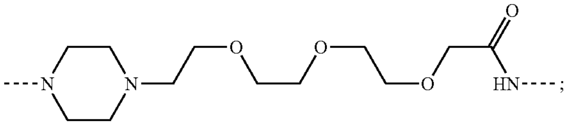
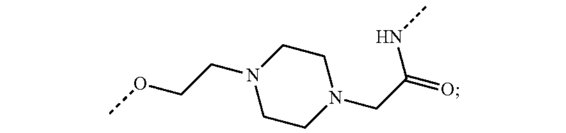
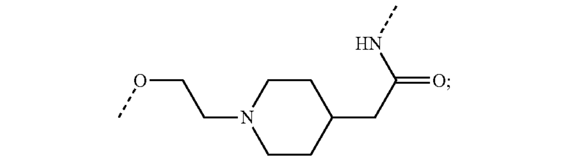
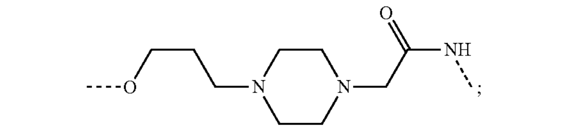

-continued
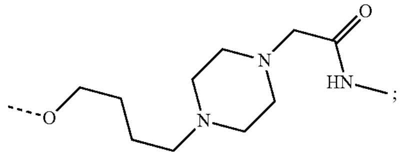
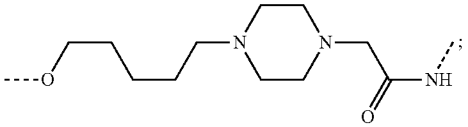
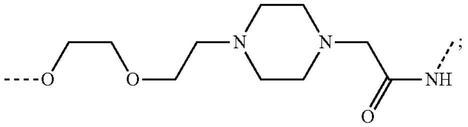
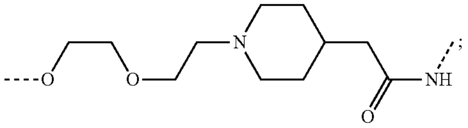
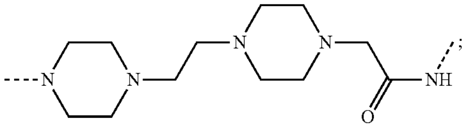
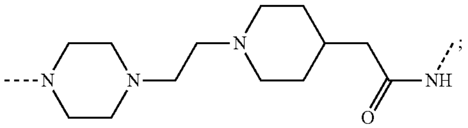
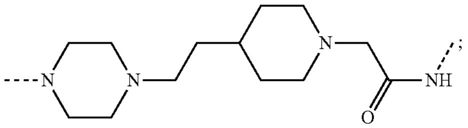
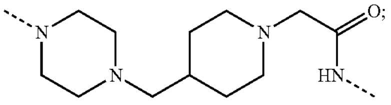
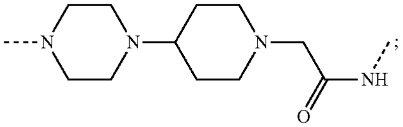
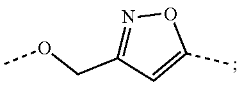
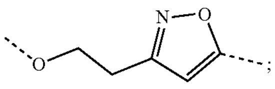
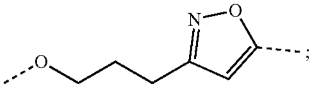
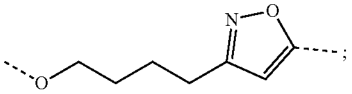
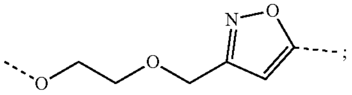
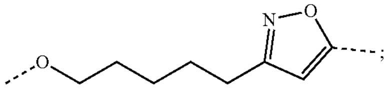
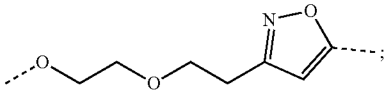
-continued
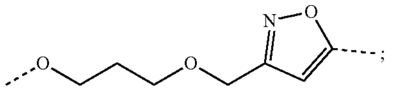
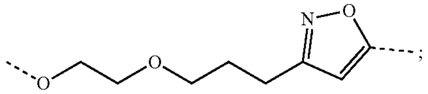
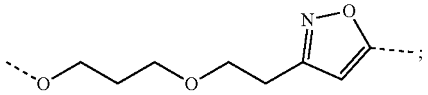
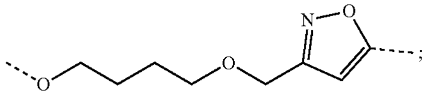
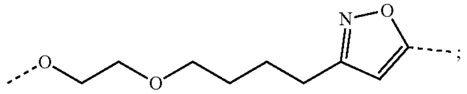
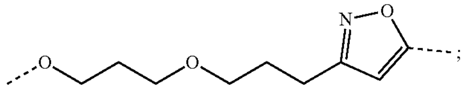
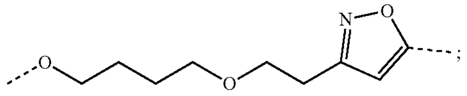
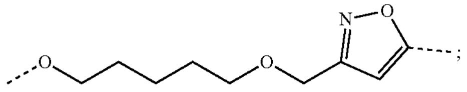
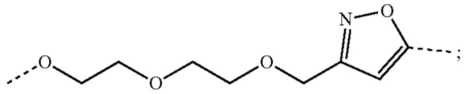
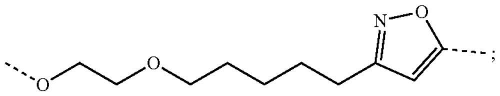
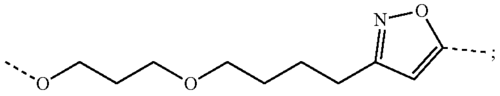
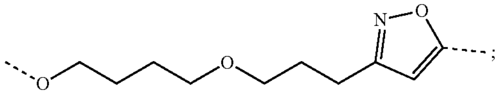
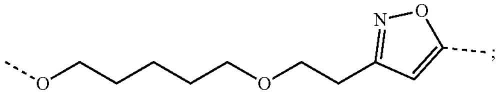
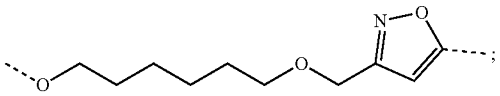
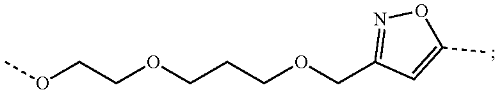
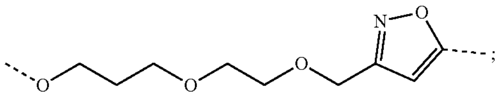
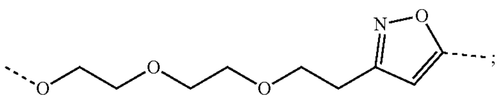
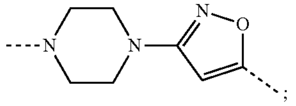

-continued

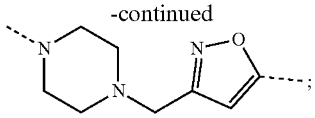

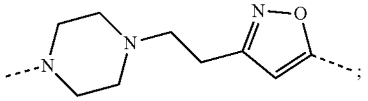

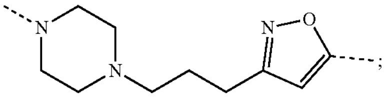

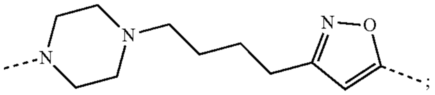

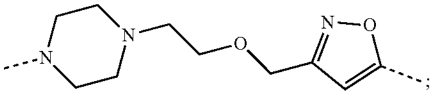

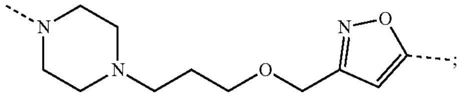

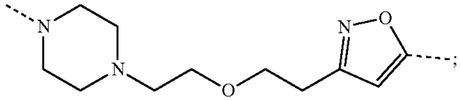

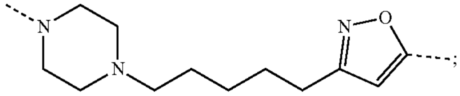

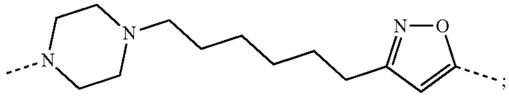

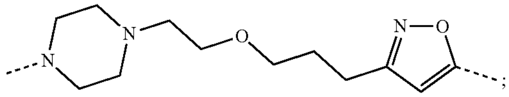

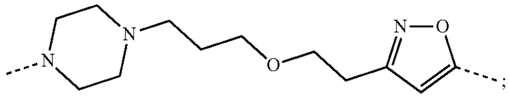

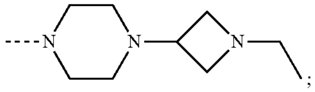

and

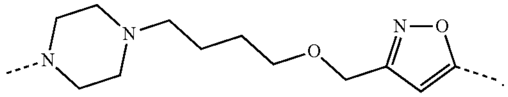

In any aspect or embodiment described herein, the linker (L) comprises a structure selected from, but not limited to the structure shown below, where a dashed line indicates the attachment point to the PTM or ULM moieties.

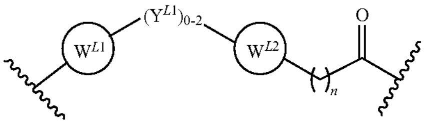

or

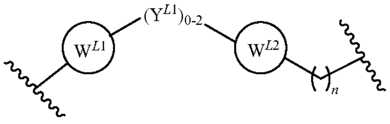

, wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, $C_1$-$C_6$ optionally substituted linear or branched alkyl, optionally substituted linear or branched $C_1$-$C_6$ alkoxy, or 2 $R^Q$ groups taken together with the atom they are attached to, form a 4-8 membered ring system containing 0-4 heteroatoms;

$Y^{L1}$ is each independently a bond, optionally substituted linear or branched $C_1$-$C_6$ alkyl, and optionally one or more C atoms are replaced with O; or optionally substituted linear or branched $C_1$-$C_6$ alkoxy;

n is 0-10; and

 indicates the attachment point to the PTM or ULM moieties.

In any aspect or embodiment described herein, the linker (L) comprises a structure selected from, but not limited to the structure shown below, where a dashed line indicates the attachment point to the PTM or ULM moieties.

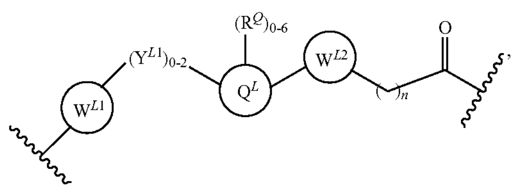

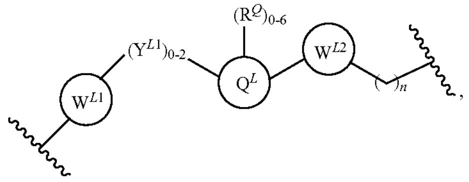

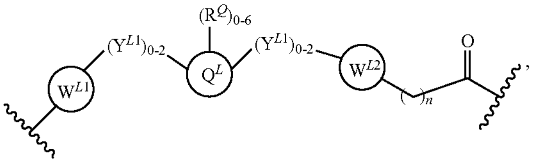

or

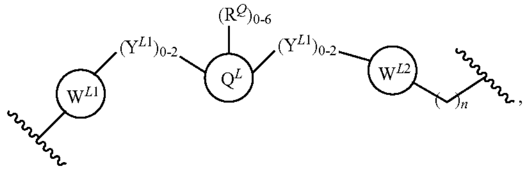

wherein:

$W^{L1}$ and $W^{L2}$ are each independently absent, aryl, heteroaryl, cyclic, heterocyclic, $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C ≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, optionally substituted linear or branched $C_1$-$C_6$ alkyl and optionally one or more C atoms are replaced with O; optionally substituted linear or branched $C_1$-$C_6$ alkoxy;

$Q^L$ is a 3-6 membered alicyclic or aromatic ring with 0-4 heteroatoms, optionally bridged, optionally substituted with 0-6 $R^Q$, each $R^Q$ is independently H, optionally substituted linear or branched $C_{1-6}$ alkyl (e.g., optionally substituted by 1 or more halo or $C_{1-6}$ alkoxy 1), or 2 $R^Q$ groups taken together with the atom they are attached to, form a 3-8 membered ring system containing 0-2 heteroatoms;

$R^{YL1}$, $R^{YL2}$ are each independently H, OH, optionally substituted linear or branched $C_{1-6}$ alkyl (e.g., optionally substituted by 1 or more halo or $C_{1-6}$ alkoxyl), or $R^1$, $R^2$ together with the atom they are attached to, form a 3-8 membered ring system containing 0-2 heteroatoms; n is 0-10; and

indicates the attachment point to the PTM or ULM moieties.

In additional embodiments, the linker group is optionally substituted (poly)ethyleneglycol having between 1 and about 100 ethylene glycol units (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc., ethylene glycol units), between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In any aspect or embodiment described herein, the linker (L) includes an optionally substituted $C_1$-$C_{100}$ alkyl (e.g., e.g., $C_1$, $C_2$, $C_3$, $C_4$, $C_5$, $C_6$, $C_7$, $C_8$, $C_9$, $C_{10}$, Cn, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, $C_{60}$, $C_{61}$, $C_{62}$, $C_{63}$, $C_{64}$, $C_{65}$, $C_{66}$, $C_{67}$, $C_{68}$, $C_{69}$, $C_{70}$, $C_{71}$, $C_{72}$, $C_{73}$, $C_{74}$, $C_{75}$, $C_{76}$, $C_{77}$, $C_{78}$, $C_{79}$, $C_{80}$, $C_{81}$, $C_{82}$, $C_{83}$, $C_{84}$, $C_{85}$, $C_{86}$, $C_{87}$, $C_{88}$, $C_{89}$, $C_{90}$, $C_{91}$, $C_{92}$, $C_{93}$, $C_{94}$, $C_{95}$, $C_{96}$, $C_{97}$, $C_{98}$, $C_{99}$, or $C_{100}$ alkyl), wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linker or adjacently located).

In any aspect or embodiment describe herein, the linker (L) includes an optionally substituted $C_1$-$C_{100}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, $C_{60}$, $C_{61}$, $C_{62}$, $C_{63}$, $C_{64}$, $C_{65}$, $C_{66}$, $C_{67}$, $C_{68}$, $C_{69}$, $C_{70}$, $C_{71}$, $C_{72}$, $C_{73}$, $C_{74}$, $C_{75}$, $C_{76}$, $C_{77}$, $C_{78}$, $C_{79}$, $C_{80}$, $C_{81}$, $C_{82}$, $C_{83}$, $C_{84}$, $C_{85}$, $C_{86}$, $C_{87}$, $C_{88}$, $C_{89}$, $C_{90}$, $C_{91}$, $C_{92}$, $C_{93}$, $C_{94}$, $C_{95}$, $C_{96}$, $C_{97}$, $C_{98}$, $C_{99}$, or $C_{100}$ alkyl), wherein:

each carbon is optionally substituted with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{14}$, CO, $CR^{L1}$═$CR^{L2}$, C≡C, $SiR^{L1}R^{L2}$, $P(O)R^{L1}$, $P(O)OR^{11}$, $NR^{L3}C$(═NCN)$NR^{14}$, $NR^{L3}C$(═NCN), $NR^{L3}C(═CNO_2)NR^{14}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$ heteocyclyl optionally substituted with 0-6 $R^{11}$ and/or $R^{L2}$ groups, $C_{5-13}$ spiroheterocyclyl optionally substituted with 0-8 $R^{L1}$ and/or $R^{12}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$ alkyl, CCH, CH═CH($C_{1-8}$alkyl), C($C_{1-8}$alkyl)═CH($C_{1-8}$alkyl), C($C_{1-8}$alkyl)═C$(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In any aspect or embodiment described herein, the linker (L) does not have heteroatom-heteroatom bonding (e.g., no heteroatoms are covalently linker or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

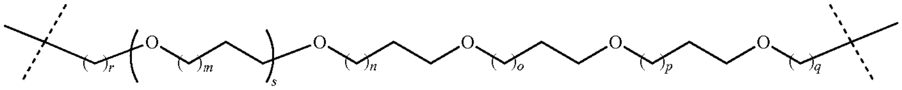
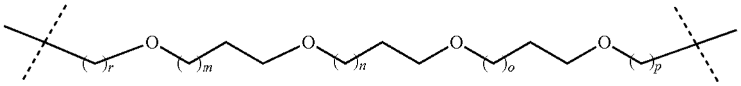
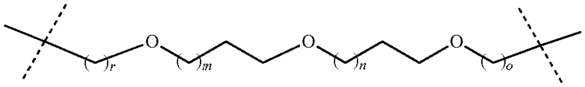 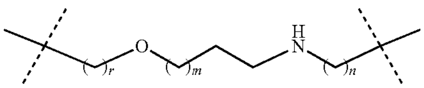
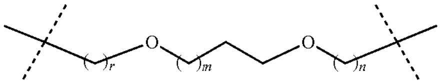 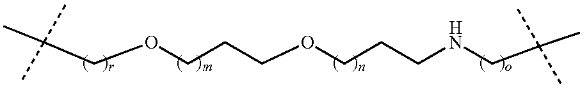
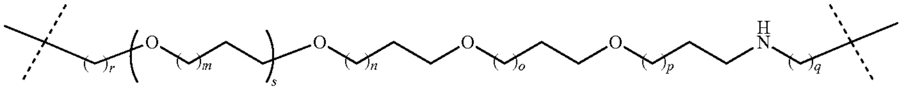
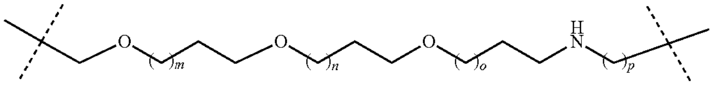
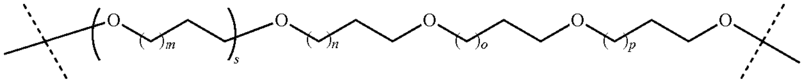
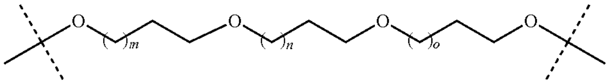 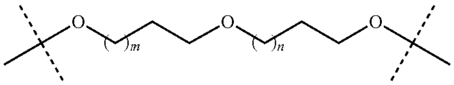
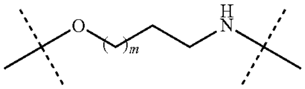 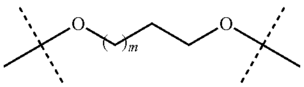 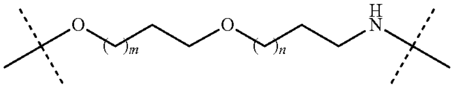
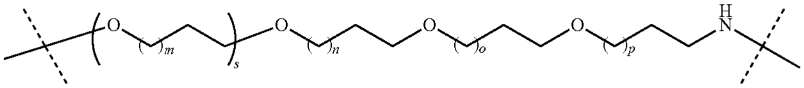
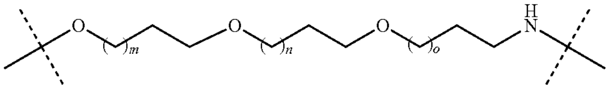
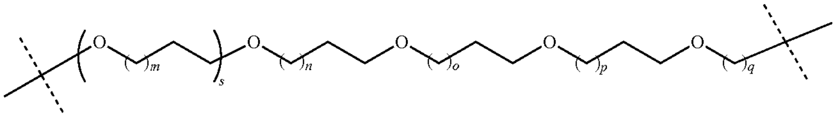
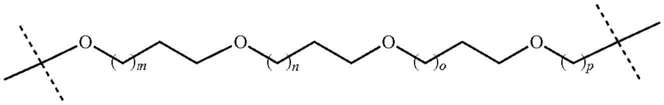
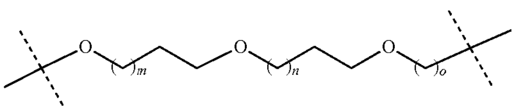 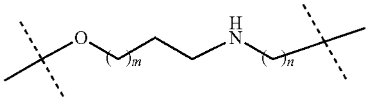
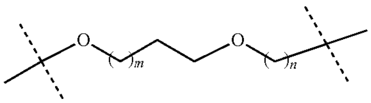 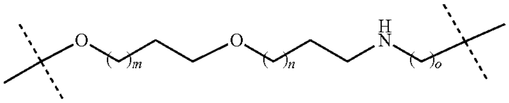
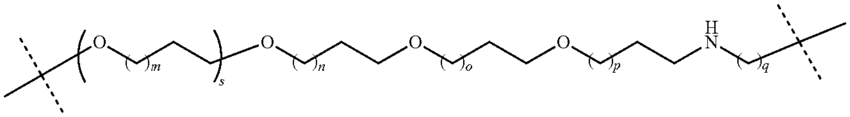
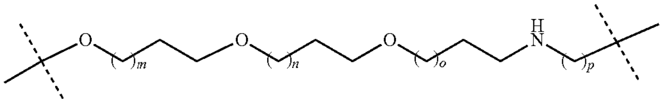, wherein carbon or oxygen may be substituted with a heteroatom selected from N, S, P, or Si atoms with an appropriate number of hydrogens to complete valency, and m, n, o, p, q, r, and s are independently selected from 0, 1, 2, 3, 4, 5, 6, 7, 8, 9, 10, 11, 12, 13, 14, 15, 16, 17, 18, 19, and 20.

In any aspect or embodiment described herein, the present disclosure is directed to a compound which comprises a PTM group as described above, which binds to a target protein or polypeptide (e.g., RAF), which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In any aspect or embodiment described herein, the linker group L is a group comprising one or more covalently connected structural units independently selected from the group consisting of:

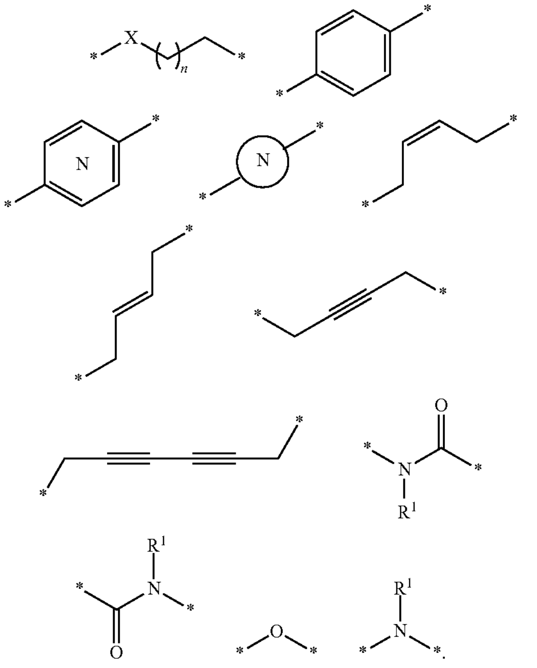

The X is selected from the group consisting of O, N, S, S(O) and $SO_2$; n is integer from 1-5, 5; $R^{L1}$ is hydrogen or alkyl,

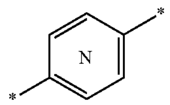

is a mono- or bicyclic aryl or heteroaryl optionally substituted with 1-3 substituents selected from alkyl, halogen, haloalkyl, hydroxy, alkoxy or cyano;

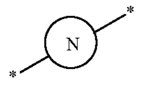

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosore. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: RAF inhibitors, Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase (e.g., RAF) is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes (e.g., c-RAF, A-RAF, and/or B-RAF) and prokaryotes including humans as targets for drug therapy, other animals, including domesticated animals, microbials for the determination of targets for antibiotics and other antimicrobials and plants, and even viruses (e.g., v-RAF and/or v-Mil), among numerous others.

The present disclosure may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer, cardiofaciocutaneous syndrome, neurofibromatosis type 1, Costello syndrome, Noonan Syndrome, LEOPARD syndrome. In certain additional embodiments, the disease is renal cell carcinoma, pancreatic cancer, colorectal cancer, lung cancer, ovarian cancer, thyroid cancer, pilocytic astrocytoma, prostate cancer, gastric cancer, hepatocellular carcinoma, and melanoma.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, cardiofaciocutaneous syndrome, neurofibromatosis type 1, Costello syndrome, Noonan Syndrome, LEOPARD syndrome, by virtue of the administration of effective amounts of at least one compound described herein. The disease state or condition may be a disease caused by a microbial agent or other exogenous agent such as a virus (e.g., murine retrovirus or avian retrovirus, such as avian retrovirus MH2), bacteria, fungus, protozoa or other microbe or may be a disease state, which is caused by overexpression of a protein and/or the presence of a protein that is constitutively activated, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFRlm, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras/Raf/MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose)

polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include RAF inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins.

Exemplary protein target moieties according to the present disclosure include, RAF inhibitors, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM is a small molecule comprising a B-RAF protein targeting moiety.

In any aspect or embodiment described herein, the PTM targets and/or binds RAF. For example, in any aspect or embodiment described herein, the PTM may comprise a chemical group selected from the group of chemical structures consisting of PTM-Ia or PTM-Ib:

PTM-Ia

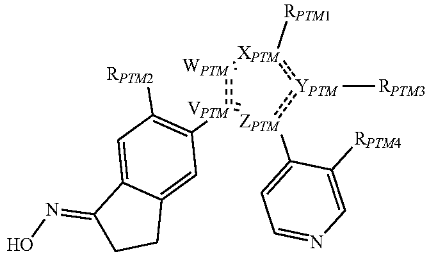

PTM-Ib

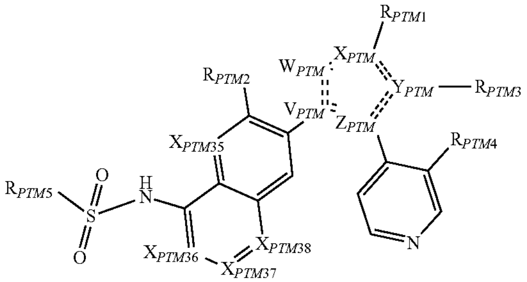

PTM-Ic

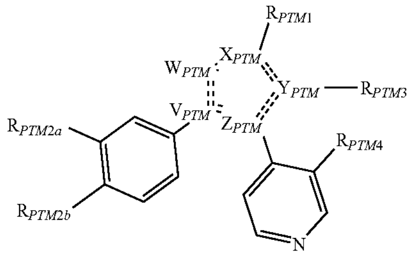

, wherein:

double dotted bonds are aromaric bonds;

$V_{PTM}$, $W_{PTM}$, $X_{PTM}$, $Y_{PTM}$, $Z_{PTM}$ is one of the following combinations: C, CH, N, N, C; C, N, N, CH, C; C, O, C, CH, C; C, S, C, CH, C; C, CH, C, O, C; C, CH, C, S, C; C, CH, N, CH, C; N, CH, C, CH, C; C, CH, C, CH, N; N, N, C, CH, C; N, CH, C, N, C; C, CH, C, N, N; C, N, C, CH, N; C, N, C, N, C; and C, N, N, N, C;

$X_{PTM35}$, $X_{PTM36}$, $X_{PTM37}$, and $X_{PTM38}$ are independently selected from CH and N;

$R_{PTM1}$ is covalently joined to a ULM, a chemical linker group (L), a CLM, an ILM, a VLM, MLM, a ULM', a CLM', a ILM', a VLM', a MLM', or combination thereof;

$R_{PTM2}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM2a}$ and $R_{PTM2b}$ is hydrogen, OH, halogen;

$R_{PTM3}$ is absent, hydrogen, aryl, methyl, ethyl, other alkyl, cyclic alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM4}$ is hydrogen, halogen, aryl, methyl, ethyl, $OCH_3$, $NHCH_3$ or MI-$CH_2$—$CH_2$-M2, wherein M1 is $CH_2$, O and NH, and M2 is hydrogen, alkyl, cyclic alkyl, aryl or heterocycle; and $R_{PTM5}$ is selected from the group consisting of

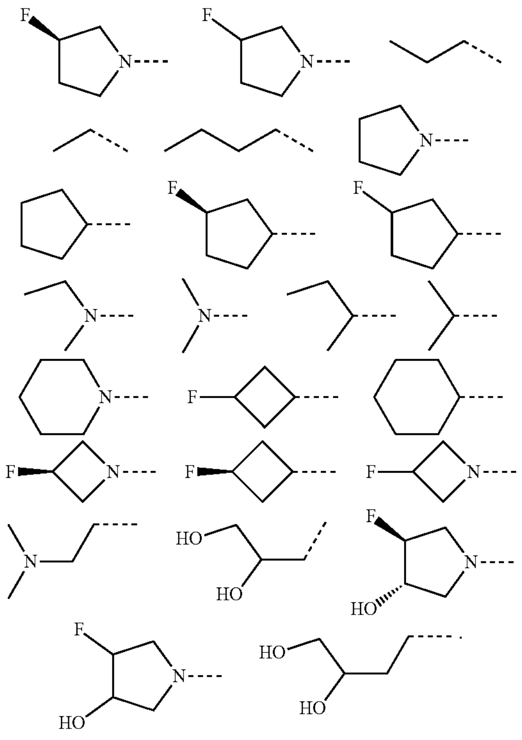

In any aspect or embodiment described herein, the PTM may comprise a chemical group selected from the group of chemical structures consisting of PTM-IIa or PTM-IIb:

PTM-IIa

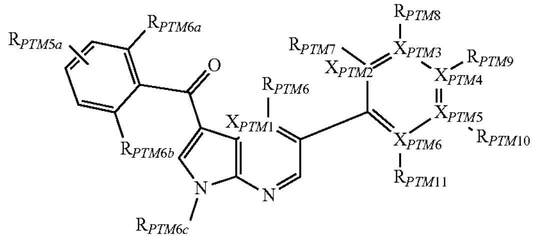

or

PTM-IIb

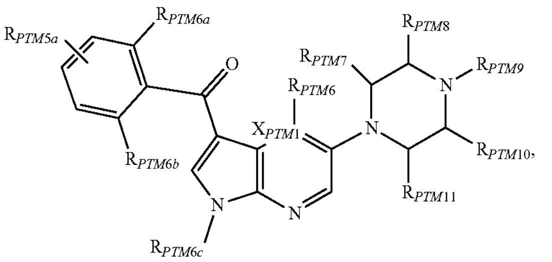

wherein:

$X_{PTM1}$, $X_{PTM2}$, $X_{PTM3}$, $X_{TMP4}$, $X_{PTM5}$, and $X_{PTM6}$ are independently selected from CH or N;

$R_{PTM5a}$ is selected from the group consisting of: bond, optionally substituted amine, optionally substituted amide (e.g., optionally substituted with an alkyl, methyl, ethyl, propyl, or butyl group), H,

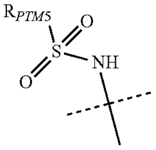,
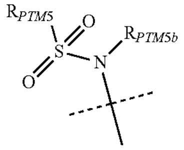,

—NHC(O)$R_{PTM5}$;

$R_{PTM5}$ is selected from the group consisting of

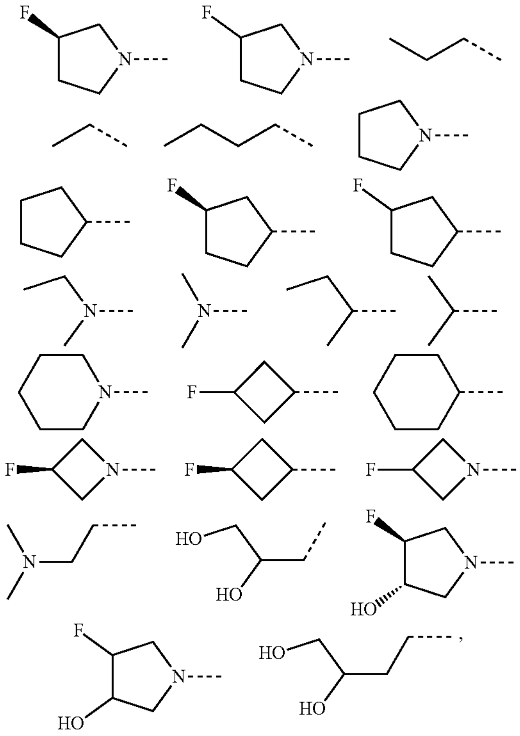

$R_{PTM5b}$ is hydrogen or a linear or branched C1-C4 alkyl (e.g., methyl or ethyl);

$R_{PTM6a}$ and $R_{PTM6b}$ are each independently selected from hydrogen, halogen, or optionally substituted linear or branched $C_1$-$C_6$ alkyl;

$R_{PTM6}$ is absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM6C}$ is hydrogen or a linear or branched C1-C4 alkyl (e.g., methyl or ethyl);

$R_{PTM7}$ is absent, hydrogen, halogen, aryl, methyl, ethyl, $OCH_3$, $NHCH_3$ or M1-$CH_2$—$CH_2$-M2, wherein M1 is $CH_2$, O or NH, and M2 is hydrogen, alkyl, cyclic alkyl, aryl or heterocycle;

$R_{PTM5}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM11}$ is absent, hydrogen, halogen, methyl, ethyl, $OCH_3$, NH $CH_3$ or M1-$CH_2$—$CH_2$-M2, wherein M1 is $CH_2$, O or NH, and M2 is hydrogen, alkyl, cyclic alkyl, aryl or heterocycle; and at least one of $R_{PTM8}$, $R_{PTM9}$ or $R_{PTM10}$ is modified to be covalently joined to a ULM, a chemical linker group (L), a CLM, an ILM, a VLM, MLM, a ULM', a CLM', a ILM', a VLM', a MLM', or combination thereof, or two of $R_{PTM5}$, $R_{PTM9}$, and RPTMW are modified to form a polycyclic (e.g., bicyclic) fused ring with a chemical linker group.

In certain embodiments, the PTM may comprise a chemical group selected from the group of chemical structures consisting of:

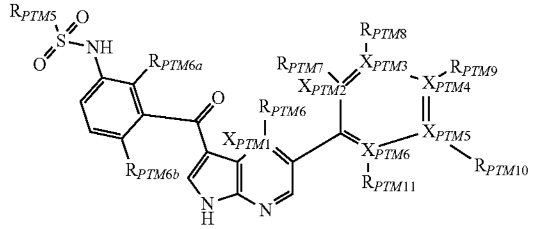

or

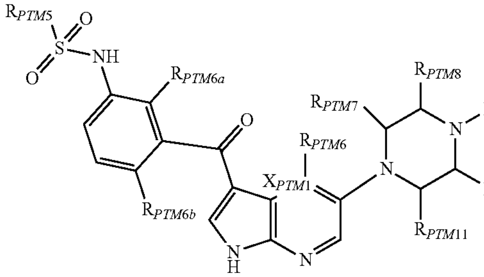

wherein $R_{PTM5}$, $R_{PTM6a}$, $R_{PTM6b}$, $R_{PTM6}$, $R_{PTM7}$, $R_{PTM8}$, $R_{PTM9}$, $R_{PTM10}$, $R_{PTM11}$ are as described herein.

In some embodiments, when $R_{PTM9}$ is the covalently joined position, $R_{PTM7}$ and $R_{PTM8}$ can be connected together via a covalent bond in a way to form a bicyclic group with the ring to which $R_{PTM7}$ and $R_{PTM8}$ are attached.

In other embodiments, when $R_{PTM8}$ is the covalently joined position, $R_{PTM9}$ and $R_{PTM10}$ can be connected together via a covalent bond in a way to form a bicyclic group with the ring to which $R_{PTM9}$ and $R_{PTM10}$ are attached.

In further embodiments, when $R_{PTM10}$ is the covalently joined position, $R_{PTM8}$ and $R_{PTM9}$ can be connected together via a covalent bond in a way to form a bicyclic group with the ring to which $R_{PTM8}$ and $R_{PTM9}$ are attached.

In any aspect or embodiment described herein, the PTM may comprise a chemical group selected from the group of chemical structures consisting of PTM-III:

wherein:

$X_{PTM7}$, $X_{PTM8}$, $X_{PTM9}$, $X_{PTM10}$, $X_{PTM11}$, $X_{PTM12}$, $X_{PTM13}$, $X_{PTM14}$, $X_{PTM15}$, $X_{PTM16}$, $X_{PTM17}$, $X_{PTM18}$, $X^{PTM19}$, $X_{PTM20}$ are independently CH or N;

$R_{PTM12}$, $R_{PTM13}$, $R_{PTM14}$, $R_{PTM15}$, $R_{PTM16}$, $R_{PTM17}$, $R_{PTM18}$, $R_{PTM19}$ are independently selected from the group consisting of absent, hydrogen, halogen, aryl, heteroaryl, cycloalkyl, heterocycle, methyl, ethyl, other alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM20}$ is a small group containing less than four non-hydrogen atoms;

$R_{PTM21}$ is selected from the group consisting of trifluoromethyl, chloro, bromo, fluoro, methyl, ethyl, propyl, isopropyl, tert-butyl, butyl, iso-butyl, cyclopropyl, cyclobutyl, cyclopentyl, cyclohexyl, $OCH_3$, $NHCH_3$, dimethylamino or M1-$CH_2$—$CH_2$-M2, wherein M1 is $CH_2$, O or NH, and M2 is hydrogen, alkyl, cyclic alkyl, aryl or heterocycle; and at least one of $R_{PTM12}$, $R_{PTM13}$ and $R_{PTM16}$ is modified to be covalently joined to a ULM, a chemical linker group (L), a CLM, an ILM, a VLM, MLM, a ULM', a CLM', a ILM', a VLM', a MLM', or combination thereof.

In some embodiments, when $R_{PTM12}$ is the covalently joined position, $R_{PTM13}$ and $R_{PTM14}$ can be connected together via a covalent bond in a way to form a bicyclic group with the ring to which $R_{PTM13}$ and $R_{PTM14}$ are attached; and/or $R_{PTM15}$ and $R_{PTM16}$ can be connected together via a covalent bond in a way to form a bicyclic group with the ring to which $R_{PTM15}$ and $R_{PTM16}$ are attached.

In other embodiments, when $R_{PTM13}$ is the covalently joined position, $R_{PTM12}$ and $R_{PTM16}$ can be connected together via a covalent bond in a way to form a bicyclic group with the ring to which $R_{PTM12}$ and $R_{PTM16}$ are attached; and/or $R_{PTM15}$ and $R_{PTM16}$ can be connected together via a covalent bond in a way to form a bicyclic group with the ring to which $R_{PTM15}$ and $R_{PTM16}$ are attached.

In further embodiments, when $R_{PTM16}$ is the covalently joined position, $R_{PTM12}$ and $R_{PTM13}$ can be connected together via a covalent bond in a way to form a bicyclic group with the ring to which $R_{PTM12}$ and $R_{PTM13}$ are attached; and/or $R_{PTM13}$ and $R_{PTM14}$ can be connected together via a covalent bond in a way to form a bicyclic group with the ring to which $R_{PTM13}$ and $R_{PTM14}$ are attached.

PTM-III

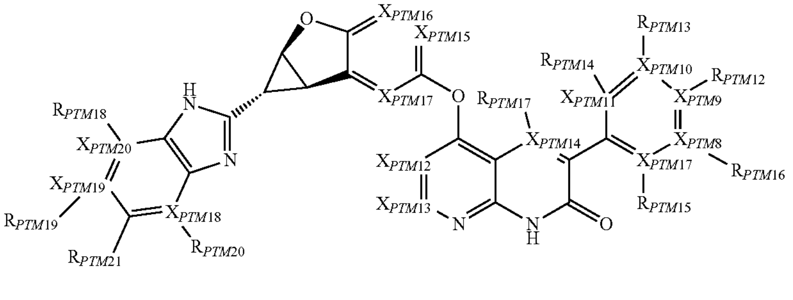

In any aspect or embodiment described herein, the PTM may comprise a chemical group selected from the group of chemical structures consisting of PTM-IVa or PTM-IVb:

PTM-IVa

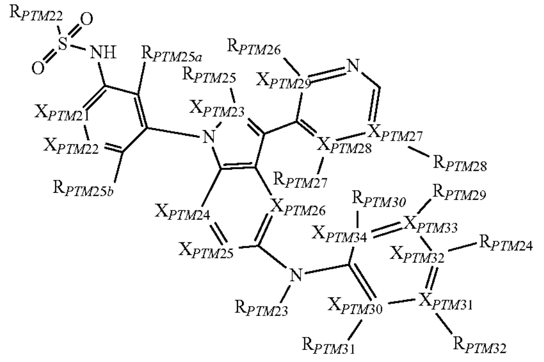

or

PTM-IVb

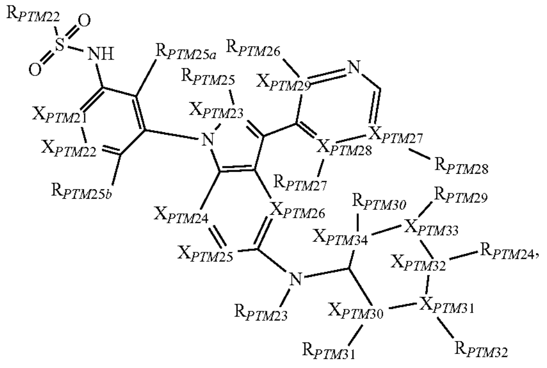

wherein:

$X_{PTM21}$, $X_{PTM22}$, $X_{PTM23}$, $X_{PTM24}$, $X_{PTM25}$, $X_{PTM26}$, $X_{PTM27}$, $X_{PTM28}$, $X_{PTM29}$, $X_{PTM30}$, $X_{PTM31}$, $X_{PTM32}$, $X_{PTM33}$, $X_{TMP34}$ are independently CH or N;

$R_{PTM22}$ is selected from the group consisting of

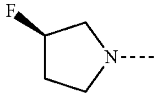 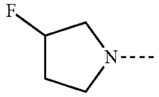 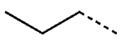

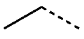 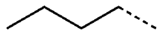 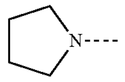

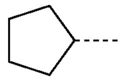 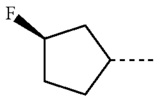 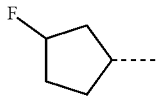

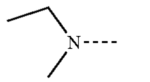 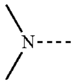 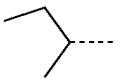 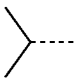

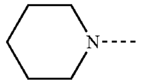 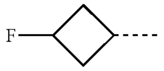 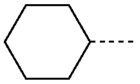

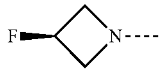 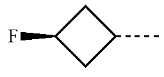 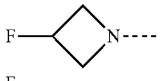

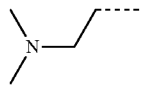 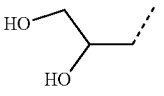 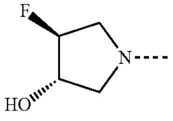

-continued

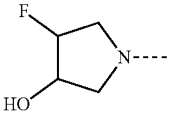 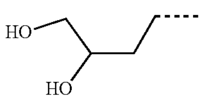

$R_{PTM25a}$ and $R_{PTM25b}$ are each independently selected from hydrogen, halogen, or $C_1$-$C_6$ alkyl (linear, branched, optionally substituted);

$R_{PTM23}$, $R_{PTM24}$, $R_{PTM28}$, $R_{PTM29}$, $R_{PTM30}$, $R_{PTM31}$, $R_{PTM32}$ are independently selected from the group consisting of absent, bond, hydrogen, halogen, aryl (optionally substituted), heteroaryl (optionally substituted), cycloalkyl (optionally substituted), heterocycle (optionally substituted), methyl, ethyl (optionally substituted), other alkyl (linear, branched, optionally substituted), $OCH_3$, $NHCH_3$ or M1-$CH_2$—$CH_2$-M2, wherein M1 is $CH_2$, O and NH, and M2 is hydrogen, alkyl (linear, branched, optionally substituted), cyclic alkyl (optionally substituted), aryl (optionally substituted) or heterocycle (optionally substituted); and $R_{PTM25}$ is absent, hydrogen, halogen, $C_1$-$C_6$ alkyl (linear, branched, optionally substituted), $OCH_3$, $NHCH_3$ or $SCH_3$;

$R_{PTM26}$ is absent, hydrogen, halogen, $C_1$-$C_6$ alkyl (linear, branched, optionally substituted), $OCH_3$, $NHCH_3$ or $SCH_3$;

$R_{PTM27}$ is selected from the group consisting of absent, hydrogen, halogen, $C_1$-$C_6$ alkyl (linear, branched, optionally substituted), $OCH_3$, $NHCH_3$ or $SCH_3$; and at least one of $R_{PTM24}$, $R_{PTM29}$, $R_{PTM32}$ is modified to be covalently joined to a ULM, a chemical linker group (L), a CLM, an ILM, a VLM, MLM, a ULM', a CLM', a ILM', a VLM', a MLM', or combination thereof.

In some embodiments, when $R_{PTM24}$ is the covalently joined position, $R_{PTM31}$ and $R_{PTM32}$ can be connected together via a covalent bond in a way to form a bicyclic group with the ring to which $R_{PTM31}$ and $R_{PTM32}$ are attached; or $R_{PTM29}$ and $R_{PTM30}$ can be connected together via a covalent bond in a way to form a bicyclic group with the ring to which $R_{PTM29}$ and $R_{PTM30}$ are attached.

In other embodiments, when $R_{PTM29}$ is the covalently joined position, $R_{PTM24}$ and $R_{PTM32}$ can be connected together via a covalent bond in a way to form a bicyclic group with the ring to which $R_{PTM24}$ and $R_{PTM32}$ are attached; and/or $R_{PTM31}$ and $R_{PTM32}$ can be connected together via a covalent bond in a way to form a bicyclic group with the ring to which $R_{PTM31}$ and $R_{PTM32}$ are attached.

In further embodiments, when $R_{PTM32}$ is the covalently joined position, $R_{PTM24}$ and $R_{PTM29}$ can be connected together via a covalent bond in a way to form a bicyclic group with the ring to which $R_{PTM24}$ and $R_{PTM29}$ are attached; and/or $R_{PTM29}$ and $R_{PTM30}$ can be connected together via a covalent bond in a way to form a bicyclic group with the ring to which $R_{PTM29}$ and $R_{PTM30}$ are attached.

In any aspect or embodiment described herein, the PTM may comprise a chemical group selected from the group of chemical structures consisting of PTM-Va or PTM-Vb:

PTM-Va

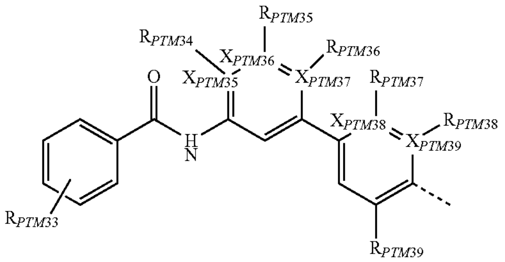

or

PTM-Vb

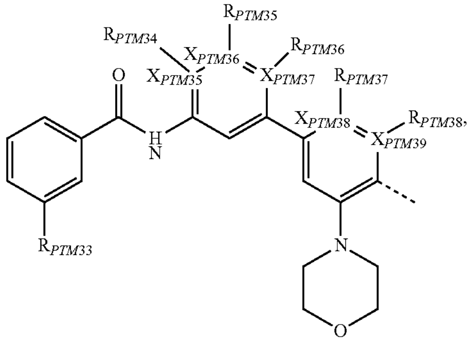

wherein:

$X_{PTM35}$, $X_{PTM36}$, $X_{PTM37}$, $X_{PTM38}$, and $X_{PTM39}$ are independently CH or N;

$R_{PTM33}$ is a halogen or a linear or branched C1-C4 haloalkyl;

$R_{PTM34}$, $R_{PTM35}$, $R_{PTM36}$, $R_{PTM37}$, and $R_{PTM38}$ are each independently selected from hydrogen, halogen, or linear or branched $C_1$-$C_4$ alkyl (e.g., methyl, ethyl, propyl, or butyl);

$R_{PTM39}$ is an optionally substituted C4-C7 heterocycloalkyl (e.g., an optionally substituted C5 or C6 heterocycloalkyl); and

 is the point of attachment with a ULM, a chemical linker group (L), a CLM, an ILM, a VLM, MLM, a ULM', a CLM', a ILM', a VLM', a MLM', or combination thereof.

In any aspect or embodiments described herein, the PTM is selected from the group consisting of chemical structures PTM-1, PTM-2, PTM-3, PTM-4, PTM-5, PTM-6, PTM-7, PTM-8, PTM-9, PTM-10, PTM-11, PTM-12, and PTM-13:

PTM-1

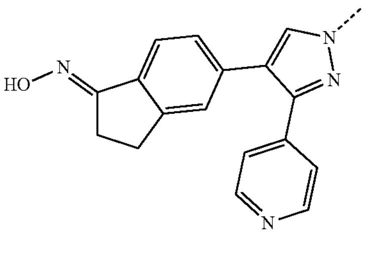

-continued

PTM-2

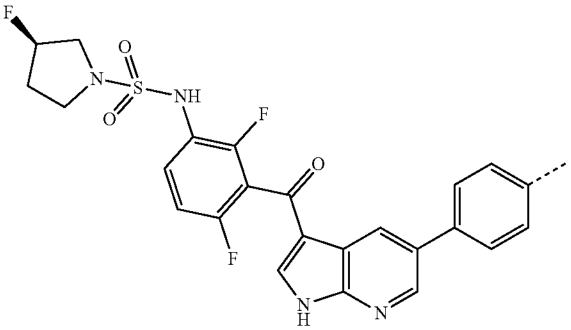

PTM-3

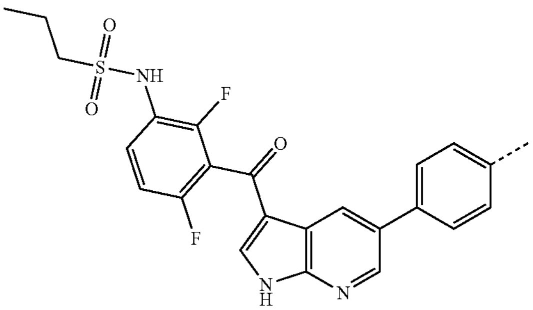

PTM-4

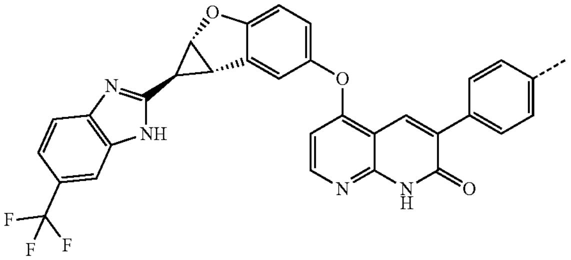

PTM-5

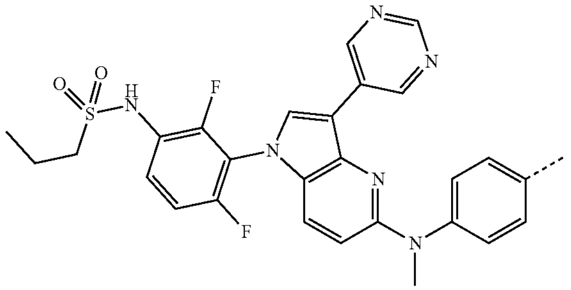

PTM-6

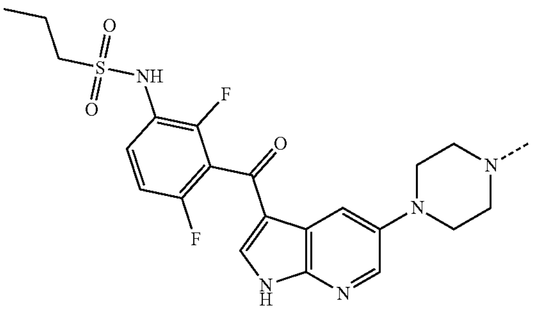

-continued
PTM-7
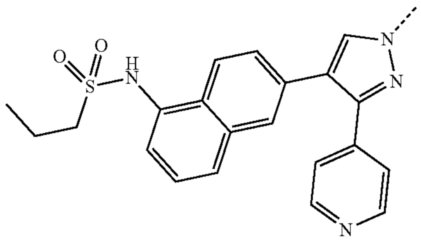
PTM-8
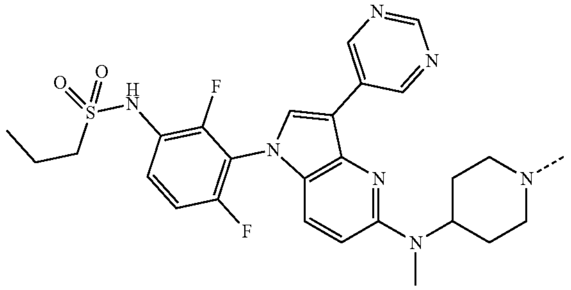
PTM-9
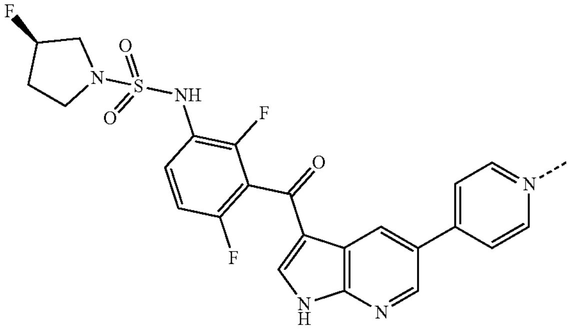
PTM-10
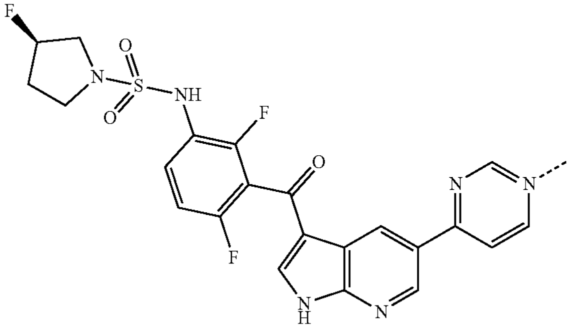
PTM-11
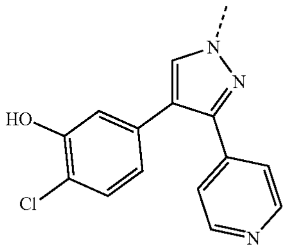
-continued
PTM-12
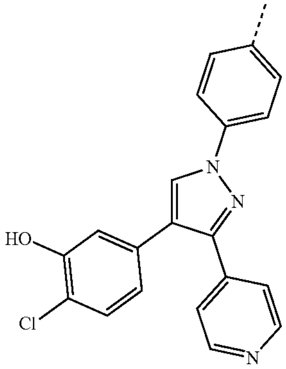
PTM-13
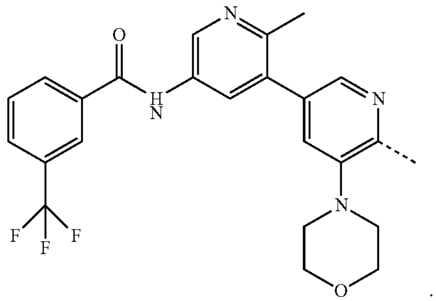
In any aspect or embodiment described herein, the ULM is selected from the group consisting of:
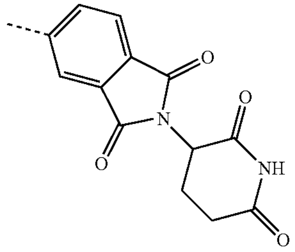
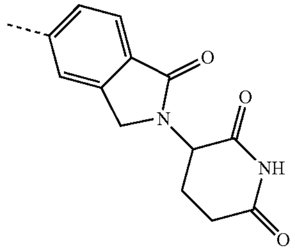
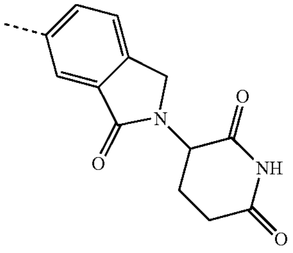
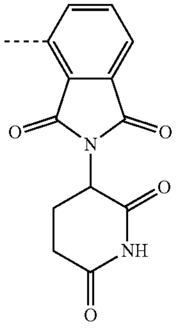

-continued

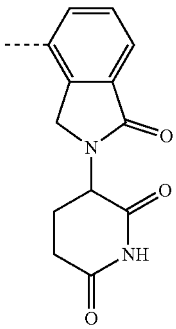

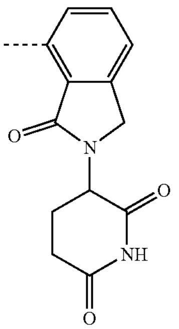

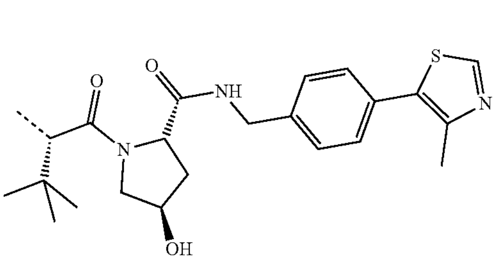

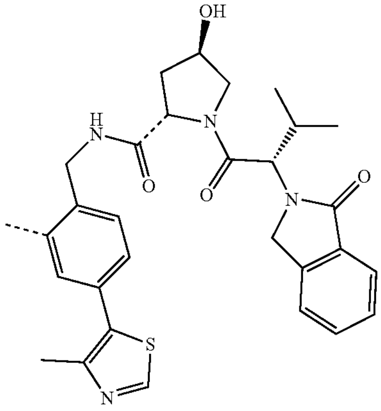

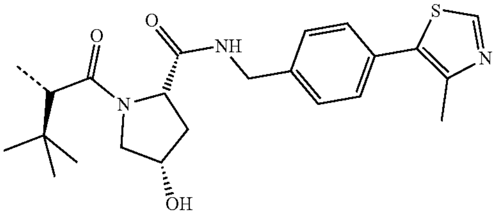

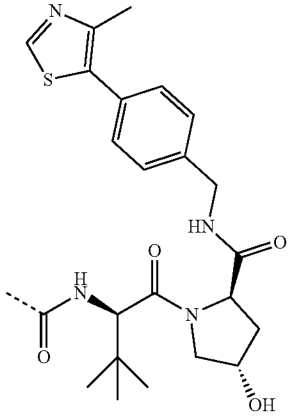

-continued

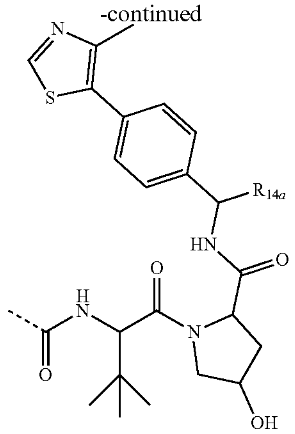

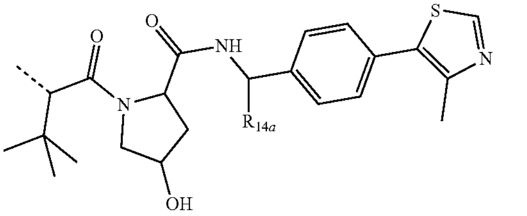

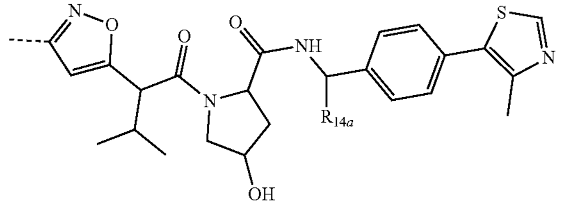

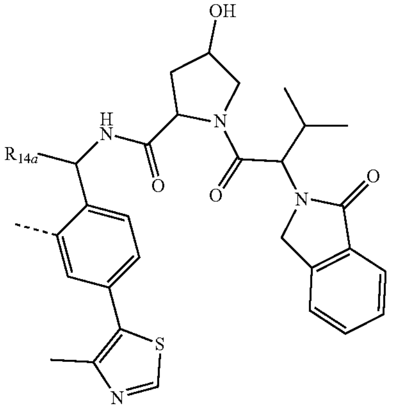

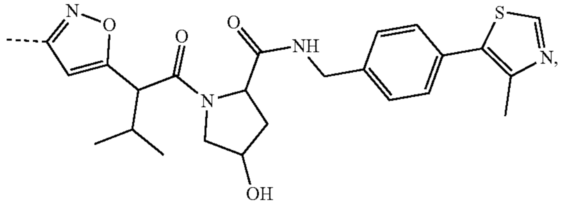

wherein the $R_{14a}$ is a H, methyl or hydroxymethyl.

In any aspect or embodiment described herein, at least one of: (i) the PTM is selected from the PTMs of compounds 1-873 or 307-873 of the present disclosure; (ii) the chemical linker group (L) is selected from the linkers of compounds 1-873 or 307-873 of the present disclosure; (iii) the ULM is selected from the ULMs of compounds 1-873 or 307-873 of the present disclosure; (iv) the compound further comprises a prodrug chemical moiety selected from the PTMs of compounds 796-873, or (v) a combination thereof.

In any aspect or embodiment described herein, the ULM is selected from the group consisting of:
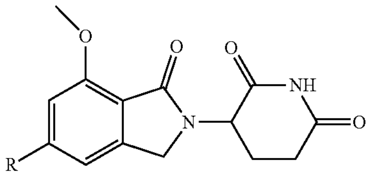
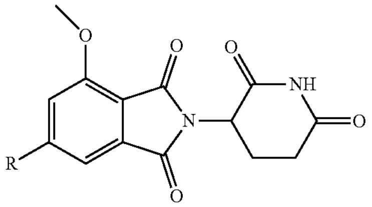
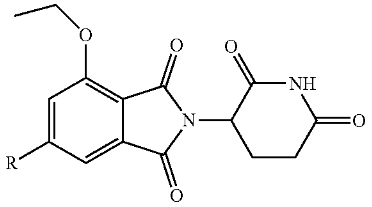
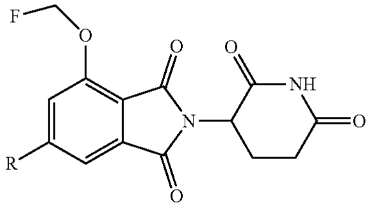
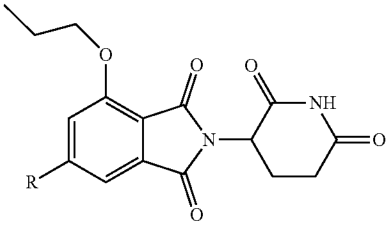
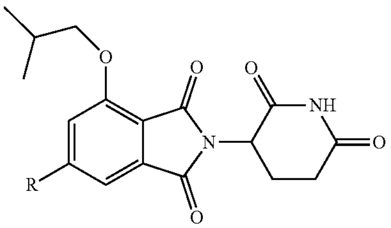
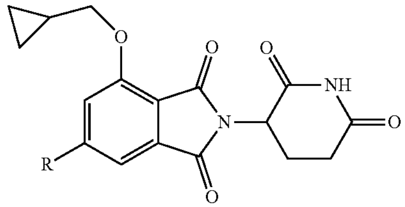
-continued
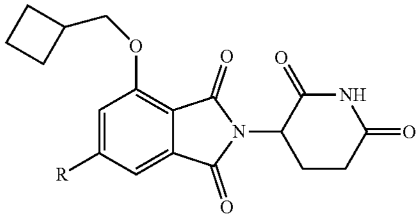
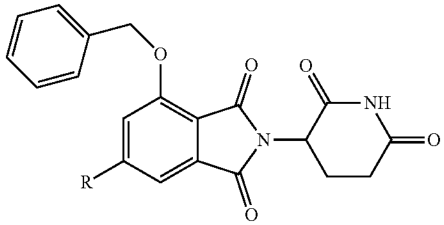
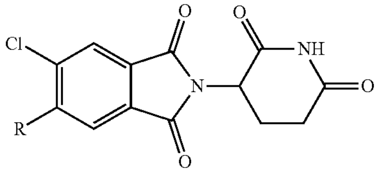
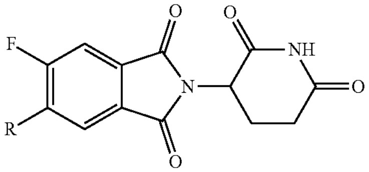
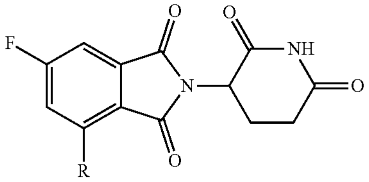
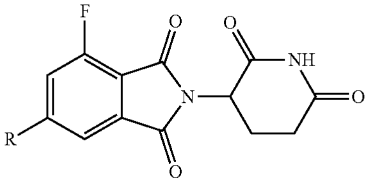
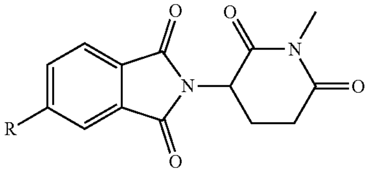
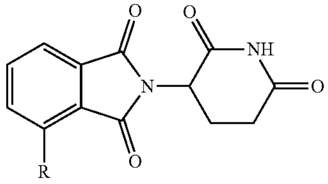
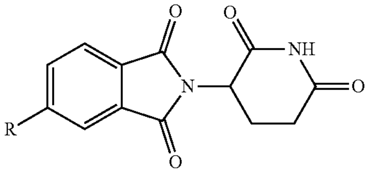

-continued
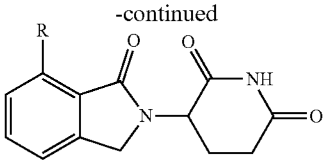
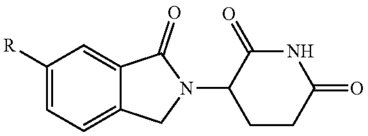
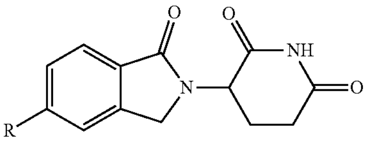
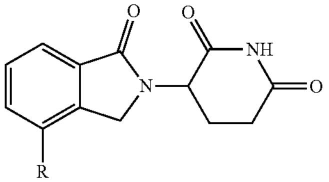
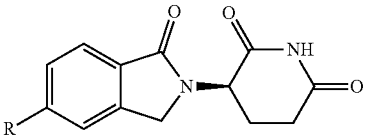
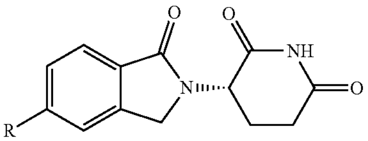
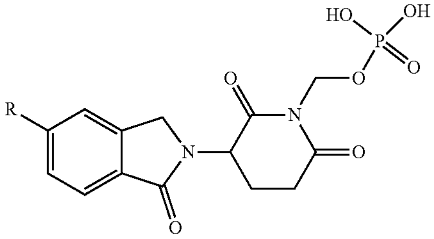
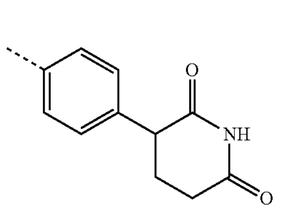
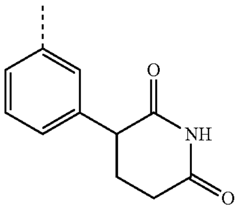
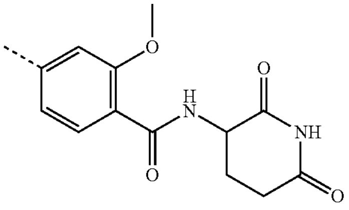
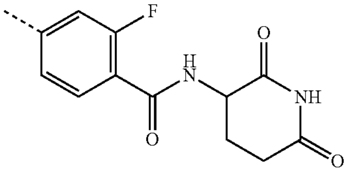
-continued
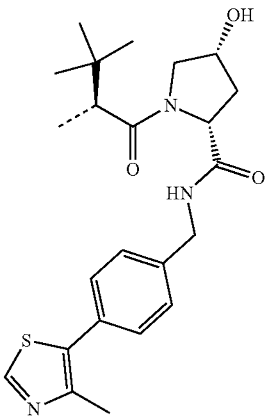
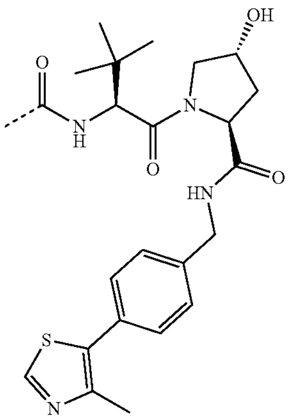
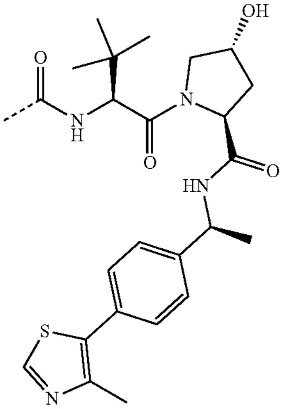
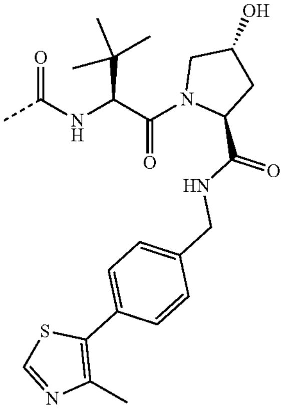
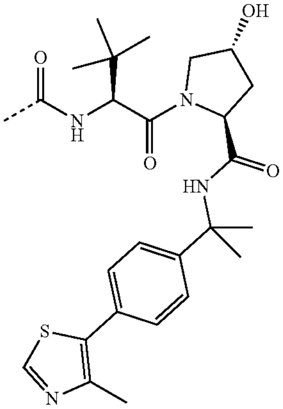
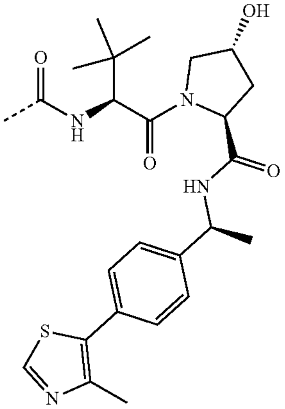
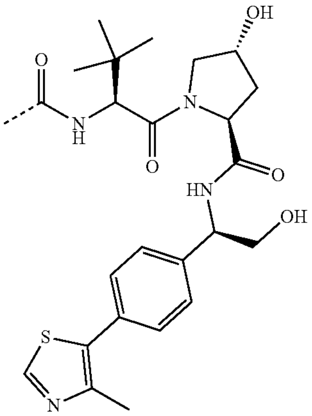

-continued
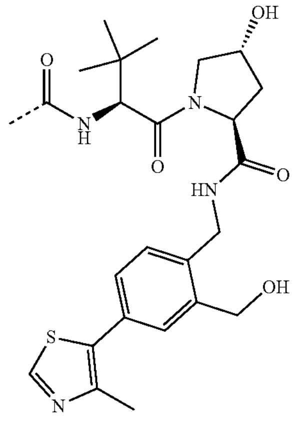
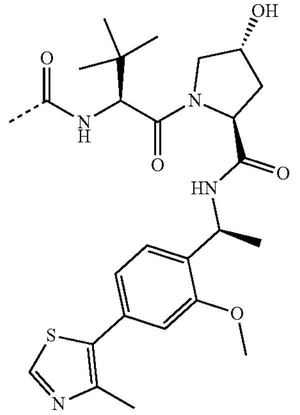
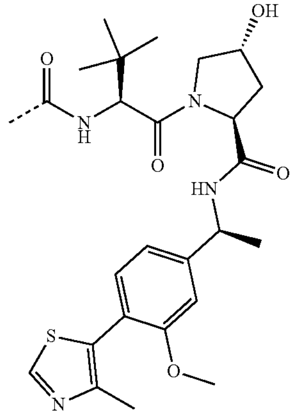
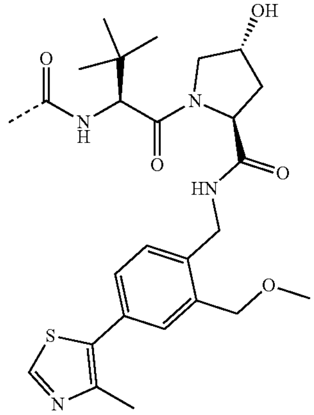
-continued
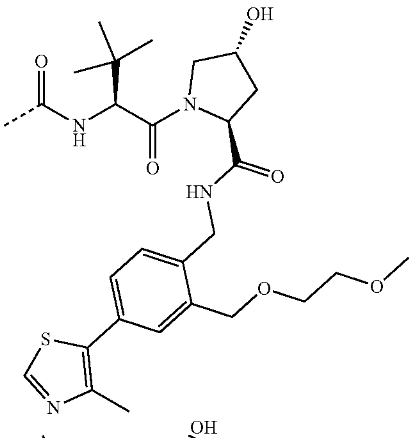
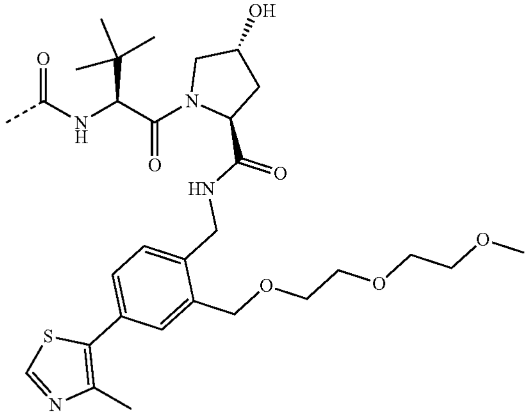
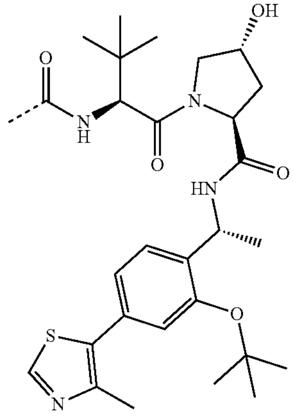
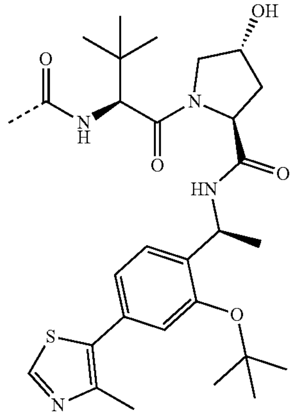

-continued
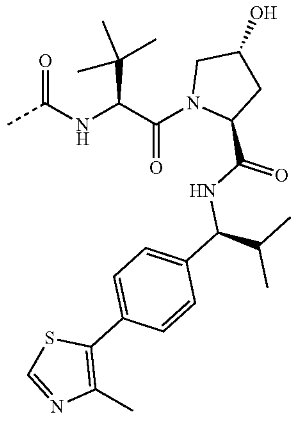
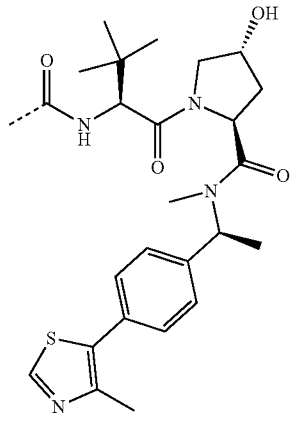
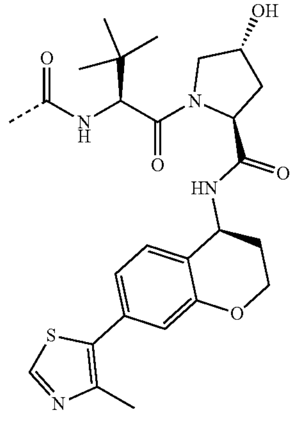
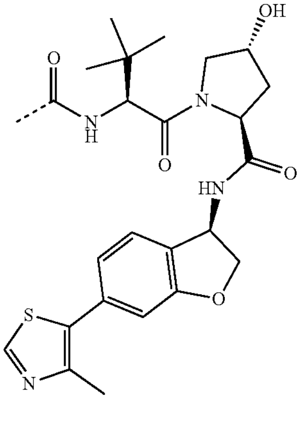
-continued
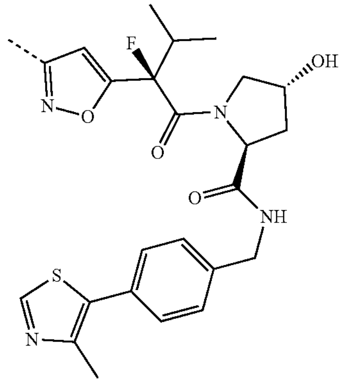
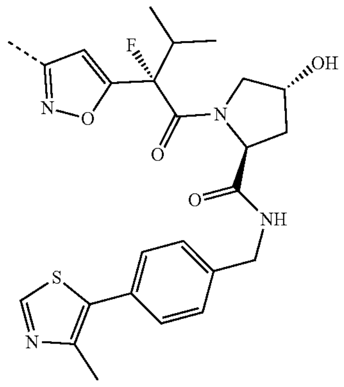
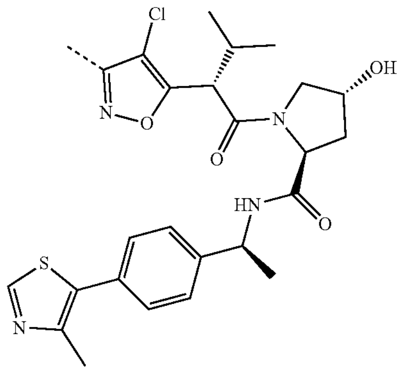
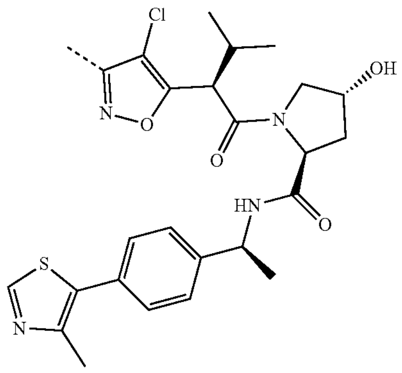

-continued
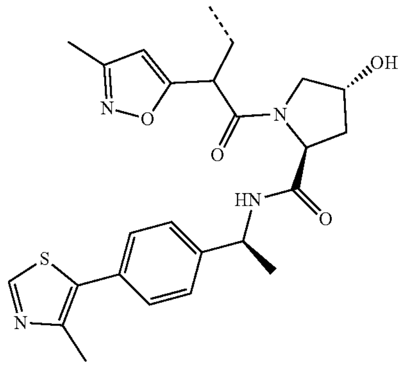
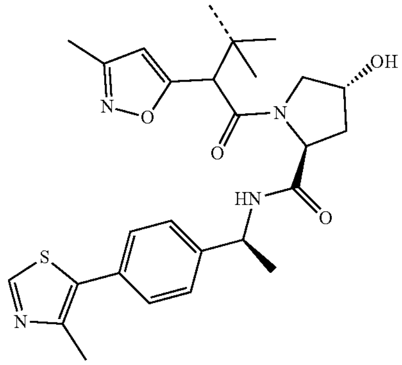
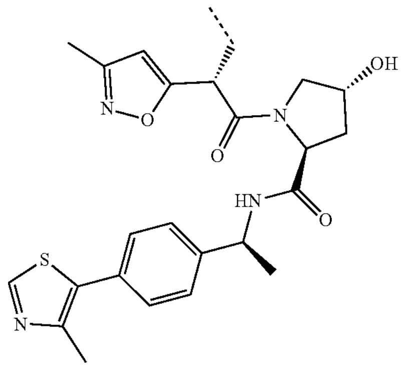
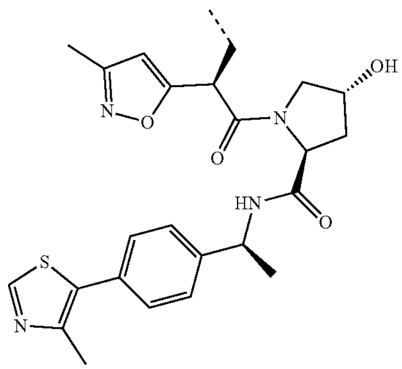
-continued
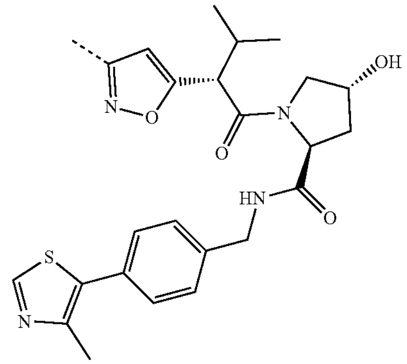
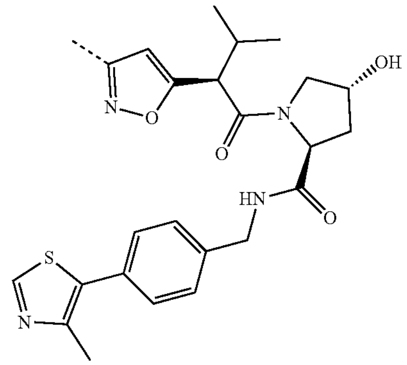
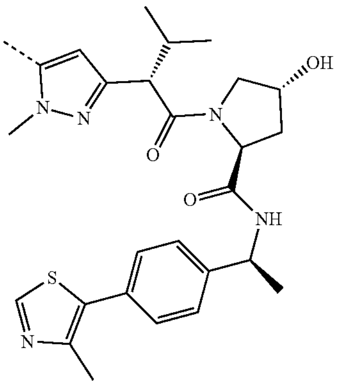
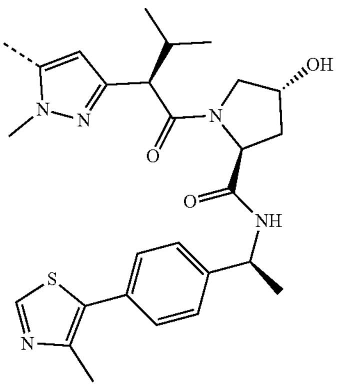

-continued
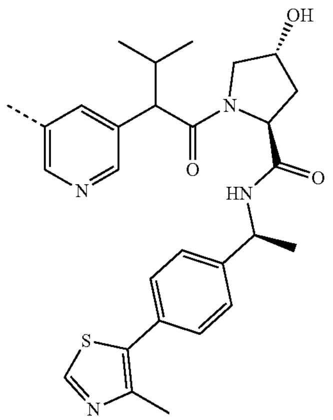
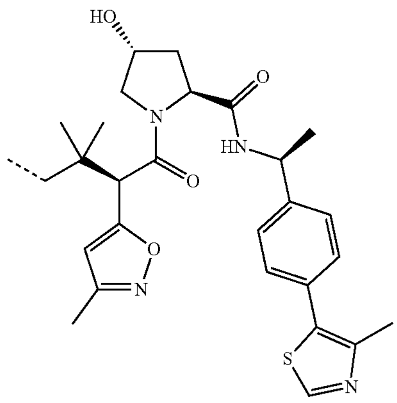
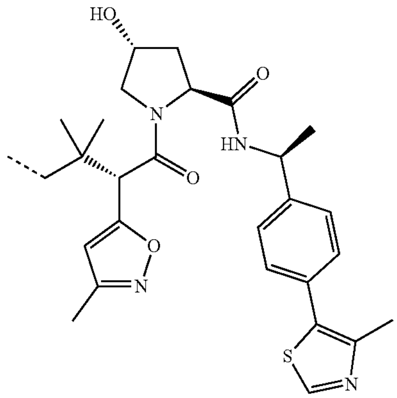
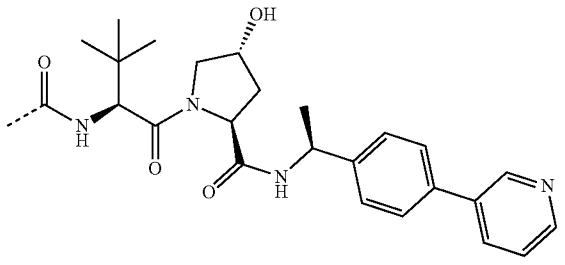
-continued
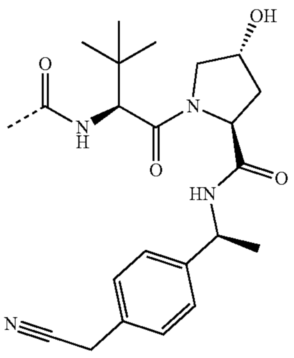
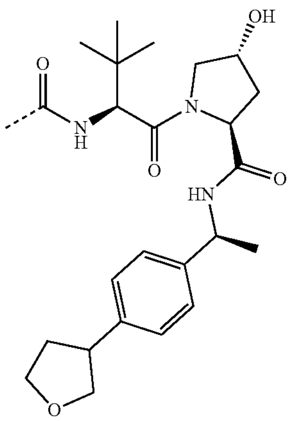
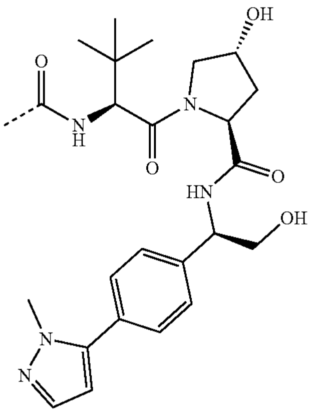
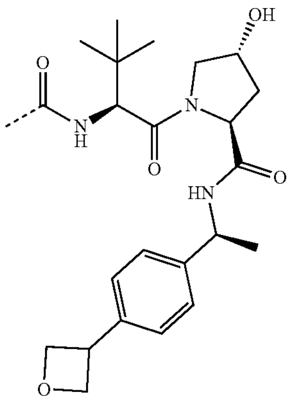

-continued

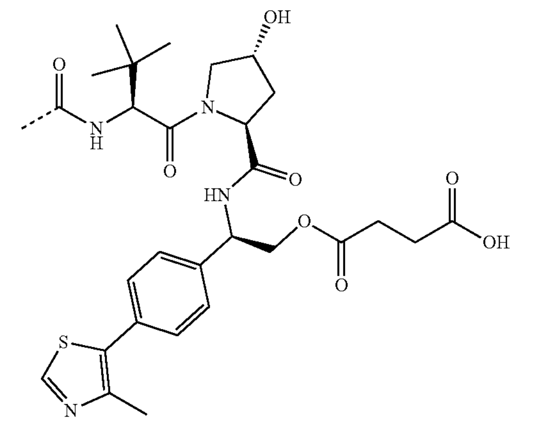

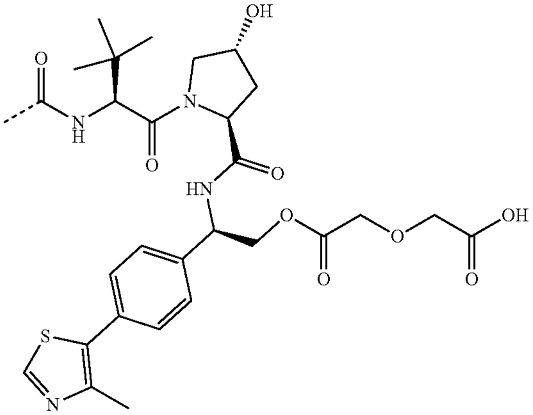

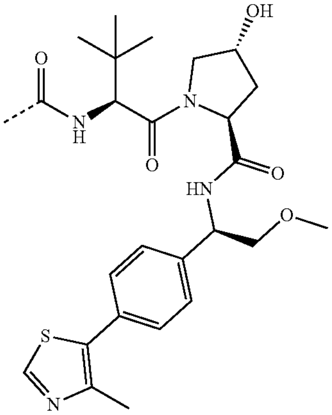

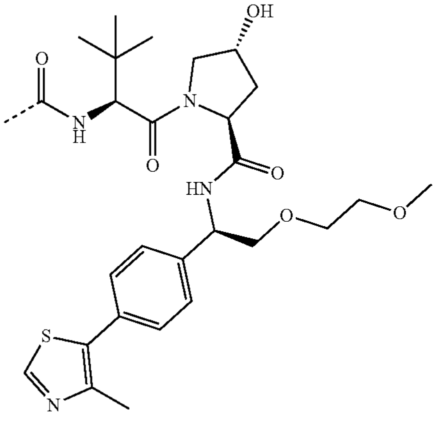

and

-continued

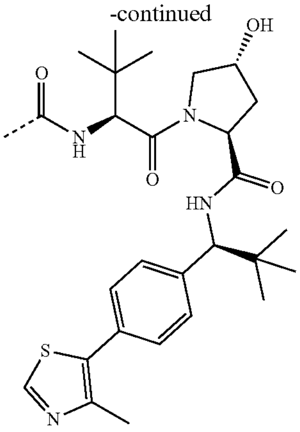

.

Prodrug Bifunctional Compounds

In any aspect or embodiment described herein, the bifunctional compound of the present disclosure or the prodrug thereof further includes a plurality of ethylene glycol units. In any aspect or embodiment described herein, the bifunctional compounds of the present disclosure or the prodrug thereof further includes at least one (e.g., 1, 2, 3, 4, 5, 6, 7, 8, or more) polyethylene glycol (PEG) chain. In any aspect or embodiment described herein, the bifunctional compound of the present disclosure or the prodrug thereof further includes a plurality (e.g., 2, 3, 4, 5, 6, 7, 8, or more) polyethylene glycol chains that have uniform chain length or a mixture of chain lengths. In any aspect or embodiment described herein, the bifunctional compound or the prodrug thereof further includes a prodrug portion selected from exemplary compounds 796-873.

In any aspect or embodiment described herein, the bifunctional compound of the present disclosure or the prodrug thereof further includes at least one (e.g., 1, 2, 3, 4, 5, 6, 7, 8, or more) polyethyelene glycol chain as described herein, wherein each polyethylene glycol chain is covalently linked to the bifunctional compound at the same point as the PEG chain attachment in a compound selected from exemplary compounds 796-873. In any aspect or embodiment described herein, each PEG chain is attached directly or indirectly via a variable (e.g., via a methyl group or an O) or in place of a variable of the VLM described herein (e.g., $R^P$, $R^{14a}$, $R^{14b}$, W4, W5, $R^{1'}$, $R^{2'}$, $R^{3'}$), the CLM described herein (e.g., G or G'), or a PTM as described herein (e.g., $R_{PTM6C}$). For example, in any aspect or embodiment described herein with a VLM, the $R^P$, $R^{14A}$, $R^{14b}$, or a combination thereof is modified to be covalently linked (e.g., the hydroxyl group of $R^P$ or $R^{1'}$, the methyl group of $R^{14a}$, $R^{14b}$, or W5 is modified to be covalently linked) directly or indirectly to a moiety that includes a PEG chain or is replaced with a moiety that includes a PEG chain. Additionally, in any aspect or embodiment described herein with a CLM, the G, G', or a combination thereof is modified to be covalently linked (e.g., they methyl of G or G' is modified to be covalently linked) directly or indirectly to a moiety that includes a PEG chain or is replaced with a moiety that includes a PEG chain.

In any aspect or embodiment described herein, the bifunctional compound of the present disclosure or the prodrug thereof includes at least one (e.g., 1, 2, 3, 4, 5, 6, 7, 8, or more)

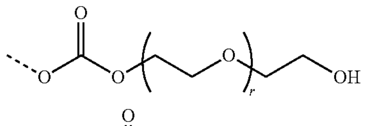

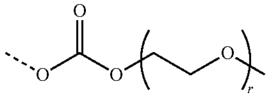

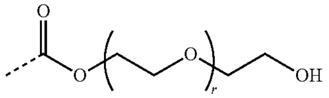

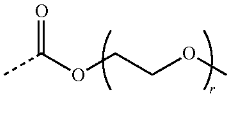

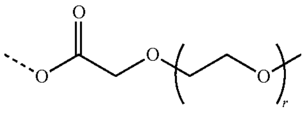

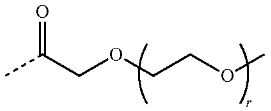

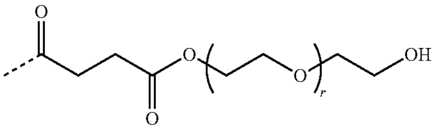

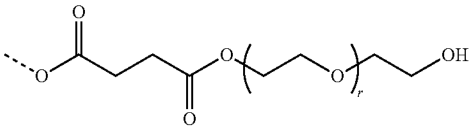

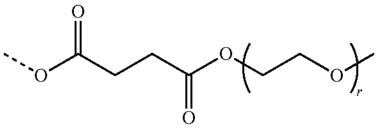

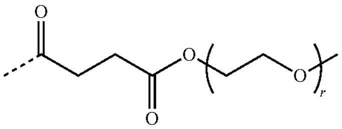

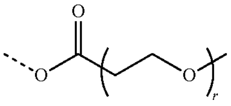

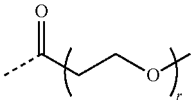

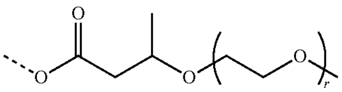

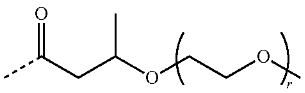

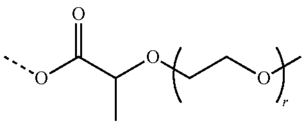

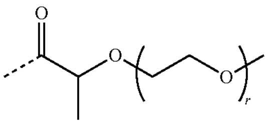

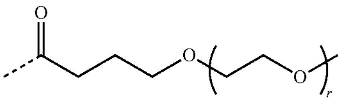

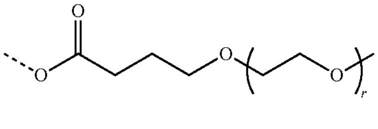

-continued

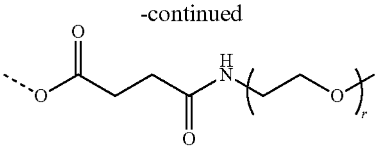

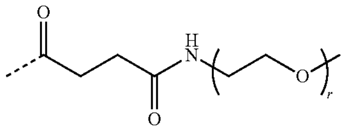

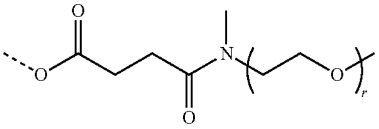

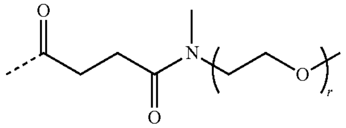

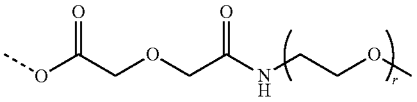

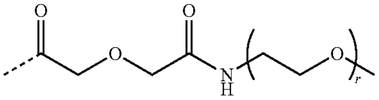

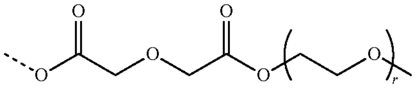

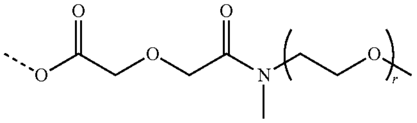

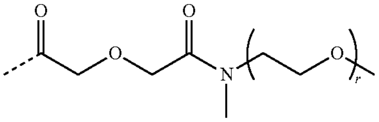

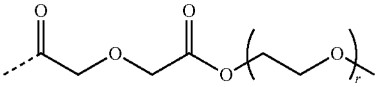

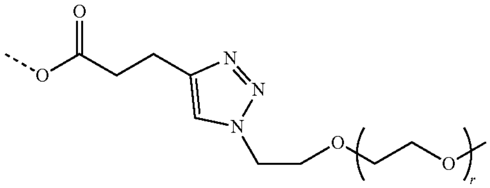

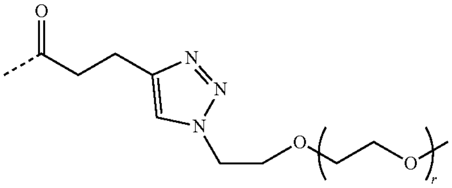, wherein r is an integer from 8 to 35 (e.g., 8, 9, 10, 11, 12, 13, 14, 15, 16, 17, 18, 19, 20, 21, 22, 23, 24, 25, 26, 27, 28, 29, 30, 31, 32, 33, 34, or 35). For example, in any aspect or embodiment described herein with a VLM, the $R^P$, $R^{14A}$, $R^{14b}$, or a combination thereof is modified to be covalently linked (e.g., the hydroxyl group of $R^P$, the methyl group of $R^{14a}$, $R^{14b}$, or W5 is modified to be covalently linked) directly or indirectly to one of the above recited structures or is replaced with one of the above recited structures. Additionally, in any aspect or embodiment described herein with a CLM, the G, G', or a combination thereof is modified to be covalently linked (e.g., they methyl of G or G' is modified to be covalently linked) directly or indirectly to one of the above recited structures or is replaced with one of the above recited structures. For example, in any aspect or embodiment described herein, each PEG chain can be attached to the VLM, CLM, or PTM via a chemical group selected from:

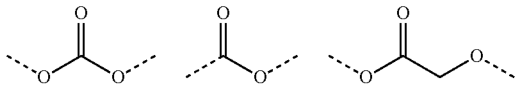

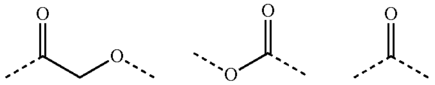

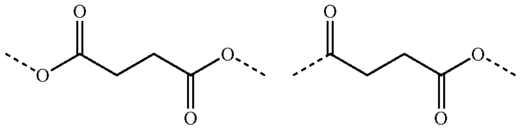

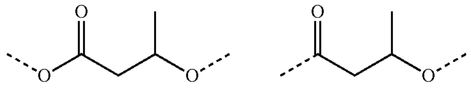

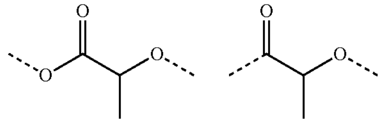

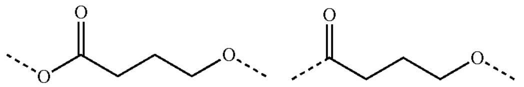

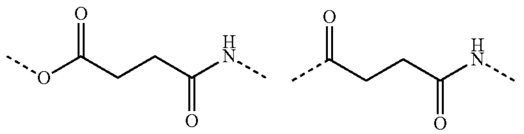

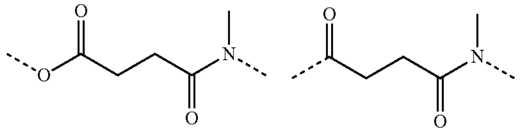

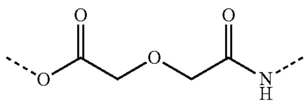

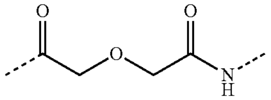

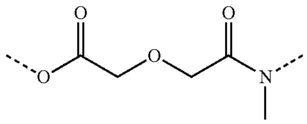

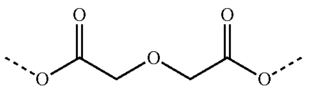

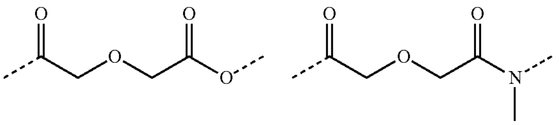

-continued

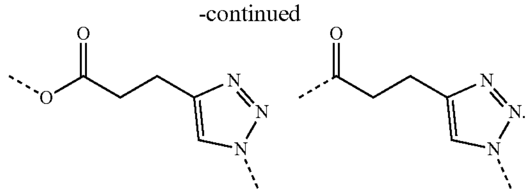

In any aspect or embodiment described herein, the polyethylene glycol chain of the bifunctional compound or prodrug thereof includes or is about 8 ethylene glycol units to about 35 (e.g., 8, 9, 10, 11, 12, 13, 14, 15, 16, 17, 18, 19, 20, 21, 22, 23, 24, 25, 26, 27, 28, 29, 30, 31, 32, 33, 34, or 35), about 10 ethylene glycol units to about 35 ethylene glycol units (e.g., about 10 to about 35 ethylene glycol units, about 10 to about 30 ethylene glycol units, about 10 to about 25 ethylene glycol units, about 10 to about 20 ethylene glycol units, about 10 to about 15 ethylene glycol units, about 15 to about 35 ethylene glycol units, about 15 to about 30 ethylene glycol units, about 15 to about 25 ethylene glycol units, about 15 to about 20 ethylene glycol units, about 20 to about 35 ethylene glycol units, about 20 to about 30 ethylene glycol units, about 20 to about 25 ethylene glycol units, about 25 to about 35 ethylene glycol units, about 25 to about 30 ethylene glycol units, or about 30 to about 35 ethylene glycol units).

In any aspect or embodiment described herein, methoxy polyethylene glycol, or polyethylene-glycol capped with a methyl group on one end, having an average molecular weight of 1000 (such as mPEG-1000) may be used to prepare a prodrug bifunctional compounds of the present disclosure. For example, in any aspect or embodiment, methoxy polyethylene glycol, or polyethylene-glycol capped with a methyl group on one end, having an average chain length of 22 units (such as mPEG-1000) may be used to prepare a prodrug bifunctional compounds of the present disclosure. The methods described herein can be used to make longer or shorter PEG chains, of uniform or diverse chain lengths.

In any aspect or embodiment described herein, the prodrug bifunctional compound of the present disclosure has a percent release of at least about 10%. For example, in any aspect or embodiment described herein, the prodrug bifunctional compound of the present disclosure has a percent release of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, about 10% to about 90%, about 10% to about 80%, about 10% to about 70%, about 10% to about 60%, about 10% to about 50%, about 10% to about 40%, about 10% to about 30%, about 20% to about 90%, about 20% to about 80%, about 20% to about 70%, about 20% to about 60%, about 20% to about 50%, about 20% to about 40%, about 30% to about 90%, about 30% to about 80%, about 30% to about 70%, about 30% to about 60%, about 30% to about 50%, about 40% to about 90%, about 40% to about 80%, about 40% to about 70%, about 40% to about 60%, about 50% to about 90%, about 50% to about 80%, about 50% to about 70%, about 60% to about 90%, or about 60% to about 80%, about 70% to about 90%, at about 30 minues, about 60 minues, about 1.5 hours, about 2 hours, about 2.5 hours, about 3 hours, about 3.5 hours, about 4 hours, about 4.5 hours, about 5 hours, about 4.5 hours, about 6 hours, about 6.5 hours, about 7 hours, about 7.5 hours, about 8 hours, about 8.5 hours, about 9 hours, about 9.5 hours, or about 10 hours.

In any aspect or embodiment described herein, the prodrug bifunctional compound of the present disclosure has a half life of at least about 60 minutes. For example, in any aspect of embodiment described herein, the prodrug bifunctional compound of the present disclosure has a half life serum or plasma (e.g., human, cyano monkey, rat, mouse, pig, dog, cat, etc., serum or plasma) of less than or equal to about 1 minute, less than or equal to about 5 minutes, less than or equal to 10 minutes, less than or equal to about 15 minutes, less than or equal to about 30 minutes, less than or equal to about 45 minutes, less than or equal to about 1 hour, less than or equal to 1.5 hours, less than or equal to about 2 hours, less than or equal to about 2.5 hours, less than or equal to about 3 hours, less than or equal to about 3.5 hours, less than or equal to about 4 hours, less than or equal to 4.5 hours, less than or equal to about 5 hours, less than or equal to about 5.5 hours, less than or equal to about 6 hours, less than or equal to about 6.5 hours, less than or equal to about 7 hours, less than or equal to about 7.5 hours, less than or equal to about 8 hours, less than or equal to 8.5 hours, less than or equal to about 9 hours, less than or equal to 9.5 hours, less than or equal to about 10 hours, less than or equal to about 11 hours, less than or equal to about 12 hours, less than or equal to about 14 hours, less than or equal to about 16 hours, less than or equal to about 18 hours, less than or equal to about 20 hours, less than or equal to about 22 hours, less than or equal to about 24 hours, less than or equal to about 26 hours, less than or equal to about 28 hours, less than or equal to about 30 hours, less than or equal to about 32 hours, less than or equal to about 34 hours, less than or equal to about 36 hours, less than or equal to about 38 hours, less than or equal to about 40 hours, less than or equal to about 42 hours, less than or equal to about 44 hours, less than or equal to about 46 hours, less than or equal to about 48 hours, less than or equal to about 50 hours, about 15 seconds to about 50 hours, about 15 seconds to about 45 hours, about 15 seconds to about 40 hours, about 15 seconds to about 35 hours, about 15 seconds to about 30 hours, about 15 seconds to about 25 hours, about 15 seconds to about 20 hours, about 15 seconds to about 15 hours, about 15 seconds to about 10 hours, about 15 seconds to about 5 hours, about 30 seconds to about 50 hours, about 30 seconds to about 45 hours, about 30 seconds to about 40 hours, about 30 seconds to about 35 hours, about 30 seconds to about 30 hours, about 30 seconds to about 25 hours, about 30 seconds to about 20 hours, about 30 seconds to about 15 hours, about 30 seconds to about 10 hours, about 30 seconds to about 5 hours, about 1 minute to about 50 hours, about 1 minute to about 45 hours, about 1 minute to about 40 hours, about 1 minute to about 35 hours, about 1 minute to about 30 hours, about 1 minute to about 25 hours, about 1 minute to about 20 hours, about 1 minute to about 15 hours, about 1 minute to about 10 hours, about 1 minute to about 5 hours, about 1 to about 50 hours, about 1 to about 45 hours, about 1 to about 40 hours, about 1 to about 35 hours, about 1 to about 30 hours, about 1 to about 25 hours, about 1 to about 20 hours, about 1 to about 15 hours, about 1 to about 10 hours, about 1 to about 5 hours, about 5 to about 50 hours, about 5 to about 45 hours, about 5 to about 40 hours, about 5 to about 35 hours, about 5 to about 30 hours, about 5 to about 25 hours, about 5 to about 20 hours, about 5 to about 15 hours, about 5 to about 10 hours, about 10 to about 50 hours, about 10 to about 45 hours, about 10 to about 40 hours, about 10 to about 35 hours, about 10 to about 30 hours, about 10 to about 25 hours, about 10 to about 20 hours, about 15 to about 50 hours, about 15 to about 45 hours, about 15 to about 40 hours, about 15 to about 35 hours, about 15 to about 30 hours, about 15 to about 25 hours, about 20 to about 50 hours, about 20 to about 45 hours, about 20 to about 40 hours, about 20 to about 35 hours, about 20 to about 30 hours, about 25 to about 50 hours, about 25 to about 45 hours, about 25 to about 40 hours, about 25 to about 35 hours, about 30 to about 50 hours, about 30 to about 45 hours, about 30 to about 40 hours, about 35 to about 50 hours, about 35 to about 45 hours, about 40 to about 50 hours, in serum (e.g., human sera, monkey sera, dog sera, cat sera, pig sera, horse sera, etc.).

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the dmg. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, poly orthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, cardiofaciocutaneous syndrome, neurofibromatosis type 1, Costello syndrome, Noonan Syndrome, LEOPARD (Lentigo, Electrocardiographic abnormalities, Ocular hypertelorism, or Pulmonary stenosis, Abnormal genitalia, Retarded growth, Deafness) syndrome, which may be treated using compounds according to the present disclosure are set forth hereinabove.

The description provides therapeutic compositions as described herein for effectuating the degradation of proteins of interest for the treatment or amelioration of a disease, e.g., cancer, cardiofaciocutaneous syndrome, neurofibromatosis type 1, Costello syndrome, Noonan syndrome, or LEOPARD (Lentigo, Electrocardiographic abnormalities, Ocular hypertelorism, Pulmonary stenosis, Abnormal genitalia, Retarded growth, Deafness) syndrome. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharamaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a vims, bacteria, fungus, protozoa or other microbe or may be a disease state, which is caused by overexpression and/or overactivation (e.g., a constitutively active) of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents, anti-retrovirus and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HD AC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORCl/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent", "anti-retroviral", or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, F-FddC, F-FD4C, NVP (Nevirapine), DFV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), FPV (Fopinavir), fusion inhibitors such as T20, among others, fuseon and mixtures thereof, including anti-HIV compounds presently in clinical trials or in development.

Other anti-HIV/anti-retrovirual agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Fy300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscamet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea[PETT derivative), N-[2-(2,6-Difluorophenethyl]-N'-[2-(5-methylpyridyl)]thiourea {PETT Pyridyl derivative), N-[2-(3-Fluorofuranyl)ethyl]-N'—[2-(5-chloropyridyl)] thiourea, N—[2-(2-Fluoro-6-ethoxyphenethyl)]-N'-[2-(5-bromopyridyl)]thiourea, N-(2-Phenethyl)-N'-(2-thiazolyl) thiourea (LY-73497), L-697,639, L-697,593, L-697,661, 3-[2-(4,7-Difluorobenzoxazol-2-yl)ethyl]-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

List of Abbreviations

AcOH, acetic acid
aq., aqueous
BINAP, 2,2'-bis(diphenylphosphino)-1,1'-binaphthalene
Boc, tert-butoxycarbonyl
$BOC_2O$, di-tert-butyl dicarbonate BOP, (benzotriazol-1-yloxy)tris(dimethylamino)phosphonium hexafluorophosphate
$CDCl_3$, deuteriochloroform
CD3OD, deuteriomethanol
$CH_3CN$, acetonitrile
$CH_3OH$, methanol
CsF, cesium fluoride
$Cs_2CO_3$, cesium carbonate
$CU(OAC)_2$, copper (II) acetate
$Cy_2NMe$, dicyclohexylmethylamine
DCM, dichloromethane
DIAD, diisopropyl azodicarboxylate
DIEA or DIPEA, diisopropylethylamine
DMAP, N,N-dimethylaminopyridine
DMF, N,N-dimethylformamide
DMSO, dimethylsulfoxide
DMSO-$d_6$, hexadeuterodimethyl sulfoxide
$Et_2NH$, diethylamine
EtOAc or EA, ethyl acetate
HCl, hydrochloric acid
$H_2O$, water
HPLC, high performance liquid chromatography
IBX, 2-iodoxybenzoic acid
KOAc, potassium acetate
LCMS, liquid chromatography/mass spectrometry
LiOH, lithium hydroxide
MeOH, methanol
MsCl, methanesulfonyl chloride
$N_2$, nitrogen
NaH, sodium hydride
$NaBH_3CN$, sodium cyanoborohydride
$NaBH(OAc)_3$, sodium triacetoxyborohydride
NaCl, sodium chloride
NaHCOs, sodium bicarbonate
NaI, sodium iodide
$Na_2SO_4$, sodium sulfate
n-BuLi, n-butyllithium
$NH_3$, ammonia
$NH_4Cl$, ammonium chloride
$NH_2OH$ HCl, hydroxylamine hydrochloride
NMP, N-methylpyrrolidone
NMR, nuclear magnetic resonance
$O_2$, oxygen
Pd(aMPhos)$Cl_2$, bis(di-tert-butyl(4-dimethylaminophenyl)phosphine)dichloropalladium(II)
$Pd_2(dba)_3$, tris(dibenzylideneacetone)dipalladium(0)
Pd(dppf)$Cl_2$, [1,1'-bis(diphenylphosphino)ferrocene]dichloropalladium(II)
$Pd(OH)_2$, palladium hydroxide
$Pd(PPh_3)_4$, tetrakis(triphenylphosphine)palladium(0)
PE, petroleum ether
$Ph_3P$, triphenylphosphine
Py, pyridine
PyBOP, (benzotriazol-1-yloxy)tripyrrolidinophosphonium hexafluorophosphate
rt, room temperature
TBAF, tetra-n-butylammonium fluoride
TBDPSCl, tert-butyldiphenylsilyl chloride
TBS, tert-butyldimethylsilyl
tBuOK, potassium tert-butoxide
$[tBu_3PH]BF_4$, tri-tert-butyl phosphonium tetrafluoroborate
TEA, triethylamine
THF, tetrahydrofuran
TLC, thin layer chromatography
TMSOTf, trimethylsilyl trifluoromethanesulfonate
TsCl, p-toluenesufonyl chloride
TsOH, p-toluenesulfonic acid Scheme 1A.

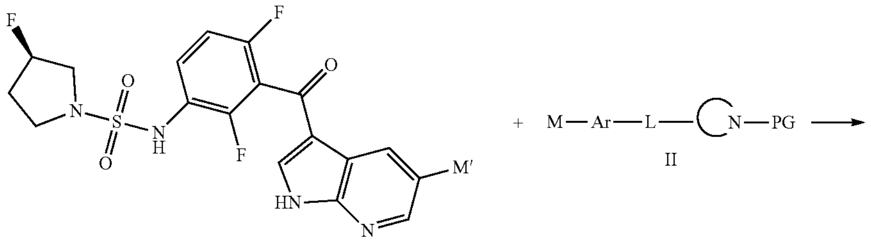

I

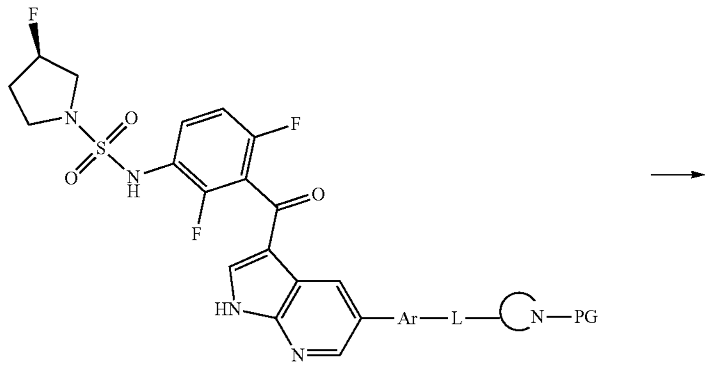

III

-continued

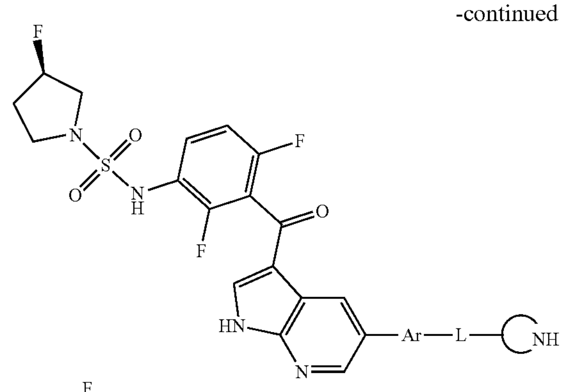

IV

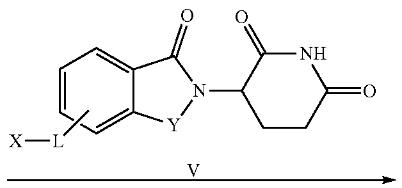

V

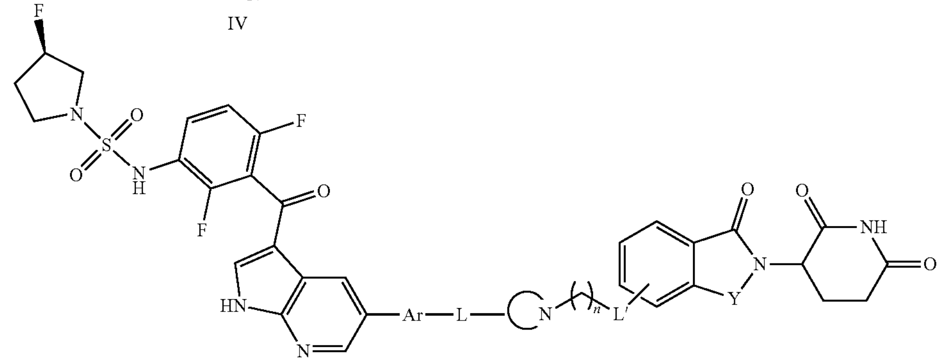

VI

A compound of formula I may be reacted with a reagent II (commercially available or readily prepared using standard reaction techniques known to one skilled in the art) under palladium-catalyzed cross-coupling conditions, e.g. with a suitable palladium catalyst such as bis(di-tert-butyl(4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula III. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker,

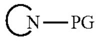

represents a primary or secondary amine, optionally cyclized into a 4 to 8 membered heterocyclic ring, wherein PG represents a suitable protecting group, including but not limited to t-butoxycarbonyl or benzyl. Compounds of formula III may be converted to a compound of formula IV by treatment with a reagent suitable for the removal of PG, e.g. hydrogen chloride in 1,4-dioxane when PG is t-butoxycarbonyl. Compound IV may then be reacted with compound V to produce compound VI, wherein L' represents an optional linker or portion of a linker, Y is $CH_2$ or C═O, and X is either a suitable leaving group (e.g. OMs, OTs, Cl, etc.) or an aldehyde (CHO). When X is a leaving group, n is 0, and suitable reaction conditions are those for an alkylation reaction, e.g. diisopropylethylamine, potassium iodide, DMSO or acetonitrile, 80° C. When X is an aldehyde, n is 1, and suitable reaction conditions are those for a reductive amination reaction, e.g. sodium cyanoborohydride, methanol, dichloromethane, acetic acid, room temperature.

Scheme 1B.

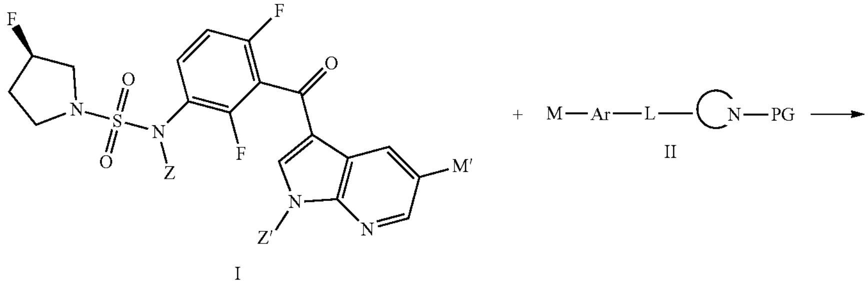

II

I

-continued

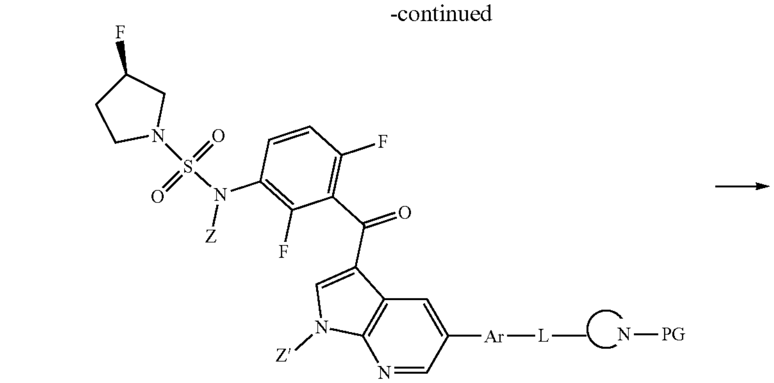

III

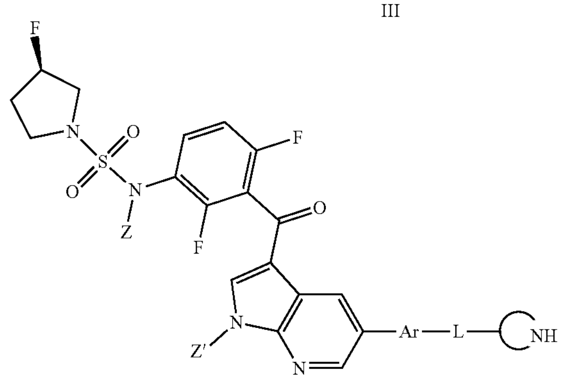

IV

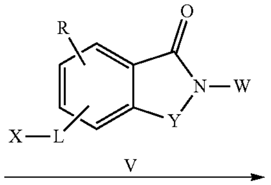

V

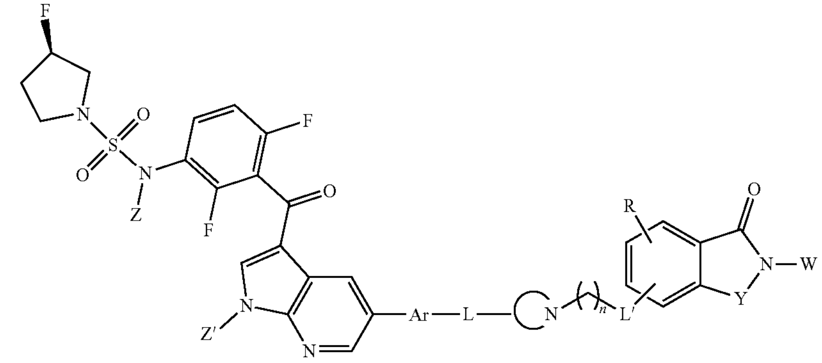

VI

A compound of formula I may be reacted with a reagent II (commercially available or readily prepared using standard reaction techniques known to one skilled in the art) under palladium-catalyzed cross-coupling conditions, e.g. with a suitable palladium catalyst such as bis(di-tert-butyl (4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula III. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Z and Z' are each independently H or a suitable protecting group such as t-butoxycarbonyl; Ar represents an aromatic or heteroaromatic ring system; L represents an optional linker or portion of a linker,

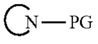

represents a primary or secondary amine, optionally cyclized into a 4 to 8 membered heterocyclic ring and/or fused to Ar, wherein PG represents a suitable protecting group, including but not limited to t-butoxycarbonyl or benzyl. Compounds of formula III may be converted to a compound of formula IV by treatment with a reagent suitable for the removal of PG, e.g. hydrogen chloride in 1,4-dioxane when PG is t-butoxycarbonyl. Compound IV may then be reacted with compound V to produce compound VI, wherein L' represents an optional linker or portion of a linker, Y is $CH_2$ or C═O, X is either a suitable leaving group (e.g. OMs, OTs, Cl, etc.) or an aldehyde (CHO), and R is an optional substituent (e.g. F or $OCH_3$), and W is:

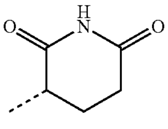

or

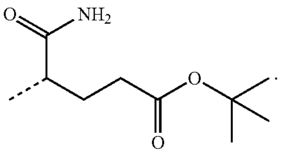

When X is a leaving group, n is 0, and suitable reaction conditions are those for an alkylation reaction, e.g. diisopropylethylamine, potassium iodide, DMSO or acetonitrile, 80° C. When X is an aldehyde, n is 1, and suitable reaction conditions are those for a reductive amination reaction, e.g. sodium cyanoborohydride, methanol, dichloromethane, acetic acid, room temperature. As needed, mixtures of enantiomers or diastereomers of any compounds IV, V, or VI may be resolved into their constituent enantiomers or diastereomers using techniques known to one skilled in the art, including but not limited to preparative high performance liquid chromatography or preparative supercritical fluid chromatography.

In cases where W is

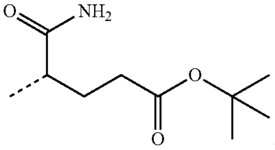

, the compound VI may be treated with conditions suitable for imide cyclization, e.g. benzenesulfonic acid in acetonitrile or N-methylpyrrolidone at 100° C. to afford a different compound of formula VI where W is

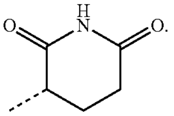

In cases where one or both of Z or Z' are a protecting group, such protecting group may be removed from a compound VI, e.g. by treatment with trifluoroacetic acid when Z and/or Z' are t-butoxycarbonyl, to afford a different compound of formula VI wherein Z and Z' are H.

It will further be apparent to one skilled in the art that the positions of

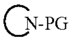

in II and X in V may be reversed throughout the synthetic sequence, such that the positions of

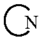

and are reversed in compound VI. In such cases, X may also be $CH_2OH$ or an aldehyde protected e.g. as its acetal, and may be converted to a compound where X is CHO by oxidation of the alcohol, e.g. with Dess-Martin periodinane, or deprotection of the acetal, e.g. with Amberlyst 15 in acetone and water at reflux, prior to reaction with V.

Scheme 2.

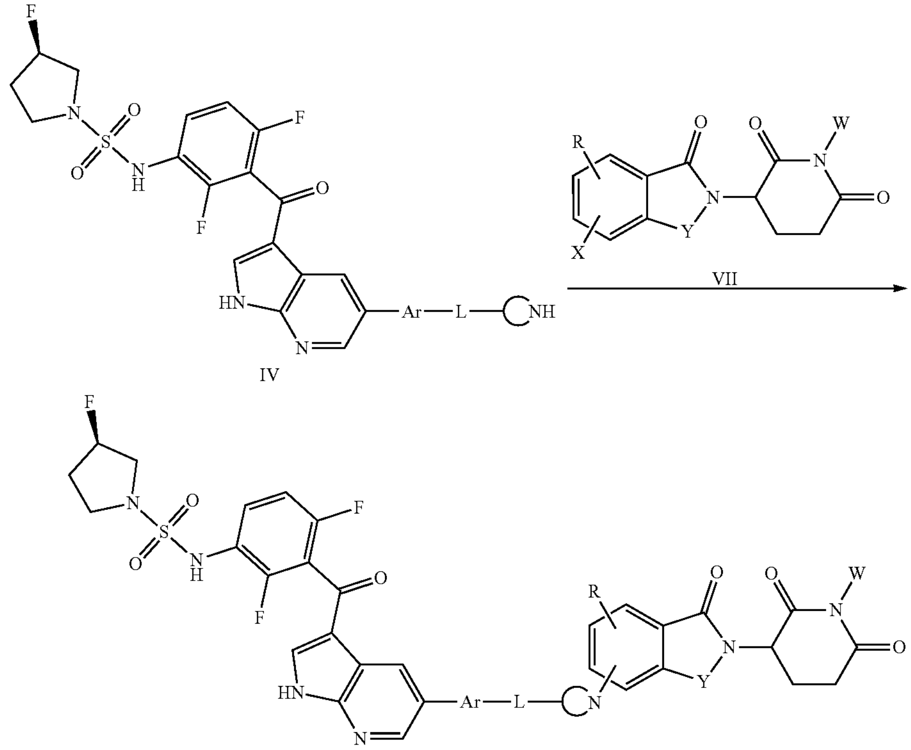

VIII

A compound of formula IV may also be reacted with a compound of formula VII to provide compounds of formula VIII, wherein X is a suitable leaving group such as fluorine or chlorine, Y is C═O, R represents one or more optional substituents, W is H or $CH_3$, and reaction conditions are those for a nucleophilic aromatic substitution, e.g. triethylamine, DMSO, 70° C.

Scheme 3A.

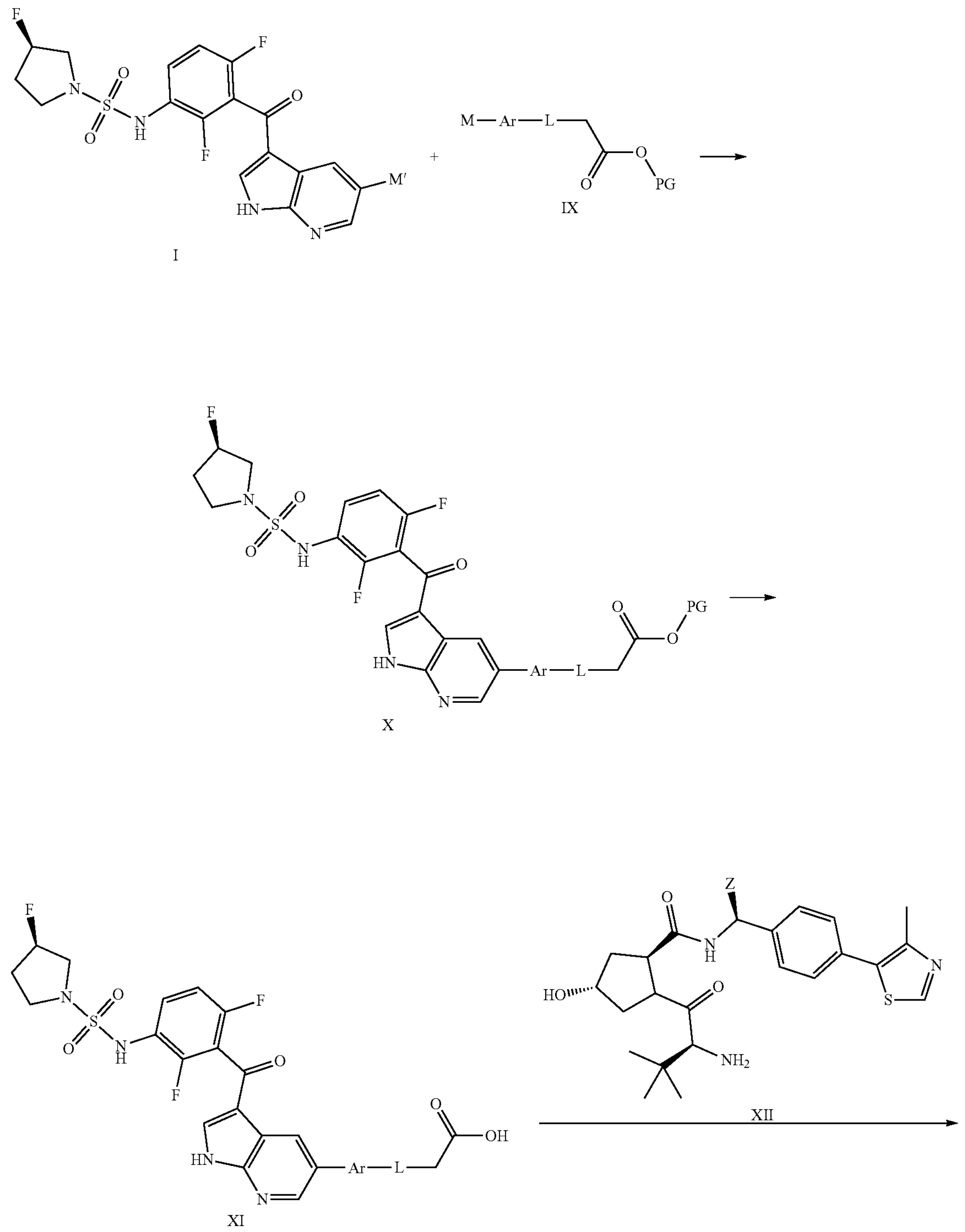

I + IX

X

XI XII

-continued

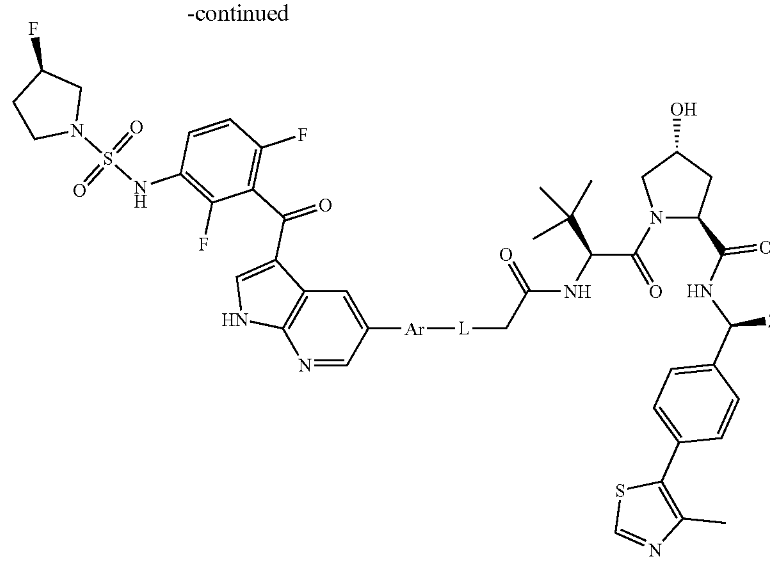

XIII

A compound of formula I may be reacted with a reagent IX (commercially available or readily prepared using standard reaction techniques known to one skilled in the art) under palladium-catalyzed cross-coupling conditions, e.g. as shown in Scheme 1A or 1B, to produce a compound of formula X. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker, and PG represents a suitable ester protecting group, e.g. methyl, ethyl, or t-butyl. Compounds of formula X may be converted to a compound of formula XI by treatment with a reagent suitable for the removal of PG, e.g. hydrogen chloride in 1,4-dioxane when PG is t-butyl. Compound XI may then be reacted with compound XII, wherein Z is an optional substituent, e.g. H, methyl, or hydroxymethyl, to produce compounds of formula XIII under amide formation conditions, e.g. (benzotriazol-1-yloxy)tripyrrolidinophosphonium hexafluorophosphate, diisopropylethylamine, DMF, room temperature.

Scheme 3B.

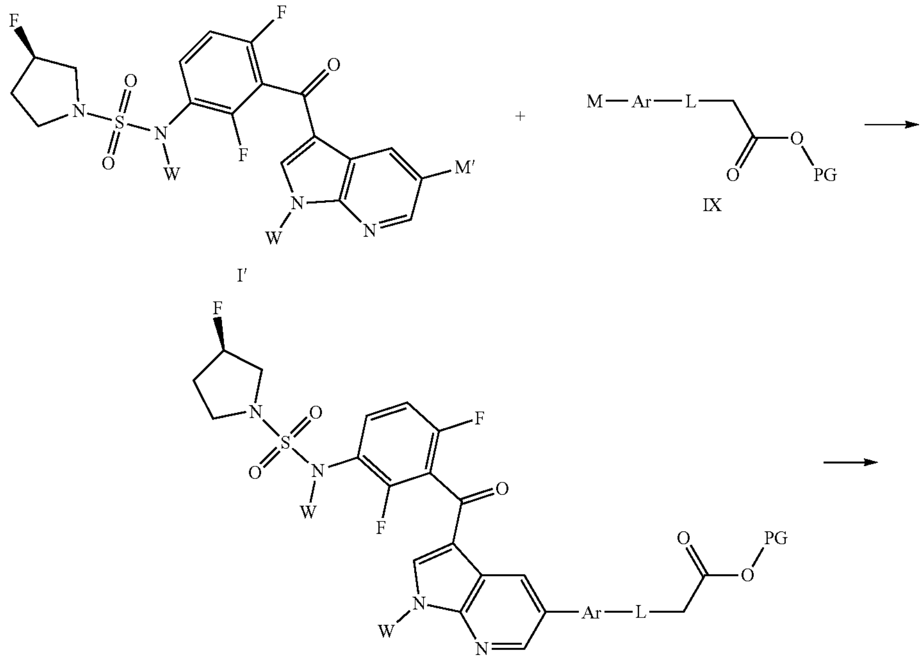

I'

IX

X

-continued

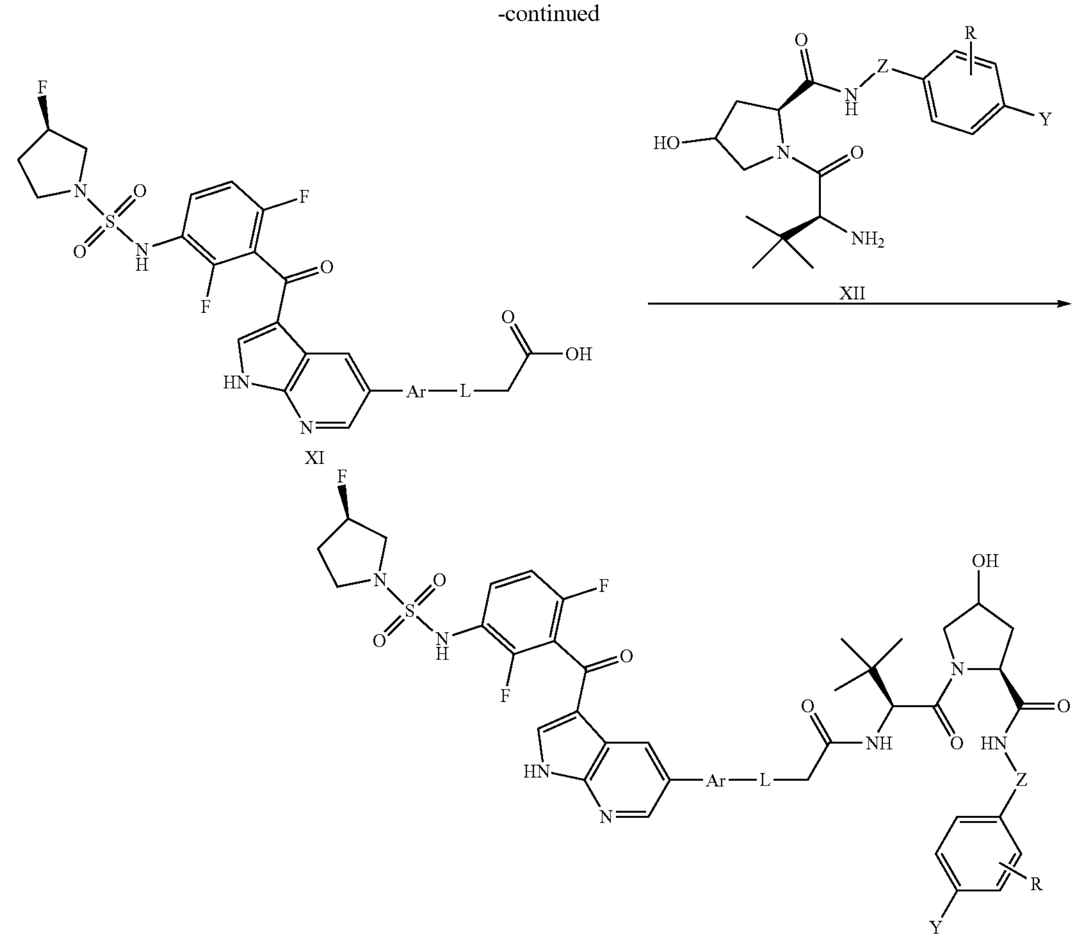

XI

XII

XIII

A compound of formula I' may be reacted with a reagent IX (commercially available or readily prepared using standard reaction techniques known to one skilled in the art) under palladium-catalyzed cross-coupling conditions, e.g. as shown in Scheme 1A or 1B, to produce a compound of formula X. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker; PG represents a suitable ester protecting group, e.g. methyl, ethyl, or t-butyl; and W represents an optional protecting group, e.g. 2-(trimethylsilyl)ethoxymethyl. Where necessary, e.g. when L contains a primary or secondary amine or an alcohol, such functional groups may be optionally protected with a suitable protecting group, e.g. t-butoxycarbonyl when the functional group is an amine or t-butyldimethylsilyl when the functional group is an alcohol. Compounds of formula X may be converted to a compound of formula XI by treatment with a reagent suitable for the removal of the optional W, e.g. hydrogen chloride in 1,4-dioxane and methanol or ethylenediamine and tetra-n-butylammonium fluoride when W is 2-(trimethylsilyl)ethoxymethyl; followed by treatment with a reagent suitable for the removal of PG, e.g. hydrogen chloride in 1,4-dioxane when PG is t-butyl. Compound XI may then be reacted with compound XII, wherein Z is an optionally substituted carbon, e.g. $CH_2$, $CD_2$, CH(Me), $CH(CH_2OH)$, $C(CH_3)_2$, R is an optional substituent, e.g. F or $CH_2OH$, and Y is an optional substituent, e.g. halogen, CN, or optionally substituted aryl or heterocyclyl, to produce compounds of formula XIII under amide formation conditions, e.g. (benzotriazol-1-yloxy)tripyrrolidinophosphonium hexafluorophosphate, diisopropylethylamine, DMF, room temperature. It will be apparent to one skilled in the art that when L contains a protected amine or alcohol, such protecting group may be removed as needed at the stage of compound X, XI, or XIII, e.g. by treatment with trifluoroacetic acid when said protecting group is t-butoxycarbonyl or hydrochloric acid in methanol when said protecting group is t-butyldimethylsilyl.

Scheme 4A.

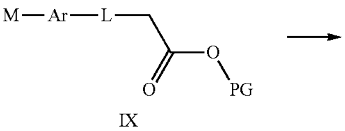

IX

-continued

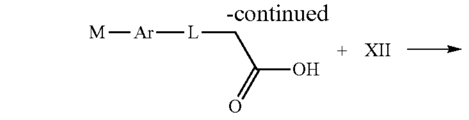

XIV

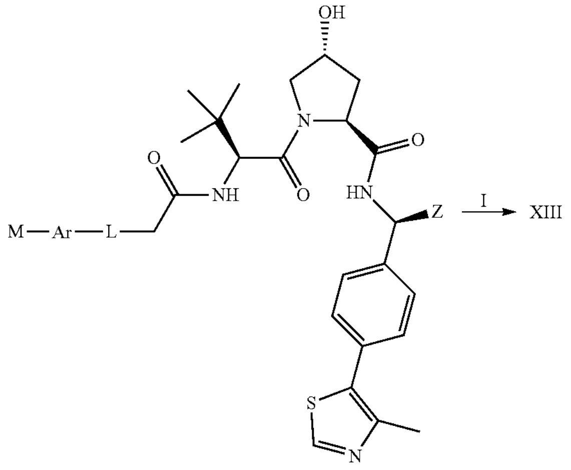

XV

Alternatively, a compound of formula IX may be converted to a compound of formula XIV by using conditions analogous to those for the conversion of X to XI in Scheme 3A or 3B. A compound of formula XIV may be converted to a compound of formula XV by using conditions analogous to those for the conversion of XI to XIII in Scheme 3A or 3B. A compound of formula XV may then be converted to a compound of formula XIII by reaction with a compound of formula I using conditions analogous to those for the conversion of I and IX to X in Scheme 3A or 3B.

Scheme 4B.

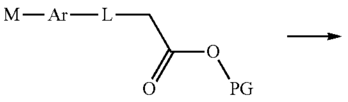

IX

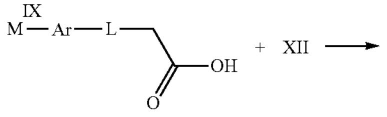

XIV

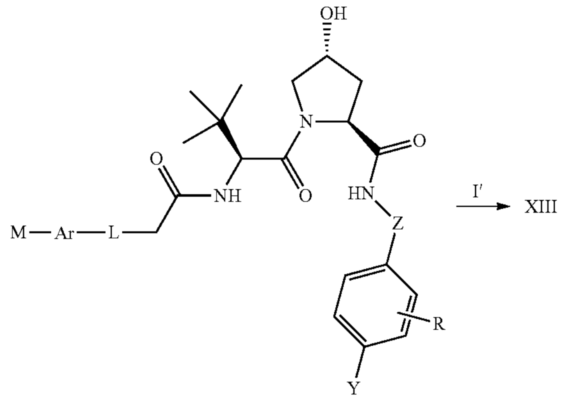

XV

Alternatively, a compound of formula IX may be converted to a compound of formula XIV by using conditions analogous to those for the conversion of X to XI in Scheme 3A or 3B. A compound of formula XIV may be converted to a compound of formula XV by using conditions analogous to those for the conversion of XI to XIII in Scheme 3A or 3B. A compound of formula XV may then be converted to a compound of formula XIII by reaction with a compound of formula I' using conditions analogous to those for the conversion of I' and IX to X, followed by optional deprotection of W, in Scheme 3B.

Scheme 5.

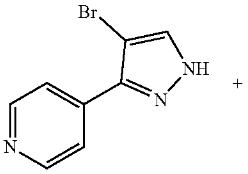

XVI

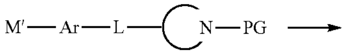

II'

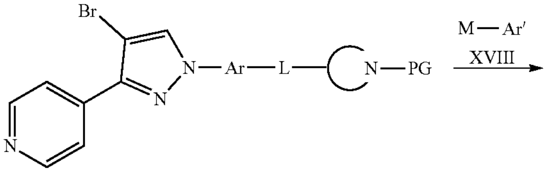

XVII

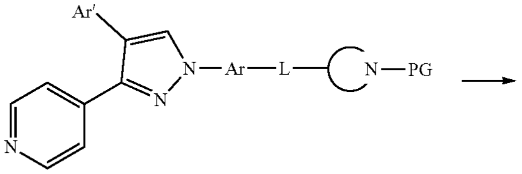

XIX

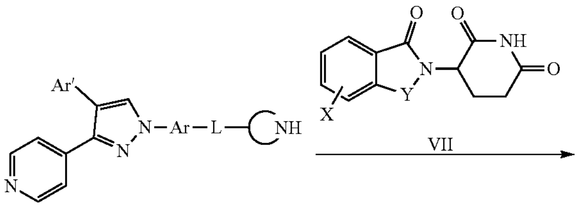

XX

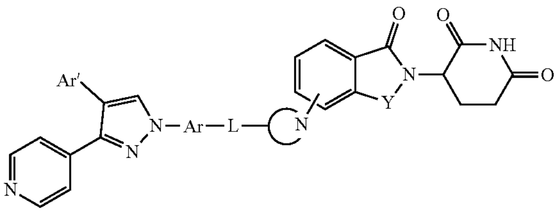

XXI

A compound of formula XVI may be reacted with a reagent II' (commercially available or readily prepared using standard reaction techniques known to one skilled in the art) under Chan-Lam cross-coupling conditions, e.g. copper (II) acetate, pyridine or diethylamine or triethylamine, 100° C., to produce a compound of formula XVII. M' represents a boronic acid or boronic ester; Ar represents an aromatic or heteroaromatic ring system; L represents an optional linker,

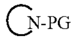

represents a primary or secondary amine, optionally cyclized into a 4 to 8 membered heterocyclic ring, wherein PG represents a suitable protecting group, including but not limited to t-butoxycarbonyl or benzyl. Compounds of formula XVII may be may be reacted with a reagent XVIII under palladium-catalyzed cross-coupling conditions, e.g. [1,1'-bis(diphenylphosphino)ferrocene]dichloropalladium, tri-tert-butylphosphine tetrafluoroborate, cesium fluoride, 1,4-dioxane, 90° C., to produce a compound of formula XIX. M represents a functional group capable of undergoing palladium-catalyzed transmetallation, e.g. a boronic acid, boronic ester, or trialkylstannane and Ar' represents an aromatic or heteroaromatic ring system with optional substituents. A compound of formula XIX may then be converted to a compound of formula XX by treatment with a reagent suitable for the removal of PG, e.g. hydrogen chloride in 1,4-dioxane or methanol when PG is t-butyl. A compound of formula XX may also be reacted with a compound of formula VII to provide compounds of formula XXI, wherein X is a suitable leaving group such as fluorine or chlorine, Y is C═O, the aromatic ring of VII may have further optional substituents, and reaction conditions are those for a nucleophilic aromatic substitution, e.g. triethylamine, DMSO, 80° C. In cases where the group Ar' contains optional substituents, e.g. a ketone, these may undergo further functionalization, e.g. by treatment with hydroxylamine hydrochloride and pyridine at room temperature, to provide further compounds of formula XXI.

Scheme 6.

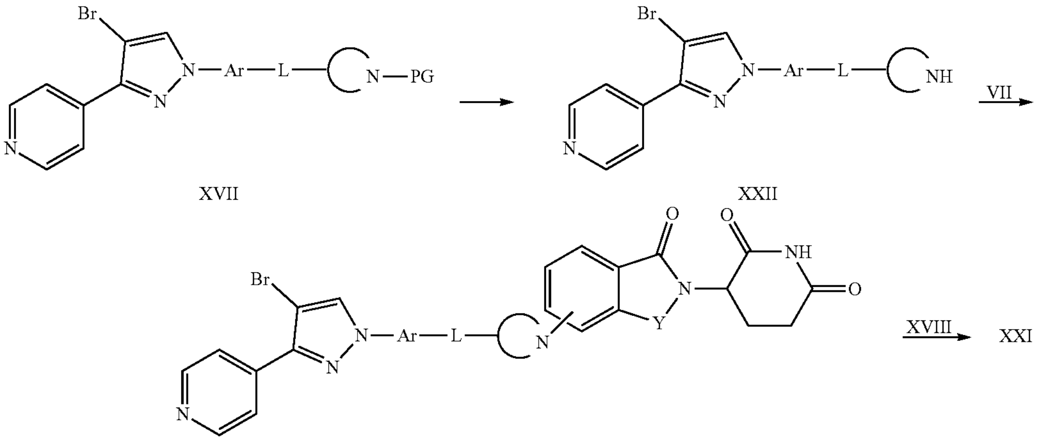

XVII XXII XXIII XXI

Alternatively, a compound of formula XVII may be converted to a compound of formula XXII by using conditions analogous to those for the conversion of XIX to XX in Scheme 5. A compound of formula XXII may then be treated with a compound of formula VII as defined in Scheme 5 to produce a compound of formula XXIII. The compound of formula XXIII may then be treated with a reagent XVIII as defined in Scheme 5 to produce a compound of formula XXI. In cases where the group Ar' contains optional substituents, e.g. a ketone, these may undergo further functionalization, e.g. by treatment with hydroxylamine hydrochloride and pyridine at room temperature, to provide further compounds of formula XXI.

Scheme 7.

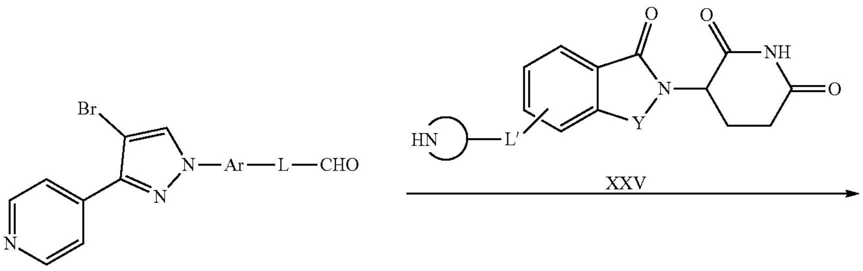

XXIV

-continued

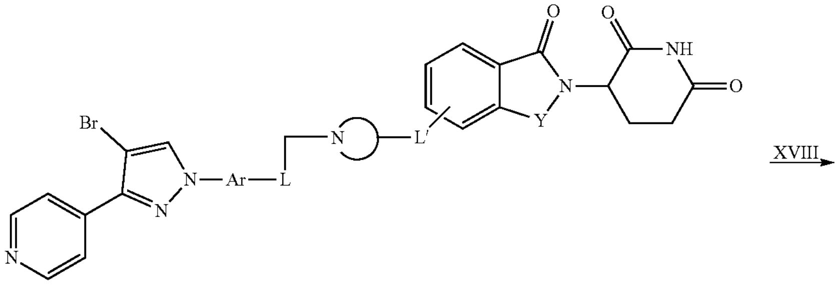

XXVI

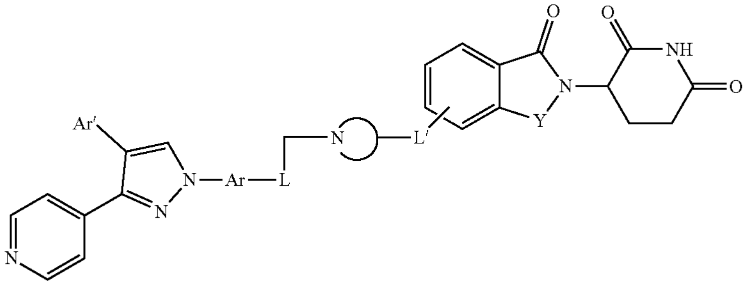

XXVII

A compound of formula XXIV (prepared in an analogous manner to the preparation of XVII from XVI and II' in Scheme 5, with additional functional group transformations as necessary, which are well known to one skilled in the art) may be reacted with a compound of formula XXV to prepare a compound of formula XXVI under reductive amination conditions, e.g. sodium cyanoborohydride, acetic acid, methanol, room temperature. Herein Ar represents an aromatic or heteroaromatic ring system; L and L' represent an optional linker or portion of a linker,

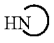

represents a primary or secondary amine, optionally cyclized into a 4 to 8 membered heterocyclic ring, and Y is $CH_2$ or C═O. A compound of formula XXVI may then be treated with a reagent XVIII as defined in Scheme 5 to produce a compound of formula XXVII. In cases where the group Ar' contains optional substituents, e.g. a ketone, these may undergo further functionalization, e.g. by treatment with hydroxylamine hydrochloride and pyridine at room temperature, to provide further compounds of formula XVII.

Scheme 8.

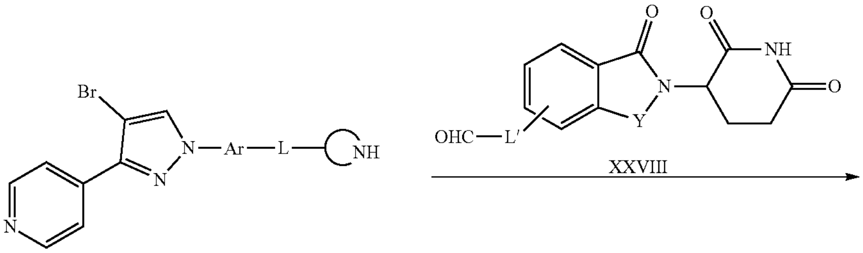

XXII

-continued

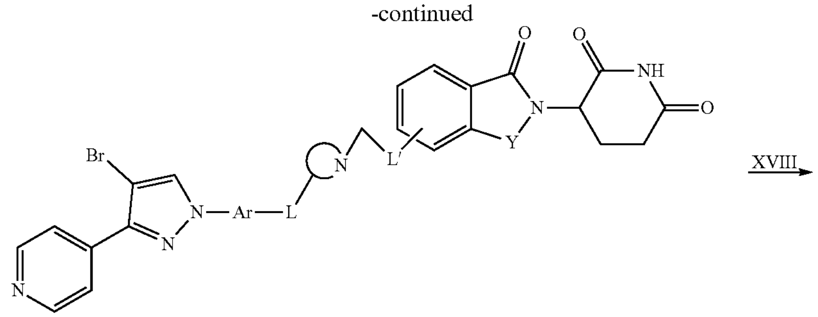

XXVI'

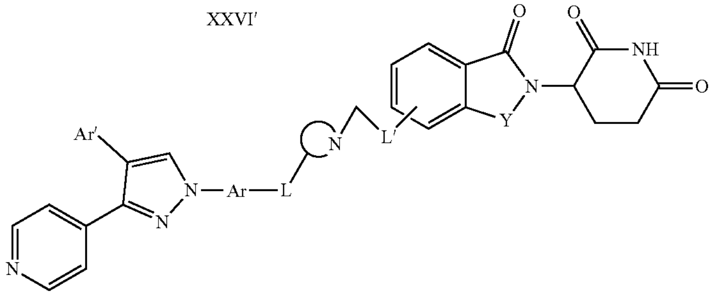

XXVII'

Alternatively, a compound of formula XXII may be treated with a compound of formula XXVIII under reductive amination conditions, e.g. as in Scheme 7, to provide a compound of formula XXVI'. Herein Ar, L, L',

and Y are defined as in Scheme 7. A compound of formula XXVI' may then be treated with a reagent XVIII as defined in Scheme 5 to produce a compound of formula XXVII'. In cases where the group Ar' contains optional substituents, e.g. a ketone, these may undergo further functionalization, e.g. by treatment with hydroxylamine hydrochloride and pyridine at room temperature, to provide further compounds of formula XVII'.

Scheme 9.

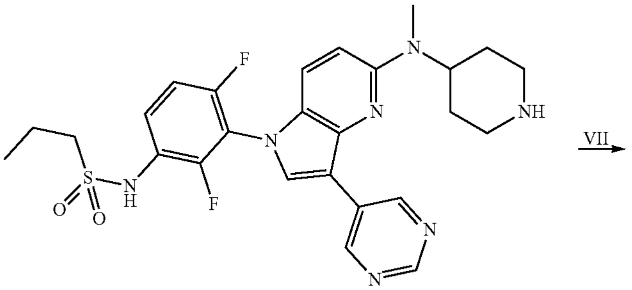

XIX

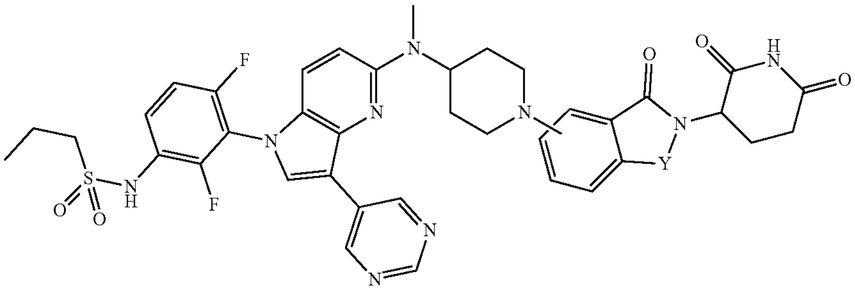

XXX

A compound of formula XIX may be reacted with a compound of formula VII to provide compounds of formula XXX, wherein X is a suitable leaving group such as fluorine or chlorine, Y is C═O, the aromatic ring of VII may have further optional substituents, and reaction conditions are those for a nucleophilic aromatic substitution, e.g. diisopropylethylamine, NMP, 130° C., with or without microwave irradiation.

Scheme 10.

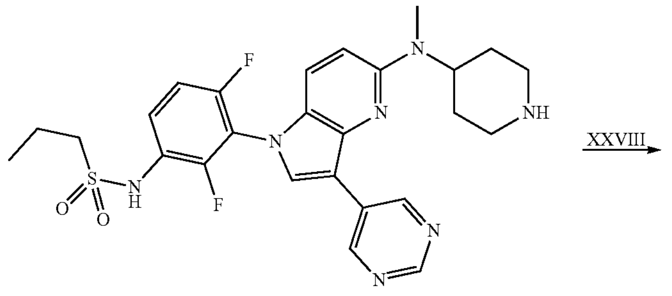

XIX

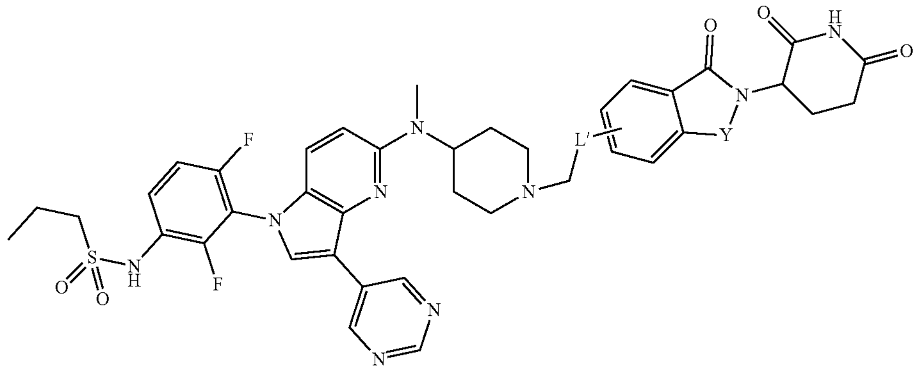

XXXI

Alternatively, a compound of formula XIX may be treated with a compound of formula XXVIII to provide a compound of formula XXXI under reductive amination conditions, e.g. sodium triacetoxyborohydride, ethanol, dichloromethane, room temperature.

Scheme 11.

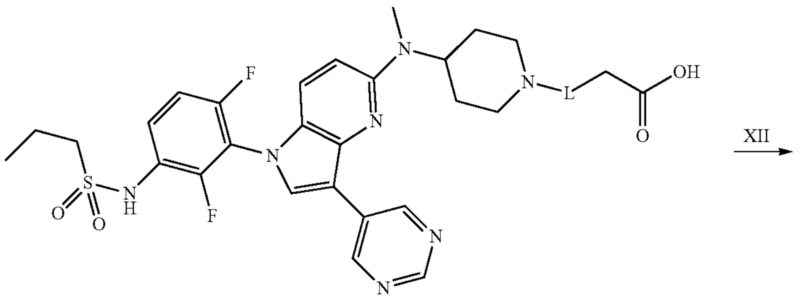

XXXII

-continued

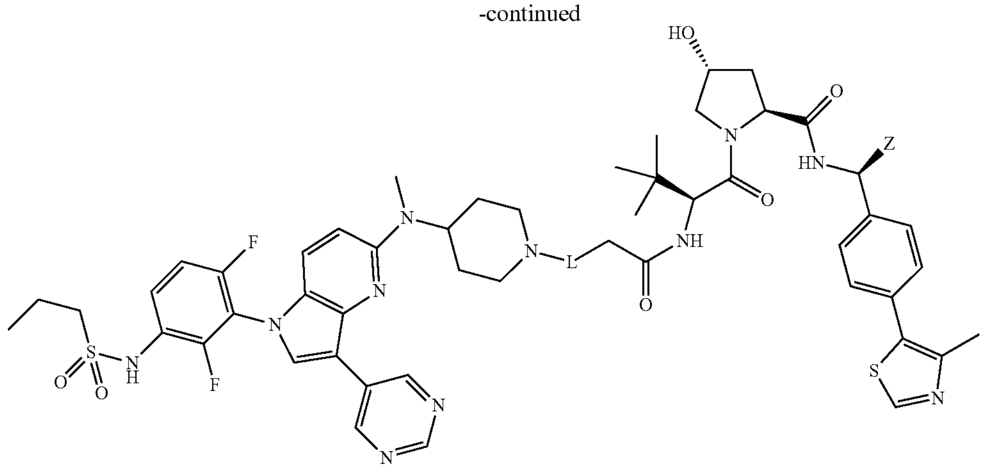

or

XXXIII

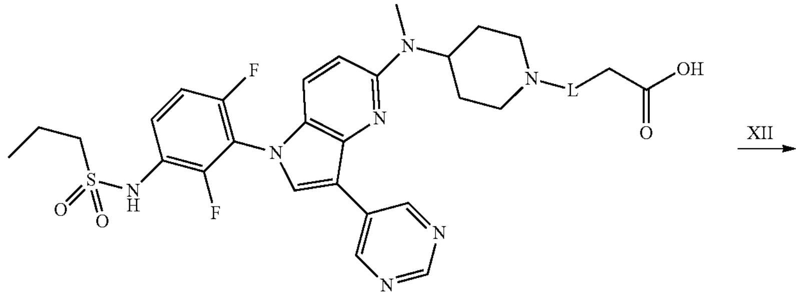

XXXII

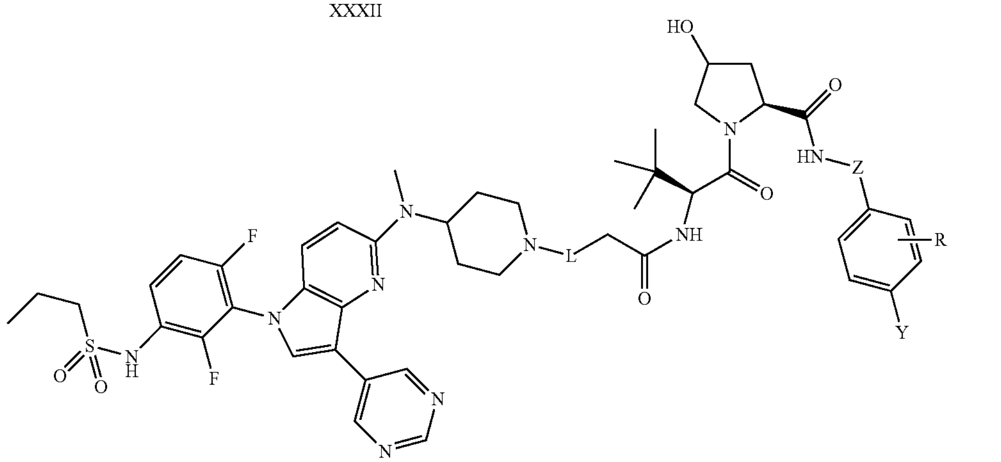

XXXIII

Alternatively, a compound of formula XXXII, prepared from a compound of formula XIX through simple transformations well-known by one skilled in the art, e.g. alkylation or reductive amination, may be reacted with a compound of formula XII to provide a compound of formula XXXIII under amide formation conditions, e.g. (benzotriazol-1-yloxy)tripyrrolidinophosphonium hexafluorophosphate, diisopropylethylamine, DMF, room temperature Scheme 12A.

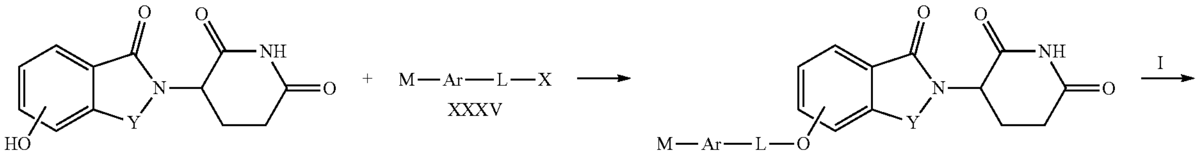

XXXIV XXXV XXXVI

-continued

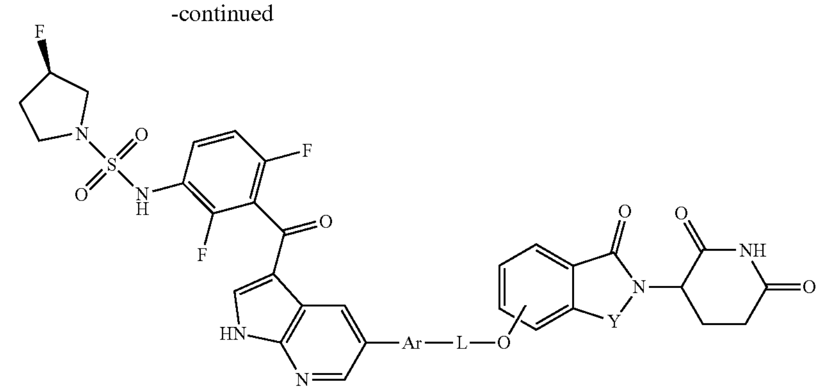

XXXVII

A compound of formula XXXIV may be reacted with a reagent XXXV (commercially available or readily prepared using standard reaction techniques known to one skilled in the art) under nucleophilic substitution conditions, e.g. potassium carbonate, potassium iodide, DMSO, 60° C., to produce a compound of formula XXXVI. Alternatively, the reaction conditions may be those for a Mitsunobu reaction, e.g. triphenylphosphine, diethylazodicarboxylate, THF. Herein Y is $CH_2$ or C═O; one of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; and L represents a linker. When the reaction is a nucleophilic substitution reaction, X represents a suitable leaving group, e.g. p-toluenesulfonate, methanesulfonate, iodide, bromide, or chloride; when the reaction is a Mitsunobu reaction, X is OH. A compound of formula XXXVI may then be further transformed by reaction with compound I under palladium-catalyzed cross-coupling conditions, e.g. with a suitable palladium catalyst such as bis(di-tert-butyl (4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula XXXVII.

Scheme 12B.

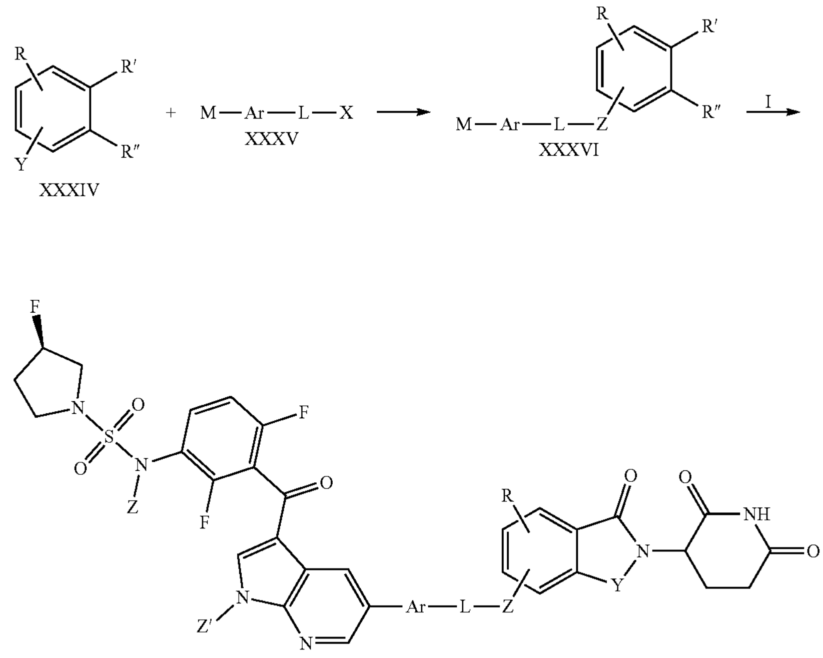

XXXIV XXXV XXXVI XXXVII

A compound of formula XXXIV may be reacted with a reagent XXXV (commercially available or readily prepared using standard reaction techniques known to one skilled in the art) to prepare a compound of formula XXXVI. In all cases, M represents a functional group capable of undergoing palladium-catalyzed transmetallation, e.g. a boronic acid, boronic ester, or trialkylstannane; or alternatively M represents a functional group capable of undergoing palladium-catalyzed oxidative addition, e.g. an iodide, bromide, chloride, or trifluoromethanesulfonate; Ar represents an aromatic or heteroaromatic ring system; L represents a linker; R represents one or more optional substituents; and R' and R" are either both carboxylic esters, e.g. $CO_2CH_2CH_3$, R is a carboxylic ester e.g. $CO_2CH_3$ and R' is CN, or together R and R' form either:

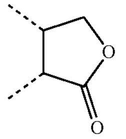

or

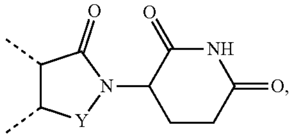

wherein Y is either $CH_2$ or C═O.

In some cases, X is a primary or secondary amine, optionally cyclized into a 4 to 8 membered heterocyclic ring, Y is a suitable leaving group such as fluorine or chlorine, and reaction conditions are those for a nucleophilic aromatic substitution, e.g. triethylamine, DMSO, 70° C. In these cases, Z becomes the corresponding secondary or tertiary amine derived from X. In other cases, X is a suitable leaving group, e.g. p-toluenesulfonate, methanesulfonate, iodide, bromide, or chloride, Y is OH, and reaction conditions are those for a nucleophilic substitution, e.g. potassium carbonate, potassium iodide, DMSO, 60° C. In these cases, Z is O. In other cases, X is OH, Y is OH, and reaction conditions may be those for a Mitsunobu reaction, e.g. triphenylphosphine, diethylazodicarboxylate, THF. In these cases, Z is O.

A compound of formula XXXVI may be further transformed into a different compound of formula XXXVI. When R' is a carboxylic ester and R" is CN, reduction of R" to CHO may be accomplished, e.g. by treatment with sodium hypophosphite and Raney nickel in a mixture of pyridine, acetic acid, and water. When R' and R" together form

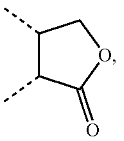

solvolysis e.g. with sodium hydroxide in an alcoholic solvent and tetrahydrofuran may afford a compound where R' is a carboxylic ester and R" is $CH_2OH$. This compound may be further oxidized, e.g. with manganese dioxide, to afford an equivalent compound XXXVI where R' is a carboxylic ester and R" is CHO. Such compounds where R' is a carboxylic ester and R" is CHO may then be reacted with 3-aminoglutarimide in the presence of e.g. sodium triacetoxyborohydride, diisopropylethylamine, and acetic acid in methanol and dichloromethane to afford a new compound of formula XXXVI wherein R' and R" together are

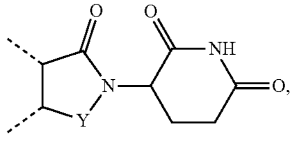

wherein Y is $CH_2$.

A compound of formula XXXVI may then be further transformed by reaction with a compound I under palladium-catalyzed cross-coupling conditions, e.g. with a suitable palladium catalyst such as bis(di-tert-butyl(4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula XXXVII. Herein M', Z, and Z' are as defined in Scheme 1B.

In cases where one or both of Z or Z' are a protecting group, such protecting group may be removed from a compound XXXVII, e.g. by treatment with trifluoroacetic acid when Z and/or Z' are t-butoxycarbonyl, to afford a different compound of formula XXXVII wherein Z and Z' are H.

In cases where in R' and R" are both carboxylic esters in a compound XXXVII, hydrolysis e.g. with sodium hydroxide in methanol and water may afford a different compound XXXVII where R' and R" are $CO_2H$. Such a compound may subsequently be reacted with e.g. 3-aminoglutarimide, (benzotriazol-1-yloxy)tris(dimethylamino)phosphonium hexafluorophosphate, and diisopropylamine in N,N-dimethylformamide to afford a new compound of formula XXXVII wherein R' and R" together are

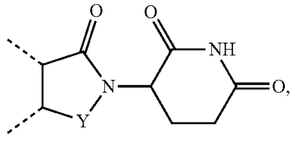

wherein Y is C═O.

Scheme 13A.

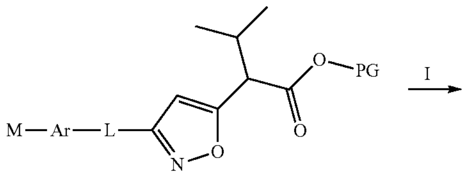

XXXVIII

-continued

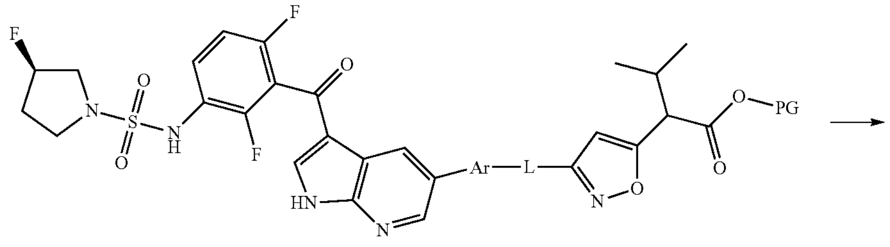

XXXIX

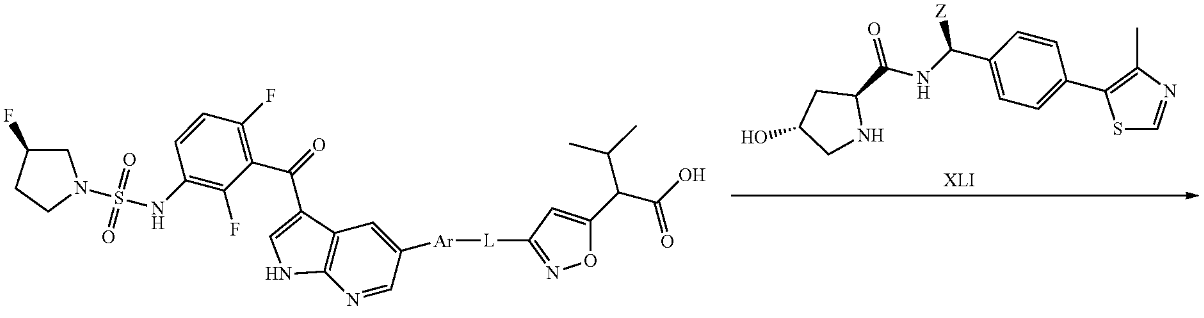

XL

XLI

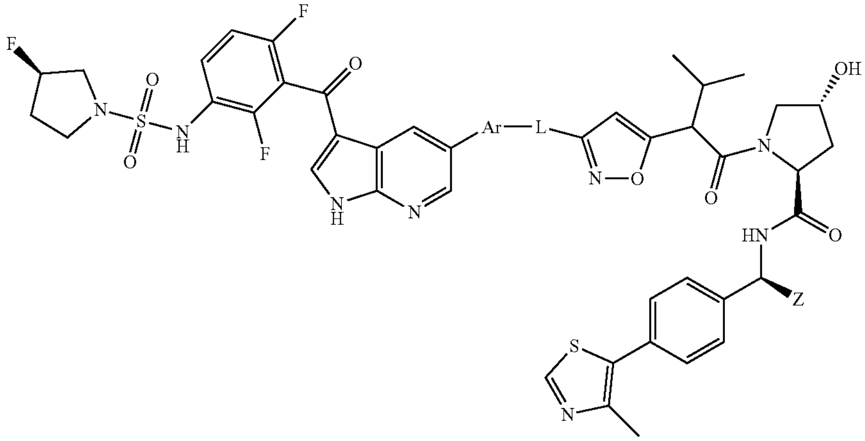

XLII

A compound of formula I may be reacted with a reagent XXXVIII (readily prepared using standard reaction techniques known to one skilled in the art) under palladium-catalyzed cross-coupling conditions, e.g. [1,1'-bis(diphenylphosphino)ferrocene]dichloropalladium(II), sodium carbonate, in a suitable solvent such as 1,4-dioxane/water mixture, at a suitable temperature such as 100° C., with or without microwave heating, to produce a compound of formula XXXIX. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker, and PG represents a suitable ester protecting group, e.g. methyl, ethyl, or t-butyl. Compounds of formula XXXIX may be converted to a compound of formula XL by treatment with a reagent suitable for the removal of PG, e.g. sodium hydroxide in methanol and water at 40° C. when PG is methyl or ethyl. Compound XL may then be reacted with compound XLI, wherein Z is an optional substituent, e.g. H, methyl, or hydroxymethyl, to produce compounds of formula XLII under amide formation conditions, e.g. N-[(dimethylamino)-1H-1,2,3-triazolo-[4,5-b]pyridin-1-ylmethylene]-N-methylmethanaminium hexafluorophosphate N-oxide, diisopropylethylamine, DMF, room temperature.

Scheme 13B.

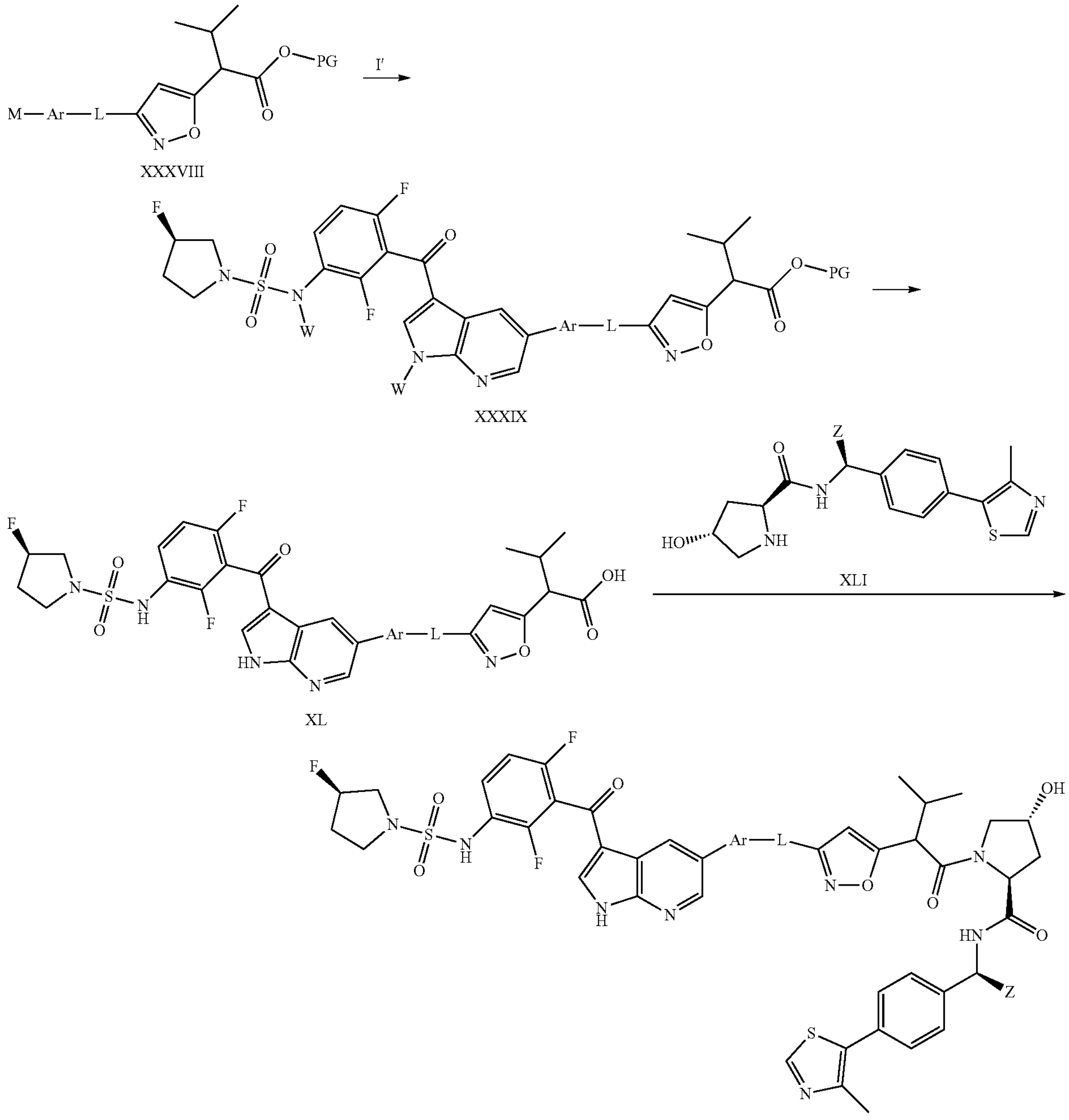

XXXVIII

XXXIX

XL

XLI

XLII

A compound of formula I' may be reacted with a reagent XXXVIII (readily prepared using standard reaction techniques known to one skilled in the art) under palladium-catalyzed cross-coupling conditions, e.g. [1,1'-bis(diphenylphosphino)ferrocene]dichloropalladium(II), sodium carbonate, in a suitable solvent such as 1,4-dioxane/water mixture, at a suitable temperature such as 100° C., with or without microwave heating, to produce a compound of formula XXXIX. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker; PG represents a suitable ester protecting group, e.g. methyl, ethyl, or t-butyl; W represents an optional protecting group, e.g. 2-(trimethylsilyl)ethoxymethyl; and the isoxazole of compound XXXVIII and following structures may have an optional substituent. Compounds of formula XXXIX may be converted to a compound of formula XL by treatment with a reagent suitable for the removal of the optional W, e.g. hydrogen chloride in 1,4-dioxane and methanol or ethylenediamine and tetra-n-butylammonium fluoride when W is 2-(trimethylsilyl)ethoxymethyl; followed by treatment with a reagent suitable for the removal of PG, e.g. sodium hydroxide in methanol and water at 40° C. when PG is methyl or ethyl. Compound XL may then be reacted with compound XLI, wherein Z is an optional substituent, e.g. H, methyl, or hydroxymethyl, to produce compounds of formula XLII under amide formation conditions, e.g. N-[(dimethylamino)-1H-1,2,3-triazolo-[4,5-b]pyridin-1-ylmethylene]-N-methylmethanaminium hexafluorophosphate N-oxide, diisopropylethylamine, DMF, room temperature. Optionally, as will be apparent to one skilled in the art, the order of the amide coupling and palladium-catalyzed cross-coupling steps may be reversed in the reaction sequence via suitable manipulations of M, M', and PG.

Scheme 14.

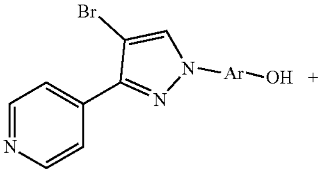

XLIII

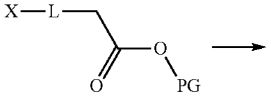

XLIV

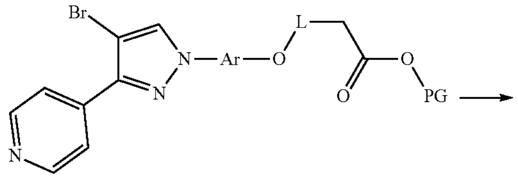

XLV

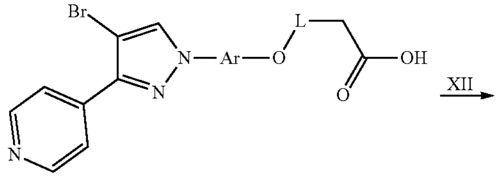

XLVI

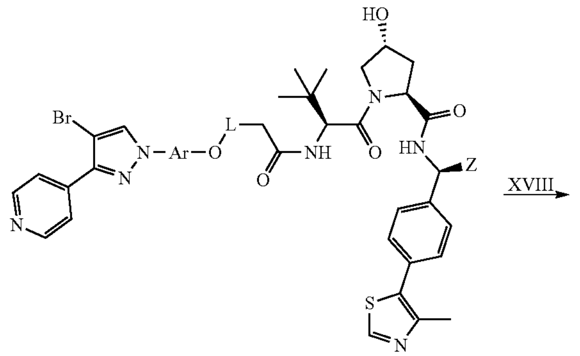

XLVII

-continued

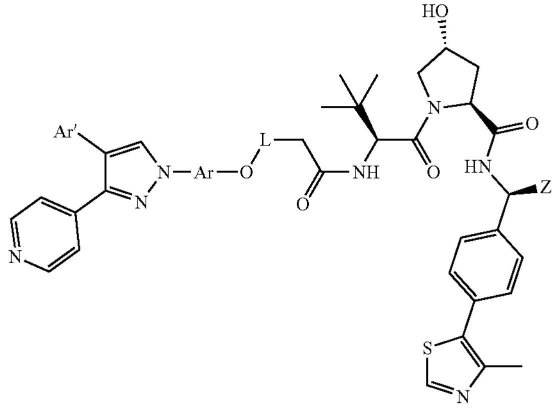

XLVIII

A compound of formula XLIII may be reacted with a reagent XLIV (commercially available or readily prepared using standard reaction techniques known to one skilled in the art) under nucleophilic substitution conditions, e.g. cesium carbonate, DMF, 75° C., to produce a compound of formula XLV. Ar represents an aromatic or heteroaromatic ring system; X represents a suitable leaving group, e.g. p-toluenesulfonate, methanesulfonate, iodide, bromide, or chloride; L represents an optional linker; and PG represents a suitable ester protecting group, e.g. methyl, ethyl, or t-butyl. Compounds of formula XLV may be converted to a compound of formula XLVI by treatment with a reagent suitable for the removal of PG, e.g. 3 N hydrochloric acid in 1,4-dioxane at room temperature when PG is t-butyl. Compound XLVI may then be reacted with compounds XII as defined in Scheme 3A or 3B to produce compounds of formula XLVII under amide formation conditions, e.g. (benzotriazol-1-yloxy)tripyrrolidinophosphonium hexafluorophosphate, diisopropylethylamine, DMF, room temperature. The compound of formula XLVII may then be treated with a reagent XVIII as defined in Scheme 5 to produce a compound of formula XLVIII. In cases where the group Ar' contains optional substituents, e.g. a ketone, these may undergo further functionalization, e.g. by treatment with hydroxylamine hydrochloride and pyridine at room temperature, to provide further compounds of formula XLVIII.

Intermediate 1: (3R)—N-[3-([5-bromo-1H-pyrrolo[2,3-b]pyridin-3-yl]carbonyl)-2,4-difluorophenyl]-3-fluoropyrrolidine-1-sulfonamide

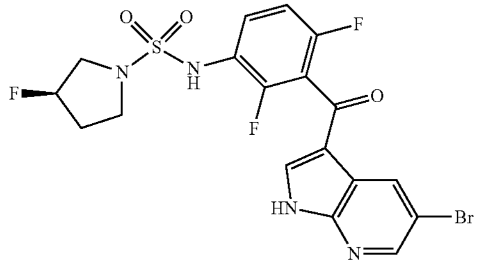 [SMILES: O=C(c1c(F)ccc(NS(=O)(=O)N2CC[C@@H](F)C2)c1F)c1c[nH]c2ncc(Br)cc12]

Step A: 2,6-difluoro-3-nitrobenzoyl chloride

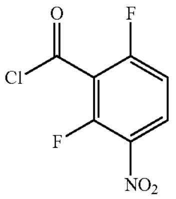 [SMILES: O=C(Cl)c1c(F)ccc([N+](=O)[O-])c1F]

Into a 150-mL round-bottom flask, was placed 2,6-difluoro-3-nitrobenzoic acid (15.0 g, 73.8 mmol, 1.0 equiv), toluene (80 mL), thionyl chloride (80 mL). The resulting mixture was stirred at 80° C. overnight and concentrated under reduced pressure. This resulted in 14.1 g (86%) of 2,6-difluoro-3-nitrobenzoyl chloride as a brown oil.

Step B: 5-bromo-3-[(2,6-difluoro-3-nitrophenyl) carbonyl]-1H-pyrrolo[2,3-b]pyridine

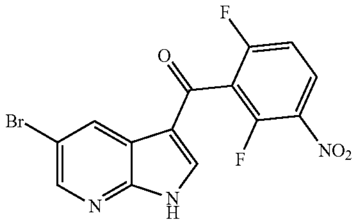 [SMILES: O=C(c1c(F)ccc([N+](=O)[O-])c1F)c1c[nH]c2ncc(Br)cc12]

5-bromo-1H-pyrrolo[2,3-b]pyridine (11.0 g, 55.8 mmol, 1.1 equiv) was mixed with 200 mL of chloromethane and aluminum trichloride (42.0 g, 318.2 mmol, 6.4 equiv) was added portionwise. The reaction was stirred at room temperature for 1 hour and 2,6-difluoro-3-nitrobenzoyl chloride (11.0 g, 49.6 mmol, 1.0 equiv) was added. The reaction was heated at 50° C. overnight, then reaction mixture was cooled to room temperature and poured to ice-water (500 mL), extracted with ethyl acetate (500 mL×3). The combined organic layer was washed with brine (500 mL×2), dried over anhydrous sodium sulfate. The solvent was concentrated to give (5-bromo-1H-pyrrolo[2,3-b]pyridin-3-yl)(2,6-difluoro-3-nitrophenyl) methanone (12.2 g) as a yellow solid, which was directly used to the next step without further purification. LCMS ($ES^+$): m/z 381.30 $[M+H]^+$.

Step C: 3-([5-bromo-1H-pyrrolo[2,3-b]pyridin-3-yl] carbonyl)-2,4-difluoroaniline

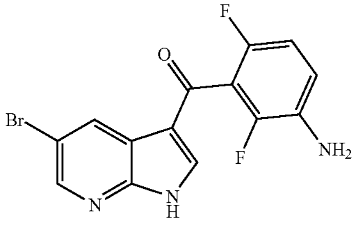

A mixture of (5-bromo-1H-pyrrolo[2,3-b]pyridin-3-yl)(2,6-difluoro-3-nitrophenyl)methanone (7.8 g, 20.4 mmol, 1.0 equiv), iron (5.6 g, 100.2 mmol, 4.9 equiv), ammonium chloride (3.6 g, 68 mmol), hydrochloric acid (25.0 mL) in ethanol (40 mL) and tetrahydrofuran (40 mL) was refluxed overnight. After cooling to room temperature, the mixture was filtered via a pad of Celite. The filtrate was concentrated in vacuo and the residue was purified by column chromatography on silica gel (petroleum ether/ethyl acetate=1/2) to give (3-amino-2,6-difluorophenyl)(5-bromo-1H-pyrrolo[2,3-b]pyridin-3-yl)methanone (4.3 g, 60% yield) as a yellow solid. LCMS ($ES^+$): m/z 351.80 $[M+H]^+$.

Step D: (R)-3-fluoropyrrolidine-1-sulfonyl chloride

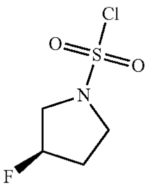

An oven dried flask was charged with (R)-3-fluoropyrrolidine hydrochloride (3.0 g, 24 mmol). tRiethylamine (7.2 g, 72 mmol) and dichloromethane (150 mL). The mixture was stirred for 15 minutes at room temperature and then cooled to about −30° C. in a dryice/acetonitrile bath for 10 minutes. Sulfuryl chloride (6.0 g, 48 mmol) was added dropwise over 10 minutes. The reaction mixture was stirred at about −30° C. for an hour, then stirred at room temperature for 5 hours. The reaction mixture was diluted with aqueous HCl (1 N, 70 mL). The layers were separated and the aqueous layers were extracted with dichloromethane (50 mL×3). The combined organic layer was washed with aqueous HCl (1 N, 50 mL) and brine (50 mL), dried over anhydrous sodium sulfate. The solvent was concentrated to give (R)-3-fluoropyrrolidine-1-sulfonyl chloride (4.5 g) as a white solid, which was directly used to the next step without further purification.

Step E: (3R)—N-[3-([5-bromo-1H-pyrrolo[2,3-b] pyridin-3-yl]carbonyl)-2,4-difluorophenyl]-3-fluoropyrrolidine-1-sulfonamide

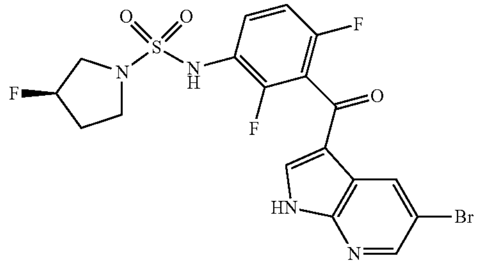 [SMILES: O=C(c1c(F)ccc(NS(=O)(=O)N2CC[C@@H](F)C2)c1F)c1c[nH]c2ncc(Br)cc12]

To a solution of (3-amino-2,6-difluorophenyl)(5-bromo-1H-pyrrolo[2,3-b]pyridin-3-yl)methanone (8.0 g, 22.79 mmol, 1.0 eq) in pyridine (25.0 g) was added (R)-3-fluoropyrrolidine-1-sulfonyl chloride (4.6 g, 24.60 mmol, 1.08 eq) and 4-dimethylaminopyridine (560.0 mg, 4.59 mmol, 0.2 eq). The reaction mixture was stirred for 12 hours at 40° C. The solvent was removed and water (20 mL) was added, adjusted pH=7~8 with aqueous sodium bicarbonate, extracted with ethyl acetate (100 mL×2). The combined organic layer was washed with brine (50 mL×2), dried over anhydrous sodium sulfate. The solvent was removed in vacuo and the residue was purified by column chromatography on silica gel with ethyl acetate/petroleum ether (3:1) to give (R)—N-(3-(5-bromo-1H-pyrrolo[2,3-b]pyridine-3-carbonyl)-2,4-difluorophenyl)-3-fluoropyrrolidine-1-sulfonamide (6.4 g) as a yellow solid LCMS ($ES^+$): m/z 505.05 $[M+H]^+$.

Intermediate 2: (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide

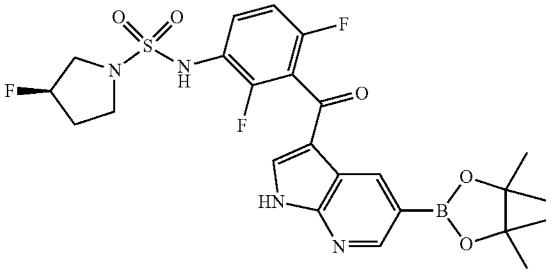 [SMILES: CC1(C)OB(c2cnc3[nH]cc(C(=O)c4c(F)ccc(NS(=O)(=O)N5CC[C@@H](F)C5)c4F)c3c2)OC1(C)C]

Step A: (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide To a solution of (R)—N-(3-(5-bromo-1H-pyrrolo[2,3-b]pyridine-3-carbonyl)-2,4-difluorophenyl)-3-fluoropyrrolidine-1-sulfonamide (1.0 g, 2.0 mmol) in 1,4-dioxane were added KOAc (392.0 mg, 4.0 mmol), Pd(dppf)$Cl_2$ (163.0 mg, 0.2 mmol), and 4,4,4',4',5,5,5',5'-octamethyl-2,2'-bi(1,3,2-dioxaborolane) (1.02 g, 4.0 mmol) subsequently. The resulting solution was heated to 90° C. overnight under $N_2$. After cooling to room temperature, the solvent was removed under reduced pressure. The residue was purified by column chromatography on silica gel eluting with ethyl acetate/petroleum ether (1:1). This resulted in 551.0 mg (50%) (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide as a light brown solid. LCMS ($ES^+$): m/z 551.15 $[M+H]^+$.

Intermediate 3: N-(3-[5-bromo-1H-pyrrolo[2,3-b]pyridine-3-carbonyl]-2,4-difluorophenyl)-2-(dimethylamino)ethane-1-sulfonamide

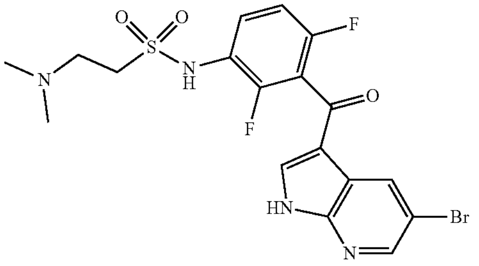 [SMILES: CN(C)CCS(=O)(=O)Nc1ccc(F)c(C(=O)c2c[nH]c3ncc(Br)cc23)c1F]

Step A: N-(3-[5-bromo-1H-pyrrolo[2,3-b]pyridine-3-carbonyl]-2,4-difluorophenyl)ethene-1-sulfonamide

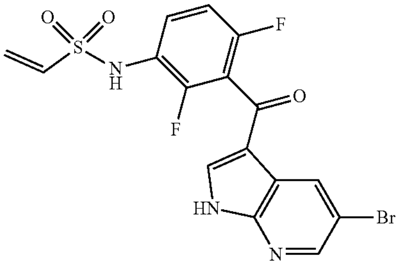 [SMILES: C=CS(=O)(=O)Nc1ccc(F)c(C(=O)c2c[nH]c3ncc(Br)cc23)c1F]

Into a 100 mL round-bottom flask, was placed 3-[5-bromo-1H-pyrrolo[2,3-b]pyridine-3-carbonyl]-2,4-difluoroaniline (500 mg, 1.42 mmol, 1 equiv), pyridine (20 mL, 248.47 mmol, 174.99 equiv), DMAP (35 mg, 0.29 mmol, 0.20 equiv), ethenesulfonyl chloride (360 mg, 2.84 mmol, 2.00 equiv), dichloromethane (20 mL). The resulting solution was stirred for 0.5 hour at room temperature. The reaction mixture was concentrated under reduced pressure. The residue was applied onto a silica gel column eluting with ethyl acetate/petroleum ether (1:1). This resulted in 300 mg (48%) of N-(3-[5-bromo-1H-pyrrolo[2,3-b]pyridine-3-carbonyl]-2,4-difluorophenyl)ethene-1-sulfonamide as a white solid. LCMS ($ES^+$): m/z 443.80$[M+H]^+$.

Step B: N-(3-5-bromo-1H-pyrrolo[2,3-b]pyridine-3-carbonyl 1-2,4-difluorophenyl)-2-(dimethylamino)ethane-1-sulfonamide

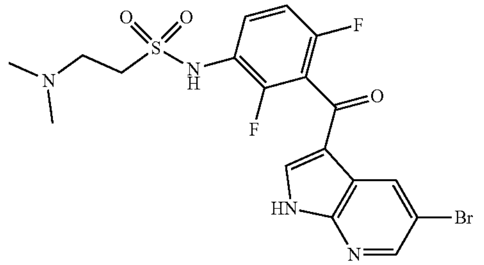 [SMILES: CN(C)CCS(=O)(=O)Nc1ccc(F)c(C(=O)c2c[nH]c3ncc(Br)cc23)c1F]

Into a 100 mL round-bottom flask, was placed N-(3-[5-bromo-1H-pyrrolo[2,3-b]pyridine-3-carbonyl]-2,4-difluorophenyl)ethene-1-sulfonamide (300 mg, 0.68 mmol, 1 equiv), dichloromethane (20 mL), dimethylamine (2.0 mL). The resulting solution was stirred for 2 hours at room temperature. The reaction mixture was concentrated under reduced pressure. This resulted in 360 mg (crude) of N-(3-[5-bromo-1H-pyrrolo[2,3-b]pyridine-3-carbonyl]-2,4-difluorophenyl)-2-(dimethylamino)ethane-1-sulfonamide as a white solid. LCMS ($ES^+$): m/z 488.85 $[M+H]^+$.

Intermediate 4: N-(3-[5-bromo-1H-pyrrolo[2,3-b]pyridine-3-carbonyl]-2,4-difluorophenyl)-2,3-dihydroxypropane-1-sulfonamide

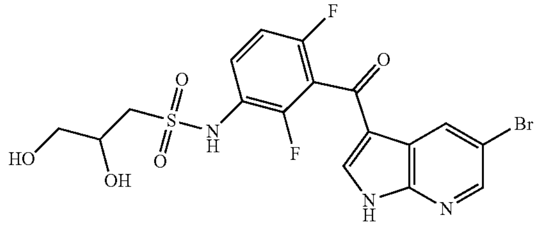 [SMILES: O=C(c1c(F)ccc(NS(=O)(=O)CC(O)CO)c1F)c1c[nH]c2ncc(Br)cc12]

Step A: N-(3-[5-bromo-1H-pyrrolo[2,3-b]pyridine-3-carbonyl]-2,4-difluorophenyl)prop-2-ene-1-sulfonamide

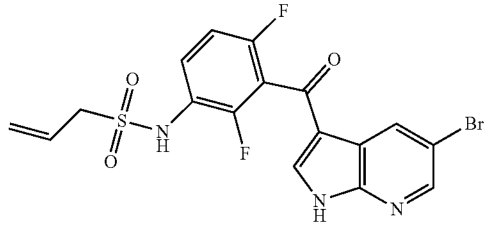 [SMILES: C=CCS(=O)(=O)Nc1ccc(F)c(C(=O)c2c[nH]c3ncc(Br)cc23)c1F]

Into a 25 mL round-bottom flask, was placed 3-[5-bromo-1H-pyrrolo[2,3-b]pyridine-3-carbonyl]-2,4-difluoroaniline (500 mg, 1.42 mmol, 1 equiv), pyridine (2 mL, 15 equiv), prop-2-ene-1-sulfonyl chloride (399.2 mg, 2.84 mmol, 2 equiv), DMAP (52.0 mg, 0.43 mmol, 0.3 equiv). The resulting solution was stirred overnight at 45° C. in an oil bath. The resulting mixture was concentrated. The residue was applied onto a silica gel column eluting with ethyl acetate/petroleum ether (1/1). This resulted in 480 mg (74%) of N-(3-[5-bromo-1H-pyrrolo[2,3-b]pyridine-3-carbonyl]-2,4-difluorophenyl)prop-2-ene-1-sulfonamide as a yellow solid.

Step B: N-(3-[5-bromo-1H-pyrrolo[2,3-b]pyridine-3-carbonyl]-2,4-difluorophenyl)-2,3-dihydroxypropane-1-sulfonamide

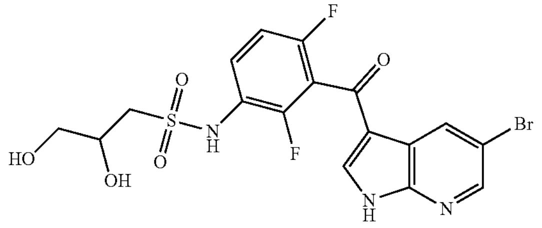 [SMILES: O=C(c1c(F)ccc(NS(=O)(=O)CC(O)CO)c1F)c1c[nH]c2ncc(Br)cc12]

Into a 50 mL round-bottom flask, was placed N-(3-[5-bromo-1H-pyrrolo[2,3-b]pyridine-3-carbonyl]-2,4-difluorophenyl)prop-2-ene-1-sulfonamide (430 mg, 0.94 mmol, 1 equiv), acetone (20 mL), N-methylmorpholine N-oxide (226 mg), water (5 mL), tetraoxoosmium (4 mL). The resulting solution was stirred overnight at room temperature. The reaction was then quenched by the addition of water (20 mL). The resulting solution was extracted with ethyl acetate (30 mL×3). The resulting mixture was washed with brine (20 mL×1), dried over anhydrous sodium sulfate and concentrated under reduced pressure. The residue was applied onto a silica gel column eluting with ethyl acetate/petroleum ether (1/1). This resulted in 377 mg (82%) of N-(3-[5-bromo-1H-pyrrolo[2,3-b]pyridine-3-carbonyl]-2,4-difluorophenyl)-2,3-dihydroxypropane-1-sulfonamide as a white solid.

Intermediate 5: (R)—N-(3-(5-bromo-1H-pyrrolo[2,3-b]pyridine-3-carbonyl)-2,4-difluorophenyl)-3-fluoropyrrolidine-1-carboxamide

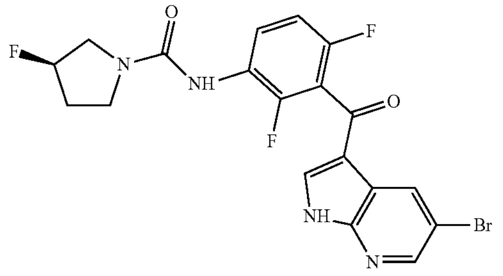 [SMILES: O=C(c1c(F)ccc(NC(=O)N2CC[C@@H](F)C2)c1F)c1c[nH]c2ncc(Br)cc12]

To the solution of (3-amino-2,6-difluorophenyl)(5-bromo-1H-pyrrolo[2,3-b]pyridin-3-yl)methanone (2.0 g, 5.70 mmol, 1.00 equiv), triethylamine (8.6 g, 85.5 mmol, 15.00 equiv) in dichloromethane (80 mL) was slowly added a solution of bis(trichloromethyl) carbonate (2.5 g, 8.55 mmol, 1.50 equiv) in dichloromethane (40 mL), followed by dropwise addition of a solution of (R)-3-fluoropyrrolidine (761.0 mg, 8.55 mmol, 1.50 equiv) in dichloromethane (40 mL) at 0° C. The resulting solution was stirred for 30 minutes at 0° C. in a water/ice bath. The resulting solution was quenched by the aqueous solution of ammonium chloride (40 mL), extracted with dichloromethane (40 mL×2). Then the organic layers were combined and concentrated. The residue was applied onto a silica gel column with chloroform/methanol (10:1). This resulted in 541.0 mg (20%) of (R)—N-(3-(5-bromo-1H-pyrrolo[2,3-b]pyridine-3-carbonyl)-2,4-difluorophenyl)-3-fluoropyrrolidine-1-carboxamide as a tawny solid. LCMS ($ES^+$): m/z 467.10 $[M+H]^+$.

Scheme 15.

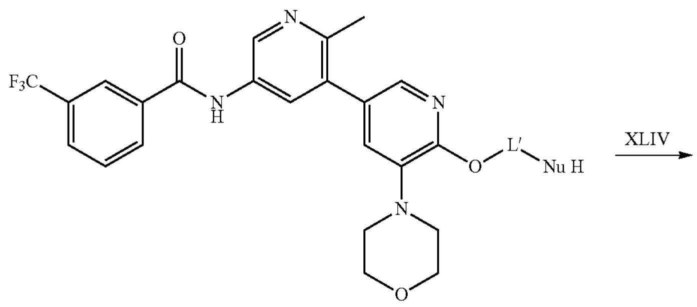

XLIX

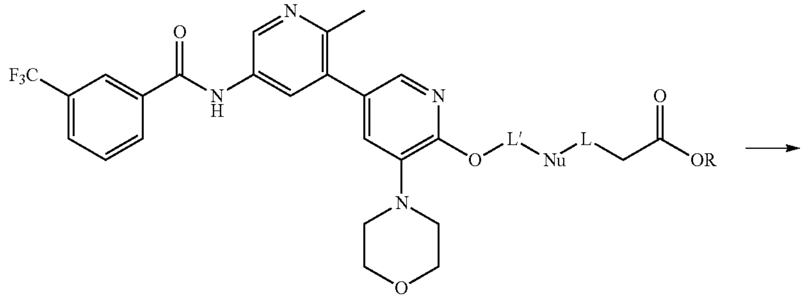

L

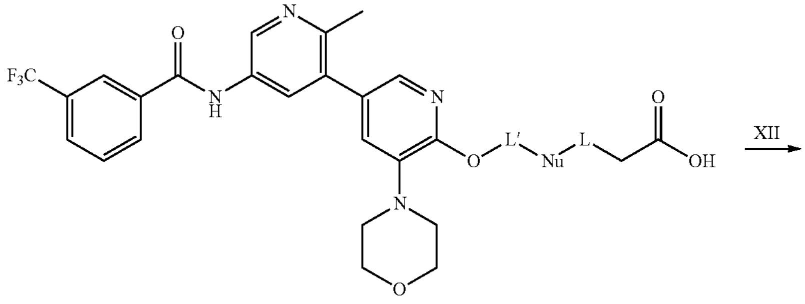

LI

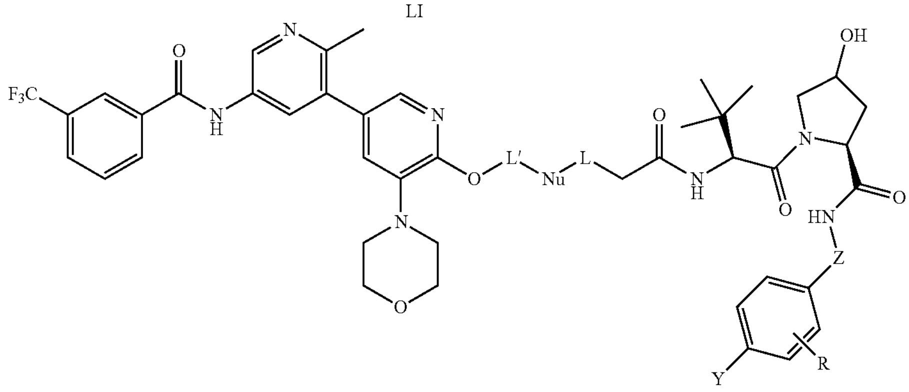

LII

A compound of formula XLIX (readily prepared using standard reaction techniques known to one skilled in the art) may be reacted with a compound of formula.

A compound of formula XLIX may be reacted with a reagent XLIV under nucleophilic substitution conditions, e.g. diisopropylethylamine, potassium iodide, acetonitrile, 100° C., to produce a compound of formula L. L' represents an optional linker or portion of a linker; Nu-H represents a suitable nucleophile such as an alcohol or secondary amine; X represents a suitable leaving group, e.g. p-toluenesulfonate, methanesulfonate, iodide, bromide, or chloride; L represents an optional linker; and PG represents a suitable ester protecting group, e.g. methyl, ethyl, or t-butyl. Compounds of formula L may be converted to a compound of formula LI by treatment with a reagent suitable for the removal of PG, e.g. trifluoroacetic acid, dichloromethane, 30° C. when PG is t-butyl. Compound LI may then be reacted with compounds XII as defined in Scheme 3A or 3B to produce compounds of formula LII under amide formation conditions, e.g. 1-ethyl-3-(3-dimethylaminopropyl)carbodiimide, 1-hydroxybenzotriazole, triethylamine, DMF, 30° C.

Scheme 16.

XLIX +

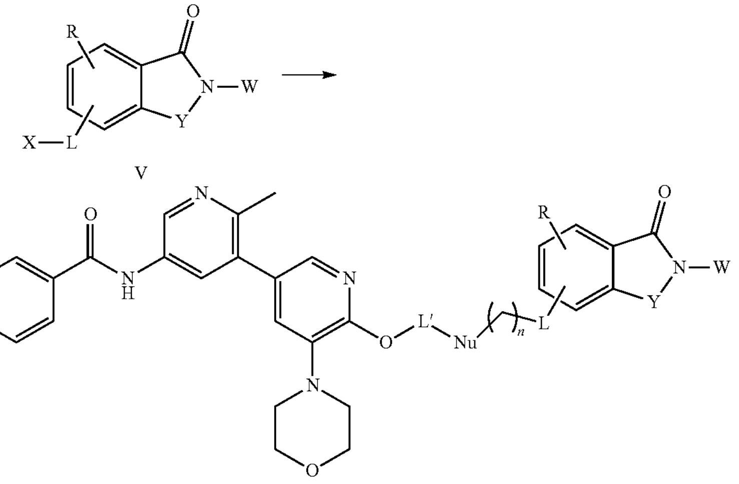

V

LIII

A compound of formula XLIX as defined in Scheme 15 may be reacted with compound V to produce compound LIII, wherein L represents an optional linker or portion of a linker, Y is $CH_2$ or C═O, X is either a suitable leaving group (e.g. OMs, OTs, Cl, etc.) or an aldehyde (CHO); R is an optional substituent (e.g. F or $OCH_3$); and W is:

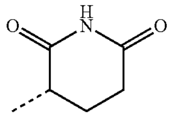

when Y is C═O; or

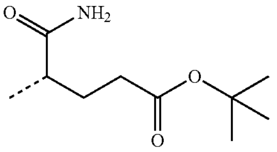

when Y is $CH_2$.

When X is a leaving group, n is 0, Nu-H is a primary or secondary amine or alcohol, and suitable reaction conditions are those for an alkylation reaction, e.g. potassium carbonate, DMF, 70° C. When X is an aldehyde, n is 1, Nu-H is a primary or secondary amine, and suitable reaction conditions are those for a reductive amination reaction, e.g. sodium cyanoborohydride, methanol, dichloromethane, acetic acid, room temperature. It will be apparent to one skilled in the art that the positions of Nu-H in XLIX and X in V' may also be reversed, such that the positions of Nu and $(CH_2)_n$ are reversed in compound LIII. A compound of formula LIII where W is in an open chain form may be further transformed to another compound of formula LIII where W is a glutarimide by cyclization under appropriate conditions, e.g. benzenesulfonic acid, acetonitrile, 100° C.

Scheme 17.

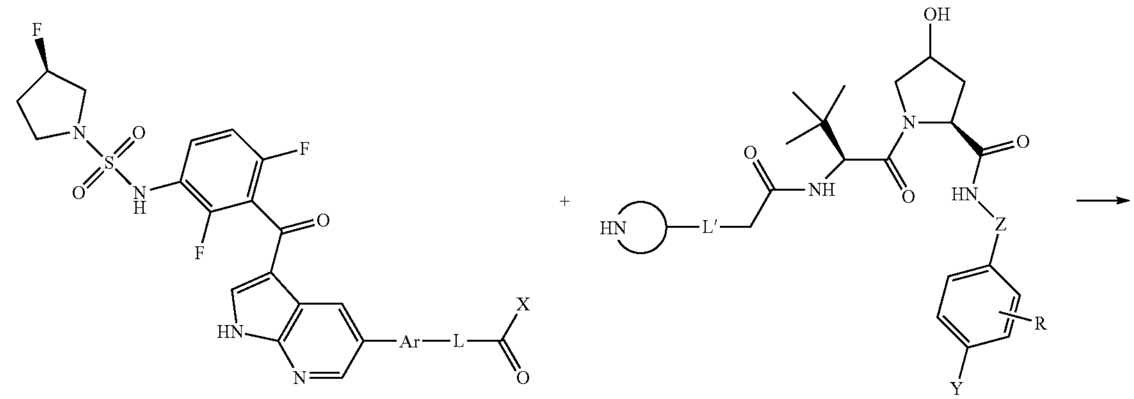

LIV

+

LV

-continued

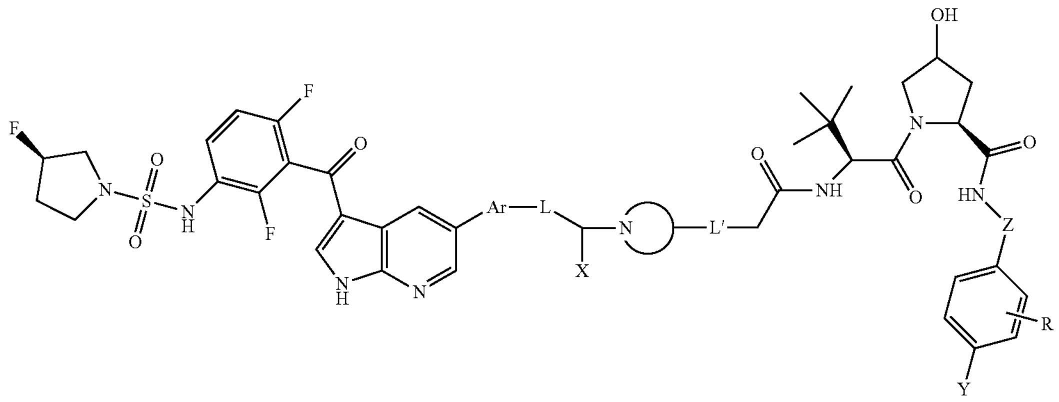

LVI

A compound of formula LIV (prepared using standard conditions known to one skilled in the art, analogous to the synthesis of compounds III in Scheme 1A or 1B) may be reacted with a compound of formula LV (prepared using standard conditions known to one skilled in the art, analogous to the synthesis of compounds XV in Scheme 2) under reductive amination conditions, e.g. sodium triacetoxyborohydride, triethylamine, dichloroethane, 30° C., to produce a compound of formula LVI. Herein, Ar is an aromatic or heteroaromatic ring system; L and L' are an optional linker or portion of a linker; X is H or an optional substituent, which may be optionally cyclized into L to form a ring;

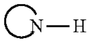

represents a primary or secondary amine, optionally cyclized into a 4 to 8 membered heterocyclic ring; and R, Z, and Y are as defined for compound XII in Scheme 3B. It will be apparent to one skilled in the art that the positions of C(O)X in LIV and

in LV may be reversed, with X optionally cyclized into L' to form a ring, such that the positions of CHX and

are reversed in compound LVI.

Scheme 18.

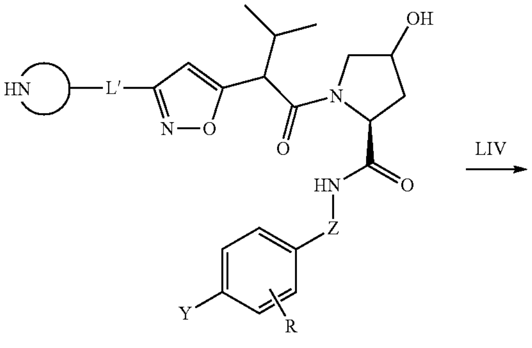

LVII

-continued

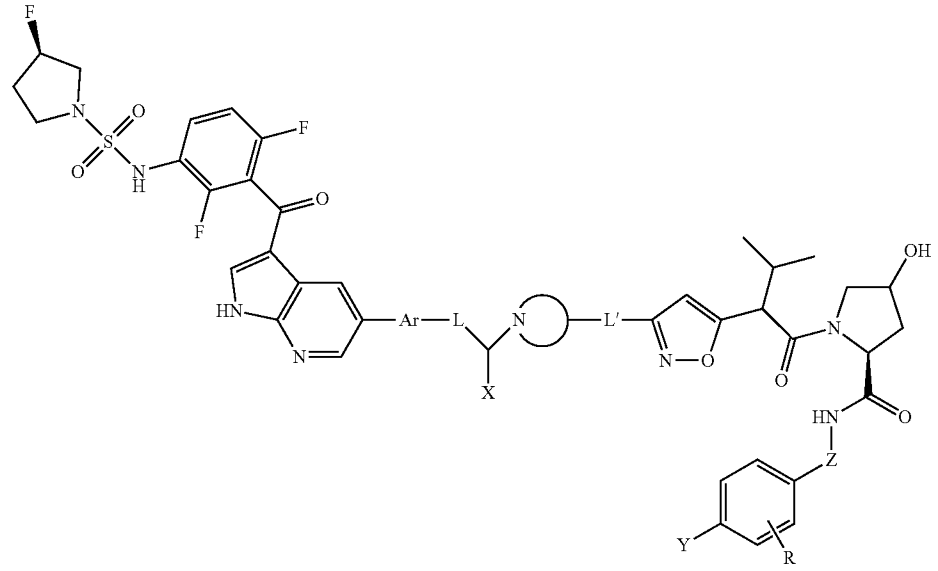

LVIII

A compound of formula LIV (prepared using standard conditions known to one skilled in the art, analogous to the synthesis of compounds III in Scheme 1A or 1B) may be reacted with a compound of formula LVII (prepared using standard conditions known to one skilled in the art) under reductive amination conditions, e.g. sodium triacetoxyborohydride, acetic acid, dichloromethane, methanol, 30° C., to produce a compound of formula LVIII. Herein, Ar is an aromatic or heteroaromatic ring system; L and L' are an optional linker or portion of a linker; X is H or an optional substituent, which may be optionally cyclized into L to form a ring;

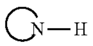

represents a primary or secondary amine, optionally cyclized into a 4 to 8 membered heterocyclic ring; R, Z, and Y are as defined for compound XII in Scheme 3B; and the isoxazole of compound LVII and following structures may have an optional substituent. It will be apparent to one skilled in the art that the positions of C(O)X in LIV and

in LVII may be reversed, with X optionally cyclized into L' to form a ring, such that the positions of CHX and

are reversed in compound LVIII.

Example Synthesis of Compound 86

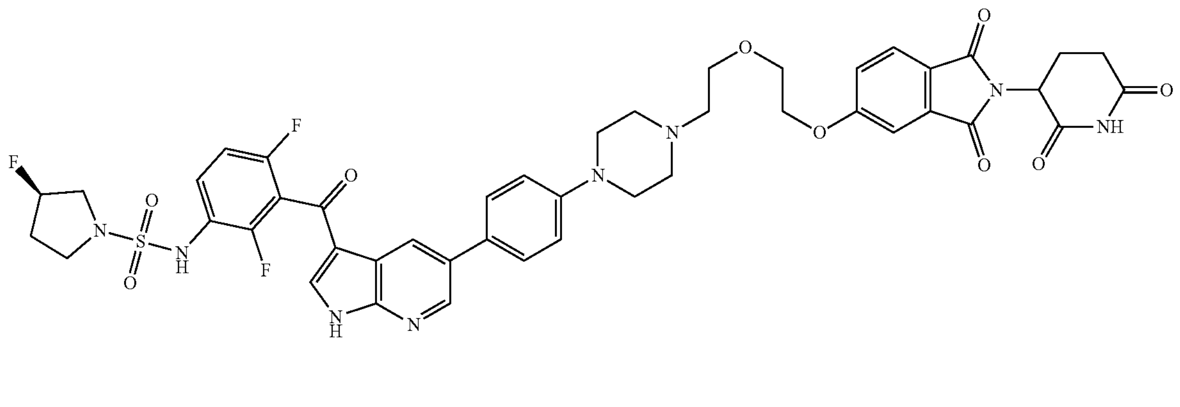 [SMILES: O=C1CCC(N2C(=O)c3ccc(OCCOCCN4CCN(c5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

Step A: (R)-tert-butyl 4-(4-(3-(2,6-difluoro-3-(3-fluoropyrrolidine-1-sulfonamido)benzoyl)-1H-pyrrolo[2,3-b]pyridin-5-yl)phenyl)piperazine-1-carboxylate

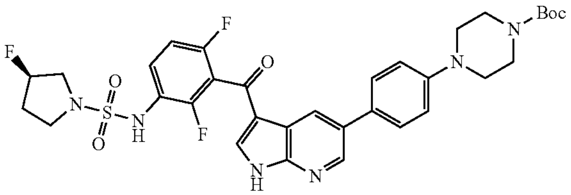 [SMILES: CC(C)(C)OC(=O)N1CCN(c2ccc(-c3cnc4[nH]cc(C(=O)c5c(F)ccc(NS(=O)(=O)N6CC[C@@H](F)C6)c5F)c4c3)cc2)CC1]

A solution of (R)—N-(3-(5-bromo-1H-pyrrolo[2,3-b]pyridine-3-carbonyl)-2,4-difluorophenyl)-3-fluoropyrrolidine-1-sulfonamide (0.50 g, 1.0 mmol) in 1,4-dioxane/$H_2O$ (20 mL/2 mL), was added tert-butyl 4-(4-(4,4,5,5-tetramethyl-1,3,2-dioxaborolan-2-yl)phenyl)piperazine-1-carboxylate (0.43 g, 1.2 mmol), cesium fluoride (0.23 g, 1.5 mmol) and Pd(aMPhos)$Cl_2$ (0.11 g, 0.15 mmol) under an argon atmosphere. The mixture was stirred at 100° C. for 3 hours. After being cooled to room temperature, water was added. The aqueous phase was extracted with ethyl acetate (20 mL×3), and the combined organic phases were dried over anhydrous sodium sulfate, filtered, and concentrated in vacuo. The crude product was purified by silica gel (dichloromethane/methanol=12:1) to give compound (R)-tert-butyl 4-(4-(3-(2,6-difluoro-3-(3-fluoropyrrolidine-1-sulfonamido)benzoyl)-1H-pyrrolo[2,3-b]pyridin-5-yl)phenyl)piperazine-1-carboxylate (0.39 g, 57%) as a yellow solid. LCMS: m/z 685.2 $[M+H]^+$; NMR (400 MHz, DMSO-$d_6$) δ 1.43 (9H, s), 2.06-2.12 (1H, m), 3.18-3.20 (4H, m), 3.26-3.30 (1H, m), 3.37-3.53 (8H, m), 5.30 (1H, d, J=52.0 Hz), 7.10 (2H, d, J=8.8 Hz), 7.28 (1H, t, J=8.4 Hz), 7.60-7.64 (3H, m), 8.09 (1H, d, J=2.8 Hz), 8.55 (1H, brs.), 8.66 (1H, d, J=2.4 Hz), 9.87 (1H, s), 12.93 (1H, s).

Step B: (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide

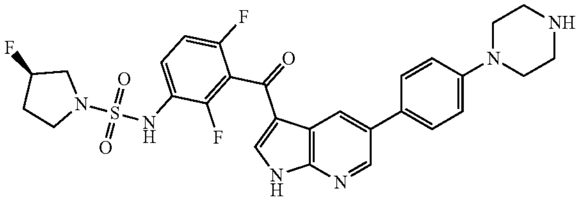 [SMILES: O=C(c1c(F)ccc(NS(=O)(=O)N2CC[C@@H](F)C2)c1F)c1c[nH]c2ncc(-c3ccc(N4CCNCC4)cc3)cc12]

To a solution of (R)-tert-butyl 4-(4-(3-(2,6-difluoro-3-(3-fluoropyrrolidine-1-sulfonamido)benzoyl)-1H-pyrrolo[2,3-b]pyridin-5-yl)phenyl)piperazine-1-carboxylate (0.39 g, 0.57 mmol) in hydrochloric acid/1,4-dioxane (5 mL, 4.0 N) was stirred at room temperature for 3 hours. Then the solvent was directly removed, then water (10 mL) was added and the pH of the mixture was adjusted to 8-9 by saturated sodium bicarbonate. The aqueous phase was extracted with ethyl acetate (10 mL×3), and the combined organic phases were dried over anhydrous sodium sulfate, filtered, and concentrated in vacuo to give (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide (0.30 g, 91%) as a yellow solid.

Step C: 2-(2-chloroethoxy)ethyl 4-methylbenzenesulfonate

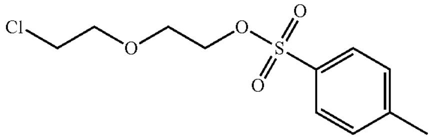 [SMILES: Cc1ccc(S(=O)(=O)OCCOCCCl)cc1]

The mixture of 2-(2-chloroethoxy)ethanol (0.5 g, 4.0 mmol), tosyl chloride (0.8 g, 4.0 mmol) and triethylamine (810 mg, 8.1 mmol) in dichloromethane (10 mL) was stirred at room temperature overnight. The mixture was poured into saturated sodium bicarbonate solution (20 mL) and extracted with dichloromethane (20 mL×3). The combined organic phase was concentrated in vacuo and the residue was purified by column chromatography on silica gel (petroleum ether/ethyl acetate=10/1) to give 2-(2-chloroethoxy)ethyl 4-methylbenzenesulfonate (0.9 g, 80% yield) as colorless oil. LCMS: m/z 279.1 $[M+H]^+$.

Step D: 5-(2-(2-chloroethoxy)ethoxy)-2-(2,6-dioxopiperidin-3-yl)isoindoline-1,3-dione

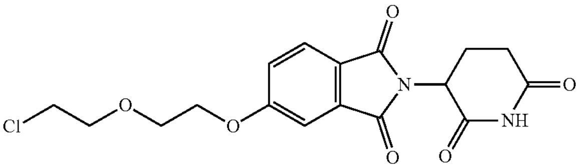 [SMILES: O=C1CCC(N2C(=O)c3ccc(OCCOCCCl)cc3C2=O)C(=O)N1]

The mixture of 2-(2-chloroethoxy)ethyl 4-methylbenzenesulfonate (100 mg, 0.36 mmol), 2-(2,6-dioxopiperidin-3-yl)-5-hydroxyisoindoline-1,3-dione (98 mg, 0.36 mmol), ethyldiisopropylamine (93 mg, 0.72 mmol) and potassium iodide (59 mg, 0.36 mmol) in dimethyl sulfoxide (5 mL) was heated at 45° C. for 2 hours and then cooled to room temperature. The reaction mixture was poured into water (10 mL) and extracted with dichloromethane (15 mL×3). The combined organic phase was concentrated in vacuo and the residue was purified by column chromatography on silica gel (dichloromethane/methanol=20/1) to give 5-(2-(2-chloroethoxy)ethoxy)-2-(2,6-dioxopiperidin-3-yl)isoindoline-1,3-dione (48 mg, 35% yield) as a white solid. LCMS: m/z 381.2 $[M+H]^+$.

Step E: (3R)—N-(3-(5-(4-(4-(2-(2-(2-(2,6-dioxopiperidin-3-yl)-1,3-dioxoisoindolin-5-yloxy)ethoxy)ethyl)piperazin-1-yl)phenyl)-1H-pyrrolo[2,3-b]pyridine-3-carbonyl)-2,4-difluorophenyl)-3-fluoropyrrolidine-1-sulfonamide

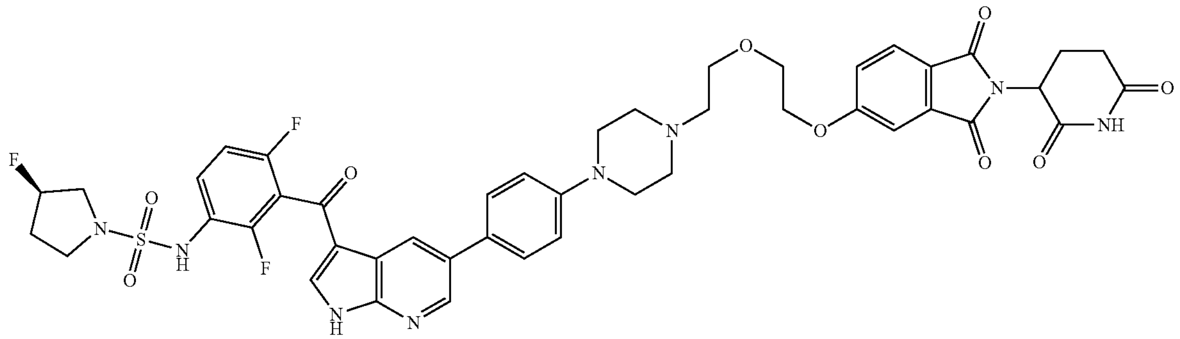 [SMILES: O=C1CCC(N2C(=O)c3ccc(OCCOCCN4CCN(c5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

The mixture of 5-(2-(2-chloroethoxy)ethoxy)-2-(2,6-dioxopiperidin-3-yl)isoindoline-1,3-dione (40 mg, 0.11 mmol), (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide (61 mg, 0.11 mmol), ethyldiisopropylamine (28 mg, 0.22 mmol) and potassium iodide (18 mg, 0.11 mmol) in dimethyl sulfoxide (5 mL) was heated at 80° C. overnight. The mixture was poured into water (10 mL) and extracted with dichloromethane (10 mL×3). The organic phase was concentrated in vacuo and the residue was purified by pre-HPLC to give (3R)—N-(3-(5-(4-(4-(2-(2-(2-(2,6-dioxopiperidin-3-yl)-1,3-dioxoisoindolin-5-yloxy)ethoxy)ethyl)piperazin-1-yl)phenyl)-1H-pyrrolo[2,3-b]pyridine-3-carbonyl)-2,4-difluorophenyl)-3-fluoropyrrolidine-1-sulfonamide (31 mg, 30% yield) as a yellow solid. LCMS: m/z 929.3 $[M+H]^+$; NMR (400 MHz, DMSO-$d_6$) δ 1.95-2.10 (3H, m), 2.53-2.59 (8H, m), 3.18-3.23 (4H, m), 3.24-3.31 (2H, m), 3.36-3.39 (2H, m), 3.47 (1H, s), 3.64 (2H, t, J=6.0 Hz), 3.80 (2H, t, J=4.0 Hz), 4.35 (2H, t, J=4.0 Hz), 5.12 (1H, dd, J=5.6, 9.6 Hz), 5.29 (1H, d, J=12.8 Hz), 7.05 (2H, d, J=8.8 Hz), 7.26 (1H, d, J=8.8 Hz), 7.39 (1H, dd, J=2.0, 8.4 Hz), 7.48 (1H, d, J=2.4 Hz), 7.58-7.65 (3H, m), 7.85 (1H, d, J=8.4 Hz), 8.07 (1H, s), 8.53 (1H, d, J=2.4 Hz), 8.65 (1H, d, J=2.4 Hz), 9.85 (1H, brs), 11.1 (1H, s), 12.9 (1H, s).

Compounds 87-90 may be prepared in an analogous manner.

Example Synthesis of Compound 91

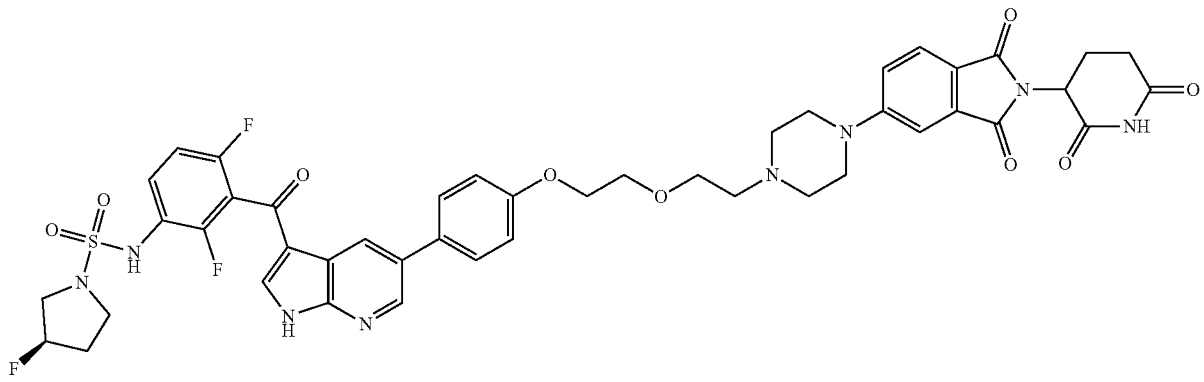 [SMILES: O=C1CCC(N2C(=O)c3ccc(N4CCN(CCOCCOc5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

Step A: 2-(2-(4-(4,4,5,5-tetramethyl-1,3,2-dioxaborolan-2-yl)phenoxy)ethoxy)ethanol

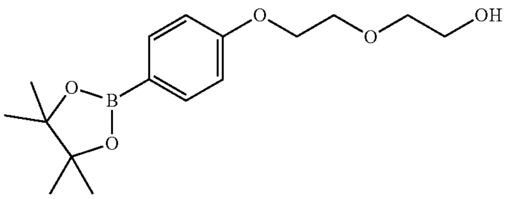 [SMILES: CC1(C)OB(c2ccc(OCCOCCO)cc2)OC1(C)C]

To a solution of 2-(2-chloroethoxy)ethanol (2.0 g, 16.1 mmol) in N,N-dimethylformamide (15.0 mL) was added 4-(4,4,5,5-tetramethyl-1,3,2-dioxaborolan-2-yl)phenol (3.54 g, 16.1 mmol), cesium carbonate (10.5 g, 32.2 mmol) and potassium iodide (267 mg, 1.61 mmol). The reaction mixture was stirred at 60° C. overnight. Then water (50 mL) was added and extracted with ethyl acetate (50 mL×3), washed with brine (5 mL×4). The combined organic phases were dried over anhydrous sodium sulfate, filtered, and concentrated in vacuo. The residue was purified by silica gel (petroleum ether/ethyl acetate=2:1) to give 2-(2-(4-(4,4,5,5-tetramethyl-1,3,2-dioxaborolan-2-yl)phenoxy)ethoxy)ethanol (2.1 g, 42%) as yellow oil. $^1$H NMR (400 MHz, DMSO-$d_6$) δ 1.28 (12H, s), 3.49-3.52 (4H, m), 3.74 (2H, t, J=4.8 Hz), 4.10-4.12 (2H, m), 4.62-4.64 (1H, m), 6.93 (2H, d, J=9.2 Hz), 7.60 (2H, d, J=8.4 Hz).

Step B: 2-(2-(4-(4,4,5,5-tetramethyl-1,3,2-dioxaborolan-2-yl)phenoxy)ethoxy)ethyl methanesulfonate

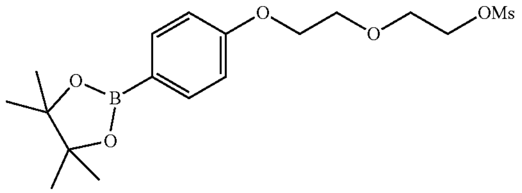 [SMILES: CC1(C)OB(c2ccc(OCCOCCOS(C)(=O)=O)cc2)OC1(C)C]

To a solution of 2-(2-(4-(4,4,5,5-tetramethyl-1,3,2-dioxaborolan-2-yl)phenoxy)ethoxy)ethanol (350 mg, 1.14 mmol) in dichloromethane (15.0 mL) was added triethylamine (231 mg, 2.28 mmol) and methanesulfonyl chloride (157 mg, 1.37 mmol) under nitrogen. The resulting reaction mixture was stirred at room temperature for 1 hour. Then aq. sodium bicarbonate (20.0 mL) was added and extracted with dichloromethane (20 mL×3), washed by brine, dried and concentrated in vacuo to give crude 2-(2-(4-(4,4,5,5-tetramethyl-1,3,2-dioxaborolan-2-yl)phenoxy)ethoxy)ethyl methanesulfonate as yellow oil, which was used for the next step without further purification. LCMS: m/z 404.2 $[M+18]^+$.

Step C: tert-butyl 4-(2-(2-(4-(4,4,5,5-tetramethyl-1,3,2-dioxaborolan-2-yl)phenoxy)ethoxy)ethyl)piperazine-1-carboxylate

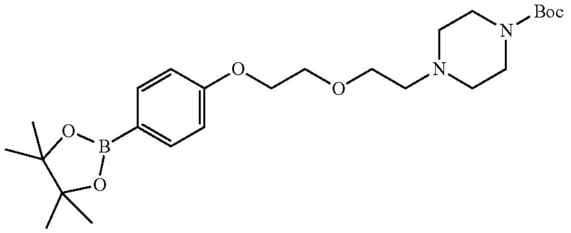 [SMILES: CC(C)(C)OC(=O)N1CCN(CCOCCOc2ccc(B3OC(C)(C)C(C)(C)O3)cc2)CC1]

To a solution of 2-(2-(4-(4,4,5,5-tetramethyl-1,3,2-dioxaborolan-2-yl)phenoxy)ethoxy)ethyl methanesulfonate (1.14 mmol) in acetonitrile (20 mL) was added potassium carbonate (315 mg, 2.28 mmol) and tert-butyl piperazine-1-carboxylate (234 mg, 1.25 mmol). The resulting reaction mixture was stirred at 80° C. overnight. The solvent was concentrated in vacuo. The residue was extracted with ethyl acetate (20 mL×3) and water (20 mL). The organic phase was dried and concentrated in vacuo. The residue was purified by preparative TLC (petroleum ether/ethyl acetate=1:2) to give tert-butyl 4-(2-(2-(4-(4,4,5,5-tetramethyl-1,3,2-dioxaborolan-2-yl)phenoxy)ethoxy)ethyl)piperazine-1-carboxylate (280 mg, 52% for two steps) as a pale yellow solid. $^1$H NMR (400 MHz, DMSO-$d_6$) δ 1.27 (12H, s), 1.38 (9H, s), 2.35 (4H, t, J=5.2 Hz), 2.47-2.50 (2H, m), 3.25-3.26 (4H, m), 3.57 (2H, t, J=6.0 Hz), 3.70-3.73 (2H, m), 4.10-4.12 (2H, m), 6.92 (2H, d, J=8.8 Hz), 7.59 (2H, d, J=8.4 Hz).

Step D: (R)-tert-butyl 4-(2-(2-(4-(3-(2,6-difluoro-3-(3-fluoropyrrolidine-1-sulfonamido)benzoyl)-1H-pyrrolo[2,3-b]pyridin-5-yl)phenoxy)ethoxy)ethyl)piperazine-1-carboxylate

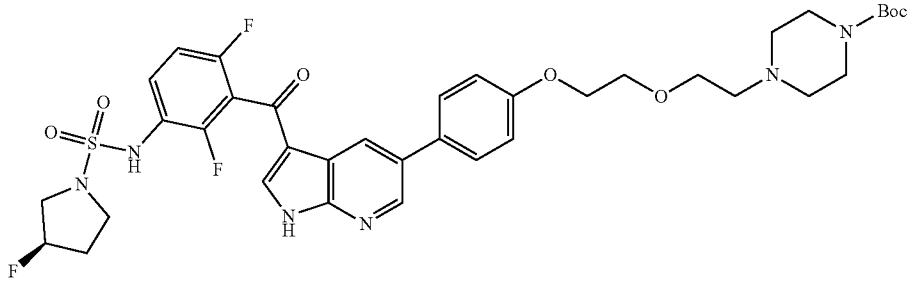 [SMILES: CC(C)(C)OC(=O)N1CCN(CCOCCOc2ccc(-c3cnc4[nH]cc(C(=O)c5c(F)ccc(NS(=O)(=O)N6CC[C@@H](F)C6)c5F)c4c3)cc2)CC1]

To a solution of tert-butyl 4-(2-(2-(4-(4,4,5,5-tetramethyl-1,3,2-dioxaborolan-2-yl)phenoxy)ethoxy)ethyl)piperazine-1-carboxylate (114 mg, 0.238 mmol) in 1, 4-dioxane/water (10 mL/1 mL) was added (R)—N-(3-(5-bromo-1H-pyrrolo[2,3-b]pyridine-3-carbonyl)-2,4-difluorophenyl)-3-fluoro-pyrrolidine-1-sulfonamide (120 mg, 0.238 mmol), cesium fluoride (72.4 mg, 0.476 mmol) and Pd(aMPhos)$Cl_2$ (16.9 mg, 0.0238 mmol). The resulting reaction mixture was stirred at 95° C. for 16 hours. After cooling, water (20 mL) was added and extracted with ethyl acetate (15 mL×3). The organic phase was dried and concentrated in vacuo. The residue was purified by preparative TLC (dichloromethane/methanol=20:1) to give (R)-tert-butyl 4-(2-(2-(4-(3-(2,6-difluoro-3-(3-fluoropyrrolidine-1-sulfonamido)benzoyl)-1H-pyrrolo[2,3-b]pyridin-5-yl)phenoxy)ethoxy)ethyl) piperazine-1-carboxylate (60 mg, 33%) as a pale yellow solid. LCMS: m/z 773.3 $[M+H]^+$.

Step E: (R)—N-(2,4-difluoro-3-(5-(4-(2-(2-(piperazin-1-yl)ethoxy)ethoxy)phenyl)-1H-pyrrolo[2,3-b]pyridine-3-carbonyl)phenyl)-3-fluoropyrrolidine-1-sulfonamide hydrochloride

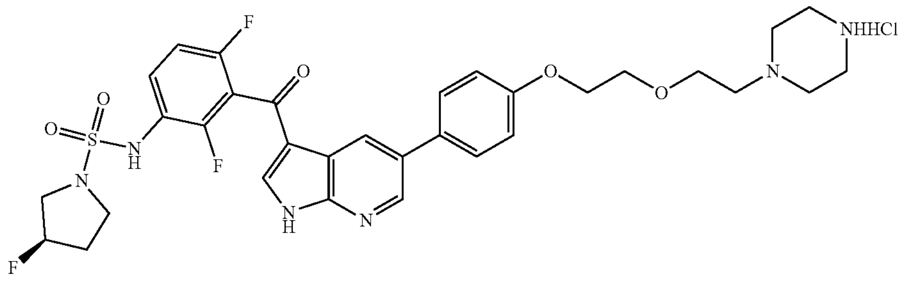

A solution of (R)-tert-butyl 4-(2-(2-(4-(3-(2,6-difluoro-3-(3-fluoropyrrolidine-1-sulfonamido)benzoyl)-1H-pyrrolo[2,3-b]pyridin-5-yl)phenoxy)ethoxy)ethyl)piperazine-1-carboxylate (60 mg, 0.0517 mmol) in hydrochloric acid/1,4-dioxane (5 mL, 4 M) was stirred at room temperature for 1 hour. The solvent was concentrated in vacuo to give compound (R)—N-(2,4-difluoro-3-(5-(4-(2-(2-(piperazin-1-yl)ethoxy)ethoxy)phenyl)-1H-pyrrolo[2,3-b]pyridine-3-carbonyl)phenyl)-3-fluoropyrrolidine-1-sulfonamide hydrochloride as a pale yellow solid, which was used to next step without further purification. LCMS: m/z 673.2 $[M+H]^+$.

Step F: (3R)—N-(3-(5-(4-(2-(2-(4-(2-(2,6-dioxopiperidin-3-yl)-1,3-dioxoisoindolin-5-yl)piperazin-1-yl)ethoxy)ethoxy)phenyl)-1H-pyrrolo[2,3-b]pyridine-3-carbonyl)-2,4-difluorophenyl)-3-fluoropyrrolidine-1-sulfonamide

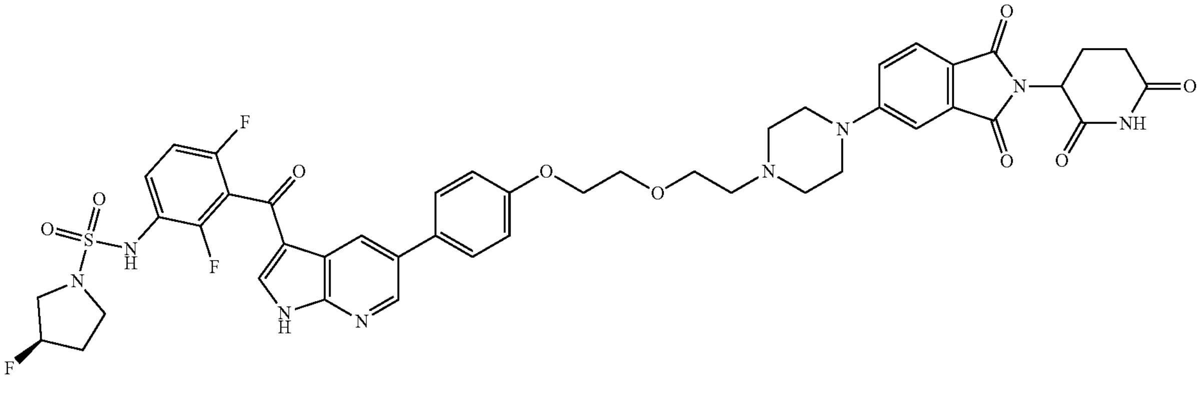 [SMILES: O=C1CCC(N2C(=O)c3ccc(N4CCN(CCOCCOc5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

To a solution of (R)—N-(2,4-difluoro-3-(5-(4-(2-(2-(piperazin-1-yl)ethoxy)ethoxy)phenyl)-1H-pyrrolo[2,3-b]pyridine-3-carbonyl)phenyl)-3-fluoropyrrolidine-1-sulfonamide hydrochloride (0.0517 mmol) in dimethyl sulfoxide (3 mL) was added 2-(2,6-dioxopiperidin-3-yl)-5-fluoroisoindoline-1,3-dione (14.3 mg, 0.0517 mmol) and triethylamine (10.5 mg, 0.104 mmol). The reaction mixture was stirred at 70° C. for 24 hours. After cooling to room temperature, water (10 mL) was added and extracted with ethyl acetate (10.0 mL×3). The combined organic phase was washed with brine (2.0 mL×4), dried over anhydrous sodium sulfate, filtered, and concentrated in vacuo. The residue was purified by preparative TLC (dichloromethane/methanol=20:1) twice to give (3R)—N-(3-(5-(4-(2-(2-(4-(2-(2,6-dioxopiperidin-3-yl)-1,3-dioxoisoindolin-5-yl)piperazin-1-yl)ethoxy)ethoxy)phenyl)-1H-pyrrolo[2,3-b]pyridine-3-carbonyl)-2,4-difluorophenyl)-3-fluoropyrrolidine-1-sulfonamide (6.7 mg, 14%) as a yellow solid. LCMS: m/z 929.3 $[M+H]^+$. NMR (400 MHz, DMSO-$d_6$) δ 1.96-2.13 (3H, m), 2.58 (7H, s), 2.83-2.92 (1H, m), 3.26-3.30 (2H, m), 3.40-3.43 (6H, m), 3.48 (1H, s), 3.63-3.67 (2H, m), 3.76-3.80 (2H, m), 4.17-4.19 (2H, m), 5.05-5.09 (1H, m), 5.23-5.36 (1H, m), 7.11 (2H, d, J=8.4 Hz), 7.24-7.29 (2H, m), 7.34 (1H, s), 7.60-7.69 (4H, m), 8.10 (1H, s), 8.57 (1H, brs), 8.66 (1H, d, J=2.4 Hz), 9.88 (1H, s), 11.09 (1H, s), 12.95 (1H, s).

Compounds 92-97 may be prepared in an analogous manner.

Example Synthesis of Compound 99

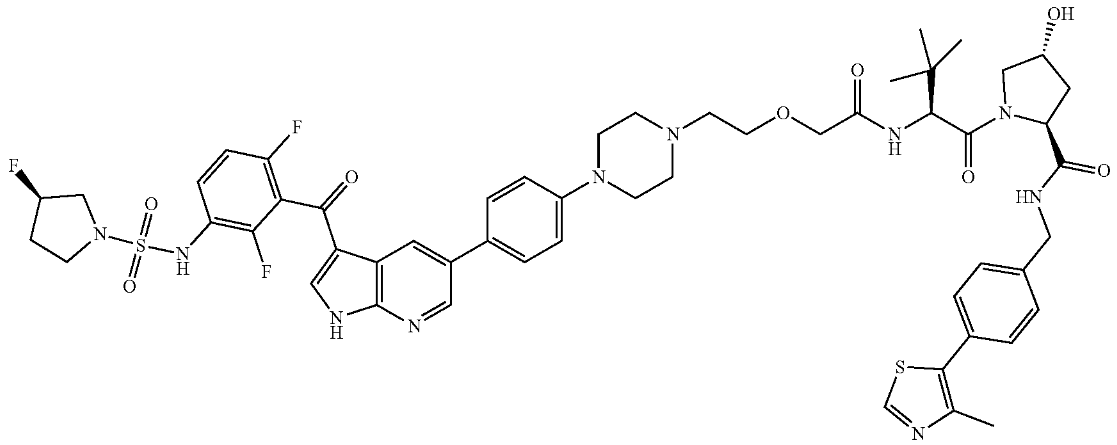 [SMILES: Cc1ncsc1-c1ccc(CNC(=O)[C@@H]2C[C@@H](O)CN2C(=O)[C@@H](NC(=O)COCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

Step A: tert-butyl 4-(4-bromophenyl)piperazine-1-carboxylate

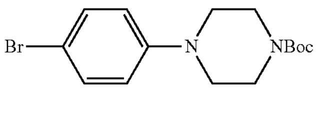 [SMILES: CC(C)(C)OC(=O)N1CCN(c2ccc(Br)cc2)CC1]

To a solution of 1,4-dibromobenzene (5.0 g, 21.2 mmol) in toluene (100 mL) were added tert-butyl piperazine-1-carboxylate (3.04 g, 16.3 mmol), $Pd_2(dba)_3$ (485 mg, 0.53 mmol), t-BuOK (5.95 g, 53 mmol) and BINAP (485 mg, 0.53 mmol). The resulting solution was stirred at 90° C. for 3 hours under $N_2$ atmosphere. After cooling to room temperature, the reaction was quenched with $H_2O$ (50 mL), and the mixture was extracted with EA. The combined organic layer was dried over anhydrous sodium sulfate, and concentrated in vacuo. The residue was purified by silica gel to afford the desired product (1.2 g, 17% yield) as a white solid. $^1H$ NMR (400 MHz, $CDCl_3$): δ 7.35 (d, J=8.8 Hz, 2H), 6.78 (d, J=9.2 Hz, 2H), 3.57 (t, J=4.8 Hz, 4H), 3.09 (t, J=4.8 Hz, 4H), 1.48 (s, 9H).

Step B: tert-butyl 4-(4-(4,4,5,5-tetramethyl-1,3,2-dioxaborolan-2-yl)phenyl)piperazine-1-carboxylate

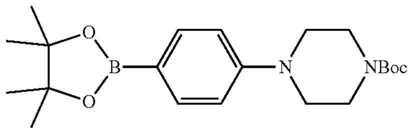 [SMILES: CC(C)(C)OC(=O)N1CCN(c2ccc(B3OC(C)(C)C(C)(C)O3)cc2)CC1]

To a solution of tert-butyl 4-(4-bromophenyl)piperazine-1-carboxylate (1.2 g, 3.53 mmol) in 1,4-dioxane (24 mL) were added 4,4,4',4',5,5,5',5'-octamethyl-2,2'-bi(1,3,2-dioxaborolane) (1.8 g, 7.06 mmol), Pd(dppf)$Cl_2$ (258 mg, 0.35 mmol) and KOAc (1.04 g, 10.59 mmol). The resulting solution was stirred at 90° C. overnight under $N_2$ atmosphere. TLC showed the reaction was completed. After cooled to room temperature, the reaction was diluted with 50 mL of EA, and the mixture was washed with water and brine. The organic phase was dried over anhydrous sodium sulfate. The residue was purified by chromatography column to afford the desired product (1.0 g, 73% yield). LCMS ($ES^+$): m/z 482.0.

Step C: tert-butyl 2-(2-(4-(4-(4,4,5,5-tetramethyl-1,3,2-dioxaborolan-2-yl)phenyl)piperazin-1-yl)ethoxy)acetate

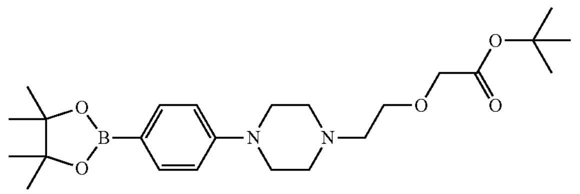 [SMILES: CC(C)(C)OC(=O)COCCN1CCN(c2ccc(B3OC(C)(C)C(C)(C)O3)cc2)CC1]

To a solution of tert-butyl 4-(4-(4,4,5,5-tetramethyl-1,3,2-dioxaborolan-2-yl)phenyl)piperazine-1-carboxylate (550 mg, 1.42 mmol) in DCM (5 mL) was added TFA (1.5 mL, 20.2 mmol). The resulting solution was stirred at 5° C. for 2 hours. The solvent was removed under vacuum to afford a residue (547 mg, calculated), which was used directly in next step. To a solution of the residue (547 mg, 1.42 mmol) in dry DMF (5 mL) were added $K_2CO_3$ (977 mg, 7.08 mmol), KI (470 mg, 2.83 mmol) and tert-butyl 2-(2-chloroethoxy)acetate (550 mg, 2.83 mmol). The resulting solution was stirred at 90° C. for 3 hours. After cooling to room temperature, the reaction was quenched with 20 mL of saturated NaCl solution, and the mixture was extracted with EA twice. The combined organic layer was concentration in vacuo, and the residue was purified by silica gel to afford the desired product (300 mg, 47% yield in two steps) as oil. NMR (400 MHz, $CDCl_3$): δ 7.70 (d, J=8.4 Hz, 2H), 6.88 (d, J=8.8 Hz, 2H), 4.01 (m, 3H), 3.69 (m, 4H), 3.30 (m, 4H), 2.68 (m, 6H), 1.48 (s, 9H), 1.32 (s, 12H).

Step D: (R)-tert-butyl 2-(2-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)ethoxy)acetate

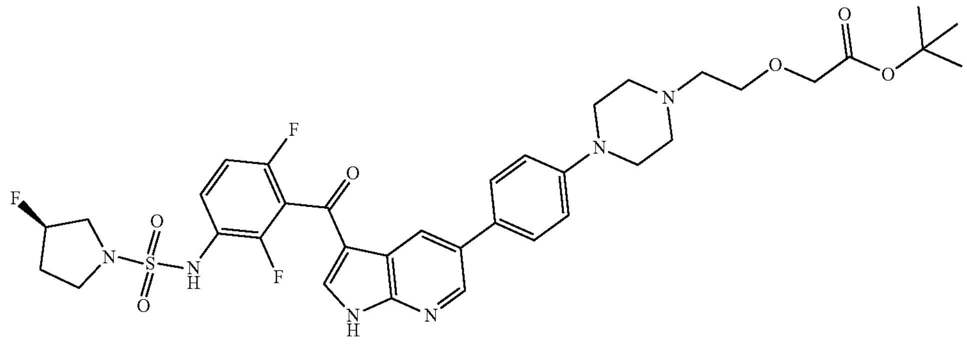 [SMILES: CC(C)(C)OC(=O)COCCN1CCN(c2ccc(-c3cnc4[nH]cc(C(=O)c5c(F)ccc(NS(=O)(=O)N6CC[C@@H](F)C6)c5F)c4c3)cc2)CC1]

To a solution of tert-butyl 2-(2-(4-(4-(4,4,5,5-tetramethyl-1,3,2-dioxaborolan-2-yl)phenyl)piperazin-1-yl)ethoxy)acetate (100 mg, 0.20 mmol) in 1,4-dioxane/$H_2O$ (10 ml/1 mL) were added (3R)—N-[3-([5-bromo-1H-pyrrolo[2,3-b]pyridin-3-yl]carbonyl)-2,4-difluorophenyl]-3-fluoropyrrolidine-1-sulfonamide (134 mg, 0.36 mmol), Pd(aMphos)$Cl_2$ (15 mg, 0.02 mmol) and CsF (121 mg, 0.80 mmol). The resulting solution was stirred at 95° C. for 3 hours under $N_2$ atmosphere. TLC showed the reaction was completed. After cooling to room temperature, the reaction was diluted with 50 mL of EA, and the mixture was washed with water and brine. The organic phase was dried over anhydrous sodium sulfate and concentrated in vacuo. The residue was purified by chromatography column to afford the desired product (100 mg, 66% yield). LCMS ($ES^+$): m/z 743.2 $[M+H-16]^+$.

Step E: (2S,4R)-1-((S)-2-(2-(2-(4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-(4-(4-methylthiazol-5-yl)benzyl)pyrrolidine-2-carboxamide

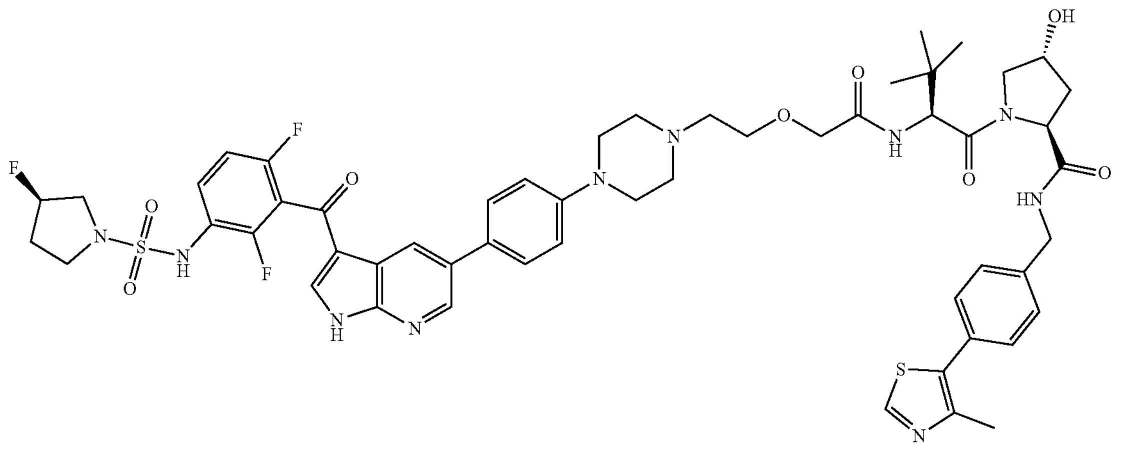 [SMILES: Cc1ncsc1-c1ccc(CNC(=O)[C@@H]2C[C@@H](O)CN2C(=O)[C@@H](NC(=O)COCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

To a solution of (R)-tert-butyl 2-(2-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)ethoxy)acetate compound with methanol (100 mg, 0.13 mmol) in 1,4-dioxane (2 mL) was added HCl (g), 1,4-dioxane (1 mL, 8 M). The resulting solution was stirred at 50° C. for 3 hours. TLC showed the reaction was completed. After cooled to room temperature, the reaction mixture was concentrated to afford a crude product (93 mg, 100% yield, calculated), which was used into next reaction. To a solution of crude product (93 mg, 0.13 mmol) in dry NMP (5 mL) were added (2S,4R)—N-(4-(4-methylthiazol-5-yl)benzyl)-1-((S)-2-amino-3,3-dimethylbutanoyl)-4-hydroxypyrrolidine-2-carboxamide hydrochloride (91 mg, 0.19 mmol), DIEA (167 mg, 1.30 mmol) and PyBOP (203 mg, 0.39 mmol) subsequently. The resulting solution was stirred at 10° C. for 1 hour. After the reaction was quenched with brine (20 mL), the mixture was extracted with EA twice. The organic layers was concentrated, and the residue was purified by silica gel and preparative HPLC to afford the desired product (39 mg, 27% yield in two steps) as a yellow solid. NMR (400 MHz, $CD_3OD$): δ 8.80 (s, 1H), 8.65 (s, 1H), 8.56 (s, 1H), 7.89 (s, 1H), 7.73 (m, 1H), 7.54 (d, J=8.8 Hz, 2H), 7.44 (d, J=7.6 Hz, 2H), 7.36 (d, J=8.0 Hz, 2H), 7.07-7.14 (m, 3H), 5.13-5.30 (m, 1H), 4.71 (s, 1H), 4.50-4.65 (m, 4H), 4.34 (d, J=15.6 Hz, 1H), 4.12 (m, 2H), 3.78-3.95 (m, 4H), 3.40-3.65 (m, 9H), 3.10 (m, 6H), 2.42 (s, 3H), 2.00-2.30 (m, 4H), 1.04 (s, 9H); LCMS ($ES^+$): m/z 550.3 $[M/2+H]^+$.

Compounds 98, 100-101, 102, 103-106, and 223-252 may be prepared in an analogous manner.

Example Synthesis of Compound 114

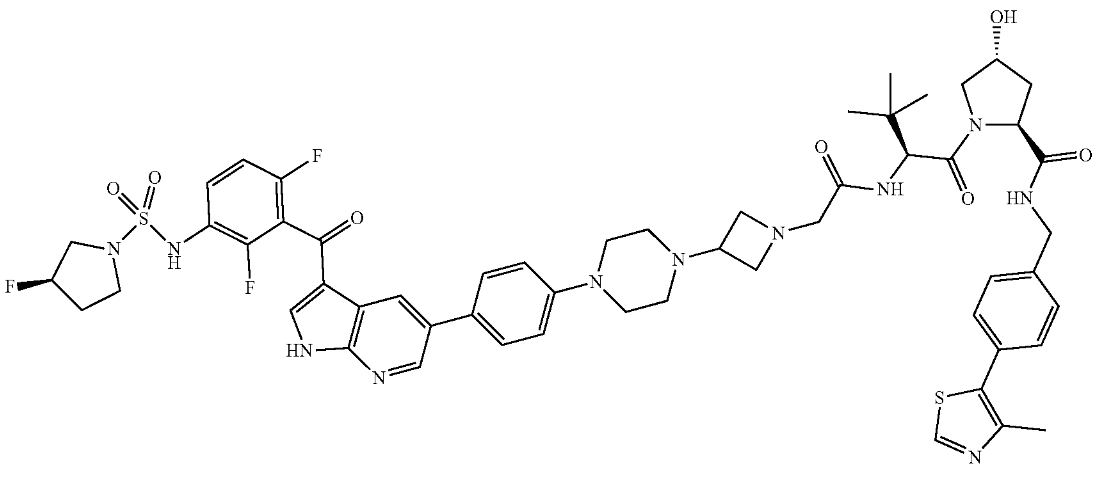 [SMILES: Cc1ncsc1-c1ccc(CNC(=O)[C@@H]2C[C@@H](O)CN2C(=O)[C@@H](NC(=O)CN2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)C(C)(C)C)cc1]

Step A: 1-(azetidin-3-yl)-4-(4-bromophenyl)piperazine hydrochloride

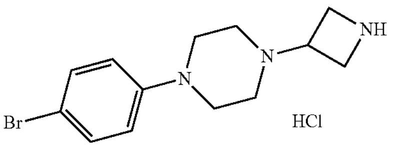 [SMILES: Brc1ccc(N2CCN(C3CNC3)CC2)cc1 ; Cl]

To a solution of 1-(4-bromophenyl)piperazine hydrochloride (2.0 g, 7.21 mmol) in $CH_3OH$/DCM (v/v=1/1, 30 mL) was added KOAc (1.4 g, 14.4 mmol) and cat. AcOH (0.1 mL) at room temperature. After stirring for 30 minutes, $NaBH(OAc)_3$ (7.6 g, 36.1 mmol). The mixture was stirred at 30° C. overnight. After the reaction was quenched with aqu.$NaHCO_3$ (50 mL), the mixture was extracted with DCM (100 mL×2). The combined organic layer was washed with brine (50 mL), dried over anhydrous sodium sulfate and concentrated under vacuum to afford crude the desired product (2.5 g) as a light brown solid, which was used to next step without further purification. To a solution of the above intermediates in methanol (20 mL) was added HCl (g)/$CH_3OH$ (10 mL). The resulting solution was stirred for 2 hours at room temperature. The solvent was removed under vacuum. The residue was triturated with DCM and filtered to afford the desired product 1-(azetidin-3-yl)-4-(4-bromophenyl)piperazine hydrochloride (2.0 g) as a brown solid.

Step B: ethyl 2-(3-(4-(4-bromophenyl)piperazin-1-yl)azetidin-1-yl)acetate

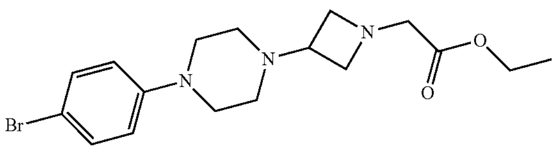 [SMILES: CCOC(=O)CN1CC(N2CCN(c3ccc(Br)cc3)CC2)C1]

To a solution of 1-(azetidin-3-yl)-4-(4-bromophenyl)piperazine hydrochloride (2.0 g, 6.01 mmol) in $CH_3OH$/DCM (v/v=1/1, 10 mL) was added KOAc (1.2 g, 12.1 mmol) and cat. AcOH (0.1 mL) at room temperature. After stirring for 30 minutes, $NaBH(OAc)_3$ (6.3 g, 30.1 mmol). The mixture was stirred at 30° C. overnight. After the reaction was quenched with aq. $NaHCO_3$ (30 mL), the mixture was extracted with DCM (50 mL×3). The combined organic layer was washed with brine (50 mL), dried over anhydrous sodium sulfate and concentrated under vacuum to afford the desired product ethyl 2-(3-(4-(4-bromophenyl)piperazin-1-yl)azetidin-1-yl)acetate (1.0 g, crude) as a light brown solid, which was used to next step without further purification. LCMS ($ES^+$): m/z 384.1; 382.1 $[M+H]^+$.

Step C: methyl 2-(3-(4-(4-(4,4,5,5-tetramethyl-1,3,2-dioxaborolan-2-yl)phenyl)piperazin-1-yl)azetidin-1-yl)acetate

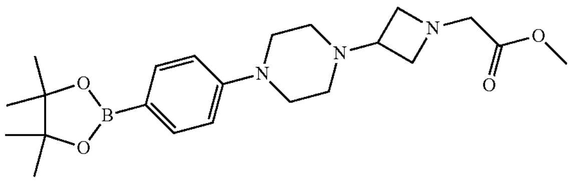

To a solution of ethyl 2-(3-(4-(4-bromophenyl)piperazin-1-yl)azetidin-1-yl) acetate (1.0 g, crude) in methanol (20 mL) was added HCl (g)/$CH_3OH$ (10 mL). The resulting solution was stirred at 60° C. for 2 hours. The solvent was removed under vacuum. The residue was taken up with DCM (100 mL), and the mixture was washed with $NaHCO_3$ (30 mL×3). The organic phase was concentrated under vacuum. The residue (500 mg) was used into next reaction without further purification. To a solution of the above intermediates (500 mg, 1.4 mmol) in 1,4-dioxane (20 mL) was added KOAc (267 mg, 2.8 mmol), $Pd(dppf)Cl_2$ (190 mg, 0.14 mmol), 4,4,5,5-tetramethyl-2-(4,4,5,5-tetramethyl-1,3,2-dioxaborolan-2-yl)-1, 3,2-dioxaborolane (700 mg, 2.8 mmol). The resulting solution was purged with $N_2$ at room temperature for 10 minutes to remove the excess $O_2$. The mixture was stirred at 100° C. overnight. After cooling to room temperature, the reaction was taken up with EtOAc. The organic phase was concentrated under vacuum. The residue was purified by silica gel with PE/EA (10-1/1) to afford the desired product methyl 2-(3-(4-(4-(4,4,5,5-tetramethyl-1,3,2-dioxaborolan-2-yl)phenyl)piperazin-1-yl)azetidin-1-yl)acetate (300 mg) as a brown solid. LCMS ($ES^+$): m/z 416.3 $[M+H]^+$.

Step D: (2S,4R)—N-(4-(4-methylthiazol-5-yl)benzyl)-1-((S)-3,3-dimethyl-2-(2-(3-(4-(4-(4,4,5,5-tetramethyl-1,3,2-dioxaborolan-2-yl)phenyl)piperazin-1-yl)azetidin-1-yl)acetamido)butanoyl)-4-hydroxypyrrolidine-2-carboxamide

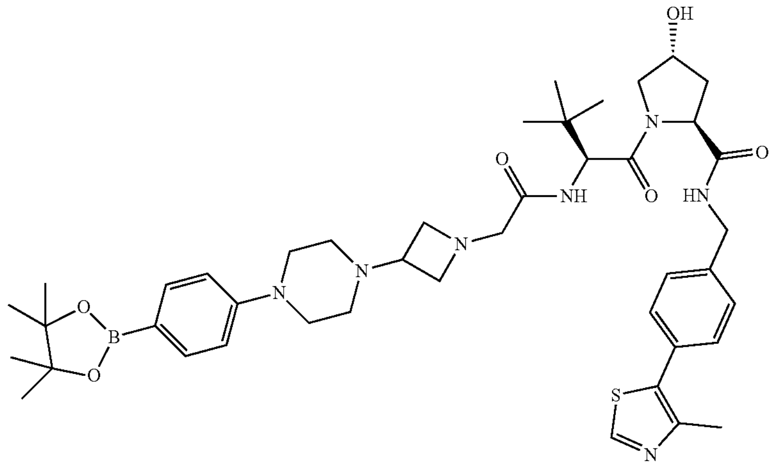 [SMILES: Cc1ncsc1-c1ccc(CNC(=O)[C@@H]2C[C@@H](O)CN2C(=O)[C@@H](NC(=O)CN2CC(N3CCN(c4ccc(B5OC(C)(C)C(C)(C)O5)cc4)CC3)C2)C(C)(C)C)cc1]

To a solution of methyl 2-(3-(4-(4-(4,4,5,5-tetramethyl-1,3,2-dioxaborolan-2-yl)phenyl)piperazin-1-yl)azetidin-1-yl) acetate (300 mg, 0.72 mmol) in $H_2O$/THF (v/v=1/5, 5 mL) was added LiOH (34 mg, 1.5 mmol). The resulting solution was stirred at room temperature for 1 hour. Then the solvent was removed under vacuum. The residue was used into next reaction without further purification. To a solution of the above intermediates in DMF (5.0 mL) were added DIEA (300 mg, 2.2 mmol), (2S,4R)—N-(4-(4-methylthiazol-5-yl) benzyl)-1-((S)-2-amino-3,3-dimethylbutanoyl)-4-hydroxy-pyrrolidine-2-carboxamide hydrochloride (338 mg, 0.72 mmol) and PyBOP (564 mg, 1.1 mmol) at room temperature. The resulting solution was stirred at 20° C. for 2 hours. The reaction was quenched with $H_2O$ (10 mL), and the mixture was extracted with EtOAc (20 mL×3). The combined organic layer was concentrated under vacuum. The residue was purified by preparative TEC with DCM/$CH_3OH$ (20/1) to afford the desired product (2S,4R)-1-((S)-3,3-dimethyl-2-(2-(3-(4-(4-(4,4,5,5-tetramethyl-1,3,2-dioxaborolan-2-yl)phenyl)piperazin-1-yl)azetidin-1-yl)acetamido) butanoyl)-4-hydroxy-N-(4-(4-methylthiazol-5-yl) benzyl)pyrrolidine-2-carboxamide (80 mg) as a light brown solid. LCMS ($ES^+$): m/z 814.4 $[M+H]^+$.

Step E: (2S,4R)—N-(4-(4-methylthiazol-5-yl)benzyl)-1-((S)-2-(2-(3-(4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl) azetidin-1-yl)acetamido)-3,3-dimethylbutanoyl)-4-hydroxypyrrolidine-2-carboxamide

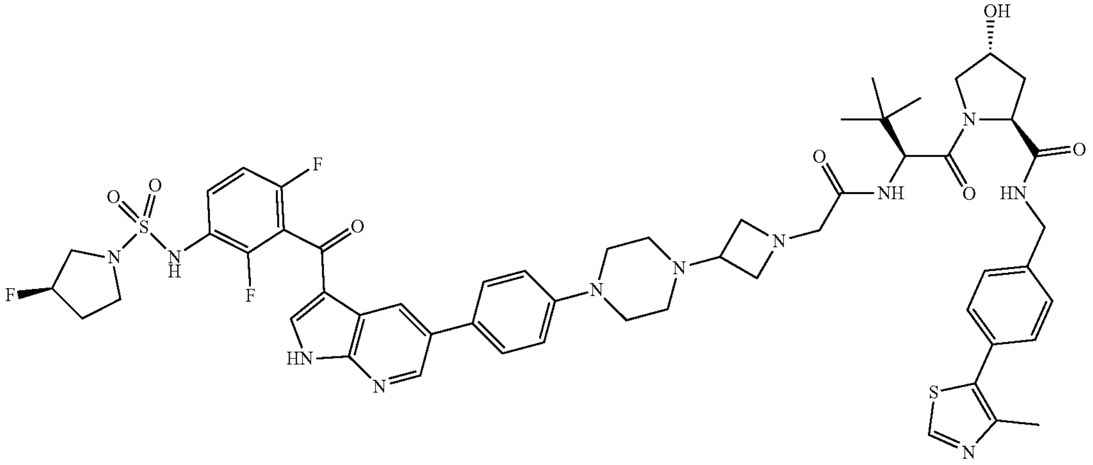 [SMILES: Cc1ncsc1-c1ccc(CNC(=O)[C@@H]2C[C@@H](O)CN2C(=O)[C@@H](NC(=O)CN2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)C(C)(C)C)cc1]

To a solution of (2S,4R)-1-((S)-3,3-dimethyl-2-(2-(3-(4-(4-(4,4,5,5-tetramethyl-1,3,2-dioxaborolan-2-yl)phenyl)piperazin-1-yl)azetidin-1-yl)acetamido)butanoyl)-4-hydroxy-N-(4-(4-methylthiazol-5-yl)benzyl)pyrrolidine-2-carboxamide (80 mg, 0.098 mmol) in $H_2O$/1,4-dioxane (v/v=1/5, 5.0 mL) were added CsF (45 mg, 0.29 mmol), Pd(amphos)$Cl_2$ (8 mg, 0.01 mmol), (R)—N-(3-(5-bromo-1H-pyrrolo[2,3-b]pyridine-3-carbonyl)-2,4-difluorophenyl)-3-fluoropyrrolidine-1-sulfonamide (70 mg, 0.14 mmol) at room temperature. The solution was purged with $N_2$ at room temperature for 10 minutes to remove the excess $O_2$. The resulting solution was stirred at 80° C. overnight. After cooling to room temperature, the reaction was taken up with EtOAc. The combined organic layer was concentrated under vacuum. The residue was purified by preparative TLC with DCM/$CH_3OH$ (20/1) to afford the desired product (2S,4R)-1-((S)-2-(2-(3-(4-(4-(3-(2,6-difluoro-3-(((R)-3-fluoro-pyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide (35 mg) as a light yellow solid. $^1$H NMR (400 MHz, DMSO-$d_6$): δ 9.02 (s, 1H), 8.71-8.75 (m, 2H), 8.68 (br, 1H), 8.12 (s, 1H), 7.61-7.66 (m, 4H), 7.42-7.46 (m, 5H), 7.19-7.21 (m, 2H), 7.06 (d, J=8.0 Hz, 2H), 5.33-5.35 (m, 0.5H), 5.22-5.23 (m, 0.5H), 5.16 (d, J=7.2 Hz, 1H), 4.53 (d, J=9.6 Hz, 1H), 4.34-4.47 (m, 5H), 4.24-4.29 (m, 1H), 4.04 (s, 1H), 3.65-3.66 (m, 3H), 3.51-3.61 (m, 5H), 3.22-3.34 (m, 6H), 3.08 (br, 3H), 2.41-2.47 (m, 3H), 1.93-2.07 (m, 5H), 0.94 (s, 9H); LCMS ($ES^+$): m/z 1111.3 $[M+H]^+$, 1108.3 $[M-H]^+$.

Compounds 107-113, 115, 116, and 253-269 may be prepared in an analogous manner.

Example Synthesis of Compound 117

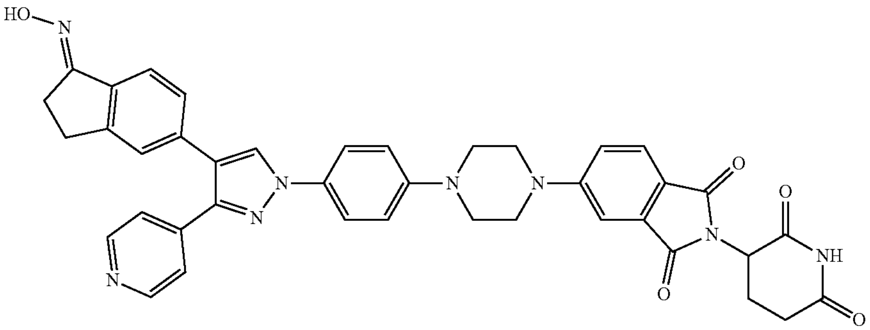 [SMILES: O=C1CCC(N2C(=O)c3ccc(N4CCN(c5ccc(-n6cc(-c7ccc8c(c7)CC/C8=N\O)c(-c7ccncc7)n6)cc5)CC4)cc3C2=O)C(=O)N1]

Step A: tert-butyl 4-(4-(4-bromo-3-(pyridin-4-yl)-1H-pyrazol-1-yl)phenyl)piperazine-1-carboxylate

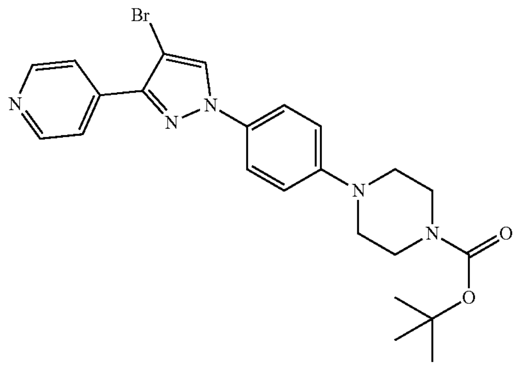 [SMILES: CC(C)(C)OC(=O)N1CCN(c2ccc(-n3cc(Br)c(-c4ccncc4)n3)cc2)CC1]

The mixture of 4-(4-bromo-1H-pyrazol-3-yl)pyridine (5.0 g, 22.3 mmol) (previously described in *Bioorg. Med. Chem. Lett.* 2008, 18, 4692-4695), tert-butyl 4-(4-(4,4,5,5-tetramethyl-1,3,2-dioxaborolan-2-yl)phenyl)piperazine-1-carboxylate (8.7 g, 22.3 mmol) and cupric acetate (4.0 g, 22.3 mmol) in pyridine (30 mL) was stirred at 100° C. overnight. The mixture was concentrated in vacuo and the residue was purified by column chromatography on silica gel (petroleum ether/ethyl acetate=5/1) to give tert-butyl 4-(4-(4-bromo-3-(pyridin-4-yl)-1H-pyrazol-1-yl)phenyl)piperazine-1-carboxylate (10.8 g, 70% yield) as a brown solid.

Step B: tert-butyl 4-(4-(4-(1-oxo-2,3-dihydro-1H-inden-5-yl)-3-(pyridin-4-yl)-1H-pyrazol-1-yl)phenyl)piperazine-1-carboxylate

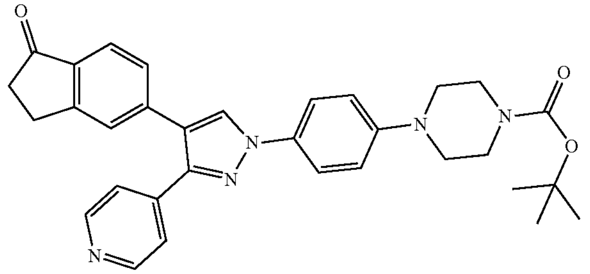 [SMILES: CC(C)(C)OC(=O)N1CCN(c2ccc(-n3cc(-c4ccc5c(c4)CCC5=O)c(-c4ccncc4)n3)cc2)CC1]

The mixture of tert-butyl 4-(4-(4-bromo-3-(pyridin-4-yl)-1H-pyrazol-1-yl)phenyl)piperazine-1-carboxylate (2.4 g, 5.0 mmol), 5-(4,4,5,5-tetramethyl-1,3,2-dioxaborolan-2-yl)-2,3-dihydro-1H-inden-1-one (1.3 g, 5.0 mmol), [1,1'-bis(diphenylphosphino)ferrocene]dichloropalladium (366 mg, 0.5 mmol), tri-tert-butylphosphine tetrafluoroborate (145 mg, 0.5 mmol) and cesium fluoride (2.3 g, 15.0 mmol) in 1,4-dioxane/water (20 mL, 10/1) was stirred at 90° C. overnight. The mixture was poured into water (30 mL) and extracted with dichloromethane (30 mL×3). The combined organic phase was concentrated in vacuo and the residue was purified by column chromatography on silica gel (dichloromethane/methanol=20/1) to give tert-butyl 4-(4-(4-(1-oxo-2,3-dihydro-1H-inden-5-yl)-3-(pyridin-4-yl)-1H-pyrazol-1-yl)phenyl)piperazine-1-carboxylate (1.6 g, 60% yield) as a yellow solid. LCMS: m/z 536.3 $[M+H]^+$.

Step C: 5-(1-(4-(piperazin-1-yl)phenyl)-3-(pyridin-4-yl)-1H-pyrazol-4-yl)-2,3-dihydro-1H-inden-1-one hydrochloride

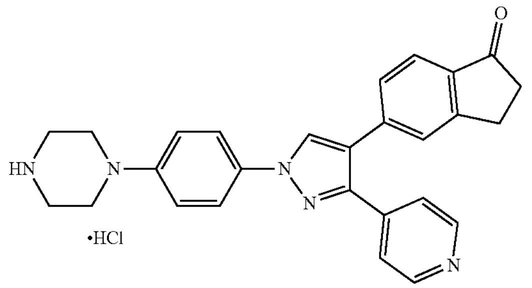 [SMILES: O=C1CCc2cc(-c3cn(-c4ccc(N5CCNCC5)cc4)nc3-c3ccncc3)ccc21 ; Cl]

The solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (1.6 g, 3.0 mmol) in dry hydrochloride acid/methanol (30 mL, 1.0 M.) was stirred at room temperature overnight. The reaction mixture was concentrated in vacuo to give 5-(1-(4-(piperazin-1-yl)phenyl)-3-(pyridin-4-yl)-1H-pyrazol-4-yl)-2,3-dihydro-1H-inden-1-one hydrochloride (1.0 g, 80% yield) as a white solid, which was directly used to the next step without further purification.

Step D: 2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione

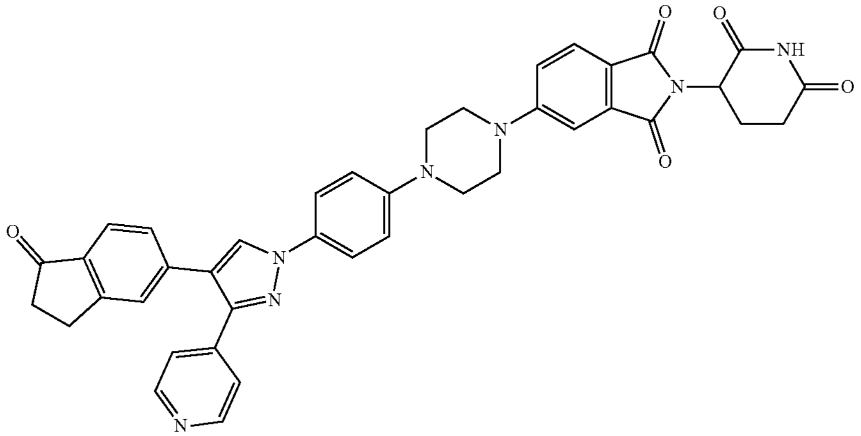 [SMILES: O=C1CCC(N2C(=O)c3ccc(N4CCN(c5ccc(-n6cc(-c7ccc8c(c7)CCC8=O)c(-c7ccncc7)n6)cc5)CC4)cc3C2=O)C(=O)N1]

The mixture of 5-(1-(4-(piperazin-1-yl)phenyl)-3-(pyridin-4-yl)-1H-pyrazol-4-yl)-2,3-dihydro-1H-inden-1-one hydrochloride (1.0 g, 2.3 mmol), 2-(2,6-dioxopiperidin-3-yl)-5-fluoroisoindoline-1,3-dione (635 mg, 2.3 mmol) and triethylamine (697 mg, 6.9 mmol) in dimethyl sulfoxide (10 mL) was stirred at 80° C. overnight. The mixture was poured into water (20 mL) and extracted with ethyl acetate (20 mL×3). The combined organic phase was concentrated in vacuo and the residue was purified by column chromatography on silica gel (dichloromethane/methanol=20/1) to give 2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (1.1 g, 70% yield) as a yellow solid. LCMS: m/z 692.3 $[M+H]^+$.

Step E: (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione

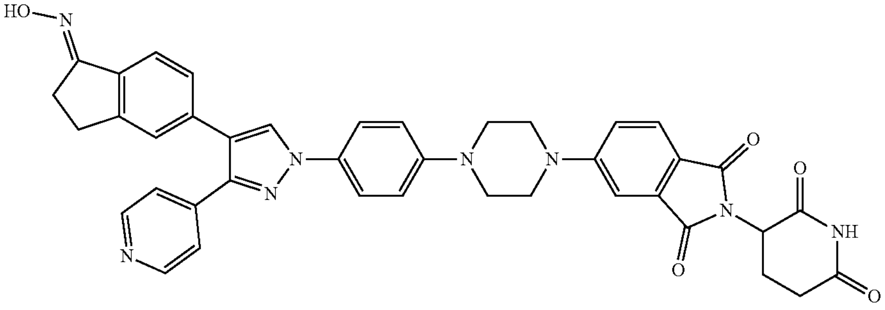 [SMILES: O=C1CCC(N2C(=O)c3ccc(N4CCN(c5ccc(-n6cc(-c7ccc8c(c7)CC/C8=N\O)c(-c7ccncc7)n6)cc5)CC4)cc3C2=O)C(=O)N1]

The mixture of 2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (300 mg, 0.43 mmol) and hydroxylamine hydrochloride (300 mg, 4.3 mmol) in pyridine (10 mL) was stirred at room temperature overnight. The reaction mixture was concentrated in vacuo. The residue was purified by preparative HPLC to give (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione (182 mg, 60% yield) as a yellow solid. LCMS: m/z 707.3 $[M+H]^+$; $^1H$ NMR (400 MHz, DMSO-$d_6$) δ 2.01-2.07 (1H, m), 2.54-2.61 (2H, m), 2.80-2.89 (3H, m), 2.98-3.02 (2H, m), 3.39 (4H, brs), 3.66 (4H, brs), 5.06-5.11 (1H, m), 7.16 (2H, d, J=8.8 Hz), 7.21 (1H, d, J=7.6 Hz), 7.33-7.35 (1H, m), 7.42 (2H, d, J=8.0 Hz), 7.47 (2H, dd, J=5.6, 1.6 Hz), 7.55 (1H, J=7.6 Hz), 7.72 (1H, d, J=8.4 Hz), 7.83 (2H, d, J=8.8 Hz), 8.57 (2H, dd, J=4.4, 1.2 Hz), 8.73 (1H, s), 10.9 (1H, s), 11.0-11.1 (1H. m).

Compounds 118-132 and 271 may be prepared in an analogous manner.

Example Synthesis of Compound 137

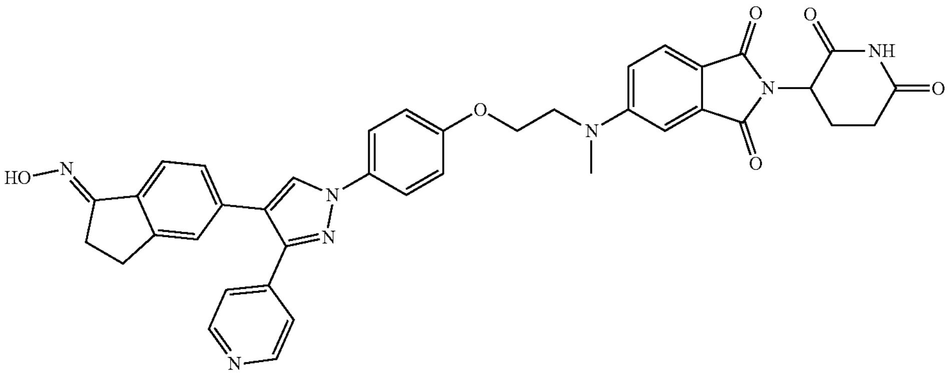 [SMILES: CN(CCOc1ccc(-n2cc(-c3ccc4c(c3)CC/C4=N\O)c(-c3ccncc3)n2)cc1)c1ccc2c(c1)C(=O)N(C1CCC(=O)NC1=O)C2=O]

Step A: tert-butyl (2-(4-(4-bromo-3-(pyridin-4-yl)-1H-pyrazol-1-yl)phenoxy)ethyl)(methyl)carbamate

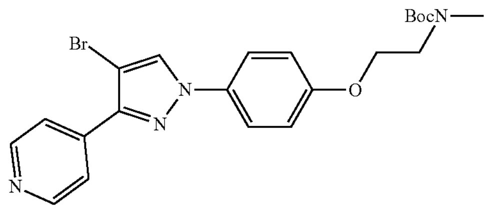 [SMILES: CN(CCOc1ccc(-n2cc(Br)c(-c3ccncc3)n2)cc1)C(=O)OC(C)(C)C]

To a solution of tert-butyl methyl(2-(4-(4,4,5,5-tetramethyl-1,3,2-dioxaborolan-2-yl)phenoxy)ethyl)carbamate (3.57 g, 9.47 mmol) and 4-(4-bromo-1H-pyrazol-3-yl)pyridine (2.12 g, 9.47 mmol) in DCM (20 mL) were added $Et_2NH$ (6.91 g, 94.72 mmol), $Cu(OAc)_2$ (1.72 g, 9.47 mmol). The resulting mixture was stirred at 30° C. for 16 hours under the atmosphere of $O_2$. The mixture was diluted with DCM (30 mL), and then the mixture was washed with $NH_3 \cdot H_2O$ thrice. The organic phase was evaporated under reduced pressure, The residue was purified by silica gel column chromatography on silica gel (DCM/MeOH=80/1) to afford tert-butyl (2-(4-(4-bromo-3-(pyridin-4-yl)-1H-pyrazol-1-yl) phenoxy)ethyl)(methyl)carbamate (3.0 g, 66.9% yield) as a brown oil.

Step B: 2-(4-(4-bromo-3-(pyridin-4-yl)-1H-pyrazol-1-yl)phenoxy)-N-methylethan-1-amine

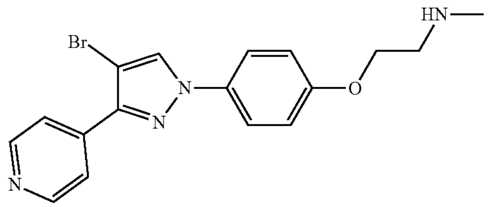 [SMILES: CNCCOc1ccc(-n2cc(Br)c(-c3ccncc3)n2)cc1]

To a solution of tert-butyl (2-(4-(4-bromo-3-(pyridin-4-yl)-1H-pyrazol-1-yl)phenoxy)ethyl)(methyl)carbamate (1.56 g, 3.31 mmol) in MeOH (6 mL) was added HCl/Dioxane (6 N, 10 mL) at room temperature slowly. The mixture was stirred at room temperature for 2 hours. The mixture was evaporated under reduced pressure to afford 2-(4-(4-bromo-3-(pyridin-4-yl)-1H-pyrazol-1-yl)phenoxy)-N-methylethan-1-amine as a colorless solid (1.23 g, 100% yield).

Step C: 5-((2-(4-(4-bromo-3-(pyridin-4-yl)-1H-pyrazol-1-yl)phenoxy)ethyl)(methyl)amino)-2-(2,6-dioxopiperidin-3-yl)isoindoline-1,3-dione

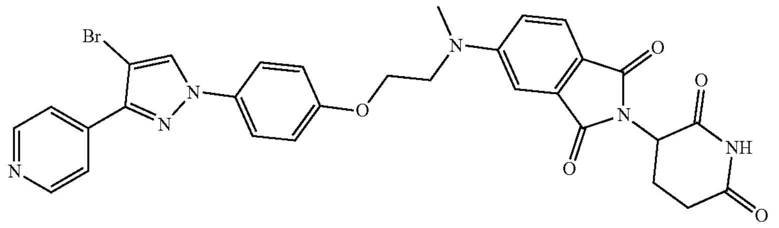 [SMILES: CN(CCOc1ccc(-n2cc(Br)c(-c3ccncc3)n2)cc1)c1ccc2c(c1)C(=O)N(C1CCC(=O)NC1=O)C2=O]

-

To a solution of 2-(4-(4-bromo-3-(pyridin-4-yl)-1H-pyrazol-1-yl)phenoxy)-N-methylethan-1-amine (400 mg, 1.07 mmol) and 2-(2,6-dioxopiperidin-3-yl)-5-fluoroisoindoline-1,3-dione (591.9 mg, 2.14 mmol) in NMP (2 mL) was added DIPEA (1.38 g, 10.7 mmol). The resulting mixture was stirred at 130° C. for 12 hours under the atmosphere of $N_2$. The mixture was diluted with EA (30 mL), and then the mixture was washed with brine twice. The organic phase was evaporated under reduced pressure, The residue was purified by column chromatography on silica gel (PE/EtOAc=1/3) to afford 5-((2-(4-(4-bromo-3-(pyridin-4-yl)-1H-pyrazol-1-yl)phenoxy)ethyl)(methyl)amino)-2-(2,6-dioxopiperidin-3-yl)isoindoline-1,3-dione (500 mg, 74.1% yield).

Step D: 2-(2,6-dioxopiperidin-3-yl)-5-(methyl(2-(4-(4-(1-oxo-2,3-dihydro-1H-inden-5-yl)-3-(pyridin-4-yl)-1H-pyrazol-1-yl)phenoxy)ethyl)amino)isoindoline-1,3-dione

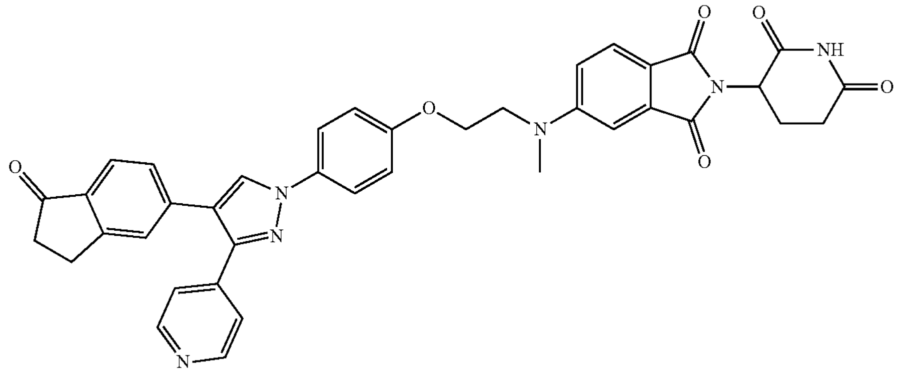 [SMILES: CN(CCOc1ccc(-n2cc(-c3ccc4c(c3)CCC4=O)c(-c3ccncc3)n2)cc1)c1ccc2c(c1)C(=O)N(C1CCC(=O)NC1=O)C2=O]

To a solution of 5-((2-(4-(4-bromo-3-(pyridin-4-yl)-1H-pyrazol-1-yl)phenoxy)ethyl)(methyl)amino)-2-(2,6-dioxopiperidin-3-yl)isoindoline-1,3-dione (500 mg, 0.79 mmol) and 5-(4,4,5,5-tetramethyl-1,3,2-dioxaborolan-2-yl)-2,3-dihydro-1H-inden-1-one (307.6 mg, 1.19 mmol) in 1,4-dioxane/$H_2O$ (9 mL, 8:1) were added t-$Bu_3PHBF_4$ (92.2 mg, 0.32 mmol), CsF (483.3 mg, 3.18 mmol), $Cy_2NMe$ (5 drop) and $Pd_2(dba)_3$ (145.6 mg, 0.16 mmol). The resulting mixture was stirred at 100° C. for 2 hour under the atmosphere of $N_2$. The solvent was evaporated under reduced pressure. The residue was diluted with EA (30 mL), and then the mixture was washed with brine twice. The organic phase was evaporated under reduced pressure, The residue was purified by column chromatography on silica gel (PE/DCM/MeOH=800/200/25) to afford 2-(2,6-dioxopiperidin-3-yl)-5-(methyl(2-(4-(4-(1-oxo-2,3-dihydro-1H-inden-5-yl)-3-(pyridin-4-yl)-1H-pyrazol-1-yl)phenoxy)ethyl)amino)isoindoline-1,3-dione (500 mg, 92.4% yield).

Step E: (E)-2-(2,6-dioxopiperidin-3-yl)-5-((2-(4-(4-(1-(hydroxyimino)-2,3-dihydro-1H-inden-5-yl)-3-(pyridin-4-yl)-1H-pyrazol-1-yl)phenoxy)ethyl)(methyl)amino)isoindoline-1,3-dione To a solution of 2-(2,6-dioxopiperidin-3-yl)-5-(methyl(2-(4-(4-(1-oxo-2,3-dihydro-1H-inden-5-yl)-3-(pyridin-4-yl)-1H-pyrazol-1-yl)phenoxy)ethyl)amino)isoindoline-1,3-dione (200 mg, 0.294 mmol) in $CH_3CN$/Py (3 mL/3 mL) was added $NH_2OH$— HCl (200 mg, 2.877 mmol), the mixture was stirred at 40° C. for 0.5 hour. The mixture was diluted with DCM (30 mL), washed with brine twice. The organic layer was evaporated under reduced pressure. The residue was purified by TLC (DCM/EA/MeOH=50/100/15) to afford (E)-2-(2,6-dioxopiperidin-3-yl)-5-((2-(4-(4-(1-(hydroxyimino)-2,3-dihydro-1H-inden-5-yl)-3-(pyridin-4-yl)-1H-pyrazol-1-yl)phenoxy)ethyl)(methyl)amino)isoindoline-1,3-dione as a yellow-green solid (103 mg, 49.9% yield). NMR (400 MHz, $CDCl_3$): δ 8.56 (d, J=4.0 Hz, 2H), 8.16 (s, 1H), 7.94 (s, 1H), 7.66-7.72 (m, 4H), 7.50 (d, J=4.8 Hz, 2H), 7.43 (s, 1H), 7.29 (s, 1H), 7.19-7.26 (m, 2H), 6.93-6.98 (m, 3H), 4.92-4.96 (m, 1H), 4.24 (t, J=4.8 Hz, 2H), 3.94 (t, J=10 Hz, 2H), 3.23 (s, 3H), 3.00-3.04 (m, 4H), 2.77-2.92 (m, 4H), 2.12-2.15 (d, J=8.4 Hz, 1H); LCMS ($ES^+$): m/z 696.2 $[M+H]^+$.

Compounds 133-136, 138-149, and 273-281 may be prepared in an analogous manner.

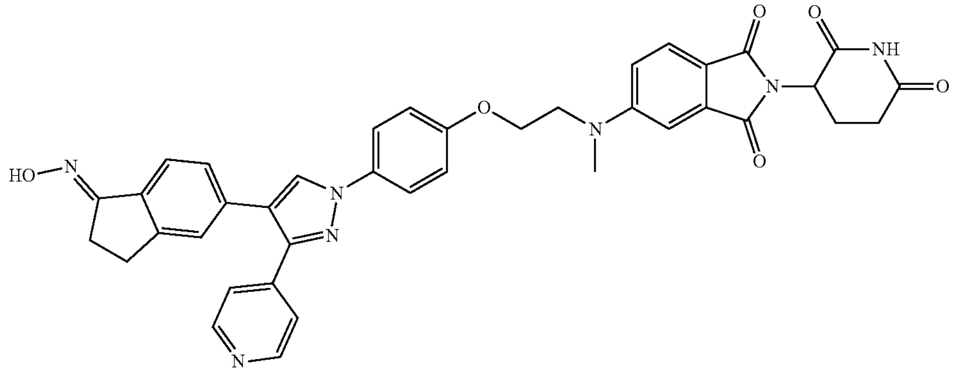 [SMILES: CN(CCOc1ccc(-n2cc(-c3ccc4c(c3)CC/C4=N\O)c(-c3ccncc3)n2)cc1)c1ccc2c(c1)C(=O)N(C1CCC(=O)NC1=O)C2=O]

Example Synthesis of Compound 150

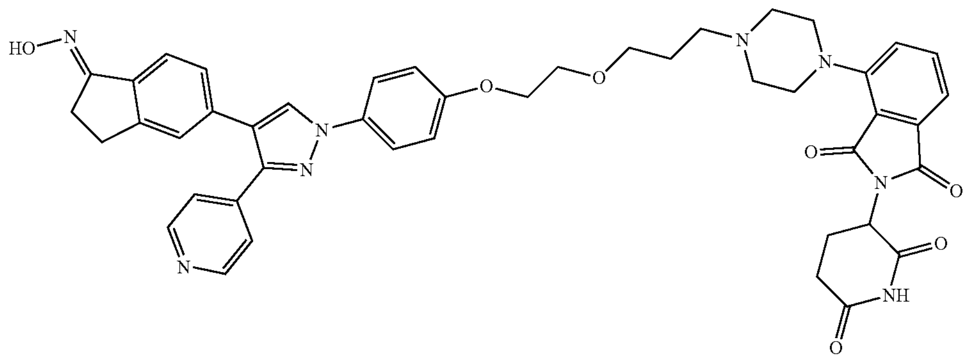 [SMILES: O=C1CCC(N2C(=O)c3cccc(N4CCN(CCCOCCOc5ccc(-n6cc(-c7ccc8c(c7)CC/C8=N\O)c(-c7ccncc7)n6)cc5)CC4)c3C2=O)C(=O)N1]

Step A: 4-(4-bromo-1-(4-(2-(3-((tert-butyldimethylsilyl)oxy)propoxy)ethoxy)phenyl)-1H-pyrazol-3-yl) pyridine

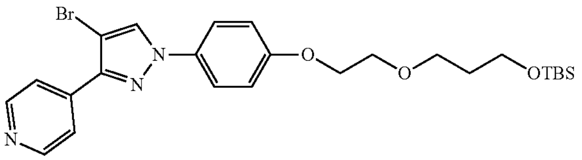 [SMILES: CC(C)(C)[Si](C)(C)OCCCOCCOc1ccc(-n2cc(Br)c(-c3ccncc3)n2)cc1]

To a solution of 2-(3-((tert-butyldimethylsilyl)oxy) propoxy)ethyl4-methylbenzene-esulfonate (420 mg, 1.08 mmol) in dry DMF (10 mL) were added $K_2CO_3$ (299 mg, 2.16 mmol) and 4-(4-bromo-1H-pyrazol-3-yl)pyridine (342 mg, 1.08 mmol) subsequently. The resulting solution was stirred at 80° C. for 3 hours. The reaction mixture was diluted with EA (30 mL) and washed with brine. The organic phase was dried over anhydrous sodium sulfate and concentrated under vacuum. The residue was purified to afford the desired product 4-(4-bromo-1-(4-(2-(3-((tert-butyldimethylsilyl)oxy)propoxy) ethoxy) phenyl)-1H-pyrazol-3-yl) pyridine (DCM:MeOH=20:1) (430 mg) as colorless solid. NMR (400 MHz, $CDCl_3$): δ 8.66 (br, 2H), 7.89-7.93 (m, 3H), 7.55 (d, J=8.8 Hz, 2H), 6.96-6.98 (m, 2H), 4.04-4.14 (m, 2H), 3.76 (d, J=4.8 Hz, 2H), 3.67 (d, J=6 Hz, 3H), 3.58 (d, J=6.4 Hz, 2H), 1.71-1.79 (m, 2H), 0.84 (s, 9H), 0.0 (s, 6H).

Step B: 3-(2-(4-(4-bromo-3-(pyridin-4-yl)-1H-pyrazol-1-yl)phenoxy)ethoxy)propan-1-ol

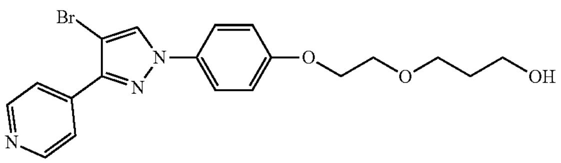 [SMILES: OCCCOCCOc1ccc(-n2cc(Br)c(-c3ccncc3)n2)cc1]

To a solution of 4-(4-bromo-1-(4-(2-(3-((tert-butyldimethylsilyl)oxy) propoxy)ethoxy)phenyl)-1H-pyrazol-3-yl) pyridine (430 mg, 0.808 mmol) in 1,4-dioxane (2 mL) was added 6 M HCl in 1,4-dioxane (4 mL). The resulting solution was stirred at 25° C. for 1 hour. The solvent was removed under reduced pressure to afford crude the desired product 3-(2-(4-(4-bromo-3-(pyridin-4-yl)-1H-pyrazol-1-yl)phenoxy)ethoxy)propan-1-ol (270 mg crude), which was used in next step without further purification. LCMS ($ES^+$): m/z 420.0 $[M+H]^+$.

Step C: 3-(2-(4-(4-bromo-3-(pyridin-4-yl)-1H-pyrazol-1-yl)phenoxy)ethoxy)propanal

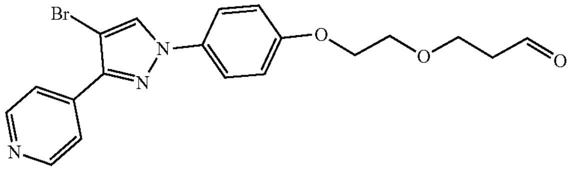 [SMILES: O=CCCOCCOc1ccc(-n2cc(Br)c(-c3ccncc3)n2)cc1]

To a solution of 3-(2-(4-(4-bromo-3-(pyridin-4-yl)-1H-pyrazol-1-yl)phenoxy)ethoxy)propan-1-ol (135 mg, 0.32 mmol), IBX (136 mg, 0.48 mmol) in $CH_3CN$ (4 mL) was added at room temperature. The mixture was stirred at 80° C. for 2 hours. After the reaction was completed, the mixture was filtrated. The filtrate was concentrated under vacuum to afford crude desired product 3-(2-(4-(4-bromo-3-(pyridin-4-yl)-1H-pyrazol-1-yl)phenoxy) ethoxy)propanal (140 mg crude), which was used in next step without further purification. LCMS ($ES^+$): m/z 416.0 $[M+H]^+$.

Step D: tert-butyl 4-(2-(2,6-dioxopiperidin-3-yl)-1,3-dioxoisoindolin-4-yl)piperazine-1-carboxylate

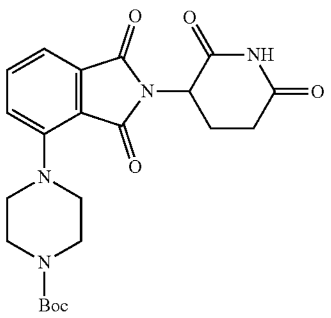 [SMILES: CC(C)(C)OC(=O)N1CCN(c2cccc3c2C(=O)N(C2CCC(=O)NC2=O)C3=O)CC1]

To a solution of tert-butyl piperazine-1-carboxylate (1.35 g, 7.25 mmol) in NMP (10 mL) were added 2-(2,6-dioxopiperidin-3-yl)-4-fluoroisoindoline-1,3-dione (1 g, 3.62 mmol) and DIEA (1.87 g, 14.5 mmol). The resulting solution was stirred at 90° C. under $N_2$ for 4 hours. The reaction mixture was diluted with EA (30 mL) and washed with brine. The organic phase was dried over anhydrous sodium sulfate and concentrated under vacuum. The residue was purified to afford the desired product tert-butyl 4-(2-(2,6-dioxopiperidin-3-yl)-1,3-dioxoisoindolin-4-yl)piperazine-1-carboxylate (DCM:EA=1:1) (1.4 g) as yellow solid. $^1$H NMR (400 MHz, DMSO-d6): δ 7.73 (d, J=7.2 Hz, 1H), 7.35-7.41 (m, 2H), 5.09-5.13 (m, 1H), 3.52 (s, 4H), 3.26 (s, 4H), 2.84-2.89 (m, 1H), 2.56~2.63 (m, 2H), 2.00-2.05 (m, 2H), 1.45 (s, 9H).

Step E: 2-(2,6-Dioxopiperidin-3-yl)-4-(piperazin-1-yl)isoindoline-1,3-dione hydrochloride

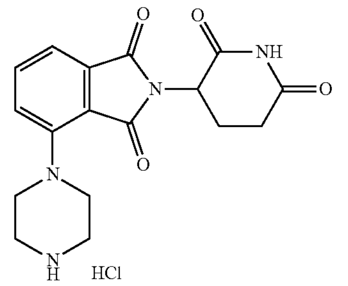 [SMILES: O=C1CCC(N2C(=O)c3cccc(N4CCNCC4)c3C2=O)C(=O)N1 ; Cl]

To a solution of tert-butyl 4-(2-(2,6-dioxopiperidin-3-yl)-1,3-dioxoisoindolin-4-yl)piperazine-1-carboxylate (1.4 g, 3.16 mmol) in 1,4-dioxane (4 mL) was added 6 M HCl in 1,4-dioxane (6 mL). The resulting solution was stirred at 25° C. for 1 hour. The solution was concentrated under reduced pressure. The residue afforded the desired product 2-(2,6-dioxopiperidin-3-yl)-4-(piperazin-1-yl)isoindoline-1,3-dione hydrochloride (1.4 g crude), which was used in next step without further purification. LCMS (ES$^+$): m/z 343.1 [M+H]$^+$.

Step F: 4-(4-(3-(2-(4-(4-bromo-3-(pyridin-4-yl)-1H-pyrazol-1-yl)phenoxy)ethoxy)propyl)piperazin-1-yl)-2-(2,6-dioxopiperidin-3-yl)isoindoline-1,3-dione

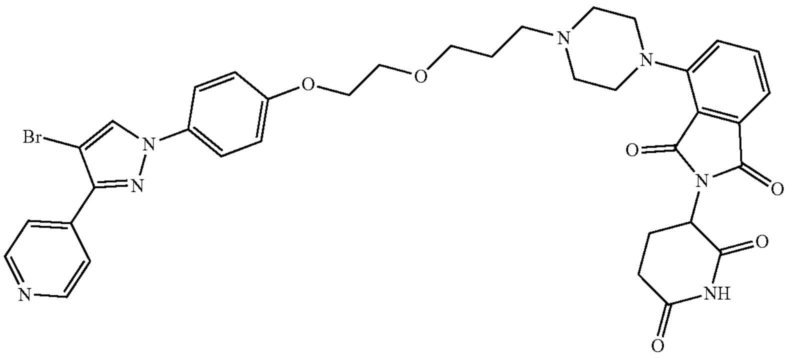 [SMILES: O=C1CCC(N2C(=O)c3cccc(N4CCN(CCCOCCOc5ccc(-n6cc(Br)c(-c7ccncc7)n6)cc5)CC4)c3C2=O)C(=O)N1]

To a solution of 3-(2-(4-(4-bromo-3-(pyridin-4-yl)-1H-pyrazol-1-yl)phenoxy)ethoxy)propanal (140 mg crude, 0.32 mmol), 2-(2,6-dioxopiperidin-3-yl)-4-(piperazin-1-yl) isoindoline-1,3-dione (123 mg, 0.32 mmol), $NaBH_3CN$ (41 mg, 0.64 mmol), acetic acid (3.8 mg, 0.062 mmol) in MeOH. The resulting solution was stirred atrt for overnight. The mixture was diluted with EA, washed with water, and brine. The organic phase was dried over anhydrous sodium sulfate and concentrated under vacuum. The residue was purified to afford the desired product 4-(4-(3-(2-(4-(4-bromo-3-(pyridin-4-yl)-1H-pyrazol-1-yl)phenoxy)ethoxy)propyl)piperazin-1-yl)-2-(2,6-dioxopiperidin-3-yl)isoindoline-1,3-dione (DCM:MeOH=15:1) (70 mg) as yellow solid. LCMS (ES$^+$): m/z 742.1 [M+H]$^+$.

Step G: 2-(2,6-dioxopiperidin-3-yl)-4-(4-(3-(2-(4-(4-(1-oxo-2,3-dihydro-1H-inden-5-yl)-3-(pyridin-4-yl)-1H-pyrazol-1-yl)phenoxy)ethoxy)propyl)piperazin-1-yl)isoindoline-1,3-dione

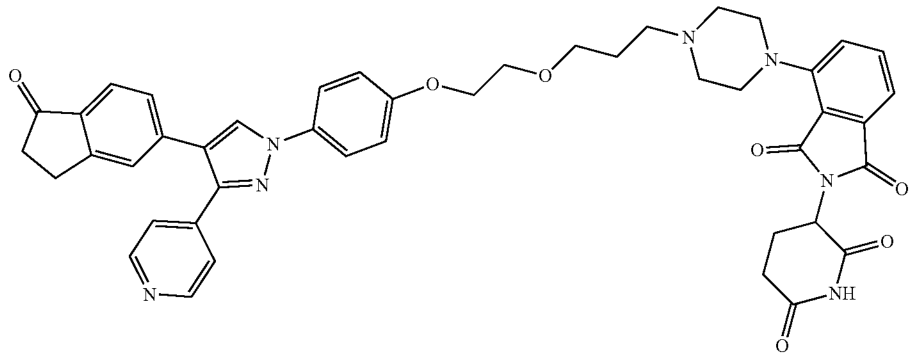 [SMILES: O=C1CCC(N2C(=O)c3cccc(N4CCN(CCCOCCOc5ccc(-n6cc(-c7ccc8c(c7)CCC8=O)c(-c7ccncc7)n6)cc5)CC4)c3C2=O)C(=O)N1]

To a solution of 4-(4-(3-(2-(4-(4-bromo-3-(pyridin-4-yl)-1H-pyrazol-1-yl)phenoxy)ethoxy)propyl)piperazin-1-yl)-2-(2,6-dioxopiperidin-3-yl)isoindoline-1,3-dione (70 mg, 0.094 mmol), 5-(4,4,5,5-tetramethyl-1,3,2-dioxaborolan-2-yl)-2,3-dihydro-1H-inden-1-one (191 mg, 0.74 mmol), $Pd_2(dba)_3$ (181 mg, 0.198 mmol), CsF (300 mg, 1.97 mmol), tri-tert-butylphosphine tetrafluoroborate (115 mg, 0.39 mmol), N,N-dicyclohexylmethylamine (9 mg, 0.047 mmol) in 1,4-dioxane/H2O (6 mL, 10/1). The resulting solution was irradiated at 100° C. with microwave under $N_2$ for 2 hours. After cooling to room temperature, the mixture was diluted with EA, washed with water, and brine. The organic phase was dried over anhydrous sodium sulfate and concentrated under vacuum. The residue was purified to afford the desired product 2-(2,6-dioxopiperidin-3-yl)-4-(4-(3-(2-(4-(4-(1-oxo-2,3-dihydro-1H-inden-5-yl)-3-(pyridin-4-yl)-1H-pyrazol-1-yl)phenoxy)ethoxy)propyl)piperazin-1-yl)isoindoline-1,3-dione (DCM:MeOH=20:1) (33 mg) as yellow solid. LCMS ($ES^+$): m/z 795.3 $[M+H]^+$.

Step H: (E)-2-(2,6-dioxopiperidin-3-yl)-4-(4-(3-(2-(4-(4-(1-(hydroxyimino)-2,3-dihydro-1H-inden-5-yl)-3-(pyridin-4-yl)-1H-pyrazol-1-yl)phenoxy)ethoxy)propyl)piperazin-1-yl)isoindoline-1,3-dione To a solution of 2-(2,6-dioxopiperidin-3-yl)-4-(4-(3-(2-(4-(4-(1-oxo-2,3-dihydro-1H-inden-5-yl)-3-(pyridin-4-yl)-1H-pyrazol-1-yl)phenoxy)ethoxy)propyl)piperazin-1-yl) isoindoline-1,3-dione (33 mg, 0.042 mmol) in acetonitrile (2 mL) and pyridine (1.5 mL), added hydroxylamine hydrochloride (27 mg, 0.42 mmol). The mixture was stirred at 40° C. for 20 minutes, and it was diluted with DCM 20 mL, washed with brine (10 mL). The organic layer was concentrated and purified by preparative TLC to afford (E)-2-(2,6-dioxopiperidin-3-yl)-4-(4-(3-(2-(4-(4-(1-(hydroxyimino)-2,3-dihydro-1H-inden-5-yl)-3-(pyridin-4-yl)-1H-pyrazol-1-yl)phenoxy)ethoxy)propyl)piperazin-1-yl)isoindoline-1,3-dione (22 mg, 66.6% yield) as yellow solid. NMR (400 MHz, $CDCl_3$): δ 8.56 (d, J=5.6 Hz, 2H), 8.37 (s, 1H), 7.94 (s, 1H), 7.68 (d, J=9.2 Hz, 3H), 7.55-7.57 (m, 1H), 7.51 (d, J=5.6 Hz, 2H), 7.38-7.40 (m, 1H), 7.21-7.28 (m, 2H), 7.15 (d, J=8.4 Hz, 1H), 7.04 (d, J=8.8 Hz, 2H), 4.91-4.98 (m, 1H), 4.18 (d, J=4.8 Hz, 2H), 3.82-3.84 (m, 2H), 3.63 (d, J=6.4 Hz, 2H), 3.49 (s, 2H), 3.36-3.38 (m, 4H), 3.02 (d, J=10.8 Hz, 4H), 2.69-2.87 (m, 8H), 2.52-2.56 (m, 2H), 1.85-1.88 (m, 1H); LCMS ($ES^+$): m/z 810.2 $[M+H]^+$.

Compounds 151-172 and 282-284 may be prepared in an analogous manner.

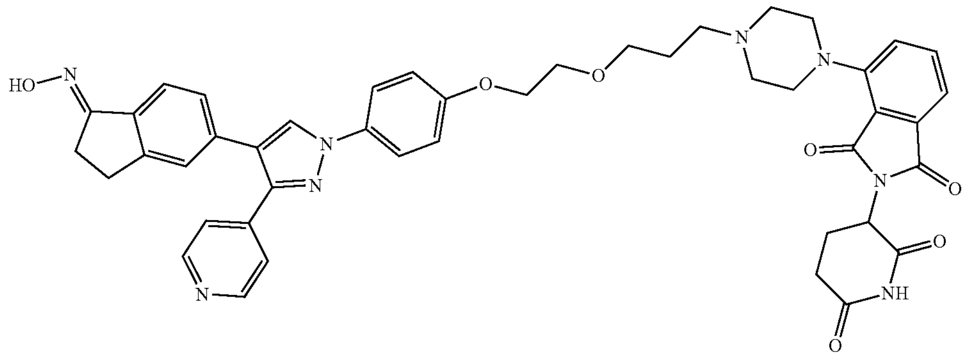 [SMILES: O=C1CCC(N2C(=O)c3cccc(N4CCN(CCCOCCOc5ccc(-n6cc(-c7ccc8c(c7)CC/C8=N\O)c(-c7ccncc7)n6)cc5)CC4)c3C2=O)C(=O)N1]

Example Synthesis of Compound 174

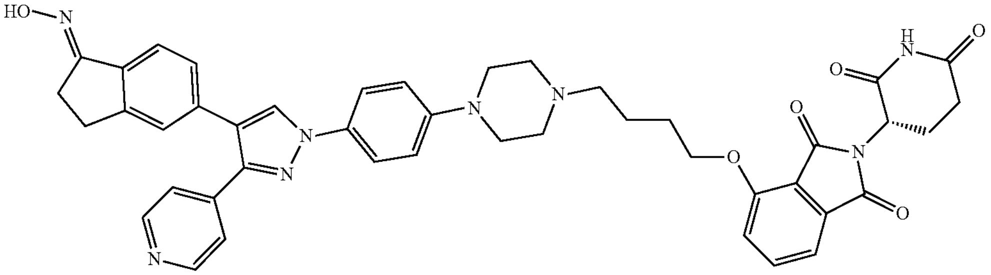 [SMILES: O=C1CC[C@H](N2C(=O)c3cccc(OCCCCN4CCN(c5ccc(-n6cc(-c7ccc8c(c7)CC/C8=N\O)c(-c7ccncc7)n6)cc5)CC4)c3C2=O)C(=O)N1]

Step A: 4-(benzyloxy)butyl 4-methylbenzenesulfonate

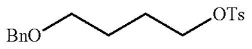 [SMILES: Cc1ccc(S(=O)(=O)OCCCCOCc2ccccc2)cc1]

To a solution of 4-(benzyloxy)butyl 4-methylbenzenesulfonate (5 g, 27.76 mmol), DMAP (0.34 g, 2.78 mmol) and TEA (8.4 g, 83.28 mmol) in DCM (50 mL) was added TsCl (7.94 g, 41.64 mmol) batches. The resulting solution was stirred at 15° C. for 2 hours. The reaction was quenched by addition of saturated $NH_4Cl$ (50 mL). The mixture was extracted with DCM (50 mL×2). The combined organic layer was dried over anhydrous sodium sulfate, concentrated under vacuum. The residue was purified by silica gel to afford desired product 4-(benzyloxy)butyl 4-methylbenzenesulfonate (5.6 g, 60% yield) as a light yellow oil. $^1H$ NMR (400 MHz, $CDCl_3$): δ 7.77 (d, J=8.4 Hz, 2H), 7.26-7.33 (m, 7H), 4.45 (s, 2H), 4.05 (t, J=6.4 Hz, 2H), 3.42 (t, J=6.4 Hz, 2H), 2.44 (s, 3H), 1.59-1.78 (m, 4H).

Step B: (S)-tert-butyl 5-amino-4-(4-(4-(benzyloxy) butoxy)-1,3-dioxoisoindolin-2-yl)-5-oxopentanoate

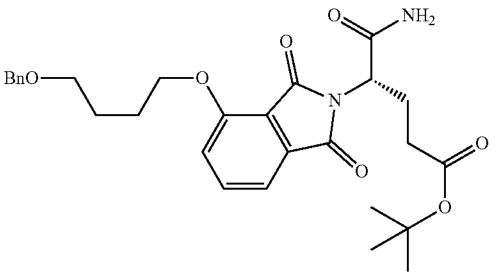 [SMILES: CC(C)(C)OC(=O)CC[C@@H](C(N)=O)N1C(=O)c2cccc(OCCCCOCc3ccccc3)c2C1=O]

To a solution of 4-(benzyloxy)butyl 4-methylbenzenesulfonate (0.63 g, 1.87 mmol) in dry DML (8.0 mL) was added $K_2CO_3$ (0.4 g, 2.88 mmol), tert-butyl (S)-5-amino-4-(4-hydroxy-1,3-dioxoisoindolin-2-yl)-5-oxopentanoate (0.5 g, 1.44 mmol) subsequently. The resulting solution was stirred at 70° C. for 2 hours. After cooling to room temperature, the reaction was quenched with water (30 mL), and the mixture was extracted with EA (40 mL×2). The combined organic layer was washed with brine, dried over anhydrous sodium sulfate, concentrated under vacuum. The residue was purified by silica gel column to afford (S)-tert-butyl 5-amino-4-(4-(4-(benzyloxy)butoxy)-1,3-dioxoisoindolin-2-yl)-5-oxopentanoate (0.4 g, 55% yield). NMR (400 MHz, $CDCl_3$): δ 7.63 (t, J=8.4 Hz, 1H), 7.43 (m, 1H), 1.25-1.85 (m, 5H), 7.18 (s, 1H), 6.41 (br, 1H), 5.66 (br, 1H), 4.79 (m, 1H), 4.52 (s, 2H), 4.19 (t, J=6.4 Hz, 2H), 3.58 (t, J=6.4 Hz, 2H), 3.47 (m, 2H), 2.50 (m, 2H), 2.25 (m, 2H), 2.00 (m, 2H), 1.85 (m, 1H), 1.43 (s, 9H).

Step C: (S)-2-(2,6-dioxopiperidin-3-yl)-4-(4-hydroxybutoxy)isoindoline-1,3-dione

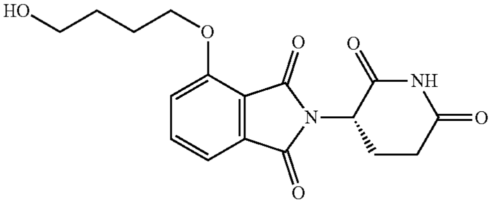 [SMILES: O=C1CC[C@H](N2C(=O)c3cccc(OCCCCO)c3C2=O)C(=O)N1]

To a solution of (S)-Tert-butyl 5-amino-4-(4-(4-(benzyloxy)butoxy)-1,3-dioxoisoindolin-2-yl)-5-oxopentanoate (400 mg, 0.784 mmol) in acetonitrile (5 mL) was added TSOH $H_2O$ (1.48 g, 7.84 mmol). The resulting solution was stirred at 80° C. for 2 hours. The reaction was quenched by saturated $NaHCO_3$ and extracted with EA. The organic layer was dried over anhydrous sodium sulfate, concentrated and purified by column to afford (S)-4-(4-(benzyloxy)butoxy)-2-(2,6-dioxopiperidin-3-yl)isoindoline-1,3-dione (370 mg). To a solution of (S)-4-(4-(benzyloxy)butoxy)-2-(2,6-dioxopiperidin-3-yl)isoindoline-1,3-dione (370 mg, 0.85 mmol) in THF/MeOH (4 mL/1 mL) was added $Pd(OH)_2$ (185 mg) and two drops of concentrated HCl. The resulting mixture was stirred at 20° C. for 1 hour under $H_2$ 1 atm. The resulting solution was filtered and evaporated. The residue was purified by preparative TLC to afford the desired product (S)-2-(2,6-dioxopiperidin-3-yl)-4-(4-hydroxybutoxy)isoindoline-1,3-dione (250 mg, 92% yield in two steps). LCMS ($ES^+$, Neg): m/z 345.0 $[M-H]^+$.

Step D: (S)-4-((2-(2,6-Dioxopiperidin-3-yl)-1,3-dioxoisoindolin-4-yl)oxy)butanal

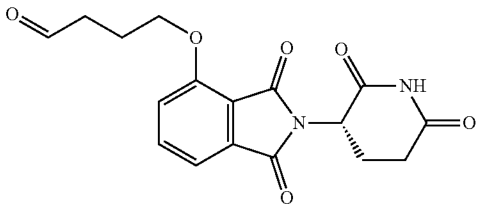 [SMILES: O=CCCCOc1cccc2c1C(=O)N([C@H]1CCC(=O)NC1=O)C2=O]

To a solution of (S)-2-(2,6-dioxopiperidin-3-yl)-4-(4-hydroxybutoxy)isoindoline-1,3-dione (0.25 g, 0.72 mmol) in $CH_3CN$ (5 mL) was added IBX (607 mg, 2.16 mmol). The resulting solution was stirred at 75° C. for 1 hour. After cooling to room temperature, the reaction mixture was filtered and concentrated under vacuum to afford crude desired product (240 mg crude, calculated, 100% yield), which was used in next step directly.

Step E: (S)-4-(4-(4-(4-(4-Bromo-3-(pyridin-4-yl)-1H-pyrazol-1-yl)phenyl)piperazin-1-yl)butoxy)-2-(2,6-dioxopiperidin-3-yl)isoindoline-1,3-dione

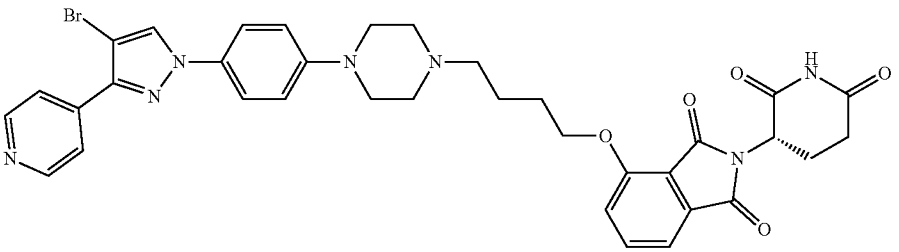 [SMILES: O=C1CC[C@H](N2C(=O)c3cccc(OCCCCN4CCN(c5ccc(-n6cc(Br)c(-c7ccncc7)n6)cc5)CC4)c3C2=O)C(=O)N1]

To a solution of (S)-4-((2-(2,6-dioxopiperidin-3-yl)-1,3-dioxoisoindolin-4-yl)oxy)butanal (240 mg crude, 0.72 mmol) in MeOH (6 mL) was added 1-(4-(4-bromo-3-(pyridin-4-yl)-1H-pyrazol-1-yl)phenyl)piperazine (276 mg, 0.72 mmol) and two drops of AcOH. Then $NaBH_3CN$ (134 mg, 2.16 mmol) was added. The resulting solution was stirred at 18° C. for 2 hours. After quenched with water (30 mL), and the mixture was extracted with EA (40 mL×2). The combined organic layer was dried over anhydrous sodium sulfate and concentrated under vacuum. The residue was applied onto a silica gel column to afford desired product (S)-4-(4-(4-(4-(4-bromo-3-(pyridin-4-yl)-1H-pyrazol-1-yl)phenyl)piperazin-1-yl)butoxy)-2-(2,6-dioxopiperidin-3-yl)isoindoline-1,3-dione (350 mg, 68% yield in two steps). LCMS ($ES^+$): m/z 713.1 $[M+H]^+$.

Step F: (S)-2-(2,6-Dioxopiperidin-3-yl)-4-(4-(4-(4-(4-(1-oxo-2,3-dihydro-1H-inden-5-yl)-3-(pyridin-4-yl)-1H-pyrazol-1-yl)phenyl)piperazin-1-yl)butoxy)isoindoline-1,3-dione To a solution of (S)-4-(4-(4-(4-(4-bromo-3-(pyridin-4-yl)-1H-pyrazol-1-yl)phenyl)piperazin-1-yl)butoxy)-2-(2,6-dioxopiperidin-3-yl)isoindoline-1,3-dione (0.35 g, 0.52 mmol) and 5-(4,4,5,5-tetramethyl-1,3,2-dioxaborolan-2-yl)-2,3-dihydro-1H-inden-1-one (147 mg, 0.57 mmol) in 1,4-dioxane (15 mL)/$H_2O$ (1.5 mL) was added CsF (316 mg, 2.08 mmol), $Pd_2(dba)_3$ (190 mg, 0.21 mmol), tri-tert-butylphosphine tetrafluoroborate (121 mg, 0.42 mmol) and two drops of N-cyclohexyl-N-methylcyclohexanamine subsequently. The reaction was heated to 100° C. for 2 hour under $N_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (S)-2-(2,6-dioxopiperidin-3-yl)-4-(4-(4-(4-(4-(1-oxo-2,3-dihydro-1H-inden-5-yl)-3-(pyridin-4-yl)-1H-pyrazol-1-yl)phenyl)piperazin-1-yl)butoxy)isoindoline-1,3-dione (0.3 g, 80% yield) as yellow solid. LCMS (ES+): m/z 382.8 $[(M+H)/2]^+$.

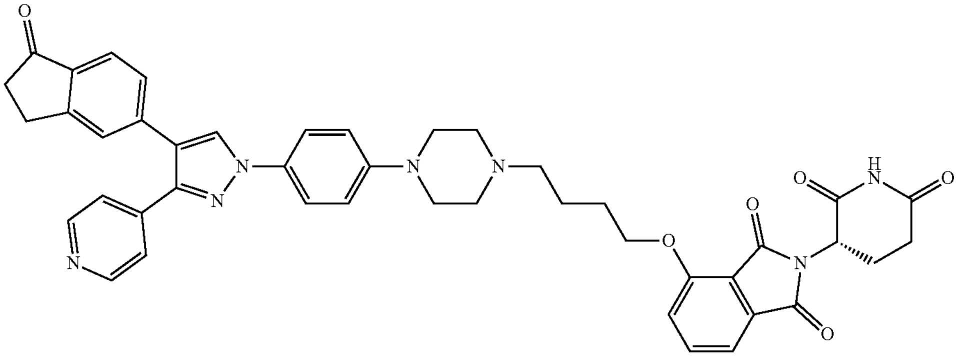 [SMILES: O=C1CC[C@H](N2C(=O)c3cccc(OCCCCN4CCN(c5ccc(-n6cc(-c7ccc8c(c7)CCC8=O)c(-c7ccncc7)n6)cc5)CC4)c3C2=O)C(=O)N1]

Step G: (S,E)-2-(2,6-dioxopiperidin-3-yl)-4-(4-(4-(4-(4-(1-(hydroxyimino)-2,3-dihydro-1H-inden-5-yl)-3-(pyridin-4-yl)-1H-pyrazol-1-yl)phenyl)piperazin-1-yl)butoxy)isoindoline-1,3-dione

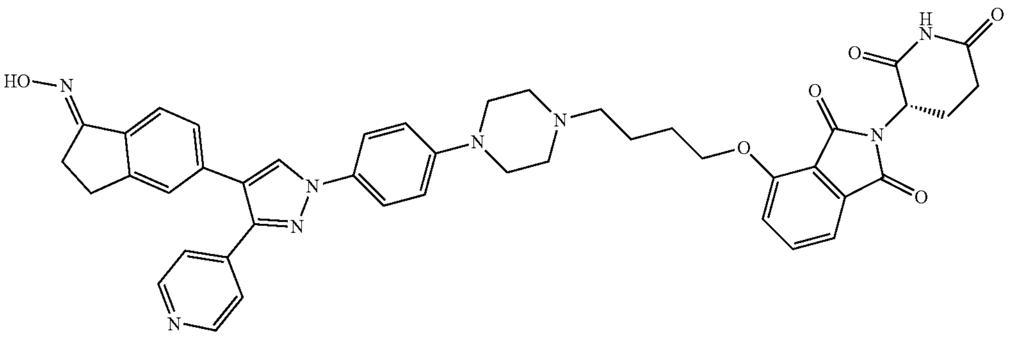 [SMILES: O=C1CC[C@H](N2C(=O)c3cccc(OCCCCN4CCN(c5ccc(-n6cc(-c7ccc8c(c7)CC/C8=N\O)c(-c7ccncc7)n6)cc5)CC4)c3C2=O)C(=O)N1]

To a solution of (S)-2-(2,6-dioxopiperidin-3-yl)-4-(4-(4-(4-(4-(1-oxo-2,3-dihydro-1H-inden-5-yl)-3-(pyridin-4-yl)-1H-pyrazol-1-yl)phenyl)piperazin-1-yl)butoxy)isoindoline-1,3-dione (165 mg, 0.22 mmol) in acetonitrile/pyridine (6 ml/3 ml) was added hydroxylamine hydrochloride (150 mg, 2.16 mmol). The mixture was stirred at 45° C. for 1 hour. The solvent was removed under vacuum, and the residue was purified by preparative TLC with DCM/MeOH (20/1) to afford the desired product (S,E)-2-(2,6-dioxopiperidin-3-yl)-4-(4-(4-(4-(4-(1-(hydroxyimino)-2,3-dihydro-1H-inden-5-yl)-3-(pyridin-4-yl)-1H-pyrazol-1-yl)phenyl)piperazin-1-yl)butoxy)isoindoline-1,3-dione (60 mg, 38% yield) as a white solid. $^1$H NMR (400 MHz, DMSO-d6): δ 11.11 (s, 1H), 10.88 (d, J=3.6 Hz, 1H), 8.69 (s, 1H), 8.56 (m, 2H), 7.81 (m, 3H), 7.35-7.62 (m, 6H), 7.20 (s, 1H), 7.09 (m, 2H), 5.10 (m, 1H), 4.25 (t, J=6.4 Hz, 2H), 3.32 (m, 4H), 3.19 (m, 4H), 2.75-3.05 (m, 5H), 2.40 (m, 2H), 1.60-2.10 (m, 8H); LCMS (ES+): m/z 779.3 $[M+H]^+$.

Compounds 173 and 175-181 may be prepared in an analogous manner.

Example Synthesis of Compound 182

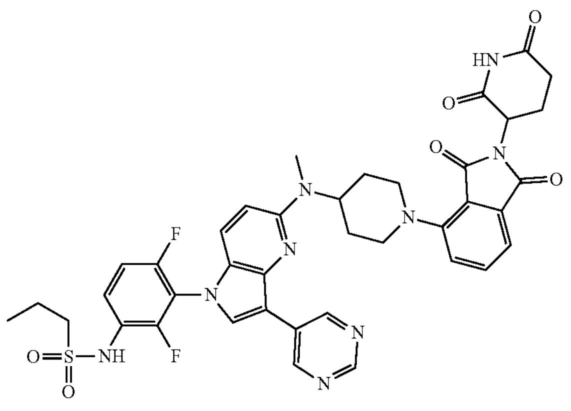 [SMILES: CCCS(=O)(=O)Nc1ccc(F)c(-n2cc(-c3cncnc3)c3nc(N(C)C4CCN(c5cccc6c5C(=O)N(C5CCC(=O)NC5=O)C6=O)CC4)ccc32)c1F]

Step A: N-(3-(5-((1-(2-(2,6-dioxopiperidin-3-yl)-1,3-dioxoisoindolin-4-yl)piperidin-4-yl)(methyl)amino)-3-(pyrimidin-5-yl)-1H-pyrrolo[3,2-b]pyridin-1-yl)-2,4-difluorophenyl)propane-1-sulfonamide

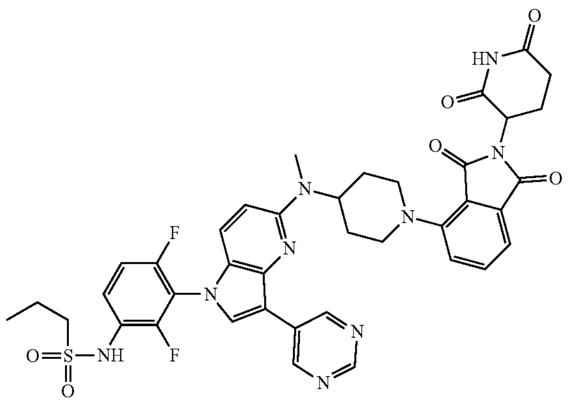 [SMILES: CCCS(=O)(=O)Nc1ccc(F)c(-n2cc(-c3cncnc3)c3nc(N(C)C4CCN(c5cccc6c5C(=O)N(C5CCC(=O)NC5=O)C6=O)CC4)ccc32)c1F]

A mixture of N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide (100.0 mg, 0.18 mmol) (previously described in WO2012/104388), 2-(2,6-dioxopiperidin-3-yl)-4-fluoroisoindoline-1,3-dione (102 mg, 0.36 mmol), DIEA (239 mg, 1.80 mmol) in anhydrous NMP (2.0 mL) was radiated at 130° C. with microwave for 1 hour. After cooling to room temperature, the reaction was quenched with water, and the mixture was extracted with EA (10 mL×3). The combined organic layer was washed with water (10 mL×3), brine (20 mL), dried over anhydrous sodium sulfate and concentrated under vacuum. The residue was purified by preparative TLC to afford the desired product N-(3-(5-((1-(2-(2,6-dioxopiperidin-3-yl)-1,3-dioxoisoindolin-4-yl)piperidin-4-yl)(methyl)amino)-3-(pyrimidin-5-yl)-1H-pyrrolo[3,2-b]pyridin-1-yl)-2,4-difluorophenyl)propane-1-sulfonamide (DCM:MeOH=10:1) (45 mg, yield=30.6%) as white solid. NMR (400 MHz, $CDCl_3$): δ 9.58 (s, 1H), 9.10 (s, 1H), 8.03 (s, 1H), 7.67-7.59 (m, 2H), 7.42 (d, J=7.2 Hz, 1H), 7.34 (d, J=8 Hz, 1H), 7.23-7.18 (m, 1H), 6.66 (d, J=12 Hz, 1H), 5.02-4.81 (m, 1H), 3.90-3.89 (m, 1H), 3.18-3.14 (m, 3H), 3.05 (s, 2H), 2.96-2.87 (m, 3H), 2.13 (dd, J=2.8 Hz, 4 Hz, 2H), 2.00-1.90 (m, 3H), 1.30 (s, 8H), 1.09 (t, J=12.0 Hz, 3H), 0.84-0.088 (m, 4H); LCMS ($ES^+$): m/z 798.2 $[M+H]^+$.

Compound 183 may be prepared in an analogous manner.

Example Synthesis of Compound 184

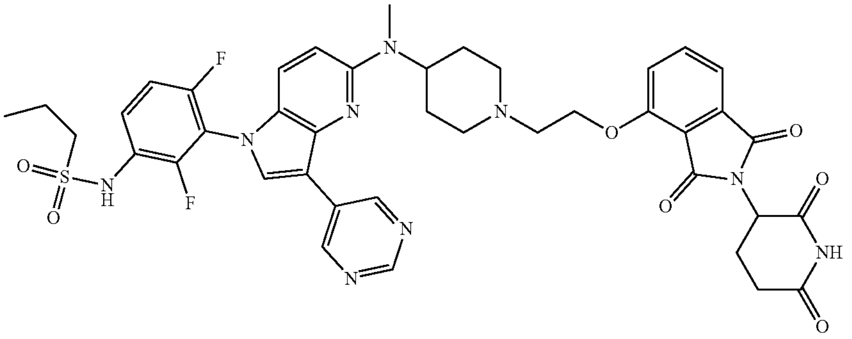 [SMILES: CCCS(=O)(=O)Nc1ccc(F)c(-n2cc(-c3cncnc3)c3nc(N(C)C4CCN(CCOc5cccc6c5C(=O)N(C5CCC(=O)NC5=O)C6=O)CC4)ccc32)c1F]

Step. A: tert-butyl (S)-5-amino-4-(4-(2-(benzyloxy) ethoxy)-1,3-dioxoisoindolin-2-yl)-5-oxopentanoate

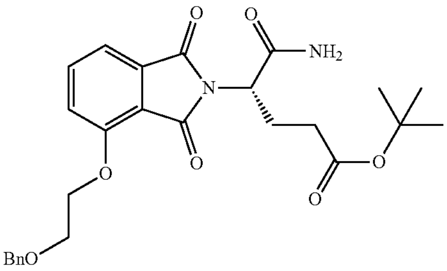 [SMILES: CC(C)(C)OC(=O)CC[C@@H](C(N)=O)N1C(=O)c2cccc(OCCOCc3ccccc3)c2C1=O]

A mixture of tert-butyl (S)-5-amino-4-(4-hydroxy-1,3-dioxoisoindolin-2-yl)-5-oxopentanoate (1.22 g, 3.51 mmol), 2-(benzyloxy)ethyl methanesulfonate (900 mg, 3.91 mmol), $K_2CO_3$ (1.08 g, 7.83 mmol) in DMF (10 mL) was stirred at 70° C. for 6 hours. After quenched with water, the mixture was extracted with EA. The organic phase was dried over anhydrous sodium sulfate and concentrated under vacuum. The residue was purified to afford the desired product tert-butyl (S)-5-amino-4-(4-(2-(benzyloxy)ethoxy)-1,3-dioxoisoindolin-2-yl)-5-oxopentanoate (PE:EtOAc=1:5) (907 mg).

Step B: (S)-4-(2-(benzyloxy)ethoxy)-2-(2,6-dioxopiperidin-3-yl)isoindoline-1,3-dione

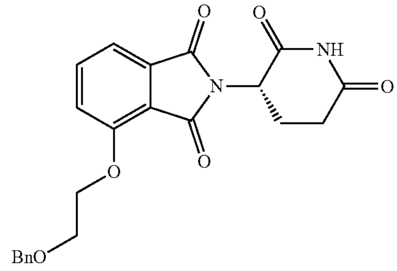 [SMILES: O=C1CC[C@H](N2C(=O)c3cccc(OCCOCc4ccccc4)c3C2=O)C(=O)N1]

To a solution of tert-butyl (S)-5-amino-4-(4-(2-(benzyloxy)ethoxy)-1,3-dioxoisoindolin-2-yl)-5-oxopentanoate (907 mg, 1.88 mmol), p-TsOH (1.5 g, 7.89 mmol) in MeCN (10 mL) was stirred with at 80° C. for 8 hours. After quenched with water, the mixture was diluted with EA, washed with water, brine. The organic phase was dried over anhydrous sodium sulfate and concentrated under vacuum. The residue was purified to afford the desired product (S)-4-(2-(benzyloxy)ethoxy)-2-(2,6-dioxopiperidin-3-yl) isoindoline-1,3-dione (PE:EtOAc=1:1) (1.23 g, crude).

Step C: (S)-2-(2,6-dioxopiperidin-3-yl)-4-(2-hydroxyethoxy)isoindoline-1,3-dione

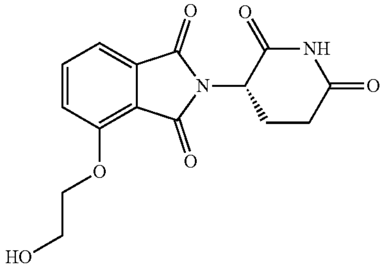 [SMILES: O=C1CC[C@H](N2C(=O)c3cccc(OCCO)c3C2=O)C(=O)N1]

To a solution of (S)-4-(2-(benzyloxy)ethoxy)-2-(2,6-dioxopiperidin-3-yl) isoindoline-1,3-dione (1.23 g, 3.01 mmol), $Pd(OH)_2/C$ (0.7 g), HCl/dioxane (6N, 6 drops) in MeOH/EtOAc (1:1, 40 mL) was stirred with at room temperature for 12 hours under $H_2$ 1 atm. The mixture was filtered through Celite and the filtrate was concentrated under vacuum to afford the desired product (S)-2-(2,6-dioxopiperidin-3-yl)-4-(2-hydroxyethoxy)isoindoline-1,3-dione (700 mg, crude).

Step D: (S)-2-((2-(2,6-dioxopiperidin-3-yl)-1,3-dioxoisoindolin-4-yl)oxy)acetaldehyde

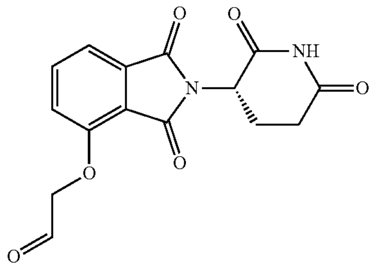 [SMILES: O=CCOc1cccc2c1C(=O)N([C@H]1CCC(=O)NC1=O)C2=O]

To a solution of (S)-2-(2,6-dioxopiperidin-3-yl)-4-(2-hydroxyethoxy)isoindoline-1,3-dione (200 mg, 0.63 mmol) in $CH_3CN$ (10 mL) was added IBX (352 mg, 1.26 mmol). The resulting solution was stirred at 80° C. for 2 hours. After cooling to room temperature, the mixture was filtered, and the filtrate was concentrated under vacuum to afford crude desired product (S)-2-((2-(2,6-dioxopiperidin-3-yl)-1,3-dioxoisoindolin-4-yl)oxy) acetaldehyde (200 mg crude) as yellow solid, which was used into next reaction without further purification.

Step E: N-(3-(5-((1-(2-((2-(2,6-dioxopiperidin-3-yl)-1,3-dioxoisoindolin-4-yl)oxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide

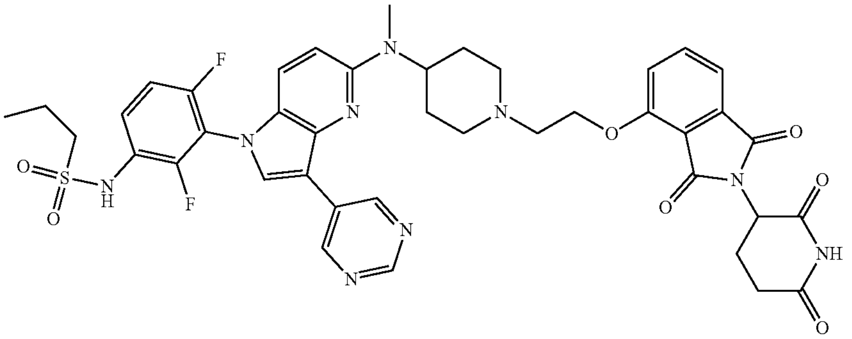 [SMILES: CCCS(=O)(=O)Nc1ccc(F)c(-n2cc(-c3cncnc3)c3nc(N(C)C4CCN(CCOc5cccc6c5C(=O)N(C5CCC(=O)NC5=O)C6=O)CC4)ccc32)c1F]

To a solution of (S)-2-((2-(2,6-dioxopiperidin-3-yl)-1,3-dioxoisoindolin-4-yl)oxy)acetaldehyde (200 mg crude, 0.631 mmol), N-(2,4-difluoro-3-(5-(methyl (piperidin-4-yl) amino)-3-(pyrimidin-5-yl)-1H-pyrrolo[3,2-b]pyridin-1-yl) phenyl)propane-1-sulfonamide hydrochloride (80 mg, 0.148 mmol), $CH_3COOH$ (3.8 mg, 0.062 mmol) in EtOH/DCM (v/v=1/1, 20 mL) was added $NaBH(OAc)_3$ (400 mg, 1.88 mmol). The resulting solution was stirred at room temperature overnight. After quenched with water, the mixture was extracted with EtOAc. The organic phase was dried over anhydrous sodium sulfate and concentrated under vacuum. The residue was purified by prep-TLC (DCM/EtOAc/MeOH=10/1/1) to afford the desired product (S)—N-(3-(5-((1-(2-((2-(2,6-dioxopiperidin-3-yl)-1,3-dioxoisoindolin-4-yl)-oxy)ethyl)piperidin-4-yl)(methyl)amino)-3-(pyrimidin-5-yl)-1H-pyrrolo[3,2-b]pyridin-1-yl)-2,4-difluorophenyl) propane-1-sulfonamide (20.1 mg) as white solid. $^1H$ NMR (400 MHz, DMSO-$d_6$) δ 11.07 (s, 1H), 9.80-10.02 (m, 1H), 9.66 (s, 1H), 9.01 (s, 1H), 8.40 (s, 1H), 7.80-7.89 (m, 1H), 7.61-7.63 (m, 2H), 7.44-7.48 (m, 2H), 6.76 (d, J=9.3 Hz, 1H), 5.08 (dd, J=12.9, 5.2 Hz, 1H), 4.33-4.49 (m, 3H), 3.45 (s, 6H), 3.06-3.25 (m, 3H), 2.94 (s, 2H), 2.83 (s, 2H), 2.55-2.73 (m, 4H), 2.29 (d, J=10.3 Hz, 2H), 1.77 (m, 2H), 1.68 (d, J=10.1 Hz, 2H), 0.99 (t, J=7.4 Hz, 3H); LC-MS: ($ES^+$): m/z 842.3 $[M+H]^+$.

Compounds 185-189 may be prepared in an analogous manner.

Example Synthesis of Compound 191

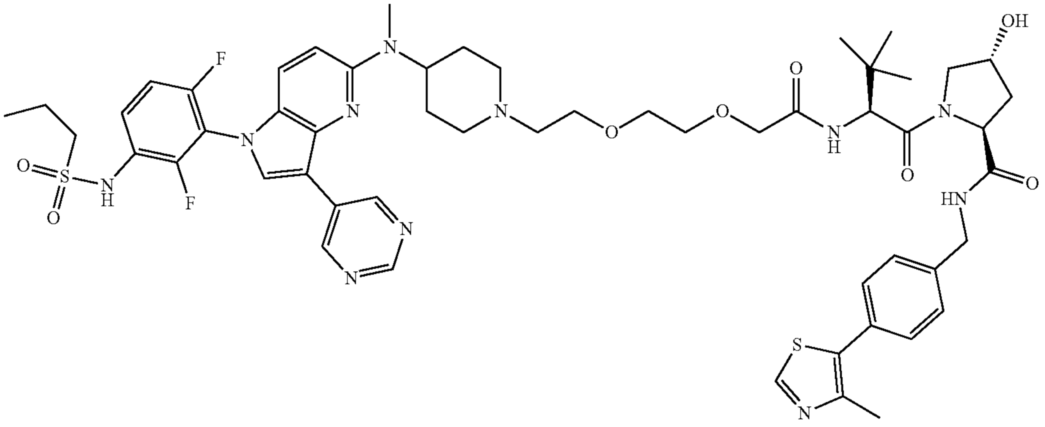 [SMILES: CCCS(=O)(=O)Nc1ccc(F)c(-n2cc(-c3cncnc3)c3nc(N(C)C4CCN(CCOCCOCC(=O)N[C@H](C(=O)N5C[C@H](O)C[C@H]5C(=O)NCc5ccc(-c6scnc6C)cc5)C(C)(C)C)CC4)ccc32)c1F]

Step A: tert-butyl 2-(2-(2-oxoethoxy)ethoxy)acetate

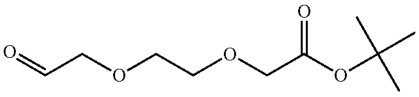

To a solution of tert-butyl 2-(2-(2-hydroxyethoxy)ethoxy) acetate (1 g, 4.55 mmol) in $CH_3CN$ (15 mL) was added IBX (3.8 g, 13.64 mmol). The resulting solution was stirred at 75° C. for 1 hour. After cooling to room temperature, the mixture was filtered and the filtrate was concentrated under vacuum to afford crude desired product tert-butyl 2-(2-(2-oxoethoxy) ethoxy)acetate (1 g crude, 100% yield), which was used in next step directly. $^1H$ NMR (400 MHz, $CDCl_3$): δ 9.75 (s, 1H), 4.18 (s, 2H), 4.03 (s, 2H), 3.77 (s, 4H), 1.48 (s, 9H).

Step B: tert-butyl-2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetate To a solution of tert-butyl 2-(2-(2-oxoethoxy)ethoxy) acetate (181 mg crude, 0.83 mmol) in EtOH/DCM (1/1) was added N-(2,4-difluoro-3-(5-(methyl(piperidin-4-yl)amino)-3-(pyrimidin-5-yl)-1H-pyrrolo[3,2-b]pyridin-1-yl)phenyl) propane-1-sulfonamide hydrochloride (150 mg, 0.28 mmol) and cat. AcOH. KOAc was added if pH was below 5~6. After stirring for 30 minutes, $NaBH(OAc)_3$ (235 mg, 1.11 mmol) was added. The resulting solution was stirred at 30° C. for 1 hour. After quenched with water (20 mL), the mixture was extracted with DCM (30 mL×2). The combined organic layer was dried over anhydrous sodium sulfate and concentrated under vacuum. The residue was applied onto a silica gel column to afford desired product 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetate (120 mg, 58% yield). LCMS: ($ES^+$): m/z 744.3 $[M+H]^+$.

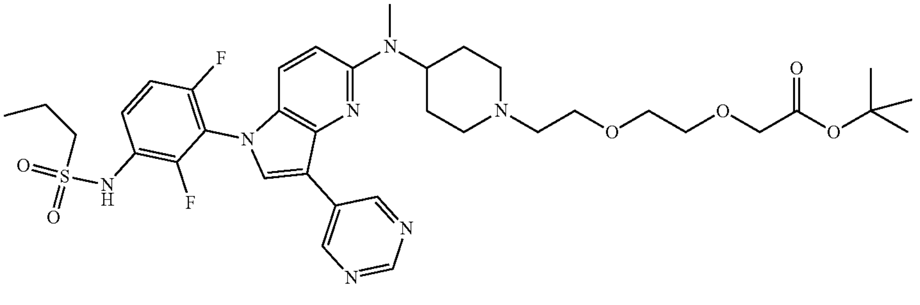 [SMILES: CCCS(=O)(=O)Nc1ccc(F)c(-n2cc(-c3cncnc3)c3nc(N(C)C4CCN(CCOCCOCC(=O)OC(C)(C)C)CC4)ccc32)c1F]

Step C: 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetic acid

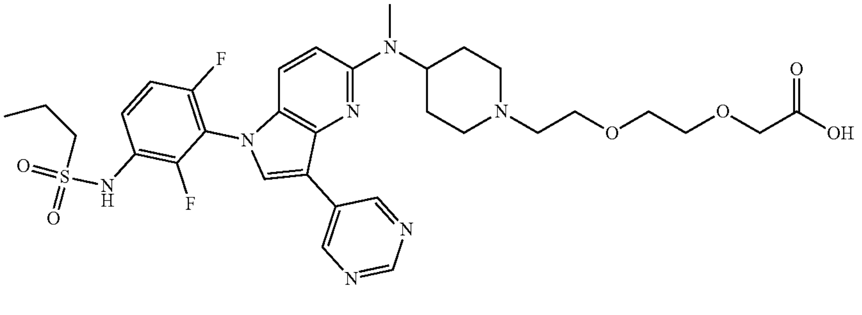 [SMILES: CCCS(=O)(=O)Nc1ccc(F)c(-n2cc(-c3cncnc3)c3nc(N(C)C4CCN(CCOCCOCC(=O)O)CC4)ccc32)c1F]

To a solution of tert-butyl 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetate (0.12 g, 0.16 mmol) in DCM (3 mL) was added TFA (1 mL). The resulting solution was stirred at 30° C. for 1 hour. The solvent was removed under vacuum to afford the desired product 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetic acid (111 mg crude, calculated), which was used into next reaction without further purification. LCMS: ($ES^+$): m/z 688.2 $[M+H]^+$.

Step D: (2S,4R)-1-((S)-2-(2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide To a solution of 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetic acid (111 mg crude, 0.16 mmol) in DCM (10 mL) was added (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (150 mg, 0.32 mmol), DIPEA (209 mg, 1.62 mmol) and PyBOP (250 mg, 0.48 mmol) subsequently. After stirring at 30° C. for 1 hour, the reaction mixture was diluted with DCM (30 mL), washed with water (10 mL×2), brine (10 mL). The organic phase was dried over anhydrous sodium sulfate and concentrated under vacuum. The residue was purified by column (DCM/MeOH 19/1) first and further purified by prep-HPLC to afford the desired product (2S,4R)-1-((S)-2-(2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide (55 mg, 31% yield in two steps) as white solid. $^1H$ NMR (400 MHz, DMSO-$d_6$): δ 9.65 (s, 2H), 9.02 (s, 1H), 8.94 (s, 1H), 8.57 (t, J=4.8 Hz, 1H), 8.40 (m, 1H), 7.55-7.65 (m, 1H), 7.35-7.50 (m, 7H), 6.74 (d, J=9.2 Hz, 1H), 4.57 (d, J=9.6 Hz, 1H), 4.20-4.50 (m, 5H), 4.00 (s, 2H), 3.50-3.70 (m, 2H), 3.00-3.20 (m, 7H), 2.93 (s, 3H), 2.50-2.70 (m, 4H), 2.43 (s, 3H), 1.60-2.25 (m, 13H), 0.90-1.05 (m, 12H); LCMS: ($ES^+$): m/z 1101.4 $[M+H]^+$.

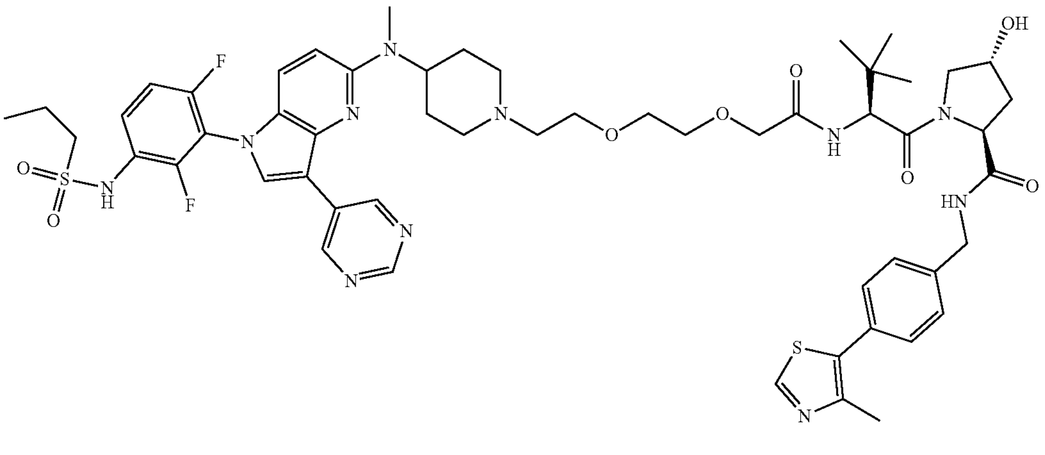 [SMILES: CCCS(=O)(=O)Nc1ccc(F)c(-n2cc(-c3cncnc3)c3nc(N(C)C4CCN(CCOCCOCC(=O)N[C@H](C(=O)N5C[C@H](O)C[C@H]5C(=O)NCc5ccc(-c6scnc6C)cc5)C(C)(C)C)CC4)ccc32)c1F]

Compounds 190 and 192 may be prepared in an analogous manner.

Example Synthesis of Compound 195 [(3R)—N-(3-(5-(4-(2-(2-(2,6-dioxopiperidin-3-yl)-1,3-dioxoisoindolin-5-yloxy)ethoxy)phenyl)-1H-pyrrolo[2,3-b]pyridine-3-carbonyl)-2,4-difluorophenyl)-3-fluoropyrrolidine-1-sulfonamide]

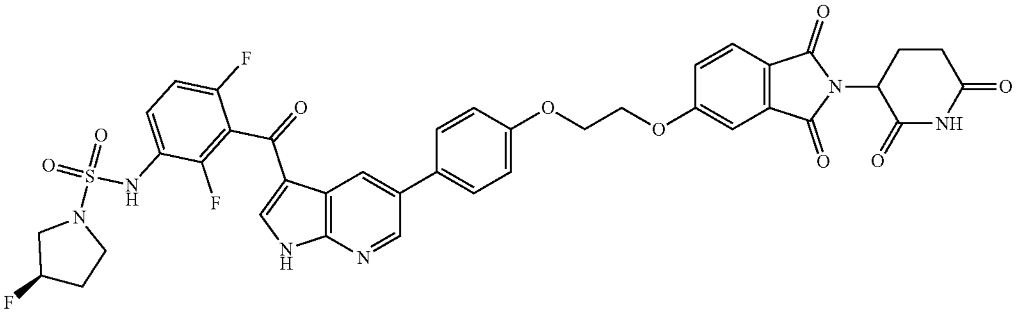 [SMILES: O=C1CCC(N2C(=O)c3ccc(OCCOc4ccc(-c5cnc6[nH]cc(C(=O)c7c(F)ccc(NS(=O)(=O)N8CC[C@@H](F)C8)c7F)c6c5)cc4)cc3C2=O)C(=O)N1]

Step A: ethyl 2-(4-(4,4,5,5-tetramethyl-1,3,2-dioxaborolan-2-yl)phenoxy)acetate

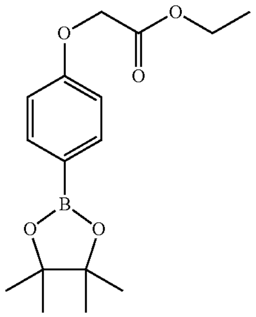 [SMILES: CCOC(=O)COc1ccc(B2OC(C)(C)C(C)(C)O2)cc1]

To a solution of 4-(4,4,5,5-tetramethyl-1,3,2-dioxaborolan-2-yl)phenol (5 g, 22.7 mmol) in N,N-dimethylformamide (50 mL) was added ethyl 2-bromoacetate (4.52 g, 27.2 mmol) and potassium carbonate (6.27 g, 45.4 mmol). The mixture was stirred overnight under nitrogen gas. The reaction mixture was added to water (200 mL), and extracted with ethyl acetate (150 mL×3). The organic layer was washed with brine (100 mL×3). The combined organic phases were dried over anhydrous sodium sulfate, filtered, and concentrated in vacuo to give ethyl 2-(4-(4,4,5,5-tetramethyl-1,3,2-dioxaborolan-2-yl)phenoxy)acetate (5.2 g, 75%) as colorless oil.

Step B: methyl 2-(4-(4,4,5,5-tetramethyl-1,3,2-dioxaborolan-2-yl)phenoxy)ethanol

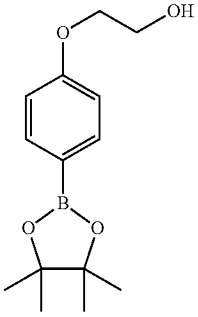 [SMILES: CC1(C)OB(c2ccc(OCCO)cc2)OC1(C)C]

To a solution of ethyl 2-(4-(4,4,5,5-tetramethyl-1,3,2-dioxaborolan-2-yl)phenoxy)acetate (1 g, 3.27 mmol) in tetrahydrofuran/ethanol (10 mL/10 mL) was added sodium borohydride (124 mg, 3.27 mmol) under ice-water bath. The mixture was allowed to warm to room temperature and stirred for 2 hours. The mixture was partitioned between ethyl acetate (100 mL) and water (50 mL). The organic layer was separated, washed with brine (20 mL×3), dried over anhydrous sodium sulfate, filtered, and concentrated in vacuo to give methyl 2-(4-(4,4,5,5-tetramethyl-1,3,2-dioxaborolan-2-yl)phenoxy)ethanol (0.8 g, 93%) as colorless oil.

Step C: 2-(4-(4,4,5,5-tetramethyl-1,3,2-dioxaborolan-2-yl)phenoxy)ethyl methanesulfonate

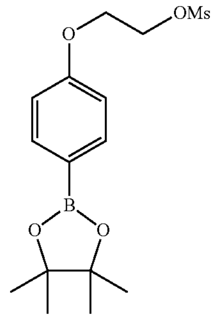 [SMILES: CC1(C)OB(c2ccc(OCCOS(C)(=O)=O)cc2)OC1(C)C]

To a solution of 2-(4-(4,4,5,5-tetramethyl-1,3,2-dioxaborolan-2-yl)phenoxy)ethanol (200 mg, 0.76 mmol) and ehyldiisopropylamine (293 mg, 2.27 mol) in dichloromethane (10.0 mL) was added methanesulfonyl chloride (105 mg, 0.91 mmol) under cooling, and the mixture was stirred at 0° C. for 30 minutes. The mixture was quenched with cold water (10.0 mL), the organic layer was washed with sodium bicarbonate solution (10.0 mL×3) and brine (10.0 mL×3), dried over anhydrous saturated sodium sulfate, filtered and concentrated in vacuo to afford (2-(4-(4,4,5,5-tetramethyl-1,3,2-dioxaborolan-2-yl)phenoxy)ethyl methanesulfonate which was used for next step directly.

Step D: 2-(2,6-dioxopiperidin-3-yl)-5-(2-(4-(4,4,5,5-tetramethyl-1,3,2-dioxaborolan-2-yl)phenoxy)ethoxy)isoindoline-1,3-dione

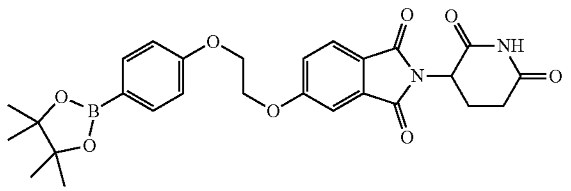 [SMILES: CC1(C)OB(c2ccc(OCCOc3ccc4c(c3)C(=O)N(C3CCC(=O)NC3=O)C4=O)cc2)OC1(C)C]

The mixture of (2-(4-(4,4,5,5-tetramethyl-1,3,2-dioxaborolan-2-yl)phenoxy)ethyl methanesulfonate (260 mg, 0.76 mmol), potassium carbonate (210 mg, 1.52 mol), potassium iodide (126 mg, 0.76 mmol) and 2-(2,6-dioxopiperidin-3-yl)-5-hydroxyisoindoline-1,3-dione (208 mg, 0.76 mmol) in dimethyl sulfoxide (10 mL) was stirred at 60° C. overnight. The resulting mixture was cooled down to room temperature. Water (20 mL) and ethyl acetate (20 mL) was added. The organic layer was separated, washed with brine (10 mL×2), dried over anhydrous sodium sulfate, filtered, and concentrated in vacuo to give the crude product which was purified by pre-TLC (dichloromethane/methanol=20:1) to give 2-(2,6-dioxopiperidin-3-yl)-5-(2-(4-(4,4,5,5-tetramethyl-1,3,2-dioxaborolan-2-yl)phenoxy)ethoxy)isoindoline-1,3-dione (140 mg, 36% two steps) as a white solid. LCMS ($ES^+$): m/z 521.2 $[M+H]^+$, 538.2 $[M+18]^+$.

Step E: (3R)—N-(3-(5-(4-(2-(2-(2,6-dioxopiperidin-3-yl)-1,3-dioxoisoindolin-5-yloxy)ethoxy)phenyl)-1H-pyrrolo[2,3-b]pyridine-3-carbonyl)-2,4-difluorophenyl)-3-fluoropyrrolidine-1-sulfonamide

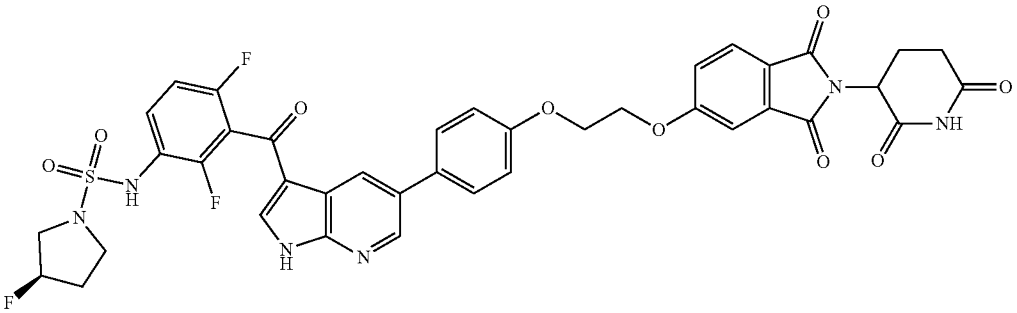 [SMILES: O=C1CCC(N2C(=O)c3ccc(OCCOc4ccc(-c5cnc6[nH]cc(C(=O)c7c(F)ccc(NS(=O)(=O)N8CC[C@@H](F)C8)c7F)c6c5)cc4)cc3C2=O)C(=O)N1]

To a solution of 2-(2,6-dioxopiperidin-3-yl)-5-(2-(4-(4,4,5,5-tetramethyl-1,3,2-dioxaborolan-2-yl)phenoxy)ethoxy)isoindoline-1,3-dione (136 mg, 0.26 mmol), (R)—N-(3-(5-bromo-1H-pyrrolo[2,3-b]pyridine-3-carbonyl)-2,4-difluorophenyl)-3-fluoropyrrolidine-1-sulfonamide (120 mg, 0.24 mmol) and CsF (0.18 mg, 0.012 mmol) in 1,4-dioxane (10 mL) and water (2 mL) was added Pd(aMPhos)$Cl_2$ (17 mg, 0.024 mmol) under argon atmosphere, and the mixture was stirred at 100° C. for 6 hours. When it was cooled to room temperature, water (20 mL) was added and the resultant mixture was extracted by EA (20 mL×3), washed by brine (10 mL×3), dried over anhydrous sodium sulfate, filtered and concentrated. The residue was purified by pre-HPLC to give (3R)—N-(3-(5-(4-(2-(2-(2,6-dioxopiperidin-3-yl)-1,3-dioxoisoindolin-5-yloxy)ethoxy)phenyl)-1H-pyrrolo[2,3-b]pyridine-3-carbonyl)-2,4-difluorophenyl)-3-fluoropyrrolidine-1-sulfonamide (8.1 mg, 4% yield) as a white solid. LCMS ($ES^+$): m/z 817.2 $[M+H]^+$; NMR (400 MHz, DMSO-$d_6$) δ 2.06-2.09 (3H, m), 2.55-2.62 (2H, m), 2.85-2.93 (1H, m), 3.24-3.27 (1H, m), 3.38-3.50 (3H, m), 4.42-4.46 (2H, m), 4.58-4.62 (2H, m), 5.12-5.16 (1H, m), 5.23-5.36 (1H, m), 7.15 (2H, d, J=8.8 Hz), 7.25 (1H, t, J=8.8 Hz), 7.45 (1H, dd, J=2.4, 8.4 Hz), 7.55 (1H, d, J=2.0 Hz), 7.59-7.63 (1H, m), 7.70 (2H, d, J=8.4 Hz), 7.87 (1H, d, J=8.4 Hz), 8.10 (1H, s), 8.58 (1H, s), 8.68 (1H, d, J=2.4 Hz), 9.89 (1H, brs.), 11.14 (1H, s), 12.96 (1H, brs.).

Compounds 194 and 195 may be prepared in an analogous manner.

Example Synthesis of Compound 285 [(2S,4R)-1-((S)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide] and compound 286 [(2S,4R)-1-((R)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methyl thiazol-5-yl)benzyl)pyrrolidine-2-carboxamide]

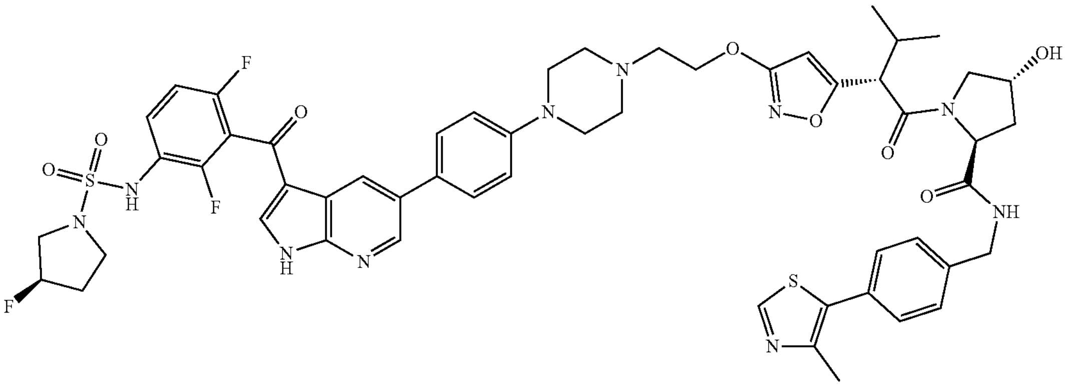

and

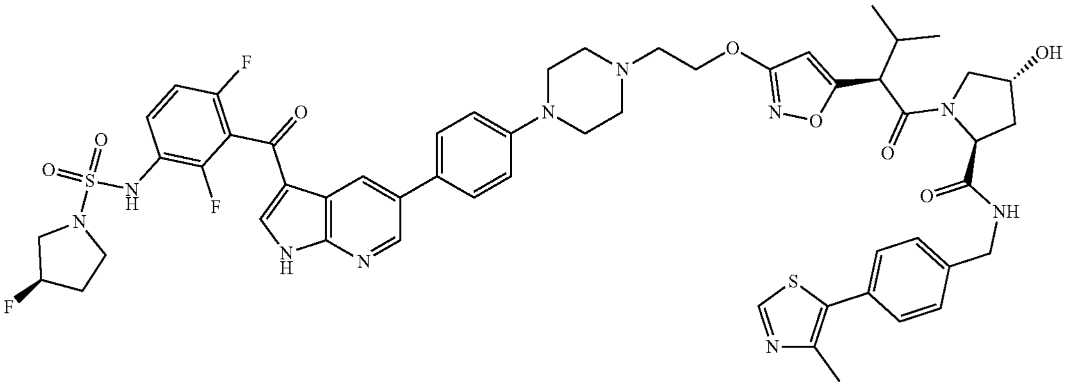

Step A: 2-(3-hydroxy-1,2-oxazol-5-yl)-3-methylbutanoic acid

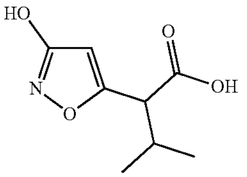

Into a 100 mL round-bottom flask, was placed 2-(3-methoxy-1,2-oxazol-5-yl)-3-methylbutanoic acid (1.0 g, 5.02 mmol, 1.0 equiv) and a solution of hydrobromic acid (11.9 g, 147.07 mmol, 29.30 equiv) in acetic acid (20 mL). The resulting solution was stirred overnight at 60° C. in an oil bath. The reaction mixture was concentrated under reduced pressure. This resulted in 650.0 mg (crude) of 2-(3-hydroxy-1,2-oxazol-5-yl)-3-methylbutanoic acid as a white solid.

LCMS ($ES^+$): m/z 186.05 $[M+H]^+$.

Step B: ethyl 2-(3-hydroxy-1,2-oxazol-5-yl)-3-methylbutanoate

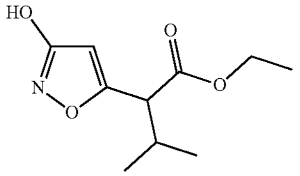

Into a 50 mL round-bottom flask purged and maintained with an inert atmosphere of nitrogen, was placed a solution of 2-(3-hydroxy-1,2-oxazol-5-yl)-3-methylbutanoic acid (650.0 mg, 3.51 mmol, 1.00 equiv) in ethanol (30 mL), sulfuric acid (1 mL). The resulting solution was stirred overnight at 70° C. The reaction mixture was then quenched by the addition of 20 mL water and extracted with ethyl acetate (20 mL×2). The combined organic layer was dried over anhydrous sodium sulfate. Filtered and the filtrate was concentrated under reduced pressure. This resulted in 720.0 mg (96%) of ethyl 2-(3-hydroxy-1,2-oxazol-5-yl)-3-methylbutanoate as light yellow oil.

Step C: ethyl 2-[3-(2-bromoethoxy)-1,2-oxazol-5-yl]-3-methylbutanoate

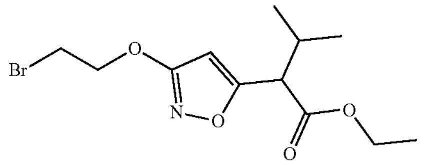 [SMILES: CCOC(=O)C(c1cc(OCCBr)no1)C(C)C]

Into a 50 mL round-bottom flask purged and maintained with an inert atmosphere of nitrogen, was placed a solution of ethyl 2-(3-hydroxy-1,2-oxazol-5-yl)-3-methylbutanoate (380.0 mg, 1.78 mmol, 1.00 equiv) in acetone (15 mL), 1,2-dibromoethane (994.8 mg, 5.30 mmol, 3.00 equiv), $Cs_2CO_3$ (1.17 g, 3.59 mmol, 2.00 equiv). The resulting mixture was stirred overnight at room temperature. The reaction mixture was then quenched by the addition of water (15 mL), and extracted with ethyl acetate (20 mL×3). The combined organic layer was dried over anhydrous sodium sulfate and concentrated under reduced pressure. The residue was applied onto a silica gel column eluting with ethyl acetate/petroleum ether (1:5). This resulted in 450.0 mg (79%) of ethyl 2-[3-(2-bromoethoxy)-1,2-oxazol-5-yl]-3-methylbutanoate as a colorless solid.

Step D: 1-[4-(4,4,5,5-tetramethyl-1,3,2-dioxaborolan-2-yl)phenyl]piperazine

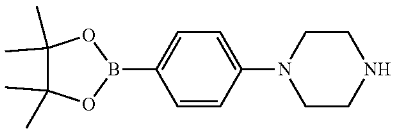

Into a 100 mL round-bottom flask purged and maintained with an inert atmosphere of nitrogen, was placed a solution of tert-butyl 4-[4-(4,4,5,5-tetramethyl-1,3,2-dioxaborolan-2-yl)phenyl]piperazine-1-carboxylate (1.6 g, 4.12 mmol, 1.00 equiv) in dichloromethane (40 mL), followed by the addition of TMSOTf (1.5 g, 6.75 mmol, 1.60 equiv) dropwise with stirring at 0° C. To the above solution was added 6-dimethylpyridine (132.5 mg, 1.00 mmol, 0.30 equiv). The resulting solution was stirred for 3 hours at room temperature. The reaction was then quenched by the addition of 50 mL of saturated sodium bicarbonate aqueous. The resulting solution was extracted with ethyl acetate (30 mL×3). The combined organic layer was dried over anhydrous sodium sulfate and concentrated under reduced pressure. The residue was applied onto a silica gel column eluting with dichloromethane/methanol (10:1). This resulted in 854.0 mg (72%) of 1-[4-(4,4,5,5-tetramethyl-1,3,2-dioxaborolan-2-yl)phenyl]piperazine as off-white solid. LCMS ($ES^+$): m/z 289.15 $[M+H]^+$.

Step E: ethyl 3-methyl-2-[3-(2-[4-[4-(tetramethyl-1,3,2-dioxaborolan-2-yl)phenyl]piperazin-1-yl]ethoxy)-1,2-oxazol-5-yl]butanoate

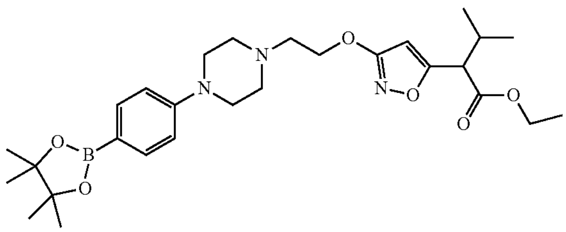 [SMILES: CCOC(=O)C(c1cc(OCCN2CCN(c3ccc(B4OC(C)(C)C(C)(C)O4)cc3)CC2)no1)C(C)C]

Into a 30 mL sealed tube purged and maintained with an inert atmosphere of nitrogen, was placed a solution of ethyl 2-[3-(2-bromoethoxy)-1,2-oxazol-5-yl]-3-methylbutanoate (576.0 mg, 1.80 mmol, LOO equiv) in N,N-dimethylformamide (6 mL), 1-[4-(tetramethyl-1,3,2-dioxaborolan-2-yl)phenyl]piperazine (624.0 mg, 2.17 mmol, 1.20 equiv), DIEA (17 mL), NaI (20 mg). The resulting solution was stirred for 16 hours at 130° C. The reaction mixture was then quenched by the addition of 30 mL of water. The resulting solution was extracted with ethyl acetate (30 mL×3). The combined organic layer was washed with brine (30 mL×3), dried over anhydrous sodium sulfate and concentrated under reduced pressure. The residue was applied onto a silica gel column eluting with ethyl acetate/petroleum ether (1:2). This resulted in 720.0 mg (76%) of ethyl 3-methyl-2-[3-(2-[4-[4-(tetramethyl-1,3,2-dioxaborolan-2-yl)phenyl]piperazin-1-yl]ethoxy)-1,2-oxazol-5-yl]butanoate as alight yellow solid. LCMS ($ES^+$): m/z 528.25 $[M+H]^+$.

Step F: ethyl 2-(3-[2-[4-(4-[3-[(2,6-difluoro-3-[[(3R)-3-fluoropyrrolidinesulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoate

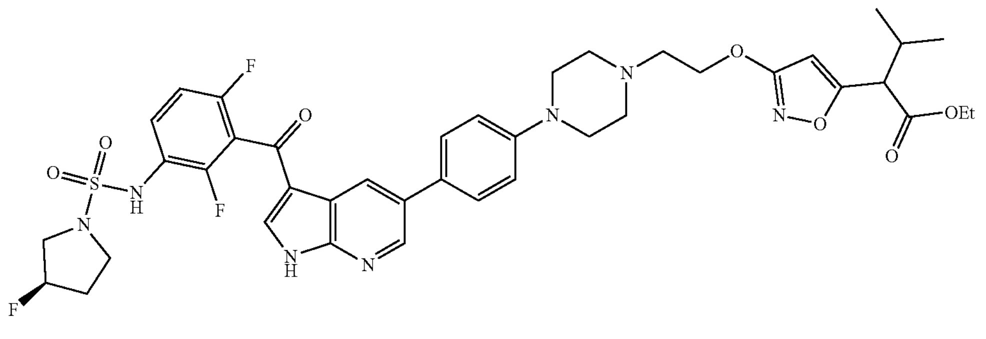 [SMILES: CCOC(=O)C(c1cc(OCCN2CCN(c3ccc(-c4cnc5[nH]cc(C(=O)c6c(F)ccc(NS(=O)(=O)N7CC[C@@H](F)C7)c6F)c5c4)cc3)CC2)no1)C(C)C]

Into a 30 mL sealed tube purged and maintained with an inert atmosphere of nitrogen, was placed a solution of ethyl 3-methyl-2-[3-(2-[4-[4-(tetramethyl-1,3,2-dioxaborolan-2-yl)phenyl]piperazin-1-yl]ethoxy)-1,2-oxazol-5-yl]butanoate (527.0 mg, 1.00 mmol, 1.00 equiv) in 20 mL of 1,4-dioxane/water (4:1), (3R)—N-[3-(5-bromo-1H-pyrrolo[2,3-b]pyridin-3-ylcarbonyl)-2,4-difluorophenyl]-3-fluoropyrrolidine-1-sulfonamide (503.0 mg, 1.00 mmol, 1.00 equiv), sodium carbonate (318.0 mg, 3.00 mmol, 3.00 equiv), $Pd(dppf)Cl_2$ (82.0 mg, 0.10 mmol, 0.10 equiv). The reaction mixture was reacted under microwave radiation for 2 hours at 100° C. The reaction mixture was then quenched by the addition of 20 mL of water. The resulting solution was extracted with ethyl acetate (30 mL×3). The combined organic layer was dried over anhydrous sodium sulfate and concentrated under reduced pressure. The residue was applied onto a silica gel column eluting with dichloromethane/methanol (10:1). This resulted in 460.0 mg (56%) of ethyl 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoate as a light yellow solid. LCMS ($ES^+$): m/z 824.15 $[M+H]^+$.

Step G: 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoic acid

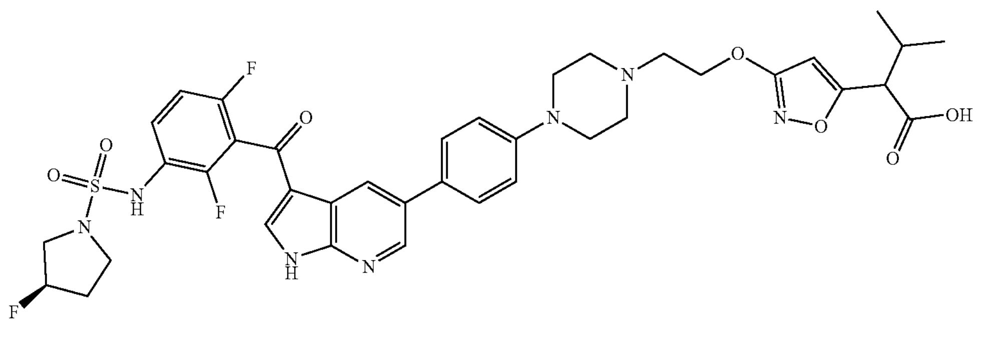 [SMILES: CC(C)C(C(=O)O)c1cc(OCCN2CCN(c3ccc(-c4cnc5[nH]cc(C(=O)c6c(F)ccc(NS(=O)(=O)N7CC[C@@H](F)C7)c6F)c5c4)cc3)CC2)no1]

Into a 50 mL round-bottom flask purged and maintained with an inert atmosphere of nitrogen, was placed a solution of ethyl 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoate (420.0 mg, 0.51 mmol, 1.00 equiv) in methanol (10 mL) and then a solution of sodium hydroxide (102.0 mg, 2.55 mmol, 5.00 equiv) in water (2 mL) was added. The resulting solution was stirred at 40° C. for 5 hours. The pH value of the solution was adjusted to pH 6 with hydrogen chloride (1 mol/L). The solids were collected by filtration. The solid was dried in an oven under reduced pressure. This resulted in 366.0 mg (90%) of 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoic acid as a solid. LCMS ($ES^+$): m/z 796.10 $[M+H]^+$.

Step H: (2S,4R)-1-[2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoyl]-4-hydroxy-N-[[4-(4-methyl-1,3-thiazol-5-yl)phenyl-methyl]pyrrolidine-2-carboxamide

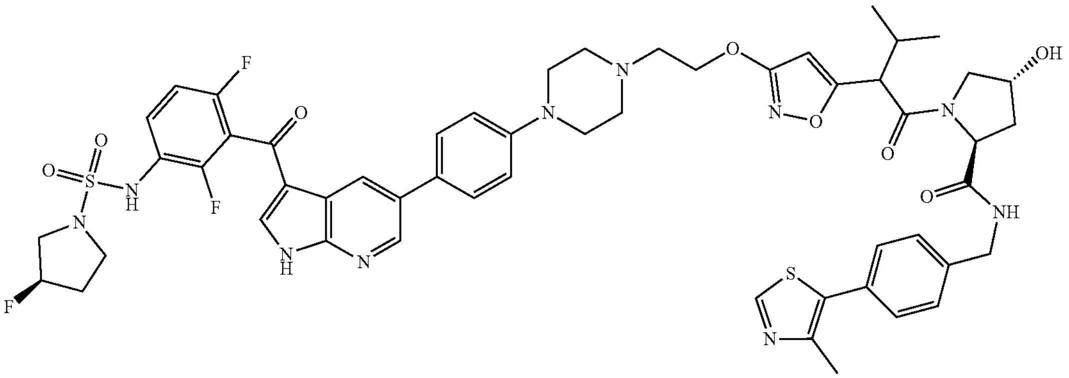 [SMILES: Cc1ncsc1-c1ccc(CNC(=O)[C@@H]2C[C@@H](O)CN2C(=O)C(c2cc(OCCN3CCN(c4ccc(-c5cnc6[nH]cc(C(=O)c7c(F)ccc(NS(=O)(=O)N8CC[C@@H](F)C8)c7F)c6c5)cc4)CC3)no2)C(C)C)cc1]

To a solution of 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoic acid (300.0 mg, 0.38 mmol, 1.00 equiv) and (2S,4R)-4-hydroxy-N-[4-(4-methyl-1,3-thiazol-5-yl)phenyl]methylpyrrolidine-2-carboxamide hydrochloride (199.9 mg, 0.56 mmol, 1.50 equiv) in N,N-dimethylformamide (10 mL), was added DIEA (3.0 mL) and BOP (200.3 mg, 0.45 mmol, 1.20 equiv). The resulting mixture was stirred for 1 hour at room temperature. The reaction was then quenched by the addition of 20 mL of water. The resulting solution was extracted with ethyl acetate (30 mL×3). The combined organic layer was washed with brine (30 mL×3), dried over anhydrous sodium sulfate and concentrated under reduced pressure. The residue was applied onto a silica gel column eluting with dichloromethane/methanol (10:1). This resulted in 265.0 mg (64%) of (2S,4R)-1-[2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide as a solid. LCMS ($ES^+$): m/z 1095.30 $[M+H]^+$.

Step I: (2S,4R)-4-hydroxy-N-[[4-(4-methyl-1,3-thiazol-5-yl)phenyl]methyl]-1-(2-[3-[2-(methylamino)ethoxy]-1,2-oxazol-5-yl]butanoyl)pyrrolidine-2-carboxamide

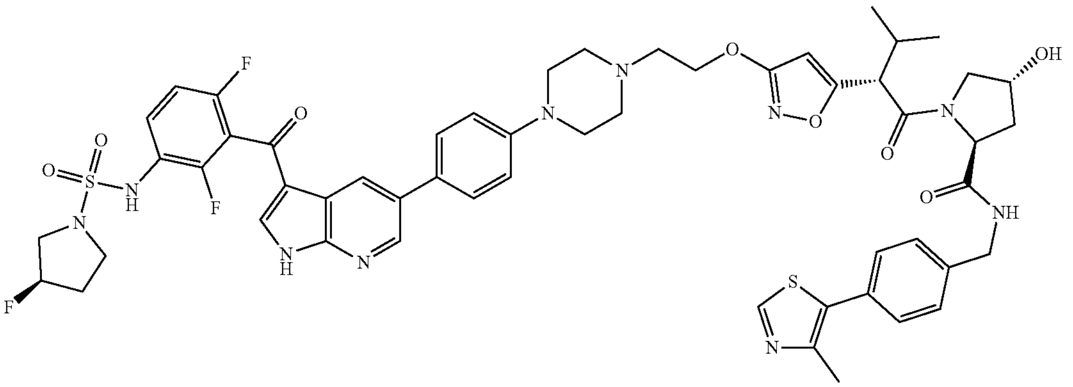

and

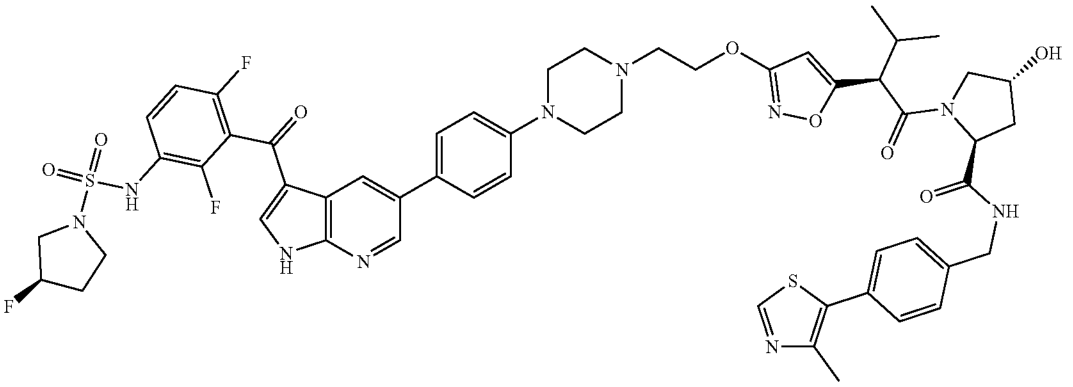

(2S,4R)-1-[2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide was separated by chiral HPLC resulting in:

25.7 mg (10%) of (2S,4R)-1-((S)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide. $^1$H NMR (300 MHz, DMSO-$d_6$): δ9.10-8.97 (m, 1H), 8.65 (d, J=2.0 Hz, 1H), 8.60-8.53 (m, 2H), 8.10-8.07 (m, 1H), 7.70-7.56 (m, 3H), 7.51-7.21 (m, 5H), 7.18-7.07 (m, 2H), 6.18-6.12 (m, 1H), 5.38-5.21 (m, 1H), 4.44-4.31 (m, 6H), 3.78 (d, J=8.6 Hz, 1H), 3.62-3.45 (m, 4H), 3.32-3.01 (m, 8H), 2.98-2.60 (m, 4H), 2.55-2.43 (m, 3H), 2.34-1.82 (m, 6H), 0.97-0.62 (m, 6H). LCMS (ES$^+$): m/z 1095.60 [M+H]$^+$.

57.5 mg (22%) of (2S,4R)-1-((R)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide. $^1$H NMR (300 MHz, DMSO-$d_6$): δ12.90 (brs, 1H), 9.84 (brs, 1H), 8.99-8.95 (m, 1H), 8.69-8.66 (m, 1H), 8.60-8.53 (m, 2H), 8.07 (s, 1H), 7.70-7.61 (m, 3H), 7.54-7.39 (m, 4H), 7.38-7.30 (m, 1H), 7.21-7.08 (m, 2H), 6.18-5.80 (m, 1H), 5.40-5.15 (m, 1H), 4.74-4.28 (m, 6H), 3.90-3.62 (m, 6H), 3.41-3.22 (m, 7H), 3.21-2.81 (m, 5H) 2.45-2.42 (m, 3H), 2.32-2.20 (m, 1H), 2.17-1.80 (m, 4H), 0.95 (d, J=6.5 Hz, 3H), 0.81 (d, J=6.7 Hz, 3H). LCMS (ES$^+$): m/z 1095.60 [M+H]$^+$.

Exemplary compounds 287 and 288 may be prepared in an analogous manner.

Example Synthesis of Compound 291 [(2S,4R)-4-hydroxy-1-((S)-2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide]

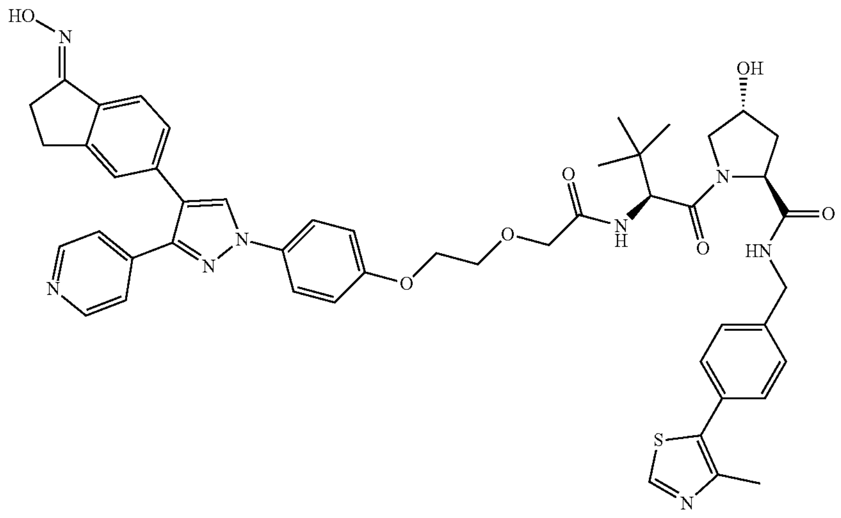 [SMILES: Cc1ncsc1-c1ccc(CNC(=O)[C@@H]2C[C@@H](O)CN2C(=O)[C@@H](NC(=O)COCCOc2ccc(-n3cc(-c4ccc5c(c4)CC/C5=N\O)c(-c4ccncc4)n3)cc2)C(C)(C)C)cc1]

Step A: tert-butyl 2-(2-(4-(4-bromo-3-(pyridin-4-yl)-1H-pyrazol-1-yl)phenoxy)ethoxy)acetatethoxy)acetate

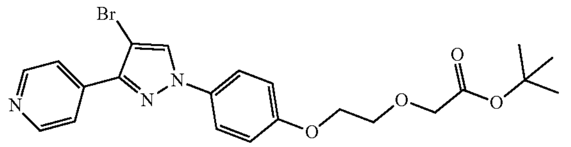 [SMILES: CC(C)(C)OC(=O)COCCOc1ccc(-n2cc(Br)c(-c3ccncc3)n2)cc1]

To a solution of tert-butyl 2-(2-chloroethoxy)acetate (400 mg, 2.06 mmol) and $Cs_2CO_3$ in DMF (15 mL) was added tert-butyl 4-(4-bromo-3-(pyridin-4-yl)-1H-pyrazol-1-yl) phenol (525 mg, 1.66 mmol). The mixture was stirred at 75° C. for 3 hours. The solution was diluted with EA (100 mL). The mixture was washed with water, brine. The organic phase was dried over anhydrous sodium sulfate, filtered and concentrated under reduced pressure. The residue was purified by silica gel column chromatography to afford 2-(2-(4-(4-bromo-3-(pyridin-4-yl)-1H-pyrazol-1-yl) phenoxy) ethoxy)acetatethoxy)acetate (290 mg, 0.62 mmol). LCMS ($ES^+$): m/z 475.21 $[M+H]^+$, 476.1 $[M+2H]^+$.

Step B: (2S,4R)-1-((S)-2-(2-(2-(4-(4-bromo-3-(pyridin-4-yl)-1H-pyrazol-1-yl)phenoxy)ethoxy)acetamido)-3,3-dimethylbutanoyl)-4-hydroxy-N-(4-(4-methylthiazol-5-yl)benzyl)pyrrolidine-2-carboxamide

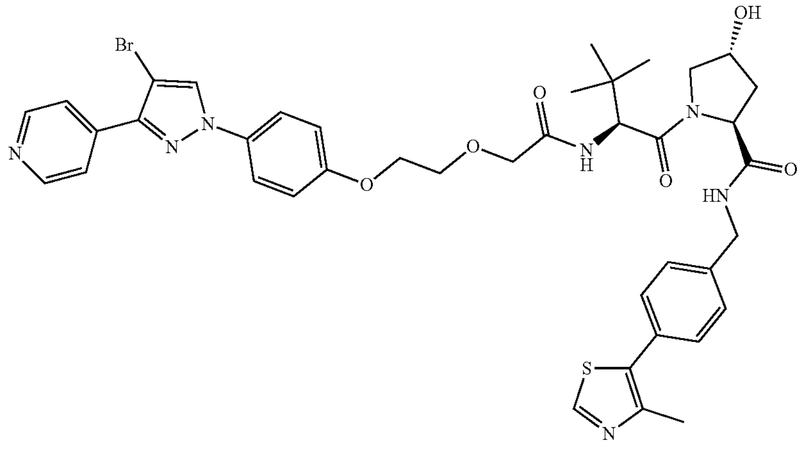 [SMILES: Cc1ncsc1-c1ccc(CNC(=O)[C@@H]2C[C@@H](O)CN2C(=O)[C@@H](NC(=O)COCCOc2ccc(-n3cc(Br)c(-c4ccncc4)n3)cc2)C(C)(C)C)cc1]

To a solution of 2-(2-(4-(4-bromo-3-(pyridin-4-yl)-1H-pyrazol-1-yl) phenoxy)ethoxy)acetatethoxy)acetate (290 mg, 0.61 mmol) in 1,4-dioxane (5 mL) was added HCl (g) in 1,4-dioxane (3 M, 5 mL). The reaction was stirred at room temperature for 2 hours. The solvent was removed under reduced pressure. The residue was dissolved in DCM (20 mL). (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (394 mg, 0.92 mmol), DIPEA (394 mg, 3.05 mmol) and PyBOP (954 g, 1.83 mmol) were added to the solution subsequently. After stirring 30 minutes, it was diluted with DCM (50 mL). The mixture was washed with water, brine. The organic phase was dried over anhydrous sodium sulfate, filtered and concentrated under reduced pressure. The residue was purified by silica gel column chromatography to afford (2S,4R)-1-((S)-2-(2-(2-(4-(4-bromo-3-(pyridin-4-yl)-1H-pyrazol-1-yl)phenoxy)ethoxy) acetamido)-3,3-dimethylbutanoyl)-4-hydroxy-N-(4-(4-methylthiazol-5-yl)benzyl)pyrrolidine-2-carboxamide (390 mg, 0.46 mmol). LCMS ($ES^+$): m/z 830.2 $[M+H]^+$.

Step C: (2S,4R)-1-((S)-3,3-dimethyl-2-(2-(2-(4-(4-(1-oxo-2,3-dihydro-1H-inden-5-yl)-3-(pyridin-4-yl)-1H-pyrazol-1-yl)phenoxy)ethoxy)acetamido)butanoyl)-4-hydroxy-N-(4-(4-methylthiazol-5-yl)benzyl)pyrrolidine-2-carboxamide

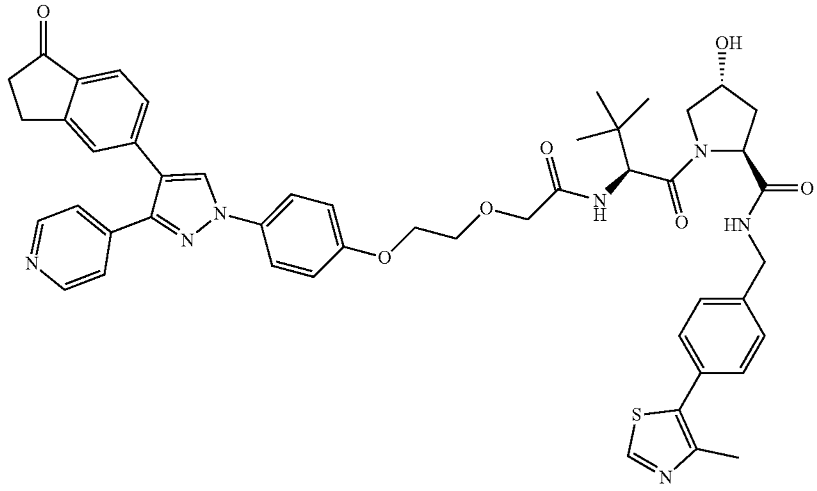 [SMILES: Cc1ncsc1-c1ccc(CNC(=O)[C@@H]2C[C@@H](O)CN2C(=O)[C@@H](NC(=O)COCCOc2ccc(-n3cc(-c4ccc5c(c4)CCC5=O)c(-c4ccncc4)n3)cc2)C(C)(C)C)cc1]

To a solution of (2S,4R)-1-((S)-2-(2-(2-(4-(4-bromo-3-(pyridin-4-yl)-1H-pyrazol-1-yl)phenoxy)ethoxy)acetamido)-3,3-dimethylbutanoyl)-4-hydroxy-N-(4-(4-methylthiazol-5-yl)benzyl)pyrrolidine-2-carboxamide (390 mg, 0.46 mmol) and 5-(4,4,5,5-tetramethyl-1,3,2-dioxaborolan-2-yl)-2,3-dihydro-1H-inden-1-one (248 mg, 0.92 mmol) in 1,4-dioxane/water (20 mL/1 mL) were added Pd(aMPhos) $Cl_2$ (36 mg, 0.046 mmol), CsF (360 mg, 2.30 mmol) subsequently. The reaction mixture was stirred at 90° C. overnight under nitrogen atmosphere. After cooled to room temperature, it was diluted with ethyl acetate (100 mL). The mixture was washed with brine (50 mL×2). The organic phase was dried over anhydrous sodium sulfate, filtered and concentrated under vacuum. The residue was purified by silica gel column chromatography (DCM/MeOH) to afford (2S,4R)-1-((S)-3,3-dimethyl-2-(2-(2-(4-(4-(1-oxo-2,3-dihydro-1H-inden-5-yl)-3-(pyridin-4-yl)-1H-pyrazol-1-yl) phenoxy)ethoxy)acetamido)butanoyl)-4-hydroxy-N-(4-(4-methylthiazol-5-yl)benzyl)pyrrolidine-2-carboxamide (230 mg, 0.26 mmol). LCMS ($ES^+$): m/z 882.3 $[M+H]^+$.

Step D: (2S,4R)-4-hydroxy-1-((S)-2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide

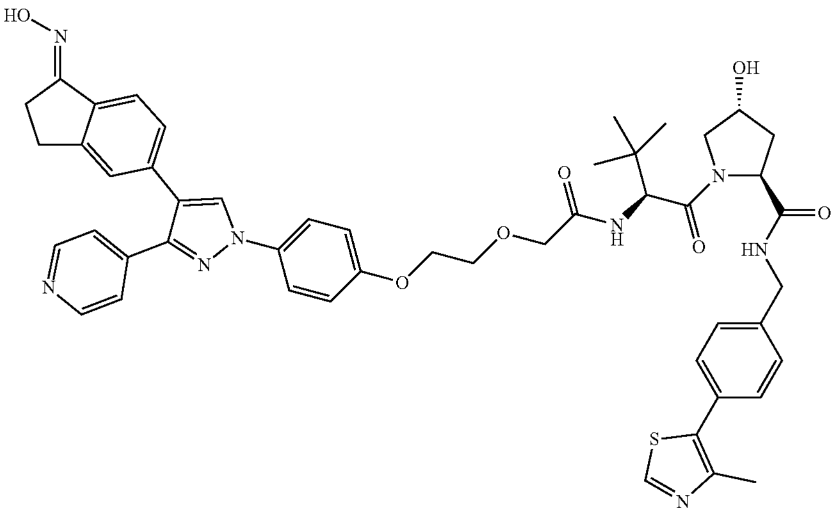 [SMILES: Cc1ncsc1-c1ccc(CNC(=O)[C@@H]2C[C@@H](O)CN2C(=O)[C@@H](NC(=O)COCCOc2ccc(-n3cc(-c4ccc5c(c4)CC/C5=N\O)c(-c4ccncc4)n3)cc2)C(C)(C)C)cc1]

To a solution of (2S,4R)-1-((S)-3,3-dimethyl-2-(2-(2-(4-(4-(1-oxo-2,3-dihydro-1H-inden-5-yl)-3-(pyridin-4-yl)-1H-pyrazol-1-yl)phenoxy)ethoxy)acetamido)butanoyl)-4-hydroxy-N-(4-(4-methylthiazol-5-yl)benzyl)pyrrolidine-2-carboxamide (230 mg, 0.26 mmol) in $CH_3CN$ and pyridine (v/v=1/1, 5 mL) was added $NH_2OH{\cdot}HCl$ (179 mg, 2.6 mmol). The solution was stirred at 20° C. for 3 hours. The mixture was filtered through Celite. The filtrate was concentrated under vacuum. The residue was purified by silica gel column chromatography (DCM/MeOH) to afford (2S,4R)-4-hydroxy-1-((S)-2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide (21 mg, 0.023 mmol). $^1$H NMR (400 MHz, DMSO-$d_6$): δ 10.89 (s, 1H), 8.97 (s, 1H), 8.72 (s, 1H), 8.56-8.58 (m, 3H), 7.86 (d, J=8.4 Hz, 2H), 7.49-7.57 (m, 3H), 7.39 (m, 6H), 7.22 (s, 1H), 7.09-7.12 (m, 2H), 5.17 (m, 1H), 4.52-4.65 (m, 1H), 4.32-4.50 (m, 3H), 4.08-4.29 (s, 4H), 3.95-4.05 (m, 2H), 3.73-3.82 (m, 2H), 3.56-3.70 (m, 2H), 2.95-3.08 (m, 2H), 2.76-2.85 (s, 2H), 2.40-2.51 (m, 3H), 1.87-2.16 (s, 1H), 0.91-1.07 (s, 9H). LCMS (ES$^+$): m/z 898.4 $[M+H]^+$.

Exemplary compounds 289, 290, 292, and 293 may be prepared in an analogous manner.

Example 15-Synthetic Scheme A: Compounds 305, 298, 299, 300, 301, 302, 514, and 303

Method A
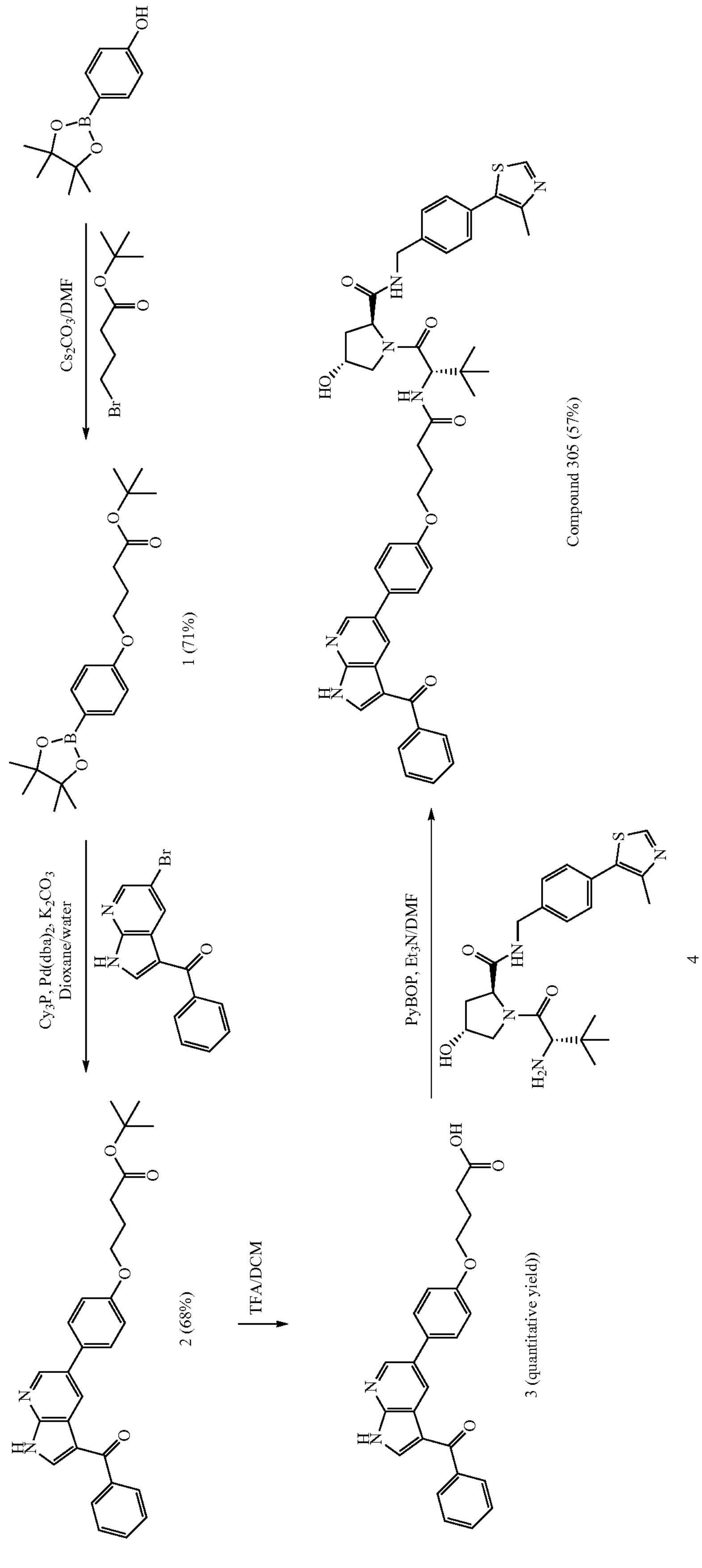

tert-Butyl 4-(4-(4,4,5,5-tetramethyl-1,3,2-dioxaborolan-2-yl)phenoxy)butanoate (1). To a mixture of 4-(4,4,5,5-tetramethyl-1,3,2-dioxaborolan-2-yl)phenol (209.12 mg, 0.95 mmol) and tert-butyl 4-bromobutanoate (212 mg, 0.95 mmol) in N,N-Dimethylformamide (2 mL) was added $Cs_2CO_3$ (402.47 mg, 1.24 mmol). Reaction mixture was heated at 65° C. for 12 hours (overnight). By TLC small amounts of starting material (Hex:AcOEt, 7:3). Crude product was purified by flash CC ($SiO_2$-25 g, Hex:AcOEt, gradient 9:1 to 4:6) to give 198 mg (57% yield) of product as an oil: $^1$H NMR (500 MHz, DMSO-d6) δ 7.59 (d, J=8.2 Hz, 2H), 6.91 (d, J=7.9 Hz, 2H), 3.99 (t, J=6.3 Hz, 2H), 2.35 (t, J=7.3 Hz, 2H), 1.92 (p, J=6.7 Hz, 2H), 1.39 (s, 9H), 1.27 (s, 12H). $^{13}$C NMR (101 MHz, dmso) δ 172.25, 161.56, 136.66, 114.37, 83.77, 80.12, 66.81, 31.72, 28.20, 25.12, 24.71. LC-MS (ESI); m/z $[M+Na]^+$: Calcd. for $C_{20}H_{31}BO_5Na$, 385.2162. Found 385.2194.

tert-Butyl 4-(4-(3-benzoyl-1H-pyrrolo[2,3-b]pyridin-5-yl)phenoxy)butanoate (2). To a solution of tert-butyl 4-[4-(4,4,5,5-tetramethyl-1,3,2-dioxaborolan-2-yl)phenoxy]-butanoate (72 mg, 0.2 mmol) and (5-bromo-1H-pyrrolo[2,3-b]pyridin-3-yl)-phenyl-methanone (59.85 mg, 0.2 mmol) in Dioxane (6 mL) was de-gassed under vacuum and purged with argon. Then $K_2CO_3$ (82.4 mg, 0.6 mmol) was added, follow by water (2 mL), the reaction mixture was de-gassed under vacuum and purged with argon again. Tricyclohexylphosphine (5.57 mg, 0.02 mmol) and $Pd(dba)_2$ (5.71 mg, 0.01 mmol) was added into and the reaction mixture and the reaction mixture was de-gassed under vacuum and purged with argon again. Then reaction mixture was heated at 90° C. for 2 hours. By TLC some SM (Hex:AcOEt, 3:7), an additional amounts of Tricyclohexylphosphine (5.57 mg, 0.02 mmol) and $Pd(dba)_2$ (5.71 mg, 0.01 mmol) was added twice and reaction mixture stirred for an additional 2 hours. The reaction mixture was diluted with AcOEt (20 mL), dried ($Na_2SO_4$), and filtered in vacuum over a celite pad, filtrate was dried ($Na_2SO_4$) and concentrated under vacuum. The crude material was diluted in DCM and purified by flash chromatography ($SiO_2$-40 g, gradient Hex:AcOEt, gradient 9:1 to 100% AcOEt) to give 69 mg (68%) of product as off-white solid. NMR (500 MHz, DMSO-d6) δ 12.68 (s, 1H), 8.65 (s, 1H), 8.60 (s, 1H), 8.10 (s, 1H), 7.82 (d, J=7.5 Hz, 2H), 7.58 (dt, J=36.0, 7.9 Hz, 5H), 7.04 (d, J=8.1 Hz, 2H), 4.16-3.83 (m, 2H), 2.37 (t, J=6.5 Hz, 2H), 1.95 (dd, J=11.4, 5.5 Hz, 2H), 1.39 (s, 9H). $^{13}$C NMR (126 MHz, dmso) δ 189.81, 171.86, 158.13, 148.26, 143.24, 139.62, 136.43, 131.45, 130.82, 130.66, 128.52, 128.48, 128.16, 127.01, 118.77, 115.13, 113.73, 79.68, 66.63, 31.36, 27.77, 24.37. LC-MS (ESI); m/z: $[M+H]^+$ Calcd. for $C_{28}H_{29}N_2O_4$, 457.2127. Found 457.2156.

4-(4-(3-Benzoyl-1H-pyrrolo[2,3-b]pyridin-5-yl)phenoxy)butanoic acid (3). A solution of tert-butyl 4-(4-(3-(2,6-difluorobenzoyl)-1H-pyrrolo[2,3-b]pyridin-5-yl)-phenoxy)butanoate (30 mg, 0.06 mmol) in a mixture of TFA (1 ml, 13.46 mmol) and dichloromethane (3 ml) was stirred for 1 hour. Then the solvent was removed under vacuum and crude product was dried under high vacuum for 2 hours. Crude product was used in the next step without any further purification (26.5 mg, quantitative yield). LC-MS (ESI); m/z: $[M+H]^+$ Calcd. for $C_{24}H_{21}N_2O_4$, 401.1501. Found 401.1420.

(2S,4R)-1-((S)-2-(4-(4-(3-benzoyl-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide (Compound 305). To a solution of 4-[4-(3-benzoyl-1H-pyrrolo[2,3-b]pyridin-5-yl)-phenoxy]butanoic acid (26.5 mg, 0.07 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (30.91 mg, 0.07 mmol) in DMF (2 ml) was added TEA (0.2 ml, 1.43 mmol) and PyBOP (37.88 mg, 0.07 mmol) at room temperature. The reaction mixture was stirred for 12 hours (overnight) at the same temperature. TLC (DCM:MeOH:$NH_4OH$, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTLC (MeOH:DCM, 9:1), to give 31 mg of product (58% yield). $^1$H NMR (400 MHz, DMSO-d6) δ 12.70 (s, 1H), 8.97 (s, 1H), 8.68 (d, J=2.2 Hz, 1H), 8.62 (d, J=2.3 Hz, 1H), 8.60-8.51 (m, 1H), 8.12 (s, 1H), 8.00 (d, J=9.3 Hz, 1H), 7.90-7.77 (m, 1H), 7.72-7.51 (m, 5H), 7.48-7.29 (m, 4H), 7.07 (d, J=8.7 Hz, 2H), 5.15 (d, J=3.5 Hz, 1H), 4.59 (d, J=9.3 Hz, 1H), 4.50-4.32 (m, 3H), 4.22 (dd, J=15.9, 5.4 Hz, 1H), 4.03 (td, J=6.5, 2.6 Hz, 2H), 3.80-3.60 (m, 2H), 2.44 (s, 3H), 2.48-2.28 (m, 5H), 2.13-1.84 (m, 4H), 0.96 (s, 9H). $^{13}$C NMR (101 MHz, dmso) δ 189.87, 172.00, 171.63, 169.69, 158.23, 151.48, 148.29, 147.73, 143.29, 139.64, 139.53, 136.54, 131.52, 131.19, 130.74, 129.65, 128.66, 128.58, 128.55, 128.21, 127.44, 127.05, 118.81, 115.19, 113.74, 68.93, 67.13, 58.75, 56.47, 48.64, 41.68, 38.01, 35.29, 31.33, 26.43, 25.08, 15.99. LC-MS (ESI); m/z $[M+H]^+$: Calcd. for $C_{46}H_{49}N_6O_6S$, 813.3434. Found 813.3478.

(2S,4S)-1-((S)-2-(4-(4-(3-(2,6-difluoro-3-(propylsulfonamido)benzoyl)-1H-pyrrolo[2,3-b]-pyridine-5-yl)phenoxy)butanamido)-3,3-dimethylbutanoyl)-4-hydroxy-N-(4-(4-methylthiazol-5-yl)-benzyl) pyrrolidine-2-carboxamide (Compound 514)

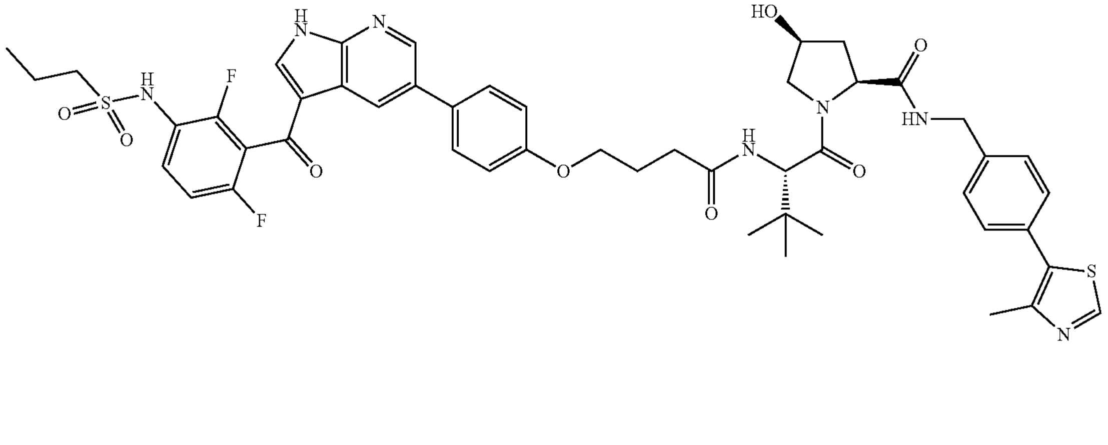 [SMILES: CCCS(=O)(=O)Nc1ccc(F)c(C(=O)c2c[nH]c3ncc(-c4ccc(OCCCC(=O)N[C@H](C(=O)N5C[C@@H](O)C[C@H]5C(=O)NCc5ccc(-c6scnc6C)cc5)C(C)(C)C)cc4)cc23)c1F]

To a solution of 4-[4-[3-[2,6-difluoro-3-(propyl-sulfonylamino)benzoyl]-1H-pyrrolo[2,3-b]pyridin-5-yl]phenoxy]butanoic acid (4.08 mg, 0.00732 mmol) and (2S,4S)-1-((S)-2-amino-3,3-dimethylbutanoyl)-4-hydroxy-N-(4-(4-methylthiazol-5-yl)benzyl)-pyrrolidine-2-carboxamide (3.76 mg, 0.00873 mmol) in DMF (1.5 ml) was added TEA (0.200 mL, 1.43 mmol) and PyBOP (4.19 mg, 0.00805 mmol) at room temperature. The reaction mixture was stirred for 4 h at the same temperature. TLC (DCM:MB, 1:1) shows no starting materials. The DMF was removed under high vacuum (product is partially soluble in water). Crude product was filtered over a silica-carbonate cartridge using DCM:MeOH (9:1) as a eluent. Filtrate was evaporated under vacuum and crude product was purified by PTLC (DCM:MeOH:$NH_4OH$, 90:9:1) to give 3.1 mg of product (43% yield). (500 MHz, DMSO-d6) δ 12.83 (bs, 1H), 9.64 (bs, 1H), 8.96 (s, 1H), 8.77-8.41 (m, 3H), 8.18 (s, 1H), 7.97 (d, J=8.6 Hz, 1H), 7.65 (d, J=8.5 Hz, 2H), 7.61-7.48 (m, 1H), 7.38 (q, J=8.2 Hz, 4H), 7.26 (t, J=8.7 Hz, 1H), 7.04 (d, J=8.7 Hz, 2H), 5.43 (d, J=7.2 Hz, 1H), 4.54-4.31 (m, 3H), 4.30-4.15 (m, 2H), 4.08-3.88 (m, 3H), 3.50-3.40 (m, 1H), 3.16-3.02 (m, 2H), 2.44-2.26 (m, 3H), 2.42 (s, 3H), 2.04-1.88 (m, 2H), 1.79-1.63 (m, 3H), 0.95 (s, 9H), 0.94 (t, 3H). $^{13}C$ NMR (151 MHz, DMSO-d6) δ 181.03, 172.89, 172.34, 170.35, 158.75, 156.44 (dd, J=246.1, 6.7 Hz), 152.78 (dd, J=249.5, 8.6 Hz), 151.89, 148.94, 148.15, 144.15, 139.63, 139.07, 131.74, 131.55, 130.82, 130.14, 129.36-129.11 (m), 129.08, 128.68, 127.86, 126.85, 122.35 (dd, J=13.6, 3.4 Hz), 117.94, 116.03, 115.59, 69.53, 67.52, 58.95, 57.24, 56.04, 53.86, 42.21, 37.36, 35.11, 31.62, 26.82, 25.42, 17.26, 16.37, 13.04. LC-MS (ESI); m/z $[M+H]^+$: Calcd. for $C_{49}H_{54}F_2N_7O_8S_2$, 970.3443. Found 970.3422

Example 16-Synthetic Scheme B: 217, 220, 510, and 221

Method B
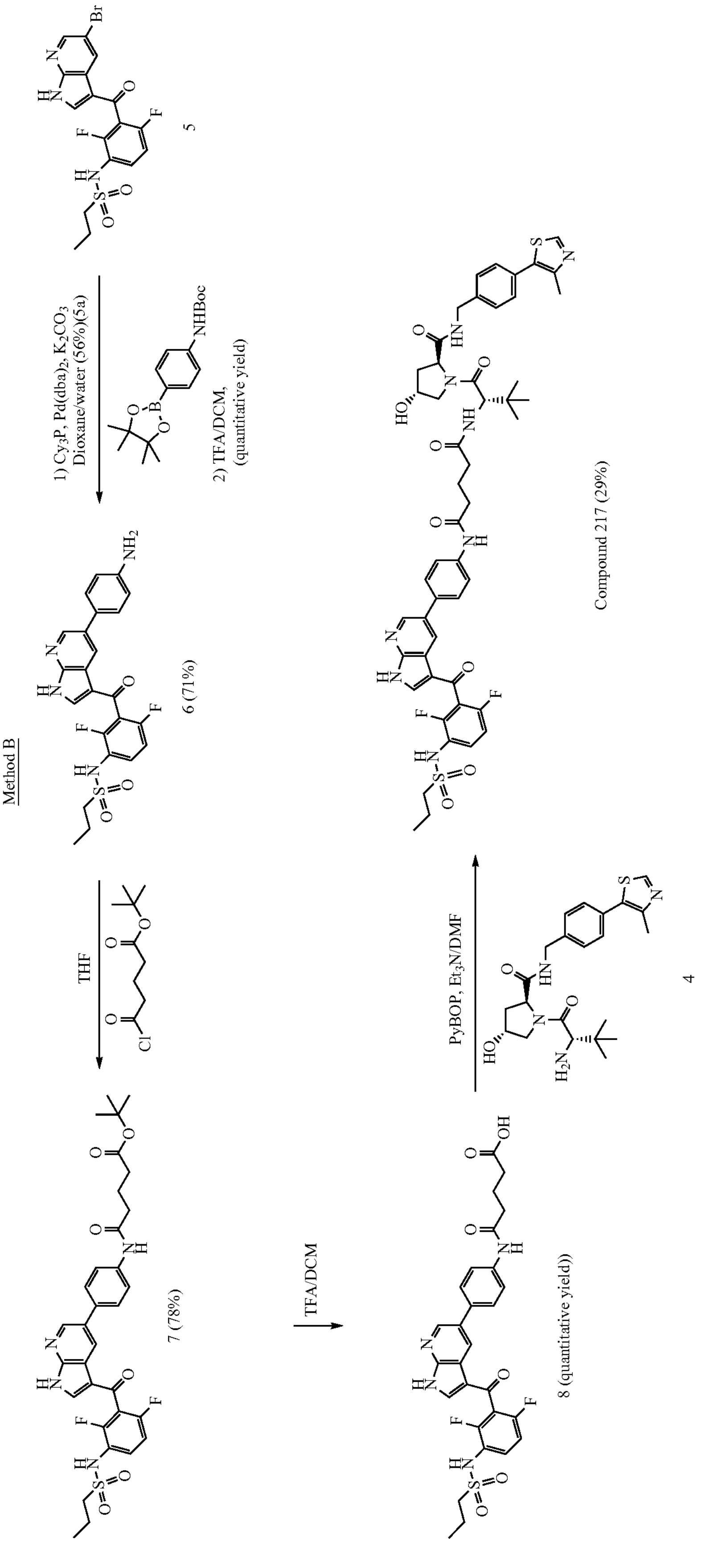
5
6 (71%)
7 (78%)
8 (quantitative yield))
4
Compound 217 (29%)

tert-Butyl(4-(3-(2,6-difluoro-3-(propylsulfonamido)benzoyl)-1H-pyrrolo[2,3-b]pyridin-5-yl)phenyl)carbamate (5a). To a solution of tert-butyl (4-(4,4,5,5-tetramethyl-1,3,2-dioxaborolan-2-yl)phenyl)-carbamate (50.99 mg, 0.16 mmol) in Dioxane (3 ml) was added N-[3-(5-bromo-1-H-pyrrolo[2,3-b]pyridine-3-carbonyl)-2,4-difluoro-phenyl] propane-1-sulfonamide (0.06 ml, 0.13 mmol), $K_2CO_3$ (55.19 mg, 0.4 mmol), Tricyclohexylphosphine (3.73 mg, 0.01 mmol) and water (1 mF). Then the reaction mixture was de-gassed under vacuum and purged with argon, $Pd(dba)_2$ (3.83 mg, 0.01 mmol) was added into and the reaction mixture was heated at 80° C. for 3 hours. By TEC small amounts of SM (Hex:AcOEt, 3:7), the reaction mixture was filtered in vacuum over a celite pad, filtrate was poured onto an aqueous saturated solution of NaCl (20 mL) and the product was extracted with EtOAc (2×20 mL). The EtOAc layers were combined, dried ($Na_2SO_4$) and concentrated in vacuum. The crude material was diluted in DCM and purified by flash chromatography ($SiO_2$-12 g, Hexane:AcOEt, gradient 8:2 to 100% AcOEt) to give 47 mg (56%) of product as a off-white solid. NMR (400 MHz, DMSO-d6) δ 12.96 (bs, 1H), 9.77 (bs, 1H), 9.49 (s, 1H), 8.68 (d, J=2.1 Hz, 1H), 8.57 (bs, 1H), 8.21 (s, 1H), 7.79-7.46 (m, 5H), 7.28 (td, J=8.7, 1.5 Hz, 1H), 3.19-3.07 (m, 2H), 1.74 (dq, J=14.9, 7.4 Hz, 2H), 1.50 (s, 9H), 0.96 (t, J=7.4 Hz, 3H). $^{13}C$ NMR (151 MHz, dmso) δ 180.61, 156.03 (dd, J=246.5, 7.1 Hz), 152.77, 152.34 (dd, J=249.5, 8.5 Hz), 148.60, 143.76, 139.22, 138.64, 131.66, 131.31, 128.79 (d, J=9.7 Hz), 127.35, 126.38, 121.94 (dd, J=13.7, 3.6 Hz), 118.66, 118.24 (t, J=23.5 Hz), 117.53, 115.63, 112.35 (dd, J=22.6, 3.9 Hz), 79.19, 53.46, 28.15, 16.85, 12.62. LC-MS (ESI); m/z: $[M+H]^+$ Calcd. for $C_{28}H_{29}F_2N_4O_5S$, 571.1826. Found 571.1917.

N-(3-(5-(4-aminophenyl)-1H-pyrrolo[2,3-b]pyridine-3-carbonyl)-2,4-difluorophenyl)propane-1-sulfonamide (6). To a solution of tert-butyl (4-(3-(2,6-difluoro-3-(propylsulfonamido)benzoyl)-1H-pyrrolo-[2,3-b]pyridin-5-yl)phenyl)carbamate (30 mg, 0.05 mmol) in TFE (2 mL) was heated at 140° C., for 3 hours under microwave assisted conditions. The reaction mixture was evaporated to dryness under vacuum, to give 23 mg of product in quantitative yields. The crude product was used in the next step without any further purification. LC-MS (ESI); m/z: $[M+H]^+$ Calcd. for $C_{23}H_{21}F_2N_4O_3S$, 471.1302. Found 471.1351.

tert-Butyl-5-((4-(3-(2,6-difluoro-3-(propylsulfonamido)benzoyl)-1H-pyrrolo[2,3-b]pyridin-5-yl)phenyl)amino)-5-oxopentanoate (7). To a solution of tert-butyl 5-chloro-5-oxopentanoate (21.96 mg, 0.11 mmol) in THF (2 mL) was added N-(3-(5-(4-aminophenyl)-1H-pyrrolo[2,3-b]-pyridine-3-carbonyl)-2,4-difluorophenyl)propane-1-sulfonamide (10 mg, 0.02 mmol). The resulting suspension was heated to reflux for 12 hours (overnight). The reaction mixture was evaporated in vacuum and the crude product was purified by PTLC (MB:DCM, 4:6) to give a white powder 10.7 mg (79% yield). $^1H$ NMR (500 MHz, DMSO-d6) δ 12.96 (bs, 1H), 10.04 (s, 1H), 9.76 (bs, 1H), 8.69 (d, J=2.2 Hz, 1H), 8.59 (s, 1H), 8.21 (s, 1H), 7.75 (d, J=8.7 Hz, 2H), 7.69 (d, J=8.6 Hz, 2H), 7.59 (td, J=9.0, 5.8 Hz, 1H), 7.28 (t, J=9.2 Hz, 1H), 3.13 (dd, J=8.7, 6.7 Hz, 2H), 2.39 (t, J=7.4 Hz, 2H), 2.28 (t, J=7.4 Hz, 2H), 1.83 (p, J=7.4 Hz, 2H), 1.75 (h, J=7.5 Hz, 2H), 1.41 (s, 9H), 0.96 (t, J=7.4 Hz, 3H). $^{13}C$ NMR (101 MHz, dmso) δ 181.01, 172.37, 171.16, 156.02 (dd, J=246.3, 7.0 Hz), 152.34 (dd, J=249.5, 8.5 Hz), 149.05, 144.18, 139.30, 139.05, 133.00, 131.62, 128.77 (d, J=9.5 Hz), 127.75, 126.88, 121.96 (dd, J=13.7, 3.5 Hz), 120.04, 118.74-117.84 (m), 117.94, 116.05, 112.34 (dd, J=22.8, 3.0 Hz). 79.98, 53.89, 35.72, 34.53, 28.20, 20.93, 17.25, 13.02. LC-MS (ESI); m/z: $[M+H]^+$ Calcd. for $C_{32}H_{35}F_2N_4O_6S$, 641.2245. Found 641.2473.

5-((4-(3-(2,6-difluoro-3-(propylsulfonamido)benzoyl)-1H-pyrrolo[2,3-b]pyridin-5-yl)phenyl)amino)-5-oxopentanoic acid (8). A solution of tert-butyl 5-((4-(3-(2,6-difluoro-3-(propylsulfonamido)benzoyl)-1H-pyrrolo[2,3-b] pyridin-5-yl)phenyl)amino)-5-oxopentanoate (10.7 mg, 0.02 mmol) in a mixture of TFA (1 ml, 13.46 mmol) and Dichloromethane (2 ml) was stirred for 2 hours. Then the solvent was removed under vacuum and crude product was dried under high vacuum for 2 hours. Crude product was used in the next step without any further purification (9.7 mg, quantitative yield). FC-MS (ESI); m/z: $[M+H]^+$ Calcd. for $C_{28}H_{27}F_2N_4O_6S$, 585.1619. Found 585.1636.

N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)glutaramide (Compound 217). To a solution of 5-((4-(3-(2,6-difluoro-3-(propylsulfonamido)-benzoyl)-1H-pyrrolo[2,3-b]pyridin-5-yl)phenyl)amino)-5-oxopentanoic acid (9.7 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.52 mg, 0.02 mmol) in DMF (1 ml) was added TEA (0.1 ml, 0.72 mmol) and PyBOP (9.5 mg, 0.02 mmol) at room temperature. The reaction mixture was stirred for 4 hours at the same temperature. TEC (DCM:MeOH:$NH_4OH$, 90:9:1) shows no starting materials. The reaction mixture was diluted with EtOAc (10 mF) and washed with brine (5 mF, 4×), organic phase was dried ($Na_2SO_4$), and evaporated under vacuum. Crude product was purified by PTFC (DCM:MeOH:$NH_4OH$, 90:9:1) to give 4.8 mg of product (29% yield). NMR (500 MHz, DMSO-d6) δ 10.02 (s, 1H), 8.97 (s, 1H), 8.68 (d, 1H), 8.64-8.52 (m, 2H), 8.21 (s, 1H), 7.95 (d, J=9.2 Hz, 1H), 7.72 (dd, J=36.7, 8.5 Hz, 4H), 7.62-7.54 (m, 1H), 7.40 (dd, 4H), 7.28 (t, J=8.7 Hz, 1H), 5.16 (d, 2H), 4.56 (d, J=9.3 Hz, 1H), 4.50-4.40 (m, 2H), 4.40-4.33 (m, 1H), 4.22 (dd, J=15.8, 5.3 Hz, 1H), 3.76-3.62 (m, 2H), 3.16-3.05 (m, 2H), 2.44 (s, 3H), 2.41-2.17 (m, 4H), 2.09-2.01 (m, 1H), 1.98-1.80 (m, 3H), 1.74 (dq, J=14.9, 7.4 Hz, 2H), 0.96 (s, 9H), 0.95 (t, 3H). $^{13}C$ NMR (151 MHz, dmso) δ 181.06, 172.39, 172.17, 171.46, 170.15, 156.37 (dd, J=246.6, 6.3 Hz), 152.73 (dd, J=249.4, 8.1 Hz), 151.86, 149.05, 148.13, 144.19, 139.91, 139.37, 139.13, 132.97, 131.64, 131.59, 130.05, 129.22 (d, J=14.7 Hz), 129.06, 127.84, 127.74, 126.89, 122.47 (d, J=14.1 Hz), 120.07, 119.02-118.20 (m), 117.95, 116.06, 112.75 (dd, J=23.4, 2.8 Hz), 69.34, 59.15, 56.90, 56.81, 53.87, 42.08, 38.38, 36.36, 35.63, 34.63, 26.85, 21.91, 17.27, 16.37, 13.04. LC-MS (ESI); m/z $[M+H]^+$: Calcd. for $C_{50}H_{55}F_2N_8O_8S_2$, 997.3552. Found 997.3524.

N1-(4-(3-(2,6-difluoro-3-(propylsulfonamido)benzoyl)-1H-pyrrolo[2,3-b]pyridin-5-yl)phenyl)-N4-((S)-1-((2S,4R)-4-hydroxy-2-((4-(4-methylthiazol-5-yl)benzyl)carbamoyl)pyrrolidin-1-yl)-3,3-dimethyl-1-oxo-butan-2-yl)-N1-methylsuccinamide (Compound 510)

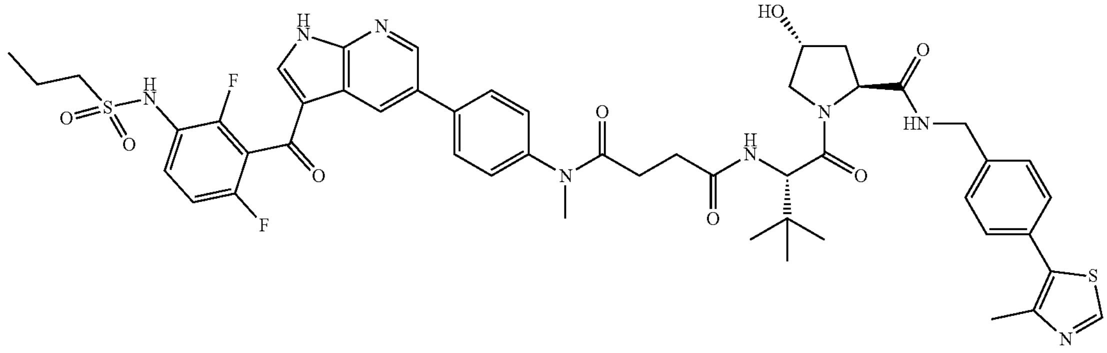 [SMILES: CCCS(=O)(=O)Nc1ccc(F)c(C(=O)c2c[nH]c3ncc(-c4ccc(N(C)C(=O)CCC(=O)N[C@H](C(=O)N5C[C@H](O)C[C@H]5C(=O)NCc5ccc(-c6scnc6C)cc5)C(C)(C)C)cc4)cc23)c1F]

To a solution of 4-[4-[3-[2,6-difluoro-3-(propylsulfonylamino)-benzoyl]-1H-pyrrolo[2,3-b]pyridin-5-yl]-N-methyl-anilino]-4-oxo-butanoic acid (33.7 mg, 0.06 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (4) (32.31 mg, 0.07 mmol) in DMF (2 ml) was added TEA (0.2 ml, F43 mmol) and PyBOP (36 mg, 0.07 mmol) at room temperature. The reaction mixture was stirred for 4 h at the same temperature. TEC (DCM:MeOH:$NH_4OH$, 90:9:1) shows some starting material (acid). The reaction mixture was evaporated to dryness under high vacuum. Crude product was purified by PTLC (DCM:MeOH:$NH_4OH$, 90:9:1) to give 4.6 mg of product (8% yield). NMR (400 MHz, DMSO-d6) δ 13.01 (bs, 1H), 9.70 (bs, 1H), 8.95 (s, 1H), 8.73 (d, J=2.3 Hz, 1H), 8.66 (bs, 1H), 8.54 (t, J=5.9 Hz, 1H), 8.22 (s, 1H), 7.84 (dd, J=19.4, 8.6 Hz, 2H), 7.57 (td, J=9.0, 6.1 Hz, 1H), 7.52-7.30 (m, 6H), 7.26 (t, J=8.5 Hz, 1H), 5.08 (d, J=3.2 Hz, 1H), 4.47 (d, J=9.2 Hz, 1H), 4.44-4.25 (m, 3H), 4.19 (dd, J=16.0, 5.4 Hz, 1H), 3.66-3.54 (m, 2H), 3.19 (s, 3H), 3.16-3.00 (m, 2H), 2.75-2.16 (m, 4H), 2.42 (s, 3H), 2.06-1.96 (m, 1H), 1.93-1.80 (m, 1H), 1.79-1.64 (m, 2H), 0.94 (t, 3H), 0.90 (s, 9H). $^{13}C$ NMR (151 MHz, DMSO-d6) δ 181.08, 172.37, 171.90, 171.57, 170.00, 156.45 (dd, J=246.4, 7.0 Hz), 152.76 (dd, J=249.3, 8.9 Hz), 151.88, 149.37, 148.13, 144.49, 143.73, 139.91, 139.34, 137.64, 131.59, 131.11, 130.04, 129.53-129.16 (m), 129.06, 127.84, 127.55, 122.35 (d, J=15.0 Hz), 119.06-118.23 (m), 117.93, 116.13, 112.77 (d, J=22.0 Hz), 69.31, 59.13, 56.87, 56.75, 53.86, 42.07, 38.32, 35.76, 30.61, 29.66, 26.77, 22.93, 17.26, 16.37, 13.04. LC-MS (ESI); m/z $[M+H]^+$: Calcd. for $C_{50}H_{55}F_2N_8O_8S_2$, 997.3552. Found 997.3572.

Example 17-Synthetic Scheme C: Compound 218, 219, and 222

Method C
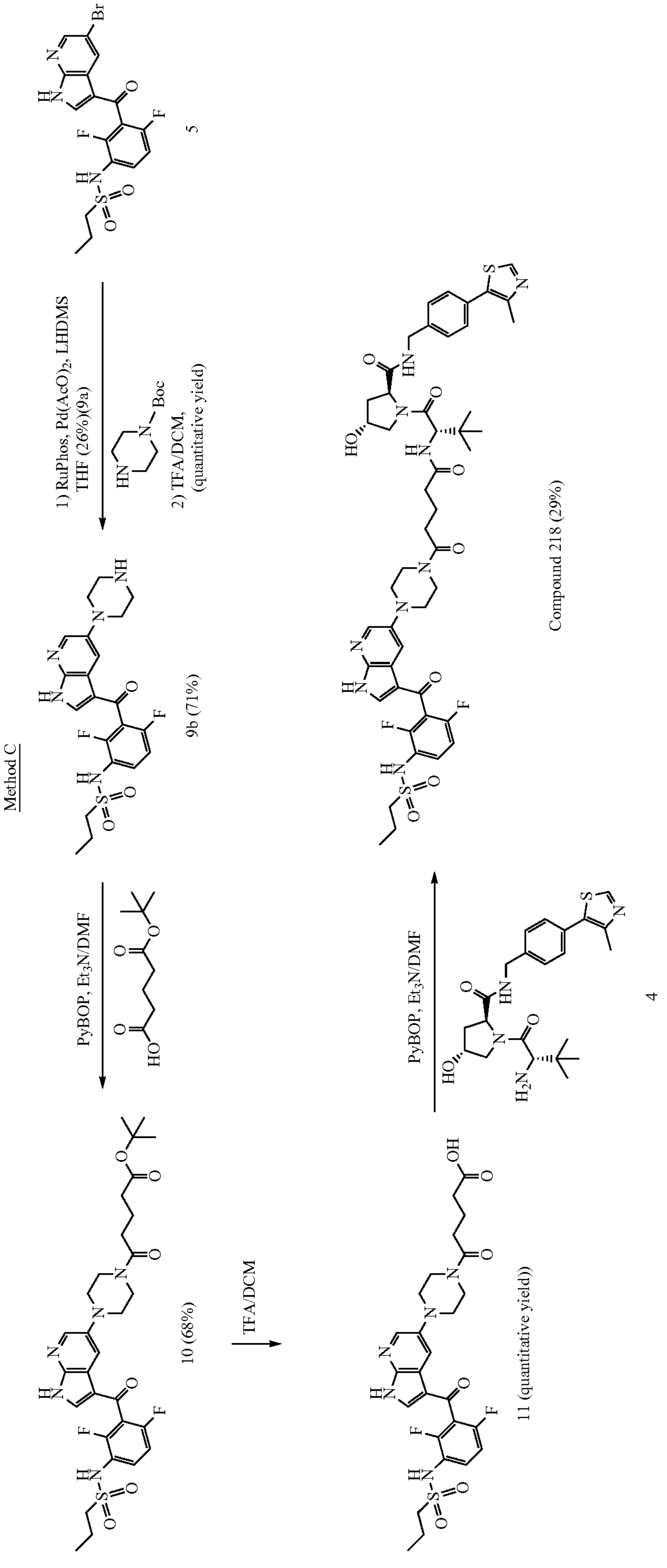
5
9b (71%)
10 (68%)
11 (quantitative yield))
4
Compound 218 (29%)

tert-Butyl 4-(3-(2,6-difluoro-3-(propylsulfonamido)benzoyl)-1H-pyrrolo[2,3-b]pyridin-5-yl)piperazine-1-carboxylate (9a). A solution of N-[3-(5-bromo-1H-pyrrolo[2,3-b]pyridine-3-carbonyl)-2,4-difluoro-phenyl]propane-1-sulfonamide (61 mg, 0.13 mmol) and tert-butyl piperazine-1-carboxylate (37.19 mg, 0.2 mmol) in THF (3 mF) was purged with argon (5×). RuPhos (18.63 mg, 0.04 mmol) and $Pd(OAc)_2$ (2.99 mg, 0.01 mmol) were added followed by 1 M FHMDS in THF (0.53 ml) The reaction mixture was heated to 60° C. and stirred for 6 hours. The reaction was cooled and poured into an aqueous solution of oxalic acid (5%, 2 ml), then a saturated aqueous $NaHCO_3$ solution was added (5 ml), the product was extracted with DCM (3×10 ml). Organic extracts were combined, dried (Na2SO4) and evaporated under vacuum. Crude product was purified by PTFC (DCM:MeOH:$NH_4OH$, 90:9:1) (20 mg, 26%). $^1H$ NMR (400 MHz, DMSO-d6) δ 12.61 (bs, 1H), 9.73 (bs, 1H), 8.27 (d, J=2.6 Hz, 1H), 8.03 (s, 1H), 7.94 (bs, 1H), 7.57 (td, J=9.0, 5.9 Hz, 1H), 7.26 (td, J=8.7, F5 Hz, 1H), 3.63-3.46 (m, 4H), 3.42-3.24 (m, 4H), 3.20-3.06 (m, 2H), F74 (dq, J=15.0, 7.4 Hz, 2H), F43 (s, 9H), 0.96 (t, J=7.4 Hz, 3H). $^{13}C$ NMR (101 MHz, dmso) δ 180.37, 155.96 (dd, J=246.2, 7.2 Hz), 153.87, 152.31 (dd, J=249.1, 8.6 Hz), 144.72, 144.31, 138.06, 137.78, 128.59 (d, J=7.8 Hz), 121.94 (dd, J=13.6, 3.7 Hz), 119.35-117.93 (m), 117.56, 115.58, 115.17, 112.25 (dd, J=22.7, 3.8 Hz), 79.01, 53.49, 50.03, 43.56, 28.07, 16.84, 12.61. LC-MS (ESI); m/z: $[M+H]^+$ Calcd. for $C_{26}H_{32}F_2N_5O_5S$, 564.2092. Found 564.2

N-(2,4-difluoro-3-(5-(piperazin-1-yl)-1H-pyrrolo[2,3-b]pyridine-3-carbonyl)phenyl)propane-1-sulfonamide (9b). A solution of tert-butyl 4-(3-(2,6-difluoro-3-(propylsulfonamido)benzoyl)-1H-pyrrolo-[2,3-b]pyridin-5-yl)piperazine-1-carboxylate (20 mg, 0.04 mmol) in a mixture of DCM:TFA (3 mF: 1 mF) was stirred for 1 hour at room temperature. By TFC no more starting material (DCM:MeOH:$NH_4OH$, 90:9:1). 16.4 mg of product (quantitative yield), crude product was used in the next step without any further purification. FC-MS (ESI); m/z $[M+H]^+$: Calcd. for $C_{21}H_{24}F_2N_5O_3S$, 464.1567. Found 464.1712.

tert-butyl 5-(4-(3-(2,6-difluoro-3-(propylsulfonamido)benzoyl)-1H-pyrrolo[2,3-b]pyridin-5-yl)piperazin-1-yl)-5-oxopentanoate (10). To a solution of N-(2,4-difluoro-3-(5-(piperazin-1-yl)-1H-pyrrolo[2,3-b]pyridine-3-carbonyl)-phenyl)propane-1-sulfonamide (16.4 mg, 0.04 mmol) and 5-(tert-butoxy)-5-oxopentanoic acid (7.99 mg, 0.04 mmol) in DMF (2 ml) was added TEA (0.1 ml, 0.72 mmol) and PyBOP (20.25 mg, 0.04 mmol) at room temperature. The reaction mixture was stirred for 3 hours at the same temperature. TFC (DCM:MeOH:$NH_4OH$, 90:9:1) shows no starting materials. The reaction mixture was dissolved in EtOAc (10 mF) and washed with brine/water (3×5 mF). Organic extract was concentrated under vacuum and crude product was purified by PTFC (DCM:MeOH:$NH_4OH$, 90:9:1) to give 15.4 mg of product (69% yield). NMR (400 MHz, DMSO-d6) δ 12.67 (bs, 1H), 9.71 (bs, 1H), 8.29 (s, 1H), 8.03 (s, 1H), 7.95 (s, 1H), 7.56 (q, J=8.8 Hz, 1H), 7.26 (t, J=8.7 Hz, 1H), 3.71-3.57 (m, 4H), 3.24-3.06 (m, 6H), 2.39 (t, J=7.3 Hz, 2H), 2.26 (t, J=7.3 Hz, 2H), 1.84-1.66 (m, 4H), 1.40 (s, 9H), 0.96 (t, J=7.4 Hz, 3H). $^{13}C$ NMR (101 MHz, dmso) δ 180.79, 172.52, 170.57, 156.37 (dd, J=246.4, 7.1 Hz), 152.72 (dd, J=249.2, 8.7 Hz), 145.03, 144.70, 138.44, 138.20, 129.01 (d, J=10.4 Hz), 122.34 (dd, J=13.7, 3.7 Hz), 119.28-118.29 (m), 117.97, 115.84, 115.58, 112.66 (dd, J=22.8, 3.3 Hz), 79.92, 53.89, 50.66, 45.18, 41.39, 34.57, 31.72, 28.21, 20.83, 17.25, 13.02. FC-MS (ESI); m/z $[M+H]^+$: Calcd. for $C_{30}H_{38}F_2N_5O_6S$, 634.2510. Found 634.2621.

5-((4-(3-(2,6-difluoro-3-(propylsulfonamido)benzoyl)-1H-pyrrolo[2,3-b]pyridin-5-yl)phenyl)amino)-5-oxopentanoic acid (11). A solution of tert-butyl 5-((4-(3-(2,6-difluoro-3-(propylsulfonamido)benzoyl)-1H-pyrrolo[2,3-b]pyridin-5-yl)phenyl)amino)-5-oxopentanoate (10.7 mg, 0.02 mmol) in a mixture of TFA (1 ml, 13.46 mmol) and Dichloromethane (2 ml) was stirred for 2 hours at room temperature. Then the solvent was removed under vacuum and crude product was dried under high vacuum for 2 hours. Crude product was used in the next step without any further purification (9.7 mg, quantitative yield). LC-MS (ESI); m/z: $[M+H]^+$ Calcd. for $C_{28}H_{27}F_2N_4O_6S$, 585.1619. Found 585.1636.

(2S,4R)-1-((S)-2-(5-(4-(3-(2,6-difluoro-3-(propylsulfonamido)benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide (Compound 218). To a solution of 5-(4-(3-(2,6-difluoro-3-(propylsulfonamido)-benzoyl)-1H-pyrrolo[2,3-b]pyridin-5-yl)piperazin-1-yl)-5-oxopentanoic acid (9.3 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.27 mg, 0.018 mmol) in DMF (1 ml) was added TEA (0.1 ml, 0.72 mmol) and PyBOP (9.22 mg, 0.018 mmol) at room temperature. The reaction mixture was stirred for 4 hours at the same temperature. TLC (DCM:MeOH:$NH_4OH$, 90:9:1) shows no starting materials. The reaction mixture was diluted with EtOAc (10 mL) and washed with brine (5 mL, 4×), organic phase was dried ($Na_2SO_4$), and evaporated under vacuum. Crude mixture did not show product by TLC, just some VHL starting material (4) (Product is soluble in water). Water extracts were lyophilized for overnight, the solid residue was filtered using a mixture of DCM:MeOH:$NH_4OH$ (90:9:1, 30 mL). Filtrate was evaporated to dryness and crude product was purified by PTLC (DCM:MeOH:$NH_4OH$, 90:9:1) to give 13 mg of product (81% yield). NMR (500 MHz, DMSO-d6) δ 12.64 (bs, 1H), 9.74 (bs, 1H), 8.97 (s, 1H), 8.62-8.52 (m, 3H), 8.28 (d, J=2.0 Hz, 1H), 8.00 (s, 1H), 7.95 (bs, 1H), 7.90 (d, J=9.2 Hz, 1H), 7.59-7.49 (m, 1H), 7.47-7.27 (m, 4H), 7.20 (t, J=8.7 Hz, 1H), 5.13 (bs, 1H), 4.56 (d, J=9.3 Hz, 1H), 4.48-4.32 (m, 3H), 4.22 (dd, J=15.8, 5.3 Hz, 1H), 3.75-3.57 (m, 5H), 3.23-3.02 (m, 7H), 2.44 (s, 3H), 2.41-2.17 (m, 4H), 2.07-2.01 (m, 1H), 1.96-1.87 (m, 1H), 1.81-1.66 (m, 4H), 0.95 (s, 9H), 0.94 (t, 3H). $^{13}C$ NMR (151 MHz, dmso) δ 180.70, 171.99, 171.92, 170.44, 169.75, 155.24 (dd, J=248.1, 5.5 Hz), 152.12 (dd, J=248.8, 8.5 Hz), 151.47, 147.73, 144.63, 144.31, 139.52, 138.02, 137.75, 131.19, 129.65, 128.65, 127.98-127.64 (m), 127.44, 123.91-123.09 (m), 118.86-117.72 (m), 117.60, 115.50, 115.23, 112.02 (dd, J=22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72. LC-MS (ESI); m/z $[M+H]^+$: Calcd. for $C_{48}H_{58}F_2N_9O_8S_2$, 990.3817. Found 990.3889.

Example 18-Synthetic Scheme C: compound 304, and 306

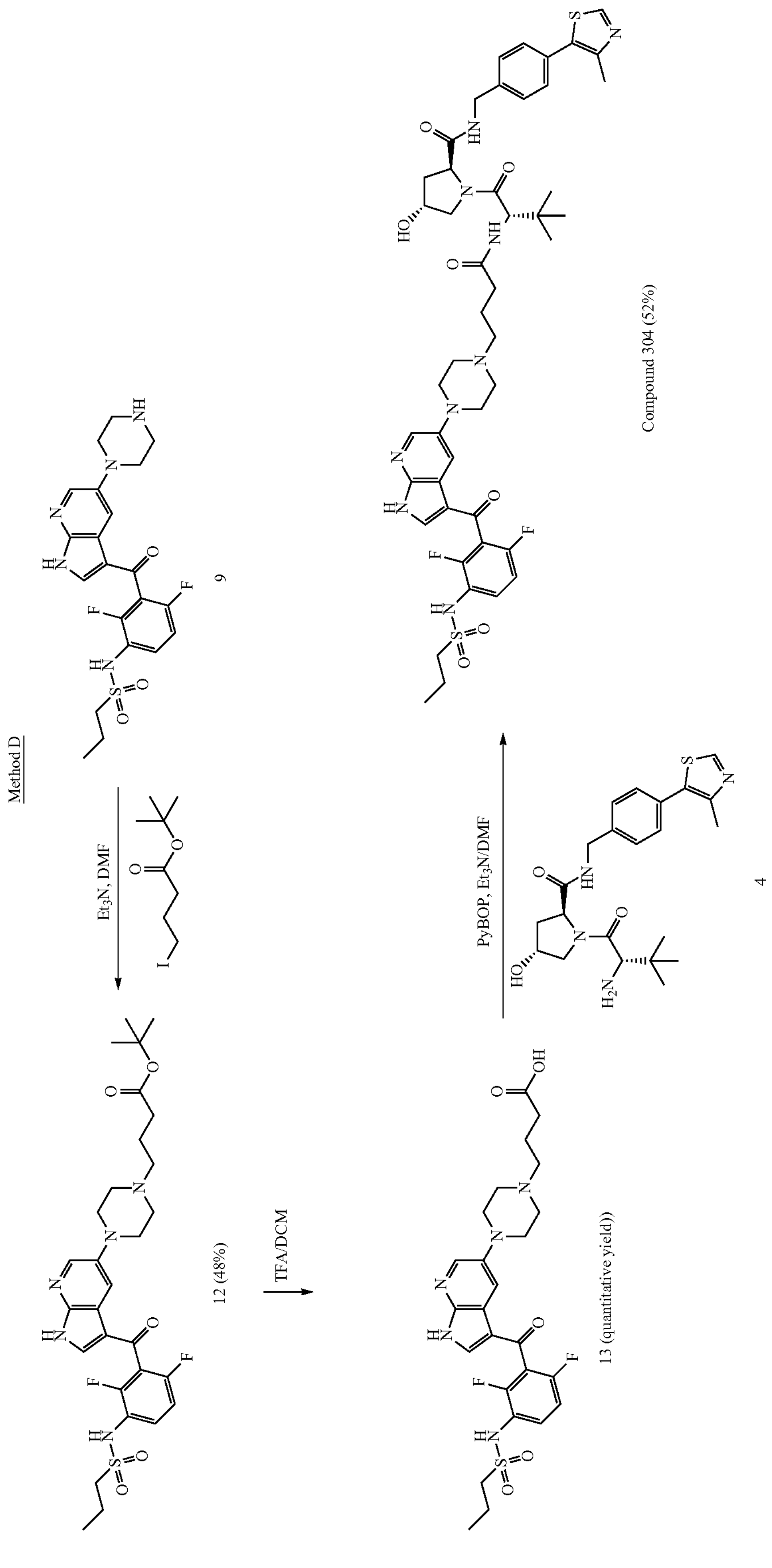
Method D
Et$_3$N, DMF
9
12 (48%)
TFA/DCM
13 (quantitative yield))
PyBOP, Et$_3$N/DMF
4
Compound 304 (52%)

tert-Butyl 4-[4-[3-[2,6-difluoro-3-(propylsulfonylamino) benzoyl]-1H-pyrrolo[2,3-b]pyridin-5-yl]piperazin-1-yl]butanoate (12). To a solution of methyl N-[2,4-difluoro-3-(5-piperazin-1-yl-1H-pyrrolo[2,3-b]-pyridine-3-carbonyl) phenyl]propane-1-sulfonamide; 2,2,2-trifluoroacetic acid (17.4 mg, 0.03 mmol) and tert-butyl 4-iodobutanoate (8.95 mg, 0.03 mmol) in DMF (1 ml) was added TEA (0.03 ml, 0.15 mmol), the resulting solution stirred for 16 hours at 50° C. (overnight). The solvent was evaporated under high vacuum and the residue was filtered over a silica-carbonate cartridge (1 g) using DCM:MeOH (9:1) as a eluent. Filtrate was evaporated under vacuum and crude product was purified by PTFC (DCM:MeOH:$NH_4OH$, 90:9:1), to give 8.8 mg of product (48% yield). $^1H$ NMR (400 MHz, DMSO-d6) δ 12.63 (bs, 1H), 9.73 (bs, 1H), 8.25 (d, J=2.7 Hz, 1H), 8.00 (s, 1H), 7.89 (bs, 1H), 7.56 (td, J=9.0, 6.0 Hz, 2H), 7.34-7.16 (m, 1H), 3.25-3.04 (m, 6H), 2.68-2.52 (m, 4H), 2.34 (t, J=7.1 Hz, 2H), 2.24 (t, J=7.2 Hz, 2H), 1.85-1.61 (m, 4H), 1.40 (s, 9H), 0.96 (t, J=7.4 Hz, 3H). $^{13}C$ NMR (151 MHz, DMSO-d6) δ 180.34, 172.23, 155.99 (dd, J=246.1, 7.0 Hz), 152.31 (dd, J=249.3, 8.6 Hz), 144.80, 143.96, 137.64, 137.36, 128.60 (d, J=9.9 Hz), 121.91 (dd, J=13.6, 3.7 Hz), 118.41 (t, J=23.8 Hz), 117.63, 115.12, 114.54, 112.26 (dd, J=22.8, 3.7 Hz), 56.95, 53.47, 52.70, 49.72, 32.69, 27.83, 21.79, 16.86, 12.63. LC-MS (ESI); m/z: $[M+H]^+$ Calcd. for $C_{29}H_{38}F_2N_5O_5S$, 606.2561. Found 606.2504.

4-[4-[3-[2,6-Difluoro-3-(propylsulfonylamino)benzoyl]-1H-pyrrolo[2,3-b]pyridin-5-yl]piperazin-1-yl]butanoic acid (13). A solution of tert-butyl 4-[4-[3-[2,6-difluoro-3-(propylsulfonylamino)benzoyl]-1H-pyrrolo[2,3-b]pyridin-5-yl] piperazin-1-yl]butanoate (8.8 mg, 0.01 mmol) in a mixture of TFA (1 ml, 13.46 mmol) and Dichloromethane (3 ml) was stirred for 1 hour. Then the solvent was removed under vacuum and crude product was dried under high vacuum for 2 hours. Crude product was used in the next step without any further purification (7.9 mg, quantitative yield). FC-MS (ESI); m/z: [M+H]+ Calcd. for $C_{25}H_{30}F_2N_5O_5S$, 550.1936. Found 550.1865.

(2S,4R)-1-((S)-2-(4-(4-(3-(2,6-difluoro-3-(propylsulfonamido)benzoyl)-1H-pyrrolo[2,3-b]pyridin-5-yl)piperazin-1-yl)butanamido)-3,3-dimethylbutanoyl)-4-hydroxy-N-(4-(4-methylthiazol-5-yl)benzyl)pyrrolidine-2-carboxamide (Compound 304). To a solution of 4-[4-[3-[2,6-difluoro-3-(propylsulfonyl-amino)benzoyl]-1H-pyrrolo[2,3-b]pyridin-5-yl]piperazin-1-yl]butanoic acid (7.9 mg, 0.01 mmol) and (2S,4R)-1-[(2S)-2-amino-3,3-dimethyl-butanoyl]-4-hydroxy-N-[[4-(4-methylthiazo-1-5-yl)phenyl]methyl]pyrrolidine-2-carboxamide;hydrochloride (7.38 mg, 0.02 mmol) in DMF (1 ml) was added TEA (0.1 ml, 0.72 mmol) and PyBOP (8.23 mg, 0.02 mmol) at room temperature. The reaction mixture was stirred for 12 hours (overnight) at the same temperature. TEC (DCM:MeOH:$NH_4OH$, 90:9:1) shows no starting materials. The reaction mixture was evaporated to dryness. Crude product was filtered over a silica-carbonate cartridge (1 g) using DCM:MeOH (9:1) as eluent (washed a few times, product has high affinity for the stationary phase). Filtrate was evaporated under vacuum and crude product was purified by PTFC (DCM:MeOH, 9:1) to give 7.2 mg of product (52% yield). NMR (500 MHz, DMSO-d6) δ 12.66 (bs, 1H), 9.73 (bs, 1H), 8.96 (s, 1H), 8.61-8.50 (m, 1H), 8.25 (s, 1H), 8.00 (s, 1H), 7.93 (bs, 1H), 7.88 (d, J=9.1 Hz, 1H), 7.63-7.49 (m, 1H), 7.40 (dd, 4H), 7.25 (t, J=8.7 Hz, 1H), 5.14 (s, 1H), 4.56 (d, J=9.1 Hz, 1H), 4.46-4.34 (m, 3H), 4.22 (dd, J=15.8, 4.7 Hz, 1H), 3.75-3.60 (m, 2H), 3.23-3.14 (m, 4H), 3.13-3.08 (m, 2H), 2.65-2.53 (m, 4H), 2.43 (s, 3H), 2.38-2.31 (m, 2H), 2.31-2.25 (m, 1H), 2.24-2.16 (m, 1H), 2.07-1.99 (m, 1H), 1.95-1.87 (m, 1H), 1.72 (dq, J=16.3, 10.5, 8.9 Hz, 4H), 0.95 (t, J=5.3 Hz, 3H), 0.95 (s, 9H). $^{13}C$ NMR (151 MHz, DMSO-d6) δ 180.77, 172.43, 172.39, 170.12, 156.38 (dd, J=246.2, 7.1 Hz), 152.75 (dd, J=249.8, 9.0 Hz), 151.87, 148.13, 145.23, 144.35, 139.92, 138.09, 137.78, 131.59, 130.05, 129.21-128.76 (m), 127.84, 122.32 (d, J=13.1 Hz), 119.83-118.25 (m), 118.03, 115.53, 114.96, 112.68 (d, J=22.7 Hz), 69.30, 59.13, 57.62, 56.79, 55.33, 53.88, 53.06, 50.11, 42.07, 38.38, 35.68, 33.27, 26.83, 23.09, 17.26, 16.37, 13.04. LC-MS (ESI); m/z $[M+H]^+$: Calcd. for $C_{47}H_{58}F_2N_9O_7S_2$, 962.3868. Found 962.3986.

Example 19-Synthetic Scheme E: Compound 511, and 513

Method E
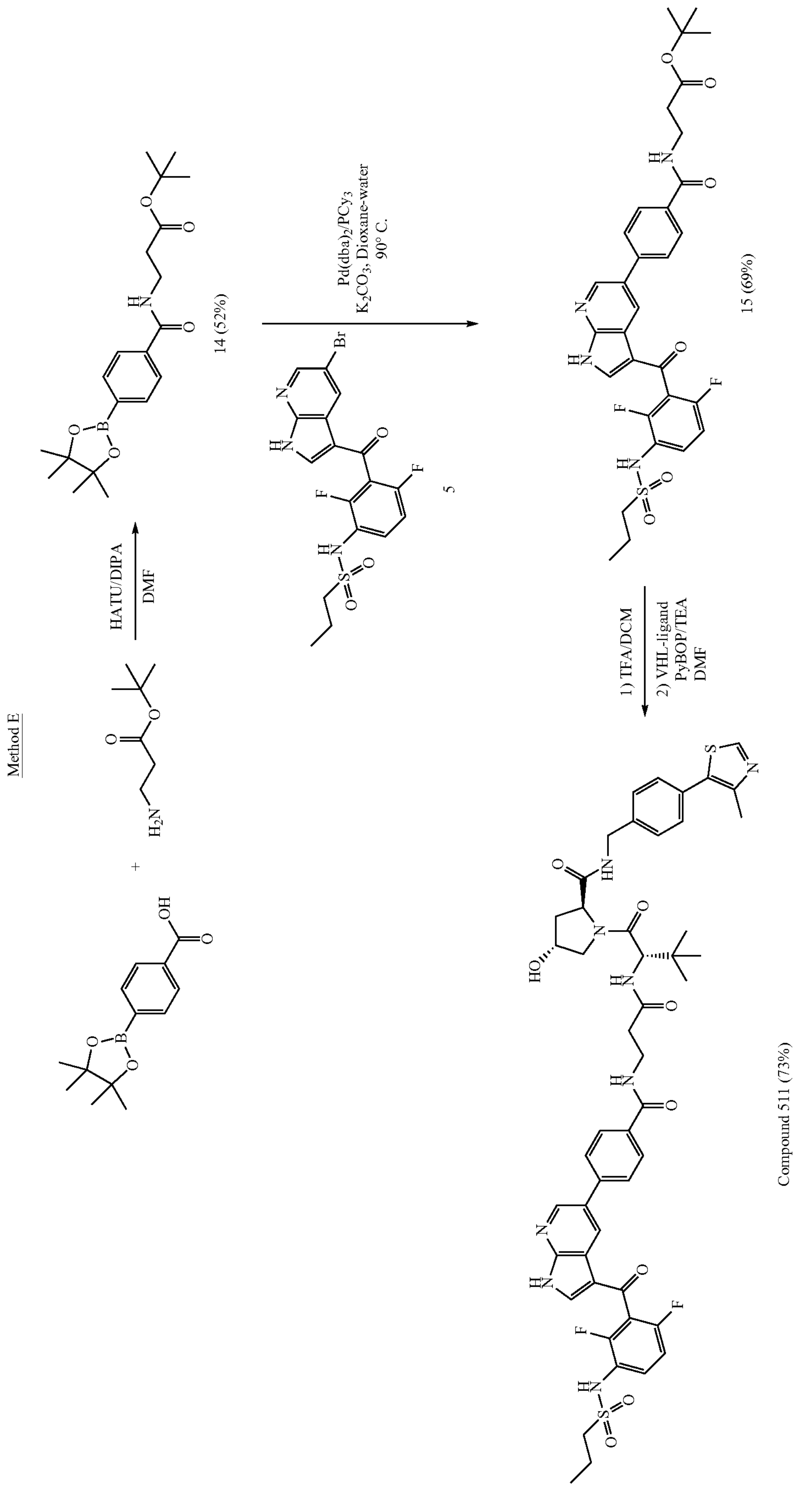
14 (52%)
5
15 (69%)
Compound 511 (73%)

tert-butyl 3-(4-(4,4,5,5-tetramethyl-1,3,2-dioxaborolan-2-yl)benzamido)propanoate (14)

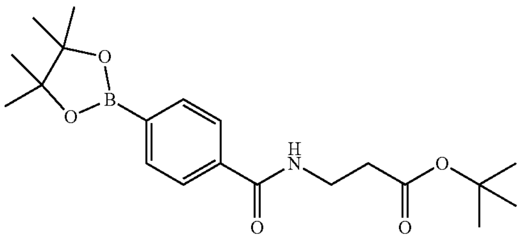 [SMILES: CC(C)(C)OC(=O)CCNC(=O)c1ccc(B2OC(C)(C)C(C)(C)O2)cc1]

To a solution of 4-(4,4,5,5-tetramethyl-1,3,2-dioxaborolan-2-yl)benzoic acid (538 mg, 2.17 mmol) and tert-butyl 3-aminopropanoate (315 mg, 2.17 mmol) in N,N-Dimethylformamide (10 ml) was added N,N-Diisopropylethylamine (1.13 mL, 6.51 mmol) and O-(7-Azabenzotriazol-1-yl)-N,N,N',N'-tetramethyluronium hexafluorophosphate (825 mg, 2.17 mmol) at room temperature. The reaction mixture was stirred for 4 h at the same temperature. TLC (DCM:MeOH:$NH_4OH$, 90:9:1) shows no starting materials. Reaction mixture was diluted with EtOAc (50 mL), washed with water/brine (4×30 mL), dried ($Na_2SO_4$) and evaporated under vacuum. Crude product was purified by flash chromatography ($SiO_2$-25 g, gradient Hex:EtOAc, 1:9 to 100% EtOAc in 15 min), to give 471 mg of product (~90% pure by NMR, 52% yield). This product was used in the next step without any further purification. $^1H$ NMR (500 MHz, Chloroform-d) δ 7.86 (d, J=7.9 Hz, 2H), 7.74 (d, J=7.9 Hz, 2H), 6.87 (t, 1H) z 3.69 (q, J=5.9 Hz, 2H), 2.56 (t, J=5.8 Hz, 2H), 1.45 (s, 9H), 1.35 (s, 12H). LC-MS (ESI); m/z $[M+H]^+$: Calcd. for $C_{20}H_{31}BNO_5$, 376.2295. Found 376.2259.

tert-butyl 3-(4-(3-(2,6-difluoro-3-(propylsulfonamido)benzoyl)-1H-pyrrolo[2,3-b]pyridin-5-yl)benzamido)-propanoate (15)

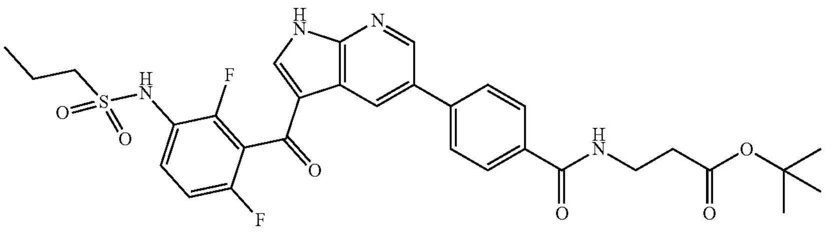 [SMILES: CCCS(=O)(=O)Nc1ccc(F)c(C(=O)c2c[nH]c3ncc(-c4ccc(C(=O)NCCC(=O)OC(C)(C)C)cc4)cc23)c1F]

To a solution of N-[3-(5-bromo-1H-pyrrolo[2,3-b]pyridine-3-carbonyl)-2,4-difluoro-phenyl]propane-1-sulfonamide (5) (87.3 mg, 0.191 mmol) in Dioxane (6 ml) was added tert-butyl 2-[2-[2-[2-[4-(4,4,5,5-tetramethyl-1,3,2-dioxaborolan-2-yl)phenoxy]ethoxy]ethoxy]ethoxy]acetate (14) (65.0 mg, 0.173 mmol), $K_2CO_3$ (71.8 mg, 0.520 mmol), Tricyclohexyl phosphine (4.86 mg, 0.017 mmol) and water (2 mL). Then the reaction mixture was de-gassed under vacuum and purged with argon (5×), $Pd(dba)_2$ (4.98 mg, 0.080 mmol) was added into and the reaction mixture was heated at 90° C. for 3 h. By TLC small amounts of SM (Hex:EtOAc, 3:7), the reaction mixture was filtered in vacuum over a celite pad, filtrate was poured into an aqueous saturated solution of NaCl (20 mL) and the product was extracted with EtOAc (2×20 mL). The EtOAc layers were combined, dried ($Na_2SO_4$) and concentrated in vacuum. The crude material was diluted in $CH_2Cl_2$ and purified by flash chromatography ($SiO_2$-12 g, Hexane:EtOAc, 9:1 to 100% EtOAc in 15 min) to give 75 mg (71%) of product. $^{13}C$ NMR (101 MHz, DMSO-d6) δ 181.08, 171.05, 166.24, 156.44 (dd, J=246.3, 6.9 Hz), 152.76 (dd, J=249.7, 8.2 Hz), 149.55, 144.57, 141.15, 139.40, 133.71, 130.98, 129.65-128.79 (m), 128.43, 127.64, 127.55-126.10 (m), 122.66-122.12 (m), 119.00-118.20 (m), 117.93, 116.15, 112.78 (dd, J=22.9, 3.5 Hz), 80.28, 53.88, 36.10, 35.45, 28.17, 17.25, 13.03. $^1H$ NMR (500 MHz, DMSO-d6) δ 13.03 (bs, 1H), 9.76 (bs, 1H), 8.78 (s, 1H), 8.69 (s, 1H), 8.61 (t, J=4.6 Hz, 1H), 8.26 (s, 1H), 7.98 (d, J=7.1 Hz, 2H), 7.87 (d, J=7.2 Hz, 2H), 7.59 (q, J=7.6 Hz, 1H), 7.29 (t, J=8.7 Hz, 1H), 3.50 (q, J=5.7 Hz, 2H), 3.13 (t, 2H), 2.64-2.44 (m, 2H), 1.74 (dq, J=13.9, 7.3 Hz, 2H), 1.40 (s, 9H), 0.96 (t, J=7.4 Hz, 3H). LC-MS (ESI); m/z $[M+H]^+$: Calcd. for $C_{31}H_{33}F_2N_4O_6S$, 627.2088. Found 627.2485.

(2S,4R)-1-((S)-2-(3-(4-(3-(2,6-difluoro-3-(propylsulfonamido)benzoyl)-1H-pyrrolo[2,3-b]pyridin-5-yl)-benzamido)propanamido)-3,3-dimethylbutanoyl)-4-hydroxy-N-(4-(4-methylthiazol-5-yl)benzyl)pyrrole-dine-2-carboxamide (Compound 511)

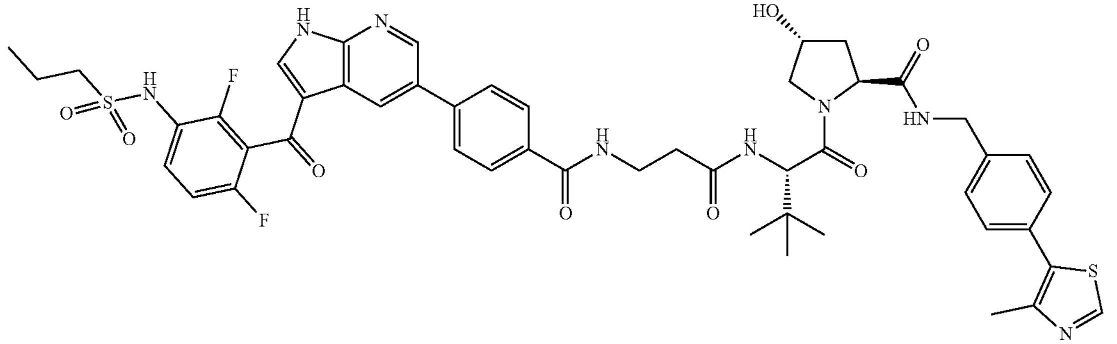 [SMILES: CCCS(=O)(=O)Nc1ccc(F)c(C(=O)c2c[nH]c3ncc(-c4ccc(C(=O)NCCC(=O)N[C@H](C(=O)N5C[C@H](O)C[C@H]5C(=O)NCc5ccc(-c6scnc6C)cc5)C(C)(C)C)cc4)cc23)c1F]

A solution of tert-butyl 4-[4-(3-benzoyl-1H-pyrrolo[2,3-b]pyridin-5-yl)phenoxy]butanoate (15) (26.0 mg, 0.0415 mmol) in a mixture of TFA (1 ml, 13.46 mmol) and Dichloromethane (3 ml) was stirred for F5 h. Then the solvent was removed under vacuum and crude product was dried under high vacuum for 2 h. Crude product was used in the next step without any further purification (23.5 mg, quantitative yield). FS-MS (ESI); m/z: $[M+H]^+$ Calcd. for $C_{27}H_{25}F_2N_4O_6S$, 571.1462. Found 571.1812. To a solution of crude product from above; 4-[4-[3-[2,6-difluoro-3-(propylsulfonylamino)benzoyl]-1H-pyrrolo[2,3-b]pyridin-5-yl]-N-methyl-anilino]-4-oxo-butanoic acid (23.5 mg, 0.0402 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (4) (21.0 mg, 0.0450 mmol) in DMF (1 ml) was added TEA (0.139 mF, 1.00 mmol) and PyBOP (23.4 mg, 0.0450 mmol) at room temperature. The reaction mixture was stirred for 4 h at the same temperature. TEC (DCM:MB, 1:1) shows no starting material (acid). The reaction mixture was evaporated to dryness under high vacuum (Product may be soluble in water). Crude product was filtered over a silica-carbonate cartridge (100 mg) using DCM:MeOH (9:1) as a eluent. Filtrate was evaporated under vacuum and crude product was purified by PTFC (MBFDCM, 1:1). A second purification was performed by PTFC (DCM:MeOH:$NH_4OH$, 90:9:1), to give 27 mg of product (73% yield). $^1H$ NMR (500 MHz, DMSO-d6) δ 13.03 (bs, 1H), 9.77 (bs, 1H), 8.96 (s, 1H), 8.77 (s, 1H), 8.69 (s, 1H), 8.57 (t, J=5.7 Hz, 1H), 8.53 (t, J=4.9 Hz, 1H), 8.26 (s, 1H), 8.03 (d, J=9.1 Hz, 1H), 7.98 (d, J=8.0 Hz, 1H), 7.86 (d, J=8.0 Hz, 1H), 7.59 (q, J=8.8 Hz, 1H), 7.40 (dd, 4H), 7.28 (t, J=8.6 Hz, 1H), 5.16 (d, J=2.8 Hz, 1H), 4.58 (d, J=9.1 Hz, 1H), 4.50-4.34 (m, 3H), 4.22 (dd, J=15.8, 5.1 Hz, 1H), 3.80-3.61 (m, 2H), 3.58-3.40 (m, 2H), 3.15-3.06 (m, 2H), 2.69-2.49 (m, 2H), 2.43 (s, 3H), 2.11-1.99 (m, 1H), 1.96-1.86 (m, 1H), 1.83-1.66 (m, 2H), 0.95 (t, 3H), 0.94 (s, 9H). $^{13}C$ NMR (151 MHz, DMSO-d6) δ 180.69, 171.95, 170.40, 169.62, 165.76, 156.00 (dd, J=246.6, 6.9 Hz), 152.34 (dd, J=249.4, 8.3 Hz), 151.42, 149.13, 147.71, 144.14, 140.67, 139.50, 138.99, 133.39, 131.16, 130.58, 129.64, 128.81 (d, J=9.8 Hz), 128.64, 128.03, 127.42, 127.23, 126.91, 122.26-121.63 (m), 118.52-117.80 (m), 117.52, 115.75, 112.77-111.89 (m), 68.92, 58.75, 56.53, 56.40, 53.47, 41.67, 37.97, 36.32, 35.26, 34.89, 26.40, 16.85, 15.95, 12.63. LC-MS (ESI); m/z $[M+H]^+$: Calcd. for $C_{49}H_{53}F_2N_8O_8S_2$, 983.3395. Found 983.3963.

Example 20-Synthetic Scheme F: Compound 512, 513, and 516

Method F
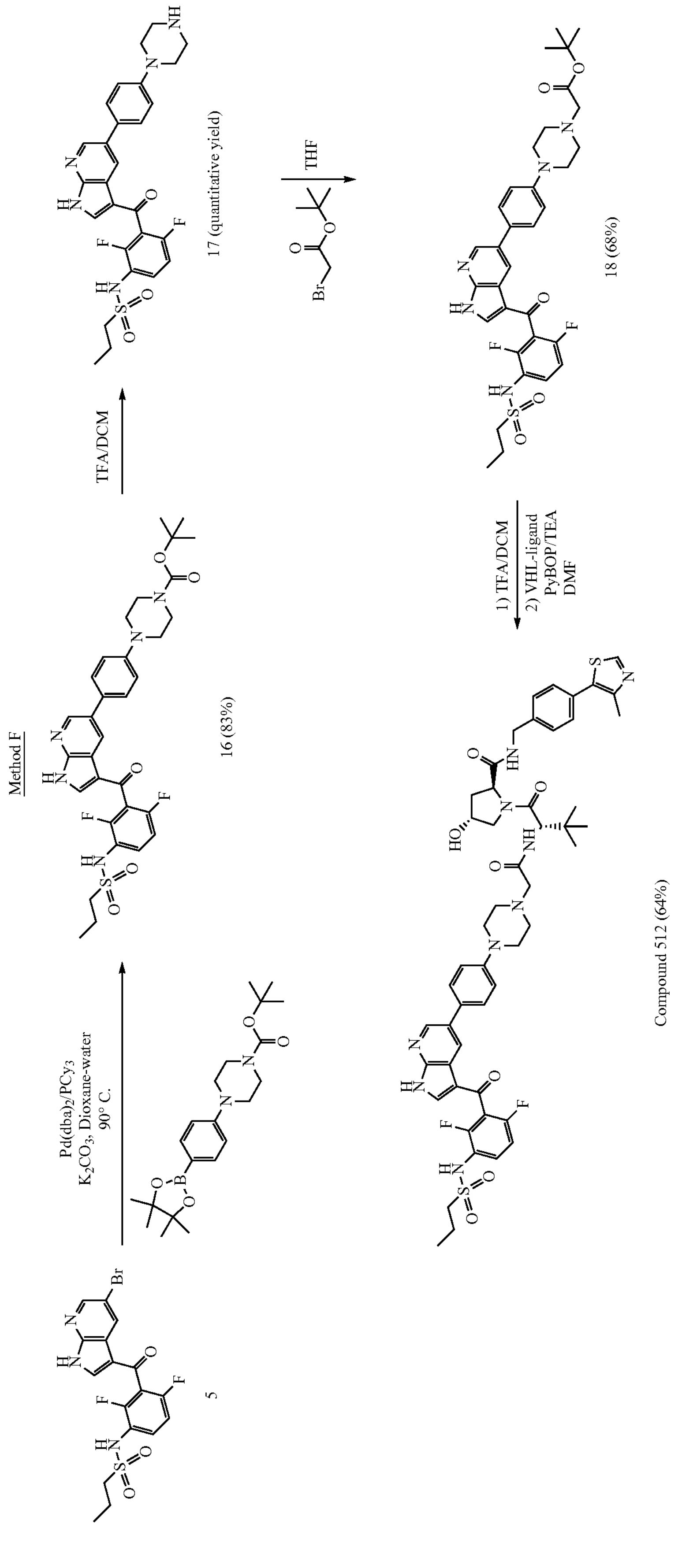
5
16 (83%)
17 (quantitative yield)
18 (68%)
Compound 512 (64%)

tert-butyl 4-(4-(3-(2,6-difluoro-3-(propylsulfonamido)benzoyl)-1H-pyrrolo[2,3-b]pyridin-5-yl)phenyl)-piperazine-1-carboxylate (16)

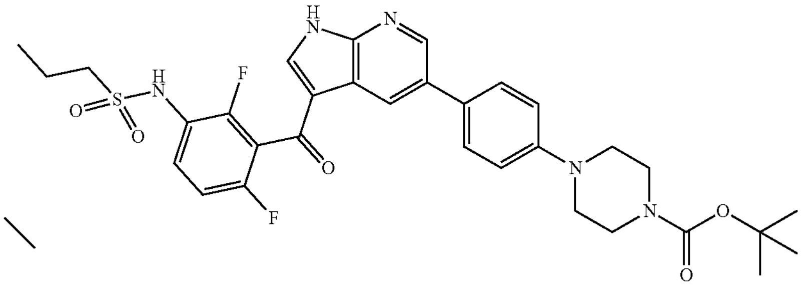

To a solution of N-[3-(5-bromo-1H-pyrrolo[2,3-b]pyridine-3-carbonyl)-2,4-difluoro-phenyl]propane-1-sulfonamide (5) (70.8 mg, 0.155 mmol) in Dioxane (6 ml) was added tert-butyl 4-(4-(4,4,5,5-tetramethyl-1,3,2-dioxaborolan-2-yl)phenyl)piperazine-1-carboxylate (60.0 mg, 0.155 mmol), $K_2CO_3$ (64.2 mg, 0.465 mmol), Tricyclohexyl phosphine (4.33 mg, 0.0155 mmol) and water (2 mL). Then the reaction mixture was de-gassed under vacuum and purged with argon (5×), $Pd(dba)_2$ (4.44 mg, 0.00773 mmol) was added into and the reaction mixture was heated at 90° C. for 3 h. By TLC small amounts of SM (Hex:AcOEt, 3:7), the reaction mixture was filtered in vacuum over a celite pad, filtrate was poured into an aqueous saturated solution of NaCl (20 mL) and the product was extracted with EtOAc (2×20 mL). The EtOAc layers were combined, dried ($Na_2SO_4$) and concentrated in vacuum. The crude material was diluted in $CH_2Cl_2$ and purified by flash chromatography ($SiO_2$-12 g, Hexane:EtOAc, 9:1 to 100% EtOAc in 15 min) to give 82 mg (83%) of product. $^{13}C$ NMR (151 MHz, DMSO-d6) δ 180.61, 156.04 (dd, J=246.5, 6.9 Hz), 153.88, 152.34 (dd, J=249.4, 8.6 Hz), 150.35, 148.44, 143.61, 138.60, 131.47, 128.92-128.75 (m), 128.19 (d, J=161.3 Hz), 126.05, 121.94 (dd, J=13.6, 3.6 Hz), 118.96-117.87 (m), 117.60, 116.33, 115.61, 112.36 (dd, J=22.6, 3.2 Hz), 79.03, 53.42, 48.08, 43.72, 42.58, 28.09, 16.87, 12.64. NMR (500 MHz, DMSO-d6) δ 12.92 (bs, 1H), 9.76 (bs, 1H), 8.66 (d, J=2.2 Hz, 1H), 8.55 (s, 1H), 8.19 (s, 1H), 7.75-7.46 (m, 3H), 7.28 (t, J=8.7 Hz, 1H), 7.10 (d, J=8.7 Hz, 2H), 3.49 (t, 4H), 3.19 (t, J=5.2 Hz, 4H), 3.16-3.05 (m, 2H), 1.74 (h, J=7.5 Hz, 2H), 1.43 (s, 9H), 0.96 (t, J=7.4 Hz, 3H). LC-MS (ESI); m/z $[M+H]^+$: Calcd. for $C_{32}H_{36}F_2N_5O_5S$, 640.2405. Found 640.2541.

N-(2,4-difluoro-3-(5-(4-(piperazin-1-yl)phenyl)-1H-pyrrolo[2,3-b]pyridine-3-carbonyl)phenyl)propane-1-sulfonamide (17)

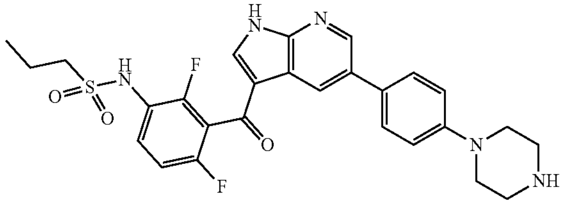 [SMILES: CCCS(=O)(=O)Nc1ccc(F)c(C(=O)c2c[nH]c3ncc(-c4ccc(N5CCNCC5)cc4)cc23)c1F]

A solution of tert-butyl 4-[4-[3-[2,6-difluoro-3-(propylsulfonylamino)benzoyl]-1H-pyrrolo[2,3-b]pyridin-5-yl] phenyl]piperazine-1-carboxylate (16) (28.0 mg, 0.0438 mmol) in a mixture of DCM/TFA (3:1, 4 mL) was stirred for 1 h at room temperature (by TLC no SM "A"). The solvent was removed under vacuum and the residue was dried under high vacuum foe 2 h (23 mg of product, quantitative yield). Crude product was used in the next step without any further purification. LC-MS (ESI); m/z $[M+H]^+$: Calcd. for $C_{27}H_{28}F_2N_5O_3S$, 540.1880. Found 540.1949.

tert-butyl 2-(4-(4-(3-(2,6-difluoro-3-(propylsulfonamido)benzoyl)-1H-pyrrolo[2,3-b]pyridin-5-yl)-phenyl) piperazin-1-yl)acetate (18)

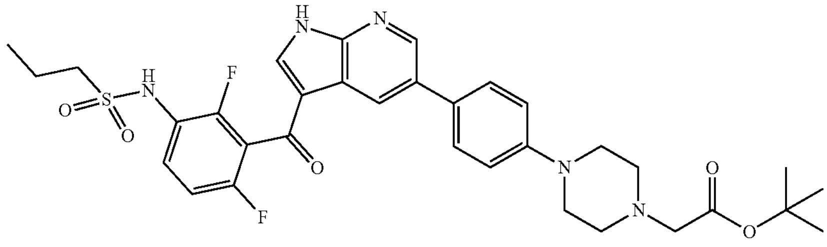 [SMILES: CCCS(=O)(=O)Nc1ccc(F)c(C(=O)c2c[nH]c3ncc(-c4ccc(N5CCN(CC(=O)OC(C)(C)C)CC5)cc4)cc23)c1F]

To a solution of N-[2,4-difluoro-3-[5-(4-piperazin-1-ylphenyl)-1H-pyrrolo[2,3-b]pyridine-3-carbonyl]-phenyl] propane-1-sulfonamide (17) (23.0 mg, 0.0426 mmol) and TEA (0.0594 mL, 0.426 mmol) in DMF (1 ml) was added tert-butyl 2-bromoacetate (9.15 mg, 0.0469 mmol) and the resulting solution stirred for 3 h at rt. The reaction mixture was evaporated under vacuum. Crude product was purified by PTLC (DCM:MeOH:$NH_4$OH, 90:9:1, 2×) to give 19 mg of pure product (69% yield). NMR (500 MHz, DMSO-d6) δ 12.92 (bs, 1H), 9.76 (bs, 1H), 8.65 (t, J=2.6 Hz, 1H), 8.55 (s, 1H), 8.18 (s, 1H), 7.76-7.42 (m, 3H), 7.28 (t, J=8.3 Hz, 1H), 7.07 (d, J=6.5 Hz, 2H), 3.33 (s, 2H), 3.30-3.16 (m, 4H), 3.16-3.04 (m, 2H), 2.81-2.55 (m, 4H), 1.84-1.67 (m, 2H), 1.43 (s, 9H), 0.96 (t, J=7.2 Hz, 3H). $^{13}$C NMR (151 MHz, DMSO-d6) δ 180.57, 169.22, 156.02 (dd, J=246.3, 7.0 Hz), 152.33 (dd, J=249.4, 8.6 Hz), 150.42, 148.37, 143.55, 138.50, 131.53, 128.75 (d, J=9.6 Hz), 128.17, 127.58, 125.93, 121.92 (dd, J=13.6, 3.6 Hz), 118.25 (t, J=23.6 Hz), 117.58, 115.80, 115.58, 112.33 (dd, J=21.9, 3.0 Hz), 80.23, 59.21, 53.44, 51.81, 47.93, 27.82, 16.84, 12.62. LC-MS (ESI); m/z [M+H]$^+$: Calcd. for $C_{33}H_{38}F_2N_5O_5S$, 654.2561. Found 654.2675.

(2S,4R)-1-((S)-2-(2-(4-(4-(3-(2,6-difluoro-3-(propylsulfonamido)benzoyl)-1H-pyrrolo[2,3-b]pyridin-5-yl)phenyl)piperazin-1-yl)acetamido)-3,3-dimethylbutanoyl)-4-hydroxy-N-(4-(4-methylthiazol-5-yl)benzyl)pyrrolidine-2-carboxamide (Compound 512)

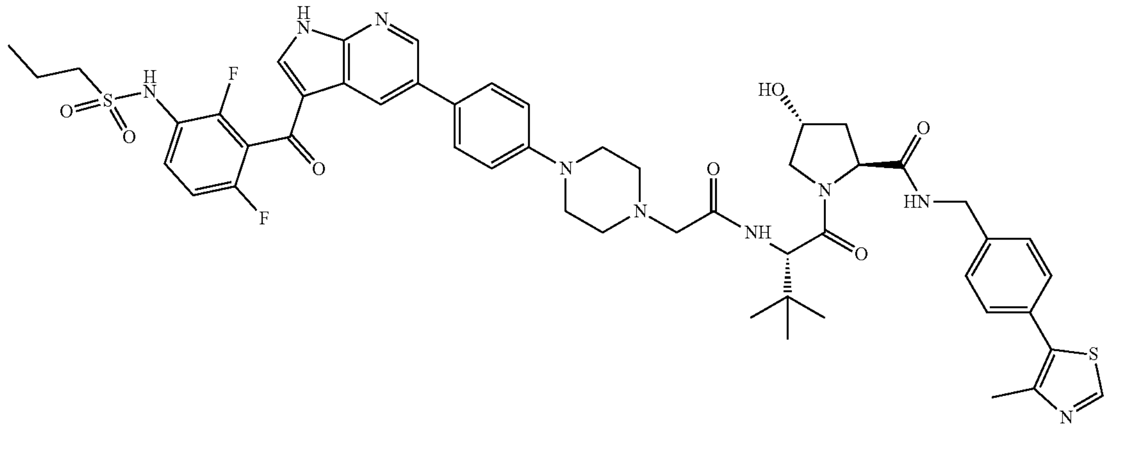 [SMILES: CCCS(=O)(=O)Nc1ccc(F)c(C(=O)c2c[nH]c3ncc(-c4ccc(N5CCN(CC(=O)N[C@H](C(=O)N6C[C@H](O)C[C@H]6C(=O)NCc6ccc(-c7scnc7C)cc6)C(C)(C)C)CC5)cc4)cc23)c1F]

A solution of tert-butyl 2-(4-(4-(3-(2,6-difluoro-3-(propylsulfonamido)benzoyl)-1H-pyrrolo[2,3-b]pyridin-5-yl)phenyl)piperazin-1-yl)acetate (18) (20.0 mg, 0.0306 mmol) in a mixture of TFA (2 ml, 13.46 mmol) and Dichloromethane (2 ml) was stirred for 5 h. Then the solvent was removed under vacuum and crude product was dried under high vacuum for 1 h. Crude product was used in the next step without any further purification (18.3 mg, quantitative yield). FC-MS (ESI); m/z: [M+H]$^+$ Calcd. for $C_{29}H_{30}F_2N_5O_5S$, 598.1935. Found 598.1953. To a solution of crude product from above; 2-(4-(4-(3-(2,6-difluoro-3-(propylsulfonamido)benzoyl)-1H-pyrrolo[2,3-b]pyridin-5-yl)phenyl)-piperazin-1-yl)acetic acid (18.3 mg, 0.0306 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (4) (17.2 mg, 0.0367 mmol) in DMF (1 ml) was added TEA (0.106 mL, 0.762 mmol) and PyBOP (19.1 mg, 0.0367 mmol) at room temperature. The reaction mixture was stirred for 4 h at the same temperature. TEC (DCM:MeOH:$NH_4$OH, 90:9:1) shows no starting material (acid). The reaction mixture was evaporated to dryness under high vacuum. Crude product was diluted with EtOAc (10 mF) and washed with a saturated-aqueous solution of $NaHCO_3$ (2×5 mF), organic extract was dried ($Na_2SO_4$), and evaporated under vacuum. Crude product was purified by PTFC DCM:MeOH:$NH_4$OH, 90:9:1, 2×) to give 20 mg of product (65% yield). NMR (500 MHz, DMSO-d6) δ 12.92 (bs, 1H), 9.76 (bs, 1H), 8.91 (s, 1H), 8.66 (s, 1H), 8.65-8.45 (m, 2H), 7.85 (d, J=9.1 Hz, 1H), 7.74-7.52 (m, 3H), 7.49-7.32 (m, 4H), 7.28 (t, J=8.6 Hz, 1H), 7.09 (d, J=8.5 Hz, 2H), 5.16 (d, J=3.0 Hz, 1H), 4.54 (d, J=9.6 Hz, 1H), 4.52-4.32 (m, 3H), 4.26 (dd, J=15.7, 5.4 Hz, 1H), 3.76-3.58 (m, 2H), 3.27 (s, 4H), 3.21-2.95 (m, 4H), 2.68 (s, 4H), 2.40 (s, 3H), 2.07 (dd, J=12.9, 7.7 Hz, 1H), 1.92 (ddd, J=13.1, 9.0, 4.6 Hz, 1H), 1.75 (h, J=7.5 Hz, 2H), 0.97 (s, 9H), 0.96 (t, J=7.4 Hz, 3H). $^{13}$C NMR (126 MHz, DMSO-d6) δ 180.56, 171.77, 169.28, 168.48, 156.02 (dd, J=246.6, 7.0 Hz), 152.37 (dd, J=240.8, 8.8 Hz), 151.30, 150.27, 148.38, 147.68, 143.55, 139.42, 138.47, 131.48, 131.12, 129.68, 129.10-128.66 (m), 128.63, 128.33, 127.57, 127.51, 125.96, 121.92 (dd, J=13.7, 3.6 Hz), 118.60-117.95 (m), 117.57, 115.84, 115.59, 112.32 (dd, J=23.0, 2.7 Hz), 68.91, 60.59, 58.81, 56.56, 55.86, 48.16, 41.67, 37.87, 35.80, 26.26, 16.83, 15.90, 12.61. LC-MS (ESI); m/z [M+H]$^+$: Calcd. for $C_{51}H_{58}F_2N_9O_7S_2$, 1010.3868. Found 1010.4036

(2S,4R)-1-((S)-2-(4-(4-(3-(2,6-difluoro-3-(propylsulfonamido)benzoyl)-1H-pyrrolo[2,3-b]-pyridine-5-yl)benzamido)butanamido)-3,3-dimethylbutanoyl)-4-hydroxy-N-(4-(4-methylthiazol-5-yl)benzyl)pyrrolidine-2-carboxamide (Compound 513)

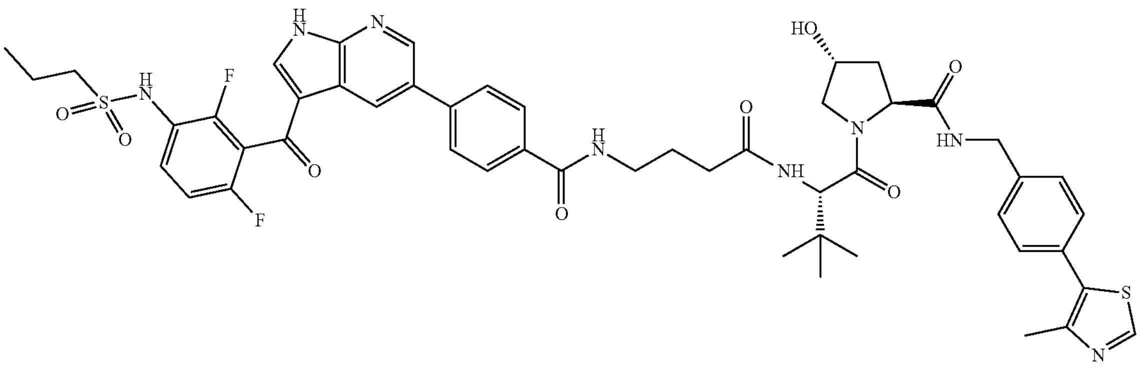 [SMILES: CCCS(=O)(=O)Nc1ccc(F)c(C(=O)c2c[nH]c3ncc(-c4ccc(C(=O)NCCCC(=O)N[C@H](C(=O)N5C[C@H](O)C[C@H]5C(=O)NCc5ccc(-c6scnc6C)cc5)C(C)(C)C)cc4)cc23)c1F]

To a solution of crude product from SJF-0633; 4-(4-(3-(2,6-difluoro-3-(propylsulfonamido)benzoyl)-1H-pyrrolo[2,3-b]pyridin-5-yl)benzamido)butanoic acid (29.0 mg, 0.0496 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (27.8 mg, 0.0595 mmol) in DMF (2 ml) was added TEA (0.172 mF, 1.23 mmol) and PyBOP (31.0 mg, 0.0595 mmol) at room temperature. The reaction mixture was stirred for 4 h at the same temperature. TEC (DCM:MeOH:$NH_4OH$, 90:9:1) shows no starting material (acid). The reaction mixture was evaporated to dryness under high vacuum. Crude product was filtered over a silica-carbonate cartridge (1 g) using DCM:MeOH (9:1) as a eluent. Filtrate was evaporated under vacuum and crude product was purified by PTLC (DCM:MeOH:$NH_4OH$, 85:14:1) to give 35 mg of product (71% yield). $^1$H NMR (400 MHz, DMSO-d6) δ 12.96 (bs, 1H), 9.70 (bs, 1H), 8.97 (s, 1H), 8.77 (d, J=2.0 Hz, 1H), 8.69 (bs, 1H), 8.56 (t, J=5.6 Hz, 2H), 8.26 (s, 1H), 8.08-7.92 (m, 3H), 7.86 (d, J=8.2 Hz, 2H), 7.65-7.53 (m, 1H), 7.40 (dd, J=8.2 Hz, 4H), 7.29 (t, J=8.7 Hz, 1H), 5.14 (d, J=3.5 Hz, 1H), 4.57 (d, J=9.3 Hz, 1H), 4.51-4.31 (m, 3H), 4.22 (dd, J=15.9, 5.4 Hz, 1H), 3.77-3.59 (m, 2H), 3.32-3.21 (m, 2H), 3.17-3.05 (m, 2H), 2.44 (s, 3H), 2.42-2.14 (m, 2H), 2.08-1.98 (m, 1H), 1.97-1.84 (m, 1H), 1.88-1.61 (m, 4H), 0.96 (s, 9H), 0.95 (t, 3H). $^{13}$C NMR (151 MHz, DMSO-d6) δ 181.11, 172.38, 172.30, 170.10, 166.19, 156.45 (dd, J=246.3, 7.1 Hz), 152.78 (dd, J=249.6, 8.2 Hz), 151.86, 149.54, 148.13, 144.57, 141.04, 139.92, 139.43, 133.94, 131.59, 131.04, 130.05, 129.46-129.15 (m), 129.06, 128.49, 127.84, 127.63, 127.32, 122.35 (dd, J=13.4, 3.8 Hz), 118.94-118.30 (m), 117.94, 116.15, 112.79 (d, J=22.6 Hz), 69.32, 59.14, 56.87, 56.82, 53.87, 42.08, 40.46, 38.39, 35.69, 33.08, 26.84, 26.10, 17.26, 16.38, 13.04. LC-MS (ESI); m/z $[M+H]^+$: Calcd. for $C_{50}H_{55}F_2N_8O_8S_2$, 997.3552. Found 997.2761.

(2S,4S)-1-((S)-2-(2-(4-(4-(3-(2,6-difluoro-3-(propylsulfonamido)benzoyl)-1H-pyrrolo[2,3-b]pyridin-5-yl)phenyl)piperazin-1-yl)acetamido)-3,3-dimethylbutanoyl)-4-hydroxy-N-(4-(4-methylthiazol-5-yl)benzyl)pyrrolidine-2-carboxamide (Compound 516)

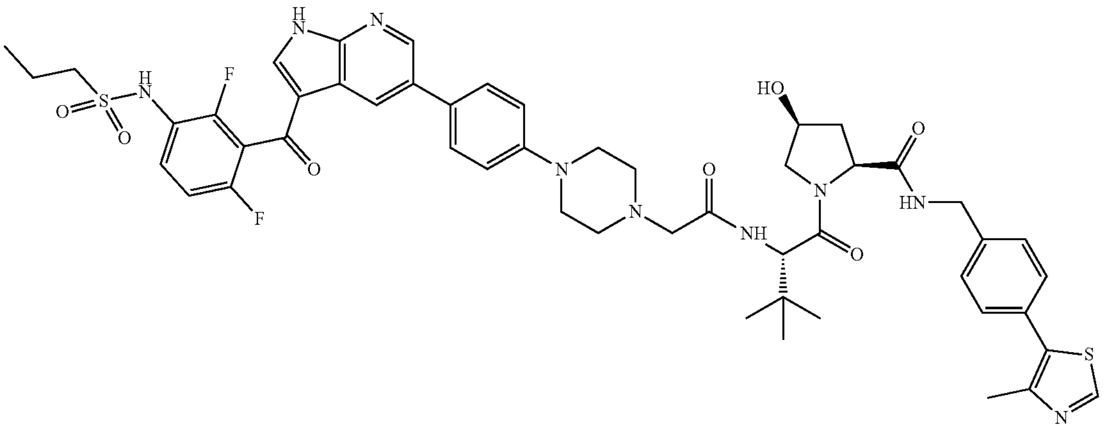 [SMILES: CCCS(=O)(=O)Nc1ccc(F)c(C(=O)c2c[nH]c3ncc(-c4ccc(N5CCN(CC(=O)N[C@H](C(=O)N6C[C@@H](O)C[C@H]6C(=O)NCc6ccc(-c7scnc7C)cc6)C(C)(C)C)CC5)cc4)cc23)c1F]

To a solution of crude product from SJF-0660; 2-(4-(4-(3-(2,6-difluoro-3-(propylsulfonamido)benzoyl)-1H-pyrrolo[2,3-b]pyridin-5-yl)phenyl)-piperazin-1-yl)acetic acid (5.70 mg, 0.00954 mmol) and (2S,4S)-1-((S)-2-amino-3,3-dimethylbutanoyl)-4-hydroxy-N-(4-(4-methylthiazol-5-yl)

benzyl)pyrrolidine-2-carboxamide (5.35 mg, 0.0124 mmol) in DMF (1 ml) was added TEA (0.1 mL, 0.762 mmol) and PyBOP (5.96 mg, 0.0114 mmol) at room temperature. The reaction mixture was stirred for 4 h at the same temperature. TEC (DCM:MeOH:$NH_4OH$, 85:14:1) shows no starting material (acid). The reaction mixture was evaporated to dryness under high vacuum (Product may be soluble in water). Crude product was filtered over a silica-carbonate cartridge (100 mg) using DCM:MeOH (9:1) as a eluent and evaporated under vacuum. Crude product was purified by PTLC (DCM:MeOH:$NH_4OH$, 85:14:1) to give 6.1 mg of product (63% yield). NMR (500 MHz, DMSO-d6) δ 12.93 (bs, 1H), 9.76 (bs, 1H), 8.93 (s, 1H), 8.69 (t, J=5.8 Hz, 1H), 8.66 (s, 1H), 8.56 (bs, 1H), 8.18 (s, 1H), 7.81 (d, J=8.6 Hz, 1H), 7.65-7.50 (m, 3H), 7.51-7.32 (m, 4H), 7.28 (t, J=8.7 Hz, 1H), 7.09 (d, J=8.2 Hz, 2H), 5.48 (d, J=7.2 Hz, 1H), 4.49 (d, J=9.2 Hz, 1H), 4.46-4.33 (m, 2H), 4.32-4.18 (m, 2H), 3.96-3.88 (m, 1H), 3.54-3.42 (m, 1H), 3.30-3.19 (m, 4H), 3.17-3.00 (m, 4H), 2.78-2.56 (m, 4H), 2.41 (s, 3H), 2.39-2.30 (m, 1H), 1.82-1.68 (m, 3H), 0.98 (s, 9H), 0.95 (t, 3H). $^{13}C$ NMR (151 MHz, DMSO-d6) δ 180.60, 172.29, 169.55, 168.84, 156.04 (dd, J=246.5, 6.9 Hz), 152.38 (dd, J=249.4, 8.3 Hz), 151.40, 150.29, 148.40, 147.75, 143.57, 139.16, 138.53, 131.50, 131.12, 129.79, 128.78 (d, J=7.4 Hz), 128.70, 128.36, 127.54, 125.99, 121.93 (dd, J=13.4, 3.6 Hz), 118.52-117.94 (m), 117.59, 115.87, 115.60, 112.35 (dd, J=23.0, 3.9 Hz), 69.09, 60.50, 58.62, 56.01, 55.63, 53.46, 52.70, 48.17, 41.83, 36.90, 35.21, 26.25, 16.85, 15.93, 12.63. LC-MS (ESI); m/z $[M+H]^+$: Calcd. for $C_{51}H58F_2N_9O_7S_2$, 1010.3868. Found 1010.3542.

Example 21-Synthetic Scheme G: Compound 515

Method G
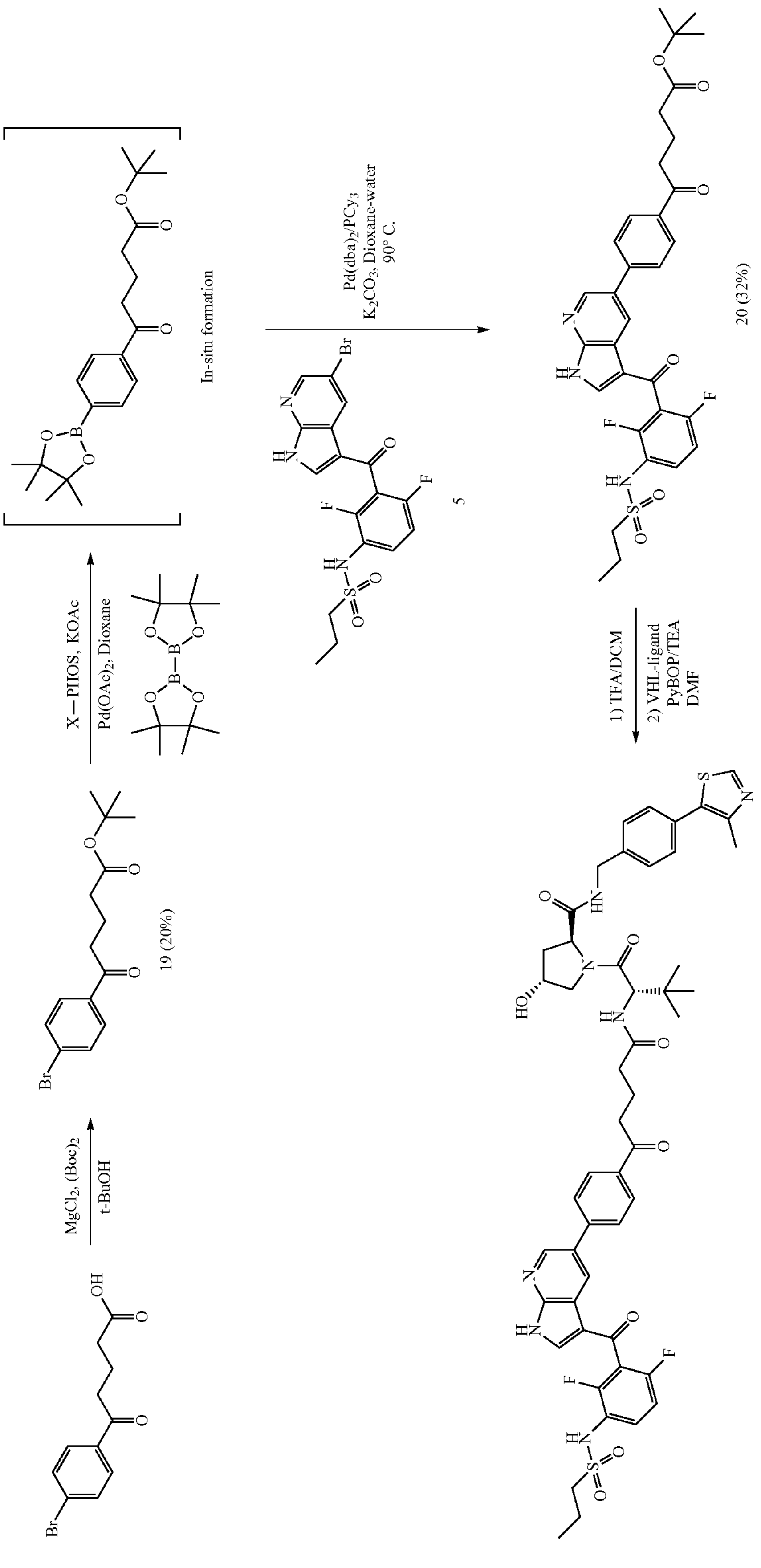
19 (20%)
5
20 (32%)
Compound 515 (64%)

tert-butyl 5-(4-bromophenyl)-5-oxopentanoate (19)

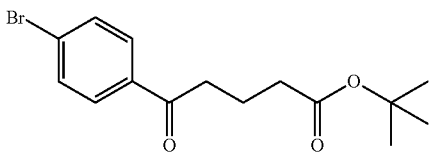 [SMILES: CC(C)(C)OC(=O)CCCC(=O)c1ccc(Br)cc1]

In a flask equipped with a magnetic stirring bar, 5-(4-bromophenyl)-5-oxopentanoic acid (0.460 g, 1.70 mmol), and Boc Anhydride (0.481 g, 2.21 mmol) were dissolved in t-Butanol (1.00 mL, 10.5 mmol) and then Magnesium Chloride (0.0162 g, 0.170 mmol) was added into. The mixture was stirred at 40° C. for 16 h (overnight). The crude reaction mixture was diluted with EtOAc (100 mL), washed with water (2×100 mL), aqueous $NaHCO_3$ (2×100 mL), dried ($Na_2SO_4$) and evaporated by rotary evaporation. Crude product was purified by flash chromatography ($SiO_2$-25 g, Gradient Hex 100% to Hex:EtOAc, 1:1, in 15 min) to give 198 mg of product (35% yield). $^1H$ NMR (500 MHz, Chloroform-d) δ 7.82 (d, J=8.3 Hz, 2H), 7.60 (d, J=8.4 Hz, 2H), 2.99 (t, J=7.2 Hz, 2H), 2.33 (t, J=7.1 Hz, 2H), 2.01 (p, J=7.2 Hz, 2H), 1.44 (s, 9H). $^{13}C$ NMR (101 MHz, cdcl3) δ 198.68, 172.67, 135.69, 132.04, 129.72, 128.33, 80.54, 37.64, 34.68, 28.27, 19.68. LC-MS (ESI); m/z $[M+Na]^+$: Calcd. for $C_{15}H_{19}BrO_3Na$, 349.0415. Found 349.0676, and 351.0609.

tert-Butyl 5-(4-(3-(2,6-difluoro-3-(propylsulfonamido)benzoyl)-1H-pyrrolo[2,3-b]pyridin-5-yl)phenyl)-5-oxopentanoate (20)

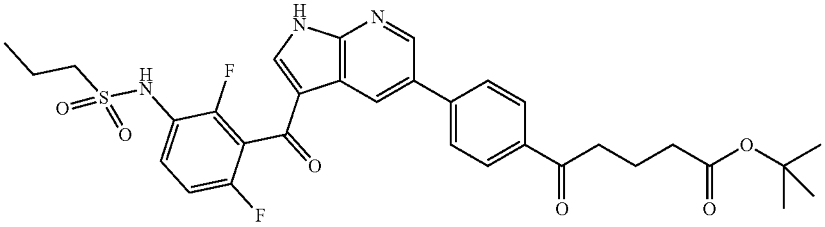 [SMILES: CCCS(=O)(=O)Nc1ccc(F)c(C(=O)c2c[nH]c3ncc(-c4ccc(C(=O)CCCC(=O)OC(C)(C)C)cc4)cc23)c1F]

To a solution of tert-butyl 5-(4-bromophenyl)-5-oxo-pentanoate (19) (74.0 mg, 0.226 mmol) in Dioxane (5 mL) was added 4,4,5,5-tetramethyl-2-(4,4,5,5-tetramethyl-1,3,2-dioxaborolan-2-yl)-1,3,2-dioxaborolane (63.2 mg, 0.249 mmol), $CH_3CO_2K$ (66.6 mg, 0.678 mmol), and the reaction mixture was degassed under argon. X-PHOS (16.2 mg, 0.0339 mmol) and Palladium(II) acetate (2.54 mg, 0.0113 mmol) were added and the reaction mixture was stirred at 100° C. (external temperature) for 1 h. under a argon atmosphere. After 1 h. the temperature of the heating bath was turned down to 90° C. and the flask was raised out of the heating bath, but continued stirring. N-[3-(5-bromo-1H-pyrrolo[2,3-b]pyridine-3-carbonyl)-2,4-difluoro-phenyl]propane-1-sulfonamide (5) (104 mg, 0.226 mmol) and Potassium carbonate (93.8 mg, 0.678 mmol) were added, followed by water (2.00 ml). Tricyclohexyl phosphine (6.34 mg, 0.0226 mmol, 2×) and $Pd(dba)_2$ (6.50 mg, 0.0113 mmol) were added, and the reaction mixture was heated with vigorous stirring at 90° C. and stirred for 3 h, then the reaction mixture was cooled to ambient temperature. The reaction mixture was diluted with EtOAc (30 mL) and poured into brine (20 mL), the organic extract was dried ($Na_2SO_4$), and evaporated under vacuum. Crude product was purified by flash chromatography ($SiO_2$-40 g, gradient Hex:EtOAc, 1:9 to 100% EtOAc in 20 min). Product was about 85% pure, it was purified again by PTLC (DCM: $MeOH:NH_4OH$, 90:9:1) to give 45 mg of product (32% yield). NMR (500 MHz, DMSO-d6) δ 12.98 (bs, 1H), 9.68 (bs, 1H), 8.78 (s, 1H), 8.69 (s, 1H), 8.26 (s, 1H), 8.07 (d, J=8.3 Hz, 2H), 7.92 (d, J=8.3 Hz, 2H), 7.65-7.49 (m, 1H), 7.27 (t, J=8.7 Hz, 1H), 3.10 (q, J=7.8, 7.3 Hz, 4H), 2.29 (t, J=7.4 Hz, 2H), 1.85 (p, J=7.3, 6.8 Hz, 2H), 1.79-1.62 (m, 2H), 1.39 (s, 9H), 0.95 (t, J=7.4 Hz, 3H). $^{13}C$ NMR (151 MHz, DMSO-d6) δ 199.09, 180.72, 172.08, 156.04 (dd, J=246.5, 6.9 Hz), 152.37 (dd, J=249.6, 8.5 Hz), 149.29, 144.21, 142.60, 139.11, 135.42, 130.30, 128.97-128.74 (m), 128.78, 127.40, 127.35, 122.00 (dd, J=13.6, 3.7 Hz), 118.66-117.86 (m), 117.55, 115.79, 112.38 (dd, J=22.7, 3.8 Hz), 79.61, 53.48, 37.08, 34.03, 27.80, 19.46, 16.86, 12.64. LC-MS (ESI); m/z: $[M+H]^+$ Calcd. for $C_{32}H_{34}F_2N_3O_6S$, 626.2136. Found 626.2191.

(2S,4R)-1-((S)-2-(5-(4-(3-(2,6-difluoro-3-(propylsulfonamido)benzoyl)-1H-pyrrolo[2,3-b]pyridin-5-yl)-phenyl)-5-oxopentanamido)-3,3-dimethylbutanoyl)-4-hydroxy-N-(4-(4-methylthiazol-5-yl)benzyl)-pyrrolidine-2-carboxamide (Compound 515)

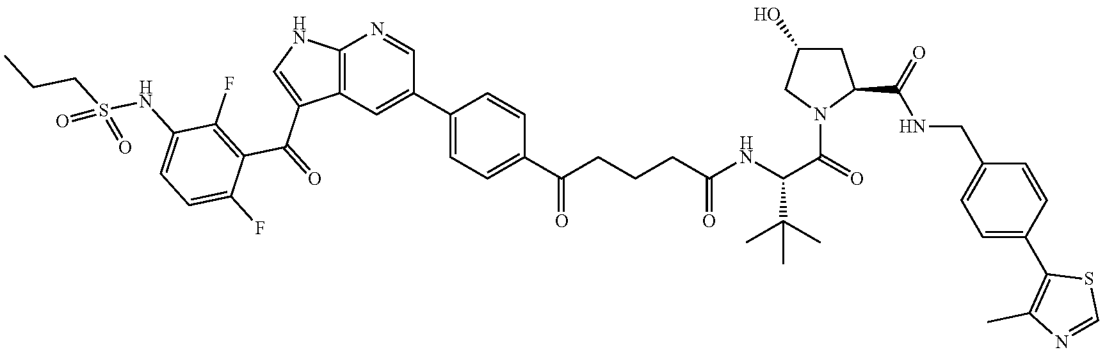 [SMILES: CCCS(=O)(=O)Nc1ccc(F)c(C(=O)c2c[nH]c3ncc(-c4ccc(C(=O)CCCC(=O)N[C@H](C(=O)N5C[C@H](O)C[C@H]5C(=O)NCc5ccc(-c6scnc6C)cc5)C(C)(C)C)cc4)cc23)c1F]

A solution of tert-butyl 5-(4-(3-(2,6-difluoro-3-(propylsulfonamido)benzoyl)-1H-pyrrolo[2,3-b]pyridin-5-yl)phenyl)-5-oxopentanoate (20) (22.0 mg, 0.0352 mmol) in a mixture of TFA (1.50 mL, 20.2 mmol) and Dichloromethane (3 ml) was stirred for 2 h at room temperature. Then the solvent was removed under vacuum and crude product was dried under high vacuum for 2 h. Crude product was used in the next step without any further purification (19.9 mg, quantitative yield). LC-MS (ESI); m/z: $[M+H]^+$ Calcd. for $C_{28}H_{26}F_2N_3O_6S$, 570.1510. Found 570.1553. To a solution of crude product from above; 5-(4-(3-(2,6-difluoro-3-(propylsulfonamido)benzoyl)-1H-pyrrolo[2,3-b]pyridin-5-yl)phenyl)-5-oxopentanoic acid (22.0 mg, 0.0386 mmol) and (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (4)(19.8 mg, 0.0425 mmol) in DMF (2 ml) was added TEA (0.200 mL, 1.43 mmol) and PyBOP (22.1 mg, 0.0425 mmol) at room temperature. The reaction mixture was stirred for 4 h at the same temperature. TLC (DCM:MeOH:$NH_4OH$, 90:9:1) shows no starting materials. The DMF was removed under high vacuum. Crude product was filtered over a silica-carbonate cartridge using DCM:MeOH (9:1) as a eluent. Filtrate was evaporated under vacuum and crude product was purified by PTLC (DCM:MeOH:$NH_4OH$, 85:14:1) to give 25 mg of product (64% yield. ~97% pure by NMR). NMR (600 MHz, DMSO-d6) δ 13.03 (bs, 1H), 9.73 (bs, 1H), 8.94 (s, 1H), 8.76 (d, J=2.1 Hz, 1H), 8.69 (bs, 1H), 8.55 (t, J=6.0 Hz, 1H), 8.25 (s, 1H), 8.06 (d, J=8.3 Hz, 2H), 7.93 (d, J=9.3 Hz, 1H), 7.90 (d, J=8.2 Hz, 2H), 7.63-7.50 (m, 1H), 7.37 (dd, 4H), 7.26 (t, J=8.6 Hz, 1H), 5.11 (d, J=3.5 Hz, 1H), 4.54 (d, J=9.3 Hz, 1H), 4.46-4.36 (m, 2H), 4.36-4.30 (m, 1H), 4.19 (dd, J=15.8, 5.5 Hz, 1H), 3.78-3.55 (m, 2H), 3.13-3.07 (m, 2H), 3.04 (t, J=7.4 Hz, 2H), 2.40 (s, 3H), 2.37-2.21 (m, 2H), 2.08-1.95 (m, 1H), 1.96-1.79 (m, 3H), 1.71 (h, J=7.5 Hz, 2H), 0.93 (s, 9H), 0.92 (t, 3H). $^{13}C$ (151 MHz, DMSO-d6) δ 199.32, 180.72, 171.98, 171.86, 169.74, 156.03 (dd, J=246.6, 6.9 Hz), 152.36 (dd, J=249.4, 8.4 Hz), 151.43, 149.28, 147.71, 144.21, 142.52, 139.52, 139.12, 135.48, 131.17, 130.32, 129.63, 129.00-128.81 (m), 128.79, 128.64, 127.43, 127.36, 127.36, 121.98 (dd, J=13.6, 3.6 Hz), 118.75-117.76 (m), 117.54, 115.78, 112.37 (dd, J=22.4, 3.6 Hz), 68.92, 58.74, 53.46, 41.67, 37.99, 37.47, 35.20, 34.11, 26.43, 20.38, 16.86, 15.95, 12.63. LC-MS (ESI); m/z $[M+H]^+$: Calcd. for $C_{50}H_{54}F_2N_7O_8S_2$, 982.3443. Found 982.3535.

Example Synthesis of Compound 196: (Z)-2-(2,6-Dioxopiperidin-3-yl)-5-(3-(4-(4-(4-(1-(hydroxyimino)-2,3-dihydro-1H-inden-5-yl)-3-(pyridin-4-yl)-1H-pyrazol-1-yl)phenoxy)butoxy)phenyl)isoindoline-1,3-dione

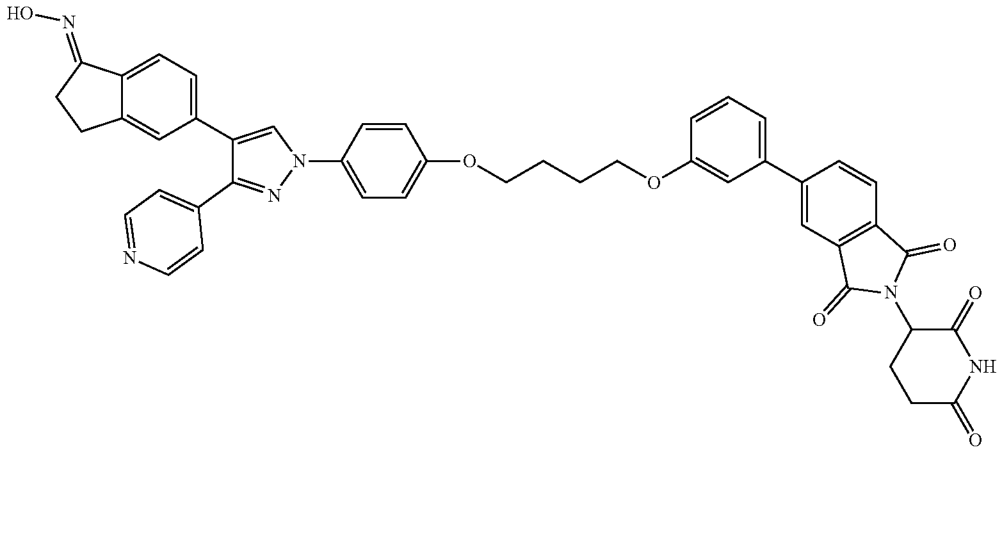 [SMILES: O=C1CCC(N2C(=O)c3ccc(-c4cccc(OCCCCOc5ccc(-n6cc(-c7ccc8c(c7)CC/C8=N\O)c(-c7ccncc7)n6)cc5)c4)cc3C2=O)C(=O)N1]

Step A: 5-(1-(4-(4-hydroxybutoxy)phenyl)-3-(pyridin-4-yl)-1H-pyrazol-4-yl)-2,3-dihydro-1H-inden-1-one

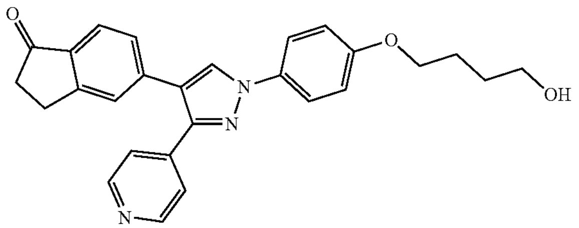 [SMILES: O=C1CCc2cc(-c3cn(-c4ccc(OCCCCO)cc4)nc3-c3ccncc3)ccc21]

To a solution of 4-(4-(4-bromo-3-(pyridin-4-yl)-1H-pyrazol-1-yl)phenoxy)butan-1-ol (150 mg, 0.39 mmol) and 5-(4,4,5,5-tetramethyl-1,3,2-dioxaborolan-2-yl)-2,3-dihydroinden-1-one (120 mg, 0.46 mmol) in 1,4-dioxane/$H_2O$ (10 mL, v/v=10/1) were added t-$Bu_3PHBF_4$ (44.8 mg, 0.15 mmol), CsF (234.9 mg, 1.54 mmol), $Cy_2NCH_3$ (5 drops) and $Pd_2$ $(dba)_3$ (70.7 mg, 0.077 mmol). The resulting solution was stirred at 100° C. for 2 hours under $N_2$. The solvent was evaporated under reduced pressure. The residue was diluted with EA (30 mL), and the mixture was washed with brine. The organic phase was evaporated under reduced pressure, and the residue was purified by silica gel column chromatography on silica gel (DCM/MeOH=80/1) to afford the desired product (140 mg, 82.4% yield) as a colorless oil.

Step B: tert-butyl 5-(3-(pyridin-4-yl)-1-(4-(4-(3-(4,4,5,5-tetramethyl-1,3,2-dioxaborolan-2-yl)phenoxy)butoxy)phenyl)-1H-pyrazol-4-yl)-2,3-dihydro-1H-inden-1-one

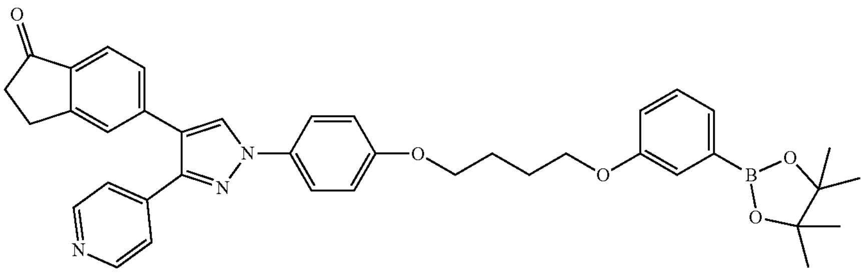 [SMILES: CC1(C)OB(c2cccc(OCCCCOc3ccc(-n4cc(-c5ccc6c(c5)CCC6=O)c(-c5ccncc5)n4)cc3)c2)OC1(C)C]

To a solution of 5-(1-(4-(4-hydroxybutoxy)phenyl)-3-(pyridin-4-yl)-1H-pyrazol-4-yl)-2,3-dihydro-1H-inden-1-one (140 mg, 0.32 mmol) and triethylamine (96.8 mg, 0.96 mmol) in DCM (10 mL) was added MsCl (43.8 mg, 0.38 mmol) at 0° C. After stirring at 30° C. for 1 hour, the solvent was removed under vacuum. The residue was diluted with EA (30 mL), and the mixture was washed with brine. The organic phase was concentrated to give the intermediate mesylate (180 mg, 0.34 mmol, 109%). To a solution of mesylate (90 mg, 0.17 mmol) in dry DMF (10 mL) were added 3-(4,4,5,5-tetramethyl-1,3,2-dioxaborolan-2-yl)phenol (449.7 mg, 0.22 mmol) and $K_2CO_3$ (47.9 mg, 0.34 mmol). The resulting mixture was stirred at 68° C. for 4 hours. The mixture was diluted by EtOAc (40 mL), and the mixture was washed with brine, and dried over anhydrous sodium sulfate. The organic phase was concentrated under reduced pressure. The residue was purified by preparative TLC (PE/EtOAc=1/3) to afford the desired product (80 mg, 71.7% yield). NMR (400 MHz, $CDCl_3$): δ 8.65-8.55 (m, 2H), 8.00 (s, 1H), 7.76 (d, J=7.7 Hz, 1H), 7.68 (d, J=9.1 Hz, 2H), 7.51 (s, 2H), 7.44 (s, 1H), 7.29-7.41 (m, 4H), 7.02 (d, J=7.0 Hz, 3H), 4.12 (dd, J=14.0, 6.9 Hz, 4H), 3.60-3.67 (m, 1H), 3.13 (s, 2H), 2.74 (s, 2H), 2.01 (s, 2H), 1.34 (s, 12H).

Step C: tert-butyl 2-(2,6-dioxopiperidin-3-yl)-5-(3-(4-(4-(4-(1-oxo-2,3-dihydro-1H-inden-5-yl)-3-(pyridin-4-yl)-1H-pyrazol-1-yl)phenoxy)butoxy)phenyl) isoindoline-1,3-dione

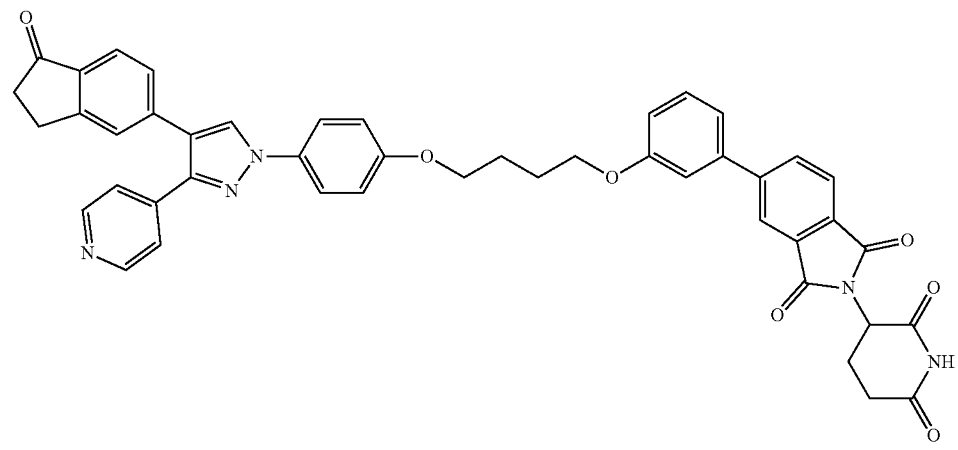 [SMILES: O=C1CCC(N2C(=O)c3ccc(-c4cccc(OCCCCOc5ccc(-n6cc(-c7ccc8c(c7)CCC8=O)c(-c7ccncc7)n6)cc5)c4)cc3C2=O)C(=O)N1]

To a solution of tert-butyl 5-(3-(pyridin-4-yl)-1-(4-(4-(3-(4,4,5,5-tetramethyl-1,3,2-dioxaborolan-2-yl)phenoxy)butoxy)phenyl)-1H-pyrazol-4-yl)-2,3-dihydro-1H-inden-1-one (80 mg, 0.12 mmol) and 5-(3-bromophenyl)-2-(2,6-dioxopiperidin-3-yl)isoindoline-1,3-dione (46.3 mg, 0.14 mmol) in 1,4-dioxane/$H_2O$ (9 mL, 8:1) were added t-$Bu_3PHBF_4$ (14.5 mg, 0.050 mmol), CsF (75.8 mg, 0.50 mmol), $Cy_2NMe$ (1 drop) and $Pd_2(dba)_3$ (22.8 mg, 0.025 mmol). The resulting mixture was stirred at 100° C. for 2 hours under $N_2$. The solvent was evaporated under reduced pressure. The residue was diluted with EA (30 mL), and the mixture was washed with brine. The organic phase was evaporated under reduced pressure. The residue was purified by TLC (PE/EtOAc=1/8) to afford the desired product (40 mg, 41.5% yield).

Step D: (Z)-2-(2,6-Dioxopiperidin-3-yl)-5-(3-(4-(4-(4-(1-(hydroxyimino)-2,3-dihydro-1H-inden-5-yl)-3-(pyridin-4-yl)-1H-pyrazol-1-yl)phenoxy)butoxy) phenyl)isoindoline-1,3-dione To a solution of tert-butyl 2-(2,6-dioxopiperidin-3-yl)-5-(3-(4-(4-(4-(1-oxo-2,3-dihydro-1H-inden-5-yl)-3-(pyridin-4-yl)-1H-pyrazol-1-yl)phenoxy)butoxy)phenyl)isoindoline-1,3-dione (40 mg, 0052 mmol) in $CH_3CN$/Py (5 mL/2 mL) was added $NH_2OH{\cdot}HCl$ (40 mg, 0.57 mmol). The reaction was stirred at 40° C. for 0.5 hours. The mixture was diluted with EtOAc (30 mL), and washed with brine twice. The organic layer was evaporated under reduced pressure. The residue was purified by preparative HPLC to afford the desired product as a white solid (13.5 mg, 8.6% yield). NMR (400 MHz, $CDCl_3$): δ 8.47-8.86 (m, 3H), 8.27 (s, 1H), 8.09 (s, 1H), 7.94 (d, J=4.9 Hz, 3H), 7.68 (d, J=8.7 Hz, 3H), 7.52 (s, 2H), 7.36-7.47 (m, 2H), 7.29 (s, 1H), 7.21 (s, 1H), 7.15 (s, 1H), 7.02 (d, J=8.4 Hz, 3H), 4.97-5.04 (m, 1H), 4.13 (s, 4H), 2.74-3.12 (m, 8H), 2.21 (d, J=7.7 Hz, 2H), 2.01-2.09 (m, 3H). LCMS ($ES^+$): m/z 787.2 $[M+H]^+$.

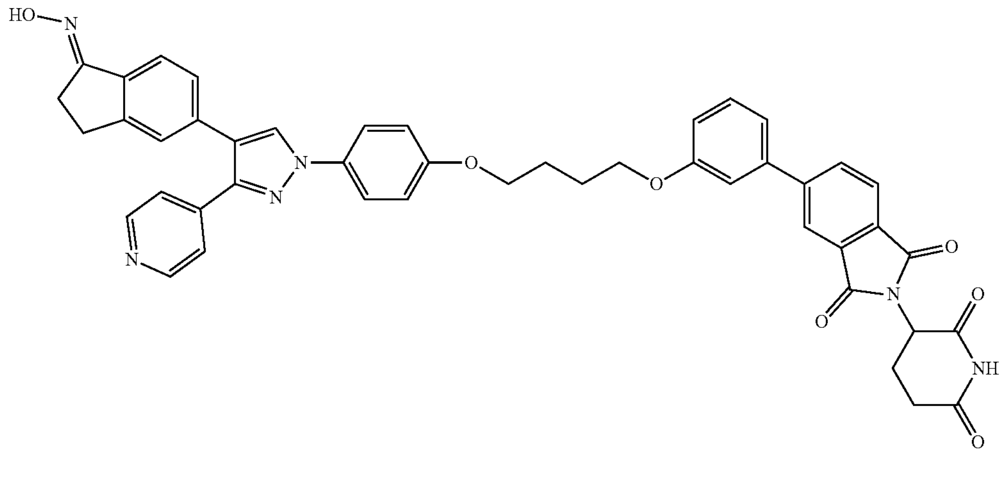 [SMILES: O=C1CCC(N2C(=O)c3ccc(-c4cccc(OCCCCOc5ccc(-n6cc(-c7ccc8c(c7)CC/C8=N\O)c(-c7ccncc7)n6)cc5)c4)cc3C2=O)C(=O)N1]

Example Synthesis of Compound 197: (E)-2-(2,6-Dioxopiperidin-3-yl)-5-(4-(2-(2-(4-(4-(1-(hydroxyimino)-2,3-dihydro-1H-inden-5-yl)-3-(pyridin-4-yl)-1H-pyrazol-1-yl)phenoxy)ethoxy)ethyl)piperazin-1-yl)isoindoline-1,3-dione

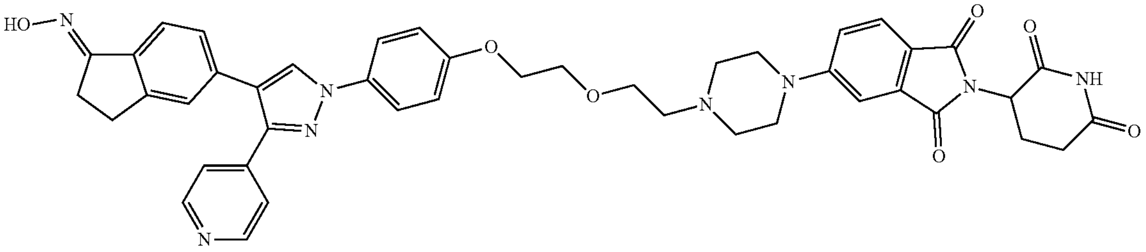 [SMILES: O=C1CCC(N2C(=O)c3ccc(N4CCN(CCOCCOc5ccc(-n6cc(-c7ccc8c(c7)CC/C8=N\O)c(-c7ccncc7)n6)cc5)CC4)cc3C2=O)C(=O)N1]

Step A: 2-(2-(4-(4-bromo-3-(pyridin-4-yl)-1H-pyrazol-1-yl)phenoxy)ethoxy)ethanol

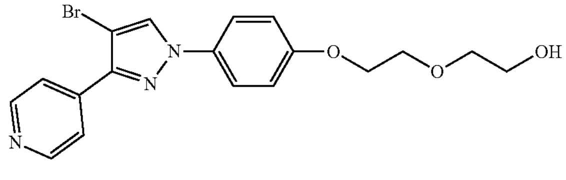 [SMILES: OCCOCCOc1ccc(-n2cc(Br)c(-c3ccncc3)n2)cc1]

To a solution of 4-(4-bromo-3-(pyridin-4-yl)-1H-pyrazol-1-yl)phenol (500 mg, 1.58 mmol) in dry DMF (5 mL) were added $Cs_2CO_3$ (1.55 g, 4.75 mmol) and 2-(2-hydroxyethoxy)ethyl 4-methylbenzenesulfonate (1.23 g, 4.75 mmol) subsequently. The resulting solution was stirred at 70° C. for 3 hours. After cooling to room temperature, the reaction was quenched with water (20 mL), and the mixture was extracted with EtOAc (20 mL×3). The combined organic layer was dried over anhydrous sodium sulfate and concentrated under vacuum. The residue was purified by silica gel column to afford the desired product (500 mg, 78% yield) as a yellow solid. NMR (400 MHz, $CDCl_3$): δ 8.69 (s, 2H), 7.91-7.96 (m, 3H), 7.62 (d, J=8.8 Hz, 2H), 7.05 (d, J=8.4 Hz, 2H), 4.19 (t, J=4.4 Hz, 2H), 3.90 (t, J=4.0 Hz, 2H), 3.78 (t, J=4.8 Hz, 2H), 3.70 (t, J=4.4 Hz, 2H).

Step B: 2-(2-(4-(4-bromo-3-(pyridin-4-yl)-1H-pyrazol-1-yl)phenoxy)ethoxy)ethyl methanesulfonate

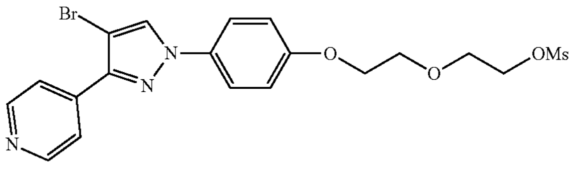 [SMILES: CS(=O)(=O)OCCOCCOc1ccc(-n2cc(Br)c(-c3ccncc3)n2)cc1]

To a solution of 2-(2-(4-(4-bromo-3-(pyridin-4-yl)-1H-pyrazol-1-yl)phenoxy)ethoxy)ethanol (500 mg, 1.24 mmol) and TEA (249 mg, 2.47 mmol) in DCM (5 mL) was added MsCl (169 mg, 1.48 mmol) dropwise at 0° C. The resulting solution was stirred at 5° C. for 0.5 hours. After it was quenched with saturated $NaHCO_3$ (20 mL), the mixture was extracted with DCM (20 mL×2). The combined organic layer was dried over anhydrous sodium sulfate and concentrated to afford the desired product (550 mg crude, calculated) as oil, which was used in next step directly. LCMS (ES+): m/z 482.0 $[M+H]^+$.

Step C: tert-butyl 4-(2-(2-(4-(4-bromo-3-(pyridin-4-yl)-1H-pyrazol-1-yl)phenoxy)ethoxy)ethyl)piperazine-1-carboxylate

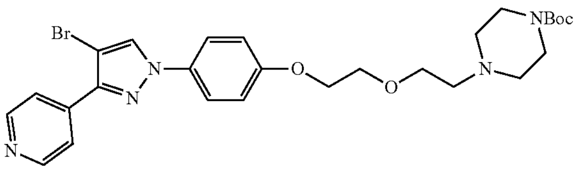 [SMILES: CC(C)(C)OC(=O)N1CCN(CCOCCOc2ccc(-n3cc(Br)c(-c4ccncc4)n3)cc2)CC1]

To a solution of 2-(2-(4-(4-bromo-3-(pyridin-4-yl)-1H-pyrazol-1-yl)phenoxy)ethoxy)ethyl methanesulfonate (0.5 g, 1.04 mmol) and tert-butyl piperazine-1-carboxylate (385 mg, 2.08 mmol) in DMF (5 mL) were added $K_2CO_3$ (715 mg, 5.20 mmol) and KI (860 mg, 5.20 mmol) subsequently. The resulting solution was stirred at 75° C. for 3 hours. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (0.4 g, 56% yield in two steps) as brown oil. $^1H$ NMR (400 MHz, $CDCl_3$): δ 8.69 (d, J=4.8 Hz, 2H), 7.97 (m, 3H), 7.61 (d, J=9.2 Hz, 2H), 7.01 (d, J=8.8 Hz, 2H), 4.05-4.20 (m, 3H), 3.84 (t, J=4.8 Hz, 2H), 3.71 (t, J=5.6 Hz, 2H), 3.44 (m, 4H), 2.63 (t, J=5.6 Hz, 2H), 2.45 (m, 4H), 1.46 (s, 9H).

Step D: tert-butyl 4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazine-1-carboxylate

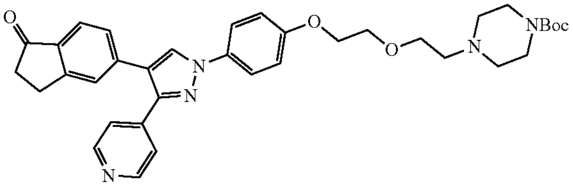 [SMILES: CC(C)(C)OC(=O)N1CCN(CCOCCOc2ccc(-n3cc(-c4ccc5c(c4)CCC5=O)c(-c4ccncc4)n3)cc2)CC1]

To a solution of tert-butyl 4-(2-(2-(4-(4-bromo-3-(pyridin-4-yl)-1H-pyrazol-1-yl)phenoxy)ethoxy)ethyl)piperazine-1-carboxylate (0.4 g, 0.70 mmol) and 5-(4,4,5,5-tetramethyl-1,3,2-dioxaborolan-2-yl)-2,3-dihydro-1H-inden-1-one (271 mg, 1.05 mmol) in 1,4-dioxane (15 mL)/$H_2O$ (1.5 mL) were added CsF (425 mg, 2.80 mmol), $Pd_2$ $(dba)_3$ (256 mg, 0.28 mmol), tri-tert-butylphosphine tetrafluoroborate (162 mg, 0.56 mmol) and cat. N-cyclohexyl-N-methylcyclohexanamine subsequently. The reaction was heated to 100° C. for 2 h under $N_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (0.4 g crude) as brown oil. LCMS ($ES^+$): m/z 624.7 [M+H]+.

Step E: 2-(2,6-dioxopiperidin-3-yl)-5-(4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazin-1-yl)isoindoline-1,3-dione

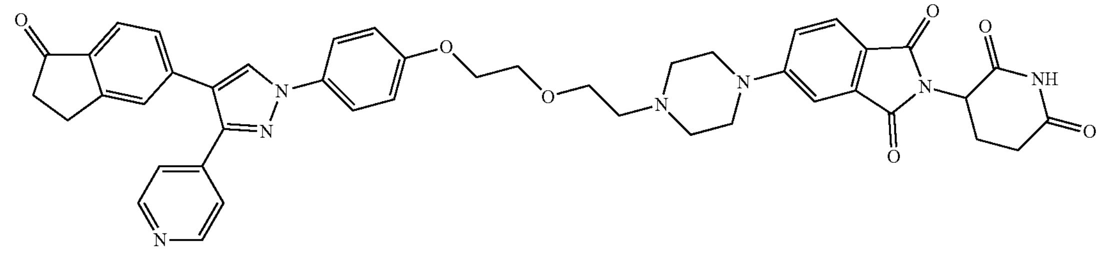 [SMILES: O=C1CCC(N2C(=O)c3ccc(N4CCN(CCOCCOc5ccc(-n6cc(-c7ccc8c(c7)CCC8=O)c(-c7ccncc7)n6)cc5)CC4)cc3C2=O)C(=O)N1]

To a solution of tert-butyl 4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazine-1-carboxylate (400 mg, 0.64 mmol) in MeOH (5 mL) was added HCl in 1,4-dioxane (5 mL, 8 mol/L). The resulting solution was stirred at 10° C. for 1 hours. The solvent was removed under vacuum to afford the desired product (359 mg, calculated), which was used directly in next step. To a solution of crude product (359 mg, 0.64 mmol) in NMP (5 mL) were added DIEA (825 mg, 6.40 mmol) and 2-(2,6-dioxopiperidin-3-yl)-5-fluoroisoindoline-1,3-dione (530 mg, 1.92 mmol) subsequently. The reaction was irritated to 150° C. with microwave for 60 minutes. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (3 g crude, NMP included) as brown oil. LCMS (ES+): m/z 780.8 $[M+H]^+$.

Step F: (E)-2-(2,6-Dioxopiperidin-3-yl)-5-(4-(2-(2-(4-(4-(1-(hydroxyimino)-2,3-dihydro-1H-inden-5-yl)-3-(pyridin-4-yl)-1H-pyrazol-1-yl)phenoxy)ethoxy)ethyl)piperazin-1-yl)isoindoline-1,3-dione

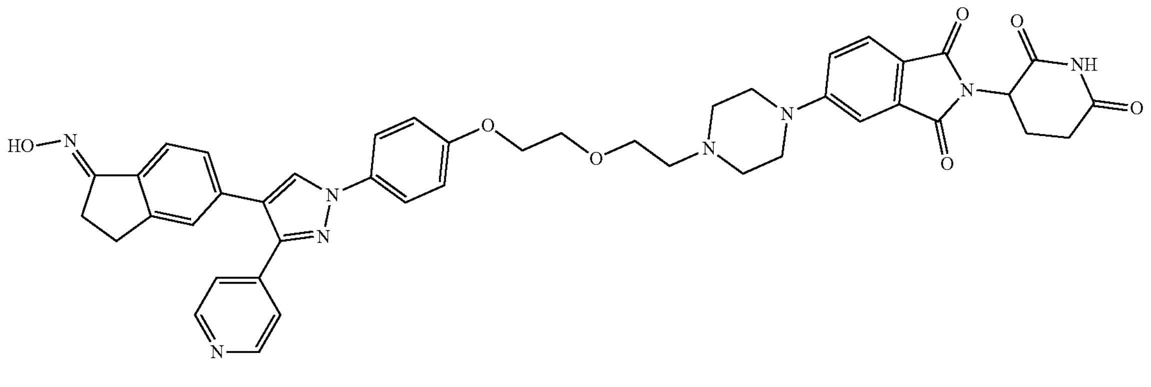 [SMILES: O=C1CCC(N2C(=O)c3ccc(N4CCN(CCOCCOc5ccc(-n6cc(-c7ccc8c(c7)CC/C8=N\O)c(-c7ccncc7)n6)cc5)CC4)cc3C2=O)C(=O)N1]

To a solution of 2-(2,6-dioxopiperidin-3-yl)-5-(4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazin-1-yl) isoindoline-1,3-dione (625 mg, 0.64 mmol, calculated) and hydroxylamine hydrochloride (667 mg, 9.60 mmol) in MeOH/DCM (4 mL/1 mL) was added $NaHCO_3$ (1.21 g, 14.4 mmol) at 50° C. The mixture was stirred at 50° C. for 10 minutes. The residue was purified by preparative TLC with DCM/MeOH=20/1, and then it was further purified by preparative HPLC to afford the desired product (34 mg) as a yellow solid. $^1$H NMR (400 MHZ, DMSO-$d_6$): δ 11.09 (s, 1H), 10.93 (s, 1H), 9.93 (br, 1H), 8.79 (s, 1H), 8.68 (s, 2H), 7.91 (d, J=8.4 Hz, 2H), 7.65-7.80 (m, 3H), 7.58 (d, J=8.0 Hz, 1H), 7.49 (s, 1H), 7.44 (s, 1H), 7.34 (d, J=8.4 Hz, 1H), 7.25 (d, J=8.0 Hz, 1H), 7.16 (d, J=8.8 Hz, 2H), 5.09 (m, 1H), 4.25 (m, 4H), 3.88 (m, 4H), 3.01 (m, 2H), 2.86 (m, 3H), 2.50 (m, 3H), 2.03 (m, 1H); LCMS (ES+): m/z 796.3 $[M+H]^+$.

Example Synthesis of Compound 198: (E)-2-(2,6-Dioxopiperidin-3-yl)-5-(2-(2-(4-(4-(4-(1-(hydroxy-imino)-2,3-dihydro-1H-inden-5-yl)-3-(pyridin-4-yl)-1H-pyrazol-1-yl)phenyl)piperazin-1-yl)ethoxy) ethoxy)isoindoline-1,3-dione

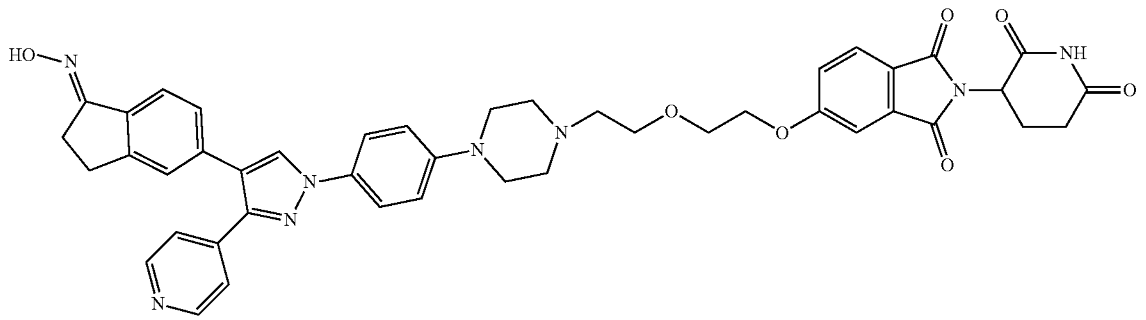 [SMILES: O=C1CCC(N2C(=O)c3ccc(OCCOCCN4CCN(c5ccc(-n6cc(-c7ccc8c(c7)CC/C8=N\O)c(-c7ccncc7)n6)cc5)CC4)cc3C2=O)C(=O)N1]

Step A: 5-(1-(4-(4-(2-(2-hydroxyethoxy)ethyl)piperazin-1-yl)phenyl)-3-(pyridin-4-yl)-1H-pyrazol-4-yl)-2,3-dihydro-1H-inden-1-one

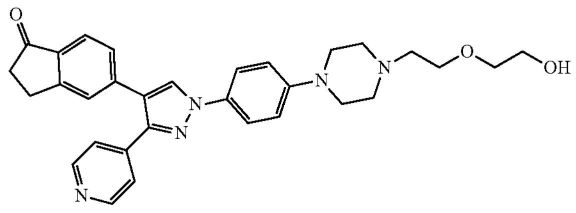 [SMILES: O=C1CCc2cc(-c3cn(-c4ccc(N5CCN(CCOCCO)CC5)cc4)nc3-c3ccncc3)ccc21]

To a solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (200 mg, 0.37 mmol) in MeOH (3 mL) was added 6 M HCl (g) in 1,4-dioxane (1 mL). The resulting solution was stirred at 25° C. for 1 hour. The solvent was removed under vacuum. The residue was diluted with 20 mL DCM, and the pH was adjusted to around 9 by progressively adding $NaHCO_3$ aqueous solution. The mixture was extracted with DCM. The combined organic layer was dried over $Na_2SO_4$, filtered and concentrated under reduced pressure to give the desired product, which was used directly in next step. To a solution of above intermediate (180 mg crude, 0.37 mmol) in DMF (3 mL) were added 2-(2-hydroxyethoxy)ethyl 4-methylbenzenesulfonate (194 mg, 0.75 mmol) and $K_2CO_3$ (153.2 mg, 1.11 mmol). The resultant solution was stirred at 70° C. for 2 hours. After cooling to room temperature, the reaction was diluted with DCM (20 mL), and the mixture was washed with brine. The organic phase was dried over $Na_2SO_4$, filtered and concentrated under reduced pressure. The residue was purified by preparative TLC to afford the desired product (53 mg, 27.2% yield) as a yellow solid. LCMS ($ES^+$): m/z 524.2 $[M+H]^+$.

Step B: tert-butyl 2-(2,6-dioxopiperidin-3-yl)-5-(2-(2-(4-(4-(4-(1-oxo-2,3-dihydro-1H-inden-5-yl)-3-(pyridin-4-yl)-1H-pyrazol-1-yl)phenyl)piperazin-1-yl)ethoxy)ethoxy)isoindoline-1,3-dione

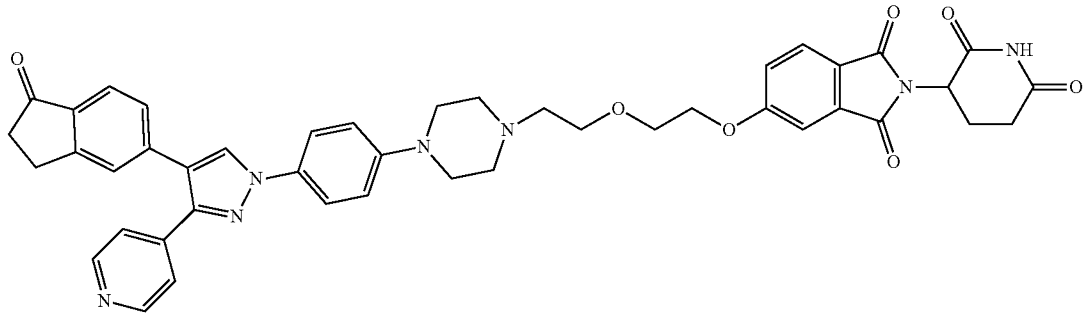 [SMILES: O=C1CCC(N2C(=O)c3ccc(OCCOCCN4CCN(c5ccc(-n6cc(-c7ccc8c(c7)CCC8=O)c(-c7ccncc7)n6)cc5)CC4)cc3C2=O)C(=O)N1]

To a solution of 5-(1-(4-(4-(2-(2-hydroxyethoxy)ethyl)piperazin-1-yl)phenyl)-3-(pyridin-4-yl)-1H-pyrazol-4-yl)-2,3-dihydro-1H-inden-1-one (53 mg, 0.10 mmol), $Ph_3P$ (78.7 mg, 0.3 mmol) and 2-(2,6-dioxopiperidin-3-yl)-5-fluoroisoindoline-1,3-dione (41.1 mg, 0.15 mmol) in dry THF (3.0 mL) was added DIAD (60.7 mg, 0.3 mmol) dropwise under $N_2$. The mixture was stirred at 20° C. for 1.5 hours. After it was quenched with $H_2O$ (20 mL), the mixture was extracted with DCM (20 mL×3). The combined organic layer was washed with brine, dried over $Na_2SO_4$, and concentrated under vacuum. The residue was purified by preparative TLC to afford the desired product (crude, 45 mg, 34.7% yield) as a yellow solid. LCMS ($ES^+$): m/z 780.3 $[M+H]^+$.

Step C: (E)-2-(2,6-dioxopiperidin-3-yl)-5-(2-(2-(4-(4-(4-(1-(hydroxyimino)-2,3-dihydro-1H-inden-5-yl)-3-(pyridin-4-yl)-1H-pyrazol-1-yl)phenyl)piperazin-1-yl)ethoxy)ethoxy)isoindoline-1,3-dione To a solution of tert-butyl 2-(2,6-dioxopiperidin-3-yl)-5-(2-(2-(4-(4-(4-(1-oxo-2,3-dihydro-1H-inden-5-yl)-3-(pyridin-4-yl)-1H-pyrazol-1-yl)phenyl)piperazin-1-yl)ethoxy)ethoxy)isoindoline-1,3-dione (45 mg, 0.058 mmol) in $CH_3CN$/pyridine (3.0 mL, v/v=2/1) was added hydroxylamine hydrochloride (40.1 mg, 0.58 mmol). The mixture was stirred at 40° C. for 20 minutes. Then the reaction was diluted with DCM (20 mL), and the mixture was washed with brine (10 mL×3). The combined organic layer was removed under vacuum, and the residue was purified by preparative TLC and preparative HPLC to afford the desired product (5.5 mg, 12% yield) as a yellow solid. NMR (400 MHz, $CDCl_3$): δ 8.55 (s, 2H), 8.04 (s, 1H), 7.94 (s, 1H), 7.79 (d, J=8.0 Hz, 1H), 7.65 (d, J=8.8 Hz, 3H), 7.39 (s, 2H), 7.30 (s, 1H), 7.23 (s, 1H), 7.01 (d, J=8.8 Hz, 2H), 4.98-4.93 (m, 1H), 4.27 (s, 2H), 3.90 (s, 2H), 3.77 (s, 2H), 3.28 (s, 4H), 3.06-3.01 (m, 4H), 2.93-2.81 (m, 2H), 2.74 (s, 7H), 2.17-2.13 (br, 1H). LCMS ($ES^+$): m/z 795.3 $[M+H]^+$.

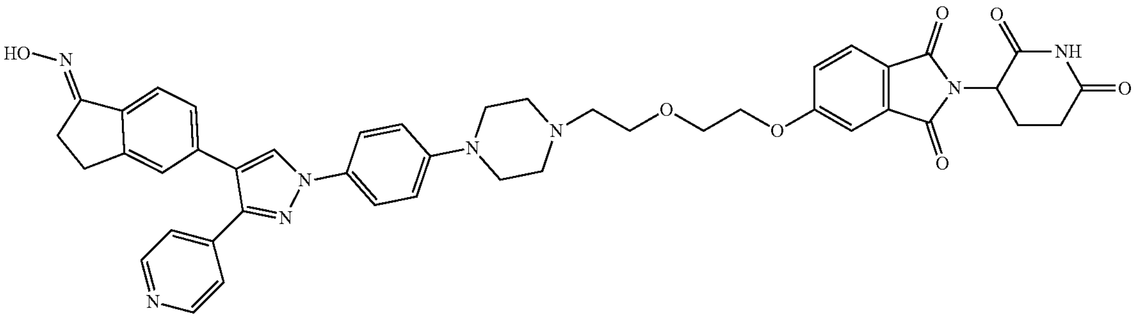 [SMILES: O=C1CCC(N2C(=O)c3ccc(OCCOCCN4CCN(c5ccc(-n6cc(-c7ccc8c(c7)CC/C8=N\O)c(-c7ccncc7)n6)cc5)CC4)cc3C2=O)C(=O)N1]

Example Synthesis of Compound 199: (E)-2-(2,6-dioxopiperidin-3-yl)-4-(3-(4-(4-(4-(1-(hydroxyimino)-2,3-dihydro-1H-inden-5-yl)-3-(pyridin-4-yl)-1H-pyrazol-1-yl)phenyl)piperazin-1-yl)propoxy)isoindoline-1,3-dione

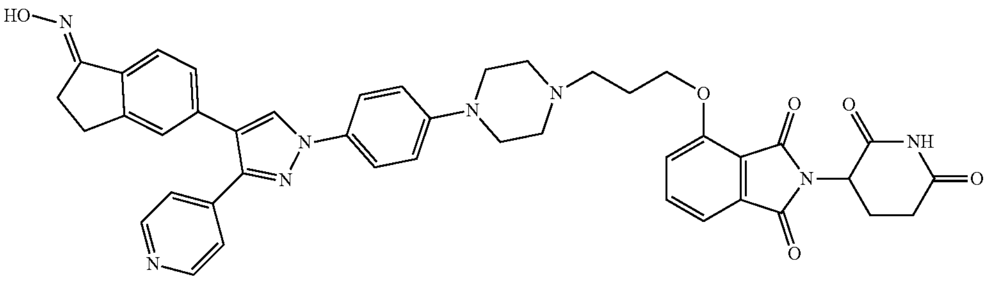 [SMILES: O=C1CCC(N2C(=O)c3cccc(OCCCN4CCN(c5ccc(-n6cc(-c7ccc8c(c7)CC/C8=N\O)c(-c7ccncc7)n6)cc5)CC4)c3C2=O)C(=O)N1]

Step A: 5-(1-(4-(4-(3-hydroxypropyl)piperazin-1-yl)phenyl)-3-(pyridin-4-yl)-1H-pyrazol-4-yl)-2,3-dihydro-1H-inden-1-one

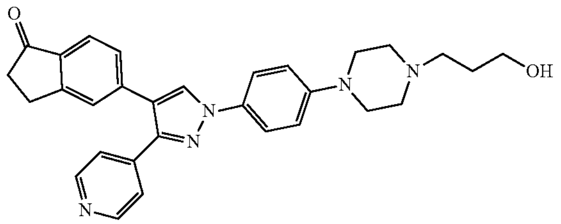 [SMILES: O=C1CCc2cc(-c3cn(-c4ccc(N5CCN(CCCO)CC5)cc4)nc3-c3ccncc3)ccc21]

To a solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (270 mg, 0.50 mmol) in MeOH (5 mL) was added 6 M HCl in 1,4-dioxane (1 mL). The resulting solution was stirred at 25° C. for 1 hour. The solvent was removed in vacuo. The residue was diluted with 20 mL DCM, and the pH was adjusted to ~ 9 by addition of $NaHCO_3$ aqueous. The mixture was extracted with DCM. The combined organic layer was dried over $Na_2SO_4$, filtered and concentrated under reduced pressure. The residue (240 mg crude) was used directly in next step without further purification.

To a solution of above intermediate (240 mg crude, 0.50 mmol) in DMF (5 mL) was added 3-hydroxypropyl 4-methylbenzenesulfonate (230 mg, 1 mmol) and $K_2CO_3$ (207 mg, 1.5 mmol). The resulting solution was stirred at 70° C. for 2 hours. After cooling to room temperature, the reaction was diluted with DCM (20 mL). The mixture was washed with brine, dried over $Na_2SO_4$. The solution was filtered and concentrated under reduced pressure. The residue was purified by preparative TLC to afford the desired product (100 mg, 30.5% yield) as a yellow solid. LCMS ($ES^+$): m/z 494.3 $[M+H]^+$.

Step B: tert-butyl 5-amino-4-(1,3-dioxo-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindolin-2-yl)-5-oxopentanoate

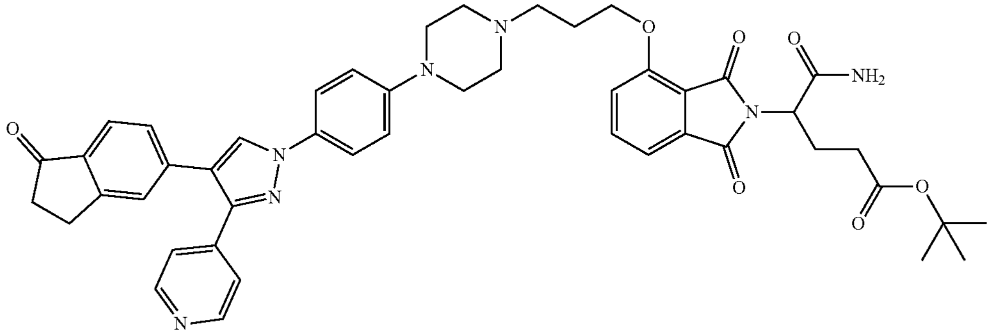 [SMILES: CC(C)(C)OC(=O)CCC(C(N)=O)N1C(=O)c2cccc(OCCCN3CCN(c4ccc(-n5cc(-c6ccc7c(c6)CCC7=O)c(-c6ccncc6)n5)cc4)CC3)c2C1=O]

To a solution of 5-(1-(4-(4-(3-hydroxypropyl)piperazin-1-yl)phenyl)-3-(pyridin-4-yl)-1H-pyrazol-4-yl)-2,3-dihydro-1H-inden-1-one (100 mg, 0.20 mmol) triphenylphosphine (157.2 mg, 0.60 mmol), and tert-butyl 5-amino-4-(4-hydroxy-1,3-dioxoisoindolin-2-yl)-5-oxopentanoate (104.4 mg, 0.30 mmol) in dry THF (5.0 mL) was added DIAD (121.2 mg, 0.60 mmol) dropwise under $N_2$. The mixture was stirred at 20° C. for 1.5 hours. The reaction was quenched with DCM (20 mL), and the mixture was washed with brine (10 mL×3). The organic phase was concentrated under vacuum. The residue was purified by preparative TLC to afford the desired product (120 mg, 43.1% yield) as a yellow solid. LCMS ($ES^+$): m/z 824.3 $[M+H]^+$.

Step C: 2-(2,6-dioxopiperidin-3-yl)-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindoline-1,3-dione

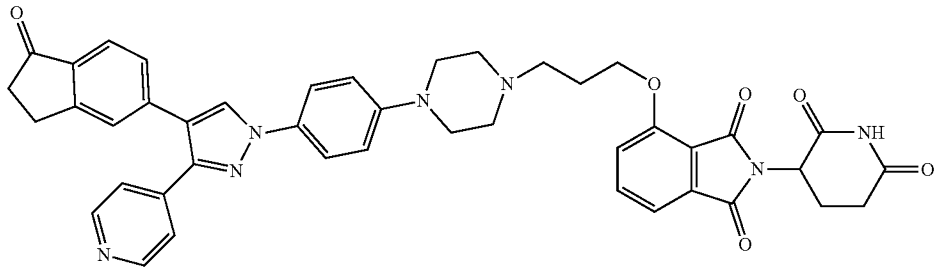 [SMILES: O=C1CCC(N2C(=O)c3cccc(OCCCN4CCN(c5ccc(-n6cc(-c7ccc8c(c7)CCC8=O)c(-c7ccncc7)n6)cc5)CC4)c3C2=O)C(=O)N1]

To a solution of tert-butyl 5-amino-4-(1,3-dioxo-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindolin-2-yl)-5-oxopentanoate (crude 120 mg, 0.087 mmol) in acetonitrile (5 mL) was added p-toluenesulfonic acid (45.2 mg, 0.26 mmol). The mixture was stirred at 80° C. for 3 hours. After cooling to room temperature, the reaction was diluted with DCM (30 mL), and the mixture was washed with brine (10 mL×2). The organic phase was dried over $Na_2SO_4$, and concentrated under vacuum. The residue was purified by preparative TLC to afford the desired product (40 mg, 61.1% yield) as a yellow solid. LCMS ($ES^+$): m/z 750.3 $[M+H]^+$.

Step D: (E)-2-(2,6-dioxopiperidin-3-yl)-4-(3-(4-(4-(4-(1-(hydroxyimino)-2,3-dihydro-1H-inden-5-yl)-3-(pyridin-4-yl)-1H-pyrazol-1-yl)phenyl)piperazin-1-yl)propoxy)isoindoline-1,3-dione

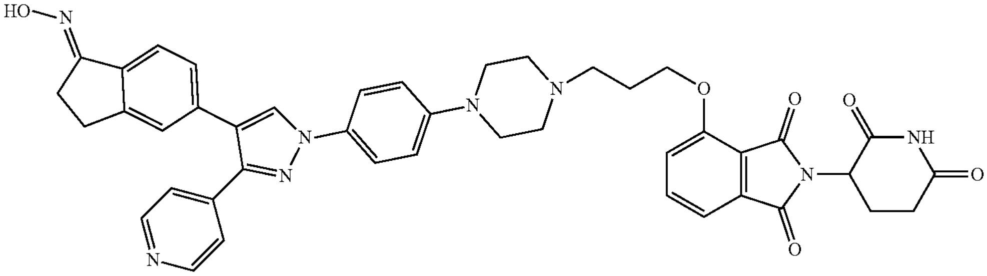 [SMILES: O=C1CCC(N2C(=O)c3cccc(OCCCN4CCN(c5ccc(-n6cc(-c7ccc8c(c7)CC/C8=N\O)c(-c7ccncc7)n6)cc5)CC4)c3C2=O)C(=O)N1]

To a solution of 2-(2,6-dioxopiperidin-3-yl)-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindoline-1,3-dione (40 mg, 0.053 mmol) in acetonitrile/pyridine (v/v=3/1, 4 mL) was added hydroxylamine hydrochloride (36.8 mg, 0.53 mmol). The mixture was stirred at 40° C. for 20 minutes, and then it was diluted with DCM (20 mL). The mixture was washed with brine (10 mL×2). The organic phase was dried over $Na_2SO_4$, and concentrated under vacuum. The residue was purified by preparative TLC and preparative HPLC to afford the desired product (7.5 mg, 18.4% yield) as yellow solid. NMR (400 MHz, DMSO-$d_6$): δ 11.11 (s, 1H), 10.90 (s, 1H), 8.70 (s, 1H), 8.57-8.56 (m, 2H), 7.85-7.77 (m, 3H), 7.56 (d, J=8.0 Hz, 2H), 7.49-7.45 (m, 3H), 7.41 (s, 1H), 7.22 (d, J=8.0 Hz, 1H), 7.10-7.08 (m, 2H), 5.12-5.08 (m, 1H), 4.32-4.28 (m, 2H), 3.22 (s, 5H), 3.03-2.97 (m, 2H), 2.89-2.80 (m, 3H), 2.62-2.57 (m, 7H), 2.06-1.99 (m, 3H). LCMS ($ES^+$): m/z 765.2 $[M+H]^+$.

Example Synthesis of Compound 200: (E)-2-(2,6-Dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl)phenoxy)propoxy)phenyl) isoindoline-1,3-dione

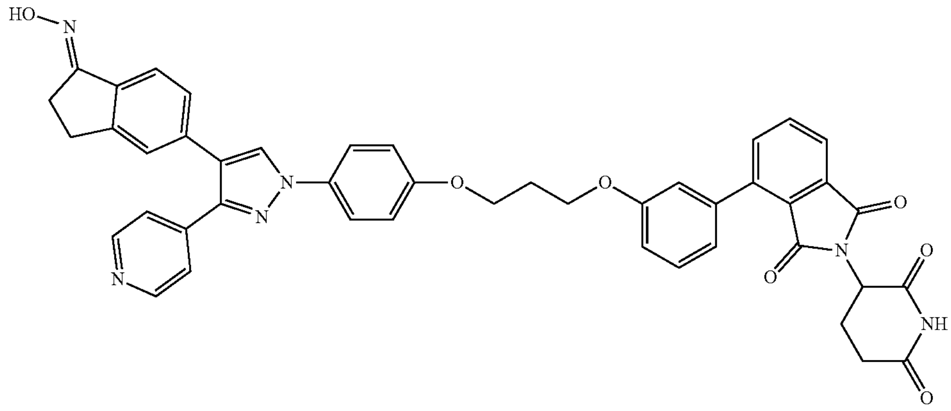 [SMILES: O=C1CCC(N2C(=O)c3cccc(-c4cccc(OCCCOc5ccc(-n6cc(-c7ccc8c(c7)CC/C8=N\O)c(-c7ccncc7)n6)cc5)c4)c3C2=O)C(=O)N1]

Step A: 3-(4-(4-bromo-3-(pyridin-4-yl)-1H-pyrazol-1-yl)phenoxy)propan-1-ol

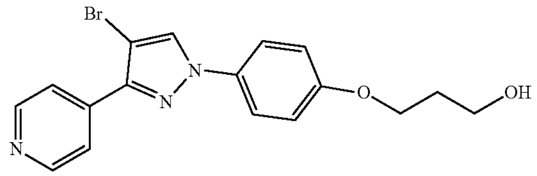 [SMILES: OCCCOc1ccc(-n2cc(Br)c(-c3ccncc3)n2)cc1]

To a solution of 4-(4-bromo-1H-pyrazol-3-yl) pyridine (500 mg, 1.58 mmol) in dry DMF (10.0 mL) were added $K_2CO_3$ (434 mg, 3.16 mmol) and 3-hydroxypropyl 4-methylbenzenesulfonate (400 mg, 1.74 mmol) subsequently. The resulting solution was stirred at 80° C. for 3 hours. The reaction mixture was diluted with EA (30 mL) and washed with brine. The organic phase was dried over anhydrous sodium sulfate and concentrated under vacuum. The residue was purified to afford the desired product 3-(4-(4-bromo-3-(pyridin-4-yl)-1H-pyrazol-1-yl)phenoxy)propan-1-ol (PE: EA=1:1) (400 mg, 67% yield) as light yellow oil. LCMS ($ES^+$): m/z 376.0 $[M+H]^+$.

Step B: 3-(4-(4-bromo-3-(pyridin-4-yl)-1H-pyrazol-1-yl)phenoxy)propan-1-ol

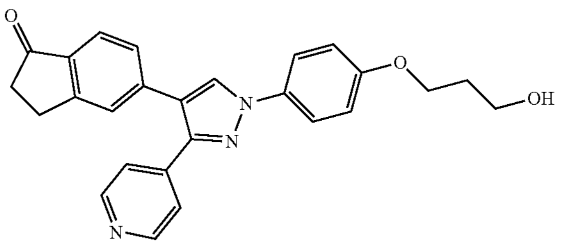 [SMILES: O=C1CCc2cc(-c3cn(-c4ccc(OCCCO)cc4)nc3-c3ccncc3)ccc21]

To a solution of 3-(4-(4-bromo-3-(pyridin-4-yl)-1H-pyrazol-1-yl)phenoxy) propan-1-ol (400 mg, 1.07 mmol), 5-(4,4,5,5-tetramethyl-1,3,2-dioxaborolan-2-yl)-2,3-dihydro-1H-inden-1-one (414 mg, 1.6 mmol), $Pd_2(dba)_3$ (392 mg, 0.427 mmol), CsF (650 mg, 4.28 mmol), tri-tert-butylphosphine tetrafluoroborate (248 mg, 0.855 mmol), N,N-dicyclohexylmethylamine (9.0 mg, 0.047 mmol) in a mixture of 10% of water in 1,4-dioxane (10 mL) was irradiated with at 100° C. with microwave under $N_2$ for 2 hours. The mixture was cooled to room temperature and quenched with water. The mixture was diluted with EA and washed with water, and brine. The organic phase was dried over anhydrous sodium sulfate and concentrated under vacuum. The residue was purified to afford the desired product 3-(4-(4-bromo-3-(pyridin-4-yl)-1H-pyrazol-1-yl)phenoxy) propan-1-ol (DCM:MeOH=50:1) (450 mg, 87% yield) as yellow solid. LCMS ($ES^+$): m/z 426.1 $[M+H]^+$.

Step C: 5-(3-(pyridin-4-yl)-1-(4-(3-(3-(4,4,5,5-tetramethyl-1,3,2-dioxaborolan-2-yl)phenoxy)propoxy)phenyl)-1H-pyrazol-4-yl)-2,3-dihydro-1H-inden-1-one

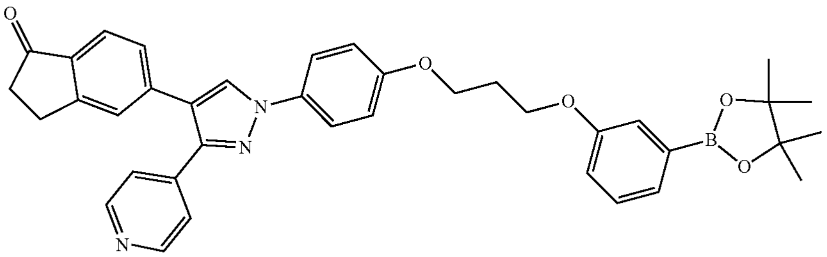 [SMILES: CC1(C)OB(c2cccc(OCCCOc3ccc(-n4cc(-c5ccc6c(c5)CCC6=O)c(-c5ccncc5)n4)cc3)c2)OC1(C)C]

To a solution of 3-(4-(4-bromo-3-(pyridin-4-yl)-1H-pyrazol-1-yl)phenoxy) propan-1-ol (450 mg, 1.06 mmol) and TEA (214 mg, 2.12 mmol) in DCM (10.0 mL) was added MsCl (145 mg, 1.27 mmol) dropwise at 0° C. The resulting solution was stirred at 25° C. for 1 hours. The solvent was evaporated and the residue was diluted with EA (50 mL). The solution was washed with saturated $NaHCO_3$ and brine. The organic layer was dried over anhydrous sodium sulfate. The solvent was removed under vacuum to afford crude desired product (520 mg crude), which was used in next step directly. To a solution of above desired product (520 mg, 1.03 mmol) in dry DMF (10 mL) were added $K_2CO_3$ (285 mg, 2.07 mmol) and 3-(4,4,5,5-tetramethyl-1,3,2-dioxaborolan-2-yl)phenol (341 mg, 1.55 mmol). The resulting solution was stirred at 70° C. overnight. After cooling to room temperature, the reaction mixture was diluted with EA (50 mL), and the mixture was washed with water, brine. The organic layer was dried over anhydrous sodium sulfate. The residue was purified by chromatography column to afford 5-(3-(pyridin-4-yl)-1-(4-(3-(3-(4,4,5,5-tetramethyl-1,3,2-dioxaborolan-2-yl)phenoxy)propoxy)phenyl)-1H-pyrazol-4-yl)-2,3-dihydro-1H-inden-1-one (200 g, 32% yield in two steps). $^1$H NMR (400 MHz, $CDCl_3$): δ 8.62 (d, J=6 Hz, 2H), 8.00 (s, 1H), 7.76 (d, J=7.6 Hz, 1H), 7.68 (d, J=7.6 Hz, 2H), 7.51 (d, J=4.4 Hz, 2H), 7.27-7.44 (m, 4H), 7.02-7.04 (m, 3H), 4.15-4.22 (m, 3H), 4.11-4.13 (m, 4H), 3.12-3.14 (m, 2H), 2.72-2.75 (m, 2H), 2.10 (s, 1H), 1.34 (s, 11H), 2.83 (s, 1H).

Step D: 2-(2,6-dioxopiperidin-3-yl)-4-(3-(3-(4-(4-(1-oxo-2,3-dihydro-1H-inden-5-yl)-3-(pyridin-4-yl)-1H-pyrazol-1-yl)phenoxy)propoxy)phenyl)isoindoline-1,3-dione

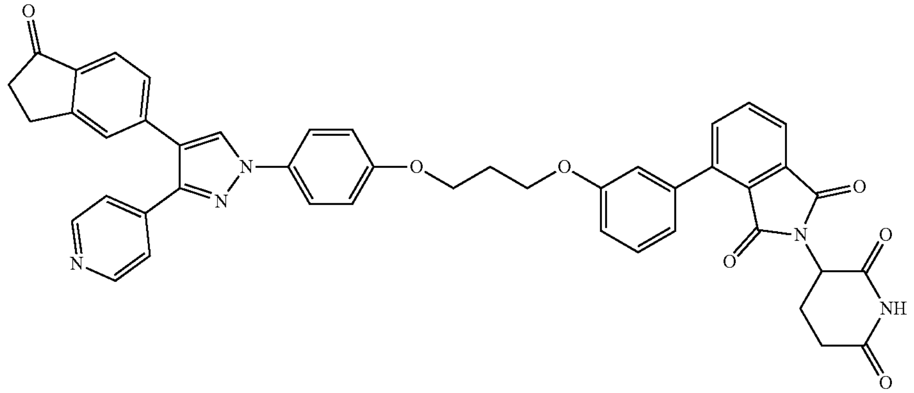 [SMILES: O=C1CCC(N2C(=O)c3cccc(-c4cccc(OCCCOc5ccc(-n6cc(-c7ccc8c(c7)CCC8=O)c(-c7ccncc7)n6)cc5)c4)c3C2=O)C(=O)N1]

To a solution of 4-chloro-2-(2,6-dioxopiperidin-3-yl) isoindoline-1,3-dione (47 mg, 0.159 mmol) and 5-(3-(pyridin-4-yl)-1-(4-(3-(3-(4,4,5,5-tetramethyl-1,3,2-dioxaborolan-2-yl)phenoxy)propoxy)phenyl)-1H-pyrazol-4-yl)-2,3-dihydro-1H-inden-1-one (47 mg, 0.159 mmol) in dioxane (5 mL)/$H_2O$ (0.5 mL) were added CsF (97 mg, 0.64 mmol), Pd(aMphos)$Cl_2$ (12 mg, 0.016 mmol). After stirring at 100° C. for 2 hours under nitrogen atmosphere, the reaction mixture was diluted with 30 mL of ethyl acetate, and the solution was washed with brine (10 mLx3). The organic phase was dried over anhydrous sodium sulfate and concentrated under vacuum. The residue was purified by preparative TLC (DCM/MeOH=20/1) to afford the desired product 2-(2,6-dioxopiperidin-3-yl)-4-(3-(3-(4-(4-(1-oxo-2,3-dihydro-1H-inden-5-yl)-3-(pyridin-4-yl)-1H-pyrazol-1-yl)phenoxy)propoxy)phenyl)isoindoline-1,3-dione (50 mg, 40% yield) as yellow solid. LCMS ($ES^+$): m/z 758.2 $[M+H]^+$.

Step E: (E)-2-(2,6-dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl)phenoxy)propoxy) phenyl)isoindoline-1,3-dione

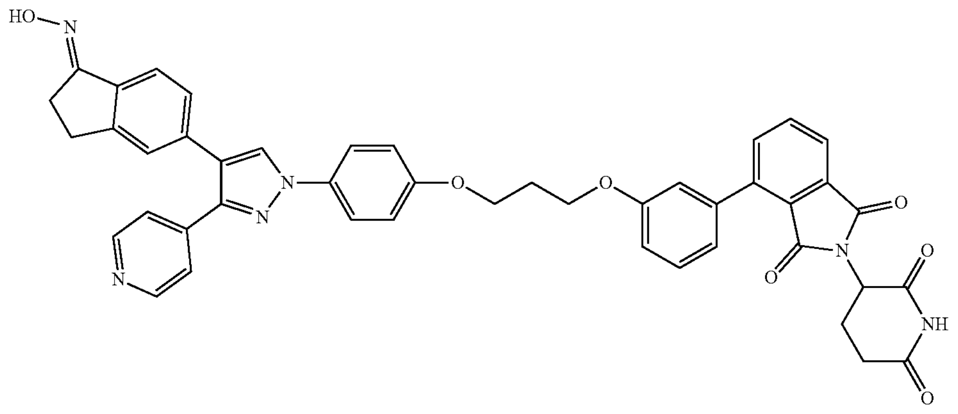 [SMILES: O=C1CCC(N2C(=O)c3cccc(-c4cccc(OCCCOc5ccc(-n6cc(-c7ccc8c(c7)CC/C8=N\O)c(-c7ccncc7)n6)cc5)c4)c3C2=O)C(=O)N1]

To a solution of 2-(2,6-dioxopiperidin-3-yl)-4-(3-(3-(4-(4-(1-oxo-2,3-dihydro-1H-inden-5-yl)-3-(pyridin-4-yl)-1H-pyrazol-1-yl)phenoxy)propoxy) phenyl)isoindoline-1,3-dione (50 mg, 0.053 mmol) in acetonitrile (2 mL) and pyridine (1 mL) was added hydroxylamine hydrochloride (34 mg, 0.53 mmol). After stirring 20 minutes at 40° C., the reaction was diluted with DCM (20 mL), and the mixture was washed with brine (10 mL×2). The organic phase was dried over $Na_2SO_4$, and concentrated under vacuum, The residue was purified by preparative TLC to afford (E)-2-(2,6-dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl) phenoxy)propoxy) phenyl)isoindolin-e-1,3-dione (26 mg, 51% yield) as yellow solid. NMR (400 MHz, DMSO-d6): δ 11.09 (s, 1H), 10.89 (s, 1H), 8.73 (s, 1H), 8.57 (d, J=5.2 Hz, 2H), 7.82-7.92 (m, 5H), 7.56 (d, J=8.0 Hz, 1H), 7.48 (d, J=4.8 Hz, 2), 7.37-7.41 (m, 2), 7.09-7.23 (m, 6H), 5.05-5.10 (m, 1H), 4.22-4.29 (m, 4H), 4.10 (s, 1H), 3.17 (d, J=4.8 Hz, 1H), 2.99-3.01 (m, 2H), 2.81-2.84 (m, 3H), 2.22-2.54 (m, 1H), 2.02-2.08 (m, 1H); LCMS ($ES^+$): m/z 773.2 $[M+H]^+$.

Example Synthesis of Compound 201

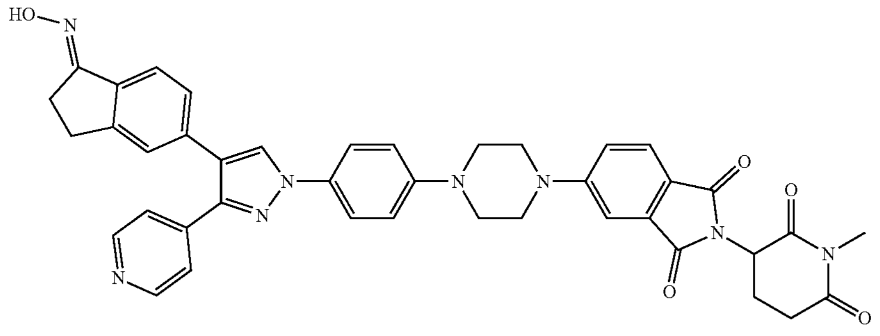 [SMILES: CN1C(=O)CCC(N2C(=O)c3ccc(N4CCN(c5ccc(-n6cc(-c7ccc8c(c7)CC/C8=N\O)c(-c7ccncc7)n6)cc5)CC4)cc3C2=O)C1=O]

Step A: 5-fluoro-2-(1-methyl-2,6-dioxopiperidin-3-yl)isoindoline-1,3-dione

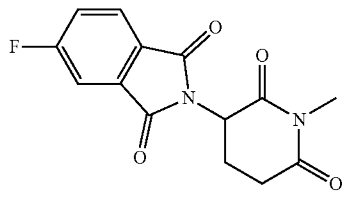 [SMILES: CN1C(=O)CCC(N2C(=O)c3ccc(F)cc3C2=O)C1=O]

To a solution of 2-(2,6-dioxopiperidin-3-yl)-5-fluoroisoindoline-1,3-dione (500 mg, 1.81 mmol) in dry DMF (10.0 mL) was added NaH (145 mg, 3.62 mmol) at 0° C. After stirring for 0.5 h, $CH_3I$ (513.7 mg, 3.62 mmol) was added at 0° C. The resulting solution was stirred for 2 hours. After quenched with $NH_4Cl$ aq., the mixture was diluted with 30 mL EA, and washed with brine (20 mL×3). The organic phase was dried over $Na_2SO_4$, concentrated to afford 5-Fluoro-2-(1-methyl-2,6-dioxopiperidin-3-yl)isoindoline-1,3-dione (500 mg, 95.2% yield) as brown solid, which was used next step directly. LCMS ($ES^+$): m/z 291.1 $[M+H]^+$.

Step B: 2-(1-methyl-2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione

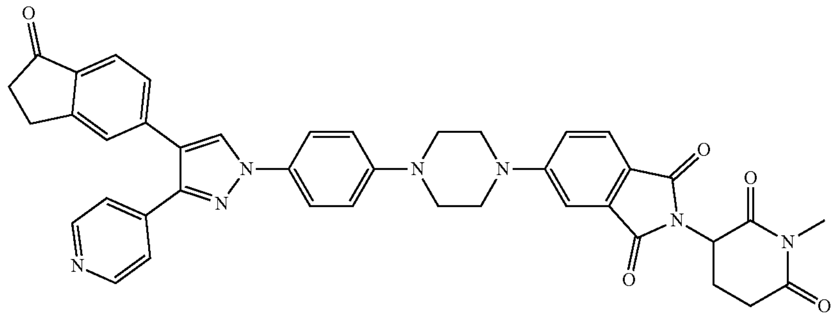 [SMILES: CN1C(=O)CCC(N2C(=O)c3ccc(N4CCN(c5ccc(-n6cc(-c7ccc8c(c7)CCC8=O)c(-c7ccncc7)n6)cc5)CC4)cc3C2=O)C1=O]

To a solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (100 mg, 0.19 mmol) in MeOH (3 mL) was added 6 M HCl in 1,4-dioxane (1 mL). The resulting solution was stirred at 25° C. for 1 hour. The solution was concentrated and diluted with 20 mL DCM, added $NaHCO_3$ aq. to pH>7. The mixture was extracted with DCM. The organic layer was dried over $Na_2SO_4$, filtered and concentrated under reduced pressure which was used directly in next step. To a solution of above intermediate (90 mg crude, 0.19 mmol) in NMP (5 mL) was added 5-fluoro-2-(1-methyl-2,6-dioxopiperidin-3-yl)isoindoline-1,3-dione (100 mg, 0.29 mmol) and DIEA (245.1 mg, 1.9 mmol). The resulting solution was irradiated at 150° C. with microwave for 2 hours. After cooing to room temperature, it was diluted with DCM (20 mL), and the mixture was washed with brine. The organic phase was dried over $Na_2SO_4$, filtered and concentrated under reduced pressure. The residue was purified by silica gel column to afford 2-(1-methyl-2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (43 mg, 26.5% yield). LCMS ($ES^+$): m/z 706.3 $[M+H]^+$.

Step C: (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione

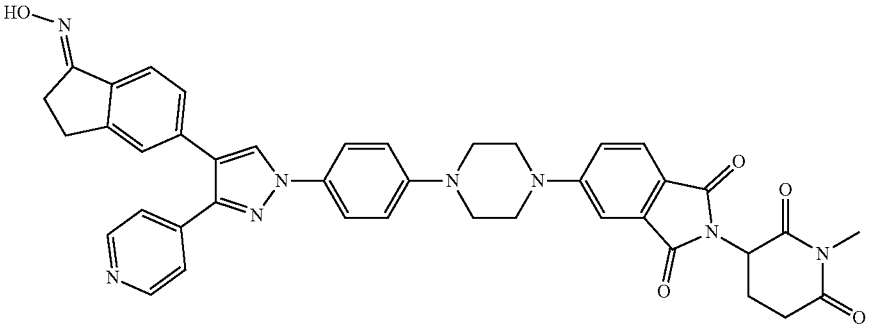 [SMILES: CN1C(=O)CCC(N2C(=O)c3ccc(N4CCN(c5ccc(-n6cc(-c7ccc8c(c7)CC/C8=N\O)c(-c7ccncc7)n6)cc5)CC4)cc3C2=O)C1=O]

To a solution of 2-(1-methyl-2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (43 mg, 0.061 mmol) in acetonitrile/pyridine (3 mL, v/v=2/1) was added hydroxylamine hydrochloride (42.4 mg, 0.61 mmol) at room temperature. The mixture was heated to 40° C. for 40 minutes. After cooling to room temperature, it was diluted with DCM (20 mL), washed with brine (10 mL). The organic phase was concentrated under vacuum. The residue was purified by preparative TLC to afford (E)-2-(2, 6-dioxopiperidin-3-yl)-5-(4-(4-(4-(1-(hydroxyimino)-2,3-dihydro-1H-inden-5-yl)-3-(pyridin-4-yl)-1H-pyrazol-1-yl) phenyl)piperazin-1-yl)isoindoline-1,3-dione (23 mg, 52.3% yield) as a yellow solid. NMR (400 MHz, DMSO-d6): δ 10.90 (s, 1H), 8.73 (s, 1H), 8.58-8.56 (d, J=8.0 Hz, 2H), 7.84-7.82 (d, J=8.8 Hz, 2H), 7.74-7.72 (d, J=8.4 Hz, 1H), 7.56-7.55 (d, J=8.4 Hz, 1H), 7.49-7.48 (m, 2H), 7.43-7.41 (m, 2H), 7.36-7.34 (m, 1H), 7.22-7.21 (d, J=8.0 Hz, 1H), 7.17-7.15 (d, J=10 Hz, 2H), 5.18-5.14 (m, 1H), 3.66 (s, 4H), 3.42 (s, 4H), 3.02-2.91 (m, 6H), 2.85-2.74 (m, 3H), 2.60-2.53 (m, 1H), 2.09-2.00 (br, 1H). LCMS ($ES^+$): m/z 721.3 $[M+H]^+$.

Example Synthesis of Compound 202: (3R)—N-(3-(5-(4-(4-(2-(4-(2-(2,6-Dioxopiperidin-3-yl)-1,3-dioxoisoindolin-5-yl)piperazin-1-yl)ethyl)piperazin-1-yl)phenyl)-1H-pyrrolo[2,3-b]pyridine-3-carbonyl)-2,4-difluorophenyl)-3-fluoropyrrolidine-1-sulfonamide

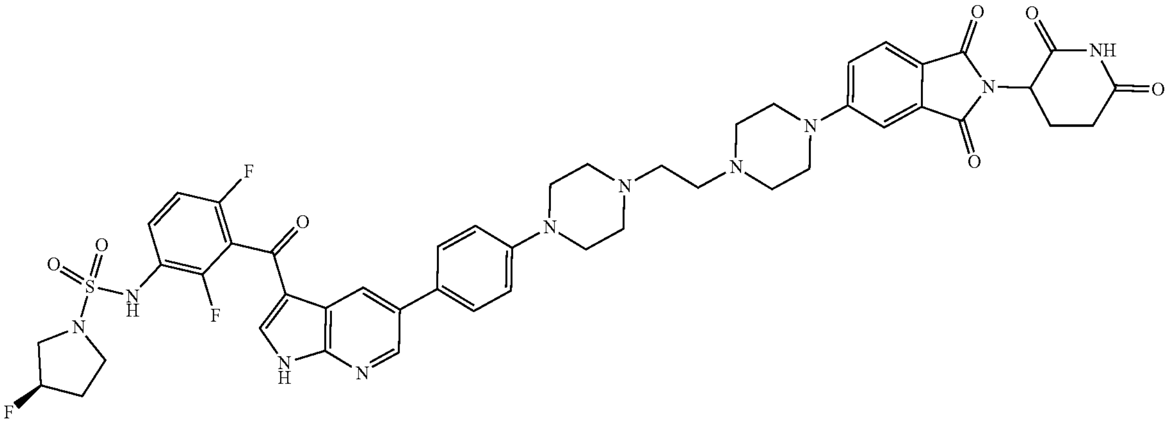 [SMILES: O=C1CCC(N2C(=O)c3ccc(N4CCN(CCN5CCN(c6ccc(-c7cnc8[nH]cc(C(=O)c9c(F)ccc(NS(=O)(=O)N%10CC[C@@H](F)C%10)c9F)c8c7)cc6)CC5)CC4)cc3C2=O)C(=O)N1]

Step A: 1-(4-bromophenyl)-4-(2,2-diethoxyethyl)piperazine

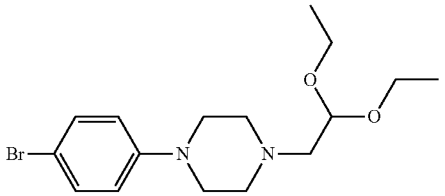 [SMILES: CCOC(CN1CCN(c2ccc(Br)cc2)CC1)OCC]

To a solution of 1-(4-bromophenyl)piperazine (5 g, 20.8 mmol) in dry DMF (50 ml) was added 2-bromo-1,1-diethoxyethane (4.1 g, 20.8 mmol) and $K_2CO_3$ (8.6 g, 62.4 mmol). The resulting solution was stirred at 90° C. for 16 hours. The reaction was diluted with EA (50 mL) and the mixture was washed (20 mL×2). The organic layer was dried over anhydrous sodium sulfate and concentrated under vacuum. The residue was applied onto a silica gel column to afford desired product (6 g, 81% yield) as oil.

$^1$H NMR (400 MHz, $CDCl_3$): δ 7.32 (d, J=9.2 Hz, 2H), 6.77 (d, J=8.8 Hz, 2H), 4.67 (t, J=5.2 Hz, 1H), 3.69-3.72 (m, 2H), 3.54-3.58 (m, 2H), 3.15 (m, 4H), 2.68-2.71 (m, 4H), 2.60 (d, J=5.2 Hz, 2H), 1.22 (t, J=7.2 Hz, 6H).

Step B: 1-(2,2-diethoxyethyl)-4-(4-(4,4,5,5-tetramethyl-1,3,2-dioxaborolan-2-yl)phenyl) piperazine

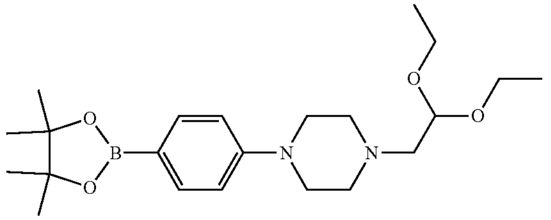 [SMILES: CCOC(CN1CCN(c2ccc(B3OC(C)(C)C(C)(C)O3)cc2)CC1)OCC]

To a solution of 1-(4-bromophenyl)-4-(2,2-diethoxyethyl) piperazine (7.8 g crude, 21.9 mmol) in 1,4-dioxane (70 mL) were added 4,4,4',4',5,5,5',5'-octamethyl-2,2'-bi(1,3,2-dioxaborolane) (8.3 g, 32.8 mmol), Pd(dppf)$Cl_2$ (1.6 g, 2.2 mmol) and KOAc (6.4 g, 65.6 mmol). The resulting solution was stirred overnight at 90° C. under $N_2$ atmosphere. TLC showed completion of the reaction. After cooled to room temperature, the reaction mixture was concentrated and purified by chromatography column to afford 1-(2,2-diethoxy ethyl)-4-(4-(4,4,5,5-tetramethyl-1,3,2-dioxaborolan-2-yl)phenyl)piperazine (5 g, 74% yield). $^1$H NMR (400 MHz, $CDCl_3$): δ 7.69 (d, J=8.4 Hz, 2H), 6.87 (d, J=8.4 Hz, 2H), 4.70 (m, 1H), 3.50-3.72 (m, 4H), 3.26 (m, 4H), 2.72 (m, 4H), 2.60 (d, J=5.2 Hz, 2H), 1.32 (s, 12H), 1.22 (t, J=7.2 Hz, 6H).

Step C: (R)—N-(3-(5-(4-(4-(2,2-diethoxyethyl)piperazin-1-yl)phenyl)-1H-pyrrolo[2,3-b]pyridine-3-carbonyl)-2,4-difluorophenyl)-3-fluoropyrrolidine-1-sulfonamide

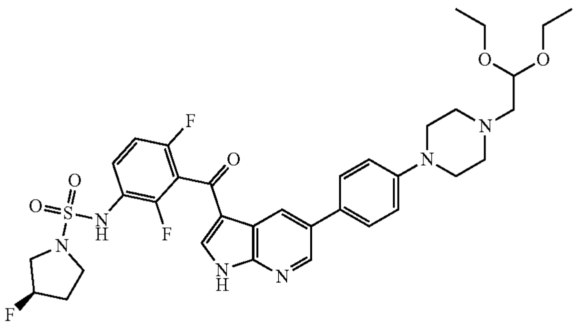 [SMILES: CCOC(CN1CCN(c2ccc(-c3cnc4[nH]cc(C(=O)c5c(F)ccc(NS(=O)(=O)N6CC[C@@H](F)C6)c5F)c4c3)cc2)CC1)OCC]

To a solution of (R)—N-(3-(5-bromo-1H-pyrrolo[2,3-b]pyridine-3-carbonyl)-2,4-difluorophenyl)-3-fluoropyrrolidine-1-sulfonamide (300 mg, 0.60 mmol) in 1,4-dioxane/$H_2O$ (10 mL/2 mL) was added 1-(2,2-diethoxyethyl)-4-(4-(4,4,5,5-tetramethyl-1,3,2-dioxaborolan-2-yl)phenyl)piperazine (726 mg, 1.80 mmol), Pd(aMphos)$Cl_2$ (42 mg, 0.06 mmol) and CsF (363 mg, 3.20 mmol). The resulting solution was stirred at 95° C. for 3 hours under $N_2$ atmosphere. TLC showed completion of the reaction. After cooling to room temperature, the reaction mixture was diluted with EA (50 mL), washed with water and brine. The organic layer was dried over anhydrous sodium sulfate. The residue was purified by chromatography column to afford (R)—N-(3-(5-(4-(4-(2,2-Diethoxyethyl)piperazin-1-yl)phenyl)-1H-pyrrolo[2,3-b]pyridine-3-carbonyl)-2,4-difluorophenyl)-3-fluoropyrrolidine-1-sulfonamide (350 mg, 70% yield). LCMS ($ES^+$): m/z 701.3 $[M+H]^+$.

Step D: (R)—N-(2,4-difluoro-3-(5-(4-(4-(2-oxoethyl)piperazin-1-yl)phenyl)-1H-pyrrolo[2,3-b]pyridine-3-carbonyl)phenyl)-3-fluoropyrrolidine-1-sulfonamide

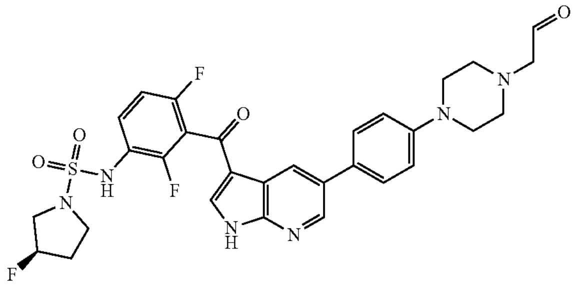 [SMILES: O=CCN1CCN(c2ccc(-c3cnc4[nH]cc(C(=O)c5c(F)ccc(NS(=O)(=O)N6CC[C@@H](F)C6)c5F)c4c3)cc2)CC1]

To a solution of (R)—N-(3-(5-(4-(4-(2,2-diethoxyethyl)piperazin-1-yl)phenyl)-1H-pyrrolo[2,3-b]pyridine-3-carbonyl)-2,4-difluorophenyl)-3-fluoropyrrolidine-1-sulfonamide (350 mg, 0.50 mmol) in $CH_3CN$ (10 mL) was added concentrated HCl (3 mL, which was diluted with 9 mL $H_2O$). The resulting solution was stirred at 55° C. for 16 hours. After cooled to room temperature, the reaction mixture was added sat. $NaHCO_3$ to adjust pH to 7~8. Lots of solid was observed. The suspension was extracted by DCM. The organic phase was dried over anhydrous sodium sulfate and concentrated to afford (R)—N-(2,4-Difluoro-3-(5-(4-(4-(2-oxoethyl)piperazin-1-yl)phenyl)-1H-pyrrolo[2,3-b]pyridine-3-carbonyl)phenyl)-3-fluoropyrrolidine-1-sulfonamide (490 mg, crude). LCMS ($ES^+$): m/z 645.2 $[M+H+18]^+$.

Step E: (3R)—N-(3-(5-(4-(4-(2-(4-(2-(2,6-Dioxopiperidin-3-yl)-1,3-dioxoisoindolin-5-yl)piperazin-1-yl)ethyl)piperazin-1-yl)phenyl)-1H-pyrrolo[2,3-b]pyridine-3-carbonyl)-2,4-difluorophenyl)-3-fluoropyrrolidine-1-sulfonamide

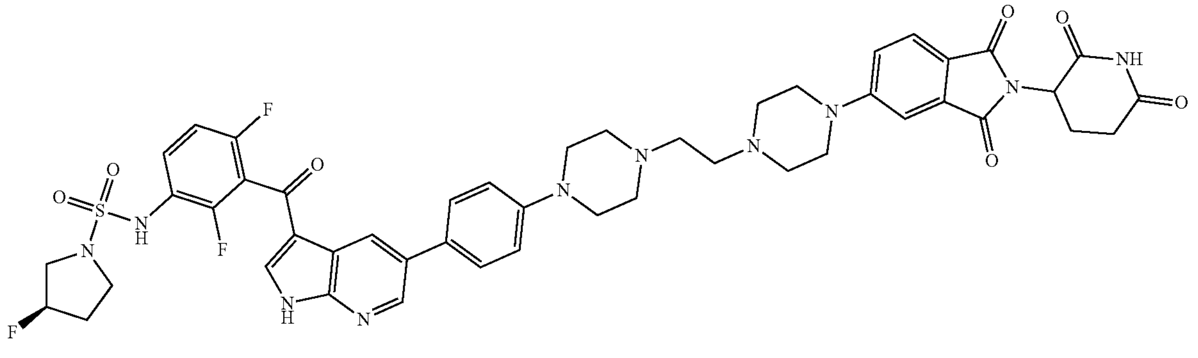 [SMILES: O=C1CCC(N2C(=O)c3ccc(N4CCN(CCN5CCN(c6ccc(-c7cnc8[nH]cc(C(=O)c9c(F)ccc(NS(=O)(=O)N%10CC[C@@H](F)C%10)c9F)c8c7)cc6)CC5)CC4)cc3C2=O)C(=O)N1]

To a solution of (R)—N-(2,4-difluoro-3-(5-(4-(4-(2-oxoethyl)piperazin-1-yl)phenyl)-1H-pyrrolo[2,3-b]pyridine-3-carbonyl)phenyl)-3-fluoropyrrolidine-1-sulfonamide (490 mg crude, 0.80 mmol) in THF/MeOH/DMSO (15 mL, 1/1/1) was added 2-(2,6-dioxopiperidin-3-yl)-5-(piperazin-1-yl)isoindoline-1,3-dione hydrochloride (364 mg, 0.96 mmol) and two drops of AcOH. Then $NaBH_3CN$ (248 mg, 4.00 mmol) was added. The resultant solution was stirred at 20° C. for 2 hours. The reaction mixture was diluted with 20 mL of saturated NaCl solution and extracted with DCM. The organic phase was dried over anhydrous sodium sulfate and concentrated. Crude was applied onto a silica gel column first and then by preparative HPLC to afford desired product (3R)—N-(3-(5-(4-(4-(2-(4-(2-(2,6-Dioxopiperidin-3-yl)-1,3-dioxoisoindolin-5-yl)piperazin-1-yl)ethyl)piperazin-1-yl)phenyl)-1H-pyrrolo[2,3-b]pyridine-3-carbonyl)-2,4-difluorophenyl)-3-fluoropyrrolidine-1-sulfonamide (75 mg, 16% yield in two steps) as yellow solid. NMR (400 MHz, DMSO-d6): δ 12.92 (s, 1H), 11.08 (s, 1H), 9.80 (br, 1H), 8.54-8.66 (m, 2H), 8.07 (s, 1H), 7.59-7.69 (m, 4H), 7.25-7.35 (m, 3H), 7.07 (d, J=8.4 Hz, 2H), 5.05-5.36 (m, 2H), 3.22-3.48 (m, 14H), 2.55-3.00 (m, 14H), 1.90-2.20 (m, 4H); LCMS ($ES^+$): m/z 954.3 $[M+H]^+$.

Step B: 5-(1-(3-(2-(Benzyloxy)ethoxy)phenyl)-3-(pyridin-4-yl)-1H-pyrazol-4-yl)-2,3-dihydro-1H-inden-1-one

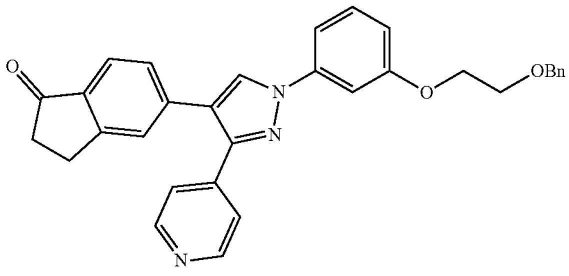

Example Synthesis of Compound 203: (E)-2-(2,6-Dioxopiperidin-3-yl)-5-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione

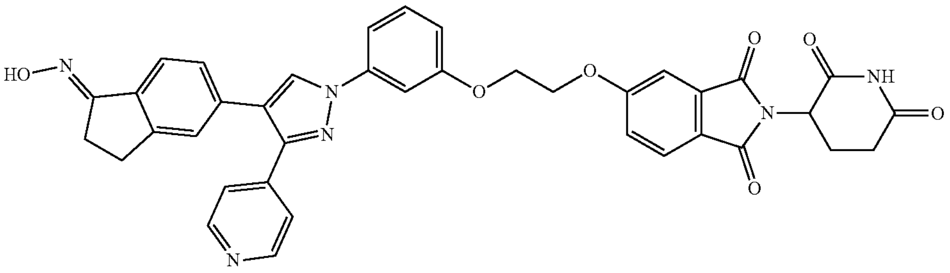 [SMILES: O=C1CCC(N2C(=O)c3ccc(OCCOc4cccc(-n5cc(-c6ccc7c(c6)CC/C7=N\O)c(-c6ccncc6)n5)c4)cc3C2=O)C(=O)N1]

Step A: 4-(1-(3-(2-(benzyloxy)ethoxy)phenyl)-4-bromo-1H-pyrazol-3-yl)pyridine

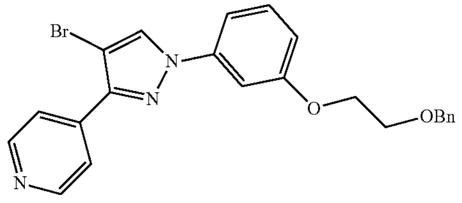 [SMILES: Brc1cn(-c2cccc(OCCOCc3ccccc3)c2)nc1-c1ccncc1]

To a solution of 2-(3-(2-(benzyloxy)ethoxy)phenyl)-4,4,5,5-tetramethyl-1,3,2-

Dioxaborolane (1.2 g, 3.39 mmol) in DCM (50 mL) was added 4-(4-bromo-1H-pyrazol-3-yl)pyridine (831.53 mg, 3.73 mmol), $Cu(OAc)_2$ (615.6 mg, 3.39 mmol), $Et_2NH$ (2.47 g, 33.9 mmol) subsequently. The resulting solution was stirred at 30° C. overnight. The mixture was washed with ammonium hydroxide (30 mL×3). The organic phase was dried over and concentrated under vacuum. The residue was purified by silica gel column with PE/EA to afford desired product 4-(1-(3-(2-(benzyloxy)ethoxy)phenyl)-4-bromo-1H-pyrazol-3-yl)pyridine (900 mg, 59% yield) as purple solid. LCMS ($ES^+$): m/z 450.1 $[M+H]^+$.

To a solution of 4-(1-(3-(2-(benzyloxy)ethoxy)phenyl)-4-bromo-1H-pyrazol-3-yl)pyridine (900 mg, 2.0 mmol) in 1,4-dioxane/$H_2O$ (20 mL, v/v=10/1) were added 5-(4,4,5,5-tetramethyl-1,3,2-dioxaborolan-2-yl)-2,3-dihydro-1H-inden-1-one (774 mg, 3.0 mmol), $Pd_2(dba)_3$ (183.14 mg, 0.2 mmol), CsF (3.14 g, 20.64 mmol) $[(t\text{-}Bu)_3PH]BF_4$ (609 mg, 2.1 mmol), N,N-dicyclohexylmethylamine (503 mg, 2.58 mmol) subsequently. The resulting solution was stirred at 100° C. for 2 hours under $N_2$. After cooling to room temperature, the reaction was diluted with EA (50 mL), washed with water and brine. The organic layer was dried over anhydrous sodium sulfate, concentrated under vacuum. The residue was purified by silica gel column to afford 5-(1-(3-(2-(benzyloxy)ethoxy)phenyl)-3-(pyridin-4-yl)-1H-pyrazol-4-yl)-2,3-dihydro-1H-inden-1-one (750 mg, 74.9% yield) as yellow solid. LCMS ($ES^+$): m/z 502.2 $[M+H]^+$.

Step C: 5-(1-(3-(2-hydroxyethoxy)phenyl)-3-(pyridin-4-yl)-1H-pyrazol-4-yl)-2,3-dihydro-1H-inden-1-one

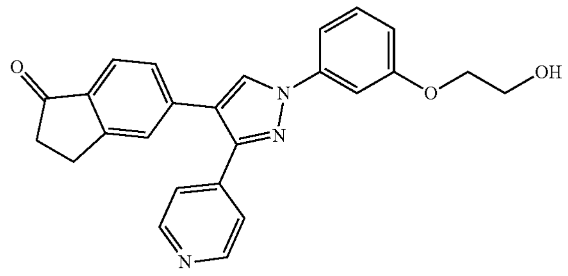 [SMILES: O=C1CCc2cc(-c3cn(-c4cccc(OCCO)c4)nc3-c3ccncc3)ccc21]

To a solution of 5-(1-(3-(2-(benzyloxy)ethoxy)phenyl)-3-(pyridin-4-yl)-1H-pyrazol-4-yl)-2,3-dihydro-1H-inden-1-one (750 mg, 1.50 mmol) in DCM (10 mL), was added $BBr_3$ (1.13 g, 4.50 mmol) in DCM (5 mL) dropwised at −60° C. under $N_2$. After stirred for 1 hour, the mixture was diluted with DCM (20 mL) and washed with brine (10 ml×2). The organic phaser was concentrated and purified by silica gel column to afford 5-(1-(3-(2-hydroxyethoxy)phenyl)-3-(pyridin-4-yl)-1H-pyrazol-4-yl)-2,3-dihydro-1H-inden-1-one (150 mg, 24.4% yield) as yellow solid. LCMS ($ES^+$): m/z 412.1 $[M+H]^+$.

Step D: 2-(2,6-dioxopiperidin-3-yl)-5-(2-(3-(4-(1-oxo-2,3-dihydro-1H-inden-5-yl)-3-(pyridin-4-yl)-1H-pyrazol-1-yl)phenoxy)ethoxy)isoindoline-1,3-dione

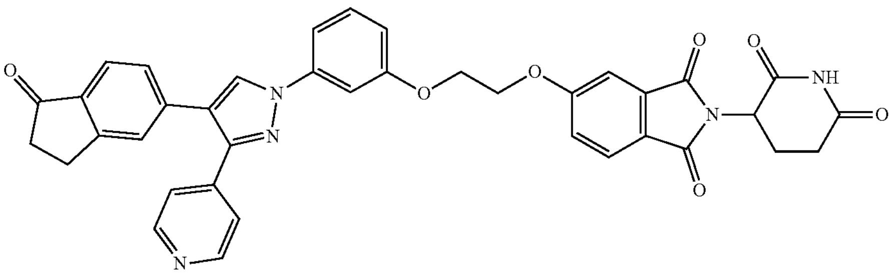 [SMILES: O=C1CCC(N2C(=O)c3ccc(OCCOc4cccc(-n5cc(-c6ccc7c(c6)CCC7=O)c(-c6ccncc6)n5)c4)cc3C2=O)C(=O)N1]

To a solution of 5-(1-(3-(2-hydroxyethoxy)phenyl)-3-(pyridin-4-yl)-1H-pyrazol-4-yl)-2,3-dihydro-1H-inden-1-one (150 mg, 0.36 mmol) in DCM (10 mL) and TEA (109.08 mg, 1.08 mmol) was added MsCl (61.56 mg, 0.54 mmol) dropwise at 0° C. The resulting solution was stirred at 25° C. for 0.5 hours. Then water was added and extracted with DCM. The organic layer was washed with water and brine, dried over anhydrous sodium sulfate and concentrated to afford crude desired product (170 mg crude, 95.5% yield) as yellow oil, which was used in next step directly. To a solution of above desired product (170 mg, 0.35 mmol) in DMF (10 ml) were added $K_2CO_3$ (144.9 mg, 1.05 mmol), 2-(2,6-dioxopiperidin-3-yl)-5-hydroxyisoindoline-1,3-dione (191.8 mg, 0.70 mmol). The resulting solution was stirred at 70° C. for 2 hours. After quenched with water, the mixture was extracted with EA (30 mL), washed with water and brine. The organic phase was dried over anhydrous sodium sulfate, concentrated and purified by silica gel column to afford 2-(2,6-dioxopiperidin-3-yl)-5-(2-(3-(4-(1-oxo-2,3-dihydro-1H-inden-5-yl)-3-(pyridin-4-yl)-1H-pyrazol-1-yl)phenoxy)ethoxy)isoindoline-1,3-dione (60 mg, 25.9% yield) as white solid. LCMS ($ES^+$): m/z 668.2 $[M+H]^+$.

Step E: (E)-2-(2,6-Dioxopiperidin-3-yl)-5-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione

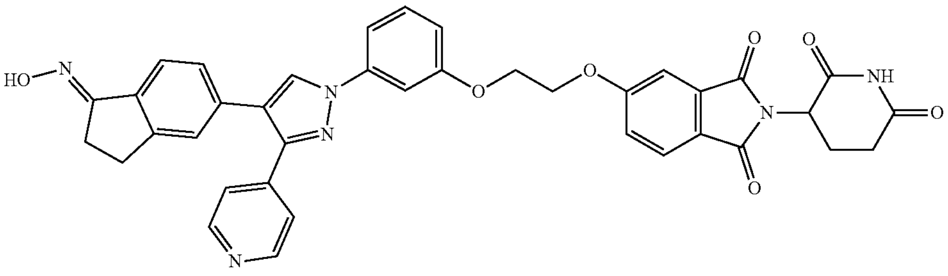 [SMILES: O=C1CCC(N2C(=O)c3ccc(OCCOc4cccc(-n5cc(-c6ccc7c(c6)CC/C7=N\O)c(-c6ccncc6)n5)c4)cc3C2=O)C(=O)N1]

To a solution of S2-(2,6-dioxopiperidin-3-yl)-5-(2-(3-(4-(1-oxo-2,3-dihydro-1H-inden-5-yl)-3-(pyridin-4-yl)-1H-pyrazol-1-yl)phenoxy)ethoxy)isoindoline-1,3-dione (60 mg, 0.090 mmol) in acetonitrile/pyridine (3.0 mL, v/v=2/1) was added hydroxylamine hydrochloride (58.41 mg, 0.90 mmol). The mixture was stirred at 40° C. for 20 minutes. Then it was diluted with DCM (20 mL), and washed with brine (10 mL). The organic phase was concentrated and purified by preparative HPLC to afford (E)-2-(2,6-dioxopiperidin-3-yl)-5-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione (8 mg, 65.6% yield) as white solid. $^1$H NMR (400 MHz, CDCl3): δ 8.58 (s, 2H), 8.04 (s, 2H), 7.83-7.81 (d, J=8.4 Hz, 1H), 7.68-7.66 (d, J=7.6 Hz, 1H), 7.52 (m, 2H), 7.48 (m, 1H), 7.44-7.43 (m, 2H), 7.41-7.36 (m, 2H), 7.30 (s, 2H), 7.23 (s, 2H), 4.99-4.94 (m, 1H), 4.49 (s, 4H), 3.05-2.94 (m, 4H), 2.90-2.73 (m, 3H), 2.04-2.00 (m, 1H); LCMS: (ES$^+$): m/z 683.2 [M+H]$^+$.

Compounds 204 and 205 may be prepared in a manner analogous to compound 203.

Example Synthesis of Compound 206: (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy)isoindoline-1,3-dione

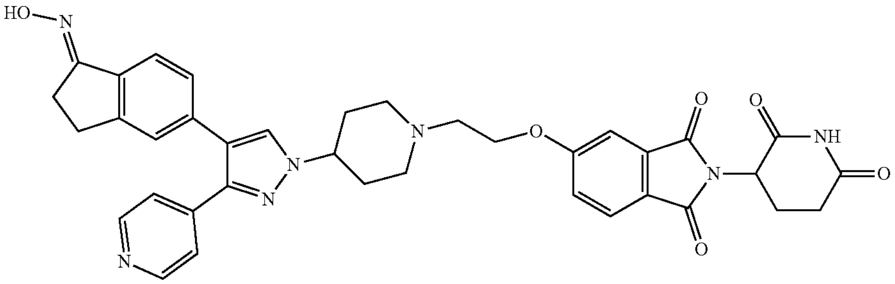 [SMILES: O=C1CCC(N2C(=O)c3ccc(OCCN4CCC(n5cc(-c6ccc7c(c6)CC/C7=N\O)c(-c6ccncc6)n5)CC4)cc3C2=O)C(=O)N1]

Step A: tert-butyl 4-(4-bromo-3-(pyridin-4-yl)-1H-pyrazol-1-yl)piperidine-1-carboxylate

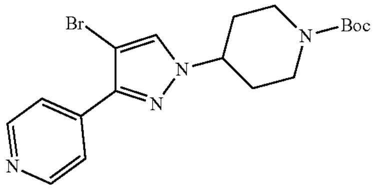 [SMILES: CC(C)(C)OC(=O)N1CCC(n2cc(Br)c(-c3ccncc3)n2)CC1]

The solution of 4-(4-bromo-1H-pyrazol-3-yl)pyridine (5.0 g, 22.4 mmol), tert-butyl 4-bromopiperidine-1-carboxylate (7.1 g, 26.9 mmol) and $Cs_2CO_3$ (11.0 g, 33.6 mmol) in DMF (50 mL) was stirred at 55° C. overnight. When it was cooled to room temperature, water (50 mL) was added. The resultant mixture was extracted by ethyl acetate (20 mL×3) and the combined organic layer was washed by brine (20 mL×3), dried over anhydrous sodium sulfate, filtered and concentrated. The residue was purified by column chromatography on silica (petroleum ether/ethyl acetate=1/1) to give tert-butyl 4-(4-bromo-3-(pyridin-4-yl)-1H-pyrazol-1-yl)piperidine-1-carboxylate (3.7 g, 41% yield) as brown oil. LCMS: m/z 407.1 [M+H]$^+$.

Step B: tert-butyl 4-(4-(1-oxo-2,3-dihydro-1H-inden-5-yl)-3-(pyridin-4-yl)-1H-pyrazol-1-yl)piperidine-1-carboxylate

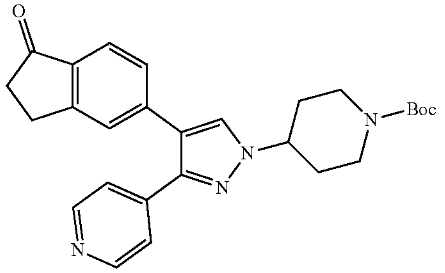 [SMILES: CC(C)(C)OC(=O)N1CCC(n2cc(-c3ccc4c(c3)CCC4=O)c(-c3ccncc3)n2)CC1]

To a solution of tert-butyl 4-(4-bromo-3-(pyridin-4-yl)-1H-pyrazol-1-yl)piperidine-1-carboxylate (2.0 g, 4.9 mmol), 5-(4,4,5,5-tetramethyl-1,3,2-dioxaborolan-2-yl)-2,3-dihydro-1H-inden-1-one (1.4 g, 5.4 mmol) and $K_2CO_3$ (1.4 g, 9.8 mmol) in 1,4-dioxane (40 mL) and water (8 mL) was added $Pd(PPh_3)_4$ (200 mg) under Ar atmosphere, and the mixture was stirred at 80° C. for 2 hours. When it was cooled to room temperature, the mixture was extracted by ethyl acetate (20 mL×3) and the combined organic layer was washed by brine (20 mL×3), dried over anhydrous sodium sulfate, filtered, and concentrated in vacuo. The residue was purified by flash column chromatography (petroleum ether/ethyl acetate=1/10) to give tert-butyl 4-(4-(1-oxo-2,3-dihydro-1H-inden-5-yl)-3-(pyridin-4-yl)-1H-pyrazol-1-yl)piperidine-1-carboxylate (1.9 g, 84% yield) as yellow oil. LCMS: m/z 459.3 [M+H]$^+$.

Step C: 5-(1-(piperidin-4-yl)-3-(pyridin-4-yl)-1H-pyrazol-4-yl)-2,3-dihydro-1H-inden-1-one

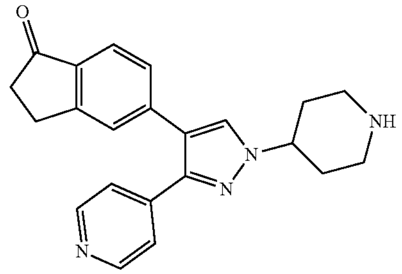 [SMILES: O=C1CCc2cc(-c3cn(C4CCNCC4)nc3-c3ccncc3)ccc21]

A mixture of tert-butyl 4-(4-(1-oxo-2,3-dihydro-1H-inden-5-yl)-3-(pyridin-4-yl)-1H-pyrazol-1-yl)piperidine-1-carboxylate (1.9 g, 4.1 mmol) in HCl/1,4-dioxane (20 mL) was stirred at room temperature for 2 hours. Then the solvent was directly removed in vacuum, and the crude product (1.6 g, 100% yield) was obtained as hydrochloride salt, which was directly used to the next step without further purification.

Step D: 2-(2,6-dioxopiperidin-3-yl)-5-(2-(4-(4-(1-oxo-2,3-dihydro-1H-inden-5-yl)-3-(pyridin-4-yl)-1H-pyrazol-1-yl)piperidin-1-yl)ethoxy)isoindoline-1,3-dione

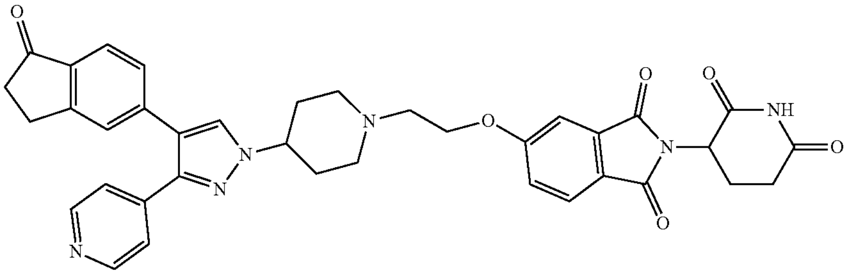 [SMILES: O=C1CCC(N2C(=O)c3ccc(OCCN4CCC(n5cc(-c6ccc7c(c6)CCC7=O)c(-c6ccncc6)n5)CC4)cc3C2=O)C(=O)N1]

A solution of 5-(1-(piperidin-4-yl)-3-(pyridin-4-yl)-1H-pyrazol-4-yl)-2,3-dihydro-1H-inden-1-one (440 mg, 1.2 mmol), 5-(2-chloroethoxy)-2-(2,6-dioxopiperidin-3-yl) isoindoline-1,3-dione (410 mg, 1.2 mmol), KI (304 mg, 1.8 mmol) and DIPEA (476 mg, 3.6 mmol) in DMSO (8 mL) was stirred at 100° C. overnight. When it was cooled to room temperature, water (10 mL) was added and the mixture was extracted by ethyl acetate (5 mL×3) and the combined organic layer was washed by brine (5 mL×3), dried over anhydrous sodium sulfate, filtered, and concentrated. The residue was purified by preparative TLC (DCM/MeOH=10/1) to give 2-(2,6-dioxopiperidin-3-yl)-5-(2-(4-(4-(1-oxo-2,3-dihydro-1H-inden-5-yl)-3-(pyridin-4-yl)-1H-pyrazol-1-yl)piperidin-1-yl)ethoxy)isoindoline-1,3-dione (180 mg, 22% yield) as a white solid. LCMS: m/z 659.3 $[M+H]^+$.

Step E: (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy)isoindoline-1,3-dione

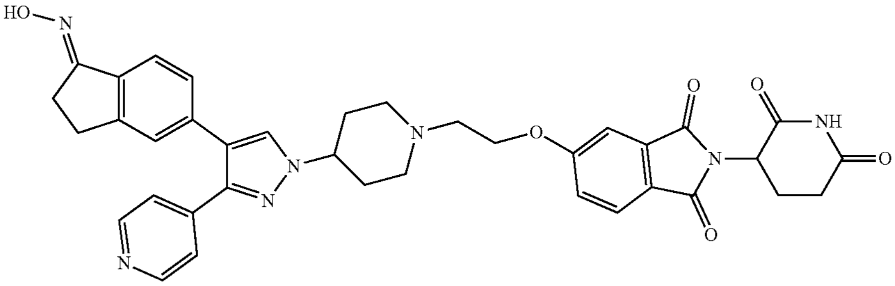 [SMILES: O=C1CCC(N2C(=O)c3ccc(OCCN4CCC(n5cc(-c6ccc7c(c6)CC/C7=N\O)c(-c6ccncc6)n5)CC4)cc3C2=O)C(=O)N1]

To a solution of 2-(2,6-dioxopiperidin-3-yl)-5-(2-(4-(4-(1-oxo-2,3-dihydro-1H-inden-5-yl)-3-(pyridin-4-yl)-1H-pyrazol-1-yl)piperidin-1-yl)ethoxy)isoindoline-1,3-dione (120 mg, 0.2 mmol) in pyridine (2 mL) was added hydroxylamine hydrochloride (126 mg, 1.8 mmol), and the mixture was stirred at room temperature for 2 hours. Then the solvent was removed in vacuo and the residue was purified by Preparative HPLC to give (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy) isoindoline-1,3-dione (52 mg, 42% yield). LCMS: m/z 674.2 $[M+H]^+$; $^1H$ NMR (400 MHz, DMSO-$d_6$) δ 2.03-2.11 (5H, m), 2.25-2.30 (2H, m), 2.50-2.62 (2H, m), 2.78-2.86 (5H, m), 2.88-2.99 (2H, m), 3.08-3.11 (2H, m), 4.22-4.28 (1H, m), 4.33 (2H, t, J=5.2 Hz), 5.12 (1H, dd, J=12.8, 5.2 Hz), 7.12 (1H, d, J=8.0 Hz), 7.30 (1H, s), 7.38-7.40 (3H, m), 7.49-7.52 (2H, m), 7.84 (1H, d, J=8.4 Hz), 8.14 (1H, s), 8.50 (2H, dd, J=4.4, 1.6 Hz), 10.86 (1H, s), 11.10 (1H, s).

Example Synthesis of Compound 207: (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-1,4'-bipiperidin-1'-yl)isoindoline-1,3-dione

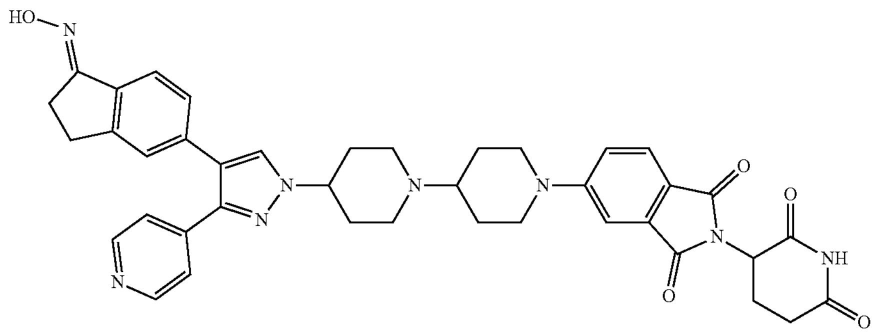 [SMILES: O=C1CCC(N2C(=O)c3ccc(N4CCC(N5CCC(n6cc(-c7ccc8c(c7)CC/C8=N\O)c(-c7ccncc7)n6)CC5)CC4)cc3C2=O)C(=O)N1]

Step A: tert-butyl 4-(4-(1-oxo-2,3-dihydro-1H-inden-5-yl)-3-(pyridin-4-yl)-1H-pyrazol-1-yl)-1,4'-bipiperidine-1'-carboxylate

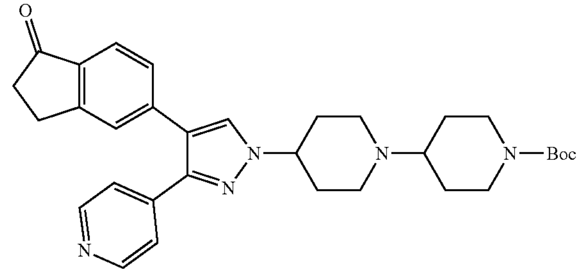 [SMILES: CC(C)(C)OC(=O)N1CCC(N2CCC(n3cc(-c4ccc5c(c4)CCC5=O)c(-c4ccncc4)n3)CC2)CC1]

The solution of 5-(1-(piperidin-4-yl)-3-(pyridin-4-yl)-1H-pyrazol-4-yl)-2,3-dihydro-1H-inden-1-one (2.5 g, 7.0 mmol), tert-butyl 4-bromopiperidine-1-carboxylate (2.0 g, 7.7 mmol), KI (1.2 g, 7.0 mmol) and $K_2CO_3$ (2.9 g, 20.9 mmol) in DMF (20 mL) was stirred at 110° C. overnight. When it was cooled to room temperature, water (30 mL) was added. The resultant mixture was extracted by ethyl acetate (20 mL×3) and the combined organic layer was washed by brine (20 mL×3), dried over anhydrous sodium sulfate, filtered and concentrated. The residue was purified by column chromatography on silica (DCM/MeOH=20/1) to give tert-butyl 4-(4-(1-oxo-2,3-dihydro-1H-inden-5-yl)-3-(pyridin-4-yl)-1H-pyrazol-1-yl)-1,4'-bipiperidine-r-carboxylate (360 mg, 10% yield) as brown oil. LCMS: m/z 542.3 $[M+H]^+$.

Step B: 5-(1-(L4'-bipiperidin-4-yl)-3-(pyridin-4-yl)-1H-pyrazol-4-yl)-2,3-dihydro-1H-inden-1-one

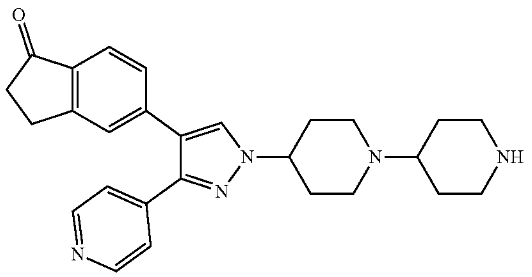 [SMILES: O=C1CCc2cc(-c3cn(C4CCN(C5CCNCC5)CC4)nc3-c3ccncc3)ccc21]

A mixture of tert-butyl 4-(4-(1-oxo-2,3-dihydro-1H-inden-5-yl)-3-(pyridin-4-yl)-1H-pyrazol-1-yl)-1,4'-bipiperidine-r-carboxylate (360 mg, 0.7 mmol) in HCl/1,4-dioxane (10 mL) was stirred at room temperature for 30 minutes. Then the solvent was directly removed in vacuum, and the crude product (300 mg, 100% yield) was obtained as hydrochloride salt, which was directly used to the next step without further purification.

Step C: 2-(2,6-dioxopiperidin-3-yl)-5-(4-(4-(1-oxo-2,3-dihydro-1H-inden-5-yl)-3-(pyridin-4-yl)-1H-pyrazol-1-yl)-1,4'-bipiperidin-1'-yl)isoindoline-1,3-dione

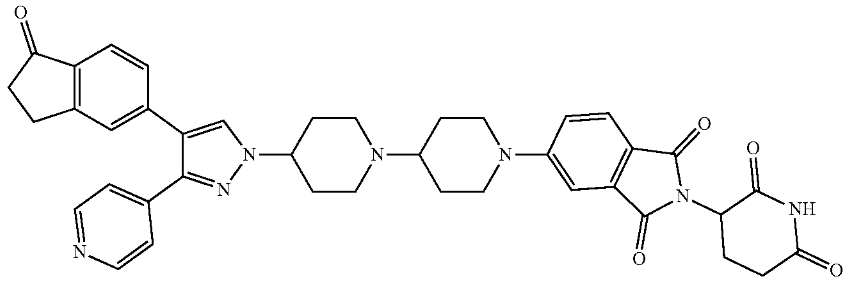 [SMILES: O=C1CCC(N2C(=O)c3ccc(N4CCC(N5CCC(n6cc(-c7ccc8c(c7)CCC8=O)c(-c7ccncc7)n6)CC5)CC4)cc3C2=O)C(=O)N1]

A solution of 5-(1-(1,4'-bipiperidin-4-yl)-3-(pyridin-4-yl)-1H-pyrazol-4-yl)-2,3-dihydro-1H-inden-1-one (290 mg, 0.7 mmol), 2-(2,6-dioxopiperidin-3-yl)-5-fluoroisoindoline-1,3-dione (183 mg, 0.7 mmol), and $Et_3N$ (336 mg, 3.3 mmol) in DMSO (5 mL) was stirred at 80° C. overnight. When it was cooled to room temperature, water (10 mL) was added and the mixture was extracted by ethyl acetate (5 mL×3) and the combined organic layer was washed by brine (5 mL×3), dried over anhydrous sodium sulfate, filtered, and concentrated. The residue was purified by preparative TLC (DCM/MeOH=20/1) to give 2-(2,6-dioxopiperidin-3-yl)-5-(4-(4-(1-oxo-2,3-dihydro-1H-inden-5-yl)-3-(pyridin-4-yl)-1H-pyrazol-1-yl)-1,4'-bipiperidin-r-yl)isoindoline-1,3-dione (195 mg, 42% yield) as a white solid. LCMS: m/z 698.3 $[M+H]^+$.

Step D: (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-1,4'-bipiperidin-1'-yl) isoindoline-1,3-dione

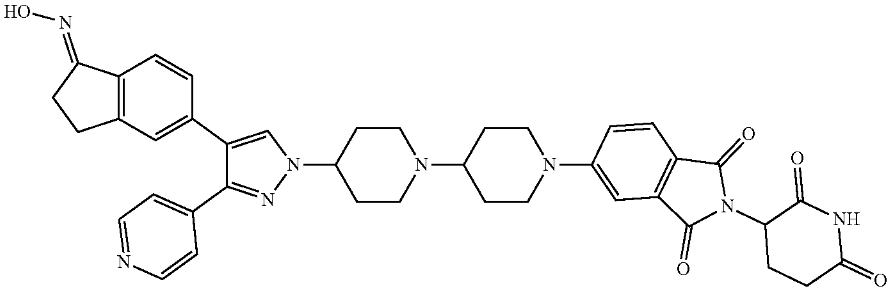 [SMILES: O=C1CCC(N2C(=O)c3ccc(N4CCC(N5CCC(n6cc(-c7ccc8c(c7)CC/C8=N\O)c(-c7ccncc7)n6)CC5)CC4)cc3C2=O)C(=O)N1]

To a solution of 2-(2,6-dioxopiperidin-3-yl)-5-(4-(4-(1-oxo-2,3-dihydro-1H-inden-5-yl)-3-(pyridin-4-yl)-1H-pyrazol-1-yl)-1,4'-bipiperidin-r-yl)isoindoline-1,3-dione (95 mg, 0.1 mmol) in pyridine (2 mL) was added hydroxylamine hydrochloride (94 mg, 1.3 mmol), and the mixture was stirred at room temperature for 2 hours. Then the solvent was removed in vacuo and the residue was purified by preparative HPLC to give (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-1,4'-bipiperidin-1'-yl)isoindoline-1,3-dione (53 mg, 55% yield). LCMS: m/z 713.4 $[M+H]^+$; NMR (400 MHz, DMSO-$d_6$) δ 1.51-1.53 (2H, m), 1.84-1.87 (2H, m), 1.97-2.03 (3H, m), 2.09-2.11 (2H, m), 2.32-2.37 (2H, m), 2.57-2.67 (2H, m), 2.78-2.89 (3H, m), 2.90-2.99 (6H, m), 4.11 (2H, d, J=12.8 Hz), 4.20-4.22 (1H, m), 5.06 (1H, dd, J=12.8, 5.6 Hz), 7.12 (1H, d, J=8.8 Hz), 7.25 (1H, d, J=6.0 Hz), 7.27 (1H, s), 7.30 (1H, s), 7.38 (2H, dd, J=4.8, 1.2 Hz), 7.50 (1H, d, J=8.0 Hz), 7.56 (1H, d, J=8.8 Hz), 8.13 (1H, s), 8.24 (1H, s), 8.50 (2H, dd, J=4.8, 1.6, Hz), 10.86 (1H, s), 11.08 (1H, s).

Example Synthesis of Compound 208: (3R)—N-(3-(5-(4-(2-(2-(2-(2-(4-(2-(2,6-Dioxopiperidin-3-yl)-1,3-dioxoisoindolin-5-yl)piperazin-1-yl)ethoxy)ethoxy)ethoxy)ethoxy)phenyl)-1H-pyrrolo[2,3-b]pyridine-3-carbonyl)-2,4-difluorophenyl)-3-fluoropyrrolidine-1-sulfonamide

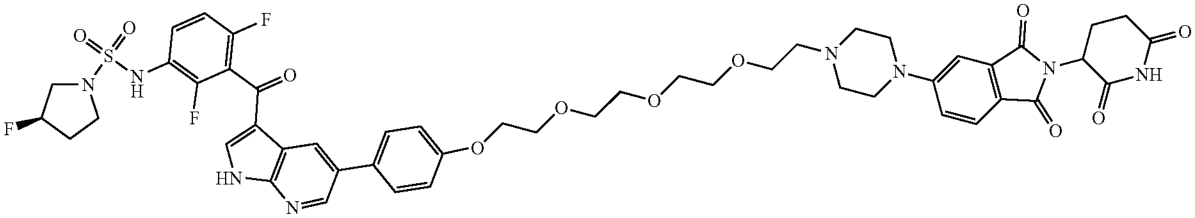 [SMILES: O=C1CCC(N2C(=O)c3ccc(N4CCN(CCOCCOCCOCCOc5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

Step A: 2-(2-(2-(2-(4-bromophenoxy)ethoxy)ethoxy)ethoxy)acetaldehyde

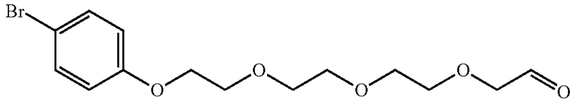 [SMILES: O=CCOCCOCCOCCOc1ccc(Br)cc1]

To a solution of 2-(2-(2-(2-(4-bromophenoxy)ethoxy)ethoxy)ethoxy)ethan-1-ol (3.1 g, 8.90 mmol) in acetonitrile (30 mL), was added IBX (3.7 g, 13.40 mmol). The mixture was heated to 80° C. for 1 hour. After cooling to room temperature, the mixture was filtered through Celite, and concentrated to afford crude desired product 2-(2-(2-(2-(4-bromophenoxy)ethoxy)ethoxy)ethoxy)acetaldehyde (3.2 g, crude) as oil.

Step B: 5-(4-(2-(2-(2-(2-(4-bromophenoxy)ethoxy)ethoxy)ethoxy)ethyl)piperazin-1-yl)-2-(2,6-dioxopiperidin-3-yl)isoindoline-1,3-dione

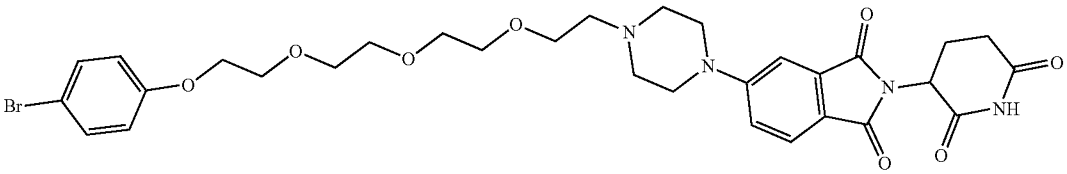 [SMILES: O=C1CCC(N2C(=O)c3ccc(N4CCN(CCOCCOCCOCCOc5ccc(Br)cc5)CC4)cc3C2=O)C(=O)N1]

To a solution of 2-(2-(2-(2-(4-bromophenoxy)ethoxy)ethoxy)ethoxy)acetaldehyde (3.2 g, 9.20 mmol) and 2-(2,6-dioxopiperidin-3-yl)-5-(piperazin-1-yl)isoindoline-1,3-dione hydrochloride (3.1 g, 9.20 mmol) in methano 1 (100 mL) and two drops AcOH was added $NaBH_3CN$ (0.58 g, 9.20 mmol). The mixture was stirred at room temperature overnight. After quenched with water (50 mL), the mixture was extracted with DCM (100 mL×2). The combined organic layer was washed with brine (200 mL), dried over $Na_2SO_4$ and filtered. The solvent was evaporated under reduced pressure. The residue was purified by column chromatography (DCM:MeOH=20:1) to afford the desired compound 5-(4-(2-(2-(2-(2-(4-bromophenoxy)ethoxy)ethoxy)ethoxy)ethyl)piperazin-1-yl)-2-(2,6-dioxopiperidin-3-yl)isoindoline-1,3-dione (1.1 g, 18%) as yellow solid. LC-MS: ($ES^+$): m/z 675.1 $[M+H]^+$.

Step C: 2-(2,6-dioxopiperidin-3-yl)-5-(4-(2-(2-(2-(2-(4-(4,4,5,5-tetramethyl-1,3,2-dioxaborolan-2-yl)phenoxy)ethoxy)ethoxy)ethoxy)ethyl)piperazin-1-yl)isoindoline-1,3-dione

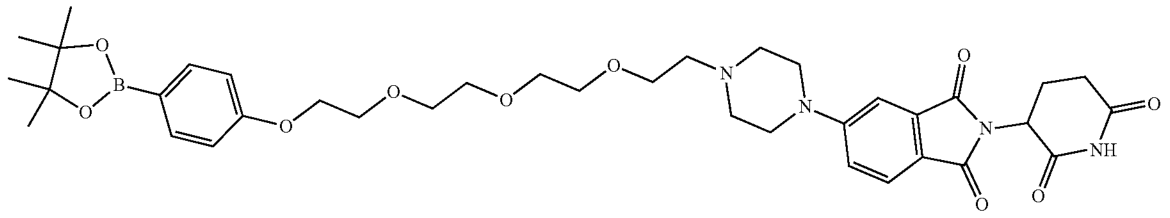 [SMILES: CC1(C)OB(c2ccc(OCCOCCOCCOCCN3CCN(c4ccc5c(c4)C(=O)N(C4CCC(=O)NC4=O)C5=O)CC3)cc2)OC1(C)C]

A solution of 5-(4-(2-(2-(2-(2-(4-bromophenoxy)ethoxy)ethoxy)ethoxy)ethyl)piperazin-1-yl)-2-(2,6-dioxopiperidin-3-yl)isoindoline-1,3-dione (400 mg, 0.60 mmol), 4,4,4',4',5,5,5',5'-octamethyl-2,2'-bi(1,3,2-dioxaborolane) (227 mg, 0.89 mmol), Pd(dppf)$Cl_2$ (88 mg, 0.12 mmol) and KOAc (118 mg, 1.20 mmol) in dioxane (10 mL) was heated to 90° C. overnight under $N_2$ atmosphere. After the reaction was quenched with water (15 mL), the mixture was extracted with DCM (50 mL×2). The combined layers were washed with water and brine. The combined organic layer was dried ($Na_2SO_4$), filtered, and concentrated under reduced pressure. The residue was purified by silica gel chromatography to afford 2-(2,6-Dioxopiperidin-3-yl)-5-(4-(2-(2-(2-(2-(4-(4,4,5,5-tetramethyl-1,3,2-dioxaborolan-2-yl)phenoxy)ethoxy)ethoxy)ethoxy)ethyl)piperazin-1-yl)isoindoline-1,3-dione (200 mg, 47%) as yellow solid. LCMS ($ES^+$): m/z 721.3 $[M+H]^+$.

Step D: (3R)—N-(3-(5-(4-(2-(2-(2-(2-(4-(2-(2,6-dioxopiperidin-3-yl)-1,3-dioxoisoindolin-5-yl)piperazin-1-yl)ethoxy)ethoxy)ethoxy)ethoxy)phenyl)-1H-pyrrolo[2,3-b]pyridine-3-carbonyl)-2,4-difluorophenyl)-3-fluoropyrrolidine-1-sulfonamide

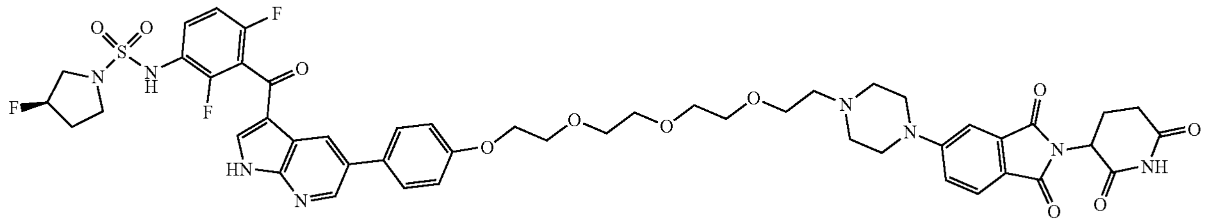 [SMILES: O=C1CCC(N2C(=O)c3ccc(N4CCN(CCOCCOCCOCCOc5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

A solution of 2-(2,6-dioxopiperidin-3-yl)-5-(4-(2-(2-(2-(2-(4-(4,4,5,5-tetramethyl-1,3,2-dioxaborolan-2-yl)phenoxy)ethoxy)ethoxy)ethoxy)ethyl)piperazin-1-yl)isoindoline-1,3-dione (200 mg, 0.28 mmol), (R)—N-(3-(5-bromo-1H-pyrrolo[2,3-b]pyridine-3-carbonyl)-2,4-difluorophenyl)-3-fluoropyrrolidine-1-sulfonamide (116 mg, 0.23 mmol), Pd(aMPhos)$C_{1-2}$ (66 mg, 0.09 mmol) and CsF (141 mg, 0.93 mmol) in dioxane/$H_2O$ (5 mL/I mL) was heated to 100° C. for 4 hours under $N_2$ atmosphere. After the reaction was quenched with water (15 mL), the mixture was extracted with DCM (50 mL×2). The combined layers were washed with water and brine. The combined organic layer was dried ($Na_2SO_4$), filtered, and concentrated under reduced pressure. The residue was purified by silica gel chromatography to afford (3R)—N-(3-(5-(4-(2-(2-(2-(2-(4-(2-(2,6-dioxopiperidin-3-yl)-1,3-dioxoisoindolin-5-yl)piperazin-1-yl) ethoxy)ethoxy)ethoxy)ethoxy)phenyl)-1H-pyrrolo[2,3-b]pyridine-3-carbonyl)-2,4-difluorophenyl)-3-fluoropyrrolidine-1-sulfonamide (40 mg, 17%) as yellow solid. $^1H$ NMR (400 MHz, $CDCl_3$): δ 11.23 (bs, 1H), 10.56 (s, 1H), 8.73 (s, 1H), 8.54 (s, 1H), 7.68-7.62 (m, 3H), 7.44 (s, 1H), 7.28 (s, 1H), 7.09 (d, J=8.8 Hz, 2H), 7.01 (t, J=8.8 Hz, 1H), 6.84 (s, 1H), 6.54 (d, J=7.6 Hz, 1H), 5.17 (s, 1H), 5.11-4.95 (m, 1H), 4.23 (s, 2H), 3.92 (s, 2H), 3.77-3.76 (m, 2H), 3.69-3.67 (m, 4H), 3.64-3.57 (m, 4H), 3.54-3.51 (m, 2H), 3.42-3.39 (m, 2H), 3.13 (s, 4H), 2.93 (s, 3H), 2.50-2.35 (m, 6H), 2.10 (s, 2H); LCMS ($ES^+$): m/z 1018.3 [M+H]+.

Example Synthesis of Compound 209

Step. A: 3-(tert-butyldimethylsilyloxy)cyclohexanol

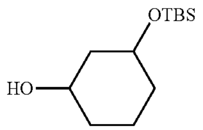 [SMILES: CC(C)(C)[Si](C)(C)OC1CCCC(O)C1]

To a solution of 1,3-cyclohexanediol (cis and trans mixture, 25 g, 0.216 mmol) and imidazole (8.8 g, 0.129 mmol)) in a mixture of dichloromethane (150 mL) and tetrahydrofuran (150 mL) was added dropwise a solution of tert-butyldimethylsilyl chloride (16.2 g, 0.107 mmol) in a mixture of dichloromethane (40 mL) and tetrahydrofuran (40 mL) at 0° C. The reaction mixture was allowed to warm to ambient temperature and stirred overnight. Insoluble material was removed by filtration and mother liquor was concentrated under reduced pressure to give residue, which was dissolved in ethyl acetate (300 mL) and washed in turn with 1 N aqueous hydrochloric acid (100 mL), brine (100 mL), saturated sodium hydrogen carbonate in water (100 mL), and saturated sodium chloride (100 mL), and dried over dried over anhydrous sodium sulfate. Evaporation of the solvent gave a residue, which was chromatographed on silica gel (ethyl acetate/n-hexane=1:5) to give 3-(tert-butyldimethylsilyloxy)cyclohexanol (cis and trans mixture) (12.5 g, 51% yield) as colorless oil.

Step B: 3-(pyridin-4-yloxy)cyclohexanol

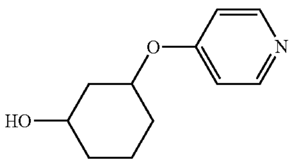 [SMILES: OC1CCCC(Oc2ccncc2)C1]

A mixture of 3-(tert-butyldimethylsilyloxy)cyclohexanol (10 g, 43.4 mmol), pyridin-4-ol (3.9 g, 41.2 mmol). tRiphenylphosphine (14.8 g, 56.42 mmol) in THF (40 mL, dry) were added diisopropyl azodicarboxylate (10.5 g, 52.1 mmol) dropwise during a period of 0.5 hours at room temperature under nitrogen atmosphere. The mixture was stirred for 3 h at room temperature under nitrogen atmosphere. HCl aq (70 mL, 1N) was added and stirred for 0.5 hours. The mixture was extracted with DCM (60 mL×3). The liquid layer was basified with KOH and extracted with ethyl acetate (60 mL×4). The combined organic layer was dried over anhydrous sodium sulfate, filtered and concentrated in vacuo to give 3-(pyridin-4-yloxy)cyclohexanol (3.3 g, 40% yield) as yellow oil. LCMS: m/z 194.1 $[M+H]^+$.

Step C: 3-(piperidin-4-yloxy)cyclohexanol

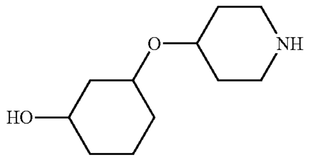 [SMILES: OC1CCCC(OC2CCNCC2)C1]

A mixture of solution of 3-(pyridin-4-yloxy)cyclohexanol (3.3 g, 17 mmol) in ethanol (30 mL) was added platinum dioxide (660 mg, 2.9 mmol), sulfuric acid (2.5 g, 26 mmol), then the reaction mixture was stirred at 50° C. for 2 days under hydrogen 2.0 MPa. The mixture was filtrated and concentrated, brine (30 mL×3) was added and extracted with DCM/MeOH (10/1, 30 mL×3). The combined organic layer was dried over anhydrous sodium sulfate, filtered and concentrated in vacuo. The residue was purified by column chromatography on silica (dichloromethane/methanol=10/1) to give 3-(piperidin-4-yloxy)cyclohexanol (330 mg, 10% yield) as pale yellow oil.

Step C: tert-butyl 4-(3-hydroxycyclohexyloxy)piperidine-1-carboxylate

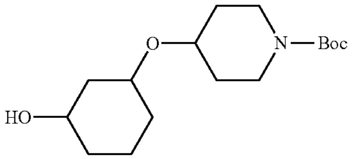

To a solution of 3-(piperidin-4-yloxy)cyclohexanol (330 mg, 1.66 mmol) and DIEA (642 mg, 4.9 mmol) in dichloromethane (15 mL) was added $Boc_2O$ (436 mg, 2.0 mmol), then it was stirred at room temperature overnight. The solvent was remove in vacuo at room temperature and the residue was purified by column chromatography on silica gel (ethyl acetate/petroleum ether=1/1) to give tert-butyl 4-(3-hydroxycyclohexyloxy)piperidine-1-carboxylate (352 mg, 71% yield) as yellow oil.

Step D: tert-butyl 4-(3-(methylsulfonyloxy)cyclohexyloxy)piperidine-1-carboxylate

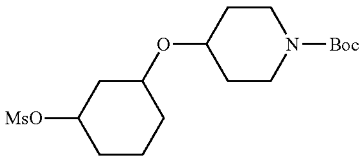 [SMILES: CC(C)(C)OC(=O)N1CCC(OC2CCCC(OS(C)(=O)=O)C2)CC1]

To a solution of tert-butyl 4-(3-hydroxycyclohexyloxy) piperidine-1-carboxylate (352 mg, 1.18 mmol) and DIEA (457 mg, 3.5 mmol) in dichloromethane (15 mL) was added MsCl (162 mg, 1.4 mmol) and the mixture was stirred at 0° C. for 1 hour. It was washed with aqueous $NaHCO_3$ (15 mL×2), brine (10 mL×2) successively. The organic phase was dried over anhydrous $Na_2SO_4$, filtered and concentrated in vacuo to give crude tert-butyl 4-(3-(methylsulfonyloxy) cyclohexyloxy)piperidine-1-carboxylate (351 mg, 79% yield) as pale yellow oil.

Step E: cis-tert-butyl-3-(4-bromo-3-(pyridin-4-yl)-1H-pyrazol-1-yl)cyclohexyloxy)piperidine-1-carboxylate and trans-tert-butyl-3-(4-bromo-3-(pyridin-4-yl)-1H-pyrazol-1-yl)cyclohexyloxylpiperidine-1-carboxylate

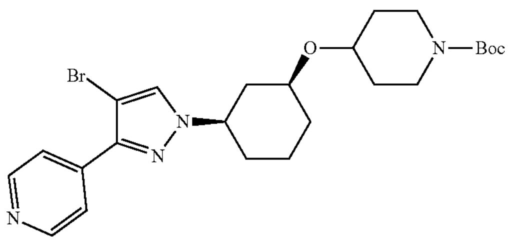

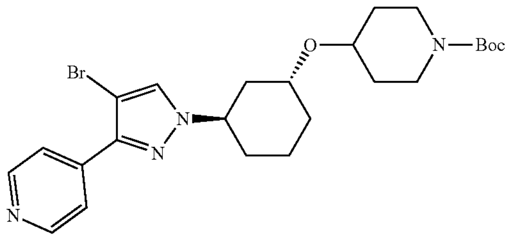

A mixture of tert-butyl 4-(3-(methylsulfonyloxy)cyclohexyloxy)piperidine-1-carboxylate (450 mg, 1.19 mmol), 4-(4-bromo-1H-pyrazol-3-yl)pyridine (252 mg, 1.13 mmol), $Cs_2CO_3$ (1.16 g, 3.57 mmol) in N,N-dimethylformamide (5 mL) were stirred at 80° C. for two days. It was diluted with brine (15 mL) and extracted with ethyl acetate (15 mL×3). The combined organic layer was washed by brine (15 mL×3), dried over anhydrous sodium sulfate, filtered and concentrated in vacuo. The residue was purified by column chromatography on silica gel (ethyl acetate/petroleum ether=1/1) to give cis-tert-butyl-3-(4-bromo-3-(pyridin-4-yl)-1H-pyrazol-1-yl)cyclohexyloxy)piperidine-1-carboxylate (140 mg) and trans-tert-butyl-3-(4-bromo-3-(pyridin-4-yl)-1H-pyrazol-1-yl)cyclohexyloxy)piperidine-1-carboxylate (130 mg) as pale yellow solid. For cis-tert-butyl-3-(4-bromo-3-(pyridin-4-yl)-1H-pyrazol-1-yl) cyclohexyloxy)piperidine-1-carboxylate: LCMS: m/z 505.3 $[M+H]^+$; $^1H$ NMR (400 MHz, $CDCl_3$) δ 1.38 (9H, s), 1.53-1.72 (6H, m), 1.89-2.11 (6H, m), 2.97-3.04 (2H, m), 3.41-3.47 (1H, m), 3.53-3.55 (1H, m), 3.69 (2H, brs), 4.09-4.15 (1H, m), 7.52 (1H, s), 7.84 (2H, d, J=6.0 Hz), 8.59 (2H, s). For trans-tert-butyl-3-(4-bromo-3-(pyridin-4-yl)-1H-pyrazol-1-yl)cyclohexyloxy)piperidine-1-carboxylate: LCMS: m/z 505.3 $[M+H]^+$; $^1H$ NMR (400 MHz, $CDCl_3$) δ 1.39 (9H, s), 1.42-1.92 (9H, m), 2.05-2.18 (3H, m), 3.04-3.11 (2H, m), 3.46-3.50 (1H, m), 3.66 (2H, brs), 3.90 (1H, s), 4.42-4.46 (1H, m), 7.47 (1H, s), 7.85 (2H, d, J=5.6 Hz), 8.58 (2H, s).

Step F: tert-butyl 4-((1S,3R)-3-(4-(1-oxo-2,3-dihydro-1H-inden-5-yl)-3-(pyridin-4-yl)-1H-pyrazol-1-yl)cyclohexyloxy)piperidine-1-carboxylate

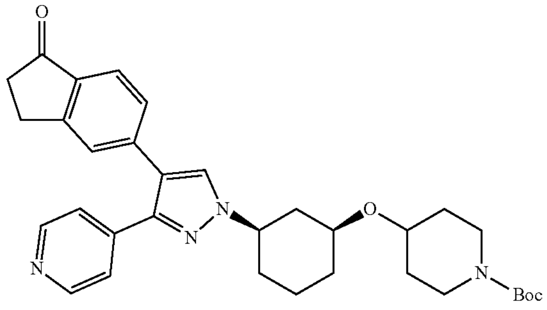 [SMILES: CC(C)(C)OC(=O)N1CCC(O[C@H]2CCC[C@@H](n3cc(-c4ccc5c(c4)CCC5=O)c(-c4ccncc4)n3)C2)CC1]

A mixture of tert-butyl 4-((1S,3R)-3-(4-bromo-3-(pyridin-4-yl)-1H-pyrazol-1-yl)cyclohexyloxy)piperidine-1-carboxylate (40 mg, 0.08 mmol), 5-(4,4,5,5-tetramethyl-1,3,2-dioxaborolan-2-yl)-2,3-dihydro-1H-inden-1-one (26 mg, 0.1 mmol), $K_2CO_3$ (33 mg, 0.24 mmol), tetrakis(triphenylphosphine)palladium (10 mg, 10 M %) were stirred in 1,4-dioxane/water (6 mL, 5/1) at 80° C. for 2 hours under nitrogen atmosphere. After the mixture was cooling, it was diluted with water (10 mL), extracted with ethyl acetate (15 mL×3). The combined organic layer was washed by brine (20 mL), dried over anhydrous sodium sulfate, filtered, and concentrated in vacuo. The residue was purified by column chromatography (petroleum ether/ethyl acetate=45/55) to give tert-butyl 4-((1S,3R)-3-(4-(1-oxo-2,3-dihydro-1H-inden-5-yl)-3-(pyridin-4-yl)-1H-pyrazol-1-yl)cyclohexyloxy) piperidine-1-carboxylate (20 mg, 44% yield) as a yellow solid. LCMS: m/z 557.3 $[M+H]^+$.

Step G: 5-(1-((1R,3S)-3-(piperidin-4-yloxy)cyclohexyl)-3-(pyridin-4-yl)-1H-pyrazol-4-yl)-2,3-dihydro-1H-inden-1-one

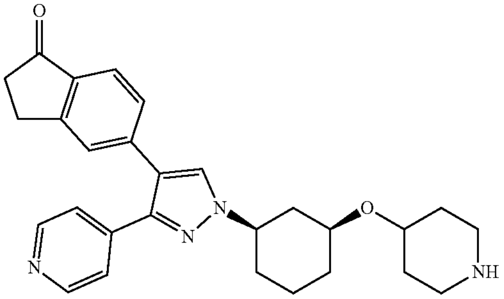 [SMILES: O=C1CCc2cc(-c3cn([C@@H]4CCC[C@H](OC5CCNCC5)C4)nc3-c3ccncc3)ccc21]

A solution of tert-butyl 4-((1S,3R)-3-(4-(1-oxo-2,3-dihydro-1H-inden-5-yl)-3-(pyridin-4-yl)-1H-pyrazol-1-yl)cyclohexyloxy)piperidine-1-carboxylate (40 mg, 0.08 mmol) in the solution of 4 N HCl in 1,4-dioxane (3 mL) was stirred at 0° C. for 5 hours. Then the solvent was directly removed to give 5-(1-((1R,3S)-3-(piperidin-4-yloxy)cyclohexyl)-3-(pyridin-4-yl)-1H-pyrazol-4-yl)-2,3-dihydro-1H-inden-1-one (38 mg, crude, 100% yield), which was directly used to the next step without further purification.

Step H: 2-(2,6-dioxopiperidin-3-yl)-5-(4-((1S,3R)-3-(4-(1-oxo-2,3-dihydro-1H-inden-5-yl)-3-(pyridin-4-yl)-1H-pyrazol-1-yl)cyclohexyloxy)piperidin-1-yl)isoindoline-1,3-dione

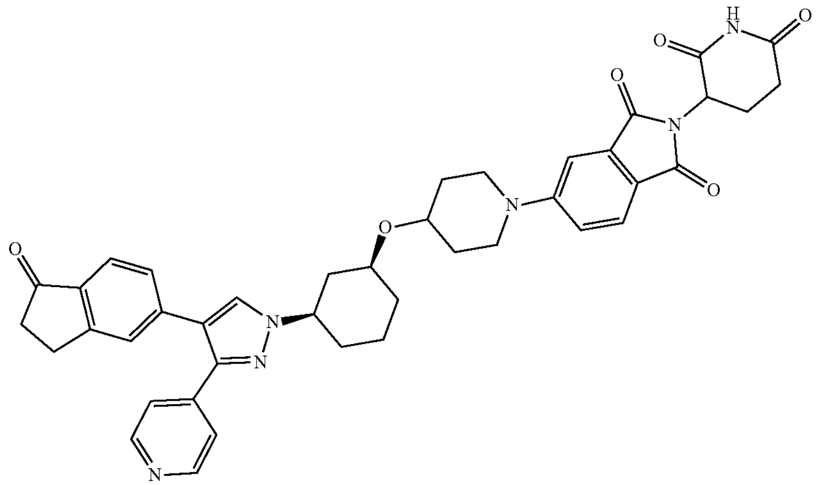 [SMILES: O=C1CCC(N2C(=O)c3ccc(N4CCC(O[C@H]5CCC[C@@H](n6cc(-c7ccc8c(c7)CCC8=O)c(-c7ccncc7)n6)C5)CC4)cc3C2=O)C(=O)N1]

A mixture of 5-(1-((1R,3S)-3-(piperidin-4-yloxy)cyclohexyl)-3-(pyridin-4-yl)-1H-pyrazol-4-yl)-2,3-dihydro-1H-inden-1-one (20 mg, 0.044 mmol), 2-(2,6-dioxopiperidin-3-yl)-5-fluoroisoindoline-1,3-dione (18 mg, 0.066 mmol), DIEA (17 mg, 0.13 mmol) in DMSO (3 mL) were stirred at 80° C. overnight. It was diluted with brine (15 mL) and extracted with ethyl acetate (15 mL×3). The combined organic layer was washed by brine (15 mL×3), dried over anhydrous sodium sulfate, filtered and concentrated in vacuo. The residue was purified by Preparative TLC (DCM/MeOH=20/1) to give 2-(2,6-dioxopiperidin-3-yl)-5-(4-((1S,3R)-3-(4-(1-oxo-2,3-dihydro-1H-inden-5-yl)-3-(pyridin-4-yl)-1H-pyrazol-1-yl)cyclohexyloxy)piperidin-1-yl)isoindoline-1,3-dione (15 mg, 50% yield) as a yellow solid. LCMS: m/z 713.3 $[M+H]^+$.

Step I: 2-(2,6-dioxopiperidin-3-yl)-5-(4-((1S,3R)-3-(4-((E)-1-(hydroxyimino)-2,3-dihydro-1H-inden-5-yl)-3-(pyridin-4-yl)-1H-pyrazol-1-yl)cyclohexyloxy)piperidin-1-yl)isoindoline-1,3-dione

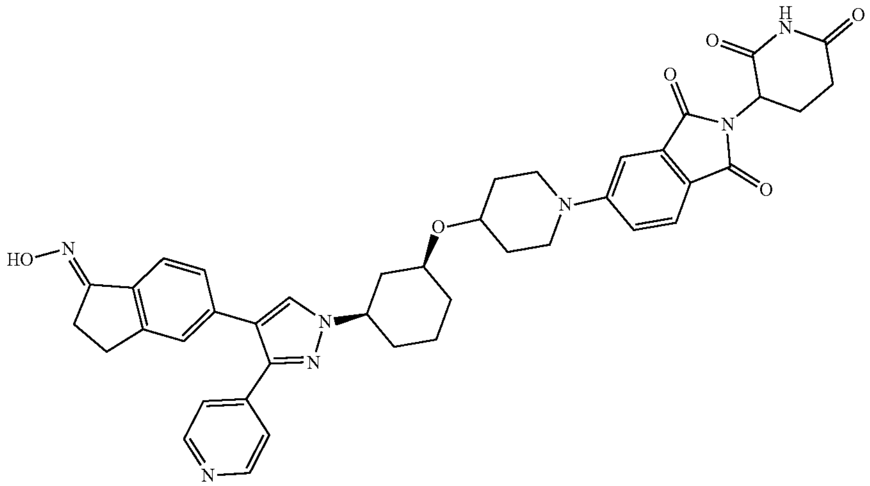 [SMILES: O=C1CCC(N2C(=O)c3ccc(N4CCC(O[C@H]5CCC[C@@H](n6cc(-c7ccc8c(c7)CC/C8=N\O)c(-c7ccncc7)n6)C5)CC4)cc3C2=O)C(=O)N1]

A mixture of 2-(2,6-dioxopiperidin-3-yl)-5-(4-((1S,3R)-3-(4-(1-oxo-2,3-dihydro-1H-inden-5-yl)-3-(pyridin-4-yl)-1H-pyrazol-1-yl)cyclohexyloxy)piperidin-1-yl)isoindoline-1,3-dione (15 mg, 0.021 mmol), hydroxylamine hydrochloride (15 mg, 0.21 mmol) in pyridine (3 mL) was stirred at room temperature overnight. The solvent was directly removed in vacuo at room temperature, and the residue was purified by preparative HPLC to give 2-(2,6-dioxopiperidin-3-yl)-5-(4-((1S,3R)-3-(4-((E)-1-(hydroxyimino)-2,3-dihydro-1H-inden-5-yl)-3-(pyridin-4-yl)-1H-pyrazol-1-yl)cyclohexyloxy)piperidin-1-yl)isoindoline-1,3-dione (2.8 mg, 18% yield) as a yellow solid. LCMS: m/z 728.3 $[M+H]^+$; NMR (400 MHz, $CDCl_3$) δ 1.73-2.08 (12H, m), 2.17-2.19 (1H, m), 2.51-2.53 (1H, m), 2.66-2.96 (7H, m), 3.17-3.23 (2H, m), 3.48-354 (1H, m), 3.61-3.73 (3H, m), 4.16-4.22 (1H, m), 4.84-4.89 (1H, m), 6.98 (1H, dd, J=8.4, 2.0 Hz), 7.09 (1H, d, J=8.0 Hz), 7.15 (1H, s), 7.21 (1H, d, J=2.4 Hz), 7.45-7.51 (3H, m), 7.59 (2H, t, J=8.8 Hz), 8.14 (1H, d, J=12.8 Hz), 8.46 (1H, d, J=4.8 Hz).

Compound 210 may be prepared in a manner analogous to compound 209.

Example Synthesis of Compound 211: (E)-2-(2,6-dioxopiperidin-3-yl)-5-(3-(1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione

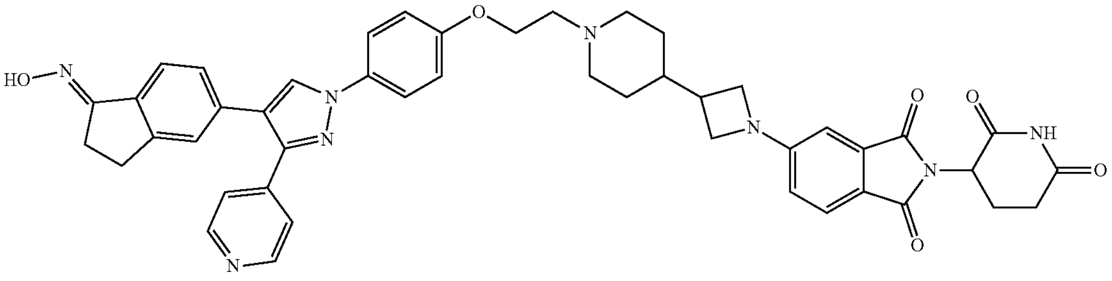 [SMILES: O=C1CCC(N2C(=O)c3ccc(N4CC(C5CCN(CCOc6ccc(-n7cc(-c8ccc9c(c8)CC/C9=N\O)c(-c8ccncc8)n7)cc6)CC5)C4)cc3C2=O)C(=O)N1]

Step A: tert-butyl-3-(1-(2-(4-(4-bromo-3-(pyridin-4-yl)-1H-pyrazol-1-yl)phenoxy)ethyl) piperidin-4-yl)azetidine-1-carboxylate

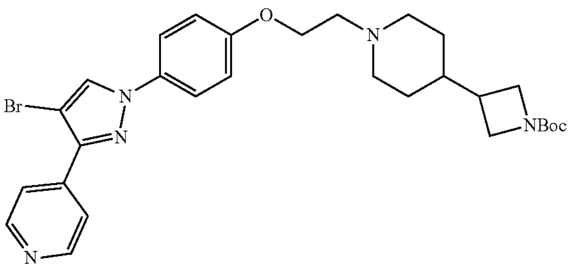 [SMILES: CC(C)(C)OC(=O)N1CC(C2CCN(CCOc3ccc(-n4cc(Br)c(-c5ccncc5)n4)cc3)CC2)C1]

To a solution of 2-(4-(4-bromo-3-(pyridin-4-yl)-1H-pyrazol-1-yl)phenoxy) acetaldehyde (0.34 g, 0.95 mmol) in EtOH/DCM (6 mL/6 mL) were added tert-butyl-3-(piperidin-4-yl)azetidine-1-carboxylate (272 mg, 1.14 mmol) and cat. AcOH. AcOK was added if pH was below 5~6. Then $NaBH(OAc)_3$ (810 mg, 3.80 mmol) was added. The resulting solution was stirred at 30° C. for 1 hour. After quenched the reaction with aq.$NaHCO_3$ (20 mL), the mixture was extracted with DCM (30 ml×2). The combined organic layer was dried over anhydrous sodium sulfate and concentrated under vacuum. The residue was applied onto a silica gel column to afford desired product tert-butyl-3-(1-(2-(4-(4-bromo-3-(pyridin-4-yl)-1H-pyrazol-1-yl)phenoxy) ethyl)piperidin-4-yl)azetidine-1-carboxylate (270 mg). LCMS: ($ES^+$): m/z 583.3 $[M+H]^+$.

Step B: 4-(1-(4-(2-(4-(azetidin-3-yl)piperidin-1-yl) ethoxy)phenyl)-4-bromo-1H-pyrazol-3-yl)pyridine

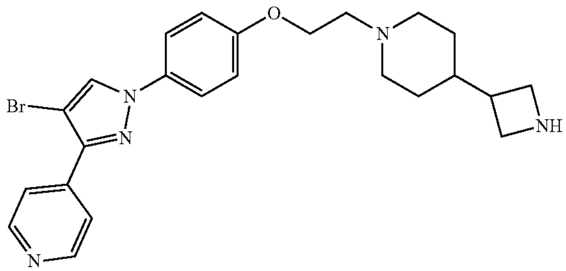 [SMILES: Brc1cn(-c2ccc(OCCN3CCC(C4CNC4)CC3)cc2)nc1-c1ccncc1]

To a solution of tert-butyl 3-(1-(2-(4-(4-bromo-3-(pyridin-4-yl)-1H-pyrazol-1-yl)-phenoxy)ethyl)piperidin-4-yl) azetidine-1-carboxylate (0.27 g, 0.46 mmol) in DCM (6 mL) was added TFA (2 mL). The resulting mixture was stirred at 30° C. for 1 hours. The solvent was removed under vacuum, and the residue was co-evaporated with DCM twice to afford the desired product 4-(1-(4-(2-(4-(azetidin-3-yl)piperidin-1-yl)ethoxy)-phenyl)-4-bromo-1H-pyrazol-3-yl)pyridine (224 mg crude, calculated, 0.46 mmol), which was used into next reaction without further purification. LCMS: ($ES^+$): m/z 482.0 $[M+H]^+$.

Step C: 5-(3-(1-(2-(4-(4-bromo-3-(pyridin-4-yl)-1H-pyrazol-1-yl)phenoxy)ethyl)piperidin-4-yl)azetidin-1-yl)-2-(2,6-dioxopiperidin-3-yl)isoindoline-1,3-dione

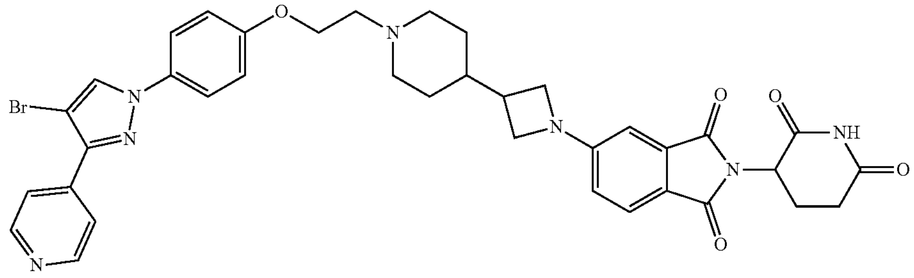 [SMILES: O=C1CCC(N2C(=O)c3ccc(N4CC(C5CCN(CCOc6ccc(-n7cc(Br)c(-c8ccncc8)n7)cc6)CC5)C4)cc3C2=O)C(=O)N1]

To a solution of 4-(1-(4-(2-(4-(azetidin-3-yl)piperidin-1-yl)ethoxy)phenyl)-4-bromo-1H-pyrazol-3-yl)pyridine (224 mg crude, 0.46 mmol) in NMP (5 mL) were added 2-(2,6-dioxopiperidin-3-yl)-5-fluoroisoindoline-1,3-dione (254 mg, 0.92 mmol) and DIEA (0.6 g, 4.6 mmol). The resultant solution was irradiated at 150° C. with microwave for 2 hours. After cooling to room temperature, the mixture was diluted with EA (50 mL). The mixture was washed with brine (10 mL×3). The organic phase was dried over $Na_2SO_4$, filtered and concentrated under reduced pressure. The residue was purified by prep-TLC to afford 5-(3-(1-(2-(4-(4-bromo-3-(pyridin-4-yl)-1H-pyrazol-1-yl) phenoxy)ethyl)piperidin-4-yl)azetidin-1-yl)-2-(2,6-dioxopiperidin-3-yl) isoindoline-1,3-dione (60 mg). LCMS: ($ES^+$): m/z 739.3 $[M+H]^+$.

Step D: 2-(2,6-dioxopiperidin-3-yl)-5-(3-(1-(2-(4-(4-(1-oxo-2,3-dihydro-1H-inden-5-yl)-3-(pyridin-4-yl)-1H-pyrazol-1-yl)phenoxy)ethyl)piperidin-4-yl) azetidin-1-yl)isoindoline-1,3-dione To a solution of 5-(3-(1-(2-(4-(4-bromo-3-(pyridin-4-yl)-1H-pyrazol-1-yl)phenoxy) ethyl)piperidin-4-yl)azetidin-1-yl)-2-(2,6-dioxopiperidin-3-yl)isoindoline-1,3-dione (60 mg, 0.081 mmol) and 5-(4,4,5,5-tetramethyl-1,3,2-dioxaborolan-2-yl)-2,3-dihydro-1H-inden-1-one (84 mg, 0.325 mmol) in dioxane (15 mL)/$H_2O$ (3 mL) were added CsF (49 mg, 0.325 mmol), $Pd_2(dba)_3$ (30 mg, 0.033 mmol), tri-tert-butylphosphine tetrafluoroborate (20 mg, 0.066 mmol) and two drops of $Cy_2NCH_3$ subsequently. The resulting solution was heated to 100° C. for 16 hours under $N_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was purified by prep-TLC to afford desired product 2-(2,6-dioxopiperidin-3-yl)-5-(3-(1-(2-(4-(4-(1-oxo-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione (30 mg, 47% yield) as yellow solid. LCMS: (ES+): m/z 790.3 $[M+H]^+$.

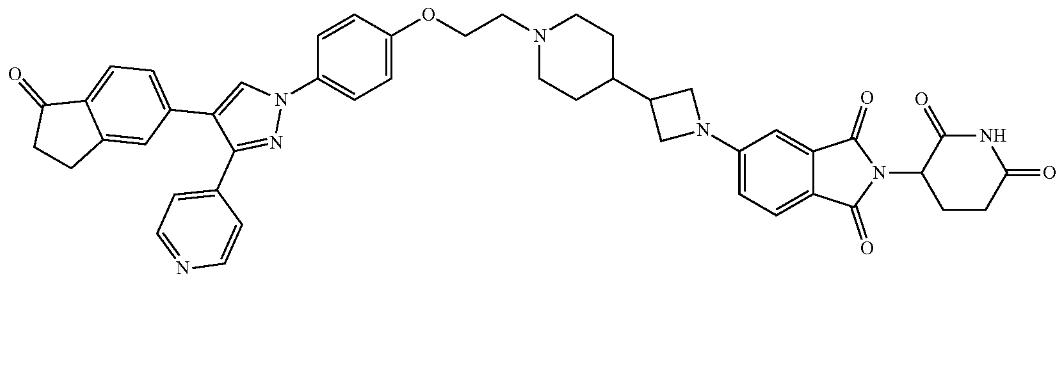 [SMILES: O=C1CCC(N2C(=O)c3ccc(N4CC(C5CCN(CCOc6ccc(-n7cc(-c8ccc9c(c8)CCC9=O)c(-c8ccncc8)n7)cc6)CC5)C4)cc3C2=O)C(=O)N1]

Step E: (E)-2-(2,6-dioxopiperidin-3-yl)-5-(3-(1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione

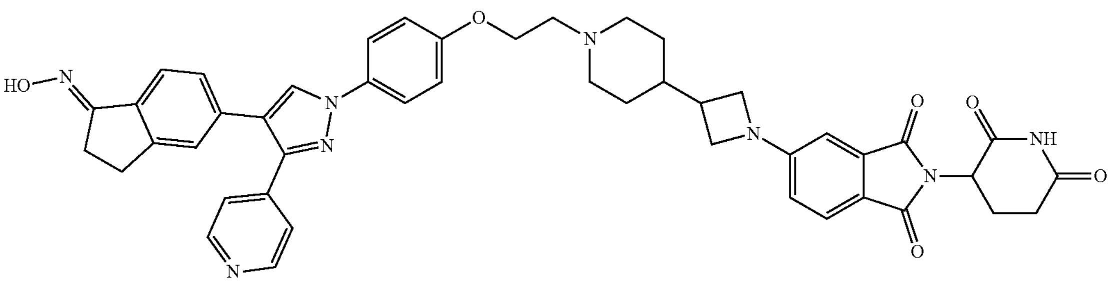 [SMILES: O=C1CCC(N2C(=O)c3ccc(N4CC(C5CCN(CCOc6ccc(-n7cc(-c8ccc9c(c8)CC/C9=N\O)c(-c8ccncc8)n7)cc6)CC5)C4)cc3C2=O)C(=O)N1]

To a solution of 2-(2,6-dioxopiperidin-3-yl)-5-(3-(1-(2-(4-(4-(1-oxo-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione (30 mg, 0.038 mmol) in $CH_3CN$/pyridine (6 mL/3 mL) was added hydroxylamine hydrochloride (26 mg, 0.38 mmol). The mixture was stirred at 50° C. for 1 hour. The solvent was removed under vacuum, and the residue was purified by prep-TLC with DCM/MeOH (15/1) to afford the desired product (E)-2-(2,6-dioxopiperidin-3-yl)-5-(3-(1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione (15 mg, 50% yield) as yellow solid. NMR (400 MHz, DMSO-$d_6$): δ 11.07 (s, 1H), 10.91 (s, 1H), 8.75 (s, 1H), 8.57 (d, J=5.6 Hz, 2H), 7.87 (d, J=8.8 Hz, 2H), 7.65 (d, J=4.8 Hz, 1H), 7.55 (d, J=4.8 Hz, 1H), 7.49 (d, J=5.6 Hz, 2H), 7.41 (s, 1H), 7.21 (d, J=4.8 Hz, 1H), 7.12 (d, J=9.2 Hz, 2H), 6.77 (s, 1H), 6.63 (d, J=4.4 Hz, 1H), 5.00-5.10 (m, 1H), 4.05-4.20 (m, 4H), 3.70-3.80 (m, 2H), 2.70-3.10 (m, 7H), 2.55-2.65 (m, 4H), 1.70-2.05 (m, 10H); LCMS: (ES+): m/z 806.3 $[M+H]^+$.

Example Synthesis of Compound 213: (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy)propoxy)isoindoline-1,3-dione Step. A: (2-(2-(3-((tert-butyldimethylsilyl)oxy)propoxy)ethoxy)phenyl)methanol

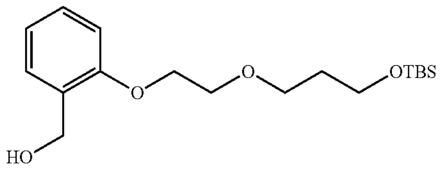

To a solution of 2-(3-((tert-butyldimethylsilyl)oxy)propoxy)ethyl 4-methylbenzenesulfonate (1 g, 2.58 mmol) in DMF (10 mL) were added 2-(hydroxymethyl)phenol (0.38 g, 3.09 mol) and $K_2CO_3$ (1.07 g, 2.74 mmol). The resulting solution was stirred at 70° C. for 3 hours. After cooling to room temperature, the reaction was quenched with $NH_4Cl$ aq, and the mixture was extracted EtOAc. The organic phase was dried over anhydrous sodium sulfate, concentrated under vacuum. The residue was purified by chromatography column to afford (2-(2-(3-((tert-butyldimethylsilyl)oxy)-propoxy)ethoxy)phenyl)methanol (400 mg, 45.6% yield) as colorless oil. NMR (400 MHz, $CDCl_3$): δ 7.36-7.34 (d, J=7.2 Hz, 1H), 7.18-7.14 (t, J=7.2 Hz, 1H), 6.93-6.90 (m, 2H), 4.90-4.87 (t, J=5.6 Hz, 1H), 4.49-4.47 (m, 2H), 4.07-4.05 (m, 2H), 3.68-3.61 (m, 4H), 3.52-2.90 (t, J=6.4 Hz, 2H), 1.70-1.64 (m, 2H), 0.83 (s, 9H), 0.00 (s, 6H).

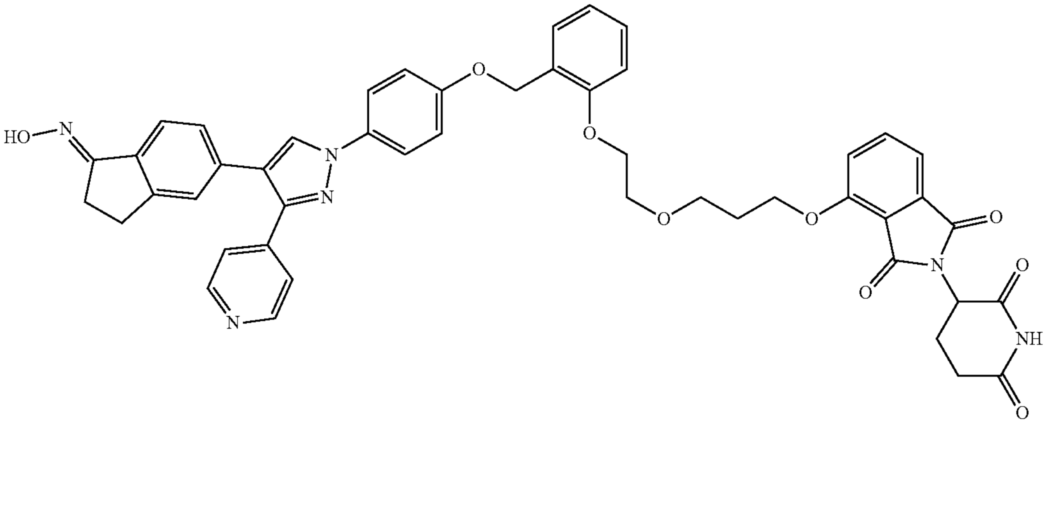 [SMILES: O=C1CCC(N2C(=O)c3cccc(OCCCOCCOc4ccccc4COc4ccc(-n5cc(-c6ccc7c(c6)CC/C7=N\O)c(-c6ccncc6)n5)cc4)c3C2=O)C(=O)N1]

Step B: 4-(4-bromo-1-(4-((2-(2-(3-((tert-butyldimethylsilyl)oxy)propoxy)ethoxy) benzyl)oxy)phenyl)-1H-pyrazol-3-yl)pyridine

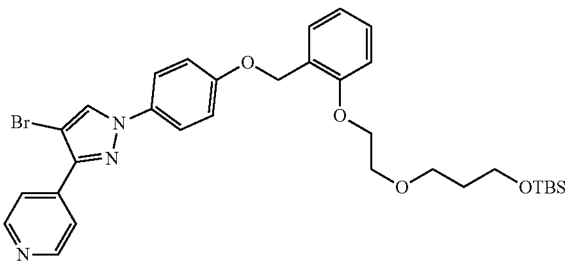 [SMILES: CC(C)(C)[Si](C)(C)OCCCOCCOc1ccccc1COc1ccc(-n2cc(Br)c(-c3ccncc3)n2)cc1]

To a solution of (2-(2-(3-((tert-butyldimethylsilyl)oxy)propoxy)ethoxy)phenyl)-methanol (400 mg, 1.18 mmol) in DCM (20 mL) and DIPEA (457 mg, 3.54 mmol) was added MsCl (268 mg, 2.36 mmol) at 0° C. The resulting solution was stirred at room temperature for 1 hour. The reaction was diluted with DCM (100 mL), washed with water, brine. The organic phase was dried over anhydrous sodium sulfate, concentrated under vacuum to afford crude desired product (320 mg, 100% yield), which was used in next step directly. To a solution of above desired product (320 mg, 0.89 mmol) in dry DMF (20 ml) was added $K_2CO_3$ (368.5 mg, 2.67 mmol) and 4-(4-bromo-3-(pyridin-4-yl)-1H-pyrazol-1-yl)phenol (309.7 mg, 0.98 mmol). The resulting solution was stirred at 70° C. for 2 hours. After cooled to room temperature, the reaction mixture was diluted with EtOAc (100 mL), washed with water and brine. The organic phase was dried over anhydrous sodium sulfate. The residue was purified by chromatography column to afford 4-(4-bromo-1-(4-((2-(2-(3-((tert-butyldimethylsilyl)oxy)propoxy)ethoxy)benzyl)oxy)phenyl)-1H-pyrazol-3-yl)-pyridine (300 mg, 40.1% yield 2 steps) as red oil. NMR (400 MHz, $CDCl_3$): δ 8.73-8.67 (m, 2H), 8.00-7.90 (m, 3H), 7.63-7.59 (d, J=9.2 Hz, 1H), 7.50-7.42 (m, 1H), 7.33-7.27 (m, 2H), 7.12-7.08 (m, 2H), 7.02-6.91 (m, 2H), 5.20 (s, 2H), 4.22-4.17 (t, J=4.8 Hz, 2H), 3.84-3.76 (t, J=5.2 Hz, 2H), 3.70-3.67 (t, J=6.4 Hz, 2H), 3.62-3.59 (t, J=6.4 Hz, 2H), 1.82-1.75 (m, 2H), 0.87 (s, 9H), 0.02 (s, 6H).

Step C: 3-(2-(2-((4-(4-bromo-3-(pyridin-4-yl)-1H-pyrazol-1-yl)phenoxy)methyl)phenoxy)ethoxy)propan-1-ol

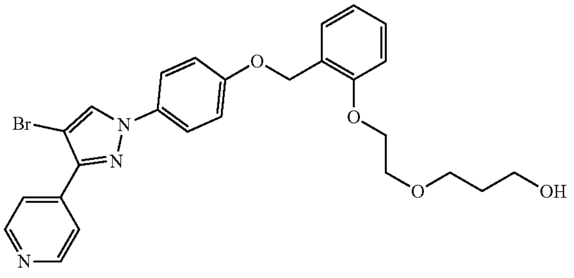 [SMILES: OCCCOCCOc1ccccc1COc1ccc(-n2cc(Br)c(-c3ccncc3)n2)cc1]

To a solution of 4-(4-bromo-1-(4-((2-(2-(3-((tert-butyldimethylsilyl)oxy)-propoxy)ethoxy)benzyl)oxy)phenyl)-1H-pyrazol-3-yl)pyridine (300 mg, 0.47 mmol) in MeOH (10 mL) was added HCl in 1,4-dioxane (1 mL, 6 M/L, 6 mmol) at room temperature. The resulting solution was stirred at room temperature for 0.5 hours. The solution was concentrated and diluted with 100 ml of DCM, washed with $NaHCO_3$ (50 mL×3). The organic phase was dried over anhydrous sodium sulfate and concentrated under vacuum. The residue was purified by preparative TLC to afford desired product 3-(2-(2-((4-(4-Bromo-3-(pyridin-4-yl)-1H-pyrazol-1-yl)phenoxy)methyl)phenoxy)ethoxy)propan-1-ol (160 mg, 65% yield) as white solid. LCMS ($ES^+$): m/z 524.1 $[M+H]^+$.

Step D: tert-butyl 5-amino-4-(4-(3-(2-(2-((4-(4-bromo-3-(pyridin-4-yl)-1H-pyrazol-1-yl)phenoxy)methyl)phenoxy)ethoxy)propoxy)-1,3-dioxoisoindolin-2-yl)-5-oxopentanoate

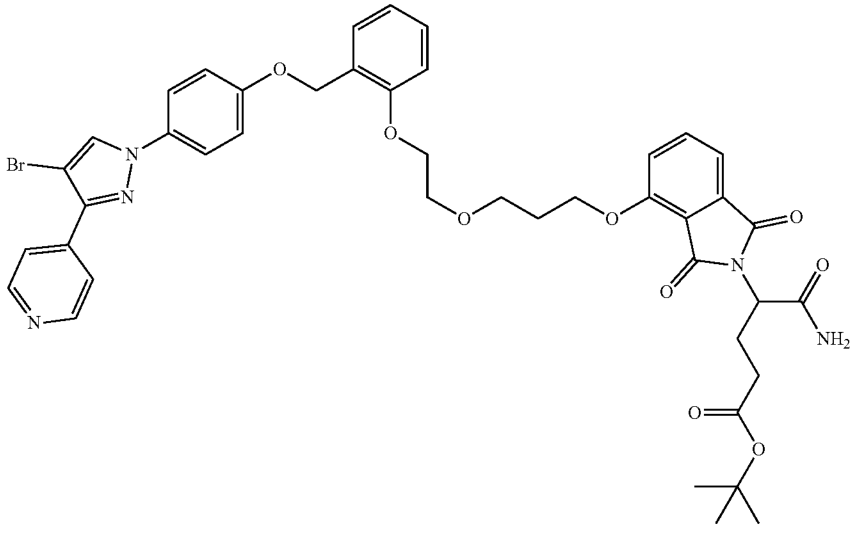 [SMILES: CC(C)(C)OC(=O)CCC(C(N)=O)N1C(=O)c2cccc(OCCCOCCOc3ccccc3COc3ccc(-n4cc(Br)c(-c5ccncc5)n4)cc3)c2C1=O]

To a solution of 3-(2-(2-((4-(4-bromo-3-(pyridin-4-yl)-1H-pyrazol-1-yl)phenoxy) methyl)phenoxy)ethoxy)propan-1-ol (160 mg, 0.31 mmol) $PPh_3$ (244 mg, 0.93 mmol) and tert-butyl 5-amino-4-(4-hydroxy-1,3-dioxoisoindolin-2-yl)-5-oxopentanoate (159.4 mg, 0.46 mmol) in dry THF (10 mL) was added DIAD (188 mg, 0.93 mmol) under $N_2$. The resulting solution was stirred at room temperature for 2 hours. After quenched with water, the mixture was extracted with DCM. The combined organic layer was washed with water and brine, dried over anhydrous sodium sulfate and concentrated. The residue was purified by preparative TLC to afford desired product tert-butyl 5-amino-4-(4-(3-(2-(2-((4-(4-bromo-3-(pyridin-4-yl)-1H-pyrazol-1-yl)phenoxy)

methyl)phenoxy)ethoxy)-propoxy)-1,3-dioxoisoindolin-2-yl)-5-oxopentanoate (110 mg, 42.2% yield) as white solid. LCMS (ES+): m/z 854.2 [M+H]+.

Step D: 4-(3-(2-(2-((4-(4-bromo-3-(pyridin-4-yl)-1H-pyrazol-1-yl)phenoxy)methyl) phenoxy)ethoxy) propoxy)-2-(2,6-dioxopiperidin-3-yl)isoindoline-1,3-dione

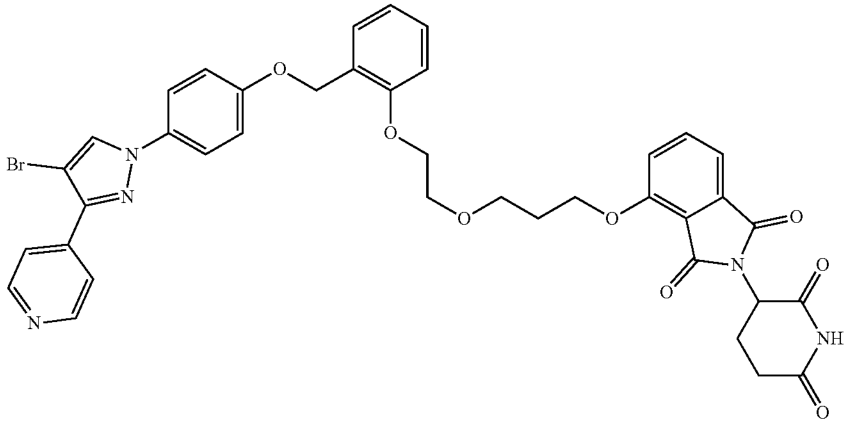 [SMILES: O=C1CCC(N2C(=O)c3cccc(OCCCOCCOc4ccccc4COc4ccc(-n5cc(Br)c(-c6ccncc6)n5)cc4)c3C2=O)C(=O)N1]

To a solution of tert-butyl 5-amino-4-(4-(3-(2-(2-((4-(4-bromo-3-(pyridin-4-yl)-1H-pyrazol-1-yl)phenoxy)methyl) phenoxy)ethoxy)propoxy)-1,3-dioxoisoindolin-2-yl)-5-oxo-pentanoate (80 mg, 0.094 mmol) in acetonitrile (15 mL), add 4-methylbenzenesulfonic acid (32.3 mg, 0.28 mmol). The solution was stirred at 60° C. for 48 hours. After cooling to room temperature, the reaction was quenched with $NaHCO_3$ aq. (to pH>7), and the mixture was extracted with DCM (20 mL×3). The combined organic layer was dried over $Na_2SO_4$ and concentrated under vacuum. The residue was purified by perp-TLC to afford desired product 4-(3-(2-(2-((4-(4-bromo-3-(pyridin-4-yl)-1H-pyrazol-1-yl)phenoxy)methyl) phenoxy)ethoxy)propoxy)-2-(2,6-dioxopiperidin-3-yl)-isoindoline-1,3-dione (40 mg, 54.8% yield) as white solid. LCMS (ES+): m/z 781.1 [M+H]+.

Step E: 2-(2,6-dioxopiperidin-3-yl)-4-(3-(2-(2-((4-(4-(1-oxo-2,3-dihydro-1H-inden-5-yl)-3-(pyridin-4-yl)-1H-pyrazol-1-yl)phenoxy)methyl)phenoxy) ethoxy)propoxy) isoindoline-1,3-dione

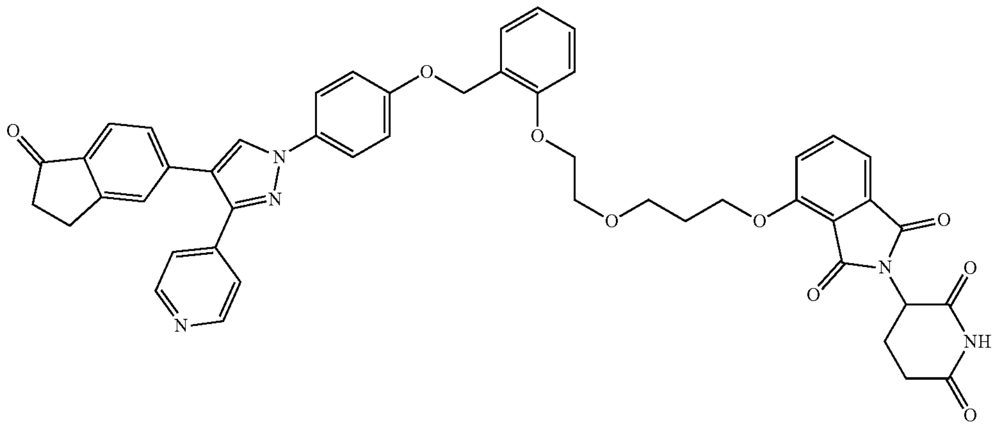 [SMILES: O=C1CCC(N2C(=O)c3cccc(OCCCOCCOc4ccccc4COc4ccc(-n5cc(-c6ccc7c(c6)CCC7=O)c(-c6ccncc6)n5)cc4)c3C2=O)C(=O)N1]

To a solution of 4-(3-(2-(2-((4-(4-bromo-3-(pyridin-4-yl)-1H-pyrazol-1-yl)phenoxy)methyl)phenoxy)ethoxy)propoxy)-2-(2,6-dioxopiperidin-3-yl)isoindoline-1,3-dione (40 mg, 0.051 mmol) in 1,4-dioxane/$H_2O$ (5 mL, v/v=10/1) was added 5-(4,4,5,5-tetramethyl-1,3,2-dioxaborolan-2-yl)-2,3-dihydro-1H-inden-1-one (19.87 mg, 0.077 mmol), $Pd_2$(dba)$_3$ (4.67 mg, 0.0051 mmol), CsF (31.0 mg, 0.20 mmol) [(t-Bu)$_3$PH]$BF_4$ (0.59 mg, 0.0020 mmol), N,N-dicyclohexylmethylamine (0.50 mg, 0.0026 mmol). The resulting solution was stirred at 100° C. for 2 hours under $N_2$. After cooling to room temperature, the reaction was diluted with DCM (50 mL), washed with water and brine. The organic phase was dried over anhydrous sodium sulfate, concentrated under vacuum. The residue was purified by preparative TLC to afford desired product 2-(2,6-dioxopiperidin-3-yl)-4-(3-(2-(2-((4-(4-(1-oxo-2,3-dihydro-1H-inden-5-yl)-3-(pyridin-4-yl)-1H-pyrazol-1-yl)phenoxy)methyl)phenoxy)ethoxy)propoxy)isoindoline-1,3-dione (30 mg, 70.3% yield) as white solid. LCMS ($ES^+$): m/z 832.3 $[M+H]^+$.

Step F: (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy)propoxy)isoindoline-1,3-dione

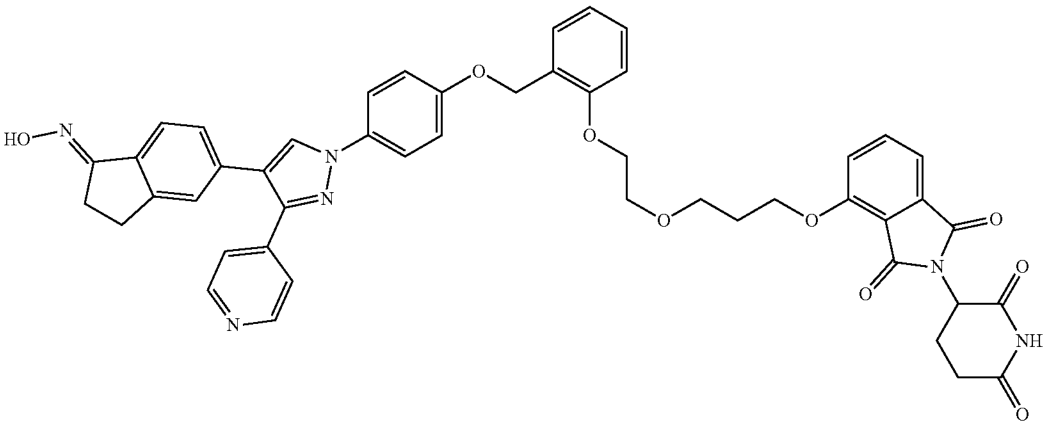 [SMILES: O=C1CCC(N2C(=O)c3cccc(OCCCOCCOc4ccccc4COc4ccc(-n5cc(-c6ccc7c(c6)CC/C7=N\O)c(-c6ccncc6)n5)cc4)c3C2=O)C(=O)N1]

To a solution of 2-(2,6-dioxopiperidin-3-yl)-4-(3-(2-(2-((4-(4-(1-oxo-2,3-dihydro-1H-inden-5-yl)-3-(pyridin-4-yl)-1H-pyrazol-1-yl)phenoxy)methyl)phenoxy)ethoxy)-propoxy)isoindoline-1,3-dione (30 mg, 0.036 mmol) in acetonitrile/pyridine (3 mL, v/v=2/1) was added hydroxylamine hydrochloride (25.1 mg, 0.36 mmol). The mixture was stirred at 40° C. for 20 minutes, the it was diluted with DCM (20 mL), and washed with brine (10 mL). The organic phase was concentrated under vacuum. The residue was purified by preparative TLC to afford (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy) propoxy)isoindoline-1,3-dione (6.2 mg, 20.3% yield) as white solid. NMR (400 MHz, $CDCl_3$): δ 8.57-8.56 (m, 2H), 8.32 (s, 1H), 7.93 (s, 1H), 7.69-7.63 (m, 3H), 7.57-7.51 (m, 3H), 7.43-7.41 (m, 1H), 7.38-7.36 (d, J=7.2 Hz, 1H), 7.28 (s, 2H), 7.23 (s, 2H), 7.15-7.13 (d, J=7.6 Hz, 1H), 7.08-7.06 (m, 2H), 7.00-6.97 (m, 1H), 6.91-6.89 (d, J=7.6 Hz, 1H), 5.15 (s, 2H), 4.92-4.88 (m, 1H), 4.26-4.23 (t, J=6.4 Hz, 2H), 4.20-4.17 (t, J=4.4 Hz, 2H), 3.86-3.84 (t, J=4.8 Hz, 2H), 3.79-3.76 (t, J=6.0 Hz, 2H), 3.08-2.96 (m, 4H), 2.90-2.82 (m, 1H), 2.81-2.66 (m, 2H), 2.16-2.05 (m, 3H); LCMS ($ES^+$): m/z 847.3 $[M+H]^+$.

Compound 212 may be prepared in a manner analogous to compound 213.

Example Synthesis of Compound 215: (E)-2-(2,6-Dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione

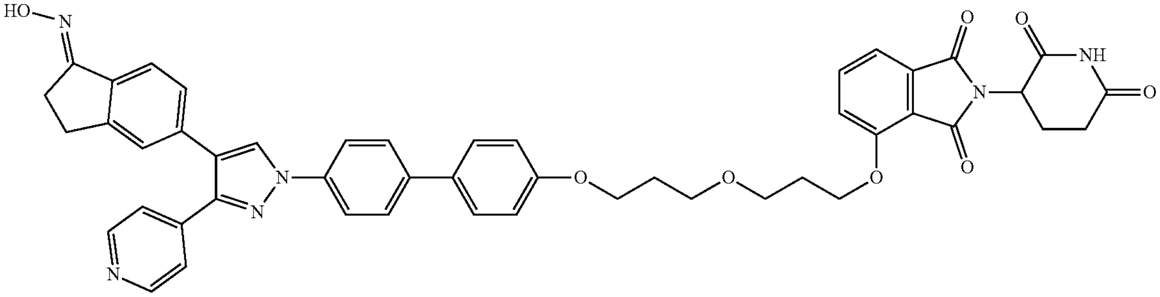 [SMILES: O=C1CCC(N2C(=O)c3cccc(OCCCOCCCOc4ccc(-c5ccc(-n6cc(-c7ccc8c(c7)CC/C8=N\O)c(-c7ccncc7)n6)cc5)cc4)c3C2=O)C(=O)N1]

Step A: 4-bromo-4'-methoxy-1,1'-biphenyl

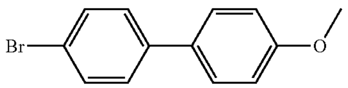

To a solution of (4-methoxyphenyl)boronic acid (5 g, 32.9 mmol) in toluene/MeOH (200 mL/100 mL) was added 1,4-dibromobenzene (11.6 g, 49.4 mmol), $Pd(PPh_3)_4$ (1.9 g, 1.65 mmol) and $Cs_2CO_3$ (21.4 g, 65.8 mmol). The resulting solution was stirred at 100° C. for 16 hours under $N_2$ atmosphere. TLC showed the reaction was completed. After cooled to room temperature, the reaction mixture was diluted with 50 mL of EA, washed with water, brine. The organic phase was dried over anhydrous sodium sulfate and concentrated in vacuo. The residue was purified by chromatography column to afford 4-bromo-4'-methoxy-1,1'-biphenyl (7.0 g, 80% yield). LCMS (ES+): m/z 263.1 $[M+H]^+$.

Step B: (4'-methoxy-[1,1'-biphenyl]-4-yl)boronic acid

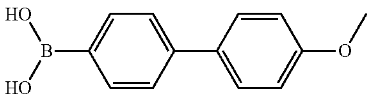 [SMILES: COc1ccc(-c2ccc(B(O)O)cc2)cc1]

To a solution of 4-bromo-4'-methoxy-1,1'-biphenyl (2 g, 7.63 mmol) in dry THF (30 mL) was added n-BuLi (9.2 ml, 22.9 mmol, 2.5 M in hexane) dropwise at −78° C. under $N_2$ atmosphere. 1 hour later, $(CH_3O)_3B$ (2.38 g, 22.9 mmol) was added dropwise at −78° C. The resulting solution was stirred for 1 hour at −78° C. and overnight at 5° C. After quenched with saturated $NH_4Cl$ solution, the mixture was extracted with EA (30 mL×2.) The combined organic layer was dried over anhydrous sodium sulfate. The residue was purified by chromatography column to afford (4'-methoxy-[1,1'-biphenyl]-4-yl)boronic acid (1.0 g, 58% yield). NMR (400 MHz, DMSO-d6): δ 8.06 (s, 2H), 7.84 (d, J=7.6 Hz, 2H), 7.63 (d, J=7.6 Hz, 2H), 7.58 (d, J=7.6 Hz, 2H), 7.02 (d, J=7.6 Hz, 2H), 3.80 (s, 3H).

Step C: 4-(4-bromo-1-(4'-methoxy-[1,1'-biphenyl]-4-yl)-1H-pyrazol-3-yl)pyridine

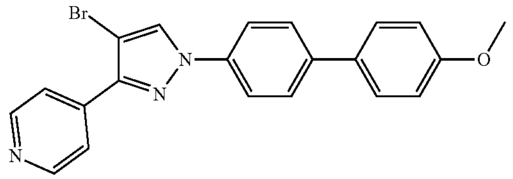 [SMILES: COc1ccc(-c2ccc(-n3cc(Br)c(-c4ccncc4)n3)cc2)cc1]

To a solution of (4'-methoxy-[1,1'-biphenyl]-4-yl)boronic acid (1 g, 4.39 mmol) in DCM/pyridine (40 ml/4 ml) was added $Cu(OAc)_2$ (0.8 g, 4.39 mmol) and 4-(4-bromo-1H-pyrazol-3-yl)pyridine (1.5 g, 6.58 mmol). The resulting solution was stirred at 5° C. for 16 hours under $O_2$ atmosphere. The reaction mixture was washed with ammonia (20 mL×2). The organic phase was dried over $Na_2SO_4$, concentrated under vacuum. The residue was applied onto a silica gel column to afford desired product 4-(4-bromo-1-(4'-methoxy-[1,1'-biphenyl]-4-yl)-1H-pyrazol-3-yl)pyridine (1 g crude, 56% yield). LCMS ($ES^+$): m/z 407.4 [M+H]+.

Step D: 4-(1-(4'-(3-(3-(benzyloxy)propoxy)propoxy)-[1,1'-biphenyl]-4-yl)-4-bromo-1H-pyrazol-3-yl)pyridine

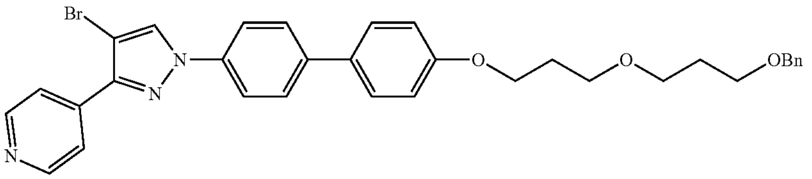 [SMILES: Brc1cn(-c2ccc(-c3ccc(OCCCOCCCOCc4ccccc4)cc3)cc2)nc1-c1ccncc1]

To a solution of 4-(4-Bromo-1-(4'-methoxy-[1,1'-biphenyl]-4-yl)-1H-pyrazol-3-yl)

pyridine (1 g, 2.46 mmol) in DCM (40 mL) was added $BBr_3$ (1.85 g, 7.38 mmol) dropwise. The resulting solution was stirred at 10° C. for 2 hour. After quenched with MeOH and concentrated, crude was applied onto a silica gel column to afford desired product 4'-(4-bromo-3-(pyridin-4-yl)-1H-pyrazol-1-yl)-[1,1'-biphenyl]-4-ol (0.6 g, 62% yield). To a solution of 4'-(4-bromo-3-(pyridin-4-yl)-1H-pyrazol-1-yl)-[1,1'-biphenyl]-4-ol (375 mg, 0.96 mmol) in dry DMF (5 mL) was added $Cs_2CO_3$ (1.56 g, 4.80 mmol) and 3-(3-(benzyloxy)propoxy)propyl methanesulfonate (0.58 g, 1.92 mmol). The resulting solution was stirred at 75° C. for 2 hours. After cooled to room temperature, the reaction mixture was diluted with EA (50 mL), washed with water and brine. The organic layer was dried over anhydrous sodium sulfate. The residue was purified by chromatography column to afford 4-(1-(4'-(3-(3-(benzyloxy)propoxy)propoxy)-[1,1'-biphenyl]-4-yl)-4-bromo-1H-pyrazol-3-yl)pyridine (400 mg, 70% yield). $^1H$ NMR (400 MHz, DMSO-d6): δ 9.02 (s, 1H), 8.73 (br, 2H), 8.00 (m, 2H), 7.80 (d, J=8.0 Hz, 2H), 7.67 (d, J=8.4 Hz, 2H), 7.30 (m, 5H), 7.03 (d, J=8.4 Hz, 2H), 4.45 (m, 2H), 4.06 (t, J=5.6 Hz, 2H), 3.53 (m, 7H), 1.97 (m, 2H), 1.77 (m, 2H).

Step E: 5-(1-(4'-(3-(3-hydroxypropoxy)propoxy)-[1,1'-biphenyl]-4-yl)-3-(pyridin-4-yl)-1H-pyrazol-4-yl)-2,3-dihydro-1H-inden-1-one

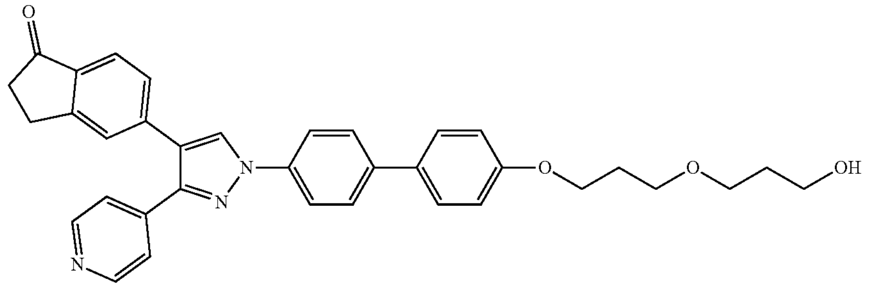 [SMILES: O=C1CCc2cc(-c3cn(-c4ccc(-c5ccc(OCCCOCCCO)cc5)cc4)nc3-c3ccncc3)ccc21]

To a solution of 4-(1-(4'-(3-(3-(benzyloxy)propoxy)propoxy)-[1,1'-biphenyl]-4-yl)-4-bromo-1H-pyrazol-3-yl) pyridine (0.4 g, 0.67 mmol) and 5-(4,4,5,5-tetramethyl-1,3,2-dioxaborolan-2-yl)-2,3-dihydro-1H-inden-1-one (260 mg, 1.01 mmol) in 1,4-dioxane (15 mL)/$H_2O$ (1.5 mL) was added CsF (328 mg, 2.16 mmol), $Pd_2(dba)_3$ (196 mg, 0.216 mmol), tri-tert-butylphosphine tetrafluoroborate (124 mg, 0.43 mmol) and two drops of N-cyclohexyl-N-methylcyclohexanamine subsequently. The reaction was heated to 100° C. for 2 hours under $N_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product 5-(1-(4'-(3-(3-(benzyloxy)propoxy)propoxy)-[1,1'-biphenyl]-4-yl)-3-(pyridin-4-yl)-1H-pyrazol-4-yl)-2,3-dihydro-1H-inden-1-one (0.4 g, 92% yield) as brown oil. To a solution of 5-(1-(4'-(3-(3-(benzyloxy)propoxy)propoxy)-[1,1'-biphenyl]-4-yl)-3-(pyridin-4-yl)-1H-pyrazol-4-yl)-2,3-dihydro-1H-inden-1-one (400 mg, 0.16 mmol) in THF/MeOH (10 mL/1 mL and two drops of concentrated HCl was added $Pd(OH)_2$ on carbon (200 mg). The mixture was stirred at 5° C. for 1 hour under $H_2$ 1 atm. The mixture was filtered and the solid was washed with THF. The organic layer was concentrated and purified by column to afford 5-(1-(4'-(3-(3-hydroxypropoxy) propoxy)-[1,1'-biphenyl]-4-yl)-3-(pyridin-4-yl)-1H-pyrazol-4-yl)-2,3-dihydro-1H-inden-1-one (250 mg, 72% yield). $^1H$ NMR (400 MHz, $CDCl_3$): δ 8.73 (d, J=5.6 Hz, 2H), 8.64 (s, 3H), 8.10 (m, 2H), 7.85 (m, 3H), 7.68 (d, J=6.0 Hz, 2H), 7.55 (m, 4H), 7.28-7.50 (m, 6H), 7.00 (d, J=8.4 Hz, 2H), 5.68 (m, 1H), 4.49 (s, 2H), 4.15 (m, 3H), 3.45-3.70 (m, 6H), 3.18 (m, 2H), 2.78 (m, 2H)

Step F: tert-butyl 5-amino-4-(1,3-dioxo-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindolin-2-yl)-5-oxopentanoate

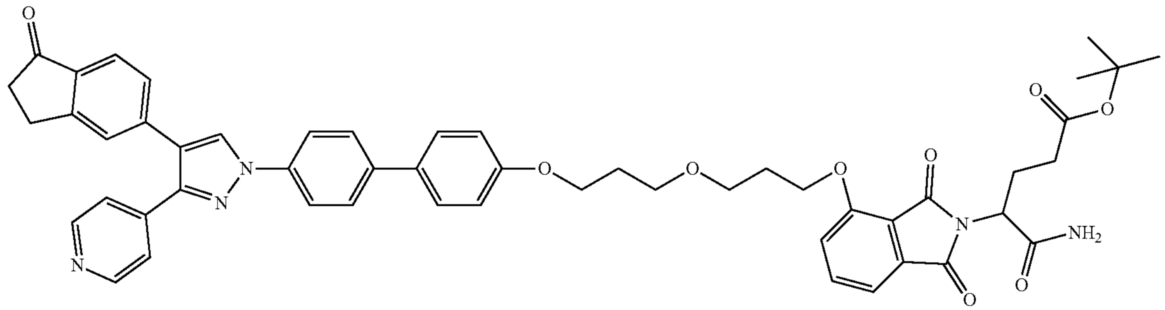 [SMILES: CC(C)(C)OC(=O)CCC(C(N)=O)N1C(=O)c2cccc(OCCCOCCCOc3ccc(-c4ccc(-n5cc(-c6ccc7c(c6)CCC7=O)c(-c6ccncc6)n5)cc4)cc3)c2C1=O]

To a solution of 5-(1-(4'-(3-(3-hydroxypropoxy)propoxy)-[1,1'-biphenyl]-4-yl)-3-(pyridin-4-yl)-1H-pyrazol-4-yl)-2,3-dihydro-1H-inden-1-one (250 mg, 0.45 mmol), $Ph_3P$ (351 mg, 1.35 mmol) and tert-butyl 5-amino-4-(4-hydroxy-1,3-dioxoisoindolin-2-yl)-5-oxopentanoate (233 mg, 0.67 mmol) in dry THF (20 mL) was DIAD (266 mg, 1.35 mmol) in THF (3 mL) dropwise at 0° C. The resulting solution was stirred at 0~10° C. for 2 hours. The reaction was diluted with EA (50 mL), washed with water and brine. The organic layer was dried over anhydrous sodium sulfate, concentrated and applied onto a silica gel column to afford tert-butyl 5-amino-4-(1,3-dioxo-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindolin-2-yl)-5-oxopentanoate (150 mg, 38% yield) as oil. LCMS (ES+): m/z 890.4 $[M+H]^+$.

Step G: 2-(2,6-dioxopiperidin-3-yl)-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione

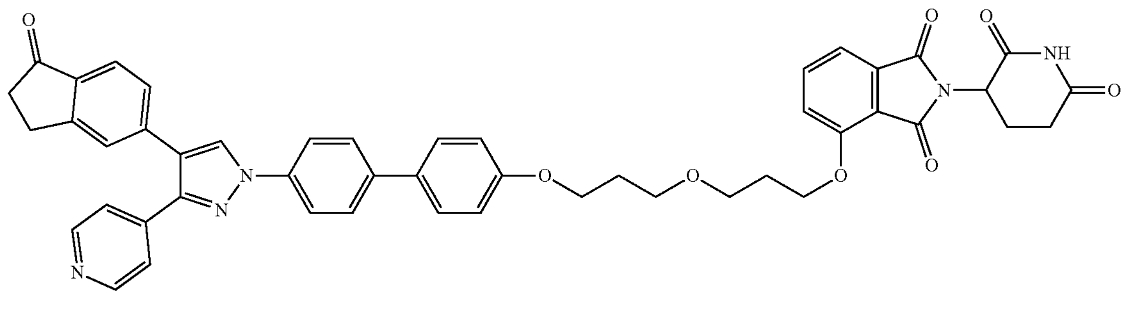 [SMILES: O=C1CCC(N2C(=O)c3cccc(OCCCOCCCOc4ccc(-c5ccc(-n6cc(-c7ccc8c(c7)CCC8=O)c(-c7ccncc7)n6)cc5)cc4)c3C2=O)C(=O)N1]

To a solution of tert-butyl 5-amino-4-(1,3-dioxo-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindolin-2-yl)-5-oxopentanoate (150 mg, 0.168 mmol) in $CH_3CN$ (5 mL) was added TsOH (289 mg, 1.68 mmol). The resulting solution was stirred at 80° C. for 3 hours. The reaction was quenched by saturated $NaHCO_3$ and extracted with EA. The organic layer was dried over anhydrous sodium sulfate, concentrated and purified by preparative TLC to afford 2-(2,6-dioxopiperidin-3-yl)-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione (100 mg, 73% yield). LCMS (ES+): m/z 816.3 $[M+H]^+$.

Step H: (E)-2-(2,6-dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione

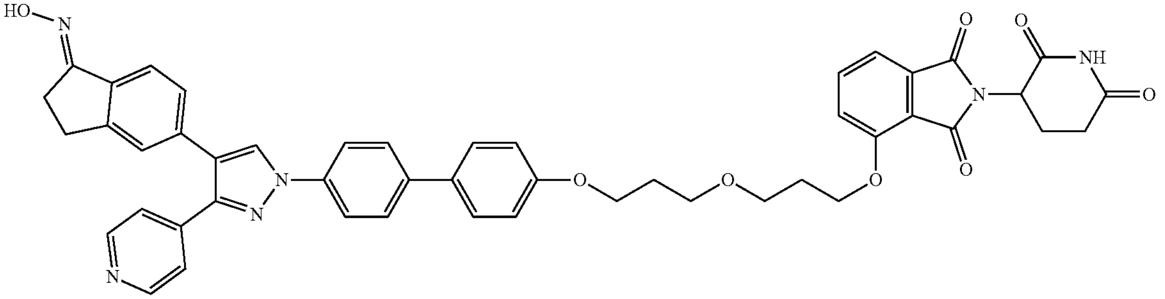 [SMILES: O=C1CCC(N2C(=O)c3cccc(OCCCOCCCOc4ccc(-c5ccc(-n6cc(-c7ccc8c(c7)CC/C8=N\O)c(-c7ccncc7)n6)cc5)cc4)c3C2=O)C(=O)N1]

To a solution of 2-(2,6-dioxopiperidin-3-yl)-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione (100 mg, 0.123 mmol) and hydroxylamine hydrochloride (256 mg, 3.681 mmol) in MeOH/DCM (4 mL/1 mL) was added $NaHCO_3$ (464 mg, 5.521 mmol) at 50° C. The mixture was stirred at 50° C. for 1 hour. The residue was purified by preparative TLC with DCM/MeOH (20:1) to afford the desired product (E)-2-(2,6-dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione (24 mg, 24% yield) as a yellow solid. NMR (400 MHz, DMSO-d6): δ 11.09 (s, 1H), 10.90 (s, 1H), 8.90 (s, 1H), 8.59 (d, J=5.6 Hz, 2H), 8.02 (d, J=8.4 Hz, 2H), 7.79 (m, 3H), 7.38-7.70 (m, 8H), 7.25 (d, J=6.0 Hz, 1H), 6.98 (d, J=8.8 Hz, 2H), 5.09 (m, 1H), 4.26 (m, 2H), 4.05 (m, 2H), 3.60 (m, 4H), 3.05 (m, 2H), 2.86 (m, 3H), 2.50 (m, 3H), 2.03 (m, 5H); LCMS ($ES^+$): m/z 831.3 $[M+H]^+$.

Compound 214 may be prepared in a manner analogous to compound 215.

Example Synthesis of Compound 100: (2S,4R)-1-((S)-2-(2-(3-(4-(4-(3-(2,6-Difluoro-3-((R)-3-fluoropyrrolidine-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide

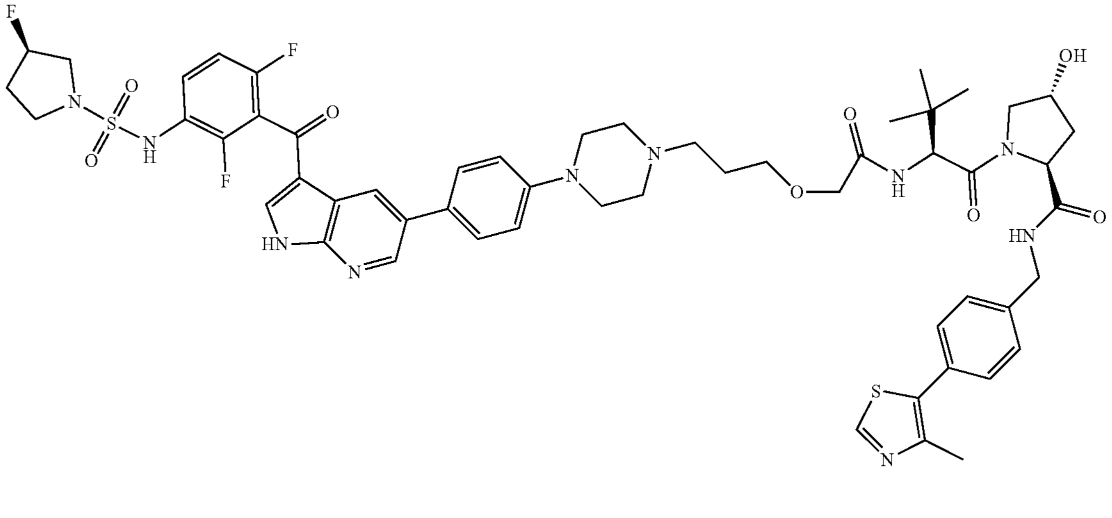 [SMILES: Cc1ncsc1-c1ccc(CNC(=O)[C@@H]2C[C@@H](O)CN2C(=O)[C@@H](NC(=O)COCCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

Step A: tert-butyl 2-(3-chloropropoxy)acetate

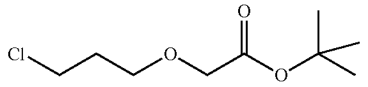

To a solution of tert-butyl 2-bromoacetate (5.0 g, 26 mmol) and 3-chloropropan-1-ol (2.9 g, 31 mmol) in dry DMF (15 mL) was added NaOH (1.2 g, 31 mmol) at 0° C. After stirring for 2 hours at 0° C., it was warmed to room temperature overnight. The reaction was quenched with $H_2O$ (20 mL) at 0° C., and the mixture was extracted with PE (20 mL×2). The combined organic layer was washed with water, brine. The organic phase was concentrated under vacuum to afford desired product tert-butyl 2-(3-chloropropoxy)-acetate (2.8 g, 52% yield) as oil, which was used directly in next step. $^1$H NMR (400 MHz, $CDCl_3$): δ 3.97 (s, 2H), 3.65-3.70 (m, 4H), 2.05-2.08 (m, 2H), 1.49 (s, 9H).

Step B: tert-butyl 2-(3-(4-(4-(4,4,5,5-tetramethyl-1,3,2-dioxaborolan-2-yl)phenyl)piperazin-1-yl)propoxy)acetate

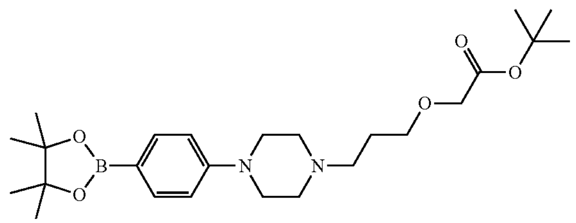 [SMILES: CC(C)(C)OC(=O)COCCCN1CCN(c2ccc(B3OC(C)(C)C(C)(C)O3)cc2)CC1]

To a solution of 1-(4-(4,4,5,5-tetramethyl-1,3,2-dioxaborolan-2-yl)phenyl)piperazine 2,2,2-trifluoroacetate (530 mg, 1.32 mmol) in dry DMF (5 mL) were added $K_2CO_3$ (911 mg, 6.60 mmol), KI (438 mg, 2.64 mmol) and tert-butyl 2-(3-chloropropoxy)acetate (550 mg, 2.64 mmol) subsequently. The resulting solution was stirred at 90° C. for 3 hours. After cooling to room temperature, the reaction was diluted with EA (50 mL), and the mixture was washed with water, brine. The organic phase was concentrated under vacuum. The residue was purified by prep-TLC to afford desired product tert-butyl 2-(3-(4-(4-(4,4,5,5-tetramethyl-1,3,2-dioxaborolan-2-yl)phenyl) piperazin-1-yl)propoxy)acetate (300 mg, crude). $^1$H NMR (400 MHz, $CDCl_3$): δ 7.70 (d, J=8.0 Hz, 2H), 6.89 (d, J=8.0 Hz, 2H), 3.96 (br, 2H), 3.27 (br, 4H), 3.21 (br, 2H), 2.60 (br, 4H), 2.51-2.53 (m, 2H), 1.82-1.85 (m, 2H), 1.42 (s, 9H), 1.24 (s, 12H).

Step C: (R)-tert-butyl 2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetate

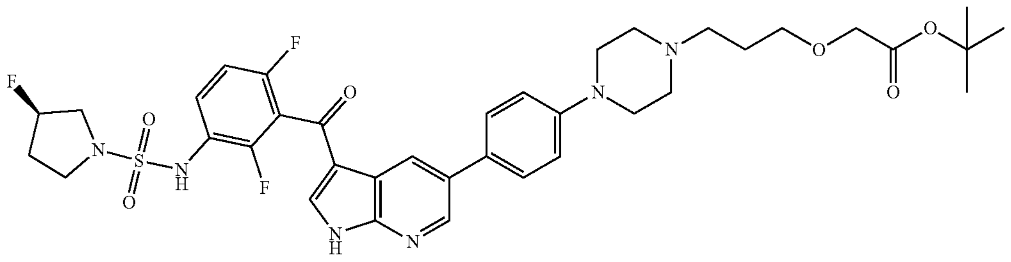 [SMILES: CC(C)(C)OC(=O)COCCCN1CCN(c2ccc(-c3cnc4[nH]cc(C(=O)c5c(F)ccc(NS(=O)(=O)N6CC[C@@H](F)C6)c5F)c4c3)cc2)CC1]

To a solution of (R)—N-(3-(5-bromo-1H-pyrrolo[2,3-b]pyridine-3-carbonyl)-2,4-difluorophenyl)-3-fluoropyrrolidine-1-sulfonamide (100 mg, 0.20 mmol) in dioxane/$H_2O$ (10 mL/1 mL) was added tert-Butyl 2-(3-(4-(4-(4,4,5,5-tetramethyl-1,3,2-dioxaborolan-2-yl)phenyl)piperazin-1-yl)propoxy)acetate (200 mg, 0.43 mmol), Pd(aMphos)$Cl_2$ (15 mg, 0.02 mmol) and CsF (121 mg, 0.80 mmol). The resulting solution was stirred at 95° C. for 16 hours under $N_2$ atmosphere. TLC showed completion of the reaction. After cooled to room temperature, the reaction mixture was diluted with 50 ml of EA, washed with water and brine. The organic layer was dried over anhydrous sodium sulfate. The residue was purified by pre-TLC to afford desired product (R)-tert-butyl 2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetate (80 mg, 53% yield). NMR (400 MHz, $CDCl_3$): δ 12.00 (br, 1H), 8.87 (s, 1H), 8.60 (s, 1H), 7.75 (s, 2H), 7.54 (d, J=8.0 Hz, 2H), 6.98-7.05 (m, 3H), 5.15-5.30 (m, 1H), 3.97 (s, 2H), 3.71-3.75 (m, 2H), 3.49-3.65 (m, 6H), 3.28 (s, 4H), 2.58-2.67 (m, 6H), 1.80-2.30 (m, 3H), 1.49 (s, 9H).

Step D: (2S,4R)-1-((S)-2-(2-(3-(4-(4-(3-(2,6-Difluoro-3-((R)-3-fluoropyrrolidine-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide

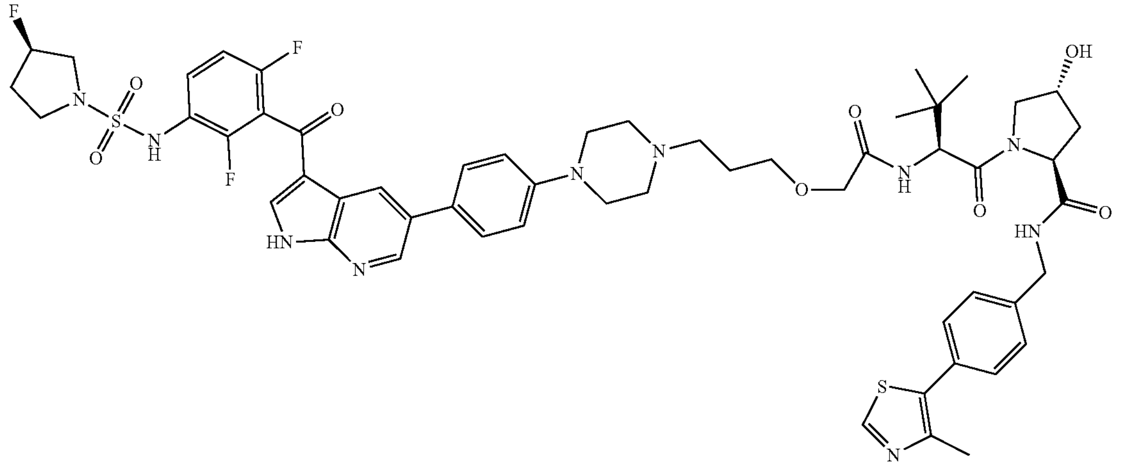 [SMILES: Cc1ncsc1-c1ccc(CNC(=O)[C@@H]2C[C@@H](O)CN2C(=O)[C@@H](NC(=O)COCCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

To a solution of (R)-tert-butyl 2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetate (80 mg, 0.13 mmol) in dioxane (2 mL) was added HCl in dioxane (2 mL, 8 M). The resulting solution was stirred at 50° C. for 5 hours. After cooling to room temperature, the solvent was removed under vacuum to afford (R)-2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetic acid (74 mg, 100% yield, calculated). To a solution of (R)-2-(3-(4-(4-(3-(2,6-difluoro-3-(3-fluoropyrrolidine-1-sulfonamido)-benzoyl)-1H-pyrrolo[2,3-b]pyridin-5-yl)phenyl)piperazin-1-yl)propoxy)acetic acid (74 mg, 0.11 mmol) (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (91 mg, 0.19 mmol) and DIEA (142 mg, 1.10 mmol) in dry NMP (5.0 mL) was added PyBOP (172 mg, 0.33 mmol) at room temperature. After stirring at 10° C. for 1 hour, the reaction was quenched with brine (20 mL), and the mixture was taken up with EA. The organic phase was concentrated under vacuum, and the residue was purified by prep-TLC and prep-HPLC to afford desired product (2S,4R)-1-((S)-2-(2-(3-(4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide (20 mg, 17% yield 2 steps) as white solid. $^1H$ NMR (400 MHz, $CD_3OD$): δ 8.82 (s, 1H), 8.65 (s, 1H), 8.59 (s, 1H), 7.89 (s, 1H), 7.74 (m, 1H), 7.59 (d, J=8.8 Hz, 2H), 7.30-7.50 (m, 4H), 7.07-7.20 (m, 3H), 5.15-5.30 (m, 1H), 4.62 (s, 1H), 4.50-4.60 (m, 3H), 4.30 (d, J=7.8 Hz, 1H), 4.12 (m, 2H), 3.78-3.95 (m, 2H), 3.40-3.80 (m, 14H), 3.10 (m, 5H), 2.42 (s, 3H), 1.98-2.30 (m, 8H), 1.03 (s, 9H); LCMS ($ES^+$): m/z 1113.3 $[M+H]^+$.

Example Synthesis of Compound 152: (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione

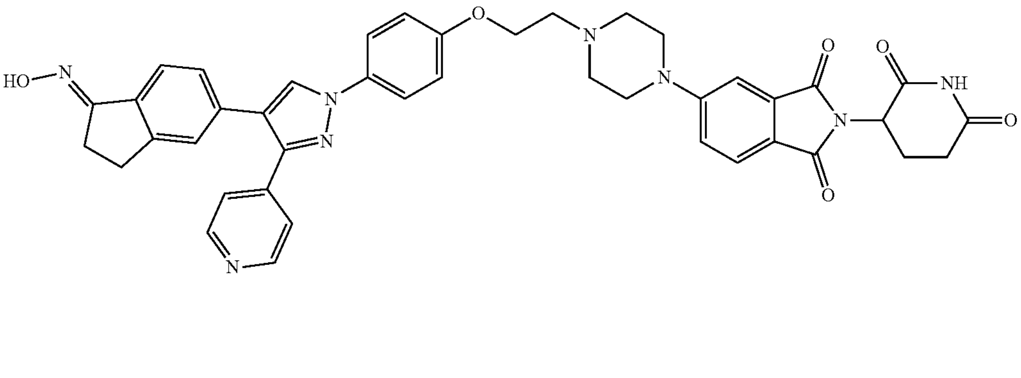 [SMILES: O=C1CCC(N2C(=O)c3ccc(N4CCN(CCOc5ccc(-n6cc(-c7ccc8c(c7)CC/C8=N\O)c(-c7ccncc7)n6)cc5)CC4)cc3C2=O)C(=O)N1]

Step A: 2-(4-(4-bromo-3-(pyridin-4-yl)-1H-pyrazol-1-yl)phenoxy)acetaldehyde

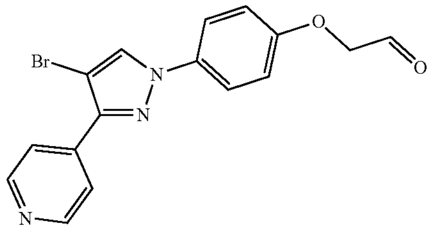 [SMILES: O=CCOc1ccc(-n2cc(Br)c(-c3ccncc3)n2)cc1]

To a solution of 4-(4-bromo-1-(4-(2,2-diethoxyethoxy)phenyl)-1H-pyrazol-3-yl)pyridine (1 g, 2.32 mmol) in $CH_3CN$ (10 mL) was added cone. HCl (2 mL, diluted in 6 mL $H_2O$). The resulting solution was stirred at 55° C. for 1 hour. After cooling to 0° C., The pH was adjusted to around 9 by progressively adding saturated $NaHCO_3$ aqueous solution. The solid was filtered and co-evaporated with $CH_3CN$ to afford 2-(4-(4-bromo-3-(pyridin-4-yl)-1H-pyrazol-1-yl)phenoxy)acetaldehyde (0.3 g, 66.9% yield) as a white solid. LCMS ($ES^+$): m/z 358.0, 376.0/378.0 $[M+H]^+$, $[M+18]^+$.

Step B: 5-(4-(2-(4-(4-bromo-3-(pyridin-4-yl)-1H-pyrazol-1-yl)phenoxy)ethyl)piperazin-1-yl)-2-(2,6-dioxopiperidin-3-yl)isoindoline-1,3-dione

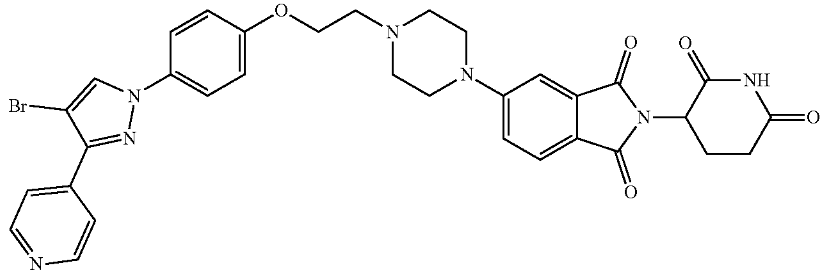 [SMILES: O=C1CCC(N2C(=O)c3ccc(N4CCN(CCOc5ccc(-n6cc(Br)c(-c7ccncc7)n6)cc5)CC4)cc3C2=O)C(=O)N1]

To a solution of 2-(4-(4-bromo-3-(pyridin-4-yl)-1H-pyrazol-1-yl)phenoxy) acetaldehyde (0.1 g, 0.28 mmol) in MeOH (10 mL) were added 2-(2,6-dioxopiperidin-3-yl)-5-(piperazin-1-yl)isoindoline-1,3-dione hydrochloride (127 mg, 0.34 mmol) and cat. HOAc. AcOK was added if pH was below 5~6. Then $NaBH_3CN$ (87 mg, 1.40 mmol) was added. The resulting solution was stirred at 20° C. for 1 hour. After quenched with saturated $NH_4Cl$ (20 mL), and the mixture was extracted with DCM (30 mL×2). The combined organic layer was dried over anhydrous sodium sulfate and concentrated under vacuum. The residue was purified by prep-TLC to afford desired product 5-(4-(2-(4-(4-bromo-3-(pyridin-4-yl)-1H-pyrazol-1-yl)-phenoxy)ethyl)piperazin-1-yl)-2-(2,6-dioxopiperidin-3-yl)isoindoline-1,3-dione (90 mg, 35% yield). LCMS ($ES^+$): m/z 684.1/686.1 $[M+H]^+$.

Step C: 2-(2,6-dioxopiperidin-3-yl)-5-(4-(2-(4-(4-(1-oxo-2,3-dihydro-1H-inden-5-yl)-3-(pyridin-4-yl)-1H-pyrazol-1-yl)phenoxy)ethyl)piperazin-1-yl)isoindoline-1,3-dione

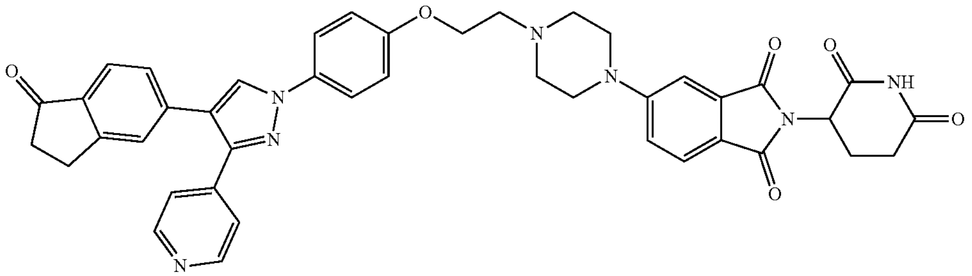 [SMILES: O=C1CCC(N2C(=O)c3ccc(N4CCN(CCOc5ccc(-n6cc(-c7ccc8c(c7)CCC8=O)c(-c7ccncc7)n6)cc5)CC4)cc3C2=O)C(=O)N1]

To a solution of 5-(4-(2-(4-(4-bromo-3-(pyridin-4-yl)-1H-pyrazol-1-yl)phenoxy) ethyl)piperazin-1-yl)-2-(2,6-dioxopiperidin-3-yl)isoindoline-1,3-dione (90 mg, 0.13 mmol) and 5-(4,4,5,5-tetramethyl-1,3,2-dioxaborolan-2-yl)-2,3-dihydro-1H-inden-1-one (37 mg, 0.15 mmol) in dioxane/$H_2O$ (10 mL/1 mL) were added t-$Bu_3PHBF_4$ (31 mg, 0.11 mmol), CsF (80 mg, 0.53 mmol), $Cy_2NMe$ (5 drops) and $Pd_2(dba)_3$ (48 mg, 0.05 mmol) subsequently. The resulting mixture was stirred at 90° C. for 2 hours under $N_2$. After cooling to room temperature, the solvent was removed under reduced pressure. The residue was diluted with EA (30 mF), and then the mixture was washed with brine. The organic phase was evaporated under vacuum. The residue was purified by prep-TFC and prep-HPFC to afford desired product 2-(2,6-Dioxopiperidin-3-yl)-5-(4-(2-(4-(4-(1-oxo-2,3-dihydro-1H-inden-5-yl)-3-(pyridin-4-yl)-1H-pyrazol-1-yl)phenoxy)ethyl)piperazin-1-yl)isoindoline-1,3-dione (60 mg, 69% yield). LCMS ($ES^+$): m/z 736.3 $[M+H]^+$.

Step D: (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione

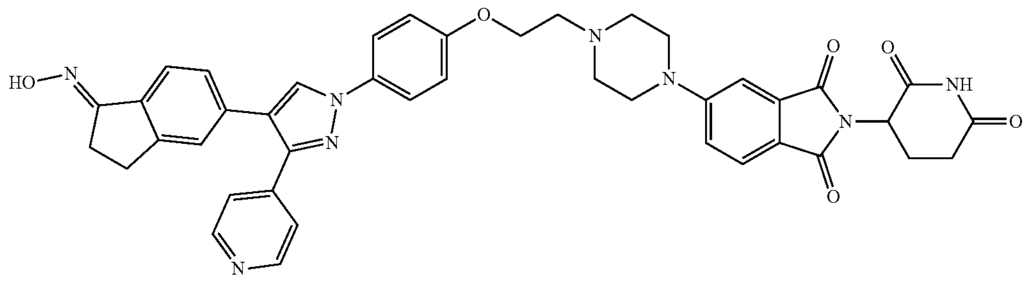 [SMILES: O=C1CCC(N2C(=O)c3ccc(N4CCN(CCOc5ccc(-n6cc(-c7ccc8c(c7)CC/C8=N\O)c(-c7ccncc7)n6)cc5)CC4)cc3C2=O)C(=O)N1]

To a solution of 2-(2,6-dioxopiperidin-3-yl)-5-(4-(2-(4-(4-(1-oxo-2,3-dihydro-1H-inden-5-yl)-3-(pyridin-4-yl)-1H-pyrazol-1-yl)phenoxy)ethyl)piperazin-1-yl)isoindoline-1,3-dione (60 mg, 0.08 mmol) in $CH_3CN$/pyridine (6 mL/3 mL) was added $NH_2OH \cdot HCl$ (57 mg, 0.82 mmol). The mixture was stirred at 45° C. for 0.5 hours. The mixture was diluted with DCM (30 mL) and washed with brine. The organic phase was concentrated under reduced pressure. The residue was purified by prep-TLC (DCM/MeOH 15/1) to afford desired product (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl) isoindoline-1,3-dione as a yellow solid (45 mg, 73% yield). NMR (400 MHz, DMSO-$d_6$): δ 11.07 (s, 1H), 10.89 (s, 1H), 8.75 (s, 1H), 8.58 (d, J=5.6 Hz, 2H), 7.87 (d, J=8.8 Hz, 2H), 7.68 (d, J=8.4 Hz, 1H), 7.55 (d, J=8.0 Hz, 1H), 7.48 (d, J=4.4 Hz, 2H), 7.20-7.41 (m, 4H), 7.14 (d, J=9.2 Hz, 2H), 5.08 (m, 1H), 4.21 (t, J=5.6 Hz, 2H), 3.47 (m, 4H), 2.99-3.02 (m, 2H), 2.67-2.89 (m, 10H), 2.05 (m, 1H); LCMS ($ES^+$): m/z 751.3 $[M+H]^+$.

Example Synthesis of Compound 216: (2S,4R)-1-((S)-2-(3-(2-(3-(3-(2,6-difluoro-3-(propylsulfonamido)benzoyl)-1H-pyrrolo[2,3-b]pyridin-5-yl)phenoxy)ethoxy)propanamido)-3,3-dimethylbutanoyl)-4-hydroxy-N-(4-(4-methylthiazol-5-yl)benzyl) pyrrolidine-2-carboxamide To a solution of 3-[2-[3-[3-[2,6-difluoro-3-(propylsulfonyl-amino)benzoyl]-1H-pyrrolo[2,3-b]pyridin-5-yl]phenoxy]ethoxy]-propanoic acid (22.8 mg, 0.04 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (19.93 mg, 0.043 mmol) in DMF (2 ml) was added TEA (0.1 ml, 0.72 mmol) and PyBOP (22.21 mg, 0.043 mmol) at room temperature. The reaction mixture was stirred for 12 h (overnight) at the same temperature. TLC (DCM:MEOH:$NH_4OH$, 90:9:1) shows no starting materials. The DMF was removed under high vacuum. Crude product was filtered over a silica-carbonate cartridge using DCM:MeOH (9:1) as a eluent. Filtrate was evaporated under vacuum and crude product was purified by PTLC (MeOH:DCM, 1:9, 2×) to give 20 mg of product (52% yield), $^1H$ NMR (500 MHz, DMSO-d6) δ 13.00 (bs, 1H), 9.78 (bs, 1H), 8.96 (s, 1H), 8.71 (s, 1H), 8.62 (s, 1H), 8.55 (t, J=5.5 Hz, 1H), 8.23 (s, 1H), 7.96 (d, J=9.2 Hz, 1H), 7.59 (q, J=8.3 Hz, 1H), 7.52-7.18 (m, 8H), 6.99 (d, J=8.2 Hz, 1H), 5.13 (d, J=3.8 Hz, 1H), 4.57 (d, J=9.4 Hz, 1H), 4.48-4.32 (m, 3H), 4.23 (d, J=5.5 Hz, 1H), 4.19 (t, J=5.1 Hz, 2H), 3.86-3.57 (m, 6H), 3.19-3.06 (m, 2H), 2.61 (m, 1H), 2.43 (s, 3H), 2.43-2.37 (m, 1H), 2.08-2.00 (m, 1H), 1.95-1.87 (m, 1H), 1.80-1.69 (m, 2H), 0.94 (s, 9H), 0.95 (t, 3H). NMR (151 MHz, dmso) δ 180.64, 171.95, 169.97, 169.57, 159.10, 156.03 (dd, J=246.6, 6.9 Hz), 152.34 (dd, J=249.6, 8.4 Hz), 151.42, 148.97, 147.72, 144.17, 139.67, 139.50, 138.81, 131.46, 131.17, 130.28, 129.64, 128.94-128.71 (m), 128.64, 127.42, 127.17, 121.98 (dd, J=13.6, 3.4 Hz), 119.57, 118.54-117.84 (m), 117.47, 115.72, 113.74, 113.11, 112.53-112.23 (m), 68.91, 68.69, 67.21, 67.13, 58.74, 56.37, 53.46, 41.68, 37.97, 35.70, 35.37, 26.36, 16.86, 15.95, 12.63. LC-MS (ESI); m/z $[M+H]^+$: Calcd. for $C_{50}H_{56}F_2N_7O_9S_2$, 1000.3548. Found 1000.3536.

Example Synthesis of Compound of 217: N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)glutaramide To a solution of 5-((4-(3-(2,6-difluoro-3-(propylsulfonamido)-benzoyl)-1H-pyrrolo[2,3-b]pyridin-5-yl)phenyl) amino)-5-oxopentanoic acid (9.7 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.52 mg, 0.02 mmol) in DMF (1 ml) was added TEA (0.1 ml, 0.72 mmol) and PyBOP (9.5 mg, 0.02 mmol) at room temperature. The reaction mixture was stirred for 4 h at the same temperature. TLC (DCM:MEOH:$NH_4OH$, 90:9:1) shows no starting materials. The reaction mixture was diluted with EtOAc (10 mL) and washed with brine (5 mL, 4×), organic phase was dried ($Na_2SO_4$), and evaporated under vacuum. Crude product was purified by PTLC (DCM:MEOH:$NH_4OH$, 90:9:1, 2×) to give 4.8 mg of product (29% yield). $^1H$ NMR (500 MHz, DMSO-d6) δ 10.02 (s, 1H), 8.97 (s, 1H), 8.68 (d, 1H), 8.64-8.52 (m, 2H), 8.21 (s, 1H), 7.95 (d, J=9.2 Hz, 1H), 7.72 (dd, J=36.7, 8.5 Hz, 4H), 7.62-7.54 (m, 1H), 7.40 (dd, 4H), 7.28 (t, J=8.7 Hz, 1H), 5.16 (d, 2H), 4.56 (d, J=9.3 Hz, 1H), 4.50-4.40 (m, 2H), 4.40-4.33 (m, 1H), 4.22 (dd, J=15.8, 5.3 Hz, 1H), 3.76-3.62 (m, 2H), 3.16-3.05 (m, 2H), 2.44 (s, 3H), 2.41-2.17 (m, 4H), 2.09-2.01 (m, 1H), 1.98-1.80 (m, 3H), 1.74 (dq, J=14.9, 7.4 Hz, 2H), 0.96 (s, 9H), 0.95 (t, 3H). NMR (151 MHz, dmso) δ 181.06, 172.39, 172.17, 171.46, 170.15, 156.37 (dd, J=246.6, 6.3 Hz), 152.73 (dd, J=249.4, 8.1 Hz), 151.86, 149.05, 148.13, 144.19, 139.91, 139.37, 139.13, 132.97, 131.64, 131.59, 130.05, 129.22 (d, J=14.7 Hz), 129.06, 127.84, 127.74, 126.89, 122.47 (d, J=14.1 Hz), 120.07, 119.02-118.20 (m), 117.95, 116.06, 112.75 (dd, J=23.4, 2.8 Hz), 69.34, 59.15, 56.90, 56.81, 53.87, 42.08, 38.38, 36.36, 35.63, 34.63, 26.85, 21.91, 17.27, 16.37, 13.04. LC-MS (ESI); m/z $[M+H]^+$: Calcd. for $C_{50}H_{55}F_2N_8O_8S_2$, 997.3552. Found 997.3524.

Example Synthesis of Compound 218: (2S,4R)-1-((S)-2-(5-(4-(3-(2,6-difluoro-3-(propylsulfonamido)benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide To a solution of 5-(4-(3-(2,6-difluoro-3-(propylsulfonamido)-benzoyl)-1H-pyrrolo[2,3-b]pyridin-5-yl)piperazin-1-yl)-5-oxopentanoic acid (9.3 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.27 mg, 0.018 mmol) in DMF (1 ml) was added TEA (0.1 ml, 0.72 mmol) and PyBOP (9.22 mg, 0.018 mmol) at room temperature. The reaction mixture was stirred for 4 h at the same temperature. TLC (DCM:MEOH:$NH_4OH$, 90:9:1) shows no starting materials. The reaction mixture was diluted with EtOAc (10 mL) and washed with brine (5 mL, 4×), organic phase was dried ($Na_2S_{04}$), and evaporated under vacuum. Crude mixture did not show product by TLC, just some starting material (product is soluble in water). Water extracts were lyophilized for overnight, solid residue was filtered using (DCM:MEOH:$NH_4OH$, 90:9:1, 30 mL). Filtrate was evaporated to dryness and crude product was purified by PTLC (DCM:MEOH:NH4OH, 90:9:1, 2×) to give 13 mg of product (81% yield). $^1H$ NMR (500 MHz, DMSO-d6) δ 12.64 (bs, 1H), 9.74 (bs, 1H), 8.97 (s, 1H), 8.62-8.52 (m, 3H), 8.28 (d, J=2.0 Hz, 1H), 8.00 (s, 1H), 7.95 (bs, 1H), 7.90 (d, J=9.2 Hz, 1H), 7.59-7.49 (m, 1H), 7.47-7.27 (m, 4H), 7.20 (t, J=8.7 Hz, 1H), 5.13 (bs, 1H), 4.56 (d, J=9.3 Hz, 1H), 4.48-4.32 (m, 3H), 4.22 (dd, J=15.8, 5.3 Hz, 1H), 3.75-3.57 (m, 5H), 3.23-3.02 (m, 7H), 2.44 (s, 3H), 2.41-2.17 (m, 4H), 2.07-2.01 (m, 1H), 1.96-1.87 (m, 1H), 1.81-1.66 (m, 4H), 0.95 (s, 9H), 0.94 (t, 3H). NMR (151 MHz, dmso) δ 180.70, 171.99, 171.92, 170.44, 169.75, 155.24 (dd, J=248.1, 5.5 Hz), 152.12 (dd, J=248.8, 8.5 Hz), 151.47, 147.73, 144.63, 144.31, 139.52, 138.02, 137.75, 131.19, 129.65, 128.65, 127.98-127.64 (m), 127.44, 123.91-123.09 (m), 118.86-117.72 (m), 117.60, 115.50, 115.23, 112.02 (dd, J=22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72. LC-MS (ESI); m/z $[M+H]^+$: Calcd. for $C_{48}H_{58}F_2N_9O_8S_2$, 990.3817. Found 990.3889.

Example Synthesis of Compound 219: (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide To a solution of 4-(4-(3-(2,6-difluoro-3-(propylsulfonamido)-benzoyl)-1H-pyrrolo[2,3-b]pyridin-5-yl)piperazin-1-yl)-4-oxobutanoic acid (9 mg, 0.016 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.2 mg, 0.018 mmol) in DMF (1 ml) was added TEA (0.1 ml, 0.72 mmol) and PyBOP (9.14 mg, 0.018 mmol) at room temperature. The reaction mixture was stirred for 12 h (overnight) at the same temperature. TLC (DCM:MEOH:$NH_4OH$, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (DCM:MEOH:$NH_4OH$, 90:9:1, 2×) to give 11 mg of product (75% yield). $^1H$ NMR (500 MHz, DMSO-d6) δ 12.66 (bs, 1H), 9.45 (bs, 1H), 8.98 (s, 1H), 8.60 (bs, 1H), 8.29 (s, 1H), 8.04 (s, 1H), 8.01-7.88 (m, 2H), 7.62-7.49 (m, 1H), 7.40 (q, J=8.0 Hz, 4H), 7.26 (t, J=8.8 Hz, 1H), 5.15 (d, J=3.5 Hz, 1H), 4.54 (d, J=9.3 Hz, 1H), 4.49-4.31 (m, 3H), 4.22 (dd, J=16.1, 5.6 Hz, 1H), 3.81-3.53 (m, 6H), 3.26-3.03 (m, 6H), 2.73-2.52 (m, 3H), 2.44 (s, 3H), 2.42-2.33 (m, 1H), 2.09-1.98 (m, 1H), 1.95-1.84 (m, 1H), 1.74 (q, J=7.5 Hz, 2H), 0.96 (t, 3H), 0.94 (s, 9H). NMR (126 MHz, dmso) δ 180.45, 172.02, 171.35, 170.07, 169.64, 156.00 (dd, J=245.9, 6.5 Hz), 152.34 (dd, J=249.7, 8.3 Hz), 151.52, 147.75, 144.70, 144.30, 139.55, 138.08, 137.91, 131.22, 129.66, 128.69, 128.53 (d, J=2.4 Hz), 127.46, 121.96 (d, J=14.1 Hz), 118.61-117.82 (m), 117.60, 115.44, 115.20, 112.32 (dd, J=23.0, 3.3 Hz), 68.95, 58.78, 56.50, 56.39, 53.46, 50.25, 50.13, 44.76, 41.69, 41.17, 37.99, 35.43, 30.18, 28.05, 26.44, 16.89, 16.00, 12.67. LC-MS (ESI); m/z $[M+H]^+$: Calcd. for $C_{47}H_{56}F_2N_9O_8S_2$, 976.3661. Found 976.3712.

Example Synthesis of Compound 220: N1-(4-(3-(2,6-difluoro-3-(propylsulfonamido)benzoyl)-1H-pyrrolo[2,3-b]pyridin-5-yl)phenyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-succinamide. To a solution of 4-((4-(3-(2,6-difluoro-3-(propylsulfonamido)-benzoyl)-1H-pyrrolo[2,3-b]pyridin-5-yl)phenyl)amino)-4-oxobutanoic acid (15 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (13.51 mg, 0.03 mmol) in DMF (1 ml) was added TEA (0.1 ml, 0.72 mmol) and PyBOP (15.05 mg, 0.03 mmol) at room temperature. The reaction mixture was stirred for 4 h at the same temperature. TLC (DCM:MEOH:NH4OH, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MEOH:NH4OH, 90:9:1, 2×) to give 12 mg of product (~85% pure). This product was purified again by PTLC (DCM:MeOH, 9:1) to give 8 mg of product (31% yield). 1H NMR (500 MHz, DMSO-d6) δ 12.97 (bs, 1H), 10.11 (s, 1H), 9.79 (bs, 1H), 8.98 (d, J=2.3 Hz, OH), 8.69 (s, 1H), 8.66-8.49 (m, 2H), 8.23 (s, 1H), 8.02 (d, J=9.0 Hz, 1H), 7.84-7.64 (m, 4H), 7.63-7.53 (m, 1H), 7.51-7.33 (m, 4H), 7.29 (t, J=8.4 Hz, 1H), 5.17 (s, 1H), 4.56 (d, J=7.8 Hz, 1H), 4.50-4.39 (m, 2H), 4.40-4.31 (m, 1H), 4.26-4.16 (m, 1H), 3.66 (q, J=10.1 Hz, 2H), 3.19-3.06 (m, 2H), 2.72-2.52 (m, 4H), 2.44 (s, 3H), 2.12-1.97 (m, 1H), 1.96-1.84 (m, 1H), 1.74 (dq, J=13.2, 8.3, 7.3 Hz, 2H), 0.96 (t, 3H), 0.95 (s, 9H). 13C NMR (126 MHz, dmso) δ 180.66, 172.02, 171.24, 170.67, 169.64, 156.05 (dd, J=246.9, 7.0 Hz), 152.37 (dd, J=249.3, 8.1 Hz), 151.49, 148.66, 147.75, 143.82, 139.53, 139.00, 138.70, 132.54, 131.27, 131.22, 129.68, 129.22-128.38 (m), 128.69, 127.47, 127.39, 126.53, 121.99 (dd, J=12.9, 4.5 Hz), 119.59, 118.72-117.87 (m), 117.57, 115.68, 112.90-112.05 (m), 68.95, 58.79, 56.56, 56.41, 53.51, 41.71, 37.98, 35.45, 31.98, 30.14, 26.43, 16.88, 15.99, 12.65. LC-MS (ESI); m/z [M+H]+: Calcd. for C49H53F2N808S2, 983.3395. Found 983.3569.

Example Synthesis of Compound 221: N1-(4-(3-(2,6-difluoro-3-(propylsulfonamido)benzoyl)-1H-pyrrolo[2,3-b]pyridin-5-yl)phenyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-malonamide. To a solution 3-((4-(3-(2,6-difluoro-3-(propylsulfonamido)-benzoyl)-1H-pyrrolo[2,3-b]pyridin-5-yl)phenyl)amino)-3-oxopropanoic acid (16.8 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (15.5 mg, 0.033 mmol) in DMF (1 ml) was added TEA (0.1 ml, 0.72 mmol) and PyBOP (17.28 mg, 0.033 mmol) at room temperature. The reaction mixture was stirred for 12 h (overnight) at the same temperature. TLC (DCM:MEOH:$NH_4OH$, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MEOH:$NH_4OH$, 90:9:1, 2×), product was purified again by PTLC (DCM:MeOH, 9:1) to give 19.5 mg of product (67% yield). 1H NMR (400 MHz, DMSO-d6) δ 12.96 (bs, 1H), 10.23 (s, 1H), 9.75 (bs, 1H), 8.97 (s, 1H), 8.69 (s, 1H), 8.66-8.51 (m, 2H), 8.26 (d, J=9.1 Hz, 1H), 8.22 (s, 1H), 7.73 (dd, J=8.5 Hz, 4H), 7.59 (q, J=8.6 Hz, 1H), 7.41 (dd, J=8.0 Hz, 4H), 7.28 (t, J=8.7 Hz, 1H), 5.16 (d, 1H), 4.59 (d, J=9.2 Hz, 1H), 4.52-4.33 (m, 3H), 4.24 (dd, J=15.7, 5.0 Hz, 1H), 3.68 (q, J=10.6 Hz, 2H), 3.44 (q, 2H), 3.20-3.05 (m, 2H), 2.45 (s, 3H), 2.10-2.01 (m, 1H), E96-1.89 (m, 1H), E74 (dq, J=14.8, 7.3 Hz, 2H), 0.98 (s, 9H), 0.97 (t, J=8.3 Hz, 3H). 13C NMR (101 MHz, dmso) δ 180.62, 171.91, 169.34, 166.16, 166.03, 156.02 (dd, J=246.8, 7.1 Hz), 152.34 (dd, J=249.4, 8.1 Hz), 151.43, 148.69, 147.73, 143.79, 139.50, 138.69, 138.54, 132.98, 131.17, 131.13, 129.68, 129.11-128.65 (m), 128.67, 128.01, 127.45, 126.53, 122.21-121.73 (m), 119.70, 118.63-117.89 (m), 117.54, 115.66, 112.35 (dd, J=23.5, 3.0 Hz), 68.93, 58.79, 56.66, 56.52, 53.49, 44.32, 41.70, 37.97, 35.60, 26.33, 16.85, 15.96, 12.62. LC-MS (ESI); m/z [M+H]+: Calcd. for C48H51F2N8O8S2, 969.3239. Found 969.3272.

Example Synthesis of Compound 222: (2S,4R)-1-((S)-2-(3-(4-(3-(2,6-difluoro-3-(propylsulfonamido)benzoyl)-1H-pyrrolo[2,3-b]pyridin-5-yl)piperazin-1-yl)-3-oxopropanamido)-3,3-dimethylbutanoyl)-4-hydroxy-N-(4-(4-methylthiazol-5-yl)benzyl)pyrrolidine-2-carboxamide. To a solution of 3-(4-(3-(2,6-difluoro-3-(propylsulfonamido)-benzoyl)-1H-pyrrolo[2,3-b]pyridin-5-yl)piperazin-1-yl)-3-oxopropanoic acid (12.5 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (11.69 mg, 0.03 mmol) in DMF (1 ml) was added TEA (0.1 ml, 0.72 mmol) and PyBOP (13.02 mg, 0.03 mmol) at room temperature. The reaction mixture was stirred for 12 h (overnight) at the same temperature. TLC (DCM:MEOH:$NH_4OH$, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (MeOH:DCM, 1:9, 2×) to give 14.1 mg of product (64% yield). 1H NMR (500 MHz, DMSO-d6) δ 12.71 (bs, 1H), 9.74 (bs, 1H), 8.98 (s, 1H), 8.59 (t, J=5.7 Hz, 1H), 8.29 (s, 1H), 8.26 (d, J=9.1 Hz, 1H), 8.03 (s, 1H), 7.96 (bs, 1H), 7.57 (q, J=7.4, 6.3 Hz, 1H), 7.41 (dd, J=8.0 Hz, 4H), 7.26 (t, J=8.7 Hz, 1H), 5.22-5.05 (m, 1H), 4.58 (d, J=9.3 Hz, 1H), 4.51-4.32 (m, 3H), 4.23 (dd, J=15.8, 5.3 Hz, 1H), 3.67 (q, J=12.3, 10.6 Hz, 8H), 3.52 (dd, J=53.7, 15.5 Hz, 2H), 3.27-3.05 (m, 6H), 2.45 (s, 3H), 2.09-2.00 (m, 1H), 1.96-1.86 (m, 1H), 1.74 (h, J=7.3 Hz, 2H), 0.97 (s, 9H), 0.96 (t, 3H). 13C NMR (101 MHz, dmso) δ 180.41, 171.91, 169.38, 166.32, 166.06, 156.01 (dd, J=246.5, 6.7 Hz), 152.34 (dd, J=249.2, 8.3 Hz), 151.44, 147.73, 144.60, 144.28, 139.50, 138.06, 137.84, 131.17, 129.66, 128.75 (d, J=8.0 Hz), 128.65, 127.43, 121.86 (dd, J=13.5, 3.5 Hz), 118.34 (m), 117.58, 115.42, 115.18, 112.28 (dd, J=23.1, 3.5 Hz), 68.89, 58.75, 56.54, 56.43, 53.49, 50.10, 45.56, 41.68, 41.19, 40.95, 37.95, 35.52, 26.36, 16.85, 15.96, 12.62. LC-MS (ESI); m/z [M+H]+: Calcd. for C46H54F2N9O8S2, 962.3504. Found 962.3694.

Example Synthesis of Compound 294: (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)[1,3'-biazetidin]-1'-yl)isoindoline-1,3-dione

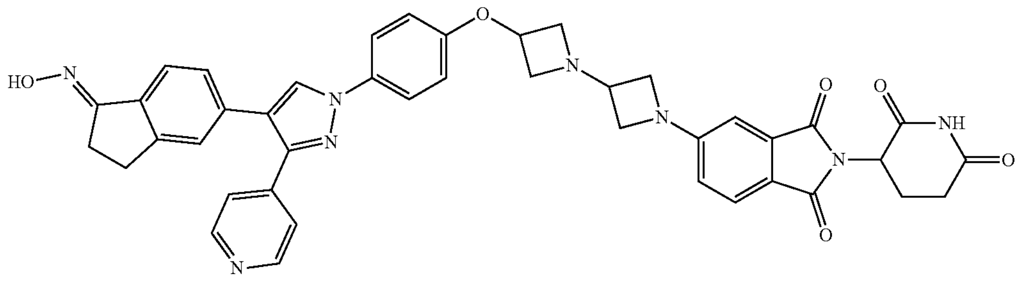 [SMILES: O=C1CCC(N2C(=O)c3ccc(N4CC(N5CC(Oc6ccc(-n7cc(-c8ccc9c(c8)CC/C9=N\O)c(-c8ccncc8)n7)cc6)C5)C4)cc3C2=O)C(=O)N1]

Step A: tert-butyl-3-(4-(4, 4, 5, 5-tetramethyl-1, 3, 2-dioxaborolan-2-yl) phenoxy) azetidine-1-carboxylate

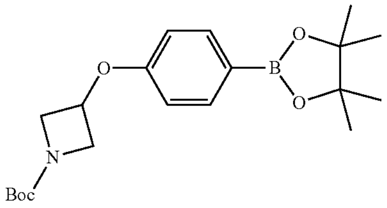 [SMILES: CC(C)(C)OC(=O)N1CC(Oc2ccc(B3OC(C)(C)C(C)(C)O3)cc2)C1]

A mixture of tert-butyl-3-iodoazetidine-1-carboxylate (2.8 g, 12.6 mmol), 4-(4, 4, 5, 5-tetramethyl-1, 3, 2-dioxaborolan-2-yl) phenol (3.9 g, 13.8 mmol) and $K_2CO_3$ (3.5 g, 25.2 mmol) in dry DMF (20 mL) was stirred at 80° C. overnight. After cooled to room temperature, DCM (50 mL) and water (25 mL) were added. The layers were separated, and the organic phase was washed with water and brine. The organic phase was dried ($Na_2SO_4$), filtered, and concentrated under vacuum. The residue was purified via flash column on silica gel (PE:EA=9:1) to afford desired product (2.4 g, 65% yield).

Step B: tert-butyl3-(4-(4-bromo-3-(pyridin-4-yl)-1H-pyrazol-1-yl) phenoxy) azetidine-1-carboxylate

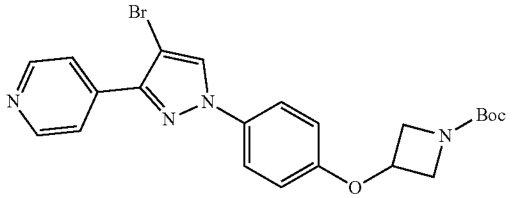 [SMILES: CC(C)(C)OC(=O)N1CC(Oc2ccc(-n3cc(Br)c(-c4ccncc4)n3)cc2)C1]

To a solution of tert-butyl 3-(4-(4,4,5,5-tetramethyl-1,3,2-dioxaborolan-2-yl)phenoxy)azetidine-1-carboxylate (2.4 g, 6.4 mmol) and 4-(4-bromo-1H-pyrazol-3-yl)pyridine (1.71 g, 7.68 mmol) in DCM (20 mL) were added $Et_2NH$ (4.7 g, 64 mmol), $Cu(OAc)_2$ (1.75 g, 9.6 mmol). The resulting mixture was stirred at 30° C. for 16 hours under $O_2$. The mixture was diluted with DCM (30 mL), and the mixture was washed with aqueous ammonia (10 mL×3). The organic phase was evaporated under reduced pressure, and the residue was purified by silica gel column chromatography on silica gel (DCM/MeOH=20/1) to afford tert-butyl 3-(4-(4-bromo-3-(pyridin-4-yl)-1H-pyrazol-1-yl) phenoxy) azetidine-1-carboxylate (1.5 g. 50% yield) as a brown oil. LCMS ($ES^+$): m/z 471 $[M+H]^+$.

Step C: 4-(1-(4-(azetidin-3-yloxy) phenyl)-4-bromo-1H-pyrazol-3-yl) pyridine

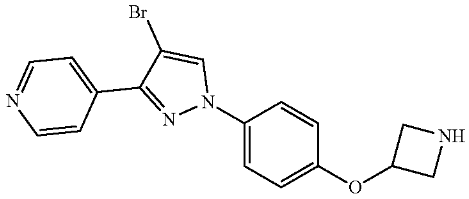 [SMILES: Brc1cn(-c2ccc(OC3CNC3)cc2)nc1-c1ccncc1]

To a solution of tert-butyl 3-(4-(4-bromo-3-(pyridin-4-yl)-1H-pyrazol-1-yl) phenoxy) azetidine-1-carboxylate (700 mg) in DCM (3 mL) was added 3 m HCl in 1,4-dioxane (3 mL). The resulting solution was stirred at room temperature for 2 hours. The solvent was removed under reduced pressure to afford crude desired product (600 mg, crude). LCMS ($ES^+$): m/z 371 $[M+H]^+$.

Step D: tert-butyl-3-(4-(4-bromo-3-(pyridin-4-yl)-1H-pyrazol-1-yl) phenoxy)-[1,3'-biazetidine]-1'-carboxylate

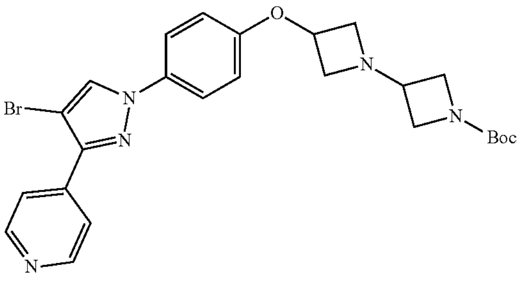 [SMILES: CC(C)(C)OC(=O)N1CC(N2CC(Oc3ccc(-n4cc(Br)c(-c5ccncc5)n4)cc3)C2)C1]

To a solution of 4-(1-(4-(azetidin-3-yloxy) phenyl)-4-bromo-1H-pyrazol-3-yl) pyridine (50 mg, 0.14 mmol) and tert-butyl 3-oxoazetidine-1-carboxylate (48 mg, 0.28 mmol) in DCE (1.0 mL) were added AcOH (1 drop), $NaBH(OAc)_3$ (74 mg, 0.35 mmol). The resulting solution was stirred at 30° C. overnight. The mixture was diluted with EA (5 mL), and the mixture was washed with aq. $NaHCO_3$ thrice. The organic phase was evaporated under reduced pressure, the residue was purified by silica gel column chromatography on silica gel (PE/EA=1/1) to afford tert-butyl 3-(4-(4-bromo-3-(pyridin-4-yl)-1H-pyrazol-1-yl)-phenoxy)-[1,3'-biazetidine]-1'-carboxylate (30 mg, 42% yield) as a brown oil. LCMS ($ES^+$): m/z 526 $[M+H]^+$.

Step E: 5-(3-(4-(4-bromo-3-(pyridin-4-yl)-1H-pyrazol-1-yl) phenoxy)-[1, 3'-biazetidin]-1'-yl)-2-(2,6-dioxopiperidin-3-yl) isoindoline-1, 3-dione

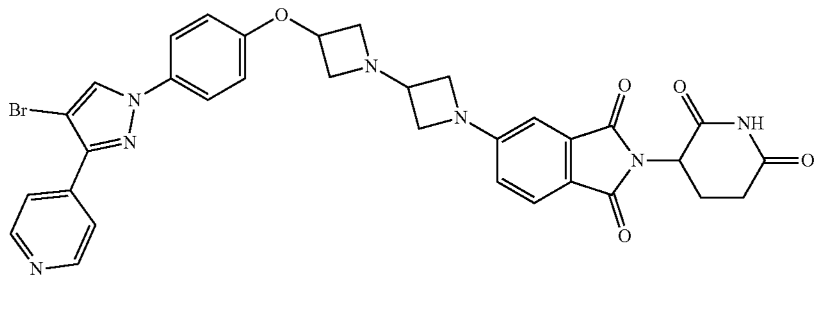 [SMILES: O=C1CCC(N2C(=O)c3ccc(N4CC(N5CC(Oc6ccc(-n7cc(Br)c(-c8ccncc8)n7)cc6)C5)C4)cc3C2=O)C(=O)N1]

To a solution of tert-butyl 3-(4-(4-bromo-3-(pyridin-4-yl)-1H-pyrazol-1-yl) phenoxy)-[1, 3'-biazetidine]-r-carboxylate (160 mg) in DCM (2 mL) was added 3 M HCl in 1,4-dioxane (1 mL). The resulting solution was stirred at room temperature for 2 hours. The solvent was removed under reduced pressure to afford the desired product (150 mg, crude). To a solution of 3-(4-(4-bromo-3-(pyridin-4-yl)-1H-pyrazol-1-yl)phenoxy)-1,3'-biazetidine (7.0 mg, 0.0165 mmol) and 2-(2,6-dioxopiperidin-3-yl)-5-fluoroisoindoline-1,3-dione (9.0 mg, 0.033 mmol) in NMP (1.0 mL) was added DIPEA (1 drop). The resulting solution was stirred at 130° C. for 1 hour under $N_2$. After cooled to rt, the mixture was diluted with EA (3 mL), and the mixture was washed with brine twice. The organic phase was evaporated under reduced pressure, The residue was purified by column chromatography on silica gel (DCM/MeOH=15/1) to afford 5-(3-(4-(4-bromo-3-(pyridin-4-yl)-1H-pyrazol-1-yl)phenoxy)-[1,3'-biazetidin]-1'-yl)-2-(2,6-dioxopiperidin-3-yl) isoindoline-1,3-dione (4 mg, 36% yield). LCMS ($ES^+$): m/z 682 $[M+H]^+$.

Step F: 2-(2,6-dioxopiperidin-3-yl)-5-(3-(4-(4-(1-oxo-2,3-dihydro-1H-inden-5-yl)-3-(pyridin-4-yl)-1H-pyrazol-1-yl)phenoxy)-[1,3'-biazetidin]-1'-yl) isoindoline-1,3-dione To a solution of 5-(3-(4-(4-bromo-3-(pyridin-4-yl)-1H-pyrazol-1-yl)phenoxy)-[1,3'-biazetidin]-1'-yl)-2-(2,6-dioxopiperidin-3-yl)isoindoline-1,3-dione (200 mg, 0.29 mmol) in 1,4-dioxane/$H_2O$ (v/v=10/1, 5 mL) were added 5-(4,4,5,5-tetramethyl-1,3,2-dioxaborolan-2-yl)-2,3-dihydro-1H-inden-1-one (83 mg, 0.32 mmol), $Pd_2(dba)_3$ (110 mg, 0.12 mmol), CsF (176 mg, 1.20 mmol), $[(t-Bu)_3PH]BF_4$ (68 mg, 0.12 mmol), and N,N-dicyclohexylmethylamine (2.9 mg, 0.015 mmol) subsequently. The resulting solution was heated to 100° C. for 2 hours under $N_2$. After cooling to room temperature, the reaction was diluted with EA (10 mL), and the mixture was washed with water, brine. The organic phase was dried over anhydrous sodium sulfate, concentrated under vacuum. The residue was purified by prep-HPLC to afford 2-(2,6-dioxopiperidin-3-yl)-5-(3-(4-(4-(1-oxo-2,3-dihydro-1H-inden-5-yl)-3-(pyridin-4-yl)-1H-pyrazol-1-yl)phenoxy)-[1,3'-biazetidin]-1'-yl)isoindoline-1,3-dione (90 mg, 41.9% yield) as yellow solid. LCMS ($ES^+$): m/z 733 $[M+H]^+$.

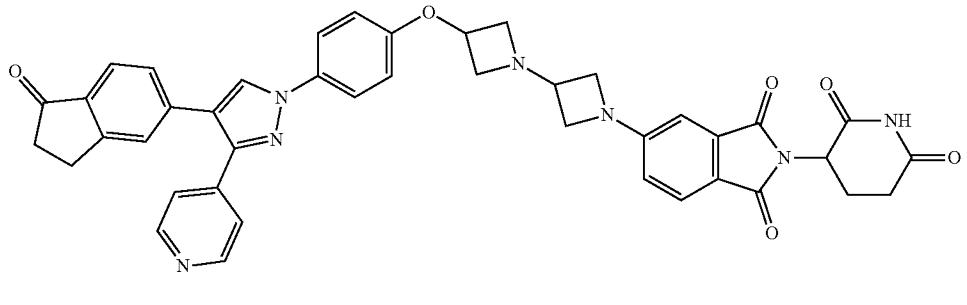 [SMILES: O=C1CCC(N2C(=O)c3ccc(N4CC(N5CC(Oc6ccc(-n7cc(-c8ccc9c(c8)CCC9=O)c(-c8ccncc8)n7)cc6)C5)C4)cc3C2=O)C(=O)N1]

Step G: (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)-[1,3'-biazetidin]-1'-yl)isoindoline-1,3-dione

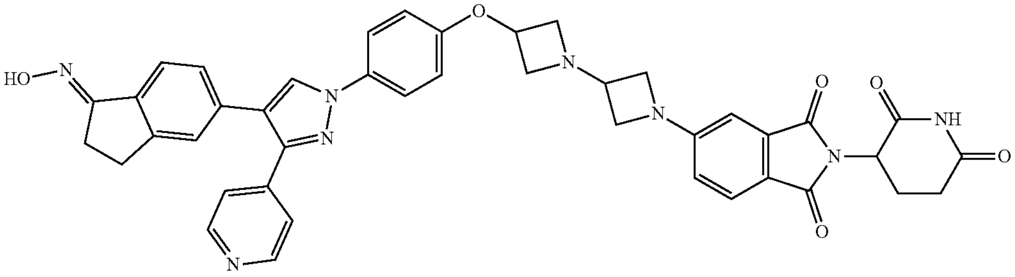 [SMILES: O=C1CCC(N2C(=O)c3ccc(N4CC(N5CC(Oc6ccc(-n7cc(-c8ccc9c(c8)CC/C9=N\O)c(-c8ccncc8)n7)cc6)C5)C4)cc3C2=O)C(=O)N1]

To a solution of 2-(2,6-dioxopiperidin-3-yl)-5-(3-(4-(4-(1-oxo-2,3-dihydro-1H-inden-5-yl)-3-(pyridin-4-yl)-1H-pyrazol-1-yl)phenoxy)-[1,3'-biazetidin]-1'-yl)isoindoline-1,3-dione (90 mg, 0.12 mmol) in acetonitrile/pyridine (v/v=1/1, 6.0 mL) was added hydroxylamine hydrochloride (83.4 mg, 1.2 mmol). The mixture was stirred at 40° C. for 20 minutes. After quenched with DCM (20 mL), the mixture was washed with brine (10 mL×2). The organic phase was concentrated under vacuum, and the residue was purified by prep-TLC to afford (E)-2-(2,6-dioxopiperidin-3-yl)-5-(3-(4-(4-(1-(hydroxyimino)-2,3-Dihydro-1H-inden-5-yl)-3-(pyridin-4-yl)-1H-pyrazol-1-yl)phenoxy)-[1,3'-biazetidin]-1'-yl)isoindoline-1,3-dione (25 mg, 27% yield) as yellow solid.

$^1$H NMR (400 MHz, $CDCl_3$): δ 11.06 (s, 1H), 10.89 (s, 1H), 8.73 (s, 1H), 8.57 (d, J=4.8 Hz, 2H), 7.87 (d, J=8.8 Hz, 2H), 7.65 (d, J=8.0 Hz, 1H), 7.56 (d, J=8.0 Hz, 1H), 7.48 (d, J=4.8 Hz, 2H), 7.40 (s, 1H), 7.22 (d, J=8.0 Hz, 1H), 7.03 (d, J=8.8 Hz, 2H), 6.80 (s, 1H), 6.68 (d, J=8.4 Hz, 1H), 5.02-5.07 (m, 1H), 4.96 (t, J=2.4 Hz, 1H), 4.09 (t, J=8.4 Hz, 2H), 3.80-3.87 (m, 4H), 3.73 (s, 1H), 3.22 (s, 4H), 3.01 (d, J=5.2 Hz, 2H), 2.84 (d, J=5.6 Hz, 2H), 2.01 (d, J=9.2 Hz, 2H); LCMS ($ES^+$): m/z 748.79 $[M+H]^+$.

Example Synthesis of Compound 226: (2S,4R)-1-((S)-2-(2-(4-((4-(4-(3-(2,6-difluoro-3-((R)-3-fluoro-pyrrolidine-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

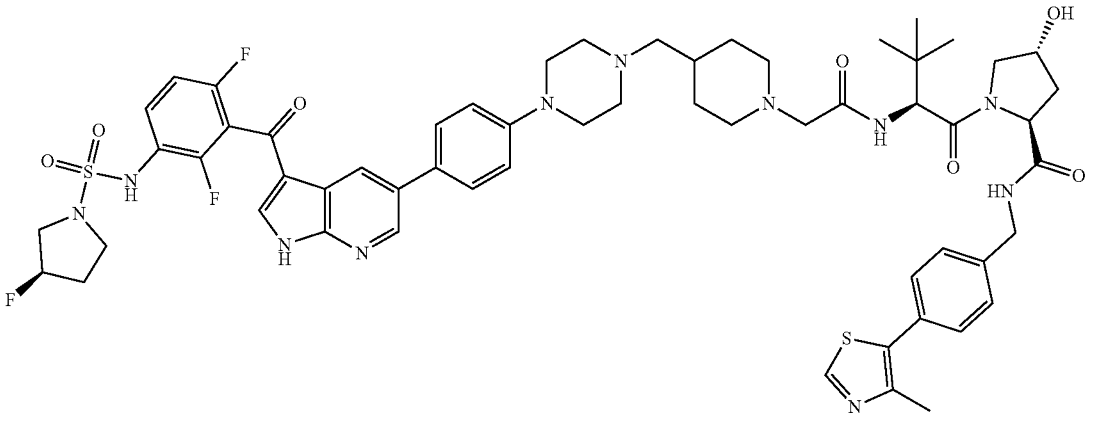 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Step A: tert-butyl 2-(4-formylpiperidin-1-yl)acetate

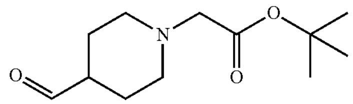 [SMILES: CC(C)(C)OC(=O)CN1CCC(C=O)CC1]

To a solution of tert-butyl 2-(4-(hydroxymethyl)piperidin-1-yl)acetate (1.5 g, 6.55 mmol) in $CH_3CN$ (10 mL) was added IBX (2.7 g, 9.85 mmol). The resulting solution was stirred at 80° C. for 5 hours. After cooling to room temperature, the reaction mixture was diluted with EA (30 mL), and the solution was washed with sodium sulfite and sodium bicarbonate. The organic layer was dried over anhydrous sodium sulfate. The organic phase was concentrated under vacuum. The residue was purified by silica gel chromatography (PE:EA=5:1) to afford the desired product tert-butyl 2-(4-formylpiperidin-1-yl)acetate (350 mg, 25% yield) as a yellow oil. $^1$H NMR (400 MHz, $CDCl_3$): δ 9.64 (s, 1H), 3.12 (s, 2H), 2.85-2.89 (m, 2H), 2.31-2.37 (m, 2H), 2.20-2.26 (m, 1H), 1.89-1.93 (m, 2H), 1.74-1.77 (m, 2H), 1.47 (s, 9H).

Step B: tert-butyl-2-(4-((4-(4-bromophenyl)piperazin-1-yl)methyl)piperidin-1-yl)acetate

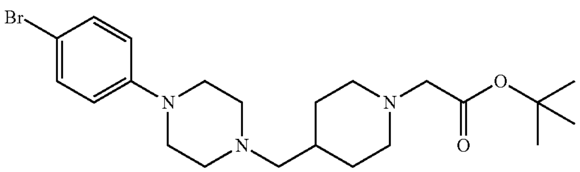 [SMILES: CC(C)(C)OC(=O)CN1CCC(CN2CCN(c3ccc(Br)cc3)CC2)CC1]

Step C: tert-butyl 2-(4-((4-(4-(4,4,5,5-tetramethyl-1,3,2-dioxaborolan-2-yl)phenyl)piperazin-1-yl)methyl)piperidin-1-yl)acetate

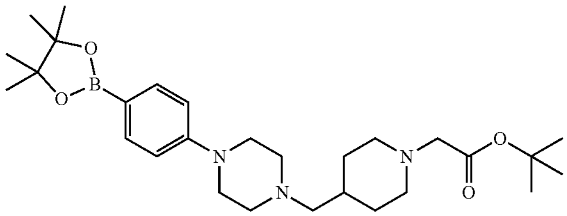 [SMILES: CC(C)(C)OC(=O)CN1CCC(CN2CCN(c3ccc(B4OC(C)(C)C(C)(C)O4)cc3)CC2)CC1]

To a solution of 4,4,4',4',5,5,5',5'-octamethyl-2,2'-bi(1,3,2-dioxaborolane) (242 mg, 0.951 mmol) and tert-butyl 2-(4-((4-(4-bromophenyl)piperazin-1-yl)methyl)-piperidin-1-yl)acetate (330 mg, 0.732 mmol) in 1,4-dioxane (5 mL) were added KOAc (145 mg, 1.46 mmol) and Pd(dppf)$Cl_2$ (54 mg, 0.0732 mmol). After stirring at 90° C. overnight under nitrogen atmosphere, the reaction mixture was diluted with 30 mL of ethyl acetate, and the solution was washed with brine (10 mL×3). The organic phase was dried over anhydrous sodium sulfate and concentrated under vacuum. The residue was purified by silica gel (DCM:MeOH=100:3) to afford the desired product tert-butyl 2-(4-((4-(4-(4,4,5,5-tetramethyl-1,3,2-dioxaborolan-2-yl)phenyl)piperazin-1-yl)methyl)piperidin-1-yl)acetate (100 mg, 27% yield) as yellow solid. LCMS ($ES^+$): m/z 499.4 $[M+H]^+$.

Step D: (R)-tert-butyl-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate

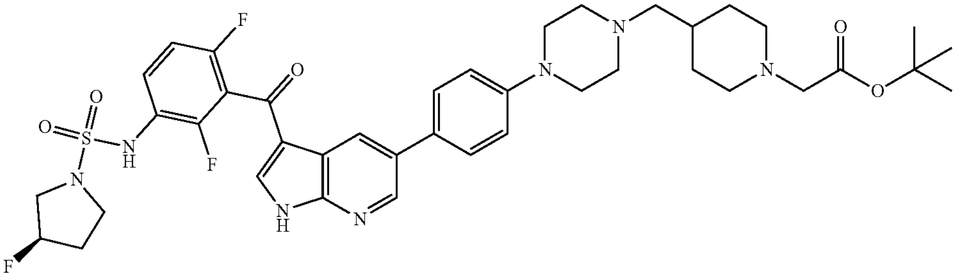 [SMILES: CC(C)(C)OC(=O)CN1CCC(CN2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-(4-formylpiperidin-1-yl)acetate (370 mg, 1.54 mmol) and 1-(4-bromophenyl)piperazine (350 mg, 1.54 mmol) in $CH_3OH$/DCM (v/v=1/1, 10 mL) was added catalytic AcOH (0.1 mL) at room temperature. After stirring for 30 minutes, NaBH$(OAc)_3$ (1.3 g, 6.17 mmol) was added. The mixture was stirred at 30° C. for 1 hours. After quenched with aqu.$NaHCO_3$ (20 mL), the mixture was extracted with DCM (10 mL×3). The combined organic layer was washed with brine (20 mL), dried over anhydrous sodium sulfate and concentrated under vacuum. The residue was purified by silica gel (DCM:MeOH=50:1), get tert-butyl 2-(4-((4-(4-bromophenyl)piperazin-1-yl)methyl) piperidin-1-yl)acetate (330 mg, 47% yield) as a yellow oil. LCMS ($ES^+$): m/z 454.2 $[M+H]^+$.

To a solution of tert-butyl 2-(4-((4-(4-(4,4,5,5-tetramethyl-1,3,2-dioxaborolan -2-yl)phenyl)piperazin-1-yl)methyl)piperidin-1-yl)acetate (100 mg, 0.199 mmol) in $H_2O$/dioxane (v/v=1/5, 5.0 mL) were added CsL (121 mg, 0.796 mmol), Pd(aMPhos)$Cl_2$ (14 mg, 0.0199 mmol) and (R)—N-(3-(5-bromo-1H-pyrrolo[2,3-b]pyridine-3-carbonyl)-2,4-difluorophenyl)-3-fluoropyrrolidine-1-sulfonamide (100 mg, 0.199 mmol) at room temperature. The solution was purged with $N_2$ at room temperature for 10 minutes to remove the excess $O_2$. The resulting solution was stirred at 100° C. for 4 hours. After cooling to room temperature, the reaction was taken up with EtOAc. The combined organic layers were concentrated under vacuum. The residue was purified by prep-TLC (DCM:$CH_3OH$=20:1) to afford the desired product (R)-tert-butyl 2-(4-((4-(4-(3-(2,6-difluoro- 3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate (50 mg, 32% yield) as a light yellow solid. LCMS (ES$^+$): m/z 797.6 [M+H]$^+$.

Step E: (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetic acid

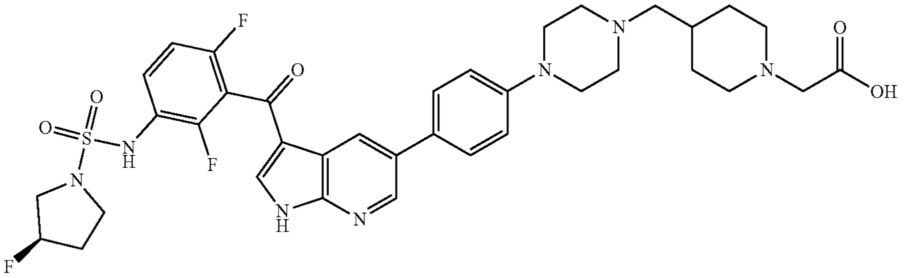 [SMILES: O=C(O)CN1CCC(CN2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of (R)-tert-butyl 2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl) piperidin-1-yl)acetate (50 mg, 0.0629 mmol) in DCM (1 mL) was added TFA (0.5 mL). The resulting solution was stirred for 2 hours at room temperature. The solvent was removed under vacuum. The residue is desired product (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetic acid (80 mg, crude) as a yellow solid. LCMS (ES$^+$): m/z 740.2 [M+H]$^+$.

Step G: (2S,4R)-1-((S)-2-(2-(4-((4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide To a solution of (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl) piperidin-1-yl)acetic acid (47 mg, 0.0629 mmol) in DCM (5.0 mL) were added DIEA (25 mg, 0.189 mmol), (2S,4R)-1-((S)-2-((13-chloranyl)diazenyl)-3,3-dimethylbutanoyl)-4-hydroxy-N-(4-(4-methylthiazol-5-yl)benzyl)pyrrolidine-2-carboxamide (30 mg, 0.0691 mmol) and PyBOP (40 mg, 0.0755 mmol) at room temperature. The resulting solution was stirred at 20° C. for 1 hour. The reaction was quenched with $H_2O$ (10 mL), and the mixture was extracted with DCM (20 mL×3). The combined organic layer was concentrated under vacuum. The residue was purified by prep-TLC (DCM:$CH_3OH$=10:1) to afford the desired product (2S,4R)-1-((S)-2-(2-(4-((4-(4-(3-(2,6-difluoro-3-((R)-3-fluoropyrrolidine-1-sulfonamido)benzoyl)-1H-pyrrolo[2,3-b]pyridin-5-yl)phenyl) piperazin-1-yl)methyl)piperidin-1-yl)acetamido)-3,3-dimethylbutanoyl)-4-hydroxy-N-(4-(4-methylthiazol-5-yl) benzyl)pyrrolidine-2-carboxamide (33 mg) as a white solid. $^1$H NMR (400 MHz, $CD_3OD$): δ 8.77 (s, 1H), 8.59 (s, 1H), 8.49 (s, 1H), 7.79 (s, 1H), 7.61-7.69 (m, 1H), 7.49 (d, J=8.8 Hz, 2H), 7.31-7.39 (m, 4H), 6.98-7.04 (m, 3H), 5.18 (s, 0.5H), 5.02 (s, 0.5H), 4.56 (s, 1H), 4.41-4.53 (m, 2H), 4.22-4.29 (m, 1H), 3.76-3.81 (m, 1H), 3.68-3.73 (m, 1H), 3.23-3.52 (m, 4H), 3.16 (s, 4H), 2.94 (s, 2H), 2.90 (s, 1H), 2.72-2.81 (m, 2H), 2.50 (br, 4H), 2.38 (s, 3H), 1.92-2.20 (m, 10H), 1.66-1.79 (m, 2H), 0.95 (s, 9H); LCMS (ES$^+$): m/z 1154.3 [M+H]$^+$.

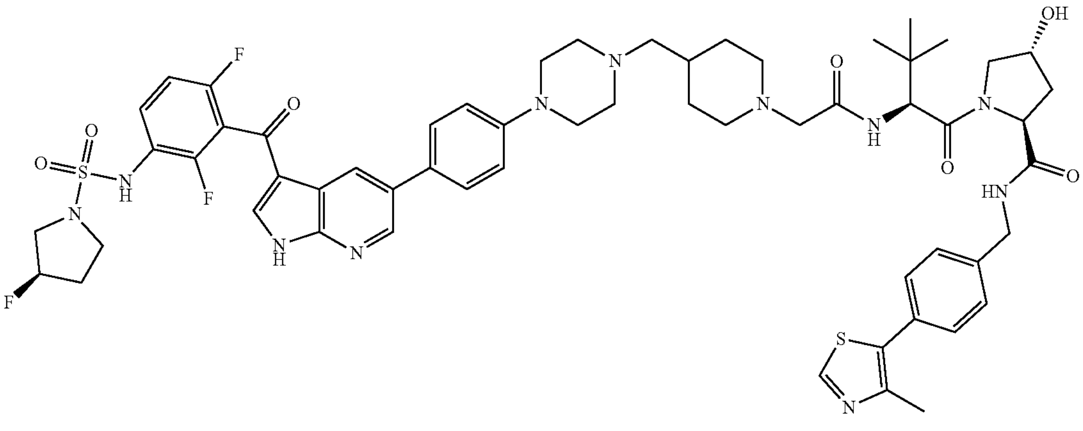 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Example Synthesis of Compound 227: (2S,4R)-1-((S)-2-(2-(4-((1-(4-(3-(2,6-difluoro-3-((R)-3-fluoro-pyrrolidine-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide was added cat. AcOH (0.1 mL) at room temperature. After stirring for 30 minutes, $NaBH(OAc)_3$ (2.7 g, 12.7 mmol) was added. The resulting solution was stirred at 30° C. overnight. After quenched with aq. $NaHCO_3$ (20 mL), the mixture was extracted with DCM (10 mL×3). The combined organic layers were washed with brine (20 mL), dried over anhydrous sodium sulfate and concentrated under vacuum. The residue was purified by silica gel with PE/EA (8/1)

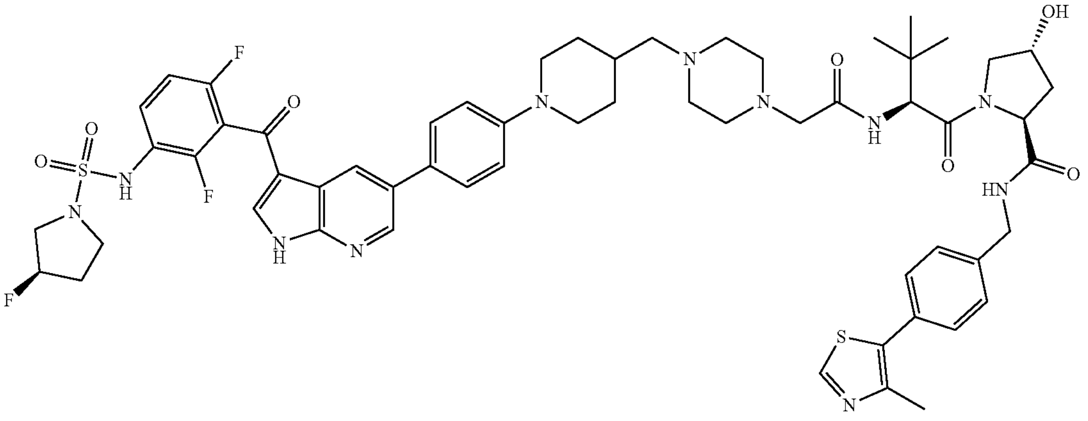 [SMILES: Cc1ncsc1-c1ccc(CNC(=O)[C@@H]2C[C@@H](O)CN2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

tert-butyl 4-((1-(4-bromophenyl)piperidin-4-yl)methyl)piperazine-1-carboxylate (800 mg) as a yellow oil. LCMS ($ES^+$): m/z 440.2 $[M+H]^+$.

Step A: 1-(4-bromophenyl)piperidine-4-carbaldehyde

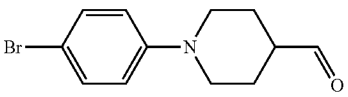

To a solution of 1-(4-bromophenyl)-4-(dimethoxymethyl)piperidine (1 g, 3.18 mmol) in MeCN (10 mL) were added hydrochloric acid (3 N). The resulting solution was stirred at 50° C. for 4 hours. After cooling to room temperature, the pH of the mixture was adjusted to 8~9 with aq. $NaHCO_3$. The reaction mixture was diluted with 30 mL of EA, and the mixture was washed with sodium sulfite, sodium bicarbonate. The organic phase was dried over anhydrous sodium sulfate. The organic phase was concentrated under vacuum. The residue is desired product 1-(4-bromophenyl)piperidine-4-carbaldehyde (1 g crude) as yellow solid. LCMS ($ES^+$): m/z 268.0 $[M+H]^+$.

Step B: tert-butyl 4-((1-(4-bromophenyl)piperidin-4-yl)methyl)piperazine-1-carboxylate

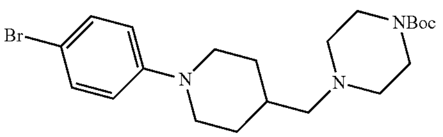 [SMILES: CC(C)(C)OC(=O)N1CCN(CC2CCN(c3ccc(Br)cc3)CC2)CC1]

To a solution of 1-(4-bromophenyl)piperidine-4-carbaldehyde (1 g, crude) and tert-butyl piperazine-1-carboxylate (590 mg, 3.18 mmol) in $CH_3OH$/DCM (v/v=1/1, 10 mL)

Step C: tert-butyl 2-(4-((1-(4-bromophenyl)piperidin-4-yl)methyl)piperazin-1-yl)acetate

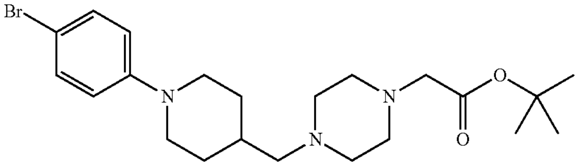 [SMILES: CC(C)(C)OC(=O)CN1CCN(CC2CCN(c3ccc(Br)cc3)CC2)CC1]

To a solution of tert-butyl 4-((1-(4-bromophenyl)piperidin-4-yl)methyl) piperazine-1-carboxylate (800 mg, 1.83 mmol) in DCM (4 mL) was added TFA (2 mL). The resulting solution was stirred for 2 hours at room temperature. The solvent was removed under vacuum to afford crude desired product (1 g, crude), which was used in next step directly. To a solution of above crude product (500 g, crude) and tert-butyl 2-bromoacetate (176 mg, 0.913 mmol) in dry DMF (5 mF) was added $K_2CO_3$ (190 mg, 1.37 mmol). The resulting solution was stirred at room temperature overnight. The reaction mixture was diluted with 40 mF of EA, and the mixture was washed with water, brine. The organic phase was dried over anhydrous sodium sulfate. The residue is desired product tert-butyl-2-(4-((1-(4-bromophenyl)piperidin-4-yl)methyl)piperazin-1-yl) acetate (410 mg, crude) as a yellow oil. FCMS ($ES^+$): m/z 453.2 $[M+H]^+$.

Step D: tert-butyl 2-(4-((1-(4-(4,4,5,5-tetramethyl-1,3,2-dioxaborolan-2-yl)phenyl)piperidin-4-yl)methyl)piperazin-1-yl)acetate

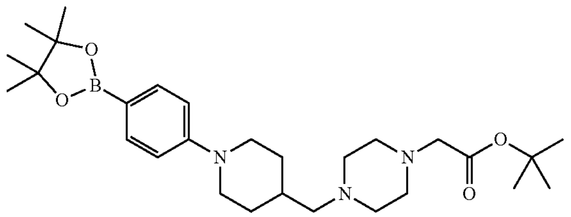 [SMILES: CC(C)(C)OC(=O)CN1CCN(CC2CCN(c3ccc(B4OC(C)(C)C(C)(C)O4)cc3)CC2)CC1]

To a solution of 4,4,4',4',5,5,5',5'-octamethyl-2,2'-bi(1,3,2-dioxaborolane) (300 mg, 1.18 mmol) and tert-butyl 2-(4-((1-(4-bromophenyl)piperidin-4-yl)methyl)-piperazin-1-yl) acetate (410 mg, 0.913 mmol) in 1,4-dioxane (5 mF) were added KOAc (178 mg, 1.82 mmol) and Pd(dppf)$Cl_2$ (67 mg, 0.0913 mmol). After stirring at 90° C. overnight under nitrogen atmosphere, the reaction mixture was diluted with 30 mF of ethyl acetate, and the solution was washed with brine (10 mF×3). The organic phase was dried over anhydrous sodium sulfate and concentrated under vacuum. The residue was purified by silica gel with DCM/MeOH (100/3) to afford the desired product tert-butyl 2-(4-((1-(4-(4,4,5,5-tetramethyl-1,3,2-dioxaborolan-2-yl)phenyl)-piperidin-4-yl)methyl)piperazin-1-yl)acetate (200 mg, crude) as yellow solid. LCMS ($ES^+$): m/z 500.4 $[M+H]^+$.

Step E: (R)-tert-butyl 2-(4-((1-(4-(3-(2,6-difluoro-3-(3-fluoropyrrolidine-1-sulfonamido)benzoyl)-1H-pyrrolo[2,3-b]pyridin-5-yl)phenyl)piperidin-4-yl)methyl)piperazin-1-yl)acetate

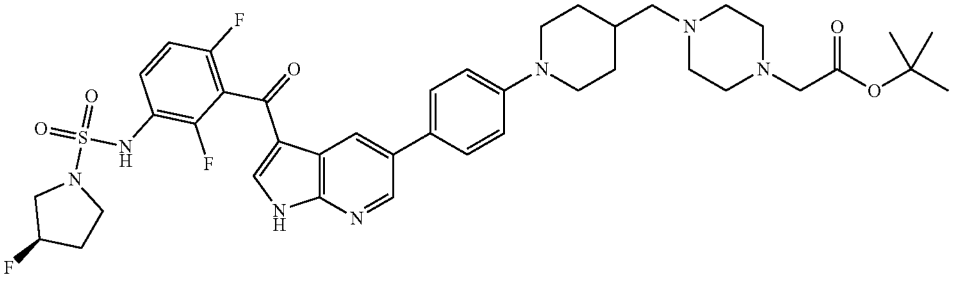 [SMILES: CC(C)(C)OC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-(4-((1-(4-(4,4,5,5-tetramethyl-1,3,2-dioxaborolan-2-yl)phenyl)piperidin-4-yl)methyl)piperazin-1-yl)acetate (200 mg, crude) in $H_2O$/dioxane (v/v=1/5, 5.0 mL) were added CsF (121 mg, 0.796 mmol), Pd(aMPhos)$Cl_2$ (14 mg, 0.0199 mmol), (R)—N-(3-(5-bromo-1H-pyrrolo[2,3-b]pyridine-3-carbonyl)-2,4-difluorophenyl)-3-fluoropyrrolidine-1-sulfonamide (100 mg, 0.199 mmol) at room temperature. The solution was purged with $N_2$ at room temperature for 10 minutes to remove the excess $O_2$. The resulting solution was stirred at 100° C. for 4 hours. After cooling to room temperature, the reaction was taken up with EtOAc. The combined organic layers were concentrated under vacuum. The residue was purified by prep-TLC with DCM/$CH_3OH$ (20/1) to afford the desired product (R)-tert-butyl 2-(4-((1-(4-(3-(2,6-difluoro-3-(3-fluoropyrrolidine-1-sulfonamido)benzoyl)-1H-pyrrolo[2,3-b]pyridin-5-yl)phenyl)piperidin-4-yl)methyl)piperazin-1-yl)acetate (110 mg, 69% yield) as a light yellow solid. LCMS ($ES^+$): m/z 796.3 $[M+H]^+$.

Step F: (2S,4R)-1-((S)-2-(2-(4-((1-(4-(3-(2,6-Difluoro-3-((R)-3-fluoropyrrolidine-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide

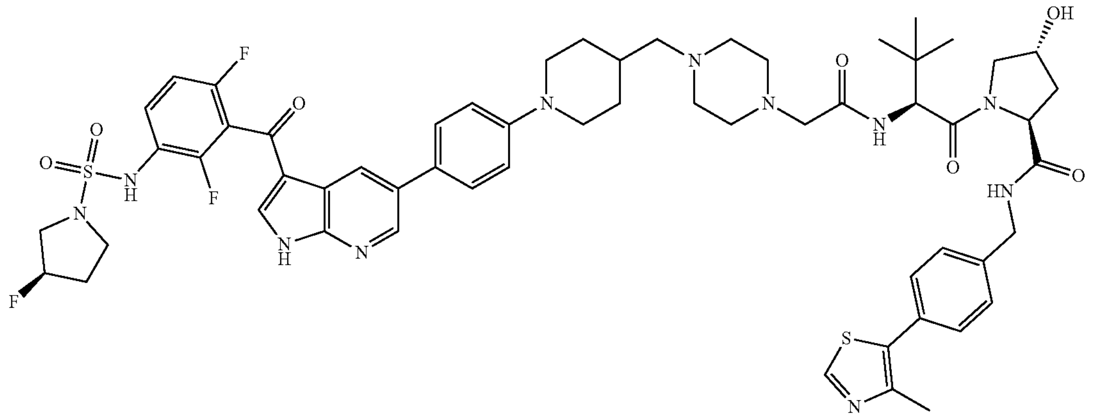 [SMILES: Cc1ncsc1-c1ccc(CNC(=O)[C@@H]2C[C@@H](O)CN2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

To a solution of (R)-tert-butyl 2-(4-((1-(4-(3-(2,6-difluoro-3-(3-fluoropyrrolidine-1-sulfonamido)benzoyl)-1H-pyrrolo[2,3-b]pyridin-5-yl)phenyl)piperidin-4-yl)methyl)piperazin-1-yl)acetate (110 mg, 0.139 mmol) in DCM (3 mL) was added TFA (1.5 mL). The resulting solution was stirred at room temperature for 2 hours. The solvent was removed under vacuum to afford crude desired product (180 mg, crude), which was used in next step directly. To a solution of above acid (180 mg, crude) in DMF (5.0 mL) were added DIEA (54 mg, 0.418 mmol), (2S,4R)-1-((S)-2-((13-chloranyl)diazenyl)-3,3-dimethyl-butanoyl)-4-hydroxy-N-(4-(4-methylthiazol-5-yl)benzyl)pyrrolidine-2-carboxamide (66 mg, 0.153 mmol) and PyBOP (87 mg, 0.167 mmol) at room temperature. The resulting solution was stirred at 20° C. for 1 hour. After quenched with $H_2O$ (10 mL), and the mixture was extracted with EA (20 mL×3). The combined organic layer was concentrated under vacuum. The residue was purified by prep-HPLC to afford the desired product desired product (42 mg) as a yellow solid. $^1H$ NMR (400 MHz, MeOD-$d_4$): δ 8.89 (s, 1H), 8.70 (s, 1H), 8.61 (s, 1H), 7.91 (s, 1H), 7.71-7.80 (m, 1H), 7.60 (d, J=8.4 Hz, 2H), 7.43-7.50 (m, 4H), 7.12-7.16 (m, 3H), 5.23 (s, 0.5H), 5.18 (s, 0.5H), 4.95 (m, 4H), 4.56 (s, 1H), 4.53-4.66 (m, 4H), 4.35-4.41 (m, 1H), 3.79-3.90 (m, 4H), 3.44-3.60 (m, 6H), 3.08-3.19 (m, 2H), 2.72-2.81 (m, 10H), 2.50 (s, 3H), 2.03-2.25 (m, 5H), 1.87-1.92 (m, 3H), 1.52-1.63 (m, 2H), 1.04 (s, 9H); LCMS ($ES^+$): m/z 1101.3 $[M+H]^+$.

Example Synthesis of Compound 295: (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

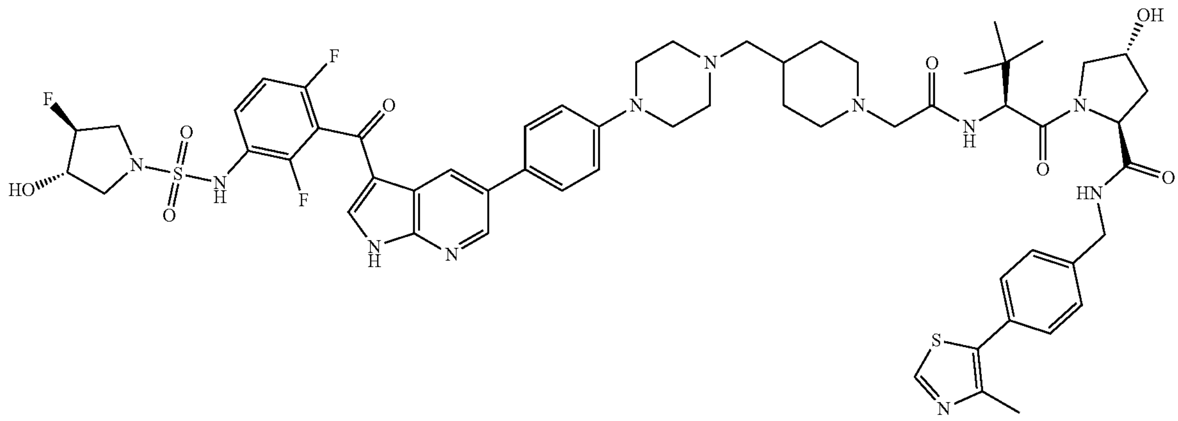 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8C[C@H](O)[C@@H](F)C8)c7F)c6c5)cc4)CC3)CC2)C(C)(C)C)cc1]

Step A: (3S,4S)-3-[(tert-butyldiphenylsilyl)oxy]-4-fluoropyrrolidine

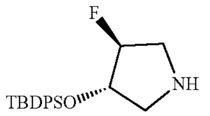

Into a 50 mL round-bottom flask, was placed (3S,4S)-4-fluoropyrrolidin-3-ol (500 mg, 4.76 mmol, 1 equiv), dichloromethane (10 mL), imidazole (323.8 mg, 4.76 mmol, 1 equiv), TBDPSCl (1307.5 mg, 4.76 mmol, 1 equiv). The resulting solution was stirred overnight at room temperature. The resulting mixture was concentrated. The residue was applied onto a silica gel column eluting with dichloromethane/methanol (10/1). This resulted in 470 mg (29%) of (3S,4S)-3-[(tert-butyldiphenylsilyl)oxy]-4-fluoropyrrolidine as yellow oil.

Step. B: (3S,4S)-3-[(tert-butyldiphenylsilyl)oxy]-4-fluoropyrrolidine-1-sulfonyl chloride

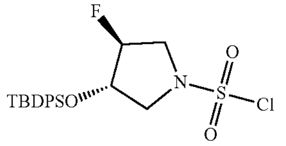

Step C: (3S,4S)—N-(3-[5-bromo-1H-pyrrolo[2,3-b]pyridine-3-carbonyl]-2,4-difluorophenyl)-3-[(tert-butyldiphenylsilyl)oxy]-4-fluoropyrrolidine-1-sulfonamide

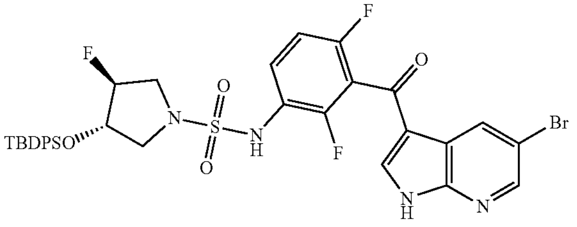

Into a 25 mL round-bottom flask, was placed (3S,4S)-3-[(tert-butyldiphenylsilyl)oxy]-4-fluoropyrrolidine-1-sulfonyl chloride (449.4 mg, 1.02 mmol, 2.00 equiv), pyridine (0.7 mL), 3-[5-bromo-1H-pyrrolo[2,3-b]pyridine-3-carbonyl]-2,4-difluoroaniline (179 mg, 0.51 mmol, 1 equiv), dimethylaminopyridine (18.6 mg, 0.15 mmol, 0.30 equiv). The resulting solution was stirred for 3 hours at 45° C. in an oil bath. The resulting mixture was concentrated. The residue was applied onto a silica gel column eluting with ethyl acetate/petroleum ether (1/1). This resulted in 120 mg (31%) of (3S,4S)—N-(3-[5-bromo-1H-pyrrolo[2,3-b]pyridine-3-carbonyl]-2,4-difluorophenyl)-3-[(tert-butyldiphenylsilyl)oxy]-4-fluoropyrrolidine-1-sulfonamide as yellow oil.

Step D: Synthesis of tert-butyl 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidine

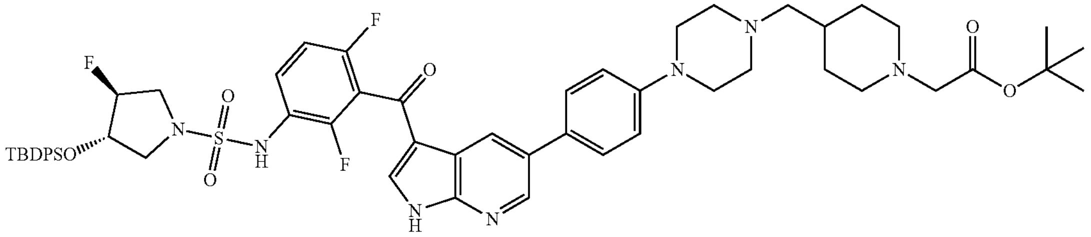

Into a 50 mL round-bottom flask, was placed (3S,4S)-3-[(tert-butyldiphenylsilyl)oxy]-4-fluoropyrrolidine (370 mg, 1 equiv), dichloromethane (5 mL), Diisopropylethylamine (279 mg, 2 equiv), dichloro sulfoxide (290 mg, 2 equiv). The resulting solution was stirred for 4 hours at −30° C. The reaction was then quenched by the addition of water (20 mL). The resulting solution was extracted with dichloromethane (20 mL×3). The resulting mixture was washed with brine (20 mL×1), was dried over anhydrous sodium sulfate and concentrated. This resulted in 450 mg of (3S,4S)-3-[(tert-butyldiphenylsilyl)oxy]-4-fluoropyrrolidine-1-sulfonyl chloride as yellow oil.

Into a 50 mL round-bottom flask, was placed (3S,4S)—N-(3-[5-bromo-1H-pyrrolo[2,3-b]pyridine-3-carbonyl]-2,4-difluorophenyl)-3-[(tert-butyldiphenylsilyl)oxy]-4-fluoropyrrolidine-1-sulfonamide (120 mg, 0.16 mmol, 1 equiv), 1,4-dioxane (5 mL, 0.06 mmol), water (0.0 mL, 0.06 mmol), tert-butyl 2-[4-([4-[4-(4,4,5,5-tetramethyl-1,3,2-dioxaborolan-2-yl)phenyl]piperazin-1-yl]methyl)piperidin-1-yl]acetate (79.1 mg, 0.16 mmol, 1 equiv), $Na_2CO_3$ (50.4 mg, 0.48 mmol, 3 equiv), Pd(dppf)$Cl_2$ (39 mg). The resulting solution was stirred for 2 hours at 110° C. in an oil bath. The resulting mixture was concentrated. The residue was applied onto a silica gel column eluting with dichloromethane/methanol (10/1). This resulted in 90 mg (54%) of tert-butyl 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperid as yellow oil.

Step E: Synthesis of 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidin-1-yl)acetic acid

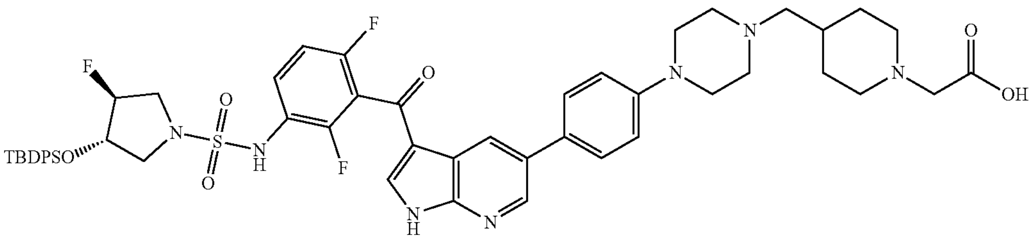

Into a 25 mL round-bottom flask, was placed tert-butyl 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperid (90 mg, 0.09 mmol, 1 equiv), dichloromethane (5 mL), trifluoroacetic acid (2 mL, 0.02 mmol). The resulting solution was stirred overnight at room temperature. The resulting mixture was concentrated under reduced pressure. This resulted in 60 mg (70.43%) of 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidin-1-yl)acetic acid as a yellow solid.

Step F: Synthesis of 2-(4-[[4-(4-[3-[2,6-difluoro-3-([[(3S,4S)-3-fluoro-4-hydroxypyrrolidin-1-yl]sulfonyl]amino)benzoyl]-1H-pyrrolo[2,3-b]pyridin-5-yl]phenyl)piperazin-1-yl]methyl]piperidin-1-yl)acetic acid

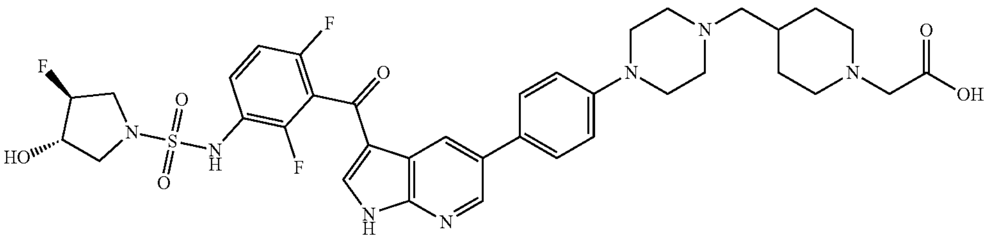 [SMILES: O=C(O)CN1CCC(CN2CCN(c3ccc(-c4cnc5[nH]cc(C(=O)c6c(F)ccc(NS(=O)(=O)N7C[C@H](O)[C@@H](F)C7)c6F)c5c4)cc3)CC2)CC1]

Into a 25 mL round-bottom flask, was placed 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidin-1-yl)acetic acid (60 mg, 0.06 mmol, 1 equiv), tetrahydrofuran (3 mL), TBAF (1 mL, 0.06 equiv). The resulting solution was stirred for 2 hours at 40° C. The resulting mixture was concentrated under reduced pressure. The residue was applied onto a silica gel column eluting with dichloromethane/methanol (10/1). This resulted in 50 mg (109.62%) of 2-(4-[[4-(4-[3-[2,6-difluoro-3-([[(3S,4S)-3-fluoro-4-hydroxypyrrolidin-1-yl]sulfonyl]amino)benzoyl]-1H-pyrrolo[2,3-b]pyridin-5-yl]phenyl)piperazin-1-yl]methyl]piperidin-1-yl)acetic acid as yellow oil.

Step G: (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl)methyl)piperidin-1-yl) acetamido)-3,3-dimethylbutanoyl)-4-hydroxy-N-(4-(4-methylthiazol-5-yl)benzyl)pyrrolidine-2-carboxamide

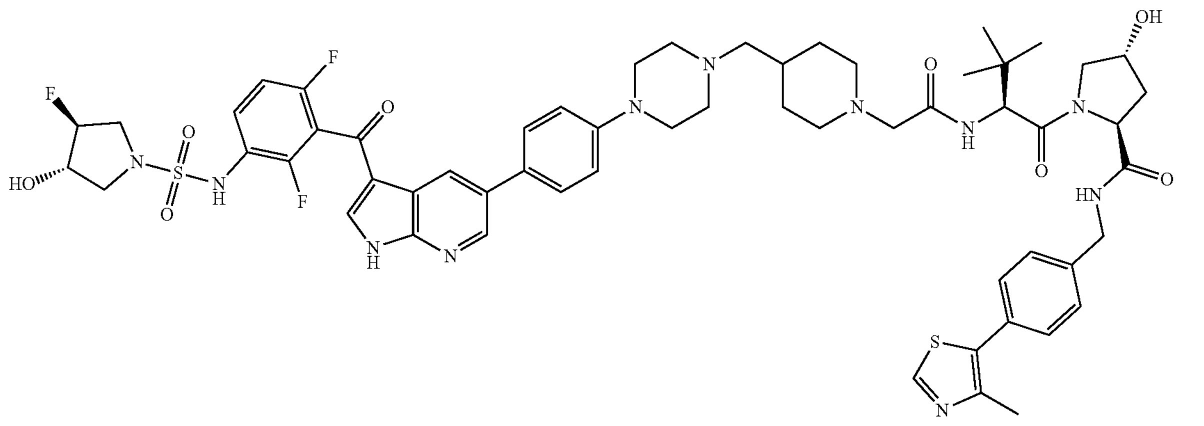 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8C[C@H](O)[C@@H](F)C8)c7F)c6c5)cc4)CC3)CC2)C(C)(C)C)cc1]

Into a 25 mL round-bottom flask, was placed 2-(4-[[4-(4-[3-[2,6-difluoro-3-([[(3 S,4S)-3-fluoro-4-hydroxypyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (50 mg, 0.066 mmol, 1 equiv), DMF (5 mL), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (30.8 mg, 0.066 mmol, 1 equiv), Diisopropylethylamine (34.1 mg, 0.264 mmol, 4.00 equiv), BOP (35 mg, 0.079 mmol, 1.2 equiv). The resulting solution was stirred for 3 hours at room temperature. The reaction was then quenched by water (30 mL), extracted with dichloromethane (30 mL×3), washed with water (30 mL) and concentrated under reduced pressure. The crude product was purified by prep-HPLC. This resulted in 32.6 mg (42%) of (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl) methyl)piperidin-1-yl)acetamido)-3,3-dimethylbutanoyl)-4-hydroxy-N-(4-(4-methylthiazol-5-yl)benzyl)pyrrolidine-2-carboxamide as a yellow solid. $^1$H NMR (400 MHz, $CD_3OD$): δ 8.87 (s, 1H), 8.69 (s, 1H), 8.58 (s, 1H), 7.89 (s, 1H), 7.73-7.72 (m, 1H), 7.58 (d, J=8.8 Hz, 2H), 7.48-7.40 (m, 4H), 7.10-7.05 (m, 3H), 4.93 (s, 1H), 4.63 (s, 1H), 4.57 (d, J=6 Hz, 1H), 4.52-4.50 (m, 1H), 4.38-4.34 (m, 2H), 3.87-3.86 (m, 1H), 3.82-3.81 (m, 1H), 3.57-3.50 (m, 3H), 3.36-3.33 (m, 1H), 3.31-3.20 (m, 5H), 3.02 (s, 2H), 3.01-2.90 (m, 2H), 2.56 (s, 3H), 2.74 (s, 3H), 2.26-2.20 (m, 4H), 2.10-2.01 (m, 1H), 1.82-1.71 (m, 2H), 1.67-1.61 (m, 3H), 1.44-1.28 (m, 2H), 1.05-1.02 (m, 9H); LCMS ($ES^+$): m/z 1168.30 $[M+H]^+$.

Example Synthesis of Compound 298: (2S,4R)-1-((S)-2-(2-(4-(3-(2,6-difluoro-3-(propylsulfonamido) benzoyl)-1H-pyrrolo[2,3-b]pyridin-5-yl)phenoxy) acetamido)-3,3-dimethylbutanoyl)-4-hydroxy-N-(4-(4-methylthiazol-5-yl)benzyl)-pyrrolidine-2-carboxamide

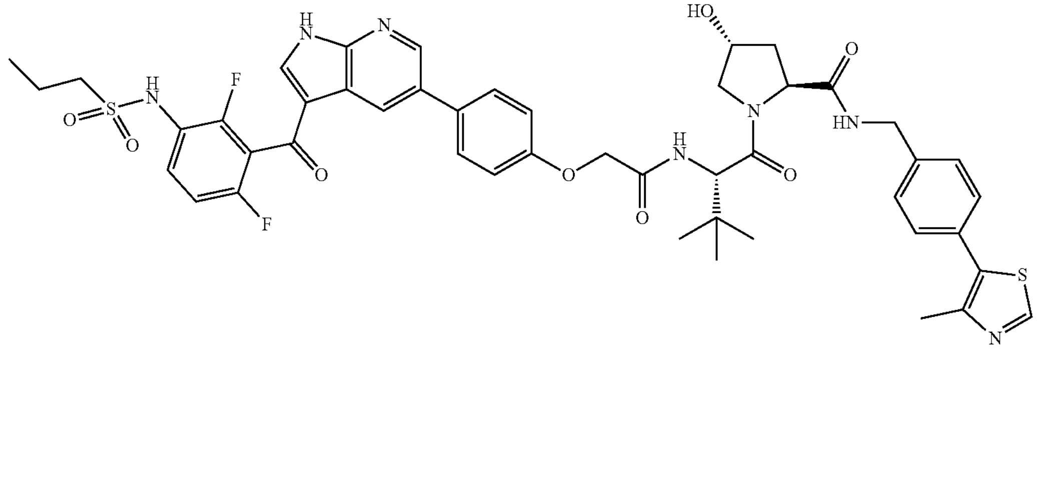 [SMILES: CCCS(=O)(=O)Nc1ccc(F)c(C(=O)c2c[nH]c3ncc(-c4ccc(OCC(=O)N[C@H](C(=O)N5C[C@H](O)C[C@H]5C(=O)NCc5ccc(-c6scnc6C)cc5)C(C)(C)C)cc4)cc23)c1F]

To a solution of 2-[4-[3-[2,6-difluoro-3-(propylsulfonylamino)-benzoyl]-1H-pyrrolo[2,3-b]pyridin-5-yl]phenoxy]acetic acid (10.8 mg, 0.02 mmol) and (2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide;hydrochloride (9.5 mg, 0.02 mmol) in DMF (1 ml) was added TEA (0.1 ml, 0.717 mmol) and PyBOP (11 mg, 0.021 mmol) at room temperature. The reaction mixture was stirred for 4 hours at the same temperature. TLC (DCM:MeOH:NH4OH, 90:9:1) shows no starting materials. The DMF was removed under high vacuum. Crude product was filtered over a silica-carbonate cartridge (100 mg) using a mixture of DCM:MeOH (90:10) as a eluent. Filtrate was evaporated under vacuum and crude product was purified by PTLC (DCM:MeOH:NH4OH, 90:9:1) to give 8.5 mg of product (44% yield). 1H NMR (500 MHz, DMSO-d6) δ 12.88 (s, 1H), 9.67 (s, 1H), 8.98 (s, 1H), 8.76-8.50 (m, 3H), 8.23 (s, 1H), 7.98 (d, J=9.4 Hz, 1H), 7.69 (d, J=8.6 Hz, 2H), 7.59 (td, J=9.0, 5.8 Hz, 1H), 7.49-7.34 (m, 4H), 7.33-7.20 (m, 1H), 7.10 (d, J=8.7 Hz, 2H), 5.20 (d, J=3.3 Hz, 1H), 4.72 (s, 2H), 4.62 (d, J=9.4 Hz, 1H), 4.54-4.34 (m, 3H), 4.25 (dd, J=15.9, 5.5 Hz, 1H), 3.74-3.59 (m, 2H), 3.19-3.07 (m, 2H), 2.44 (s, 3H), 2.07 (dd, J=12.9, 7.7 Hz, 1H), 1.91 (ddd, J=12.8, 8.8, 4.5 Hz, 1H), 1.80-1.65 (m, 2H), 0.96 (s, 9H), 0.94 (t, 3H). 13C NMR (151 MHz, dmso) δ 180.62, 171.82, 169.13, 167.11, 157.51, 156.02 (dd, J=246.1, 7.0 Hz), 152.34 (dd, J=249.6, 8.5 Hz), 151.45, 148.60, 147.74, 143.80, 139.47, 138.70, 131.16, 129.70, 129.00-128.42 (m), 128.81, 128.69, 128.31, 128.00, 127.48, 126.53, 121.96 (dd, J=13.6, 3.5 Hz), 118.61-117.85 (m), 117.53, 115.63, 115.34, 112.34 (dd, J=22.4, 3.4 Hz), 68.91, 66.58, 58.80, 56.58, 56.17, 53.45, 41.69, 37.95, 35.79, 26.28, 16.85, 15.96, 12.63. LC-MS (ESI); m/z [M+H]+: Calcd. for C47H50F2N7O8S2, 942.3130. Found 942.3134.

Example Synthesis of Compound 299: (2S,4R)-1-((S)-2-(4-(3-(3-(2,6-difluoro-3-(propylsulfonamido)benzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide To a solution of 4-[3-[3-[2,6-difluoro-3-(propylsulfonylamino) -benzoyl]-1H-pyrrolo[2,3-b]pyridin-5-yl]phenoxy]butanoic acid (18 mg, 0.03 mmol) and (2S,4R)-1-[(2S)-2-amino-3,3-dimethyl-butanoyl]-4-hydroxy-N-[[4-(4-methylthiazol-5-yl) phenyl]methyl]pyrrolidine-2-carboxamide;hydrochloride (16.8 mg, 0.036 mmol) in DMF (2 ml) was added TEA (0.1 ml, 0.72 mmol) and PyBOP (18.48 mg, 0.04 mmol) at room temperature. The reaction mixture was stirred for 4 hours at the same temperature. TLC (DCM:MeOH:$NH_4OH$, 90:9:1) shows no starting materials. The DMF was removed under high vacuum (product could be partially soluble in water). Crude product was filtered over a silica-carbonate cartridge using DCM:MeOH (9:1) as a eluent. Filtrate was evaporated under vacuum and crude product was purified by PTFC (DCM:MeOH:$NH_4OH$, 90:9:1), a second purification was performed by PTFC (DCM:MeOH, 9:1) to give 8 mg of product (25% yield). NMR (500 MHz, DMSO-d6) δ 12.97 (bs, 1H), 9.72 (bs, 1H), 8.97 (s, 1H), 8.71 (d, J=2.1 Hz, 1H), 8.61 (s, 2H), 8.56 (t, J=6.0 Hz, 2H), 8.23 (s, 1H), 7.99 (d, J=9.3 Hz, 1H), 7.59 (td, J=9.0, 5.9 Hz, 1H), 7.50-7.16 (m, 8H), 6.98 (d, J=8.2 Hz, 1H), 5.13 (d, J=3.4 Hz, 1H), 4.58 (d, J=9.3 Hz, 1H), 4.48-4.40 (m, 2H), 4.35 (s, 1H), 4.22 (dd, J=15.9, 5.5 Hz, 1H), 4.08 (ddt, J=9.6, 7.1, 3.2 Hz, 2H), 3.74-3.62 (m, 2H), 3.15-3.06 (m, 2H), 2.50-2.45 (m, 1H), 2.44 (s, 3H), 2.41-2.33 (m, 1H), 2.09-1.86 (m, 4H), 1.79-1.67 (m, 2H), 0.97 (t, 3H), 0.94 (s, 9H). $^{13}C$ NMR (151 MHz, dmso) δ 181.05, 172.38, 172.05, 170.09, 159.63, 156.44 (dd, J=246.5, 6.8 Hz), 152.74 (dd, J=249.6, 8.6 Hz), 151.86, 149.36, 148.13, 140.05, 139.92, 139.24, 131.87, 131.59, 130.71, 130.05, 129.20 (t, J=5.0 Hz), 129.06, 127.84, 127.52, 122.37 (dd, J=13.5, 3.5 Hz), 119.87, 118.95-118.24 (m), 117.88, 116.11, 114.12, 113.60, 112.91-112.65 (m), 69.32, 67.53, 59.14, 56.88, 56.83, 53.86, 42.08, 38.38, 35.67, 31.76, 26.80, 25.52, 17.26, 16.37, 13.04. LC-MS (ESI); m/z $[M+H]^+$: Calcd. for $C_{49}H_{54}F_2N_7O_8S_2$, 970.3443. Found 970.3787.

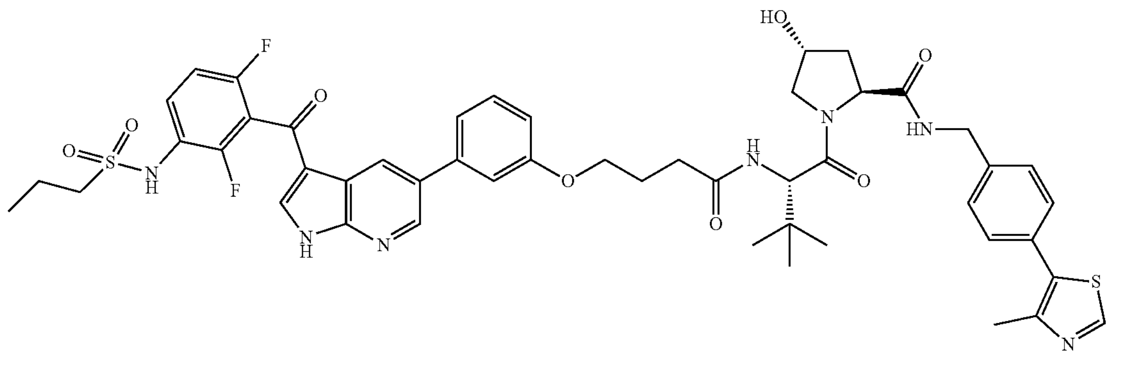 [SMILES: CCCS(=O)(=O)Nc1ccc(F)c(C(=O)c2c[nH]c3ncc(-c4cccc(OCCCC(=O)N[C@H](C(=O)N5C[C@H](O)C[C@H]5C(=O)NCc5ccc(-c6scnc6C)cc5)C(C)(C)C)c4)cc23)c1F]

Example Synthesis of Compound 300: (2S,4R)-1-((S)-2-(2-(2-(3-(3-(2,6-difluoro-3-(propylsulfonamido)benzoyl)-1H-pyrrolo[2,3-b]pyridin-5-yl)phenoxy)ethoxy)acetamido)-3,3-dimethylbutanoyl)-4-hydroxy-N-(4-(4-methylthiazol-5-yl)benzyl) pyrrolidine-2-carboxamide

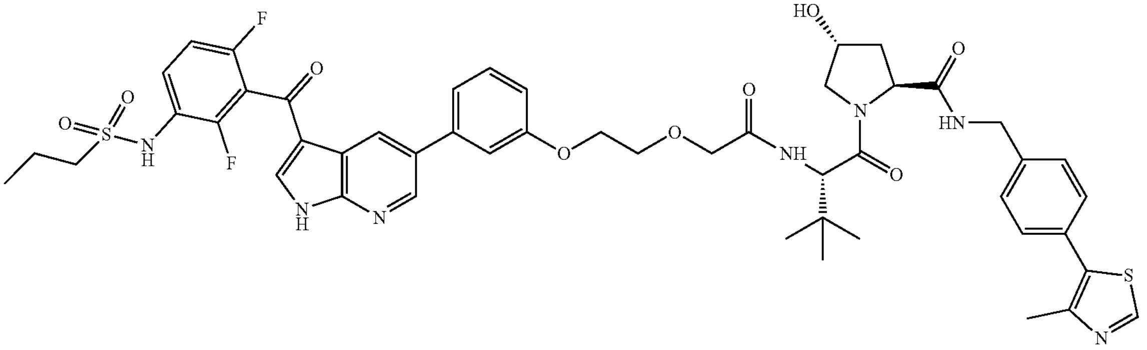 [SMILES: CCCS(=O)(=O)Nc1ccc(F)c(C(=O)c2c[nH]c3ncc(-c4cccc(OCCOCC(=O)N[C@H](C(=O)N5C[C@H](O)C[C@H]5C(=O)NCc5ccc(-c6scnc6C)cc5)C(C)(C)C)c4)cc23)c1F]

To a solution of 2-[2-[3-[3-[2,6-difluoro-3-(propylsulfonylaminobenzoyl]-1H-pyrrolo[2,3-b]pyridin-5-yl]phenoxy] ethoxy]acetic acid (19.1 mg, 0.03 mmol) and (2S,4R)-1-[(2S)-2-amino-3, 3-dimethyl-butanoyl]-4-hydroxy-N-[[4-(4-methylthiazol-5-yl)phenyl]methyl]pyrrolidine-2-carboxamide;hydrochloride (17.11 mg, 0.04 mmol) in DMF (2 ml) was added TEA (0.1 ml, 0.72 mmol) and PyBOP (19.06 mg, 0.04 mmol) at room temperature. The reaction mixture was stirred for 2 hours at the same temperature. TLC (DCM:MeOH:$NH_4OH$, 90:9:1) shows no starting materials. The DMF was removed under high vacuum (product could be partially soluble in water). Crude product was filtered over a silica-carbonate cartridge using DCM:MeOH (9:1) as a eluent. Filtrate was evaporated under vacuum and crude product was purified by PTLC (DCM:MeOH:$NH_4OH$, 90:9:1) to give 13 mg of product (40% yield). NMR (400 MHz, DMSO-d6) δ 12.95 (bs, 1H), 9.74 (bs, 1H), 8.91 (s, 1H), 8.67 (d, J=2.0 Hz, 1H), 8.55 (dd, J=12.8, 6.8 Hz, 2H), 8.19 (s, 1H), 7.56 (td, J=9.0, 6.0 Hz, 1H), 7.49 (d, J=9.5 Hz, 1H), 7.42-7.20 (m, 8H), 7.07-7.00 (m, 1H), 5.13 (d, J=3.5 Hz, 1H), 4.58 (d, J=9.6 Hz, 1H), 4.44 (t, J=8.1 Hz, 1H), 4.36 (dd, J=15.8, 6.2 Hz, 2H), 4.30-4.16 (m, 3H), 4.06 (s, 2H), 3.86 (t, J=4.3 Hz, 2H), 3.13-3.04 (m, 2H), 2.37 (s, 3H), 2.07-1.99 (m, 1H), 1.94-1.83 (m, 1H), 1.78-1.64 (m, 2H), 0.94 (t, 3H), 0.93 (s, 9H). $^{13}C$ NMR (126 MHz, dmso) δ 181.03, 172.20, 169.60, 168.98, 159.52, 156.46 (dd, J=246.7, 7.1 Hz), 152.75 (dd), 151.81, 149.36, 148.14, 144.59, 140.08, 139.80, 139.21, 131.85, 131.56, 130.66, 130.08, 129.62-128.89 (m), 129.08, 127.82, 122.38 (dd, J=13.5, 3.6 Hz), 120.09, 118.98-118.30 (m), 117.89, 116.15, 114.40, 113.50, 112.78 (dd, J=22.9, 3.8 Hz), 70.05, 70.00, 69.34, 67.49, 59.18, 57.04, 56.16, 53.89, 42.12, 38.34, 36.22, 26.65, 17.28, 16.32, 13.05. LC-MS (ESI); m/z $[M+H]^+$: Calcd. for $C_{49}H_{54}F_2N_7O_9S_2$, 986.3392. Found 986.3679.

Example Synthesis of Compound 217: N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)glutaramide

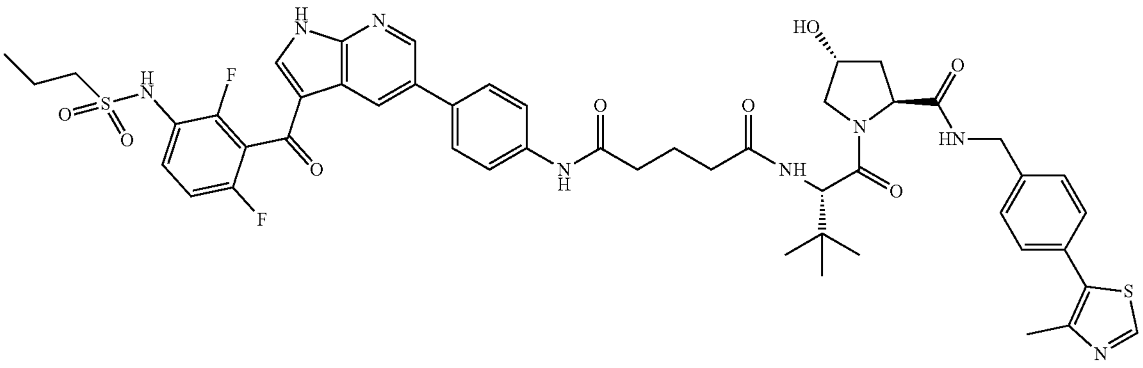 [SMILES: CCCS(=O)(=O)Nc1ccc(F)c(C(=O)c2c[nH]c3ncc(-c4ccc(NC(=O)CCCC(=O)N[C@H](C(=O)N5C[C@H](O)C[C@H]5C(=O)NCc5ccc(-c6scnc6C)cc5)C(C)(C)C)cc4)cc23)c1F]

To a solution of 5-((4-(3-(2,6-difluoro-3-(propylsulfonamido)-benzoyl)-1H-pyrrolo[2,3-b]pyridin-5-yl)phenyl) amino)-5-oxopentanoic acid (9.7 mg, 0.02 mmol) and (2S, 4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.52 mg, 0.02 mmol) in DMF (1 ml) was added TEA (0.1 ml, 0.72 mmol) and PyBOP (9.5 mg, 0.02 mmol) at room temperature. The reaction mixture was stirred for 4 hours at the same temperature. TLC (DCM:MeOH:$NH_4OH$, 90:9:1) shows no starting materials. The reaction mixture was diluted with EtOAc (10 mL) and washed with brine (5 mL, 4×), organic phase was dried ($Na_2SO_4$), and evaporated under vacuum. Crude product was purified by PTLC (DCM:MeOH:$NH_4OH$, 90:9:1) to give 4.8 mg of product (29% yield). NMR (500 MHz, DMSO-d6) δ 10.02 (s, 1H), 8.97 (s, 1H), 8.68 (d, 1H), 8.64-8.52 (m, 2H), 8.21 (s, 1H), 7.95 (d, J=9.2 Hz, 1H), 7.72 (dd, J=36.7, 8.5 Hz, 4H), 7.62-7.54 (m, 1H), 7.40 (dd, 4H), 7.28 (t, J=8.7 Hz, 1H), 5.16 (d, 2H), 4.56 (d, J=9.3 Hz, 1H), 4.50-4.40 (m, 2H), 4.40-4.33 (m, 1H), 4.22 (dd, J=15.8, 5.3 Hz, 1H), 3.76-3.62 (m, 2H), 3.16-3.05 (m, 2H), 2.44 (s, 3H), 2.41-2.17 (m, 4H), 2.09-2.01 (m, 1H), 1.98-1.80 (m, 3H), 1.74 (dq, J=14.9, 7.4 Hz, 2H), 0.96 (s, 9H), 0.95 (t, 3H). $^{13}C$ NMR (151 MHz, dmso) δ 181.06, 172.39, 172.17, 171.46, 170.15, 156.37 (dd, J=246.6, 6.3 Hz), 152.73 (dd, J=249.4, 8.1 Hz), 151.86, 149.05, 148.13, 144.19, 139.91, 139.37, 139.13, 132.97, 131.64, 131.59, 130.05, 129.22 (d, J=14.7 Hz), 129.06, 127.84, 127.74, 126.89, 122.47 (d, J=14.1 Hz), 120.07, 119.02-118.20 (m), 117.95, 116.06, 112.75 (dd, J=23.4, 2.8 Hz), 69.34, 59.15, 56.90, 56.81, 53.87, 42.08, 38.38, 36.36, 35.63, 34.63, 26.85, 21.91, 17.27, 16.37, 13.04. LC-MS (ESI); m/z $[M+H]^+$: Calcd. for $C_{50}H_{55}F_2N_8O_8S_2$, 997.3552. Found 997.3524.

Example Synthesis of Compound 218: (2S,4R)-1-((S)-2-(5-(4-(3-(2,6-difluoro-3-(propylsulfonamido) benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl) pyrrolidine-2-carboxamide To a solution of 5-(4-(3-(2,6-difluoro-3-(propylsulfonamido)-benzoyl)-1H-pyrrolo[2,3-b]pyridin-5-yl)piperazin-1-yl)-5-oxopentanoic acid (9.3 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.27 mg, 0.018 mmol) in DMF (1 ml) was added TEA (0.1 ml, 0.72 mmol) and PyBOP (9.22 mg, 0.018 mmol) at room temperature. The reaction mixture was stirred for 4 hours at the same temperature. TLC (DCM:MeOH:$NH_4OH$, 90:9:1) shows no starting materials. The reaction mixture was diluted with EtOAc (10 mL) and washed with brine (5 mL, 4×), organic phase was dried ($Na_2SO_4$), and evaporated under vacuum. Crude mixture did not show product by TLC, just some VHL starting material (4) (Product is soluble in water). Water extracts were lyophilized for overnight, the solid residue was filtered using a mixture of DCM:MeOH:$NH_4OH$ (90:9:1, 30 mL). Filtrate was evaporated to dryness and crude product was purified by PTLC (DCM:MeOH:$NH_4OH$, 90:9:1) to give 13 mg of product (81% yield). NMR (500 MHz, DMSO-d6) δ 12.64 (bs, 1H), 9.74 (bs, 1H), 8.97 (s, 1H), 8.62-8.52 (m, 3H), 8.28 (d, J=2.0 Hz, 1H), 8.00 (s, 1H), 7.95 (bs, 1H), 7.90 (d, J=9.2 Hz, 1H), 7.59-7.49 (m, 1H), 7.47-7.27 (m, 4H), 7.20 (t, J=8.7 Hz, 1H), 5.13 (bs, 1H), 4.56 (d, J=9.3 Hz, 1H), 4.48-4.32 (m, 3H), 4.22 (dd, J=15.8, 5.3 Hz, 1H), 3.75-3.57 (m, 5H), 3.23-3.02 (m, 7H), 2.44 (s, 3H), 2.41-2.17 (m, 4H), 2.07-2.01 (m, 1H), 1.96-1.87 (m, 1H), 1.81-1.66 (m, 4H), 0.95 (s, 9H), 0.94 (t, 3H). $^{13}C$ NMR (151 MHz, dmso) δ 180.70, 171.99, 171.92, 170.44, 169.75, 155.24 (dd, J=248.1, 5.5 Hz), 152.12 (dd, J=248.8, 8.5 Hz), 151.47, 147.73, 144.63, 144.31, 139.52, 138.02, 137.75, 131.19, 129.65, 128.65, 127.98-127.64 (m), 127.44, 123.91-123.09 (m), 118.86-117.72 (m), 117.60, 115.50, 115.23, 112.02 (dd, J=22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72. LC-MS (ESI); m/z $[M+H]^+$: Calcd. for $C_{48}H_{58}F_2N_9O_8S_2$, 990.3817. Found 990.3889.

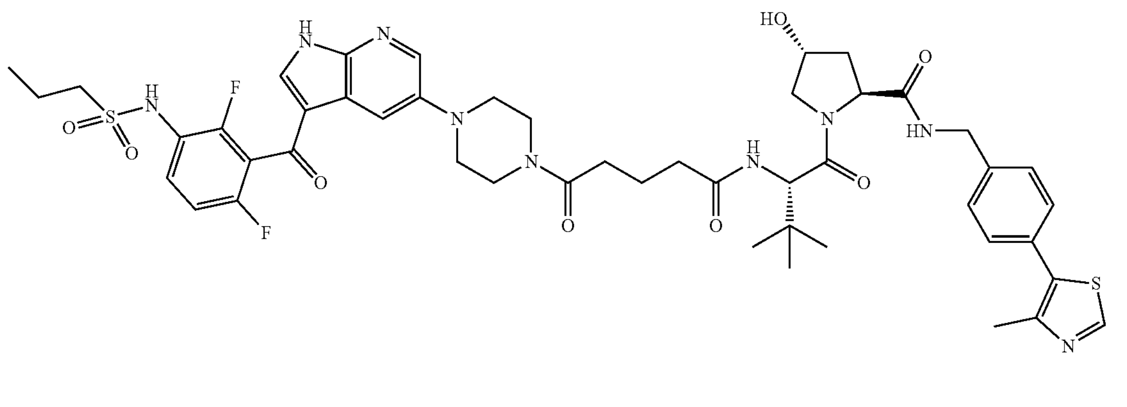 [SMILES: CCCS(=O)(=O)Nc1ccc(F)c(C(=O)c2c[nH]c3ncc(N4CCN(C(=O)CCCC(=O)N[C@H](C(=O)N5C[C@H](O)C[C@H]5C(=O)NCc5ccc(-c6scnc6C)cc5)C(C)(C)C)CC4)cc23)c1F]

Example Synthesis of Compound 219: (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide

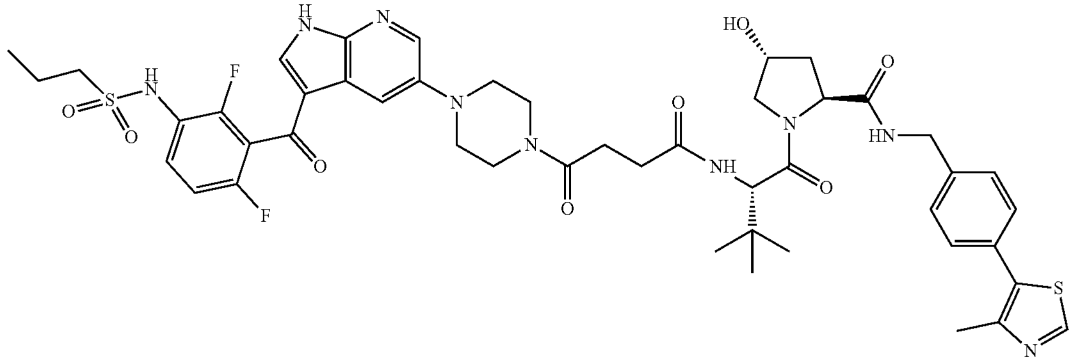 [SMILES: CCCS(=O)(=O)Nc1ccc(F)c(C(=O)c2c[nH]c3ncc(N4CCN(C(=O)CCC(=O)N[C@H](C(=O)N5C[C@H](O)C[C@H]5C(=O)NCc5ccc(-c6scnc6C)cc5)C(C)(C)C)CC4)cc23)c1F]

4-(4-(3-(2,6-difluoro-3-(propylsulfonamido)-benzoyl)-1H-pyrrolo[2,3-b]pyridin-5-yl)piperazin-1-yl)-4-oxobutanoic acid (9 mg, 0.016 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (8.2 mg, 0.018 mmol) in DMF (1 ml) was added TEA (0.1 ml, 0.72 mmol) and PyBOP (9.14 mg, 0.018 mmol) at room temperature. The reaction mixture was stirred for 12 hours (overnight) at the same temperature. TLC (DCM:MeOH:$NH_4OH$, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (DCM:MeOH:$NH_4OH$, 90:9:1) to give 11 mg of product (75% yield). NMR (500 MHz, DMSO-d6) δ 12.66 (bs, 1H), 9.45 (bs, 1H), 8.98 (s, 1H), 8.60 (bs, 1H), 8.29 (s, 1H), 8.04 (s, 1H), 8.01-7.88 (m, 2H), 7.62-7.49 (m, 1H), 7.40 (q, J=8.0 Hz, 4H), 7.26 (t, J=8.8 Hz, 1H), 5.15 (d, J=3.5 Hz, 1H), 4.54 (d, J=9.3 Hz, 1H), 4.49-4.31 (m, 3H), 4.22 (dd, J=16.1, 5.6 Hz, 1H), 3.81-3.53 (m, 6H), 3.26-3.03 (m, 6H), 2.73-2.52 (m, 3H), 2.44 (s, 3H), 2.42-2.33 (m, 1H), 2.09-1.98 (m, 1H), 1.95-1.84 (m, 1H), 1.74 (q, J=7.5 Hz, 2H), 0.96 (t, 3H), 0.94 (s, 9H). $^{13}C$ NMR (126 MHz, dmso) δ 180.45, 172.02, 171.35, 170.07, 169.64, 156.00 (dd, J=245.9, 6.5 Hz), 152.34 (dd, J=249.7, 8.3 Hz), 151.52, 147.75, 144.70, 144.30, 139.55, 138.08, 137.91, 131.22, 129.66, 128.69, 128.53 (d, J=2.4 Hz), 127.46, 121.96 (d, J=14.1 Hz), 118.61-117.82 (m), 117.60, 115.44, 115.20, 112.32 (dd, J=23.0, 3.3 Hz), 68.95, 58.78, 56.50, 56.39, 53.46, 50.25, 50.13, 44.76, 41.69, 41.17, 37.99, 35.43, 30.18, 28.05, 26.44, 16.89, 16.00, 12.67. LC-MS (ESI); m/z $[M+H]^+$: Calcd. for $C_{47}H_{56}F_2N_9O_8S_2$, 976.3661. Found 976.3712.

Example Synthesis of Compound 220: $N^1$-(4-(3-(2,6-difluoro-3-(propylsulfonamido)benzoyl)-1H-pyrrolo[2,3-b]pyridin-5-yl)phenyl)-$N^4$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamid

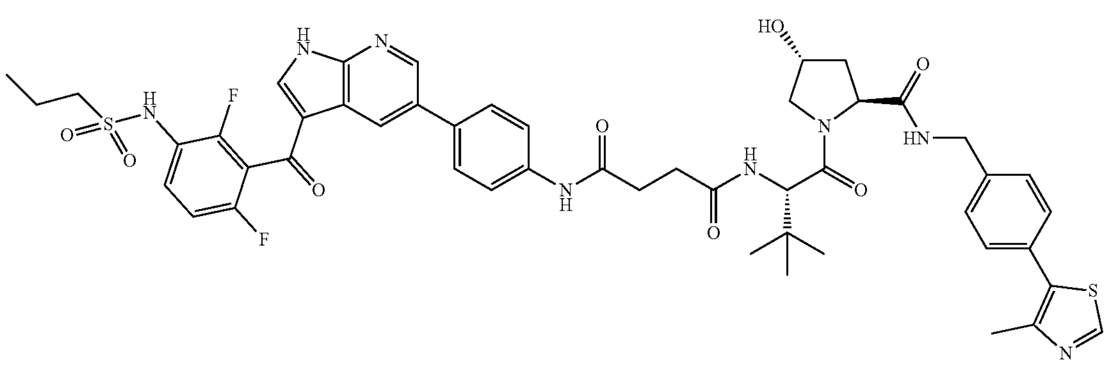 [SMILES: CCCS(=O)(=O)Nc1ccc(F)c(C(=O)c2c[nH]c3ncc(-c4ccc(NC(=O)CCC(=O)N[C@H](C(=O)N5C[C@H](O)C[C@H]5C(=O)NCc5ccc(-c6scnc6C)cc5)C(C)(C)C)cc4)cc23)c1F]

To a solution of the product from the synthesis of compound 218 [(2S,4R)-1-((S)-2-(5-(4-(3-(2,6-difluoro-3-(propylsulfonamido)benzoyl)-1H-pyrrolo[2,3-b]pyridin-5-yl) piperazin-1-yl)-5-oxopentanamido)-3,3-dimethylbutanoyl)-4-hydroxy-N-(4-(4-methylthiazol-5-yl)benzyl)pyrrolidine-2-carboxamide]; 4-((4-(3-(2,6-difluoro-3-(propylsulfonamido)-benzoyl)-1H-pyrrolo[2,3-b]pyridin-5-yl)phenyl)amino)-4-oxobutanoic acid (15 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (13.51 mg, 0.03 mmol) in DMF (1 ml) was added TEA (0.1 ml, 0.72 mmol) and PyBOP (15.05 mg, 0.03 mmol) at room temperature. The reaction mixture was stirred for 4 hours at the same temperature. TLC (DCM:MeOH:$NH_4OH$, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MeOH:$NH_4OH$, 90:9:1) to give 8 mg of product (31% yield). NMR (500 MHz, DMSO-d6) δ 12.97 (bs, 1H), 10.11 (s, 1H), 9.79 (bs, 1H), 8.98 (d, J=2.3 Hz, OH), 8.69 (s, 1H), 8.66-8.49 (m, 2H), 8.23 (s, 1H), 8.02 (d, J=9.0 Hz, 1H), 7.84-7.64 (m, 4H), 7.63-7.53 (m, 1H), 7.51-7.33 (m, 4H), 7.29 (t, J=8.4 Hz, 1H), 5.17 (s, 1H), 4.56 (d, J=7.8 Hz, 1H), 4.50-4.39 (m, 2H), 4.40-4.31 (m, 1H), 4.26-4.16 (m, 1H), 3.66 (q, J=10.1 Hz, 2H), 3.19-3.06 (m, 2H), 2.72-2.52 (m, 4H), 2.44 (s, 3H), 2.12-1.97 (m, 1H), 1.96-1.84 (m, 1H), 1.74 (dq, J=13.2, 8.3, 7.3 Hz, 2H), 0.96 (t, 3H), 0.95 (s, 9H). $^{13}C$ NMR (126 MHz, dmso) δ 180.66, 172.02, 171.24, 170.67, 169.64, 156.05 (dd, J=246.9, 7.0 Hz), 152.37 (dd, J=249.3, 8.1 Hz), 151.49, 148.66, 147.75, 143.82, 139.53, 139.00, 138.70, 132.54, 131.27, 131.22, 129.68, 129.22-128.38 (m), 128.69, 127.47, 127.39, 126.53, 121.99 (dd, J=12.9, 4.5 Hz), 119.59, 118.72-117.87 (m), 117.57, 115.68, 112.90-112.05 (m), 68.95, 58.79, 56.56, 56.41, 53.51, 41.71, 37.98, 35.45, 31.98, 30.14, 26.43, 16.88, 15.99, 12.65. LC-MS (ESI); m/z $[M+H]^+$: Calcd. for $C_{49}H_{53}F_2N_8O_8S_2$, 983.3395. Found 983.3569.

Example Synthesis of Compound 221: N1-(4-(3-(2,6-difluoro-3-(propylsulfonamido)benzoyl)-1H-pyrrolo[2,3-b]pyridin-5-yl)phenyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)malonamide To a solution of 3-((4-(3-(2,6-difluoro-3-(propylsulfonamido)-benzoyl)-1H-pyrrolo[2,3-b]pyridin-5-yl)phenyl) amino)-3-oxopropanoic acid (16.8 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (15.5 mg, 0.033 mmol) in DMF (1 ml) was added TEA (0.1 ml, 0.72 mmol) and PyBOP (17.28 mg, 0.033 mmol) at room temperature. The reaction mixture was stirred for 12 hours (overnight) at the same temperature. TLC (DCM:MeOH:$NH_4OH$, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MeOH:$NH_4OH$, 90:9:1) to give 19.5 mg of product (67% yield). NMR (400 MHz, DMSO-d6) δ 12.96 (bs, 1H), 10.23 (s, 1H), 9.75 (bs, 1H), 8.97 (s, 1H), 8.69 (s, 1H), 8.66-8.51 (m, 2H), 8.26 (d, J=9.1 Hz, 1H), 8.22 (s, 1H), 7.73 (dd, J=8.5 Hz, 4H), 7.59 (q, J=8.6 Hz, 1H), 7.41 (dd, J=8.0 Hz, 4H), 7.28 (t, J=8.7 Hz, 1H), 5.16 (d, 1H), 4.59 (d, J=9.2 Hz, 1H), 4.52-4.33 (m, 3H), 4.24 (dd, J=15.7, 5.0 Hz, 1H), 3.68 (q, J=10.6 Hz, 2H), 3.44 (q, 2H), 3.20-3.05 (m, 2H), 2.45 (s, 3H), 2.10-2.01 (m, 1H), 1.96-1.89 (m, 1H), 1.74 (dq, J=14.8, 7.3 Hz, 2H), 0.98 (s, 9H), 0.97 (t, J=8.3 Hz, 3H). $^{13}C$ NMR (101 MHz, dmso) δ 180.62, 171.91, 169.34, 166.16, 166.03, 156.02 (dd, J=246.8, 7.1 Hz), 152.34 (dd, J=249.4, 8.1 Hz), 151.43, 148.69, 147.73, 143.79, 139.50, 138.69, 138.54, 132.98, 131.17, 131.13, 129.68, 129.11-128.65 (m), 128.67, 128.01, 127.45, 126.53, 122.21-121.73 (m), 119.70, 118.63-117.89 (m), 117.54, 115.66, 112.35 (dd, J=23.5, 3.0 Hz), 68.93, 58.79, 56.66, 56.52, 53.49, 44.32, 41.70, 37.97, 35.60, 26.33, 16.85, 15.96, 12.62. LC-MS (ESI); m/z $[M+H]^+$: Calcd. for $C_{45}H_{51}F_2N_8O_8S_2$, 969.3239. Found 969.3272.

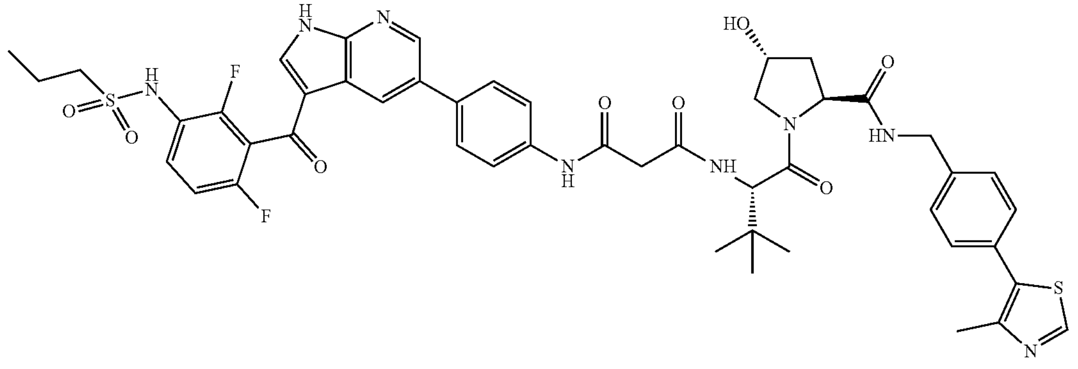 [SMILES: CCCS(=O)(=O)Nc1ccc(F)c(C(=O)c2c[nH]c3ncc(-c4ccc(NC(=O)CC(=O)N[C@H](C(=O)N5C[C@H](O)C[C@H]5C(=O)NCc5ccc(-c6scnc6C)cc5)C(C)(C)C)cc4)cc23)c1F]

Example Synthesis of Compound 222: (2S,4R)-1-((S)-2-(3-(4-(3-(2,6-difluoro-3-(propylsulfonamido)benzoyl)-1H-pyrrolo[2,3-b]pyridin-5-yl)piperazin-1-yl)-3-oxopropanamido)-3,3-dimethylbutanoyl)-4-hydroxy-N-(4-(4-methylthiazol-5-yl)benzyl)pyrrolidine-2-carboxamide

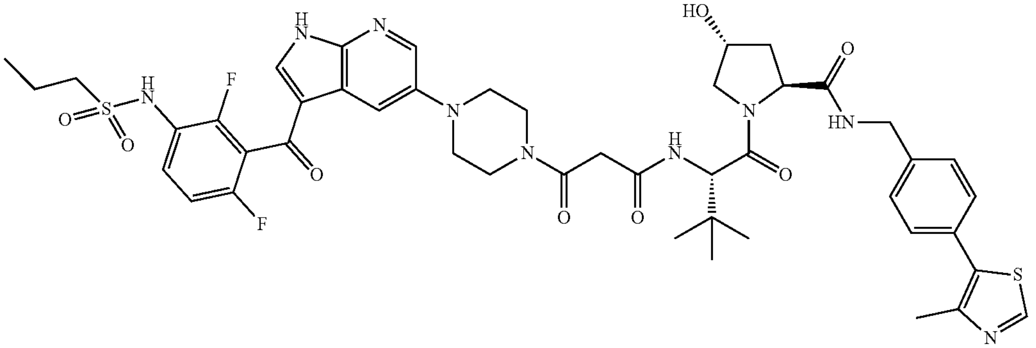 [SMILES: CCCS(=O)(=O)Nc1ccc(F)c(C(=O)c2c[nH]c3ncc(N4CCN(C(=O)CC(=O)N[C@H](C(=O)N5C[C@H](O)C[C@H]5C(=O)NCc5ccc(-c6scnc6C)cc5)C(C)(C)C)CC4)cc23)c1F]

To a solution of 3-(4-(3-(2,6-difluoro-3-(propylsulfonamido)-benzoyl)-1H-pyrrolo[2,3-b]pyridin-5-yl)piperazin-1-yl)-3-oxopropanoic acid (12.5 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (11.69 mg, 0.03 mmol) in DMF (1 ml) was added TEA (0.1 ml, 0.72 mmol) and PyBOP (13.02 mg, 0.03 mmol) at room temperature. The reaction mixture was stirred for 12 hours (overnight) at the same temperature. TLC (DCM:MeOH:$NH_4OH$, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (DCM:MeOH:$NH_4OH$, 90:9:1) to give 14.1 mg of product (64% yield). $^1H$ NMR (500 MHz, DMSO-d6) δ 12.71 (bs, 1H), 9.74 (bs, 1H), 8.98 (s, 1H), 8.59 (t, J=5.7 Hz, 1H), 8.29 (s, 1H), 8.26 (d, J=9.1 Hz, 1H), 8.03 (s, 1H), 7.96 (bs, 1H), 7.57 (q, J=7.4, 6.3 Hz, 1H), 7.41 (dd, J=8.0 Hz, 4H), 7.26 (t, J=8.7 Hz, 1H), 5.22-5.05 (m, 1H), 4.58 (d, J=9.3 Hz, 1H), 4.51-4.32 (m, 3H), 4.23 (dd, J=15.8, 5.3 Hz, 1H), 3.67 (q, J=12.3, 10.6 Hz, 8H), 3.52 (dd, J=53.7, 15.5 Hz, 2H), 3.27-3.05 (m, 6H), 2.45 (s, 3H), 2.09-2.00 (m, 1H), 1.96-1.86 (m, 1H), 1.74 (h, J=7.3 Hz, 2H), 0.97 (s, 9H), 0.96 (t, 3H). $^{13}C$ NMR (101 MHz, dmso) δ 180.41, 171.91, 169.38, 166.32, 166.06, 156.01 (dd, J=246.5, 6.7 Hz), 152.34 (dd, J=249.2, 8.3 Hz), 151.44, 147.73, 144.60, 144.28, 139.50, 138.06, 137.84, 131.17, 129.66, 128.75 (d, J=8.0 Hz), 128.65, 127.43, 121.86 (dd, J=13.5, 3.5 Hz), 118.34 (m), 117.58, 115.42, 115.18, 112.28 (dd, J=23.1, 3.5 Hz), 68.89, 58.75, 56.54, 56.43, 53.49, 50.10, 45.56, 41.68, 41.19, 40.95, 37.95, 35.52, 26.36, 16.85, 15.96, 12.62. LC-MS (ESI); m/z $[M+H]^+$: Calcd. for $C_{46}H_{54}F_2N_9O_8S_2$, 962.3504. Found 962.3694.

Example Synthesis of Compound 301: (2S,4R)-1-((S)-2-(4-(4-(3-(3-butyramido-2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide

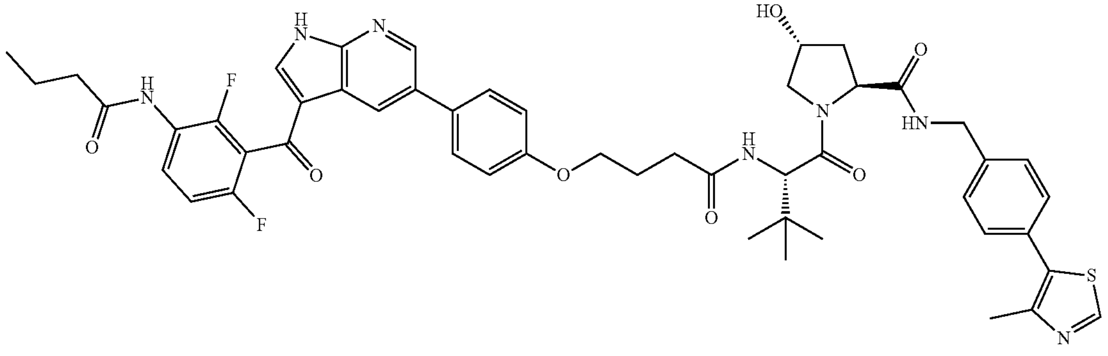 [SMILES: CCCC(=O)Nc1ccc(F)c(C(=O)c2c[nH]c3ncc(-c4ccc(OCCCC(=O)N[C@H](C(=O)N5C[C@H](O)C[C@H]5C(=O)NCc5ccc(-c6scnc6C)cc5)C(C)(C)C)cc4)cc23)c1F]

To a solution of 4-(4-(3-(3-butyramido-2,6-difluorobenzoyl)-1H-pyrrolo[2,3-b]pyridin-5-yl)phenoxy)butanoic acid (27 mg, 0.05 mmol) and (2S,4R)-1-[(2S)-2-amino-3,3-dimethyl-butanoyl]-4-hydroxy-N-[[4-(4-methylthiazol-5-yl) phenyl]methyl]pyrrolidine-2-carboxamide;hydrochloride (26.6 mg, 0.06 mmol) in DMF (2 ml) was added TEA (0.1 ml, 0.72 mmol) and PyBOP (29.64 mg, 0.06 mmol) at room temperature. The reaction mixture was stirred for 4 hours at the same temperature. TLC (DCM:MeOH:$NH_4OH$, 90:9:1) shows no starting materials. The DMF was removed under high vacuum. Crude product was filtered over a silica-carbonate cartridge using DCM:MeOH (9:1) as a eluent. Filtrate was evaporated under vacuum and crude product was purified by PTFC (DCM:MeOH:$NH_4OH$, 90:9:1) to give 37 mg of product (76% yield). NMR (400 MHz, DMSO-d6) δ 12.91 (bs, 1H), 9.79 (s, 1H), 8.97 (s, 1H), 8.65 (d, J=2.2 Hz, 1H), 8.62-8.47 (m, 2H), 8.15 (s, 1H), 8.06-7.89 (m, 2H), 7.67 (d, J=8.7 Hz, 2H), 7.40 (dd, J=8.3 Hz, 4H), 7.23 (t, J=8.8 Hz, 1H), 7.07 (d, J=8.8 Hz, 2H), 5.14 (d, J=3.5 Hz, 1H), 4.58 (d, J=9.3 Hz, 1H), 4.49-4.40 (m, 2H), 4.37 (bs, 1H), 4.22 (dd, J=15.9, 5.4 Hz, 1H), 4.03 (t, J=7.2 Hz, 2H), 3.77-3.62 (m, 2H), 2.44 (s, 3H), 2.43-2.30 (m, 4H), 2.09-1.87 (m, 4H), 1.61 (h, J=7.4 Hz, 2H), 0.96 (s, 9H), 0.92 (t, J=7.4 Hz, 3H). $^{13}C$ NMR (151 MHz, dmso) δ 180.92, 171.97, 171.67, 171.61, 169.68, 158.33, 154.61 (dd, J=244.6, 7.1 Hz), 151.44, 150.34 (dd, J=248.8, 8.2 Hz), 148.52, 147.72, 143.71, 139.52, 138.48, 131.32, 131.17, 130.42, 129.64, 128.65, 128.28, 127.43, 126.50, 126.06 (d, J=10.1 Hz), 123.23 (dd, J=12.4, 3.6 Hz), 118.47-117.44 (m), 117.55, 115.65, 115.18, 111.60 (d, J=25.0 Hz), 68.92, 67.13, 58.74, 56.48, 56.42, 41.67, 37.99, 37.57, 35.26, 31.32, 26.41, 25.07, 18.56, 15.96, 13.57. FC-MS (ESI); m/z $[M+H]^+$: Calcd. for $C_{50}H_{54}F_2N_7O_7S$, 934.3773. Found 934.2690.

Example Synthesis of Compound 302: (2S,4R)-1-((S)-2-(4-(4-(3-(3-amino-2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide To a solution of 4-(4-(3-(3-amino-2,6-difluorobenzoyl)-1H-pyrrolo[2,3-b]pyridin-5-yl)phenoxy)butanoic acid (11.5 mg, 0.03 mmol) and (2S,4R)-1-[(2S)-2-amino-3,3-dimethyl-butanoyl]-4-hydroxy-N-[[4-(4-methylthiazol-5-yl) phenyl]methyl]pyrrolidine-2-carboxamide;hydrochloride (23.79 mg, 0.05 mmol) in DMF (2 ml) was added TEA (0.1 ml, 0.72 mmol) and PyBOP (14.58 mg, 0.03 mmol) at room temperature. The reaction mixture was stirred for 4 h at the same temperature. TLC (DCM:MeOH:$NH_4OH$, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTFC (MeOH:DCM, 9:1), to give 17.5 mg of product (80% yield). NMR (500 MHz, DMSO-d6) δ 12.68 (bs, 1H), 8.97 (s, 1H), 8.64 (d, J=2.2 Hz, 1H), 8.61-8.47 (m, 2H), 8.06 (s, 1H), 8.00 (d, J=9.3 Hz, 1H), 7.65 (d, J=8.6 Hz, 2H), 7.40 (dd, 4H), 7.07 (d, J=8.7 Hz, 2H), 6.99-6.82 (m, 2H), 5.21 (s, 2H), 5.15 (d, J=3.6 Hz, 1H), 4.58 (d, J=9.3 Hz, 1H), 4.50-4.40 (m, 2H), 4.37 (bs, 1H), 4.23 (dd, J=15.8, 5.3 Hz, 1H), 4.10-3.93 (m, 2H), 3.78-3.54 (m, 2H), 2.58-2.26 (m, 2H), 2.44 (s, 3H), 2.11-1.82 (m, 4H), 0.94 (s, 9H). $^{13}C$ NMR (126 MHz, dmso) δ 182.20, 171.97, 171.63, 169.69, 158.31, 151.43, 149.20 (dd, J=234.8, 6.5 Hz), 148.45, 147.72, 146.01 (dd, J=241.2, 7.9 Hz), 143.55, 139.51, 137.92, 133.42 (dd, J=12.9, 2.4 Hz), 131.18, 130.49, 129.65, 128.65, 128.24, 127.44, 126.47, 118.32-117.22 (m), 117.57, 116.91-116.23 (m), 115.84, 115.19, 111.36 (dd, J=22.3, 2.9 Hz), 68.92, 67.14, 58.74, 56.50, 56.41, 41.68, 37.97, 35.25, 31.33, 26.41, 25.07, 15.95. FC-MS (ESI); m/z $[M+H]^+$: Calcd. for $C_{46}H_{48}F_2N_7O_6S$, 864.3354. Found 864.3437.

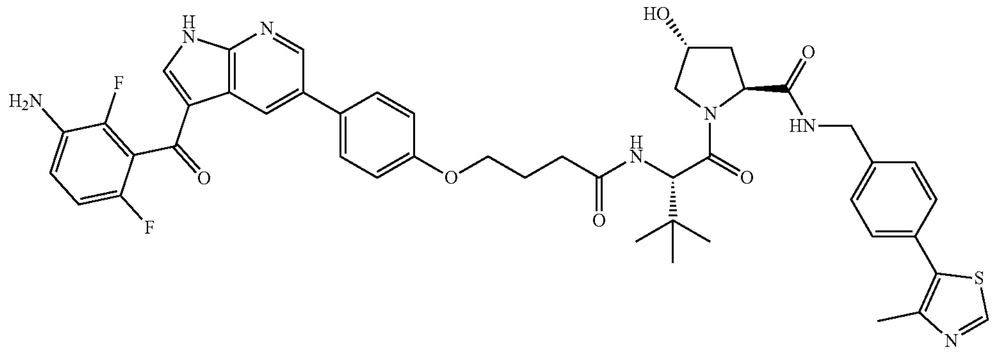 [SMILES: Cc1ncsc1-c1ccc(CNC(=O)[C@@H]2C[C@@H](O)CN2C(=O)[C@@H](NC(=O)CCCOc2ccc(-c3cnc4[nH]cc(C(=O)c5c(F)ccc(N)c5F)c4c3)cc2)C(C)(C)C)cc1]

Example Synthesis of Compound 303: (2S,4R)-1-((S)-2-(4-(4-(3-(2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide

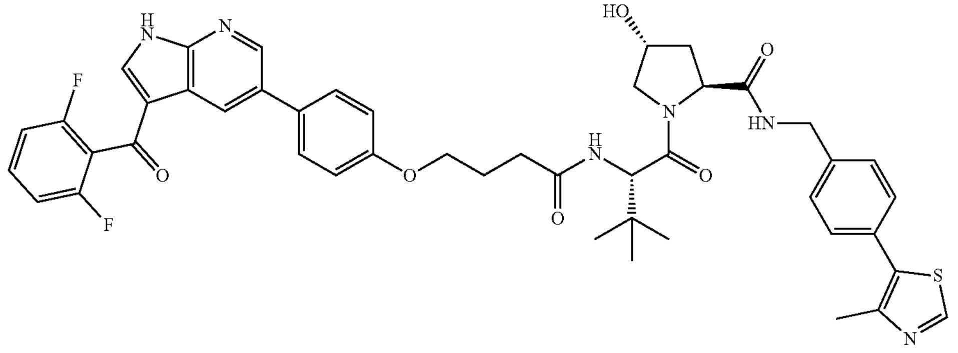 [SMILES: Cc1ncsc1-c1ccc(CNC(=O)[C@@H]2C[C@@H](O)CN2C(=O)[C@@H](NC(=O)CCCOc2ccc(-c3cnc4[nH]cc(C(=O)c5c(F)cccc5F)c4c3)cc2)C(C)(C)C)cc1]

To a solution of 4-(4-(3-(2,6-difluorobenzoyl)-1H-pyrrolo-[2,3-b]pyridin-5-yl)phenoxy)butanoic acid (19.4 mg, 0.04 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (20.76 mg, 0.04 mmol) in DMF (2 ml) was added TEA (0.1 ml, 0.72 mmol) and PyBOP (25.45 mg, 0.05 mmol) at room temperature. The reaction mixture was stirred for 4 hours at the same temperature. TLC (DCM:MeOH:$NH_4OH$, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTFC (DCM:MeOH:$NH_4OH$, 90:9:1), to give 29 mg of product (77% yield). NMR (500 MHz, DMSO-d6) δ 12.89 (bs, 1H), 8.97 (s, 1H), 8.65 (d, J=1.9 Hz, 1H), 8.62-8.54 (m, 2H), 8.13 (s, 1H), 8.00 (d, J=9.3 Hz, 1H), 7.75-7.55 (m, 3H), 7.43 (d, J=8.1 Hz, 3H), 7.38 (d, J=8.1 Hz, 2H), 7.28 (t, J=7.9 Hz, 2H), 7.07 (d, J=8.6 Hz, 2H), 5.15 (d, J=3.3 Hz, 1H), 4.59 (d, J=9.3 Hz, 1H), 4.49-4.40 (m, 2H), 4.39-4.33 (m, 1H), 4.23 (dd, J=15.9, 5.4 Hz, 1H), 4.09-3.97 (m, 2H), 3.77-3.61 (m, 2H), 1H NMR (500 MHz, DMSO-d6) δ 2.48-2.31 (m, 2H), 2.44 (s, 3H), 2.11-1.86 (m, 4H), 0.96 (s, 9H). $^{13}C$ NMR (151 MHz, dmso) δ 181.30, 171.97, 171.61, 169.68, 158.80 (dd, J=247.2, 7.9 Hz), 158.33, 151.44, 148.52, 147.72, 143.70, 139.51, 138.38, 132.14 (t, J=9.9 Hz), 131.30, 131.17, 130.44, 129.64, 128.64, 128.27, 127.43, 126.48, 117.76 (t, J=23.3 Hz), 117.54, 115.78, 115.18, 112.29 (dd, J=21.0, 4.2 Hz), 68.92, 67.13, 58.74, 56.48, 56.42, 41.67, 37.98, 35.26, 31.32, 26.41, 25.06, 15.96. FC-MS (ESI); m/z $[M+H]^+$: Calcd. for $C_{46}H_{47}F_2N_6O_6S$, 849.3245. Found 849.3378.

Example Synthesis of Compound 304: (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)butanamido)-3,3-di methyl butanoyl)-4-hydroxy-N-(4-(4-methylthiazol-5-yl)benzyl)pyrrolidine-2-carboxamide

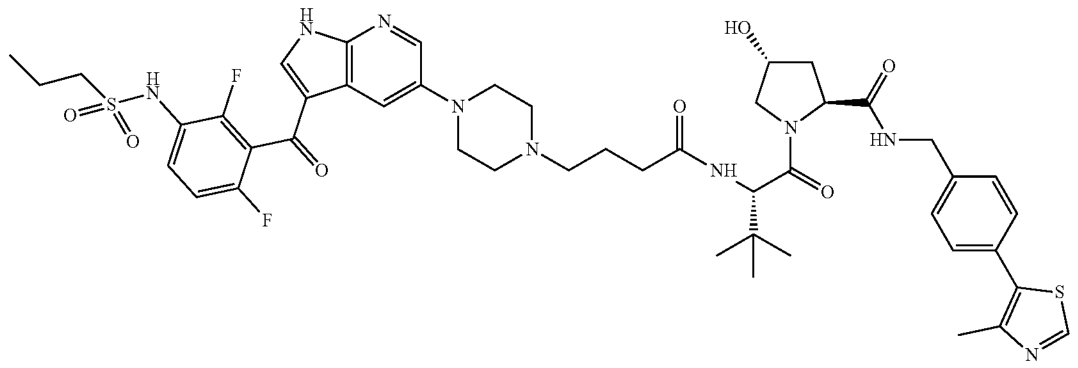 [SMILES: CCCS(=O)(=O)Nc1ccc(F)c(C(=O)c2c[nH]c3ncc(N4CCN(CCCC(=O)N[C@H](C(=O)N5C[C@H](O)C[C@H]5C(=O)NCc5ccc(-c6scnc6C)cc5)C(C)(C)C)CC4)cc23)c1F]

To a solution of 4-[4-[3-[2,6-difluoro-3-(propylsulfonylamino)benzoyl]-1H-pyrrolo[2,3-b]pyridin-5-yl]piperazin-1-yl]butanoic acid (7.9 mg, 0.01 mmol) and (2S,4R)-1-[(2S)-2-amino-3,3-dimethyl-butanoyl]-4-hydroxy-N-[[4-(4-methylthiazo-1-5-yl)phenyl]methyl]pyrrolidine-2-carboxamide;hydrochloride (7.38 mg, 0.02 mmol) in DMF (1 ml) was added TEA (0.1 ml, 0.72 mmol) and PyBOP (8.23 mg, 0.02 mmol) at room temperature. The reaction mixture was stirred for 12 hours (overnight) at the same temperature. TLC (DCM:MeOH:$NH_4OH$, 90:9:1) shows no starting materials. The reaction mixture was evaporated to dryness. Crude product was filtered over a silica-carbonate cartridge (1 g) using DCM:MeOH (9:1) as eluent (washed a few times, product has high affinity for the stationary phase). Filtrate was evaporated under vacuum and crude product was purified by PTLC (DCM:MeOH, 9:1) to give 7.2 mg of product (52% yield). NMR (500 MHz, DMSO-d6) δ 12.66 (bs, 1H), 9.73 (bs, 1H), 8.96 (s, 1H), 8.61-8.50 (m, 1H), 8.25 (s, 1H), 8.00 (s, 1H), 7.93 (bs, 1H), 7.88 (d, J=9.1 Hz, 1H), 7.63-7.49 (m, 1H), 7.40 (dd, 4H), 7.25 (t, J=8.7 Hz, 1H), 5.14 (s, 1H), 4.56 (d, J=9.1 Hz, 1H), 4.46-4.34 (m, 3H), 4.22 (dd, J=15.8, 4.7 Hz, 1H), 3.75-3.60 (m, 2H), 3.23-3.14 (m, 4H), 3.13-3.08 (m, 2H), 2.65-2.53 (m, 4H), 2.43 (s, 3H), 2.38-2.31 (m, 2H), 2.31-2.25 (m, 1H), 2.24-2.16 (m, 1H), 2.07-1.99 (m, 1H), 1.95-1.87 (m, 1H), 1.72 (dq, J=16.3, 10.5, 8.9 Hz, 4H), 0.95 (t, J=5.3 Hz, 3H), 0.95 (s, 9H). $^{13}C$ NMR (151 MHz, DMSO-d6) δ 180.77, 172.43, 172.39, 170.12, 156.38 (dd, J=246.2, 7.1 Hz), 152.75 (dd, J=249.8, 9.0 Hz), 151.87, 148.13, 145.23, 144.35, 139.92, 138.09, 137.78, 131.59, 130.05, 129.21-128.76 (m), 127.84, 122.32 (d, J=13.1 Hz), 119.83-118.25 (m), 118.03, 115.53, 114.96, 112.68 (d, J=22.7 Hz), 69.30, 59.13, 57.62, 56.79, 55.33, 53.88, 53.06, 50.11, 42.07, 38.38, 35.68, 33.27, 26.83, 23.09, 17.26, 16.37, 13.04. LC-MS (ESI); m/z $[M+H]^+$: Calcd. for $C_{47}H_{58}F_2N_9O_7S_2$, 962.3868. Found 962.3986.

Example Synthesis of Compound 305: (2S,4R)-1-((S)-2-(4-(4-(3-benzoyl-1H-pyrrolo[2,3-b]pyridin-5-yl)phenoxy)butanamido)-3,3-dimethylbutanoyl)-4-hydroxy-N-(4-(4-methylthiazol-5-yl)benzyl) pyrrolidine-2-carboxamide

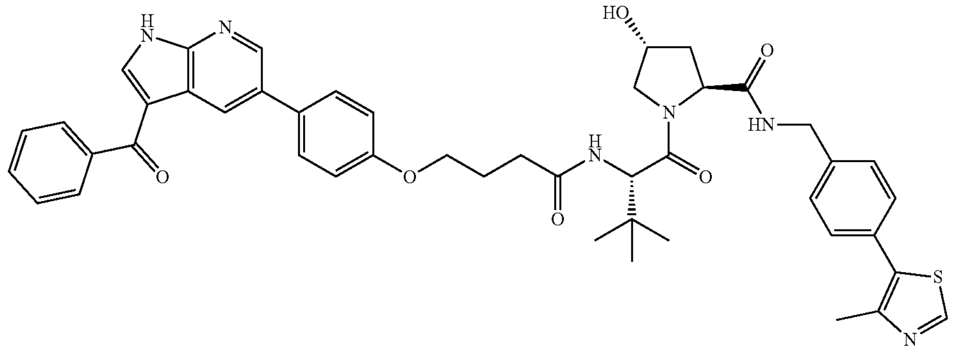 [SMILES: Cc1ncsc1-c1ccc(CNC(=O)[C@@H]2C[C@@H](O)CN2C(=O)[C@@H](NC(=O)CCCOc2ccc(-c3cnc4[nH]cc(C(=O)c5ccccc5)c4c3)cc2)C(C)(C)C)cc1]

To a solution of 4-[4-(3-benzoyl-1H-pyrrolo[2,3-b]pyridin-5-yl)-phenoxy]butanoic acid (26.5 mg, 0.07 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (30.91 mg, 0.07 mmol) in DMF (2 ml) was added TEA (0.2 ml, 1.43 mmol) and PyBOP (37.88 mg, 0.07 mmol) at room temperature. The reaction mixture was stirred for 12 hours (overnight) at the same temperature. TLC (DCM:MeOH:$NH_4OH$, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTLC (MeOH:DCM, 9:1), to give 31 mg of product (58% yield). $^1H$ NMR (400 MHz, DMSO-d6) δ 12.70 (s, 1H), 8.97 (s, 1H), 8.68 (d, J=2.2 Hz, 1H), 8.62 (d, J=2.3 Hz, 1H), 8.60-8.51 (m, 1H), 8.12 (s, 1H), 8.00 (d, J=9.3 Hz, 1H), 7.90-7.77 (m, 1H), 7.72-7.51 (m, 5H), 7.48-7.29 (m, 4H), 7.07 (d, J=8.7 Hz, 2H), 5.15 (d, J=3.5 Hz, 1H), 4.59 (d, J=9.3 Hz, 1H), 4.50-4.32 (m, 3H), 4.22 (dd, J=15.9, 5.4 Hz, 1H), 4.03 (td, J=6.5, 2.6 Hz, 2H), 3.80-3.60 (m, 2H), 2.44 (s, 3H), 2.48-2.28 (m, 5H), 2.13-1.84 (m, 4H), 0.96 (s, 9H). $^{13}C$ NMR (101 MHz, dmso) δ 189.87, 172.00, 171.63, 169.69, 158.23, 151.48, 148.29, 147.73, 143.29, 139.64, 139.53, 136.54, 131.52, 131.19, 130.74, 129.65, 128.66, 128.58, 128.55, 128.21, 127.44, 127.05, 118.81, 115.19, 113.74, 68.93, 67.13, 58.75, 56.47, 48.64, 41.68, 38.01, 35.29, 31.33, 26.43, 25.08, 15.99. LC-MS (ESI); m/z $[M+H]^+$: Calcd. for $C_{46}H_{49}N_6O_6S$, 813.3434. Found 813.3478.

Example Synthesis of Compound 306: (2S,4R)-1-((S)-2-(2-(2-(4-(3-(2,6-difluoro-3-(propylsulfonamido)benzoyl)-1H-pyrrolo[2,3-b]pyridin-5-yl)piperazin-1-yl)ethoxy)acetamido)-3,3-dimethylbutanoyl)-4-hydroxy-N-(4-(4-methylthiazol-5-yl)benzyl) pyrrolidine-2-carboxamide

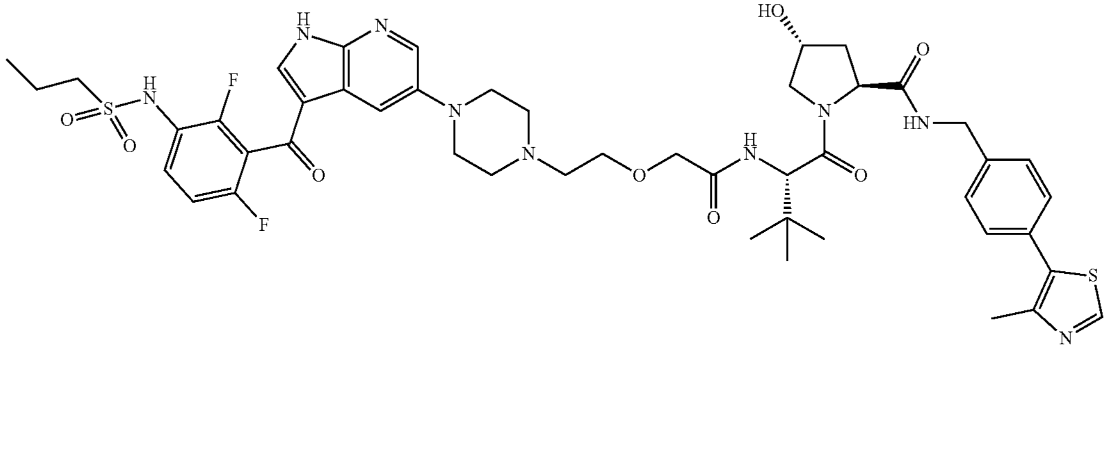 [SMILES: CCCS(=O)(=O)Nc1ccc(F)c(C(=O)c2c[nH]c3ncc(N4CCN(CCOCC(=O)N[C@H](C(=O)N5C[C@H](O)C[C@H]5C(=O)NCc5ccc(-c6scnc6C)cc5)C(C)(C)C)CC4)cc23)c1F]

To a solution of 2-[2-[4-[3-[2,6-difluoro-3-(propyl-sulfonylamino)benzoyl]-1H-pyrrolo[2,3-b]pyridin-5-yl]piperazin-1-yl]ethoxy]acetic acid (7.9 mg, 0.01 mmol) and (2S, 4R)-1-[(2S)-2-amino-3,3-dimethyl-butanoyl]-4-hydroxy-N-[[4-(4-methylthiazol-5-yl)phenyl]methyl]pyrrolidine-2-carboxamide;hydrochloride (7.18 mg, 0.02 mmol) in DMF (1 ml) was added TEA (0.1 ml, 0.72 mmol) and PyBOP (8 mg, 0.02 mmol) at room temperature. The reaction mixture was stirred for 12 hours (overnight) at the same temperature. TLC (DCM:MeOH:$NH_4OH$, 90:9:1) shows no starting materials. The reaction mixture was evaporated to dryness under high vacuum. Crude product was evaporated under vacuum and crude product was purified by PTLC (DCM: MeOH:$NH_4OH$, 90:9:1) to give 8.1 mg of product (59% yield). NMR (500 MHz, DMSO-d6) δ 12.66 (bs, 1H), 9.72 (bs, 1H), 8.93 (s, 1H), 8.59 (bs, 1H), 8.22 (s, 1H), 7.99 (s, 1H), 7.89 (bs, 1H), 7.56 (dh, J=9.1, 3.4, 2.9 Hz, 1H), 7.51-7.31 (m, 5H), 7.25 (t, J=8.6 Hz, 1H), 5.17 (s, 1H), 4.57 (dd, J=9.7, 2.4 Hz, 1H), 4.50-4.33 (m, 3H), 4.28-4.19 (m, 1H), 4.07-3.92 (m, 2H), 3.65 (d, J=15.4 Hz, 4H), 3.22-3.05 (m, 6H), 2.64 (d, J=21.6 Hz, 6H), 2.42 (s, 3H), 2.11-2.03 (m, 1H), 1.91 (dd, J=13.3, 5.8 Hz, 1H), 1.80-1.67 (m, 2H), 0.96 (s/t overlapping, 12H). $^{13}C$ NMR (151 MHz, DMSO-d6) δ 180.38, 171.80, 169.18, 168.58, 156.01 (dd, J=246.2, 6.8 Hz), 152.34 (dd, J=249.1, 8.7 Hz), 151.39, 147.73, 144.79, 143.97, 139.43, 137.73, 137.38, 131.16, 129.70, 128.68, 128.60 (d), 127.47, 121.93 (dd, J=13.8, 3.7 Hz), 118.89-118.05 (m), 117.64, 115.15, 114.62, 112.29 (dd, J=22.2, 3.2 Hz), 69.65, 68.94, 68.76, 58.81, 57.13, 56.64, 55.73, 53.49, 53.09, 49.72, 41.71, 37.93, 35.87, 26.24, 16.88, 15.95, 12.65. LC-MS (ESI); m/z $[M+H]^+$: Calcd. for $C_{47}H_{58}F_2N_9O_8S_2$, 978.3817. Found 978.3933.

Exemplary Synthesis of (R)—N-(2,4-difluoro-3-(5-(4,4,5,5-tetramethyl-1,3,2-dioxaborolan-2-yl)-1-((2-(trimethylsilyl)ethoxy)methyl)-1H-pyrrolo[2,3-b]pyridine-3-carbonyl)phenyl)-3-fluoro-N-((2-(trimethylsilyl)ethoxy)methyl)pyrrolidine-1-sulfonamide (Intermediate 6)

Step 1: Preparation of 2,6-difluoro-3-nitrobenzoyl chloride

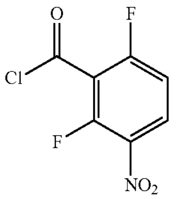 [SMILES: O=C(Cl)c1c(F)ccc([N+](=O)[O-])c1F]

Into a 500-mF round-bottom flask, was placed 2,6-difluoro-3-nitrobenzoic acid (30.0 g, 147.6 mmol, 1.0 equiv), toluene (160 mF), thionyl chloride (160 mF). The resulting mixture was stirred at 80° C. overnight and concentrated under reduced pressure. This resulted in 28.2 g (86%) of 2,6-difluoro-3-nitrobenzoyl chloride as a brown oil.

Step 2: Preparation of (5-bromo-1H-pyrrolo[2,3-b]pyridin-3-yl)(2,6-difluoro-3-nitrophenyl)methanone

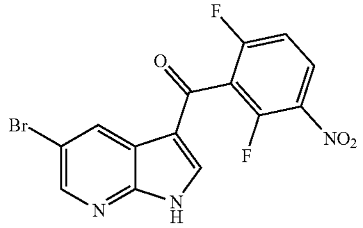 [SMILES: O=C(c1c(F)ccc([N+](=O)[O-])c1F)c1c[nH]c2ncc(Br)cc12]

A mixture of 5-bromo-1H-pyrrolo[2,3-b]pyridine (22.0 g, 111.6 mmol, 1.1 equiv) in 300 mF of chloromethane was charged with aluminum trichloride (84.0 g, 0.64 mol, 6.4 equiv) portion wise. The reaction was stirred at room temperature for 1 hour and 2,6-difluoro-3-nitrobenzoyl chloride (22.0 g, 100.0 mmol, 1.0 equiv) was added. The reaction was heated at 50° C. overnight, then the reaction mixture was cooled to room temperature and poured into ice-water (500 mF), extracted with ethyl acetate (500 mF×3). The combined organic layers were washed with brine (500 mF×2), dried over anhydrous sodium sulfate. The solvent was concentrated to give (5-bromo-1H-pyrrolo[2,3-b]pyridin-3-yl)(2,6-difluoro-3-nitrophenyl) methanone (24.4 g) as a yellow solid. FC/MS (ESI) m/z: 381.30 $[M+1]^+$.

Step 3: Preparation of (3-amino-2,6-difluorophenyl)(5-bromo-1H-pyrrolo[2,3-b]pyridin-3-yl)methanone

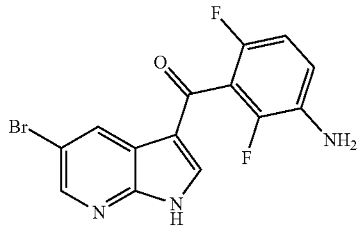

A mixture of (5-bromo-1H-pyrrolo[2,3-b]pyridin-3-yl)(2,6-difluoro-3-nitrophenyl)methanone (15.8 g, 40.8 mmol, 1.0 equiv), iron (12.0 g, 200.2 mmol, 4.9 equiv), ammonium chloride (7.2 g, 140.0 mmol), hydrochloric acid (50.0 mL) in ethanol (80 mL) and tetrahydrofuran (80 mL) was refluxed overnight. After cooling to room temperature, the mixture was filtered through a pad of Celite. The filtrate was concentrated in vacuo and the residue was purified by column chromatography on silica gel (petroleum ether/ethyl acetate=1/2) to give (3-amino-2,6-difluorophenyl)(5-bromo-1H-pyrrolo[2,3-b]pyridin-3-yl)methanone (8.6 g, 60% yield) as a yellow solid. LC/MS (ESI) m/z: 351.80 $[M+1]^+$.

Step 4: Preparation of (R)-3-fluoropyrrolidine-1-sulfonyl chloride

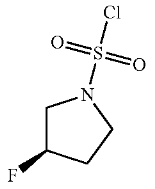

An oven dried flask was charged with (R)-3-fluoropyrrolidine hydrochloride (3.0 g, 24 mmol), triethylamine (7.2 g, 72 mmol) and dichloromethane (150 mL). The mixture was stirred for 15 min at room temperature and then cooled to about −30° C. in a dry ice/acetonitrile bath for 10 min. Sulfuryl chloride (6.0 g, 48 mmol) was added dropwise over 10 min. The reaction mixture was stirred at about −30° C. for an hour, then stirred at room temperature for 5 hours. The reaction mixture was diluted with aqueous HCl (1 N, 70 mL). The layers were separated and the aqueous layers were extracted with dichloromethane (50 mL×3). The combined organic layers were washed with aqueous HCl (1 N, 50 mL), washed with brine (50 mL), and dried over anhydrous sodium sulfate. The solvent was concentrated to give (R)-3-fluoropyrrolidine-1-sulfonyl chloride (4.5 g) as a white solid.

Step 5: Preparation of (R)—N-(3-(5-bromo-1H-pyrrolo[2,3-b]pyridine-3-carbonyl)-2,4-difluorophenyl)-3-fluoropyrrolidine-1-sulfonamide

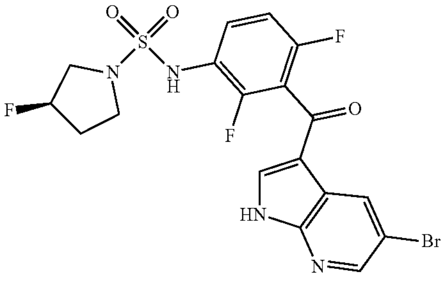 [SMILES: O=C(c1c(F)ccc(NS(=O)(=O)N2CC[C@@H](F)C2)c1F)c1c[nH]c2ncc(Br)cc12]

To a solution of (3-amino-2,6-difluorophenyl)(5-bromo-1H-pyrrolo[2,3-b]pyridin-3-yl)methanone (8.0 g, 22.79 mmol, 1.0 eq) in pyridine (25.0 g) was added (R)-3-fluoropyrrolidine-1-sulfonyl chloride (4.6 g, 24.60 mmol, 1.08 eq) and 4-dimethylaminopyridine (560.0 mg, 4.59 mmol, 0.2 eq). The reaction mixture was stirred for 12 h at 40° C. The solvent was removed and water (20 mL) was added. Aqueous sodium bicarbonate was added to adjust the pH=7~8 and then extracted with ethyl acetate (100 mL×2). The combined organic layers were washed with brine (50 mL×2), dried over anhydrous sodium sulfate. The solvent was removed under reduced pressure and the residue was purified by column chromatography on silica gel with ethyl acetate/petroleum ether (3:1) to give (R)—N-(3-(5-bromo-1H-pyrrolo[2,3-b]pyridine-3-carbonyl)-2,4-difluorophenyl)-3-fluoropyrrolidine-1-sulfonamide (6.4 g) as a yellow solid. LC/MS (ESI) m/z: 505.05 [M+1]$^+$.

Step 6: Preparation of (R)—N-(3-(5-bromo-1-((2-(trimethylsilyl)ethoxy)methyl)-1H-pyrrolo[2,3-b]pyridine-3-carbonyl)-2,4-difluorophenyl)-3-fluoro-N-((2-(trimethylsilyl)ethoxy)methyl)pyrrolidine-1-sulfonamide

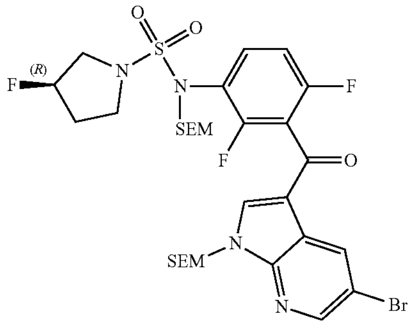

To a mixture of (3R)—N-[3-(5-bromo-1H-pyrrolo[2,3-b]pyridine-3-carbonyl)-2,4-difluoro-phenyl]-3-fluoro-pyrrolidine-1-sulfonamide (5.82 g, 11.56 mmol, 1 eq) in dimethylformamide (70 mL) was added sodium hydride (925 mg, 23.13 mmol, 60% purity in mineral oil, 2 eq) in portions at 0° C. The mixture was then stirred at 0~20° C. for 0.5 h. Then 2-(trimethylsilyl)ethoxymethyl chloride (4.24 g, 25.44 mmol, 4.5 mL, 2.2 eq) was added dropwise to the mixture at 20° C. The mixture was stirred at 50° C. for 1.5 h. Water (150 mL) was poured into the mixture and stirred for 1 min. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel column chromatography (petroleum ether/ethyl acetate=100/1, 10/1). The product (3R)—N-[3-[5-bromo-1-(2-trimethylsilylethoxymethyl) pyrrolo[2,3-b]pyridine-3-carbonyl]-2,4-difluoro-phenyl]-3-fluoro-N-(2-trimethylsilylethoxymethyl)pyrrolidine-1-sulfonamide (5.01 g, 6.51 mmol, 56% yield, 99% purity) was obtained as a light yellow oil. LC/MS (ESI) m/z: 765.0 [M+1]$^+$.

Step 7: Preparation of (R)—N-(2,4-difluoro-3-(5-(4,4,5,5-tetramethyl-1,3,2-dioxaborolan-2-yl)-1-((2-(trimethylsilyl)ethoxy)methyl)-1H-pyrrolo[2,3-b]pyridine-3-carbonyl)phenyl)-3-fluoro-N-((2-(trimethylsilyl)ethoxy)methyl)pyrrolidine-1-sulfonamide

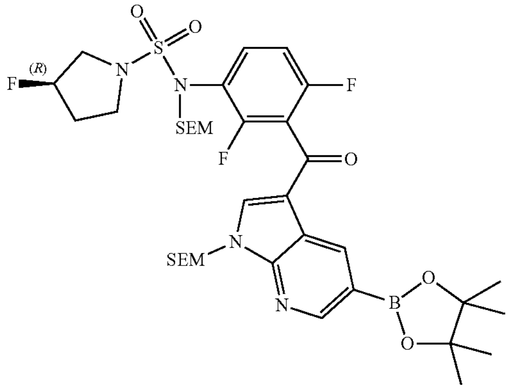

To a mixture of 4,4,5,5-tetramethyl-2-(4,4,5,5-tetramethyl-1,3,2-dioxaborolan-2-yl)-1,3,2-dioxaborolane (349 mg, 1.37 mmol, 1.05 eq) and (3R)—N-[3-[5-bromo-1-(2-trimethylsilyl ethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (1 g, 1.31 mmol, 1 eq) in dioxane (7 mL) was added potassium acetate (256.97 mg, 2.62 mmol, 2 eq) and [1,1'-bis(diphenylphosphino)]ferrocene dichloropalladium(II) (96 mg, 0.13 mmol, 0.1 eq) in one portion at 15° C. under nitrogen atmosphere. The mixture was stirred at 85° C. for 12 h. Water (50 mL) was poured into the mixture and stirred for 1 min. The aqueous phase was extracted with ethyl acetate (50 mL×3). The combined organic phase was washed with brine (50 mL×2), dried with anhydrous sodium sulfate, filtered and concentrated in vacuum. The residue was purified by silica gel column chromatography (petroleum ether/ethyl acetate=20/1, 3/1). The product (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (1.02 g, 1.22 mmol, 93% yield, 96% purity) was obtained as a colorless oil. LC/MS (ESI) m/z: 811.1 $[M+1]^+$.

Exemplary Synthesis of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 7)

Step 1: Preparation of tert-butyl (S)-(1-(4-bromophenyl)ethyl)carbamate

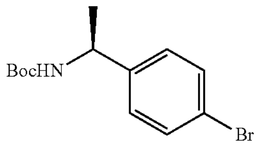 [SMILES: C[C@H](NC(=O)OC(C)(C)C)c1ccc(Br)cc1]

Into a 250-mL round-bottom flask, was placed (1S)-1-(4-bromophenyl)ethan-1-amine (10.0 g, 49.98 mmol, 1.00 equiv) in dichloromethane (100 mL), triethylamine (10.0 g, 99.01 mmol, 2.00 equiv), di-tert-butyl dicarbonate (13.0 g, 59.63 mmol, 1.20 equiv). The resulting solution was stirred for 2 h at room temperature. The resulting mixture was concentrated under vacuum. The residue was applied onto a silica gel column with ethyl acetate/petroleum ether (1:10). This resulted in 15.0 g of tert-butyl N-[(1S)-1-(4-bromophenyl)ethyl]carbamate as a white solid.

Step 2: Preparation of tert-butyl (S)-(1-(4-(4-methylthiazol-5-yl)phenyl)ethyl)carbamate

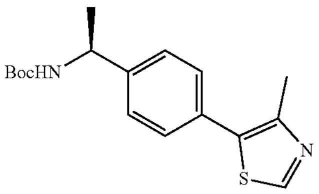 [SMILES: Cc1ncsc1-c1ccc([C@H](C)NC(=O)OC(C)(C)C)cc1]

Into a 250-mL round-bottom flask purged and maintained with an inert atmosphere of nitrogen, was placed a solution of tert-butyl N-[(1S)-1-(4-bromophenyl)ethyl]carbamate (15.0 g, 49.97 mmol, 1.00 equiv) in N,N-Dimethylacetamide (100 mL), 4-methyl-1,3-thiazole (9.9 g, 99.84 mmol, 2.00 equiv), potassium acetate (9.8 g, 99.86 mmol, 2.00 equiv), palladium(II) acetate (112.5 mg, 0.50 mmol, 0.01 equiv). The resulting solution was stirred for 2 h at 120° C. The reaction mixture was quenched by the addition of water (500 mL). The resulting solution was extracted with ethyl acetate (200 mL×3) and the organic layers combined and concentrated under vacuum. The residue was applied onto a silica gel column with ethyl acetate/petroleum ether (1:5). This resulted in 7.5 g (47%) of tert-butyl N-[(1S)-1-[4-(4-methyl-1,3-thiazol-5-yl)phenyl]ethyl]carbamate as a white solid. LC/MS (ESI) m/z: 319.13 $[M+Na]^+$.

Step 3: Preparation of (S)-1-(4-(4-methylthiazol-5-yl)phenyl)ethan-1-amine hydrochloride

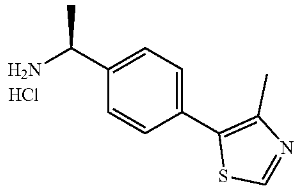

Into a 100-mL round-bottom flask, was placed a solution of tert-butyl N-[(1S)-1-[4-(4-methyl-1,3-thiazol-5-yl)phenyl]ethyl]carbamate (7.5 g, 23.55 mmol, 1.00 equiv) in methanol (20 mL), hydrogen chloride (gas) was bubbled in at room temperature. The resulting solution was stirred for 2 h at room temperature. The resulting mixture was concentrated under vacuum. This resulted in 4.4 g (86%) of (1S)-1-[4-(4-methyl-1,3-thiazol-5-yl)phenyl]ethan-1-amine as a white solid.

Step 4: Preparation of tert-butyl (2S,4R)-4-hydroxy-2-(((S)-1-(4-(4-methylthiazol-5-yl)phenyl)ethyl)carbamoyl)pyrrolidine-1-carboxylate

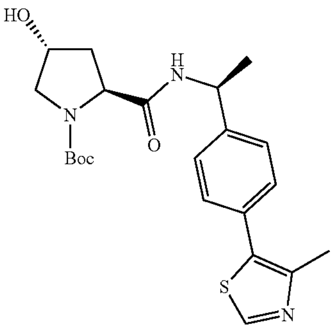 [SMILES: Cc1ncsc1-c1ccc([C@H](C)NC(=O)[C@@H]2C[C@@H](O)CN2C(=O)OC(C)(C)C)cc1]

Into a 100-mL round-bottom flask, was placed (2S,4R)-1-[(tert-butoxy)carbonyl]-4-hydroxypyrrolidine-2-carboxylic acid (4.7 g, 20.32 mmol, 1.00 equiv) in N,N-dimethylformamide (20 mL), N-ethyl-N-isopropylpropan-2-amine (7.8 g, 60.35 mmol, 3.00 equiv), o-(7-Azabenzotriazol-1-yl)-N,N,N',N'-te-tramethyluronium hexafluorophosphate (11.5 g, 30.26 mmol, 1.50 equiv), (1S)-1-[4-(4-methyl-1,3- thiazol-5-yl)phenyl]ethan-1-amine (4.4 g, 20.15 mmol, 1.00 equiv). The resulting solution was stirred for 12 h at room temperature. The reaction mixture was quenched by the addition of water (20 mL). The resulting solution was extracted with ethyl acetate (100 mL×3) and the organic layers combined and dried in an oven under reduced pressure, concentrated under vacuum. The residue was applied onto a silica gel column with ethyl acetate/petroleum ether (1:1). This resulted in 5.0 g (57%) of tert-butyl (2S,4R)-4-hydroxy-2-[[(1S)-1-[4-(4-methyl-1,3-thiazol-5-yl)phenyl]ethyl]carbamoyl]pyrrolidine-1-carboxylate as a yellow solid. LC/MS (ESI) m/z: 432.15 $[M+1]^+$.

Step 5: Preparation of (2S,4R)-4-hydroxy-N—((S)-1-(4-(4-methylthiazol-5-yl)phenyl)ethyl)pyrrolidine-2-carboxamide hydrochloride

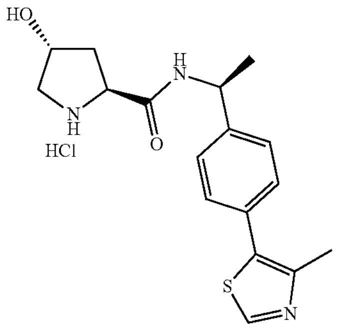 [SMILES: Cc1ncsc1-c1ccc([C@H](C)NC(=O)[C@@H]2C[C@@H](O)CN2)cc1 ; Cl]

Into a 500-mL round-bottom flask, was placed a solution of tert-butyl (2S,4R)-4-hydroxy-2-[[(1S)-1-[4-(4-methyl-1,3-thiazol-5-yl)phenyl]ethyl]carbamoyl]pyrrolidine-1-carboxylate (5.0 g, 11.59 mmol, 1.00 equiv) in methanol (200 mL), then hydrogen chloride (gas) was bubbled into the reaction mixture for 2 h at room temperature. The resulting mixture was concentrated under vacuum. This resulted in 3.2 g (83%) of (2S,4R)-4-hydroxy-N-[(1S)-1-[4-(4-methyl-1,3-thiazol-5-yl)phenyl]ethyl]pyrrolidine-2-carboxamide as a red solid.

Step 6: Preparation of tert-butyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate

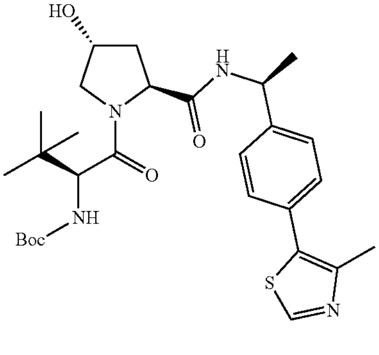 [SMILES: Cc1ncsc1-c1ccc([C@H](C)NC(=O)[C@@H]2C[C@@H](O)CN2C(=O)[C@@H](NC(=O)OC(C)(C)C)C(C)(C)C)cc1]

Into a 25-mL round-bottom flask, was placed (2S)-2-[(tert-butoxy)carbonyl]amino-3,3-dimethylbutanoic acid (2.0 g, 8.65 mmol, 0.99 equiv) in N,N-dimethylformamide (30 mL). N-ethyl-N-isopropylpropan-2-amine (3.4 g, 3.00 equiv), o-(7-Azabenzotriazol-1-yl)-N,N,N',N'-te-tramethyluronium hexafluorophosphate (5.0 g, 1.50 equiv), (2S,4R)-4-hydroxy-N-[(1S)-1-[4-(4-methyl-1,3-thiazol-5-yl)phenyl]ethyl]pyrrolidine-2-carboxamide hydrochloride (3.2 g, 8.70 mmol, 1.00 equiv). The resulting solution was stirred for 12 h at room temperature. The resulting solution was extracted with ethyl acetate (60 mL×3) and washed with water (100 mL×2). The organic layers combined and dried, concentrated under vacuum. The residue was applied onto a silica gel column with ethyl acetate/petroleum ether (1:3). This resulted in 4.0 g (84%) of tert-butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate as a yellow solid. LC/MS (ESI) m/z: 545.30 $[M+1]^+$.

Step 7: Preparation of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride

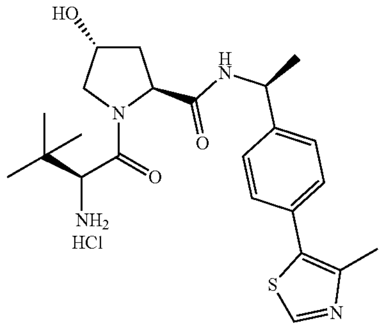 [SMILES: Cc1ncsc1-c1ccc([C@H](C)NC(=O)[C@@H]2C[C@@H](O)CN2C(=O)[C@@H](N)C(C)(C)C)cc1 ; Cl]

Into a 100-mL round-bottom flask, was placed a solution of tert-butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate (4.0 g, 7.34 mmol, 1.00 equiv) in methanol (30 mL), then hydrogen chloride (gas) was bubbled into the reaction mixture for 2 h at room temperature. The resulting mixture was concentrated under vacuum. This resulted in 3.5 g of (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride as a yellow solid. LC/MS (ESI) m/z: 445.05 $[M+1]^+$; $^1$H-NMR (400 MHz, DMSO-$d_6$) δ 8.99 (s, 1H), 8.57-8.55 (d, J=7.8 Hz, 1H), 8.01 (b, 3H), 7.46-7.43 (d, J=8.4 Hz, 2H), 7.39-7.37 (d, J=8.4 Hz, 2H), 4.98-4.90 (m, 1H), 4.57-4.51 (m, 1H), 4.34 (b, 1H), 3.94-3.92 (m, 1H), 3.69-3.66 (m, 1H), 3.53-3.49 (m, 1H), 2.52 (s, 3H), 2.10-2.07 (m, 1H), 1.83-1.81 (m, 1H), 1.40-1.30 (m, 3H), 1.03 (s, 9H).

Exemplary Synthesis of N-(2-methyl-5'-morpholino-6'-(piperidin-4-yloxy)-[3,3'-bipyridin]-5-yl)-3-(trifluoromethyl)benzamide hydrochloride (Intermediate 8)

Step 1: Preparation of 4-(5-bromo-2-fluoropyridin-3-yl)morpholine

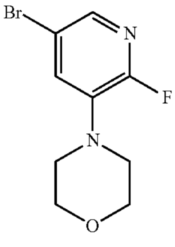

To the mixture of 5-bromo-2-fluoro-pyridin-3-amine (4 g, 20.94 mmol, 1 eq) in dimethyl formamide (40 mL) was added sodium hydride (2.51 g, 62.83 mmol, 60% in mineral oil, 3 eq) at 0° C. The mixture was stirred at 25° C. for 0.5 hour. Then 1-bromo-2-(2-bromoethoxy) ethane (7.29 g, 31.41 mmol, 3.94 mL, 1.5 eq) was added to the mixture. The mixture was stirred at 80° C. for 1.5 hours. The mixture was diluted with water (200 mL), extracted with ethyl acetate (70 mL×2). The combined organic layer was washed with water (100 mL×2), brine (100 mL), dried over anhydrous sodium sulfate, filtered and concentrated under reduced pressure to give a residue. The residue was purified by silica gel chromatography (petroleum ether:ethyl acetate=15:1 to 8:1). Compound 4-(5-bromo-2-fluoro-3-pyridyl)morpholine (3.4 g, 13.02 mmol, 62% yield) was obtained as a light green solid. $^1$H-NMR (400 MHz, $CDCl_3$) δ 7.80-7.79 (m, 1H), 7.33-7.30 (m, 1H), 3.87-3.82 (m, 4H), 3.13-3.08 (m, 4H).

Step 2: Preparation of 4-(2-fluoro-5-(4,4,5,5-tetramethyl-1,3,2-dioxaborolan-2-yl)pyridin-3-yl)morpholine

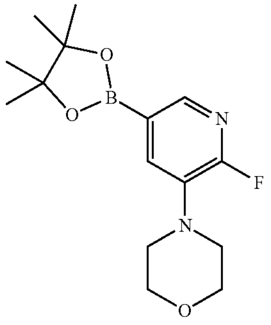 [SMILES: CC1(C)OB(c2cnc(F)c(N3CCOCC3)c2)OC1(C)C]

To the mixture of 4-(5-bromo-2-fluoro-3-pyridyl)morpholine (2.0 g, 7.66 mmol, 1 eq) and 4,4,5,5-tetramethyl-2-(4,4,5,5-tetramethyl-1,3,2-dioxaborolan-2-yl)-1,3,2-dioxaborolane (2.92 g, 11.49 mmol, 1.5 eq) in dioxane (25 mL) was added potassium acetate (2.26 g, 22.98 mmol, 3 eq) and 1,1'-bis(diphenylphosphino)ferrocene-palladium(ii)dichloride dichloromethane complex (625 mg, 0.76 mmol, 0.1 eq). The mixture was degassed and refilled with nitrogen for 3 times and stirred at 100° C. for 2 hr under nitrogen atmosphere. The mixture was filtered and concentrated under reduced pressure to give a crude product. The crude product was used into next step without further purification. Crude product 4-[2-fluoro-5-(4,4,5,5-tetramethyl-1,3,2-dioxaborolan-2-yl)-3-pyridyl]morpholine (5.0 g, crude) was obtained as a yellow oil. LC/MS (ESI) m/z: 309.1 $[M+1]^+$.

Step 3: Preparation of N-(6'-fluoro-2-methyl-5'-morpholino-[3,3'-bipyridin]-5-yl)-3-(trifluoromethyl)benzamide

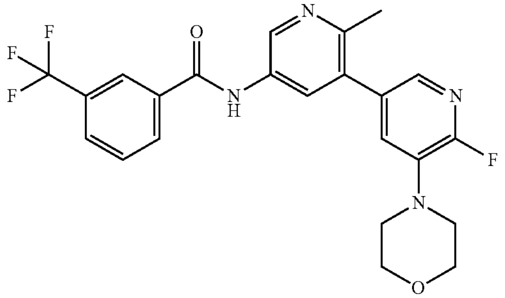 [SMILES: Cc1ncc(NC(=O)c2cccc(C(F)(F)F)c2)cc1-c1cnc(F)c(N2CCOCC2)c1]

To the mixture of N-(5-bromo-6-methyl-3-pyridyl)-3-(trifluoromethyl)benzamide (1.5 g, 4.18 mmol, 1 eq) and 4-[2-fluoro-5-(4,4,5,5-tetramethyl-1,3,2-dioxaborolan-2-yl)-3-pyridyl]morpholine (2.70 g, 8.77 mmol, 2.1 eq) in dioxane (15 mL) was added potassium carbonate (1.73 g, 12.53 mmol, 3 eq), 1,1'-bis(diphenylphosphino)ferrocene-palladium(ii)dichloride dichloromethane complex (341 mg, 0.41 mmol, 0.1 eq) and water (3 mL). The mixture was degassed and refilled with nitrogen for 3 times. Then it was stirred at 100° C. for 4 hr under nitrogen atmosphere. The mixture was concentrated under reduced pressure to give a residue. The residue was purified by silica gel chromatography (petroleum ether:ethyl acetate=3:2 to 1:4). Compound N-[5-(6-fluoro-5-morpholino-3-pyridyl)-6-methyl-3-pyridyl]-3-(trifluoromethyl)benzamide (1.3 g, 2.82 mmol, 67% yield) was obtained as a yellow solid. $^1$H-NMR (400 MHz, $CDCl_3$) δ 8.63 (d, J=2.4 Hz, 1H), 8.32 (s, 1H), 8.20 (d, J=3.2 Hz, 1H), 8.15 (s, 1H), 7.85-7.83 (m, 1H), 7.76-7.74 (m, 1H), 7.66 (t, J=8.0 Hz, 1H), 7.24-7.20 (m, 1H), 3.91-3.89 (m, 4H), 3.18-3.16 (m, 4H), 2.49 (s, 3H).

Step 4: Preparation of tert-butyl 4-((2'-methyl-5-morpholino-5'-(3-(trifluoromethyl)benzamido)-[3,3'-bipyridin]-6-yl)oxy)piperidine-1-carboxylate

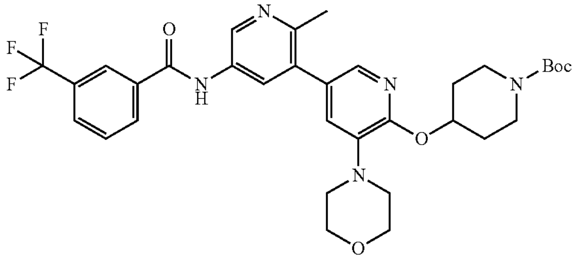 [SMILES: Cc1ncc(NC(=O)c2cccc(C(F)(F)F)c2)cc1-c1cnc(OC2CCN(C(=O)OC(C)(C)C)CC2)c(N2CCOCC2)c1]

To a mixture of tert-butyl 4-hydroxypiperidine-1-carboxylate (2.62 g, 13.03 mmol, 1.5 eq) in dimethylformamide (100 mL) was added sodium hydride (764 mg, 19.11 mmol, 60% purity, 2.2 eq) at 15° C. The mixture stirred at 15° C. for 0.5 hr and N-[5-(6-fluoro-5-morpholino-3-pyridyl)-6-methyl-3-pyridyl]-3-(trifluoromethyl)benzamide (4 g, 8.69 mmol, 1 eq) was added to the reaction mixture and stirred at 80° C. for 2 hr. The mixture was quenched by addition water (200 mL), diluted with ethyl acetate (20 mL) and extracted with ethyl acetate (40 mL×4), the combined organic phase washed with brine (50 mL), dried over anhydrous sodium sulfate, filtered and concentrated under reduced pressure. The residue was triturated with petroleum ether/ethyl acetate (V/V=5:1, 30 mL) and collected by filtration. Compound tert-butyl 4-[[5-[2-methyl-5-[[3-(trifluoromethyl)benzoyl]amino]-3-pyridyl]-3-morpholino-2-pyridyl]oxy]piperidine-1-carboxylate (4.5 g, 7.01 mmol, 80% yield) as a brown solid was obtained. LC/MS (ESI) m/z: 642.2 $[M+1]^+$; $^1$H-NMR (400 MHz, $CDCl_3$) δ 8.64 (d, J=2.4 Hz, 1H), 8.23-8.09 (m, 4H), 7.86 (d, J=7.6 Hz, 1H), 7.78 (d, J=1.8 Hz, 1H), 7.72-7.63 (m, 1H), 7.07 (d, J=1.7 Hz, 1H), 5.48-5.34 (m, 1H), 3.96-3.86 (m, 4H), 3.78-3.66 (m, 2H), 3.52-3.39 (m, 2H), 3.16 (s, 4H), 2.54 (s, 3H), 2.12-2.03 (m, 2H), 1.86 (m, 2H), 1.51 (s, 9H).

Step 5: Preparation of N-(2-methyl-5'-morpholino-6'-(piperidin-4-yloxy)-[3,3'-bipyridin]-5-yl)-3-(trifluoromethyl)benzamide hydrochloride

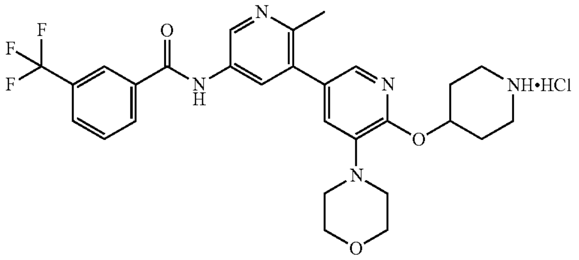

To a mixture of tert-butyl 4-[[5-[2-methyl-5-[[3-(trifluoromethyl)benzoyl]amino]-3-pyridyl]-3-morpholino-2-pyridyl]oxy]piperidine-1-carboxylate (4.5 g, 7.01 mmol, 1 eq) in dichloromethane (100 mL) was added hydrogen chloride/dioxane (4 M, 17 mL, 10 eq). The mixture stirred at 15° C. for 1 hr. The mixture was concentrated under reduced pressure. Compound N-[6-methyl-5-[5-morpholino-6-(4-piperidyloxy)-3-pyridyl]-3-pyridyl]-3-(trifluoromethyl)benzamide (4.5 g, crude, hydrochloride) as a brown solid was obtained. LC/MS (ESI) m/z: 542.2 $[M+1]^+$.

Exemplary Synthesis of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (Intermediate 9)

Step 1: Preparation of 4-(4-methylthiazol-5-yl)benzonitrile

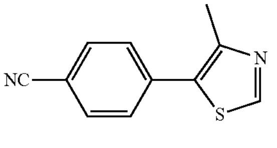

Into a 1-L round-bottom flask purged and maintained with an inert atmosphere of nitrogen, was placed a solution of 4-bromobenzonitrile (20 g, 109.88 mmol, 1.00 equiv) in DMA (250 mL), 4-methyl-1,3-thiazole (21.88 g, 220.67 mmol, 2.00 equiv), $Pd(OAc)_2$ (743 mg, 3.31 mmol, 0.03 equiv) and KOAc (21.66 g, 220.71 mmol, 2.00 equiv). The resulting solution was stirred for 5 h at 150° C. The reaction mixture was cooled with a water/ice bath and diluted with 1 L of water. The resulting solution was extracted with 3×300 mL of ethyl acetate. The combined organic layers were washed with 3×300 mL of water and 1×300 mL of brine, then dried over anhydrous sodium sulfate and concentrated under vacuum. The residue was purified on combi-flash with ethyl acetate/petroleum ether (1:100-1:5). This resulted in 20 g (91%) of 4-(4-methyl-1,3-thiazol-5-yl)benzonitrile as a beige solid.

Step 2: Preparation of (4-(4-methylthiazol-5-yl)phenyl)methanamine

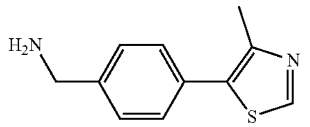

Into a 3-L 3-necked round-bottom flask purged and maintained with an inert atmosphere of nitrogen, was placed 4-(4-methyl-1,3-thiazol-5-yl)benzonitrile (35 g, 174.77 mmol, 1.00 equiv) in tetrahydrofuran (1000 mL). This was followed by the addition of $LiAlH_4$ (20 g, 526.32 mmol, 3.00 equiv) in portions at 0° C. in 10 min. The resulting solution was stirred for 3 h at 60° C. in an oil bath. The reaction was cooled to 0° C. with a water/ice bath, then quenched by the addition of 20 mL of water, 20 mL of NaOH (15%) and 60 mL of water. The resulting solution was diluted with 200 mL of ethyl acetate. The solids were filtered out. The filtrate was dried over anhydrous sodium sulfate and concentrated under vacuum. The residue was applied onto a silica gel column with dichloromethane/methanol (10:1). This resulted in 20 g (56%) of [4-(4-methyl-1,3-thiazol-5-yl)phenyl]methanamine as yellow oil.

Step 3: Preparation of tert-butyl (2S,4R)-4-hydroxy-2-((4-(4-methylthiazol-5-yl)benzyl)carbamoyl)pyrrolidine-1-carboxylate

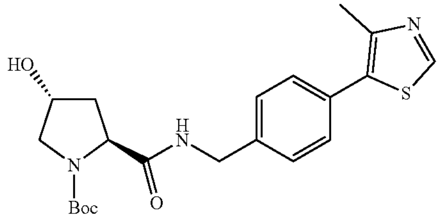 [SMILES: Cc1ncsc1-c1ccc(CNC(=O)[C@@H]2C[C@@H](O)CN2C(=O)OC(C)(C)C)cc1]

Into a 50-mL round-bottom flask, was placed (2S,4R)-1-[(tert-butoxy)carbonyl]-4-hydroxypyrrolidine-2-carboxylic acid (2.7 g, 11.68 mmol, 1.20 equiv) in N,N-dimethylformamide (30 mL), DIEA (2.52 g, 19.50 mmol, 1.20 equiv), HATU (4.47 g, 11.76 mmol, 1.20 equiv), [4-(4-methyl-1,3-thiazol-5-yl)phenyl]methanamine (2 g, 9.79 mmol, 1.00 equiv). The resulting solution was stirred overnight at 25° C. The reaction was then quenched by the addition of 20 mL of water and extracted with 3×20 mL of ethyl acetate. The organic layers combined, dried over anhydrous sodium sulfate and concentrated under vacuum. The residue was applied onto a silica gel column with dichloromethane/methanol (20:1). This resulted in 1 g (24%) of tert-butyl (2S,4R)-4-hydroxy-2-([[4-(4-methyl-1,3-thiazol-5-yl)phenyl]methyl]carbamoyl)pyrrolidine-1-carboxylate as a yellow solid.

Step 4: Preparation of (2S,4R)-4-hydroxy-N-(4-(4-methylthiazol-5-yl)benzyl)pyrrolidine-2-carboxamide hydrochloride

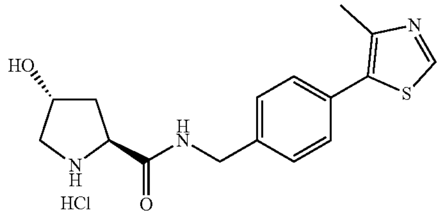 [SMILES: Cc1ncsc1-c1ccc(CNC(=O)[C@@H]2C[C@@H](O)CN2)cc1 ; Cl]

Into a 1000-mL round-bottom flask, was placed tert-butyl (2S,4R)-4-hydroxy-2-([[4-(4-methyl-1,3-thiazol-5-yl)phenyl]methyl]carbamoyl)pyrrolidine-1-carboxylate (45 g, 107.78 mmol, 1.00 equiv), a solution of hydrogen chloride (13.44 L) in dioxane (300 mL). The resulting solution was stirred for 2 h at 20° C. The solids were collected by filtration. This resulted in 37.3 g (98%) of (2S,4R)-4-hydroxy-N-[[4-(4-methyl-1,3-thiazol-5-yl)phenyl]methyl]pyrrolidine-2-carboxamide hydrochloride as a yellow solid.

Step 5: Preparation of tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate

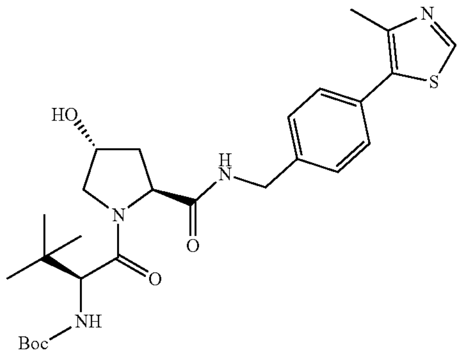 [SMILES: Cc1ncsc1-c1ccc(CNC(=O)[C@@H]2C[C@@H](O)CN2C(=O)[C@@H](NC(=O)OC(C)(C)C)C(C)(C)C)cc1]

Into a 1000-mL round-bottom flask, was placed (2S)-2-[[(tert-butoxy)carbonyl]amino]-3,3-dimethylbutanoic acid (15.73 g, 68.01 mmol, 1.20 equiv) in N,N-dimethylformamide (500 mL), DIEA (29.2 g, 225.94 mmol, 4.00 equiv), HATU (25.9 g, 68.12 mmol, 1.20 equiv) and (2S,4R)-2-amino-5-chloro-4-hydroxy-N-[[4-(4-methyl-1,3-thiazol-5-yl)phenyl]methyl]pentanamide (20 g, 56.52 mmol, 1.00 equiv). The resulting solution was stirred 16 h at 20° C. The reaction was then quenched by the addition of 200 mL of water and extracted with 3×100 mL of ethyl acetate. The combined organic layers were dried over anhydrous sodium sulfate and concentrated under vacuum. The residue was applied onto a silica gel column with ethyl acetate/petroleum ether (2:1). This resulted in 15.2 g (51%) of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate as a yellow solid.

Step 6: Preparation of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride

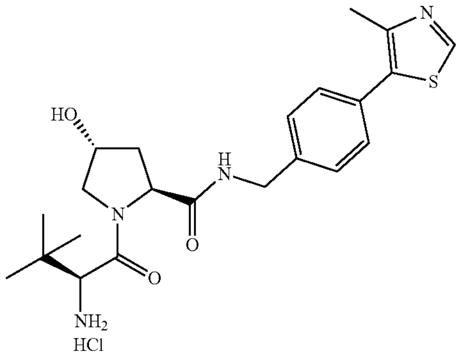 [SMILES: Cc1ncsc1-c1ccc(CNC(=O)[C@@H]2C[C@@H](O)CN2C(=O)[C@@H](N)C(C)(C)C)cc1 ; Cl]

Into a 500-mL round-bottom flask, was placed tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol, 1.00 equiv) in dioxane (20 mL) and a solution of hydrogen chloride (3.584 L) in dioxane (80 mL). The resulting solution was stirred for 2 h at 25° C. The solids were collected by filtration. This resulted in 5.1 g (48%) of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride as a yellow solid. LC/MS (ESI) m/z: 431 $[M+1]^+$; $^1$H-NMR (400 MHz, $CD_3OD$) δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H).

Exemplary Synthesis of tert-butyl 2-(4-((4-(4-(4,4,5,5-tetramethyl-1,3,2-dioxaborolan-2-yl)phenyl)piperazin-1-yl)methyl)piperidin-1-yl)acetate (Intermediate 10)

Step 1: Preparation of tert-butyl 4-((4-(4-bromophenyl)piperazin-1-yl)methyl)piperidine-1-carboxylate

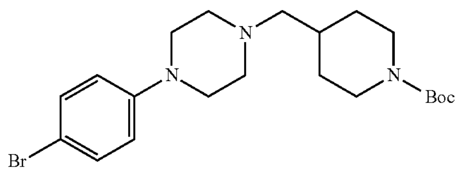 [SMILES: CC(C)(C)OC(=O)N1CCC(CN2CCN(c3ccc(Br)cc3)CC2)CC1]

Into a 100-mL round-bottom flask, was placed a solution of 1-(4-bromophenyl)piperazine hydrochloride (900.0 mg, 3.26 mmol, 1.00 equiv) in dichloromethane (20 mL). DIEA (841.0 mg, 6.52 mmol, 2.00 equiv) and tert-butyl 4-formylpiperidine-1-carboxylate (694.4 mg, 3.26 mmol, 1.00 equiv) was added. A few minutes later sodium triacetoxyborohydride (2.1 g, 9.78 mmol, 3.00 equiv) was added. The resulting solution was stirred for 1 h at room temperature. The reaction was then quenched by water (30 mL), extracted with dichloromethane (30 mL×2). The organic phase was evaporated concentrated under reduced pressure and the residue was applied onto a silica gel column with ethyl acetate/petroleum ether (1:4). This resulted in 1.3 g (91%) of tert-butyl 4-((4-(4-bromophenyl)piperazin-1-yl)methyl)piperidine-1-carboxylate as a white solid. LC/MS (ESI) m/z: 438.30 [M+1]$^+$.

Step 2: Preparation of 1-(4-bromophenyl)-4-(piperidin-4-ylmethyl)piperazine

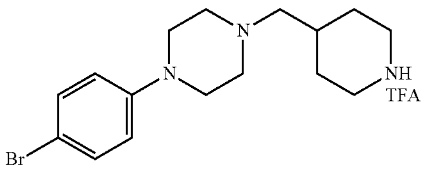 [SMILES: Brc1ccc(N2CCN(CC3CCNCC3)CC2)cc1]

Into a 100-mL round-bottom flask, was placed a solution of tert-butyl 4-((4-(4-bromophenyl)piperazin-1-yl)methyl)piperidine-1-carboxylate (1.3 g, 0.64 mmol, 1.00 equiv), 2,2,2-trifluoroacetaldehyde (5 ml) in dichloromethane (10 mL). The resulting solution was stirred for 2 h at room temperature. The resulting mixture was concentrated under reduced pressure. This resulted in 1.3 g (97%) of 1-(4-bromophenyl)-4-(piperidin-4-ylmethyl)piperazine compound with 2,2,2-trifluoroacetic acid (1:1) as a white solid. LC/MS (ESI) m/z: 338.05 [M+1]$^+$.

Step 3: Preparation of tert-butyl 2-(4-((4-(4-bromophenyl)piperazin-1-yl)methyl)piperidin-1-yl)acetate

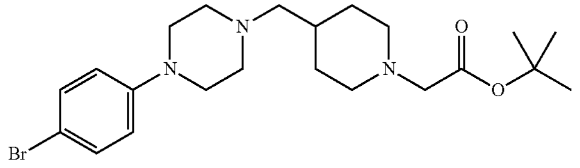 [SMILES: CC(C)(C)OC(=O)CN1CCC(CN2CCN(c3ccc(Br)cc3)CC2)CC1]

Into a 100-mL round-bottom flask, was placed a solution of 1-(4-bromophenyl)-4-(piperidin-4-ylmethyl)piperazine compound with 2,2,2-trifluoroacetic acid (1:1) (1.3 g, 2.88 mmol, 1.00 equiv) in THF (20 mL). Sodium hydroxide (1 M, 10 mL), tert-butyl 2-bromoacetate (782.2 mg, 4.03 mmol, 1.40 equiv) was added. The resulting solution was stirred for 30 minutes at 0° C. in an ice bath. The resulting solution was diluted with water (40 mL), extracted with ethyl acetate (40 mL×2). The organic phase was evaporated concentrated under reduced pressure and the residue was applied onto a silica gel column with ethyl acetate/petroleum ether (2:3). This resulted in 983.4 mg (76%) of tert-butyl 2-(4-((4-(4-bromophenyl)piperazin-1-yl)methyl)piperidin-1-yl)acetate as a white solid. LC/MS (ESI) m/z: 452.15 [M+1]$^+$.

Step 4: Preparation of tert-butyl 2-(4-((4-(4-(4,4,5,5-tetramethyl-1,3,2-dioxaborolan-2-yl)phenyl)piperazin-1-yl)methyl)piperidin-1-yl)acetate

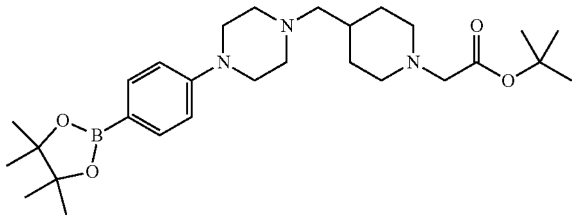 [SMILES: CC(C)(C)OC(=O)CN1CCC(CN2CCN(c3ccc(B4OC(C)(C)C(C)(C)O4)cc3)CC2)CC1]

Into a 100-mL round-bottom flask, was placed a solution of tert-butyl 2-(4-((4-(4-bromophenyl)piperazin-1-yl)methyl)piperidin-1-yl)acetate (983.4 mg, 2.18 mmol, 1.00 equiv), 4,4,4',4',5,5,5',5'-octamethyl-2,2'-bi(1,3,2-dioxaborolane) (1.1 g, 4.36 mmol, 2.00 equiv), Pd(dppf)$Cl_2$ (358.1 mg, 0.44 mmol, 0.20 equiv), potassium acetate (641.0 g, 6.54 mmol, 3.00 equiv) in 1,4-dioxane (30 mL). Under nitrogen the resulting solution was stirred overnight at 85° C. in an oil bath. The solids were filtered out. The filtrate was evaporated concentrated under reduced pressure and the residue was applied onto a silica gel column with ethyl acetate/petroleum ether (1:1). This resulted in 783.4 mg (72%) of tert-butyl 2-(4-((4-(4-(4,4,5,5-tetramethyl-1,3,2-dioxaborolan-2-yl)phenyl)piperazin-1-yl)methyl)piperidin-1-yl)acetate as a yellow solid. LC/MS (ESI) m/z: 500.30 [M+1]$^+$.

Exemplary Synthesis of (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Example 320)

Step 1: Preparation of tert-butyl 4-(4-(4-bromophenyl)piperazin-1-yl)piperidine-1-carboxylate

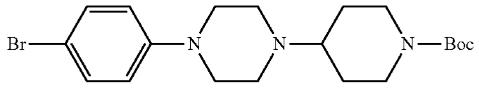 [SMILES: CC(C)(C)OC(=O)N1CCC(N2CCN(c3ccc(Br)cc3)CC2)CC1]

Into a 250 mL round-bottom flask, was placed a solution of 1-(4-bromophenyl)piperazine hydrochloride (5.0 g, 18.0 mmol, 1.0 equiv) in dichloromethane (10 mL), tert-butyl 4-oxopiperidine-1-carboxylate (4.9 g, 24.9 mmol, 1.4 equiv), acetyl ethaneperoxoate; sodioboranyl acetate (13.2 g, 62.3 mmol, 3.5 equiv). The resulting solution was stirred overnight at room temperature. The reaction was then quenched by the addition of 1 mL of water/ice. The resulting solution was extracted with dichloromethane (20 mL×2) and the organic layers combined and dried over anhydrous sodium sulfate and concentrated under vacuum. The residue was applied onto a silica gel column with ethyl acetate/petroleum ether (1:0). This resulted in 4.2 g (54%) of tert-butyl 4-[4-(4-bromophenyl) piperazin-1-yl]piperidine-1-carboxylate as a white solid. LC/MS (ESI) m/z: 426.10 [M+1]$^+$.

Step 2: Preparation of 1-(4-bromophenyl)-4-(piperidin-4-yl)piperazine hydrochloride

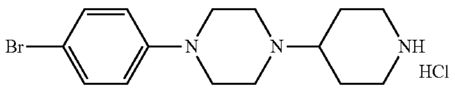 [SMILES: Brc1ccc(N2CCN(C3CCNCC3)CC2)cc1 ; Cl]

Into a 100 mL round-bottom flask, was placed a solution of tert-butyl 4-[4-(4-bromophenyl)piperazin-1-yl]piperidine-1-carboxylate (4.2 g, 9.8 mmol, 1.0 equiv) in dichloromethane (10 mL), hydrogen chloride (5 ml). The resulting solution was stirred for 1 h at room temperature. The resulting mixture was concentrated under vacuum. This resulted in 3.0 g (85%) of 1-(4-bromophenyl)-4-(piperidin-4-yl)piperazine hydrochloride as a white solid. LC/MS (ESI) m/z: 325.95 $[M+1]^+$.

Step 3: Preparation of tert-butyl 2-(4-(4-(4-bromophenyl)piperazin-1-yl)piperidin-1-yl)acetate

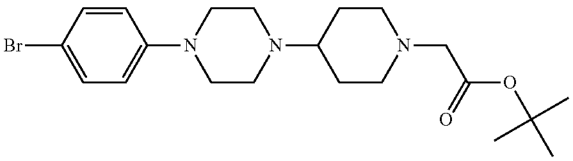 [SMILES: CC(C)(C)OC(=O)CN1CCC(N2CCN(c3ccc(Br)cc3)CC2)CC1]

Into a 100 mL round-bottom flask, was placed a solution of 1-(4-bromophenyl)-4-(piperidin-4-yl)piperazine hydrochloride (3.0 g, 8.3 mmol, 1.0 equiv) in dichloromethane (10 mL), triethylamine (2.0 g, 19.8 mmol, 2.4 equiv), tert-butyl 2-bromoacetate (2.3 g, 11.8 mmol, 1.4 equiv). The resulting solution was stirred overnight at room temperature. The reaction was then quenched by the addition of 1 mL of water/ice. The resulting solution was extracted with dichloromethane (20 mL×2) and the organic layers combined and dried over anhydrous sodium sulfate and concentrated under vacuum. The residue was applied onto a silica gel column with ethyl acetate/petroleum ether (1:0). This resulted in 2.0 g (53%) of tert-butyl 2-[4-[4-(4-bromophenyl) piperazin-1-yl]piperidin-1-yl]acetate as a white solid. LC/MS (ESI) m/z: 440.30 $[M+1]^+$.

Step 4: Preparation of tert-butyl 2-(4-(4-(4-(4,4,5,5-tetramethyl-1,3,2-dioxaborolan-2-yl)phenyl)piperazin-1-yl)piperidin-1-yl)acetate

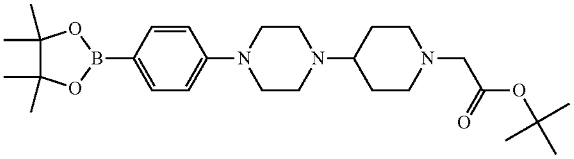 [SMILES: CC(C)(C)OC(=O)CN1CCC(N2CCN(c3ccc(B4OC(C)(C)C(C)(C)O4)cc3)CC2)CC1]

Into a 20-30-mL sealed tube, was placed a solution of tert-butyl 2-[4-[4-(4-bromophenyl)piperazin-1-yl]piperidin-1-yl]acetate (2.0 g, 4.5 mmol, 1.0 equiv) in dioxane (10 mL), 4,4,5,5-tetramethyl-2-(4,4,5,5-tetramethyl-1,3,2-dioxaborolan-2-yl)-1,3,2-dioxaborolane (2.3 g, 9.1 mmol, 2.0 equiv), KOAc (874.6 mg, 8.9 mmol, 2.0 equiv), $Pd(dppf)Cl_2$ (700.6 mg, 0.9 mmol, 0.2 equiv). The resulting solution was stirred overnight at 85° C. in an oil bath. The reaction was then quenched by the addition of 1 mL of water/ice. The resulting solution was extracted with ethyl acetate (20 ml×2) and the organic layers combined and dried over anhydrous sodium sulfate and concentrated under vacuum. The residue was applied onto a silica gel column with ethyl acetate/petroleum ether (1:0). This resulted in 630.0 mg (29%) of tert-butyl 2-(4-[4-[4-(4, 4, 5, 5-tetramethyl-1,3, 2-dioxaborolan-2-yl) phenyl]piperazin-1-yl]piperidin-1-yl)acetate as a black solid. LC/MS (ESI) m/z: 486.25 $[M+1]^+$.

Step 5: Preparation of tert-butyl (R)-2-(4-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)piperidin-1-yl)acetate

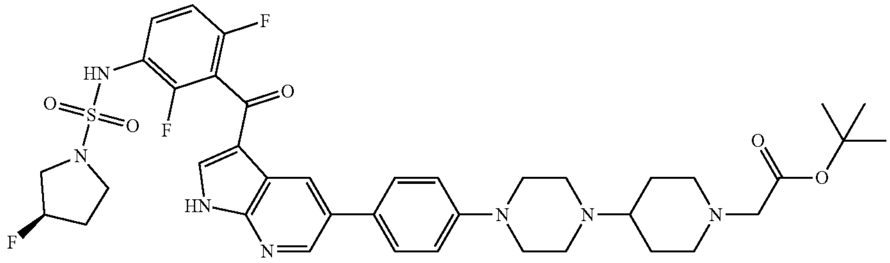 [SMILES: CC(C)(C)OC(=O)CN1CCC(N2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 20-30 mL sealed tube, was placed a solution of tert-butyl 2-(4-[4-[4-(4,4,5,5-tetramethyl-1,3,2-dioxaborolan-2-yl)phenyl]piperazin-1-yl]piperidin-1-yl)acetate (630.0 mg, 1.3 mmol, 1.0 equiv) in dioxane/$H_2O$ (4:1 mL), (3R)—N-(3-5-bromo-1H-pyrrolo[2,3-b]pyridine-3-carbonyl-2,4-difluorophenyl)-3-fluoropyrrolidine-1-sulfonamide (300.0 mg, 0.6 mmol, 0.5 equiv), $Pd(dppf)Cl_2$ (46.9 mg), sodium carbonate (99.2 mg, 0.9 mmol, 0.7 equiv). The resulting solution was stirred for 2 h at 105° C. The reaction was then quenched by the addition of 1 mL of water/ice. The resulting solution was extracted with ethyl acetate (20 mL×2) and the organic layers combined and dried over anhydrous sodium sulfate and concentrated under vacuum. The residue was applied onto a silica gel column with dichloromethane/methanol (10:1). This resulted in 256.0 mg (25%) of tert-butyl 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetate as a yellow solid. LC/MS (ESI) m/z: 782.05 $[M+1]^+$.

Step 6: Preparation of (R)-2-(4-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)piperidin-1-yl)acetic acid

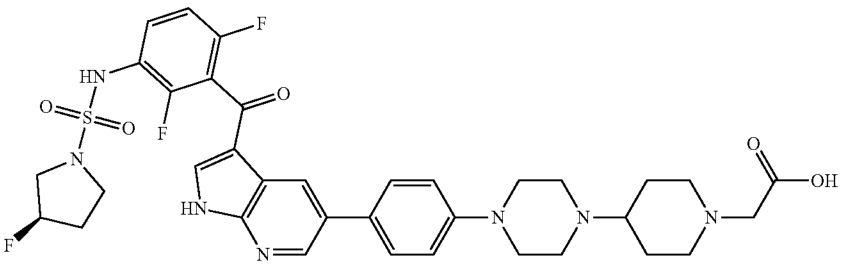 [SMILES: O=C(O)CN1CCC(N2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 100 mL round-bottom flask, was placed a solution of tert-butyl 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetate (256.0 mg, 0.3 mmol, 1.0 equiv) in dichloromethane (10 mL), trifluoroacetic acid (2 mL). The resulting solution was stirred overnight at room temperature. The resulting mixture was concentrated under vacuum. This resulted in 120.0 mg (50%) of 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetic acid as a yellow solid. LC/MS (ESI) m/z: 726.15 $[M+1]^+$.

Step 7: Preparation of (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

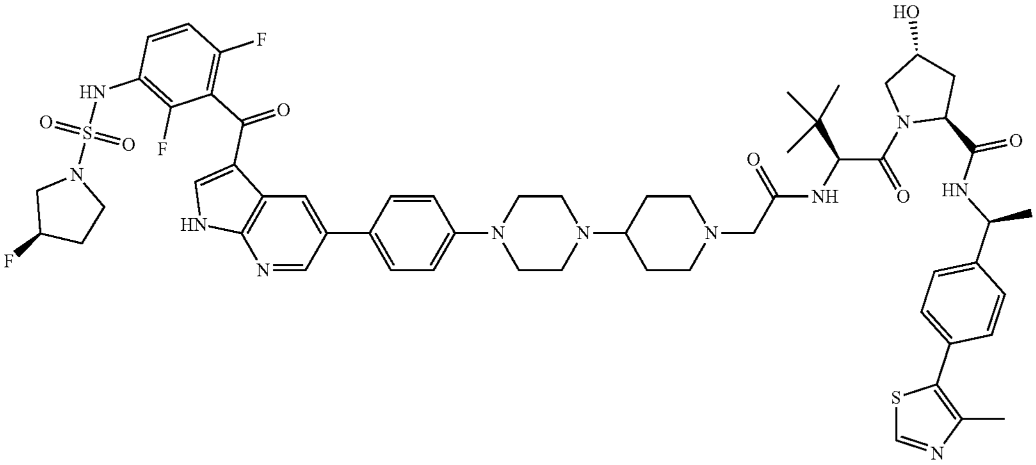 [SMILES: Cc1ncsc1-c1ccc([C@H](C)NC(=O)[C@@H]2C[C@@H](O)CN2C(=O)[C@@H](NC(=O)CN2CCC(N3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 100 mL round-bottom flask, was placed a solution of 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetic acid (120.0 mg, 0.3 mmol, 1.0 equiv) in N,N-dimethylformamide (5 mL), (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide (88.2 mg, 0.4 mmol, 1.2 equiv), N,N-Diisopropylethylamine (64.1 mg, 1.0 mmol, 3.0 equiv), (Benzotriazole-1-yloxy) tris(dimethylamino) phosphonium hexafluorophosphate (87.8 mg). The resulting solution was stirred for 1 h at room temperature. The reaction was then quenched by the addition of 1 mL of water/ice. The resulting solution was extracted with ethyl acetate (20 mL×2) and the organic layers combined and dried over anhydrous sodium sulfate and concentrated under vacuum. The crude product was purified by Prep-HPLC resulting in 42.9 mg (23%) of (2S,4R)-1-[(2S)-2-(2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetamido)-3,3-dimethylbutanoyl]-4-hydroxy-N-[(1S)-1-[4-(4-methyl-1,3-thiazol-5-yl)phenyl]ethyl]pyrrolidine-2-carboxamide as an off-white solid. LC/MS (ESI) m/z: 1152.20 $[M+1]^+$; $^1$H-NMR (400 MHz, DMSO-$d_6$) δ 12.87 (brs, 1H), 9.96 (brs, 1H), 8.96 (d, J=2.1 Hz, 1H), 8.63 (d, J=2.3 Hz, 1H), 8.51 (s, 1H), 8.40 (d, J=7.6 Hz, 1H), 8.04 (s, 1H), 7.74 (d, J=9.6 Hz, 1H), 7.70-7.60 (m, 3H), 7.47-7.42 (m, 2H), 7.40-7.31 (m, 2H), 7.23 (t, J=8.9 Hz, 1H), 7.05 (d, J=8.5 Hz, 2H), 5.36-5.15 (m, 1H), 5.19 (s, 1H), 4.88 (t, J=7.1 Hz, 1H), 4.54-4.38 (m, 2H), 4.27-4.21 (m, 1H), 3.60-3.52 (m, 2H), 3.47-3.41 (m, 1H), 3.37-3.31 (m, 2H), 3.30-3.24 (m, 5H), 3.03 (d, J=16.1 Hz, 1H), 2.89-2.80 (m, 3H), 2.70-2.55 (m, 5H), 2.34-2.03 (m, 7H), 1.87-1.72 (m, 3H), 1.47-1.37 (m, 6H), 0.93 (s, 9H).

Exemplary Synthesis of (2S,4R)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Example 360)

Step 1: Preparation of tert-butyl bis(2-hydroxypropyl)carbamate

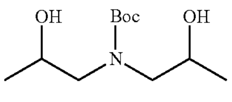 [SMILES: CC(O)CN(CC(C)O)C(=O)OC(C)(C)C]

To a solution of 1-(2-hydroxypropylamino)propan-2-ol (10 g, 75.08 mmol, 10 mL, 1 eq) in tetrahydrofuran (200 mL) was added Boc-anhydride (17.2 g, 78.84 mmol, 18 mL, 1.05 eq) and triethylamine (22.8 g, 225.25 mmol, 31.3 mL, 3 eq). The mixture was stirred at 15° C. for 12 hours. Water (400 mL) was poured into the mixture and stirred for 1 minute. The aqueous phase was extracted with ethyl acetate (200 mL×3). The combined organic phase was washed with brine (100 mL×2), dried with anhydrous sodium sulfate, filtered and concentrated in vacuum. The residue was purified by silica gel chromatography (petroleum ether:ethyl acetate=10:1 to 2:1) to give tert-butyl N,N-bis(2-hydroxypropyl)carbamate (14.7 g, 63.01 mmol, 83% yield) as a white solid. LC/MS (ESI) m/z: 256.1 $[M+23]^+$.

Step 2: Preparation of tert-butyl bis(2-oxopropyl)carbamate

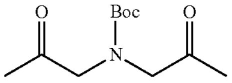 [SMILES: CC(=O)CN(CC(C)=O)C(=O)OC(C)(C)C]

To a solution of oxalyl chloride (16.3 g, 128.5 mmol, 3 eq) in dichloromethane (100 mL) was added a solution of dimethylsulfoxide (13.4 g, 171.45 mmol, 4 eq) in dichloromethane (100 mL) dropwise at −70° C. The mixture was stirred at −70° C. for 0.5 hour. A solution of tert-butyl N,N-bis(2-hydroxypropyl)carbamate (10 g, 42.86 mmol, 1 eq) in dichloromethane (100 mL) was added into to the mixture dropwise and the mixture was stirred at −70° C. for another 0.5 hours. Then triethylamine (21.7 g, 214.31 mmol, 5 eq) was added to the reaction mixture at −70° C. The mixture was allowed warm to 15° C. and stirred at 15° C. for 2 hours. The reaction mixture was diluted with water (500 mL) and extracted with dichloromethane (300 mL×2). The combined organic phase was washed with saturated brine (300 mL×2), dried with anhydrous sodium sulfate, filtered and concentrated in vacuum. The residue was purified by silica gel chromatography (petroleum ether:ethyl acetate=10:1 to 2:1) to give tert-butyl N,N-diacetonylcarbamate (6.4 g, 27.91 mmol, 65% yield) as an colorless oil.

Step 3: Preparation of tert-butyl 4-(4-bromophenyl)-3,5-dimethylpiperazine-1-carboxylate

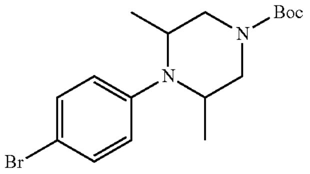 [SMILES: CC1CN(C(=O)OC(C)(C)C)CC(C)N1c1ccc(Br)cc1]

To a solution of tert-butyl N,N-diacetonylcarbamate (6.4 g, 27.91 mmol, 1.2 eq) and 4-bromoaniline (4 g, 23.26 mmol, 1 eq) in methanol (70 mL) was added acetic acid (7 mL). The mixture was stirred at 15° C. for 0.5 hours. Borane;2-methylpyridine (4.98 g, 46.52 mmol, 2 eq) was added, then the mixture was stirred at 15° C. for 12 hours. The reaction mixture was diluted with water (120 mL) and extracted with ethyl acetate (80 mL×3). The combined organic phase was washed with saturated brine (100 mL×2), dried with anhydrous sodium sulfate, filtered and concentrated in vacuum. The residue was purified by silica gel chromatography (petroleum ether:ethyl acetate=20:1 to 5:1) to give tert-butyl 4-(4-bromophenyl)-3,5-dimethyl-piperazine-1-carboxylate (8 g, 21.66 mmol, 93% yield) as a colorless oil. LC/MS (ESI) m/z: 369.0 $[M+1]^+$; $^1$H-NMR (400 MHz, $CDCl_3$) δ 7.44-7.40 (m, 2H), 7.00-6.94 (m, 2H), 3.88 (s, 1H), 3.49 (s, 1H), 3.11-2.97 (m, 2H), 2.93-2.77 (m, 2H), 1.50 (s, 9H), 0.79 (d, J=6.0 Hz, 6H).

Step 4: Preparation of 1-(4-bromophenyl)-2,6-dimethylpiperazine

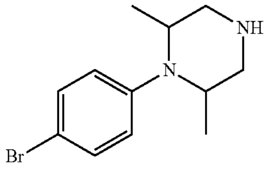

To a solution of tert-butyl 4-(4-bromophenyl)-3,5-dimethyl-piperazine-1-carboxylate (8 g, 21.66 mmol, 1 eq) in dichloromethane (100 mL) was added 4 M hydrochloric acid in dioxane (90 mL). The mixture was stirred at 15° C. for 2 hours. The reaction mixture was concentrated under reduced pressure to give the crude product 1-(4-bromophenyl)-2,6-dimethyl-piperazine (6.6 g, 21.59 mmol, 99% yield, hydrochloride) as a white solid was used into the next step without further purification.

Step 5: Preparation of tert-butyl 4-((4-(4-bromophenyl)-3,5-dimethylpiperazin-1-yl(methyl(piperidine-1-carboxylate

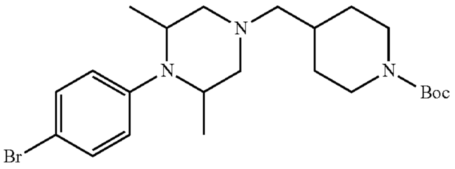 [SMILES: CC1CN(CC2CCN(C(=O)OC(C)(C)C)CC2)CC(C)N1c1ccc(Br)cc1]

To a solution of 1-(4-bromophenyl)-2,6-dimethyl-piperazine (6.6 g, 21.59 mmol, 1 eq, hydrochloride) in methanol (100 mL) was added sodium acetate (5.31 g, 64.78 mmol, 3 eq). The mixture was stirred at 15° C. for 10 min. Tert-butyl 4-formylpiperidine-1-carboxylate (5.99 g, 28.07 mmol, 1.3 eq) was added, the mixture was stirred at 15° C. for 20 min. Sodium cyanoborohydride (2.71 g, 43.19 mmol, 2 eq) was added then the mixture was stirred at 15° C. for another 12 hours. The reaction mixture was diluted with water (500 mL) and extracted with ethyl acetate (300 mL×2). The combined organic phase was washed with saturated brine (300 mL×2), dried with anhydrous sodium sulfate, filtered and concentrated under reduced pressure. The residue was purified by silica gel chromatography (petroleum ether:ethyl acetate=10:1 to 3:1) to give tert-butyl 4-[[4-(4-bromophenyl)-3,5-dimethyl-piperazin-1-yl]methyl]piperidine-1-carboxylate (6.6 g, 14.01 mmol, 64% yield, 99% purity) as a white solid. LC/MS (ESI) m/z: 466.1 $[M+1]^+$; $^1$H-NMR (400 MHz, $CDCl_3$) δ 7.38 (d, J=8.0 Hz, 2H), 6.89 (d, J=8.0 Hz, 2H), 4.32 (d, J=6.0 Hz, 1H), 4.21 (s, 1H), 3.58-3.45 (m, 2H), 2.72 (s, 3H), 2.63 (d, J=8.8 Hz, 2H), 2.29 (dd, J=6.4, 10.4 Hz, 2H), 1.95-1.82 (m, 2H), 1.80-1.71 (m, 2H), 1.70-1.57 (m, 1H), 1.47 (s, 9H), 1.17-1.02 (m, 2H), 0.94 (d, J=6.0 Hz, 6H).

Step 6: Preparation of 1-(4-bromophenyl)-2,6-dimethyl-4-(piperidin-4-ylmethyl)piperazine

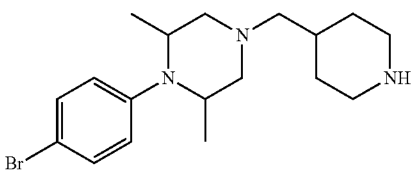 [SMILES: CC1CN(CC2CCNCC2)CC(C)N1c1ccc(Br)cc1]

To a solution of tert-butyl 4-[[4-(4-bromophenyl)-3,5-dimethyl-piperazin-1-yl]methyl]piperidine-1-carboxylate (6.6 g, 14.15 mmol, 1 eq) in dichloromethane (50 mL) was added 4 M hydrochloric acid in dioxane (50 mL, 14.13 eq). The mixture was stirred at 15° C. for 2 hours. The reaction mixture was concentrated under reduced pressure. The crude product was triturated with ethyl acetate (100 mL) to give 1-(4-bromophenyl)-2,6-dimethyl-4-(4-piperidylmethyl)piperazine (6 g, crude, hydrochloride) as a white solid.

Step 7: Preparation of tert-butyl 2-(4-(((3R,5S)-4-(4-bromophenyl)-3,5-dimethylpiperazin-1-yl)methyl)piperidin-1-yl)acetate

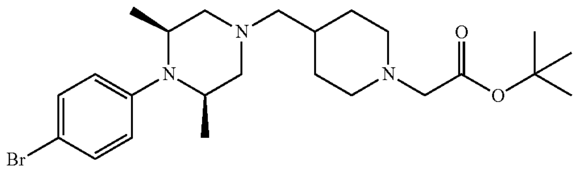 [SMILES: C[C@@H]1CN(CC2CCN(CC(=O)OC(C)(C)C)CC2)C[C@H](C)N1c1ccc(Br)cc1]

To a solution of 1-(4-bromophenyl)-2,6-dimethyl-4-(4-piperidylmethyl)piperazine (6 g, 14.90 mmol, 1 eq, hydrochloride) in acetonitrile (100 mL) was added diisopropylethylamine (9.63 g, 74.48 mmol, 12.9 mL, 5 eq) and tert-butyl 2-bromoacetate (2.91 g, 14.9 mmol, 2.2 mL, 1 eq). The mixture was stirred at 80° C. for 1.5 hours. The reaction mixture was diluted with water (200 mL) and extracted with ethyl acetate (100 mL×2). The combined organic phase was washed with saturated brine (100 mL×2), dried with anhydrous sodium sulfate, filtered and concentrated under reduced pressure. The residue was purified by silica gel chromatography (petroleum ether:ethyl acetate=10:1 to 2:1) to give tert-butyl 2-[4-[[(3S,5S)-4-(4-bromophenyl)-3,5-dimethyl-piperazin-1-yl]methyl]-1-piperidyl]acetate (580 mg, 1.21 mmol, 16% yield) as a white solid and 2-[4-[[(3R,5S)-4-(4-bromophenyl)-3,5-dimethyl-piperazin-1-yl]methyl]-1-piperidyl]acetate (2.7 g, 5.62 mmol, 75% yield) as a white solid. $^1$H-NMR (400 MHz, $CDCl_3$) δ 7.39 (d, J=8.4 Hz, 2H), 6.96 (d, J=8.4 Hz, 2H), 3.22 (s, 2H), 3.12 (s, 2H), 2.95 (d, J=11.2 Hz, 2H), 2.67 (d, J=10.4 Hz, 2H), 2.25-2.14 (m, 4H), 2.09 (t, J=9.6 Hz, 2H), 1.77 (d, J=12.0 Hz, 2H), 1.55-1.44 (m, 10H), 1.40-1.27 (m, 2H), 0.84 (d, J=6.0 Hz, 6H).

Step 8: Preparation of tert-butyl 2-(4-(((3R,5S)-4-(4-(3-(2,6-difluoro-3-(((R)-3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenyl)-3,5-dimethylpiperazin-1-yl)methyl)piperidin-1-yl)acetate

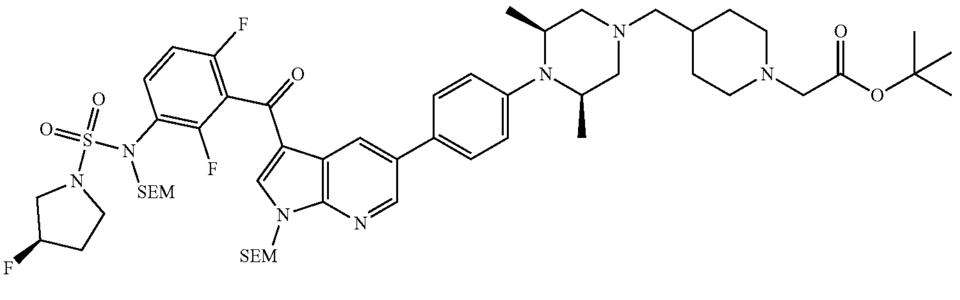 [SMILES: C[C@@H]1CN(CC2CCN(CC(=O)OC(C)(C)C)CC2)C[C@H](C)N1c1ccc(-c2cnc3c(c2)c(C(=O)c2c(F)ccc(N(COCC[Si](C)(C)C)S(=O)(=O)N4CC[C@@H](F)C4)c2F)cn3COCC[Si](C)(C)C)cc1]

A mixture of tert-butyl 2-[4-[[(3R,5S)-4-(4-bromophenyl)-3,5-dimethyl-piperazin-1-1]methyl]-1-piperidyl]acetate (150 mg, 0.31 mmol eq), (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (253 mg, 0.31 mmol, 1 eq), cesium fluoride (190 mg, 1.25 mmol, 4 eq) and 4-ditert-butylphosphanyl-N,N-dimethyl-aniline;

dichloropalladium (22 mg, 0.03 mmol, 0.1 eq) in dioxane (4 mL) and water (0.4 mL) was degassed and purged with nitrogen (3×), and then the mixture was stirred at 95° C. for 3 hours under nitrogen atmosphere. The reaction mixture was diluted with water (15 mL) and extracted with ethyl acetate (10 mL×2). The combined organic phase was washed with saturated brine (10 mL×2), dried with anhydrous sodium sulfate, filtered and concentrated under reduced pressure. The residue was purified by silica gel chromatography (dichloromethane:methanol=100:1 to 50:1)) to give tert-butyl 2-[4-[[(3S,5S)-4-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]-3,5-dimethyl-piperazin-1-yl]methyl]-1-piperidyl]acetate (170 mg, 0.15 mmol, 50% yield) as a light yellow solid. LC/MS (ESI) m/z: 543.0 [M/2+1]$^+$.

Step 9: Preparation of methyl 2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetate

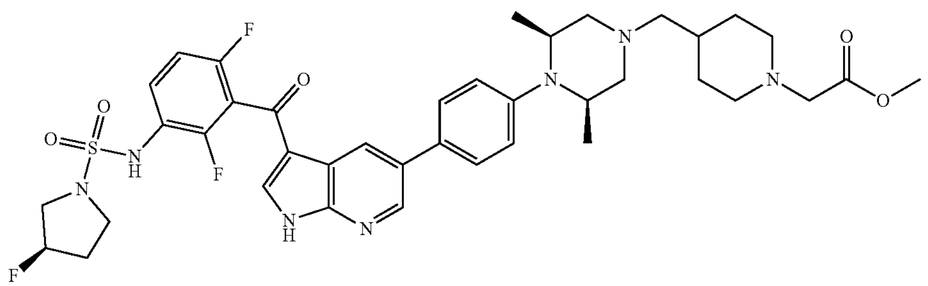 [SMILES: COC(=O)CN1CCC(CN2C[C@@H](C)N(c3ccc(-c4cnc5[nH]cc(C(=O)c6c(F)ccc(NS(=O)(=O)N7CC[C@@H](F)C7)c6F)c5c4)cc3)[C@@H](C)C2)CC1]

To a solution of tert-butyl 2-[4-[[(3R,5S)-4-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]-3,5-dimethyl-piperazin-1-yl]methyl]-1-piperidyl]acetate (170 mg, 0.15 mmol, 1 eq) in methanol (4 mL) was added 4 M hydrochloric acid in dioxane (8 mL). The mixture was stirred at 40° C. for 12 hours. The reaction mixture was concentrated under reduced pressure to remove dioxane, methanol and hydrochloric acid to give the crude product methyl 2-[4-[[(3R,5S)-4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-3,5-dimethyl-piperazin-1-yl]methyl]-1-piperidyl]acetate (120 mg, 0.15 mmol, 97% yield) as a light yellow solid was used into the next step without further purification. LC/MS (ESI) m/z: 782.5 [M+1]$^+$.

Step 10: Preparation of 2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetic acid

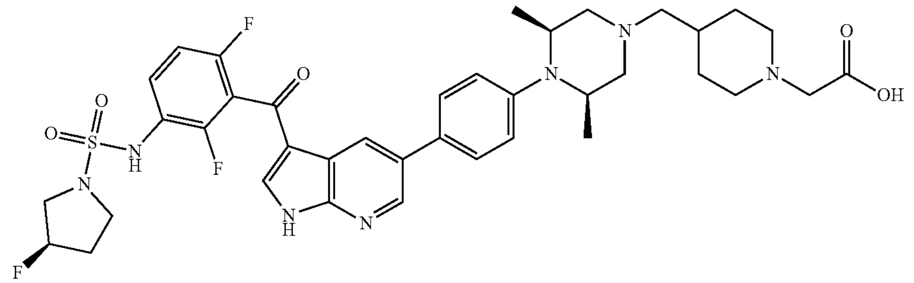 [SMILES: C[C@@H]1CN(CC2CCN(CC(=O)O)CC2)C[C@H](C)N1c1ccc(-c2cnc3[nH]cc(C(=O)c4c(F)ccc(NS(=O)(=O)N5CC[C@@H](F)C5)c4F)c3c2)cc1]

To a solution of methyl 2-[4-[[(3R,5S)-4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-3,5-dimethyl-piperazin-1-yl]methyl]-1-piperidyl]acetate (120 mg, 0.15 mmol, 1 eq) in methanol (3 mL) and water (1 mL) was added lithium hydroxide monohydrate (32 mg, 0.76 mmol, 5 eq). The mixture was stirred at 40° C. for 2 hours. The reaction mixture was concentrated under reduced pressure to remove methanol. The mixture was adjusted to pH 4~5 with hydrochloric acid (2 M) and concentrated under reduced pressure to remove water. The residue was purified by Semi-preparative reverse phase HPLC to give 2-[4-[[(3R,5S)-4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-3,5-dimethyl-piperazin-1-yl]methyl]-1-piperidyl]acetic acid (90 mg, 0.11 mmol, 76% yield) as a yellow solid. LC/MS (ESI) m/z: 768.4 $[M+1]^+$.

Step 11: Preparation of (2S,4R)-1-((S)-2-(2-(4-(((3R,5S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-3,5-dimethylpiperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide (2S,4R)-1-[(2S)-2-[[2-[4-[[(3R,5S)-4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-3,5-dimethyl-piperazin-1-yl]methyl]-1-piperidyl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (66.1 mg, 0.05 mmol, 44% yield, 97% purity, formate) as a white solid. LC/MS (ESI) m/z: 597.8 $[M/2+1]^+$; $^1H$-NMR (400 MHz, DMSO-$d_6$) δ 12.92 (s, 1H), 8.99 (s, 1H), 8.68 (d, J=2.0 Hz, 1H), 8.57 (s, 1H), 8.44 (d, J=7.6 Hz, 1H), 8.19 (s, 1H), 8.07 (s, 1H), 7.78 (d, J=10.0 Hz, 1H), 7.67-7.59 (m, 3H), 7.49-7.42 (m, 2H), 7.40-7.35 (m, 2H), 7.26 (t, J=8.0 Hz, 1H), 7.08 (d, J=8.4 Hz, 2H), 5.39-5.21 (m, 1H), 4.91 (q, J=7.2 Hz, 1H), 4.52 (d, J=10.0 Hz, 1H), 4.46 (t, J=8.4 Hz, 1H), 4.30 (s, 1H), 3.69-3.56 (m, 3H), 3.33-3.25 (m, 6H), 3.08-3.00 (m, 2H), 2.94-2.79 (m, 3H), 2.46 (s, 3H), 2.44-2.37 (m, 2H), 2.21 (d, J=6.4 Hz, 3H), 2.17-1.94 (m, 6H), 1.88-1.72 (m, 3H), 1.68-1.51 (m, 1H), 1.40 (d, J=7.2 Hz, 3H), 1.31-1.16 (m, 2H), 1.03 (br d, J=6.0 Hz, 6H), 0.96 (s, 10H).

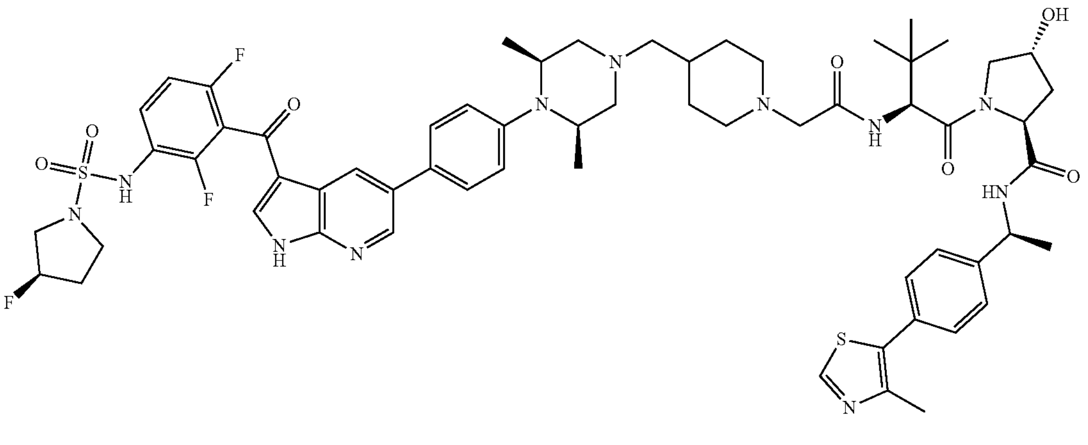 [SMILES: Cc1ncsc1-c1ccc([C@H](C)NC(=O)[C@@H]2C[C@@H](O)CN2C(=O)[C@@H](NC(=O)CN2CCC(CN3C[C@@H](C)N(c4ccc(-c5cnc6[nH]cc(C(=O)c7c(F)ccc(NS(=O)(=O)N8CC[C@@H](F)C8)c7F)c6c5)cc4)[C@@H](C)C3)CC2)C(C)(C)C)cc1]

A mixture of 2-[4-[[(3R,5S)-4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-3,5-dimethyl-piperazin-1-yl]methyl]-1-piperidyl]acetic acid (90 mg, 0.11 mmol, 1 eq), (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (56 mg, 0.11 mmol, 1 eq, hydrochloride), triethylamine (23 mg, 0.23 mmol, 2 eq) and hydroxybenzotriazole (19 mg, 0.14 mmol, 1.2 eq) in dimethylformamide (2 mL) was stirred at 40° C. for 0.5 hour. 1-(3-dimethylaminopropyl)-3-ethylcarbodiimide hydrochloride (33 mg, 0.17 mmol, 1.5 eq) was added, and then the mixture was stirred at 40° C. for 2.5 hours. The solution was purified by Semi-preparative reverse phase HPLC to give Exemplary Synthesis of (2S,4R)-4-hydroxy-1-((2-(2-(2-(2-(4-((2'-methyl-5-morpholino-5'-(3-(trifluoromethyl)benzamido)-[3,3'-bipyridin]-6-yl)oxy)piperidin-1-yl)ethoxy)ethoxy)ethoxy)acetyl)-L-valyl)-N—((S)-1-(4-(4-methylthiazol-5-yl)phenyl)ethyl)pyrrolidine-2-carboxamide (Example 346)

Step 1: Preparation of tert-butyl 2-(2-(2-(2-hydroxyethoxy)ethoxy)ethoxy)acetate

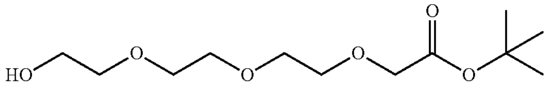 [SMILES: CC(C)(C)OC(=O)COCCOCCOCCO]

To a solution of 2-[2-(2-hydroxyethoxy)ethoxy]ethanol (38 g, 256.34 mmol, 34 mL, 5 eq) in tetrahydrofuran (200 mL) was added sodium hydride (2.46 g, 61.52 mmol, 60% purity, 1.2 eq) at 0° C. over a period of 1 h under nitrogen. The reaction mixture was stirred for 1 h. Then a solution of tert-butyl 2-bromoacetate (10 g, 51.27 mmol, 7.58 mL, 1 eq) in tetrahydrofuran (100 mL) was added to the solution drop-wise at 0° C. and the reaction mixture was stirred for another 12 h at 20° C. The mixture was quenched with water (50 mL) and extracted with ethyl acetate (50 mL×3). The organic layer was dried over sodium sulfate and concentrated. The residue was purified with silica gel chromatography (Petroleum ether:Ethyl acetate=10:1 to 1:1). Tert-butyl 2-[2-[2-(2-hydroxyethoxy)ethoxy]ethoxy]acetate (3 g, 11.35 mmol, 22% yield) was obtained as a yellow oil. $^{1}$H-NMR (400 MHz, $CDCl_3$) δ 4.02 (s, 2H), 3.81-3.57 (m, 12H), 2.61 (br s, 1H), 1.47 (s, 9H).

Step 2: Preparation of tert-butyl 2-(2-(2-(2-(tosyloxy)ethoxy)ethoxy)ethoxy)acetate

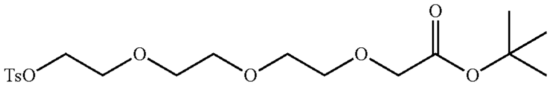 [SMILES: Cc1ccc(S(=O)(=O)OCCOCCOCCOCC(=O)OC(C)(C)C)cc1]

To a solution of tert-butyl 2-[2-[2-(2-hydroxyethoxy)ethoxy]ethoxy]acetate (1 g, 3.78 mmol, 1 eq) in dichloromethane (20 mL) was added paratoluensulfonyl chloride (2.1 g, 11.35 mmol, 3 eq) and triethylamine (1.9 g, 18.92 mmol, 5 eq) 4-dimethylaminopyridine (462 mg, 3.78 mmol, 1 eq). The mixture was stirred at 30° C. for 12 h. The mixture was quenched with water (30 mL) and extracted with dichloromethane (30 mL*3). The organic layer was dried over sodium sulfate and concentrated. The residue was purified with silica gel chromatography (Petroleum ether: Ethyl acetate=10:1 to 1:1). Tert-butyl 2-[2-[2-[2-(p-tolylsulfonyloxy)ethoxy]ethoxy]ethoxy]acetate (500 mg, 1.19 mmol, 31% yield) was obtained as a yellow oil. LC/MS (ESI) m/z: 441.1 [M+23]$^+$.

Step 3: Preparation of tert-butyl 2-(2-(2-(2-(4-((2'-methyl-5-morpholino-5'-(3-(trifluoromethyl)benzamido)-[3,3'-bipyridin]-6-yl)oxy)piperidin-1-yl)ethoxy)ethoxy)ethoxy)acetate

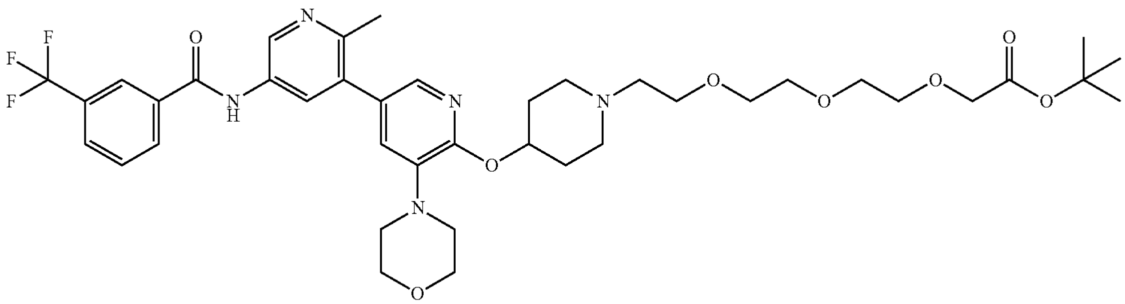 [SMILES: Cc1ncc(NC(=O)c2cccc(C(F)(F)F)c2)cc1-c1cnc(OC2CCN(CCOCCOCCOCC(=O)OC(C)(C)C)CC2)c(N2CCOCC2)c1]

To a solution of tert-butyl 2-[2-[2-[2-(p-tolylsulfonyloxy)ethoxy]ethoxy]ethoxy]acetate (200 mg, 0.477 mmol, 1 eq) in acetonitrile (5 mL) was added N,N-diisopropylethylamine (370 mg, 2.87 mmol, 6 eq) N-[6-methyl-5-[5-morpholino-6-(4-piperidyloxy)-3-pyridyl]-3-pyridyl]-3-(trifluoromethyl)benzamide;hydrochloride and potassium iodide (79 mg, 0.477 mmol, 1 eq). The mixture was stirred at 100° C. for 12 h. The mixture was quenched with water (30 mL) and extracted with ethyl acetate (30 mL*3). The organic layer was dried over sodium sulfate and concentrated. The residue was purified with prep-TLC (Dichloromethane:Methanol=10:1). tert-butyl 2-[2-[2-[2-[4-[[5-[2-methyl-5-[[3-(trifluoromethyl)benzoyl]amino]-3-pyridyl]-3-morpholino-2-pyridyl]oxy]-1-piperidyl]ethoxy]ethoxy]ethoxy]acetate (200 mg, 0.253 mmol, 53% yield) was obtained as a yellow oil. LC/MS (ESI) m/z: 788.2 [M+1]$^+$.

Step 4: Preparation of 2-(2-(2-(2-(4-((2'-methyl-5-morpholino-5'-(3-(trifluoromethyl)benzamido)-[3,3'-bipyridin]-6-yl)oxy)piperidin-1-yl)ethoxy)ethoxy)ethoxy)acetic acid

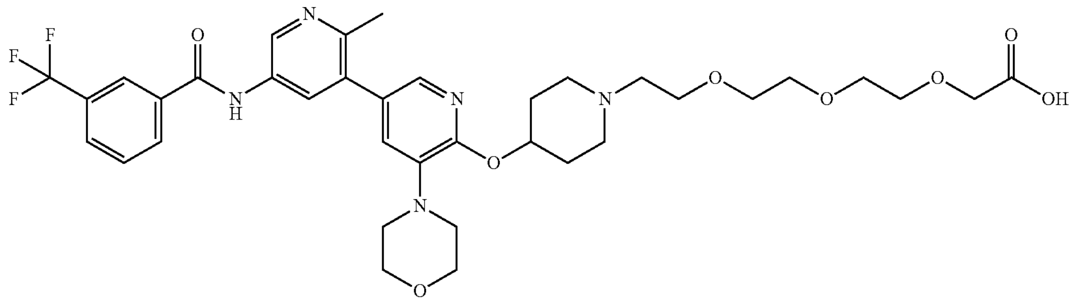 [SMILES: Cc1ncc(NC(=O)c2cccc(C(F)(F)F)c2)cc1-c1cnc(OC2CCN(CCOCCOCCOCC(=O)O)CC2)c(N2CCOCC2)c1]

To a solution of tert-butyl 2-[2-[2-[2-[4-[[5-[2-methyl-5-[[3-(trifluoromethyl)benzoyl]amino]-3-pyridyl]-3-morpholino-2-pyridyl]oxy]-1-piperidyl]ethoxy]ethoxy]ethoxy]acetate (200 mg, 0.253 mmol, 1 eq) in dichloromethane (2 mL) was added trifluoroacetic acid (578 mg, 5.08 mmol, 20 eq). The mixture was stirred at 20° C. for 12 h. The mixture was concentrated. The residue was used in the next step without further purification. 2-[2-[2-[2-[4-[[5-[2-methyl-5-[[3-(trifluoromethyl)benzoyl]amino]-3-pyridyl]-3-morpholino-2-pyridyl]oxy]-1-piperidyl]ethoxy]ethoxy]ethoxy]acetic acid (200 mg, crude, trifluoroacetic acid) was obtained as a yellow oil. LC/MS (ESI) m/z: 732.2 $[M+1]^+$.

Step 5: Preparation of (2S,4R)-4-hydroxy-1-((2-(2-(2-(2-(4-((2'-methyl-5-morpholino-5'-(3-(trifluoromethyl)benzamido)-[3,3'-bipyridin]-6-yl)oxy)piperidin-1-yl)ethoxy)ethoxy)ethoxy)acetyl)-L-valyl)-N—((S)-1-(4-(4-methylthiazol-5-yl)phenyl)ethyl)pyrrolidine-2-carboxamide

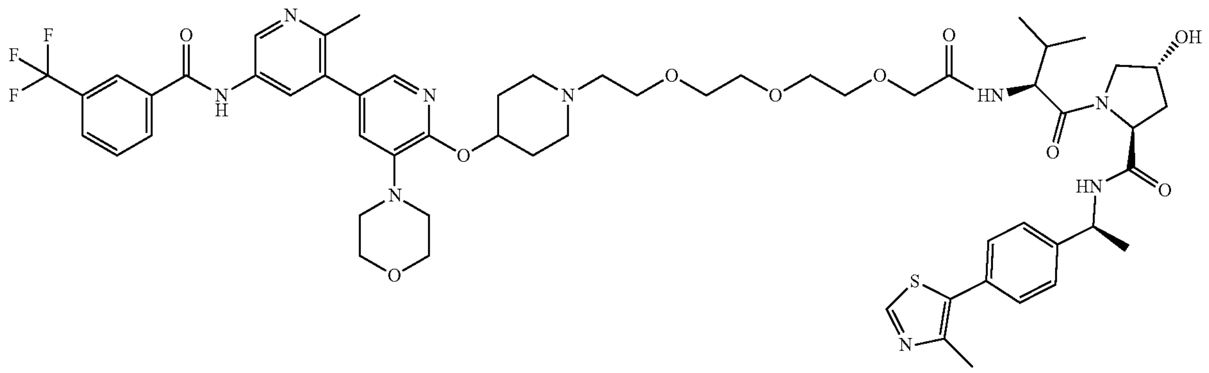 [SMILES: Cc1ncc(NC(=O)c2cccc(C(F)(F)F)c2)cc1-c1cnc(OC2CCN(CCOCCOCCOCC(=O)N[C@H](C(=O)N3C[C@H](O)C[C@H]3C(=O)N[C@@H](C)c3ccc(-c4scnc4C)cc3)C(C)C)CC2)c(N2CCOCC2)c1]

To a solution of 2-[2-[2-[2-[4-[[5-[2-methyl-5-[[3-(trifluoromethyl)benzoyl]amino]-3-pyridyl]-3-morpholino-2-pyridyl]oxy]-1-piperidyl]ethoxy]ethoxy]ethoxy]acetic acid (200 mg, 0.236 mmol, 1 eq, trifluoroacetic acid) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (170 mg, 0.354 mmol, 1.5 eq, hydrochloride) in N,N-dimethylformamide (2 mL) was added hydroxybenzotriazole (38 mg, 0.283 mmol, 1.2 eq) triethylamine (119 mg, 1.18 mmol, 5 eq) and 1-(3-dimethylaminopropyl)-3-ethylcarbodiimide hydrochloride (68 mg, 0.354 mmol, 1.5 eq). The mixture was stirred at 20° C. for 12 h. The mixture was quenched with water (30 mL*3) and extracted with dichloromethane/methanol (10:1.30 mL*3). The organic layer was dried over sodium sulfate and concentrated. The residue was purified with preparative-HPLC. (2S,4R)-1-[(2S)-3,3-dimethyl-2-[[2-[2-[2-[2-[4-[[5-[2-methyl-5-[[3-(trifluoromethyl)benzoyl]amino]-3-pyridyl]-3-morpholino-2-pyridyl]oxy]-1-piperidyl]ethoxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (136.7 mg, 0.107 mmol, 45% yield, 98% purity, 2 formic acid) was obtained as a yellow solid. LC/MS (ESI) m/z: 1144.5 $[M+1]^+$; $^1$H-NMR (400 MHz, DMSO-$d_6$) δ 10.66 (s, 1H), 8.97 (s, 1H), 8.84 (d, J=2.4 Hz, 1H), 8.43 (d, J=7.6 Hz, 1H), 8.32 (s, 1H), 8.28 (d, J=8.0 Hz, 1H), 8.16 (s, 2H), 8.03 (d, J=2.4 Hz, 1H), 7.99 (d, J=7.6 Hz, 1H), 7.84-7.74 (m, 2H), 7.46-7.32 (m, 5H), 7.20 (d, J=2.0 Hz, 1H), 5.19 (br s, 1H), 4.95-4.85 (m, 1H), 4.55 (d, J=9.6 Hz, 1H), 4.44 (t, J=8.0 Hz, 1H), 4.28 (br s, 1H), 3.96 (s, 2H), 3.75 (br s, 4H), 3.67-3.49 (m, 12H), 3.09 (br s, 4H), 2.75-2.64 (m, 2H), 2.55 (br t, J=5.6 Hz, 1H), 2.44 (d, J=4.4 Hz, 9H), 2.09-1.94 (m, 3H), 1.82-1.70 (m, 3H), 1.37 (d, J=7.2 Hz, 3H), 0.94 (s, 9H).

Exemplary Synthesis of N-(6'-((1-(2-(2-(2-((2-(2,6-dioxopiperidin-3-yl)-1-oxoisoindolin-5-yl)oxy)ethoxy)ethoxy)ethyl)piperidin-4-yl)oxy)-2-methyl-5'-morpholino-[3,3'-bipyridin]-5-yl)-3-(trifluoromethyl)benzamide (Example 356)

Step 1: Preparation of 2-(2-(2-hydroxyethoxy)ethoxy)ethyl 4-methylbenzenesulfonate

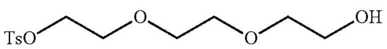 [SMILES: Cc1ccc(S(=O)(=O)OCCOCCOCCO)cc1]

To a mixture of 2-[2-(2-hydroxyethoxy)ethoxy]ethanol (5.00 g, 33.29 mmol, 1.00 eq) and 4-methylbenzenesulfonyl chloride (1.59 g, 8.32 mmol, 0.25 eq) in dichloromethane (50 mL) was added triethylamine (1.68 g, 16.65 mmol, 2.3 mL, 0.5 eq) in one portion at 25° C. under nitrogen. The mixture was stirred at 25° C. for 12 h. The mixture was washed with brine (30 mL×2), dried with anhydrous sodium sulfate, filtered and concentrated in vacuum. The residue was purified by silica gel chromatography (Petroleum ether/Ethyl acetate=1/1 to 0:1) to afford 2-[2-(2-hydroxyethoxy)ethoxy]ethyl 4-methylbenzenesulfonate (1.72 g, 5.65 mmol, 17% yield) as a colorless oil. $^1$H-NMR (400 MHz, $CDCl_3$) δ 7.81 (d, J=8.3 Hz, 2H), 7.35 (d, J=8.0 Hz, 2H), 4.22-4.15 (m, 2H), 3.79-3.67 (m, 4H), 3.67-3.56 (m, 6H), 2.46 (s, 3H).

Step 2: Preparation of tert-butyl 5-amino-4-(((benzyloxy)carbonyl)amino)-5-oxopentanoate

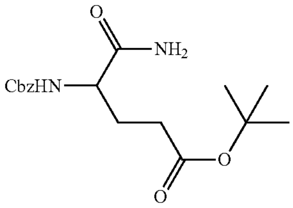 [SMILES: CC(C)(C)OC(=O)CCC(NC(=O)OCc1ccccc1)C(N)=O]

A mixture of 2-(benzyloxycarbonylamino)-5-tert-butoxy-5-oxo-pentanoic acid (40 g, 118.56 mmol, 1 eq), pyridine (18.76 g, 237.13 mmol, 2 eq) and di-tert-butyl dicarbonate (41.40 g, 189.70 mmol, 1.6 eq) in dioxane (400 mL) stirred at 0° C. for 0.5 hr. Then ammonium bicarbonate (28.12 g, 355.69 mmol, 3 eq) was added to the reaction mixture at 0° C. The mixture stirred at 15° C. for 12 hr. The mixture was quenched by addition water (1000 mL), extracted with ethyl acetate (200 mL*4), the combined organic phase washed with brine (200 mL), dried over anhydrous sodium sulfate, filtered and concentrated under reduced pressure. The residue was triturated with petroleum ether/ethyl acetate (V/V=3:1, 100 mL) and collected by filtration. Compound tert-butyl 5-amino-4-(benzyloxycarbonylamino)-5-oxo-pentanoate (35 g, 104.05 mmol, 87% yield) as a white solid was obtained. $^1$H-NMR (400 MHz, $CDCl_3$) δ 7.44-7.31 (m, 5H), 6.34 (d, J=2.8 Hz, 1H), 5.83-5.63 (m, 1H), 5.45 (s, 1H), 5.13 (s, 2H), 4.50-4.17 (m, 1H), 2.57-2.45 (m, 1H), 2.41-2.31 (m, 1H), 2.19-2.06 (m, 1H), 1.96 (d, J=7.2, 14.4 Hz, 1H), 1.49-1.43 (m, 9H).

Step 3: Preparation of tert-butyl 4,5-diamino-5-oxopentanoate

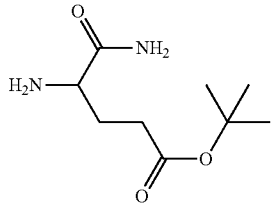

To a solution of tert-butyl 5-amino-4-(benzyloxycarbonylamino)-5-oxo-pentanoate (30 g, 89.18 mmol, 1 eq) in methanol (300 mL) was added palladium on carbon (8 g, 10% purity) under nitrogen. The suspension was degassed under vacuum and purged with hydrogen several times. The mixture was stirred under hydrogen (45 PSI) at 40° C. for 12 hours. The mixture was filtered and concentrated under reduced pressure. The residue was used for next step without further purification. Compound tert-butyl 4,5-diamino-5-oxo-pentanoate (17 g, 84.05 mmol, 94% yield) as a gray solid was obtained. $^1$H-NMR (400 MHz, DMSO-$d_6$) δ 7.32 (s, 1H), 6.98 (s, 1H), 3.10 (m, 1H), 3.04-2.58 (m, 2H), 2.24 (m, 2H), 1.84-1.70 (m, 1H), 1.65-1.50 (m, 1H), 1.40 (s, 9H).

Step 4: Preparation of methyl 4-((tert-butyldimethylsilyl)oxy)-2-methylbenzoate

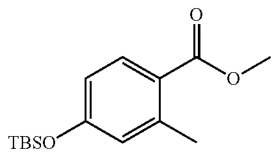 [SMILES: COC(=O)c1ccc(O[Si](C)(C)C(C)(C)C)cc1C]

To a solution of methyl 4-hydroxy-2-methyl-benzoate (5.00 g, 30.09 mmol, 1.00 eq) in dimethylformamide (100 mL) was added imidazole (6.15 g, 90.27 mmol, 3.00 eq). The mixture was stirred at 15° C. for 0.5 h, and then chlorotrimethylsilane (6.80 g, 45.14 mmol, 5.5 mL, 1.50 eq) was added. The resulting mixture was stirred at 15° C. for another 14.5 h. The mixture was poured into saturated brine (300 mL), and then extracted with ethyl acetate (300 mL*2). The combined organic layers were washed with 1 M hydrochloric acid (300 mL*2), brine (300 mL*3), dried over sodium sulfate, filtered and concentrated in vacuum to afford methyl 4-[tert-butyl(dimethyl)silyl]oxy-2-methyl-benzoate (8.00 g, 28.53 mmol, 95% yield) as colorless oil, which was used into the next step without further purification. LC/MS (ESI) m/z: 281.2 $[M+1]^+$.

Step 5: Preparation of methyl 2-(bromomethyl)-4-((tert-butyldimethylsilyl)oxy)benzoate

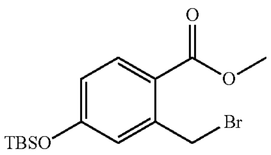 [SMILES: COC(=O)c1ccc(O[Si](C)(C)C(C)(C)C)cc1CBr]

To a solution of methyl 4-[tert-butyl(dimethyl)silyl]oxy-2-methyl-benzoate (3.00 g, 10.70 mmol, 1.00 eq) in carbon-tetrachloride (40 mL) was added N-bromosuccinimide (2.29 g, 12.84 mmol, 1.20 eq) and 2,2-azobisisobutyronitrile (88 mg, 0.54 mmol, 0.05 eq). The mixture was stirred at 15° C. for 0.5 h, then heated to 80° C. and stirred at 80° C. for another 2.5 h. The mixture was poured into water (300 mL), the organic layer was separated. The aqueous layer was extracted with dichloromethane (200 mL*2). The combined organic layers were washed with saturated brine (300 mL*3), dried over sodium sulfate, filtered and concentrated in vacuum to afford methyl 2-(bromomethyl)-4-[tert-butyl(dimethyl)silyl]oxy-benzoate (4.00 g, 8.39 mmol, 78% yield, 75% purity) as a light yellow oil, which was directly used into the next step without further purification. LC/MS (ESI) m/z: 359.0/361.0 $[M+1]^+$.

Step 6: Preparation of tert-butyl 5-amino-4-(5-hydroxy-1-oxoisoindolin-2-yl)-5-oxopentanoate

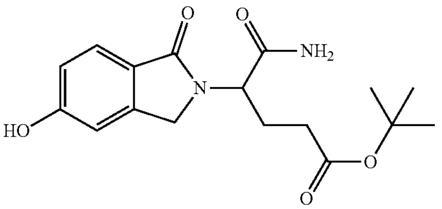 [SMILES: CC(C)(C)OC(=O)CCC(C(N)=O)N1Cc2cc(O)ccc2C1=O]

To a mixture of methyl 2-(bromomethyl)-4-[tert-butyl(dimethyl)silyl]oxy-benzoate (10 g, 27.83 mmol, 1 eq) and tert-butyl 4,5-diamino-5-oxo-pentanoate (5.63 g, 27.83 mmol, 1 eq) in acetonitrile (150 mL) was added Diisopropylethylamine (14.39 g, 111.32 mmol, 4 eq). The mixture stirred at 80° C. for 12 hr. The mixture was quenched by addition water (200 mL), extracted with ethyl acetate (40 mL*6), the combined organic phase washed with brine (50 mL), dried over anhydrous sodium sulfate, filtered and concentrated under reduced pressure. The residue was purified by prep-HPLC to obtain tert-butyl 5-amino-4-[5-[tert-butyl(dimethyl)silyl]oxy-1-oxo-isoindolin-2-yl]-5-oxo-pentanoate (3 g, 6.69 mmol, 24% yield) as a yellow oil and tert-butyl 5-amino-4-(5-hydroxy-1-oxo-isoindolin-2-yl)-5-oxo-pentanoate (4 g, 11.96 mmol, 42% yield) as a yellow solid.

Step 7: Preparation of tert-butyl 5-amino-4-(5-(2-(2-(2-hydroxyethoxy)ethoxy)ethoxy)-1-oxoisoindolin-2-yl)-5-oxopentanoate

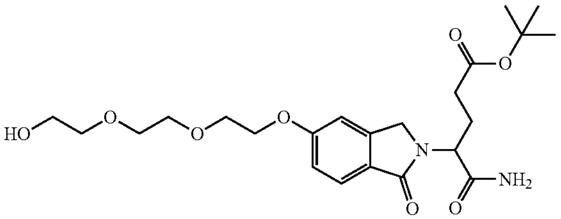 [SMILES: CC(C)(C)OC(=O)CCC(C(N)=O)N1Cc2cc(OCCOCCOCCO)ccc2C1=O]

To a solution of 2-[2-(2-hydroxyethoxy)ethoxy]ethyl 4-methylbenzenesulfonate (251 mg, 0.82 mmol, 1.2 eq) in N,N-dimethyl formamide (4 mL) was added potassium carbonate (285 mg, 2.06 mmol, 3 eq), potassium iodide (114 mg, 0.68 mmol, 1 eq) and tert-butyl 5-amino-4-(5-hydroxy-1-oxo-isoindolin-2-yl)-5-oxo-pentanoate (230 mg, 0.68 mmol, 1 eq). The mixture was stirred at 80° C. for 1 hour. The solution was quenched with water (20 ml) and extracted with dichloromethane/methanol=10:1 (20 mL×8). The organic layer was washed with saturated brine (20 mL×1) dried over sodium sulfate and filtered and concentrated under reduced pressure to give a residue. The residue was purified by prep-thin-layer chromatography (dichloromethane:methanol=10:1) to give tert-butyl 5-amino-4-[5-[2-[2-(2-hydroxyethoxy)ethoxy]ethoxy]-1-oxo-isoindolin-2-yl]-5-oxo-pentanoate (275 mg, 0.58 mmol, 85% yield) as a yellow oil. LC/MS (ESI) m/z: 467.4 $[M+1]^+$.

Step 8: Preparation of tert-butyl 5-amino-5-oxo-4-(1-oxo-5-(2-(2-(2-(tosyloxy)ethoxy)ethoxy)ethoxy)isoindolin-2-yl)pentanoate

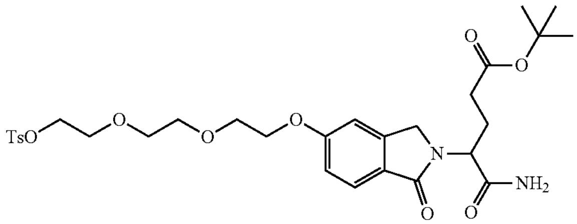 [SMILES: Cc1ccc(S(=O)(=O)OCCOCCOCCOc2ccc3c(c2)CN(C(CCC(=O)OC(C)(C)C)C(N)=O)C3=O)cc1]

To a solution of methanesulfonyl chloride (224 mg, 1.18 mmol, 2 eq) in N,N-dimethyl formamide (4 mL) was added triethylamine (178 mg, 1.77 mmol, 3 eq) and dimethylaminopyridine (14 mg, 0.11 mmol, 0.2 eq) and tert-butyl 5-amino-4-[5-[2-[2-(2-hydroxyethoxy)ethoxy]ethoxy]-1-oxo-isoindolin-2-yl]-5-oxo-pentanoate (275 mg, 0.58 mmol, 1 eq). The mixture was stirred at 20° C. for 1 hour. The solution was quenched with water (10 ml) and extracted with dichloromethane:methanol=10:1 (10 mL×4). The organic layer was dried over sodium sulfate and filtered and concentrated under reduced pressure to give a residue. The residue was purified by prep-thin-layer chromatography (dichloromethane:methanol=10:1) to give tert-butyl 5-amino-5-oxo-4-[1-oxo-5-[2-[2-[2-(p-tolylsulfonyloxy)ethoxy]ethoxy]ethoxy]isoindolin-2-yl]pentanoate (220 mg, 0.35 mmol, 60% yield) as a yellow oil. LC/MS (ESI) m/z: 621.4 $[M+1]^+$.

Step 9: Preparation of tert-butyl 5-amino-4-(5-(2-(2-(2-(4-((2'-methyl-5-morpholino-5'-(3-(trifluoromethyl)benzamido)-[3,3'-bipyridin]-6-yl)oxy)piperidin-1-yl)ethoxy)ethoxy)ethoxy)-1-oxoisoindolin-2-yl)-5-oxopentanoate

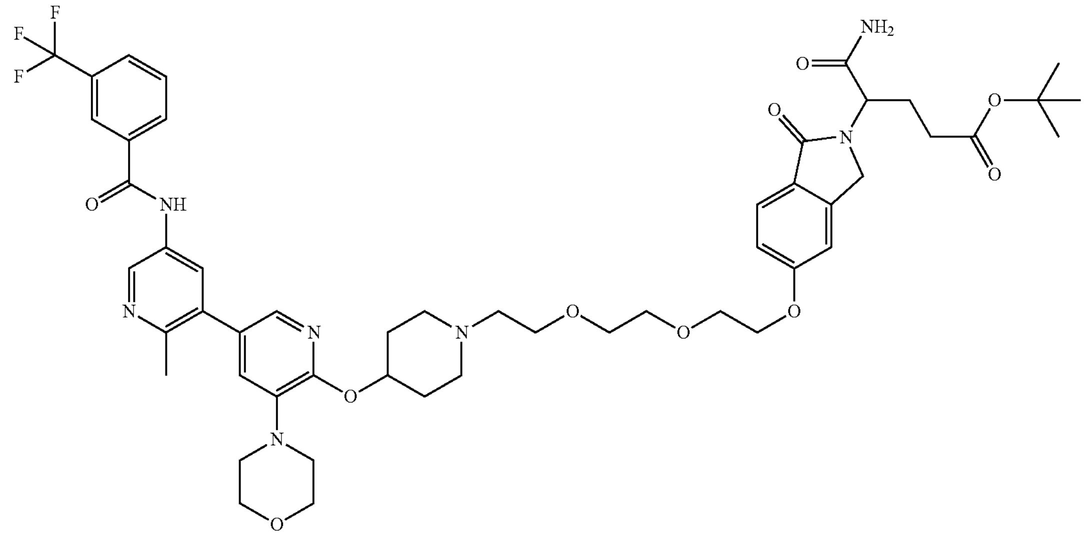 [SMILES: Cc1ncc(NC(=O)c2cccc(C(F)(F)F)c2)cc1-c1cnc(OC2CCN(CCOCCOCCOc3ccc4c(c3)CN(C(CCC(=O)OC(C)(C)C)C(N)=O)C4=O)CC2)c(N2CCOCC2)c1]

To a solution of N-[6-methyl-5-[5-morpholino-6-(4-piperidyloxy)-3-pyridyl]-3-pyridyl]-3-(trifluoromethyl)benzamide (204 mg, 0.35 mmol, 1 eq, hydrogen chloride) in acetonitrile (5 mL) was added N,N-diisopropylethylamine (137 mg, 1.06 mmol, 3 eq) and potassium iodide (58 mg, 0.35 mmol, 1 eq) and tert-butyl 5-amino-5-oxo-4-[1-oxo-5-[2-[2-[2-(p-tolylsulfonyloxy)ethoxy]ethoxy]ethoxy]isoindolin-2-yl]pentanoate (220 mg, 0.35 mmol, 1 eq). The mixture was stirred at 100° C. for 1 hour. The solution was quenched with water (10 ml) and extracted with dichloromethane:methanol=10:1 (10 mL×3). The organic layer was dried over sodium sulfate and filtered and concentrated under reduced pressure to give a residue. The residue was purified by prep-thin-layer chromatography (dichloromethane:methanol=10:1) to give tert-butyl 5-amino-4-[5-[2-[2-[2-[4-[[5-[2-methyl-5-[[3-(trifluoromethyl)benzoyl]amino]-3-pyridyl]-3-morpholino-2-pyridyl]oxy]-1-piperidyl]ethoxy]ethoxy]ethoxy]-1-oxo-isoindolin-2-yl]-5-oxo-pentanoate (141 mg, 0.13 mmol, 37% yield, 93% purity) was obtained as a yellow oil. LC/MS (ESI) m/z: 991.5 $[M+1]^+$.

Step 10: Preparation of N-(6'-((1-(2-(2-(2-((2-(2,6-dioxopiperidin-3-yl)-1-oxoisoindolin-5-yl)oxy)ethoxy)ethoxy)ethyl)piperidin-4-yl)oxy)-2-methyl-5'-morpholino-[3,3'-bipyridin]-5-yl)-3-(trifluoromethyl)benzamide

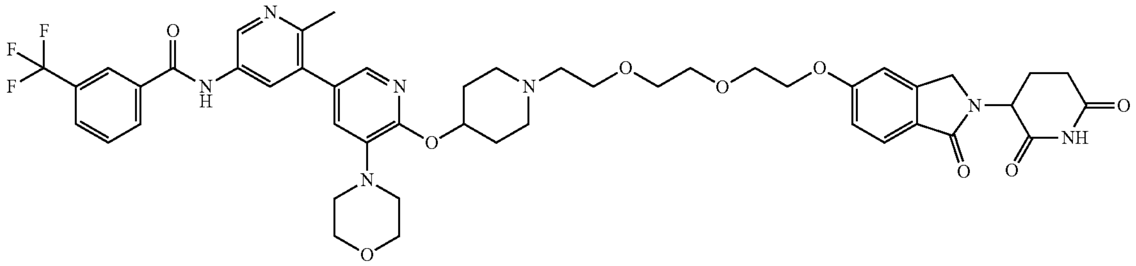 [SMILES: Cc1ncc(NC(=O)c2cccc(C(F)(F)F)c2)cc1-c1cnc(OC2CCN(CCOCCOCCOc3ccc4c(c3)CN(C3CCC(=O)NC3=O)C4=O)CC2)c(N2CCOCC2)c1]

To a solution of tert-butyl 5-amino-4-[5-[2-[2-[2-[4-[[5-[2-methyl-5-[[3-(trifluoromethyl) benzoyl]amino]-3-pyridyl]-3-morpholino-2-pyridyl]oxy]-1-piperidyl]ethoxy]ethoxy]ethoxy]-1-oxo-isoindolin-2-yl]-5-oxo-pentanoate (141 mg, 0.14 mmol, 1 eq) in acetonitrile (1 mL) was added benzenesulfonic acid (80 mg, 0.42 mmol, 3 eq). The mixture was stirred at 100° C. for 1 hour. The solution was quenched with water (10 ml) and extracted with dichloromethane:methanol=10:1 (10 mL×3). The organic layer was dried over sodium sulfate and filtered and concentrated under reduced pressure to give a residue. The residue was purified by prep-thin-layer chromatography (dichloromethane:methanol=10:1) to give N-[5-[6-[[1-[2-[2-[2-[2-(2,6-dioxo-3-piperidyl)-1-oxo-isoindolin-5-yl]oxyethoxy]ethoxy]ethyl]-4-piperidyl]oxy]-5-morpholino-3-pyridyl]-6-methyl-3-pyridyl]-3-(trifluoromethyl)benzamide (54.1 mg, 0.057 mmol, 40% yield, 97% purity) was obtained as a white solid. LC/MS (ESI) m/z: 916.3 $[M+1]^+$; $^1$H-NMR (400 MHz, DMSO-$d_6$) δ 10.94 (s, 1H), 10.65 (s, 1H), 8.84 (s, 1H), 8.36-8.23 (m, 2H), 8.08-7.94 (m, 2H), 7.87-7.74 (m, 2H), 7.61 (d, J=8.8 Hz, 1H), 7.24-7.14 (m, 2H), 7.06 (d, J=8.4 Hz, 1H), 5.20 (s, 1H), 5.06 (dd, J=5.2, 13.2 Hz, 1H), 4.39-4.17 (m, 4H), 3.84-3.73 (m, 6H), 3.66-3.50 (m, 6H), 3.09 (s, 5H), 2.59 (s, 4H), 2.45-2.36 (m, 7H), 1.99 (s, 3H), 1.75 (s, 2H), 1.82-1.68 (m, 1H)

Exemplary Synthesis of N-(6'-(4-(2-(2-(2-((2-(2,6-dioxopiperidin-3-yl)-1,3-dioxoisoindolin-5-yl)oxy)ethoxy)ethoxy)ethoxy)phenoxy)-2-methyl-5'-morpholino-[3,3'-bipyridin]-5-yl)-3-(trifluoromethyl)benzamide (Example 468)

Step 1: Preparation of N-(2-methyl-5'-morpholino-6'-(4-((tetrahydro-2H-pyran-2-yl)oxy)phenoxy)-[3,3'-bipyridin]-5-yl)-3-(trifluoromethyl)benzamide

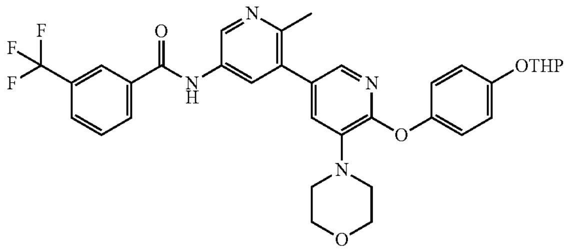

To a mixture of 4-tetrahydropyran-2-yloxyphenol (949 mg, 4.89 mmol, 1.5 eq) in 1-Methyl-2-pyrrolidinone (15 mL) was added potassium tert-butoxide (731 mg, 6.52 mmol, 2 eq) and N-[5-(6-fluoro-5-morpholino-3-pyridyl)-6-methyl-3-pyridyl]-3-(trifluoromethyl) benzamide (1.5 g, 3.26 mmol, 1 eq) in one portion at 15° C. The mixture was stirred at 140° C. under microwave for 2 hr. The mixture was washed with water (50 mL). The aqueous layer was extracted with ethyl acetate (30 mL×7). All the combined organic layers were washed with brine, dried over sodium sulfate, filtered and concentrated. The residue was purified by prep-High Performance Liquid Chromatography to give a brown solid. N-[6-methyl-5-[5-morpholino-6-(4-tetrahydropyran-2-yloxyphenoxy)-3-pyridyl]-3-pyridyl]-3-(trifluoromethyl)benzamide (600 mg, 0.94 mmol, 29% yield) was obtained as brown solid. LC/MS (ESI) m/z: 635.1 $[M+1]^+$.

Step 2: Preparation of N-(6'-(4-hydroxyphenoxy)-2-methyl-5'-morpholino-[3,3'-bipyridin]-5-yl)-3-(trifluoromethyl)benzamide

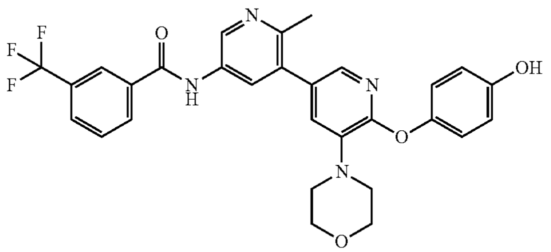 [SMILES: Cc1ncc(NC(=O)c2cccc(C(F)(F)F)c2)cc1-c1cnc(Oc2ccc(O)cc2)c(N2CCOCC2)c1]

To a mixture of N-[6-methyl-5-[5-morpholino-6-(4-tetrahydropyran-2-yloxyphenoxy)-3-pyridyl]-3-pyridyl]-3-(trifluoromethyl)benzamide (200 mg, 0.31 mmol, 1 eq) in dichloromethane (5 mL) was added hydrochloric acid/dioxane (4 M, 2 mL, 20 eq). The mixture was stirred at 15° C. for 30 min. The mixture was concentrated under reduced pressure. The residue was used for next step without further purification. Compound N-[5-[6-(4-hydroxyphenoxy)-5-morpholino-3-pyridyl]-6-methyl-3-pyridyl]-3-(trifluoromethyl)benzamide (200 mg, crude, Hydrochloride) was obtained as a brown solid.

Step 3: Preparation of N-(6'-(4-(2-(2-(2-bromoethoxy)ethoxy)ethoxy)phenoxy)-2-methyl-5'-morpholino-[3,3'-bipyridin]-5-yl)-3-(trifluoromethyl)benzamide

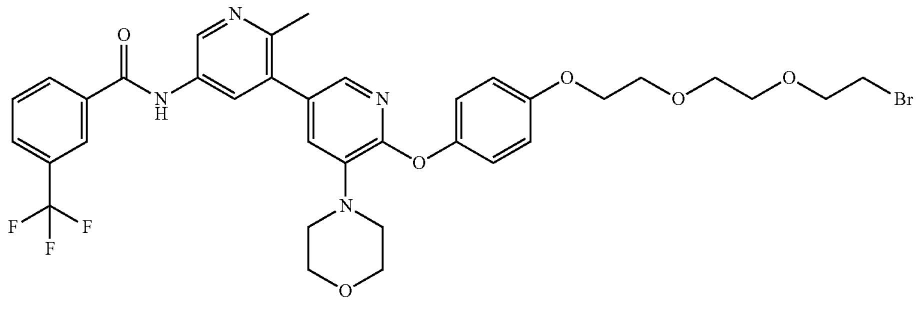 [SMILES: Cc1ncc(NC(=O)c2cccc(C(F)(F)F)c2)cc1-c1cnc(Oc2ccc(OCCOCCOCCBr)cc2)c(N2CCOCC2)c1]

To a solution of N-[5-[6-(4-hydroxyphenoxy)-5-morpholino-3-pyridyl]-6-methyl-3-pyridyl]-3-(trifluoromethyl) benzamide (200 mg, 0.36 mmol, 1 eq) in acetonitrile (5 mL) was added potassium carbonate (151 mg, 1.09 mmol, 3 eq) and 1,2-bis(2-bromoethoxy)ethane (250.64 mg, 908.22 umol, 2.5 eq). The mixture was stirred at 60° C. for 2 h. The reaction mixture was filtered and the filtrate was concentrated. The residue was purified by prep-TLC (dichloromethane:methanol=10:1). Compound N-[5-[6-[4-[2-[2-(2-bromoethoxy)ethoxy]ethoxy]phenoxy]-5-morpholino-3-pyridyl]-6-methyl-3-pyridyl]-3-(trifluoromethyl)benzamide (160 mg, 0.21 mmol, 59% yield) was obtained as a yellow solid. LC/MS (ESI) m/z: 747.0 $[M+1]^+$.

Step 4: Preparation of 2-(2,6-dioxopiperidin-3-yl)-5-hydroxyisoindoline-1,3-dione

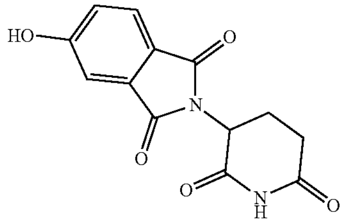 [SMILES: O=C1CCC(N2C(=O)c3ccc(O)cc3C2=O)C(=O)N1]

To a solution of 3-aminopiperidine-2,6-dione (4.1 g, 24.7 mmol, 1.50 eq, HCl salt) in acetic acid (45 mL) was added sodium acetate (4.1 g, 49.4 mmol, 3.00 eq), then the mixture was stirred at 25° C. for 1 h. Then 4-hydroxyphthalic acid (3.0 g, 16.5 mmol, 1.00 eq) was added into the mixture and heated to 120° C., stirred for additional 11 h. The mixture was concentrated and then poured into water (20 mL), and then filtered. The crude product was purified by column chromatography (dichloromethane:methanol=50:1 to 10:1) to afford 2-(2,6-dioxo-3-piperidyl)-5-hydroxy-isoindoline-1,3-dione (3.9 g, 14.3 mmol, 86% yield) as a colorless solid.

LC/MS (ESI) m/z: 275 $[M+1]^+$; $^1$H NMR (400 MHz, $CDCl_3$) δ 11.19-10.94 (m, 2H), 7.75 (d, J=8.0 Hz, 1H), 7.20-7.08 (m, 2H), 5.08 (dd, J=5.2, 12.8 Hz, 1H), 3.34 (br s, 1H), 2.95-2.81 (m, 1H), 2.64-2.55 (m, 1H), 2.08-1.98 (m, 1H).

Step 5: Preparation of N-(6'-(4-(2-(2-(2-((2-(2,6-dioxopiperidin-3-yl)-1,3-dioxoisoindolin-5-yl)oxy)ethoxy)ethoxy)ethoxy)phenoxy)-2-methyl-5'-morpholino-[3,3'-bipyridin]-5-yl)-3-(trifluoromethyl) benzamide

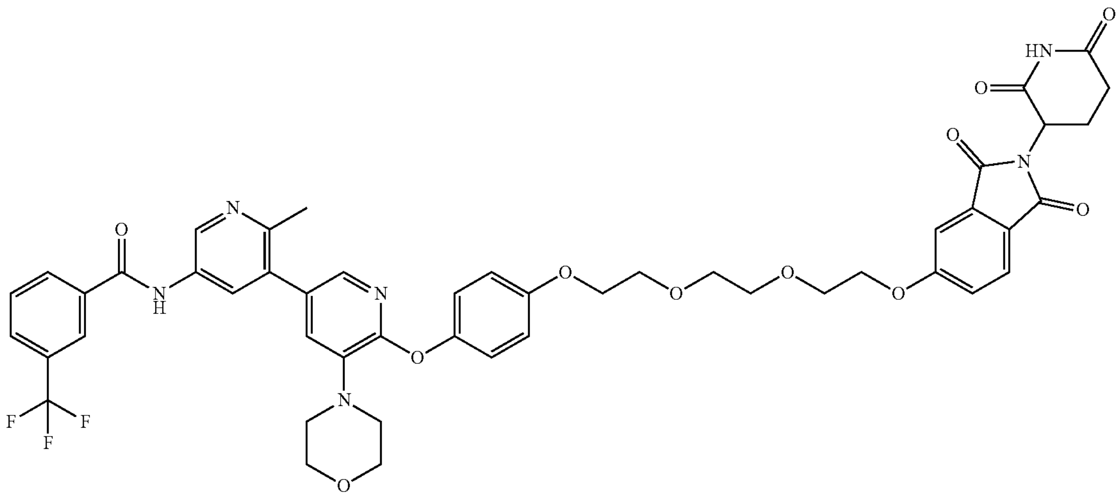 [SMILES: Cc1ncc(NC(=O)c2cccc(C(F)(F)F)c2)cc1-c1cnc(Oc2ccc(OCCOCCOCCOc3ccc4c(c3)C(=O)N(C3CCC(=O)NC3=O)C4=O)cc2)c(N2CCOCC2)c1]

To a solution of N-[5-[6-[4-[2-[2-(2-bromoethoxy) ethoxy]ethoxy]phenoxy]-5-morpholino-3-pyridyl]-6-methyl-3-pyridyl]-3-(trifluoromethyl)benzamide (80 mg, 0.11 mmol, 1 eq) in dimethyl formamide (2 mL) was added potassium carbonate (44 mg, 0.32 mmol, 3 eq) and 2-(2,6-dioxo-3-piperidyl)-5-hydroxy-isoindoline-1,3-dione (44 mg, 0.16 mmol, 1.5 eq). The mixture was stirred at 60° C. for 2 hours. The reaction mixture was filtered and the filtrate was concentrated. The residue was purified by prep-HPLC. Compound N-[5-[6-[4-[2-[2-[2-[2-(2,6-dioxo-3-piperidyl)-1,3-dioxo-isoindolin-5-yl]oxyethoxy]ethoxy]ethoxy]phenoxy]-5-morpholino-3-pyridyl]-6-methyl-3-pyridyl]-3-(trifluoromethyl)benzamide (25.8 mg, 0.02 mmol, 25% yield, 97% purity) was obtained as a grey solid. LC/MS (ESI) m/z: 939.2 $[M+1]^+$; $^1$H-NMR (400 MHz, DMSO-$d_6$) δ 11.10 (d, J=1.0 Hz, 1H), 10.73-10.60 (m, 1H), 8.85 (d, J=2.4 Hz, 1H), 8.32 (s, 1H), 8.28 (d, J=7.7 Hz, 1H), 8.05 (d, J=2.3 Hz, 1H), 7.99 (d, J=8.0 Hz, 1H), 7.86-7.77 (m, 2H), 7.71 (d, J=2.1 Hz, 1H), 7.46 (d, J=2.2 Hz, 1H), 7.41-7.33 (m, 2H), 7.13-7.05 (m, 2H), 7.00-6.93 (m, 2H), 5.11 (dd, J=5.6, 12.9 Hz, 1H), 4.32 (dd, J=3.6, 5.2 Hz, 2H), 4.16-4.02 (m, 2H), 3.84-3.79 (m, 2H), 3.78-3.73 (m, 6H), 3.64 (s, 4H), 3.56 (d, J=8.8 Hz, 1H), 3.48-3.37 (m, 1H), 3.21-3.17 (m, 3H), 2.94-2.81 (m, 1H), 2.60 (d, J=2.4 Hz, 1H), 2.44 (s, 3H), 2.08-1.98 (m, 1H)

Exemplary Synthesis of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) acetamido)-3,3-dimethylbutanoyl)-4-hydroxy-N—((S)-1-(4-(4-(hydroxymethyl)thiazol-5-yl)phenyl) ethyl)pyrrolidine-2-carboxamide (Example 498)

Step 1: Preparation of (1-(4-bromophenyl)piperidin-4-yl)methanol

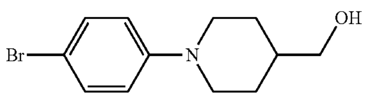

To a solution of 4-piperidylmethanol (100 g, 868 mmol, 1 eq), 1-bromo-4-iodo-benzene (245 g, 868 mmol, 1 eq), L-PROLINE (40 g, 347 mmol, 0.4 eq) in dimethylsulfoxide (1.8 L) was added copper(I) iodide (33 g, 173 mmol, 0.2 eq) and potassium carbonate (240 g, 1.74 mol, 2 eq). The mixture was de-gassed in vacuum and purged with nitrogen for 3 times. Then the mixture was heated to 90° C. for 12 hours under nitrogen. The reaction mixture was poured into 1.0 L water and stirred for 1 hour. Then the mixture was extracted with ethyl acetate (1000 mL*3). The combined organic layers were washed with brine (1 L*3), dried over anhydrous sodium sulfate, filtered and concentrated under reduced pressure. The residue was purified by silica gel column chromatography (Petroleum ether/Ethyl acetate=10:1 to 3:1). [1-(4-bromophenyl)-4-piperidyl] methanol (120 g, 444 mmol, 51% yield) was obtained as a white solid. $^1$H-NMR (400 MHz, DMSO-$d_6$) δ 7.46-7.28 (m, 2H), 6.88-6.75 (m, 2H), 4.49 (t, J=5.2 Hz, 1H), 3.69-3.66 (m, 2H), 3.28 (t, J=6.0 Hz, 2H), 2.66-2.60 (m, 2H), 1.75-1.70 (m, 2H), 1.52-1.51 (m, 1H), 1.24-1.18 (m, 2H).

Step 2: Preparation of 1-(4-bromophenyl)piperidine-4-carbaldehyde

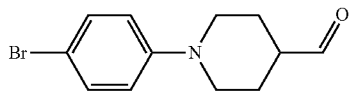 [SMILES: O=CC1CCN(c2ccc(Br)cc2)CC1]

To a solution of oxalyl chloride (140.94 g, 1.11 mol, 3 eq) in dichloromethane (550 mL) was added a solution of dimethylsulfoxide (115.68 g, 1.48 mol, 4 eq) in dichloromethane (550 mL) drop-wise at −68° C. over a period of 0.5 hour under nitrogen. The mixture was stirred at −68° C. for half an hour and then a solution of [1-(4-bromophenyl)-4-piperidyl]methanol (100 g, 370.14 mmol, 1 eq) in dichloromethane (1000 mL) was added dropwise at −68° C. The mixture was stirred at −68° C. for another 0.5 hour. Triethylamine (299.64 g, 2.96 mol, 8 eq) was added dropwise at −68° C. to the reaction mixture. The resulting mixture was stirred at −68° C. for 2 hours. The reaction mixture was quenched by ammonium chloride 500 mL at 25° C. and extracted with ethyl acetate (600 mL×3). The combined organic layers were washed with brine (400 mL×3), dried over anhydrous sodium sulfate, filtered and concentrated under reduced pressure. The residue was triturated with petroleum ether (300 mL). 1-(4-bromophenyl)piperidine-4-carbaldehyde (93 g, 346.82 mmol, 93% yield) was obtained as a yellow solid. $^1$H-NMR (400 MHz, $CDCl_3$) δ 9.72 (s, 1H), 7.54-7.34 (m, 2.0H), 6.85-6.74 (m, 2.0H), 3.61-3.56 (m, 2H), 2.91-2.86 (m, 2H), 2.48-2.33 (m, 1H), 2.07-2.04 (m, 2H), 1.82-1.80 (m, 2H).

Step 3: Preparation of 1-(4-bromophenyl)-4-(dimethoxymethyl)piperidine

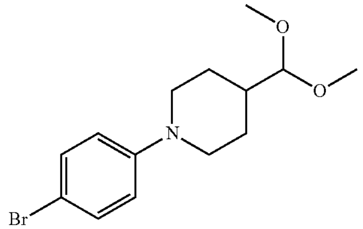 [SMILES: COC(OC)C1CCN(c2ccc(Br)cc2)CC1]

To a solution of 1-(4-bromophenyl)piperidine-4-carbaldehyde (370 g, 1.38 mol, 1 eq) in methyl alcohol (1200 mL) was added trimethoxymethane (732.14 g, 6.90 mol, 5 eq) and 4-methylbenzenesulfonic acid; hydrate (52.49 g, 275.97 mmol, 0.2 eq). The mixture was stirred at 25° C. for 12 hours. The reaction mixture was quenched by addition sodium bicarbonate 500 mL at 25° C. and extracted with dichloromethane (500 mL×3). The combined organic layers were washed with brine (300 mL×3), dried over anhydrous sodium sulfate, filtered and concentrated under reduced pressure. The residue was triturated with petroleum ether and ethyl acetate (1.5 L petroleum ether:ethyl acetate=20:1). 1-(4-bromophenyl)-4-(dimethoxymethyl)piperidine (366 g, 1.16 mol, 84% yield) was obtained as a red solid. The mother liquid (45 g) was further purified by flash chromatography. $^1$H-NMR (400 MHz, $CDCl_3$) δ 7.52-7.33 (m, 2H), 6.83-6.70 (m, 2H), 4.10 (dd, J=2.4 Hz, J=7.2 Hz, 1H), 3.69-3.66 (m, 2H), 3.40 (s, 6H), 2.71-2.65 (m, 2H), 1.88-1.87 (m, 2H), 1.85-1.84 (m, 1H), 1.48-1.44 (m, 2H).

Step 4: Preparation of 4-(dimethoxymethyl)-1-(4-(4,4,5,5-tetramethyl-1,3,2-dioxaborolan-2-yl)phenyl) piperidine

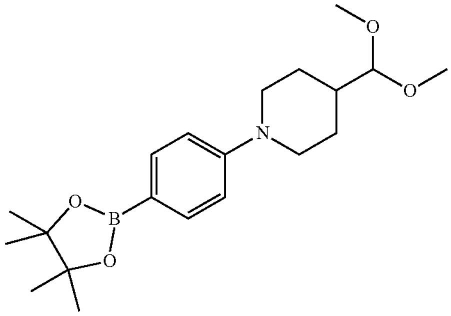

1-(4-bromophenyl)-4-(dimethoxymethyl)piperidine (1 g, 3.18 mmol, 1 eq), 4,4,5,5-tetramethyl-2-(4,4,5,5-tetramethyl-1,3,2-dioxaborolan-2-yl)-1,3,2-dioxaborolane (969 mg, 3.82 mmol, 1.2 eq), ditert-butyl(cyclopentyl)phosphane; dichloropalladium; iron (207 mg, 0.31 mmol, 0.1 eq) and potassium acetate (624 mg, 6.37 mmol, 2 eq) in dioxane (10 mL) was de-gassed and then heated to 100° C. for 12 hours under nitrogen. The reaction mixture was diluted with ethyl acetate (50 mL), filtered and concentrated under reduced pressure. The residue was purified by silica gel column chromatography (Petroleum ether/Ethyl acetate=50/1 to 10/1). 4-(dimethoxymethyl)-1-[4-(4,4,5,5-tetramethyl-1,3,2-dioxaborolan-2-yl)phenyl]piperidine (500 mg, 1.38 mmol, 43% yield) was obtained as a white solid. LC/MS (ESI) m/z: 362.2 $[M+1]^+$; $^1$H-NMR (400 MHz, $CDCl_3$) δ 7.71 (d, J=8.8 Hz, 2H), 6.92 (d, J=8.8 Hz, 2H), 4.08 (d, J=6.9 Hz, 1H), 3.85 (d, J=12.5 Hz, 2H), 3.39 (s, 6H), 2.75 (dt, J=2.2, 12.5 Hz, 2H), 1.91-1.75 (m, 3H), 1.49-1.38 (m, 2H), 1.35 (s, 12H).

Step 5: Preparation of (R)—N-(3-(5-(4-(4-(dimethoxymethyl)piperidin-1-yl)phenyl)-1-((2-(trimethylsilyl)ethoxy)methyl)-1H-pyrrolo[2,3-b]pyridine-3-carbonyl)-2,4-difluorophenyl)-3-fluoro-N-((2-(trimethylsilyl)ethoxy)methyl)pyrrolidine-1-sulfonamide

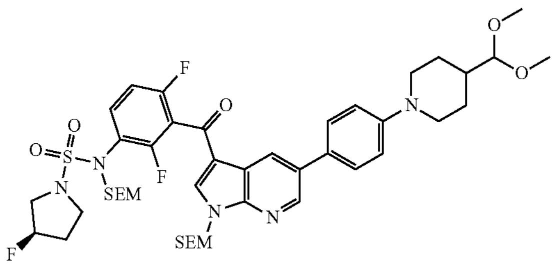 [SMILES: COC(OC)C1CCN(c2ccc(-c3cnc4c(c3)c(C(=O)c3c(F)ccc(N(COCC[Si](C)(C)C)S(=O)(=O)N5CC[C@@H](F)C5)c3F)cn4COCC[Si](C)(C)C)cc2)CC1]

4-(dimethoxymethyl)-1-[4-(4,4,5,5-tetramethyl-1,3,2-dioxaborolan-2-yl)phenyl]piperidine (800 mg, 2.21 mmol, 1 eq), (3R)—N-[3-[5-bromo-1-(2-trimethylsilylethoxymethyl) pyrrolo[2,3-b]pyridine-3-carbonyl]-2,4-difluoro-phenyl]-3-fluoro-N-(2-trimethylsilylethoxymethyl)pyrrolidine-1-sulfonamide (1.69 g, 2.21 mmol, 1 eq), cesium fluoride (1.35 g, 8.86 mmol, 4 eq) and 4-ditert-butylphosphanyl-N,N-dimethyl-aniline;dichloropalladium (156 mg, 0.22 mmol, 0.1 eq) in dioxane (15 mL) and water (1.5 mL) was de-gassed and then heated to 85° C. for 12 hours under nitrogen. The reaction mixture was diluted with water (50 mL) and extracted with ethyl acetate (50 mL×3). The combined organic layers were washed with brine (50 mL×3), dried over anhydrous sodium sulfate, filtered and concentrated under reduced pressure. The residue was purified by silica gel column chromatography (Petroleum ether/Ethyl acetate=50/1 to 5/1). (3R)—N-[3-[5-[4-[4-(dimethoxymethyl)-1-piperidyl]phenyl]-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (1.5 g, 1.63 mmol, 73% yield) was obtained as a yellow solid. LC/MS (ESI) m/z 918.1 $[M+1]^+$; $^1$H-NMR (400 MHz, DMSO-$d_6$) δ 8.72 (d, J=2.0 Hz, 1H), 8.55 (s, 1H), 8.34 (s, 1H), 7.77 (dt, J=6.0, 8.8 Hz, 1H), 7.59 (d, J=8.8 Hz, 2H), 7.43-7.36 (m, 1H), 7.06 (d, J=8.8 Hz, 2H), 5.68 (s, 2H), 5.43-5.21 (m, 1H), 5.01-4.89 (m, 2H), 4.12-4.07 (m, 1H), 3.81 (d, J=12.4 Hz, 2H), 3.68-3.61 (m, 2H), 3.57 (t, J=8.0 Hz, 2H), 3.50 (s, 1H), 3.45-3.38 (m, 2H), 3.30-3.25 (m, 7H), 2.20-2.00 (m, 2H), 1.78-1.66 (m, 3H), 1.42-1.27 (m, 2H), 1.21-1.13 (m, 1H), 0.91-0.77 (m, 4H), −0.02 (s, 9H), −0.09-−0.14 (m, 9H).

Step 6: Preparation of (R)—N-(3-(5-(4-(4-(dimethoxymethyl)piperidin-1-yl)phenyl)-1H-pyrrolo[2,3-b]pyridine-3-carbonyl)-2,4-difluorophenyl)-3-fluoropyrrolidine-1-sulfonamide

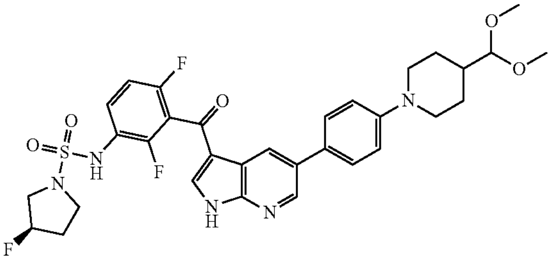 [SMILES: COC(OC)C1CCN(c2ccc(-c3cnc4[nH]cc(C(=O)c5c(F)ccc(NS(=O)(=O)N6CC[C@@H](F)C6)c5F)c4c3)cc2)CC1]

To a solution of (3S)—N-[3-[5-[4-[4-(dimethoxymethyl)-1-piperidyl]phenyl]-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (1.4 g, 1.52 mmol, 1 eq) in methanol (10 mL) was added hydrochloric acid (4 M in dioxane, 20 mL). The reaction mixture was stirred at 50° C. for 24 h. The reaction mixture was concentrated under reduced pressure. (3R)—N-[3-[5-[4-[4-(dimethoxymethyl)-1-piperidyl]phenyl]-1H-pyrrolo[2,3-b]pyridine-3-carbonyl]-2,4-difluoro-phenyl]-3-fluoro-pyrrolidine-1-sulfonamide (900 mg, 1.37 mmol, 89% yield) was obtained as a yellow solid. LC/MS (ESI) m/z: 658.1 $[M+1]^+$.

Step 7: Preparation of (R)—N-(2,4-difluoro-3-(5-(4-(4-formylpiperidin-1-yl)phenyl)-1H-pyrrolo[2,3-b]pyridine-3-carbonyl)phenyl)-3-fluoropyrrolidine-1-sulfonamide

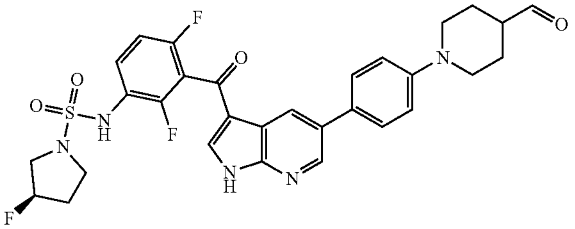 [SMILES: O=CC1CCN(c2ccc(-c3cnc4[nH]cc(C(=O)c5c(F)ccc(NS(=O)(=O)N6CC[C@@H](F)C6)c5F)c4c3)cc2)CC1]

To a solution of (3R)—N-[3-[5-[4-[4-(dimethoxymethyl)-1-piperidyl]phenyl]-1H-pyrrolo[2,3-b]pyridine-3-carbonyl]-2,4-difluoro-phenyl]-3-fluoro-pyrrolidine-1-sulfonamide (900 mg, 1.37 mmol, 1 eq) in tetrahydrofuran (18 mL) was added sulfuric acid (3 M, 18 mL, 40 eq). The reaction mixture was stirred at 50° C. for 0.5 hour. The pH was adjusted to 8 with sodium hydroxide (1 M in water), then extracted with ethyl acetate (50 mL×3). The combined organic layers were washed with brine (100 mL×2), dried over anhydrous sodium sulfate, filtered and concentrated under reduced pressure. The residue was triturated with ethyl acetate (15 mL). (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (710 mg, 1.16 mmol, 84% yield) was obtained as a yellow solid. LC/MS (ESI) m/z: 630.1 $[M+19]^+$; $^1$H-NMR (400 MHz, DMSO-$d_6$) δ 12.91 (s, 1H), 9.87 (s, 1H), 9.65 (s, 1H), 8.76-8.46 (m, 2H), 8.23-8.01 (m, 1H), 7.72-7.51 (m, 3H), 7.35-7.22 (m, 1H), 7.15-6.97 (m, 2H), 5.48-5.13 (m, 1H), 3.70 (d, J=12.8 Hz, 2H), 3.60 (t, J=6.0 Hz, 1H), 3.48 (s, 1H), 3.36-3.24 (m, 2H), 2.98-2.83 (m, 2H), 2.09 (dd, J=7.6, 12.8 Hz, 1H), 1.99-1.87 (m, 3H), 1.75 (t, J=6.4 Hz, 1H), 1.67-1.51 (m, 2H), 0.91-0.75 (m, 2H).

Step 8: Preparation of tert-butyl (S)-(1-(4-(4,4,5,5-tetramethyl-1,3,2-dioxaborolan-2-yl)phenyl)ethyl) carbamate

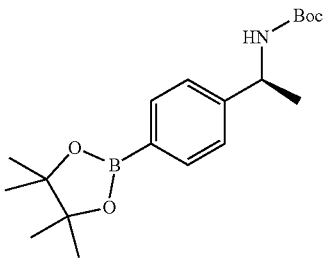 [SMILES: C[C@H](NC(=O)OC(C)(C)C)c1ccc(B2OC(C)(C)C(C)(C)O2)cc1]

To a solution of tert-butyl N-[(1S)-1-(4-bromophenyl) ethyl]carbamate (5 g, 16.66 mmol, 1 eq) and 4,4,5,5-tetramethyl-2-(4,4,5,5-tetramethyl-1,3,2-dioxaborolan-2-yl)-1,3,2-dioxaborolane (5.08 g, 19.99 mmol, 1.2 eq) in dioxane (100 mL) was added [1,1'-bis(diphenylphosphino)ferrocene] dichloropalladium(II) (974.98 mg, 1.33 mmol, 0.08 eq) and potassium acetate (3.27 g, 33.31 mmol, 2 eq). The mixture was stirred at 90° C. for 2 hours. The reaction mixture was concentrated to give crude product. The crude product was purified by silica gel chromatography (petroleum ether:ethyl acetate=1:0 to 10:1). Compound tert-butyl N-[(1S)-1-[4-(4,4,5,5-tetramethyl-1,3,2-dioxaborolan-2-yl)phenyl]ethyl] carbamate (8.2 g, 16.44 mmol, 98.7% yield, 69.6% purity) was obtained as a yellow oil. LC/MS (ESI) m/z: 370.26 $[M+23]^+$.

Step 9: Preparation of ethyl (S)-5-(4-(1-((tert-butoxycarbonyl)amino)ethyl)phenyl)thiazole-4-carboxylate

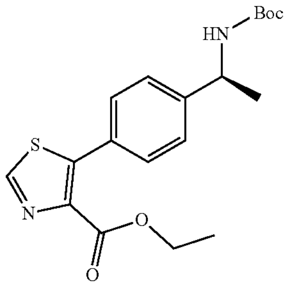 [SMILES: CCOC(=O)c1ncsc1-c1ccc([C@H](C)NC(=O)OC(C)(C)C)cc1]

A mixture of ethyl 5-bromothiazole-4-carboxylate (3.49 g, 14.77 mmol, 0.9 eq), tert-butyl N-[(1S)-1-[4-(4,4,5,5-tetramethyl-1,3,2-dioxaborolan-2-yl)phenyl]ethyl]carbamate (5.70 g, 16.41 mmol, 1 eq), [1,1'-bis(diphenylphosphino) ferrocene]dichloropalladium(II) (120 mg, 0.16 mmol, 0.01 eq), potassium carbonate (4.54 g, 32.83 mmol, 2 eq) in mixture of dioxane (130 mL) and water (22 mL) was degassed and purged with nitrogen for three times, and then the mixture was stirred at 80° C. for 10 hours under nitrogen atmosphere. The reaction mixture was concentrated and quenched with water (50 mL), then extracted with ethyl acetate (60 mL) two times. The combined organic layers were washed with saturated aqueous sodium chloride (50 mL) two times, dried over anhydrous sodium sulfate, concentrated to give crude product. The crude product was purified by silica gel chromatography (petroleum ether:ethyl acetate=1:0 to 1:1). Compound ethyl 5-[4-[(1S)-1-(tert-butoxycarbonylamino)ethyl]phenyl]thiazole-4-carboxylate (5.07 g, 13.48 mmol, 82.1% yield) was obtained as a yellow solid. LC/MS (ESI) m/z: 377.1 $[M+1]^+$; $^1H$ NMR (400 MHz, $CDCl_3$) δ 8.76 (s, 1H), 7.49 (d, J=8.0 Hz, 2H), 7.37 (d, J=8.0 Hz, 2H), 4.85 (s, 2H), 4.35-4.29 (m, 2H), 1.44 (s, 9H), 1.28 (t, J=7.2 Hz, 3H), 1.24 (s, 3H).

Step 10: Preparation of tert-butyl (S)-(1-(4-(4-(hydroxymethyl)thiazol-5-yl)phenyl)ethyl)carbamate

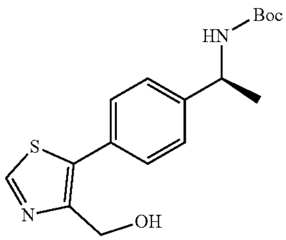 [SMILES: C[C@H](NC(=O)OC(C)(C)C)c1ccc(-c2scnc2CO)cc1]

To a mixture of ethyl 5-[4-[(1S)-1-(tert-butoxycarbonylamino)ethyl]phenyl]thiazole-4-carboxylate (900 mg, 2.39 mmol, 1 eq) and calcium chloride (796 mg, 7.17 mmol, 3 eq) in water (40 mL) and tetrahydrofuran (20 mL) was added sodium borohydride (181 mg, 4.78 mmol, 2 eq) at 0° C. under nitrogen. The mixture was warmed to 5° C. stirred for 2 hours. Then hydrochloric acid (5 M, 4.50 mL) and acetone (4.95 mL) was added at 0° C., the reaction mixture was stirred at 5° C. for another 0.5 h. The pH was adjusted to 5 with 5 M sodium hydroxide. The aqueous phase was extracted with ethyl acetate (20 mL×4). The combined organic phase was washed with brine (20 mL×2), dried with anhydrous sodium sulfate, filtered and concentrated under vacuum. The residue was purified by semi-preparative reverse phase HPLC. Compound tert-butyl N-[(1S)-1-[4-[4-(hydroxymethyl)thiazol-5-yl]phenyl]ethyl]carbamate (400 mg, 1.20 mmol, 50.0% yield) was obtained as a white solid. LC/MS (ESI) m/z: 335.2 $[M+1]^+$.

Step 11: Preparation of (S)-(5-(4-(1-aminoethyl) phenyl)thiazol-4-yl)methanol

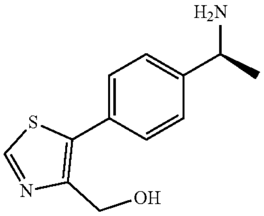 [SMILES: C[C@H](N)c1ccc(-c2scnc2CO)cc1]

A mixture of tert-butyl N-[(1S)-1-[4-[4-(hydroxymethyl) thiazol-5-yl]phenyl]ethyl]carbamate (0.4 g, 1.20 mmol, 1 eq) in dichloromethane (1.5 mL) was added hydrochloric acid/dioxane (4 M, 10 mL) at 15° C. The mixture was stirred at 15° C. for 2 h. The mixture was concentrated in reduced pressure at 45° C. Compound [5-[4-[(1S)-1-aminoethyl]phenyl]thiazol-4-yl]methanol (380 mg, crude, hydrochloride) was obtained as a white solid.

Step 12: Preparation of tert-butyl (2S,4R)-4-hydroxy-2-(((S)-1-(4-(4-(hydroxymethyl)thiazol-5-yl)phenyl)ethyl)carbamoyl)pyrrolidine-1-carboxylate

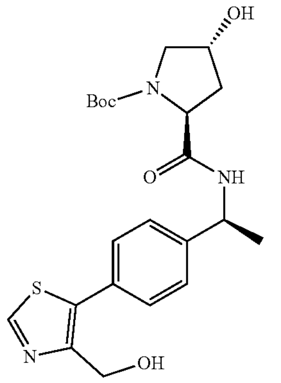 [SMILES: C[C@H](NC(=O)[C@@H]1C[C@@H](O)CN1C(=O)OC(C)(C)C)c1ccc(-c2scnc2CO)cc1]

To a mixture of [5-[4-[(1S)-1-aminoethyl]phenyl]thiazol-4-yl]methanol (328 mg, 1.21 mmol, 1.00 eq, hydrochloride) and (2S,4R)-1-tert-butoxycarbonyl-4-hydroxy-pyrrolidine-2-carboxylic acid (280 mg, 1.21 mmol, 1 eq) in N,N-dimethylformamide (15 mL) was added 1-(3-dimethylaminopropyl)-3-ethylcarbodiimide hydrochloride (348 mg, 1.82 mmol, 1.5 eq), 1-hydroxybenzotriazole (245 mg, 1.82 mmol, 1.5 eq) and N,N-diisopropylethylamine (782 mg, 6.05 mmol, 1.05 mL, 5 eq) in one portion at 15° C. under nitrogen. The mixture was stirred at 15° C. for 16 hours. The mixture was concentrated under reduced pressure at 45° C. The residue was purified by semi-preparative reverse phase HPLC. Compound tert-butyl (2S,4R)-4-hydroxy-2-[[(1S)-1-[4-[4-(hydroxymethyl)thiazol-5-yl]phenyl]ethyl]carbamoyl]pyrrolidine-1-carboxylate (370 mg, 0.83 mmol, 68% yield) was obtained as a white solid. LC/MS (ESI) m/z: 448.2 $[M+1]^+$.

Step 13: Preparation of (2S,4R)-4-hydroxy-N—((S)-1-(4-(4-(hydroxymethyl)thiazol-5-yl)phenyl)ethyl)pyrrolidine-2-carboxamide

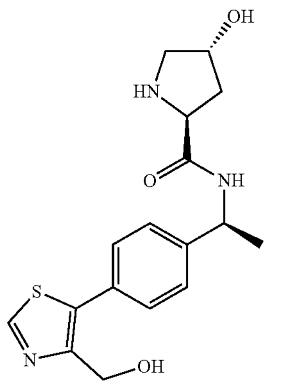 [SMILES: C[C@H](NC(=O)[C@@H]1C[C@@H](O)CN1)c1ccc(-c2scnc2CO)cc1]

A solution of tert-butyl (2S,4R)-4-hydroxy-2-[[(1S)-1-[4-[4-(hydroxymethyl)thiazol-5-yl]phenyl]ethyl]carbamoyl]pyrrolidine-1-carboxylate (0.39 g, 0.87 mmol, 1 eq) in dichloromethane (1 mL) was added hydrochloric acid/dioxane (4 M, 10 mL) was stirred at 15° C. for 1 h. The mixture was concentrated under reduced pressure at 45° C. (2S,4R)-4-hydroxy-N-[(1S)-1-[4-[4-(hydroxymethyl)thiazol-5-yl]phenyl]ethyl]pyrrolidine-2-carboxamide (360 mg, crude, hydrochloride) was obtained as white solid.

Step 14: Preparation of tert-butyl ((S)-1-((2S,4R)-4-hydroxy-2-(((S)-1-(4-(4-(hydroxymethyl)thiazol-5-yl)phenyl)ethyl)carbamoyl)pyrrolidin-1-yl)-3,3-dimethyl-1-oxobutan-2-yl)carbamate

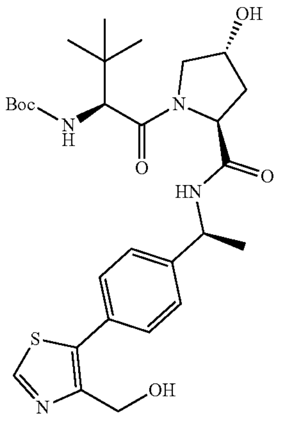 [SMILES: C[C@H](NC(=O)[C@@H]1C[C@@H](O)CN1C(=O)[C@@H](NC(=O)OC(C)(C)C)C(C)(C)C)c1ccc(-c2scnc2CO)cc1]

A solution of (2S,4R)-4-hydroxy-N-[(1S)-1-[4-[4-(hydroxymethyl)thiazol-5-yl]phenyl]ethyl]pyrrolidine-2-carboxamide (706 mg, 1.84 mmol, 1 eq, hydrochloride), (2S)-2-(tert-butoxycarbonylamino)-3,3-dimethyl-butanoic acid (425 mg, 1.84 mmol, 1 eq), hydroxybenzotriazole (298 mg, 2.21 mmol, 1.2 eq), diisopropylethylamine (1.43 g, 11.04 mmol, 6 eq), carbodiimide hydrochloride (705 mg, 3.68 mmol, 2 eq) in N, N-dimethyl formamide (40 mL) was stirred at 20° C. for 12 h. The reaction solution was washed with water (100 mL). The aqueous layer was extracted with ethyl acetate (40 mL×8). All the combined organic layers were washed with brine, dried over sodium sulfate, filtered and concentrated under reduced pressure. The residue (dichloromethane:methanol=10:1) was purified by column chromatography on silica gel (ethyl acetate:methanol=1:0) to give a white solid. Tert-butyl N-[(1S)-1-[(2S,4R)-4-hydroxy-2-[[(1S)-1-[4-[4-(hydroxymethyl)thiazol-5-yl]phenyl]ethyl]carbamoyl]pyrrolidine-1-carbonyl]-2,2-dimethyl-propyl]carbamate (400 mg, 0.71 mmol, 38% yield, 99% purity) was obtained as a white solid. LC/MS (ESI) m/z: 561.3 $[M+1]^+$.

Step 15: Preparation of (2S,4R)-1-((S)-2-amino-3,3-dimethylbutanoyl)-4-hydroxy-N—((S)-1-(4-(4-(hydroxymethyl)thiazol-5-yl)phenyl)ethyl)pyrrolidine-2-carboxamide

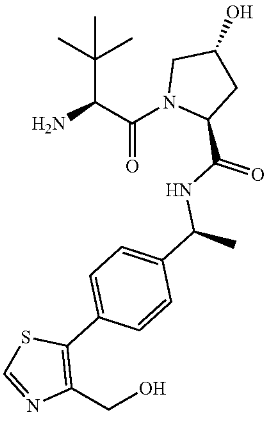 [SMILES: C[C@H](NC(=O)[C@@H]1C[C@@H](O)CN1C(=O)[C@@H](N)C(C)(C)C)c1ccc(-c2scnc2CO)cc1]

To a solution of tert-butyl N-[(1S)-1-[(2S,4R)-4-hydroxy-2-[[(1S)-1-[4-[4-(hydroxymethyl) thiazol-5-yl]phenyl] ethyl]carbamoyl]pyrrolidine-1-carbonyl]-2,2-dimethyl-propyl]carbamate (400 mg, 0.71 mmol, 1 eq) in dichloromethane (20 mL) was added hydrochloric acid/dioxane (4 M, 20 mL, 113.10 eq). The mixture was stirred at 20° C. for 20 min. The mixture was concentrated to give a white solid. The white solid was used for next step without further purification. (2S,4R)-1-[(2S)-2-amino-3,3-dimethyl-butanoyl]-4-hydroxy-N-[(1S)-1-[4-[4-(hydroxymethyl)thiazol-5-yl]phenyl]ethyl]pyrrolidine-2-carboxamide (351 mg, crude, hydrochloride) was obtained as a white solid. LC/MS (ESI) m/z: 461.2 [M+1]$^+$.

Step 16: Preparation of tert-butyl 4-(2-(((S)-1-((2S,4R)-4-hydroxy-2-(((S)-1-(4-(4-(hydroxymethyl)thiazol-5-yl)phenyl)ethyl)carbamoyl)pyrrolidin-1-yl)-3,3-dimethyl-1-oxobutan-2-yl(amino)-2-oxoethyl (piperazine-1-carboxylate

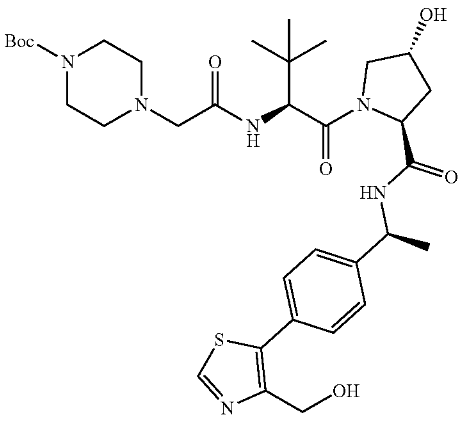 [SMILES: C[C@H](NC(=O)[C@@H]1C[C@@H](O)CN1C(=O)[C@@H](NC(=O)CN1CCN(C(=O)OC(C)(C)C)CC1)C(C)(C)C)c1ccc(-c2scnc2CO)cc1]

A solution of (2S,4R)-1-[(2S)-2-amino-3,3-dimethyl-butanoyl]-4-hydroxy-N-[(1S)-1-[4-[4-(hydroxymethyl)thiazol-5-yl]phenyl]ethyl]pyrrolidine-2-carboxamide (351 mg, 0.70 mmol, 1 eq, hydrochloride), 2-(4-tert-butoxycarbonylpiperazin-1-yl)acetic acid (172 mg, 0.70 mmol, 1 eq), hydroxybenzotriazole (114 mg, 0.85 mmol, 1.2 eq), diisopropylethylamine (548 mg, 4.24 mmol, 6 eq), carbodiimide hydrochloride (271 mg, 1.41 mmol, 2 eq) in N, N-dimethyl formamide (20 mL) was stirred at 20° C. for 12 h. The reaction solution was washed with water (100 mL). The aqueous layer was extracted with ethyl acetate (40 mL×8). All the combined organic layers were washed with brine, dried over sodium sulfate, filtered and concentrated under reduced pressure. The residue (dichloromethane:methanol=10:1) was purified by column chromatography on silica gel (ethyl acetate:methanol=1:0) to give tert-butyl 4-[2-[[(1S)-1-[(2S,4R)-4-hydroxy-2-[[(1S)-1-[4-[4-(hydroxymethyl)thiazol-5-yl]phenyl]ethyl]carbamoyl]pyrrolidine-1-carbonyl]-2,2-dimethyl-propyl]amino]-2-oxo-ethyl] piperazine-1-carboxylate (340 mg, 0.48 mmol, 68% yield, 97% purity) as a white solid. LC/MS (ESI) m/z: 687.4 [M+1]$^+$.

Step 17: Preparation of (2S,4R)-1-((S)-3,3-dimethyl-2-(2-(piperazin-1-yl)acetamido)butanoyl)-4-hydroxy-N—((S)-1-(4-(4-(hydroxymethyl)thiazol-5-yl)phenyl)ethyl)pyrrolidine-2-carboxamide

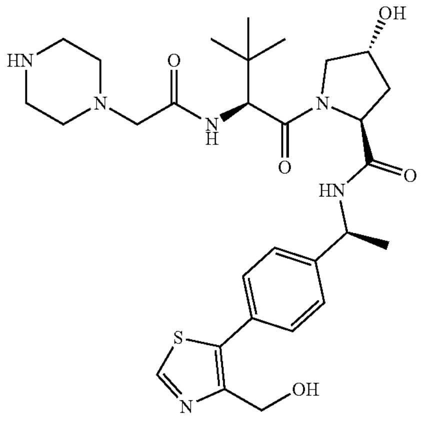 [SMILES: C[C@H](NC(=O)[C@@H]1C[C@@H](O)CN1C(=O)[C@@H](NC(=O)CN1CCNCC1)C(C)(C)C)c1ccc(-c2scnc2CO)cc1]

To a solution of tert-butyl 4-[2-[[(1S)-1-[(2S,4R)-4-hydroxy-2-[[(1S)-1-[4-[4-(hydroxymethyl) thiazol-5-yl]phenyl]ethyl]carbamoyl]pyrrolidine-1-carbonyl]-2,2-dimethyl-propyl]amino]-2-oxo-ethyl]piperazine-1-carboxylate (340 mg, 0.48 mmol, 1 eq) in dichloromethane (10 mL) was added hydrochloric acid/dioxane (4 M, 20 mL, 165.66 eq). The mixture was stirred at 20° C. for 20 min. The mixture was concentrated to give a white solid. The white solid was used for next step without further purification. (2S,4R)-1-[(2S)-3,3-dimethyl-2-[(2-piperazin-1-ylacetyl)amino]butanoyl]-4-hydro xy-N-[(1S)-1-[4-[4-(hydroxymethyl)thiazol-5-yl]phenyl]ethyl]pyrrolidine-2-carboxamide (300 mg, crude, hydrochloride) was obtained as a white solid. LC/MS (ESI) m/z: 587.4 [M+1]$^+$.

Step 18: Preparation of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N—((S)-1-(4-(4-(hydroxymethyl)thiazol-5-yl)phenyl)ethyl)pyrrolidine-2-carboxamide

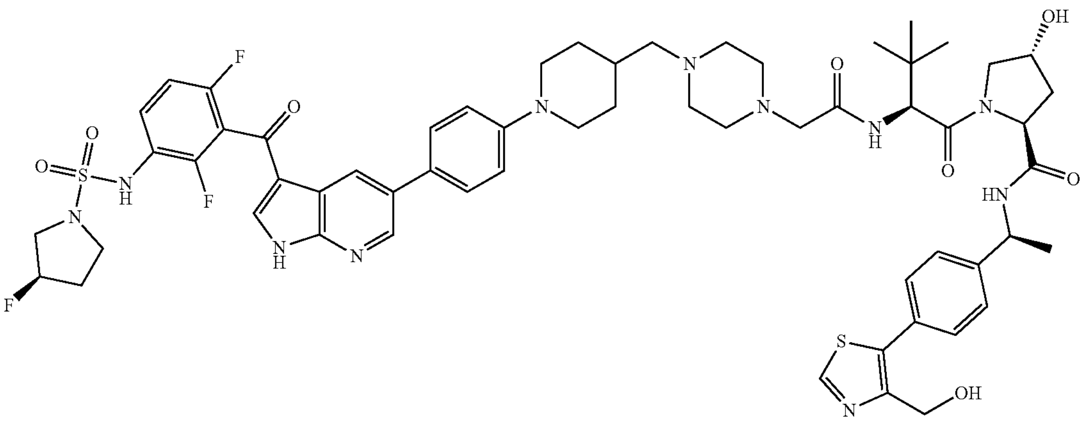 [SMILES: C[C@H](NC(=O)[C@@H]1C[C@@H](O)CN1C(=O)[C@@H](NC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1)C(C)(C)C)c1ccc(-c2scnc2CO)cc1]

A solution of (2S,4R)-1-[(2S)-3,3-dimethyl-2-[(2-piperazin-1-ylacetyl)amino]butanoyl]-4-hydroxy-N-[(1S)-1-[4-[4-(hydroxymethyl)thiazol-5-yl]phenyl]ethyl]pyrrolidine-2-carboxamide (200 mg, 0.32 mmol, 1 eq, hydrochloride) in dichloroethane (8 mL) was added triethylamine (195 mg, 1.93 mmol, 6 eq). The mixture was stirred at 20° C. for 20 min. Then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (196 mg, 0.32 mmol, 1 eq) was added to the mixture. The mixture was stirred at 20° C. for 20 min. Then Sodium triacetoxyborohydride (204 mg, 0.96 mmol, 3 eq) was added to the mixture. The mixture was stirred at 20° C. for 3 h. The reaction solution was washed with water (20 mL). The aqueous layer was extracted with ethyl acetate (20 mL×6). All the combined organic layers were washed with brine, dried over sodium sulfate, filtered and concentrated under reduced pressure. The residue was purified by prep-High Performance Liquid Chromatography to give a yellow solid. (2S,4R)-1-[(2S)-2-[[2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]acetyl]amino]-3,3-dimethyl-butanoyl]-4-hydroxy-N-[(1S)-1-[4-[4-(hydroxymethyl)thiazol-5-yl]phenyl]ethyl]pyrrolidine-2-carboxamide (148 mg, 0.12 mmol, 37% yield, 95% purity) was obtained as a yellow solid. LC/MS (ESI) m/z: 1182.4 $[M+1]^+$; $^1$H-NMR (400 MHz, DMSO-$d_6$) δ 12.94 (s, 1H), 9.85 (s, 1H), 9.03 (d, J=2.8 Hz, 1H), 8.66 (d, J=2.0 Hz, 1H), 8.56 (s, 1H), 8.41 (d, J=8.0 Hz, 1H), 8.09 (s, 1H), 7.70-7.58 (m, 3H), 7.58-7.51 (m, 2H), 7.43-7.32 (m, 2H), 7.27 (m, 1H), 7.16 (d, J=8.0 Hz, 2H), 5.43-5.19 (m, 2H), 5.01-4.83 (m, 1H), 4.61-4.48 (m, 10H), 4.47-4.40 (m, 4H), 4.33-4.02 (m, 1H), 3.82 (br d, J=11.6 Hz, 2H), 3.69-3.46 (m, 5H), 3.06-2.79 (m, 6H), 2.24-1.58 (m, 8H), 1.52-1.29 (m, 5H), 1.04-0.88 (m, 9H).

Exemplary Synthesis of (2S,4R)-1-((R)-2-(3-(4-((1-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperidin-4-yl)methyl)piperazin-1-yl)isoxazol-5-yl)-3-methylbutanoyl)-4-hydroxy-N—((S)-1-(4-(4-methylthiazol-5-yl)phenyl)ethyl)pyrrolidine-2-carboxamide (Example 403)

Step 1: Preparation of benzyl 4-(dimethoxymethyl)piperidine-1-carboxylate

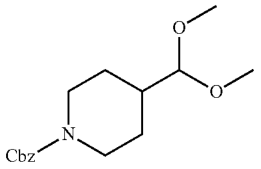 [SMILES: COC(OC)C1CCN(C(=O)OCc2ccccc2)CC1]

To a solution of benzyl 4-formylpiperidine-1-carboxylate (25 g, 101.10 mmol, 1 eq) in methanol (230 mL) was added p-toluenesulfonic acid (961 mg, 5.05 mmol, 0.05 eq) and trimethoxymethane (53.64 g, 505.48 mmol, 55 mL, 5 eq). The mixture was stirred at 25° C. for 12 hours. Saturated aqueous sodium bicarbonate (50 mL) was poured into the mixture to pH=8. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=30:1 to 10:1). Compound benzyl 4-(dimethoxymethyl)piperidine-1-carboxylate (29 g, 98.86 mmol, 97% yield) was obtained as a colorless oil. LC/MS (ESI) m/z: 316 $[M+23]^+$.

Step 2: Preparation of 4-(dimethoxymethyl)piperidine

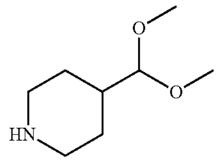

To a solution of benzyl 4-(dimethoxymethyl)piperidine-1-carboxylate (29 g, 98.86 mmol, 1 eq) in methanol (200 mL) was added palladium on carbon (2 g, 10% purity) under nitrogen atmosphere. The suspension was degassed and purged with hydrogen for 3 times. The mixture was stirred under hydrogen (50 Psi) at 25° C. for 12 hours. The reaction mixture was filtered and the filter was concentrated. The crude product was used into the next step without further purification. Compound 4-(dimethoxymethyl)piperidine (14.9 g, 93.58 mmol, 94% yield) was obtained as a light yellow oil. LC/MS (ESI) m/z: 160.2 $[M+1]^+$; $^1$H-NMR (400 MHz, $CDCl_3$) δ 4.03 (d, J=7.2 Hz, 1H), 3.34 (s, 6H), 3.28 (s, 1H), 3.17-3.10 (m, 2H), 2.60 (dt, J=2.4, 12.4 Hz, 2H), 1.79-1.67 (m, 3H), 1.33-1.20 (m, 2H).

Step 3: Preparation of 5-bromo-2-(4-(dimethoxymethyl)piperidin-1-yl)pyrimidine

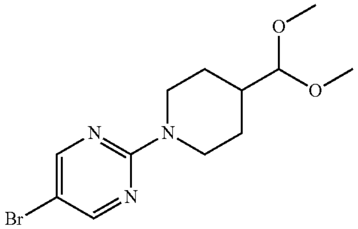 [SMILES: COC(OC)C1CCN(c2ncc(Br)cn2)CC1]

To a solution of 5-bromo-2-chloro-pyrimidine (1.21 g, 6.28 mmol, 1 eq) and 4-(dimethoxymethyl)piperidine (1.0 g, 6.28 mmol, 1 eq) in acetonitrile (20 mL) was added potassium carbonate (1.74 g, 12.56 mmol, 2 eq). The mixture was stirred at 70° C. for 12 h. The reaction mixture was extracted with ethyl acetate (40 mL×2) and washed with saturated aqueous brine (25 mL×2). The combined organic layers were dried over anhydrous sodium sulfate, filtered and concentrated under reduced pressure. The residue was purified by silica gel chromatography (petroleum ether/ethyl acetate=10:1 to 2:1). Compound 5-bromo-2-[4-(dimethoxymethyl)-1-piperidyl]pyrimidine (1.46 g, 4.62 mmol, 73% yield) was obtained as a white solid. $^1$H NMR (400 MHz, $CDCl_3$) δ 8.27 (s, 2H), 4.77-4.67 (m, 2H), 4.05 (d, J=7.2 Hz, 1H), 3.37 (s, 6H), 2.83 (dt, J=2.8, 13.2 Hz, 2H), 1.95-1.79 (m, 3H), 1.33-1.22 (m, 2H).

Step 4: Preparation of (R)—N-(3-(5-(2-(4-(dimethoxymethyl)piperidin-1-yl)pyrimidin-5-yl)-1-((2-(trimethylsilyl)ethoxy)methyl)-1H-pyrrolo[2,3-b]pyridine-3-carbonyl)-2,4-difluorophenyl)-3-fluoro-N-((2-(trimethylsilyl)ethoxy)methyl)pyrrolidine-1-sulfonamide

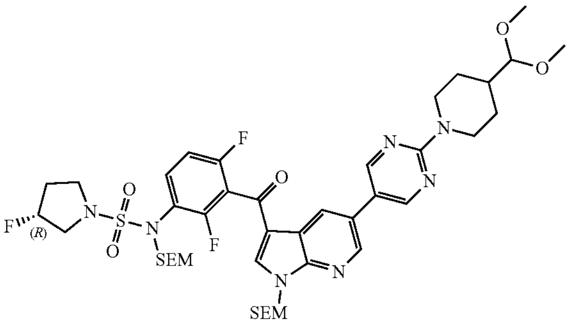

A mixture of 5-bromo-2-[4-(dimethoxymethyl)-1-piperidyl]pyrimidine (327 mg, 1.04 mmol, 1.2 eq), (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (700 mg, 0.86 mmol, 1 eq), cesium fluoride (524 mg, 3.45 mmol, 0.1 mL, 4 eq) and 4-ditert-butylphosphanyl-N,N-dimethyl-aniline; dichloropalladium (61 mg, 0.09 mmol, 0.1 eq) in dioxane (5 mL) and water (1 mL) was degassed and purged with nitrogen for 3 times, and then the mixture was stirred at 90° C. for 12 h under nitrogen atmosphere. The reaction mixture was extracted with ethyl acetate (30 mL×2) and washed with saturated aqueous brine (30 mL×2). The combined organic layers were dried over anhydrous sodium sulfate, filtered and concentrated under reduced pressure. The residue was purified by preparative reverse phase HPLC. Compound (3R)—N-[3-[5-[2-[4-(dimethoxymethyl)-1-piperidyl]pyrimidin-5-yl]-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (445 mg, 0.45 mmol, 52% yield, 97% purity, formate) was obtained as a brown solid. LC/MS (ESI) m/z: 920.5 $[M+1]^+$.

Step 5: Preparation of (R)—N-(3-(5-(2-(4-(dimethoxymethyl)piperidin-1-yl)pyrimidin-5-yl)-1H-pyrrolo[2,3-b]pyridine-3-carbonyl)-2,4-difluorophenyl)-3-fluoropyrrolidine-1-sulfonamide

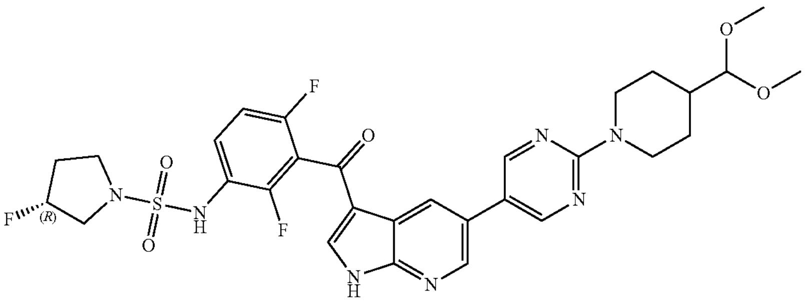

To a solution of (3R)—N-[3-[5-[2-[4-(dimethoxymethyl)-1-piperidyl]pyrimidin-5-yl]-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (680 mg, 0.70 mmol, 1 eq, formate) in methanol (3 mL) was added hydrochloric acid (4 M in dioxane, 8 mL). The mixture was stirred at 50° C. for 24 h. The reaction mixture was concentrated under vacuum. Compound (3R)—N-[3-[5-[2-[4-(dimethoxymethyl)-1-piperidyl]pyrimidin-5-yl]-1H-pyrrolo[2,3-b]pyridine-3-carbonyl]-2,4-difluoro-phenyl]-3-fluoro-pyrrolidine-1-sulfonamide (560 mg, crude) was obtained as a yellow solid, which was directly used into the next step without further purification. LC/MS (ESI) m/z: 684.4 $[M+23]^+$.

Step 6: Preparation of (R)—N-(2,4-difluoro-3-(5-(2-(4-formylpiperidin-1-yl)pyrimidin-5-yl)-1H-pyrrolo[2,3-b]pyridine-3-carbonyl)phenyl)-3-fluoropyrrolidine-1-sulfonamide

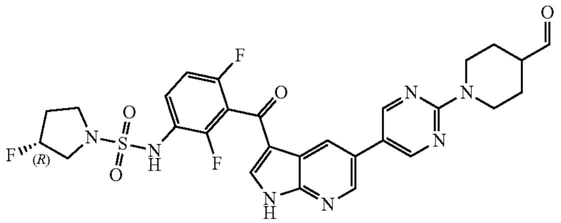

To a solution of (3R)—N-[3-[5-[2-[4-(dimethoxymethyl)-1-piperidyl]pyrimidin-5-yl]-1H-pyrrolo[2,3-b]pyridine-3-carbonyl]-2,4-difluoro-phenyl]-3-fluoro-pyrrolidine-1-sulfonamide (560 mg, 0.85 mmol, 1 eq) in tetrahydrofuran (10 mL) was added sulfuric acid (2 M, 15 mL, 35.34 eq). The mixture was stirred at 70° C. for 4 h. The reaction mixture was basified with saturated sodium bicarbonate to pH=7~8. Then the reaction mixture was extracted with ethyl acetate (30 mL×2) and washed with saturated brine (25 mL×2). The combined organic layers were dried over anhydrous sodium sulfate, filtered and concentrated under reduced pressure. The residue was purified by Semi-preparative reverse phase HPLC. Compound (3R)—N-[2,4-difluoro-3-[5-[2-(4-formyl-1-piperidyl)pyrimidin-5-yl]-1H-pyrrolo[2,3-b]pyridine-3-carbonyl]phenyl]-3-fluoro-pyrrolidine-1-sulfonamide (340 mg, 0.55 mmol, 65% yield) was obtained as a yellow solid. LC/MS (ESI) m/z: 614.3 $[M+1]^+$; $^1$H-NMR (400 MHz, DMSO-$d_6$) δ 12.95 (s, 1H), 9.65 (s, 1H), 8.75 (s, 2H), 8.65 (s, 1H), 8.54 (s, 1H), 8.09 (s, 1H), 7.67-7.53 (m, 1H), 7.23 (t, J=8.8 Hz, 1H), 5.40-5.18 (m, 1H), 4.52 (d, J=13.2 Hz, 2H), 3.46 (s, 1H), 3.38 (s, 3H), 3.27-3.20 (m, 3H), 2.75-2.60 (m, 1H), 2.08 (d, J=13.2 Hz, 2H), 2.00-1.88 (m, 2H), 1.58-1.41 (m, 2H).

Step 7: Preparation of methyl 3-(benzyloxy)isoxazole-5-carboxylate

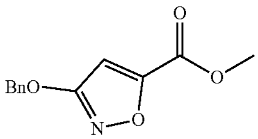 [SMILES: COC(=O)c1cc(OCc2ccccc2)no1]

To a solution of methyl 3-hydroxyisoxazole-5-carboxylate (7.20 g, 50.31 mmol, 1.00 eq) in acetone (150 mL) was added potassium carbonate (13.91 g, 100.62 mmol, 2.00 eq). The mixture was heated to 80° C. for 1 hr, then (bromomethyl) benzene (10.33 g, 60.37 mmol, 1.20 eq) was added. The resulting mixture was stirred at 80° C. for another 3 hr. The solid was filtered off and the filtrated was concentrated in vacuum. The residue was further purified by silica gel column chromatography (Petroleum ether:Ethyl acetate=15:1 to 10:1) to afford methyl 3-benzyloxyisoxazole-5-carboxylate (9.50 g, 40.73 mmol, 81% yield) as a colorless oil. The oil was solidified after standing at 15° C. for 15 hr. LC/MS (ESI) m/z: 256.0 $[M+23]^+$; $^1$H-NMR (400 MHz, $CDCl_3$) δ 7.49-7.41 (m, 5H), 6.60 (s, 1H), 5.34 (s, 2H), 3.97 (s, 3H).

Step 8: Preparation of (3-(benzyloxy)isoxazol-5-yl)methanol

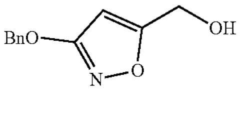 [SMILES: OCc1cc(OCc2ccccc2)no1]

To a solution of methyl 3-benzyloxyisoxazole-5-carboxylate (2.33 g, 9.99 mmol, 1.00 eq) in methanol (50 mL) was added sodium borohydride (756 mg, 19.98 mmol, 2.00 eq) in portions. The resulting mixture was stirred at 15° C. for 3 hr. The mixture was poured into hydrochloric acid (0.2 M, 200 mL), and then extracted with ethyl acetate (150 mL×2). The combined organic layers were washed with saturated brine (200 mL×2), dried over anhydrous sodium sulfate, filtered and concentrated in vacuum to afford (3-benzyloxyisoxazol-5-yl)methanol (1.85 g, 9.02 mmol, 90% yield) as colorless oil. LC/MS (ESI) m/z: 206.1 $[M+1]^+$.

Step 9: Preparation of 2-(3-(benzyloxy)isoxazol-5-yl)acetonitrile

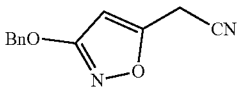 [SMILES: N#CCc1cc(OCc2ccccc2)no1]

To a solution of cyanic bromide (334 mg, 3.15 mmol, 1.05 eq) and triphenylphosphine (787 mg, 3.00 mmol, 1.00 eq) in dichloromethane (10 mL) was added a solution of (3-benzyl oxyisoxazol-5-yl)methanol (616 mg, 3.00 mmol, 1.00 eq) in dichloromethane (10 mL). The mixture was stirred at 15° C. for 1 hour, then 2,3,4,6,7,8,9,10-octahydropyrimido [1,2-a] azepine (480 mg, 3.15 mmol, 1.05 eq) was added at 0° C. The resulting mixture was stirred at 0~15° C. for another 14 hr. The solvent was concentrated in vacuum. The residue was further purified by silica gel column chromatography (Petroleum ether:Ethyl acetate=5:1 to 4:1) to afford 2-(3-benzyloxyisoxazol-5-yl)acetonitrile (320 mg, 1.49 mmol, 50% yield) as a colorless oil. LC/MS (ESI) m/z: 215.0 $[M+1]^+$; $^1$H-NMR (400 MHz, $CDCl_3$) δ 7.48-7.41 (m, 5H), 6.06 (s, 1H), 5.30 (s, 2H), 3.82 (s, 2H).

Step 10: Preparation of 2-(3-(benzyloxy)isoxazol-5-yl)-3-methylbutanenitrile

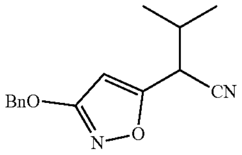 [SMILES: CC(C)C(C#N)c1cc(OCc2ccccc2)no1]

To a solution of 2-(3-benzyloxyisoxazol-5-yl)acetonitrile (214 mg, 1.00 mmol, 1.00 eq) in N,N-dimethylformamide (3 mL) was added potassium carbonate (138 mg, 1.00 mmol, 1.00 eq). The mixture was stirred at 15° C. for half an hour, then 2-iodopropane (170 mg, 1.00 mmol, 1.00 eq) was added. The resulting mixture was stirred at 15° C. for another 2.5 hr. Then potassium;2-methylpropan-2-olate (90 mg, 0.8 mmol, 0.80 eq) was added to the mixture, the mixture was stirred at 15° C. for another 12 hr. The mixture was poured into hydrochloric acid (0.2 M, 30 mL), then extracted with ethyl acetate (30 mL×2). The combined organic layers were dried over anhydrous sodium sulfate, filtered and concentrated in vacuum. The residue was purified by silica gel column chromatography (Petroleum ether: Ethyl acetate=10:1 to 8:1) to afford 2-(3-benzyloxyisoxazol-5-yl)-3-methyl-butanenitrile (150 mg, 0.56 mmol, 59% yield) as a colorless oil. $^1$H-NMR (400 MHz, $CDCl_3$) δ 7.48-7.41 (m, 5H), 6.04 (s, 1H), 5.28 (s, 2H), 3.85 (d, J=5.6 Hz, 1H), 2.42-2.37 (m, 1H), 1.18 (d, J=6.8 Hz, 3H), 1.10 (d, J=6.8 Hz, 3H).

Step 11: Preparation of 2-(3-hydroxyisoxazol-5-yl)-3-methylbutanoic acid

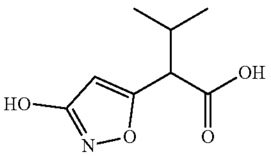

To a solution of 2-(3-benzyloxyisoxazol-5-yl)-3-methyl-butanenitrile (3.40 g, 13.27 mmol, 1.00 eq) in dioxane (30 mL) was added hydrochloric acid (11.8 M, 120 mL). The mixture was heated to 100° C. and stirred at 100° C. for 15 hr. The mixture was cooled to 15° C., and then extracted with ethyl acetate (150 mL×3). The combined organic layers were dried over anhydrous sodium sulfate, filtered and concentrated in vacuum. The crude product was further purified by prep-HPLC to afford 2-(3-hydroxyisoxazol-5-yl)-3-methyl-butanoic acid (230 mg, 1.19 mmol, 9% yield) as a yellow solid. LC/MS (ESI) m/z: 186.1 $[M+1]^+$.

Step 12: Preparation of methyl 2-(3-hydroxyisoxazol-5-yl)-3-methylbutanoate

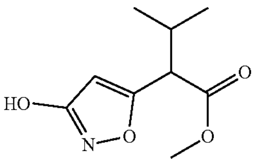

To a solution of 2-(3-hydroxyisoxazol-5-yl)-3-methyl-butanoic acid (1 g, 5.40 mmol, 1 eq) in methanol (10 mL) was added thionyl chloride (2.57 g, 21 mmol, 1.57 mL, 4 eq) at 0° C. The reaction mixture was stirred at 70° C. for 3 hours. The reaction mixture was concentrated under reduced pressure. The residue was diluted with water (50 ml) and extracted with ethyl acetate (30 mL×3). The combined organic layers were washed with brine (80 mL×2), dried over anhydrous sodium sulfate, filtered and concentrated under reduced pressure. Methyl 2-(3-hydroxyisoxazol-5-yl)-3-methyl-butanoate (1 g, 5.02 mmol, 92% yield) was obtained as a yellow oil. LC/MS (ESI) m/z: 200.1 $[M+1]^+$.

Step 13: Preparation of methyl 3-methyl-2-(3-(((perfluorobutyl)sulfonyl)oxy)isoxazol-5-yl)butanoate

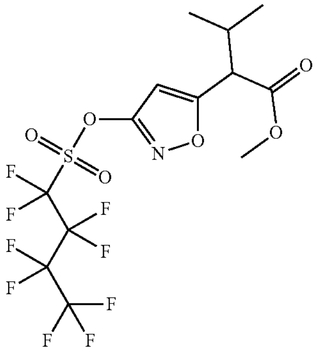 [SMILES: COC(=O)C(c1cc(OS(=O)(=O)C(F)(F)C(F)(F)C(F)(F)C(F)(F)F)no1)C(C)C]

To a solution of methyl 2-(3-hydroxyisoxazol-5-yl)-3-methyl-butanoate (800 mg, 4.02 mmol, 1 eq) in acetonitrile (5 mL) was added potassium carbonate (1.11 g, 8.03 mmol, 2 eq) and perfluorobutyl sulfonyl fluoride (1.46 g, 4.82 mmol, 1.2 eq). The reaction mixture was stirred at 25° C. for 12 hours. The reaction mixture was diluted with water (50 mL) and extracted with ethyl acetate (30 mL×3). The combined organic layers were washed with brine (80 mL×3), dried over anhydrous sodium sulfate, filtered and concentrated under reduced pressure. The residue was purified by silica gel column chromatography (Petroleum ether/Ethyl acetate=100/1 to 20/1). methyl 3-methyl-2-[3-(1,1,2,2,3,3,4,4,4-nonafluorobutylsulfonyloxy)isoxazol-5-yl] butanoate (530 mg, 1.10 mmol, 27% yield) was obtained as a colorless oil. $^1$H NMR (400 MHz, DMSO-$d_6$) δ 6.44 (s, 1H), 3.79 (s, 3H), 3.68 (d, J=8.0 Hz, 1H), 2.49-2.33 (m, 1H), 1.04 (d, J=6.8 Hz, 3H), 0.96 (d, J=6.8 Hz, 3H).

Step 14: Preparation of tert-butyl 4-(5-(1-methoxy-3-methyl-1-oxobutan-2-yl)isoxazol-3-yl)piperazine-1-carboxylate

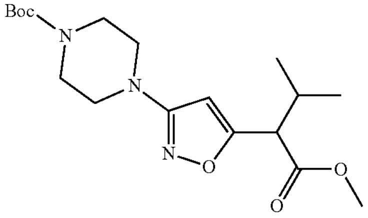 [SMILES: COC(=O)C(c1cc(N2CCN(C(=O)OC(C)(C)C)CC2)no1)C(C)C]

A solution of methyl 3-methyl-2-[3-(1,1,2,2,3,3,4,4,4-nonafluorobutylsulfonyloxy) isoxazol-5-yl]butanoate (400 mg, 0.83 mmol, 1 eq) and tert-butyl piperazine-1-carboxylate (154 mg, 0.83 mmol, 1 eq) in dimethyl formamide (5 mL) was stirred at 130° C. for 12 hours. The reaction mixture was diluted with water (30 mL) and extracted with ethyl acetate (30 mL×3). The combined organic layers were washed with brine (30 mL×3), dried over anhydrous sodium sulfate, filtered and concentrated under reduced pressure. The residue was purified by prep-TLC (Petroleum ether: Ethyl acetate=3:1). Tert-butyl 4-[5-(1-methoxycarbonyl-2-methyl-propyl)isoxazol-3-yl]piperazine-1-carboxylate (130 mg, 0.35 mmol, 42% yield) was obtained as a colorless oil. $^1$H NMR (400 MHz, $CDCl_3$) δ 5.93 (s, 1H), 3.73 (s, 3H), 3.58-3.47 (m, 5H), 3.29-3.19 (m, 4H), 2.43-2.17 (m, 1H), 1.48 (s, 9H), 1.00 (d, J=6.8 Hz, 3H), 0.93 (d, J=6.8 Hz, 3H).

Step 15: Preparation of 2-(3-(4-(tert-butoxycarbonyl)piperazin-1-yl)isoxazol-5-yl)-3-methylbutanoic acid

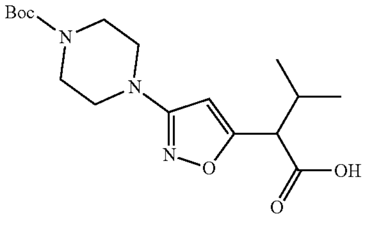 [SMILES: CC(C)C(C(=O)O)c1cc(N2CCN(C(=O)OC(C)(C)C)CC2)no1]

To a solution of tert-butyl 4-[5-(1-methoxycarbonyl-2-methyl-propyl)isoxazol-3-yl]piperazine-1-carboxylate (130 mg, 0.35 mmol, 1 eq) in methanol (2 mL), tetrahydrofuran (2 mL) and water (2 mL) was added lithium hydroxide (44 mg, 1.06 mmol, 3 eq). The reaction mixture was stirred at 15° C. for 1 hour. Water (3 mL) was added. The pH was adjusted to 6 with hydrochloric acid (1 M in water) and extracted with ethyl acetate (10 mL×5). The combined organic layers were washed with brine (50 mL×1), dried over anhydrous sodium sulfate, filtered and concentrated under reduced pressure. 2-[3-(4-tert-butoxycarbonylpiperazin-1-yl) isoxazol-5-yl]-3-methyl-butanoic acid (100 mg, 0.28 mmol, 79% yield) was obtained as a white solid. $^1$H-NMR (400 MHz, DMSO-$d_6$) δ 12.83 (s, 1H), 6.23 (s, 1H), 3.45-3.36 (m, 5H), 3.20-3.09 (m, 4H), 2.30-2.16 (m, 1H), 1.41 (s, 9H), 0.95 (d, J=6.8 Hz, 3H), 0.82 (d, J=6.8 Hz, 3H).

Step 16: Preparation of tert-butyl (S)-(1-(4-bromophenyl)ethyl)carbamate

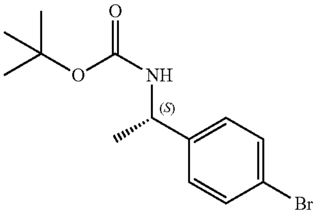

To a solution of (1S)-1-(4-bromophenyl)ethanamine (24.9 g, 124.45 mmol, 1 eq) in tetrahydrofuran (350 mL) was added triethylamine (37.78 g, 373.36 mmol, 3 eq). Then di-tert-butyldicarbonate (28.52 g, 130.68 mmol, 30 mL, 1.05 eq) was dropwise at 0° C. under nitrogen. Then the mixture was stirred at 25° C. for 12 h. The reaction mixture was concentrated under reduced pressure to remove tetrahydrofuran. Water (400 mL) was poured into the mixture and stirred for 1 minute. The aqueous phase was extracted with ethyl acetate (200 mL×3). The combined organic phase was washed with brine (200 mL×2), dried with anhydrous sodium sulfate, filtered and concentrated in vacuum. The crude product was triturated with petroleum ether (250 mL). Compound tert-butyl N-[(1S)-1-(4-bromophenyl)ethyl]carbamate (34.5 g, 114.93 mmol, 92% yield) was obtained as a white solid. LC/MS (ESI) m/z: 246.0 $[M+1-56]^+$.

Step 17: Preparation of tert-butyl (S)-(1-(4-(4-methylthiazol-5-yl)phenyl)ethyl)carbamate

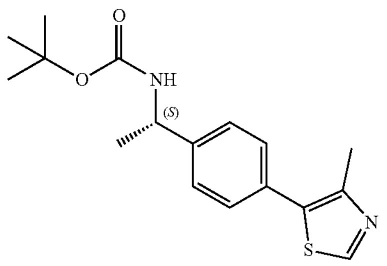

To a solution of tert-butyl N-[(1S)-1-(4-bromophenyl) ethyl]carbamate (14.5 g, 48.30 mmol, 1 eq) and 4-methylthiazole (7.18 g, 72.45 mmol, 1.5 eq) in dimethylacetamide (15 mL) was added Palladium(II) acetate (542 mg, 2.42 mmol, 0.05 eq) and potassium acetate (9.48 g, 96.61 mmol, 2 eq). The mixture was stirred at 90° C. for 12 h. Water (300 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by flash C18 column chromatography [ACN/H2O (0.5% FA)=5%~50%]. Compound tert-butyl N-[(1S)-1-[4-(4-methylthiazol-5-yl)phenyl]ethyl]carbamate (9.8 g, 29.85 mmol, 61% yield, 97% purity) was obtained as a gray solid. LC/MS (ESI) m/z: 319.0 $[M+1]^+$.

Step 18: Preparation of (S)-1-(4-(4-methylthiazol-5-yl)phenyl)ethan-1-amine

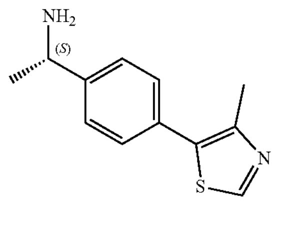

To a solution of tert-butyl N-[(1S)-1-[4-(4-methylthiazol-5-yl)phenyl]ethyl]carbamate (1.5 g, 4.71 mmol, 1 eq) in dichloromethane (20 mL) was added hydrochloride acid/dioxane (4 M, 20 mL, 16.98 eq). The mixture was stirred at 12 h. The reaction mixture was concentrated under reduced pressure to remove dichloromethane. The crude product was triturated with petroleum ether (100 mL). Compound (1S)-1-[4-(4-methylthiazol-5-yl)phenyl]ethanamine (1.1 g, crude, HCl) was obtained as a yellow solid. LC/MS (ESI) m/z: 219.1 $[M+1]^+$.

Step 19: Preparation of tert-butyl (2S,4R)-4-hydroxy-2-(((S)-1-(4-(4-methylthiazol-5-yl)phenyl) ethyl)carbamoyl)pyrrolidine-1-carboxylate

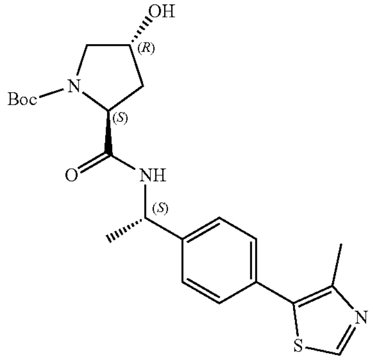

To a solution of (2S,4R)-1-tert-butoxycarbonyl-4-hydroxy-pyrrolidine-2-carboxylic acid (998 mg, 4.32 mmol, 1.1 eq) and o-(7-azabenzotriazol-1-yl)-n,n,n',n'-tetramethyluronium hexafluorophosphate (1.79 g, 4.71 mmol, 1.2 eq) in dimethyl formamide (10 mL) were added (1S)-1-[4-(4-methylthiazol-5-yl)phenyl]ethanamine (1 g, 3.92 mmol, 1 eq, Hydrochloride) and diisopropyl ethyl amine (1.52 g, 11.77 mmol, 2.05 mL, 3 eq). The reaction mixture was stirred at 15° C. for 0.5 hour. The reaction mixture was poured into water (20 mL), extracted with ethyl acetate (30 mL×3). The combined organic layers were washed with brine (50 mL×3), dried over anhydrous sodium sulfate, filtered and concentrated under reduced pressure. The residue was purified by silica gel column chromatography (Petroleum ether/Ethyl acetate=100/1 to 30/1). Tert-butyl (2S,4R)-4-hydroxy-2-[[(1S)-1-[4-(4-methylthiazol-5-yl) phenyl]ethyl]carbamoyl]pyrrolidine-1-carboxylate (1.2 g, 2.78 mmol, 70% yield) was obtained as a white solid. LC/MS (ESI) m/z: 432.3 $[M+1]^+$; $^1$H-NMR (400 MHz, DMSO-$d_6$) δ 8.98 (s, 1H), 8.52-8.28 (m, 1H), 7.46-7.36 (m, 4H), 5.03-4.93 (m, 2H), 4.27-4.13 (m, 2H), 3.45-3.22 (m, 5H), 2.88 (s, 1H), 2.75-2.67 (m, 1H), 2.44 (s, 3H), 2.04 (q, J=10.8 Hz, 1H), 1.80-1.69 (m, 1H), 1.42-1.37 (m, 5H), 1.31 (s, 7H).

Step 20: Preparation of (2S,4R)-4-hydroxy-N—((S)-1-(4-(4-methylthiazol-5-yl)phenyl)ethyl)pyrrolidine-2-carboxamide

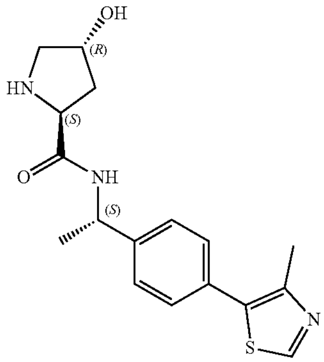

To a solution of tert-butyl (2S,4R)-4-hydroxy-2-[[(1S)-1-[4-(4-methylthiazol-5-yl) phenyl]ethyl]carbamoyl]pyrrolidine-1-carboxylate (1 g, 2.32 mmol, 1 eq) in dichloromethane (10 mL) was added hydrochloric acid (2.5 M in dioxane, 5 mL, 5.39 eq). The reaction mixture was stirred at 15° C. for 0.5 hour. The reaction mixture was concentrated under reduced pressure. (2S,4R)-4-hydroxy-N-[(1S)-1-[4-(4-methylthiazol-5-yl)phenyl]ethyl]pyrrolidine-2-carboxamide (800 mg, 2.17 mmol, 93% yield, hydrochloride) was obtained as a colorless oil. LC/MS (ESI) m/z: 332.1 $[M+1]^+$.

Step 21: Preparation of tert-butyl 4-(5-(1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)piperazine-1-carboxylate

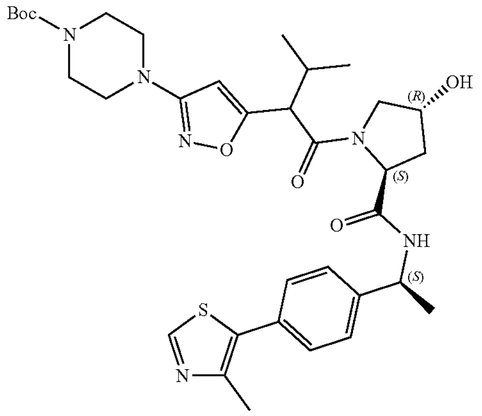

To a solution of 2-[3-(4-tert-butoxycarbonylpiperazin-1-yl)isoxazol-5-yl]-3-methyl-butanoic acid (100 mg, 0.28 mmol, 1 eq) and o-(7-azabenzotriazol-1-yl)-n,n,n',n'-tetramethyluronium hexafluorophosphate (129 mg, 0.33 mmol, 1.2 eq) in dimethyl formamide (5 mL) were added (2S,4R)-4-hydroxy-N-[(1S)-1-[4-(4-methylthiazol-5-yl)phenyl]ethyl] pyrrolidine-2-carboxamide (104 mg, 0.28 mmol, 1 eq, Hydrochloride) and diisopropyl ethyl amine (109 mg, 0.84 mmol, 3 eq). The reaction mixture was stirred at 15° C. for 0.5 h. The reaction mixture was poured into water (20 mL), extracted with ethyl acetate (30 mL×3). The combined organic layers were washed with brine (50 mL×3), dried over anhydrous sodium sulfate, filtered and concentrated under reduced pressure. The residue was purified by prep-TLC (dichloromethane:methanol=10:1). tert-butyl 4-[5-[1-[(2S,4R)-4-hydroxy-2-[[(1S)-1-[4-(4-methylthiazol-5-yl) phenyl]ethyl]carbamoyl]pyrrolidine-1-carbonyl]-2-methyl-propyl]isoxazol-3-yl]piperazine-1-carboxylate (180 mg, 0.26 mmol, 92% yield, 97% purity) was obtained as a colorless oil. LC/MS (ESI) m/z: 667.4 $[M+1]^+$; $^1$H-NMR (400 MHz, $CDCl_3$) δ 8.70 (d, J=1.2 Hz, 1H), 8.03 (s, 1H), 7.45-7.39 (m, 3H), 7.38-7.31 (m, 2H), 5.94 (d, J=10.0 Hz, 1H), 5.13-4.95 (m, 1H), 4.79 (dd, J=4.4, 8.4 Hz, 1H), 4.70-4.59 (m, 2H), 3.84-3.71 (m, 1H), 3.67-3.55 (m, 4H), 3.54-3.47 (m, 5H), 3.21 (td, J=5.2, 13.2 Hz, 4H), 2.98 (s, 4H), 2.90 (s, 4H), 2.82 (s, 6H), 2.55 (d, J=1.6 Hz, 4H), 2.45 (ddd, J=6.4, 9.6, 16.0 Hz, 1H), 2.08-1.92 (m, 1H), 1.53-1.37 (m, 13H), 1.06 (dd, J=2.4, 6.4 Hz, 3H), 0.94 (d, J=6.8 Hz, 3H).

Step 22: Preparation of tert-butyl 4-(5-((R)-1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)piperazine-1-carboxylate

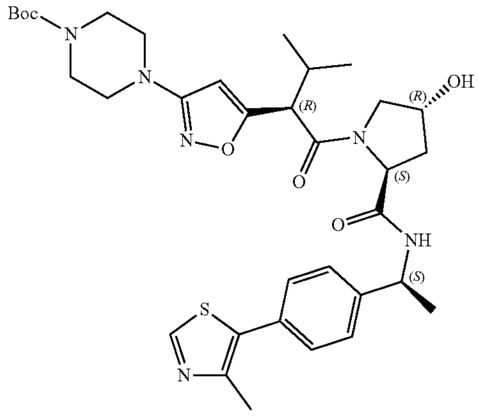

Tert-butyl 4-[5-[1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]isoxazol-3-yl]piperazine-1-carboxylate (200 mg, 0.29 mmol, 1 eq) was separated by chiral supercritical fluid chromatography, tert-butyl 4-[5-[(1S)-1-[(2S,4R)-4-hydroxy-2-[[(1S)-1-[4-(4-methylthiazol-5-yl) phenyl]ethyl]carbamoyl]pyrrolidine-1-carbonyl]-2-methyl-propyl]isoxazol-3-yl]piperazine-1-carboxylate (80 mg, 0.11 mmol, 76% yield, 95% purity) was obtained as a white solid, tert-butyl 4-[5-[(1R)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]isoxazol-3-yl]piperazine-1-carboxylate (70 mg, 0.1 mmol, 68% yield, 98% purity) was obtained as a white solid.

Step 23: Preparation of (2S,4R)-4-hydroxy-1-((R)-3-methyl-2-(3-(piperazin-1-yl)isoxazol-5-yl)butanoyl)-N—((S)-1-(4-(4-methylthiazol-5-yl)phenyl)ethyl)pyrrolidine-2-carboxamide

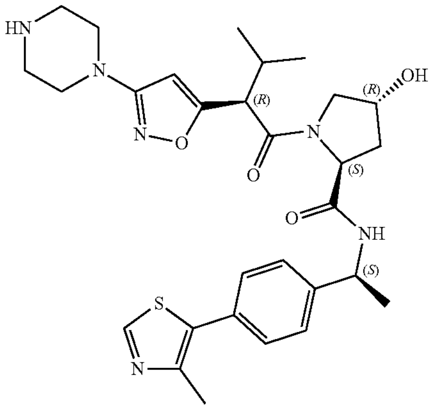

To a solution of tert-butyl 4-[5-[(1R)-1-[(2S,4R)-4-hydroxy-2-[[(1S)-1-[4-(4-methylthiazol-5-yl)phenyl]ethyl] carbamoyl]pyrrolidine-1-carbonyl]-2-methyl-propyl]isoxazol-3-yl]piperazine-1-carboxylate (70 mg, 0.1 mmol, 1 eq) in dichloromethane (2 mL) was added hydrochloric acid (4 M in dioxane, 3 mL). The reaction mixture was stirred at 15° C. for 1 hour. The reaction mixture was concentrated under reduced pressure. (2S,4R)-4-hydroxy-1-[(2R)-3-methyl-2-(3-piperazin-1-ylisoxazol-5-yl)butanoyl]-N-[(1S)-1-[4-(4-methylthiazol-5-yl)phenyl]ethyl]pyrrolidine-2-carboxamide (55 mg, 0.09 mmol, 91% yield, 99% purity) was obtained as a white solid. LC/MS (ESI) m/z: 567.2 $[M+1]^+$.

Step 24: Preparation of (2S,4R)-1-((R)-2-(3-(4-((1-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperidin-4-yl)methyl)piperazin-1-yl)isoxazol-5-yl)-3-methylbutanoyl)-4-hydroxy-N—((S)-1-(4-(4-methylthiazol-5-yl)phenyl)ethyl) pyrrolidine-2-carboxamide

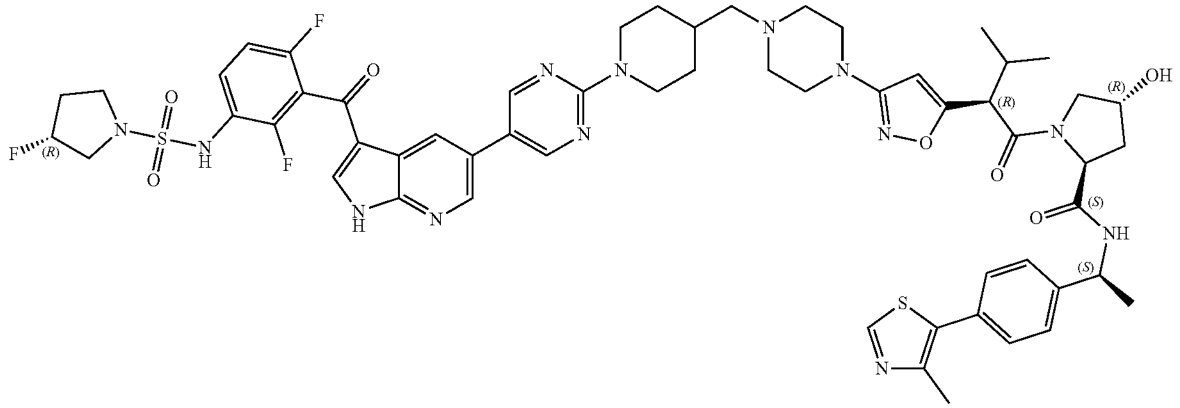

To a solution of (2S,4R)-4-hydroxy-1-[(2R)-3-methyl-2-(3-piperazin-1-ylisoxazol-5-yl) butanoyl]-N-[(1S)-1-[4-(4-methylthiazol-5-yl)phenyl]ethyl]pyrrolidine-2-carboxamide (68.81 mg, 0.11 mmol, 1 eq, hydrochloride) in methanol (0.5 mL) and dichloromethane (0.5 mL) was added sodium acetate (19 mg, 0.22 mmol, 2 eq) to adjust the pH ~8.0. Then (3R)—N-[2,4-difluoro-3-[5-[2-(4-formyl-1-piperidyl)pyrimidin-5-yl]-1H-pyrrolo[2,3-b]pyridine-3-carbonyl]phenyl]-3-fluoro-pyrrolidine-1-sulfonamide (70 mg, 0.11 mmol, 1 eq) was added. The mixture was stirred at 30° C. for 15 min, followed by acetic acid (14 mg, 0.22 mmol, 2 eq) was added to adjust the pH ~5.0. The mixture was stirred at 15° C. for 15 min. And then sodium cyanoborohydride (14 mg, 0.22 mmol, 2 eq) was added in portions. The reaction mixture was stirred at 30° C. for 2.5 hours. Dichloromethane (30 mL×2), methanol (5 mL) and water (25 mL×2) were added and organic layers were separated. The combined organic phase was concentrated under vacuum. The residue was purified by Semi-preparative reverse phase HPLC. Compound (2S,4R)-1-[(2R)-2-[3-[4-[[1-[5-[3-[2,6-difluoro-3-[(3R)-3-fluoropyrrolidin-1-yl]sulfonylamino]benzoyl]-1H-pyrrolo[2,3-b]pyridin-5-yl]yrimidin-2-yl]-4-piperidyl] methyl]piperazin-1-yl]isoxazol-5-yl]-3-methyl-butanoyl]-4-hydroxy-N-[(1S)-1-[4-(4-methylthiazol-5-yl)phenyl]ethyl] pyrrolidine-2-carboxamide (56.9 mg, 0.04 mmol, 37% yield, 95% purity, trifluoroacetic acid) was obtained as an off-white solid. LC/MS (ESI) m/z: 582.8 $[M/2+1]^+$; $^1$H-NMR (400 MHz, DMSO-$d_6$) δ 12.99 (s, 1H), 9.82 (s, 1H), 8.98 (s, 1H), 8.76 (s, 2H), 8.66 (s, 1H), 8.56 (s, 1H), 8.37 (d, J=6.8 Hz, 1H), 8.11 (s, 1H), 7.69-7.56 (m, 1H), 7.51-7.41 (m, 2H), 7.40-7.33 (m, 2H), 7.27 (t, J=8.8 Hz, 1H), 6.34-6.16 (m, 1H), 5.43-5.21 (m, 1H), 5.11 (s, 1H), 4.99-4.84 (m, 1H), 4.75 (d, J=12.0 Hz, 2H), 4.52-4.20 (m, 2H), 3.80 (s, 2H), 3.73 (d, J=6.4 Hz, 1H), 3.63 (d, J=9.2 Hz, 3H), 3.47 (d, J=13.6 Hz, 3H), 3.41 (s, 3H), 3.24 (s, 2H), 3.13 (s, 3H), 3.07-2.96 (m, 2H), 2.49-2.44 (m, 1H), 2.46 (s, 3H), 2.30-2.10 (m, 4H), 2.08-1.97 (m, 2H), 1.92-1.76 (m, 2H), 1.52-1.34 (m, 3H), 1.24 (s, 3H), 0.98 (d, J=6.0 Hz, 2H), 0.90-0.77 (m, 3H).

Exemplary Synthesis of (2S,4R)-1-(2-(3-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl) isoxazol-5-yl)-3-methylbutanoyl)-4-hydroxy-N-(4-(4-methylthiazol-5-yl)benzyl)pyrrolidine-2-carboxamide (Example 322)

Step 1: Preparation of tert-butyl 4-(1-((benzyloxy) carbonyl)azetidin-3-yl)piperazine-1-carboxylate

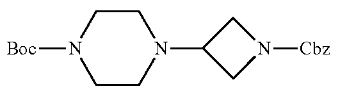 [SMILES: CC(C)(C)OC(=O)N1CCN(C2CN(C(=O)OCc3ccccc3)C2)CC1]

Into a 250-mL round-bottom flask, was placed tert-butyl piperazine-1-carboxylate (10.0 g, 53.69 mmol, 1 equiv) and benzyl 3-oxoazetidine-1-carboxylate (11.0 g, 53.60 mmol, 1.00 equiv) in dichloromethane (150 mL), to which NaBH (OAc)3 (34.1 g, 161.07 mmol, 3 equiv) was added. The resulting mixture was stirred for 3 h at room temperature. The reaction was then quenched by water (100 mL), extracted with dichloromethane (100 mL×3), washed with water (100 mL) and brine (100 mL), dried over anhydrous sodium sulfate and concentrated under reduced pressure. The residue was applied onto a silica gel column with ethyl acetate/petroleum ether (v:v=2:1). This resulted in 10.0 g (49.61%) of tert-butyl 4-[1-[(benzyloxy)carbonyl]azetidin-3-yl]piperazine-1-carboxylate as a light brown solid. LC/MS (ESI) m/z: 376.35 $[M+1]^+$.

Step 2: Preparation of tert-butyl 4-(azetidin-3-yl)piperazine-1-carboxylate

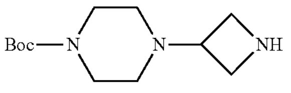 [SMILES: CC(C)(C)OC(=O)N1CCN(C2CNC2)CC1]

To a solution of tert-butyl 4-[1-[(benzyloxy)carbonyl]azetidin-3-yl]piperazine-1-carboxylate (10.0 g, 26.63 mmol, 1 equiv) in 30 mL MeOH was added Pd/C (10%, 2.0 g) under nitrogen atmosphere in a 250 mL round bottom flask. The flask was then vacuumed and flushed with hydrogen. The reaction mixture was hydrogenated at room temperature for 2 hours under hydrogen atmosphere using a hydrogen balloon, then filtered through a Celite pad and the filtration was concentrated under reduced pressure. This resulted in 5.9 g (91.79%) of tert-butyl 4-(azetidin-3-yl)piperazine-1-carboxylate as yellow oil. LC/MS (ESI) m/z: 242.20 $[M+1]^+$.

Step 3: Preparation of tert-butyl 2-isopropylbut-3-enoate

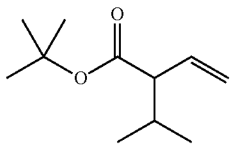

Into a 1000-mL round-bottom flask purged and maintained with an inert atmosphere of nitrogen, was placed a solution of tert-butyl but-3-enoate (20.0 g, 140.6 mmol, 1.0 equiv) in tetrahydrofuran (400 mL). Lithium diisopropylamide (30.0 g, 280.1 mmol, 2.0 equiv) was added to the above mixture at −78° C. After stirring for 30 min at −78° C., the reaction mixture was charged with 2-iodopropane (36.0 g, 211.8 mmol, 1.5 equiv) in portions at −78° C. The resulting mixture was warmed up to room temperature and stirred overnight at room temperature. The reaction was then quenched by the addition of 300 mL saturated $NH_4Cl$ solution. The resulting solution was extracted with ethyl acetate (300 mL×3), and the organic layers were combined and concentrated under vacuum. The residue was applied onto a silica gel column eluting with ethyl acetate/petroleum ether (20:1). This resulted in 18.0 g (69.0%) of tert-butyl 2-(propan-2-yl)but-3-enoate as a light yellow liquid.

Step 4: Preparation of tert-butyl 2-(3-bromo-4,5-dihydroisoxazol-5-yl)-3-methylbutanoate

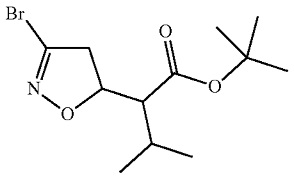 [SMILES: CC(C)C(C(=O)OC(C)(C)C)C1CC(Br)=NO1]

Into a 1000-mL round-bottom flask purged and maintained with an inert atmosphere of nitrogen, was placed a solution of tert-butyl 2-(propan-2-yl)but-3-enoate (18.0 g, 97.7 mmol, 1.0 equiv), potassium methaneperoxoate (29.0 g, 289.7 mmol, 3.0 equiv) in DMF/$H_2O$ (200/200 mL) at −10° C. Then 1-bromo-N-hydroxymethanecarbonimidoyl bromide (35.0 g, 172.6 mmol, 1.8 equiv) was added to the above mixture at −10° C. The resulting mixture was stirred overnight at room temperature. The reaction was then quenched by the addition of 300 mL water/ice. The resulting mixture was extracted with ethyl acetate (300 mL×3), and the organic layers were combined and concentrated under vacuum. The residue was applied onto a silica gel column eluting with ethyl acetate/petroleum ether (10:1). This resulted in 8.6 g (29.0%) of tert-butyl 2-(3-bromo-4,5-dihydro-1,2-oxazol-5-yl)-3-methylbutanoate as a solid. LC/MS (ESI) m/z: 306.40 $[M+1]^+$.

Step 5: Preparation of tert-butyl 4-(1-(5-(1-(tert-butoxy)-3-methyl-1-oxobutan-2-yl)-4,5-dihydroisoxazol-3-yl)azetidin-3-yl)piperazine-1-carboxylate

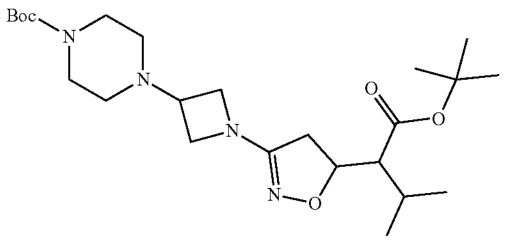 [SMILES: CC(C)C(C(=O)OC(C)(C)C)C1CC(N2CC(N3CCN(C(=O)OC(C)(C)C)CC3)C2)=NO1]

Into a 60-mL sealed tube purged and maintained with an inert atmosphere of nitrogen, was placed tert-butyl 4-(azetidin-3-yl)piperazine-1-carboxylate (4.0 g, 16.57 mmol, 1 equiv), tert-butyl 2-(3-bromo-4,5-dihydro-1,2-oxazol-5-yl)-3-methylbutanoate (10.2 g, 33.15 mmol, 2 equiv), DIEA (6.4 g, 49.72 mmol, 3 equiv) in n-BuOH (20.0 mL). The resulting mixture was stirred for 2 h at 110° C. in an oil bath. The reaction was then quenched by water (50 mL), extracted with ethyl acetate (50 mL×3), washed with water (50 mL) and brine (50 mL), dried over anhydrous sodium sulfate and concentrated. The residue was applied onto a silica gel column with ethyl acetate/petroleum ether (v:v=1:4). This resulted in 2.2 g (28.45%) of tert-butyl 4-(1-[5-[1-(tert-butoxy)-3-methyl-1-oxobutan-2-yl]-4,5-dihydro-1,2-oxazol-3-yl]azetidin-3-yl)piperazine-1-carboxylate as yellow oil. LC/MS (ESI) m/z: 467.45 $[M+1]^+$.

Step 6: Preparation of tert-butyl 4-(1-(5-(1-(tert-butoxy)-3-methyl-1-oxobutan-2-yl)isoxazol-3-yl)azetidin-3-yl)piperazine-1-carboxylate

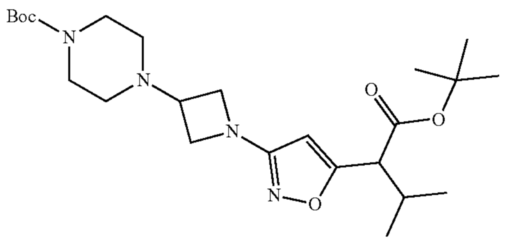 [SMILES: CC(C)C(C(=O)OC(C)(C)C)c1cc(N2CC(N3CCN(C(=O)OC(C)(C)C)CC3)C2)no1]

Into a 30-mL vial purged and maintained with an inert atmosphere of nitrogen, was placed tert-butyl 4-(1-[5-[1-(tert-butoxy)-3-methyl-1-oxobutan-2-yl]-4,5-dihydro-1,2-oxazol-3-yl]azetidin-3-yl)piperazine-1-carboxylate (2.2 g, 4.71 mmol, 1 equiv), pyridine (1.9 g, 23.57 mmol, 5 equiv), 12 (2.4 g, 9.46 mmol, 2.01 equiv) in toluene (20 mL). The resulting solution was stirred for 2 h at 110° C. in an oil bath. The reaction was then quenched by saturated $Na_2S_2O_3$ (50 mL), extracted with ethyl acetate (50 mL×3), washed with saturated $NaHCO_3$ (50 mL) and brine (50 mL), dried over anhydrous sodium sulfate and concentrated. The residue was applied onto a silica gel column with ethyl acetate/petroleum ether (v:v=1:1). This resulted in 1.0 g (45.65%) of tert-butyl 4-(1-[5-[1-(tert-butoxy)-3-methyl-1-oxobutan-2-yl]-1,2-oxazol-3-yl]azetidin-3-yl)piperazine-1-carboxylate as yellow oil. LC/MS (ESI) m/z: 465.1 [M+1]$^+$.

Step 7: Preparation of 3-methyl-2-(3-(3-(piperazin-1-yl)azetidin-1-yl)isoxazol-5-yl)butanoic acid

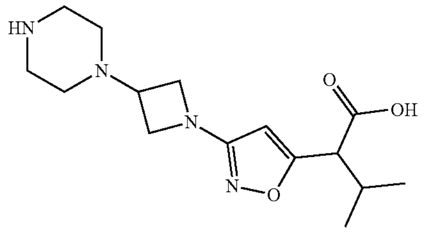 [SMILES: CC(C)C(C(=O)O)c1cc(N2CC(N3CCNCC3)C2)no1]

Step 8: Preparation of (R)—N-(3-(5-(2-chloropyrimidin-5-yl)-1H-pyrrolo[2,3-b]pyridine-3-carbonyl)-2,4-difluorophenyl)-3-fluoropyrrolidine-1-sulfonamide

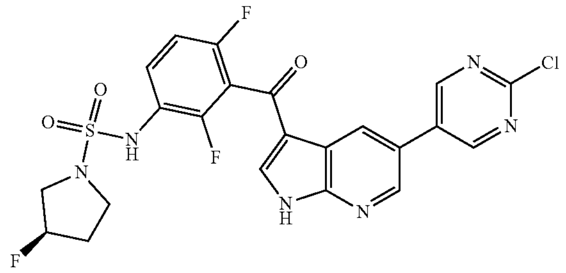 [SMILES: O=C(c1c(F)ccc(NS(=O)(=O)N2CC[C@@H](F)C2)c1F)c1c[nH]c2ncc(-c3cnc(Cl)nc3)cc12]

Into a 30-mL sealed tube, was placed (3R)—N-(3-[5-bromo-1H-pyrrolo[2,3-b]pyridine-3-carbonyl]-2,4-difluorophenyl)-3-fluoropyrrolidine-1-sulfonamide (450.0 mg, 0.89 mmol, 1 equiv), 2-chloro-5-(4,4,5,5-tetramethyl-1,3,2-dioxaborolan-2-yl)pyrimidine (645.0 mg, 2.68 mmol, 3.00 equiv), $Na_2CO_3$ (284.0 mg, 2.68 mmol, 3.00 equiv) and $Pd(dppf)Cl_2CH_2Cl_2$ (15.0 mg, 0.02 mmol, 0.02 equiv) in dioxane (5 mL) and H2O (1 mL) under nitrogen atmosphere. The resulting mixture was stirred for 3 hours at 105° C. in an oil bath under nitrogen atmosphere. The resulting mixture was concentrated under reduced pressure. The residue was applied onto a silica gel column eluting with ethyl acetate/petroleum ether (1:2). This resulted in 70.0 mg (14.58%) of (3R)—N-[3-[5-(2-chloropyrimidin-5-yl)-1H-pyrrolo[2,3-b]pyridine-3-carbonyl]-2,4-difluorophenyl]-3-fluoropyrrolidine-1-sulfonamide as a light yellow solid. LC/MS (ESI) m/z: 537.05 [M+1]$^+$.

Step 9: Preparation of 2-(3-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl)isoxazol-5-yl)-3-methylbutanoic acid

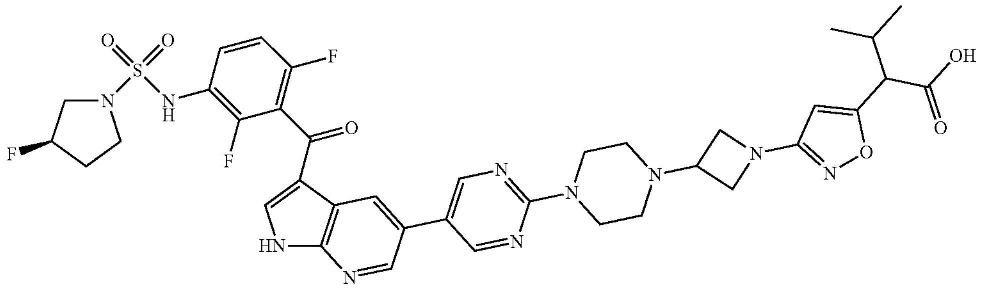 [SMILES: CC(C)C(C(=O)O)c1cc(N2CC(N3CCN(c4ncc(-c5cnc6[nH]cc(C(=O)c7c(F)ccc(NS(=O)(=O)N8CC[C@@H](F)C8)c7F)c6c5)cn4)CC3)C2)no1]

Into a 100-mL round-bottom flask, was placed tert-butyl 4-(1-[5-[1-(tert-butoxy)-3-methyl-1-oxobutan-2-yl]-1,2-oxazol-3-yl]azetidin-3-yl)piperazine-1-carboxylate (500.0 mg, 1.08 mmol, 1 equiv) in DCM (20 mL), to which 2,2,2-trifluoroacetic acid (8 mL) was added. The resulting mixture was stirred for 5 hours at room temperature and concentrated under reduced pressure. This resulted in 270.0 mg of 3-methyl-2-[3-[3-(piperazin-1-yl)azetidin-1-yl]-1,2-oxazol-5-yl]butanoic acid as yellow oil. LC/MS (ESI) m/z: 309.30 [M+1]$^+$.

Into a 50-mL round-bottom flask, was placed 3-methyl-2-[3-[3-(piperazin-1-yl)azetidin-1-yl]-1,2-oxazol-5-yl]butanoic acid (40 mg, 0.13 mmol, 1 equiv), (3R)—N-[3-[5-(2-chloropyrimidin-5-yl)-1H-pyrrolo[2,3-b]pyridine-3-carbonyl]-2,4-difluorophenyl]-3-fluoropyrrolidine-1-sulfonamide (69.6 mg, 0.13 mmol, 1 equiv), $Et_3N$ (50.3 mg, 0.39 mmol, 3 equiv) in DCM (2 mL). The resulting mixture was stirred for 48 h at room temperature. The resulting mixture was concentrated under vacuum. The residue was applied onto a silica gel column with dichloromethane/methanol (v:v=4:1). This resulted in 53.0 mg (50.52%) of 2-(3-[3-[4-(5-[3-[2,6-difluoro-3-([[(3R)-3-fluoropyrrolidin-1-yl]sulfonyl]amino)benzoyl]-1H-pyrrolo[2,3-b]pyridin-5-yl]pyrimidin-2-yl)piperazin-1-yl]azetidin-1-yl]-1,2-oxazol-5-yl)-3-methylbutanoic acid as yellow oil. LC/MS (ESI) m/z: 809.05 [M+1]$^+$.

Step 10: Preparation of (2S,4R)-1-(2-(3-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl)isoxazol-5-yl)-3-methylbutanoyl)-4-hydroxy-N-(4-(4-methylthiazol-5-yl)benzyl)pyrrolidine-2-carboxamide

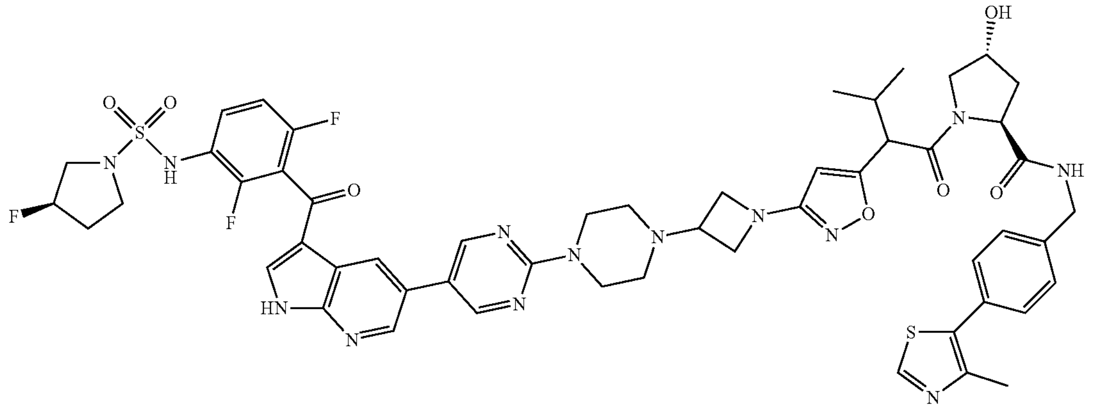 [SMILES: Cc1ncsc1-c1ccc(CNC(=O)[C@@H]2C[C@@H](O)CN2C(=O)C(c2cc(N3CC(N4CCN(c5ncc(-c6cnc7[nH]cc(C(=O)c8c(F)ccc(NS(=O)(=O)N9CC[C@@H](F)C9)c8F)c7c6)cn5)CC4)C3)no2)C(C)C)cc1]

Into a 50-mL flask, was placed 2-(3-[3-[4-(5-[3-[2,6-difluoro-3-([[(3R)-3-fluoropyrrolidin-1-yl]sulfonyl]amino)benzoyl]-1H-pyrrolo[2,3-b]pyridin-5-yl]pyrimidin-2-yl)piperazin-1-yl]azetidin-1-yl]-1,2-oxazol-5-yl)-3-methylbutanoic acid (53 mg, 0.07 mmol, 1 equiv), (2S,4R)-4-hydroxy-N-[[4-(4-methyl-1,3-thiazol-5-yl)phenyl]methyl]pyrrolidine-2-carboxamide (20.8 mg, 0.07 mmol, 1 equiv), DIEA (25.4 mg, 0.20 mmol, 3 equiv), BOP (43.5 mg, 0.10 mmol, 1.5 equiv) in DMF (5 mL). The resulting mixture was stirred for 2 hours at room temperature. The reaction was then quenched by the addition of 20 mL of water and extracted with dichloromethane (20 mL×2), washed with 20 ml of water and 20 mL of brine. The organic phase was dried over anhydrous sodium sulfate and concentrated under reduced pressure. The residue was purified by HPLC. This resulted in 31.0 mg (42.69%) of (2S,4R)-1-[2-(3-[3-[4-(5-[3-[2,6-difluoro-3-([[(3R)-3-fluoropyrrolidin-1-yl]sulfonyl]amino)benzoyl]-1H-pyrrolo[2,3-b]pyridin-5-yl]pyrimidin-2-yl)piperazin-1-yl]azetidin-1-yl]-1,2-oxazol-5-yl)-3-methylbutanoyl]-4-hydroxy-N-[[4-(4-methyl-1,3-thiazol-5-yl)phenyl]methyl]pyrrolidine-2-carboxamide as yellow oil. LC/MS (ESI) m/z: 1108.10 [M+1]$^+$; $^1$H-NMR (400 MHz, DMSO-$d_6$) δ 13.00 (s, 1H), 11.30 (brs, 1H), 9.80 (s, 1H), 8.97 (s, 1H), 8.85 (s, 2H), 8.67 (d, J=2.2 Hz, 1H), 8.58 (s, 1H), 8.50-8.46 (m, 1H), 8.14-8.06 (m, 1H), 7.69-7.55 (m, 1H), 7.46-6.91 (m, 5H), 5.97 (d, J=2.7 Hz, 1H), 5.38 (s, 1H), 5.20 (s, 1H), 4.85-4.60 (m, 2H), 4.43-4.26 (m, 4H), 4.25-4.15 (m, 4H), 3.83-3.74 (m, 2H), 3.69-3.28 (m, 10H), 3.12-2.98 (m, 1H), 2.43-2.40 (m, 3H), 2.27-1.83 (m, 5H), 1.23 (d, J=10.7 Hz, 1H), 0.95-0.90 (m, 2H), 0.85-0.71 (m, 2H), 0.63-0.52 (m, 1H).

Exemplary Synthesis of (2S,4R)-1-((S)-2-(2-(4-((4-(4-(3-(2,6-difluoro-3-((3-hydroxy propyl) sulfonamido)benzoyl)-1H-pyrrolo[2,3-b]pyridin-5-yl)phenyl)piperazin-1-yl)methyl)piperidin-1-yl) acetamido)-3,3-dimethylbutanoyl)-4-hydroxy-N-(4-(4-methylthiazol-5-yl)benzyl)pyrrolidine-2-carboxamide (Example 321)

Step 1: Preparation of sodium 3-acetoxypropane-1-sulfonate

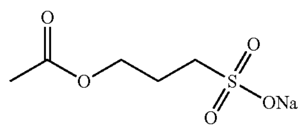

Into a 100-mL round-bottom flask purged and maintained with an inert atmosphere of nitrogen, was placed sodium 3-hydroxypropane-1-sulfonate (5 g, 30.84 mmol, 1 equiv) in acetic anhydride (40 mL). The resulting solution was stirred for 7 hr at 120° C. in an oil bath. After cooling to room temperature, the precipitated-out solids were collected by filtration and dried under vacuum. This resulted in 6.2 g (98.47%) of sodium 3-acetoxypropane-1-sulfonate as a white solid.

Step 2: Preparation of 3-(chlorosulfonyl)propyl acetate

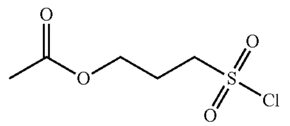

Into a 50-mL round-bottom flask, was placed sodium 3-acetoxypropane-1-sulfonate (3 g, 14.69 mmol, 1 equiv) in oxalyl dichloride (20 mL). Catalytic amount of DMF (0.1 mL) was added to the above mixture. The resulting mixture was stirred for 5 hr at 68° C. in an oil bath. The reaction mixture was concentrated under vacuum. The residue was re-dissolved in EtOAc (100 mL). The insoluble solids were filtered out and the filtrate was concentrated under vacuum. This resulted in 2.3 g (78.02%) of 3-(chlorosulfonyl)propyl acetate as yellow oil.

Step 3: Preparation of 3-(N-(3-(5-bromo-1H-pyrrolo [2,3-b]pyridine-3-carbonyl)-2,4-difluorophenyl)sulfamoyl)propyl acetate

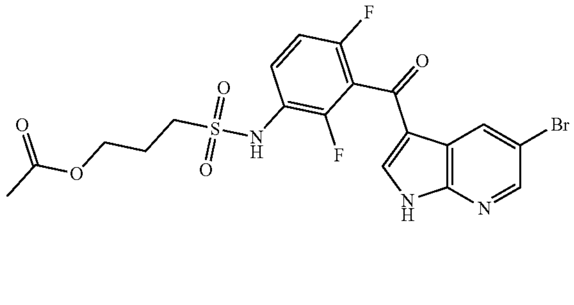 [SMILES: CC(=O)OCCCS(=O)(=O)Nc1ccc(F)c(C(=O)c2c[nH]c3ncc(Br)cc23)c1F]

Into a 50-mL round-bottom flask, was placed 3-(chlorosulfonyl)propyl acetate (200 mg, 1.00 mmol, 1 equiv), 3-[5-bromo-1H-pyrrolo[2,3-b]pyridine-3-carbonyl]-2,4-difluoroaniline (351.0 mg, 1.00 mmol, 1 equiv) and DMAP (12.2 mg, 0.10 mmol, 0.1 equiv) in pyridine (10 mL). The resulting solution was stirred overnight at 40° C. in an oil bath. The mixture was concentrated under vacuum. The residue was applied onto a silica gel column eluting with dichloromethane/methanol (20:1). This resulted in 293 mg (56.93%) of 3-(N-(3-(5-bromo-1H-pyrrolo[2,3-b]pyridine-3-carbonyl)-2,4-difluorophenyl)sulfamoyl)propyl acetate as a yellow solid. LC/MS (ESI) m/z: 515.90/517.90.20 $[M+1]^+$.

Step 4: Preparation of tert-butyl 2-(4-((4-(4-(3-(3-((3-acetoxypropyl)sulfonamido)-2,6-difluorobenzoyl)-1H-pyrrolo[2,3-b]pyridin-5-yl)phenyl)piperazin-1-yl)methyl)piperidin-1-yl)acetate

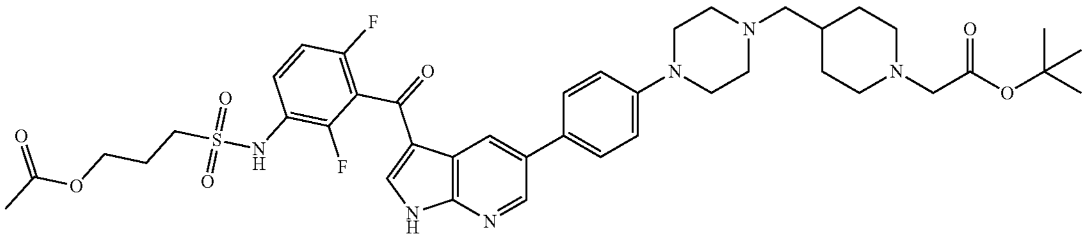 [SMILES: CC(=O)OCCCS(=O)(=O)Nc1ccc(F)c(C(=O)c2c[nH]c3ncc(-c4ccc(N5CCN(CC6CCN(CC(=O)OC(C)(C)C)CC6)CC5)cc4)cc23)c1F]

Into a 10-mL vial purged and maintained with an inert atmosphere of nitrogen, was placed 3-[(3-[5-bromo-1H-pyrrolo[2,3-b]pyridine-3-carbonyl]-2,4-difluorophenyl)sulfamoyl]propyl acetate (293 mg, 0.57 mmol, 1 equiv), tert-butyl 2-[4-([4-[4-(4,4,5,5-tetramethyl-1,3,2-dioxaborolan-2-yl)phenyl]piperazin-1-yl]methyl)piperidin-1-yl]acetate (340.2 mg, 0.68 mmol, 1.2 equiv), $Na_2CO_3$ (180.4 mg, 1.70 mmol, 3 equiv), $Pd(dppf)Cl_2$ (41.5 mg, 0.06 mmol, 0.1 equiv) in dioxane (5 mL) and $H_2O$ (1 mL) under nitrogen atmosphere. The resulting mixture was stirred for 2 hr at 105° C. in an oil bath. The reaction was cooled to room temperature and diluted with water (20 mL). The resulting mixture was extracted with ethyl acetate (40 mL×3). The combined organic layer was washed with brine (20 mL×1), dried over anhydrous sodium and concentrated under vacuum. The residue was applied onto a silica gel column eluting with dichloromethane/methanol (10:1). This resulted in 287 mg (62.52%) of tert-butyl 2-(4-((4-(4-(3-(3-(3-acetoxypropylsulfonamido)-2,6-difluorobenzoyl)-1H-pyrrolo [2,3-b]pyridin-5-yl)phenyl)piperazin-1-yl)methyl)piperidin-1-yl)acetate as a yellow solid. LC/MS (ESI) m/z: 809.55 $[M+1]^+$.-

Step 5: Preparation of 2-(4-((4-(4-(3-(3-((3-acetoxypropyl)sulfonamido)-2,6-difluorobenzoyl)-1H-pyrrolo[2,3-b]pyridin-5-yl)phenyl)piperazin-1-yl)methyl)piperidin-1-yl)acetic acid

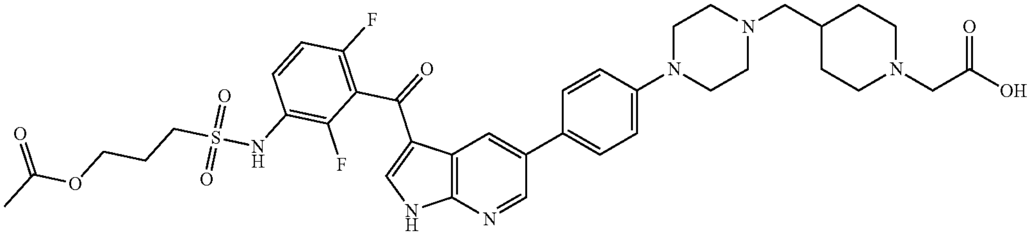 [SMILES: CC(=O)OCCCS(=O)(=O)Nc1ccc(F)c(C(=O)c2c[nH]c3ncc(-c4ccc(N5CCN(CC6CCN(CC(=O)O)CC6)CC5)cc4)cc23)c1F]

Into a 50-mL round-bottom flask, was placed 3-[[3-(5-[4-[4-([1-[2-(tert-butoxy)-2-oxoethyl]piperidin-4-yl]methyl)piperazin-1-yl]phenyl]-1H-pyrrolo[2,3-b]pyridine-3-carbonyl)-2,4-difluorophenyl]sulfamoyl]propyl acetate (287 mg, 0.35 mmol, 1 equiv) in dichloromethane (20 mL). Then TFA (5 mL) was added at room temperature. The resulting solution was stirred overnight at room temperature. The mixture was concentrated under vacuum. This resulted in 267 mg (99.97%) of 2-(4-((4-(4-(3-(3-(3-acetoxypropylsulfonamido)-2,6-difluorobenzoyl)-1H-pyrrolo[2,3-b]pyridin-5-yl)phenyl)piperazin-1-yl)methyl)piperidin-1-yl)acetic acid HCl salt as yellow oil. LC/MS (ESI) m/z: 753.10 $[M+1]^+$.

Step 6: Preparation of 3-(N-(2,4-difluoro-3-(5-(4-(4-((1-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)piperidin-4-yl)methyl)piperazin-1-yl)phenyl)-1H-pyrrolo[2,3-b]pyridine-3-carbonyl)phenyl)sulfamoyl)propyl acetate Into a 50-mL round-bottom flask, was placed 2-(4-((4-(4-(3-(3-(3-acetoxypropylsulfonamido)-2,6-difluorobenzoyl)-1H-pyrrolo[2,3-b]pyridin-5-yl)phenyl)piperazin-1-yl)methyl)piperidin-1-yl)acetic acid (267 mg, 0.35 mmol, 1 equiv) in DMF (20 mL). Then BOP (188.2 mg, 0.43 mmol, 1.2 equiv) and DIEA (137.5 mg, 1.06 mmol, 3 equiv) was successively added into the above solution. After stirring for 5 min at room temperature, the reaction mixture was charged with a solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide HCl salt (152.7 mg, 0.35 mmol, 1 equiv) in DMF (5 mL). The reaction mixture was stirred for 2 hr at room temperature. The reaction was then quenched by the addition of water (20 mL). The resulting mixture was extracted with dichloromethane/methanol (v:v=10:1, 40 mL×3). The combined organic layer was washed with brine (10 mL), dried over anhydrous sodium sulfate and concentrated. The residue was applied onto a silica gel column eluting with dichloromethane/methanol (10:1). This resulted in 283 mg (68.47%) of 3-(N-(2,4-difluoro-3-(5-(4-(4-((1-(2-((S)-1-((2S,4R)-4-hydroxy-2-(4-(4-methylthiazol-5-yl)benzylcarbamoyl)pyrrolidin-1-yl)-3,3-dimethyl-1-oxobutan-2-ylamino)-2-oxoethyl)piperidin-4-yl)methyl)piperazin-1-yl)phenyl)-1H-pyrrolo[2,3-b]pyridine-3-carbonyl)phenyl)sulfamoyl)propyl acetate as a yellow solid. LC/MS (ESI) m/z: 1187.05 $[M+23]^+$.

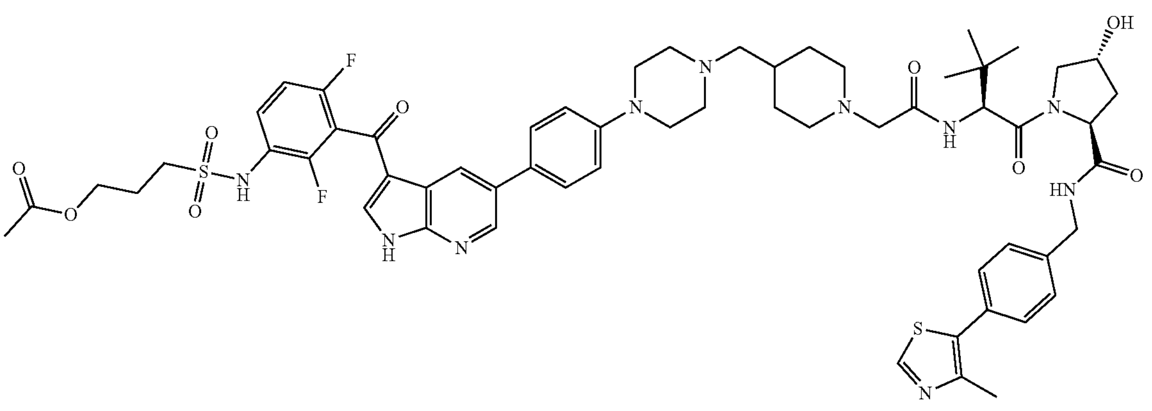 [SMILES: CC(=O)OCCCS(=O)(=O)Nc1ccc(F)c(C(=O)c2c[nH]c3ncc(-c4ccc(N5CCN(CC6CCN(CC(=O)N[C@H](C(=O)N7C[C@H](O)C[C@H]7C(=O)NCc7ccc(-c8scnc8C)cc7)C(C)(C)C)CC6)CC5)cc4)cc23)c1F]

Step 7: Preparation of (2S,4R)-1-((S)-2-(2-(4-((4-(4-(3-(2,6-difluoro-3-((3-hydroxypropyl) sulfonamido)benzoyl)-1H-pyrrolo[2,3-b]pyridin-5-yl)phenyl)piperazin-1-yl)methyl)piperidin-1-yl) acetamido)-3,3-dimethylbutanoyl)-4-hydroxy-N-(4-(4-methylthiazol-5-yl)benzyl)pyrrolidine-2-carboxamide

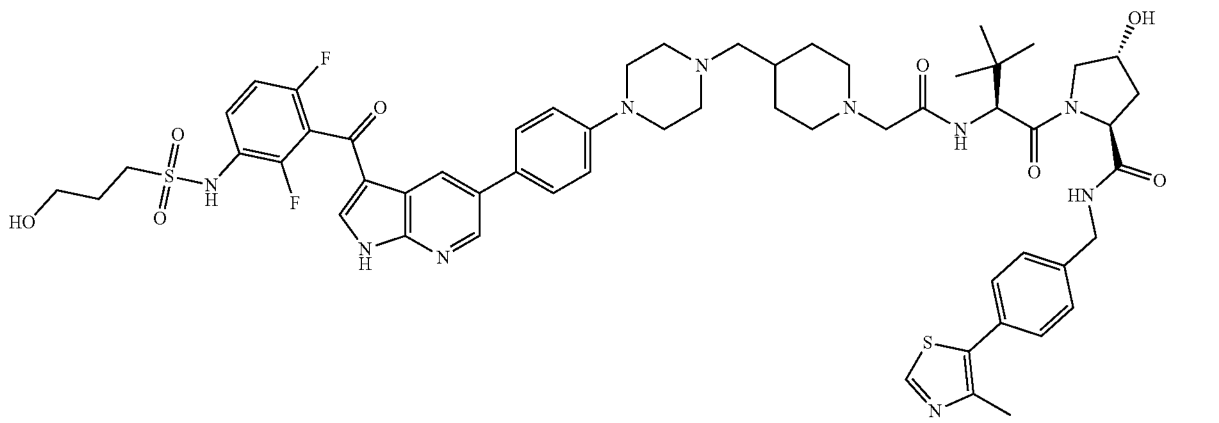 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)CCCO)c7F)c6c5)cc4)CC3)CC2)C(C)(C)C)cc1]

Into a 50-mL round-bottom flask, was placed 3-[(2,4-difluoro-3-[5-[4-(4-[[1-([[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl] methyl)piperidin-4-yl]met (273 mg, 0.23 mmol, 1 equiv), MeOH (20 mL, 493.98 mmol, 2108.71 equiv), $H_2O$ (1 mL, 55.51 mmol, 236.96 equiv), LiOH (16.8 mg, 0.70 mmol, 3 equiv). The resulting solution was stirred for 2 hr at 40° C. in an oil bath. The crude product (263 mg) was purified by Prep-HPLC. This resulted in 31.6 mg (11.93%) of (2S,4R)-1-[(2S)-2-[2-(4-[[4-(4-[3-[2,6-difluoro-3-(3-hydroxypropanesulfonamido)benzoyl]-1H-pyrrolo[2,3-b]pyridin-5-yl] phenyl)piperazin-1-yl]methyl]piperidin-1-yl)acetamido]-3, 3-dimethylbutanoyl]-4-hyd as alight yellow solid. LC/MS (ESI) m/z: 1123.20 $[M+1]^+$; $^1$H-NMR (400 MHz, $CD_3OD$) δ 8.90 (s, 1H), 8.73 (s, 1H), 8.62 (d, J=2.1 Hz, 1H), 7.98 (s, 1H), 7.72-7.54 (m, 3H), 7.48-7.34 (m, 4H), 7.25-7.07 (m, 3H), 4.65 (d, J=10.9 Hz, 1H), 4.62-4.51 (m, 3H), 4.39 (d, J=15.5 Hz, 1H), 3.98-3.79 (m, 2H), 3.66 (t, J=6.0 Hz, 2H), 3.34-3.12 (m, 8H), 3.06-2.90 (m, 2H), 2.86-2.69 (m, 4H), 2.54-2.45 (m, 3H), 2.44-2.18 (m, 5H), 2.17-1.97 (m, 3H), 1.94-1.62 (m, 3H), 1.49-1.22 (m, 2H), 1.06 (d, J=8.1 Hz, 9H).

Exemplary Synthesis of (2S,4R)-1-((2S)-2-(2-(4-((4-(4-(3-(3-((1-cyclopentyl-2,2,2-trifluoroethyl) amino)-2,6-difluorobenzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide (Example 365)

Step 1: Preparation of (E)-N-benzyl-1-cyclopentylmethanimine

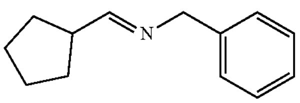 [SMILES: C(=N\Cc1ccccc1)/C1CCCC1]

A suspension of cyclopentanecarbaldehyde (11.2 g, 114.1 mmol, 1 equiv), 1-phenylmethanamine (12.8 g, 119.7 mmol, 1.05 equiv) and $MgSO_4$ (69.9 g, 580.7 mmol, 5.09 equiv) in dichloromethane (350 mL) was stirred for 21 hr at room temperature. The solids were filtered out. The filtrate was evaporated to dryness and dried under vacuum. This resulted in 21.5 g (100%) of (E)-benzyl(cyclopentylmethylidene) amine as a light yellow liquid. LC/MS (ESI) m/z: 188.4 $[M+1]^+$.

Step 2: Preparation of A-benzyl-1-cyclopentyl-2,2,2-trifluoroethan-1-amine

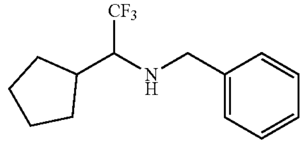 [SMILES: FC(F)(F)C(NCc1ccccc1)C1CCCC1]

To a solution of (E)-benzyl(cyclopentylmethylidene) amine (21.8 g, 116.2 mmol, 1 equiv) in MeCN (220 mL) were added TFA (11.2 mL, 150.8 mmol, 1.30 equiv), $KHF_2$ (7.35 g, 94.1 mmol, 0.81 equiv) and DMF (33 mL) at 0° C. The reaction mixture was stirred for 5 min at 0° C. Then $Me_3SiCF_3$ (24.9 g, 175.2 mmol, 1.51 equiv) was added to the above mixture and the resulting mixture was allowed to react, with stirring, for an additional 17 hr at room temperature. The reaction was then quenched by the addition of 43 mL of sat. $Na_2CO_3$. The mixture was stirred for 5 minutes and then diluted with water (300 mL). The resulting mixture was extracted with ethyl acetate (200 mL×3). The combined organic layers were washed with water (100 mL×2) and brine (100 mL×1) and dried over anhydrous sodium sulfate. The crude was subjected to a silica gel column with ethyl acetate/petroleum ether (1:20). This resulted in 7.34 g (24.6%) of benzyl(1-cyclopentyl-2,2,2-trifluoroethyl)amine as a light yellow liquid. LC/MS (ESI) m/z 258.10 $[M+1]^+$;

$^1$H-NMR (400 MHz, $CDCl_3$) δ 1.44-1.87 (m, 9H), 2.09-2.23 (m, 1H), 2.97-3.06 (m, 1H), 3.86 (d, J=12.9 Hz, 1H), 4.11 (d, J=13.2 Hz, 1H), 7.29-7.41 (m, 5H); $^1$H-NMR (300 MHz, $CDCl_3$) δ 71.5, 72.1, 72.2.

Step 3: Preparation of 1-cyclopentyl-2,2,2-trifluoroethan-1-amine hydrochloride

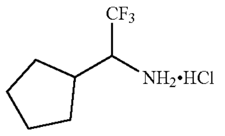

To a solution of benzyl (1-cyclopentyl-2,2,2-trifluoroethyl)amine (6.31 g, 24.52 mmol, 1 equiv) in MeOH (80 mL) in a 500-mL pressure tank reactor was added Pd/C (2.17 g). The mixture was charged with 50 atm $H_2$ and stirred for 19 hr at 50° C. The mixture was filtered and to the filtrate was added HCl in methanol (30 mL). The combined filtrate was concentrated and dried under vacuum. This resulted in 4.81 g (96.3%) of 1-cyclopentyl-2,2,2-trifluoroethan-1-amine hydrochloride as a white solid. LC/MS (ESI) m/z: 168.10 $[M+1]^+$.

Step 4: Preparation of methyl 3-bromo-2,6-difluorobenzoate

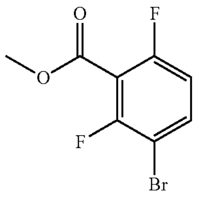

To a solution of 3-bromo-2, 6-difluorobenzoic acid (10 g, 42.2 mmol, 1 equiv) in methanol (100 mL) was added sulfuric acid (4 mL). The reaction solution was heated to reflux for 17 hr. The reaction mixture was cooled to room temperature with a water bath. The resulting mixture was concentrated. The residue was extracted with of ethyl acetate (100 mL×3) and the organic layers combined. The resulting mixture was washed with brine (100 mL×2). The mixture was dried over anhydrous sodium sulfate. The residue was subjected to a silica gel column with ethyl acetate/petroleum ether (1:20). This resulted in 9.04 g (85.4%) of methyl 3-bromo-2, 6-difluorobenzoate as a white solid. $^1$H-NMR (400 MHz, $CDCl_3$) δ 3.98 (d, J=8.7 Hz, 3H), 6.90-6.96 (m, 1H), 7.62-7.70 (m, 1H); $^1$H-NMR (300 MHz, $CDCl_3$) δ 102.0, 110.9.

Step 5: Preparation of methyl 3-((1-cyclopentyl-2,2,2-trifluoroethyl)amino)-2,6-difluorobenzoate

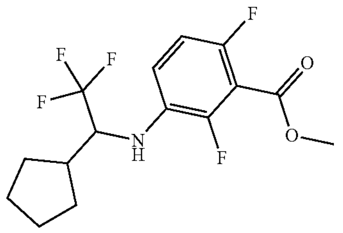 [SMILES: COC(=O)c1c(F)ccc(NC(C2CCCC2)C(F)(F)F)c1F]

A mixture of methyl 3-bromo-2, 6-difluorobenzoate 1.86 g, 7.41 mmol, 1.49 equiv), 1-cyclopentyl-2, 2, 2-trifluoroethan-1-amine hydrochloride (1.01 g, 4.96 mmol, 1 equiv) and $Cs_2CO_3$ (4.83 g, 14.8 mmol, 2.99 equiv) in toluene (15 mL) was purged with $N_2$. Then to this was added RuPhos-PdCl-2nd G (386.9 mg, 0.50 mmol, 0.10 equiv) and the sealed tube was closed and the resulting mixture was stirred for 3 hr at 100° C. The crude was pre-purified by flash chromatography (silica gel, PE:EtOAc=15:1) and then further purified by Prep-TLC (PE:EtOAc=15:1). This resulted in 319.6 mg (19.1%) of methyl 3-[(1-cyclopentyl-2,2,2-trifluoroethyl)amino]-2,6-difluorobenzoate as colorless oil. LC/MS (ESI) m/z: 338.05 $[M+1]^+$.

Step 6: Preparation of 3-((1-cyclopentyl-2,2,2-trifluoroethyl)amino)-2,6-difluorobenzoic acid

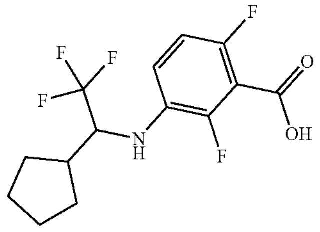 [SMILES: O=C(O)c1c(F)ccc(NC(C2CCCC2)C(F)(F)F)c1F]

To a stirred solution of methyl 3-[(1-cyclopentyl-2, 2, 2-trifluoroethyl) amino]-2, 6-difluorobenzoate (298.4 mg, 0.88 mmol, 1 equiv) in THF (10 mL), methanol (5 mL) and $H_2O$ (5 mL) was added LiOH $H_2O$ (374.1 mg, 8.91 mmol, 10.1 equiv). The resulting solution was stirred for 19 hr at room temperature. The mixture was then evaporated to dryness. To the residue was added 20 mL $H_2O$. 1 M HCl was added to adjust pH to 6. The mixture was extracted by ethyl acetate (40 mL×3). The combined organic layers were washed by water, brine and dried over $Na_2SO_4$. The organic phase was concentrated and dried under vacuum. This resulted in 287 mg (100%) of 3-[(1-cyclopentyl-2,2,2-trifluoroethyl)amino]-2,6-difluorobenzoic acid as a colorless oil. LC/MS (ESI) m/z: 324.05 $[M+1]^+$.

Step 7: Preparation of 3-((1-cyclopentyl-2,2,2-trifluoroethyl)amino)-2,6-difluorobenzoyl chloride

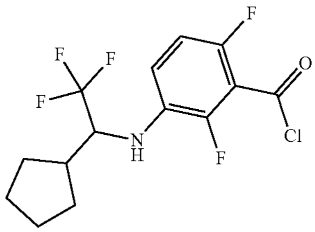 [SMILES: O=C(Cl)c1c(F)ccc(NC(C2CCCC2)C(F)(F)F)c1F]

To a solution of 3-[(1-cyclopentyl-2,2,2-trifluoroethyl)amino]-2,6-difluorobenzoic acid (306.3 mg, 0.95 mmol, 1 equiv) in toluene (10 mL) was added sulfurooyl dichloride (2.8 mL, 38.6 mmol, 40.7 equiv) and DMF (0.06 mL, 0.78 mmol, 0.82 equiv). The resulting solution was heated to reflux for 3 hr. The solution was evaporated to dryness and dried under vacuum. This resulted in 323.8 mg (100%) of 3-[(1-cyclopentyl-2,2,2-trifluoroethyl)amino]-2,6-difluorobenzoyl chloride as light brown oil.

Step 8: Preparation of (5-bromo-1H-pyrrolo[2,3-b]pyridin-3-yl)(3-((1-cyclopentyl-2,2,2-trifluoroethyl)amino)-2,6-difluorophenyl)methanone

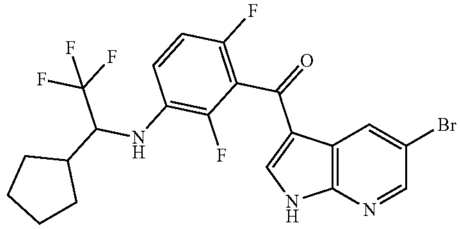 [SMILES: O=C(c1c(F)ccc(NC(C2CCCC2)C(F)(F)F)c1F)c1c[nH]c2ncc(Br)cc12]

To a mixture of $AlCl_3$ (1.03 g, 7.73 mmol, 8.16 equiv) in dichloromethane (7 mL) at 0° C. was added 5-bromo-1H-pyrrolo[2,3-b]pyridine (187.2 mg, 0.95 mmol, 1.00 equiv). The mixture was stirred at 0° C. for 1 hr. Then to this was added 3-[(1-cyclopentyl-2,2,2-trifluoroethyl)amino]-2,6-difluorobenzoyl chloride (323.8 mg, 0.95 mmol, 1 equiv) in dichloromethane (7 mL) at 0° C. The mixture was stirred for 1 hr at 0° C. and then warmed to room temperature for an additional 15 hr. The reaction was then quenched by the addition of 15 mL of water and sat. $NaHCO_3$ aq (15 mL). The mixture was extracted with ethyl acetate (30 mL×3). The combined organic layers were washed with brine (10 mL×1) and dried over anhydrous sodium sulfate. The crude was subjected to a silica gel column with ethyl acetate/petroleum ether (2:5). This resulted in 395.3 mg (83.1%) of 3-[5-bromo-1H-pyrrolo[2,3-b]pyridine-3-carbonyl]-N-(1-cyclopentyl-2,2,2-trifluoroethyl)-2,4-difluoroaniline as a light yellow solid. LC/MS (ESI) m/z: 501.95 $[M+1]^+$.

Step 9: Preparation of tert-butyl 2-(4-((4-(4-(3-(3-((1-cyclopentyl-2,2,2-trifluoroethyl)amino)-2,6-difluorobenzoyl)-1H-pyrrolo[2,3-b]pyridin-5-yl)phenyl)piperazin-1-yl)methyl)piperidin-1-yl)acetate

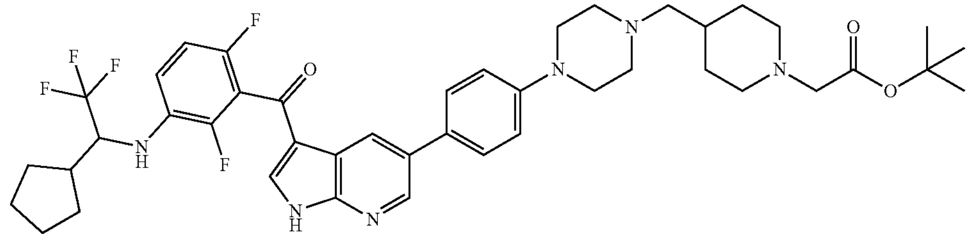 [SMILES: CC(C)(C)OC(=O)CN1CCC(CN2CCN(c3ccc(-c4cnc5[nH]cc(C(=O)c6c(F)ccc(NC(C7CCCC7)C(F)(F)F)c6F)c5c4)cc3)CC2)CC1]

A mixture of 3-[5-bromo-1H-pyrrolo[2,3-b]pyridine-3-carbonyl]-N-(1-cyclopentyl-2,2,2-trifluoroethyl)-2,4-difluoroaniline (200.7 mg, 0.40 mmol, 1 equiv), tert-butyl 2-[4-([4-[4-(4,4,5,5-tetramethyl-1,3,2-dioxaborolan-2-yl)phenyl]piperazin-1-yl]methyl)piperidin-1-yl]acetate (358 mg, 0.72 mmol, 1.79 equiv) and $Na_2CO_3$ (127.9 mg, 1.21 mmol, 3.02 equiv) in dioxane (10 mL) and $H_2O$ (2.5 mL) was purged with $N_2$. Then to this was added Pd(dppf) $Cl_2 \cdot CH_2Cl_2$ (51.4 mg, 0.06 mmol, 0.16 equiv). The sealed tube was closed and reaction mixture was stirred for 4 hr at 105° C. The reaction was then quenched by the addition of water (50 mL). The mixture was extracted with ethyl acetate (40 mL×3) and the combined organic layers were washed with brine (30 mL×1) and dried over anhydrous sodium sulfate. The crude was subjected to a silica gel column with dichloromethane/methanol (15:1). This resulted in 240.2 mg (75.6%) of tert-butyl 2-[4-([4-[4-(3-[3-[(1-cyclopentyl-2,2,2-trifluoroethyl)amino]-2,6-difluorobenzoyl]-1H-pyrrolo[2,3-b]pyridin-5-yl)phenyl]piperazin-1-yl]methyl)piperidin-1-yl]acetate as a light brown solid. LC/MS (ESI) m/z: 795.30 $[M+1]^+$.

Step 10: Preparation of 2-(4-((4-(4-(3-(3-((1-cyclopentyl-2,2,2-trifluoroethyl)amino)-2,6-difluorobenzoyl)-1H-pyrrolo[2,3-b]pyridin-5-yl)phenyl)piperazin-1-yl)methyl)piperidin-1-yl)acetic acid

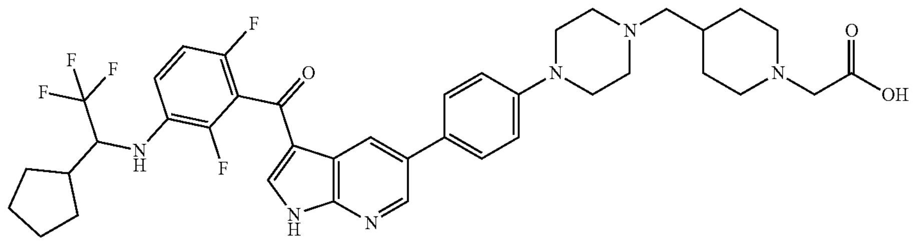 [SMILES: O=C(O)CN1CCC(CN2CCN(c3ccc(-c4cnc5[nH]cc(C(=O)c6c(F)ccc(NC(C7CCCC7)C(F)(F)F)c6F)c5c4)cc3)CC2)CC1]

To a solution of tert-butyl 2-[4-([4-[4-(3-[3-[(1-cyclopentyl-2,2,2-trifluoroethyl)amino]-2,6-difluorobenzoyl]-1H-pyrrolo[2,3-b]pyridin-5-yl)phenyl]piperazin-1-yl]methyl)piperidin-1-yl]acetate (185 mg, 0.23 mmol, 1 equiv) in dichloromethane (15 mL) was added TFA (4.0 mL). The reaction solution was stirred for 15 hr at room temperature. The resulting solution was evaporated to dryness and dried under vacuum. This resulted in 171.9 mg (100%) of 2-[4-([4-[4-(3-[3-[(1-cyclopentyl-2,2,2-trifluoroethyl)amino]-2,6-difluorobenzoyl]-1H-pyrrolo[2,3-b]pyridin-5-yl)phenyl]piperazin-1-yl]methyl)piperidin-1-yl]acetic acid as light yellow oil. LC/MS (ESI) m/z: 739.25 $[M+1]^+$.

Step 11: Preparation of (2S,4R)-1-((2S)-2-(2-(4-((4-(4-(3-(3-((1-cyclopentyl-2,2,2-trifluoroethyl)amino)-2,6-difluorobenzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

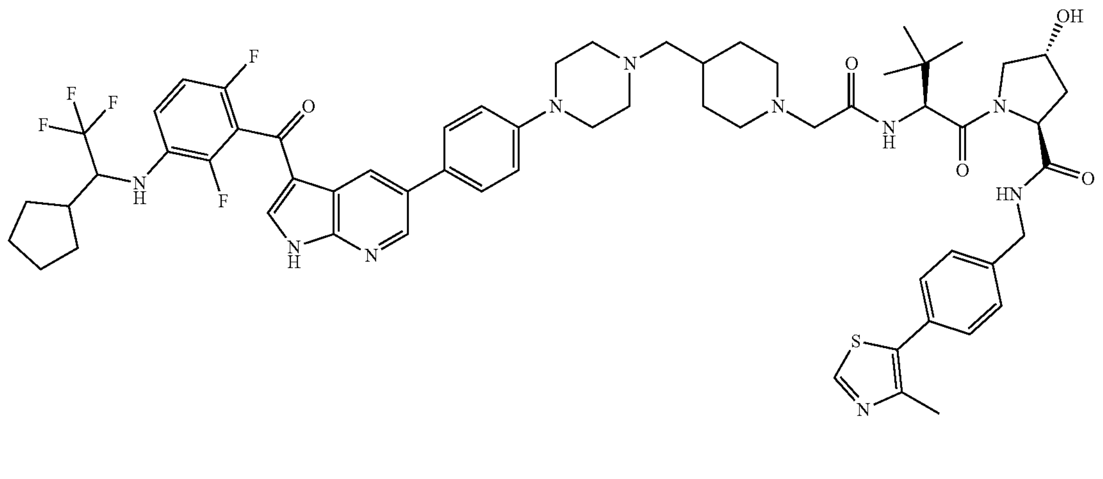 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NC(C8CCCC8)C(F)(F)F)c7F)c6c5)cc4)CC3)CC2)C(C)(C)C)cc1]

To a solution of 2-[4-([4-[4-(3-[3-[(1-cyclopentyl-2,2,2-trifluoroethyl)amino]-2,6-difluorobenzoyl]-1H-pyrrolo[2,3-b]pyridin-5-yl)phenyl]piperazin-1-yl]methyl)piperidin-1-yl]acetic acid (171.9 mg, 0.23 mmol, 1 equiv) and (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (175.4 mg, 0.38 mmol, 1.61 equiv) in DMF (6 mL) was added DIEA (0.4 mL, 2.42 mmol, 10.40 equiv) and BOP (200.3 mg, 0.45 mmol, 1.95 equiv). The reaction solution was stirred for 3 hr at room temperature. The reaction was then quenched by the addition of 30 mL of water. The resulting mixture was extracted with ethyl acetate (50 mL×3). The combined organic layers were washed with water (40 mL×1), brine (40 mL×1), dried over anhydrous sodium sulfate and concentrated. The crude product was purified by Prep-HPLC. This resulted in 109.3 mg (40.8%) of (2S,4R)-1-[(2S)-2-[2-[4-([4-[4-(3-[3-[(1-cyclopentyl-2,2,2-trifluoroethyl)amino]-2,6-difluorobenzoyl]-1H-pyrrolo[2,3-b]pyridin-5-yl)phenyl]piperazin-1-yl]methyl)piperidin-1-yl]acetamido]-3,3-dimethylbutanoyl]-4-hydroxy-N-[[4-(4-methyl-1,3-thiazol-5-yl)phenyl]methyl]pyrrolidine-2-carboxamide as a light yellow solid. LC/MS (ESI) m/z: 1152.20 $[M+1]^+$; $^1H$ NMR (400 MHz, DMSO-$d_6$) δ 0.96 (s, 9H), 1.10-1.27 (m, 2H), 1.28-1.62 (m, 6H), 1.63-1.98 (m, 6H), 1.99-2.38 (m, 6H), 2.47 (s, 6H), 2.75-3.09 (m, 4H), 3.11-3.26 (m, 4H), 3.56-3.78 (m, 3H), 4.13-4.57 (m, 6H), 5.17 (s, 1H), 5.73 (d, J=7.5 Hz, 1H), 6.96-7.27 (m, 4H), 7.43 (s, 4H), 7.59 (d, J=7.5 Hz, 2H), 7.83 (d, J=9.6 Hz, 1H), 8.10 (s, 1H), 8.48 (s, 1H), 8.65 (s, 2H), 9.01 (s, 1H), 12.8 (br., 1H).

Exemplary Synthesis of (2S,4R)-1-((S)-2-(2-(4-((4-(4-(3-(2,6-difluoro-3-(((R)-3-fluoropyridine)-1-sulfonamido)phenoxy)-1H-pyrrolo[2,3-b]pyridin-5-yl)phenyl)piperazin-1-yl)methyl)piperidin-1-yl) acetamido)-3,3-dimethylbutanoyl)-4-hydroxy-N-(4-(4-methylthiazol-5-yl)benzyl)pyrrolidine-2-carboxamide (Example 371)

Step 1: Preparation of 5-bromo-1-tosyl-1H-pyrrolo [2,3-b]pyridine

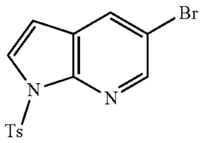 [SMILES: Cc1ccc(S(=O)(=O)n2ccc3cc(Br)cnc32)cc1]

Into a 250-mL 3-necked round-bottom flask purged and maintained with an inert atmosphere of nitrogen, was placed 5-bromo-1H-pyrrolo[2,3-b]pyridine (5.91 g, 29.99 mmol, 1 equiv) in THF (120 mL), to which was added NaH (1.80 g, 45.00 mmol, 1.50 equiv, 60%) in portions at 0° C. in a water/ice bath. The resulting mixture was stirred for 0.5 h at 0° C. Then TsCl (6.29 g, 32.99 mmol, 1.10 equiv) was added and the resulting mixture was allowed to stir for additional 2 h at room temperature. The reaction mixture was then quenched by the addition of water (200 mL) and extracted with ethyl acetate (200 mL×3). The combined organic layer was washed with brine, dried over anhydrous sodium sulfate and concentrated under vacuum. The residue was applied onto a silica gel column eluting with ethyl acetate/petroleum ether (1:2). This resulted in 10.48 g (99.48%) of 5-bromo-1-(4-methylbenzenesulfonyl)-1H-pyrrolo[2,3-b]pyridine as a light yellow solid. LC/MS (ESI) m/z: 350.75 $[M+1]^+$.

Step 2: Preparation of (2S,3R)-5-bromo-N,N,N-triethyl-2-hydroxy-1-tosyl-2,3-dihydro-1H-pyrrolo [2,3-b]pyridin-3-aminium bromide

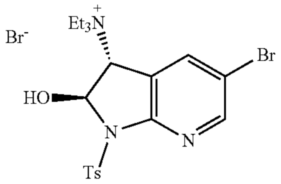

Into a 250-mL round-bottom flask, was placed 5-bromo-1-(4-methylbenzenesulfonyl)-1H-pyrrolo[2,3-b]pyridine (7.02 g, 19.99 mmol, 1 equiv) and $H_2O$ (3.60 mL, 199.83 mmol, 10.00 equiv) in acetone (130 mL), to which was added NBS (3.91 g, 21.97 mmol, 1.10 equiv). The resulting solution was stirred for 4.5 h at room temperature, and then was added by TEA (3.0 mL, 21.58 mmol, 1.08 equiv). The reaction mixture was allowed to stir for additional 1 h at room temperature, and then was concentrated under vacuum. The residue was applied onto a silica gel column eluting with ethyl acetate/petroleum ether (1:1). This resulted in 13.70 g (124.78%) of (2S,3R)-5-bromo-N,N,N-triethyl-2-hydroxy-1-(4-methylbenzenesulfonyl)-1H,2H,3H-pyrrolo[2,3-b]pyridin-3-aminium bromide as a brown solid. LC/MS (ESI) m/z: 467.90 $[M+1]^+$.

Step 3: Preparation of 2-(difluoromethoxy)-1,3-difluorobenzene

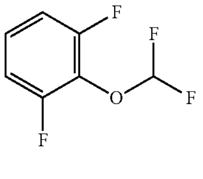 [SMILES: Fc1cccc(F)c1OC(F)F]

Into a 500-mL round-bottom flask purged and maintained with an inert atmosphere of nitrogen, was placed 2,6-difluorophenol (20.00 g, 153.73 mmol, 1 equiv), sodium 2-chloro-2,2-difluoroacetate (46.89 g, 307.56 mmol, 2.00 equiv), $K_2CO_3$ (25.49 g, 184.44 mmol, 1.20 equiv) in DMF (200 mL) and $H_2O$ (20 mL). The resulting mixture was stirred for 3 h at 100° C. in an oil bath. The reaction mixture was cooled to room temperature and quenched by HCl solution (13 mol/L, 30 mL). The mixture was diluted with water (300 mL) and extracted with ethyl acetate (300 mL×3). The combined organic layer was washed with brine (300 mL×2), dried over anhydrous sodium sulfate and concentrated under vacuum. This resulted in 17.17 g (62.01%) of 2-(difluoromethoxy)-1,3-difluorobenzene as a yellow liquid. $^1$H-NMR (300 MHz, $CDCl_3$) δ 7.24-7.09 (m, 1H), 7.03-6.93 (m, 2H), 6.69 (t, J=73.4 Hz, 1H).

Step 4: Preparation of 2-(difluoromethoxy)-1,3-difluoro-4-nitrobenzene

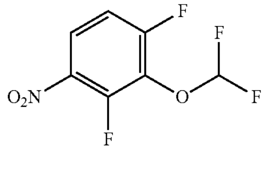 [SMILES: O=[N+]([O-])c1ccc(F)c(OC(F)F)c1F]

Into a 100-mL 3-necked round-bottom flask, was placed $H_2SO_4$ (35 mL), to which was added $HNO_3$ (35 mL, 65%) at −10° C. in a liquid nitrogen/EtOH bath. Then 2-(difluoromethoxy)-1,3-difluorobenzene (7.00 g, 38.87 mmol, 1 equiv) was added slowly at −10° C. The resulting mixture was stirred for 0.5 h at −10° C. The reaction mixture was diluted with cold water (800 mL) and extracted with ethyl acetate (300 mL×3). The combined organic layer was washed with $NaHCO_3$ (200 mL), dried over anhydrous sodium sulfate and concentrated under vacuum. The residue was applied onto a silica gel column eluting with ethyl acetate/petroleum ether (1:50). This resulted in 4.68 g (53.49%) of 2-(difluoromethoxy)-1,3-difluoro-4-nitrobenzene as a yellow oil. $^1$H NMR (300 MHz, $CDCl_3$) δ 8.15-8.07 (m, 1H), 7.29-7.17 (m, 1H), 6.69 (t, J=72.0 Hz, 1H).

Step 5: Preparation of 2,6-difluoro-3-nitrophenol

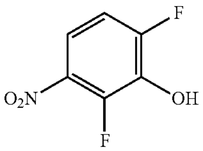 [SMILES: O=[N+]([O-])c1ccc(F)c(O)c1F]

Into a 250-mL round-bottom flask, was placed 2-(difluoromethoxy)-1,3-difluoro-4-nitrobenzene (6.68 g, 29.68 mmol, 1 equiv) in acetic acid (6 mL), to which was added hydrogen bromide solution (40%, 90 mL) at room temperature. The resulting solution was stirred for 40 h at 130° C. in an oil bath. The reaction mixture was cooled to room temperature and diluted with water (500 mL). The resulting mixture was extracted with ethyl acetate (400 mL×2) and the combined organic layer was washed with brine (400 mL), dried over anhydrous sodium sulfate and concentrated under vacuum. The residue was applied onto a silica gel column eluting with ethyl acetate/petroleum ether (1:4). This resulted in 3.50 g (67.36%) of 2,6-difluoro-3-nitrophenol as a yellow solid. LC/MS (ESI) m/z: 173.65 $[M-1]^+$.

Step 6: Preparation of 5-bromo-3-(2,6-difluoro-3-nitrophenoxy)-1-tosyl-1H-pyrrolo[2,3-b]pyridine

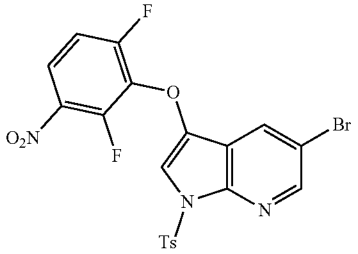 [SMILES: Cc1ccc(S(=O)(=O)n2cc(Oc3c(F)ccc([N+](=O)[O-])c3F)c3cc(Br)cnc32)cc1]

Into a 250-mL round-bottom flask, was placed 2,6-difluoro-3-nitrophenol (1.05 g, 6.00 mmol, 1 equiv), (2S,3R)-5-bromo-N,N,N-triethyl-2-hydroxy-1-(4-methylbenzenesulfonyl)-1H,2H,3H-pyrrolo[2,3-b]pyridin-3-aminium bromide (3.95 g, 7.19 mmol, 1.20 equiv), TEA (1.21 g, 11.96 mmol, 1.99 equiv) in ethyl acetate (70 mL), to which was added dry 4 A MS (5 g). The resulting mixture was stirred for 4 h at 80° C. in an oil bath, and then was cooled to room temperature and was added by ethoxyethane trifluoroborane (4.26 g, 30.01 mmol, 5.01 equiv). The resulting mixture was allowed to stir for additional 2 h at 50° C. in an oil bath. The reaction mixture was cooled to room temperature and the solids were filtered out. The filtrate was diluted with ethyl acetate (250 mL) and washed with saturated $Na_2CO_3$ solution (100 mL) and brine (100 mL), dried over anhydrous sodium sulfate and concentrated under vacuum. The residue was applied onto a silica gel column eluting with ethyl acetate/petroleum ether (1:7). This resulted in 1.13 g (35.94%) of 5-bromo-3-(2,6-difluoro-3-nitrophenoxy)-1-(4-methylbenzenesulfonyl)-1H-pyrrolo[2,3-b]pyridine as a yellow solid. LC/MS (ESI) m/z: 523.75 $[M+1]^+$.

Step 7: Preparation of 3-((5-bromo-1-tosyl-1H-pyrrolo[2,3-b]pyridin-3-yl)oxy)-2,4-difluoroaniline

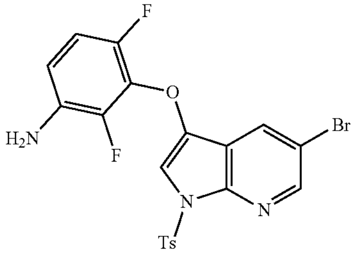

Into a 50-mL round-bottom flask, was placed 5-bromo-3-(2,6-difluoro-3-nitrophenoxy)-1-(4-methylbenzenesulfonyl)-1H-pyrrolo[2,3-b]pyridine (1.13 g, 2.16 mmol, 1 equiv) in acetic acid (10 mL). This was followed by the addition of iron powder (965.6 mg, 17.29 mmol, 8.02 equiv) at room temperature. The resulting mixture was stirred for 3 h at 50° C. in an oil bath. The reaction mixture was cooled to room temperature and the pH value of the mixture was adjusted to 8 with saturated $Na_2CO_3$ solution. The mixture was extracted with ethyl acetate (250 mL×3) and the combined organic layer was dried over anhydrous sodium sulfate and concentrated under vacuum. The residue was applied onto a silica gel column eluting with ethyl acetate/petroleum ether (1/5). This resulted in 510 mg (47.87%) of 3-[[5-bromo-1-(4-methylbenzenesulfonyl)-1H-pyrrolo[2,3-b]pyridin-3-yl]oxy]-2,4-difluoroaniline as a pink solid. LC/MS (ESI) m/z: 493.75 $[M+1]^+$.

Step 8: Preparation of 3-((5-bromo-1H-pyrrolo[2,3-b]pyridin-3-yl)oxy)-2,4-difluoroaniline

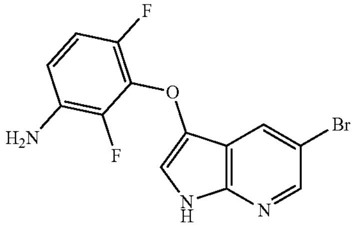 [SMILES: Nc1ccc(F)c(Oc2c[nH]c3ncc(Br)cc23)c1F]

Into a 50-mL round-bottom flask, was placed 3-[[5-bromo-1-(4-methylbenzenesulfonyl)-1H-pyrrolo[2,3-b]pyridin-3-yl]oxy]-2,4-difluoroaniline (510 mg, 1.03 mmol, 1 equiv), TBAF (3.5 mL) in THF (7 mF). The resulting solution was stirred for 24 h at room temperature. The reaction mixture was diluted with water (100 mF) and extracted with ethyl acetate (120 mF×3). The combined organic layer was washed with brine, dried over anhydrous sodium sulfate and concentrated under vacuum. The residue was applied onto a silica gel column eluting with ethyl acetate/petroleum ether (2/3). This resulted in 290 mg (82.64%) of 3-([5-bromo-1H-pyrrolo[2,3-b]pyridin-3-yl]oxy)-2,4-difluoroaniline as a light brown solid. FC/MS (ESI) m/z: 339.80 $[M+1]^+$.

Step 9: Preparation of (R)—N-(3-((5-bromo-1H-pyrrolo[2,3-b]pyridin-3-yl)oxy)-2,4-difluorophenyl)-3-fluoropyrrolidine-1-sulfonamide

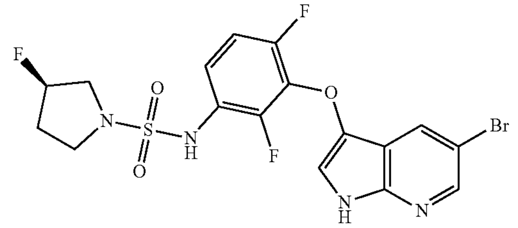 [SMILES: O=S(=O)(Nc1ccc(F)c(Oc2c[nH]c3ncc(Br)cc23)c1F)N1CC[C@@H](F)C1]

Into a 8-mF sealed tube, was placed 3-([5-bromo-1H-pyrrolo[2,3-b]pyridin-3-yl]oxy)-2,4-difluoroaniline (200 mg, 0.59 mmol, 1 equiv), DMAP (14.4 mg, 0.12 mmol, 0.20 equiv) in pyridine (660 mF), to which was added (3R)-3-fluoropyrrolidine-1-sulfonyl chloride (220.6 mg, 1.18 mmol, 2.00 equiv) slowly at room temperature. The resulting solution was stirred for 24 h at 45° C. in an oil bath. The reaction mixture was cooled to room temperature and diluted with water (50 mL). The mixture was extracted with ethyl acetate (50 mL×2) and the organic layers was combined, dried over anhydrous sodium sulfate and concentrated under vacuum. The residue was applied onto a silica gel column eluting with ethyl acetate/petroleum ether (1/1). This resulted in 216 mg (74.77%) of (3R)—N-[3-([5-bromo-1H-pyrrolo[2,3-b]pyridin-3-yl]oxy)-2,4-difluorophenyl]-3-fluoropyrrolidine-1-sulfonamide as a light brown solid. LC/MS (ESI) m/z: 490.75 [M+1]$^+$.

Step 10: Preparation of tert-butyl (R)-2-(4-((4-(4-(3-(2,6-difluoro-3-((3-fluoropyrrolidine)-1-sulfonamido)phenoxy)-1H-pyrrolo[2,3-b]pyridin-5-yl)phenyl)piperazin-1-yl)methyl)piperidin-1-yl)acetate

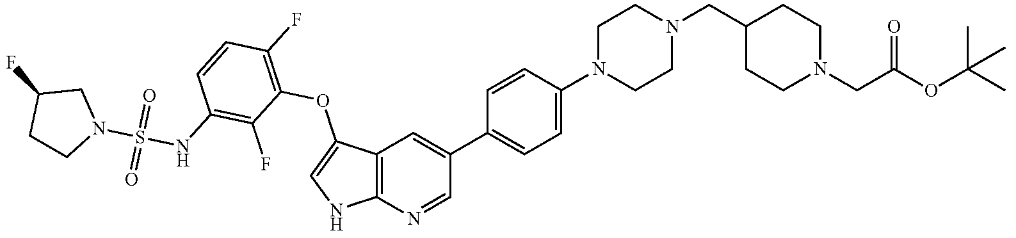 [SMILES: CC(C)(C)OC(=O)CN1CCC(CN2CCN(c3ccc(-c4cnc5[nH]cc(Oc6c(F)ccc(NS(=O)(=O)N7CC[C@@H](F)C7)c6F)c5c4)cc3)CC2)CC1]

Into a 30-mL sealed tube purged and maintained with an inert atmosphere of nitrogen, was placed (3R)—N-[3-([5-bromo-1H-pyrrolo[2,3-b]pyridin-3-yl]oxy)-2,4-difluorophenyl]-3-fluoropyrrolidine-1-sulfonamide (300 mg, 0.61 mmol, 1 equiv), tert-butyl 2-[4-([4-[4-(4,4,5,5-tetramethyl-1,3,2-dioxaborolan-2-yl)phenyl]piperazin-1-yl]methyl)piperidin-1-yl]acetate (366 mg, 0.73 mmol, 1.20 equiv), $Na_2CO_3$ (194.2 mg, 1.83 mmol, 3.00 equiv), Pd(dppf)$C_{1-2}$—$CH_2Cl_2$ (49.9 mg, 0.06 mmol, 0.10 equiv) in dioxane (12 mL) and $H_2O$ (2 mL). The resulting mixture was stirred for 2 h at 105° C. in an oil bath. The reaction mixture was cooled to room temperature and diluted with water (80 mL). The resulting mixture was extracted with ethyl acetate (80 mL×2). The combined organic layers were dried over anhydrous sodium sulfate and concentrated under vacuum. The residue was applied onto a silica gel column eluting with dichloromethane/methanol (15/1). This resulted in 454 mg (94.84%) of tert-butyl 2-(4-[[4-(4-[3-[2,6-difluoro-3-([[(3R)-3-fluoropyrrolidin-1-yl]sulfonyl]amino)phenoxy]-1H-pyrrolo[2,3-b]pyridin-5-yl]phenyl)piperazin-1-yl] methyl]piperidin-1-yl)acetate as a brown solid. LC/MS (ESI) m/z: 784.05 [M+1]$^+$.

Step 11: Preparation of (R)-2-(4-((4-(4-(3-(2,6-difluoro-3-((3-fluoropyrrolidine)-1-sulfonamido)phenoxy)-1H-pyrrolo[2,3-b]pyridin-5-yl)phenyl)piperazin-1-yl)methyl)piperidin-1-yl)acetic acid

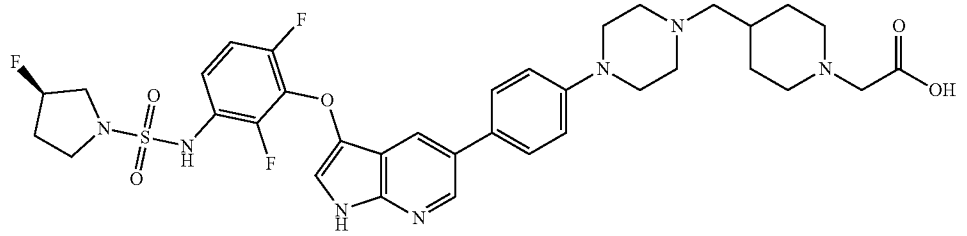 [SMILES: O=C(O)CN1CCC(CN2CCN(c3ccc(-c4cnc5[nH]cc(Oc6c(F)ccc(NS(=O)(=O)N7CC[C@@H](F)C7)c6F)c5c4)cc3)CC2)CC1]

Into a 50-mL round-bottom flask, was placed tert-butyl 2-(4-[[4-(4-[3-[2,6-difluoro-3-([[(3R)-3-fluoropyrrolidin-1-yl]sulfonyl]amino)phenoxy]-1H-pyrrolo[2,3-b]pyridin-5-yl]phenyl)piperazin-1-yl]methyl]piperidin-1-yl)acetate (398 mg, 0.51 mmol, 1 equiv) in dichloromethane (6 mL), to which was added TFA (3 mL) at room temperature. The resulting solution was stirred for 3 h at 35° C. in an oil bath, and then was concentrated under vacuum. This resulted in 369 mg (99.86%) of 2-(4-[[4-(4-[3-[2,6-difluoro-3-([[(3R)-3-fluoropyrrolidin-1-yl]sulfonyl]amino)phenoxy]-1H-pyrrolo[2,3-b]pyridin-5-yl]phenyl)piperazin-1-yl]methyl]piperidin-1-yl)acetic acid as a brown oil. LC/MS (ESI) m/z: 728.05 [M+1]$^+$.

Step 12: Preparation of (2S,4R)-1-((S)-2-(2-(4-((4-(4-(3-(2,6-difluoro-3-(((R)-3-fluoropyrrolidine)-1-sulfonamido)phenoxy)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

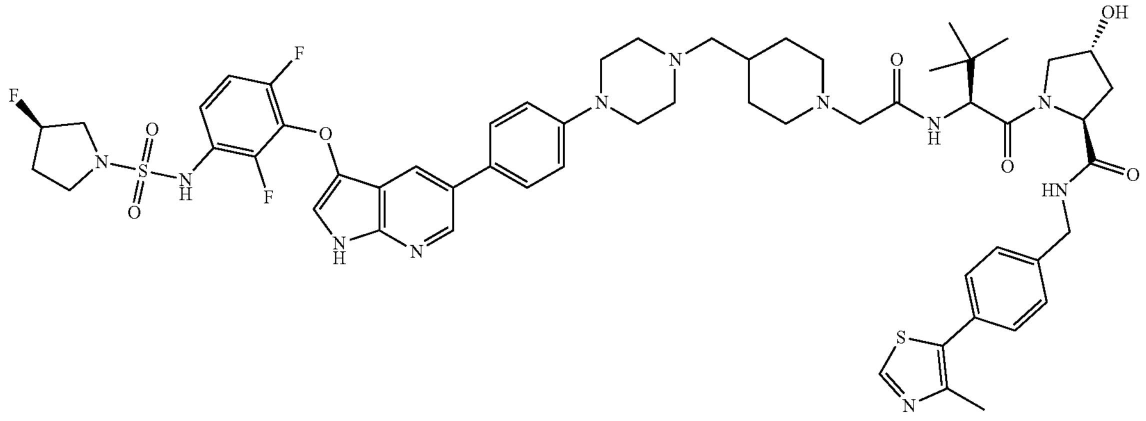 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(Oc7c(F)ccc(NS(=O)(=O)N8CC[C@@H](F)C8)c7F)c6c5)cc4)CC3)CC2)C(C)(C)C)cc1]

Into a 8-mL tube, was placed 2-(4-[[4-(4-[3-[2,6-difluoro-3-([[(3R)-3-fluoropyrrolidin-1-yl]sulfonyl]amino)phenoxy]-1H-pyrrolo[2,3-b]pyridin-5-yl]phenyl)piperazin-1-yl]methyl]piperidin-1-yl)acetic acid (218.3 mg, 0.30 mmol, 1 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (168.1 mg, 0.39 mmol, 1.30 equiv), DIEA (155 mg, 1.20 mmol, 4.00 equiv), BOP (159.1 mg, 0.36 mmol, 1.20 equiv) in DMF (5 mL). The resulting solution was stirred for 1 h at room temperature. The reaction mixture was diluted with water (50 mL) and extracted with a mixture of dichloromethane/methanol (10/1, 50 mL×2). The organic layers were combined and washed with brine (50 mL×2), dried over anhydrous sodium sulfate and concentrated under vacuum. The residue was applied onto a silica gel column eluting with dichloromethane/methanol (13/1). The obtained product was further purified by Prep-HPLC. This resulted in 64.2 mg (18.77%) of (2S,4R)-1-[(2S)-2-[2-(4-[[4-(4-[3-[2,6-difluoro-3-([[(3R)-3-fluoropyrrolidin-1-yl]sulfonyl]amino)phenoxy]-1H-pyrrolo[2,3-b]pyridin-5-yl]phenyl)piperazin-1-yl]methyl]piperidin-1-yl)acetamido]-3,3-dimethylbutanoyl]-4-hydroxy-N-[[4-(4-methyl-1,3-thiazol-5-yl)phenyl]methyl]pyrrolidine-2-carboxamide as a white solid. LC/MS (ESI) m/z: 1140.2 $[M+1]^+$; $^1$H-NMR (300 MHz, $CD_3OD$) δ 8.87 (s, 1H), 8.43 (s, 1H), 7.99 (s, 1H), 7.51-7.40 (m, 7H), 7.09-7.03 (m, 4H), 5.08 (d, J=53.0 Hz, 1H), 4.63-4.48 (m, 4H), 4.38-4.33 (m, 1H), 3.91-3.76 (m, 2H), 3.63-3.34 (m, 4H), 3.22-3.19 (m, 4H), 3.02 (s, 2H), 2.91-2.84 (m, 2H), 2.57-2.54 (m, 4H), 2.47 (s, 3H), 2.25-2.16 (m, 5H), 2.12-1.97 (m, 2H), 1.87-1.76 (m, 3H), 1.60 (s, 1H), 1.36-1.27 (m, 2H), 1.04 (s, 9H).

Exemplary Synthesis of (2S,4R)-1-((S)-2-(2-(3-(2-(3-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-1-yl)ethyl)azetidin-1-yl)acetamido)-3,3-dimethylbutanoyl)-4-hydroxy-N-(4-(4-methylthiazol-5-yl)benzyl)pyrrolidine-2-carboxamide (Example 441)

Step 1: Preparation of tert-butyl 3-(4-(benzyloxy)phenyl)azetidine-1-carboxylate

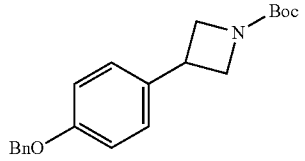 [SMILES: CC(C)(C)OC(=O)N1CC(c2ccc(OCc3ccccc3)cc2)C1]

Into a 1000-mL 3-necked round-bottom flask purged and maintained with an inert atmosphere of nitrogen, was placed zinc (11 g, 168.25 mmol, 2.95 equiv) in DMF (400 mL), to which was added $I_2$ (2.23 g, 8.79 mmol, 0.15 equiv) at room temperature. The resulting mixture was stirred about 5 min at room temperature, and then was charged with tert-butyl 3-iodoazetidine-1-carboxylate (16.2 g, 57.22 mmol, 1.00 equiv) in portions. The reaction mixture was allowed to stir about 1 h at room temperature. Then to the above mixture was added 1-(benzyloxy)-4-bromobenzene (15 g, 57.01 mmol, 1.00 equiv), SPhos (2.4 g, 5.85 mmol, 0.10 equiv), $Pd_2(dba)_3$ (3.6 g, 3.93 mmol, 0.07 equiv). The resulting mixture was stirred for another 3 hours at 50° C. under nitrogen atmosphere. The reaction was then quenched by the addition of 2000 mL water and the resulting mixture was extracted with ethyl acetate (3×700 mL). The organic layers were combined and washed with brine (3×700 ml), dried over anhydrous sodium sulfate and concentrated under vacuum. The residue was applied onto a silica gel column eluting with ethyl acetate/petroleum ether (0% to 33% gradient). This resulted in 13 g (67.25%) of tert-butyl 3-[4-(benzyloxy)phenyl]azetidine-1-carboxylate as a yellow solid. LC/MS (ESI) m/z: 340.10 $[M+1]^+$.

Step 2: Preparation of tert-butyl 3-(4-hydroxyphenyl)azetidine-1-carboxylate

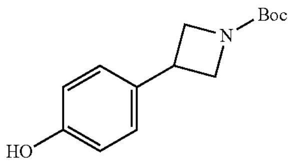 [SMILES: CC(C)(C)OC(=O)N1CC(c2ccc(O)cc2)C1]

Into a 100-mL round-bottom flask, was placed tert-butyl 3-[4-(benzyloxy)phenyl]azetidine-1-carboxylate (3 g, 8.84 mmol, 1.00 equiv) and Pd/C (10%, 3 g, 28.18 mmol, 3.19 equiv)) in MeOH (30 mL) under nitrogen atmosphere. The flask was then vacuumed and flushed with hydrogen. The reaction mixture was hydrogenated at room temperature for 3 hours under hydrogen atmosphere using a hydrogen balloon. Then the reaction mixture was filtered through a celite pad and the filtrate was concentrated under reduced pressure. This resulted in 1.5 g (68.18%) of tert-butyl 3-(4-hydroxyphenyl)azetidine-1-carboxylate as a white solid. LC/MS (ESI) m/z: 250.10 $[M+1]^+$.

Step 3: Preparation of tert-butyl 3-(4-(((trifluoromethyl)sulfonyl)oxy)phenyl)azetidine-1-carboxylate

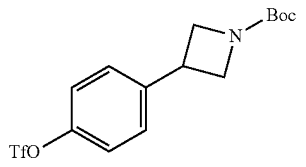 [SMILES: CC(C)(C)OC(=O)N1CC(c2ccc(OS(=O)(=O)C(F)(F)F)cc2)C1]

Into a 100-mL round-bottom flask, was placed tert-butyl 3-(4-hydroxyphenyl)azetidine-1-carboxylate (1.5 g, 0.006 mmol, 1.00 equiv), phenyl(trifluoromethanesulfonyloxy) amino trifluoromethanesulfonate (4.6 g, 11.82 mmol, 1.96 equiv), DIEA (2.30 g, 17.80 mmol, 2.96 equiv) in DCM (30 mL). The resulting solution was stirred for 12 hours at room temperature. The mixture was concentrated. The residue was applied onto a silica gel column eluting with ethyl acetate/petroleum ether (1:100 to 3:100 gradient). This resulted in 1.5 g (65.36%) of tert-butyl 3-[4-(trifluoromethanesulfonyloxy)phenyl]azetidine-1-carboxylate as off-white oil. LC/MS (ESI) m/z: 382.10 $[M+1]^+$.

Step 4: Preparation of tert-butyl 3-(4-(4,4,5,5-tetramethyl-1,3,2-dioxaborolan-2-yl)phenyl)azetidine-1-carboxylate

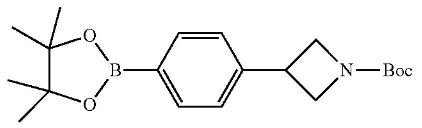 [SMILES: CC(C)(C)OC(=O)N1CC(c2ccc(B3OC(C)(C)C(C)(C)O3)cc2)C1]

Into a 100-mL round-bottom flask, was placed tert-butyl 3-[4-(trifluoromethanesulfonyloxy)phenyl]azetidine-1-carboxylate (1.5 g, 3.93 mmol, 1.00 equiv), 4,4,5,5-tetramethyl-2-(4,4,5,5-tetramethyl-1,3,2-dioxaborolan-2-yl)-1,3,2-dioxaborolane (1.5 g, 5.90 mmol, 1.50 equiv), KOAc (1.2 g, 12.23 mmol, 3.11 equiv), $Pd(dppf)Cl_2$ (140 mg, 0.19 mmol, 0.05 equiv) in dioxane (10 ml) under nitrogen atmosphere. The resulting solution was stirred for 1 hour at 100° C. under nitrogen atmosphere. The mixture was concentrated and the residue was applied onto a silica gel column eluting with ethyl acetate/petroleum ether (1:100 to 1:10 gradient). This resulted in 500 mg (35.38%) of tert-butyl 3-[4-(4,4,5,5-tetramethyl-1,3,2-dioxaborolan-2-yl)phenyl] azetidine-1-carboxylate as yellow oil. LC/MS (ESI) m/z: 360.23 $[M+1]^+$.

Step 5: Preparation of 3-(4-(4,4,5,5-tetramethyl-1,3,2-dioxaborolan-2-yl)phenyl)azetidine

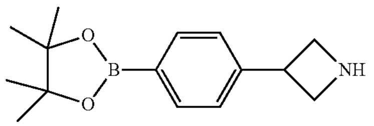 [SMILES: CC1(C)OB(c2ccc(C3CNC3)cc2)OC1(C)C]

Into a 100-mL round-bottom flask, was placed tert-butyl 3-[4-(4,4,5,5-tetramethyl-1,3,2-dioxaborolan-2-yl)phenyl] azetidine-1-carboxylate (500 mg, 1.39 mmmo, 1.00 equiv) in DCM (10 mL), to which was added TFA (3 mL). The resulting solution was stirred for 1 hr at room temperature. The mixture was concentrated under reduced pressure. This resulted in 350 mg (crude) of 3-[4-(4,4,5,5-tetramethyl-1,3,2-dioxaborolan-2-yl)phenyl]azetidine as yellow oil.

Step 6: Preparation of tert-butyl 3-(2-hydroxyethyl)azetidine-1-carboxylate

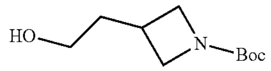 [SMILES: CC(C)(C)OC(=O)N1CC(CCO)C1]

Into a 250-mL 3-necked round-bottom flask, was placed 2-[1-[(tert-butoxy)carbonyl]azetidin-3-yl]acetic acid (10 g, 46.46 mmol, 1.00 equiv) in THF (100 mL), to which was added $BH_3 \cdot THF$ (70 mL) dropwise at 0° C. The resulting solution was stirred for 12 hr at room temperature. The reaction was then quenched by the addition of NaOH solution (2 M, 100 mL). The resulting mixture was extracted with ethyl acetate (3×100 mL) and the combined organic layer was washed with brine, dried over anhydrous sodium sulfate and concentrated. This resulted in 8.5 g (90.91%) of tert-butyl 3-(2-hydroxyethyl)azetidine-1-carboxylate as light yellow oil.

Step 7: Preparation of tert-butyl 3-(2-(tosyloxy)ethyl)azetidine-1-carboxylate

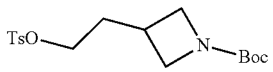 [SMILES: Cc1ccc(S(=O)(=O)OCCC2CN(C(=O)OC(C)(C)C)C2)cc1]

Into a 500-mL 3-necked round-bottom flask, was placed tert-butyl 3-(2-hydroxyethyl)azetidine-1-carboxylate (8.5 g, 42.23 mmol, 1.00 equiv), TEA (12.8 g, 0.13 mmol, 3.00 equiv) in DCM (100 mL), to which was added TsCl (10.5 g, 55.08 mmol, 1.30 equiv) slowly. The resulting solution was stirred for 12 hr at room temperature. The reaction was then quenched by the addition of 100 mL water. The resulting mixture was extracted with dichloromethane (2×50 mL). The combined organic phase was washed with brine, dried over anhydrous sodium sulfate and concentrated. The residue was applied onto a silica gel column eluting with ethyl acetate/petroleum ether (1:100 to 40:100 gradient). This resulted in 8 g (53.33%) of tert-butyl 3-(2-(tosyloxy)ethyl) azetidine-1-carboxylate as a yellow oil.

Step 8: Preparation of tert-butyl 3-(2-(3-(4-(4,4,5,5-tetramethyl-1,3,2-dioxaborolan-2-yl)phenyl)azetidin-1-yl)ethyl)azetidine-1-carboxylate

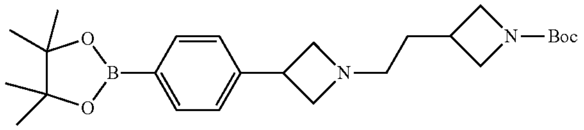 [SMILES: CC(C)(C)OC(=O)N1CC(CCN2CC(c3ccc(B4OC(C)(C)C(C)(C)O4)cc3)C2)C1]

Into a 100-mL round-bottom flask, was placed 3-[4-(4,4,5,5-tetramethyl-1,3,2-dioxaborolan-2-yl)phenyl]azetidine (350 mg, 1.35 mmol, 1.00 equiv), tert-butyl 3-[2-[(4-methylbenzenesulfonyl)oxy]ethyl]azetidine-1-carboxylate (480 mg, 1.35 mmol, 1.00 equiv), $K_2CO_3$ (932 mg, 6.74 mmol, 4.99 equiv), NaI (20 mg, 0.133 mmol, 0.10 equiv) in MeCN (50 mL). The resulting solution was stirred for 12 hr at 70° C. in an oil bath. The insoluble solids were filtered out and the filtrate was concentrated. The residue was applied onto a silica gel column eluting with dichloromethane/methanol (100:1 to 100:7 gradient). This resulted in 180 mg (30.13%) of tert-butyl 3-(2-[3-[4-(4,4,5,5-tetramethyl-1,3,2-dioxaborolan-2-yl)phenyl]azetidin-1-yl]ethyl)azetidine-1-carboxylate as a yellow solid. LC/MS (ESI) m/z: 443.25 $[M+1]^+$.

Step 9: Preparation of tert-butyl (R)-3-(2-(3-(4-(3-(2,6-difluoro-3-((3-fluoropyrrolidine)-1-sulfonamido)benzoyl)-1H-pyrrolo[2,3-b]pyridin-5-yl)phenyl)azetidin-1-yl)ethyl)azetidine-1-carboxylate

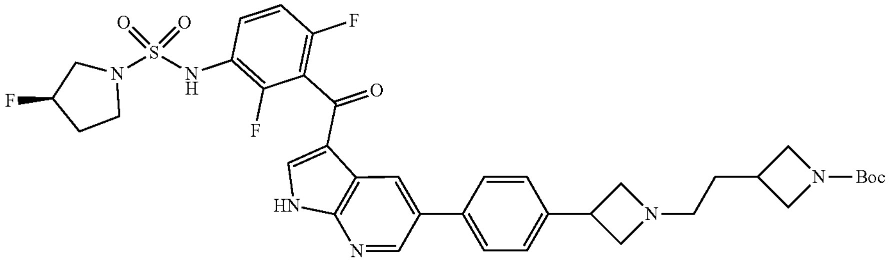 [SMILES: CC(C)(C)OC(=O)N1CC(CCN2CC(c3ccc(-c4cnc5[nH]cc(C(=O)c6c(F)ccc(NS(=O)(=O)N7CC[C@@H](F)C7)c6F)c5c4)cc3)C2)C1]

Into a 100-mL round-bottom flask, was placed tert-butyl 3-(2-[3-[4-(4,4,5,5-tetramethyl-1,3,2-dioxaborolan-2-yl) phenyl]azetidin-1-yl]ethyl)azetidine-1-carboxylate (180 mg, 0.41 mmol, 1.00 equiv), (3R)—N-(3-[5-bromo-1H-pyrrolo[2,3-b]pyridine-3-carbonyl]-2,4-difluorophenyl)-3-fluoropyrrolidine-1-sulfonamide (204 mg, 0.41 mmol, 1.00 equiv), $Na_2CO_3$ (130 mg, 1.227 mmol, 3.01 equiv), Pd(dppf)$Cl_2$ (60 mg, 0.082 mmol, 0.20 equiv) in dioxane (17 mL) and water (3 mL) under nitrogen atmosphere. The resulting mixture was stirred for 2 hr at 85° C. in an oil bath. The residue was applied onto a silica gel column eluting with dichloromethane/methanol (100:1 to 100:8 gradient). This resulted in 100 mg (33.27%) of tert-butyl 3-[2-[3-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)azetidin-1-yl]ethyl]azetidine-1-carboxylate as a yellow solid. LC/MS (ESI) m/z: 739.25 $[M+1]^+$.

Step 10: Preparation of (R)—N-(3-(5-(4-(1-(2-(azetidin-3-yl)ethyl)azetidin-3-yl)phenyl)-1H-pyrrolo[2,3-b]pyridine-3-carbonyl)-2,4-difluorophenyl)-3-fluoropyrrolidine-1-sulfonamide

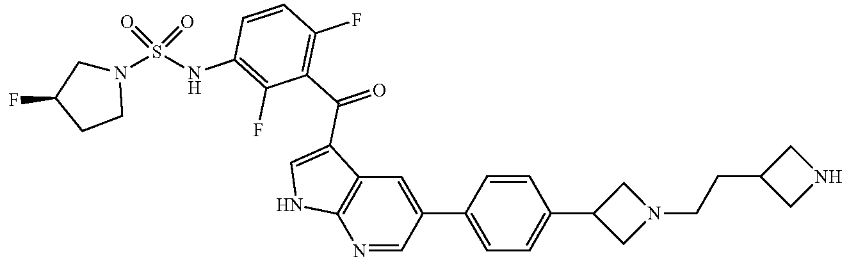 [SMILES: O=C(c1c(F)ccc(NS(=O)(=O)N2CC[C@@H](F)C2)c1F)c1c[nH]c2ncc(-c3ccc(C4CN(CCC5CNC5)C4)cc3)cc12]

Into a 50-mL round-bottom flask, was placed tert-butyl 3-[2-[3-(4-[3-[2,6-difluoro-3-([[(3R)-3-fluoropyrrolidin-1-yl]sulfonyl]amino)benzoyl]-1H-pyrrolo[2,3-b]pyridin-5-yl] phenyl)azetidin-1-yl]ethyl]azetidine-1-carboxylate (20 mg, 0.027 mmol, 1 equiv) in DCM (3 mL), to which was added TFA (0.2 mL) at room temperature. The resulting solution was stirred for 1 hr at room temperature. The mixture was concentrated under vacuum. This resulted in 15 mg (crude) of (3R)—N-[3-[5-(4-[1-[2-(azetidin-3-yl)ethyl]azetidin-3-yl]phenyl)-1H-pyrrolo[2,3-b]pyridine-3-carbonyl]-2,4-difluorophenyl]-3-fluoropyrrolidine-1-sulfonamide as a yellow solid.

Step 11: Preparation of (R)-2-(3-(2-(3-(4-(3-(2,6-difluoro-3-((3-fluoropyrrolidine)-1-sulfonamido)benzoyl)-1H-pyrrolo[2,3-b]pyridin-5-yl)phenyl)azetidin-1-yl)ethyl)azetidin-1-yl)acetic acid

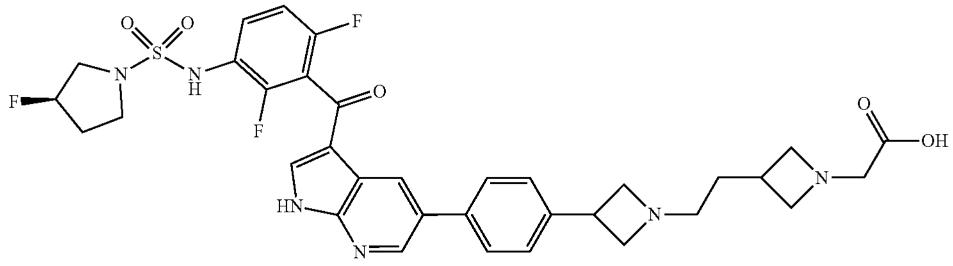 [SMILES: O=C(O)CN1CC(CCN2CC(c3ccc(-c4cnc5[nH]cc(C(=O)c6c(F)ccc(NS(=O)(=O)N7CC[C@@H](F)C7)c6F)c5c4)cc3)C2)C1]

Into a 50-mL round-bottom flask, was placed (3R)—N-[3-[5-(4-[1-[2-(azetidin-3-yl)ethyl]azetidin-3-yl]phenyl)-1H-pyrrolo[2,3-b]pyridine-3-carbonyl]-2,4-difluorophenyl]-3-fluoropyrrolidine-1-sulfonamide (100 mg, 0.157 mmol, 1 equiv), 2-oxoacetic acid (13 mg, 0.176 mmol, 1.12 equiv) in DCE (10 mL). The resulting mixture was stirred for 10 min at room temperature, and then was added by $NaBH(OAc)_3$ (100 mg, 0.472 mmol, 3.01 equiv). The reaction mixture was stirred for 1 hr at room temperature. The reaction was then quenched by the addition of 1 mL water. The resulting mixture was extracted with dichloromethane (2×10 mL). The combined organic phase was washed with brine, dried over anhydrous sodium sulfate and concentrated. The crude product was purified by prep-HPLC. This resulted in 20 mg (18.33% for 2 steps) of 2-(3-[2-[3-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)azetidin-1-yl]ethyl]azetidin-1-yl)acetic acid as a colorless oil. LC/MS (ESI) m/z: 696.95 $[M+1]^+$.

Step 12: Preparation of (2S,4R)-1-((S)-2-(2-(3-(2-(3-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-1-yl)ethyl)azetidin-1-yl)acetamido)-3,3-dimethylbutanoyl)-4-hydroxy-N-(4-(4-methylthiazol-5-yl)benzyl)pyrrolidine-2-carboxamide

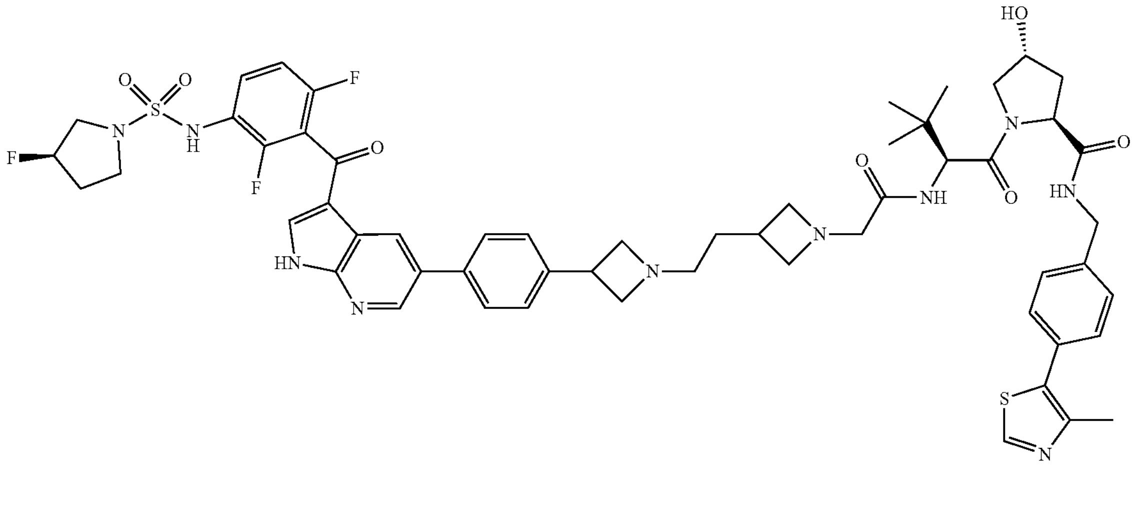 [SMILES: Cc1ncsc1-c1ccc(CNC(=O)[C@@H]2C[C@@H](O)CN2C(=O)[C@@H](NC(=O)CN2CC(CCN3CC(c4ccc(-c5cnc6[nH]cc(C(=O)c7c(F)ccc(NS(=O)(=O)N8CC[C@@H](F)C8)c7F)c6c5)cc4)C3)C2)C(C)(C)C)cc1]

Into a 100-mL round-bottom flask, was placed (3R)—N-[3-[5-(4-[1-[2-(azetidin-3-yl)ethyl]azetidin-3-yl]phenyl)-1H-pyrrolo[2,3-b]pyridine-3-carbonyl]-2,4-difluorophenyl]-3-fluoropyrrolidine-1-sulfonamide (120 mg, 0.172 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (74 mg, 0.172 mmol, 1.00 equiv), DIEA (111 mg, 0.859 mmol, 4.99 equiv), BOP (114 mg, 0.26 mmol, 1.50 equiv) in DMF (5 mL). The resulting solution was stirred for 1 hr at room temperature. The mixture was concentrated. The crude product was purified by prep-HPLC. This resulted in 46.2 mg (18.33%) of (2S,4R)-1-((S)-2-(2-(3-(2-(3-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-1-yl)ethyl)azetidin-1-yl)acetamido)-3,3-dimethylbutanoyl)-4-hydroxy-N-(4-(4-methylthiazol-5-yl)benzyl)pyrrolidine-2-carboxamide as a yellow solid. LC/MS (ESI) m/z: 1109.35 $[M+1]^+$; $^1$H-NMR (300 MHz, DMSO-$d_6$) δ 8.96 (m, 1H), 8.67 (s, 1H), 8.56-8.54 (m, 2H), 8.01 (s, 1H), 7.95-7.89 (d, 1H), 7.78-7.75 (m, 2H), 7.54-7.45 (m, 4H), 7.39-7.37 (m, 4H), 6.86 (m, 1H), 5.32 (m, 1H), 5.18 (m, 2H), 4.66-4.39 (m, 10H), 4.30-4.28 (m, 1H), 3.69-3.62 (m, 6H), 3.20-3.07 (m, 6H), 2.60 (m, 2H), 2.43-2.41 (m, 2H), 2.12-1.65 (m, 7H), 0.97 (s, 9H).

Exemplary Synthesis of 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N—((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)acetamide (Example 386)

Step 1: Preparation of benzyl (2S,4R)-1-((S)-2-((tert-butoxycarbonyl)amino)-3,3-dimethylbutanoyl)-4-hydroxypyrrolidine-2-carboxylate

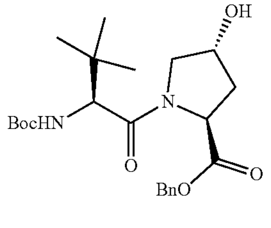 [SMILES: CC(C)(C)OC(=O)N[C@H](C(=O)N1C[C@H](O)C[C@H]1C(=O)OCc1ccccc1)C(C)(C)C]

Into a 1000-mL 3-necked round-bottom flask purged and maintained with an inert atmosphere of nitrogen, was placed N,N-dimethylformamide (200 mL), (2S)-2-[[(tert-butoxy)carbonyl]amino]-3,3-dimethylbutanoic acid (48.98 g, 211.77 mmol, 1.00 equiv), This was followed by the addition of HATU (96.69 g, 254.29 mmol, 1.20 equiv) and DIEA (109.4 g, 846.49 mmol, 4.00 equiv) at 0° C., after stirred 20 min. To this was added benzyl (2S,4R)-4-hydroxypyrrolidine-2-carboxylate (100.0 g, 254.45 mmol, 1.20 equiv) in several batches at 0° C. The resulting solution was stirred for 2 h at room temperature. The resulting solution was extracted with ethyl acetate (300 mL×3) and the organic layers combined. The resulting mixture was washed with brine (100 mL×2). The mixture was dried over anhydrous sodium sulfate and concentrated under vacuum. The residue was applied onto a silica gel column with ethyl acetate/petroleum ether (7/3). This resulted in 80 g (87%) of benzyl (2S,4R)-1-[(2S)-2-[[(tert-butoxy)carbonyl]amino]-3,3-dimethylbutanoyl]-4-hydroxypyrrolidine-2-carboxylate as a light yellow solid.

Step 2: Preparation of (2S,4R)-1-((S)-2-((tert-butoxycarbonyl)amino)-3,3-dimethylbutanoyl)-4-hydroxypyrrolidine-2-carboxylic acid

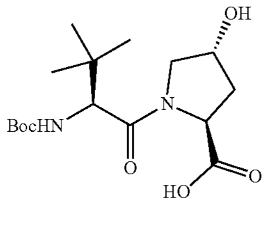 [SMILES: CC(C)(C)OC(=O)N[C@H](C(=O)N1C[C@H](O)C[C@H]1C(=O)O)C(C)(C)C]

Into a 100 mL round-bottom flask were added benzyl (2S,4R)-1-[(2S)-2-[[(tert-butoxy)carbonyl]amino]-3,3-dimethylbutanoyl]-4-hydroxypyrrolidine-2-carboxylate (3 g, 6.90 mmol, 1 equiv) and menthol (50 mL, 1.56 mmol, 0.23 equiv) at room temperature under nitrogen atmosphere. To the stirred solution was added Pd/C (200 mg, 1.88 mmol, 0.27 equiv) in portions at room temperature under nitrogen atmosphere. The flask was then vacuumed and flushed with hydrogen. The reaction mixture was hydrogenated at room temperature for 16 hours under hydrogen atmosphere using a hydrogen balloon, then filtered through a Celite pad, the filter cake was washed with menthol (120 mL) and concentrated under reduced pressure. This resulted in (2S,4R)-1-[(2S)-2-[[(tert-butoxy)carbonyl]amino]-3,3-dimethylbutanoyl]-4-hydroxypyrrolidine-2-carboxylic acid (1.67 g, 70.23%) as a white solid.

Step 3: Preparation of 2-(4-bromophenyl)-2-oxoethyl (2S,4R)-1-((S)-2-((tert-butoxycarbonyl)amino)-3,3-dimethylbutanoyl)-4-hydroxypyrrolidine-2-carboxylate

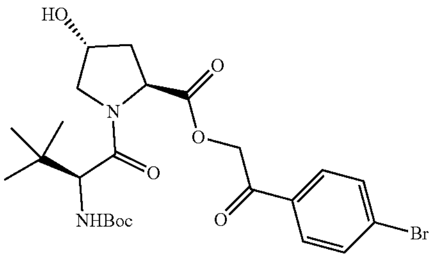 [SMILES: CC(C)(C)OC(=O)N[C@H](C(=O)N1C[C@H](O)C[C@H]1C(=O)OCC(=O)c1ccc(Br)cc1)C(C)(C)C]

Into a 50 mL round-bottom flask were added 2-bromo-1-(4-bromophenyl)ethan-1-one (1.04 g, 3.74 mmol, 1 equiv), N,N-Diisopropylethylamine (1.5 g, 11.61 mmol, 3.10 equiv) and (2S,4R)-1-[(2S)-2-[[(tert-butoxy)carbonyl]amino]-3,3-dimethylbutanoyl]-4-hydroxypyrrolidine-2-carboxylic acid (1.3 g, 3.77 mmol, 1.01 equiv) in acetonitrile (40 mL) at room temperature. The resulting mixture was stirred for 3 h at room temperature, and then was concentrated under vacuum. The residue was purified by silica gel column chromatography eluting with petroleum ether/ethyl acetate (1:1) to afford 2-(4-bromophenyl)-2-oxoethyl (2S,4R)-1-[(2S)-2-[[(tert-butoxy)carbonyl]amino]-3,3-dimethylbutanoyl]-4-hydroxypyrrolidine-2-carboxylate (2.16 g, 74.63%) as a white solid. LC/MS (ESI) m/z: 541.00 $[M+1]^+$.

Step 4: Preparation of tert-butyl ((S)-1-((2S,4R)-2-(5-(4-bromophenyl)-1H-imidazol-2-yl)-4-hydroxypyrrolidin-1-yl)-3,3-dimethyl-1-oxobutan-2-yl)carbamate

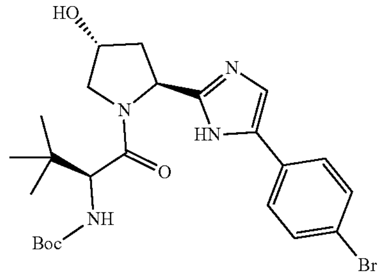 [SMILES: CC(C)(C)OC(=O)N[C@H](C(=O)N1C[C@H](O)C[C@H]1c1ncc(-c2ccc(Br)cc2)[nH]1)C(C)(C)C]

Into a 100 mL round-bottom flask were added 2-(4-bromophenyl)-2-oxoethyl (2S,4R)-1-[(2S)-2-[[(tert-butoxy) carbonyl]amino]-3,3-dimethylbutanoyl]-4-hydroxypyrrolidine-2-carboxylate (2.06 g, 3.80 mmol, 1 equiv) and ammonium acetate (2.3 g, 29.84 mmol, 7.84 equiv) in xylene (40 mL) at room temperature. The resulting mixture was stirred for 3 h at 140° C. The reaction mixture was cooled to room temperature and diluted with water (100 mL). The mixture was extracted with ethyl acetate (50 mL×3). The combined organic layer was washed with brine (50 mL), dried over sodium sulfate and concentrated under vacuum. The residue was purified by silica gel column chromatography eluting with ethyl acetate (100%) to afford tert-butyl N-[(2S)-1-[(2S,4R)-2-[5-(4-bromophenyl)-1H-imidazol-2-yl]-4-hydroxypyrrolidin-1-yl]-3,3-dimethyl-1-oxobutan-2-yl]carbamate (1.5 g, 75.61%) as a yellow solid. LC/MS (ESI) m/z: 522.95 $[M+1]^+$.

Step 5: Preparation of tert-butyl ((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)carbamate

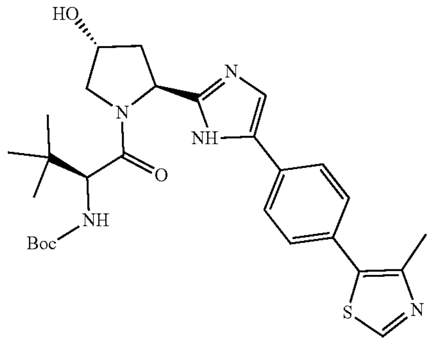 [SMILES: Cc1ncsc1-c1ccc(-c2cnc([C@@H]3C[C@@H](O)CN3C(=O)[C@@H](NC(=O)OC(C)(C)C)C(C)(C)C)[nH]2)cc1]

Into a 10 mL sealed tube were added tert-butyl N-[(2S)-1-[(2S,4R)-2-[5-(4-bromophenyl)-1H-imidazol-2-yl]-4-hydroxypyrrolidin-1-yl]-3,3-dimethyl-1-oxobutan-2-yl]carbamate (1.4 g, 2.68 mmol, 1 equiv), potassium carbonate (1.1 g, 7.96 mmol, 2.96 equiv), $Pd(dppf)Cl_2 \cdot CH_2Cl_2$ (219.3 mg, 0.27 mmol, 0.1 equiv) and 4-methyl-5-(4,4,5,5-tetramethyl-1,3,2-dioxaborolan-2-yl)-1,3-thiazole (785.7 mg, 3.49 mmol, 1.3 equiv) in dioxane (50 mL) and water (10 mL) at room temperature under nitrogen atmosphere. The resulting mixture was stirred for 3 h at 90° C. under nitrogen atmosphere. The mixture was allowed to cool down to room temperature. The aqueous layer was extracted with Ethyl acetate (100 mL×3). The combined organic layer was washed with of brine (50 mL×2), dried over sodium sulfate and concentrated under vacuum. The residue was purified in a silica gel column eluting with dichloromethane/methyl alcohol (10:1) to afford tert-butyl N-[(2S)-1-[(2S,4R)-4-hydroxy-2-[5-[4-(4-methyl-1,3-thiazol-5-yl)phenyl]-1H-imidazol-2-yl]pyrrolidin-1-yl]-3,3-dimethyl-1-oxobutan-2-yl]carbamate (1.3 g, 89.72%) as a yellow solid. LC/MS (ESI) m/z: 540.10 $[M+1]^+$.

Step 6: Preparation of (S)-2-amino-1-((2S,4R)-4-hydroxy-2-(5-(4-(4-methylthiazol-5-yl)phenyl)-1H-imidazol-2-yl)pyrrolidin-1-yl)-3,3-dimethylbutan-1-one hydrochloride

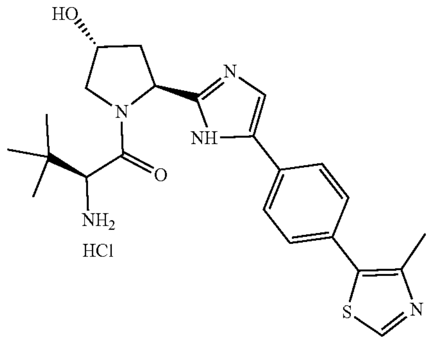 [SMILES: Cc1ncsc1-c1ccc(-c2cnc([C@@H]3C[C@@H](O)CN3C(=O)[C@@H](N)C(C)(C)C)[nH]2)cc1 ; Cl]

Into a 50 mL round-bottom flask were added tert-butyl N-[(2S)-1-[(2S,4R)-4-hydroxy-2-[5-[4-(4-methyl-1,3-thiazol-5-yl)phenyl]-1H-imidazol-2-yl]pyrrolidin-1-yl]-3,3-dimethyl-1-oxobutan-2-yl]carbamate (1.3 g, 2.41 mmol, 1 equiv) and hydrochloric acid in dioxane (20 mL, 4 mol/L) at room temperature. The resulting mixture was stirred for 2 h at room temperature, and then was concentrated under reduced pressure. This resulted in (2S)-2-amino-1-[(2S,4R)-4-hydroxy-2-[5-[4-(4-methyl-1,3-thiazol-5-yl)phenyl]-1H-imidazol-2-yl]pyrrolidin-1-yl]-3,3-dimethylbutan-1-one hydrochloride (1.25 g, crude) as a yellow solid. LC/MS (ESI) m/z: 440.30 $[M+1]^+$.

Step 7: Preparation of tert-butyl 4-((1-((benzyloxy) carbonyl)piperidin-4-yl)methyl)piperazine-1-carboxylate

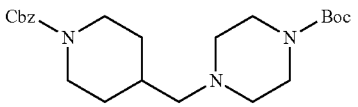 [SMILES: CC(C)(C)OC(=O)N1CCN(CC2CCN(C(=O)OCc3ccccc3)CC2)CC1]

Into a 500-mL round-bottom flask, was placed benzyl 4-formylpiperidine-1-carboxylate (5 g, 20.22 mmol, 1.00 equiv), tert-butyl piperazine-1-carboxylate (3.8 g, 20.40 mmol, 1.01 equiv), dichloromethane (200 mL). This was followed by the addition of sodium triacetoxyborohydride (5.15 g) in portions at 25° C. in 10 min. The resulting solution was stirred for 3 h at 25° C. The reaction was then quenched by the addition of water (50 mL) and extracted with dichloromethane (50 mL×3). The combined organic layers were washed with brine (150 mL), dried over anhydrous sodium sulfate and concentrated under vacuum. The residue was applied onto a silica gel column with ethyl acetate/petroleum ether (3:7-9:1). This resulted in 7.62 g (90%) of tert-butyl 4-([1-[(benzyloxy)carbonyl]piperidin-4-yl]methyl)piperazine-1-carboxylate as a light yellow solid. LC/MS (ESI) m/z: 418.20 [M+1]$^+$.

Step 8: Preparation of tert-butyl 4-(piperidin-4-ylmethyl)piperazine-1-carboxylate

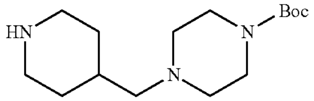

Into a 500-mL round-bottom flask purged and maintained with an inert atmosphere of nitrogen, was placed tert-butyl 4-([1-[(benzyloxy)carbonyl]piperidin-4-yl]methyl)piperazine-1-carboxylate (7.62 g, 18.25 mmol, 1.00 equiv), ethanol (200 mL), Palladium carbon (500 mg). The flask was then vacuumed and flushed with hydrogen using a hydrogen balloon. The reaction mixture was stirred for 16 h at room temperature. The reaction mixture was filtered through a Celite pad and the filtrate was concentrated under reduced pressure. This resulted in 4.66 g (crude) of tert-butyl 4-(piperidin-4-ylmethyl)piperazine-1-carboxylate as colorless oil. LC/MS (ESI) m/z: 284.10 [M+1]$^+$.

Step 9: Preparation of tert-butyl 4-((1-(4-bromophenyl)piperidin-4-yl)methyl)piperazine-1-carboxylate

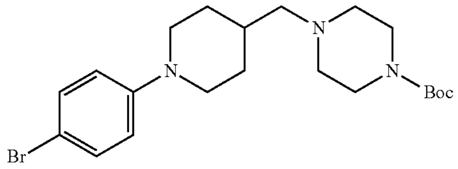 [SMILES: CC(C)(C)OC(=O)N1CCN(CC2CCN(c3ccc(Br)cc3)CC2)CC1]

Into a 250-mL 3-necked round-bottom flask, was placed tert-butyl 4-[(piperidin-4-yl)methyl]piperazine-1-carboxylate (4.27 g, 15.07 mmol, 1 equiv), (4-bromophenyl)boronic acid (3.63 g, 18.07 mmol, 1.20 equiv), dichloromethane (100 mL), 4 A MS (5 g), (acetyloxy)cuprio acetate (4.10 g, 22.57 mmol, 1.50 equiv), TEA (8.4 mL, 60.43 mmol, 4.01 equiv). The resulting mixture was purged with air and stirred for 20 h at room temperature. The solids were filtered out and the filtrate was concentrated under vacuum. The residue was applied onto a silica gel column with ethyl acetate/petroleum ether (1:2). This resulted in 3.87 g (58.59%) of tert-butyl 4-[[1-(4-bromophenyl)piperidin-4-yl]methyl]piperazine-1-carboxylate as a light brown solid. LC/MS (ESI) m/z: 438.00 [M+1]$^+$.

Step 10: Preparation of 1-((1-(4-bromophenyl)piperidin-4-yl)methyl)piperazine

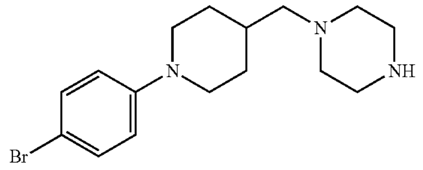 [SMILES: Brc1ccc(N2CCC(CN3CCNCC3)CC2)cc1]

Into a 100-mL round-bottom flask, was placed tert-butyl 4-[[1-(4-bromophenyl)piperidin-4-yl]methyl]piperazine-1-carboxylate (3.87 g, 8.83 mmol, 1 equiv), dichloromethane (20 mL), trifluoroacetic acid (10 mL). The resulting solution was stirred for 1 h at room temperature. The resulting mixture was concentrated under vacuum. This resulted in 7.56 g (189.34%) of 1-[[1-(4-bromophenyl)piperidin-4-yl]methyl]piperazine; trifluoroacetic acid as a brown solid. LC/MS (ESI) m/z: 337.95 [M+1]$^+$.

Step 11: Preparation of tert-butyl 2-(4-((1-(4-bromophenyl)piperidin-4-yl)methyl)piperazin-1-yl)acetate

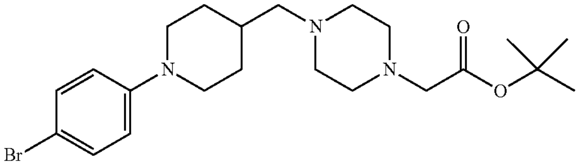 [SMILES: CC(C)(C)OC(=O)CN1CCN(CC2CCN(c3ccc(Br)cc3)CC2)CC1]

Into a 500-mL round-bottom flask, was placed 1-[[1-(4-bromophenyl)piperidin-4-yl]methyl]piperazine; trifluoroacetic acid (7.56 g, 16.71 mmol, 1 equiv), TEA (23 mL, 165.47 mmol, 9.90 equiv), dichloromethane (130 mL). This was followed by the addition of tert-butyl 2-bromoacetate (3.59 g, 18.40 mmol, 1.10 equiv) dropwise with stirring. The resulting solution was stirred for 2 h at room temperature. The resulting solution was diluted with dichloromethane (200 mL) and washed with water (100 mL). The organic was dried over anhydrous sodium sulfate and concentrated under vacuum. The residue was applied onto a silica gel column with ethyl acetate/petroleum ether (1:1). This resulted in 3.43 g (45.36%) of tert-butyl 2-(4-[[1-(4-bromophenyl)piperidin-4-yl]methyl]piperazin-1-yl)acetate as a yellow solid. LC/MS (ESI) m/z: 451.95 [M+1]$^+$.

Step 12: Preparation of tert-butyl 2-(4-((1-(4-(4,4,5,5-tetramethyl-1,3,2-dioxaborolan-2-yl)phenyl)piperidin-4-yl)methyl)piperazin-1-yl)acetate

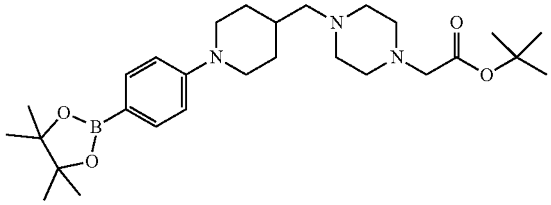 [SMILES: CC(C)(C)OC(=O)CN1CCN(CC2CCN(c3ccc(B4OC(C)(C)C(C)(C)O4)cc3)CC2)CC1]

Into a 250-mL round-bottom flask purged and maintained with an inert atmosphere of nitrogen, was placed tert-butyl 2-(4-[[1-(4-bromophenyl)piperidin-4-yl]methyl]piperazin-1-yl)acetate (3.90 g, 8.62 mmol, 1 equiv), 4,4,5,5-tetramethyl-2-(4,4,5,5-tetramethyl-1,3,2-dioxaborolan-2-yl)-1,3,2-dioxaborolane (4.38 g, 17.25 mmol, 2.00 equiv), KOAc (2.53 g, 25.78 mmol, 2.99 equiv), Pd(dppf)$Cl_2$·$CH_2Cl_2$ (704 mg, 0.86 mmol, 0.10 equiv), DMSO (70 mL). The resulting mixture was stirred for 16 h at 90° C. in an oil bath. The reaction mixture was cooled to room temperature and diluted with ethyl acetate (500 mL). The mixture was washed with water (200 mL) and brine (100 mL×1). The organic was dried over anhydrous sodium sulfate and concentrated under vacuum. The residue was applied onto a silica gel column with ethyl acetate/petroleum ether (2:1). This resulted in 2.57 g (59.69%) of tert-butyl 2-[4-([1-[4-(4,4,5,5-tetramethyl-1,3,2-dioxaborolan-2-yl)phenyl]piperidin-4-yl]methyl)piperazin-1-yl]acetate as a light brown solid. LC/MS (ESI) m/z: 500.15 $[M+1]^+$.

Step 13: Preparation of tert-butyl (R)-2-(4-((1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)methyl)piperazin-1-yl)acetate

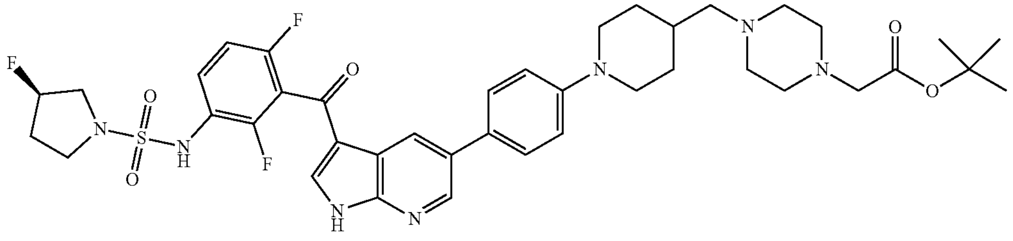 [SMILES: CC(C)(C)OC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 30-mL sealed tube purged and maintained with an inert atmosphere of nitrogen, was placed tert-butyl 2-[4-([1-[4-(4,4,5,5-tetramethyl-1,3,2-dioxaborolan-2-yl)phenyl]piperidin-4-yl]methyl)piperazin-1-yl]acetate (1.09 g, 2.18 mmol, 1.10 equiv), (3R)—N-(3-[5-bromo-1H-pyrrolo[2,3-b]pyridine-3-carbonyl]-2,4-difluorophenyl)-3-fluoropyrrolidine-1-sulfonamide (1.00 g, 1.99 mmol, 1 equiv), dioxane (20 mL), $H_2O$ (4 mL), $Na_2CO_3$ (632 mg, 5.96 mmol, 3.00 equiv), Pd(dppf)$Cl_2$·$CH_2Cl_2$ (162 mg, 0.20 mmol, 0.10 equiv). The resulting mixture was stirred for 2 h at 105° C. in an oil bath. The reaction mixture was cooled to room temperature and diluted with ethyl acetate (150 mL). The mixture was washed with water (50 mL). The organic layer was dried over anhydrous sodium sulfate and concentrated under vacuum. The residue was applied onto a silica gel column with dichloromethane/methanol (28:1). This resulted in 1.15 g (72.72%) of tert-butyl 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetate as a brown solid. LC/MS (ESI) m/z: 796.00 $[M+1]^+$.

Step 14: Preparation of (R)-2-(4-((1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)methyl)piperazin-1-yl)acetic acid

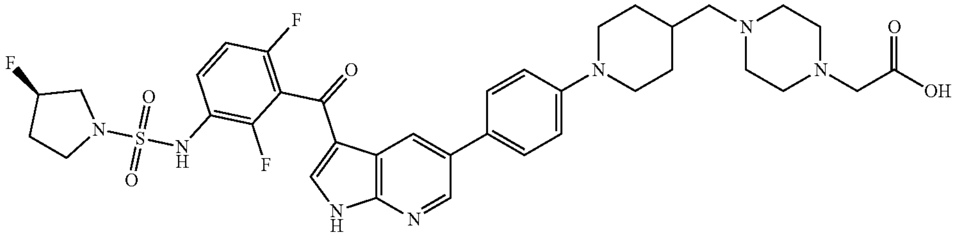 [SMILES: O=C(O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 100-mL round-bottom flask, was placed tert-butyl 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetate (1.11 g, 1.39 mmol, 1 equiv), dichloromethane (10 mL), trifluoroacetic acid (5 mL). The resulting solution was stirred for 3 h at 35° C. in an oil bath. The resulting mixture was concentrated under vacuum. This resulted in 1.12 g (108.55%) of 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid as a brown solid. LC/MS (ESI) m/z: 740.40 $[M+1]^+$.

Step 15: Preparation of 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N—((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)acetamide

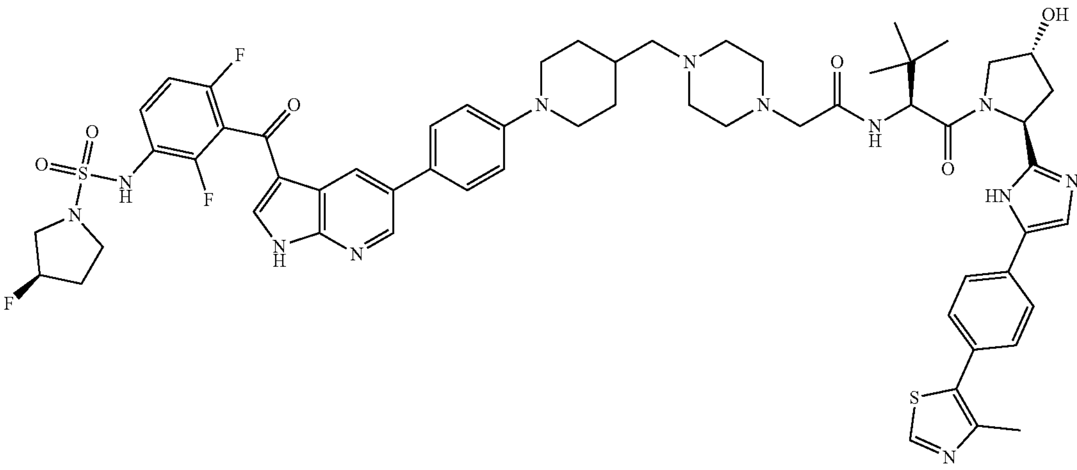 [SMILES: Cc1ncsc1-c1ccc(-c2cnc([C@@H]3C[C@@H](O)CN3C(=O)[C@@H](NC(=O)CN3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)C(C)(C)C)[nH]2)cc1]

Into a 100 mL round-bottom flask were added (2S)-2-amino-1-[(2S,4R)-4-hydroxy-2-[5-[4-(4-methyl-1,3-thiazol-5-yl)phenyl]-1H-imidazol-2-yl]pyrrolidin-1-yl]-3,3-dimethylbutan-1-one hydrochloride (100 mg, 1 equiv), 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid (336 mg, 2.0 equiv, 60%), N,N-Diisopropylethylamine (1 mL, 3.0 equiv) and (Benzotriazole-1-yloxy)tris(dimethylamino)phosphonium hexafluorophosphate (201 mg, 2.0 equiv) in N,N-Dimethylformamide (20 mL) at room temperature under nitrogen atmosphere. The resulting mixture was stirred for 2 h at room temperature under nitrogen atmosphere. The reaction mixture was diluted with water and extracted with ethyl acetate (50 mL×2). The combined organic layer was washed with of brine (20 mL×2), dried over sodium sulfate and concentrated under vacuum. The crude product was purified by Prep-HPLC to afford 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)-N-[(2S)-1-[(2S,4R)-4-hydroxy-2-[5-[4-(4-methyl-1,3-thiazol-5-yl)phenyl]-1H-imidazol-2-yl]pyrrolidin-1-yl]-3,3-dimethyl-1-oxobutan-2-yl]acetamide (53.8 mg, 22.05%) as a yellow solid. LC/MS (ESI) m/z: 1161.20 $[M+1]^+$; $^1$H-NMR (400 MHz, $CD_3OD$) δ 8.88 (s, 1H), 8.69 (s, 1H), 8.61 (s, 1H), 7.90 (s, 1H), 7.82-7.71 (m, 3H), 7.63-7.58 (m, 2H), 7.51-7.46 (m, 2H), 7.41-7.37 (m, 1H), 7.15-7.08 (m, 3H), 5.33-5.24 (m, 2H), 4.65-4.48 (m, 2H), 3.99 (s, 2H), 3.80-3.75 (m, 2H), 3.61-3.39 (m, 5H), 3.09 (s, 1H), 2.84-2.72 (m, 2H), 2.63 (s, 3H), 2.55-2.38 (m, 8H), 2.36-2.02 (m, 5H), 1.93-1.86 (m, 2H), 1.81-1.69 (m, 1H), 1.40-1.26 (m, 3H), 1.05 (s, 2H), 0.98 (s, 7H).

Exemplary Synthesis of N—((S)-1-((2S,4R)-2-(5-benzyl-1H-imidazol-2-yl)-4-hydroxypyrrolidin-1-yl)-3,3-dimethyl-1-oxobutan-2-yl)-2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamide (Example 459)

Step 1: Preparation of 1-bromo-3-phenylpropan-2-one

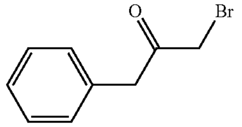 [SMILES: O=C(CBr)Cc1ccccc1]

To a stirred solution of 2-phenylacetyl chloride (6 g, 38.812 mmol, 1 equiv) in acetonitrile (50 mL) was added TMSCHN2 (13.30 g, 116.441 mmol, 3.00 equiv) dropwise at room temperature under nitrogen atmosphere. The resulting mixture was stirred for 1 h at room temperature. The mixture was allowed to cool down to 0° C. and was added by a solution of HBr in AcOH (40%, 12.56 g, 155.249 mmol, 4.0 equiv) dropwise. The reaction mixture as stirred for another 15 min at room temperature under nitrogen atmosphere. The mixture was then concentrated under reduced pressure and the residue was purified by silica gel column chromatography, eluted with DCM/PE (1:1) to afford 1-bromo-3-phenylpropan-2-one (4.5 g, 54.41%) as light yellow oil.

Step 2: Preparation of 2-oxo-3-phenylpropyl (2S,4R)-1-((S)-2-((tert-butoxycarbonyl)amino)-3,3-dimethylbutanoyl)-4-hydroxypyrrolidine-2-carboxylate

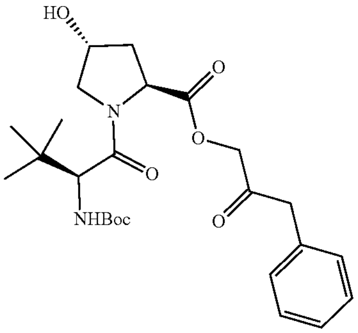 [SMILES: CC(C)(C)OC(=O)N[C@H](C(=O)N1C[C@H](O)C[C@H]1C(=O)OCC(=O)Cc1ccccc1)C(C)(C)C]

To a stirred solution of 1-bromo-3-phenylpropan-2-one (2.72 g, 12.766 mmol, 1 equiv) and (2S,4R)-1-[(2S)-2-[[(tert-butoxy)carbonyl]amino]-3,3-dimethylbutanoyl]-4-hydroxypyrrolidine-2-carboxylic acid (5.28 g, 15.319 mmol, 1.20 equiv) in acetonitrile (50 mL) was added DIEA (7 mL, 40.188 mmol, 3.15 equiv) dropwise at room temperature under nitrogen atmosphere. The resulting mixture was stirred for 3 hours at room temperature under nitrogen atmosphere. The mixture was concentrated under reduced pressure. The residue was purified by silica gel column chromatography, eluted with petroleum ether/ethyl acetate (1:2) to afford 2-oxo-3-phenylpropyl(2S,4R)-1-[(2S)-2-[[(tert-butoxy)carbonyl]amino]-3,3-dimethylbutanoyl]-4-hydroxypyrrolidine-2-carboxylate (4.3 g, 70.68%) as off-white solid. LC/MS (ESI) m/z: 477.25 [M+1]$^+$.

Step 3: Preparation of tert-butyl ((S)-1-((2S,4R)-2-(5-benzyl-1H-imidazol-2-yl)-4-hydroxypyrrolidin-1-yl)-3,3-dimethyl-1-oxobutan-2-yl)carbamate

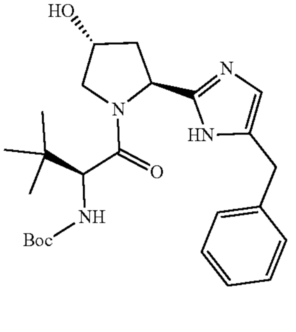 [SMILES: CC(C)(C)OC(=O)N[C@H](C(=O)N1C[C@H](O)C[C@H]1c1ncc(Cc2ccccc2)[nH]1)C(C)(C)C]

Into a 100-mL microwave vial, was placed a solution of 2-oxo-3-phenylpropyl (2S,4R)-1-[(2S)-2-[[(tert-butoxy)carbonyl]amino]-3,3-dimethylbutanoyl]-4-hydroxypyrrolidine-2-carboxylate (952 mg, 1.998 mmol, 1 equiv) and $NH_4OAc$ (1.23 g, 16.0 mmol, 8.0 equiv) in xylene (50 mL) under nitrogen atmosphere. The resulting mixture was irradiated under microwave for 1 hour at 140° C. The reaction mixture was diluted with water (30 mL) and extracted with ethyl acetate (30 mL×3). The combined organic layer was washed with brine (50 mL), dried over anhydrous $Na_2SO_4$ and concentrated under reduced pressure. The residue was purified by silica gel column chromatography, eluted with dichloromethane/methyl alcohol (10:1) to afford tert-butylN-[(2S)-1-[(2S,4R)-2-(5-benzyl-1H-imidazol-2-yl)-4-hydroxypyrrolidin-1-yl]-3,3-dimethyl-1-oxobutan-2-yl]carbamate (260.0 mg, 15.08%) as off-white solid. LC/MS (ESI) m/z: 457.30 [M+1]$^+$.

Step 4: Preparation of (S)-2-amino-1-((2S,4R)-2-(5-benzyl-1H-imidazol-2-yl)-4-hydroxypyrrolidin-1-yl)-3,3-dimethylbutan-1-one hydrochloride

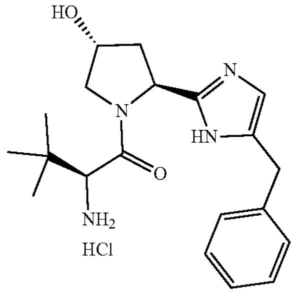 [SMILES: CC(C)(C)[C@H](N)C(=O)N1C[C@H](O)C[C@H]1c1ncc(Cc2ccccc2)[nH]1 ; Cl]

To a solution of tert-butyl N-[(2S)-1-[(2S,4R)-2-(5-benzyl-1H-imidazol-2-yl)-4-hydroxypyrrolidin-1-yl]-3,3-dimethyl-1-oxobutan-2-yl]carbamate (260.0 mg, 0.569 mmol, 1 equiv) in 1,4-dioxane (5 mL) was added hydrogen chloride in 1,4-dioxane solution (4.0 M, 5 mL) slowly. The resulting mixture was stirred for 1 hour at room temperature, and then was concentrated under reduced pressure. This resulted in 200.0 mg (2S)-2-amino-1-[(2S,4R)-2-(5-benzyl-1H-imidazol-2-yl)-4-hydroxypyrrolidin-1-yl]-3,3-dimethylbutan-1-one-hydrochloride as off-white solid. LC/MS (ESI) m/z: 357.15 [M+1]$^+$.

Step 5: Preparation of N—((S)-1-((2S,4R)-2-(5-benzyl-1H-imidazol-2-yl)-4-hydroxypyrrolidin-1-yl)-3,3-dimethyl-1-oxobutan-2-yl)-2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamide

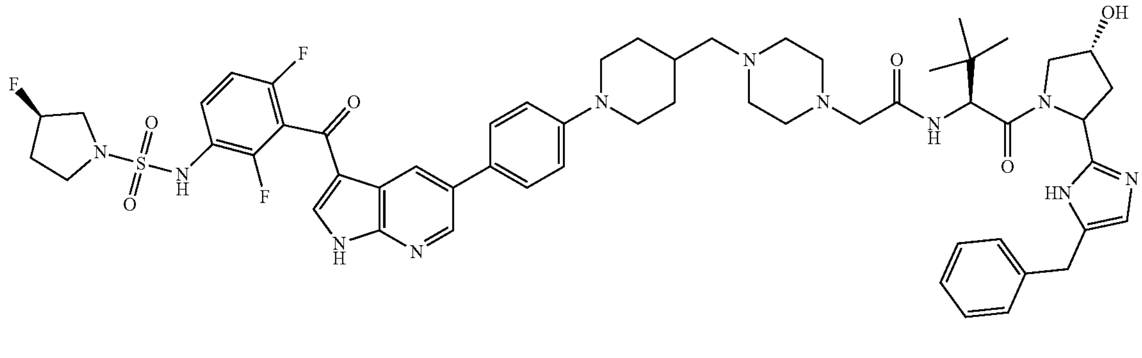 [SMILES: CC(C)(C)[C@H](NC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1)C(=O)N1C[C@H](O)CC1c1ncc(Cc2ccccc2)[nH]1]

To a stirred solution of (2S)-2-amino-1-[(2S,4R)-2-(5-benzyl-1H-imidazol-2-yl)-4-hydroxypyrrolidin-1-yl]-3,3-dimethylbutan-1-one hydrochloride (110 mg, 0.280 mmol, 1 equiv) and 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid (207.11 mg, 0.280 mmol, 1.00 equiv) in DMF (5 mL) were added DIEA (1 mL, 5.741 mmol, 20.51 equiv) and BOP (148.58 mg, 0.336 mmol, 1.2 equiv) at room temperature under nitrogen atmosphere. The resulting mixture was stirred for 1 hour at room temperature under nitrogen atmosphere. The reaction was then quenched by the addition of water (50 mL) and extracted with ethyl acetate (30 mL×3). The combined organic layer was washed with brine (30 mL×2), dried over anhydrous $Na_2SO_4$ and concentrated under reduced pressure. The residue was purified by silica gel column chromatography, eluted with dichloromethane/methyl alcohol (10:1) to afford crude product which was further purified by Prep-HPLC. This resulted in N-[(2S)-1-[(2S,4R)-2-(5-benzyl-1H-imidazol-2-yl)-4-hydroxypyrrolidin-1-yl]-3,3-dimethyl-1-oxobutan-2-yl]-2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamide (50.6 mg, 16.76%) as light yellow solid. LC/MS (ESI) m/z: 1078.35 $[M+1]^+$; $^1$H-NMR (300 MHz, DMSO-$d_6$) δ 12.92 (s, 1H), δ 11.50 (brs, 1H), 9.88 (brs, 1H), 8.65 (d, J=2.2 Hz, 1H), 8.53 (s, 1H), 8.08 (s, 1H), 7.80-7.64 (m, 1H), 7.68-7.54 (m, 3H), 7.30-7.20 (m, 4H), 7.20-7.10 (m, 3H), 7.07 (d, J=8.5 Hz, 2H), 6.64 (s, 1H), 5.39-5.01 (m, 3H), 4.46 (d, J=9.1 Hz, 2H), 3.98-3.78 (m, 5H), 3.65-3.55 (m, 3H), 3.53-3.40 (m, 2H), 3.06-2.96 (m, 3H), 2.73 (t, J=11.9 Hz, 3H), 2.60 (s, 1H), 2.40-2.20 (m, 4H), 2.19-2.03 (m, 4H), 1.90-1.71 (m, 3H), 1.31-1.12 (m, 3H), 0.92-0.89 (m, 1H), 0.79 (s, 9H).

Exemplary Synthesis of 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N—((S)-1-((2S,4R)-4-hydroxy-2-(5-(4-(4-methylthiazol-5-yl)benzyl)-1H-imidazol-2-yl)pyrrolidin-1-yl)-3,3-dimethyl-1-oxobutan-2-yl)acetamide (Example 444)

Step 1: Preparation of 1-bromo-3-(4-bromophenyl)propan-2-one

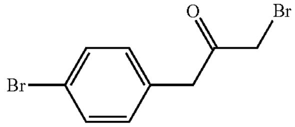 [SMILES: O=C(CBr)Cc1ccc(Br)cc1]

Into a 250-mL three-necked round-bottom flask purged and maintained with an inert atmosphere of nitrogen, was placed a solution of 2-(4-bromophenyl)acetic acid (2.50 g, 11.63 mmol, 1.0 equiv) in dichloromethane (150 mL), to which were added oxalyl chloride (1.77 g, 13.95 mmol, 1.20 equiv) and N,N-dimethylformamide (170 mg, 2.33 mmol, 0.20 equiv). The resulting mixture was stirred for 4 hours at room temperature. The reaction mixture was concentrated under reduced pressure and the residue was dissolved in acetonitrile (150 mL). To the above solution was added a solution of (trimethylsilyl)diazomethane (3.98 g, 34.85 mmol, 3.00 equiv) in hexanes (17.4 mL) at room temperature. The resulting solution was stirred for another 2 hours at room temperature, and then was cooled to 0° C. in an ice/water bath. To the cooled mixture was added a solution of hydrogen bromide in acetic acid (40%, 8.48 g, 41.85 mmol, 3.60 equiv) slowly. Then reaction mixture was allowed to react for an additional 2 hours at room temperature. The reaction was quenched by the addition of 100 mL water. The resulting mixture was extracted with ethyl acetate (250 mL×3) and the combined organic layer was washed with brine (150 ml), dried over anhydrous sodium sulfate and concentrated under reduced pressure. The residue was applied onto a silica gel column eluting with dichloromethane/petroleum ether (1:10). This resulted in 1.80 g (53.03%) of 1-bromo-3-(4-bromophenyl)propan-2-one as a light yellow oil.

Step 2: Preparation of 3-(4-bromophenyl)-2-oxopropyl (2S,4R)-1-((S)-2-((tert-butoxycarbonyl)amino)-3,3-dimethylbutanoyl)-4-hydroxypyrrolidine-2-carboxylate

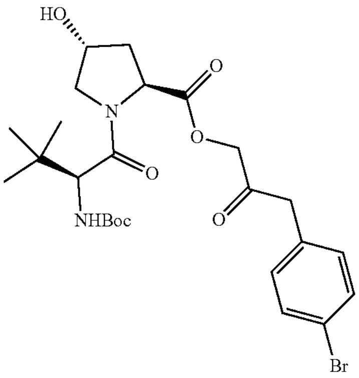 [SMILES: CC(C)(C)OC(=O)N[C@H](C(=O)N1C[C@H](O)C[C@H]1C(=O)OCC(=O)Cc1ccc(Br)cc1)C(C)(C)C]

Into a 100-mL round-bottom flask, was placed 1-bromo-3-(4-bromophenyl)propan-2-one (1.80 g, 6.155 mmol, 1.06 equiv), (2S,4R)-1-[(2S)-2-[[(tert-butoxy)carbonyl]amino]-3,3-dimethylbutanoyl]-4-hydroxypyrrolidine-2-carboxylic acid (2.00 g, 5.807 mmol, 1 equiv) and N,N-diisopropylethylamine (10 mL) in acetonitrile (30 mL). The resulting mixture was stirred overnight at room temperature. The reaction was then quenched by the addition of 100 mL water. The resulting mixture was extracted with ethyl acetate (250 mL×3). The combined organic layer was washed with brine (150 ml), and then concentrated under reduced pressure. The residue was applied onto a silica gel column eluting with dichloromethane/methanol (9:1). This resulted in 1.57 g (48.67%) of 3-(4-bromophenyl)-2-oxopropyl (2S,4R)-1-[(2S)-2-[[(tert-butoxy)carbonyl]amino]-3,3-dimethylbutanoyl]-4-hydroxypyrrolidine-2-carboxylate as light yellow solid. LC/MS (ESI) m/z: 555.20 $[M+1]^+$.

Step 3: Preparation of tert-butyl ((S)-1-((2S,4R)-2-(5-(4-bromobenzyl)-1H-imidazol-2-yl)-4-hydroxypyrrolidin-1-yl)-3,3-dimethyl-1-oxobutan-2-yl)carbamate

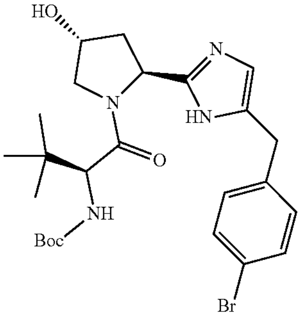 [SMILES: CC(C)(C)OC(=O)N[C@H](C(=O)N1C[C@H](O)C[C@H]1c1ncc(Cc2ccc(Br)cc2)[nH]1)C(C)(C)C]

Into a 30-mL sealed tube purged and maintained with an inert atmosphere of nitrogen, was placed 3-(4-bromophenyl)-2-oxopropyl (2S,4R)-1-[(2S)-2-[[(tert-butoxy)carbonyl]amino]-3,3-dimethylbutanoyl]-4-hydroxypyrrolidine-2-carboxylate (1.37 g, 2.466 mmol, 1 equiv), ammonium acetate (2.85 g, 36.971 mmol, 14.99 equiv) in p-xylene (20 mL). The resulting mixture was stirred for 24 hours at 140° C. in an oil bath. The mixture was concentrated under reduced pressure. The residue was applied onto a silica gel column eluting with dichloromethane/methanol (95:5). This resulted in 160.0 mg (12.11%) of tert-butyl N-[(2S)-1-[(2S,4R)-2-[5-[(4-bromophenyl)methyl]-1H-imidazol-2-yl]-4-hydroxypyrrolidin-1-yl]-3,3-dimethyl-1-oxobutan-2-yl]carbamate as a light brown semi-solid.

Step 4: Preparation of tert-butyl ((S)-1-((2S,4R)-4-hydroxy-2-(5-(4-(4-methylthiazol-5-yl)benzyl)-1H-imidazol-2-yl)pyrrolidin-1-yl)-3,3-dimethyl-1-oxobutan-2-yl)carbamate

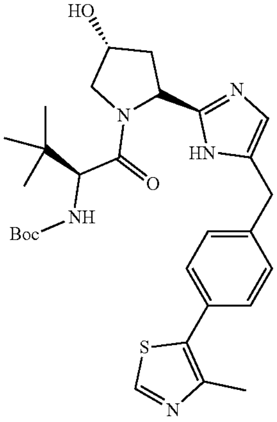

Into a 10-mL sealed tube purged and maintained with an inert atmosphere of nitrogen, was placed tert-butyl N-[(2S)-1-[(2S,4R)-2-[5-[(4-bromophenyl)methyl]-1H-imidazol-2-yl]-4-hydroxypyrrolidin-1-yl]-3,3-dimethyl-1-oxobutan-2-yl]carbamate (180.0 mg, 0.34 mmol, 1.0 equiv), 4-methyl-5-(4,4,5,5-tetramethyl-1,3,2-dioxaborolan-2-yl)-1,3-thiazole (151.0 mg, 0.67 mmol, 2.0 equiv), potassium carbonate (141.0 mg, 1.020 mmol, 3.04 equiv) and Pd(dppf)$Cl_2 \cdot CH_2Cl_2$ (28.0 mg, 0.034 mmol, 0.10 equiv) in dioxane (3 mL) and water (0.5 mL) under nitrogen atmosphere. The resulting mixture was stirred for 3 hours at 95° C. in an oil bath under nitrogen atmosphere. The mixture was concentrated under reduced pressure. The residue was applied onto a silica gel column eluting with dichloromethane/methanol (95:5). This resulted in 108.0 mg (58.02%) of tert-butyl N-[(2S)-1-[(2S,4R)-4-hydroxy-2-(5-[[4-(4-methyl-1,3-thiazol-5-yl)phenyl]methyl]-1H-imidazol-2-yl)pyrrolidin-1-yl]-3,3-dimethyl-1-oxobutan-2-yl]carbamate as red semi-solid. LC/MS (ESI) m/z: 554.30 $[M+1]^+$.

Step 5: Preparation of (S)-2-amino-1-((2S,4R)-4-hydroxy-2-(5-(4-(4-methylthiazol-5-yl)benzyl)-1H-imidazol-2-yl)pyrrolidin-1-yl)-3,3-dimethylbutan-1-one hydrochloride

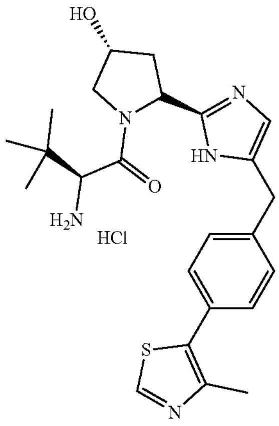

Into a 100-mL round-bottom flask, was placed a solution of tert-butyl N-[(2S)-1-[(2S,4R)-4-hydroxy-2-(5-[[4-(4-methyl-1,3-thiazol-5-yl)phenyl]methyl]-1H-imidazol-2-yl)pyrrolidin-1-yl]-3,3-dimethyl-1-oxobutan-2-yl]carbamate (108.0 mg, 0.195 mmol, 1 equiv) in dioxane (5 mL), to which was added hydrogen chloride in 1,4-dioxane solution (4.0 M, 5 mL). The resulting mixture was stirred for 1.5 hours at room temperature. The mixture was concentrated under reduced pressure. This resulted in 95.0 mg (99.39%) of (2S)-2-amino-1-[(2S,4R)-4-hydroxy-2-(5-[[4-(4-methyl-1,3-thiazol-5-yl)phenyl]methyl]-1H-imidazol-2-yl)pyrrolidin-1-yl]-3,3-dimethylbutan-1-one hydrochloride as a light brown solid. LC/MS (ESI) m/z: 454.25 $[M+1]^+$.

Step 6: Preparation of 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N—((S)-1-((2S,4R)-4-hydroxy-2-(5-(4-(4-methylthiazol-5-yl)benzyl)-1H-imidazol-2-yl)pyrrolidin-1-yl)-3,3-dimethyl-1-oxobutan-2-yl)acetamide Into a 100-mL round-bottom flask, was placed (2S)-2-amino-1-[(2S,4R)-4-hydroxy-2-(5-[[4-(4-methyl-1,3-thiazol-5-yl)phenyl]methyl]-1H-imidazol-2-yl)pyrrolidin-1-yl]-3,3-dimethylbutan-1-one hydrochloride (93.0 mg, 0.190 mmol, 1 equiv), 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid (159.0 mg, 0.190 mmol, 1.00 equiv), N,N-diisopropylethylamine (74.0 mg, 0.573 mmol, 3.02 equiv) and BOP (126.0 mg, 0.285 mmol, 1.50 equiv) in A A-dimethylformamide (10 mL). The resulting mixture was stirred for 1.5 hours at room temperature. The reaction mixture was then quenched by the addition of 100 mL water and extracted with ethyl acetate (250 mL×3). The combined organic layer was washed with brine, dried over anhydrous sodium sulfate and concentrated under reduced pressure. The residue was applied onto a silica gel column eluting with dichloromethane/methanol (9:1). The obtained product was dissolved in dichloromethane/methanol (4:1, 50 mL) and filtered through a 0.22 um syringe filter. The filtrate was concentrated under reduced pressure. This resulted in 54.2 mg (24.30%) of 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)-N-[(2S)-1-[(2S,4R)-4-hydroxy-2-(5-[[4-(4-methyl-1,3-thiazol-5-yl)phenyl]methyl]-1H-imidazol-2-yl)pyrrolidin-1-yl]-3,3-dimethyl-1-oxobutan-2-yl]acetamide as a light yellow solid. LC/MS (ESI) m/z: 1175.50 $[M+1]^+$; $^1$H-NMR (300 MHz, DMSO-$d_6$) δ 12.89 (s, 1H), 9.90 (brs, 1H), 8.95 (s, 1H), 8.62 (s, 1H), 8.50 (s, 1H), 8.05 (s, 1H), 7.80-7.52 (m, 4H), 7.50-7.29 (m, 5H), 7.12-7.03 (m, 2H), 6.73 (s, 1H), 5.43-4.90 (m, 3H), 4.50-4.42 (m, 2H), 3.91-3.75 (m, 5H), 3.59-3.40 (m, 5H), 3.20-2.80 (m, 2H), 2.81-2.67 (m, 3H), 2.45-2.41 (m, 4H), 2.40-1.96 (m, 7H), 1.94-1.71 (m, 3H), 1.42-1.10 (m, 7H), 0.97-0.90 (m, 1H), 0.73 (s, 9H).

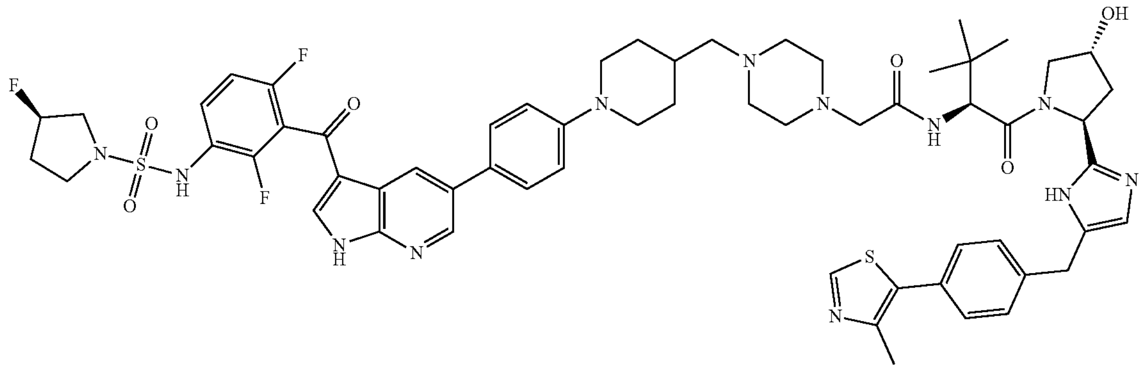 [SMILES: Cc1ncsc1-c1ccc(Cc2cnc([C@@H]3C[C@@H](O)CN3C(=O)[C@@H](NC(=O)CN3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)C(C)(C)C)[nH]2)cc1]

Exemplary Synthesis of 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N—((S)-1-((2S,4R)-4-hydroxy-2-(5-(4-(4-methylthiazol-5-yl)benzyl)thiazol-2-yl)pyrrolidin-1-yl)-3,3-dimethyl-1-oxobutan-2-yl)acetamide (Example 473)

Step 1: Preparation of tert-butyl (2S,4R)-4-((tert-butyldiphenylsilyl)oxy)-2-carbamoylpyrrolidine-1-carboxylate

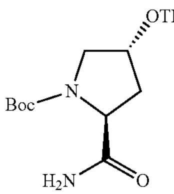

Into a 100-mL round-bottom flask, was placed tert-butyl (2S,4R)-2-carbamoyl-4-hydroxypyrrolidine-1-carboxylate (1.00 g, 4.343 mmol, 1 equiv), imidazole (739.0 mg, 10.855 mmol, 2.50 equiv) and TBDPSCl (1.43 g, 5.203 mmol, 1.20 equiv) in N,N-dimethylformamide (20 mL). The resulting mixture was stirred overnight at room temperature. The reaction was then quenched by the addition of 150 mL water and the resulting mixture was extracted with ethyl acetate (250 mL×3). The organic layers were combined, washed with brine, dried over anhydrous sodium sulfate and concentrated under reduced pressure. The residue was applied onto a silica gel column eluting with dichloromethane/methanol (98:2). This resulted in 1.55 g (76.15%) of tert-butyl (2S,4R)-4-[(tert-butyldiphenylsilyl)oxy]-2-carbamoylpyrrolidine-1-carboxylate as colorless oil. LC/MS (ESI) m/z: 469.25 $[M+1]^+$.

Step 2: Preparation of tert-butyl (2S,4R)-4-((tert-butyldiphenylsilyl)oxy)-2-carbamothioylpyrrolidine-1-carboxylate

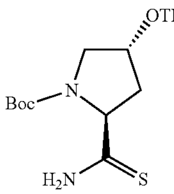

Into a 250-mL 3-necked round-bottom flask purged and maintained with an inert atmosphere of nitrogen, was placed tert-butyl (2S,4R)-4-[(tert-butyldiphenylsilyl)oxy]-2-carbamoylpyrrolidine-1-carboxylate (1.80 g, 3.841 mmol, 1 equiv) and Lawesson Reagent (1.71 g, 4.228 mmol, 1.10 equiv) in THF (60 mL). The resulting mixture was stirred for 12 hours at 70° C. in an oil bath. The mixture was then concentrated under reduced pressure. The residue was applied onto a silica gel column eluting with ethyl acetate/petroleum ether (1:4). This resulted in 1.1 g (59.09%) of tert-butyl (2S,4R)-4-[(tert-butyldiphenylsilyl)oxy]-2-carbamothioylpyrrolidine-1-carboxylate as a white solid. LC/MS (ESI) m/z: 485.30 $[M+1]^+$.

Step 3: Preparation of tert-butyl (2S,4R)-2-(5-(4-bromobenzyl)thiazol-2-yl)-4-((tert-butyldiphenylsilyl)oxy)pyrrolidine-1-carboxylate

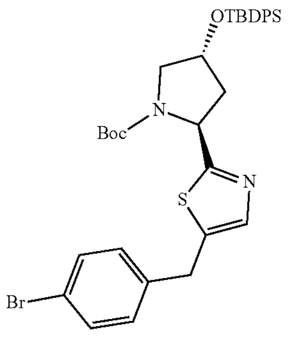

Into a 100-mL round-bottom flask, was placed tert-butyl (2S,4R)-4-[(tert-butyldiphenylsilyl)oxy]-2-carbamothioylpyrrolidine-1-carboxylate (1.0 g, 2.1 mmol, 1 equiv), pyridine (244 mg, 3.085 mmol, 1.50 equiv) and 1-bromo-3-(4-bromophenyl)propan-2-one (904.0 mg, 3.1 mmol, 1.50 equiv) in ethanol (50 mL). The resulting solution was stirred for 1 hour at 80° C. in an oil bath. The mixture was then concentrated under reduced pressure. The residue was applied onto a silica gel column eluting with ethyl acetate/petroleum ether (1:9). This resulted in 960.0 mg (68.66%) of tert-butyl (2S,4R)-2-[5-[(4-bromophenyl)methyl]-1,3-thiazol-2-yl]-4-[(tert-butyldiphenylsilyl)oxy]pyrrolidine-1-carboxylate as light yellow oil. LC/MS (ESI) m/z: 677.20 $[M+1]^+$.

Step 4: Preparation of tert-butyl (2S,4R)-4-((tert-butyldiphenylsilyl)oxy)-2-(5-(4-(4-methylthiazol-5-yl)benzyl)thiazol-2-yl)pyrrolidine-1-carboxylate

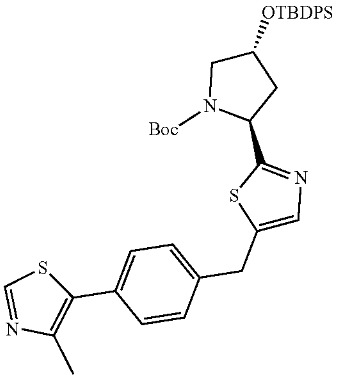

Into a 30-mL sealed tube purged and maintained with an inert atmosphere of nitrogen, was placed tert-butyl (2S,4R)-2-[5-[(4-bromophenyl)methyl]-1,3-thiazol-2-yl]-4-[(tert-butyldiphenylsilyl)oxy]pyrrolidine-1-carboxylate (800.0 mg, 1.180 mmol, 1 equiv), 4-methyl-5-(4,4,5,5-tetramethyl-1,3,2-dioxaborolan-2-yl)-1,3-thiazole (398.0 mg, 1.768 mmol, 1.50 equiv), potassium carbonate (489.0 mg, 3.538 mmol, 3.00 equiv) and $Pd(dppf)Cl_2$ (86.0 mg, 0.118 mmol, 0.10 equiv) in dioxane (15 mL) and water (3 mL). The resulting mixture was stirred for 3 hours at 95° C. in an oil bath. Then the mixture was concentrated under reduced pressure. The residue was applied onto a silica gel column eluting with ethyl acetate/petroleum ether (1:4). This resulted in 590.0 mg (71.82%) of tert-butyl (2S,4R)-4-[(tert-butyldiphenylsilyl)oxy]-2-(5-[[4-(4-methyl-1,3-thiazol-5-yl)phenyl]methyl]-1,3-thiazol-2-yl)pyrrolidine-1-carboxylate as a light yellow solid. LC/MS (ESI) m/z: 696.20 $[M+1]^+$.

Step 5: Preparation of 2-((2S,4R)-4-((tert-butyldiphenylsilyl)oxy)pyrrolidin-2-yl)-5-(4-(4-methylthiazol-5-yl)benzyl)thiazole hydrochloride

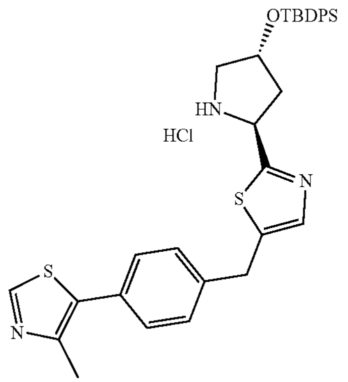

Into a 100-mL round-bottom flask, was placed tert-butyl (2S,4R)-4-[(tert-butyldiphenylsilyl)oxy]-2-(5-[[4-(4-methyl-1,3-thiazol-5-yl)phenyl]methyl]-1,3-thiazol-2-yl) pyrrolidine-1-carboxylate (600.0 mg, 0.862 mmol, 1 equiv) in dioxane (10 mL), to which was added hydrogen chloride in 1,4-dioxane solution (4.0 M, 10 mL). The resulting mixture was stirred for 2 hours at room temperature. Then the mixture was concentrated under reduced pressure. This resulted in 540.0 mg (99.06%) of 2-[(2S,4R)-4-[(tert-butyldiphenylsilyl)oxy]pyrrolidin-2-yl]-5-[[4-(4-methyl-1,3-thiazol-5-yl) phenyl]methyl]-1,3-thiazole hydrochloride as light yellow semi-solid. LC/MS (ESI) m/z: 596.30 $[M+1]^+$.

Step 6: Preparation of tert-butyl ((S)-1-((2S,4R)-4-((tert-butyldiphenylsilyl)oxy)-2-(5-(4-(4-methylthiazol-5-yl)benzyl)thiazol-2-yl)pyrrolidin-1-yl)-3,3-dimethyl-1-oxobutan-2-yl)carbamate

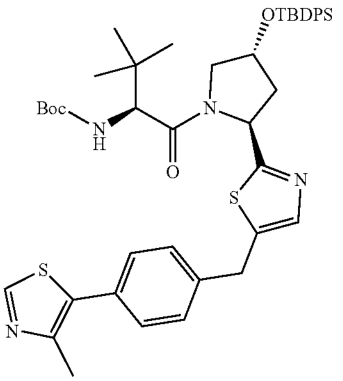

Into a 100-mL round-bottom flask, was placed 2-[(2S,4R)-4-[(tert-butyldiphenylsilyl)oxy]pyrrolidin-2-yl]-5-[[4-(4-methyl-1,3-thiazol-5-yl)phenyl]methyl]-1,3-thiazole hydrochloride (530.0 mg, 0.838 mmol, 1 equiv), (2S)-2-[[(tert-butoxy)carbonyl]amino]-3,3-dimethylbutanoic acid (582.0 mg, 2.516 mmol, 3.00 equiv), N,N-diisopropylethylamine (650.0 mg, 5.029 mmol, 6.00 equiv) and BOP (1.11 g, 2.510 mmol, 2.99 equiv) in N,N-dimethylformamide (35 mL). The resulting mixture was stirred for 12 hours at room temperature. The reaction was then quenched by the addition of 100 mL water. The resulting mixture was extracted with ethyl acetate (250 mL×3). The organic layers were combined, washed with brine, dried over anhydrous sodium sulfate and concentrated under reduced pressure. The residue was applied onto a silica gel column eluting with ethyl acetate/petroleum ether (1:3). This resulted in 340.0 mg (50.13%) of tert-butyl N-[(2S)-1-[(2S,4R)-4-[(tert-butyldiphenylsilyl)oxy]-2-(5-[[4-(4-methyl-1,3-thiazol-5-yl)phenyl]methyl]-1,3-thiazol-2-yl)pyrrolidin-1-yl]-3,3-dimethyl-1-oxobutan-2-yl]carbamate as light yellow oil. LC/MS (ESI) m/z: 809.30 $[M+1]^+$.

Step 7: Preparation of tert-butyl ((S)-1-((2S,4R)-4-hydroxy-2-(5-(4-(4-methylthiazol-5-yl)benzyl)thiazol-2-yl)pyrrolidin-1-yl)-3,3-dimethyl-1-oxobutan-2-yl)carbamate

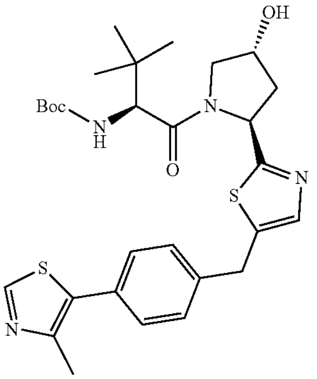 [SMILES: Cc1ncsc1-c1ccc(Cc2cnc([C@@H]3C[C@@H](O)CN3C(=O)[C@@H](NC(=O)OC(C)(C)C)C(C)(C)C)s2)cc1]

Into a 100-mL round-bottom flask, was placed tert-butyl N-[(2S)-1-[(2S,4R)-4-[(tert-butyldiphenylsilyl)oxy]-2-(5-[[4-(4-methyl-1,3-thiazol-5-yl)phenyl]methyl]-1,3-thiazol-2-yl)pyrrolidin-1-yl]-3,3-dimethyl-1-oxobutan-2-yl]carbamate (390.0 mg, 0.482 mmol, 1 equiv) in tetrahydrofuran (20 mL), to which a solution of $Bu_4N$ F (1.0 M, 1.45 mL in THF) was added. The resulting mixture was stirred for 2 hours at room temperature. The reaction was then quenched by the addition of 100 mL water. The resulting mixture was extracted with ethyl acetate (250 mL×3). The organic layers were combined, washed with brine, dried over anhydrous sodium sulfate and concentrated under reduced pressure. The residue was applied onto a silica gel column eluting with ethyl acetate/petroleum ether (3:1). This resulted in 250 mg (90.88%) of tert-butyl N-[(2S)-1-[(2S,4R)-4-hydroxy-2-(5-[[4-(4-methyl-1,3-thiazol-5-yl)phenyl]methyl]-1,3-thiazol-2-yl)pyrrolidin-1-yl]-3,3-dimethyl-1-oxobutan-2-yl] carbamate as a light yellow semi-solid. LC/MS (ESI) m/z: 571.25 $[M+1]^+$.

Step 8: Preparation of (S)-2-amino-1-((2S,4R)-4-hydroxy-2-(5-(4-(4-methylthiazol-5-yl)benzyl)thiazol-2-yl)pyrrolidin-1-yl)-3,3-dimethylbutan-1-one hydrochloride

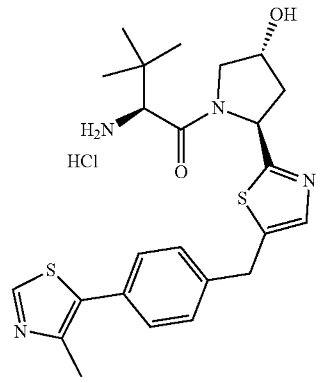 [SMILES: Cc1ncsc1-c1ccc(Cc2cnc([C@@H]3C[C@@H](O)CN3C(=O)[C@@H](N)C(C)(C)C)s2)cc1 ; Cl]

Into a 100-mL round-bottom flask, was placed tert-butyl N-[(2S)-1-[(2S,4R)-4-hydroxy-2-(5-[[4-(4-methyl-1,3-thiazol-5-yl)phenyl]methyl]-1,3-thiazol-2-yl)pyrrolidin-1-yl]-3,3-dimethyl-1-oxobutan-2-yl]carbamate (250 mg, 0.438 mmol, 1 equiv) in dioxane (20 mL), to which hydrogen chloride in 1,4-dioxane solution (4.0 M, 15 mL) was added. The resulting mixture was stirred for 2 hours at room temperature. The mixture was concentrated under reduced pressure. This resulted in 220.0 mg (99.05%) of (2S)-2-amino-1-[(2S,4R)-4-hydroxy-2-(5-[[4-(4-methyl-1,3-thiazol-5-yl) phenyl]methyl]-1,3-thiazol-2-yl)pyrrolidin-1-yl]-3,3-dimethylbutan-1-one hydrochloride as a white solid. LC/MS (ESI) m/z: 471.15 $[M+1]^+$.

Step 9: Preparation of 2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-N—((S)-1-((2S,4R)-4-hydroxy-2-(5-(4-(4-methylthiazol-5-yl)benzyl)thiazol-2-yl)pyrrolidin-1-yl)-3,3-dimethyl-1-oxobutan-2-yl)acetamide Into a 100-mL round-bottom flask, was placed 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid (459.55 mg, 0.621 mmol, 1.50 equiv), (2S)-2-amino-1-[(2S,4R)-4-hydroxy-2-(5-[[4-(4-methyl-1,3-thiazol-5-yl)phenyl]methyl]-1,3-thiazol-2-yl)pyrrolidin-1-yl]-3,3-dimethylbutan-1-one hydrochloride (210 mg, 0.414 mmol, 1 equiv), N,N-diisopropylethylamine (161 mg, 1.246 mmol, 3.01 equiv) and BOP (275 mg, 0.622 mmol, 1.50 equiv) in N,N-dimethylformamide (30 mL). The resulting solution was stirred for 2 hours at room temperature. The reaction was then quenched by the addition of 100 mL water. The resulting mixture was extracted with ethyl acetate (250 mL×3). The organic layers were combined, washed with brine, dried over anhydrous sodium sulfate and concentrated under reduced pressure. The residue was applied onto a silica gel column eluting with dichloromethane/methanol (8:1). The obtained product was dissolved in 50 mL dichloromethane and the solution was filtered through 0.22 um syringe filter. The filtrate was concentrated under reduced pressure. This resulted in 57.1 mg (11.56%) of 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)-N-[(2S)-1-[(2S,4R)-4-hydroxy-2-(5-[[4-(4-methyl-1,3-thiazol-5-yl)phenyl]methyl]-1,3-thiazol-2-yl)pyrrolidin-1-yl]-3,3-dimethyl-1-oxobutan-2-yl]acetamide as a yellow solid. LC/MS (ESI) m/z: 1192.60 $[M+1]^+$; $^1$H-NMR (300 MHz, DMSO-$d_6$) δ 12.88 (s, 1H), 9.83 (s, 1H), 8.96 (s, 1H), 8.63 (s, 1H), 8.51 (s, 1H), 8.05 (s, 1H), 7.80-7.70 (m, 1H), 7.69-7.56 (m, 3H), 7.39 (d, J=8.0 Hz, 2H), 7.35-7.18 (m, 4H), 7.04 (d, J=8.4 Hz, 2H), 5.74 (s, 1H), 5.44-5.06 (m, 3H), 4.51 (d, J=9.3 Hz, 1H), 4.49-4.38 (m, 1H), 4.03 (s, 2H), 3.85-3.72 (m, 3H), 3.70-3.62 (m, 1H), 3.48-3.39 (m, 3H), 3.16-2.82 (m, 2H), 2.69 (t, J=11.8 Hz, 2H), 2.45-2.35 (m, 6H), 2.25-2.05 (m, 7H), 1.80-1.60 (m, 3H), 1.23-1.19 (m, 6H), 0.83 (s, 9H).

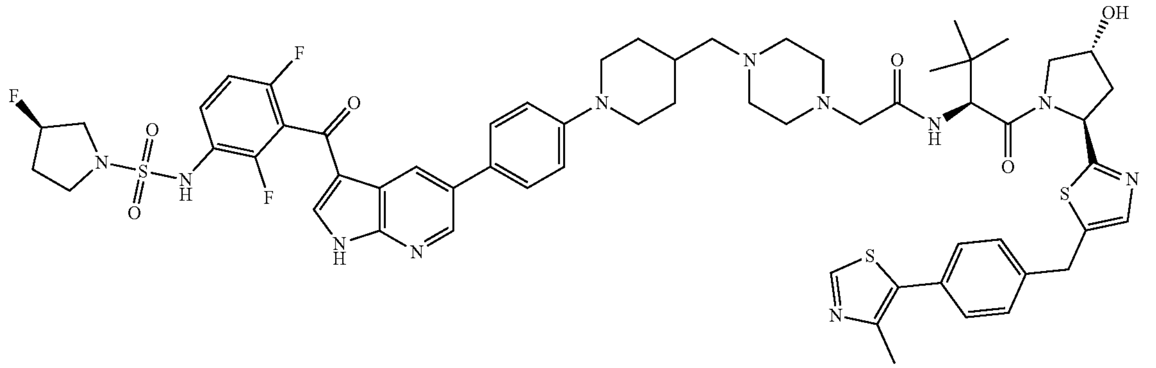 [SMILES: Cc1ncsc1-c1ccc(Cc2cnc([C@@H]3C[C@@H](O)CN3C(=O)[C@@H](NC(=O)CN3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)C(C)(C)C)s2)cc1]

Exemplary Synthesis of 2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)-N—((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)acetamide (Example 445)

Step 1: Preparation of 2-(4-((4-(4-(3-(2,6-difluoro-3-(((R)-3-fluoropyrrolidine)-yl-sulfonamido)benzoyl)-1H-pyrrolo[2,3-b]pyridin-5-yl)phenyl)piperazin-1-yl)methyl)piperidin-1-yl)-N—((S)-1-((2S,4R)-4-hydroxy-2-(5-(4-(4-methylthiazol-5-yl)phenyl)-1H-imidazol-2-yl)pyrrolidin-1-yl)-3,3-dimethyl-1-oxobutan-2-yl)acetamide

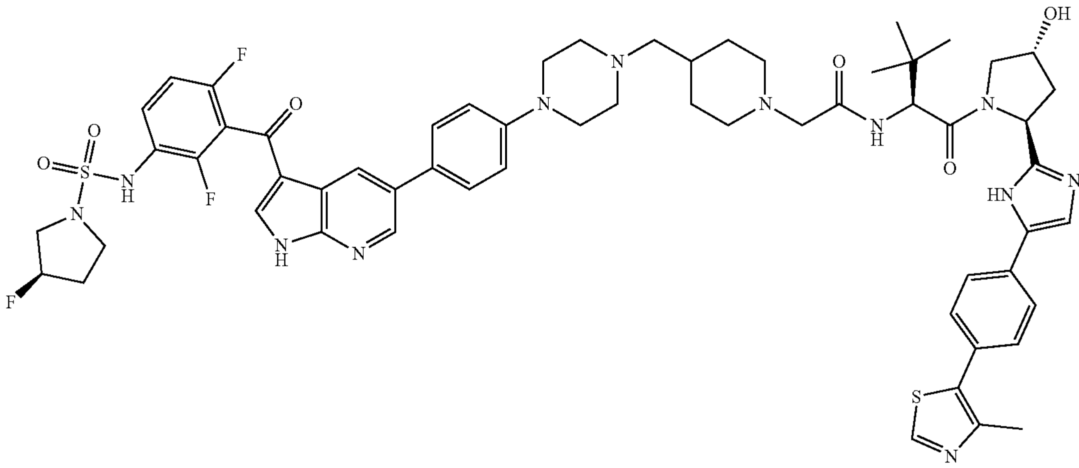 [SMILES: Cc1ncsc1-c1ccc(-c2cnc([C@@H]3C[C@@H](O)CN3C(=O)[C@@H](NC(=O)CN3CCC(CN4CCN(c5ccc(-c6cnc7[nH]cc(C(=O)c8c(F)ccc(NS(=O)(=O)N9CC[C@@H](F)C9)c8F)c7c6)cc5)CC4)CC3)C(C)(C)C)[nH]2)cc1]

Into a 100-mL round-bottom flask, was placed 2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (252.45 mg, 0.341 mmol, 1.00 equiv), (2S)-2-amino-1-[(2S,4R)-4-hydroxy-2-[5-[4-(4-methyl-1,3-thiazol-5-yl)phenyl]-1H-imidazol-2-yl]pyrrolidin-1-yl]-3,3-dimethylbutan-1-one (150 mg, 0.341 mmol, 1 equiv), DIEA (88.20 mg, 0.682 mmol, 2 equiv), BOP (226.38 mg, 0.512 mmol, 1.5 equiv) in DMF (5 mL). The resulting mixture was stirred for 1 hour at room temperature. The reaction was then quenched by the addition of 20 mL water and the mixture was extracted with ethyl acetate (20 mL×2). The combined organic layer was washed with brine, dried over anhydrous sodium sulfate and concentrated under reduced pressure. The residue was applied onto a silica gel column eluting with ethyl acetate/MeOH (5:1). This resulted in 72.0 mg (18.17%) of 2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)-N-[(2S)-1-[(2S,4R)-4-hydroxy-2-[5-[4-(4-methyl-1,3-thiazol-5-yl)phenyl]-1H-imidazol-2-yl]pyrrolidin-1-yl]-3,3-dimethyl-1-oxobutan-2-yl]acetamide as yellow solid. LC/MS (ESI) m/z: 1161.35 $[M+1]^+$; $^1$H-NMR (300 MHz, DMSO-$d_6$) δ 12.89 (br s, 1H), 11.95 (s, 1H), 9.83 (br s, 1H), 8.95 (s, 1H), 8.62 (d, J=2.2 Hz, 1H), 8.51 (s, 1H), 8.05 (s, 1H), 7.78-7.70 (m, 3H), 7.57-7.50 (m, 4H), 7.42 (d, J=8.0 Hz, 2H), 7.24-7.20 (m, 1H), 7.10-7.01 (m, 2H), 5.49-5.27 (m, 2H), 5.11-5.03 (m, 1H), 4.61-4.50 (m, 2H), 3.95-3.84 (m, 1H), 3.71-3.61 (m, 1H), 3.47-3.42 (m, 1H), 3.41-3.37 (m, 2H), 3.30-3.20 (m, 1H), 3.19-3.10 (m, 4H), 2.93-2.72 (m, 4H), 2.46 (s, 3H), 2.41-1.89 (m, 9H), 1.89-1.70 (m, 2H), 1.68-1.52 (m, 1H), 1.28-1.22 (m, 1H), 1.21-1.11 (m, 3H), 0.95-0.91 (m, 1H), 0.85-0.72 (m, 9H).

Exemplary Synthesis of (2S,4R)-1-((S)-5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoyl)-4-hydroxy-N—((S)-1-(4-(4-methylthiazol-5-yl)phenyl)ethyl)pyrrolidine-2-carboxamide (Example 4751 and (2S,4R)-1-((R)-5-(4-(3-(2,6-difluoro-3-(((R)-3-fluoropyrrolidine)-1-sulfonamido) be n zo v 1)-1H-pyrrolo[2,3-b]pyridin-5-yl)phenoxy)-2-(3-methylisoxazol-5-yl)pentanoyl)-4-hydroxy-N—((S)-1-(4-(4-methylthiazol-5-yl)phenyl)ethyl)pyrrolidine-2-carboxamide (Example 476)

Step 1: Preparation of 3-(4-bromophenoxy)propan-1-ol

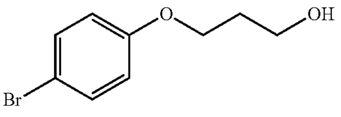 [SMILES: OCCCOc1ccc(Br)cc1]

To a solution of 4-bromophenol (3 g, 17.34 mmol, 1 eq) in N,N-dimethylformamide (100 mL) was added 3-bromopropan-1-ol (2.89 g, 20.81 mmol, 1.2 eq) and potassium carbonate (7.19 g, 52.02 mmol, 3 eq), and the mixture was stirred at 70° C. for 2 hrs. The mixture was diluted with water (100 mL) and extracted with ethyl acetate (100 mL×3) and washed with brine (300 mL). The organic phase was dried by anhydrous sodium sulfate, filtered and the filtrate was condensed to give crude product. The residue was purified by silica gel column chromatography (pure petroleum ether). The product 3-(4-bromophenoxy)propan-1-ol (3.10 g, 13.41 mmol, 77% yield) was obtained as colorless oil. $^1$H-NMR (400 MHz, $CDCl_3$) δ 7.41-7.30 (m, 2H), 6.84-6.69 (m, 2H), 4.16-3.95 (m, 2H), 3.83 (t, J=6.0 Hz, 2H), 2.23-1.90 (m, 4H).

Step 2: Preparation of 1-bromo-4-(3-bromopropoxy)benzene

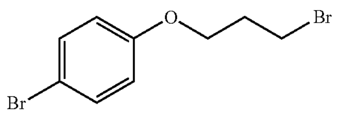 [SMILES: BrCCCOc1ccc(Br)cc1]

To a solution of 3-(4-bromophenoxy)propan-1-ol (3.1 g, 13.41 mmol, 1 eq) in tetrahydrofuran (150 mL) was added carbon tetrabromide (6.67 g, 20.12 mmol, 1.5 eq) and triphenylphosphine (5.28 g, 20.12 mmol, 1.5 eq). The reaction mixture was stirred at 20° C. for 1 h. The mixture was diluted with water (70 mL) and extracted with ethyl acetate (40 mL×3) and washed with brine (60 mL×2). The organic phase was dried by anhydrous sodium sulfate, filtered and the filtrate was condensed to give crude product. The residue was purified by silica gel column chromatography (pure petroleum ether). The product 1-bromo-4-(3-bromopropoxy)benzene (3 g, 10.20 mmol, 76% yield) was obtained as yellow solid. $^1$H-NMR (400 MHz, $CDCl_3$) δ 7.43-7.35 (m, 2H), 6.83-6.75 (m, 2H), 4.18-4.01 (m, 2H), 3.60 (t, J=6.4 Hz, 2H), 2.32 (quin, J=6.0 Hz, 2H).

Step 3: Preparation of 2-(3-methylisoxazol-5-yl)acetic acid

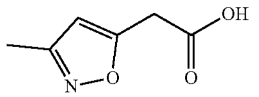

To a solution of 3,5-dimethylisoxazole (4.85 g, 49.94 mmol, 4.93 mL, 1 eq) in tetrahydrofuran (80 mL) was added n-butyllithium (2.5 M, 19.98 mL, 1 eq) dropwised at −70° C. When addition was completed, the mixture was stirred at −70° C. for half an hour. Then carbon dioxide (2.20 g, 49.94 mmol, 1 eq) gas was bubbled into the mixture at −70° C. for half an hour. The resulting mixture was stirred at −70~0° C. for another 3 hours. The mixture was poured into 100 mL ice-water, and adjust the pH to 3.0 with 1.0 M hydrochloric acid. The mixture was extracted with ethyl acetate (100 mL×2). The combined organic layers were washed with brine (200 mL), dried over sodium sulfate, filtered and concentrated in vacuum. The residue was directly used for next step without further purification. 2-(3-methylisoxazol-5-yl)acetic acid (4.5 g, crude) as an off-white solid was obtained.

Step 4: Preparation of methyl 2-(3-methylisoxazol-5-yl)acetate

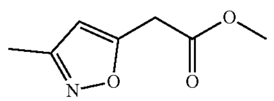

To a solution of 2-(3-methylisoxazol-5-yl)acetic acid (4.2 g, 29.76 mmol, 1 eq) in methanol (50 mL) was added thionyl chloride (7.08 g, 59.52 mmol, 4.32 mL, 2 eq) dropwise at 0° C. When addition was completed, the mixture was heated to 80° C. and stirred at 80° C. for 2 hours. The solvent was concentrated in vacuum, the residue diluted with ethyl acetate (100 mL). The mixture was washed with saturated sodium bicarbonate solution (100 mL), brine (100 mL), dried over sodium sulfate, filtered and concentrated in vacuum. The residue was purified by silica gel chromatography (petroleum ether:ethyl acetate=10:1~5:1) to give methyl 2-(3-methylisoxazol-5-yl)acetate (3.6 g, 23.20 mmol, 77% yield) as a colorless oil. $^1$H-NMR (400 MHz, $CDCl_3$) δ 6.11 (s, 1H), 3.80 (s, 2H), 3.77 (s, 3H), 2.30 (s, 3H).

Step 5: Preparation of methyl 5-(4-bromophenoxy)-2-(3-methylisoxazol-5-yl)pentanoate

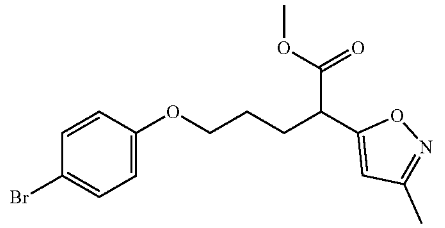 [SMILES: COC(=O)C(CCCOc1ccc(Br)cc1)c1cc(C)no1]

To a solution of methyl 2-(3-methylisoxazol-5-yl)acetate (0.95 g, 6.12 mmol, 1 eq) in tetrahydrofuran (20 mL) was added potassium tert-butoxide (825 mg, 7.35 mmol, 1.2 eq) and stirred at 15° C. for 30 min, then 1-bromo-4-(4-bromobutoxy)benzene (1.98 g, 6.74 mmol, 1.1 eq) was added into the mixture at 20° C. with the $N_2$ protection for 2 hrs. The mixture was diluted with water (50 mL) and extracted with ethyl acetate (50 mL×3) and washed with brine (100 mL). The organic phase was dried by anhydrous sodium sulfate, filtered and the filtrate was condensed to give crude product. The residue was purified by silicon dioxide column chromatography (Petroleum ether/Ethyl acetate=1/0 to 60/1). The product methyl 5-(4-bromophenoxy)-2-(3-methylisoxazol-5-yl)pentanoate (370 mg, 1.00 mmol, 17% yield) was obtained as colorless oil. LC/MS (ESI) m/z: 368.1 $[M+1]^+$; $^1$H NMR (400 MHz, $CDCl_3$) δ 7.39-7.31 (m, 2H), 6.80-6.69 (m, 2H), 6.11-6.02 (m, 1H), 4.16-3.82 (m, 3H), 3.81-3.74 (m, 1H), 3.73 (s, 2H), 2.27-2.27 (m, 1H), 2.30-2.26 (m, 2H), 2.26-2.02 (m, 1H), 1.86-1.73 (m, 1H), 1.73-1.71 (m, 1H), 1.88-1.69 (m, 1H).

Step 6: Preparation of methyl 5-(4-(3-(2,6-difluoro-3-(((R)-3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenoxy)-2-(3-methylisoxazol-5-yl)pentanoate

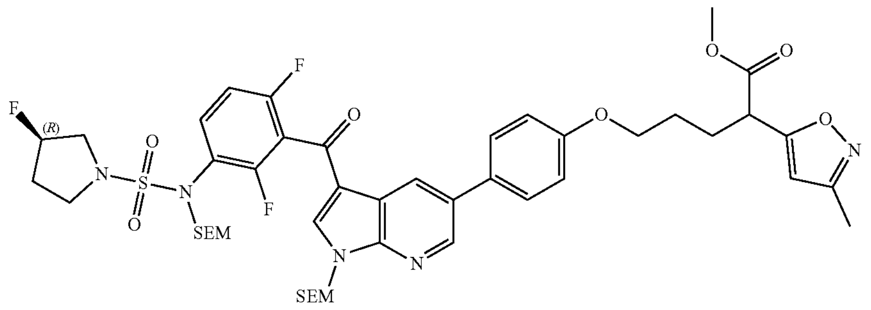

A flask was charged with methyl 5-(4-bromophenoxy)-2-(3-methylisoxazol-5-yl)pentanoate (100 mg, 0.27 mmol, 1 eq), cesium fluoride (165 mg, 1.09 mmol, 4 eq), 4-ditert-butylphosphanyl-N,N-dimethyl-aniline;dichloropalladium (19 mg, 0.03 mmol, 0.1 eq), (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (220 mg, 0.27 mmol, 1 eq), dioxane (10 mL) and water (2 mL). The mixture was heated to 120° C. for 1 hr under nitrogen atmosphere. The reaction mixture was quenched by addition water (30 mL) and extracted with ethyl acetate (20 mL×3). The combined organic layers were washed with brine (20 mL×2), dried over anhydrous sodium sulfate, filtered and concentrated under reduced pressure to give a residue. The residue was purified by pre-TLC (petroleum ether:ethyl acetate=1:1). The desired product methyl 5-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]-2-(3-methylisoxazol-5-yl)pentanoate (50 mg, 0.05 mmol, 19% yield)) was obtained as yellow oil. LC/MS (ESI) m/z: 972.4 $[M+1]^+$.

Step 7: Preparation of methyl 5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoate

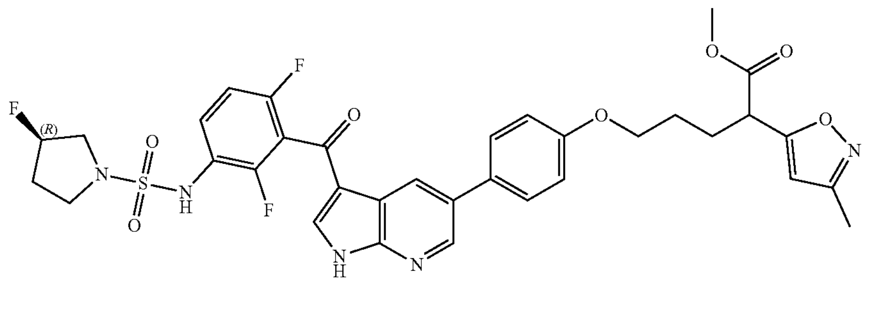

To a solution of methyl methyl 5-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]-2-(3-methylisoxazol-5-yl)pentanoate (200 mg, 0.20 mmol, 1 eq) in methanol (5 mL) was added hydrogen chloride/dioxane (4 M, 10 mL, 464.12 eq). The solution was stirred at 40° C. for 20 hr. The reaction mixture was concentrated in the vacuum. The residue was used into the next reaction and has no purification. The product methyl 5-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)pentanoate (150 mg, crude, HCl) was obtained as yellow oil. LC/MS (ESI) m/z: 712.2 $[M+1]^+$.

Step 8: Preparation of 5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoic acid

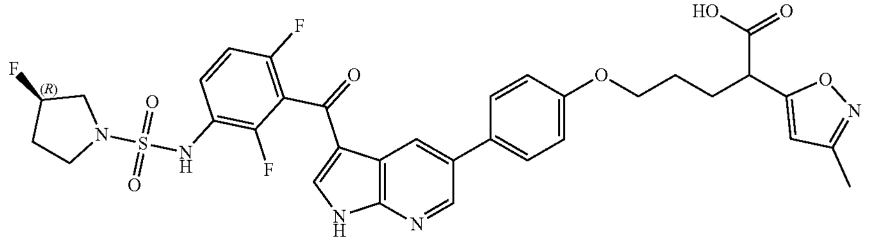

To a solution of methyl 5-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)pentanoate (150 mg, 0.20 mmol, 1 eq, HCl) in methanol (2 mL) and water (2 mL) was added lithium hydroxide (42 mg, 1.00 mmol, 5 eq) and the mixture was stirred at 15° C. for 2 h. The reaction mixture charged with hydrogen chloride (1 M) slowly to adjust the pH to 4-5, and the mixture was washed with water (20 mL), then extracted with ethyl acetate (15 mL×3) and washed with brine (15 mL), then the organic phase was concentrated in the vacuum to get the residue. The product 5-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methyl isoxazol-5-yl)pentanoic acid (130 mg, crude) was obtained as yellow solid. LC/MS (ESI) m/z: 698.2 $[M+1]^+$.

Step 9: Preparation of (2S,4R)-1-((S)-5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoyl)-4-hydroxy-N—((S)-1-(4-(4-methylthiazol-5-yl)phenyl)ethyl)pyrrolidine-2-carboxamide and (2S,4R)-1-((R)-5-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)pentanoyl)-4-hydroxy-N—((S)-1-(4-(4-methylthiazol-5-yl)phenyl)ethyl)pyrrolidine-2-carboxamide

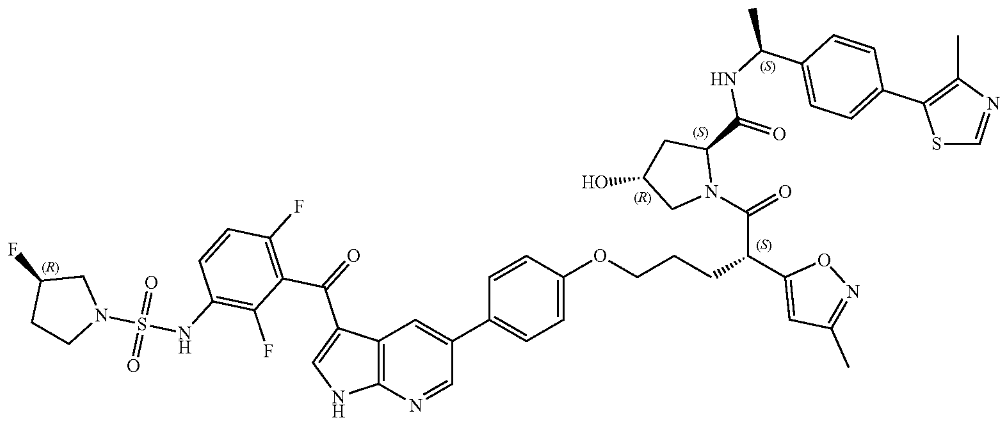

+

-continued

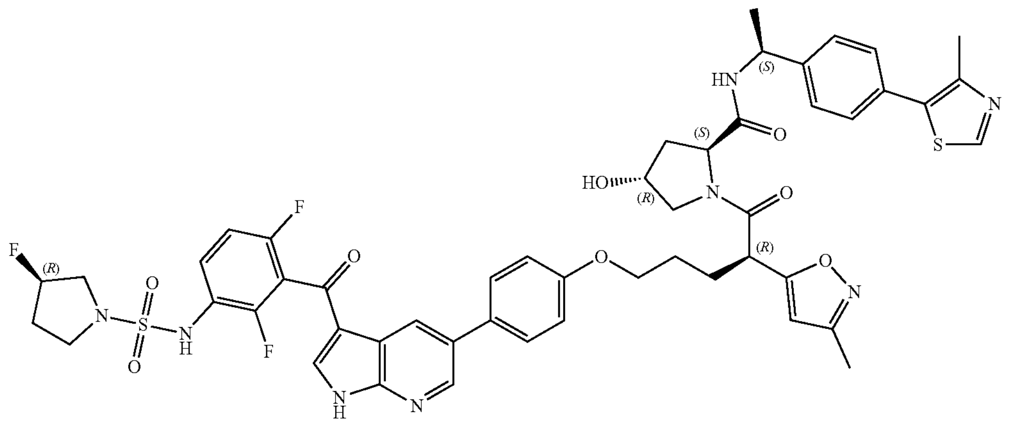

To a solution of 5-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)pentanoic acid (130 mg, 0.19 mmol, 1 eq) and (2S,4R)-4-hydroxy-N-[(1S)-1-[4-(4-methylthiazol-5-yl)phenyl]ethyl]pyrrolidine-2-carboxamide (69 mg, 0.19 mmol, 1 eq, HCl) in N,N-dimethylformamide (5 mL) was added 1-hydroxybenzotriazole (31 mg, 0.23 mmol, 1.2 eq) and N,N-diisopropylethylamine (73 mg, 0.56 mmol, 3 eq), and the mixture was stirred at 15° C. for 30 min, and N-(3-dimethylaminopropyl)-N-ethylcarbodiimide hydrochloride (43 mg, 0.23 mmol, 1.2 eq) was added into the mixture, then stirred at 40° C. for 2 h. The mixture was concentrated in the vacuum. The residue was purified by pre-HPLC. The first product, (2S,4R)-1-[(2S)-5-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)pentanoyl]-4-hydroxy-N-[(1S)-1-[4-(4-methylthiazol-5-yl)phenyl]ethyl]pyrrolidine-2-carboxamide (23.7 mg, 0.02 mmol, 12% yield, 99% purity), was obtained as white solid. LC/MS (ESI) m/z: 1011.3 $[M+1]^+$; $^1$H-NMR (300 MHz, DMSO-$d_6$) δ 9.04-8.91 (m, 1H), 8.65 (s, 1H), 8.56 (s, 1H), 8.41 (d, J=7.5 Hz, 1H), 8.07 (s, 1H), 7.72-7.55 (m, 3H), 7.49-7.31 (m, 5H), 7.21 (s, 1H), 7.13-7.00 (m, 2H), 6.36-6.03 (m, 1H), 5.40-5.19 (m, 1H), 5.13 (s, 1H), 5.00-4.84 (m, 1H), 4.48-4.37 (m, 1H), 4.31 (s, 1H), 4.18 (t, J=7.1 Hz, 1H), 4.11-3.95 (m, 2H), 3.78 (dd, J=4.5, 10.5 Hz, 1H), 3.58 (d, J=11.4 Hz, 1H), 3.45 (s, 1H), 2.47-2.39 (m, 4H), 2.27-2.16 (m, 4H), 2.15-2.00 (m, 4H), 2.00-1.88 (m, 2H), 1.88-1.65 (m, 3H), 1.25-0.98 (m, 1H), 1.38 (d, J=6.8 Hz, 3H). The second product, (2S,4R)-1-[(2R)-5-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)pentanoyl]-4-hydroxy-N-[(1S)-1-[4-(4-methylthiazol-5-yl)phenyl]ethyl]pyrrolidine-2-carboxamide (15.7 mg, 0.02 mmol, 8% yield, 98% purity), was obtained as white solid. LC/MS (ESI) m/z: 1011.3 $[M+1]^+$; $^1$H-NMR (300 MHz, DMSO-$d_6$) δ 9.04-8.94 (m, 1H), 8.65 (d, J=2.1 Hz, 1H), 8.56 (s, 1H), 8.40 (d, J=7.7 Hz, 1H), 8.05 (s, 1H), 7.67 (d, J=8.7 Hz, 2H), 7.62-7.53 (m, 1H), 7.48-7.41 (m, 2H), 7.40-7.30 (m, 3H), 7.21-7.01 (m, 1H), 7.11-7.01 (m, 2H), 6.28-6.22 (m, 1H), 6.33 (s, 1H), 5.43-5.19 (m, 1H), 5.17 (s, 1H), 5.03 (s, 1H), 4.92 (t, J=7.3 Hz, 1H), 4.65-4.56 (m, 1H), 4.54-4.37 (m, 1H), 4.29 (s, 1H), 4.21 (t, J=7.2 Hz, 1H), 4.06 (t, J=6.1 Hz, 2H), 4.02-3.90 (m, 1H), 3.73 (t, J=7.7 Hz, 1H), 3.60 (d, J=10.0 Hz, 1H), 2.47-2.43 (m, 4H), 2.33 (d, J=1.8 Hz, 1H), 2.25-2.16 (m, 4H), 2.13-1.91 (m, 5H), 1.78 (dd, J=7.5, 12.5 Hz, 3H), 1.26-1.13 (m, 1H), 1.44-1.10 (m, 5H).

Exemplary Synthesis of (2S,4R)-1-((S)-6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoyl)-4-hydroxy-N—((S)-1-(4-(4-methylthiazol-5-yl)phenyl)ethyl)pyrrolidine-2-carboxamide (Example 452) and (2S,4R)-1-((R)-6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoyl)-4-hydroxy-N—((S)-1-(4-(4-methylthiazol-5-yl)phenyl)ethyl)pyrrolidine-2-carboxamide (Example 4531

Step 1: Preparation of 1-bromo-4-(4-bromobutoxy)benzene

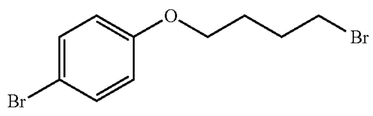 [SMILES: BrCCCCOc1ccc(Br)cc1]

To a solution of 4-bromophenol (3 g, 17.34 mmol, 1 eq) in N,N-dimethylformamide (100 mL) was added 1,4-dibromobutane (18.72 g, 86.70 mmol, 5 eq) and potassium carbonate (7.19 g, 52.02 mmol, 3 eq), and the mixture was stirred at 70° C. for 2 hrs. The mixture was diluted with water (100 mL) and extracted with ethyl acetate (100 mL×3) and washed with brine (300 mL). The organic phase was dried by anhydrous sodium sulfate, filtered and the filtrate was condensed to give crude product. The residue was purified by silica gel column chromatography (pure petroleum ether). The product 1-bromo-4-(4-bromobutoxy)benzene (4.1 g, 13.31 mmol, 77% yield) was obtained as colorless oil. LC/MS (ESI) m/z: 308.1 $[M+1]^+$; $^1$H-NMR (400 MHz, $CDCl_3$) δ 7.44-7.31 (m, 2H), 6.87-6.71 (m, 2H), 4.03-3.88 (m, 2H), 3.55-3.37 (m, 2H), 2.12-1.87 (m, 4H).

Step 2: Preparation of methyl 6-(4-bromophenoxy)-2-(3-methylisoxazol-5-yl)hexanoate

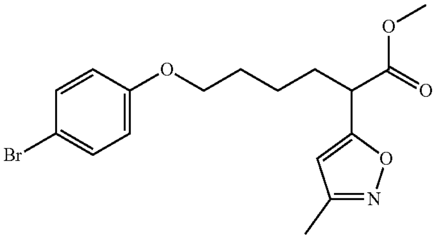 [SMILES: COC(=O)C(CCCCOc1ccc(Br)cc1)c1cc(C)no1]

To a solution of methyl 2-(3-methylisoxazol-5-yl)acetate (420 mg, 2.71 mmol, 1 eq) in tetrahydrofuran (20 mL) was added potassium tert-butoxide (456 mg, 4.06 mmol, 1.5 eq) and stirred at 15° C. for 30 min, then 1-bromo-4-(4-bromobutoxy)benzene (1 g, 3.25 mmol, 1.2 eq) was added into the mixture at 20° C. with $N_2$ protection for 2 hrs. The mixture was diluted with water (50 mL) and extracted with ethyl acetate (50 mL×3) and washed with brine (100 mL). The organic phase was dried by anhydrous sodium sulfate, filtered and the filtrate was condensed to give crude product. The residue was purified by pre-HPLC. The product methyl 6-(4-bromophenoxy)-2-(3-methylisoxazol-5-yl)hexanoate (150 mg, 0.39 mmol, 15% yield) was obtained as white solid. LC/MS (ESI) m/z: 382.0 $[M+1]^+$; $^1$H-NMR (400 MHz, $CDCl_3$) δ 7.41-7.31 (m, 2H), 6.81-6.71 (m, 2H), 6.08 (s, 1H), 3.96-3.82 (m, 3H), 3.74 (s, 3H), 2.34 (s, 3H), 2.20-2.07 (m, 1H), 2.06-1.90 (m, 1H), 1.89-1.69 (m, 2H), 1.58-1.41 (m, 2H).

Step 3: Preparation of methyl 6-(4-(3-(2,6-difluoro-3-(((R)-3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenoxy)-2-(3-methylisoxazol-5-yl)hexanoate

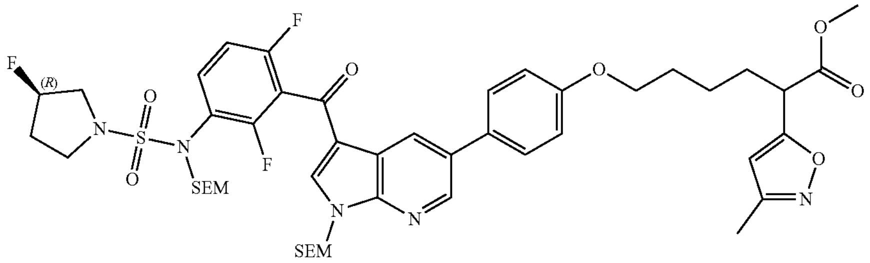

A flask was charged with methyl 6-(4-bromophenoxy)-2-(3-methylisoxazol-5-yl)hexanoate (150 mg, 0.39 mmol, 1 eq), cesium fluoride (239 mg, 1.57 mmol, 4 eq), 4-ditert-butylphosphanyl-N,N-dimethyl-aniline;dichloropalladium (28 mg, 0.04 mmol, 0.1 eq), (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (318 mg, 0.39 mmol, 1 eq), dioxane (10 mL) and water (2 mL). The mixture was heated to 120° C. for 1 hr under nitrogen atmosphere. The reaction mixture was quenched by addition water (10 mL), and then diluted with water (20 mL) and extracted with ethyl acetate (40 mL×3). The combined organic layers were washed with brine (30 mL×2), dried over anhydrous sodium sulfate, filtered and concentrated under reduced pressure to give a residue. The residue was purified by pre-TLC (petroleum ether:ethyl acetate=1:1). The product methyl 6-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]-2-(3-methylisoxazol-5-yl)hexanoate (170 mg, 0.17 mmol, 44% yield) was obtained as yellow oil.

Step 4: Preparation of methyl 6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoate

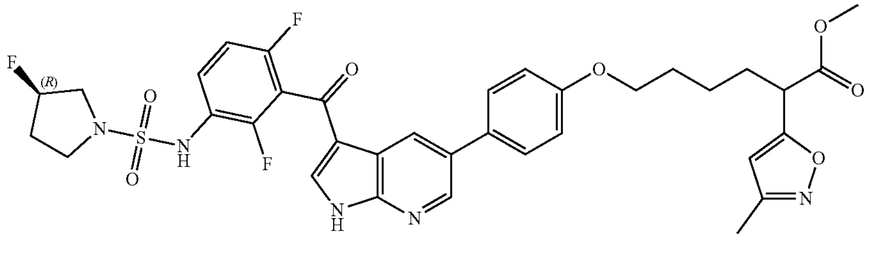

To a solution of methyl 6-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]-2-(3-methylisoxazol-5-yl)hexanoate (170 mg, 0.17 mmol, 1 eq) in methanol (5 mL) was added hydrogen chloride/dioxane (4 M, 20 mL, 464.12 eq). The solution was stirred at 40° C. for 68 hr. The reaction mixture was concentrated in the vacuum. The residue was used into the next reaction without further purification. The desired product methyl 6-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)hexanoate (120 mg, 0.16 mmol, 91% yield, HCl) was obtained as colorless solid. LC/MS (ESI) m/z: 726.1 $[M+1]^+$.

Step 5: Preparation of 6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoic acid

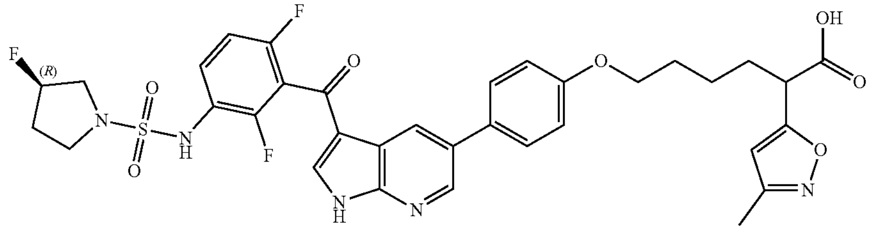

To a solution of methyl 6-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)hexanoate (120 mg, 0.16 mmol, 1 eq, HCl) in methanol (2 mL) and water (2 mL) was added lithium hydroxide (33 mg, 0.79 mmol, 5 eq) and the mixture was stirred at 15° C. for 2 h. The reaction mixture was added hydrogen chloride (1 M) slowly to adjust the pH to 4-5, and the mixture was washed with water (20 mL), then extracted with ethyl acetate (15 mL×3) and washed with brine (15 mL), then the organic phase was concentrated in the vacuum to get the residue. The product 6-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)hexanoic acid (110 mg, crude) was obtained as yellow solid. LC/MS (ESI) m/z: 712.1 $[M+1]^+$.

Step 6: Preparation of (2S,4R)-1-((S)-6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoyl)-4-hydroxy-N—((S)-1-(4-(4-methylthiazol-5-yl)phenyl)ethyl)pyrrolidine-2-carboxamide and (2S,4R)-1-((R)-6-(4-(3-(2,6-difluoro-3-(((R)-3-fluoropyrrolidine)-1-sulfonamido)benzoyl)-1H-pyrrolo[2,3-b]pyridin-5-yl)phenoxy)-2-(3-methylisoxazol-5-yl)hexanoyl)-4-hydroxy-N—((S)-1-(4-(4-methylthiazol-5-yl)phenyl)ethyl)pyrrolidine-2-carboxamide

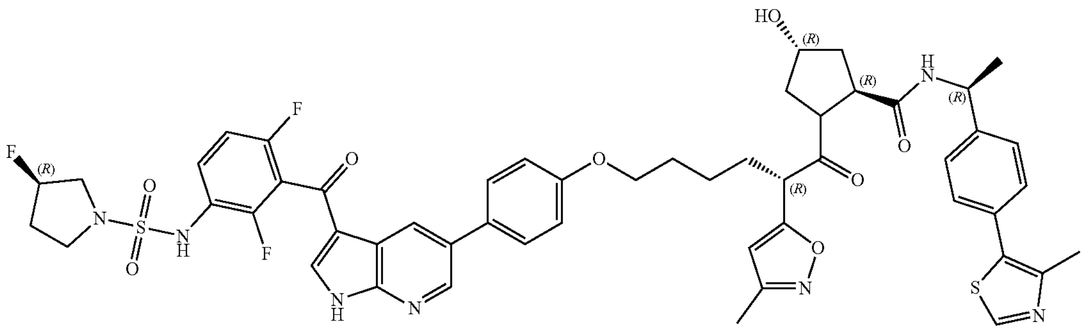

+

-continued

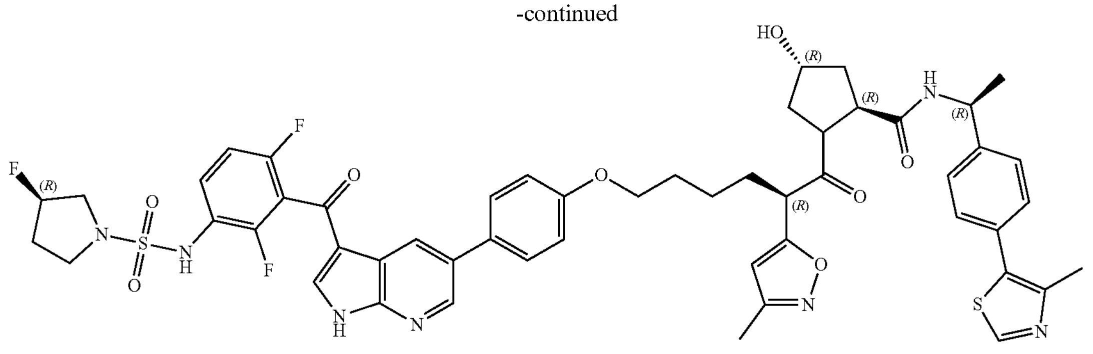

To a solution of 6-[4-[3-[2,6-difluoro-3-[[(3R)-3-fluoro-pyrrolidin-1-yl]sulfonylamino]benzoyl]-1H-pyrrolo[2,3-b]pyridin-5-yl]phenoxy]-2-(3-methylisoxazol-5-yl)hexanoic acid (110 mg, 0.16 mmol, 1 eq) and (2S,4R)-4-hydroxy-N-[(1S)-1-[4-(4-methylthiazol-5-yl)phenyl]ethyl]pyrrolidine-2-carboxamide (57 mg, 0.16 mmol, 1 eq, HCl) in N,N-dimethylformamide (5 mL) was added 1-hydroxybenzotriazole (25 mg, 0.19 mmol, 1.2 eq) and N,N-diisopropylethylamine (60 mg, 0.47 mmol, 3 eq), and the mixture was stirred at 15° C. for 30 min, and N-(3-dimethylaminopropyl)-N-ethylcarbodiimide hydrochloride (36 mg, 0.19 mmol, 1.2 eq) was added into the mixture, then stirred at 40° C. for 2 h. The mixture was concentrated in the vacuum. The residue was purified by pre-HPLC. The product 1 (2S,4R)-1-[(2S)-6-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)hexanoyl]-4-hydroxy-N-[(1S)-1-[4-(4-methylthiazol-5-yl)phenyl]ethyl]pyrrolidine-2-carboxamide (45.2 mg, 0.04 mmol, 28% yield, 98% purity) was obtained as white solid. LC/MS (ESI) m/z: 1025.3 $[M+1]^+$; $^1$H-NMR (400 MHz, DMSO-$d_6$) δ 9.04-8.92 (m, 1H), 8.64 (d, J=2.0 Hz, 1H), 8.55 (s, 1H), 8.38 (d, J=8.0 Hz, 1H), 8.06 (s, 1H), 7.75-7.54 (m, 3H), 7.52-7.27 (m, 4H), 7.19 (t, J=8.8 Hz, 1H), 7.11-6.99 (m, 2H), 6.34-6.02 (m, 1H), 5.38-5.04 (m, 2H), 5.01-4.80 (m, 1H), 4.76-4.58 (m, 1H), 4.51-4.35 (m, 1H), 4.30 (s, 1H), 4.10 (t, J=7.6 Hz, 1H), 4.05-3.86 (m, 3H), 3.76 (dd, J=4.4, 10.0 Hz, 1H), 3.56-3.49 (m, 2H), 3.51-3.43 (m, 1H), 2.47-2.35 (m, 5H), 2.26-2.14 (m, 3H), 2.13-1.89 (m, 4H), 1.88-1.64 (m, 4H), 1.59-1.09 (m, 5H). The product 2 (2S,4R)-1-[(2R)-6-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]-2-(3-methylisoxazol-5-yl)hexanoyl]-4-hydroxy-N-[(1S)-1-[4-(4-methylthiazol-5-yl)phenyl]ethyl]pyrrolidine-2-carboxamide (18.6 mg, 0.02 mmol, 11% yield, 97% purity) was obtained as white solid. LC/MS (ESI) m/z: 1026.2 $[M+1]^+$; $^1$H-NMR (400 MHz, DMSO-$d_6$) δ 9.02-8.94 (m, 1H), 8.65 (d, J=1.6 Hz, 1H), 8.56 (s, 1H), 8.38 (d, J=7.6 Hz, 1H), 8.20 (s, 1H), 8.07 (s, 1H), 7.72-7.56 (m, 3H), 7.48-7.37 (m, 3H), 7.36-7.27 (m, 2H), 7.22 (t, J=8.8 Hz, 1H), 7.07 (d, J=8.8 Hz, 2H), 6.34-6.17 (m, 1H), 5.35 (s, 1H), 5.22 (s, 1H), 5.13 (s, 1H), 5.04-4.86 (m, 1H), 4.51-4.38 (m, 1H), 4.28 (s, 1H), 4.16-3.90 (m, 2H), 3.73 (d, J=7.6 Hz, 1H), 3.62-3.51 (m, 1H), 3.46 (s, 2H), 2.42 (d, J=8.8 Hz, 5H), 2.27-2.14 (m, 3H), 2.07 (d, J=15.2 Hz, 2H), 2.12-2.01 (m, 1H), 1.99-1.88 (m, 2H), 1.87-1.69 (m, 3H), 1.52-1.35 (m, 5H).

Exemplary Synthesis of (2S,4R)-1-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide (Example 460)

Step 1: Preparation of 1-bromo-4-(2-(2-bromoethoxy)ethoxy)benzene

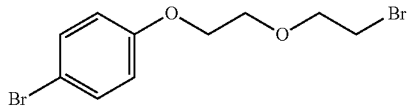 [SMILES: BrCCOCCOc1ccc(Br)cc1]

To a solution of 4-bromophenol (3 g, 17.34 mmol, 1 eq) and 1-bromo-2-(2-bromoethoxy)eth-ane (4.02 g, 17.34 mmol, 1 eq) in N,N-dimethylformamide (10 mL) was added potassium carbonate (4.79 g, 34.68 mmol, 2 eq). The reaction mixture was stirred at 60° C. for 12 h. The reaction mixture was quenched by addition water (10 mL), and then diluted with water (20 mL) and extracted with ethyl acetate (40 mL×3). The combined organic layers were washed with brine (30 mL×2), dried over anhydrous sodium sulfate, filtered and concentrated under reduced pressure to give a residue. The residue was purified by silica gel chromatography (petroleum ether:ethyl acetate=1:0 to 50:1) to give 1-bromo-4-[2-(2-bromoethoxy)ethoxy]benzene (2.8 g, 8.64 mmol, 49% yield) as colorless oil. $^1$H-NMR (400 MHz, $CDCl_3$) δ 7.43-7.34 (m, 2H), 6.86-6.77 (m, 2H), 4.17-4.08 (m, 2H), 3.94-3.87 (m, 4H), 3.50 (t, J=6.2 Hz, 2H).

Step 2: Preparation of methyl 4-(2-(4-bromophenoxy)ethoxy)-2-(3-methylisoxazol-5-yl)butanoate

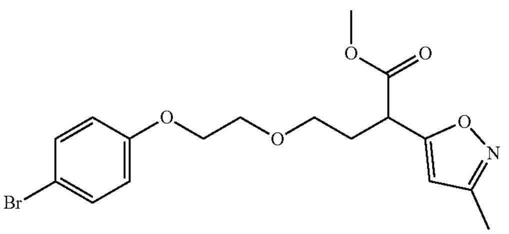 [SMILES: COC(=O)C(CCOCCOc1ccc(Br)cc1)c1cc(C)no1]

To a solution of methyl 2-(3-methylisoxazol-5-yl)acetate (239 mg, 1.54 mmol, 1 eq) in N,N-dimethylformamide (5 mL) was added postassium tert-butoxide (190 mg, 1.70 mmol, 1.1 eq) and potassium iodide (25 mg, 0.15 mmol, 0.1 eq). Then 1-bromo-4-[2-(2-bromoethoxy)ethox-y]benzene (500 mg, 1.54 mmol, 1 eq) was added. The mixture was stirred at 40° C. for 2 hr. The mixture was diluted with saturated ammonia hydrochloride (20 mL) and extracted with ethyl acetate (20 mL×3), The combined organic phase was washed with saturated brine (30 mL), dried over sodium sulfate, filtered and concentrated. The residue was purified by silica gel chromatography (petroleum ether:ethyl acetate=1:0 to 15:1) to give methyl 4-[2-(4-bromophenoxy) ethoxy]-2-(3-methylisoxazol-5-yl)butanoate (125 mg, crude) as a colorless oil. $^1$H-NMR (400 MHz, $CDCl_3$) δ 7.42-7.32 (m, 2H), 6.84-6.76 (m, 2H), 6.01 (s, 1H), 4.10-4.03 (m, 3H), 3.79-3.69 (m, 5H), 3.63-3.56 (m, 1H), 3.52-3.44 (m, 1H), 2.46-2.32 (m, 1H), 2.27 (s, 3H), 2.21-2.11 (m, 1H).

Step 3: Preparation of methyl 4-(2-(4-(3-(2,6-difluoro-3-(((R)-3-fluoro-N-((2-(trimethylsilyl)ethoxy) methyl)pyrrolidine)-1-sulfonamido)benzoyl)-1-((2-(trimethylsilyl)ethoxy)methyl)-1H-pyrrolo[2,3-b] pyridin-5-yl)phenoxy)ethoxy)-2-(3-methylisoxazol-5-yl)butanoate

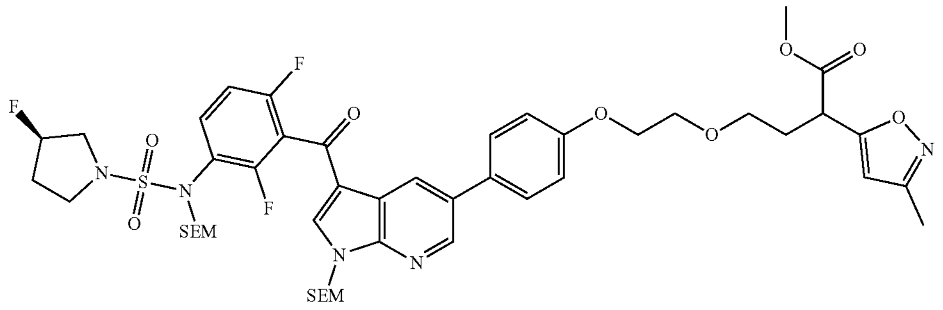 [SMILES: COC(=O)C(CCOCCOc1ccc(-c2cnc3c(c2)c(C(=O)c2c(F)ccc(N(COCC[Si](C)(C)C)S(=O)(=O)N4CC[C@@H](F)C4)c2F)cn3COCC[Si](C)(C)C)cc1)c1cc(C)no1]

A mixture of methyl 4-[2-(4-bromophenoxy)ethoxy]-2-(3-methylisoxazol-5-yl)butanoate (125 mg, 0.31 mmol, 1 eq), (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (305 mg, 0.37 mmol, 1.2 eq), CsF (190 mg, 1.26 mmol, 0.05 uL, 4 eq), 4-ditert-butylphosphanyl-N,N-dimethyl-aniline;dichloro-palladium (22 mg, 0.03 mmol, 0.02 mL, 0.1 eq) in dioxane (10 mL) and water (2 mL) was degassed and purged with nitrogen (3 times), and then the mixture was stirred at 120° C. for 1 hr under nitrogen atmosphere. The reaction mixture diluted with water (20 mL) and extracted with ethyl acetate (40 mL×3). The combined organic layers were washed with brine (30 mL×2), dried over anhydrous sodium sulfate, filtered and concentrated under reduced pressure to give a residue. The residue was purified by pre-TLC (petroleum ether:ethyl acetate=1:1) to give methyl 4-[2-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy] ethoxy]-2-(3-methylisoxazol-5-yl)butanoate (130 mg, 0.12 mmol, 40% yield, 98% purity) as a colorless oil. $^1$H-NMR (400 MHz, $CDCl_3$) δ 8.84 (d, J=1.6 Hz, 1H), 8.65 (d, J=2.2 Hz, 1H), 7.79-7.68 (m, 2H), 7.62 (d, J=8.8 Hz, 2H), 7.12-6.91 (m, 3H), 6.04 (s, 1H), 5.33-5.28 (m, 1H), 4.22-4.06 (m, 4H), 3.84-3.40 (m, 16H), 2.27 (s, 3H), 2.24-2.12 (m, 2H), 1.65 (s, 3H), 1.53 (s, 1H), 1.00-0.89 (m, 4H), 0.03 (s, 9H), −0.05 (s, 9H).

Step 4: Preparation of methyl 4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)-2-(3-methylisoxazol-5-yl)butanoate

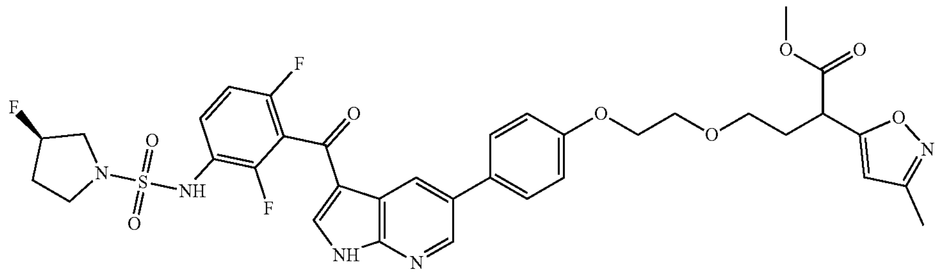 [SMILES: COC(=O)C(CCOCCOc1ccc(-c2cnc3[nH]cc(C(=O)c4c(F)ccc(NS(=O)(=O)N5CC[C@@H](F)C5)c4F)c3c2)cc1)c1cc(C)no1]

To a solution of methyl 4-[2-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]ethoxy]-2-(3-methylisoxazol-5-yl)butanoate (120 mg, 0.12 mmol, 1 eq) in methanol (1 mL) was added hydrogen chloride/dioxane (4 M, 4 mL, 133.63 eq). The mixture was stirred at 40° C. for 24 hr. The reaction mixture was concentrated under reduced pressure to give methyl 4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]-2-(3-methylisoxazol-5-yl)butanoate (130 mg, crude, hydrogen chloride) as a colorless liquid, which was used into the next step without further purification.

Step 5: Preparation of 4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)-2-(3-methylisoxazol-5-yl)butanoic acid

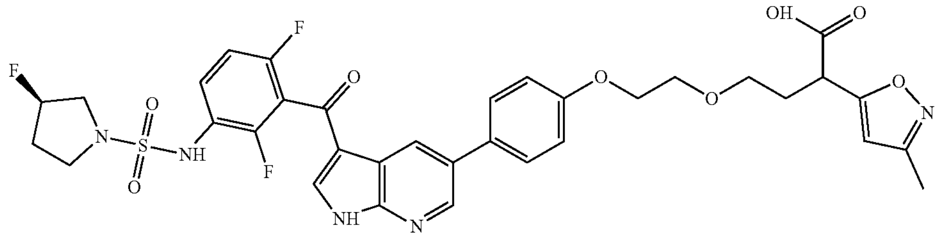 [SMILES: Cc1cc(C(CCOCCOc2ccc(-c3cnc4[nH]cc(C(=O)c5c(F)ccc(NS(=O)(=O)N6CC[C@@H](F)C6)c5F)c4c3)cc2)C(=O)O)on1]

To a solution of methyl 4-[2-[4-[3-[2,6-difluoro-3-[[(3R)-3-fluoropyrrolidin-1-yl]sulfonylam-ino]benzoyl]-1H-pyrrolo[2,3-b]pyridin-5-yl]phenoxy]ethoxy]-2-(3-methylisoxazol-5-yl)butanoate (130 mg, 0.17 mmol, 1 eq) in water (2 mL) and methanol (2 mL) was added lithium hydroxide (80 mg, 1.91 mmol, 10.88 eq). The mixture was stirred at 20° C. for 0.5 hr. The mixture solution was adjusted to PH(5) with hydrogen chloride (1 M), and extracted with ethyl acetate (10 mL×2), dried over anhydrous sodium sulfate, filtered and concentrated under reduced pressure to give 4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]-2-(3-methylisoxazol-5-yl)butanoic acid (50 mg, crude) as a colorless oil, which was used into the next step without further purification.

Step 6: Preparation of (2S,4R)-1-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide

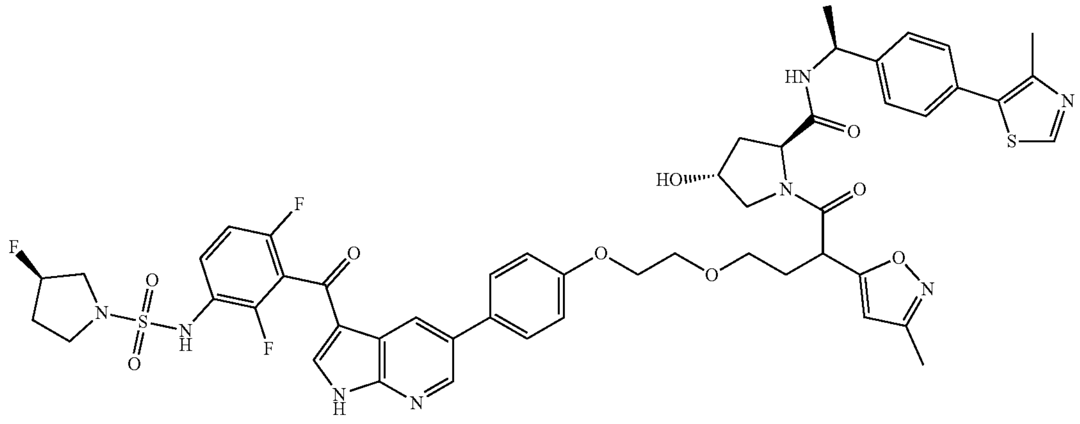 [SMILES: Cc1cc(C(CCOCCOc2ccc(-c3cnc4[nH]cc(C(=O)c5c(F)ccc(NS(=O)(=O)N6CC[C@@H](F)C6)c5F)c4c3)cc2)C(=O)N2C[C@H](O)C[C@H]2C(=O)N[C@@H](C)c2ccc(-c3scnc3C)cc2)on1]

To a solution of (2S,4R)-4-hydroxy-N-[(1S)-1-[4-(4-methylthiazol-5-yl)phenyl]ethyl]py-rrolidine-2-carboxamide (25 mg, 0.07 mmol, 1 eq, hydrogen chloride) in N,N-dimethylformamide (1 mL) was added N,N-diisopropylethylamine (26 mg, 0.21 mmol, 3 eq). The mixture was stirred at 20° C. for 10 min. Then 4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]-2-(3-methylisoxazol-5-yl)butanoic acid (50 mg, 0.07 mmol, 1 eq) and 1-hydroxybenzotriazole (11 mg, 0.08 mmol, 1.2 eq) was added, the mixture was stirred at 20° C. for 10 min. Then N-(3-dimethylamino-propyl)-N-ethyl-carbodiimide hydrochloride (16 mg, 0.08 mmol, 1.2 eq) was added. The mixture was stirred at 20° C. for 2 h 40 min. The mixture was quenched with water (5 mL), extracted with (dichloromethane:methanol=10:1) (10 mL×2), washed with brine (20 mL), dried over anhydrous sodium sulfate, filtered and then concentrated. The residue was purified by prep-HPLC to give (2S,4R)-1-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (11.9 mg, 0.01 umol, 16% yield, 100% purity) as an off-white solid. LC/MS (ESI) m/z: 521.3 $[M/2+1]^+$; $^1$H-NMR (400 MHz, DMSO-cL) S 9.01-8.91 (m, 1H), 8.64 (dd, J=2.2, 13.6 Hz, 1H), 8.55 (s, 1H), 8.47-8.35 (m, 1H), 8.06 (s, 1H), 7.67 (d, J=8.6 Hz, 1H), 7.64-7.55 (m, 2H), 7.46-7.32 (m, 5H), 7.19 (t, J=8.4 Hz, 1H), 7.08 (dd, J=8.8, 18.2 Hz, 2H), 6.32-6.21 (m, 1H), 5.41-5.06 (m, 2H), 4.99-4.85 (m, 1H), 4.50-4.35 (m, 1H), 4.32-4.14 (m, 4H), 3.76 (d, J=4.6 Hz, 3H), 3.57-3.41 (m, 5H), 2.47-2.39 (m, 4H), 2.18 (d, J=6.4 Hz, 4H), 2.12-1.94 (m, 5H), 1.84-1.64 (m, 1H), 1.42-1.32 (m, 4H), 1.23 (s, 1H).

Exemplary Synthesis of (2S,4R)-1-((S)-4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide (Example 461) and (2S,4R)-1-((R)-4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide (Example 4621

Step 1: Preparation of 2-(2-(2-hydroxyethoxy)ethoxy)ethyl 4-methylbenzenesulfonate

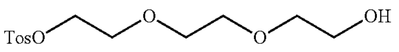

To a mixture of 2-[2-(2-hydroxyethoxy)ethoxy]ethanol (5.00 g, 33.29 mmol, 1.00 eq) and 4-methylbenzenesulfonyl chloride (1.59 g, 8.32 mmol, 0.25 eq) in dichloromethane (50 mL) was added triethylamine (1.68 g, 16.65 mmol, 2.3 mL, 0.5 eq) in one portion at 25° C. under nitrogen. The mixture was stirred at 25° C. for 12 h. The mixture was washed with brine (30 mL×2), dried with anhydrous sodium sulfate, filtered and concentrated in vacuum. The residue was purified by silica gel chromatography (Petroleum ether/Ethyl acetate=1/1 to 0:1) to afford 2-[2-(2-hydroxyethoxy)ethoxy]ethyl 4-methylbenzenesulfonate (1.72 g, 5.65 mmol, 17% yield) as a colorless oil. LC/MS (ESI) m/z: 327.0 $[M+23]^+$; $^1$H-NMR (400 MHz, $CDCl_3$) δ 7.81 (d, J=8.3 Hz, 2H), 7.35 (d, J=8.0 Hz, 2H), 4.22-4.15 (m, 2H), 3.79-3.67 (m, 4H), 3.67-3.56 (m, 6H), 2.46 (s, 3H).

Step 2: Preparation of 2-(2-(2-(4-bromophenoxy) ethoxy)ethoxy)ethan-1-ol

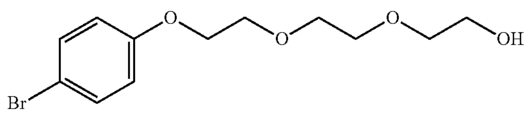 [SMILES: OCCOCCOCCOc1ccc(Br)cc1]

To a solution of 2-[2-(2-hydroxyethoxy)ethoxy]ethyl 4-methylbenzenesulfonate (2 g, 6.57 mmol, 1 eq) and 4-bromophenol (1.36 g, 7.89 mmol, 1.2 eq) in N,N-dimethylformamide (10 mL) was added potassium carbonate (1.82 g, 13.14 mmol, 2 eq). The reaction mixture was stirred at 60° C. for 12 h. The reaction mixture was quenched by addition water (20 mL), and then diluted with water (30 mL), filtered and extracted with ethyl acetate (40 mL×3). The combined organic layers were washed with brine (80 mL), dried over anhydrous sodium sulfate, filtered and concentrated under reduced pressure to give a residue. The residue was purified by silica gel chromatography (petroleum ether:ethyl acetate=20:1 to 3:1). The desired compound 2-[2-[2-(4-bromophenoxy)ethoxy]ethoxy]ethanol (1.09 g, 3.57 mmol, 54% yield) was obtained as colorless oil. $^1$H NMR (400 MHz, $CDCl_3$) δ 7.44-7.33 (m, 2H), 6.81 (d, J=8.8 Hz, 2H), 4.18-4.06 (m, 2H), 3.92-3.83 (m, 2H), 3.79-3.67 (m, 6H), 3.65-3.60 (m, 2H).

Step 3: Preparation of 1-bromo-4-(2-(2-(2-bromoethoxy)ethoxy)ethoxy)benzene

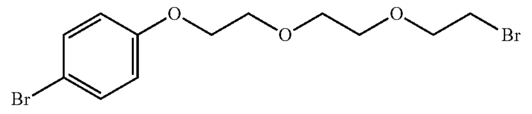 [SMILES: BrCCOCCOCCOc1ccc(Br)cc1]

To a solution of 2-[2-[2-(4-bromophenoxy)ethoxy] ethoxy]ethanol (1.09 g, 3.57 mmol, 1 eq) and triphenylphosphine (1.41 g, 5.36 mmol, 1.5 eq) in tetrahydrofuran (10 mL) was added perbromomethane (1.78 g, 5.36 mmol, 1.5 eq). The reaction mixture was stirred at 20° C. for 1 h. The reaction mixture was concentrated under reduced pressure to give a residue. The residue was purified by silica gel chromatography (petroleum ether:ethyl acetate=50:1 to 10:1). The desired compound 1-bromo-4-[2-[2-(2-bromoethoxy)ethoxy]ethoxy]benzene (1.2 g, 3.26 mmol, 91% yield) was obtained as light yellow oil. $^1$H-NMR (400 MHz, $CDCl_3$) δ 7.43-7.31 (m, 2H), 6.86-6.70 (m, 2H), 4.16-4.06 (m, 2H), 3.92-3.79 (m, 4H), 3.76-3.66 (m, 4H), 3.48 (t, J=6.4 Hz, 2H).

Step 4: Preparation of methyl 4-(2-(2-(4-bromophenoxy)ethoxy)ethoxy)-2-(3-methylisoxazol-5-yl)butanoate

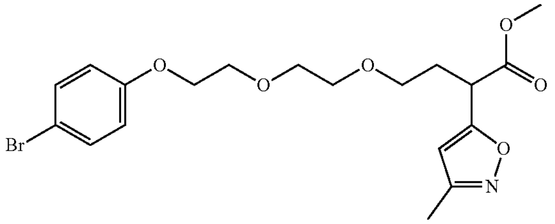 [SMILES: COC(=O)C(CCOCCOCCOc1ccc(Br)cc1)c1cc(C)no1]

To a solution of methyl 2-(3-methylisoxazol-5-yl)acetate (211 mg, 1.36 mmol, 1 eq) and potassium iodide (23 mg, 0.14 mmol, 0.1 eq) in N,N-dimethylformamide (5 mL) was added potassium tert-butoxide (183 mg, 1.63 mmol, 1.2 eq) and 1-bromo-4-[2-[2-(2-bromoethoxy)ethoxy]ethoxy]benzene (500 mg, 1.36 mmol, 1 eq). The reaction mixture was stirred at 40° C. for 2 h. The reaction mixture was quenched by addition water (10 mL), and then diluted with water (20 mL), filtered and extracted with ethyl acetate (30 mL×3). The combined organic layers were washed with brine (50 mL), dried over anhydrous sodium sulfate, filtered and concentrated under reduced pressure to give a residue. The residue was purified by silica gel chromatography (petroleum ether:ethyl acetate=20:1 to 3:1). The desired compound methyl 4-[2-[2-(4-bromophenoxy)ethoxy]ethoxy]-2-(3-methylisoxazol-5-yl)butanoate (250 mg, 0.57 mmol, 41% yield) was obtained as colorless oil. $^1$H-NMR (400 MHz, $CDCl_3$) δ 7.44-7.32 (m, 2H), 6.87-6.77 (m, 2H), 6.03 (s, 1H), 4.16-4.08 (m, 3H), 3.87-3.82 (m, 2H), 3.72 (s, 3H), 3.70-3.67 (m, 2H), 3.64-3.50 (m, 3H), 3.48-3.38 (m, 1H), 2.42-2.31 (m, 1H), 2.28 (s, 3H), 2.20-2.09 (m, 1H).

Step 5: Preparation of methyl 4-(2-(2-(4-(3-(2,6-difluoro-3-(((R)-3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenoxy)ethoxy)ethoxy)-2-(3-methylisoxazol-5-yl)butanoate

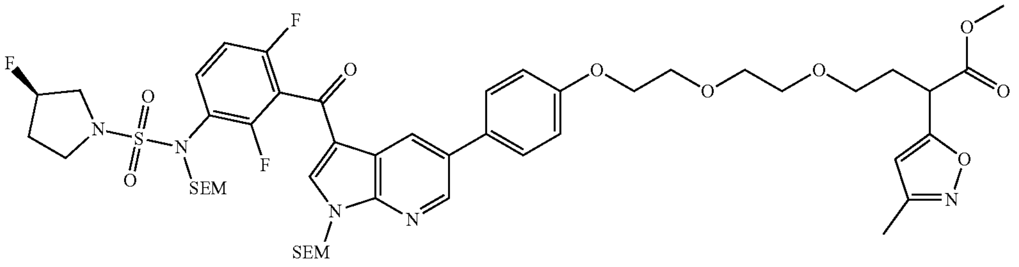 [SMILES: COC(=O)C(CCOCCOCCOc1ccc(-c2cnc3c(c2)c(C(=O)c2c(F)ccc(N(COCC[Si](C)(C)C)S(=O)(=O)N4CC[C@@H](F)C4)c2F)cn3COCC[Si](C)(C)C)cc1)c1cc(C)no1]

To a solution of methyl 4-[2-[2-(4-bromophenoxy)ethoxy]ethoxy]-2-(3-methylisoxazol-5-yl)butanoate (180 mg, 0.41 mmol, 1 eq) and (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (330 mg, 0.41 mmol, 1 eq) in dioxane (10 mL) and water (2 mL) was added 4-ditert-butylphosphanyl-N,N-dimethyl-aniline;dichloropalladium (29 mg, 0.04 mmol, 0.1 eq) and cesium fluoride (247 mg, 1.63 mmol, 4 eq). The reaction mixture was stirred at 120° C. for 1 h. The reaction mixture was quenched by addition water (10 mL), and then diluted with water (20 mL), filtered and extracted with ethyl acetate (30 mL×3). The combined organic layers were washed with brine (50 mL), dried over anhydrous sodium sulfate, filtered and concentrated under reduced pressure to give a residue. The residue was purified by prep-TLC (petroleum ether:ethyl acetate=1:1). The desired compound methyl 4-[2-[2-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]ethoxy]ethoxy]-2-(3-methylisoxazol-5-yl)butanoate (160 mg, 0.14 mmol, 35% yield, 92% purity) was obtained as light yellow oil. LC/MS (ESI) m/z: 1046.0 [M+1]+.

Step 6: Preparation of methyl 4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoate

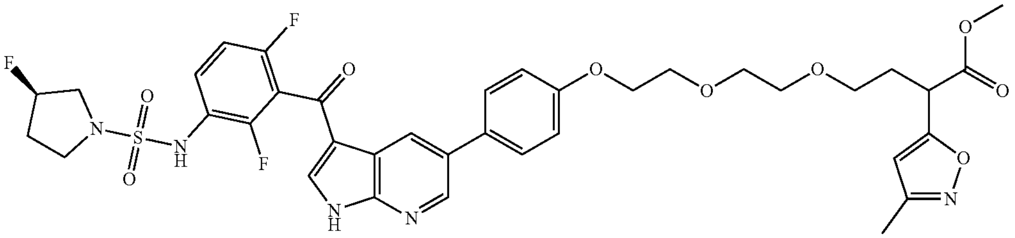 [SMILES: COC(=O)C(CCOCCOCCOc1ccc(-c2cnc3[nH]cc(C(=O)c4c(F)ccc(NS(=O)(=O)N5CC[C@@H](F)C5)c4F)c3c2)cc1)c1cc(C)no1]

To a solution of methyl 4-[2-[2-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]ethoxy]ethoxy]-2-(3-methylisoxazol-5-yl)butanoate (160 mg, 0.15 mmol, 1 eq) in methanol (1 mL) was added hydrogen chloride/dioxane (4 M, 2 mL, 52.32 eq). The reaction mixture was stirred at 40° C. for 2 h. The reaction mixture was concentrated under reduced pressure to give a residue. The product was taken to the next step without purification. The desired compound methyl 4-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]-2-(3-methylisoxazol-5-yl)butanoate (120 mg, crude) was obtained as light yellow oil. LC/MS (ESI) m/z: 786.3 [M+1]+.

Step 7: Preparation of 4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoic acid

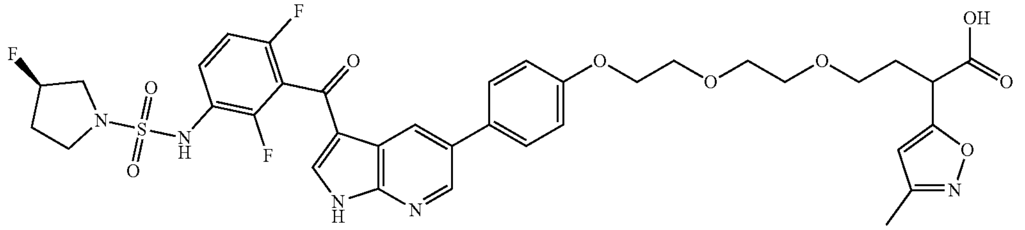 [SMILES: Cc1cc(C(CCOCCOCCOc2ccc(-c3cnc4[nH]cc(C(=O)c5c(F)ccc(NS(=O)(=O)N6CC[C@@H](F)C6)c5F)c4c3)cc2)C(=O)O)on1]

To a solution of methyl 4-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]-2-(3-methylisoxazol-5-yl)butanoate (120 mg, 0.15 mmol, 1 eq) in methanol (4 mL) and water (1 mL) was added lithium hydroxide (26 mg, 0.61 mmol, 4 eq). The reaction mixture was stirred at 20° C. for 1 h. The residue was adjusted to pH=4~5 with 1 M hydrogen chloride, then extracted with ethyl acetate (30 mL×2). The combined organic layers were dried over sodium sulfate, filtered and concentrated under reduced pressure to give a residue. The product was taken to the next step without purification. The desired compound 4-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]-2-(3-methylisoxazol-5-yl)butanoic acid (110 mg, crude) was obtained as light yellow oil.

Step 8: Preparation of (2S,4R)-1-((S)-4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide and (2S,4R)-1-((R)-4-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide

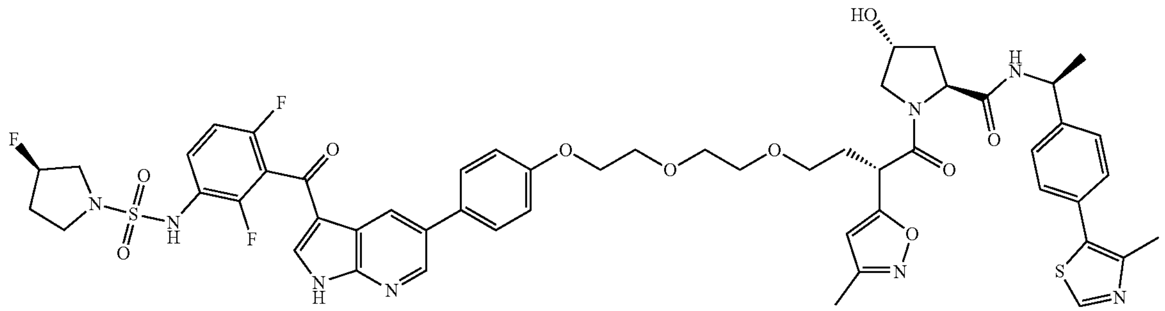

+

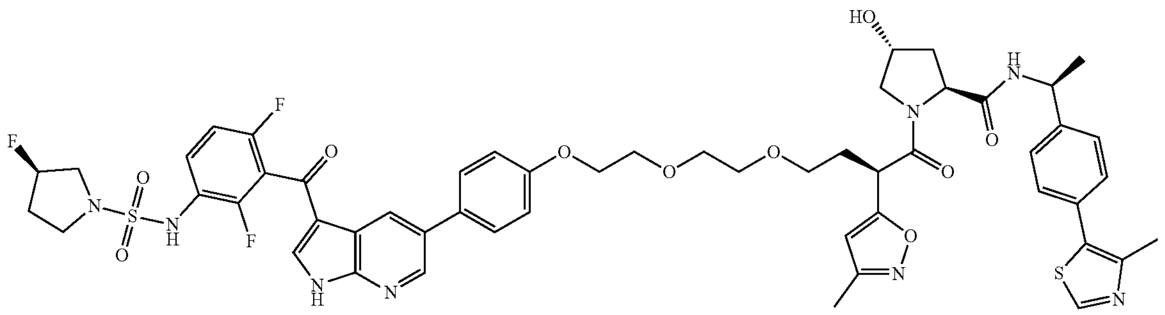

To a solution of 4-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]-2-(3-methylisoxazol-5-yl)butanoic acid (110 mg, 0.14 mmol, 1 eq) and (2S,4R)-4-hydroxy-N-[(1S)-1-[4-(4-methylthiazol-5-yl)phenyl]ethyl]pyrrolidine-2-carboxamide (52 mg, 0.14 mmol, 1 eq, HCl) in N,N-dimethylformamide (1 mL) was added N,N-diisopropylethylamine (55 mg, 0.43 mmol, 3 eq) and hydroxybenzotriazole (23 mg, 0.17 mmol, 1.2 eq). The mixture was stirred at 20° C. for 0.15 h, then 1-(3-dimethylaminopropyl)-3-ethylcarbodiimide hydrochloride (33 mg, 0.17 mmol, 1.2 eq) was added to the mixture. The reaction mixture was stirred at 20° C. for 1 h. The reaction mixture was quenched by addition water (10 mL), and then diluted with water (20 mL) and extracted with ethyl acetate (20 mL×3). The combined organic layers were dried over anhydrous sodium sulfate, filtered and concentrated under reduced pressure to give a residue. The residue was purified by prep-TLC (dichloromethane:methanol=10:1). The desired compounds were obtained as white solids. Product 1, (2S,4R)-1-[(2S)-4-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (22.7 mg, 0.021 mmol, 29% yield, 100% purity). LC/MS (ESI) m/z: 543.2 $[M/2+1]^+$; $^1$H NMR (400 MHz, DMSO-$d_6$) δ 12.93 (s, 1H), 9.84 (s, 1H), 8.96 (s, 1H), 8.72-8.52 (m, 2H), 8.41 (d, J=7.6 Hz, 1H), 8.08 (s, 1H), 7.71-7.54 (m, 3H), 7.48-7.31 (m, 4H), 7.26 (t, J=8.8 Hz, 1H), 7.07 (d, J=8.8 Hz, 2H), 6.26-6.01 (m, 1H), 5.41-5.20 (m, 1H), 5.15-5.02 (m, 1H), 5.00-4.86 (m, 1H), 4.40 (t, J=7.6 Hz, 1H), 4.33-4.08 (m, 4H), 3.84-3.34 (m, 13H), 2.45-2.40 (m, 3H), 2.23-1.93 (m, 6H), 1.88-1.71 (m, 1H), 1.38 (d, J=6.8 Hz, 3H). Product 2, (2S,4R)-1-[(2R)-4-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (14.7 mg, 0.013 mmol, 18% yield, 99% purity). LC/MS (ESI) m/z: 543.2 $[M/2+1]^+$; $^1$H-NMR (400 MHz, DMSO-$d_6$) δ 12.92 (s, 1H), 9.84 (s, 1H), 9.03-8.92 (m, 1H), 8.69-8.49 (m, 2H), 8.35 (d, J=7.6 Hz, 1H), 8.08 (s, 1H), 7.77-7.53 (m, 3H), 7.47-7.20 (m, 5H), 7.09 (d, J=8.4 Hz, 2H), 6.37-6.19 (m, 1H), 5.43-5.20 (m, 1H), 5.12 (d, J=3.2 Hz, 1H), 5.04-4.85 (m, 1H), 4.65-4.38 (m, 1H), 4.34-4.09 (m, 4H), 3.79 (s, 2H), 3.66-3.36 (m, 11H), 2.47-2.38 (m, 3H), 2.24-1.97 (m, 6H), 1.83-1.70 (m, 1H), 1.47-1.29 (m, 3H).

Exemplary Synthesis of (2S,4R)-1-((S)-4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide (Example 463) and (2S,4R)-1-((R)-4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide (Example 464)

Step 1: Preparation of 2-(2-(2-(2-hydroxyethoxy)ethoxy)ethoxy)ethyl 4-methylbenzenesulfonate

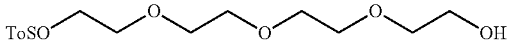

To a mixture of 2-[2-[2-(2-hydroxyethoxy)ethoxy]ethoxy]ethanol (5 g, 25.74 mmol, 4.4 mL, 1 eq) and 4-methylbenzenesulfonyl chloride (1.23 g, 6.44 mmol, 0.25 eq) in dichloromethane (50 mL) was added triethylamine (1.30 g, 12.87 mmol, 1.8 mL, 0.5 eq) in one portion at 25° C. under nitrogen. The mixture was stirred at 25° C. for 12 h. The mixture was washed with brine (30 mL×2), dried with anhydrous sodium sulfate, filtered and concentrated in vacuum. The residue was purified by silica gel chromatography (Petroleum ether/Ethyl acetate=1/1 to 0/1) to afford 2-[2-[2-(2-hydroxyethoxy)ethoxy]ethoxy]ethyl 4-methylbenzenesulfonate (1.98 g, 5.68 mmol, 22% yield) as colorless oil. LC/MS (ESI) m/z: 371.0 $[M+23]^+$; $^1H$ NMR (400 MHz, $CDCl_3$) δ 7.82 (d, J=8.3 Hz, 2H), 7.36 (d, J=8.2 Hz, 2H), 4.21-4.11 (m, 2H), 3.75-3.61 (m, 14H), 2.47 (s, 3H).

Step 2: Preparation of 2-(2-(2-(2-(4-bromophenoxy)ethoxy)ethoxy)ethoxy)ethan-1-ol

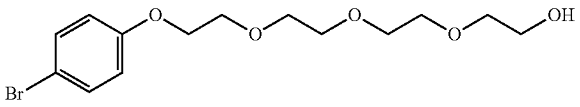 [SMILES: OCCOCCOCCOCCOc1ccc(Br)cc1]

To a solution of 2-[2-[2-(2-hydroxyethoxy)ethoxy]ethoxy]ethyl 4-methylbenzenesulfonate (2 g, 5.74 mmol, 1 eq) and 4-bromophenol (1.09 g, 6.31 mmol, 1.1 eq) in N,N-dimethylformamide (10 mL) was added potassium carbonate (1.59 g, 11.48 mmol, 2 eq). The reaction mixture was stirred at 60° C. for 12 h. The reaction mixture was quenched by addition water (20 mL), and then diluted with water (30 mL), filtered and extracted with ethyl acetate (40 mL×3). The combined organic layers were washed with brine (80 mL), dried over anhydrous sodium sulfate, filtered and concentrated under reduced pressure to give a residue. The residue was purified by silica gel chromatography (petroleum ether:ethyl acetate=20:1 to 3:1). The desired compound 2-[2-[2-[2-(4-bromophenoxy)ethoxy]ethoxy]ethoxy]ethanol (1.34 g, 3.84 mmol, 66% yield) was obtained as colorless oil. LC/MS (ESI) m/z: 351.1 $[M+1]^+$; $^1H$-NMR (400 MHz, $CDCl_3$) δ 7.44-7.33 (m, 2H), 6.87-6.75 (m, 2H), 4.17-4.07 (m, 2H), 3.91-3.81 (m, 2H), 3.79-3.57 (m, 12H).

Step 3: Preparation of 1-bromo-4-(2-(2-(2-(2-bromoethoxy)ethoxy)ethoxy)ethoxy)benzene

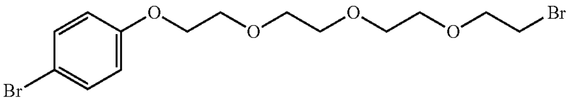 [SMILES: BrCCOCCOCCOCCOc1ccc(Br)cc1]

To a solution of 2-[2-[2-[2-(4-bromophenoxy)ethoxy]ethoxy]ethoxy]ethanol (1.34 g, 3.84 mmol, 1 eq) in tetrahydrofuran (10 mL) was added perbromomethane (1.91 g, 5.76 mmol, 1.5 eq) and triphenylphosphine (1.51 g, 5.76 mmol, 1.5 eq). The reaction mixture was stirred at 20° C. for 1 h. The reaction mixture was quenched by addition water (10 mL), and then diluted with water (20 mL) and extracted with ethyl acetate (40 mL×3). The combined organic layers were washed with brine (30 mL×2), dried over anhydrous sodium sulfate, filtered and concentrated under reduced pressure to give a residue. The residue was purified by silica gel chromatography (petroleum ether:ethyl acetate=50:1 to 10:1). The desired compound 1-bromo-4-[2-[2-[2-(2-bromoethoxy)ethoxy]ethoxy]ethoxy]benzene (1.1 g, 2.67 mmol, 69% yield) was obtained as colorless oil. $^1H$ NMR (400 MHz, $CDCl_3$) δ 7.42-7.33 (m, 2H), 6.87-6.73 (m, 2H), 4.14-4.07 (m, 2H), 3.91-3.77 (m, 4H), 3.76-3.66 (m, 8H), 3.47 (t, J=6.4 Hz, 2H).

Step 4: Preparation of methyl 4-(2-(2-(2-(4-bromophenoxy)ethoxy)ethoxy)ethoxy)-2-(3-methylisoxazol-5-yl)butanoate

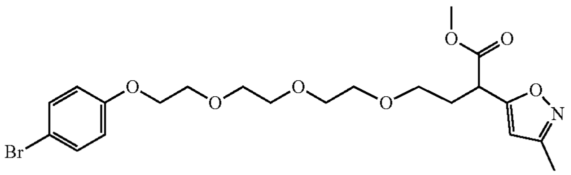 [SMILES: COC(=O)C(CCOCCOCCOCCOc1ccc(Br)cc1)c1cc(C)no1]

To a solution of methyl 2-(3-methylisoxazol-5-yl)acetate (188 mg, 1.21 mmol, 1 eq) in N,N-dimethylformamide (6 mL) was added potassium tert-butoxide (150 mg, 1.33 mmol, 1.1 eq) and potassium iodide (20 mg, 0.12 mmol, 0.1 eq), and then 1-bromo-4-[2-[2-[2-(2-bromoethoxy)ethoxy]ethoxy]ethoxy]benzene (500 mg, 1.21 mmol, 1 eq). The reaction mixture was stirred at 40° C. for 2 h. The reaction mixture was quenched by addition water (10 mL), and then diluted with water (20 mL), filtered and extracted with ethyl acetate (30 mL×3). The combined organic layers were washed with brine (50 mL), dried over anhydrous sodium sulfate, filtered and concentrated under reduced pressure to give a residue. The residue was purified by silica gel chromatography (petroleum ether:ethyl acetate=20:1 to 3:1). The desired compound methyl 4-[2-[2-[2-(4-bromophenoxy)ethoxy]ethoxy]ethoxy]-2-(3-methylisoxazol-5-yl)butanoate (220 mg, 0.45 mmol, 37% yield) was obtained as colorless oil. $^1H$-NMR (400 MHz, $CDCl_3$) δ 7.37 (d, J=8.4 Hz, 2H), 6.80 (d, J=8.8 Hz, 2H), 6.03 (s, 1H), 4.16-4.07 (m, 3H), 3.90-3.81 (m, 2H), 3.76-3.71 (m, 5H), 3.70-3.65 (m, 2H), 3.65-3.60 (m, 2H), 3.58-3.49 (m, 3H), 3.46-3.36 (m, 1H), 2.41-2.31 (m, 1H), 2.30-2.27 (m, 3H), 2.20-2.07 (m, 1H).

Step 5: Preparation of methyl 4-(2-(2-(2-(4-(3-(2,6-difluoro-3-(((R)-3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenoxy)ethoxy)ethoxy)ethoxy)-2-(3-methylisoxazol-5-yl)butanoate

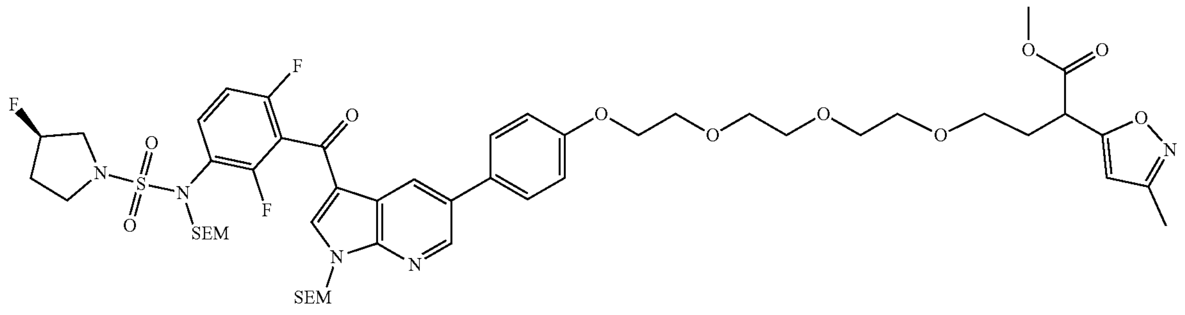 [SMILES: COC(=O)C(CCOCCOCCOCCOc1ccc(-c2cnc3c(c2)c(C(=O)c2c(F)ccc(N(COCC[Si](C)(C)C)S(=O)(=O)N4CC[C@@H](F)C4)c2F)cn3COCC[Si](C)(C)C)cc1)c1cc(C)no1]

To a solution of methyl 4-[2-[2-[2-(4-bromophenoxy)ethoxy]ethoxy]ethoxy]-2-(3-methylisoxazol-5-yl)butanoate (220 mg, 0.45 mmol, 1 eq) and (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (367 mg, 0.45 mmol, 1 eq) in dioxane (10 mL) and water (2 mL) was added cesium fluoride (275 mg, 1.81 mmol, 4 eq) and 4-ditert-butylphosphanyl-N,N-dimethyl-aniline;dichloropalladium (32 mg, 0.04 umol, 0.1 eq). The reaction mixture was stirred at 100° C. for 12 h. The reaction mixture was quenched by addition water (10 mL), and then diluted with water (20 mL), filtered and extracted with ethyl acetate (30 mL×3). The combined organic layers were washed with brine (50 mL), dried over anhydrous sodium sulfate, filtered and concentrated under reduced pressure to give a residue. The residue was purified by prep-TLC (Petroleum ether:Ethyl acetate=1:1). The desired compound methyl 4-[2-[2-[2-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]ethoxy]ethoxy]ethoxy]-2-(3-methylisoxazol-5-yl)butanoate (270 mg, 0.23 mmol, 51% yield, 94% purity) was obtained as light yellow oil. LC/MS (ESI) m/z: 546.2 $[M/2+1]^+$; $^1$H-NMR (400 MHz, $CDCl_3$) δ 8.84 (d, J=1.6 Hz, 1H), 8.65 (d, J=2.0 Hz, 1H), 7.83-7.68 (m, 2H), 7.61 (d, J=8.8 Hz, 2H), 7.16-7.01 (m, 3H), 6.04 (s, 1H), 5.70 (s, 2H), 5.33-5.13 (m, 1H), 5.07-4.93 (m, 2H), 4.26-4.18 (m, 2H), 3.98-3.88 (m, 2H), 3.81-3.37 (m, 22H), 2.46-2.32 (m, 1H), 2.31-2.09 (m, 6H), 1.31-1.19 (m, 4H), 0.03 (s, 9H), −0.05 (s, 9H).

Step 6: Preparation of methyl 4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoate

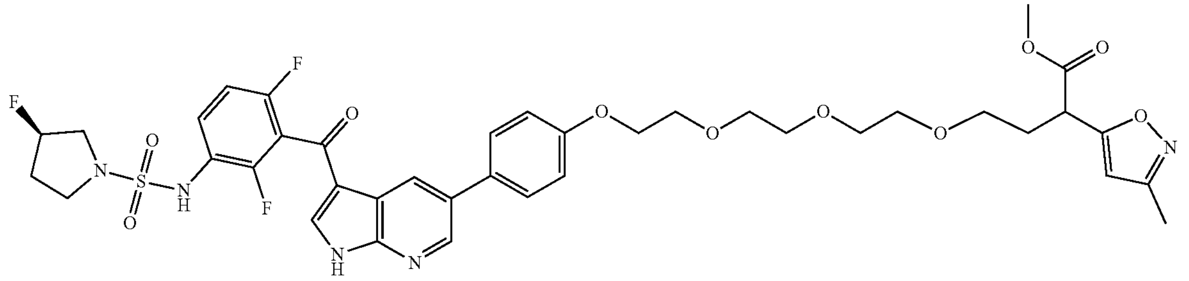 [SMILES: COC(=O)C(CCOCCOCCOCCOc1ccc(-c2cnc3[nH]cc(C(=O)c4c(F)ccc(NS(=O)(=O)N5CC[C@@H](F)C5)c4F)c3c2)cc1)c1cc(C)no1]

To a solution of methyl 4-[2-[2-[2-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenoxy]ethoxy]ethoxy]ethoxy]-2-(3-methylisoxazol-5-yl)butanoate (270 mg, 0.25 mmol, 1 eq) in methanol (2 mL) was added hydrogen chloride/dioxane (4 M, 2 mL, 32.31 eq). The reaction mixture was stirred at 40° C. for 12 h. The reaction mixture was concentrated under reduced pressure to give a residue. The product was taken to the next step without purification. The desired compound methyl 4-[2-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]ethoxy]-2-(3-methylisoxazol-5-yl)butanoate (250 mg, crude) was obtained as light yellow oil. LC/MS (ESI) m/z: 830.1 $[M+1]^+$.

Step 7: Preparation of 4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoic acid

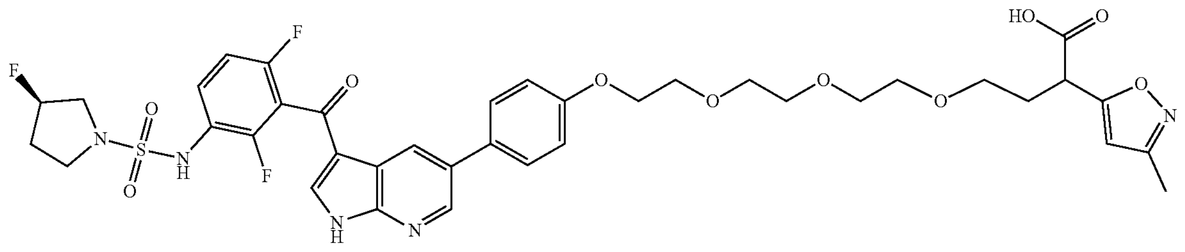 [SMILES: Cc1cc(C(CCOCCOCCOCCOc2ccc(-c3cnc4[nH]cc(C(=O)c5c(F)ccc(NS(=O)(=O)N6CC[C@@H](F)C6)c5F)c4c3)cc2)C(=O)O)on1]

To a solution of methyl 4-[2-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]ethoxy]-2-(3-methylisoxazol-5-yl)butanoate (250 mg, 0.3 mmol, 1 eq) in tetrahydrofuran (10 mL) and water (2 mL) was added lithium hydroxide (51 mg, 1.21 mmol, 4 eq). The reaction mixture was stirred at 20° C. for 1 h. The residue was adjusted to pH=4~5 with 1 M hydrogen chloride, then extracted with ethyl acetate (30 mL×2). The combined organic layers were dried over sodium sulfate, filtered and concentrated under reduced pressure to give a residue. The product was taken to the next step without purification. The desired compound 4-[2-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]ethoxy]-2-(3-methylisoxazol-5-yl)butanoic acid (200 mg, crude) was obtained as light yellow solid. LC/MS (ESI) m/z: 816.0 $[M+1]^+$.

Step 8: Preparation of (2S,4R)-1-((S)-4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide and (2S,4R)-1-((R)-4-(2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)ethoxy)ethoxy)-2-(3-methylisoxazol-5-yl)butanoyl)-4-hydroxy-N—((S)-1-(4-(4-methylthiazol-5-yl)phenyl)ethyl)pyrrolidine-2-carboxamide

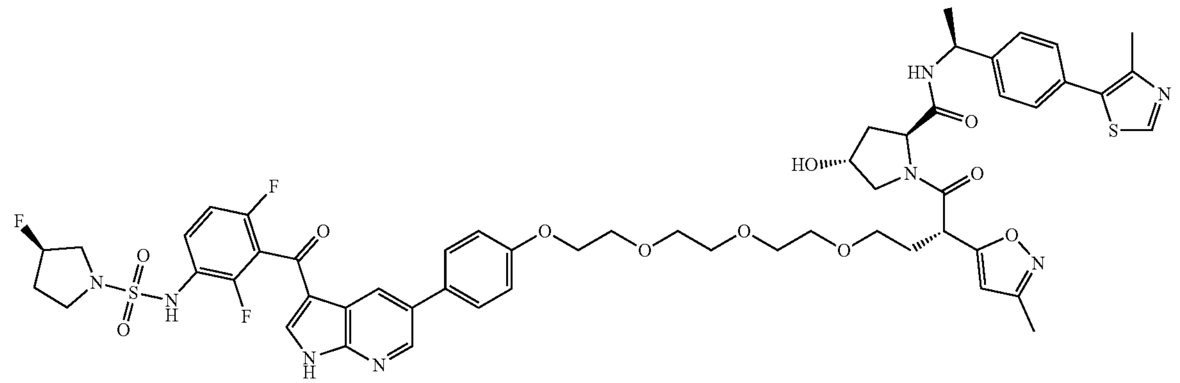

+

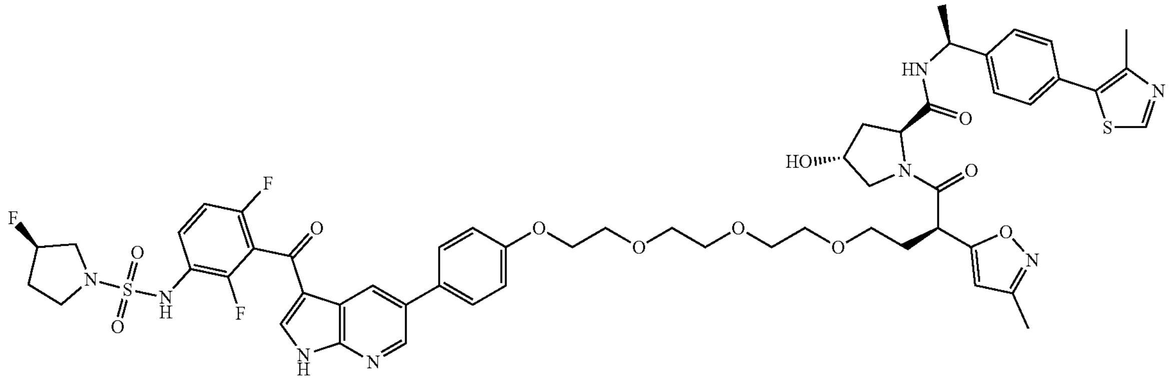

To a solution of 4-[2-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]ethoxy]-2-(3-methylisoxazol-5-yl)butanoic acid (100 mg, 0.12 mmol, 1 eq) and (2S,4R)-4-hydroxy-N-[(1S)-1-[4-(4-methylthiazol-5-yl)phenyl]ethyl]pyrrolidine-2-carboxamide (45 mg, 0.12 mmol, 1 eq, HCl) in N,N-dimethylformamide (2 mL) was added N,N-diisopropylethylamine (48 mg, 0.37 mmol, 3 eq) and hydroxybenzotriazole (20 mg, 0.15 mmol, 1.2 eq). The mixture was stirred at 20° C. for 0.25 h, 1-(3-dimethylaminopropyl)-3-ethylcarbodiimide hydrochloride (28 mg, 0.15 mmol, 1.2 eq) was added to the mixture. The reaction mixture was stirred at 20° C. for 1.25 h. The reaction mixture was quenched by addition water (10 mL), and then diluted with water (20 mL) and extracted with ethyl acetate (20 mL×3). The combined organic layers were dried over anhydrous sodium sulfate, filtered and concentrated under reduced pressure to give a residue. The residue was purified by prep-HPLC (basic condition). Then the residue was purified by prep-TLC (dichloromethane:methanol=10:1). The desired compounds were obtained as white solids. Product 1, (2S,4R)-1-[(2S)-4-[2-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (16.97 mg, 0.014 mmol, 24% yield, 99% purity). LC/MS (ESI) m/z: 562.4 $[M/2+1]^+$; $^1$H-NMR (400 MHz, DMSO-$d_6$) δ 8.96 (s, 1H), 8.71-8.52 (m, 2H), 8.43 (s, 1H), 8.08 (s, 1H), 7.64 (s, 3H), 7.49-7.19 (m, 6H), 7.08 (s, 2H), 6.34-6.04 (m, 1H), 5.41-4.81 (m, 3H), 4.45-4.07 (m, 4H), 3.77 (s, 2H), 3.62-3.50 (m, 12H), 2.43 (s, 3H), 2.28-1.91 (m, 10H), 1.81 (s, 1H), 1.37 (s, 4H). Product 2, (2S,4R)-1-[(2R)-4-[2-[2-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenoxy]ethoxy]ethoxy]ethoxy]-2-(3-methylisoxazol-5-yl)butanoyl]-4-hydroxy-N-[(1S)-1-[4-(4-methylthiazol-5-yl)phenyl]ethyl]pyrrolidine-2-carboxamide (15.25 mg, 0.013 mmol, 22% yield, 100% purity). LC/MS (ESI) m/z: 562.4 $[M/2+1]^+$; $^1$H-NMR (400 MHz, DMSO-$d_6$) δ 12.93 (s, 1H), 9.86 (s, 1H), 9.08-8.91 (m, 1H), 8.73-8.53 (m, 2H), 8.36 (d, J=8.0 Hz, 1H), 8.08 (s, 1H), 7.73-7.55 (m, 3H), 7.50-7.22 (m, 5H), 7.15-7.03 (m, 2H), 6.36-6.20 (m, 1H), 5.41-5.18 (m, 2H), 5.12 (d, J=3.6 Hz, 1H), 5.05-4.84 (m, 1H), 4.69-4.38 (m, 3H), 4.32-4.12 (m, 4H), 3.79 (d, J=4.8 Hz, 2H), 3.68-3.37 (m, 9H), 2.44 (s, 3H), 2.36-1.85 (m, 8H), 1.84-1.68 (m, 1H), 1.48-1.17 (m, 4H).

Exemplary Synthesis of (2S,4R)-1-(4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N—((S)-1-(4-(4-methylthiazol-5-yl)phenyl)ethyl)pyrrolidine-2-carboxamide (Example 477)

Step 1: Preparation of 1-(tert-butyl) 4-methyl 2,2-dimethyl-3-(3-methylisoxazol-5-yl)succinate

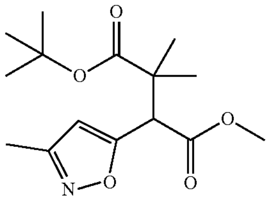 [SMILES: COC(=O)C(c1cc(C)no1)C(C)(C)C(=O)OC(C)(C)C]

To a solution of methyl 2-(3-methylisoxazol-5-yl)acetate (4 g, 25.78 mmol, 1 eq) and tert-butyl 2-bromo-2-methylpropanoate (11.50 g, 51.56 mmol, 2 eq) in N,N-dimethylformamide (30 mL) was added potassium tert-butoxide (4.34 g, 38.67 mmol, 1.5 eq), the mixture was stirred at 50° C. for 2 h. The mixture was diluted with water (100 mL) and extracted with ethyl acetate (100 mL, twice), the organic phase was dried by anhydrous sodium sulfate, filtered and the filtrate was concentrated to give crude product. This crude material was purified by prep-HPLC, the mixture was adjusted with sodium bicarbonate until pH=8, the mixture was extracted with ethyl acetate (500 mL, twice), the organic phase was dried by anhydrous sodium sulfate, filtered and the filtrate was concentrated to give product. Compound 1-tert-butyl 4-methyl 2,2-dimethyl-3-(3-methylisoxazol-5-yl)succinate (5 g, 16.82 mmol, 65% yield) was obtained as a brown oil. $^1$H NMR (400 MHz, $CDCl_3$) δ 6.08 (s, 1H), 4.36 (s, 1H), 3.73-3.67 (m, 3H), 2.30 (s, 3H), 1.45 (s, 9H), 1.28 (s, 3H), 1.16 (s, 3H).

Step 2: Preparation of 4-methoxy-2,2-dimethyl-3-(3-methylisoxazol-5-yl)-4-oxobutanoic acid

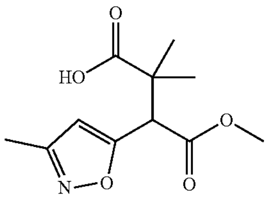

To a solution of 1-tert-butyl 4-methyl 2,2-dimethyl-3-(3-methylisoxazol-5-yl)succinate (4.9 g, 16.48 mmol, 1 eq) in dichloromethane (5 mL) was added hydrochloric acid/dioxane (4 M, 10 mL, 2.43 eq), the mixture was stirred at 20° C. for 11 h. The mixture was concentrated to give product. Compound 4-methoxy-2,2-dimethyl-3-(3-methylisoxazol-5-yl)-4-oxo-butanoic acid (4.0 g, crude) was obtained as a pale yellow oil. $^1$H-NMR (400 MHz, DMSO-$d_6$) δ 12.65 (br s, 1H), 6.35 (s, 1H), 4.40 (s, 1H), 3.62 (s, 3H), 2.23 (s, 3H), 1.21 (s, 3H), 1.08 (s, 3H).

Step 3: Preparation of tert-butyl 4-(4-methoxy-2,2-dimethyl-3-(3-methylisoxazol-5-yl)-4-oxobutanoyl)piperazine-1-carboxylate

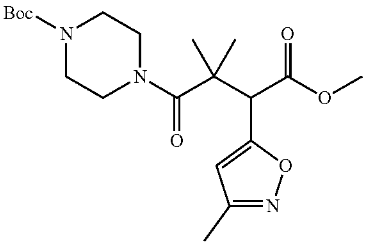 [SMILES: COC(=O)C(c1cc(C)no1)C(C)(C)C(=O)N1CCN(C(=O)OC(C)(C)C)CC1]

To a solution of 4-methoxy-2,2-dimethyl-3-(3-methylisoxazol-5-yl)-4-oxo-butanoic acid (3.4 g, 14.09 mmol, 1 eq) and tert-butyl piperazine-1-carboxylate (3.41 g, 18.32 mmol, 1.3 eq) in N,N-dimethylformamide (30 mL) was added diisopropylethylamine (3.64 g, 28.19 mmol, 2 eq) and then 0-(7-azabenzotriazol-1-yl)-N,N,N,N-tetramethyluronium hexafluorophosphate (5.89 g, 15.50 mmol, 1.1 eq) was added, the mixture was stirred at 20° C. for 1 h. The mixture was diluted with water (100 mL) and extracted with dichloromethane (100 mL, twice), the organic phase was dried by anhydrous sodium sulfate, filtered and the filtrate was concentrated to give crude product. This crude was purified by silica gel chromatography (ethyl acetate:petroleum ether=0:1 to 1:20) to give product, tert-butyl 4-[4-methoxy-2,2-dimethyl-3-(3-methylisoxazol-5-yl)-4-oxo-butanoyl] piperazine-1-carboxylate (5.3 g, 12.94 mmol, 91% yield) as a pale yellow oil. $^1$H NMR (400 MHz, $CDCl_3$) δ 6.16-6.01 (m, 1H), 4.39 (s, 1H), 3.70 (s, 3H), 3.67-3.56 (m, 4H), 3.50-3.41 (m, 4H), 2.36-2.24 (m, 3H), 1.53 (s, 3H), 1.47 (s, 9H), 1.31 (s, 3H).

Step 4: Preparation of tert-butyl 4-(4-methoxy-2,2-dimethyl-3-(3-methylisoxazol-5-yl)-4-oxobutyl)piperazine-1-carboxylate

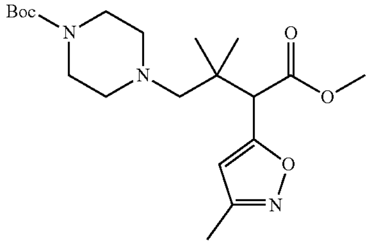 [SMILES: COC(=O)C(c1cc(C)no1)C(C)(C)CN1CCN(C(=O)OC(C)(C)C)CC1]

To a solution of tert-butyl 4-[4-methoxy-2,2-dimethyl-3-(3-methylisoxazol-5-yl)-4-oxo-butanoyl]piperazine-1-carboxylate (4.3 g, 10.50 mmol, 1 eq) in tetrahydrofuran (60 mL) was added dimethylsulfide borane (10 M, 10.5 mL, 10 eq) at 0° C., the mixture was stirred at 40° C. for 1 h. The mixture was quenched by methanol (20 mL), the residue was concentrated to give crude product. The crude material was purified by prep-HPLC, the mixture was adjusted with saturated sodium bicarbonate aqueous solution until pH=8, the mixture was extracted with ethyl acetate (200 mL, twice), the organic phase was dried by anhydrous sodium sulfate, filtered and the filtrate was concentrated to give product. Compound tert-butyl 4-[4-methoxy-2,2-dimethyl-3-(3-methylisoxazol-5-yl)-4-oxo-butyl]piperazine-1-carboxylate (2.7 g, 6.83 mmol, 65% yield) was obtained as a colorless oil. $^1$H-NMR (400 MHz, $CDCl_3$) δ 6.16 (s, 1H), 4.24-4.06 (m, 1H), 3.70 (s, 3H), 3.40 (br s, 4H), 2.51 (s, 4H), 2.31-2.15 (m, 5H), 1.46 (s, 9H), 1.05 (s, 3H), 0.92 (s, 3H).

Step 5: Preparation of 4-(4-(tert-butoxycarbonyl) piperazin-1-yl)-3,3-dimethyl-2-(3-methylisoxazol-5-yl)butanoic acid

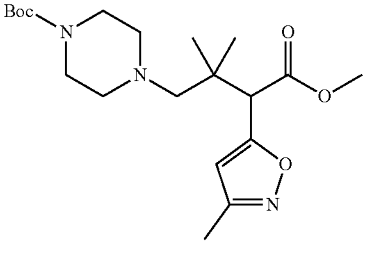 [SMILES: COC(=O)C(c1cc(C)no1)C(C)(C)CN1CCN(C(=O)OC(C)(C)C)CC1]

To a solution of tert-butyl 4-[4-methoxy-2,2-dimethyl-3-(3-methylisoxazol-5-yl)-4-oxo-butyl]piperazine-1-carboxylate (2.7 g, 6.83 mmol, 1 eq) in methanol (10 mL) and tetrahydrofuran (10 mL) was added lithium hydroxide monohydrate (2.86 g, 68.27 mmol, 10 eq) in water (10 mL), the mixture was stirred at 20° C. for 10 h. The mixture was adjusted with aqueous solution of hydrochloric acid (1 M) until pH=5, the mixture was extracted with dichloromethane (100 mL, three times), the organic phase was dried by anhydrous sodium sulfate, filtered and the filtrate was concentrated to give product. This product was purified by prep-HPLC, the fraction of acetonitrile was removed and the residue was lyophilized to give product. Compound 4-(4-tert-butoxycarbonylpiperazin-1-yl)-3,3-dimethyl-2-(3-methylisoxazol-5-yl)butanoic acid (1.2 g, 3.15 mmol) was obtained as a white solid. $^1$H NMR (400 MHz, DMSO-$d_6$) δ 6.25 (s, 1H), 3.87 (s, 1H), 3.27-3.21 (m, 4H), 2.53 (s, 4H), 2.29 (d, J=8.9 Hz, 2H), 2.20 (s, 3H), 1.38 (s, 9H), 0.99 (s, 3H), 0.92 (s, 3H).

Step 6: Preparation of tert-butyl 4-(4-((2S,4R)-4-hydroxy-2-(((S)-1-(4-(4-methylthiazol-5-yl)phenyl) ethyl)carbamoyl)pyrrolidin-1-yl)-2,2-dimethyl-3-(3-methylisoxazol-5-yl)-4-oxobutyl)piperazine-1-carboxylate

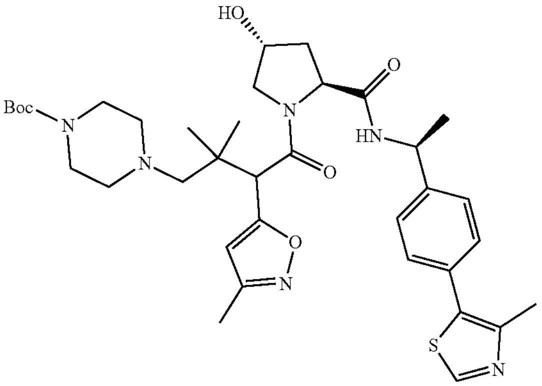 [SMILES: Cc1cc(C(C(=O)N2C[C@H](O)C[C@H]2C(=O)N[C@@H](C)c2ccc(-c3scnc3C)cc2)C(C)(C)CN2CCN(C(=O)OC(C)(C)C)CC2)on1]

To a solution of 4-(4-tert-butoxycarbonylpiperazin-1-yl)-3,3-dimethyl-2-(3-methylisoxazol-5-yl)butanoic acid (1.2 g, 3.15 mmol, 1 eq) and (2S,4R)-4-hydroxy-N-[(1S)-1-[4-(4-methylthiazol-5-yl)phenyl]ethyl]pyrrolidine-2-carboxamide (1.5 g, 4.08 mmol, 1.30 eq, hydrochloride) in 1,2-dichloroethane (15 mL) was added diisopropylethylamine (1.22 g, 9.44 mmol, 1.64 mL, 3 eq), and then 1-hydroxybenzotriazole (510 mg, 3.77 mmol, 1.2 eq) and N-(3-dimethylaminopropyl)-N-ethylcarbodiimide hydrochloride (724 mg, 3.77 mmol, 1.2 eq) was added, the mixture was stirred at 80° C. for 5 h. The mixture was diluted with dichloromethane (100 mL) and washed water (100 mL), the organic phase was dried by anhydrous sodium sulfate, filtered and the filtrate was concentrated to give crude product. The crude material was purified by silica gel chromatography (dichloromethane:methanol=50:1 to 10:1) to give the product. The product was further purified by prep-HPLC, the fraction of acetonitrile was removed and the residue was lyophilized to give the product. The product was purified even further by prep-HPLC, the fraction of acetonitrile was removed and the residue was lyophilized to give the final product. Compound tert-butyl 4-[4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate (490 mg, 0.71 mmol, 22.4% yield) was obtained as a white solid. $^1$H-NMR (400 MHz, $CDCl_3$) δ 8.68 (s, 1H), 7.50-7.34 (m, 5H), 6.27-6.08 (m, 1H), 5.13-4.97 (m, 1H), 4.71-4.55 (m, 2H), 4.47-4.32 (m, 1H), 3.90 (dd, J=5.4, 10.5 Hz, 1H), 3.53 (dd, J=4.2, 10.4 Hz, 1H), 3.41 (s, 4H), 2.67-2.43 (m, 8H), 2.31-2.25 (m, 3H), 2.22 (d, J=3.3 Hz, 2H), 1.97-1.85 (m, 1H), 1.52 (d, J=6.8 Hz, 2H), 1.48-1.40 (m, 10H), 1.11 (s, 3H), 1.04-0.96 (m, 3H).

Step 7: Preparation of (2S,4R)-1-(3,3-dimethyl-2-(3-methylisoxazol-5-yl)-4-(piperazin-1-yl)butanoyl)-4-hydroxy-N—((S)-1-(4-(4-methylthiazol-5-yl)phenyl)ethyl)pyrrolidine-2-carboxamide

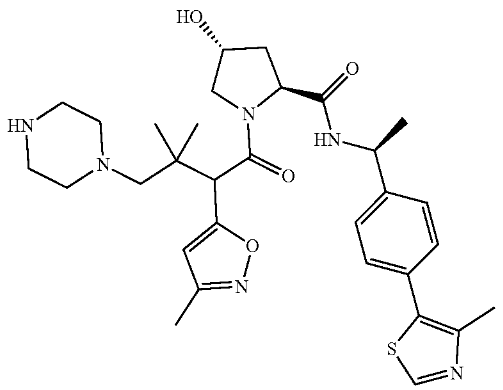 [SMILES: Cc1cc(C(C(=O)N2C[C@H](O)C[C@H]2C(=O)N[C@@H](C)c2ccc(-c3scnc3C)cc2)C(C)(C)CN2CCNCC2)on1]

To a solution of tert-butyl 4-[4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate (200 mg, 0.29 mmol, 1 eq) in dichloromethane (3 mL) was added hydrochloric acid/dioxane (4 M, 3 mL, 41.69 eq), the mixture was stirred at 20° C. for 1 h. The mixture was concentrated to give (2S,4R)-1-[3,3-dimethyl-2-(3-methylisoxazol-5-yl)-4-piperazin-1-yl-butanoyl]-4-hydroxy-N-[(1S)-1-[4-(4-methylthiazol-5-yl)phenyl]ethyl]pyrrolidine-2-carboxamide (230 mg, crude, hydrochloride) as a white solid. LC/MS (ESI) m/z: 595.2 $[M+1]^+$.

Step 8: Preparation of (2S,4R)-1-(4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N—((S)-1-(4-(4-methylthiazol-5-yl)phenyl)ethyl)pyrrolidine-2-carboxamide

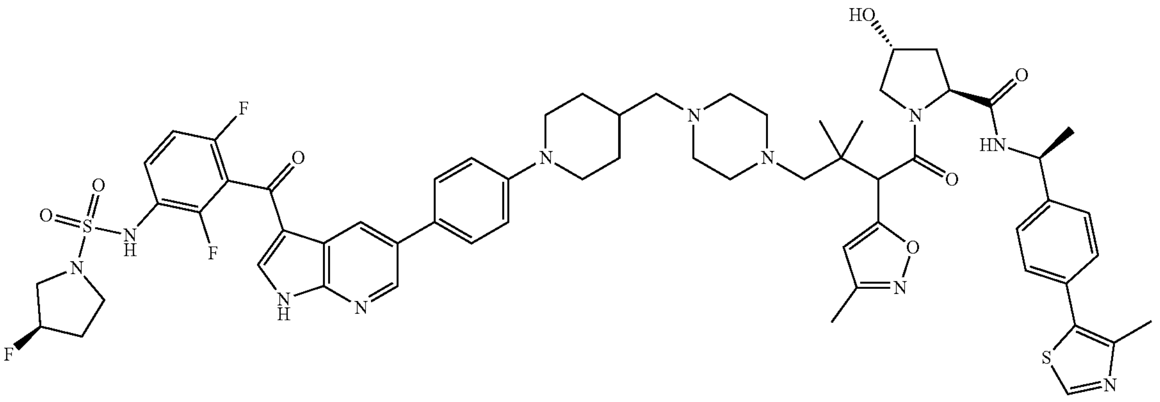 [SMILES: Cc1cc(C(C(=O)N2C[C@H](O)C[C@H]2C(=O)N[C@@H](C)c2ccc(-c3scnc3C)cc2)C(C)(C)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)on1]

To a mixture of (2S,4R)-1-[3,3-dimethyl-2-(3-methylisoxazol-5-yl)-4-piperazin-1-yl-butanoyl]-4-hydroxy-N-[(1S)-1-[4-(4-methylthiazol-5-yl)phenyl]ethyl]pyrrolidine-2-carboxamide (50 mg, 0.08 mmol, 1 eq, hydrochloride) in methanol (2 mL) was added sodium acetate (13 mg, 0.16 mmol, 2 eq) in one portion at 15° C. The mixture was stirred at 15° C. for 1 min, then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (44 mg, 0.071 mmol, 0.9 eq) in dichloromethane (0.5 mL) was added. The mixture was stirred at 15° C. for another 30 min, acetic acid (0.87 mmol, 0.05 mL, 11.04 eq) was added to adjust the pH=4~5. And then sodium cyanoborohydride (10 mg, 0.16 mmol, 2 eq) was added and stirred at 30° C. for 1 h. The reaction mixture was diluted with water 10 mL and extracted with dichloromethane (5 mL×3). The combined organic layers were washed with brine (10 mL×3), dried over anhydrous sodium sulfate, filtered and concentrated under reduce pressure. The residue was purified by Semi-preparative reverse phase HPLC. Compound (2S,4R)-1-[4-[4-[[1-[4-[3-[2,6-difluoro-3-[[(3R)-3-fluoro pyrrolidin-1-yl] sulfonylamino]benzoyl]-1H-pyrrolo[2,3-b]pyridin-5-yl] phenyl]-4-piperidyl]methyl]piperazin-1-yl]-3,3-dimethyl-2-(3-methylisoxazol-5-yl)butanoyl]-4-hydroxy-N-[(1S)-1-[4-(4-methylthiazol-5-yl)phenyl]ethyl]pyrrolidine-2-carboxamide (22 mg, 0.01 mmol, 21% yield, 96% purity, formate) was obtained as a light yellow solid. LC/MS (ESI) m/z: 1190.4 $[M+1]^+$; $^1$H-NMR (400 MHz, DMSO-$d_6$) δ 12.94 (s, 1H), 8.97-9.03 (m, 1H), 8.65 (d, J=2.0 Hz, 1H), 8.53 (s, 1H), 8.41 (d, J=8.0 Hz, 1H), 8.18 (s, 1H), 8.06 (s, 1H), 7.56-7.66 (m, 3H), 7.34-7.48 (m, 4H), 7.25 (t, J=8.8 Hz, 1H), 7.06 (d, J=8.8 Hz, 2H), 6.11-6.28 (m, 1H), 5.20-5.40 (m, 1H), 4.87-4.99 (m, 1H), 4.21-4.43 (m, 3H), 4.10 (s, 1H), 3.77 (d, J=10.4 Hz, 4H), 3.47 (s, 8H), 3.17 (s, 5H), 2.71-2.75 (m, 1H), 2.47 (s, 6H), 2.05-2.27 (m, 8H), 1.75-1.86 (m, 3H), 1.70 (s, 1H), 1.36-1.47 (m, 3H), 1.21 (d, J=8.8 Hz, 2H), 0.98-1.07 (m, 3H), 0.88 (s, 3H).

Exemplary Synthesis of (2S,4R)-1-((S)-2-(2-(4-((4-(4-(3-(2,6-difluoro-3-(((R)-3-fluoro-N-methylpyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide (Example 3301

Step 1: Preparation of (5-bromo-1-((2-(trimethylsilyl)ethoxy)methyl)-1H-pyrrolo[2,3-b]pyridin-3-yl)(2,6-difluoro-3-nitrophenyl)methanone

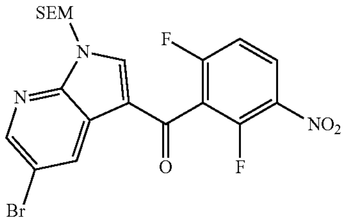 [SMILES: C[Si](C)(C)CCOCn1cc(C(=O)c2c(F)ccc([N+](=O)[O-])c2F)c2cc(Br)cnc21]

To a solution of (5-bromo-1H-pyrrolo[2,3-b]pyridin-3-yl)-(2,6-difluoro-3-nitro-phenyl) methanone (2 g, 5.23 mmol, 1 eq) in dimethylformamide (25 mL) was added 2-(chloromethoxy)ethyl-trimethyl-silane (1.05 g, 6.28 mmol, 1 mL, 1.2 eq) and diisopropylethylamine (1.01 g, 7.85 mmol, 1 mL, 1.5 eq). The mixture was stirred at 80° C. for 1.5 hr. The reaction mixture were washed with saturated brine (30 mL×2) and extracted with ethyl acetate (50 mL×2). The combined organic layers were dried over anhydrous sodium sulfate, filtered and concentrated under reduced pressure. The residue was purified by silica gel chromatography (Petroleum ether/Ethyl acetate=12/1 to 10:1). Compound [5-bromo-1-(2-trimethylsilylethoxymethyl)pyrrolo [2,3-b]pyridin-3-yl]-(2,6-difluoro-3-nitro-phenyl) methanone (1.74 g, 3.40 mmol, 64% yield) was obtained as a yellow solid. LC/MS (ESI) m/z: 513.9 $[M+1]^+$; $^1$H-NMR (400 MHz, $CDCl_3$) δ 8.87 (d, J=2.0 Hz, 1H), 8.52 (d, J=2.0 Hz, 1H), 8.28 (ddd, J=5.6, 8.4, 9.2 Hz, 1H), 7.70 (s, 1H), 7.20 (ddd, J=1.6, 7.2, 9.2 Hz, 1H), 5.68 (s, 2H), 3.63-3.55 (m, 2H), 0.96-0.87 (m, 2H), −0.04-−0.06 (m, 9H).

Step 2: Preparation of (3-amino-2,6-difluorophenyl)(5-bromo-1-((2-(trimethylsilyl)ethoxy)methyl)-1H-pyrrolo[2,3-b]pyridin-3-yl)methanone

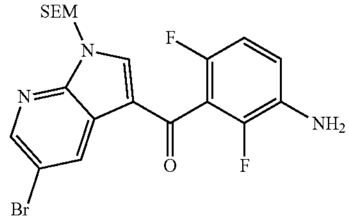 [SMILES: C[Si](C)(C)CCOCn1cc(C(=O)c2c(F)ccc(N)c2F)c2cc(Br)cnc21]

To a solution of [5-bromo-1-(2-trimethylsilylethoxymethyl)pyrrolo[2,3-b]pyridin-3-yl]-(2,6-difluoro-3-nitro-phenyl)methanone (1.72 g, 3.36 mmol, 1 eq) in ethyl alcohol (5 mL) and tetrahydrofuran (5 mL) and water (5 mL) was added iron (1.87 g, 33.57 mmol, 10 eq) and ammonium chloride (898 mg, 16.78 mmol, 0.6 mL, 5 eq). The mixture was stirred at 80° C. for 5 hour. The reaction mixture were filtered, washed with brine (30 mL×2) and extracted with ethyl acetate (50 mL×2). The combined organic layers were dried over anhydrous sodium sulfate, filtered and concentrated under reduced pressure. The residue was purified by silica gel chromatography (Petroleum ether/Ethyl acetate=10/1 to 4:1). Compound (3-amino-2,6-difluoro-phenyl)-[5-bromo-1-(2-trimethylsilylethoxymethyl)pyrrolo[2,3-b]pyridin-3-yl]methanone (1.33 g, 2.56 mmol, 76% yield, 93% purity) was obtained as a yellow oil. LC/MS (ESI) m/z: 484.1 $[M+2]^+$; $^1$H NMR (400 MHz, $CDCl_3$) δ 8.86 (d, J=2.0 Hz, 1H), 8.48 (d, J=2.4 Hz, 1H), 7.74 (s, 1H), 6.90-6.80 (m, 2H), 5.66 (s, 2H), 3.60-3.54 (m, 2H), 0.94-0.88 (m, 2H), −0.04-−0.07 (m, 9H).

Step 3: Preparation of (R)—N-(3-(5-bromo-1-((2-(trimethylsilyl)ethoxy)methyl)-1H-pyrrolo[2,3-b]pyridine-3-carbonyl)-2,4-difluorophenyl)-3-fluoropyrrolidine-1-sulfonamide

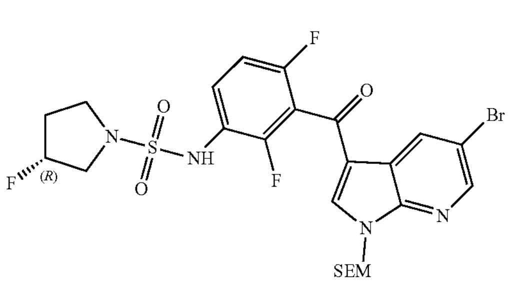

To a solution of (3-amino-2,6-difluoro-phenyl)-[5-bromo-1-(2-trimethylsilylethoxymethyl) pyrrolo[2,3-b]pyridin-3-yl]methanone (985 mg, 1.90 mmol, 1 eq) in pyridine (15 mL) was added dimethylaminopyridine (464 mg, 3.80 mmol, 2 eq) and (3R)-3-fluoropyrrolidine-1-sulfonyl chloride (712 mg, 3.80 mmol, 2 eq). The mixture was stirred at 50° C. for 12 hours. The reaction mixture was washed with saturated brine (30 mL×2) and extracted with ethyl acetate (40 mL×2). The combined organic layers were dried over anhydrous sodium sulfate, filtered and concentrated under reduced pressure. The residue was purified by Semi-preparative reverse phase HPLC. Saturated aqueous sodium bicarbonate was added to adjust the pH=9. The aqueous phase was extracted with ethyl acetate (50 mL×3). The combined organic phase was washed with brine (30 mL×3), dried with anhydrous sodium sulfate, filtered and concentrated in vacuum. Compound (3R)—N-[3-[5-bromo-1-(2-trimethylsilylethoxymethyl)pyrrolo[2,3-b]pyridine-3-carbonyl]-2,4-difluoro-phenyl]-3-fluoro-pyrrolidine-1-sulfonamide (210 mg, 0.33 mmol, 17% yield) was obtained as a colorless oil. $^1$H-NMR (400 MHz, $CDCl_3$) δ 8.85 (d, J=2.0 Hz, 1H), 8.49 (d, J=2.4 Hz, 1H), 7.78-7.68 (m, 2H), 7.10-6.99 (m, 1H), 6.54 (s, 1H), 5.65 (s, 2H), 5.31 (s, 1H), 3.66-3.60 (m, 2H), 3.57 (d, J=8.4 Hz, 2H), 3.55-3.43 (m, 2H), 2.38-2.23 (m, 1H), 2.16-1.96 (m, 1H), 0.94-0.88 (m, 2H), −0.05 (s, 9H).

Step 4: Preparation of (R)—N-(3-(5-bromo-1-((2-(trimethylsilyl)ethoxy)methyl)-1H-pyrrolo[2,3-b]pyridine-3-carbonyl)-2,4-difluorophenyl)-3-fluoro-N-methylpyrrolidine-1-sulfonamide

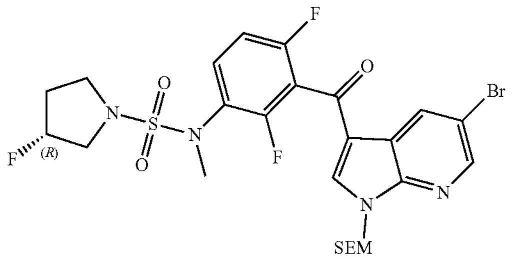

To a solution of (3R)—N-[3-[5-bromo-1-(2-trimethylsilylethoxymethyl) pyrrolo[2,3-b]pyridine-3-carbonyl]-2,4-difluoro-phenyl]-3-fluoro-pyrrolidine-1-sulfonamide (210 mg, 0.33 mmol, 1 eq) and in dimethylformamide (2 mL) was added diisopropylethylamine (64 mg, 0.50 mmol, 1.5 eq) and iodomethane (70 mg, 0.50 mmol, 1.5 eq). The mixture was stirred at 50° C. for 2 hours. The reaction mixture was washed with saturated aqueous brine (30 mL×2) and extracted with ethyl acetate (30 mL×2). The combined organic layers were dried over anhydrous sodium sulfate, filtered and concentrated under reduced pressure. The residue was purified by preparative—thin layer chromatography (Petroleum ether/Ethyl acetate=1:1, Rf=0.6). Compound (3R)—N-[3-[5-bromo-1-(2-trimethylsilylethoxymethyl)pyrrolo[2,3-b]pyridine-3-carbonyl]-2,4-difluoro-phenyl]-3-fluoro-N-methyl-pyrrolidine-1-sulfonamide (165 mg, 0.25 mmol, 76% yield) was obtained as a colorless oil. LC/MS (ESI) m/z: 649.2 $[M+2]^+$; $^1$H-NMR (400 MHz, $CDCl_3$) δ 8.85 (d, J=2.0 Hz, 1H), 8.49 (d, J=2.4 Hz, 1H), 7.74 (s, 1H), 7.66 (dt, J=6.0, 8.8 Hz, 1H), 7.08-7.01 (m, 1H), 5.65 (s, 2H), 5.34-5.14 (m, 1H), 3.71-3.64 (m, 1H), 3.64-3.59 (m, 2H), 3.59-3.53 (m, 2H), 3.53-3.47 (m, 1H), 3.25 (s, 3H), 2.39-2.06 (m, 2H), 0.95-0.88 (m, 2H), −0.06 (s, 9H).

Step 5: Preparation of tert-butyl (R)-2-(4-((4-(4-(3-(2,6-difluoro-3-((3-fluoro-N-methylpyrrolidine)-1-sulfonamido)benzoyl)-1-((2-(trimethylsilyl)ethoxy)methyl)-1H-pyrrolo[2,3-b]pyridin-5-yl)phenyl)piperazin-1-yl)methyl)piperidin-1-yl)acetate

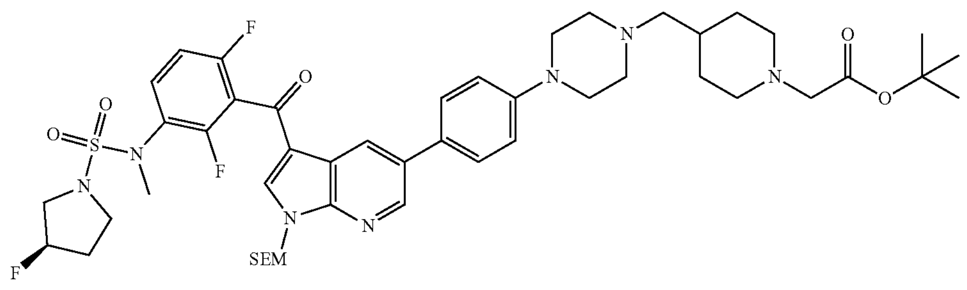 [SMILES: CN(c1ccc(F)c(C(=O)c2cn(COCC[Si](C)(C)C)c3ncc(-c4ccc(N5CCN(CC6CCN(CC(=O)OC(C)(C)C)CC6)CC5)cc4)cc23)c1F)S(=O)(=O)N1CC[C@@H](F)C1]

A mixture of (3R)—N-[3-[5-bromo-1-(2-trimethylsilylethoxymethyl)pyrrolo[2,3-b]pyridine-3-carbonyl]-2,4-difluoro-phenyl]-3-fluoro-N-methyl-pyrrolidine-1-sulfonamide (165 mg, 0.25 mmol, 1 eq), tert-butyl 2-[4-[[4-[4-(4,4,5,5-tetramethyl-1,3,2-dioxaborolan-2-yl)phenyl]piperazin-1-yl]methyl]-1-piperidyl]acetate (152 mg, 0.30 mmol, 1.2 eq), cesium fluoride (154 mg, 1.02 mmol, 4 eq) and 4-ditert-butylphosphanyl-N,N-dimethyl-aniline;dichloropalladium (18 mg, 0.02 mmol, 0.1 eq) in dioxane (2 mL) and water (0.5 mL) was degassed and purged with nitrogen for 3 times, and then the mixture was stirred at 100° C. for 12 hours under nitrogen atmosphere. The reaction mixture was washed with saturated aqueous brine (15 mL×2) and extracted with ethyl acetate (30 mL×2). The combined organic layers were dried over anhydrous sodium sulfate, filtered and concentrated under reduced pressure. The residue was purified by preparative—thin layer chromatography (Dichloromethane:Methanol=10:1, Rf=0.5). Compound tert-butyl 2-[4-[[4-[4-[3-[2,6-difluoro-3-[[(3R)-3-fluoropyrrolidin-1-yl]sulfonyl-methyl-amino]benzoyl]-1-(2-trimethylsilylethoxymethyl)pyrrolo[2,3-b]pyridin-5-yl]phenyl]piperazin-1-yl]methyl]-1-piperidyl]acetate (93 mg, 0.09 mmol, 38% yield) was obtained as a white solid. LC/MS (ESI) m/z: 940.5 $[M]^+$.

Step 6: Preparation of methyl (R)-2-(4-((4-(4-(3-(2,6-difluoro-3-((3-fluoro-N-methylpyrrolidine)-1-sulfonamido)benzoyl)-1H-pyrrolo[2,3-b]pyridin-5-yl)phenyl)piperazin-1-yl)methyl)piperidin-1-yl) acetate

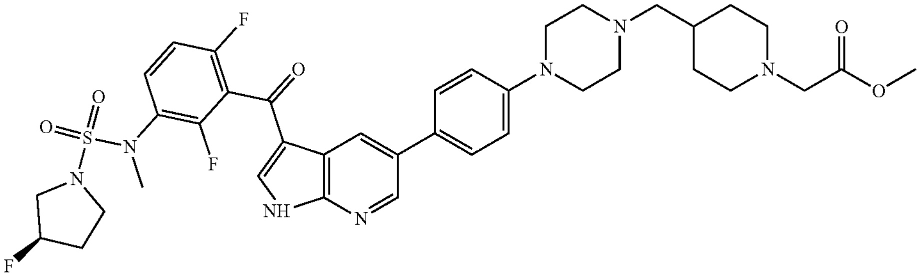 [SMILES: COC(=O)CN1CCC(CN2CCN(c3ccc(-c4cnc5[nH]cc(C(=O)c6c(F)ccc(N(C)S(=O)(=O)N7CC[C@@H](F)C7)c6F)c5c4)cc3)CC2)CC1]

To a solution of tert-butyl 2-[4-[[4-[4-[3-[2,6-difluoro-3-[[(3R)-3-fluoropyrrolidin-1-yl]sulfonyl-methyl-amino]benzoyl]-1-(2-trimethylsilylethoxymethyl)pyrrolo[2,3-b]pyridin-5-yl]phenyl]piperazin-1-yl]methyl]-1-piperidyl]acetate (93 mg, 0.10 mmol, 1 eq) in methanol (2 mL) was added hydrochloric acid/dioxane (4 M, 4 mL, 161.75 eq). The mixture was stirred at 40° C. for 14 hours. The reaction mixture was concentrated under vacuum to give a residue. Compound methyl 2-[4-[[4-[4-[3-[2,6-difluoro-3-[[(3R)-3-fluoropyrrolidin-1-yl]sulfonyl-methyl-amino]benzoyl]-1H-pyrrolo[2,3-b]pyridin-5-yl]phenyl]piperazin-1-yl]methyl]-1-piperidyl]acetate (120 mg, crude, hydrochloride) was obtained as a yellow solid. LC/MS (ESI) m/z: 768.1 $[M+1]^+$.

Step 7: Preparation of (R)-2-(4-((4-(4-(3-(2,6-difluoro-3-((3-fluoro-N-methylpyrrolidine)-1-sulfonamido)benzoyl)-1H-pyrrolo[2,3-b]pyridin-5-yl)phenyl)piperazin-1-yl)methyl)piperidin-1-yl)acetic acid

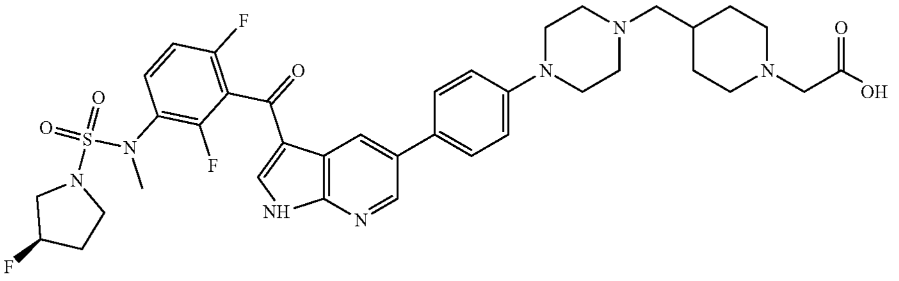 [SMILES: CN(c1ccc(F)c(C(=O)c2c[nH]c3ncc(-c4ccc(N5CCN(CC6CCN(CC(=O)O)CC6)CC5)cc4)cc23)c1F)S(=O)(=O)N1CC[C@@H](F)C1]

To a solution of methyl 2-[4-[[4-[4-[3-[2,6-difluoro-3-[[(3R)-3-fluoropyrrolidin-1-yl]sulfonyl-methyl-amino]benzoyl]-1H-pyrrolo[2,3-b]pyridin-5-yl]phenyl]piperazin-1-yl]methyl]-1-piperidyl]acetate (120 mg, 0.15 mmol, 1 eq, hydrochloride) in methanol (1 mL) water (0.5 mL) and tetrahydrofuran (1 mL) added lithium hydrate (11 mg, 0.45 mmol, 3 eq). The mixture was stirred at 20° C. for 1 hr. The reaction mixture was concentrated under vacuum to give a residue. The residue was diluted with water 20 mL, then acidified with hydrochloric acid (1 M) to pH=5~6. The suspension was concentrated under vacuum to give a residue. Compound 2-[4-[[4-[4-[3-[2,6-difluoro-3-[[(3R)-3-fluoropyrrolidin-1-yl]sulfonyl-methyl-amino]benzoyl]-1H-pyrrolo[2,3-b]pyridin-5-yl]phenyl]piperazin-1-yl]methyl]-1-piperidyl]acetic acid (0.1 g, crude, hydrochloride) was obtained as a yellow solid. LC/MS (ESI) m/z: 754.3 $[M+1]^+$.

Step 8: Preparation of (2S,4R)-1-((S)-2-(2-(4-((4-(4-(3-(2,6-difluoro-3-(((R)-3-fluoro-N-methylpyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

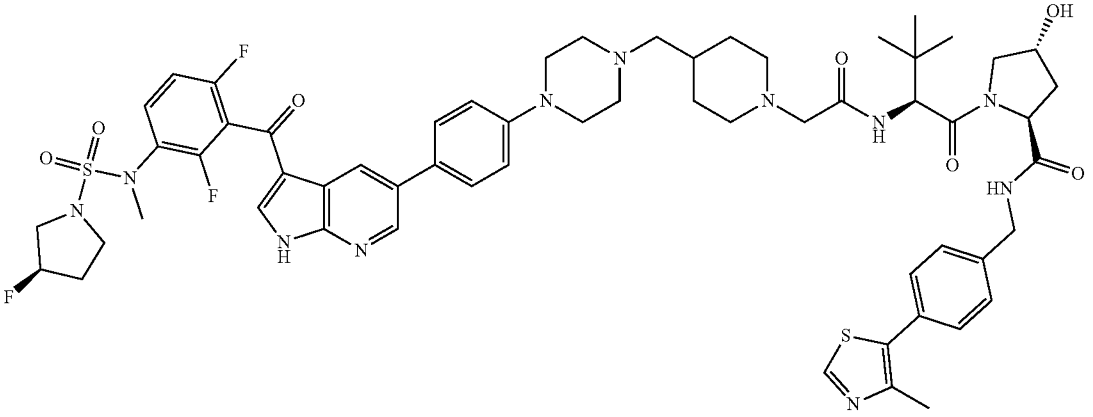 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(N(C)S(=O)(=O)N8CC[C@@H](F)C8)c7F)c6c5)cc4)CC3)CC2)C(C)(C)C)cc1]

To a solution of 2-[4-[[4-[4-[3-[2,6-difluoro-3-[[(3R)-3-fluoropyrrolidin-1-yl]sulfonyl-methyl-amino]benzoyl]-1H-pyrrolo[2,3-b]pyridin-5-yl]phenyl]piperazin-1-yl]methyl]-1-piperidyl]acetic acid (0.1 g, 0.13 mmol, 1 eq, hydrochloride) in dimethylformamide (2 mL) was added hydroxybenzotriazole (20 mg, 0.15 mmol, 1.2 eq), diisopropylethylamine (49 mg, 0.38 mmol, 3 eq) and (2S,4R)-1-[(2S)-2-amino-3,3-dimethyl-butanoyl]-4-hydroxy-N-[[4-(4-methylthiazol-5-yl) phenyl]methyl]pyrrolidine-2-carboxamide (59 mg, 0.13 mmol, 1 eq, hydrochloride) at 20° C., over 15 min. After addition, and then carbon dimethylamine hydrochloride (36 mg, 0.19 mmol, 1.5 eq) was added. The resulting mixture was stirred at 35° C. for 1.75 hours. The reaction mixture were washed with saturated brine (25 mL×2) and extracted with dichloromethane (30 mL×2). The combined organic layers were dried over anhydrous sodium sulfate, filtered and concentrated under reduced pressure. The residue was purified by Semi-preparative reverse phase HPLC. Compound (2S,4R)-1-[(2S)-2-[[2-[4-[[4-[4-[3-[2,6-difluoro-3-[[(3R)-3-fluoropyrrolidin-1-yl]sulfonyl-methyl-amino]benzoyl]-1H-pyrrolo[2,3-b]pyridin-5-yl]phenyl]piperazin-1-yl]methyl]-1-piperidyl]acetyl]amino]-3,3-dimethyl-butanoyl]-4-hydroxy-N-[[4-(4-methylthiazol-5-yl)phenyl]methyl]pyrrolidine-2-carboxamide (19.1 mg, 0.01 mmol, 11% yield, 100% purity, trifluoroacetic acid) was obtained as a yellow solid. LC/MS (ESI) m/z: 583.8 $[M/2+1]^+$; $^1$H-NMR (400 MHz, DMSO-$d_6$) δ 12.98 (s, 1H), 10.12-9.59 (m, 2H), 9.03-8.97 (m, 1H), 8.78 (d, J=8.4 Hz, 1H), 8.61 (d, J=6.0 Hz, 2H), 8.12 (s, 1H), 7.76 (dt, J=6.0, 8.8 Hz, 1H), 7.68 (d, J=8.8 Hz, 2H), 7.41 (q, J=8.4 Hz, 4H), 7.33 (t, J=8.8 Hz, 1H), 7.17 (d, J=8.8 Hz, 2H), 5.41 (s, 1H), 5.28 (s, 1H), 4.60 (d, J=9.2 Hz, 2H), 4.52-4.34 (m, 5H), 4.22 (dd, J=5.2, 15.6 Hz, 1H), 4.15-3.84 (m, 5H), 3.71 (d, J=7.2 Hz, 1H), 3.68-3.55 (m, 4H), 3.54-3.44 (m, 4H), 3.43-3.34 (m, 1H), 3.14 (s, 3H), 3.06 (s, 1H), 2.20 (d, J=6.4 Hz, 2H), 2.13 (d, J=7.6 Hz, 2H), 2.10-2.02 (m, 3H), 2.01-1.84 (m, 5H), 1.56 (s, 3H), 0.99-0.93 (m, 9H).

Exemplary Synthesis of (2S,4R)-1-((S)-2-(2-(4-((4-(4-(3-(2-fluoro-5-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide (Example 312)

Step 1: Preparation of 2-fluoro-5-nitrobenzoyl chloride

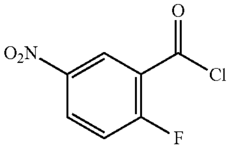 [SMILES: O=C(Cl)c1cc([N+](=O)[O-])ccc1F]

To a solution of 2-fluoro-5-nitro-benzoic acid (5 g, 27 mmol, 1 eq) and thionyl chloride (49 g, 413 mmol, 30 mL, 15 eq) in toluene (30 mL) and dimethyl formamide (1.5 mL). The mixture was stirred at 80° C. for 12 hours. The reaction mixture was quenched by addition methanol. The reaction mixture was concentrated under reduced pressure to remove solvent. Compound 2-fluoro-5-nitro-benzoyl chloride (5.8 g, crude) was obtained as a yellow oil.

Step 2: Preparation of (5-bromo-1H-pyrrolo[2,3-b]pyridin-3-yl)(2-fluoro-5-nitrophenyl)methanone

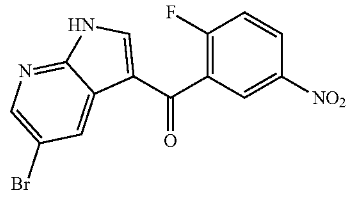 [SMILES: O=C(c1cc([N+](=O)[O-])ccc1F)c1c[nH]c2ncc(Br)cc12]

To a solution of 5-bromo-1H-pyrrolo[2,3-b]pyridine (5.86 g, 29.72 mmol, 1.1 eq) in 1,2-dichloroethane (100 mL), aluminium trichloride (23 g, 172.93 mmol, 9 mL, 6.4 eq) was added portion-wise. The reaction was stirred at 20° C. for 1 hour and 2-fluoro-5-nitro-benzoyl chloride (5.5 g, 27.02 mmol, 1 eq) was added. The mixture was stirred at 50° C. for another 12 hours. The reaction mixture was washed with saturated aqueous brine (35 mL×2) and extracted with ethyl acetate (50 mL×3). The combined organic layers were dried over anhydrous sodium sulfate, filtered and concentrated under reduced pressure to give a residue. The residue was purified by triturated with ethyl acetate (15 mL) and methanol (15 mL). Compound (5-bromo-1H-pyrrolo[2,3-b]pyridin-3-yl)-(2-fluoro-5-nitro-phenyl)methanone (2.11 g, 5.79 mmol, 21% yield) was obtained as a brown solid. LC/MS (ESI) m/z: 365.8 $[M+1]^+$.

Step 3: Preparation of (5-amino-2-fluorophenyl)(5-bromo-1H-pyrrolo[2,3-b]pyridin-3-yl)methanone

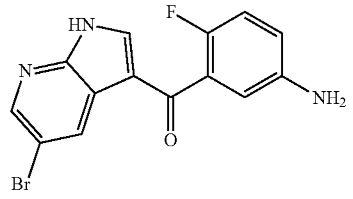 [SMILES: Nc1ccc(F)c(C(=O)c2c[nH]c3ncc(Br)cc23)c1]

A mixture of (5-bromo-1H-pyrrolo[2,3-b]pyridin-3-yl)-(2-fluoro-5-nitro-phenyl)methanone (2.11 g, 5.79 mmol, 1 eq), hydrochloric acid (12 M, 14.5 mL, 30 eq), iron powder (1.62 g, 28.97 mmol, 5 eq), ammonium chloride (930 mg, 17.38 mmol, 3 eq) in tetrahydrofuran (10 mL) and ethanol (10 mL) was stirred at 80° C. for 16 h. Aqueous sodium hydroxide (1 M) was added to adjust the pH=8~9. (50 mL) ethyl acetate was added and the mixture was stirred for 5 min. The mixture was filtered and the filtrate was extracted with ethyl acetate (50 mL×3). The combined organic phase was washed with brine (50 mL×3), dried with anhydrous sodium sulfate, filtered and concentrated in vacuum. The residue was slurried by a solution of petroleum ether and ethyl acetate (30 mL, v:v=1:1). The product (5-amino-2-fluoro-phenyl)-(5-bromo-1H-pyrrolo[2,3-b]pyridin-3-yl) methanone (730 mg, 2.06 mmol, 35% yield, 94% purity) was obtained as a brown solid. LC/MS (ESI) m/z: 333.9 $[M+1]^+$; $^1H$ NMR (400 MHz, DMSO-$d_6$) δ 12.93 (br s, 1H), 8.57 (d, J=2.4 Hz, 1H), 8.46 (d, J=2.4 Hz, 1H), 8.07 (d, J=1.6 Hz, 1H), 7.08-6.95 (m, 1H), 6.79-6.66 (m, 2H), 5.20 (s, 2H).

Step 4: Preparation of (R)—N-(3-(5-bromo-1H-pyrrolo[2,3-b]pyridine-3-carbonyl)-4-fluorophenyl)-3-fluoropyrrolidine-1-sulfonamide

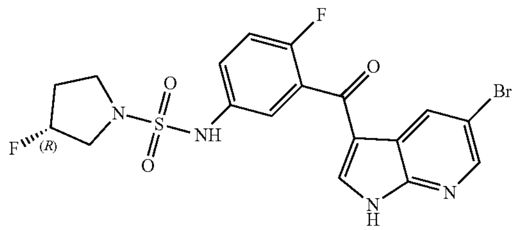

To a solution of (5-amino-2-fluoro-phenyl)-(5-bromo-1H-pyrrolo[2,3-b]pyridin-3-yl) methanone (680 mg, 2.04 mmol, 1 eq) and (3R)-3-fluoropyrrolidine-1-sulfonyl chloride (572 mg, 3.05 mmol, 1.5 eq) in pyridine (15 mL) was added 4-dimethylaminopyridine (49 mg, 0.4 mmol, 0.2 eq). The mixture was stirred at 40° C. for 12 hours. The reaction mixture was adjusted pH to 8 with saturated aqueous sodium bicarbonate. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by column chromatography (dichloromethane:methanol=400:1 to 10:1). Compound (3R)—N-[3-(5-bromo-1H-pyrrolo[2,3-b]pyridine-3-carbonyl)-4-fluoro-phenyl]-3-fluoro-pyrrolidine-1-sulfonamide (780 mg, 1.61 mmol, 78% yield) was obtained as a brown solid. LC/MS (ESI) m/z: 486.9 $[M+1]^+$; $^1H$-NMR (400 MHz, $CDCl_3$) δ 8.89 (s, 1H), 8.47 (s, 1H), 7.77 (s, 1H), 7.46-7.36 (m, 2H), 7.18 (t, J=9.2 Hz, 1H), 6.69 (s, 1H), 5.42-5.14 (m, 1H), 3.78-3.59 (m, 4H), 3.54-3.43 (m, 2H), 2.97-2.88 (m, 1H).

Step 5: Preparation of tert-butyl (R)-2-(4-((4-(4-(3-(2-fluoro-5-((3-fluoropyrrolidine)-1-sulfonamido)benzoyl)-1H-pyrrolo[2,3-b]pyridin-5-yl)phenyl)piperazin-1-yl)methyl)piperidin-1-yl)acetate

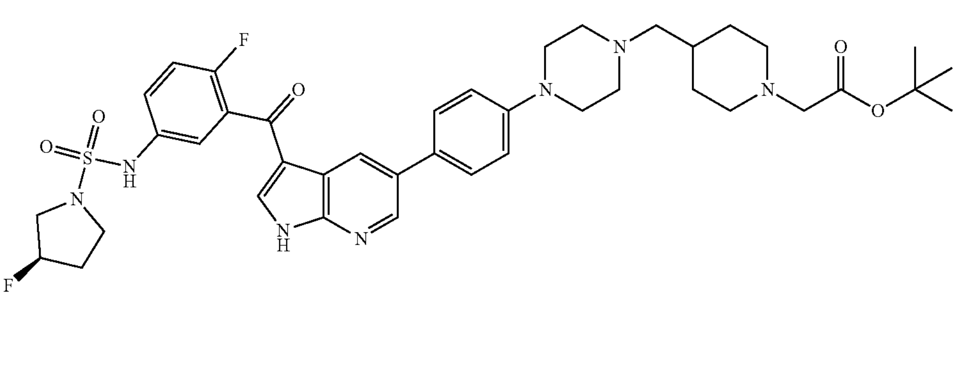 [SMILES: CC(C)(C)OC(=O)CN1CCC(CN2CCN(c3ccc(-c4cnc5[nH]cc(C(=O)c6cc(NS(=O)(=O)N7CC[C@@H](F)C7)ccc6F)c5c4)cc3)CC2)CC1]

To a solution of (3R)—N-[3-(5-bromo-1H-pyrrolo[2,3-b]pyridine-3-carbonyl)-4-fluoro-phenyl]-3-fluoro-pyrrolidine-1-sulfonamide (430 mg, 0.88 mmol, 1 eq) and tert-butyl 2-[4-[[4-[4-(4,4,5,5-tetramethyl-1,3,2-dioxaborolan-2-yl)phenyl]piperazin-1-yl]methyl]-1-piperidyl]acetate (442 mg, 0.88 mmol, 1 eq) in water (1 mL) and dioxane (10 mL) was added 4-ditert-butylphosphanyl-N,N-dimethyl-aniline; dichloropalladium (62 mg, 0.08 mmol, 0.1 eq) and cesium fluoride (538 mg, 3.54 mmol, 4 eq). The mixture was stirred at 100° C. for 5 h. Water (100 mL) was poured into the mixture and stirred for 1 minute. The aqueous phase was extracted with ethyl acetate (40 mL×3). The combined organic phase was washed with brine (100 mL×2), dried with anhydrous sodium sulfate, filtered and concentrated in vacuum. The residue was purified by prep-Thin layer chromatography (dichloromethane:methanol=10:1). Compound tert-butyl 2-[4-[[4-[4-[3-[2-fluoro-5-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetate (260 mg, 0.30 mmol, 34% yield, 92% purity) was obtained as a brown solid. LC/MS (ESI) m/z: 778.1 $[M+1]^+$.

Step 6: Preparation of (R)-2-(4-((4-(4-(3-(2-fluoro-5-((3-fluoropyrrolidine)-1-sulfonamido)benzoyl)-1H-pyrrolo[2,3-b]pyridin-5-yl)phenyl)piperazin-1-yl)methyl)piperidin-1-yl)acetic acid

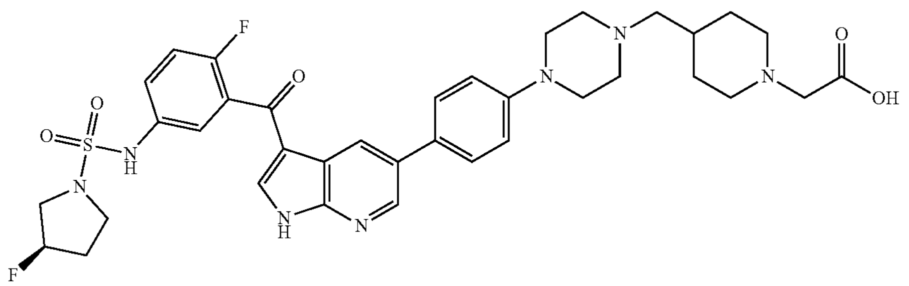 [SMILES: O=C(O)CN1CCC(CN2CCN(c3ccc(-c4cnc5[nH]cc(C(=O)c6cc(NS(=O)(=O)N7CC[C@@H](F)C7)ccc6F)c5c4)cc3)CC2)CC1]

To a solution of tert-butyl 2-[4-[[4-[4-[3-[2-fluoro-5-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetate (200 mg, 0.25 mmol, 1 eq) in dioxane (10 mL) was added 4 M hydrochloric acid in dioxane (6.67 mL, 103.72 eq). The mixture was stirred at 50° C. for 3 h. The reaction mixture was concentrated under reduced pressure to remove hydrochloric acid, dioxane and dioxane. The crude product was used into the next step without further purification. Compound 2-[4-[[4-[4-[3-[2-fluoro-5-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetic acid (194 mg, 0.25 mmol, 99% yield, hydrochloride) was obtained as a yellow solid.

Step 7: Preparation of (2S,4R)-1-((S)-2-(2-(4-((4-(4-(3-(2-fluoro-5-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

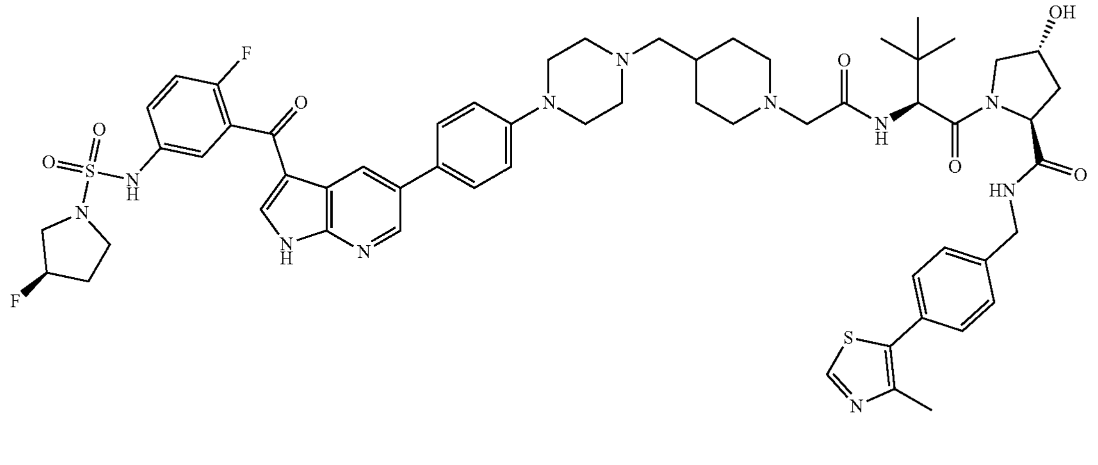 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7cc(NS(=O)(=O)N8CC[C@@H](F)C8)ccc7F)c6c5)cc4)CC3)CC2)C(C)(C)C)cc1]

To a solution of 2-[4-[[4-[4-[3-[2-fluoro-5-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl] acetic acid (194 mg, 0.25 mmol, 1 eq, hydrochloride) in N,N-dimethylformamide (3 mL) was added triethylamine (39 mg, 0.38 mmol, 1.5 eq), hydroxybenzotriazole (41 mg, 0.30 mmol, 1.2 eq), 1-(3-dimethylaminopropyl)-3-ethylcarbodiimide hydrochloride (74 mg, 0.38 mmol, 1.5 eq) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (119 mg, 0.25 mmol, 1 eq, hydrochloride acid). The mixture was stirred at 20° C. for 3 hour. Water (10 mL) was poured into the mixture and stirred for 1 minute. The aqueous phase was extracted with dichloromethane (10 mL×3). The combined organic phase was washed with brine (10 mL×2), dried with anhydrous sodium sulfate, filtered and concentrated in vacuum. The residue was purified by Semi-preparative reverse phase HPLC. Compound (2S,4R)-1-[(2S)-2-[[2-[4-[[4-[4-[3-[2-fluoro-5-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetyl]amino]-3,3-dimethyl-butanoyl]-4-hydroxy-N-[[4-(4-methylthiazol-5-yl)phenyl]methyl] pyrrolidine-2-carboxamide (119 mg, 0.09 mmol, 38% yield, 96% purity, formate) was obtained as a yellow solid. LC/MS (ESI) m/z: 567.7 $[M/2]^+$; $^1$H-NMR (400 MHz, DMSO-$d_6$) δ 12.91 (s, 1H), 9.00 (s, 1H), 8.65-8.55 (m, 3H), 8.19 (s, 1H), 7.97 (s, 1H), 7.81 (d, J=9.2 Hz, 1H), 7.59 (d, J=8.8 Hz, 2H), 7.45-7.40 (m, 4H), 7.40-7.31 (m, 3H), 7.06 (d, J=8.8 Hz, 2H), 5.34 (s, 1H), 5.21 (s, 1H), 4.50 (d, J=9.6 Hz, 1H), 4.47-4.41 (m, 1H), 4.41-4.32 (m, 2H), 4.30-4.24 (m, 1H), 3.71-3.54 (m, 2H), 3.47 (d, J=3.2 Hz, 2H), 3.18 (s, 5H), 3.05-2.87 (m, 3H), 2.83 (s, 2H), 2.52 (d, J=2.0 Hz, 3H), 2.45 (s, 3H), 2.25-1.85 (m, 10H), 1.81-1.69 (m, 2H), 1.55 (s, 1H), 1.23-1.09 (m, 2H), 0.99-0.91 (m, 9H).

Exemplary Synthesis of (2S,4R)-1-((S)-2-(2-(4-((4-(4-(3-(2-fluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide (Example 313)

Step 1: Preparation of (5-bromo-1H-pyrrolo[2,3-b]pyridin-3-yl)(2-fluoro-3-nitrophenyl)methanone

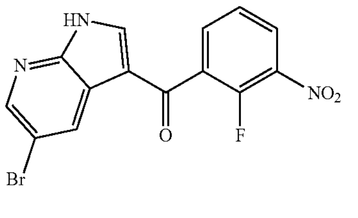 [SMILES: O=C(c1cccc([N+](=O)[O-])c1F)c1c[nH]c2ncc(Br)cc12]

To a solution of 2-fluoro-3-nitro-benzoic acid (10 g, 54 mmol, 1 eq) in dichloromethane (100 mL) was added thionyl chloride (14 g, 118.85 mmol, 8.6 mL, 2.2 eq) and N,N-dimethylformamide (1 mL). The mixture was stirred at 60° C. for 12 h. The mixture was concentrated. 2-fluoro-3-nitro-benzoyl chloride (11 g, crude) was obtained as a yellow oil. To a solution of 5-bromo-1H-pyrrolo[2,3-b]pyridine (11.7 g, 59.44 mmol, 1.1 eq) in dichloromethane (100 mL) was added Aluminium trichloride (46.1 g, 345.85 mmol, 6.4 eq). Then a solution of 2-fluoro-3-nitro-benzoyl chloride (11 g, 54.04 mmol, 1 eq) in dichloromethane (50 mL) was added into the mixture. The mixture was stirred at 60° C. for 12 h. The mixture was added to water (300 mL) and extracted with ethyl acetate (300 mL×3). The organic layer was dried over anhydrous sodium sulfate and concentrated. The residue was added ethyl acetate (30 mL) and filtered to give desired product. (5-bromo-1H-pyrrolo[2,3-b]pyridin-3-yl)-(2-fluoro-3-nitro-phenyl) methanone (12 g, 32.96 mmol, 60% yield) was obtained as a yellow solid. LC/MS (ESI) m/z: 363.8 $[M+1]^+$.

Step 2: Preparation of (3-amino-2-fluorophenyl)(5-bromo-1H-pyrrolo[2,3-b]pyridin-3-yl)methanone

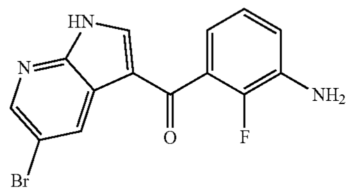 [SMILES: Nc1cccc(C(=O)c2c[nH]c3ncc(Br)cc23)c1F]

A mixture of (5-bromo-1H-pyrrolo[2,3-b]pyridin-3-yl)-(2-fluoro-3-nitro-phenyl)methanone (6 g, 16.48 mmol, 1 eq) ammonium chloride (3 g, 57.67 mmol, 3.5 eq) iron (4.5 g, 80.74 mmol, 4.9 eq) hydrochloride (12 M, 20 mL, 14.57 eq) in ethanol (50 mL) and tetrahydrofuran (50 mL) was stirred at 78° C. for 2 h. The mixture was added sodium hydroxide (1 M) to pH=8. The mixture was extracted with ethyl acetate (200 mL×3). The organic layer was dried over anhydrous sodium sulfate and concentrated. The residue was triturated with ethyl acetate (30 mL) to give desired product. (3-amino-2-fluoro-phenyl)-(5-bromo-1H-pyrrolo[2,3-b] pyridin-3-yl)methanone (2.7 g, 8.08 mmol, 49% yield) was obtained as a yellow solid. LC/MS (ESI) m/z: 335.9 $[M+1]^+$; $^1$H NMR (400 MHz, $CDCl_6$) δ 8.89 (d, J=2.0 Hz, 1H), 8.47 (d, J=2.0 Hz, 1H), 7.77 (d, J=3.2 Hz, 1H), 7.08-7.02 (m, 1H), 6.99-6.86 (m, 2H), 3.89 (br s, 2H).

Step 3: Preparation of (R)—N-(3-(5-bromo-1H-pyrrolo[2,3-b]pyridine-3-carbonyl)-2-fluorophenyl)-3-fluoropyrrolidine-1-sulfonamide

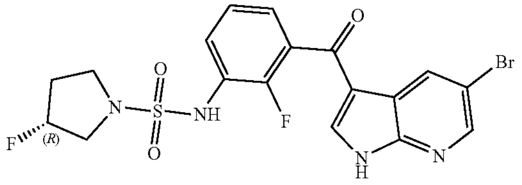

To a solution of (3-amino-2-fluoro-phenyl)-(5-bromo-1H-pyrrolo[2,3-b]pyridin-3-yl) methanone (700 mg, 2.09 mmol, 1 eq) in pyridine (7 mL) was added (3R)-3-fluoropyrrolidine-1-sulfonyl chloride (589 mg, 3.14 mmol, 1.5 eq) and 4-dimethylaminopyridine (51 mg, 0.418 mmol, 0.2 eq). The mixture was stirred at 40° C. for 12 h. The mixture was added saturated sodium bicarbonate (50 mL) and extracted with ethyl acetate (50 mL×3). The organic layer was dried over sodium sulfate and concentrated. The residue was purified with prep-TLC (Dichloromethane:Methanol=20:1).

(3R)—N-[3-(5-bromo-1H-pyrrolo[2,3-b]pyridine-3-carbonyl)-2-fluoro-phenyl]-3-fluoro-pyrrolidine-1-sulfonamide (400 mg, 0.824 mmol, 39% yield) was obtained as a yellow solid. LC/MS (ESI) m/z: 486.9 $[M+1]^+$; $^1$H-NMR (400 MHz, $CDCl_3$) δ 11.12 (br s, 1H), 8.91 (d, J=2.0 Hz, 1H), 8.52-8.44 (m, 1H), 7.86-7.72 (m, 2H), 7.38-7.31 (m, 1H), 7.13-6.94 (m, 1H), 5.36-5.14 (m, 1H), 3.68-3.58 (m, 2H), 3.57-3.46 (m, 2H), 2.36-2.22 (m, 1H), 2.18-1.97 (m, 1H).

Step 4: Preparation of tert-butyl (R)-2-(4-((4-(4-(3-(2-fluoro-3-((3-fluoropyrrolidine)-1-sulfonamido)benzoyl)-1H-pyrrolo[2,3-b]pyridin-5-yl)phenyl)piperazin-1-yl)methyl)piperidin-1-yl)acetate

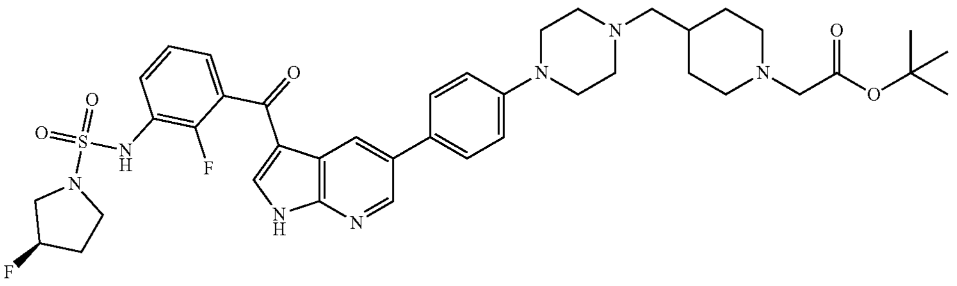 [SMILES: CC(C)(C)OC(=O)CN1CCC(CN2CCN(c3ccc(-c4cnc5[nH]cc(C(=O)c6cccc(NS(=O)(=O)N7CC[C@@H](F)C7)c6F)c5c4)cc3)CC2)CC1]

To a solution of (3R)—N-[3-(5-bromo-1H-pyrrolo[2,3-b]pyridine-3-carbonyl)-2-fluoro-phenyl]-3-fluoro-pyrrolidine-1-sulfonamide (100 mg, 0.20 mmol, 1 eq) and tert-butyl 2-[4-[[4-[4-(4,4,5,5-tetramethyl-1,3,2-dioxaborolan-2-yl)phenyl]piperazin-1-yl]methyl]-1-piperidyl]acetate (102 mg, 0.20 mmol, 1 eq) in dioxane (2 mL) and water (0.2 mL) was added 4-ditert-butylphosphanyl-N,N-dimethyl-aniline; dichloropalladium (29 mg, 0.041 mmol, 0.2 eq) and caesium fluoride (125 mg, 0.82 mmol, 4 eq). The mixture was stirred at 110° C. for 6 h. The mixture was added water (30 mL×3) and extracted with ethyl acetate (30 mL×3). The organic layer was dried over anhydrous sodium sulfate and concentrated. The residue was purified with prep-TLC (Dichloromethane:Methanol=20:1). Tert-butyl 2-[4-[[4-[4-[3-[2-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetate (40 mg, 0.038 mmol, 18% yield, 74% purity) was obtained as a yellow solid. LC/MS (ESI) m/z: 778.5 $[M+1]^+$.

Step 5: Preparation of (R)-2-(4-((4-(4-(3-(2-fluoro-3-((3-fluoropyrrolidine)-1-sulfonamido)benzoyl)-1H-pyrrolo[2,3-b]pyridin-5-yl)phenyl)piperazin-1-yl)methyl)piperidin-1-yl)acetic acid

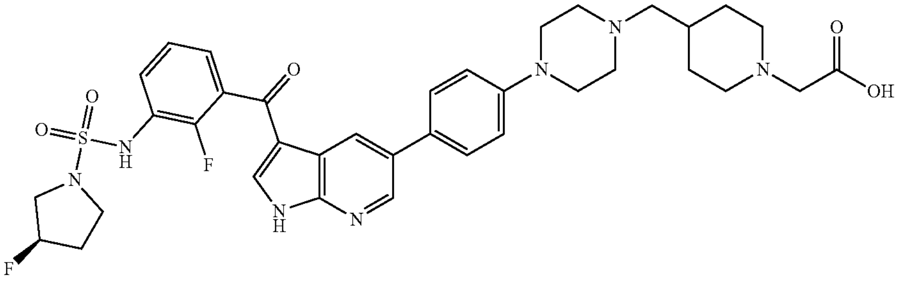 [SMILES: O=C(O)CN1CCC(CN2CCN(c3ccc(-c4cnc5[nH]cc(C(=O)c6cccc(NS(=O)(=O)N7CC[C@@H](F)C7)c6F)c5c4)cc3)CC2)CC1]

To a solution of tert-butyl 2-[4-[[4-[4-[3-[2-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetate (100 mg, 0.128 mmol, 1 eq) in dichloromethane (5 mL) was added hydrochloride/dioxane (4 M, 7.50 mL). The mixture was stirred at 20° C. for 12 h. The mixture was concentrated. The residue was used into next step without further purification. 2-[4-[[4-[4-[3-[2-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetic acid (100 mg, crude, hydrochloride) was obtained as a yellow solid. LC/MS (ESI) m/z: 722.4 $[M+1]^+$.

Step 6: Preparation of (2S,4R)-1-((S)-2-(2-(4-((4-(4-(3-(2-fluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

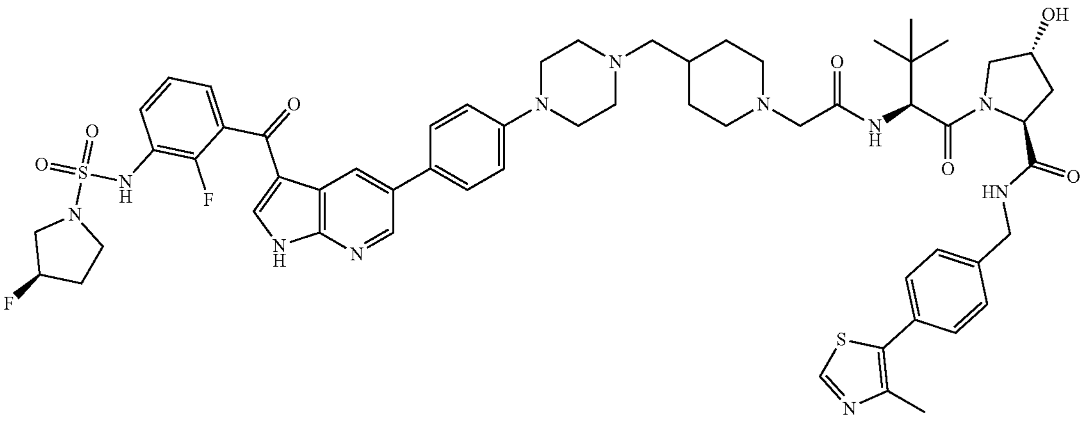 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7cccc(NS(=O)(=O)N8CC[C@@H](F)C8)c7F)c6c5)cc4)CC3)CC2)C(C)(C)C)cc1]

To a solution of 2-[4-[[4-[4-[3-[2-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetic acid (100 mg, 0.138 mmol, 1 eq) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (59 mg, 0.138 mmol, 1 eq) in N,N-dimethylformamide (2 mL) was added hydroxybenzotriazole (22 mg, 0.166 mmol, 1.2 eq) triethylamine (21 mg, 0.207 mmol, 1.5 eq) and 1-(3-dimethylaminopropyl)-3-ethylcarbodiimide hydrochloride (39 mg, 0.207 mmol, 1.5 eq). The mixture was stirred at 20° C. for 0.5 h. The mixture was quenched with water (30 mL×3) and extracted with dichloromethane/methanol (10:1, 30 mL×3). The organic layer was dried over sodium sulfate and concentrated. The residue was purified with prep-HPLC. (2S,4R)-1-[(2S)-2-[[2-[4-[[4-[4-[3-[2-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetyl]amino]-3,3-dimethyl-butanoyl]-4-hydroxy-N-[[4-(4-methylthiazol-5-yl)phenyl]methyl]pyrrolidine-2-carboxamide (5.9 mg, 0.0.04 mmol, 3.47% yield, 100% purity, 2 formic acid) was obtained as a yellow solid. LC/MS (ESI) m/z: 1134.4 $[M+1]^+$; $^1$H NMR (400 MHz, DMSO-$d_6$) δ 9.00 (s, 1H), 8.63 (s, 2H), 8.56 (s, 1H), 8.25 (s, 2H), 7.92 (s, 1H), 7.82 (br d, J=9.6 Hz, 1H), 7.67-7.56 (m, 3H), 7.48-7.38 (m, 4H), 7.35-7.23 (m, 2H), 7.06 (br d, J=8.8 Hz, 2H), 5.37-5.20 (m, 1H), 4.54-4.21 (m, 7H), 3.63 (br d, J=14.2 Hz, 1H), 3.18 (br s, 3H), 3.04-2.76 (m, 4H), 2.45 (br s, 7H), 2.23-1.85 (m, 12H), 1.82-1.69 (m, 2H), 1.56 (br s, 1H), 1.25-1.07 (m, 3H), 0.94 (s, 10H).

Exemplary Synthesis of (2S,4R)-1-((S)-2-(2-(4-((4-(4-(3-(2-chloro-6-fluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide (Example 352)

Step 1: Preparation of 2-chloro-6-fluoro-3-nitrobenzoic acid

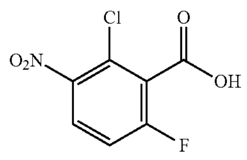 [SMILES: O=C(O)c1c(F)ccc([N+](=O)[O-])c1Cl]

To a solution of 2-chloro-6-fluoro-benzoic acid (10 g, 57.29 mmol, 1 eq) in sulfuric acid (100 mL) was added nitric acid (7.22 g, 114.58 mmol, 5.16 mL, 2 eq) at 0° C. The reaction mixture was warmed to 20° C. and stirred for 1 h. The reaction solution was poured into ice-water (1000 mL) and stirred for 10 minutes and then extracted with ethyl acetate (200 mL×3). The organic layers were combined and washed with water (200 mL×2), then brine (100 mL). The organic layer was dried over sodium sulfate, filtered and filtrate was concentrated in vacuum. 2-chloro-6-fluoro-3-nitro-benzoic acid (11.7 g, 53.29 mmol, 93% yield) was obtained as a white solid.

Step 2: Preparation of (5-bromo-1H-pyrrolo[2,3-b]pyridin-3-yl)(2-chloro-6-fluoro-3-nitrophenyl)methanone

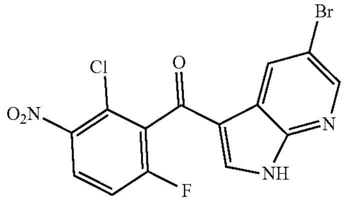 [SMILES: O=C(c1c(F)ccc([N+](=O)[O-])c1Cl)c1c[nH]c2ncc(Br)cc12]

To a solution of 2-chloro-6-fluoro-3-nitro-benzoic acid (11.3 g, 51.47 mmol, 1 eq) in toluene (100 mL) was added sulfoxide chloride (30.62 g, 257.34 mmol, 5 eq) and N,N-dimethylformamide (1 mL). The mixture was heated to 110° C. for 2 h. The solvent was removed in vacuum. The residue was dissolved in dichloromethane (200 mL) and 5-bromo-1H-pyrrolo[2,3-b]pyridine (11.15 g, 56.61 mmol, 1.1 eq), aluminium trichloride (20.59 g, 154.40 mmol, 3 eq) was added to the solution. The mixture was heated to 40° C. for 3 hr. The solvent was removed in vacuum and residue was poured into ice-water (500 mL) and stirred for 30 minutes. The mixture was extracted with tetrahydrofuran (300 mL×3). The organic layer was washed with brine (300 mL×2) and dried over sodium sulfate. The mixture was filtered and filtrate was concentrated in vacuum. The crude product was triturated with methanol (50 mL) to give (5-bromo-1H-pyrrolo[2,3-b]pyridin-3-yl)-(2-chloro-6-fluoro-3-nitro-phenyl) methanone (9.3 g, 22.40 mmol, 43% yield, 96% purity) as a yellow solid. LC/MS (ESI) m/z: 399.8 [M+1]$^+$.

Step 3: Preparation of (3-amino-2-chloro-6-fluoro-phenyl)(5-bromo-1H-pyrrolo[2,3-b]pyridin-3-yl)methanone

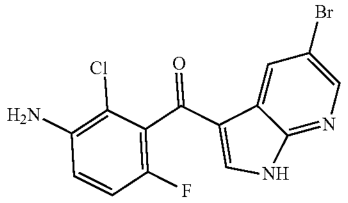

To a solution of (5-bromo-1H-pyrrolo[2,3-b]pyridin-3-yl)-(2-chloro-6-fluoro-3-nitro-phenyl) methanone (9.3 g, 23.33 mmol, 1 eq) in tetrahydrofuran (60 mL) and ethyl alcohol (60 mL) was added hydrochloride acid (12 M, 3.89 mL, 2 eq), ammonium chloride (3.74 g, 70.00 mmol, 3 eq) and iron powder (6.52 g, 116.67 mmol, 5 eq). The mixture was stirred at 80° C. for 12 h. The reaction mixture was adjusted pH to 8 with saturated aqueous sodium bicarbonate solution. The reaction mixture was filtered and the filtrate was concentrated. Water (100 mL) was poured into the mixture and stirred for 1 minute. The aqueous phase was extracted with tetrahydrofuran (100 mL×3). The combined organic phase was washed with brine (100 mL×2), dried with anhydrous sodium sulfate, filtered and concentrated in vacuum. The crude product was triturated with petroleum ether:ethyl acetate=1:1 (30 mL) to give (3-amino-2-chloro-6-fluoro-phenyl)-(5-bromo-1H-pyrrolo[2,3-b]pyridin-3-yl) methanone (8.03 g, 21.13 mmol, 90% yield, 97% purity) as a yellow solid. LC/MS (ESI) m/z: 369.8 [M+1]$^+$.

Step 4: Preparation of (R)—N-(3-(5-bromo-1H-pyrrolo[2,3-b]pyridine-3-carbonyl)-2-chloro-4-fluorophenyl)-3-fluoropyrrolidine-1-sulfonamide

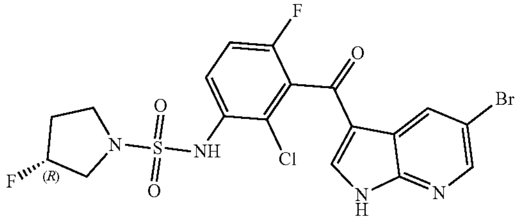

To a solution of (3-amino-2-chloro-6-fluoro-phenyl)-(5-bromo-1H-pyrrolo[2,3-b]pyridin-3-yl) methanone (1 g, 2.71 mmol, 1 eq) and (3R)-3-fluoropyrrolidine-1-sulfonyl chloride (610 mg, 3.26 mmol, 1.2 eq) in pyridine (10 mL) was added 4-dimethylaminopyridine (66 mg, 0.54 mmol, 0.2 eq). The mixture was stirred at 40° C. for 12 hours. The reaction mixture was adjusted pH to 8 with saturated aqueous sodium bicarbonate. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by preparative reverse phase HPLC. Compound (3R)—N-[3-(5-bromo-1H-pyrrolo[2,3-b]pyridine-3-carbonyl)-2-chloro-4-fluoro-phenyl]-3-fluoro-pyrrolidine-1-sulfonamide (270 mg, 0.51 mmol, 19% yield) was obtained as a yellow solid. LC/MS (ESI) m/z: 521.1 [M+1]$^+$.

Step 5: Preparation of (R)—N-(3-(5-bromo-1-((2-(trimethylsilyl)ethoxy)methyl)-1H-pyrrolo[2,3-b]pyridine-3-carbonyl)-2-chloro-4-fluorophenyl)-3-fluoro-N-((2-_(trimethylsilyl)ethoxy)methyl)pyrrolidine-1-sulfonamide

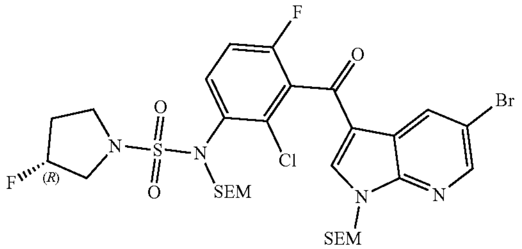

To a solution of (3R)—N-[3-(5-bromo-1H-pyrrolo[2,3-b]pyridine-3-carbonyl)-2-chloro-4-fluoro-phenyl]-3-fluoro-pyrrolidine-1-sulfonamide (410 mg, 0.78 mmol, 1 eq) in N,N-dimethylformamide (4.5 mL) was added sodium hydride (78 mg, 1.97 mmol, 60% in mineral oil, 2.5 eq) at 0° C. Then (2-(chloromethoxy)ethyl)trimethylsilane (328 mg, 1.97 mmol, 2.5 eq) was added to the mixture at 15° C. The mixture was stirred at 0-15° C. for 12 h. Saturated ammonium chloride aqueous solution (10 mL) was added to the mixture. Water (10 mL) was poured into the mixture and stirred for 1 minute. The aqueous phase was extracted with ethyl acetate (15 mL×3). The combined organic phase was washed with brine (15 mL×2), dried with anhydrous sodium sulfate, filtered and concentrated in vacuum. The residue was purified by preparative reverse phase thin layer chromatography (petroleum ether/ethyl acetate=3/1). (3R)—N-[3-[5-bromo-1-(2-trimethylsilylethoxymethyl)pyrrolo[2,3-b]pyridine-3-carbonyl]-2-chloro-4-fluoro-phenyl]-3-fluoro-N-(2-trimethylsilylethoxymethyl)pyrrolidine-1-sulfonamide (330 mg, 0.42 mmol, 53% yield) was obtained as a yellow oil. LC/MS (ESI) m/z: 781.0 [M+1]$^+$.

Step 6: Preparation of tert-butyl (R)-2-(4-((4-(4-(3-(2-chloro-6-fluoro-3-((3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenyl)piperazin-1-yl)methyl)piperidin-1-yl)acetate

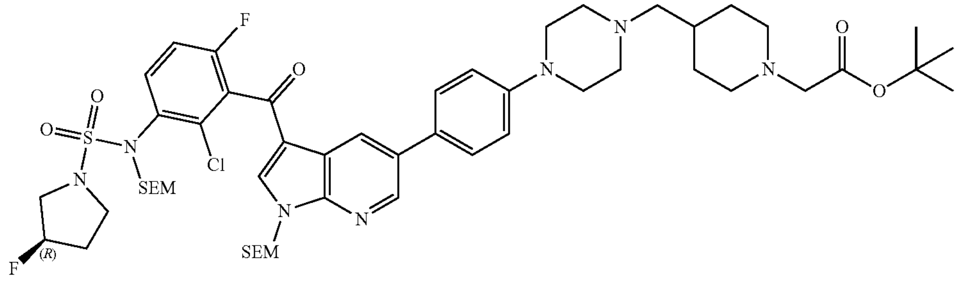

To a solution of (3R)—N-[3-[5-bromo-1-(2-trimethylsilylethoxymethyl)pyrrolo[2,3-b]pyridine-3-carbonyl]-2-chloro-4-fluoro-phenyl]-3-fluoro-N-(2-trimethylsilylethoxymethyl)pyrrolidine-1-sulfonamide (330 mg, 0.42 mmol, 1 eq) and tert-butyl 2-[4-[[4-[4-(4,4,5,5-tetramethyl-1,3,2-dioxaborolan-2-yl)phenyl]piperazin-1-yl]methyl]-1-piperidyl]acetate (211 mg, 0.42 mmol, 1 eq) in dioxane (5 mL) and water (0.5 mL) was added 4-ditert-butylphosphanyl-N,N-dimethyl-aniline;dichloropalladium (29 mg, 0.04 mmol, 0.1 eq) and cesium fluoride (256 mg, 1.69 mmol, 4 eq). The mixture was stirred at 90° C. for 3 h. Water (100 mL) was poured into the mixture and stirred for 1 minute. The aqueous phase was extracted with ethyl acetate (50 mL×3). The combined organic phase was washed with brine (100 mL×2), dried with anhydrous sodium sulfate, filtered and concentrated in vacuum. The residue was purified by prep-TLC (dichloromethane:methanol=10:1). Compound tert-butyl 2-[4-[[4-[4-[3-[2-chloro-6-fluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]piperazin-1-yl]methyl]-1-piperidyl]acetate (340 mg, 0.28 mmol, 68% yield, 91% purity) was obtained as a yellow oil. LC/MS (ESI) m/z: 537.8 $[M/2+1]^+$.

Step 7: Preparation of methyl (R)-2-(4-((4-(4-(3-(2-chloro-6-fluoro-3-((3-fluoropyrrolidine)-1-sulfonamido)benzoyl)-1H-pyrrolo[2,3-b]pyridin-5-yl)phenyl)piperazin-1-yl)methyl)piperidin-1-yl)acetate

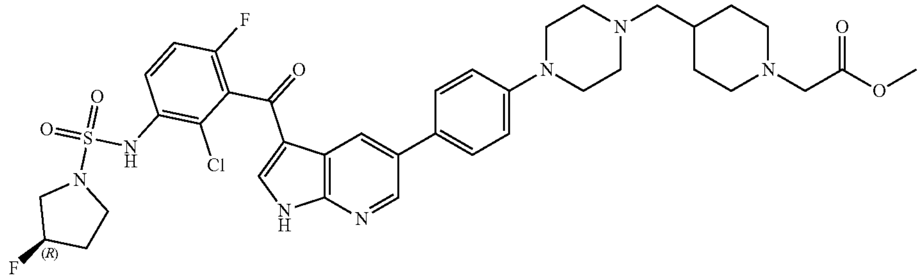

To a solution of tert-butyl 2-[4-[[4-[4-[3-[2-chloro-6-fluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]piperazin-1-yl]methyl]-1-piperidyl]acetate (340 mg, 0.31 mmol, 1 eq) in methanol (7 mL) was added hydrochloride acid/dioxane (4 M, 14 mL). The mixture was stirred at 40° C. for 12 h. The reaction mixture was filtered and concentrated under reduced pressure. The crude product was used into the next step without further purification, methyl 2-[4-[[4-[4-[3-[2-chloro-6-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetate (250 mg, 0.30 mmol, 97% yield, hydrochloride) was obtained as a yellow solid. LC/MS (ESI) m/z: 770.1 $[M+1]^+$.

Step 8: Preparation of (R)-2-(4-((4-(4-(3-(2-chloro-6-fluoro-3-((3-fluoropyrrolidine)-1-sulfonamido)benzoyl)-1H-pyrrolo[2,3-b]pyridin-5-yl)phenyl)piperazin-1-yl)methyl)piperidin-1-yl) acetic acid

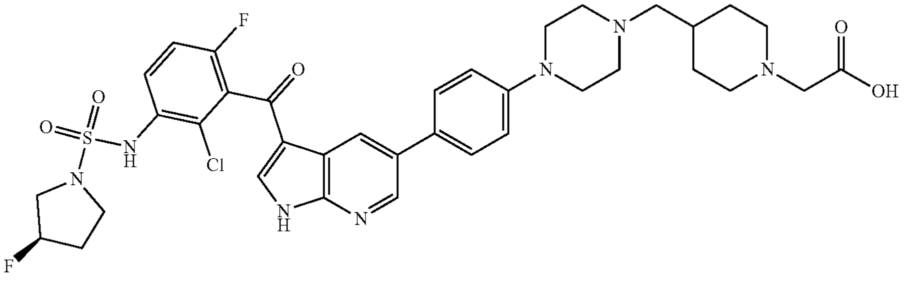 [SMILES: O=C(O)CN1CCC(CN2CCN(c3ccc(-c4cnc5[nH]cc(C(=O)c6c(F)ccc(NS(=O)(=O)N7CC[C@@H](F)C7)c6Cl)c5c4)cc3)CC2)CC1]

To a solution of methyl 2-[4-[[4-[4-[3-[2-chloro-6-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetate (250 mg, 0.30 mmol, 1 eq, hydrochloride) in water (3 mL), tetrahydrofuran (8 mL) and methanol (8 mL) was added lithium hydroxide monohydrate (78 mg, 1.86 mmol, 6 eq). The mixture was stirred at 15° C. for 2 h. Sodium hydroxide (24 mg, 0.61 mmol, 2 eq) was added to the mixture, the mixture was stirred at 40° C. for 12 h. The reaction mixture was filtered and concentrated under reduced pressure to give a residue. Then the reaction mixture was adjusted pH to 7 with hydrochloric acid (1 M). The residue was purified by preparative reverse phase HPLC. Compound 2-[4-[[4-[4-[3-[2-chloro-6-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetic acid (100 mg, 0.12 mmol, 80% yield, formate) was obtained as a yellow solid. LC/MS (ESI) m/z: 756.1 $[M+1]^+$.

Step 9: Preparation of (2S,4R)-1-((S)-2-(2-(4-((4-(4-(3-(2-chloro-6-fluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide To a solution of 2-[4-[[4-[4-[3-[2-chloro-6-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetic acid (100 mg, 0.12 mmol, 1 eq, formate) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (58 mg, 0.12 mmol, 1 eq, hydrochloride) in N,N-dimethylformamide (3 mL) was added hydroxybenzotriazole (20 mg, 0.14 mmol, 1.2 eq) and triethylamine (18 mg, 0.18 mmol, 1.5 eq). The mixture was stirred at 15° C. for 0.5 h. 1-(3-dimethylaminopropyl)-3-ethylcarbodiimide hydrochloride (28 mg, 0.14 mmol, 1.2 eq) was added to the mixture, the mixture was stirred at 15° C. for 11.5 h. Water (30 mL) was poured into the mixture and stirred for 1 minute. The aqueous phase was extracted with dichloromethane (10 mL×3). The combined organic phase was dried with anhydrous sodium sulfate, filtered and concentrated in vacuum. The residue was purified by preparative reverse phase HPLC. Compound (2S,4R)-1-[(2S)-2-[[2-[4-[[4-[4-[3-[2-chloro-6-fluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]acetyl]amino]-3,3-dimethyl-butanoyl]-4-hydroxy-N-[[4-(4-methylthiazol-5-yl)phenyl]methyl]pyrrolidine-2-carboxamide (72.1 mg, 0.05 mmol, 45% yield, 100% purity, 2 formate) was obtained as a yellow solid. LC/MS (ESI) m/z: 1168.4 $[M+1]^+$; $^1$H-NMR (400 MHz, DMSO-$d_6$) δ 13.04-12.70 (m, 1H), 9.00 (s, 1H), 8.66-8.61 (m, 2H), 8.17 (s, 1H), 8.19-8.15 (m, 1H), 7.98 (s, 1H), 7.83 (d, J=9.6 Hz,

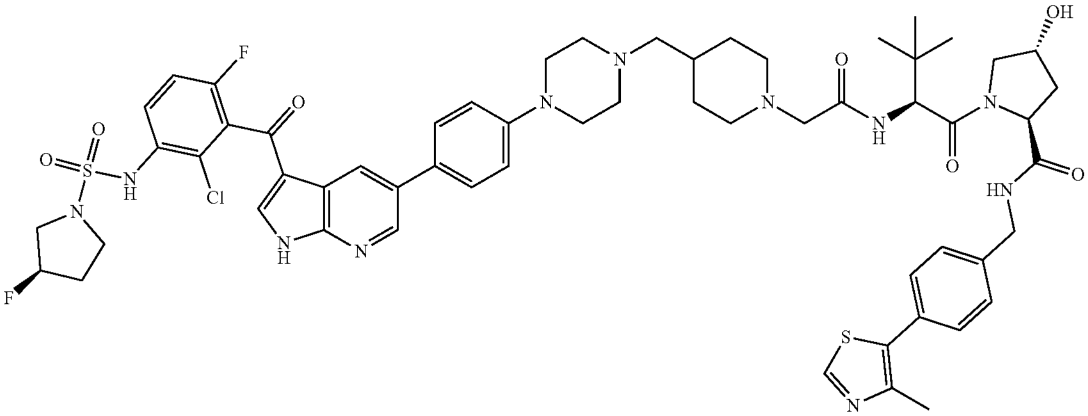 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7Cl)c6c5)cc4)CC3)CC2)C(C)(C)C)cc1]

1H), 7.66 (dd, J=6.0, 8.8 Hz, 1H), 7.58 (d, J=7.6 Hz, 2H), 7.48-7.30 (m, 6H), 7.06 (d, J=8.0 Hz, 2H), 5.37-5.21 (m, 1H), 4.50 (d, J=9.2 Hz, 1H), 4.48-4.40 (m, 2H), 4.37 (d, J=6.4 Hz, 2H), 4.32-4.23 (m, 2H), 3.70-3.57 (m, 1H), 3.46 (s, 4H), 3.19 (s, 2H), 3.02 (d, J=16.0 Hz, 3H), 2.94-2.79 (m, 3H), 2.21-2.02 (m, 13H), 1.90 (s, 2H), 1.73 (d, J=14.8 Hz, 2H), 1.55 (s, 1H), 1.22-1.10 (m, 2H), 0.95 (s, 9H).

Exemplary Synthesis of (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propyl)ureido)-3,3-dimethylbutanoyl)-4-hydroxy-N—((S)-1-(4-(4-methylthiazol-5-yl)phenyl)ethyl)pyrrolidine-2-carboxamide (Example 366)

Step 1: Preparation of benzyl (3,3-dimethoxypropyl)carbamate

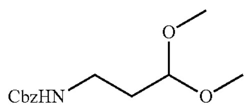 [SMILES: COC(CCNC(=O)OCc1ccccc1)OC]

To a solution of benzyl N-(3-oxopropyl)carbamate (1 g, 4.83 mmol, 1 eq) in methanol (10 mL) was added p-methylbenzene sulfonic acid (166 mg, 0.96 mmol, 0.2 eq) and trimethoxymethane (2.56 g, 24.1 mmol, 2.6 mL, 5 eq). The mixture was stirred at 30° C. for 2 hours. The reaction mixture was diluted with water (15 mL) and extracted with ethyl acetate (10 mL×2). The combined organic phase was washed with saturated brine (10 mL×2), dried with anhydrous sodium sulfate, filtered and concentrated in vacuum. The residue was purified by silica gel chromatography (petroleum ether:ethyl acetate=20:1 to 5:1) to give benzyl N-(3,3-dimethoxypropyl)carbamate (1.1 g, 4.34 mmol, 89% yield) as an colorless oil.

Step 2: Preparation of 3,3-dimethoxypropan-1-amine

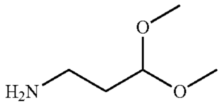

To a solution of benzyl N-(3,3-dimethoxypropyl)carbamate (1 g, 3.95 mmol, 1 eq) in tetrahydrofuran (15 mL) was added palladium on activated carbon catalyst (300 mg, 10%, 1.00 eq) under nitrogen atmosphere. The suspension was degassed and purged with hydrogen 3 times. The mixture was stirred under hydrogen (15 Psi) at 15° C. for 12 hours. The reaction mixture was filtered and the filter was concentrated to give 3,3-dimethoxypropan-1-amine (340 mg, 2.85 mmol, 72% yield) as a colorless oil. $^1$H NMR (400 MHz, $CDCl_3$) δ 4.48 (t, J=5.6 Hz, 1H), 3.34 (s, 6H), 2.79 (t, J=6.4 Hz, 2H), 1.77 (q, J=6.4 Hz, 2H), 1.21 (s, 2H).

Step 3: Preparation of (2S,4R)-1-((S)-2-(3-(3,3-dimethoxypropyl)ureido)-3,3-dimethylbutanoyl)-4-hydroxy-N—((S)-1-(4-(4-methylthiazol-5-yl)phenyl)ethyl)pyrrolidine-2-carboxamide

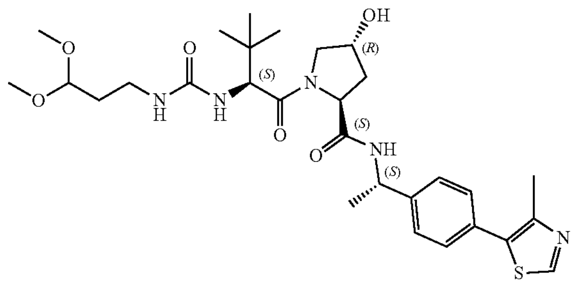

To a solution of 3,3-dimethoxypropan-1-amine (240 mg, 2.01 mmol, 1 eq) in tetrahydrofuran (4 mL) was added N,N-Carbonyldiimidazole (490 mg, 3.02 mmol, 1.5 eq) and triethylamine (407 mg, 4.03 mmol, 0.56 mL, 2 eq). The mixture was stirred at 15° C. for 4 hours. A solution of (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (484 mg, 1.01 mmol, 0.5 eq, hydrochloride) in tetrahydrofuran (4 mL) was dropwise added to the mixture and the mixture was stirred at 40° C. for another 12 hours. The reaction mixture was diluted with water (20 mL) and extracted with ethyl acetate (10 mL×3). The combined organic phase was washed with saturated brine (10 mL×2), dried with anhydrous sodium sulfate, filtered and concentrated in vacuum. The residue was purified by silica gel chromatography (dichloromethane:methanol=100:1 to 30:1) to give (2S,4R)-1-[(2S)-2-(3,3-dimethoxypropylcarbamoylamino)-3,3-dimethyl-butanoyl]-4-hydroxy-N-[(1S)-1-[4-(4-methylthiazol-5-yl)phenyl]ethyl]pyrrolidine-2-carboxamide (380 mg, 0.65 mmol, 31% yield) as a white solid.

Step 4: Preparation of (2S,4R)-1-((S)-3,3-dimethyl-2-(3-(3-oxopropyl)ureido)butanoyl)-4-hydroxy-N—((S)-1-(4-(4-methylthiazol-5-yl)phenyl)ethyl)pyrrolidine-2-carboxamide

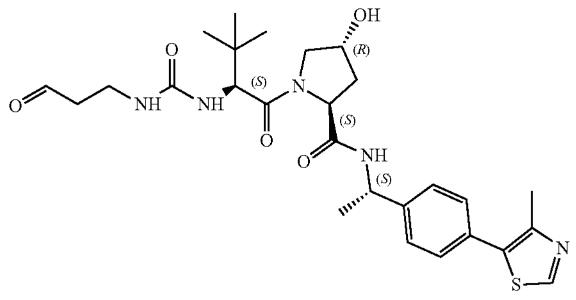

To a solution of (2S,4R)-1-[(2S)-2-(3,3-dimethoxypropylcarbamoylamino)-3,3-dimethyl-butanoyl]-4-hydroxy-N-[(1S)-1-[4-(4-methylthiazol-5-yl)phenyl]ethyl]pyrrolidine-2-carboxamide (200 mg, 0.33 mmol, 1 eq) in tetrahydrofuran (30 mL) was added sulfuric acid (2 M, 6.8 mL, 40 eq). The mixture was stirred at 60° C. for 10 min. The reaction mixture was adjusted to pH 8~9 with saturated sodium bicarbonate and with water (15 mL), and then the mixture was extracted with ethyl acetate (10 mL×2). The combined organic phase was washed with saturated brine (10 mL×2), dried with anhydrous sodium sulfate, filtered and concentrated in vacuum to give the crude product (2S,4R)-1-[(2S)-3,3-dimethyl-2-(3-oxopropylcarbamoylamino)butanoyl]-4-hydroxy-N-[(1S)-1-[4-(4-methylthiazol-5-yl)phenyl]ethyl]pyrrolidine-2-carboxamide (180 mg, crude) as a white solid was used into the next step without further purification.

Step 5: Preparation of tert-butyl 4-(4-(4,4,5,5-tetramethyl-1,3,2-dioxaborolan-2-yl)phenyl)piperazine-1-carboxylate

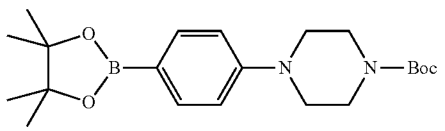 [SMILES: CC(C)(C)OC(=O)N1CCN(c2ccc(B3OC(C)(C)C(C)(C)O3)cc2)CC1]

A mixture of 4,4,5,5-tetramethyl-2-(4,4,5,5-tetramethyl-1,3,2-dioxaborolan-2-yl)-1,3,2-dioxaborolane (893 mg, 3.52 mmol, 1.2 eq), tert-butyl 4-(4-bromophenyl)piperazine-1-carboxylate (1 g, 2.93 mmol, 1 eq), potassium acetate (575 mg, 5.86 mmol, 2 eq) and [1,1'-bis(diphenylphosphino)ferrocene]dichloropalladium(ii) (214 mg, 0.29 mmol, 0.1 eq) in dioxane (15 mL) was degassed and purged with nitrogen 3 times, and then the mixture was stirred at 90° C. for 12 hours under nitrogen atmosphere. The reaction mixture was filtered, washed with saturated aqueous brine (30 mL×3) and extracted with ethyl acetate (50 mL×3). The combined organic layers were dried over anhydrous sodium sulfate, filtered and concentrated under reduced pressure. The residue was purified by silica gel chromatography (Petroleum ether/Ethyl acetate=15/1 to 5:1). Compound tert-butyl 4-[4-(4,4,5, 5-tetramethyl-1,3,2-dioxaborolan-2-yl)phenyl]piperazine-1-carboxylate (1.07 g, 2.59 mmol, 88% yield, 94% purity) was obtained as a white solid. LC/MS (ESI) m/z: 389.3 $[M+1]^+$.

Step 6: Preparation of tert-butyl (R)-4-(4-(3-(2,6-difluoro-3-((3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenyl)piperazine-1-carboxylate

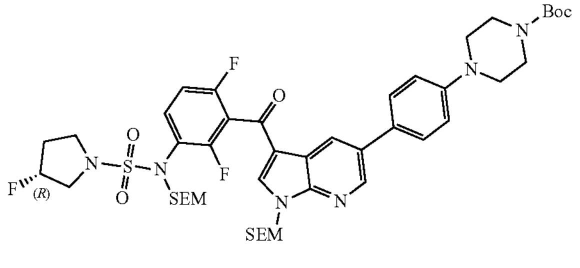

A mixture of tert-butyl 4-[4-(4,4,5,5-tetramethyl-1,3,2-dioxaborolan-2-yl)phenyl]piperazine-1-carboxylate (1.07 g, 2.59 mmol, 1 eq), (3R)—N-[3-[5-bromo-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (2.2 g, 2.88 mmol, 1.11 eq), 4-ditert-butylphosphanyl-N,N-dimethyl-aniline;dichloropalladium (183 mg, 0.26 mmol, 0.2 mL, 0.1 eq) and cesium fluoride (1.57 g, 10.35 mmol, 0.4 mL, 4 eq) in dioxane (10 mL) and water (2 mL) was degassed and purged with nitrogen 3 times, and then the mixture was stirred at 100° C. for 12 hr under nitrogen atmosphere. The reaction mixture was poured into water (30 mL) and extracted with ethyl acetate (50 mL×2). The combined organic layers were dried over anhydrous sodium sulfate, filtered and concentrated under reduced pressure. The residue was purified by silica gel chromatography (Petroleum ether/Ethyl acetate=15:1 to 2:1). Compound tert-butyl 4-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]piperazine-1-carboxylate (1.54 g, 1.59 mmol, 62% yield, 97% purity) was obtained as a yellow oil. LC/MS (ESI) m/z: 945.2 $[M]^+$.

Step 7: Preparation of (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide

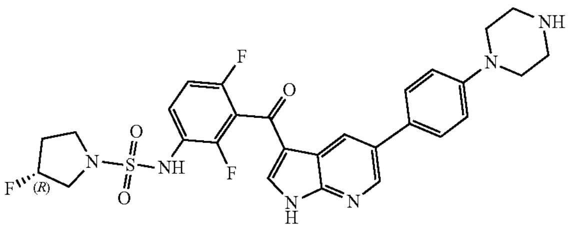

To a solution of tert-butyl 4-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]piperazine-1-carboxylate (1.54 g, 1.59 mmol, 1 eq) in dichloromethane (5 mL) was added hydrochloric acid/dioxane (4 M, 15 mL, 37.85 eq. The mixture was stirred at 40° C. for 4 h. Then methyl alcohol (5 mL) was added, and the mixture was stirred at 40° C. for another 12 hours. The reaction mixture concentrated under vacuum to give a residue. Compound (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (1.22 g, crude, 2 hydrochloride) was obtained as a yellow solid. LC/MS (ESI) m/z: 585.1 $[M]^+$; $^1$H-NMR (400 MHz, DMSO-$d_6$) δ 12.98 (s, 1H), 9.87 (s, 1H), 9.18 (s, 2H), 8.67 (d, J=2.4 Hz, 1H), 8.57 (s, 1H), 8.08 (s, 1H), 7.66 (d, J=8.8 Hz, 2H), 7.27 (t, J=8.8 Hz, 1H), 7.14 (d, J=8.8 Hz, 2H), 5.39-5.21 (m, 1H), 3.64 (s, 1H), 3.61-3.55 (m, 1H), 3.49-3.43 (m, 6H), 3.40 (s, 3H), 3.24 (s, 5H).

Step 8: Preparation of (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propyl)ureido)-3,3-dimethylbutanoyl)-4-hydroxy-N—((S)-1-(4-(4-methylthiazol-5-yl)phenyl)ethyl)pyrrolidine-2-carboxamide

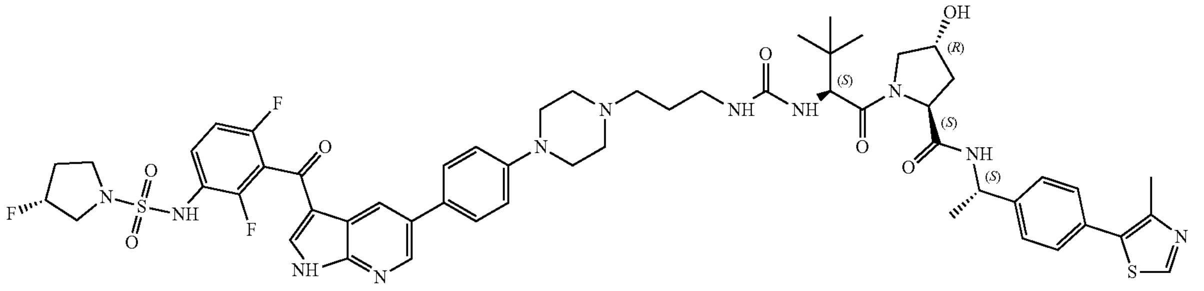

To a solution of (2S,4R)-1-[(2S)-3,3-dimethyl-2-(3-oxopropylcarbamoylamino)butanoyl]-4-hydroxy-N-[(1S)-1-[4-(4-methylthiazol-5-yl)phenyl]ethyl]pyrrolidine-2-carboxamide (140 mg, 0.25 mmol, 1 eq) in 1,2-dichloroethane (5 mL) was added triethylamine (78 mg, 0.77 mmol, 3 eq) and (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (160 mg, 0.25 mmol, 1 eq, hydrochloride). The mixture was stirred at 15° C. for 0.5 hour. Sodium triacetoxyborohydride (109 mg, 0.51 mmol, 2 eq) was added then the mixture was stirred at 15° C. for 3 hours. The reaction mixture was diluted with water (10 mL) and extracted with dichloromethane (10 mL×2). The combined organic phase was washed with saturated brine (5 mL×2), dried with anhydrous sodium sulfate, filtered and concentrated in vacuum. The residue was purified by Semi-preparative reverse phase HPLC to give (2S,4R)-1-[(2S)-2-[3-[4-[4-[3-[2,6-difluoro-3-[[(3R)-3-fluoropyrrolidin-1-yl] sulfonylamino]benzoyl]-1H-pyrrolo[2,3-b]pyridin-5-yl] phenyl]piperazin-1-yl]propylcarbamoylamino]-3,3-dimethyl-butanoyl]-4-hydroxy-N-[(1S)-1-[4-(4-methylthiazol-5-yl)phenyl]ethyl]pyrrolidine-2-carboxamide (89.5 mg, 0.07 mmol, 30% yield, 100% purity, formate) as a white solid. LC/MS (ESI) m/v 1112.3 $[M+1]^+$; $^1$H-NMR (400 MHz, DMSO-$d_6$) δ 12.90 (s, 1H), 8.97 (s, 1H), 8.65 (d, J=2.0 Hz, 1H), 8.53 (s, 1H), 8.36 (d, J=7.6 Hz, 1H), 8.19 (s, 1H), 8.05 (s, 1H), 7.66-7.56 (m, 3H), 7.46-7.41 (m, 2H), 7.40-7.35 (m, 2H), 7.25 (t, J=8.0 Hz, 1H), 7.12-7.01 (m, 2H), 6.15 (t, J=5.6 Hz, 1H), 6.08 (d, J=9.6 Hz, 1H), 5.38-5.19 (m, 1H), 4.91 (q, J=7.2 Hz, 1H), 4.44 (t, J=8.0 Hz, 1H), 4.35-4.26 (m, 2H), 3.66-3.57 (m, 2H), 3.48 (s, 1H), 3.43-3.36 (m, 2H), 3.33-3.27 (m, 1H), 3.26-3.12 (m, 5H), 3.11-2.97 (m, 2H), 2.55-2.53 (m, 2H), 2.45 (s, 3H), 2.35 (br t, J=7.2 Hz, 2H), 2.15-1.94 (m, 3H), 1.80 (ddd, J=4.8, 8.4, 12.8 Hz, 1H), 1.62-1.53 (m, 2H), 1.38 (d, J=7.2 Hz, 3H), 1.00 (s, 2H), 0.93 (s, 9H).

Exemplary Synthesis of (2S,4R)-1-(4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-2-(3-methylisoxazol-5-yl)butanoyl)-4-hydroxy-N—((S)-1-(4-(4-methylthiazol-5-yl)phenyl)ethyl)pyrrolidine-2-carboxamide (Example 440)

Step 1: Preparation of methyl 4,4-dimethoxy-2-(3-methylisoxazol-5-yl)butanoate

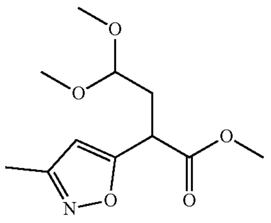

To a solution of methyl 2-(3-methylisoxazol-5-yl)acetate (1 g, 6.45 mmol, 1 eq) in dimethyl formamide (10 mL) was added potassium tert-butoxide (867 mg, 7.73 mmol, 1.2 eq). The mixture was stirred at 15° C. for half an hour, then 2-bromo-1,1-dimethoxy-ethane (1.31 g, 7.73 mmol, 1.2 eq) was added. The resulting mixture was stirred at 15° C. for another 1.5 hours. Then the mixture was heated to 50° C. and stirred at 50° C. for another 1 hour. The mixture was poured into 100 mL brine and the pH was adjusted to 5.0 with 2.0 M hydrochloric acid. The mixture was extracted with ethyl acetate (50 mL×2). The combined organic layers were washed with brine (50 mL×2), dried over sodium sulfate, filtered and concentrated in vacuum. The residue was further purified by column chromatography (petroleum ether:ethyl acetate=10:1 to 5:1) to give methyl 4,4-dimethoxy-2-(3-methylisoxazol-5-yl)butanoate (620 mg, 1.53 mmol, 23% yield, 60% purity) as a colorless oil. LC/MS (ESI) m/z: 244.1 $[M+1]^+$.

Step 2: Preparation of 2-(3-methylisoxazol-5-yl)-4-oxobutanoic acid

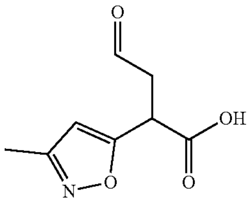

To a solution of methyl 4,4-dimethoxy-2-(3-methylisoxazol-5-yl)butanoate (0.4 g, 1.64 mmol, 1 eq) in dioxane (2 mL) was added sulfuric acid (2 mL). The mixture was heated to 50° C. and stirred at 50° C. for 2 hours. The mixture was poured into 20 mL brine, and the pH was adjusted to 4.0 with 2.0 M hydrochloric acid. The mixture was extracted with ethyl acetate (30 mL×2). The combined organic layers were dried over sodium sulfate, filtered and concentrated in vacuum. The residue was directly used for next step without further purification. 2-(3-methylisoxazol-5-yl)-4-oxo-butanoic acid (340 mg, crude) as colorless oil was obtained. LC/MS (ESI) m/z: 184.1 $[M+1]^+$.

Step 3: Preparation of 4-(4-(tert-butoxycarbonyl)piperazin-1-yl)-2-(3-methylisoxazol-5-yl)butanoic acid

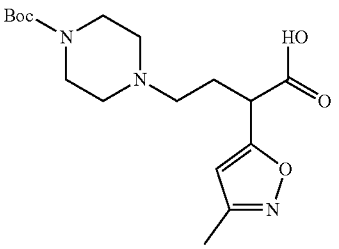 [SMILES: Cc1cc(C(CCN2CCN(C(=O)OC(C)(C)C)CC2)C(=O)O)on1]

To a solution of 2-(3-methylisoxazol-5-yl)-4-oxo-butanoic acid (330 mg, 1.80 mmol, 1 eq) and tert-butyl piperazine-1-carboxylate (335 mg, 1.80 mmol, 1 eq) in a mixture of methanol (3 mL) and dichloromethane (1 mL) was added acetic acid (10 mg, 0.18 mmol, 0.1 eq). The mixture was stirred at 15° C. for half an hour, then sodium cyanoborohydride (169 mg, 2.70 mmol, 1.5 eq) was added to the mixture. The resulting mixture was stirred at 15° C. for another half an hour. The mixture was poured into 20 mL water and the pH was adjusted to 8.0 with saturated sodium bicarbonate solution. The mixture was then extracted with ethyl acetate (20 mL), the organic layer was discard. The aqueous layer was adjusted with 2.0 M sulfuric acid to pH~4.0, extracted with ethyl acetate (30 mL×3). The combined organic layer was dried over sodium sulfate, filtered and concentrated in vacuum. The residue was directly used for next step without further purification. 4-(4-tert-butoxycarbonylpiperazin-1-yl)-2-(3-methylisoxazol-5-yl) butanoic acid (320 mg, crude) as a colorless oil was obtained. LC/MS (ESI) m/z: 354.1 $[M+1]^+$.

Step 4: Preparation of tert-butyl 4-(4-((2S,4R)-4-hydroxy-2-(((S)-1-(4-(4-methylthiazol-5-yl)phenyl)ethyl)carbamoyl)pyrrolidin-1-yl)-3-(3-methylisoxazol-5-yl)-4-oxobutyl)piperazine-1-carboxylate

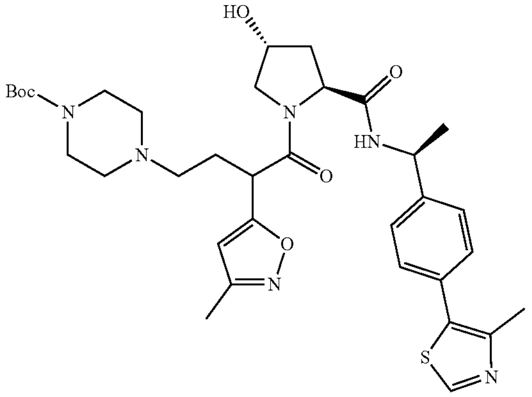 [SMILES: Cc1cc(C(CCN2CCN(C(=O)OC(C)(C)C)CC2)C(=O)N2C[C@H](O)C[C@H]2C(=O)N[C@@H](C)c2ccc(-c3scnc3C)cc2)on1]

To a solution of 4-(4-tert-butoxycarbonylpiperazin-1-yl)-2-(3-methylisoxazol-5-yl)butanoic acid (300 mg, 0.84 mmol, 1 eq), hydroxybenzotriazole (137 mg, 1.02 mmol, 1.2 eq) and carbon diylamine hydrochloride. (244 mg, 1.27 mmol, 1.5 eq) in dimethyl formamide (4 mL) was added (2S,4R)-4-hydroxy-N-[(1S)-1-[4-(4-methylthiazol-5-yl)phenyl]ethyl]pyrrolidine-2-carboxamide (312 mg, 0.84 mmol, 1 eq, hydrochloride) and diisopropylethylamine (219 mg, 1.70 mmol, 2 eq). The mixture was stirred at 20° C. for 2 hours. The mixture was poured into 30 ml saturated brine, extracted with ethyl acetate (30 mL×2). The combined organic layers were washed with brine (30 mL×3), dried over sodium sulfate, filtered and concentrated in vacuum. The residue was further purified prep-HPLC, the fraction was neutralized with sodium bicarbonate solution, extracted with ethyl acetate (50 mL×2). The combined organic layers were washed with saturated brine (30 mL×3), dried over sodium sulfate, filtered and concentrated in vacuum, tert-butyl 4-[4-[(2S,4R)-4-hydroxy-2-[[(1S)-1-[4-(4-methylthiazol-5-yl)phenyl]ethyl]carbamoyl]pyrrolidin-1-yl]-3-(3-methylisoxazol-5-yl)-4-oxo-butyl]piperazine-1-carboxylate (180 mg, 0.27 mmol, 31% yield) as an off-white solid was obtained. $^1H$ NMR (400 MHz, DMSO-$d_6$) δ 8.99 (s, 1H), 8.46-8.35 (m, 1H), 7.47-7.28 (m, 4H), 6.28-6.21 (s, 1H), 5.14 (d, J=3.6 Hz, 1H), 5.02-4.84 (m, 1H), 4.44 (t, J=7.6 Hz, 1H), 4.32-4.09 (m, 2H), 3.63-3.57 (m, 1H), 3.55-3.35 (m, 2H), 3.30 (s, 3H), 2.52 (s, 2H), 2.47-2.45 (m, 3H), 2.31-2.25 (m, 4H), 2.21-2.16 (m, 3H), 2.12-2.00 (m, 2H), 1.95-1.86 (m, 1H), 1.84-1.74 (m, 1H), 1.45-1.30 (m, 12H).

Step 5: Preparation of (2S,4R)-4-hydroxy-1-(2-(3-methylisoxazol-5-yl)-4-(piperazin-1-yl)butanoyl)-N—((S)-1-(4-(4-methylthiazol-5-yl)phenyl)ethyl) pyrrolidine-2-carboxamide

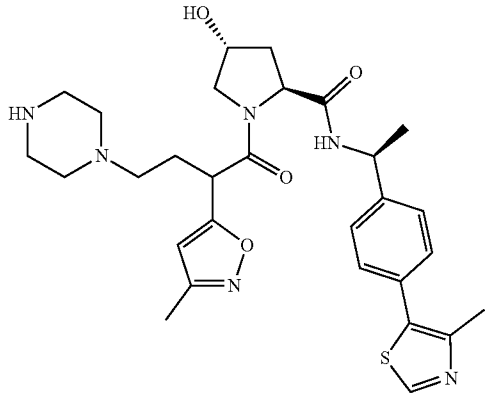 [SMILES: Cc1cc(C(CCN2CCNCC2)C(=O)N2C[C@H](O)C[C@H]2C(=O)N[C@@H](C)c2ccc(-c3scnc3C)cc2)on1]

To a solution of tert-butyl 4-[4-[(2S,4R)-4-hydroxy-2-[[(1S)-1-[4-(4-methylthiazol-5-yl)phenyl]ethyl]carbamoyl] pyrrolidin-1-yl]-3-(3-methylisoxazol-5-yl)-4-oxo-butyl]piperazine-1-carboxylate (80 mg, 0.12 mmol, 1 eq) in dichloromethane (2 mL) was added hydrogen chloride/methanol (4 M, 5 mL, 166.71 eq), and the mixture was stirred at 15° C. for 1 hr. The reaction mixture was concentrated in vacuum to get the residue. The crude product was used into the next step without further purification. The product (2S,4R)-4-hydroxy-1-[2-(3-methylisoxazol-5-yl)-4-piperazin-1-yl-butanoyl]-N-[(1S)-1-[4-(4-methylthiazol-5-yl)phenyl]ethyl]pyrrolidine-2-carboxamide (70 mg, 0.12 mmol, 97% yield, HCl) was obtained as yellow solid. LC/MS (ESI) m/z: 567.2 $[M+1]^+$.

Step 6: Preparation of (2S,4R)-1-(4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-2-(3-methylisoxazol-5-yl)butanoyl)-4-hydroxy-N—((S)-1-(4-(4-methylthiazol-5-yl)phenyl)ethyl)pyrrolidine-2-carboxamide A solution of (2S,4R)-4-hydroxy-1-[2-(3-methylisoxazol-5-yl)-4-piperazin-1-yl-butanoyl]-N-[(1S)-1-[4-(4-methylthiazol-5-yl)phenyl]ethyl]pyrrolidine-2-carboxamide (98 mg, 0.16 umol, 1 eq, Hydrochloride) and sodium acetate (40 mg, 0.49 mmol, 3 eq) in dichloromethane (2 mL) and methanol (3 mL) was stirred at 25° C. for 0.5 h. Then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (100 mg, 0.16 mmol, 1 eq) and acetic acid (9 mg, 0.16 mmol, 1 eq) was added and stirred at 0.5 h. Then sodium cyanoborohydride (30 mg, 0.49 mmol, 3 eq) was added. The reaction mixture was stirred at 25° C. for 0.5 h. The reaction mixture was filtered and concentrated under reduced pressure. The residue was purified by prep-HPLC. The residue was purified by prep-TLC (dichloromethane:methanol=10:1). (2S,4R)-1-[4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]-2-(3-methylisoxazol-5-yl)butanoyl]-4-hydroxy-N-[(1S)-1-[4-(4-methylthiazol-5-yl)phenyl]ethyl]pyrrolidine-2-carboxamide (59 mg, 51.02 umol, 31% yield, 99% purity) was obtained as a yellow solid. LC/MS (ESI) m/z: 1165.3 $[M+1]^+$; $^1$H-NMR (400 MHz, DMSO-$d_6$) δ 12.89 (s, 1H), 9.03-8.94 (m, 1H), 8.64 (s, 1H), 8.53 (s, 1H), 8.44-8.28 (m, 1H), 8.06 (s, 1H), 7.68-7.53 (m, 3H), 7.50-7.22 (m, 6H), 7.06 (d, J=8.8 Hz, 2H), 6.30-6.18 (m, 1H), 5.43-5.10 (m, 2H), 4.98-4.87 (m, 1H), 4.52-4.37 (m, 1H), 4.30 (d, J=4.0 Hz, 1H), 4.24-4.12 (m, 1H), 3.95-3.72 (m, 3H), 3.63-3.51 (m, 2H), 3.44 (s, 6H), 2.72 (t, J=11.6 Hz, 2H), 2.46 (d, J=1.6 Hz, 4H), 2.45-2.25 (m, 10H), 2.22-2.19 (m, 2H), 2.18-1.95 (m, 9H), 1.88-1.62 (m, 5H), 1.39-1.33 (m, 5H), 1.24-1.19 (m, 2H).

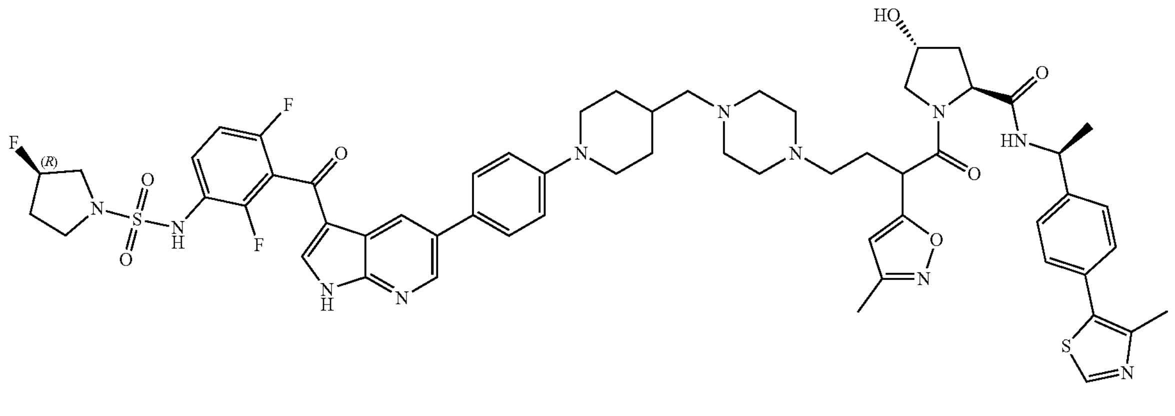

Exemplary Synthesis of (2S,4R)-1-((S)-2-(2-(4-(4-(4-(3-(3-((N-ethyl-N-methylsulfamoyl)amino)-2,6-difluorobenzoyl)-1H-pyrrolo[2,3-b]pyridin-5-yl)phenyl)piperazin-1-yl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Example 480)

Step 1: Preparation of ethyl(methyl)sulfamoyl chloride

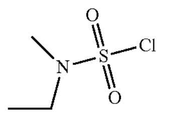

To a solution of N-methylethanamine (500 mg, 8.46 mmol, 1 eq) and triethylamine (856 mg, 8.46 mmol, 1.18 mL, 1 eq) in dichloromethane (8 mL). Then sulfuryl chloride (1.14 g, 8.46 mmol, 1 eq) in dichloromethane (3 mL) was added to the mixture at 0° C. The mixture was stirred at 0° C. for 2 h. The reaction was poured into ice hydrochloric acid (1N, 30 mL). The combined organic phase was washed with brine (50 mL×1) and hydrochloric acid (1 N, 20 mL), dried with anhydrous sodium sulfate, filtered and concentrated in vacuum. The crude product was used into the next step without further purification. Compound N-ethyl-N-methyl-sulfamoyl chloride (1 g, crude) was obtained as a colorless oil.

Step 2: Preparation of [(3-{5-bromo-1H-pyrrolo[2,3-b]pyridine-3-carbonyl}-2,4-difluorophenyl)sulfamoyl](ethyl)methylamine

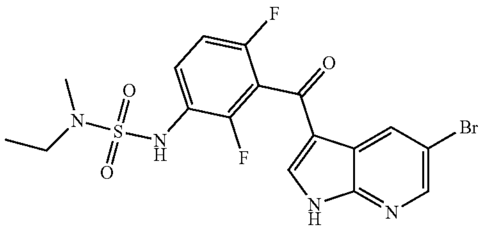 [SMILES: CCN(C)S(=O)(=O)Nc1ccc(F)c(C(=O)c2c[nH]c3ncc(Br)cc23)c1F]

To a solution of (3-amino-2,6-difluoro-phenyl)-(5-bromo-1H-pyrrolo[2,3-b]pyridin-3-yl) methanone (1.19 g, 3.38 mmol, 1 eq) in PYRIDINE (5 mL) was added 4-dimethylaminopyridine (82 mg, 0.67 mmol, 0.2 eq) and N-ethyl-N-methyl-sulfamoyl chloride (800 mg, 5.08 mmol, 1.5 eq). The mixture was stirred at 40° C. for 12 h. The reaction mixture was adjusted pH to 8 with saturated aqueous sodium bicarbonate. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by prep-HPLC. Compound 5-bromo-3-[3-[[ethyl(methyl)sulfamoyl]amino]-2,6-difluoro-benzoyl]-1H-pyrrolo[2,3-b]pyridine (550 mg, 1.16 mmol, 34% yield) was obtained as a yellow solid. LC/MS (ESI) m/z: 474.9 [M+1]$^+$.

Step 3: Preparation of {[3-(5-bromo-1-{[2-(trimethylsilyl)ethoxy]methyl}-1H-pyrrolo[2,3-b]pyridine-3-carbonyl)-2,4-difluorophenyl]({[2-(trimethylsilyl)ethoxy]methyl}) sulfamoyl}(ethyl)methylamine

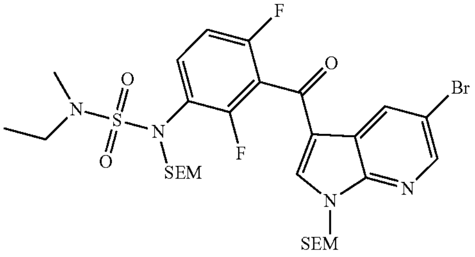 [SMILES: CCN(C)S(=O)(=O)N(COCC[Si](C)(C)C)c1ccc(F)c(C(=O)c2cn(COCC[Si](C)(C)C)c3ncc(Br)cc23)c1F]

To a solution of 5-bromo-3-[3-[[ethyl(methyl)sulfamoyl]amino]-2,6-difluoro-benzoyl]-1H-pyrrolo[2,3-b]pyridine (550 mg, 1.16 mmol, 1 eq) in N,N-dimethylformamide (6 mL) was added sodium hydride (139 mg, 3.49 mmol, 60% purity, 3 eq) and (2-(chloromethoxy)ethyl)trimethylsilane (484 mg, 2.91 mmol, 2.5 eq). The mixture was stirred at 40° C. for 12 h. Water (100 mL) was poured into the mixture and stirred for 1 minute. The aqueous phase was extracted with ethyl acetate (70 mL×3). The combined organic phase was washed with brine (100 mL×2), dried with anhydrous sodium sulfate, filtered and concentrated in vacuum. The residue was purified by column chromatography (petroleum ether:ethyl acetate=1:0 to 20:1). Compound [5-bromo-1-(2-trimethylsilylethoxymethyl)pyrrolo[2,3-b]pyridin-3-yl]-[3-[[ethyl(methyl)sulfamoyl]-(2-trimethylsilylethoxymethyl)amino]-2,6-difluoro-phenyl]methanone (550 mg, 0.74 mmol, 64% yield) was obtained as a light yellow oil. LC/MS (ESI) m/z: 734.8 [M+1]$^+$.

Step 4: Preparation of tert-butyl 2-(4-(4-(4-(3-(3-((N-ethyl-N-methylsulfamoyl)((2-(trimethylsilyl)ethoxy)methyl)amino)-2,6-difluorobenzoyl)-1-((2-(trimethylsilyl)ethoxy)methyl)-1H-pyrrolo[2,3-b]pyridin-5-yl)phenyl)piperazin-1-yl)piperidin-1-yl)acetate

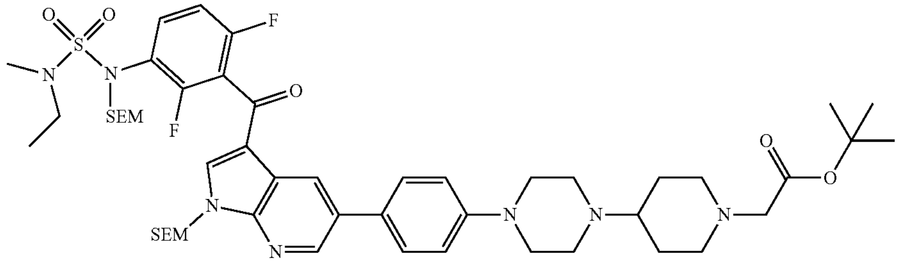 [SMILES: CCN(C)S(=O)(=O)N(COCC[Si](C)(C)C)c1ccc(F)c(C(=O)c2cn(COCC[Si](C)(C)C)c3ncc(-c4ccc(N5CCN(C6CCN(CC(=O)OC(C)(C)C)CC6)CC5)cc4)cc23)c1F]

To a solution of [5-bromo-1-(2-trimethylsilylethoxymethyl)pyrrolo[2,3-b]pyridin-3-yl]-[3-[[ethyl(methyl)sulfamoyl]-(2-trimethylsilylethoxymethyl)amino]-2,6-difluoro-phenyl]methanone (350 mg, 0.47 mmol, 1 eq) and tert-butyl 2-[4-[4-[4-(4,4,5,5-tetramethyl-1,3,2-dioxaborolan-2-yl)phenyl]piperazin-1-yl]-1-piperidyl]acetate (231 mg, 0.47 mmol, 1 eq) in dioxane (3 mL) and water (0.3 mL) was added cesium fluoride (289 mg, 1.91 mmol, 4 eq) and 4-ditert-butylphosphanyl-N,N-dimethyl-aniline;dichloropalladium (33 mg, 0.04 mmol, 0.1 eq). The mixture was stirred at 90° C. for 3 h. Water (80 mL) was poured into the mixture and stirred for 1 minute. The aqueous phase was extracted with ethyl acetate (40 mL×3). The combined organic phase was washed with brine (100 mL×2), dried with anhydrous sodium sulfate, filtered and concentrated in vacuum. The residue was purified by column chromatography (petroleum ether:ethyl acetate=1:0 to 5:1) Compound tert-butyl 2-[4-[4-[4-[3-[3-[[ethyl(methyl)sulfamoyl]-(2-trimethylsilylethoxymethyl)amino]-2,6-difluoro-benzoyl]-1-(2-trimethylsilylethoxymethyl)pyrrolo[2,3-b]pyridin-5-yl]phenyl]piperazin-1-yl]-1-piperidyl]acetate (250 mg, 0.24 mmol, 51% yield) was obtained as a yellow solid. LC/MS (ESI) m/z: 506.3 $[M/2]^+$.

Step 5: Preparation of methyl 2-(4-(4-(4-(3-(3-((N-ethyl-N-methylsulfamoyl)amino)-2,6-difluorobenzoyl)-1H-pyrrolo[2,3-b]pyridin-5-yl)phenyl)piperazin-1-yl)piperidin-1-yl)acetate

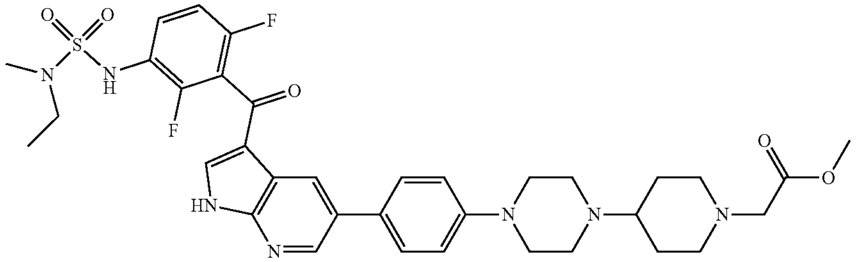

To a solution of tert-butyl 2-[4-[4-[4-[3-[3-[[ethyl(methyl)sulfamoyl]-(2-trimethylsilylethoxymethyl)amino]-2,6-difluoro-benzoyl]-1-(2-trimethylsilylethoxymethyl)pyrrolo[2,3-b]pyridin-5-yl]phenyl]piperazin-1-yl]-1-piperidyl]acetate (250 mg, 0.24 mmol, 1 eq) in methanol (2 mL) was added hydrochloric acid/dioxane (4 M, 10 mL, 161.98 eq). The mixture was stirred at 40° C. for 12 h. The reaction mixture concentrated under reduced pressure. The crude product was used into the next step without further purification. Compound methyl 2-[4-[4-[4-[3-[3-[[ethyl(methyl)sulfamoyl]amino]-2,6-difluoro-benzoyl]-1H-pyrrolo[2,3-b]pyridin-5-yl]phenyl]piperazin-1-yl]-1-piperidyl]acetate (175 mg, crude) was obtained as a yellow oil. LC/MS (ESI) m/z: 701.1 $[M/2+1]^+$.

Step 6: Preparation of 2-(4-(4-(4-(3-(3-((N-ethyl-N-methylsulfamoyl)amino)-2,6-difluorobenzoyl)-1H-pyrrolo[2,3-b]pyridin-5-yl)phenyl)piperazin-1-yl)piperidin-1-yl)acetic acid

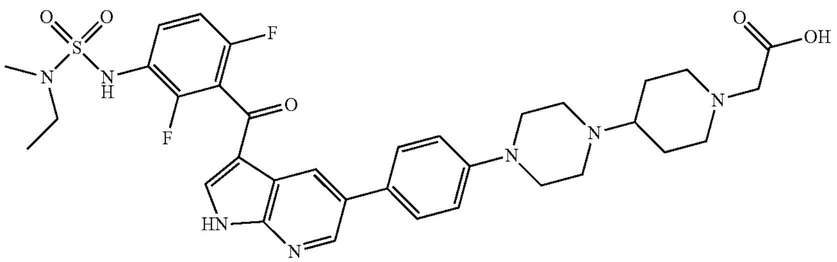 [SMILES: CCN(C)S(=O)(=O)Nc1ccc(F)c(C(=O)c2c[nH]c3ncc(-c4ccc(N5CCN(C6CCN(CC(=O)O)CC6)CC5)cc4)cc23)c1F]

To a solution of methyl 2-[4-[4-[4-[3-[3-[[ethyl(methyl) sulfamoyl]amino]-2,6-difluoro-benzoyl]-1H-pyrrolo[2,3-b] pyridin-5-yl]phenyl]piperazin-1-yl]-1-piperidyl]acetate (175 mg, 0.24 mmol, 1 eq) in tetrahydrofuran (2 mL), methanol (2 mL) and water (1 mL) was added lithium hydroxide monohydrate (41 mg, 0.98 mmol, 4 eq). The mixture was stirred at 40° C. for 1 h. The reaction mixture concentrated under reduced pressure. The reaction mixture was adjusted pH to 7 with hydrochloric acid (1 M). The precipitate was collected by filtration. The crude product was used into the next step without further purification. Compound 2-[4-[4-[4-[3-[3-[[ethyl(methyl)sulfamoyl] amino]-2,6-difluoro-benzoyl]-1H-pyrrolo[2,3-b]pyridin-5-yl]phenyl]piperazin-1-yl]-1-piperidyl]acetic acid (100 mg, 0.14 mmol, 58% yield) was obtained as a yellow solid. LC/MS (ESI) m/z: 696.1 $[M+1]^+$.

Step 7: Preparation of (2S,4R)-1-((S)-2-(2-(4-(4-(4-(3-(3-((N-ethyl-N-methylsulfamoyl)amino)-2,6-difluorobenzoyl)-1H-pyrrolo[2,3-b]pyridin-5-yl)phenyl)piperazin-1-yl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

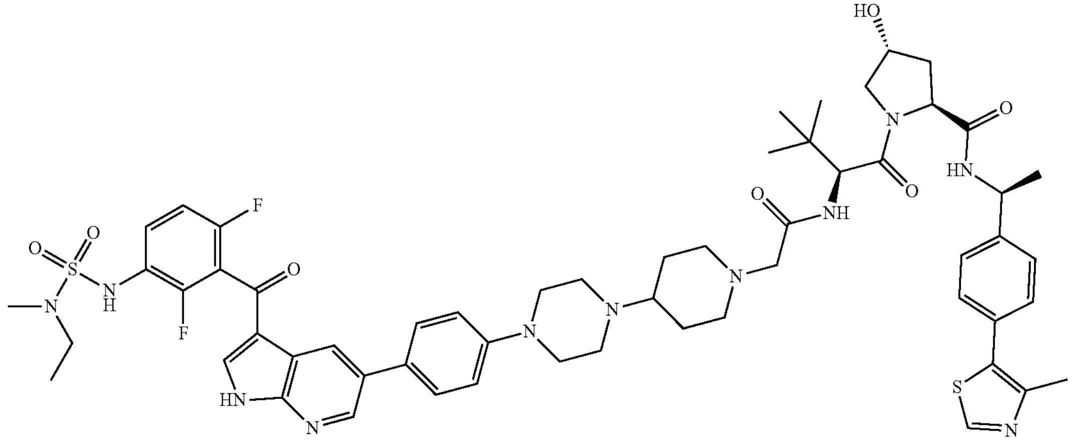

To a solution of 2-[4-[4-[4-[3-[3-[[ethyl(methyl)sulfamoyl]amino]-2,6-difluoro-benzoyl]-1H-pyrrolo[2,3-b]pyridin-5-yl]phenyl]piperazin-1-yl]-1-piperidyl]acetic acid (100 mg, 0.14 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (69 mg, 0.14 mmol, 1.00 eq, hydrochloride) in N,N-dimethylformamide (2 mL) was added hydroxybenzotriazole (23 mg, 0.17 mmol, 1.2 eq), triethylamine (22 mg, 0.21 mmol, 1.5 eq) and 1-(3-dimethylaminopropyl)-3-ethylcarbodiimide hydrochloride (33 mg, 0.17 mmol, 1.2 eq). The mixture was stirred at 30° C. for 12 h. Water (50 mL) was poured into the mixture and stirred for 1 minute. The aqueous phase was extracted with dichloromethane (20 mL×3). The combined organic phase was washed with brine (20 mL×2), dried with anhydrous sodium sulfate, filtered and concentrated in vacuum. The residue was purified by prep-HPLC. Compound (2S,4R)-1-[(2S)-2-[[2-[4-[4-[4-[3-[3-[[ethyl(methyl) sulfamoyl]amino]-2,6-difluoro-benzoyl]-1H-pyrrolo[2,3-b] pyridin-5-yl]phenyl]piperazin-1-yl]-1-piperidyl]acetyl] amino]-3,3-dimethyl-butanoyl]-4-hydroxy-N-[(1S)-1-[4-(4-methylthiazol-5-yl)phenyl]ethyl]pyrrolidine-2-carboxamide (105.2 mg, 0.093 mmol, 65% yield, 100% purity) was obtained as a yellow solid. LC/MS (ESI) m/z: 562.0 $[M/2+1]^+$; $^1$H-NMR (400 MHz, DMSO-$d_6$) δ 13.15-12.64 (m, 1H), 8.98 (s, 1H), 8.65 (d, J=2.0 Hz, 1H), 8.57-8.43 (m, 2H), 8.18 (s, 1H), 8.09 (s, 1H), 7.77 (d, J=9.2 Hz, 1H), 7.64-7.55 (m, 3H), 7.47-7.41 (m, 2H), 7.40-7.33 (m, 2H), 7.27 (t, J=8.4 Hz, 1H), 7.07 (d, J=8.8 Hz, 2H), 4.94-4.85 (m, 1H), 4.53-4.41 (m, 2H), 4.28 (s, 1H), 3.14-3.06 (m, 4H), 3.03 (s, 1H), 2.90 (d, J=16.0 Hz, 3H), 2.72 (s, 3H), 2.67 (s, 4H), 2.45 (s, 4H), 2.30-2.18 (m, 2H), 2.17 (s, 1H), 2.14-2.02 (m, 2H), 2.14-2.02 (m, 1H), 1.86 (s, 2H), 1.79-1.72 (m, 1H), 1.57-1.42 (m, 3H), 1.38 (d, J=7.2 Hz, 3H), 1.01 (t, J=7.2 Hz, 3H), 0.95 (s, 9H).

Exemplary Synthesis of (2S,4R)-1-((S)-2-(2-((2S,6R)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-dimethylpiperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Example 351)

Step 1: Preparation of tert-butyl (3S,5R)-4-(2-ethoxy-2-oxoethyl)-3,5-dimethylpiperazine-1-carboxylate

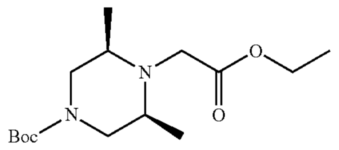 [SMILES: CCOC(=O)CN1[C@H](C)CN(C(=O)OC(C)(C)C)C[C@@H]1C]

To a solution of tert-butyl (3S, 5R)-3,5-dimethylpiperazine-1-carboxylate (1 g, 4.67 mmol, 1 eq) and ethyl 2-bromoacetate (701 mg, 4.20 mmol, 0.9 eq) in acetonitrile (10 mL) was added diisopropyl ethyl amine (1.81 g, 14.00 mmol, 3 eq). The reaction mixture was stirred at 80° C. for 12 hours. The reaction mixture was diluted with water (50 mL) and extracted with ethyl acetate (50 mL×3). The combined organic layers were washed with brine (80 mL×2), dried over anhydrous sodium sulfate, filtered and concentrated under reduced pressure. The residue was purified by silica gel column chromatography (Petroleum ether/Ethyl acetate=30/1 to 1/1). tert-butyl (3S,5R)-4-(2-ethoxy-2-oxo-ethyl)-3,5-dimethyl-piperazine-1-carboxylate (1.09 g, 3.63 mmol, 77% yield) was obtained as a white solid. LC/MS (ESI) m/z: 301.1 $[M+1]^+$; $^1$H-NMR (400 MHz, $CDCl_3$) δ 4.16 (q, J=7.2 Hz, 2H), 4.02-3.72 (m, 2H), 3.56 (s, 2H), 2.96-2.82 (m, 2H), 2.53 (s, 2H), 1.46 (s, 9H), 1.27 (t, J=7.2 Hz, 3H), 1.08 (d, J=6.4 Hz, 6H).

Step 2: Preparation of ethyl 2-((2S,6R)-2,6-dimethylpiperazin-1-yl)acetate

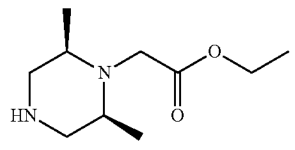

To a solution of tert-butyl (3S, 5R)-4-(2-ethoxy-2-oxo-ethyl)-3,5-dimethyl-piperazine-1-carboxylate (200 mg, 0.66 mmol, 1 eq) in dichloromethane (10 mL) was added hydrochloric acid (4 M in dioxane, 2 mL, 10 eq). The reaction mixture was stirred at 15° C. for 1 hour. The reaction mixture was concentrated under reduced pressure, ethyl 2-[(2S,6R)-2,6-dimethylpiperazin-1-yl]acetate (140 mg, 0.59 mmol, 88% yield, Hydrochloride) was obtained as a white solid.

Step 3: Preparation of ethyl 2-((2S,6R)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-dimethylpiperazin-1-yl)acetate

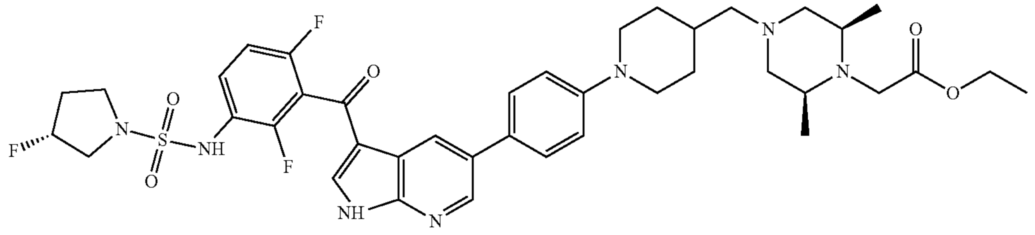 [SMILES: CCOC(=O)CN1[C@H](C)CN(CC2CCN(c3ccc(-c4cnc5[nH]cc(C(=O)c6c(F)ccc(NS(=O)(=O)N7CC[C@@H](F)C7)c6F)c5c4)cc3)CC2)C[C@@H]1C]

To a solution ethyl 2-[(2S,6R)-2,6-dimethylpiperazin-1-yl]acetate (69 mg, 0.29 mmol, 1.2 eq, Hydrochloride) and triethylamine (74 mg, 0.73 mmol, 3 eq) in methanol (2 mL) and dichloromethane (2 mL) was added (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (150 mg, 0.24 mmol, 1 eq). The reaction mixture was stirred at 15° C. for 0.5 hour. Sodium triacetoxyborohydride (155 mg, 0.73 mmol, 3 eq) was added. The reaction mixture was stirred at 15° C. for 0.5 hour. The reaction mixture was diluted with water (50 mL) and extracted with ethyl acetate (50 mL×3). The combined organic layers were washed with brine (50 mL×3), dried over anhydrous sodium sulfate, filtered and concentrated under reduced pressure. The residue was purified by silica gel column chromatography (Petroleum ether/Ethyl acetate=100/1 to 30/1). ethyl 2-[(2S,6R)-4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-dimethyl-piperazin-1-yl]acetate (180 mg, 0.22 mmol, 92% yield) was obtained as a yellow solid. LC/MS (ESI) m/z: 796.1 $[M+1]^+$; $^1$H-NMR (400 MHz, DMSO-$d_6$) δ 12.91 (s, 1H), 9.87 (s, 1H), 8.64 (d, J=2.0 Hz, 1H), 8.53 (s, 1H), 8.07 (s, 1H), 7.67-7.52 (m, 3H), 7.27 (t, J=8.4 Hz, 1H), 7.05 (d, J=8.8 Hz, 2H), 5.46-5.12 (m, 1H), 4.16-4.00 (m, 3H), 3.77 (d, J=12.0 Hz, 2H), 3.50-3.43 (m, 3H), 3.39 (s, 2H), 3.32-3.24 (m, 2H), 3.16 (d, J=5.2 Hz, 1H), 2.85 (s, 2H), 2.76-2.62 (m, 4H), 2.09 (d, J=7.2 Hz, 4H), 1.84-1.59 (m, 5H), 1.25-1.13 (m, 5H), 0.96 (d, J=6.0 Hz, 6H).

Step 4: Preparation of 2-((2S,6R)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-dimethylpiperazin-1-yl)acetic acid

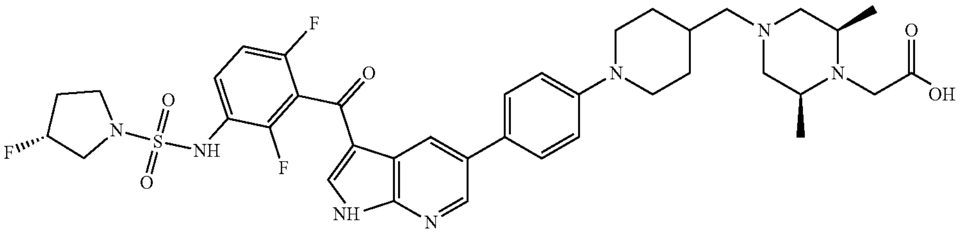 [SMILES: C[C@@H]1CN(CC2CCN(c3ccc(-c4cnc5[nH]cc(C(=O)c6c(F)ccc(NS(=O)(=O)N7CC[C@@H](F)C7)c6F)c5c4)cc3)CC2)C[C@H](C)N1CC(=O)O]

To a solution of ethyl 2-[(2S,6R)-4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-dimethyl-piperazin-1-yl]acetate (150 mg, 0.18 mmol, 1 eq) in methanol (4 mL), water (4 mL) and tetrahydrofuran (4 mL) was added lithium hydroxide monohydrate (31 mg, 0.75 mmol, 4 eq). The reaction mixture was stirred at 15° C. for 2 hours. The pH was adjusted to 6 with 1 M hydrochloric acid, concentrated under reduced pressure. The residue was purified by prep-HPLC. 2-[(2S,6R)-4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-dimethyl-piperazin-1-yl]acetic acid (110 mg, 0.13 mmol, 71% yield, formate) was obtained as a yellow solid.

Step 5: Preparation of (2S,4R)-1-((S)-2-(2-((2S,6R)-4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-dimethylpiperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide To a solution of 2-[(2S,6R)-4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-dimethyl-piperazin-1-yl]acetic acid (70 mg, 0.09 mmol, 1 eq), hydroxybenzotriazole (24 mg, 0.18 mmol, 2 eq), 1-(3-dimethylaminopropyl)-3-ethylcarbodiimide hydrochloride (34 mg, 0.18 mmol, 2 eq) in dimethylformamide (5 mL) was added (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (65 mg, 0.13 mmol, 1.5 eq, Hydrochloride) and triethylamine (46 mg, 0.45 mmol, 5 eq). The reaction mixture was stirred at 40° C. for 12 hours. The pH was adjusted to 6 with 1 M hydrochloric acid. The residue was purified by prep-HPLC. (2S,4R)-1-[(2S)-2-[[2-[(2S,6R)-4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-dimethyl-piperazin-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (41 mg, 0.032 mmol, 35% yield, 97% purity, formate) was obtained as a yellow solid. LC/MS (ESI) m/z: 848.2 $[M+1]^+$; $^1$H-NMR (400 MHz, DMSO-$d_6$) δ 8.98 (s, 1H), 8.64 (d, J=2.0 Hz, 1H), 8.49 (d, J=7.5 Hz, 1H), 8.21 (s, 1H), 8.07 (s, 1H), 8.02-7.94 (m, 1H), 7.67-7.53 (m, 3H), 7.47-7.41 (m, 2H), 7.39-7.32 (m, 2H), 7.25 (t, J=8.4 Hz, 1H), 7.06 (d, J=8.8 Hz, 2H), 5.39-5.19 (m, 1H), 4.93-4.86 (m, 1H), 4.51-4.42 (m, 2H), 4.27 (s, 1H), 3.79 (s, 1H), 3.32-3.24 (m, 4H), 3.14 (d, J=18.0 Hz, 3H), 2.96 (d, J=18.0 Hz, 2H), 2.82-2.67 (m, 4H), 2.57 (s, 2H), 2.45 (s, 4H), 2.17-1.92 (m, 6H), 1.90-1.61 (m, 7H), 1.41-1.35 (m, 3H), 1.21 (d, J=11.6 Hz, 2H), 0.98 (d, J=6.0 Hz, 3H), 0.94 (s, 10H), 0.86 (d, J=6.0 Hz, 3H), 0.89-0.83 (m, 1H).

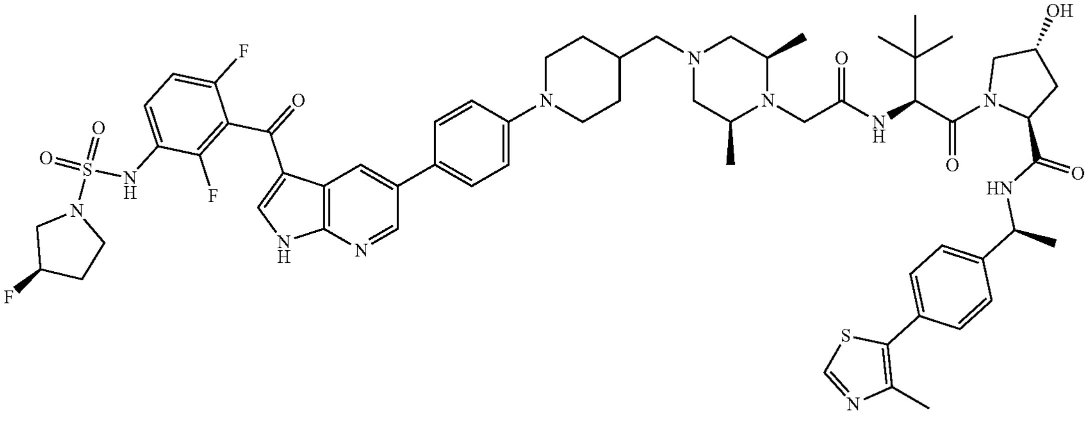 [SMILES: Cc1ncsc1-c1ccc([C@H](C)NC(=O)[C@@H]2C[C@@H](O)CN2C(=O)[C@@H](NC(=O)CN2[C@H](C)CN(CC3CCN(c4ccc(-c5cnc6[nH]cc(C(=O)c7c(F)ccc(NS(=O)(=O)N8CC[C@@H](F)C8)c7F)c6c5)cc4)CC3)C[C@@H]2C)C(C)(C)C)cc1]

Exemplary Synthesis of (2S,4R)-1-((S)-2-(1-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)cyclopropane-1-carboxamido)-3,3-dimethylbutanoyl)-4-hydroxy-N—((S)-1-(4-(4-methylthiazol-5-yl)phenyl)ethyl)pyrrolidine-2-carboxamide (Example 361)

Step 1: Preparation of benzyl 3,4-dihydroxypyrrolidine-1-carboxylate

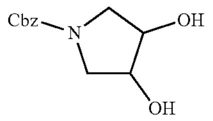 [SMILES: O=C(OCc1ccccc1)N1CC(O)C(O)C1]

To a solution of benzyl 2,5-dihydropyrrole-1-carboxylate (10 g, 49.20 mmol, 1 eq) in tertiary butanol (120 mL) and water (100 mL) was added potassium ferricyanide (40.50 g, 123.01 mmol, 2.5 eq), potassium carbonate (17.00 g, 123.01 mmol, 2.5 eq), methanesulfonamide (4.68 g, 49.20 mmol, 1 eq) and potassium osmate(vi) dihydrate (1.81 g, 4.92 mmol, 0.1 eq). The mixture was stirred at 0-5° C. for 12 hours. The reaction mixture was quenched with saturated sodium sulfite (50 mL). The reaction mixture was diluted with water (500 mL) and extracted with ethyl acetate (200 mL×2). The combined organic phase was washed with saturated brine (200 mL×2), dried with anhydrous sodium sulfate, filtered and concentrated in vacuum. The residue was purified by silica gel chromatography (dichloromethane:methanol=100:1 to 30:1). benzyl 3,4-dihydroxypyrrolidine-1-carboxylate (14 g, crude) was obtained as a yellow oil. LC/MS (ESI) m/z: 260.0 $[M+23]^+$.

Step 2: Preparation of benzyl bis(2-oxoethyl)carbamate

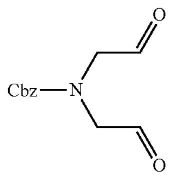 [SMILES: O=CCN(CC=O)C(=O)OCc1ccccc1]

To a solution of benzyl 3,4-dihydroxypyrrolidine-1-carboxylate (1 g, 4.21 mmol, 1 eq) in tetrahydrofuran (20 mL) and water (10 mL) was added sodium periodate (1.35 g, 6.32 mmol, 1.5 eq). The mixture was stirred at 15° C. for 2 h. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The crude product was used into the next step without further purification. Benzyl N,N-bis(2-oxoethyl)carbamate (900 mg, 3.83 mmol, 90% yield) was obtained as a yellow oil.

Step 3: Preparation of benzyl 4-(1-(methoxycarbonyl)cyclopropyl)piperazine-1-carboxylate

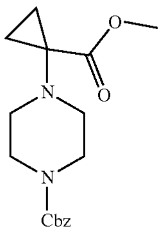 [SMILES: COC(=O)C1(N2CCN(C(=O)OCc3ccccc3)CC2)CC1]

To a solution of benzyl N,N-bis(2-oxoethyl)carbamate (3.29 g, 13.99 mmol, 2 eq) in methanol (30 mL) was added methyl 1-aminocyclopropanecarboxylate (805 mg, 6.99 mmol, 1 eq) and acetic acid (2 mL). The mixture as stirred at 15° C. for 30 min. borane;2-methylpyridine (1.50 g, 13.99 mmol, 2 eq) was added, then the mixture was stirred at 15° C. for another 11.5 hours. The reaction mixture concentrated under reduced pressure. The residue was purified by Flash C18 chromatography (acetonitrile/water (0.5% TFA)=5%~90%). The mixture was concentrated in reduced pressure. Saturated aqueous sodium bicarbonate (30 mL) was added. The aqueous phase was extracted with ethyl acetate (50 mL×3). The combined organic phase was washed with brine (50 mL×2), dried with anhydrous sodium sulfate, filtered and concentrated in vacuum. Compound benzyl 4-(1-methoxycarbonylcyclopropyl)piperazine-1-carboxylate (2.20 g, 6.91 mmol, 98% yield) was obtained as a colorless oil. LC/MS (ESI) m/z 319.1 $[M+1]^+$; $^1$H NMR (400 MHz, $CDCl_3$) δ 7.39-7.35 (m, 4H), 7.35-7.30 (m, 1H), 5.15 (s, 2H), 3.66 (s, 3H), 3.62-3.04 (m, 4H), 2.92 (s, 4H), 1.33-1.28 (m, 2H), 0.96 (q, J=3.6 Hz, 2H).

Step 4: Preparation of methyl 1-(piperazin-1-yl)cyclopropane-1-carboxylate

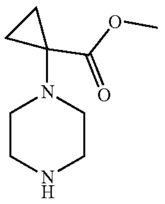

To a solution of benzyl 4-(1-methoxycarbonylcyclopropyl)piperazine-1-carboxylate (2.2 g, 6.91 mmol, 1 eq) in tetrahydrofuran (30 mL) was added palladium on carbon (30 mg, 10%) under nitrogen. The suspension was degassed under vacuum and purged with hydrogen several times. The mixture was stirred under hydrogen (15 psi) at 30° C. for 12 hours. The mixture was then stirred under hydrogen (50 psi) at 30° C. for 16 hours. The reaction mixture was filtered and the filtrate was concentrated, methyl 1-piperazin-1-ylcyclopropanecarboxylate (1.05 g, crude) was obtained as colorless oil. LC/MS (ESI) m/z: 185.1 $[M+1]^+$; $^1$H-NMR (400 MHz, $CDCl_3$) δ 3.74-3.59 (m, 3H), 3.02-2.81 (m, 4H), 2.79-2.73 (m, 3H), 2.43-2.22 (m, 1H), 1.73-1.49 (m, 1H), 1.30-1.22 (m, 2H), 0.98-0.87 (m, 2H).

Step 5: Preparation of methyl (R)-1-(4-((1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)methyl)piperazin-1-yl)cyclopropane-1-carboxylate

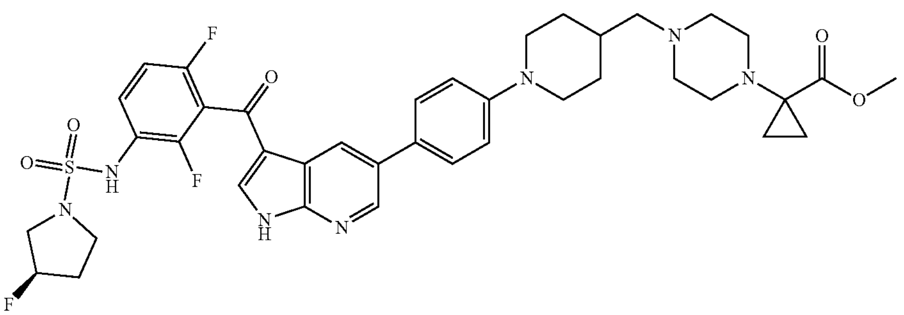 [SMILES: COC(=O)C1(N2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)CC1]

To a solution of methyl 1-piperazin-1-ylcyclopropanecarboxylate (72 mg, 0.39 mmol, 1.2 eq) and (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (200 mg, 0.32 mmol, 1 eq) in 1,2-dichloroethane (2 mL) was added sodium triacetoxyborohydride (207 mg, 0.98 mmol, 3 eq). The mixture was stirred at 15° C. for 1 hour. Water (50 mL) was poured into the mixture and stirred for 1 minute. The aqueous phase was extracted with dichloromethane (30 mL×3). The combined organic phase was washed with brine (30 mL×2), dried with anhydrous sodium sulfate, filtered and concentrated in vacuum. The residue was purified by silica gel chromatography (dichloromethane:methanol=200:1 to 50:1). Compound methyl 1-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]cyclopropanecarboxylate (210 mg, 0.26 mmol, 82% yield) was obtained as a yellow solid. LC/MS (ESI) m/z: 780.1 $[M+1]^+$.

Step 6: Preparation of (R)-1-(4-((1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)methyl)piperazin-1-yl)cyclopropane-1-carboxylic acid

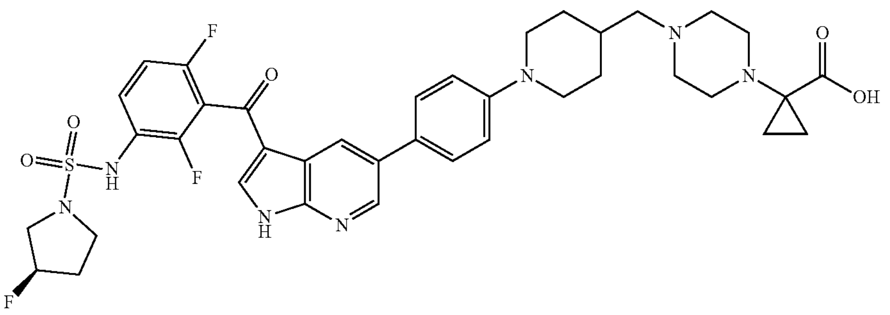 [SMILES: O=C(c1c(F)ccc(NS(=O)(=O)N2CC[C@@H](F)C2)c1F)c1c[nH]c2ncc(-c3ccc(N4CCC(CN5CCN(C6(C(=O)O)CC6)CC5)CC4)cc3)cc12]

To a solution of methyl 1-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]cyclopropanecarboxylate (210 mg, 0.26 mmol, 1 eq) in methanol (2 mL), tetrahydrofuran (2 mL) and water (2 mL) was added lithium hydroxide monohydrate (45 mg, 1.08 mmol, 4 eq). The mixture was stirred at 40° C. for 12 hours. The reaction mixture was adjusted pH to 5 with hydrochloride acid (1 M) and then concentrated under reduced. The crude product was used into the next step without further purification. Compound 1-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]cyclopropanecarboxylic acid (200 mg, contained inorganic salt) was obtained as a yellow oil. LC/MS (ESI) m/z: 766.4 $[M+1]^+$.

Step 7: Preparation of (2S,4R)-1-((S)-2-(1-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) cyclopropane-1-carboxamido)-3,3-dimethylbutanoyl)-4-hydroxy-N—((S)-1-(4-(4-methylthiazol-5-yl)phenyl)ethyl)pyrrolidine-2-carboxamide

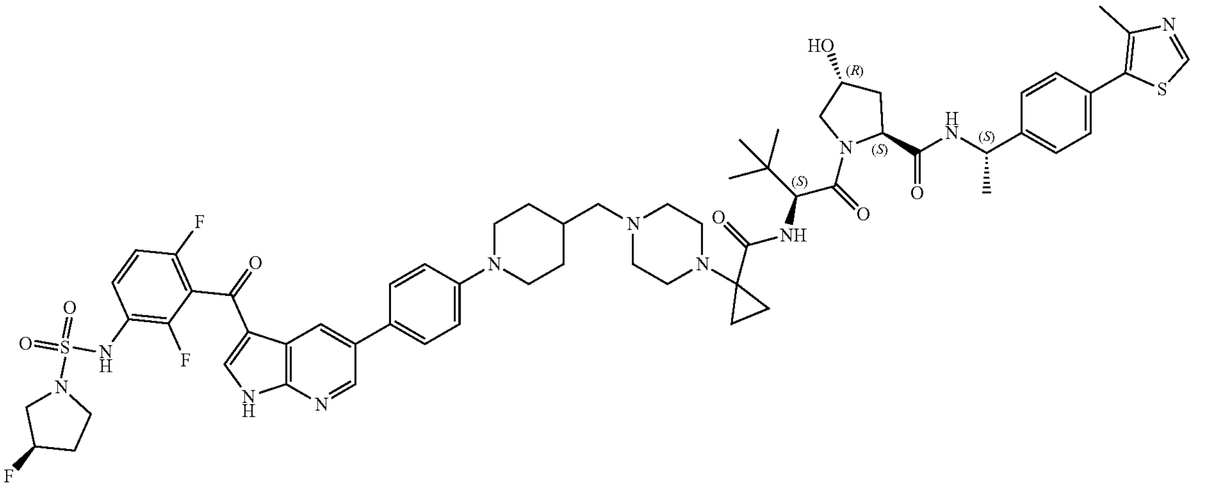

To a solution of 1-[4-[[1-[4-[3-[2,6-difluoro-3-[[(3R)-3-fluoropyrrolidin-1-yl]sulfonylamino]benzoyl]-1H-pyrrolo [2,3-b]pyridin-5-yl]phenyl]-4-piperidyl]methyl]piperazin-1-yl]cyclopropanecarboxylic acid (200 mg, 0.26 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl] pyrrolidine-2-carboxamide (125 mg, 0.26 mmol, 1 eq, hydrochloride) in N,N-dimethylformamide (5 mL) was added hydroxybenzotriazole (42 mg, 0.31 mmol, 1.2 eq), triethylamine (39 mg, 0.39 mmol, 1.5 eq) and 1-(3-dimethylaminopropyl)-3-ethylcarbodiimide hydrochloride (60 mg, 0.31 mmol, 1.2 eq). The mixture was stirred at 40° C. for 12 hours. Water (50 mL) was poured into the mixture and stirred for 1 minute. The aqueous phase was extracted with dichloromethane (10 mL×3). The combined organic phase was washed with brine (10 mL×2), dried with anhydrous sodium sulfate, filtered and concentrated in vacuum. The residue was purified by prep-HPLC. Compound (2S,4R)-1-[(2S)-2-[[1-[4-[[1-[4-[3-[2,6-difluoro-3-[[(3R)-3-fluoropyrrolidin-1-yl]sulfonylamino]benzoyl]-1H-pyrrolo[2,3-b] pyridin-5-yl]phenyl]-4-piperidyl]methyl]piperazin-1-yl] cyclopropanecarbonyl]amino]-3,3-dimethyl-butanoyl]-4-hydroxy-N-[(1S)-1-[4-(4-methylthiazol-5-yl)phenyl]ethyl] pyrrolidine-2-carboxamide (27.3 mg, 0.022 mmol, 8% yield for 2 steps, 99% purity, formate) was obtained as a yellow solid. LC/MS (ESI) m/z: 596.9 $[M/2+1]^+$; $^1$H-NMR (400 MHz, DMSO-$d_6$) δ 13.16-12.44 (m, 1H), 8.98 (s, 1H), 8.64 (d, J=2.0 Hz, 1H), 8.51 (s, 1H), 8.45 (d, J=7.6 Hz, 1H), 8.36 (d, J=10.0 Hz, 1H), 8.23 (s, 1H), 8.04 (s, 1H), 7.65-7.55 (m, 3H), 7.46-7.41 (m, 2H), 7.40-7.32 (m, 2H), 7.21 (t, J=8.8 Hz, 1H), 7.06 (d, J=8.8 Hz, 2H), 5.39-5.18 (m, 1H), 4.95-4.83 (m, 1H), 4.53-4.40 (m, 2H), 4.28 (s, 1H), 3.77 (d, J=12.8 Hz, 2H), 3.58 (d, J=7.6 Hz, 1H), 3.45 (s, 1H), 3.27 (d, J=6.8 Hz, 3H), 2.72 (t, J=11.2 Hz, 2H), 2.46 (s, 3H), 2.40 (s, 6H), 2.21 (d, J=6.8 Hz, 3H), 2.13-2.00 (m, 4H), 1.85-1.65 (m, 5H), 1.40 (d, J=7.2 Hz, 3H), 1.30-1.15 (m, 2H), 1.08 (d, J=7.0 Hz, 1H), 1.04-0.89 (m, 13H).

Exemplary Synthesis of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-1,4-diazepan-1-yl) acetamido)-3,3-dimethylbutanoyl)-4-hydroxy-N—((S)-1-(4-(4-methylthiazol-5-yl)phenyl)ethyl) pyrrolidine-2-carboxamide (Example 412)

Step 1: Preparation of benzyl 4-(2-(tert-butoxy)-2-oxoethyl)-1,4-diazepane-1-carboxylate

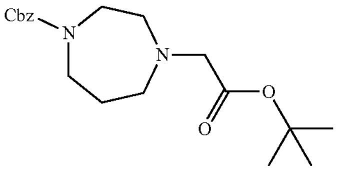 [SMILES: CC(C)(C)OC(=O)CN1CCCN(C(=O)OCc2ccccc2)CC1]

To a solution of benzyl 1,4-diazepane-1-carboxylate (0.85 g, 3.63 mmol, 1 eq) in acetonitrile (10 mL) was added N,N-diisopropylethylamine (938 mg, 7.26 mmol, 2 eq), tert-butyl 2-bromoacetate (707 mg, 3.63 mmol, 0.5 mL, 1 eq). The mixture was stirred at 70° C. for 2 h. The reaction mixture was extracted with ethyl acetate (40 mL×2). The combined organic layers were washed with saturated aqueous brine (30 mL×2) and dried over anhydrous sodium sulfate, filtered and concentrated under reduced pressure. The residue was purified by silica gel column chromatography (petroleum ether/ethyl acetate=10/1 to 2:1). Compound benzyl 4-(2-tert-butoxy-2-oxo-ethyl)-1,4-diazepane-1-carboxylate (1.08 g, 2.82 mmol, 77% yield, 91% purity) was obtained as a colorless oil. LC/MS (ESI) m/z: 349.1 $[M+1]^+$.

Step 2: Preparation of tert-butyl 2-(1,4-diazepan-1-yl)acetate

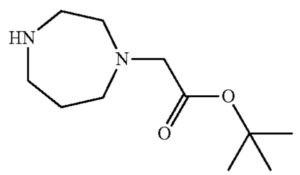

To a solution of benzyl 4-(2-tert-butoxy-2-oxo-ethyl)-1,4-diazepane-1-carboxylate (1.31 g, 3.42 mmol, 1 eq) in tetrahydrofuran (10 mL) was added palladium on activated carbon catalyst (0.2 g, 10% purity) under nitrogen. The suspension was degassed under vacuum and purged with hydrogen several times. The mixture was stirred under hydrogen (15 psi) at 40° C. for 24 hours. The reaction mixture was filtered and the filtrate was concentrated. Compound tert-butyl 2-(1,4-diazepan-1-yl)acetate (750 mg, 2.06 mmol, 60% yield, 59% purity) was obtained as a yellow oil, which was directly used into the next step without further purification. LC/MS (ESI) m/z: 215.2 $[M+1]^+$.

Step 3: Preparation of tert-butyl (R)-2-(4-((1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)methyl)-1,4-diazepan-1-yl)acetate

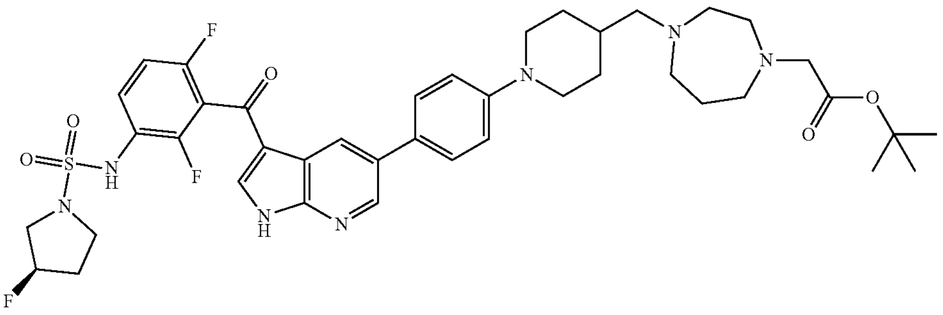 [SMILES: CC(C)(C)OC(=O)CN1CCCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1]

To a mixture of tert-butyl 2-(1,4-diazepan-1-yl)acetate (131 mg, 0.36 mmol, 1.1 eq) in 1,2-dichloromethane (2 mL) and methanol (1 mL) was added triethylamine (33 mg, 0.32 mmol, 1 eq) and (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (0.2 g, 0.32 mmol, 1 eq). The mixture was stirred at 30° C. for 10 minutes, then sodium triacetoxyborohydride (139 mg, 0.65 mmol, 2 eq) was added. The mixture was stirred at 30° C. for 110 min. The reaction mixture was extracted with ethyl acetate (30 mL×2). The combined organic layers were washed with brine (20 mL×2), dried over anhydrous sodium sulfate, filtered and concentrated under reduced pressure. The crude product was purified by preparative thin layer chromatography (dichloromethane:methanol=10:1, Rf=0.4). Compound tert-butyl 2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-1,4-diazepan-1-yl]acetate (192 mg, 0.22 mmol, 68% yield, 94% purity) was obtained as a yellow solid. LC/MS (ESI) m/z: 810.4 $[M+1]^+$.

Step 4: Preparation of (R)-2-(4-((1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)methyl)-1,4-diazepan-1-yl)acetic acid

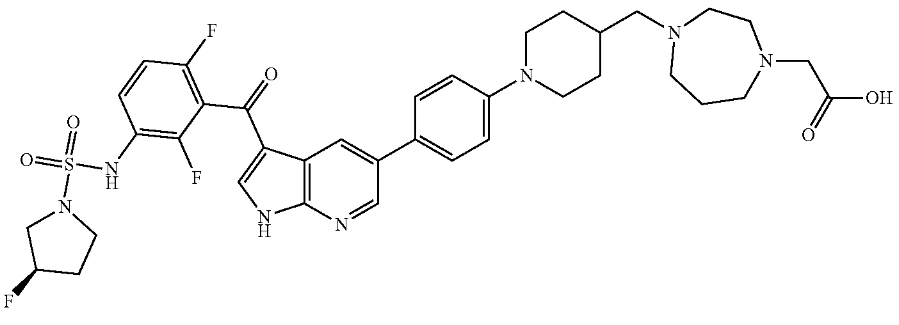 [SMILES: O=C(O)CN1CCCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-1,4-diazepan-1-yl]acetate (240 mg, 0.27 mmol, 1 eq) in dichloromethane (5 mL) was added trifluoroacetic acid (1 mL). The mixture was stirred at 15° C. for 16 h. The reaction mixture was concentrated under reduced pressure. Compound 2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-1,4-diazepan-1-yl]acetic acid (240 mg, crude, trifluoroacetic acid) was obtained as a yellow solid, which was directly used into the next step without further purification. LC/MS (ESI) m/z: 754.2 $[M+1]^+$.

Step 5: Preparation of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-1,4-diazepan-1-yl)acetamido)-3,3-dimethylbutanoyl)-4-hydroxy-N—((S)-1-(4-(4-methylthiazol-5-yl)phenyl)ethyl)pyrrolidine-2-carboxamide To a solution of 2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-1,4-diazepan-1-yl]acetic acid (240 mg, 0.27 mmol, 1 eq, trifluoroacetic acid) in N,N-dimethylformamide (2 mL) was added hydroxybenzotriazole (45 mg, 0.33 mmol, 1.2 eq) N,N-diisopropylethylamine (72 mg, 0.55 mmol, 2 eq) and 1-(3-dimethylaminopropyl)-3-ethylcarbodiimide hydrochloride (79 mg, 0.41 mmol, 1.5 eq). The mixture was stirred at 30° C. 10 min, then (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (159 mg, 0.33 mmol, 1.20 eq, hydrochloride) was added. The mixture was stirred at 30° C. for another 110 min. The reaction mixture was extracted with ethyl acetate (30 mL×2). The combined organic layers were washed with brine (15 mL×2), dried over anhydrous sodium sulfate, filtered and concentrated under reduced pressure. The residue was purified by Semi-preparative reverse phase HPLC. Compound (2S,4R)-1-[(2S)-2-[[2-[4-[[1-[4-[3-[2,6-difluoro-3-[[(3R)-3-fluoro pyrrolidin-1-yl]sulfonylamino]benzoyl]-1H-pyrrolo[2,3-b]pyridin-5-yl]phenyl]-4-piperidyl]methyl]-1,4-diazepan-1-

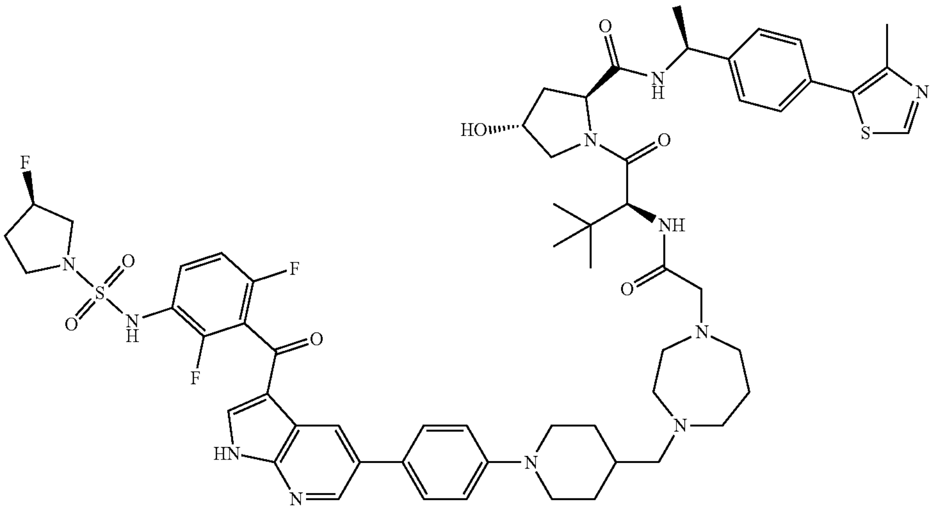 [SMILES: Cc1ncsc1-c1ccc([C@H](C)NC(=O)[C@@H]2C[C@@H](O)CN2C(=O)[C@@H](NC(=O)CN2CCCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (89.4 mg, 0.07 mmol, 25% yield, 97% purity, formate) was obtained as a pink solid. LC/MS (ESI) m/z: 591.0 $[M/2+1]^+$; $^1$H-NMR (400 MHz, DMSO-$d_6$) δ 8.97 (s, 1H), 8.64 (d, J=2.0 Hz, 1H), 8.52 (s, 1H), 8.42 (d, J=8.4 Hz, 1H), 8.20 (s, 1H), 8.03 (s, 1H), 7.81 (d, J=10.0 Hz, 1H), 7.64-7.54 (m, 3H), 7.45-7.41 (m, 2H), 7.39-7.34 (m, 2H), 7.24-7.17 (m, 1H), 7.06 (d, J=8.8 Hz, 2H), 5.41-5.17 (m, 1H), 5.02-4.83 (m, 1H), 4.61-4.39 (m, 2H), 4.29 (s, 1H), 3.78 (d, J=12.4 Hz, 3H), 3.64-3.52 (m, 2H), 3.13-3.10 (m, 2H), 2.73-2.65 (m, 10H), 2.45 (s, 4H), 2.40-2.25 (m, 5H), 2.17-1.96 (m, 4H), 1.91-1.68 (m, 6H), 1.64 (s, 1H), 1.43-1.34 (m, 3H), 1.29-1.15 (m, 2H), 0.95 (s, 9H).

Exemplary Synthesis of (2S,4R)-1-((S)-2-(2-(4-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)-1,4-diazepan-1-yl)acetamido)-3,3-dimethylbutanoyl)-4-hydroxy-N—((S)-1-(4-(4-methylthiazol-5-yl)phenyl)ethyl)pyrrolidine-2-carboxamide (Example 4371

Step 1: Preparation of 8-(4-bromophenyl)-1,4-dioxa-8-azaspiro[4.5]decane

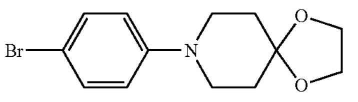

To a solution of 1-bromo-4-iodo-benzene (5 g, 17.67 mmol, 1 eq) and 1,4-dioxa-8-azaspiro[4.5]decane (2.53 g, 17.67 mmol, 2.26 mL, 1 eq) in dimethylsulfoxide (40 mL) was added L-PROLINE (813 mg, 7.07 mmol, 0.4 eq), copper iodide (673 mg, 3.53 mmol, 0.2 eq) and potassium carbonate (4.89 g, 35.35 mmol, 2 eq). The mixture was stirred at 80° C. for 12 h. Water (300 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=1:0 to 10:1). Compound 8-(4-bromophenyl)-1,4-dioxa-8-azaspiro[4.5]decane (3.2 g, 10.73 mmol, 60% yield) was obtained as a yellow solid. LC/MS (ESI) m/z: 297.9 $[M+1]^+$.

Step 2: Preparation of 8-(4-(4,4,5,5-tetramethyl-1,3,2-dioxaborolan-2-yl)phenyl)-1,4-dioxa-8-azaspiro[4.5]decane

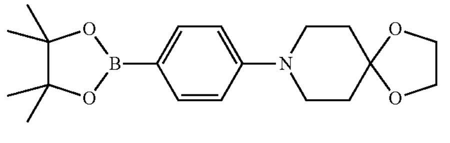 [SMILES: CC1(C)OB(c2ccc(N3CCC4(CC3)OCCO4)cc2)OC1(C)C]

To a solution of 8-(4-bromophenyl)-1,4-dioxa-8-azaspiro[4.5]decane (3.2 g, 10.73 mmol, 1 eq) and 4,4,5,5-tetramethyl-2-(4,4,5,5-tetramethyl-1,3,2-dioxaborolan-2-yl)-1,3,2-dioxaborolane (2.73 g, 10.73 mmol, 1 eq) in dioxane (90 mL) was added potassium acetate (2.11 g, 21.46 mmol, 2 eq) and ditert-butyl(cyclopentyl)phosphane;dichloropalladium; iron (699.45 mg, 1.07 mmol, 0.1 eq). The mixture was stirred at 80° C. for 12 h. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=1:0 to 30:1). Compound 8-[4-(4,4,5,5-tetramethyl-1,3,2-dioxaborolan-2-yl)phenyl]-1,4-dioxa-8-azaspiro[4.5]decane (2.2 g, 6.37 mmol, 59% yield) was obtained as a brown oil. LC/MS (ESI) m/z: 346.1 $[M+1]^+$.

Step 3: Preparation of (R)—N-(3-(5-(4-(1,4-dioxa-8-azaspiro[4.5]decan-8-yl)phenyl)-1-((2-(trimethylsilyl)ethoxy)methyl)-1H-pyrrolo[2,3-b]pyridine-3-carbonyl)-2,4-difluorophenyl)-3-fluoro-N-((2-(trimethylsilyl)ethoxy)methyl)pyrrolidine-1-sulfonamide

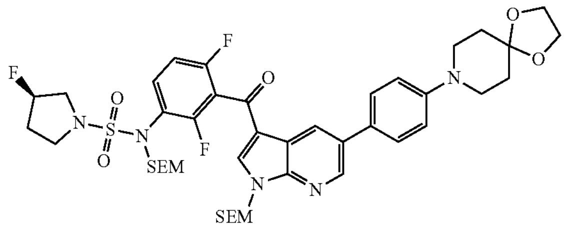 [SMILES: C[Si](C)(C)CCOCN(c1ccc(F)c(C(=O)c2cn(COCC[Si](C)(C)C)c3ncc(-c4ccc(N5CCC6(CC5)OCCO6)cc4)cc23)c1F)S(=O)(=O)N1CC[C@@H](F)C1]

To a solution of 8-[4-(4,4,5,5-tetramethyl-1,3,2-dioxaborolan-2-yl)phenyl]-1,4-dioxa-8-azaspiro[4.5]decane (1.4 g, 4.06 mmol, 1 eq) and (3R)—N-[3-[5-bromo-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (3.10 g, 4.06 mmol, 1 eq) in dioxane (10 mL) and water (1 mL) was added 4-ditert-butylphosphanyl-N,N-dimethyl-aniline;dichloropalladium (287 mg, 0.40 mmol, 0.1 eq), and cesium fluoride (2.46 g, 16.22 mmol, 4 eq). The mixture was stirred at 90° C. for 12 h. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=1:0 to 20:1). Compound (3R)—N-[3-[5-[4-(1,4-dioxa-8-azaspiro[4.5]decan-8-yl)phenyl]-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (2.2 g, 2.44 mmol, 60% yield) was obtained as a brown oil. LC/MS (ESI) m/z: 902.4 $[M+1]^+$.

Step 4: Preparation of (R)—N-(3-(5-(4-(1,4-dioxa-8-azaspiro[4.5]decan-8-yl)phenyl)-1H-pyrrolo[2,3-b]pyridine-3-carbonyl)-2,4-difluorophenyl)-3-fluoro-pyrrolidine-1-sulfonamide

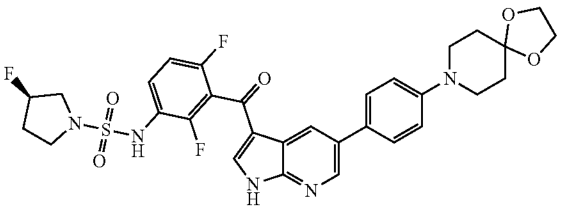 [SMILES: O=C(c1c(F)ccc(NS(=O)(=O)N2CC[C@@H](F)C2)c1F)c1c[nH]c2ncc(-c3ccc(N4CCC5(CC4)OCCO5)cc3)cc12]

To a solution of (3R)—N-[3-[5-[4-(1,4-dioxa-8-azaspiro[4.5]decan-8-yl)phenyl]-1-(2-trimethylsilylethoxymethyl)pyrrolo[2,3-b]pyridine-3-carbonyl]-2,4-difluoro-phenyl]-3-fluoro-N-(2-trimethylsilylethoxymethyl)pyrrolidine-1-sulfonamide (2.2 g, 2.44 mmol, 1 eq) in methanol (30 mL) was added 4 M hydrochloride in dioxane (55 mL, 90.22 eq). The mixture was stirred at 50° C. for 12 h. The reaction mixture concentrated under reduced pressure to give a residue. The crude product was used into the next step without further purification. Compound (3R)—N-[3-[5-[4-(1,4-dioxa-8-azaspiro[4.5]decan-8-yl)phenyl]-1H-pyrrolo[2,3-b]pyridine-3-carbonyl]-2,4-difluoro-phenyl]-3-fluoro-pyrrolidine-1-sulfonamide (1.5 g, crude) was obtained as a yellow solid. LC/MS (ESI) m/z: 642.1 $[M+1]^+$.

Step 5: Preparation of (R)—N-(2,4-difluoro-3-(5-(4-(4-oxopiperidin-1-yl)phenyl)-1H-pyrrolo[2,3-b]pyridine-3-carbonyl)phenyl)-3-fluoropyrrolidine-1-sulfonamide

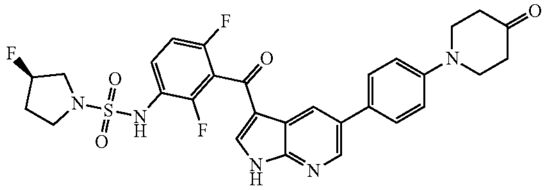 [SMILES: O=C1CCN(c2ccc(-c3cnc4[nH]cc(C(=O)c5c(F)ccc(NS(=O)(=O)N6CC[C@@H](F)C6)c5F)c4c3)cc2)CC1]

To a solution of (3R)—N-[3-[5-[4-(1,4-dioxa-8-azaspiro[4.5]decan-8-yl)phenyl]-1H-pyrrolo[2,3-b]pyridine-3-carbonyl]-2,4-difluoro-phenyl]-3-fluoro-pyrrolidine-1-sulfonamide (1.5 g, 2.34 mmol, 1 eq) in tetrahydrofuran (20 mL) was added hydrochloride (3 M, 34.09 mL, 43.75 eq). The mixture was stirred at 50° C. for 2 h. The reaction mixture concentrated under reduced pressure to give a residue. The residue was purified by preparative reverse phase HPLC. Compound (3R)—N-[2,4-difluoro-3-[5-[4-(4-oxo-1-piperidyl)phenyl]-1H-pyrrolo[2,3-b]pyridine-3-carbonyl]phenyl]-3-fluoro-pyrrolidine-1-sulfonamide (450 mg, 0.75 mmol, 64% yield) was obtained as a yellow solid. LC/MS (ESI) m/z: 598.1 $[M+1]^+$.

Step 6: Preparation of tert-butyl (R)-2-(4-(1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)-1,4-diazepan-1-yl)acetate

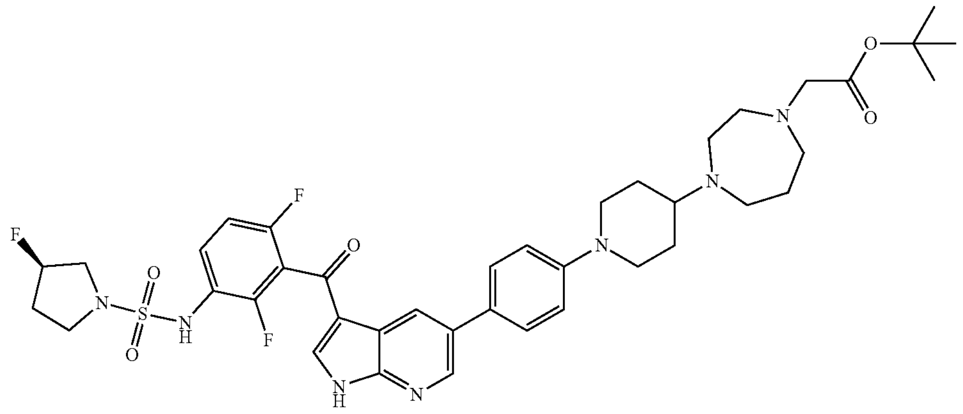 [SMILES: CC(C)(C)OC(=O)CN1CCCN(C2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-(1,4-diazepan-1-yl)acetate (149 mg, 0.41 mmol, 1 eq) and (3R)—N-[2,4-difluoro-3-[5-[4-(4-oxo-1-piperidyl)phenyl]-1H-pyrrolo[2,3-b]pyridine-3-carbonyl]phenyl]-3-fluoro-pyrrolidine-1-sulfonamide (300 mg, 0.41 mmol, 1 eq) in N,N-dimethylformamide (6 mL) and acetic acid (0.6 mL) was added sodium cyanoborohydride (77 mg, 1.23 mmol, 3 eq). The mixture was stirred at 15° C. for 12 h. Water (50 mL) was poured into the mixture and stirred for 1 minute. The aqueous phase was extracted with ethyl acetate (20 mL×3). The combined organic phase was washed with brine (40 mL×2), dried with anhydrous sodium sulfate, filtered and concentrated in vacuum. The residue was purified by prep-thin layer chromatography (dichloromethane:methanol=10:1). Compound tert-butyl 2-[4-[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]-1,4-diazepan-1-yl]acetate (140 mg, 0.17 mmol, 42% yield) was obtained as a yellow solid. LC/MS (ESI) m/z: 796.2 $[M+1]^+$.

Step 7: Preparation of (R)-2-(4-(1-(4-(3-(2,6-difluoro-3-((3-fluoropyrrolidine)-1-sulfonamido)benzoyl)-1H-pyrrolo[2,3-b]pyridin-5-yl)phenyl)piperidin-4-yl)-1,4-diazepan-1-yl)acetic acid

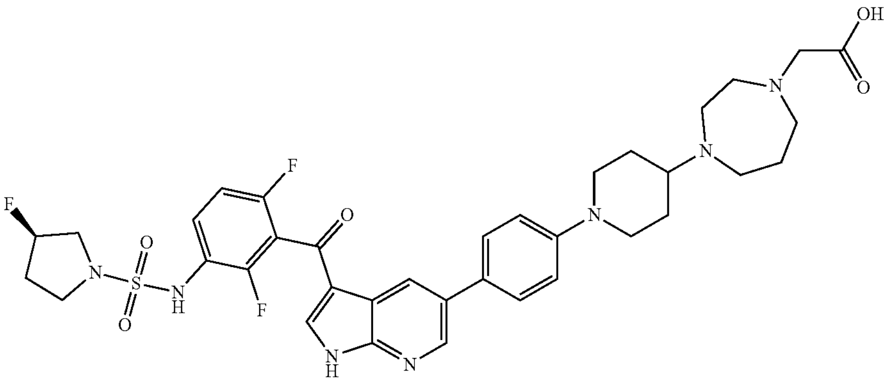 [SMILES: O=C(O)CN1CCCN(C2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-[4-[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]-1,4-diazepan-1-yl]acetate (200 mg, 0.25 mmol, 1 eq) in dichloromethane (3 mL) was added 4 M hydrochloric acid in dioxane (4.4 mL, 70.75 eq). The mixture was stirred at 15° C. for 1 h. The reaction mixture concentrated under reduced pressure. The crude product was used into the next step without further purification. Compound 2-[4-[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]-1,4-diazepan-1-yl]acetic acid (200 mg, crude, hydrochloride) was obtained as a yellow solid.

Step 8: Preparation of (2S,4R)-1-((S)-2-(2-(4-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)-1,4-diazepan-1-yl)acetamido)-3,3-dimethylbutanoyl)-4-hydroxy-N—((S)-1-(4-(4-methylthiazol-5-yl)phenyl)ethyl)pyrrolidine-2-carboxamide

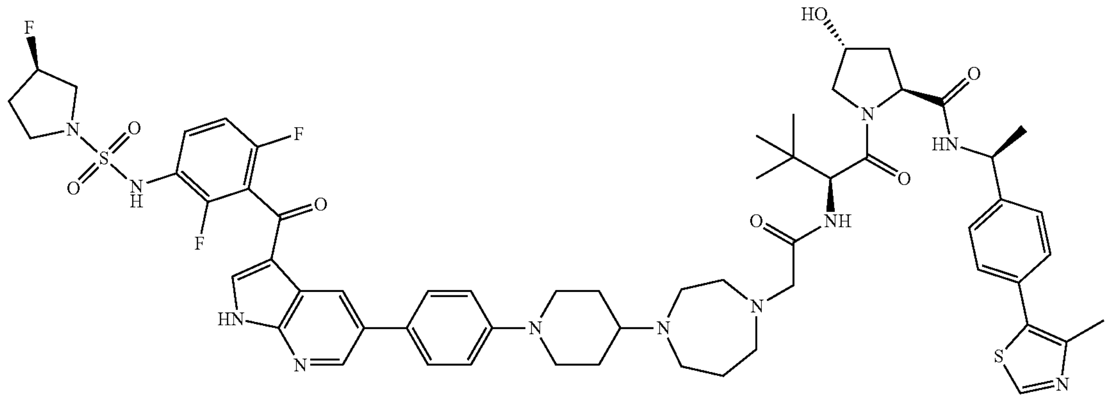 [SMILES: Cc1ncsc1-c1ccc([C@H](C)NC(=O)[C@@H]2C[C@@H](O)CN2C(=O)[C@@H](NC(=O)CN2CCCN(C3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

To a solution of (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (123 mg, 0.25 mmol, 1.00 eq, hydrochloride) and 2-[4-[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]-1,4-diazepan-1-yl]acetic acid (200 mg, 0.25 mmol, 1 eq, hydrochloride) in N,N-dimethylformamide (3 mL) was added triethylamine (130 mg, 1.29 mmol, 5 eq), 1-(3-dimethylaminopropyl)-3-ethylcarbodiimide hydrochloride (59 mg, 0.30 mmol, 1.2 eq) and hydroxybenzotriazole (41 mg, 0.30 mmol, 1.2 eq). The mixture was stirred at 30° C. for 12 h. Water (50 mL) was poured into the mixture and stirred for 1 minute. The aqueous phase was extracted with ethyl acetate (20 mL×3). The combined organic phase was washed with brine (20 mL×2), dried with anhydrous sodium sulfate, filtered and concentrated in vacuum. The residue was purified by prep-HPLC. Compound (2S,4R)-1-[(2S)-2-[[2-[4-[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]-1,4-diazepan-1-yl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (57.8 mg, 0.04 mmol, 17% yield, 97% purity, formate) was obtained as a yellow solid. LC/MS (ESI) m/z: 583.9 $[M/2]^+$; $^1$H-NMR (400 MHz, DMSO-$d_6$) δ 12.94 (s, 1H), 8.98 (s, 1H), 8.64 (d, J=2.0 Hz, 1H), 8.53 (s, 1H), 8.45 (d, J=7.6 Hz, 1H), 8.17 (s, 2H), 8.06 (s, 1H), 7.82 (d, J=9.6 Hz, 1H), 7.66-7.54 (m, 3H), 7.46-7.40 (m, 2H), 7.40-7.33 (m, 2H), 7.25 (t, J=8.4 Hz, 1H), 7.07 (d, J=8.8 Hz, 2H), 5.39-5.20 (m, 1H), 4.98-4.84 (m, 1H), 4.50 (d, J=9.6 Hz, 1H), 4.44 (t, J=8.4 Hz, 1H), 4.28 (s, 1H), 3.84 (d, J=11.2 Hz, 2H), 3.63-3.53 (m, 2H), 3.47 (s, 3H), 3.11 (d, J=8.8 Hz, 2H), 2.79 (d, J=15.2 Hz, 4H), 2.75-2.68 (m, 6H), 2.45 (s, 4H), 2.14-2.01 (m, 3H), 1.85-1.69 (m, 6H), 1.63-1.44 (m, 3H), 1.38 (d, J=6.8 Hz, 3H), 0.95 (s, 9H).

Exemplary Synthesis of (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)phenyl)acetamido)-3,3-dimethylbutanoyl)-4-hydroxy-N—((S)-1-(4-(4-methylthiazol-5-yl)phenyl)ethyl)pyrrolidine-2-carboxamide (Example 377)

Step 1: Preparation of methyl (R)-2-(4-((4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)methyl)phenyl)acetate

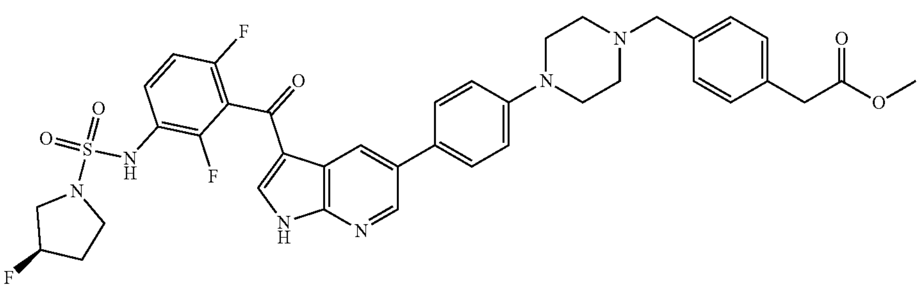 [SMILES: COC(=O)Cc1ccc(CN2CCN(c3ccc(-c4cnc5[nH]cc(C(=O)c6c(F)ccc(NS(=O)(=O)N7CC[C@@H](F)C7)c6F)c5c4)cc3)CC2)cc1]

To a solution of (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (200 mg, 0.30 mmol, 1 eq, 2 hydrochloride) in methyl alcohol (2 mL) and dichloromethane (1 mL) was added sodium acetate (50 mg, 0.61 mmol, 2 eq) to adjust the pH ~8.0. Then methyl 2-(4-formylphenyl)acetate (108 mg, 0.61 mmol, 2 eq) was added. The mixture was stirred at 30° C. for 15 min, followed by acetic acid (36 mg, 0.61 mmol, 2 eq) was added to adjust the pH ~5.0. The mixture was stirred at 15° C. for 15 min. And then sodium cyanoborohydride (38 mg, 0.61 mmol, 2 eq) was added in portions. The reaction mixture was stirred at 30° C. for 1.5 hours. The reaction mixture was poured into water (30 mL) and extracted with ethyl acetate (30 mL×2). The combined organic layers were dried over anhydrous sodium sulfate, filtered and concentrated under reduced pressure. The residue was purified by prep-thin layer chromatography (Dichloromethane:Methanol=10:1, Rf=0.4). Compound methyl 2-[4-[[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]phenyl]acetate (140 mg, 0.18 mmol, 60% yield, 98% purity) was obtained as a colorless oil. LC/MS (ESI) m/z: 747.2 $[M+1]^+$.

Step 2: Preparation of (R)-2-(4-((4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)methyl)phenyl)acetic acid

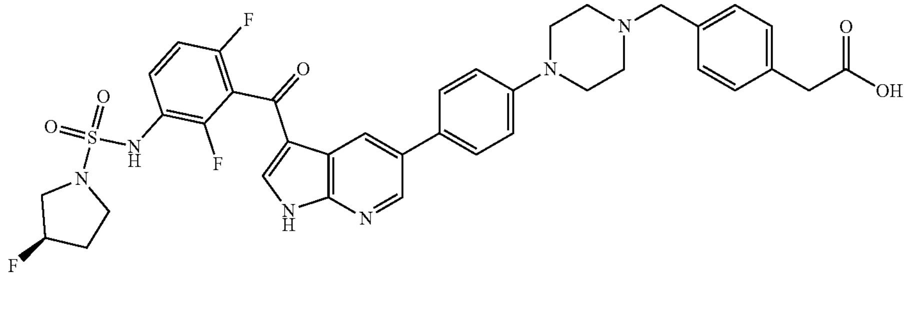 [SMILES: O=C(O)Cc1ccc(CN2CCN(c3ccc(-c4cnc5[nH]cc(C(=O)c6c(F)ccc(NS(=O)(=O)N7CC[C@@H](F)C7)c6F)c5c4)cc3)CC2)cc1]

To a solution of methyl 2-[4-[[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]phenyl]acetate (140 mg, 0.19 mmol, 1 eq) in tetrahydrofuran (2 mL) and water (0.5 mL) was added lithium hydrate (14 mg, 0.56 mmol, 3 eq). The mixture was stirred at 30° C. for 12 hr. The reaction mixture was concentrated under vacuum. The residue was diluted with water 5 mL, then acidified with hydrochloric acid (1 M) to pH=5~6. The suspension was concentrated under vacuum. The residue was purified by Semi-preparative reverse phase HPLC. Compound 2-[4-[[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]phenyl]acetic acid (65 mg, 0.1 mmol, 44% yield, 94% purity) was obtained as a yellow solid. LC/MS (ESI) m/z: 733.1 $[M+1]^+$.

Step 3: Preparation of (2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)phenyl)acetamido)-3,3-dimethylbutanoyl)-4-hydroxy-N—((S)-1-(4-(4-methylthiazol-5-yl)phenyl)ethyl)pyrrolidine-2-carboxamide

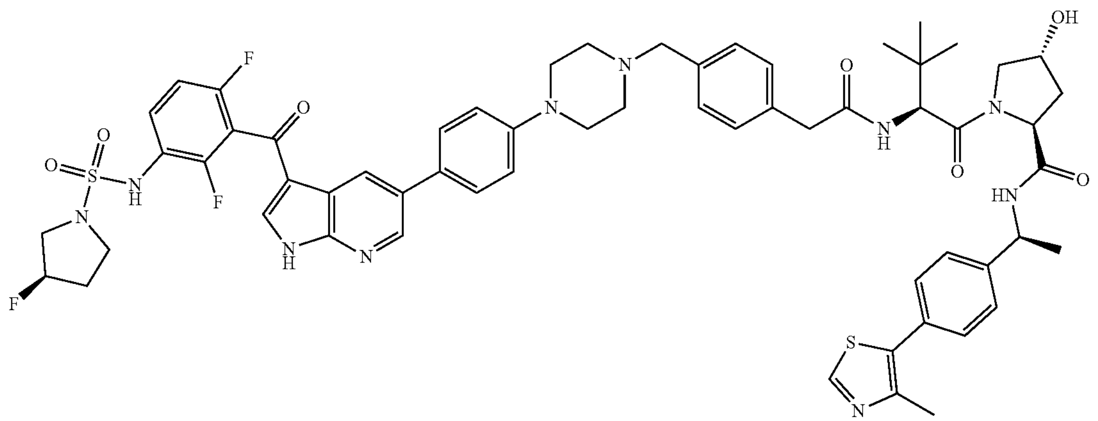 [SMILES: Cc1ncsc1-c1ccc([C@H](C)NC(=O)[C@@H]2C[C@@H](O)CN2C(=O)[C@@H](NC(=O)Cc2ccc(CN3CCN(c4ccc(-c5cnc6[nH]cc(C(=O)c7c(F)ccc(NS(=O)(=O)N8CC[C@@H](F)C8)c7F)c6c5)cc4)CC3)cc2)C(C)(C)C)cc1]

To a solution of 2-[4-[[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]phenyl]acetic acid (115 mg, 0.15 mmol, 1 eq) and (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (71 mg, 0.15 mmol, 1.00 eq, hydrochloride) in N,N-dimethylformamide (1 mL) was added hydroxybenzotriazole (24 mg, 0.18 mmol, 1.2 eq), N,N-diisopropylethylamine (57 mg, 0.44 mmol, 3 eq) and 1-(3-dimethylaminopropyl)-3-ethylcarbodiimide hydrochloride (42.42 mg, 0.22 mmol, 1.5 eq. The mixture was stirred at 30° C. for 2 hr. The reaction mixture was poured into water (30 mL) and extracted with ethyl acetate (40 mL×2). The combined organic layers were dried over anhydrous sodium sulfate, filtered and concentrated under reduced pressure. The residue was purified by Semi-preparative reverse phase HPLC. Compound (2S,4R)-1-[(2S)-2-[[2-[4-[[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]phenyl]acetyl]amino]-3,3-dimethyl-butanoyl]-4-hydroxy-N-[(1S)-1-[4-(4-methylthiazol-5-yl)phenyl]ethyl]pyrrolidine-2-carboxamide (93.8 mg, 0.07 mmol, 51% yield, 97% purity, formic acid) was obtained as a yellow solid. LC/MS (ESI) m/z: 580.3 $[M/2+1]^+$; $^1$H-NMR (400 MHz, DMSO-$d_6$) δ 12.90 (s, 1H), 9.01-8.95 (m, 1H), 8.64 (d, J=2.4 Hz, 1H), 8.53 (s, 1H), 8.44-8.36 (m, 1H), 8.15 (s, 1H), 8.06 (s, 1H), 7.99 (d, J=9.2 Hz, 1H), 7.69-7.53 (m, 3H), 7.47-7.41 (m, 2H), 7.41-7.35 (m, 2H), 7.30-7.21 (m, 5H), 7.06 (d, J=8.8 Hz, 2H), 5.41-5.19 (m, 1H), 5.10 (s, 1H), 5.00-4.84 (m, 1H), 4.50 (d, J=9.2 Hz, 1H), 4.43 (t, J=8.0 Hz, 1H), 4.27 (s, 1H), 3.66-3.55 (m, 3H), 3.49 (d, J=14.4 Hz, 4H), 3.39 (s, 3H), 3.21 (s, 3H), 2.56-2.53 (m, 2H), 2.52 (s, 3H), 2.45 (s, 3H), 2.25-1.87 (m, 4H), 1.84-1.67 (m, 1H), 1.38 (d, J=7.2 Hz, 3H), 1.00-0.80 (m, 9H).

Exemplary Synthesis of (2S,4R)-1-((S)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoyl)-4-hydroxy-N—((S)-1-(4-(4-methylthiazol-5-yl)phenyl)ethyl)pyrrolidine-2-carboxamide (Example 383) and (2S,4R)-1-((R)-2-(3-(4-(4-(4-(3-(2,6-difluoro-3-(((R)-3-fluoropyrrolidine)-1-sulfonamide)benzoyl)-1H-pyrrolo[2,3-b]pyridin-5-yl)phenyl)piperazin-1-yl)butoxy)isoxazol-5-yl)-3-methylbutanoyl)-4-hydroxy-N—((S)-1-(4-(4-methylthiazol-5-yl)phenyl)ethyl)pyrrolidine-2-carboxamide (Example 384)

Step 1: Preparation of methyl 2-(3-(4,4-dimethoxybutoxy)isoxazol-5-yl)-3-methylbutanoate

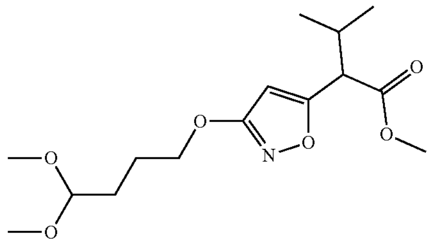

To a solution of 4-chloro-1,1-dimethoxy-butane (383 mg, 2.51 mmol, 1 eq) and methyl 2-(3-hydroxyisoxazol-5-yl)-3-methyl-butanoate (500 mg, 2.51 mmol, 1 eq) in N,N-dimethylformamide (10 mL) was added cesium carbonate (1.64 g, 5.02 mmol, 2 eq). The mixture was stirred at 80° C. for 2 h. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=1:0 to 30:1). Compound methyl 2-[3-(4,4-dimethoxybutoxy) isoxazol-5-yl]-3-methyl-butanoate (500 mg, 1.36 mmol, 54% yield, 86% purity) was obtained as a colorless oil. LC/MS (ESI) m/z: 338.4 $[M+23]^+$.

Step 2: Preparation of methyl 3-methyl-2-(3-(4-oxobutoxy)isoxazol-5-yl)butanoate

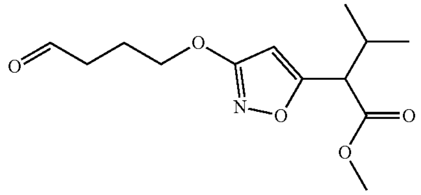 [SMILES: COC(=O)C(c1cc(OCCCC=O)no1)C(C)C]

To a solution of methyl 2-[3-(4,4-dimethoxybutoxy) isoxazol-5-yl]-3-methyl-butanoate (500 mg, 1.36 mmol, 1 eq) in tetrahydrofuran (20 mL) was added sulfuric acid (2 M, 27 mL, 40 eq). The mixture was stirred at 70° C. for 0.5 h. The reaction mixture was adjusted to pH 8 with saturated aqueous sodium bicarbonate. Water (50 mL) was poured into the mixture and stirred for 1 minute. The aqueous phase was extracted with ethyl acetate (30 mL×3). The combined organic phase was washed with brine (30 mL×2), dried with anhydrous sodium sulfate, filtered and concentrated in vacuum. The crude product was used into the next step without further purification. Compound methyl 3-methyl-2-[3-(4-oxobutoxy)isoxazol-5-yl]butanoate (270 mg, 1.00 mmol, 73% yield) was obtained as a colorless oil.

Step 3: Preparation of methyl 2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoate

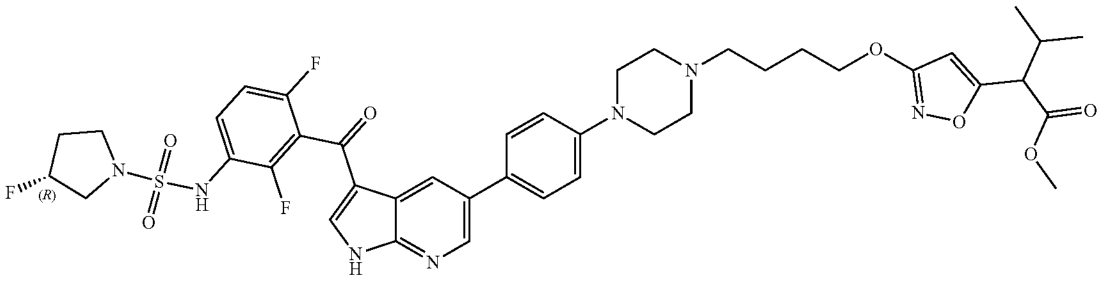

To a solution of methyl 3-methyl-2-[3-(4-oxobutoxy) isoxazol-5-yl]butanoate (150 mg, 0.55 mmol, 1 eq) and (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (345 mg, 0.55 mmol, 1 eq, hydrochloride) in 1,2-dichloroethane (5 mL) was added triethylamine (112 mg, 1.11 mmol, 2 eq) and sodium triacetoxyborohydride (354 mg, 1.67 mmol, 3 eq). The mixture was stirred at 15° C. for 2 hours. Water (100 mL) was poured into the mixture and stirred for 1 minute. The aqueous phase was extracted with ethyl acetate (30 mL×3). The combined organic phase was washed with brine (30 mL×2), dried with anhydrous sodium sulfate, filtered and concentrated in vacuum. The residue was purified by prep-TLC (dichloromethane:methanol=10:1). Compound methyl 2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoate (300 mg, 0.35 mmol, 64% yield) was obtained as a yellow solid. LC/MS (ESI) m/z: 838.1 $[M+1]^+$; $^1$H-NMR (400 MHz, DMSO-$d_6$) δ 12.89 (s, 1H), 9.82 (s, 1H), 8.65 (d, J=2.4 Hz, 1H), 8.53 (s, 1H), 8.06 (s, 1H), 7.66-7.56 (m, 3H), 7.26 (t, J=8.8 Hz, 1H), 7.07 (d, J=8.8 Hz, 2H), 6.20 (s, 1H), 5.23 (s, 1H), 4.20 (t, J=6.4 Hz, 2H), 3.67-3.65 (m, 3H), 3.48 (s, 1H), 3.43-3.36 (m, 2H), 3.21 (s, 4H), 2.89 (s, 1H), 2.60-2.51 (m, 6H), 2.40 (t, J=6.8 Hz, 2H), 2.33-2.25 (m, 1H), 2.14-2.06 (m, 1H), 1.81-1.72 (m, 2H), 1.59 (quin, J=7.2 Hz, 2H), 0.93 (d, J=6.8 Hz, 3H), 0.85 (d, J=6.8 Hz, 3H).

Step 4: Preparation of 2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoic acid

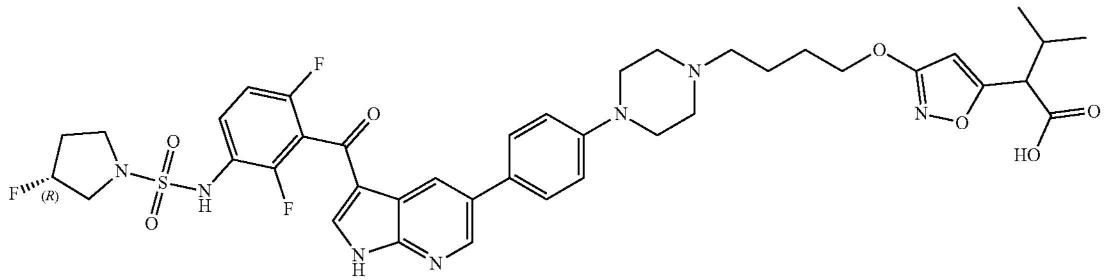

To a solution of methyl 2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoate (300 mg, 0.35 mmol, 1 eq) in tetrahydrofuran (5 mL), methanol (5 mL) and water (3 mL) was added lithium hydroxide monohydrate (30 mg, 0.71 mmol, 2 eq). The mixture was stirred at 40° C. for 1 h. The reaction mixture concentrated under reduced pressure to give a residue. The reaction mixture was adjusted pH to 5 with hydrochloride acid (1 M). The residue was purified by prep-HPLC. Compound 2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoic acid (200 mg, 0.24 mmol, 67% yield) was obtained as a yellow solid. LC/MS (ESI) m/z: 824.4 $[M+1]^+$.

Step 5: Preparation of (2S,4R)-1-(2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoyl)-4-hydroxy-N—((S)-1-(4-(4-methylthiazol-5-yl)phenyl)ethyl)pyrrolidine-2-carboxamide

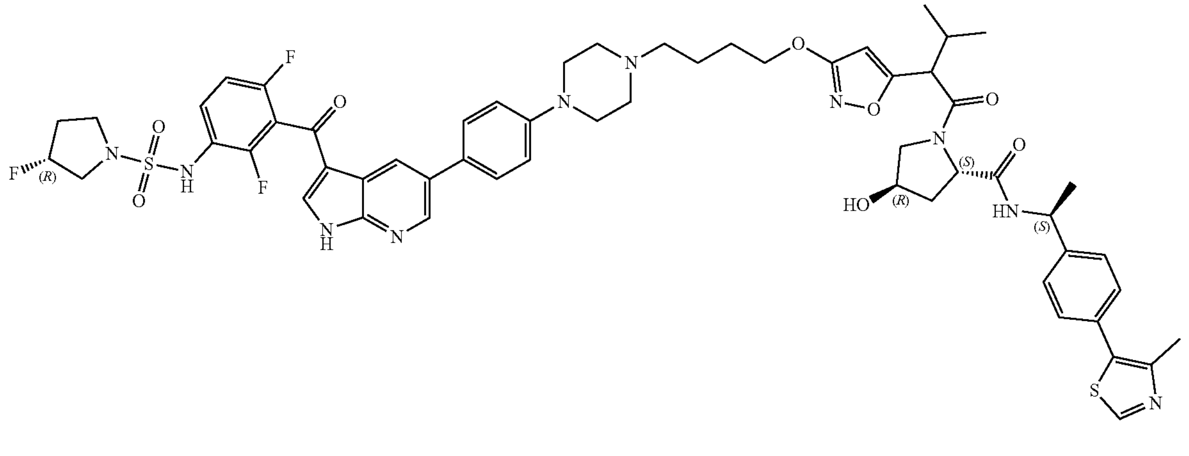

To a solution of 2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoic acid (200 mg, 0.24 mmol, 1 eq) and (2S,4R)-4-hydroxy-N-[(1S)-1-[4-(4-methylthiazol-5-yl)phenyl]ethyl]pyrrolidine-2-carboxamide (89. mg, 0.24 mmol, 1.00 eq, HCl) in N,N-dimethylformamide (5 mL) was added triethylamine (36 mg, 0.36 mmol, 1.5 eq), 1-(3-dimethylaminopropyl)-3-ethylcarbodiimide hydrochloride (55 mg, 0.29 mmol, 1.2 eq) and hydroxybenzotriazole (39 mg, 0.29 mmol, 1.2 eq). The mixture was stirred at 30° C. for 12 hours. Water (50 mL) was poured into the mixture and stirred for 1 minute. The aqueous phase was extracted with dichloromethane (20 mL×3). The combined organic phase was washed with brine (20 mL×2), dried with anhydrous sodium sulfate, filtered and concentrated in vacuum. The residue was purified by prep-HPLC. Compound (2S,4R)-1-[2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoyl]-4-hydroxy-N-[(1S)-1-[4-(4-methylthiazol-5-yl)phenyl]ethyl]pyrrolidine-2-carboxamide (130 mg, 0.10 mmol, 43% yield, 96% purity, formate) was obtained as a white solid. LC/MS (ESI) m/z: 569.4 $[M/2+1]^+$.

Step 6: Preparation of (2S,4R)-1-((S)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoyl)-4-hydroxy-N—((S)-1-(4-(4-methylthiazol-5-yl)phenyl)ethyl)pyrrolidine-2-carboxamide and (2S,4R)-1-((R)-2-(3-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)isoxazol-5-yl)-3-methylbutanoyl)-4-hydroxy-N—((S)-1-(4-(4-methylthiazol-5-yl)phenyl)ethyl)pyrrolidine-2-carboxamide

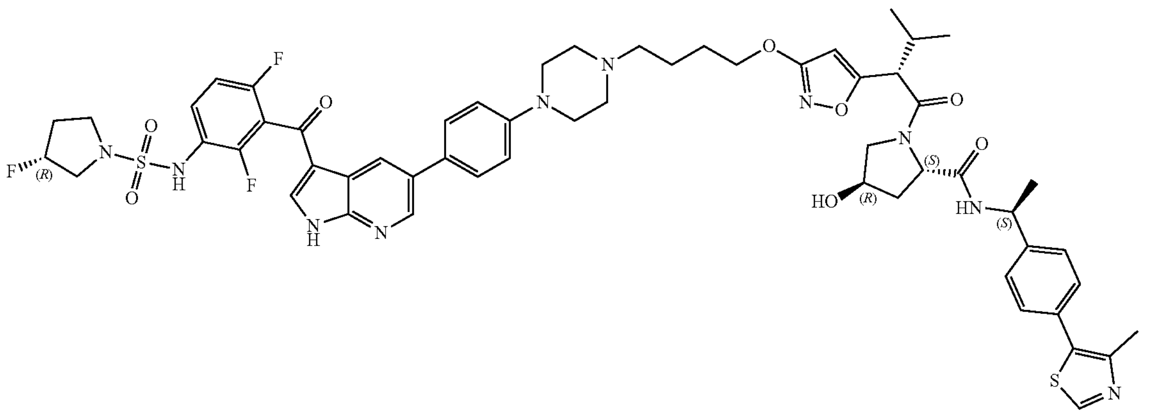

+

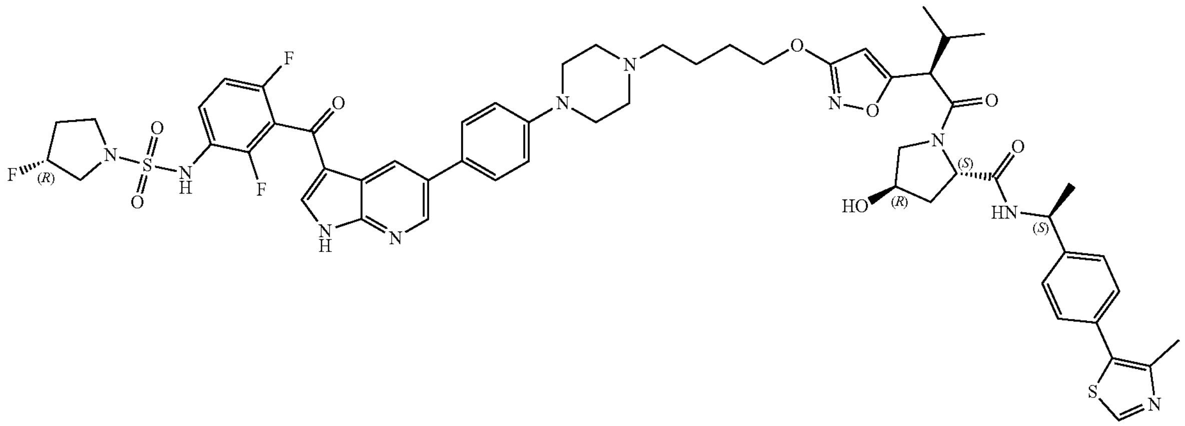

(2S,4R)-1-[2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoyl]-4-hydroxy-N-[(1S)-1-[4-(4-methylthiazol-5-yl)phenyl]ethyl]pyrrolidine-2-carboxamide (130 mg, 0.10 mmol, 1 eq, formate) was separated by chiral supercritical fluid chromatography. Compound (2S,4R)-1-[(2S)-2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoyl]-4-hydroxy-N-[(1S)-1-[4-(4-methylthiazol-5-yl)phenyl]ethyl]pyrrolidine-2-carboxamide (22.68 mg, 0.01 mmol, 32% yield, 91% purity, formate) was obtained as a yellow solid. LC/MS (ESI) m/z: 569.3 $[M/2+1]^+$; $^1$H-NMR (400 MHz, DMSO-$d_6$) δ 12.86 (s, 1H), 9.01-8.96 (m, 1H), 8.95-8.82 (m, 1H), 8.63 (d, J=2.1 Hz, 1H), 8.52 (s, 1H), 8.30 (d, J=7.6 Hz, 1H), 8.03 (s, 1H), 7.63-7.46 (m, 4H), 7.45-7.38 (m, 2H), 7.35-7.30 (m, 2H), 7.13 (s, 1H), 7.05 (d, J=8.8 Hz, 2H), 6.16-6.07 (m, 1H), 5.37-5.17 (m, 1H), 5.11 (d, J=3.2 Hz, 1H), 5.05-4.96 (m, 1H), 4.90 (t, J=7.2 Hz, 1H), 4.42 (t, J=7.6 Hz, 1H), 4.26 (s, 1H), 4.22-4.11 (m, 2H), 3.75 (d, J=8.8 Hz, 1H), 3.59-3.36 (m, 4H), 3.29-3.12 (m, 6H), 2.45 (s, 3H), 2.41-2.31 (m, 3H), 2.30-2.22 (m, 1H), 2.11-2.02 (m, 3H), 1.82-1.68 (m, 3H), 1.56 (dd, J=7.6, 14.5 Hz, 2H), 1.48-1.41 (m, 1H), 1.35 (d, J=7.2 Hz, 3H), 0.96 (d, J=6.4 Hz, 3H), 0.83 (d, J=6.8 Hz, 3H). Compound (2S,4R)-1-[(2R)-2-[3-[4-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]butoxy]isoxazol-5-yl]-3-methyl-butanoyl]-4-hydroxy-N-[(1S)-1-[4-(4-methylthiazol-5-yl)phenyl]ethyl]pyrrolidine-2-carboxamide (52.44 mg, 0.04 mmol, 76% yield, 95% purity, formate) was obtained as a yellow solid. LC/MS (ESI) m/z: 569.3 $[M/2+1]^+$; $^1$H-NMR (400 MHz, DMSO-$d_6$) δ 12.95 (s, 1H), 9.90 (s, 1H), 8.99 (s, 1H), 8.92 (s, 1H), 8.67 (d, J=2.0 Hz, 1H), 8.56 (s, 1H), 8.44 (d, J=7.6 Hz, 1H), 8.17-8.06 (m, 1H), 7.69-7.58 (m, 3H), 7.50-7.42 (m, 2H), 7.41-7.34 (m, 2H), 7.28 (t, J=8.0 Hz, 1H), 7.12 (d, J=8.4 Hz, 2H), 6.14-5.93 (m, 1H), 5.39-5.22 (m, 1H), 5.39-5.22 (m, 1H), 5.15-5.01 (m, 1H), 4.99-4.84 (m, 1H), 4.37 (t, J=8.0 Hz, 1H), 4.29 (s, 1H), 4.20 (s, 2H), 3.75-3.62 (m, 2H), 3.53-3.36 (m, 6H), 2.54-2.52 (m, 3H), 2.46 (s, 3H), 2.35 (td, J=2.0, 8.4 Hz, 2H), 2.30-2.17 (m, 2H), 2.10-2.01 (m, 2H), 1.84-1.72 (m, 5H), 1.49-1.42 (m, 1H), 1.41-1.34 (m, 3H), 1.24 (s, 1H), 1.00-0.94 (m, 3H), 0.87-0.78 (m, 4H).

Exemplary Synthesis of (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide (Example 493) and (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide (Example 479)

Step 1: Preparation of tert-butyl (R)-(1-(4-bromophenyl)-2-hydroxyethyl)carbamate

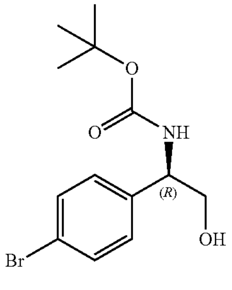

To a solution of (2R)-2-amino-2-(4-bromophenyl)ethanol (1.74 g, 6.89 mmol, 1 eq, hydrochloride) in tetrahydrofuran (25 mL) was added triethylamine (2.79 g, 27.56 mmol, 3.84 mL, 4 eq) and tert-butoxycarbonyl tert-butyl carbonate (1.80 g, 8.27 mmol, 1.90 mL, 1.2 eq). The mixture was stirred at 30° C. for 12 h. The reaction mixture was concentrated under reduced pressure to remove tetrahydrofuran. The residue was extracted with ethyl acetate (50 mL×2). The combined organic layers were washed with aqueous brine (40 mL×2), dried over anhydrous sodium sulfate, filtered and concentrated under reduced pressure. The crude product was triturated with Petroleum ether/Ethyl acetate (22 mL, v:v=10:1). Compound tert-butyl N-[(1R)-1-(4-bromophenyl)-2-hydroxy-ethyl]carbamate (2 g, 6.33 mmol, 91% yield) was obtained as a white solid. $^1$H NMR (400 MHz, $CDCl_3$) δ 7.51-7.46 (m, 2H), 7.20 (d, J=8.4 Hz, 2H), 5.27 (s, 1H), 4.73 (s, 1H), 3.92-3.75 (m, 2H), 2.12 (s, 1H), 1.51-1.32 (m, 9H).

Step 2: Preparation of tert-butyl (R)-(2-hydroxy-1-(4-(4-methylthiazol-5-yl)phenyl)ethyl)carbamate

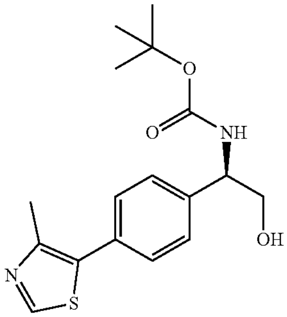 [SMILES: Cc1ncsc1-c1ccc([C@H](CO)NC(=O)OC(C)(C)C)cc1]

A mixture of tert-butyl N-[(1R)-1-(4-bromophenyl)-2-hydroxy-ethyl]carbamate (2.0 g, 6.33 mmol, 1 eq), 4-methylthiazole (1.25 g, 12.65 mmol, 1.15 mL, 2 eq), potassium acetate (1.24 g, 12.65 mmol, 2 eq) and palladium acetate (142 mg, 0.63 mmol, 0.1 eq) in dimethylacetamide (40 mL) was degassed and purged with nitrogen for 3 times, and then the mixture was stirred at 100° C. for 12 h under nitrogen atmosphere. The reaction mixture was concentrated under reduced pressure to remove dimethylacetamide. The residue was extracted with ethyl acetate (40 mL×2) and washed with saturated brine (40 mL×2). The combined organic layers were dried over anhydrous sodium sulfate, filtered and concentrated under reduced pressure. The residue was purified by silica gel chromatography (Petroleum ether/Ethyl acetate=5/1 to 1/2). Compound tert-butyl N-[(1R)-2-hydroxy-1-[4-(4-methylthiazol-5-yl) phenyl]ethyl]carbamate (1.45 g, 3.98 mmol, 63% yield, 91% purity) was obtained as a yellow oil. LC/MS (ESI) m/z: 335.1 $[M+1]^+$.

Step 3: Preparation of (R)-2-amino-2-(4-(4-methylthiazol-5-yl)phenyl)ethan-1-ol

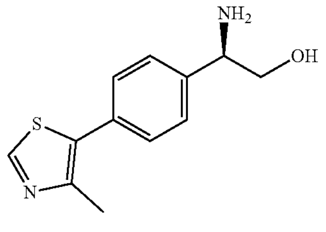 [SMILES: Cc1ncsc1-c1ccc([C@@H](N)CO)cc1]

To a solution of tert-butyl N-[(1R)-2-hydroxy-1-[4-(4-methylthiazol-5-yl)phenyl]ethyl]carbamate (1.45 g, 3.98 mmol, 1 eq) in dichloromethane (5 mL) was added hydrochloric acid (4 M in dioxane, 18 mL, 18.33 eq). The mixture was stirred at 20° C. for 2 h. The reaction mixture was concentrated under reduced pressure. The crude product was triturated with Ethyl acetate (10 mL) at 15° C. for 10 min. Compound (2R)-2-amino-2-[4-(4-methylthiazol-5-yl)phenyl]ethanol (1.08 g, 3.99 mmol, 100% yield, hydrochloride) was obtained as a yellow solid. LC/MS (ESI) m/z: 235.0 $[M+1]^+$.

Step 4: Preparation of tert-butyl (2S,4R)-4-hydroxy-2-(((R)-2-hydroxy-1-(4-(4-methylthiazol-5-yl)phenyl)ethyl)carbamoyl)pyrrolidine-1-carboxylate

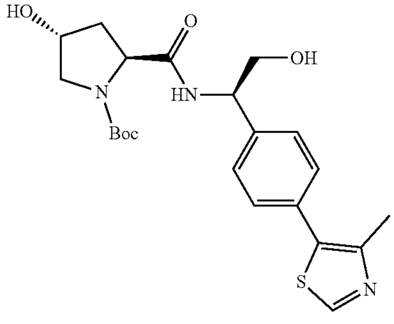 [SMILES: Cc1ncsc1-c1ccc([C@H](CO)NC(=O)[C@@H]2C[C@@H](O)CN2C(=O)OC(C)(C)C)cc1]

To a solution of (2R)-2-amino-2-[4-(4-methylthiazol-5-yl)phenyl]ethanol (1.08 g, 3.99 mmol, 1 eq, hydrochloride) and (2S,4R)-1-tert-butoxycarbonyl-4-hydroxy-pyrrolidine-2-carboxylic acid (922 mg, 3.99 mmol, 1 eq) in N,N-dimethylformamide (15 mL) was added hydroxybenzotriazole (647 mg, 4.79 mmol, 1.2 eq), N,N-diisopropylethylamine (1.55 g, 11.97 mmol, 2 mL, 3 eq) and 1-(3-dimethylaminopropyl)-3-ethylcarbodiimide hydrochloride (1.15 g, 5.98 mmol, 1.5 eq). The mixture was stirred at 30° C. for 12 h. The reaction mixture was extracted with dichloromethane (30 mL×3) and washed with saturated brine (25 mL×3). The combined organic layers were dried over anhydrous sodium sulfate, filtered and concentrated under reduced pressure. The residue was purified by silica gel column chromatography (Ethyl acetate/Methanol=50/1 to 20:1). Compound tert-butyl (2S, 4R)-4-hydroxy-2-[[(1R)-2-hydroxy-1-[4-(4-methylthiazol-5-yl)phenyl]ethyl]carbamoyl]pyrrolidine-1-carboxylate (1.67 g, 2.90 mmol, 72% yield, 77% purity) was obtained as a yellow solid. LC/MS (ESI) m/z: 448.1 $[M+1]^+$.

Step 5: Preparation of (2S,4R)-4-hydroxy-N—((R)-2-hydroxy-1-(4-(4-methylthiazol-5-yl)phenyl)ethyl)pyrrolidine-2-carboxamide

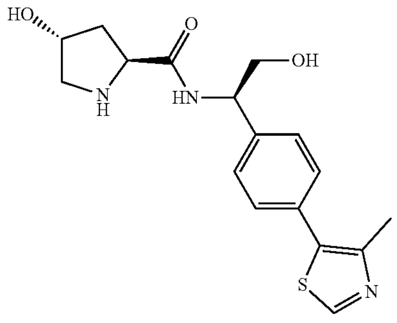 [SMILES: Cc1ncsc1-c1ccc([C@H](CO)NC(=O)[C@@H]2C[C@@H](O)CN2)cc1]

To a solution of tert-butyl (2S,4R)-4-hydroxy-2-[[(1R)-2-hydroxy-1-[4-(4-methylthiazol-5-yl)phenyl]ethyl]carbamoyl]pyrrolidine-1-carboxylate (1.67 g, 2.90 mmol, 1 eq) in dichloromethane (8 mL) was added hydrochloric acid/dioxane (4 M, 20 mL). The mixture was stirred at 15° C. for 2 h. The reaction mixture was concentrated under vacuum. The residue was purified by Semi-preparative reverse phase HPLC. Compound (2S,4R)-4-hydroxy-N-[(1R)-2-hydroxy-1-[4-(4-methylthiazol-5-yl) phenyl]ethyl]pyrrolidine-2-carboxamide (930 mg, 2.42 mmol, 83% yield, hydrochloride) was obtained as a white solid. LC/MS (ESI) m/z: 348.0 $[M+1]^+$; $^1$H-NMR (400 MHz, DMSO-$d_6$) δ 9.84 (s, 1H), 9.17 (s, 1H), 9.00 (s, 1H), 8.61 (s, 1H), 7.51-7.35 (m, 4H), 4.96-4.88 (m, 1H), 4.48-4.37 (m, 3H), 3.69-3.55 (m, 2H), 3.29 (d, J=6.4 Hz, 1H), 3.09 (s, 1H), 2.46 (s, 3H), 2.41 (dd, J=7.6, 13.1 Hz, 1H), 1.89-1.74 (m, 1H).

Step 6: Preparation of methyl 2-(3-(3,3-dimethoxypropoxy)isoxazol-5-yl)-3-methylbutanoate

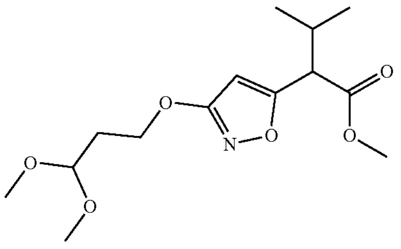

To a solution of methyl 2-(3-hydroxyisoxazol-5-yl)-3-methyl-butanoate (2 g, 10.04 mmol, 1 eq) in N,N-dimethylformamide (40 mL) was added potassium carbonate (2.08 g, 15.06 mmol, 1.5 eq) and 3-bromo-1,1-dimethoxy-propane (2.02 g, 11.04 mmol, 1.5 mL, 1.1 eq). The mixture was stirred at 70° C. for 12 h. The reaction mixture was extracted with ethyl acetate (50 mL×3). The combined organic layers were washed with brine (40 mL×2), dried over anhydrous sodium sulfate, filtered and concentrated under reduced pressure. The residue was purified by silica gel chromatography (petroleum ether/ethyl acetate=50/1 to 20:1). Compound methyl 2-[3-(3,3-dimethoxypropoxy)isoxazol-5-yl]-3-methyl-butanoate (1.97 g, 6.54 mmol, 65% yield) was obtained as a colorless oil. LC/MS (ESI) m/z: 324.1 $[M+23]^+$; $^1$H-NMR (400 MHz, DMSO-$d_6$) δ 6.19 (s, 1H), 4.53 (t, J=5.6 Hz, 1H), 4.17 (t, J=6.4 Hz, 2H), 3.76-3.61 (m, 4H), 3.24 (s, 6H), 2.34-2.22 (m, 1H), 1.99 (q, J=6.4 Hz, 2H), 0.93 (d, J=6.8 Hz, 3H), 0.85 (d, J=6.7 Hz, 3H).

Step 7: Preparation of methyl 3-methyl-2-(3-(3-oxopropoxy)isoxazol-5-yl)butanoate

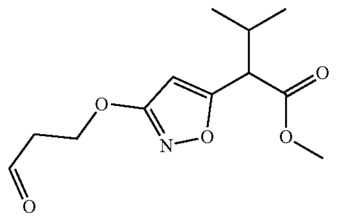 [SMILES: COC(=O)C(c1cc(OCCC=O)no1)C(C)C]

To a mixture of methyl 2-[3-(3,3-dimethoxypropoxy) isoxazol-5-yl]-3-methyl-butanoate (1.97 g, 6.54 mmol, 1 eq) in tetrahydrofuran (100 mL) was added sulfuric acid (1 M, 100 mL, 15.30 eq) in one portion at 20° C. The mixture was stirred at 70° C. for 0.5 hour. The reaction mixture was basified with saturated sodium bicarbonate to pH=7~8. The aqueous phase was extracted with ethyl acetate (50 mL×3). The combined organic phase was washed with brine (30 mL×2), dried with anhydrous an hydrous sodium sulfate, filtered and concentrated in vacuum. Compound methyl 3-methyl-2-[3-(3-oxopropoxy) isoxazol-5-yl]butanoate (1.47 g, 5.76 mmol, 88% yield) was obtained as a colorless oil, which was directly used into the next step and without further purification.

Step 8: Preparation of methyl 2-(3-(3-(4-(4-(3-(2,6-difluoro-3-(((R)-3-fluoropyrrolidine)-1-sulfonamido) benzoyl)-1H-pyrrolo[2,3-b]pyridin-5-yl)phenyl)piperazin-1-yl)propoxy)isoxazol-5-yl)-3-methylbutanoate

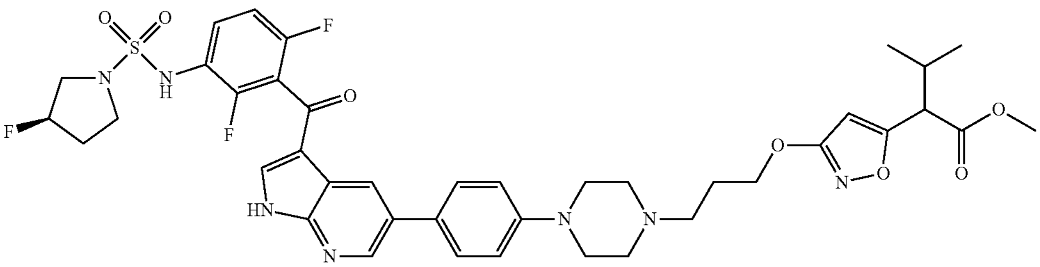 [SMILES: COC(=O)C(c1cc(OCCCN2CCN(c3ccc(-c4cnc5[nH]cc(C(=O)c6c(F)ccc(NS(=O)(=O)N7CC[C@@H](F)C7)c6F)c5c4)cc3)CC2)no1)C(C)C]

To a mixture of (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (1.45 g, 2.33 mmol, 0.7 eq, hydrochloride) in methanol (8 mL) was added sodium acetate (547 mg, 6.67 mmol, 2 eq) in one portion at 15° C. The mixture was stirred at 15° C. for 15 min, then methyl 3-methyl-2-[3-(3-oxopropoxy)isoxazol-5-yl]butanoate (852 mg, 3.34 mmol, 1 eq) in dichloromethane (5 mL) was added. The mixture was stirred at 15° C. for another 15 min, acetic acid (0.5 mL) was added to adjust the pH=4~5. And then sodium cyanoborohydride (419 mg, 6.67 mmol, 2 eq) was added and stirred at 15° C. for 11.5 hours. The reaction mixture was extracted with dichloromethane (40 mL×2). The combined organic layers were washed with brine (25 mL×2), dried over anhydrous sodium sulfate, filtered and concentrated under reduced pressure. The residue was purified by Semi-preparative reverse phase HPLC. Compound methyl 2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]propoxy]isoxazol-5-yl]-3-methyl-butanoate (0.7 g, 0.84 mmol, 25% yield, 99% purity) was obtained as a yellow solid. LC/MS (ESI) m/z: 824.3 $[M+1]^+$.

Step 9: Preparation of 2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoic acid

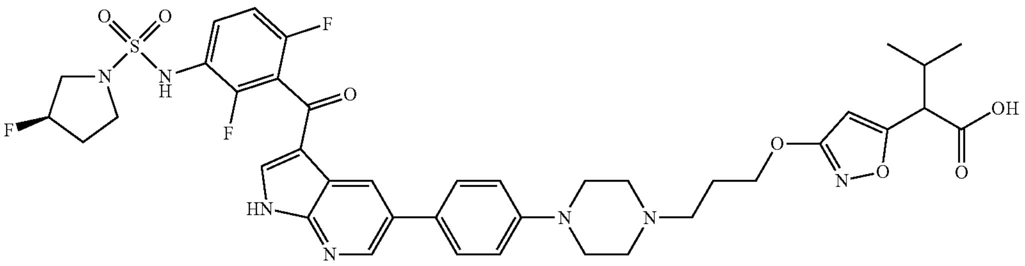 [SMILES: CC(C)C(C(=O)O)c1cc(OCCCN2CCN(c3ccc(-c4cnc5[nH]cc(C(=O)c6c(F)ccc(NS(=O)(=O)N7CC[C@@H](F)C7)c6F)c5c4)cc3)CC2)no1]

To a solution of methyl 2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]propoxy]isoxazol-5-yl]-3-methyl-butanoate (320 mg, 0.40 mmol, 1 eq) in tetrahydrofuran (1 mL) water (0.5 mL) and methanol (2 mL) was added lithium hydrate (28 mg, 1.17 mmol, 3 eq). The mixture was stirred at 40° C. for 2 h. The reaction mixture was acidified with hydrochloric acid (2 M) to pH=5~6. Then the reaction mixture was concentrated under vacuum. The residue was purified by Semi-preparative reverse phase HPLC. Compound 2-[3-[3-[4-[4-[3-[2,6-difluoro-3-[[(3R)-3-fluoropyrrolidin-1-yl]sulfonyl amino]benzoyl]-1H-pyrrolo[2,3-b]pyridin-5-yl]phenyl]piperazin-1-yl]propoxy]isoxazol-5-yl]-3-methyl-butanoic acid (195 mg, 0.23 mmol, 60% yield, 97% purity) was obtained as a yellow solid. LC/MS (ESI) m/z: 810.4 $[M+1]^+$.

Step 10: Preparation of (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide and (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide

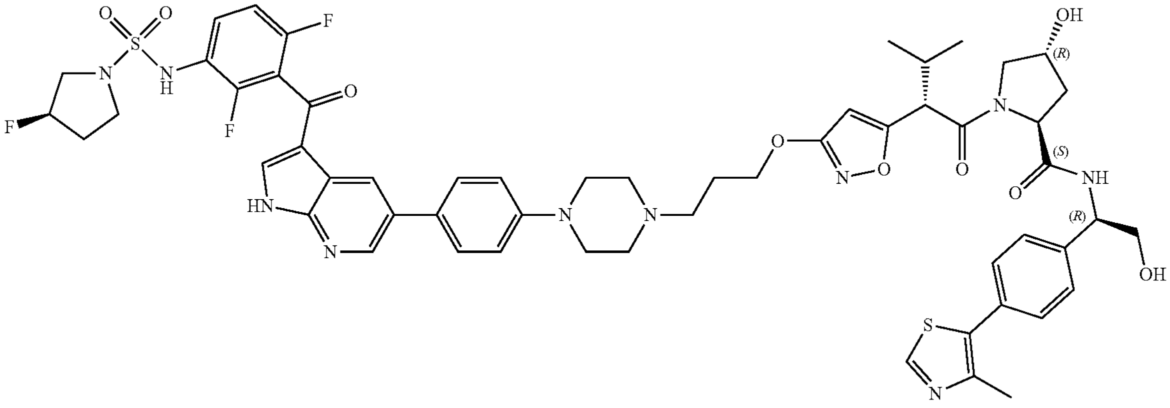

+

-continued

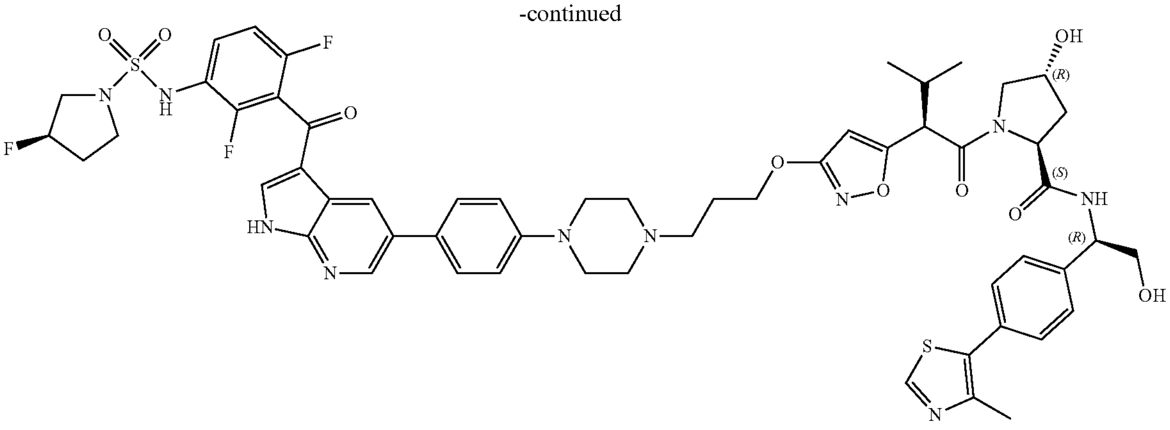

A mixture of 2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]propoxy]isoxazol-5-yl]-3-methyl-butanoic acid (340 mg, 0.42 mmol, 1 eq), (2S,4R)-4-hydroxy-N-[(1R)-2-hydroxy-1-[4-(4-methylthiazol-5-yl)phenyl]ethyl]pyrrolidine-2-carboxamide (161 mg, 0.42 mmol, 1.00 eq, hydrochloride), hydroxybenzotriazole (68 mg, 0.50 mmol, 1.2 eq), N,N-diisopropylethylamine (109 mg, 0.84 mmol, 0.2 mL, 2 eq) and 1-(3-dimethylaminopropyl)-3-ethylcarbodiimide hydrochloride (121 mg, 0.63 mmol, 1.5 eq) in N,N-dimethylformamide (2 mL) and then the mixture was stirred at 15° C. for 2 h. The reaction mixture was extracted with dichloromethane (30 mL×3). The combined organic layers were washed with brine (20 mL×2), dried over anhydrous sodium sulfate, filtered and concentrated under reduced. The residue was purified by Semi-preparative reverse phase HPLC. Compound (2S,4R)-1-[(2S)-2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]propoxy]isoxazol-5-yl]-3-methyl-butanoyl]-4-hydroxy-N-[(1R)-2-hydroxy-1-[4-(4-methylthiazol-5-yl)phenyl]ethyl]pyrrolidine-2-carboxamide (44.9 mg, 0.04 mmol, 10% yield, 95% purity) was obtained as a yellow solid. LC/MS (ESI) m/z: 570.3 $[M/2+1]^+$; $^1$H-NMR (400 MHz, DMSO-$d_6$) δ 12.87 (s, 1H), 9.83 (s, 1H), 9.03-8.94 (m, 1H), 8.67-8.61 (m, 1H), 8.53 (s, 1H), 8.29 (d, J=8.0 Hz, 1H), 8.05 (s, 1H), 7.66-7.54 (m, 3H), 7.50-7.33 (m, 4H), 7.24 (t, J=8.8 Hz, 1H), 7.09-7.02 (m, 2H), 5.95-5.72 (m, 1H), 5.41-5.18 (m, 1H), 5.14 (d, J=3.6 Hz, 1H), 5.10-4.91 (m, 1H), 4.89-4.80 (m, 1H), 4.61-4.43 (m, 1H), 4.34-4.19 (m, 1H), 3.92-3.77 (m, 2H), 3.71-3.64 (m, 1H), 3.62-3.49 (m, 4H), 3.47 (s, 3H), 3.31-3.24 (m, 3H), 3.23-3.15 (m, 4H), 2.56-2.52 (m, 2H), 2.47-2.43 (m, 3H), 2.39-2.26 (m, 3H), 2.13-2.04 (m, 2H), 2.02-1.88 (m, 1H), 1.86-1.67 (m, 3H), 0.99 (d, J=6.4 Hz, 2H), 0.91 (d, J=6.8 Hz, 2H), 0.89-0.77 (m, 2H). Compound (2S,4R)-1-[(2R)-2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]propoxy]isoxazol-5-yl]-3-methyl-butanoyl]-4-hydroxy-N-[(1R)-2-hydroxy-1-[4-(4-methylthiazol-5-yl)phenyl]ethyl]pyrrolidine-2-carboxamide (97.1 mg, 0.09 mmol, 22% yield, 100% purity) was obtained as a yellow solid. LC/MS (ESI) m/z: 570.3 $[M/2+1]^+$; $^1$H-NMR (400 MHz, DMSO-$d_6$) δ 12.91 (s, 1H), 9.86 (s, 1H), 9.04-8.91 (m, 1H), 8.65 (d, J=2.4 Hz, 1H), 8.54 (s, 1H), 8.42 (d, J=8.0 Hz, 1H), 8.07 (s, 1H), 7.66-7.57 (m, 3H), 7.48-7.36 (m, 4H), 7.26 (t, J=8.8 Hz, 1H), 7.15-7.00 (m, 2H), 5.77 (s, 1H), 5.41-5.19 (m, 1H), 5.13 (d, J=3.6 Hz, 1H), 4.84 (t, J=5.6 Hz, 2H), 4.46 (t, J=8.0 Hz, 1H), 4.34-4.21 (m, 1H), 3.90-3.80 (m, 2H), 3.75-3.52 (m, 4H), 3.48 (s, 2H), 3.43-3.35 (m, 3H), 3.32-3.25 (m, 3H), 3.24-3.15 (m, 4H), 2.47-2.42 (m, 4H), 2.40-2.34 (m, 2H), 2.26 (d, J=16.0 Hz, 2H), 2.14-1.98 (m, 3H), 1.85-1.73 (m, 3H), 1.00-0.94 (m, 3H), 0.93-0.86 (m, 3H).

Exemplary Synthesis of (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide (Example 507) and (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide (Example 508)

Step 1: Preparation of tert-butyl 3-(4-(4-bromophenyl)piperazin-1-yl)azetidine-1-carboxylate

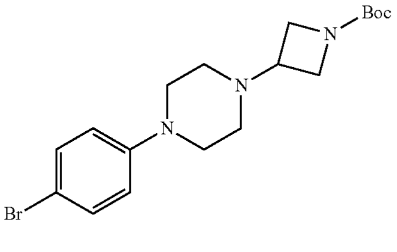 [SMILES: CC(C)(C)OC(=O)N1CC(N2CCN(c3ccc(Br)cc3)CC2)C1]

To a solution of 1-(4-bromophenyl)piperazine (8 g, 28.82 mmol, 1 eq, hydrochloride) and tert-butyl 3-oxoazetidine-1-carboxylate (5.92 g, 34.58 mmol, 1.2 eq) in methanol (130 mL) and acetic acid (13 mL) was added borane;2-methylpyridine (6.17 g, 57.64 mmol, 2 eq). The mixture was stirred at 15° C. for 12 hours. The reaction mixture was extracted with dichloromethane (80 mL×3). The combined organic layers were washed with brine (50 mL×2), dried over anhydrous sodium sulfate, filtered and concentrated under reduced pressure. The residue was purified by silica gel column chromatography (petroleum ether/ethyl acetate=15/1 to 1/1). Compound tert-butyl 3-[4-(4-bromophenyl) piperazin-1-yl]azetidine-1-carboxylate (11.29 g, 26.49 mmol, 91% yield, 93% purity) was obtained as a white solid. LC/MS (ESI) m/z: 341.9 [M−56+1]$^+$.

Step 2: Preparation of 1-(azetidin-3-yl)-4-(4-bromophenyl)piperazine

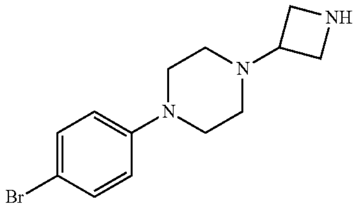 [SMILES: Brc1ccc(N2CCN(C3CNC3)CC2)cc1]

To a solution of tert-butyl 3-[4-(4-bromophenyl)piperazin-1-yl]azetidine-1-carboxylate (11.29 g, 26.49 mmol, 1 eq) in dichloromethane (100 mL) was added trifluoroacetic acid (22 mL). The mixture was stirred at 15° C. for 12 h. The reaction mixture was concentrated under reduced pressure to give a residue. The pH of the residue was adjusted to 8 with saturated aqueous sodium bicarbonate (100 mL). During this period, white precipitate was formed. It was collected by filtration and concentrated. Compound 1-(azetidin-3-yl)-4-(4-bromophenyl) piperazine (8.6 g, crude) was obtained as a white solid. LC/MS (ESI) m/z: 298.0 [M+1]$^+$; $^1$H-NMR (400 MHz, DMSO-$d_6$) δ 8.74 (s, 1H), 7.34 (d, J=8.8 Hz, 2H), 6.91 (d, J=8.8 Hz, 2H), 4.04-3.95 (m, 2H), 3.87 (dd, J=6.4, 10.8 Hz, 2H), 3.31-3.27 (m, 1H), 3.19-3.10 (m, 4H), 2.47-2.42 (m, 4H).

Step 3: Preparation of methyl 2-(3-(3-(4-(4-bromophenyl)piperazin-1-yl)azetidin-1-yl)isoxazol-5-yl)-3-methylbutanoate

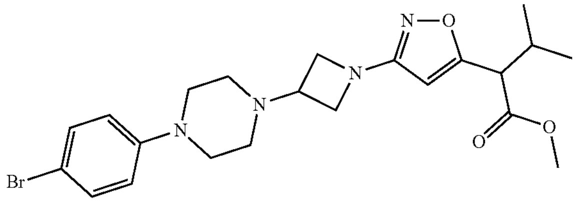 [SMILES: COC(=O)C(c1cc(N2CC(N3CCN(c4ccc(Br)cc4)CC3)C2)no1)C(C)C]

To a solution of 1-(azetidin-3-yl)-4-(4-bromophenyl)piperazine (5 g, 16.88 mmol, 1 eq) in N-Methyl pyrolidone (80 mL) was added N,N-diisopropylethylamine (6.54 g, 50.64 mmol, 8.82 mL, 3 eq) and methyl 3-methyl-2-[3-(1,1,2,2,3,3,4,4,4-nonafluorobutylsulfonyloxy) isoxazol-5-yl]butanoate (8.12 g, 16.88 mmol, 1 eq). The mixture was stirred at 110° C. for 2 h. The reaction mixture was extracted with ethyl acetate (40 mL×3). The combined organic layers were washed with brine (30 mL×3), dried over anhydrous sodium sulfate, filtered and concentrated under reduced pressure. The residue was purified by preparative reverse phase HPLC. The mixture was basified with saturated sodium bicarbonate to pH=7~8. And then the mixture was extracted with ethyl acetate (60 mL×2). The combined organic layers were washed with saturated aqueous brine (30 mL×2) and dried over anhydrous sodium sulfate, filtered and concentrated under reduced pressure. Compound methyl 2-[3-[3-[4-(4-bromophenyl)piperazin-1-yl]azetidin-1-yl]isoxazol-5-yl]-3-methyl-butanoate (1.43 g, 2.78 mmol, 16% yield, 92% purity) was obtained as a yellow solid. Compound methyl 2-(3-hydroxyisoxazol-5-yl)-3-methyl-butanoate (2 g, 10.04 mmol, 59% yield) was obtained as a yellow oil. LC/MS (ESI) m/z: 478.9 [M+1]$^+$.

Step 4: Preparation of methyl 2-(3-(3-(4-(4-(3-(2,6-difluoro-3-(((R)-3-fluoro-N-((2-(trimethylsilyl)ethoxy)methyl)pyrrolidine)-1-sulfonamido)benzoyl)-1-((2-(trimethylsilyl)ethoxy)methyl)-1H-pyrrolo[2,3-b]pyridin-5-yl)phenyl)piperazin-1-yl)azetidin-1-yl)isoxazol-5-yl)-3-methylbutanoate

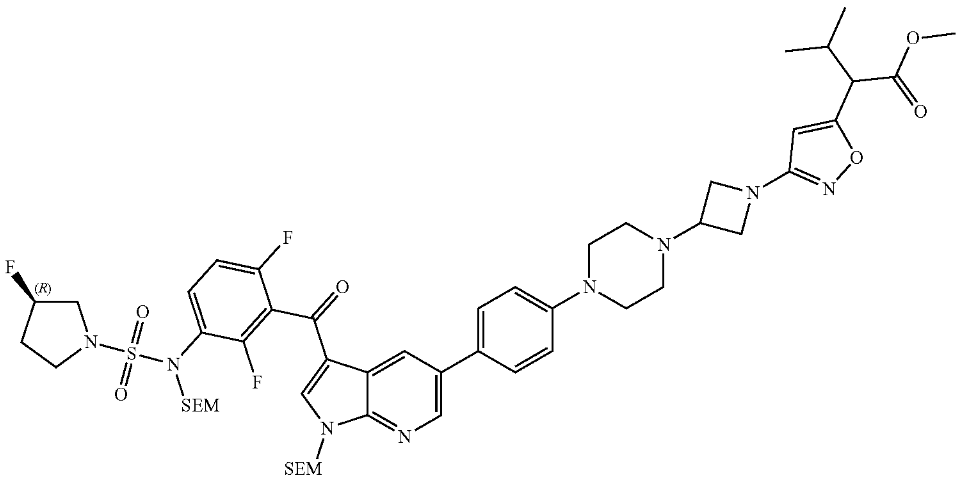

A mixture of methyl 2-[3-[3-[4-(4-bromophenyl)piperazin-1-yl]azetidin-1-yl]isoxazol-5-yl]-3-methyl-butanoate (1.43 g, 3.00 mmol, 1 eq), (3R)—N-[2,4-difluoro-3-[5-(4,4,5,5-tetramethyl-1,3,2-dioxaborolan-2-yl)-1-(2-trimethylsilylethoxymethyl)pyrrolo[2,3-b]pyridine-3-carbonyl]phenyl]-3-fluoro-N-(2-trimethylsilylethoxymethyl)pyrrolidine-1-sulfonamide (2.43 g, 3.00 mmol, 1 eq), 4-ditert-butylphosphanyl-N,N-dimethyl-aniline;dichloropalladium (212 mg, 0.30 mmol, 0.1 eq), cesium fluoride (1.82 g, 11.98 mmol, 4 eq) in dioxane (10 mL) and water (2 mL) was degassed and purged with nitrogen for 3 times, and then the mixture was stirred at 100° C. for 12 h under nitrogen atmosphere. The reaction mixture was extracted with ethyl acetate (40 mL×2). The combined organic layers were washed with brine (25 mL×2), dried over anhydrous sodium sulfate, filtered and concentrated under reduced pressure. The residue was purified by silica gel column chromatography (petroleum ether/ethyl acetate=10/1 to 1/1). Compound methyl 2-[3-[3-[4-[4-[3-[2,6-difluoro-3-[[(3R)-3-fluoropyrrolidin-1-yl]sulfonyl-(2-trimethyl silylethoxymethyl)amino]benzoyl]-1-(2-trimethylsilylethoxymethyl)pyrrolo[2,3-b]pyridin-5-yl]phenyl]piperazin-1-yl]azetidin-1-yl]isoxazol-5-yl]-3-methyl-butanoate (1.95 g, 1.78 mmol, 59% yield, 98% purity) was obtained as a yellow oil. LC/MS (ESI) m/z: 541.3 [M/2+1]$^+$.

Step 5: Preparation of methyl 2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoate

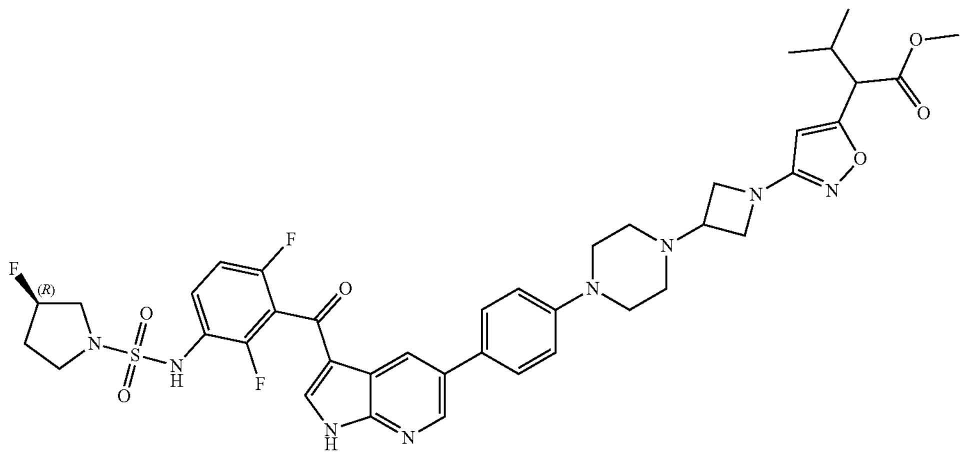

To a solution of methyl 2-[3-[3-[4-[4-[3-[2,6-difluoro-3-[[(3R)-3-fluoropyrrolidin-1-yl]sulfonyl-(2-trimethylsilylethoxymethyl)amino]benzoyl]-1-(2-trimethylsilylethoxymethyl)pyrrolo[2,3-b]pyridin-5-yl]phenyl]piperazin-1-yl]azetidin-1-yl]isoxazol-5-yl]-3-methyl-butanoate (1.95 g, 1.78 mmol, 1 eq) in 1,2-dichloromethane (6 mL) was added trifluoroacetic acid (3.05 g, 26.74 mmol, 2 mL, 15 eq). The mixture was stirred at 30° C. for 16 h. The reaction mixture was concentrated under reduced pressure. Compound methyl 2-[3-[3-[4-[4-[3-[2,6-difluoro-3-[[(3R)-3-fluoropyrrolidin-1-yl]sulfonyl amino]benzoyl]-1H-pyrrolo[2,3-b]pyridin-5-yl]phenyl]piperazin-1-yl]azetidin-1-yl]isoxazol-5-yl]-3-methyl-butanoate (1.67 g, crude, trifluoroacetic acid) was obtained as a yellow oil, which was directly used into the next step and without further purification. LC/MS (ESI) m/z: 411.4 [M/2+1]$^+$.

Step 6: Preparation of 2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoic acid

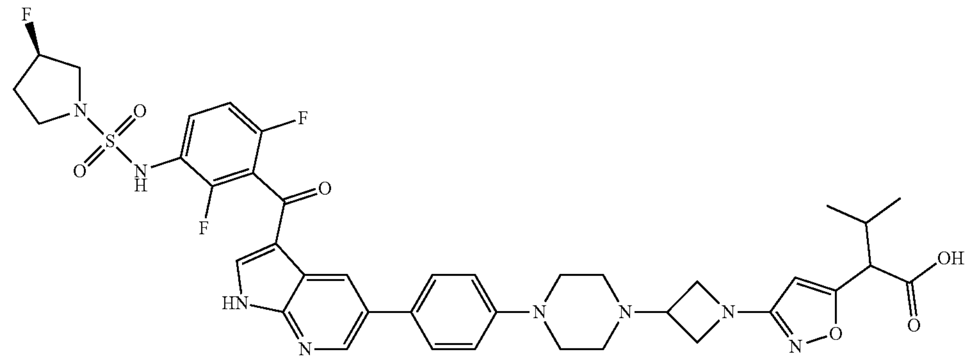 [SMILES: CC(C)C(C(=O)O)c1cc(N2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)no1]

To a solution of methyl 2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoate (1.67 g, 1.79 mmol, 1 eq, trifluoroacetate) in tetrahydrofuran (8 mL) and water (2 mL) was added sodium hydroxide (285 mg, 7.15 mmol, 4 eq). The mixture was stirred at 40° C. for 2 hours. The reaction mixture was acidified with sulfuric acid (1 M) to pH=5~6. Then the reaction mixture was concentrated under vacuum. The residue was purified by Semi-preparative reverse phase HPLC. Compound 2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoic acid (520 mg, 0.64 mmol, 36% yield, 99% purity) was obtained as a yellow solid. LC/MS (ESI) m/z: 807.3 [M+1]$^+$.

Step 7: Preparation of (2S,4R)-1-(2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide

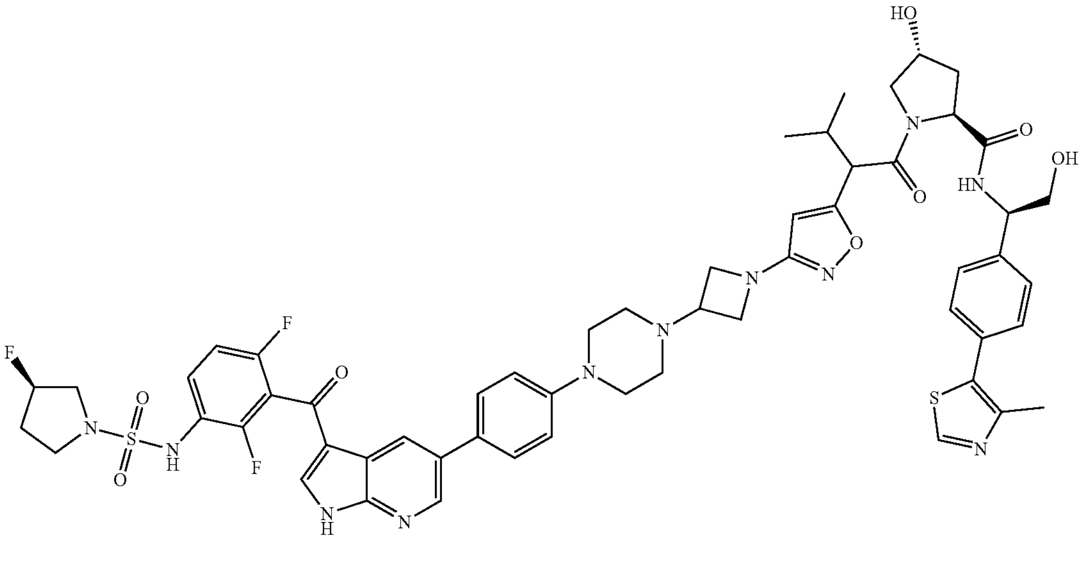 [SMILES: Cc1ncsc1-c1ccc([C@H](CO)NC(=O)[C@@H]2C[C@@H](O)CN2C(=O)C(c2cc(N3CC(N4CCN(c5ccc(-c6cnc7[nH]cc(C(=O)c8c(F)ccc(NS(=O)(=O)N9CC[C@@H](F)C9)c8F)c7c6)cc5)CC4)C3)no2)C(C)C)cc1]

To a solution of 2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoic acid (170 mg, 0.21 mmol, 1 eq) and (2S,4R)-4-hydroxy-N-[(1R)-2-hydroxy-1-[4-(4-methylthiazol-5-yl)phenyl]ethyl]pyrrolidine-2-carboxamide (89 mg, 0.23 mmol, 1.1 eq, hydrochloride) in N,N-dimethylformamide (1 mL) was added hydroxybenzotriazole (34 mg, 0.25 mmol, 1.2 eq) N,N-diisopropylethylamine (82 mg, 0.63 mmol, 0.1 mL, 3 eq) and 1-(3-dimethylaminopropyl)-3-ethylcarbodiimide hydrochloride (61 mg, 0.32 mmol, 1.5 eq). The mixture was stirred at 15° C. for 12 h. The reaction mixture was extracted with dichloromethane (30 mL×2). The combined organic layers were washed with brine (20 mL×2), dried over anhydrous sodium sulfate, filtered and concentrated under reduced pressure. The residue was purified by prep-HPLC. Compound (2S,4R)-1-[(2R)-2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoyl]-4-hydroxy-N-[(1R)-2-hydroxy-1-[4-(4-methylthiazol-5-yl)phenyl]ethyl]pyrrolidine-2-carboxamide (160 mg, 0.14 mmol, 65% yield, 97% purity) was obtained as a yellow solid. LC/MS (ESI) m/v 568.9 $[M/2+1]^+$.

Step 8: Preparation of (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide and (2S,4R)-1-((R)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide

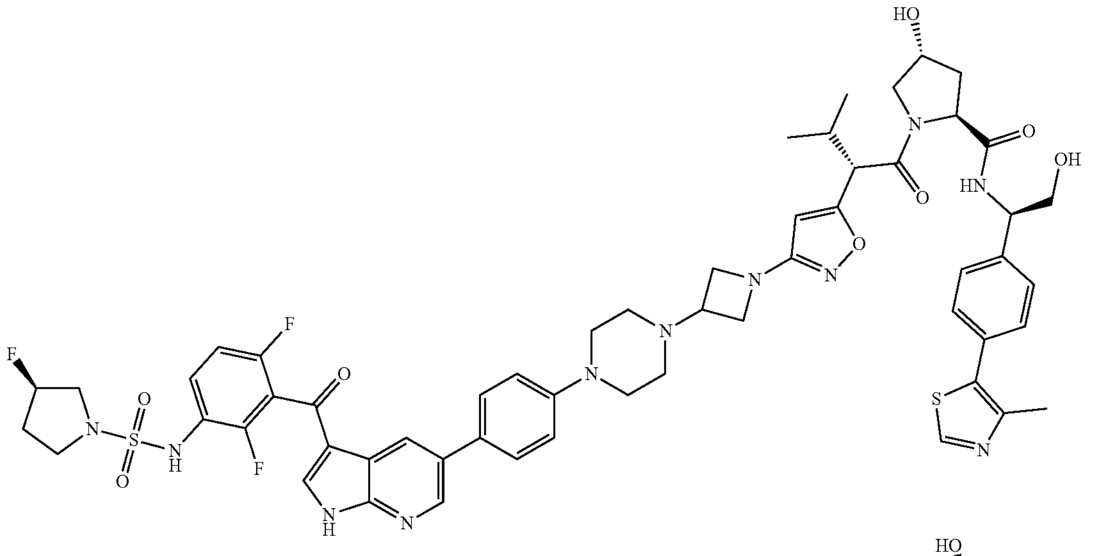

+

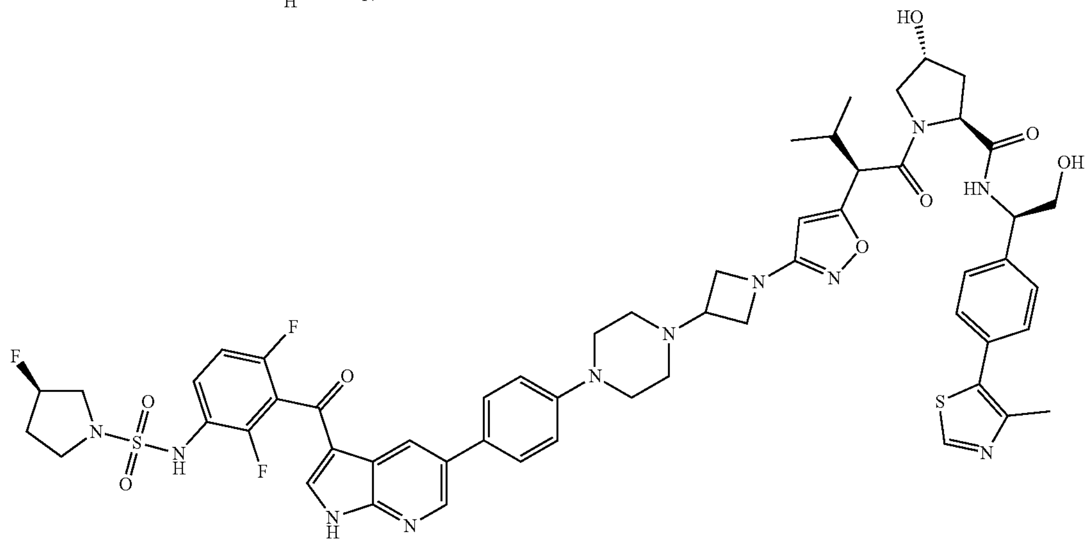

The (2S,4R)-1-[(2R)-2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoyl]-4-hydroxy-N-[(1R)-2-hydroxy-1-[4-(4-methylthiazol-5-yl)phenyl]ethyl]pyrrolidine-2-carboxamide (160 mg, 0.15 mmol, 1 eq) was separated by SFC. The fraction was concentrated in vacuum and the residue was purified by prep-HPLC. Compound (2S,4R)-1-[(2S)-2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoyl]-4-hydroxy-N-[(1R)-2-hydroxy-1-[4-(4-methylthiazol-5-yl)phenyl]ethyl]pyrrolidine-2-carboxamide (38 mg, 0.03 mmol, 43% yield, 98% purity) was obtained as a yellow solid. LC/MS (ESI) m/z: 568.8 $[M/2+1]^+$; $^1$H-NMR (400 MHz, DMSO-$d_6$) δ 12.73 (s, 1H), 8.99 (s, 1H), 8.88 (d, J=8.4 Hz, 1H), 8.63 (d, J=2.0 Hz, 1H), 8.49 (s, 1H), 8.11 (d, J=8.4 Hz, 1H), 7.96 (s, 1H), 7.60 (d, J=8.4 Hz, 2H), 7.56-7.46 (m, 2H), 7.43 (d, J=8.0 Hz, 2H), 7.38-7.33 (m, 1H), 7.07 (d, J=8.8 Hz, 2H), 6.96 (s, 1H), 5.96-5.88 (m, 1H), 5.36-5.16 (m, 1H), 5.14 (d, J=3.6 Hz, 1H), 5.08-4.91 (m, 1H), 4.89-4.79 (m, 1H), 4.65-4.44 (m, 1H), 4.34-4.19 (m, 1H), 4.03-3.87 (m, 2H), 3.81-3.64 (m, 4H), 3.58 (dd, J=6.0, 12.0 Hz, 4H), 3.30-3.04 (m, 3H), 2.47 (d, J=2.4 Hz, 9H), 2.31-2.22 (m, 1H), 2.11 (s, 1H), 2.09-2.00 (m, 2H), 2.00-1.89 (m, 2H), 1.88-1.80 (m, 1H), 1.06-0.79 (m, 6H), 0.76 (d, J=6.8 Hz, 1H). Compound (2S,4R)-1-[(2R)-2-[3-[3-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]azetidin-1-yl]isoxazol-5-yl]-3-methyl-butanoyl]-4-hydroxy-N-[(1R)-2-hydroxy-1-[4-(4-methylthiazol-5-yl)phenyl]ethyl]pyrrolidine-2-carboxamide (61.1 mg, 0.05 mmol, 71% yield, 98% purity) was obtained as a yellow solid. LC/MS (ESI) m/z: 568.7 $[M/2+1]^+$; $^1$H-NMR (400 MHz, DMSO-$d_6$) δ 12.88 (s, 1H), 8.98 (s, 1H), 8.93-8.68 (m, 1H), 8.65 (d, J=2.0 Hz, 1H), 8.52 (s, 1H), 8.38 (d, J=8.0 Hz, 1H), 8.03 (s, 1H), 7.69-7.55 (m, 3H), 7.50-7.34 (m, 4H), 7.17 (t, J=8.8 Hz, 1H), 7.09 (d, J=8.8 Hz, 2H), 5.94-5.82 (m, 1H), 5.41-5.18 (m, 1H), 5.13 (d, J=3.6 Hz, 1H), 5.03-4.73 (m, 2H), 4.43 (t, J=8.0 Hz, 1H), 4.29 (s, 1H), 3.97 (br t, J=6.8 Hz, 2H), 3.83-3.67 (m, 4H), 3.67-3.54 (m, 4H), 3.29-3.20 (m, 6H), 3.17 (d, J=5.2 Hz, 1H), 2.57-2.52 (m, 3H), 2.46 (s, 4H), 2.28-2.17 (m, 1H), 2.11 (s, 1H), 2.09-1.91 (m, 3H), 1.87-1.76 (m, 1H), 1.04-0.74 (m, 6H).

Exemplary Synthesis of 3-(1-oxo-5-(piperazin-1-yl)isoindolin-2-yl)piperidine-2,6-dione (Intermediate X)

Step 1: Preparation of methyl 2-bromo-4-fluorobenzoate

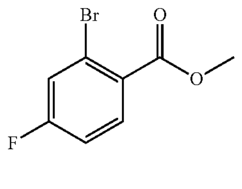

To a solution of 2-bromo-4-fluoro-benzoic acid (100 g, 456.60 mmol, 1 eq) in methanol (800 mL) was added sulfurous dichloride (108.64 g, 913.21 mmol, 2 eq) at 0° C. The mixture was stirred at 80° C. for 12 hours. The reaction mixture was concentrated under reduced pressure. The residue was diluted with water 500 mL and extracted with ethyl acetate (200 mL×2). The combined organic phase was washed with saturated sodium bicarbonate (200 mL) and saturated brine (200 mL×2), dried with anhydrous sodium sulfate, filtered and concentrated in vacuum to give methyl 2-bromo-4-fluoro-benzoate (102 g, 437.70 mmol, 95% yield) as a brown oil.

Step 2: Preparation of tert-butyl 4-(3-bromo-4-(methoxycarbonyl)phenyl)piperazine-1-carboxylate

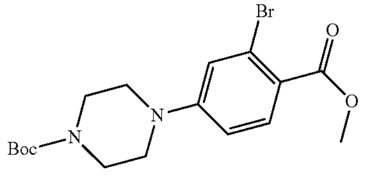 [SMILES: COC(=O)c1ccc(N2CCN(C(=O)OC(C)(C)C)CC2)cc1Br]

To a solution of methyl 2-bromo-4-fluoro-benzoate (90 g, 386.21 mmol, 1 eq) in dimethylsulfoxide (500 mL) was added tert-butyl piperazine-1-carboxylate (111.82 g, 502.07 mmol, 1.3 eq, hydrochloric salt) and N,N-diisopropylethylamine (199.66 g, 1.54 mol, 269 mL, 4 eq). The mixture was heated to 130° C. and stirred at 130° C. for 36 hours. The mixture was poured into 1.0 L water, and extracted with ethyl acetate (500 mL×2). The organic layer was washed with water (1000 mL), 0.5 M hydrochloric acid (500 mL), saturated brine (500 mL) and then dried over anhydrous sodium sulfate, filtered and concentrated in vacuum. The residue was triturated with (petroleum ether:ethyl acetate=5:1, 300 mL), the solid was filtered and dried in vacuum, tert-butyl 4-(3-bromo-4-methoxycarbonyl-phenyl)piperazine-1-carboxylate (93 g, 232.92 mmol, 60% yield) was obtained as an off-white solid. LC/MS (ESI) m/z: 422.1 $[M+23]^+$; $^1$H-NMR (400 MHz, DMSO-$d_6$) δ 7.73 (d, J=8.8 Hz, 1H), 7.18 (d, J=2.4 Hz, 1H), 6.98 (dd, J=8.8, 2.4 Hz, 1H), 3.77 (s, 3H), 3.45-3.42 (m, 4H), 3.34-3.31 (m, 4H), 1.42 (s, 9H).

Step 3: Preparation of 2-bromo-4-(4-(tert-butoxycarbonyl)piperazin-1-yl)benzoic acid

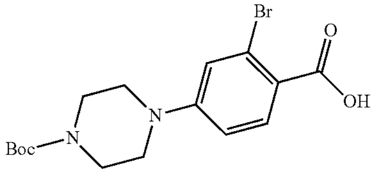 [SMILES: CC(C)(C)OC(=O)N1CCN(c2ccc(C(=O)O)c(Br)c2)CC1]

To a solution of tert-butyl 4-(3-bromo-4-methoxycarbonyl-phenyl)piperazine-1-carboxylate (92 g, 230.42 mmol, 1 eq) in a mixture of tetrahydrofuran (400 mL), water (200 mL) and methanol (200 mL) was added sodium hydroxide (27.65 g, 691.25 mmol, 3 eq). The mixture was stirred at 60° C. for 2 hours. The mixture was poured into 1.0 L water, adjust the pH to 5.0 with 11.8 M hydrochloric acid, and then extracted with ethyl acetate (800 mL×2). The combined organic layers were dried over anhydrous sodium sulfate, filtered and concentrated in vacuum. 2-bromo-4-(4-tert-butoxycarbonylpiperazin-1-yl) benzoic acid (85 g, 220.63 mmol, 95% yield) was obtained as an off-white solid. LC/MS (ESI) m/z: 406.9 $[M+23]^+$; $^1$H-NMR (400 MHz, DMSO-$d_6$) δ 7.75 (d, J=8.8 Hz, 1H), 7.15 (d, J=2.0 Hz, 1H), 6.96 (dd, J=8.8, 2.0 Hz, 1H), 3.44-3.42 (m, 4H), 3.34-3.31 (m, 4H), 1.42 (s, 9H).

Step 4: Preparation of 4-(4-(tert-butoxycarbonyl) piperazin-1-yl)-2-formylbenzoic acid

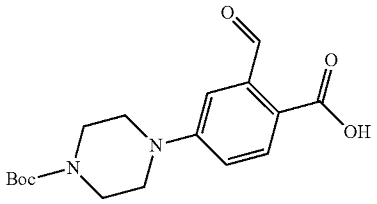 [SMILES: CC(C)(C)OC(=O)N1CCN(c2ccc(C(=O)O)c(C=O)c2)CC1]

To a solution of 2-bromo-4-(4-tert-butoxycarbonylpiperazin-1-yl)benzoic acid (54 g, 140.17 mmol, 1 eq) in tetrahydrofuran (600 mL) was added methyl lithium (1.6 M, 88 mL, 1.0 eq) at −70° C. The mixture was stirred at −70° C. for half an hour, n-butyl lithium (2.5 M, 67 mL, 1.2 eq) was added at −70° C. The mixture was stirred at −70° C. for half an hour, and then dimethylformamide (30.74 g, 420.50 mmol, 32 mL, 3 eq) was added. The resulting mixture was stirred at −70~-50° C. for another 1 hr. The mixture was poured into 1.0 L water, adjust the pH to 5.0 with 2.0 M hydrochloric acid, and then extracted with ethyl acetate (800 mL×3). The organic layer was dried over anhydrous sodium sulfate, filtered and concentrated in vacuum. The residue was triturated with petroleum ether:ethyl acetate (V/V=1:3, 500 mL). 4-(4-tert-butoxycarbonylpiperazin-1-yl)-2-formyl-benzoic acid (36 g, 107.67 mmol, 77% yield) was obtained as a brown solid. LC/MS (ESI) m/z: 357.1 $[M+23]^+$; $^1$H-NMR (400 MHz, DMSO-$d_6$) δ 7.98 (d, J=8.4 Hz, 1H), 7.58 (d, J=8.4 Hz, 1H), 7.12 (dd, J=8.4, 2.0 Hz, 1H), 6.48 (d, J=6.4 Hz, 1H), 3.60-3.39 (m, 8H), 1.43 (s, 9H).

Step 5: Preparation of 4-(4-(tert-butoxycarbonyl) piperazin-1-yl)-2-(((2,6-dioxopiperidin-3-yl)amino) methyl)benzoic acid

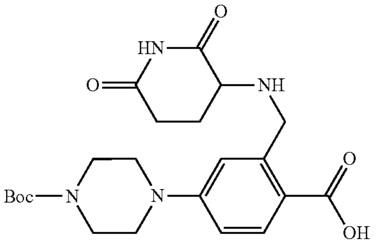 [SMILES: CC(C)(C)OC(=O)N1CCN(c2ccc(C(=O)O)c(CNC3CCC(=O)NC3=O)c2)CC1]

A solution of 3-aminopiperidine-2,6-dione (11.81 g, 71.78 mmol, 1.2 eq, hydrochloric salt) and sodium acetate (9.81 g, 119.63 mmol, 2 eq) in methanol (250 mL) was stirred at 15° C. for half an hour, then 4-(4-tert-butoxycarbonylpiperazin-1-yl)-2-formyl-benzoic acid (20 g, 59.81 mmol, 1 eq) was added. The mixture was stirred at 15° C. for another half an hour, sodium cyanoborohydride (7.52 g, 119.63 mmol, 2 eq) was added. The resulting mixture was stirred at 15° C. for another 2 hr. The mixture was poured into 800 mL water, and adjust the pH to 5.0 with 2.0 M hydrochloric acid, and then extracted with ethyl acetate (400 mL×3). The organic layer was dried over anhydrous sodium sulfate, filtered and concentrated in vacuum. The residue was triturated with petroleum ether:ethyl acetate (V/V=3:1, 200 mL). 4-(4-tert-butoxycarbonylpiperazin-1-yl)-2-[[(2,6-dioxo-3-piperidyl)amino]methyl]benzoic acid (26 g, 49.38 mmol, 82% yield, 84% purity) was obtained as a gray solid. LC/MS (ESI) m/z: 447.1 $[M+1]^+$.

Step 6: Preparation of tert-butyl 4-(2-(2,6-dioxopiperidin-3-yl)-1-oxoisoindolin-5-yl)piperazine-1-carboxylate

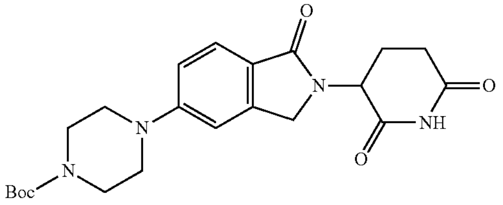 [SMILES: CC(C)(C)OC(=O)N1CCN(c2ccc3c(c2)CN(C2CCC(=O)NC2=O)C3=O)CC1]

To a solution of 4-(4-tert-butoxycarbonylpiperazin-1-yl)-2-[[(2,6-dioxo-3-piperidyl)amino]methyl]benzoic acid (27 g, 51.10 mmol, 1 eq) and O-Benzotriazol-1-yl-tetramethyluronium hexafluorophosphate (23.31 g, 61.32 mmol, 1.2 eq) in dimethylformamide (250 mL) was added diisopropylethylamine (19.81 g, 153.29 mmol, 3 eq). The mixture was stirred at 15° C. for 1 h. The mixture was poured into 800 mL water, the mixture was stirred at 15° C. for half an hour. The solid formed was filtered and washed with ethyl acetate 100 mL, and then dried in vacuum. tert-butyl 4-[2-(2,6-dioxo-3-piperidyl)-1-oxo-isoindolin-5-yl]piperazine-1-carboxylate (14.5 g, 33.84 mmol, 66% yield) was obtained as a yellow solid. LC/MS (ESI) m/z: 429.2 $[M+1]^+$; $^1$H NMR (400 MHz, DMSO-$d_6$) δ 10.97 (s, 1H), 7.54 (d, J=8.4 Hz, 1H), 7.08-7.06 (m, 2H), 5.03 (dd, J=13.2, 5.2 Hz, 1H), 4.36-4.19 (m, 2H), 3.48-3.45 (m, 4H), 3.27-3.26 (m, 4H), 2.89-2.87 (m, 1H), 2.60-2.56 (m, 1H), 2.38-2.34 (m, 1H), 1.98-1.96 (m, 1H), 1.43 (s, 9H).

Step 7: Preparation of 3-(1-oxo-5-(piperazin-1-yl) isoindolin-2-yl)piperidine-2,6-dione

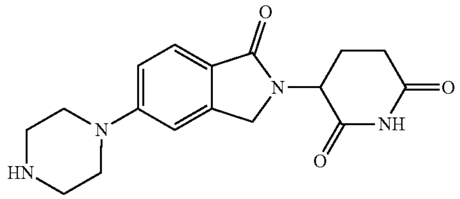 [SMILES: O=C1CCC(N2Cc3cc(N4CCNCC4)ccc3C2=O)C(=O)N1]

A suspension of tert-butyl 4-[2-(2,6-dioxo-3-piperidyl)-1-oxo-isoindolin-5-yl]piperazine-1-carboxylate (14.5 g, 33.84 mmol, 1 eq) in hydrochloride/dioxane (4.0 M, 250 mL) was stirred at 15° C. for 3 hr. The solvent was concentrated in vacuum; the residue was triturated with ethyl acetate (50 mL). 3-(1-oxo-5-piperazin-1-yl-isoindolin-2-yl) piperidine-2,6-dione (12 g, 32.89 mmol, 97% yield, hydrochloric salt) was obtained as a white solid. LC/MS (ESI) m/z: 329.1 $[M+1]^+$; $^1$H-NMR (400 MHz, DMSO-$d_6$) δ 10.98 (s, 1H), 9.43 (s, 2H), 7.58 (d, J=8.8 Hz, 1H), 7.16-7.11 (m, 2H), 5.07 (dd, J=13.2, 5.2 Hz, 1H), 4.38-4.21 (m, 2H), 3.55-3.53 (m, 4H), 3.20-3.19 (m, 4H), 2.90-2.86 (m, 1H), 2.60-2.56 (m, 1H), 2.38-2.34 (m, 1H), 1.98-1.96 (m, 1H).

Exemplary Synthesis of (3R)—N-(3-(5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridine-3-carbonyl)-2,4-difluorophenyl)-3-fluoropyrrolidine-1-sulfonamide (Exemplary Compound 522)

Step 1: Preparation of 5-(4-(dimethoxymethyl)piperidin-1-yl)isobenzofuran-1(3H)-one

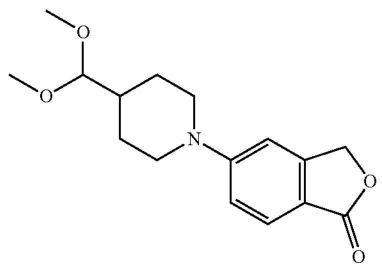 [SMILES: COC(OC)C1CCN(c2ccc3c(c2)COC3=O)CC1]

To a solution of 5-fluoro-3H-isobenzofuran-1-one (1.6 g, 10.52 mmol, 1 eq) in dimethyl sulfoxide (20 mL) was added 4-(dimethoxymethyl)piperidine (1.67 g, 10.52 mmol, 1 eq) and N,N-diisopropylethylamine (2.72 g, 21.04 mmol, 2 eq), and the reaction was stirred at 120° C. for 2 hr. The residue was washed with water (30 mL) and extracted with ethyl acetate (30 mL×3). The combined organic layers were washed with brine (30×3 mL), dried over anhydrous sodium sulfate, filtered and concentrated under reduced pressure. The residue was purified by column chromatography (Petroleum ether:Ethyl acetate=20:1 to pure Ethyl acetate). The product 5-[4-(dimethoxymethyl)-1-piperidyl]-3H-isobenzofuran-1-one (1.9 g, 6.52 mmol, 62% yield) was obtained as yellow solid. LC/MS (ESI) m/z: 292.2 $[M+1]^+$; $^1H$-NMR (400 MHz, $CDCl_3$) δ 7.70-7.48 (m, 1H), 7.15-6.91 (m, 2H), 5.23 (s, 2H), 4.06 (d, J=6.8 Hz, 1H), 3.96 (d, J=13.2 Hz, 2H), 3.26 (s, 5H), 3.14-3.13 (m, 1H), 3.11-2.97 (m, 1H), 2.95-2.76 (m, 2H), 2.00-1.78 (m, 1H), 1.70 (d, J=12.8 Hz, 2H), 1.39-1.16 (m, 2H).

Step 2: Preparation of 4-(4-(dimethoxymethyl)piperidin-1-yl)-2-(hydroxymethyl)benzoic acid

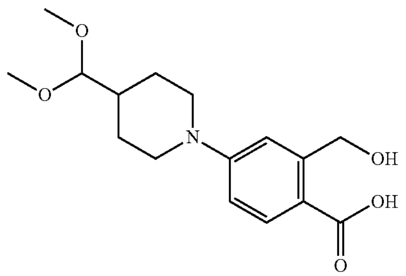 [SMILES: COC(OC)C1CCN(c2ccc(C(=O)O)c(CO)c2)CC1]

To a solution of 5-[4-(dimethoxymethyl)-1-piperidyl]-3H-isobenzofuran-1-one (1.9 g, 6.52 mmol, 1 eq) in methanol (10 mL) was added sodium hydroxide (1.30 g, 32.61 mmol, 5 eq), water (10 mL) and the mixture was stirred at 20° C. for 1 hr. The residue was washed with water (30 mL) and extracted with Ethyl acetate (30 mL×3). The combined organic layers were washed with brine (30 mL×3), dried over anhydrous sodium sulfate, filtered and concentrated under reduced pressure. The organic phase was dried by anhydrous sodium sulfate, filtered and the filtrate was condensed to give the product, 4-[4-(dimethoxymethyl)-1-piperidyl]-2-(hydroxymethyl)benzoic acid (1.64 g) as colorless oil.

Step 3: Preparation of methyl 4-(4-(dimethoxymethyl)piperidin-1-yl)-2-(hydroxy methyl)benzoate

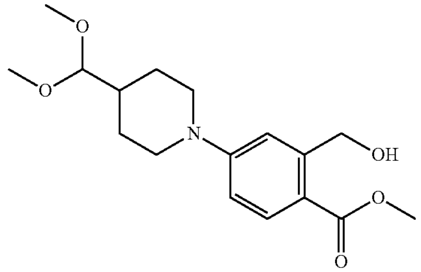

To a solution of 4-[4-(dimethoxymethyl)-1-piperidyl]-2-(hydroxymethyl)benzoic acid (1.64 g, 5.30 mmol, 1 eq) in methanol (10 mL) and Ethyl acetate (10 mL) was added (diazomethyl)trimethlsilane (2 M, 7.95 mL, 3 eq) at −10° C. The reaction mixture was stirred at −10° C. for 0.25 h. The solution was quenched with water (20 mL) and extracted with ethyl acetate (30 mL×3). The organic layer was dried over sodium sulfate and filtered. The filtrate was concentrated to give the product, methyl 4-[4-(dimethoxymethyl)-1-piperidyl]-2-(hydroxy methyl)benzoate (1.7 g, 5.26 mmol, 99% yield) as colorless oil.

Step 4: Preparation of methyl 2-(bromomethyl)-4-(4-(dimethoxymethyl)piperidin-1-yl)benzoate

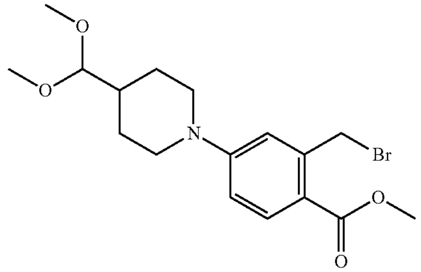

To a solution of methyl 4-[4-(dimethoxymethyl)-1-piperidyl]-2-(hydroxymethyl)benzoate (1.7 g, 5.26 mmol, 1 eq) in tetrahydrofuran (20 mL) was added perbromomethane (2.62 g, 7.89 mmol, 1.5 eq) and triphenylphosphine (2.07 g, 7.89 mmol, 1.5 eq). The reaction was stirred at 20° C. for 1 h. The solution was quenched with water (20 mL) and extracted with ethyl acetate (30 mL×3). The organic layer was dried over sodium sulfate and filtered. The filtrate was concentrated to give crude product. The residue was purified by column chromatography (silicon dioxide, Petroleum ether:Ethyl acetate=40:1 to 20:1). The product methyl 2-(bromomethyl)-4-[4-(dimethoxymethyl)-1-piperidyl]benzoate (1.2 g, 3.11 mmol, 59% yield) was obtained as yellow solid. LC/MS (ESI) m/z: 388.1 $[M+1]^+$; $^1H$-NMR (400 MHz, $CDCl_3$) δ 7.96-7.87 (m, 1H), 6.95-6.74 (m, 2H), 4.97

(s, 2H), 4.07 (d, J=6.8 Hz, 1H), 3.94-3.83 (m, 5H), 3.38 (s, 6H), 2.84 (dt, J=2.0, 12.8 Hz, 2H), 1.94-1.76 (m, 3H), 1.61-1.33 (m, 3H).

Step 5: Preparation of 3-(5-(4-(dimethoxymethyl) piperidin-1-yl)-1-oxoisoindolin-2-yl)piperidine-2,6-dione

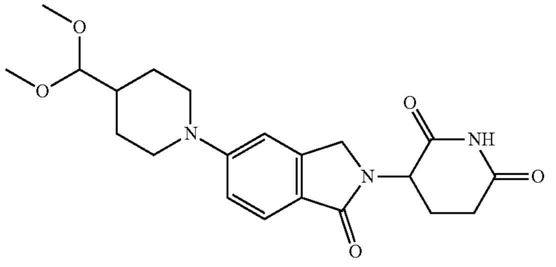 [SMILES: COC(OC)C1CCN(c2ccc3c(c2)CN(C2CCC(=O)NC2=O)C3=O)CC1]

To a solution of 3-[5-[4-(dimethoxymethyl)-1-piperidyl]-1-oxo-isoindolin-2-yl]piperidine-2,6-dione (50 mg, 0.13 mmol, 1 eq) in tetrahydrofuran (1 mL) and water (0.2 mL) was added pyridinium p-toluenesulfonate (63 mg, 0.25 umol, 2 eq) and the mixture was stirred at 70° C. for 8 hr. The mixture was concentrated in the vacuum to get the product, 1-[2-(2,6-dioxo-3-piperidyl)-1-oxo-isoindolin-5-yl]piperidine-4-carbaldehyde (40 mg) as a colorless oil. LC/MS (ESI) m/z: 356.2 $[M+1]^+$.

Step 7: Preparation of (3R)—N-(3-(5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridine-3-carbonyl)-2,4-difluorophenyl)-3-fluoropyrrolidine-1-sulfonamide

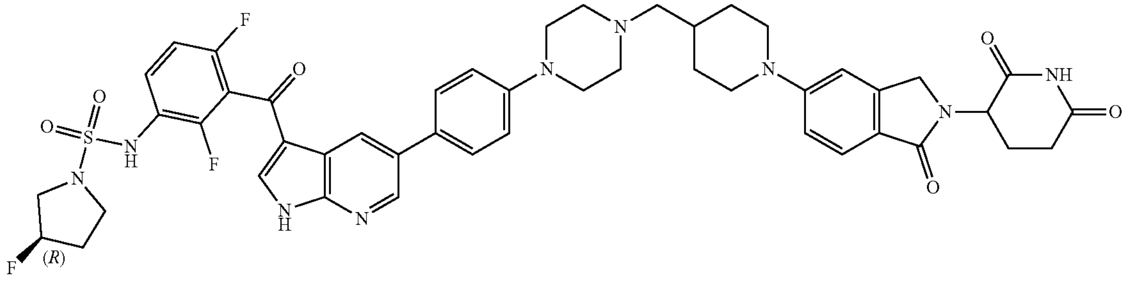

To a solution of methyl 2-(bromomethyl)-4-[4-(dimethoxymethyl)-1-piperidyl]benzoate (300 mg, 0.78 mmol, 1 eq) and 3-aminopiperidine-2,6-dione (192 mg, 1.16 mmol, 1.5 eq, HCl) in acetonitrile (20 mL) was added N,N-diisopropylethylamine (301 mg, 2.33 mmol, 3 eq). The reaction mixture was stirred at 100° C. for 15 h. Water (20 mL) was added to the solution and extracted with dichloromethane (30 mL×3). The organic layer was dried over sodium sulfate and filtered. The filtrate was concentrated to give crude product. The crude product was triturated with ethyl acetate (50 mL) at 25° C. for 10 min. The product 3-[5-[4-(dimethoxymethyl)-1-piperidyl]-1-oxo-isoindolin-2-yl]piperidine-2,6-dione (200 mg, 0.50 mmol, 64% yield) was obtained as gray solid. LC/MS (ESI) m/z: 402.1 $[M+1]^+$.

Step 6: Preparation of 1-(2-(2,6-dioxopiperidin-3-yl)-1-oxoisoindolin-5-yl)piperidine-4-carbaldehyde

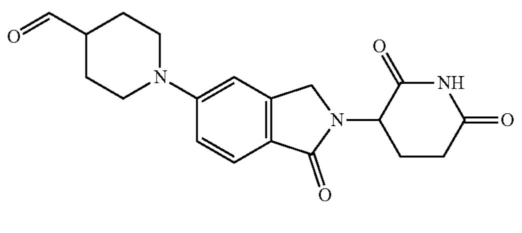 [SMILES: O=CC1CCN(c2ccc3c(c2)CN(C2CCC(=O)NC2=O)C3=O)CC1]

To a solution of 1-[2-(2,6-dioxo-3-piperidyl)-1-oxo-isoindolin-5-yl]piperidine-4-carbaldehyde (50 mg, 0.14 mmol, 1 eq) and (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (83 mg, 0.14 mmol, 1 eq) in N,N-dimethylformamide (2 mL) was added acetic acid (0.85 mg, 0.02 mmol, 0.1 eq) to adjust the pH to 5 at 25° C. and stirred for 20 min, then the mixture was added sodium cyanoborohydride (18 mg, 0.28 mmol, 2 eq), and the mixture was stirred at 25° C. for 1 hr. The residue was filtered to get the crude product. The residue was purified by pre-HPLC. The product ((3R)—N-[3-[5-[4-[4-[[1-[2-(2,6-dioxo-3-piperidyl)-1-oxo-isoindolin-5-yl]-4-piperidyl] methyl]piperazin-1-yl]phenyl]-1H-pyrrolo[2,3-b]pyridine-3-carbonyl]-2,4-difluoro-phenyl]-3-fluoro-pyrrolidine-1-sulfonamide (37.7 mg, 0.04 mmol, 28% yield, 98% purity) was obtained as green solid. LC/MS (ESI) m/z: 924.5 $[M+1]^+$; $^1$H-NMR (400 MHz, DMSO-$d_6$) δ 10.93 (s, 1H), 8.65 (d, J=2.0 Hz, 1H), 8.53 (s, 1H), 8.20 (s, 1H), 8.05 (s, 1H), 7.67-7.55 (m, 3H), 7.50 (d, J=8.8 Hz, 1H), 7.24 (t, J=8.3 Hz, 1H), 7.13-6.99 (m, 4H), 5.43-5.19 (m, 1H), 5.03 (dd, J=5.2, 13.2 Hz, 1H), 4.37-4.12 (m, 1H), 4.16-4.12 (m, 1H), 3.88 (d, J=12.4 Hz, 2H), 3.35-3.29 (m, 15H), 3.00-2.72 (m, 3H), 2.22 (d, J=6.4 Hz, 2H), 2.10-1.95 (m, 1H), 1.96 (dd, J=4.9, 10.0 Hz, 2H), 1.87-1.72 (m, 3H), 1.26-1.11 (m, 2H).

Exemplary Synthesis of (3-(5-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate (Exemplary Compound 862)

Step 1: Preparation of chloromethyl (2,5,8,11,14,17,20,23,26,29,32,35,38,41,44,47,50,53,56,59,62,65-docosaoxaheptahexacontan-67-yl) carbonate

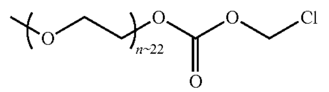

To a mixture of 2-[2-[2-[2-[2-[2-[2-[2-[2-[2-[2-[2-[2-[2-[2-[2-[2-[2-[2-[2-[2-(2-methoxy ethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethanol (20 g, 19.98 mmol, 1 eq) and pyridine (6.32 g, 79.90 mmol, 6.5 mL, 4 eq) in tetrahydrofuran (200 mL) was added chloromethyl carbonochloridate (5.15 g, 39.95 mmol, 3.5 mL, 2 eq) dropwise at 0° C. under nitrogen atmosphere. The mixture was stirred at 30° C. for 12 hours. Water (300 mL) was poured into the mixture and stirred for 1 minute. The aqueous phase was extracted with dichloromethane (200 mL×3). The combined organic phase was washed with brine (200 mL×2), dried with anhydrous sodium sulfate, filtered and concentrated in vacuum. The residue was purified by silica gel chromatography (1000 mesh silica gel, dichloromethane/methanol=100/1, 20/1). The product chloromethyl 2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (18 g, 16.46 mmol, 82% yield) was obtained as a light yellow solid. $^1$H-NMR (400 MHz, $CDCl_3$) δ 5.73 (s, 2H), 4.43-4.29 (m, 2H), 3.85-3.44 (m, 86H), 3.38 (s, 3H).

Step 2: Preparation of (3-(5-(4-(dimethoxymethyl)piperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate

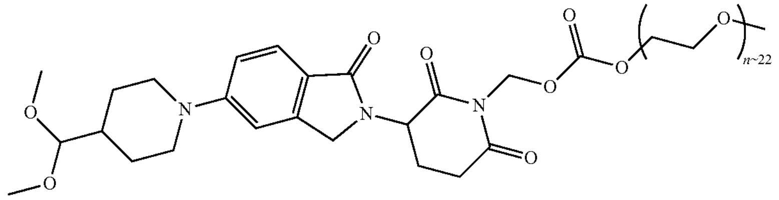

To a mixture of 3-[5-[4-(dimethoxymethyl)-1-piperidyl]-1-oxo-isoindolin-2-yl]piperidine-2,6-dione (1 g, 2.49 mmol, 1 eq) and chloromethyl 2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (3.23 g, 2.95 mmol, 1.19 eq) in dry dimethylformamide (10 mL) was added cesium carbonate powder (1.62 g, 4.98 mmol, 2 eq) in one portion at 15° C. The mixture was stirred at 15° C. for 12 hours. The mixture was filtered. The filtrate was purified by preparative reverse phase HPLC. The product [3-[5-[4-(dimethoxymethyl)-1-piperidyl]-1-oxo-isoindolin-2-yl]-2,6-dioxo-1-piperidyl]methyl 2-[2-[2-[2-[2-[2-[2-[2-[2-[2-[2-[2-[2-[2-[2-[2-[2-[2-[2-[2-[2-(2-methoxy ethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (1.4 g, 0.96 mmol, 38% yield, 100% purity) was obtained as an off-white oil by lyophilization. $^1$H-NMR (400 MHz, $CDCl_3$) δ 9.72 (s, 1H), 7.80-7.66 (m, 1H), 7.06-6.95 (m, 1H), 6.93-6.82 (m, 1H), 5.98-5.76 (m, 2H), 5.31 (s, 2H), 5.22 (dd, J=5.2, 13.6 Hz, 1H), 4.49-4.20 (m, 4H), 4.08 (d, J=6.8 Hz, 1H), 3.95-3.44 (m, 87H), 3.38 (s, 8H), 3.11-2.76 (m, 4H), 2.33 (dq, J=4.4, 13.2 Hz, 1H), 2.24-2.12 (m, 1H), 1.93-1.83 (m, 2H), 1.54-1.34 (m, 2H).

Step 3: Preparation of (3-(5-(4-formylpiperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate

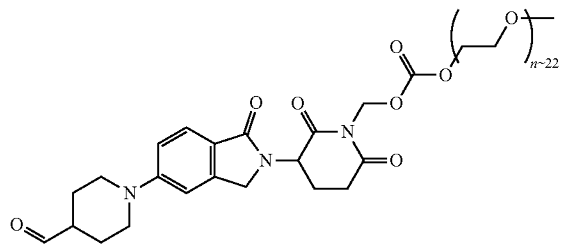

To a mixture of [3-[5-[4-(dimethoxymethyl)-1-piperidyl]-1-oxo-isoindolin-2-yl]-2,6-dioxo-1-piperidyl]methyl 2-[2-[2-[2-[2-[2-[2-[2-[2-[2-[2-[2-[2-[2-[2-[2-[2-[2-[2-[2-[2-(2-methoxy ethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (1.4 g, 0.96 mmol, 1 eq) in dichloromethane (20 mL) was added trifluoroacetic acid (5.47 g, 47.99 mmol, 3.5 mL, 50 eq) in one portion at 15° C. The mixture was stirred at 15° C. for 12 hours. The mixture was concentrated in vacuum. The product [3-[5-(4-formyl-1-piperidyl)-1-oxo-isoindolin-2-yl]-2,6-dioxo-1-piperidyl]methyl 2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]

ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (1.4 g, crude) was obtained as a brown oil. LC/MS (ESI) m/z: 707.3 [M/2+1]$^+$.

Step 4: Preparation of (3-(5-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)-1-oxoisoindolin-2-yl)-2,6-dioxopiperidin-1-yl)methyl (2,5,8,11,14,17,20,23,26,29,32,35,38,41,44,47,50,53,56,59,62,65-docosaoxaheptahexacontan-67-yl) carbonate

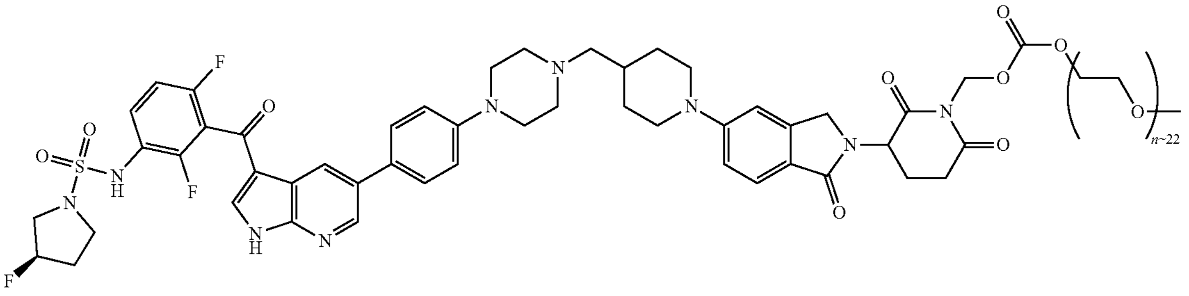

To a mixture of [3-[5-(4-formyl-1-piperidyl)-1-oxo-isoindolin-2-yl]-2,6-dioxo-1-piperidyl]methyl 2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (200 mg, 0.14 mmol, 1 eq) and (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (83 mg, 0.14 mmol, 1 eq) in dimethylformamide (2 mL) was added sodium acetate (12 mg, 0.14 mmol, 1 eq) to adjusted the pH=8. And then acetic acid (42 mg, 0.71 mmol, 5 eq) was added in one portion. The mixture was stirred at 30° C. for 10 min. Then sodium cyanoborohydride (18 mg, 0.28 mmol, 2 eq) was added in one portion. The mixture was stirred at 30° C. for 1 hour. The mixture was filtered to get the filtrate. The yellow filtrate was purified by Semi-preparative reverse phase HPLC. The product [3-[5-[4-[[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]methyl]-1-piperidyl]-1-oxo-isoindolin-2-yl]-2,6-dioxo-1-piperidyl]methyl 2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl carbonate (203.4 mg, 0.10 mmol, 46% yield, 99% purity, formate) was obtained as a yellow resin. LC/MS (ESI) m/z: 991.7 [M/2+1]$^+$; $^1$H-NMR (400 MHz, $CDCl_3$) δ 8.87 (s, 1H), 8.62 (d, J=2.0 Hz, 1H), 8.26 (s, 1H), 7.80-7.67 (m, 3H), 7.60 (d, J=8.8 Hz, 2H), 7.09-6.96 (m, 4H), 6.89 (s, 1H), 5.97-5.75 (m, 2H), 5.31 (s, 1H), 5.30-5.13 (m, 2H), 4.49-4.17 (m, 4H), 3.86 (d, J=12.4 Hz, 2H), 3.74-3.53 (m, 90H), 3.38 (s, 3H), 3.31 (s, 4H), 3.07-3.00 (m, 1H), 2.93-2.84 (m, 3H), 2.69-2.62 (m, 4H), 2.38-1.84 (m, 10H), 1.42-1.32 (m, 2H).

Exemplary Synthesis of (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 69-methyl-2,5,8,11,14,17,20,23,26,29,32,35,38,41,44,47,50,53,56,59,62,65,68-tricosaoxaheptacontan-70-oate (Exemplary Compound 866)

Step 1: Preparation of chloromethyl 69-methyl-2,5,8,11,14,17,20,23,26,29,32,35,38,41,44,47,50,53,56,59,62,65,68-tricosaoxaheptacontan-70-oate

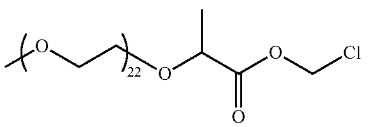

2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoic acid (0.90 g, 0.84 mmol, 1 eq) was added to a mixture of hydrogensulfate;tetrabutylammonium (28 mg, 0.08 mmol, 0.1 eq) and potassium carbonate (579 mg, 4.19 mmol, 5 eq) in dichloromethane (10 mL) and water (10 mL). Then a mixture of chloro(chlorosulfonyloxy)methane (415 mg, 2.52 mmol, 3 eq) in dichloromethane (5 mL) was added drop-wise to the mixture. The mixture was stirred at 20° C. for 10 h under nitrogen. The mixture was diluted with dichloromethane (20 mL) and water (10 mL), and the layers were separated. The aqueous layer was extracted with dichloromethane (50 mL×3). The combined organic layers were dried over anhydrous sodium sulfate, filtered and concentrated under reduced pressure to give a residue. The residue was purified by silica gel column chromatography (dichloromethane:methanol=1:0 to 15:1) to give chloromethyl 2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoate (0.50 g, 0.45 mmol, 53% yield) as a yellow solid. $^1$H NMR (400 MHz, $CDCl_3$) δ 5.82-5.72 (m, 2H), 4.15 (q, J=6.8 Hz, 1H), 3.71-3.63 (m, 114H), 3.58-3.54 (m, 2H), 3.39 (s, 3H), 1.45 (d, J=6.8 Hz, 3H).

Step 2: Preparation of (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 69-methyl-2,5,8,11,14,17,20,23,26,29,32,35,38,41,44,47,50,53,56,59,62,65,68-tricosaoxaheptacontan-70-oate

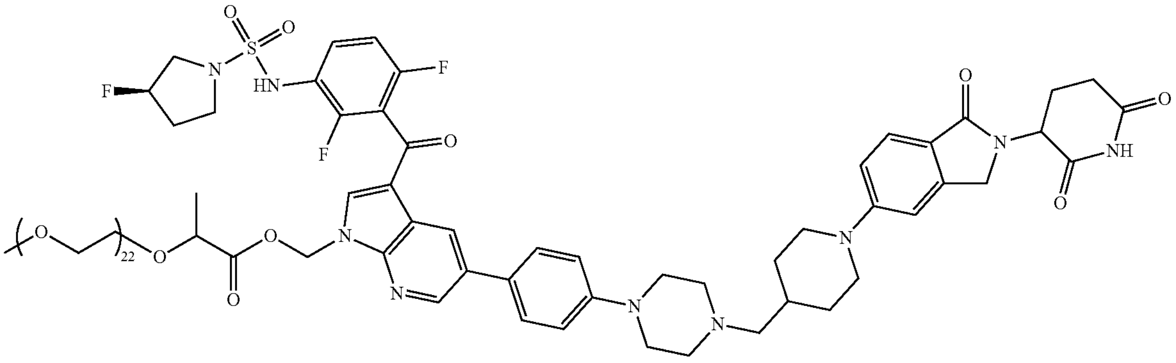

To a mixture of (3R)—N-[3-[5-[4-[4-[[1-[2-(2,6-dioxo-3-piperidyl)-1-oxo-isoindolin-5-yl]-4-piperidyl]methyl]piperazin-1-yl]phenyl]-1H-pyrrolo[2,3-b]pyridine-3-carbonyl]-2,4-difluoro-phenyl]-3-fluoro-pyrrolidine-1-sulfonamide (0.23 g, 0.25 mmol, 1 eq) and chloromethyl 2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoate (418 mg, 0.37 mmol, 1.5 eq) in N,N-dimethylformamide (3 mL) was added potassium carbonate (103 mg, 0.75 mmol, 3 eq). The mixture was stirred at 40° C. for 5 h. The mixture was filtered to give a residue. The residue was purified by semi-preparative reverse phase HPLC, then further purified by preparative thin layer chromatography (dichloromethane:methanol=15:1) to give [3-[2,6-difluoro-3-[[(3R)-3-fluoropyrrolidin-1-yl]sulfonylamino]benzoyl]-5-[4-[4-[[1-[2-(2,6-dioxo-3-piperidyl)-1-oxo-isoindolin-5-yl]-4-piperidyl]methyl]piperazin-1-yl]phenyl]pyrrolo[2,3-b]pyridin-1-yl]methyl2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoate (36.3 mg, 0.02 mmol, 6% yield, 95% purity, formic acid) as a yellow resin. $^1$H-NMR (400 MHz, $CDCl_3$) δ 8.84 (d, J=2.0 Hz, 1H), 8.68 (d, J=2.0 Hz, 1H), 8.11 (s, 1H), 7.86 (s, 1H), 7.80-7.70 (m, 2H), 7.60 (d, J=8.8 Hz, 2H), 7.08-6.97 (m, 4H), 6.89 (s, 1H), 6.38-6.26 (m, 2H), 5.36-5.16 (m, 2H), 4.46-4.36 (m, 1H), 4.29-4.23 (m, 1H), 4.07 (q, J=6.8 Hz, 1H), 3.90-3.78 (m, 4H), 3.73-3.44 (m, 112H), 3.38 (s, 3H), 3.36-3.22 (m, 2H), 2.98-2.50 (m, 7H), 2.44-2.14 (m, 6H), 2.09-1.91 (m, 6H), 1.38-1.32 (m, 5H).

Exemplary Synthesis of (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 2,5,8,11,14,17,20,23,26,29,32,35,38,41,44,47,50,53,56,59,62,65,68-tricosaoxaheptacontan-70-oate (Exemplary Compound 860)

Step 1: Preparation of tert-butyl 2,5,8,11,14,17,20,23,26,29,32,35,38,41,44,47,50,53,56,59,62,65,68-tricosaoxaheptacontan-70-oate

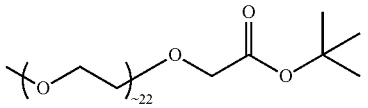

A mixture of 2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethanol (50.00 g, 49.94 mmol, 1 eq) and sodium;2-methylpropan-2-olate (24.00 g, 249.70 mmol, 5.0 eq) in toluene (500 mL) was stirred at 125° C. for 2 h, then the reaction mixture was cooled to 80° C., tert-butyl 2-bromoacetate (97.41 g, 499.40 mmol, 73.80 mL, 10.0 eq) was added to the mixture. The mixture was stirred at 125° C. for 28 h. The mixture was filtered hot through a pad of celite. The pad was rinsed with hot toluene (~70° C., 100 mL×3) and the combined filtrates were concentrated in vacuo. The resulting oil was taken up in ethyl acetate (100 mL) and added to petroleum ether (600 mL) under vigorous stirring. After standing for 15 min, the precipitate was collected, washed copiously with petroleum ether and dried in vacuo to give tert-butyl 2-[2-[2-[2-[2-[2-[2-[2-[2-[2-[2-[2-[2-[2-[2-[2-[2-[2-[2-[2-[2-[2-(2-methoxyethoxy) ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]acetate (40.00 g, 35.86 mmol, 71% yield) as a yellow solid. The product was purified by silica gel column chromatography (petroleum ether:ethyl acetate:dichloromethane:methanol=5:1:0:0 to 0:0:20:1) to give tert-butyl 2-[2-[2-[2-[2-[2-[2-[2-[2-[2-[2-[2-[2-[2-[2-[2-[2-[2-[2-[2-[2- [2-(2-methoxyethoxy) ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]acetate (92% yield) as a yellow solid. $^1$H-NMR (400 MHz, $CDCl_3$) δ 4.02 (s, 2H), 3.67-3.62 (m, 90H), 3.57-3.52 (m, 2H), 3.38 (s, 3H), 1.47 (s, 9H).

Step 2: Preparation of 2,5,8,11,14,17,20,23,26,29,32,35,38,41,44,47,50,53,56,59,62,65,68-tricosaoxaheptacontan-70-oic acid

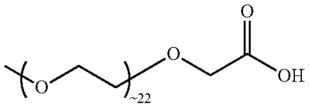

To a mixture of tert-butyl 2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]acetate (12.00 g, 10.76 mmol, 1 eq) in dichloromethane (100 mL) was added trifluoroacetic acid (405.18 mmol, 30 mL, 37.66 eq). The mixture was stirred at 20° C. for 6 h. The mixture was concentrated under reduced pressure to give a residue. The residue was charged with methyl tert-butyl ether (100 mL) and stirred at 20° C. for 2 h. The mixture was filtered and the cake was washed with methyl tert-butyl ether (50 mL×3), then concentrated under reduced pressure to give 2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]acetic acid (11.00 g, 10.38 mmol, 96% yield) as a yellow gum. $^1$H NMR (400 MHz, $CDCl_3$) δ 4.19 (s, 2H), 3.81-3.75 (m, 2H), 3.67 (s, 100H), 3.61-3.57 (m, 2H), 3.41 (s, 3H).

Step 3: Preparation of chloromethyl 2,5,8,11,14,17,20,23,26,29,32,35,38,41,44,47,50,53,56,59,62,65,68-tricosaoxaheptacontan-70-oate

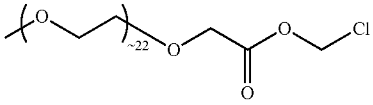

2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]acetic acid (5.00 g, 4.72 mmol, 1 eq) was added to a mixture of hydrogensulfate;tetrabutylammonium (160 mg, 0.47 mmol, 0.1 eq) and potassium carbonate (2.61 g, 18.88 mmol, 4 eq) in dichloromethane (20 mL) and water (20 mL). Then a solution of chloro(chlorosulfonyloxy)methane (1.17 g, 7.08 mmol, 1.5 eq) in dichloromethane (5 mL) was added drop-wise to the mixture. The mixture was stirred at 20° C. for 10 h under nitrogen. The mixture was then diluted in water (20 mL) and dichloromethane (30 mL), and the layers were separated. The aqueous layer was extracted with dichloromethane (50 mL×3). The combined organic layers were dried over anhydrous sodium sulfate, filtered and concentrated under reduced pressure to give a residue. The residue was purified by silica gel column chromatography (dichloromethane:methanol=1:0 to 10:1) to give chloromethyl 2-[2-[2-[2-[2-[2-[2-[2-[2-[2-[2-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]acetate (3.00 g, 2.71 mmol, 57% yield) as a yellow gum. $^1$H-NMR (400 MHz, $CDCl_3$) δ 5.72-5.68 (m, 2H), 4.26-4.15 (m, 2H), 3.72-3.67 (m, 2H), 3.58 (d, J=4.6 Hz, 86H), 3.51-3.45 (m, 2H), 3.34-3.29 (m, 3H).

Step 4: Preparation of (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl 2,5,8,11,14,17,20,23,26,29,32,35,38,41,44,47,50,53,56,59,62,65,68-tricosaoxaheptacontan-70-oate

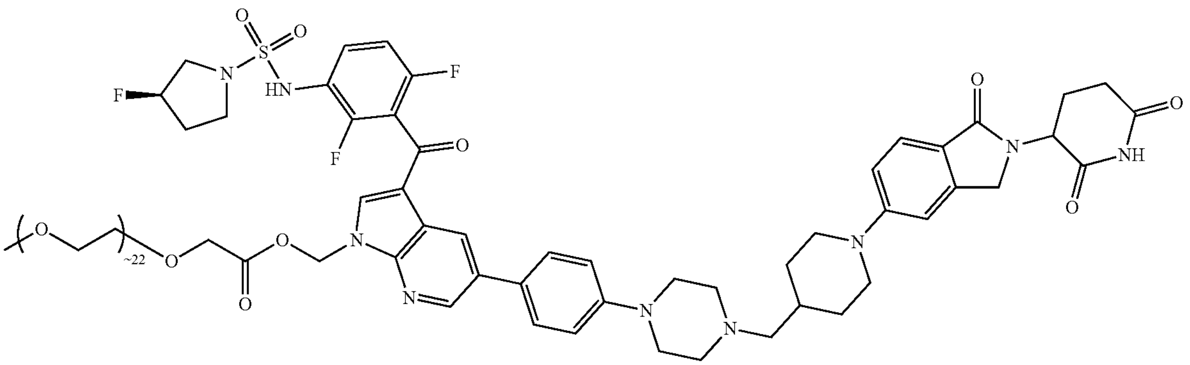

To a mixture of (3R)—N-[3-[5-[4-[4-[[1-[2-(2,6-dioxo-3-piperidyl)-1-oxo-isoindolin-5-yl]-4-piperidyl]methyl]piperazin-1-yl]phenyl]-1H-pyrrolo[2,3-b]pyridine-3-carbonyl]-2,4-difluoro-phenyl]-3-fluoro-pyrrolidine-1-sulfonamide (120 mg, 0.13 mmol, 1 eq) and chloromethyl 2-[2-[2-[2-[2-[2-[2-[2-[2-[2-[2-[2-[2-[2-[2-[2-[2-[2-[2-[2-(2-methoxy ethoxy)ethoxy]ethoxy]ethoxy]ethoxy]ethoxy]ethoxy] ethoxy]ethoxy]ethoxy]ethoxy]ethoxy]ethoxy]ethoxy] ethoxy]ethoxy]ethoxy]ethoxy]ethoxy]ethoxy]ethoxy] ethoxy]acetate (172 mg, 0.16 mmol, 1.2 eq) in DMF (1 mL) was added potassium carbonate (54 mg, 0.39 mmol, 3 eq). The mixture was stirred at 40° C. for 5 h. The mixture was filtered to give a residue. The residue was purified by semi-preparative reverse phase HPLC. The compound was purified further by preparative TLC (dichloromethane: methanol=15:1). The compound was purified further by semi-preparative reverse phase HPLC to give [3-[2,6-difluoro-3-[[(3R)-3-fluoropyrrolidin-1-yl]sulfonylamino]benzoyl]-5-[4-[4-[[1-[2-(2,6-dioxo-3-piperidyl)-1-oxo-isoindolin-5-yl]-4-piperidyl]methyl]piperazin-1-yl]phenyl]pyrrolo [2,3-b]pyridin-1-yl]methyl 2-[2-[2-[2-[2-[2-[2-[2-[2-[2-[2-[2-[2-[2-[2-[2-[2-[2-[2-[2-(2-methoxy ethoxy) ethoxy] ethoxy]ethoxy]ethoxy]ethoxy]ethoxy]ethoxy]ethoxy] ethoxy]ethoxy]ethoxy]ethoxy]ethoxy]ethoxy]ethoxy] ethoxy]ethoxy]ethoxy]ethoxy]ethoxy]ethoxy]acetate (36.53 mg, 0.02 mmol, 13% yield, 96% purity, formic) as a yellow resin. LC/MS (ESI) m/z: 1020.2 $[M/2+1]^+$; $^1$H-NMR (400 MHz, $CDCl_3$) δ 8.84 (d, J=2.0 Hz, 1H), 8.69 (d, J=2.0 Hz, 1H), 8.50-8.16 (m, 1H), 7.86 (s, 1H), 7.80-7.68 (m, 2H), 7.60 (d, J=8.4 Hz, 2H), 7.10-6.97 (m, 4H), 6.90 (s, 1H), 6.37-6.29 (m, 2H), 5.37-5.13 (m, 2H), 4.46-4.35 (m, 1H), 4.31-4.16 (m, 3H), 3.91-3.79 (m, 2H), 3.73-3.54 (m, 100H), 3.52-3.43 (m, 2H), 3.39 (s, 3H), 3.34-3.24 (m, 4H), 2.95-2.81 (m, 4H), 2.67-2.59 (m, 4H), 2.36-1.76 (m, 10H), 1.42-1.29 (m, 2H).

Exemplary Synthesis of (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl (2,5,8,11,14,17,20,23,26,29,32,35,38,41,44,47,50,53,56,59,62,65-docosaoxaheptahexacontan-67-yl) carbonate (Exemplary Compound 857)

Step 1: Preparation of (3-(2,6-difluoro-3-(((R)-3-fluoropyrrolidine)-1-sulfonamido)benzoyl)-5-(4-(4-((1-(2-(2,6-dioxopiperidin-3-yl)-1-oxoisoindolin-5-yl)piperidin-4-yl)methyl)piperazin-1-yl)phenyl)-1H-pyrrolo[2,3-b]pyridin-1-yl)methyl (2,5,8,11,14,17,20,23,26,29,32,35,38,41,44,47,50,53,56,59,62,65-docosaoxaheptahexacontan-67-yl) carbonate

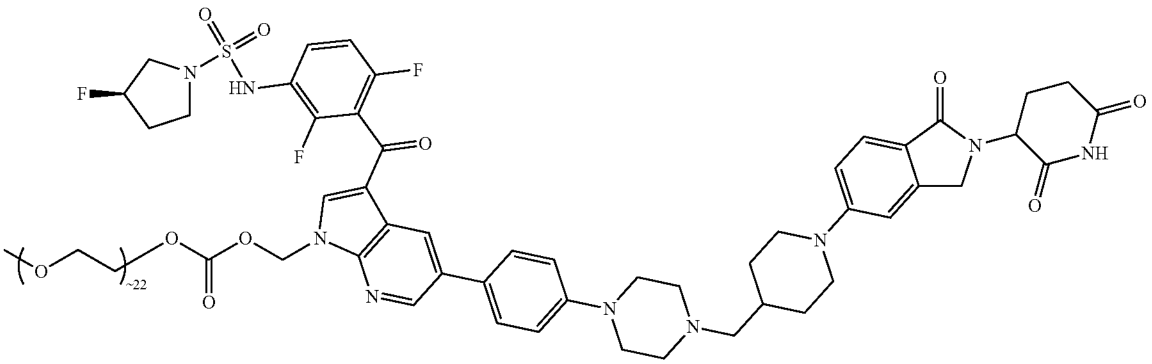

A mixture of chloromethyl 2-[2-[2-[2-[2-[2-[2-[2-[2-[2-[2-[2-[2-[2-[2-[2-[2-[2-[2-[2-[2-(2-methoxyethoxy)ethoxy] ethoxy]ethoxy]ethoxy]ethoxy]ethoxy]ethoxy]ethoxy] ethoxy]ethoxy]ethoxy]ethoxy]ethoxy]ethoxy]ethoxy] ethoxy]ethoxy]ethoxy]ethoxy]ethoxy]ethyl carbonate (189 mg, 0.17 mmol, 1.00 eq), (3R)—N-[3-[5-[4-[4-[[1-[2-(2,6-dioxo3-piperidyl)-1-oxo-isoindolin-5-yl]-4-piperidyl] methyl]piperazin-1-yl]phenyl]-1H-pyrrolo[2,3-b]pyridine-3-carbonyl]-2,4-difluoro-phenyl]-3-fluoro-pyrrolidine-1-sulfonamide (160 mg, 0.17 mmol, 1.00 eq) and potassium carbonate (71 mg, 0.52 mmol, 3.00 eq) in N,N-dimethyl-formamide (3 mL) was stirred at 40° C. for 5 h. The mixture was filtered and concentrated under reduced pressure to give a residue. The residue was purified first by semi-preparative reverse phase HPLC, then by preparative TLC (dichloromethane:methanol=15:1, Rf=0.2) to give [3-[2,6-difluoro-3-[[(3R)-3-fluoropyrrolidin-1-yl]sulfonylamino]benzoyl]-5-[4-[4-[[1-[2-(2,6-dioxo-3-piperidyl)-1-oxo-isoindolin-5-yl]-4-piperidyl]methyl]piperazin-1-yl]phenyl]pyrrolo[2,3-b] pyridin-1-yl]methyl-2-[2-[2-[2-[2-[2-[2-[2-[2-[2-[2-[2-[2-[2-[2-[2-[2-[2-[2-[2-(2-methoxyethoxy)ethoxy]ethoxy] ethoxy]ethoxy]ethoxy]ethoxy]ethoxy]ethoxy]ethoxy]

ethoxy]ethoxy]ethoxy]ethoxy]ethoxy]ethoxy]ethoxy]ethoxy]ethoxy]ethoxy]ethoxy]ethyl carbonate (49.4 mg, 0.02 mmol, 14% yield, 95% purity) as a yellow solid. LC/MS (ESI) m/z: 881.0 $[M/2+1]^+$; $^1$H-NMR (400 MHz, $CDCl_3$) δ 8.82 (d, J=2.0 Hz, 1H), 8.68 (d, J=2.0 Hz, 1H), 8.21 (br s, 1H), 7.86 (s, 1H), 7.78-7.69 (m, 2H), 7.59 (d, J=8.8 Hz, 2H), 7.09-6.97 (m, 5H), 6.89 (s, 1H), 6.28 (s, 2H), 5.33-5.16 (m, 2H), 4.44-4.36 (m, 1H), 4.31-4.22 (m, 3H), 3.86 (d, J=12.8 Hz, 3H), 3.73-3.42 (m, 76H), 3.38 (s, 3H), 3.32-3.25 (m, 4H), 2.95-2.59 (m, 9H), 2.40-1.73 (m, 15H), 1.42-1.23 (m, 3H).

Exemplary Synthesis of (3R)—N-(3-(5-(4-(6-((1-(2-(2,6-dioxopiperidin-3-yl)-1-oxoisoindolin-5-yl)piperidin-4-yl)methyl)-2,6-diazaspiro[3.3]heptan-2-yl)phenyl)-1H-pyrrolo[2,3-b]pyridine-3-carbonyl)-2,4-difluorophenyl)-3-fluoropyrrolidine-1-sulfonamide (Exemplary Compound 536)

Step 1: Preparation of tert-butyl 6-(4-bromophenyl)-2,6-diazaspiro[3.3]heptane-2-carboxylate

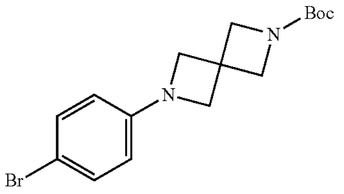 [SMILES: CC(C)(C)OC(=O)N1CC2(C1)CN(c1ccc(Br)cc1)C2]

Into a 250-mL 3-necked round-bottom flask, was placed oxalic acid; tert-butyl 2,6-diazaspiro[3.3]heptane-2-carboxylate (1.45 g, 5.029 mmol, 1 equiv), (4-bromophenyl) boronic acid (1.20 g, 5.975 mmol, 1.19 equiv), TEA (2.53 g, 25.002 mmol, 4.97 equiv), $Cu(OAc)_2$ (1.36 g, 7.488 mmol, 1.49 equiv), DCM (150 mL), 4 A MS (5 g). To the mixture was purged with air and stirred for 12 h at room temperature. The solids were filtered out. The filtrate was washed with water (100 mL), dried over anhydrous sodium sulfate and concentrated under vacuum. The residue was applied onto a silica gel column with ethyl acetate/petroleum ether (1/5). This resulted in 1.02 g (57%) of tert-butyl 6-(4-bromophenyl)-2,6-diazaspiro[3.3]heptane-2-carboxylate as a light yellow solid. LC/MS (ESI) m/z: 352.90/354.90 $[M+1]^+$.

Step 2: Preparation of tert-butyl 6-(4-(4,4,5,5-tetramethyl-1,3,2-dioxaborolan-2-yl)phenyl)-2,6-diazaspiro[3.3]heptane-2-carboxylate

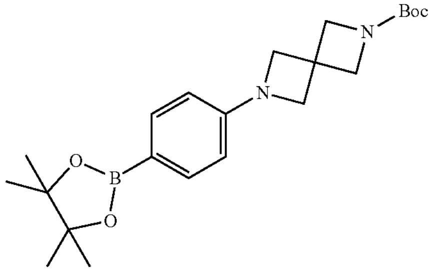 [SMILES: CC(C)(C)OC(=O)N1CC2(C1)CN(c1ccc(B3OC(C)(C)C(C)(C)O3)cc1)C2]

Into a 30-mL sealed tube purged and maintained with an inert atmosphere of nitrogen, was placed tert-butyl 6-(4-bromophenyl)-2,6-diazaspiro[3.3]heptane-2-carboxylate (706.40 mg, 2.000 mmol, 1.00 equiv), 4,4,5,5-tetramethyl-2-(4,4,5,5-tetramethyl-1,3,2-dioxaborolan-2-yl)-1,3,2-dioxaborolane (761.70 mg, 3.000 mmol, 1.50 equiv), KOAc (588.00 mg, 5.991 mmol, 3.00 equiv), $Pd(dppf)Cl_2 \cdot CH_2Cl_2$ (163.30 mg, 0.200 mmol, 0.10 equiv), DMSO (12.00 mL). The resulting mixture was stirred for 5 h at 90° C. in an oil bath. The reaction mixture was cooled to room temperature and diluted with water (100 mL). The resulting mixture was extracted with ethyl acetate (100 mL×2) and the organic layers combined. The organic was washed with brine (100 mL×2), dried over anhydrous sodium sulfate and concentrated under vacuum. The residue was applied onto a silica gel column with ethyl acetate/petroleum ether (1/5). This resulted in 743 mg (93%) of tert-butyl 6-[4-(4,4,5,5-tetramethyl-1,3,2-dioxaborolan-2-yl)phenyl]-2,6-diazaspiro[3.3]heptane-2-carboxylate as a yellow solid. LC/MS (ESI) m/z: 401.05 $[M+1]^+$.

Step 3: Preparation of tert-butyl (R)-6-(4-(3-(2,6-difluoro-3-((3-fluoropyrrolidine)-1-sulfonamido)benzoyl)-1H-pyrrolo[2,3-b]pyridin-5-yl)phenyl)-2,6-diazaspiro[3.3]heptane-2-carboxylate

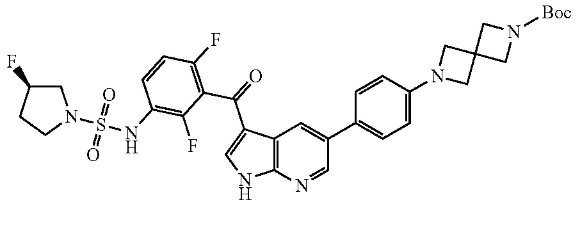 [SMILES: CC(C)(C)OC(=O)N1CC2(C1)CN(c1ccc(-c3cnc4[nH]cc(C(=O)c5c(F)ccc(NS(=O)(=O)N6CC[C@@H](F)C6)c5F)c4c3)cc1)C2]

Into a 30-mL sealed tube purged and maintained with an inert atmosphere of nitrogen, was placed tert-butyl 6-[4-(4,4,5,5-tetramethyl-1,3,2-dioxaborolan-2-yl)phenyl]-2,6-diazaspiro[3.3]heptane-2-carboxylate (288.20 mg, 0.720 mmol, 1.20 equiv), (3R)—N-(3-[5-bromo-1H-pyrrolo[2,3-b]pyridine-3-carbonyl]-2,4-difluorophenyl)-3-fluoropyrrolidine-1-sulfonamide (302.00 mg, 0.600 mmol, 1.00 equiv), $K_2CO_3$ (248.80 mg, 1.800 mmol, 3.00 equiv), $Pd(dppf)Cl_2 \cdot CH_2Cl_2$ (49.00 mg, 0.060 mmol, 0.10 equiv), dioxane (12.00 mL), H2O (2.00 mL). The resulting mixture was stirred for 2 h at 95° C. in an oil bath. The reaction mixture was cooled to room temperature and diluted with water (50 mL). The resulting mixture was extracted with ethyl acetate (80 mL×2) and the organic layers combined and dried over anhydrous sodium sulfate and concentrated under vacuum. The residue was purified by flash chromatography ($CH_2Cl_2$/MeOH 30:1) and followed by Prep-TLC ($CH_2Cl_2$/MeOH 10:1). This resulted in 203 mg (49%) of tert-butyl 6-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)-2,6-diazaspiro[3.3]heptane-2-carboxylate as a yellow solid. LC/MS (ESI) m/z: 697.10 $[M+1]^+$.

Step 4: Preparation of (R)—N-(3-(5-(4-(2,6-diazaspiro[3.3]heptan-2-yl)phenyl)-1H-pyrrolo[2,3-b]pyridine-3-carbonyl)-2,4-difluorophenyl)-3-fluoropyrrolidine-1-sulfonamide

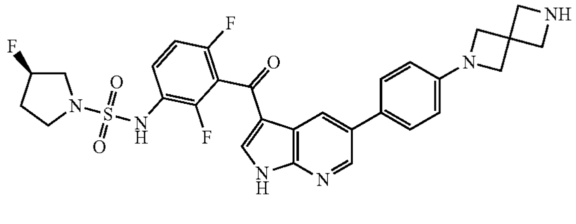 [SMILES: O=C(c1c(F)ccc(NS(=O)(=O)N2CC[C@@H](F)C2)c1F)c1c[nH]c2ncc(-c3ccc(N4CC5(CNC5)C4)cc3)cc12]

Into a 100-mL round-bottom flask, was placed tert-butyl 6-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)-2,6-diazaspiro[3.3]heptane-2-carboxylate (203.00 mg, 0.291 mmol, 1.00 equiv), DCM (6.00 mL), TFA (1.50 mL). The resulting solution was stirred for 1 h at room temperature. DIEA was employed to neutralize the acid. This resulted in a solution of 173.8 mg (99.98%) of (3R)—N-[3-[5-(4-[2,6-diazaspiro[3.3]heptan-2-yl]phenyl)-1H-pyrrolo[2,3-b]pyridine-3-carbonyl]-2,4-difluorophenyl]-3-fluoropyrrolidine-1-sulfonamide in DCM as a light brown solution. LC/MS (ESI) m/z: 597.10 [M+1]$^+$.

Step 5: Preparation of methyl 2-cyano-4-(4-(hydroxymethyl)piperidin-1-yl)benzoate

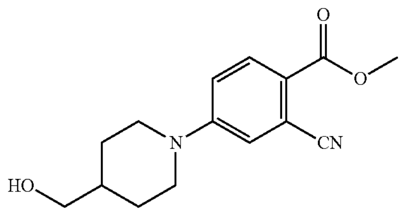 [SMILES: COC(=O)c1ccc(N2CCC(CO)CC2)cc1C#N]

Into a 100-mL round-bottom flask, was placed methyl 2-cyano-4-fluorobenzoate (3.58 g, 19.983 mmol, 1 equiv), (piperidin-4-yl)methanol (3.45 g, 29.954 mmol, 1.50 equiv), DIEA (9.9 mL, 56.837 mmol, 2.84 equiv), DMSO (40 mL). The resulting mixture was stirred for 2 h at 110° C. in an oil bath. The reaction mixture was cooled to room temperature and diluted with water (200 mL). The resulting mixture was extracted with ethyl acetate (200 mL×2) and the organic layers combined. The combined organic layers were washed with brine (200 mL×2), dried over anhydrous sodium sulfate and concentrated under vacuum. The residue was applied onto a silica gel column with ethyl acetate/petroleum ether (1/1). This resulted in 5.21 g (95%) of methyl 2-cyano-4-[4-(hydroxymethyl)piperidin-1-yl]benzoate as a yellow green semi-solid. LC/MS (ESI) m/z: 274.95 [M+1]$^+$.

Step 6: Preparation of methyl 2-formyl-4-(4-(hydroxymethyl)piperidin-1-yl)benzoate

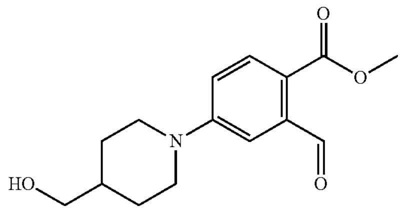 [SMILES: COC(=O)c1ccc(N2CCC(CO)CC2)cc1C=O]

Into a 100-mL round-bottom flask purged and maintained with an inert atmosphere of nitrogen, was placed $H_2O$ (10 mL), AcOH (10 mL), pyridine (20 mL), methyl 2-cyano-4-[4-(hydroxymethyl)piperidin-1-yl]benzoate (2.3 g, 8.384 mmol, 1 equiv), sodium hypophosphite monohydrate (8.89 g, 83.873 mmol, 10.00 equiv), Raney-Ni (1 g, 11.672 mmol, 1.39 equiv). The resulting mixture was stirred for 16 h at 70° C. in an oil bath. The reaction mixture was cooled to room temperature and the solids were filtered out. The filtrate was diluted with water (100 mL) and extracted with ethyl acetate (100 mL×2). The organic layers were combined and washed with brine (100 mL×2). The organic was dried over anhydrous sodium sulfate and concentrated under vacuum. The residue was applied onto a silica gel column with ethyl acetate/petroleum ether (1/1). This resulted in 553 mg (24%) of methyl 2-formyl-4-[4-(hydroxymethyl)piperidin-1-yl] benzoate as yellow green oil. LC/MS (ESI) m/z: 277.95 [M+1]$^+$.

Step 7: Preparation of 3-(5-(4-(hydroxymethyl)piperidin-1-yl)-1-oxoisoindolin-2-yl)piperidine-2,6-dione

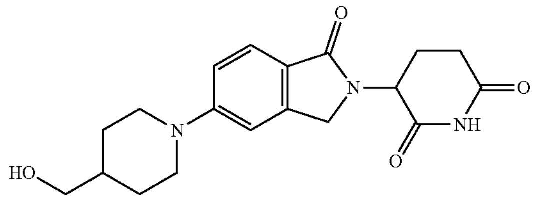 [SMILES: O=C1CCC(N2Cc3cc(N4CCC(CO)CC4)ccc3C2=O)C(=O)N1]

Into a 100-mL round-bottom flask, was placed methyl 2-formyl-4-[4-(hydroxymethyl)piperidin-1-yl]benzoate (500 mg, 1.803 mmol, 1 equiv), 3-aminopiperidine-2,6-dione hydrochloride (356.1 mg, 2.164 mmol, 1.20 equiv), DIEA (0.6 mL), DCM (30 mL), AcOH (1 mL). The resulting mixture was stirred for 4 h at 35° C. in an oil bath. This was followed by the addition of $NaBH(OAc)_3$ (1.15 g, 5.426 mmol, 3.01 equiv) and the resulting mixture was allowed to react, with stirring, for an additional 16 h at room temperature. The reaction was then quenched by the addition of water (50 mL) and saturated $NaHCO_3$ was employed to adjust the pH to 8. The resulting mixture was extracted with DCM/MeOH (10/1, 100 mL×6) and the organic layers combined. The organic was dried over anhydrous sodium sulfate and concentrated under vacuum. The residue was applied onto a silica gel column with dichloromethane/methanol (20/1). This resulted in 504 mg (78%) of 3-[5-[4-(hydroxymethyl)piperidin-1-yl]-1-oxo-2,3-dihydro-1H-isoindol-2-yl]piperidine-2,6-dione as a light green solid. LC/MS (ESI) m/z: 358.00 [M+1]$^+$.

Step 8: Preparation of 1-(2-(2,6-dioxopiperidin-3-yl)-1-oxoisoindolin-5-yl)piperidine-4-carbaldehyde

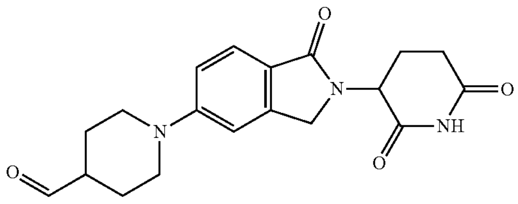 [SMILES: O=CC1CCN(c2ccc3c(c2)CN(C2CCC(=O)NC2=O)C3=O)CC1]

Into a 250-mL round-bottom flask, was placed 3-[5-[4-(hydroxymethyl)piperidin-1-yl]-1-oxo-2,3-dihydro-1H-isoindol-2-yl]piperidine-2,6-dione (150.00 mg, 0.420 mmol, 1.00 equiv), DCM (40.00 mL), DMP (356.00 mg, 0.839 mmol, 2.00 equiv). The resulting mixture was stirred for 1 h at 35° C. in an oil bath. The solids were filtered out and the filtrate was concentrated under vacuum. The residue was purified by Prep-TLC ($CH_2Cl_2$/MeOH 8:1). This resulted in 115 mg (77%) of 1-[2-(2,6-dioxopiperidin-3-yl)-1-oxo-2,3-dihydro-1H-isoindol-5-yl]piperidine-4-carbaldehyde as a yellow solid. LC/MS (ESI) m/z: 355.95 [M+1]$^+$.

Step 9: Preparation of (3R)—N-(3-(5-(4-(6-((1-(2-(2,6-dioxopiperidin-3-yl)-1-oxoisoindolin-5-yl)piperidin-4-yl)methyl)-2,6-diazaspiro[3.3]heptan-2-yl)phenyl)-1H-pyrrolo[2,3-b]pyridine-3-carbonyl)-2,4-difluorophenyl)-3-fluoropyrrolidine-1-sulfonamide

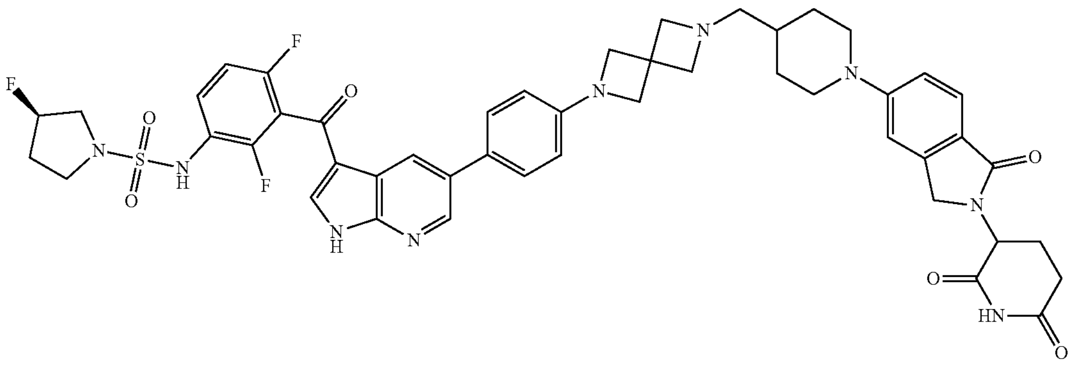 [SMILES: O=C1CCC(N2Cc3cc(N4CCC(CN5CC6(C5)CN(c5ccc(-c7cnc8[nH]cc(C(=O)c9c(F)ccc(NS(=O)(=O)N%10CC[C@@H](F)C%10)c9F)c8c7)cc5)C6)CC4)ccc3C2=O)C(=O)N1]

Into a 100-mL round-bottom flask, was placed (3R)—N-[3-[5-(4-[2,6-diazaspiro[3.3]heptan-2-yl]phenyl)-1H-pyrrolo[2,3-b]pyridine-3-carbonyl]-2,4-difluorophenyl]-3-fluoropyrrolidine-1-sulfonamide (173.80 mg, 0.291 mmol, 1.00 equiv), 1-[2-(2,6-dioxopiperidin-3-yl)-1-oxo-2,3-dihydro-1H-isoindol-5-yl]piperidine-4-carbaldehyde (113.90 mg, 0.320 mmol, 1.10 equiv), DCM (40.00 mL). The resulting solution was stirred for 2 h at 35° C. in an oil bath. This was followed by the addition of $NaBH_3CN$ (54.80 mg, 0.872 mmol, 2.99 equiv) and the resulting mixture was allowed to react, with stirring, for an additional 0.5 h at room temperature. The reaction was then quenched by the addition of water (50 mL) and extracted with DCM/MeOH (10/1, 60 mL×2). The organic layers were combined and dried over anhydrous sodium sulfate and concentrated under vacuum. The residue was purified by Prep-TLC ($CH_2Cl_2$/MeOH 8:1). This resulted in 69.0 mg (25%) of (3R)—N-[3-(5-[4-[6-([1-[2-(2,6-dioxopiperidin-3-yl)-1-oxo-2,3-dihydro-1H-isoindol-5-yl]piperidin-4-yl]methyl)-2,6-diazaspiro[3.3]heptan-2-yl]phenyl]-1H-pyrrolo[2,3-b]pyridine-3-carbonyl)-2,4-difluorophenyl]-3-fluoropyrrolidine-1-sulfonamide as a yellow green solid. LC/MS (ESI) m/z: 936.25 $[M+1]^+$; $^1$H-NMR (400 MHz, DMSO-$d_6$) δ 12.90 (s, 1H), 10.96 (s, 1H), 8.62 (s, 1H), 8.50 (s, 1H), 8.07 (s, 1H), 7.66-7.49 (m, 4H), 7.29-7.23 (m, 1H), 7.05-7.02 (m, 2H), 6.58-6.55 (m, 2H), 5.30 (d, J=52.8 Hz, 1H), 5.08-5.02 (m, 1H), 4.35-4.16 (m, 2H), 3.94-3.84 (m, 6H), 3.51-3.49 (m, 1H), 3.39-3.38 (m, 5H), 3.30-3.23 (m, 1H), 2.91-2.76 (m, 3H), 2.61-2.55 (m, 1H), 2.39-2.35 (m, 3H), 2.18-1.93 (m, 3H), 1.77-1.73 (m, 2H), 1.52 (s, 1H), 1.23-1.18 (m, 4H).

Exemplary Synthesis of (3R)—N-(3-(5-(4-(4-((6-(2-(2,6-dioxopiperidin-3-yl)-1-oxoisoindolin-5-yl)-2,6-diazaspiro[3.3]heptan-2-yl)methyl)piperidin-1-yl)phenyl)-1H-pyrrolo[2,3-b]pyridine-3-carbonyl)-2,4-difluorophenyl)-3-fluoropyrrolidine-1-sulfonamide (Exemplary Compound 537)

Step 1: Preparation of tert-butyl 6-(3-cyano-4-(methoxycarbonyl)phenyl)-2,6-diazaspiro[3.3]heptane-2-carboxylate

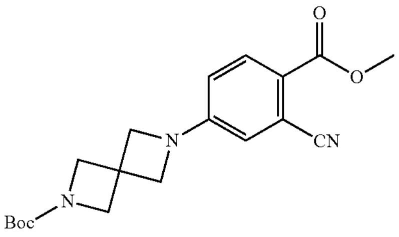 [SMILES: COC(=O)c1ccc(N2CC3(CN(C(=O)OC(C)(C)C)C3)C2)cc1C#N]

Into a 30-mL sealed tube, was placed methyl 2-cyano-4-fluorobenzoate (896.00 mg, 5.001 mmol, 1.00 equiv), oxalic acid; tert-butyl 2,6-diazaspiro[3.3]heptane-2-carboxylate (1.59 g, 5.515 mmol, 1.10 equiv), DIEA (4.20 mL, 24.113 mmol, 4.82 equiv), DMSO (12.00 mL). The resulting mixture was stirred for 2 h at 110° C. in an oil bath. The reaction mixture was cooled to room temperature and diluted with water (100 mL). The resulting mixture was extracted with ethyl acetate (100 mL×2) and the organic layers combined. The organic was washed with brine (100 mL×2), dried over anhydrous sodium sulfate and concentrated under vacuum. The residue was applied onto a silica gel column with ethyl acetate/petroleum ether (1/1). This resulted in 1.75 g (98%) of tert-butyl 6-[3-cyano-4-(methoxycarbonyl)phenyl]-2,6-diazaspiro[3.3]heptane-2-carboxylate as a yellow green solid. LC/MS (ESI) m/z: 358.00 $[M+1]^+$.

Step 2: Preparation of tert-butyl 6-(3-formyl-4-(methoxycarbonyl)phenyl)-2,6-diazaspiro[3.3]heptane-2-carboxylate

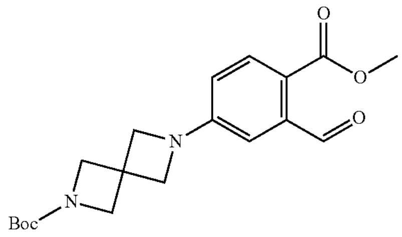 [SMILES: COC(=O)c1ccc(N2CC3(CN(C(=O)OC(C)(C)C)C3)C2)cc1C=O]

Into a 250-mL round-bottom flask purged and maintained with an inert atmosphere of nitrogen, was placed $H_2O$ (15.00 mL), AcOH (15.00 mL), pyridine (30.00 mL), tert-butyl 6-[3-cyano-4-(methoxycarbonyl)phenyl]-2,6-diazaspiro[3.3]heptane-2-carboxylate (1.66 g, 4.645 mmol, 1.00 equiv), sodium hypophosphite monohydrate (4.89 g, 46.135 mmol, 9.93 equiv), Raney-Ni (1.00 g, 11.672 mmol, 2.51 equiv). The resulting mixture was stirred for 4 h at 70° C. in an oil bath. The reaction mixture was cooled to room temperature and diluted with water (150 mL). The solids were filtered out and to the filtrate was added saturated $NaHCO_3$ to adjust the pH to 8. The resulting mixture was extracted with ethyl acetate (200 mL×2) and the organic layers combined. The organic was washed with brine (200 mL×2), dried over anhydrous sodium sulfate and concentrated under vacuum. The residue was applied onto a silica gel column with ethyl acetate/petroleum ether (1/1). This resulted in 500 mg (45%) of tert-butyl 6-[3-formyl-4-(methoxycarbonyl)phenyl]-2,6-diazaspiro[3.3]heptane-2-carboxylate as a yellow green solid. LC/MS (ESI) m/z: 361.00 $[M+1]^+$.

Step 3: Preparation of tert-butyl 6-(2-(2,6-dioxopiperidin-3-yl)-1-oxoisoindolin-5-yl)-2,6-diazaspiro[3.3]heptane-2-carboxylate

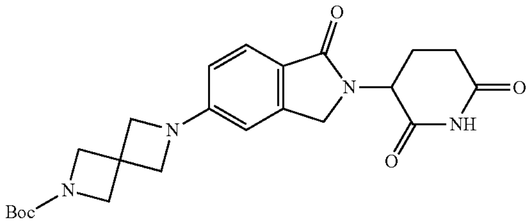 [SMILES: CC(C)(C)OC(=O)N1CC2(C1)CN(c1ccc3c(c1)CN(C1CCC(=O)NC1=O)C3=O)C2]

Into a 100-mL round-bottom flask, was placed tert-butyl 6-[3-formyl-4-(methoxycarbonyl)phenyl]-2,6-diazaspiro[3.3]heptane-2-carboxylate (684.80 mg, 1.900 mmol, 1.00 equiv), 3-aminopiperidine-2,6-dione hydrochloride (375.30 mg, 2.280 mmol, 1.20 equiv), DCM (30.00 mL), DIEA (0.80 mL, 4.593 mmol, 2.42 equiv), AcOH (1.50 mL, 26.177 mmol, 13.78 equiv). The resulting mixture was stirred for 4 h at 35° C. in an oil bath. This was followed by the addition of $NaBH(OAc)_3$ (1.21 g, 5.709 mmol, 3.00 equiv) and the resulting mixture was allowed to react, with stirring, for an additional 3 h while the temperature was maintained at 35° C. in an oil bath. The reaction was then quenched by the addition of water (50 mL) and the pH value of the solution was adjusted to 8 with saturated $NaHCO_3$. The resulting mixture was extracted with DCM/MeOH (10/1, 100 mL×2) and the organic layers combined and dried over anhydrous sodium sulfate and concentrated under vacuum. The residue was applied onto a silica gel column with dichloromethane/methanol (25/1). This resulted in 620 mg (74%) of tert-butyl 6-[2-(2,6-dioxopiperidin-3-yl)-1-oxo-2,3-dihydro-1H-isoindol-5-yl]-2,6-diazaspiro[3.3]heptane-2-carboxylate as a light green solid. LC/MS (ESI) m/z: 441.00 $[M+1]^+$.

Step 4: Preparation of 3-(1-oxo-5-(2,6-diazaspiro[3.3]heptan-2-yl)isoindolin-2-yl)piperidine-2,6-dione

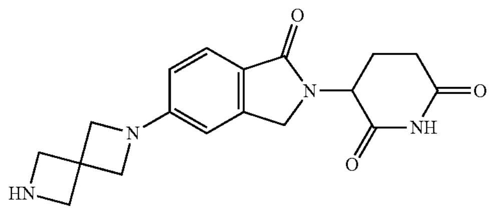 [SMILES: O=C1CCC(N2Cc3cc(N4CC5(CNC5)C4)ccc3C2=O)C(=O)N1]

Into a 50-mL round-bottom flask, was placed tert-butyl 6-[2-(2,6-dioxopiperidin-3-yl)-1-oxo-2,3-dihydro-1H-isoindol-5-yl]-2,6-diazaspiro[3.3]heptane-2-carboxylate (110.10 mg, 0.250 mmol, 1.00 equiv), DCM (8.00 mL), TFA (1.50 mL). The resulting solution was stirred for 1 h at room temperature. The acid was neutralized with DIEA. This resulted in a solution of 85.1 mg of 3-(5-[2,6-diazaspiro[3.3]heptan-2-yl]-1-oxo-2,3-dihydro-1H-isoindol-2-yl)piperidine-2,6-dione in DCM as a light brown solution. LC/MS (ESI) m/z: 341.00 $[M+1]^+$.

Step 5: Preparation of (3R)—N-(3-(5-(4-(4-((6-(2-(2,6-dioxopiperidin-3-yl)-1-oxoisoindolin-5-yl)-2,6-diazaspiro[3.3]heptan-2-yl)methyl)piperidin-1-yl)phenyl)-1H-pyrrolo[2,3-b]pyridine-3-carbonyl)-2,4-difluorophenyl)-3-fluoropyrrolidine-1-sulfonamide

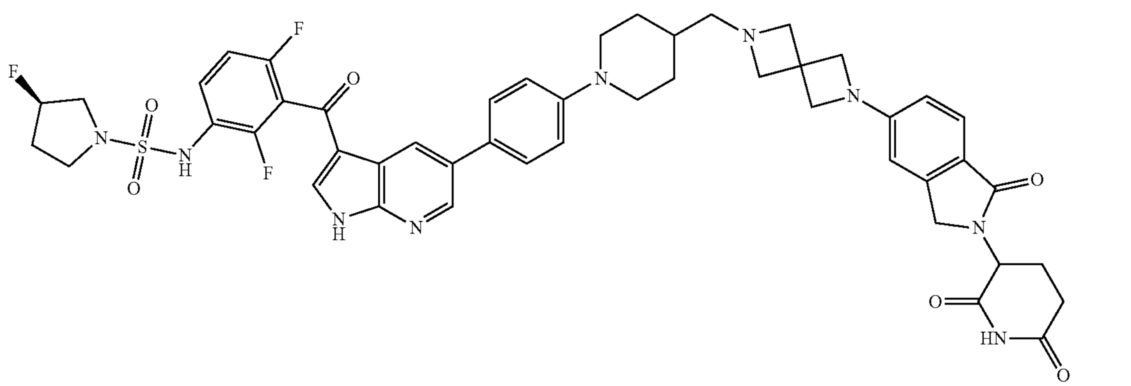 [SMILES: O=C1CCC(N2Cc3cc(N4CC5(CN(CC6CCN(c7ccc(-c8cnc9[nH]cc(C(=O)c%10c(F)ccc(NS(=O)(=O)N%11CC[C@@H](F)C%11)c%10F)c9c8)cc7)CC6)C5)C4)ccc3C2=O)C(=O)N1]

Into a 50-mL round-bottom flask, was placed (3R)—N-(2,4-difluoro-3-[5-[4-(4-formylpiperidin-1-yl)phenyl]-1H-pyrrolo[2,3-b]pyridine-3-carbonyl]phenyl)-3-fluoropyrrolidine-1-sulfonamide (113.00 mg, 0.185 mmol, 1.00 equiv), 3-(5-[2,6-diazaspiro[3.3]heptan-2-yl]-1-oxo-2,3-dihydro-1H-isoindol-2-yl)piperidine-2,6-dione (75.50 mg, 0.222 mmol, 1.20 equiv), DCM (45.00 mL). The resulting solution was stirred for 2 h at 35° C. in an oil bath. This was followed by the addition of $NaBH_3CN$ (34.80 mg, 0.554 mmol, 3.00 equiv) and the resulting mixture was allowed to react, with stirring, for an additional 0.5 h at room temperature. The reaction was then quenched by the addition of water (50 mL) and extracted with DCM/MeOH (10/1, 60 mL×2). The organic layers were combined and dried over anhydrous sodium sulfate and concentrated under vacuum. The residue was purified by Prep-TLC ($CH_2Cl_2$/MeOH=7:1). The crude product was purified by Prep-HPLC. This resulted in 27 mg (16%) of (3R)—N-[3-(5-[4-[4-([6-[2-(2,6-dioxopiperidin-3-yl)-1-oxo-2,3-dihydro-1H-isoindol-5-yl]-2,6-diazaspiro[3.3]heptan-2-yl]methyl)piperidin-1-yl]phenyl]-1H-pyrrolo[2,3-b]pyridine-3-carbonyl)-2,4-difluorophenyl]-3-fluoropyrrolidine-1-sulfonamide as a yellow green solid. LC/MS (ESI) m/z: 936.30 $[M+1]^+$; $^1$H-NMR (300 MHz, DMSO-$d_6$) δ 12.91 (s, 1H), 10.95 (s, 1H), 8.65 (s, 1H), 8.53 (s, 1H), 8.16 (s, 1H), 8.07 (s, 1H), 7.66-7.57 (m, 3H), 7.51-7.48 (m, 1H), 7.30-7.24 (m, 1H), 7.08-7.05 (m, 2H), 6.53-6.48 (m, 2H), 5.30 (d, J=53.1 Hz, 1H), 5.06-5.00 (m, 1H), 4.34-4.15 (m, 3H), 4.00 (s, 5H), 3.79-3.75 (m, 3H), 2.96-2.81 (m, 2H), 2.74-2.66 (m, 3H), 2.61-2.56 (m, 1H), 2.44-2.28 (m, 4H), 2.14-1.94 (m, 4H), 1.79-1.75 (m, 2H), 1.49 (s, 1H), 1.30-1.19 (m, 3H).

Exemplary Synthesis of (3R)—N-(3-(5-(4-(4-((4-(2-(2,6-dioxopiperidin-3-yl)-1-oxoisoindolin-5-yl)piperidin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide (Exemplary Compound 579)

Step 1: Preparation of 3-(5-bromo-1-oxoisoindolin-2-yl)piperidine-2,6-dione

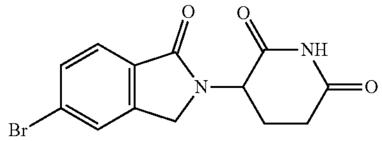 [SMILES: O=C1CCC(N2Cc3cc(Br)ccc3C2=O)C(=O)N1]

Into a 100-mL round-bottom flask purged and maintained with an inert atmosphere of nitrogen, was placed a solution of methyl 4-bromo-2-(bromomethyl)benzoate (10.0 g, 32.47 mmol, 1.00 equiv) in N,N-dimethylformamide (30 mL), 3-aminopiperidine-2,6-dione (4.2 g, 32.78 mmol, 1.00 equiv), triethylamine (8.2 g, 81.04 mmol, 2.50 equiv). The resulting solution was stirred for 12 h at 80° C. The reaction was then quenched by the addition of water. The solid was collected, and the resulting solution was extracted with ethyl acetate and the organic layers combined. The resulting mixture was washed with brine. The mixture was dried over anhydrous sodium sulfate. The residue was applied onto a silica gel column with ethyl acetate/petroleum ether (1:5). The collected fractions were combined and concentrated under vacuum. This resulted in 5.6 g (53%) of 3-(5-bromo-1-oxo-2,3-dihydro-1H-isoindol-2-yl)piperidine-2,6-dione as a purple solid. LC/MS (ESI) m/z: 323.00/325.00 $[M+1]^+$.

Step 2: Preparation of tert-butyl 4-(2-(2,6-dioxopiperidin-3-yl)-1-oxoisoindolin-5-yl)-3,6-dihydropyridine-1 (2H)-carboxylate

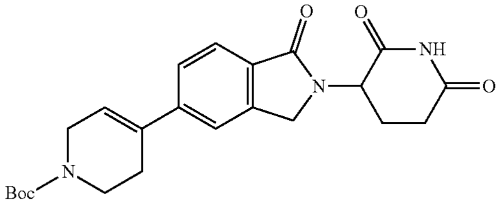 [SMILES: CC(C)(C)OC(=O)N1CC=C(c2ccc3c(c2)CN(C2CCC(=O)NC2=O)C3=O)CC1]

Into a 250-mL 3-necked round-bottom flask purged and maintained with an inert atmosphere of nitrogen, was placed a solution of tert-butyl 4-(tetramethyl-1,3,2-dioxaborolan-2-yl)-1,2,3,6-tetrahydropyridine-1-carboxylate (2.9 g, 9.38 mmol, 3.00 equiv) in dioxane (60 mL), potassium carbonate (1.3 g, 9.41 mmol, 3.00 equiv), 3-(5-bromo-1-oxo-2,3-dihydro-1H-isoindol-2-yl)piperidine-2,6-dione (1.0 g, 3.09 mmol, 1.00 equiv), tetrakis(triphenylphosphine)palladium (358.0 mg, 0.31 mmol, 0.10 equiv). The resulting solution was stirred for overnight at 90° C. in an oil bath under nitrogen atmosphere. The filtrates were collected by filtration. The resulting mixture was concentrated under vacuum. The residue was applied onto a silica gel column with ethyl acetate/petroleum ether (1/1). The collected fractions were combined and concentrated under vacuum. This resulted in 260.0 mg (20%) of tert-butyl 4-[2-(2,6-dioxopiperidin-3-yl)-1-oxo-2,3-dihydro-1H-isoindol-5-yl]-1,2,3,6-tetrahydropyridine-1-carboxylate as a yellow solid. LC/MS (ESI) m/z: 426.15 $[M+1]^+$.

Step 3: Preparation of tert-butyl 4-(2-(2,6-dioxopiperidin-3-yl)-1-oxoisoindolin-5-yl)piperidine-1-carboxylate

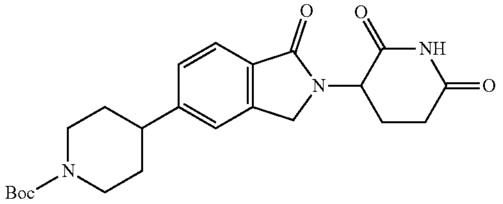 [SMILES: CC(C)(C)OC(=O)N1CCC(c2ccc3c(c2)CN(C2CCC(=O)NC2=O)C3=O)CC1]

Into a 50-mL round-bottom flask, was placed a solution of tert-butyl 4-[2-(2,6-dioxopiperidin-3-yl)-1-oxo-2,3-dihydro-1H-isoindol-5-yl]-1,2,3,6-tetrahydropyridine-1-carboxylate (200.0 mg, 0.47 mmol, 1.00 equiv) in tetrahydrofuran (mL), Palladium carbon (300.0 mg, 1.69 mmol, 8.00 equiv) under nitrogen atmosphere. The flask was then vacuumed and flushed with hydrogen. The reaction mixture was hydrogenated at room temperature for 4 h under hydrogen atmosphere using a hydrogen balloon, then filtered through a Celite pad and concentrated under reduced pressure. This resulted in 190.0 mg (95%) of tert-butyl 4-[2-(2,6-dioxopiperidin-3-yl)-1-oxo-2,3-dihydro-1H-isoindol-5-yl]piperidine-1-carboxylate as a yellow solid.

Step 4: Preparation of 3-(1-oxo-5-(piperidin-4-yl)isoindolin-2-yl)piperidine-2,6-dione

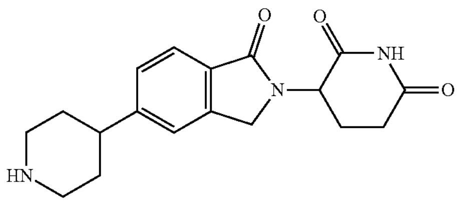 [SMILES: O=C1CCC(N2Cc3cc(C4CCNCC4)ccc3C2=O)C(=O)N1]

Into a 50-mL round-bottom flask, was placed a solution of tert-butyl 4-[2-(2,6-dioxopiperidin-3-yl)-1-oxo-2,3-dihydro-1H-isoindol-5-yl]piperidine-1-carboxylate (90.0 mg, 0.21 mmol, 1.00 equiv) in dichloromethane (4 mL), trifluoroacetic acid (2.0 mL). The resulting solution was stirred for 2 h at room temperature. The resulting mixture was concentrated under vacuum. This resulted in 80.0 mg (86%) of 3-(1-oxo-5-(piperidin-4-yl)isoindolin-2-yl)piperidine-2,6-dione (TFA salt) as a yellow oil.

Step 5: Preparation of (3R)—N-(3-(5-(4-(4-((4-(2-(2,6-dioxopiperidin-3-yl)-1-oxoisoindolin-5-yl)piperidin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide

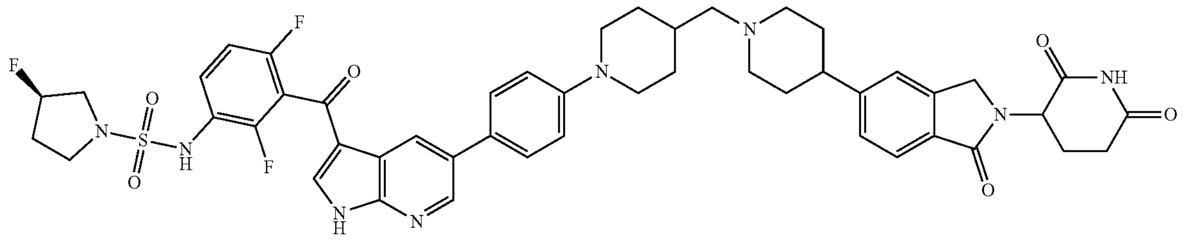 [SMILES: O=C1CCC(N2Cc3cc(C4CCN(CC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]

Into a 50-mL round-bottom flask, was placed 3-[1-oxo-5-(piperidin-4-yl)-3H-isoindol-2-yl]piperidine-2,6-dione; trifluoroacetic acid (91.00 mg, 0.206 mmol, 1.00 equiv), dichloromethane (15.00 mL), (3R)—N-(2,4-difluoro-3-[5-[4-(4-formylpiperidin-1-yl)phenyl]-1H-pyrrolo[2,3-b]pyridine-3-carbonyl]phenyl)-3-fluoropyrrolidine-1-sulfonamide (126.10 mg, 0.206 mmol, 1.00 equiv). The mixture was stirring for 2 h at room temperature, to this was added $NaBH_3CN$ (64.78 mg, 1.031 mmol, 5.00 equiv). The resulting solution was stirred overnight at room temperature. The reaction was then quenched by the addition of water (20 mL). The resulting solution was extracted with dichloromethane (2×20 mL), dried over anhydrous sodium sulfate. The residue was applied onto a silica gel column with dichloromethane/methanol (10/1). The crude product was purified by Prep-HPLC. The collected fractions were combined and concentrated under vacuum. This resulted in 56.1 mg (29.48%) of (3R)—N-[3-(5-[4-[4-([4-[2-(2,6-dioxopiperidin-3-yl)-1-oxo-3H-isoindol-5-yl]piperidin-1-yl]methyl)piperidin-1-yl]phenyl]-1H-pyrrolo[2,3-b]pyridine-3-carbonyl)-2,4-difluorophenyl]-3-fluoropyrrolidine-1-sulfonamide as a yellow solid. LC/MS (ESI) m/z: 923.30 $[M+1]^+$; $^1$H-NMR (300 MHz, DMSO-$d_6$) δ 12.91 (s, 1H), 10.99 (s, 1H), 9.85 (s, 1H), 8.67 (s, 1H), 8.66 (s, 1H), 8.08 (s, 1H), 7.68-7.52 (m, 5H), 7.44-7.41 (d, J=7.8 Hz, 1H), 7.30-7.25 (m, 1H), 7.10-7.07 (d, J=8.4 Hz, 2H), 5.40-5.09 (m, 2H), 4.47-4.28 (m, 2H), 3.83-3.79 (m, 2H), 3.51-3.29 (m, 4H), 3.04-3.00 (d, J=10.5 Hz, 2H), 2.93-2.52 (m, 5H), 2.27-2.25 (d, J=6.3 Hz, 2H), 2.15-1.99 (m, 5H), 1.87-1.73 (m, 7H), 1.28-1.25 (d, J=9.6 Hz, 2H).

Exemplary Synthesis of (3R)—N-(3-(5-(4-(2-(4-(2-(2,6-dioxopiperidin-3-yl)-1-oxoisoindolin-5-yl)piperazin-1-yl)ethyl)phenyl)-1H-indole-3-carbonyl)-2,4-difluorophenyl)-3-fluoropyrrolidine-1-sulfonamide (Exemplary compound 596)

Step 1: Preparation of 1-bromo-4-(2,2-dimethoxyethyl)benzene

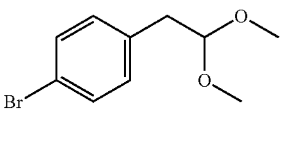

To a mixture of 2-(4-bromophenyl) acetaldehyde (2 g, 10.05 mmol, 1 eq) and trimethoxymethane (5.33 g, 50.24 mmol, 5.51 mL, 5 eq) in methanol (30 mL) was added p-Toluensulfonic Acid aquo-complex (96 mg, 0.50 mmol, 0.05 eq) in one portion at 15° C. under nitrogen. The mixture was stirred at 15° C. for 16 h. Saturated aqueous sodium bicarbonate was added to adjust the pH=8~9. The mixture was poured into water (20 mL) and stirred for 1 min. The aqueous phase was extracted with ethyl acetate (60 mL*2). The combined organic phase was washed with brine (30 mL*2), dried with anhydrous sodium sulfate, filtered and concentrated in vacuum. The residue was purified by column chromatography (Petroleum ether/Ethyl acetate=15/1 to 5:1). Compound 1-bromo-4-(2,2-dimethoxyethyl) benzene (1.97 g, 8.04 mmol, 80% yield) was obtained as a colorless oil. $^1$H-NMR (400 MHz, $CDCl_3$) δ 7.47-7.34 (m, 2H), 7.16-7.05 (m, 2H), 4.55-4.44 (m, 1H), 3.39-3.30 (m, 6H), 2.92-2.79 (m, 2H).

Step 2: Preparation of 2-(4-(2,2-dimethoxyethyl) phenyl)-4,4,5,5-tetramethyl-1,3,2-dioxaborolane

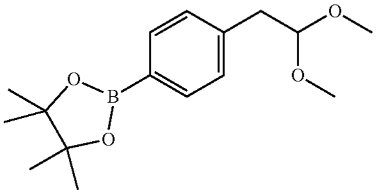

A mixture of 1-bromo-4-(2,2-dimethoxyethyl)benzene (1.63 g, 6.65 mmol, 1 eq), 4,4,5,5-tetramethyl-2-(4,4,5,5-tetramethyl-1,3,2-dioxaborolan-2-yl)-1,3,2-dioxaborolane (2.20 g, 8.65 mmol, 1.3 eq), potassium acetate (1.31 g, 13.30 mmol, 2 eq) and ditert-butyl(cyclopentyl)phosphane;dichloropalladium;iron (433 mg, 0.66 mmol, 0.1 eq) in dioxane (25 mL) was degassed and purged with nitrogen for 3 times, and then the mixture was stirred at 95° C. for 12 h under nitrogen atmosphere. The reaction mixture was concentrated under reduced pressure. The residue was purified by column chromatography (Petroleum ether/Ethyl acetate=50/1 to 20:1). Compound 2-[4-(2,2-dimethoxyethyl)phenyl]-4,4,5,5-tetramethyl-1,3,2-dioxaborolane (1.9 g, 6.50 mmol, 98% yield) was obtained as a brown oil. $^1$H-NMR (400 MHz, $CDCl_3$) δ 7.71-7.64 (m, 2H), 7.19 (s, 2H), 4.51-4.42 (m, 1H), 3.29-3.19 (m, 6H), 2.89-2.80 (m, 2H), 1.28-1.25 (m, 12H).

Step 3: Preparation of (R)—N-(3-(5-(4-(2,2-dimethoxyethyl)phenyl)-1H-pyrrolo[2,3-b]pyridine-3-carbonyl)-2,4-difluorophenyl)-3-fluoropyrrolidine-1-sulfonamide

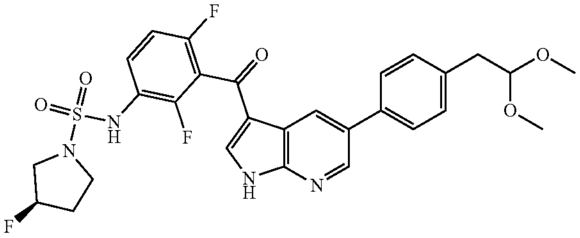 [SMILES: COC(Cc1ccc(-c2cnc3[nH]cc(C(=O)c4c(F)ccc(NS(=O)(=O)N5CC[C@@H](F)C5)c4F)c3c2)cc1)OC]

A mixture of (3R)—N-[3-(5-bromo-1H-pyrrolo[2,3-b]pyridine-3-carbonyl)-2,4-difluoro-phenyl]-3-fluoro-pyrrolidine-1-sulfonamide (1.95 g, 3.87 mmol, 1 eq), 2-[4-(2,2-dimethoxyethyl) phenyl]-4,4,5,5-tetramethyl-1,3,2-dioxaborolane (1.25 g, 4.26 mmol, 1.1 eq), 4-ditert-butylphosphanyl-N,N-dimethyl-aniline;dichloropalladium (274 mg, 0.39 mmol, 0.3 mL, 0.1 eq), cesium fluoride (2.35 g, 15.50 mmol, 0.6 mL, 4 eq) in dioxane (20 mL) and water (4 mL) was degassed and purged with nitrogen for 3 times, and then the mixture was stirred at 90° C. for 12 hours under nitrogen atmosphere. The reaction mixture was diluted with water (30 mL) and extracted with ethyl acetate (50 mL*2). The combined organic layers were washed with brine (40 mL*2), dried over anhydrous sodium sulfate, filtered and concentrated under reduced pressure. The residue was purified by column chromatography (Dichloromethane:Methanol=1/0 to 10:1). Then the crude product was further purified by prep-HPLC. Compound (3R)—N-[3-[5-[4-(2,2-dimethoxyethyl) phenyl]-1H-indole-3-carbonyl]-2,4-difluoro-phenyl]-3-fluoro-pyrrolidine-1-sulfonamide (1.31 g, 2.23 mmol, 57% yield) was obtained as a yellow solid. LC/MS (ESI) m/z: 589.2 [M+1]$^+$.

Step 4: Preparation of (R)—N-(2,4-difluoro-3-(5-(4-(2-oxoethyl)phenyl)-1H-pyrrolo[2,3-b]pyridine-3-carbonyl)phenyl)-3-fluoropyrrolidine-1-sulfonamide

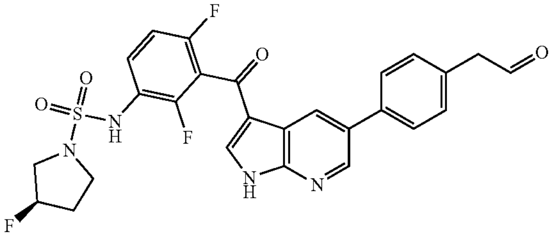 [SMILES: O=CCc1ccc(-c2cnc3[nH]cc(C(=O)c4c(F)ccc(NS(=O)(=O)N5CC[C@@H](F)C5)c4F)c3c2)cc1]

To a solution of (3R)—N-[3-[5-[4-(2,2-dimethoxyethyl) phenyl]-1H-indole-3-carbonyl]-2,4-difluoro-phenyl]-3-fluoro-pyrrolidine-1-sulfonamide (1.31 g, 2.23 mmol, 1 eq) in tetrahydrofuran (15 mL) was added sulfuric acid (2 M, 15 mL, 13.46 eq). The mixture was stirred at 70° C. for 2 hours. The reaction mixture was basified with saturated aqueous sodium bicarbonate to pH=8. Then the reaction mixture was diluted with water (40 mL), extracted with tetrahydrofuran (30 mL) and ethyl acetate (30 mL*2). The combined organic layers were washed with brine (30 mL*2), dried over anhydrous sodium sulfate, filtered and concentrated under reduced pressure. Compound (3R)—N-[2, 4-difluoro-3-[5-[4-(2-oxoethyl) phenyl]-1H-indole-3-carbonyl]phenyl]-3-fluoro-pyrrolidine-1-sulfonamide (1.26 g) was obtained as a yellow solid. LC/MS (ESI) m/z: 543.2 [M+1]$^+$.

Step 5: Preparation of (3R)—N-(3-(5-(4-(2-(4-(2-(2,6-dioxopiperidin-3-yl)-1-oxoisoindolin-5-yl)piperazin-1-yl)ethyl)phenyl)-1H-indole-3-carbonyl)-2,4-difluorophenyl)-3-fluoropyrrolidine-1-sulfonamide

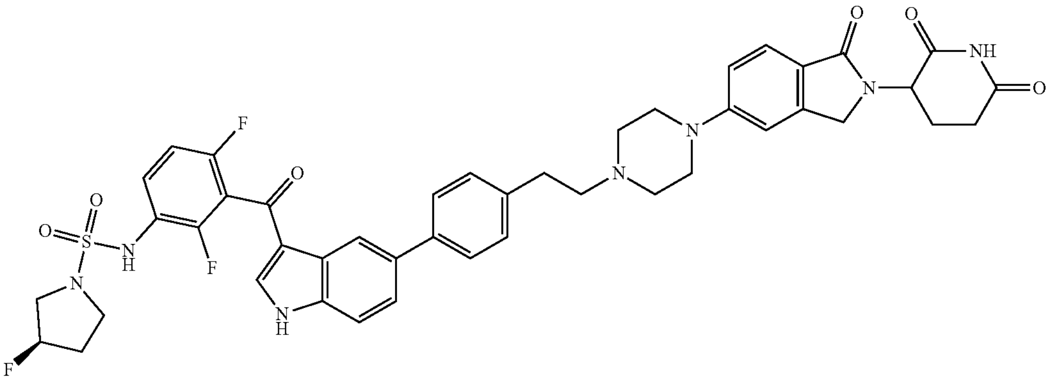 [SMILES: O=C1CCC(N2Cc3cc(N4CCN(CCc5ccc(-c6ccc7[nH]cc(C(=O)c8c(F)ccc(NS(=O)(=O)N9CC[C@@H](F)C9)c8F)c7c6)cc5)CC4)ccc3C2=O)C(=O)N1]

To a solution of 3-(1-oxo-5-piperazin-1-yl-isoindolin-2-yl)piperidine-2,6-dione (70 mg, 0.19 mmol, 1 eq, hydrochloride) in methanol (2 mL) and dichloromethane (1 mL) was added sodium acetate (31 mg, 0.38 mmol, 2 eq) to adjust the PH~8. The mixture was stirred at 30° C. for 5 min, then (3R)—N-[2,4-difluoro-3-[5-[4-(2-oxoethyl)phenyl]-1H-pyrrolo[2,3-b]pyridine-3-carbonyl]phenyl]-3-fluoro-pyrrolidine-1-sulfonamide (104 mg, 0.19 mmol, 1 eq) was added. The mixture was stirred at 30° C. for 5 min. followed by the addition of acetic acid (23.04 mg, 0.38 mmol, 2 eq) to adjust the pH ~5.0. The mixture was stirred at 15° C. for 20 min. Then sodium cyanoborohydride (24 mg, 0.38 mmol, 2 eq) was added in portions. The reaction mixture was stirred at 30° C. for 1.5 h. The reaction mixture was diluted with water (30 mL), extracted with ethyl acetate (25 mL*2) and tetrahydrofuran (20 mL). The combined organic layers were washed with saturated brine (20 mL*2), dried over anhydrous sodium sulfate, filtered and concentrated under reduced pressure. The residue was purified by prep-HPLC. Compound 3R)—N-[3-[5-[4-[2-[4-[2-(2,6-dioxo-3-piperidyl)-1-oxo-isoindolin-5-yl]piperazin-1-yl]ethyl]phenyl]-1H-pyrrolo[2,3-b]pyridine-3-carbonyl]-2,4-difluoro-phenyl]-3-fluoro-pyrrolidine-1-sulfonamide (104.5 mg, 0.10 mmol, 55% yield, 98% purity, trifluoroacetate) was obtained as a white solid. LC/MS (ESI) m/z: 855.3 $[M+1]^+$; $^1$H-NMR (400 MHz, DMSO-$d_6$) δ 13.05-12.95 (m, 1H), 10.96 (s, 1H), 9.85 (s, 1H), 8.72 (d, J=2.4 Hz, 1H), 8.64 (d, J=0.8 Hz, 1H), 8.13 (d, J=2.8 Hz, 1H), 7.81-7.73 (m, 2H), 7.67-7.56 (m, 2H), 7.47 (d, J=8.0 Hz, 2H), 7.28 (t, J=8.4 Hz, 1H), 7.24-7.15 (m, 2H), 5.41-5.18 (m, 1H), 5.07 (dd, J=5.2, 13.2 Hz, 1H), 4.42-4.33 (m, 1H), 4.29-4.22 (m, 1H), 4.14-4.02 (m, 3H), 3.72 (d, J=11.2 Hz, 3H), 3.42-3.38 (m, 2H), 3.37-3.21 (m, 4H), 3.20-3.09 (m, 4H), 2.99-2.85 (m, 1H), 2.64-2.54 (m, 2H), 2.39 (dd, J=4.8, 13.2 Hz, 1H), 2.13-2.07 (m, 1H), 2.01-1.95 (m, 1H).

Exemplary Synthesis of (3R)—N-(3-(5-(4-(((1R, 3S)-3-((1-(2-(2,6-dioxopiperidin-3-yl)-1-oxoisoindolin-5-yl)piperidin-4-yl)oxy)cyclohexyl)oxy)phenyl)-1H-pyrrolo[2,3-b]pyridine-3-carbonyl)-2,4-difluorophenyl)-3-fluoropyrrolidine-1-sulfonamide (Exemplary Compound 709)

Step 1: Preparation of tert-butyl (R)-5-bromo-3-(2,6-difluoro-3-((3-fluoropyrrolidine)-1-sulfonamido)benzoyl)-1H-pyrrolo[2,3-b]pyridine-1-carboxylate

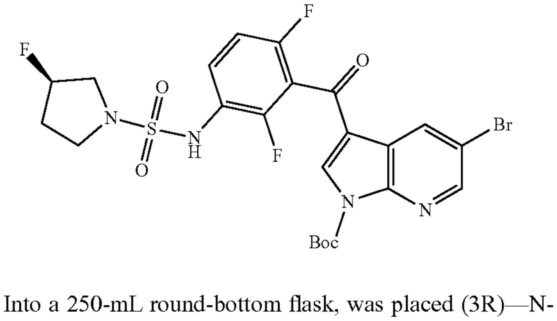

Into a 250-mL round-bottom flask, was placed (3R)—N-(3-[5-bromo-1H-pyrrolo[2,3-b]pyridine-3-carbonyl]-2,4-difluoro-phenyl)-3-fluoropyrrolidine-1-sulfonamide (10.0 g, 19.9 mmol, 1.0 equiv), DCM (120 mL), TEA (6.0 g, 59.3 mmol, 3.0 equiv) and $(Boc)_2O$ (6.0 g, 29.7 mmol, 1.5 equiv). The resulting mixture was stirred for 6 hrs at room temperature. The resulting mixture was concentrated under vacuum. The residue was applied onto a silica gel column with ethyl acetate/petroleum ether (1;3). This resulted in 9.0 g (75.1%) of tert-butyl 5-bromo-3-(2,6-difluoro-3-[[(3R)-3-fluoropyrrolidin-1-ylsulfonyl]amino]benzoyl)pyrrolo[2,3-b]pyridine-1-carboxylate as an off-white solid. LC/MS (ESI) m/z: 605.10 $[M+1]^+$.

Step 2: Preparation of tert-butyl (R)-3-(2,6-difluoro-3-((3-fluoropyrrolidine)-1-sulfonamido)benzoyl)-5-(4,4,5,5-tetramethyl-1,3,2-dioxaborolan-2-yl)-1H-pyrrolo[2,3-b]pyridine-1-carboxylate

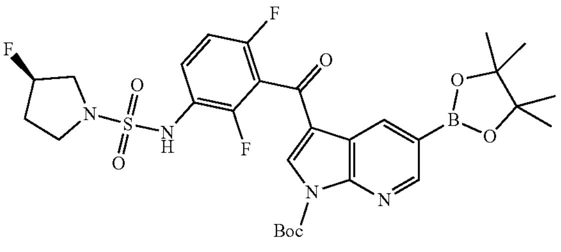 [SMILES: CC(C)(C)OC(=O)n1cc(C(=O)c2c(F)ccc(NS(=O)(=O)N3CC[C@@H](F)C3)c2F)c2cc(B3OC(C)(C)C(C)(C)O3)cnc21]

Into a 250-mL round-bottom flask purged and maintained with an inert atmosphere of nitrogen, was placed tert-butyl 5-bromo-3-(2,6-difluoro-3-[[(3R)-3-fluoropyrrolidin-1-ylsulfonyl]amino]benzoyl)pyrrolo[2,3-b]pyridine-1-carboxylate (9.0 g, 14.9 mmol, 1.0 equiv), bis(pinacolato) diboron (7.6 g, 29.9 mmol, 2.0 equiv), $Pd(dppf)Cl_2$ (1.6 g, 2.2 mmol, 0.15 equiv), KOAc (4.4 g, 44.8 mmol, 3.0 equiv) and dioxane (150 mL). The resulting suspension was stirred for 5 hrs at 90° C. in an oil bath. The solids were filtered out, and then washed with DCM (3×100 mL). The combined filtrate was concentrated under vacuum. The residue was applied onto a silica gel column with ethyl acetate/petroleum ether (1:1). This resulted in 5.5 g (57%) of tert-butyl 3-(2,6-difluoro-3-[[(3R)-3-fluoropyrrolidin-1-ylsulfonyl]amino]benzoyl)-5-(4,4,5,5-tetramethyl-1,3,2-dioxaborolan-2-yl)pyrrolo[2,3-b]pyridine-1-carboxylate as a light yellow solid. LC/MS (ESI) m/z: 651.20 $[M+1]^+$.

Step 3: Preparation of 3-(4-iodophenoxy)cyclohexan-1-ol

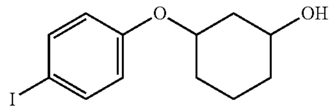 [SMILES: OC1CCCC(Oc2ccc(I)cc2)C1]

Into a 1-L 3-necked round-bottom flask purged and maintained with an inert atmosphere of nitrogen, was placed $PPh_3$ (17.9 g, 68.2 mmol, 1.5 equiv), THF (500 mL) and DIAD (13.8 g, 68.2 mmol, 1.5 equiv) at 0° C. in a water/ice bath. After the reaction mixture was stirred for 30 min at 0° C., cyclohexane-1,3-diol (7.9 g, 68.0 mmol, 1.5 equiv) and 4-iodophenol (10.0 g, 45.4 mmol, 1.0 equiv) were added into the flask. The resulting mixture was stirred for 30 min at 0° C., and then the cooling bath was removed. The resulting mixture was allowed to react, with stirring, overnight at room temperature. The resulting mixture was concentrated under vacuum. The residue was then quenched by the addition of 200 mL of water. The resulting mixture was extracted with 3×250 mL of ethyl acetate. The organic phase was combined, washed with 3×150 ml of brine, dried over anhydrous sodium sulfate, and concentrated under vacuum. The residue was applied onto a silica gel column with ethyl acetate/petroleum ether (1:4). This resulted in 5.5 g (38.0%) of 3-(4-iodophenoxy)cyclohexan-1-ol as a white solid.

Step 4: Preparation of ((3-(4-iodophenoxy)cyclohexyl)oxy)trimethylsilane

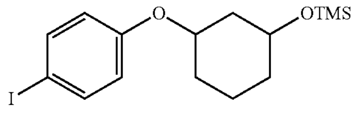

Into a 250-mL round-bottom flask, was placed 3-(4-iodophenoxy)cyclohexan-1-ol (5.5 g, 17.3 mmol, 1.0 equiv), DCM (100 mL), TEA (5.5 g, 54.4 mmol, 3.1 equiv) and TMSCl (2.8 g, 25.8 mmol, 1.5 equiv). The resulting mixture was stirred for 5 hrs at room temperature. The reaction was then quenched by the addition of 150 mL of $NaHCO_3$ (aq). The resulting mixture was extracted with 2×100 mL of dichloromethane. The organic phase was combined, dried over anhydrous sodium sulfate and concentrated under vacuum. This resulted in 6.5 g (96.3%) of ((3-(4-iodophenoxy)cyclohexyl)oxy)trimethylsilane as a white semi-solid.

Step 5: Preparation of (((1S,3R)-3-(4-iodophenoxy)cyclohexyl)oxy)trimethylsilane

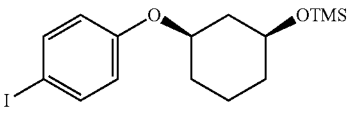

[[3-(4-iodophenoxy)cyclohexyl]oxy]trimethylsilane (6.5 g, 16.65 mmol, 1.0 equiv) was purified by Flash-Prep-HPLC. This resulted in 2.0 g (30.8%) of [[(1S,3R)-3-(4-iodophenoxy)cyclohexyl]oxy]trimethylsilane as white solid.

Step 6: Preparation of 4-(((1S,3R)-3-(4-iodophenoxy)cyclohexyl)oxy)piperidine

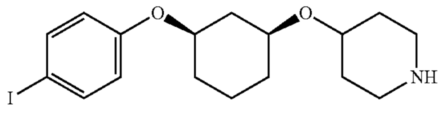 [SMILES: Ic1ccc(O[C@@H]2CCC[C@H](OC3CCNCC3)C2)cc1]

Into a 100-mL 3-necked round-bottom flask purged and maintained with an inert atmosphere of nitrogen, was placed [[(1S,3R)-3-(4-iodophenoxy)cyclohexyl]oxy]trimethylsilane (1.9 g, 4.8 mmol, 1.0 equiv) and DCM (50 mL). The solution was cooled to −70° C. with an $EtOH/N_2$ (liquid) bath. Into the flask, was then successively added tert-butyl 4-oxopiperidine-1-carboxylate (0.97 g, 4.8 mmol, 1.0 equiv), $Et_3SiH$ (0.62 g, 5.4 mmol, 1.1 equiv) and TMSOTf (0.54 g, 2.4 mmol, 0.5 equiv), maintaining the temperature below −60° C. The resulting mixture was allowed to warm up to room temperature over 2 hrs and stirred for another 2 hrs at room temperature. The reaction was then quenched by the addition of 150 mL of $NaHCO_3$(aq). The resulting mixture was extracted with 3×150 mL of dichloromethane. The organic phase was combined, dried over anhydrous sodium sulfate and concentrated under vacuum. The residue was applied onto a silica gel column with dichloromethane/methanol/$Et_3N$ (80:15:5). This resulted in 580 mg (29.7%) of 4-[[(1S,3R)-3-(4-iodophenoxy)cyclohexyl]oxy]piperidine as light brown oil. LC/MS (ESI) m/z: 402.10 $[M+1]^+$.

Step 7: Preparation of methyl 4-fluoro-2-formylbenzoate

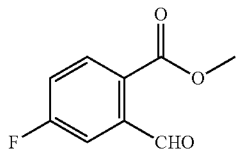

Into a 250-mL round-bottom flask, was placed methyl 2-cyano-4-fluorobenzoate (5.38 g, 30.031 mmol, 1.00 equiv), formic acid (50.00 mL, 88%), $H_2O$ (5.00 mL), $PtO_2$ (1.36 g, 5.989 mmol, 0.20 equiv). The resulting mixture was stirred for 2 h at 80° C. in an oil bath. The rest of $PtO_2$ (0.10 equiv) was added and the resulting mixture was allowed to react, with stirring, for an additional 2 h while the temperature was maintained at 80° C. in an oil bath. The reaction mixture was cooled to room temperature. The resulting mixture was diluted with water (100 mL) and ethyl acetate (200 mL). The solids were filtered out. The aqueous layer was back extracted with ethyl acetate (100 mL). The organic layers were combined and washed with brine (150 mL×2). The organic was dried over anhydrous sodium sulfate and concentrated under vacuum. The residue was applied onto a silica gel column with ethyl acetate/petroleum ether (1/25). This resulted in 2.17 g (40%) of methyl 4-fluoro-2-formylbenzoate as a white crystal. LC/MS (ESI) m/z: 182.95 $[M+1]^+$; $^1H$ NMR (300 MHz, $CDCl_3$) δ 10.68-10.65 (m, 1H), 8.10-8.03 (m, 1H), 7.64-7.60 (m, 1H), 7.36-7.28 (m, 1H), 3.99 (s, 3H).

Step 8: Preparation of methyl 2-formyl-4-(4-(((1S,3R)-3-(4-iodophenoxy)cyclohexyl)oxy)piperidin-1-yl)benzoate

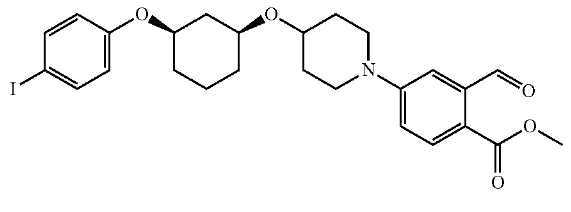 [SMILES: COC(=O)c1ccc(N2CCC(O[C@H]3CCC[C@@H](Oc4ccc(I)cc4)C3)CC2)cc1C=O]

Into a 30-mL sealed tube, was placed 4-[[(1S,3R)-3-(4-iodophenoxy)-cyclohexyl]oxy]piperidine (550 mg, 1.4 mmol, 1.0 equiv), methyl 4-fluoro-2-formylbenzoate (380 mg, 2.1 mmol, 1.5 equiv), DMSO (10 mL) and DIEA (2 mL, 11.5 mmol, 8.4 equiv). The tube was purged and maintained with an inert atmosphere of nitrogen. The resulting mixture was stirred overnight at 110° C. in an oil bath. The reaction was then quenched by the addition of 150 mL of water. The resulting mixture was extracted with 3×150 mL of ethyl acetate. The organic phase was combined, washed with 3×100 ml of brine, dried over anhydrous sodium sulfate, and concentrated under vacuum. The residue was applied onto a silica gel column with ethyl acetate/petroleum ether (1;4). This resulted in 95 mg (12.3%) of methyl 2-formyl-4-(4-[[(1S,3R)-3-(4-iodophenoxy)cyclohexyl]oxy]piperidin-1-yl)benzoate as a yellow solid. LC/MS (ESI) m/z: 564.05 $[M+1]^+$.

Step 9: Preparation of 3-(5-(4-(((1S,3R)-3-(4-iodophenoxy)cyclohexyl)oxy)piperidin-1-yl)-1-oxoisoindolin-2-yl)piperidine-2,6-dione

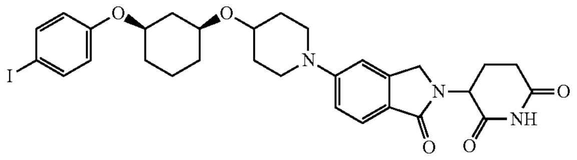 [SMILES: O=C1CCC(N2Cc3cc(N4CCC(O[C@H]5CCC[C@@H](Oc6ccc(I)cc6)C5)CC4)ccc3C2=O)C(=O)N1]

Into a 100-mL round-bottom flask, was placed 3-aminopiperidine-2,6-dione hydrochloride (33 mg, 0.20 mmol, 1.2 equiv), MeOH (1.5 mL), DIEA (44 mg, 0.34 mmol, 2.0 equiv), DCM (25 mL), methyl 2-formyl-4-(4-[[(1S,3R)-3-(4-iodophenoxy)cyclohexyl]-oxy]piperidin-1-yl)benzoate (95 mg, 0.17 mmol, 1.0 equiv) and HOAc (81 mg, 1.35 mmol, 8.0 equiv). After the resulting mixture was stirred for 4 hrs at 35° C. in an oil bath, $NaBH_3CN$ (32 mg, 0.51 mmol, 3.0 equiv) was added into the flask. The resulting mixture was stirred overnight while the temperature was maintained at 35° C. in an oil bath. The reaction was then quenched by the addition of 50 mL of $NaHCO_3$ (aq). The resulting mixture was extracted with 3×150 mL of dichloromethane. The organic phase was combined, dried over anhydrous sodium sulfate, and concentrated under vacuum. The crude product was purified by Flash-Prep-HPLC. This resulted in 65 mg (59.9%) of 3-[5-(4-[[(1S,3R)-3-(4-iodophenoxy)cyclohexyl]oxy]piperidin-1-yl)-1-oxo-3H-isoindol-2-yl]piperidine-2,6-dione as a white solid. LC/MS (ESI) m/z: 644.15 $[M+1]^+$.

Step 10: Preparation of tert-butyl 3-(2,6-difluoro-3-(((R)-3-fluoropyrrolidine)-1-sulfonamido)benzoyl)-5-(4-(((1R,3S)-3-((1-(2-(2,6-dioxopiperidin-3-yl)-1-oxoisoindolin-5-yl)piperidin-4-yl)oxy)cyclohexyl)oxy)phenyl)-1H-pyrrolo[2,3-b]pyridine-1-carboxylate

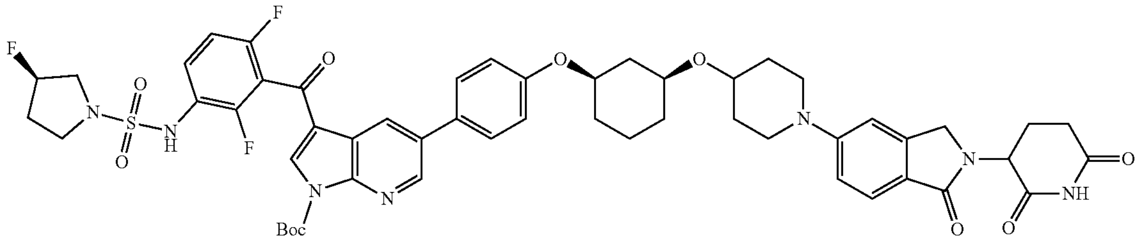 [SMILES: CC(C)(C)OC(=O)n1cc(C(=O)c2c(F)ccc(NS(=O)(=O)N3CC[C@@H](F)C3)c2F)c2cc(-c3ccc(O[C@@H]4CCC[C@H](OC5CCN(c6ccc7c(c6)CN(C6CCC(=O)NC6=O)C7=O)CC5)C4)cc3)cnc21]

Into a 8-mL sealed tube, was placed 3-[5-(4-[[(1S,3R)-3-(4-iodophenoxy)cyclohexyl]oxy]piperidin-1-yl)-1-oxo-3H-isoindol-2-yl]-piperidine-2,6-dione (60 mg, 0.09 mmol, 1.0 equiv), tert-butyl 3-(2,6-difluoro-3-[[(3R)-3-fluoropyrrolidin-1-ylsulfonyl]amino]benzoyl)-5-(4,4,5,5-tetramethyl-1,3,2-dioxaborolan-2-yl)pyrrolo[2,3-b]pyridine-1-carboxylate (91 mg, 0.14 mmol, 1.5 equiv), $K_2CO_3$ (39 mg, 0.28 mmol, 3.0 equiv), $Pd(dtbpf)Cl_2$ (6 mg, 0.009 mmol, 0.1 equiv), dixoane (2.1 mL), and $H_2O$ (0.3 mL). The tube was purged and maintained with an inert atmosphere of nitrogen. The resulting mixture was stirred for 1.5 hrs at 90° C. in an oil bath. The crude product was purified by Flash-Prep-HPLC. This resulted in 75 mg (77.3%) of tert-butyl 3-(2,6-difluoro-3-[[(3R)-3-fluoro-pyrrolidin-1-ylsulfonyl]amino]benzoyl)-5-(4-[[(1R,3S)-3-([1-[2-(2,6-dioxopiperidin-3-yl)-1-oxo-3H-isoindol-5-yl]piperidin-4-yl]oxy)cyclohexyl]oxy]phenyl)pyrrolo[2,3-b]pyridine-1-carboxylate as an off-white solid. LC/MS (ESI) m/z: 1040.35 $[M+1]^+$.

Step 11: Preparation of (3R)—N-(3-(5-(4-(((1R,3S)-3-((1-(2-(2,6-dioxopiperidin-3-yl)-1-oxoisoindolin-5-yl)piperidin-4-yl)oxy)cyclohexyl)oxy)phenyl)-1H-pyrrolo[2,3-b]pyridine-3-carbonyl)-2,4-difluorophenyl)-3-fluoropyrrolidine-1-sulfonamide

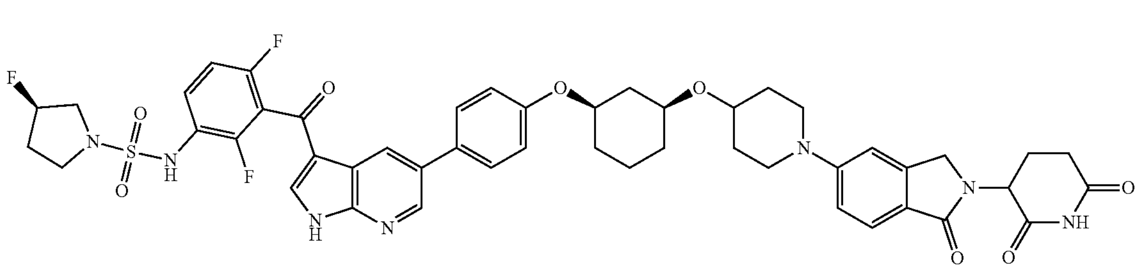 [SMILES: O=C1CCC(N2Cc3cc(N4CCC(O[C@H]5CCC[C@@H](Oc6ccc(-c7cnc8[nH]cc(C(=O)c9c(F)ccc(NS(=O)(=O)N%10CC[C@@H](F)C%10)c9F)c8c7)cc6)C5)CC4)ccc3C2=O)C(=O)N1]

Into a 100-mL round-bottom flask, was placed tert-butyl 3-(2,6-difluoro-3-[[(3R)-3-fluoropyrrolidin-1-ylsulfonyl]amino]benzoyl)-5-(4-[[(1R,3S)-3-([1-[2-(2,6-dioxopiperidin-3-yl)-1-oxo-3H-isoindol-5-yl]piperidin-4-yl]oxy)cyclohexyl]oxy]phenyl)pyrrolo[2,3-b]pyridine-1-carboxylate (75 mg, 0.07 mmol, 1.0 equiv), DCM (10 mL) and TFA (2 mL). The resulting solution was stirred for 1 hr at room temperature, and then concentrated under vacuum. The crude product was purified by Flash-Prep-HPLC. This resulted in 25.0 mg (36.9%) of (3R)—N-[3-[5-(4-[[(1R,3S)-3-([1-[2-(2,6-dioxopiperidin-3-yl)-1-oxo-3H-isoindol-5-yl]piperidin-4-yl]oxy)cyclohexyl]oxy]phenyl)-1H-pyrrolo[2,3-b]pyridine-3-carbonyl]-2,4-difluorophenyl]-3-fluoropyrrolidine-1-sulfonamide as a white solid. LC/MS (ESI) m/z: 940.25 $[M+1]^+$; $^1$H-NMR (400 MHz, DMSO-$d_6$) δ 12.94 (brs, 1H), 10.95 (s, 1H), 9.87 (brs, 1H), 8.68 (s, 1H), 8.57 (brs, 1H), 8.11 (s, 1H), 7.72-7.60 (m, 3H), 7.51 (d, J=8.4 Hz, 1H), 7.29 (t, J=8.8 Hz, 1H), 7.17-7.03 (m, 4H), 5.31 (d, J=53.4 Hz, 1H), 5.05 (d, J=12.6 Hz, 1H), 4.41 (s, 1H), 4.33 (d, J=16.7 Hz, 1H), 4.21 (d, J=16.4 Hz, 1H), 3.79-3.55 (m, 4H), 3.50-3.39 (m, 3H), 3.13-3.03 (m, 2H), 2.98-2.84 (m, 1H), 2.45-2.32 (s, 2H), 2.20-1.85 (m, 8H), 1.84-1.72 (m, 1H), 1.58-1.45 (m, 2H), 1.43-1.05 (m, 5H).

Exemplary Synthesis of (3R)—N-(3-(5-(4-(4-(3-(2-(2,6-dioxopiperidin-3-yl)-1-oxoisoindolin-5-yl)-3-hydroxypropyl)piperazin-1-yl)phenyl)-1H-pyrrolo[2,3-b]pyridine-3-carbonyl)-2,4-difluorophenyl)-3-fluoropyrrolidine-1-sulfonamide (Exemplary Compound 766)

Step 1: Preparation of 3-(5-(3,3-diethoxyprop-1-yn-1-yl)-1-oxoisoindolin-2-yl)piperidine-2,6-dione

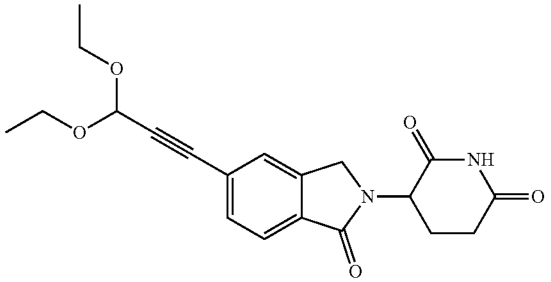 [SMILES: CCOC(C#Cc1ccc2c(c1)CN(C1CCC(=O)NC1=O)C2=O)OCC]

Into a 30-mL sealed tube, was placed 3-(5-bromo-1-oxo-3H-isoindol-2-yl)piperidine-2,6-dione (2.00 g, 6.189 mmol, 1.00 equiv), Dimethyl Formamide (15.00 mL), CuI (0.12 g, 0.619 mmol, 0.10 equiv), Diisopropylethylamine (2.40 g, 18.567 mmol, 3.00 equiv), $Pd(PPh_3)_2C_{1-2}$ (0.43 g, 0.619 mmol, 0.10 equiv), 3,3-diethoxy-propyne (1.19 g, 9.284 mmol, 1.50 equiv). The resulting solution was stirred for 3 h at 65° C. in an oil bath. The reaction was then quenched by the addition of water (20 mL). The resulting solution was extracted with ethyl acetate (2×20 mL). The resulting mixture was washed with brine (2×10 mL). The mixture was dried over anhydrous sodium sulfate. The residue was applied onto a silica gel column with dichloromethane/methanol (10/1). The collected fractions were combined and concentrated under vacuum. This resulted in 1.2 g (52.34%) of 3-[5-(3,3-diethoxyprop-1-yn-1-yl)-1-oxo-3H-isoindol-2-yl]piperidine-2,6-dione as a yellow solid. LC/MS (ESI) m/z: 371.05 $[M+1]^+$.

Step 2: Preparation of 3-(2-(2,6-dioxopiperidin-3-yl)-1-oxoisoindolin-5-yl)propiolaldehyde

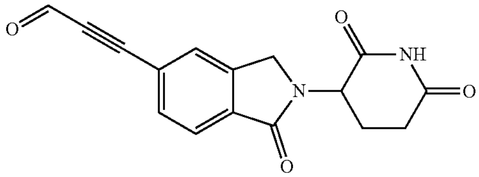 [SMILES: O=CC#Cc1ccc2c(c1)CN(C1CCC(=O)NC1=O)C2=O]

Into a 50-mL round-bottom flask, was placed 3-[5-(3,3-diethoxyprop-1-yn-1-yl)-1-oxo-3H-isoindol-2-yl]piperidine-2,6-dione (200.00 mg, 0.540 mmol, 1.00 equiv), Tetrahydrofuran (5.00 mL), $H_2SO_4$ (5.00 mL, 93.803 mmol, 173.73 equiv). The resulting solution was stirred for 2 h at room temperature. The reaction was then quenched by the addition of water (10 mL). The pH value of the solution was adjusted to 8 with $Na_2CO_3$ (1 mol/L). The resulting solution was extracted with dichloromethane (2×20 mL). The collected fractions were combined and concentrated under vacuum. This resulted in 120 mg (75.01%) of 3-[2-(2,6-dioxopiperidin-3-yl)-1-oxo-3H-isoindol-5-yl]prop-2-ynal as a yellow solid.

Step 3: Preparation of (3R)—N-(3-(5-(4-(4-(3-(2-(2,6-dioxopiperidin-3-yl)-1-oxoisoindolin-5-yl)-3-hydroxypropyl)piperazin-1-yl)phenyl)-1H-pyrrolo[2,3-b]pyridine-3-carbonyl)-2,4-difluorophenyl)-3-fluoropyrrolidine-1-sulfonamide

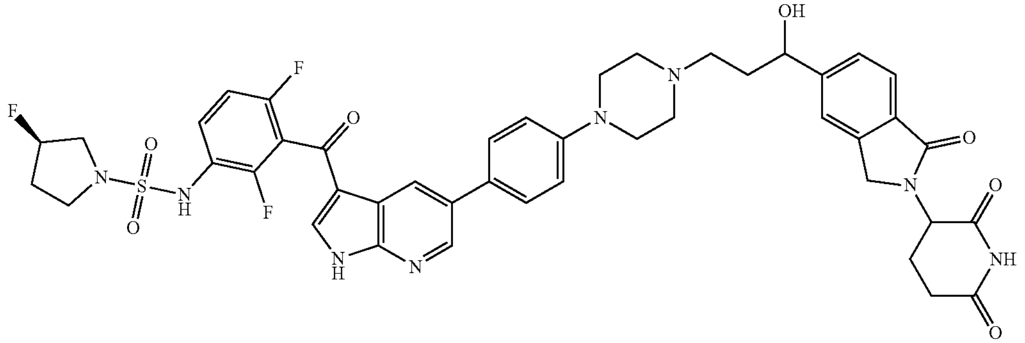 [SMILES: O=C1CCC(N2Cc3cc(C(O)CCN4CCN(c5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]

Into a 50-mL round-bottom flask, was placed (3R)—N-(2,4-difluoro-3-[5-[4-(piperazin-1-yl)phenyl]-1H-pyrrolo[2,3-b]pyridine-3-carbonyl]phenyl)-3-fluoropyrrolidine-1-sulfonamide; trifluoroacetic acid (254.67 mg, 0.365 mmol, 1.20 equiv), dichloromethane (15.00 mL), Diisopropylethylamine (117.78 mg, 0.911 mmol, 3.00 equiv), 3-[2-(2,6-dioxopiperidin-3-yl)-1-oxo-3H-isoindol-5-yl]prop-2-ynal (90.00 mg, 0.304 mmol, 1.00 equiv), HOAc (36.48 mg, 0.608 mmol, 2.00 equiv), $NaBH_3CN$ (57.27 mg, 0.911 mmol, 3.00 equiv). The resulting solution was stirred for overnight at 35° C. in an oil bath. The reaction was then quenched by the addition of water (20 mL). The resulting solution was extracted with dichloromethane (2×20 mL), dried over anhydrous sodium sulfate. The residue was applied onto a silica gel column with dichloromethane/methanol (10/1). The crude product was purified by Prep-HPLC. The collected fractions were combined and concentrated under vacuum. This resulted in 29.5 mg (10.97%) of (3R)—N-(3-[5-[4-(4-[3-[2-(2,6-dioxopiperidin-3-yl)-1-oxo-3H-isoindol-5-yl]-3-hydroxypropyl]piperazin-1-yl)phenyl]-1H-pyrrolo[2,3-b]pyridine-3-carbonyl]-2,4-difluorophenyl)-3-fluoropyrrolidine-1-sulfonamide as a yellow solid. LC/MS (ESI) m/z: 885.20 $[M+1]^+$; $^1$H-NMR (400 MHz, DMSO-$d_6$) δ 12.91 (s, 1H), 10.99 (s, 1H), 9.81 (s, 1H), 8.66 (s, 1H), 8.54 (s, 1H), 8.07 (s, 1H), 7.70-7.50 (m, 6H), 7.29-7.24 (m, 1H), 7.09-7.07 (d, J=8.8 Hz, 2H), 5.62 (s, 1H), 5.37-5.10 (m, 2H), 4.83-4.79 (m, 1H), 4.49-4.31 (m, 2H), 3.48-3.32 (m, 3H), 3.29-3.23 (m, 5H), 2.92-2.86 (m, 1H), 2.63-2.38 (m, 8H), 2.12-2.00 (m, 3H), 1.88-1.83 (m, 2H).

Exemplary Synthesis of (2S,4R)-1-((S)-2-(2-(4-(((S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-2-(hydroxymethyl)piperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Exemplary Compound 773)

Step 1: Preparation of tert-butyl (S)-2-(hydroxymethyl)-4-(4-iodophenyl)piperazine-1-carboxylate

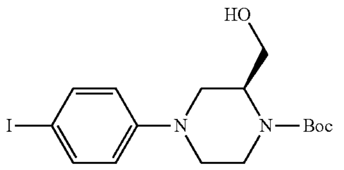 [SMILES: CC(C)(C)OC(=O)N1CCN(c2ccc(I)cc2)C[C@H]1CO]

Into a 250-mL round-bottom flask purged and maintained with an inert atmosphere of nitrogen, was placed a solution of tert-butyl (2S)-2-(hydroxymethyl)piperazine-1-carboxylate (11.4 g, 52.7 mmol, 1.0 equiv) in DMSO (60 mL), 1,4-diiodobenzene (19.1 g, 59.9 mmol, 1.1 equiv), CuI (0.9 g, 5.2 mmol, 0.1 equiv), $K_2CO_3$ (14.5 g, 105.4 mmol, 2.0 equiv), L-Proline (1.2 g, 10.4 mmol, 0.2 equiv). The resulting mixture was stirred for 12 hours at 90° C. in an oil bath. The reaction was then quenched by the addition of 200 mL of water/ice. The resulting solution was extracted with ethyl acetate (200 mL×2). The residue was applied onto a silica gel column eluting with ethyl acetate/petroleum ether (1:1). This resulted in 4.2 g (18.8%) of tert-butyl (2S)-2-(hydroxymethyl)-4-(4-iodophenyl) piperazine-1-carboxylate as a solid. LC/MS (ESI) m/z: 419.05 $[M+1]^+$.

Step 2: Preparation of (S)-(4-(4-iodophenyl)piperazin-2-yl)methanol

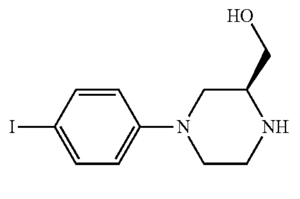 [SMILES: OC[C@@H]1CN(c2ccc(I)cc2)CCN1]

Into a 50-mL round-bottom flask, was placed tert-butyl (2S)-2-(hydroxymethyl)-4-(4-iodophenyl)piperazine-1-carboxylate (4.2 g, 9.9 mmol, 1 equiv) in DCM (20 mL) and TFA (2 mL). The resulting mixture was stirred for 2 hours at room temperature. The resulting mixture was concentrated under reduced pressure. This resulted in 3.2 g of [(2S)-4-(4-iodophenyl) piperazin-2-yl]methanol as a solid. LC/MS (ESI) m/z: 318.95 $[M+1]^+$.

Step 3: Preparation of tert-butyl (S)-4-((2-(hydroxymethyl)-4-(4-iodophenyl)piperazin-1-yl) methyl)piperidine-1-carboxylate

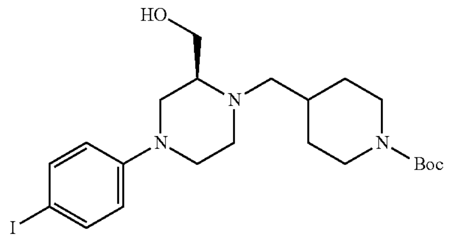 [SMILES: CC(C)(C)OC(=O)N1CCC(CN2CCN(c3ccc(I)cc3)C[C@H]2CO)CC1]

Into a 100-mL round-bottom flask, was placed a solution of [(2S)-4-(4-iodophenyl)piperazin-2-yl]methanol (3.2 g, 9.9 mmol, 1.0 equiv), tert-butyl 4-formylpiperidine-1-carboxylate (2.5 g, 12.1 mmol, 1.2 equiv), trimethyl orthoformate (1.1 g, 9.9 mmol, 1.0 equiv) in DCM (30 mL). The resulting mixture was stirred for 16 hours at room temperature and $NaBH(OAc)_3$ (3.2 g, 15.2 mmol, 1.5 equiv) was added and the reaction was stirred for 3 hours at room temperature. The reaction was then quenched by the addition of 100 mL of water/ice. The resulting solution was extracted with dichloromethane (50 mL×3). The residue was applied onto a silica gel column with ethyl acetate/petroleum ether (1:1). This resulted in 3.6 g (67.1%) of tert-butyl 4-[[(2S)-2-(hydroxymethyl)-4-(4-iodophenyl) piperazin-1-yl] methyl]piperidine-1-carboxylate as a solid. LC/MS (ESI) m/z: 516.15 $[M+1]^+$.

Step 4: Preparation of (S)-(4-(4-iodophenyl)-1-(piperidin-4-ylmethyl)piperazin-2-yl)methanol

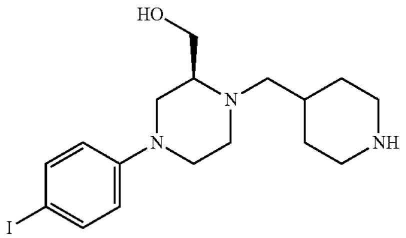 [SMILES: OC[C@@H]1CN(c2ccc(I)cc2)CCN1CC1CCNCC1]

Into a 100-mL round-bottom flask, was placed tert-butyl 4-[[(2S)-2-(hydroxymethyl)-4-(4-iodophenyl)piperazin-1-yl]methyl]piperidine-1-carboxylate (3.6 g, 6.2 mmol, 1.0 equiv in DCM (30 mL) and TFA (3 mL). The resulting mixture was stirred for 2 hours at room temperature. The resulting mixture was concentrated. This resulted in 2.5 g (85.6%) of [(2S)-4-(4-iodophenyl)-1-[(piperidin-4-yl)methyl]piperazin-2-yl]methanol as a solid. LC/MS (ESI) m/z: 416.10 $[M+1]^+$.

Step 5: Preparation of tert-butyl (S)-2-(4-((2-(hydroxymethyl)-4-(4-iodophenyl)piperazin-1-yl)methyl)piperidin-1-yl)acetate

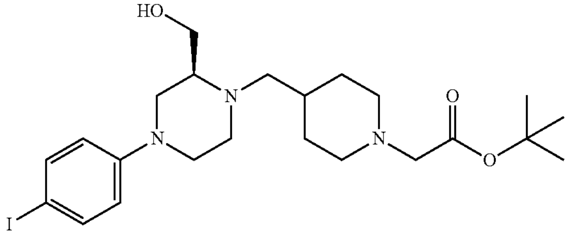 [SMILES: CC(C)(C)OC(=O)CN1CCC(CN2CCN(c3ccc(I)cc3)C[C@H]2CO)CC1]

Into a 100-mL round-bottom flask, was placed [(2S)-4-(4-iodophenyl)-1-[(piperidin-4-yl)methyl]piperazin-2-yl]methanol (2.5 g, 5.7 mmol, 1.0 equiv), tert-butyl 2-bromoacetate (1.1 g, 5.7 mmol, 1.0 equiv), N,N-Diisopropylethylamine (1.4 g, 11.5 mmol, 2.0 equiv) in DCM (30 mL). The resulting mixture was stirred for 16 hours at room temperature. The reaction was then quenched by the addition of 100 mL of water. The resulting solution was extracted with dichloromethane (50 mL×3). The residue was applied onto a silica gel column eluting with ethyl acetate/petroleum ether (1:1). This resulted in 1.2 g (44.2%) of tert-butyl 2-(4-[[(2S)-2-(hydroxymethyl)-4-(4-iodophenyl) piperazin-1-yl]methyl]piperidin-1-yl)acetate as a solid. LC/MS (ESI) m/z: 530.25 $[M+1]^+$.

Step 6: Preparation of tert-butyl (S)-2-(4-((2-(((tert-butyldiphenylsilyl)oxy)methyl)-4-(4-iodophenyl) piperazin-1-yl)methyl)piperidin-1-yl)acetate

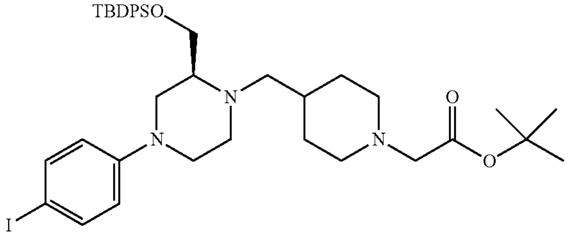

Into a 100-mL round-bottom flask, was placed a solution of tert-butyl 2-(4-[[(2S)-2-(hydroxymethyl)-4-(4-iodophenyl)piperazin-1-yl]methyl]piperidin-1-yl)acetate (1.2 g, 2.4 mmol, 1.0 equiv), tert-butyl(chloro)diphenylsilane (754.6 mg, 2.5 mmol, 1.1 equiv), Imidazole (339.6 mg, 4.9 mmol, 2.0 equiv) in DCM (30 mL). The resulting mixture was stirred for 2 hours at room temperature. The reaction was then quenched by the addition of 50 mL of water. The resulting mixture was extracted with dichloromethane (50 mL×3). The residue was applied onto a silica gel column eluting with ethyl acetate/petroleum ether (1:1). This resulted in 920.0 mg (61.1%) of tert-butyl 2-(4-[[(2S)-2-[[(tert-butyldiphenylsilyl) oxy]methyl]-4-(4-iodophenyl) piperazin-1-yl]methyl]piperidin-1-yl)acetate as a solid. LC/MS (ESI) m/z: 768.35 $[M+1]^+$.

Step 7: Preparation of (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide

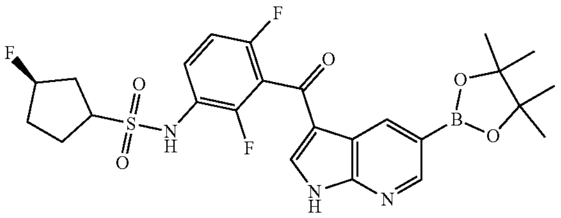 [SMILES: CC1(C)OB(c2cnc3[nH]cc(C(=O)c4c(F)ccc(NS(=O)(=O)C5CC[C@@H](F)C5)c4F)c3c2)OC1(C)C]

Into a 250-mL round-bottom flask purged and maintained with an inert atmosphere of nitrogen, was placed (3R)—N-(3-[5-bromo-1H-pyrrolo[2,3-b]pyridine-3-carbonyl]-2,4-difluorophenyl)-3-fluoropyrrolidine-1-sulfonamide (5 g, 9.93 mmol, 1.0 equiv), bis(pinacolato)diboron (13 g, 51.19 mmol, 5.15 equiv), KOAc (5 g, 50.94 mmol, 5.13 equiv), $Pd(dppf)Cl_2$ (1.7 g, 2.32 mmol, 0.23 equiv), dioxane (100 mL). The resulting solution was stirred for 16 h at 100° C. in an oil bath under the nitrogen atmosphere. The resulting mixture was concentrated under the reduced pressure. The residue was applied onto a silica gel column with dichloromethane/ethyl acetate (1:1). This resulted in 4.05 g (74%) of (3R)—N-[2,4-difluoro-3-[5-(4,4,5,5-tetramethyl-1,3,2-dioxaborolan-2-yl)-1H-pyrrolo[2,3-b]pyridine-3-carbonyl] phenyl]-3-fluoropyrrolidine-1-sulfonamide as a light brown solid. LC/MS (ESI) m/z: 551.10 $[M+1]^+$.

Step 8: Preparation of tert-butyl 2-(4-(((S)-2-(((tert-butyldiphenylsilyl)oxy)methyl)-4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetate

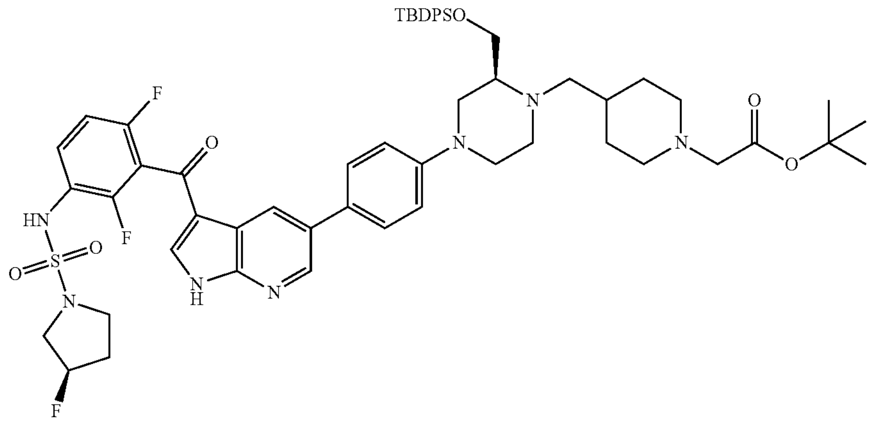

Into a 30-mL sealed tube purged and maintained with an inert atmosphere of nitrogen, was placed a solution of tert-butyl 2-(4-[[(2S)-2-[[(tert-butyldiphenylsilyl)oxy]methyl]-4-(4-iodophenyl)piperazin-1-yl]methyl]piperidin-1-yl)acetate (920.0 mg, 1.1 mmol, 1.0 equiv) in dioxane/$H_2O$ (4/1=10 mL), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (1.0 mg, 1.9 mmol, 1.5 equiv), Potassiumphosphatetribasic (796.2 mg, 3.4 mmol, 3.0 equiv), Pd(DtBPF)$Cl_2$ (162.9 mg, 0.3 mmol, 0.2 equiv). The final reaction mixture was irradiated with microwave radiation for 1 hour at 95° C. under $N_2$. The resulting mixture was concentrated under reduced pressure. The residue was applied onto a silica gel column with dichloromethane/methanol (15:1). This resulted in 465.0 mg of tert-butyl 2-(4-[[(2S)-2-[[(tert-butyldiphenylsilyl)oxy]methyl]-4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetate as a solid. LC/MS (ESI) m/z: 1064.40 $[M+1]^+$.

Step 9: Preparation of 2-(4-(((S)-2-(((tert-butyldiphenylsilyl)oxy)methyl)-4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetic acid

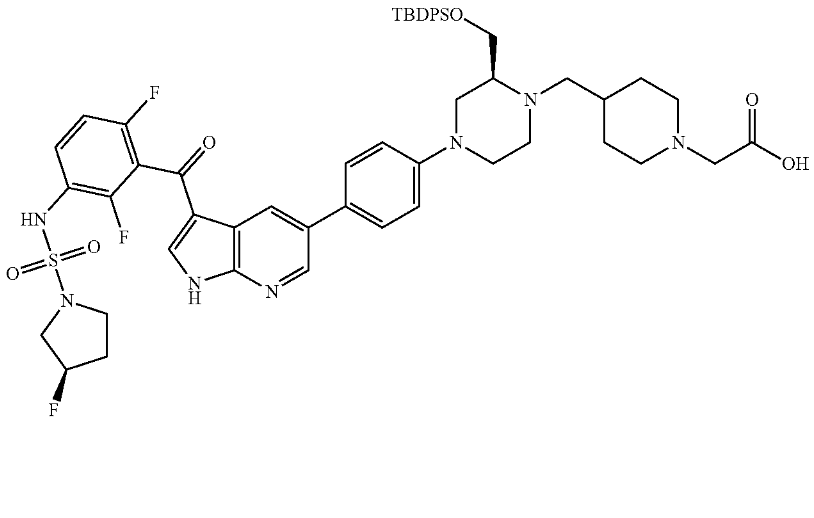

Into a 50-mL round-bottom flask, was placed a solution of tert-butyl 2-(4-[[(2S)-2-[[(tert-butyldiphenylsilyl)oxy]methyl]-4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetate (465.0 mg, 0.5 mmol, 1.0 equiv) in DCM (10 mL) and TFA (2.0 mL). The resulting mixture was stirred for 4 hours at room temperature. The resulting mixture was concentrated under reduced pressure. This resulted in 415.0 mg (98.0%) of 2-(4-[[(2S)-2-[[(tert-butyldiphenylsilyl) oxy]methyl]-4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid as a solid. LC/MS (ESI) m/z: 1008.45 $[M+1]^+$.

Step 10: Preparation of (2S,4R)-1-((S)-2-(2-(4-(((S)-2-(((tert-butyldiphenylsilyl)oxy)methyl)-4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

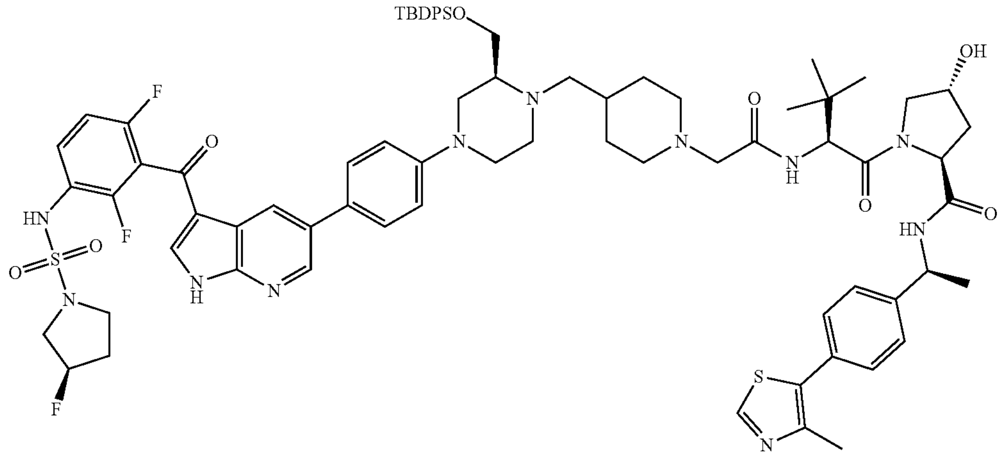

Into a 50-mL round-bottom flask, was placed a solution of 2-(4-[[(2S)-2-[[(tert-butyldiphenylsilyl)oxy]methyl]-4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (415.0 mg, 0.5 mmol, 1.0 equiv), (2S,4R)-1-[(2S)-2-amino-3,3-dimethylbutanoyl]-4-hydroxy-N-[(1S)-1-[4-(4-methyl-1,3-thiazol-5-yl) phenyl]ethyl]pyrrolidine-2-carboxamide (225.2 mg, 0.5 mmol, 1.1 equiv), N,N-Diisopropylethylamine (120.9 mg, 0.8 mmol, 2.0 equiv), BOP (249.4 mg, 0.6 mmol, 1.3 equiv) in DMF (10 mL). The resulting mixture was stirred for 30 min at room temperature. The reaction was then quenched by the addition of 50 mL of water. The resulting solution was extracted with ethyl acetate (50 mL×3). The residue was applied onto a silica gel column with dichloromethane/methanol (10:1). This resulted in 365.0 mg (63.3%) of (2S,4R)-1-[(2S)-2-[2-(4-[[(2S)-2-[[(tert-butyl diphenylsilyl) oxy]methyl]-4-(4-[3-[2,6-difluoro-3-([[(3R)-3-fluoropyrrolidin-1-yl]sulfonyl]amino) benzoyl]-1H-pyrrolo[2,3-b]pyridin-5-yl]phenyl)piperazin-1-yl]methyl]piperidin-1-yl)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide as a solid. LC/MS (ESI) m/z: 1435.75 $[M+1]^+$.

Step 11: Preparation of (2S,4R)-1-((S)-2-(2-(4-(((S)-4-(4-(3-(2,6-difluoro-3-(((R)-3-fluoropyrrolidine)-1-sulfonamido)benzoyl)-1H-pyrrolo[2,3-b]pyridin-5-yl)phenyl)-2-(hydroxymethyl)piperazin-1-yl)methyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

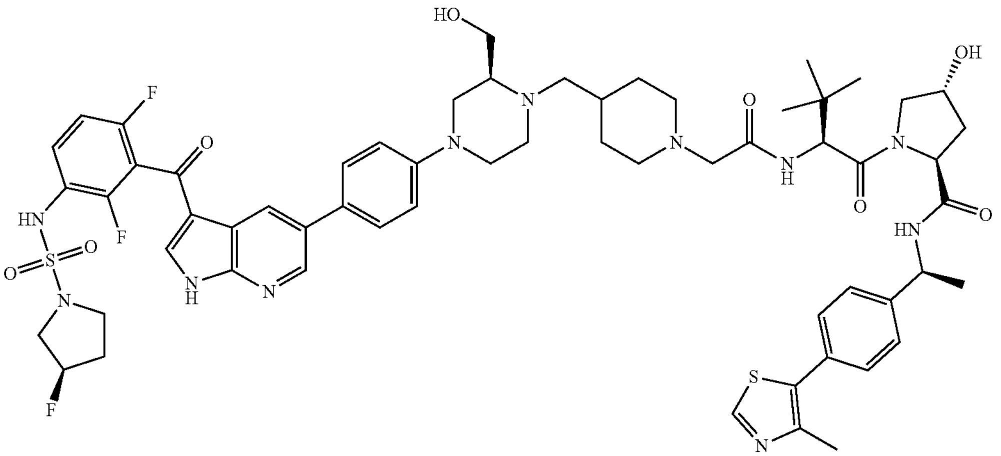 [SMILES: Cc1ncsc1-c1ccc([C@H](C)NC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)C[C@H]3CO)CC2)C(C)(C)C)cc1]

Into a 50-mL round-bottom flask, was placed a solution of (2S,4R)-1-[(2S)-2-[2-(4-[[(2S)-2-[[(tert-butyldiphenylsilyl)oxy]methyl]-4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide (365.0 mg, 0.2 mmol, 1.0 equiv) and CsF (88.2 mg, 0.4 mmol, 2.0 equiv) in DMSO (10 mL). The resulting mixture was stirred for 48 hours at 40° C. in an oil bath. The reaction was then quenched by the addition of 50 mL of water. The resulting solution was extracted with ethyl acetate (50 mL×3) concentrated. The crude product was purified by Prep-HPLC. This resulted in 69.8 mg (23.9%) of (2S,4R)-1-[(2S)-2-[2-(4-[[(2S)-4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)-2-(hydroxymethyl)piperazin-1-yl]methyl]piperidin-1-yl)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide as a solid. LC/MS (ESI) m/z: 1196.55 $[M+1]^+$; $^1$H-NMR (400 MHz, DMSO-$d_6$) δ 12.90 (s, 1H), 8.98 (s, 1H), 8.72 (s, 1H), 8.60-8.53 (m, 1H), 8.10 (s, 1H), 7.78-7.72 (m, 1H), 7.62-7.55 (m, 3H), 7.47 (d, J=8.0 Hz, 2H), 7.35 (d, J=9.5 Hz, 2H), 7.25-7.16 (m, 1H), 7.10-7.08 (m, 2H), 5.35-5.20 (m, 1H), 5.12 (s, 1H), 4.93-4.80 (m, 1H), 4.65-4.60 (m, 1H), 4.51-4.45 (m, 1H), 4.30-4.20 (m, 1H), 3.75-3.70 (m, 1H), 3.65-3.57 (m, 2H), 3.55-3.52 (m, 3H), 3.45-3.33 (m, 3H), 3.32-3.16 (m, 1H), 3.11-3.02 (m, 2H), 3.00-2.56 (m, 7H), 2.50-2.46 (m, 4H), 2.33 (s, 1H), 2.29-2.07 (m, 6H), 1.90-1.70 (m, 3H), 1.51 (m, 1H), 1.38 (s, 3H), 1.25-1.06 (s, 3H), 0.94 (s, 9H).

Exemplary Synthesis of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N—((S)-1-(4-(pyridin-4-yl)phenyl)ethyl)pyrrolidine-2-carboxamide (Exemplary Compound 776)

Step 1: Preparation of methyl (2S,4R)-4-hydroxypyrrolidine-2-carboxylate

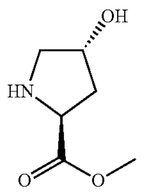

To a mixture of 1-tert-butyl 2-methyl (2S,4R)-4-hydroxypyrrolidine-1,2-dicarboxylate (10 g, 40.77 mmol, 1 eq) in dichloromethane (10 mL) was added hydrogen chloride/dioxane (4 M, 10 eq) at 20° C. The mixture stirred at 20° C. for 1 h. The mixture was concentrated under reduced pressure to give methyl (2S,4R)-4-hydroxypyrrolidine-2-carboxylate (7.4 g, hydrochloride) as a yellow oil.

Step 2: Preparation of methyl (2S,4R)-1-((S)-2-((tert-butoxycarbonyl)amino)-3,3-dimethylbutanoyl)-4-hydroxypyrrolidine-2-carboxylate

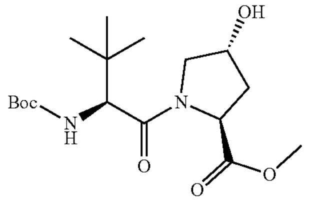 [SMILES: COC(=O)[C@@H]1C[C@@H](O)CN1C(=O)[C@@H](NC(=O)OC(C)(C)C)C(C)(C)C]

To a mixture of methyl (2S,4R)-4-hydroxypyrrolidine-2-carboxylate (7.4 g, 40.75 mmol, 1 eq, hydrochloride), (2S)-2-(tert-butoxycarbonylamino)-3,3-dimethyl-butanoic acid (9.42 g, 40.75 mmol, 1 eq) in dimethylformamide (200 mL) was added carbodiimide hydrochloride (15.62 g, 81.49 mmol, 2 eq), Hydroxybenzotriazole (6.61 g, 48.89 mmol, 1.2 eq) and Diisopropylethylamine (31.60 g, 244.47 mmol, 6 eq). The mixture stirred at 20° C. for 12 h. The mixture was quenched by addition water (1000 mL), extracted with ethyl acetate (200 mL*4), the combined organic phase washed with brine (100 mL*2), dried over anhydrous sodium sulfate, filtered and concentrated under reduced pressure. The residue was purified by silica gel column chromatography (petroleum ether:ethyl acetate=5:1-1:1). Compound methyl (2S,4R)-1-[(2S)-2-(tert-butoxycarbonylamino)-3,3-dimethyl-butanoyl]-4-hydroxy-pyrrolidine-2-carboxylate (13.5 g, 37.66 mmol, 92% yield) was obtained as a yellow oil. LC/MS (ESI) m/z: 381.2 $[M+23]^+$.

Step 3: Preparation of methyl (2S,4R)-1-((S)-2-amino-3,3-dimethylbutanoyl)-4-hydroxypyrrolidine-2-carboxylate

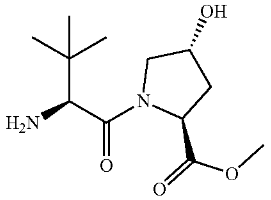 [SMILES: COC(=O)[C@@H]1C[C@@H](O)CN1C(=O)[C@@H](N)C(C)(C)C]

To a mixture of methyl (2S,4R)-1-[(2S)-2-(tert-butoxycarbonylamino)-3,3-dimethyl-butanoyl]-4-hydroxy-pyrrolidine-2-carboxylate (13 g, 36.27 mmol, 1 eq) in dichloromethane (5 mL) was added hydrochloride/dioxane (4 M, 10 eq). The mixture stirred at 20° C. for 20 minutes. The mixture was concentrated under reduced pressure to give methyl (2S,4R)-1-[(2S)-2-amino-3,3-dimethyl-butanoyl]-4-hydroxy-pyrrolidine-2-carboxylate (11 g, hydrochloride) as a colorless oil.

Step 4: Preparation of tert-butyl 4-(2-(((S)-1-((2S,4R)-4-hydroxy-2-(methoxycarbonyl)pyrrolidin-1-yl)-3,3-di methyl-1-oxobutan-2-yl)amino)-2-oxoethyl)piperazine-1-carboxylate

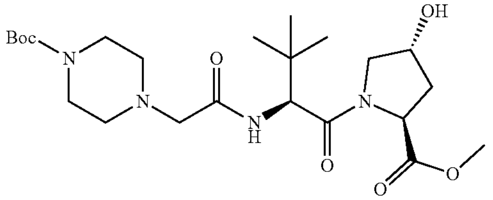 [SMILES: COC(=O)[C@@H]1C[C@@H](O)CN1C(=O)[C@@H](NC(=O)CN1CCN(C(=O)OC(C)(C)C)CC1)C(C)(C)C]

To a mixture of methyl (2S,4R)-1-[(2S)-2-amino-3,3-dimethyl-butanoyl]-4-hydroxy-pyrrolidine-2-carboxylate (11 g, 37.32 mmol, 1 eq, hydrochloride), 2-(4-tert-butoxycarbonylpiperazin-1-yl)acetic acid (10.03 g, 41.05 mmol, 1.1 eq) in dimethylformamide (400 mL) was added carbonamide hydrochloride (14.31 g, 74.63 mmol, 2 eq), Hydroxybenzotriazole (6.05 g, 44.78 mmol, 1.2 eq) and Diisopropylethylamine (28.94 g, 223.90 mmol, 6 eq). The mixture stirred at 20° C. for 12 h. The mixture was quenched by addition water (1000 mL), extracted with ethyl acetate (100 mL*6), the combined organic phase washed with brine (100 mL*2), dried over anhydrous sodium sulfate, filtered and concentrated under reduced pressure. The residue was purified by silica gel column chromatography (petroleum ether:ethyl acetate=3:1-0:1). Compound tert-butyl 4-[2-[[(1S)-1-[(2S,4R)-4-hydroxy-2-methoxycarbonyl-pyrrolidine-1-carbonyl]-2,2-dimethyl-propyl]amino]-2-oxo-ethyl]piperazine-1-carboxylate (5 g, 10.32 mmol, 27% yield) was obtained as a white solid. LC/MS (ESI) m/z: 485.3 $[M+1]^+$.

Step 5: Preparation of methyl (2S,4R)-1-((S)-3,3-dimethyl-2-(2-(piperazin-1-yl)acetamido)butanoyl)-4-hydroxypyrrolidine-2-carboxylate

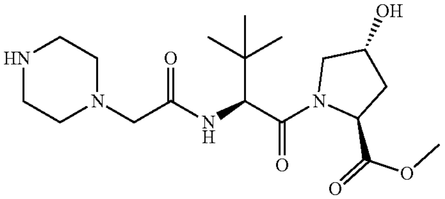 [SMILES: COC(=O)[C@@H]1C[C@@H](O)CN1C(=O)[C@@H](NC(=O)CN1CCNCC1)C(C)(C)C]

To a mixture of tert-butyl 4-[2-[[(1S)-1-[(2S,4R)-4-hydroxy-2-methoxycarbonyl-pyrrolidine-1-carbonyl]-2,2-dimethyl-propyl]amino]-2-oxo-ethyl]piperazine-1-carboxylate (600 mg, 1.24 mmol, 1 eq) in dichloromethane (50 mL) was added hydrogen chloride/dioxane (4 M, 10 eq). The mixture stirred at 25° C. for 30 min. The mixture was concentrated under reduced pressure to give methyl (2S,4R)-1-[(2S)-3,3-dimethyl-2-[(2-piperazin-1-ylacetyl)amino]butanoyl]-4-hydroxy-pyrrolidine-2-carboxylate (520 mg, hydrochloride) as a white solid. LC/MS (ESI) m/z: 385.1 $[M+1]^+$.

Step 6: Preparation of methyl (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxylate

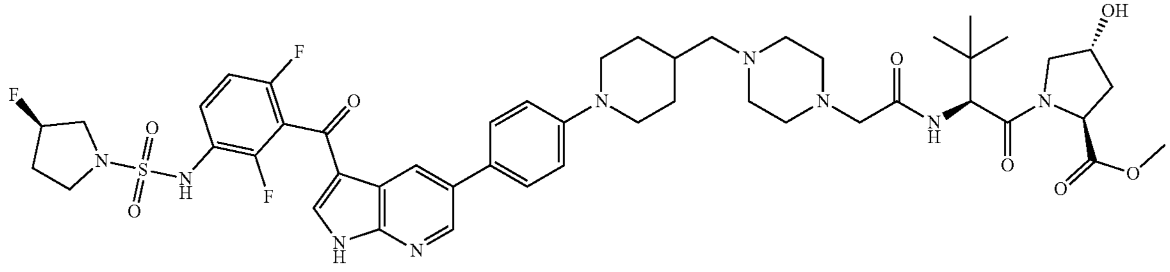 [SMILES: COC(=O)[C@@H]1C[C@@H](O)CN1C(=O)[C@@H](NC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1)C(C)(C)C]

To a mixture of methyl (2S,4R)-1-[(2S)-3,3-dimethyl-2-[(2-piperazin-1-ylacetyl)amino]butanoyl]-4-hydroxy-pyrrolidine-2-carboxylate (520 mg, 1.24 mmol, 1.2 eq, hydrochloride) in dichloroethane (20 mL) was added triethylamine (625 mg, 6.18 mmol, 6 eq). The mixture stirred at 25° C. for 15 min. Then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (629 mg, 1.03 mmol, 1 eq) was added to the reaction and the mixture stirred at 25° C. for 15 min. Then Sodium borohydride acetate (436 mg, 2.06 mmol, 2 eq) was added to the reaction mixture and the mixture stirred at 25° C. for 12 h. The mixture was quenched by addition water (150 mL), extracted with ethyl acetate (30 mL*5), the combined organic phase washed with brine (30 mL), dried over anhydrous sodium sulfate, filtered and concentrated under reduced pressure. The residue was purified by silica gel column chromatography (petroleum ether:ethyl acetate=5:1-0:1). Compound methyl (2S,4R)-1-[(2S)-2-[[2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]acetyl]amino]-3,3-dimethyl-butanoyl]-4-hydroxy-pyrrolidine-2-carboxylate (500 mg, 0.51 mmol, 49% yield) was obtained as a white solid. LC/MS (ESI) m/z: 980.5 [M]$^+$.

Step 7: Preparation of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxypyrrolidine-2-carboxylic acid

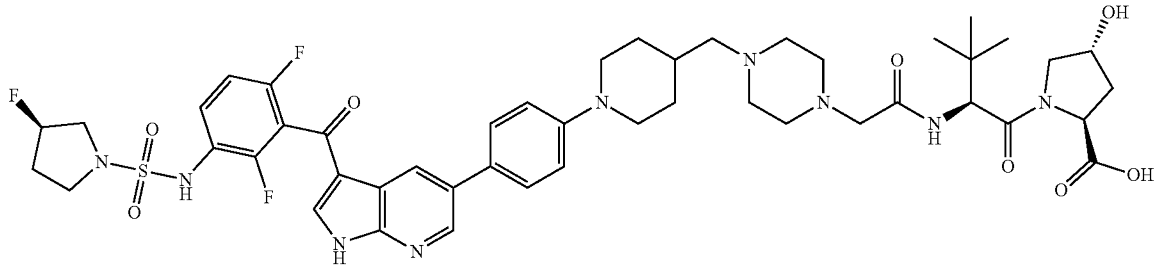 [SMILES: CC(C)(C)[C@H](NC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1)C(=O)N1C[C@H](O)C[C@H]1C(=O)O]

To a mixture of methyl (2S,4R)-1-[(2S)-2-[[2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]acetyl]amino]-3,3-dimethyl-butanoyl]-4-hydroxy-pyrrolidine-2-carboxylate (500 mg, 0.51 mmol, 1 eq) in methanol (10 mL) was added sodium hydroxide (4 M, 4 eq). The mixture stirred at 40° C. for 1 h. The mixture was concentrated under reduced pressure to remove the methanol, and the residue was adjusted to pH=3~4. The solution was purified by prep-HPLC. Compound (2S,4R)-1-[(2S)-2-[[2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl] piperazin-1-yl]acetyl]amino]-3,3-dimethyl-butanoyl]-4-hydroxy-pyrrolidine-2-carboxylic acid (400 mg, 0.41 mmol, 81% yield) was obtained as a yellow solid. LC/MS (ESI) m/z: 966.1 $[M]^+$.

Step 8: Preparation of tert-butyl (S)-(1-(4-(pyridin-4-yl)phenyl)ethyl)carbamate

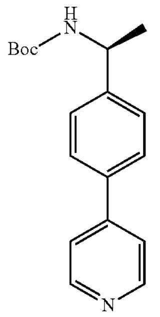 [SMILES: C[C@H](NC(=O)OC(C)(C)C)c1ccc(-c2ccncc2)cc1]

A mixture of tert-butyl N-[(1S)-1-(4-bromophenyl)ethyl] carbamate (500 mg, 1.67 mmol, 1 eq), 4-pyridylboronic acid (245 mg, 2.00 mmol, 1.2 eq), [1,1-Bis(diphenylphosphino) ferrocene]dichloropalladium(II) (121 mg, 0.16 mmol, 0.1 eq) and potassium phosphate (707 mg, 3.33 mmol, 2 eq) in dioxane (50 mL) and water (5 mL) was de-gassed and then heated to 80° C. for 12 hours under nitrogen. The mixture was filtered and concentrated under reduced pressure. The residue was purified by silica gel column chromatography (petroleum ether:ethyl acetate=15:1-5:1). Compound tert-butyl N-[(1S)-1-[4-(4-pyridyl)phenyl]ethyl]carbamate (400 mg, 1.34 mmol, 80% yield) was obtained as a white solid. LC/MS (ESI) m/z: 299.2 $[M+1]^+$.

Step 9: Preparation of (S)-1-(4-(pyridin-4-yl)phenyl)ethan-1-amine

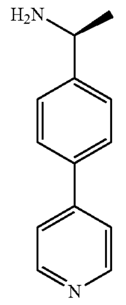

To a mixture of tert-butyl N-[(1S)-1-[4-(4-pyridyl)phenyl]ethyl]carbamate (400 mg, 1.34 mmol, 1 eq) in dichloromethane (10 mL) was added hydrogen chloride/dioxane (4 M, 3.35 mL, 10 eq). The mixture stirred at 25° C. for 30 min. The mixture was concentrated under reduced pressure to give (1S)-1-[4-(4-pyridyl)phenyl]ethanamine (380 mg, hydrochloride) as a white solid. LC/MS (ESI) m/z: 199.1 $[M+1]^+$.

Step 10: Preparation of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) acetamido)-3,3-dimethylbutanoyl)-4-hydroxy-N—((S)-1-(4-(pyridin-4-yl)phenyl)ethyl)pyrrolidine-2-carboxamide

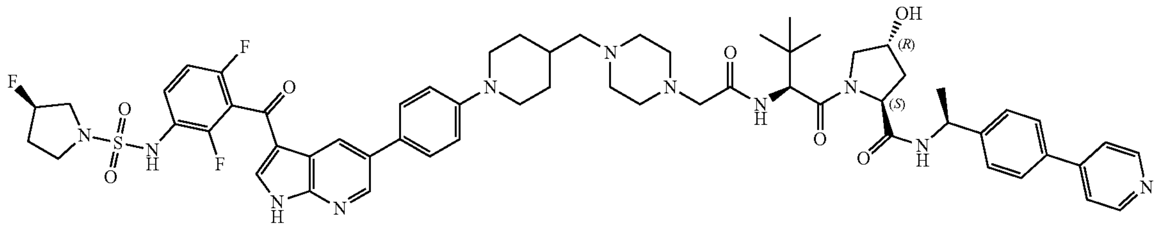

To a mixture of (1S)-1-[4-(4-pyridyl)phenyl]ethanamine (54 mg, 0.23 mmol, 1.5 eq, hydrochloride), (2S,4R)-1-[(2S)-2-[[2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]acetyl] amino]-3,3-dimethyl-butanoyl]-4-hydroxy-pyrrolidine-2-carboxylic acid (150 mg, 0.15 mmol, 1 eq) in dimethylformamide (10 mL) was added Hydroxybenzotriazole (25 mg, 0.18 mmol, 1.2 eq), diisopropylethylamine (120 mg, 0.93 mmol, 6 eq) and carbodiimide hydrochloride (59 mg, 0.31 mmol, 2 eq). The mixture stirred at 25° C. for 12 h. The mixture was quenched by addition water (100 mL), extracted with ethyl acetate (30 mL*3), the combined organic phase washed with brine (30 mL), dried over anhydrous sodium sulfate, filtered and concentrated under reduced pressure. The residue was purified by prep-HPLC.

Compound (2S,4R)-1-[(2S)-2-[[2-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]acetyl]amino]-3,3-dimethyl-butanoyl]-4-hydroxy-N-[(1S)-1-[4-(4-pyridyl)phenyl]ethyl]pyrrolidine-2-carboxamide (61 mg, 0.04 mmol, 31% yield, 99% purity, 2Fomate) was obtained as a yellow solid. LC/MS (ESI) m/z: 573.8 $[M/2+1]^+$; $^1$H-NMR (400 MHz, DMSO-$d_6$) δ 13.14-12.31 (m, 1H), 8.68-8.59 (m, 3H), 8.56-8.43 (m, 2H), 8.22-8.13 (m, 2H), 8.06 (s, 1H), 7.81-7.67 (m, 5H), 7.64-7.54 (m, 3H), 7.47-7.37 (m, 2H), 7.25 (t, J=9.2 Hz, 1H), 7.07 (d, J=8.8 Hz, 2H), 5.41-5.19 (m, 1H), 5.18-4.87 (m, 2H), 4.55-4.37 (m, 2H), 4.31-4.23 (m, 1H), 3.83-3.75 (m, 2H), 3.63-3.53 (m, 6H), 3.01-2.94 (m, 2H), 2.78-2.68 (m, 3H), 2.44 (s, 3H), 2.21 (d, J=6.8 Hz, 3H), 2.14-1.99 (m, 4H), 1.86-1.66 (m, 5H), 1.48-1.37 (m, 3H), 1.30-1.13 (m, 3H), 0.95 (s, 9H).

Exemplary Synthesis of (2S,4R)-1-(2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)pyridin-3-yl)-3-methylbutanoyl)-4-hydroxy-N—((S)-1-(4-(4-methylthiazol-5-yl)phenyl)ethyl)pyrrolidine-2-carboxamide (Exemplary Compound 752)

Step 1: Preparation of ethyl 2-(5-bromopyridin-3-yl)acetate

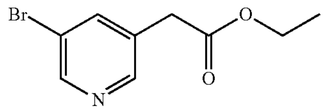

To a solution of 2-(5-bromopyridin-3-yl)acetonitrile (510 mg, 2.6 mmol) in ethanol (13 mL) was added con.$H_2SO_4$ (4.0 mL). The reaction was stirred at 90° C. for 16 h. After the reaction was completed, the mixture's pH was adjusted to 10 with saturated $NaHCO_3$, then extracted with ethyl acetate (10×3 mL), washed with brine (5 mL). The organic phase was concentrated under vacuum. The residue was purified by column chromatography (PE:EA=2:1-1:5) to afford ethyl 2-(5-bromopyridin-3-yl)acetate (550 mg) as a yellow oil. LC/MS (ESI) m/z: 244.1 $[M+1]^+$.

Step 2: Preparation of ethyl 2-(5-bromopyridin-3-yl)-3-methylbutanoate

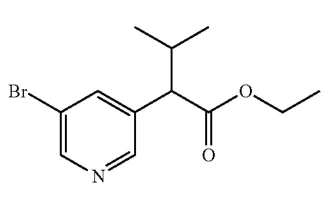 [SMILES: CCOC(=O)C(c1cncc(Br)c1)C(C)C]

A solution of ethyl 2-(5-bromopyridin-3-yl)acetate (100 mg, 0.41 mmol) in anhydrous THF 1 mL was cooled to −78° C., LiHMDS (0.45 mL, 0.45 mmol) was added dropwise. After 30 min, 2-iodopropane (76.5 mg, 0.45 mmol) was added. The mixture was stirred at −78° C. for 1 h, then left it to room temperature for 12 h. After the reaction was completed, it was quenched with water at 0° C. The mixture was extracted with EA (5 mL*3) and washed with brine (2 mL). The organic phase was concentrated under vacuum. The residue was purified by column chromatography (PE: EA=1:5~1:1) to afford 2-(5-bromopyridin-3-yl)-3-methylbutanoate (320 mg) as a yellow oil. LC/MS (ESI) m/z: 287.0 $[M+1]^+$.

Step 3: Preparation of tert-butyl 4-(5-(1-ethoxy-3-methyl-1-oxobutan-2-yl)pyridin-3-yl)piperazine-1-carboxylate

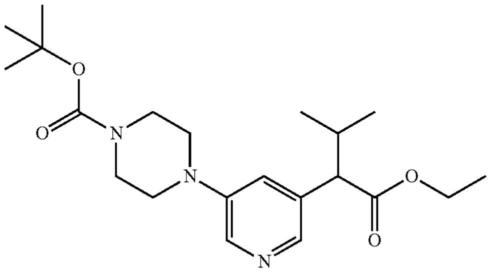 [SMILES: CCOC(=O)C(c1cncc(N2CCN(C(=O)OC(C)(C)C)CC2)c1)C(C)C]

A mixture of 2-(5-bromopyridin-3-yl)-3-methylbutanoate (220 mg, 0.77 mmol), tert-butyl piperazine-1-carboxylate (216 mg, 1.16 mmol), Ru(phos) (145 mg, 0.31 mmol), $Cs_2CO_3$ (378 mg, 1.16 mmol) and $Pd(OAc)_2$ (34 mg, 0.15 mmol) in toluene (4 mL) was stirred at 100° C. for 4 h under $N_2$. The mixture was concentrated and purified by chromatography column with PE:EA=1:10-1:1 to give the tert-butyl 4-(5-(1-ethoxy-3-methyl-1-oxobutan-2-yl)pyridin-3-yl)piperazine-1-carboxylate (280 mg) as a white solid. LC/MS (ESI) m/z: 392.2 $[M+1]^+$.

Step 4: Preparation of ethyl 3-methyl-2-(5-(piperazin-1-yl)pyridin-3-yl)butanoate

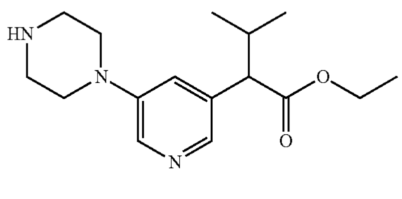 [SMILES: CCOC(=O)C(c1cncc(N2CCNCC2)c1)C(C)C]

Into a 50-mL round-bottom flask, was placed a solution of tert-butyl 4-[5-(1-ethoxy-3-methyl-1-oxobutan-2-yl)pyridin-3-yl]piperazine-1-carboxylate (450 mg, 1.149 mmol, 1 equiv) in dioxane (15 mL), to which HCl in 1,4-dioxane ((4 M, 15 mL) was added. The resulting solution was stirred for 7 h at room temperature. The resulting mixture was concentrated under reduced pressure. This resulted in 460 mg of ethyl 3-methyl-2-[5-(piperazin-1-yl)pyridin-3-yl]butanoate hydrochloride as a yellow solid. LC/MS (ESI) m/z: 292.20 $[M+1]^+$.

Step 5: Preparation of ethyl 2-(5-(4-((1-(4-bromophenyl)piperidin-4-yl)methyl)piperazin-1-yl)pyridin-3-yl)-3-methylbutanoate

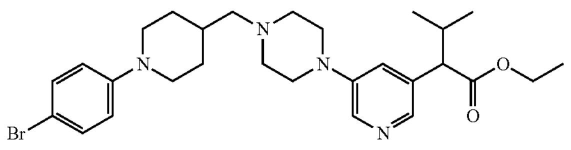 [SMILES: CCOC(=O)C(c1cncc(N2CCN(CC3CCN(c4ccc(Br)cc4)CC3)CC2)c1)C(C)C]

Into a 100-mL round-bottom flask, was placed a solution of ethyl 3-methyl-2-[5-(piperazin-1-yl)pyridin-3-yl]butanoate (146.70 mg, 0.503 mmol, 1 equiv), DIEA (195.20 mg, 1.510 mmol, 3 equiv), 1-(4-bromophenyl)piperidine-4-carbaldehyde (135 mg, 0.503 mmol, 1 equiv), acetyl ethaneperoxoate sodioboranyl acetate (320.10 mg, 1.510 mmol, 3 equiv) in DCM (50 mL). The resulting solution was stirred for 8 h at room temperature. The reaction was then quenched by the addition of 20 mL of water/ice. The resulting solution was extracted with (40 mL×3) of ethyl acetate and the organic layers combined. The resulting mixture was washed with (20 mL×1) of brine, dried over anhydrous sodium sulfate and concentrated under reduced pressure. The residue was applied onto a silica gel column eluting with dichloromethane/methanol (20/1). The collected fractions were combined and concentrated under vacuum. This resulted in 105 mg (38.37%) of ethyl 2-[5-(4-[[1-(4-bromophenyl)piperidin-4-yl]methyl]piperazin-1-yl)pyridin-3-yl]-3-methylbutanoate as a yellow solid. LC/MS (ESI) m/z: 545.30 $[M+1]^+$.

Step 6: Preparation of ethyl 2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)pyridin-3-yl)-3-methylbutanoate

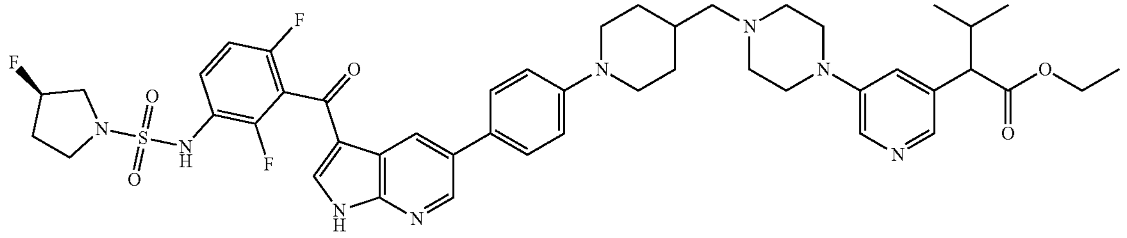 [SMILES: CCOC(=O)C(c1cncc(N2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)c1)C(C)C]

Into a 20-mL sealed tube purged and maintained with an inert atmosphere of nitrogen, was placed ethyl 2-[5-(4-[[1-(4-bromophenyl)piperidin-4-yl]methyl]piperazin-1-yl)pyridin-3-yl]-3-methylbutanoate (105 mg, 0.193 mmol, 1 equiv), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (159.47 mg, 0.290 mmol, 1.50 equiv), $K_3PO_4$ (123.01 mg, 0.580 mmol, 3.00 equiv) in $H_2O$ (2 ml), $Pd(DtBPF)Cl_2$ (62.95 mg, 0.097 mmol, 0.5 equiv) in dioxane (8 ml). The final reaction mixture was irradiated with microwave radiation for 1 h at 85° C. The reaction was then quenched by the addition of 10 mL of water/ice. The resulting solution was extracted with (40 mL×3) of ethyl acetate. The combined organic layer was washed with (20 mL×1) of brine, dried over anhydrous sodium sulfate and concentrated. The residue was applied onto a silica gel column eluting with dichloromethane/methanol (10/1). This resulted in 31 mg of ethyl 2-[5-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)pyridin-3-yl]-3-methylbutanoate as a brown solid. LC/MS (ESI) m/z: 887.20 $[M+1]^+$.

Step 7: Preparation of 2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)pyridin-3-yl)-3-methylbutanoic acid

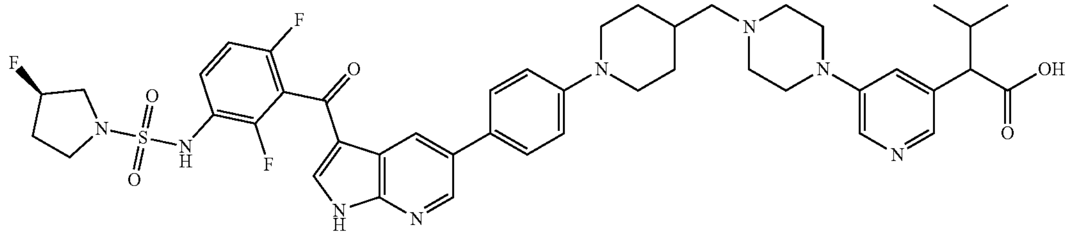 [SMILES: CC(C)C(C(=O)O)c1cncc(N2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)c1]

Into a 50-mL round-bottom flask, was placed a solution of ethyl 2-[5-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)pyridin-3-yl]-3-methylbutanoate (31 mg, 0.035 mmol, 1 equiv) in MeOH (5 mL), to which was added LiOH $H_2O$ (14.67 mg, 0.349 mmol, 10 equiv) in $H_2O$ (2 mL). The resulting solution was stirred for 8 h at 40° C. in an oil bath. The pH value of the solution was adjusted to 5 with HCl (2 mol/L). The resulting mixture was concentrated under vacuum. This resulted in 79 mg of 2-[5-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)pyridin-3-yl]-3-methylbutanoic acid; lithiumol as a brown solid.

Step 8: Preparation of (2S,4R)-1-(2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)pyridin-3-yl)-3-methylbutanoyl)-4-hydroxy-N—((S)-1-(4-(4-methylthiazol-5-yl)phenyl)ethyl)pyrrolidine-2-carboxamide

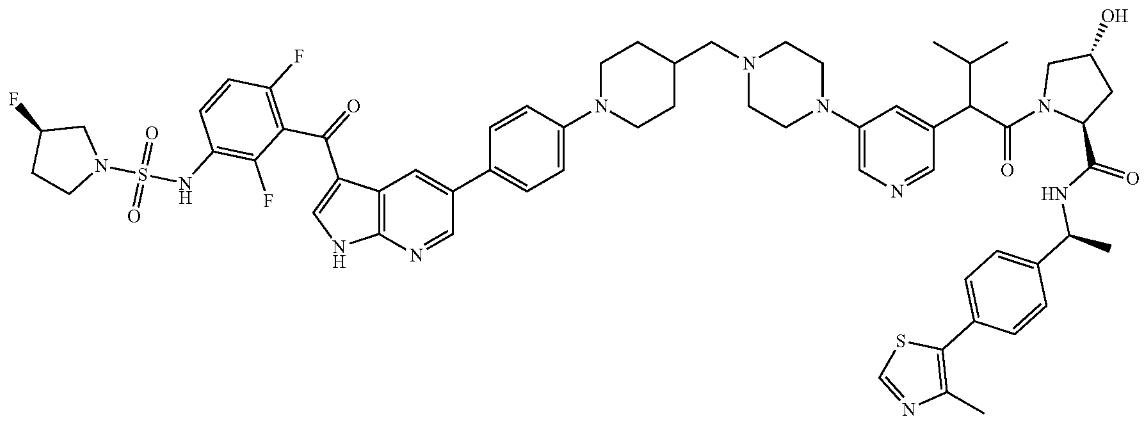 [SMILES: Cc1ncsc1-c1ccc([C@H](C)NC(=O)[C@@H]2C[C@@H](O)CN2C(=O)C(c2cncc(N3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)c2)C(C)C)cc1]

Into a 25-mL round-bottom flask, was placed 2-[5-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)pyridin-3-yl]-3-methylbutanoic acid (79 mg, 0.092 mmol, 1 equiv), DIEA (35.66 mg, 0.276 mmol, 3 equiv), (2S,4R)-4-hydroxy-N-[(1S)-1-[4-(4-methyl-1,3-thiazol-5-yl)phenyl]ethyl]pyrrolidine-2-carboxamide (60.96 mg, 0.184 mmol, 2.00 equiv), BOP (81.35 mg, 0.184 mmol, 2 equiv) In DMF (10 mL). The resulting solution was stirred for 1 h at room temperature. The reaction was then quenched by the addition of 10 mL of water/ice. The resulting solution was extracted with (40 mL×3) of ethyl acetate. The combined organic layers were washed with (20 mL×2) of brine, dried over anhydrous sodium sulfate and concentrated. The crude product was purified by Prep-HPLC. This resulted in 10.2 mg (9.46%) of (2S,4R)-1-[2-[5-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)pyridin-3-yl]-3-methylbutanoyl]-4-hydroxy-N-[(1S)-1-[4-(4-methyl-1,3-thiazol-5-yl)phenyl]ethyl]pyrrolidine-2-carboxamide as a yellow solid. LC/MS (ESI) m/z: 1172.65 $[M+1]^+$; $^1$H-NMR (400 MHz, $CD_3OD$) δ 8.77 (s, 1H), 8.76 (s, 1H), 8.50 (s, 1H), 8.02 (s, 1H), 7.79-7.48 (m, 1H), 7.47 (s, 1H), 7.39 (s, 2H), 7.36-7.32 (m, 5H), 7.12-7.00 (m, 3H), 5.21-5.11 (m, 2H), 4.62-4.55 (m, 5H), 4.51-4.31 (m, 2H), 3.67-3.63 (m, 3H), 3.47-3.39 (m, 4H), 2.64-2.56 (m, 2H), 2.55-2.51 (m, 4H), 2.47 (s, 3H), 2.39-2.37 (m, 3H), 2.14-2.10 (m, 3H), 1.86-1.82 (m, 4H), 1.76-1.72 (m, 1H), 1.43-1.45 (t, J=8 Hz, 2H), 1.35-1.18 (m, 5H), 1.18 (s, 3H), 0.65-0.61 (m, 3H).

Exemplary Synthesis of (2S,4R)-1-((S)-2-(5-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide (Exemplary Compound 753)

Step 1: Preparation of methyl 2-(5-hydroxy-1-methyl-1H-pyrazol-3-yl)acetate

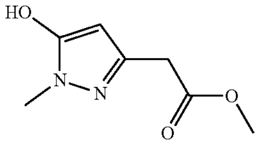

To a mixture of methylhydrazine (21.83 g, 189.49 mmol, 25 mL, 1.1 eq) in toluene (200 mL) was added dimethyl 3-oxopentanedioate (30 g, 172.26 mmol, 24.79 mL, 1 eq) and diisopropylethylamine (26.72 g, 206.72 mmol, 36 mL, 1.2 eq). The mixture stirred at 140° C. for 2 h and the water was allowed to distill off. Then the mixture stirred at 140° C. for 12 h. The mixture was quenched by addition of water (400 mL) and extracted with ethyl acetate (100 mL×3). The water phase was adjusted to PH=3~4 with 1 M hydrochloric acid, and then extracted with ethyl acetate (100 mL×10). The combined organic phase washed with brine (100 mL), dried over anhydrous sodium sulfate, filtered and concentrated under reduced pressure. Compound methyl 2-(5-hydroxy-1-methyl-pyrazol-3-yl)acetate (8.5 g, 49.95 mmol, 1.00 eq) was purified by preparative reverse phase HPLC. The product methyl 2-(5-hydroxy-1-methyl-pyrazol-3-yl)acetate (5.38 g, 31.62 mmol, 63% yield) was obtained as an off-white solid. LC/MS (ESI) m/z: 171.2 $[M+1]^+$; $^1$H NMR (400

MHz, DMSO-$d_6$) δ 10.81 (br s, 1H), 5.42-5.11 (m, 1H), 3.59 (s, 3H), 3.43 (s, 3H), 3.40 (s, 2H).

Step 2: Preparation of methyl 2-(5-(2,2-dimethoxy-ethoxy)-1-methyl-1H-pyrazol-3-yl)acetate

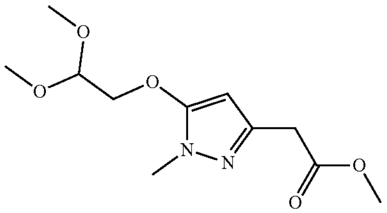

To a solution of methyl 2-(5-hydroxy-1-methyl-pyrazol-3-yl)acetate (1.38 g, 8.11 mmol, 1 eq) in dimethylformamide (30 mL) was added potassium carbonate (2.24 g, 16.22 mmol, 2 eq) and 2-bromo-1,1-dimethoxy-ethane (1.44 g, 8.52 mmol, 1 mL, 1.05 eq). The mixture was stirred at 70° C. for 12 h. Water (50 mL) was poured into the mixture and stirred for 1 min. The aqueous phase was extracted with ethyl acetate (50 mL×3). The combined organic phase was washed with brine (50 mL×3), dried with anhydrous sodium sulfate, filtered and concentrated in vacuum. The residue was purified by silica gel column chromatography (petroleum ether/ethyl acetate=20/1, 2/1). The product methyl 2-[5-(2,2-dimethoxyethoxy)-1-methyl-pyrazol-3-yl]acetate (744 mg, 2.74 mmol, 33% yield, 95% purity) was obtained as a colorless oil. LC/MS (ESI) m/z: 259.2 $[M+1]^+$; $^1H$ NMR (400 MHz, DMSO-$d_6$) δ 5.52 (s, 1H), 4.68 (t, J=5.2 Hz, 1H), 4.03 (d, J=5.2 Hz, 2H), 3.71 (s, 3H), 3.61 (s, 3H), 3.57 (s, 2H), 3.44 (s, 6H).

Step 3: Preparation of methyl 2-(5-(2,2-dimethoxy-ethoxy)-1-methyl-1H-pyrazol-3-yl)-3-methylbutanoate

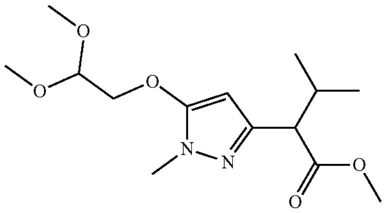

To a solution of methyl 2-[5-(2,2-dimethoxyethoxy)-1-methyl-pyrazol-3-yl]acetate (744 mg, 2.88 mmol, 1 eq) in tetrahydrofuran (12 mL) was added lithium diisopropylamide (2 M, 2.88 mL, 2 eq) at −70° C. The mixture was stirred at −70° C. for 0.5 h. Then 2-iodopropane (734 mg, 4.32 mmol, 0.45 mL, 1.5 eq) was added dropwise at −70° C. The mixture was stirred at 25° C. for 3 h. The mixture was poured into water (50 mL) and stirred for 1 min. The aqueous phase was extracted with ethyl acetate (30 mL×3). The combined organic phase was washed with brine (30 mL×2), dried with anhydrous sodium sulfate, filtered and concentrated in vacuum. The residue was purified by silica gel column chromatography (petroleum ether/ethyl acetate=20/1, 4/1). The product methyl 2-[5-(2,2-dimethoxyethoxy)-1-methyl-pyrazol-3-yl]-3-methyl-butanoate (300 mg, 0.86 mmol, 29% yield, 85% purity) was obtained as a light-yellow oil. LC/MS (ESI) m/z: 301.1 $[M+1]^+$.

Step 4: Preparation of 2-(5-(2,2-dimethoxyethoxy)-1-methyl-1H-pyrazol-3-yl)-3-methylbutanoic acid

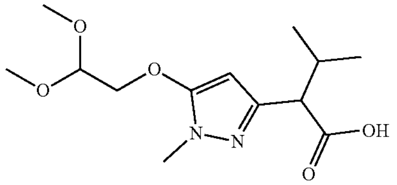 [SMILES: COC(COc1cc(C(C(=O)O)C(C)C)nn1C)OC]

To a solution of methyl 2-[5-(2,2-dimethoxyethoxy)-1-methyl-pyrazol-3-yl]-3-methyl-butanoate (300 mg, 0.99 mmol, 1 eq) in tetrahydrofuran (5 mL), methanol (2 mL) and water (1 mL) was added lithium hydroxide (167 mg, 4.00 mmol, 4 eq). The mixture was stirred at 40° C. for 12 h. Hydrochloric acid (1 M, 5 mL) was added to the reaction mixture to adjust pH to about 4~5, then the mixture was extracted by ethyl acetate (30 mL×3). The combined organic layers were washed with brine (50 mL×2), dried over anhydrous sodium sulfate, filtered and concentrated under reduced pressure. Compound 2-[5-(2,2-dimethoxyethoxy)-1-methyl-pyrazol-3-yl]-3-methyl-butanoic acid (260 mg, 0.90 mmol, 90% yield) was obtained as a brown oil. LC/MS (ESI) m/z: 287.2 $[M+1]^+$; $^1H$-NMR (400 MHz, DMSO-$d_6$) δ 5.61 (s, 1H), 4.66 (t, J=5.2 Hz, 1H), 4.06-3.98 (m, 2H), 3.52-3.47 (m, 3H), 3.34 (d, J=0.8 Hz, 6H), 2.99 (d, J=10.0 Hz, 1H), 2.12 (qd, J=6.4, 16.4 Hz, 1H), 0.94 (d, J=6.4 Hz, 3H), 0.75 (d, J=6.8 Hz, 3H).

Step 5: Preparation of (2S,4R)-1-(2-(5-(2,2-dimethoxyethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

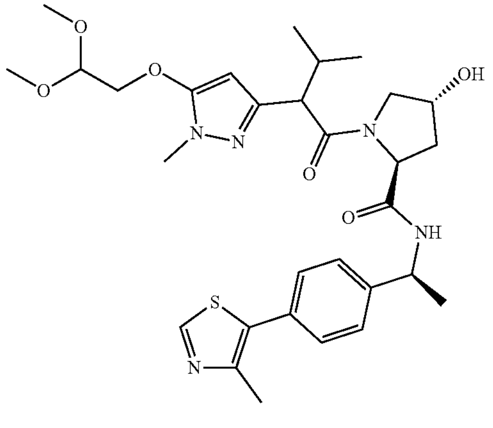 [SMILES: COC(COc1cc(C(C(=O)N2C[C@H](O)C[C@H]2C(=O)N[C@@H](C)c2ccc(-c3scnc3C)cc2)C(C)C)nn1C)OC]

To a solution of (2S,4R)-4-hydroxy-N-[(1S)-1-[4-(4-methylthiazol-5-yl)phenyl]ethyl]pyrrolidine-2-carboxamide (334 mg, 0.90 mmol, 1 eq, Hydrochloride) 2-[5-(2,2-dimethoxyethoxy)-1-methyl-pyrazol-3-yl]-3-methyl-butanoic acid (260 mg, 0.90 mmol, 1 eq) in dimethylformamide (5 mL) was added 0-(7-Azabenzotriazol-1-yl)-N,N,N',N'-tetramethyluronium hexafluorophosphate (517 mg, 1.36 mmol, 1.5 eq) and N,N-diisopropylethylamine (352 mg, 2.72 mmol, 3 eq). The mixture was stirred at 15° C. for 1 hr. The reaction mixture was diluted with water 30 mL and extracted with ethyl acetate (50 mL×3). The combined organic layers were washed with brine (50 mL×3), dried over anhydrous sodium sulfate, filtered and concentrated under reduced pressure. The residue was purified by flash silica gel chromatography (Eluent of 0-10% dichloromethane/methanol). Compound (2S,4R)-1-[2-[5-(2,2-dimethoxyethoxy)-1-methyl-pyrazol-3-yl]-3-methyl-butanoyl]-4-hydroxy-N-[(1S)-1-[4-(4-methylthiazol-5-yl)phenyl]ethyl] pyrrolidine-2-carboxamide (300 mg, 0.47 mmol, 52.33% yield, 95% purity) was obtained as a white gum. LC/MS (ESI) m/z: 600.3 $[M+1]^+$; $^1$H-NMR (400 MHz, $CDCl_3$) δ 8.68 (s, 1H), 7.44-7.30 (m, 5H), 5.57-5.53 (m, 1H), 4.82-4.95 (m, 1H), 4.74-4.53 (m, 3H), 4.11-3.95 (m, 2H), 3.93-3.82 (m, 1H), 3.58 (d, J=3.2 Hz, 4H), 3.45-3.42 (m, 3H), 3.41 (s, 2H), 3.38 (s, 2H), 2.53 (d, J=1.6 Hz, 3H), 2.39 (s, 1H), 1.48 (d, J=7.2 Hz, 1H), 1.32 (d, J=7.2 Hz, 3H), 1.03 (d, J=6.6 Hz, 3H), 0.94-0.86 (m, 2H), 0.86-0.77 (m, 3H).

Step 6: Preparation of (2S,4R)-1-((S)-2-(5-(2,2-dimethoxyethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

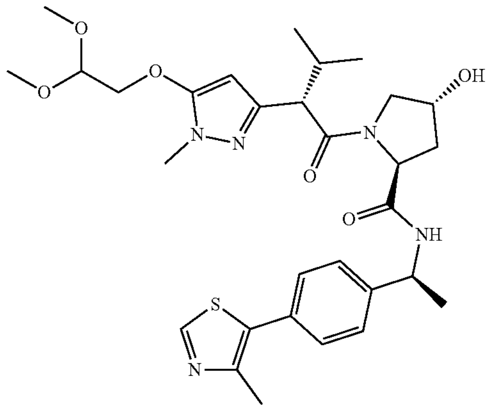 [SMILES: COC(COc1cc([C@@H](C(=O)N2C[C@H](O)C[C@H]2C(=O)N[C@@H](C)c2ccc(-c3scnc3C)cc2)C(C)C)nn1C)OC]

(2S,4R)-1-[2-[5-(2,2-dimethoxy ethoxy)-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (300 mg, 0.50 mmol, 1 eq) was purified by chiral SFC. The product (2S,4R)-1-[(2S)-2-[5-(2,2-dimethoxy ethoxy)-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (85 mg, 0.14 mmol, 84% yield, 98.1% purity) was obtained as a white solid.

Step 7: Preparation of (2S,4R)-4-hydroxy-1-((S)-3-methyl-2-(1-methyl-5-(2-oxoethoxy)-1H-pyrazol-3-yl)butanoyl)-N—((S)-1-(4-(4-methylthiazol-5-yl)phenyl)ethyl)pyrrolidine-2-carboxamide

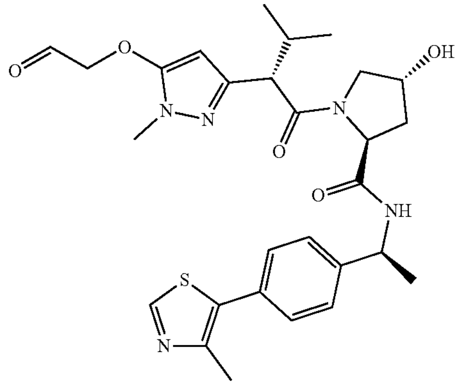 [SMILES: Cc1ncsc1-c1ccc([C@H](C)NC(=O)[C@@H]2C[C@@H](O)CN2C(=O)[C@H](c2cc(OCC=O)n(C)n2)C(C)C)cc1]

To a solution of (2S,4R)-1-[(2S)-2-[5-(2,2-dimethoxyethoxy)-1-methyl-pyrazol-3-yl]-3-methyl-butanoyl]-4-hydroxy-N-[(1S)-1-[4-(4-methylthiazol-5-yl)phenyl]ethyl] pyrrolidine-2-carboxamide (80 mg, 0.13 mmol, 1 eq) in tetrahydrofuran (5 mL) was added sulfuric acid (2 M, 2 mL, 30 eq). The mixture was stirred at 70° C. for 2 h. Water (10 mL) was added to the mixture and saturated sodium bicarbonate solution was added to adjust pH to about 8. Then the mixture was extracted with ethyl acetate 40 mL (20 mL×2). The combined organic layers were dried over anhydrous sodium sulfate, filtered and concentrated under reduced pressure. Compound (2S,4R)-4-hydroxy-1-[(2S)-3-methyl-2-[1-methyl-5-(2-oxoethoxy)pyrazol-3-yl]butanoyl]-N-[(1S)-1-[4-(4-methylthiazol-5-yl)phenyl]ethyl]pyrrolidine-2-carboxamide (55 mg, 0.10 mmol, 74% yield) was obtained as a colorless gum. LC/MS (ESI) m/z: 277.6 $[M/2+1]^+$.

Step 8: Preparation of (2S,4R)-1-((S)-2-(5-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

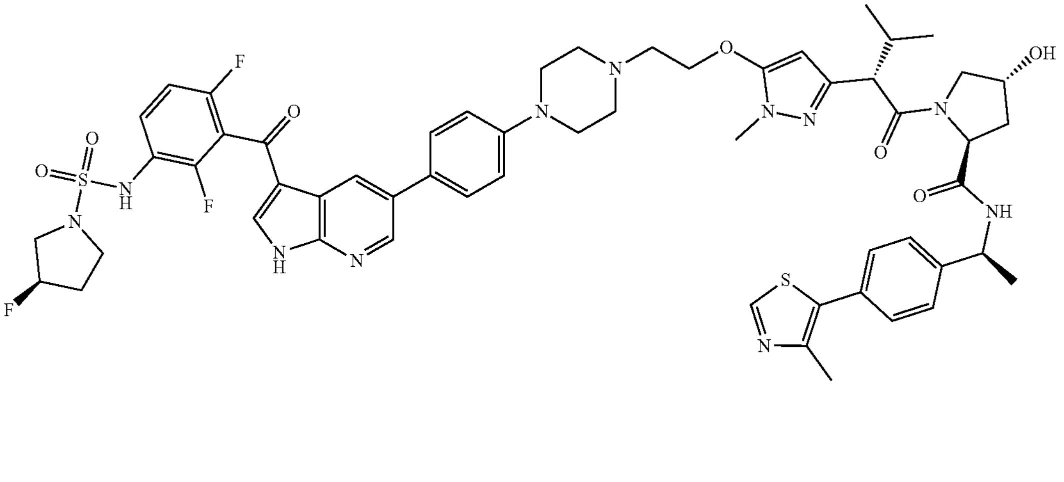 [SMILES: Cc1ncsc1-c1ccc([C@H](C)NC(=O)[C@@H]2C[C@@H](O)CN2C(=O)[C@H](c2cc(OCCN3CCN(c4ccc(-c5cnc6[nH]cc(C(=O)c7c(F)ccc(NS(=O)(=O)N8CC[C@@H](F)C8)c7F)c6c5)cc4)CC3)n(C)n2)C(C)C)cc1]

To a solution of (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (58 mg, 0.099 mmol, 1.00 eq) in dimethylformamide (1.5 mL) was added (2S,4R)-4-hydroxy-1-[(2S)-3-methyl-2-[1-methyl-5-(2-oxoethoxy)pyrazol-3-yl]butanoyl]-N-[(1S)-1-[4-(4-methylthiazol-5-yl)phenyl]ethyl]pyrrolidine-2-carboxamide (55 mg, 0.099 mmol, 1 eq). And then sodium cyanoborohydride (13 mg, 0.20 mmol, 2 eq) was added. The mixture was stirred at 30° C. for 12 h. The reaction mixture was diluted with water 10 mL and extracted with dichloromethane/methanol (10 mL×3). The combined organic layers were dried over anhydrous sodium sulfate, filtered and concentrated under reduced pressure. The residue was purified by Semi-preparative reverse phase HPLC. Compound (2S,4R)-1-[(2S)-2-[5-[2-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]ethoxy]-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (40.2 mg, 0.03 mmol, 32% yield, 95% purity, formate) was obtained as a yellow solid. LC/MS (ESI) m/z: 1122.4 $[M+1]^+$; $^1$H-NMR (400 MHz, DMSO-$d_6$) δ 12.88 (s, 1H), 8.98 (s, 1H), 8.65 (s, 1H), 8.53 (s, 1H), 8.32 (d, J=7.5 Hz, 1H), 8.05 (s, 1H), 7.60 (d, J=8.8 Hz, 3H), 7.45-7.41 (m, 2H), 7.38 (s, 2H), 7.23 (d, J=8.8 Hz, 1H), 7.08 (d, J=9.2 Hz, 2H), 5.56 (s, 1H), 5.39-5.19 (m, 1H), 5.03 (d, J=4.0 Hz, 1H), 4.95-4.87 (m, 1H), 4.34-4.24 (m, 2H), 4.18 (d, J=5.2 Hz, 2H), 3.70 (s, 1H), 3.50 (s, 4H), 3.47 (s, 3H), 3.25-3.20 (m, 7H), 2.67 (s, 5H), 2.45 (s, 4H), 2.08 (d, J=10.4 Hz, 3H), 1.96 (s, 2H), 1.80 (s, 1H), 1.39 (d, J=7.2 Hz, 3H), 0.92 (d, J=6.4 Hz, 3H), 0.71 (d, J=6.8 Hz, 3H).

Exemplary Synthesis of (2S,4R)-1-((R)-2-(5-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide (Exemplary Compound 757)

Step 1: Preparation of (2S,4R)-1-((R)-2-(5-(2,2-dimethoxyethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

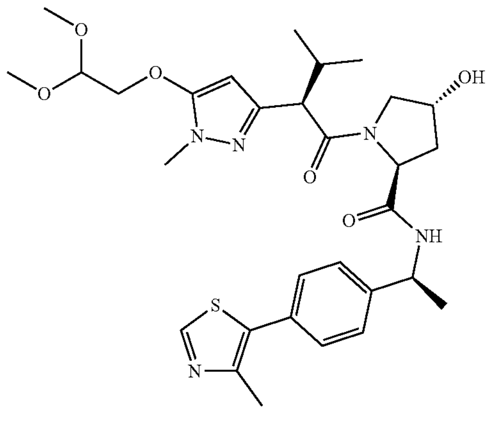 [SMILES: COC(COc1cc([C@H](C(=O)N2C[C@H](O)C[C@H]2C(=O)N[C@@H](C)c2ccc(-c3scnc3C)cc2)C(C)C)nn1C)OC]

(2S,4R)-1-[2-[5-(2,2-dimethoxy ethoxy)-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (300 mg, 0.50 mmol, 1 eq) was purified by chiral SFC. The product (2S,4R)-1-[(2R)-2-[5-(2,2-dimethoxy ethoxy)-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (150 mg, 0.24 mmol, 74% yield, 97.8% purity) was obtained as a colorless gum.

Step 2: Preparation of (2S,4R)-4-hydroxy-1-((R)-3-methyl-2-(1-methyl-5-(2-oxoethoxy)-1H-pyrazol-3-yl)butanoyl)-N—((S)-1-(4-(4-methylthiazol-5-yl(phenyl(ethyl)pyrrolidine-2-carboxamide

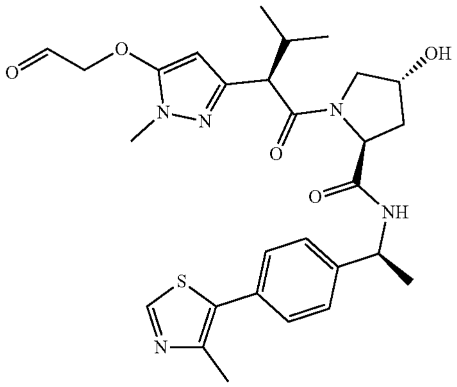 [SMILES: Cc1ncsc1-c1ccc([C@H](C)NC(=O)[C@@H]2C[C@@H](O)CN2C(=O)[C@@H](c2cc(OCC=O)n(C)n2)C(C)C)cc1]

To a solution of (2S,4R)-1-[(2R)-2-[5-(2,2-dimethoxy-ethoxy)-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (150 mg, 0.25 mmol, 1 eq) in tetrahydrofuran (2 mL) was added sulfuric acid (2 M, 1 mL, 8.00 eq). The mixture was stirred at 70° C. for 2 h. Water (10 mL) was added to the mixture and saturated sodium bicarbonate solution was added to adjust pH to about 8. Then the mixture was extracted with ethyl acetate 40 mL (20 mL×2). The combined organic layers were dried over anhydrous sodium sulfate, filtered and concentrated under reduced pressure. Compound (2S,4R)-4-hydroxy-1-[(2R)-3-methyl-2-[1-methyl-5-(2-oxoethoxy)pyrazol-3-yl]butanoyl]-N-[(1S)-1-[4-(4-methylthiazol-5-yl)phenyl]ethyl]pyrrolidine-2-carboxamide (130 mg, 0.23 mmol, 93% yield) was obtained as a colorless gum. LC/MS (ESI) m/z: 554.3 $[M+1]^+$.

Step 3: Preparation of (2S,4R)-1-((R)-2-(5-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

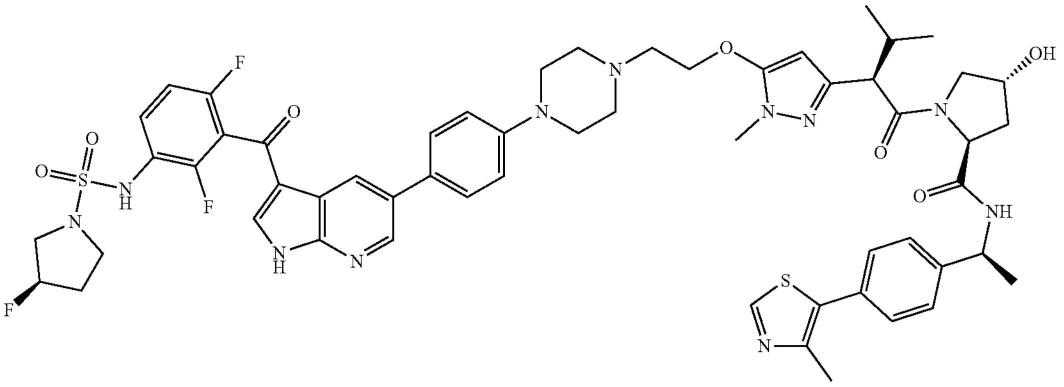 [SMILES: Cc1ncsc1-c1ccc([C@H](C)NC(=O)[C@@H]2C[C@@H](O)CN2C(=O)[C@@H](c2cc(OCCN3CCN(c4ccc(-c5cnc6[nH]cc(C(=O)c7c(F)ccc(NS(=O)(=O)N8CC[C@@H](F)C8)c7F)c6c5)cc4)CC3)n(C)n2)C(C)C)cc1]

To a solution of (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (137 mg, 0.23 mmol, 1.00 eq) in dimethylformamide (1.5 mL) was added (2S,4R)-4-hydroxy-1-[(2R)-3-methyl-2-[1-methyl-5-(2-oxoethoxy)pyrazol-3-yl]butanoyl]-N-[(1S)-1-[4-(4-methylthiazol-5-yl)phenyl]ethyl]pyrrolidine-2-carboxamide (130 mg, 0.23 mmol, 1 eq). And then sodium cyanoborohydride (29 mg, 0.46 mmol, 2 eq) was added. The mixture was stirred at 30° C. for 12 h. The reaction mixture was diluted with water 10 mL and extracted with dichloromethane/methanol (10 mL×3). The combined organic layers were dried over anhydrous sodium sulfate, filtered and concentrated under reduced pressure. The residue was purified by Semi-preparative reverse phase HPLC. Compound (2S,4R)-1-[(2R)-2-[5-[2-[4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazin-1-yl]ethoxy]-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (53.9 mg, 0.04 mmol, 19% yield, 100% purity, formate) was obtained as a yellow solid. LC/MS (ESI) m/z: 561.8 [M/2+1]$^+$; $^1$H NMR (400 MHz, DMSO-$d_6$) δ 12.88 (s, 1H), 8.99-8.96 (m, 1H), 8.64 (d, J=2.2 Hz, 1H), 8.53 (s, 1H), 8.06 (s, 1H), 7.86 (d, J=8.0 Hz, 1H), 7.65-7.56 (m, 3H), 7.44 (d, J=4.4 Hz, 1H), 7.40 (d, J=8.4 Hz, 2H), 7.35-7.25 (m, 2H), 7.11-6.99 (m, 2H), 5.62-5.52 (m, 1H), 5.41-5.17 (m, 1H), 5.05 (d, J=3.6 Hz, 1H), 4.93-4.81 (m, 1H), 4.48-4.37 (m, 1H), 4.28-4.02 (m, 3H), 3.57-3.50 (m, 2H), 3.50-3.42 (m, 5H), 3.39 (s, 2H), 3.34 (s, 2H), 3.22 (s, 1H), 3.17 (s, 3H), 2.73-2.62 (m, 3H), 2.59 (s, 3H), 2.48-2.41 (m, 4H), 2.20 (s, 1H), 2.09 (d, J=15.6 Hz, 2H), 1.99 (s, 1H), 1.85 (br d, J=5.6 Hz, 1H), 1.45 (d, J=6.4 Hz, 1H), 1.31 (d, J=7.2 Hz, 2H), 0.94 (d, J=6.4 Hz, 2H), 0.77 (d, J=6.4 Hz, 3H), 0.68 (d, J=6.4 Hz, 1H).

Exemplary Synthesis of (2S,4R)-1-((S)-4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N—((S)-1-(4-(4-methylthiazol-5-yl)phenyl)ethyl)pyrrolidine-2-carboxamide (Exemplary Compound 754)

Step 1: Preparation of tert-butyl 4-((S)-4-((2S,4R)-4-hydroxy-2-(((S)-1-(4-(4-methylthiazol-5-yl)phenyl)ethyl)carbamoyl)pyrrolidin-1-yl)-2,2-dimethyl-3-(3-methylisoxazol-5-yl)-4-oxobutyl)piperazine-1-carboxylate

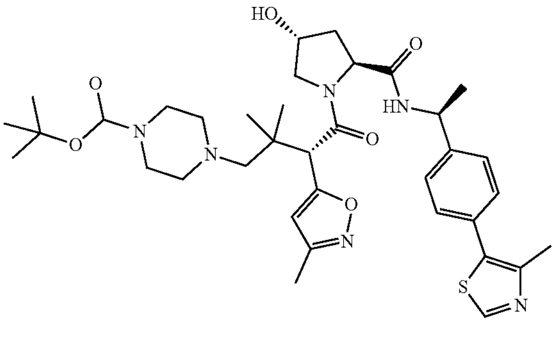 [SMILES: Cc1cc([C@@H](C(=O)N2C[C@H](O)C[C@H]2C(=O)N[C@@H](C)c2ccc(-c3scnc3C)cc2)C(C)(C)CN2CCN(C(O)OC(C)(C)C)CC2)on1]

Tert-butyl 4-[4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate (80 mg, 0.12 mmol, 1 eq) was purified by SFC to give product tert-butyl 4-[(3S)-4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate as a white solid. The product was further purified by prep-HPLC, the fraction of acetonitrile was removed and the residue was lyophilized to give tert-butyl 4-[(3S)-4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate (19.7 mg, 0.023 mmol, 20% yield, 97% purity, TFA) as a white solid. LC/MS (ESI) m/z: 695.3 [M+1]$^+$; $^1$H-NMR (400 MHz, DMSO-$d_6$) δ 8.96 (s, 1H), 7.52-7.37 (m, 4H), 6.47 (s, 1H), 5.04 (q, J=7.1 Hz, 1H), 4.65-4.55 (m, 1H), 4.48-4.39 (m, 2H), 4.32-4.14 (m, 2H), 3.89 (dd, J=3.9, 11.3 Hz, 1H), 3.70 (d, J=12.1 Hz, 1H), 3.56 (d, J=11.2 Hz, 2H), 3.44-3.30 (m, 2H), 3.23-3.02 (m, 3H), 2.97-2.87 (m, 1H), 2.49 (s, 3H), 2.32 (s, 3H), 2.30-2.23 (m, 1H), 1.97 (ddd, J=4.3, 9.5, 13.4 Hz, 1H), 1.53 (d, J=7.1 Hz, 3H), 1.50 (s, 9H), 1.48 (s, 3H), 1.11 (s, 3H).

Step 2: Preparation of (2S,4R)-1-((S)-3,3-dimethyl-2-(3-methylisoxazol-5-yl)-4-(piperazin-1-yl)butanoyl)-4-hydroxy-N—((S)-1-(4-(4-methylthiazol-5-yl)phenyl)ethyl)pyrrolidine-2-carboxamide

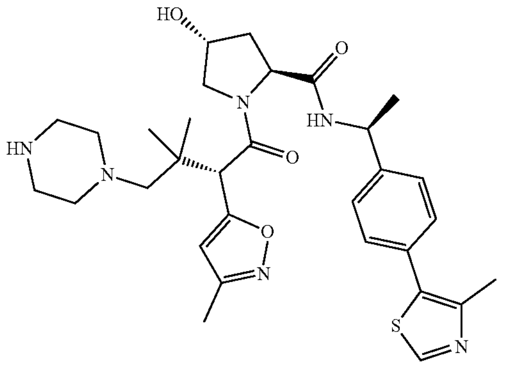 [SMILES: Cc1cc([C@@H](C(=O)N2C[C@H](O)C[C@H]2C(=O)N[C@@H](C)c2ccc(-c3scnc3C)cc2)C(C)(C)CN2CCNCC2)on1]

To a solution of tert-butyl 4-[(3S)-4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate (330 mg, 0.47 mmol, 1 eq) in dichloromethane (4 mL) was added hydrochloric acid/dioxane (4 M, 4 mL, 33.69 eq), the mixture was stirred at 20° C. for 0.5 h. The mixture was concentrated to give (2S,4R)-1-[(2S)-3,3-dimethyl-2-(3-methylisoxazol-5-yl)-4-piperazin-1-yl-butanoyl]-4-hydroxy-N-[(1S)-1-[4-(4-methylthiazol-5-yl)phenyl]ethyl]pyrrolidine-2-carboxamide (310 mg, HCl) as a yellow solid. LC/MS (ESI) m/z: 595.2 [M+1]$^+$.

Step 3: Preparation of (2S,4R)-1-((S)-4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N—((S)-1-(4-(4-methylthiazol-5-yl)phenyl)ethyl)pyrrolidine-2-carboxamide

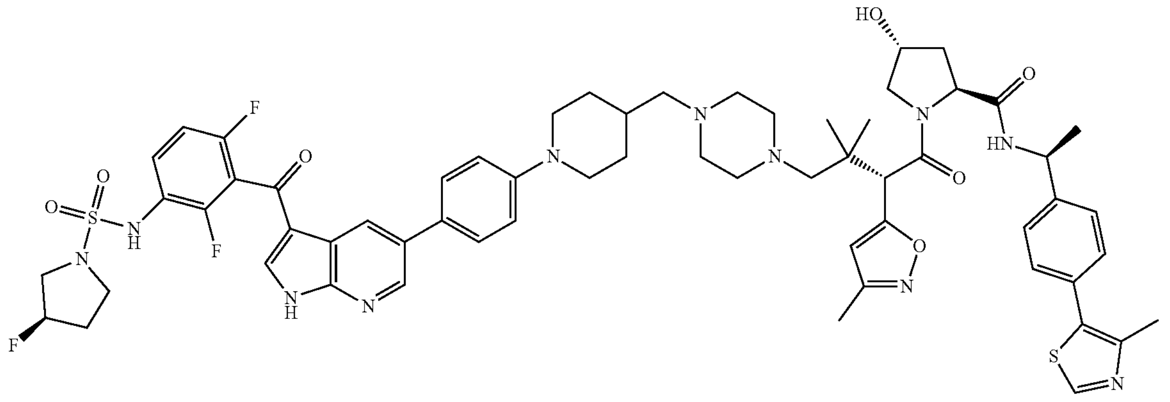 [SMILES: Cc1cc([C@@H](C(=O)N2C[C@H](O)C[C@H]2C(=O)N[C@@H](C)c2ccc(-c3scnc3C)cc2)C(C)(C)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)on1]

To a solution of (2S,4R)-1-[(2S)-3,3-dimethyl-2-(3-methylisoxazol-5-yl)-4-piperazin-1-yl-butanoyl]-4-hydroxy-N-[(1S)-1-[4-(4-methylthiazol-5-yl)phenyl]ethyl]pyrrolidine-2-carboxamide (120 mg, 0.19 mmol, 1 eq, HCl) in methanol (2 mL) and dichloromethane (2 mL) was added sodium acetate (31 mg, 0.38 mmol, 2 eq), and then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (116 mg, 0.19 mmol, 1 eq) was added, acetic acid (53 mg, 0.87 mmol, 4.60 eq) was added until pH=6, the mixture was stirred at 20° C. for 10 min, and then sodium cyanoborohydride (48 mg, 0.76 mmol, 4 eq) was added, the mixture was stirred at 20° C. for 1 h. The mixture was concentrated to give crude product, which was purified by prep-HPLC. The fraction of acetonitrile was removed and the residue was lyophilized to give product. Compound (2S,4R)-1-[(2S)-4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]-3,3-dimethyl-2-(3-methylisoxazol-5-yl)butanoyl]-4-hydroxy-N-[(1S)-1-[4-(4-methylthiazol-5-yl)phenyl]ethyl]pyrrolidine-2-carboxamide (83.7 mg, 66.41 umol, 34.9% yield, 98.1% purity, FA) was obtained as a yellow solid. LC/MS (ESI) m/z: 1190.5 [M+1]$^+$; $^1$H-NMR (400 MHz, DMSO-$d_6$) δ 12.91 (br s, 1H), 9.01-8.95 (m, 1H), 8.64 (d, J=2.2 Hz, 1H), 8.52 (br s, 1H), 8.41 (d, J=8.1 Hz, 1H), 8.18 (s, 1H), 8.07 (s, 1H), 7.65-7.52 (m, 3H), 7.48-7.32 (m, 4H), 7.25 (t, J=8.3 Hz, 1H), 7.05 (br d, J=8.8 Hz, 2H), 6.28-6.11 (m, 1H), 5.42-5.17 (m, 1H), 5.14-4.87 (m, 1H), 4.99-4.65 (m, 1H), 4.40-4.18 (m, 3H), 3.94 (s, 1H), 3.76 (br d, J=10.5 Hz, 2H), 3.47 (br s, 2H), 3.32-3.23 (m, 6H), 2.77-2.68 (m, 2H), 2.46-2.45 (m, 1H), 2.46 (s, 3H), 2.47-2.35 (m, 1H), 2.39 (br s, 2H), 2.24-1.95 (m, 11H), 1.85-1.62 (m, 4H), 1.46-1.35 (m, 3H), 1.20 (br d, J=10.1 Hz, 2H), 1.07-0.95 (m, 3H), 0.90-0.81 (m, 3H).

Exemplary Synthesis of (2S,4R)-1-((R)-4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N—((S)-1-(4-(4-methylthiazol-5-yl)phenyl) ethyl)pyrrolidine-2-carboxamide (Exemplary Compound 755)

Step 1: Preparation of tert-butyl 4-((R)-4-((2S,4R)-4-hydroxy-2-(((S)-1-(4-(4-methylthiazol-5-yl)phenyl)ethyl)carbamoyl)pyrrolidin-1-yl)-2,2-dimethyl-3-(3-methylisoxazol-5-yl)-4-oxobutyl)piperazine-1-carboxylate

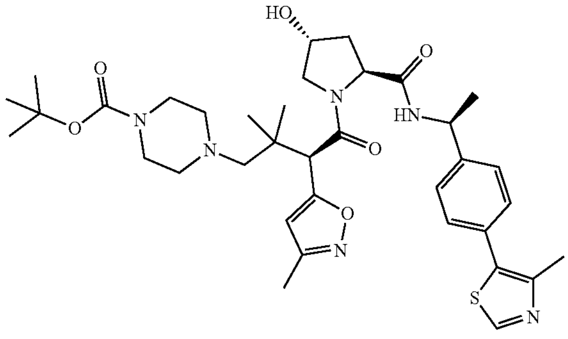 [SMILES: Cc1cc([C@H](C(=O)N2C[C@H](O)C[C@H]2C(=O)N[C@@H](C)c2ccc(-c3scnc3C)cc2)C(C)(C)CN2CCN(C(=O)OC(C)(C)C)CC2)on1]

Tert-butyl 4-[4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl] piperazine-1-carboxylate (80 mg, 0.12 mmol, 1 eq) was purified by SFC to give product tert-butyl 4-[(3R)-4-[(2S,4R)-4-hydroxy-2-[[(1S)-1-[4-(4-methylthiazol-5-yl) phenyl]ethyl]carbamoyl]pyrrolidin-1-yl]-2,2-dimethyl-3-(3-methylisoxazol-5-yl)-4-oxo-butyl]piperazine-1-carboxylate (24.3 mg, 34.03 umol, 29.6% yield, 97.3% purity) as a white solid. LC/MS (ESI) m/z: 695.4 $[M+1]^+$; $^1$H-NMR (400 MHz, DMSO-$d_6$) δ 8.87 (s, 1H), 7.48-7.36 (m, 4H), 6.24 (s, 1H), 5.06-4.98 (m, 1H), 4.61-4.50 (m, 1H), 4.41 (s, 2H), 3.78 (d, J=10.9 Hz, 1H), 3.56 (dd, J=4.2, 10.7 Hz, 1H), 3.43 (s, 4H), 2.66-2.56 (m, 2H), 2.54-2.41 (m, 6H), 2.29 (d, J=13.0 Hz, 1H), 2.24 (s, 3H), 2.22-2.14 (m, 1H), 1.92 (ddd, J=4.7, 8.3, 13.2 Hz, 1H), 1.52 (d, J=7.0 Hz, 3H), 1.45 (s, 9H), 1.10 (s, 3H), 0.98 (s, 3H).

Step 2: Preparation of (2S,4R)-1-((R)-3,3-dimethyl-2-(3-methylisoxazol-5-yl)-4-(piperazin-1-yl)butanoyl)-4-hydroxy-N—((S)-1-(4-(4-methylthiazol-5-yl)phenyl)ethyl)pyrrolidine-2-carboxamide

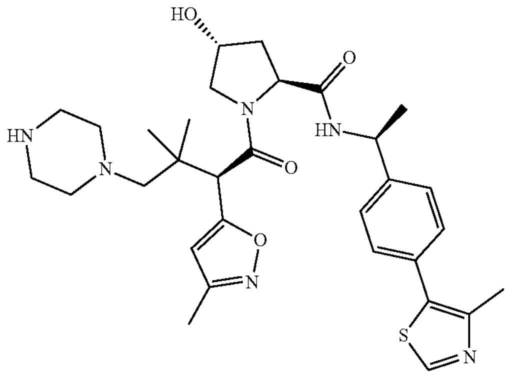 [SMILES: Cc1cc([C@H](C(=O)N2C[C@H](O)C[C@H]2C(=O)N[C@@H](C)c2ccc(-c3scnc3C)cc2)C(C)(C)CN2CCNCC2)on1]

To a solution of tert-butyl 4-[(3R)-4-[(2S,4R)-4-hydroxy-2-[[(1S)-1-[4-(4-methylthiazol-5-yl)phenyl]ethyl]carbamoyl]pyrrolidin-1-yl]-2,2-dimethyl-3-(3-methylisoxazol-5-yl)-4-oxo-butyl]piperazine-1-carboxylate (120 mg, 0.17 mmol, 1 eq) in dichloromethane (2 mL) was added hydrochloric acid/dioxane (2 M, 2.9 mL, 33.69 eq), the mixture was stirred at 20° C. for 0.5 h. The mixture was concentrated to give product (2S,4R)-1-[(2R)-3,3-dimethyl-2-(3-methylisoxazol-5-yl)-4-piperazin-1-yl-butanoyl]-4-hydroxy-N-[(1S)-1-[4-(4-methylthiazol-5-yl)phenyl]ethyl]pyrrolidine-2-carboxamide (125 mg, HCl) as a yellow solid. LC/MS (ESI) m/z: 595.2 $[M+1]^+$.

Step 3: Preparation of (2S,4R)-1-((R)-4-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-3,3-dimethyl-2-(3-methylisoxazol-5-yl)butanoyl)-4-hydroxy-N—((S)-1-(4-(4-methylthiazol-5-yl)phenyl) ethyl)pyrrolidine-2-carboxamide

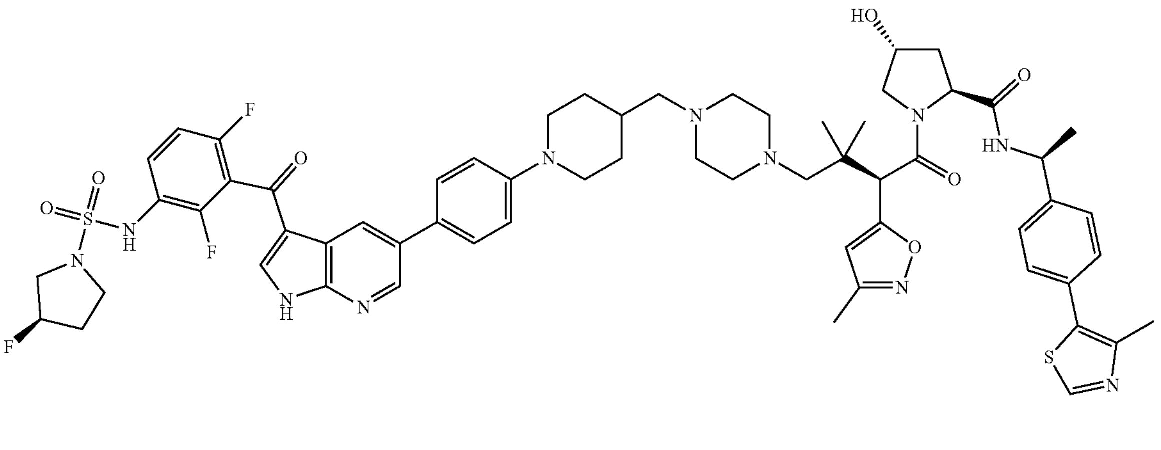 [SMILES: Cc1cc([C@H](C(=O)N2C[C@H](O)C[C@H]2C(=O)N[C@@H](C)c2ccc(-c3scnc3C)cc2)C(C)(C)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)on1]

To a solution of (2S,4R)-1-[(2R)-3,3-dimethyl-2-(3-methylisoxazol-5-yl)-4-piperazin-1-yl-butanoyl]-4-hydroxy-N-[(1S)-1-[4-(4-methylthiazol-5-yl)phenyl]ethyl]pyrrolidine-2-carboxamide (100 mg, 0.17 mmol, 1 eq, HCl) in methanol (2 mL) and dichloromethane (2 mL) was added sodium acetate (28 mg, 0.34 mmol, 2 eq), and then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (103 mg, 0.17 mmol, 1 eq) was added, acetic acid (46 mg, 0.77 mmol, 4.60 eq) was added until pH=6, the mixture was stirred at 20° C. for 10 min, and then sodium cyanoborohydride (42 mg, 0.67 mmol, 4 eq) was added, the mixture was stirred at 20° C. for 1 h. The mixture was concentrated to give crude product, which was purified by prep-HPLC. The fraction of acetonitrile was removed and the residue was lyophilized to give product. Compound (2S,4R)-1-[(2R)-4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]-3,3-dimethyl-2-(3-methylisoxazol-5-yl)butanoyl]-4-hydroxy-N-[(1S)-1-[4-(4-methylthiazol-5-yl)phenyl]ethyl]pyrrolidine-2-carboxamide (90.4 mg, 73.11 umol, 43.5% yield, 100% purity, FA) was obtained as a yellow solid. LC/MS (ESI) m/z: 1190.5 $[M+1]^+$; $^1$H-NMR (400 MHz, DMSO-$d_6$) δ 12.91 (br s, 1H), 9.01-8.96 (m, 1H), 8.64 (d, J=2.2 Hz, 1H), 8.53 (br s, 1H), 8.31 (d, J=7.8 Hz, 1H), 8.18 (s, 1H), 8.07 (s, 1H), 7.66-7.54 (m, 3H), 7.48-7.31 (m, 4H), 7.25 (t, J=8.7 Hz, 1H), 7.06 (br d, J=8.8 Hz, 2H), 6.19 (s, 1H), 5.40-5.20 (m, 1H), 4.90 (quin, J=7.1 Hz, 1H), 4.41 (t, J=7.3 Hz, 1H), 4.27 (br s, 1H), 4.22 (s, 1H), 3.77 (br d, J=11.9 Hz, 2H), 3.59 (br d, J=9.0 Hz, 1H), 3.47 (br s, 2H), 3.33-3.28 (m, 4H), 2.76-2.68 (m, 2H), 2.46-2.28 (m, 10H), 2.20-1.94 (m, 10H), 1.83-1.63 (m, 4H), 1.37 (d, J=7.0 Hz, 2H), 1.48 (br d, J=7.2 Hz, 1H), 1.28-1.11 (m, 2H), 1.04-0.94 (m, 3H), 0.87 (s, 3H).

Exemplary Synthesis of (2S,4R)-1-((S)-3,3-dimethyl-2-(2-(2-(((1R,3R)-3-((2'-methyl-5-morpholino-5'-(3-(trifluoromethyl)benzamido)-[3,3'-bipyridin]-6-yl)oxy)cyclohexyl)oxy)ethoxy)acetamido)butanoyl)-4-hydroxy-N—((S)-1-(4-(4-methylthiazol-5-yl)phenyl)ethyl)pyrrolidine-2-carboxamide (Exemplary Compound 756)

Step 1: Preparation of N-(5-bromo-6-methylpyridin-3-yl)-3-(trifluoromethyl)benzamide

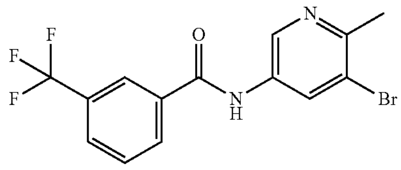 [SMILES: Cc1ncc(NC(=O)c2cccc(C(F)(F)F)c2)cc1Br]

To a mixture of 3-(trifluoromethyl)benzoic acid (10.16 g, 53.47 mmol, 1 eq) and 5-bromo-6-methyl-pyridin-3-amine (10 g, 53.47 mmol, 1 eq) in dimethyl formamide (100 mL) was added [dimethylamino(triazolo[4,5-b]pyridin-3-yloxy)methylene]-dimethyl-ammonium; hexafluorophosphate (30.49 g, 80.20 mmol, 1.5 eq) and triethylamine (10.82 g, 106.93 mmol, 2 eq). The mixture was stirred at 20° C. for 12 hours. The mixture was quenched with water (300 mL). The aqueous layer was extracted with ethyl acetate (200 mL×3). All the combined organic layers were washed with brine (300 mL), dried over sodium sulfate, filtered and concentrated. The residue was triturated in a solution of Petroleum ether/Ethyl acetate=50:1 (100 mL) to give N-(5-bromo-6-methyl-3-pyridyl)-3-(trifluoromethyl)benzamide (17 g, 46.01 mmol, 86% yield, 97% purity) as a yellow solid. LC/MS (ESI) m/z: 360.9 $[M+1]^+$.

Step 2: Preparation of (2-methyl-5-(3-(trifluoromethyl)benzamido)pyridin-3-yl)boronic acid

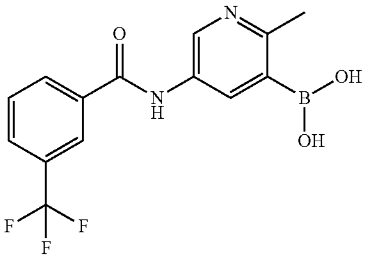 [SMILES: Cc1ncc(NC(=O)c2cccc(C(F)(F)F)c2)cc1B(O)O]

A mixture of 4,4,5,5-tetramethyl-2-(4,4,5,5-tetramethyl-1,3,2-dioxaborolan-2-yl)-1,3,2-dioxaborolane (7.07 g, 27.84 mmol, 2 eq), N-(5-bromo-6-methyl-3-pyridyl)-3-(trifluoromethyl)benzamide (5 g, 13.92 mmol, 1 eq), [1,1'-bis(diphenylphosphino)ferrocene]dichloropalladium(II) (1.14 g, 1.39 mmol, 0.1 eq), potassium acetate (4.10 g, 41.76 mmol, 3 eq) in dioxane (100 mL) was degassed and purged with nitrogen for 3 times, and then the mixture was stirred at 100° C. for 12 hours under nitrogen atmosphere. The reaction mixture was filtered, and the filtrate was concentrated. Compound [2-methyl-5-[[3-(trifluoromethyl)benzoyl]amino]-3-pyridyl]boronic acid (5.5 g) was obtained as a black brown oil. LC/MS (ESI) m/z: 325.1 $[M+1]^+$.

Step 3: Preparation of (1S,3R)-3-(benzyloxy)cyclohexan-1-ol

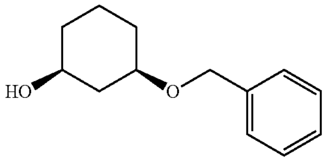 [SMILES: O[C@H]1CCC[C@@H](OCc2ccccc2)C1]

To a solution of cyclohexane-1,3-diol (18 g, 154.96 mmol, 1 eq) in dimethyl formamide (250 mL) was added sodium-hydrogen (6.20 g, 154.96 mmol, 60% purity, 1 eq) and boron tribromide (26.50 g, 154.96 mmol, 18.41 mL, 1 eq). The mixture was stirred at 0~60° C. for 12 hours. The reaction mixture was quenched by water 1500 mL at 0° C., and then extracted with ethyl acetate (500 mL×3). The combined organic layers were washed with brines (500 mL×3), dried over anhydrous sodium sulfate, filtered and concentrated under reduced pressure. The residue was purified by column chromatography. Compound (1S,3R)-3-benzyloxycyclohexanol (10 g, 48.48 mmol, 62% yield) was obtained as a yellow oil. LC/MS (ESI) m/z: 259.0 $[M-56]^+$.

Step 4: Preparation of 2-(((1R,3R)-3-(benzyloxy) cyclohexyl)oxy)-5-bromo-3-nitropyridine

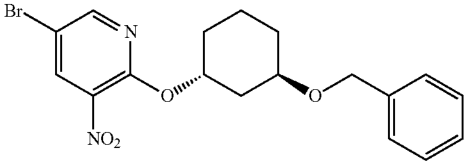 [SMILES: O=[N+]([O-])c1cc(Br)cnc1O[C@@H]1CCC[C@@H](OCc2ccccc2)C1]

To a solution of 5-bromo-3-nitro-pyridin-2-ol (8.76 g, 39.99 mmol, 1.1 eq) and (1S,3R)-3-benzyloxycyclohexanol (7.5 g, 36.36 mmol, 1 eq) in tetrahydrofuran (150 mL) was added triphenylphosphine (14.30 g, 54.54 mmol, 1.5 eq) and isopropyl (NE)-N-isopropoxycarbonyliminocarbamate (11.03 g, 54.54 mmol, 10.60 mL, 1.5 eq). The mixture was stirred at 0~25° C. for 12 hours. The reaction mixture was quenched by water 300 mL at 20° C., and then extracted with ethyl acetate (100 mL×3). The combined organic layers were washed with brines (100 mL×3), dried over anhydrous sodium sulfate, filtered and concentrated under reduced pressure. The residue was purified by column chromatography (Petroleum ether:Ethyl acetate=1:0 to 50:1). Compound 2-[(1R,3R)-3-benzyloxycyclohexoxy]-5-bromo-3-nitro-pyridine (7.5 g, 18.42 mmol, 50% yield) was obtained as a yellow oil.

Step 5: Preparation of 2-(((1R,3R)-3-(benzyloxy) cyclohexyl)oxy)-5-bromopyridin-3-amine

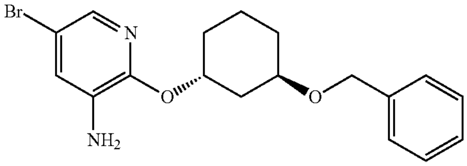 [SMILES: Nc1cc(Br)cnc1O[C@@H]1CCC[C@@H](OCc2ccccc2)C1]

A mixture of 2-[(1R,3R)-3-benzyloxycyclohexoxy]-5-bromo-3-nitro-pyridine (13.1 g, 32.17 mmol, 1 eq), iron (8.98 g, 160.83 mmol, 5 eq), ammonium chloride (8.60 g, 160.83 mmol, 5 eq) in ethyl alcohol (250 mL) and water (50 mL) was degassed and purged with nitrogen for 3 times, and then the mixture was stirred at 80° C. for 12 hour under nitrogen atmosphere. The reaction mixture was filtered and the filtrate was concentrated. The residue was purified by column chromatography (Petroleum ether/Ethyl acetate=50/1 to 10:1). Compound 2-[(1R,3R)-3-benzyloxy-cyclohexoxy]-5-bromo-pyridin-3-amine (11.5 g, 30.48 mmol, 94% yield) was obtained as a yellow oil. LC/MS (ESI) m/z: 377.1 [M+1]$^+$.

Step 6: Preparation of 4-(2-(((1R,3R)-3-(benzyloxy) cyclohexyl)oxy)-5-bromopyridin-3-yl)morpholine

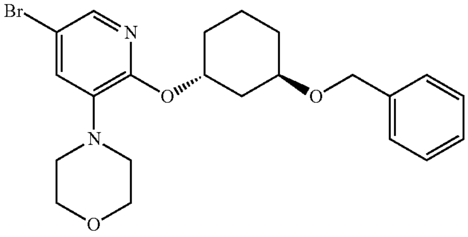 [SMILES: Brc1cnc(O[C@@H]2CCC[C@@H](OCc3ccccc3)C2)c(N2CCOCC2)c1]

To the mixture of 2-[(1R,3R)-3-benzyloxycyclohexoxy]-5-bromo-pyridin-3-amine (14.7 g, 38.96 mmol, 1 eq) in dimethyl formamide (200 mL) was added sodium hydride (7.79 g, 194.82 mmol, 60% purity, 5 eq) at 25° C. The mixture was stirred at 25° C. for 0.5 hour. Then 1-bromo-2-(2-bromoethoxy)ethane (27.11 g, 116.89 mmol, 14.65 mL, 3 eq) was added to the mixture. The mixture was stirred at 80° C. for 11.5 hours. The reaction mixture was quenched by water 1000 mL at 0° C., and then extracted with ethyl acetate (200 mL×3). The combined organic layers were washed with brines (200 mL×3), dried over anhydrous sodium sulfate, filtered and concentrated under reduced pressure. The residue was purified by column chromatography (Petroleum ether/Ethyl acetate=30:1 to 10:1). Compound 4-[2-[(1R,3R)-3-benzyloxycyclohexoxy]-5-bromo-3-pyridyl] morpholine (17 g, 38.00 mmol, 97% yield) was obtained as a yellow oil. LC/MS (ESI) m/z: 447.1 [M+1]$^+$.

Step 7: Preparation of N-(6'-(((1R,3R)-3-(benzyloxy)cyclohexyl)oxy)-2-methyl-5'-morpholino-[3,3'-bipyridin]-5-yl)-3-(trifluoromethyl)benzamide

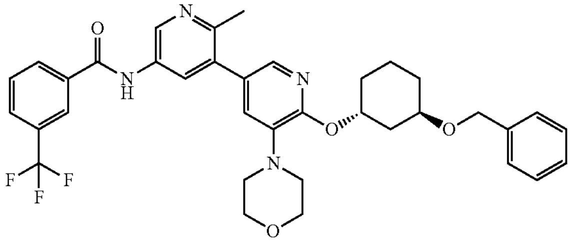 [SMILES: Cc1ncc(NC(=O)c2cccc(C(F)(F)F)c2)cc1-c1cnc(O[C@@H]2CCC[C@@H](OCc3ccccc3)C2)c(N2CCOCC2)c1]

A mixture of [2-methyl-5-[[3-(trifluoromethyl)benzoyl] amino]-3-pyridyl]boronic acid (4.78 g, 14.75 mmol, 1.1 eq), 4-[2-[(1R,3R)-3-benzyloxycyclohexoxy]-5-bromo-3-pyridyl]morpholine (6 g, 13.41 mmol, 1 eq), cyclopentyl (diphenyl)phosphane;dichloromethane; dichloropalladium; iron (1.10 g, 1.34 mmol, 0.1 eq), potassium carbonate (5.56 g, 40.24 mmol, 3 eq) and water (2 mL) in dioxane (200 mL) was degassed and purged with nitrogen for 3 times, and then the mixture was stirred at 100° C. for 12 hours under nitrogen atmosphere. The reaction mixture was quenched by water 500 mL at 25° C., and then extracted with ethyl acetate (200 mL×3). The combined organic layers were washed with brines (100 mL×2), dried over anhydrous sodium sulfate, filtered and concentrated under reduced pressure. The residue was purified by column chromatography (Petroleum ether/Ethyl acetate=20:1 to 8:1). Compound N-[5-[6-[(1R,3R)-3-benzyloxycyclohexoxy]-5-morpholino-3- pyridyl]-6-methyl-3-pyridyl]-3-(trifluoromethyl)benzamide (5.5 g, 8.50 mmol, 63% yield) was obtained as a yellow oil. LC/MS (ESI) m/z: 647.1 $[M+1]^+$.

Step 8: Preparation of N-(6'-(((1R,3R)-3-hydroxycyclohexyl)oxy)-2-methyl-5'-morpholino-[3,3'-bipyridin]-5-yl)-3-(trifluoromethyl)benzamide

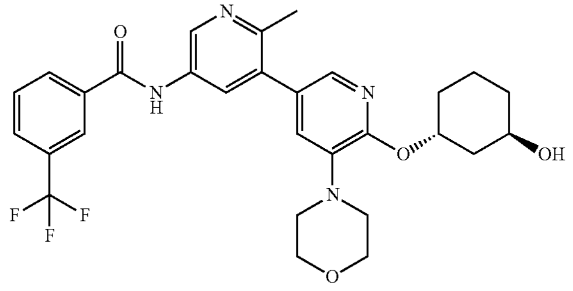 [SMILES: Cc1ncc(NC(=O)c2cccc(C(F)(F)F)c2)cc1-c1cnc(O[C@@H]2CCC[C@@H](O)C2)c(N2CCOCC2)c1]

To a solution of N-[5-[6-[(1R,3R)-3-benzyloxycyclohexoxy]-5-morpholino-3-pyridyl]-6-methyl-3-pyridyl]-3-(trifluoromethyl)benzamide (5.5 g, 8.50 mmol, 1 eq) in dichloromethane (100 mL) was added boron tribromide (6.39 g, 25.51 mmol, 2.46 mL, 3 eq). The mixture was stirred at −68° C. for 1 hour. The reaction mixture was quenched by sodium bicarbonate 100 mL at 25° C., and then diluted with water 150 mL extracted with ethyl acetate (80 mL×3). The combined organic layers were washed with brines 150 mL, dried over anhydrous sodium sulfate, filtered and concentrated under reduced pressure. The residue was purified by prep-HPLC. Compound N-[5-[6-[(1R,3R)-3-hydroxycyclohexoxy]-5-morpholino-3-pyridyl]-6-methyl-3-pyridyl]-3-(trifluoromethyl)benzamide (4.2 g, 7.55 mmol, 88% yield) was obtained as a yellow solid. LC/MS (ESI) m/z: 557.2 $[M+1]^+$.

Step 9: Preparation of ethyl 2-(((1R,3R)-3-((2'-methyl-5-morpholino-5'-(3-(trifluoromethyl)benzamido)-[3,3'-bipyridin]-6-yl)oxy)cyclohexyl)oxy) acetate

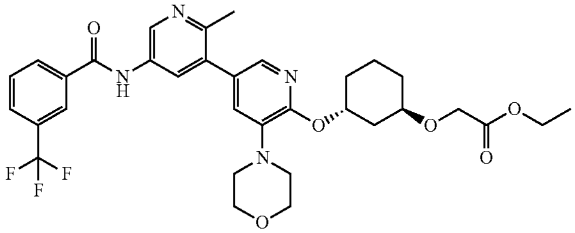 [SMILES: CCOC(=O)CO[C@@H]1CCC[C@@H](Oc2ncc(-c3cc(NC(=O)c4cccc(C(F)(F)F)c4)cnc3C)cc2N2CCOCC2)C1]

To a solution of N-[5-[6-[(1R,3R)-3-hydroxycyclohexoxy]-5-morpholino-3-pyridyl]-6-methyl-3-pyridyl]-3-(trifluoromethyl)benzamide (1 g, 1.80 mmol, 1 eq) in dichloromethane (10 mL) was added diacetoxyrhodium (39 mg, 0.18 mmol, 0.1 eq) and ethyl 2-diazoacetate (615 mg, 5.39 mmol, 3 eq). The mixture was stirred at 25° C. for 12 hours. The reaction mixture was filtered and the filtrate was concentrated. The residue was purified by column chromatography (Petroleum ether:Ethyl acetate=3:1 to 1:3). Compound ethyl 2-[(1R,3R)-3-[[5-[2-methyl-5-[[3-(trifluoromethyl)benzoyl]amino]-3-pyridyl]-3-morpholino-2-pyridyl]oxy]cyclohexoxy]acetate (500 mg, 0.18 mmol, 43% yield) was obtained as a yellow oil. LC/MS (ESI) m/v 643.1 $[M+1]^+$.

Step 10: Preparation of N-(6'-(((1R,3R)-3-(2-hydroxyethoxy)cyclohexyl)oxy)-2-methyl-5'-morpholino-[3,3'-bipyridin]-5-yl)-3-(trifluoromethyl) benzamide

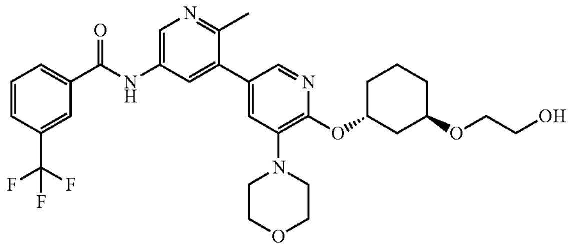 [SMILES: Cc1ncc(NC(=O)c2cccc(C(F)(F)F)c2)cc1-c1cnc(O[C@@H]2CCC[C@@H](OCCO)C2)c(N2CCOCC2)c1]

To a solution of ethyl 2-[(1R,3R)-3-[[5-[2-methyl-5-[[3-(trifluoromethyl)benzoyl]amino]-3-pyridyl]-3-morpholino-2-pyridyl]oxy]cyclohexoxy]acetate (700 mg, 1.09 mmol, 1 eq) in tetrahydrofuran (10 mL) was added lithium aluminium hydride (41 mg, 1.09 mmol, 1 eq). The mixture was stirred at 0~25° C. for 1 hour. The reaction mixture was quenched by water 2 mL at 0° C., and then dried over anhydrous sodium sulfate, filtered and concentrated under reduced pressure. The residue was purified by prep-TLC (dichloromethane:methyl alcohol=10:1). Compound N-[5-[6-[(1R,3R)-3-(2-hydroxy ethoxy)cyclohexoxy]-5-morpholino-3-pyridyl]-6-methyl-3-pyridyl]-3-(trifluoromethyl) benzamide (400 mg, 0.67 mmol, 61% yield) was obtained as a yellow oil. LC/MS (ESI) m/z: 601.1 $[M+1]^+$.

Step 11: Preparation of ethyl 2-(2-(((1R,3R)-3-((2'-methyl-5-morpholino-5'-(3-(trifluoromethyl)benzamido)-[3,3'-bipyridin]-6-yl)oxy)cyclohexyl)oxy) ethoxy)acetate

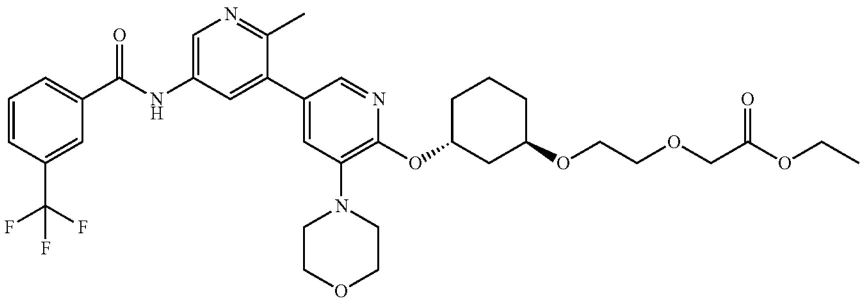 [SMILES: CCOC(=O)COCCO[C@@H]1CCC[C@@H](Oc2ncc(-c3cc(NC(=O)c4cccc(C(F)(F)F)c4)cnc3C)cc2N2CCOCC2)C1]

To a solution of N-[5-[6-[(1R,3R)-3-(2-hydroxyethoxy) cyclohexoxy]-5-morpholino-3-pyridyl]-6-methyl-3-pyridyl]-3-(trifluoromethyl)benzamide (100 mg, 0.16 mmol, 1 eq) in dichloromethane (1 mL) was added diacetoxyrhodium (7 mg, 0.03 mmol, 0.2 eq) and ethyl 2-diazoacetate (189 mg, 1.66 mmol, 10 eq). The mixture was stirred at 25° C. for 1 hour. The reaction mixture was filtered and the filter was concentrated. The residue was purified by prep-TLC (dichloromethane:methyl alcohol=10:1). Compound ethyl 2-[2-[(1R,3R)-3-[[5-[2-methyl-5-[[3-(trifluoromethyl)benzoyl]amino]-3-pyridyl]-3-morpholino-2-pyridyl]oxy]cyclohexoxy]ethoxy]acetate (81 mg, 0.11 mmol, 70% yield) was obtained as a yellow oil. LC/MS (ESI) m/z: 687.2 $[M+1]^+$.

Step 12: Preparation of 2-(2-(((1R,3R)-3-((2'-methyl-5-morpholino-5'-(3-(trifluoromethyl)benzamido)-[3,3'-bipyridin]-6-yl)oxy)cyclohexyl)oxy) ethoxy)acetic acid

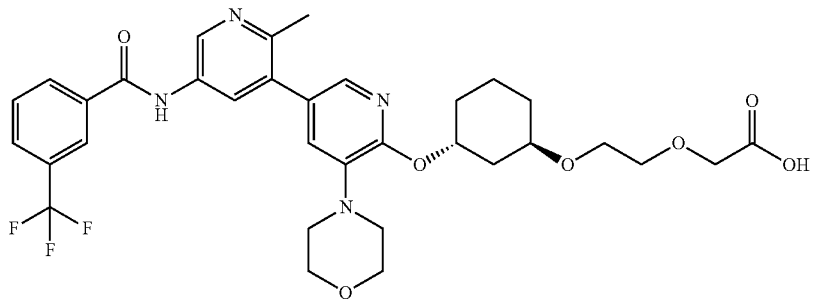 [SMILES: Cc1ncc(NC(=O)c2cccc(C(F)(F)F)c2)cc1-c1cnc(O[C@@H]2CCC[C@@H](OCCOCC(=O)O)C2)c(N2CCOCC2)c1]

To a solution of ethyl 2-[2-[(1R,3R)-3-[[5-[2-methyl-5-[[3-(trifluoromethyl)benzoyl]amino]-3-pyridyl]-3-morpholino-2-pyridyl]oxy]cyclohexoxy]ethoxy]acetate (105 mg, 0.15 mmol, 1 eq) in tetrahydrofuran (2 mL) and water (0.2 mL) was added lithium hydroxide (19 mg, 0.46 mmol, 3 eq). The mixture was stirred at 40° C. for 0.5 hour. The reaction mixture was concentrated under reduced pressure to remove tetrahydrofuran. The residue was diluted with water 2 ml and the mixture was adjusted pH=5 by hydrochloric acid (1 M) 2 mL. The residue was purified by prep-HPLC. Compound 2-[2-[(1R,3R)-3-[[5-[2-methyl-5-[[3-(trifluoromethyl)benzoyl]amino]-3-pyridyl]-3-morpholino-2-pyridyl]oxy]cyclohexoxy]ethoxy]acetic acid (60 mg, 0.09 mmol, 59% yield) was obtained as a white solid. LC/MS (ESI) m/z: 659.2 $[M+1]^+$.

Step 13: Preparation of (2S,4R)-1-((S)-3,3-dimethyl-2-(2-(2-(((1R,3R)-3-((2'-methyl-5-morpholino-5'-(3-(trifluoromethyl)benzamido)-[3,3'-bipyridin]-6-yl)oxy)cyclohexyl)oxy)ethoxy)acetamido)butanoyl)-4-hydroxy-N—((S)-1-(4-(4-methylthiazol-5-yl) phenyl)ethyl)pyrrolidine-2-carboxamide

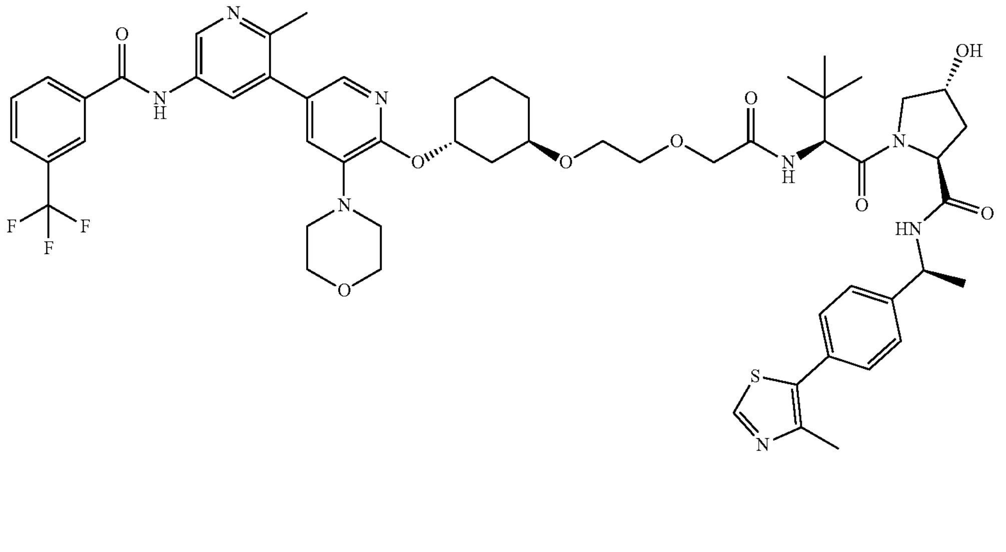 [SMILES: Cc1ncc(NC(=O)c2cccc(C(F)(F)F)c2)cc1-c1cnc(O[C@@H]2CCC[C@@H](OCCOCC(=O)N[C@H](C(=O)N3C[C@H](O)C[C@H]3C(=O)N[C@@H](C)c3ccc(-c4scnc4C)cc3)C(C)(C)C)C2)c(N2CCOCC2)c1]

A mixture of 2-[2-[(1R,3R)-3-[[5-[2-methyl-5-[[3-(trifluoromethyl)benzoyl]amino]-3-pyridyl]-3-morpholino-2-pyridyl]oxy]cyclohexoxy]ethoxy]acetic acid (60 mg, 0.09 mmol, 1 eq), (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (48 mg, 0.1 mmol, 1.1 eq, hydrochloride), hydroxybenzotriazole (14 mg, 0.10 mmol, 1.2 eq), 1-(3-dimethylaminopropyl)-3-ethylcarbodiimide (21 mg, 0.1 mmol, 1.2 eq) and triethylamine (27 mg, 0.27 mmol, 3 eq) in dimethyl formamide (3 mL) was degassed and purged with nitrogen for 3 times, and then the mixture was stirred at 40° C. for 12 hours under nitrogen atmosphere. The reaction mixture was quenched by water 50 mL at 25° C., and then extracted with ethyl acetate (20 mL×3). The combined organic layers were washed with brines (15 mL×2), dried over anhydrous sodium sulfate, filtered and concentrated under reduced pressure. The residue was purified by prep-TLC (dichloromethane:methyl alcohol=10:1). Compound (2S,4R)-1-[(2S)-3,3-dimethyl-2-[[2-[2-[(1R,3R)-3-[[5-[2-methyl-5-[[3-(trifluoromethyl)benzoyl]amino]-3-pyridyl]-3-morpholino-2-pyridyl]oxy]cyclohexoxy]ethoxy]acetyl]amino]butanoyl]-4-hydroxy-N-[(1S)-1-[4-(4-methylthiazol-5-yl)phenyl]ethyl]pyrrolidine-2-carboxamide (34.4 mg, 0.03 mmol, 34% yield, 98% purity) was obtained as a white solid. LC/MS (ESI) m/z: 1086.2 $[M+1]^+$; $^1$H-NMR (400 MHz, DMSO-$d_6$) δ 10.65 (s, 1H), 8.96 (s, 1H), 8.84 (d, J=2.4 Hz, 1H), 8.41 (d, J=7.2 Hz, 1H), 8.31 (s, 1H), 8.27 (d, J=7.3 Hz, 1H), 8.03 (d, J=2.4 Hz, 1H), 7.99 (d, J=7.6 Hz, 1H), 7.83-7.75 (m, 2H), 7.46-7.39 (m, 2H), 7.38-7.30 (m, 3H), 7.19 (d, J=1.6 Hz, 1H), 5.46 (s, 1H), 5.13 (d, J=3.2 Hz, 1H), 4.95-4.82 (m, 1H), 4.53 (d, J=10.0 Hz, 1H), 4.43 (t, J=8.4 Hz, 1H), 4.28 (s, 1H), 4.01-3.93 (m, 2H), 3.79-3.65 (m, 6H), 3.61 (dd, J=3.6, 8.4 Hz, 5H), 3.08 (s, 4H), 2.44 (s, 6H), 2.11-1.97 (m, 2H), 1.92-1.63 (m, 6H), 1.60-1.43 (m, 2H), 1.35 (dd, J=3.6, 6.8 Hz, 3H), 0.92 (d, J=3.2 Hz, 9H).

Exemplary Synthesis of 4-((R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethoxy)-4-oxobutanoic acid (Exemplary Compound 758)

Step 1: Preparation of benzyl (2S,4R)-1-((S)-2-((tert-butoxycarbonyl)amino)-3,3-dimethylbutanoyl)-4-((tert-butyldimethylsilyl)oxy)pyrrolidine-2-carboxylate

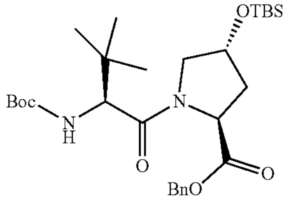 [SMILES: CC(C)(C)OC(=O)N[C@H](C(=O)N1C[C@H](O[Si](C)(C)C(C)(C)C)C[C@H]1C(=O)OCc1ccccc1)C(C)(C)C]

Into a 150-mL round-bottom flask, was placed benzyl (2S,4R)-1-[(2S)-2-[[(tert-butoxy)carbonyl]amino]-3,3-dimethylbutanoyl]-4-hydroxypyrrolidine-2-carboxylate (7 g, 16.11 mmol, 1.00 equiv), imidazole (1.6 g, 23.51 mmol, 1.46 equiv) in dichloromethane (80 mL) at 0° C. This was followed by the addition of TBDMSCl (3.6 g, 23.89 mmol, 1.48 equiv) in portions at 0° C. The resulting solution was stirred for 6 h at room temperature. The reaction was then quenched by the addition of water (60 mL). The resulting mixture was extracted with dichloromethane (50 mL×3), and the organic layers were combined, washed with brine (100 mL×2), dried over anhydrous sodium sulfate and concentrated under vacuum. The residue was applied onto a silica gel column eluting with ethyl acetate/petroleum ether (1:9). This resulted in 5.8 g (66%) of benzyl (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylate as light yellow oil. LC/MS (ESI) m/z: 549.20 $[M+1]^+$.

Step 2: Preparation of (2S,4R)-1-((S)-2-((tert-butoxycarbonyl)amino)-3,3-dimethylbutanoyl)-4-((tert-butyldimethylsilyl)oxy)pyrrolidine-2-carboxylic acid

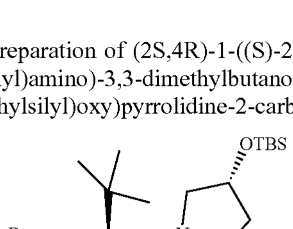

A solution of benzyl (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylate (500 mg, 0.91 mmol, 1.00 equiv) in methanol (15 mL) was charged with Pd/C (10%, 100 mg) under nitrogen atmosphere. The flask was then vacuumed and flushed with hydrogen. The reaction mixture was hydrogenated at room temperature for 16 h under hydrogen atmosphere using a hydrogen balloon, then filtered through a Celite pad and concentrated under reduced pressure. This resulted in 273 mg (65%) of (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylic acid as colorless oil. LC/MS (ESI) m/z: 459.30 $[M+1]^+$.

Step 3: Preparation of tert-butyl ((S)-1-((2S,4R)-4-((tert-butyldimethylsilyl)oxy)-2-(((R)-2-hydroxy-1-(4-(4-methylthiazol-5-yl)phenyl)ethyl)carbamoyl)pyrrolidin-1-yl)-3,3-dimethyl-1-oxobutan-2-yl)carbamate

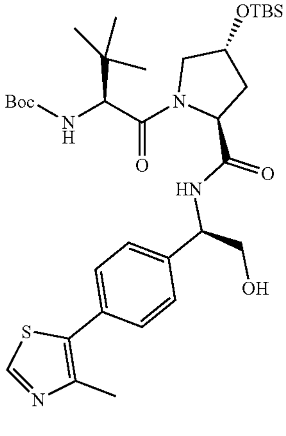 [SMILES: Cc1ncsc1-c1ccc([C@H](CO)NC(=O)[C@@H]2C[C@@H](O[Si](C)(C)C(C)(C)C)CN2C(=O)[C@@H](NC(=O)OC(C)(C)C)C(C)(C)C)cc1]

Into a 25-mL round-bottom flask, was placed (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylic acid (930 mg, 1 equiv), (2R)-2-amino-2-[4-(4-methyl-1,3-thiazol-5-yl)phenyl]ethan-1-ol hydrochloride (550 mg), HATU (930 mg), DIEA (1 g) in DMF (5 mL). The resulting solution was stirred for 1 h at room temperature. The reaction mixture was diluted with water (80 mL) and extracted with ethyl acetate (50 mL×3). The combined organic layer was dried over anhydrous sodium sulfate and concentrated. The residue was applied onto a silica gel column eluting with ethyl acetate/petroleum ether (1:0). This resulted in 460 mg of tert-butyl N-[(2S)-1-[(2S,4R)-4-[(tert-butyldimethylsilyl)oxy]-2-[[(1R)-2-hydroxy-1-[4-(4-methyl-1,3-thiazol-5-yl)phenyl]ethyl]carbamoyl]pyrrolidin-1-yl]-3,3-dimethyl-1-oxobutan-2-yl]carbamate as light yellow oil. LC/MS (ESI) m/z: 675.20 $[M+1]^+$.

Step 4: Preparation of (2S,4R)-1-((S)-2-amino-3,3-dimethylbutanoyl)-4-((tert-butyldimethylsilyl)oxy)-N—((R)-2-hydroxy-1-(4-(4-methylthiazol-5-yl)phenyl)ethyl)pyrrolidine-2-carboxamide

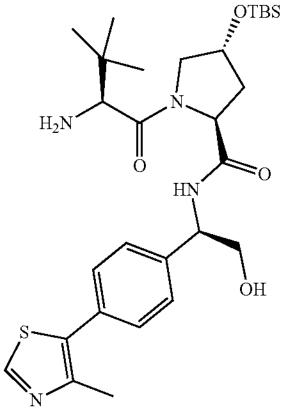 [SMILES: Cc1ncsc1-c1ccc([C@H](CO)NC(=O)[C@@H]2C[C@@H](O[Si](C)(C)C(C)(C)C)CN2C(=O)[C@@H](N)C(C)(C)C)cc1]

Into a 25 mL round-bottom flask were added tert-butyl N-[(2S)-1-[(2S,4R)-4-[(tert-butyldimethylsilyl)oxy]-2-[[(1R)-2-hydroxy-1-[4-(4-methyl-1,3-thiazol-5-yl)phenyl]ethyl]carbamoyl]pyrrolidin-1-yl]-3,3-dimethyl-1-oxobutan-2-yl]carbamate (660 mg, 980 mmol, 1 equiv) in dichloromethane (10 mL). To the above mixture was added TFA (3 mL) dropwise at 0° C. The resulting mixture was stirred for 0.5 h at 0° C., and then was quenched by the addition of saturated sodium bicarbonate solution (100 mL) at room temperature. The resulting mixture was extracted with DCM (10 mL×2). The combined organic layer was dried over sodium sulfate and concentrated under reduced pressure. This resulted in (2S,4R)-1-[(2S)-2-amino-3,3-dimethylbutanoyl]-4-[(tert-butyldimethylsilyl)oxy]-N-[(1R)-2-hydroxy-1-[4-(4-methyl-1,3-thiazol-5-yl)phenyl]ethyl]pyrrolidine-2-carboxamide, trifluoroacetic acid salt (760 mg) as a yellow oil. LC/MS (ESI) m/z: 575.20 $[M+1]^+$.

Step 5: Preparation of tert-butyl (R)-2-(4-((4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)methyl)piperidin-1-yl)acetate

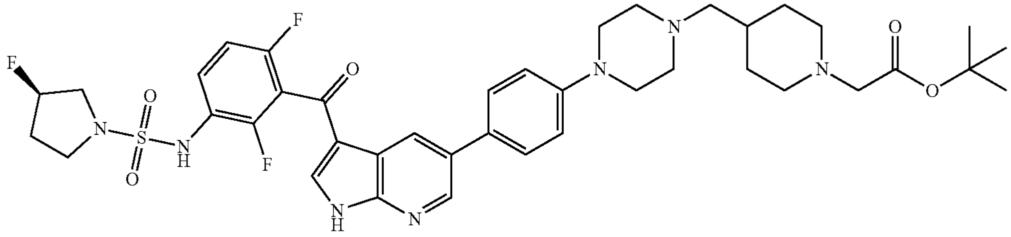 [SMILES: CC(C)(C)OC(=O)CN1CCC(CN2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 100-mL round-bottom flask, was placed a solution of tert-butyl 2-(4-((4-(4-(4,4,5,5-tetramethyl-1,3,2-dioxaborolan-2-yl)phenyl)piperazin-1-yl)methyl)piperidin-1-yl) acetate (783.4 mg, 1.57 mmol, 1.50 equiv), (R)—N-(3-(5-bromo-1H-pyrrolo[2,3-b]pyridine-3-carbonyl)-2,4-difluorophenyl)-3-fluoropyrrolidine-1-sulfonamide (525.0 mg, 1.05 mmol, 1.00 equiv), sodium carbonate (222.6 mg, 2.10 mmol, 2.00 equiv), $Pd(dppf)Cl_2$ (85.5 mg, 0.10 mmol, 0.10 equiv) in 1,4-dioxane (15 mL) and water (3 mL). Under nitrogen the resulting solution was stirred overnight at 100° C. in an oil bath. The residue was evaporated concentrated under reduced pressure and applied onto a silica gel column with ethyl acetate/petroleum ether (1:0). This resulted in 621.5 mg (75%) of (R)-tert-butyl 2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate as a yellow solid. LC/MS (ESI) m/z: 796.20 $[M+1]^+$.

Step 6: Preparation of (R)-2-(4-((4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)methyl)piperidin-1-yl)acetic acid

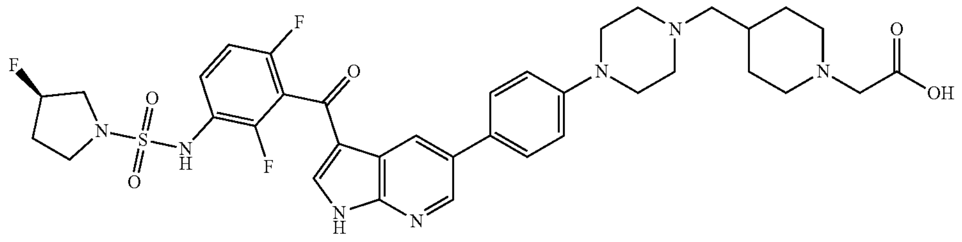 [SMILES: O=C(O)CN1CCC(CN2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 50-mL round-bottom flask, was placed a solution of (R)-tert-butyl 2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate (621.5 mg, 0.78 mmol, 1.00 equiv), 2,2,2-trifluoroacetaldehyde (8 mL) in dichloromethane (8 mL). The resulting solution was stirred for 5 h at room temperature. The residue was evaporated concentrated under reduced pressure and applied onto a silica gel column with methanol/chloroform (1:2). This resulted in 500.0 mg (87%) of (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetic acid as a yellow solid. LC/MS (ESI) m/z: 740.15 $[M+1]^+$.

Step 7: Preparation of (2S,4R)-4-((tert-butyldimethylsilyl)oxy)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-N—((R)-2-hydroxy-1-(4-(4-methylthiazol-5-yl)phenyl)ethyl)pyrrolidine-2-carboxamide Into a 50 mL round-bottom flask were added 2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (700 mg, 950 mmol, 1 equiv), (2S,4R)-1-[(2S)-2-amino-3,3-dimethylbutanoyl]-4-[(tert-butyldimethylsilyl)oxy]-N-[(1R)-2-hydroxy-1-[4-(4-methyl-1,3-thiazol-5-yl)phenyl]ethyl]pyrrolidine-2-carboxamide, trifluoroacetic acid salt (736.5 mg in 10 mL DMF, 1.07 mol, 1.13 equiv), DIEA (50 mg, 0.39 mmol, 3.25 equiv) in DMF (5 mL) at room temperature. The resulting mixture was stirred for 1 h at room temperature. The mixture was diluted with water (22 mL) and extracted with EtOAc (30 mL×3). The combined organic layers were washed with brine (10 mL), dried over sodium sulfate and concentrated under vacuum. The residue was purified by silica gel column chromatography eluting with dichloromethane/MeOH (9:1) to afford (2R)-2-[[(2S,4R)-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-(760 mg, 65.60%) as a yellow oil.

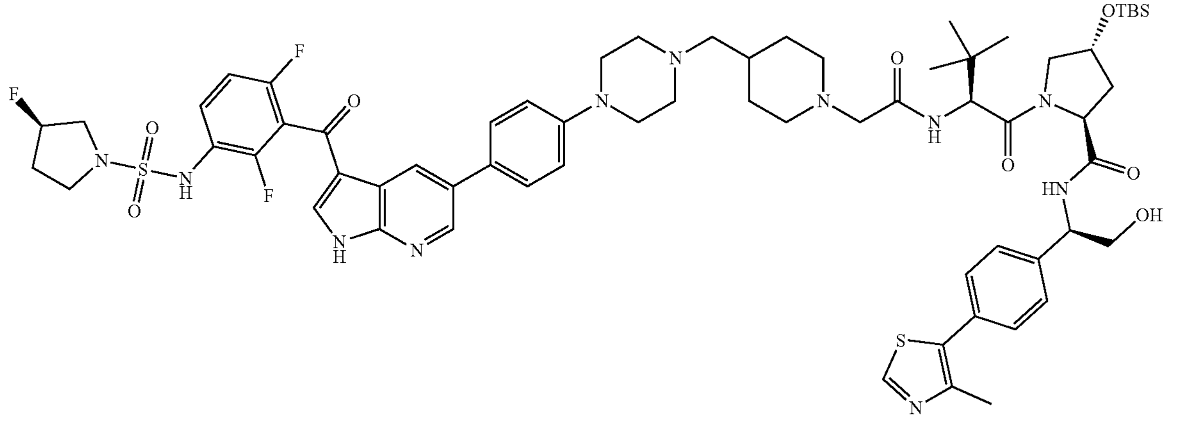 [SMILES: Cc1ncsc1-c1ccc([C@H](CO)NC(=O)[C@@H]2C[C@@H](O[Si](C)(C)C(C)(C)C)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Step 8: Preparation of 4-((R)-2-((2S,4R)-4-((tert-butyldimethylsilyl)oxy)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)pyrrolidine-2-carboxamido)-2-(4-(4-methylthiazol-5-yl)phenyl)ethoxy)-4-oxobutanoic acid

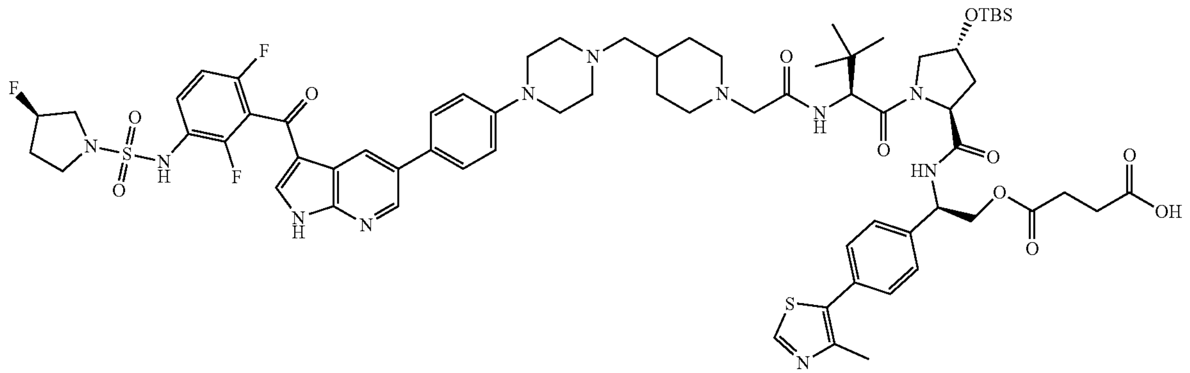 [SMILES: Cc1ncsc1-c1ccc([C@H](COC(=O)CCC(=O)O)NC(=O)[C@@H]2C[C@@H](O[Si](C)(C)C(C)(C)C)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 50-mL flask purged and maintained with an inert atmosphere of nitrogen, was placed a solution of (2S,4R)-4-[(tert-butyldimethylsilyl)oxy]-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]-N-[(1R)-2-hydroxy-1-[4-(4-methyl-1,3-thiazol-5-yl)phenyl]ethyl]pyrrolidine-2-carboxamide (100.00 mg, 0.077 mmol, 1.00 equiv), DMAP (37.69 mg, 0.308 mmol, 4 equiv), TEA (15.61 mg, 0.154 mmol, 2 equiv), oxolane-2,5-dione (30.87 mg, 0.308 mmol, 4.00 equiv) in DCM (20 mL). The resulting solution was stirred for 16 h at room temperature. The resulting solution was extracted with (50 mL×3) of dichloromethane. The combined organic layers were dried over anhydrous sodium sulfate and concentrated under reduced pressure. This resulted in 126 mg of 4-[(2R)-2-[[(2S,4R)-4-[(tert-butyldimethylsilyl)oxy]-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]pyrrolidin-2-yl]formamido]-2-[4-(4-methyl-1,3-thiazol-5-yl)phenyl]ethoxy]-4-oxobutanoic acid as a solid. LC/MS (ESI) m/z: 1396 $[M+1]^+$.

Step 9: Preparation of 4-((R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethoxy)-4-oxobutanoic acid

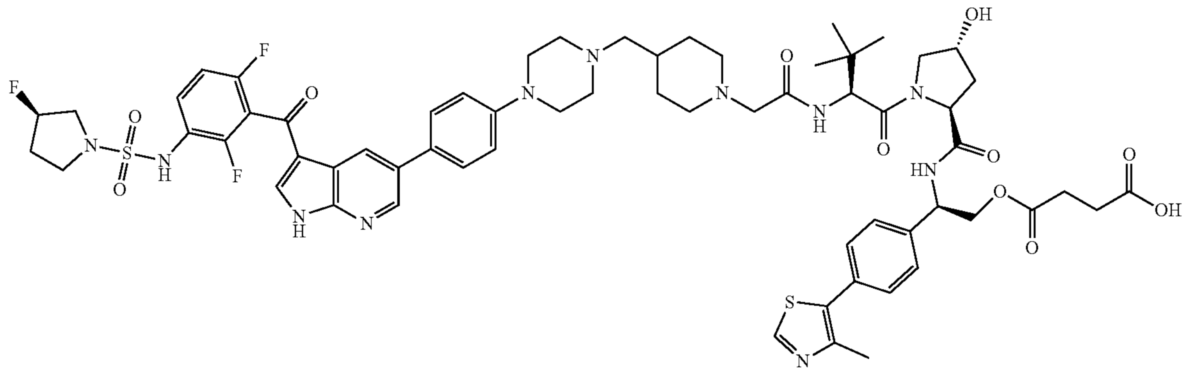 [SMILES: Cc1ncsc1-c1ccc([C@H](COC(=O)CCC(=O)O)NC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 100-mL round-bottom flask, was placed 4-[(2R)-2-[[(2S,4R)-4-[(tert-butyldimethylsilyl)oxy]-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]pyrrolidin-2-yl]formamido]-2-[4-(4-methyl-1,3-thiazol-5-yl)phenyl]ethoxy]-4-oxobutanoic acid (110.00 mg, 0.308 mmol, 1 equiv) in dioxane (8.00 mL), to which was added concentrated hydrogen chloride (1.00 mL). The resulting solution was stirred for 1 h at room temperature. The resulting solution was extracted with (50 mL×3) of dichloromethane. The combined organic layers were concentrated under reduced pressure. The residue was purified by Prep-HPLC. This resulted in 50 mg of 4-[(2R)-2-[[(2S,4R)-1-[(2S)-2-[2-(4-[[4-(4-[3-[2,6-difluoro-3-([[(3R)-3- fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]-4-hydroxypyrrolidin-2-yl]formamido]-2-[4-(4-methyl-1,3-thiazol-5-yl)phenyl]ethoxy]-4-oxobutanoic acid as a yellow solid. LC/MS (ESI) m/z: 1282 $[M+1]^+$; $^1$H-NMR (300 MHz, DMSO-$d_6$) δ 12.91 (s, 1H), 9.83 (s, 1H), 8.99 (s, 1H), 8.65 (s, 1H), 8.60-8.55 (m, 2H), 8.07 (s, 1H), 7.62 (s, 3H), 7.60-7.37 (m, 4H), 7.30-7.24 (m, 1H), 7.09-7.07 (m, 2H), 5.21-5.13 (m, 2H), 4.54-4.44 (m, 2H), 4.29-4.23 (m, 3H), 3.62-3.31 (m, 13H), 2.91-2.73 (m, 4H), 2.56-2.54 (m, 3H), 2.50-2.47 (m, 7H), 2.28-1.96 (m, 8H), 1.81-1.77 (m, 4H), 1.31-1.11 (m, 2H), 0.95-0.86 (s, 9H).

Exemplary Synthesis of 2-(2-((R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethoxy)-2-oxoethoxy)acetic acid (Exemplary Compound 759)

Step 1: Preparation of 2-(2-((R)-2-((2S,4R)-4-((tert-butyldimethylsilyl)oxy)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)pyrrolidine-2-carboxamido)-2-(4-(4-methylthiazol-5-yl)phenyl)ethoxy)-2-oxoethoxy)acetic acid

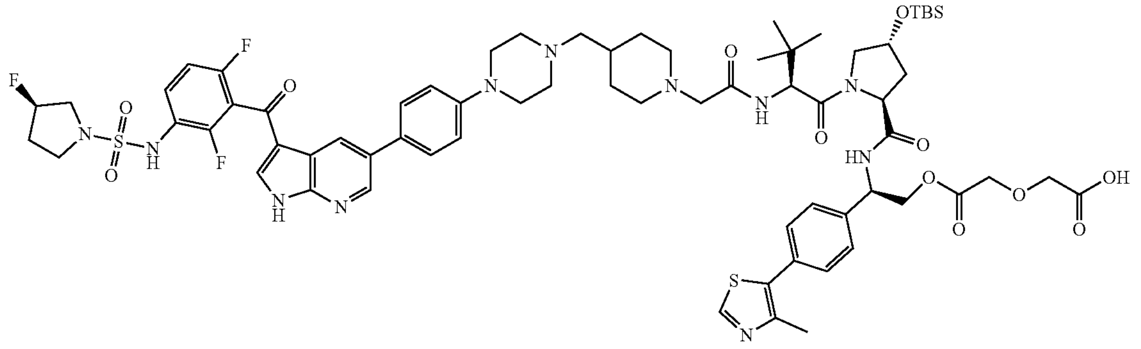 [SMILES: Cc1ncsc1-c1ccc([C@H](COC(=O)COCC(=O)O)NC(=O)[C@@H]2C[C@@H](O[Si](C)(C)C(C)(C)C)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 25-mL flask purged and maintained with an inert atmosphere of nitrogen, was placed a solution of (2S,4R)-4-[(tert-butyldimethylsilyl)oxy]-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]-N-[(1R)-2-hydroxy-1-[4-(4-methyl-1,3-thiazol-5-yl)phenyl]ethyl]pyrrolidine-2-carboxamide (100.00 mg, 0.077 mmol, 1.00 equiv), DMAP (28.27 mg, 0.231 mmol, 3.00 equiv), TEA (15.61 mg, 0.154 mmol, 2 equiv), 1,4-dioxane-2,6-dione (35.81 mg, 0.308 mmol, 4.00 equiv) in DCM (5.00 mL). The resulting solution was stirred for 16 h at room temperature. The resulting solution was extracted with (50 mL×3) of dichloromethane and the organic layers combined and dried over anhydrous sodium sulfate and concentrated under vacuum. This resulted in 137.7 mg of 2-[2-[(2R)-2-[[(2S,4R)-4-[(tert-butyldimethylsilyl)oxy]-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetamido]-3,3-dimethylbutanoyl]pyrrolidin-2-yl]formamido]-2-[4-(4-methyl-1,3-thiazol-5-yl)phenyl]ethoxy]-2-oxoethoxy]acetic acid as a solid. LC/MS (ESI) m/z: 1142 $[M+1]^+$.

Step 2: Preparation of 2-(2-((R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethoxy)-2-oxoethoxy) acetic acid

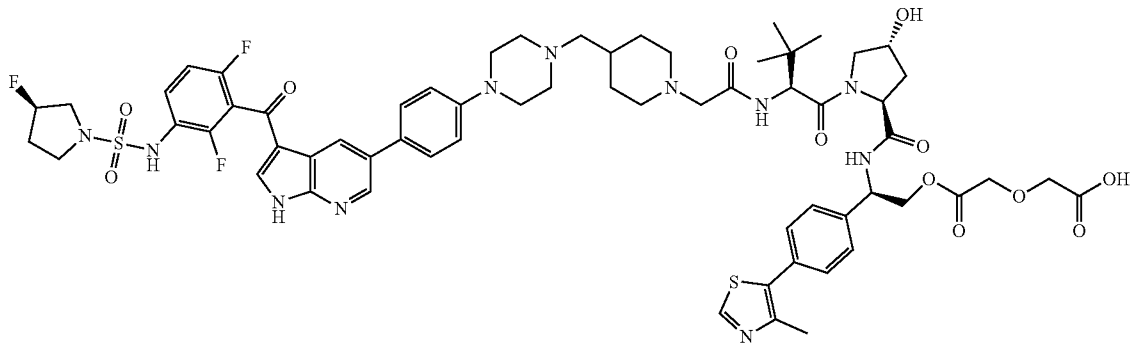 [SMILES: Cc1ncsc1-c1ccc([C@H](COC(=O)COCC(=O)O)NC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

A solution of 2-[2-[(2R)-2-[[(2S,4R)-4-[(tert-butyldimethylsilyl)oxy]-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl] methyl]piperidin-1-yl)acetamido]-3,3-dimeth ylbutanoyl] pyrrolidin-2-yl]formamido]-2-[4-(4-methyl-1,3-thiazol-5-yl)phenyl]ethoxy]-2-oxoethoxy]acetic acid (137.70 mg) in dioxane (8.00 mL) was charged with concentrated hydrogen chloride (1.00 mL). The resulting solution was stirred for 1 hr at room temperature. The resulting mixture was concentrated under reduced pressure. The residue was purified by Prep-HPLC. This resulted in 50 mg of 2-[2-[(2R)-2-[[(2S,4R)-1-[(2S)-2-[2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl] piperidin-1-yl)acetamido]-3,3-dimethylbutanoyl]-4-hydroxypyrrolidin-2-yl]formamido]-2-(4-methylphenyl) ethoxy]-2-oxoethoxy]acetic acid as a light yellow solid. LC/MS (ESI) m/z: 1298.45 $[M+1]^+$; $^1$H-NMR (300 MHz, DMSO-$d_6$) δ 8.99 (s, 1H), 8.64-8.61 (m, 2H), 8.53 (s, 1H), 8.06 (s, 1H), 7.89-7.86 (m, 1H), 7.61 (s, 3H), 7.58-7.46 (m, 4H), 7.28-7.22 (m, 1H), 7.08-7.05 (d, J=8.1 Hz, 2H), 5.31-5.19 (m, J=2H), 4.53-4.43 (m, 2H), 4.38-4.16 (m, 6H), 4.06-3.95 (m, 3H), 3.49-3.38 (m, 3H), 3.29-3.13 (m, 6H), 3.23-2.87 (m, 6H), 2.68-2.56 (m, 3H), 2.50-2.46 (m, 3H), 2.26-2.18 (m, 8H), 1.87-1.71 (m, 3H), 1.70-1.53 (m, 1H), 1.31-1.12 (m, 3H), 1.01-0.87 (s, 9H).

Exemplary Synthesis of (3R)—N-(3-(5-(4-(4-((((1r,3r)-3-((2-(2,6-dioxopiperidin-3-yl)-1,3-dioxoisoindolin-5-yl)oxy)cyclobutyl)(isopropyl)amino)methyl) piperidin-1-yl)phenyl)-1H-pyrrolo[2,3-b]pyridine-3-carbonyl)-2,4-difluorophenyl)-3-fluoropyrrolidine-1-sulfonamide (Exemplary Compound 760)

Step 1: Preparation of tert-butyl((1s,3s)-3-hydroxycyclobutyl)carbamate

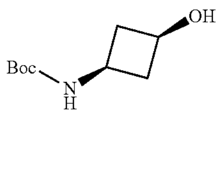 [SMILES: CC(C)(C)OC(=O)N[C@H]1C[C@@H](O)C1]

To a solution of tert-butyl N-(3-oxocyclobutyl)carbamate (15.00 g, 80.98 mmol, 1.00 eq) in tetrahydrofuran (150 mL) was added dropwise sodium borohydride (1.53 g, 40.49 mmol, 0.50 eq) in tetrahydrofuran (100 mL) and water (100 mL) at −70° C. for 2 h. The mixture was stirred at −70° C. for 2 h. Then to the mixture was added water (100 mL) and it was warmed to 20° C. The mixture was extracted with ethyl acetate (2×200 mL). The combined organic layers were washed with brine (2×400 mL), dried over anhydrous sodium sulfate, filtered and concentrated under reduced pressure to give a white solid. The solid was dissolved with a solution of petroleum ether:ethyl acetate (50 mL, v:v=20:1). The suspension solution was stirred for 0.5 h and then filtered to give tert-butyl N-(3-hydroxycyclobutyl)carbamate (13.80 g, 73.70 mmol, 91% yield). $^1$H-NMR (400 MHz, DMSO-$d_6$) δ 7.00 (d, J=7.2 Hz, 1H), 4.96 (d, J=5.6 Hz, 1H), 3.62-3.82 (m, 1H), 3.33-3.47 (m, 1H), 2.35-2.47 (m, 2H), 1.63-1.76 (m, 2H), 1.36 (s, 9H).

Step 2: Preparation of dimethyl 4-((1r,3r)-3-((tert-butoxycarbonyl)amino)cyclobutoxy)phthalate

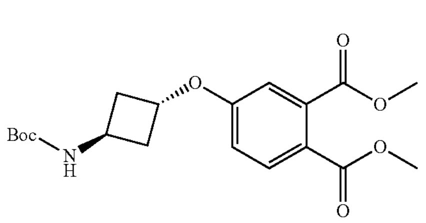 [SMILES: COC(=O)c1ccc(O[C@H]2C[C@H](NC(=O)OC(C)(C)C)C2)cc1C(=O)OC]

To a solution of dimethyl 4-hydroxybenzene-1,2-dicarboxylate (17.04 g, 81.07 mmol, 1.10 eq), tert-butyl N-(3-hydroxycyclobutyl)carbamate (13.80 g, 73.70 mmol, 1.00 eq) and triphenylphosphine (25.13 g, 95.82 mmol, 1.30 eq) in tetrahydrofuran (150 mL) was added dropwise diisopropyl azodicarboxylate (19.37 g, 95.82 mmol, 1.30 eq) at 0° C. The mixture was warmed to 15° C. The mixture was stirred at 15° C. for 15 h. The mixture was diluted with water (150 mL) and extracted with ethyl acetate (2×100 mL). The organic layers were washed with brine (2×100 mL), dried over anhydrous sodium sulfate and concentrated under reduced pressure to give a residue. The residue was purified by column chromatography (petroleum ether:ethyl acetate=10:1 to 3:1) to give dimethyl 4-[3-(tert-butoxycar bonylamino)cyclobutoxy]benzene-1,2-dicarboxylate (25.50 g, 67.21 mmol, 91% yield) as a red oil. LC/MS (ESI) m/z: 402.1 [M+23]$^+$.

Step 3: Preparation of dimethyl 4-((1r,3r)-3-aminocyclobutoxy)phthalate

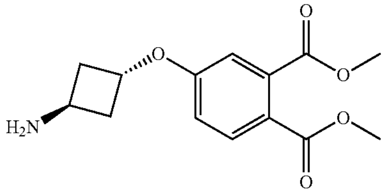 [SMILES: COC(=O)c1ccc(O[C@H]2C[C@H](N)C2)cc1C(=O)OC]

To a solution of dimethyl 4-[3-(tert-butoxycarbonylamino)cyclobutoxy]benzene-1,2-dicarboxylate (25.50 g, 67.21 mmol, 1.00 eq) in dichloromethane (30 mL) was added hydrochloric acid/ethyl acetate (4 M, 30 mL, 1.79 eq) at 20° C. The mixture was stirred at 20° C. for 1 h. The mixture was concentrated under reduced pressure to give a residue. The residue was dissolved with water (60 mL) and extracted with ethyl acetate (4×50 mL). The water phase was adjusted to pH=8 by ammonium hydroxide and concentrated under reduced pressure to give dimethyl 4-(3-aminocyclobutoxy)benzene-1,2-dicarboxylate (19.00 g) as a light red solid. $^1$H-NMR (400 MHz, DMSO-$d_6$) δ 7.92-8.60 (m, 2H), 7.75-7.80 (m, 1H), 7.02-7.06 (m, 1H), 6.98-7.01 (m, 1H), 5.09-5.18 (m, 1H), 3.80-3.84 (m, 1H), 3.80 (s, 3H), 3.77 (s, 3H), 2.58-2.69 (m, 2H), 2.37-2.46 (m, 2H).

Step 4: Preparation of dimethyl 4-((1r,3r)-3-(((1-(tert-butoxycarbonyl)piperidin-4-yl)methyl)amino) cyclobutoxy)phthalate

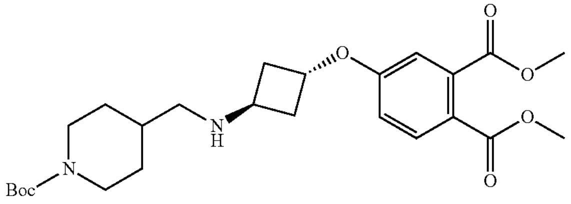 [SMILES: COC(=O)c1ccc(O[C@H]2C[C@H](NCC3CCN(C(=O)OC(C)(C)C)CC3)C2)cc1C(=O)OC]

Into a 100-mL round-bottom flask, was placed tert-butyl 4-formylpiperidine-1-carboxylate (680 mg, 3.18 mmol, 1.00 equiv), 1,2-dimethyl 4-[(1r,3r)-3-aminocyclobutoxy]benzene-1,2-dicarboxylate hydrochloride (1 g, 3.16 mmol, 0.99 equiv), dichloromethane (40 mL). This was followed by the addition of DIEA (about 0.2 mL, adjusted the PH=8~9) dropwise with stirring at room temperature in 1 hr. To this was added $NaBH(OAc)_3$ (1.4 g, 6.60 mmol, 2.1 equiv), in portions at room temperature in 5 min. HOAc (about 0.4 mL, adjusted the PH=5-6) The resulting solution was stirred for 1 h at room temperature. The reaction was then quenched by the addition of 30 mL of water. The resulting solution was extracted with 3×30 mL of dichloromethane and the organic layers combined. The resulting mixture was washed with 1×30 mL of saturated sodium chloride aqueous solution. The mixture was dried over anhydrous sodium sulfate and concentrated under vacuum. The residue was applied onto a silica gel column with dichloromethane/methanol (9:1). The desired product was obtained by concentrated under vacuum. This resulted in 1.23 g (81%) of 1,2-dimethyl 4-[(1r,3r)-3-[([1-[(tert-butoxy)carbonyl]piperidin-4-yl] methyl)amino]cyclobutoxy]benzene-1,2-dicarboxylate as light yellow oil.

Step 5: Preparation of dimethyl 4-((1r,3r)-3-(((1-(tert-butoxycarbonyl)piperidin-4-yl)methyl)(isopropyl)amino)cyclobutoxy)phthalate

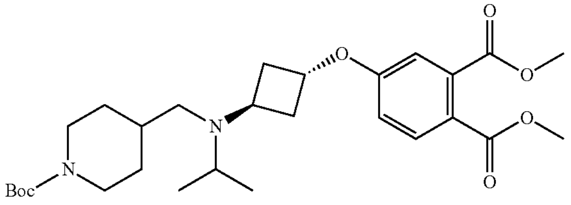 [SMILES: COC(=O)c1ccc(O[C@H]2C[C@H](N(CC3CCN(C(=O)OC(C)(C)C)CC3)C(C)C)C2)cc1C(=O)OC]

Into a 100-mL round-bottom flask purged and maintained with an inert atmosphere of nitrogen, was placed a solution of 1,2-dimethyl 4-[(1r,3r)-3-[([1-[(tert-butoxy)carbonyl]piperidin-4-yl]methyl)amino]cyclobutoxy]benzene-1,2-dicarboxylate (1.23 g, 2.44 mmol, 1.00 equiv) in $^i$PrOH/Acetone (20/20 mL). Ti($^i$PrO)$_4$ (693 mg, 2.44 mmol, 1.00 equiv) and 4 A MS 10 g were added into. $NaBH_3CN$ (461 mg, 7.32 mmol, 3.00 equiv) was added into after stirred 1 hour at rt. The resulting solution was stirred for 20 h at 60° C. The reaction mixture was cooled. The solids were filtered out. The resulting mixture was concentrated under vacuum. The residue was applied onto a silica gel column with dichloromethane/methanol (10/1). The desired product was obtained by concentrated under vacuum. This resulted in 841 mg (67%) of 1,2-dimethyl 4-[(1r,3r)-3-[([1-[(tert-butoxy)carbonyl]piperidin-4-yl]methyl)(propan-2-yl)amino] cyclobutoxy]benzene-1,2-dicarboxylate as a yellow solid. LC/MS (ESI) m/z: 518.30 [M+1]$^+$.

Step 6: Preparation of dimethyl 4-((1r,3r)-3-(isopropyl(piperidin-4-ylmethyl)amino)cyclobutoxy)phthalate

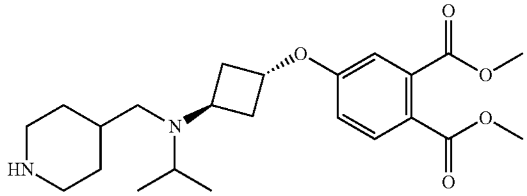 [SMILES: COC(=O)c1ccc(O[C@H]2C[C@H](N(CC3CCNCC3)C(C)C)C2)cc1C(=O)OC]

Into a 100-mL round-bottom flask, was placed 1,2-dimethyl 4-[(1r,3r)-3-[([1-[(tert-butoxy)carbonyl]piperidin-4-yl]methyl)(propan-2-yl)amino]cyclobutoxy]benzene-1,2-dicarboxylate (841 mg, 1.62 mmol, 1.00 equiv), HCl (gas) in 1,4-dioxane (20 mL, 4 mol/L). The resulting solution was stirred for 1 hour at room temperature. The desired product was obtained by concentrated under vacuum. This resulted in 863 mg of 1,2-dimethyl 4-[(1r,3r)-3-[[(piperidin-4-yl) methyl](propan-2-yl)amino]cyclobutoxy]benzene-1,2-dicarboxylate hydrogen chloride as yellow solid. LC/MS (ESI) m/z: 418.25 [M+1]$^+$.

Step 7: Preparation of dimethyl 4-((1r,3r)-3-(((1-(4-bromophenyl)piperidin-4-yl)methyl)(isopropyl)amino)cyclobutoxy)phthalate

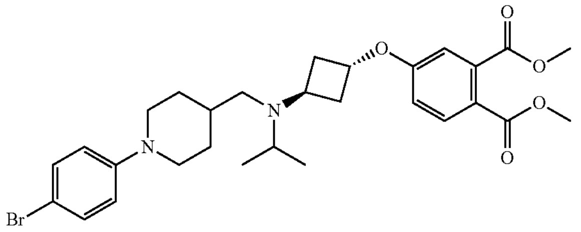 [SMILES: COC(=O)c1ccc(O[C@H]2C[C@H](N(CC3CCN(c4ccc(Br)cc4)CC3)C(C)C)C2)cc1C(=O)OC]

Into a 250-mL round-bottom flask, was placed 1,2-dimethyl 4-[(1r,3r)-3-[[(piperidin-4-yl)methyl](propan-2-yl)amino]cyclobutoxy]benzene-1,2-dicarboxylate (2.40 g, 5.734 mmol, 1.00 equiv), (4-bromophenyl)boronic acid (2.30 g, 11.469 mmol, 2.00 equiv), dichloromethane (100 mL), TEA (2.32 g, 22.937 mmol, 4.00 equiv), $Cu(OAc)_2$ (2.08 g, 11.469 mmol, 2.00 equiv). The resulting solution was stirred for 72 hours at room temperature under air atmosphere. After filtration then diluted with water (100 mL). The resulting mixture was extracted with dichloromethane (200 mL×3), the combined organic layer was dried over anhydrous sodium and concentrated under vacuum. Then eluting with ethyl acetate/petroleum ether (1:3). This resulted in 880 mg (27%) of 1,2-dimethyl 4-[(1r,3r)-3-([[1-(4-bromophenyl)piperidin-4-yl]methyl](propan-2-yl)amino)cyclobutoxy]benzene-1,2-dicarboxylate as yellow oil. LC/MS (ESI) m/z: 572.19 $[M+1]^+$.

Into a 25-mL round-bottom flask purged and maintained with an inert atmosphere of nitrogen, was placed 1,2-dimethyl 4-[(1r,3r)-3-([[1-(4-bromophenyl)piperidin-4-yl]methyl](propan-2-yl)amino)cyclobutoxy]benzene-1,2-dicarboxylate (740.00 mg, 1.290 mmol, 1.00 equiv), 4,4,5,5-tetramethyl-2-(4,4,5,5-tetramethyl-1,3,2-dioxaborolan-2-yl)-1,3,2-dioxaborolane (655.30 mg, 2.581 mmol, 2.00 equiv), dioxane (5.00 mL, 59.020 mmol, 45.74 equiv), KOAc (253.26 mg, 2.581 mmol, 2.00 equiv), $Pd(dppf)Cl_2$ (94.41 mg, 0.129 mmol, 0.10 equiv). The resulting solution was stirred for 12 hours at 90° C. in an oil bath. The reaction was cooled to room temperature and dried over anhydrous sodium and concentrated under vacuum. Then eluting with ethyl acetate/petroleum ether (1:1). This resulted in 590 mg (73%) of 1,2-dimethyl 4-[(1r,3r)-3-[(propan-2-yl)([1-[4-(4,4,5,5-tetramethyl-1,3,2-dioxaborolan-2-yl)phenyl]piperidin-4-yl]methyl)amino]cyclobutoxy]benzene-1,2-dicarboxylate as brown oil. LC/MS (ESI) m/z: 620.36 $[M+1]^+$.

Step 9: Preparation of dimethyl 4-((1r,3r)-3-(((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)(isopropyl)amino)cyclobutoxy)phthalate

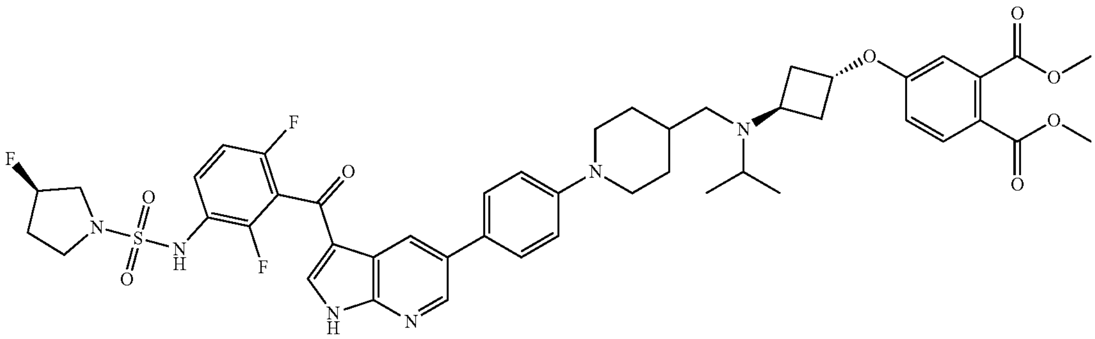

Step 8: Preparation of dimethyl 4-((1r,3r)-3-(isopropyl((1-(4-(4,4,5,5-tetramethyl-1,3,2-dioxaborolan-2-yl)phenyl)piperidin-4-yl)methyl)amino)cyclobutoxy)phthalate

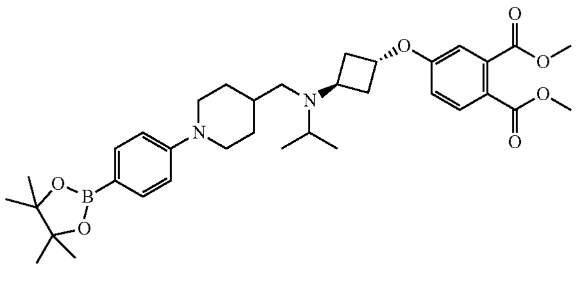

Into a 25-mL sealed tube purged and maintained with an inert atmosphere of nitrogen, was placed 1,2-dimethyl 4-[(1r,3r)-3-[isopropyl([1-[4-(4,4,5-trimethyl-1,3,2-dioxaborolan-2-yl)phenyl]piperidin-4-yl]methyl)amino]cyclobutoxy]phthalate (570.00 mg, 1.1 equiv), (3R)—N-(3-[5-bromo-1H-pyrrolo[2,3-b]pyridine-3-carbonyl]-2,4-difluorophenyl)-3-fluoropyrrolidine-1-sulfonamide (420 mg, 1.00 equiv), dioxane (5 mL), $H_2O$ (1 mL), $Na_2CO_3$ (177 mg, 2.0 equiv), $Pd(dppf)Cl_2$ (68 mg, 0.1 equiv). The final reaction mixture was irradiated with microwave radiation for 2 hours at 100° C. The reaction was cooled to room temperature and dried over anhydrous sodium and concentrated under vacuum. The residue was applied onto a silica gel column eluting with ethyl acetate (100%). This resulted in 220 mg (29%) of 1,2-dimethyl 4-[(1r,3r)-3-[[(1-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]piperidin-4-yl)methyl](isopropyl)amino]cyclobutoxy]phthalate as a yellow solid. LC/MS (ESI) m/z: 916.34 $[M+1]^+$.

Step 10: Preparation of 4-((1r,3r)-3-(((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)(isopropyl)amino)cyclobutoxy)phthalic acid

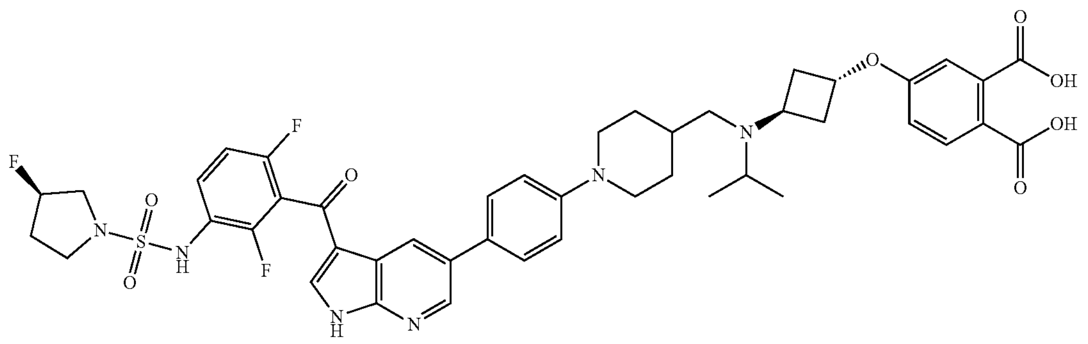 [SMILES: CC(C)N(CC1CCN(c2ccc(-c3cnc4[nH]cc(C(=O)c5c(F)ccc(NS(=O)(=O)N6CC[C@@H](F)C6)c5F)c4c3)cc2)CC1)[C@H]1C[C@H](Oc2ccc(C(=O)O)c(C(=O)O)c2)C1]

Into a 25-mL round-bottom flask, was placed 1,2-dimethyl 4-[(1r,3r)-3-[[(1-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]piperidin-4-yl)methyl](isopropyl)amino]cyclobutoxy]phthalate (200.00 mg, 0.218 mmol, 1.00 equiv), MeOH (10.00 mL), $H_2O$ (4.00 mL). This was followed by the addition of NaOH (174.47 mg, 4.362 mmol, 20.00 equiv) at 10° C. The resulting solution was stirred for 20 hours at 50° C. in an oil bath. The reaction was cooled to room temperature and dried over anhydrous sodium and concentrated under vacuum. This resulted in 210 mg of 4-[(1r,3r)-3-[[(1-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]piperidin-4-yl)methyl](isopropyl)amino]cyclobutoxy]benzene-1,2-dicarboxylic acid as a yellow solid. LC/MS (ESI) m/z: 888.31 $[M+1]^+$.

Step 11: Preparation of (3R)—N-(3-(5-(4-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)phenyl)-1H-pyrrolo[2,3-b]pyridine-3-carbonyl)-2,4-difluorophenyl)-3-fluoropyrrolidine-1-sulfonamide Into a 25-mL round-bottom flask, was placed 4-[(1r,3r)-3-[[(1-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]piperidin-4-yl)methyl](isopropyl)amino]cyclobutoxy]benzene-1,2-dicarboxylic acid (190.00 mg, 0.214 mmol, 1.00 equiv), 3-aminopiperidine-2,6-dione (27.39 mg, 0.214 mmol, 1.00 equiv), HOAc (10.00 mL), NaOAc (175.33 mg, 2.137 mmol, 10.00 equiv). The resulting solution was stirred for 1 hour at 120° C. in an oil bath. The reaction was cooled to room temperature and dried over anhydrous sodium and concentrated under vacuum. The residue was applied onto a silica gel column eluting with dichloromethane/methanol (15:1). The product was further purified by Prep-HPLC. This resulted in 23 mg (11%) of (3R)—N-[2,4-difluoro-3-(5-[4-[4-([isopropyl[(1r,3r)-3-[[2-(2,6-dioxopiperidin-3-yl)-1,3-dioxoisoindol-5-yl]oxy]cyclobutyl]amino]methyl)piperidin-1-yl]phenyl]-1H-pyrrolo[2,3-b]pyridine-3-carbonyl)phenyl]-3-fluoropyrrolidine-1-sulfonamide as a light yellow solid. LC/MS (ESI) m/z: 981.20 $[M+1]^+$; $^1$H-NMR (400 MHz, DMSO-$d_6$) δ 12.89 (s, 1H), 11.10 (s, 1H), 8.65 (s, 1H), 8.52 (s, 1H), 8.15 (s, 1H), 8.06 (s, 1H), 7.83 (d, J=8.4 Hz, 1H), 7.67-7.55 (m, 3H), 7.31-7.21 (m, 3H), 7.10-7.03 (m, 2H), 5.36 (d, J=32.6 Hz, 1H), 5.22-5.20 (m, 1H), 4.92 (t, J=6.6 Hz, 1H), 3.86-3.74 (m, 4H), 3.69 (t, J=8.1 Hz, 2H), 2.89-2.86 (m, 2H), 2.72-2.70 (m, 3H), 2.59-2.56 (m, 2H), 2.29-2.28 (m, 3H), 2.20-2.17 (m, 2H), 2.13-2.00 (m, 3H), 1.86 (d, J=12.4 Hz, 2H), 1.54 (b, 1H), 1.26-1.13 (m, 3H), 0.94 (d, J=6.6 Hz, 6H).

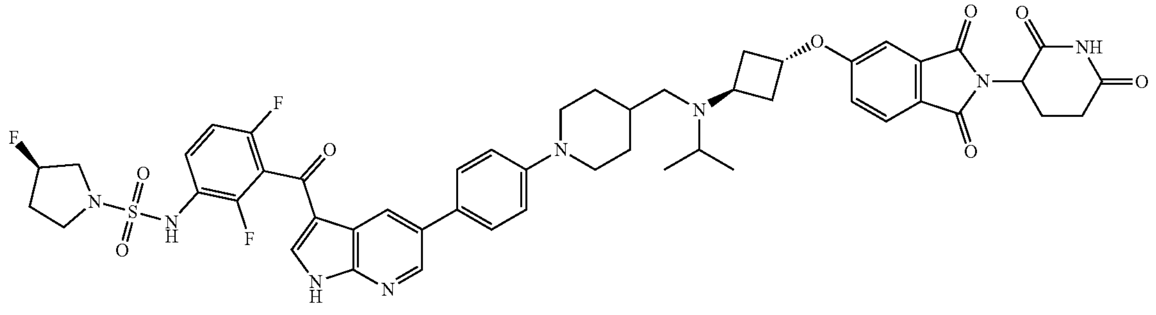 [SMILES: CC(C)N(CC1CCN(c2ccc(-c3cnc4[nH]cc(C(=O)c5c(F)ccc(NS(=O)(=O)N6CC[C@@H](F)C6)c5F)c4c3)cc2)CC1)[C@H]1C[C@H](Oc2ccc3c(c2)C(=O)N(C2CCC(=O)NC2=O)C3=O)C1]

Exemplary Synthesis of (3R)—N-(3-(5-(4-(4-((4-(4-(2,6-dioxopiperidin-3-yl)phenyl)piperazin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide (Exemplary Compound 761)

Step 1: Preparation of tert-butyl 4-(4-(2-methoxy-2-oxoethyl)phenyl)piperazine-1-carboxylate

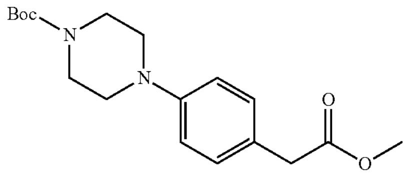 [SMILES: COC(=O)Cc1ccc(N2CCN(C(=O)OC(C)(C)C)CC2)cc1]

Into a 500-mL round-bottom flask purged and maintained with an inert atmosphere of nitrogen, was placed a solution of methyl 2-(4-bromophenyl)acetate (10.0 g, 43.6 mmol, 1.0 equiv), tert-butyl piperazine-1-carboxylate (8.1 g, 43.6 mmol, 1.0 equiv), $Cs_2CO_3$ (28.5 g, 87.3 mmol, 2.0 equiv), RuPhos-PdCl-2nd G (3.4 g, 4.3 mmol, 0.1 equiv) in PhMe (200 mL). The resulting solution was stirred for 16 hours at 110° C. in an oil bath. The resulting mixture was concentrated under reduced pressure. The residue was applied onto a silica gel column with ethyl acetate/petroleum ether (1:1). This resulted in 6.5 g of tert-butyl 4-[4-(2-methoxy-2-oxoethyl) phenyl]piperazine-1-carboxylate as a solid. LC/MS (ESI) m/z: 335.00 $[M+1]^+$.

Step 2: Preparation of tert-butyl 4-(4-(2,6-dioxopiperidin-3-yl)phenyl)piperazine-1-carboxylate

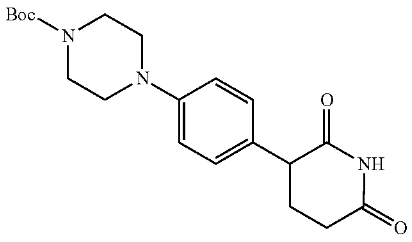 [SMILES: CC(C)(C)OC(=O)N1CCN(c2ccc(C3CCC(=O)NC3=O)cc2)CC1]

Into a 250-mL round-bottom flask purged and maintained with an inert atmosphere of nitrogen, was placed tert-butyl 4-[4-(2-methoxy-2-oxoethyl)phenyl]piperazine-1-carboxylate (6.5 g, 19.4 mmol, 1.0 equiv) and t-BuOK (2.4 g, 21.3 mmol, 1.1 equiv) in THF (60.0 mL). Then polyacrylamide (1.2 g, 17.4 mmol, 0.9 equiv) was added. The resulting mixture was stirred at 50° C. overnight in an oil bath. The reaction was then quenched by the addition of 100 mL of water. The resulting solution was extracted with ethyl acetate (100×3 mL) and concentrated under reduced pressure. The residue was applied onto a silica gel column with ethyl acetate/petroleum ether (2:1). This resulted in 2.1 g (30.0%) of tert-butyl 4-[4-(2, 6-dioxopiperidin-3-yl) phenyl] piperazine-1-carboxylate as a solid. LC/MS (ESI) m/z: 374.05 $[M+1]^+$.

Step 3: Preparation of 3-(4-(piperazin-1-yl)phenyl)piperidine-2,6-dione

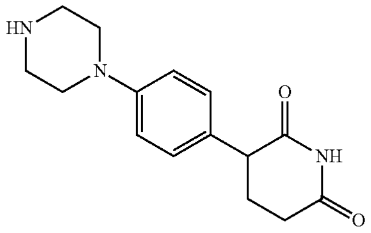 [SMILES: O=C1CCC(c2ccc(N3CCNCC3)cc2)C(=O)N1]

Into a 50-mL round-bottom flask, was placed tert-butyl 4-[4-(2,6-dioxopiperidin-3-yl)phenyl]piperazine-1-carboxylate (2.1 g, 1.0 equiv) in DCM (20.0 mL), to which hydrogen chloride in 1,4-dioxane solution (4.0 M, 20 mL) was added. The resulting mixture was stirred for 2 hours at room temperature. The resulting mixture was concentrated under reduced pressure. This resulted in 1.1 g of 3-[4-(piperazin-1-yl) phenyl] piperidine-2, 6-dione as a solid. LC/MS (ESI) m/z: 274.00 $[M+1]^+$.

Step 4: Preparation of (3R)—N-(3-(5-(4-(4-((4-(4-(2,6-dioxopiperidin-3-yl)phenyl)piperazin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide

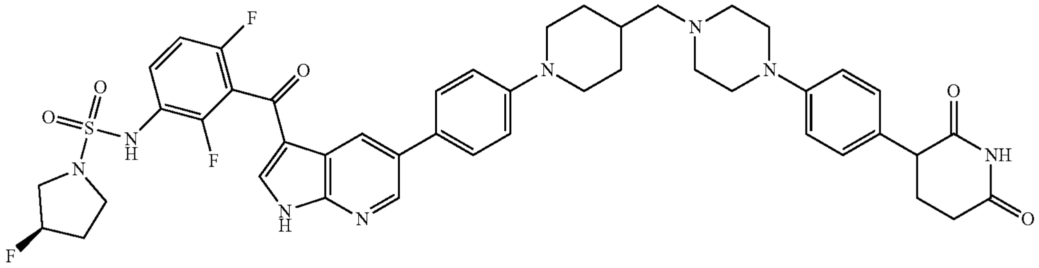 [SMILES: O=C1CCC(c2ccc(N3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)cc2)C(=O)N1]

Into a 100-mL round-bottom flask, was placed (3R)—N-(2,4-difluoro-3-[5-[4-(4-formylpiperidin-1-yl)phenyl]-1H-pyrrolo[2,3-b]pyridine-3-carbonyl]phenyl)-3-fluoropyrrolidine-1-sulfonamide (150.0 mg, 0.25 mmol, 1.0 equiv) and 3-[4-(piperazin-1-yl)phenyl]piperidine-2,6-dione (67.0 mg, 0.25 mmol, 1.0 equiv) in DCM (15.0 mL). The resulting mixture was stirred for 1 hour and then NaBH(OAc)3 (62.3 mg, 0.29 mmol, 1.2 equiv) was added. The resulting mixture was stirred for 12 hours at room temperature. The reaction was then quenched by the addition of 50 mL of water. The resulting solution was extracted with dichloromethane (50 mL×3). The organic layers were combined and concentrated under reduced pressure. The crude product was purified by Prep-HPLC. This resulted in 15.6 mg (7.3%) of (3R)—N-[3-(5-[4-[4-([4-[4-(2,6-dioxopiperidin-3-yl)phenyl]piperazin-1-yl]methyl)piperidin-1-yl]phenyl]-1H-pyrrolo[2,3-b]pyridine-3-carbonyl)-2,4-difluorophenyl]-3-fluoropyrrolidine-1-sulfonamide as a solid. LC/MS (ESI) m/z: 869.15 $[M+1]^+$; $^1$H-NMR (400 MHz, DMSO-$d_6$) δ 12.94 (s, 1H), 10.80 (s, 1H), 9.86 (s, 1H), 9.51 (s, 1H), 8.66 (d, J=2.2 Hz, 1H), 8.55 (s, 1H), 8.07 (d, J=3.0 Hz, 1H), 7.68-7.57 (m, 3H), 7.26-7.20 (m, 1H), 7.17-7.08 (m, 4H), 6.99-6.90 (m, 2H), 5.40-5.20 (m, 1H), 3.85-3.72 (m, 5H), 3.68-3.61 (m, 2H), 3.51-3.40 (m, 2H), 3.29-3.16 (m, 5H), 2.92-2.71 (m, 2H), 2.72-2.59 (m, 1H), 2.22-2.09 (m, 3H), 2.12-1.95 (m, 2H), 1.93-1.84 (m, 2H), 1.50-1.37 (m, 2H), 1.25-1.21 (s, 2H).

Exemplary Synthesis of (2S,4R)-1-((S)-2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide (Exemplary Compound 762)

Step 1: Preparation of ethyl 5-amino-1-methyl-1H-pyrazole-3-carboxylate

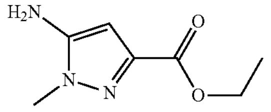

To a mixture of methylhydrazine (13.47 g, 116.92 mmol, 15.4 mL, 1.1 eq) in methanol (150 mL) was added sulfuric acid (10.42 g, 106.29 mmol, 5.6 mL, 1 eq) dropwise at 0° C. The mixture was stirred at 25° C. for 0.5 h, then ethyl 3-cyano-2-oxo-propanoate (15 g, 106.29 mmol, 1 eq) was added at 25° C. and the mixture was stirred at 25° C. for 20.5 hours. The mixture was concentrated in vacuum. The residue was purified by silica gel column chromatography (petroleum ether:ethyl acetate=20:1-1:2). The product ethyl 5-amino-1-methyl-pyrazole-3-carboxylate (11.9 g, 70.34 mmol, 66% yield) was obtained as brown oil. LC/MS (ESI) m/z: 170.2 $[M+1]^+$; $^1$H NMR (400 MHz, $CDCl_3$) δ 6.16-6.05 (m, 1H), 4.47-4.32 (m, 2H), 3.83-3.68 (m, 3H), 3.28-3.14 (m, 2H), 1.44-1.35 (m, 3H).

Step 2: Preparation of benzyl 4-(3-(ethoxycarbonyl)-1-methyl-1H-pyrazol-5-yl)piperazine-1-carboxylate

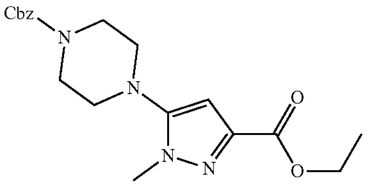 [SMILES: CCOC(=O)c1cc(N2CCN(C(=O)OCc3ccccc3)CC2)n(C)n1]

To a solution of benzyl N,N-bis(2-oxoethyl)carbamate (14.8 g, 62.92 mmol, 1.1 eq) and ethyl 5-amino-1-methyl-pyrazole-3-carboxylate (9.68 g, 57.20 mmol, 1 eq) in acetic acid (20 mL) and methanol (280 mL) was added borane;2-methylpyridine (12.24 g, 114.39 mmol, 2 eq). The mixture was stirred at 25° C. for 1 h. And then the mixture was stirred at 25° C. for 11 h. Saturated aqueous sodium bicarbonate (~180 mL) was added into the mixture to adjust the pH=8. The aqueous phase was extracted with ethyl acetate (300 mL×3). The combined organic phase was washed with brine (500 mL×2), dried with anhydrous sodium sulfate, filtered and concentrated in vacuum. The residue was purified by silica gel chromatography (petroleum ether/ethyl acetate=30/1, 1/1). The oil was further purified by preparative reverse phase HPLC. The solution was concentrated in vacuum. The aqueous phase was extracted with ethyl acetate (200 mL×3). The combined organic phase was washed with brine (200 mL×2), dried with anhydrous sodium sulfate, filtered and concentrated in vacuum. The product benzyl 4-(5-ethoxycarbonyl-2-methyl-pyrazol-3-yl)piperazine-1-carboxylate (11.55 g, 31.01 mmol, 54% yield) was obtained as a colorless oil. LC/MS (ESI) m/z: 373.3 $[M+1]^+$.

Step 3: Preparation of 5-(4-((benzyloxy)carbonyl)piperazin-1-yl)-1-methyl-1H-pyrazole-3-carboxylic acid

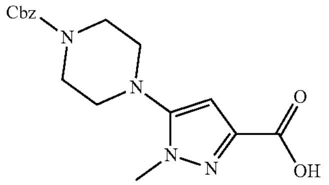 [SMILES: Cn1nc(C(=O)O)cc1N1CCN(C(=O)OCc2ccccc2)CC1]

To a mixture of benzyl 4-(5-ethoxycarbonyl-2-methyl-pyrazol-3-yl)piperazine-1-carboxylate (16.18 g, 43.45 mmol, 1 eq) in water (20 mL) and tetrahydrofuran (200 mL) was added sodium hydroxide (4.34 g, 108.61 mmol, 2.5 eq) in one portion at 25° C. The mixture was stirred at 25° C. for 12 hours. Water (100 mL) was poured into the mixture and stirred for 1 min. The aqueous phase was extracted with ethyl acetate (100 mL). Hydrochloric acid (2 M) was added to the aqueous phase to adjust the pH=3~4. And then the aqueous phase was extracted with ethyl acetate (150 mL×3). The combined organic phase was washed with brine (200 mL), dried with anhydrous sodium sulfate, filtered and concentrated in vacuum. The product 5-(4-benzyloxycarbonylpiperazin-1-yl)-1-methyl-pyrazole-3-carboxylic acid (13.12 g, 38.10 mmol, 87% yield) was obtained as a red gum. LC/MS (ESI) m/z: 345.0 [M+1]$^+$; $^1$H-NMR (400 MHz, DMSO-$d_6$) δ 8.69 (s, 1H), 7.67-7.59 (m, 2H), 7.39 (d, J=8.4 Hz, 2H), 4.85 (s, 1H), 3.50 (s, 1H), 1.48 (d, J=6.4 Hz, 3H), 1.44 (s, 9H).

Step 4: Preparation of benzyl 4-(3-(hydroxymethyl)-1-methyl-1H-pyrazol-5-yl)piperazine-1-carboxylate

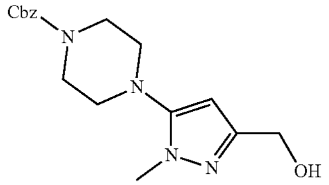

To a solid of 5-(4-benzyloxycarbonylpiperazin-1-yl)-1-methyl-pyrazole-3-carboxylic acid (5 g, 14.52 mmol, 1 eq) in tetrahydrofuran (20 mL) was added borane dimethyl sulfide complex (10 M, 7.3 mL, 5 eq) at 0° C. The mixture was stirred at 25° C. for 1 h. The mixture was added into methanol (200 mL) dropwise at 0° C. and stirred for 1 min. The mixture was concentrated in vacuum. The residue was purified by silica gel column chromatography (petroleum ether:ethyl acetate=5:1-1:2). The oil was dissolved in 100 mL of acetonitrile, 2 mL of trifluoroacetic acid was added and the mixture was stirred at 25° C. for 2 h. Then the column was flushed with a gradient (dichloromethane: methanol=50:1-25:1) to get another batch of product. The product benzyl 4-[5-(hydroxymethyl)-2-methyl-pyrazol-3-yl]piperazine-1-carboxylate (3.8 g, 11.50 mmol, 79% yield) was obtained as a colorless gum. LC/MS (ESI) m/z 331.5 [M+1]$^+$; $^1$H-NMR (400 MHz, $CDCl_3$) δ 7.44-7.30 (m, 5H), 5.83 (s, 1H), 5.17 (s, 2H), 4.60 (s, 2H), 3.71 (s, 3H), 3.68-3.61 (m, 4H), 2.87 (s, 4H), 2.05-2.03 (m, 1H).

Step 5: Preparation of benzyl 4-(1-methyl-3-(((methylsulfonyl)oxy)methyl)-1H-pyrazol-5-yl)piperazine-1-carboxylate

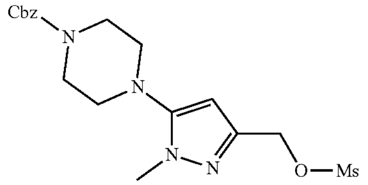 [SMILES: Cn1nc(COS(C)(=O)=O)cc1N1CCN(C(=O)OCc2ccccc2)CC1]

To a mixture of benzyl 4-[5-(hydroxymethyl)-2-methyl-pyrazol-3-yl]piperazine-1-carboxylate (2.5 g, 7.57 mmol, 1 eq) and triethylamine (1.53 g, 15.13 mmol, 2.1 mL, 2 eq) in dichloromethane (35 mL) was added methanesulfonyl chloride (1.30 g, 11.35 mmol, 1.5 eq) dropwise at 0° C. The mixture was stirred at 0° C. for 2 hours. Water (30 mL) was poured into the mixture and stirred for 1 min. The aqueous phase was extracted with dichloromethane (30 mL×2). The combined organic phase was washed with brine (30 mL×2), dried with anhydrous sodium sulfate, filtered and concentrated in vacuum. The product benzyl 4-[2-methyl-5-(methylsulfonyloxymethyl)pyrazol-3-yl]piperazine-1-carboxylate (3 g) was obtained as a light yellow oil.

Step 6: Preparation of benzyl 4-(3-(cyanomethyl)-1-methyl-1H-pyrazol-5-yl)piperazine-1-carboxylate

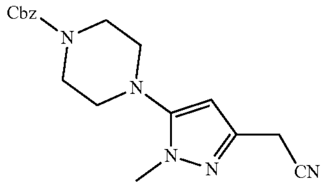 [SMILES: Cn1nc(CC#N)cc1N1CCN(C(=O)OCc2ccccc2)CC1]

To a mixture of benzyl 4-[2-methyl-5-(methylsulfonyloxymethyl)pyrazol-3-yl]piperazine-1-carboxylate (3 g, 7.34 mmol, 1 eq) in dimethylformamide (30 mL) was added sodium cyanide (720 mg, 14.69 mmol, 2 eq) in one portion at 25° C. The mixture was stirred at 50° C. for 16 hours. Water (150 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The aqueous phase was poured into the aqueous sodium hypochlorite (1500 mL). The residue was purified by silica gel chromatography (petroleum ether/ethyl acetate=3/l, 1/1). The product benzyl 4-[5-(cyanomethyl)-2-methyl-pyrazol-3-yl] piperazine-1-carboxylate (820 mg, 2.42 mmol, 32.90% yield) was obtained as a light-yellow oil. LC/MS (ESI) m/z: 340.5 [M+1]$^+$; $^1$H-NMR (400 MHz, $CDCl_3$) δ 7.43-7.30 (m, 5H), 5.85 (s, 1H), 5.17 (s, 2H), 3.70 (s, 3H), 3.68-3.62 (m, 6H), 2.88 (d, J=7.7 Hz, 4H).

Step 7: Preparation of benzyl 4-(3-(1-cyano-2-methylpropyl)-1-methyl-1H-pyrazol-5-yl)piperazine-1-carboxylate

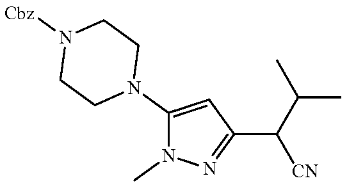 [SMILES: CC(C)C(C#N)c1cc(N2CCN(C(=O)OCc3ccccc3)CC2)n(C)n1]

To a solution of benzyl 4-[5-(cyanomethyl)-2-methyl-pyrazol-3-yl]piperazine-1-carboxylate (820 mg, 2.42 mmol, 1 eq) in dimethylformamide (15 mL) was added potassium tert-butoxide (298 mg, 2.66 mmol, 1.1 eq) at 0° C. The mixture was stirred at 25° C. for 0.5 h. Then 2-iodopropane (411 mg, 2.42 mmol, 1 eq) was added to the mixture. The mixture was stirred at 25° C. for 2 h. Water (50 mL) was poured into the mixture and stirred for 1 min. The aqueous phase was extracted with ethyl acetate (20 mL×3). The combined organic phase was washed with brine (20 mL×3), dried with anhydrous sodium sulfate, filtered and concentrated in vacuum. The residue was purified by silica gel column chromatography (petroleum ether/ethyl acetate=4/l, 1/1). The product benzyl 4-[5-(1-cyano-2-methyl-propyl)-2-methyl-pyrazol-3-yl]piperazine-1-carboxylate (360 mg, 0.94 mmol, 39% yield) was obtained as a colorless oil. LC/MS (ESI) m/z: 382.2 [M+1]$^+$; $^1$H-NMR (400 MHz, $CDCl_3$) δ 7.43-7.31 (m, 5H), 5.89-5.79 (m, 1H), 5.22-5.12

(m, 2H), 3.72-3.69 (m, 3H), 3.69-3.68 (m, 1H), 3.68-3.60 (m, 4H), 2.90-2.84 (m, 4H), 2.29-2.12 (m, 1H), 1.14-1.03 (m, 6H).

Step 8: Preparation of 3-methyl-2-(1-methyl-5-(piperazin-1-yl)-1H-pyrazol-3-yl)butanoic acid

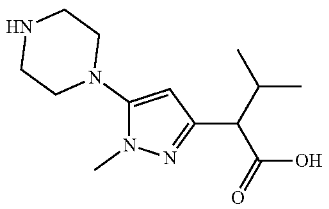 [SMILES: CC(C)C(C(=O)O)c1cc(N2CCNCC2)n(C)n1]

To a mixture of benzyl 4-[5-(1-cyano-2-methyl-propyl)-2-methyl-pyrazol-3-yl]piperazine-1-carboxylate (360 mg, 0.94 mmol, 1 eq) in dioxane (4 mL) was added hydrochloride acid (12 M, 4 mL, 50 eq) in one portion at 25° C. The mixture was stirred at 100° C. for 12 hours. The mixture was concentrated in vacuum. The product 3-methyl-2-(1-methyl-5-piperazin-1-yl-pyrazol-3-yl)butanoic acid (250 mg) was obtained as a yellow oil. LC/MS (ESI) m/z: 267.2 $[M+1]^+$.

Step 9: Preparation of 2-(5-(4-(tert-butoxycarbonyl)piperazin-1-yl)-1-methyl-1H-pyrazol-3-yl)-3-methylbutanoic acid

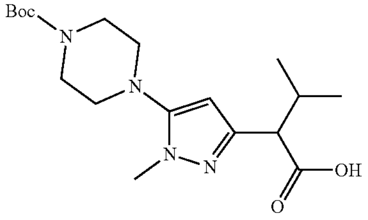 [SMILES: CC(C)C(C(=O)O)c1cc(N2CCN(C(=O)OC(C)(C)C)CC2)n(C)n1]

To a mixture of 3-methyl-2-(1-methyl-5-piperazin-1-yl-pyrazol-3-yl)butanoic acid (250 mg, 0.94 mmol, 1 eq) in water (2 mL) and tetrahydrofuran (3 mL) was added sodium carbonate (497 mg, 4.69 mmol, 5 eq), di-tert-butyl dicarbonate (410 mg, 1.88 mmol, 2 eq) in one portion at 25° C. The mixture was stirred at 25° C. for 2 hours. Water (20 mL) was poured into the mixture and stirred for 1 min. The aqueous phase was extracted with ethyl acetate (20 mL×2). Hydrochloride acid (2 M) was added to the aqueous phase to adjust the pH=3~4. And then the aqueous phase was extracted with ethyl acetate (20 mL×3). The combined organic phase was washed with brine (20 mL), dried with anhydrous sodium sulfate, filtered and concentrated in vacuum. The product 2-[5-(4-tert-butoxycarbonylpiperazin-1-yl)-1-methyl-pyrazol-3-yl]-3-methyl-butanoic acid (330 mg, 0.79 mmol, 84% yield, 87% purity) was obtained as a colorless oil. LC/MS (ESI) m/z: 5612 $[M+1]^+$.

Step 10: Preparation of tert-butyl 4-(3-(1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)-1-methyl-1H-pyrazol-5-yl)piperazine-1-carboxylate

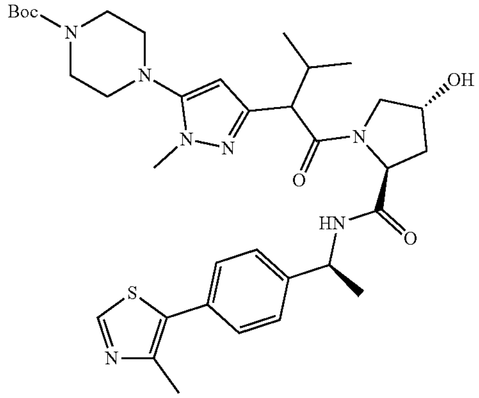 [SMILES: Cc1ncsc1-c1ccc([C@H](C)NC(=O)[C@@H]2C[C@@H](O)CN2C(=O)C(c2cc(N3CCN(C(=O)OC(C)(C)C)CC3)n(C)n2)C(C)C)cc1]

To a mixture of 2-[5-(4-tert-butoxycarbonylpiperazin-1-yl)-1-methyl-pyrazol-3-yl]-3-methyl-butanoic acid (330 mg, 0.79 mmol, 1 eq) in dimethylformamide (5 mL) was added diisopropylethylamine (306 mg, 2.37 mmol, 3 eq), 1-hydroxybenzotriazole (128 mg, 0.95 mmol, 1.2 eq) and 1-(3-dimethylaminopropyl)-3-ethylcarbodiimide (227 mg, 1.19 mmol, 1.5 eq) in one portion at 25° C. The mixture was stirred at 25° C. for 10 min, then (2S,4R)-4-hydroxy-N-[(1S)-1-[4-(4-methylthiazol-5-yl)phenyl]ethyl]pyrrolidine-2-carboxamide (291 mg, 0.79 mmol, 1 eq, hydrochloride) was added, the mixture was stirred at 25° C. for 11 hour 50 min. Water (40 mL) was poured into the mixture and stirred for 1 min. The aqueous phase was extracted with ethyl acetate (20 mL×3). The combined organic phase was washed with brine (20 mL×3), dried with anhydrous sodium sulfate, filtered and concentrated in vacuum. The residue was purified by silica gel column chromatography (dichloromethane/methanol=200/1, 40/1). The product tert-butyl 4-[5-[1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (360 mg, 0.44 mmol, 56% yield, 84% purity) was obtained as a colorless oil. LC/MS (ESI) m/z: 680.3 $[M+1]^+$.

Step 11: Preparation of tert-butyl 4-(3-((S)-1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)-1-methyl-1H-pyrazol-5-yl)piperazine-1-carboxylate

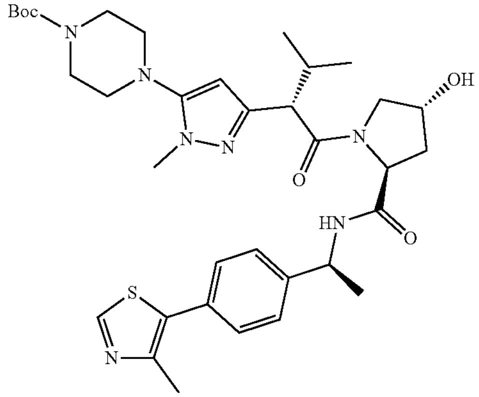 [SMILES: Cc1ncsc1-c1ccc([C@H](C)NC(=O)[C@@H]2C[C@@H](O)CN2C(=O)[C@H](c2cc(N3CCN(C(=O)OC(C)(C)C)CC3)n(C)n2)C(C)C)cc1]

Tert-butyl 4-[5-[1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (360 mg, 0.44 mmol, 1 eq) was purified by Chiral SFC. The product tert-butyl 4-[5-[(1S)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (150 mg, 0.20 mmol, 88% yield, 89% purity) was obtained as a white solid.

Step 12: Preparation of (2S,4R)-4-hydroxy-1-((S)-3-methyl-2-(1-methyl-5-(piperazin-1-yl)-1H-pyrazol-3-yl)butanoyl)-N—((S)-1-(4-(4-methylthiazol-5-yl)phenyl)ethyl)pyrrolidine-2-carboxamide

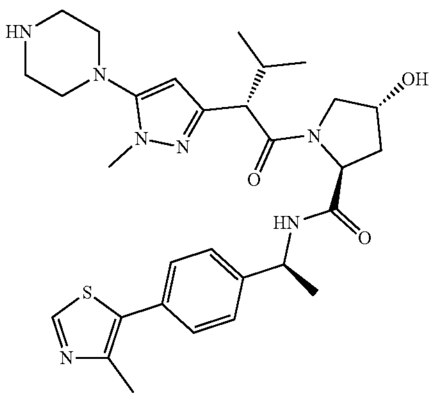 [SMILES: Cc1ncsc1-c1ccc([C@H](C)NC(=O)[C@@H]2C[C@@H](O)CN2C(=O)[C@H](c2cc(N3CCNCC3)n(C)n2)C(C)C)cc1]

To a mixture of tert-butyl 4-[5-[(1S)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (150 mg, 0.20 mmol, 1 eq) in dichloromethane (5 mL) was added hydrochloric acid (4 M in dioxane, 5 mL, 100 eq) in one portion at 25° C. The mixture was stirred at 25° C. for 2 hours. The mixture was concentrated in vacuum. The product (2S,4R)-4-hydroxy-1-[(2S)-3-methyl-2-(1-methyl-5-piperazin-1-yl-pyrazol-3-yl)butanoyl]-N-[(1S)-1-[4-(4-methylthiazol-5-yl)phenyl]ethyl]pyrrolidine-2-carboxamide (150 mg, hydrochloride) was obtained as an off-white solid. LC/MS (ESI) m/z: 580.2 [M+1]$^+$.

Step 13: Preparation of (2S,4R)-1-((S)-2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

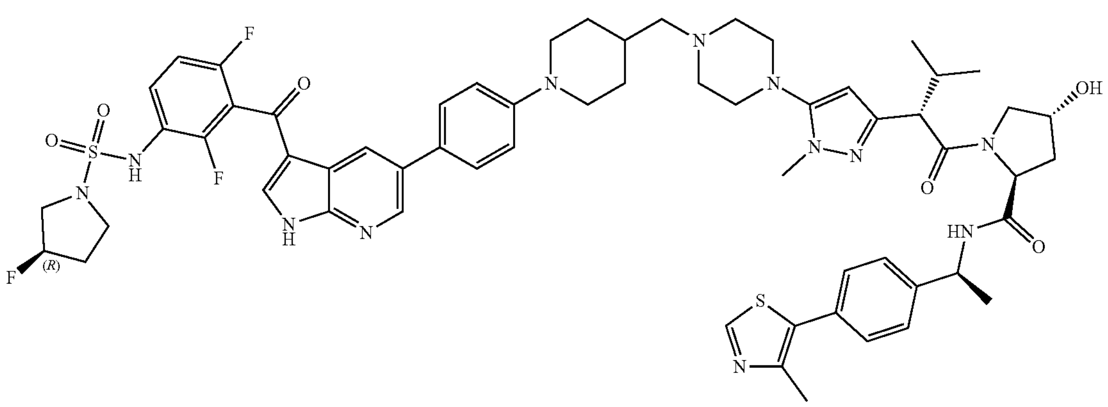

To a mixture of (2S,4R)-4-hydroxy-1-[(2S)-3-methyl-2-(1-methyl-5-piperazin-1-yl-pyrazol-3-yl)butanoyl]-N-[(1S)-1-[4-(4-methylthiazol-5-yl)phenyl]ethyl]pyrrolidine-2-carboxamide (140 mg, 0.23 mmol, 1 eq, hydrochloride) in methanol (5 mL) was added sodium acetate (74 mg, 0.91 mmol, 4 eq) in one portion at 30° C. The mixture was stirred at 30° C. for 1 min, then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (104 mg, 0.17 mmol, 0.75 eq) in dichloromethane (2 mL) was added. The mixture was stirred at 30° C. for another 1 min, acetic acid (0.02 mL) was added to adjust the pH=4~5. And then sodium cyanoborohydride (28 mg, 0.45 mmol, 2 eq) was added and stirred at 30° C. for 58 min. The mixture was concentrated in vacuum. 4 mL of dimethylformamide was added. The mixture was filtered to get the filtrate. The yellow filtrate was purified by Semi-preparative reverse phase HPLC. The product (2S,4R)-1-[(2S)-2-[5-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (103.38 mg, 0.09 mmol, 38% yield, 99% purity, trifluoroacetate) was obtained as a yellow solid. LC/MS (ESI) m/z: 588.3 $[M/2+1]^+$; $^1$H-NMR (400 MHz, DMSO-$d_6$) δ 12.95-12.88 (m, 1H), 9.84 (s, 1H), 9.43-9.20 (m, 1H), 9.06-8.95 (m, 1H), 8.66 (d, J=2.0 Hz, 1H), 8.55 (s, 1H), 8.30 (d, J=8.0 Hz, 1H), 8.13-8.01 (m, 1H), 7.74-7.56 (m, 3H), 7.48-7.34 (m, 4H), 7.27 (t, J=8.8 Hz, 1H), 7.13 (d, J=8.8 Hz, 2H), 5.83 (s, 1H), 5.40-5.19 (m, 1H), 4.99-4.84 (m, 1H), 4.38-4.23 (m, 2H), 3.85 (d, J=11.6 Hz, 2H), 3.75-3.69 (m, 2H), 3.61 (s, 4H), 3.41 (s, 2H), 3.32-3.23 (m, 6H), 3.19-3.14 (m, 2H), 3.06-2.91 (m, 2H), 2.83 (t, J=11.7 Hz, 2H), 2.46 (s, 4H), 2.18-1.75 (m, 9H), 1.50-1.30 (m, 5H), 0.94 (d, J=6.4 Hz, 3H), 0.69 (d, J=6.4 Hz, 3H).

Exemplary Synthesis of (2S,4R)-1-((R)-2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide (Exemplary Compound 763)

Step 1: Preparation of tert-butyl 4-(3-((R)-1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)-1-methyl-1H-pyrazol-5-yl)piperazine-1-carboxylate

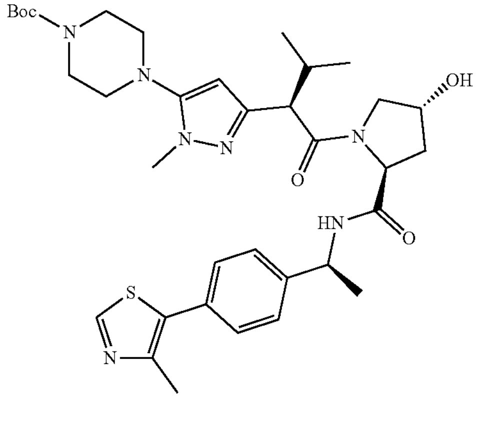 [SMILES: Cc1ncsc1-c1ccc([C@H](C)NC(=O)[C@@H]2C[C@@H](O)CN2C(=O)[C@@H](c2cc(N3CCN(C(=O)OC(C)(C)C)CC3)n(C)n2)C(C)C)cc1]

Tert-butyl 4-[5-[1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (360 mg, 0.44 mmol, 1 eq) was purified by Chiral SFC. The product tert-butyl 4-[5-[(1R)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (150 mg, 0.21 mmol, 93% yield, 94% purity) was obtained as a white solid.

Step 2: Preparation of (2S,4R)-4-hydroxy-1-((R)-3-methyl-2-(1-methyl-5-(piperazin-1-yl)-1H-pyrazol-3-yl)butanoyl)-N—((S)-1-(4-(4-methylthiazol-5-yl)phenyl)ethyl)pyrrolidine-2-carboxamide

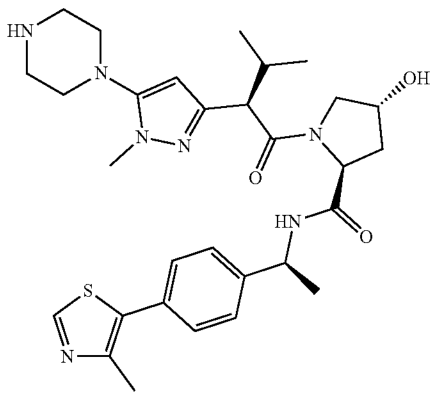 [SMILES: Cc1ncsc1-c1ccc([C@H](C)NC(=O)[C@@H]2C[C@@H](O)CN2C(=O)[C@@H](c2cc(N3CCNCC3)n(C)n2)C(C)C)cc1]

To a mixture of tert-butyl 4-[5-[(1R)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]-2-methyl-pyrazol-3-yl]piperazine-1-carboxylate (150 mg, 0.21 mmol, 1 eq) in dichloromethane (5 mL) was added hydrochloric acid (4 M in dioxane, 5 mL, 100 eq) in one portion at 25° C. The mixture was stirred at 25° C. for 2 hours. The mixture was concentrated in vacuum. The product (2S,4R)-4-hydroxy-1-[(2R)-3-methyl-2-(1-methyl-5-piperazin-1-yl-pyrazol-3-yl)butanoyl]-N-[(1S)-1-[4-(4-methylthiazol-5-yl)phenyl]ethyl]pyrrolidine-2-carboxamide (150 mg, hydrochloride) was obtained as an off-white solid. LC/MS (ESI) m/z: 580.2 $[M+1]^+$.

Step 3: Preparation of (2S,4R)-1-((R)-2-(5-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)-1-methyl-1H-pyrazol-3-yl)-3-methylbutanoyl)-4-hydroxy-N—((S)-1-(4-(4-methylthiazol-5-yl)phenyl)ethyl)pyrrolidine-2-carboxamide

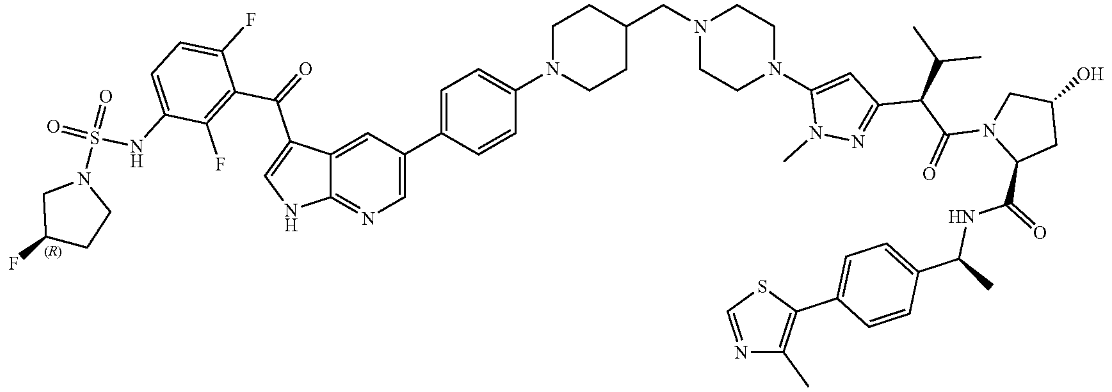

To a mixture of (2S,4R)-4-hydroxy-1-[(2R)-3-methyl-2-(1-methyl-5-piperazin-1-yl-pyrazol-3-yl)butanoyl]-N-[(1S)-1-[4-(4-methylthiazol-5-yl)phenyl]ethyl]pyrrolidine-2-carboxamide (140 mg, 0.23 mmol, 1 eq, hydrochloride) in methanol (5 mL) was added sodium acetate (74 mg, 0.91 mmol, 4 eq) in one portion at 30° C. The mixture was stirred at 30° C. for 1 min, then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (104 mg, 0.17 mmol, 0.75 eq) in dichloromethane (2 mL) was added. The mixture was stirred at 30° C. for another 1 min, acetic acid (0.02 mL) was added to adjust the pH=4~5. And then sodium cyanoborohydride (28 mg, 0.45 mmol, 2 eq) was added and stirred at 30° C. for 58 min. The mixture was concentrated in vacuum. 4 mL of dimethylformamide was added. The mixture was filtered to get the filtrate. The yellow filtrate was purified by Semi-preparative reverse phase HPLC. The product (2S,4R)-1-[(2R)-2-[5-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]piperazin-1-yl]-1-methyl-pyrazol-3-yl]-3-methyl-butanoyl]-4-hydroxy-N-[(1S)-1-[4-(4-methylthiazol-5-yl)phenyl]ethyl]pyrrolidine-2-carboxamide (135.5 mg, 0.11 mmol, 50% yield, 91% purity, trifluoroacetate). LC/MS (ESI) m/z: 1175.4 $[M+1]^+$; $^1$H-NMR (400 MHz, DMSO-$d_6$) δ 13.03-12.84 (m, 1H), 9.84 (s, 1H), 9.50-9.19 (m, 1H), 8.99 (s, 1H), 8.78 (d, J=8.0 Hz, 1H), 8.66 (d, J=2.0 Hz, 1H), 8.61-8.47 (m, 1H), 8.25-8.13 (m, 1H), 8.07 (d, J=2.4 Hz, 1H), 7.70-7.57 (m, 3H), 7.51-7.39 (m, 3H), 7.38-7.31 (m, 1H), 7.27 (t, J=9.2 Hz, 1H), 7.19-7.06 (m, 2H), 5.92-5.75 (m, 1H), 5.41-5.17 (m, 1H), 5.07-4.97 (m, 1H), 4.92-4.77 (m, 1H), 4.69-4.60 (m, 1H), 4.50-4.38 (m, 1H), 4.29-4.17 (m, 1H), 3.85-3.80 (m, 3H), 3.49 (s, 3H), 3.41-3.36 (m, 3H), 3.32-3.15 (m, 8H), 2.89-2.77 (m, 2H), 2.47-2.44 (m, 4H), 2.20-1.78 (m, 9H), 1.47-1.32 (m, 5H), 0.95 (d, J=6.8 Hz, 2H), 0.84-0.71 (m, 3H), 0.70-0.64 (m, 1H).

Exemplary Synthesis of 3-(5-(2-(2-(2-(2-(4-(4-(4-chloro-3-hydroxyphenyl)-3-(pyridin-4-yl)-1H-pyrazol-1-yl)phenoxy)ethoxy)ethoxy)ethoxy)ethoxy)-1-oxoisoindolin-2-yl)piperidine-2,6-dione (Exemplary Compound 764)

Step 1: Preparation of 4-(4-bromo-1-(4-((tetrahydro-2H-pyran-2-yl)oxy)phenyl)-1H-pyrazol-3-yl)pyridine

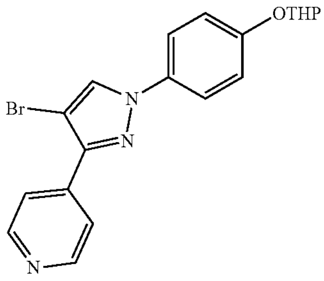

A mixture of 4-(4-bromo-1H-pyrazol-3-yl)pyridine (4 g, 17.85 mmol, 1 eq), (4-tetrahydropyran-2-yloxyphenyl)boronic acid (3.96 g, 17.85 mmol, 1 eq), (4-tetrahydropyran-2-yloxyphenyl) boronic acid (3.96 g, 17.85 mmol, 1 eq) and cupric acetate (4.86 g, 26.78 mmol, 1.5 eq) in dichloromethane (80 mL) was degassed and purged with oxygen for 3 times, and then the mixture was stirred at 15° C. for 12 h under oxygen atmosphere. The reaction mixture was diluted with dichloromethane 50 mL washed with ammonium hydroxide (100 mL×3), dried over anhydrous sodium sulfate, filtered and concentrated under reduced pressure. The residue was purified by flash silica gel chromatography. Compound 4-[4-bromo-1-(4-tetrahydropyran-2-yloxyphenyl)pyrazol-3-yl] pyridine (3.6 g, 8.63 mmol, 48% yield, 96% purity) was obtained as a light yellow solid. LC/MS (ESI) m/z: 401.9 $[M+1]^+$; $^1$H-NMR (400 MHz, $CDCl_3$) δ

8.75-8.65 (m, 2H), 8.01-7.92 (m, 3H), 7.67-7.56 (m, 2H), 7.22-7.10 (m, 2H), 5.46 (t, J=3.2 Hz, 1H), 3.91 (ddd, J=3.2, 10.0, 11.2 Hz, 1H), 3.64 (dtd, J=1.2, 4.0, 11.2 Hz, 1H), 2.05-1.97 (m, 1H), 1.90 (td, J=3.8, 7.6 Hz, 2H), 1.75-1.63 (m, 3H).

Step 2: Preparation of 4-(4-bromo-3-(pyridin-4-yl)-1H-pyrazol-1-yl)phenol

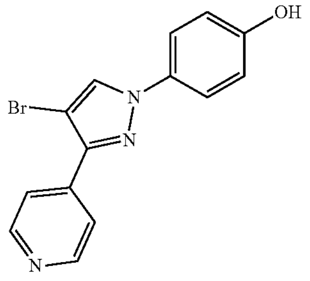 [SMILES: Oc1ccc(-n2cc(Br)c(-c3ccncc3)n2)cc1]

To a solution of 4-[4-bromo-1-(4-tetrahydropyran-2-yloxyphenyl)pyrazol-3-yl]pyridine (3.6 g, 8.45 mmol, 1 eq) in dichloromethane (20 mL) was added hydrogen chloride/dioxane (4 M, 10.57 mL, 5 eq). The mixture was stirred at 15° C. for 2 h. The reaction mixture was concentrated under reduced pressure to remove the solvent. Compound 4-[4-bromo-3-(4-pyridyl)pyrazol-1-yl]phenol (3.4 g, Hydrochloride) was obtained as a yellow solid. LC/MS (ESI) m/z: 316.1 $[M+1]^+$.

Step 3: Preparation of 2-(2-(2-(2-(4-(4-bromo-3-(pyridin-4-yl)-1H-pyrazol-1-yl)phenoxy)ethoxy)ethoxy)ethoxy)ethan-1-ol

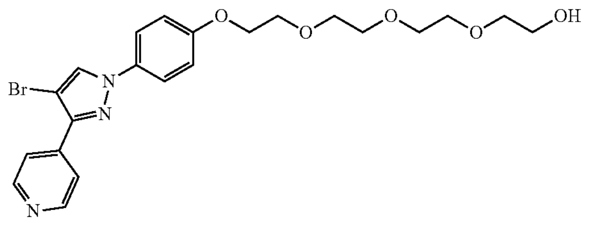 [SMILES: OCCOCCOCCOCCOc1ccc(-n2cc(Br)c(-c3ccncc3)n2)cc1]

To a solution of 4-[4-bromo-3-(4-pyridyl)pyrazol-1-yl]phenol (880 mg, 2.27 mmol, 1 eq, Hydrochloride) in N,N-dimethylformamide (20 mL) was added cesium carbonate (1.48 g, 4.54 mmol, 2 eq) and 2-[2-[2-(2-hydroxyethoxy)ethoxy]ethoxy]ethyl 4-methylbenzenesulfonate (790 mg, 2.27 mmol, 1 eq). The mixture was stirred at 80° C. for 3 h. The reaction mixture was diluted with water 30 mL and extracted with ethyl acetate (50 mL×3). The combined organic layers were washed with brine (50 mL×3), dried over anhydrous sodium sulfate, filtered and concentrated under reduced pressure. The residue was purified by silica gel chromatography (Petroleum ether/Ethyl acetate=1:1 to 0:1 Dichloromethane/Methanol=10:1). Compound 2-[2-[2-[2-[4-[4-bromo-3-(4-pyridyl)pyrazol-1-yl]phenoxy]ethoxy]ethoxy]ethoxy]ethanol (0.85 g, 1.73 mmol, 76% yield) was obtained as a brown oil. LC/MS (ESI) m/z: 494.0 $[M+1]^+$.

Step 4: Preparation of tert-butyl 5-amino-4-(5-(2-(2-(2-(2-(4-(4-bromo-3-(pyridin-4-yl)-1H-pyrazol-1-yl)phenoxy)ethoxy)ethoxy)ethoxy)ethoxy)-1-oxoisoindolin-2-yl)-5-oxopentanoate

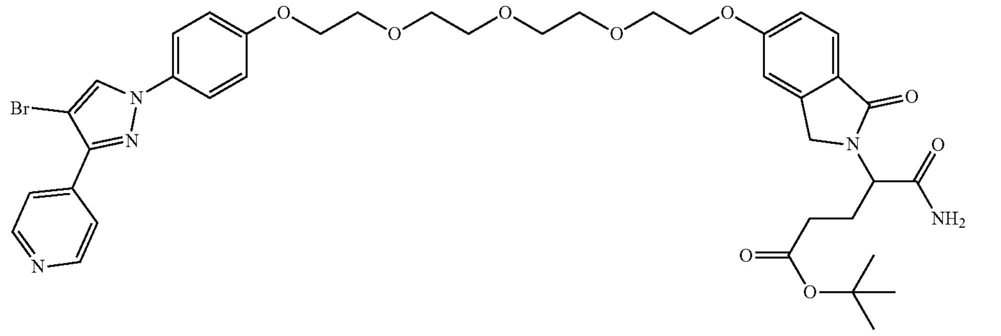 [SMILES: CC(C)(C)OC(=O)CCC(C(N)=O)N1Cc2cc(OCCOCCOCCOCCOc3ccc(-n4cc(Br)c(-c5ccncc5)n4)cc3)ccc2C1=O]

To a solution of 2-[4-[4-bromo-3-(4-pyridyl)pyrazol-1-yl]phenoxy]ethanol (880 mg, 1.62 mmol, 1 eq) in tetrahydrofuran (15 mL) was added tert-butyl 5-amino-4-(5-hydroxy-1-oxo-isoindolin-2-yl)-5-oxo-pentanoate (527 mg, 1.40 mmol, 1 eq), triphenylphosphine (554 mg, 2.11 mmol, 1.3 eq) and disopropyl azodiformate (427 mg, 2.11 mmol, 1.3 eq) at 0° C. The mixture was stirred at 60° C. for 12 h. The reaction mixture was diluted with water 20 mL and extracted with ethyl acetate (30 mL×3). The combined organic layers were washed with brine (50 mL×3), dried over anhydrous sodium sulfate, filtered and concentrated under reduced pressure. The residue was purified by flash silica gel chromatography. The product was further purified by Semi-preparative reverse phase HPLC. Compound tert-butyl 5-amino-4-[5-[2-[2-[2-[2-[4-[4-bromo-3-(4-pyridyl)pyrazol-1-yl]phenoxy]ethoxy]ethoxy]ethoxy]ethoxy]-1-oxo-isoindolin-2-yl]-5-oxo-pentanoate (850 mg, 1.05 mmol, 64% yield) was obtained as a yellow gum. LC/MS (ESI) m/z: 810.0 $[M+1]^+$; $^1$H-NMR (400 MHz, $CDCl_3$) δ 8.75-8.61 (m, 2H), 8.06-7.90 (m, 3H), 7.73 (d, J=8.4 Hz, 1H), 7.61 (d, J=9.2 Hz, 2H), 7.08-6.97 (m, 3H), 6.95 (s, 1H), 6.36 (s, 1H), 5.38 (s, 1H), 4.86 (dd, J=6.4, 8.8 Hz, 1H), 4.52-4.32 (m, 2H), 4.18 (q, J=4.8 Hz, 4H), 3.95-3.83 (m, 4H), 3.79-3.64 (m, 8H), 2.43-2.07 (m, 4H), 1.42 (s, 9H).

Step 5: Preparation of tert-butyl 5-amino-4-(5-(2-(2-(2-(2-(4-(4-(4-chloro-3-hydroxyphenyl)-3-(pyridin-4-yl)-1H-pyrazol-1-yl)phenoxy)ethoxy)ethoxy)ethoxy)ethoxy)-1-oxoisoindolin-2-yl)-5-oxopentanoate

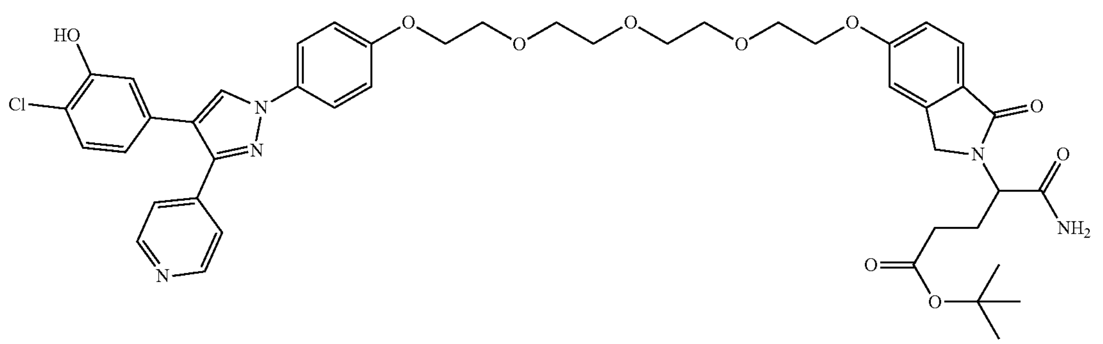 [SMILES: CC(C)(C)OC(=O)CCC(C(N)=O)N1Cc2cc(OCCOCCOCCOCCOc3ccc(-n4cc(-c5ccc(Cl)c(O)c5)c(-c5ccncc5)n4)cc3)ccc2C1=O]

A mixture of tert-butyl 5-amino-4-[5-[2-[2-[2-[2-[4-[4-bromo-3-(4-pyridyl)pyrazol-1-yl] phenoxy]ethoxy]ethoxy] ethoxy]ethoxy]-1-oxo-isoindolin-2-yl]-5-oxo-pentanoate (400 mg, 0.49 mmol, 1 eq), (4-chloro-3-hydroxy-phenyl) boronic acid (85 mg, 0.49 mmol, 1 eq), ditert-butyl(cyclopentyl)phosphane;dichloropalladium;iron (32 mg, 0.049 mmol, 0.1 eq) and cesium fluoride (300 mg, 1.98 mmol, 4 eq) in dioxane (1.5 mL) and water (0.3 mL) was degassed and purged with nitrogen for 3 times, and then the mixture was stirred at 90° C. for 3 hr under nitrogen atmosphere. The reaction mixture was diluted with water 10 mL and extracted with dichloromethane (20 mL×3). The combined organic layers were dried over anhydrous sodium sulfate, filtered and concentrated under reduced pressure. The residue was purified by flash silica gel chromatography. Compound tert-butyl 5-amino-4-[5-[2-[2-[2-[2-[4-[4-(4-chloro-3-hydroxy-phenyl)-3-(4-pyridyl)pyrazol-1-yl]phenoxy]ethoxy] ethoxy]ethoxy]ethoxy]-1-oxo-isoindolin-2-yl]-5-oxo-pentanoate (230 mg, 0.25 mmol, 51% yield, 95% purity) was obtained as a brown gum. LC/MS (ESI) m/z: 856.1 $[M+1]^+$.

Step 6: Preparation of 3-(5-(2-(2-(2-(2-(4-(4-(4-chloro-3-hydroxyphenyl)-3-(pyridin-4-yl)-1H-pyrazol-1-yl)phenoxy)ethoxy)ethoxy)ethoxy)ethoxy)-1-oxoisoindolin-2-yl)piperidine-2,6-dione

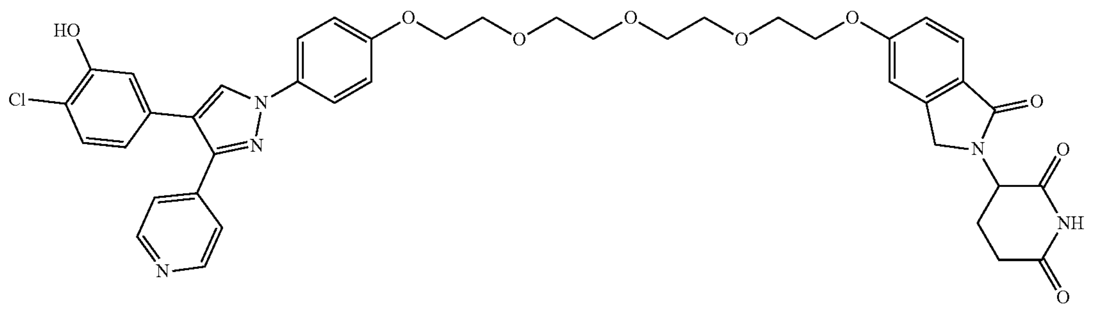 [SMILES: O=C1CCC(N2Cc3cc(OCCOCCOCCOCCOc4ccc(-n5cc(-c6ccc(Cl)c(O)c6)c(-c6ccncc6)n5)cc4)ccc3C2=O)C(=O)N1]

To a solution of tert-butyl 5-amino-4-[5-[2-[2-[2-[2-[4-[4-(4-chloro-3-hydroxy-phenyl)-3-(4-pyridyl)pyrazol-1-yl] phenoxy]ethoxy]ethoxy]ethoxy]ethoxy]-1-oxo-isoindolin-2-yl]-5-oxo-pentanoate (230 mg, 0.25 mmol, 1 eq) in acetonitrile (10 mL) was added benzenesulfonic acid (80 mg, 0.51 mmol, 2 eq). The mixture was stirred at 80° C. for 12 h. The reaction mixture concentrated under reduced pressure. The residue was purified by Semi-preparative reverse phase HPLC. Compound 3-[5-[2-[2-[2-[2-[4-[4-(4-chloro-3-hydroxy-phenyl)-3-(4-pyridyl) pyrazol-1-yl]phenoxy]ethoxy]ethoxy]ethoxy]ethoxy]-1-oxo-isoindolin-2-yl] piperidine-2,6-dione (118.4 mg, 0.12 mmol, 49% yield, 96% purity, Trifluoroacetate) was obtained as a yellow solid. LC/MS (ESI) m/z: 782.2 $[M+1]^+$; $^1$H-NMR (400 MHz, DMSO-$d_6$) δ 10.95 (s, 1H), 10.43-10.21 (m, 1H), 8.96-8.60 (m, 3H), 7.92-7.84 (m, 2H), 7.81 (d, J=5.6 Hz, 2H), 7.60 (d, J=8.4 Hz, 1H), 7.40 (d, J=8.0 Hz, 1H), 7.18-7.09 (m, 3H), 7.04 (dd, J=2.0, 8.4 Hz, 1H), 6.96 (d, J=2.0 Hz, 1H), 6.86 (dd, J=2.0, 8.0 Hz, 1H), 5.05 (dd, J=5.2, 13.3 Hz, 1H), 4.41-4.32 (m, 1H), 4.29-4.21 (m, 1H), 4.20-4.11 (m, 4H), 3.82-3.74 (m, 6H), 3.60 (d, J=2.8 Hz, 6H), 2.96-2.80 (m, 1H), 2.59 (d, J=2.2 Hz, 1H), 2.42-2.35 (m, 1H), 2.03-1.90 (m, 1H).

Exemplary Synthesis of 3-(5-((14-(4-(4-(4-chloro-3-hydroxyphenyl)-3-(pyridin-4-yl)-1H-pyrazol-1-yl)phenoxy)-3,6,9,12-tetraoxatetradecyl)oxy)-1-oxoisoindolin-2-yl)piperidine-2,6-dione (Exemplary Compound 765)

Step 1: Preparation of 14-hydroxy-3,6,9,12-tetraoxatetradecyl 4-methylbenzenesulfonate

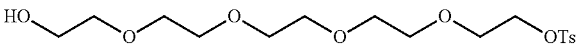 [SMILES: Cc1ccc(S(=O)(=O)OCCOCCOCCOCCOCCO)cc1]

To a cold and stirred solution of pentaethylene glycol (1 eq) in DCM (amount×10 mL) were added $Ag_2O$ (1.5 eq), TsCl (1.1 eq) and KI (0.2 eq). After stirring for 30 to 60 min, the precipitated silver salts were removed by filtration through a pad of Celite and washed thoroughly with EtOAc. The combined filtrate was concentrated under vacuum, and the residue was purified by silica gel chromatography to give a colorless oil, yield 77%. LC/MS (ESI) m/z: 393.2 $[M+1]^+$; $^1$H-NMR (400 MHz, $CDCl_3$) δ 2.45 (s, 3H), 3.59-3.73 (m, 18H), 4.16 (t, J=4.8 Hz, 2H), 7.34 (d, J=8.0 Hz, 2H), 7.80 (d, J=8.0 Hz, 2H).

Step 2: Preparation of 14-(4-(4-bromo-3-(pyridin-4-yl)-1H-pyrazol-1-yl)phenoxy)-3,6,9,12-tetraoxatetradecan-1-ol

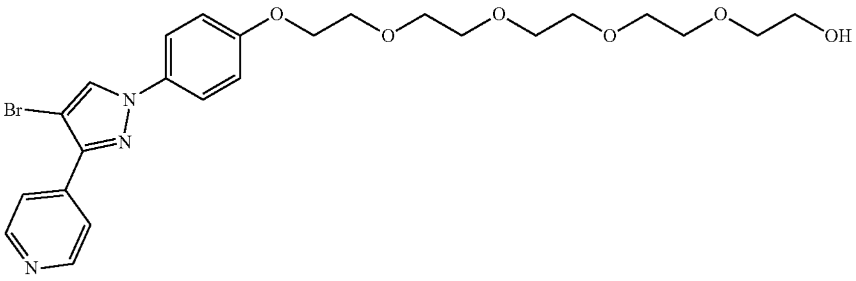 [SMILES: OCCOCCOCCOCCOCCOc1ccc(-n2cc(Br)c(-c3ccncc3)n2)cc1]

To a solution of 4-[4-bromo-3-(4-pyridyl)pyrazol-1-yl]phenol (500 mg, 1.42 mmol, 1 eq, hydrochloride) in N,N-dimethylformamide (10 mL) was added 2-[2-[2-[2-(2-hydroxyethoxy)ethoxy]ethoxy]ethoxy]ethyl 4-methylbenzenesulfonate (556 mg, E42 mmol, 1 eq) and cesium carbonate (924 mg, 2.84 mmol, 2 eq). The mixture was stirred at 80° C. for 2 hours. The mixture was diluted with water (30 mL) and extracted with ethyl acetate (30 mL×3). The combined organic layers were washed with brine (50 mL×3), dried with anhydrous sodium sulfate, filtered and concentrated in vacuum. The crude product was purified by column chromatography (petroleum ether:ethyl acetate=3:1 to dichloromethane:methanol=20:1) to give 2-[2-[2-[2-[2-[4-[4-bromo-3-(4-pyridyl)pyrazol-1-yl]phenoxy]ethoxy]ethoxy]ethoxy]ethoxy]ethanol (500 mg, 0.93 mmol, 65% yield) as a light yellow oil. LC/MS (ESI) m/z: 538.2 $[M+1]^+$; $^1$H NMR (400 MHz, DMSO-$d_6$) δ 8.86 (s, 1H), 8.75-8.65 (m, 2H), 7.96-7.88 (m, 2H), 7.82 (d, J=9.2 Hz, 2H), 7.11 (d, J=9.2 Hz, 2H), 4.56 (t, J=5.6 Hz, 1H), 4.19-4.11 (m, 2H), 3.81-3.73 (m, 2H), 3.63-3.58 (m, 2H), 3.57-3.54 (m, 2H), 3.53-3.49 (m, 8H), 3.49-3.45 (m, 2H), 3.43-3.38 (m, 2H).

Step 3: Preparation of tert-butyl 5-amino-4-(5-((14-(4-(4-bromo-3-(pyridin-4-yl)-1H-pyrazol-1-yl)phenoxy)-3,6,9,12-tetraoxatetradecyl)oxy)-1-oxoisoindolin-2-yl)-5-oxopentanoate

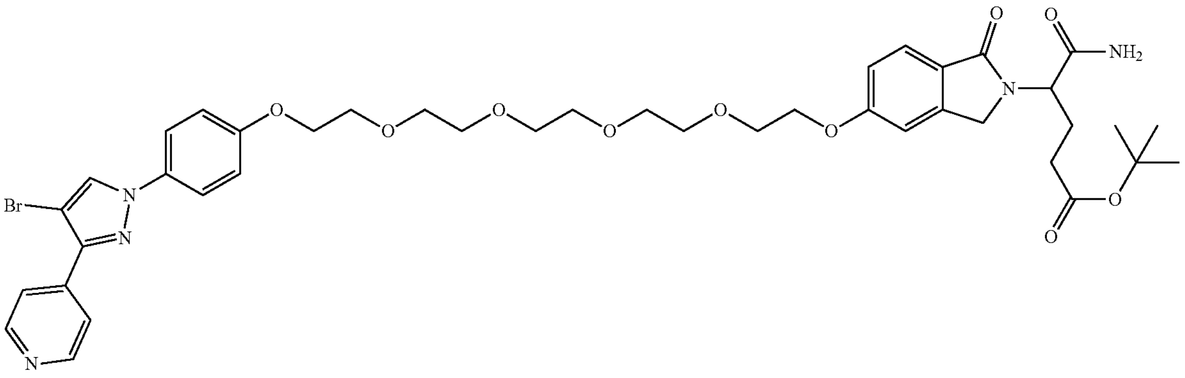 [SMILES: CC(C)(C)OC(=O)CCC(C(N)=O)N1Cc2cc(OCCOCCOCCOCCOCCOc3ccc(-n4cc(Br)c(-c5ccncc5)n4)cc3)ccc2C1=O]

To a solution of 2-[2-[2-[2-[2-[4-[4-bromo-3-(4-pyridyl)pyrazol-1-yl]phenoxy]ethoxy]ethoxy]ethoxy]ethoxy]ethanol (600 mg, 1.12 mmol, 1 eq) and tert-butyl 5-amino-4-(5-hydroxy-1-oxo-isoindolin-2-yl)-5-oxo-pentanoate (374 mg, 1.12 mmol, 1 eq) in tetrahydrofuran (12 mL) was added triphenyl phosophine (352 mg, 1.34 mmol, 1.2 eq) and diisopropyl azodicarboxylate (271 mg, 1.34 mmol, 1.2 eq) at 0° C. under nitrogen atmosphere. The mixture was stirred at 60° C. for 12 hours. The mixture was diluted with water (50 mL) and extracted with ethyl acetate (30 mL×3). The combined organic layers were washed with brine (50 mL×3), dried with anhydrous sodium sulfate, filtered and concentrated in vacuum. The crude product was purified by column chromatography (petroleum ether:ethyl acetate=1:1 to dichloromethane:methanol=10:1). The product was further purified by preparative reverse phase TLC (dichloromethane:methanol=15:1) to give tert-butyl 5-amino-4-[5-[2-[2-[2-[2-[2-[4-[4-bromo-3-(4-pyridyl)pyrazol-1-yl]phenoxy]ethoxy]ethoxy]ethoxy]ethoxy]ethoxy]-1-oxo-isoindolin-2-yl]-5-oxo-pentanoate (300 mg, 0.35 mmol, 31% yield) as a light yellow solid. LC/MS (ESI) m/z: 853.7 $[M+1]^+$; $^1$H-NMR (400 MHz, DMSO-$d_6$) δ 8.86 (s, 1H), 8.74-8.65 (m, 2H), 7.96-7.89 (m, 2H), 7.85-7.79 (m, 2H), 7.57 (d, J=8.4 Hz, 1H), 7.54 (s, 1H), 7.15 (s, 2H), 7.13-7.08 (m, 2H), 7.01 (dd, J=2.0, 8.4 Hz, 1H), 4.75-4.64 (m, 1H), 4.54 (d, J=17.6 Hz, 1H), 4.43-4.30 (m, 1H), 4.15 (td, J=2.8, 5.6 Hz, 4H), 3.79-3.71 (m, 4H), 3.61-3.56 (m, 4H), 3.56-3.53 (m, 4H), 3.52 (s, 4H), 3.17 (d, J=5.2 Hz, 2H), 2.12-2.06 (m, 1H), 2.02-1.89 (m, 1H), 1.32 (s, 9H).

Step 4: Preparation of tert-butyl 5-amino-4-(5-((14-(4-(4-(4-chloro-3-hydroxyphenyl)-3-(pyridin-4-yl)-1H-pyrazol-1-yl)phenoxy)-3,6,9,12-tetraoxatetradecyl)oxy)-1-oxoisoindolin-2-yl)-5-oxopentanoate

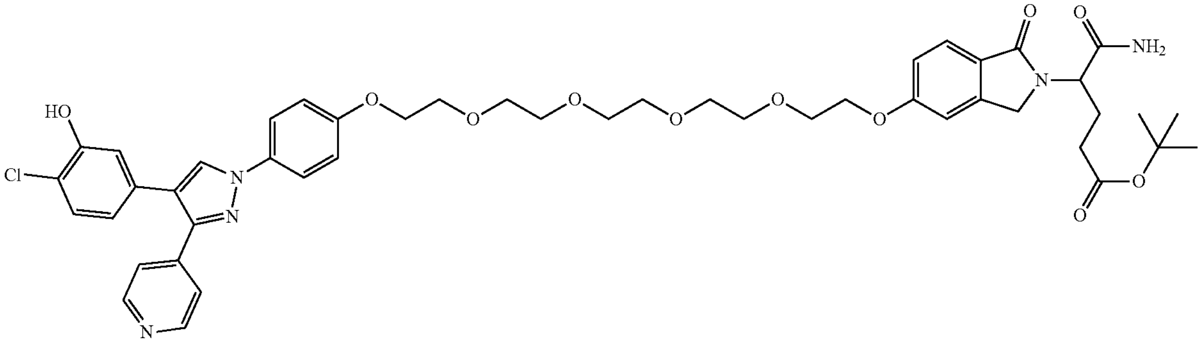 [SMILES: CC(C)(C)OC(=O)CCC(C(N)=O)N1Cc2cc(OCCOCCOCCOCCOCCOc3ccc(-n4cc(-c5ccc(Cl)c(O)c5)c(-c5ccncc5)n4)cc3)ccc2C1=O]

To a solution of tert-butyl 5-amino-4-[5-[2-[2-[2-[2-[2-[4-[4-bromo-3-(4-pyridyl)pyrazol-1-yl] phenoxy]ethoxy]ethoxy]ethoxy]ethoxy]ethoxy]-1-oxo-isoindolin-2-yl]-5-oxo-pentanoate (300 mg, 0.35 mmol, 1 eq) and (4-chloro-3-hydroxy-phenyl)boronic acid (60 mg, 0.35 mmol, 1 eq) in dioxane (6 mL) and water (1 mL) was added cesium fluoride (106 mg, 0.70 mmol, 2 eq) and ditert-butyl(cyclopentyl)phosphane;dichloropalladium;iron (23 mg, 0.035 mmol, 0.1 eq). The mixture was stirred at 90° C. for 2 hours. The mixture was diluted with water (20 mL) and extracted with ethyl acetate (15 mL×3). The combined organic layers were washed with brine (30 mL×2), dried with anhydrous sodium sulfate, filtered and concentrated in vacuum. The crude product was purified by preparative reverse phase TLC (dichloromethane:methanol=10:1) to give tert-butyl 5-amino-4-[5-[2-[2-[2-[2-[2-[4-[4-(4-chloro-3-hydroxy-phenyl)-3-(4-pyridyl)pyrazol-1-yl]phenoxy]ethoxy]ethoxy]ethoxy]ethoxy]ethoxy]-1-oxo-isoindolin-2-yl]-5-oxo-pentanoate (170 mg, 0.18 mmol, 53% yield) as a yellow oil. LC/MS (ESI) m/z: 900.2 $[M+1]^+$.

Step 5: Preparation of 3-(5-((14-(4-(4-(4-chloro-3-hydroxyphenyl)-3-(pyridin-4-yl)-1H-pyrazol-1-yl)phenoxy)-3,6,9,12-tetraoxatetradecyl)oxy)-1-oxoisoindolin-2-yl)piperidine-2,6-dione

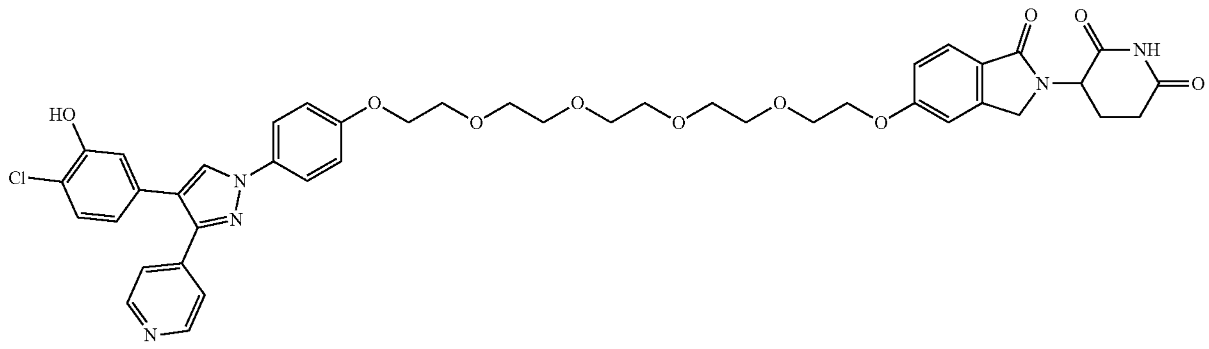 [SMILES: O=C1CCC(N2Cc3cc(OCCOCCOCCOCCOCCOc4ccc(-n5cc(-c6ccc(Cl)c(O)c6)c(-c6ccncc6)n5)cc4)ccc3C2=O)C(=O)N1]

To a solution of tert-butyl 5-amino-4-[5-[2-[2-[2-[2-[2-[4-[4-(4-chloro-3-hydroxy-phenyl)-3-(4-pyridyl)pyrazol-1-yl]phenoxy]ethoxy]ethoxy]ethoxy]ethoxy]ethoxy]-1-oxo-isoindolin-2-yl]-5-oxo-pentanoate (170 mg, 0.18 mmol, 1 eq) in acetonitrile (5 mL) was added benzenesulfonic acid (60 mg, 0.37 mmol, 2 eq). The mixture was stirred at 80° C. for 12 hours. The mixture was concentrated in vacuum. The crude product was purified by preparative reverse phase-HPLC to give 3-[5-[2-[2-[2-[2-[2-[4-[4-(4-chloro-3-hydroxy-phenyl)-3-(4-pyridyl)pyrazol-1-yl]phenoxy]ethoxy]ethoxy]ethoxy]ethoxy]ethoxy]-1-oxo-isoindolin-2-yl]piperidine-2,6-dione (111.8 mg, 0.12 mmol, 66% yield, 97% purity, formate) as a yellow solid. LC/MS (ESI) m/z: 826.3 $[M+1]^+$; $^1H$ NMR (400 MHz, DMSO-$d_6$) δ 11.07-10.85 (m, 1H), 8.66 (s, 1H), 8.61-8.54 (m, 2H), 8.40 (s, 1H), 7.87-7.82 (m, 2H), 7.61 (d, J=8.4 Hz, 1H), 7.51-7.45 (m, 2H), 7.35 (d, J=8.4 Hz, 1H), 7.15 (d, J=2.0 Hz, 1H), 7.12-7.08 (m, 2H), 7.04 (dd, J=2.0, 8.4 Hz, 1H), 6.95 (d, J=2.0 Hz, 1H), 6.80 (dd, J=2.0, 8.4 Hz, 1H), 5.06 (dd, J=5.1, 13.3 Hz, 1H), 4.41-4.32 (m, 1H), 4.29-4.21 (m, 1H), 4.20-4.13 (m, 4H), 3.78-3.74 (m, 4H), 3.60-3.57 (m, 4H), 3.56-3.54 (m, 4H), 3.52 (s, 4H), 2.93-2.83 (m, 1H), 2.62-2.57 (m, 2H), 2.41-2.33 (m, 1H), 2.02-1.92 (m, 1H).

Exemplary Synthesis of (3R)—N-(3-(5-(4-(3-((4-(2-(2,6-dioxopiperidin-3-yl)-1-oxoisoindolin-5-yl)piperazin-1-yl)methyl)azetidin-1-yl)phenyl)-1H-pyrrolo[2,3-b]pyridine-3-carbonyl)-2,4-difluorophenyl)-3-fluoropyrrolidine-1-sulfonamide (Exemplary Compound 767)

Step 1: Preparation of azetidin-3-ylmethanol

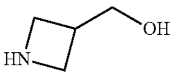

To a solution of tert-butyl 3-(hydroxymethyl)azetidine-1-carboxylate (5 g, 26.70 mmol, 1 eq) in dichloromethane (60 mL) was added trifluoroacetic acid (15 mL, 7.59 eq). The mixture was stirred at 15° C. for 0.5 hour. The reaction mixture was concentrated to give azetidin-3-ylmethanol (4.3 g, trifluoroacetate) as a light yellow oil.

Step 2: Preparation of (1-(4-iodophenyl)azetidin-3-yl)methanol

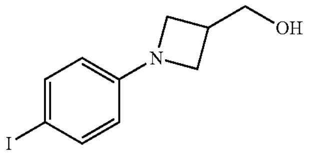 [SMILES: OCC1CN(c2ccc(I)cc2)C1]

To a solution of azetidin-3-ylmethanol (4.3 g, 21.38 mmol, 1 eq, trifluoroacetate) in dimethylsulfoxide (100 mL) was added potassium carbonate (14.77 g, 106.89 mmol, 5 eq). The mixture was stirred at 15° C. for 0.5 hour. 1,4-diiodobenzene (7.76 g, 23.52 mmol, 1.1 eq), L-proline (984 mg, 8.55 mmol, 0.4 eq) and cuprous iodide (814 mg, 4.28 mmol, 0.2 eq) was added, then the mixture was stirred at 90° C. for 12 hours. The reaction mixture was diluted with water (300 mL) and extracted with ethyl acetate (150 mL×2). The combined organic phase was washed with saturated brine (200 mL×2), dried with anhydrous sodium sulfate, filtered and concentrated. The residue was purified by column chromatography (petroleum ether:ethyl acetate=20:1 to 3:1) to give [1-(4-iodophenyl)azetidin-3-yl]methanol (3.5 g, 12.11 mmol, 56% yield) as a white solid. LC/MS (ESI) m/z: 290.4 $[M+1]^+$.

Step 3: Preparation of 1-(4-iodophenyl)azetidine-3-carbaldehyde

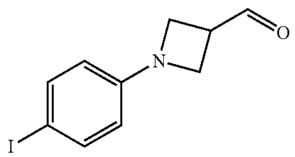 [SMILES: O=CC1CN(c2ccc(I)cc2)C1]

To a solution of oxalyl chloride (3.03 g, 23.87 mmol, 2.1 mL, 2.3 eq) in dichloromethane (40 mL) was dropwise added a solution of dimethylsulfoxide (3.73 g, 47.73 mmol, 3.73 mL, 4.6 eq) in dichloromethane (20 mL) at −70° C. The mixture was stirred at −70° C. for 0.5 hour. A solution of [1-(4-iodophenyl)azetidin-3-yl]methanol (3 g, 10.38 mmol, 1 eq) in dichloromethane (30 mL) was dropwise to the mixture and the mixture was stirred at −70° C. for 0.5 hour. Triethylamine (5.46 g, 53.96 mmol, 7.5 mL, 5.2 eq) was added at −70° C. and warmed to 15° C. The mixture was stirred at 15° C. for 2 hours. The reaction mixture was diluted with water (200 mL) and extracted with dichloromethane (150 mL×2). The combined organic phase was washed with saturated brine (150 mL×2), dried with anhydrous sodium sulfate, filtered and concentrated. The residue was purified by column chromatography (petroleum ether: ethyl acetate=20:1 to 5:1) to give 1-(4-iodophenyl)azetidine-3-carbaldehyde (870 mg, 3.03 mmol, 29% yield) as a yellow oil. LC/MS (ESI) m/z: 320.4 $[M+32+1]^+$.

Step 4: Preparation of 3-(5-(4-((1-(4-iodophenyl) azetidin-3-yl)methyl)piperazin-1-yl)-1-oxoisoindolin-2-yl)piperidine-2,6-dione

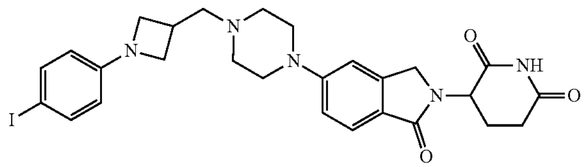 [SMILES: O=C1CCC(N2Cc3cc(N4CCN(CC5CN(c6ccc(I)cc6)C5)CC4)ccc3C2=O)C(=O)N1]

To a solution of 3-(1-oxo-5-piperazin-1-yl-isoindolin-2-yl)piperidine-2,6-dione (1.11 g, 3.03 mmol, 1 eq, hydrochloride) in methanol (20 mL) and dimethylformamide (5 mL) was added sodium acetate (745 mg, 9.09 mmol, 3 eq). The mixture was stirred at 30° C. for 0.5 hour. 1-(4-iodophenyl) azetidine-3-carbaldehyde (870 mg, 3.03 mmol, 1 eq) was added, then the mixture was stirred at 30° C. for 12 hours. Sodium cyanoborohydride (380 mg, 6.06 mmol, 2 eq) was added and the mixture was stirred at 30° C. for another 0.5 hour. The mixture reaction was poured into water (50 mL) and stirred for 10 min. The reaction mixture was filtered, and the filter cake was collected. The crude product was triturated with methanol (30 mL×3) to give 3-[5-[4-[[1-(4-iodophenyl)azetidin-3-yl]methyl]piperazin-1-yl]-1-oxo-isoindolin-2-yl]piperidine-2,6-dione (680 mg, 1.13 mmol, 37% yield) as a white solid. LC/MS (ESI) m/z: 600.1 $[M+1]^+$.

Step 5: Preparation of tert-butyl 3-(2,6-difluoro-3-(((R)-3-fluoropyrrolidine)-1-sulfonamido)benzoyl)-5-(4-(3-((4-(2-(2,6-dioxopiperidin-3-yl)-1-oxoisoindolin-5-yl)piperazin-1-yl)methyl)azetidin-1-yl) phenyl)-1H-pyrrolo[2,3-b]pyridine-1-carboxylate

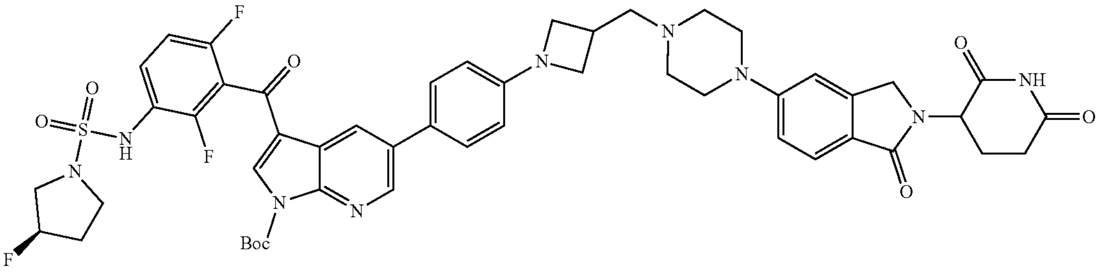 [SMILES: CC(C)(C)OC(=O)n1cc(C(=O)c2c(F)ccc(NS(=O)(=O)N3CC[C@@H](F)C3)c2F)c2cc(-c3ccc(N4CC(CN5CCN(c6ccc7c(c6)CN(C6CCC(=O)NC6=O)C7=O)CC5)C4)cc3)cnc21]

A mixture of 3-[5-[4-[[1-(4-iodophenyl)azetidin-3-yl] methyl]piperazin-1-yl]-1-oxo-isoindolin-2-yl]piperidine-2,6-dione (500 mg, 0.83 mmol, 1 eq), tert-butyl 3-[2,6-difluoro-3-[[(3R)-3-fluoropyrrolidin-1-yl]sulfonylamino] benzoyl]-5-(4,4,5,5-tetramethyl-1,3,2-dioxaborolan-2-yl) pyrrolo[2,3-b]pyridine-1-carboxylate (651 mg, 1.00 mmol, 1.2 eq), ditert-butyl(cyclopentyl)phosphane;dichloropalladium;iron (54 mg, 0.083 mmol, 0.1 eq), potassium carbonate (172 mg, 1.25 mmol, 1.5 eq) and water (2 mL) in dimethylformamide (20 mL) was degassed and purged with nitrogen for 3 times, and then the mixture was stirred at 90° C. for 1.5 hours under nitrogen atmosphere. The reaction mixture was diluted with water (50 mL) and extracted with tetrahydrofuran/ethyl acetate (V/V=2:1, 50 mL×2). The combined organic phase was washed with saturated brine (50 mL×2), dried with anhydrous sodium sulfate, filtered and concentrated. The residue was purified by column chromatography (dichloromethane:methanol=100:1 to 10:1) to give tert-butyl 3-[2,6-difluoro-3-[[(3R)-3-fluoropyrrolidin-1-yl]sulfonylamino]benzoyl]-5-[4-[3-[[4-[2-(2,6-dioxo-3-piperidyl)-1-oxo-isoindolin-5-yl]piperazin-1-yl]methyl] azetidin-1-yl]phenyl]pyrrolo[2,3-b]pyridine-1-carboxylate (210 mg, 0.17 mmol, 20% yield, 82% purity) as a yellow solid. LC/MS (ESI) m/z: 896.2 $[M-99]^+$.

Step 6: Preparation of (3R)—N-(3-(5-(4-(3-((4-(2-(2,6-dioxopiperidin-3-yl)-1-oxoisoindolin-5-yl)piperazin-1-yl)methyl)azetidin-1-yl)phenyl)-1H-pyrrolo[2,3-b]pyridine-3-carbonyl)-2,4-difluorophenyl)-3-fluoropyrrolidine-1-sulfonamide

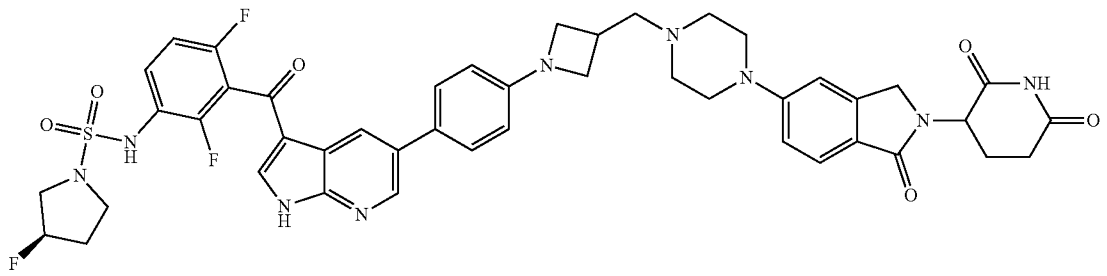 [SMILES: O=C1CCC(N2Cc3cc(N4CCN(CC5CN(c6ccc(-c7cnc8[nH]cc(C(=O)c9c(F)ccc(NS(=O)(=O)N%10CC[C@@H](F)C%10)c9F)c8c7)cc6)C5)CC4)ccc3C2=O)C(=O)N1]

To a solution of tert-butyl 3-[2,6-difluoro-3-[[(3R)-3-fluoropyrrolidin-1-yl]sulfonylamino]benzoyl]-5-[4-[3-[[4-[2-(2,6-dioxo-3-piperidyl)-1-oxo-isoindolin-5-yl]piperazin-1-yl]methyl]azetidin-1-yl]phenyl]pyrrolo[2,3-b]pyridine-1-carboxylate (210 mg, 0.17 mmol, 1 eq) in dichloromethane (10 mL) was added trifluoroacetic acid (2.46 mL, 192.18 eq). The mixture was stirred at 15° C. for 0.5 hour. The reaction mixture was concentrated. The residue was purified by prep-HPLC to give (3R)—N-[3-[5-[4-[3-[[4-[2-(2,6-dioxo-3-piperidyl)-1-oxo-isoindolin-5-yl]piperazin-1-yl]methyl]azetidin-1-yl]phenyl]-1H-pyrrolo[2,3-b]pyridine-3-carbonyl]-2,4-difluoro-phenyl]-3-fluoro-pyrrolidine-1-sulfonamide (99 mg, 0.10 mmol, 60% yield, 99% purity, formate salt) as a yellow solid. LC/MS (ESI) m/z: 896.3 $[M+1]^+$; $^1H$-NMR (400 MHz, DMSO-$d_6$) δ 12.90 (s, 1H), 10.96 (s, 1H), 8.62 (d, J=2.0 Hz, 1H), 8.50 (s, 1H), 8.15 (s, 1H), 8.06 (s, 1H), 7.62 (dt, J=6.0, 8.8 Hz, 1H), 7.54 (dd, J=8.8, 12.0 Hz, 3H), 7.26 (t, J=8.8 Hz, 1H), 7.12-7.03 (m, 2H), 6.57 (d, J=8.8 Hz, 2H), 5.39-5.19 (m, 1H), 5.05 (dd, J=5.2, 13.2 Hz, 1H), 4.38-4.29 (m, 1H), 4.25-4.17 (m, 1H), 4.01 (t, J=7.4 Hz, 2H), 3.58-3.52 (m, 2H), 3.49-3.45 (M, 2H), 3.41-3.38 (m, 4H), 3.05-2.84 (m, 3H), 2.62-2.58 (m, 1H), 2.58-2.52 (m, 8H), 2.43-2.34 (m, 1H), 2.13-2.04 (m, 1H), 1.99-1.93 (m, 1H).

Exemplary Synthesis of (3R)—N-(3-(5-(4-(4-((4-(3-(2,6-dioxopiperidin-3-yl)phenyl)piperazin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide (Exemplary Compound 768)

Step 1: Preparation of tert-butyl 4-(3-(2-methoxy-2-oxoethyl)phenyl)piperazine-1-carboxylate

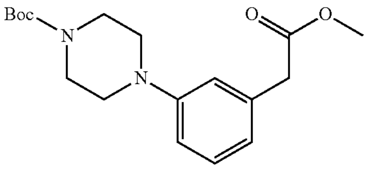 [SMILES: COC(=O)Cc1cccc(N2CCN(C(=O)OC(C)(C)C)CC2)c1]

Into a 250-mL round-bottom flask purged and maintained with an inert atmosphere of nitrogen, was placed methyl 2-(3-bromophenyl)acetate (10.0 g, 43.65 mmol, 1.0 equiv), tert-butyl piperazine-1-carboxylate (8.1 g, 43.65 mmol, 1 equiv), $Cs_2CO_3$ (28.5 g, 87.31 mmol, 2 equiv), RuPhos-PdCl-2nd G (3.4 g, 4.37 mmol, 0.1 equiv), toluene (150 mL). The resulting solution was stirred overnight at 80° C. The resulting mixture was concentrated under vacuum. The residue was applied onto a silica gel column with ethyl acetate/petroleum ether (1:19). This resulted in 10.1 g (69.2%) of tert-butyl 4-[3-(2-methoxy-2-oxoethyl)phenyl]piperazine-1-carboxylate as a yellow liquid. LC/MS (ESI) m/z: 335.19 $[M+1]^+$.

Step 2: Preparation of 5-ethyl 1-methyl 2-(3-(4-(tert-butoxycarbonyl)piperazin-1-yl(phenyl(pentanedioate

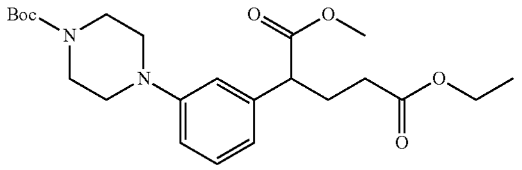 [SMILES: CCOC(=O)CCC(C(=O)OC)c1cccc(N2CCN(C(=O)OC(C)(C)C)CC2)c1]

Into a 100-mL 3-necked round-bottom flask purged and maintained with an inert atmosphere of nitrogen, was placed tert-butyl 4-[3-(2-methoxy-2-oxoethyl)phenyl]piperazine-1-carboxylate (3.0 g, 8.97 mmol, 1.0 equiv), tetrahydrofuran (30 mL) at 0° C. in a water/ice bath. The resulting mixture was stirred for 30 min at 0° C., and then tert-butoxysodium (1.7 g, 17.94 mmol, 2.0 equiv) and ethyl acrylate (1.1 g, 10.76 mmol, 1.2 equiv) was added into the flask. The resulting solution was stirred overnight at room temperature. The resulting mixture was concentrated under vacuum. The residue was applied onto a silica gel column with ethyl acetate/petroleum ether (1:1). This resulted in 1.3 g (33.4%) of 5-ethyl 1-methyl 2-[3-[4-(tert-butoxycarbonyl)piperazin-1-yl]phenyl]pentanedioate as a yellow solid. LC/MS (ESI) m/z: 435.25 $[M+1]^+$.

Step 3: Preparation of tert-butyl 4-(3-(5-amino-1-methoxy-1,5-dioxopentan-2-yl)phenyl)piperazine-1-carboxylate

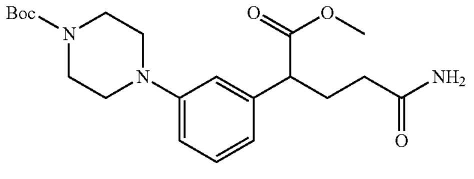 [SMILES: COC(=O)C(CCC(N)=O)c1cccc(N2CCN(C(=O)OC(C)(C)C)CC2)c1]

Into a 20-mL sealed tube purged and maintained with an inert atmosphere of nitrogen, was placed 5-ethyl 1-methyl 2-[3-[4-(tert-butoxycarbonyl)piperazin-1-yl]phenyl]pentanedioate (590.0 mg). To the above $NH_3$ (g) in MeOH (13.00 mL) was added into the solution. The resulting solution was stirred for 20 h at 35° C. The resulting mixture was concentrated under vacuum. The residue was applied onto a silica gel column with ethyl acetate/petroleum ether (100%). This resulted in 220 mg (37.3%) of 5-amino 1-methyl 2-[3-[4-(tert-butoxycarbonyl)piperazin-1-yl]phenyl]pentanedioate as a white solid. LC/MS (ESI) m/z: 406.15 $[M+1]^+$.

Step 4: Preparation of tert-butyl 4-(3-(2,6-dioxopiperidin-3-yl)phenyl)piperazine-1-carboxylate

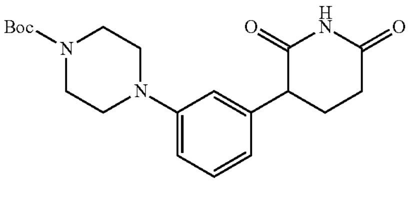 [SMILES: CC(C)(C)OC(=O)N1CCN(c2cccc(C3CCC(=O)NC3=O)c2)CC1]

Into a 8-mL sealed tube purged and maintained with an inert atmosphere of nitrogen, was placed tert-butyl 4-[3-(4-carbamoyl-1-methoxy-1-oxobutan-2-yl)phenyl]piperazine-1-carboxylate (200.0 mg, 0.49 mmol, 1.0 equiv), $Cs_2CO_3$ (322.4 mg, 0.99 mmol, 2 equiv), acetonitrile (5 mL). The resulting solution was stirred for 8 hr at 85° C. The resulting mixture was concentrated under vacuum. The residue was applied onto a silica gel column with dichloromethane/methanol (19:1). This resulted in 58 mg (31.5%) of tert-butyl 4-[3-(2,6-dioxopiperidin-3-yl)phenyl]piperazine-1-carboxylate as a yellow solid. LC/MS (ESI) m/z: 374.25 $[M+1]^+$.

Step 5: Preparation of 3-(3-(piperazin-1-yl)phenyl)piperidine-2,6-dione

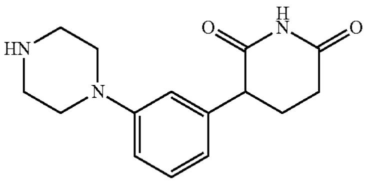 [SMILES: O=C1CCC(c2cccc(N3CCNCC3)c2)C(=O)N1]

Into a 25-mL round-bottom flask, was placed tert-butyl 4-[3-(2,6-dioxopiperidin-3-yl)phenyl]piperazine-1-carboxylate (58.00 mg, 0.155 mmol, 1.00 equiv), DCM (3.00 mL, 0.035 mmol, 0.23 equiv), trifluoroacetaldehyde (0.50 mL, 0.005 mmol, 0.03 equiv). The resulting solution was stirred for 1 h at room temperature. The resulting mixture was concentrated. This resulted in 50 mg (117.78%) of 3-[3-(piperazin-1-yl)phenyl]piperidine-2,6-dione as light yellow oil.

Step 6: Preparation of (3R)—N-(3-(5-(4-(4-((4-(3-(2,6-dioxopiperidin-3-yl)phenyl)piperazin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide

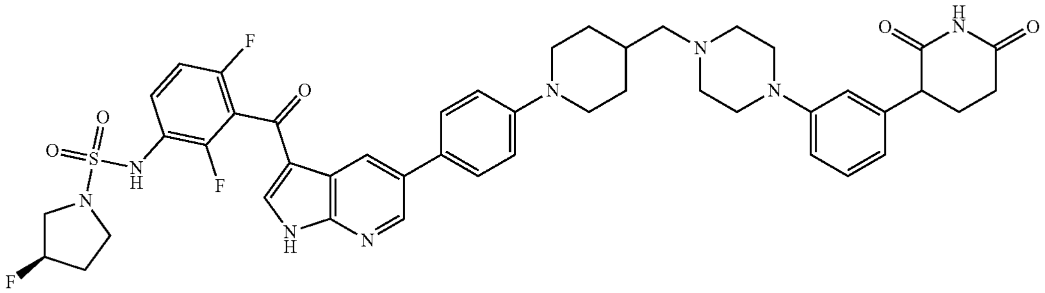 [SMILES: O=C1CCC(c2cccc(N3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)c2)C(=O)N1]

Into a 100-mL round-bottom flask, was placed 3-[3-(piperazin-1-yl)phenyl]piperidine-2,6-dione (40.22 mg, 0.147 mmol, 1.00 equiv), DCE (15.00 mL), DIEA (0.50 mL, 0.004 mmol, 0.03 equiv), (3R)—N-(2,4-difluoro-3-[5-[4-(4-formylpiperidin-1-yl)phenyl]-1H-pyrrolo[2,3-b]pyridine-3-carbonyl]phenyl)-3-fluoropyrrolidine-1-sulfonamide (90.00 mg, 0.147 mmol, 1.00 equiv), HOAc (0.50 mL, 0.008 mmol, 0.06 equiv), after stirred at 35° C. for 3 h, $NaBH_3CN$ (27.74 mg, 0.441 mmol, 3.0 equiv) was added into the solution. The resulting solution was stirred for 16 h at 35° C. in an oil bath. The resulting solution was extracted with dichloromethane (100 mL). The residue was applied onto a silica gel column with dichloromethane/methanol (10/1). The crude product was purified by Flash-Prep-HPLC. This resulted in 22.7 mg (17.75%) of (3R)—N-[3-(5-[4-[4-([4-[3-(2,6-dioxopiperidin-3-yl)phenyl]piperazin-1-yl]methyl)piperidin-1-yl]phenyl]-1H-pyrrolo[2,3-b]pyridine-3-carbonyl)-2,4-difluorophenyl]-3-fluoropyrrolidine-1-sulfonamide as a light yellow solid. LC/MS (ESI) m/z: 869.35 $[M+1]^+$; $^1H$-NMR (400 MHz, DMSO-$d_6$) δ 12.90 (s, 1H), 10.80 (s, 1H), 9.86 (s, 1H), 8.66 (s, 1H), 8.54 (s, 1H), 8.07 (s, 1H), 7.66-7.58 (m, 3H), 7.30-7.25 (m, 1H), 7.19-7.15 (m, 1H), 7.09-7.07 (d, J=8.0 Hz, 2H), 6.85-6.82 (m, 1H), 6.64-6.62 (d, J=8.0 Hz, 1H), 5.37-5.24 (m, 1H), 3.82-3.75 (m, 3H), 3.52-3.39 (m, 5H), 3.15 (m, 4H), 2.79-2.73 (m, 4H), 2.65-2.51 (m, 3H), 2.26-2.03 (m, 3H), 1.87-1.83 (m, 3H), 1.27-1.25 (m, 2H).

Exemplary Synthesis of 5-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-N-(2,6-dioxopiperidin-3-yl)-3,4-dihydro-1,8-naphthyridine-1(2H)-carboxamide (Exemplary Compound 789)

Step 1: Preparation of 3-(3-chloropropyl)-2-fluoro-4-iodopyridine

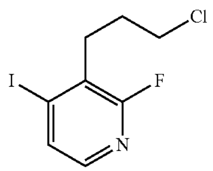 [SMILES: Fc1nccc(I)c1CCCCl]

To a solution of 2-fluoro-4-iodo-pyridine (7.70 g, 34.53 mmol, 1.00 eg) in tetrahydrofuran (80 mL) was added lithium diisopropylamide (2 M, 20.72 mL, 1.20 eq) at −78° C. for 1.5 h. Then the mixture was added a solution of 1-chloro-3-iodo-propane (14.12 g, 69.06 mmol, 7.43 mL, 2.00 eq) in tetrahydrofuran (10 mL) at −78° C. and stirred for 0.5 h. Then the mixture was warmed to 15° C. and stirred for 1 h. The mixture was quenched with saturated ammonium chloride solution (80 mL) and extracted with ethyl acetate (2×40 mL). The combined organic layers were washed with brine (50 mL), dried over sodium sulfate and concentrated to give a residue. The residue was purified by column chromatography (petroleum ether:ethyl acetate=1:0 to 10:1) to give 3-(3-chloropropyl)-2-fluoro-4-iodo-pyridine (9.00 g, 30.05 mmol, 87% yield) as a light yellow oil. $^1H$-NMR (400 MHz, $CDCl_3$) δ 7.69 (d, J=5.6 Hz, 1H), 7.61 (d, J=5.2 Hz, 1H), 3.61 (t, J=6.4 Hz, 2H), 2.90-2.97 (m, 2H), 2.04-2.08 (m, 1H), 1.99-2.03 (m, 1H).

Step 2: Preparation of 1-(2,4-dimethoxybenzyl)-5-iodo-1,2,3,4-tetrahydro-1,8-naphthyridine

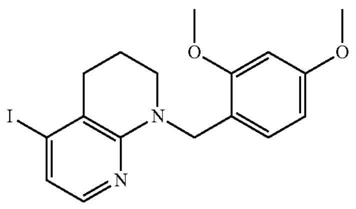 [SMILES: COc1ccc(CN2CCCc3c(I)ccnc32)c(OC)c1]

To a solution of 3-(3-chloropropyl)-2-fluoro-4-iodo-pyridine (3 g, 10.02 mmol, 1 eq) and (2,4-dimethoxyphenyl)methanamine (2.01 g, 12.02 mmol, 1.2 eq) in N,N-dimethylformamide (30 mL) was added potassium iodide (2.00 g, 12.02 mmol, 1.2 eq), pyridine (475 mg, 6.01 mmol, 0.6 eq) and potassium carbonate (2.49 g, 18.03 mmol, 1.8 eq). The mixture was stirred at 70° C. for 12 hours. The mixture was diluted with water (50 mL) and stirred at 15° C. for 15 min. The mixture was filtered, and the filtrate was extracted with ethyl acetate (50 mL×3). The combined organic layers were washed with brine (100 mL×3), dried with anhydrous sodium sulfate, filtered and concentrated in vacuum. The crude product was triturated with petroleum ether and ethyl acetate (V:V=10:1) to give 1-[(2,4-dimethoxyphenyl)methyl]-5-iodo-3,4-dihydro-2H-1,8-naphthyridine (3 g, 7.31 mmol, 73.01% yield) as a brown solid. LC/MS (ESI) m/z: 398.1 $[M-12]^+$.

Step 3: Preparation of tert-butyl 6-(8-(2,4-dimethoxybenzyl)-5,6,7,8-tetrahydro-1,8-naphthyridin-4-yl)-2,6-diazaspiro[3.3]heptane-2-carboxylate

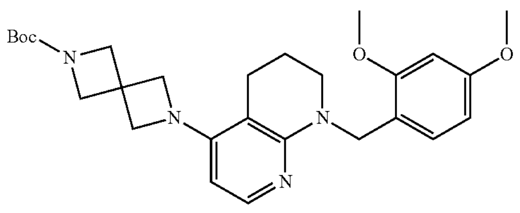 [SMILES: COc1ccc(CN2CCCc3c(N4CC5(CN(C(=O)OC(C)(C)C)C5)C4)ccnc32)c(OC)c1]

To a solution of 1-[(2,4-dimethoxyphenyl)methyl]-5-iodo-3,4-dihydro-2H-1,8-naphthyridine (1.1 g, 2.68 mmol, 1 eq) in 2-methylbutan-2-ol (8.89 g, 100.78 mmol, 37.60 eq) was added tert-butyl 2,6-diazaspiro[3.3]heptane-2-carboxylate;oxalic acid (912 mg, 1.88 mmol, 0.7 eq), sodium tert-butoxide (2 M, 4.02 mL, 3 eq) and methanesulfonato(2-dicyclohexylphosphino-2',6'-di-i-propoxy-1,1'-biphenyl)(2'-amino-1,1'-biphenyl-2-yl)palladium(II) (224 mg, 0.26 mmol, 0.1 eq) under nitrogen atmosphere. The mixture was stirred at 90° C. for 12 hours. The mixture was diluted with water (50 mL) and extracted with ethyl acetate (30 mL×3). The combined organic layers were washed with brine (50 mL×2), dried with anhydrous sodium sulfate, filtered and concentrated in vacuum. The crude product was purified by column chromatography (petroleum ether:ethyl acetate=10:1 to 5:1) to give tert-butyl 6-[8-[(2,4-dimethoxyphenyl)methyl]-6,7-dihydro-5H-1,8-naphthyridin-4-yl]-2,6-diazaspiro[3.3]heptane-2-carboxylate (1 g, 2.08 mmol, 77% yield) as a light yellow oil. LC/MS (ESI) m/z: 481.3 $[M+1]^+$.

Step 4: Preparation of 5-(2,6-diazaspiro[3.3]heptan-2-yl)-1,2,3,4-tetrahydro-1,8-naphthyridine

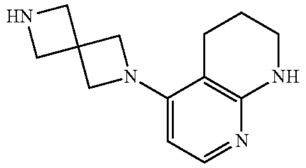 [SMILES: c1cc(N2CC3(CNC3)C2)c2c(n1)NCCC2]

To a solution of tert-butyl 6-[8-[(2,4-dimethoxyphenyl) methyl]-6,7-dihydro-5H-1,8-naphthyridin-4-yl]-2,6-diazaspiro[3.3]heptane-2-carboxylate (1 g, 2.08 mmol, 1 eq) in toluene (10 mL) was added trifluoroacetic acid (7.70 g, 67.53 mmol, 32.45 eq). The mixture was stirred at 65° C. for 1 hour. The mixture was filtered, and the filtrate was concentrated in vacuum. Compound 5-(2,6-diazaspiro[3.3] heptan-2-yl)-1,2,3,4-tetrahydro-1,8-naphthyridine (500 mg, 1.45 mmol, 69% yield, trifluoroacetates) was obtained as a brown oil. LC/MS (ESI) m/z: 231.2 $[M+1]^+$.

Step 5: Preparation of tert-butyl 6-(5,6,7,8-tetrahydro-1,8-naphthyridin-4-yl)-2,6-diazaspiro[3.3] heptane-2-carboxylate

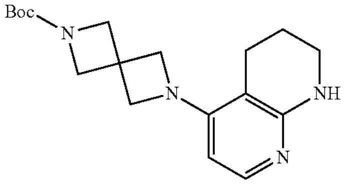 [SMILES: CC(C)(C)OC(=O)N1CC2(C1)CN(c1ccnc3c1CCCN3)C2]

To a solution of 5-(2,6-diazaspiro[3.3]heptan-2-yl)-1,2,3,4-tetrahydro-1,8-naphthyridine (500 mg, 1.45 mmol, 1 eq, trifluoroacetates) in dichloromethane (10 mL) was added di-tert-butyl dicarbonate (380 mg, 1.74 mmol, 1.2 eq), triethylamine (734 mg, 7.26 mmol, 5 eq) and 4-dimethylaminopyridine (17 mg, 0.14 mmol, 0.1 eq). The mixture was stirred at 15° C. for 1 hour. The mixture was diluted with water (20 mL) and extracted with ethyl acetate (15 mL×3). The combined organic layers were washed with brine (30 mL×2), dried with anhydrous sodium sulfate, filtered and concentrated in vacuum. The crude product was purified by preparative reverse phase TLC (dichloromethane:methanol=8:1) to give tert-butyl 6-(5,6,7,8-tetrahydro-1,8-naphthyridin-4-yl)-2,6-diazaspiro[3.3]heptane-2-carboxylate (380 mg, 1.15 mmol, 79% yield) as a light yellow solid. LC/MS (ESI) m/z: 331.5 $[M+1]^+$; $^1$H-NMR (400 MHz, DMSO-$d_6$) δ 7.48 (d, J=5.6 Hz, 1H), 6.06 (s, 1H), 5.66 (d, J=5.9 Hz, 1H), 4.07 (s, 4H), 3.99 (s, 4H), 3.16 (s, 2H), 2.47 (s, 2H), 1.74-1.65 (m, 2H), 1.37 (s, 9H).

Step 6: Preparation of tert-butyl 6-(8-((2,6-dioxopiperidin-3-yl)carbamoyl)-5,6,7,8-tetrahydro-1,8-naphthyridin-4-yl)-2,6-diazaspiro[3.3]heptane-2-carboxylate

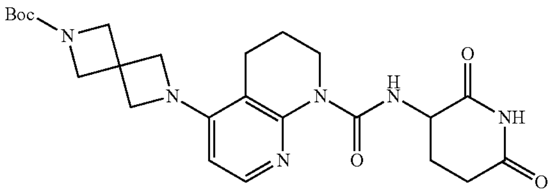 [SMILES: CC(C)(C)OC(=O)N1CC2(C1)CN(c1ccnc3c1CCCN3C(=O)NC1CCC(=O)NC1=O)C2]

To a solution of tert-butyl 6-(5,6,7,8-tetrahydro-1,8-naphthyridin-4-yl)-2,6-diazaspiro[3.3]heptane-2-carboxylate (380 mg, 1.15 mmol, 1 eq) in tetrahydrofuran (10 mL) was added triethylamine (698 mg, 6.90 mmol, 6 eq) and bis (trichloromethyl) carbonate (341 mg, 1.15 mmol, 1 eq) at 0° C. The mixture was stirred at 25° C. for 3 hours. Then 3-aminopiperidine-2,6-dione (227.14 mg, 1.38 mmol, 1.2 eq, hydrochloride) was added to the mixture. The mixture was stirred at 50° C. for 36 hours. The mixture was diluted with water (30 mL) and extracted with ethyl acetate (20 mL×3). The combined organic layers were washed with brine (40 mL×2), dried with anhydrous sodium sulfate, filtered and concentrated in vacuum. The crude product was purified by preparative reverse phase TLC (dichloromethane:methanol=15:1) to give tert-butyl 6-[8-[(2,6-dioxo-3-piperidyl)carbamoyl]-6,7-dihydro-5H-1,8-naphthyridin-4-yl]-2,6-diazaspiro[3.3]heptane-2-carboxylate (220 mg, 0.45 mmol, 39% yield) as a white solid. LC/MS (ESI) m/z: 485.2 $[M+1]^+$; $^1$H-NMR (400 MHz, DMSO-$d_6$) δ 11.19 (d, J=6.4 Hz, 1H), 10.79 (s, 1H), 7.80 (d, J=5.6 Hz, 1H), 6.12 (d, J=5.6 Hz, 1H), 4.58-4.46 (m, 1H), 4.17 (s, 4H), 4.05-3.97 (m, 4H), 3.84-3.72 (m, 2H), 2.80-2.67 (m, 1H), 2.57 (t, J=6.0 Hz, 2H), 2.20-2.09 (m, 1H), 2.07-1.89 (m, 2H), 1.81-1.66 (m, 2H), 1.38 (s, 9H).

Step 7: Preparation of N-(2,6-dioxopiperidin-3-yl)-5-(2,6-diazaspiro[3.3]heptan-2-yl)-3,4-dihydro-1,8-naphthyridine-1 (2H)-carboxamide

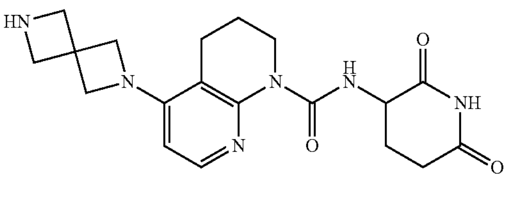 [SMILES: O=C1CCC(NC(=O)N2CCCc3c(N4CC5(CNC5)C4)ccnc32)C(=O)N1]

To a solution of tert-butyl 6-[8-[(2,6-dioxo-3-piperidyl) carbamoyl]-6,7-dihydro-5H-1,8-naphthyridin-4-yl]-2,6-diazaspiro[3.3]heptane-2-carboxylate (220 mg, 0.45 mmol, 1 eq) in dichloromethane (5 mL) was added triethylamine (3.85 g, 33.77 mmol, 74.37 eq). The mixture was stirred at 15° C. for 1 hour. The mixture was concentrated in vacuum. Compound 5-(2,6-diazaspiro[3.3]heptan-2-yl)-N-(2,6-dioxo-3-piperidyl)-3,4-dihydro-2H-1,8-naphthyridine-1-carboxamide (220 mg, 0.44 mmol, 97.21% yield, trifluoroacetates) was obtained as a light yellow solid. LC/MS (ESI) m/z: 385.3 $[M+1]^+$.

Step 8: Preparation of 5-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-N-(2,6-dioxopiperidin-3-yl)-3,4-dihydro-1,8-naphthyridine-1(2H)-carboxamide

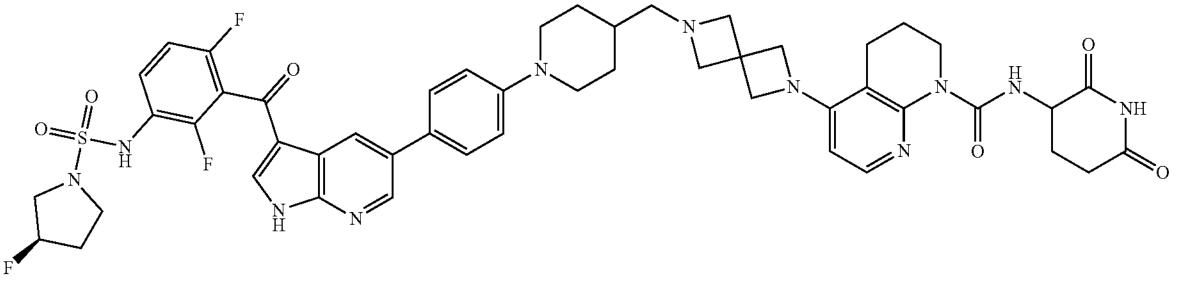 [SMILES: O=C1CCC(NC(=O)N2CCCc3c(N4CC5(CN(CC6CCN(c7ccc(-c8cnc9[nH]cc(C(=O)c%10c(F)ccc(NS(=O)(=O)N%11CC[C@@H](F)C%11)c%10F)c9c8)cc7)CC6)C5)C4)ccnc32)C(=O)N1]

To a solution of 5-(2,6-diazaspiro[3.3]heptan-2-yl)-N-(2,6-dioxo-3-piperidyl)-3,4-dihydro-2H-1,8-naphthyridine-1-carboxamide (110 mg, 0.22 mmol, 1 eq, trifluoroacetates) in N,N-dimethylformamide (5 mL) was added sodium acetate (90 mg, 1.10 mmol, 5 eq). The mixture was stirred at 15° C. for 0.5 hour. Then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (134 mg, 0.22 mmol, 1 eq) and acetic acid (26 mg, 0.44 mmol, 2 eq) was added to the mixture. The mixture was stirred at 15° C. for 0.5 hour. Then sodium cyanoborohydride (27 mg, 0.44 mmol, 2 eq) was added to the mixture. The mixture was stirred at 15° C. for 2 hours. The mixture was filtered and the filtrate was purified by prep-HPLC to give 5-[6-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-diazaspiro[3.3]heptan-2-yl]-N-(2,6-dioxo-3-piperidyl)-3,4-dihydro-2H-1,8-naphthyridine-1-carboxamide (44.5 mg, 0.04 mmol, 19% yield, 98% purity, formate) as a yellow solid. LC/MS (ESI) m/z: 981.3 $[M+1]^+$; $^1$H-NMR (400 MHz, DMSO-$d_6$)< ) 11.20 (d, J=6.8 Hz, 1H), 10.79 (s, 1H), 8.64 (s, 1H), 8.52 (d, J=2.8 Hz, 1H), 8.17 (s, 1H), 8.05 (s, 1H), 7.79 (d, J=5.2 Hz, 1H), 7.66-7.60 (m, 1H), 7.53 (d, J=2.8 Hz, 2H), 7.24 (t, J=8.4 Hz, 1H), 7.05 (d, J=8.0 Hz, 2H), 6.13 (d, J=5.6 Hz, 1H), 5.40-5.15 (m, 1H), 4.58-4.45 (m, 1H), 4.12 (s, 4H), 3.82-3.74 (m, 4H), 3.47 (s, 4H), 3.27-3.26 (m, 4H), 2.75-2.64 (m, 4H), 2.54-2.52 (m, 3H), 2.34-2.31 (m, 2H), 2.18-2.04 (m, 3H), 2.04-1.91 (m, 2H), 1.83-1.71 (m, 4H), 1.51-1.39 (m, 1H), 1.30-1.18 (m, 2H).

Exemplary Synthesis of 4-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-N-(2,6-dioxopiperidin-3-yl)-2-methoxybenzamide (Exemplary Compound 790)

Step 1: Preparation of tert-butyl 6-(3-methoxy-4-(methoxycarbonyl)phenyl)-2,6-diazaspiro[3.3]heptane-2-carboxylate

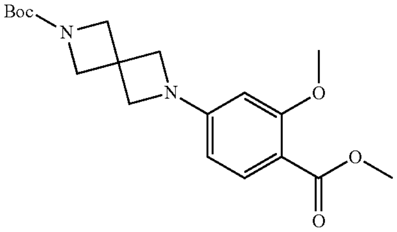 [SMILES: COC(=O)c1ccc(N2CC3(CN(C(=O)OC(C)(C)C)C3)C2)cc1OC]

To a solution of methyl 4-fluoro-2-methoxy-benzoate (500 mg, 2.71 mmol, 1 eq) and tert-butyl 2,6-diazaspiro[3.3]heptane-2-carboxylate;oxalic acid (660 mg, 1.36 mmol, 0.5 eq) in dimethylsulfoxide (10 mL) was added diisopropylethylamine (701 mg, 5.43 mmol, 945.80 uL, 2 eq). The mixture was stirred at 120° C. for 2 h. Water (50 mL) was poured into the mixture and stirred for 1 minute. The aqueous phase was extracted with ethyl acetate (20 mL×3). The combined organic phase was washed with brine (20 mL×2), dried with anhydrous sodium sulfate, filtered and concentrated in vacuum. The residue was purified by column chromatography (Petroleum ether/Ethyl acetate=10/1 to 1/1). Compound tert-butyl 6-(3-methoxy-4-methoxycarbonyl-phenyl)-2,6-diazaspiro[3.3]heptane-2-carboxylate (250 mg, 0.68 mmol, 25% yield) was obtained as a white solid. LC/MS (ESI) m/z: 363.2 $[M+1]^+$.

Step 2: Preparation of 4-(6-(tert-butoxycarbonyl)-2,6-diazaspiro[3.3]heptan-2-yl)-2-methoxybenzoic acid

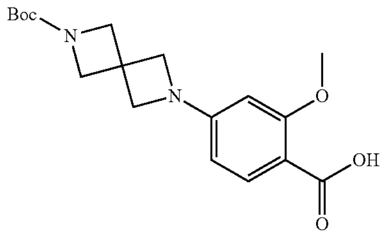 [SMILES: COc1cc(N2CC3(CN(C(=O)OC(C)(C)C)C3)C2)ccc1C(=O)O]

To a solution of tert-butyl 6-(3-methoxy-4-methoxycarbonyl-phenyl)-2,6-diazaspiro[3.3]heptane-2-carboxylate (250 mg, 0.68 mmol, 1 eq) in tetrahydrofuran (5 mL), methanol (5 mL) and water (5 mL) was added lithium hydroxide monohydrate (115. mg, 2.76 mmol, 4 eq). The mixture was stirred at 20° C. for 12 h. Water (50 mL) was poured into the mixture and stirred for 1 minute. The aqueous phase was extracted with ethyl acetate (20 mL×3). The combined organic phase was washed with brine (20 mL×2), dried with anhydrous sodium sulfate, filtered and concentrated in vacuum. The residue was purified by column chromatography (dichloromethane:methanol=1:0 to 20:1). Compound 4-(2-tert-butoxycarbonyl-2,6-diazaspiro[3.3]heptan-6-yl)-2-methoxy-benzoic acid (230 mg, 0.66 mmol, 95% yield) was obtained as a white solid. LC/MS (ESI) m/z: 349.3 $[M+1]^+$.

Step 3: Preparation of tert-butyl 6-(4-((2,6-dioxopiperidin-3-yl)carbamoyl)-3-methoxyphenyl)-2,6-diazaspiro[3.3]heptane-2-carboxylate

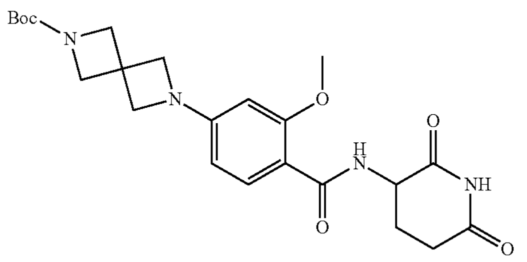 [SMILES: COc1cc(N2CC3(CN(C(=O)OC(C)(C)C)C3)C2)ccc1C(=O)NC1CCC(=O)NC1=O]

To a solution of 4-(2-tert-butoxycarbonyl-2,6-diazaspiro[3.3]heptan-6-yl)-2-methoxy-benzoic acid (230 mg, 0.66 mmol, 1 eq) in N,N-dimethylformamide (5 mL) was added o-(7-azabenzotriazol-1-yl)-n,n,n',n'-tetramethyluronium hexafluorophosphate (376 mg, 0.99 mmol, 1.5 eq) and 3-aminopiperidine-2,6-dione (108 mg, 0.66 mmol, 1 eq, hydrochloride). The mixture was stirred at 15° C. for 0.5 h. Diisopropylethylamine (170 mg, 1.32 mmol, 229.98 uL, 2 eq) was added and the mixture was stirred at 15° C. for 11.5 h. Water (40 mL) was poured into the mixture and stirred for 1 minute. The aqueous phase was extracted with ethyl acetate (10 mL×3). The combined organic phase was washed with brine (10 mL×2), dried with anhydrous sodium sulfate, filtered and concentrated in vacuum. The residue was purified by prep-TLC (dichloromethane:methanol=10:1). Compound tert-butyl 6-[4-[(2,6-dioxo-3-piperidyl) carbamoyl]-3-methoxy-phenyl]-2,6-diazaspiro[3.3]heptane-2-carboxylate (120 mg, 0.26 mmol, 39% yield) was obtained as a white solid. LC/MS (ESI) m/z: 459.2 $[M+1]^+$.

Step 4: Preparation of N-(2,6-dioxopiperidin-3-yl)-2-methoxy-4-(2,6-diazaspiro[3.3]heptan-2-yl)benzamide

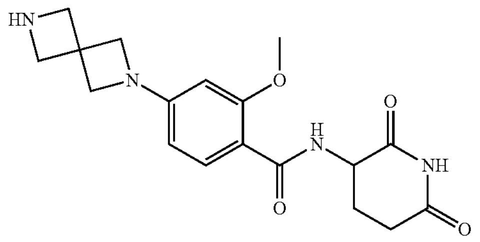 [SMILES: COc1cc(N2CC3(CNC3)C2)ccc1C(=O)NC1CCC(=O)NC1=O]

To a solution of tert-butyl 6-[4-[(2,6-dioxo-3-piperidyl) carbamoyl]-3-methoxy-phenyl]-2,6-diazaspiro[3.3]heptane-2-carboxylate (120 mg, 0.26 mmol, 1 eq) in dichloromethane (2 mL) was added trifluoroacetic acid (770 mg, 6.75 mmol, 0.5 mL, 25.80 eq). The mixture was stirred at 20° C. for 12 h. Compound 4-(2,6-diazaspiro[3.3]heptan-2-yl)-N-(2,6-dioxo-3-piperidyl)-2-methoxy-benzamide (120 mg, trifluoroacetate) was obtained as a white solid. LC/MS (ESI) m/z: 359.2 $[M+1]^+$.

Step 5: Preparation of 4-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-N-(2,6-dioxopiperidin-3-yl)-2-methoxybenzamide

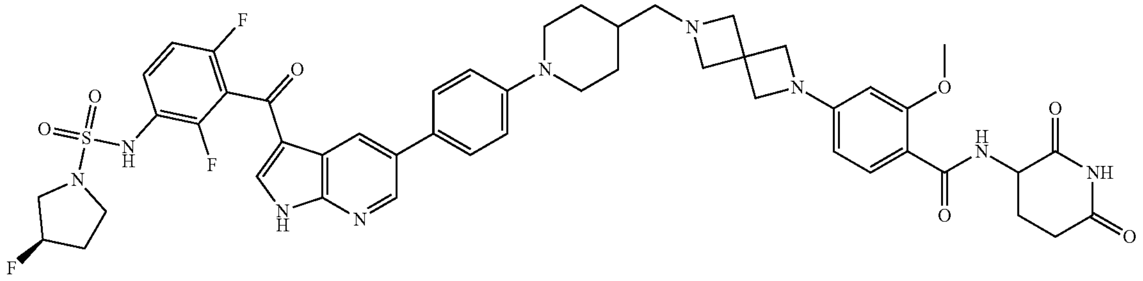 [SMILES: COc1cc(N2CC3(CN(CC4CCN(c5ccc(-c6cnc7[nH]cc(C(=O)c8c(F)ccc(NS(=O)(=O)N9CC[C@@H](F)C9)c8F)c7c6)cc5)CC4)C3)C2)ccc1C(=O)NC1CCC(=O)NC1=O]

To a solution of 4-(2,6-diazaspiro[3.3]heptan-2-yl)-N-(2,6-dioxo-3-piperidyl)-2-methoxy-benzamide (120 mg, 0.25 mmol, 1 eq, trifluoroacetate) and (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (155 mg, 0.25 mmol, 1 eq) in 1,2-dichloroethane (4 mL) was added triethylamine (51 mg, 0.50 mmol, 70.71 uL, 2 eq) the mixture was stirred at 30° C. for 0.5 h. Sodium triacetoxyborohydride (161 mg, 0.76 mmol, 3 eq) was added to the mixture, the mixture was stirred at 30° C. for 1.5 h. The residue was purified by prep-HPLC. The reaction mixture was adjusted pH to 8 with saturated aqueous sodium bicarbonate. The aqueous phase was extracted with ethyl acetate (20 mL×3). The combined organic phase was washed with brine (20 mL×2), dried with anhydrous sodium sulfate, filtered and concentrated in vacuum. Compound 4-[6-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-diazaspiro[3.3]heptan-2-yl]-N-(2,6-dioxo-3-piperidyl)-2-methoxy-benzamide (71.8 mg, 0.074 mmol, 29% yield, 98% purity) was obtained as a yellow solid. LC/MS (ESI) m/z: 954.3 $[M+1]^+$; $^1$H-NMR (400 MHz, DMSO-$d_6$) δ 1.20-1.30 (m, 2H) 1.47 (s, 1H) 1.77 (d, J=10.8 Hz, 2H) 2.02-2.17 (m, 3H) 2.52 (s, 4H) 2.69-2.83 (m, 2H) 3.24-3.30 (m, 4H) 3.34-3.42 (m, 6H) 3.47 (s, 1H) 3.76 (d, J=12.0 Hz, 2H) 3.90 (s, 3H) 3.99 (s, 3H) 4.69 (dt, J=12.4, 6.0 Hz, 1H) 5.20-5.41 (m, 1H) 6.01 (d, J=1.6 Hz, 1H) 6.07 (dd, J=8.8, 1.6 Hz, 1H) 7.05 (d, J=8.8 Hz, 2H) 7.25 (t, J=8.4 Hz, 1H) 7.54-7.66 (m, 3H) 7.76 (d, J=8.4 Hz, 1H) 8.06 (s, 1H) 8.39 (d, J=6.8 Hz, 1H) 8.53 (s, 1H) 8.64 (d, J=2.0 Hz, 1H) 10.85 (s, 1H) 12.89 (s, 1H).

Exemplary Synthesis of 4-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-N-(2,6-dioxopiperidin-3-yl)-2-fluorobenzamide (Exemplary Compound 792)

Step 1: Preparation of tert-butyl 6-(3-fluoro-4-(methoxycarbonyl)phenyl)-2,6-diazaspiro[3.3]heptane-2-carboxylate

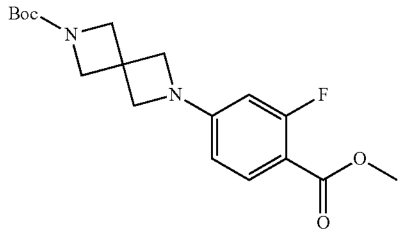 [SMILES: COC(=O)c1ccc(N2CC3(CN(C(=O)OC(C)(C)C)C3)C2)cc1F]

To a solution of methyl 2,4-difluorobenzoate (500 mg, 2.90 mmol, 1 eq) and tert-butyl 2,6-diazaspiro[3.3]heptane-2-carboxylate;oxalic acid (706 mg, 1.45 mmol, 0.5 eq) in dimethylsulfoxide (10 mL) was added diisopropylethylamine (750 mg, 5.81 mmol, 1.01 mL, 2 eq). The mixture was stirred at 120° C. for 2 h. Water (50 mL) was poured into the mixture and stirred for 1 minute. The aqueous phase was extracted with ethyl acetate (20 mL×3). The combined organic phase was washed with brine (30 mL×2), dried with anhydrous sodium sulfate, filtered and concentrated in vacuum. The residue was purified by column chromatography (Petroleum ether/Ethyl acetate=20/1 to 3/1). Compound tert-butyl 6-(3-fluoro-4-methoxycarbonyl-phenyl)-2,6-diazaspiro[3.3]heptane-2-carboxylate (350 mg, 0.99 mmol, 34% yield) was obtained as a white solid. LC/MS (ESI) m/z: 351.5 $[M+1]^+$.

Step 2: Preparation of 4-(6-(tert-butoxycarbonyl)-2,6-diazaspiro[3.3]heptan-2-yl)-2-fluorobenzoic acid

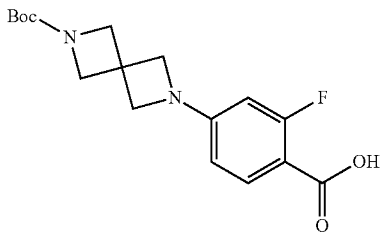 [SMILES: CC(C)(C)OC(=O)N1CC2(C1)CN(c1ccc(C(=O)O)c(F)c1)C2]

To a solution of tert-butyl 6-(3-fluoro-4-methoxycarbonyl-phenyl)-2,6-diazaspiro[3.3]heptanes-2-carboxylate (350 mg, 0.99 mmol, 1 eq) in tetrahydrofuran (6 mL), methanol (6 mL) and water (6 mL) was added sodium hydroxide (159 mg, 4.00 mmol, 4 eq). The mixture was stirred at 40° C. for 3 h. The reaction mixture was adjusted pH to 6 with sulfuric acid (2 M). Water (30 mL) was poured into the mixture and stirred for 1 minute. The aqueous phase was extracted with dichloromethane (10 mL×3). The combined organic phase was washed with brine (10 mL×2), dried with anhydrous sodium sulfate, filtered and concentrated in vacuum. Compound 4-(2-tert-butoxycarbonyl-2,6-diazaspiro[3.3]heptan-6-yl)-2-fluoro-benzoic acid (300 mg, 0.89 mmol, 89% yield) was obtained as a white solid. LC/MS (ESI) m/z: 337.4 $[M+1]^+$.

Step 3: Preparation of tert-butyl 6-(4-((2,6-dioxopiperidin-3-yl)carbamoyl)-3-fluorophenyl)-2,6-diazaspiro[3.3]heptane-2-carboxylate

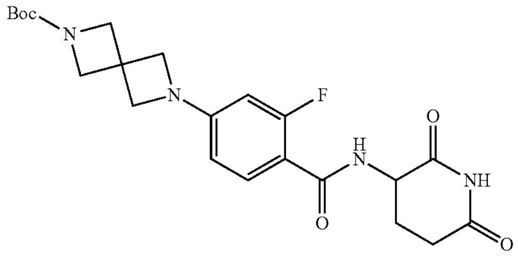 [SMILES: CC(C)(C)OC(=O)N1CC2(C1)CN(c1ccc(C(=O)NC3CCC(=O)NC3=O)c(F)c1)C2]

To a solution of 4-(2-tert-butoxycarbonyl-2,6-diazaspiro[3.3]heptan-6-yl)-2-fluoro-benzoic acid (300 mg, 0.89 mmol, 1 eq) in N,N-dimethylformamide (5 mL) was added o-(7-azabenzotriazol-1-yl)-n,n,n',n'-tetramethyluronium hexafluorophosphate (508 mg, 1.34 mmol, 1.5 eq), the mixture was stirred at 20° C. for 0.5 h. Then diisopropylethylamine (230 mg, 1.78 mmol, 310.71 uL, 2 eq) and 3-aminopiperidine-2,6-dione (146 mg, 0.89 mmol, 1 eq, hydrochloride) was added to the mixture. The mixture was stirred at 20° C. for 12 h. Water (50 mL) was poured into the mixture and stirred for 1 minute. The aqueous phase was extracted with ethyl acetate (20 mL×3). The combined organic phase was washed with brine (20 mL×2), dried with anhydrous sodium sulfate, filtered and concentrated in vacuum. The residue was purified by column chromatography (dichloromethane:methanol=200:1 to 20:1). Compound tert-butyl 6-[4-[(2,6-dioxo-3-piperidyl)carbamoyl]-3-fluoro-phenyl]-2,6-diazaspiro[3.3]heptane-2-carboxylate (250 mg, 0.55 mmol, 62% yield) was obtained as a white solid. LC/MS (ESI) m/z: 447.2 $[M+1]^+$.

Step 4: Preparation of N-(2,6-dioxopiperidin-3-yl)-2-fluoro-4-(2,6-diazaspiro[3.3]heptan-2-yl)benzamide

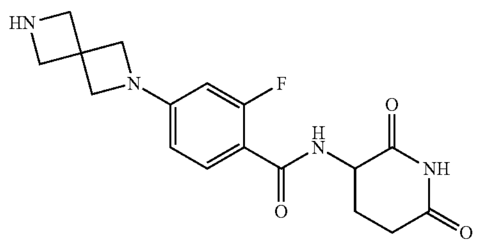 [SMILES: O=C1CCC(NC(=O)c2ccc(N3CC4(CNC4)C3)cc2F)C(=O)N1]

To a solution of tert-butyl 6-[4-[(2,6-dioxo-3-piperidyl)carbamoyl]-3-fluoro-phenyl]-2,6-diazaspiro[3.3]heptane-2-carboxylate (250 mg, 0.55 mmol, 1 eq) in dichloromethane (5 mL) was added trifluoroacetic acid (1.54 g, 13.51 mmol, 1 mL, 24.12 eq). The mixture was stirred at 20° C. for 12 h. The reaction mixture was concentrated under reduced pressure. Compound 4-(2,6-diazaspiro[3.3]heptan-2-yl)-N-(2,6- dioxo-3-piperidyl)-2-fluoro-benzamide (250 mg, trifluoroacetate) was obtained as a brown oil. LC/MS (ESI) m/z: 347.2 $[M+1]^+$.

-continued

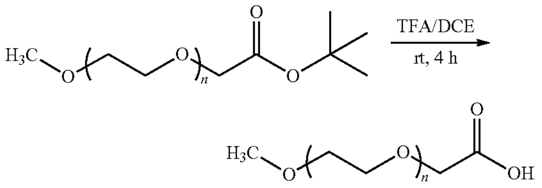

Step 5: Preparation of 4-(6-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)-2,6-diazaspiro[3.3]heptan-2-yl)-N-(2,6-dioxopiperidin-3-yl)-2-fluorobenzamide

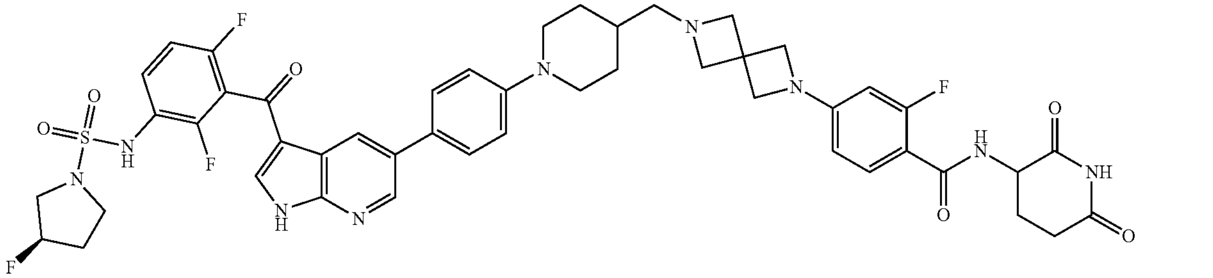 [SMILES: O=C1CCC(NC(=O)c2ccc(N3CC4(CN(CC5CCN(c6ccc(-c7cnc8[nH]cc(C(=O)c9c(F)ccc(NS(=O)(=O)N%10CC[C@@H](F)C%10)c9F)c8c7)cc6)CC5)C4)C3)cc2F)C(=O)N1]

To a solution of 4-(2,6-diazaspiro[3.3]heptan-2-yl)-N-(2,6-dioxo-3-piperidyl)-2-fluoro-benzamide (90 mg, 0.19 mmol, 1 eq, trifluoroacetate) and (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (120 mg, 0.19 mmol, 1 eq) in 1,2-dichloroethane (3 mL) was added triethylamine (39 mg, 0.39 mmol, 2 eq), the mixture was stirred at 30° C. for 0.5 h. Sodium triacetoxyborohydride (124 mg, 0.58 mmol, 3 eq), was added to the mixture, the mixture was stirred at 30° C. for 1.5 h. The residue was purified by prep-HPLC. The reaction mixture was adjusted pH to 8 with saturated aqueous sodium bicarbonate. The aqueous phase was extracted with ethyl acetate (20 mL×3). The combined organic phase was washed with brine (20 mL×2), dried with anhydrous sodium sulfate, filtered and concentrated in vacuum. Compound 4-[6-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methyl]-2,6-diazaspiro[3.3]heptan-2-yl]-N-(2,6-dioxo-3-piperidyl)-2-fluoro-benzamide (37.7 mg, 0.038 mmol, 19% yield, 95% purity) was obtained as a yellow solid. LC/MS (ESI) m/z: 942.3 $[M+1]^+$; $^1$H-NMR (400 MHz, DMSO-$d_6$) δ 1.20-1.30 (m, 2H) 1.46 (s, 1H) 1.76 (d, J=11.2 Hz, 2H) 2.02-2.17 (m, 3H) 2.52 (s, 1H) 2.64-2.82 (m, 3H) 3.26-3.33 (m, 9H) 3.39 (d, J=3.2 Hz, 2H) 3.47 (s, 1H) 3.76 (d, J=12.0 Hz, 2H) 3.93-4.06 (m, 4H) 4.72 (dt, J=12.8, 6.28 Hz, 1H) 5.17-5.41 (m, 1H) 6.20-6.31 (m, 2H) 7.05 (d, J=8.8 Hz, 2H) 7.25 (t, J=8.4 Hz, 1H) 7.54-7.66 (m, 4H) 7.97 (t, J=7.2 Hz, 1H) 8.05 (s, 1H) 8.53 (s, 1H) 8.64 (d, J=2.0 Hz, 1H) 10.82 (s, 1H) 12.88 (s, 1H).

General Synthetic Schemes for PEG Prodrugs

Scheme Prodrug 1. General synthetic scheme for PEG prodrugs linked via a alkoxy-acetate ester on the hydroxyproline of the VHL ligand

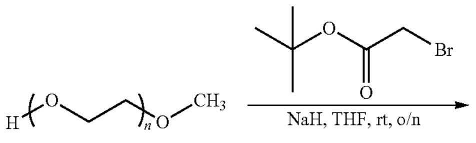

-continued

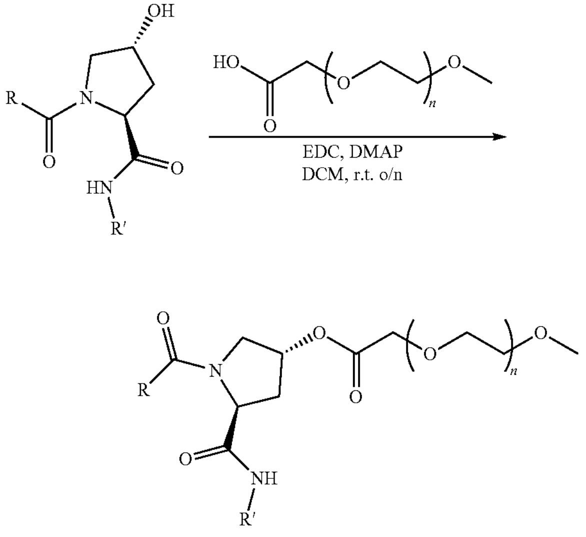

Scheme Prodrug 2. General synthetic scheme for PEG prodrugs linked via a succinate bis-ester on the hydroxyproline of the VHL ligand

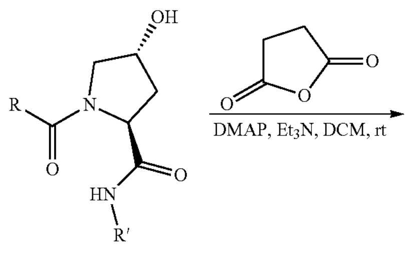

-continued

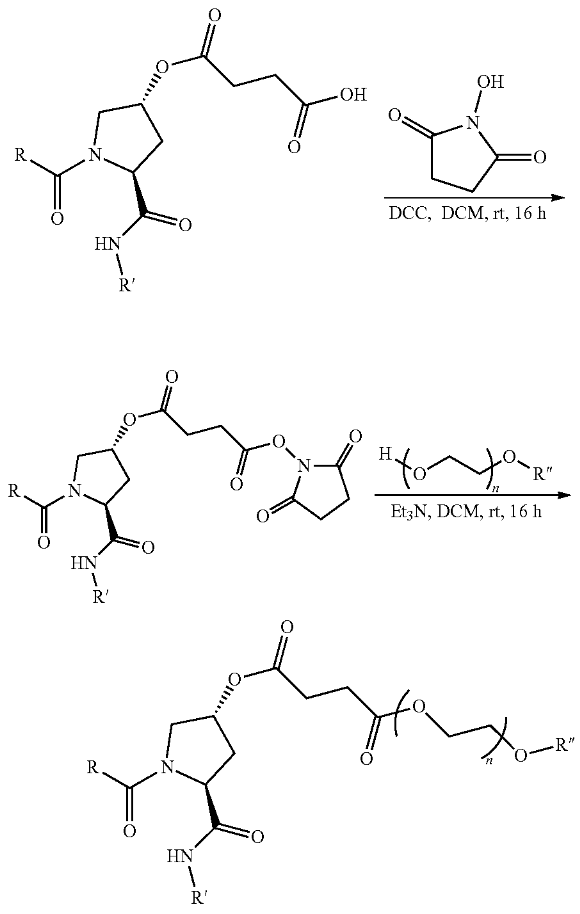

Scheme Prodrug 3. General synthetic scheme for PEG prodrugs linked via a 3-alkoxy-propionate ester on the hydroxyproline of the VHL ligand

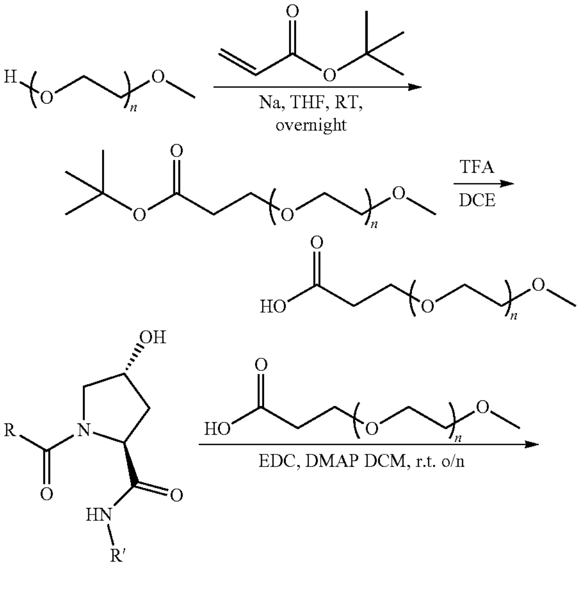

-continued

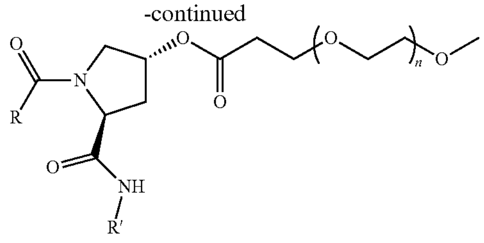

Scheme Prodrug 4. General synthetic scheme for PEG prodrugs linked via a 3-alkoxy-butyrate ester on the hydroxyproline of the VHL ligand

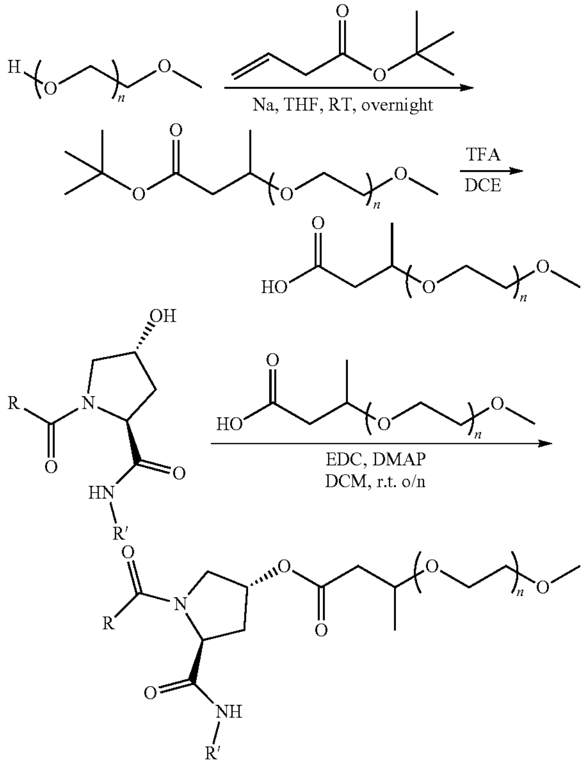

Scheme Prodrug 5. General synthetic scheme for PEG prodrugs linked via a 2-alkoxy-propionate ester on the hydroxyproline of the VHL ligand

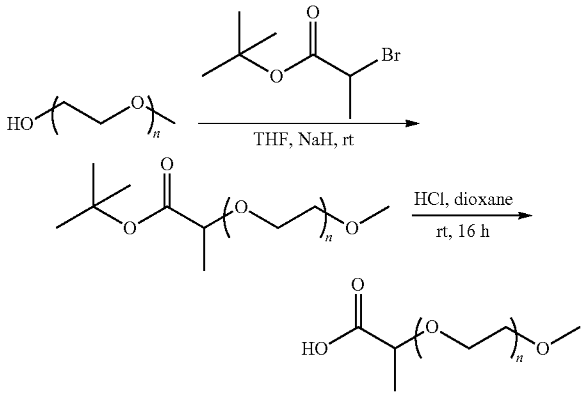

-continued

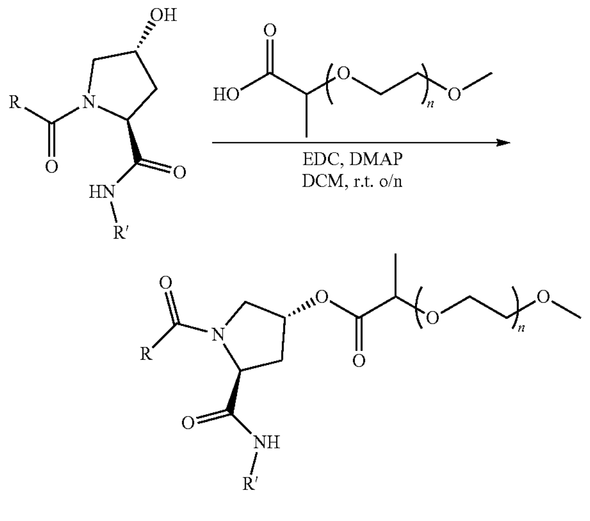

Scheme Prodrug 6. General synthetic scheme for PEG prodrugs linked via a 4-alkoxy-butyrate ester on the hydroxyproline of the VHL ligand

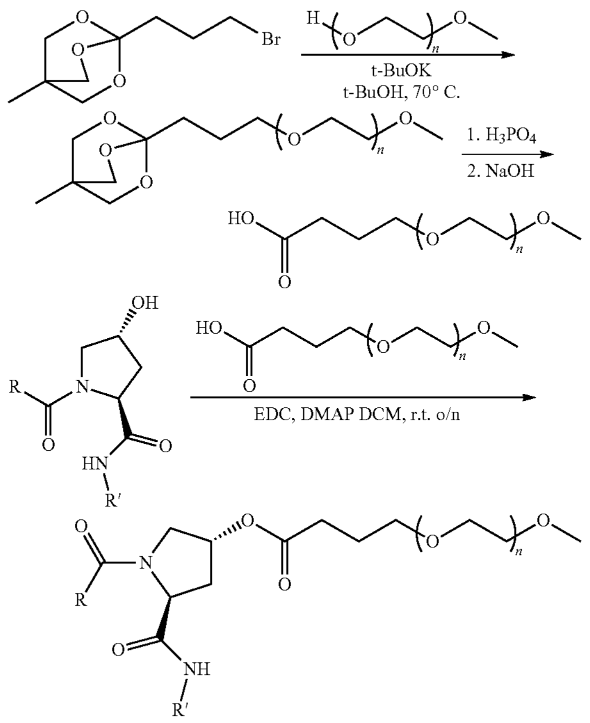

Scheme Prodrug 7. General synthetic scheme for PEG prodrugs linked via a succinate mono-ester mono-(secondary)-amide on the hydroxyproline of the VHL ligand

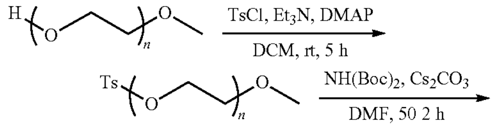

-continued

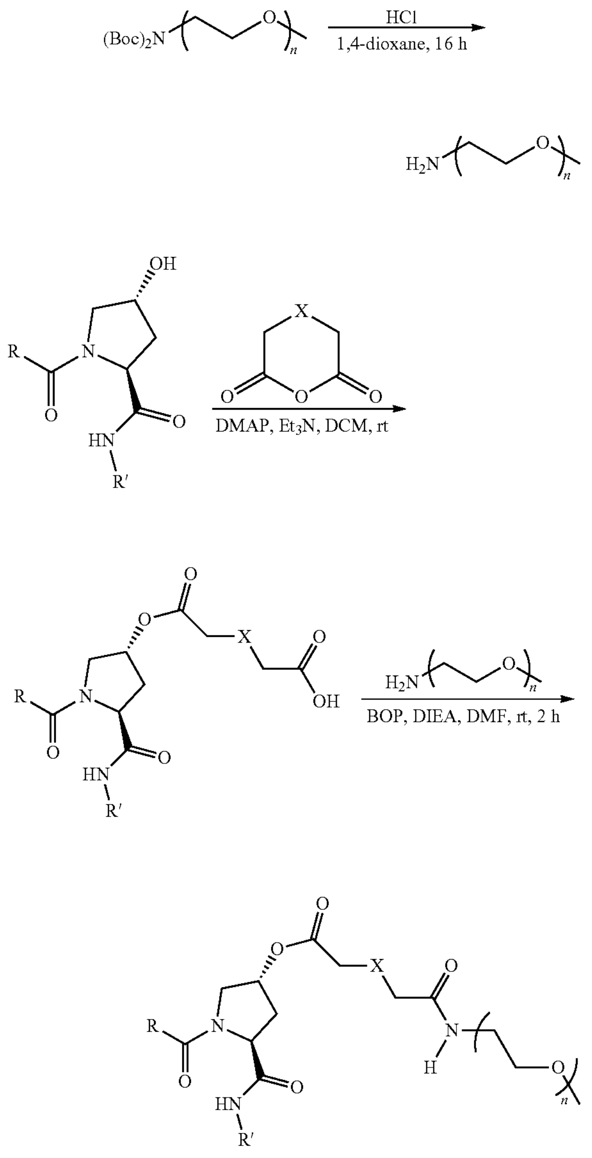

X = O or single bond

Scheme Prodrug 8. General synthetic scheme for PEG prodrugs linked via a succinate mono-ester mono-(tertiary)-amide on the hydroxyproline of the VHL ligand

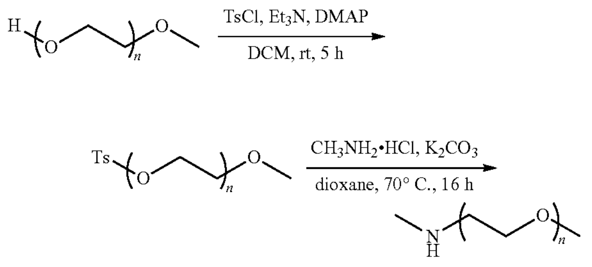

-continued
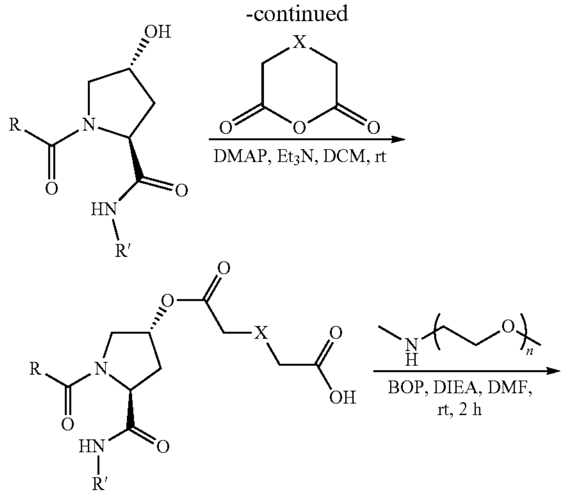
-continued
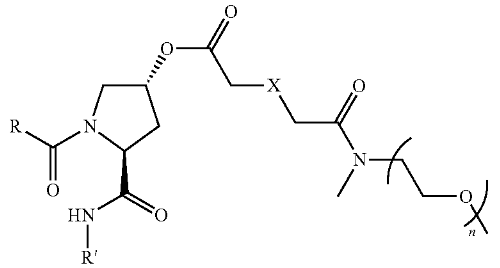
X = O or single bond
Scheme Prodrug 9. General synthetic scheme for PEG prodrugs linked via a succinate mono-ester mono-amide on the benzylic methyl group of the VHL ligand
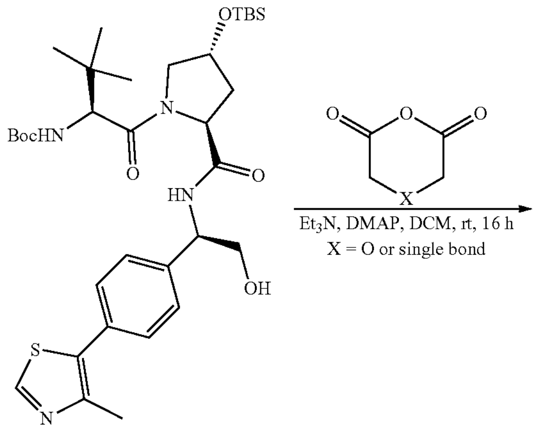
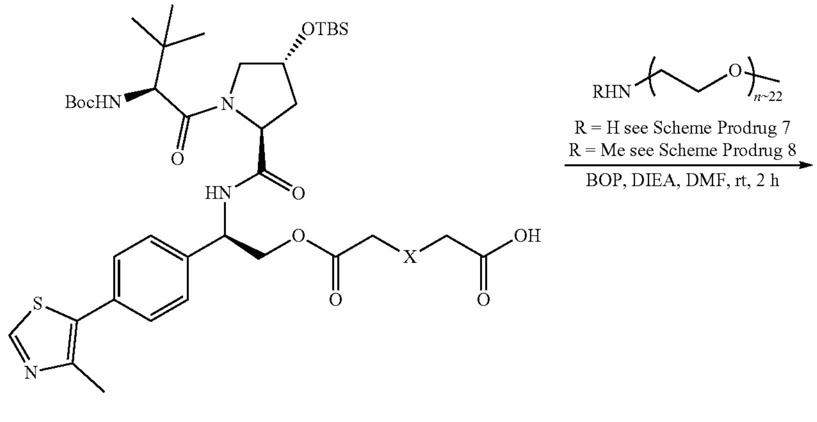

-continued
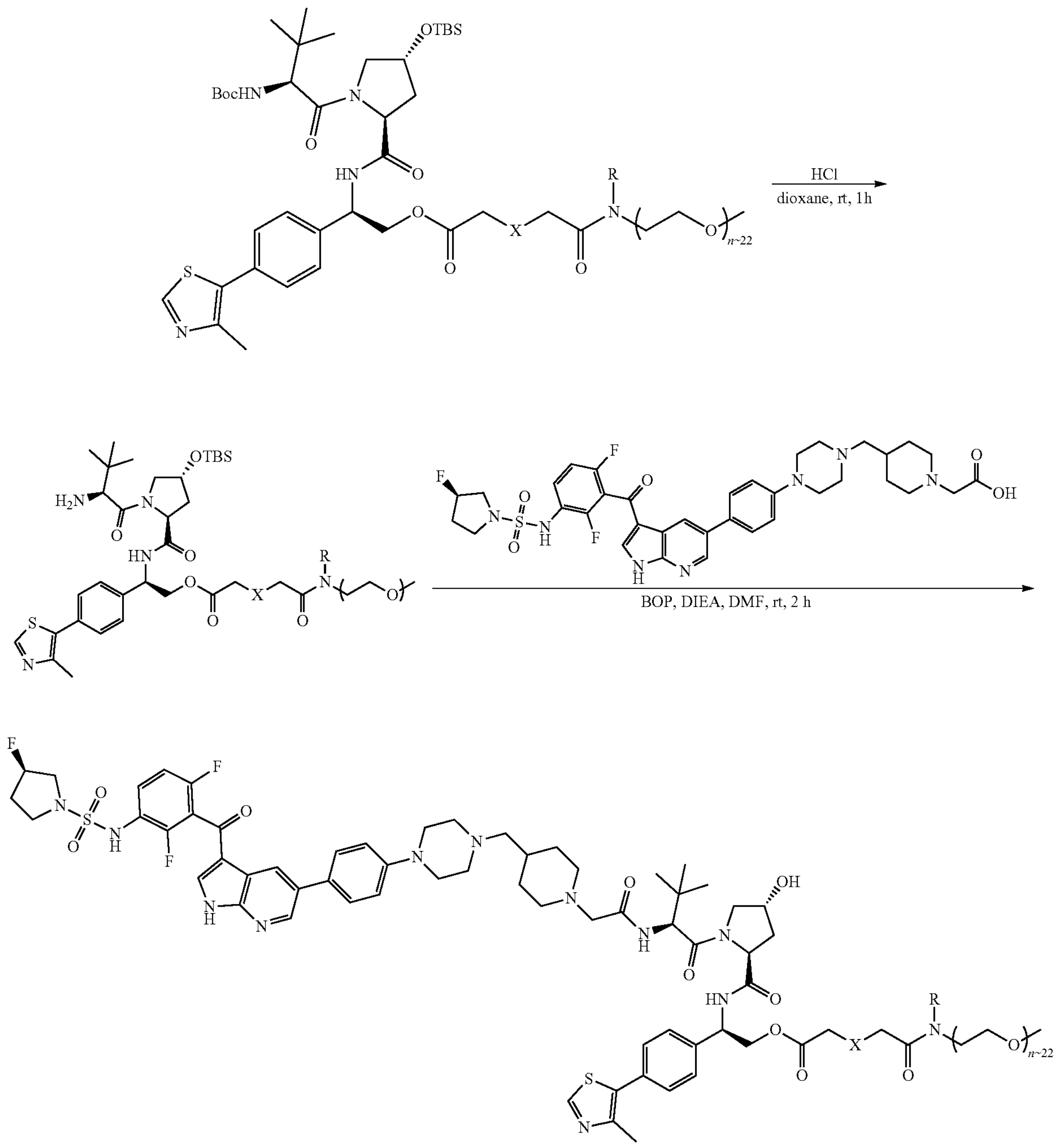
Scheme Prodrug 10. General synthetic scheme for PEG prodrugs linked via a bis-ester of 2,2'-oxydiacetic acid on the hydroxyproline of the VHL ligand
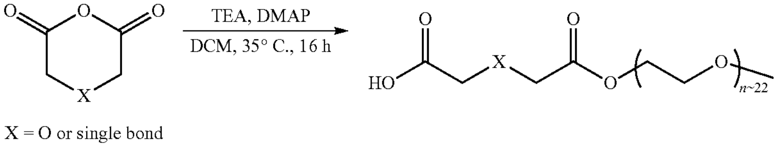
X = O or single bond -continued
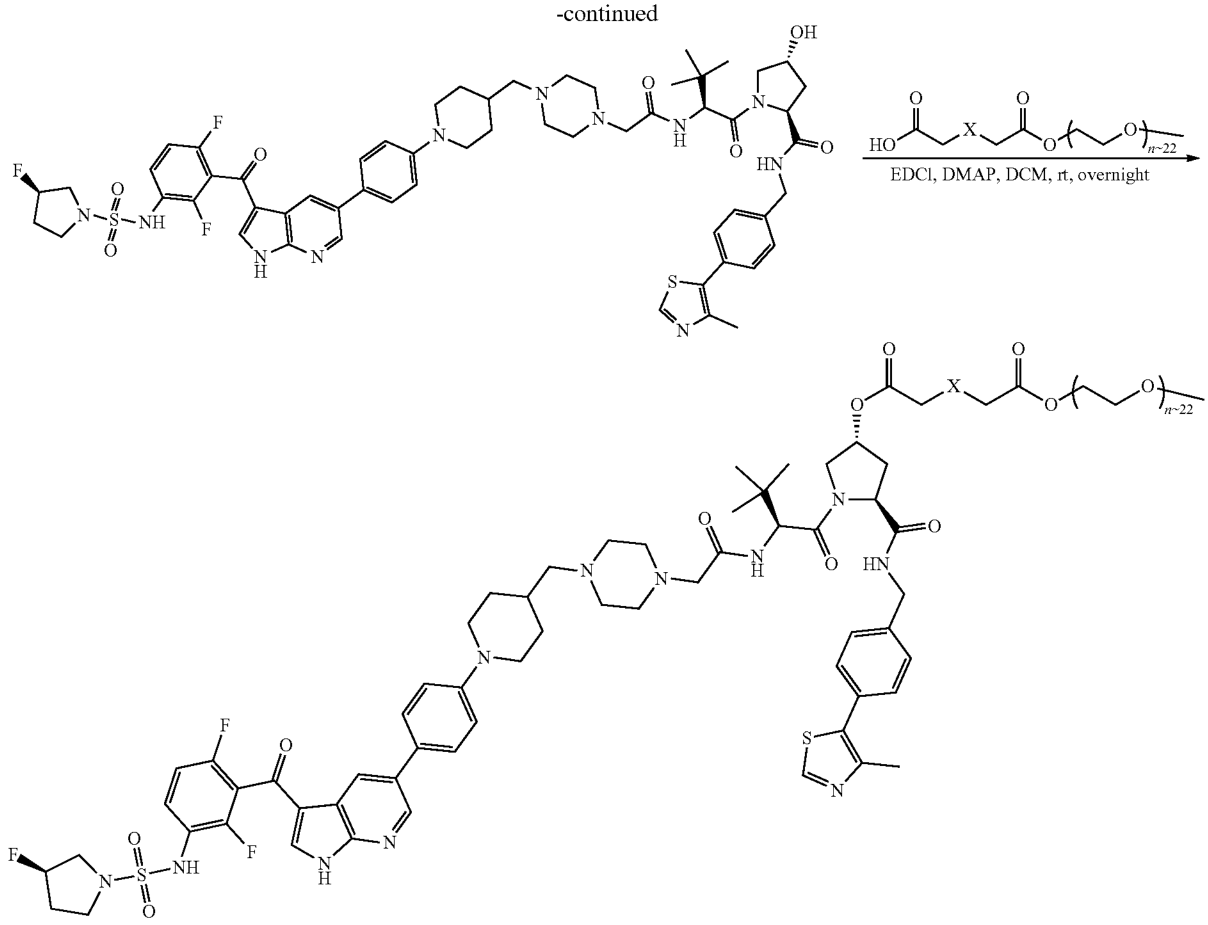
Scheme Prodrug 11. General synthetic scheme for PEG prodrugs linked via Click chemistry on the hydroxyproline of the VHL ligand
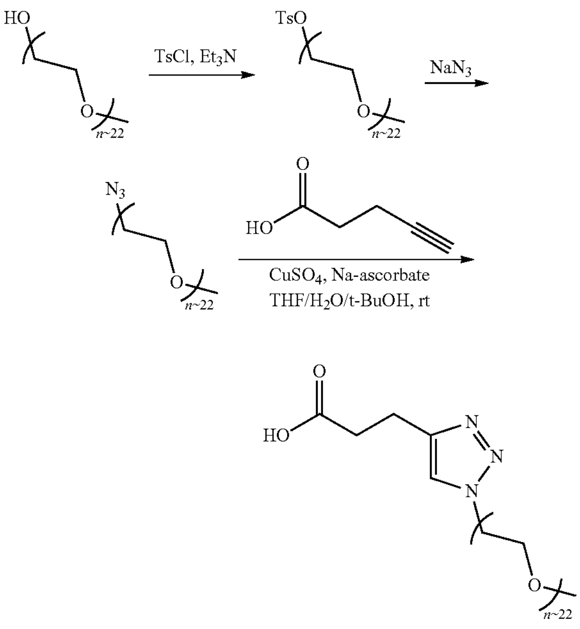
-continued
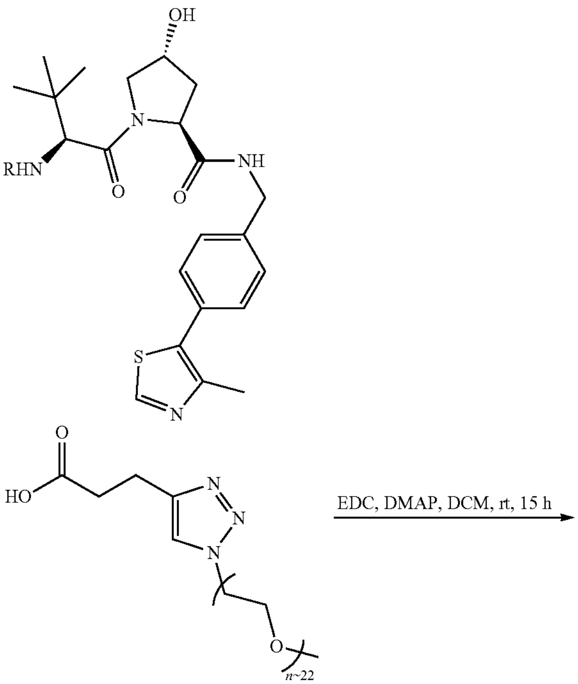

-continued
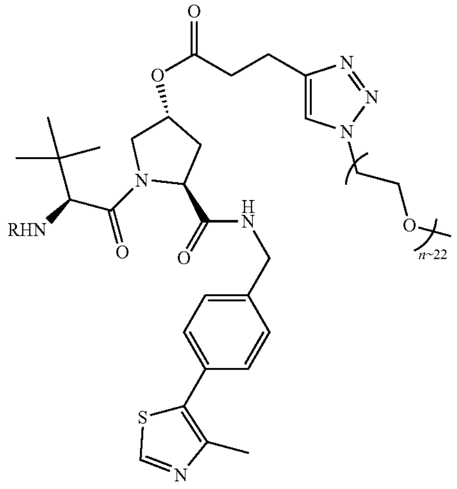
Scheme Prodrug 12. General synthetic scheme for PEG prodrugs linked via methylene carbonate on the imide N of the cereblon ligand
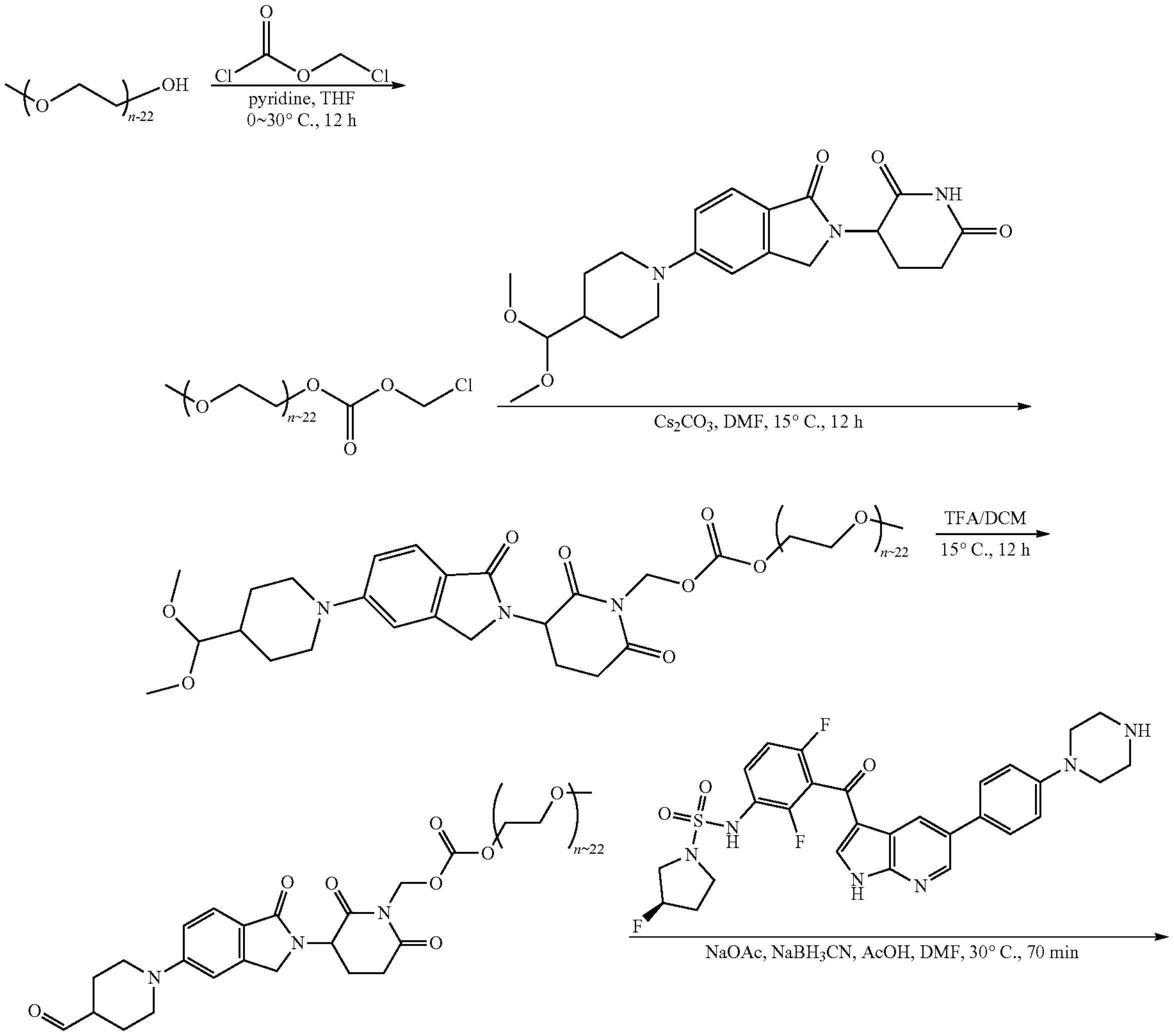

-continued
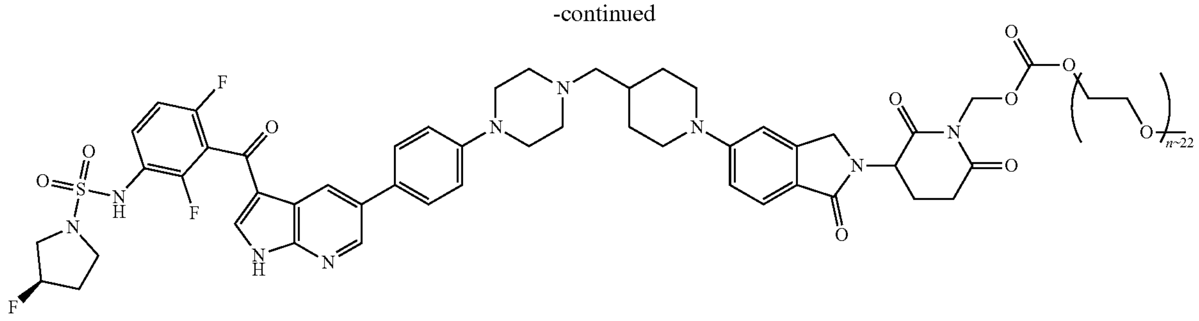
Scheme Prodrug 13. General synthetic scheme for PEG prodrugs linked via methylene 2-propionate from Indol of parent drug
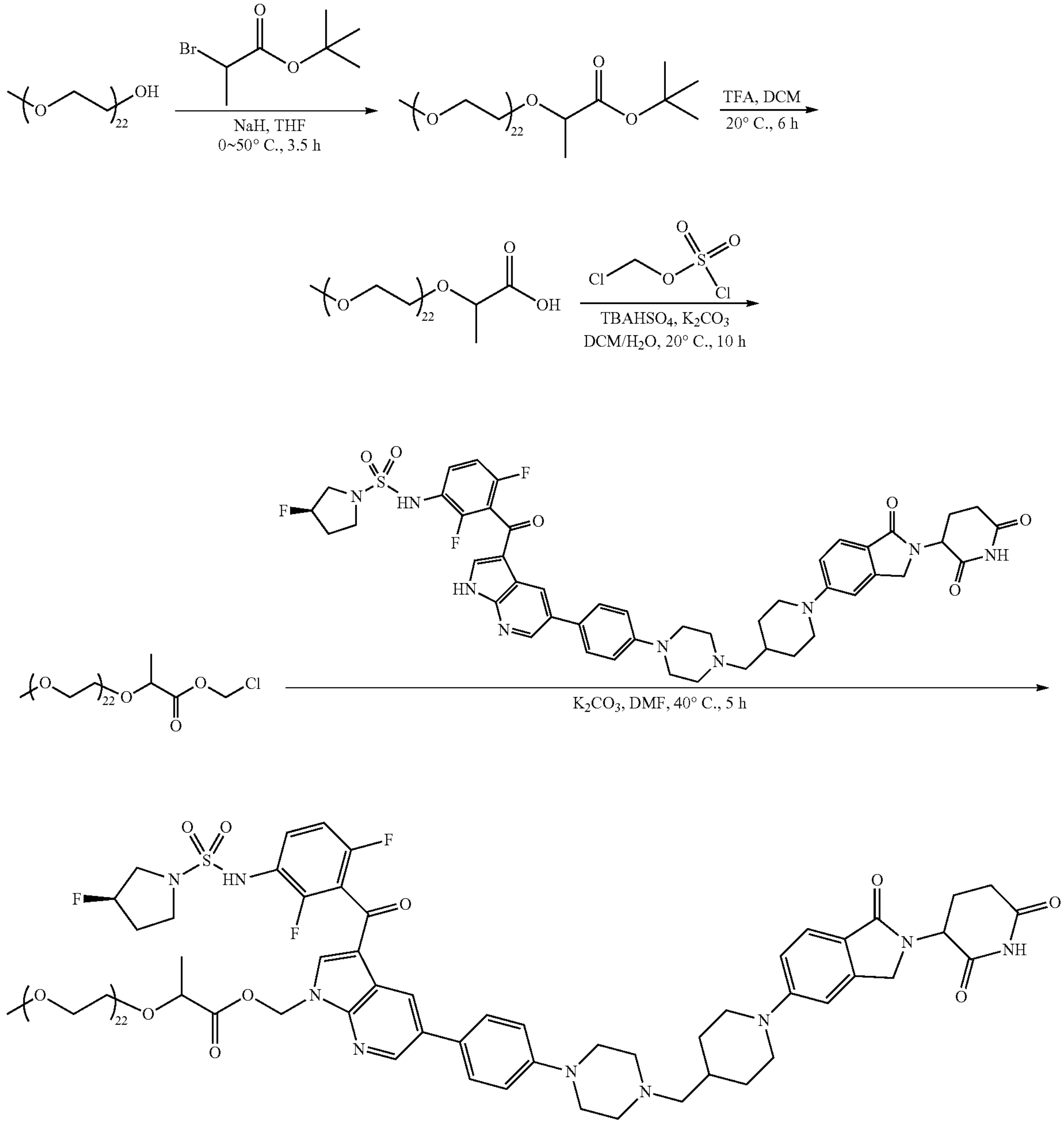

Scheme Prodrug 14. General synthetic scheme for PEG prodrugs linked via methylene aceate from Indol of parent drug
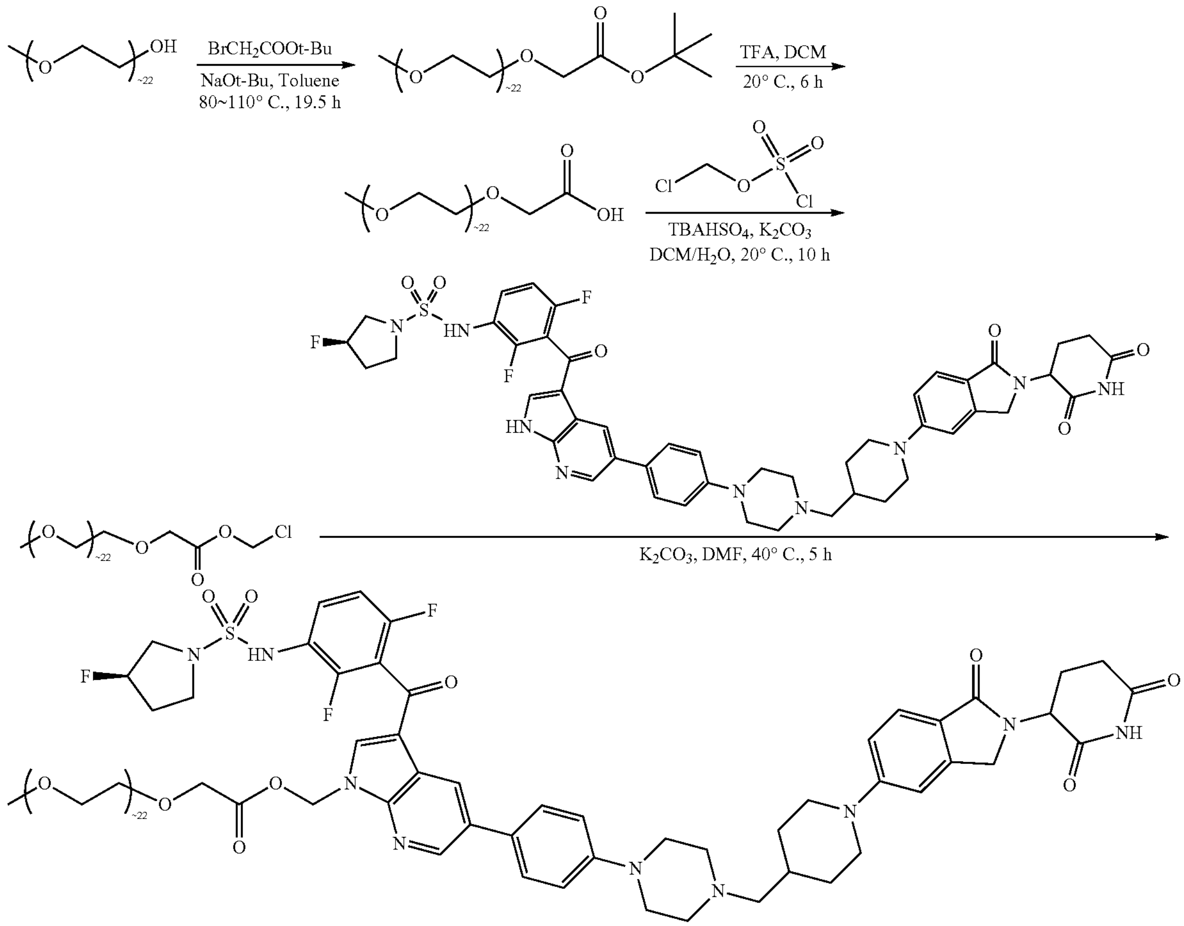
Scheme Prodrug 15. General synthetic scheme for PEG prodrugs linked via methylene carbonate from Indol of parent drug
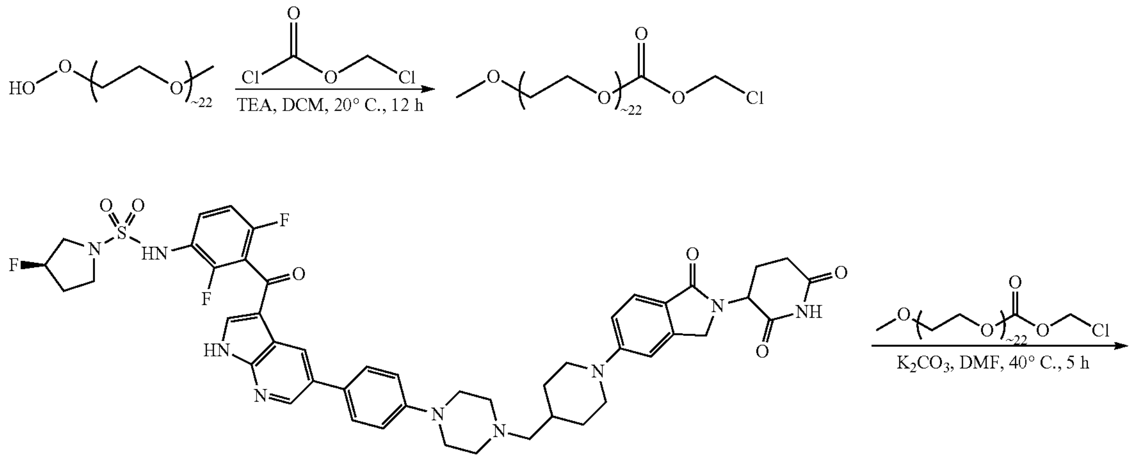

-continued

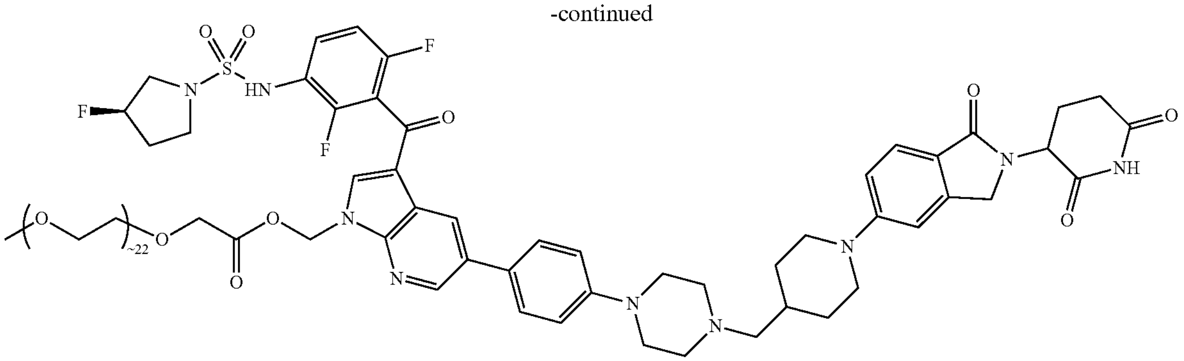

Exemplary Synthesis of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50-heptadecaoxadopentacontan-52-oate (Exemplary Compound 797)

Step 1: Preparation of tert-butyl 3-(4-(4-bromophenyl)piperazin-1-yl)azetidine-1-carboxylate

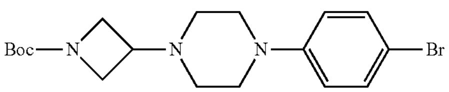 [SMILES: CC(C)(C)OC(=O)N1CC(N2CCN(c3ccc(Br)cc3)CC2)C1]

Into a 500-mL round-bottom flask, was placed 1-(4-bromophenyl)piperazine (10.0 g, 36.2 mmol 1.0 equiv), tert-butyl 3-oxoazetidine-1-carboxylate (7.0 g, 36.2 mmol, 1.0 equiv), dichloromethane (300.0 mL), N,N-Diisopropylethylamine (4.67 g, 36.2 mmol, 1.0 equiv), sodium triacetoxyborohydride (35.0 g, 0.16 mol, 4 equiv). The resulting mixture was stirred for 24 h at room temperature and extracted with dichloromethane (500.0 ml×2). The organic phase was concentrated and this resulted in 12.0 g of tert-butyl 3-(4-(4-bromophenyl)piperazin-1-yl)azetidine-1-carboxylate as a solid. LC/MS (ESI) m/z: 396.25 $[M+1]^+$.

Step 2: Preparation of 1-(azetidin-3-yl)-4-(4-bromophenyl)piperazine

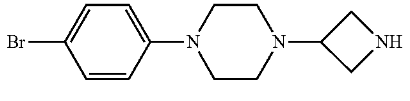 [SMILES: Brc1ccc(N2CCN(C3CNC3)CC2)cc1]

Into a 1-L round-bottom flask, was placed tert-butyl 3-[4-(4-bromophenyl)piperazin-1-yl]azetidine-1-carboxylate (15.0 g, 1 equiv) in 100 mL dichloromethane and then hydrogen chloride in 1,4-dioxane solution (4.0 M, 100 mL) was added. The resulting mixture was stirred for 2 hours at room temperature. The solids were collected by filtration and this resulted in 10.0 g of 1-(azetidin-3-yl)-4-(4-bromophenyl)piperazine as a solid. LC/MS (ESI) m/z: 296.20 $[M+1]^+$.

Step 3: Preparation of tert-butyl 2-(3-(4-(4-bromophenyl)piperazin-1-yl)azetidin-1-yl)acetate

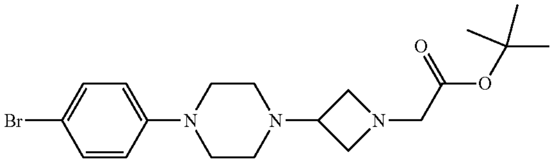 [SMILES: CC(C)(C)OC(=O)CN1CC(N2CCN(c3ccc(Br)cc3)CC2)C1]

Into a 1-L round-bottom flask purged and maintained with an inert atmosphere of nitrogen, was placed 1-(azetidin-3-yl)-4-(4-bromophenyl)piperazine (15.0 g, 50.68 mmol, 1.0 equiv), oxolane (200.0 mL), sodium hydroxide aqueous solution (2.0 M, 100.0 mL), tert-butyl 2-bromoacetate (10.0 g, 51.3 mmol 1.1 equiv). The resulting mixture was stirred for 2 h at 0° C. in an ice/salt bath. The resulting solution was extracted with ethyl acetate (500.0 ml×2) and the organic layers combined, dried over anhydrous sodium sulfate and concentrated. This resulted in 10.0 g of tert-butyl 2-[3-[4-(4-bromophenyl)piperazin-1-yl]azetidin-1-yl]acetate as a solid. LC/MS (ESI) m/z: 410.30 $[M+1]^+$.

Step 4: Preparation of tert-butyl 2-(3-(4-(4-(4,4,5,5-tetramethyl-1,3,2-dioxaborolan-2-yl)phenyl)piperazin-1-yl)azetidin-1-yl)acetate

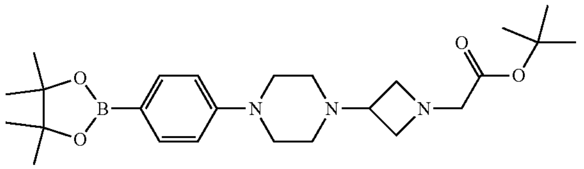 [SMILES: CC(C)(C)OC(=O)CN1CC(N2CCN(c3ccc(B4OC(C)(C)C(C)(C)O4)cc3)CC2)C1]

Into a 250-mL round-bottom flask purged and maintained with an inert atmosphere of nitrogen, was placed tert-butyl 2-[3-[4-(4-bromophenyl)piperazin-1-yl]azetidin-1-yl]acetate (10.4 g, 25.24 mmol 1.0 equiv), 4,4,5,5-tetramethyl-2-(tetramethyl-1,3,2-dioxaborolan-2-yl)-1,3,2-dioxaborolane (12.8 g, 50.48 mmol 2.0 equiv), potassium acetate (4.9 g 50.48 mmol 2.0 equiv), $Pd(dppf)Cl_2$ (2.0 g 2.52 mmol 0.1 equiv) and dioxane (200.0 mL). The resulting solution was stirred overnight at 80° C. in an oil bath. The resulting mixture was concentrated. The residue was applied onto a silica gel column eluting with dichloromethane/methanol (10:1). This resulted in 10.0 g of tert-butyl 2-(3-[4-[4-(tetramethyl-1,3,2-dioxaborolan-2-yl)phenyl]piperazin-1-yl]azetidin-1-yl)acetate as a solid. LC/MS (ESI) m/z: 458.35 $[M+1]^+$.

Step 5: Preparation of tert-butyl (R)-2-(3-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)azetidin-1-yl)acetate

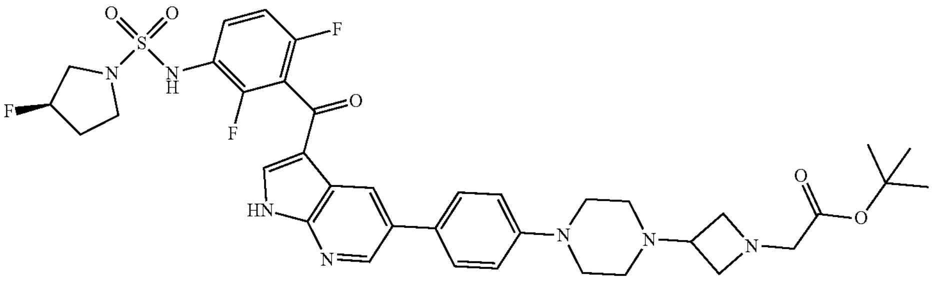 [SMILES: CC(C)(C)OC(=O)CN1CC(N2CCN(c3ccc(-c4cnc5[nH]cc(C(=O)c6c(F)ccc(NS(=O)(=O)N7CC[C@@H](F)C7)c6F)c5c4)cc3)CC2)C1]

Into a 30-mL sealed tube purged and maintained with an inert atmosphere of nitrogen, was placed (3R)—N-[3-([5-bromo-1H-pyrrolo[2,3-b]pyridin-3-yl]carbonyl)-2,4-difluorophenyl]-3-fluoropyrrolidine-1-sulfonamide (1.0 g, 2.0 mmol 1.0 equiv), tert-butyl 2-(3-[4-[4-(tetramethyl-1,3,2-dioxaborolan-2-yl)phenyl]piperazin-1-yl]azetidin-1-yl)acetate (1.9 g 4.15 mmol 2.1 equiv), $Na_2CO_3$ (0.43 g, 4.0 mmol, 2.0 equiv), $Pd(dppf)Cl_2$ (163.0 mg, 0.2 mmol, 0.1 equiv), dioxane (10 mL) and $H_2O$ (2 mL). The resulting mixture was stirred for 3 h at 105° C. under Microwave conditions. The resulting mixture was concentrated and the residue was applied onto a silica gel column eluting with dichloromethane/methanol (10:1). This resulted in 0.94 g (62.76%) of tert-butyl 2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetate as a solid. LC/MS (ESI) m/z: 754.45 $[M+1]^+$.

Step 6: Preparation of (R)-2-(3-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)azetidin-1-yl)acetic acid

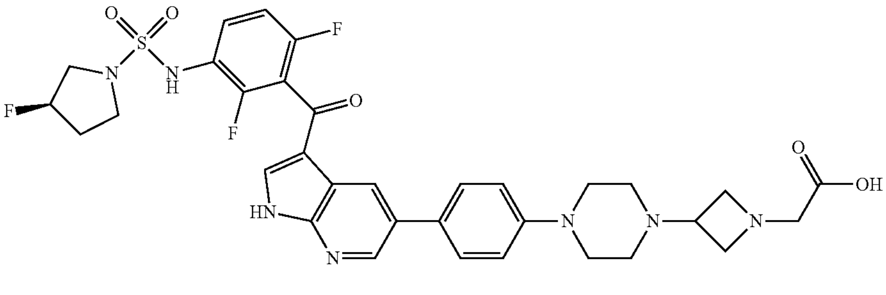 [SMILES: O=C(O)CN1CC(N2CCN(c3ccc(-c4cnc5[nH]cc(C(=O)c6c(F)ccc(NS(=O)(=O)N7CC[C@@H](F)C7)c6F)c5c4)cc3)CC2)C1]

Into a 100-mL round-bottom flask, was placed tert-butyl 2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetate (1.0 g), dichloromethane (20 mL) and trifluoroacetic acid (10 mL). The resulting solution was stirred for 12 hours at room temperature. The resulting mixture was concentrated. This resulted in 820.0 mg of 2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetic acid as a brown solid. LC/MS (ESI) m/z: 698.05 $[M+1]^+$.

Step 7: Preparation of (2S,4R)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide

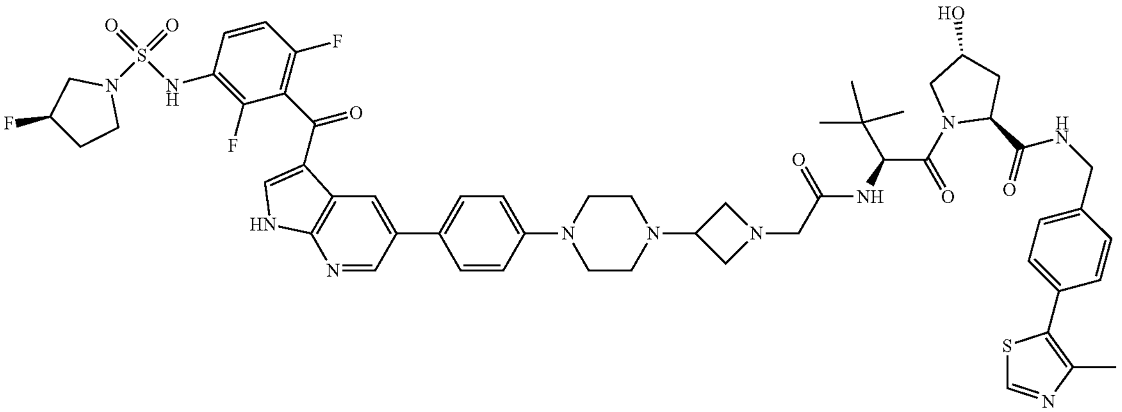 [SMILES: Cc1ncsc1-c1ccc(CNC(=O)[C@@H]2C[C@@H](O)CN2C(=O)[C@@H](NC(=O)CN2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)C(C)(C)C)cc1]

Into a 100-mL round-bottom flask, was placed 2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetic acid (1.0 g), N,N-Dimethylformamide (10 mL), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (0.61 g), N,N-Diisopropylethylamine (0.55 g), propanephosphonic acid cyclic anhydride (1.3 g). The resulting solution was stirred at room temperature for 1 hour. The reaction was then quenched by the addition of 60 mL water. The resulting solution was extracted with ethyl acetate (50 mL×2) and the organic phase was concentrated. The crude product was purified by Prep-HPLC. This resulted in 251.7 mg of (2S,4R)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethyl as a solid. LC/MS (ESI) m/z: 1110.15 $[M+1]^+$; $^1$H-NMR (300 MHz, DMSO-$d_6$) δ 12.89 (s, 1H), 8.94 (s, 1H), 8.70-8.36 (m, 3H), 8.13 (s, 1H), 8.04 (s, 1H), 7.57 (dd, J=9.0, 5.1 Hz, 4H), 7.38 (s, 4H), 7.22 (td, J=8.8, 1.6 Hz, 1H), 7.03 (d, J=8.7 Hz, 2H), 5.26 (d, J=53.1 Hz, 2H), 4.54-4.16 (m, 5H), 3.68-3.50 (m, 3H), 3.42 (d, J=19.4 Hz, 2H), 3.30 (dt, J=25.7, 4.6 Hz, 2H), 3.15 (d, J=18.7 Hz, 7H), 3.01 (s, 3H), 2.40 (d, J=8.0 Hz, 7H), 2.16-1.78 (m, 4H), 1.37 (s, 1H), 0.91 (s, 9H).

Step 8: Preparation of tert-butyl 2,5,8,11,14,17,20,23,26,29,32,35,38,41,44,47,50-heptadecaoxadopentacontan-52-oate

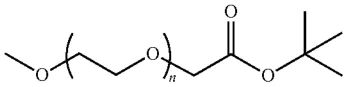

n~16

Into a 1-L round-bottom flask purged and maintained with an inert atmosphere of nitrogen, was placed 2,5,8,11,14,17,20,23,26,29,32,35,38,41,44,47-hexadecaoxanonatetracontan-49-ol (40.00 g, 54.28 mmol, 1 equiv) in THF (400 mL). The solution was cooled to 0° C. in a water/ice bath and followed by NaH (3.20 g, 80.01 mmol, 1.47 equiv) was added in portions. The resulting mixture was stirred for 0.5 h at 0° C. Then tert-butyl 2-bromoacetate (15.60 g, 79.98 mmol, 1.47 equiv) was added dropwise with stirring. The resulting mixture was allowed to react, with stirring, for an additional 14 h at room temperature. The reaction was then quenched by the addition of water (300 mL). The resulting solution was extracted with of ethyl acetate (130 mL×3). The combined organic layers were dried over anhydrous sodium sulfate and concentrated under vacuum. The residue was applied onto a silica gel column with dichloromethane/methanol (20:1). This resulted in 20 g (43.29%) of tert-butyl 2,5,8,11,14,17,20,23,26,29,32,35,38,41,44,47,50-heptadecaoxadopentacontan-52-oate as a colorless oil. $^1$H-NMR (300 MHz, $CDCl_3$) δ 4.02 (s, 2H), 3.71-3.56 (m, 75H), 3.38 (s, 3H), 1.48 (s, 9H).

Step 9: Preparation of 2,5,8,11,14,17,20,23,26,29,32,35,38,41,44,47,50-heptadecaoxadopentacontan-52-oic acid

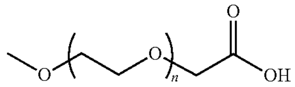

n~16

Into a 50-mL round-bottom flask, was placed tert-butyl 2,5,8,11,14,17,20,23,26,29,32,35,38,41,44,47,50-heptadecaoxadopentacontan-52-oate (500 mg), DCE (5.0 mL), TFA (1.5 mL). The resulting solution was stirred for 4 h at room temperature. The resulting mixture was concentrated under vacuum. The crude product was purified by Prep-HPLC. This resulted in 126.1 mg (27.00%) of 2,5,8,11,14,17,20,23,26,29,32,35,38,41,44,47,50-heptadecaoxadopentacontan-52-oic acid as light yellow oil. LC/MS (ESI) m/z: 398.35 $[M/2+1]^+$; $^1$H-NMR (300 MHz, $D_2O$) δ 4.8-4.15 (m, 2H), 3.70-3.55 (m, 77H), 3.30 (s, 3H).

Step 10: Preparation of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50-heptadecaoxadopentacontan-52-oate

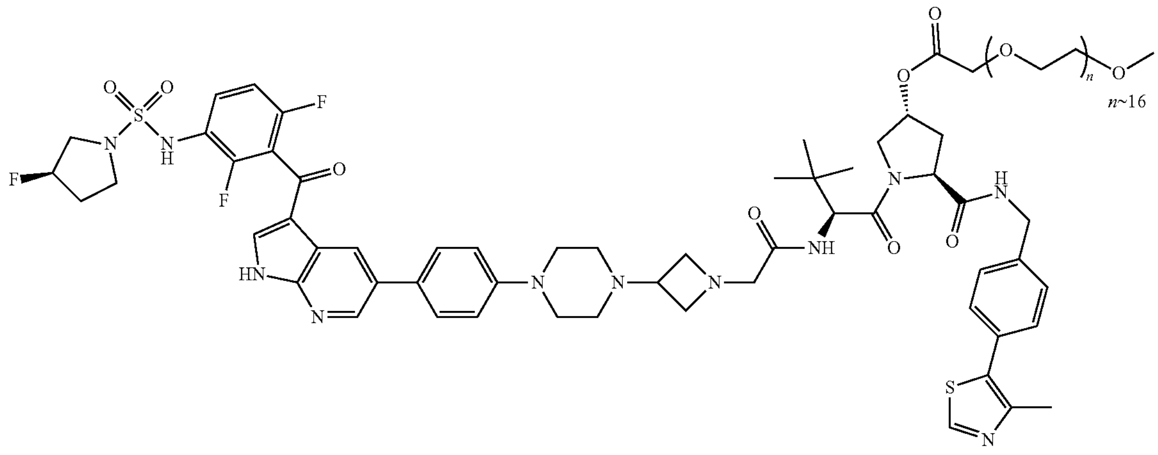

Into a 100-mL round-bottom flask, was placed (2S,4R)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethyl (300.0 mg, 270.51 mmol, 1.0 equiv), 2-(2-methoxyethoxy)acetic acid (1.074 g, 1.35 mmol 5.0 equiv), dichloromethane (20.0 mL), 4-Dimethylaminopyridine (1.5 g, 2.7 mol 10 equiv), N-(3-dimethylaminopropyl)-N'-ethylcarbodiimide hydrochloride (5.71 g, 2.7 mol 10.0 equiv). The resulting solution was stirred for 24 hr at room temperature. The resulting mixture was washed with 300× ml of $NH_4Cl$. The resulting solution was extracted with 2×200 ml of dichloromethane dried over anhydrous sodium sulfate and concentrated. The resulting mixture was concentrated. The crude product was purified by Prep-HPLC. This resulted in 31.6 mg of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50-heptadecaoxadopentacontan-52-oate as a solid. LC/MS (ESI) m/z: 1887.26 $[M+1]^+$; $^1$H-NMR (400 MHz, DMSO-$d_6$) δ 8.99 (s, 1H), 8.89-8.44 (m, 2H), 8.17 (s, 3H), 7.62 (dd, J=9.0, 6.8 Hz, 1H), 7.42 (s, 3H), 7.28 (t, J=8.9 Hz, 4H), 7.08 (d, J=8.4 Hz, 2H), 5.31 (d, J=52.8 Hz, 2H), 4.58-4.23 (m, 5H), 4.29-3.68 (m, 6H), 3.78-3.51 (m, 12H), 3.47-2.77 (m, 66H), 2.47 (s, 7H), 2.42-1.88 (m, 5H), 0.97 (s, 9H).

Exemplary Synthesis of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl (65-hydroxy-3,6,9,12,15,18,21,24,27,30,33,36,39,42,45,48,51,54,57,60,63-henicosaoxapentahexacontyl) succinate (Exemplary Compound 799)

Step 1: Preparation of 4-(((3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl)oxy)-4-oxobutanoic acid

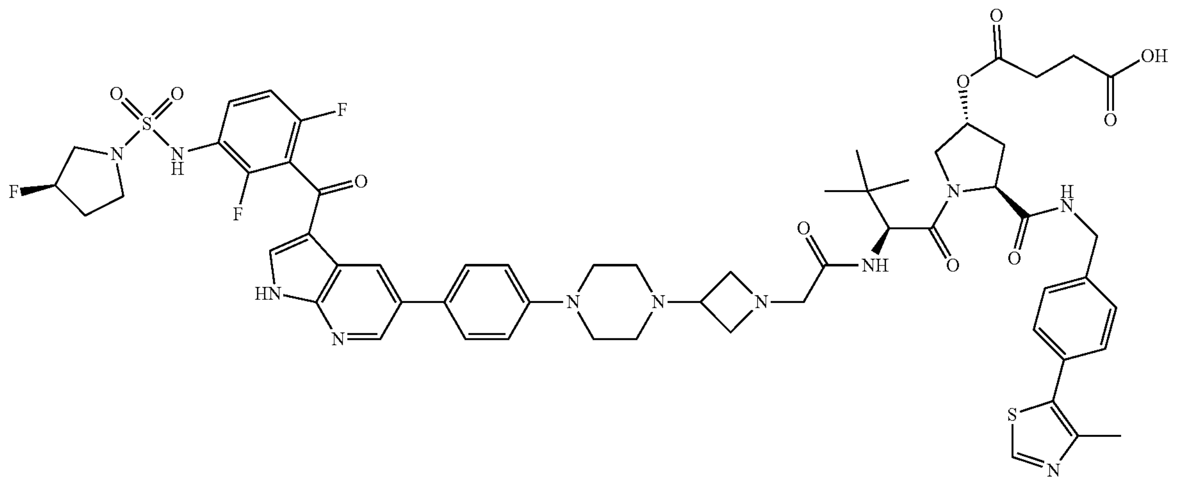 [SMILES: Cc1ncsc1-c1ccc(CNC(=O)[C@@H]2C[C@@H](OC(=O)CCC(=O)O)CN2C(=O)[C@@H](NC(=O)CN2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)C(C)(C)C)cc1]

Into a 100-mL round-bottom flask, was placed (2S,4R)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethylbutanoyl]-4-hydroxy-N-[[4-(4-methyl-1,3-thiazol-5-yl)phenyl]methyl]pyrrolidine-2-carboxamide (250.0 mg, 0.23 mmol, 1.00 equiv), dichloromethane (10 mL), 4-dimethylaminopyridine (82.50 mg, 0.68 mmol, 3.00 equiv), triethylamine (45.53 mg, 0.45 mmol, 2.00 equiv), after stirred 10 min, oxolane-2,5-dione (45.08 mg, 0.45 mmol, 2.00 equiv) was added. The resulting solution was stirred overnight at room temperature. The resulting solution was extracted with dichloromethane (100 mL) and the organic layers combined. The resulting mixture was washed with $NH_4Cl$ (aq.) (50 mL). The mixture was dried over anhydrous sodium sulfate and concentrated under vacuum. The crude product was purified by Prep-HPLC. This resulted in 38 mg (14%) of 4-[[(3R,5S)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethylbutanoyl]-5-([[4-(4-methyl-1,3-thiazol-5-yl)phenyl]methyl]carbamoyl)pyrrolidin-3-yl]oxy]-4-oxobutanoic acid as a light yellow solid. LC/MS (ESI) m/z: 1210.10 $[M+1]^+$; $^1$H-NMR (400 MHz, $CD_3OD$) δ 8.85 (s, 1H), 8.67 (s, 1H), 8.58 (d, J=2.0 Hz, 1H), 7.88 (s, 1H), 7.75-7.74 (m, 1H), 7.58 (d, J=8.8 Hz, 2H), 7.47-7.40 (m, 4H), 7.16-7.07 (m, 3H), 5.35-5.15 (m, 2H), 4.57-4.53 (m, 3H), 4.38-4.34 (m, 1H), 4.16-4.13 (m, 1H), 4.00-3.87 (m, 3H), 3.59-3.39 (m, 7H), 3.30-3.24 (m, 6H), 2.55-2.44 (m, 12H), 2.20-2.00 (m, 3H), 1.04 (s, 9H).

Step 2: Preparation of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl (2,5-dioxopyrrolidin-1-yl) succinate

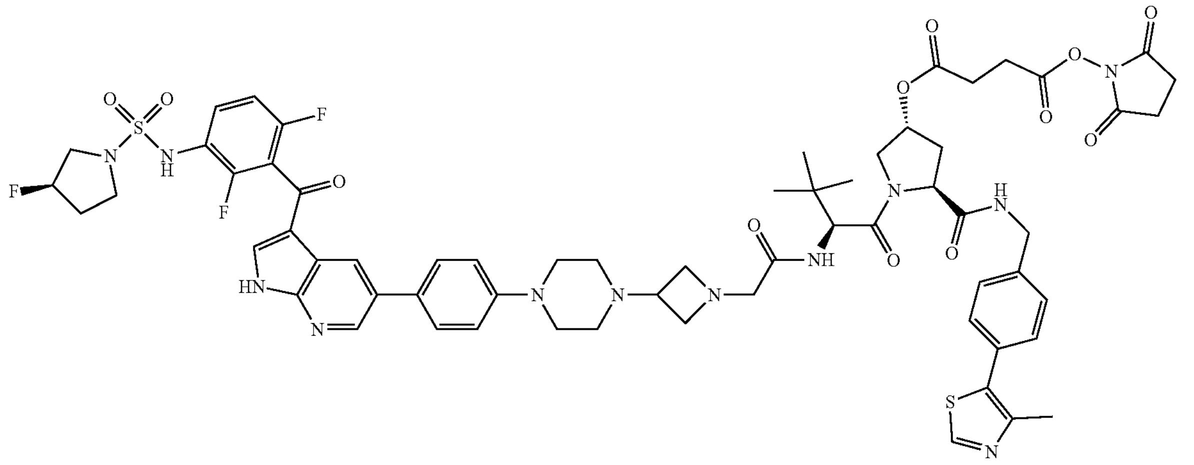 [SMILES: Cc1ncsc1-c1ccc(CNC(=O)[C@@H]2C[C@@H](OC(=O)CCC(=O)ON3C(=O)CCC3=O)CN2C(=O)[C@@H](NC(=O)CN2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)C(C)(C)C)cc1]

Into a 50-mL round-bottom flask, was placed 4-[[(3R,5S)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethylbutanoyl]-5-([[4-(4-methyl-1,3-thiazol-5-yl)phenyl]methyl]carbamoyl)pyrrolidin-3-yl]oxy]-4-oxobutanoic acid (250.0 mg, 0.21 mmol, 1.00 equiv), dichloromethane (10 mL), 1-hydroxypyrrolidine-2,5-dione (47.55 mg, 0.41 mmol, 2.00 equiv), DCC (85.19 mg, 0.41 mmol, 2.00 equiv). The resulting solution was stirred overnight at room temperature. The solids were filtered out. This resulted in 270.0 mg (100%) of (3R,5S)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethylbutanoyl]-5-([[4-(4-methyl-1,3-thiazol-5-yl)phenyl]methyl]carbamoyl)pyrrolidin-3-yl 2,5-dioxopyrrolidin-1-yl butanedioate as a light yellow solid.

Step 3: Preparation of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl (65-hydroxy-3,6,9,12,15,18,21,24,27,30,33,36,39,42,45,48,51,54,57,60,63-henicosaoxapentahexacontyl) succinate

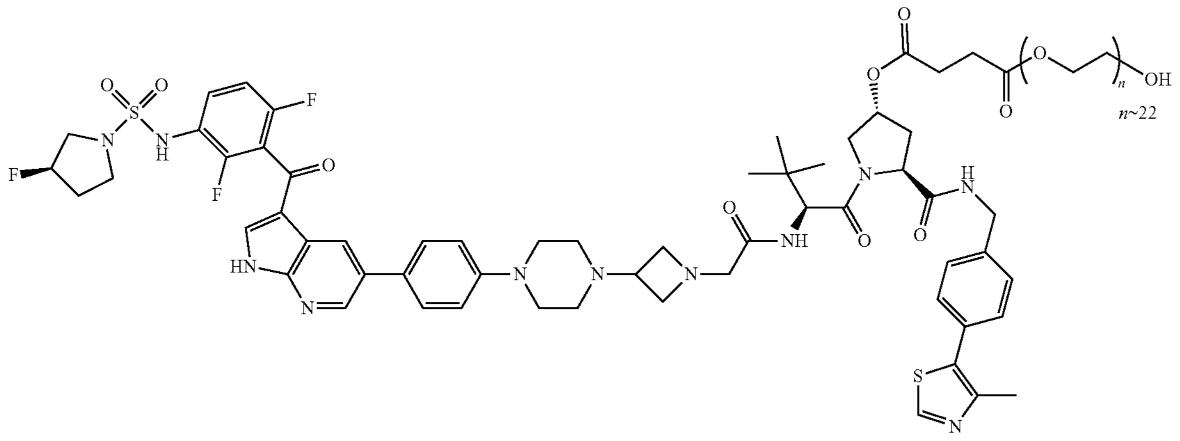

Into a 50-mL round-bottom flask purged and maintained with an inert atmosphere of nitrogen, was placed (3R,5S)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethylbutanoyl]-5-([[4-(4-methyl-1,3-thiazol-5-yl)phenyl]methyl]carbamoyl)pyrrolidin-3-yl 2,5-dioxopyrrolidin-1-yl butanedioate (290.0 mg, 0.22 mmol, 1.00 equiv), dichloromethane (5.0 mL), PEG 1000 (666.0 mg, 3.00 equiv), triethylamine (67.28 mg, 0.66 mmol, 3.00 equiv). The resulting solution was stirred overnight at room temperature. The resulting solution was extracted with dichloromethane (50 mL×2) and the organic layers combined. The resulting mixture was washed with $NH_4Cl$ (aq.) (50 mL×2). The mixture was dried over anhydrous sodium sulfate and concentrated under vacuum. The crude product was purified by Prep-HPLC. This resulted in 59.6 mg (21%) of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl (65-hydroxy-3,6,9,12,15,18,21,24,27,30,33,36,39,42,45,48,51,54,57,60,63-henicosaoxapentahexacontyl) succinate as light yellow oil. LC/MS (ESI) m/z: 2179.44 $[M+1]^+$; $^1H$ NMR (400 MHz, $CD_3OD$) δ 8.86 (s, 1H), 8.67 (s, 1H), 8.59-8.58 (d, J=2.0 Hz, 1H), 7.89 (s, 1H), 7.75-7.74 (m, 1H), 7.60-7.58 (d, J=8.8 Hz, 2H), 7.48-7.41 (m, 4H), 7.10-7.08 (m, 3H), 5.35-5.15 (m, 2H), 4.54-4.53 (m, 3H), 4.38-4.34 (m, 1H), 4.23-4.13 (m, 3H), 3.90-3.80 (m, 2H), 3.70-3.53 (m, 99H), 3.47-3.31 (m, 3H), 3.29-3.26 (m, 4H), 3.17-3.10 (m, 3H), 2.64 (s, 4H), 2.56 (s, 4H), 2.48 (s, 4H), 2.47-2.35 (m, 1H), 2.25-2.10 (m, 3H), 1.05 (s, 9H)

Exemplary Synthesis of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxahenheptacontan-71-oate (Exemplary Compound 800)

Step 1: Preparation of tert-butyl 2-(2-(benzyloxy)ethoxy)acetate

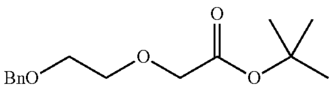 [SMILES: CC(C)(C)OC(=O)COCCOCc1ccccc1]

Into a 1000-mL round-bottom flask, was placed 2-(benzyloxy)ethan-1-ol (10.0 g, 65.71 mmol, 1.00 equiv), tert-butyl 2-bromoacetate (19.2 g, 98.43 mmol, 1.50 equiv), 37% sodium hydroxide (150 mL), Tetrabutylammonium chloride (18.3 g, 65.83 mmol, 1.00 equiv) in dichloromethane (150 mL). The resulting solution was stirred for 4 h at room temperature in a water/ice bath. The resulting solution was extracted with dichloromethane (100 mL×3) and the organic layers combined and concentrated under vacuum. The residue was applied onto a silica gel column with ethyl acetate/petroleum ether (1/15). This resulted in 15.0 g (86%) of tert-butyl 2-[2-(benzyloxy)ethoxy]acetate as yellow oil.

Step 2: Preparation of tert-butyl 2-(2-hydroxyethoxy)acetate

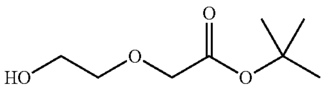

Into a 500-mL round-bottom flask, Palladium carbon (15.0 g, 92.02 mmol, 10.00 equiv) was added to a solution of tert-butyl 2-[2-(benzyloxy)ethoxy]acetate (20.9 g, 78.47 mmol, 1.00 equiv) in methanol (250 mL) at room temperature under nitrogen atmosphere. The reaction flask was vacuumed and charged with a hydrogen balloon. The resulting solution was stirred for 16 h at room temperature. Palladium carbon was removed. The resulting mixture was concentrated under vacuum. This resulted in 9.9 g (72%) of tert-butyl 2-(2-hydroxyethoxy)acetate as a light yellow solid.

Step 3: Preparation of tert-butyl 2-(2-(tosyloxy)ethoxy)acetate

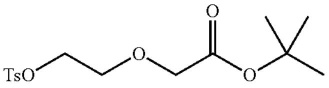 [SMILES: Cc1ccc(S(=O)(=O)OCCOCC(=O)OC(C)(C)C)cc1]

Into a 250-mL round-bottom flask, was placed a solution of tert-butyl 2-(2-hydroxyethoxy)acetate (4.5 g, 25.54 mmol, 1.00 equiv) triethylamine (5.2 g, 51.39 mmol, 2.01 equiv), 4-methylbenzene-1-sulfonyl chloride (5.8 g, 30.42 mmol, 1.20 equiv) in dichloromethane (50 mL). The resulting solution was stirred for 8 h at room temperature. The reaction was then quenched by the addition of water (100 mL). The resulting solution was extracted with dichloromethane (30 mL×3) and the organic layers combined. The resulting mixture was washed with brine (20 mL×1). The mixture was dried over anhydrous sodium sulfate and concentrated under vacuum. The residue was applied onto a silica gel column with ethyl acetate/petroleum ether (1:3). This resulted in 6.1 g (72%) of tert-butyl 2-(2-[[(4-methylbenzene)sulfonyl]oxy]ethoxy)acetate as colorless oil. LC/MS (ESI) m/z: 275.06 $[M-55]^+$.

Step 4: Preparation of tert-butyl 2-(2-(4-(4-bromophenyl)piperazin-1-yl)ethoxy)acetate

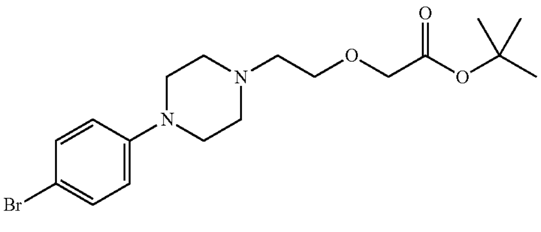 [SMILES: CC(C)(C)OC(=O)COCCN1CCN(c2ccc(Br)cc2)CC1]

Into a 500-mL round-bottom flask, was placed 1-(4-bromophenyl)piperazine hydrochloride (10.0 g, 36.02 mmol, 1.00 equiv), tert-butyl 2-2-[(4-methylbenzenesulfonyl)oxy]ethoxyacetate (14.2 g, 42.98 mmol, 1.20 equiv), acetonitrile (200 mL), potassium iodide (6.0 g, 1.00 equiv) and potassium carbonate (14.9 g, 107.81 mmol, 3.00 equiv). The resulting solution was stirred for 10 h at 70° C. in an oil bath. The solid was filtered out. The filtrate was concentrated under reduced pressure. The residue was applied onto a silica gel column eluting with ethyl acetate/petroleum ether (v:v=1:1). This resulted in 9.6 g (67%) of tert-butyl 2-[2-[4-(4-bromophenyl)piperazin-1-yl]ethoxy]acetate as a light brown solid. LC/MS (ESI) m/z: 399.10 $[M+1]^+$.

Step 5: Preparation of tert-butyl 2-(2-(4-(4-(4,4,5,5-tetramethyl-1,3,2-dioxaborolan-2-yl)phenyl)piperazin-1-yl)ethoxy)acetate

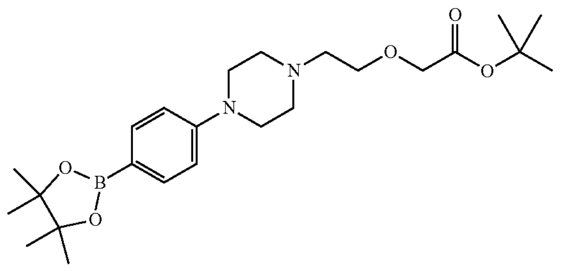 [SMILES: CC(C)(C)OC(=O)COCCN1CCN(c2ccc(B3OC(C)(C)C(C)(C)O3)cc2)CC1]

Into a 500-mL round-bottom flask purged and maintained with an inert atmosphere of nitrogen, was placed tert-butyl 2-[2-[4-(4-bromophenyl)piperazin-1-yl]ethoxy]acetate (9.6 g, 24.04 mmol, 1 equiv), 4,4,5,5-tetramethyl-2-(4,4,5,5-tetramethyl-1,3,2-dioxaborolan-2-yl)-1,3,2-dioxaborolane (12.2 g, 48.08 mmol, 2 equiv), potassium acetate (7.1 g, 72.12 mmol, 3 equiv), Pd(dppf)$Cl_2$. $CH_2Cl_2$ (3.9 g, 4.81 mmol, 0.2 equiv) and 100 mL dioxane. The resulting solution was stirred for 5 h at 85° C. in an oil bath under nitrogen atmosphere. The reaction was then quenched by water (100 mL) and extracted with dichloromethane (100 mL×3). The combined organic layers were washed with brine (100 mL) and water (100 mL), dried over anhydrous sodium sulfate and concentrated under reduced pressure. The residue was applied onto a silica gel column eluting with ethyl acetate/petroleum ether (v:v=1:1). This resulted in 8.2 g (76.41%) of tert-butyl 2-(2-[4-[4-(4,4,5,5-tetramethyl-1,3,2-dioxaborolan-2-yl)phenyl]piperazin-1-yl]ethoxy)acetate as a light brown solid. LC/MS (ESI) m/z: 447.30 $[M+1]^+$.

Step 6: Preparation of tert-butyl (R)-2-(2-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)ethoxy)acetate

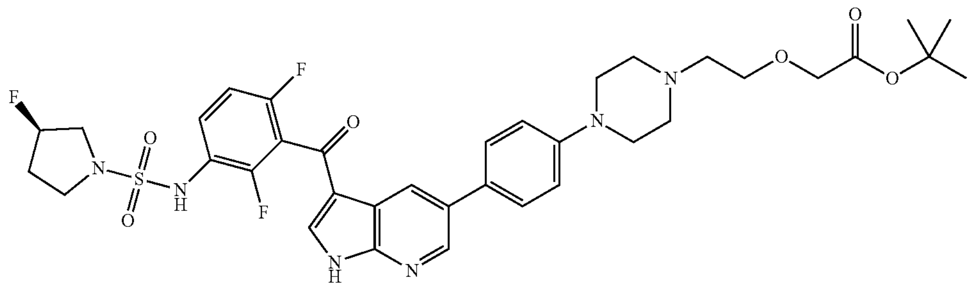 [SMILES: CC(C)(C)OC(=O)COCCN1CCN(c2ccc(-c3cnc4[nH]cc(C(=O)c5c(F)ccc(NS(=O)(=O)N6CC[C@@H](F)C6)c5F)c4c3)cc2)CC1]

Into a 100-mL round-bottom flask, purged and maintained with an inert atmosphere of nitrogen, was placed (3R)—N-(3-[5-bromo-1H-pyrrolo[2,3-b]pyridine-3-carbonyl]-2,4-difluorophenyl)-3-fluoropyrrolidine-1-sulfonamide (5.8 g, 11.52 mmol, 1 equiv), tert-butyl 2-(2-[4-[4-(4,4,5,5-tetramethyl-1,3,2-dioxaborolan-2-yl)phenyl]piperazin-1-yl]ethoxy)acetate (6.2 g, 13.83 mmol, 1.2 equiv), sodium carbonate (3.7 g, 34.57 mmol, 3 equiv), Pd(dppf)$Cl_2 \cdot CH_2Cl_2$ (1.9 g, 2.30 mmol, 0.2 equiv), dioxane (50 mL) and water (5 mL). The resulting solution was stirred for 2 h at 105° C. in an oil bath. The resulting solution was diluted with dichloromethane (100 mL) and extracted with dichloromethane (100 mL×3). The combined organic layers was washed with brine (100 mL) and water (100 mL), dried over anhydrous sodium sulfate and concentrated under reduced pressure. The residue was applied onto a silica gel column eluting with dichloromethane/methanol (10:1). This resulted in 4.8 g (56.07%) of tert-butyl 2-[2-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]ethoxy]acetate as yellow oil. LC/MS (ESI) m/z: 743.15 $[M+1]^+$.

Step 7: Preparation of (R)-2-(2-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)ethoxy)acetic acid

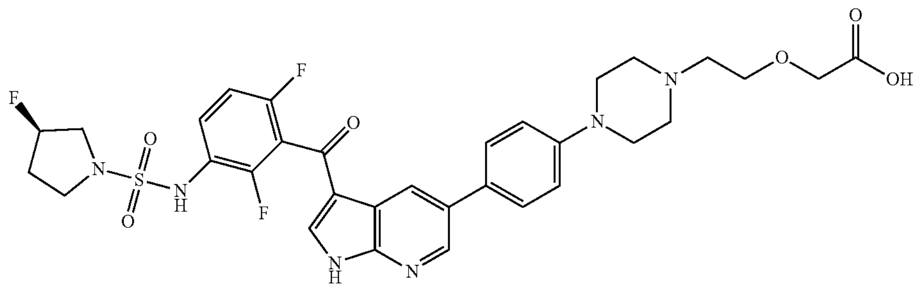 [SMILES: O=C(O)COCCN1CCN(c2ccc(-c3cnc4[nH]cc(C(=O)c5c(F)ccc(NS(=O)(=O)N6CC[C@@H](F)C6)c5F)c4c3)cc2)CC1]

Into a 250-mL round-bottom flask, was placed tert-butyl 2-[2-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]ethoxy]acetate (4.8 g, 6.46 mmol, 1 equiv), dichloromethane (50 mL, 786.50 mmol, 121.71 equiv) and TFA (10 mL). The resulting solution was stirred for 3 h at room temperature. The resulting mixture was concentrated under reduced pressure. This resulted in 3.8 g (85.64%) of 2-[2-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]ethoxy]acetic acid as yellow oil. LC/MS (ESI) m/z: 687.35 $[M+1]^+$.

Step 8: Preparation of (2S,4R)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-(4-(4-methylthiazol-5-yl)benzyl)pyrrolidine-2-carboxamide

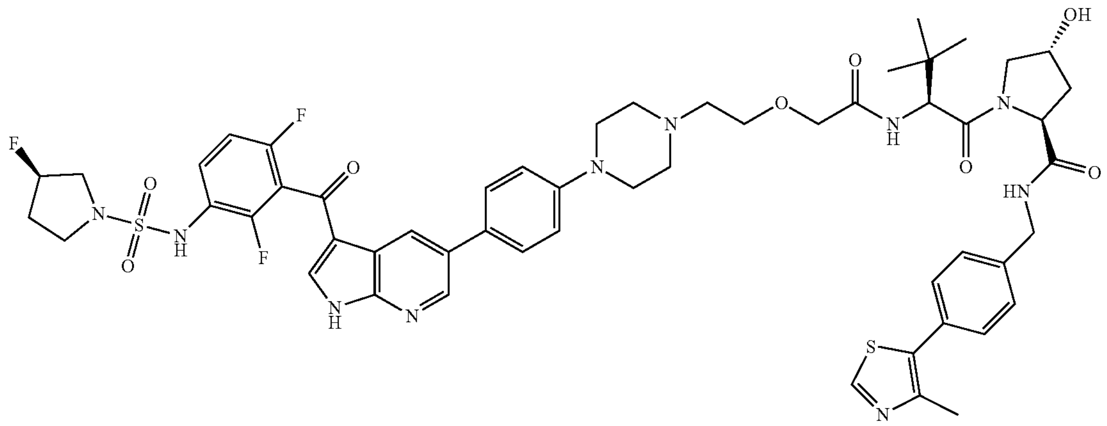 [SMILES: Cc1ncsc1-c1ccc(CNC(=O)[C@@H]2C[C@@H](O)CN2C(=O)[C@@H](NC(=O)COCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

Into a 100-mL round-bottom flask, was placed 2-[2-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]ethoxy]acetic acid (1.1 g, 1.60 mmol, 1 equiv), N,N-dimethylformamide (20 mL), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (748.1 mg, 1.60 mmol, 1 equiv), N,N-diisopropylethylamine (621.1 mg, 4.81 mmol, 3 equiv) and $T_3P$ (1.526 g, 50% solution in ethyl acetate, 2.40 mmol, 1.5 equiv). The resulting solution was stirred for 2 h at room temperature. The reaction was then quenched by water (50 mL) and extracted with dichloromethane (50 mL×3). The combined organic layers was washed with brine (50 mL) and water (50 mL), dried over anhydrous sodium sulfate and concentrated under reduced pressure. The residue was applied onto a silica gel column eluting with dichloromethane/methanol (v:v=10:1). This resulted in 256.3 mg (14.56%) of (2S,4R)-1-[(2S)-2-(2-[2-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]ethoxy]acetamido)-3,3-dimethylbutanoyl]-4-hydroxy-N-[[4-(4-methyl-1,3-thiazol-5-yl)phenyl]methyl]pyrrolidine-2-carboxamide as a yellow solid. LC/MS (ESI) m/z: 1099.60 $[M+1]^+$; $^1$H-NMR (300 MHz, DMSO-$d_6$) δ 12.94 (s, 1H), 9.81 (s, 1H), 8.96 (s, 1H), 8.74-8.60 (m, 2H), 8.60-8.49 (m, 1H), 8.08 (s, 1H), 7.72-7.53 (m, 3H), 7.51-7.33 (m, 5H), 7.32-7.22 (m, 1H), 7.04 (d, J=8.5 Hz, 2H), 5.48-5.11 (m, 2H), 4.71-4.08 (m, 6H), 4.08-3.89 (m, 2H), 3.77-3.48 (m, 4H), 3.30-3.11 (m, 6H), 2.72-2.58 (m, 6H), 2.42 (s, 3H), 2.26-1.84 (m, 5H), 0.97 (s, 9H).

Step 9: Preparation of tert-butyl 2,5,8,11,14,17,20,23,26,29,32,35,38,41,44,47,50,53,56,59,62,65,68-tricosaoxahenheptacontan-71-oate

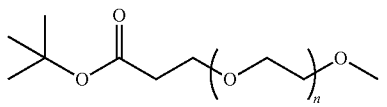

n~22

To a solution of 2,5,8,11,14,17,20,23,26,29,32,35,38,41,44,47,50,53,56,59,62,65-docosaoxaheptahexacontan-67-ol (1.00 g, 1.00 mmol, 1 equiv) in THF (10 mL) was added Na (5.8 mg, 0.25 mmol, 0.253 equiv) and tert-butyl prop-2-enoate (640.9 mg, 5.00 mmol, 5.006 equiv). The reaction mixture was stirred for 26 hr at room temperature. The reaction was then quenched by the addition of water (30 mL). THF was removed under vacuum. The residue was extracted with ethyl acetate (80 mL×4). The combined organic phase was washed with brine (30 mL×1). The organic layer was dried over anhydrous sodium sulfate. The residue was applied onto a silica gel column with dichloromethane/methanol (15:1). This resulted in 453.3 mg (40.19%) of tert-butyl 2,5,8,11,14,17,20,23,26,29,32,35,38,41,44,47,50,53,56,59,62,65,68-tricosaoxahenheptacontan-71-oate as a light brown semi-solid.

Step 10: Preparation of 2,5,8,11,14,17,20,23,26,29,32,35,38,41,44,47,50,53,56,59,62,65,68-tricosaoxahenheptacontan-71-oic acid

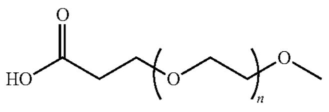

n~22

To a solution of tert-butyl 2,5,8,11,14,17,20,23,26,29,32,35,38,41,44,47,50,53,56,59,62,65,68-tricosaoxahenheptacontan-71-oate (400 mg, 0.35 mmol, 1 equiv) in 1,2-dichloroethane (4 mL) was added trifluoroacetic acid (1.2 mL). The reaction solution was stirred for 4 hr at room temperature. The resulting solution was evaporated to dryness, and then 1,2-dichloroethane was added and evaporated to dryness for several times to remove trifluoroacetic acid. This resulted in 380 mg (99.97%) of 2,5,8,11,14,17,20,23,26,29,32,35,38,41,44,47,50,53,56,59,62,65,68-tricosaoxahenheptacontan-71-oic acid as light yellow oil.

Step 11: Preparation of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxahenheptacontan-71-oate

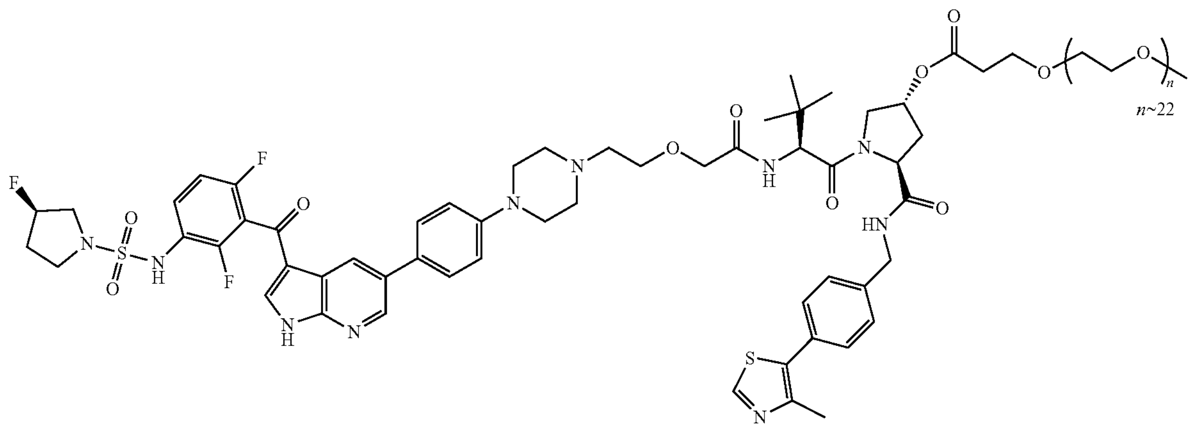

n~22

Into a 100-mL round-bottom flask, was placed (2S,4R)-1-[(2S)-2-(2-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]acetamido)-3,3-dimethylbutanoyl]-4-hydroxy-N-[[4-(4-methyl-1,3-thiazol-5-yl)phenyl]methyl]pyrrolidine-2-carboxamide (330 mg, 0.30 mmol, 1 equiv), DCM (25 mL). 2,5,8,11,14,17,20,23,26,29,32,35,38,41,44,47,50,53,56,59,62,65,68-tricosaoxahenheptacontan-71-oic acid (2.42 g, 2.25 mmol, 7.511 equiv), DMAP (550 mg, 4.50 mmol, 14.996 equiv) and EDCI (863 mg, 4.50 mmol, 14.996 equiv) were added in 5 portions in 3 h. The resulting solution was stirred for 48 h at room temperature. The resulting solution was concentrated and the residue was diluted with saturated $NH_4Cl$ (200 mL). The resulting mixture was extracted with ethyl acetate (180 mL×2) and the organic layers were combined. The combined organic layer was washed with saturated $NH_4Cl$ (200 mL) and dried over anhydrous sodium sulfate and concentrated under vacuum. The crude product was purified by Prep-HPLC. This resulted in 162.0 mg (25.05%) of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxahenheptacontan-71-oate as a yellow oil. LC/MS (ESI) m/z: 2154.45 $[M+1]^+$; $^1H$ NMR (300 MHz, $CDCl_3$) δ 11.70 (s, 1H), 8.83 (s, 1H), 8.66 (s, 1H), 8.57 (s, 1H), 7.76-7.68 (m, 2H), 7.53 (d, J=8.4 Hz, 2H), 7.41-7.32 (m, 5H), 7.23-7.20 (m, 1H), 7.06-6.96 (m, 3H), 5.42 (s, 1H), 5.23 (d, J=51.0 Hz, 1H), 4.74-4.69 (m, 1H), 4.58-4.51 (m, 2H), 4.37-4.31 (m, 1H), 4.08-3.94 (m, 3H), 3.87-3.73 (m, 2H), 3.70-3.61 (m, 93H), 3.57-3.48 (m, 2H), 3.37 (s, 3H), 3.29 (m, 4H), 2.73-2.53 (m, 9H), 2.49 (s, 3H), 2.27-2.11 (m, 4H), 0.95 (s, 9H).

Exemplary Synthesis of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxahenheptacontan-71-oate (Exemplary Compound 801)

Step 1: Preparation of tert-butyl 69-methyl-2,5,8,11,14,17,20,23,26,29,32,35,38,41,44,47,50,53,56,59,62,65,68-tricosaoxahenheptacontan-71-oate

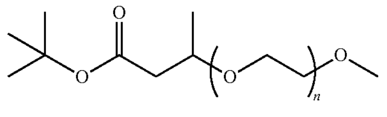

n~22

To a solution of 2,5,8,11,14,17,20,23,26,29,32,35,38,41,44,47,50,53,56,59,62,65-docosaoxaheptahexacontan-67-ol (20 g, 19.98 mmol, 1 equiv) in THF (200 mL) was added Na (236.6 mg, 10.29 mmol, 0.515 equiv). Then followed by the addition of tert-butyl but-3-enoate (65 mL, 400.89 mmol, 20.069 equiv). The resulting solution was stirred for 14 hr at room temperature. The reaction was then quenched by the addition of water (20 mL). THF was removed under vacuum. The residue was extracted with ethyl acetate (80 mL×4). The organic layer was washed with brine (20 mL×4) and dried over anhydrous sodium sulfate. The crude was applied onto a silica gel column with dichloromethane/methanol (15:1). This resulted in 14.64 g (64.10%) of tert-butyl 69-methyl-2,5,8,11,14,17,20,23,26,29,32,35,38,41,44,47,50,53,56,59,62,65,68-tricosaoxahenheptacontan-71-oate as a white semi-solid. $^1H$-NMR (300 MHz, $CDCl_3$) δ 3.90-3.84 (m, 1H), 3.80-3.53 (m, 90H), 3.38 (m, 3H), 2.56-2.48 (m, 1H), 2.33-2.24 (m, 2H), 1.45 (s, 9H), 1.21-1.19 (m, 3H).

Step 2: Preparation of 69-methyl-2,5,8,11,14,17,20,23,26,29,32,35,38,41,44,47,50,53,56,59,62,65,68-tricosaoxahenheptacontan-71-oic acid

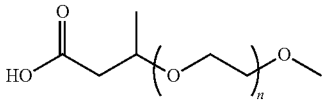

n~22

To a solution of tert-butyl 69-methyl-2,5,8,11,14,17,20,23,26,29,32,35,38,41,44,47,50,53,56,59,62,65,68-tricosaoxahenheptacontan-71-oate (10 g, 8.75 mmol, 1 equiv) in DCE (100 mL) was added TFA (30 mL, 403.89 mmol, 46.181 equiv). The resulting solution was stirred for 5 hr at room temperature. Then the resulting mixture was evaporated to dryness. DCE was added and the solution was evaporated to dryness again. This process was repeated for 3 times and then dried under vaccum to give a light brown oil. This resulted in 9.6 g (100%) of 69-methyl-2,5,8,11,14,17,20,23,26,29,32,35,38,41,44,47,50,53,56,59,62,65,68-tricosaoxahenheptacontan-71-oic acid as light brown oil.

Step 3: Preparation of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxahenheptacontan-71-oate

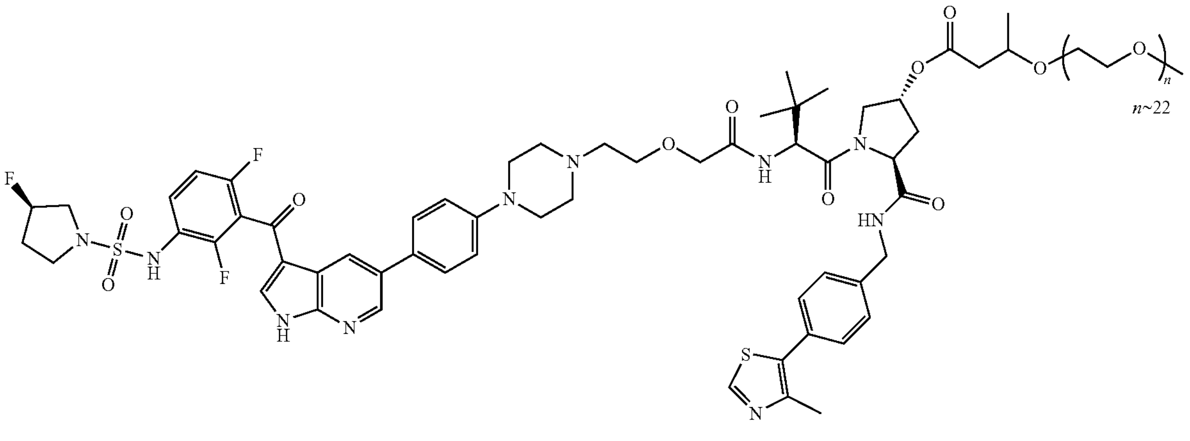

n~22

Into a 100-mL round-bottom flask, was placed (2S,4R)-1-[(2S)-2-(2-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]acetamido)-3,3-dimethylbutanoyl]-4-hydroxy-N-[[4-(4-methyl-1,3-thiazol-5-yl)phenyl]methyl]pyrrolidine-2-carboxamide (330 mg, 0.30 mmol, 1 equiv), dichloromethane (25 mL). 69-methyl-2,5,8,11,14,17,20,23,26,29,32,35,38,41,44,47,50,53,56,59,62,65,68-tricosaoxahenheptacontan-71-oic acid (2.45 g, 2.25 mmol, 7.506 equiv), DMAP (550 mg, 4.50 mmol, 14.996 equiv) and EDCI (863 mg, 4.50 mmol, 14.996 equiv) were added in 5 portions in 3 h. The resulting solution was stirred for 48 h at room temperature. The resulting solution was concentrated and the residue was diluted with saturated $NH_4Cl$ (200 mL). The resulting mixture was extracted with ethyl acetate (200 mL×2) and the organic layers combined. The organic was washed with saturated $NH_4Cl$ (200 mL), dried over anhydrous sodium sulfate and concentrated under vacuum. The crude product was purified by Prep-HPLC. This resulted in 189.9 mg (29.17%) of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxahenheptacontan-71-oate as a yellow oil. LC/MS (ESI) m/z: 2168.46 $[M+1]^+$; $^1H$ NMR (300 MHz, $CDCl_3$) δ 11.67 (s, 1H), 8.82 (s, 1H), 8.66 (s, 1H), 8.58 (s, 1H), 7.75-7.67 (m, 2H), 7.54 (d, J=8.7 Hz, 2H), 7.40-7.29 (m, 5H), 7.25-7.23 (m, 1H), 7.05-6.96 (m, 3H), 5.40 (s, 1H), 5.21 (d, J=52.2 Hz, 1H), 4.70 (m, 1H), 4.59-4.50 (m, 2H), 4.37-4.30 (m, 1H), 4.07-3.98 (m, 3H), 3.93-3.81 (m, 3H), 3.70-3.42 (m, 92H), 3.37 (s, 3H), 3.27 (m, 4H), 2.73 (m, 6H), 2.62-2.50 (m, 2H), 2.48 (s, 3H), 2.42-2.35 (m, 1H), 2.26-2.09 (m, 4H), 1.98-1.93 (m, 1H), 1.19 (d, J=6.3 Hz, 3H), 0.96 (s, 9H).

Exemplary Synthesis of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxaheptacontan-70-oate (Exemplary Compound 802)

Step 1: Preparation of tert-butyl 69-methyl-2,5,8,11,14,17,20,23,26,29,32,35,38,41,44,47,50,53,56,59,62,65,68-tricosaoxaheptacontan-70-oate

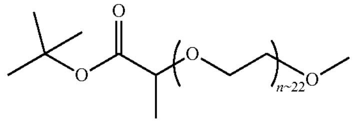

Into a 100-mL round-bottom flask purged and maintained with an inert atmosphere of nitrogen, was placed PEG1000 (10 g, 10.00 mmol, 1.00 equiv), tetrahydrofuran (100 mL). This was followed by the addition of sodium hydride (1.6 g, 66.67 mmol, 4.00 equiv) in several batches at 0° C., after stirred 1 h, to this was added tert-butyl 2-bromopropanoate (4.16 g, 19.90 mmol, 2.00 equiv) dropwise with stirring. The resulting solution was stirred overnight at room temperature. The reaction was then quenched by the addition of water/ice (100 mL). The resulting solution was extracted with ethyl acetate (200 mL×2) and the organic layers combined. The residue was applied onto a silica gel column with dichloromethane/methanol (10/1). This resulted in 4.63 g of tert-butyl 69-methyl-2,5,8,11,14,17,20,23,26,29,32,35,38,41,44,47,50,53,56,59,62,65,68-tricosaoxaheptacontan-70-oate as colorless oil Step 2: Preparation of 69-methyl-2,5,8,11,14,17,20,23,26,29,32,35,38,41,44,47,50,53,56,59,62,65,68-tricosaoxaheptacontan-70-oic acid

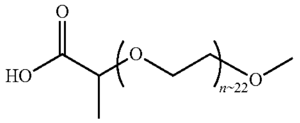

Into a 250-mL round-bottom flask, was placed tert-butyl 2-(2-methoxyethoxy)propanoate (4.63 g, 4.10 mmol, 1.00 equiv), dioxane (50 mL), hydrogen chloride (4 M) (20 mL). The resulting solution was stirred for 16 h at room temperature. The resulting mixture was concentrated under vacuum. This resulted in 4.0 g (91%) of 69-methyl-2,5,8,11,14,17,20,23,26,29,32,35,38,41,44,47,50,53,56,59,62,65,68-tricosaoxaheptacontan-70-oic acid as light-yellow oil.

Step 3: Preparation of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxaheptacontan-70-oate

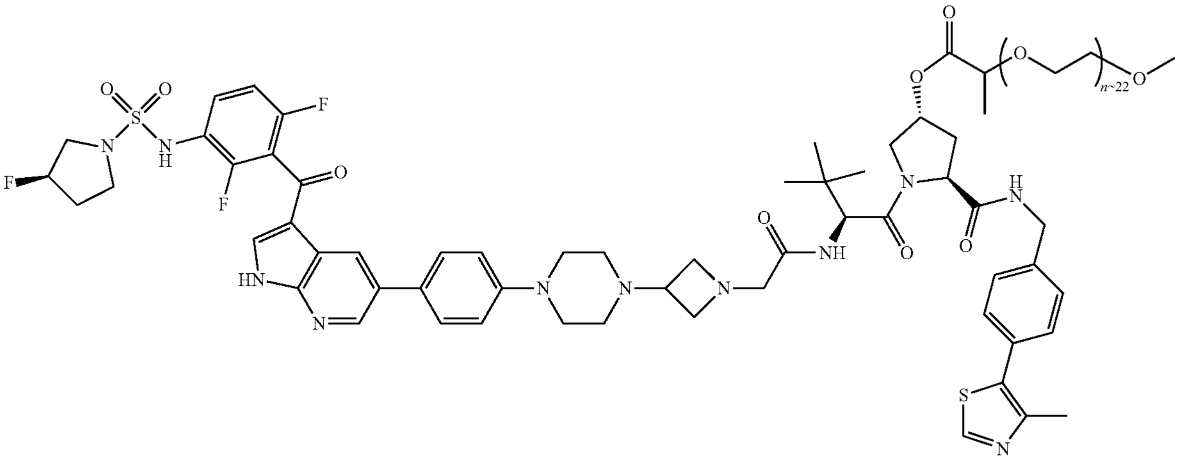

Into a 100-mL round-bottom flask, was placed (2S,4R)-1-[(2S)-2-(2-[3-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]azetidin-1-yl]acetamido)-3,3-dimethylbutanoyl]-4-hydroxy-N-[[4-(4-methyl-1,3-thiazol-5-yl)phenyl]methyl]pyrrolidine-2-carboxamide (300.0 mg, 0.27 mmol, 1.00 equiv), dichloromethane (10 mL), 4-dimethylaminopyridine (165 mg, 1.35 mmol, 5.00 equiv), 2-(2-methoxyethoxy)propanoic acid (581.0 mg, 0.54 mmol, 2.00 equiv), after stirred 10 min, added EDCI (259.0 mg, 1.35 mmol, 5.00 equiv). The resulting solution was stirred for 16 h at room temperature. Then added DMAP stirred 16 h another. The resulting mixture was concentrated under vacuum. The resulting solution was extracted with of ethyl acetate (150 mL×2) and the organic layers combined. The resulting mixture was washed with brine (50 mL×2). The crude product was purified by Prep-HPLC. This resulted in 122.8 mg (37%) of (3R,5S)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-5-((4-(4-methylthiazol-5-yl)benzyl)carbamoyl)pyrrolidin-3-yl 69-methyl-2,5,8,11,14,17,20,23,26,29,32,35,38,41,44,47,50,53,56,59,62,65,68-tricosaoxaheptacontan-70-oate as a yellow solid. LC/MS (ESI) m/z: 2165.45 $[M+1]^+$; $^1$H-NMR (400 MHz, $CD_3OD$) δ 8.86 (s, 1H), 8.67 (s, 1H), 8.59 (d, J=2.0 Hz, 1H), 7.89 (s, 1H), 7.75-7.74 (m, 1H), 7.59 (d, J=8.8 Hz, 2H), 7.46-7.43 (m, 4H), 7.10-7.08 (m, 3H), 5.35-5.15 (m, 2H), 4.56-4.54 (m, 3H), 4.38-4.34 (m, 1H), 4.23-4.13 (m, 2H), 3.90-3.80 (m, 2H), 3.63-3.44 (m, 89H), 3.34-3.31 (m, 6H), 3.29-3.16 (m, 11H), 2.56 (s, 4H), 2.48 (s, 3H), 2.30-2.25 (m, 1H), 2.20-2.10 (m, 2H), 1.36-1.34 (m, 3H), 1.05 (s, 9H).

Exemplary Synthesis of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxadoheptacontan-72-oate (Exemplary Compound 803)

Step 1: Preparation of 4-bromobutanoyl chloride

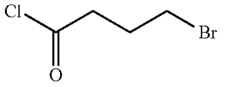

Into a 250-mL round-bottom flask, was placed 4-bromobutanoic acid (10.0 g, 59.88 mmol, 1.00 equiv), dichloromethane (100 mL), N,N-dimethylformamide (0.15 mL). This was followed by the addition of thionyl chloride (8.5 mL) dropwise with stirring at 0° C. The resulting solution was stirred for 4 h at room temperature. The resulting mixture was concentrated under vacuum. This resulted in 11.08 g (100%) of 4-bromobutanoyl chloride as light yellow oil.

Step 2: Preparation of (3-methyloxetan-3-yl)methyl 4-bromobutanoate

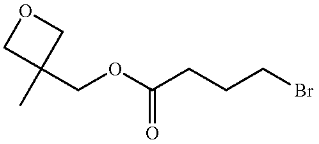

Into a 250-mL round-bottom flask, was placed (3-methyloxetan-3-yl)methanol (6.14 g, 60.12 mmol, 1.00 equiv), dichloromethane (100 mL), pyridine (5.70 g, 72.06 mmol, 1.20 equiv). This was followed by the addition of a solution of 4-bromobutanoyl chloride (11.08 g, 59.75 mmol, 0.99 equiv) in dichloromethane (100 mL) dropwise with stirring at 0° C. The resulting solution was stirred for 16 h at room temperature. The resulting solution was extracted with dichloromethane (50 mL×2) and the organic layers combined. The resulting mixture was washed with brine (10 mL×2). The mixture was dried over anhydrous sodium sulfate. The residue was applied onto a silica gel column with ethyl acetate/petroleum ether (1/3). This resulted in 11.4 g (72%) of 5-bromo-1-[(3-methyloxetan-3-yl)methoxy]pentan-2-one as light yellow oil.

Step 3: Preparation of 1-(3-bromopropyl)-4-methyl-2,6,7-trioxabicyclo[2.2.2]octane

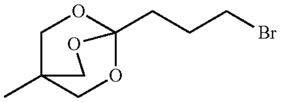

To a solution of 5-bromo-1-[(3-methyloxetan-3-yl)methoxy]pentan-2-one (9.46 g, 35.68 mmol, 1 equiv) in dichloromethane (40 mL) was added $BF_3$. $Et_2O$ (1.2 mL, 9.47 mmol, 0.265 equiv) at 0° C. The reaction mixture was then stirred for 4 hr at 0° C. The reaction was then quenched by the addition of 5.7 mL of $Et_3N$. The resulting mixture was stirred at RT for 15 min (s), and then concentrated. The residue was dissolved in $Et_2O$ (100 mL), filtered and concentrated. The residue was applied onto a basic $Al_2O_3$ column with dichloromethane/petroleum ether (1:2). This resulted in 4.68 g (52.2%) of 1-(3-bromopropyl)-4-methyl-2,6,7-trioxabicyclo[2.2.2]octane as colorless oil. $^1H$ NMR (300 MHz, $CDCl_3$) δ 3.89 (s, 6H), 3.48-3.42 (m, 2H), 2.06-1.99 (m, 2H), 1.83-1.80 (m, 2H), 0.80 (s, 3H).

Step 4: Preparation of 1-(2,5,8,11,14,17,20,23,26,29,32,35,38,41,44,47,50,53,56,59,62,65,68-tricosaoxahenheptacontan-71-yl)-4-methyl-2,6,7-trioxabicyclo[2.2.2]octane

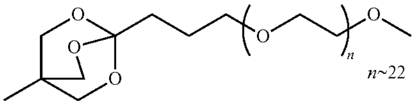

Into a 30-mL sealed tube, was placed 2,5,8,11,14,17,20,23,26,29,32,35,38,41,44,47,50,53,56,59,62,65-docosaoxaheptahexacontan-67-ol (1.1967 g, 1.20 mmol, 1.500 equiv), Toluene (2 mL), t-BuOH (1.3 mL), t-BuOK (143.6 mg, 1.28 mmol, 1.606 equiv), 1-(3-bromopropyl)-4-methyl-2,6,7-trioxabicyclo[2.2.2]octane (200.1 mg, 0.80 mmol, 1 equiv). The resulting mixture was placed under an N2 atmosphere and stirred for 12 hr at 70° C. The reaction mixture was cooled to room temperature. The mixture was filtered and the solvents were distilled off under reduced pressure. The resulting solution was extracted with ethyl acetate (10 mL×4) and the organic layers combined. Combined organic layer was washed with brine (10 mL×2) and dried over anhydrous sodium sulfate. The resulting mixture was concentrated to dryness and dried under vacuum. This resulted in 657.5 mg (70.4%) of 4-methyl-1-(2,5,8,11,14,17,20,23,26,29,32,35,38,41,44,47,50,53,56,59,62,65,68-tricosaoxahenheptacontan-71-yl)-2,6,7-trioxabicyclo[2.2.2]octane as a light yellow semi-solid.

Step 5: Preparation of 2,5,8,11,14,17,20,23,26,29,32,35,38,41,44,47,50,53,56,59,62,65,68-tricosaoxadoheptacontan-72-oic acid

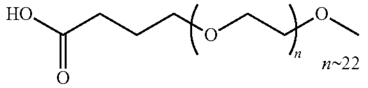

To a solution of 4-methyl-1-(2,5,8,11,14,17,20,23,26,29,32,35,38,41,44,47,50,53,56,59,62,65,68-tricosaoxahenheptacontan-71-yl)-2,6,7-trioxabicyclo[2.2.2]octane (657.5 mg, 0.56 mmol, 1 equiv) in water (2 mL) was added $H_3PO_4$ till pH=1, The reaction solution was stirred for 1 hr at room temperature. Then KOH was added to adjust pH=12. The resulting solution was stirred for 17 hr at room temperature and $H_3PO_4$ was added again to adjust pH=3. The resulting mixture was extracted with dichloromethane (20 mL×4) and the organic layers combined and dried over anhydrous sodium sulfate. The residue was applied onto a silica gel column with dichloromethane/methanol (10:1). This resulted in 555.4 mg (91.0%) of 2,5,8,11,14,17,20,23,26,29,32,35,38,41,44,47,50,53,56,59,62,65,68-tricosaoxadoheptacontan-72-oic acid as a light yellow semi-solid.

Step 6: Preparation of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxadoheptacontan-72-oate

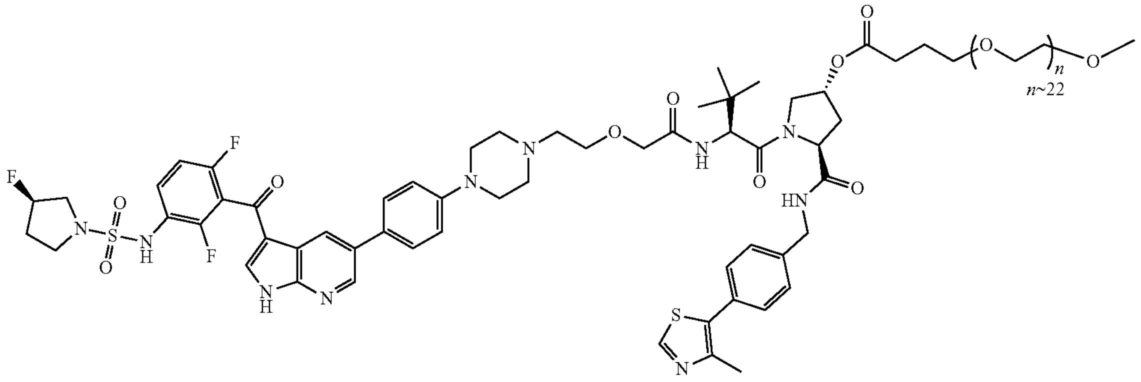

To a solution of (2S,4R)-1-[(2S)-2-(2-[2-[4-(4-[3-[(2,6-difluoro-3-[[(3R)-3-fluoropyrrolidine-1-sulfonyl]amino] phenyl)carbonyl]-1H-pyrrolo[2,3-b]pyridin-5-yl]phenyl) piperazin-1-yl]ethoxy]acetamido)-3,3-dimethylbutanoy (50.3 mg, 0.05 mmol, 1 equiv) in dichloromethane (4 mL) was added 2,5,8,11,14,17,20,23,26,29,32,35,38,41,44,47,50,53,56,59,62,65,68-tricosaoxadoheptacontan-72-oic acid (74.6 mg, 0.07 mmol, 1.4 equiv) and DMAP (17.0 mg, 0.14 mmol, 2.80 equiv). The mixture was stirred at room temperature for 10 minutes. Then to this was added EDCI (28.8 mg, 0.15 mmol, 3.0 equiv). The reaction solution was stirred for 1 hr at room temperature. Additional 2,5,8,11,14,17,20,23,26,29,32,35,38,41,44,47,50,53,56,59,62,65,68-tricosaoxadoheptacontan-72-oic acid (225 mg, 0.21 mmol, 4.1 equiv), DMAP (55.1 mg, 0.45 mmol, 9.0 equiv) and EDCI (87 mg, 0.45 mmol, 9.1 equiv) were divided into three portions and the above process was repeated for another three times. Then to this was added DMAP (58.6 mg, 0.48 mmol, 9.6 equiv). The reaction solution was stirred for another 2 hours. Dichloromethane was removed under vacuum. The residue was extracted with ethyl acetate (30 mL×3). The resulting mixture was washed with sat. $NH_4Cl$ (10 mL×2). The mixture was dried over anhydrous sodium sulfate. The crude product was purified by Prep-HPLC. This resulted in 16.6 mg (16.7%) of (3R,5S)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-5-((4-(4-methylthiazol-5-yl)benzyl)carbamoyl)pyrrolidin-3-yl 2,5,8,11,14,17,20,23,26,29,32,35,38,41,44,47,50,53,56,59,62,65,68-tricosaoxadoheptacontan-72-oate as light yellow oil. LC/MS (ESI) m/z: 2168.45 $[M+1]^+$; $^1H$ NMR (400 MHz, $CDCl_3$) δ 0.95 (s, 9H), 1.85-1.89 (m, 2H), 1.92-2.01 (m, 1H), 2.03-2.28 (m, 3H), 2.36-2.38 (m, 2H), 2.48 (s, 4H), 2.66-2.71 (m, 8H), 3.21-3.28 (m, 4H), 3.37 (s, 3H), 3.44-3.49 (m, 4H), 3.53-3.72 (m, 91H), 3.81-3.88 (m, 1H), 3.94-4.12 (m, 3H), 4.25-4.38 (m, 1H), 4.47-4.58 (m, 2H), 4.65-4.73 (m, 1H), 5.08-5.35 (m, 1H), 5.39 (s, 1H), 6.96-7.06 (m, 3H), 7.19-7.24 (m, 1H), 7.32-7.39 (m, 5H), 7.52-7.55 (m, 2H), 7.65-7.79 (m, 2H), 8.57-8.58 (m, 1H), 8.66 (s, 1H), 8.81 (s, 1H).

Exemplary Synthesis of (3R,5S)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-5-(((S)-1-(4-(4-methylthiazol-5-yl)phenyl)ethyl)carbamoyl) pyrrolidin-3-yl 69-oxo-2,5,8,11,14,17,20,23,26,29,32,35,38,41,44,47,50,53,56,59,62,65-docosaoxa-68-azadoheptacontan-72-oate (Exemplary Compound 828)

Step 1: Preparation of tert-butyl 4-(4-(4-bromophenyl)piperazin-1-yl)piperidine-1-carboxylate

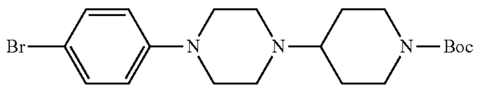 [SMILES: CC(C)(C)OC(=O)N1CCC(N2CCN(c3ccc(Br)cc3)CC2)CC1]

Into a 250 mL round-bottom flask, was placed a solution of 1-(4-bromophenyl)piperazine hydrochloride (5.0 g, 18.0 mmol, 1.0 equiv) in dichloromethane (10 mL), tert-butyl 4-oxopiperidine-1-carboxylate (4.9 g, 24.9 mmol, 1.4 equiv), acetyl ethaneperoxoate; sodioboranyl acetate (13.2 g, 62.3 mmol, 3.5 equiv). The resulting solution was stirred overnight at room temperature. The reaction was then quenched by the addition of 1 mL of water/ice. The resulting solution was extracted with dichloromethane (20 mL×2) and the organic layers combined and dried over anhydrous sodium sulfate and concentrated under vacuum. The residue was applied onto a silica gel column with ethyl acetate/petroleum ether (1:0). This resulted in 4.2 g (54%) of tert-butyl 4-[4-(4-bromophenyl) piperazin-1-yl]piperidine-1-carboxylate as a white solid. LC/MS (ESI) m/z: 426.10 $[M+1]^+$.

Step 2: Preparation of 1-(4-bromophenyl)-4-(piperidin-4-yl)piperazine hydrochloride

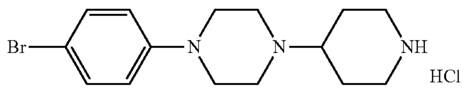 [SMILES: Brc1ccc(N2CCN(C3CCNCC3)CC2)cc1 ; Cl]

Into a 100 mL round-bottom flask, was placed a solution of tert-butyl 4-[4-(4-bromophenyl)piperazin-1-yl]piperidine-1-carboxylate (4.2 g, 9.8 mmol, 1.0 equiv) in dichloromethane (10 mL), hydrogen chloride (5 ml). The resulting solution was stirred for 1 h at room temperature. The resulting mixture was concentrated under vacuum. This resulted in 3.0 g (85%) of 1-(4-bromophenyl)-4-(piperidin-4-yl)piperazine hydrochloride as a white solid. LC/MS (ESI) m/z: 325.95 $[M+1]^+$.

Step 3: Preparation of tert-butyl 2-(4-(4-(4-bromophenyl)piperazin-1-yl)piperidin-1-yl)acetate

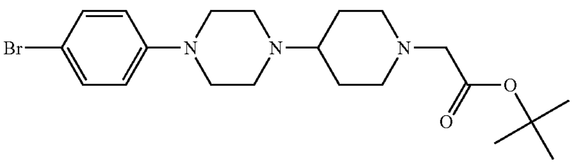 [SMILES: CC(C)(C)OC(=O)CN1CCC(N2CCN(c3ccc(Br)cc3)CC2)CC1]

Into a 100 mL round-bottom flask, was placed a solution of 1-(4-bromophenyl)-4-(piperidin-4-yl)piperazine hydrochloride (3.0 g, 8.3 mmol, 1.0 equiv) in dichloromethane (10 mL), triethylamine (2.0 g, 19.8 mmol, 2.4 equiv), tert-butyl 2-bromoacetate (2.3 g, 11.8 mmol, 1.4 equiv). The resulting solution was stirred overnight at room temperature. The reaction was then quenched by the addition of 1 mL of water/ice. The resulting solution was extracted with dichloromethane (20 mL×2) and the organic layers combined and dried over anhydrous sodium sulfate and concentrated under vacuum. The residue was applied onto a silica gel column with ethyl acetate/petroleum ether (1:0). This resulted in 2.0 g (53%) of tert-butyl 2-[4-[4-(4-bromophenyl) piperazin-1-yl]piperidin-1-yl]acetate as a white solid. LC/MS (ESI) m/z: 440.30 $[M+1]^+$.

Step 4: Preparation of tert-butyl 2-(4-(4-(4-(4,4,5,5-tetramethyl-1,3,2-dioxaborolan-2-yl)phenyl)piperazin-1-yl)piperidin-1-yl)acetate

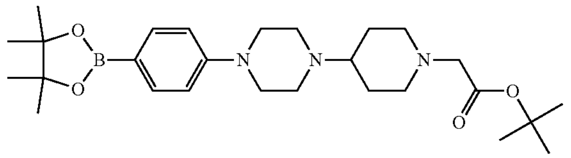 [SMILES: CC(C)(C)OC(=O)CN1CCC(N2CCN(c3ccc(B4OC(C)(C)C(C)(C)O4)cc3)CC2)CC1]

Into a 20-30-mL sealed tube, was placed a solution of tert-butyl 2-[4-[4-(4-bromophenyl)piperazin-1-yl]piperidin-1-yl]acetate (2.0 g, 4.5 mmol, 1.0 equiv) in dioxane (10 mL), 4,4,5,5-tetramethyl-2-(4,4,5,5-tetramethyl-1,3,2-dioxaborolan-2-yl)-1,3,2-dioxaborolane (2.3 g, 9.1 mmol, 2.0 equiv), KOAc (874.6 mg, 8.9 mmol, 2.0 equiv), Pd(dppf)$Cl_2$ (700.6 mg, 0.9 mmol, 0.2 equiv). The resulting solution was stirred overnight at 85° C. in an oil bath. The reaction was then quenched by the addition of 1 mL of water/ice. The resulting solution was extracted with ethyl acetate (20 ml×2) and the organic layers combined and dried over anhydrous sodium sulfate and concentrated under vacuum. The residue was applied onto a silica gel column with ethyl acetate/petroleum ether (1:0). This resulted in 630.0 mg (29%) of tert-butyl 2-(4-[4-[4-(4, 4, 5, 5-tetramethyl-1,3, 2-dioxaborolan-2-yl) phenyl]piperazin-1-yl]piperidin-1-yl)acetate as a black solid. LC/MS (ESI) m/z: 486.25 $[M+1]^+$.

Step 5: Preparation of tert-butyl (R)-2-(4-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)piperidin-1-yl)acetate

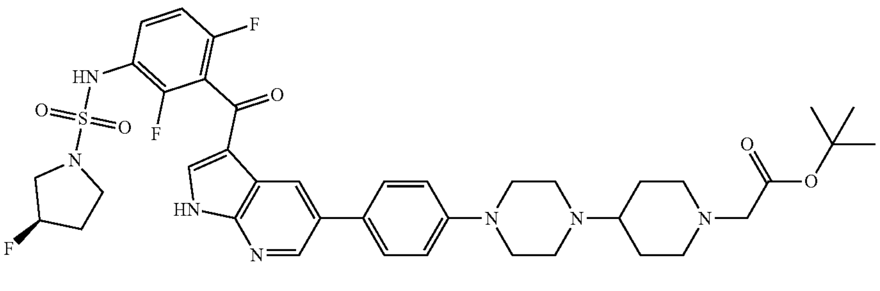 [SMILES: CC(C)(C)OC(=O)CN1CCC(N2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 20-30 mL sealed tube, was placed a solution of tert-butyl 2-(4-[4-[4-(4,4,5,5-tetramethyl-1,3,2-dioxaborolan-2-yl)phenyl]piperazin-1-yl]piperidin-1-yl)acetate (630.0 mg, 1.3 mmol, 1.0 equiv) in dioxane/$H_2O$ (4:1 mL), (3R)—N-(3-5-bromo-1H-pyrrolo[2,3-b]pyridine-3-carbonyl-2,4-difluorophenyl)-3-fluoropyrrolidine-1-sulfonamide (300.0 mg, 0.6 mmol, 0.5 equiv), Pd(dppf)$Cl_2$ (46.9 mg), sodium carbonate (99.2 mg, 0.9 mmol, 0.7 equiv). The resulting solution was stirred for 2 h at 105° C. The reaction was then quenched by the addition of 1 mL of water/ice. The resulting solution was extracted with ethyl acetate (20 mL×2) and the organic layers combined and dried over anhydrous sodium sulfate and concentrated under vacuum. The residue was applied onto a silica gel column with dichloromethane/methanol (10:1). This resulted in 256.0 mg (25%) of tert-butyl 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetate as a yellow solid. LC/MS (ESI) m/z: 782.05 $[M+1]^+$.

Step 6: Preparation of (R)-2-(4-(4-(4-(3-(2,6-difluoro-3-((3-fluoropyrrolidine)-1-sulfonamido)benzoyl)-1H-pyrrolo[2,3-b]pyridin-5-yl)phenyl)piperazin-1-yl)piperidin-1-yl)acetic acid

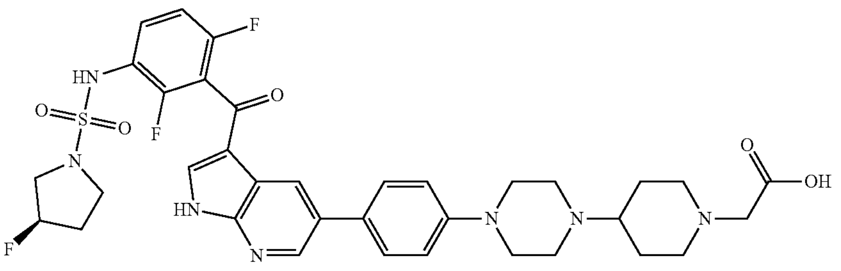 [SMILES: O=C(O)CN1CCC(N2CCN(c3ccc(-c4cnc5[nH]cc(C(=O)c6c(F)ccc(NS(=O)(=O)N7CC[C@@H](F)C7)c6F)c5c4)cc3)CC2)CC1]

Into a 100 mL round-bottom flask, was placed a solution of tert-butyl 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetate (256.0 mg, 0.3 mmol, 1.0 equiv) in dichloromethane (10 mL), trifluoroacetic acid (2 mL). The resulting solution was stirred overnight at room temperature. The resulting mixture was concentrated under vacuum. This resulted in 120.0 mg (50%) of 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetic acid as a yellow solid. LC/MS (ESI) m/z: 726.15 $[M+1]^+$.

Step 7: Preparation of (2S,4R)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

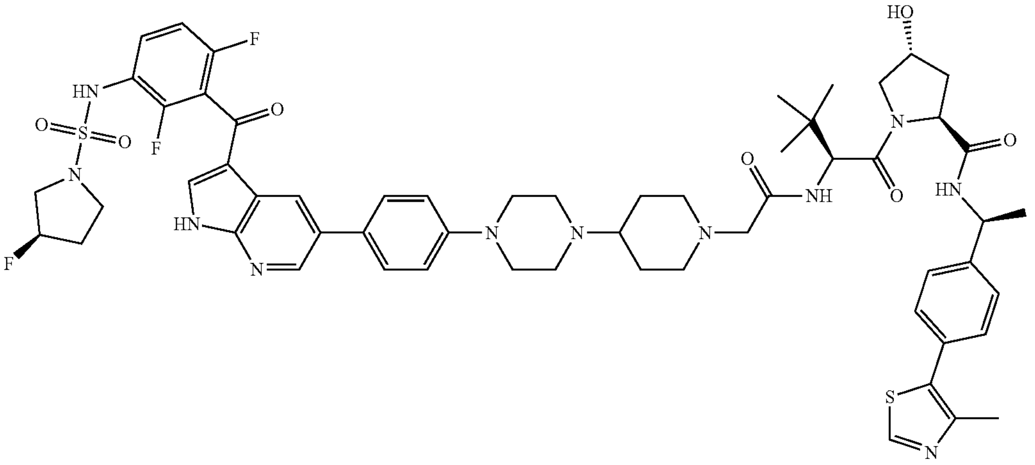 [SMILES: Cc1ncsc1-c1ccc([C@H](C)NC(=O)[C@@H]2C[C@@H](O)CN2C(=O)[C@@H](NC(=O)CN2CCC(N3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 100 mL round-bottom flask, was placed a solution of 2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetic acid (120.0 mg, 0.3 mmol, 1.0 equiv) in N,N-dimethylformamide (5 mL), (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide (88.2 mg, 0.4 mmol, 1.2 equiv), N,N-Diisopropylethylamine (64.1 mg, 1.0 mmol, 3.0 equiv), (Benzotriazole-1-yloxy) tris(dimethylamino) phosphonium hexafluorophosphate (87.8 mg). The resulting solution was stirred for 1 h at room temperature. The reaction was then quenched by the addition of 1 mL of water/ice. The resulting solution was extracted with ethyl acetate (20 mL×2) and the organic layers combined and dried over anhydrous sodium sulfate and concentrated under vacuum. The crude product was purified by Prep-HPLC resulting in 42.9 mg (23%) of (2S,4R)-1-[(2S)-2-(2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetamido)-3,3-dimethylbutanoyl]-4-hydroxy-N-[(1S)-1-[4-(4-methyl-1,3-thiazol-5-yl)phenyl]ethyl]pyrrolidine-2-carboxamide as an off-white solid. LC/MS (ESI) m/z: 1152.20 $[M+1]^+$; $^1$H-NMR (400 MHz, DMSO-$d_6$) δ 12.87 (brs, 1H), 9.96 (brs, 1H), 8.96 (d, J=2.1 Hz, 1H), 8.63 (d, J=2.3 Hz, 1H), 8.51 (s, 1H), 8.40 (d, J=7.6 Hz, 1H), 8.04 (s, 1H), 7.74 (d, J=9.6 Hz, 1H), 7.70-7.60 (m, 3H), 7.47-7.42 (m, 2H), 7.40-7.31 (m, 2H), 7.23 (t, J=8.9 Hz, 1H), 7.05 (d, J=8.5 Hz, 2H), 5.36-5.15 (m, 1H), 5.19 (s, 1H), 4.88 (t, J=7.1 Hz, 1H), 4.54-4.38 (m, 2H), 4.27-4.21 (m, 1H), 3.60-3.52 (m, 2H), 3.47-3.41 (m, 1H), 3.37-3.31 (m, 2H), 3.30-3.24 (m, 5H), 3.03 (d, J=16.1 Hz, 1H), 2.89-2.80 (m, 3H), 2.70-2.55 (m, 5H), 2.34-2.03 (m, 7H), 1.87-1.72 (m, 3H), 1.47-1.37 (m, 6H), 0.93 (s, 9H).

Step 8: Preparation of 4-(((3R,5S)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl)oxy)-4-oxobutanoic acid

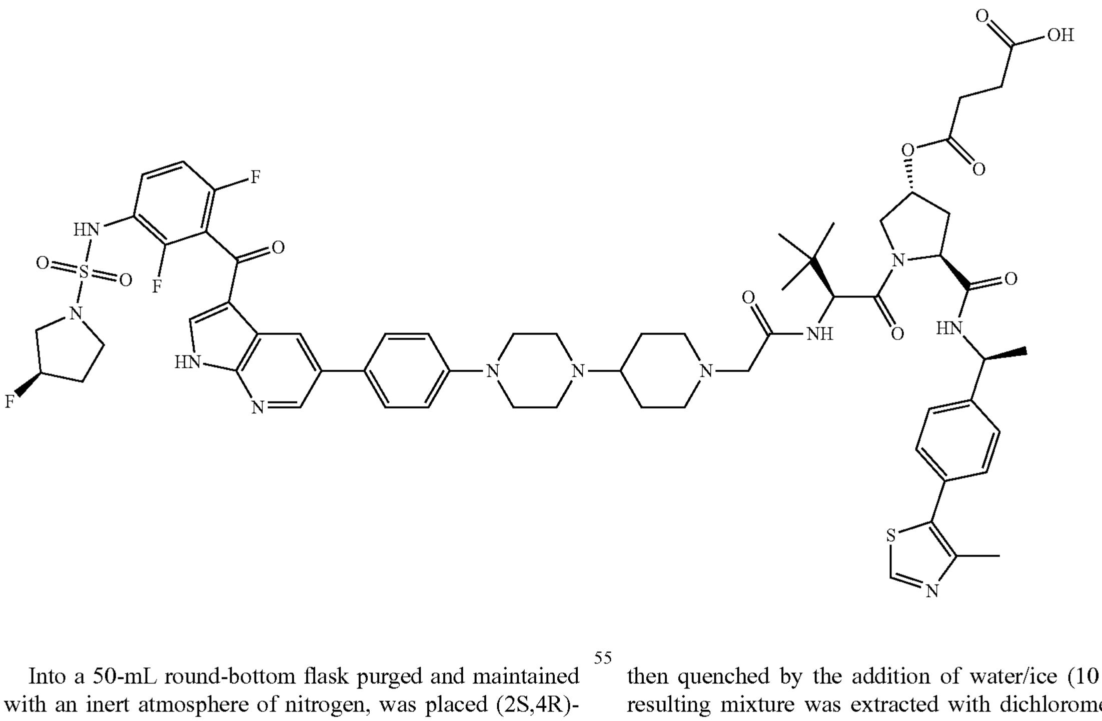

Into a 50-mL round-bottom flask purged and maintained with an inert atmosphere of nitrogen, was placed (2S,4R)-1-[(2S)-2-(2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetamido)-3,3-dimethylbutanoyl]-4-hydroxy-N-[(1S)-1-[4-(4-methyl-1,3-thiazol-5-yl)phenyl]ethyl]pyrrolidine-2-carboxamide (467 mg, 0.405 mmol, 1 equiv), $Et_3N$ (123.02 mg, 1.216 mmol, 3 equiv), DMAP (148.53 mg, 1.216 mmol, 3 equiv), oxolane-2,5-dione (202.77 mg, 2.026 mmol, 5 equiv) in dichloromethane (20 mL). The resulting solution was stirred for 16 h at 25° C. in an oil bath. The reaction was then quenched by the addition of water/ice (10 mL). The resulting mixture was extracted with dichloromethane (40 mL×3) and the organic layers were combined, washed with sat. $NH_4Cl$ solution (40 mL), dried over anhydrous sodium sulfate and concentrated under vacuum. This resulted in 353 mg (69.55%) of 4-[[(3R,5S)-1-[(2S)-2-(2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetamido)-3,3-dimethylbutanoyl]-5-[[(1S)-1-[4-(4-methyl-1,3-thiazol-5-yl)phenyl]ethyl]carbamoyl]pyrrolidin-3-yl]oxy]-4-oxobutanoic acid as a yellow solid.

Step 9: Preparation of 2,5,8,11,14,17,20,23,26,29,32,35,38,41,44,47,50,53,56,59,62,65-docosaoxaheptahexacontan-67-yl 4-methylbenzenesulfonate

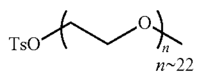

Into a 250-mL round-bottom flask, was placed PEG1000-OMe (5.0 g, 5.00 mmol, 1.00 equiv), TsCl (1.9 g, 9.97 mmol, 2.00 equiv), triethylamine (1.01 g, 9.98 mmol, 2.00 equiv), 4-dimethylaminopyridine (61.0 mg, 0.50 mmol, 0.10 equiv). The resulting solution was stirred for 5 h at room temperature. The resulting mixture was concentrated under vacuum. The residue was applied onto a silica gel column with dichloromethane/methanol (15/1). This resulted in 7.47 g of 2,5,8,11,14,17,20,23,26,29,32,35,38,41,44,47,50,53,56,59,62,65-docosaoxaheptahexacontan-67-yl 4-methylbenzenesulfonate as a light yellow solid.

Step 10: Preparation of tert-butyl (tert-butoxycarbonyl)(2,5,8,11,14,17,20,23,26,29,32,35,38,41,44,47,50,53,56,59,62,65-docosaoxaheptahexacontan-67-yl) carbamate

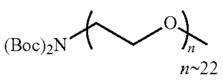

Into a 250-mL round-bottom flask, was placed 2-methoxyethyl 4-methylbenzene-1-sulfonate (7.47 g, 6.47 mmol, 1.00 equiv), acetonitrile (150 mL), tert-butyl N-[(tert-butoxy)carbonyl]carbamate (1.40 g, 6.44 mmol, 1.00 equiv), $Cs_2CO_3$ (4.20 g, 12.89 mmol, 2.00 equiv). The resulting solution was stirred overnight at 50° C. in an oil bath. The solids were filtered out. The resulting mixture was concentrated under vacuum. The residue was applied onto a silica gel column with dichloromethane/methanol (10/1). This resulted in 6.6 g (371%) of tert-butyl (tert-butoxycarbonyl)(2,5,8,11,14,17,20,23,26,29,32,35,38,41,44,47,50,53,56,59,62,65-docosaoxaheptahexacontan-67-yl)carbamate as a light yellow solid Step 11: Preparation of 2,5,8,11,14,17,20,23,26,29,32,35,38,41,44,47,50,53,56,59,62,65-docosaoxaheptahexacontan-67-amine

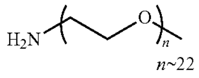

Into a 250-mL round-bottom flask, was placed tert-butyl N-[(tert-butoxy)carbonyl]-N-(2-methoxyethyl)carbamate (6.6 g, 5.50 mmol, 1.00 equiv), dioxane (60.0 mL), hydrogen chloride (4 M) (60 mL). The resulting solution was stirred for 16 h at room temperature. The resulting mixture was concentrated under vacuum. This resulted in 5.5 g of 2,5,8,11,14,17,20,23,26,29,32,35,38,41,44,47,50,53,56,59,62,65-docosaoxaheptahexacontan-67-amine hydrochloride as a light yellow solid Step 12: Preparation of (3R,5S)-1-((S)-2-(2-(4-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)piperidin-1-yl)acetamido)-3,3-dimethylbutanoyl)-5-(((S)-1-(4-(4-methylthiazol-5-yl)phenyl)ethyl)carbamoyl)pyrrolidin-3-yl 69-oxo-2,5,8,11,14,17,20,23,26,29,32,35,38,41,44,47,50,53,56,59,62,65-docosaoxa-68-azadoheptacontan-72-oate

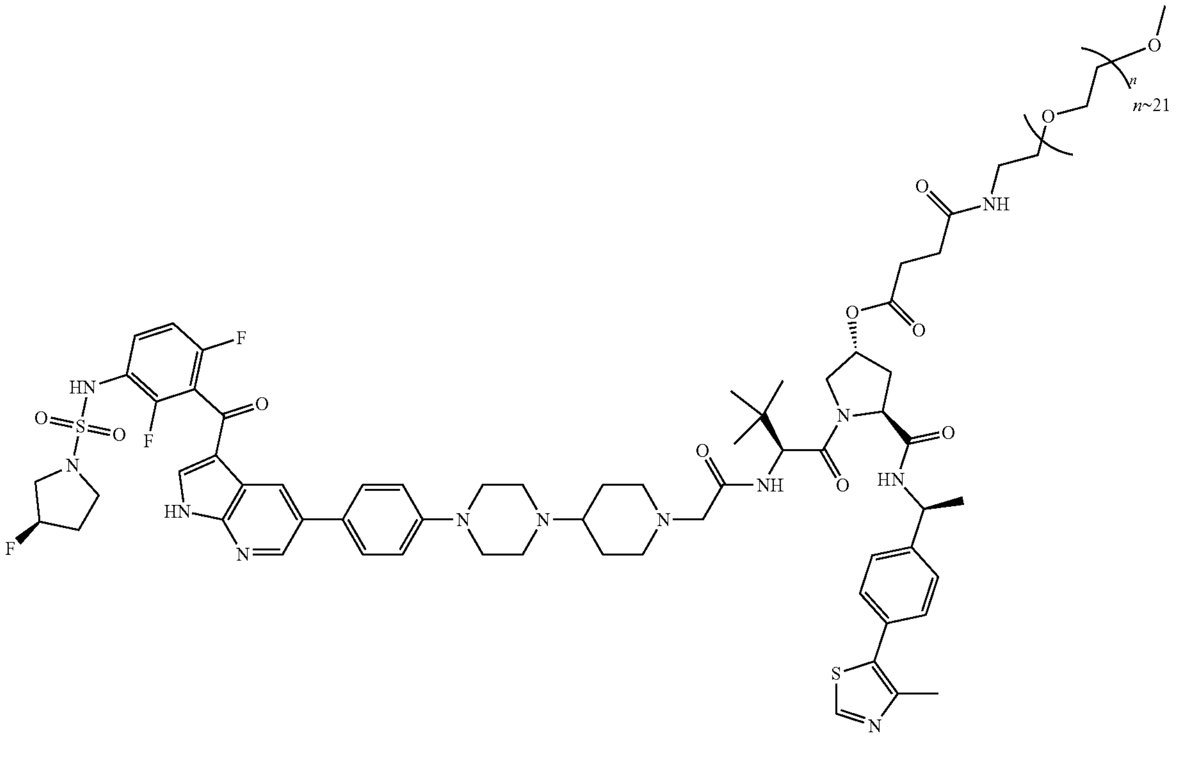

Into a 50-mL round-bottom flask, was placed a solution of 4-[[(3R,5S)-1-[(2S)-2-(2-[4-[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetamido)-3,3-dimethylbutanoyl]-5-[[(1S)-1-[4-(4-methyl-1,3-thiazol-5-yl)phenyl]ethyl]carbamoyl]pyrrolidin-3-yl]oxy]-4-oxobutanoic acid (333 mg, 0.266 mmol, 1 equiv) in DMF (25 mL), to which was added DIPEA (137.45 mg, 1.064 mmol, 4 equiv), 2,5,8,11,14,17,20,23,26,29,32,35,38,41,44,47,50,53,56,59,62,65-docosaoxaheptahexacontan-67-amine (531.88 mg, 0.532 mmol, 2.00 equiv), BOP (176.39 mg, 0.399 mmol, 1.5 equiv). The resulting solution was stirred for 3 h at 25° C. in an oil bath. The reaction was then quenched by the addition of water/ice (30 mL). The resulting mixture was extracted with ethyl acetate (40 mL×3) and the organic layers were combined, washed with brine (40 mL×2), dried over anhydrous sodium sulfate and concentrated. The crude product was purified by Prep-HPLC. This resulted in 207 mg (34.84%) of (3R,5S)-1-[(2S)-2-(2-[4-[4-(4-[3-[2,6-d]fluoro-3-([[(3R)-3-fluoropyrrolidin-1-yl]sulfonyl]amino)benzoyl]-1H-pyrrolo[2,3-b]pyridin-5-yl]phenyl)piperazin-1-yl]piperidin-1-yl]acetamido)-3,3-dimethylbutanoyl]-5-[[(1S)-1-[4-(4-methyl-1,3-thiazol-5-yl)phenyl]ethyl]carbamoyl]pyrrolidin-3-yl 3-[(2,5,8,11,14,17,20,23,26,29,32,35,38,41,44,47,50,53,56,59,62,65-docosaoxaheptahexacontan-67-yl)carbamoyl]propanoate as yellow oil. LC/MS (ESI) m/z: 2234.68 $[M+1]^+$; $^1$H NMR (400 MHz, DMSO-$d_6$) δ 9.01 (s, 1H), 8.75 (s, 1H), 8.65 (s, 1H), 7.95 (s, 1H), 7.78-7.70 (m, 3H), 7.50-7.44 (m, 4H), 7.24-7.17 (m, 3H), 5.32 (s, 2H), 5.19 (s, 1H), 5.06-5.04 (m, 1H), 4.89 (s, 1H), 4.60-4.58 (m, 1H), 4.41-4.32 (m, 2H), 4.30 (s, 5H), 4.14-4.10 (m, 91H), 3.83-3.81 (m, 7H), 3.64-3.63 (m, 5H), 3.56-3.33 (m, 4H), 2.76 (s, 1H), 2.67-2.42 (m, 4H), 2.37-2.34 (m, 4H), 2.21 (m, 3H), 2.16-2.13 (m, 3H), 1.55-1.53 (m, 3H), 1.11-1.08 (m, 9H).

Exemplary Synthesis of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 68-methyl-69-oxo-2,5,8,11,14,17,20,23,26,29,32,35,38,41,44,47,50,53,56,59,62,65-docosaoxa-68-azadoheptacontan-72-oate (Exemplary Compound 816)

Step 1: Preparation of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide

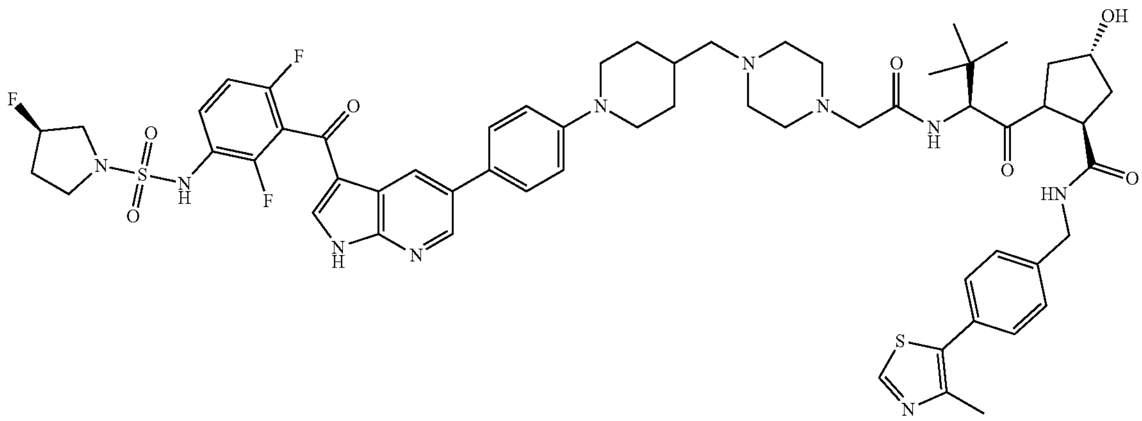 [SMILES: Cc1ncsc1-c1ccc(CNC(=O)[C@@H]2C[C@@H](O)CC2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 100-mL round-bottom flask, was placed 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid (500.0 mg, 0.67 mmol, 1 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (290.0 mg, 0.67 mmol, 1.00 equiv), DIEA (345.0 mg, 2.68 mmol, 4.0 equiv), BOP (450.0 mg, 1.01 mmol, 1.51 equiv) in DMF (15 mL). The reaction was stirred for 3 h at room temperature and then was quenched by the addition of 50 mL water. The resulting mixture was extracted with ethyl acetate (50 mL×2). The combined organic layer was dried over anhydrous sodium sulfate and concentrated under reduced pressure. The crude product was purified by Prep-HPLC. This resulted in 193 mg of (2S,4R)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-4-hydroxy-N-[[4-(4-methyl-1,3-thiazol-5-yl)phenyl]methyl]pyrrolidine-2-carboxamide as an off-white solid. LC/MS (ESI) m/z: 1152.45 $[M+1]^+$; $^1$H-NMR (300 MHz, $CD_3OD$) δ 12.90 (brs, 1H), 9.85 (brs, 1H), 8.98 (s, 1H), 8.67-8.60 (m, 2H), 8.60-8.48 (m, 1H), 8.07 (s, 1H), 7.85-7.76 (m, 1H), 7.68-7.56 (m, 3H), 7.50-7.38 (m, 4H), 7.30-7.22 (m, 1H), 7.12-7.00 (m, 2H), 5.40-5.20 (m, 1H), 5.14 (s, 1H), 4.57-4.47 (m, 1H), 4.47-4.32 (m, 3H), 4.31-4.22 (m, 1H), 3.83-3.70 (m, 2H), 3.70-3.57 (m, 2H), 3.52-3.45 (m, 1H), 3.44-3.35 (m, 2H), 3.31-3.23 (m, 1H), 3.14-2.87 (m, 2H), 2.87-2.67 (m, 2H), 2.63-2.52 (m, 4H), 2.49-2.38 (m, 7H), 2.23-2.14 (m, 2H), 2.14-1.89 (m, 4H), 1.83-1.62 (m, 3H), 1.87-1.12 (m, 2H), 1.00-0.92 (m, 9H).

Step 2: Preparation of 4-(((3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl)oxy)-4-oxobutanoic acid

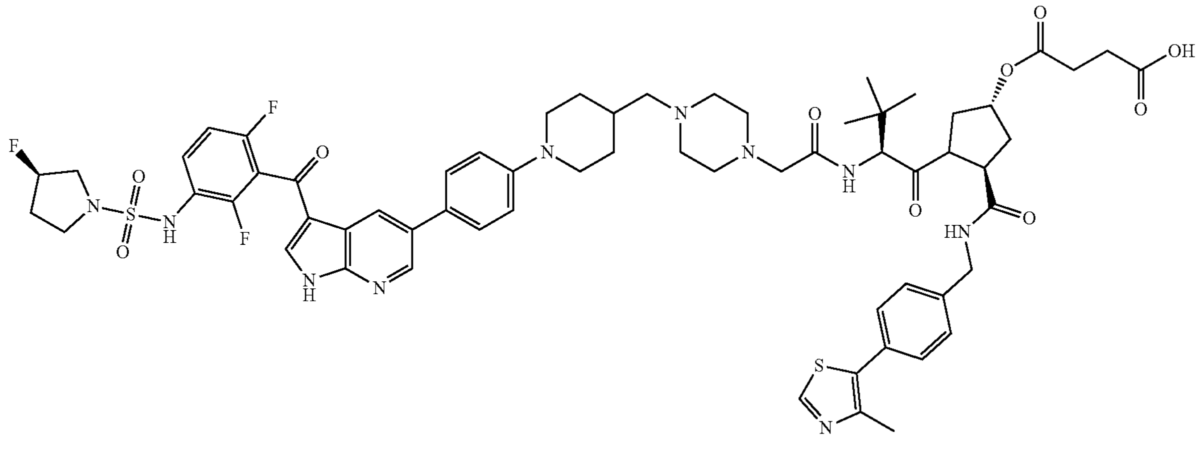 [SMILES: Cc1ncsc1-c1ccc(CNC(=O)[C@@H]2C[C@@H](OC(=O)CCC(=O)O)CC2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 30-mL sealed tube, was placed (2S,4R)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-4-hydroxy-N-[[4-(4-methyl-1,3-thiazol-5-yl)phenyl]methyl]pyrrolidine-2-carboxamide (576.2 mg, 0.50 mmol, 1 equiv), $Et_3N$ (0.14 mL, 1.01 mmol, 2.01 equiv), DMAP (183.3 mg, 1.50 mmol, 3.00 equiv), dichloromethane (16 mL), tetrahydrofuran (4 mL). The mixture was stirred for 10 min at room temperature and this was followed by the addition of oxolane-2,5-dione (250.3 mg, 2.50 mmol, 5.00 equiv). The resulting mixture was allowed to react, with stirring, for an additional 16 h while the temperature was maintained at 35° C. in an oil bath. The resulting mixture was diluted with dichloromethane (300 mL) and washed with $NH_4Cl$ sat.aq (200 ml×2). The organic was dried over anhydrous sodium sulfate and concentrated under vacuum. The resulting mixture was concentrated under vacuum. This resulted in 620 mg (99.00%) of 4-[[(3R,5S)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-5-([[4-(4-methyl-1,3-thiazol-5-yl)phenyl]methyl]carbamoyl)pyrrolidin-3-yl]oxy]-4-oxobutanoic acid as a dark yellow solid. LC/MS (ESI) m/z: 1252.20 $[M+1]^+$.

Step 3: Preparation of 2,5,8,11,14,17,20,23,26,29,32,35,38,41,44,47,50,53,56,59,62,65-docosaoxaheptahexacontan-67-yl 4-methylbenzenesulfonate

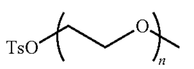

n~22

Into a 250-mL round-bottom flask, was placed 2,5,8,11,14,17,20,23,26,29,32,35,38,41,44,47,50,53,56,59,62,65-docosaoxaheptahexacontan-67-ol (5 g, 4.99 mmol, 1 equiv), Et3N (1.39 mL, 10.00 mmol, 2.00 equiv), DMAP (61 mg, 0.50 mmol, 0.10 equiv), DCM (50 mL), TsCl (1.91 g, 10.02 mmol, 2.01 equiv). The resulting solution was stirred for 4 h at 35° C. in an oil bath. The resulting mixture was concentrated under vacuum. The residue was applied onto a silica gel column with dichloromethane/methanol (23:2). This resulted in 5.73 g (99.31%) of 2,5,8,11,14,17,20,23,26,29,32,35,38,41,44,47,50,53,56,59,62,65-docosaoxaheptahexacontan-67-yl 4-methylbenzene-1-sulfonate as a white semi-solid. LC/MS (ESI) m/z: 578.30 $[M/2+1]^+$.

Step 4: Preparation of A-methyl-2,5,8,11,14,17,20,23,26,29,32,35,38,41,44,47,50,53,56,59,62,65-docosaoxaheptahexacontan-67-amine

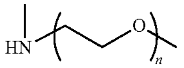

n~22

Into a 30-mL sealed tube purged and maintained with an inert atmosphere of nitrogen, was placed 2,5,8,11,14,17,20,23,26,29,32,35,38,41,44,47,50,53,56,59,62,65-docosaoxaheptahexacontan-67-yl 4-methylbenzene-1-sulfonate (1.155 g, 1.00 mmol, 1 equiv), methanamine hydrochloride (337.5 mg, 5.00 mmol, 5.00 equiv), $K_2CO_3$ (552.8 mg, 4.00 mmol, 4.00 equiv), dioxane (20 mL). The resulting mixture was stirred for 16 h at 70° C. in an oil bath. The reaction mixture was cooled to room temperature and combined. The mixture was diluted with water (200 mL). The resulting solution was extracted with dichloromethane (200 mL×2) and the organic layers combined, dried over anhydrous sodium sulfate and concentrated under vacuum. This resulted in 2.02 g (99.61%) of 2,5,8,11,14,17,20,23,26,29,32,35,38,41,44,47,50,53,56,59,62,65-docosaoxa-68-azanonahexacontane as a light yellow semi-solid. LC/MS (ESI) m/z: 507.70 $[M/2+1]^+$.

Step 5: Preparation of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 68-methyl-69-oxo-2,5,8,11,14,17,20,23,26,29,32,35,38,41,44,47,50,53,56,59,62,65-docosaoxa-68-azadoheptacontan-72-oate

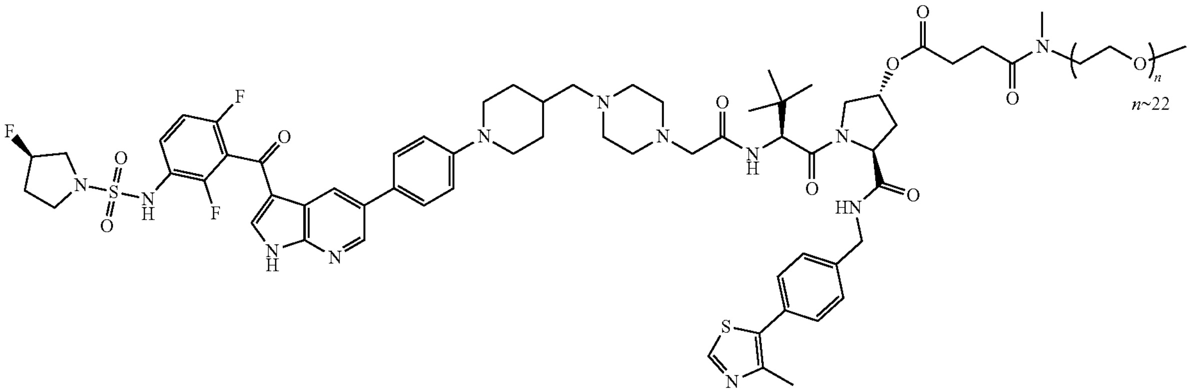

n~22

Into a 100-mL round-bottom flask, was placed 4-[[(3R,5S)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-5-([[4-(4-methyl-1,3-thiazol-5-yl)phenyl]methyl]carbamoyl)pyrrolidin-3-yl]oxy]-4-oxobutanoic acid (300 mg, 0.24 mmol, 1 equiv), 2,5,8,11,14,17,20,23,26,29,32,35,38,41,44,47,50,53,56,59,62,65-docosaoxa-68-azanonahexacontane (971.8 mg, 0.96 mmol, 4.00 equiv), DIEA (123.8 mg, 0.96 mmol, 4.00 equiv), BOP (211.8 mg, 0.48 mmol, 2.00 equiv), DMF (8 mL). The resulting solution was stirred for 2 h at room temperature. The resulting solution was diluted with water (400 mL) and extracted with EtOAc/THF (10/1, 400 mL×3) and the organic layers combined. The organic was washed with brine (400 mL×2), dried over anhydrous sodium sulfate and concentrated under vacuum. The crude product was purified by Prep-HPLC. This resulted in 87.7 mg (16.28%) of (3R,5S)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-5-([[4-(4-methyl-1,3-thiazol-5-yl)phenyl]methyl]carbamoyl)pyrrolidin-3-yl 3-[(2,5,8,11,14,17,20,23,26,29,32,35,38,41,44,47,50,53,56,59,62,65-docosaoxaheptahexacontan-67-yl)(methyl)carbamoyl]propanoate as a yellow semi-solid. LC/MS (ESI) m/z: 2248.5 $[M+1]^+$; $^1$H-NMR (400 MHz, $D_2O$) δ 9.69 (s, 1H), 8.44-8.36 (m, 2H), 7.79 (s, 1H), 7.59-7.55 (m, 5H), 7.42-7.37 (m, 4H), 7.05-7.00 (m, 1H), 5.34 (s, 1H), 5.20 (d, J=52.4 Hz, 1H), 4.55-4.51 (m, 1H), 4.41-4.38 (m, 3H), 4.11-4.03 (m, 3H), 3.90-3.88 (m, 1H), 3.37-3.46 (m, 102H), 3.40-3.27 (m, 6H), 3.01-2.99 (m, 2H), 2.84-2.57 (m, 6H), 2.47-2.41 (m, 6H), 2.22-2.06 (m, 5H), 1.98-1.83 (m, 3H), 0.92 (s, 9H).

Exemplary Synthesis of (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate (Exemplary Compound 827)

Step 1: Preparation of benzyl (2S,4R)-1-[(2S)-2-[[(tert-butoxy)carbonyl]amino]-3,3-dimethylbutanoyl]-4-hydroxypyrrolidine-2-carboxylate

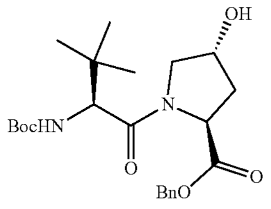 [SMILES: CC(C)(C)OC(=O)N[C@H](C(=O)N1C[C@H](O)C[C@H]1C(=O)OCc1ccccc1)C(C)(C)C]

Into a 250-mL round-bottom flask, was placed a solution of (2S)-2-{[(tert-butoxy)carbonyl]amino}-3,3-dimethylbutanoic acid (8.5 g, 36.75 mmol, 1.00 equiv) in N,N-dimethylformamide (100 mL). This was followed by the addition of HATU (15.5 g, 40.76 mmol, 1.10 equiv) in several portions at 0° C. Then DIEA (14.24 g, 110.40 mmol, 3.00 equiv) was added. The resulting mixture was stirred for 20 min at 0° C., and then was added by a solution of benzyl (2S,4R)-4-hydroxypyrrolidine-2-carboxylate hydrochloride (9.5 g, 36.86 mmol, 1.00 equiv) in N,N-dimethylformamide (20 mL) drop wise at 0° C. The reaction mixture was stirred for 1 h at room temperature, and then was quenched by the addition of water (500 mL). The resulting mixture was extracted with ethyl acetate (100 mL×3). The organic layers were combined, washed with water (100 mL×2) and brine (100 mL), dried over anhydrous sodium sulfate and concentrated under vacuum. The residue was applied onto a silica gel column eluting with ethyl acetate/petroleum ether (1:2). This resulted in 11.6 g (72%) of benzyl (2S,4R)-1-[(2S)-2-[[(tert-butoxy)carbonyl]amino]-3,3-dimethylbutanoyl]-4-hydroxypyrrolidine-2-carboxylate as a light yellow solid. LC/MS (ESI) m/z: 435.15 $[M+1]^+$.

Step 2: Preparation of benzyl (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylate

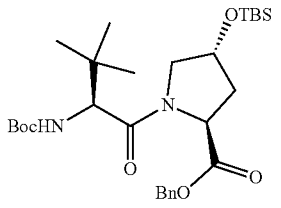 [SMILES: CC(C)(C)OC(=O)N[C@H](C(=O)N1C[C@H](O[Si](C)(C)C(C)(C)C)C[C@H]1C(=O)OCc1ccccc1)C(C)(C)C]

Into a 150-mL round-bottom flask, was placed benzyl (2S,4R)-1-[(2S)-2-[[(tert-butoxy)carbonyl]amino]-3,3-dimethylbutanoyl]-4-hydroxypyrrolidine-2-carboxylate (7 g, 16.11 mmol, 1.00 equiv), imidazole (1.6 g, 23.51 mmol, 1.46 equiv) in dichloromethane (80 mL) at 0° C. This was followed by the addition of TBDMSCl (3.6 g, 23.89 mmol, 1.48 equiv) in portions at 0° C. The resulting solution was stirred for 6 h at room temperature. The reaction was then quenched by the addition of water (60 mL). The resulting mixture was extracted with dichloromethane (50 mL×3), and the organic layers were combined, washed with brine (100 mL×2), dried over anhydrous sodium sulfate and concentrated under vacuum. The residue was applied onto a silica gel column eluting with ethyl acetate/petroleum ether (1:9). This resulted in 5.8 g (66%) of benzyl (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylate as light yellow oil. LC/MS (ESI) m/z: 549.20 $[M+1]^+$.

Step 3: Preparation of (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylic acid

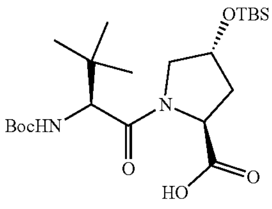 [SMILES: CC(C)(C)OC(=O)N[C@H](C(=O)N1C[C@H](O[Si](C)(C)C(C)(C)C)C[C@H]1C(=O)O)C(C)(C)C]

In a 50 ml round bottom flask, to a solution of benzyl (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylate (500 mg, 0.91 mmol, 1.00 equiv) in methanol (15 mL) was added Pd/C (10%, 100 mg) under nitrogen atmosphere. The flask was then vacuumed and flushed with hydrogen. The reaction mixture was hydrogenated at room temperature for 16 h under hydrogen atmosphere using a hydrogen balloon, then filtered through a Celite pad and concentrated under reduced pressure. This resulted in 273 mg (65%) of (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylic acid as colorless oil. LC/MS (ESI) m/z: 459.30 $[M+1]^+$.

Step 4: Preparation of tert-butyl N-[(2S)-1-[(2S,4R)-4-[(tert-butyldimethylsilyl)oxy]-2-[[(1R)-2-hydroxy-1-[4-(4-methyl-1,3-thiazol-5-yl)phenyl]ethyl]carbamoyl]pyrrolidin-1-yl]-3,3-dimethyl-1-oxobutan-2-yl]carbamate

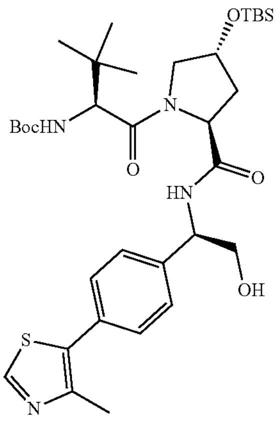 [SMILES: Cc1ncsc1-c1ccc([C@H](CO)NC(=O)[C@@H]2C[C@@H](O[Si](C)(C)C(C)(C)C)CN2C(=O)[C@@H](NC(=O)OC(C)(C)C)C(C)(C)C)cc1]

Into a 25-mL round-bottom flask, was placed (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylic acid (930 mg, 1 equiv), (2R)-2-amino-2-[4-(4-methyl-1,3-thiazol-5-yl)phenyl]ethan-1-ol hydrochloride (550 mg), HATU (930 mg), DIEA (1 g) in DMF (5 mL). The resulting solution was stirred for 1 h at room temperature. The reaction mixture was diluted with water (80 mL) and extracted with ethyl acetate (50 mL×3). The combined organic layer was dried over anhydrous sodium sulfate and concentrated. The residue was applied onto a silica gel column eluting with ethyl acetate/petroleum ether (1:0). This resulted in 460 mg of tert-butyl N-[(2S)-1-[(2S,4R)-4-[(tert-butyldimethylsilyl)oxy]-2-[[(1R)-2-hydroxy-1-[4-(4-methyl-1,3-thiazol-5-yl)phenyl]ethyl]carbamoyl]pyrrolidin-1-yl]-3,3-dimethyl-1-oxobutan-2-yl]carbamate as light yellow oil. LC/MS (ESI) m/z: 675.20 $[M+1]^+$.

Step 5: Preparation of 4-[(2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethoxy]-4-oxobutanoic acid

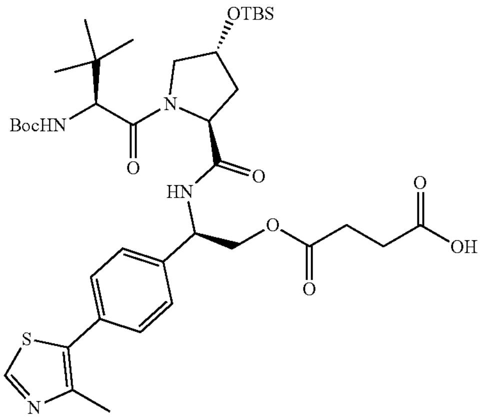 [SMILES: Cc1ncsc1-c1ccc([C@H](COC(=O)CCC(=O)O)NC(=O)[C@@H]2C[C@@H](O[Si](C)(C)C(C)(C)C)CN2C(=O)[C@@H](NC(=O)OC(C)(C)C)C(C)(C)C)cc1]

Into a 50-mL round-bottom flask, was placed tert-butyl N-[(2S)-1-[(2S,4R)-4-[(tert-butyldimethylsilyl)oxy]-2-[[(1R)-2-hydroxy-1-[4-(4-methyl-1,3-thiazol-5-yl)phenyl]ethyl]carbamoyl]pyrrolidin-1-yl]-3,3-dimethyl-1-oxobutan-2-yl]carbamate (840 mg, 1.24 mmol, 1 equiv), oxolane-2,5-dione (623 mg, 6.23 mmol, 5.00 equiv), triethylamine (380 mg, 3.76 mmol, 3.02 equiv) in dichloromethane (20 mL). This was followed by the addition of DMAP (460 mg, 3.77 mmol, 3.03 equiv) in portions at room temperature. The resulting solution was stirred for 16 h at room temperature. The mixture was diluted with water (30 mL) and extracted with dichloromethane (25 mL×3). The combined organic layer was washed with brine (40 mL), dried over anhydrous sodium sulfate and concentrated. The residue was applied onto a silica gel column with dichloromethane/methanol (10:1). This resulted in 800 mg (82.94%) of 4-[(2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethoxy]-4-oxobutanoic acid as light yellow oil. LC/MS (ESI) m/z: 775.25 $[M+1]^+$.

Step 6: Preparation of (2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)carbamoyl]propanoate

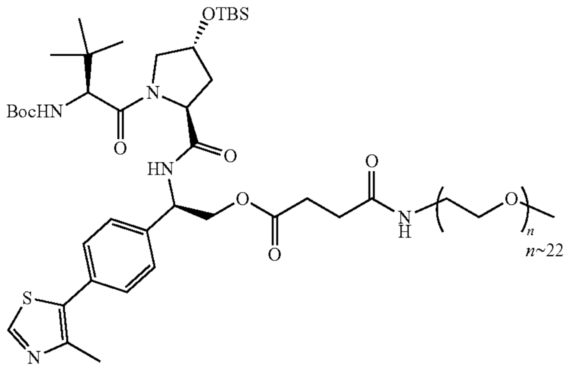

Into a 50-mL round-bottom flask, was placed 4-[(2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethoxy]-4-oxobutanoic acid (800 mg, 1.03 mmol, 1 equiv), 2,5,8,11,14,17,20,23,26,29,32,35,38,41,44,47,50,53,56,59,62,65-docosaoxaheptahexacontan-67-amine hydrochloride (2.1 g, 2.03 mmol, 1.96 equiv), DIEA (540 mg, 4.18 mmol, 4.05 equiv) in DMF (10 mL). This was followed by the addition of BOP (900 mg, 2.03 mmol, 1.97 equiv) at room temperature. The resulting solution was stirred for 2 h at room temperature. The mixture was diluted with water (30 mL) and extracted with ethyl acetate (30 mL×3). The combined organic layer was washed with brine (50 mL), dried over anhydrous sodium sulfate and concentrated. The residue was applied onto a silica gel column with dichloromethane/methanol (10:1). This resulted in 1.8 g (99.24%) of (2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)carbamoyl]propanoate as yellow oil.

Step 7: Preparation of (2R)-2-[[(2S,4R)-1-[(2S)-2-amino-3,3-dimethylbutanoyl]-4-hydroxypyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)carbamoyl]propanoate hydrochloride

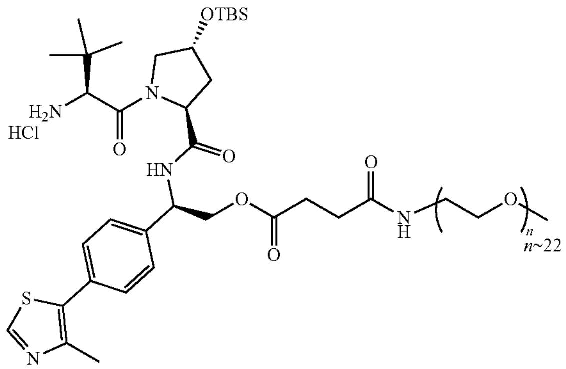

Into a 100-mL round-bottom flask, was placed (2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)carbamoyl]propanoate (1.8 g, 1.02 mmol, 1 equiv) in dioxane (20 mL). To the above was added HCl/dioxane (20 mL, 4 mol/L). The resulting solution was stirred for 1 h at room temperature under the atmosphere of hydrochloric acid gas. The mixture was concentrated. This resulted in 1.6 g (98.90%) of (2R)-2-[[(2S,4R)-1-[(2S)-2-amino-3,3-dimethylbutanoyl]-4-hydroxypyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)carbamoyl]propanoate hydrochloride as yellow oil. LC/MS (ESI) m/z: 772.30 $[M/2+1]^+$.

Step 8: Preparation of (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate

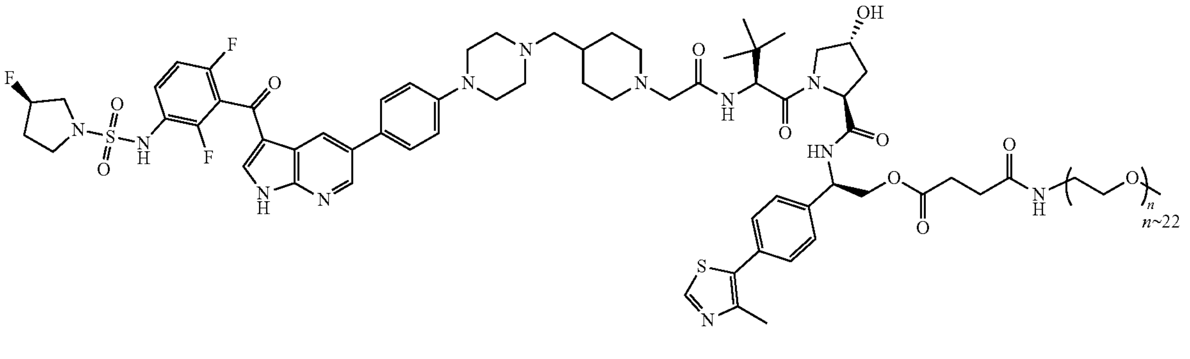

Into a 25-mL round-bottom flask, was placed 2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (280 mg, 0.378 mmol, 1 equiv), (2R)-2-[[(2S,4R)-1-[(2S)-2-amino-3,3-dimethylbutanoyl]-4-hydroxypyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)carbamoyl]propanoate hydrochloride (600 mg, 0.380 mmol, 1.00 equiv), DIEA (200 mg, 1.547 mmol, 4.09 equiv) in DMF (6 mL). This was followed by the addition of BOP (330 mg, 0.746 mmol, 1.97 equiv) at room temperature. The resulting solution was stirred for 2 h at room temperature and then was concentrated. The crude product was purified by Prep-HPLC resulting in 114.6 mg (13.37%) of (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 69-oxo-2,5,8,11,14,17,20,23,26,29,32,35,38,41,44,47,50,53,56,59,62,65-docosaoxa-68-azadoheptacontan-72-oate as a yellow oil. LC/MS (ESI) m/z: 2264.7 $[M+1]^+$; $^1$H-NMR (300 MHz, $CD_3OD$) δ 8.89 (s, 1H), 8.69 (s, 1H), 8.60 (s, 1H), 7.89 (s, 1H), 7.76-7.74 (m, 1H), 7.62 (d, J=9 Hz, 2H), 7.48-7.45 (m, 4H), 7.14-7.11 (m, 3H), 5.32-5.14 (m, 2H), 4.64-4.63 (m, 2H), 4.46-4.44 (m, 2H), 4.37-4.32 (m, 1H), 3.88-3.84 (m, 3H), 3.68-3.51 (m, 109H), 3.47-3.36 (m, 5H), 3.14 (s, 2H), 3.01-2.97 (m, 2H), 2.75-2.66 (m, 7H), 2.54-2.42 (m, 7H), 2.37-2.10 (m, 5H), 1.96-1.85 (m, 4H), 1.75-1.70 (m, 1H), 1.46-1.33 (m, 2H), 1.06-1.04 (m, 9H).

Exemplary Synthesis of (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 68-methyl-69-oxo-2,5,8,11,14,17,20,23,26,29,32,35,38,41,44,47,50,53,56,59,62,65-docosaoxa-68-azadoheptacontan-72-oate (Exemplary Compound 842)

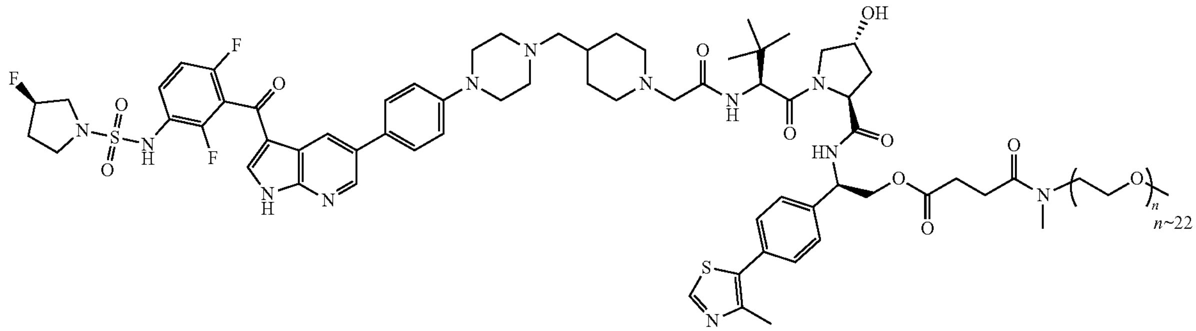

n~22

Step 1: Preparation of (2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59, 62,65-docosaoxaheptahexacontan-67-yl)(methyl)carbamoyl]propanoate

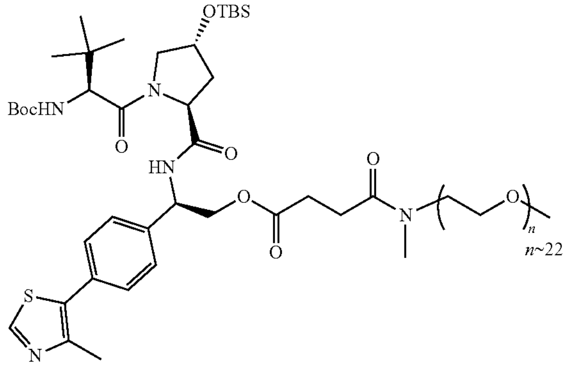

Into a 100-mL round-bottom flask, was placed a solution of 4-[(2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethoxy]-4-oxobutanoic acid (1.11 g, 1.432 mmol, 1.00 equiv), 2,5,8,11,14,17,20,23,26,29,32,35,38,41,44,47,50,53,56,59,62,65-docosaoxa-68-azanonahexacontane (1.45 g, 1.430 mmol, 1 equiv), DIEA (0.37 g, 2.863 mmol, 2.00 equiv), BOP (0.76 g, 1.718 mmol, 1.20 equiv) in DMF (50 mL). The resulting mixture was stirred for 1 hour at room temperature. Then the mixture was diluted with 50 mL of water and extracted with dichloromethane (100 mL×2). The organic layers were combined and concentrated under reduced pressure. The residue was applied onto a silica gel column eluting with dichloromethane/methanol (10:1). This resulted in 1.56 g (61.60%) of (2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59, 62,65-docosaoxaheptahexacontan-67-yl)(methyl)carbamoyl]propanoate as white solid.

Step 2: Preparation of (2R)-2-[[(2S,4R)-1-[(2S)-2-amino-3,3-dimethylbutanoyl]-4-hydroxypyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)(methyl)carbamoyl]propanoate hydrochloride

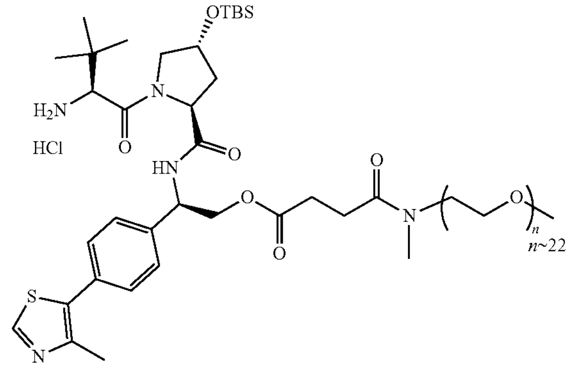

Into a 100-mL round-bottom flask, was placed a solution of (2R)-2-[[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)(methyl)carbamoyl]propanoate (1.0 g, 0.565 mmol, 1 equiv) in 50 mL dioxane. This was followed by the addition of hydrogen chloride in 1,4-dioxane solution (4.0 M, 10 mL). The resulting mixture was stirred for 1 hour at room temperature and then concentrated under reduced pressure. This resulted in 850.0 mg (94.49%) of (2R)-2-[[(2S,4R)-1-[(2S)-2-amino-3,3-dimethylbutanoyl]-4-hydroxypyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)(methyl)carbamoyl]propanoate hydrochloride as colorless oil.

Step 3: Preparation of (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 68-methyl-69-oxo-2,5,8,11,14,17,20,23,26,29,32,35,38,41,44,47,50,53,56,59,62,65-docosaoxa-68-azadoheptacontan-72-oate

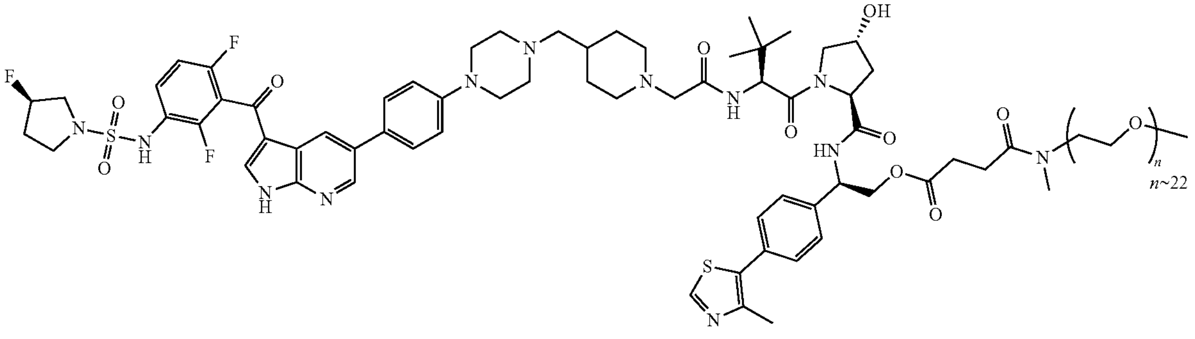

Into a 100-mL round-bottom flask, was placed a solution of 2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (417.9 mg, 0.565 mmol, 1.00 equiv), (2R)-2-[[(2S,4R)-1-[(2S)-2-amino-3,3-dimethylbutanoyl]-4-hydroxypyrrolidin-2-yl]formamido]-2-[4-(4-methyl-1,3-thiazol-5-yl)phenyl]ethyl 3-[(2,5,8,11,14,17,20,23,26,29,32,35,38,41,44,47,50,53,56,59,62,65-docosaoxaheptahexacontan-67-yl)(methyl)carbamoyl]propanoate hydrochloride (900.0 mg, 0.565 mmol, 1 equiv), DIEA (146.0 mg, 1.130 mmol, 2.00 equiv), BOP (299.8 mg, 0.678 mmol, 1.20 equiv) in DMF (30 mL). The resulting mixture was stirred for 1 hour at room temperature. Then the mixture was diluted with 50 mL of water and extracted with dichloromethane (100 mL×2). The organic layers was combined and concentrated under reduced pressure. The crude product was purified by Prep-HPLC with the following conditions: Column: X select CSH OBD Column 30*150 mm 5 um n; Mobile Phase A: Water (0.1% FA), Mobile Phase B: ACN; Flow rate: 60 mL/min; Gradient: 15% B to 38% B in 11 min; 254/220 nm; Rt: 10.27 min. This resulted in 200.3 mg (7.23%) of (R)-2-((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)-2-(4-(4-methylthiazol-5-yl)phenyl)ethyl 68-methyl-69-oxo-2,5,8,11,14,17,20,23,26,29,32,35,38,41,44,47,50,53,56,59,62,65-docosaoxa-68-azadoheptacontan-72-oate as a solid. LC/MS (ESI) m/z: 2278.71 $[M+1]^+$; $^1$H-NMR (400 MHz, DMSO-$d_6$) δ 12.91 (s, 1H), 9.85 (brs, 1H), 8.99 (s, 1H), 8.65 (d, J=2.2 Hz, 1H), 6.60-8.53 (m, 2H), 8.07 (s, 1H), 7.88-7.80 (m, 1H), 7.69-7.54 (m, 3H), 7.52-7.45 (m, 4H), 7.31-7.25 (m, 1H), 7.07 (d, J=8.4 Hz, 2H), 5.36-5.23 (m, 1H), 5.21-5.13 (m, 2H), 4.55-4.43 (m, 2H), 4.29-4.22 (m, 3H), 3.72-3.38 (m, 105H), 3.26-3.15 (m, 7H), 3.02-2.95 (m, 2H), 2.85-2.76 (m, 2H), 2.48-2.39 (m, 4H), 2.34-1.91 (m, 6H), 1.77-1.60 (m, 4H), 1.31-1.19 (m, 2H), 0.95 (s, 9H).

Exemplary Synthesis of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 2-((69-oxo-2,5,8,11,14,17,20,23,26,29,32,35,38,41,44,47,50,53,56,59,62,65,68-tricosaoxaheptacontan-70-yl)oxy)acetate (Exemplary Compound 815)

Step 1: Preparation of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide (Exemplary Compound 227)

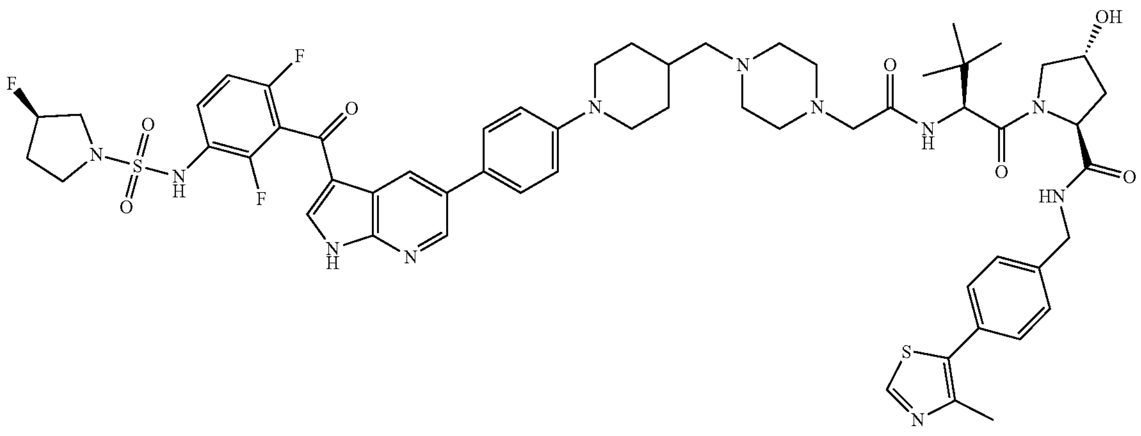 [SMILES: Cc1ncsc1-c1ccc(CNC(=O)[C@@H]2C[C@@H](O)CN2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 8-mL tube, was placed 2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetic acid (111 mg, 0.15 mmol, 1 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (84 mg, 0.18 mmol, 1.20 equiv), DIEA (77.5 mg, 0.60 mmol, 4.00 equiv), DMF (2 mL), BOP (79.6 mg, 0.18 mmol, 1.20 equiv). The resulting solution was stirred for 1 h at room temperature. The resulting solution was diluted with water (30 mL) and extracted with dichloromethane/methanol (10/1, 50 mL×2) and the organic layers combined. The organic was washed with brine (50 mL×2), dried over anhydrous sodium sulfate and concentrated under vacuum. The crude product was purified by Prep-HPLC resulting in 81.9 mg (47.37%) of (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide. LC/MS (ESI) m/z: 1152.20 $[M+1]^+$; $^1$H-NMR (300 MHz, $CD_3OD$) δ 8.87 (s, 1H), 8.67 (s, 1H), 8.58 (s, 1H), 7.88 (s, 1H), 7.78-7.70 (m, 1H), 7.56 (d, J=8.7 Hz, 2H), 7.48-7.38 (m, 4H), 7.16-7.06 (m, 3H), 5.21 (d, J=53.7 Hz, 1H), 4.63-4.50 (m, 4H), 4.37-4.32 (m, 1H), 3.91-3.70 (m, 4H), 4.63-3.35 (m, 4H), 3.05 (s, 2H), 2.72-2.46 (m, 13H), 2.27-1.95 (m, 6H), 1.84-1.80 (m, 2H), 1.65 (m, 1H), 1.35-1.24 (m, 2H), 1.04 (m, 9H).

Step 2: Preparation 69-oxo-2,5,8,11,14,17,20,23,26,29,32,35,38,41,44,47,50,53,56,59,62,65,68,71-tetracosaoxatriheptacontan-73-oic acid

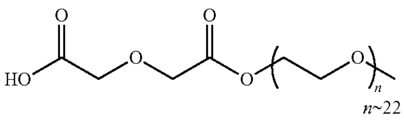

Into a 1-L round-bottom flask, was placed 2,5,8,11,14,17,20,23,26,29,32,35,38,41,44,47,50,53,56,59,62,65-docosaoxaheptahexacontan-67-ol (8 g, 7.99 mmol, 1 equiv), TEA (2.22 mL, 15.97 mmol, 2.00 equiv), DMAP (2.93 g, 23.98 mmol, 3.00 equiv), dichloromethane (250 mL), tetrahydrofuran (30 mL) and the mixture was stirred for 10 min. This was followed by the addition of 1,4-dioxane-2,6-dione (4.64 g, 39.98 mmol, 5.00 equiv) with stirring. The resulting solution was stirred for 16 h at 35° C. in an oil bath. The resulting solution was diluted with dichloromethane (800 mL) and washed with NH4Cl (800 mL×2). The organic was dried over anhydrous sodium sulfate and concentrated under vacuum. This resulted in 8.90 g (99.69%) of 69-oxo-2,5,8,11,14,17,20,23,26,29,32,35,38,41,44,47,50,53,56,59,62,65,68,71-tetracosaoxatriheptacontan-73-oic acid as a yellow semi-solid. LC/MS (ESI) m/z: 559.30 $[M/2+1]^+$.

Step 3: Preparation of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-5-((4-(4-methylthiazol-5-yl)benzyl)carbamoyl)pyrrolidin-3-yl 2-((69-oxo-2,5,8,11,14,17,20,23,26,29,32,35,38,41,44,47,50,53,56,59,62,65,68-tricosaoxaheptacontan-70-yl)oxy)acetate

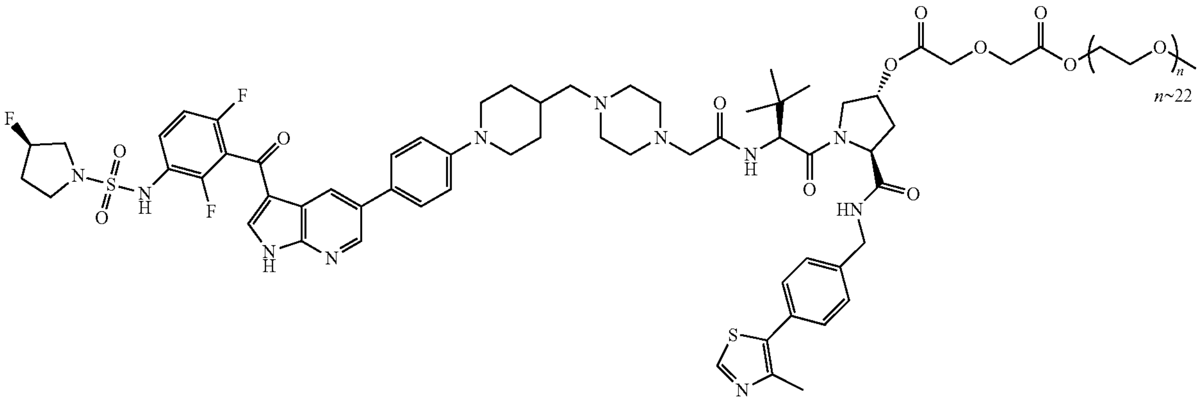

Into a 100-mL round-bottom flask, was placed (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) acetamido)-3,3-dimethylbutanoyl)-4-hydroxy-N-(4-(4-methylthiazol-5-yl)benzyl)pyrrolidine-2-carboxamide (300 mg, 0.26 mmol, 1 equiv), dichloromethane (20 mL). To the mixture was added 69-oxo-2,5,8,11,14,17,20,23,26,29,32,35,38,41,44,47,50,53,56,59,62,65,68,71-tetracosaoxatriheptacontan-73-oic acid (1.31 g, 1.17 mmol, 4.50 equiv), DMAP (285.9 mg, 2.34 mmol, 9.00 equiv) and EDCI (449 mg, 2.34 mmol, 9.00 equiv) in 3 portions in 3 h. The resulting solution was stirred for 16 h at room temperature. This was followed by addition of the rest of DMAP (636.6 mg, 5.21 mmol, 20.01 equiv) in 4 portions in 4 h. The resulting solution was allowed to react, with stirring, for an additional 2 h at room temperature. The resulting solution was concentrated and the residue was diluted with NH4Cl (300 mL). The mixture was extracted with EtOAc/THF (10/1, 300 mL×2) and the organic layers combined. The organic was washed with NH4Cl (300 mL×2), dried over anhydrous sodium sulfate and concentrated under vacuum. The crude product was purified by Prep-HPLC resulting in 125.8 mg (21.46%) of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl) methyl)piperazin-1-yl)acetamido)-3,3-dimethylbutanoyl)-5-((4-(4-methylthiazol-5-yl)benzyl)carbamoyl)pyrrolidin-3-yl 2-((69-oxo-2,5,8,11,14,17,20,23,26,29,32,35,38,41,44,47,50,53,56,59,62,65,68-tricosaoxaheptacontan-70-yl)oxy) acetate dark yellow semi-solid. LC/MS (ESI) m/z: 2251.46 $[M+1]^+$; $^1$H-NMR (300 MHz, $CDCl_3$) δ 11.49 (s, 1H), 8.84 (s, 1H), 8.69 (s, 1H), 8.60 (s, 1H), 7.74-7.66 (m, 3H), 7.56 (d, J=8.4 Hz, 2H), 7.45-7.41 (m, 1H), 7.37-7.30 (m, 4H), 7.04-6.99 (m, 3H), 5.43 (s, 1H), 5.21 (d, J=52.5 Hz, 1H), 4.76-4.71 (m, 1H), 4.59-4.52 (m, 1H), 4.35-4.18 (m, 9H), 3.86-3.68 (m, 7H), 3.64-3.62 (m, 78H), 3.55-3.44 (m, 7H), 3.37 (s, 3H), 2.96 (s, 2H), 2.81-2.68 (m, 4H), 2.51-2.43 (m, 11H), 2.26-2.19 (m, 5H), 2.02-1.95 (m, 1H), 1.86-1.82 (m, 2H), 1.61 (m, 1H), 1.35-1.30 (m, 2H), 0.93 (s, 9H).

Exemplary Synthesis of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) acetamido)-3,3-dimethylbutanoyl)-5-((4-(4-methylthiazol-5-yl)benzyl)carbamoyl)pyrrolidin-3-yl 69-oxo-2,5,8,11,14,17,20,23,26,29,32,35,38,41,44,47,50,53,56,59,62,65,71-tricosaoxa-68-azatriheptacontan-73-oate (Exemplary Compound 814)

Step 1: Preparation of 2-(2-[[(3R,5S)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-5-([[4-(4-methyl-1,3-thiazol-5-yl)phenyl]methyl]carbamoyl)pyrrolidin-3-yl]oxy]-2-oxoethoxy)acetic acid

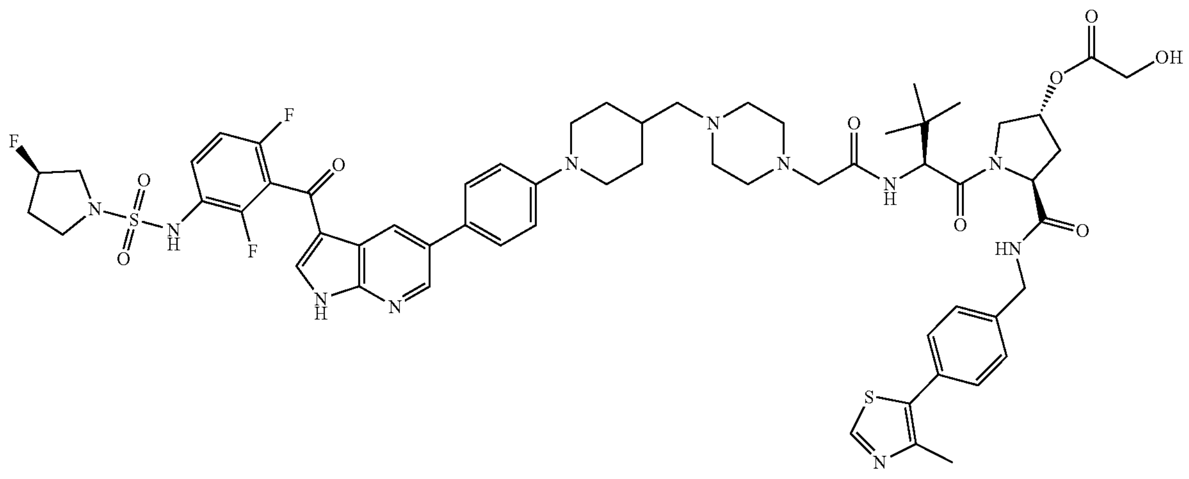 [SMILES: Cc1ncsc1-c1ccc(CNC(=O)[C@@H]2C[C@@H](OC(=O)CO)CN2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Into a 30-mL sealed tube, was placed (2S,4R)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl]piperazin-1-yl)acetamido]-3,3-dimethylbutanoyl]-4-hydroxy-N-[[4-(4-methyl-1,3-thiazol-5-yl)phenyl]methyl]pyrrolidine-2-carboxamide (230 mg, 0.20 mmol, 1 equiv), Et3N (40.4 mg, 0.40 mmol, 2.00 equiv), DMAP (73 mg, 0.60 mmol, 2.99 equiv), dichloromethane (8 mL), tetrahydrofuran (2 mL) and the mixture was stirred for 10 min. This was followed by the addition of 1,4-dioxane-2,6-dione (116.1 mg, 1.00 mmol, 5.01 equiv) with stirring. The resulting solution was stirred for 16 h at 35° C. in an oil bath. The resulting solution was diluted with dichloromethane/methanol (10/1, 200 mL) and washed with NH4Cl sat.aq (100 mL×2). The organic was dried over anhydrous sodium sulfate and concentrated under vacuum. The resulting mixture was concentrated under vacuum. The crude product was purified by Prep-HPLC resulting in 79.6 mg (31.44%) of 2-(2-[[(3R,5S)-1-[(2S)-2-[2-(4-[[1-(4-[3-[2,6-difluoro-3-([[(3R)-3-fluoropyrrolidin-1-yl]sulfonyl] amino)benzoyl]-1H-pyrrolo[2,3-b]pyridin-5-yl]phenyl)piperidin-4-yl]methyl]piperazin-1-yl)acetamido]-3,3-dimethylbutanoyl]-5-([[4-(4-methyl-1,3-thiazol-5-yl) phenyl]methyl]carbamoyl)pyrrolidin-3-yl]oxy]-2-oxoethoxy)acetic acid as a light yellow solid. LC/MS (ESI) m/z: 1268.20 $[M+1]^+$; $^1$H-NMR (300 MHz, $CD_3OD$) δ 8.90

(s, 1H), 8.69 (s, 1H), 8.62 (m, 1H), 7.94 (s, 1H), 7.82-7.74 (m, 1H), 7.63-7.60 (m, 2H), 7.49-7.42 (m, 4H), 7.22-7.14 (m, 3H), 5.50 (s, 1H), 5.26 (m, 1H), 4.66-4.56 (m, 7H), 4.42-4.29 (m, 4H), 4.13-4.00 (m, 2H), 3.92-3.79 (m, 3H), 3.61-3.44 (m, 6H), 3.17 (m, 3H), 3.03 (s, 3H), 2.90-2.79 (m, 4H), 2.50 (s, 3H), 2.28-2.22 (m, 2H), 2.07-1.96 (m, 3H), 1.49-1.45 (m, 2H), 1.07 (s, 9H).

Step 2: Preparation of (3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) acetamido)-3,3-dimethylbutanoyl)-5-((4-(4-methylthiazol-5-yl)benzyl)carbamoyl)pyrrolidin-3-yl 69-oxo-2,5,8,11,14,17,20,23,26,29,32,35,38,41,44,47,50,53,56,59,62,65,71-tricosaoxa-68-azatriheptacontan-73-oate

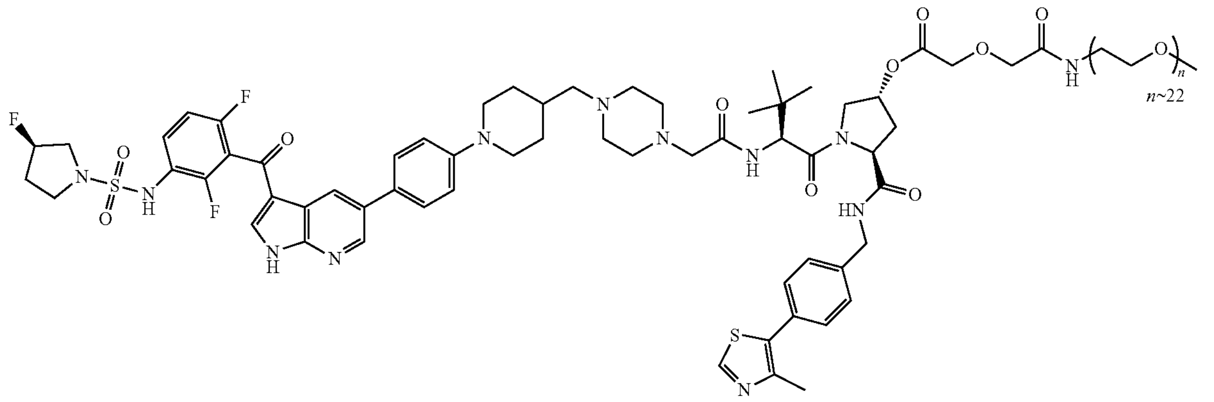

Into a 50-mL round-bottom flask, was placed 2-(2-[[(3R,5S)-1-[(2S)-2-[2-(4-[[1-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperidin-4-yl]methyl] piperazin-1-yl)acetamido]-3,3-dimethylbutanoyl]-5-([[4-(4-methyl-1,3-thiazol-5-yl)phenyl]methyl]carbamoyl) pyrrolidin-3-yl]oxy]-2-oxoethoxy)acetic acid (761 mg, 0.60 mmol, 1 equiv), 2,5,8,11,14,17,20,23,26,29,32,35,38,41,44,47,50,53,56,59,62,65-docosaoxaheptahexacontan-67-amine hydrochloride (1.244 g, 1.20 mmol, 2.00 equiv), DIEA (310 mg, 2.40 mmol, 4.00 equiv), DMF (15 mL), BOP (398 mg, 0.90 mmol, 1.50 equiv). The resulting solution was stirred for 2 h at room temperature. The resulting solution was diluted with water (200 mL) and extracted with ethyl acetate/THF (10/1, 300 mL×2) and the organic layers combined. The organic was washed with NH4Cl (300 mL×2). The organic was dried over anhydrous sodium sulfate and concentrated under vacuum. The crude product was purified by Prep-HPLC resulting in 238.0 mg (17.63%) of 3R,5S)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl) acetamido)-3,3-dimethylbutanoyl)-5-((4-(4-methylthiazol-5-yl)benzyl)carbamoyl)pyrrolidin-3-yl 69-oxo-2,5,8,11,14,17,20,23,26,29,32,35,38,41,44,47,50,53,56,59,62,65,71-tricosaoxa-68-azatriheptacontan-73-oate as a yellow solid. LC/MS (ESI) m/z: 2250.47 $[M+1]^+$; $^1$H-NMR (400 MHz, $CDCl_3$) δ 11.22 (s, 1H), 8.86 (s, 1H), 8.70 (s, 1H), 8.64 (s, 1H), 7.75-7.71 (m, 3H), 7.57 (d, J=8.0 Hz, 2H), 7.47 (m, 1H), 7.338-7.33 (m, 4H), 7.13 (m, 1H), 7.06-7.02 (m, 3H), 5.44 (s, 1H), 5.23 (d, J=54.2 Hz, 1H), 4.9-4.75 (m, 1H), 4.60-4.55 (m, 1H), 4.37-4.27 (m, 4H), 4.19-4.07 (m, 3H), 3.82-3.48 (m, 91H), 3.39 (s, 3H), 2.98 (m, 2H), 2.77-2.71 (m, 4H), 2.55-2.46 (m, 11H), 2.27-2.22 (m, 4H), 2.12-2.00 (m, 2H), 1.88-1.85 (m, 3H), 1.64 (m, 1H), 1.36-1.27 (m, 4H), 0.94 (s, 9H).

Exemplary Synthesis of 2-(((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl) acetamido)-3,3-dimethylbutanoyl)-4-hydroxypyrrolidine-2-carboxamido)methyl)-5-(4-methylthiazol-5-yl)benzyl 2,5,8,11,14,17,20,23,26,29,32,35,38,41,44,47,50,53,56,59,62,65,68-tricosaoxaheptacontan-70-oate (Exemplary Compound 813)

Step 1: Preparation of methyl 2-([bis[(tert-butoxy) carbonyl]amino]methyl)-5-bromobenzoate

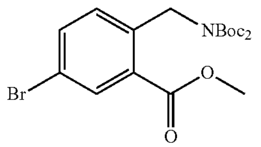

Into a 250 mL round-bottom flask were added methyl 5-bromo-2-(bromomethyl)benzoate (3.5 g, 11.36 mmol, 1 equiv), tert-butyl N-[(tert-butoxy)carbonyl]carbamate (2.65 g, 12.20 mmol, 1.07 equiv) and methyl ethyl ketone (120 mL) at room temperature. To a stirred mixture was added cesium carbonate (3.7 g, 11.36 mmol, 1.00 equiv) in portions at room temperature. The resulting mixture was stirred for 16 h at 70° C. The resulting mixture was filtered. The filtrate was concentrated under reduced pressure. The resulting mixture was diluted with water (200 mL). The aqueous layer was extracted with ethyl acetate (60 mL×3). The resulting mixture was concentrated under reduced pressure. The residue was purified by silica gel column chromatography, eluted with ethyl acetate/petroleum ether (1:10) to afford methyl 2-([bis[(tert-butoxy)carbonyl]amino]methyl)-5-bromobenzoate (4.25 g, 84.16%) as a yellow oil. LC/MS (ESI) m/z: 465.90 [M+23]$^+$.

Step 2: Preparation of methyl 2-([bis[(tert-butoxy)carbonyl]amino]methyl)-5-(4-methyl-1,3-thiazol-5-yl)benzoate

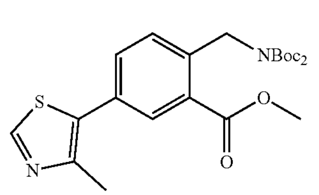

Into a 250 mL round-bottom flask were added methyl 2-([bis[(tert-butoxy)carbonyl]amino]methyl)-5-bromobenzoate (25 g, 56.27 mol, 1 equiv), 4-methyl-1,3-thiazole (12 g, 120 mmol), DMF (50 mL) and potassium acetate (25 g, 254.73 mmol, 4.53 equiv) at room temperature. To the mixture was added Pd(OAc)2 (2.5 g, 0.01 mmol) at room temperature under nitrogen atmosphere. The resulting mixture was stirred for 2 h at 100° C. under nitrogen atmosphere. The resulting mixture was diluted with water (50 mL). The aqueous layer was extracted with ethyl acetate (60 mL×4). The resulting solid was dried. The resulting mixture was concentrated under vacuum. The residue was purified by silica gel column chromatography, eluted with ethyl acetate/petroleum ether (3:1) to afford methyl 2-([bis[(tert-butoxy)carbonyl]amino]methyl)-5-(4-methyl-1,3-thiazol-5-yl)benzoate (15 g, 57.63%) as a yellow solid. LC/MS (ESI) m/z: 463.10 [M+1]$^+$.

Step 3: Preparation of tert-butyl N-[(tert-butoxy)carbonyl]-N-[[2-(hydroxymethyl)-4-(4-methyl-1,3-thiazol-5-yl)phenyl]methyl]carbamate

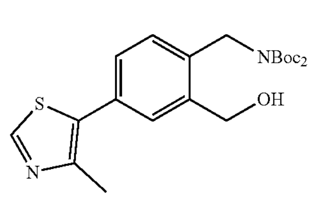

Into a 250 mL round-bottom flask were added methyl 2-([bis[(tert-butoxy)carbonyl]amino]methyl)-5-(4-methyl-1,3-thiazol-5-yl)benzoate (360 mg, 0.78 mmol, 1 equiv) and dichloromethane (20 mL, 314.60 mol, 404.23 equiv) at room temperature. To the above mixture was added DIBAl-H (3.3 mL, 19.68 mmol, 25.28 equiv) in portions over 10 min at −70° C. The resulting mixture was stirred for additional 1 h at −70° C. The reaction was quenched with ammonium chloride aqueous solution at room temperature. The resulting mixture was extracted with dichloromethane (20 mL×3). The combined organic layers were washed with brine (20 mL×1), dried over anhydrous sodium sulfate. After filtration, the filtrate was concentrated under reduced pressure. The residue was purified by silica gel column chromatography, eluted with ethyl acetate/petroleum ether (2:1) to afford tert-butyl N-[(tert-butoxy)carbonyl]-N-[[2-(hydroxy methyl)-4-(4-methyl-1,3-thiazol-5-yl)phenyl]methyl]carbamate (120 mg, 35.48%) as a yellow oil. LC/MS (ESI) m/z: 335.00 [M−100]$^+$.

Step 4: Preparation of [2-(aminomethyl)-5-(4-methyl-1,3-thiazol-5-yl)phenyl]methanol hydrochloride

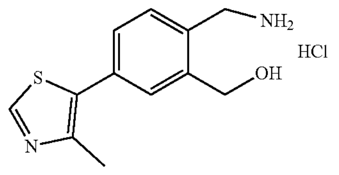 [SMILES: Cc1ncsc1-c1ccc(CN)c(CO)c1 ; Cl]

Into a 250 mL round-bottom flask were added tert-butyl N-[(tert-butoxy)carbonyl]-N-[[2-(hydroxymethyl)-4-(4-methyl-1,3-thiazol-5-yl)phenyl]methyl]carbamate (150 mg, 0.35 mmol, 1 equiv) and HCl (4 M) in dioxane (10.0 mL, 329.12 mmol, 953.46 equiv) at room temperature. The resulting mixture was stirred for 2 h at room temperature. The resulting mixture was concentrated under vacuum. This resulted in [2-(amino methyl)-5-(4-methyl-1,3-thiazol-5-yl)phenyl]methanol hydrochloride (132 mg, crude) as a brown solid. LC/MS (ESI) m/z: 234.95 [M+1]$^+$.

Step 5: Preparation of tert-butyl N-[(2S)-1-[(2S,4R)-4-[(tert-butyldimethylsilyl)oxy]-2-([[2-(hydroxymethyl)-4-(4-methyl-1,3-thiazol-5-yl)phenyl]methyl]carbamoyl)pyrrolidin-1-yl]-3,3-dimethyl-1-oxobutan-2-yl]carbamate

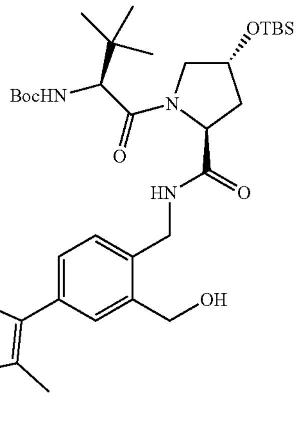

Into a 50 mL round-bottom flask were added (2S,4R)-1-[(2S)-2-[[(tert-butoxy)carbonyl]amino]-3,3-dimethylbutanoyl]-4-[(tert-butyldimethylsilyl)oxy]pyrrolidine-2-carboxylic acid (750 mg, 1.64 mmol, 1 equiv), DMF (10 mL, 0.14 mmol, 0.08 equiv), HATU (750 mg, 1.97 mmol, 1.21 equiv), DIEA (840 mg, 6.50 mmol, 3.97 equiv) and [2-(aminomethyl)-5-(4-methyl-1,3-thiazol-5-yl)phenyl]methanol hydrochloride (440 mg, 1.62 mmol, 0.99 equiv) at room temperature. The resulting mixture was stirred for 1 h at room temperature. The resulting mixture was diluted with water (60 mL). The resulting mixture was extracted with ethyl acetate (25 mL×3). The combined organic layers were washed with brine (15 mL), dried over anhydrous Na2SO4. After filtration, the filtrate was concentrated under reduced pressure. The residue was purified by silica gel column chromatography, eluted with ethyl acetate/petroleum ether (1:0) to afford 1.34 g (121.41%) of tert-butyl N-[(2S)-1-[(2S,4R)-4-[(tert-butyldimethylsilyl)oxy]-2-([[2-(hydroxymethyl)-4-(4-methyl-1,3-thiazol-5-yl)phenyl]methyl]carbamoyl)pyrrolidin-1-yl]-3,3-dimethyl-1-oxobutan-2-yl]carbamate as an orange oil. LC/MS (ESI) m/z: 675.15 $[M+1]^+$.

Step 6: Preparation of [2-([[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]methyl)-5-(4-methyl-1,3-thiazol-5-yl)phenyl]methyl 2,5,8,11,14,17,20,23,26,29,32,35,38,41,44,47,50,53,56,59,62,65,68-tricosaoxaheptacontan-70-oate

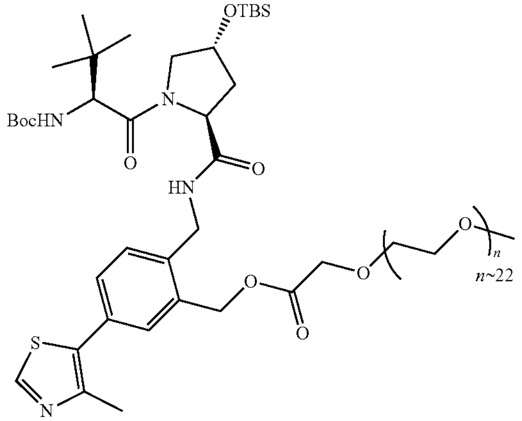

Into a 50-mL round-bottom flask, was placed tert-butyl N-[(2S)-1-[(2S,4R)-4-[(tert-butyldimethylsilyl)oxy]-2-([[2-(hydroxymethyl)-4-(4-methyl-1,3-thiazol-5-yl)phenyl]methyl]carbamoyl)pyrrolidin-1-yl]-3,3-dimethyl-1-oxobutan-2-yl]carbamate (570 mg, 0.84 mmol, 1 equiv), dichloromethane (20 mL). 2,5,8,11,14,17,20,23,26,29,32,35,38,41,44,47,50,53,56,59,62,65,68-tricosaoxaheptacontan-70-oic acid (1.34 g, 1.27 mmol, 1.50 equiv), DMAP (309.6 mg, 2.53 mmol, 3.00 equiv) and EDCI (485.6 mg, 2.53 mmol, 3.00 equiv) were added. The resulting solution was stirred for 2 h at room temperature. The resulting solution was concentrated and the residue was diluted with NH4Cl (400 mL). The mixture was extracted with ethyl acetate/THF (10/1, 300 mL×2) and the organic layers were combined. The organic was washed with NH4Cl sat. aq (300 mL×2), dried over anhydrous sodium sulfate and concentrated under vacuum. This resulted in 910 mg (62.79%) of [2-([[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]methyl)-5-(4-methyl-1,3-thiazol-5-yl)phenyl]methyl 2,5,8,11,14,17,20,23,26,29,32,35,38,41,44,47,50,53,56,59,62,65,68-tricosaoxaheptacontan-70-oate as a yellow oil.

Step 7: Preparation of [2-([[(2S,4R)-1-[(2S)-2-amino-3,3-dimethylbutanoyl]-4-hydroxypyrrolidin-2-yl]formamido]methyl)-5-(4-methyl-1,3-thiazol-5-yl)phenyl]methyl 2,5,8,11,14,17,20,23,26,29,32,35,38,41,44,47,50,53,56,59,62,65,68-tricosaoxaheptacontan-70-oate hydrochloride

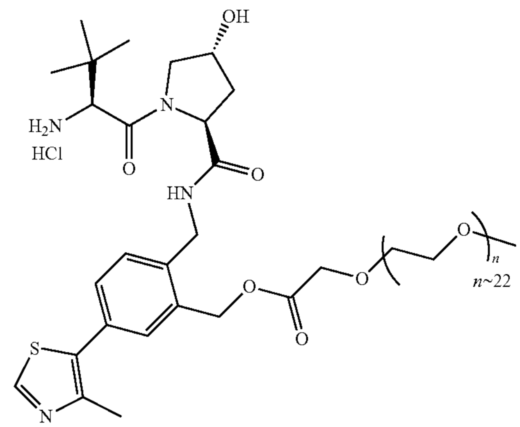

Into a 100-mL round-bottom flask, was placed [2-([[(2S,4R)-1-[(2S)-2-[[(tert-butoxy)carbonyl]amino]-3,3-dimethylbutanoyl]-4-[(tert-butyldimethylsilyl)oxy]pyrrolidin-2-yl]formamido]methyl)-5-(4-methyl-1,3-thiazol-5-yl)phenyl]methyl 2,5,8,11,14,17,20,23,26,29,32,35,38,41,44,47,50,53,56,59,62,65,68-tricosaoxaheptacontan-70-oate (950 mg, 0.55 mmol, 1 equiv), dioxane/HCl (10 mL), (4 M in dioxane). The resulting solution was stirred for 2 h at room temperature. The resulting mixture was concentrated under vacuum. This resulted in 850 mg (99.82%) of [2-([[(2S,4R)-1-[(2S)-2-amino-3,3-dimethylbutanoyl]-4-hydroxypyrrolidin-2-yl]formamido]methyl)-5-(4-methyl-1,3-thiazol-5-yl)phenyl]methyl 2,5,8,11,14,17,20,23,26,29,32,35,38,41,44,47,50,53,56,59,62,65,68-tricosaoxaheptacontan-70-oate hydrochloride as a yellow oil.

Step 8: Preparation of 2-(((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)methyl)-5-(4-methylthiazol-5-yl)benzyl 2,5,8,11,14,17,20,23,26,29,32,35,38,41,44,47,50,53,56,59,62,65,68-tricosaoxaheptacontan-70-oate

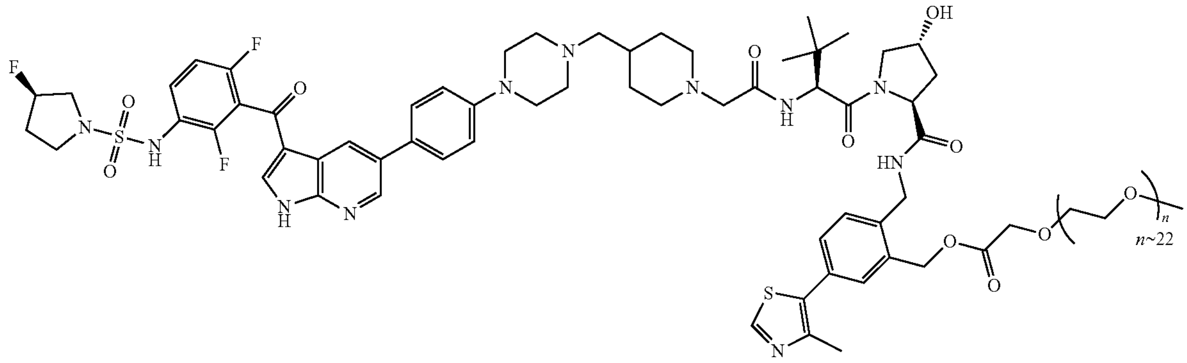

Into a 100-mL round-bottom flask, was placed 2-(4-[[4-(4-[3-[2,6-difluoro-3-([[(3R)-3-fluoropyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (408.8 mg, 0.55 mmol, 1 equiv), [2-([[(2S,4R)-1-[(2S)-2-amino-3,3-dimethylbutanoyl]-4-hydroxypyrrolidin-2-yl]formamido]methyl)-5-(4-methyl-1,3-thiazol-5-yl)phenyl]methyl 2,5,8,11,14,17,20,23,26,29,32,35,38,41,44,47,50,53,56,59,62,65,68-tricosaoxaheptacontan-70-oate hydrochloride (850 mg, 0.55 mmol, 1.00 equiv), DIEA (283.4 mg, 2.19 mmol, 3.97 equiv), BOP (293 mg, 0.66 mmol, 1.20 equiv), DMF (15 mL). The resulting solution was stirred for 2 h at room temperature. The resulting solution was diluted with ethyl acetate/THF (10/1, 500 mF) and washed with water (200 mF) and NH4Cl (sat. aq, 200 mF). The organic was dried over anhydrous sodium sulfate and concentrated under vacuum. The crude product was purified by Prep-HPFC resulting in 280.0 mg (22.79%) of 2-(((2S,4R)-1-((S)-2-(2-(4-((4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxypyrrolidine-2-carboxamido)methyl)-5-(4-methylthiazol-5-yl)benzyl 2,5,8,11,14,17,20,23,26,29,32,35,38,41,44,47,50,53,56,59,62,65,68-tricosaoxaheptacontan-70-oate as a light brown solid. FC/MS (ESI) m/z: 2223.44 $[M+1]^+$; $^1H$ NMR (400 MHz, $CDCl_3$) δ 11.61 (s, 1H), 8.84 (s, 1H), 8.70 (s, 1H), 8.59 (s, 1H), 7.90 (m, 1H), 7.76 (s, 1H), 7.73-7.68 (m, 1H), 7.57-7.55 (m, 2H), 7.44-7.33 (m, 4H), 7.04-6.97 (m, 3H), 5.27-5.15 (m, 3H), 4.74 (m, 1H), 4.61-4.44 (m, 4H), 4.20-4.13 (m, 4H), 3.81-3.66 (m, 4H), 3.64-3.62 (m, 81H), 3.58-3.54 (m, 4H), 3.50-3.46 (m, 2H), 3.38 (s, 3H), 3.24 (m, 3H), 2.95-2.77 (m, 4H), 2.55-2.46 (m, 8H), 2.28-1.98 (m, 8H), 1.80-1.72 (m, 2H), 1.52 (m, 1H), 1.27 (s, 1H), 1.17 (m, 2H), 0.97 (s, 9H), 0.88-0.82 (m, 1H).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

The following examples are used to assist in describing the disclosure, but should not be seen as limiting the disclosure in any way.

EXAMPLES

Assays and Degradation Data

Protocol for a cellular assay of target protein degradation (A375 cells). A375 cells were cultured in ATCC DMEM+10% FBS in 12 well plates, and treated with indicated compound from Tables 1-41 or 0.1% DMSO vehicle control for 16 hours. Cells were harvested in Cell Signaling lysis buffer (Cat #9803) with the addition of Roche protease inhibitor tablets (Cat #11873580001), and lysates clarified by microcentrifugation. Proteins were separated by SDS-PAGE, and transferred onto nitrocellulose membranes using an Invitrogen iBlot system. Immunoblotting was performed for BRAF (Santa Cruz Cat #9002), CRAF (BD Cat #610151), and pErk (Cell Signaling Cat #9106). GAPDH (Cat #) was used as a loading control. Quantification was carried out using the BioRad Image Fab 5 software.

Protocol for an In-Cell Western cellular assay of target protein degradation (A375 cells). A375 cells were cultured in ATCC DMEM+10% FBS in 96-well plates, and treated with indicated compounds from Tables-43 or 0.1% DMSO vehicle control for 72 hours. Cells were washed with PBS 1×, and affixed to plate using 4% PFA in phosphate buffered saline for 15 minutes; washed IX and permeabilized using 0.1% Triton-X-100 in PBS for 5 minutes; washed IX and blocked with LICOR blocker (Cat. #927-50000) for 1 hour. Cells were then incubated with B-Raf antibody (Santa Cruz Cat #9002) and tubulin antibody (Sigma #T6074) in LICOR blocker for 18 hours. Cells were washed 3× prior to adding secondary antibodies (LICOR cat #926-32210 and 926-

68071) and incubated for 1 hr. Cells were washed 3× and imaged using LICOR Odyssey Software.

The bifunctional compounds of Tables 1A, 1B, 1C, and 1D (FIGS. 2A, 2B, 2C, and 2D, respectively) are examples of the bifunctional compounds that are described in the claims of this application. Some of them have been tested to see if they would exhibit the degradation activity of BRAF protein in cells, and their results are given in the columns of $DC_{50}$ and $D_{max}$ in Tables 2A, 2B, and 2D (FIGS. 3A, 3B, and 3D). Herein, $DC_{50}$ is the compound concentration at which the BRAF concentration level reaches a midpoint between the maximum level and the minimum level in the dose-response curve measuring the BRAF protein concentration in a cell as a function of the compound concentration added to the medium incubating the cells with the compound, and $D_{max}$ is the maximum protein degradation level that can be achieved by varying the compound concentration. Many compounds in these tables are not given any values or ranges of $DC_{50}$ and $D_{max}$ because either they have not been tested or synthesized or they are prophetic examples.

Protocols for Half Life and Percent Release of Prodrugs. Chain length isomers differ slightly in retention time during chromatographic separations, which provides a mixture that is enriched for the desired PEG chain length. Thus, the chromatographic separation does not provide for isolation of homogenous chain length products. Furthermore, analysis of pegylated samples by LCMS will show a slightly different mixture of chain lengths depending on the time point within the HPLC peak that the MS signal is reported for, or the interval over which the mass signals are averaged over For pegylated compounds that are mixtures of chain length isomers, the MS data in Table 2C report the signal that matches closely to the calculated mass for a chain length of the particular compound (e.g., n=22).

Due to the natural abundance of carbon 13 and deuterium (in the order of ~ 1% each) organic molecules of the size of the prodrugs (MW~ 2000) are likely to contain a carbon-13 atom or deuterium atom in them. Therefore, the most intense mass spec signal for these molecules is one unit heavier than the calculated mass for the [M+H]+ ion that assumes carbon 12 and H-1. The lightest isotope peak (all carbon 12 and H-1) is observable in all the samples, and is reported in the data tables.

Large molecules, such as the prodrugs of the present disclosure, typically, and expected by someone skilled in the art, show m/z signals for mono-, double- and triple-protonated ions. [M+H]+, [M+2H]2+ and [M+3H]3+. Often the MS signal for the mono-charged [M+H]+ ion is weaker than the double- and triple-charged ions.

Names for the PEGylated prodrugs of Table 1C were generated by Chemdraw Pro (Version 18.0) are for the n=22 chain length form, do not represent the mixture of chain lengths, and are found in Table 2C.

PEG-Prodrugs of the present disclosure were treated with Heparin-stabilized plasma of multiple species to study release rates of parent drug.

Protocol for determination of release rates of parent drug from PEG prodrugs of this invention: A stock solution of test compound was prepared in DMSO and diluted to the final concentration of 1 mM. 1 mM lovastatin and propantheline working solution was prepared in DMSO and acetonitrile, respectively. Propantheline and lovastatin was used as positive control. 2.5 μL of this 1 mM stock solution was spiked to 497.5 μL plasma to reach a final concentration of 5 μM. The final concentration of organic solvents was 0.5%. The assay was performed in duplicated. The reaction samples were incubated at 37° C. at approximately 60 rpm in a water bath. For prodrug samples, aliquots of 50 μL were taken from the reaction samples at 0, 2, 5, 15, 30, 120, 300 and 1440 minutes. For the intermediate or parent standard, aliquots of 50 μL were taken from the reaction samples at 0 minute. The pH value was measured before and after the incubation.

The reaction was stopped by the addition of 7 volumes of cold acetonitrile containing internal standards (1S, 200 ng/mL). Alternatively, methanol with 0.1% formic acid was used for those compounds that precipitated from acetonitrile.

All samples were vortexed for 2 minutes, followed by centrifugation at 3220 g for 30 minutes to precipitate proteins. 100 μL of the supernatant was transferred to a new plate. The supernatant was diluted with ultrapure water according to the LC-MS signal response and peak shape. Samples were analyzed by LC-MS/MS.

LC system: Shimadzu Triple Quad 6500+ Low Mass from AB Inc (Canada) with an ESI interface, Column temperature: 40° C., Injection volume: 10 μL, Column: XSelect Hss T3 2.5μ (2.1×30 mm) Column XP coupled with preguard column, Mobile phase: 0.1% formic acid in acetonitrile (B) and 0.1% formic acid in water (A).

All calculations were carried out using Microsoft Excel. Remaining percentages of prodrug at each time point were determined by the peak area ratios from extracted ion chromatograms. Appearance of the intermediate or parent (μM) were calculated by the peak area ratios of the intermediate or parent of prodrug samples and intermediate or parent standard respectively.

Summary of FIGS. 4, 5, 6A, 6B, 6C, 7, 8A, 8B, 9A, 9B, and 10. Bifunctional compounds comprising PTM-IIa and PTM-IIb, such as compound 512, induces targeted degradation of BRAF mutants sensitive (Class 1) and insensitive (Class 2 and Class 3) to vemurafenib. Degradation of mutant BRAF suppresses MAPK and can halt cancer cell growth. Wild-type BRAF is spared from degradation despite the ability to engage bifunctional compounds of the present disclosure and form a ternary complex; inefficient recruitment of Cullin 2 might explain the observed results. Induced degradation may be a strategy to overcome vemuragenib resistance.

Table 1A. Exemplary protein targeting moieties and compounds of the present disclosure (see FIG. 2A).

Table 1B. Exemplary protein targeting moieties and compounds of the present disclosure (see FIG. 2B).

Table 1C. Exemplary protein targeting moieties and compounds of the present disclosure (see FIG. 2C).

Table 1D. Exemplary protein targeting moieties and compounds of the present disclosure (see FIG. 2D).

Table 2A. Degradation data for the Exemplary Compounds of Table 1A (See FIG. 3A).

Table 2B. Degradation data for the Exemplary Compounds of Table 1B (See FIG. 3B).

Table 2C. Degradation data for the Exemplary Compounds of Table 1C (See FIG. 3C).

Table 2D. Degradation data for the Exemplary Compounds of Table 1D (See FIG. 3D).

SPECIFIC EMBODIMENTS OF THE PRESENT DISCLOSURE

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

In any aspect or embodiment, the description provides the following exemplary RAF bifunctional molecules (compounds of Tables 1A, 1B, 1C, i.e., any one of the compounds of Table 1A, 1B, 1C, or a combination thereof), including salts, prodrugs, polymorphs, analogs, derivatives, and deuterated forms thereof.

As such, the description provides a compound comprising the structure of any one of the compounds of Tables 1A-1C (i.e., any one of the compounds of Table 1A, 1B, 1C, or a combination thereof), therapeutic compositions comprising the same, and methods of use as described herein.

What is claimed is:

1. A bifunctional compound having the chemical structure:

ULM-L-PTM, or a pharmaceutically acceptable salt, enantiomer, or stereoisomer thereof, wherein:

(a) the ULM is a Von Hippel-Lindau (VHL) ligase-binding moiety (VLM) with a chemical structure represented by:

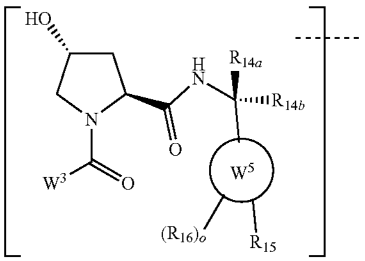

or

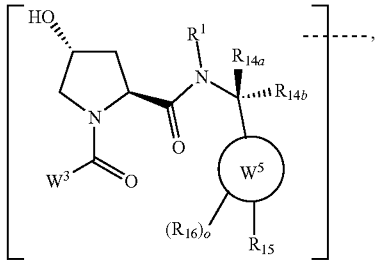

wherein:

$W^3$ is selected from the group of an optionally substituted aryl, optionally substituted heteroaryl, or

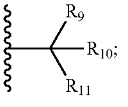

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

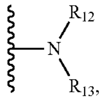

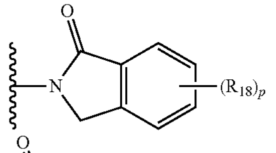

or

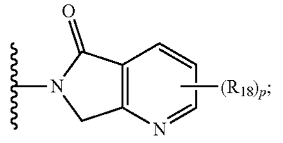

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R^1$ is H, linear or branched $C_1$-$C_6$ alkyl group optionally substituted by 1 or more halo or —OH groups;

$R_{14a}$, $R_{14b}$, are each independently selected from the group of H, haloalkyl, optionally substituted alkoxy, $(CH_2)_{m'}OCOCH_2(CH_2)_{m'}OCH_2(CH_2)_{m'}$, $CO(CH_2)_{m'}$, OH, $(CH_2)_{m'}OCOCH_2(CH_2)_{m'}CO(CH_2)_{m'}OH$, optionally substituted hydroxyl alkyl, $—(CH_2)_{m'}C(=O)(CH_2)_{m'}C(=O)(OH)$, or optionally substituted alkyl optionally with one or more carbons replaced with an oxygen;

each m' is individually an integer from 1 to 4;

$W^5$ is selected from the group of an optionally substituted phenyl or an optionally substituted 5-10 membered heteroaryl, $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

each $R_{16}$ is independently selected from the group of H, CN, halo, optionally substituted alkyl optionally having one or more carbon atoms replaced with an oxygen atom, optionally substituted haloalkyl, hydroxy, or optionally substituted haloalkoxy;

o is 0, 1, 2, 3, or 4;

$R_{18}$ is independently selected from the group of H, halo, optionally substituted alkoxy, cyano, optionally substituted alkyl, haloalkyl, haloalkoxy or a linker; and p is 0, 1, 2, 3, or 4; and the dashed line indicates the site of attachment the chemical linker group (L) coupling the ULM to the PTM;

(b) the PTM is a small molecule comprising a rapidly accelerated fibrosarcoma (RAF) protein targeting moiety wherein the PTM is represented by chemical structure PTM-IIa or PTM-IIb:

PTM-IIa

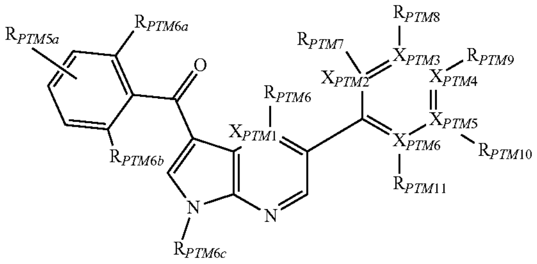

or

PTM-IIb

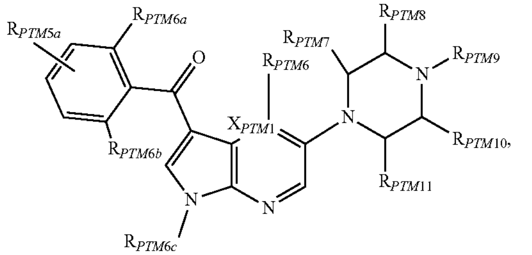

wherein:

$X_{PTM1}$, $X_{PTM2}$, $X_{PTM3}$, $X_{PTM4}$, $X_{PTM5}$, and $X_{PTM6}$ are independently selected from CH or N;

$R_{PTM5a}$ is selected from the group consisting of: H, optionally substituted —C(O)$NH_2$, optionally substituted -$NH_2$, 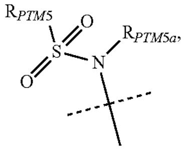 -NHC(O)$R_{PTM5}$;

$R_{PTM5}$ is selected from the group consisting of

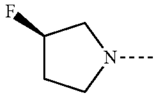 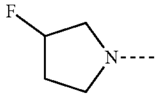 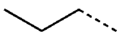 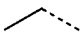

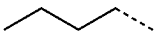 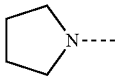 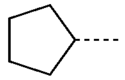

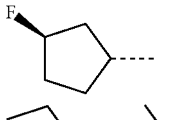 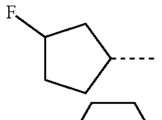 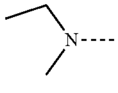 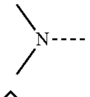

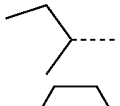 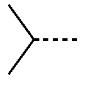 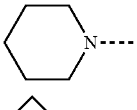 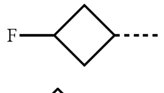

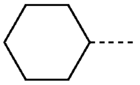 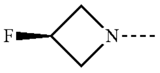 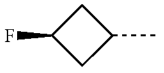

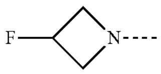 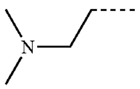 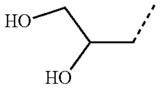

-continued

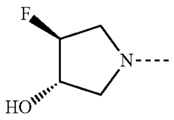 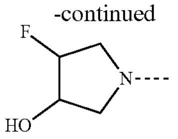 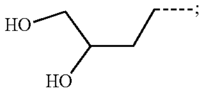;

$R_{PTM5b}$ is hydrogen or a linear or branched $C_1$-$C_4$ alkyl;

$R_{PTM6a}$ and $R_{PTM6b}$ are each independently selected from hydrogen, halogen, or optionally substituted linear or branched $C_1$-$C_6$ alkyl;

$R_{PTM6}$ is either of the following groups: absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM6c}$ is hydrogen or a linear or branched $C_1$-$C_4$ alkyl;

$R_{PTM7}$ is absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle; and $R_{PTM11}$ is absent, hydrogen, halogen, methyl, ethyl, $OCH_3$, $NHCH_3$ or M1-$CH_2$—$CH_2$-M2 in which M1, wherein $CH_2$, O and NH, and M2 is hydrogen, alkyl, cyclic alkyl, aryl or heterocycle;

at least one of $R_{PTM8}$, $R_{PTM9}$, or $R_{PTM10}$ is modified to be covalently joined to a chemical linker group (L) coupling the PTM to the ULM, or two of $R_{PTM8}$, $R_{PTM9}$, and $R_{PTM10}$ are modified to form a polycyclic (e.g., bicyclic) fused ring with a chemical linker group (L) coupling the PTM to the ULM; and (c) the L is a chemical linking moiety connecting the ULM and the PTM, wherein the linker group comprises a chemical structural unit represented by the formula:

$$-(A^L)q-,$$

wherein:

$(A^L)_q$ is a group which is connected to at least one of the ULM, the PTM, or a combination thereof;

q is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$ cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)2$, $N(C_{3-8}cycloalkyl)(C_{1-8}alkyl)$, OH, $NH_2$, SH, $SO_2C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$.

2. The bifunctional compound according to claim 1, or a pharmaceutically acceptable salt, enantiomer, or stereoisomer thereof, wherein:

$X_{PTM1}$, $X_{PTM2}$, $X_{PTM3}$, $X_{PIM4}$, $X_{PTM5}$, and $X_{PTM6}$ are independently selected from CH or N;

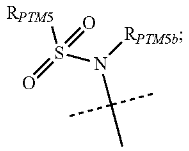

$R_{PTM5a}$ is $R_{PTM5}$ is selected from the group consisting of

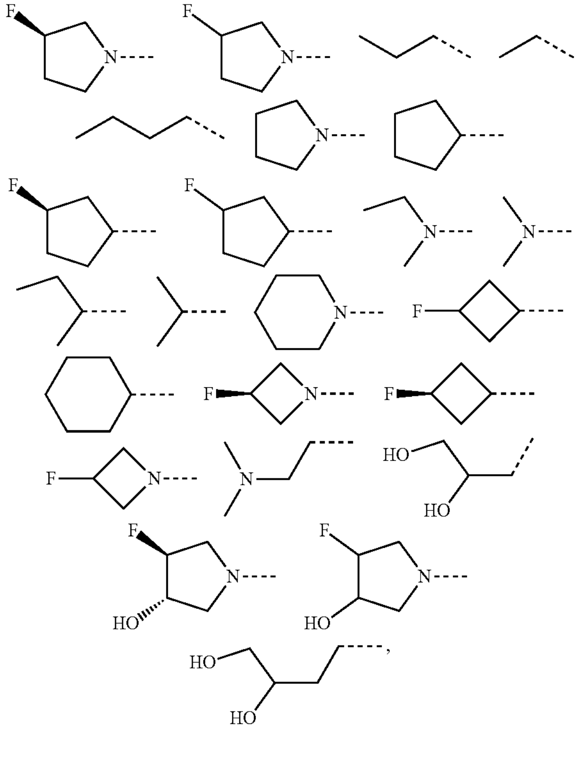

$R_{PTM5b}$ is hydrogen or a linear or branched $C_1$-$C_4$ alkyl;

$R_{PTM6a}$ and $R_{PTM6b}$ are each independently selected from hydrogen, halogen, or optionally substituted linear or branched $C_1$-$C_6$ alkyl;

$R_{PTM6}$ is either of the following groups: absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM6c}$ is hydrogen or a linear or branched $C_1$-$C_4$ alkyl;

$R_{PTM7}$ is absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle; and $R_{PTM11}$ is absent, hydrogen, halogen, methyl, ethyl, $OCH_3$, $NHCH_3$ or M1-$CH_2$—$CH_2$-M2 in which M1, wherein $CH_2$, O and NH, and M2 is hydrogen, alkyl, cyclic alkyl, aryl or heterocycle;

at least one of $R_{PTM8}$, $R_{PTM9}$, or $R_{PTM10}$ is modified to be covalently joined to a chemical linker group (L) coupling the PTM to the ULM, or two of $R_{PTM8}$, $R_{PTM9}$, and $R_{PTM10}$ are modified to form a polycyclic (e.g., bicyclic) fused ring with a chemical linker group (L) coupling the PTM to the ULM.

3. The bifunctional compound according to claim 1, or a pharmaceutically acceptable salt, enantiomer, or stereoisomer thereof, wherein:

when $R_{PTM9}$ is the covalently joined position, $R_{PTM7}$ and $R_{PTM8}$ are connected together via a covalent bond in a way to form a bicyclic group with the ring to which $R_{PTM7}$ and $R_{PTM8}$ are attached; or when $R_{PTM8}$ is the covalently joined position, $R_{PTM9}$ and $R_{PTM10}$ are connected together via a covalent bond in a way to form a bicyclic group with the ring to which $R_{PTM9}$ and $R_{PTM10}$ are attached; or when $R_{PTM10}$ is the covalently joined position, $R_{PTM8}$ and $R_{PTM9}$ are connected together via a covalent bond in a way to form a bicyclic group with the ring to which $R_{PTM8}$ and $R_{PTM9}$ are attached.

4. The bifunctional compound according to claim 1, or a pharmaceutically acceptable salt, enantiomer, or stereoisomer thereof, wherein the PTM is selected from the group consisting of:

PTM-2

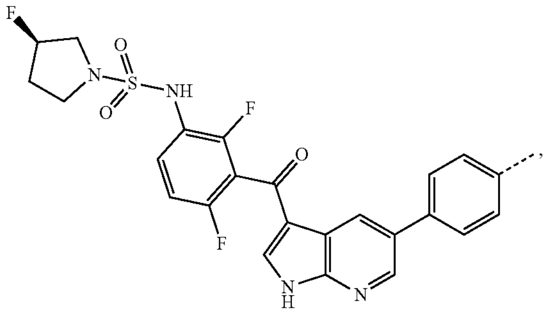

PTM-3

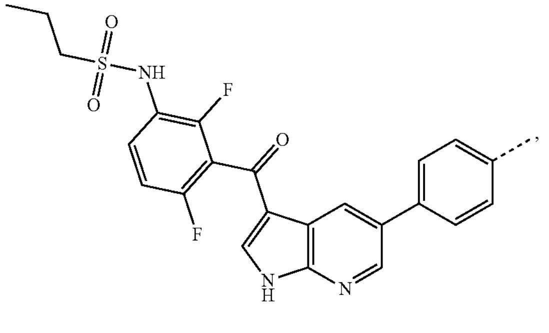

-continued
PTM-6
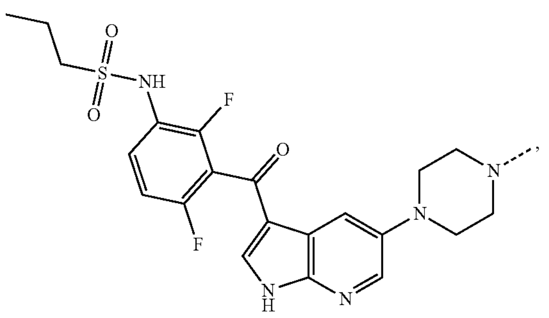
PTM-9
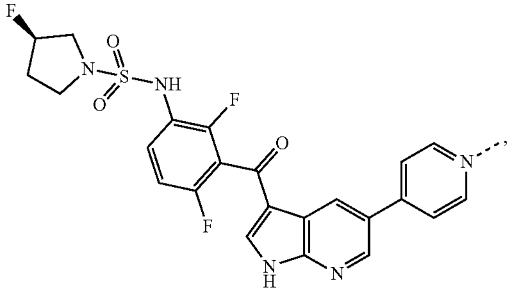
or
PTM-10
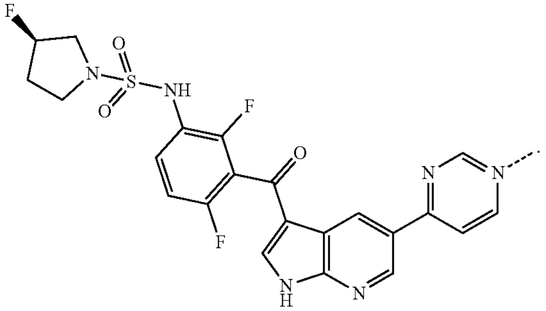
5. The bifunctional compound according to claim 1, or a pharmaceutically acceptable salt, enantiomer, or stereoisomer thereof, wherein the ULM is selected from the group consisting of:
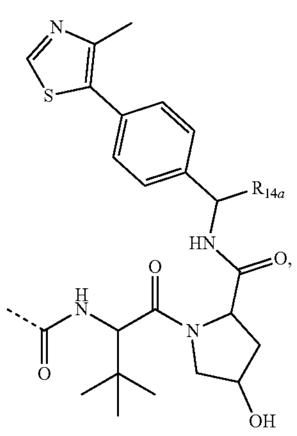
-continued
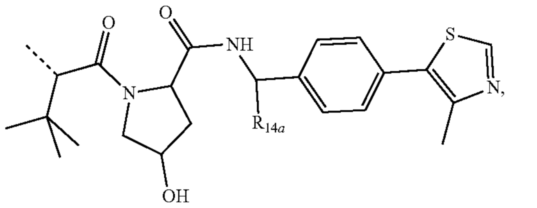
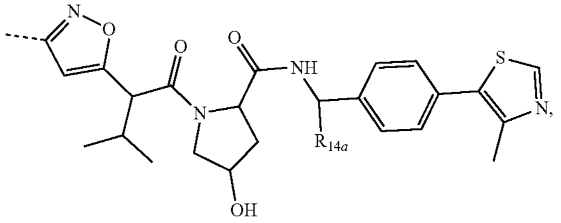
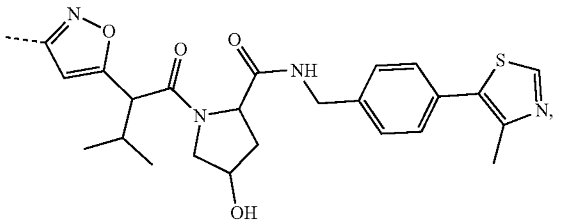
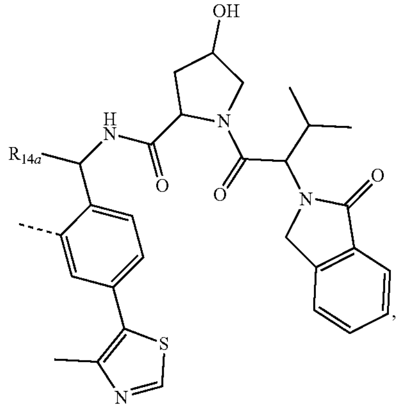
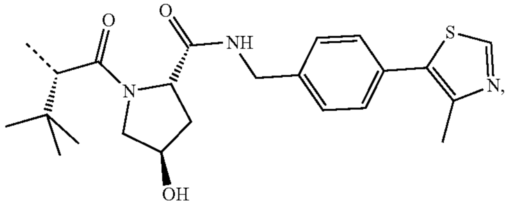
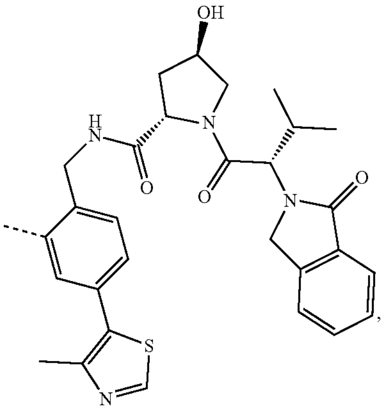

-continued

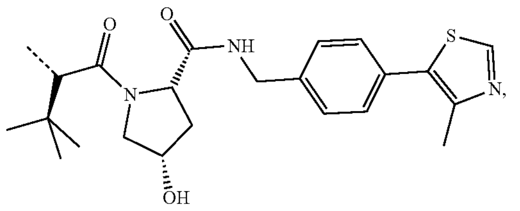

or

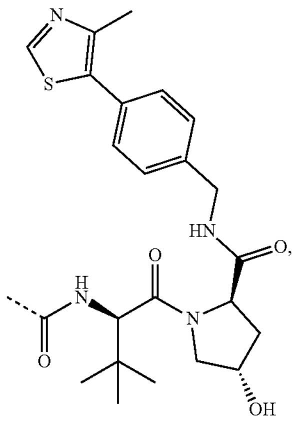

wherein $R_{14a}$ is a methyl or hydroxymethyl.

6. The bifunctional compound according to claim 1, or a pharmaceutically acceptable salt, enantiomer, or stereoisomer thereof, wherein the ULM has a chemical structure selected from the group consisting of:

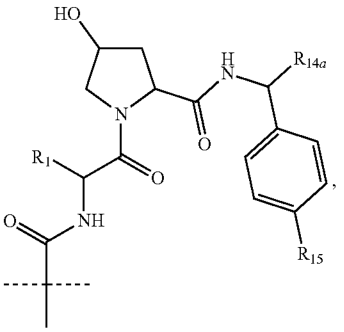

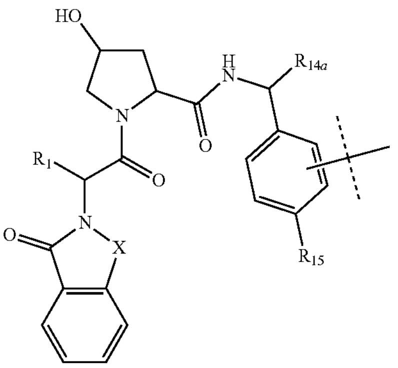

and

-continued

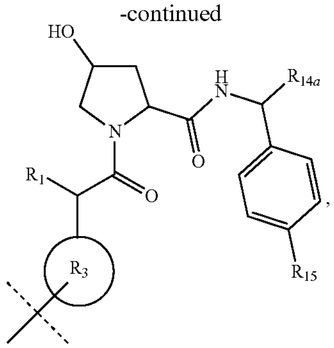

wherein:

$R_1$ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, $(CH_2)_{m'}OCOCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, or cyclopropyl;

each m' is individually an integer from 1 to 4;

$R_{15}$ is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, optionally substituted cycloalkyl, or optionally substituted cycloheteroalkyl;

X is C, $CH_2$, or C═O $R_3$ is a bond or an optionally substituted 5 or 6 membered heteroaryl; and the dashed line indicates the site of attachment the chemical linker group (L) coupling the ULM to the PTM.

7. The bifunctional compound according to claim 1, or a pharmaceutically acceptable salt, enantiomer, or stereoisomer thereof, wherein the ULM comprises a group according to the chemical structure:

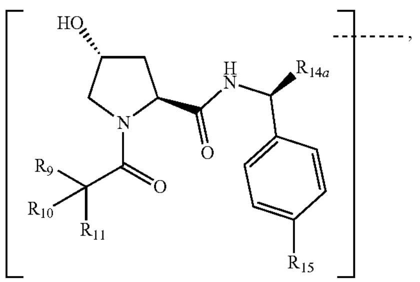

wherein:

$R_{14a}$ is H, haloalkyl, optionally substituted alkyl, methyl, fluoromethyl, hydroxymethyl, ethyl, isopropyl, $(CH_2)_{m'}OCOCH_2(CH_2)_{m'}OCH_2(CH_2)_{m'}CO(CH_2)_{m'}OH$, $(CH_2)_{m'}OCOCH_2(CH_2)_{m'}CO(CH_2)_{m'}OH$, or cyclopropyl;

each m' is individually an integer from 1 to 4;

$R_9$ is H;

$R_{10}$ is H, ethyl, isopropyl, tert-butyl, sec-butyl, cyclopropyl, cyclobutyl, cyclopentyl, or cyclohexyl;

$R_{11}$ is

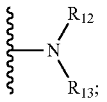

optionally substituted heteroaryl,

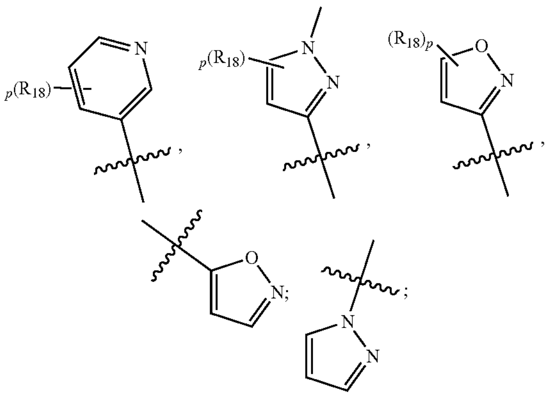

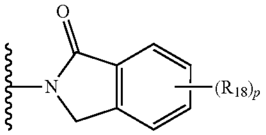

or

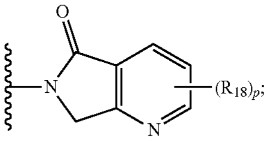

p is 0, 1, 2, 3, or 4; and each $R_{18}$ is independently halo, optionally substituted alkoxy, cyano, optionally substituted alkyl, haloalkyl, haloalkoxy or a linker;

$R_{12}$ is H, C=O $R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ is selected from the group consisting of H, halogen, Cl, CN, OH, $NO_2$, optionally substituted heteroaryl, optionally substituted aryl, optionally substituted cycloheteroalkyl,

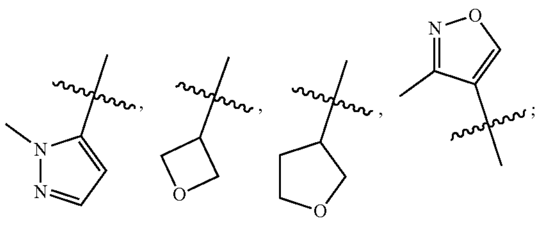

-continued

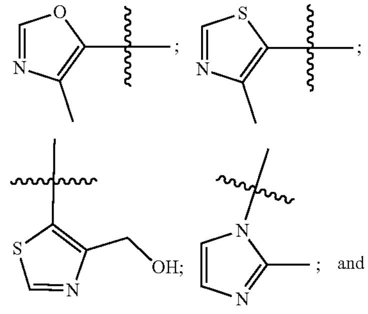

and the dashed line indicates the site of attachment the chemical linker group (L) coupling the ULM to the PTM.

8. The bifunctional compound according to claim 1, or a pharmaceutically acceptable salt, enantiomer, or stereoisomer thereof, wherein the chemical linker group (L) comprises a group represented by a general structure selected from the group consisting of:

$-N(R)-(CH2)_m-O(CH2)_n-O(CH2)_o-O(CH2)_p-O(CH2)_q-O(CH2)_r-OCH2-$, $-O-(CH2)_m-O(CH2)_n-O(CH2)_o-O(CH2)_p-O(CH2)_q-O(CH2)_r-OCH2-$, $-O-(CH2)_m-O(CH2)_n-O(CH2)_o-O(CH2)_p-O(CH2)_q-O(CH2)_r-O-$;

$-N(R)-(CH2)_m-O(CH2)_n-O(CH2)_o-O(CH2)_p-O(CH2)_q-O(CH2)_r-O-$;

$-(CH2)_m-O(CH2)_n-O(CH2)_o-O(CH2)_p-O(CH2)_q-O(CH2)_r-O-$;

$-(CH2)_m-O(CH2)_n-O(CH2)_o-O(CH2)_p-O(CH2)_q-O(CH2)_r-OCH2-$;

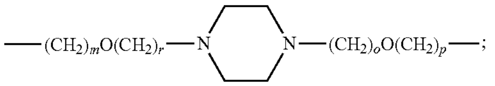

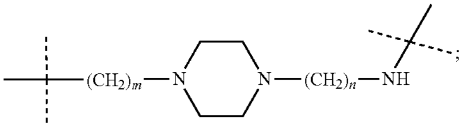

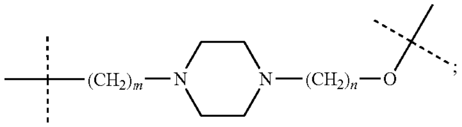

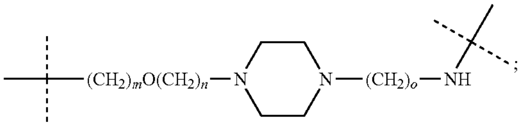

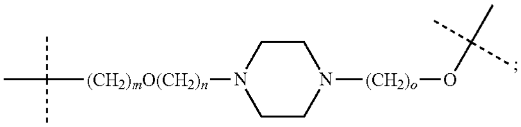

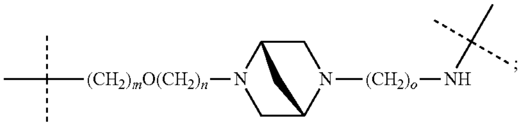

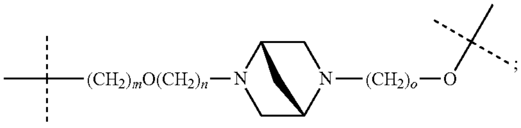

-continued
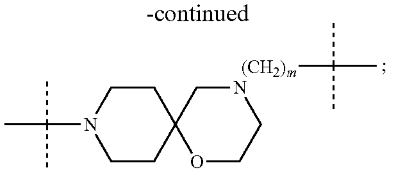
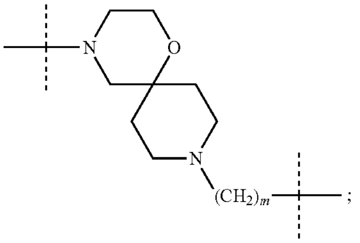
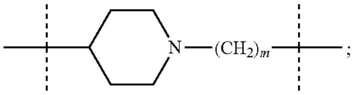
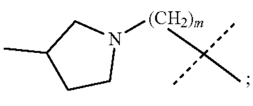
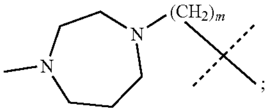
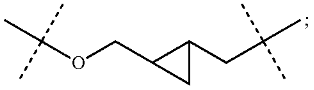
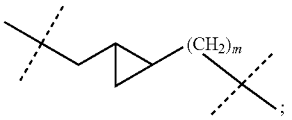
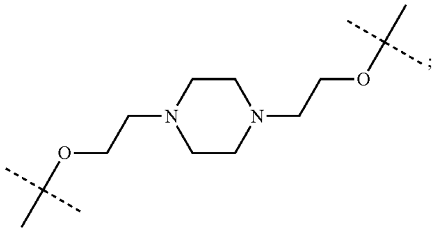
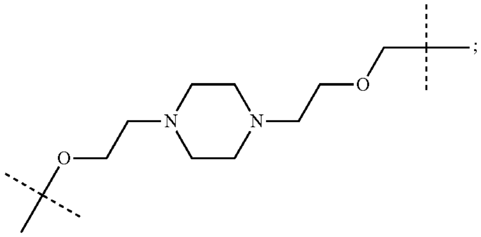
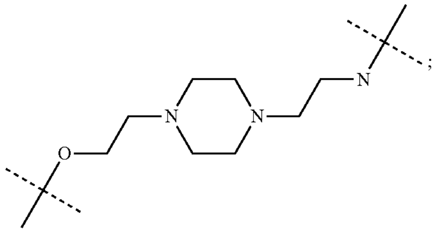
-continued
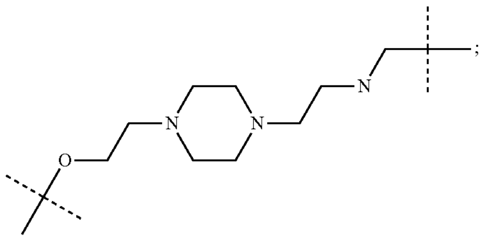
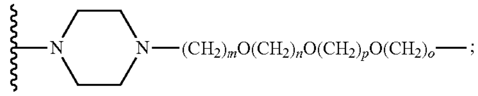
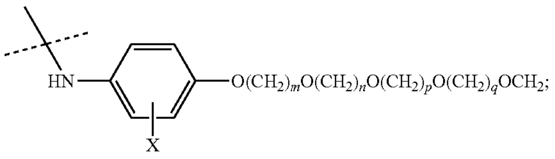
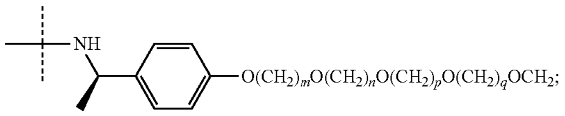
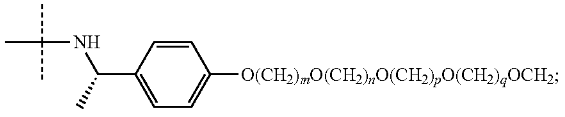
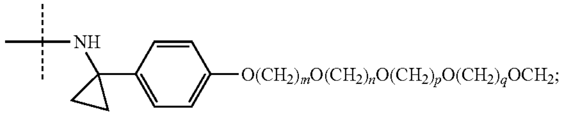
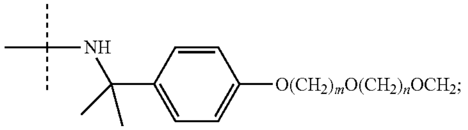
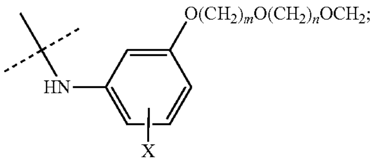
and
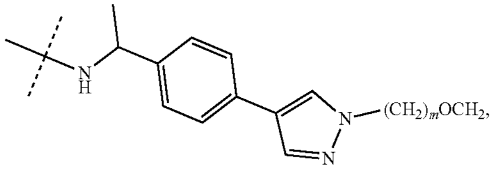
wherein m, n, o, p, q, and r, are independently 0, 1, 2, 3, 4, 5, 6, with the proviso that when the number is zero, there is no N—O or O—O bond, R is selected from the group H, methyl and ethyl, and X is selected from the group H and F;
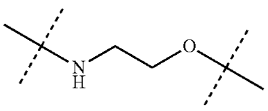
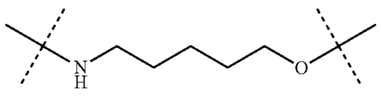

-continued
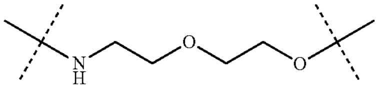
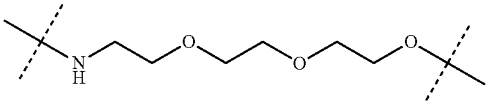
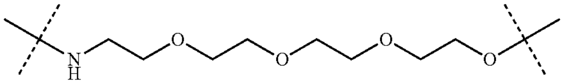
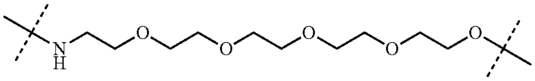
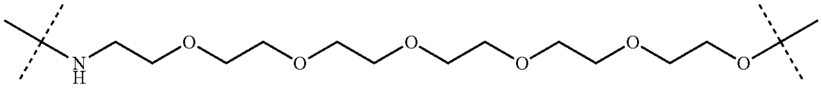
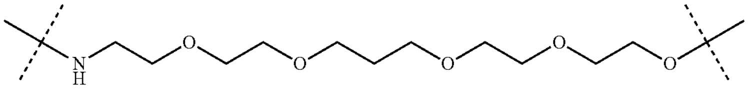
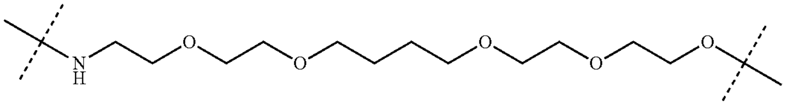
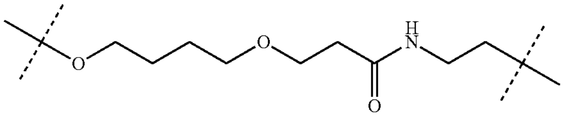
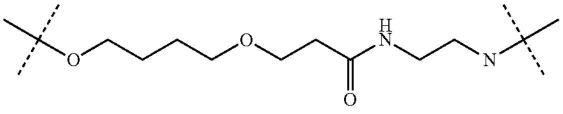
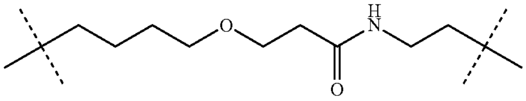
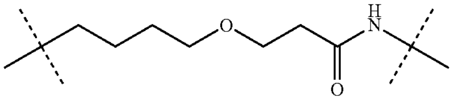
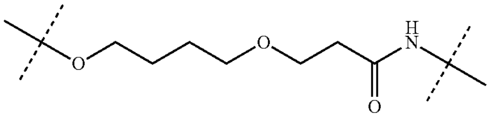
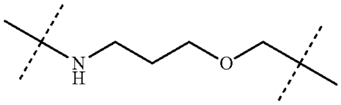
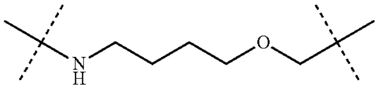
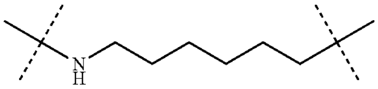
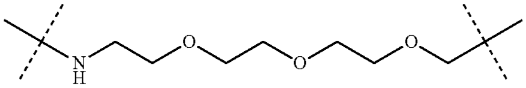
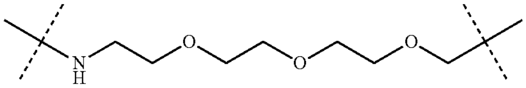
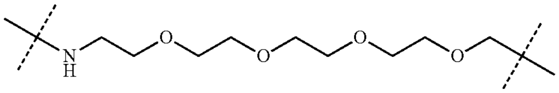
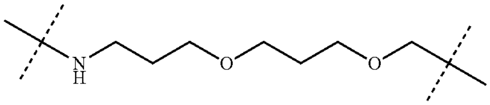
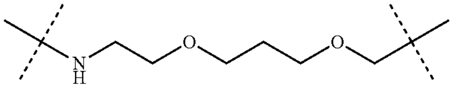
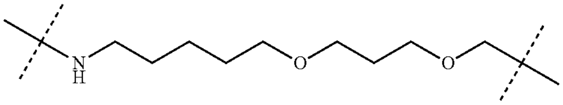
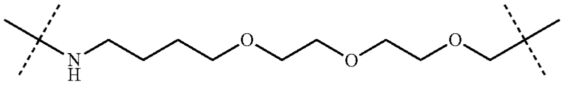
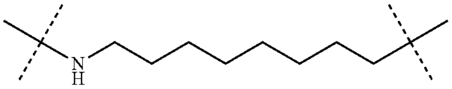
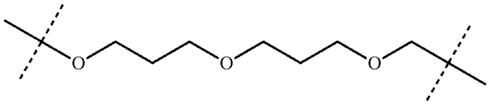
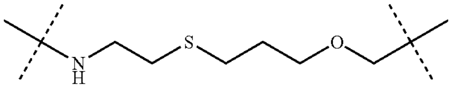
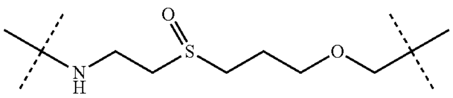
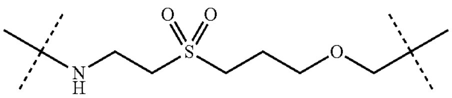
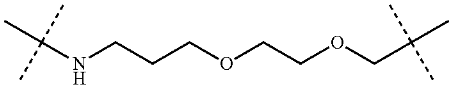
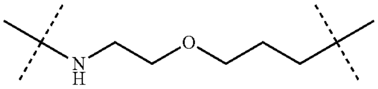
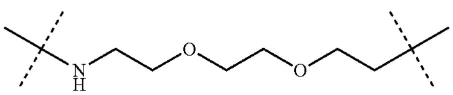
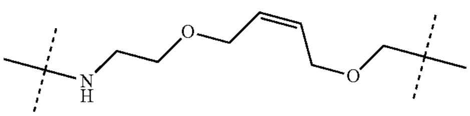

-continued
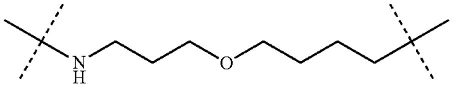
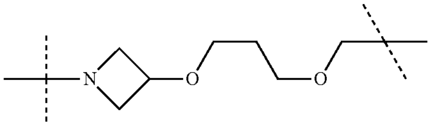
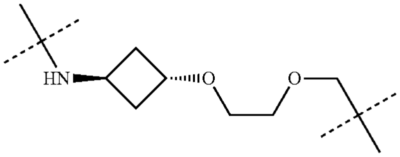
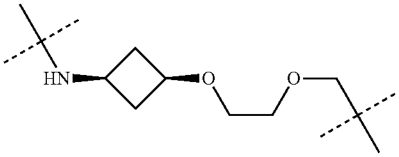
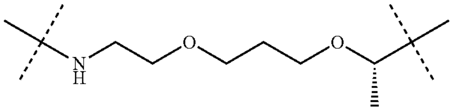
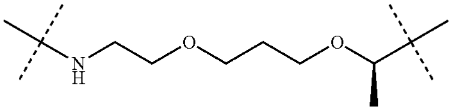
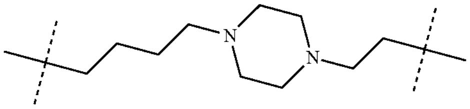
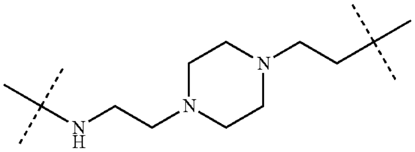
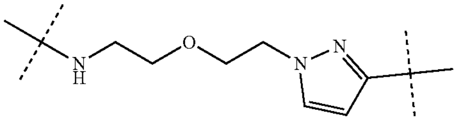
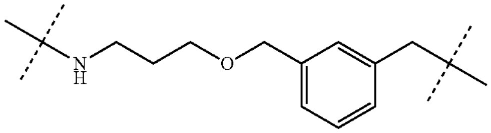
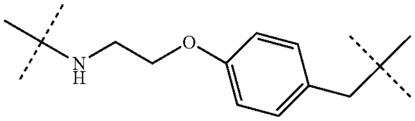
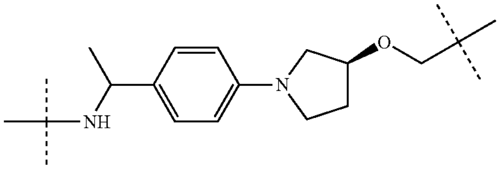
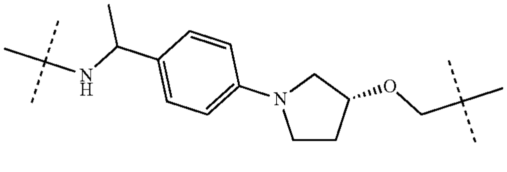
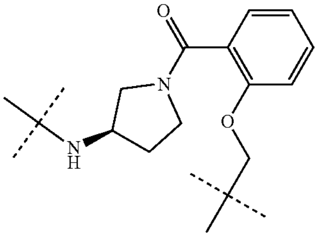
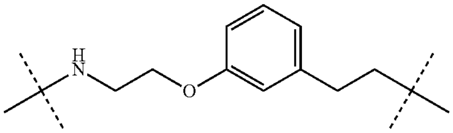
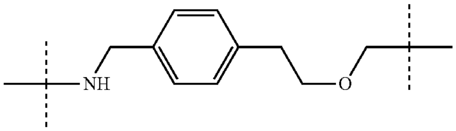
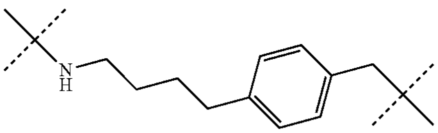
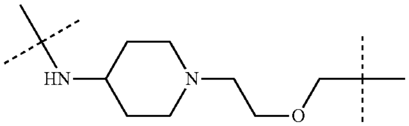
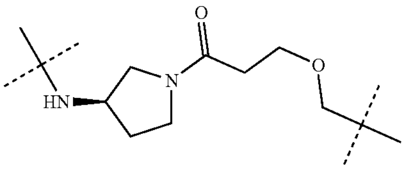
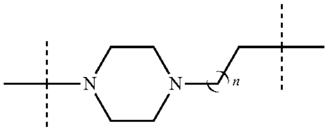
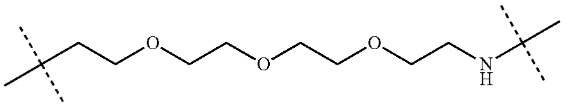
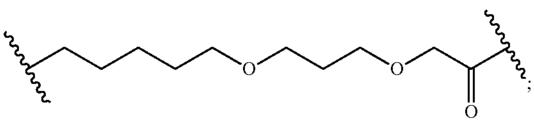
;

-continued
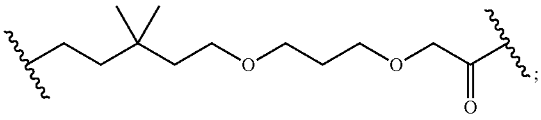
;
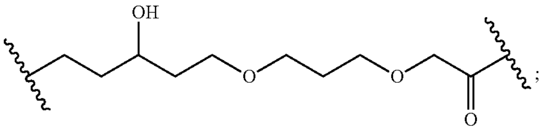
;
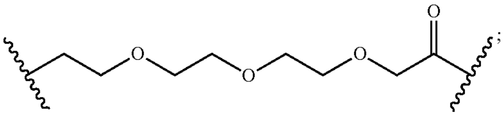
;
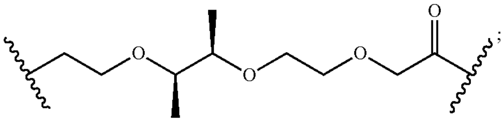
;
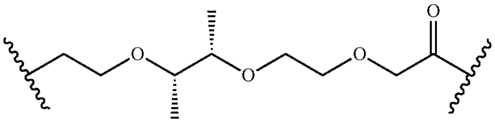
;
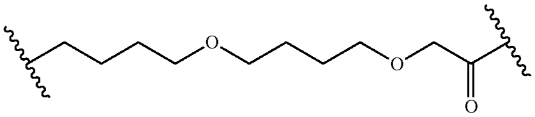
;
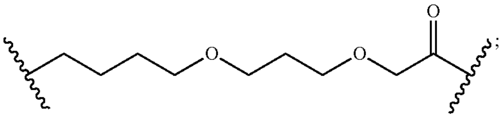
;
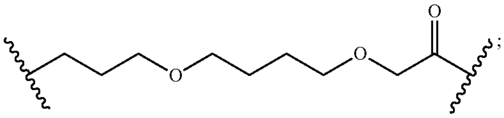
;
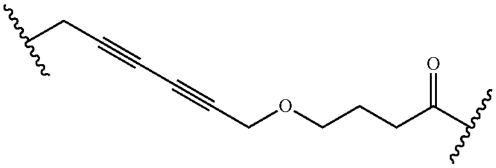
;
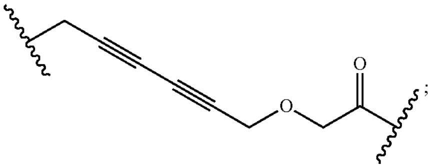
;
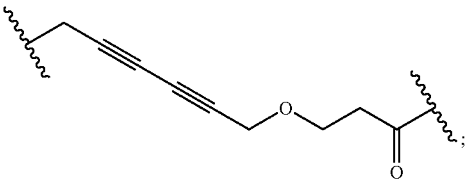
;
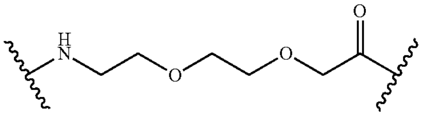
;
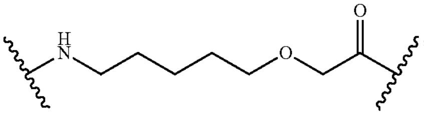
;
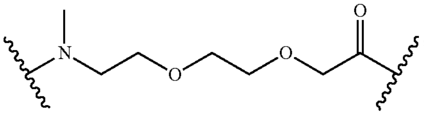
;
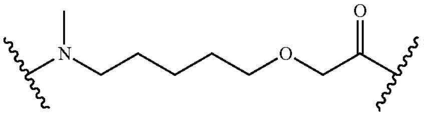
;
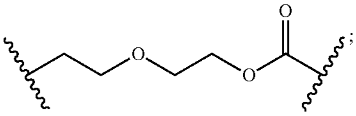
;
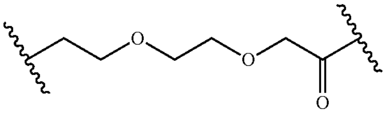
;
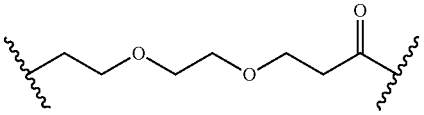
;
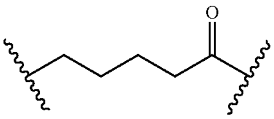
;
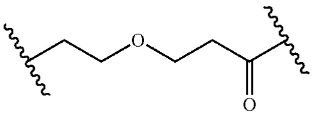
;
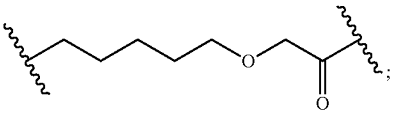
;
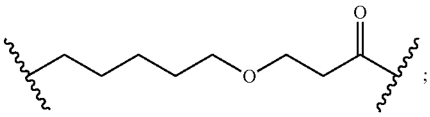
;
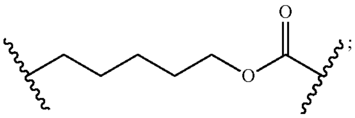
;
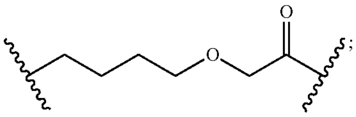
;
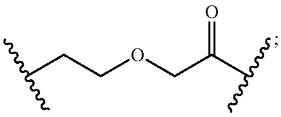
;
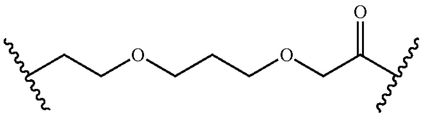
;

-continued
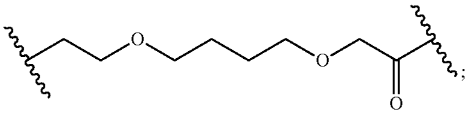;
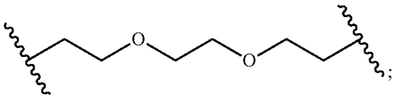;
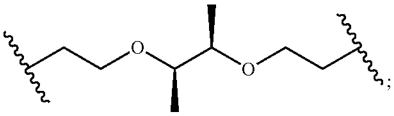;
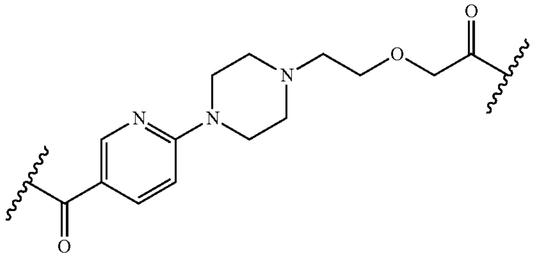;
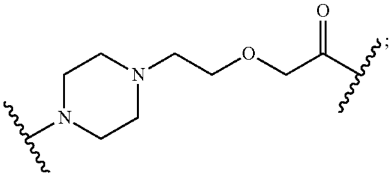;
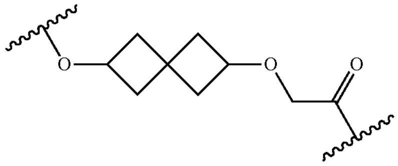;
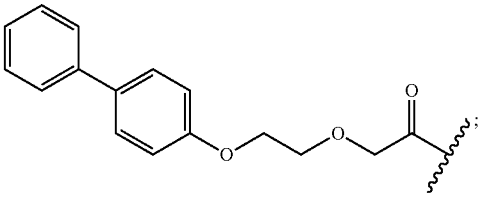;
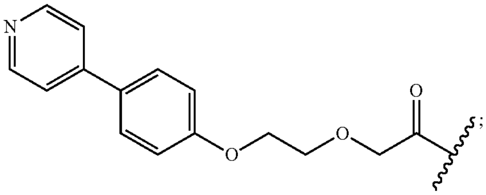;
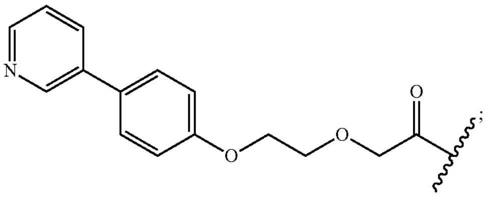;
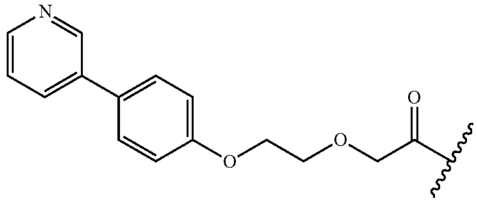;
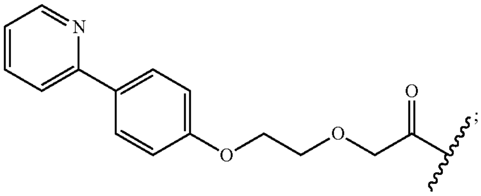;
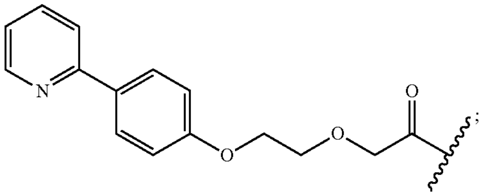;
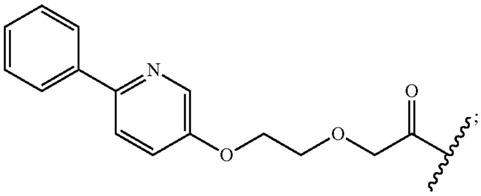;
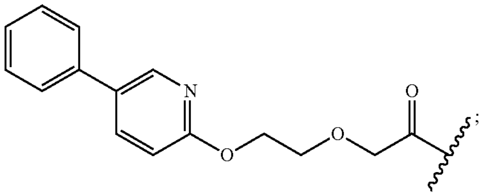;
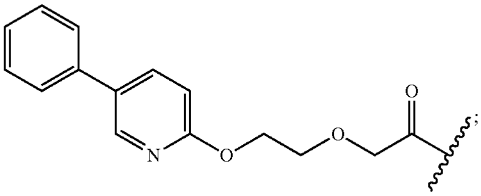;
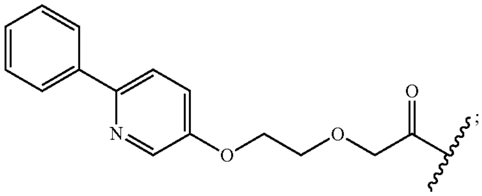;

-continued
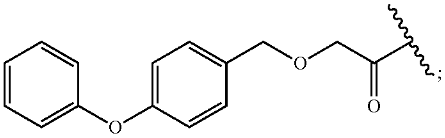;
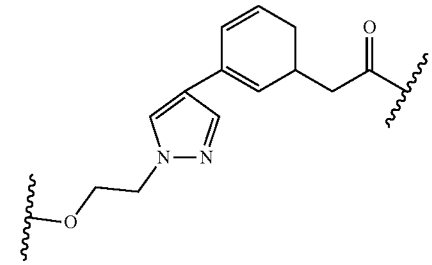;
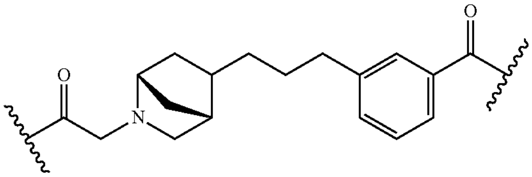;
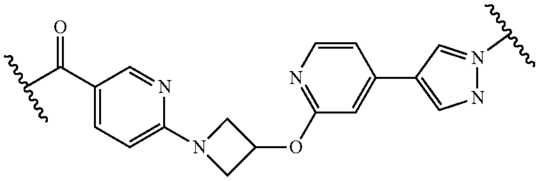;
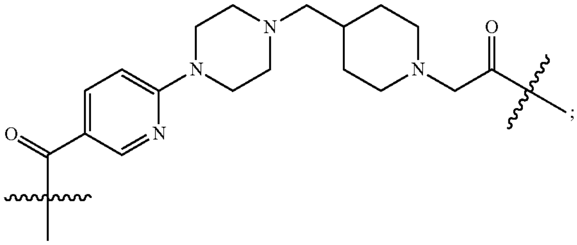;
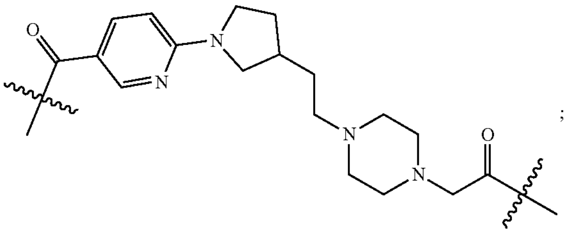;
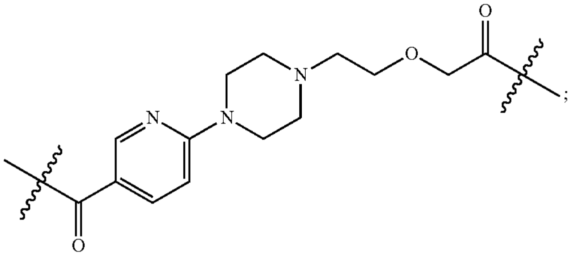;
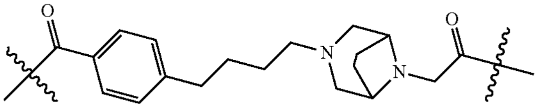;
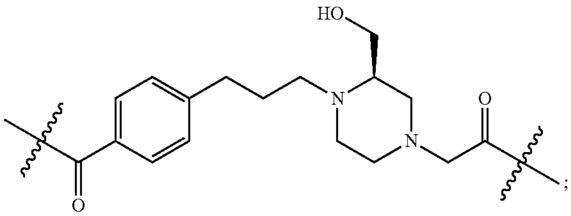;
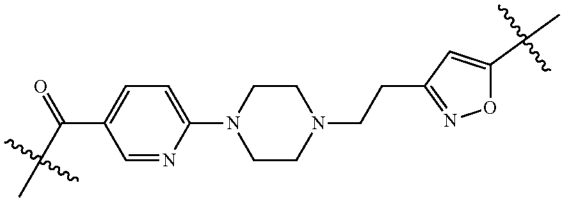;
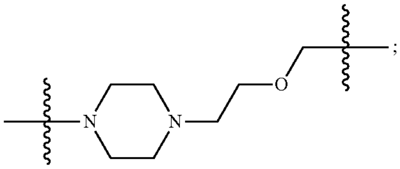;
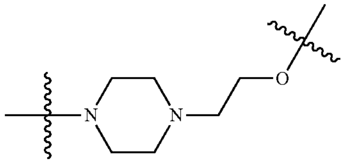;
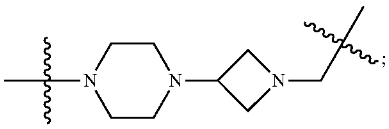;
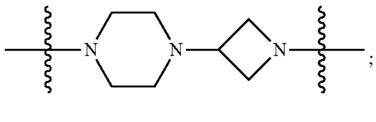;
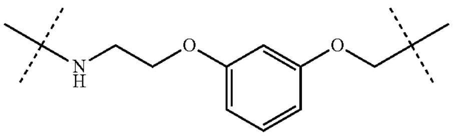
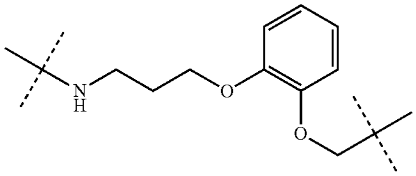

-continued
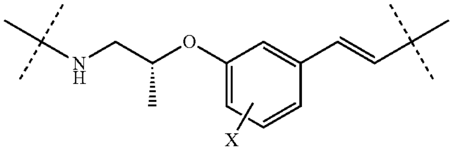
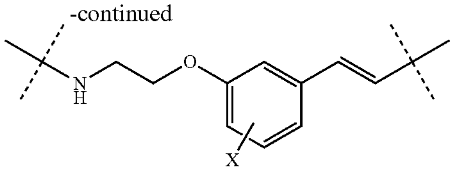
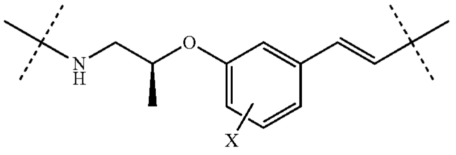
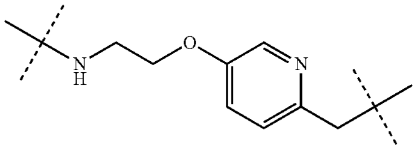
X = H, F
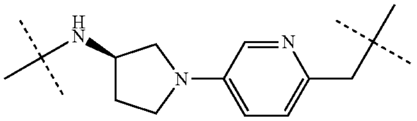
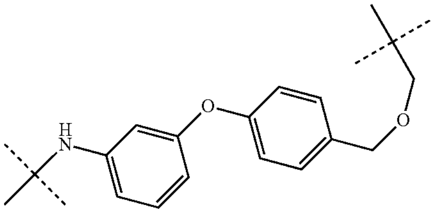
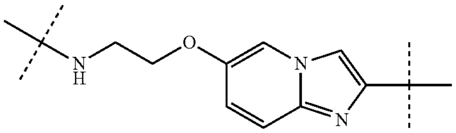
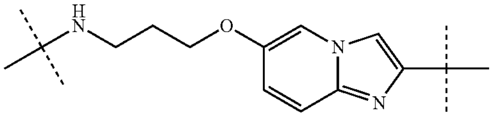
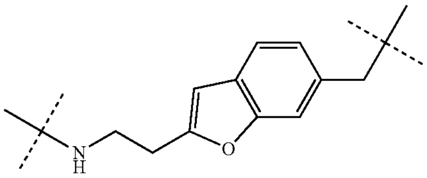
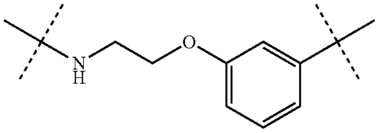
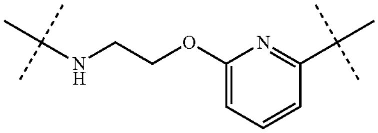
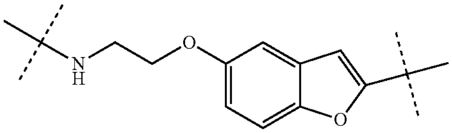
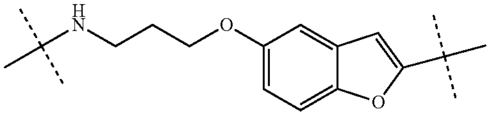
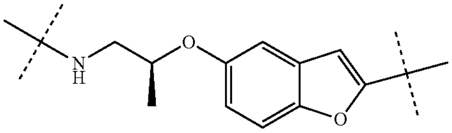
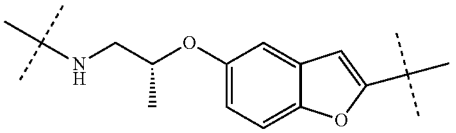
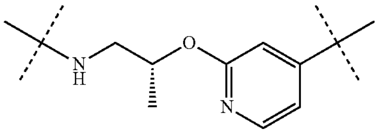
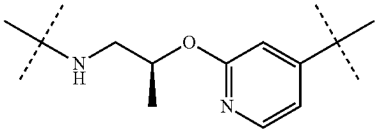
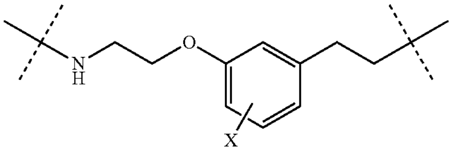
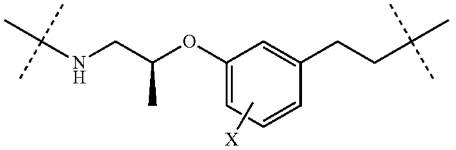
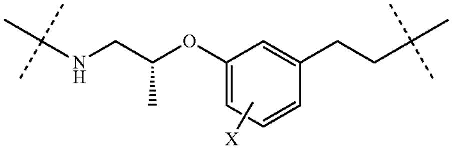
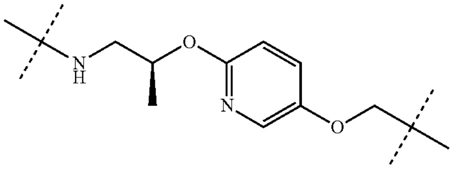
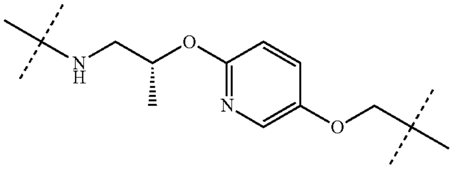

-continued
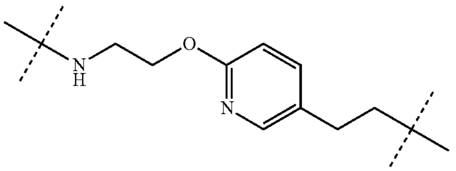
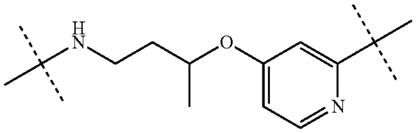
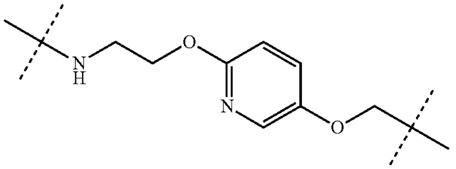
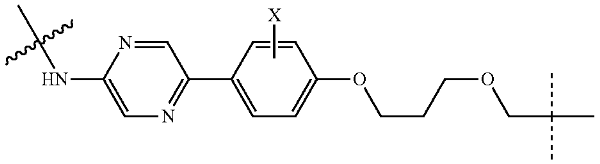
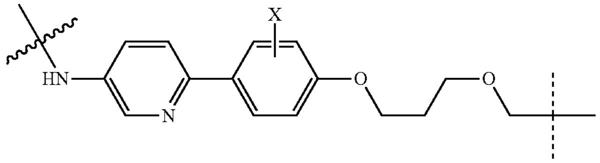
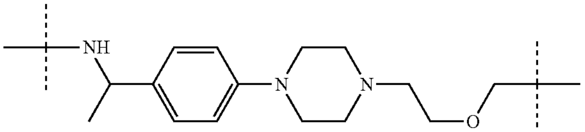
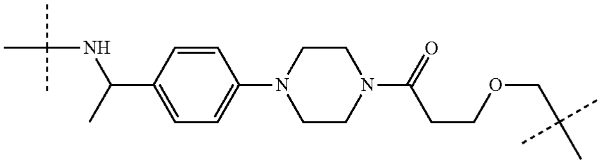
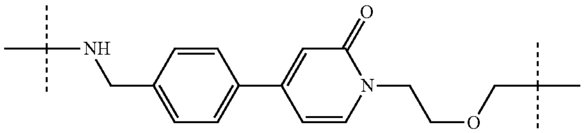
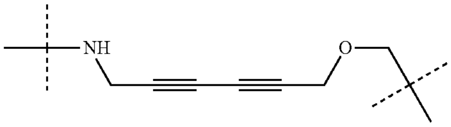
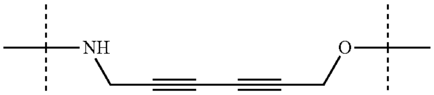
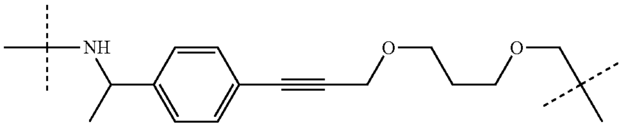
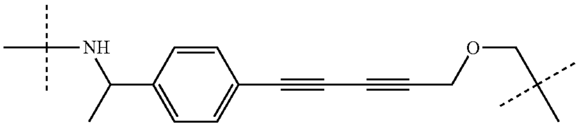
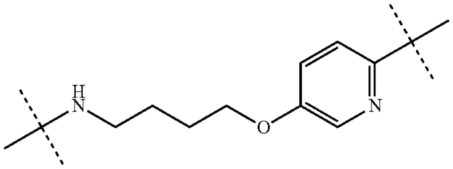
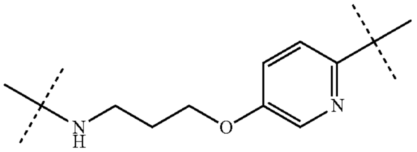
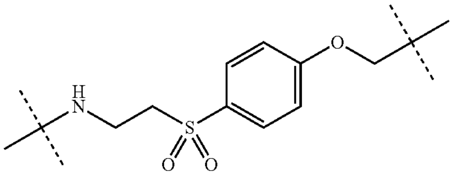
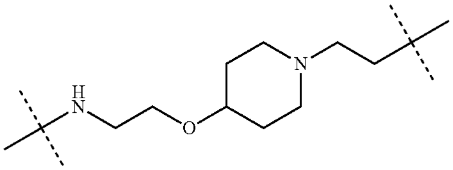
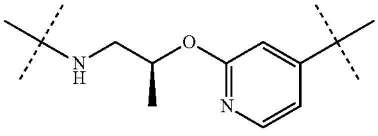
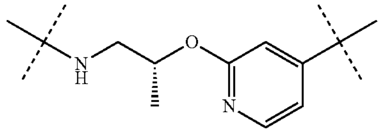
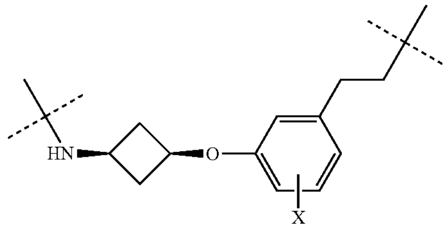
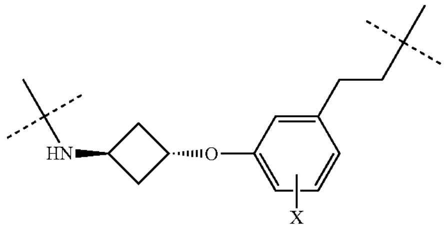
X = H, F -continued
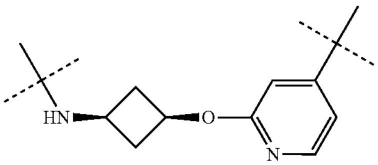
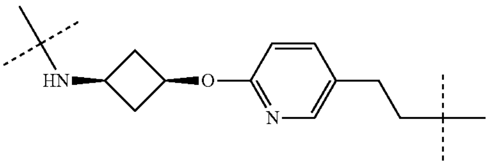
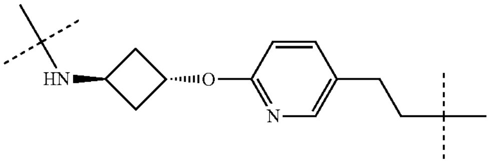
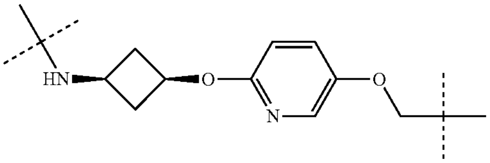
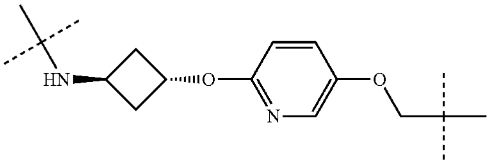
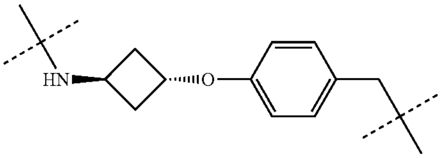
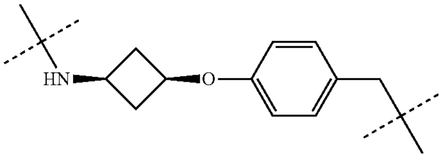
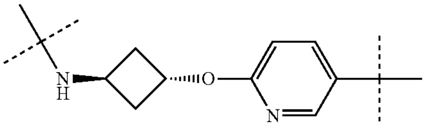
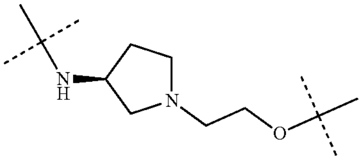
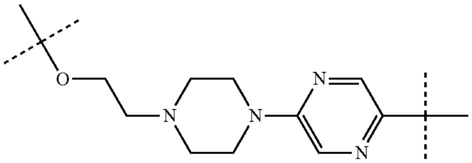
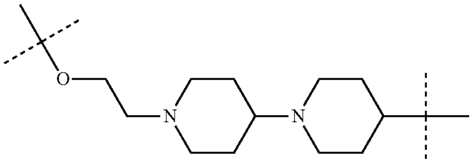
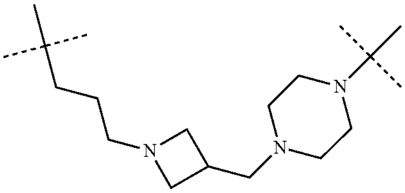
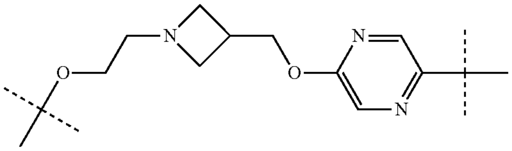
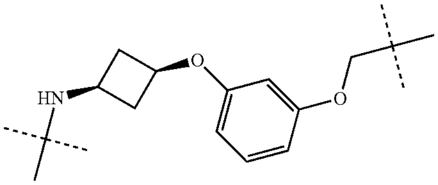
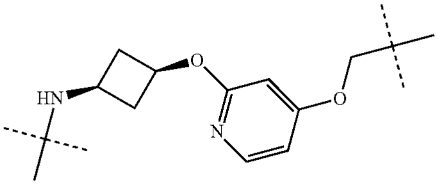
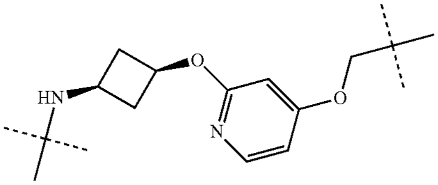
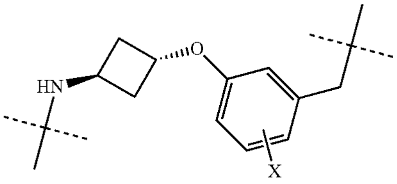

-continued
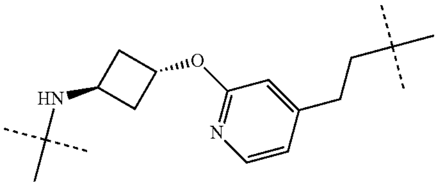
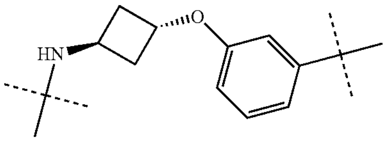
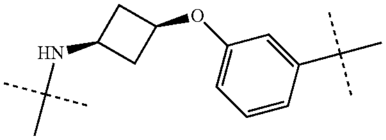
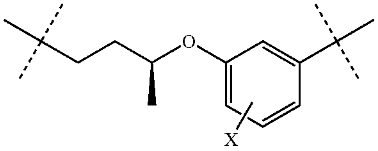
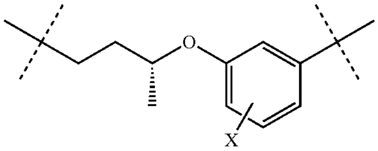
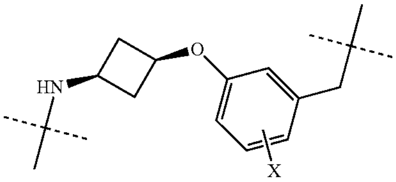
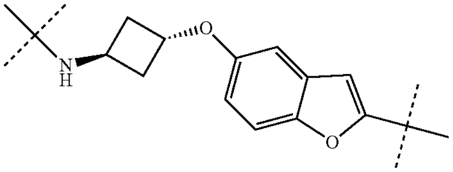
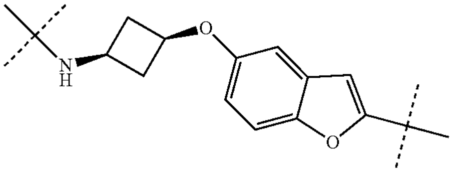
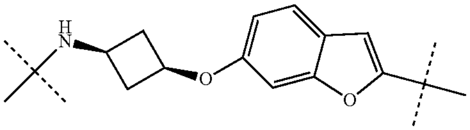
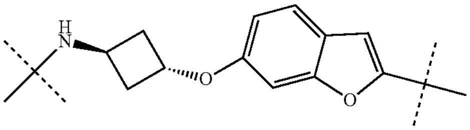
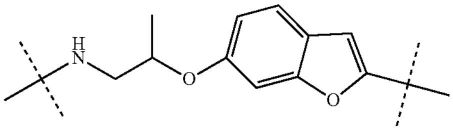
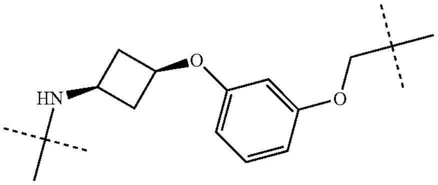
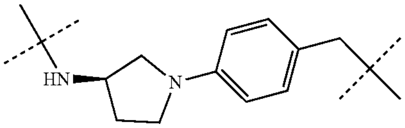
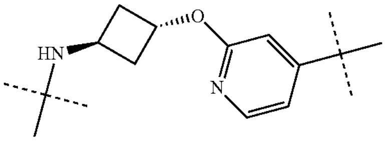
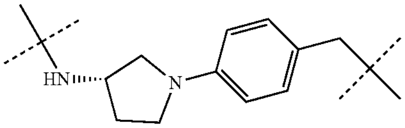
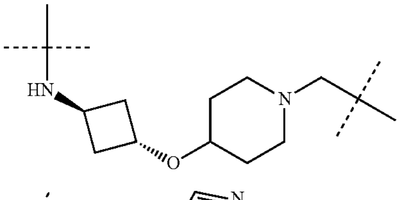
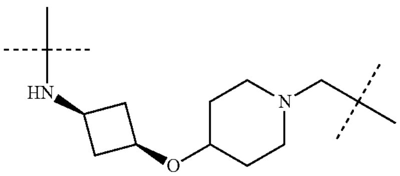
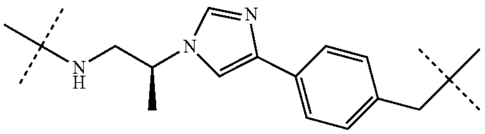
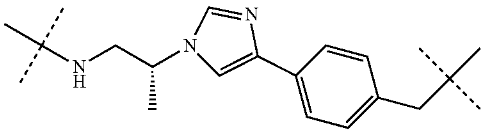
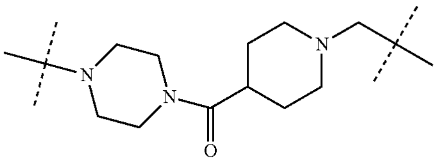

-continued
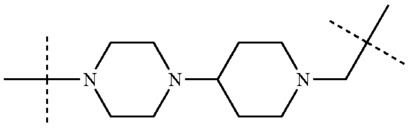
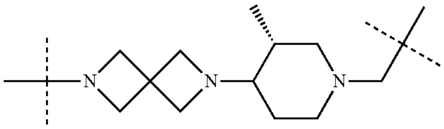
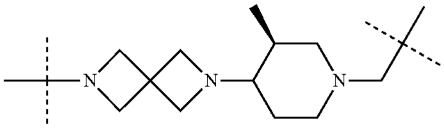
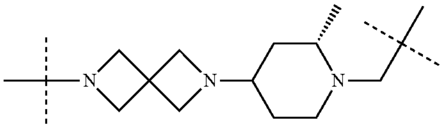
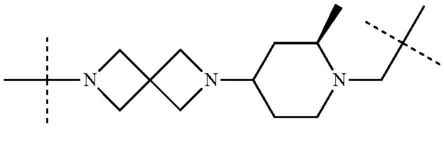
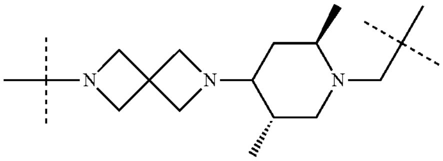
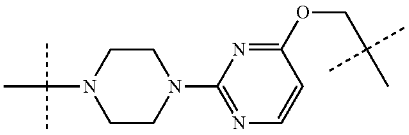
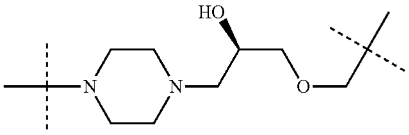
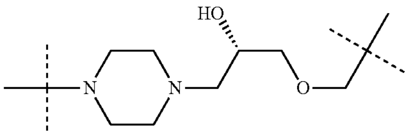
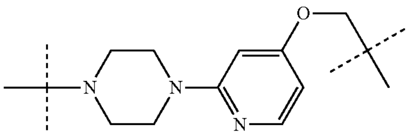
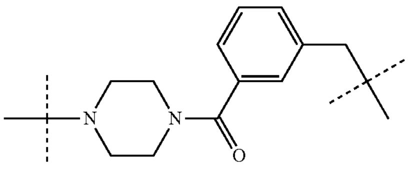
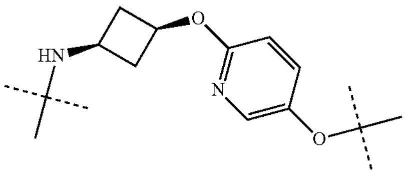
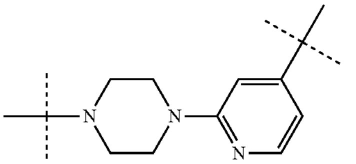
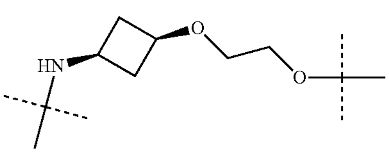
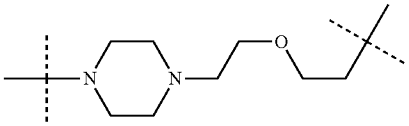
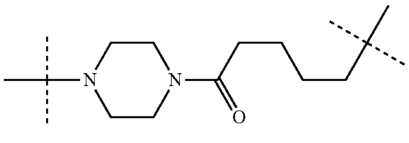
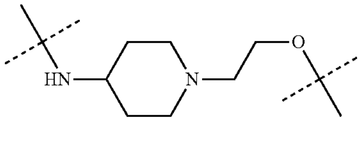
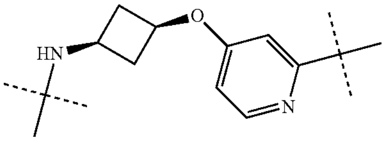
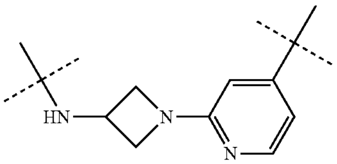
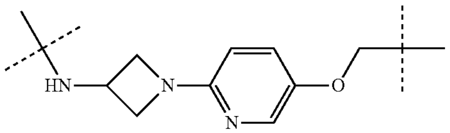
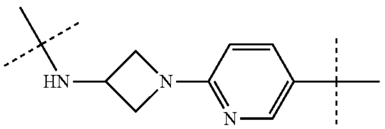
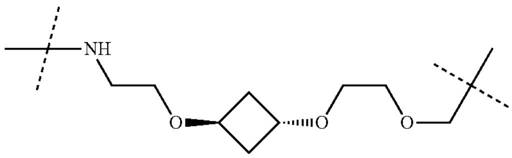
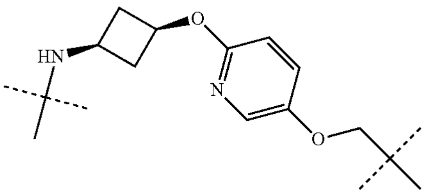
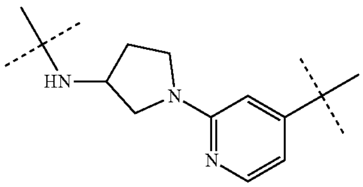
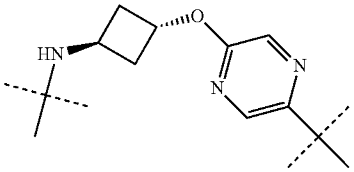

-continued
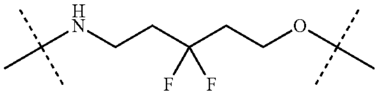
9. The bifunctional compound according to claim 1, or a pharmaceutically acceptable salt, enantiomer, or stereoisomer thereof, wherein the chemical linker group (L) is selected from the group consisting of:
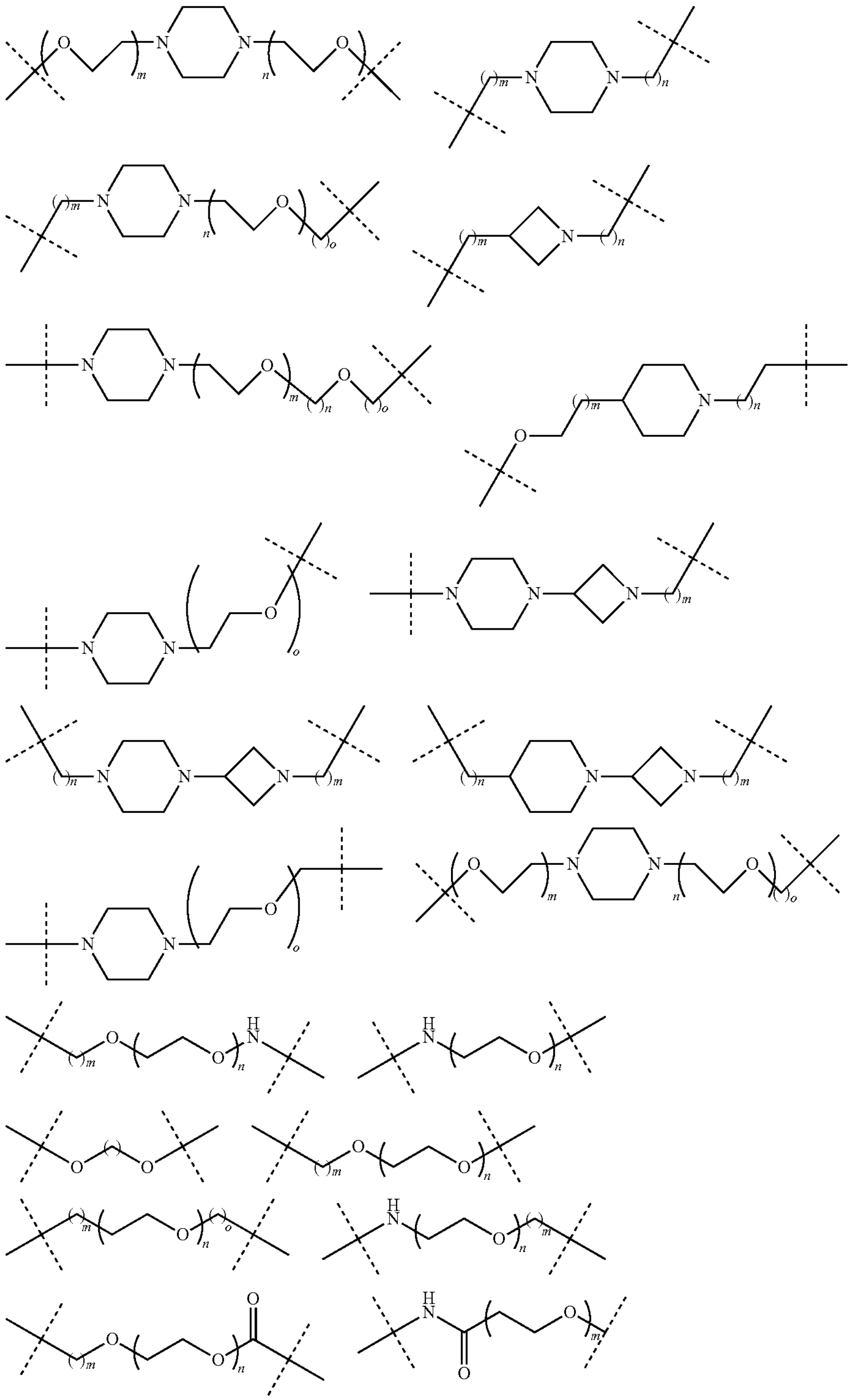

-continued
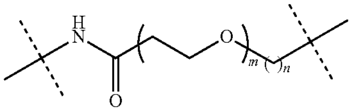
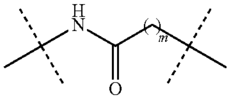
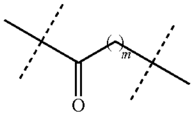
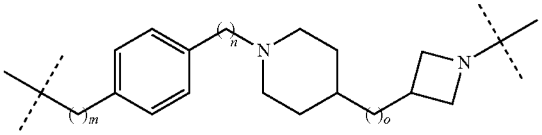
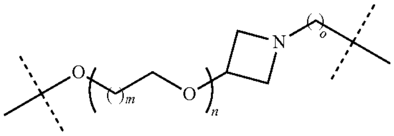
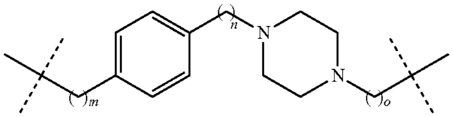
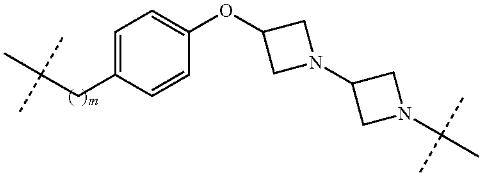
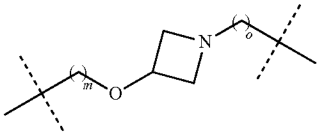
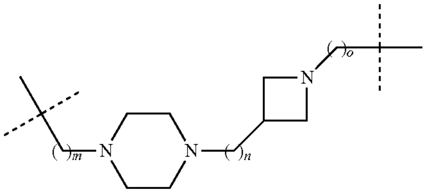
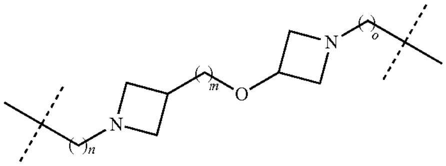
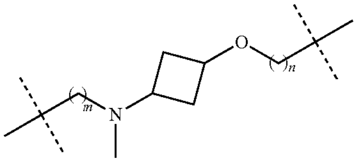
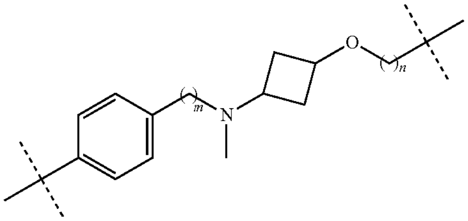
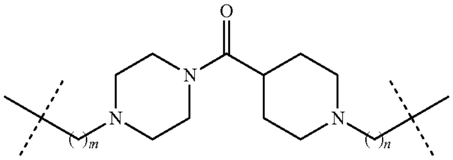
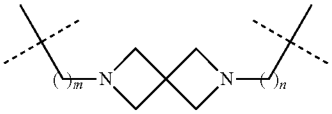
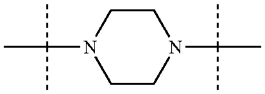
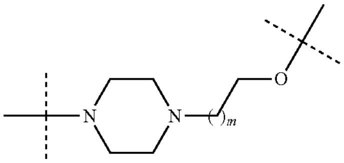
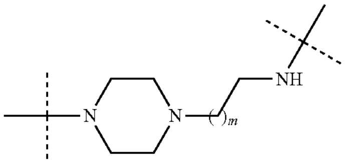
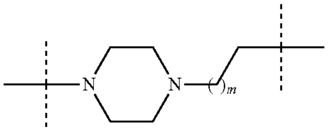
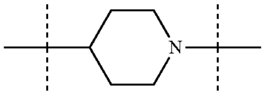
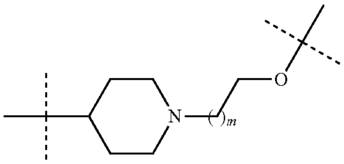

-continued
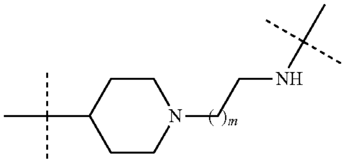
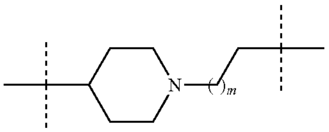
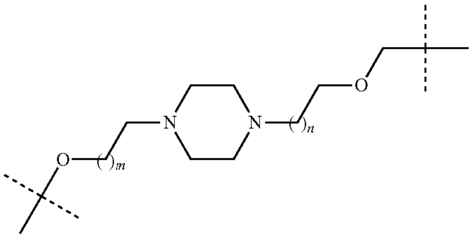
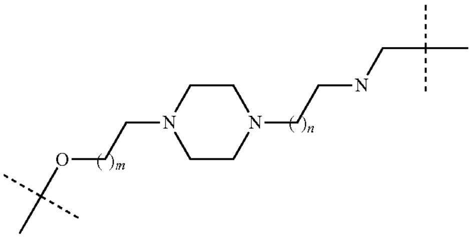
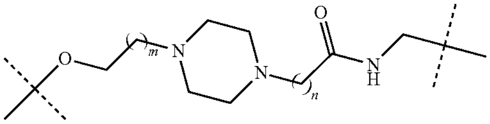
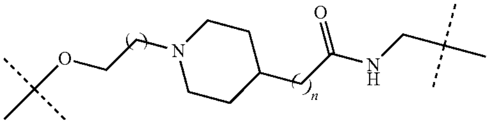
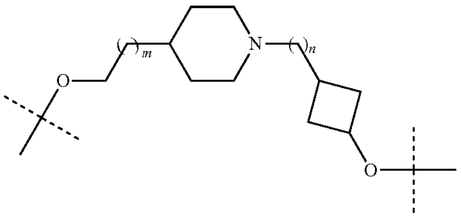
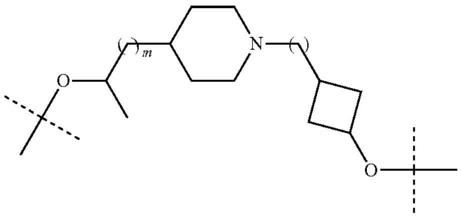
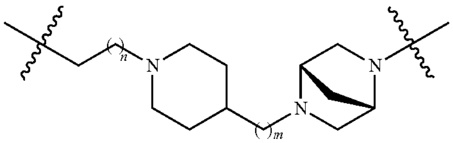
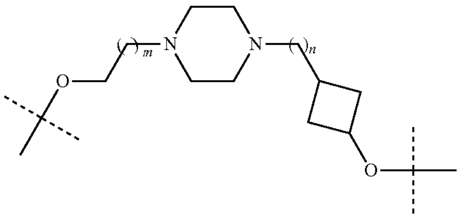
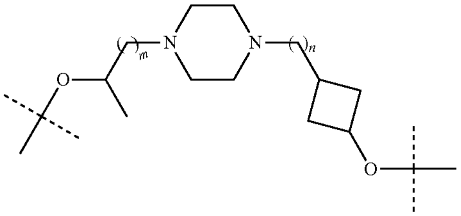
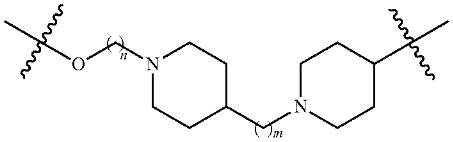
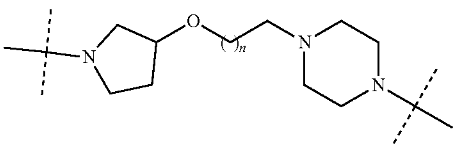
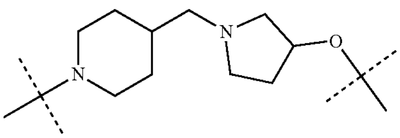
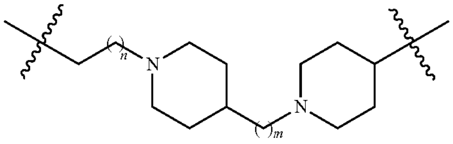
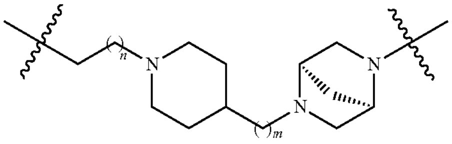
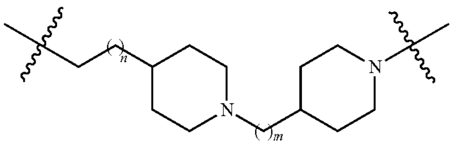
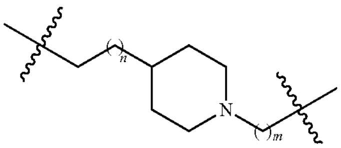

-continued
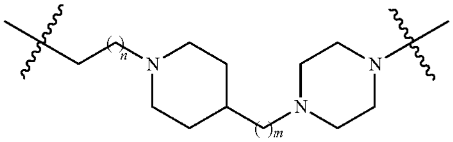
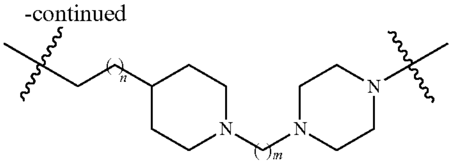
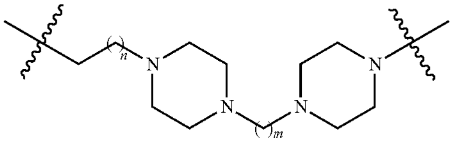
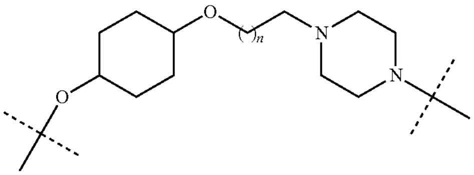
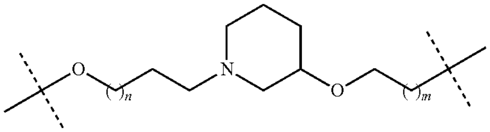
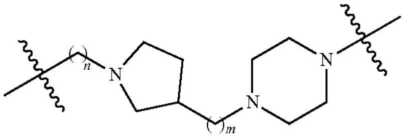
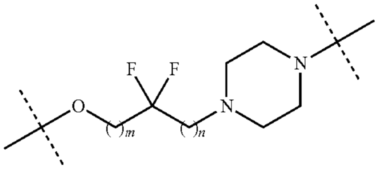
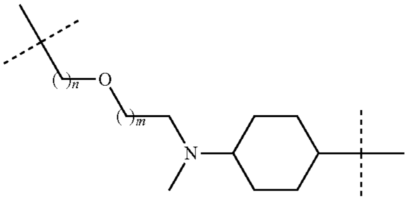
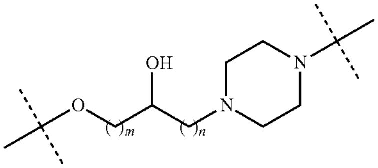
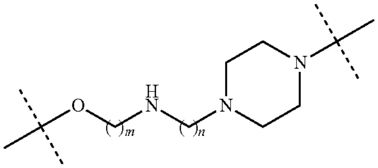
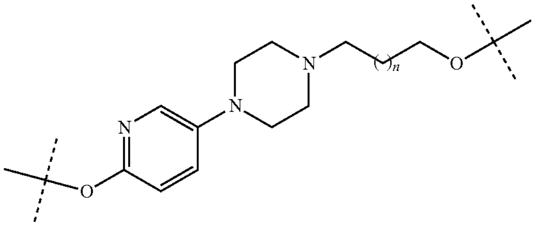
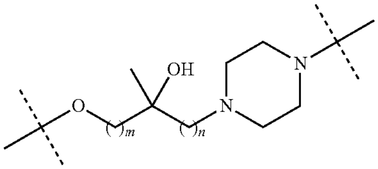
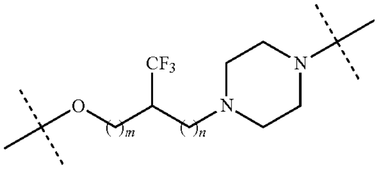
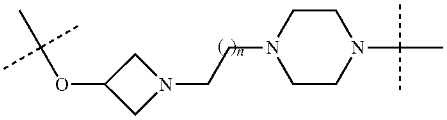
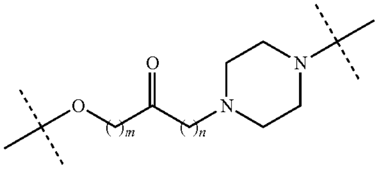
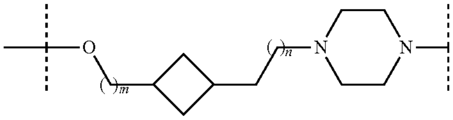
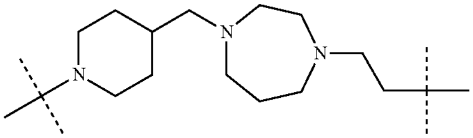
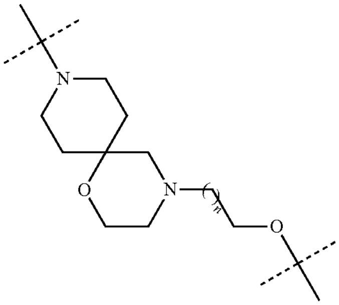

-continued
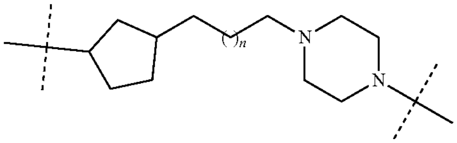
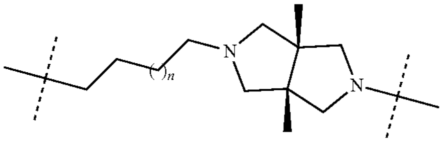
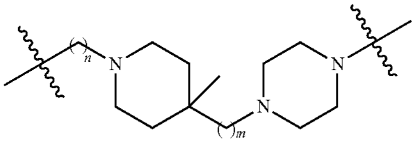
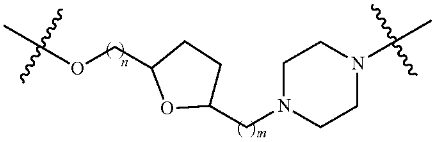
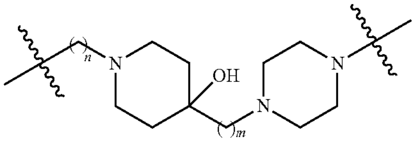
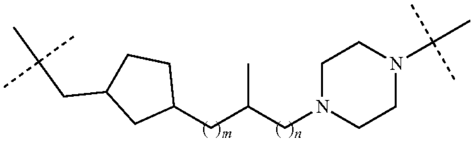
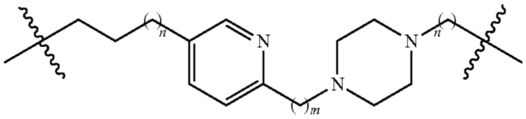
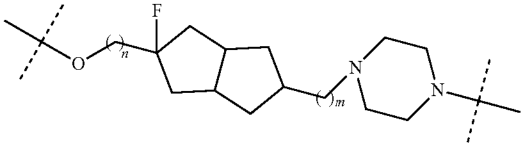
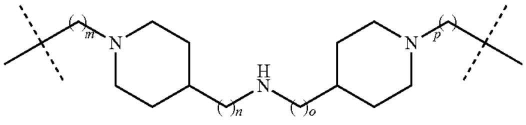
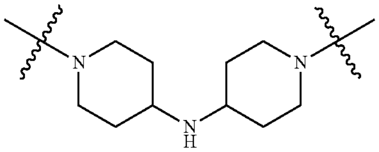
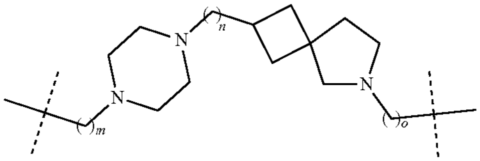
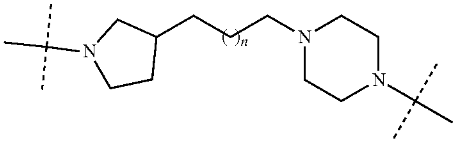
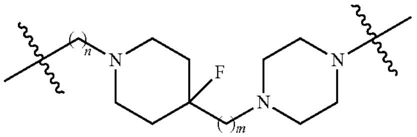
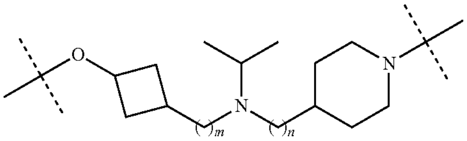
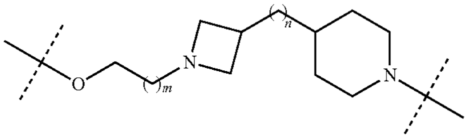
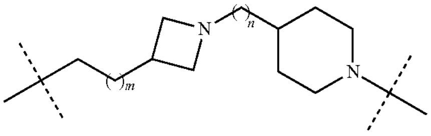
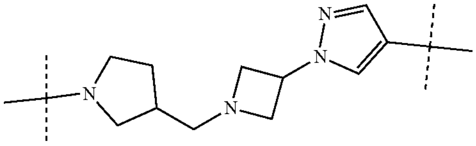
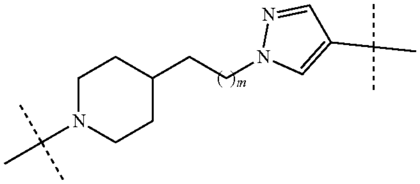
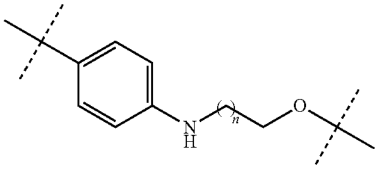
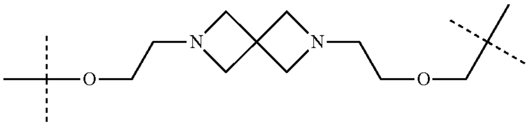
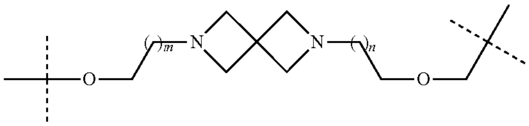
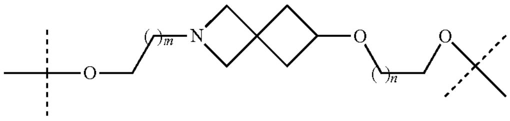

-continued
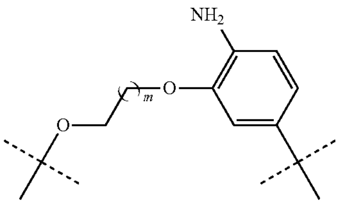
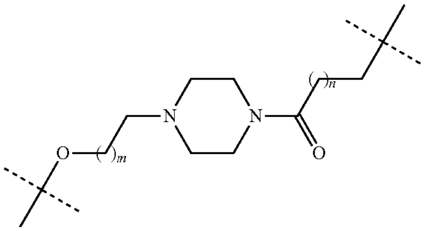
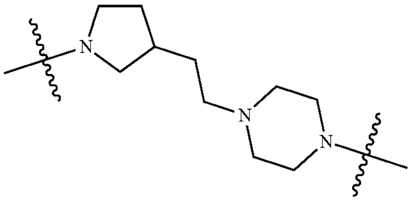
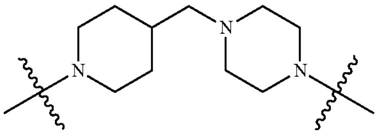
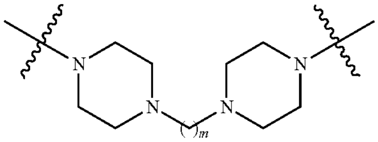
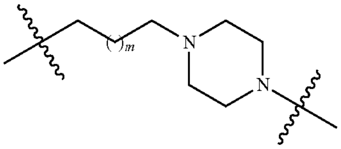
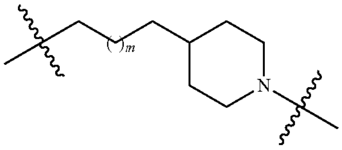
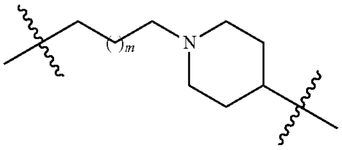
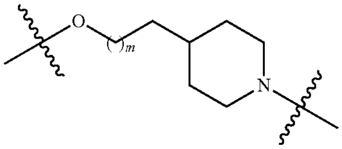
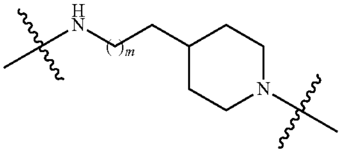
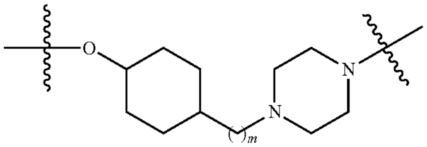
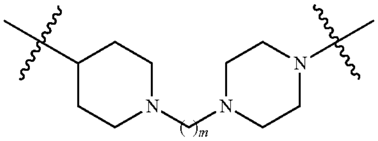
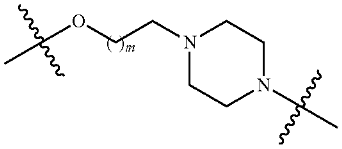
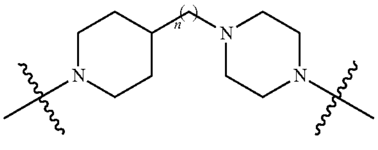
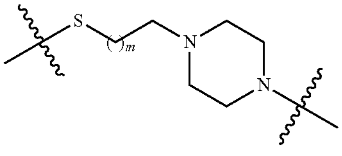
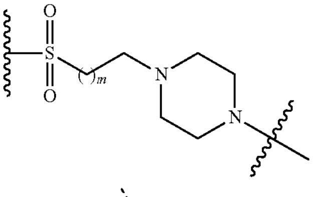
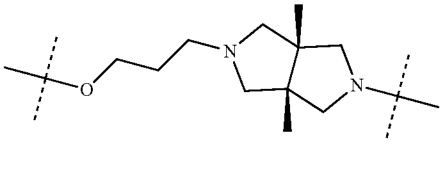
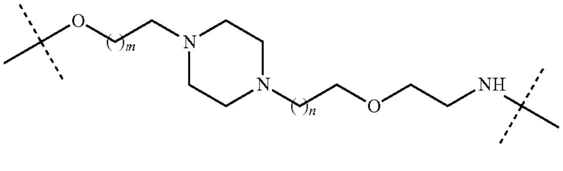

-continued
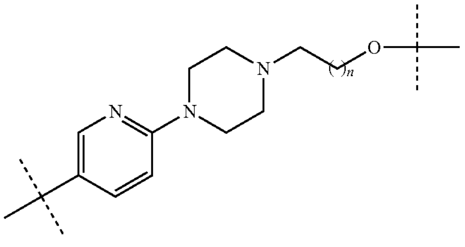
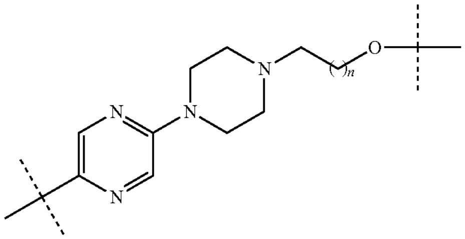
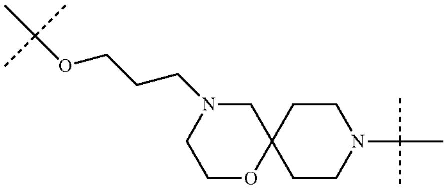
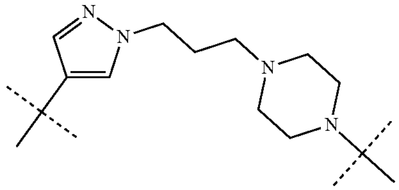
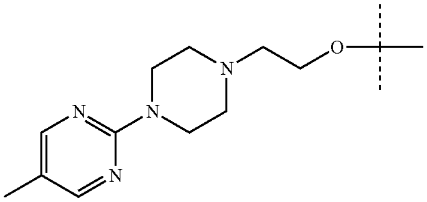
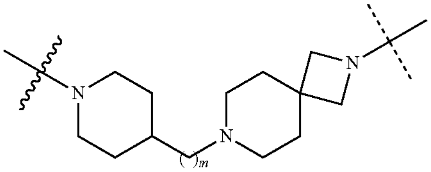
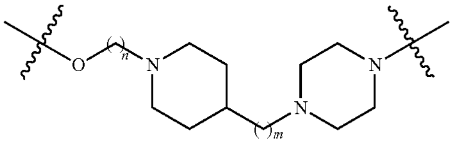
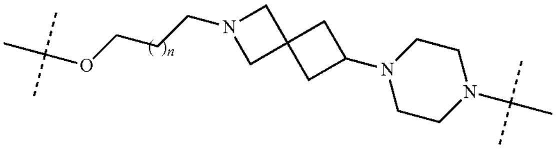
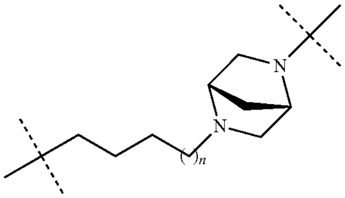
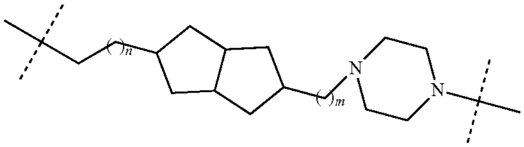
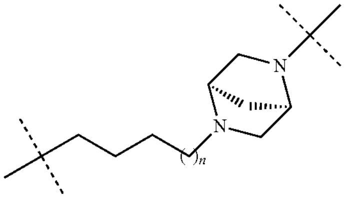
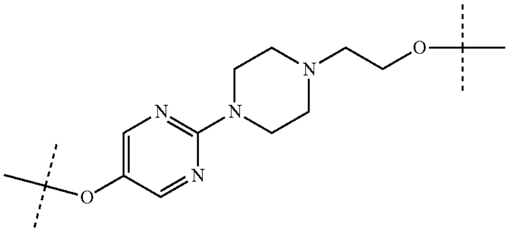
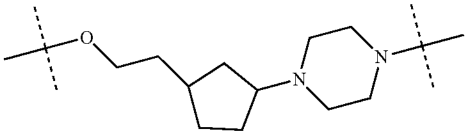
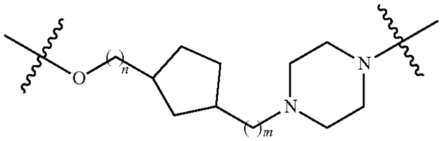
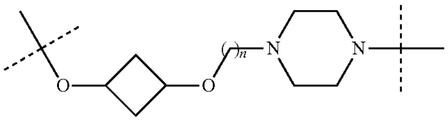
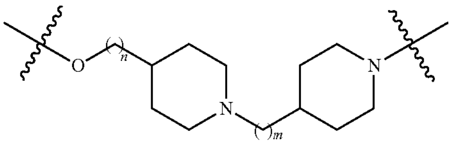
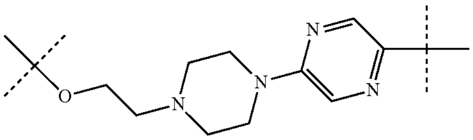
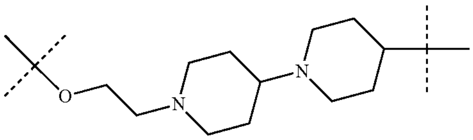

-continued
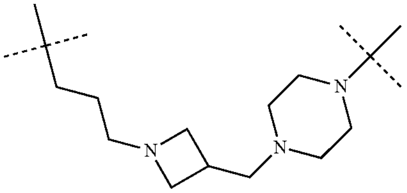
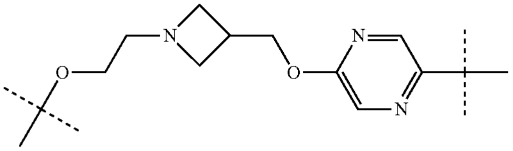
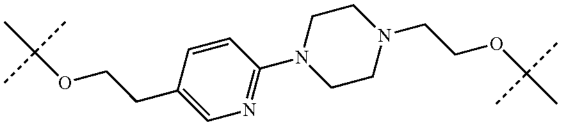
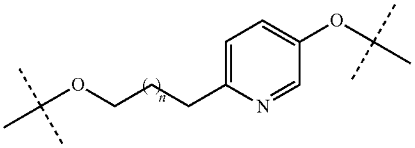
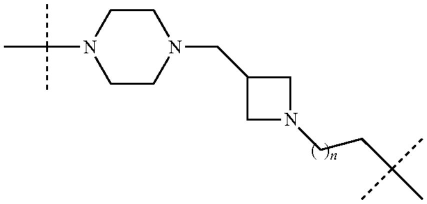
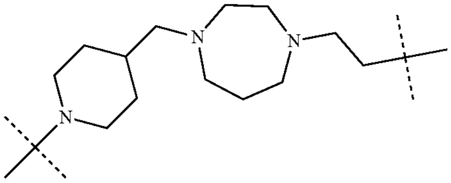
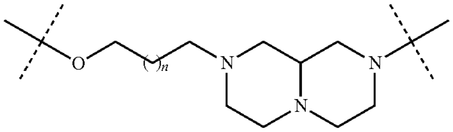
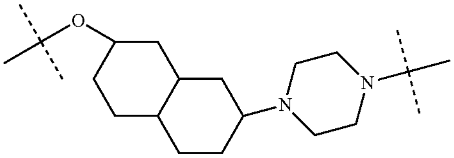
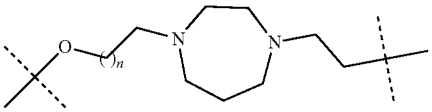
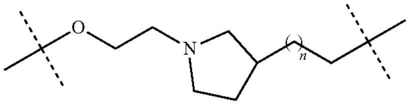
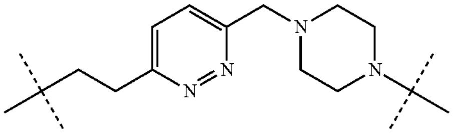
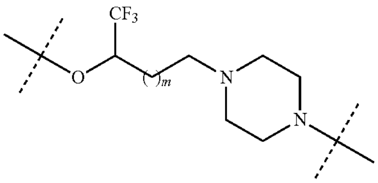
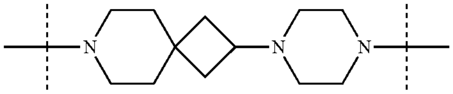
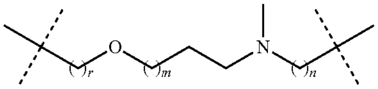
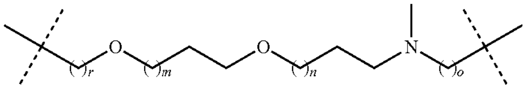
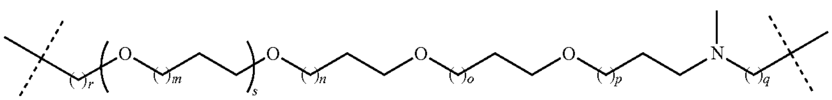
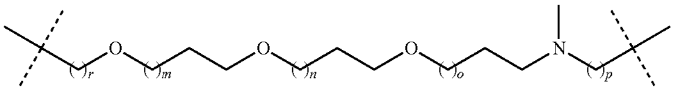
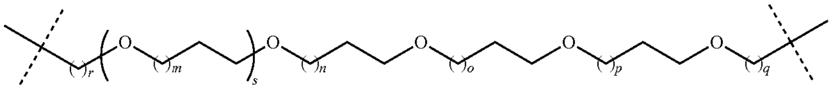
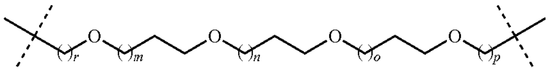
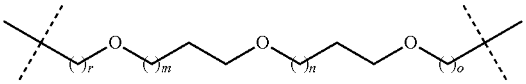
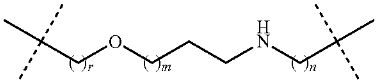
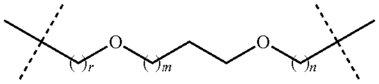
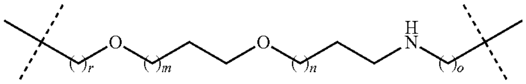

-continued
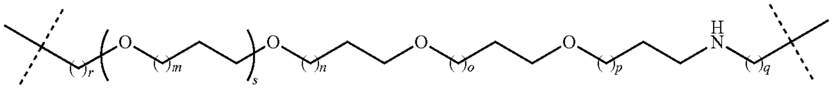
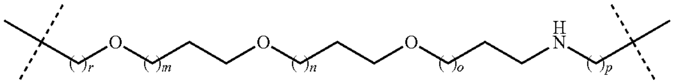
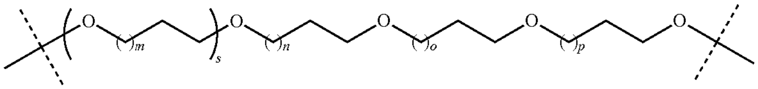
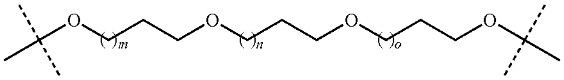
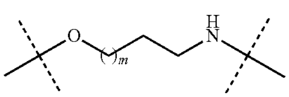
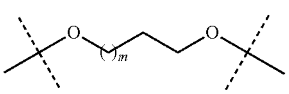
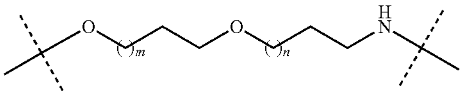
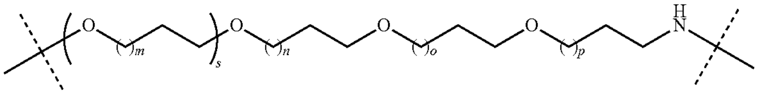
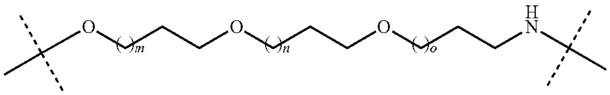
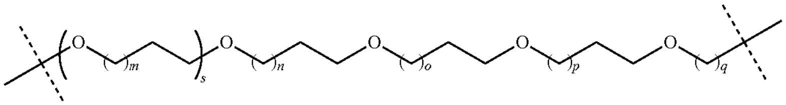
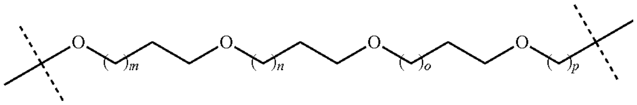
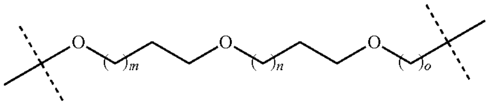
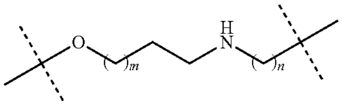
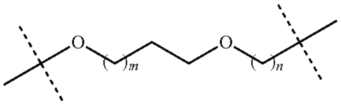
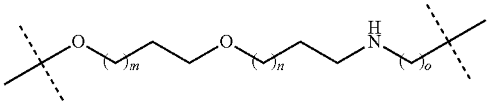
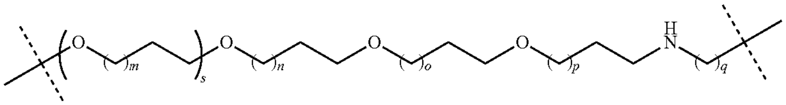
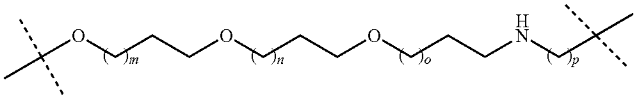
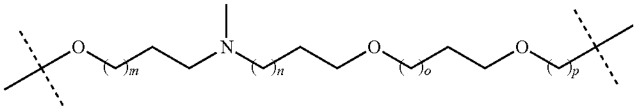
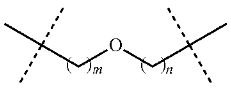
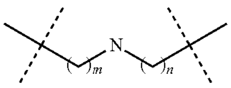
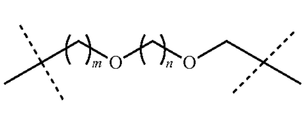
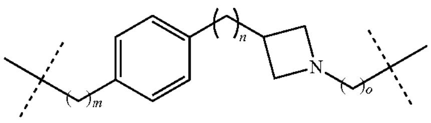
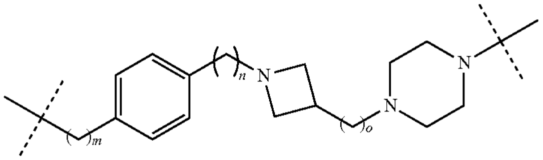
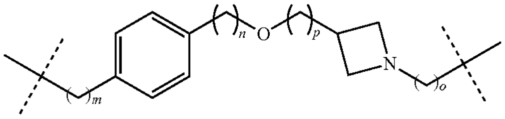

-continued
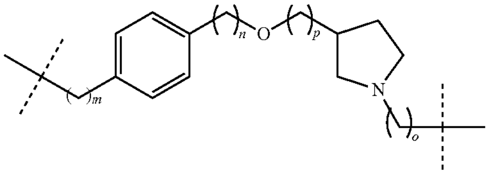
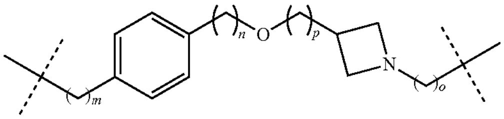
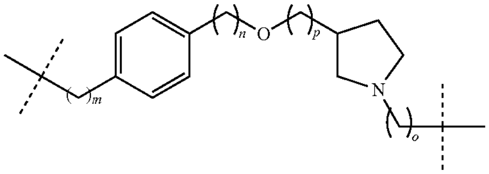
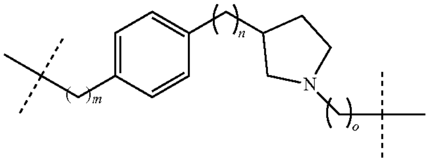
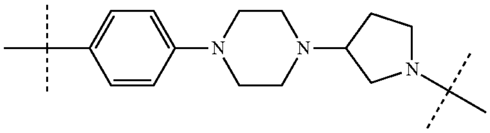
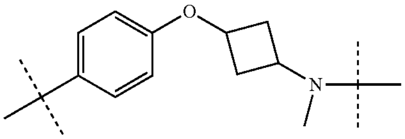
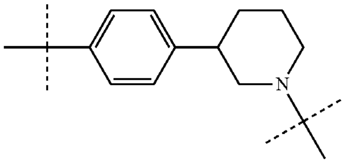
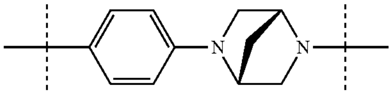
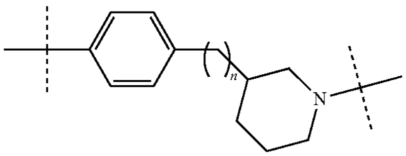
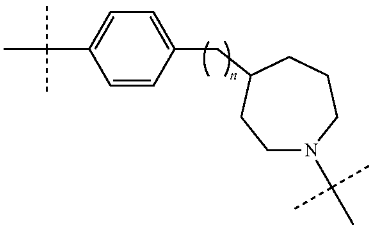
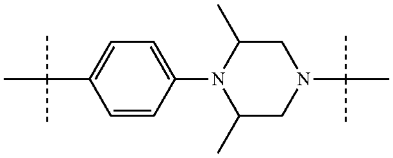
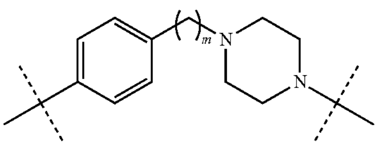
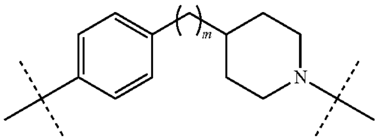
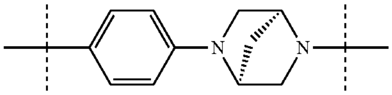
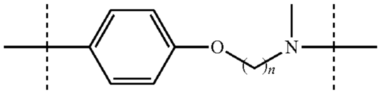
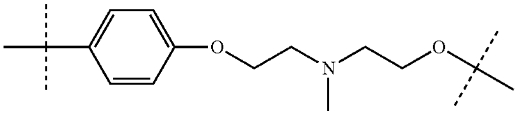
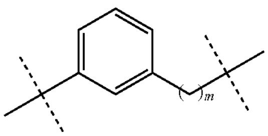
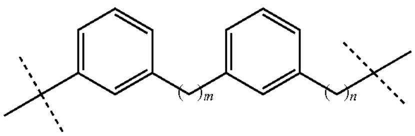
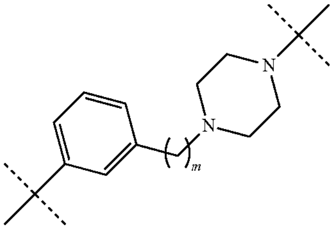
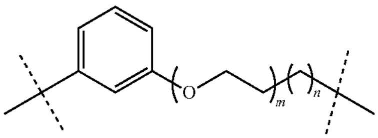
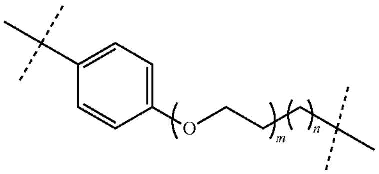

-continued
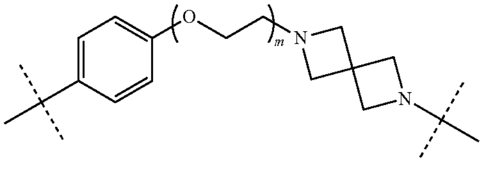
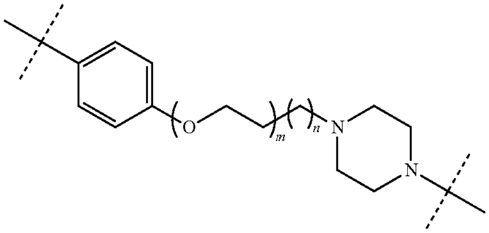
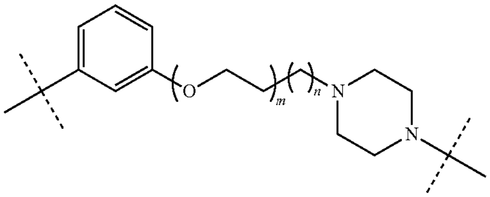
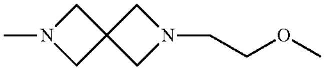
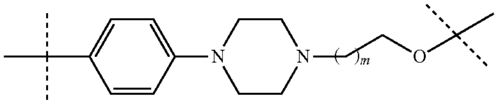
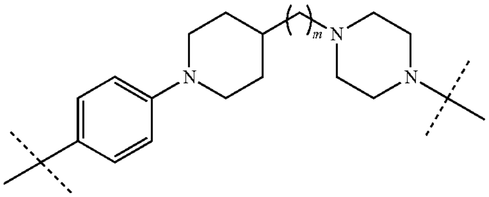
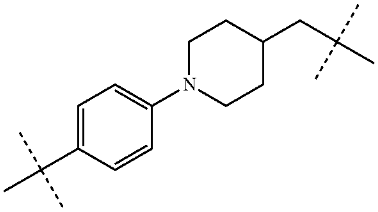
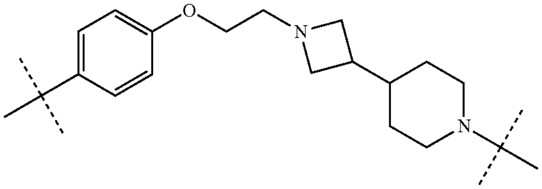
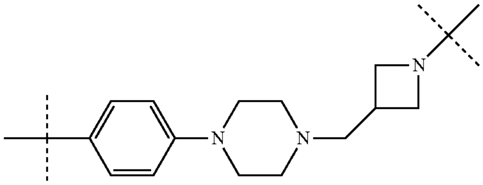
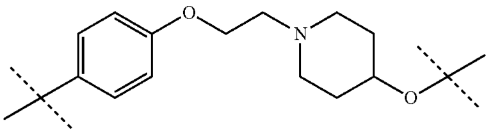
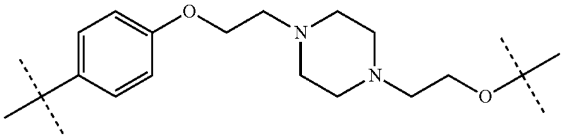
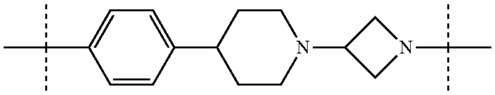
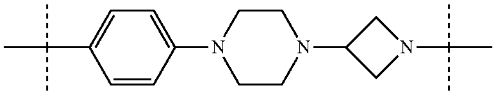
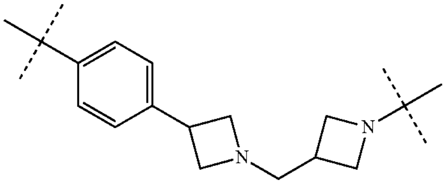
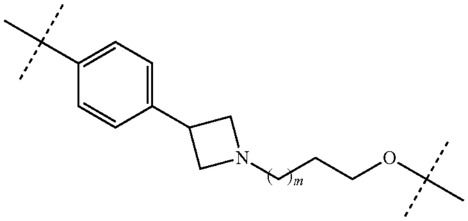
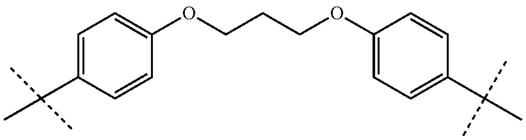
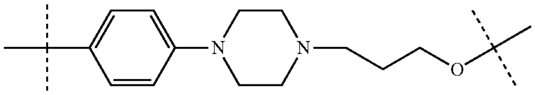
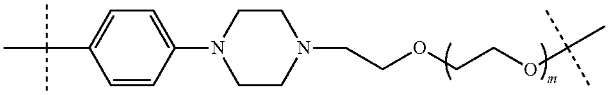

-continued
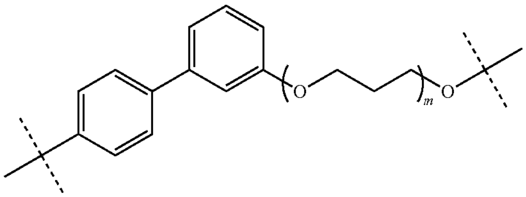
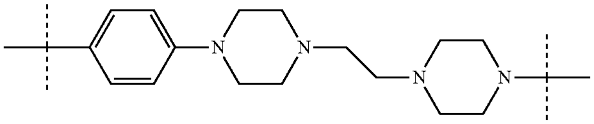
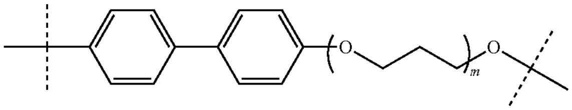
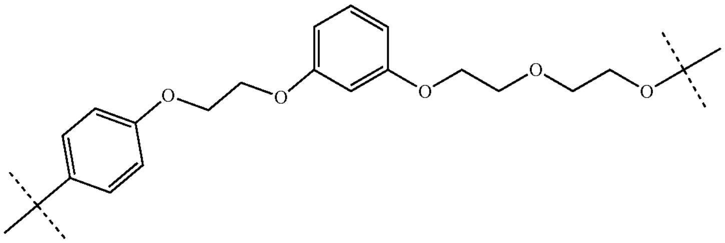
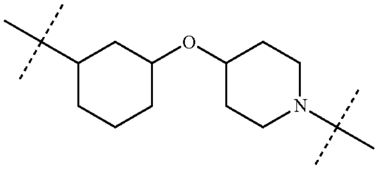
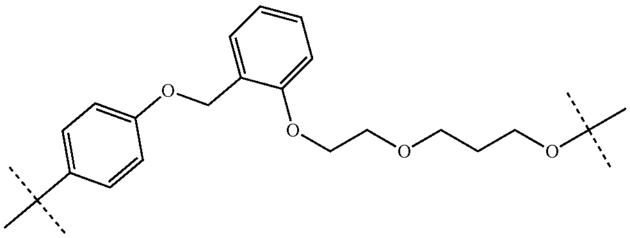
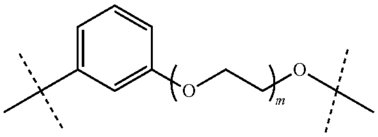
,
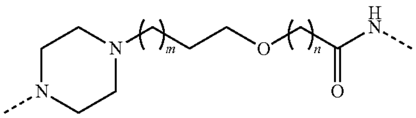
,
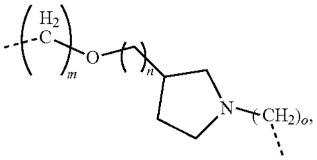
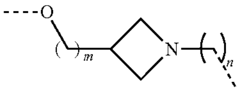
, and
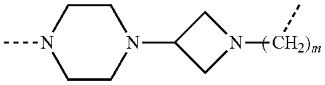
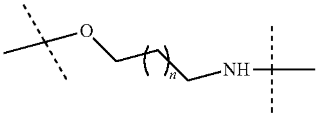
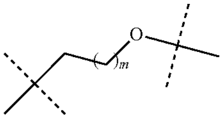
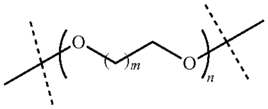
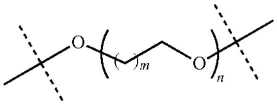
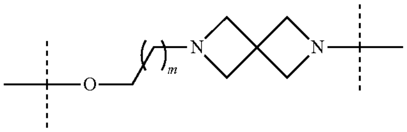
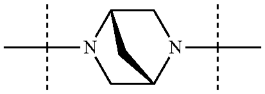
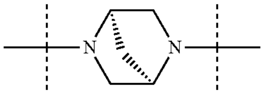
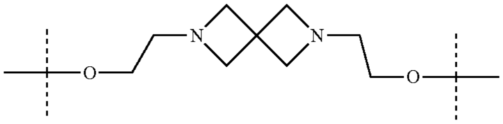
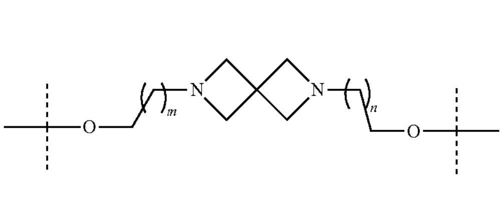
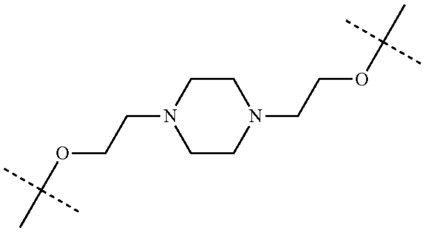

-continued
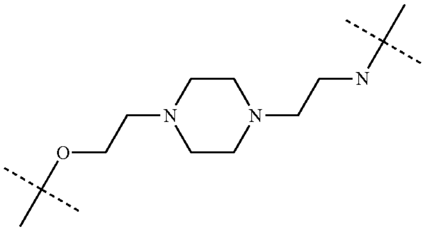
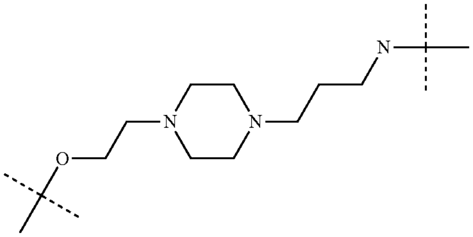
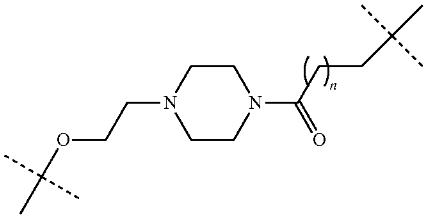
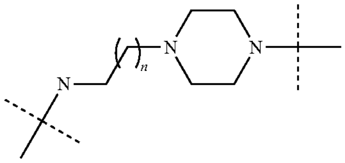
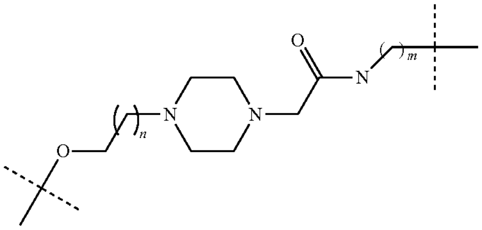
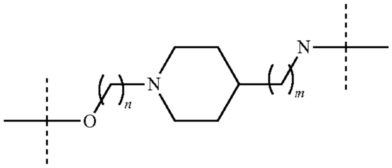
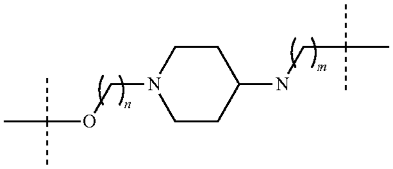
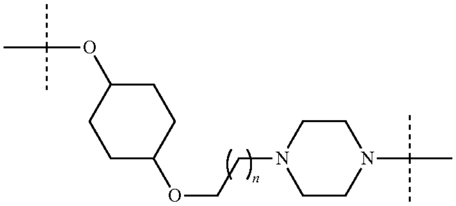
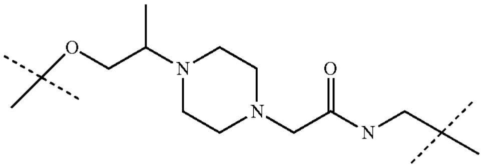
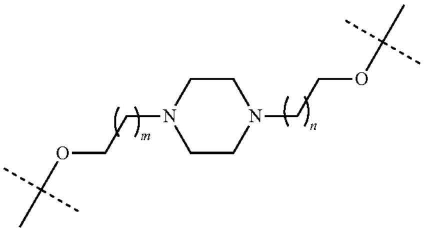
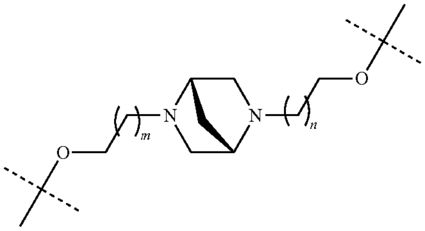
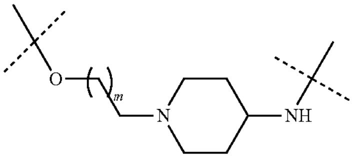
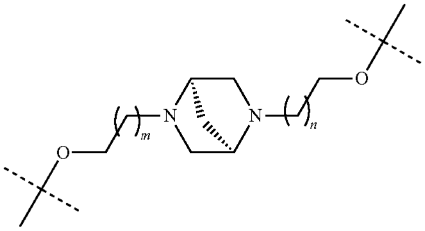
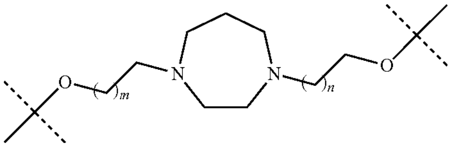

-continued
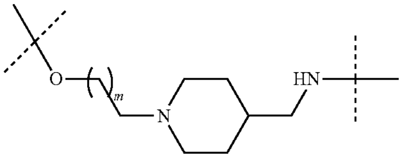
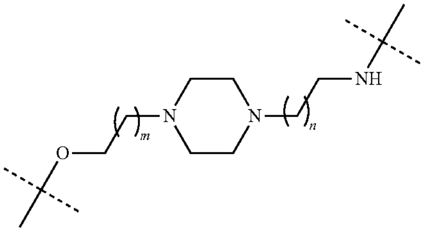
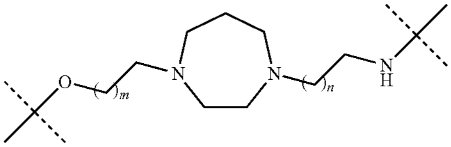
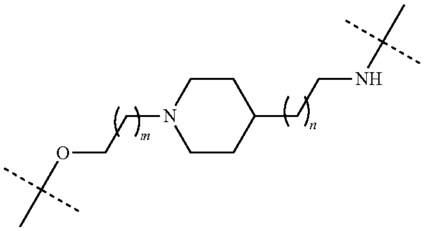
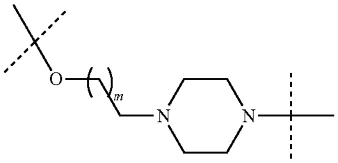
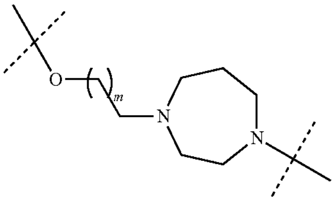
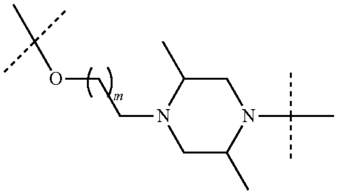
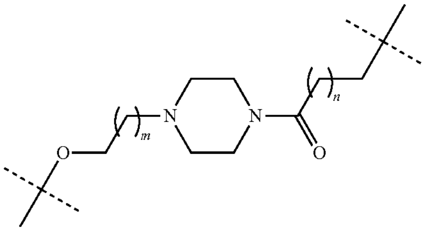
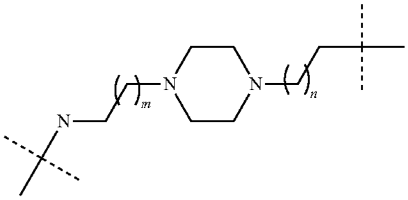
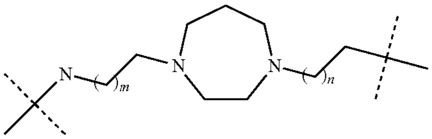
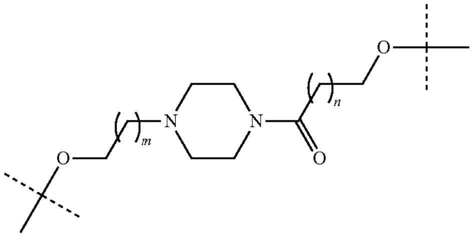
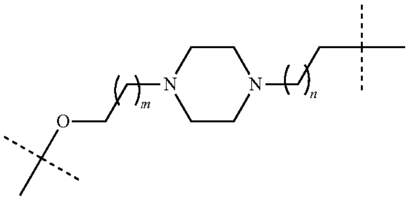
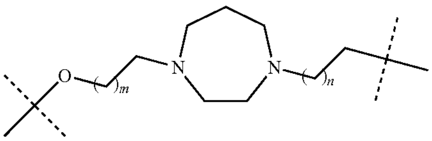
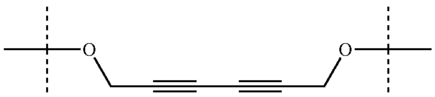
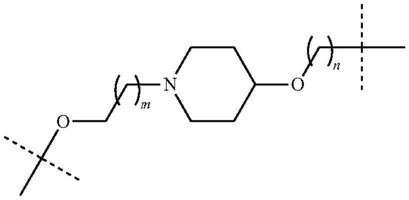

-continued
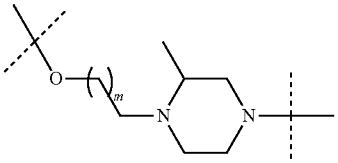
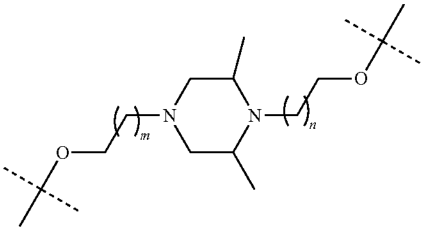
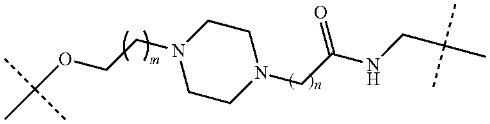
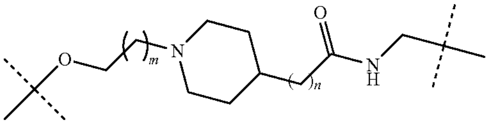
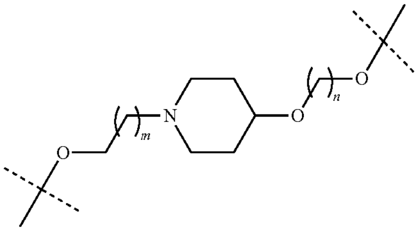
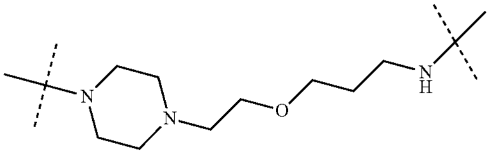
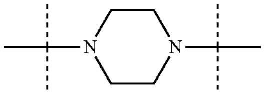
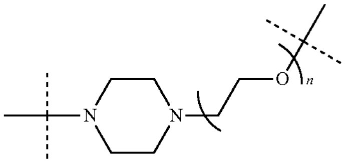
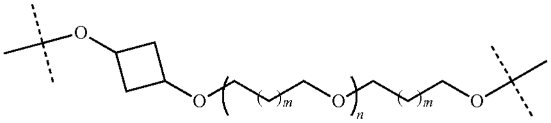
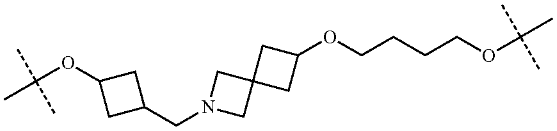
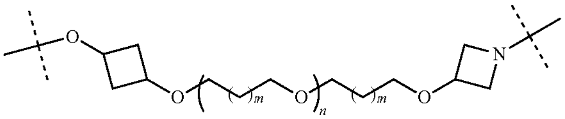
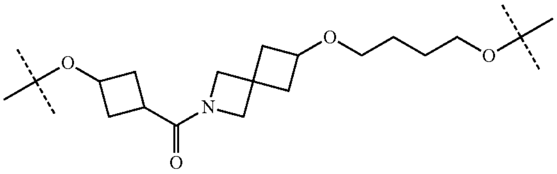
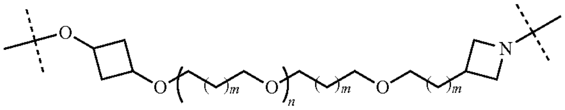
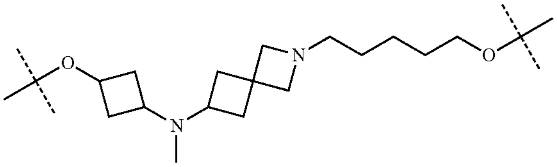
-continued
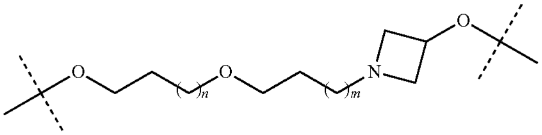
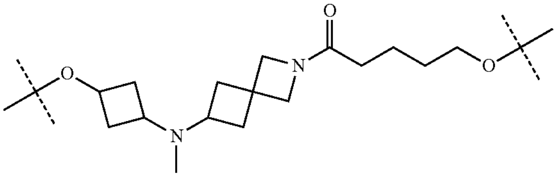
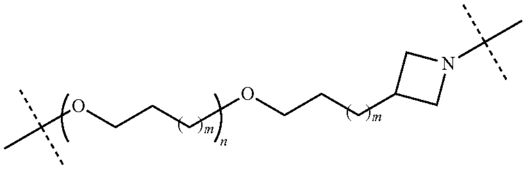
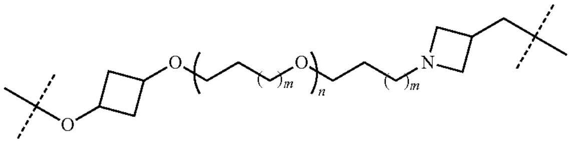
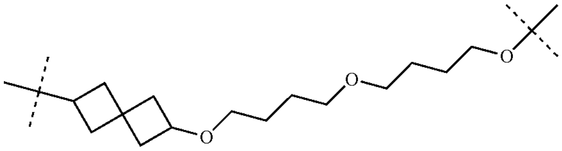

-continued
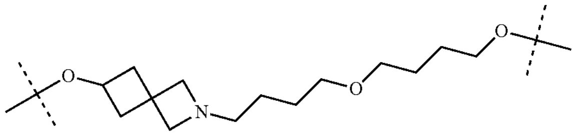
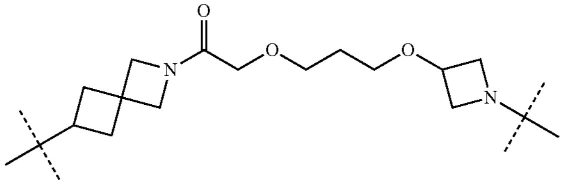
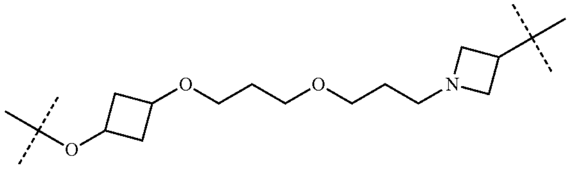
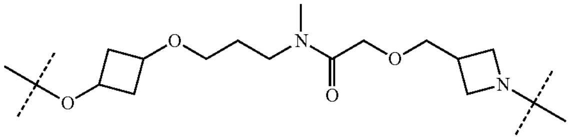
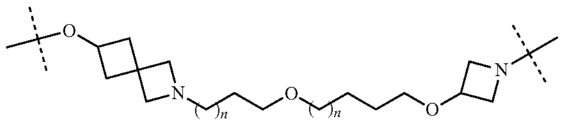
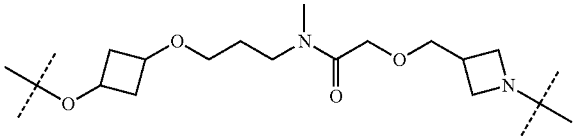
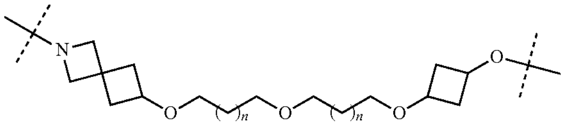
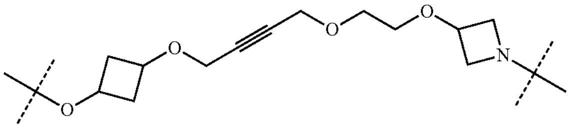
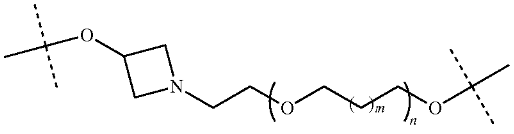
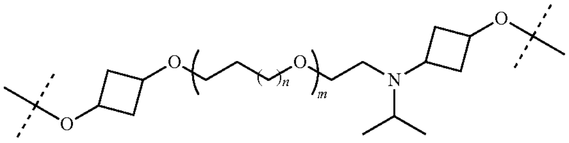
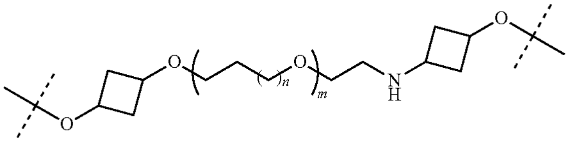
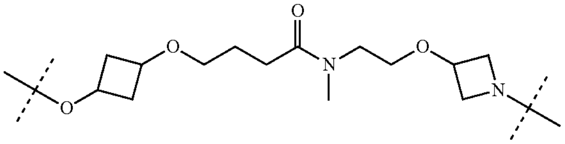
-continued
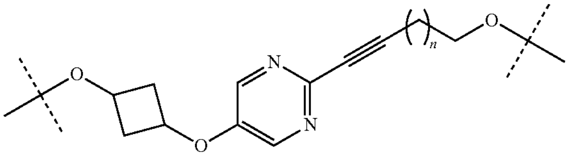
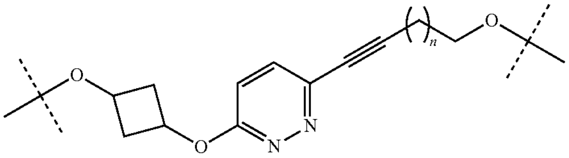
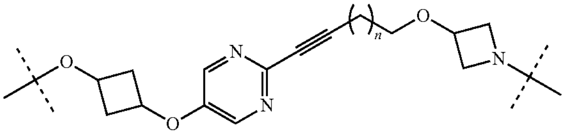
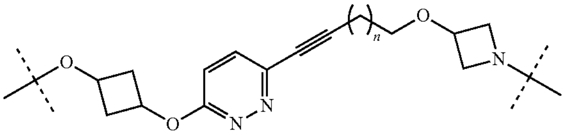
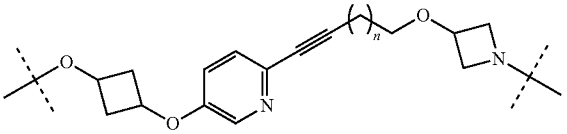
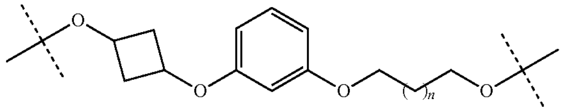
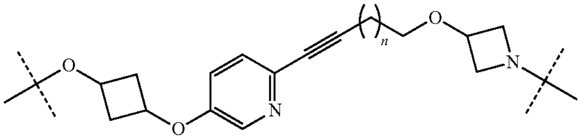
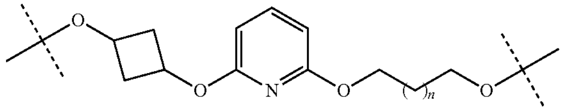
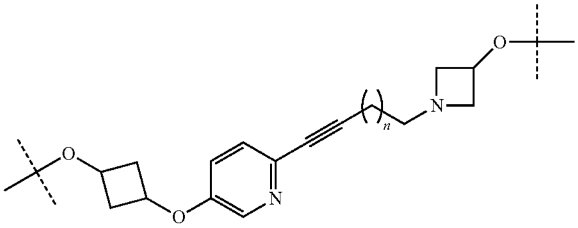
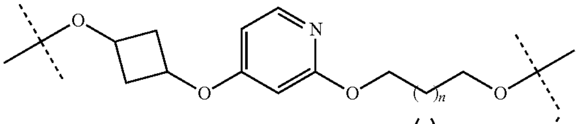
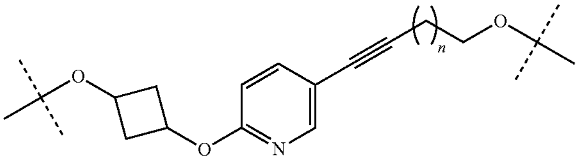
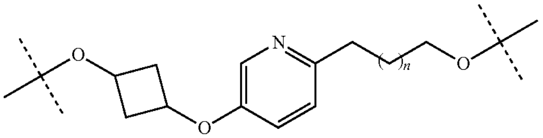

-continued
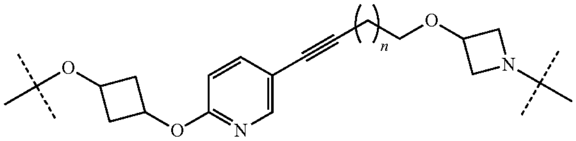
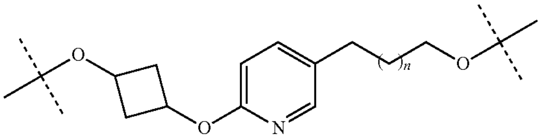
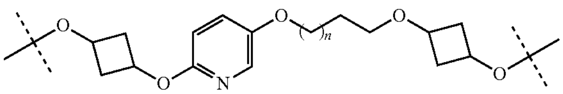
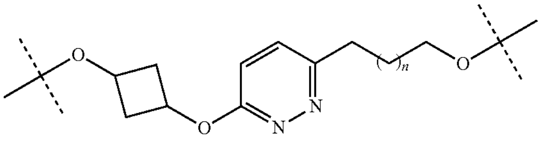
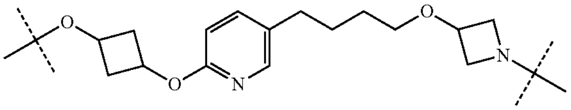
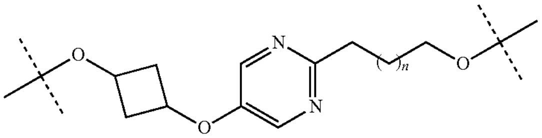
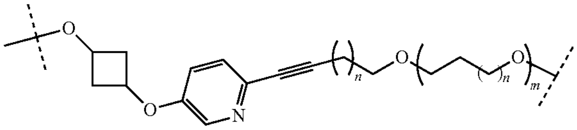
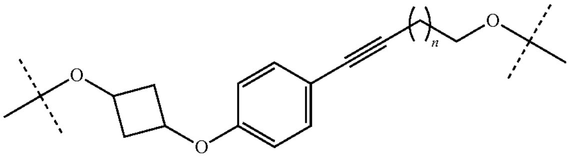
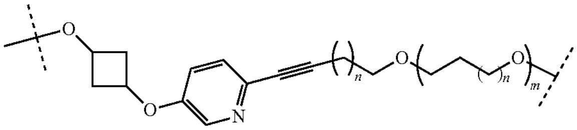
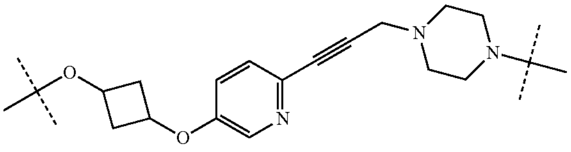
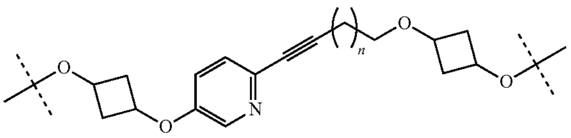
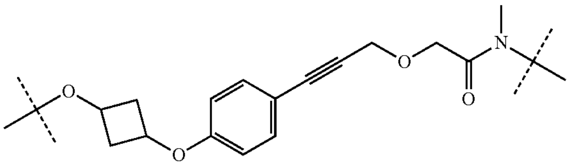
-continued
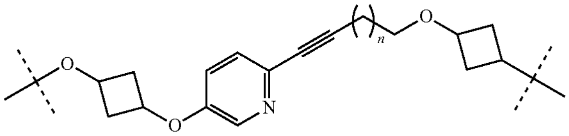
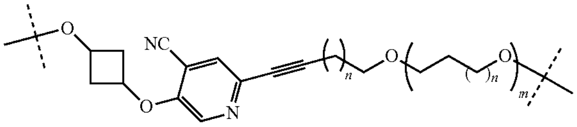
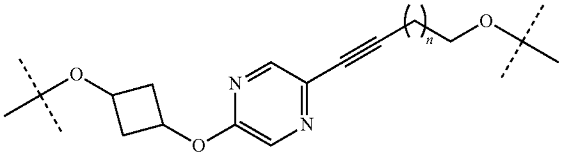
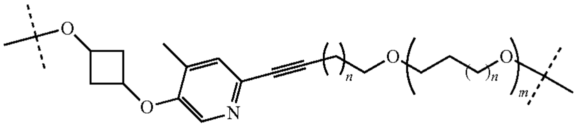
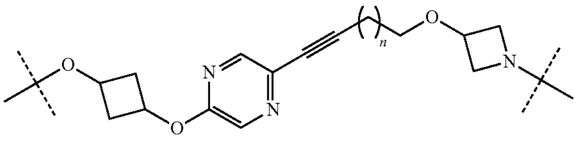
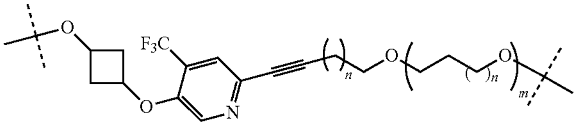
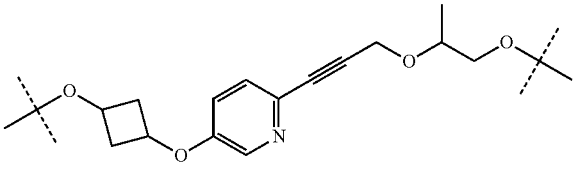
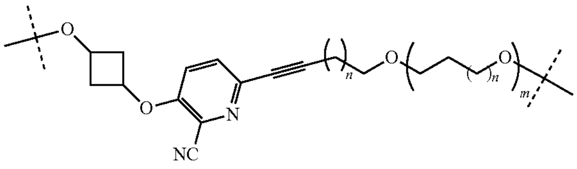
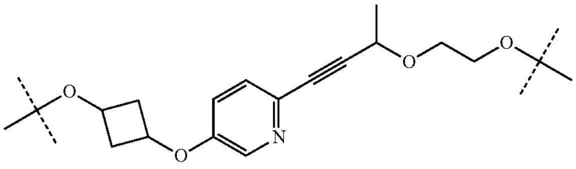
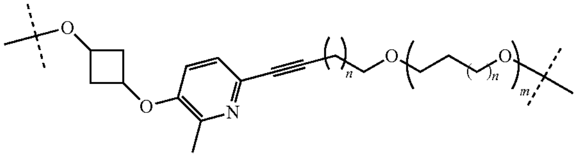
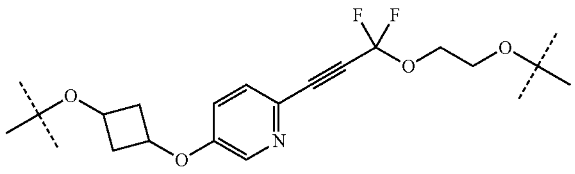

-continued
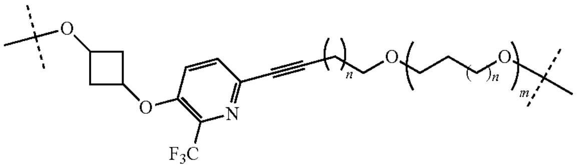
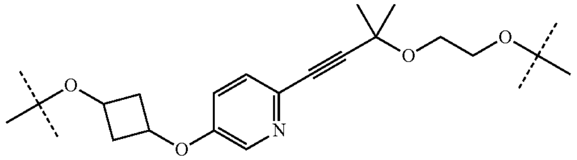
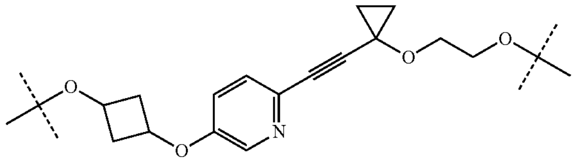
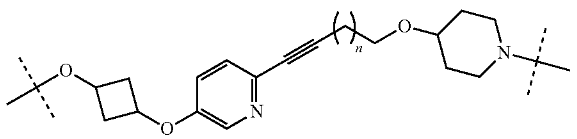
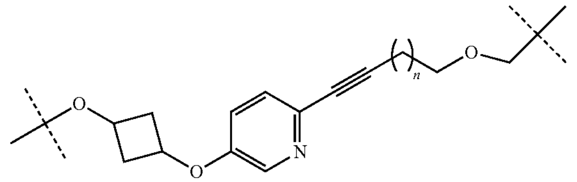
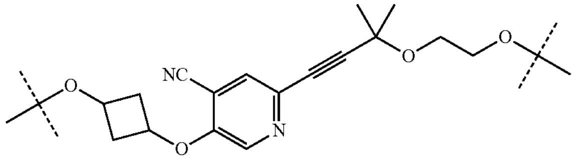
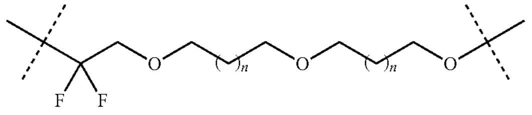
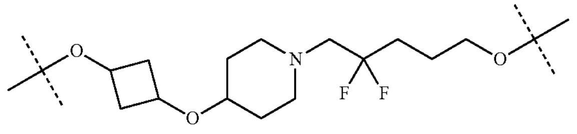
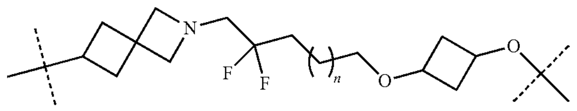
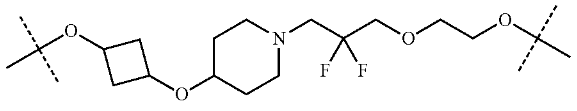
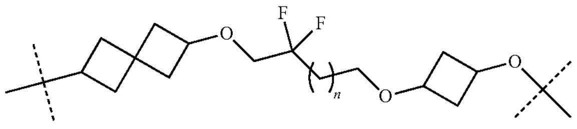
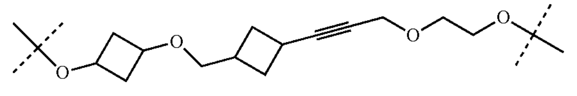
-continued
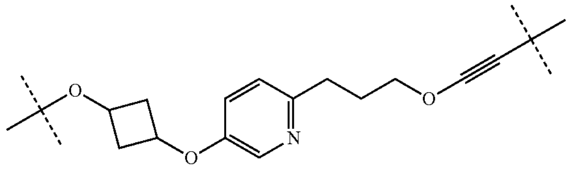
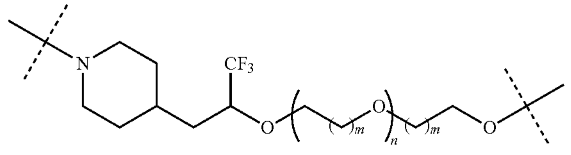
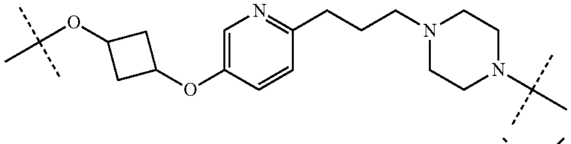
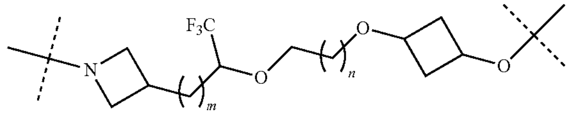
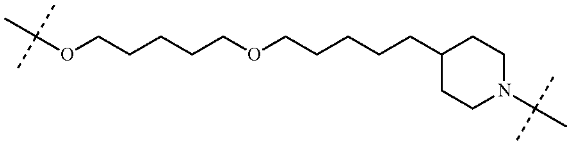
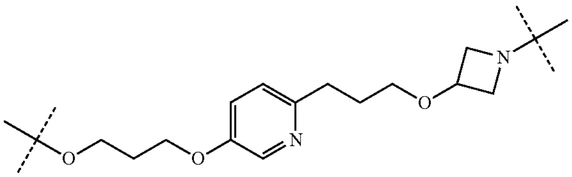
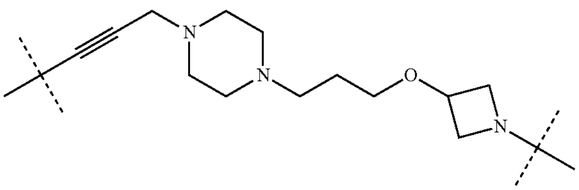
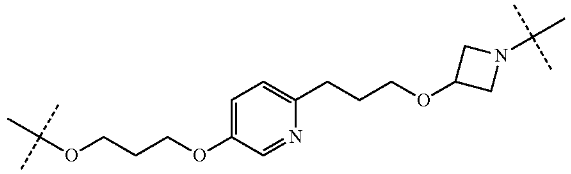
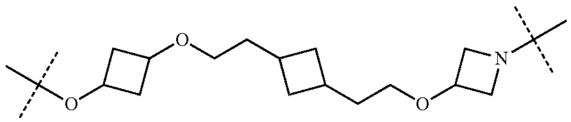
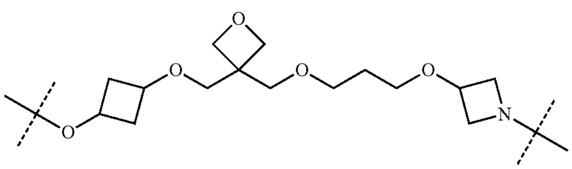
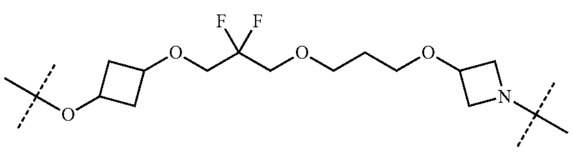

-continued
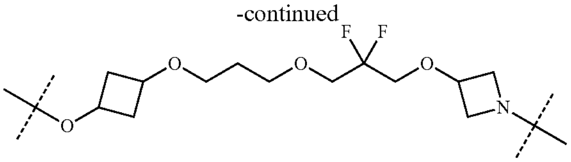
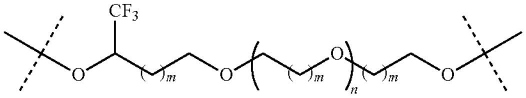
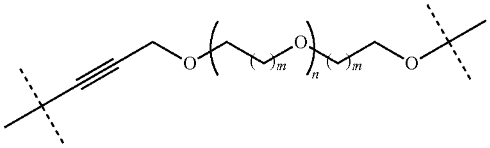
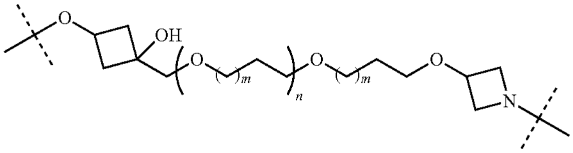
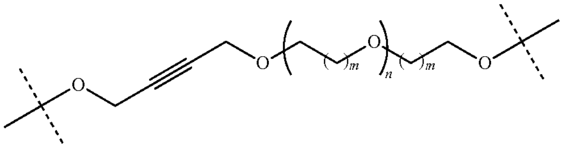
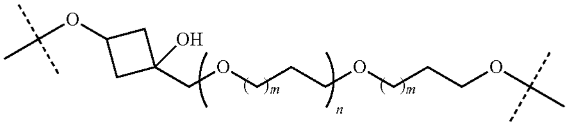
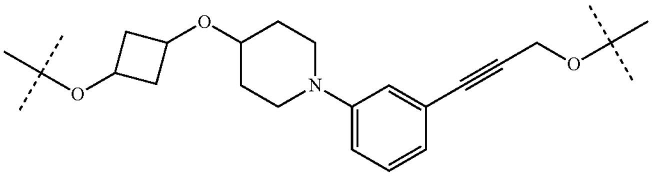
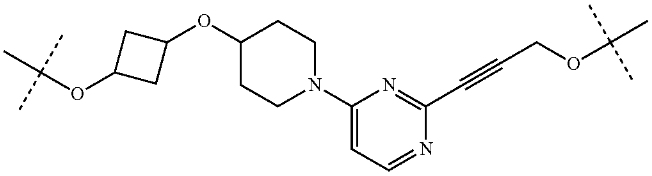
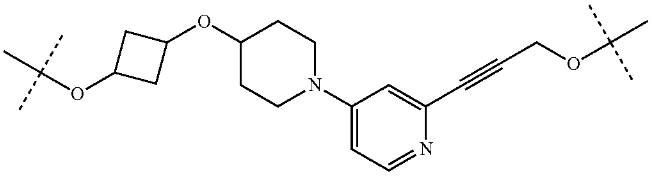
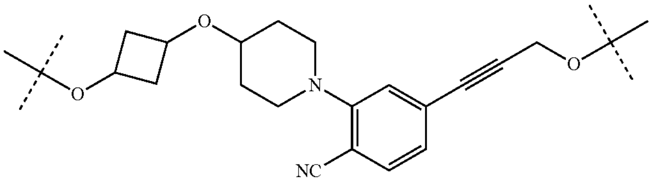
-continued
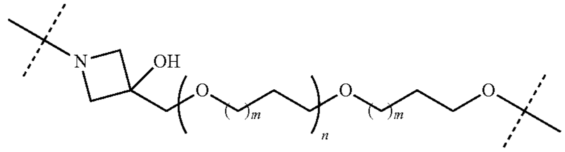
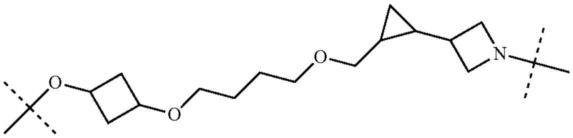
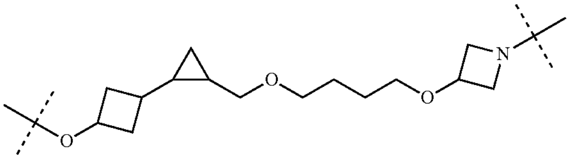
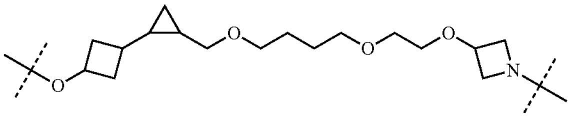
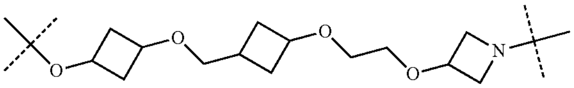

-continued
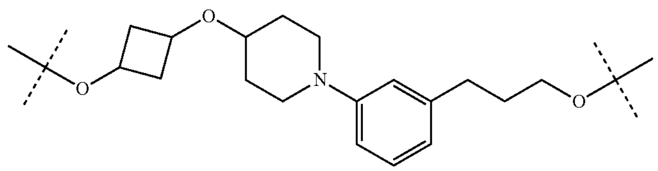
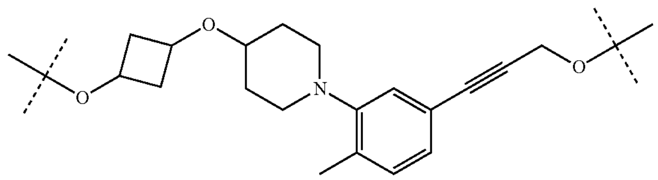
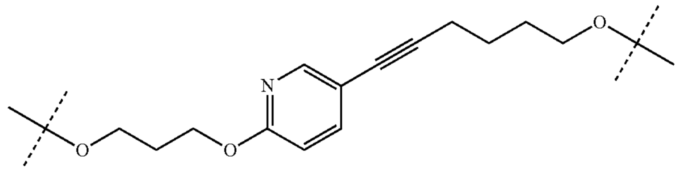
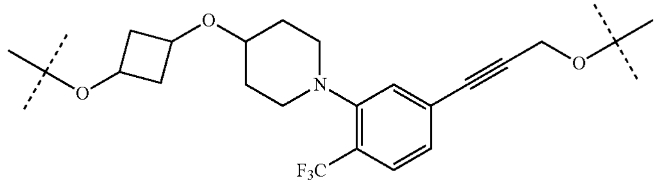
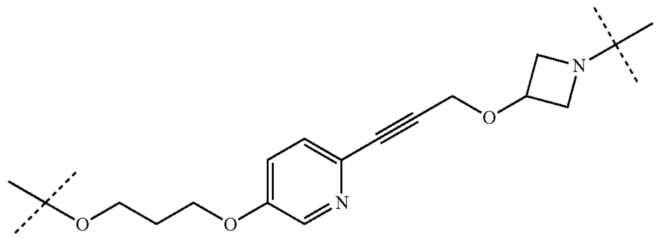
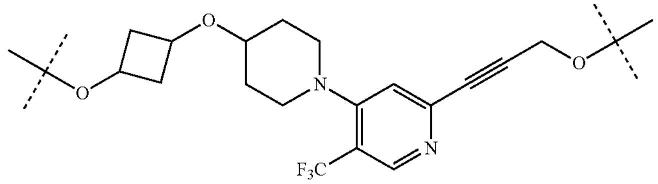
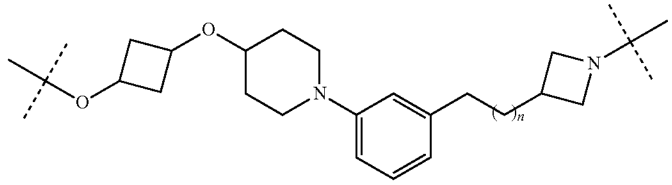
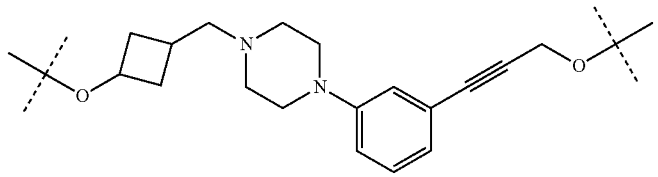
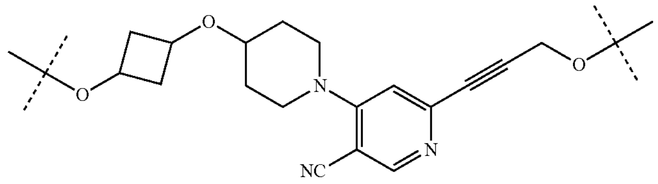

-continued
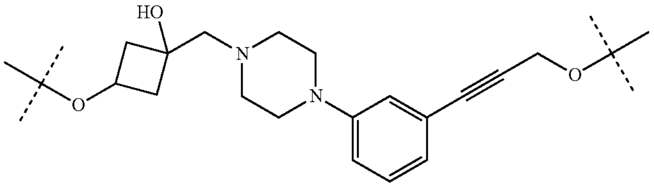
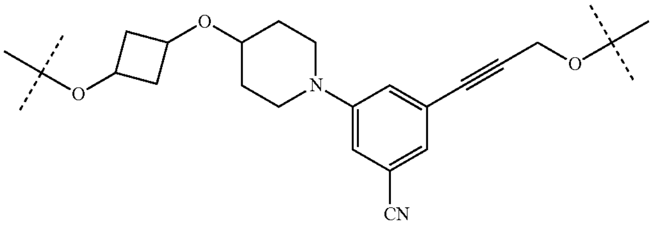
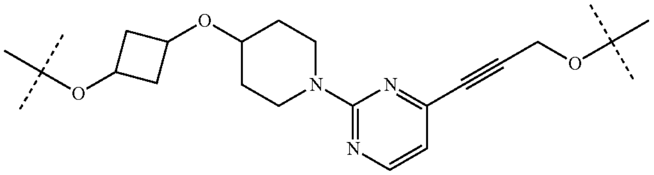
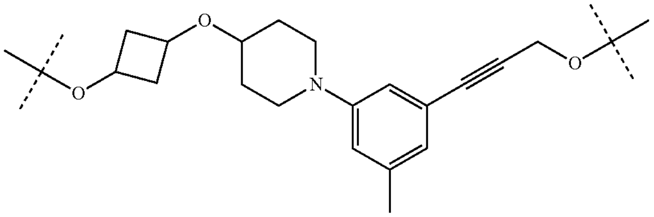
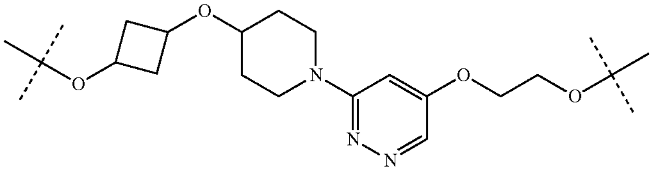
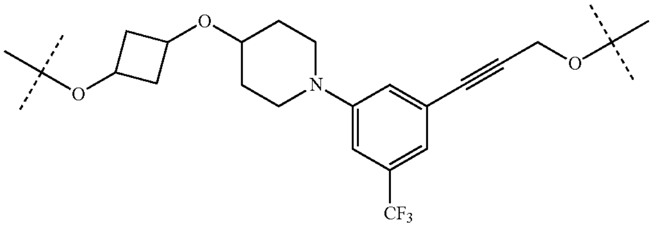
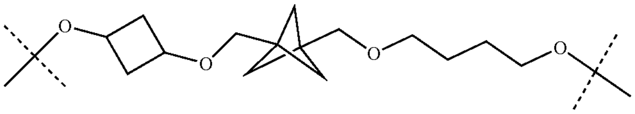
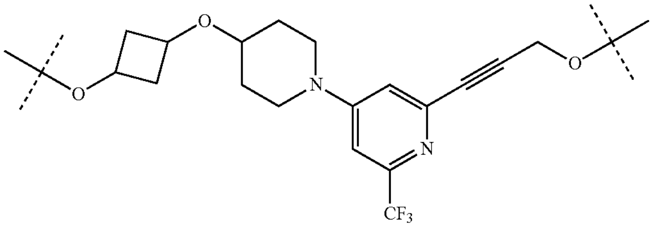

-continued
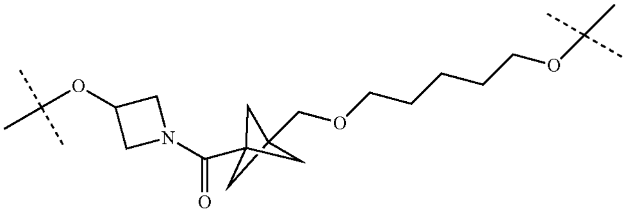
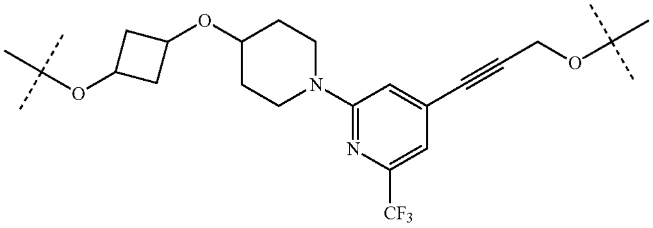
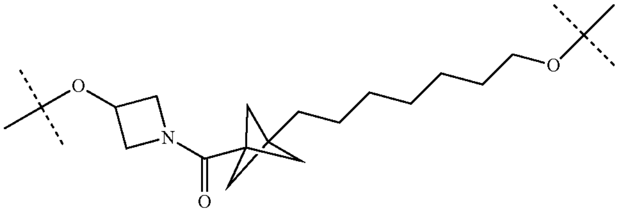
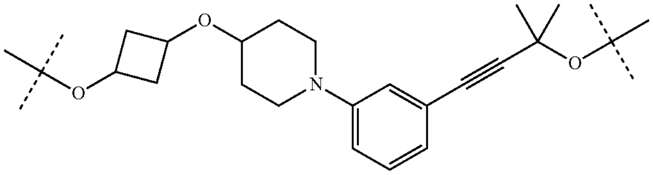
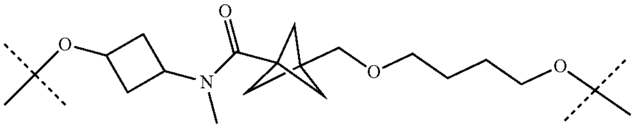
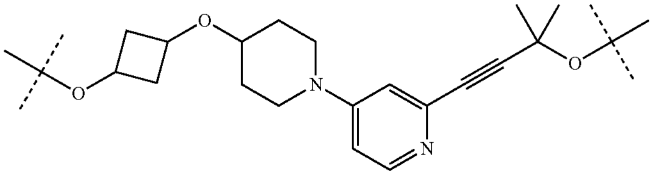
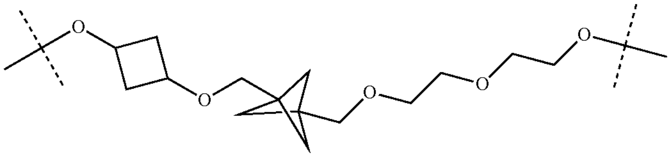
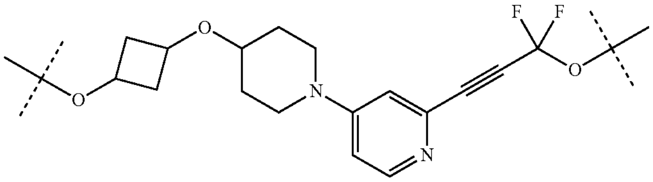
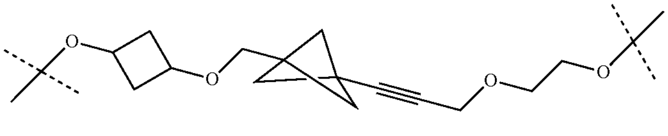

-continued
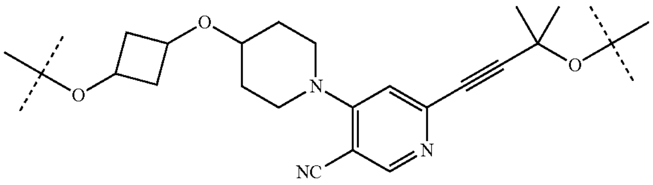
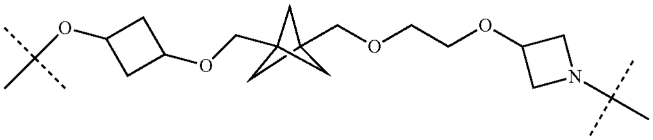
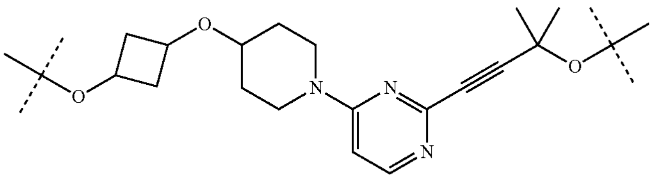
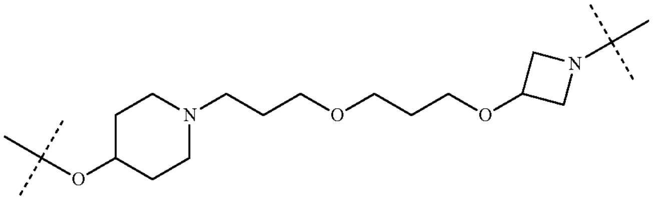
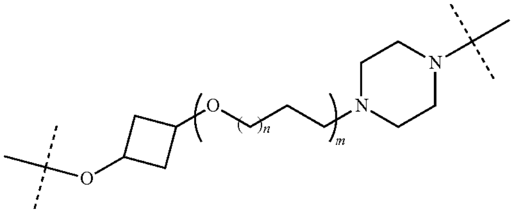
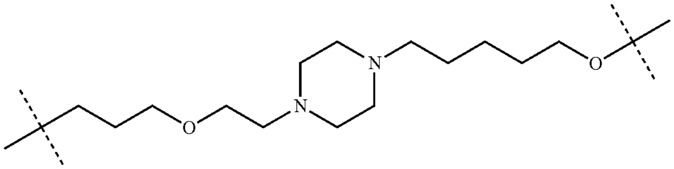
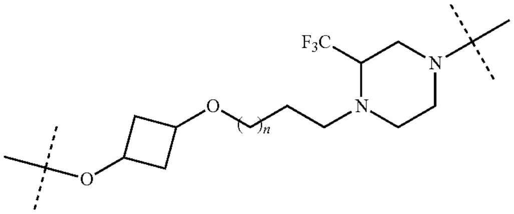
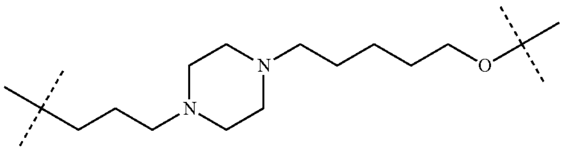
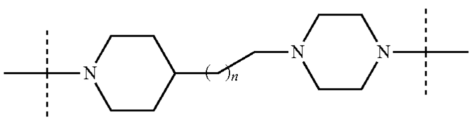
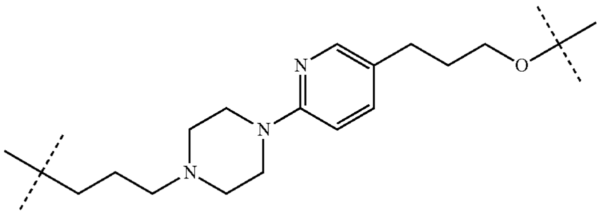
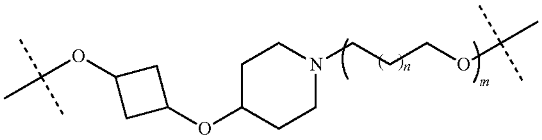

-continued
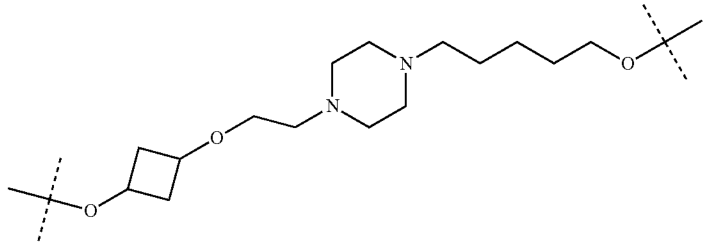
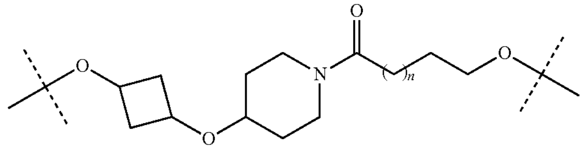
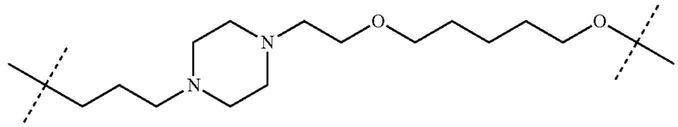
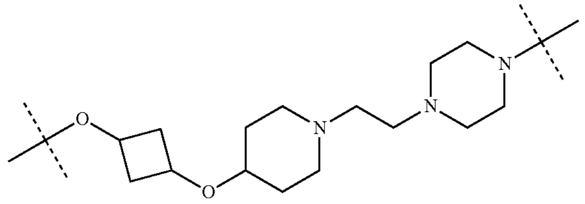
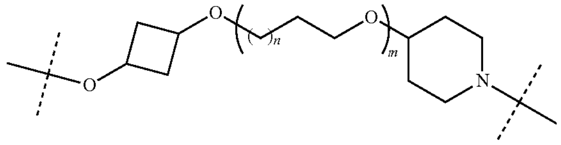
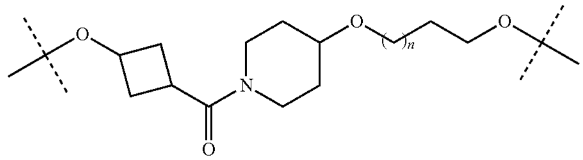
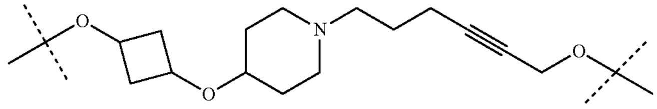
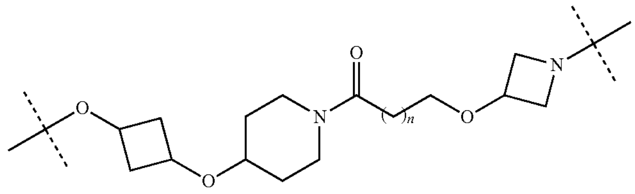
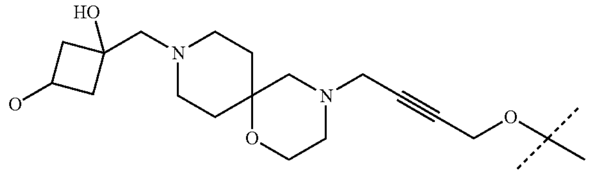
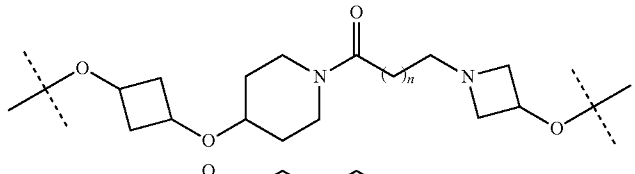
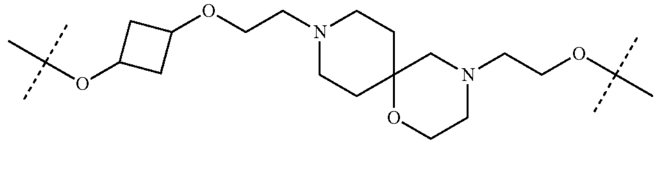

-continued
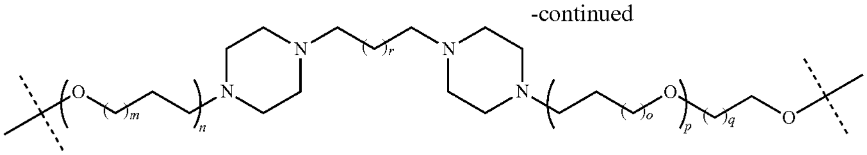
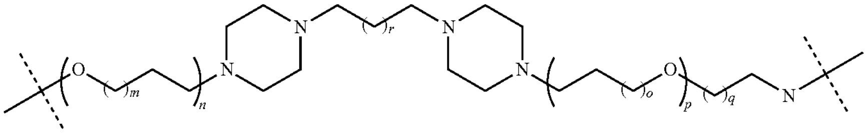
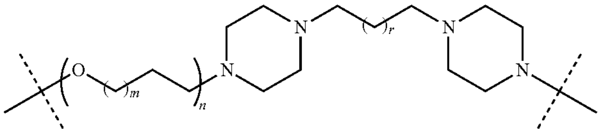
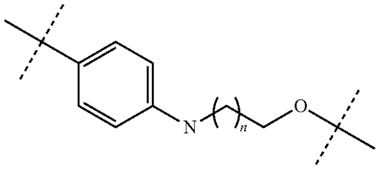
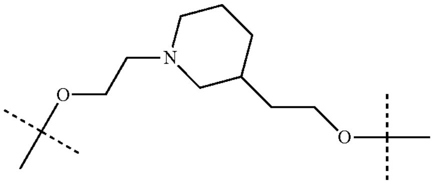
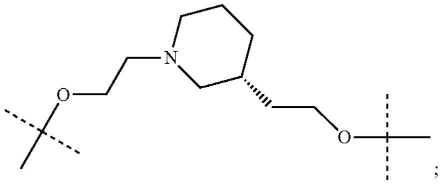
;
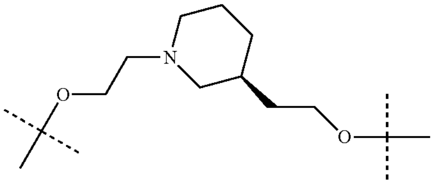
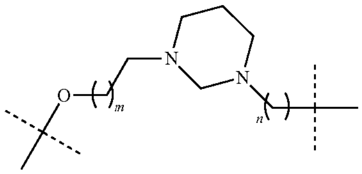
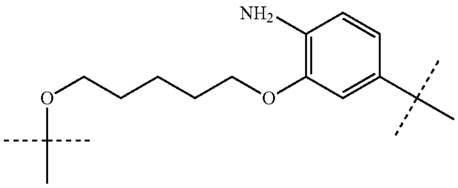
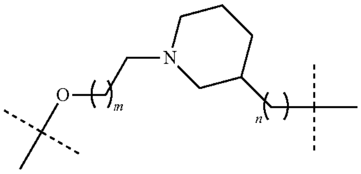
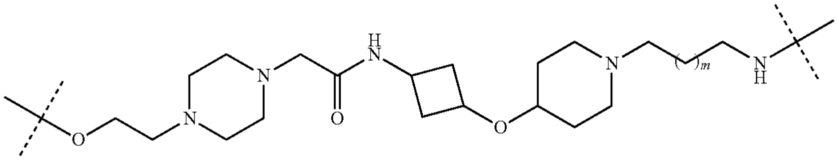
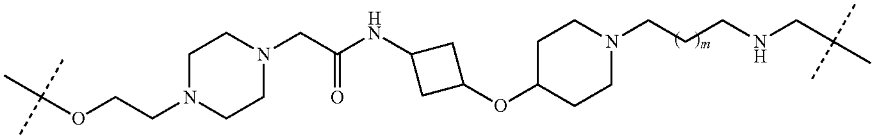
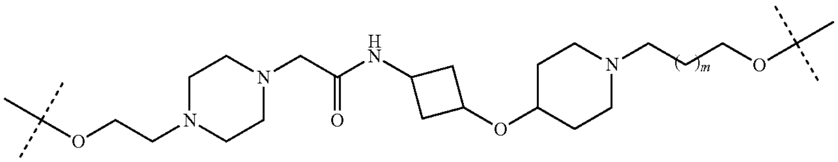
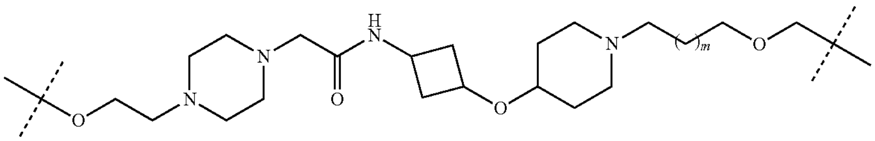
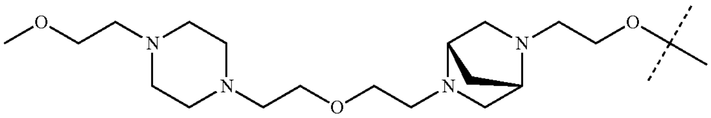

-continued
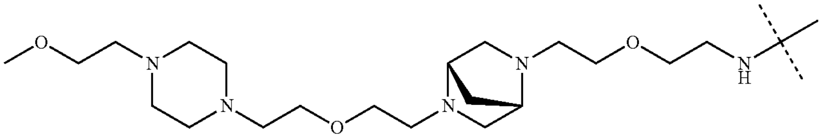
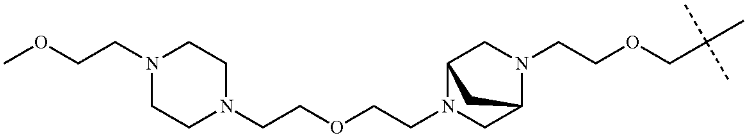
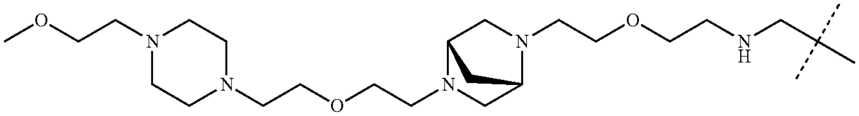
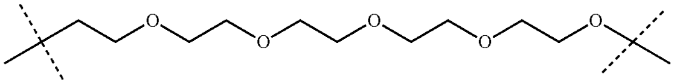
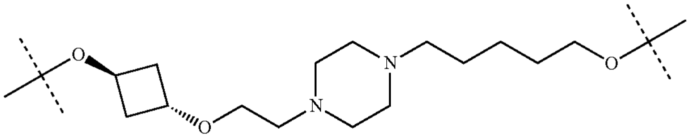
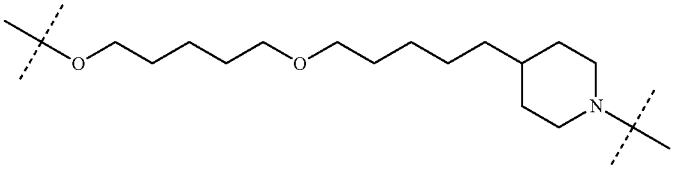
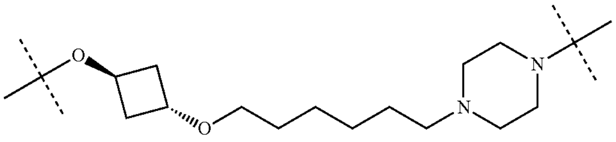
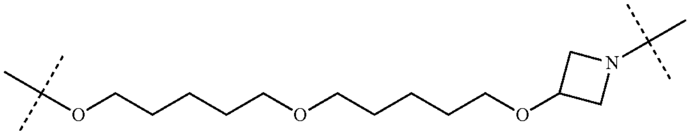
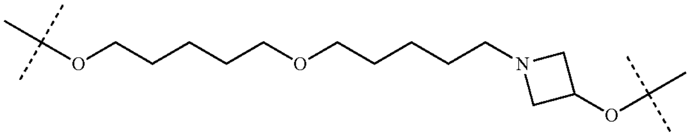
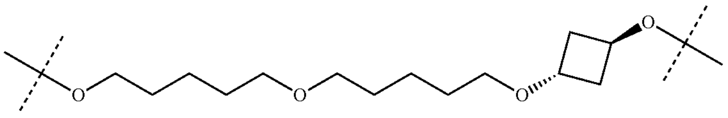
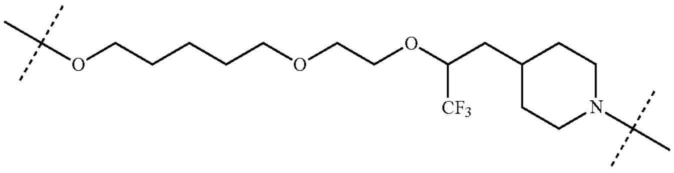
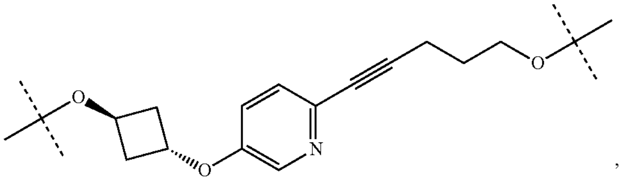
, wherein m, n, o, p, q, r, or s are independently 0, 1, 2, 3, 4, 5, 6, 7, 8, 9, 10, 11, 12, 13, 14, 15, 16, 17, 18, 19, or 20.
10. The bifunctional compound according to claim 1, or a pharmaceutically acceptable salt, enantiomer, or stereoisomer thereof, wherein the chemical linker group (L) is selected from the group consisting of:
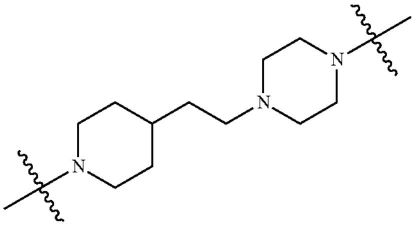
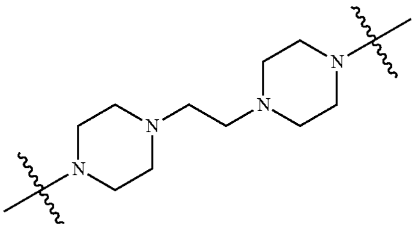
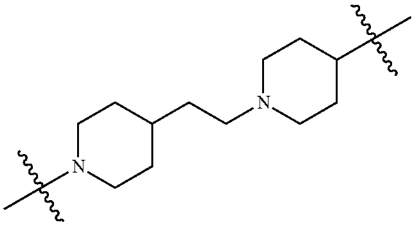
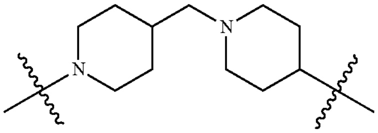
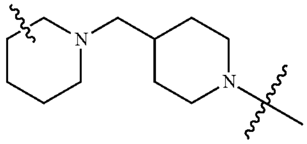
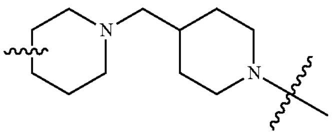
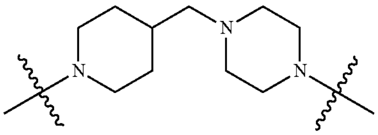
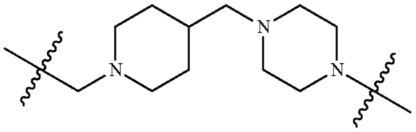
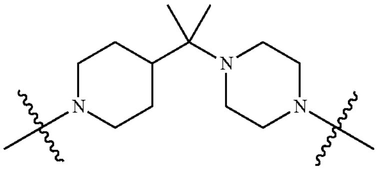
-continued
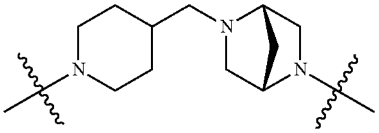
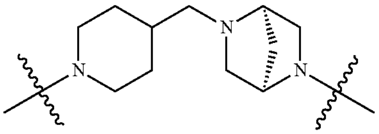
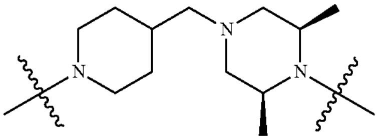
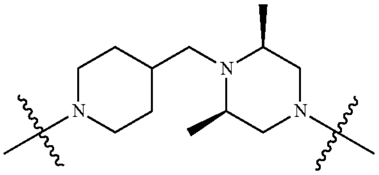
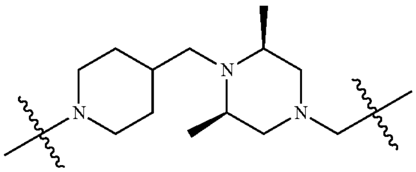
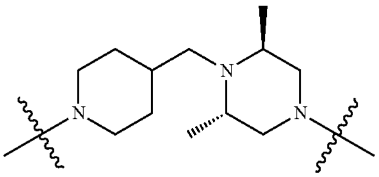
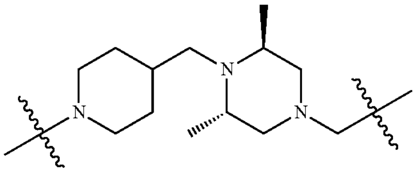
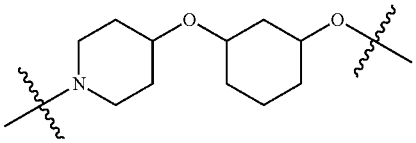
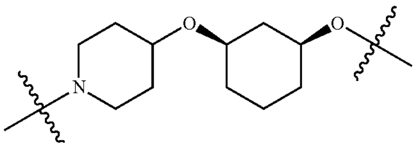
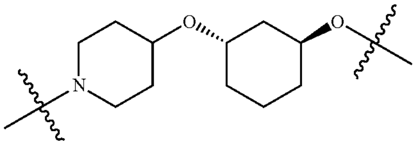
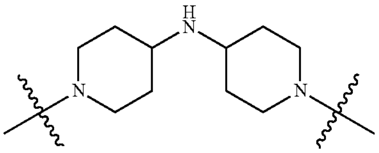

-continued
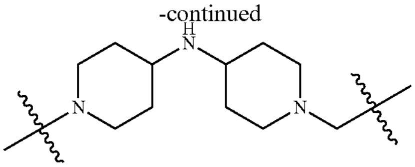
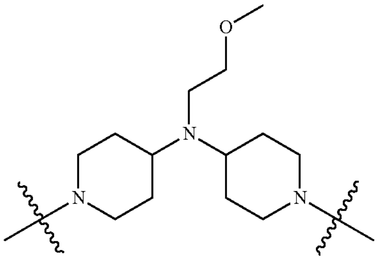
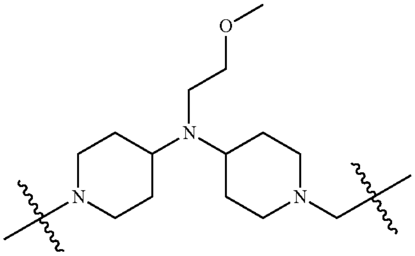
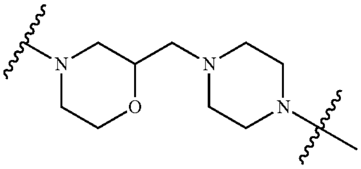
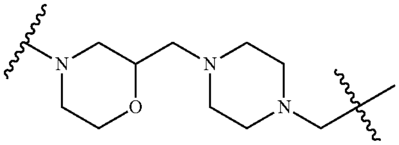
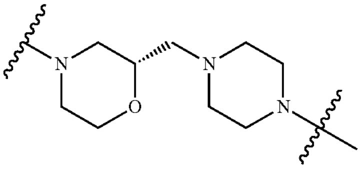
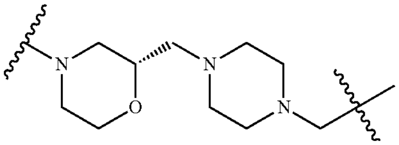
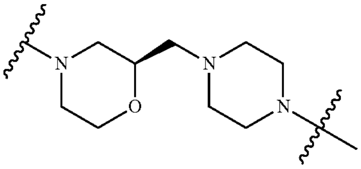
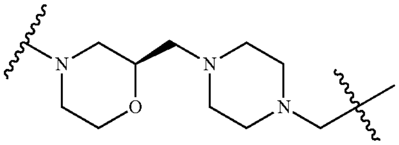
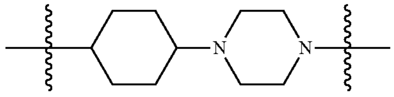
-continued
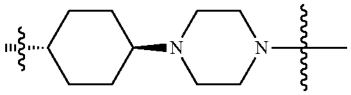
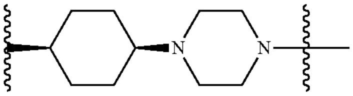
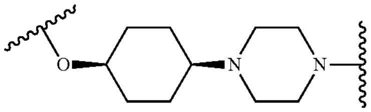
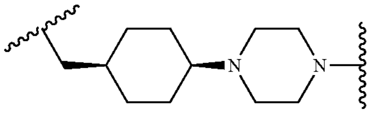
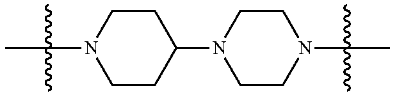
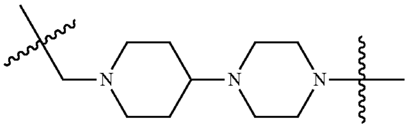
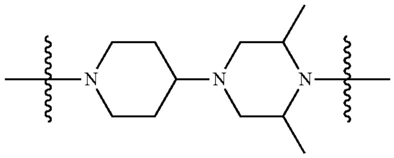
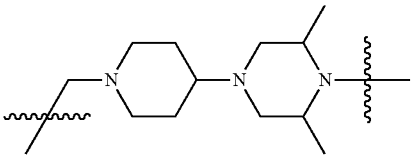
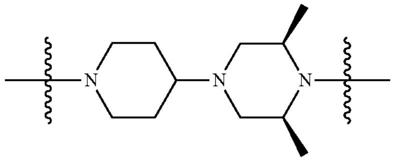
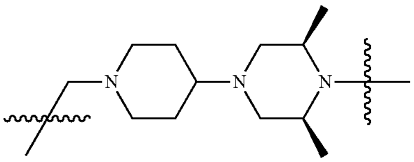
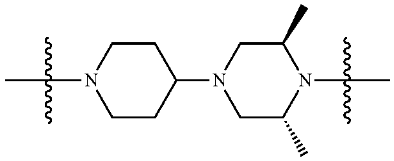
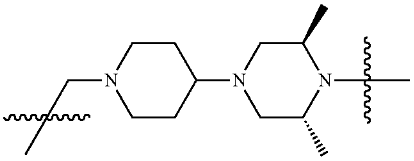

-continued
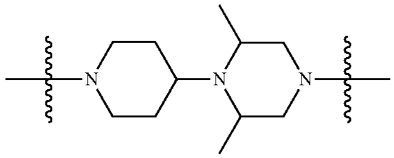
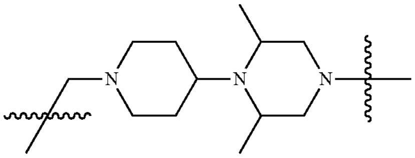
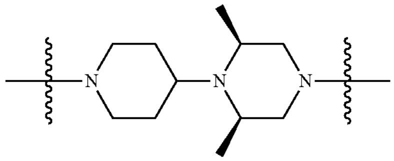
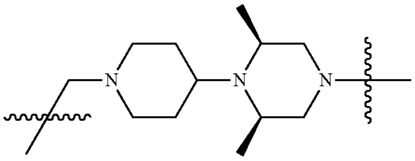
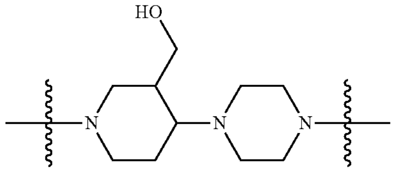
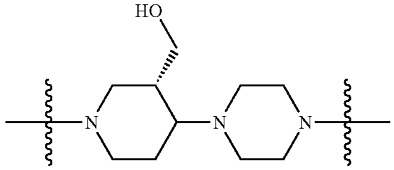
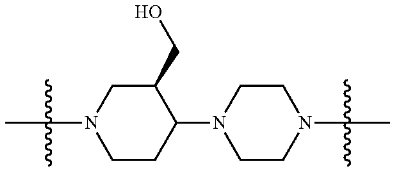
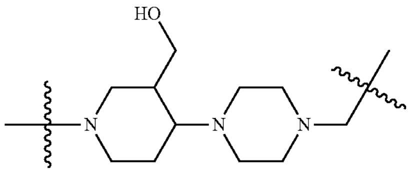
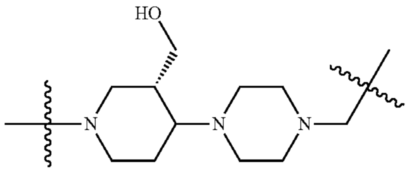
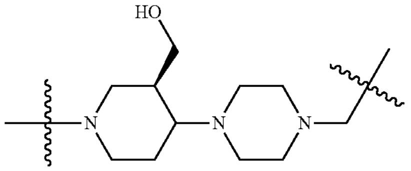
-continued
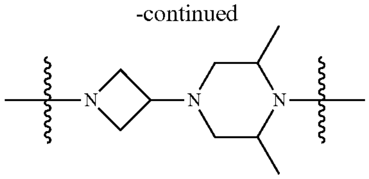
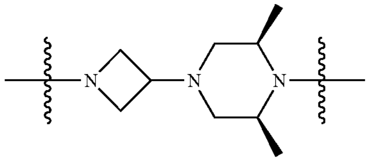
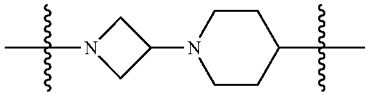
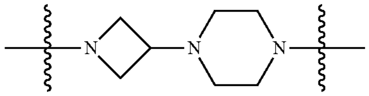
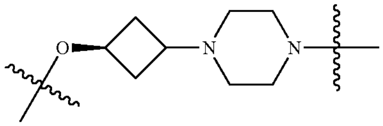
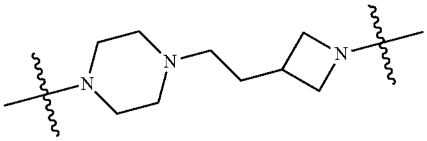
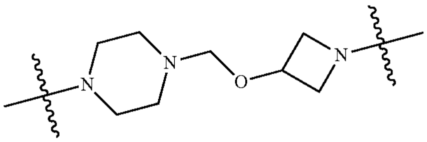
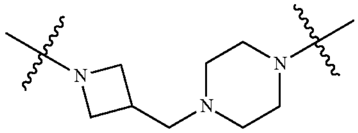
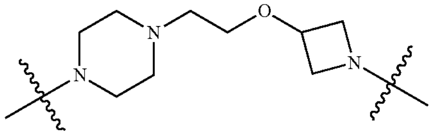
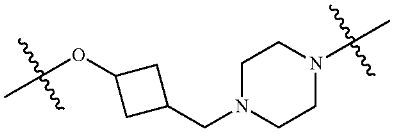
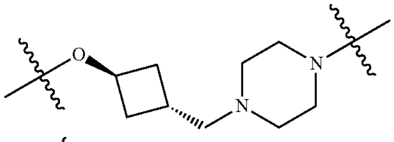
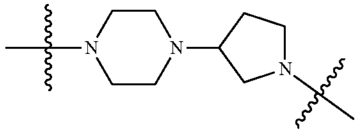
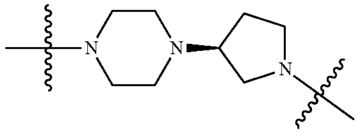

-continued
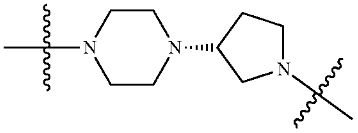
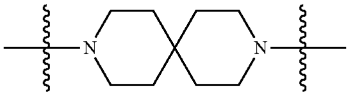
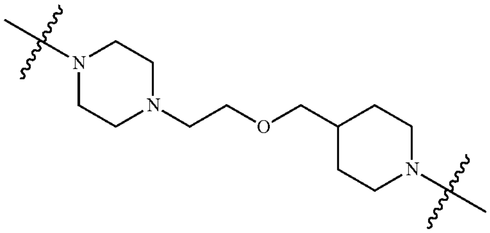
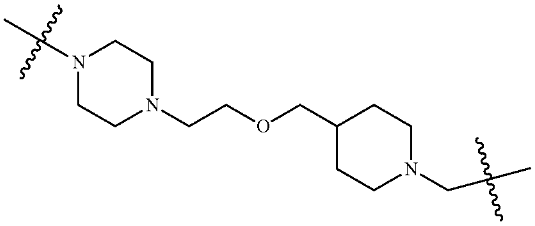
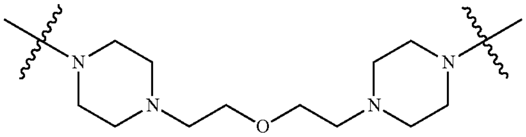
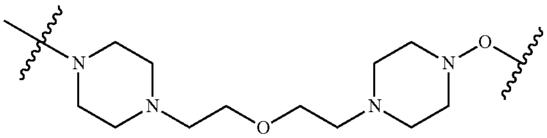
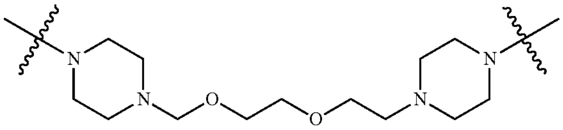
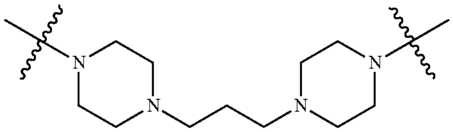
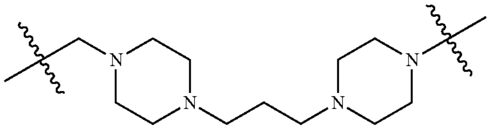
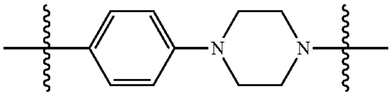
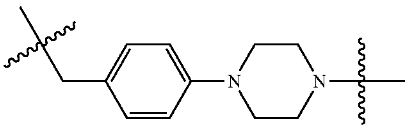
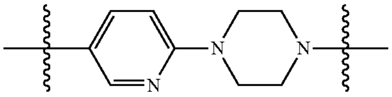
-continued
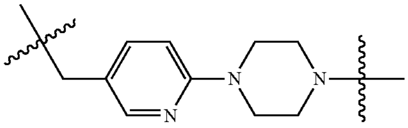
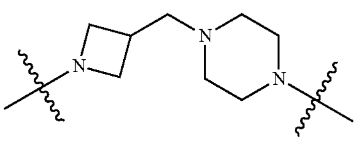
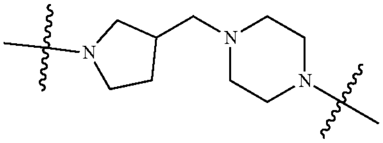
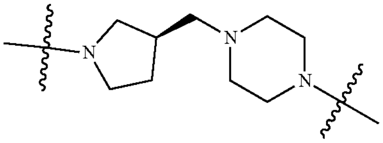
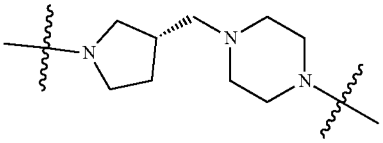
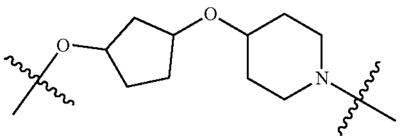
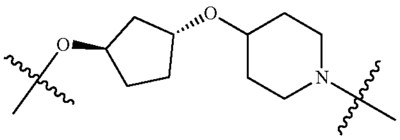
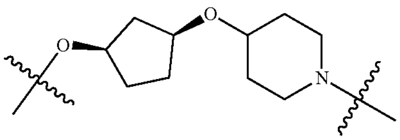
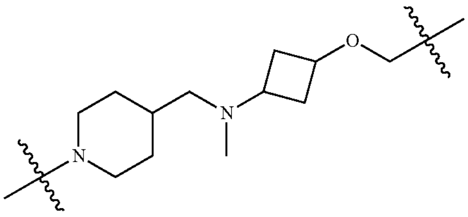
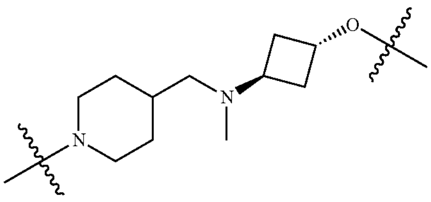

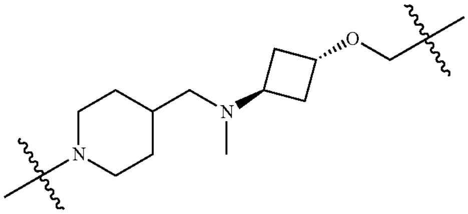
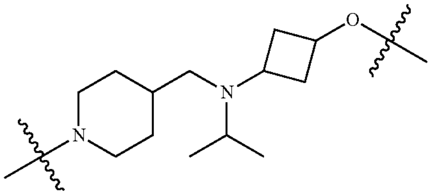
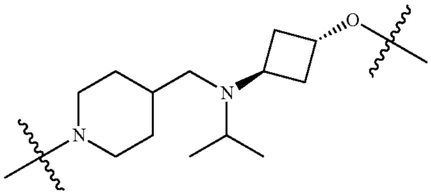
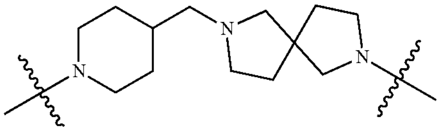
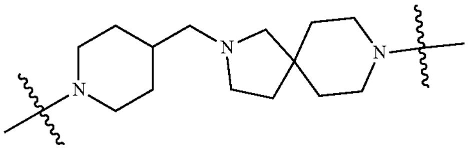
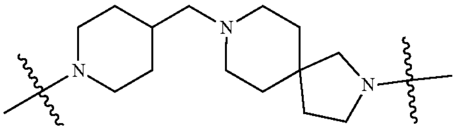
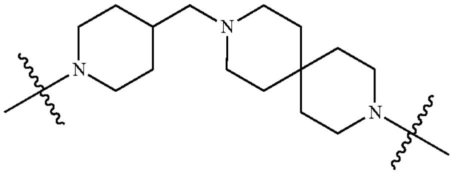
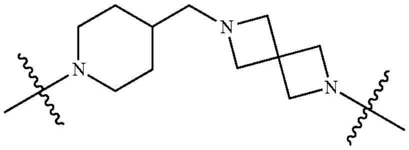
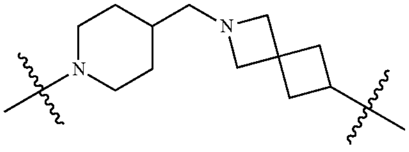
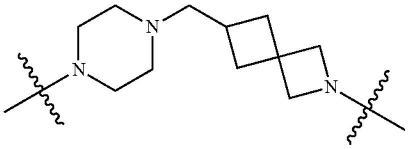
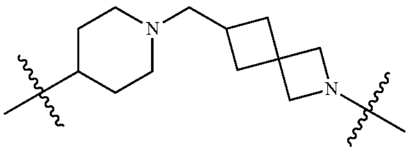
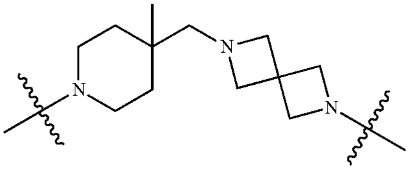
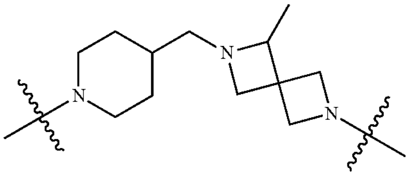
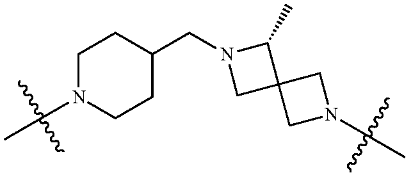
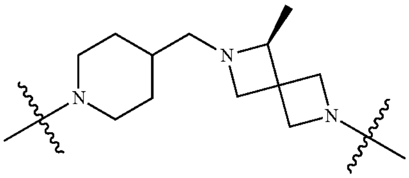
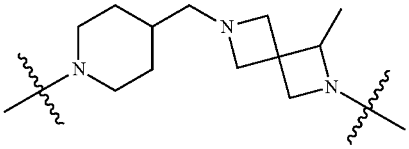
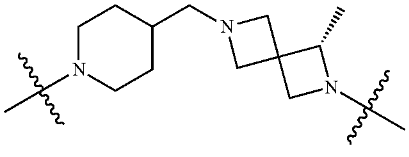
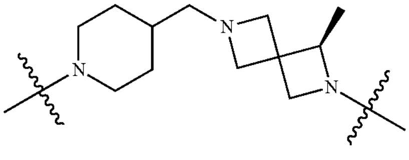
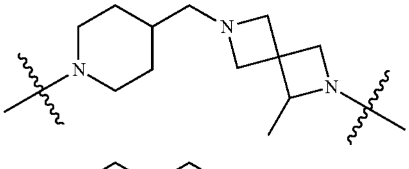
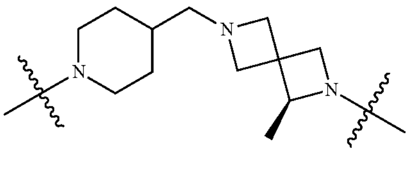

-continued
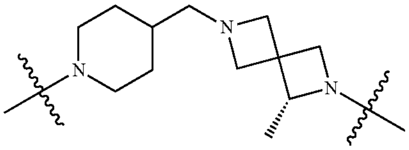
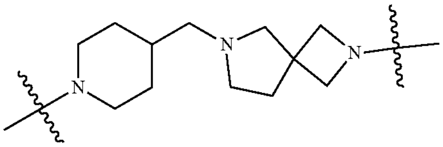
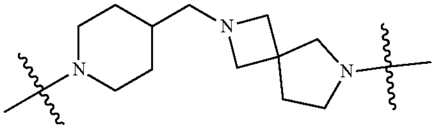
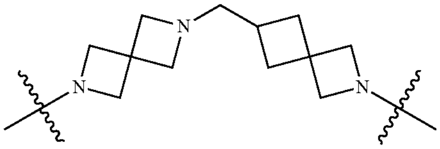
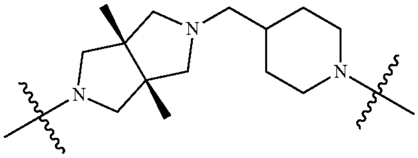
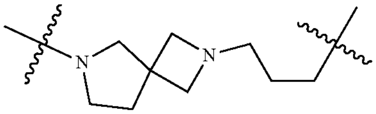
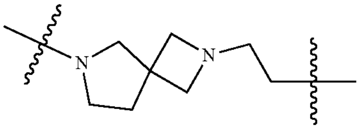
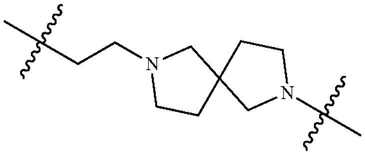
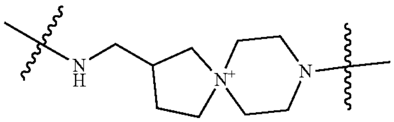
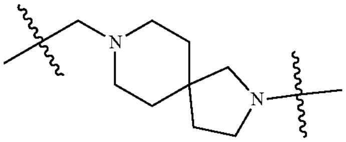
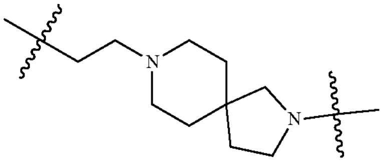
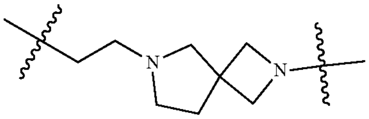
-continued
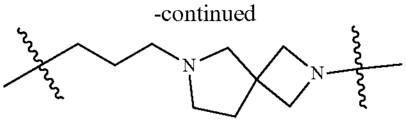
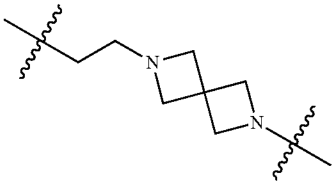
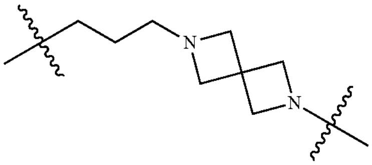
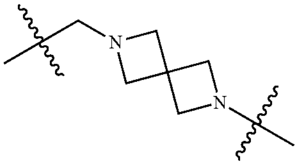
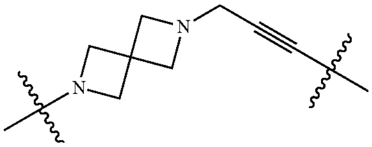
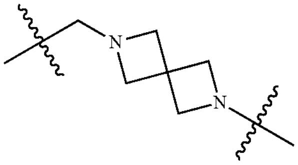
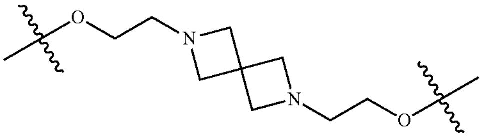
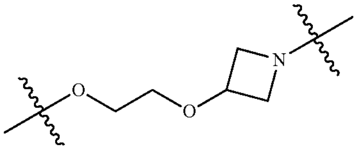
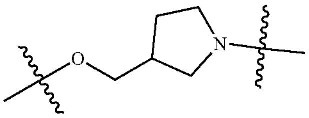
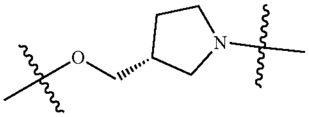
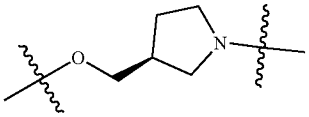
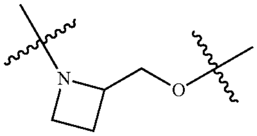

-continued
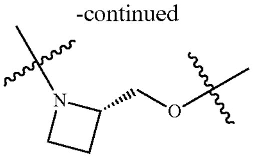
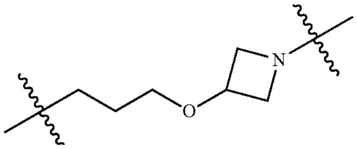
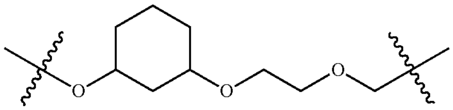
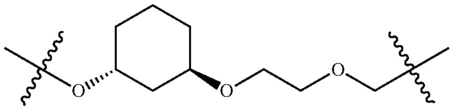
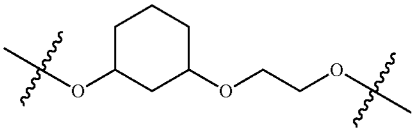
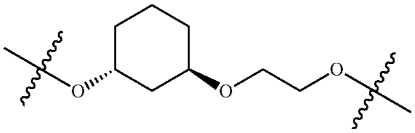
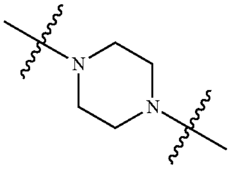
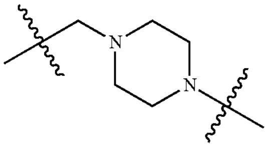
-continued
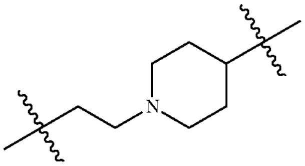
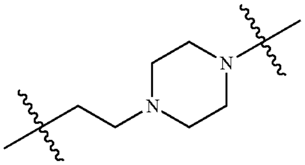
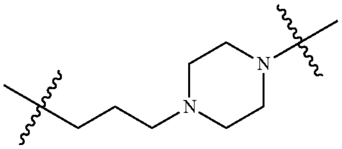
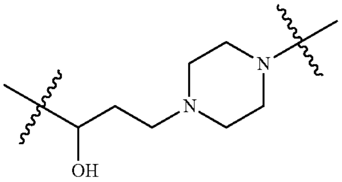
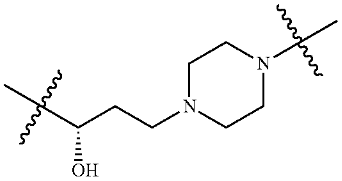
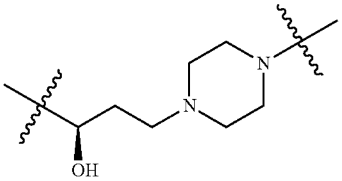
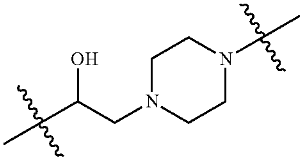
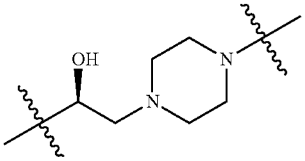
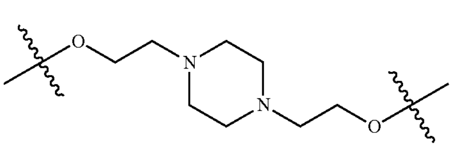
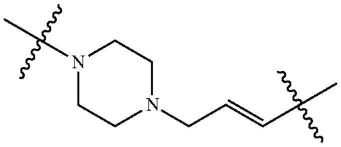
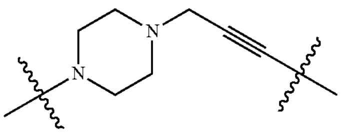
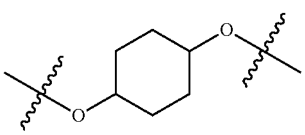
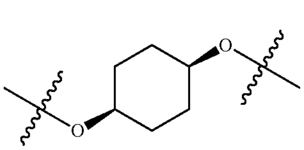
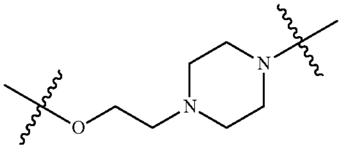
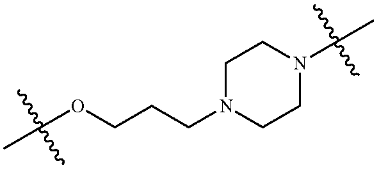

-continued
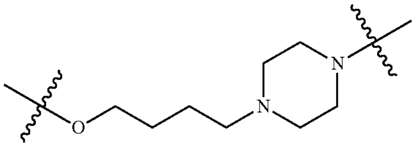
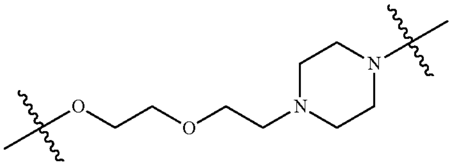
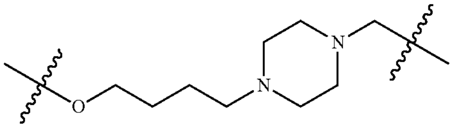
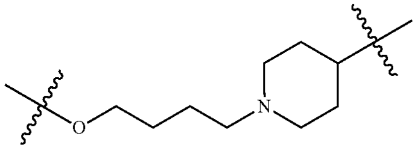
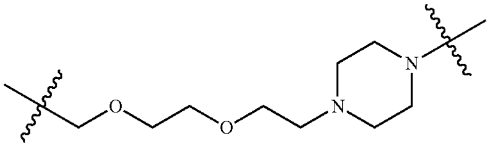
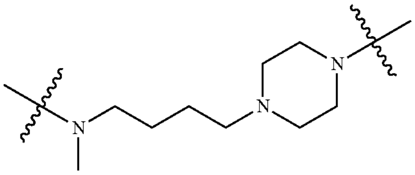
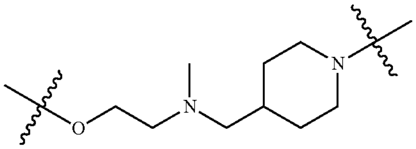
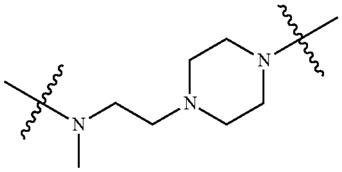
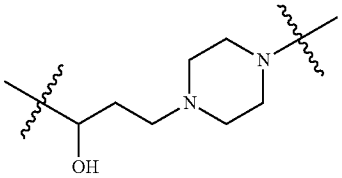
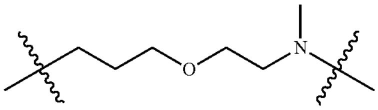
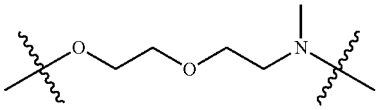
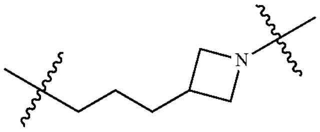
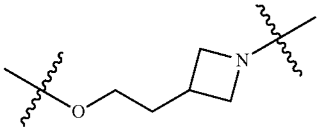
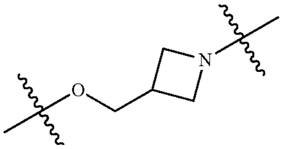
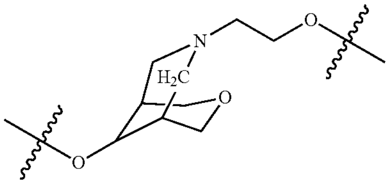
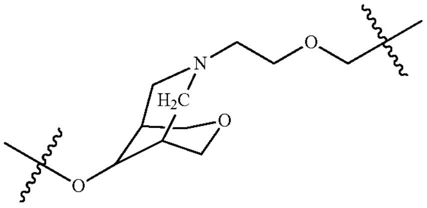
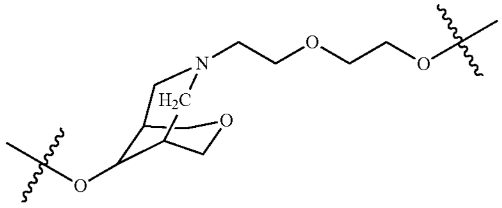
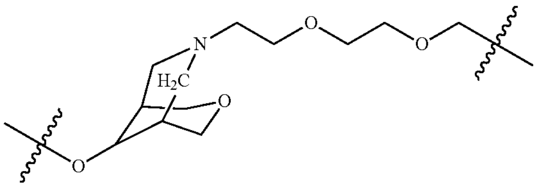
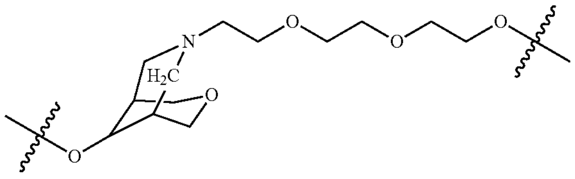
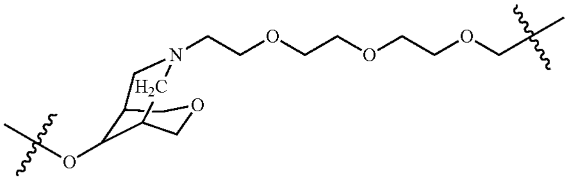
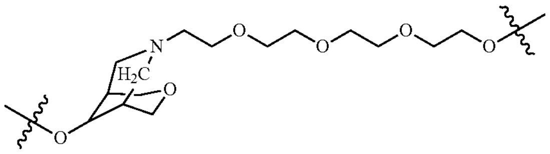

-continued
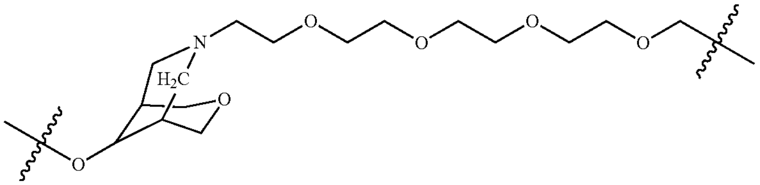
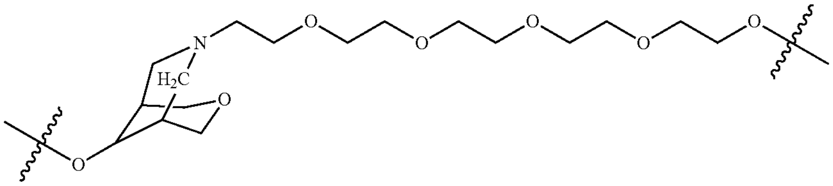
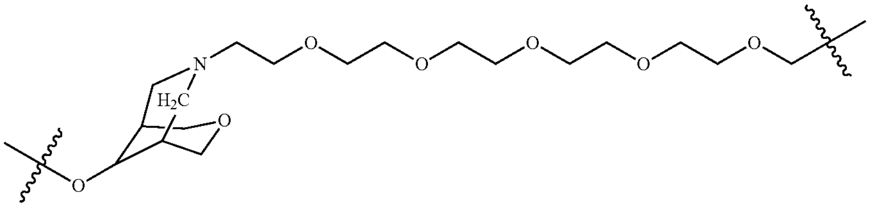
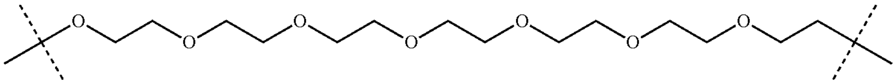
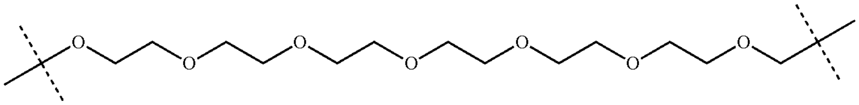
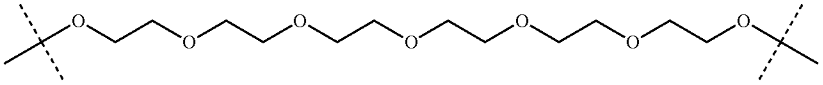
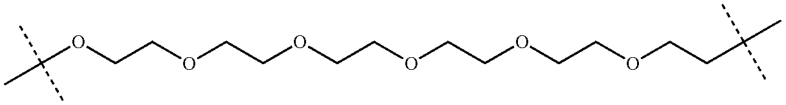
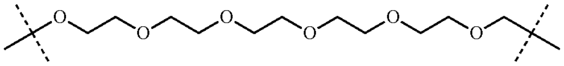 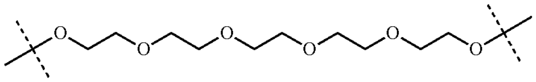
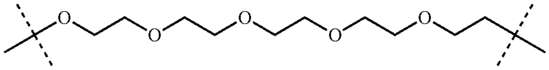 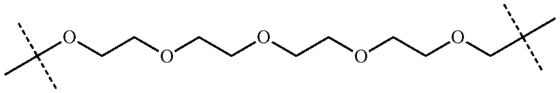
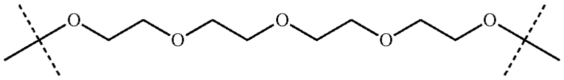 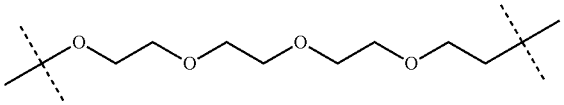
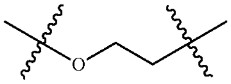 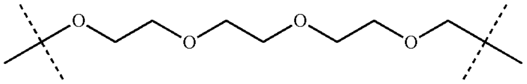
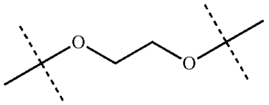 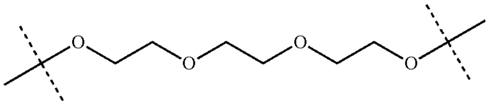
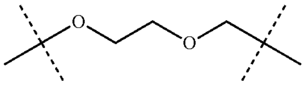 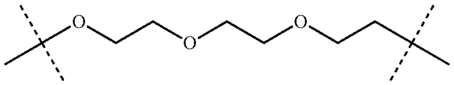
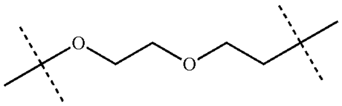 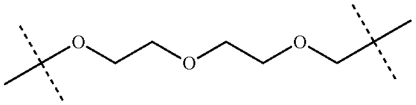

-continued
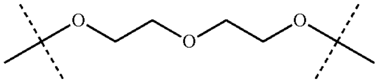
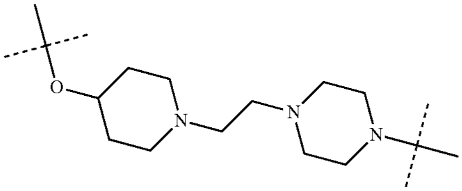
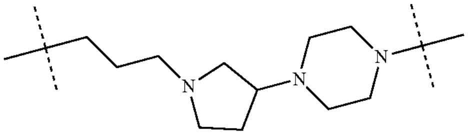
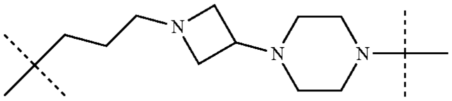
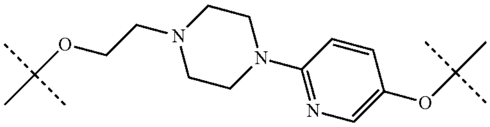
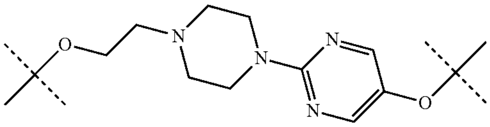
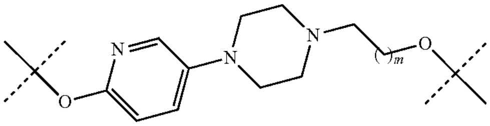
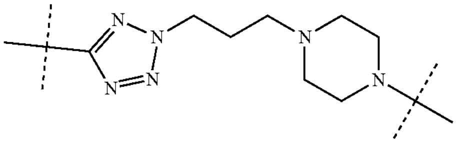
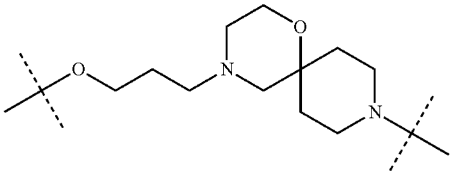
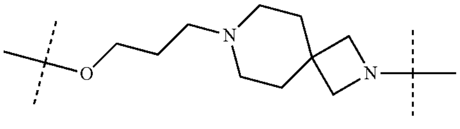
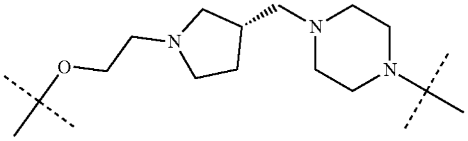
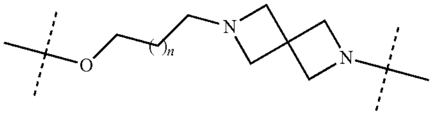
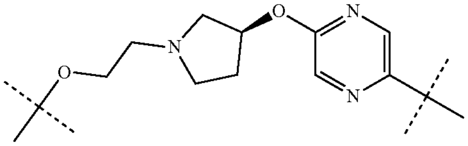
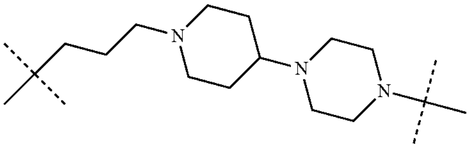
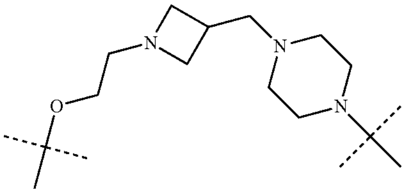
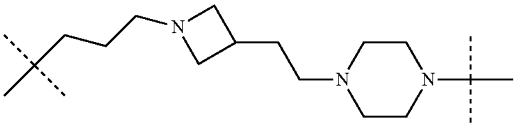
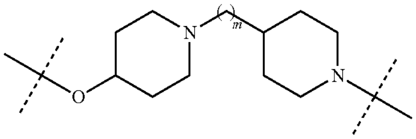
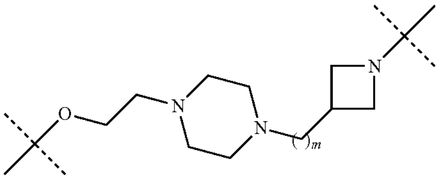
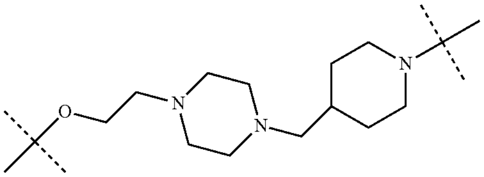
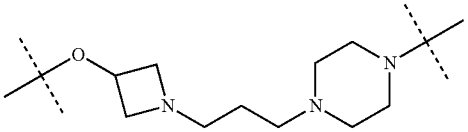

-continued
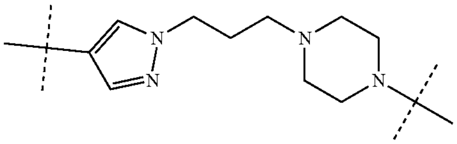
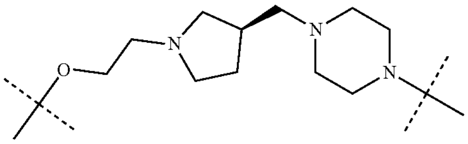
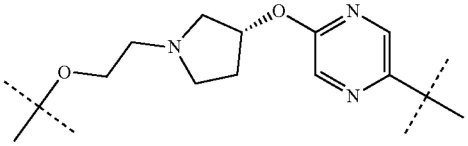
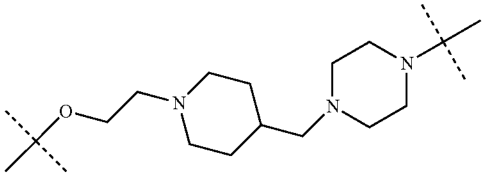
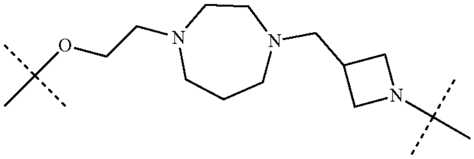
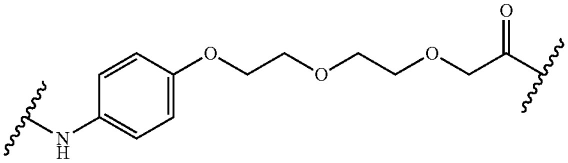
;
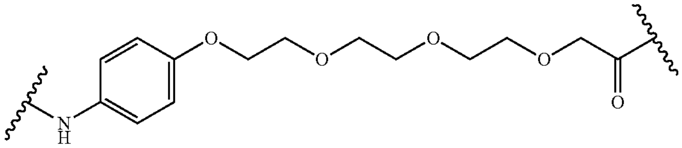
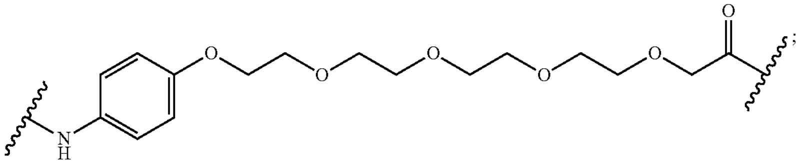
;
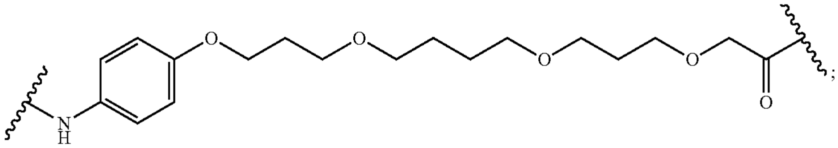
;
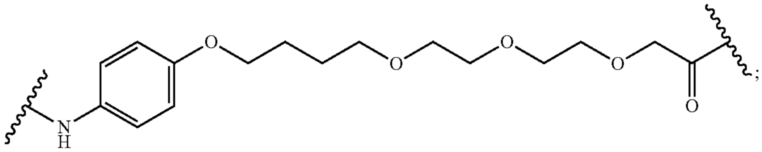
;
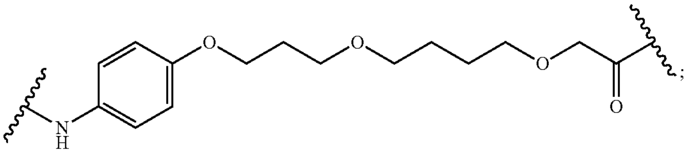
;
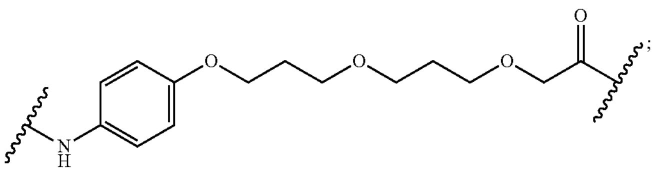
;
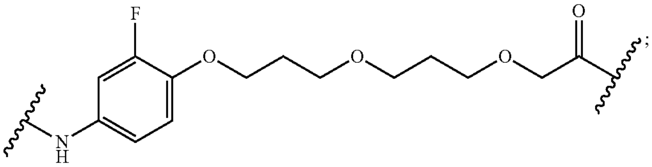
;

-continued
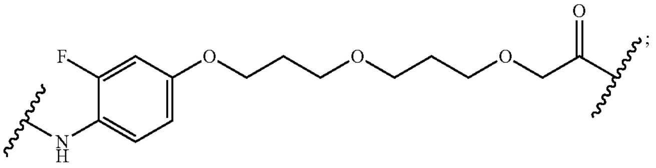
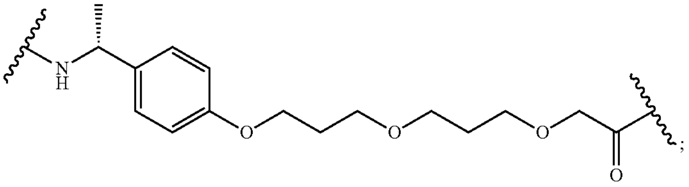
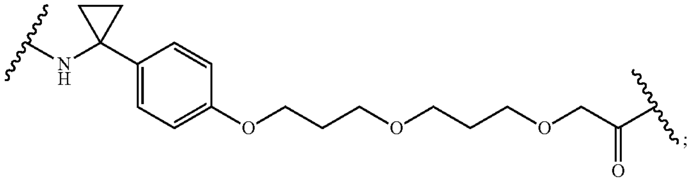
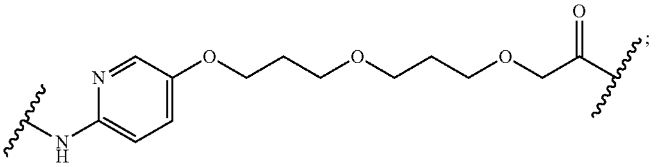
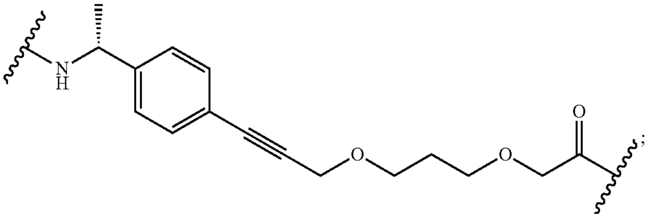
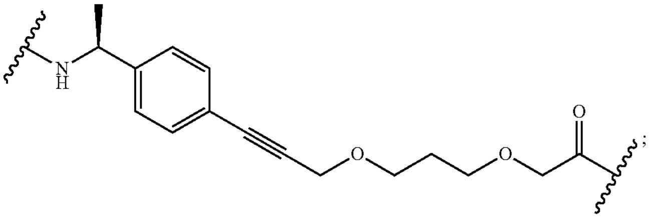
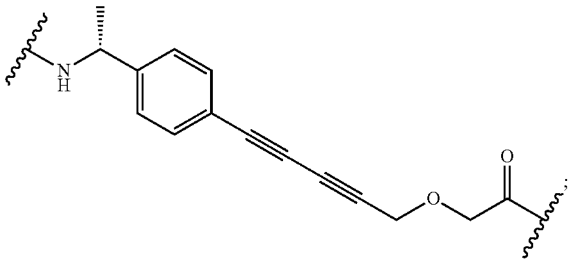
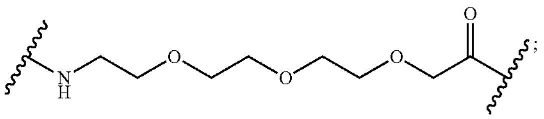
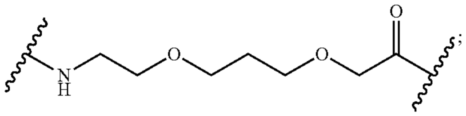
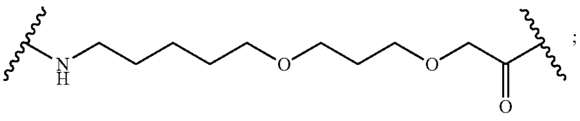
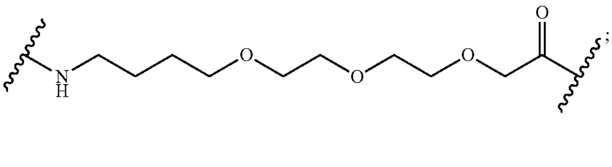
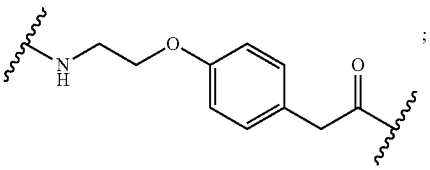

-continued
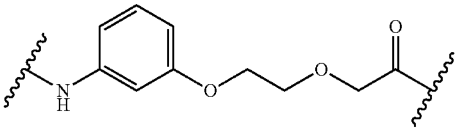 ; 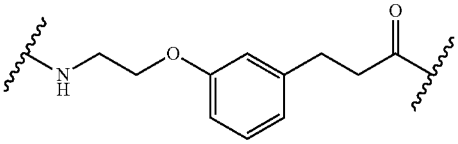 ;
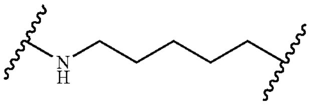 ; 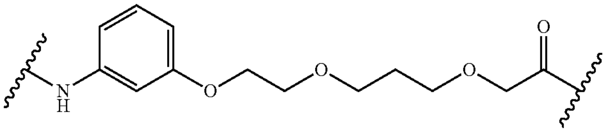 ;
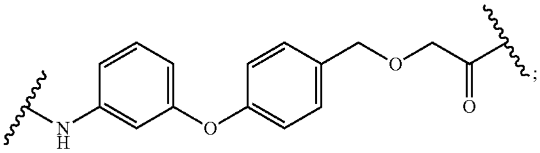 ; 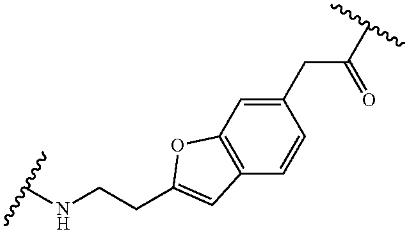 ;
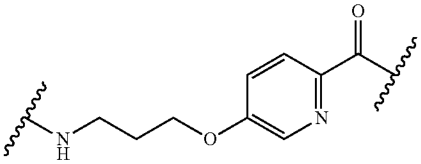 ; 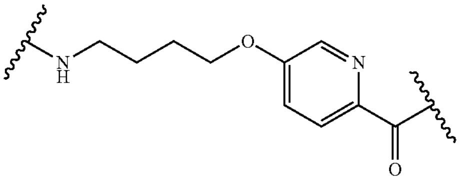 ;
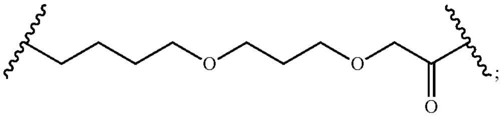 ; 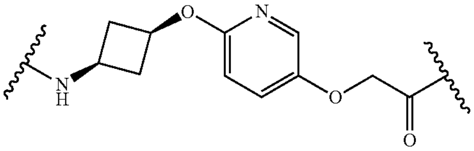 ;
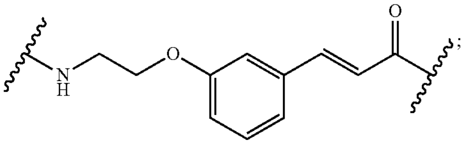 ; 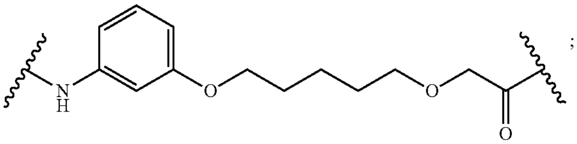 ;
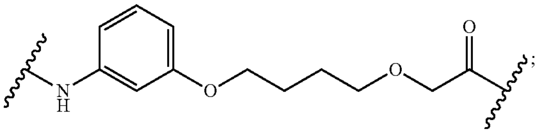 ; 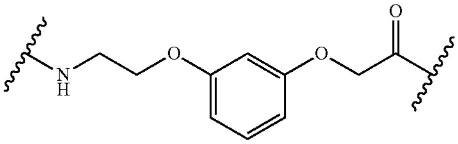 ;
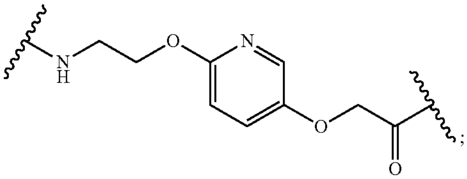 ; 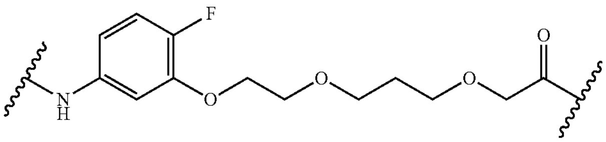 ;
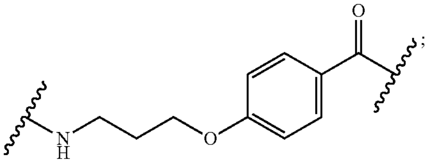 ; 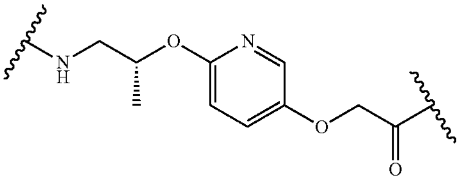 ;

-continued
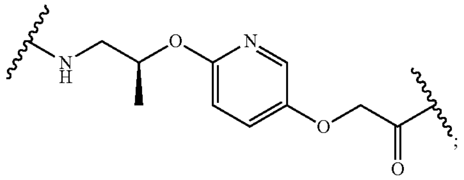
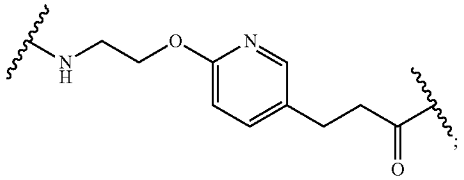
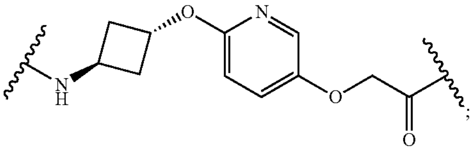
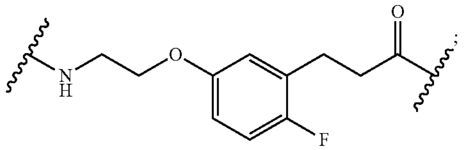
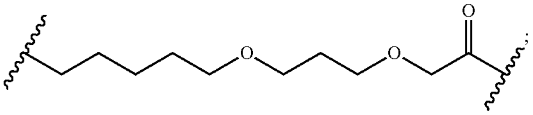
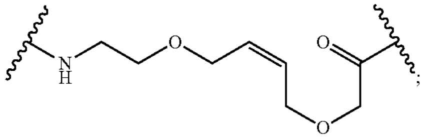
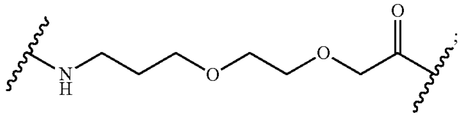
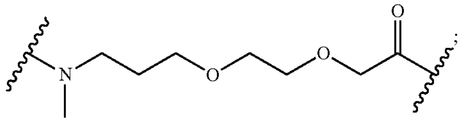
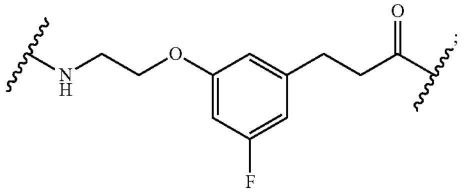
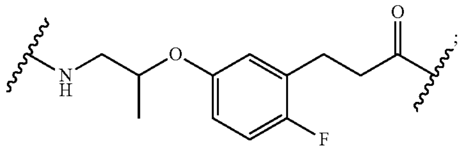
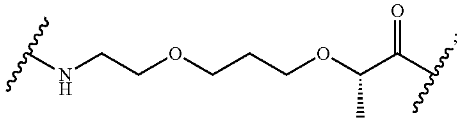
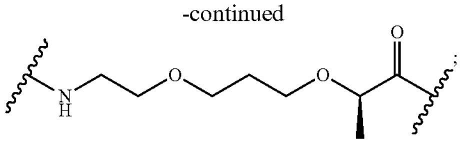
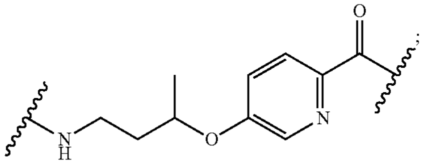
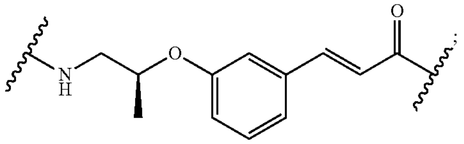
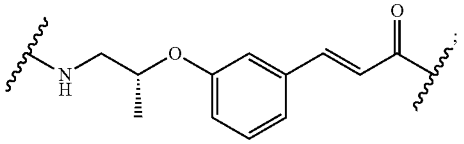
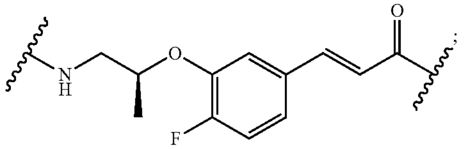
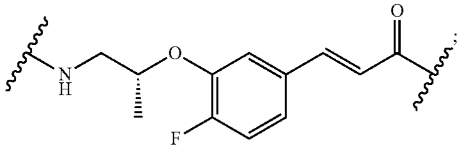
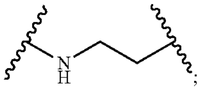
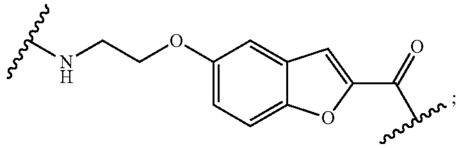
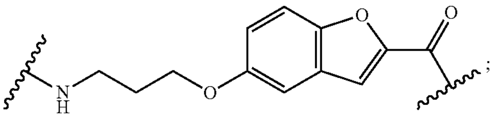
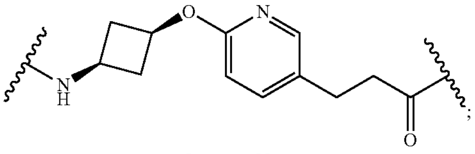
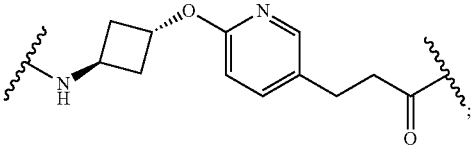
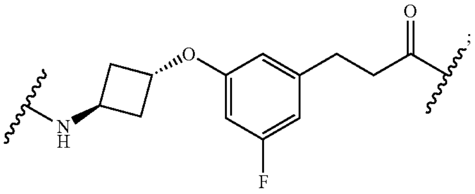

-continued
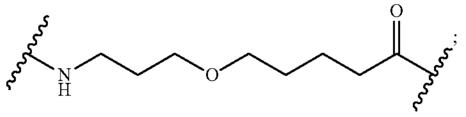
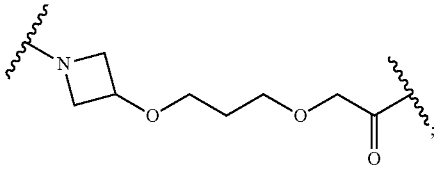
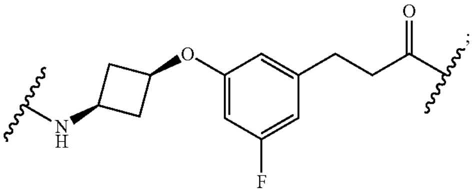
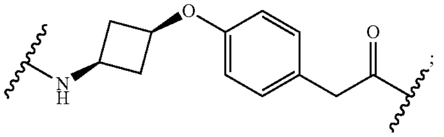
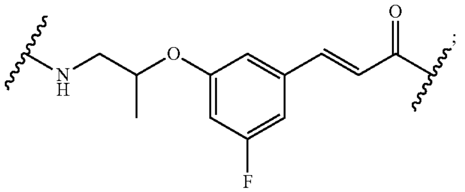
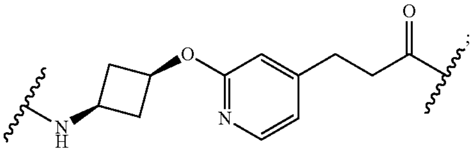
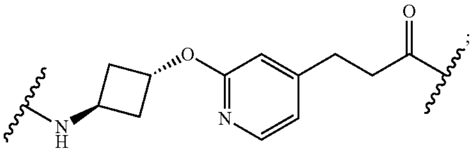
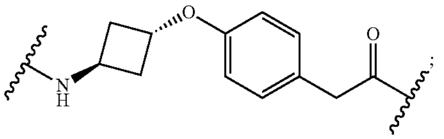
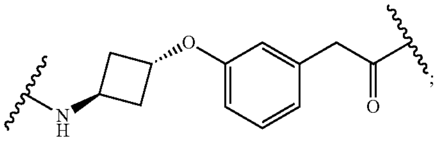
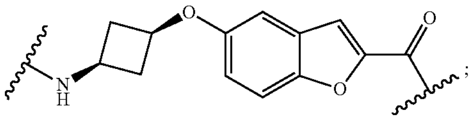
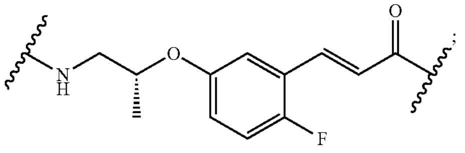
-continued
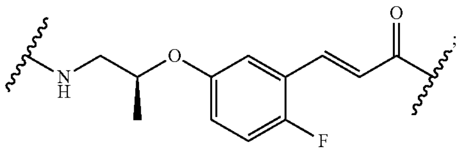
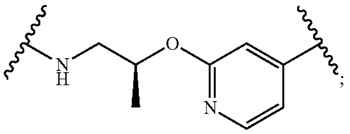
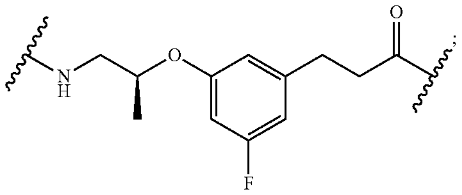
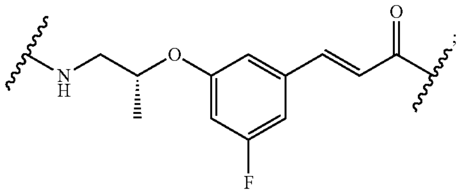
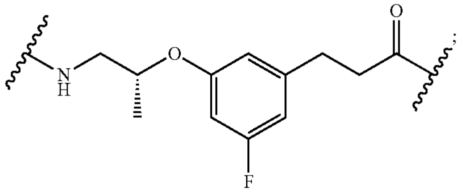
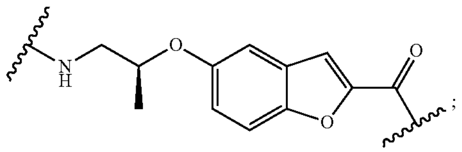
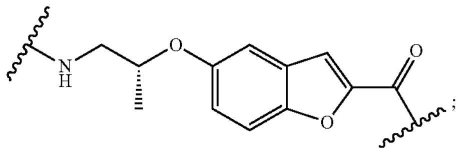
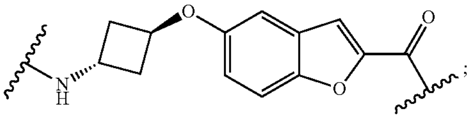
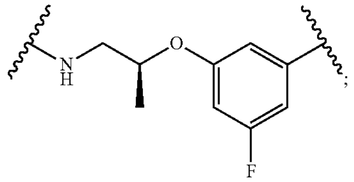
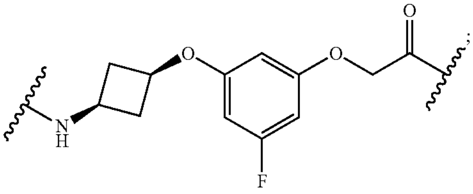

-continued
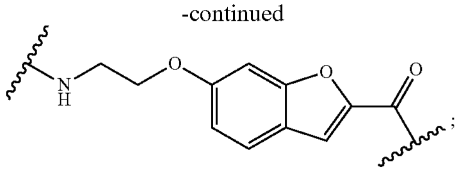
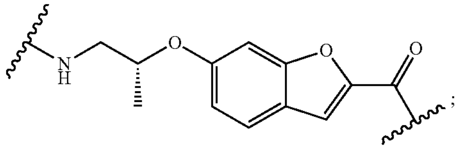
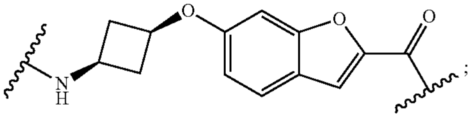
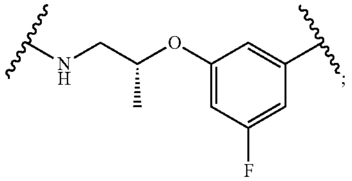
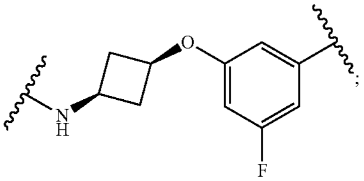
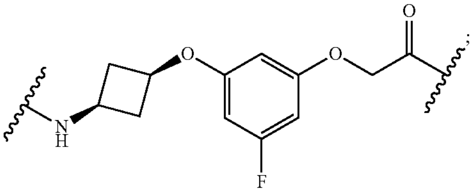
-continued
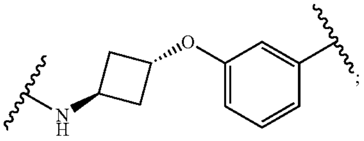
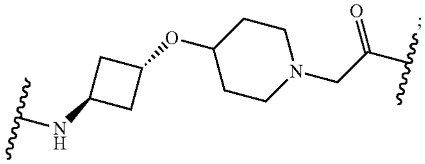
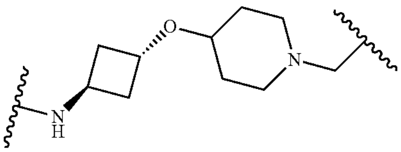
and
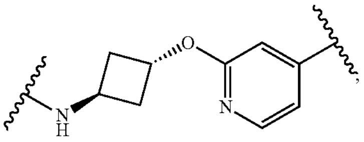
wherein each m and n is independently 0, 1, 2, 3, 4, 5, or 6.
11. The bifunctional compound according to claim 1, or a pharmaceutically acceptable salt, enantiomer, or stereoisomer thereof, wherein the chemical linker group (L) is selected from the group consisting of:
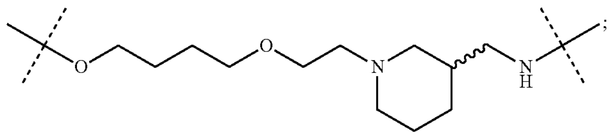
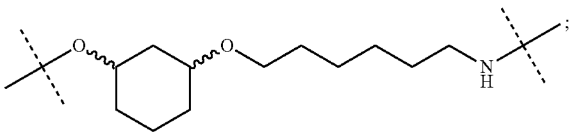
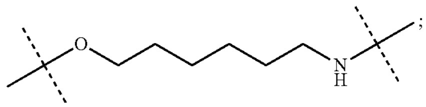
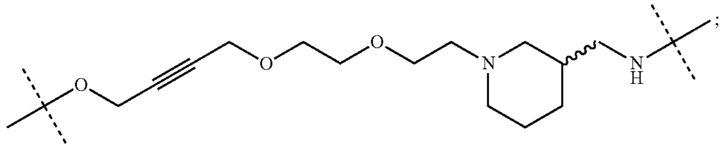
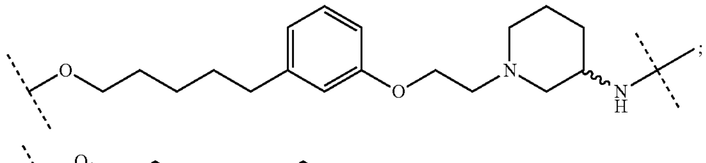
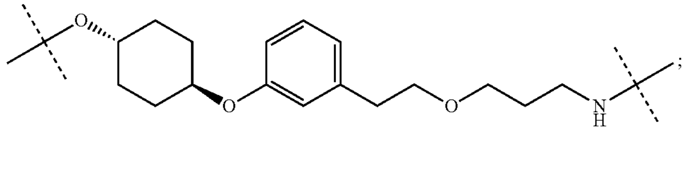

-continued
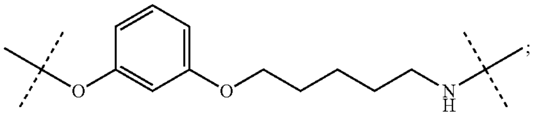 ; 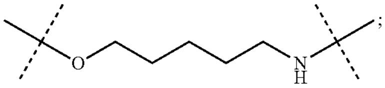 ;
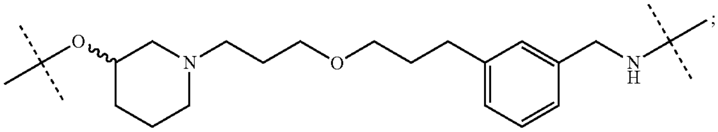 ; 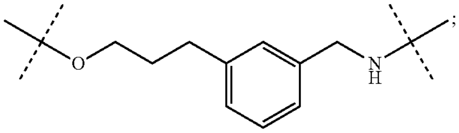 ;
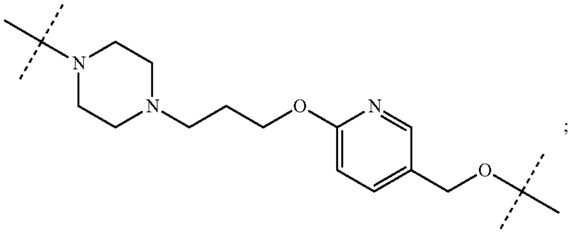 ; 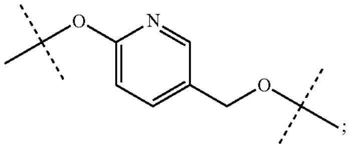 ;
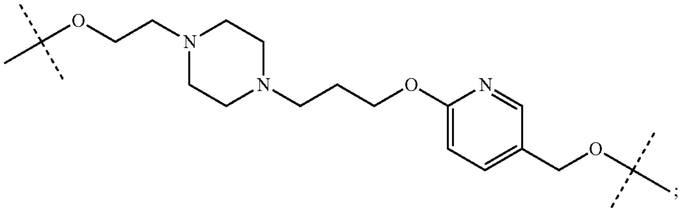 ;
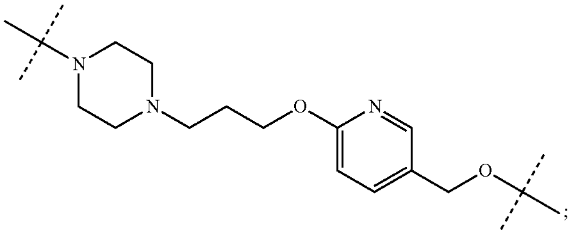 ;
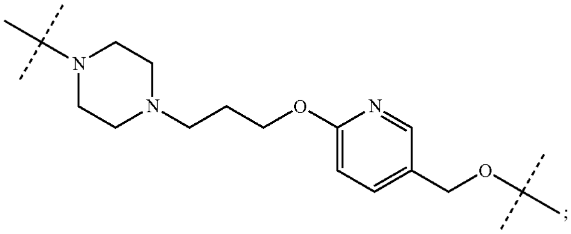 ; 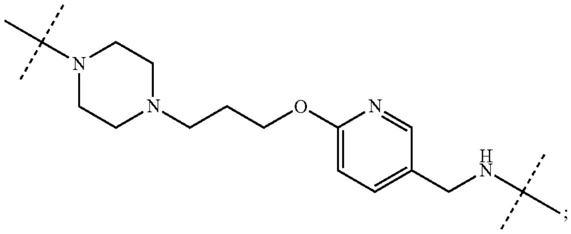 ;
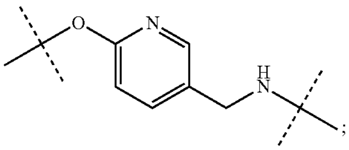 ; 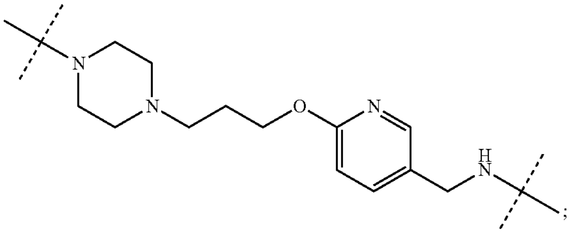 ;
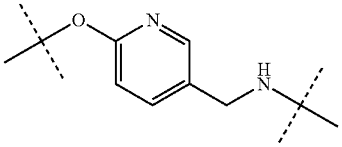 ; 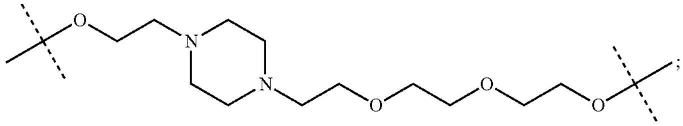 ;
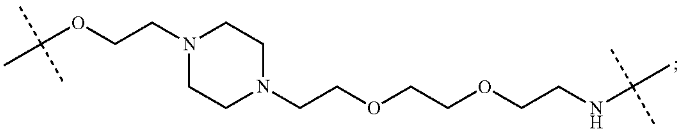 ;

-continued
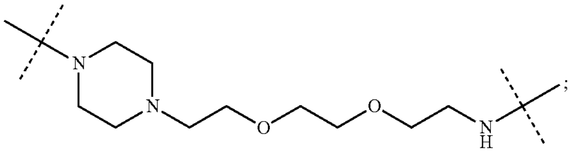
;
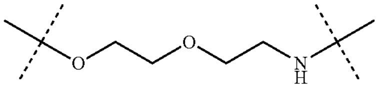
;
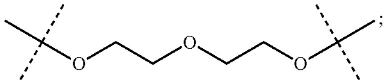
;
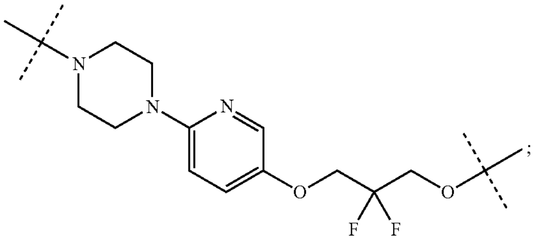
;
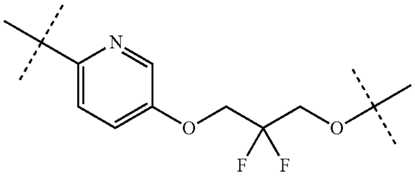
;
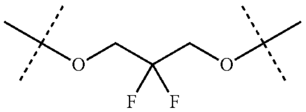
;
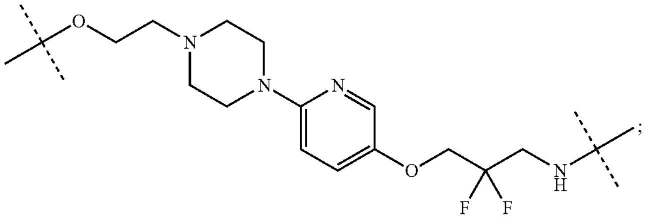
;
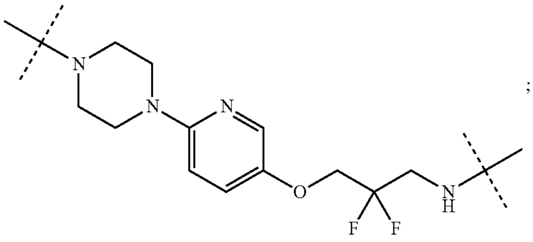
;
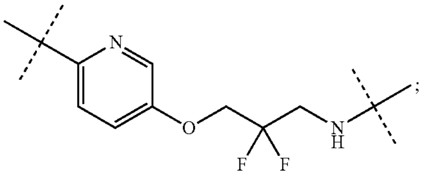
;
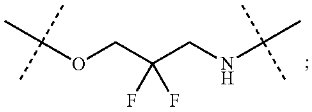
;
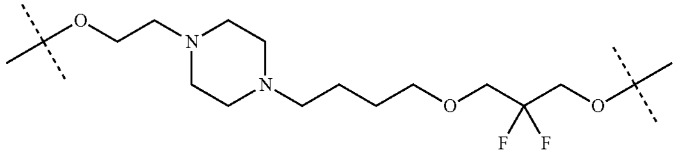
;
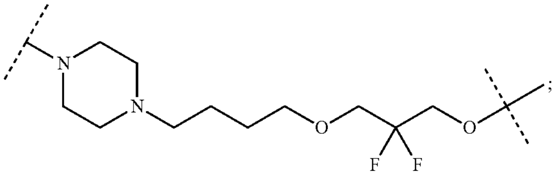
;
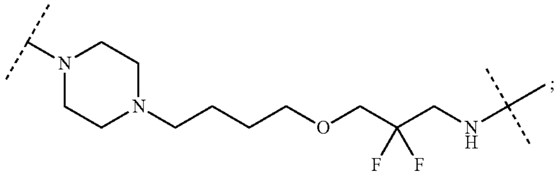
;
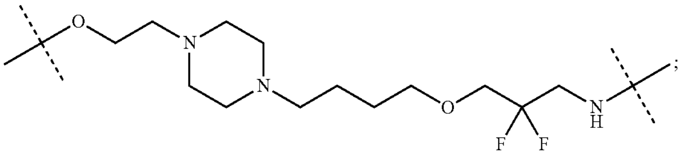
;
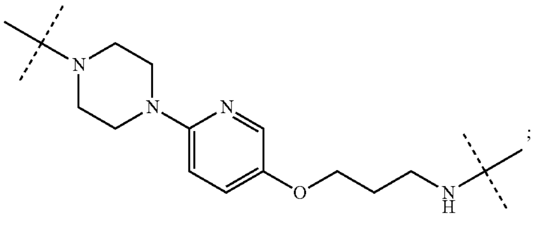
;
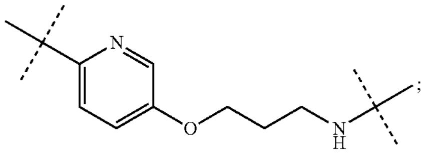
;

-continued
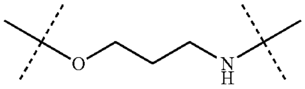 ; 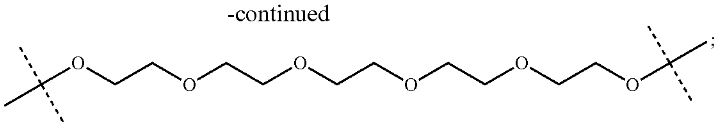 ;
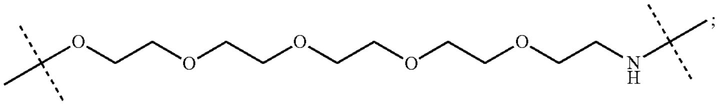 ;
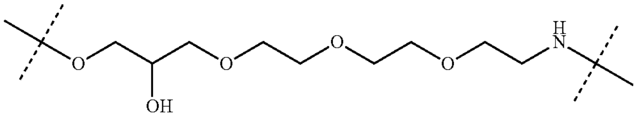 ; 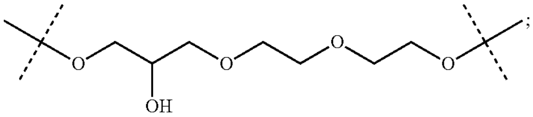 ;
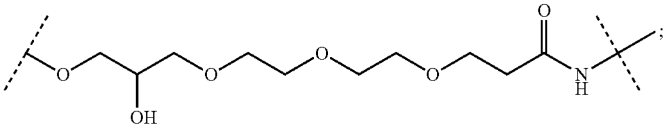 ;
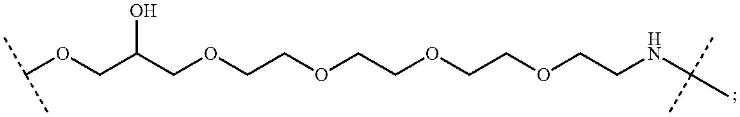 ;
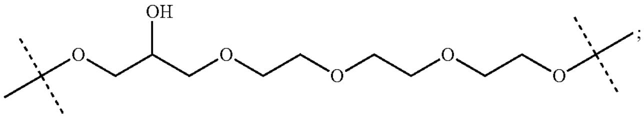 ;
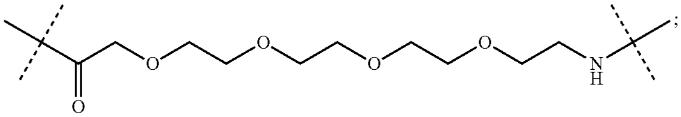 ;
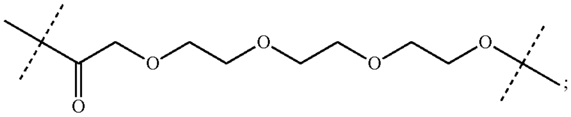 ; 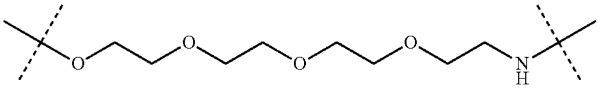 ;
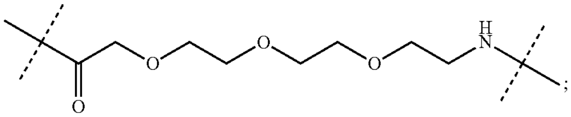 ;
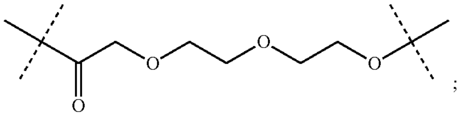 ; 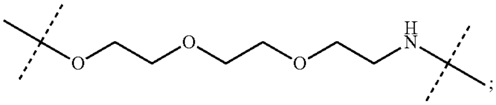 ;
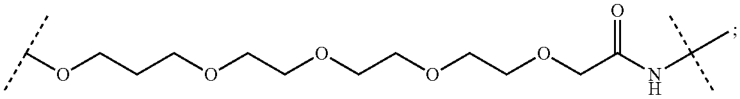 ;
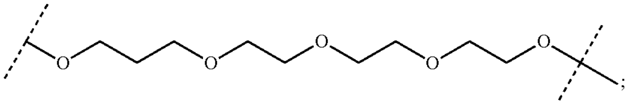 ; 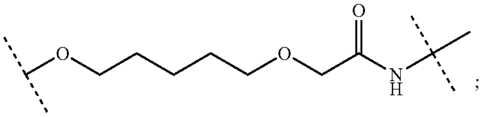 ;
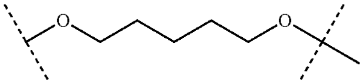 ; 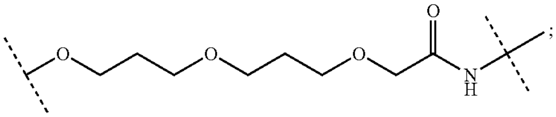 ;
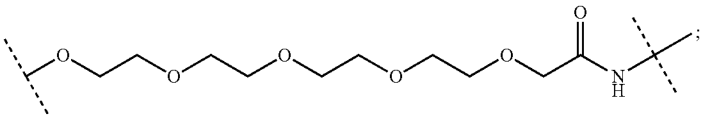 ;
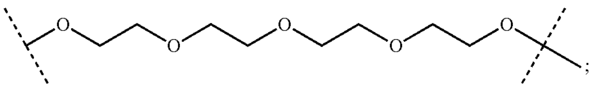 ;

-continued

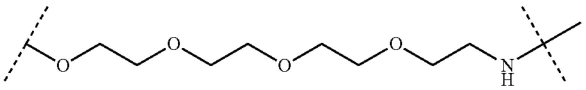 ; 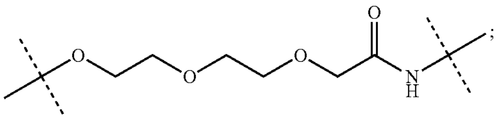 ;

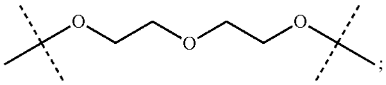 ; 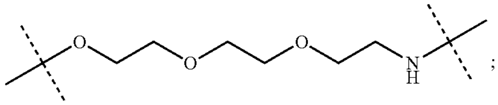 ;

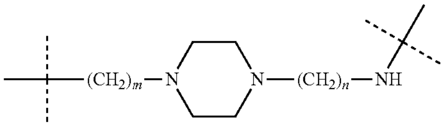 ; 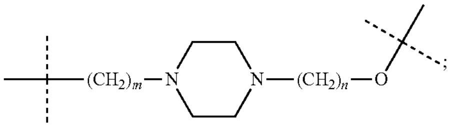 ;

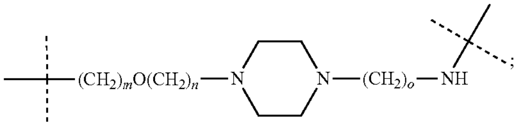 ; 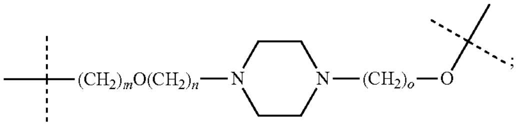 ;

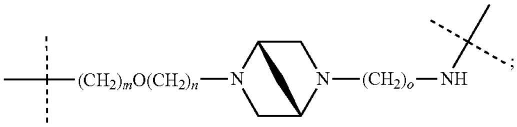 ; 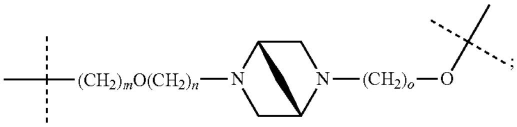 ;

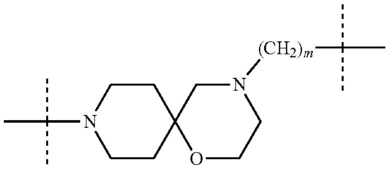 ; 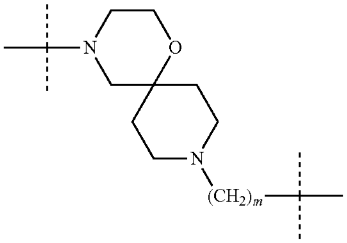 ; 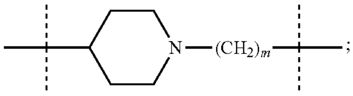 ;

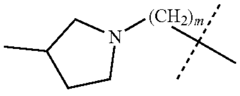 ; 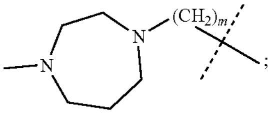 ; 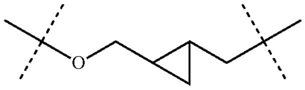 ; 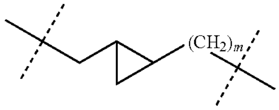 .

12. The bifunctional compound according to claim 1, or a pharmaceutically acceptable salt, enantiomer, or stereoisomer thereof, wherein the chemical linker group (L) comprises the following chemical structure:

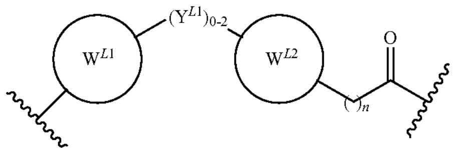 or

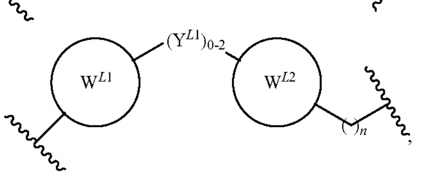 , wherein:

$W^{L1}$ and $W^{L2}$ are each independently absent or a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;

$Y^{L1}$ is each independently a bond, optionally substituted linear or branched $C_1$-$C_6$ alkyl, and optionally one or more C atoms are replaced with 0; or optionally substituted linear or branched $C_1$-$C_6$ alkoxy;

n is 0-10; and

indicates the attachment point to the PTM or ULM moieties.

13. The bifunctional compound according to claim 1, or a pharmaceutically acceptable salt, enantiomer, or stereoisomer thereof, wherein the chemical linker group (L) comprises the following chemical structure:

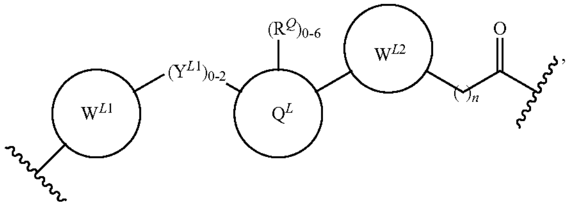

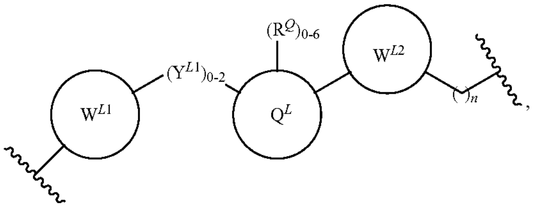

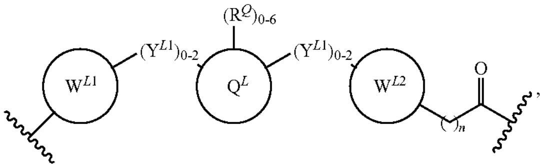

or

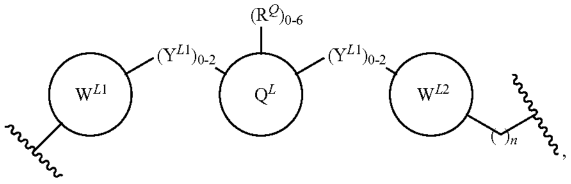

wherein:

$W^{L1}$ and $W^{L2}$ are each independently absent, aryl, heteroaryl, cyclic, heterocyclic, $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, 0, S, $NR^{YL2}$, $CR^{YL1}R^{YL2}$, C°O, C=S, SO, $SO_2$, optionally substituted linear or branched $C_1$-$C_6$ alkyl and optionally one or more C atoms are replaced with O; optionally substituted linear or branched $C_1$-$C_6$ alkoxy;

$Q^L$ is a 3-6 membered alicyclic or aromatic ring with 0-4 heteroatoms, optionally bridged, optionally substituted with 0-6 $R^Q$, each $R^Q$ is independently H, optionally substituted linear or branched $C_{1-6}$ alkyl (e.g., optionally substituted by 1 or more halo or $C_{1-6}$ alkoxyl), or 2 $R^Q$ groups taken together with the atom they are attached to, form a 3-8 membered ring system containing 0-2 heteroatoms;

$R^{YL1}$, $R^{YL2}$ are each independently H, OH, optionally substituted linear or branched $C_{1-6}$ alkyl (e.g., optionally substituted by 1 or more halo or $C_{1-6}$ alkoxyl), or $R^1$, $R^2$ together with the atom they are attached to, form a 3-8 membered ring system containing 0-2 heteroatoms;

n is 0-10; and

indicates the attachment point to the PTM or ULM moieties.

14. The bifunctional compounds according to claim 1, or a pharmaceutically acceptable salt, enantiomer, or stereoisomer thereof, wherein the chemical linker group (L) is selected from the group consisting of:

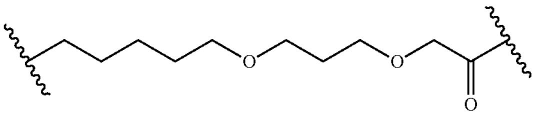;

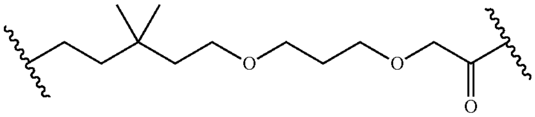;

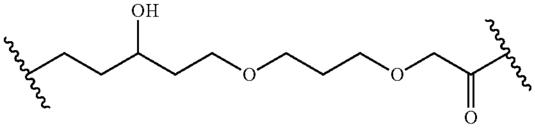;

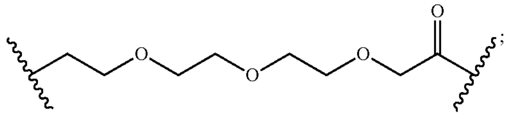;

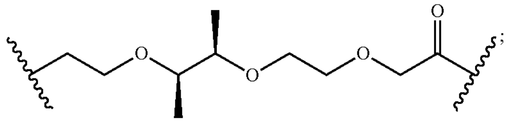;

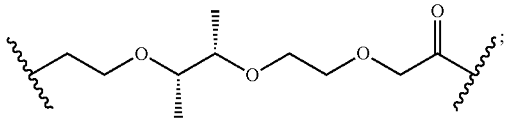;

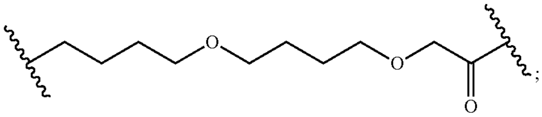;

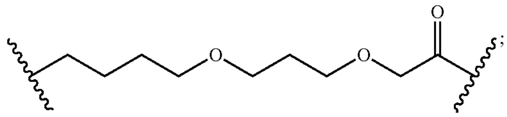;

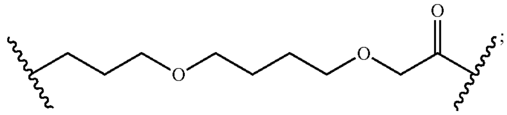;

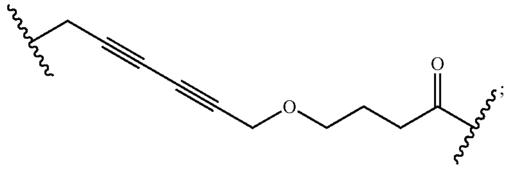;

-continued
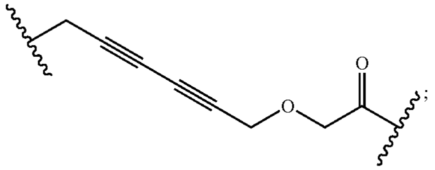
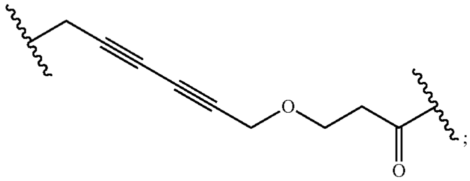
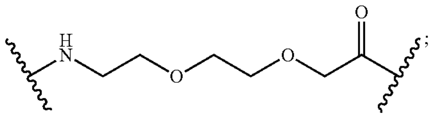
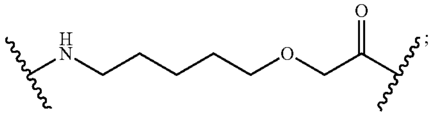
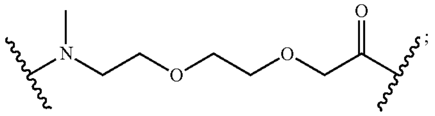
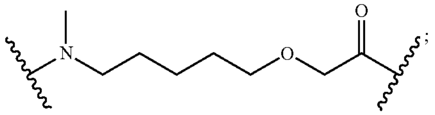
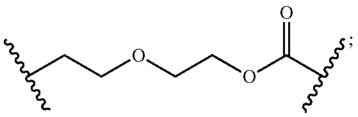
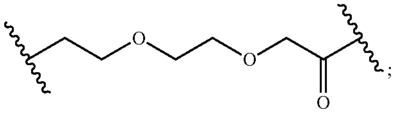
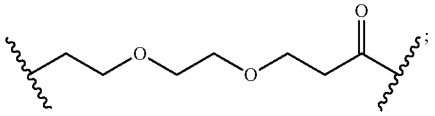
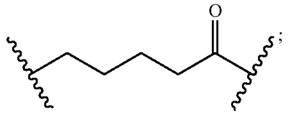
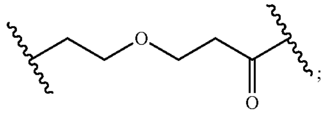
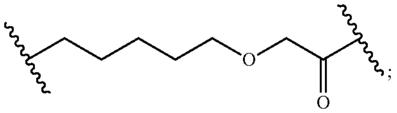
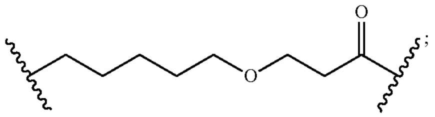
-continued
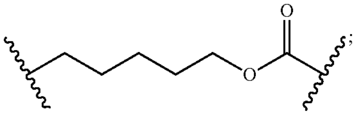
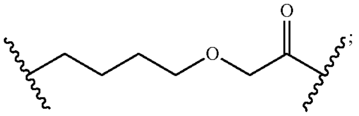
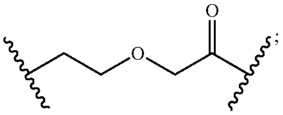
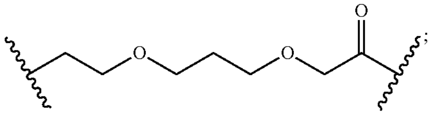
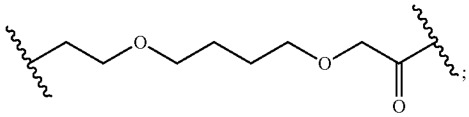
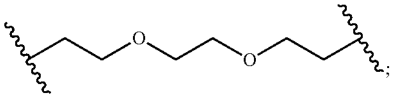
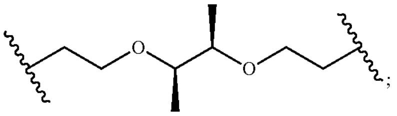
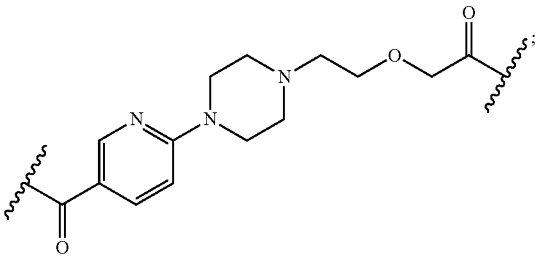
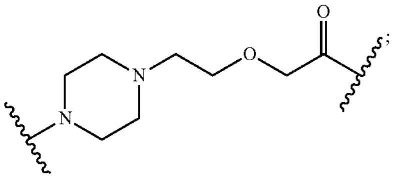
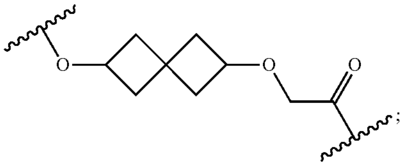
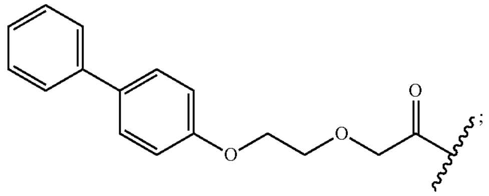

-continued
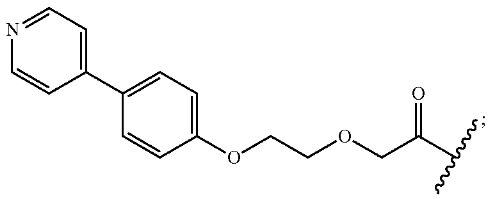
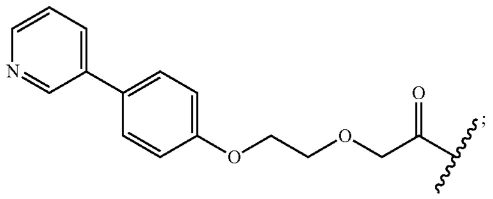
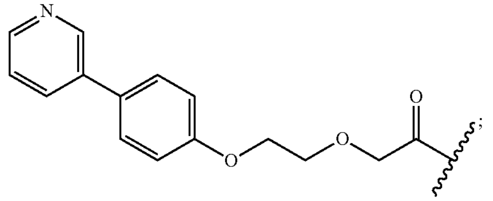
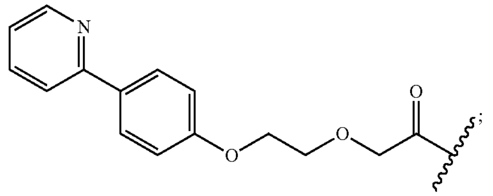
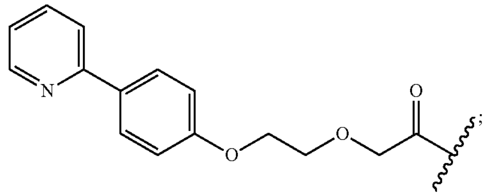
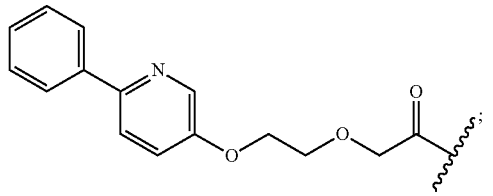
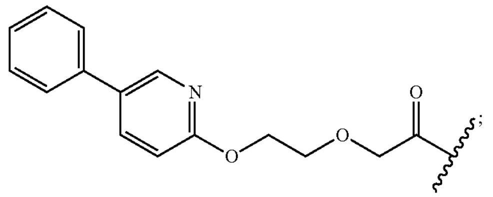
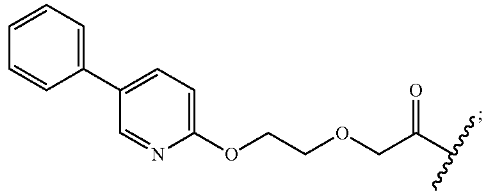
-continued
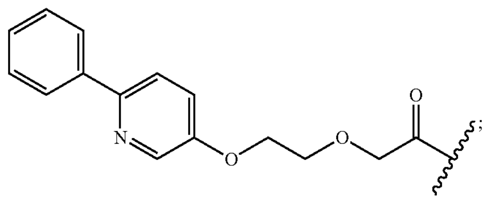
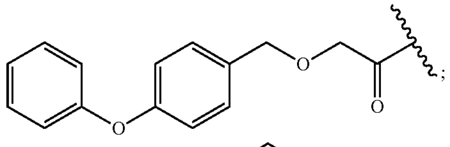
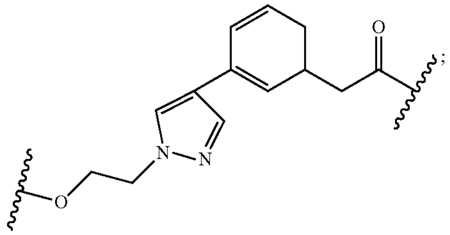
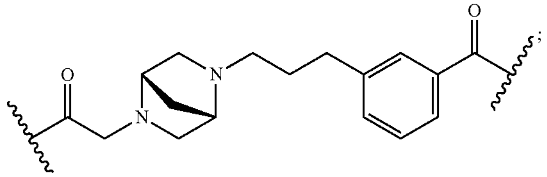
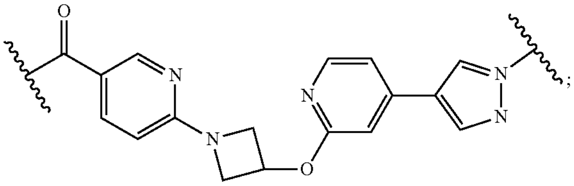
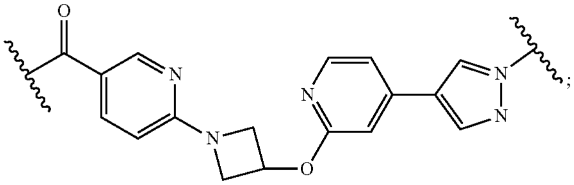
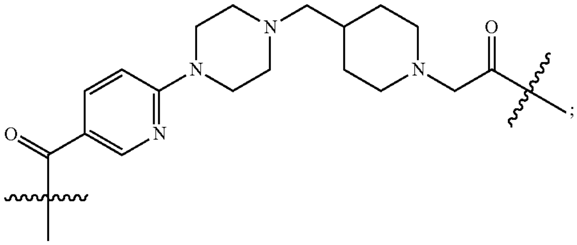
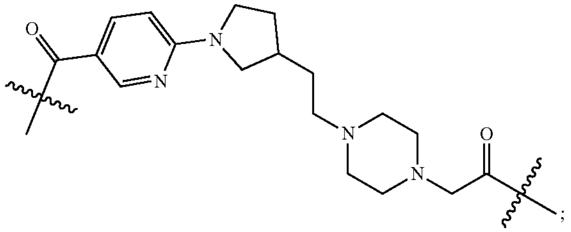

-continued

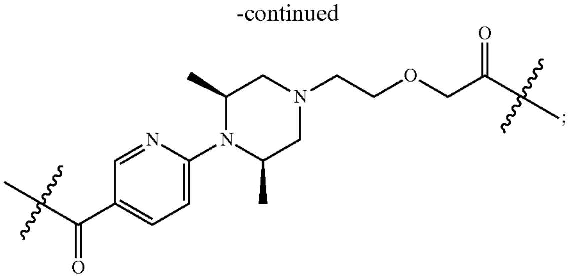

;

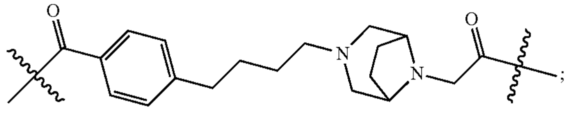

;

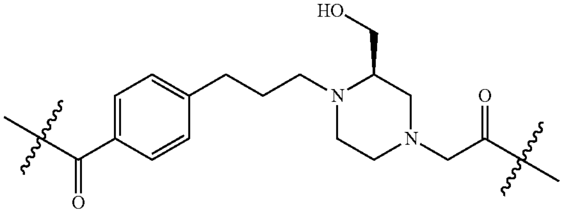

;

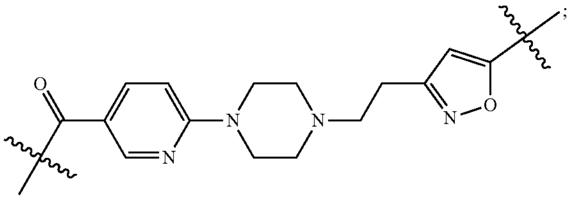

;

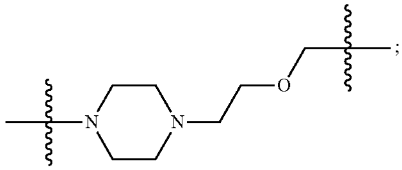

;

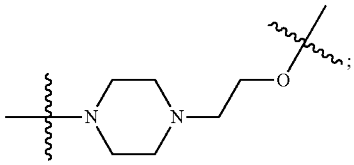

;

-continued

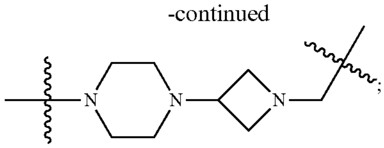

; and

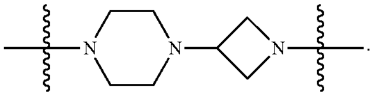

.

15. The bifunctional compound according to claim 1, or a pharmaceutically acceptable salt, enantiomer, or stereoisomer thereof, wherein the chemical linker group (L) includes an optionally substituted $C_1$-$C_{40}$ alkyl, wherein:

each carbon is optionally substituted with $CR^{L1}R^{L2}$, O, S, SO, $SO_2$, $NR^{L3}$, $SO_2NR^{L3}$, $SONR^{L3}$, $CONR^{L3}$, CO, $CR^{L1}$=$CR^{L2}$, C≡C, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$ heterocyclyl optionally substituted with 0-6 $R^{L1}$ and/or $R^{L2}$ groups, $C_{5-13}$ spiroheterocyclyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, PCC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$.

16. The bifunctional compound according to claim 1, or a pharmaceutically acceptable salt, enantiomer, or stereoisomer thereof, wherein the chemical linker group (L) is selected from the group consisting of:

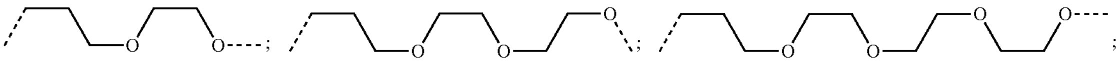

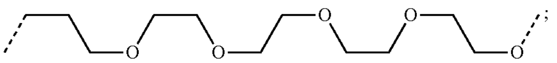

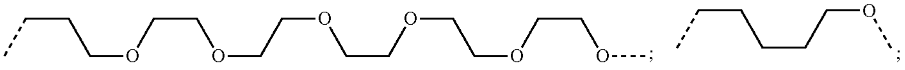

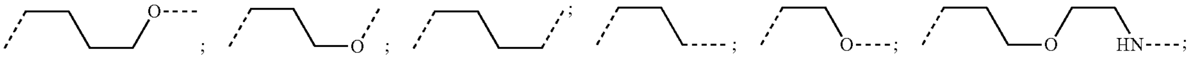

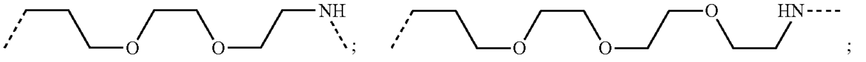

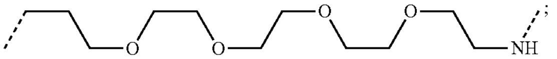

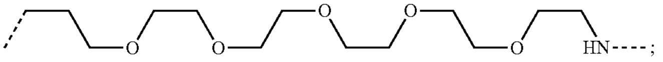

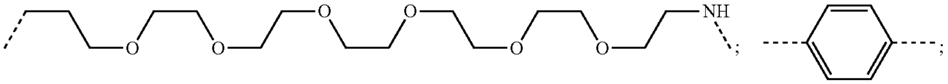

;

-continued
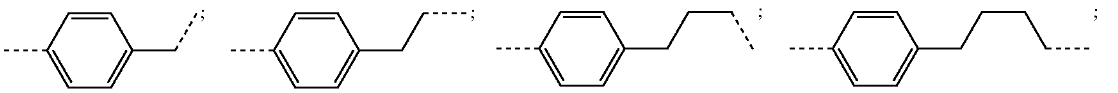
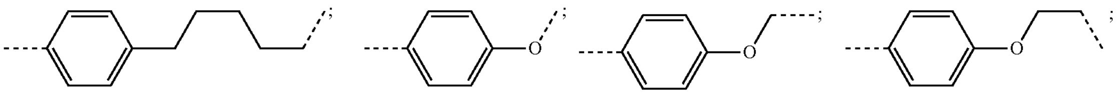
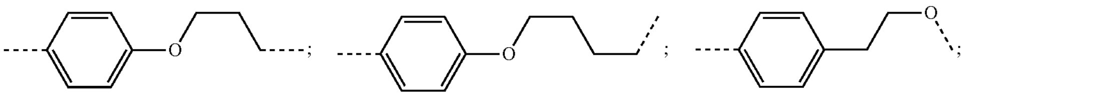
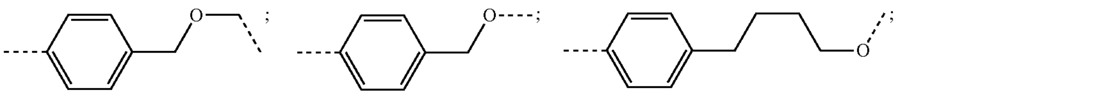
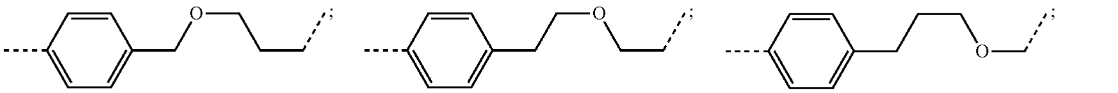
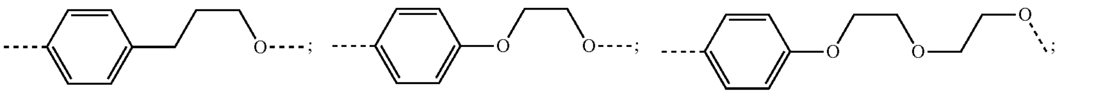
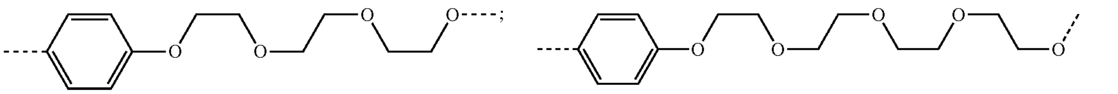
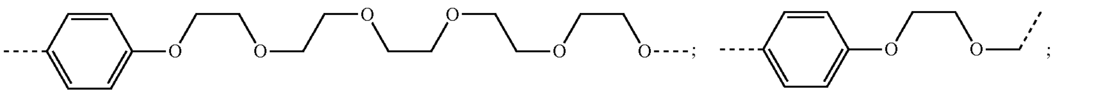
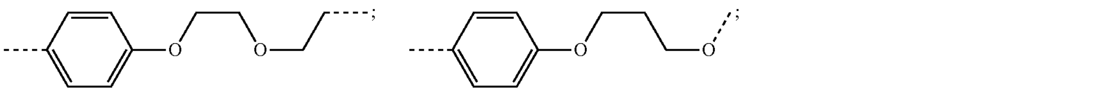
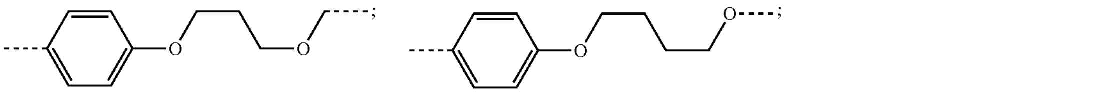
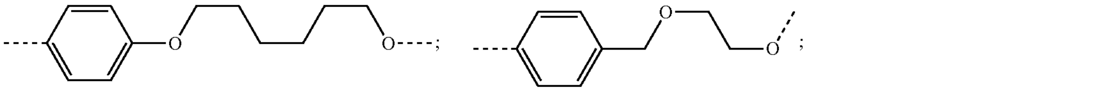
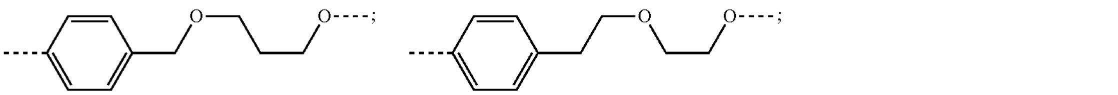
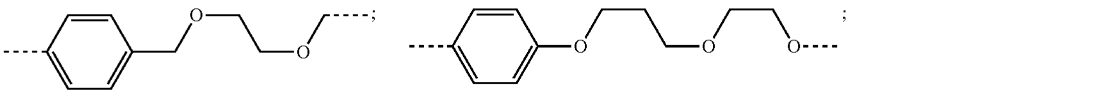
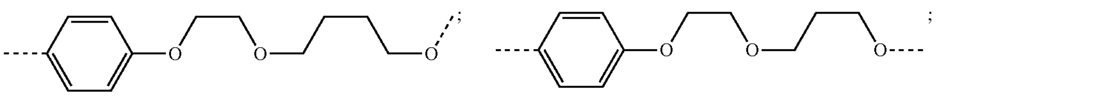
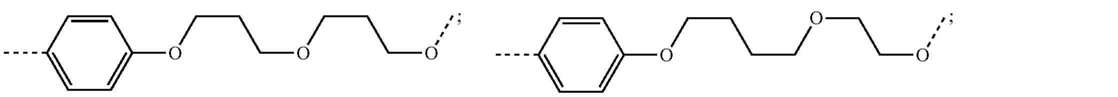
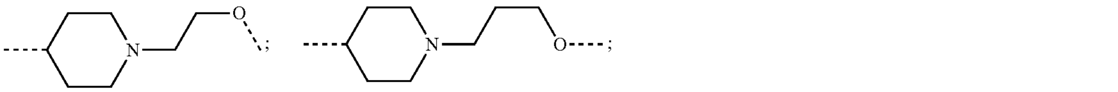
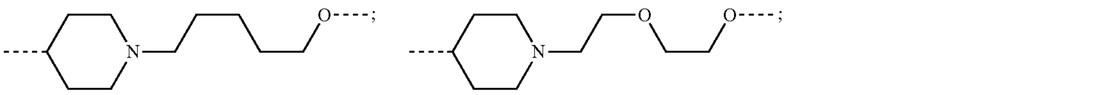
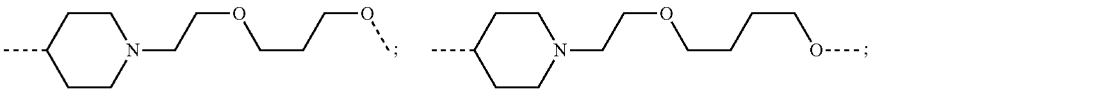

-continued
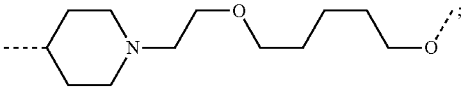 ;
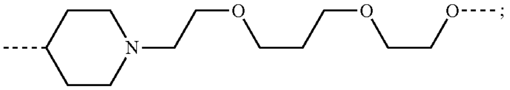 ;
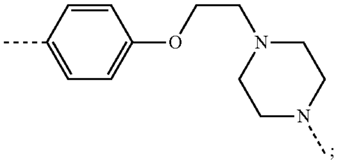 ;
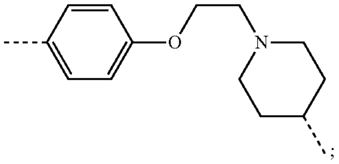 ;
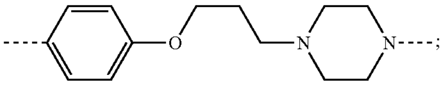 ;
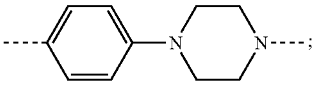 ;
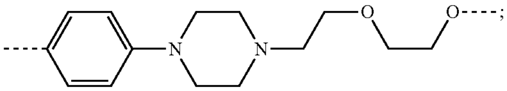 ;
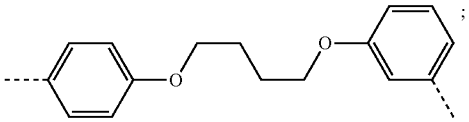 ;
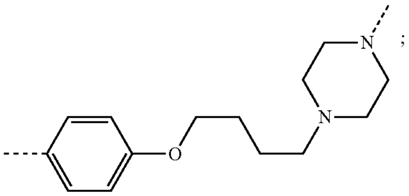 ;
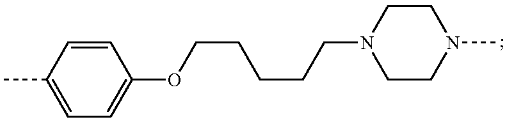 ;
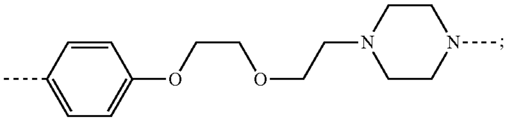 ;
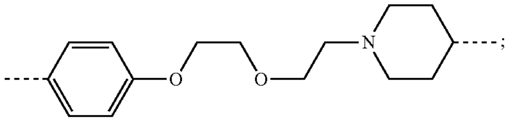 ;
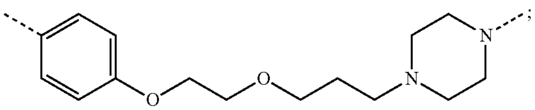 ;
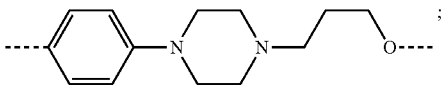 ;
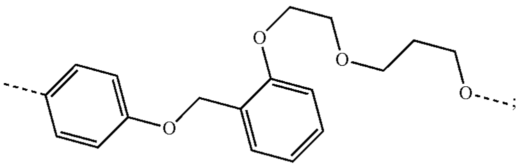 ;
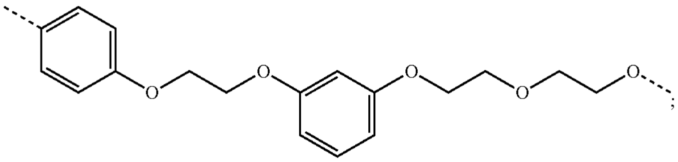 ;
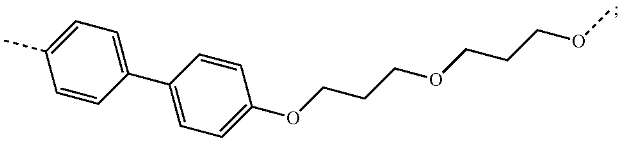 ;
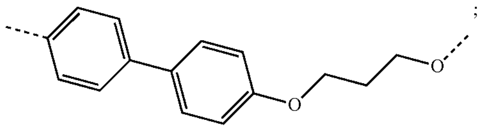 ;
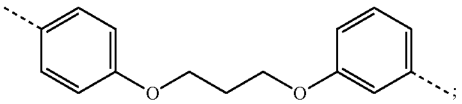 ;
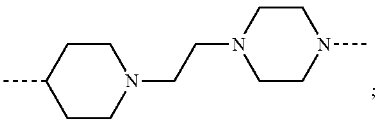 ;
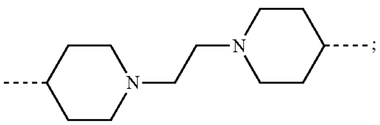 ;
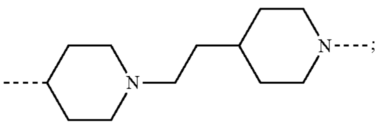 ;
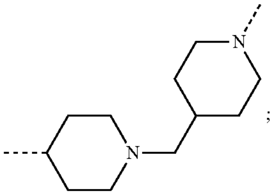 ;
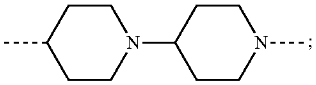 ;
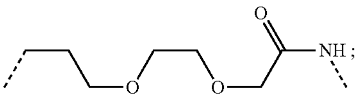 ;
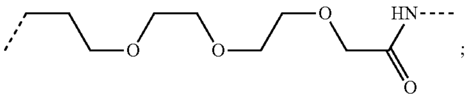 ;
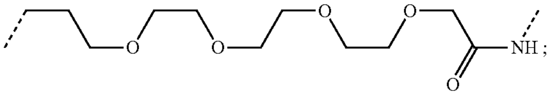 ;
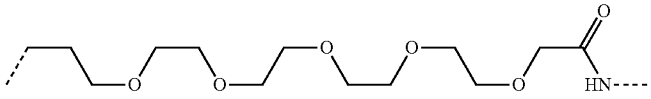

-continued
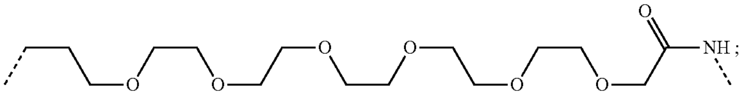 ; 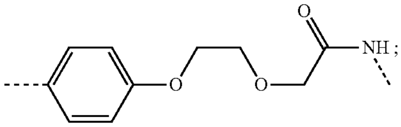 ;
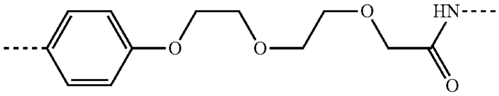 ; 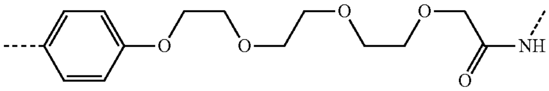 ;
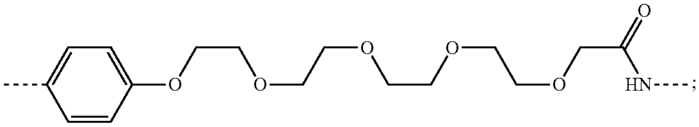 ;
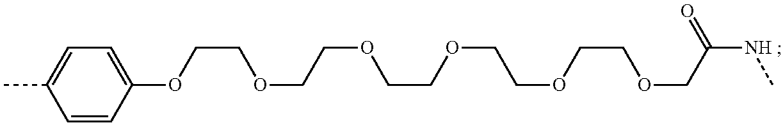 ; 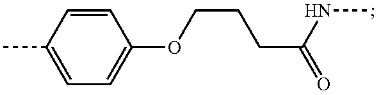 ;
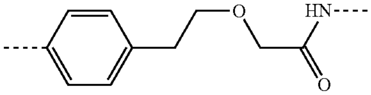 ; 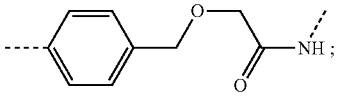 ; 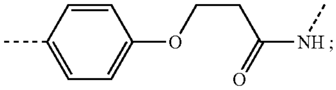 ;
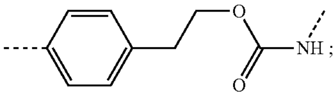 ; 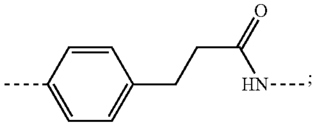 ;
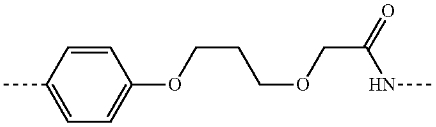 ; 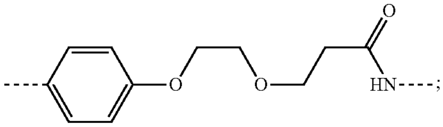 ;
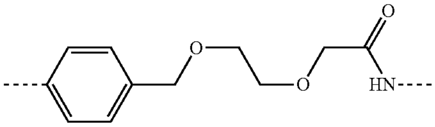 ; 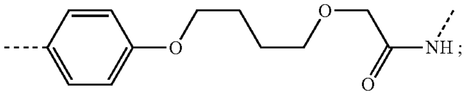 ;
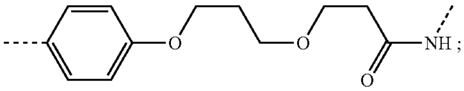 ; 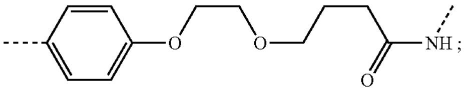 ;
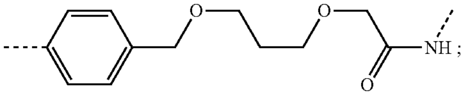 ; 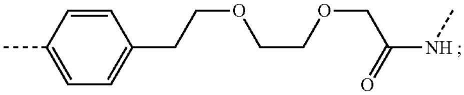 ;
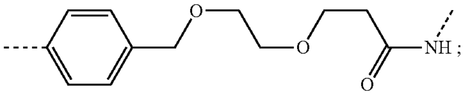 ; 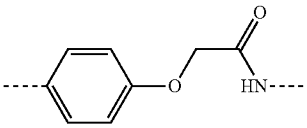 ;
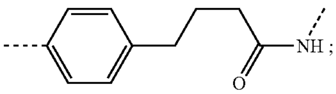 ; 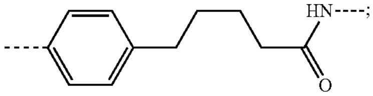 ;
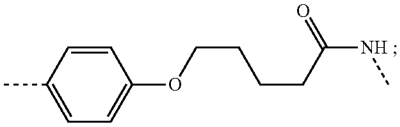 ; 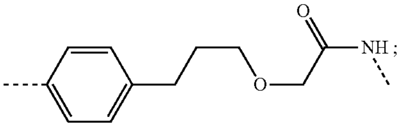 ;
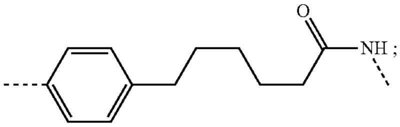 ; 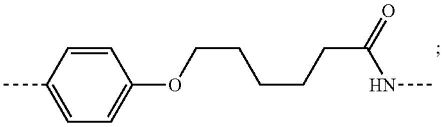 ;

-continued
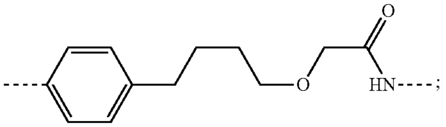
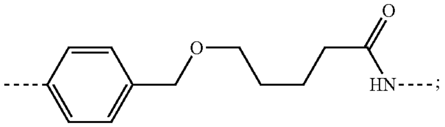
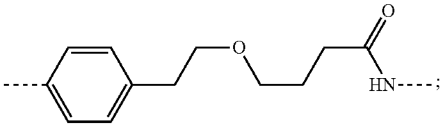
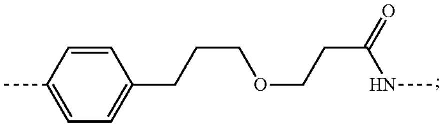
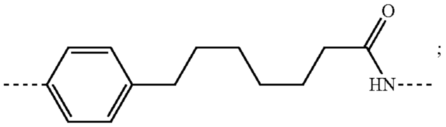
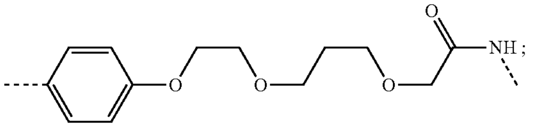
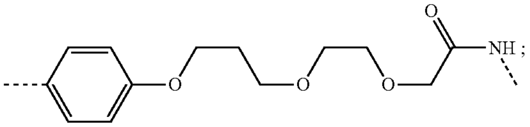
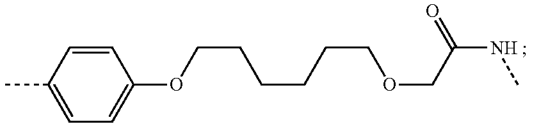
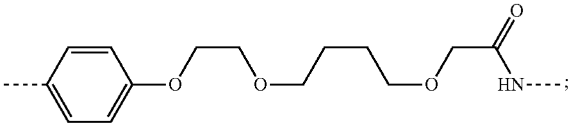
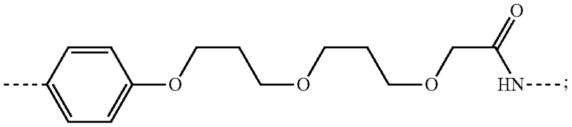
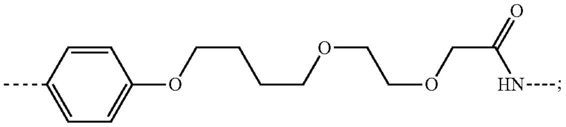
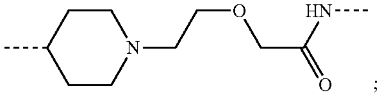
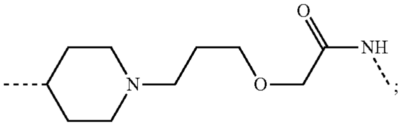
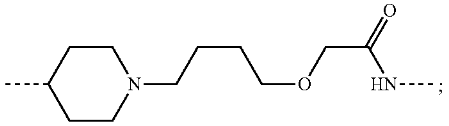
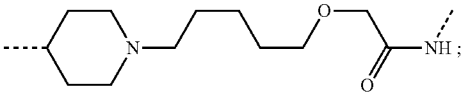
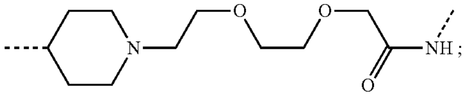
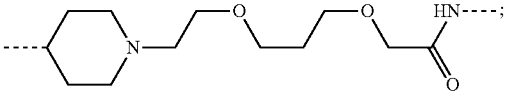
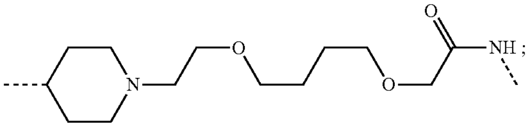
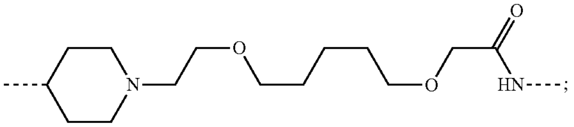
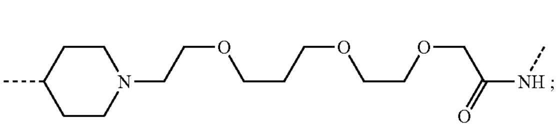
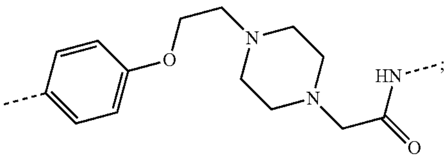
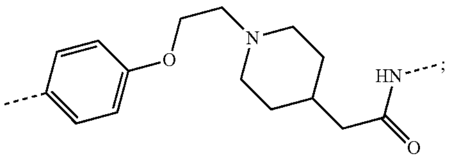
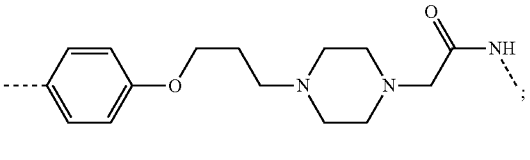
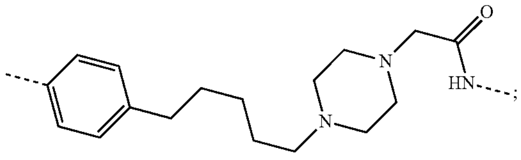
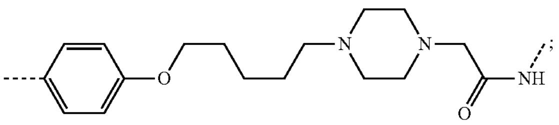
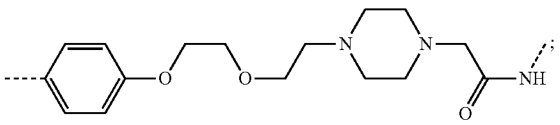

-continued
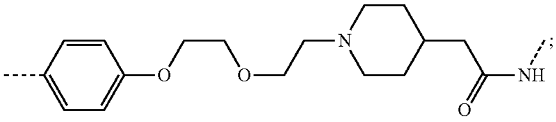;
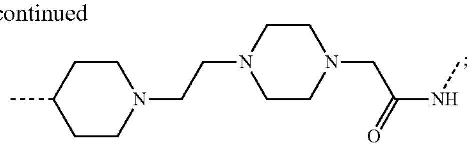;
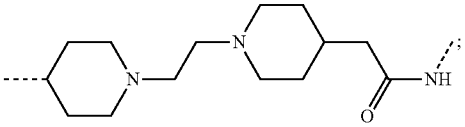;
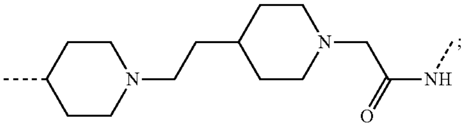;
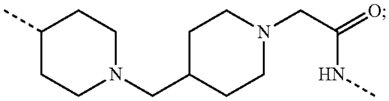;
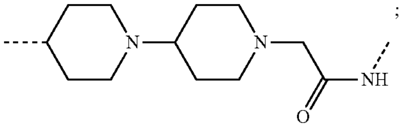;
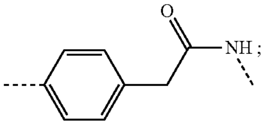;
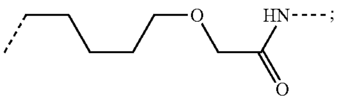;
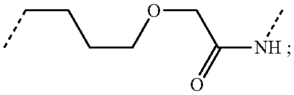;
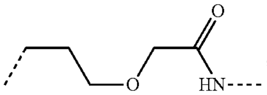;
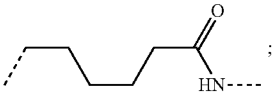;
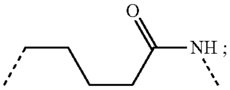;
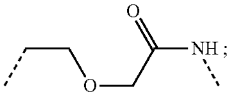;
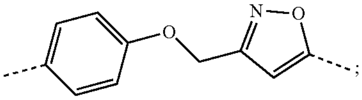;
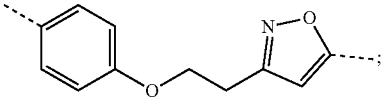;
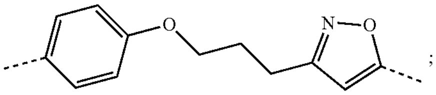;
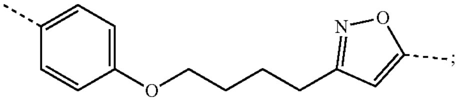;
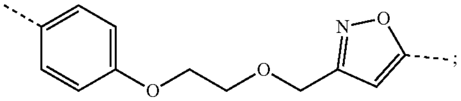;
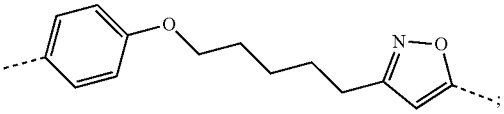;
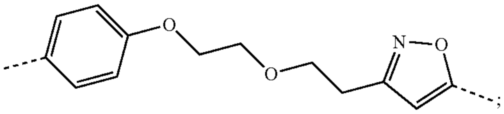;
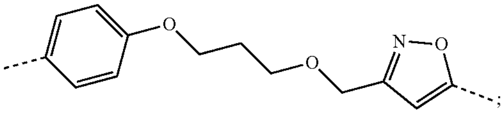;
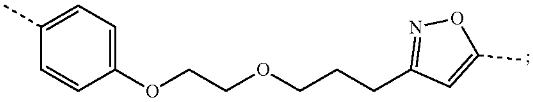;
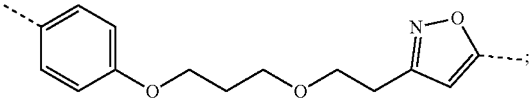;
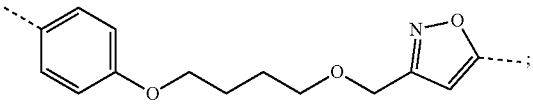;
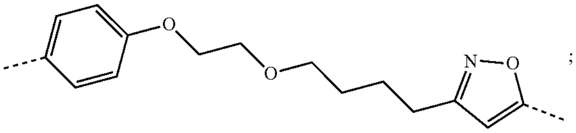;
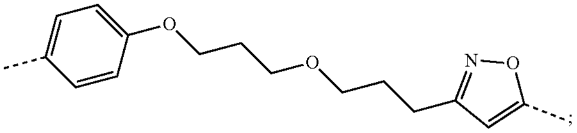;
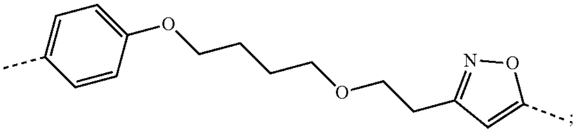;
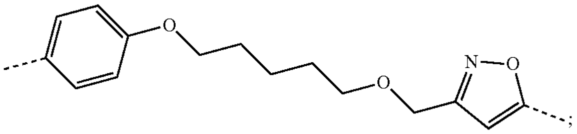;
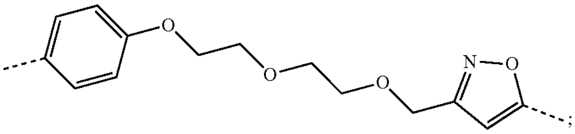;

-continued
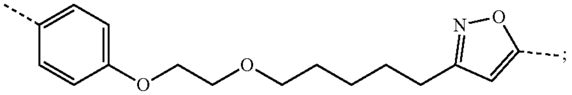 ;
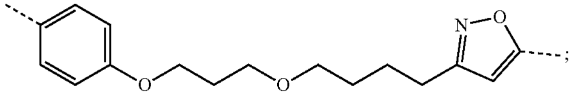 ;
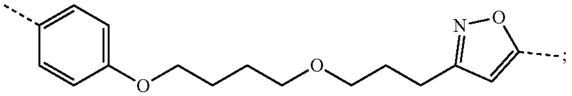 ;
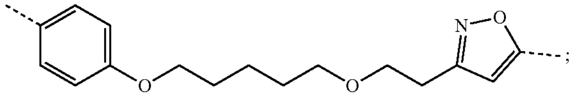 ;
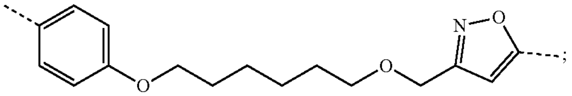 ;
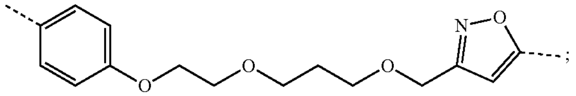 ;
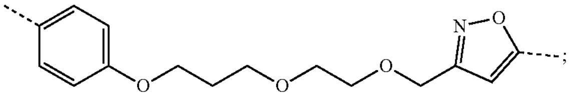 ;
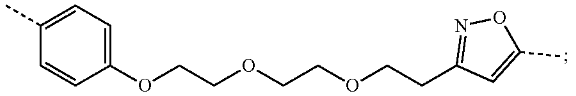 ;
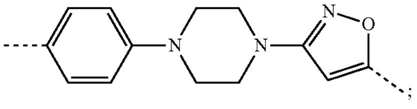 ;
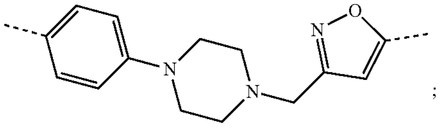 ;
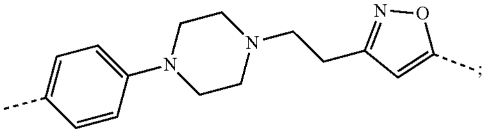 ;
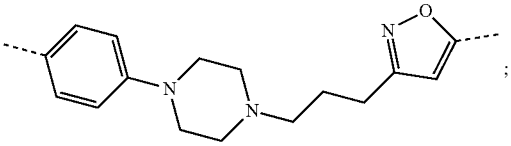 ;
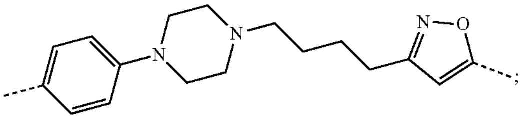 ;
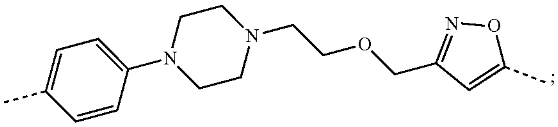 ;
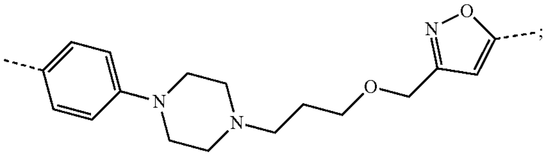 ;
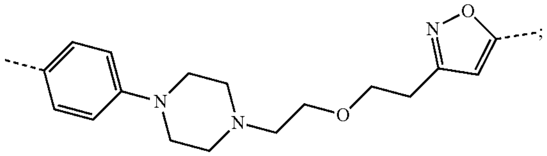 ;
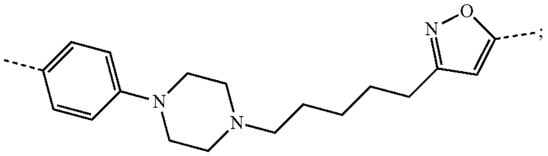 ;
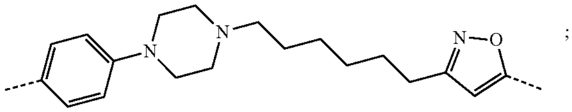 ;
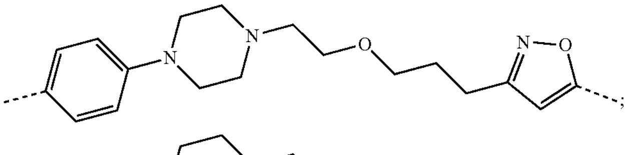 ;
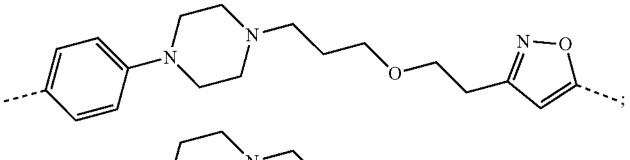 ;
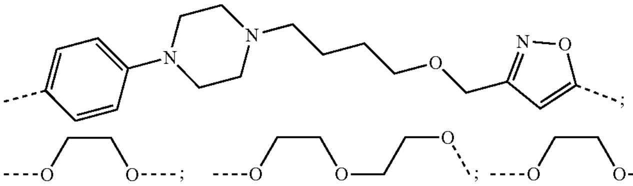 ;
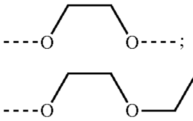 ;
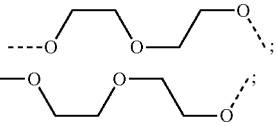 ;
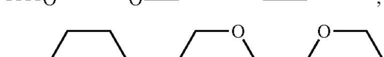 ;
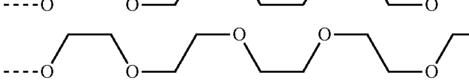 ;
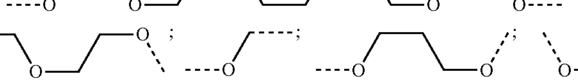 ;
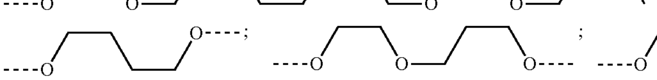 ;
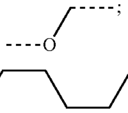 ;
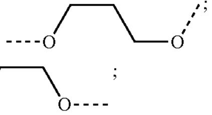 ;
 ;
 ;
 ;
 ;

-continued
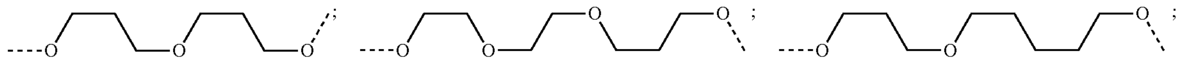
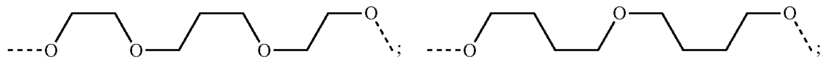
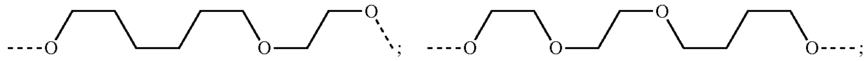
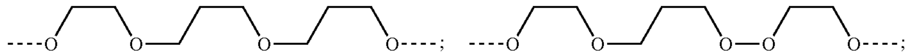
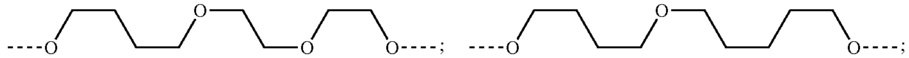
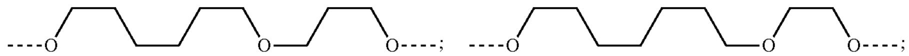
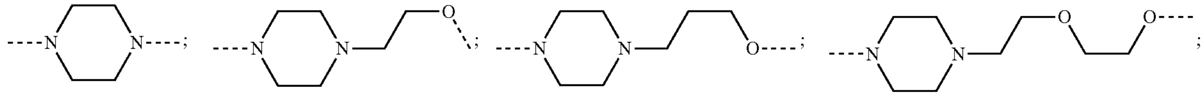
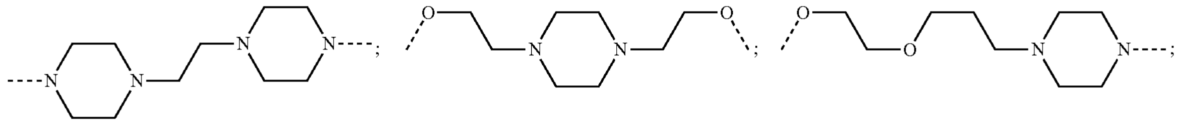
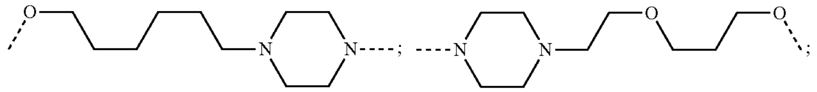
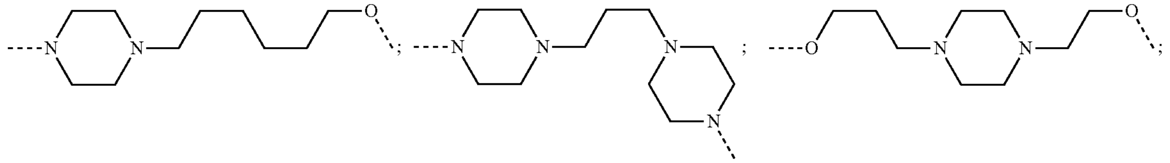
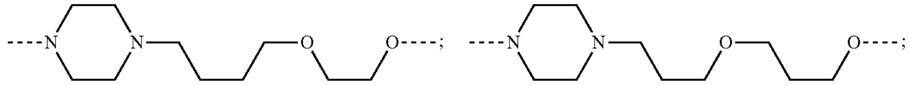
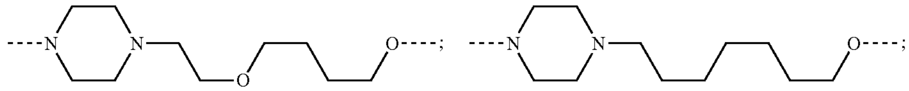
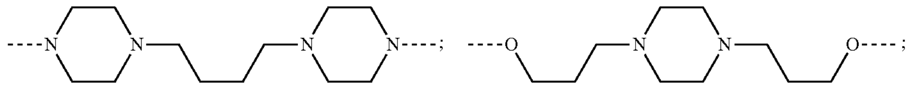
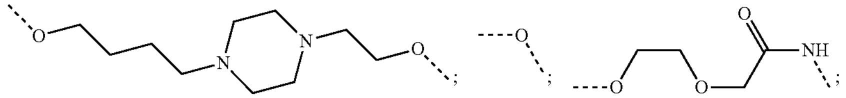
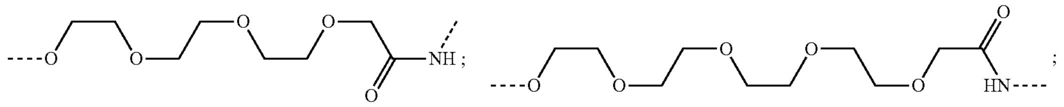
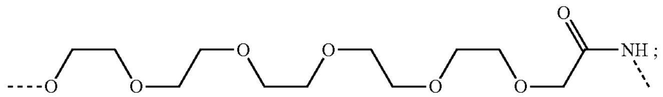
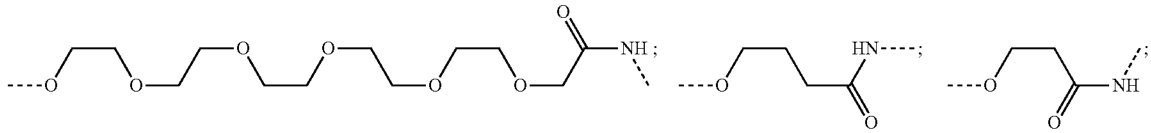
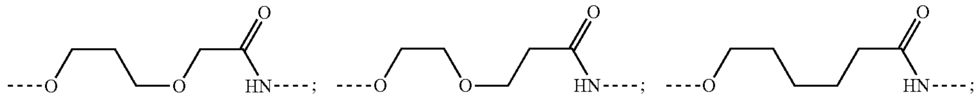
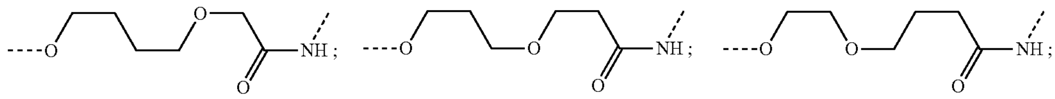

-continued
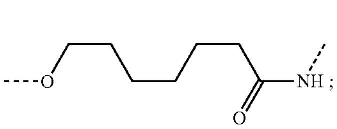
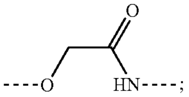
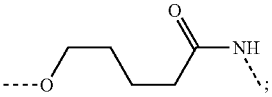
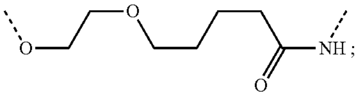
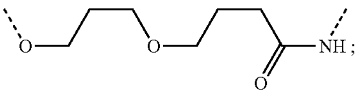
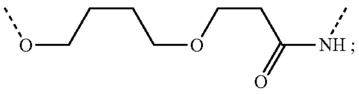
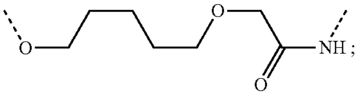
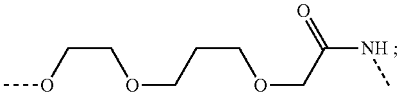
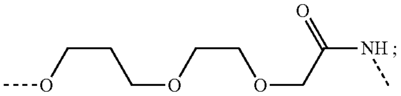
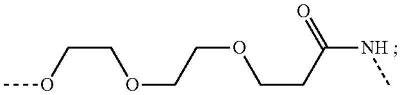
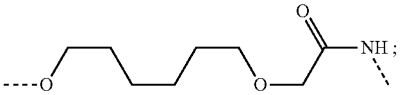
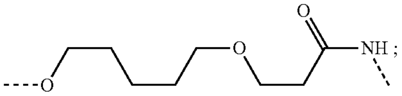
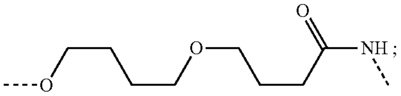
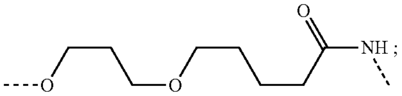
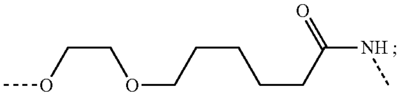
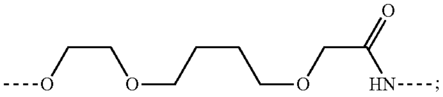
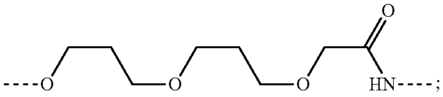
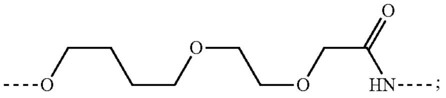
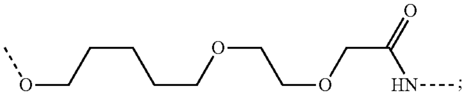
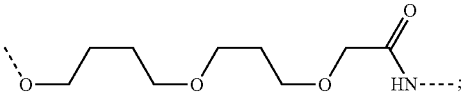
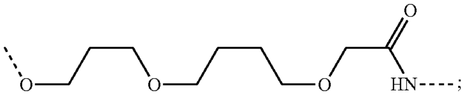
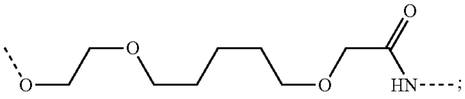
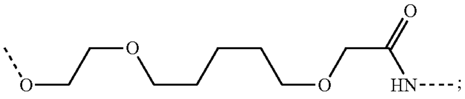
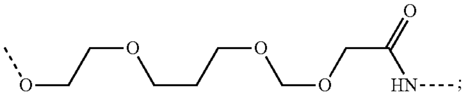
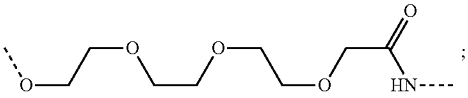
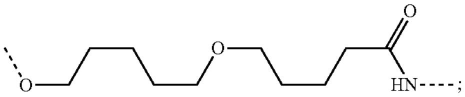
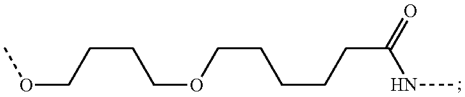
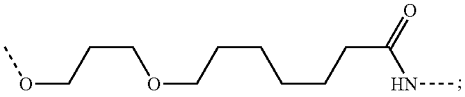
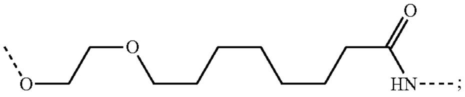
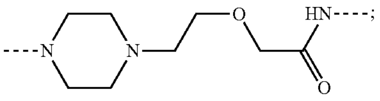
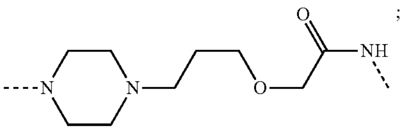
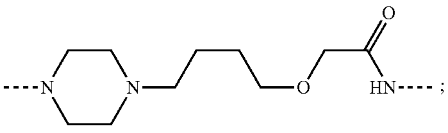
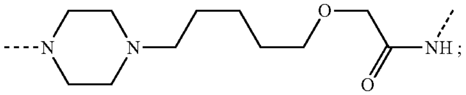

-continued
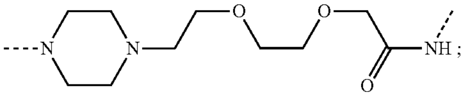 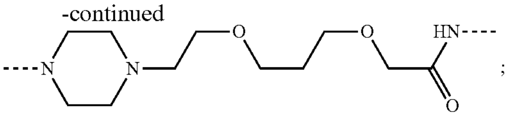
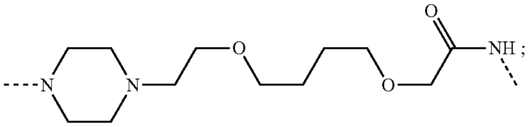 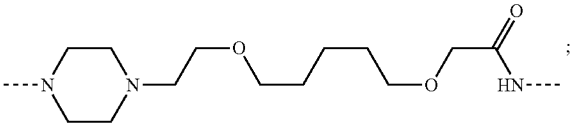
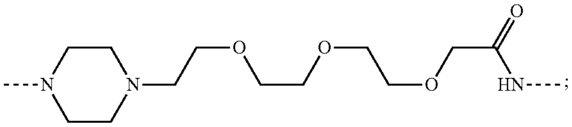 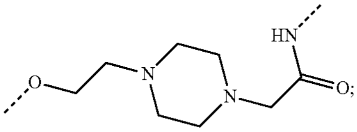
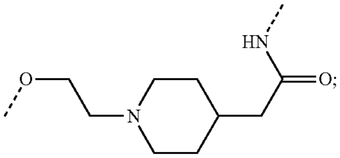 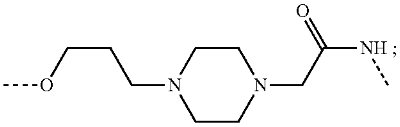
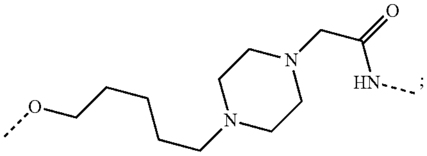 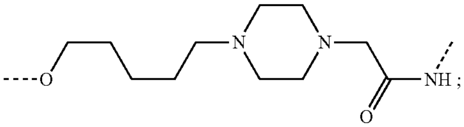
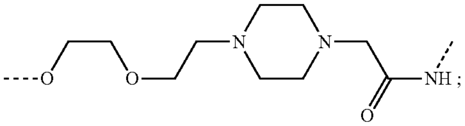 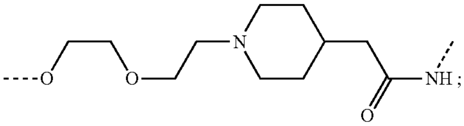
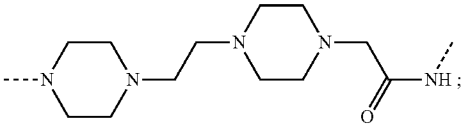 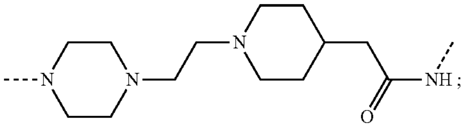
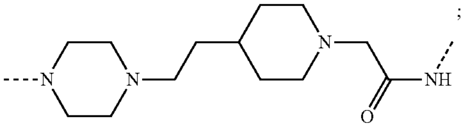 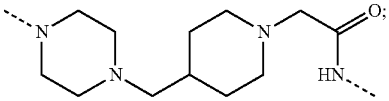
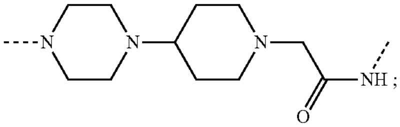 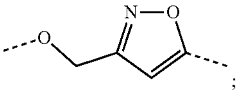
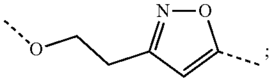 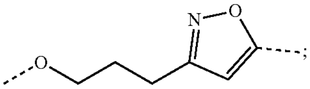
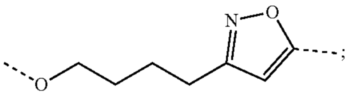 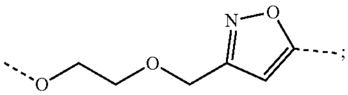
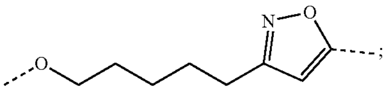 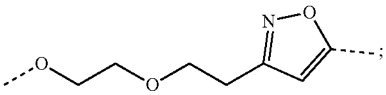
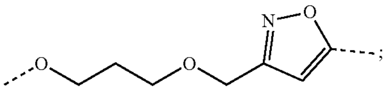 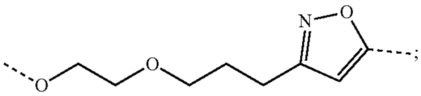
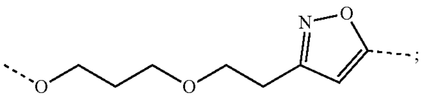 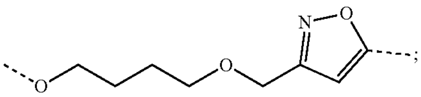
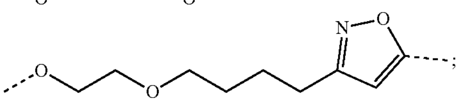 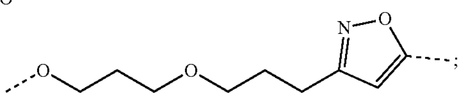

-continued
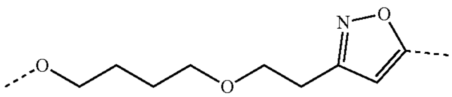;
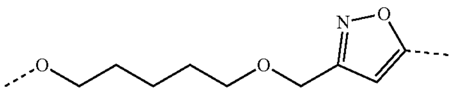;
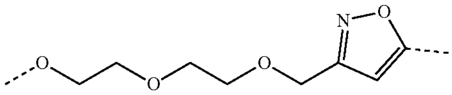;
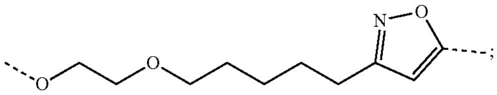;
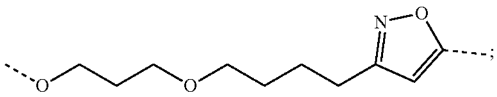;
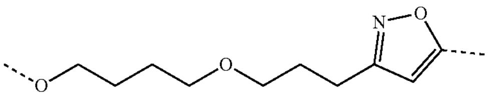;
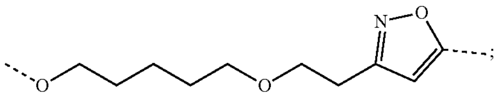;
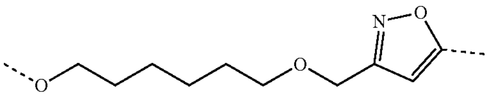;
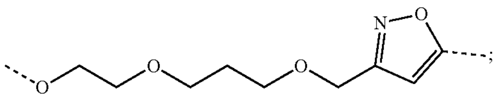;
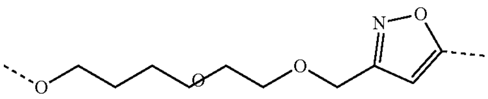;
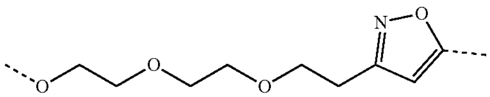;
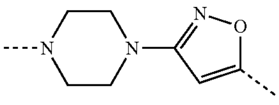;
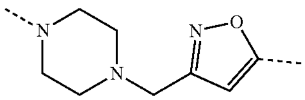;
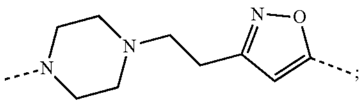;
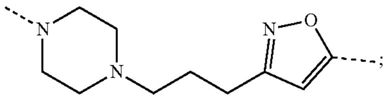;
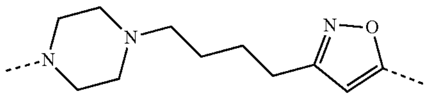;
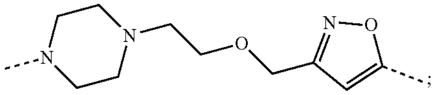;
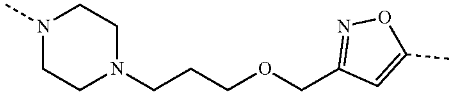;
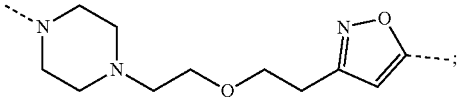;
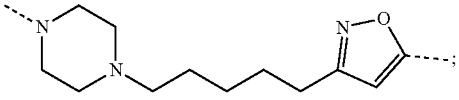;
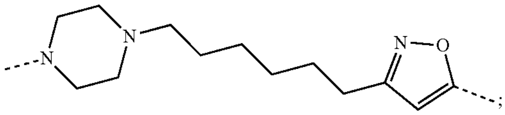;
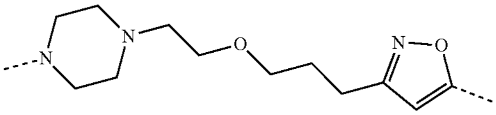;
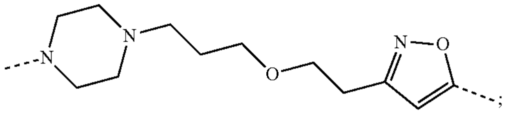; and
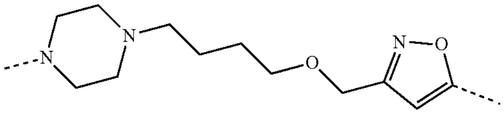.

17. The bifunctional compound according to claim 1, wherein the compound is selected from:
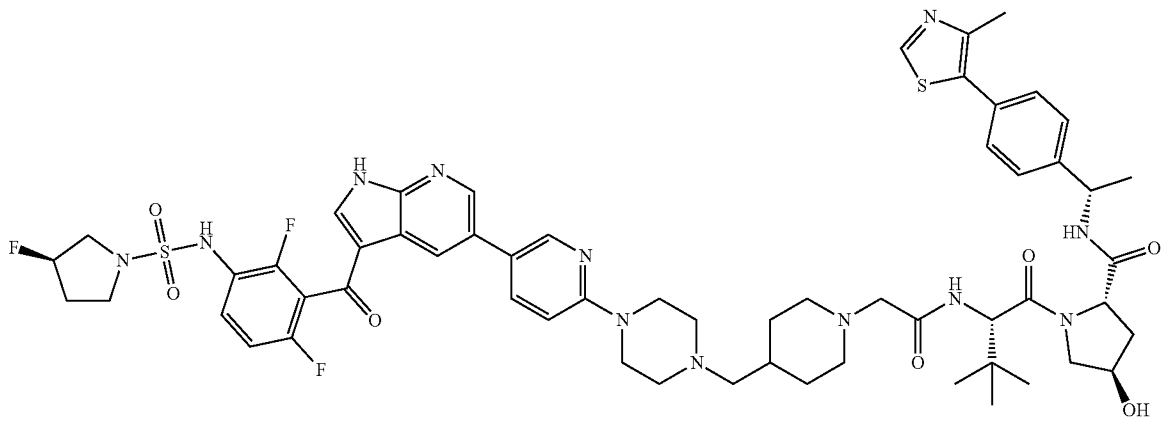
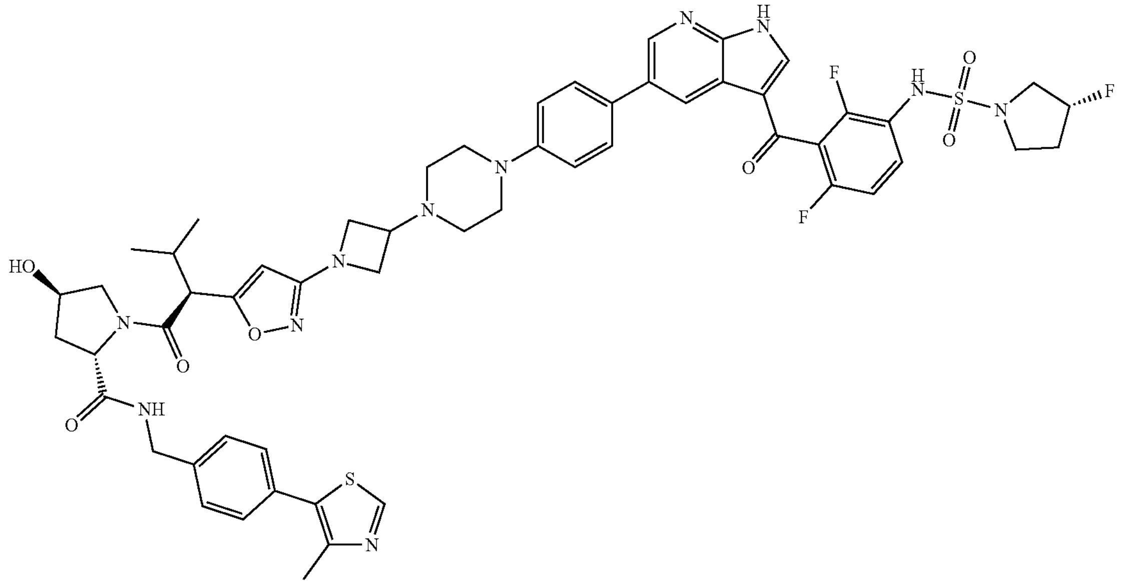
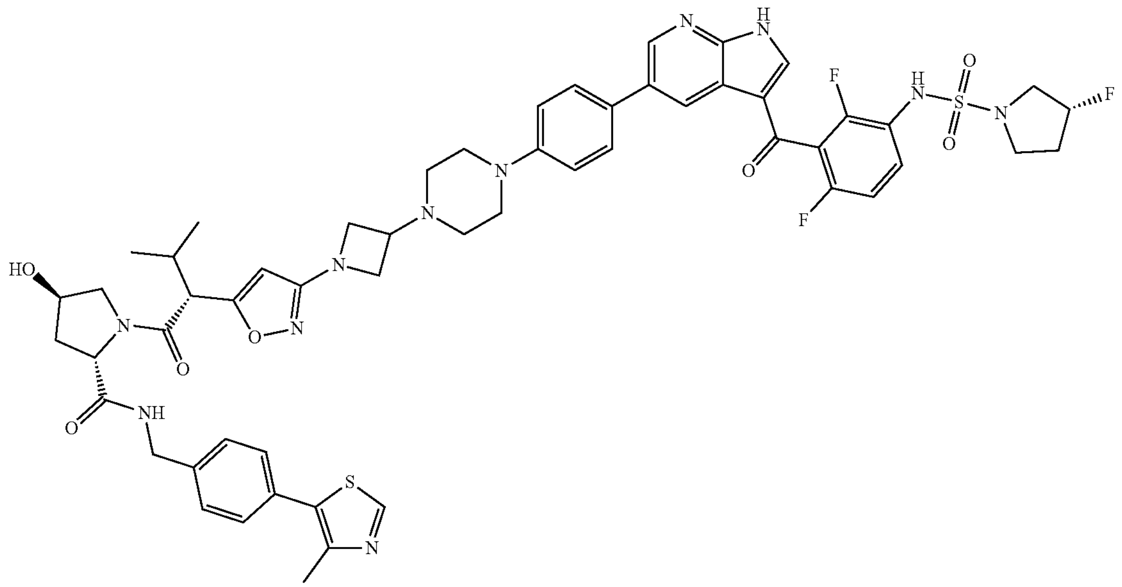

-continued
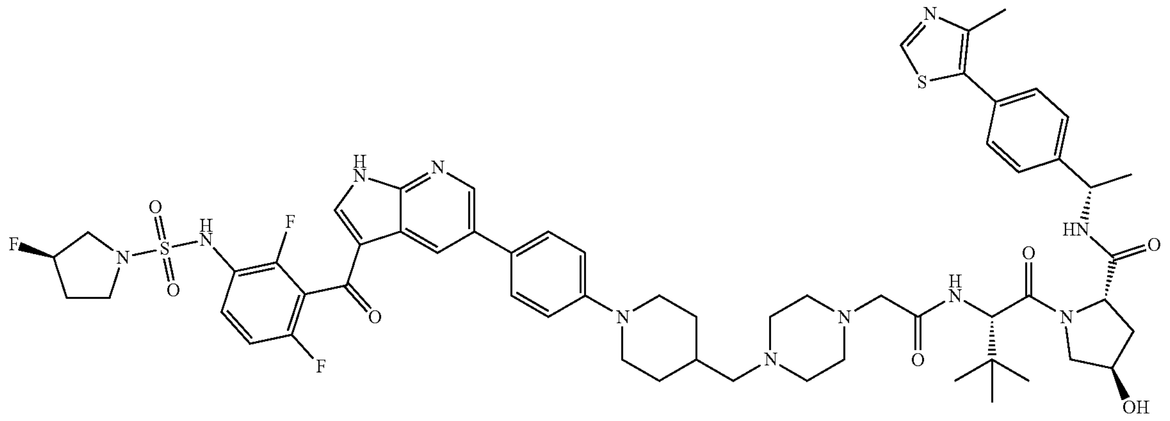
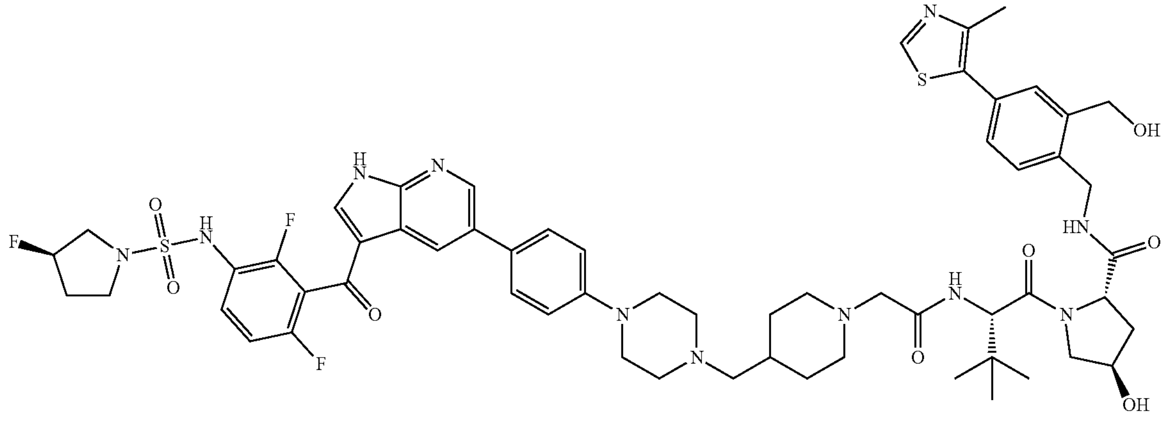
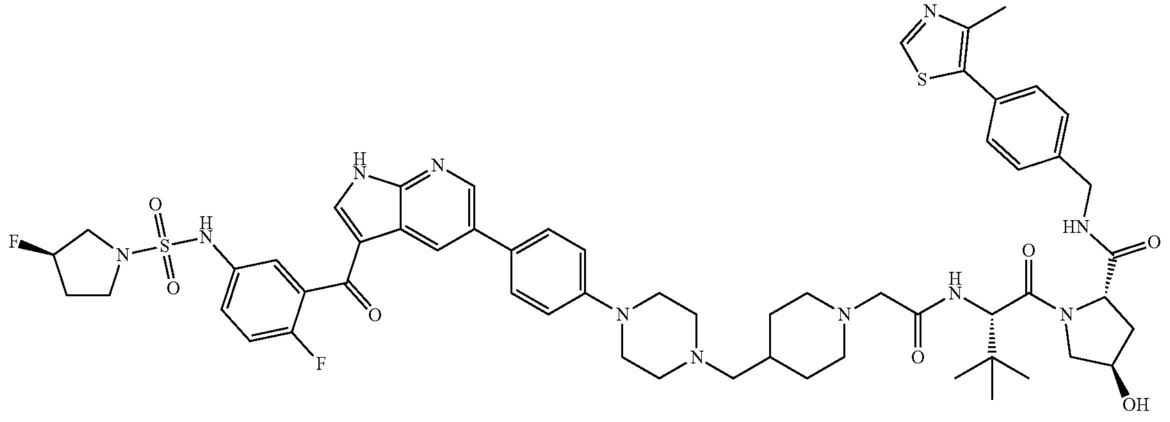
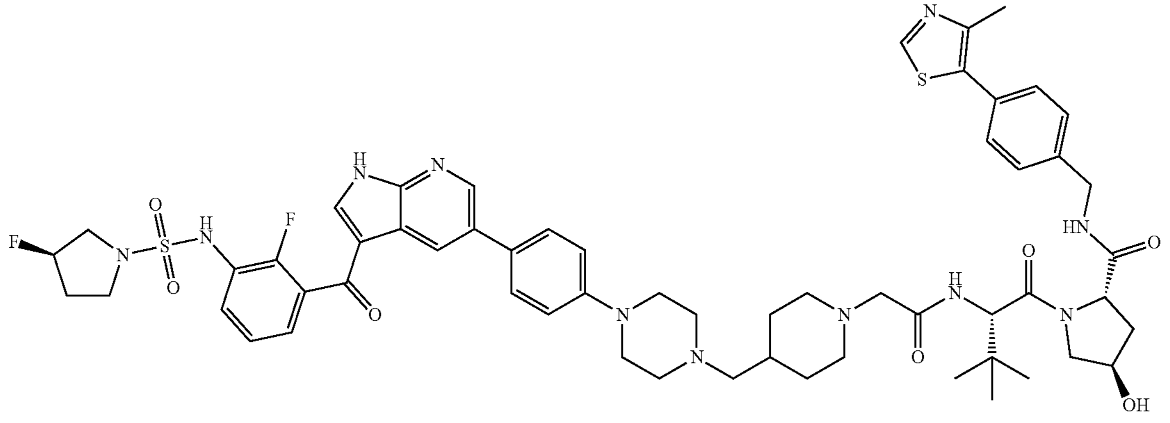

-continued
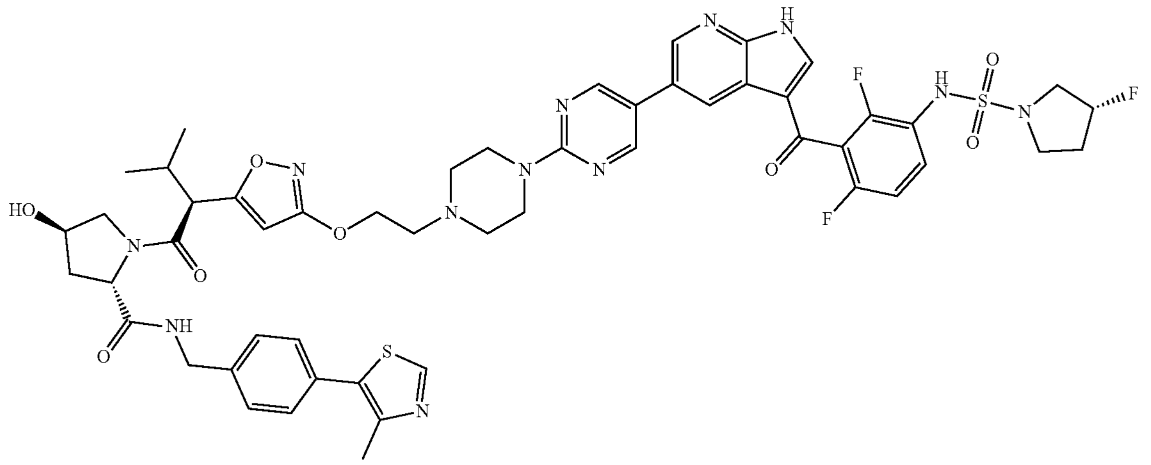
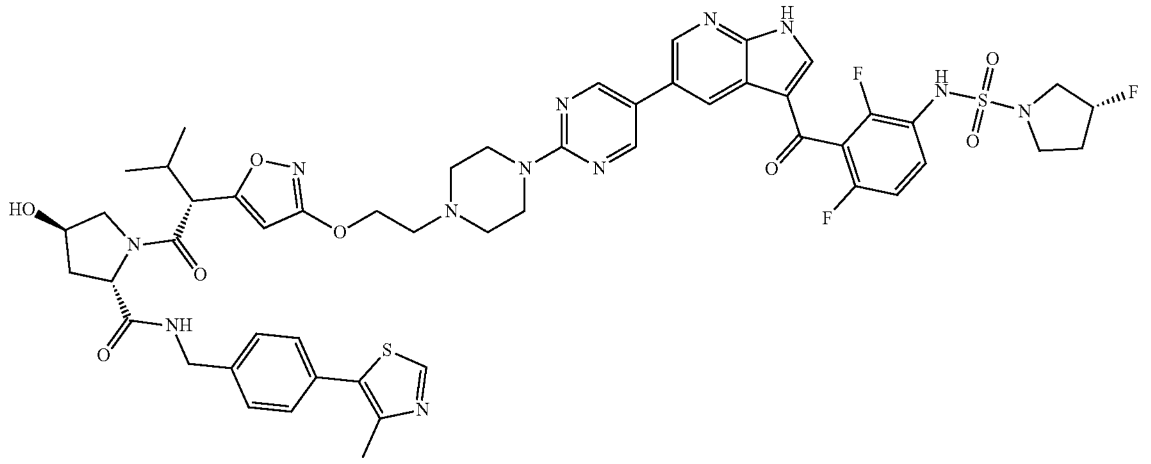
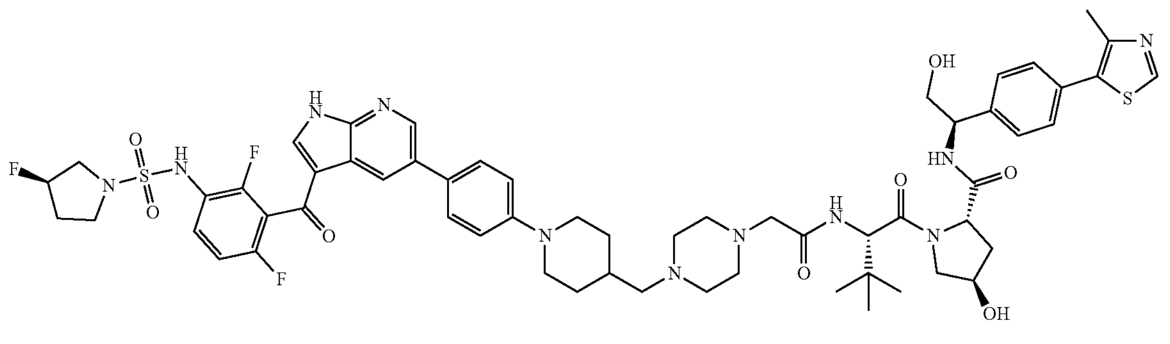

-continued
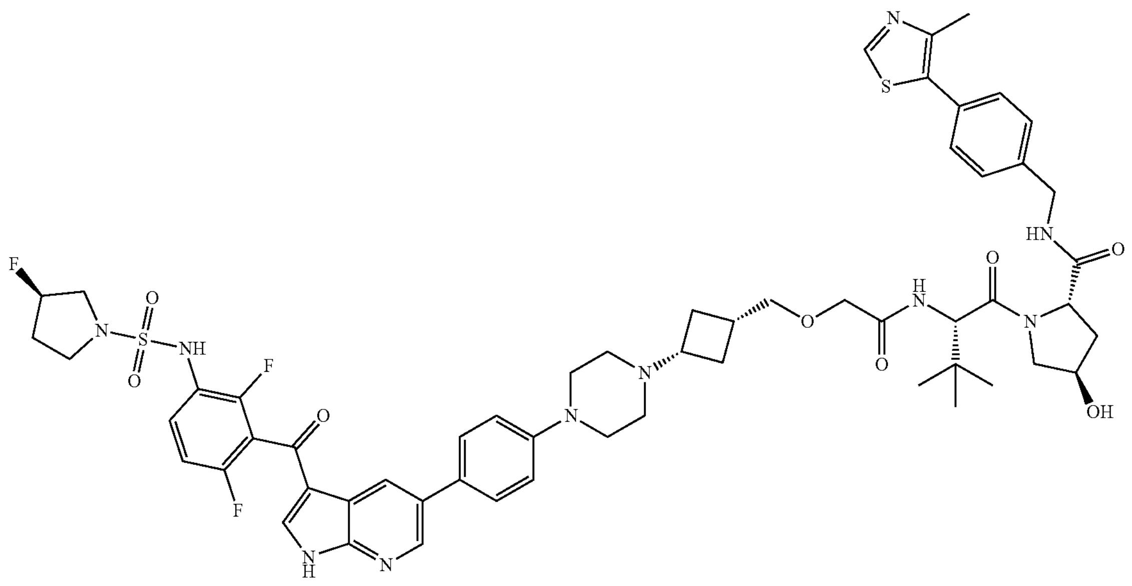
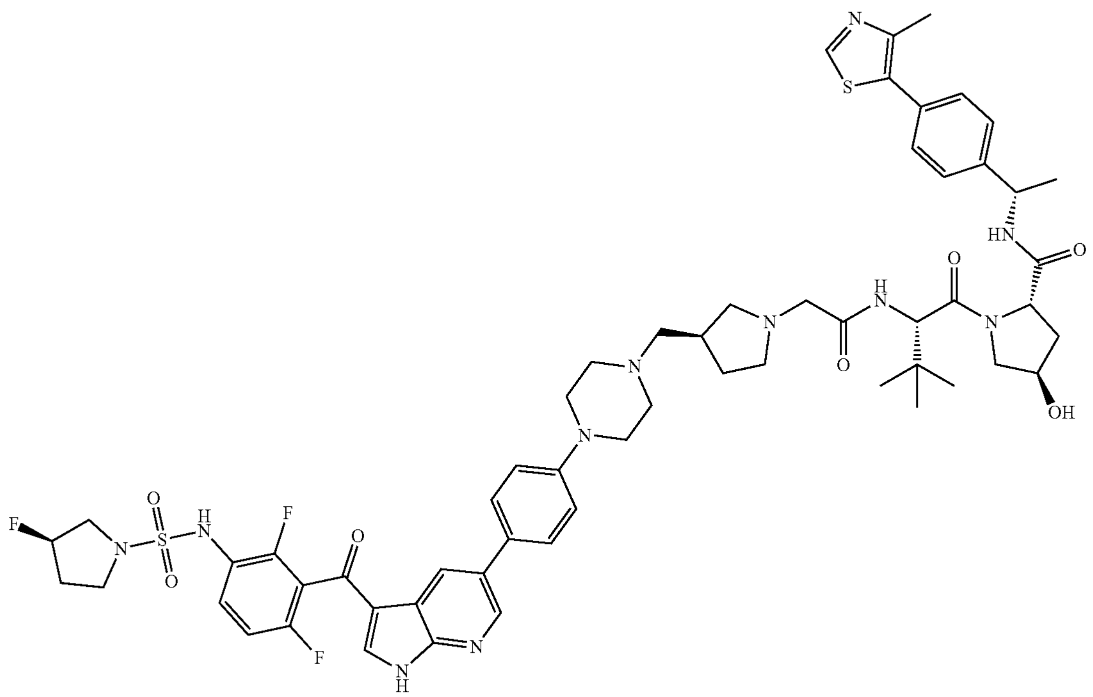

-continued
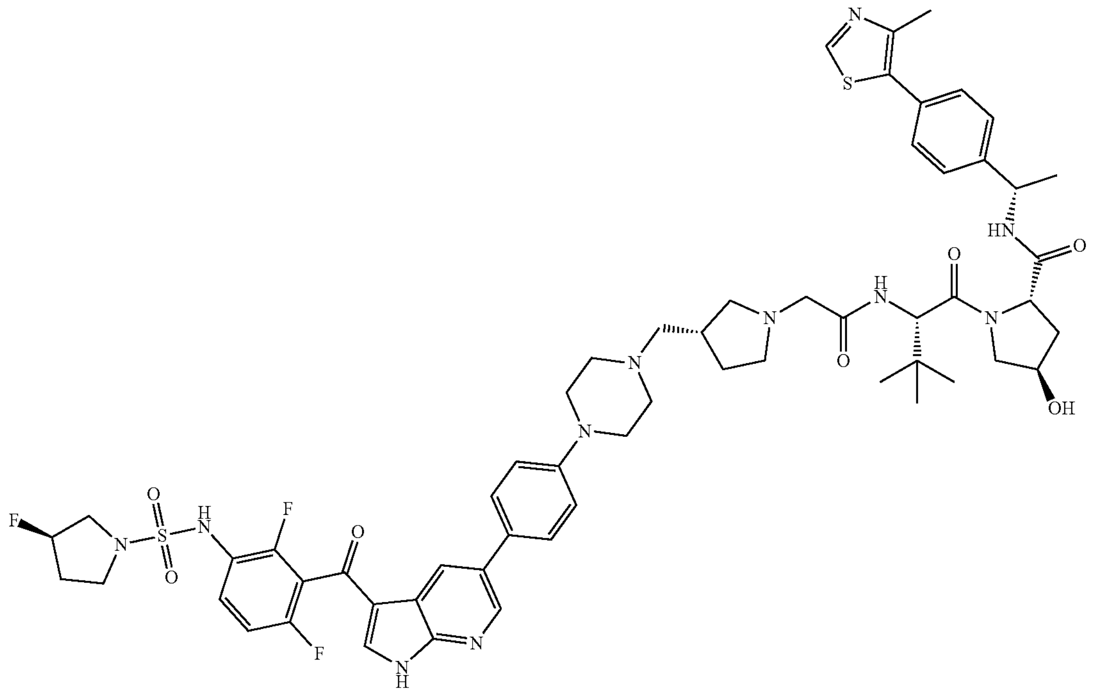
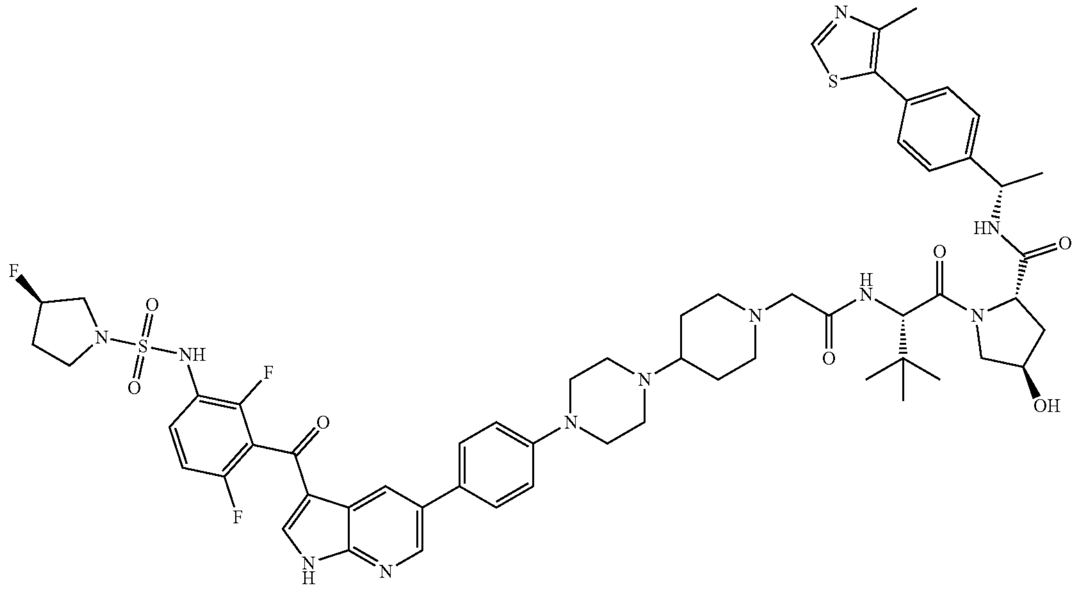
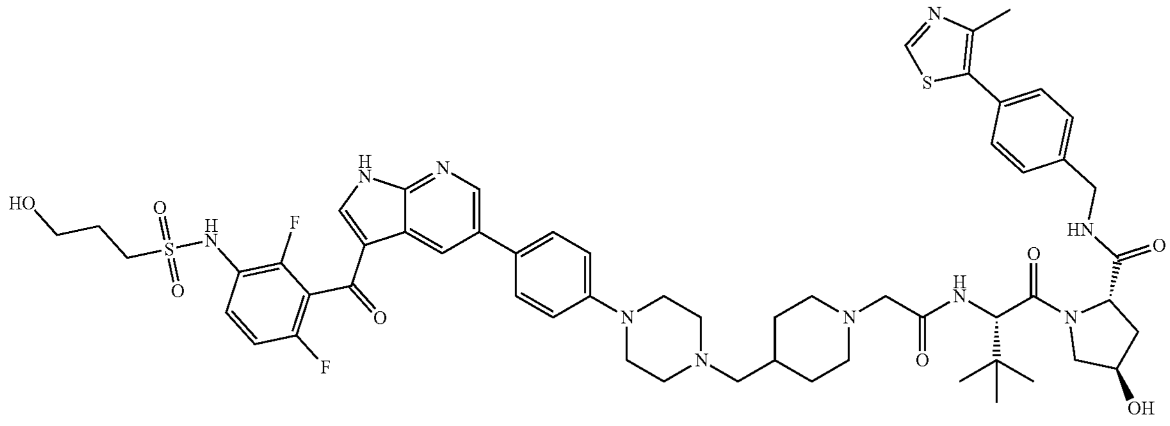

-continued
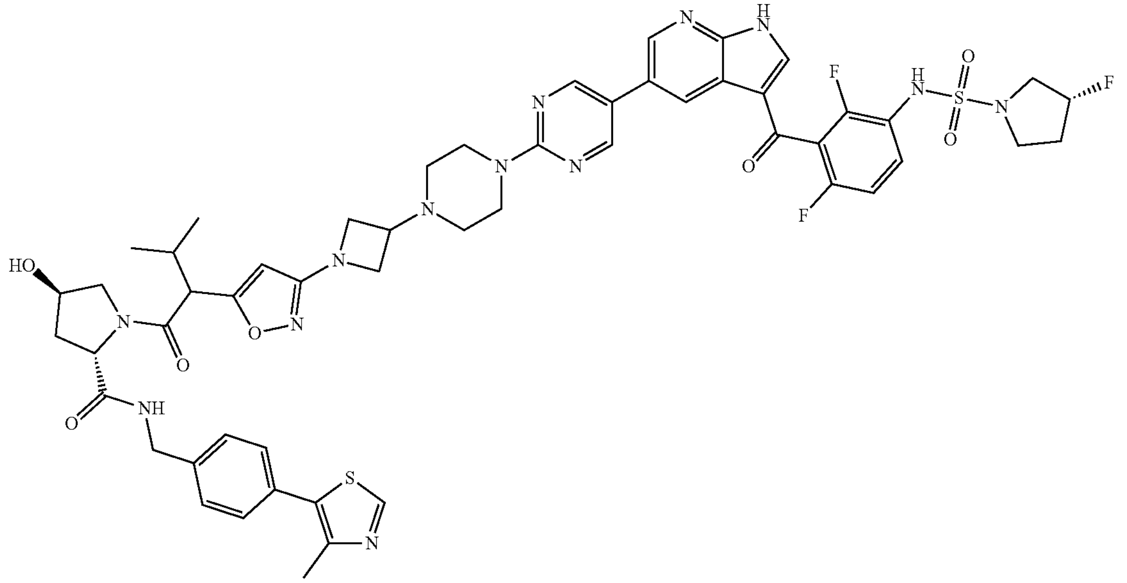
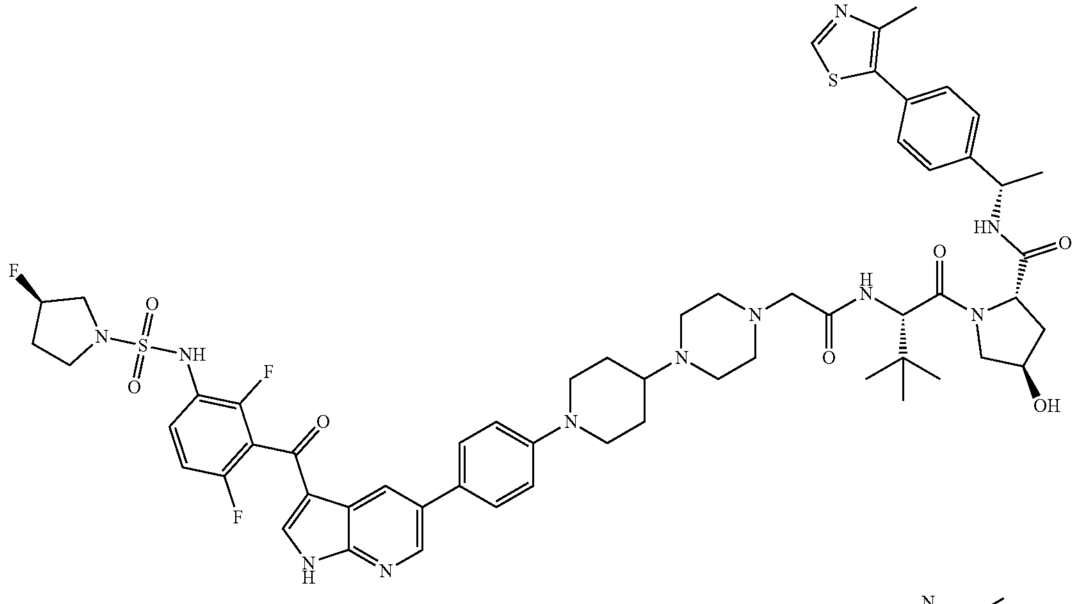
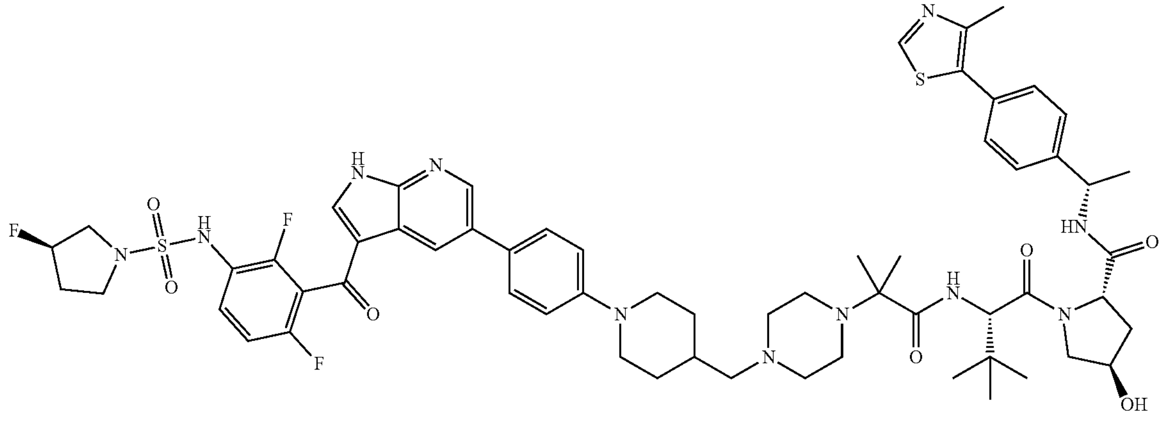

-continued
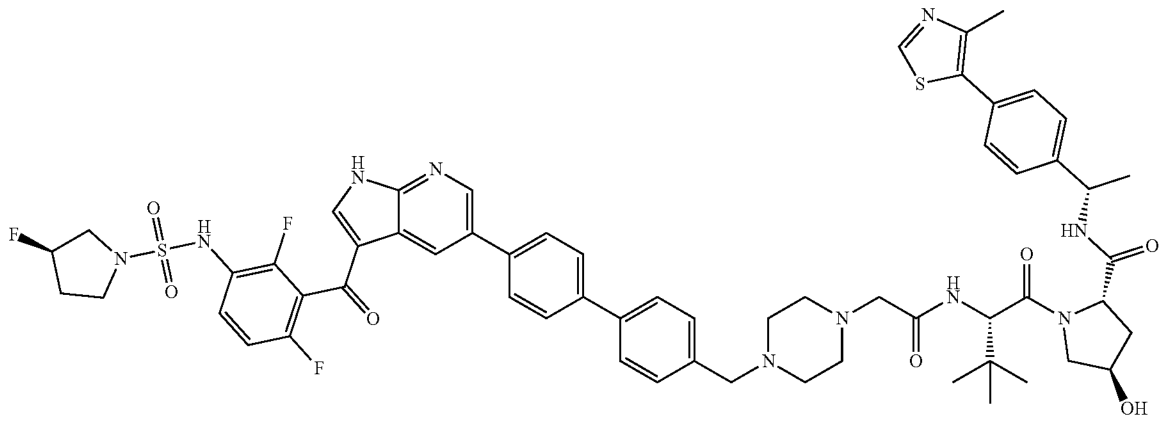
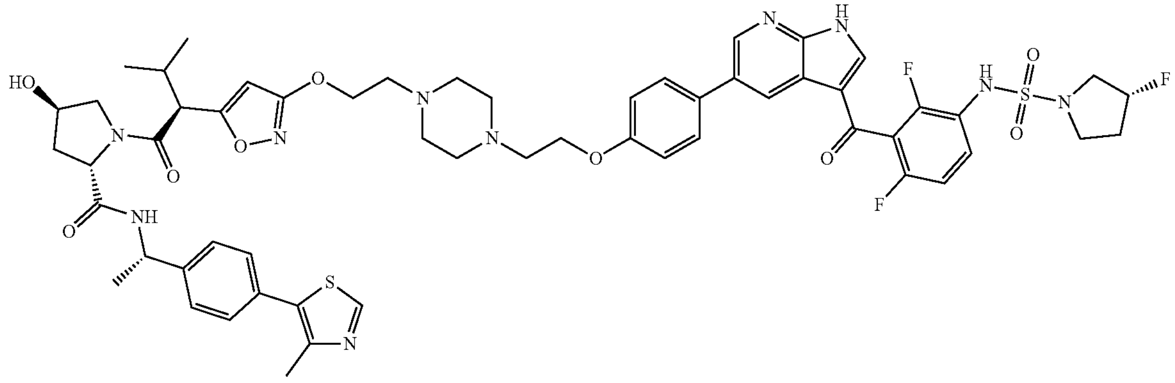
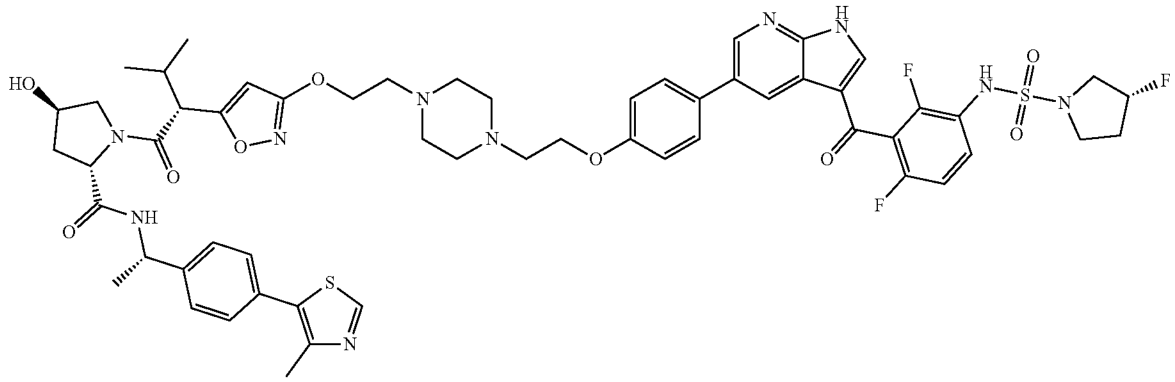
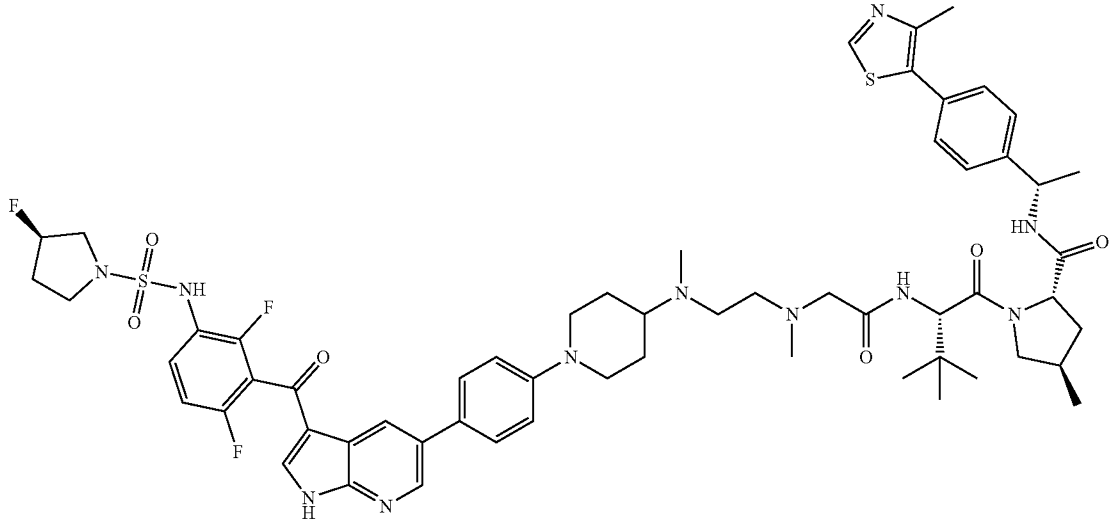

-continued
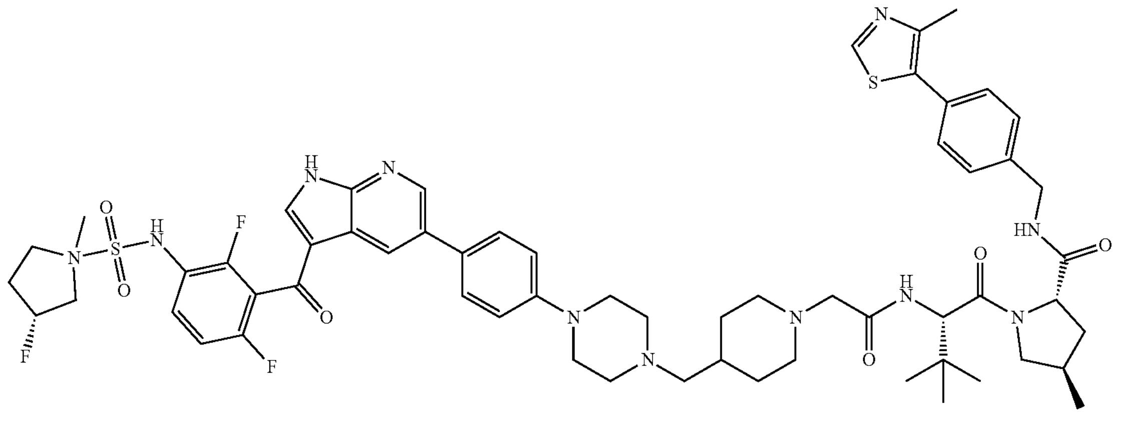
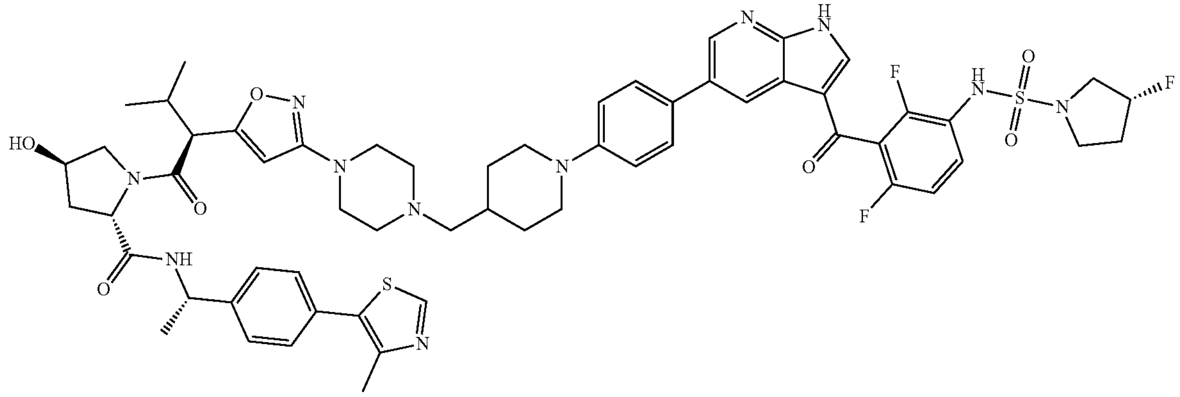
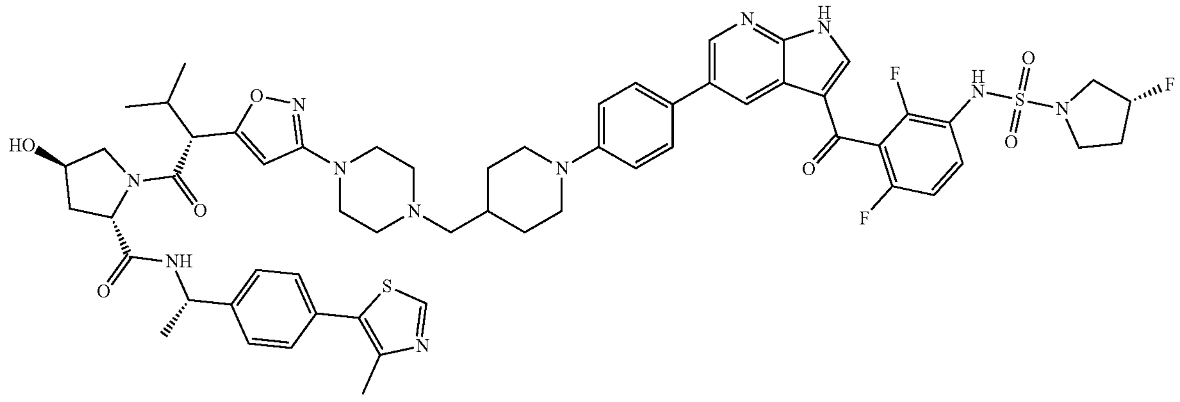
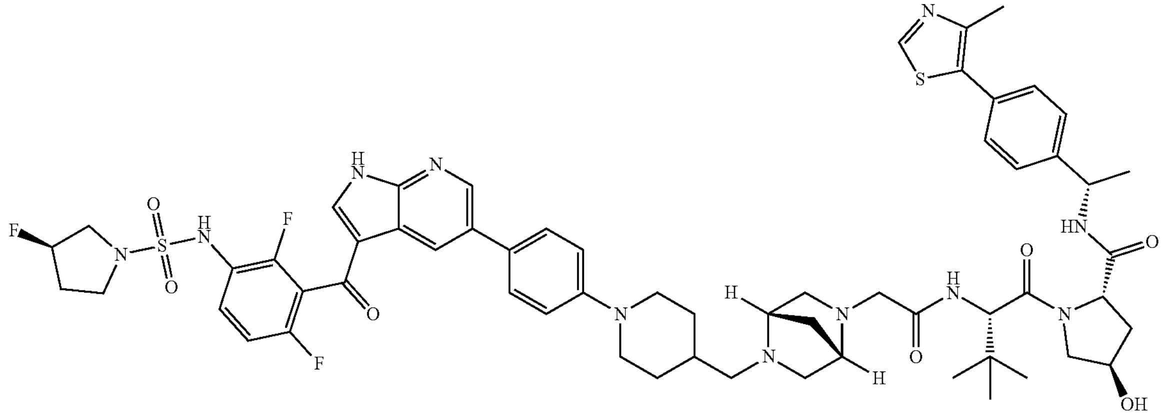

-continued
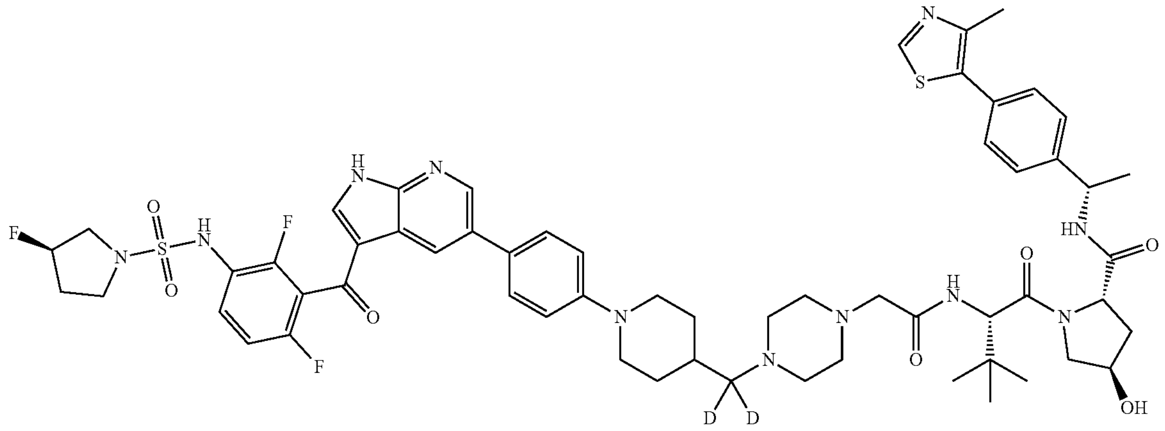
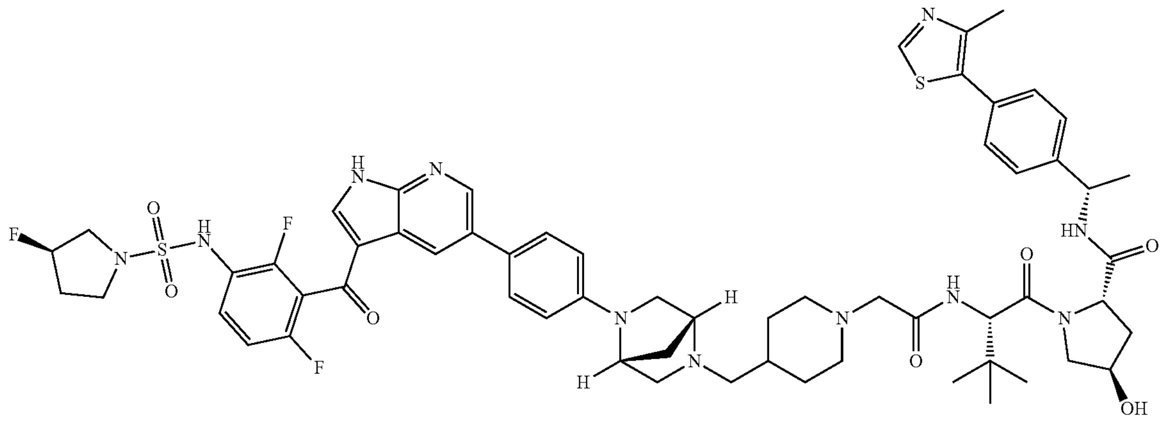
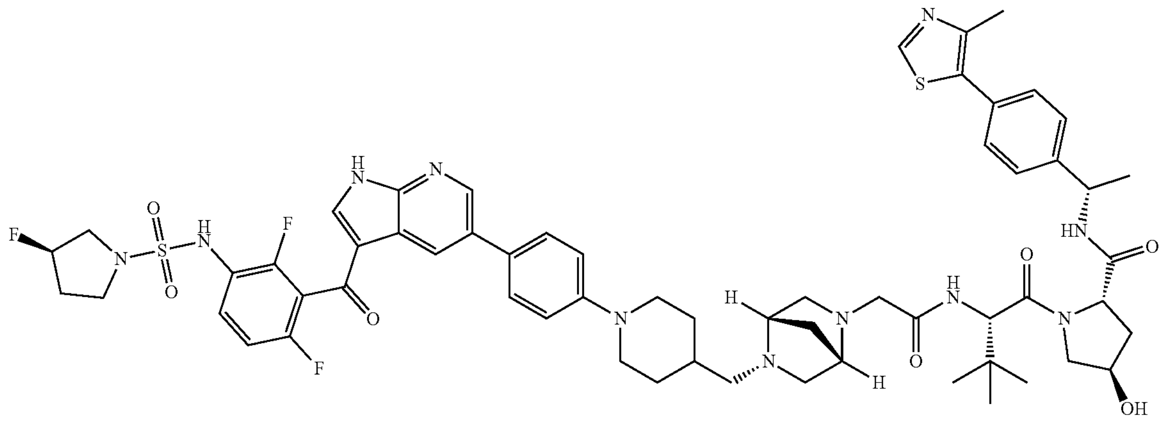
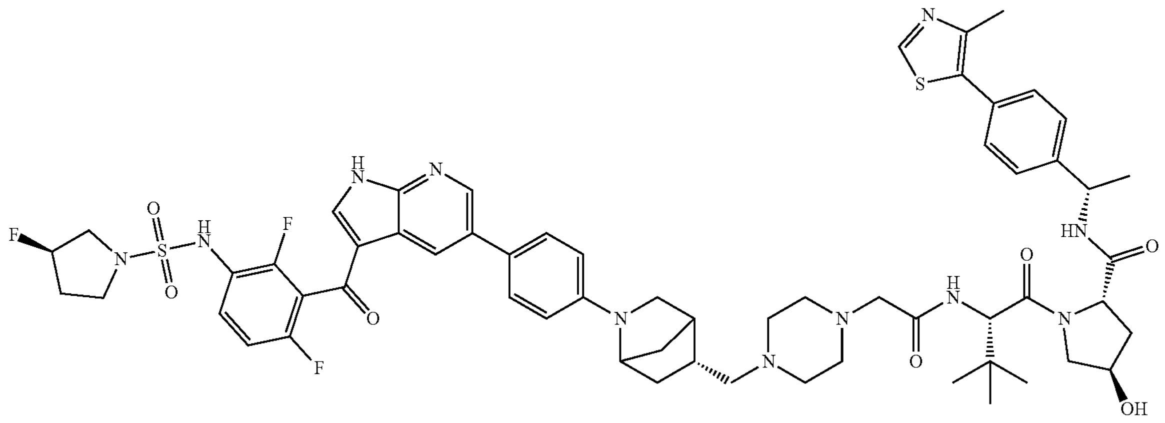

-continued
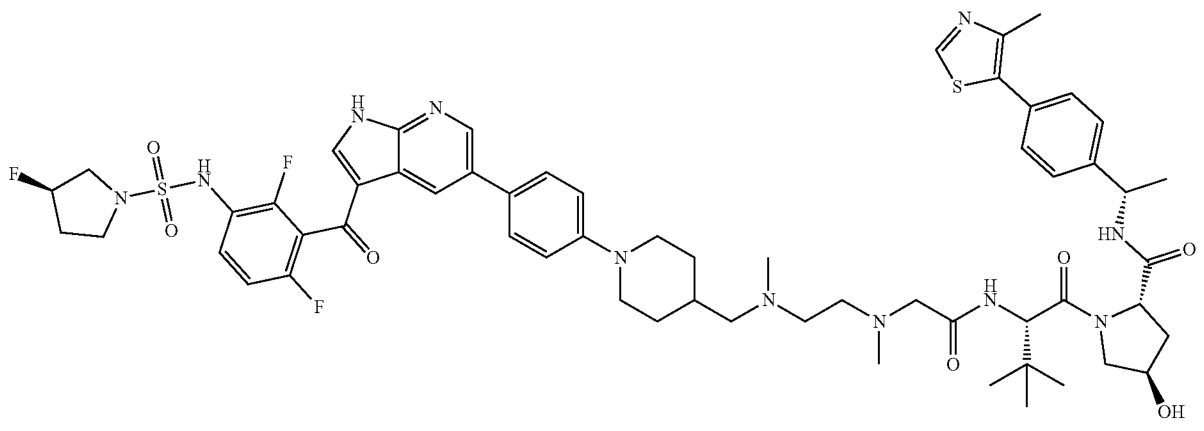
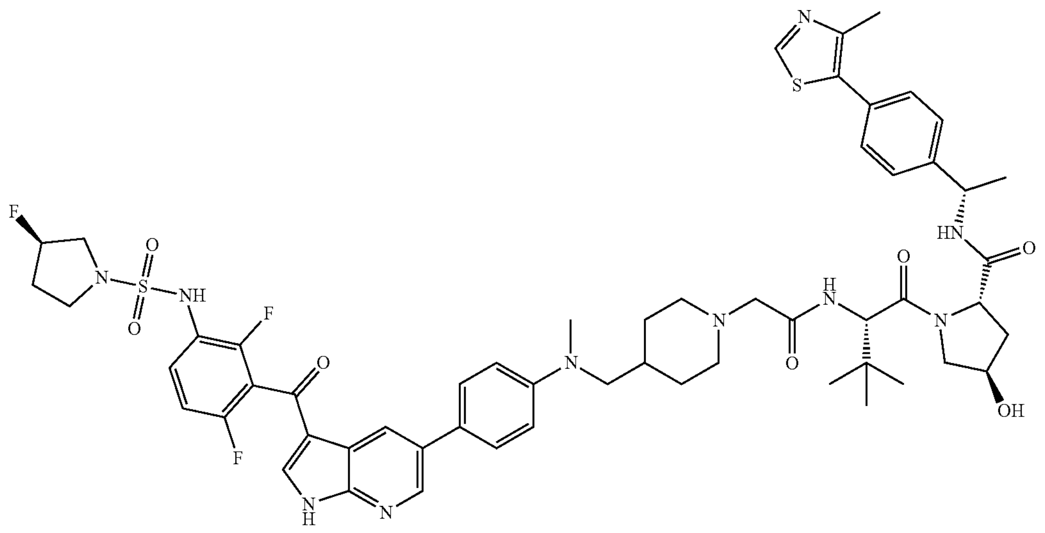
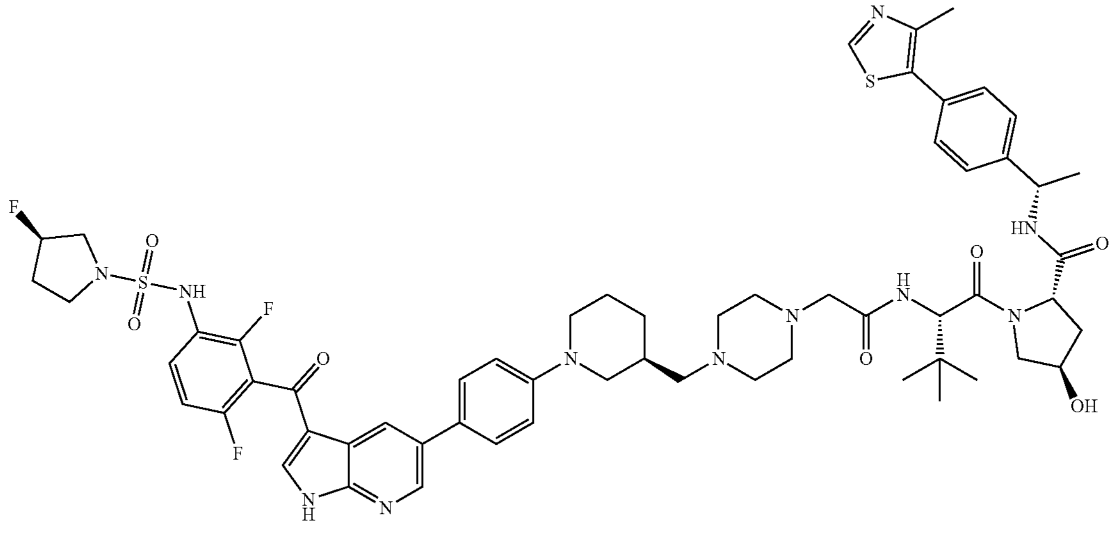

-continued
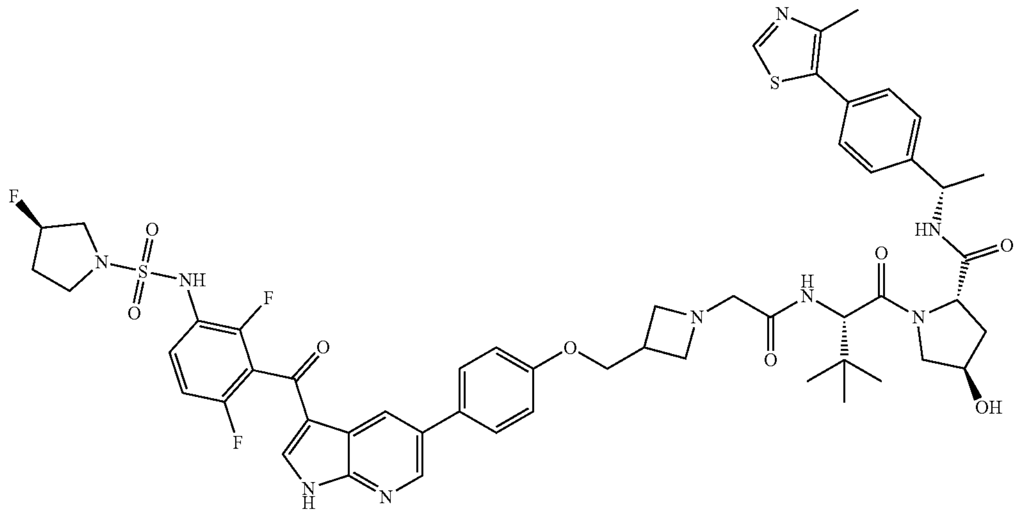
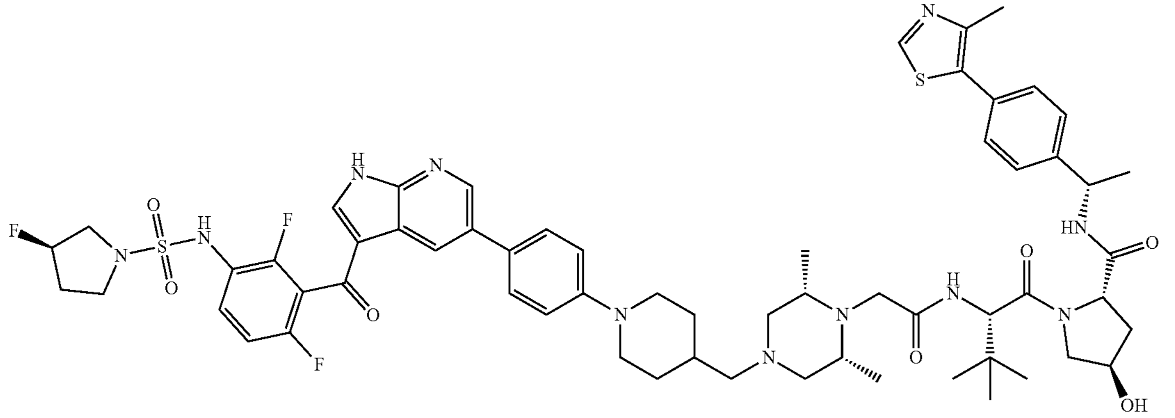
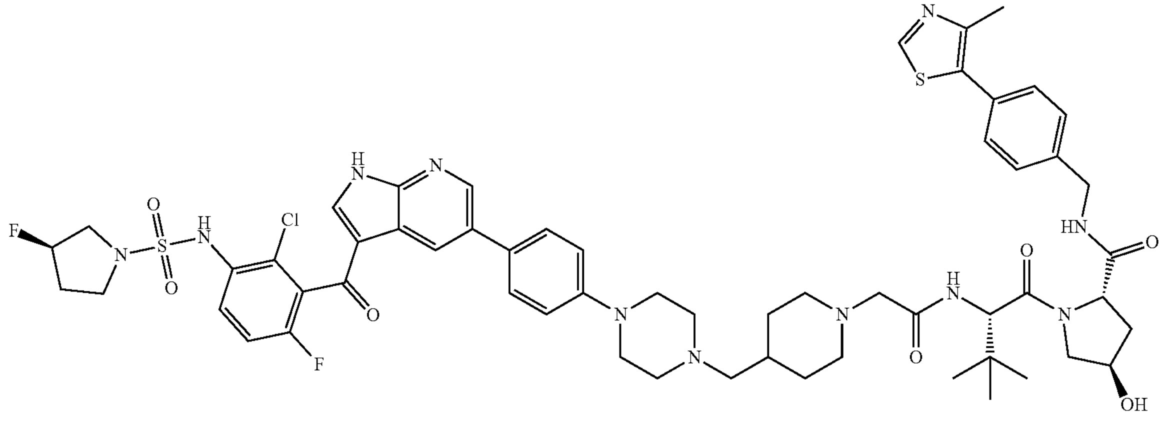

-continued
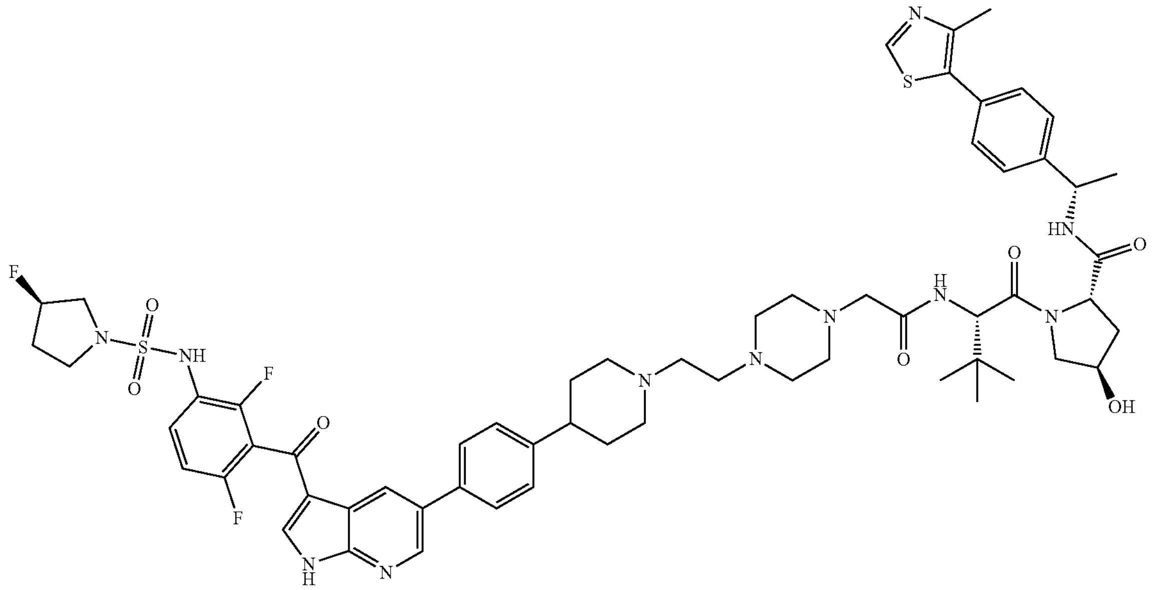
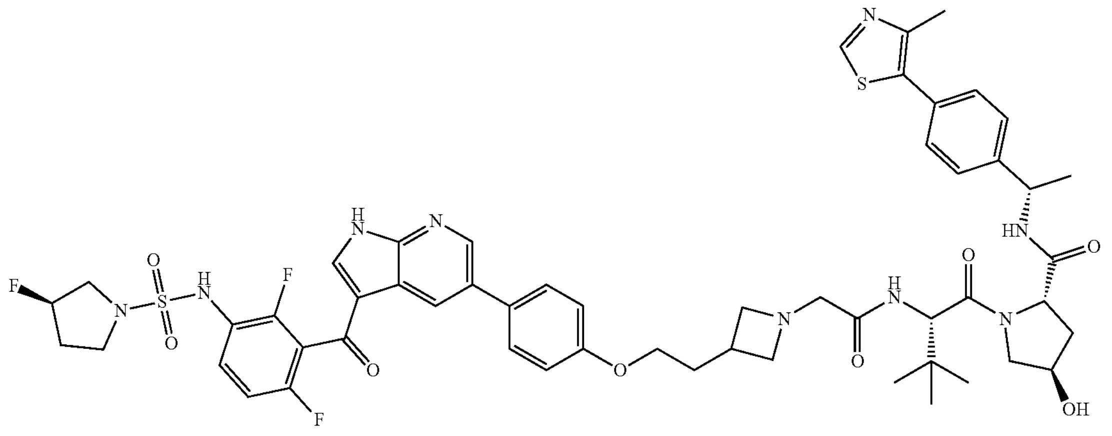
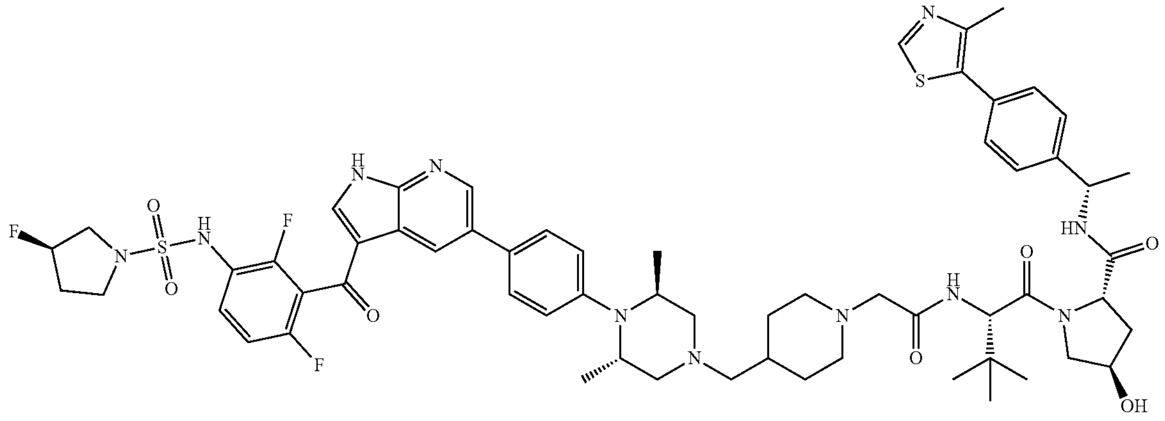

-continued
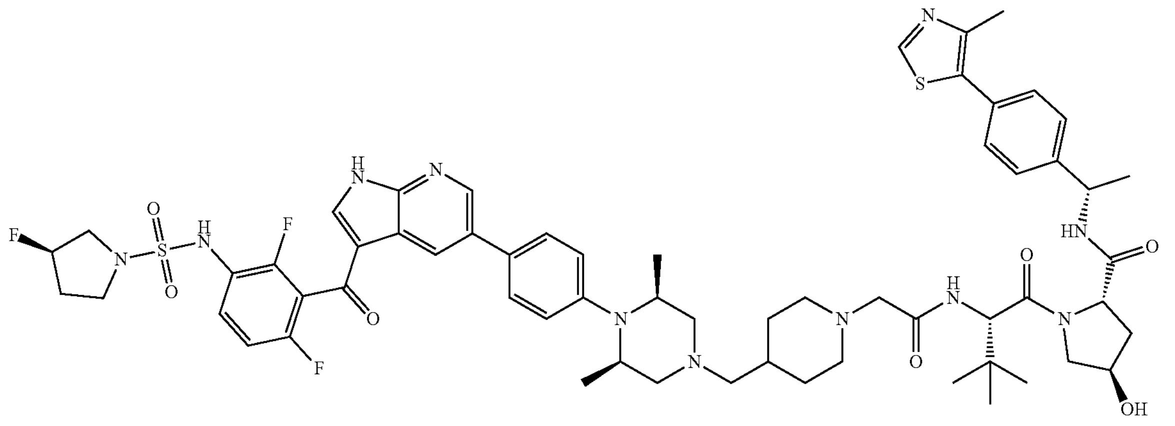
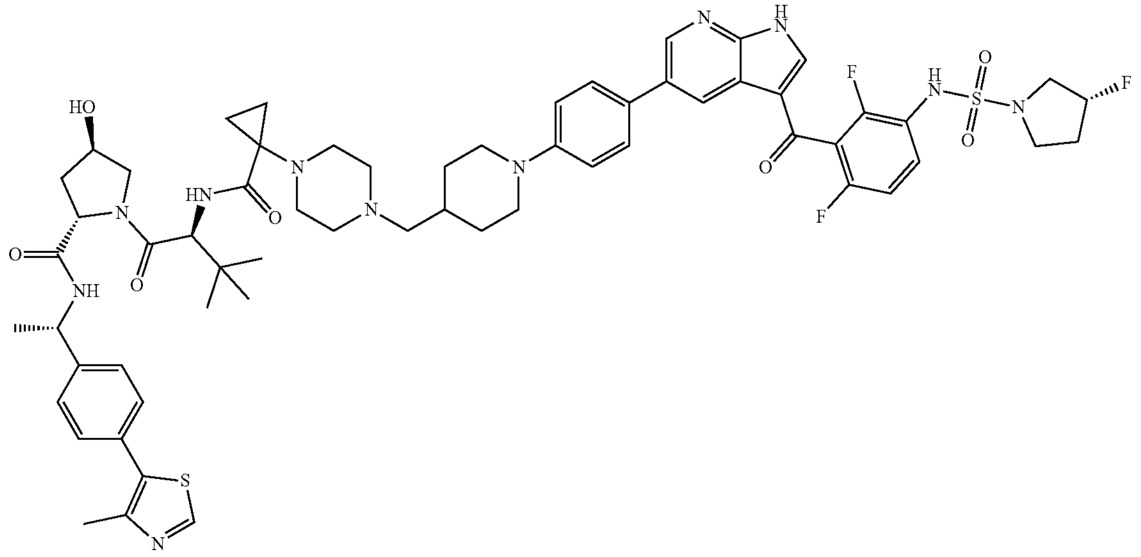
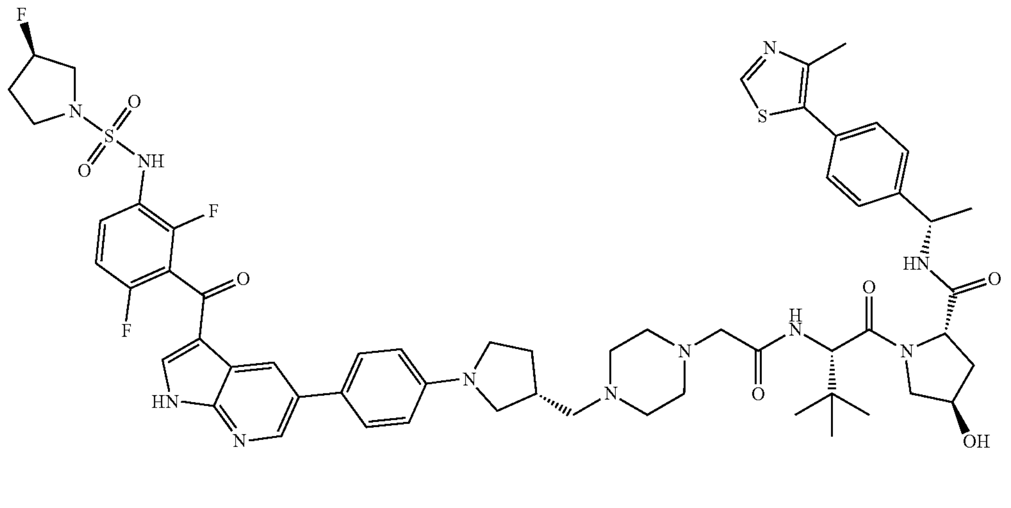

-continued
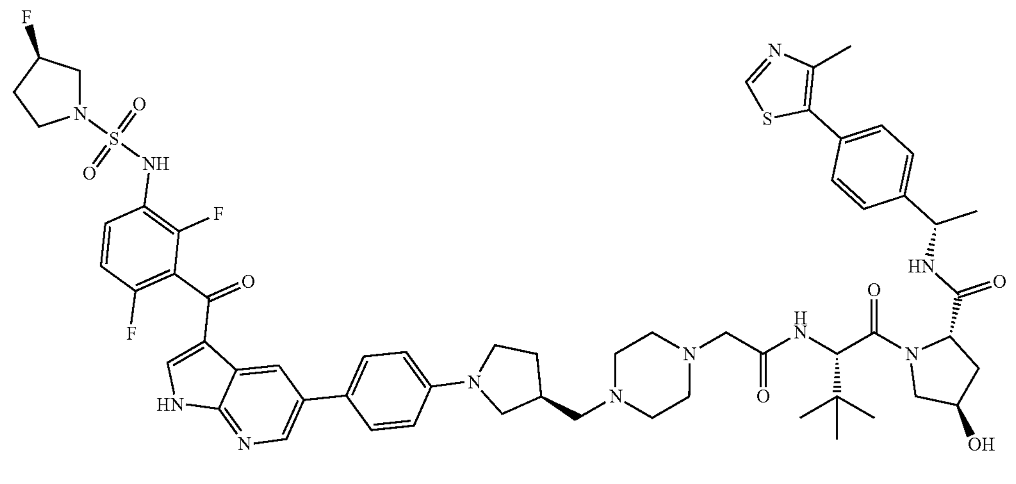
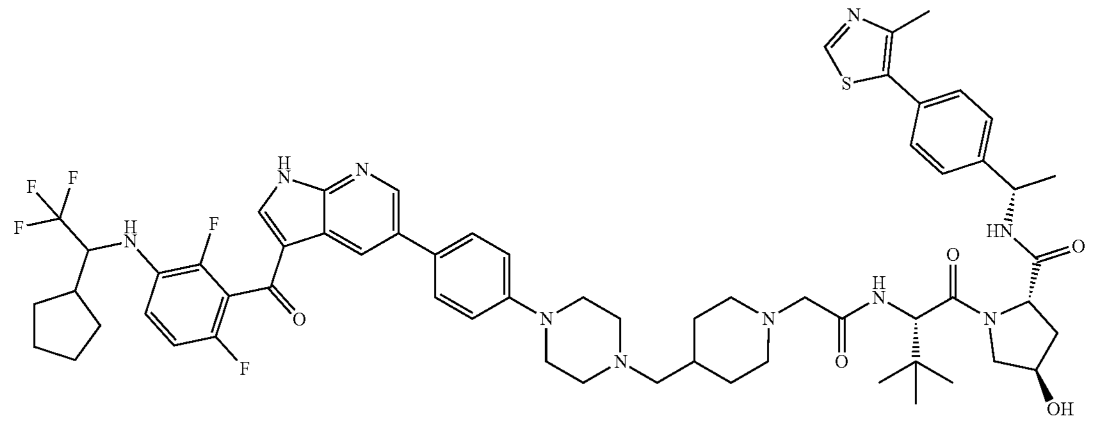
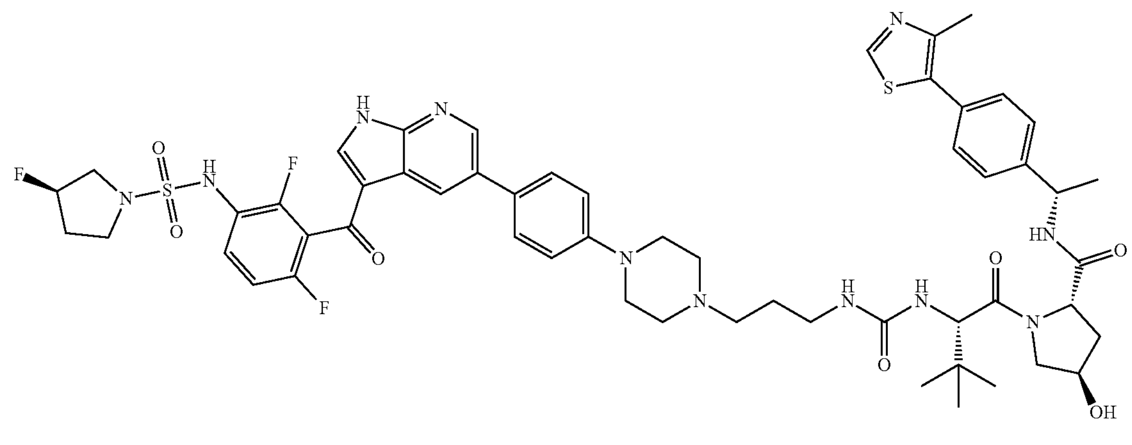

-continued
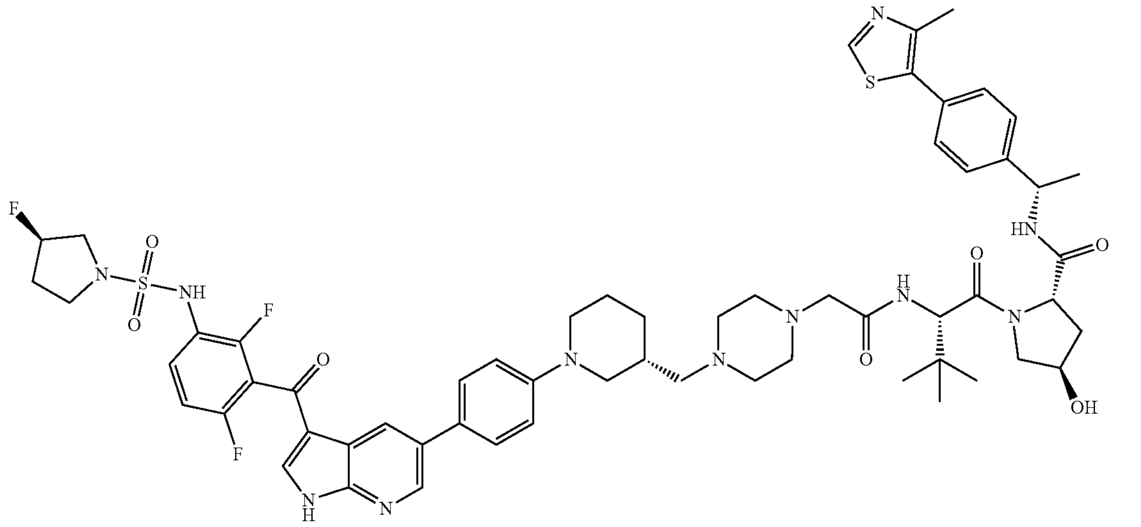
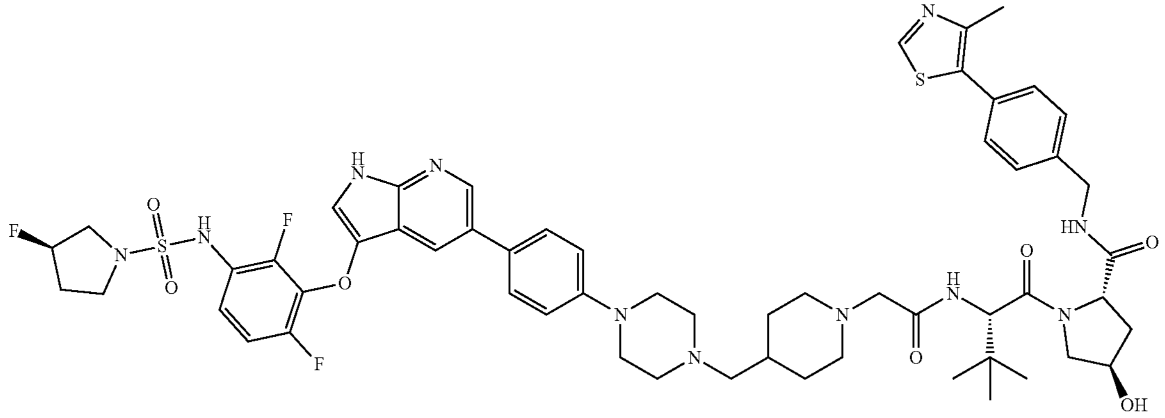
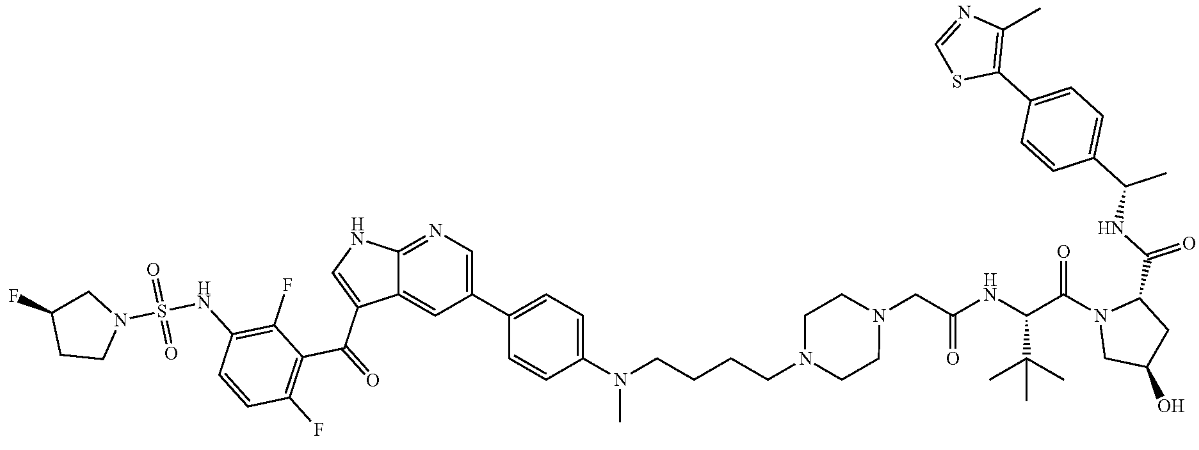

-continued
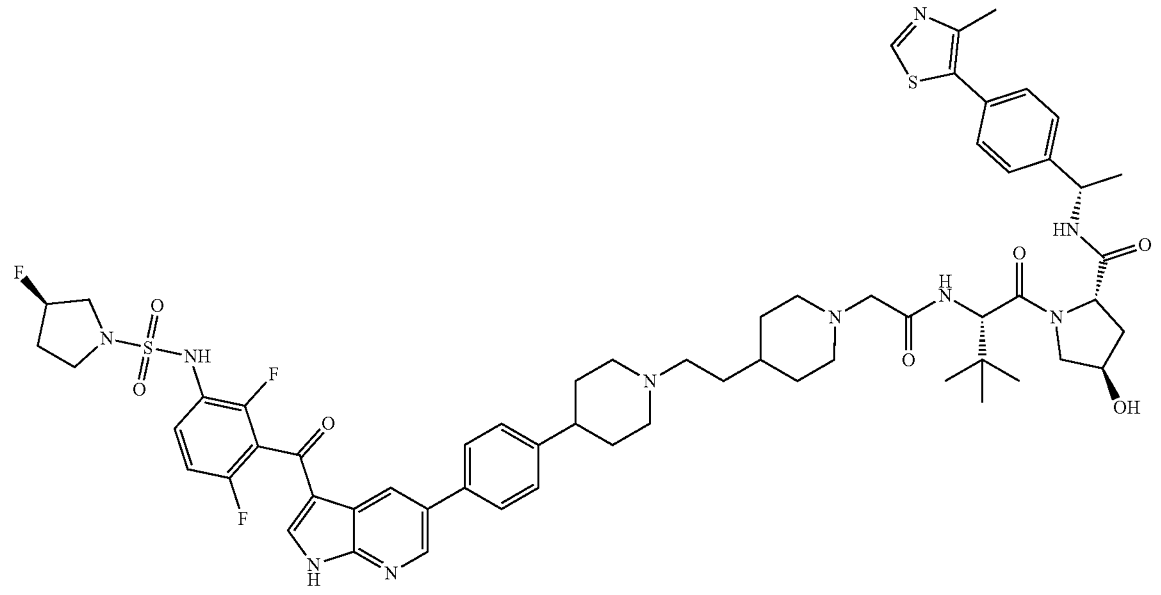
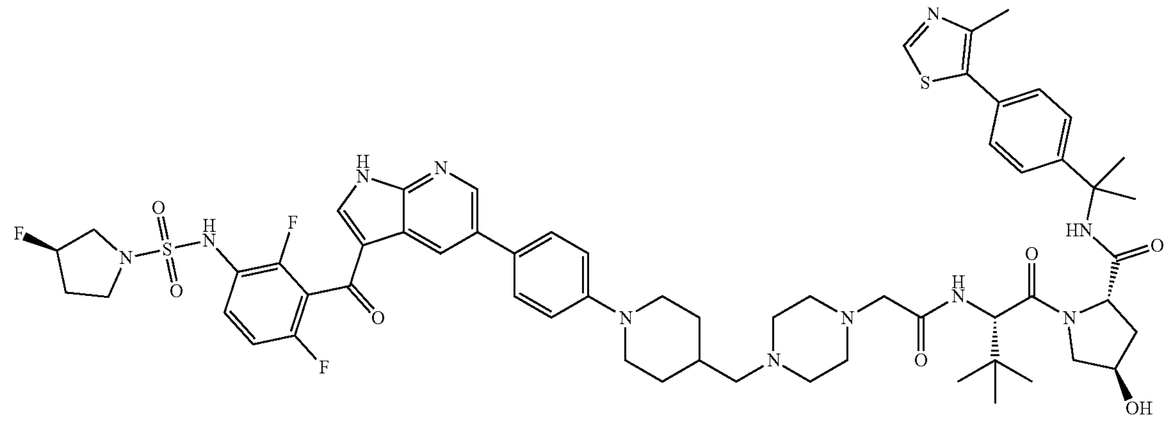
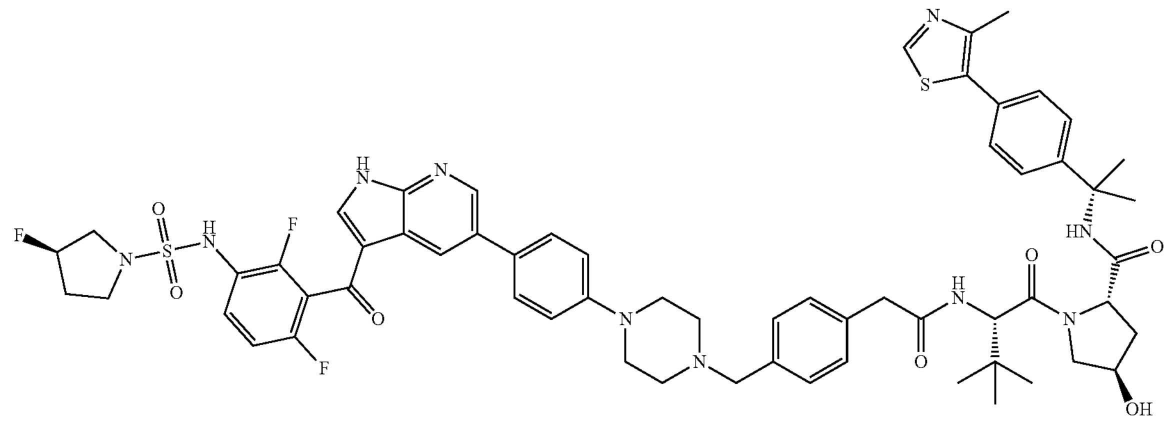

-continued
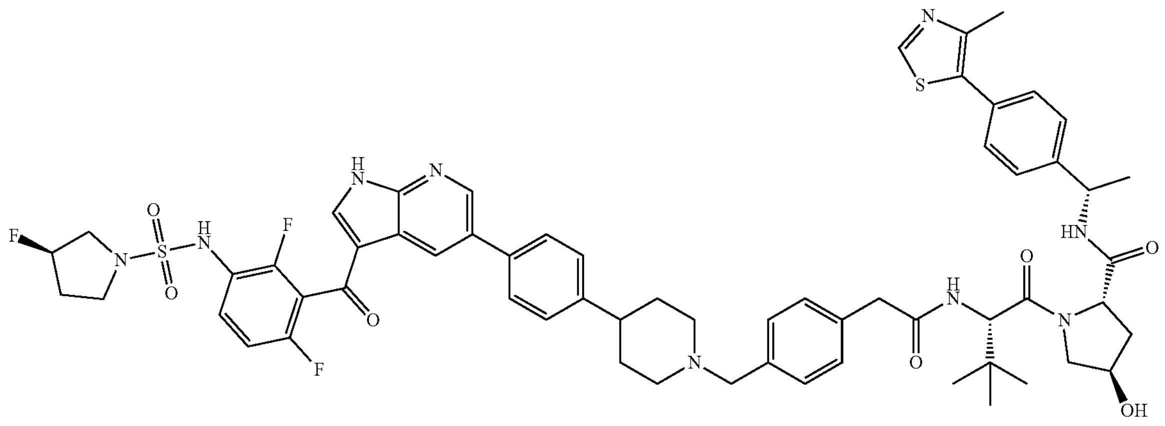
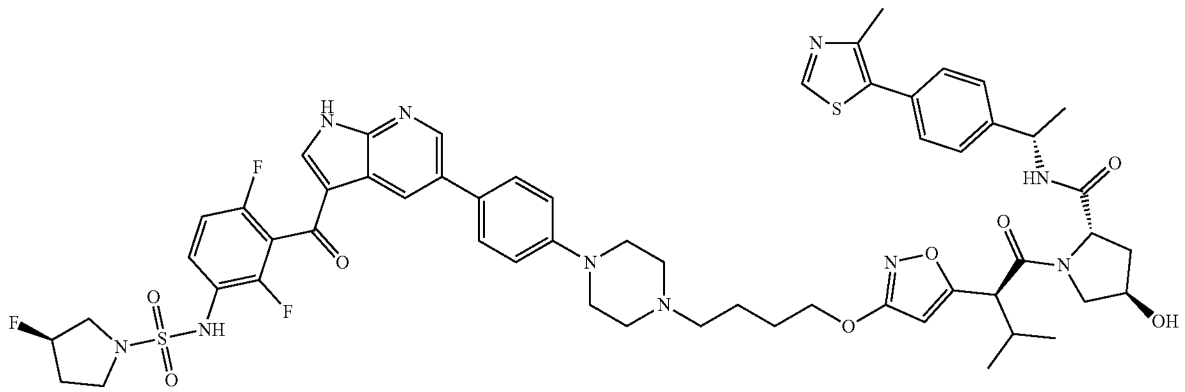
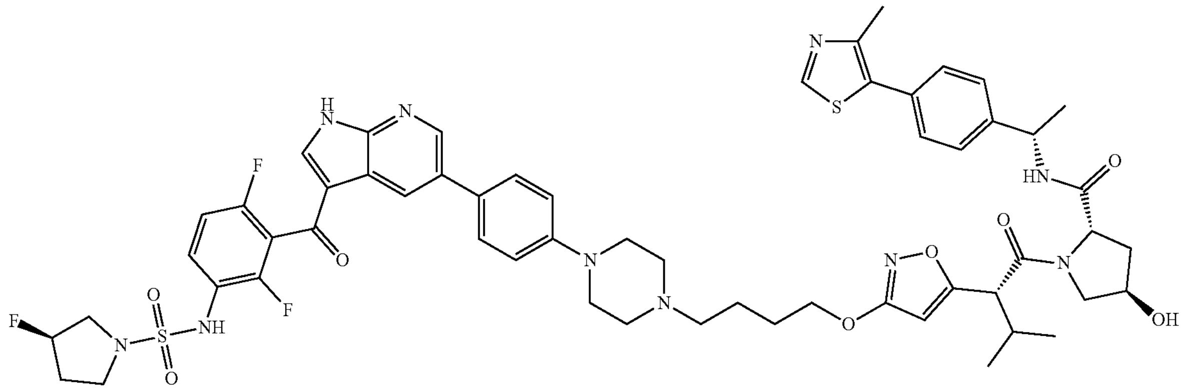

-continued
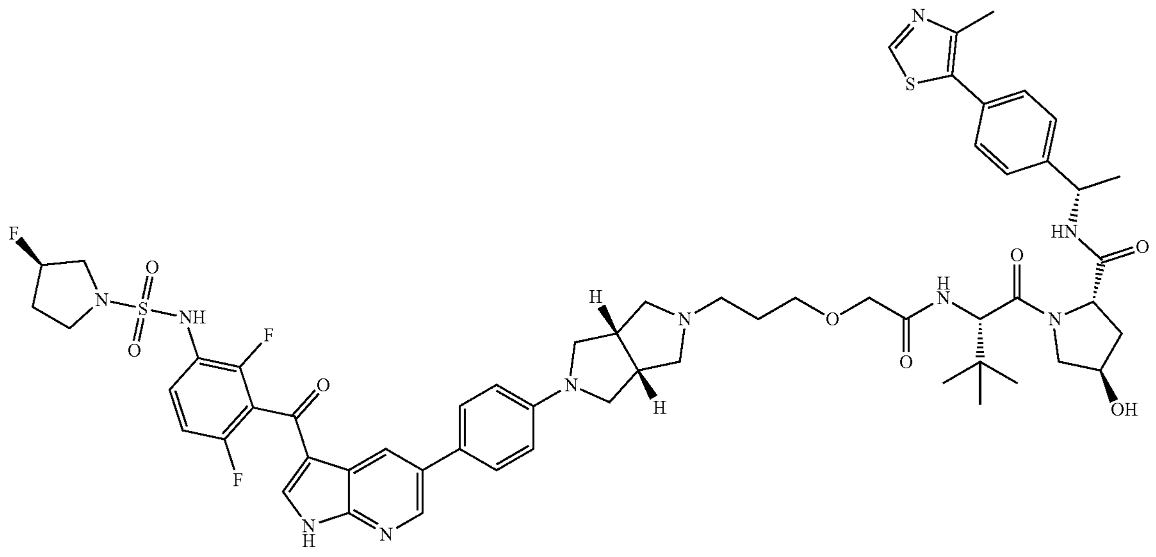
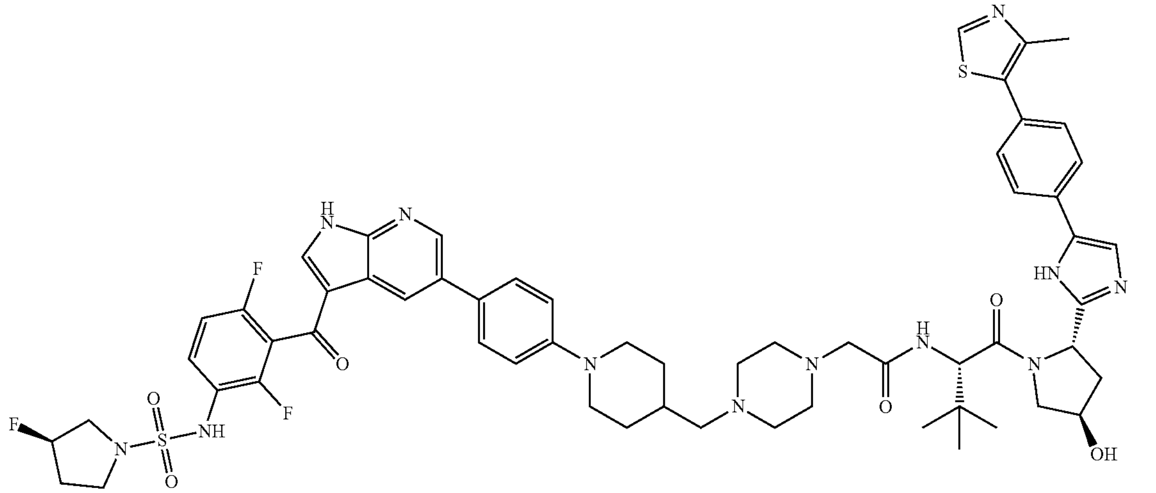
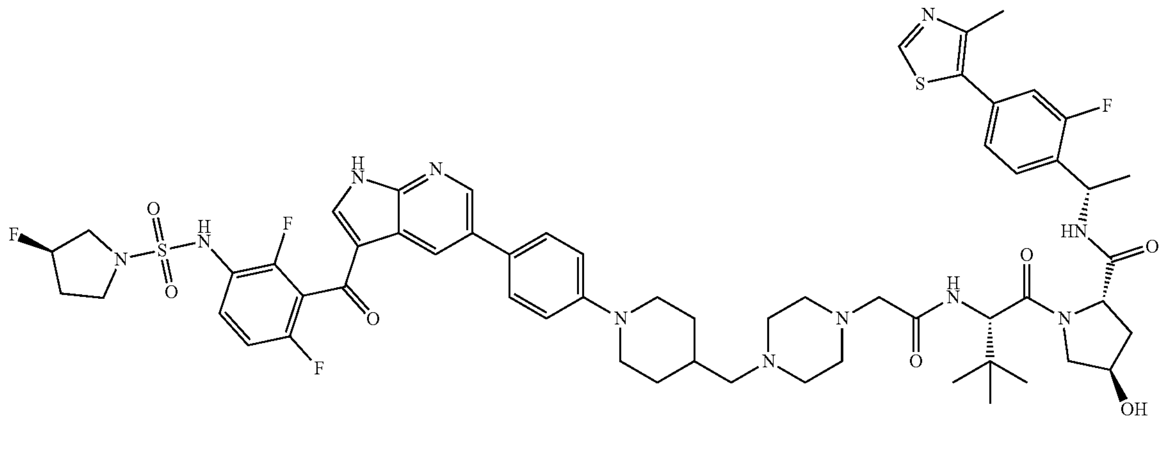

-continued
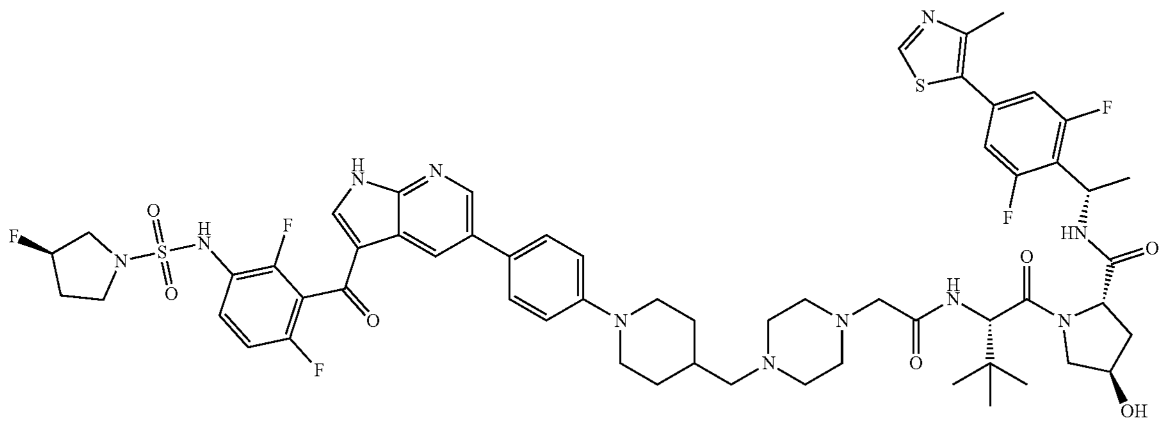
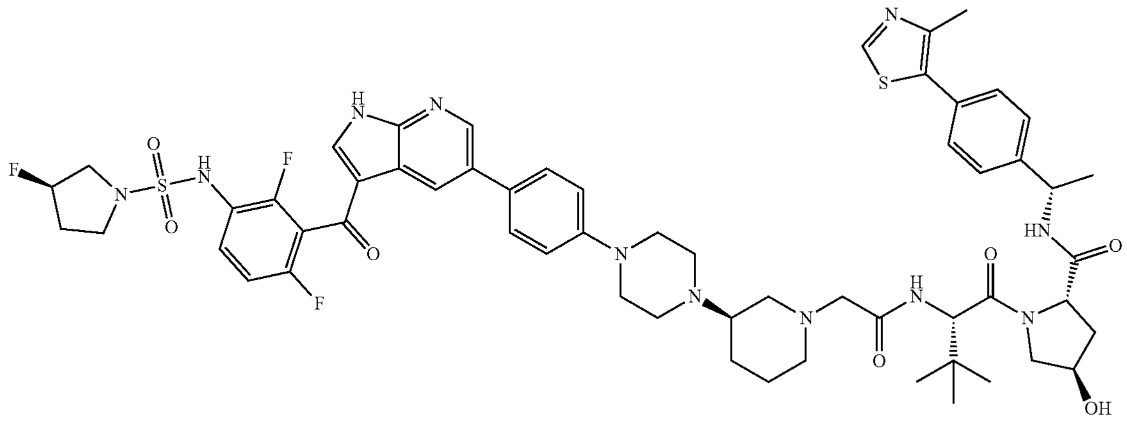
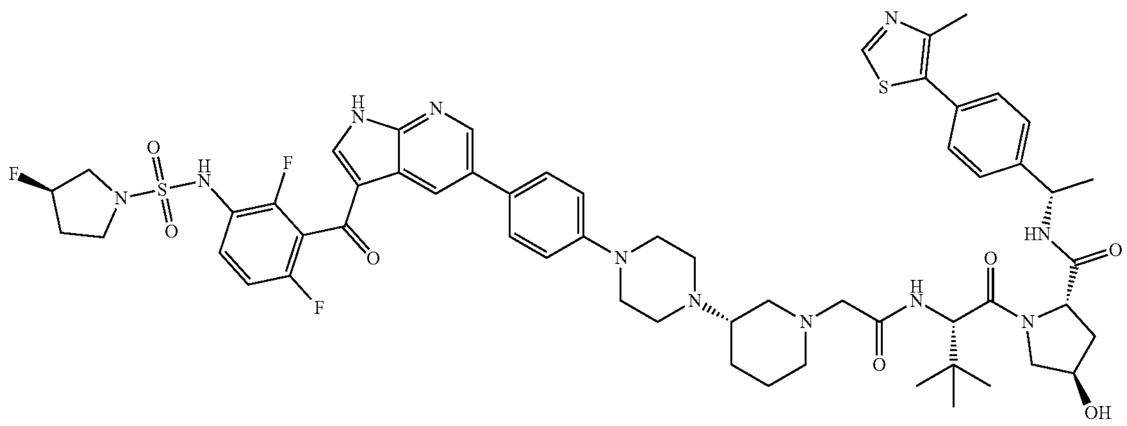

-continued
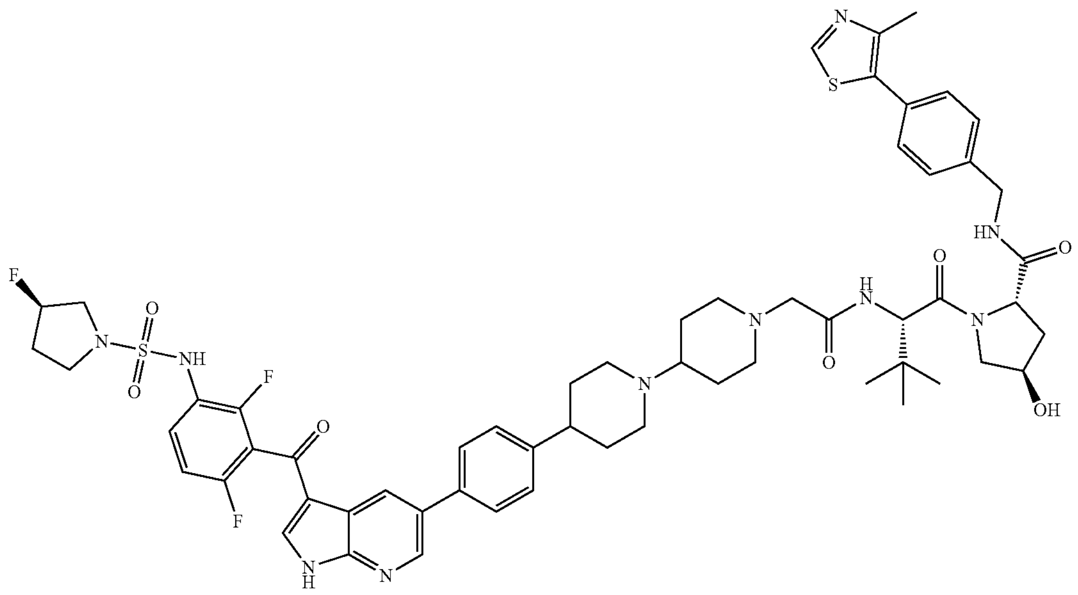
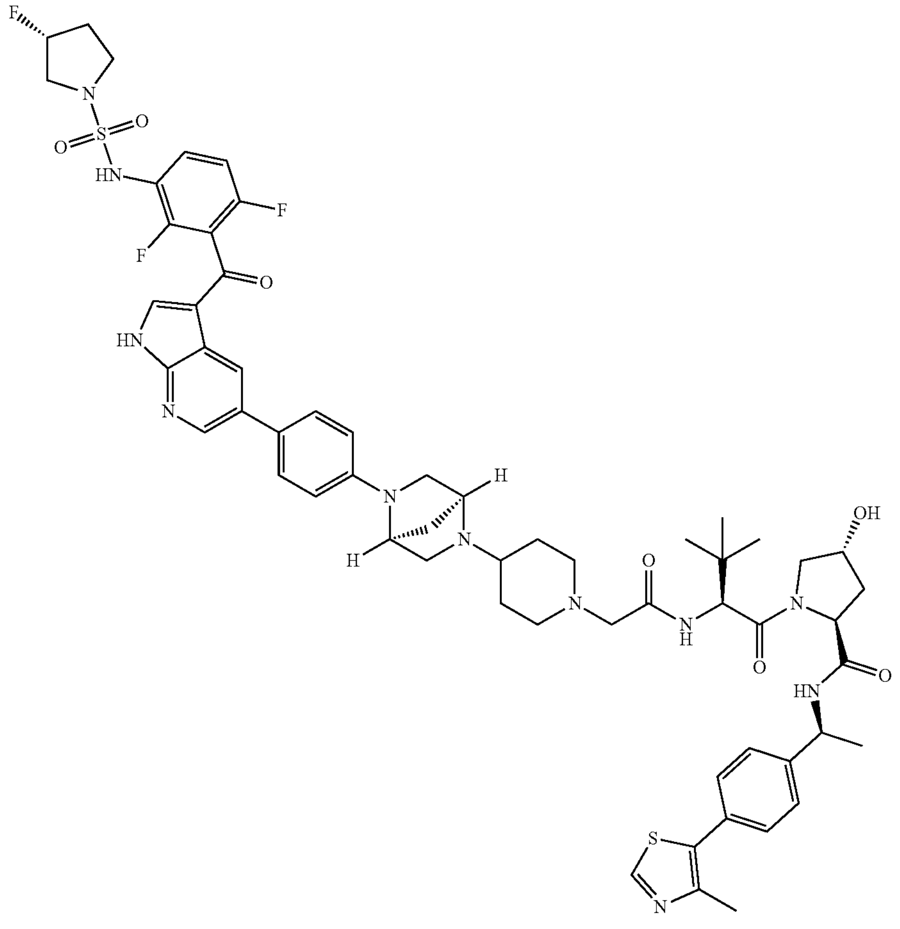

-continued
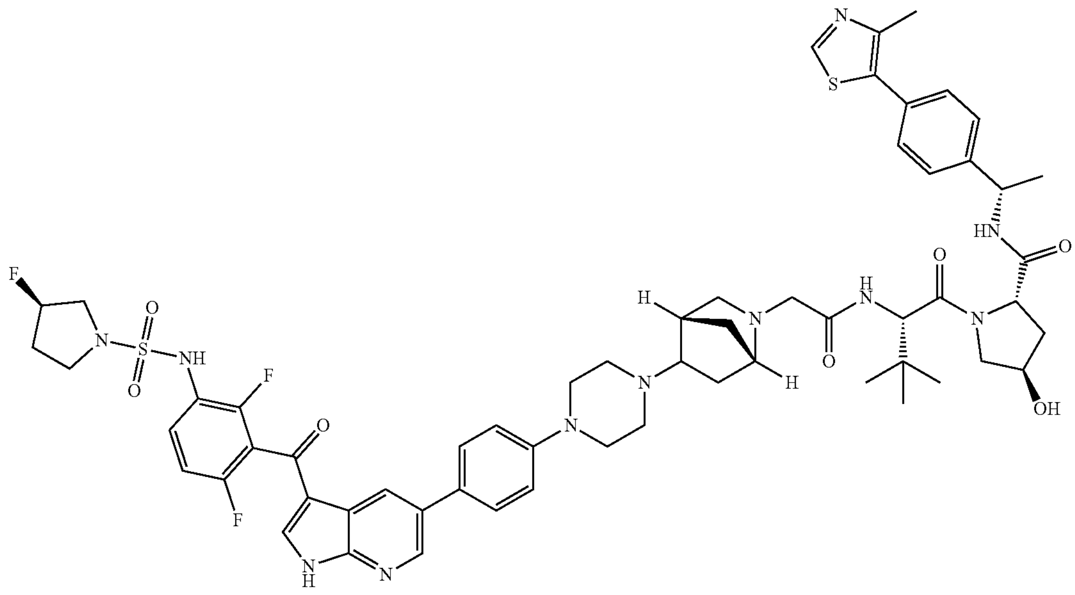
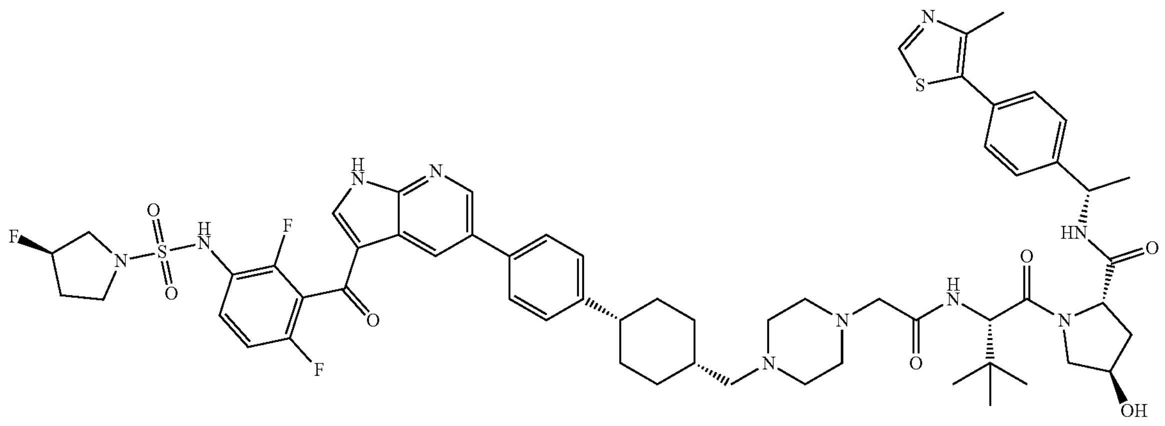
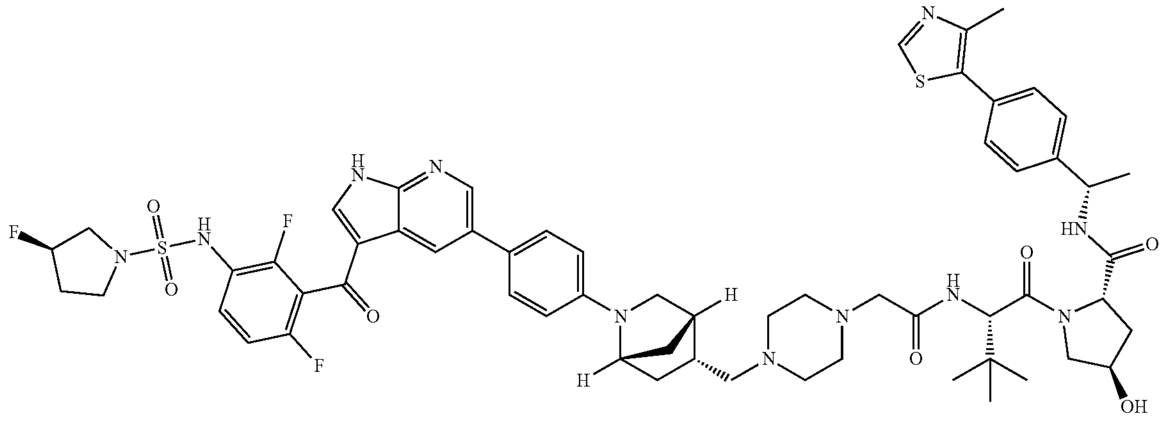

-continued
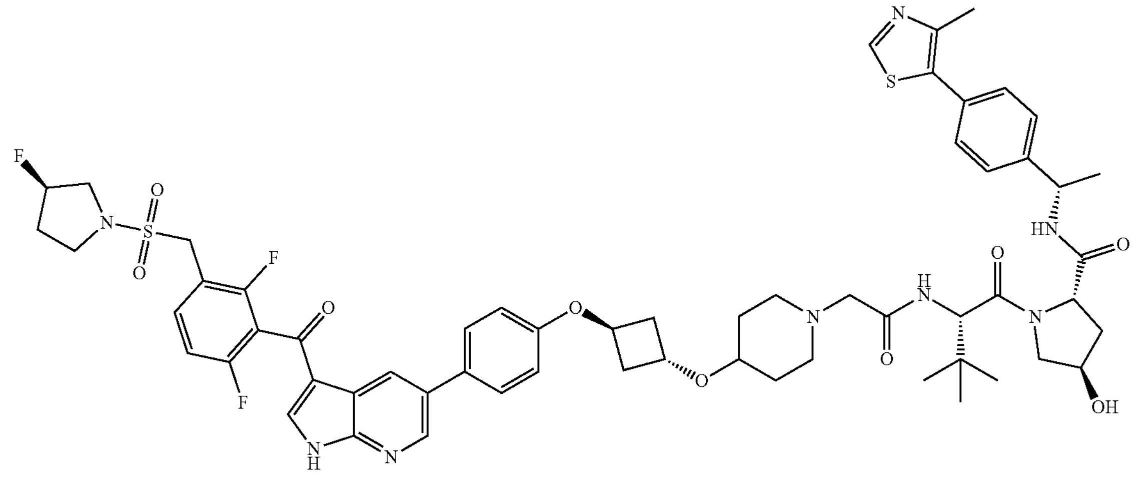
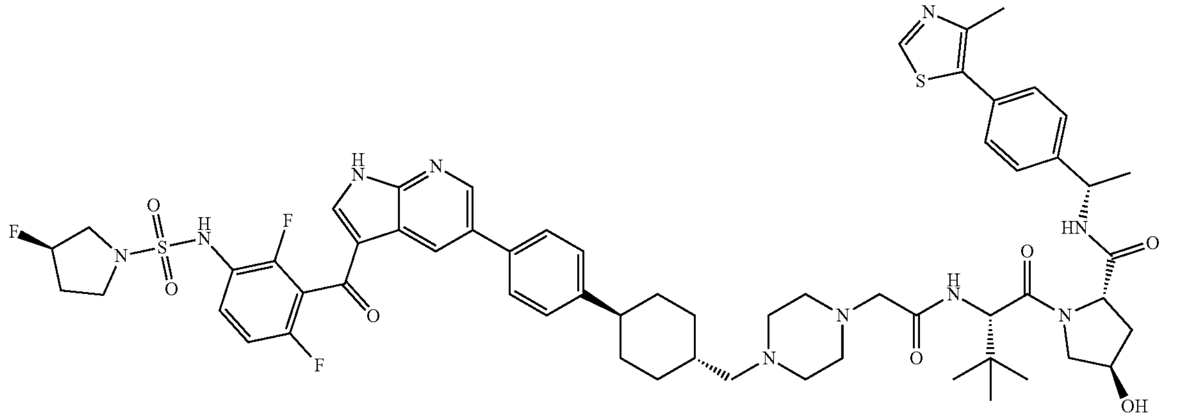
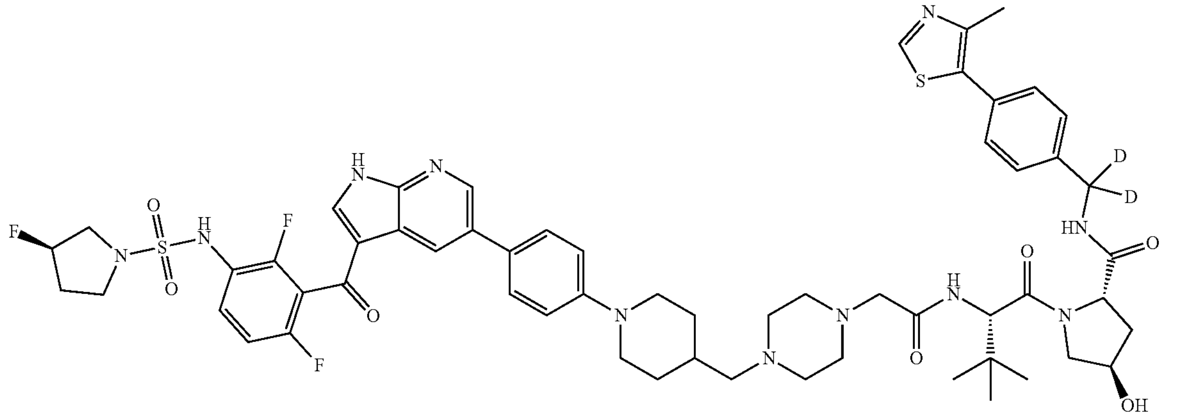
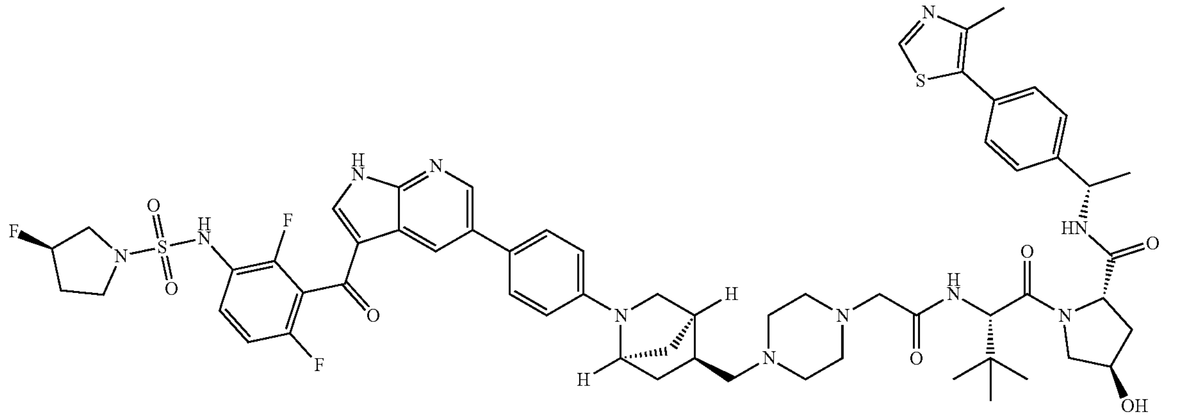

-continued
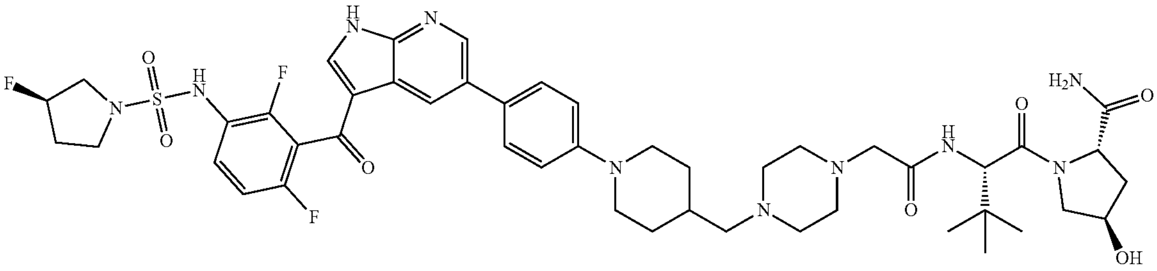
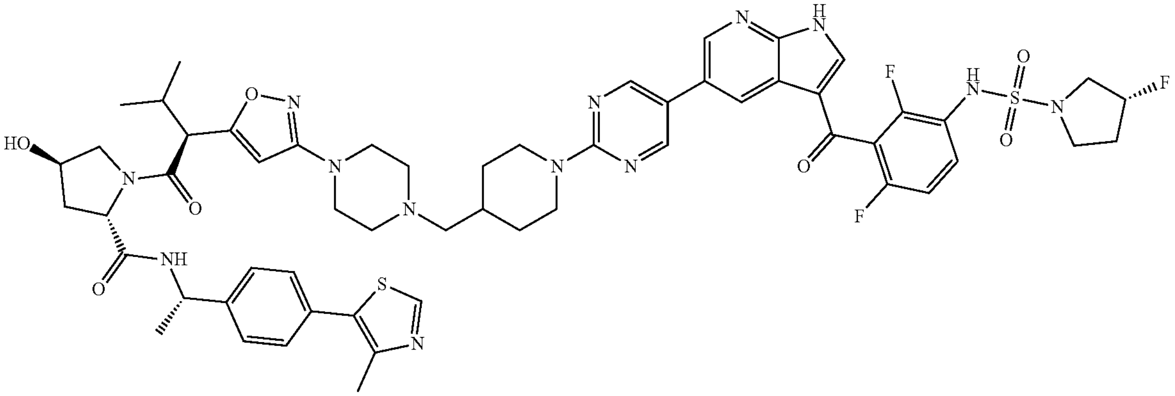
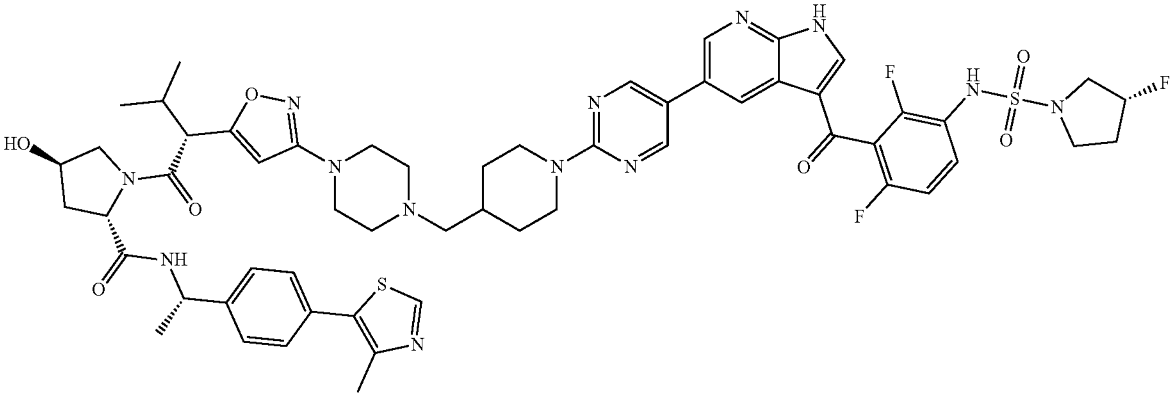
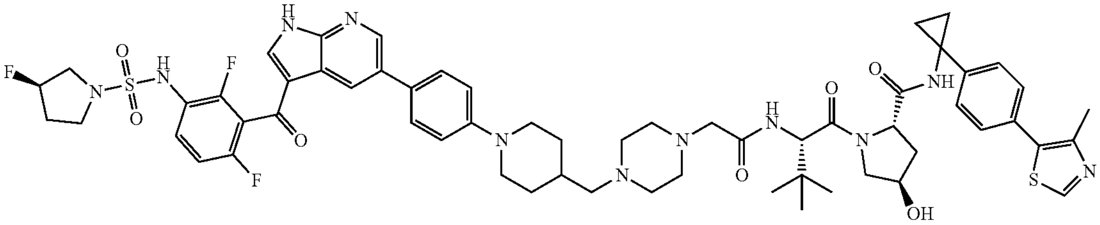
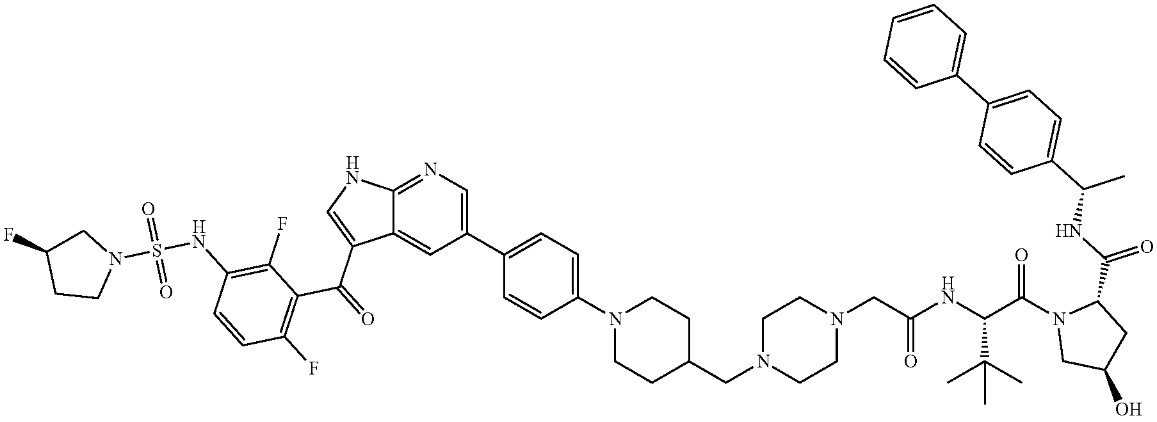

-continued
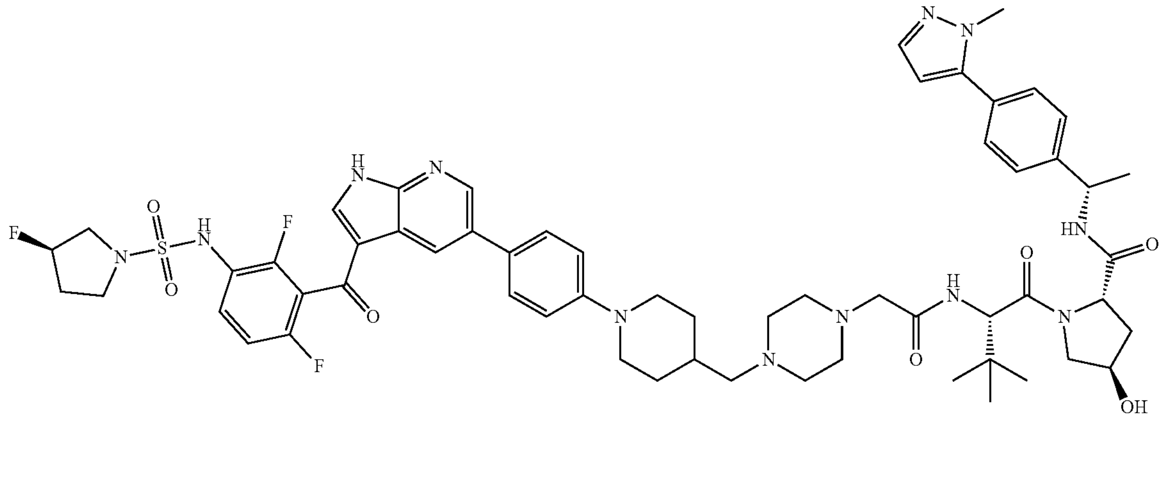
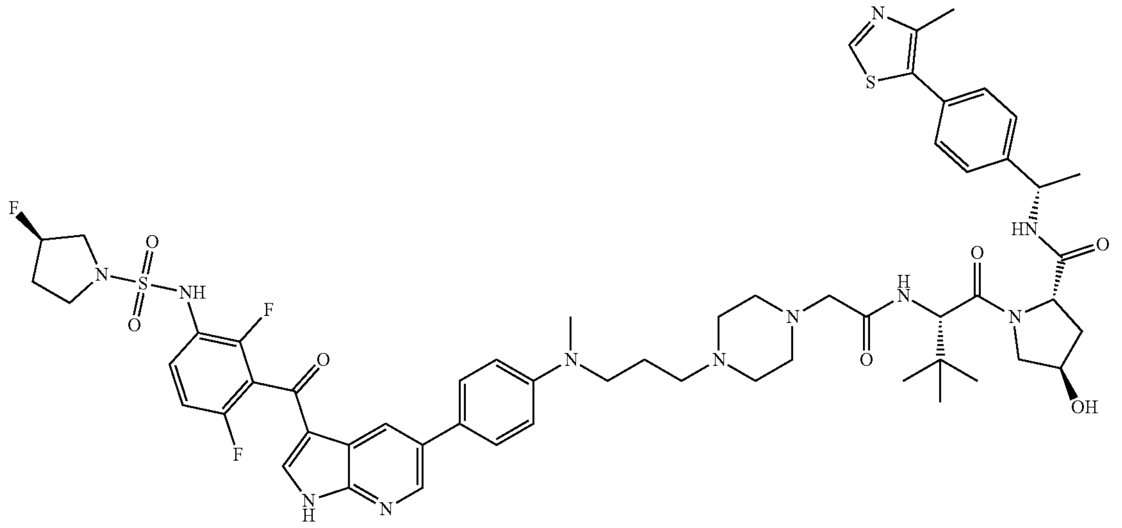
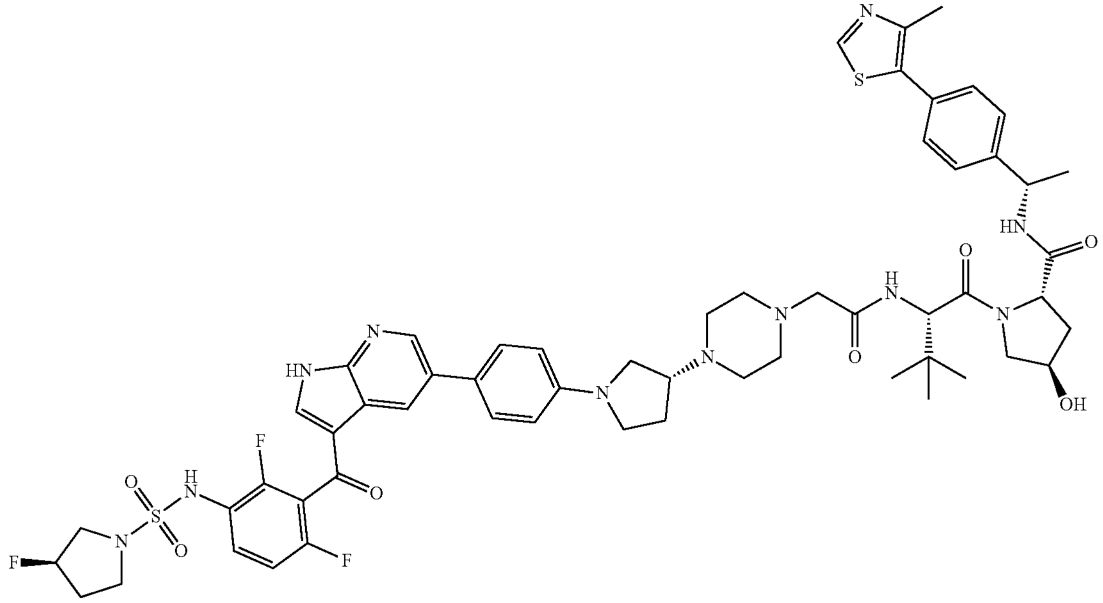

-continued
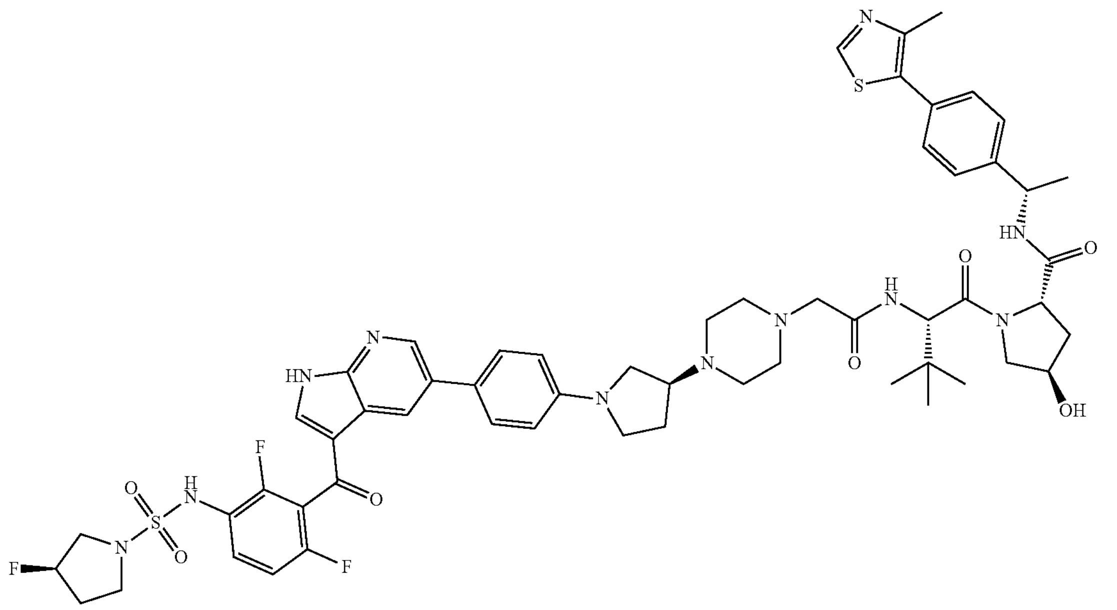
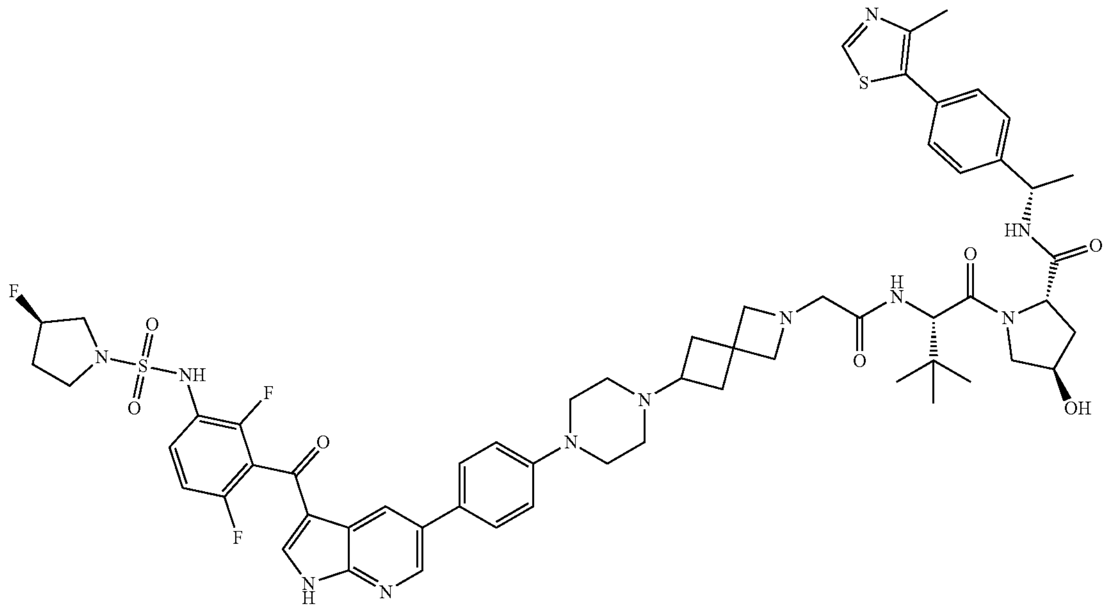
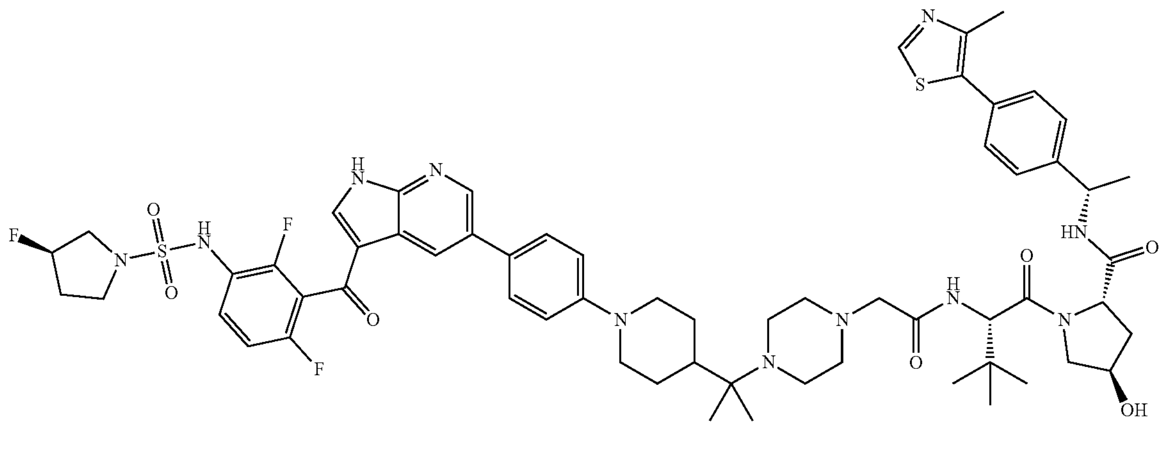

-continued
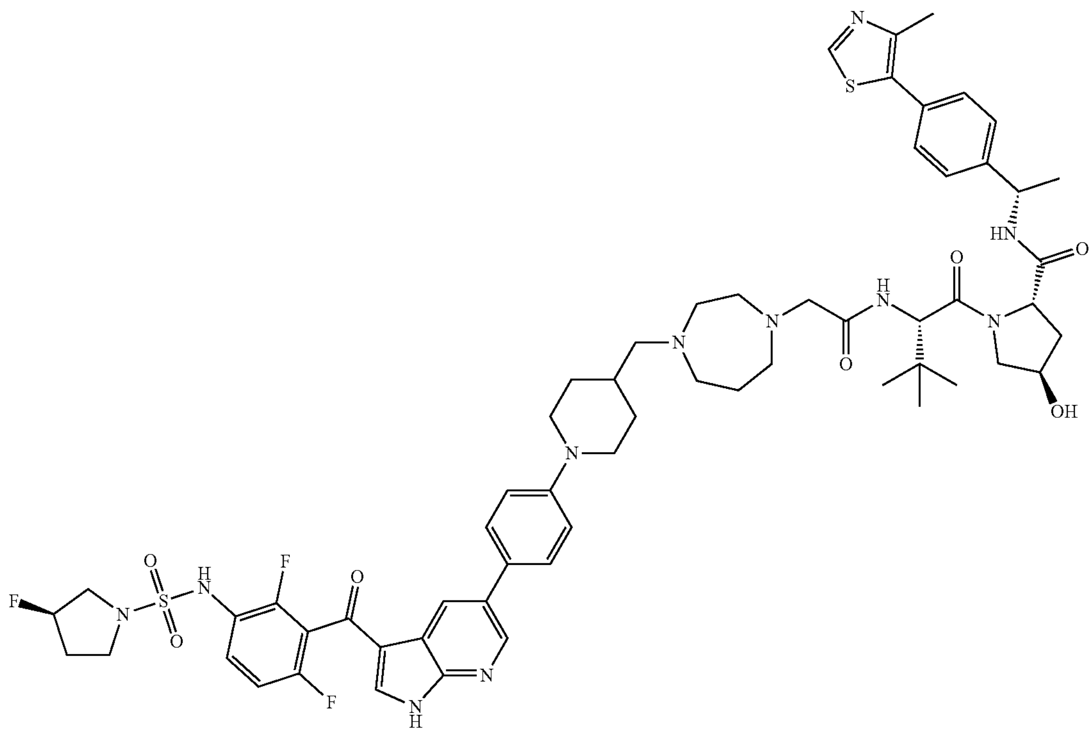
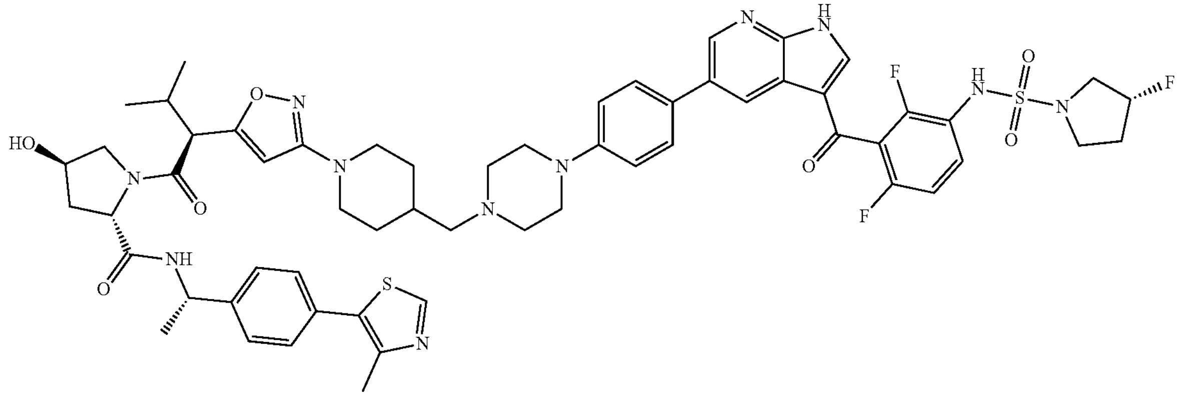
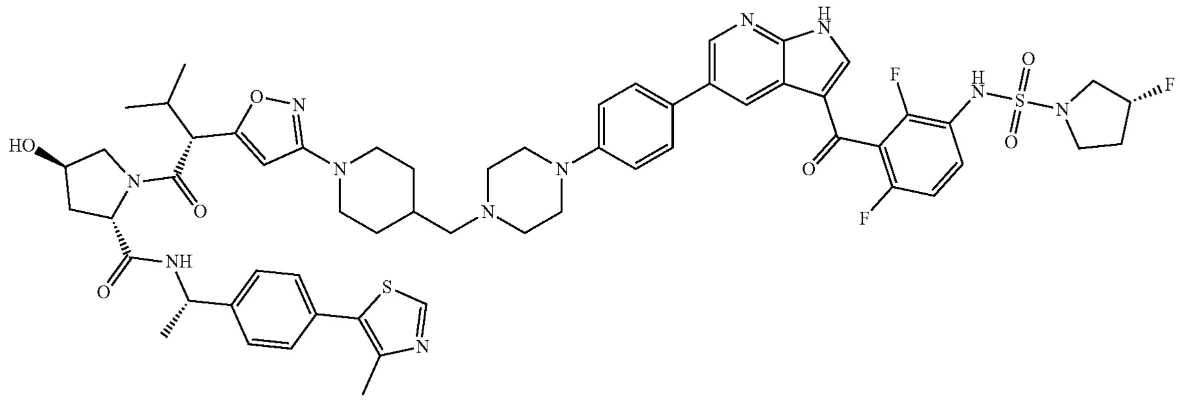

-continued
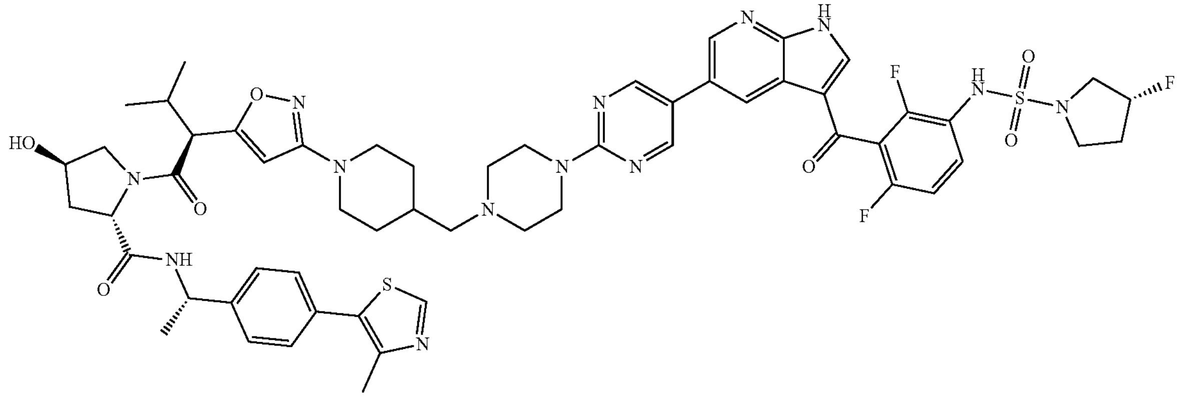
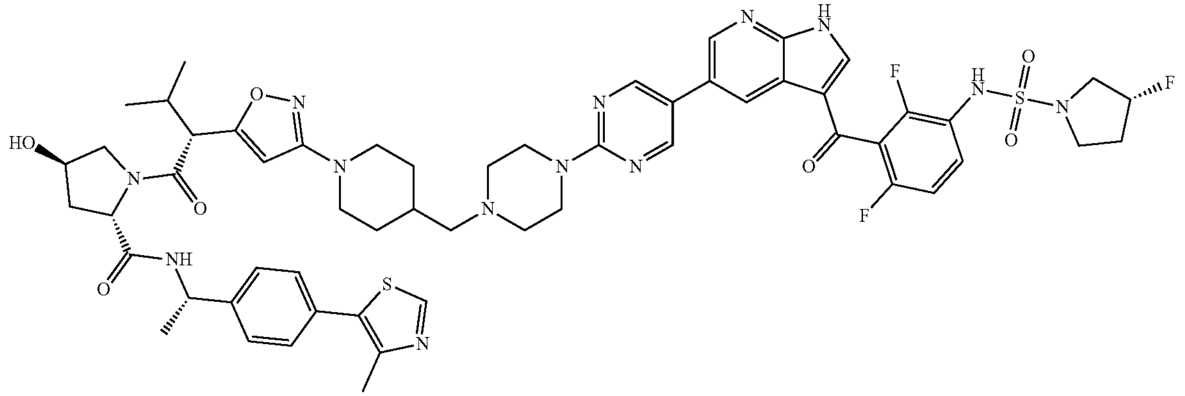
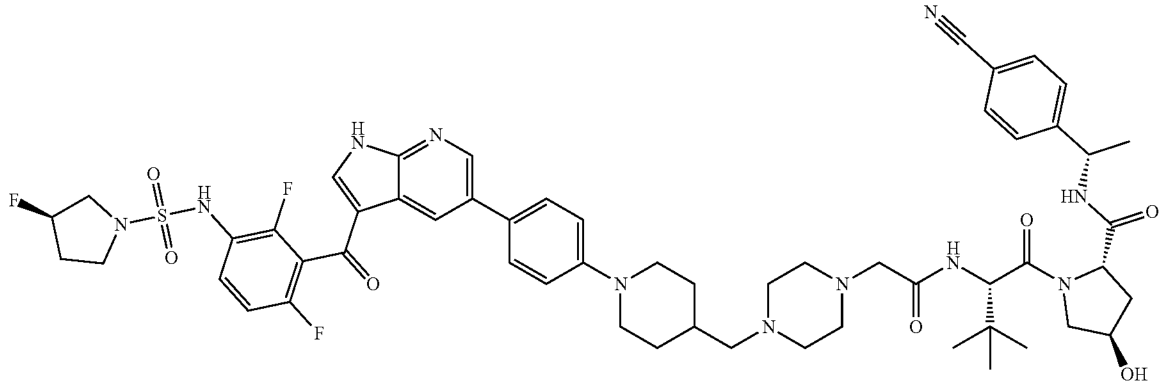
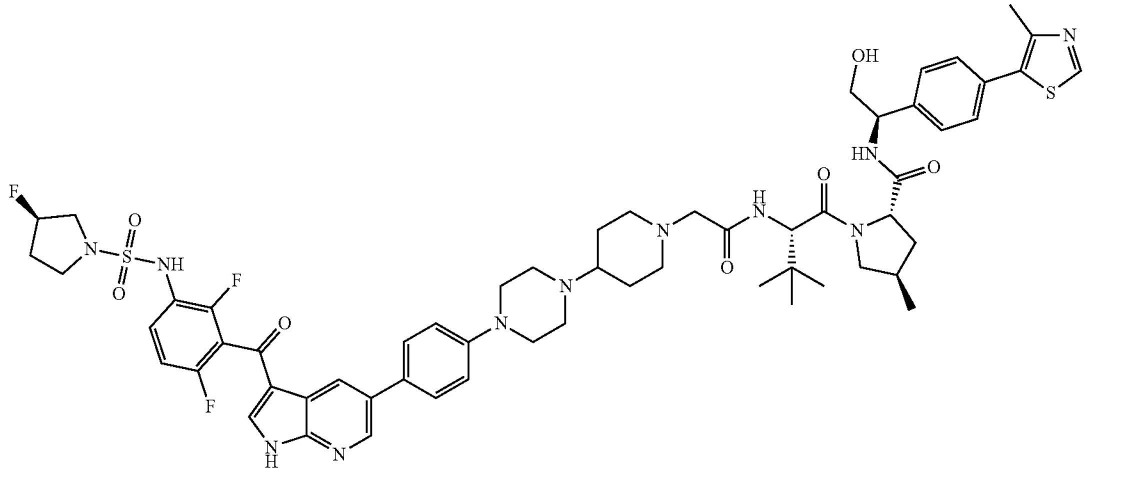

-continued
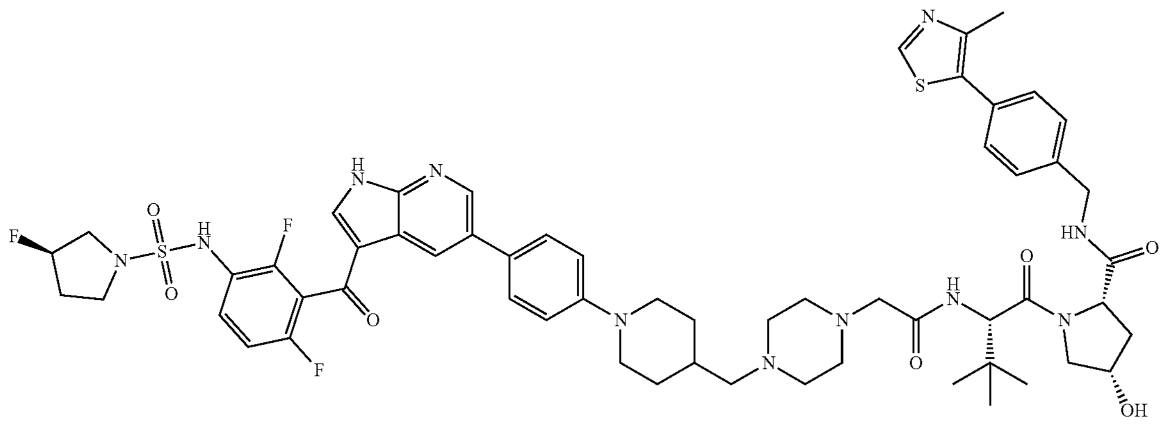
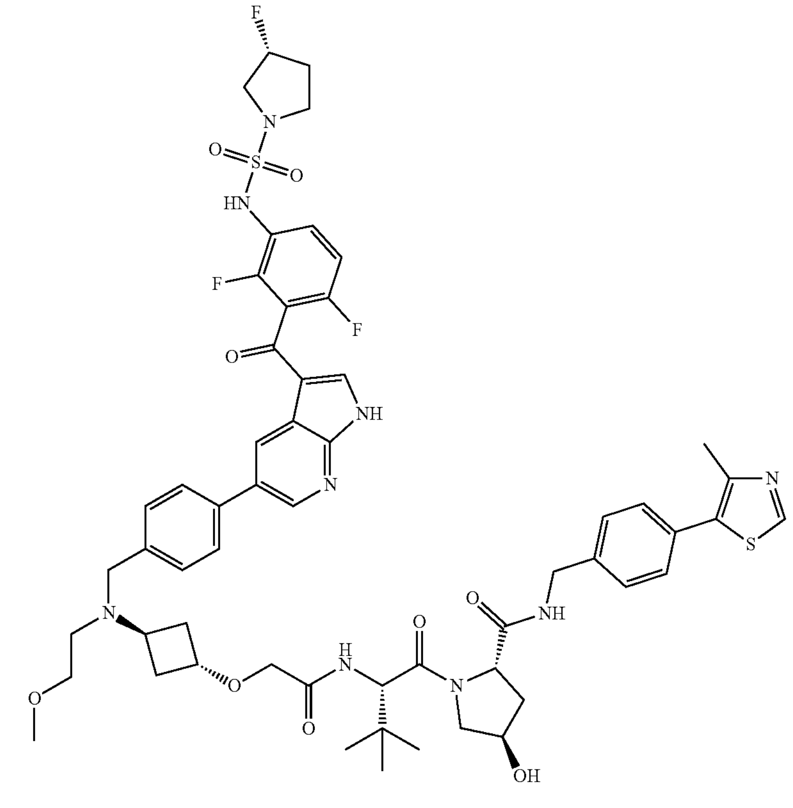
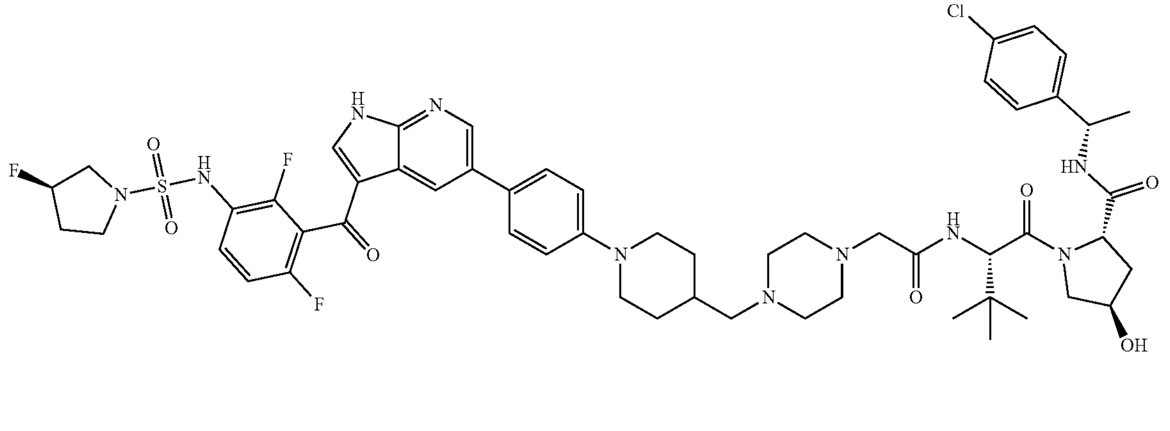

-continued
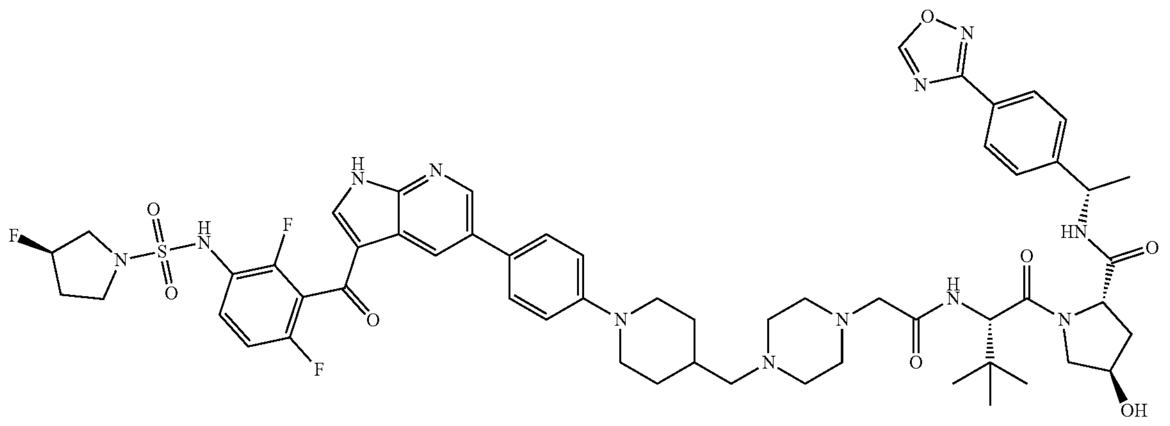
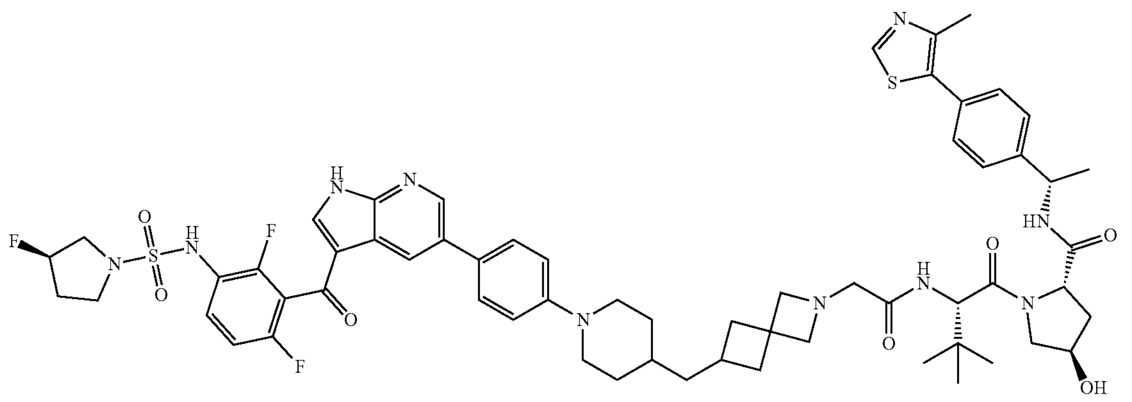
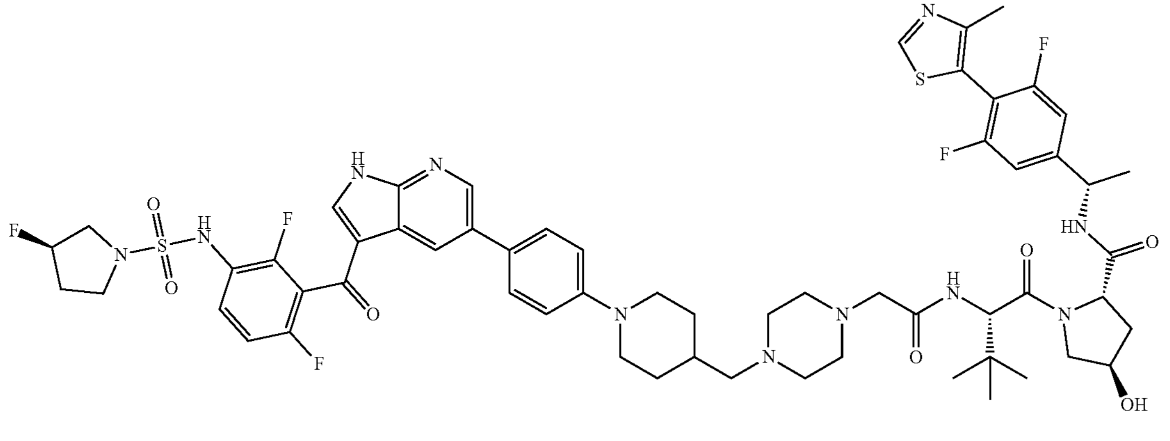

-continued
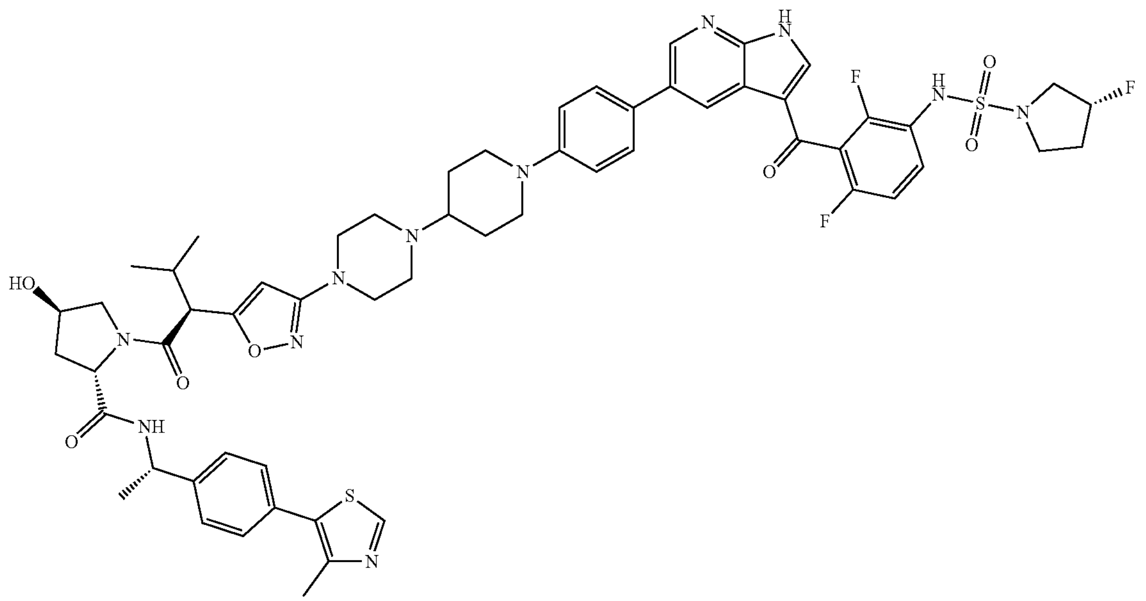
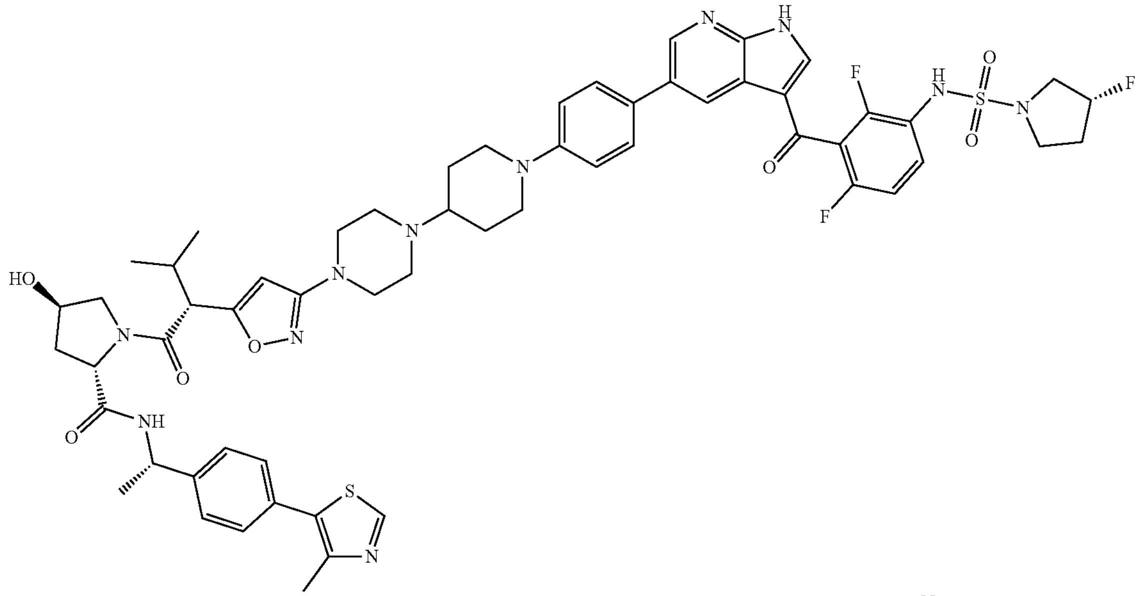
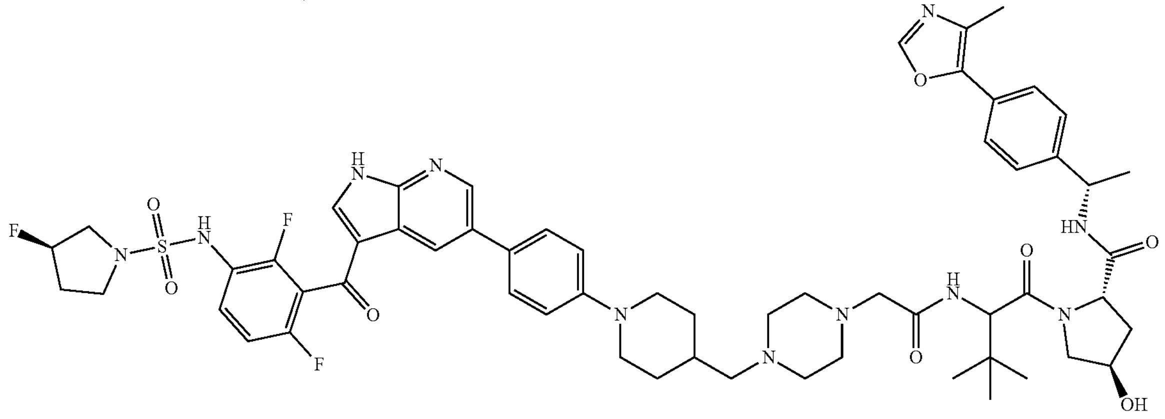

-continued
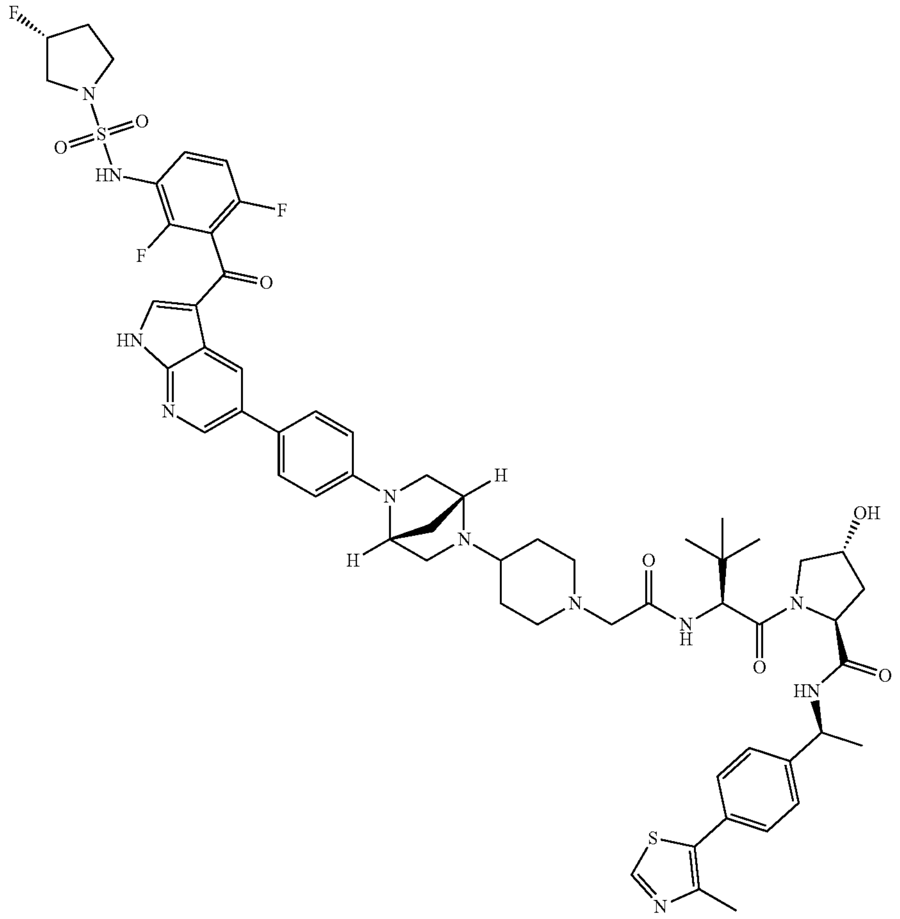
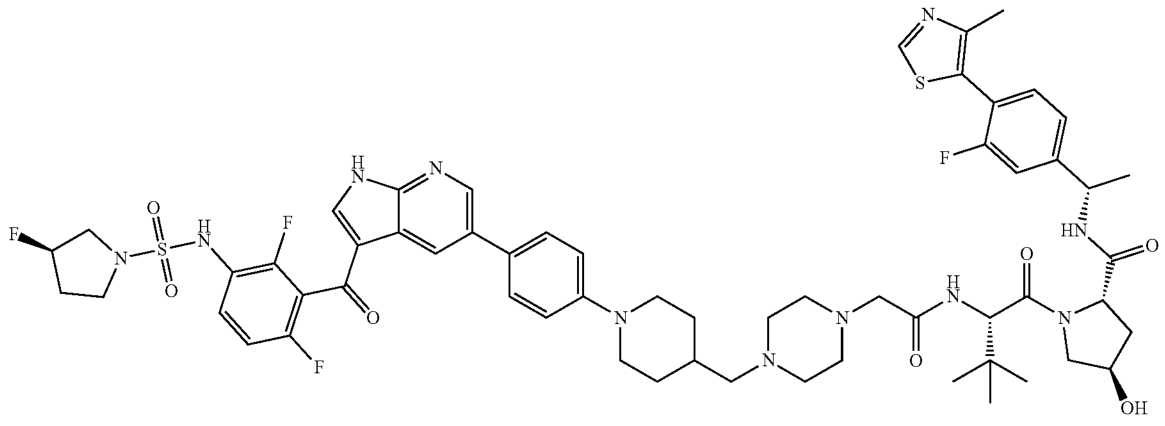

-continued
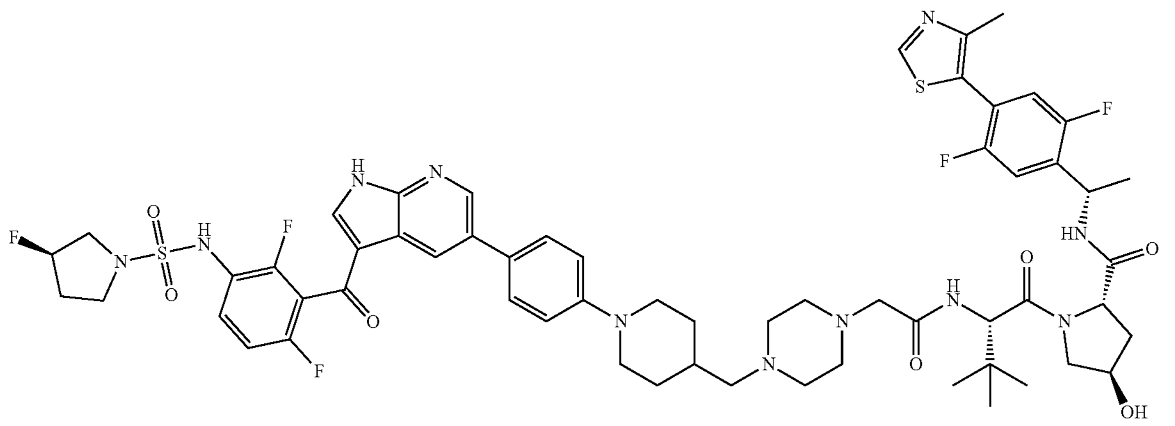
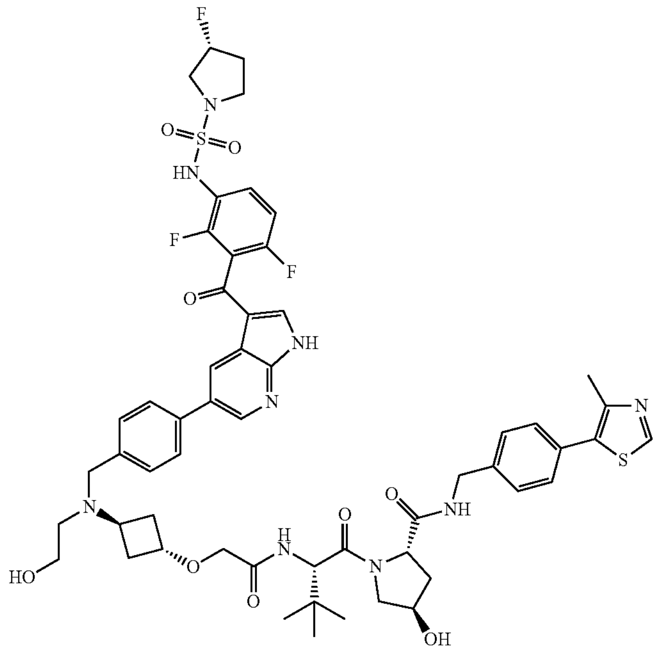
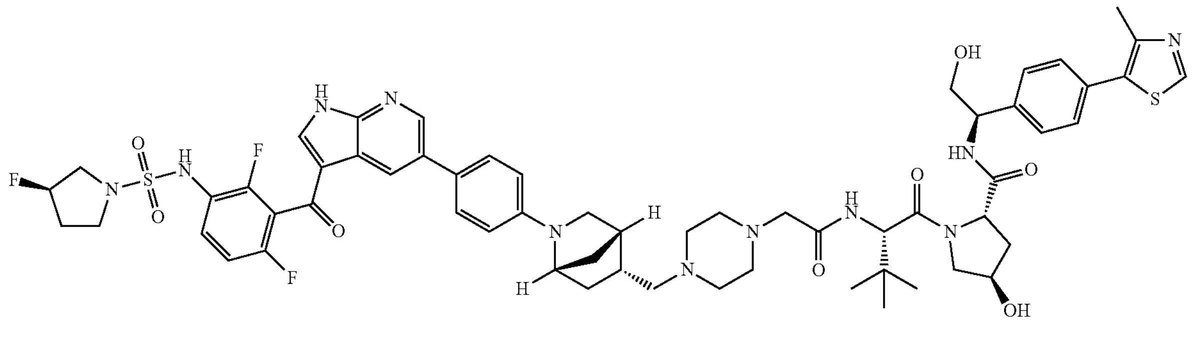

-continued
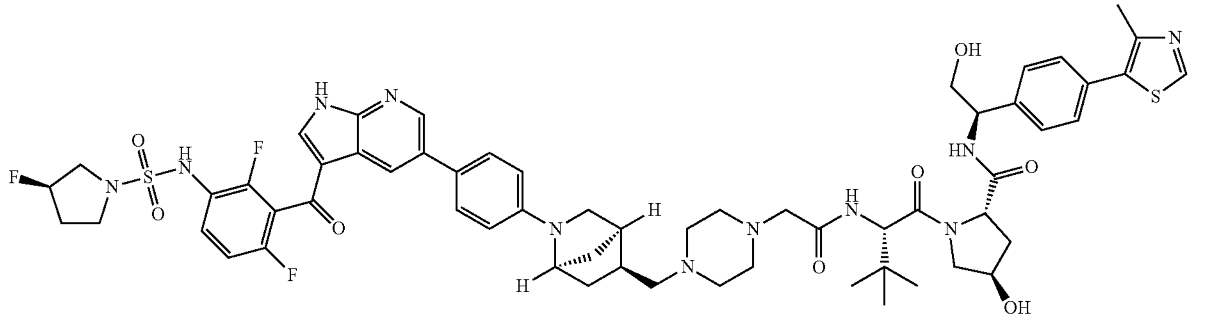
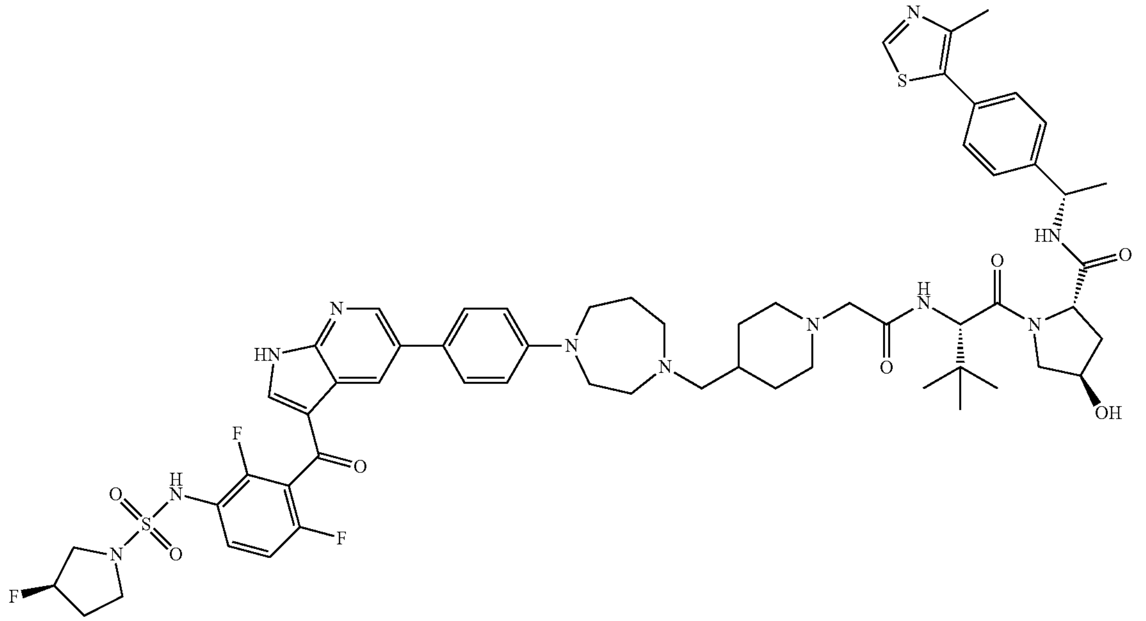
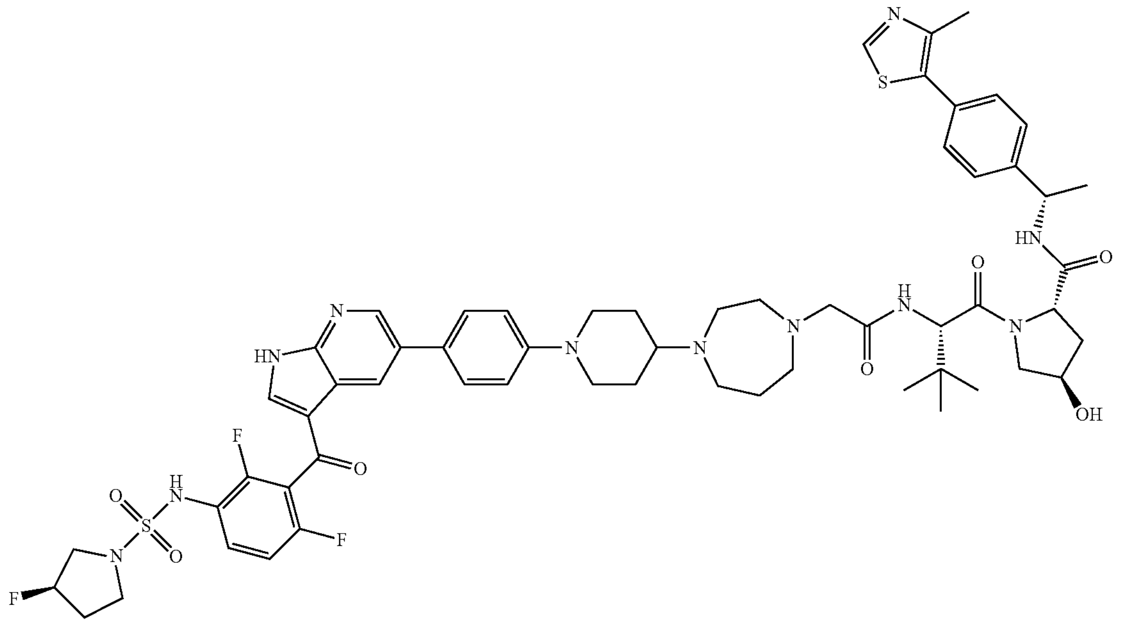

-continued
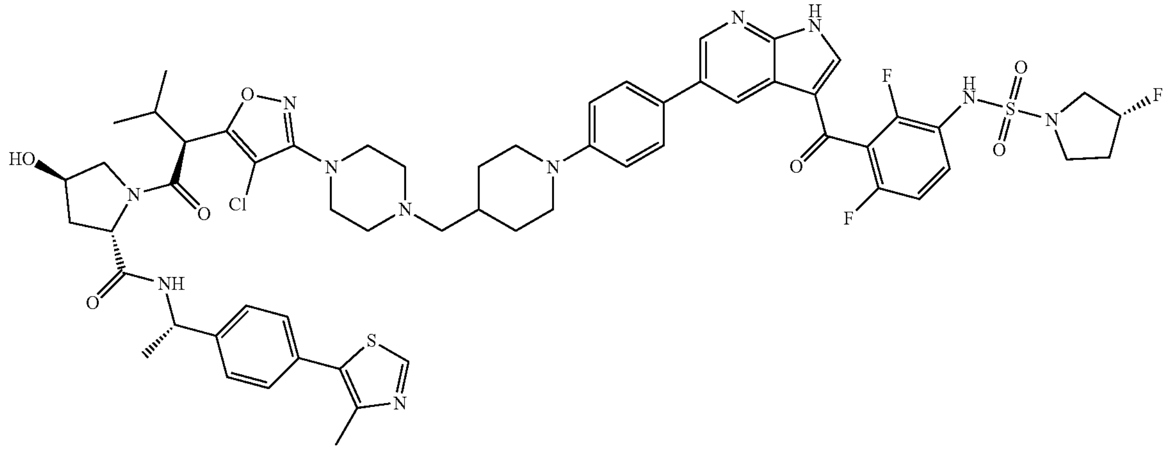
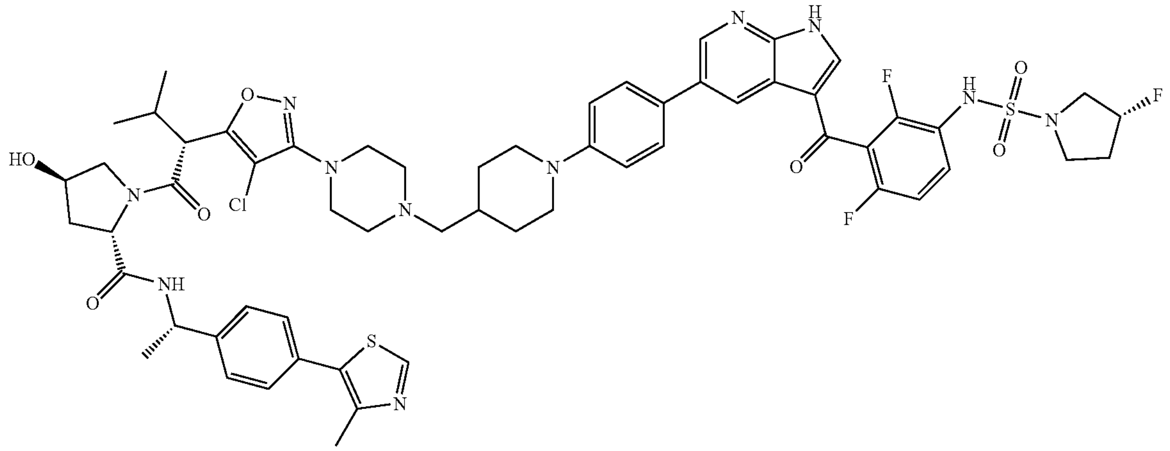
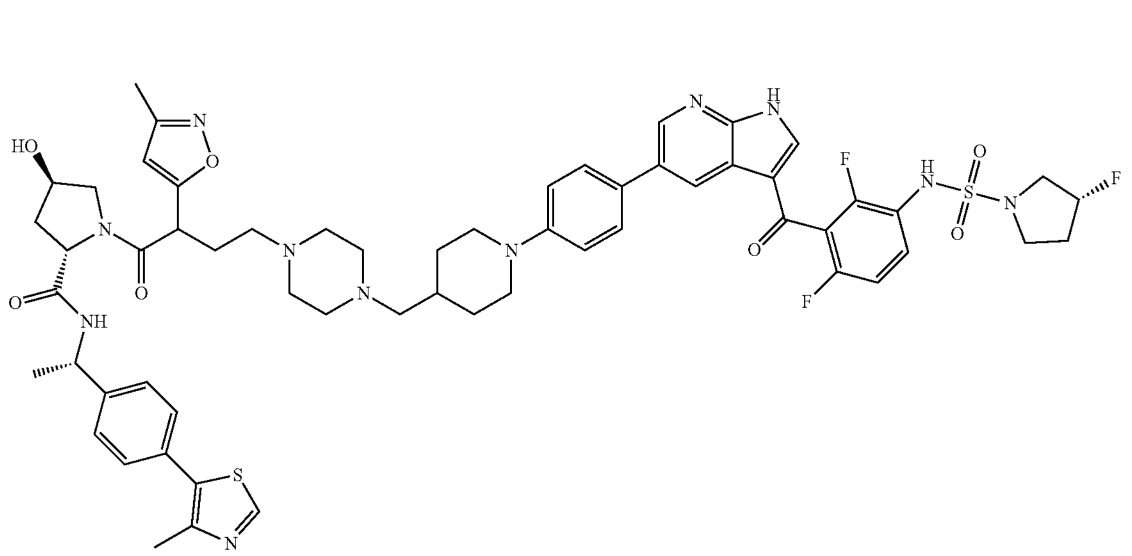

-continued
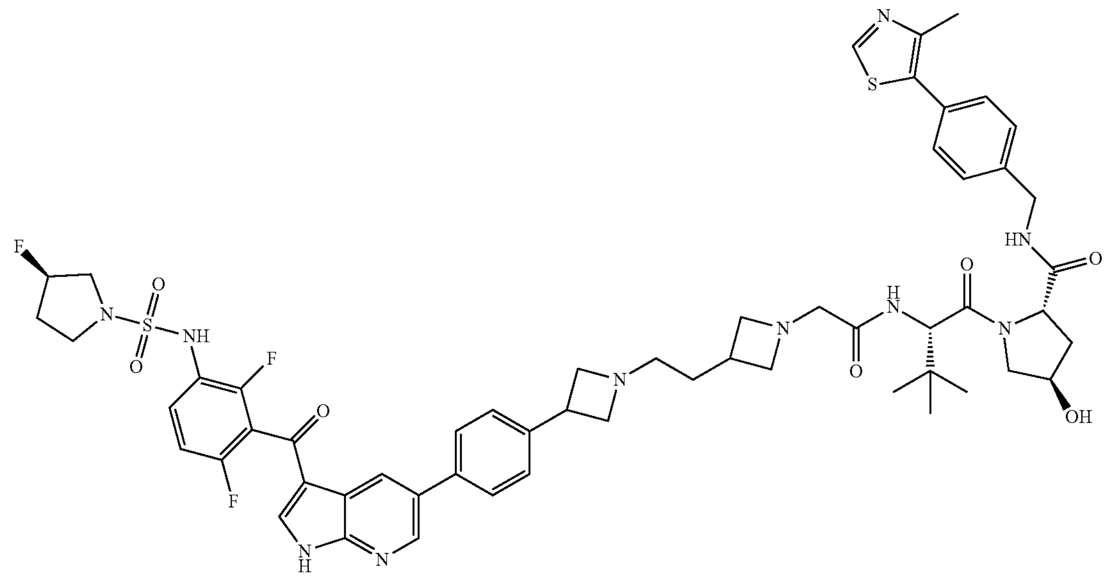
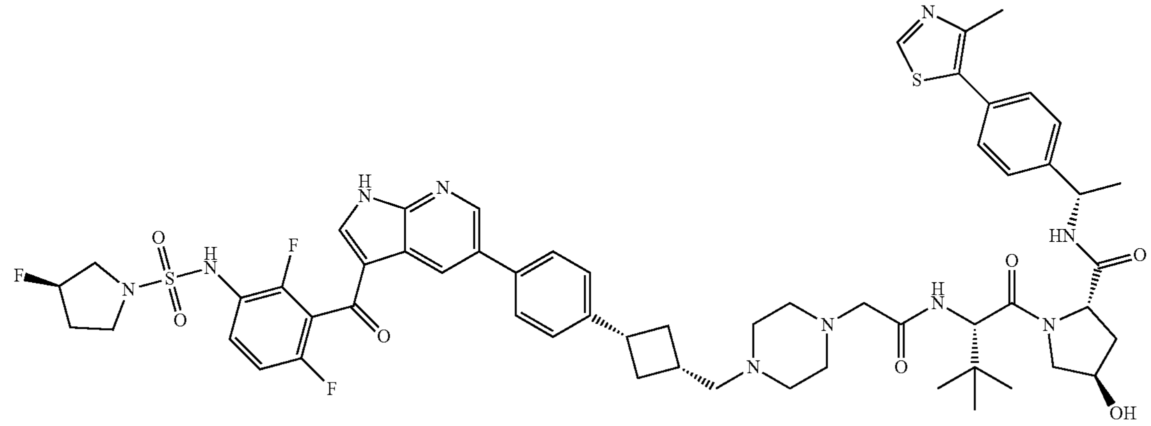
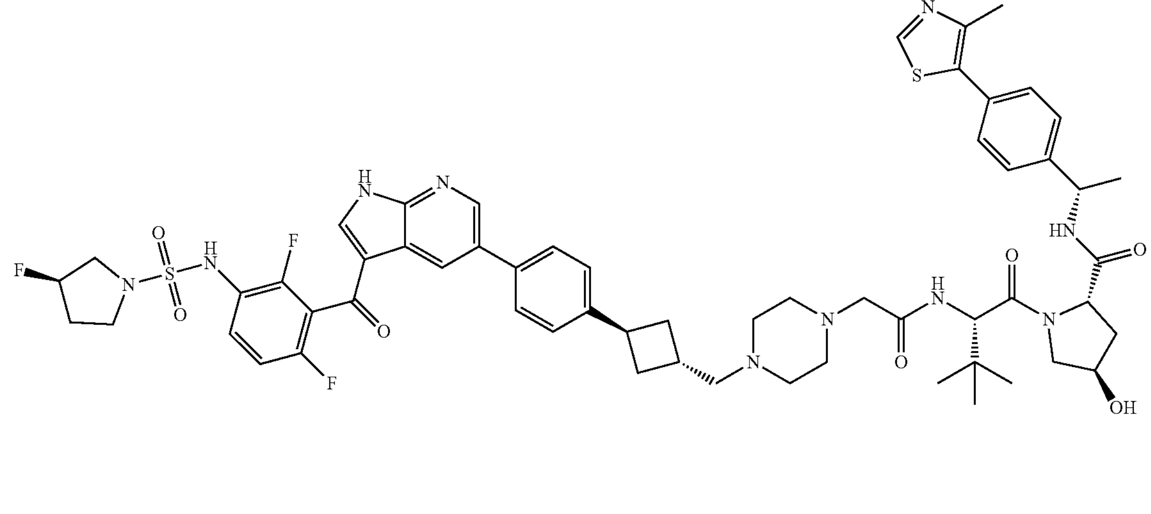

-continued
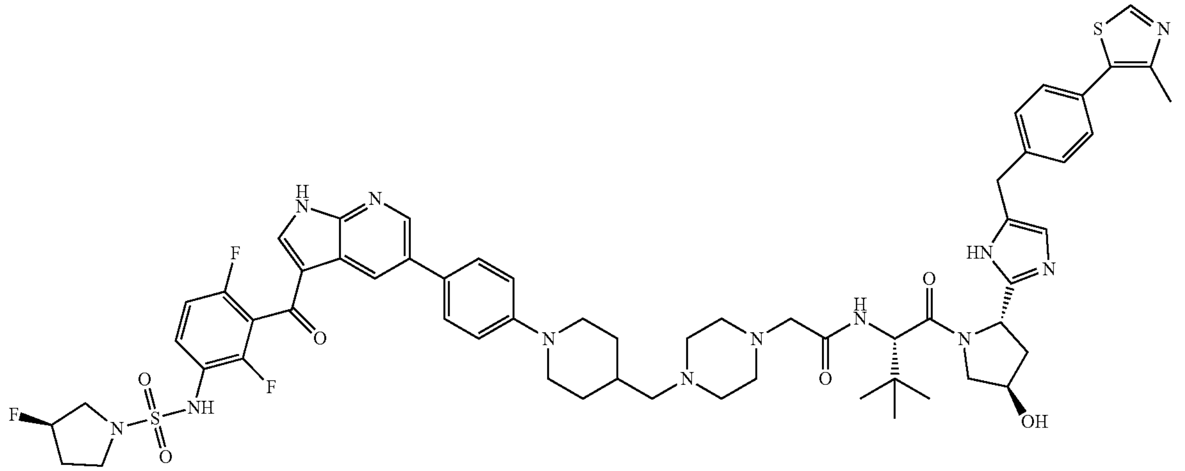
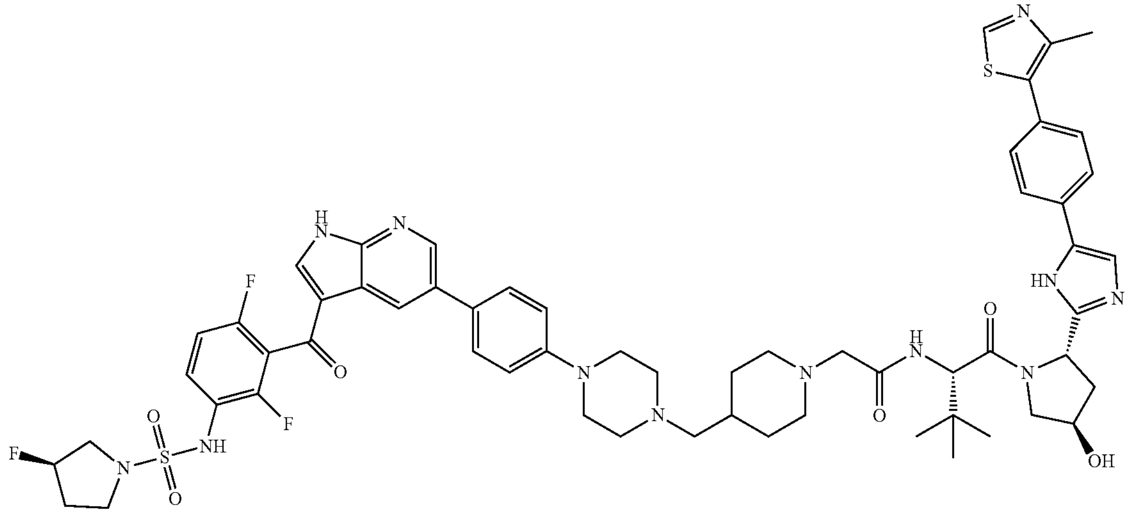
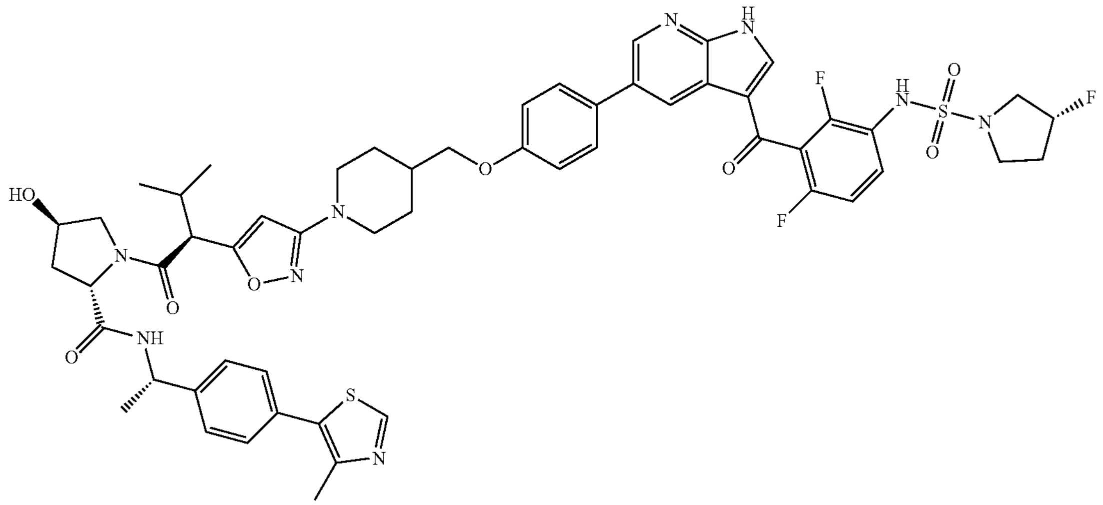

-continued
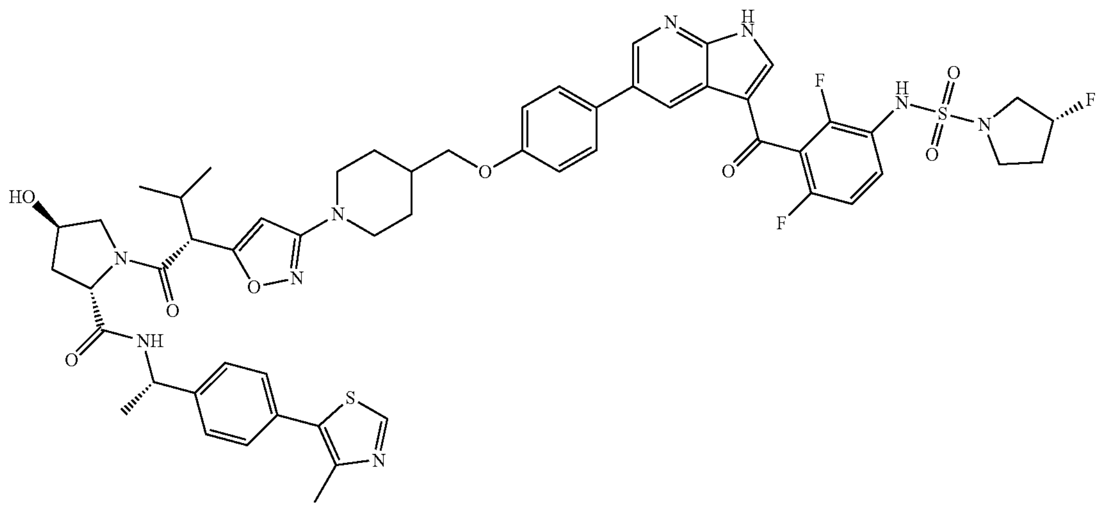
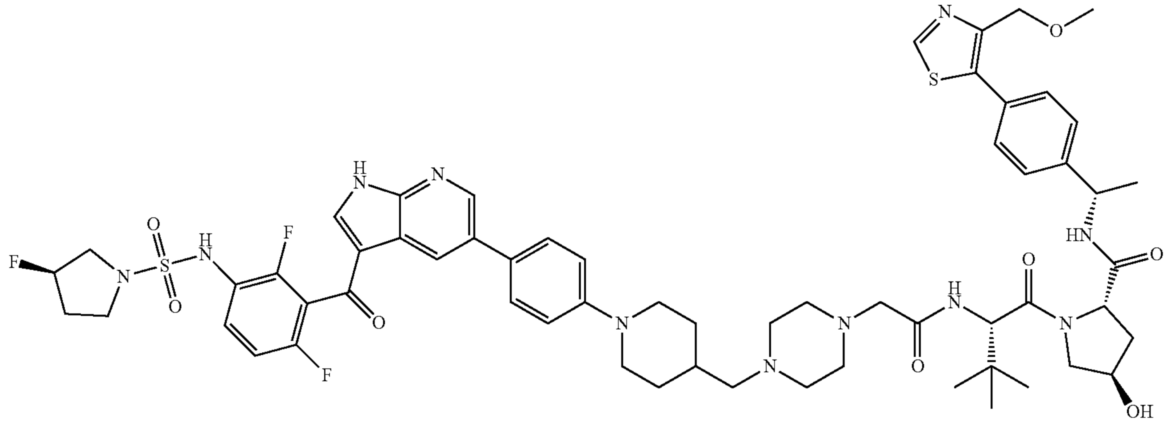
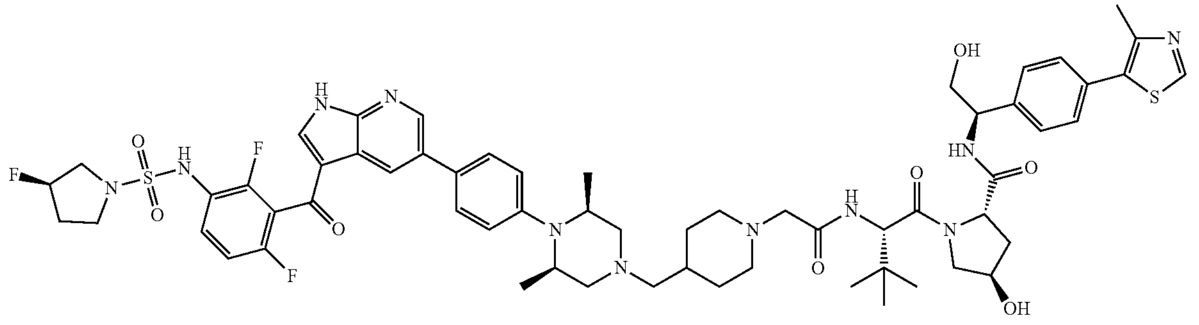

-continued
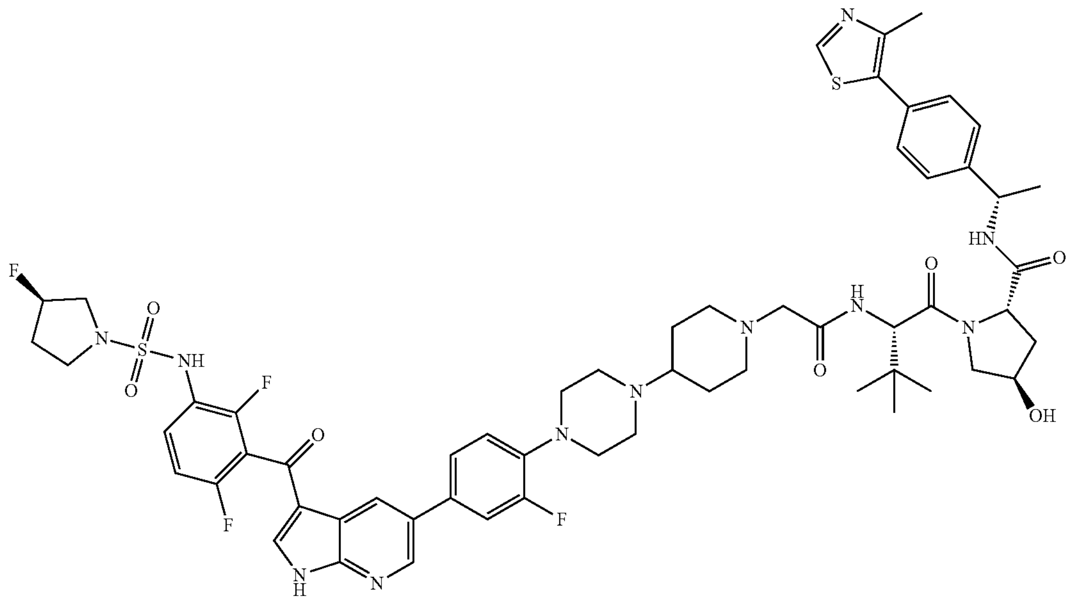
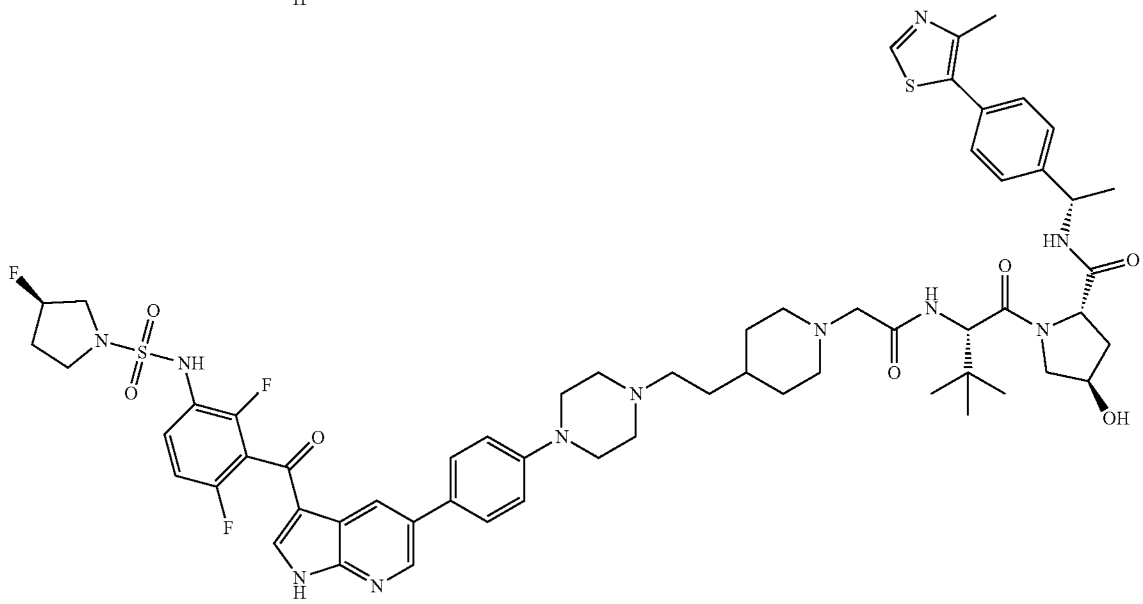
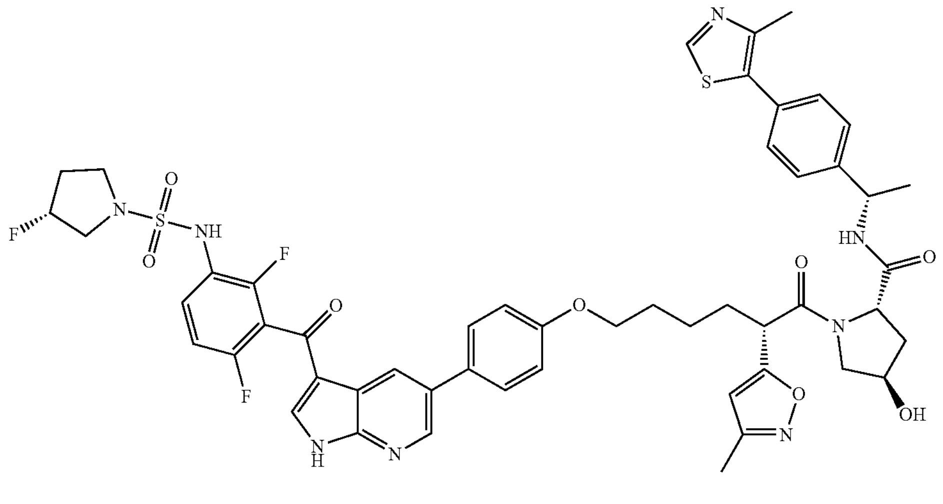

-continued
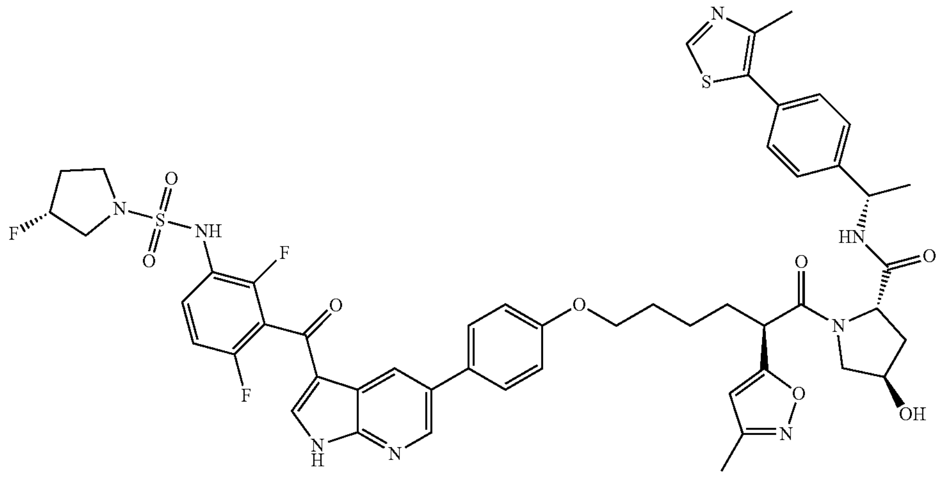
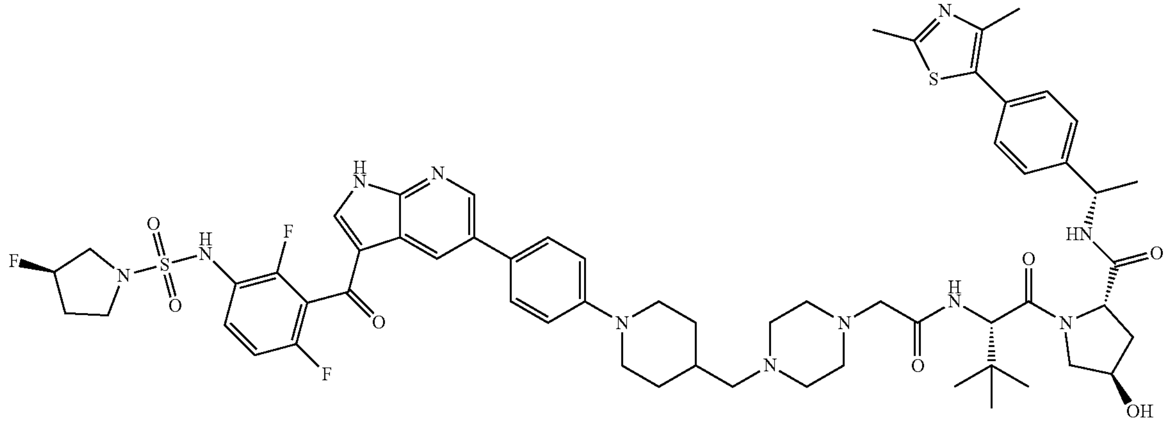
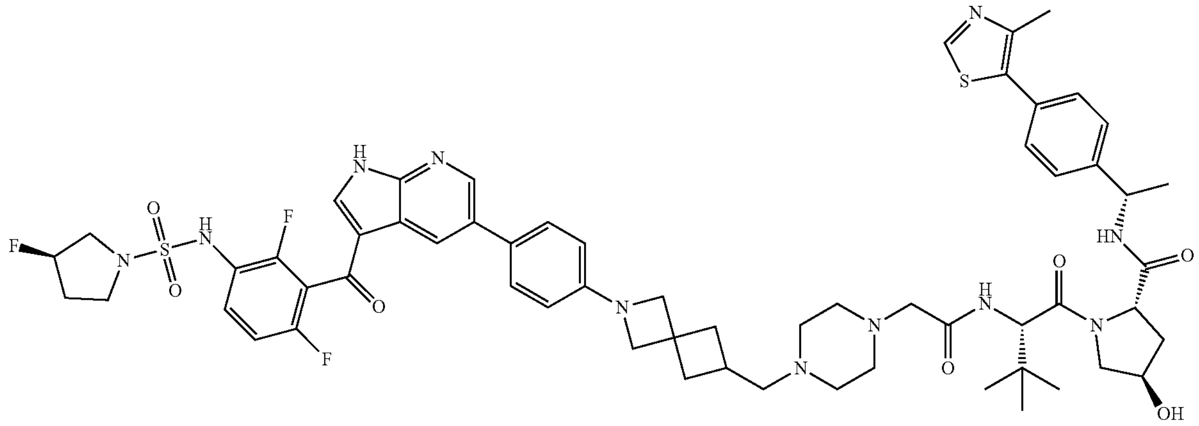
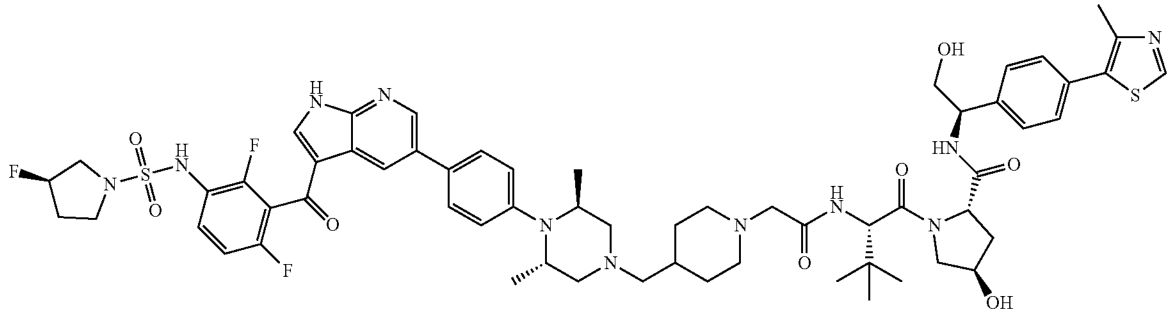

-continued
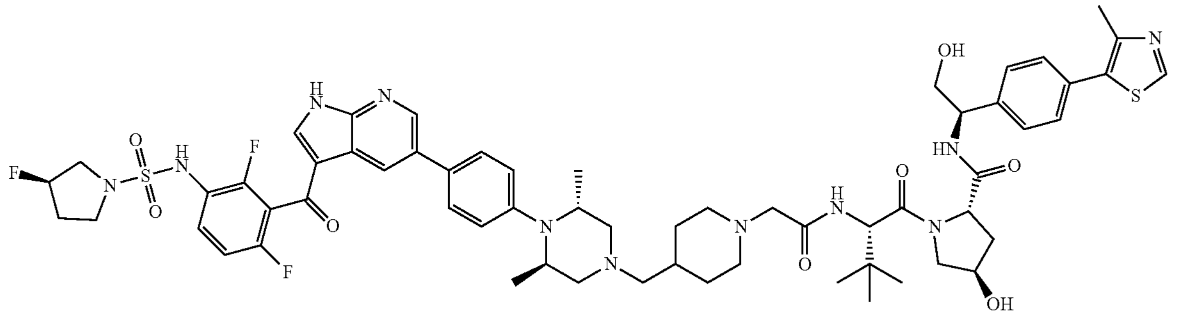
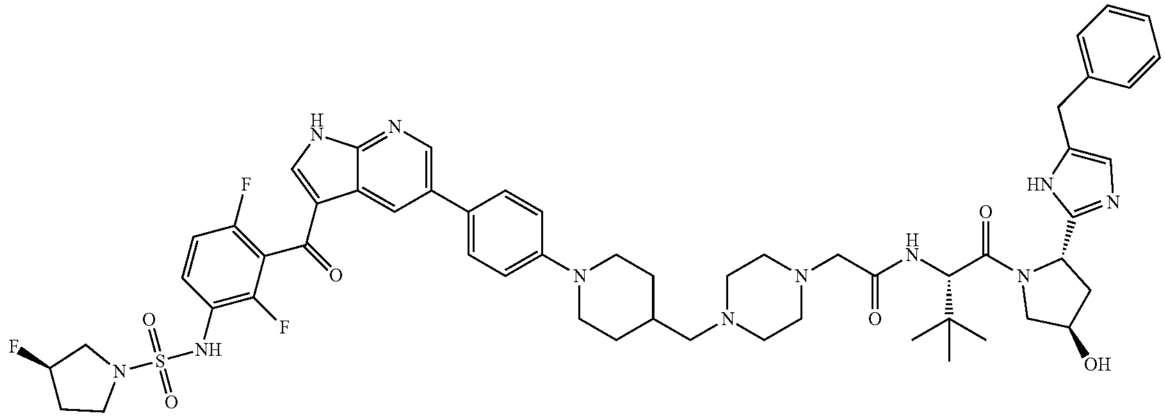
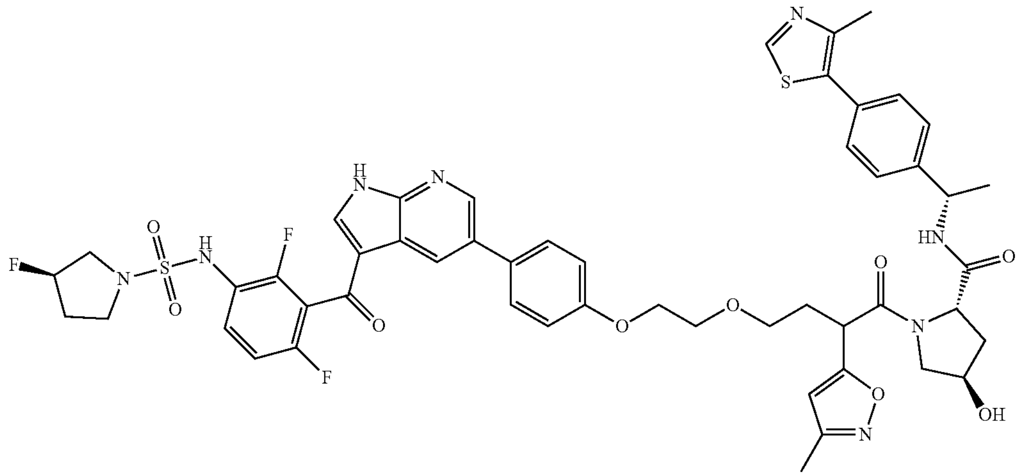
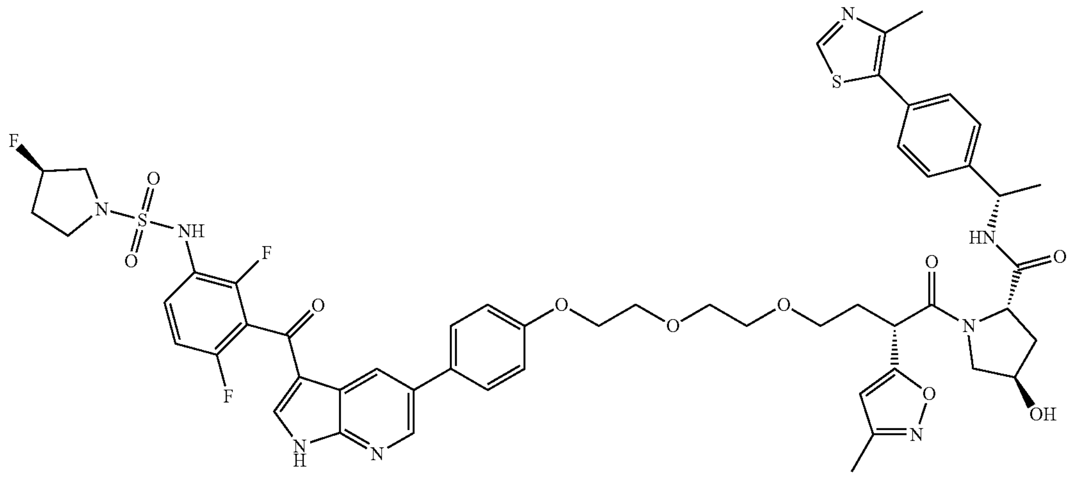

-continued
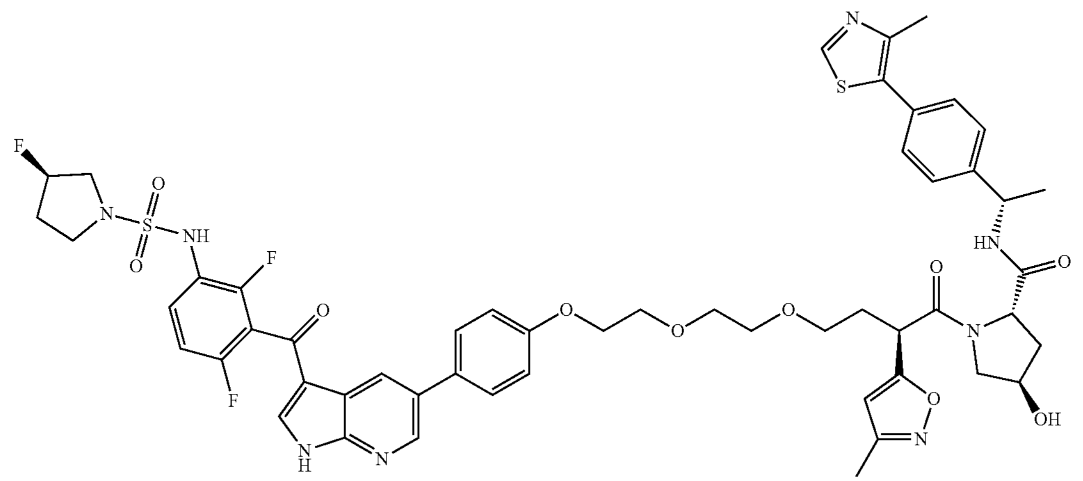
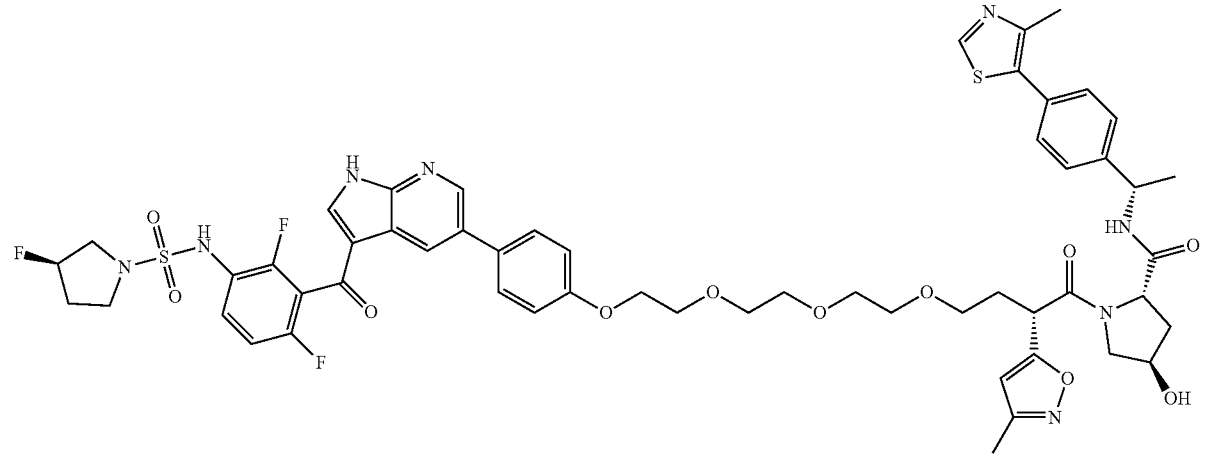
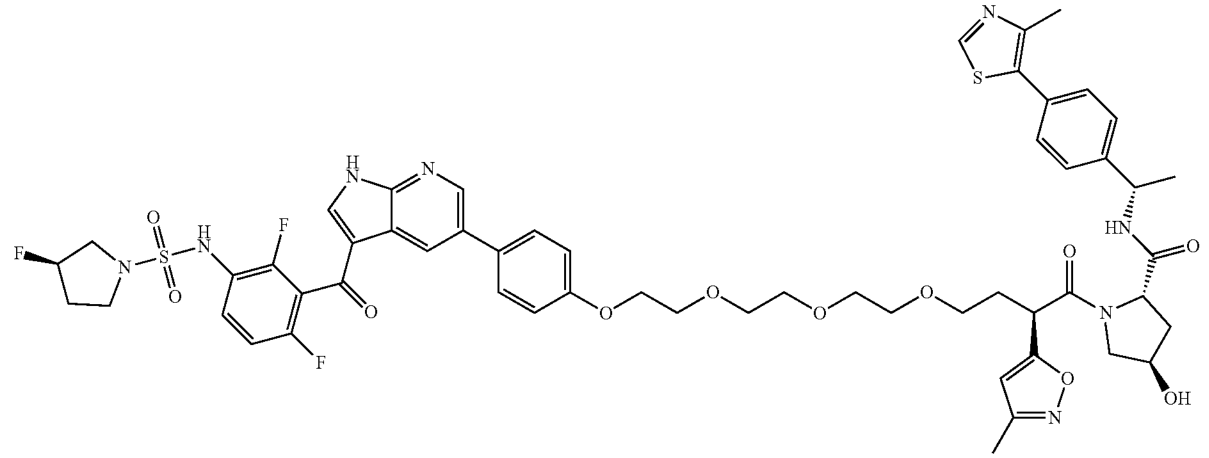

-continued
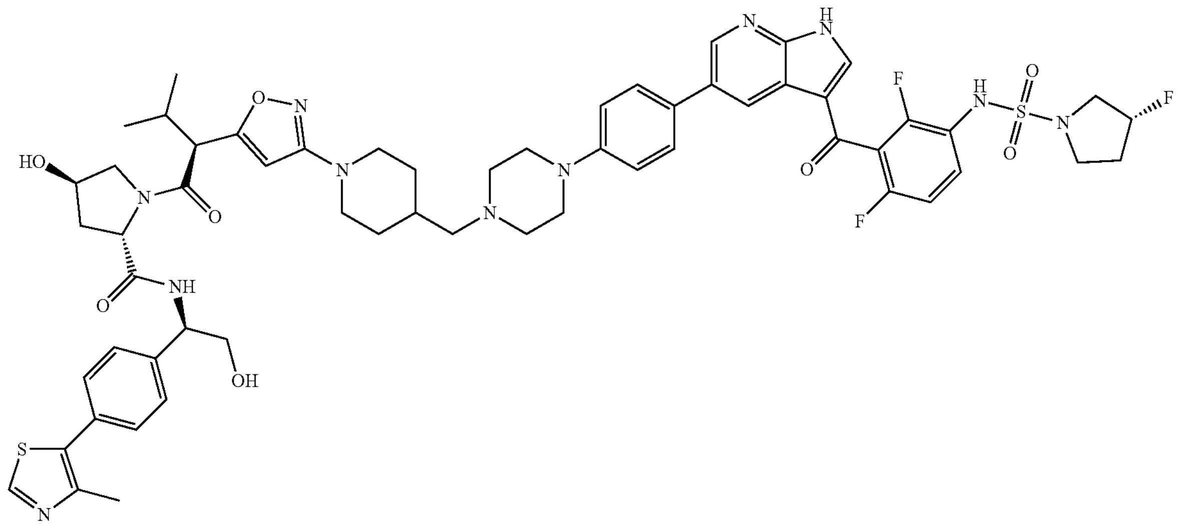
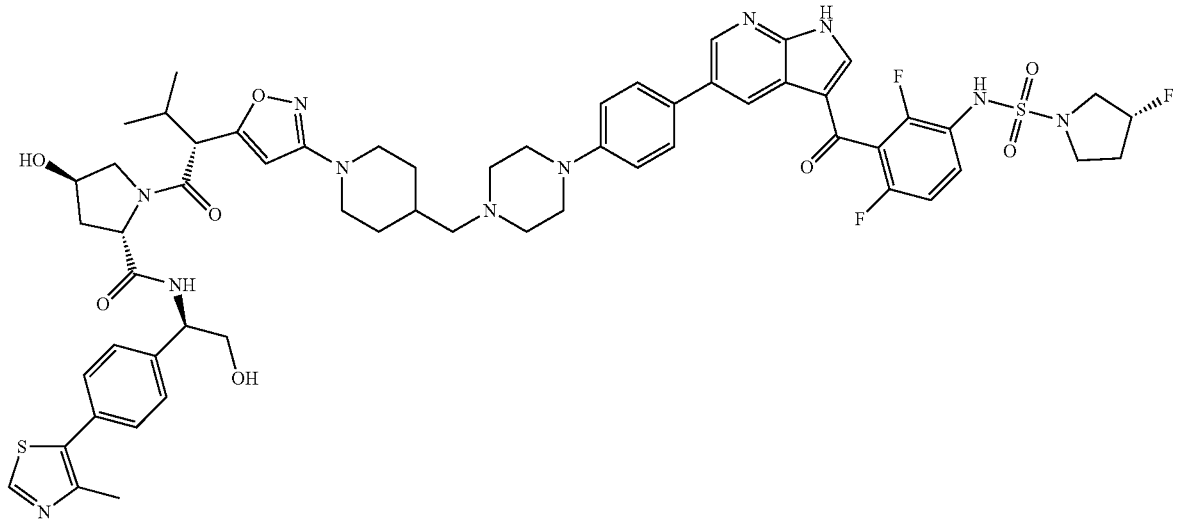
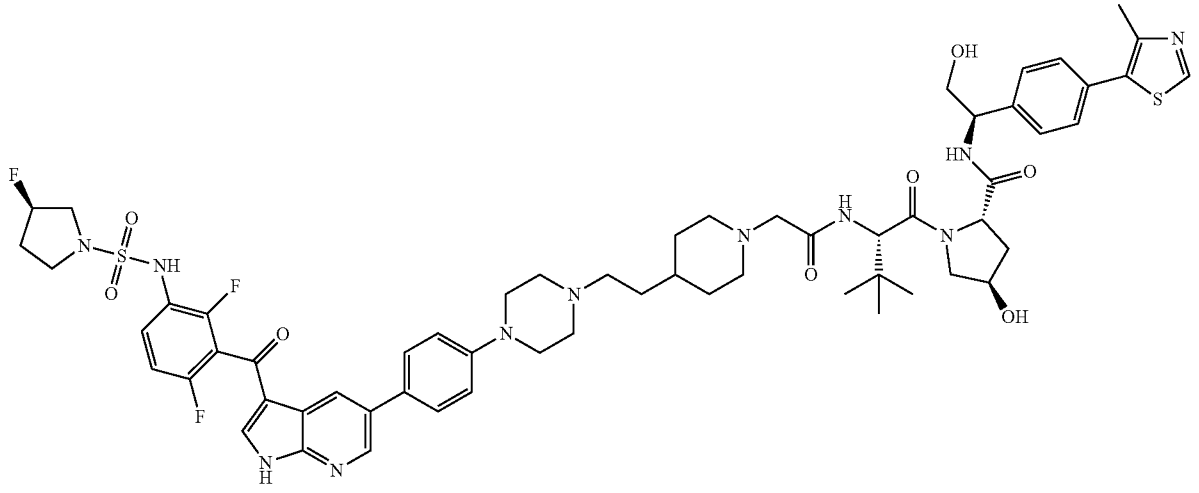

-continued
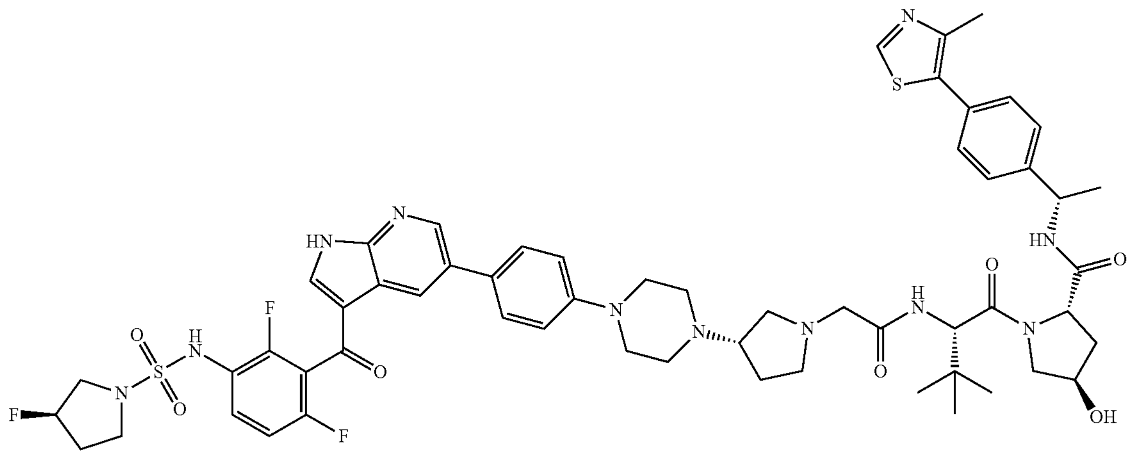
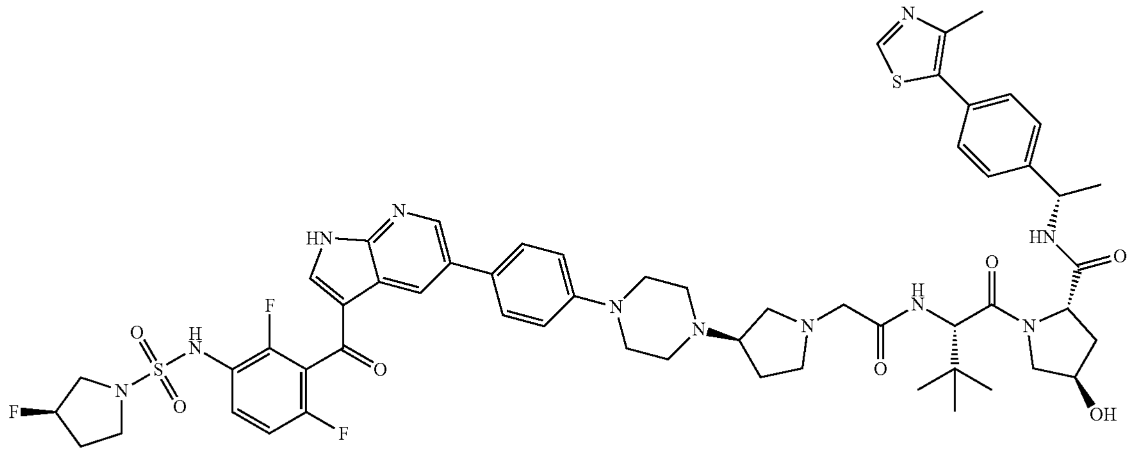
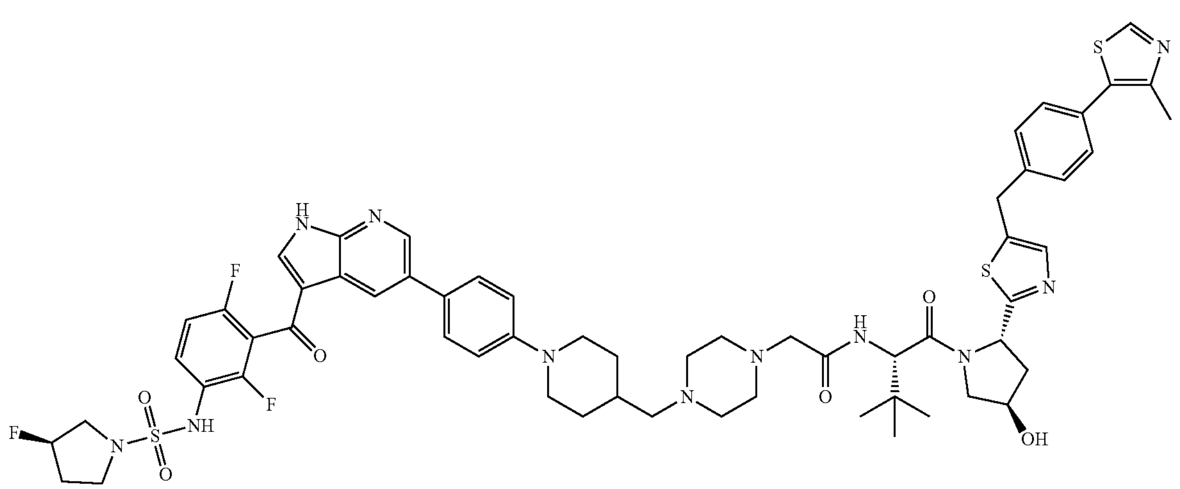

-continued
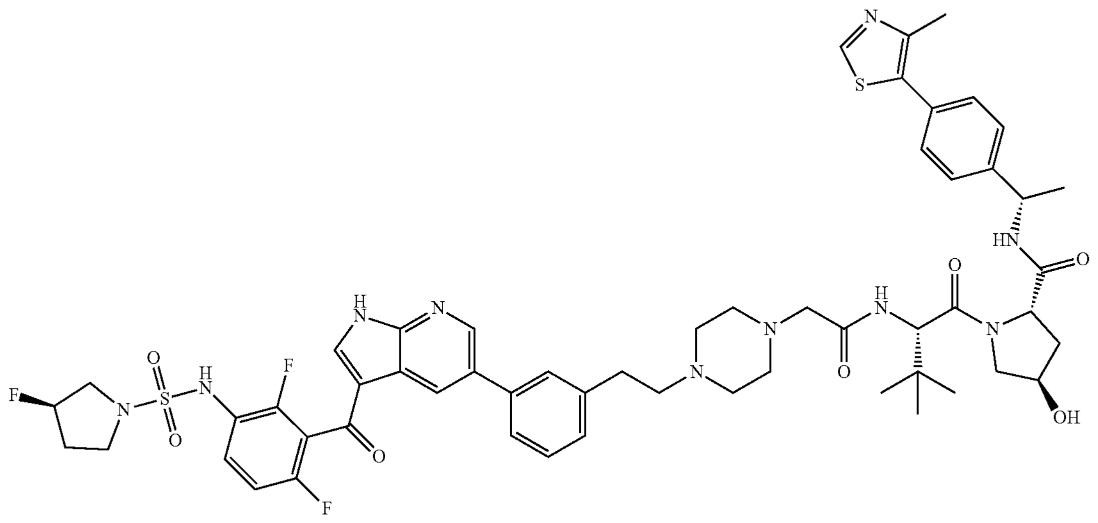
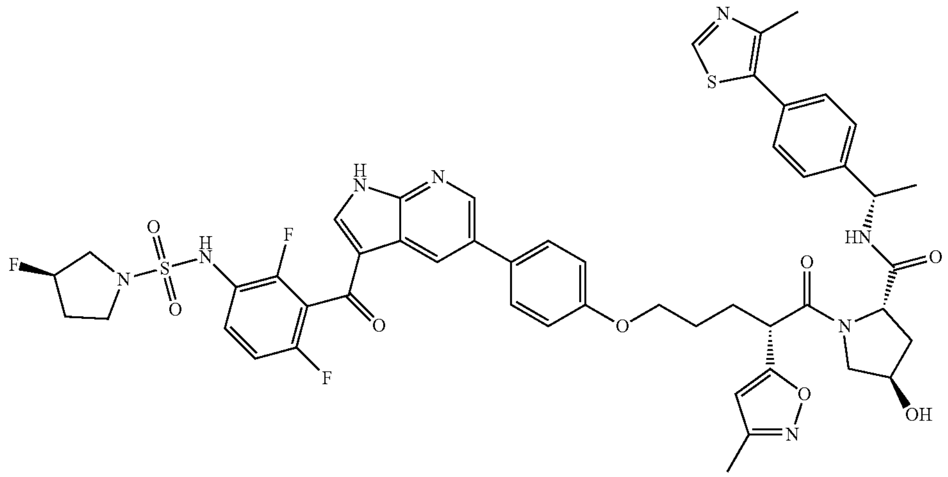
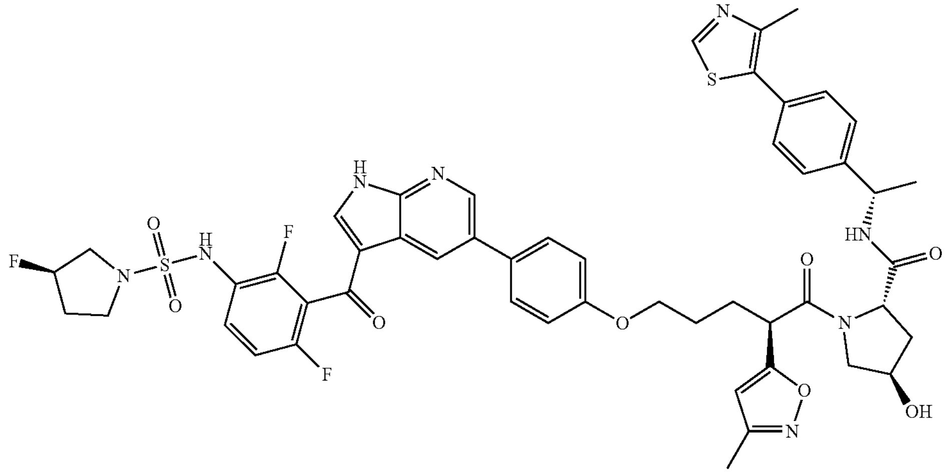

-continued
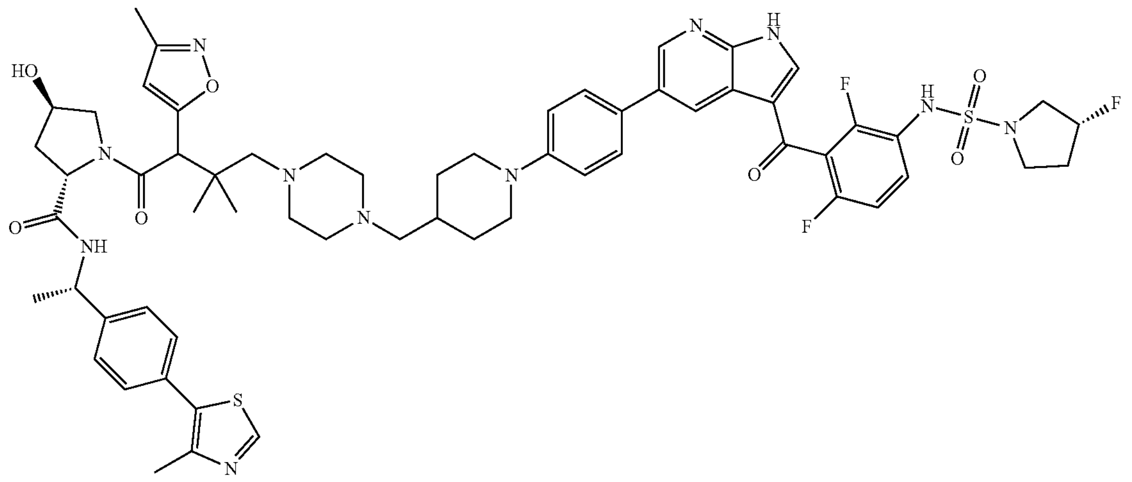
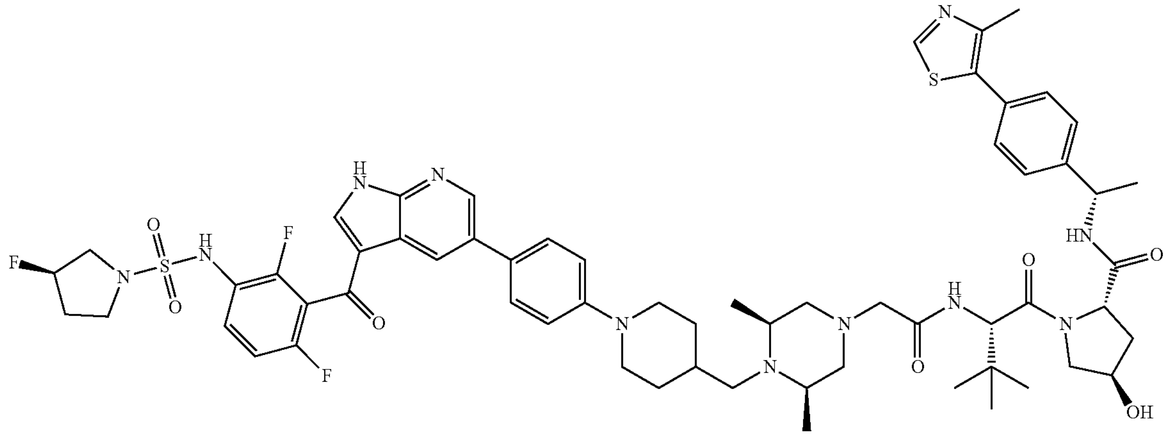
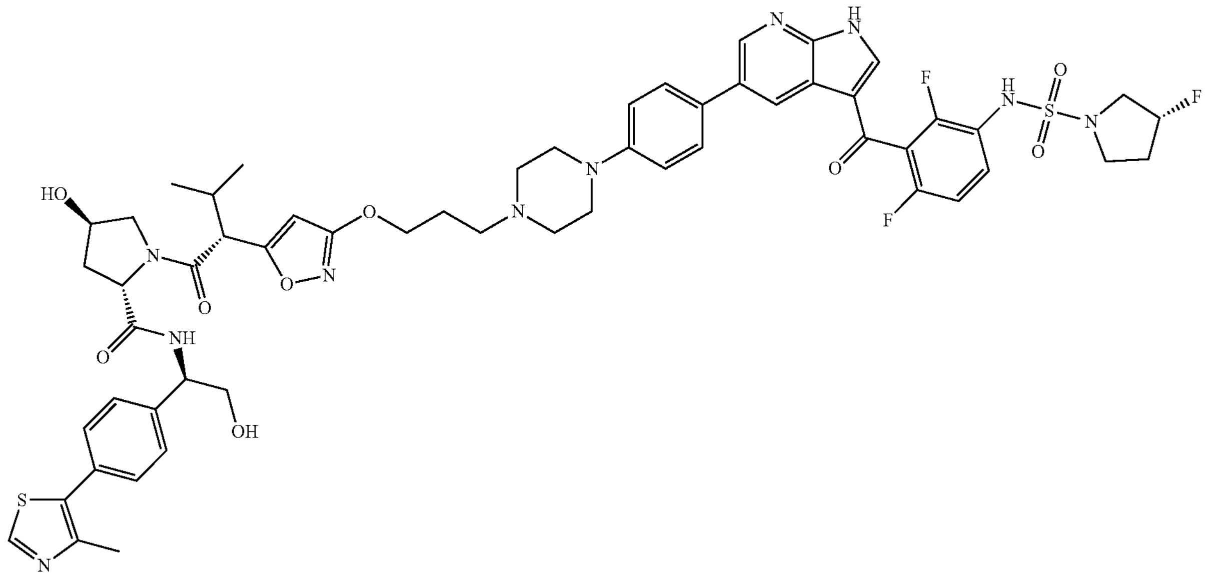

-continued
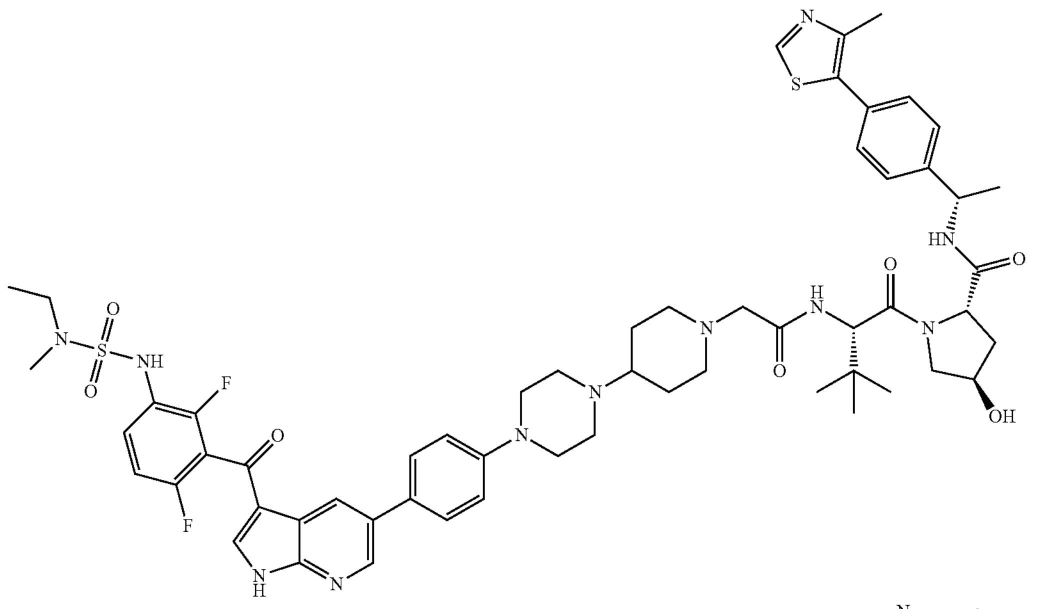
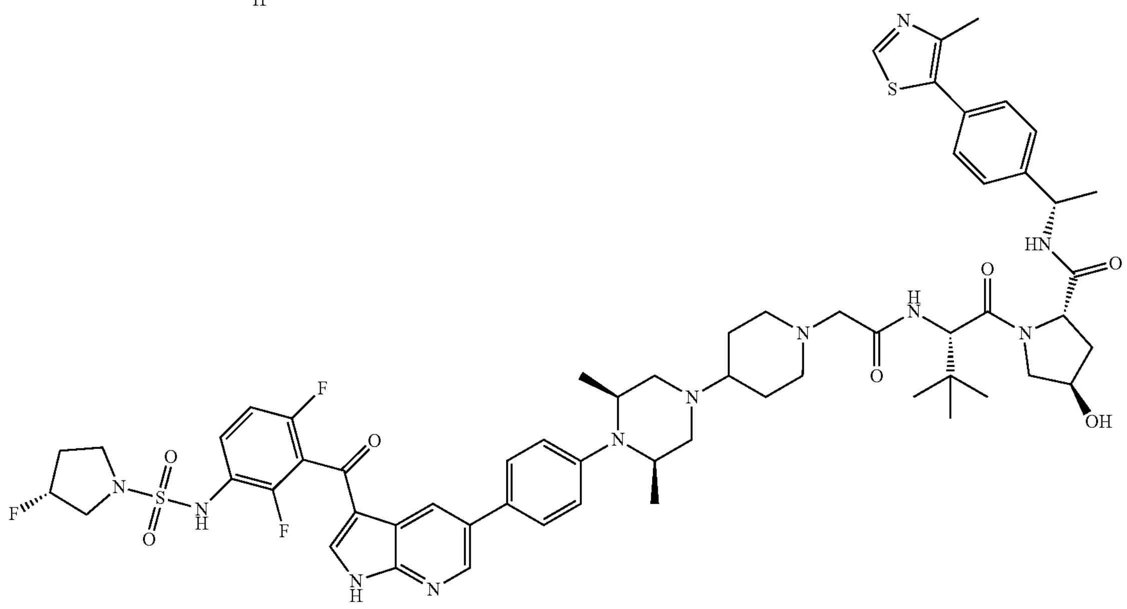
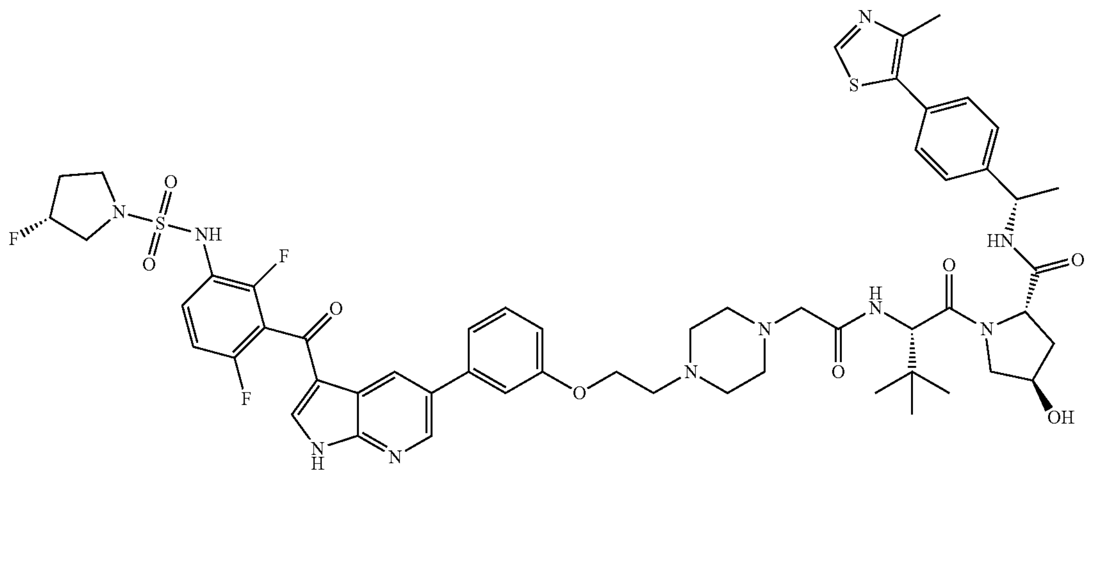

-continued
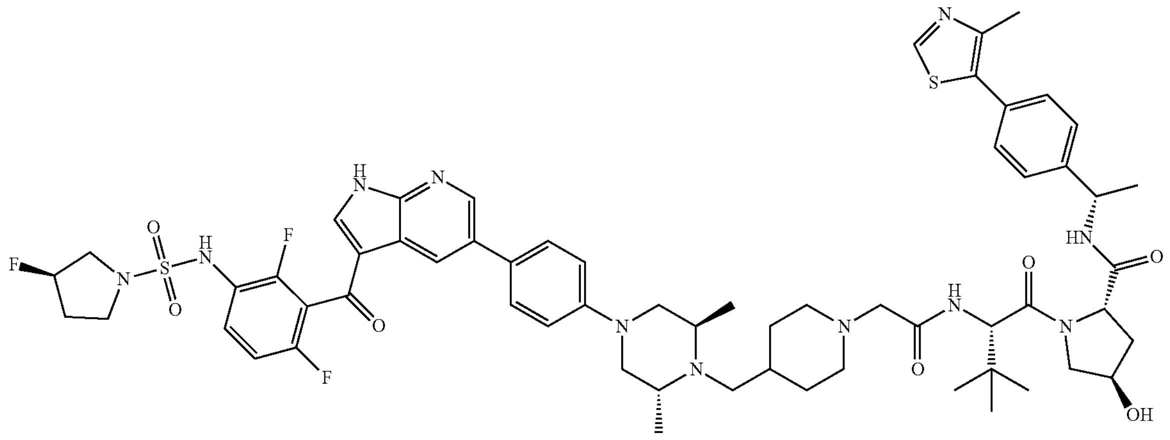
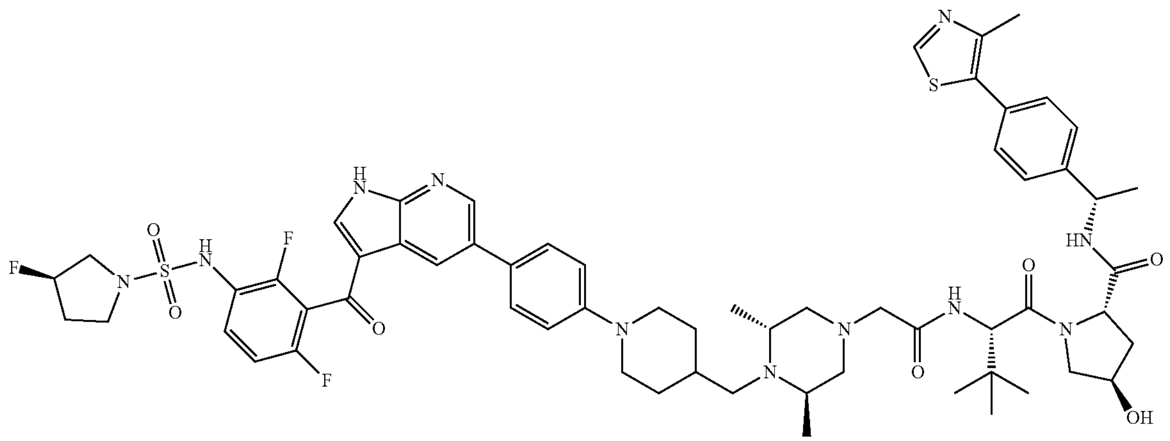
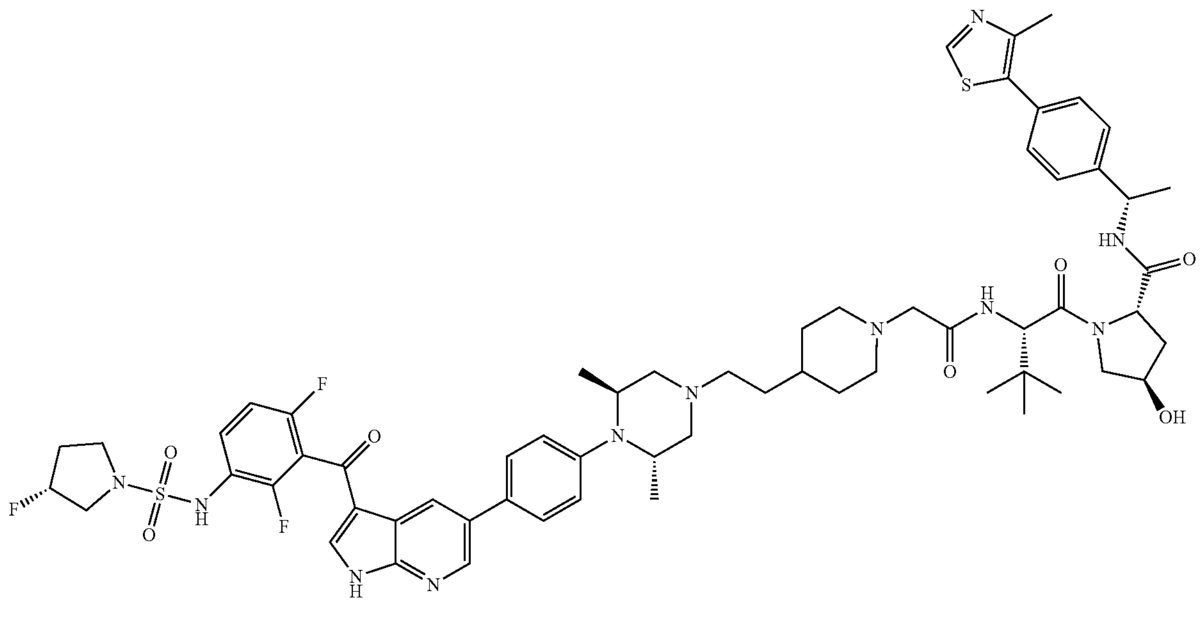

-continued
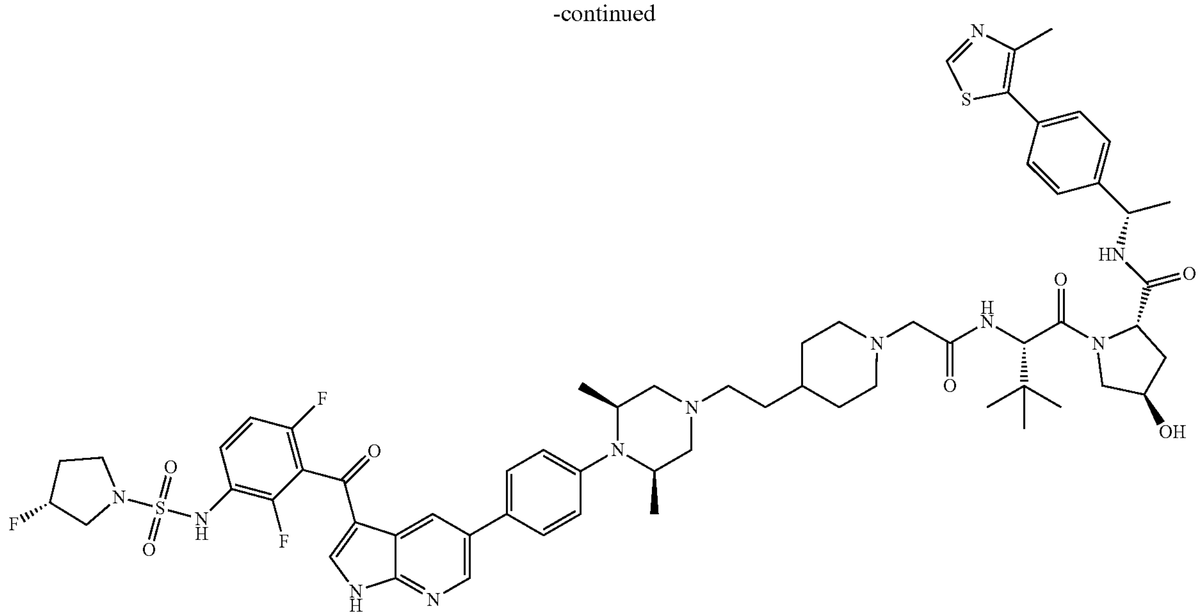
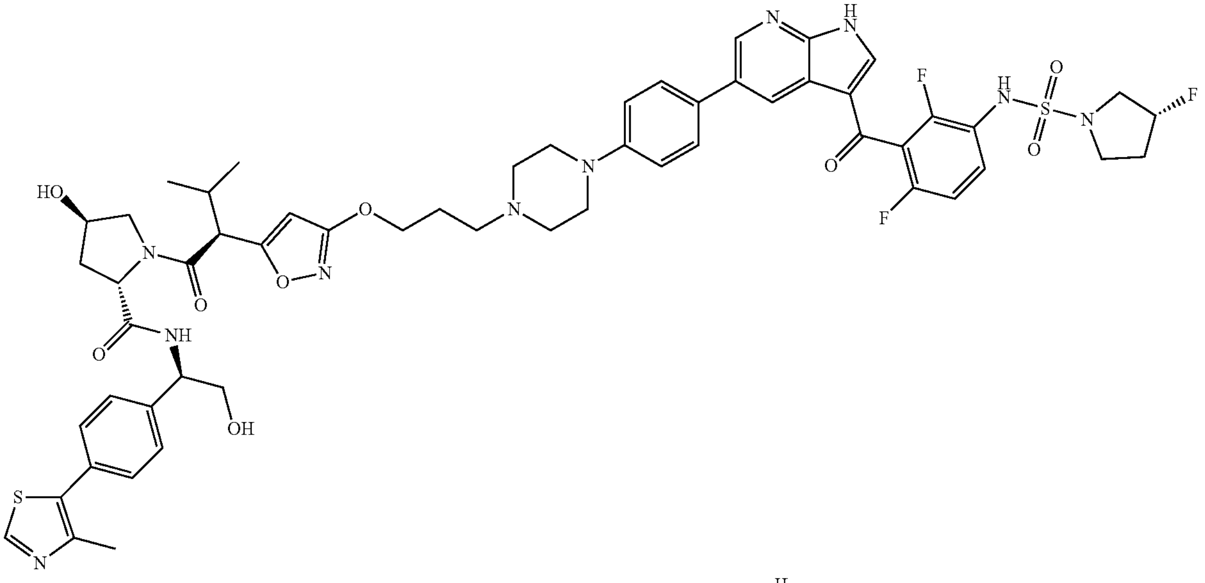
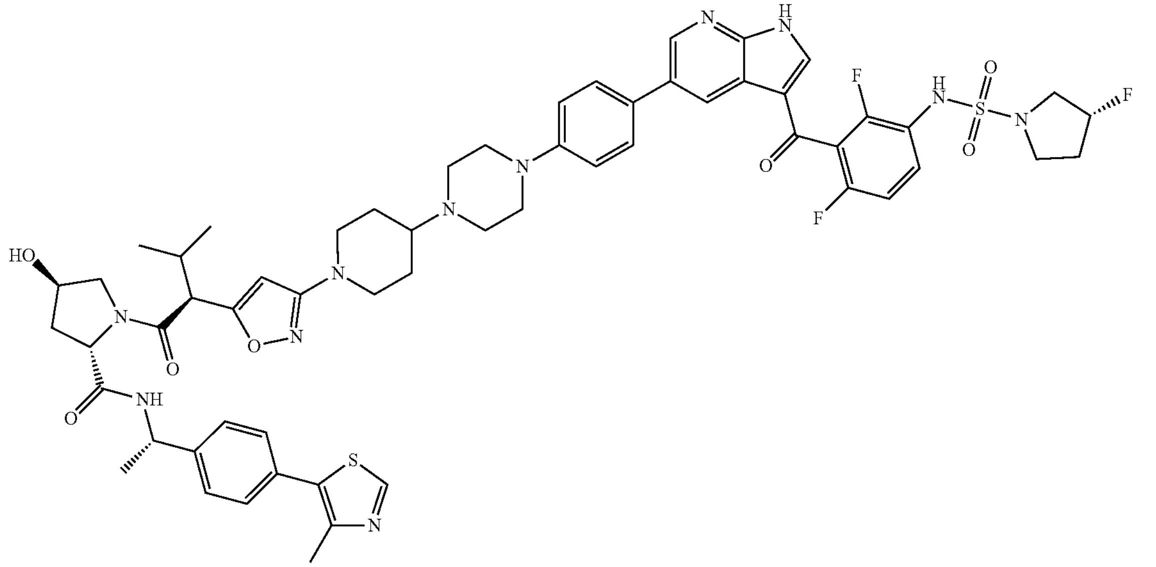

-continued
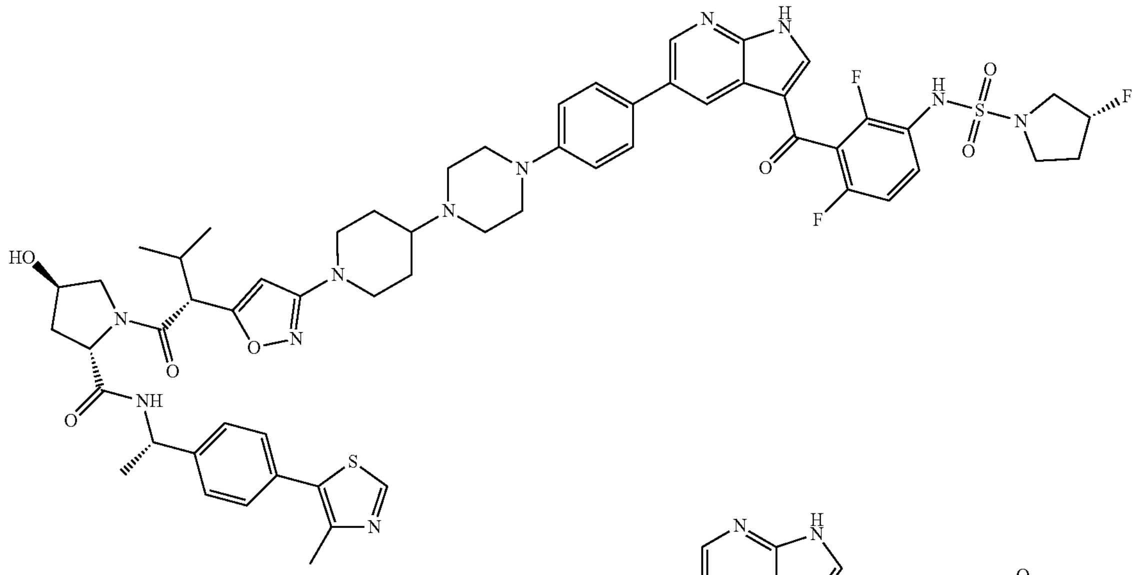
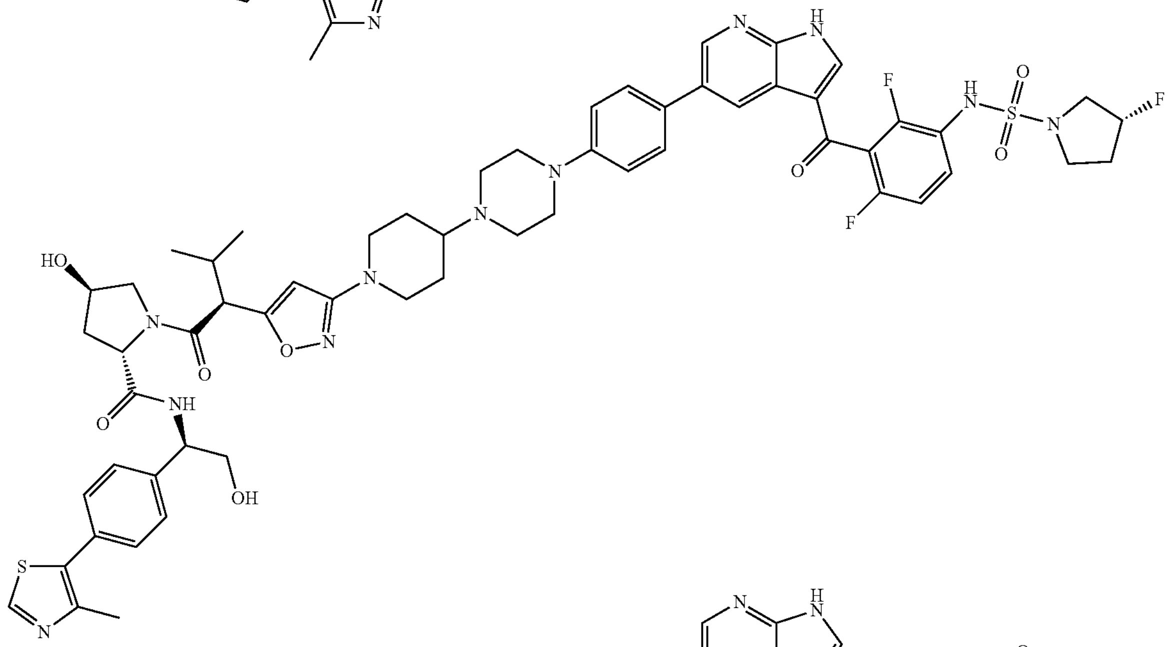
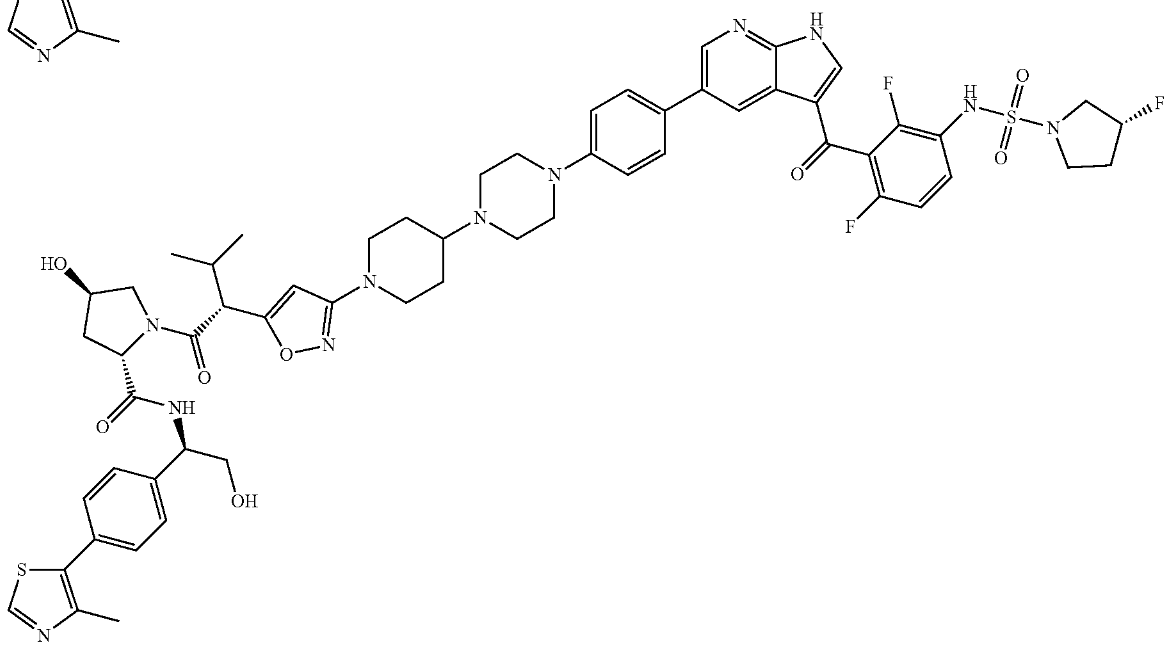

-continued
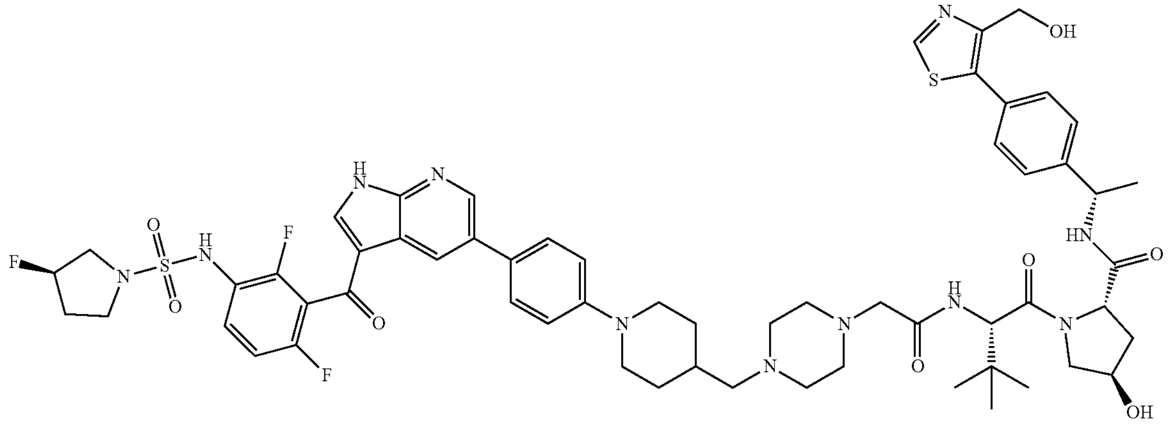
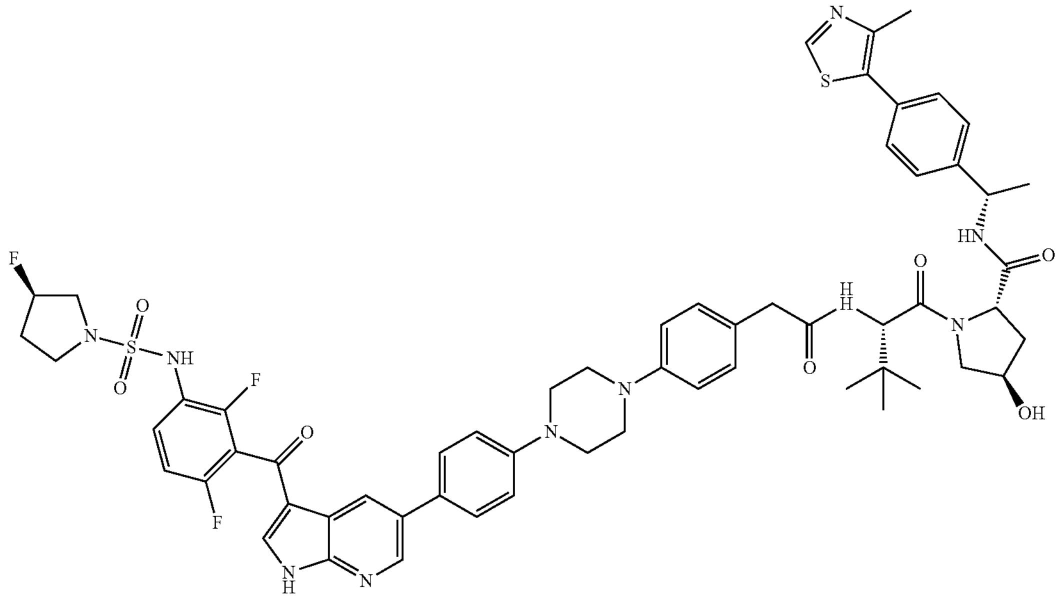
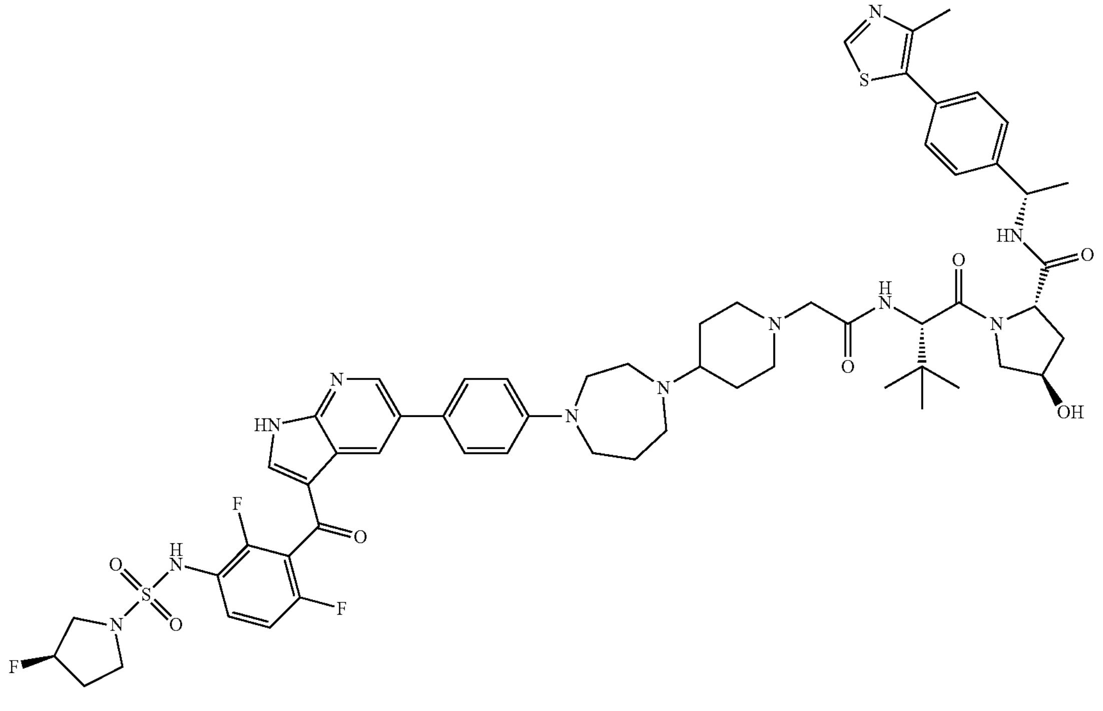

-continued
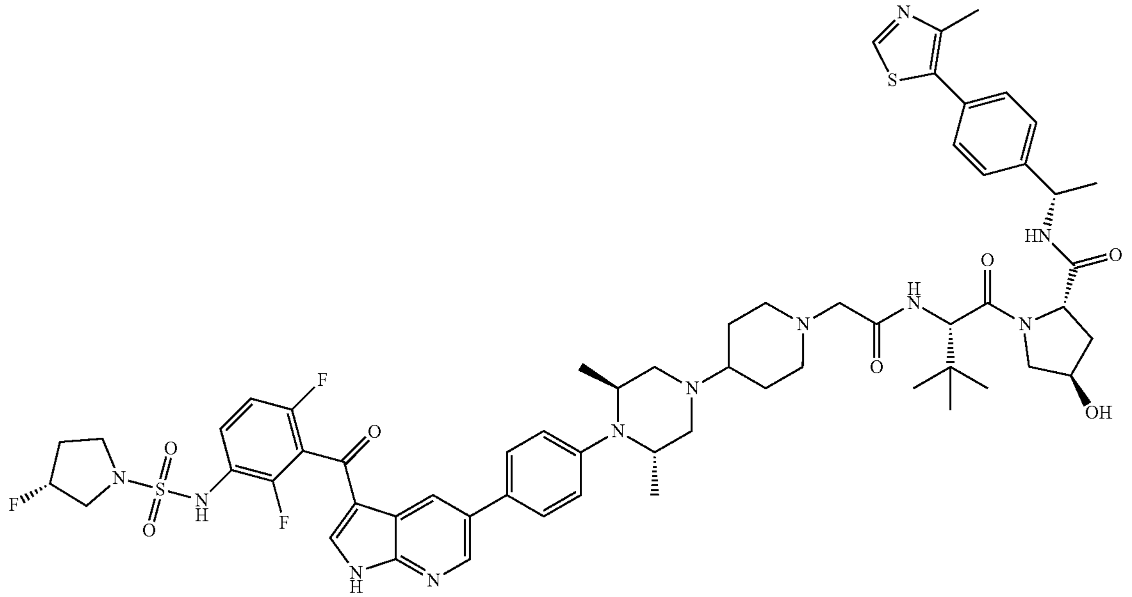
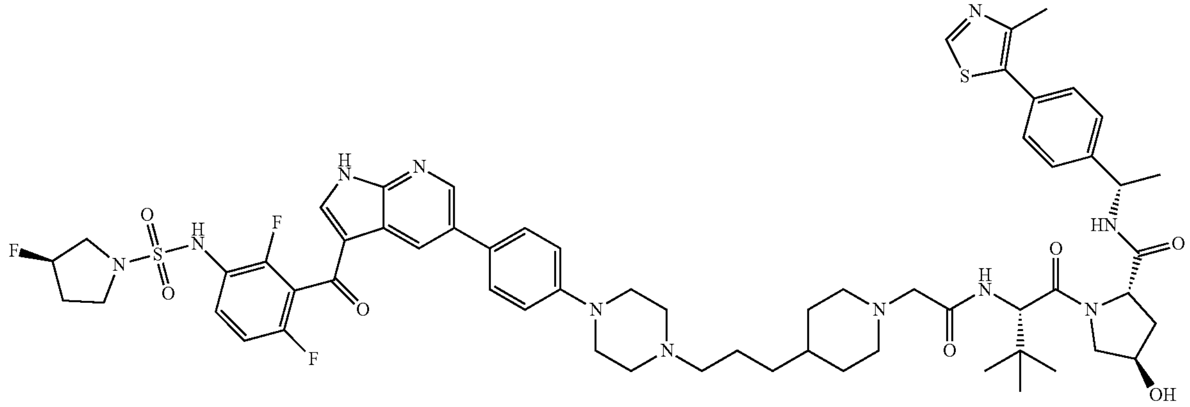
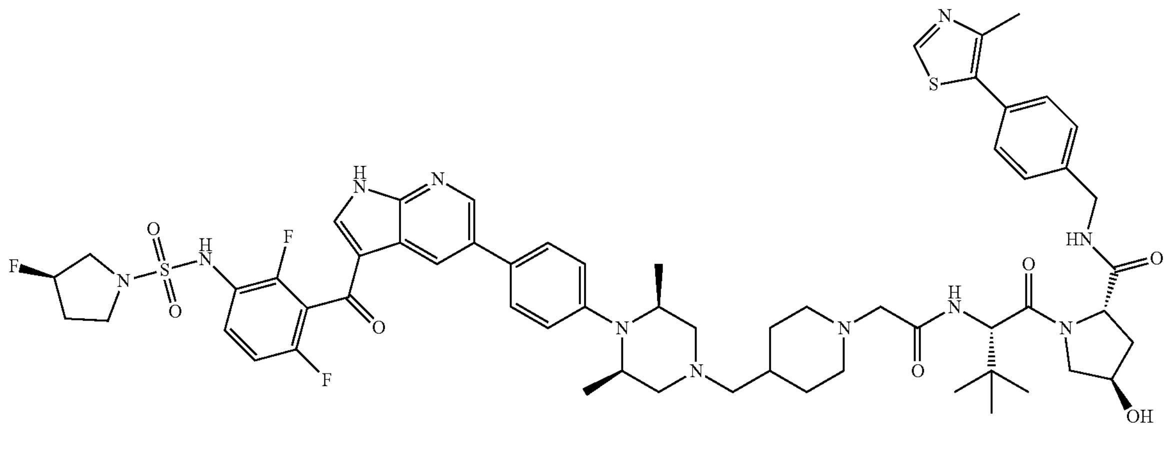

-continued
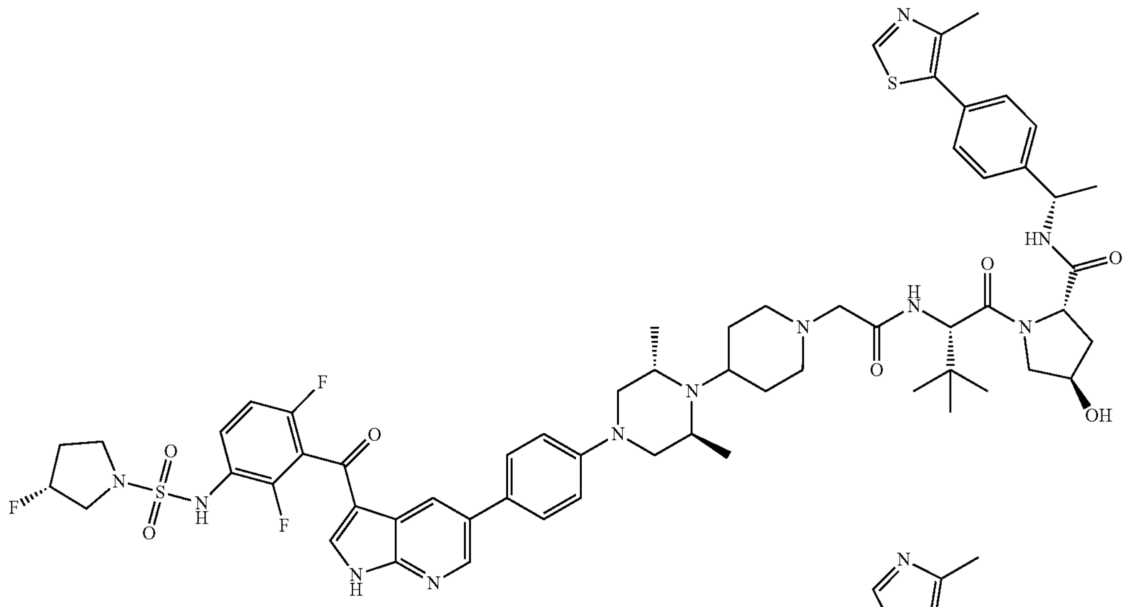
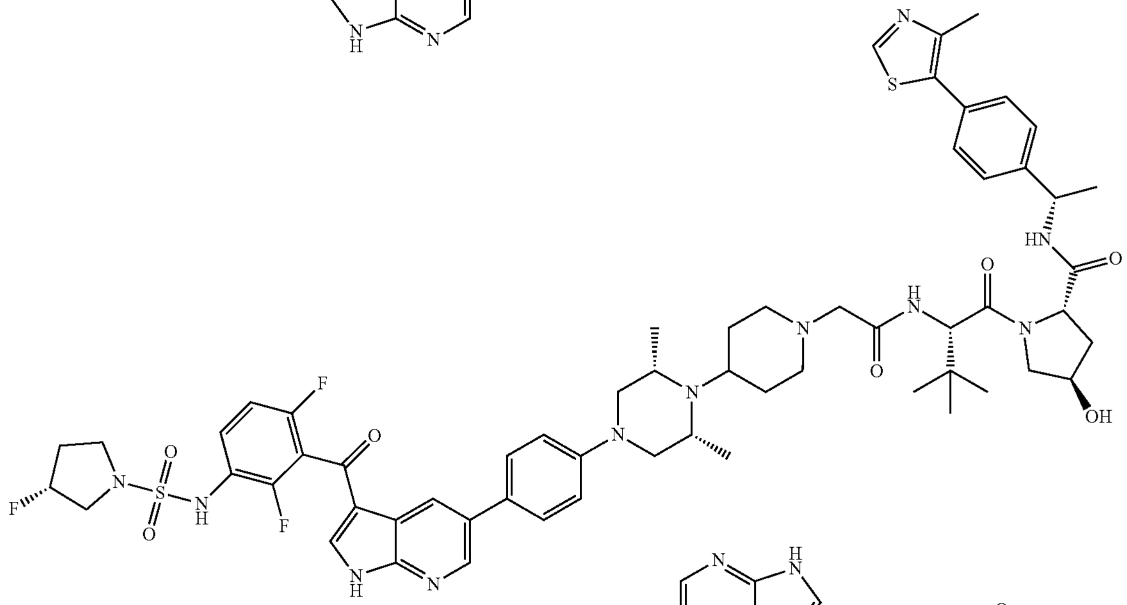
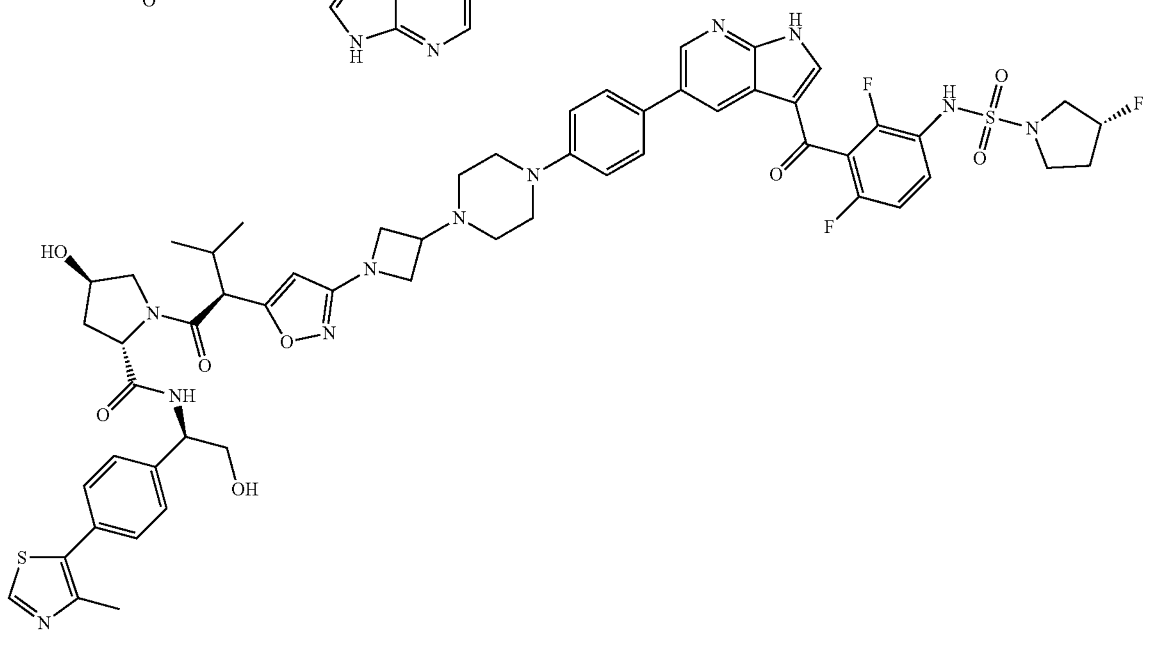

-continued
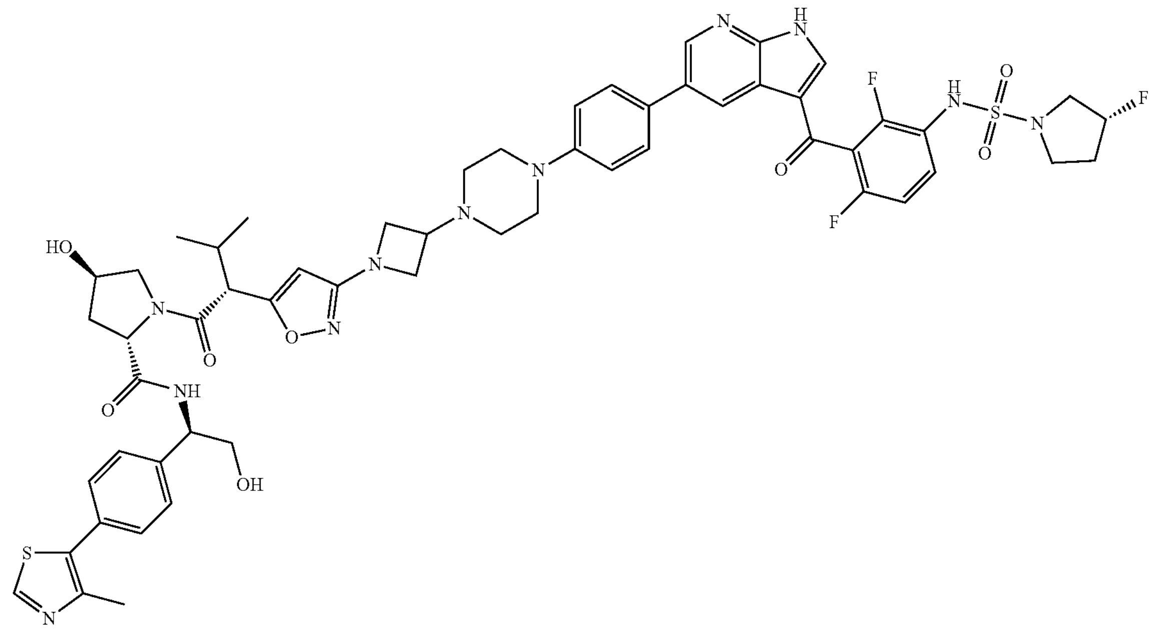
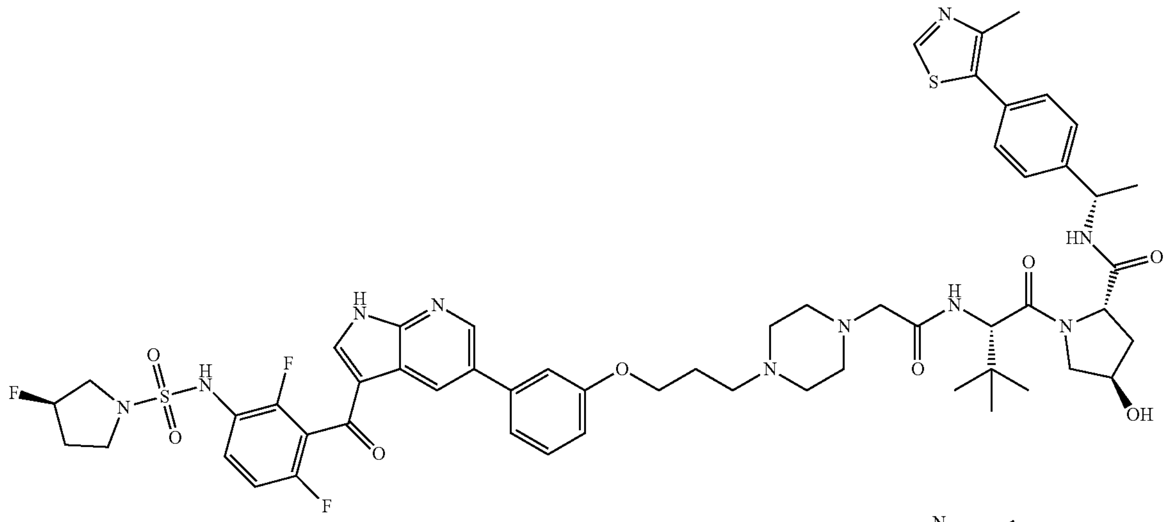
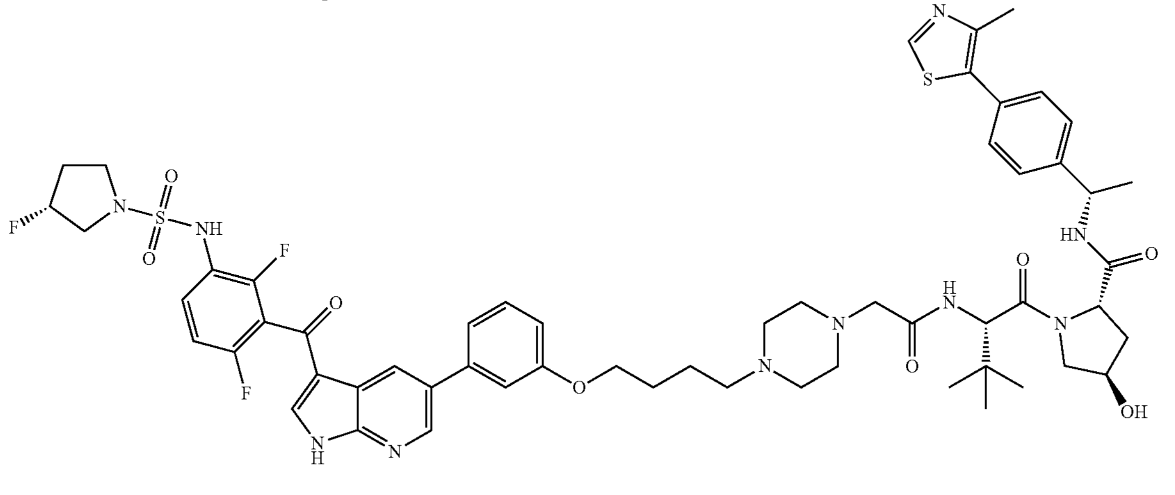

-continued
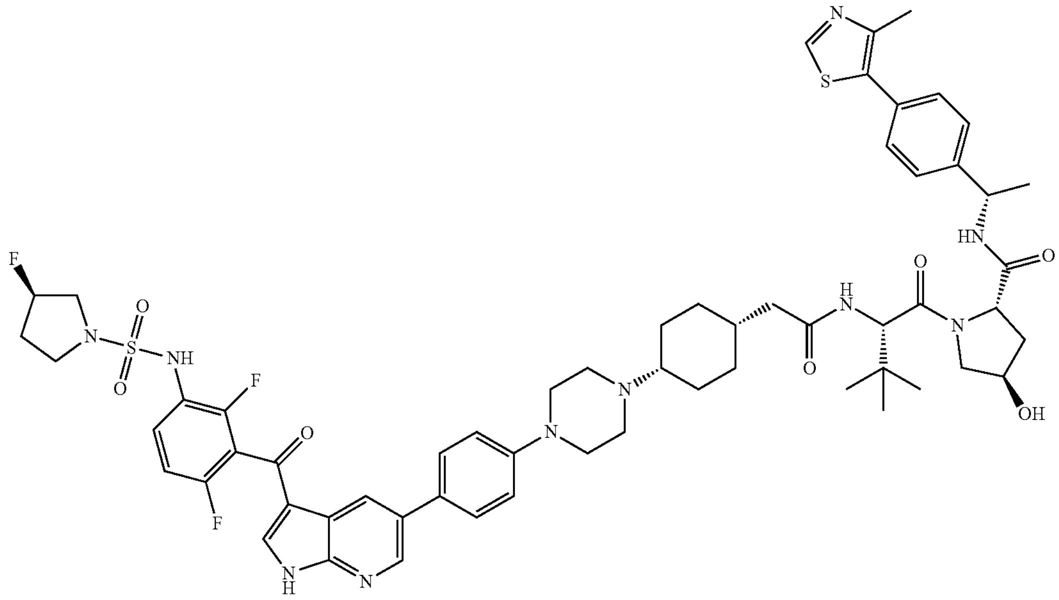
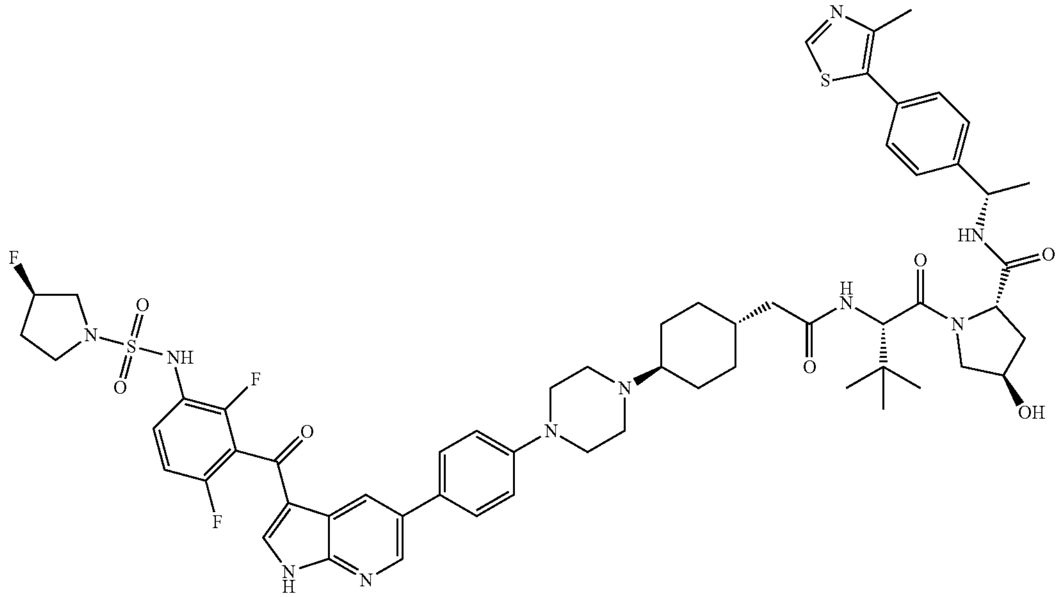
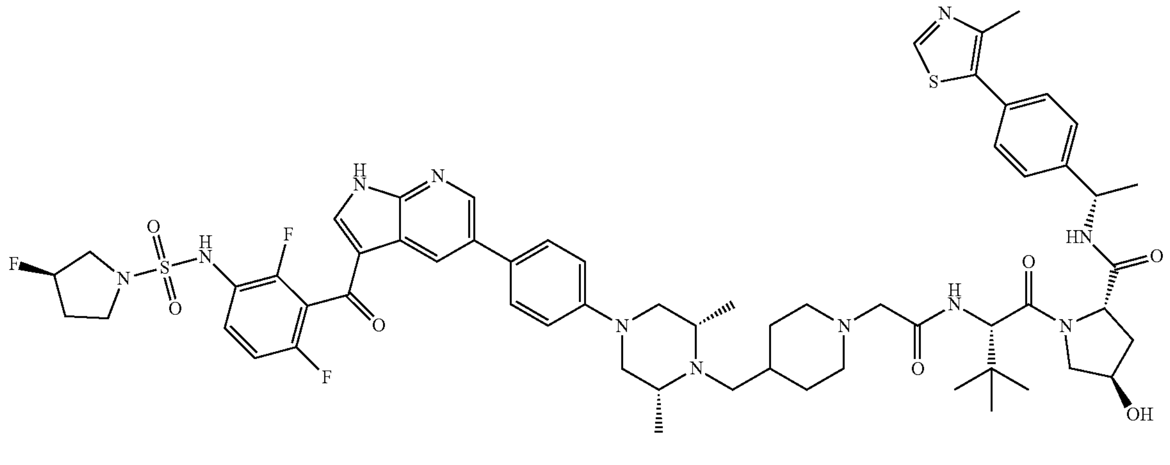

-continued
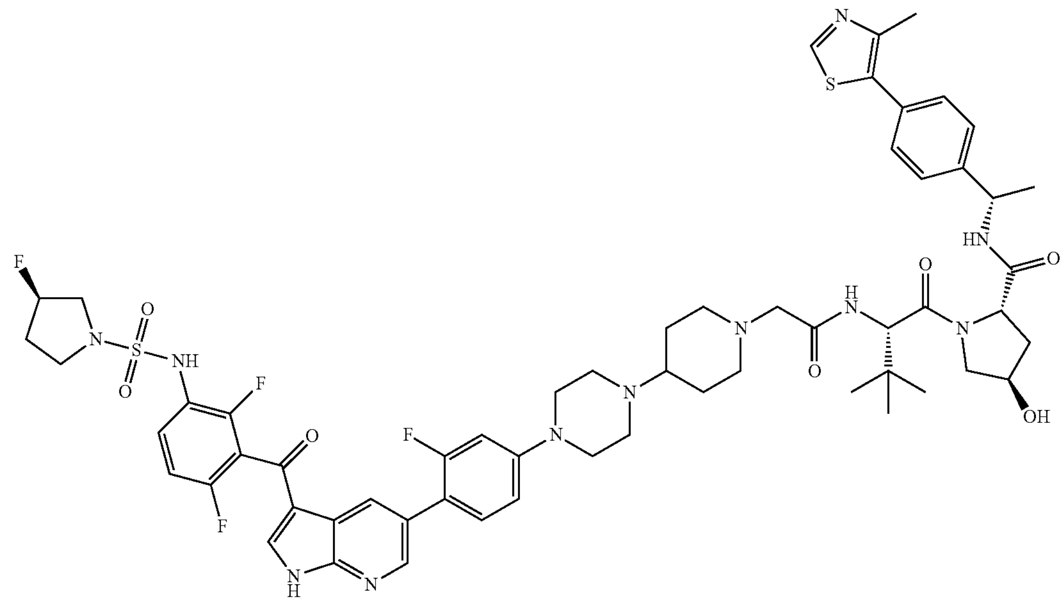
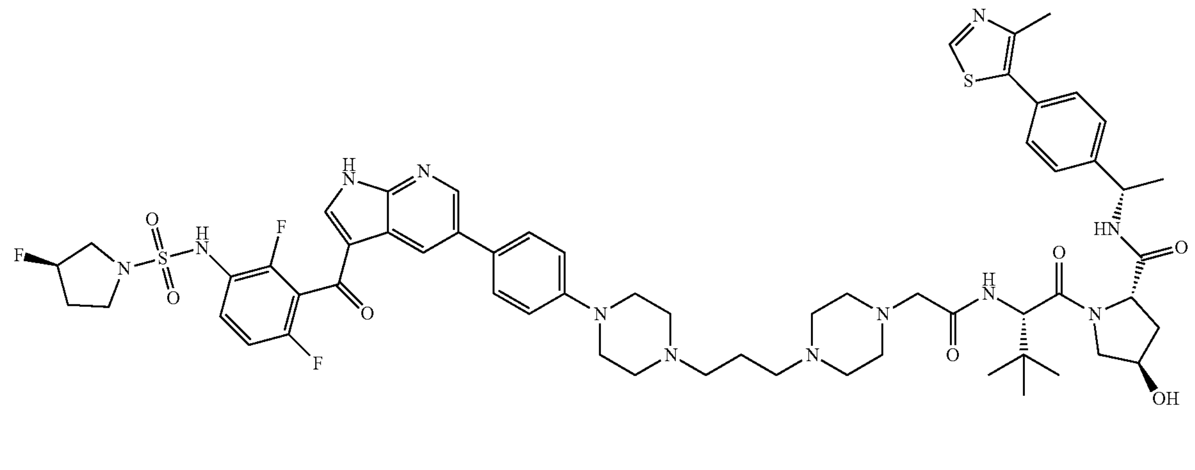
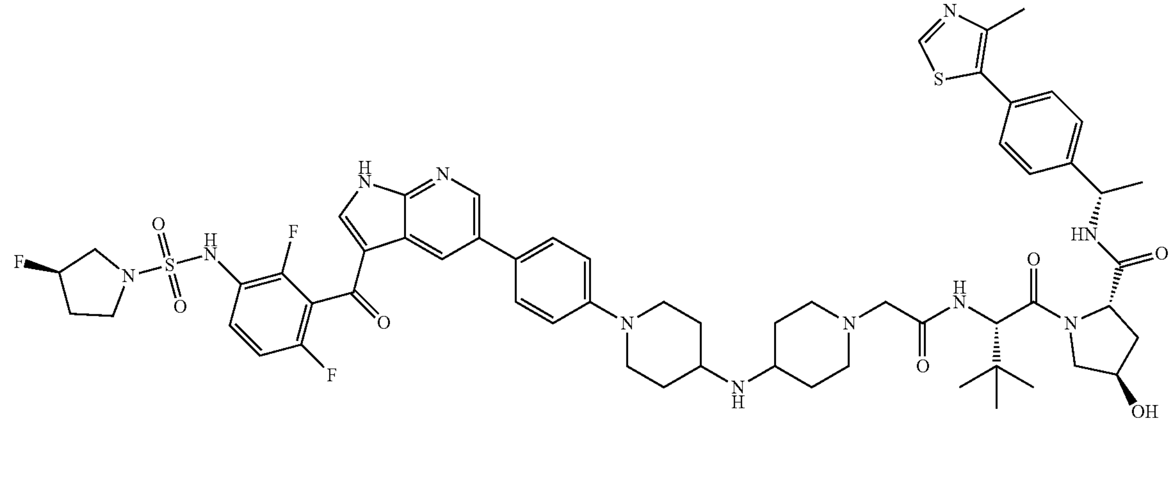

-continued
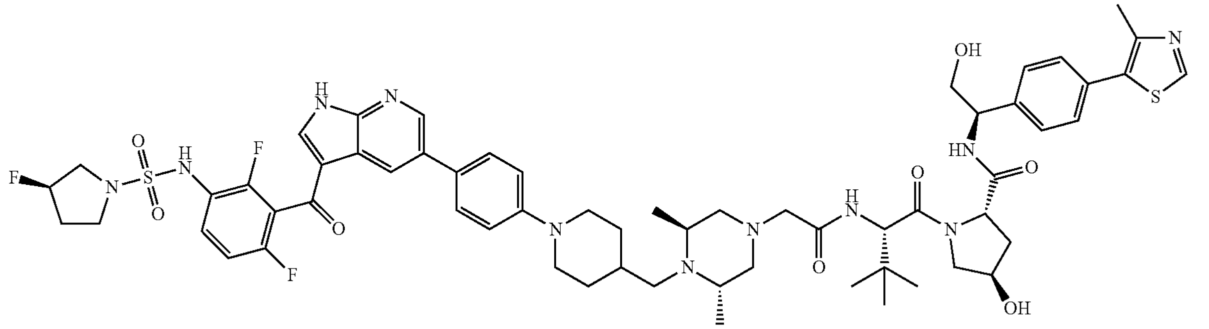
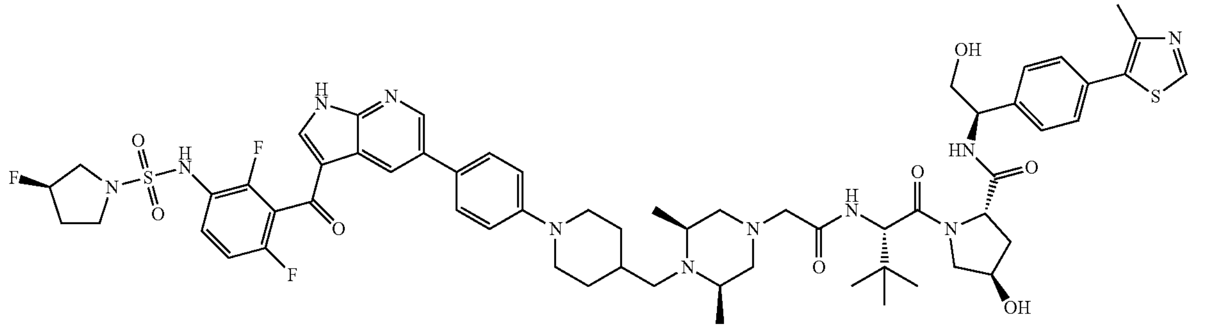
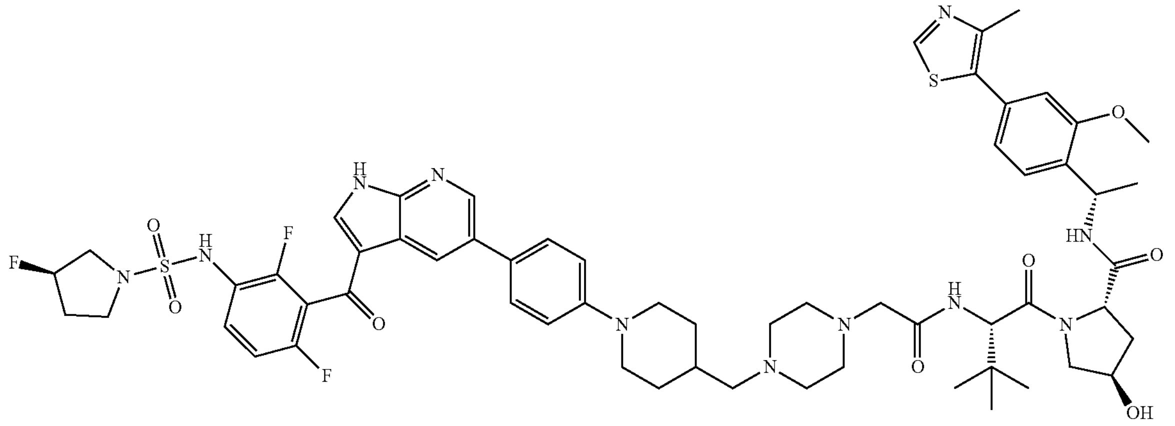
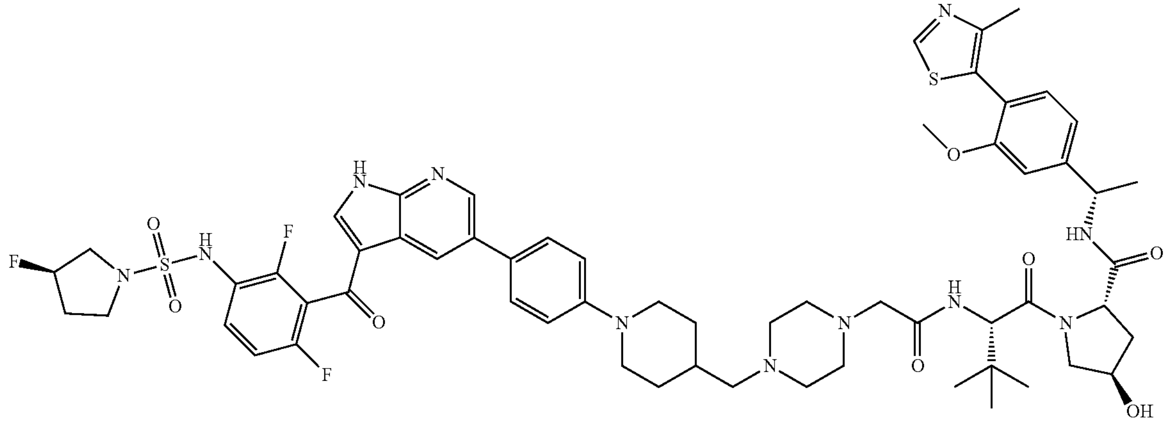

-continued
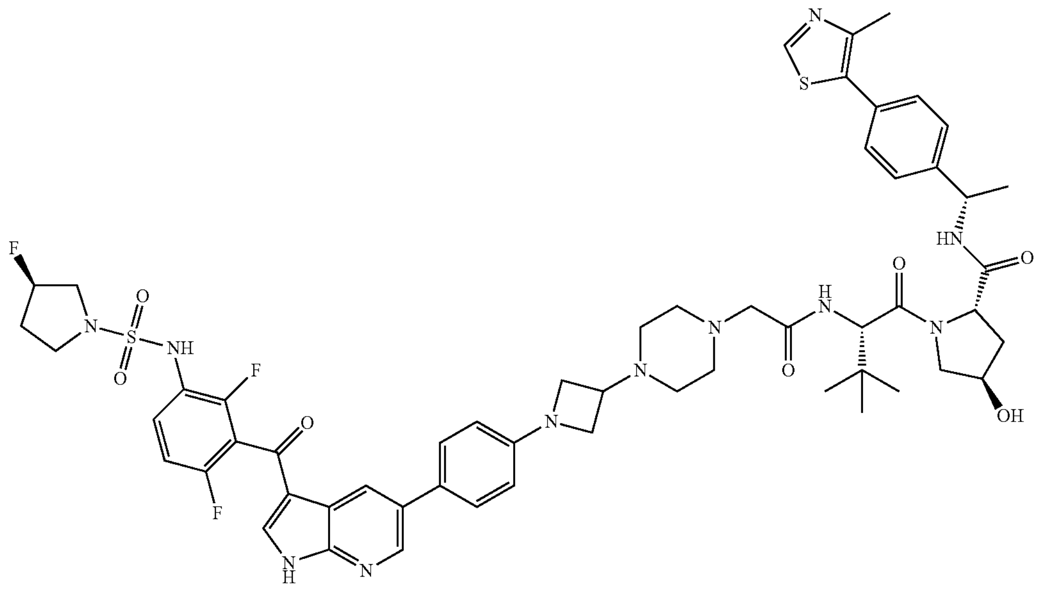
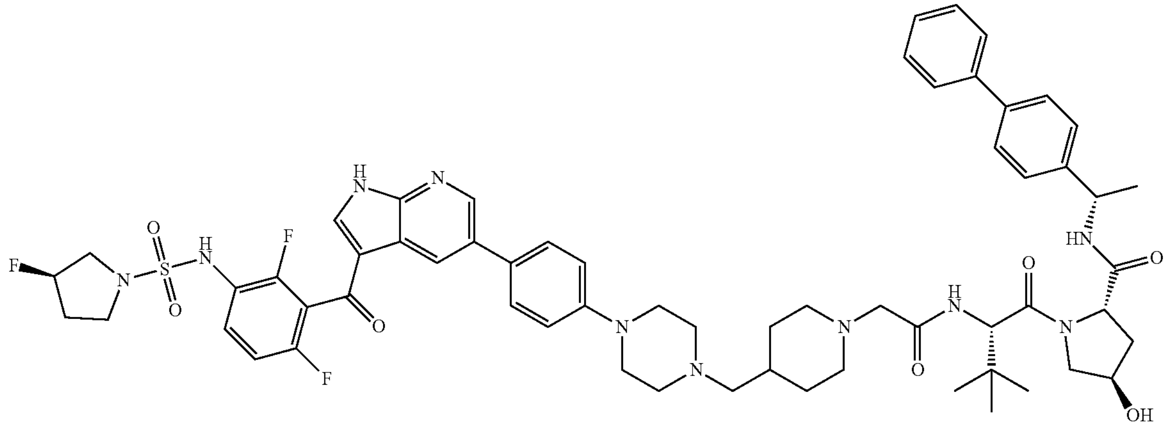
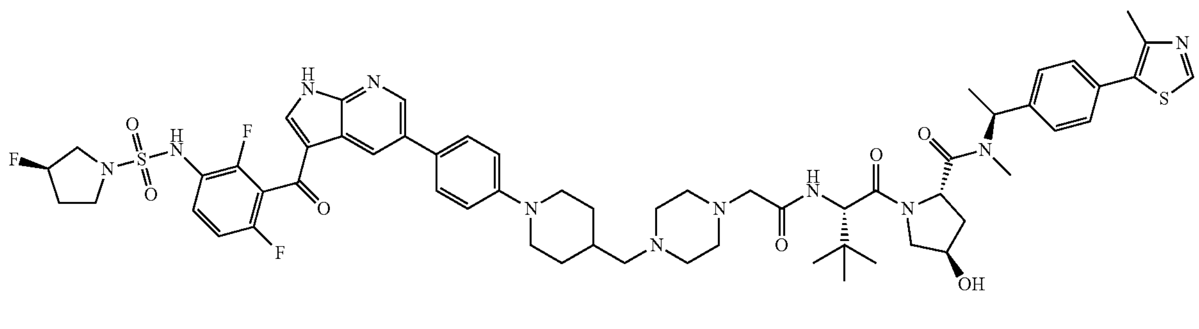

-continued
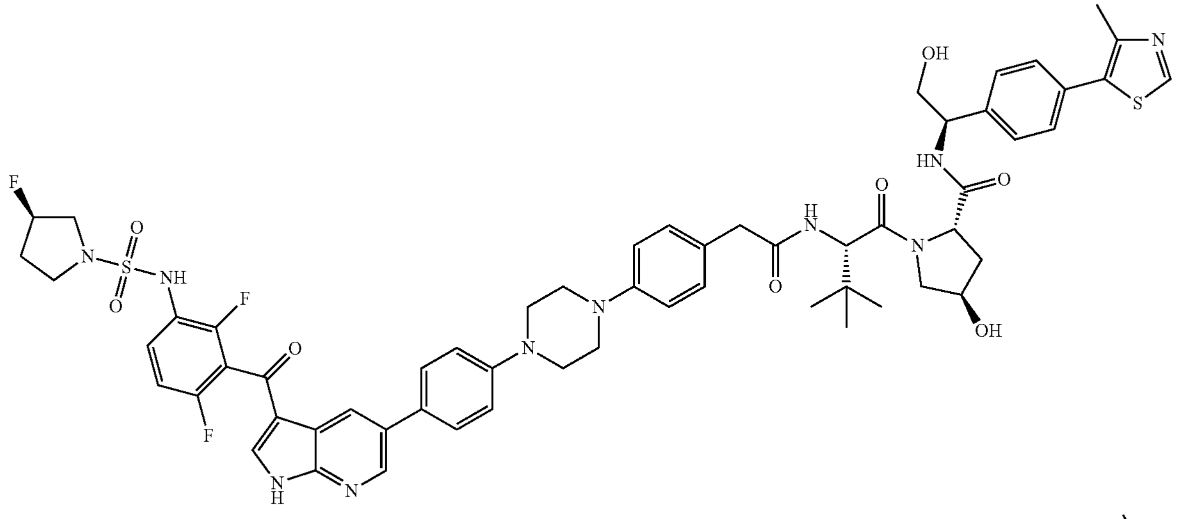
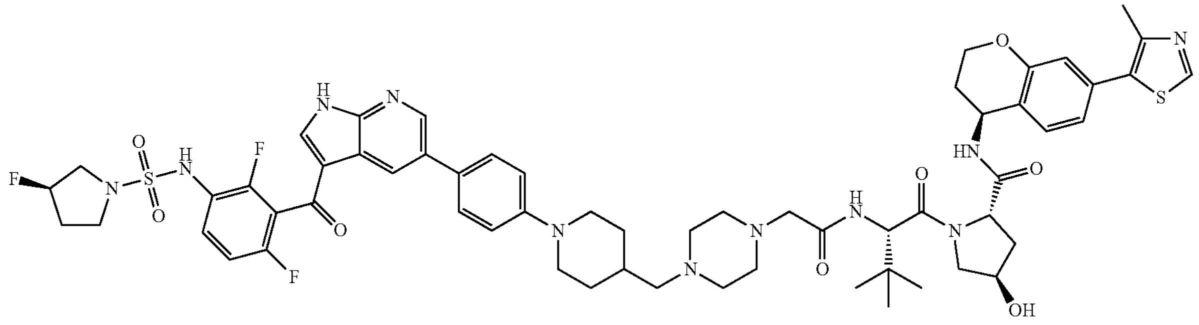
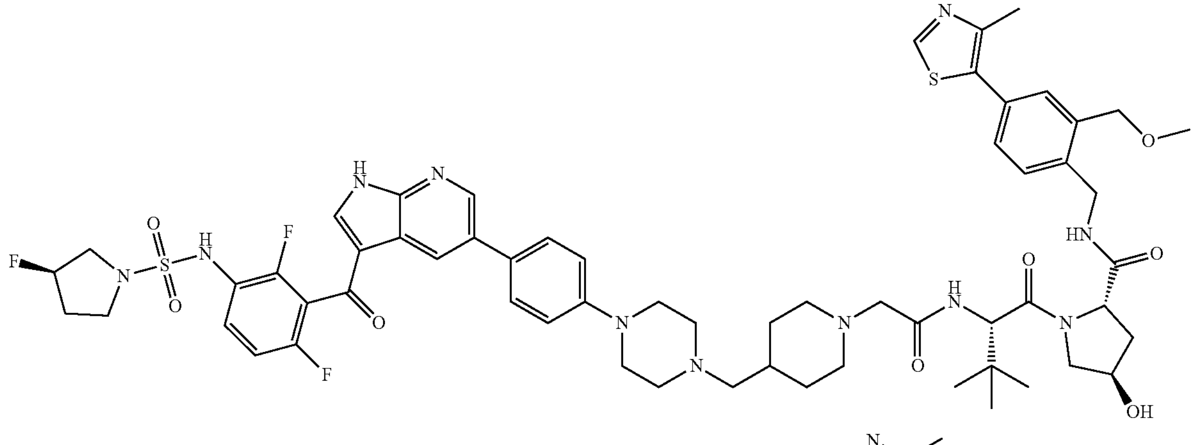
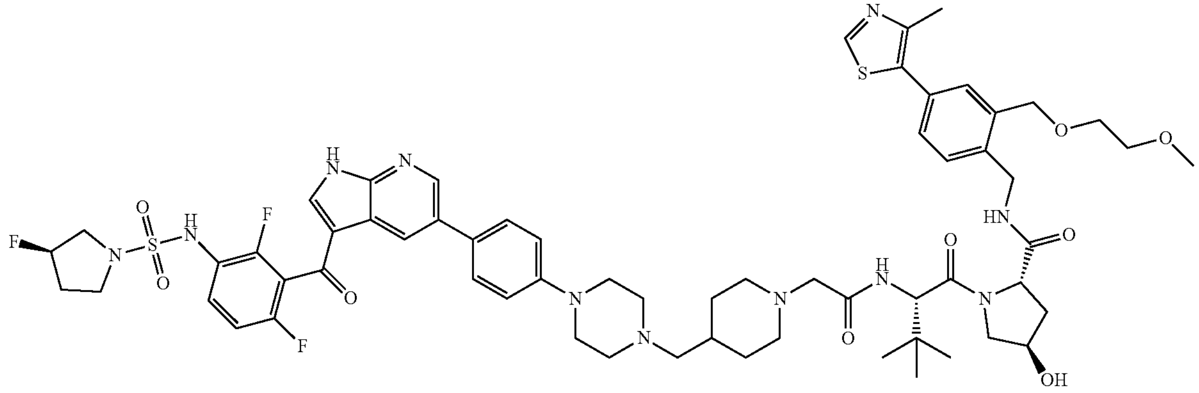

-continued
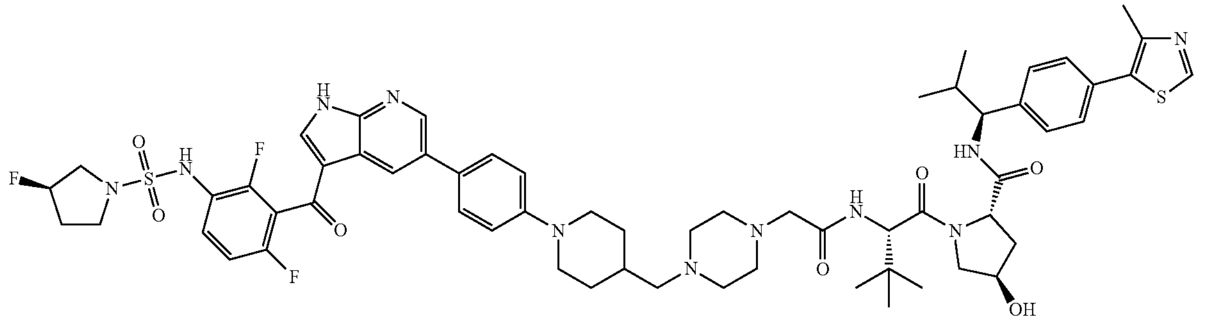
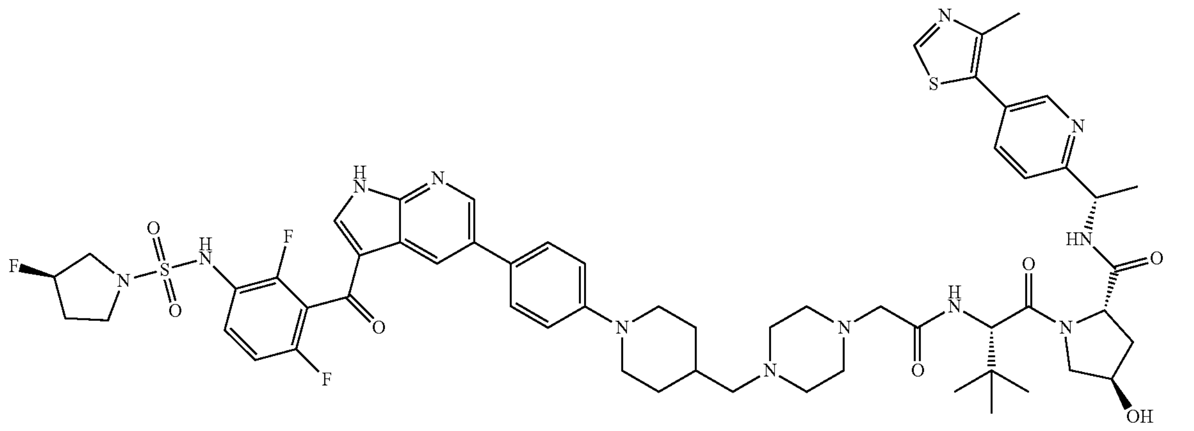
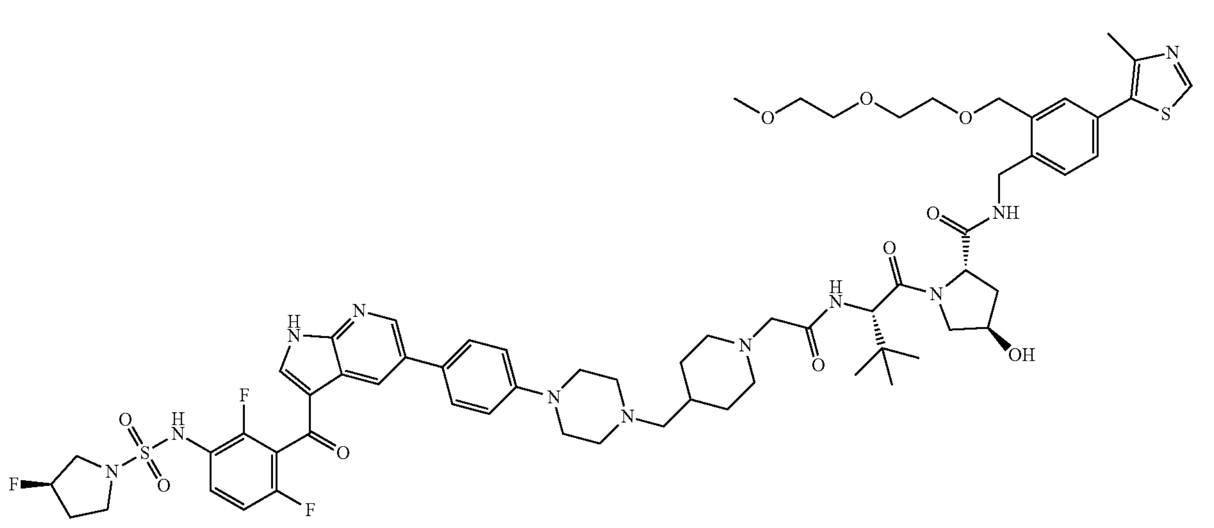

-continued
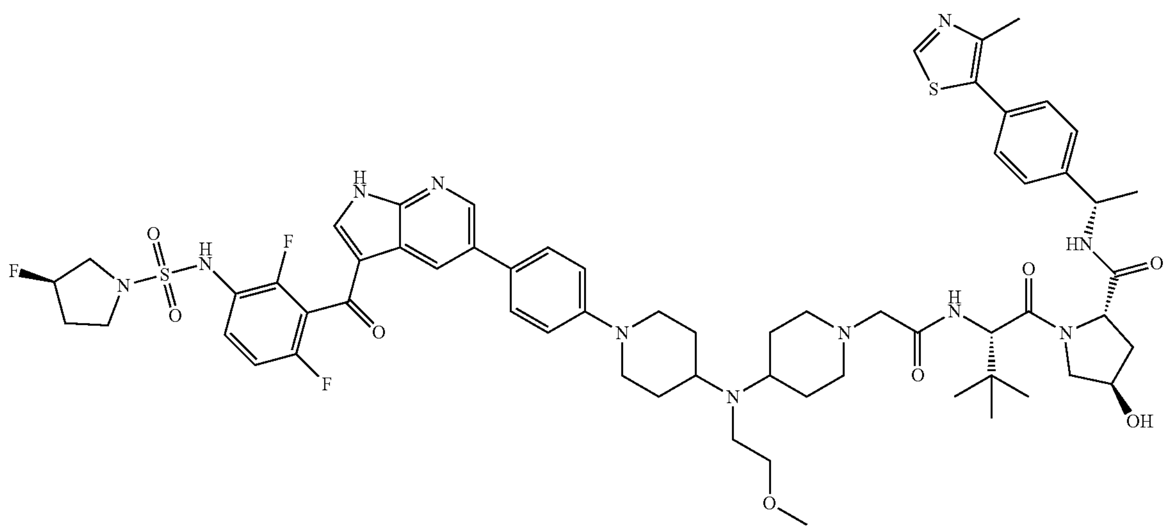
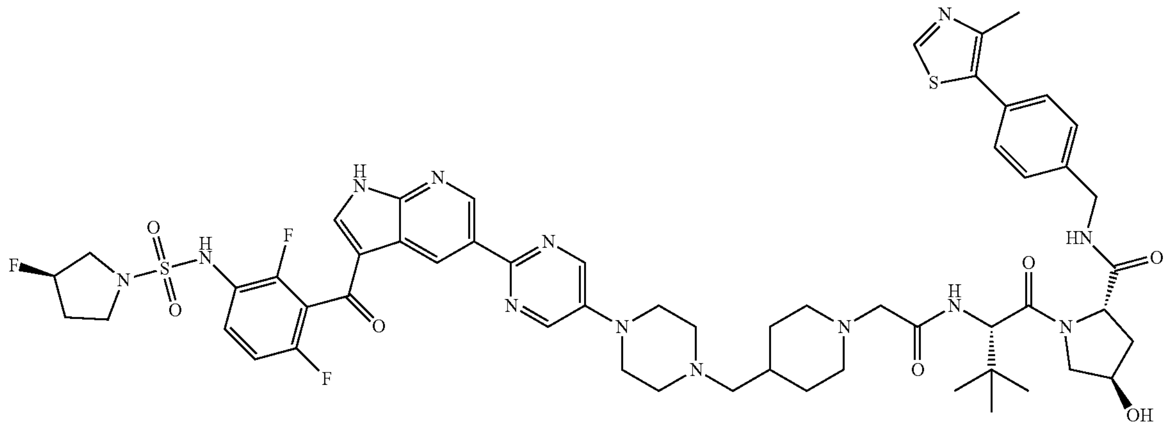
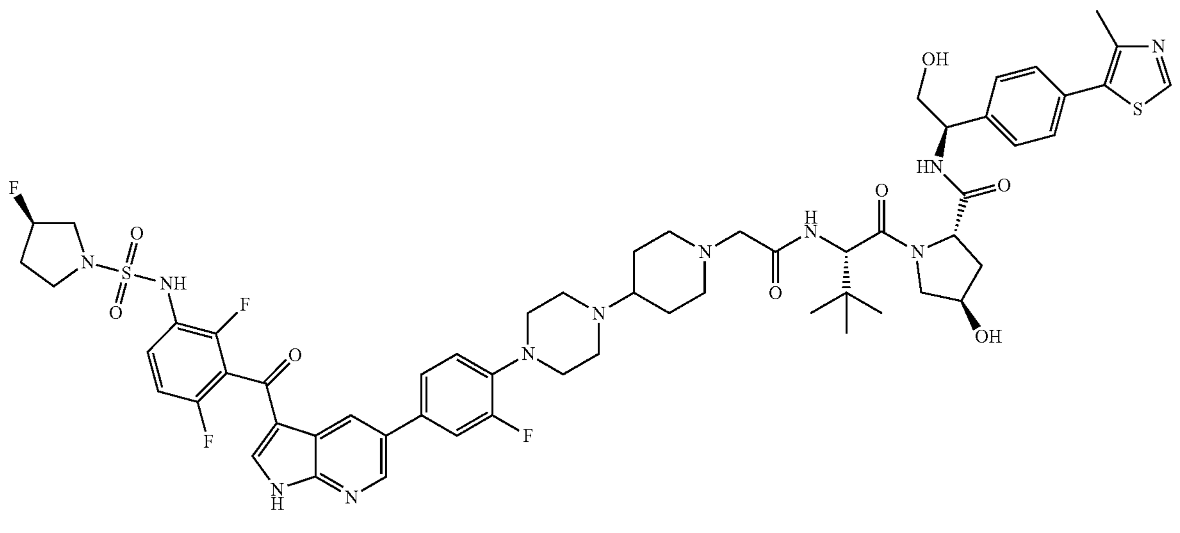

-continued
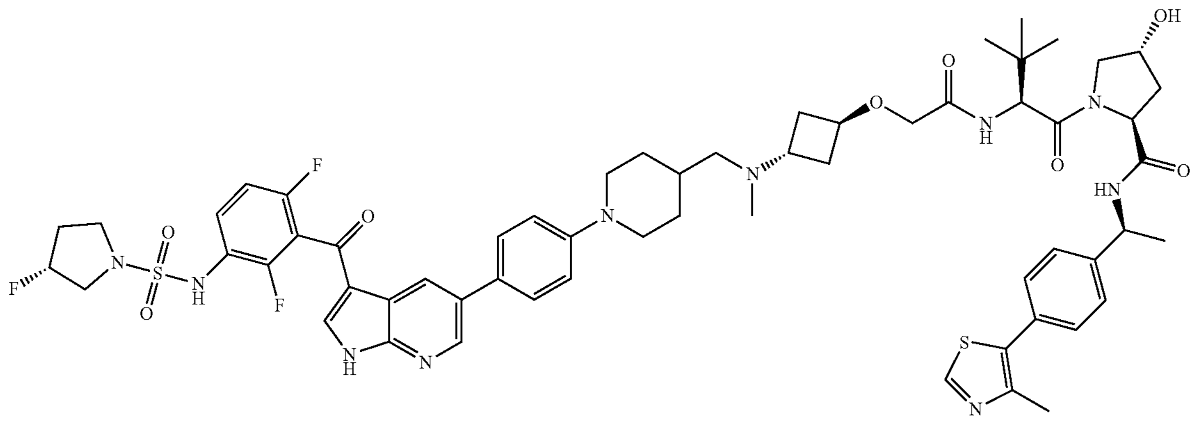
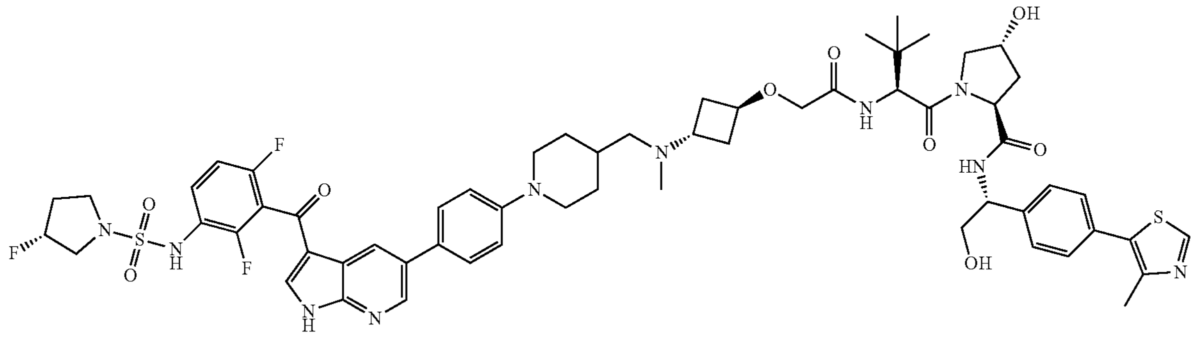
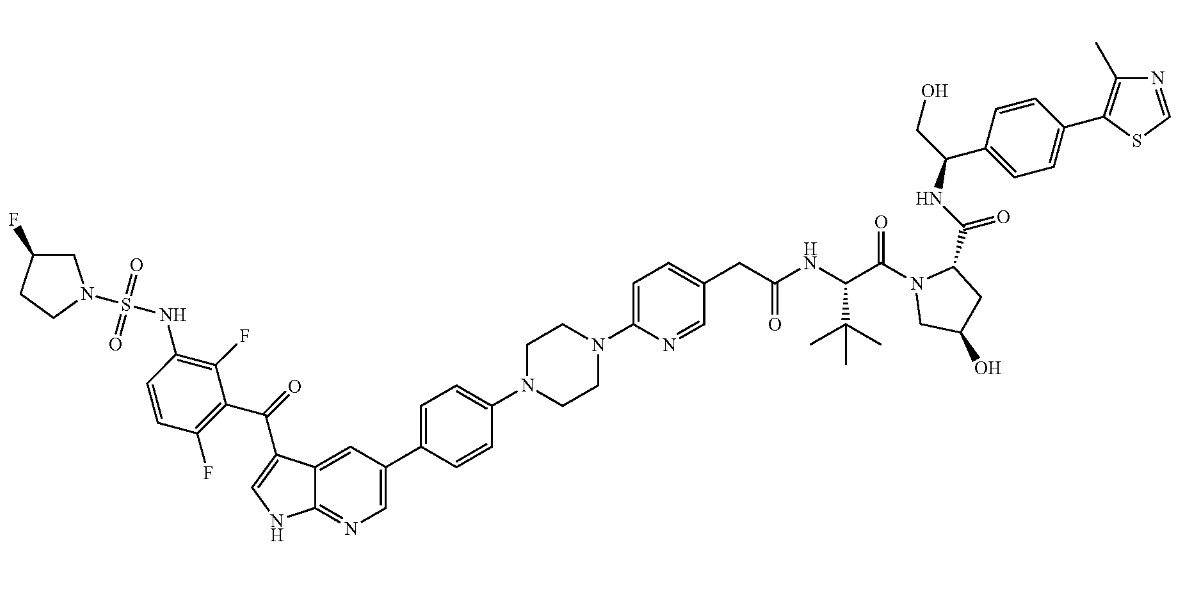

-continued
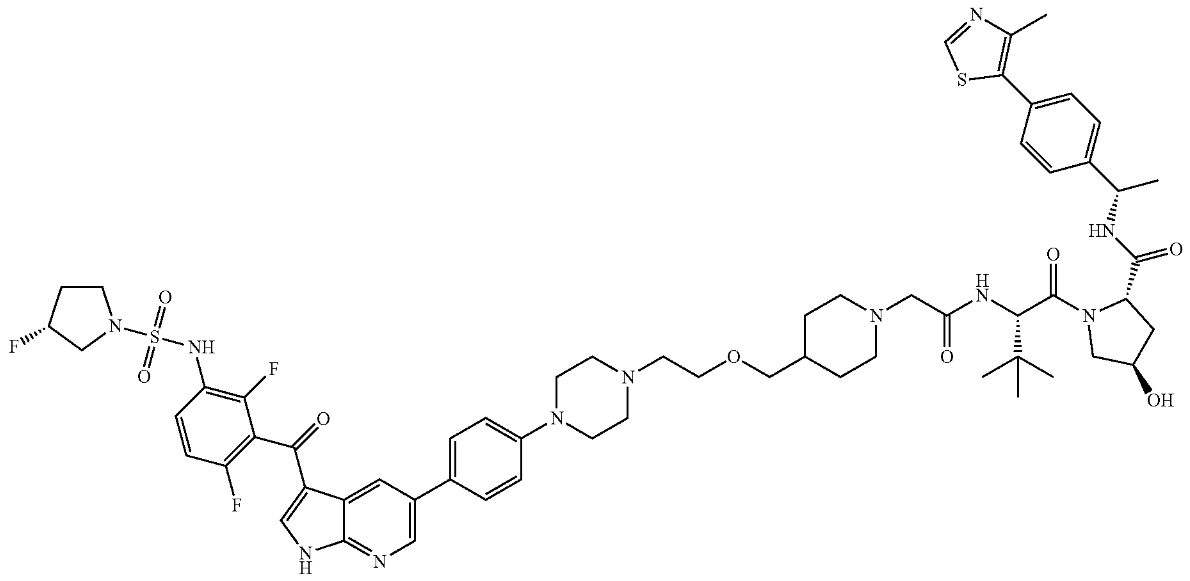
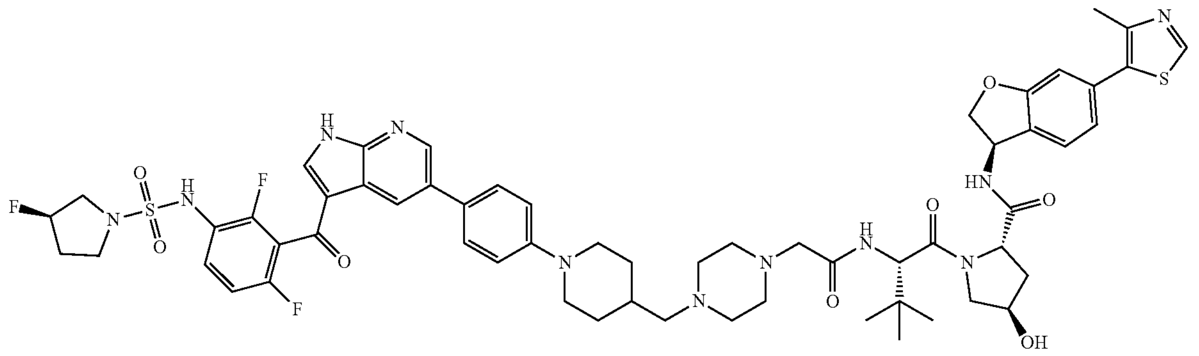
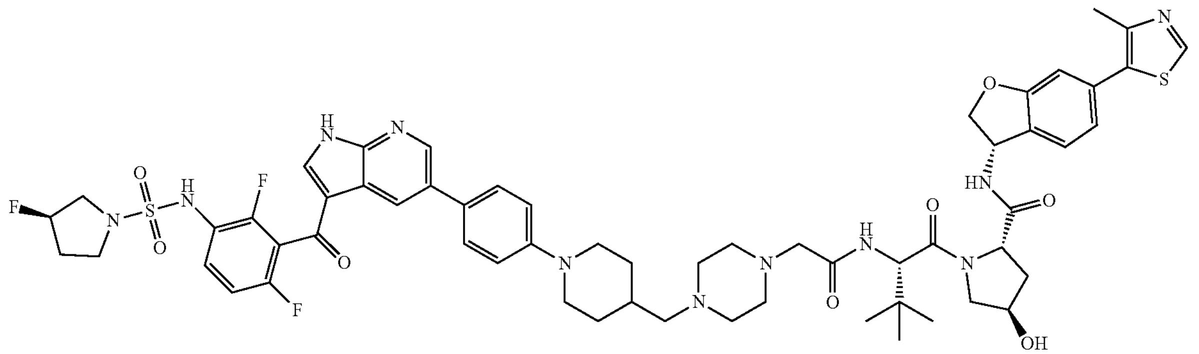
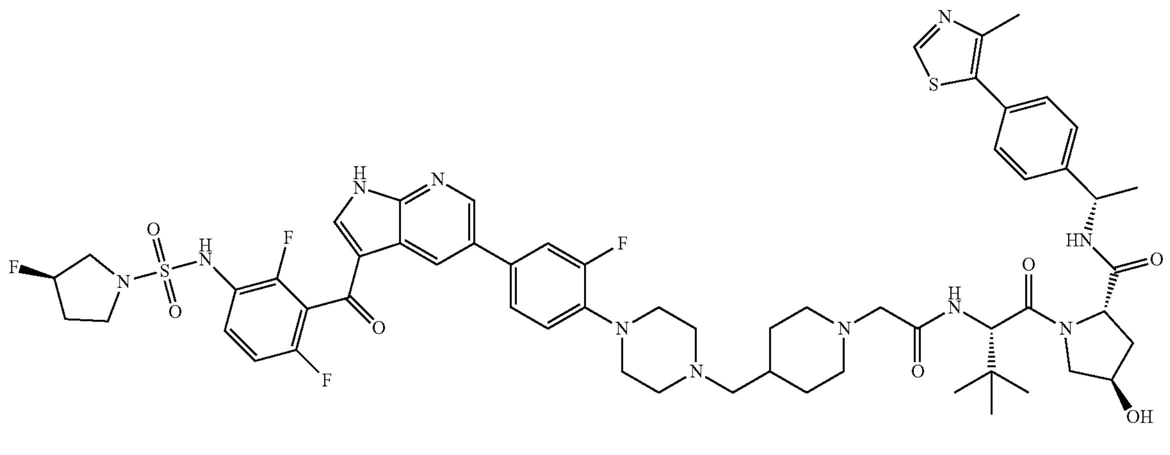

-continued
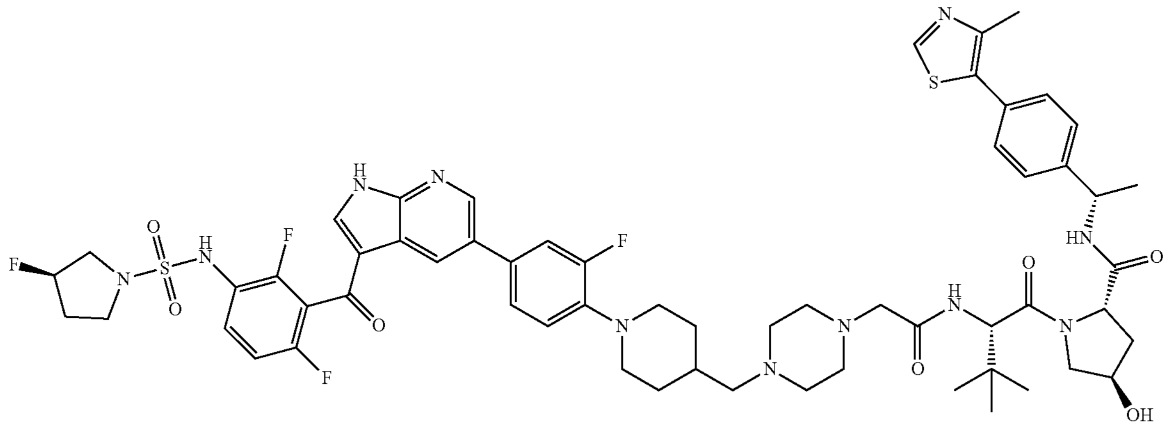
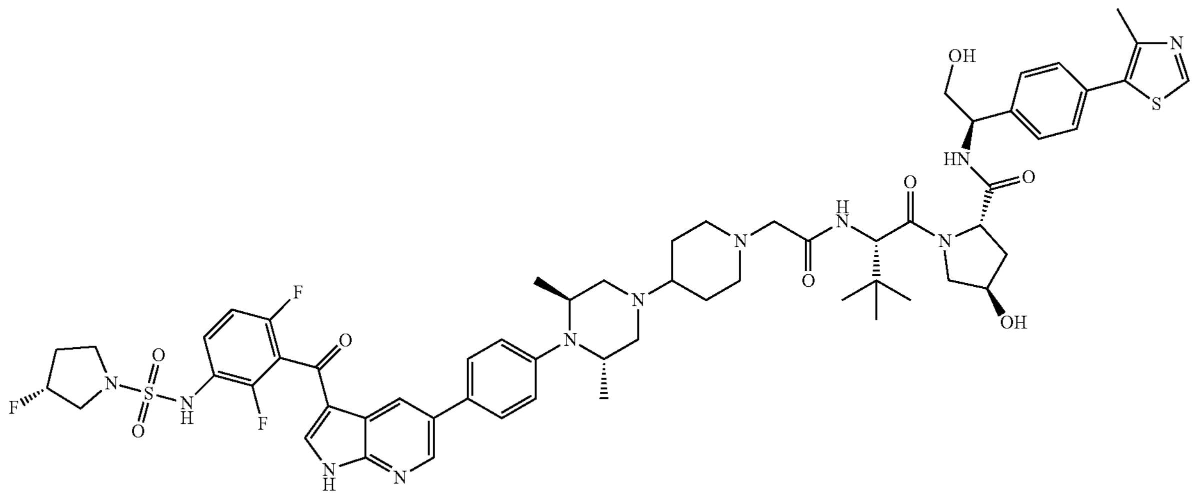
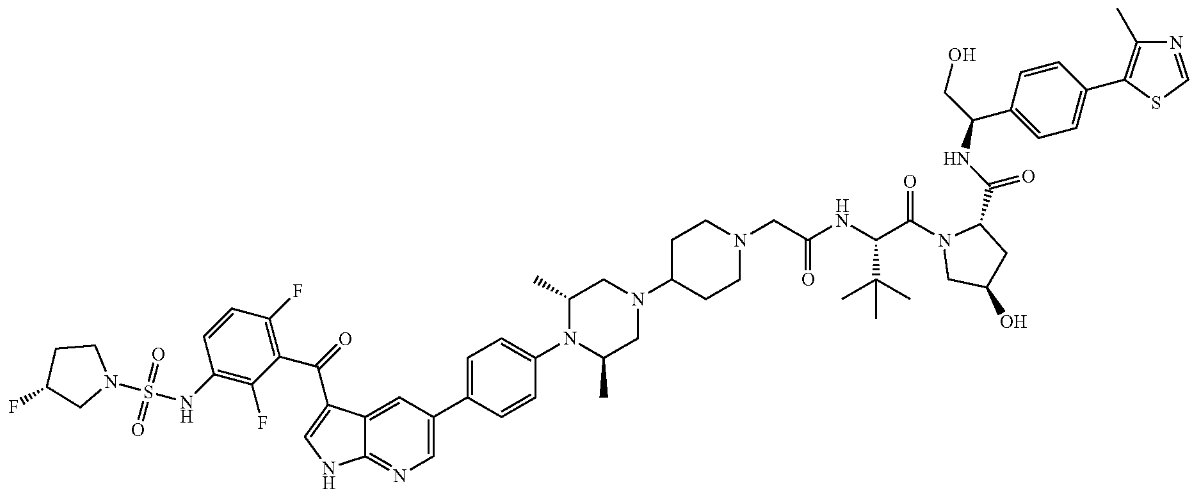

-continued
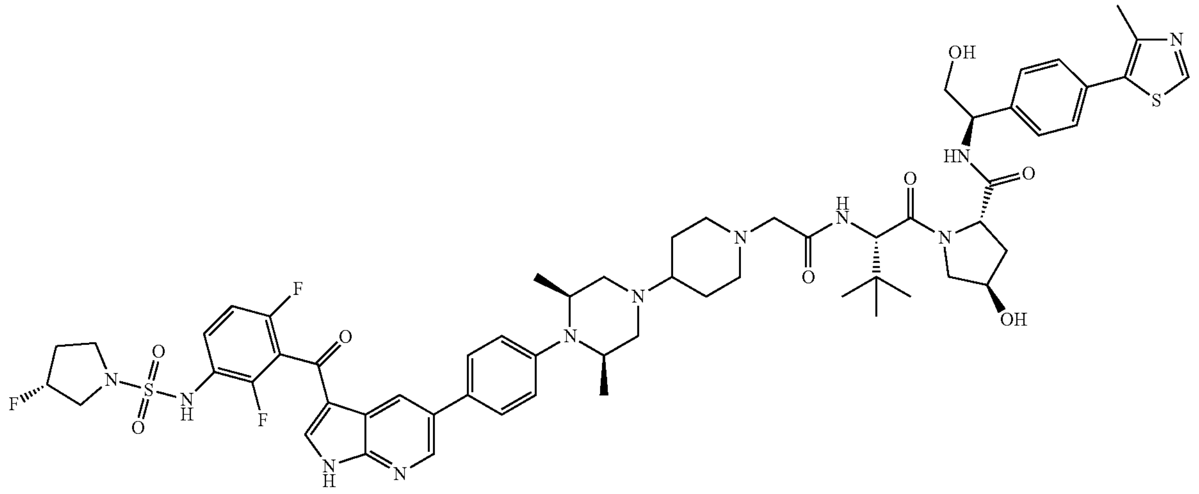
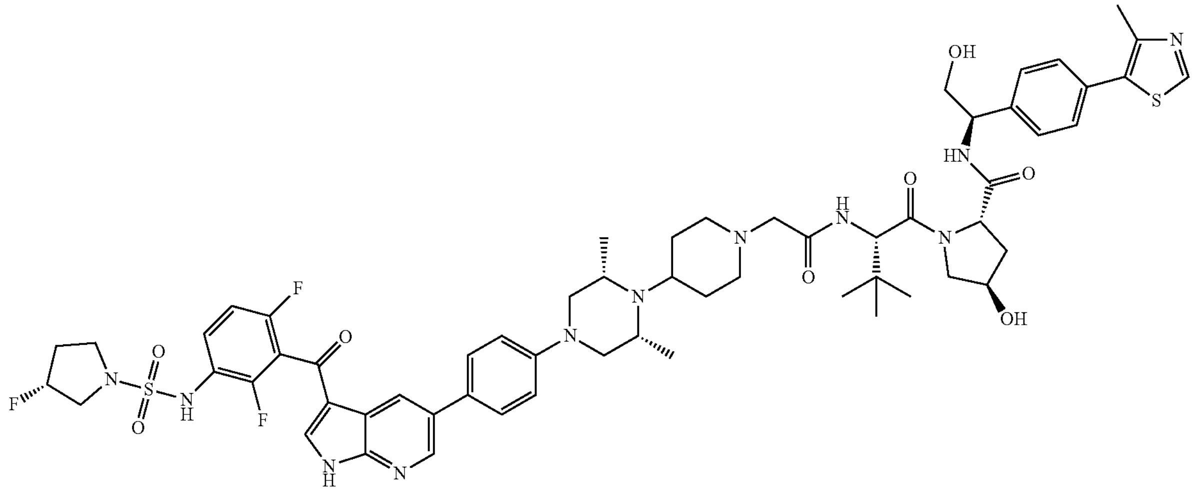
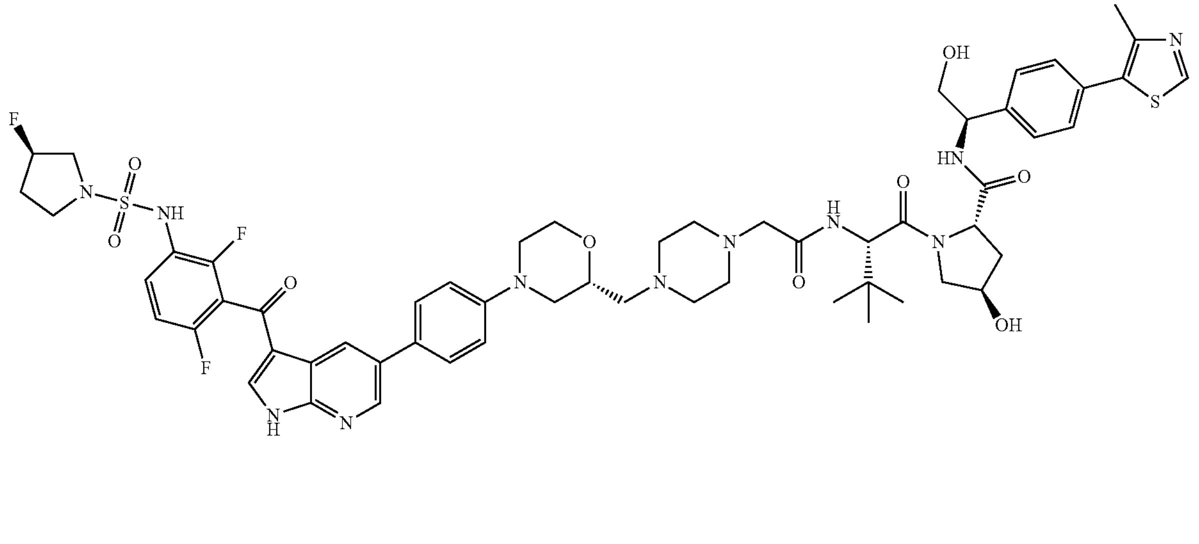

-continued
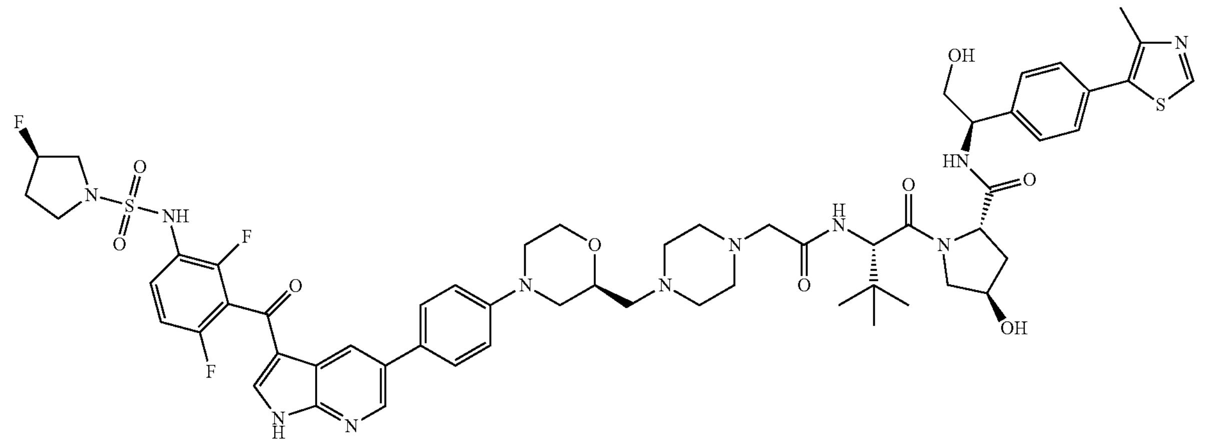
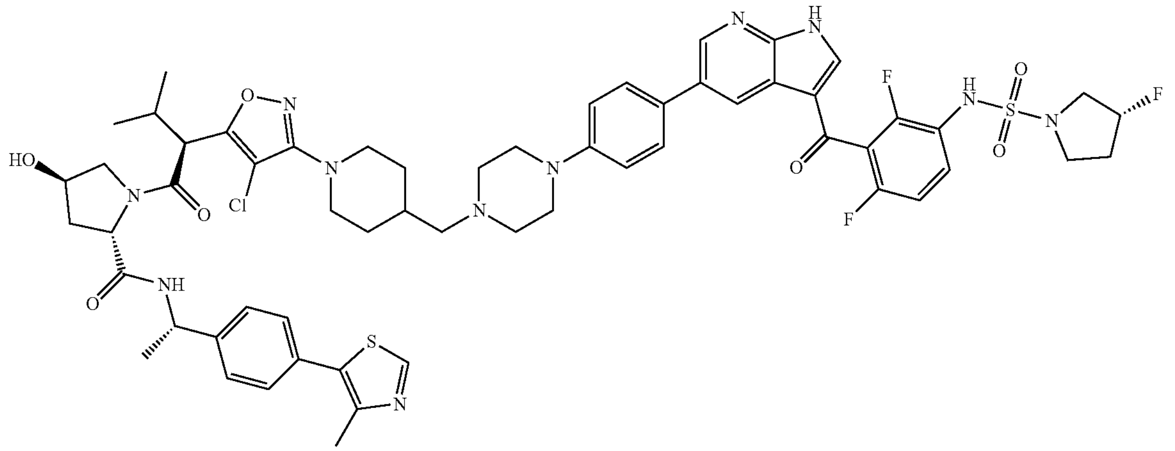
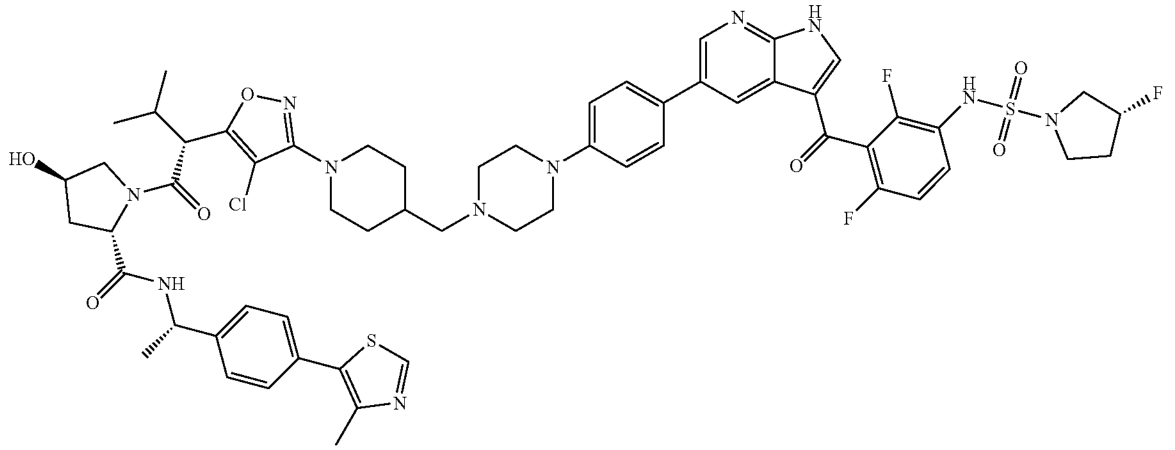

-continued
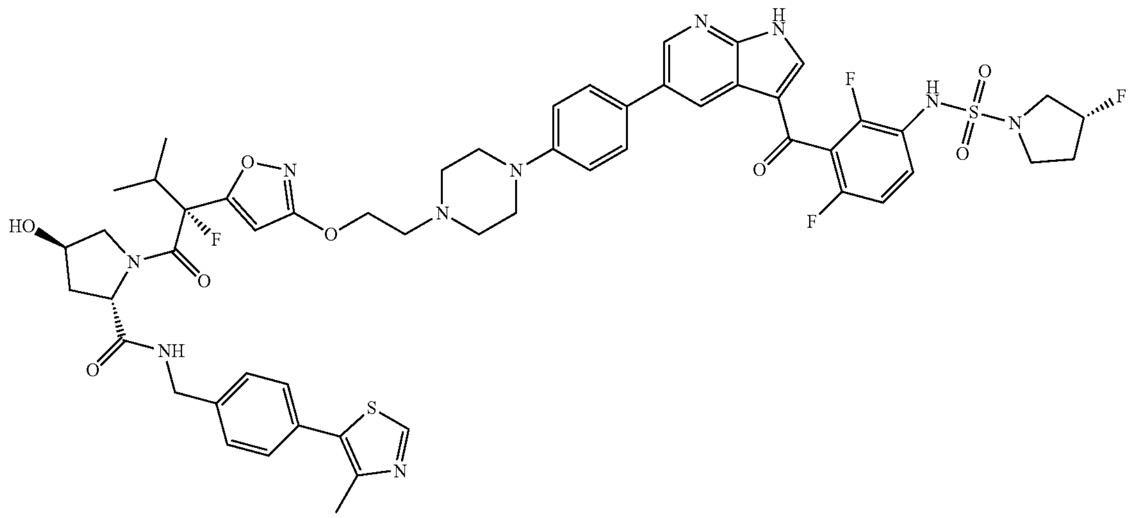
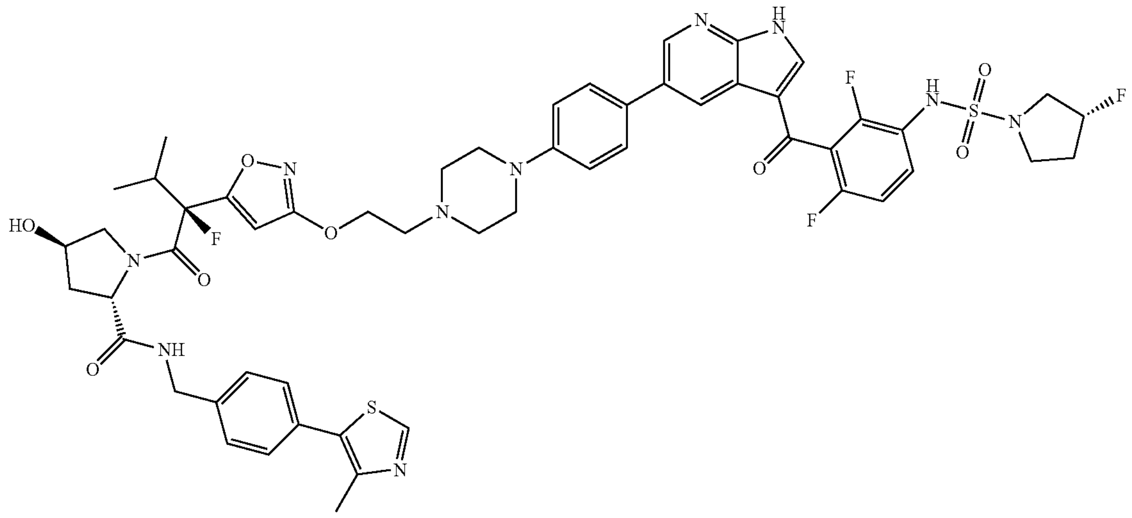
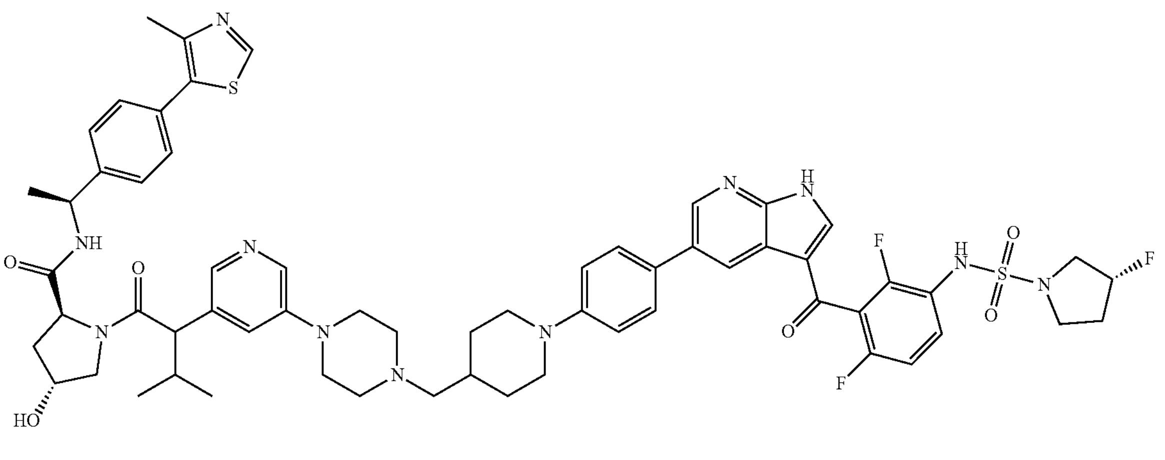

-continued
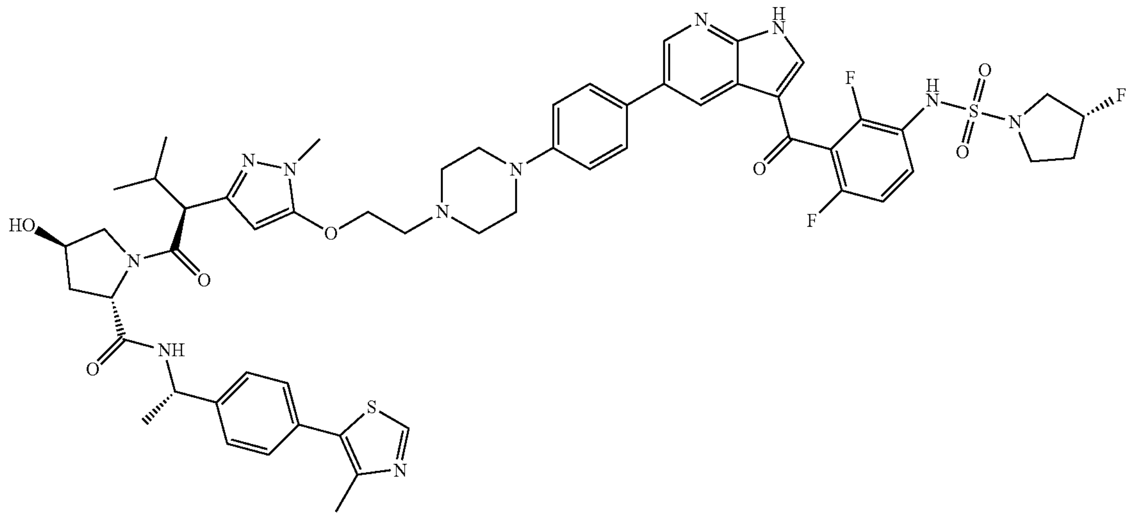
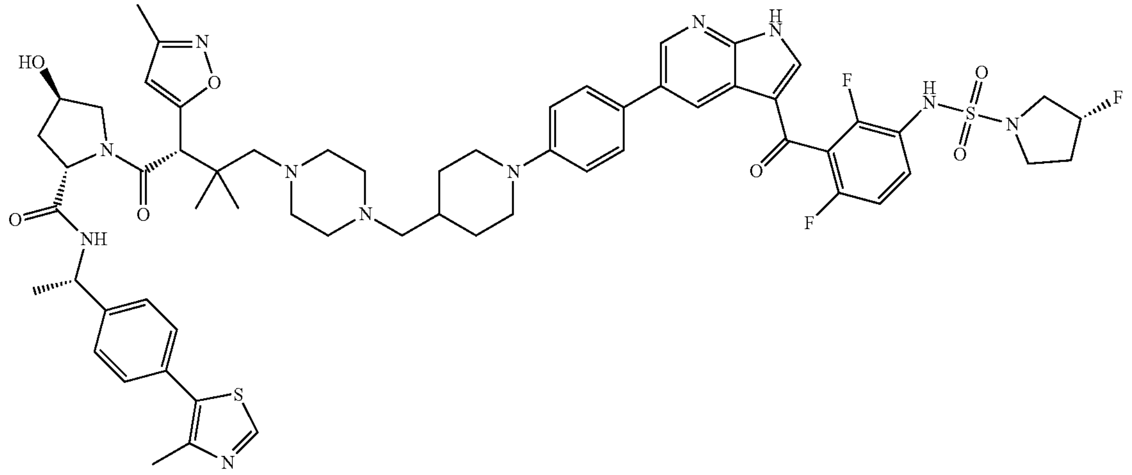
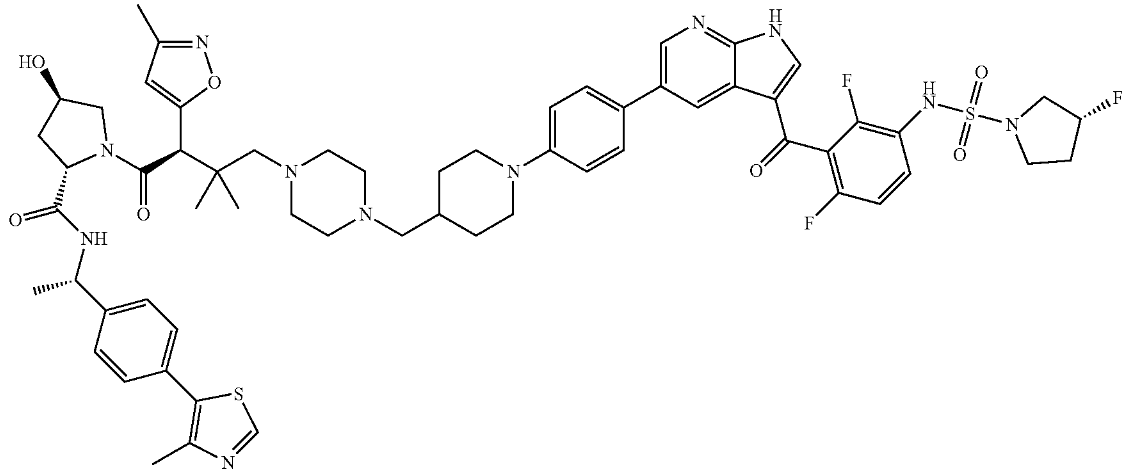

-continued
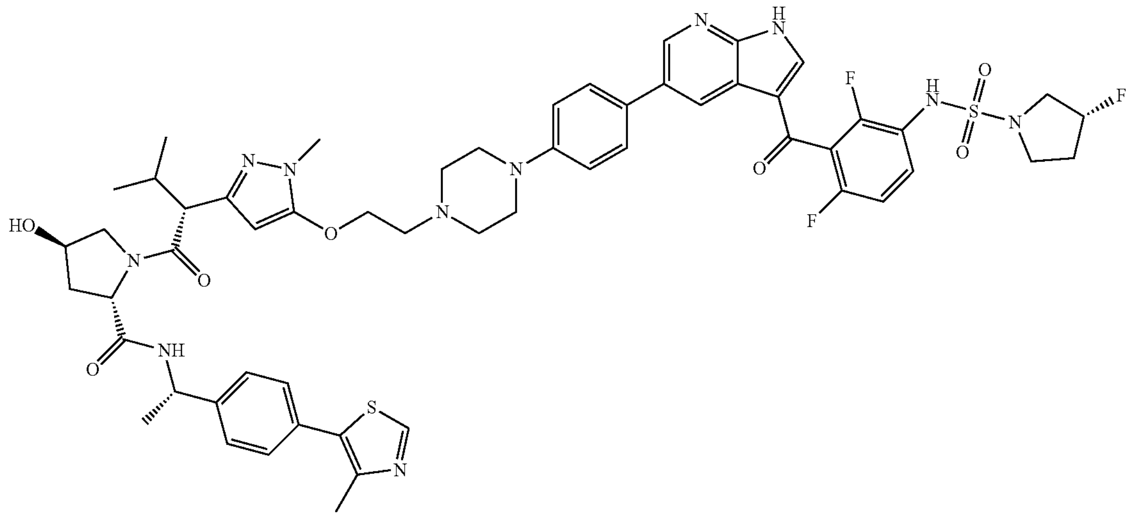
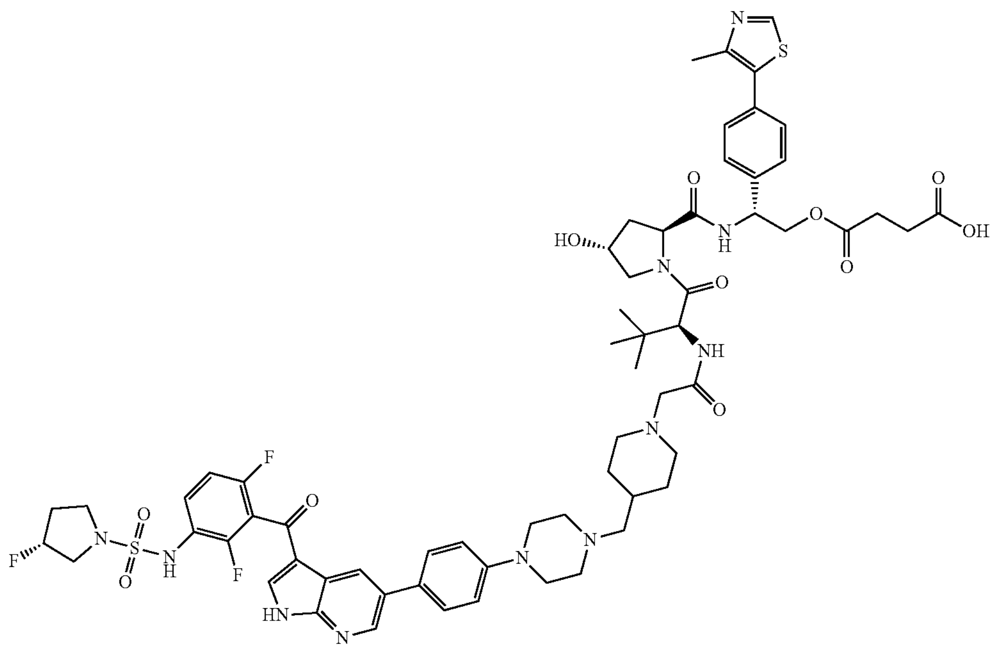

-continued
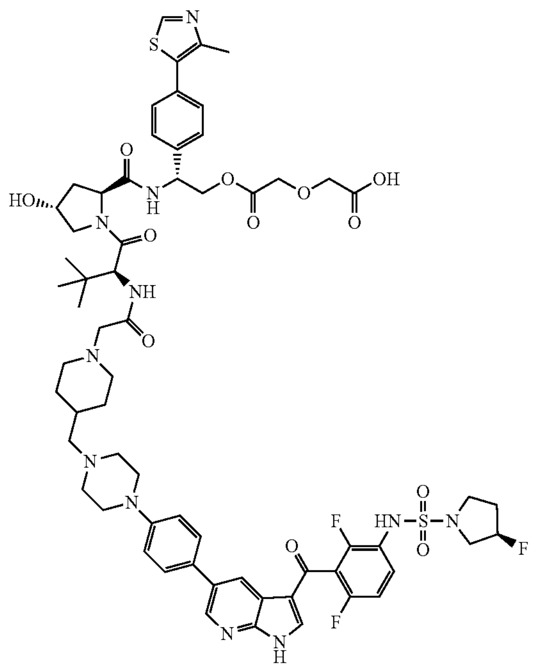
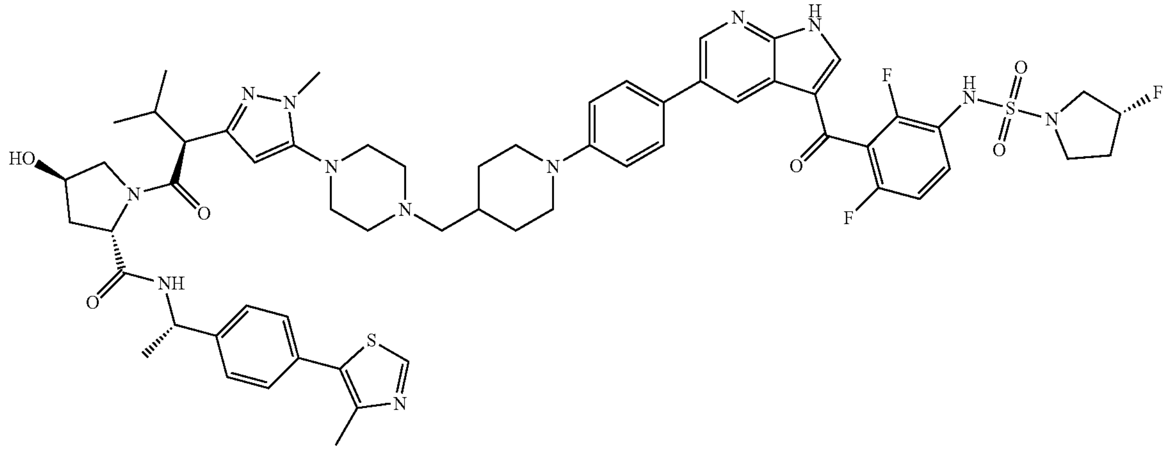
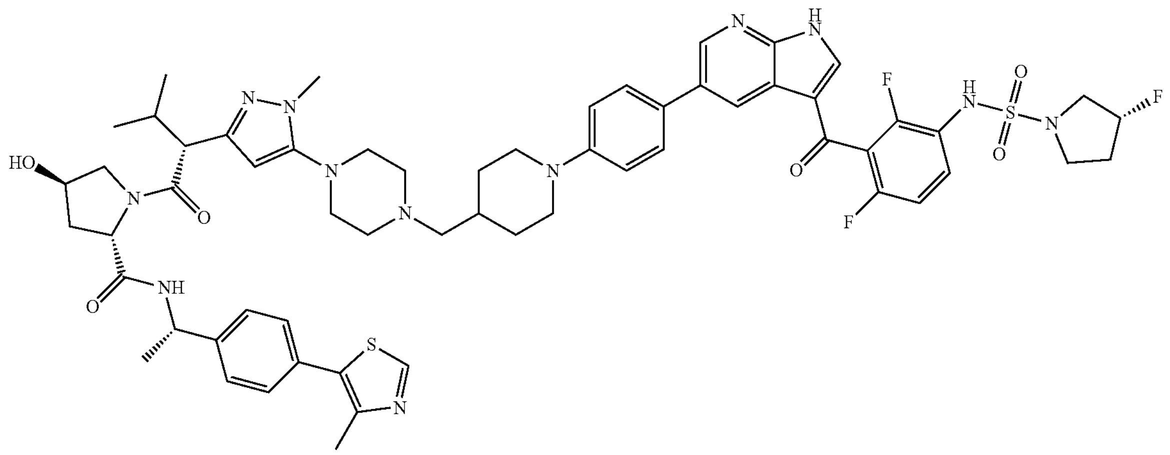

-continued
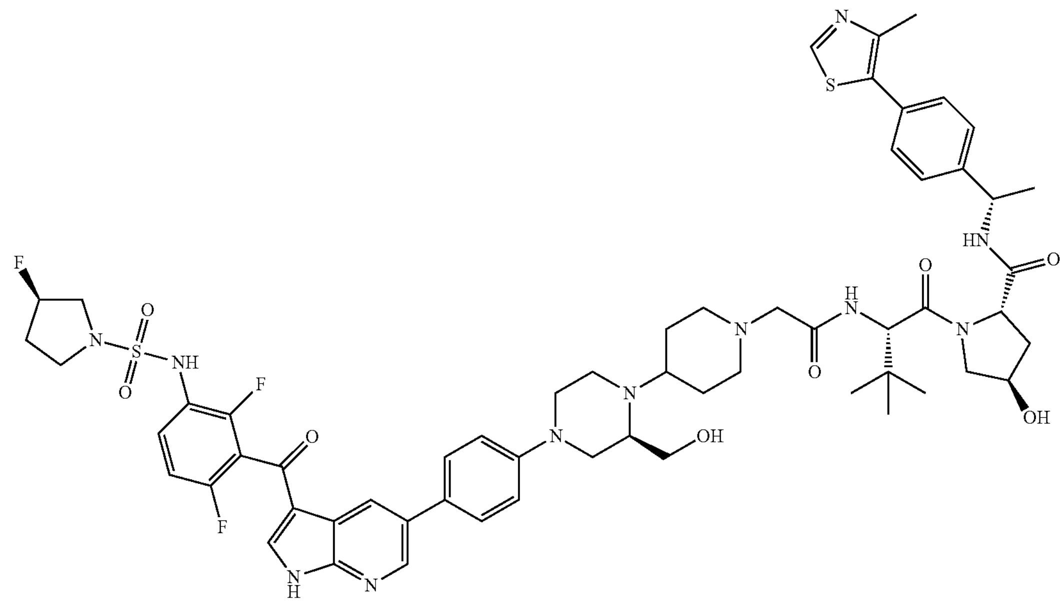
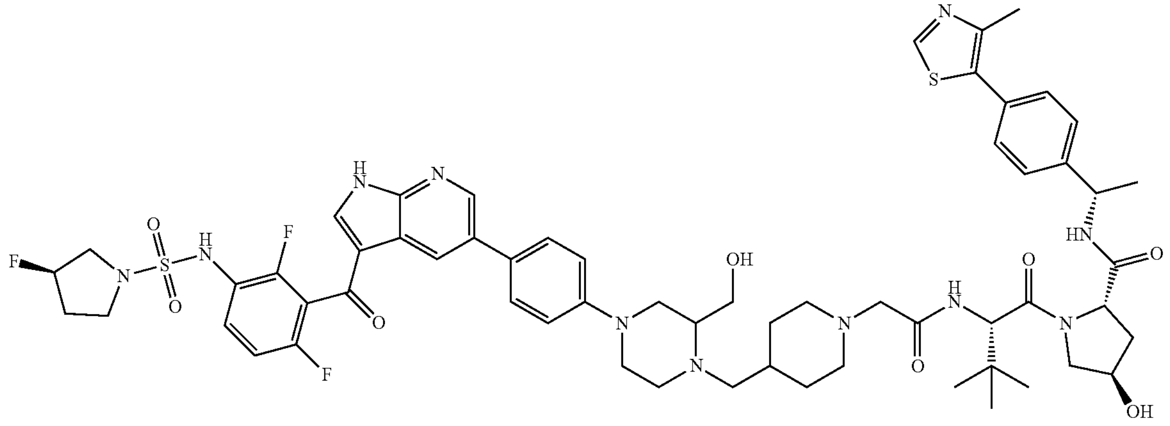
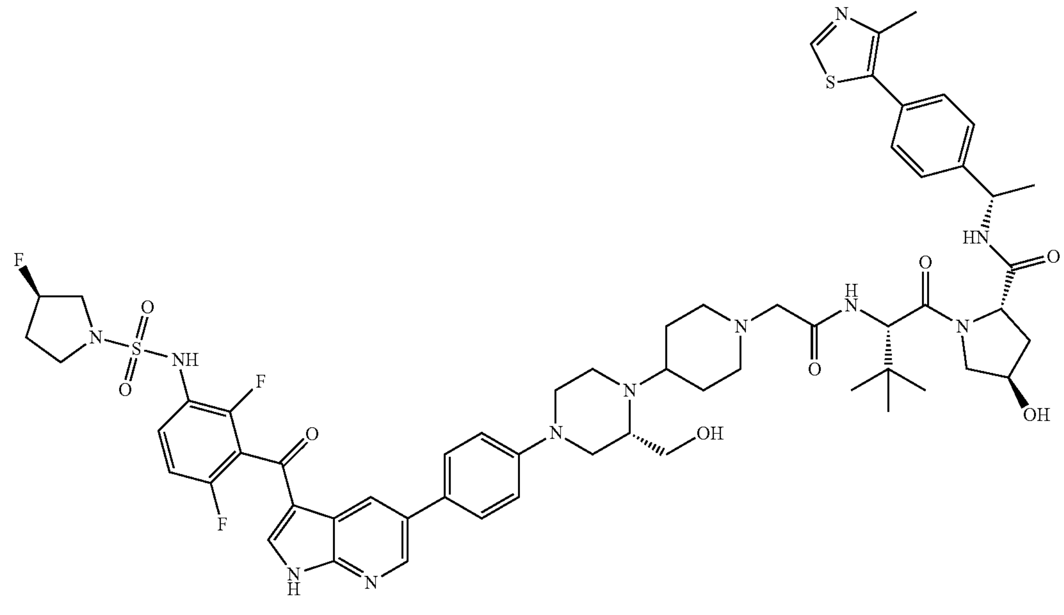

-continued
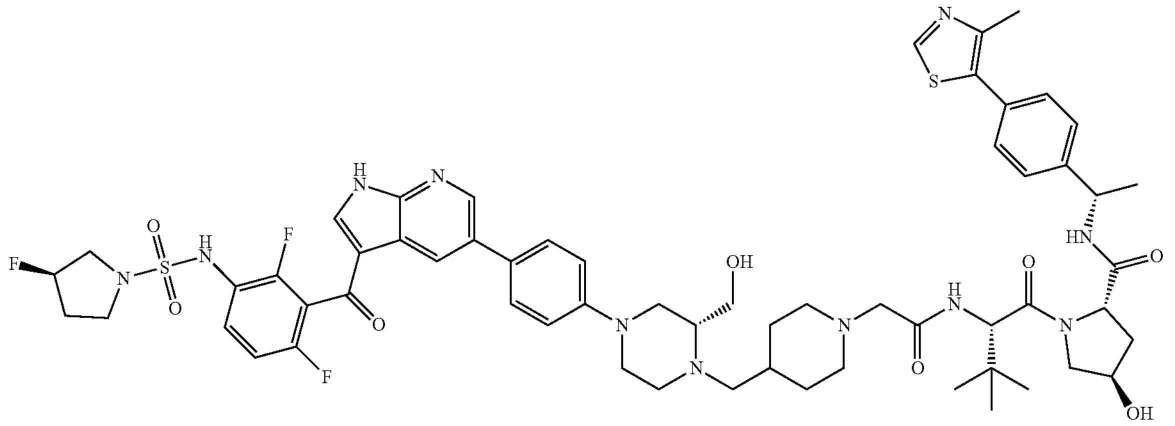
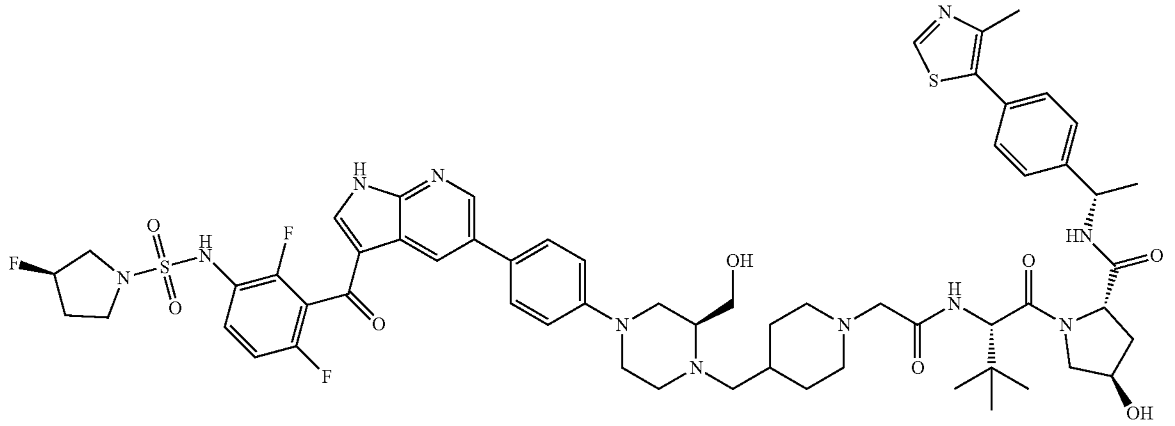
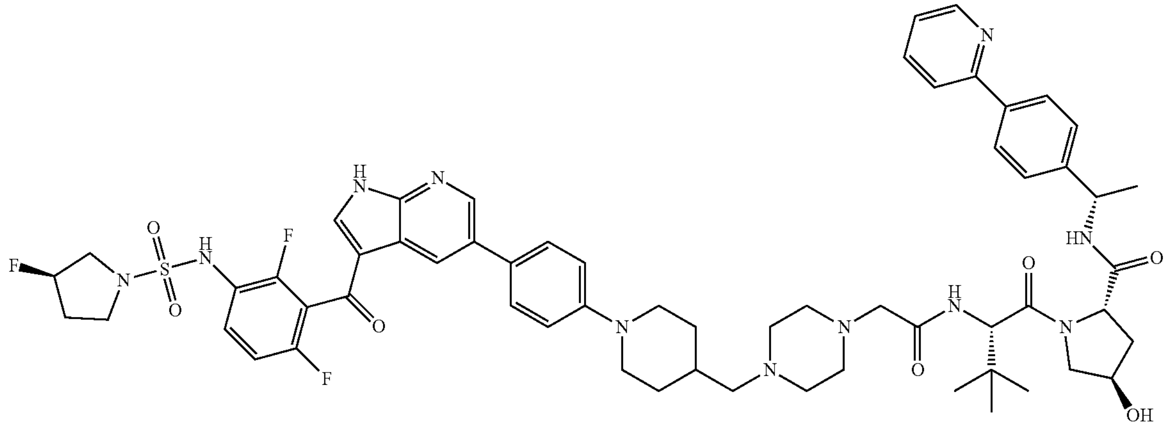
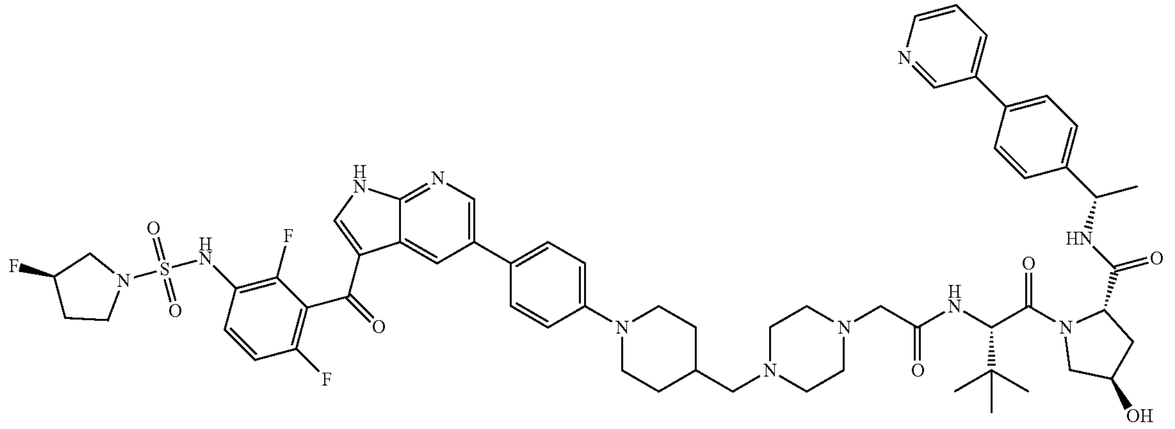

-continued
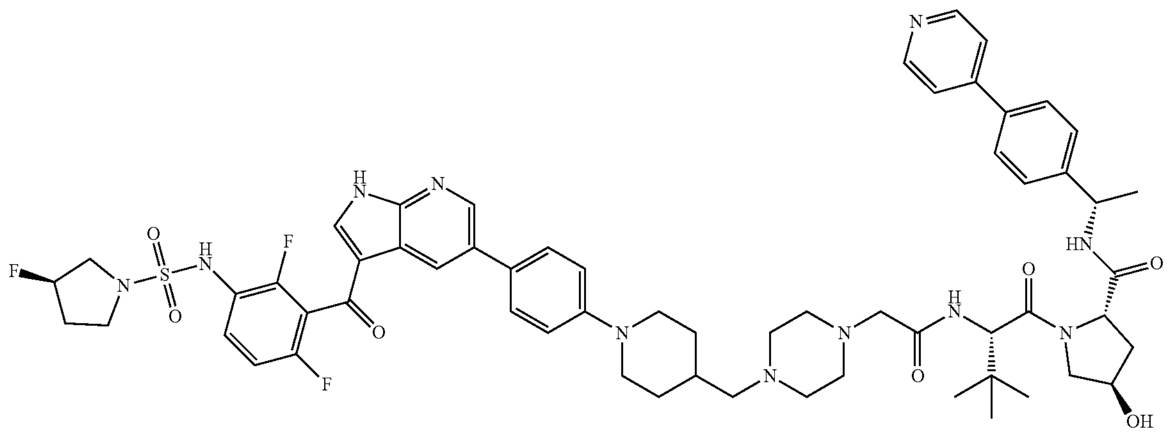
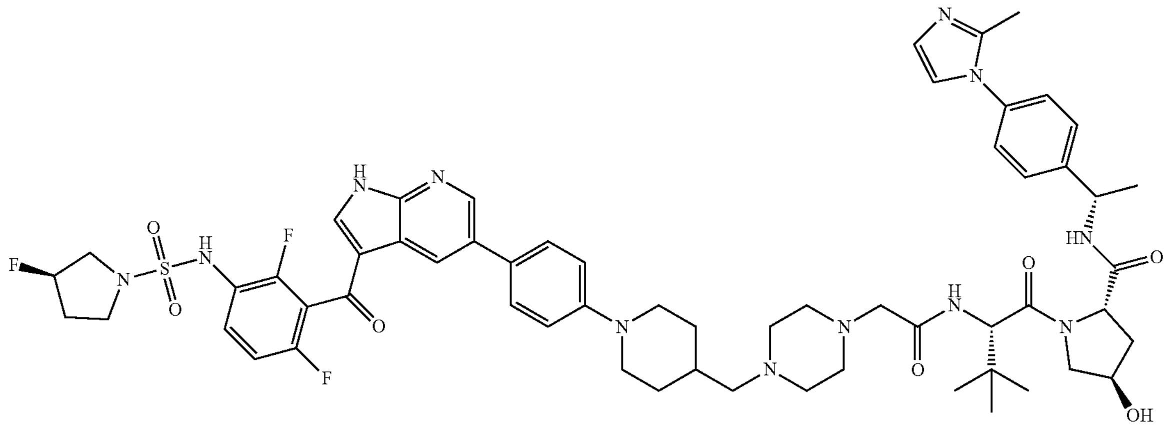
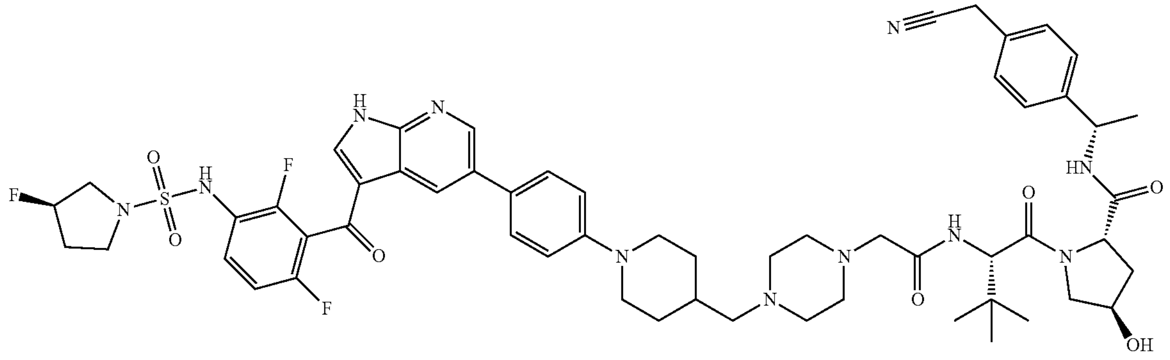
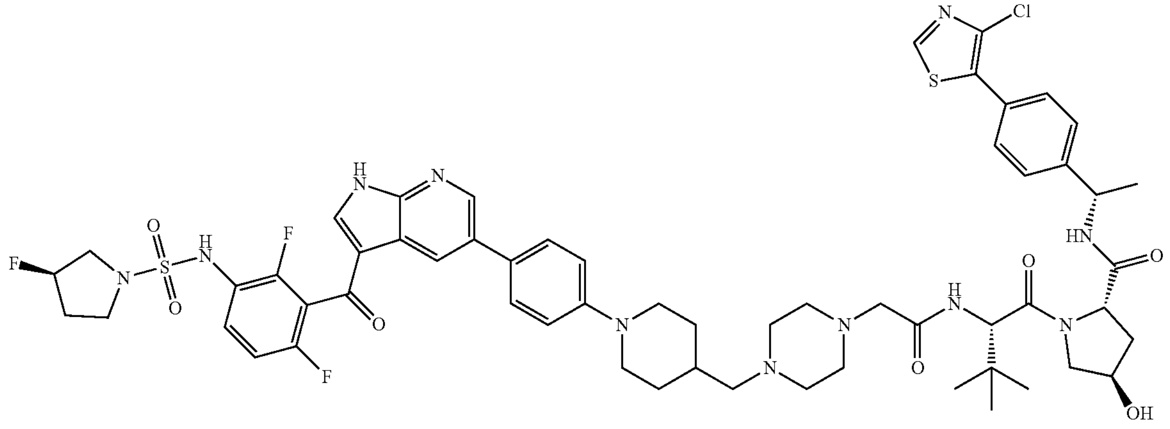

-continued
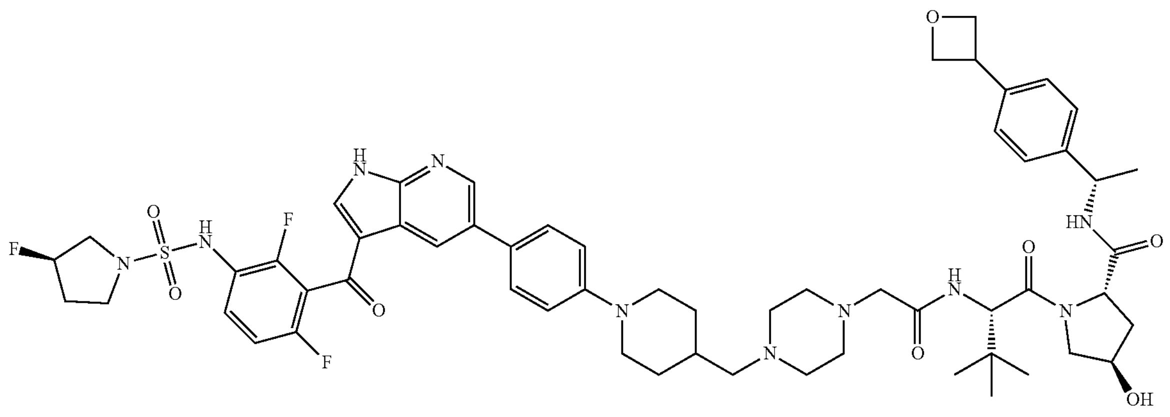
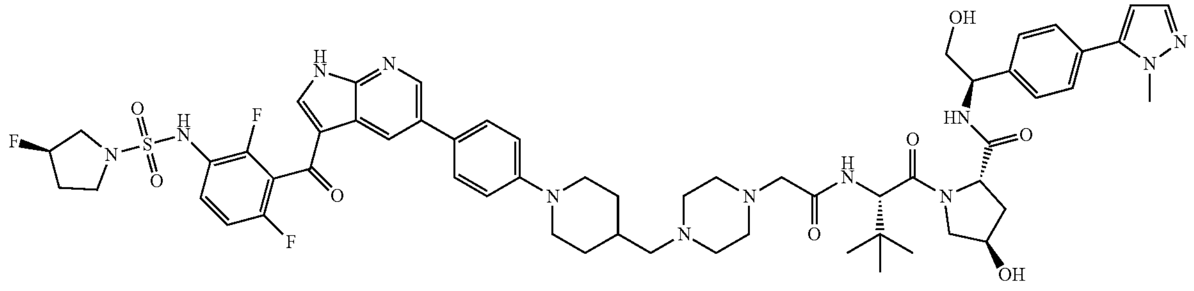
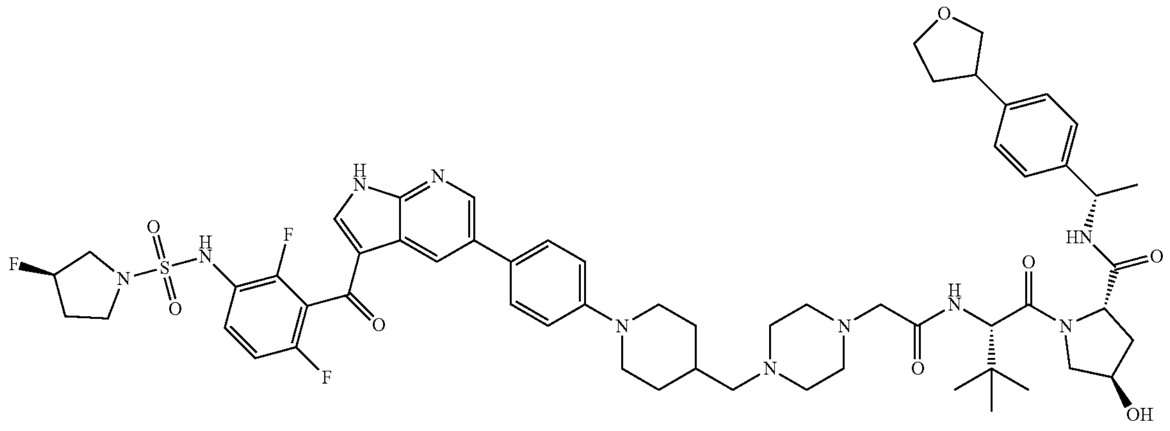

-continued
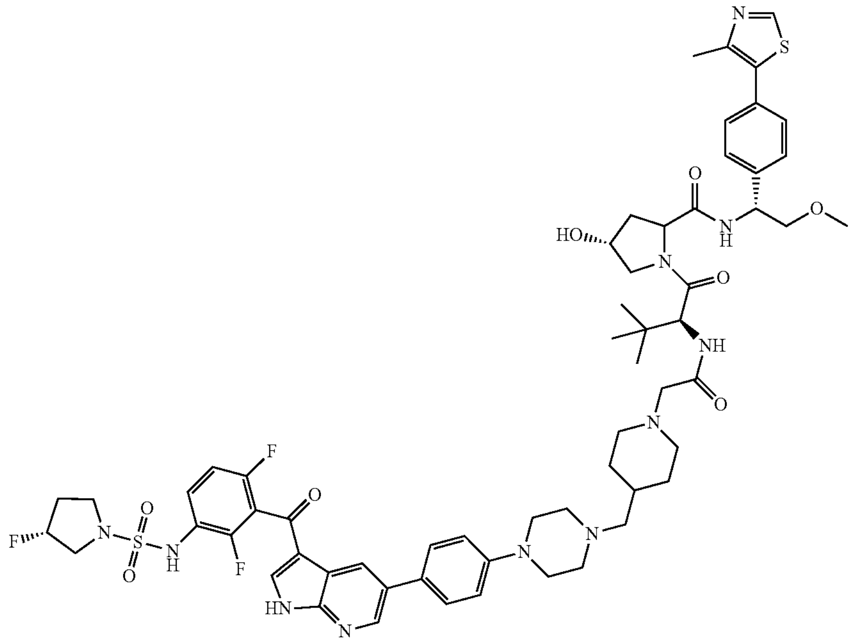
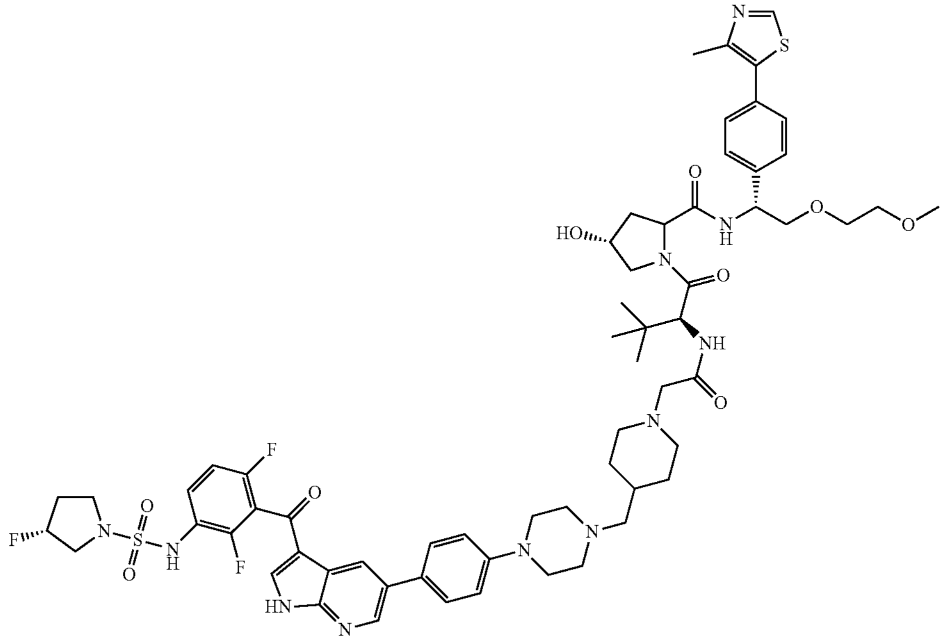
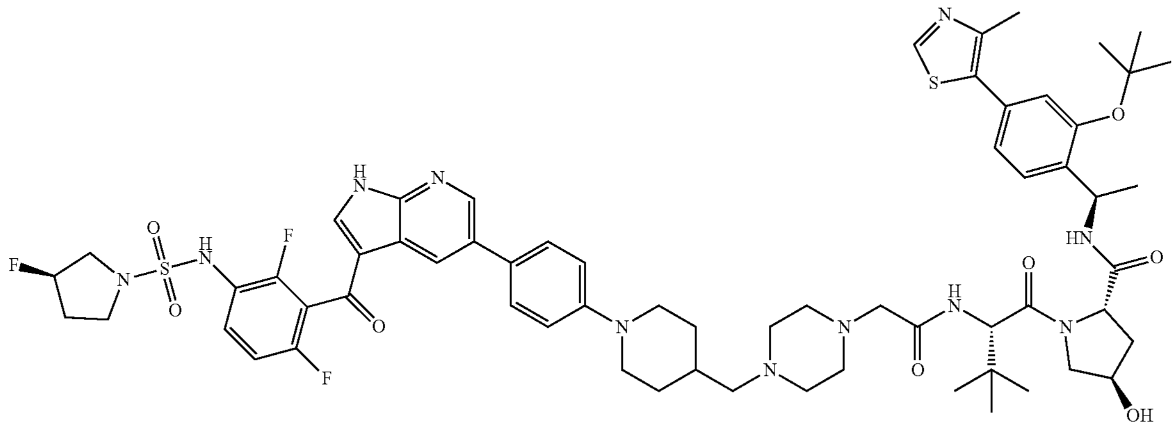

-continued

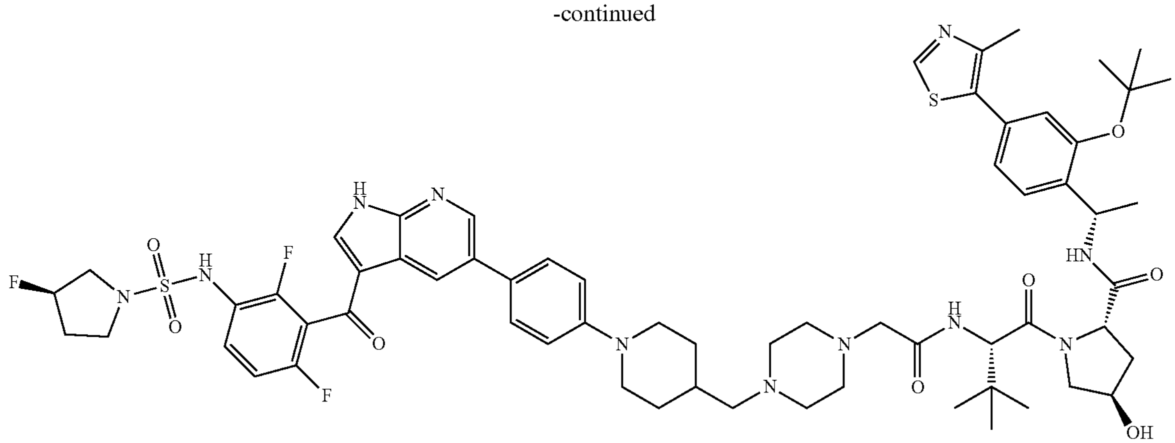

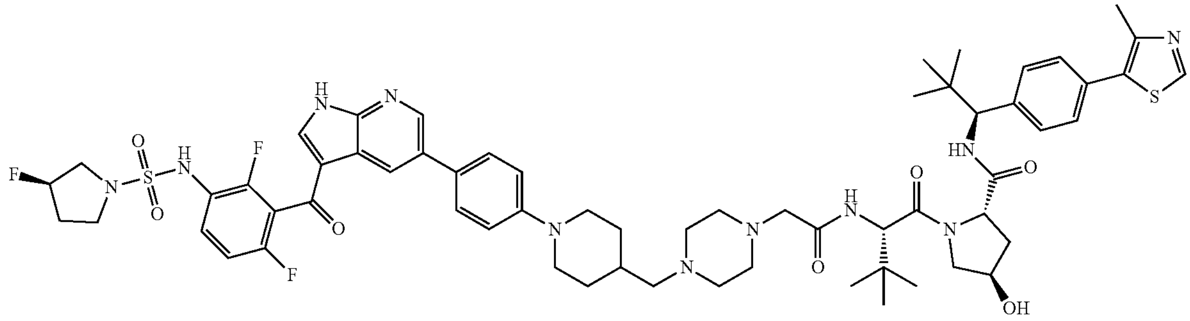

or a pharmaceutically acceptable salt thereof.

18. A pharmaceutical composition comprising an effective amount of a bifunctional compound according to claim 1, and a pharmaceutically acceptable carrier.

19. A method of treating a disease or disorder associated with BRaf accumulation and aggregation, the method comprising administering a pharmaceutical composition comprising a pharmaceutically acceptable carrier and an effective amount of at least one compound according to claim 1 to a subject, wherein the compound is effective in treating or ameliorating at least one symptom of the disease or disorder, and wherein the disease or disorder is renal cell carcinoma, pancreatic cancer, colorectal cancer, lung cancer, non-small cell lung cancer, ovarian cancer, thyroid cancer, pilocytic astrocytoma, prostate cancer, gastric cancer, hepatocellular carcinoma, or melanomacancer.

* * * * *